(12) United States Patent
Chan et al.

(10) Patent No.: US 11,034,692 B1
(45) Date of Patent: Jun. 15, 2021

(54) NAPHTHYRIDINES AS INHIBITORS OF HPK1

(71) Applicant: Genentech, Inc., South San Francisco, CA (US)

(72) Inventors: Bryan Chan, Foster City, CA (US); Blake Daniels, South San Francisco, CA (US); Joy Drobnick, Daly City, CA (US); Lewis Gazzard, Belmont, CA (US); Timothy Heffron, Burlingame, CA (US); Malcolm Huestis, San Francisco, CA (US); Jun Liang, Los Altos Hills, CA (US); Sushant Malhotra, Burlingame, CA (US); Rohan Mendonca, Pleasanton, CA (US); Naomi Rajapaksa, San Mateo, CA (US); Michael Siu, San Francisco, CA (US); Craig Stivala, San Mateo, CA (US); John Tellis, San Mateo, CA (US); Weiru Wang, Lafayette, CA (US); BinQing Wei, Belmont, CA (US); Aihe Zhou, San Jose, CA (US); Matthew W. Cartwright, Harlow (GB); Emanuela Gancia, Harlow (GB); Graham Jones, Harlow (GB); Michael Lainchbury, Harlow (GB); Andrew Madin, Harlow (GB); Eileen Seward, Harlow (GB); David Favor, Shanghai (CN); Kin Chiu Fong, Shanghai (CN); Andrew Good, Shanghai (CN); Yonghan Hu, Shanghai (CN); Baihua Hu, Beijing (CN); Aijun Lu, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/542,129

(22) Filed: Aug. 15, 2019

Related U.S. Application Data

(63) Continuation of application No. 15/942,321, filed on Mar. 30, 2018, now Pat. No. 10,407,424.

(30) Foreign Application Priority Data

Mar. 30, 2017 (WO) ................ PCT/CN2017/078792
Feb. 15, 2018 (WO) ................ PCT/CN2018/076909

(51) Int. Cl.
| | |
|---|---|
| *C07D 471/04* | (2006.01) |
| *A61K 45/06* | (2006.01) |
| *A61P 35/00* | (2006.01) |
| *A61K 31/444* | (2006.01) |
| *A61K 31/4375* | (2006.01) |
| *A61K 31/506* | (2006.01) |
| *C07D 519/00* | (2006.01) |
| *A61K 31/4545* | (2006.01) |
| *A61K 31/4725* | (2006.01) |
| *A61K 31/5383* | (2006.01) |
| *A61K 31/496* | (2006.01) |
| *A61K 31/5377* | (2006.01) |
| *A61K 31/5025* | (2006.01) |
| *A61K 31/551* | (2006.01) |
| *A61K 31/55* | (2006.01) |

(52) U.S. Cl.
CPC ........ *C07D 471/04* (2013.01); *A61K 31/4375* (2013.01); *A61K 31/444* (2013.01); *A61K 31/4545* (2013.01); *A61K 31/4725* (2013.01); *A61K 31/496* (2013.01); *A61K 31/506* (2013.01); *A61K 31/5025* (2013.01); *A61K 31/5377* (2013.01); *A61K 31/5383* (2013.01); *A61K 31/55* (2013.01); *A61K 31/551* (2013.01); *A61K 45/06* (2013.01); *A61P 35/00* (2018.01); *C07D 519/00* (2013.01)

(58) Field of Classification Search
CPC .................................................... C07D 471/04
See application file for complete search history.

(56) References Cited

U.S. PATENT DOCUMENTS

| | | | |
|---|---|---|---|
| 10,407,424 B2 * | 9/2019 | Chan ................ | A61K 31/5377 |
| 2014/0322195 A1 | 10/2014 | Voss et al. | |

FOREIGN PATENT DOCUMENTS

| | | |
|---|---|---|
| WO | 2009/023193 A1 | 2/2009 |
| WO | 2013/063068 A1 | 5/2013 |
| WO | 2016/205942 A1 | 12/2016 |

OTHER PUBLICATIONS

McMahon et al (2000).*
Pinedo et al. (2000).*
Di Bartolo et al., "A novel pathway down-modulating T cell activation involves HPK-1-dependent recruitment of 14-3-3 proteins on SLP-76" J Exp Med 204(3):681-691 (2007).
Pinedo et al., "Translational Research: The Role of VEGF in Tumor Angiogenesis" The Oncologist(5):1-2 (2000).

(Continued)

*Primary Examiner* — Paul V Ward
(74) *Attorney, Agent, or Firm* — Zong-Qiang Bill Tian

(57) ABSTRACT

Naphthyridine compounds and their use as inhibitors of HPK1 are described. The compounds are useful in treating HPK1-dependent disorders and enhancing an immune response. Also described are methods of inhibiting HPK1, methods of treating HPK1-dependent disorders, methods for enhancing an immune response, and methods for preparing the naphthyridine compounds.

20 Claims, No Drawings

Specification includes a Sequence Listing.

(56) References Cited

OTHER PUBLICATIONS

Lasserre et al., "Release of serine/threonine-phosphorylated adaptors from signaling microclusters down-regulates T cell activation" J Cell Biol 195(5):839-853 (2011).
International Search Report and Written Opinion for International Patent Application No. PCT/US2018/025562 completed on Jun. 25, 2018.
McMahon et al., "VEGF Receptor Signaling in Tumor Angiogenesis" The Oncologist(5):3-10 (2000).

* cited by examiner

SEQUENCE LISTING

```
<160> NUMBER OF SEQ ID NOS: 4

<210> SEQ ID NO 1
<211> LENGTH: 2502
<212> TYPE: DNA
<213> ORGANISM: Homo sapiens

<400> SEQUENCE: 1
atggacgtcg tggaccctga cattttcaat agagaccccc gggaccacta tgacctgcta      60
cagcggctgg gtggcggcac gtatggggaa gtctttaagg ctcgagacaa ggtgtcaggg     120
gacctggtgg cactgaagat ggtgaagatg gagcctgatg atgatgtctc caccctctcag    180 aaggaaatcc tcatattgaa aacttgccgg cacgccaaca tcgtggccta ccatgggagt     240
tatctctggt tgcagaaact ctggatctgc atggaattct gtggggctgg ttctctccag     300
gacatctacc aagtgacagg ctccctgtca gagctccaga ttagctatgt ctgccgggaa     360
gtgctccagg gactggccta tttgcactca cagaagaaga tacacaggga catcaaggga     420
gctaacatcc tcatcaatga tgctggggag gtcagattgg ctgactttgg catctcggcc     480
cagattgggg ctacactggc cagacgcctc tctttcattg ggacaccta ctggatggct     540 ccggaagtgg cagctgtggc cctgaaggga ggatacaatg agctgtgtga catctggtcc    600
ctgggcatca cggccatcga actggccgag ctacagccac cgctctttga tgtgcaccct    660
ctcagagttc tcttcctcat gaccaagagt ggctaccagc ctcccgact gaaggaaaaa     720 ggcaaatggt cggctgcctt ccacaacttc atcaaagtca ctctgactaa gagtcccaag    780
aaacgaccca gcgccaccaa gatgctcagt catcaactgt atcccagcc tgggctgaat    840 cgaggcctga tcctggatct tcttgacaaa ctgaagaatc ccgggaaagg accctccatt    900
```

-continued

```
gggggacattg aggatgagga gcccgagcta ccccctgcta tccctcggcg gatcagatcc      960
acccaccgct ccagctctct ggggatccca gatgcagact gctgtcggcg gcacatggag      1020
ttcaggaagc tccgaggaat ggagaccaga cccccagcca acaccgctcg cctacagcct      1080
cctcgagacc tcaggagcag cagccccagg aagcaactgt cagagtcgtc tgacgatgac      1140
tatgacgacg tggacatccc caccctgca gaggacacac ctcctccact tcccccaag       1200 cccaagttcc gttctccatc agacgagggt cctgggagca tggggatga tgggcagctg      1260 agcccggggg tgctggtccg gtgtgccagt gggcccccac caaacagccc ccgtcctggg      1320
cctcccccat ccaccagcag ccccccacctc accgcccatt cagaaccctc actctggaac     1380 ccacccctccc gggagcttga caagccccca cttctgcccc caagaagga aaagatgaag       1440 agaaagggat gtgcccttct cgtaaagttg ttcaatggct gccccctccg gatccacagc      1500
acggccgcct ggacacatcc ctccaccaag gaccagcacc tgctcctggg ggcagaggaa      1560
ggcatcttca tcctgaaccg gaatgaccag gaggccacgc tggaaatgct ctttcctagc      1620
cggactacgt gggtgtactc catcaacaac gttctcatgt ctctctcagg aaagacccc       1680 cacctgtatt ctcatagcat ccttggcctg ctggaacgga agagaccag agcaggaaac      1740 cccatcgctc acattagccc ccaccgccta ctggcaagga agaacatggt ttccaccaag      1800
atccaggaca ccaaaggctg ccgggcgtgc tgtgtggcgg agggtgcgag ctctgggggc      1860
ccgttcctgt gcggtgcatt ggagacgtcc gttgtcctgc ttcagtggta ccagcccatg      1920
aacaaattcc tgcttgtccg gcaggtgctg ttcccactgc cgacgcctct gtccgtgttc      1980
gcgctgctga ccgggccagg ctctgagctg cccgctgtgt gcatcggcgt gagccccggg      2040
cggccgggga agtcggtgct cttccacacg gtgcgctttg gcgcgctctc ttgctggctg      2100
ggcgagatga gcaccgagca caggggaccc gtgcaggtga cccaggtaga ggaagatatg      2160
gtgatggtgt tgatggatgg ctctgtgaag ctggtgaccc cggaggggtc cccagtccgg      2220
ggacttcgca cacctgagat ccccatgacc gaagcggtgg aggccgtggc tatggttgga      2280
ggtcagcttc aggccttctg gaagcatgga gtgcaggtgt gggctctagg ctcggatcag      2340
ctgctacagg agctgagaga ccctaccctc actttccgtc tgcttggctc ccccaggctg      2400
gagtgcagtg gcacgatctc gcctcactgc aacctcctcc tcccaggttc aagcaattct      2460
cctgcctcag cctcccgagt agctgggatt acaggcctgt ag                        2502
```

<210> SEQ ID NO 2
<211> LENGTH: 833
<212> TYPE: PRT
<213> ORGANISM: Homo sapiens

<400> SEQUENCE: 2

```
Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95
```

```
Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
            115                 120                 125

His Ser Gln Lys Lys Ile His Arg Asp Ile Lys Gly Ala Asn Ile Leu
            130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Val Ala Leu Lys Gly Gly Tyr
            180                 185                 190

Asn Glu Leu Cys Asp Ile Trp Ser Leu Gly Ile Thr Ala Ile Glu Leu
            195                 200                 205

Ala Glu Leu Gln Pro Pro Leu Phe Asp Val His Pro Leu Arg Val Leu
            210                 215                 220

Phe Leu Met Thr Lys Ser Gly Tyr Gln Pro Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270

Leu Val Ser Gln Pro Gly Leu Asn Arg Gly Leu Ile Leu Asp Leu Leu
            275                 280                 285

Asp Lys Leu Lys Asn Pro Gly Lys Gly Pro Ser Ile Gly Asp Ile Glu
            290                 295                 300

Asp Glu Glu Pro Glu Leu Pro Pro Ala Ile Pro Arg Arg Ile Arg Ser
305                 310                 315                 320

Thr His Arg Ser Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
            340                 345                 350

Ala Asn Thr Ala Arg Leu Gln Pro Pro Arg Asp Leu Arg Ser Ser Ser
            355                 360                 365

Pro Arg Lys Gln Leu Ser Glu Ser Ser Asp Asp Tyr Asp Asp Val
            370                 375                 380

Asp Ile Pro Thr Pro Ala Glu Asp Thr Pro Pro Pro Leu Pro Pro Lys
385                 390                 395                 400

Pro Lys Phe Arg Ser Pro Ser Asp Glu Gly Pro Gly Ser Met Gly Asp
                405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
            435                 440                 445

His Leu Thr Ala His Ser Glu Pro Ser Leu Trp Asn Pro Pro Ser Arg
            450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
            500                 505                 510
```

```
His Leu Leu Leu Gly Ala Glu Glu Gly Ile Phe Ile Leu Asn Arg Asn
            515                 520                 525

Asp Gln Glu Ala Thr Leu Glu Met Leu Phe Pro Ser Arg Thr Thr Trp
530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
        595                 600                 605

Ala Cys Cys Val Ala Glu Gly Ala Ser Ser Gly Gly Pro Phe Leu Cys
    610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
                645                 650                 655

Leu Ser Val Phe Ala Leu Leu Thr Gly Pro Gly Ser Glu Leu Pro Ala
            660                 665                 670

Val Cys Ile Gly Val Ser Pro Gly Arg Pro Gly Lys Ser Val Leu Phe
        675                 680                 685

His Thr Val Arg Phe Gly Ala Leu Ser Cys Trp Leu Gly Glu Met Ser
    690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                725                 730                 735

Ser Pro Val Arg Gly Leu Arg Thr Pro Glu Ile Pro Met Thr Glu Ala
            740                 745                 750

Val Glu Ala Val Ala Met Val Gly Gly Gln Leu Gln Ala Phe Trp Lys
        755                 760                 765

His Gly Val Gln Val Trp Ala Leu Gly Ser Asp Gln Leu Leu Gln Glu
    770                 775                 780

Leu Arg Asp Pro Thr Leu Thr Phe Arg Leu Leu Gly Ser Pro Arg Leu
785                 790                 795                 800

Glu Cys Ser Gly Thr Ile Ser Pro His Cys Asn Leu Leu Leu Pro Gly
                805                 810                 815

Ser Ser Asn Ser Pro Ala Ser Ala Ser Arg Val Ala Gly Ile Thr Gly
            820                 825                 830

Leu

<210> SEQ ID NO 3
<211> LENGTH: 2466
<212> TYPE: DNA
<213> ORGANISM: Homo sapiens

<400> SEQUENCE: 3
atggacgtcg tggaccctga cattttcaat agagaccccc gggaccacta tgacctgcta      60
cagcggctgg gtggcggcac gtatggggaa gtctttaagg ctcgagacaa ggtgtcaggg     120
gacctggtgg cactgaagat ggtgaagatg gagcctgatg atgatgtctc cacccttcag     180
aaggaaatcc tcatattgaa aacttgccgg cacgccaaca tcgtggccta ccatgggagt     240
tatctctggt tgcagaaact ctggatctgc atggaattct gtgggctggt tctctccag      300
```

-continued

| | |
|---|---|
| gacatctacc aagtgacagg ctccctgtca gagctccaga ttagctatgt ctgccgggaa | 360 |
| gtgctccagg gactggccta tttgcactca cagaagaaga tacacaggga catcaaggga | 420 |
| gctaacatcc tcatcaatga tgctggggag gtcagattgg ctgactttgg catctcggcc | 480 |
| cagattgggg ctacactggc cagacgcctc tctttcattg ggacacccta ctggatggct | 540 |
| ccggaagtgg cagctgtggc cctgaaggga ggatacaatg agctgtgtga catctggtcc | 600 |
| ctgggcatca cggccatcga actggccgag ctacagccac cgctctttga tgtgcaccct | 660 |
| ctcagagttc tcttcctcat gaccaagagt ggctaccagc tccccgact gaaggaaaaa | 720 |
| ggcaaatggt cggctgcctt ccacaacttc atcaaagtca ctctgactaa gagtcccaag | 780 |
| aaacgaccca gcgccaccaa gatgctcagt catcaactgg tatcccagcc tgggctgaat | 840 |
| cgaggcctga tcctggatct tcttgacaaa ctgaagaatc cggggaaagg accctccatt | 900 |
| ggggacattg aggatgagga gcccgagcta ccccctgcta tccctcggcg gatcagatcc | 960 |
| acccaccgct ccagctctct ggggatccca gatgcagact gctgtcggcg cacatggag | 1020 |
| ttcaggaagc tccgaggaat ggagaccaga ccccagcca cacccgctcg cctacagcct | 1080 |
| cctcgagacc tcaggagcag cagccccagg aagcaactgt cagagtcgtc tgacgatgac | 1140 |
| tatgacgacg tggacatccc caccctgca gaggacacac ctcctccact tcccccaag | 1200 |
| cccaagttcc gttctccatc agacgagggt cctgggagca tgggggatga tgggcagctg | 1260 |
| agcccggggg tgctggtccg gtgtgccagt gggccccac caaacagccc ccgtcctggg | 1320 |
| cctcccccat ccaccagcag ccccaccctc accgcccatt cagaaccctc actctggaac | 1380 |
| ccaccctccc gggagcttga caagccccca cttctgcccc caagaagga aagatgaag | 1440 |
| agaagggat gtgcccttct cgtaaagttg ttcaatggct gcccctccg gatccacagc | 1500 |
| acggccgcct ggacacatcc ctccaccaag gaccagcacc tgctcctggg ggcagaggaa | 1560 |
| ggcatcttca tcctgaaccg gaatgaccag gaggccacgc tggaaatgct ctttcctagc | 1620 |
| cggactacgt gggtgtactc catcaacaac gttctcatgt ctctctcagg aaagacccc | 1680 |
| cacctgtatt ctcatagcat ccttggcctg ctggaacgga aagagaccag agcaggaaac | 1740 |
| cccatcgctc acattagccc ccaccgccta ctggcaagga gaacatggt ttccaccaag | 1800 |
| atccaggaca ccaaaggctg ccgggcgtgc tgtgtggcgg agggtgcgag ctctggggc | 1860 |
| ccgttcctgt gcggtgcatt ggagacgtcc gttgtcctgc ttcagtggta ccagcccatg | 1920 |
| aacaaattcc tgcttgtccg gcaggtgctg ttcccactgc cgacgcctct gtccgtgttc | 1980 |
| gcgctgctga ccgggccagg ctctgagctg cccgctgtgt gcatcggcgt gagccccggg | 2040 |
| cggccgggga agtcggtgct cttccacacg gtgcgctttg gcgcgctctc ttgctggctg | 2100 |
| ggcgagatga gcaccgagca cagggggaccc gtgcaggtga cccaggtaga ggaagatatg | 2160 |
| gtgatggtgt tgatggatgg ctctgtgaag ctggtgaccc cggaggggtc cccagtccgg | 2220 |
| ggacttcgca cacctgagat ccccatgacc gaagcggtgg aggccgtggc tatggttgga | 2280 |
| ggtcagcttc aggccttctg gaagcatgga gtgcaggtgt gggctctagg ctcggatcag | 2340 |
| ctgctacagg agctgagaga ccctaccctc actttccgtc tgcttggctc ccccaggcct | 2400 |
| gtagtggtgg agacacgccc agtggatgat cctactgctc ccagcaacct ctacatccag | 2460 |
| gaatga | 2466 |

<210> SEQ ID NO 4
<211> LENGTH: 821
<212> TYPE: PRT

<213> ORGANISM: Homo sapiens

<400> SEQUENCE: 4

```
Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Ala Val Ala Leu Lys Gly Gly Tyr
            180                 185                 190

Asn Glu Leu Cys Asp Ile Trp Ser Leu Gly Ile Thr Ala Ile Glu Leu
        195                 200                 205

Ala Glu Leu Gln Pro Pro Leu Phe Asp Val His Pro Leu Arg Val Leu
    210                 215                 220

Phe Leu Met Thr Lys Ser Gly Tyr Gln Pro Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270

Leu Val Ser Gln Pro Gly Leu Asn Arg Gly Leu Ile Leu Asp Leu Leu
        275                 280                 285

Asp Lys Leu Lys Asn Pro Gly Lys Gly Pro Ser Ile Gly Asp Ile Glu
    290                 295                 300

Asp Glu Glu Pro Glu Leu Pro Ala Ile Pro Arg Arg Ile Arg Ser
305                 310                 315                 320

Thr His Arg Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
            340                 345                 350

Ala Asn Thr Ala Arg Leu Gln Pro Pro Arg Asp Leu Arg Ser Ser Ser
        355                 360                 365

Pro Arg Lys Gln Leu Ser Glu Ser Ser Asp Asp Tyr Asp Asp Val
    370                 375                 380

Asp Ile Pro Thr Pro Ala Glu Asp Thr Pro Pro Leu Pro Pro Lys
385                 390                 395                 400
```

```
Pro Lys Phe Arg Ser Pro Ser Asp Glu Gly Pro Gly Ser Met Gly Asp
            405                 410                 415

Asp Gly Gln Leu Ser Pro Gly Val Leu Val Arg Cys Ala Ser Gly Pro
            420                 425                 430

Pro Pro Asn Ser Pro Arg Pro Gly Pro Pro Ser Thr Ser Ser Pro
            435                 440                 445

His Leu Thr Ala His Ser Glu Pro Ser Leu Trp Asn Pro Pro Ser Arg
            450                 455                 460

Glu Leu Asp Lys Pro Pro Leu Leu Pro Lys Lys Glu Lys Met Lys
465                 470                 475                 480

Arg Lys Gly Cys Ala Leu Leu Val Lys Leu Phe Asn Gly Cys Pro Leu
                    485                 490                 495

Arg Ile His Ser Thr Ala Ala Trp Thr His Pro Ser Thr Lys Asp Gln
            500                 505                 510

His Leu Leu Leu Gly Ala Glu Gly Ile Phe Ile Leu Asn Arg Asn
            515                 520                 525

Asp Gln Glu Ala Thr Leu Glu Met Leu Phe Pro Ser Arg Thr Thr Trp
530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                    565                 570                 575

Arg Ala Gly Asn Pro Ile Ala His Ile Ser Pro His Arg Leu Leu Ala
            580                 585                 590

Arg Lys Asn Met Val Ser Thr Lys Ile Gln Asp Thr Lys Gly Cys Arg
            595                 600                 605

Ala Cys Cys Val Ala Glu Gly Ala Ser Ser Gly Gly Pro Phe Leu Cys
            610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
                    645                 650                 655

Leu Ser Val Phe Ala Leu Leu Thr Gly Pro Gly Ser Glu Leu Pro Ala
                    660                 665                 670

Val Cys Ile Gly Val Ser Pro Gly Arg Pro Gly Lys Ser Val Leu Phe
            675                 680                 685

His Thr Val Arg Phe Gly Ala Leu Ser Cys Trp Leu Gly Glu Met Ser
            690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                    725                 730                 735

Ser Pro Val Arg Gly Leu Arg Thr Pro Glu Ile Pro Met Thr Glu Ala
                    740                 745                 750

Val Glu Ala Val Ala Met Val Gly Gly Gln Leu Gln Ala Phe Trp Lys
            755                 760                 765

His Gly Val Gln Val Trp Ala Leu Gly Ser Asp Gln Leu Leu Gln Glu
            770                 775                 780
```

```
Leu Arg Asp Pro Thr Leu Thr Phe Arg Leu Leu Gly Ser Pro Arg Pro
785             790             795             800

Val Val Val Glu Thr Arg Pro Val Asp Asp Pro Thr Ala Pro Ser Asn
                805             810             815

Leu Tyr Ile Gln Glu
                820
```

NAPHTHYRIDINES AS INHIBITORS OF HPK1

CROSS REFERENCE TO RELATED APPLICATIONS

This application is a continuation of U.S. application Ser. No. 15/942,321 filed 30 Mar. 2018 (now U.S. Pat. No. 10,407,424), which claims the benefit of priority to International Patent Application No. PCT/CN2017/078792 filed 30 Mar. 2017 and International Patent Application No. PCT/CN2018/076909 filed 15 Feb. 2018, the contents of which applications are hereby incorporated by reference in their entireties.

SEQUENCE LISTING

This application contains a Sequence Listing which has been submitted electronically in ASCII format and is hereby incorporated by reference in its entirety. Said ASCII copy, created 1 Aug. 2019, is named P34139_US_SequenceListing.txt, and is 21,235 bytes in size.

FIELD OF THE INVENTION

This invention pertains to compounds that modulate the function of HPK1 and are useful for treatment of HPK1 mediated diseases and conditions such as cancer.

BACKGROUND

The major treatment modalities used by oncologists to treat cancer are surgical resection, radiation therapy, and classical chemotherapeutic drugs. Unfortunately, surgical resection is not a viable option for many tumors or forms of cancers. Further, radiation therapy and chemotherapeutic drugs do not target only diseased cells and therefore, end up damaging healthy cells. Therapeutics that more specifically target tumor cells are being developed by taking advantage of tumor-specific expression of antigens or inappropriate overexpression or activation of specific proteins within tumor cells, but tumor cells are prone to mutation and can become resistant to drugs that specifically target tumor cells.

A new cancer treatment paradigm has emerged that harnesses the patient's own immune system to overcome immunoevasive strategies utilized by many cancers and to enhance anti-tumor immunity. One such strategy is to inhibit negative regulators of immune responses that normally function to maintain peripheral tolerance, allowing tumor antigens to be recognized as non-self entities.

The hematopoietic progenitor kinase 1 (HPK1) is an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) *J Cell Biol* 195(5):839-853). HPK1 can also become activated in response to prostaglandin E2, which is often secreted by tumors, contributing to the escape of tumor cells from the immune system.

BRIEF SUMMARY

Antagonists of the enzyme HPK1 are provided herein. The compounds have a structure set forth in Formula I or Ia or are pharmaceutically acceptable salts, metabolites, prodrugs, or derivatives thereof. Also provided are Further provided are methods of preparing the compounds of Formula I or Ia.

The compounds find use in inhibiting HPK1 kinase activity, enhancing an immune response, and in the treatment of HPK1-dependent disorders. Accordingly, pharmaceutical compositions comprising a compound of Formula I or Ia or a pharmaceutically acceptable salt, prodrug, metabolite, or derivative thereof and a pharmaceutically acceptable carrier are also provided. Methods of inhibiting HPK1 comprise contacting HPK1 with an effective amount of a compound of Formula I or Ia or a pharmaceutically acceptable salt, prodrug, metabolite, or derivative thereof are provided. Methods of treating a HPK1-dependent disorder comprise administering to a subject in need thereof a compound of Formula I or Ia or a pharmaceutical formulation thereof are provided. Also provided is a kit for treating a HPK1-dependent disorder, the kit comprising a pharmaceutical composition comprising a compound of Formula I or Ia; and instructions for use.

DETAILED DESCRIPTION

Disclosed herein, are compounds of Formula I or Ia and pharmaceutical compositions thereof that are inhibitors or modulators of HPK1 (hematopoietic progenitor kinase 1). As such, the compounds and compositions are useful in treating diseases and disorders mediated by HPK1. An example of a method of treating is in the case of a subject who is suffering from cancer. The compounds can be used not only to combat cancer, but can also advantageously be used to enhance an immune response in a subject in need thereof.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

Definitions

The term "substituent" refers to an atom or a group of atoms that replaces a hydrogen atom on a molecule. The term "substituted" denotes that a specified molecule bears one or more substituents. The term "a compound of the formula" or "a compound of formula" or "compounds of the formula" or "compounds of formula" refers to any compound selected from the genus of compounds as defined by Formula I or Ia.

As used herein, the term "alkyl" refers to a straight-chained or branched hydrocarbon group containing 1 to 12 carbon atoms. The term "lower alkyl" refers to a $C_1$-$C_6$alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to linear or branched-chain monovalent hydrocarbon radical of two to eight carbon atoms ($C_2$-$C_8$), preferably ($C_{2-6}$), with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$), preferably ($C_{2-6}$), with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkoxy" refers to an —O-alkyl radical. Alkoxy groups may be optionally substituted with one or more substituents.

The term "haloalkoxy" refers to an —O-alkyl group that is substituted by one or more halo substituents. Examples of haloalkoxy groups include trifluoromethoxy, and 2,2,2-trifluoroethoxy.

The term "haloalkyl" refers to an alkyl radical that is substituted by one or more halo substituents. Examples of haloalkyl groups include difluoromethyl ($CHF_2$), trifluoromethyl ($CF_3$), and 2,2,2-trifluoroethyl.

As used herein, the term "halogen", "hal" or "halo" means —F, —Cl, —Br or —I.

As used herein, the designations "(CO)" and "C(O)" are used to indicate a carbonyl moiety. Examples of suitable carbonyl moieties include, but are not limited to, ketone and aldehyde moieties.

The term "cycloalkyl" refers to a hydrocarbon with 3-8 members or 3-7 members or 3-6 members or 3-5 members or 3-4 members and can be monocyclic or bicyclic. The ring may be saturated or may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-10 membered ring systems where the heteroatoms are selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocyclyl" or "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolanyl, THFyl, tetrahydrothienyl, thienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

The term "hydroxyalkyl" refers to an alkyl substituent which is further substituted with one or more hydroxyl groups. The alkyl portion may be further optionally substituted with one or more substituents.

Combinations of substituents and/or variables are permissible only if such combinations result in correct valences. Unless otherwise indicated by context, a hyphen (-) designates the point of attachment of the pendant group or radical.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

With respect to the nomenclature of a chiral center, the terms "d" and "l" (or plus and minus) configuration are as defined by the IUPAC Recommendations.

Furthermore the compounds described herein may include olefins having either geometry: "Z" refers to what is referred to as a "cis" (same side) configuration whereas "E" refers to what is referred to as a "trans" (opposite side) configuration.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "metabolite" is a product produced through metabolism in the body of a specified compound or salt thereof. Metabolites of a compound may be identified using routine techniques known in the art and their activities determined using tests such as those described herein. Such products may result, for example, from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the subject being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt, the salt can have multiple counter ions. Hence, a pharmaceutically acceptable salt can have one or more charged atoms and/or one or more counter ion.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Non-limiting examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ In certain embodiments, the pharmaceutically acceptable carrier is a non-naturally occurring pharmaceutically acceptable carrier.

Use of the word "inhibitor" herein is meant to mean a molecule that inhibits activity of HPK1. By "inhibit" herein is meant to decrease the activity of the target enzyme, as compared to the activity of that enzyme in the absence of the inhibitor. In some embodiments, the term "inhibit" means a decrease in HPK1 activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in HPK1 activity of about 5% to about 25%, about 25% to about 50%, about 50% to about 75%, or about 75% to 100%. In some embodiments, inhibit means a decrease in HPK1 activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "abnormal cell growth," "unregulated cell growth," and "hyperproliferative disorder" are used interchangeably in this application. "Abnormal cell growth", as used herein, unless otherwise indicated, refers to cell growth that is independent of normal regulatory mechanisms (e.g., loss of contact inhibition).

The term "cancer" refers to the condition in a subject that is characterized by unregulated cell growth, wherein the cancerous cells are capable of local invasion and/or metastasis to noncontiguous sites. As used herein, "cancer cells," "cancerous cells," or "tumor cells" refer to the cells that are characterized by this unregulated cell growth and invasive property. The term "cancer" encompasses all types of cancers, including, but not limited to, all forms of carcinomas, melanomas, blastomas, sarcomas, lymphomas and leukemias, including without limitation, bladder cancer, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

A "chemotherapeutic agent" is a chemical compound or biologic useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, and floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Additional examples of chemotherapeutic agents include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4 (5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; EGFR inhibitor such as erlotinib or cetuximab; an anti-VEGF inhibitor such as bevacizumab; arinotecan; rmRH (e.g., ABARELIX®); 17AAG (geldanamycin derivative that is a heat shock protein (Hsp) 90 poison), and pharmaceutically acceptable salts, acids or derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

In some embodiments, the chemotherapeutic agent is an immunotherapeutic agent. As used herein, an "immunotherapeutic agent" is a compound that enhances the immune system to help fight cancer, specifically or non-specifically. Immunotherapeutics include monoclonal antibodies and non-specific immunotherapies that boost the immune system, such as cytokines, interleukins (e.g., IL-2, IL-7, IL-12, IL-15, IL-21), interferons (e.g., IFN-α, IFN-β, IFN-γ), GM-CSF, thalidomide, (THALOMID®, Celgene), lenalidomide (REVLIMID®, Celgene), pomalidomide (POMALYST®, Celgene), imiquimod (ZYCLARA®, Valeant). Non-limiting examples of monoclonal antibodies that are useful as a chemotherapeutic agent include trastuzumab (HERCEP- TIN®, Genentech), bevacizumab (AVASTIN®, Genentech), cetuximab (ERBITUX®, Bristol-Myers Squibb), panitumumab (VECTIBIX®, Amgen), ipilimumab (YERVOY®, Bristol-Myers Squibb), rituximab (RITUXAN®, Genentech), alemtuzumab (CAMPATH®, Genzyme), ofatumumab (ARZERRA®, Genmab), gemtuzumab ozogamicin (MYLOTARG®, Wyeth), brentuximab vedotin (ADCETRIS®, Seattle Genetics), $^{90}$Y-labelled ibritumomab tiuxetan (ZEVALIN®, Biogen Idec), $^{131}$I-labelled tositumomab (BEXXAR®, GlaxoSmithKline), ado-trastuzumab emtansine (KADCYLA®, Genentech) blinatumomab (BLINCYTO, Amgen), pertuzumab (PERJETA®, Genentech), obinutuzumab (GAZYVA®, Genentech), nivolumab (OPDIVO®, ) Bristol-Myers Squibb), pembrolizumab (KEYTRUDA®, Merck), pidilizumab (CureTech), MPDL3280A (described in WO2010/077634, herein incorporated by reference in its entirety), MDX-1105 (described in WO2007/005874, herein incorporated by reference in its entirety), and MEDI4736 (described in WO2011/066389 and US2013/034559, each of which is herein incorporated by reference in its entirety). Another useful immunotherapeutic agent is AMP-224 (described in WO2010/027827 and WO2011/066342, each of which is incorporated herein in its entirety).

Other definitions are also provided elsewhere herein.

Compounds

The compounds of the invention are compounds of Formula I or Ia, or salts (e.g., pharmaceutically acceptable salts), prodrugs, metabolites, or derivatives thereof. These compounds are useful inhibitors of HPK1.

In one aspect, provided is a compound of Formula I:

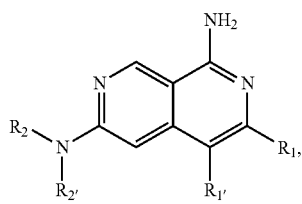

(I)

or salt (e.g., a pharmaceutically acceptable salt), solvate (e.g., hydrate), prodrug, metabolites or derivative thereof, wherein:

$R_1$ is $C_{2-9}$ heteroaryl, $C_{2-9}$ heterocyclyl, $C_{6-10}$ aryl, $C_{3-9}$ cycloalkyl, $C_{1-6}$ alkyl, $C_{2-6}$ alkenyl, $C_{2-6}$ alkynyl, —C≡C—($C_{2-9}$ heteroaryl), —C≡C—($C_6$-10 aryl), —CH(R$^{i'}$)—O—($C_{2-9}$ heteroaryl), —CH(R$^{i'}$)—O—($C_{2-9}$ heterocyclyl), —CH(R$^{i'}$)—O—($C_{6-10}$ aryl), —CH(R$^{i'}$)—O—($C_{3-9}$ cycloalkyl), —CH(R$^{i'}$)—O—($C_{1-6}$ alkyl), —C(O)N(R$^{i'}$)($C_{2-9}$ heteroaryl), —C(O)N(R$^{i'}$)($C_{2-9}$ heterocyclyl), —C(O)NR$^{24}$R$^{25}$, —C(O)OR$^{26}$, —C(=NR$^{29}$)R$^{27}$, —C(=NR$^{29}$)NR$^{24}$R$^{25}$, —C(=NOR$^{29}$)R$^{27}$, cyano, hydrogen, halogen, —R$^{24}$R$^{25}$, —NR$^{28}$C(O)R$^{27}$, —NR$^{28}$C(O)NR$^{24}$R$^{25}$, —NR$^{28}$C(O)OR$^{26}$, —NR$^{28}$S(O)R$^{29}$; —NR$^{28}$SO$_2$R$^{29}$, —NR$^{28}$SO$_2$NR$^{24}$R$^{25}$, —OR$^{26}$, —OC(O)R$^{27}$, —OC(O)NR$^{24}$R$^{25}$, —S(O)R$^{29}$; —SO$_2$R$^{29}$, or —SO$_2$NR$^{24}$R$^{25}$;

wherein the $C_{2-9}$ heteroaryl and $C_{2-9}$ heterocyclyl of $R_1$ independently have 1-4 heteroatoms selected from O, S and N; and wherein the $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl and $C_{2-9}$ heterocyclyl of $R_1$ are optionally substituted independently with one, two, three, four or five substituents;

wherein the $C_{3-9}$ cycloalkyl, $C_{6-10}$ aryl, $C_{2-9}$ heteroaryl or $C_{2-9}$ heterocyclyl of $R_1$ together with two of said substituents can form a bicyclic which is optionally substituted;

wherein a carbon embedded in said cycloalkyl, aryl, heteroaryl or heterocyclyl taken together with an oxygen to which it is bound can form a carbonyl;

each R$^{i'}$ is independently hydrogen or optionally substituted $C_{1-6}$ alkyl;

each R$^{24}$ and R$^{25}$ is independently hydrogen or optionally substituted $C_{1-6}$ alkyl; or R$^{24}$ and R$^{25}$ are taken together with the nitrogen atom to which they are attached to form a $C_{3-7}$ heterocyclyl optionally substituted with one to four substituents [e.g., optionally substituted pyrrolidine or pyrrolidinone];

each R$^{26}$, R$^{27}$ and R$^{28}$ is independently hydrogen or optionally substituted $C_{1-6}$ alkyl;

each R$^{29}$ is independently optionally substituted $C_{1-6}$ alkyl;

$R_{1'}$ is hydrogen, $C_{1-6}$ alkyl, $C_{2-6}$ alkenyl, $C_{3-6}$ cycloalkyl, $C_{6-10}$ aryl, $C_{2-9}$ heteroaryl, or halogen, wherein said alkyl, alkenyl, cycloalkyl, aryl and heteroaryl can be optionally substituted with one, two, three, four or five substituents; provided at least one of $R_1$ and $R_{1'}$ is other than hydrogen;

$R_2$ is A-C(O)— or D;

A is $C_{1-6}$ alkyl, $C_{2-6}$ alkenyl, $C_{2-6}$ alkynyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{1-6}$ alkylene)-, —NR$^g$R$^h$ or —OR$^h$;

wherein the $C_{1-6}$ alkyl, $C_{3-9}$ cycloalkyl, $C_{6-10}$ aryl, $C_{2-9}$ heteroaryl and $C_{2-9}$ heterocyclyl of A are optionally substituted independently with one, two, three, four or five substituents;

R$^g$ is H or $C_{1-6}$ alkyl optionally substituted with one to four substituents independently selected from the group consisting of hydroxyl, halogen, cyano, amino, di($C_{1-6}$ alkyl)amino, mono($C_{1-6}$ alkyl)amino; —CHF$_2$, and —CF$_3$;

R$^h$ is $C_{1-6}$ alkyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, or ($C_{2-9}$ heterocyclyl)-($C_{1-6}$ alkylene)-;

wherein the $C_{1-6}$ alkyl, $C_{3-7}$ cycloalkyl, $C_{6-10}$ aryl, $C_{2-9}$ heteroaryl and $C_{2-9}$ heterocyclyl of R$^h$ are optionally substituted independently with one, two, three, four or five substituents;

D is H, $C_{1-6}$ alkyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{1-6}$ alkylene)-, or ($C_{3-7}$ cycloalkyl)-S(O)$_2$—;

wherein the $C_{2-9}$ heteroaryl and $C_{2-9}$ heterocyclyl of D independently have 1-4 heteroatoms selected from O, S and N; and wherein the $C_{1-6}$ alkyl, $C_{3-7}$ cycloalkyl, $C_{6-10}$ aryl, $C_{2-9}$ heteroaryl and $C_{2-9}$ heterocyclyl of D are optionally substituted independently with one, two, three, four or five substituents;

wherein two of the substituents attached to different atoms are taken together with the atoms to which they attached to form a bicyclic or tricyclic, wherein said bicyclic or tricyclic is optionally substituted; and wherein a carbon embedded in said heteroaryl or heterocyclyl taken together with an oxygen to which it is bound can form a carbonyl; and $R_{2'}$ is H or optionally substituted $C_{1-6}$ alkyl.

In some embodiments of the general structure of Formula (I):

$R_1$ is $C_{2-9}$ heteroaryl, $C_{2-9}$ heterocyclyl, $C_{6-10}$ aryl, —C≡C—$C_{2-9}$ heteroaryl, —C(O)N($R^{j'}$)($C_{2-9}$ heteroaryl), —C(O)N($R^{j'}$)($C_{2-9}$ heterocyclyl), —CH($R^{j'}$)—O—($C_{2-9}$ heteroaryl), $C_{3-9}$ cycloalkyl, $C_{1-6}$ alkyl or hydrogen; wherein each $R^{j'}$ is independently hydrogen or $C_{1-6}$ alkyl;

wherein the $C_{2-9}$ heteroaryl and $C_{2-9}$ heterocyclyl of $R_1$ independently have 1-4 heteroatoms selected from O, S and N; and wherein the $C_{1-6}$ alkyl, $C_{3-9}$ cycloalkyl, $C_{6-10}$ aryl, $C_{2-9}$ heteroaryl and $C_{2-9}$ heterocyclyl of $R_1$ are optionally substituted independently with one, two, three, four or five substituents;

wherein the $C_{6-10}$ aryl, $C_{2-9}$ heteroaryl or $C_{2-9}$ heterocyclyl of $R_1$ together with two of said substituents can form a bicyclic which is optionally substituted; and wherein a carbon embedded in said aryl, heteroaryl or heterocyclyl taken together with an oxygen to which it is bound can form a carbonyl;

$R_{1'}$ is hydrogen, $C_{1-6}$ alkyl, $C_{2-6}$ alkenyl, $C_{3-6}$ cycloalkyl, $C_{2-9}$ heteroaryl, or halogen, wherein said alkyl, alkenyl, cycloalkyl, and heteroaryl are optionally substituted (e.g., with hydroxyl, halogen, and/or amino); provided at least one of $R_1$ and $R_{1'}$ is other than hydrogen;

and $R_2$ and $R_{2'}$ are as detailed above.

In one aspect of the general structure of Formula (I):

$R_1$ is:

$C_{2-9}$ heteroaryl, $C_{2-9}$ heterocyclyl, or $C_{6-10}$ aryl, wherein said heteroaryl or heterocyclyl has 1-4 heteroatoms selected from O, S and N; and wherein said aryl, heteroaryl and heterocyclyl can be optionally substituted with one, two, three or four substituents, $R_6$, $R_7$ $R_8$ and $R_{8'}$, each of which is independently selected from the group consisting of:

i. branched or linear $C_{1-6}$ alkyl, $C_{1-6}$ alkenyl, $C_{1-6}$ alkenylene, and $C_{3-9}$ cycloalkyl, wherein said alkyl, alkenyl, alkenylene, and cycloalkyl can be optionally substituted with hydroxyl, halogen, —$CF_2$, —$CF_3$, amino, di($C_{1-6}$)alkylamino, mono($C_{1-6}$)alkylamino, cyano, $C_{3-7}$ cycloalkyl, $C_{1-6}$ alkoxy, —$SO_2R'$, —$SO_2NR'R''$, —(CO)NR'R'', or —NR'(CO)R'', wherein R' and R'' are independently H or $C_{1-6}$ alkyl;

ii. $NR^aR^b$—C(O)—, wherein, $R^a$ and $R^b$ are each independently hydrogen or $C_{1-6}$ alkyl, wherein said alkyl can optionally be substituted with hydroxyl, halogen, —$CF_2$, or —$CF_3$;

iii. $C_{1-6}$ alkoxy;

iv. halogen;

v. cyano;

vi. hydroxyl;

vii. amino;

viii. di($C_{1-6}$)alkylamino;

ix. mono($C_{1-6}$)alkylamino;

x. —$NR^c(CO)R^d$, wherein $R^c$ and $R^d$ are independently H or $C_{1-6}$ alkyl;

xi. —$CF_3$;

xii. —$CF_2$, xiii. —$SO_2R'$, wherein R' is as described above;

xiv. —$SO_2NR'R''$, wherein R' and R'' are as described above;

xv. —(CO)$NR^cR^d$; wherein $R^c$ and $R^d$ are as described above;

xvi. —(CO)$OR^e$; wherein $R^e$ is H, $C_{1-6}$ alkyl, or $CH_2$-aryl;

xvii. substituted or unsubstituted $C_{3-5}$ heterocyclyl; and wherein a carbon embedded in said aryl, heteroaryl or heterocyclyl taken together with an oxygen to which it is bound can form a carbonyl;

$R_{1'}$ is:

H, $C_{1-6}$ alkyl, $C_{2-6}$ alkenyl, $C_{3-6}$ cycloalkyl, $C_{2-9}$ heteroaryl, or halogen, wherein said alkyl, alkenyl, cycloalkyl, and heteroaryl can be optionally substituted with hydroxyl, halogen, or amino;

$R_2$ is A-C(O)—, wherein, A is:

i. $C_{3-7}$ cycloalkyl($C_{1-6}$)$_j$alkyl- or $C_{2-9}$ heterocyclyl($C_{1-6}$)$_j$alkyl-, wherein, j is 1 or 0; and wherein said cycloalkyl or heterocyclyl can be optionally substituted with one, two, three or four of $R_5$, wherein $R_5$, in each instance, is independently selected from the group consisting of branched or linear $C_{1-6}$ alkyl, halogen, cyano, cyano($C_{1-6}$)alkyl-, —$CF_3$, —$CF_2$, hydroxy ($C_{1-6}$)alkyl, halo($C_{1-6}$)alkyl, hydroxyl, ($C_{1-6}$ alkyl)-O—($C_{1-6}$ alkyl)-, amino, di($C_{1-6}$)alkylamino, mono($C_{1-6}$) alkylamino, amino($C_{1-6}$)alkyl, $C_{1-6}$ alkoxy, $CH_3CO_2$—($C_{1-6}$ alkyl)-, —$SO_2R'$, —$SO_2NR'R''$, —(CO)NR'R'', —NR'(CO)R'', wherein, in each instance, R' and R'' are as described above, optionally substituted $C_{2-9}$ heteroaryl, optionally substituted $C_{2-9}$ heterocyclyl, optionally substituted $C_{6-10}$ aryl and $NR^eR^f$—C(O)—($C_{1-6}$ alkyl)$_k$-, wherein $R^e$ and $R^f$ are each independently selected from the group consisting of hydrogen and branched or linear $C_{1-6}$ alkyl, or $R^e$ and $R^f$ together with the nitrogen to which each is bound can form a $C_{3-7}$ cycloalkyl, which can be optionally substituted with branched or linear $C_{1-6}$ alkyl, $C_{3-4}$ cycloalkyl, halogen, cyano, —$CF_3$, —$CF_2$, or hydroxyl;

and k is 1 or 0;

or, said cycloalkyl or heterocyclyl together with two of $R_5$ form a bicyclic or spiro ring, wherein two of $R_5$ attached to different carbons are taken together with the carbon to which each is attached to form a bicyclic, or two of $R_5$ attached to the same carbon are taken together with the carbon to which each is attached to form a spiro ring;

ii. —$NR^gR^h$, wherein $R^g$ is H or branched or linear $C_{1-6}$ alkyl, wherein said alkyl can be optionally substituted with hydroxyl, halogen, cyano, amino, di($C_{1-6}$)alkylamino, mono ($C_{1-6}$)alkylamino; —$CF_2$, or —$CF_3$;

$R^h$ is selected from the group consisting of:

a. branched or linear $C_{1-6}$ alkyl, wherein said alkyl can be optionally substituted with hydroxyl, halogen, cyano, amino, di($C_{1-6}$)alkylamino, mono($C_{1-6}$)alkylamino, —$CF_2$, —$CF_3$, or $NR^{e'}R^{f'}$—C(O)—, wherein $R^{e'}$ and $R^{f'}$ are each independently hydrogen or branched or linear $C_{1-6}$ alkyl;

and, b. $C_{3-7}$ cycloalkyl($C_{1-6}$ alkyl)$_m$-, $C_{2-9}$ heteroaryl($C_{1-6}$ alkyl)$_m$-, $C_{6-10}$ aryl($C_{1-6}$ alkyl)$_m$- or $C_{2-9}$ heterocyclyl ($C_{1-6}$ alkyl)$_m$-, wherein, m is 1 or 0; and wherein said cycloalkyl, heteroaryl, aryl or heterocyclyl can be optionally substituted with one or two of $R_{5'}$, wherein $R_{5'}$, in each instance, is independently selected from the group consisting of branched or linear $C_{1-6}$ alkyl, halogen, cyano, —$CF_3$, —$CF_2$, hydroxy ($C_{1-6}$)alkyl, halo($C_{1-6}$)alkyl, hydroxyl, $C_{1-6}$ alkoxy, amino, amino($C_{1-6}$)alkyl, and $NR^iR^j$—C(O)—($C_{1-6}$ alkyl)$_{k'}$-, wherein $R^i$ and $R^j$ are independently selected from the group consisting of hydrogen and branched or linear $C_{1-6}$ alkyl, and k' is 1 or 0;

iii. $R_9$—($C_{1-6}$ alkyl)-, wherein $R_9$ is selected from the group consisting of hydroxyl, halogen, —$CF_2$, —$CF_3$, cyano, $C_{1-6}$ alkoxy, —$NR^oR^p$, wherein, $R^o$ and $R^p$ are each independently H or branched or linear $C_{1-6}$ alkyl, $NR^{o'}R^{p'}$—CO—, wherein $R^{o'}$ and $R^{p'}$ are each independently hydrogen or branched or linear $C_{1-6}$ alkyl;

iv. B—($C_{1-6}$ alkyl)$_t$-, wherein, B is $C_{3-9}$ heteroaryl or $C_{3-7}$ heterocyclyl, wherein, said heteroaryl or heterocyclyl has 1-3 heteroatoms selected from O, S and N; and wherein said heteroaryl or heterocyclyl can be optionally substituted with one, two or three of $R^{10}$, $R^{10'}$ and $R^{10''}$, each of which is independently selected from the group consisting of:
a. branched or linear $C_{1-6}$ alkyl or $C_{3-4}$ cycloalkyl, wherein said alkyl or cycloalkyl can be optionally substituted with hydroxyl, halogen, —$CF_2$, —$CF_3$, amino, di($C_{1-6}$)alkylamino, mono($C_{1-6}$)alkylamino, cyano, —(CO)$NR^qR^r$ or —$NR^q$(CO)$R^r$, wherein $R^q$ and $R^r$ are independently H or $C_{1-6}$ alkyl;
b. $C_{3-7}$ cycloalkyl; and
c. $C_{3-7}$ heterocyclyl;
d. hydroxyl;
e. halogen;
f. —$CF_2$;
g. —$CF_3$;
h. amino;
i. di($C_{1-6}$)alkylamino;
j. mono($C_{1-6}$)alkylamino;
k. cyano;
l. —(CO)$NR^sR^t$, wherein $R^s$ and $R^t$ are independently H or $C_{1-6}$ alkyl; and
m. —$NR^s$(CO)$R^t$, wherein $R^s$ and $R^t$ are independently H or $C_{1-6}$ alkyl; and, t is 1 or 0;

v. ($C_{6-10}$ aryl)$_{q'}$-($C_{1-6}$ alkyl)$_n$-O— or pyrrolidinyl-O—, wherein, the aryl can be optionally substituted with one, two or three of $R^{11}$, $R^{12}$ and $R^{13}$, each of which is selected from the group consisting of branched or linear $C_{1-6}$ alkyl, hydroxyl, halogen, —$CF_2$, —$CF_3$, cyano, $C_{1-6}$ alkoxy, and $NR^uR^v$—, wherein $R^u$ and $R^v$ are each independently H or branched or linear $C_{1-6}$ alkyl, and, n is 1 or 0, q' is 1 or 0, provided that one of n and q' is 1;

vi. branched or linear $C_{1-6}$ alkyl, $C_{1-6}$ alkenyl, $C_{1-6}$ alkenylene, wherein said alkyl, alkenyl, and alkenylene, can be optionally substituted with hydroxyl, halogen, —$CF_2$, —$CF_3$, amino, di($C_{1-6}$)alkylamino, mono($C_{1-6}$) alkylamino, cyano, $C_{3-7}$ cycloalkyl, $C_{1-6}$ alkoxy, —$SO_2R'$, —$SO_2NR'R''$, —(CO)$NR'R''$, or —$NR'$(CO)R'', wherein R' and R'' are independently H or $C_{1-6}$ alkyl;

or, $R_2$ is D, wherein D is:
i. $C_{6-10}$ aryl-($C_{1-6}$ alkyl)$_z$-, or $C_{3-9}$ heteroaryl-($C_{1-6}$ alkyl)$_z$-, wherein, said heteroaryl has 1-4 heteroatoms selected from O, S and N; and wherein said aryl or heteroaryl can be optionally substituted with one, two, three or four of $R^{14}$, $R^{15}$, $R^{16'}$ and $R^{16}$, each of which is independently selected from the group consisting of:
a. branched or linear $C_{1-6}$ alkyl, wherein said alkyl can be optionally substituted with hydroxyl, halogen, —$CF_2$, —$CF_3$, amino, di($C_{1-6}$)alkylamino, mono ($C_{1-6}$)alkylamino, cyano $C_{1-6}$ alkoxy, —$SO_2R'$, —$SO_2NR'R''$, —(CO)$NR^wR^x$, or —$NR^w$(CO)$R^x$, wherein $R^w$ and $R^x$ are independently H or $C_{1-6}$ alkyl, wherein two of $R^{14}$, $R^{15}$, $R^{16'}$ and $R^{16}$ attached to different atoms are taken together with the atom to which each is attached to form a bicyclic;
b. $C_{3-7}$ cycloalkyl;
c. $C_{3-7}$ heterocyclyl;
d. hydroxyl;
e. halogen;
f. —$CF_2$;
g. —$CF_3$;
h. amino;
i. di($C_{1-6}$)alkylamino;
j. mono($C_{1-6}$)alkylamino;
k. cyano;
l. —$NR^y$(CO)$R^z$, wherein $R^y$ and $R^z$ are independently H or $C_{1-6}$ alkyl;
m. —(CO)$NR^yR^z$, wherein $R^y$ and $R^z$ are independently H or $C_{1-6}$ alkyl;
n. —$SO_2NR^yR^z$, wherein $R^y$ and $R^z$ are independently H or $C_{1-6}$ alkyl; and
o. —(CO)$OR^y$, wherein $R^y$ is H or $C_{1-6}$ alkyl; and, z is 1 or 0;

ii. $C_{3-7}$ cycloalkyl-($SO_2$)—, wherein said cycloalkyl can be optionally substituted with one or two of $R^{6'}$, wherein $R^{6'}$, in each instance, is independently selected from the group consisting of branched or linear $C_{1-6}$ alkyl, halogen, cyano, —$CF_3$, —$CF_2$, hydroxy($C_{1-6}$) alkyl, halo($C_{1-6}$)alkyl, hydroxyl, ($C_{1-6}$ alkyl)-O—($C_{1-6}$ alkyl)-, $C_{1-6}$ alkoxy, amino, di($C_{1-6}$)alkylamino, mono ($C_{1-6}$)alkylamino, amino($C_{1-6}$)alkyl, and $NR^{e'}R^{f'}$—C (O)—($C_{1-6}$ alkyl)$_n$-, wherein $R^{e'}$ and $R^{f'}$ are independently selected from the group consisting of hydrogen and branched or linear $C_{1-6}$ alkyl, and n is 1 or 0; and iii. $C_{1-6}$ alkyl or pyrrolidine, wherein said alkyl is optionally substituted with halogen;

and, $R_{2'}$ is H or branched or linear $C_{1-6}$ alkyl.

In one aspect, provided is a compound of formula Ia:

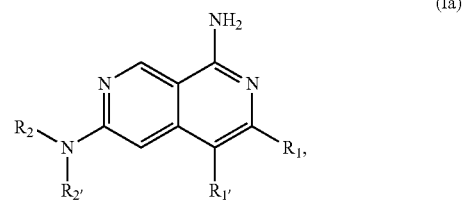

(Ia)

or salt (e.g., a pharmaceutically acceptable salt), solvate (e.g., hydrate), prodrug, metabolites or derivative thereof, wherein:

$R_1$ is:
$C_{2-9}$ heteroaryl, $C_{2-9}$ heterocyclyl, $C_{6-10}$ aryl, —C≡C— $C_{2-9}$ heteroaryl, —C(O)N($R^{j'}$)($C_{2-9}$ heteroaryl), —C(O) N($R^{j'}$)($C_{2-9}$ heterocyclyl), —CH($R^{j''}$)—O—($C_{2-9}$ heteroaryl), or $C_{1-6}$ alkyl; wherein each $R^{j'}$ is independently hydrogen or $C_{1-6}$ alkyl;
wherein the $C_{2-9}$ heteroaryl and $C_{2-9}$ heterocyclyl of $R_1$ independently have 1-4 heteroatoms selected from O, S and N; and wherein the $C_6$alkyl, $C_{6-10}$ aryl, $C_{2-9}$ heteroaryl and $C_{2-9}$ heterocyclyl of $R_1$ are optionally substituted with one, two, three or four substituents, $R_6$, $R_7R_8$ and $R_{8'}$, each of which is independently selected from the group consisting of:
i. branched or linear $C_{1-6}$ alkyl, $C_{1-6}$ alkenyl, $C_{1-6}$ alkenylene, and $C_{3-9}$ cycloalkyl, wherein said alkyl, alkenyl, alkenylene, and cycloalkyl are optionally substituted with one to four substituents independently selected from the group consisting of hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —S(O)R', —SO$_2$R', —SO$_2$NR'R", —C(O)NR'R", and —NR'C(O)R", wherein R' and R" are independently H or $C_{1-6}$ alkyl;

ii. NR$^a$R$^b$—C(O)—, wherein, R$^a$ and R$^b$ are each independently hydrogen or $C_{1-6}$ alkyl, wherein said alkyl can optionally be substituted with hydroxyl, halogen, —CHF$_2$, or —CF$_3$;

iii. $C_{1-6}$ alkoxy;

iv. halogen;

v. cyano;

vi. hydroxyl;

vii. amino;

viii. di($C_{1-6}$ alkyl)amino;

ix. mono($C_{1-6}$ alkyl)amino;

x. —NR$^c$C(O)R$^d$, wherein R$^c$ and R$^d$ are independently H or $C_{1-6}$ alkyl;

xi. —CF$_3$;

xii. —CHF$_2$;

xiii. —SO$_2$R', wherein R' is H or $C_{1-6}$ alkyl;

xiv. —SO$_2$NR'R", wherein R' and R" are independently H or $C_{1-6}$ alkyl;

xv. —C(O)NR$^c$R$^d$; wherein R$^c$ and R$^d$ are independently H or $C_{1-6}$ alkyl;

xvi. —C(O)OR$^e$; wherein R$^e$ is H, $C_{1-6}$ alkyl, or CH$_2$-aryl;

xvii. $C_{3-5}$ heterocyclyl, $C_{6-10}$ aryl, —($C_{1-6}$ alkyl)($C_{6-10}$ aryl), or $C_{2-9}$ heteroaryl, wherein said heterocyclyl, aryl, or heteroaryl can be optionally substituted with $C_{1-6}$ alkyl, $C_{6-10}$ aryl, or —C(O)OR$^e$; wherein R$^e$ is H, $C_{1-6}$ alkyl, or CH$_2$-aryl;

xviii. —O—($C_{2-9}$ heteroaryl);

xix. —NR'S(O)$_k$R", wherein k' is 1 or 2 and R' and R" are independently H or $C_{1-6}$ alkyl;

wherein the $C_{6-10}$ aryl, $C_{2-9}$ heteroaryl or $C_{2-9}$ heterocyclyl of R$_1$ together with two of R$_6$, R$_7$, R$_8$ and R$_{8'}$ can form a bicyclic; and wherein a carbon embedded in said aryl, heteroaryl or heterocyclyl taken together with an oxygen to which it is bound can form a carbonyl;

R$_1$ is:

hydrogen, $C_{1-6}$ alkyl, $C_{2-6}$ alkenyl, $C_{3-6}$ cycloalkyl, $C_{2-9}$ heteroaryl, or halogen, wherein said alkyl, alkenyl, cycloalkyl, and heteroaryl can be optionally substituted with hydroxyl, halogen, or amino;

R$_2$ is A-C(O)— or D, wherein, A is:

i. ($C_{3-7}$ cycloalkyl)($C_{1-6}$ alkyl)$_j$- or ($C_{2-9}$ heterocyclyl)($C_{1-6}$ alkyl)$_j$-, wherein, j is 1 or 0; and wherein said cycloalkyl or heterocyclyl can be optionally substituted with one, two, three or four of R$_5$, wherein R$_5$, in each instance, is independently selected from the group consisting of branched or linear $C_{1-6}$ alkyl, halogen, cyano, cyano($C_{1-6}$ alkyl)-, —CF$_3$, —CHF$_2$, hydroxy($C_{1-6}$ alkyl), halo($C_{1-6}$ alkyl), hydroxyl, ($C_{1-6}$ alkyl)-O—($C_{1-6}$ alkyl)-, —($C_{1-6}$ alkyl)-NHC(O)—($C_{1-6}$ alkyl), amino, —NR'C(O)R", acetyl, di($C_{1-6}$ alkyl)amino, mono($C_{1-6}$ alkyl)amino, amino($C_{1-6}$ alkyl), $C_{1-6}$ alkoxy, CH$_3$CO$_2$—($C_{1-6}$ alkyl)-, —NR'SO$_2$R", —SO$_2$R', —SO$_2$NR'R", —C(O)NR'R", —NR'C(O)R", optionally substituted $C_{2-9}$ heteroaryl, optionally substituted $C_{2-9}$ heterocyclyl, optionally substituted $C_{6-10}$ aryl, optionally substituted $C_{3-9}$ cycloalkyl-C(O)—, and NR$^e$R$^f$—C(O)—($C_{1-6}$ alkyl)$_k$-, wherein said $C_{2-9}$ heteroaryl, $C_{2-9}$ heterocyclyl, and $C_{6-10}$ aryl can be optionally substituted with $C_{1-6}$ alkyl or ($C_{1-6}$ alkyl)-O—($C_{1-6}$ alkyl)-, wherein said ($C_{1-6}$ alkyl)-O—($C_{1-6}$ alkyl)- may be optionally substituted with amino, wherein, in each instance, R' and R" are independently H or $C_{1-6}$ alkyl, wherein R$^e$ and R$^f$ are each independently selected from the group consisting of hydrogen and branched or linear $C_{1-6}$ alkyl, or R$^e$ and R$^f$ together with the nitrogen to which each is bound can form a $C_{3-7}$ cycloalkyl, which can be optionally substituted with branched or linear $C_{1-6}$ alkyl, $C_{3-4}$ cycloalkyl, halogen, cyano, —CF$_3$, —CHF$_2$, or hydroxyl;

and k is 1 or 0;

or, said cycloalkyl or heterocyclyl together with two of R$_5$ form a bicyclic or spiro ring, wherein two of R$_5$ attached to different carbons are taken together with the carbon to which each is attached to form a bicyclic, or two of R$_5$ attached to the same carbon are taken together with the carbon to which each is attached to form a spiro ring, wherein said bicyclic or spiro rings may be substituted with one, two, three or four of R$_5$ as described above;

ii. —NR$^g$R$^h$, wherein

R$^g$ is H or branched or linear $C_{1-6}$ alkyl, wherein said alkyl can be optionally substituted with one to four substituents independently selected from the group consisting of hydroxyl, halogen, cyano, amino, di($C_{1-6}$ alkyl)amino, mono($C_{1-6}$ alkyl)amino, —CHF$_2$, and —CF$_3$;

R$^h$ is selected from the group consisting of:

a. branched or linear $C_{1-6}$ alkyl, wherein said alkyl can be optionally substituted with hydroxyl, halogen, cyano, amino, di($C_{1-6}$ alkyl)amino, mono($C_{1-6}$ alkyl)amino, —CHF$_2$, —CF$_3$, or NR$^{e'}$R$^{f'}$—C(O)—, wherein R$^{e'}$ and R$^{f'}$ are each independently hydrogen or branched or linear $C_{1-6}$ alkyl;

and, b. ($C_{3-7}$ cycloalkyl)($C_{1-6}$ alkyl)$_m$-, ($C_{2-9}$ heteroaryl)($C_{1-6}$ alkyl)$_m$-, ($C_{6-10}$ aryl)($C_{1-6}$ alkyl)$_m$- or ($C_{2-9}$ heterocyclyl)($C_{1-6}$ alkyl)$_m$-, wherein, m is 1 or 0; and wherein said cycloalkyl, heteroaryl, aryl or heterocyclyl can be optionally substituted with one or two of R$_{5'}$, wherein R$_{5'}$, in each instance, is independently selected from the group consisting of branched or linear $C_{1-6}$ alkyl, halogen, cyano, cyano($C_{1-6}$ alkyl)-, —CF$_3$, —CHF$_2$, hydroxy($C_{1-6}$ alkyl), halo($C_{1-6}$ alkyl), hydroxyl, $C_{1-6}$ alkoxy, amino, amino($C_{1-6}$ alkyl), and NR$^i$R$^j$—C(O)—($C_{1-6}$ alkyl)$_{k'}$-, wherein R$^i$ and R$^j$ are independently selected from the group consisting of hydrogen and branched or linear $C_{1-6}$ alkyl, and k' is 1 or 0;

iii. R$_9$—($C_{1-6}$ alkyl)-, wherein R$_9$ is selected from the group consisting of hydroxyl, halogen, —CHF$_2$, —CF$_3$, cyano, $C_{1-6}$ alkoxy, —NR$^o$R$^p$, NR$^{o'}$R$^{p'}$—C(O)—; wherein R$^o$, R$^p$, R$^{o'}$ and R$^{p'}$ are each independently hydrogen or branched or linear $C_{1-6}$ alkyl;

iv. B—($C_{1-6}$ alkyl)$_r$-, wherein, B is $C_{3-9}$ heteroaryl or $C_{3-7}$ heterocyclyl, wherein, said heteroaryl or heterocyclyl has 1-3 heteroatoms selected from O, S and N; and wherein said heteroaryl or heterocyclyl can be optionally substituted with one, two or three of R$^{10}$, R$^{10'}$ and R$^{10"}$, each of which is independently selected from the group consisting of.

a. branched or linear $C_{1-6}$ alkyl or $C_{3-4}$ cycloalkyl, wherein said alkyl or cycloalkyl can be optionally substituted with hydroxyl, halogen, —CHF$_2$, —CF$_3$, amino, di($C_{1-6}$ alkyl)amino, mono($C_{1-6}$ alkyl)amino, cyano, —C(O)NR$^q$R$^r$ or —NR$^q$C(O)R$^r$, wherein R$^q$ and R$^r$ are independently H or $C_{1-6}$ alkyl;

b. $C_{3-7}$ cycloalkyl;

c. $C_{3-7}$ heterocyclyl;

d. hydroxyl;
e. halogen;
f. —$CHF_2$;
g. —$CF_3$;
h. amino;
i. di($C_{1-6}$ alkyl)amino;
j. mono($C_{1-6}$ alkyl)amino;
k. cyano;
l. —C(O)$NR^sR^t$, wherein $R^s$ and $R^t$ are independently H or $C_{1-6}$ alkyl; and
m. —$NR^sC(O)R^t$, wherein $R^s$ and $R^t$ are independently H or $C_{1-6}$ alkyl; and, t is 1 or 0;

v. ($C_{6-10}$ aryl)$_{q'}$-($C_{1-6}$ alkyl)$_n$-O— or ($C_{2-7}$ heterocyclyl)-O—, wherein, said aryl or heterocyclyl can be optionally substituted with one, two or three of $R^{11}$, $R^{12}$ and $R^{13}$, each of which is selected from the group consisting of branched or linear $C_{1-6}$ alkyl, hydroxyl, halogen, —$CHF_2$, —$CF_3$, cyano, $C_{1-6}$ alkoxy, acetyl, and $NR^uR^v$—; wherein $R^u$ and $R^v$ are each independently H or branched or linear $C_{1-6}$ alkyl; wherein, if present, a sulfur embedded in said heterocyclyl taken together with one oxygen can form a sulfoxide, or taken together with two oxygens can form a sulfone;
and, n is 1 or 0, q' is 1 or 0, provided that one of n and q' is 1;

vi. branched or linear $C_{1-6}$ alkyl, $C_{1-6}$ alkenyl, $C_{1-6}$ alkenylene, wherein said alkyl, alkenyl, and alkenylene, can be optionally substituted with hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —$SO_2R'$, —$SO_2NR'R''$, —C(O)NR'R'', or —NR'C(O)R'', wherein R' and R'' are independently H or $C_{1-6}$ alkyl;

D is:
i. ($C_{6-10}$ aryl)($C_{1-6}$ alkyl)$_z$-, ($C_{3-7}$ cycloalkyl)($C_{1-6}$ alkyl)$_z$-, or ($C_{3-9}$ heterocyclyl)($C_{1-6}$ alkyl)$_z$-, wherein, said heteroaryl has 1-4 heteroatoms selected from O, S and N; and wherein said aryl, cycloalkyl or heteroaryl can be optionally substituted with one, two, three or four of $R^{14}$, $R^{15}$, $R^{16'}$ and $R^{16}$, each of which is independently selected from the group consisting of:
  a. branched or linear $C_{1-6}$ alkyl or $C_{2-6}$ alkenyl, wherein said alkyl or alkenyl can be optionally substituted with one to four substituents independently selected from the group consisting of hydroxyl, halogen, —$CHF_2$, —$CF_3$, amino, di($C_{1-6}$ alkyl)amino, mono($C_{1-6}$ alkyl)amino, cyano $C_{1-6}$ alkoxy, —$SO_2R'$, —$SO_2NR'R''$, —C(O)$NR^wR^x$, and —$NR^wC(O)R^x$, wherein $R^w$ and $R^x$ are independently H or $C_{1-6}$ alkyl; wherein two of $R^{14}$, $R^{15}$, $R^{16'}$ and $R^{16}$ attached to different atoms are taken together with the atom to which each is attached to form a bicyclic bicyclic or tricyclic, wherein said bicyclic or tricyclic may be substituted with one, two, three or four of $R^{14}$, $R^{15}$, $R^{16'}$ and $R^{16}$ as described above;
  b. $C_{3-7}$ cycloalkyl;
  c. $C_{3-7}$ heterocyclyl, wherein said heterocyclyl can be optionally substituted by hydroxyl, acetyl, or oxetane;
  d. hydroxyl;
  e. halogen;
  f. —$CHF_2$;
  g. —$CF_3$;
  h. amino;
  i. di($C_{1-6}$ alkyl)amino;
  j. mono($C_{1-6}$ alkyl)amino;
  k. cyano;
  l. —$NR^yC(O)R^z$, wherein $R^y$ and $R^z$ are independently H or $C_{1-6}$ alkyl;
  m. —C(O)$NR^yR^z$, wherein $R^y$ and $R^z$ are independently H or $C_{1-6}$ alkyl;
  n. —$SO_2NR^yR^z$, wherein $R^y$ and $R^z$ are independently H or $C_{1-6}$ alkyl; and
  o. —C(O)$OR^y$, wherein $R^y$ is H or $C_{1-6}$ alkyl;
  and, z is 1 or 0;

ii. $C_{3-7}$ cycloalkyl-$SO_2$—, wherein said cycloalkyl can be optionally substituted with one or two of $R^{6'}$, wherein $R^{6'}$, in each instance, is independently selected from the group consisting of branched or linear $C_6$alkyl, halogen, cyano, —$CF_3$, —$ClF_2$, hydroxy($C_{1-6}$ alkyl), halo($C_{1-6}$ alkyl), hydroxyl, ($C_{1-6}$ alkyl)-O—($C_{1-6}$ alkyl)-, $C_{1-6}$ alkoxy, amino, di($C_{1-6}$ alkyl)amino, mono($C_{1-6}$ alkyl)amino, amino($C_{1-6}$ alkyl), and $NR^{e'}R^{f'}$—C(O)—($C_{1-6}$ alkyl)$_n$-, wherein $R^{e'}$ and $R^{f'}$ are independently selected from the group consisting of hydrogen and branched or linear $C_{1-6}$ alkyl, and n is 1 or 0;
or
iii. H, $C_{1-6}$ alkyl or pyrrolidine, wherein said alkyl is optionally substituted with halogen;
and, $R_{2'}$ is H or branched or linear $C_{1-6}$ alkyl.

In various embodiments of the compounds of Formula I or Ia, the alkyl, alkenyl, alkynyl, cycloalkyl, aryl, heteroaryl and heterocyclyl are optionally substituted with one to five substituents. In some embodiments, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl or $C_{2-9}$ heterocyclyl may be independently optionally substituted with one to five $R^{30}$.

In some embodiments, $R^{30}$, in each instance, is independently $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl, $C_{2-9}$ heterocyclyl, halogen, cyano, oxo, —C(O)$NR^{31}R^{32}$, —C(O)$OR^{33}$, —C(=$NR^{36}$)$R^{34}$, —C(=$NR^{36}$)$NR^{31}R^{32}$, —C(=$NOR^{36}$)$R^{34}$, cyano, hydrogen, halogen, —$R^{31}R^{32}$, —$NR^{35}C(O)R^{34}$, —$NR^{35}C(O)NR^{31}R^{32}$, —$NR^{35}C(O)OR^{33}$, —$NR^{35}S(O)R^{36}$; —$NR^{35}SO_2R^{36}$, —$NR^{35}SO_2NR^{31}R^{32}$, —$OR^{33}$, —OC(O)$R^{34}$, —OC(O)$NR^{31}R^{32}$, —S(O)$R^{36}$; —$SO_2R^{36}$, or —$SO_2NR^{31}R^{32}$; wherein the $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl, $C_{2-9}$ heterocyclyl of $R^{30}$ are optionally substituted with one to four $R^{40}$; or two $R^{30}$ groups are taken together with the parent moiety to with they are attached to form a ring which is optionally substituted with one to four $R^{40}$;

each $R^{31}$ and $R^{32}$ is independently hydrogen, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl or $C_{2-9}$ heterocyclyl, each is independently optionally substituted with one to four $R^{40}$; or $R^{31}$ and $R^{32}$ are taken together with the nitrogen atom to which they are attached to form a $C_{3-7}$ heterocyclyl optionally substituted with one to four $R^{40}$;

each $R^{33}$, $R^{34}$ and $R^{35}$ are independently hydrogen, $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl or $C_{2-9}$ heterocyclyl, each is independently optionally substituted with one to four $R^{40}$;

$R^{36}$ is $C_{1-6}$ alkyl optionally substituted with one to four $R^{40}$.

$R^{40}$ in each instance is independently selected from the group consisting of halogen, cyano, oxo, —$NR^{41}R^{42}$, —$SO_2NR^{41}R^{42}$, —C(O)$NR^{41}R^{42}$, —C(O)$OR^{43}$, —$OR^{43}$, —$NR^{43}C(O)R^{44}$, —$NR^{43}C(O)OR^{43}$, —$NR^{43}C(O)NR^{41}R^{42}$, —$NR^{43}SO_2R^{45}$, —$SO_2R^{45}$, $C_{1-6}$ alkyl, $C_{3-7}$ cycloalkyl, $C_{6-10}$ aryl, $C_{2-9}$ heteroaryl, or $C_{2-9}$ heterocyclyl; or two $R^{40}$ groups are taken together with the parent moiety to with they are attached to form a ring which is optionally substituted with one to three substituents selected from $C_{1-6}$ alkyl, $C_{1-6}$ haloalkyl, hydroxyl and oxo; the $C_{1-6}$ alkyl, $C_{3-7}$ cycloalkyl, $C_{6-10}$ aryl, $C_{2-9}$ heteroaryl, or $C_{2-9}$ heterocyclyl of $R^{40}$ are independently optionally substituted with one to three substituents selected from $C_{1-6}$ alkyl, $C_{1-6}$ haloalkyl, hydroxyl and oxo.

each $R^{41}$ and $R^{42}$ is independently hydrogen or $C_{1-6}$ alkyl; or $R^{41}$ and $R^{42}$ are taken together with the nitrogen atom to which they are attached to form a $C_{3-7}$ heterocyclyl optionally substituted with one to three substituents selected from $C_{1-6}$ alkyl, $C_{1-6}$ haloalkyl, hydroxyl and oxo;

each $R^{43}$ and $R^{44}$ are independently hydrogen or $C_{1-6}$ alkyl; and $R^{45}$ is $C_{1-6}$ alkyl.

In embodiments where all other variables are as defined above, useful values of $R_1$ are an optionally substituted $C_{2-9}$ heteroaryl, or an optionally substituted $C_{3-7}$ heterocyclyl. In some embodiments, $R_1$ is an optionally substituted $C_{2-9}$ heteroaryl, or an optionally substituted $C_{2-9}$ heterocyclyl. In embodiments where all other variables are as defined in any embodiment above, $R_1$ is selected from the group consisting of:

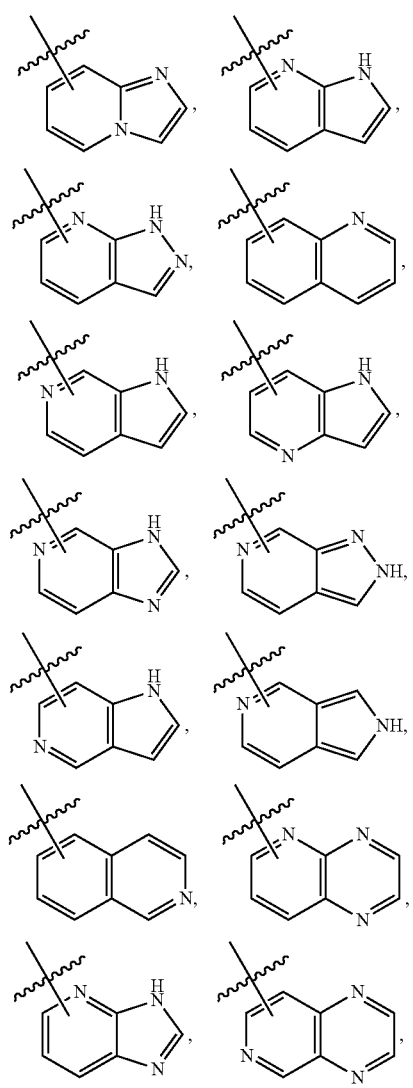

each of which can be optionally substituted with one, two, three or four substituents. In some embodiments, each of the above moieties can be optionally substituted with one, two or three substituents, $R_6$, $R_7$ and $R_8$.

In embodiments where all other variables are as defined in any embodiment above, useful values of $R_1$ are selected from the group consisting of:

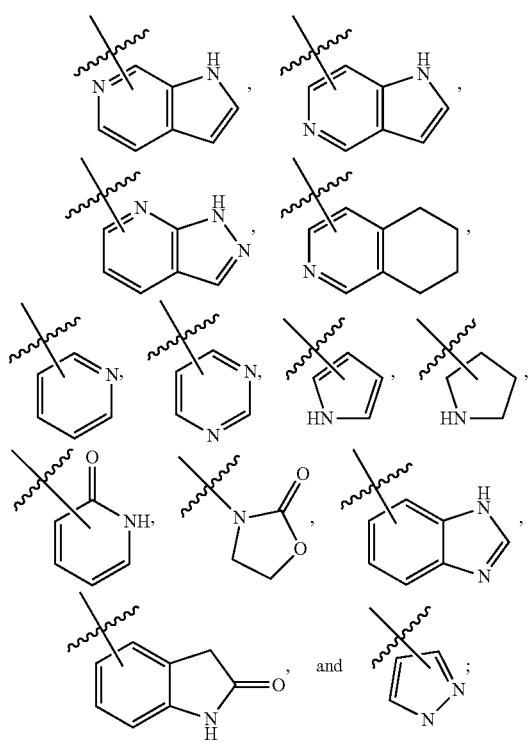

each of which can be optionally substituted with one, two, three or four substituents. In some embodiments, each of the above moieties can be optionally substituted with one, two or three substituents, $R_6$, $R_7$ and $R_8$.

In embodiments where all other variables are as defined in any embodiment above, useful values of $R_1$ are selected from the group consisting of:

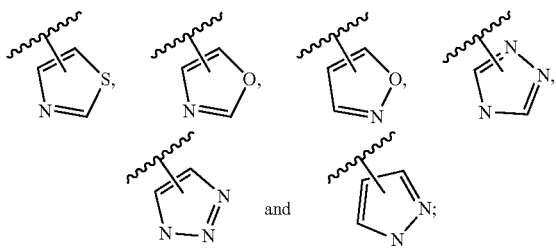

each of which can be optionally substituted with one, two, three or four substituents. In some embodiments, each of the above moieties can be optionally substituted with one, two or three substituents, $R_6$, $R_7$ and $R_8$.

In embodiments where all other variables are as defined in any embodiment above, useful values of $R_1$ are:

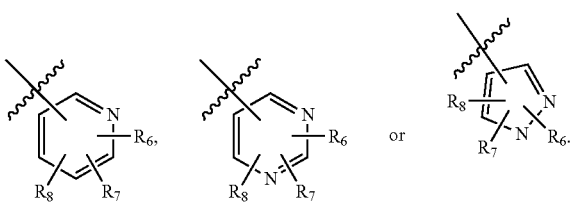

In embodiments where all other variables are as defined in any embodiment above, $R_1$ is:

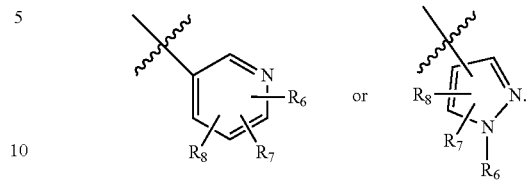

In embodiments where all other variables are as defined in any embodiment above, wherein $R_1$ is:

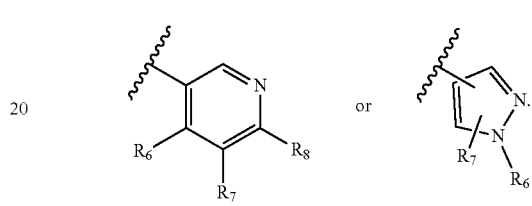

In embodiments where all other variables are as defined in any embodiment above, wherein $R_1$ is:

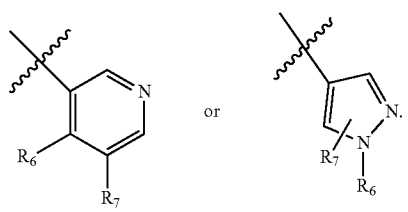

In some embodiments, $R_6$, $R_7$, and $R_8$ are each independently selected from the group consisting of:
  i. branched or linear $C_{1-6}$ alkyl, $C_{1-6}$ alkenyl, $C_{1-6}$ alkenylene, and $C_{3-9}$ cycloalkyl, wherein said alkyl, alkenyl, alkenylene, and cycloalkyl are optionally substituted with one to four substituents independently selected from the group consisting of hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —S(O)R', —$SO_2$R', —$SO_2$NR'R'', —C(O)NR'R'', and —NR'C(O)R'', wherein R' and R'' are independently H or $C_{1-6}$ alkyl;
  ii. $NR^aR^b$—C(O)—, wherein, $R^a$ and $R^b$ are each independently hydrogen or $C_{1-6}$ alkyl, wherein said alkyl can optionally be substituted with hydroxyl, halogen, —$CHF_2$, or —$CF_3$;
  iii. $C_{1-6}$ alkoxy;
  iv. halogen;
  v. cyano;
  vi. hydroxyl;
  vii. amino;
  viii. di($C_{1-6}$ alkyl)amino;
  ix. mono($C_{1-6}$ alkyl)amino;
  x. —$NR^cC(O)R^d$, wherein $R^c$ and $R^d$ are independently H or $C_{1-6}$ alkyl;
  xi. —$CF_3$;
  xii. —$CHF_2$,
  xiii. —$SO_2$R', wherein R' is H or $C_{1-6}$ alkyl;
  xiv. —$SO_2$NR'R'', wherein R' and R'' are independently H or $C_{1-6}$ alkyl;

xv. —C(O)NR$^c$R$^d$; wherein R$^c$ and R$^d$ are independently H or C$_{1-6}$ alkyl;

xvi. —C(O)OR$^e$; wherein R$^e$ is H, C$_{1-6}$ alkyl, or CH$_2$-aryl;

xvii. C$_{3-5}$ heterocyclyl, C$_{6-10}$ aryl, —(C$_{1-6}$ alkyl)(C$_{6-10}$ aryl), or C$_{2-9}$ heteroaryl, wherein said heterocyclyl, aryl, or heteroaryl can be optionally substituted with C$_{1-6}$ alkyl, C$_{6-10}$ aryl, or —C(O)OR$^e$; wherein R$^e$ is H, C$_{1-6}$ alkyl, or CH$_2$-aryl;

xviii. —O—(C$_{2-9}$ heteroaryl);

xix. —NR'S(O)$_k$R", wherein k' is 1 or 2 and R' and R" are independently H or C$_{1-6}$ alkyl;

wherein the C$_{6-10}$ aryl, C$_{2-9}$ heteroaryl or C$_{2-9}$ heterocyclyl of R$_1$ together with two of R$_6$, R$_7$, and R$_8$ can form a bicyclic; and wherein a carbon embedded in said aryl, heteroaryl or heterocyclyl taken together with an oxygen to which it is bound can form a carbonyl.

In some embodiments, one or more of R$_6$, R$_7$, and R$_8$ are independently selected from the group consisting of branched or linear C$_{1-6}$ alkyl, C$_{1-6}$ alkenyl, C$_{1-6}$ alkenylene, and C$_{3-9}$ cycloalkyl, wherein said alkyl, alkenyl, alkenylene, and cycloalkyl are optionally substituted with one to four substituents independently selected from the group consisting of hydroxyl, halogen, —CHF$_2$, —CF$_3$, amino, di(C$_{1-6}$ alkyl)amino, mono(C$_{1-6}$ alkyl)amino, cyano, C$_{3-7}$ cycloalkyl, optionally substituted C$_{6-10}$ aryl, optionally substituted C$_{2-9}$ heteroaryl, optionally substituted C$_{2-9}$ heterocyclyl, C$_{1-6}$ alkoxy, —S(O)R', —SO$_2$R', —SO$_2$NR'''R", —C(O)NR'''R", and —NR'C(O)R", —NR'C(O)OR", —NR'C(O)NR"R''', —NR'SO$_2$NR"R''' or —NR'S(O)R", wherein R' and R''' are independently H or C$_{1-6}$ alkyl and R" is independently C$_{1-6}$ alkyl, halo(C$_{1-6}$ alkyl) or C$_{6-10}$ aryl optionally substituted with C$_{1-6}$ alkyl; or R" and R''' are taken together with the nitrogen to which they are attached to form a substituted or unsubstituted heterocyclyl. In some embodiments, one or more of R$_6$, R$_7$, and R$_8$ are independently C$_{1-6}$ haloalkyl (e.g., CHF$_2$ or CF$_3$).

In some embodiments, one or more of R$_6$, R$_7$, and R$_8$ are independently —C(O)NR$^a$R$^b$, —NR$^c$C(O)R$^d$, —C(O)OR$^e$; —NR$^c$C(O)OR$^e$; NR$^c$C(O) R$^a$R$^b$; wherein R$^a$ and R$^b$ are each independently hydrogen, optionally substituted C$_{1-6}$ alkyl, optionally substituted C$_{6-10}$ aryl, optionally substituted C$_{2-9}$ heterocyclyl, or optionally substituted C$_{2-9}$ heteroaryl; or R$^a$ and R$^b$ are taken together with the nitrogen to which they are attached to form an optionally substituted heterocyclyl; wherein R$^c$ and R$^d$ are independently H, optionally substituted C$_{1-6}$ alkyl, optionally substituted C$_{6-10}$ aryl, optionally substituted C$_{2-9}$ heterocyclyl, or optionally substituted C$_{2-9}$ heteroaryl; wherein R$^e$ is H, C$_{1-6}$ alkyl, or CH$_2$-aryl. Examples of the optional substituents include, but are not limited to hydroxyl, halogen, —CHF$_2$, and —CF$_3$.

In some embodiments, one or more of R$_6$, R$_7$, and R$_8$ are independently selected from the group consisting of iii. halogen, cyano, hydroxyl, C$_{1-6}$ alkoxy, amino, mono(C$_{1-6}$ alkyl)amino, or di(C$_{1-6}$ alkyl)amino.

In some embodiments, one or more of R$_6$, R$_7$, and R$_8$ are independently —SO$_2$R', —SO$_2$NR"R''', —NR'SO$_2$NR"R''', —NR'S(O)R" or —NR'SO$_2$R"; wherein R' and R''' are independently H or optionally substituted C$_{1-6}$ alkyl; and R" is independently C$_{1-6}$ alkyl, halo(C$_{1-6}$ alkyl) or C$_{6-10}$ aryl optionally substituted with C$_{1-6}$ alkyl; or R" and R''' are taken together with the nitrogen to which they are attached to form optionally substituted C$_{2-9}$ heterocyclyl.

In some embodiments, R$_1$ is

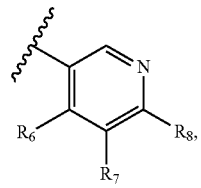

wherein R$_6$, R$_7$, and R$_8$ are each independently selected from the group consisting of hydrogen, hydroxyl, amino, C$_{1-6}$ alkyl, C$_{1-6}$ alkoxy, and mono(C$_{1-6}$ alkyl)amino; or two of R$_6$, R$_7$, and R$_8$ can form a bicyclic.

In some of these embodiments, R$_6$ is C$_{1-6}$ alkyl; R$_7$ is hydrogen, amino, or mono(C$_{1-6}$ alkyl)amino; and R$_8$ is hydrogen, hydroxyl, or C$_{1-6}$ alkoxy; or R$_6$ and R$_7$ together form a bicyclic; or R$_7$ and R$_8$ together form a bicyclic. In some embodiments, R$_6$ is methyl. In some embodiments, R$_7$ is amino. In some embodiments, R$_6$ is methyl and R$_7$ is amino.

In some embodiments, R$_1$ is

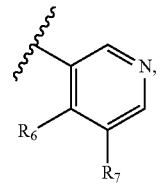

wherein R$_6$ and R$_7$ are selected from the group consisting of hydrogen, amino, and C$_{1-6}$ alkyl. In some embodiments, R$_6$ is C$_{1-6}$ alkyl (e.g., methyl). In some embodiments, R$_7$ is hydrogen or amino. In some embodiments, R$_7$ is hydrogen. In some embodiments, R$_7$ is amino. In some embodiments, R$_6$ is C$_{1-6}$ alkyl (e.g., methyl) and R$_7$ is hydrogen or amino.

In embodiments where all other variables are as defined in any embodiment above, R$_1$ is

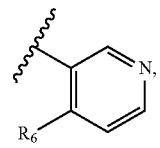

wherein, R$_6$ is C$_{1-6}$ alkyl, optionally substituted with hydroxyl, —CF$_2$, —CF$_3$, or halogen.

In embodiments where all other variables are as defined in any embodiment above, R$_6$ is methyl.

In some embodiments, R$_1$ is

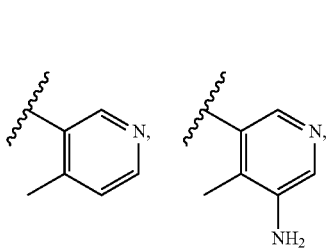 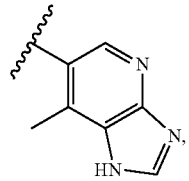

-continued

In some embodiments, $R_1$ is

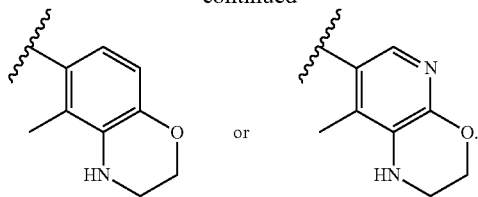

In some embodiments, $R_1$ is

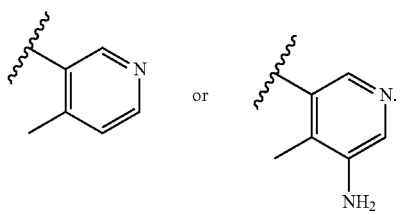

In some embodiments, $R_1$ is

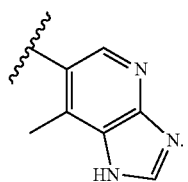 [SMILES: *c1cnc2nc[nH]c2c1C]

In some embodiments, $R_1$ is

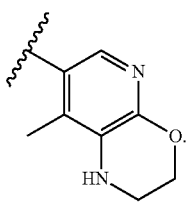 [SMILES: *c1cnc2c(c1C)NCCO2]

In some embodiments, $R_1$ is

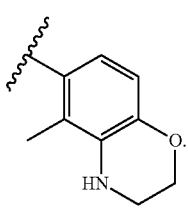 [SMILES: *c1ccc2c(c1C)NCCO2]

In embodiments where all other variables are as defined in any embodiment above, $R_2$ is -A-C(O)—. In some embodiments, A is optionally substituted $C_{1-6}$ alkyl, optionally substituted $C_{3-9}$ cycloalkyl, optionally substituted $C_{6-10}$ aryl, optionally substituted $C_{2-9}$ heteroaryl, optionally substituted $C_{2-9}$ heterocyclyl, —NR$^g$R$^h$ or —OR$^h$.

In some embodiments, A is:

i. ($C_{3-7}$ cycloalkyl)($C_{1-6}$ alkyl)$_j$- or ($C_{2-9}$ heterocyclyl)($C_{1-6}$ alkyl)$_j$-, wherein, j is 1 or 0; and wherein said cycloalkyl or heterocyclyl can be optionally substituted with one, two, three or four of $R_5$, wherein $R_5$, in each instance, is independently selected from the group consisting of branched or linear $C_{1-6}$ alkyl, halogen, cyano, cyano($C_{1-6}$ alkyl)-, —CF$_3$, —CHF$_2$, hydroxy($C_{1-6}$ alkyl), halo($C_{1-6}$ alkyl), hydroxyl, ($C_{1-6}$ alkyl)-O—($C_{1-6}$ alkyl)-, —($C_{1-6}$ alkyl)-NHC(O)—($C_{1-6}$ alkyl), amino, —NR'C(O)R", acetyl, di($C_{1-6}$ alkyl)amino, mono($C_{1-6}$ alkyl)amino, amino($C_{1-6}$ alkyl), $C_{1-6}$ alkoxy, CH$_3$CO$_2$—($C_{1-6}$ alkyl)-, —NR'SO$_2$R", —SO$_2$R', —SO$_2$NR'R", —C(O)NR'R", —NR'C(O)R", optionally substituted $C_{2-9}$ heteroaryl, optionally substituted $C_{2-9}$ heterocyclyl, optionally substituted $C_{6-10}$ aryl, optionally substituted $C_{3-9}$ cycloalkyl-C(O)—, and NR$^e$R$^f$—C(O)—($C_{1-6}$ alkyl)$_k$-, wherein said $C_{2-9}$ heteroaryl, $C_{2-9}$ heterocyclyl, and $C_{6-10}$ aryl can be optionally substituted with $C_{1-6}$ alkyl or ($C_{1-6}$ alkyl)-O—($C_{1-6}$ alkyl)-, wherein said ($C_{1-6}$ alkyl)-O—($C_{1-6}$ alkyl)- may be optionally substituted with amino, wherein, in each instance, R' and R" are independently H or $C_{1-6}$ alkyl, wherein R$^e$ and R$^f$ are each independently selected from the group consisting of hydrogen and branched or linear $C_{1-6}$ alkyl, or R$^e$ and R$^f$ together with the nitrogen to which each is bound can form a $C_{3-7}$ cycloalkyl, which can be optionally substituted with branched or linear $C_{1-6}$ alkyl, $C_{3-4}$ cycloalkyl, halogen, cyano, —CF$_3$, —CHF$_2$, or hydroxyl;

and k is 1 or 0;

or, said cycloalkyl or heterocyclyl together with two of $R_5$ form a bicyclic or spiro ring, wherein two of $R_5$ attached to different carbons are taken together with the carbon to which each is attached to form a bicyclic, or two of $R_5$ attached to the same carbon are taken together with the carbon to which each is attached to form a spiro ring, wherein said bicyclic or spiro rings may be substituted with one, two, three or four of $R_5$ as described above;

ii. —NR$^g$R$^h$, wherein

R$^g$ is H or branched or linear $C_{1-6}$ alkyl, wherein said alkyl can be optionally substituted with one to four substituents independently selected from the group consisting of hydroxyl, halogen, cyano, amino, di($C_{1-6}$ alkyl)amino, mono($C_{1-6}$ alkyl)amino; —CHF$_2$, and —CF$_3$;

R$^h$ is selected from the group consisting of:

a. branched or linear $C_{1-6}$ alkyl, wherein said alkyl can be optionally substituted with hydroxyl, halogen, cyano, amino, di($C_{1-6}$ alkyl)amino, mono($C_{1-6}$ alkyl)amino, —CHF$_2$, —CF$_3$, or NR$^{e'}$R$^{f'}$—C(O)—, wherein R' and R$^f$ are each independently hydrogen or branched or linear $C_{1-6}$ alkyl;

and, b. ($C_{3-7}$ cycloalkyl)($C_{1-6}$ alkyl)$_m$-, ($C_{2-9}$ heteroaryl)($C_{1-6}$ alkyl)$_m$-, ($C_{6-10}$ aryl)($C_{1-6}$ alkyl)$_m$- or ($C_{2-9}$ heterocyclyl)($C_{1-6}$ alkyl)$_m$-, wherein, m is 1 or 0; and wherein said cycloalkyl, heteroaryl, aryl or heterocyclyl can be optionally substituted with one or two of $R_{5'}$, wherein $R_{5'}$, in each instance, is independently selected from the group consisting of branched or linear $C_{1-6}$ alkyl, halogen, cyano, cyano($C_{1-6}$ alkyl)-, —CF$_3$, —CHF$_2$, hydroxy($C_{1-6}$ alkyl), halo($C_{1-6}$ alkyl), hydroxyl, $C_{1-6}$ alkoxy, amino, amino($C_{1-6}$ alkyl), and NR$^i$R$^j$—C(O)—($C_{1-6}$ alkyl)$_{k'}$-, wherein R$^i$ and R$^j$ are independently selected from the group consisting of hydrogen and branched or linear $C_{1-6}$ alkyl, and k' is 1 or 0;

iii. $R_9$—($C_{1-6}$ alkyl)-, wherein $R_9$ is selected from the group consisting of hydroxyl, halogen, —$CHF_2$, —$CF_3$, cyano, $C_{1-6}$ alkoxy, —$NR^oR^p$, $NR^{o'}R^{p'}$—C(O)—; wherein $R^o$, $R^p$, $R^{o'}$ and $R^{p'}$ are each independently hydrogen or branched or linear $C_{1-6}$ alkyl;

iv. B—($C_{1-6}$ alkyl)$_t$-, wherein, B is $C_{3-9}$ heteroaryl or $C_{3-7}$ heterocyclyl, wherein, said heteroaryl or heterocyclyl has 1-3 heteroatoms selected from O, S and N; and wherein said heteroaryl or heterocyclyl can be optionally substituted with one, two or three of $R^{10}$, $R^{10'}$ and $R^{10''}$, each of which is independently selected from the group consisting of:
  a. branched or linear $C_{1-6}$ alkyl or $C_{3-4}$ cycloalkyl, wherein said alkyl or cycloalkyl can be optionally substituted with hydroxyl, halogen, —$CHF_2$, —$CF_3$, amino, di($C_{1-6}$ alkyl)amino, mono($C_{1-6}$ alkyl)amino, cyano, —C(O)$NR^qR^r$ or —$NR^qC(O)R^r$, wherein $R^q$ and $R^r$ are independently H or $C_{1-6}$ alkyl;
  b. $C_{3-7}$ cycloalkyl;
  c. $C_{3-7}$ heterocyclyl;
  d. hydroxyl;
  e. halogen;
  f. —$CHF_2$;
  g. —$CF_3$;
  h. amino;
  i. di($C_{1-6}$ alkyl)amino;
  j. mono($C_{1-6}$ alkyl)amino;
  k. cyano;
  l. —C(O)$NR^sR^t$, wherein $R^s$ and $R^t$ are independently H or $C_{1-6}$ alkyl; and
  m. —$NR^sC(O)R^t$, wherein $R^s$ and $R^t$ are independently H or $C_{1-6}$ alkyl; and, t is 1 or 0;

v. ($C_{6-10}$ aryl)$_q$-($C_{1-6}$ alkyl)$_n$-O— or ($C_{2-7}$ heterocyclyl)-O—, wherein, said aryl or heterocyclyl can be optionally substituted with one, two or three of R''', $R^{12}$ and $R^{13}$, each of which is selected from the group consisting of branched or linear $C_{1-6}$ alkyl, hydroxyl, halogen, —$CHF_2$, —$CF_3$, cyano, $C_{1-6}$ alkoxy, acetyl, and $NR^uR^v$—; wherein $R^u$ and $R^v$ are each independently H or branched or linear $C_{1-6}$ alkyl; wherein, if present, a sulfur embedded in said heterocyclyl taken together with one oxygen can form a sulfoxide, or taken together with two oxygens can form a sulfone;
and, n is 1 or 0, q' is 1 or 0, provided that one of n and q' is 1;

or vi. branched or linear $C_{1-6}$ alkyl, $C_{1-6}$ alkenyl, $C_{1-6}$ alkenylene, wherein said alkyl, alkenyl, and alkenylene, can be optionally substituted with hydroxyl, halogen, —$CHF_2$, —$CF_3$, amino, di($C_{1-6}$ alkyl)amino, mono($C_{1-6}$ alkyl)amino, cyano, $C_{3-7}$ cycloalkyl, $C_{1-6}$ alkoxy, —$SO_2R'$, —$SO_2NR'R''$, —C(O)NR'R'', or —NR'C(O)R'', wherein R' and R'' are independently H or $C_{1-6}$ alkyl.

In some embodiments, A is ($C_{3-7}$ cycloalkyl)($C_{1-6}$ alkyl)$_j$- or ($C_{2-9}$ heterocyclyl)($C_{1-6}$ alkyl)$_j$-, wherein, j is 1 or 0; and wherein said cycloalkyl or heterocyclyl can be optionally substituted with one, two, three or four of $R_5$, wherein $R_5$, in each instance, is independently selected from the group consisting of branched or linear $C_{1-6}$ alkyl, halogen, cyano, cyano($C_{1-6}$ alkyl)-, —$CF_3$, —$CHF_2$, hydroxy($C_{1-6}$ alkyl), halo($C_{1-6}$ alkyl), hydroxyl, ($C_{1-6}$ alkyl)-O—($C_{1-6}$ alkyl)-, —($C_{1-6}$ alkyl)-NHC(O)—($C_{1-6}$ alkyl), amino, —NR'C(O)R'', acetyl, di($C_{1-6}$ alkyl)amino, mono ($C_{1-6}$ alkyl)amino, amino($C_{1-6}$ alkyl), $C_{1-6}$ alkoxy, $CH_3CO_2$—($C_{1-6}$ alkyl)-, —NR'$SO_2$R'', —$SO_2R'$, —$SO_2NR'R''$, —C(O)NR'R'', —NR'C(O)R'', —NR'C(O)NR'R'', optionally substituted $C_{2-9}$ heteroaryl, optionally substituted $C_{2-9}$ heterocyclyl, optionally substituted $C_{6-10}$ aryl, optionally substituted $C_{3-9}$ cycloalkyl, optionally substituted $C_{3-9}$ cycloalkyl-C(O)—, and $NR^eR^f$—C(O)—($C_{1-6}$ alkyl)$_k$-;
  wherein said $C_{2-9}$ heteroaryl, $C_{2-9}$ heterocyclyl, and $C_{6-10}$ aryl can be optionally substituted with $C_{1-6}$ alkyl or ($C_{1-6}$ alkyl)-O—($C_{1-6}$ alkyl)-, wherein said ($C_{1-6}$ alkyl)-O—($C_{1-6}$ alkyl)- may be optionally substituted with amino,
  wherein, in each instance, R' and R'' are independently H or $C_{1-6}$ alkyl,
  wherein $R^e$ and $R^f$ are each independently selected from the group consisting of hydrogen and branched or linear $C_{1-6}$ alkyl, or $R^e$ and $R^f$ together with the nitrogen to which each is bound can form a $C_{3-7}$ cycloalkyl, which can be optionally substituted (e.g., with branched or linear $C_{1-6}$ alkyl, $C_{3-4}$ cycloalkyl, halogen, cyano, —$CF_3$, —$CHF_2$, or hydroxyl);
  and k is 1 or 0;
  or, said cycloalkyl or heterocyclyl together with two of $R_5$ form a bicyclic or spiro ring, wherein two of $R_5$ attached to different carbons are taken together with the carbon to which each is attached to form a bicyclic, or two of $R_5$ attached to the same carbon are taken together with the carbon to which each is attached to form a spiro ring, wherein said bicyclic or spiro rings may be substituted with one, two, three or four substituents (e.g., $R_5$ as described above when not taken together).

In some embodiments, A is —$NR^gR^h$ or —$OR^h$, wherein $R^g$ is H or optionally substituted $C_{1-6}$ alkyl; and $R^h$ is optionally substituted $C_{1-6}$ alkyl, optionally substituted $C_{3-9}$ cycloalkyl, optionally substituted $C_{6-10}$ aryl, optionally substituted $C_{2-9}$ heteroaryl, or optionally substituted $C_{2-9}$ heterocyclyl.

In some embodiments, the $C_{1-6}$ alkyl of $R^g$ is optionally substituted with one to four substituents independently selected from the group consisting of hydroxyl, halogen, cyano, amino, di($C_{1-6}$ alkyl)amino, mono($C_{1-6}$ alkyl)amino; —$CHF_2$, and —$CF_3$.

Examples of $R^h$ include, but are not limited to,
  a. branched or linear $C_{1-6}$ alkyl, wherein said alkyl can be optionally substituted with hydroxyl, halogen, cyano, amino, di($C_{1-6}$ alkyl)amino, mono($C_{1-6}$ alkyl)amino, —$CHF_2$, —$CF_3$, —S(O)R', —$SO_2R'$, —$SO_2NR'''R''$, —C(O)NR'''R'', —NR'C(O)R'', —NR'C(O)OR'', —NR'C(O)NR'R''', —NR'$SO_2$NR'R''' or —NR'S(O)R'', wherein R' and R''' are independently H or $C_{1-6}$ alkyl and R'' is independently $C_{1-6}$ alkyl, halo($C_{1-6}$ alkyl) or $C_{6-10}$ aryl optionally substituted with $C_{1-6}$ alkyl; or R'' and R''' are taken together with the nitrogen to which they are attached to form a substituted or unsubstituted heterocyclyl; and
  b. ($C_{3-7}$ cycloalkyl)($C_{1-6}$ alkyl)$_m$-, ($C_{2-9}$ heteroaryl)($C_{1-6}$ alkyl)$_m$-, ($C_{6-10}$ aryl)($C_{1-6}$ alkyl)$_m$- or ($C_{2-9}$ heterocyclyl)($C_{1-6}$ alkyl)$_m$-, wherein, m is 1 or 0; and wherein said cycloalkyl, heteroaryl, aryl or heterocyclyl can be optionally substituted with one or two of $R_{5'}$; wherein $R_{5'}$, in each instance, is independently selected from the group consisting of branched or linear $C_{1-6}$ alkyl, halogen, cyano, cyano ($C_{1-6}$ alkyl)-, —$CF_3$, —$CHF_2$, hydroxy($C_{1-6}$ alkyl), halo ($C_{1-6}$ alkyl), hydroxyl, $C_{1-6}$ alkoxy, amino, amino($C_{1-6}$ alkyl), and $NR^iR^j$—C(O)—($C_{1-6}$ alkyl)$_{k'}$-; wherein $R^i$ and $R^j$ are independently selected from the group consisting of hydrogen and branched or linear $C_{1-6}$ alkyl, and k' is 1 or 0.

In some embodiments, A is ($C_{3-7}$ cycloalkyl)($C_{1-6}$ alkyl)$_j$-, ($C_{2-9}$ heterocyclyl)($C_{1-6}$ alkyl)$_j$-, ($C_{6-10}$ aryl)$_q$-($C_{1-6}$ alkyl)$_n$-O—, or ($C_{2-7}$ heterocyclyl)-O—, wherein said cycloalkyl, alkyl, aryl or heterocyclyl can be optionally substituted; j is 1 or 0; and n is 1 or 0 and q' is 1 or 0, provided that one of n and q' is 1. In some embodiments, A is optionally substituted $C_{3-7}$ cycloalkyl (e.g., cyclopropyl).

In embodiments where all other variables are as defined in any embodiment above, A is i (as listed above). In this embodiment, useful values of A include optionally substituted $C_{3-7}$ cycloalkyl($C_{1-6}$)alkyl-. In embodiments, j is 0.

In some embodiments, $R_2$ is:

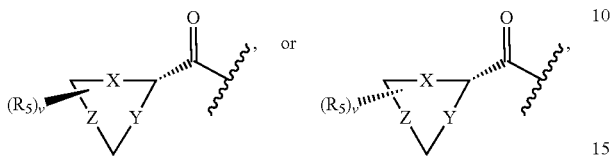

wherein, v is zero, one, two, three or four; X, Y and Z are each independently absent or —$CH_2$—, and wherein, if present, zero, one or two of H on each of X, Y and Z can be $R_5$.

In embodiments where all other variables are as defined in any embodiment above, $R_2$ is:

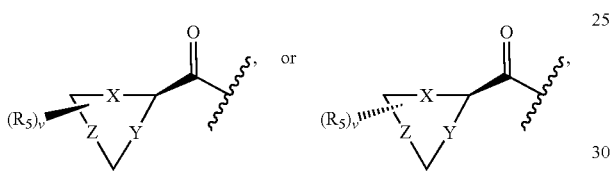

wherein, v is zero, one, two, three or four; X, Y and Z are each independently absent or —$CH_2$—, and wherein, if present, zero, one or two of H on each of X, Y and Z can be $R_5$.

In embodiments where all other variables are as defined in any embodiment above, $R_2$ is

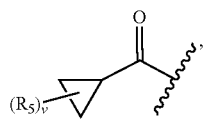

wherein, v is 0, 1, 2 or 3; and $R_5$, in each instance, is independently selected from the group consisting of $C_{1-6}$ alkyl, halogen, cyano, cyano($C_{1-6}$ alkyl)-, —$CF_3$, —$CHF_2$, hydroxy($C_{1-6}$ alkyl), halo($C_{1-6}$ alkyl), hydroxyl, ($C_{1-6}$ alkyl)-O—($C_{1-6}$ alkyl)-, —($C_{1-6}$ alkyl)-NHC(O)—($C_{1-6}$ alkyl), amino, —NR'C(O)R", acetyl, di($C_{1-6}$ alkyl)amino, mono($C_{1-6}$ alkyl)amino, amino($C_{1-6}$ alkyl), $C_{1-6}$ alkoxy, $CH_3CO_2$—($C_{1-6}$ alkyl)-, —NR'SO$_2$R", —SO$_2$R', —SO$_2$NR'R", —C(O)NR'R", —NR'C(O)OR", —NR'C(O)NR'R", optionally substituted $C_{2-9}$ heteroaryl, optionally substituted $C_{2-9}$ heterocyclyl, optionally substituted $C_{6-10}$ aryl, optionally substituted $C_{3-9}$ cycloalkyl, optionally substituted $C_{3-9}$ cycloalkyl-C(O)—, and NR'R$^f$—C(O)—($C_{1-6}$ alkyl)$_k$-, wherein said $C_{2-9}$ heteroaryl, $C_{2-9}$ heterocyclyl, and $C_{6-10}$ aryl can be optionally substituted with $C_{1-6}$ alkyl or ($C_{1-6}$ alkyl)-O—($C_{1-6}$ alkyl)-, wherein said ($C_{1-6}$ alkyl)-O—($C_{1-6}$ alkyl)- may be optionally substituted with amino, wherein, in each instance, R' and R" are independently H or $C_{1-6}$ alkyl, wherein $R^e$ and $R^f$ are each independently selected from the group consisting of hydrogen and branched or linear $C_{1-6}$ alkyl, or $R^e$ and $R^f$ together with the nitrogen to which each is bound can form a $C_{3-7}$ cycloalkyl, which can be optionally substituted (e.g., with branched or linear $C_{1-6}$ alkyl, $C_{3-4}$ cycloalkyl, halogen, cyano, —$CF_3$, —$CHF_2$, or hydroxyl);

and k is 1 or 0.

In embodiments where all other variables are as defined in any embodiment above, $R_2$ is and v is zero, one or two:

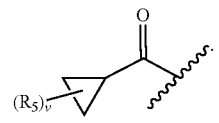

In embodiments where all other variables are as defined in any embodiment above, $R_2$ is:

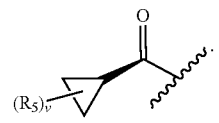

In embodiments where all other variables are as defined in any embodiment above, $R_5$ is other than hydrogen and $R_2$ is:

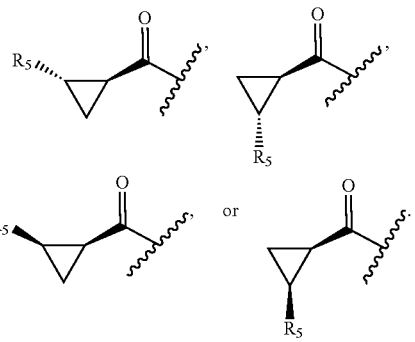

In embodiments where all other variables are as defined in any embodiment above, $R_2$ is:

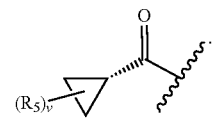

In embodiments where all other variables are as defined in any embodiment above, $R_5$ is other than hydrogen and $R_2$ is:

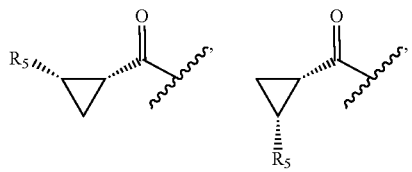

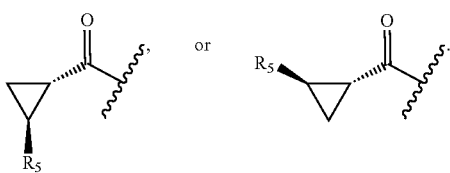

In embodiments where all other variables are as defined in any embodiment above, when A is a cycloalkyl, the cycloalkyl can be bicyclic, spiro or unsaturated.

In embodiments where all other variables are as defined in any embodiment above, $R_5$ is selected from the group consisting of hydrogen, fluorine, cyano, $NH_2$—C(O)—, alkyl-($C_{1-6}$)alkoxy-, optionally substituted $C_{2-9}$ heteroaryl, and cyano($C_{1-6}$)alkyl. In these embodiments, $R_5$ is fluoro or cyano. In these embodiments, $R_5$ is hydrogen. In these embodiments, $R_5$ is optionally substituted $C_{2-9}$ heteroaryl or cyano($C_{1-6}$)alkyl. In these embodiments, $R_5$ is cyano-$CH_2$—. In some embodiments, at least one $R_5$ is $C_{1-6}$ alkyl (e.g., methyl).

In embodiments where all other variables are as defined in any embodiment above, the compound wherein at least one $R_5$ is optionally substituted $C_{2-9}$ heteroaryl.

In embodiments where all other variables areas defined in any embodiment above, the compound wherein the at least one $R_5$ is optionally substituted $C_{2-9}$ heteroaryl is an optionally substituted 5-member heteroaryl containing 1 or 2 nitrogen atoms.

In embodiments where all other variables areas defined in any embodiment above, the compound wherein the optionally substituted 5-member heteroaryl is an optionally substituted pyrazole.

In embodiments where all other variables areas defined in any embodiment above, the compound wherein the optionally substituted pyrazole is

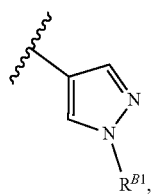

wherein the wavy line denotes the point of attachment to the cyclopropyl ring; and wherein $R^{B1}$ is branched or linear $C_{1-6}$ alkyl, wherein the alkyl can be optionally substituted with one to four hydroxyl, halogen, nitrile, amino, —O—($C_{1-6}$) alkyl, —O—($C_{1-6}$)alkylamino-, di($C_{1-6}$)alkylamino-, or —NR$^y$(CO)R$^z$, wherein R$^y$ and R$^z$, in each instance, is independently hydrogen or $C_{1-6}$ alkyl; or —SO$_2$R', wherein R' is $C_{1-6}$ alkyl.

In embodiments where all other variables areas defined in any embodiment above, the compound wherein $R^{B1}$ is optionally substituted linear $C_{1-6}$ alkyl.

In embodiments where all other variables areas defined in any embodiment above, the compound wherein the optionally substituted linear $C_{1-6}$ alkyl is methyl.

In some embodiments, $R_2$ is

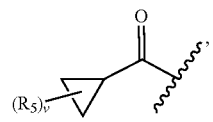

wherein v is 2, one $R_5$ is methyl and the second $R_5$ is 1-methylpyrazol-4-yl.

In some embodiments, $R_2$ is

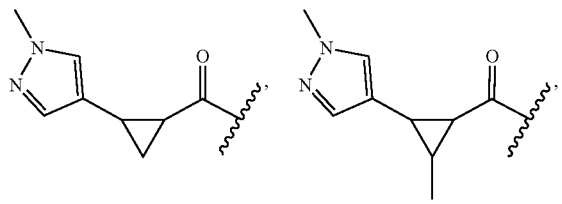

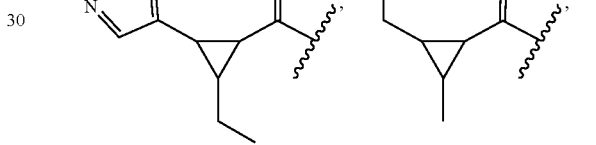

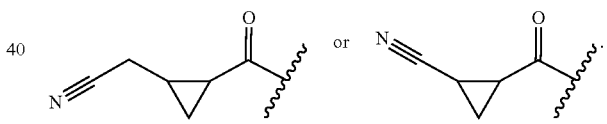

In some embodiments, $R_2$ is

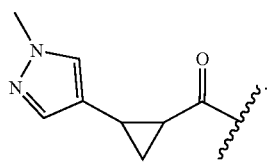 [SMILES: *C(=O)C1CC1c1cnn(C)c1]

In some embodiments, $R_2$ is

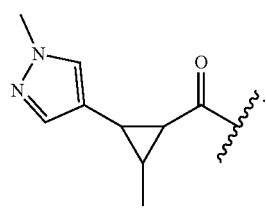 [SMILES: *C(=O)C1C(C)C1c1cnn(C)c1]

In some embodiments, $R_2$ is

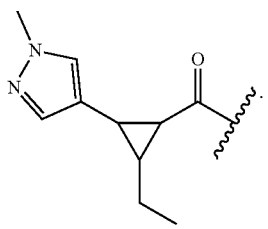 [SMILES: *C(=O)C1C(CC)C1c1cnn(C)c1]

In some embodiments, $R_2$ is

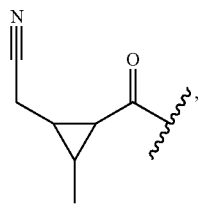 [SMILES: *C(=O)C1C(C)C1CC#N]

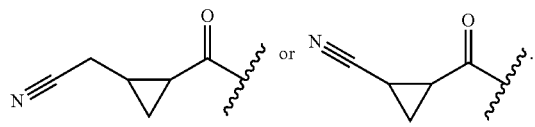 [SMILES: *C(=O)C1CC1CC#N ; *C(=O)C1CC1C#N]

In embodiments where all other variables are as defined in any embodiment above, A is —$NR^gR^h$. In these embodiments, $R^g$ is H or methyl. In particular embodiments, $R^g$ is H. In particular embodiments, m is 0.

In embodiments where all other variables areas defined in any embodiment above, A is $R_9$—($C_{1-6}$ alkyl)-. In these embodiments, particular values of $R_9$—($C_{1-6}$ alkyl)- is $R_9$—($C_{1-4}$ alkyl)-, wherein the alkyl is linear or branched and can be optionally substituted.

In embodiments where all other variables areas defined in any embodiment above, A is B—($C_{1-6}$ alkyl)$_t$-. In these embodiments, a particular value of t is 0. In these embodiments, a particular value of B is $C_{3-9}$ heteroaryl. In these embodiments, B is selected from the group consisting of:

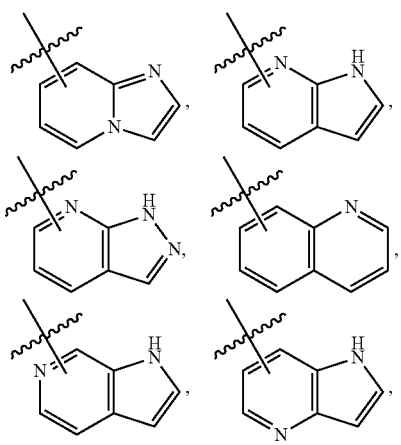

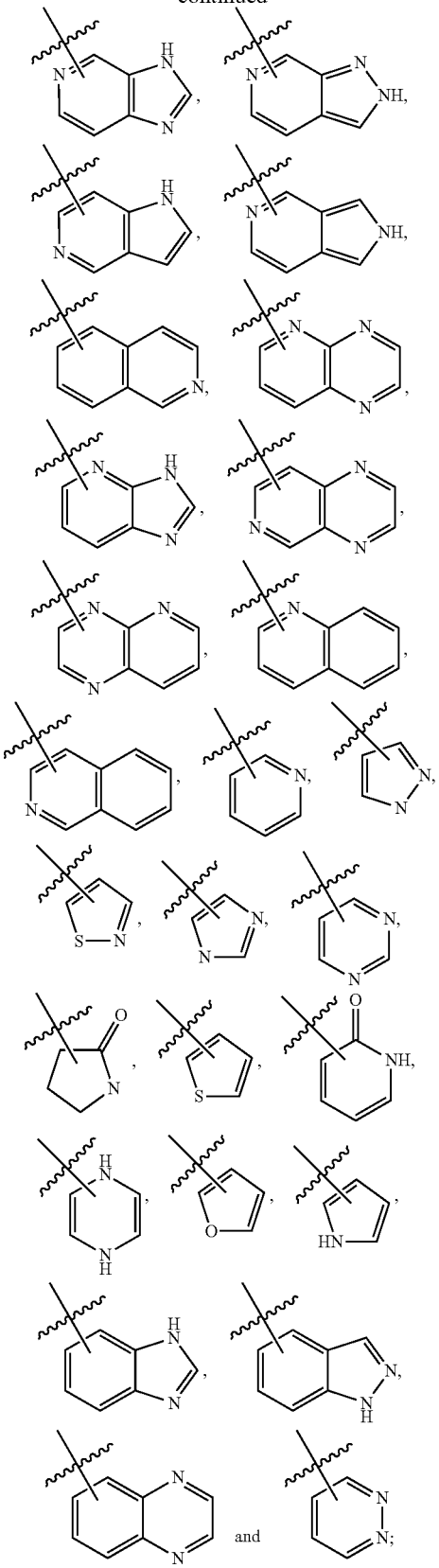

each of which can be optionally substituted with one, two, three or four substituents. In some embodiments, each of the above moieties can be optionally substituted with one, two or three substituents, $R^{10}$, $R^{10'}$ and $R^{10''}$.

In embodiments where all other variables areas defined in any embodiment above, useful values of B are selected from the group consisting of:

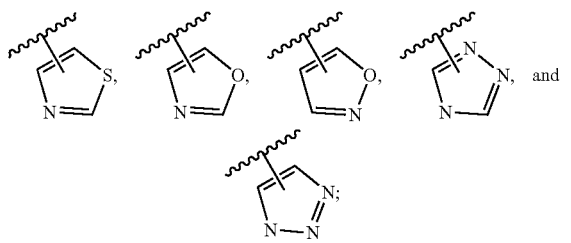

each of which can be optionally substituted with one, two, three or four substituents. In some embodiments, each of the above moieties can be optionally substituted with one, two or three substituents, $R^{10}$, $R^{10'}$ and $R^{10''}$.

In embodiments where all other variables areas defined in any embodiment above, B is selected from the group consisting of:

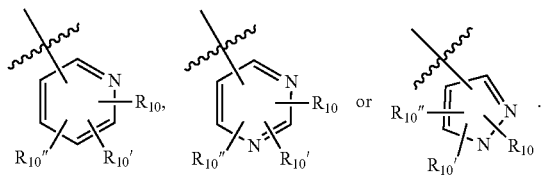

In embodiments where all other variables areas defined in any embodiment above, B is:

wherein, $R_{10}$ is $C_{1-6}$ alkyl.

In embodiments where all other variables areas defined in any embodiment above, $R_2$ is D. In some embodiments, D is:
  i. $(C_{6-10}$ aryl$)(C_{1-6}$ alkyl$)_z$-, $(C_{3-7}$ cycloalkyl$)(C_{1-6}$ alkyl$)_z$-, or $(C_{3-9}$ heteroaryl$)(C_{1-6}$ alkyl$)_z$-, wherein, said heteroaryl has 1-4 heteroatoms selected from O, S and N; and wherein said aryl, cycloalkyl or heteroaryl can be optionally substituted with one, two, three or four of $R^{14}$, $R^{15}$, $R^{16'}$ and $R^{16}$, each of which is independently selected from the group consisting of:
    a. branched or linear $C_{1-6}$ alkyl or $C_{2-6}$ alkenyl, wherein said alkyl or alkenyl can be optionally substituted with one to four substituents independently selected from the group consisting of hydroxyl, halogen, —CHF$_2$, —CF$_3$, amino, di(C$_{1-6}$ alkyl)amino, mono(C$_{1-6}$ alkyl)amino, cyano C$_{1-6}$ alkoxy, —SO$_2$R', —SO$_2$NR'R'', —NR''SO$_2$R', haloalkyl, heteroaryl, aryl, oxo, spiro alkyl, fused alkyl, —C(O)NR$^w$R$^x$, and —NR'C(O)R$^x$, wherein R$^w$ and R$^x$ are independently H or C$_{1-6}$ alkyl, or taken together to form a ring; wherein two of $R^{14}$, $R^{15}$, $R^{16'}$ and $R^{16}$ attached to different atoms are taken together with the atom to which each is attached to form a bicyclic or tricyclic, wherein said bicyclic or tricyclic may be substituted with one, two, three or four of $R^{14}$, $R^{15}$, $R^{16'}$ and $R^{16}$ as described above;
    b. $C_{3-7}$ cycloalkyl;
    c. optionally substituted $C_{3-7}$ heterocyclyl, [e.g., heterocyclyl can be optionally substituted by hydroxyl, acetyl, or oxetane];
    d. hydroxyl;
    e. halogen;
    f. —CHF$_2$;
    g. —CF$_3$;
    h. amino;
    i. di(C$_{1-6}$ alkyl)amino;
    j. mono(C$_{1-6}$ alkyl)amino;
    k. cyano;
    l. —NR$^y$C(O)R$^z$ or —NR$^y$SO$_2$R$^z$, wherein R$^y$ and R$^z$ are independently H or C$_{1-6}$ alkyl, or taken together to form a ring;
    m. —C(O)NR$^y$R$^z$, wherein R$^y$ and R$^z$ are independently H or C$_{1-6}$ alkyl, or taken together to form a ring;
    n. —SO$_2$NR$^y$R$^z$, wherein R$^y$ and R$^z$ are independently H or C$_{1-6}$ alkyl; and
    o. —C(O)OR$^y$, wherein R$^y$ is H or C$_{1-6}$ alkyl, or taken together to form a ring; and, z is 1 or 0;
  ii. $C_{3-7}$ cycloalkyl-SO$_2$—, wherein said cycloalkyl can be optionally substituted with one or two of R$^{6'}$, wherein R$^{6'}$, in each instance, is independently selected from the group consisting of branched or linear $C_{1-6}$ alkyl, halogen, cyano, —CF$_3$, —CHF$_2$, hydroxy(C$_{1-6}$ alkyl), halo(C$_{1-6}$ alkyl), hydroxyl, (C$_{1-6}$ alkyl)-O—(C$_{1-6}$ alkyl)-, C$_{1-6}$ alkoxy, amino, di(C$_{1-6}$ alkyl)amino, mono(C$_{1-6}$ alkyl)amino, amino(C$_{1-6}$ alkyl), and NR$^{e'}$R$^{f'}$—C(O)—(C$_{1-6}$ alkyl)$_n$-, wherein R$^{e'}$ and R$^{f'}$ are independently selected from the group consisting of hydrogen and branched or linear $C_{1-6}$ alkyl, and n is 1 or 0; and
  iii. H, optionally substituted $C_{1-6}$ alkyl (e.g., haloalkyl) or optionally substituted $C_{3-9}$ cycloalkyl, optionally substituted $C_{6-10}$ aryl, optionally substituted $C_{2-9}$ heteroaryl, or optionally substituted $C_{2-9}$ heterocyclyl (e.g. pyrrolidine).

In some embodiments, D is $C_{3-9}$ heteroaryl-(C$_{1-6}$ alkyl)$_z$-. In these embodiments, a particular value of z is 0. In these embodiments, particular values of the heteroaryl are

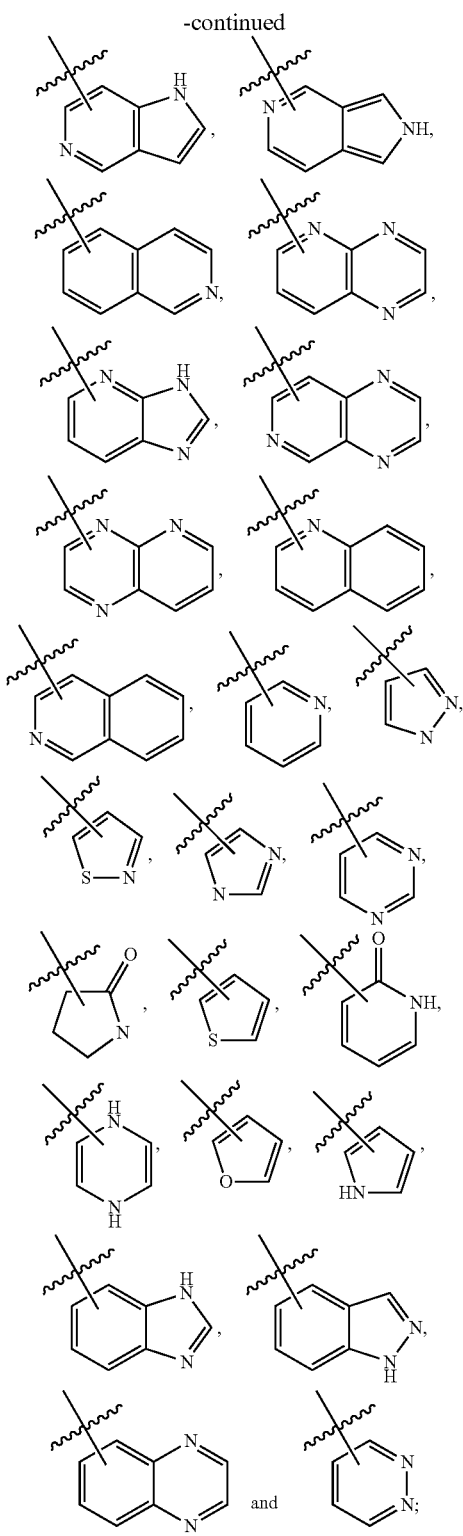

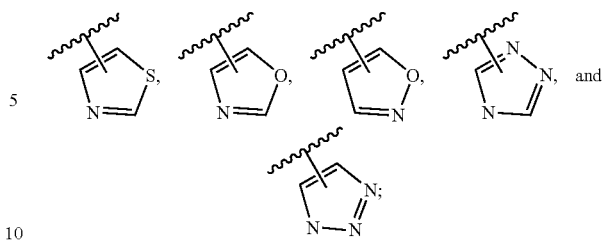

each of which can be optionally substituted with one, two, three or four substituents. In some embodiments, each of the above moieties can be optionally substituted with one, two or three substituents, $R^{14}$, $R^{15}$ and $R^{16}$.

In embodiments where all other variables areas defined in any embodiment above, useful values of D are selected from the group consisting of

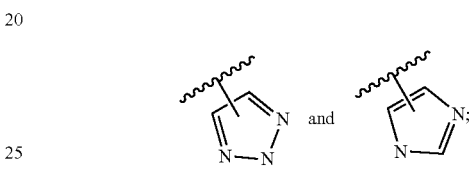

each of which can be optionally substituted with one, two, three substituents. In some embodiments, the three substituents are $R^{14}$, $R^{15}$ and $R^{16}$.

In embodiments where all other variables areas defined in any embodiment above, the heteroaryl of D is

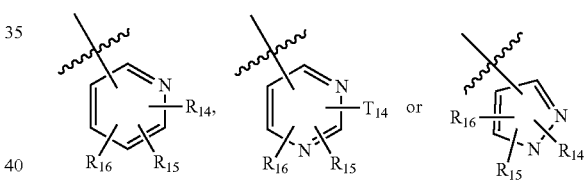

In some embodiments, D is

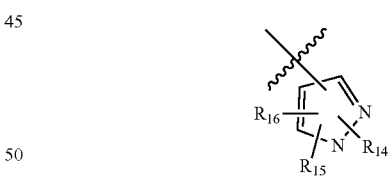

In some of these embodiments, each of $R^{14}$, $R^{15}$, and $R^{16}$ is independently selected from the group consisting of:
 a. branched or linear $C_{1-6}$ alkyl, wherein said alkyl can be optionally substituted with hydroxyl, halogen, —$CF_2$, —$CF_3$, amino, di($C_{1-6}$)alkylamino, mono($C_{1-6}$)alkylamino, cyano $C_{1-6}$ alkoxy, —$SO_2R'$, —$SO_2NR'R''$, —(CO)$NR^wR^x$, or —$NR^w$(CO)$R^x$, wherein $R^w$ and $R^x$ are independently H or $C_{1-6}$ alkyl, or wherein two of $R^{14}$, $R^{15}$, and $R^{16}$, as described herein, when attached to different atoms are taken together with the atom to which each is attached to form a bicyclic;
 b. $C_{3-7}$ cycloalkyl;
 c. $C_{3-7}$ heterocyclyl;
 d. hydroxyl;
 e. halogen;

each of which can be optionally substituted with one, two, three or four substituents. In some embodiments, each of the above moieties can be optionally substituted with one, two or three substituents, $R^{14}$, $R^{15}$ and $R^{16}$.

In embodiments where all other variables areas defined in any embodiment above, useful values of D are selected from the group consisting of:

f. —CF$_2$;
g. —CF$_3$;
h. amino;
i. di(C$_{1-6}$)alkylamino;
j. mono(C$_{1-6}$)alkylamino;
k. cyano;
l. —NR$^y$(CO)R$^z$, wherein R$^y$ and R$^z$ are independently H or C$_{1-6}$ alkyl;
m. —(CO)NR$^y$R$^z$, wherein R$^y$ and R$^z$ are independently H or C$_{1-6}$ alkyl;
n. —SO$_2$NR$^y$R$^z$, wherein R$^y$ and R$^z$ are independently H or C$_{1-6}$ alkyl; and
o. —(CO)OR$^y$, wherein R$^y$ is H or C$_{1-6}$ alkyl;
wherein two of the R$^{14}$, R$^{15}$, and R$^{16}$ attached to different atoms are taken together with the atom to which each is attached to form a bicyclic or tricyclic; wherein said bicyclic or tricyclic is optionally substituted.

In some of these embodiments, two of R$^{14}$, R$^{15}$, and R$^{16}$ attached to different atoms are taken together with the atom to which each is attached to form a bicyclic or tricyclic. In some embodiments, D is a bicyclic (or tricyclic where further ring fusion is present) which is

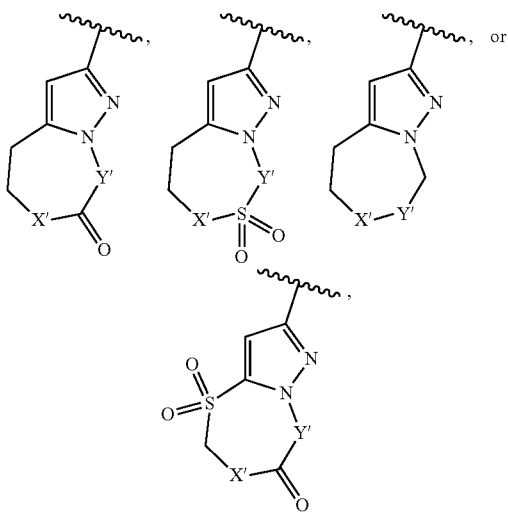

wherein X' and Y' are each independently C, N, S, or O; and wherein said bicyclic is optionally substituted with R$^{17}$, R$^{18}$, R$^{19}$, and R$^{20}$, wherein R$^{17}$, R$^{18}$, R$^{19}$, and R$^{20}$, are each independently selected from the group consisting of hydrogen, hydroxyl, amino, and C$_{1-6}$ alkyl, and where two of R$^{17}$, R$^{18}$, R$^{19}$, and R$^{20}$ taken together with the carbon to which they are attached can form a C$_3$-C$_5$ spiro or C$_{2-9}$ heteroaryl ring. In some of these embodiments, at least one of X' or Y' is N.

In some embodiments, D is a bicyclic which is

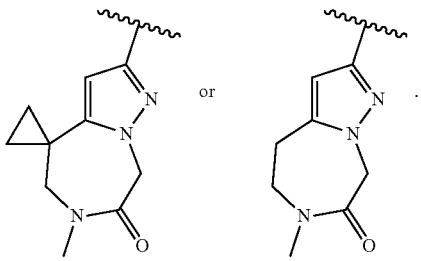 [SMILES: *c1cc2n(n1)CC(=O)N(C)CC21CC1 ; *c1cc2n(n1)CC(=O)N(C)CC2]

In embodiments where all other variables are as defined in any embodiment above, the heteroaryl of D is:

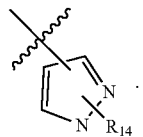

In embodiments where all other variables are as defined in any embodiment above, the compound wherein D is optionally substituted C$_{6-10}$ aryl.

In embodiments where all other variables are as defined in any embodiment above, the compound wherein the optionally substituted C$_{6-10}$ aryl is an optionally substituted phenyl.

In embodiments where all other variables are as defined in any embodiment above, the compound wherein the optionally substituted phenyl is substituted with an optionally substituted branched or linear C$_{1-6}$ alkyl or a C$_{3-7}$ heterocyclyl.

In embodiments where all other variables are as defined in any embodiment above, the compound wherein D is is a 5-membered heteroaryl having the formula

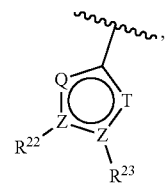

or a 6-membered heteroaryl having the formula

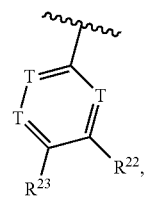

wherein:
Q is NR$^{20}$, CR$^{20}$, O or S;
each T is independently N or CR$^{21}$;
each Z is independently N or C, provided that only one Z is N;
each R$^{20}$ and R$^{21}$ is independently hydrogen, alkyl, haloalkyl, alkoxy, halogen, hydroxy, or cyano; and
R$^{22}$ and R$^{23}$ are taken together with the atoms to which they are attached to form a bicyclic; wherein the bicyclic may contain one more heteroatoms selected from N, S and O; and wherein the bicyclic is optionally substituted with one, two, three, four or five R$^{30}$;
wherein each R$^{30}$ is independently C$_{1-6}$ alkyl, C$_{2-6}$ alkenyl, C$_{3-7}$ cycloalkyl, C$_{3-7}$ heterocyclyl, halogen, cyano, oxo, —NR$^{31}$R$^{32}$, —SO$_2$NR$^{31}$R$^{32}$, —C(O)NR$^{31}$R$^{32}$, —C(O)OR$^{33}$, —OR$^{33}$, —NR$^{33}$C(O)R$^{34}$, —NR$^{33}$SO$_2$R$^{35}$ or —SO$_2$R$^{35}$; wherein the C$_{1-6}$ alkyl, C$_{2-6}$ alkenyl, C$_{3-7}$ cycloalkyl and C$_{3-7}$ heterocyclyl of R$^{30}$ are optionally substituted with one to four R$^{40}$; or two R$^{30}$ groups are taken together with the parent moiety to with they are attached to form a ring which is optionally substituted with one to four $R^{40}$;

each $R^{31}$ and $R^{32}$ is independently hydrogen or $C_{1-6}$ alkyl; or $R^{31}$ and $R^{32}$ are taken together with the nitrogen atom to which they are attached to form a $C_{3-7}$ heterocyclyl optionally substituted with one to four $R^{40}$;

each $R^{33}$ and $R^{34}$ are independently hydrogen or $C_{1-6}$ alkyl;

$R^{35}$ is $C_{1-6}$ alkyl;

each $R^{40}$ is independently selected from the group consisting of halogen, cyano, oxo, $-NR^{41}R^{42}$, $-SO_2NR^{41}R^{42}$, $-C(O)NR^{41}R^{42}$, $-C(O)OR^{43}$, $-OR^{43}$, $-NR^{43}C(O)R^{44}$, $-NR^{43}SO_2R^{45}$ or $-SO_2R^{45}$; $C_{1-6}$ alkyl, $C_{1-6}$ haloalkyl [e.g., $-CHF_2$, or $-CF_3$], $C_{2-9}$ heteroaryl, $C_{6-10}$ aryl, oxo; or two $R^{40}$ groups are taken together with the parent moiety to with they are attached to form a ring which is optionally substituted with one to three substituents selected from $C_{1-6}$ alkyl, $C_{1-6}$ haloalkyl, hydroxyl and oxo;

each $R^{41}$ and $R^{42}$ is independently hydrogen or $C_{1-6}$ alkyl; or $R^{41}$ and $R^{42}$ are taken together with the nitrogen atom to which they are attached to form a $C_{3-7}$ heterocyclyl optionally substituted with one to three substituents selected from $C_{1-6}$ alkyl, $C_{1-6}$ haloalkyl, hydroxyl and oxo;

each $R^{43}$ and $R^{44}$ are independently hydrogen or $C_{1-6}$ alkyl; and $R^{45}$ is $C_{1-6}$ alkyl.

In some embodiments, D is:

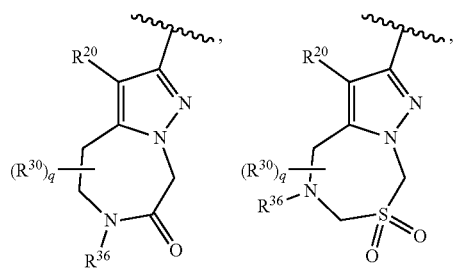

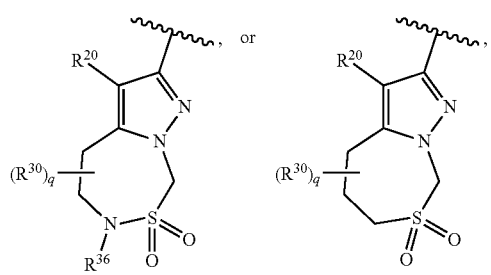

wherein q is 0, 1, 2, 3, 4, 5 or 6; $R^{36}$ is independently hydrogen or $R^{30}$; and $R^{20}$ and $R^{30}$ are as detailed herein. In some of these embodiments, $R^{20}$ is hydrogen, $C_{1-6}$ alkyl (e.g., methyl), halogen (e.g., fluoro), hydroxyl, or $C_{1-6}$ alkoxy (e.g., methoxy). In some embodiments, $R^{20}$ is H, Me, F or OH. In some of these embodiments, $R^{36}$ is hydrogen or $C_{1-6}$ alkyl (e.g., methyl). In some of these embodiments, q is 0.

In some embodiments, D is:

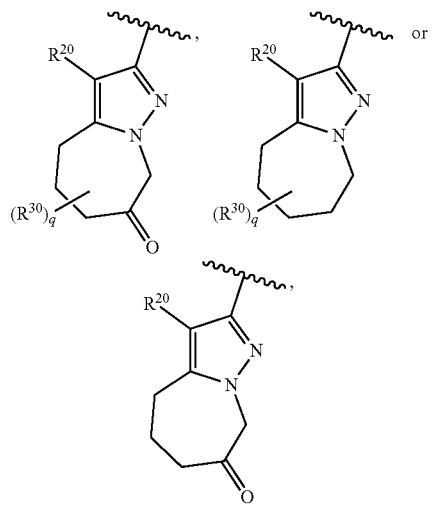

wherein q is 0, 1, 2, 3, 4, 5 or 6; and $R^{20}$ and $R^{30}$ are as detailed herein. In some of these embodiments, q is 0. In some of these embodiments, $R^2$ is hydrogen, $C_6$alkyl (e.g., methyl), halogen (e.g., fluoro), hydroxyl, or $C_{1-6}$ alkoxy (e.g., methoxy). In some embodiments, $R^{20}$ is H, Me, F or OH.

In some embodiments, D is:

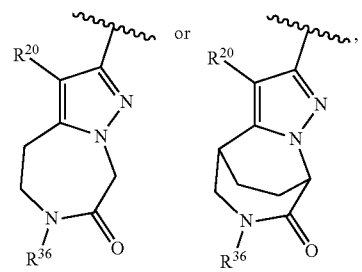

wherein $R^{36}$ is independently hydrogen or $R^{30}$; and $R^{20}$ and $R^{30}$ are as detailed herein. In some embodiments, $R^{36}$ is hydrogen or $C_{1-6}$ alkyl (e.g., methyl); and $R^{20}$ is hydrogen.

In some embodiments, wherein D is

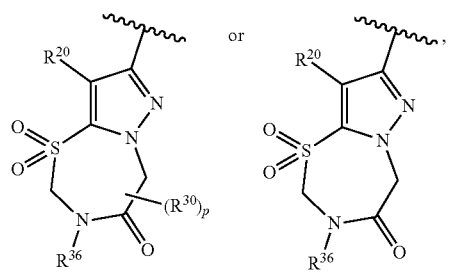

wherein p is 0, 1, 2, 3 or 4; $R^{36}$ is independently hydrogen or $R^{30}$; and $R^{20}$ and $R^{30}$ are as detailed herein. In some embodiments, p is 0. In some embodiments, $R^{36}$ is hydrogen or $C_{1-6}$ alkyl (e.g., methyl); and $R^{20}$ is hydrogen.

In some embodiments, wherein D is

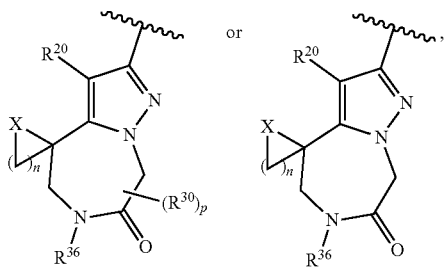

wherein X is CH$_2$, N, O or S; n is 1, 2, 3 or 4; p is 0, 1, 2, 3 or 4; R$^{36}$ is hydrogen or R$^{30}$; and R$^{20}$ and R$^{30}$ are as detailed herein. In some of these embodiments, X is CH$_2$ and n is 1. In some embodiments, R$^{36}$ is hydrogen or C$_{1-6}$ alkyl (e.g., methyl); and R$^{20}$ is hydrogen.

In some embodiments, wherein D is

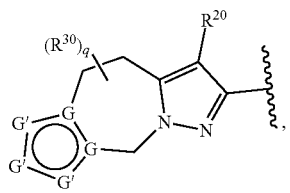

wherein q is 0, 1, 2, 3, 4, 5 or 6; G is independently C or N; G' is independently N, NR$^{46}$, CR$^{47}$, S or O; R$^{46}$ and R$^{47}$ are independently hydrogen or R$^{40}$, and R$^{20}$ and R$^{40}$ are as detailed herein. In some embodiments, R$^{46}$ and R$^{47}$ are taken together to form a ring. In some of these embodiments, one of G is C and the other one of G is N. In some embodiments, each G is C. In some embodiments, at least one of G' is N. In some embodiments, at least one of G' is CR$^{47}$. In some embodiments, R$^{47}$ is H. In some embodiments, R$^{20}$ is hydrogen.

In some embodiments, wherein D is

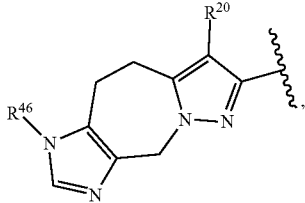

wherein R$^{20}$ and R$^{46}$ are as detailed herein. In some embodiments, R$^{46}$ is hydrogen or C$_{1-6}$ alkyl (e.g., methyl); and R$^{20}$ is hydrogen.

In some embodiments, wherein D is

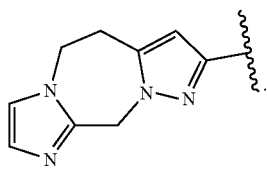 [SMILES: *c1cc2n(n1)Cc1nccn1CC2]

In some embodiments, wherein D is

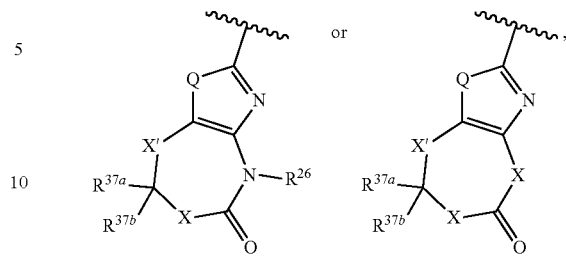

wherein Q is NR$^{20}$, O or S; X is CR$^{38a}$R$^{38b}$, NR$^{36}$, S or O; X' is CR$^{39a}$R$^{39b}$, NR$^{36}$, S, SO$_2$ or O; R$^{36}$, R$^{37a}$, R$^{37b}$, R$^{38a}$ and R$^{38b}$ are independently hydrogen or R$^{30}$; R$^{39a}$ and R$^{39b}$ are independently hydrogen or R$^{30}$, or R$^{39a}$ and R$^{39b}$ are taken together with the carbon atom to which they are attached to form a C$_{3-7}$ cycloalkyl or C$_{3-7}$ heterocyclyl; and R$^{20}$ and R$^{30}$ are as detailed herein. In some of these embodiments, Q is NR$^{20}$. In some of these embodiments, Q is S. In some embodiments, X is CH$_2$ or NR$^{36}$. In some embodiments, X' is CH$_2$. In some embodiments, X' is SO$_2$. In some embodiments, X' is CR$^{39a}$R$^{39b}$ where R$^{39a}$ and R$^{39b}$ are taken together with the carbon atom to which they are attached to form a cyclopropyl. In some embodiments, R$^{36}$ is hydrogen or C$_{1-6}$ alkyl (e.g., methyl); and R$^{20}$ is hydrogen.

In some embodiments, wherein D is

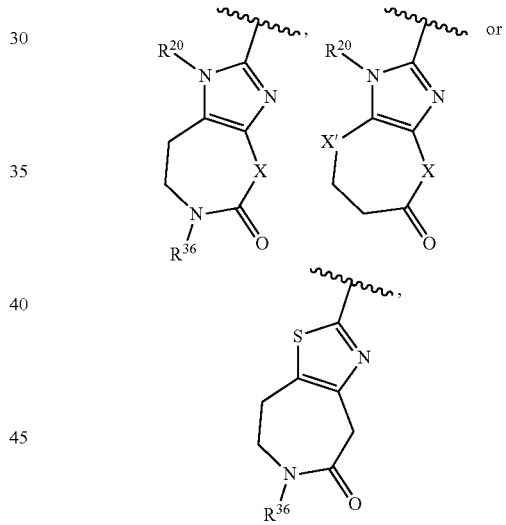

wherein X, X', R$^{20}$ and R$^{36}$ are as detailed herein. In some of these embodiments, X is CH$_2$ or NR$^{36}$. In some embodiments, X' is CH$_2$. In some embodiments, X' is SO$_2$. In some embodiments, X' is CR$^{39a}$R$^{39b}$ where R$^{39a}$ and R$^{39b}$ are taken together with the carbon atom to which they are attached to form a cyclopropyl. In some embodiments, R$^{36}$ is hydrogen or C$_{1-6}$ alkyl (e.g., methyl). In some embodiments, R$^{20}$ is hydrogen.

In embodiments where all other variables are as defined in any embodiment above, the compound wherein R$_{1'}$ is optionally substituted C$_{2-9}$ heteroaryl.

In embodiments where all other variables are as defined in any embodiment above, the compound wherein the optionally substituted C$_{2-9}$ heteroaryl is an optionally substituted 5-member heteroaryl containing 1 or 2 nitrogen atoms.

In embodiments where all other variables are as defined in any embodiment above, the compound wherein the 5-member heteroaryl is a pyrazole.

In embodiments where all other variables are as defined in any embodiment above, the compound wherein $R_1$ is halogen.

In embodiments where all other variables areas defined in any embodiment above, the compound wherein the halogen is fluoro or chloro.

In embodiments where all other variables areas defined in any embodiment above, the compound wherein $R_{1'}$ is optionally substituted $C_{1-6}$ alkyl, $C_{2-6}$ alkenyl, or $C_{3-6}$ cycloalkyl.

In embodiments where all other variables areas defined in any embodiment above, the compound wherein $R_{1'}$ is optionally substituted $C_{1-6}$ alkyl.

In embodiments where all other variables areas defined in any embodiment above, the compound wherein $R_{1'}$ is optionally substituted methyl or ethyl.

In embodiments where all other variables areas defined in any embodiment above, the compound wherein $R_{1'}$ is methyl.

In embodiments where all other variables areas defined in any embodiment above, the compound wherein $R_1$ is optionally substituted $C_{6-10}$ aryl.

In embodiments where all other variables areas defined in any embodiment above, the compound wherein the optionally substituted $C_{6-10}$ aryl is optionally substituted phenyl.

In embodiments where all other variables areas defined in any embodiment above, the compound wherein the optionally substituted phenyl is substituted with optionally substituted branched or linear $C_{1-6}$ alkyl, $C_{1-6}$ alkoxy, halogen, cyano, hydroxyl, amino, —$CF_3$, or —(CO)$NR^cR^d$; wherein $R^c$ and $R^d$ are as described above.

In embodiments, where all other variables areas defined in any embodiment above, a compound including compound number 1, 2, 3, 4, 5, 6, 7, 8, 9, 10, 11, 12, 13, 14, 15, 16, 17, 18, 19, 20, 21, 22, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 62, 63, 64, 65, 66, 67, 68, 70, 71, 72, 73, 74, 75, 76, 77, 78, 79, 80, 81, 82, 83, 84, 85, 86, 87, 88, 89, 90, 91, 92, 93, 94, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, and 348.

In some embodiments, the disclosure provides a compound of formula I or Ia, or a pharmaceutically acceptable salt thereof, wherein the compound is selected from the group consisting of one or more compounds in Table 1, Table 2 and Table 3. In some embodiments, the compound is selected from Compound Nos. 1-348 in Table 1, or a pharmaceutically acceptable salt thereof. In some embodiments, the compound is selected from Compound Nos. 349-429 in Table 2, or a pharmaceutically acceptable salt thereof. In some embodiments, the compound is selected from Compound Nos. 430-572 in Table 3, or a pharmaceutically acceptable salt thereof

TABLE 1

| Cmpd No. | Structure | Name |
|---|---|---|
| 1 | 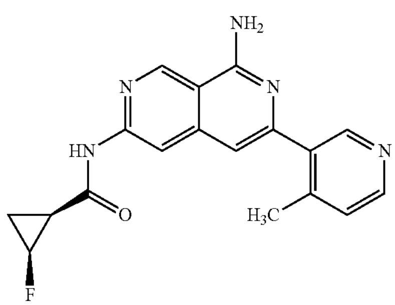 [SMILES: Cc1ccncc1-c1cc2cc(NC(=O)[C@@H]3C[C@@H]3F)ncc2c(N)n1] | cis-N-[8-amino-6-(4-methyl-3-pyridyl)-2,7-naphthyridin-3-yl]-2-fluoro-cyclopropanecarboxamide |

TABLE 1-continued

| Cmpd No. | Structure | Name |
|---|---|---|
| 2 | 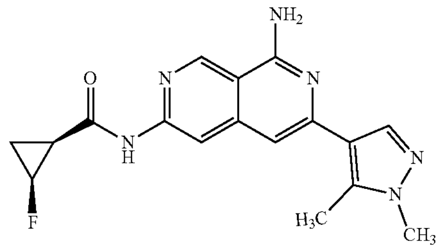 | cis-N-(8-amino-6-(1,5-dimethyl-1H-pyrazol-4-yl)-2,7-naphthyridin-3-yl)-2-fluorocyclopropanecarboxamide |
| 3 | 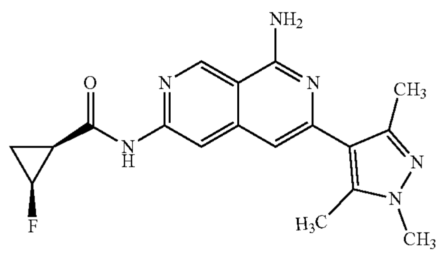 | cis-N-(8-amino-6-(1,3,5-trimethyl-1H-pyrazol-4-yl)-2,7-naphthyridin-3-yl)-2-fluorocyclopropanecarboxamide |
| 4 | 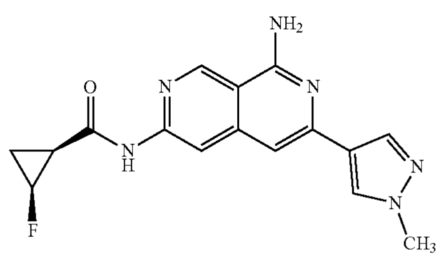 | cis-N-(8-amino-6-(1-methyl-1H-pyrazol-4-yl)-2,7-naphthyridin-3-yl)-2-fluorocyclopropanecarboxamide |

TABLE 1-continued

| Cmpd No. | Structure | Name |
|---|---|---|
| 5 | 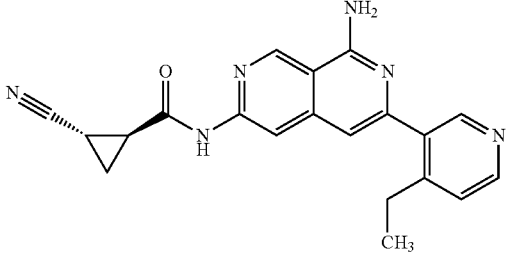 | trans-N-(8-amino-6-(4-ethylpyridin-3-yl)-2,7-naphthyridin-3-yl)-2-cyanocyclopropanecarboxamide |
| 6 | 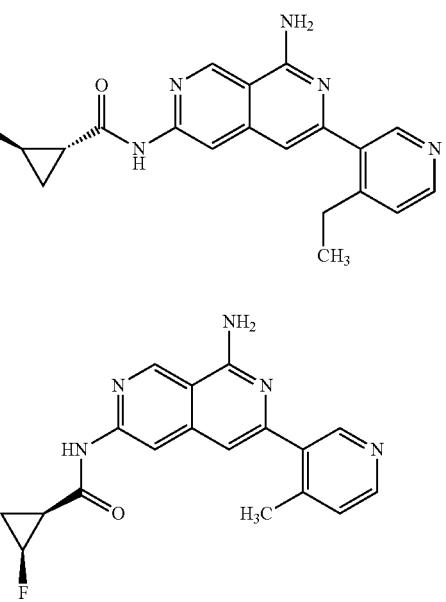 | (1S,2S)-N-(8-amino-6-(4-methylpyridin-3-yl)-2,7-naphthyridin-3-yl)-2-fluorocyclopropanecarboxamide |
| 7 | 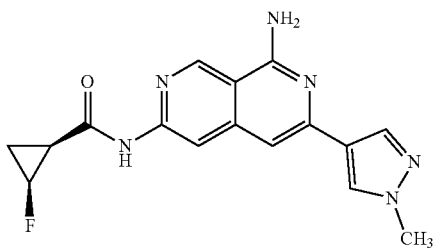 [SMILES: Cn1cc(-c2cc3cc(NC(=O)[C@@H]4C[C@@H]4F)ncc3c(N)n2)cn1] | (1S,2S)-N-(8-amino-6-(1-methyl-1H-pyrazol-4-yl)-2,7-naphthyridin-3-yl)-2-fluorocyclopropanecarboxamide |
| 8 | 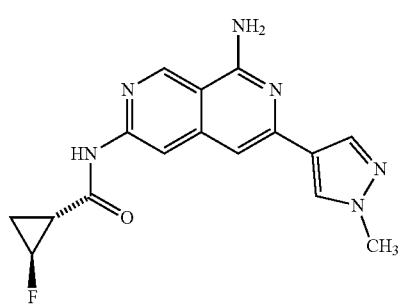 | trans-N-(8-amino-6-(1-methyl-1H-pyrazol-4-yl)-2,7-naphthyridin-3-yl)-2-fluorocyclopropanecarboxamide |

TABLE 1-continued

| Cmpd No. | Structure | Name |
|---|---|---|
| 9 | 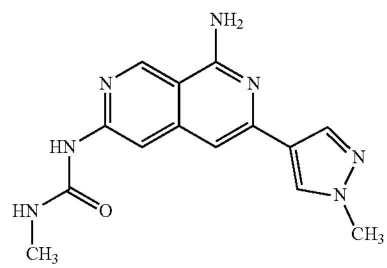 [SMILES: CNC(=O)Nc1cc2cc(-c3cnn(C)c3)nc(N)c2cn1] | 1-(8-amino-6-(1-methyl-1H-pyrazol-4-yl)-2,7-naphthyridin-3-yl)-3-methylurea |
| 10 | 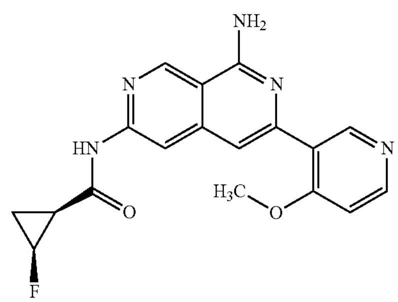 [SMILES: COc1ccncc1-c1cc2cc(NC(=O)[C@@H]3C[C@@H]3F)ncc2c(N)n1] | (1S,2S)-N-(8-amino-6-(4-methoxypyridin-3-yl)-2,7-naphthyridin-3-yl)-2-fluorocyclopropanecarboxamide |
| 11 | 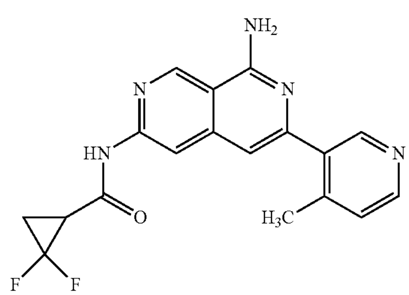 [SMILES: Cc1ccncc1-c1cc2cc(NC(=O)C3CC3(F)F)ncc2c(N)n1] | N-(8-amino-6-(4-methylpyridin-3-yl)-2,7-naphthyridin-3-yl)-2,2-difluorocyclopropanecarboxamide |
| 12 | 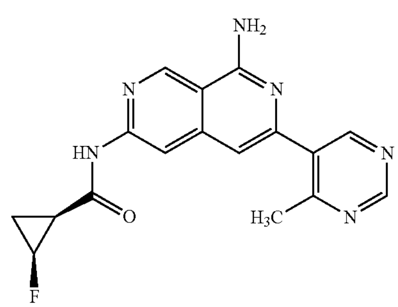 [SMILES: Cc1ncncc1-c1cc2cc(NC(=O)[C@@H]3C[C@@H]3F)ncc2c(N)n1] | (1S,2S)-N-(8-amino-6-(4-methylpyrimidin-5-yl)-2,7-naphthyridin-3-yl)-2-fluorocyclopropanecarboxamide |

TABLE 1-continued

| Cmpd No. | Structure | Name |
|---|---|---|
| 13 | 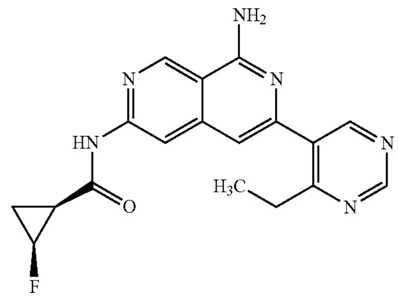 [SMILES: CCc1ncncc1-c1cc2cc(NC(=O)[C@@H]3C[C@@H]3F)ncc2c(N)n1] | (1S,2S)-N-(8-amino-6-(4-ethylpyrimidin-5-yl)-2,7-naphthyridin-3-yl)-2-fluorocyclopropanecarboxamide |
| 14 | 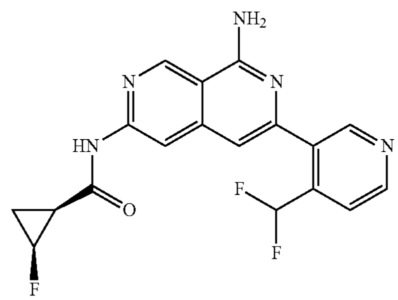 [SMILES: Nc1nc(-c2cnccc2C(F)F)cc2cc(NC(=O)[C@@H]3C[C@@H]3F)ncc12] | (1S,2S)-N-(8-amino-6-(4-(difluoromethyl)pyridin-3-yl)-2,7-naphthyridin-3-yl)-2-fluorocyclopropanecarboxamide |
| 15 | 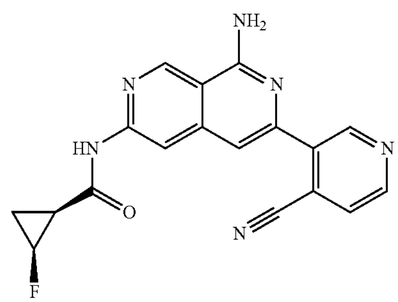 [SMILES: N#Cc1ccncc1-c1cc2cc(NC(=O)[C@@H]3C[C@@H]3F)ncc2c(N)n1] | (1S,2S)-N-(8-amino-6-(4-cyanopyridin-3-yl)-2,7-naphthyridin-3-yl)-2-fluorocyclopropanecarboxamide |
| 16 | 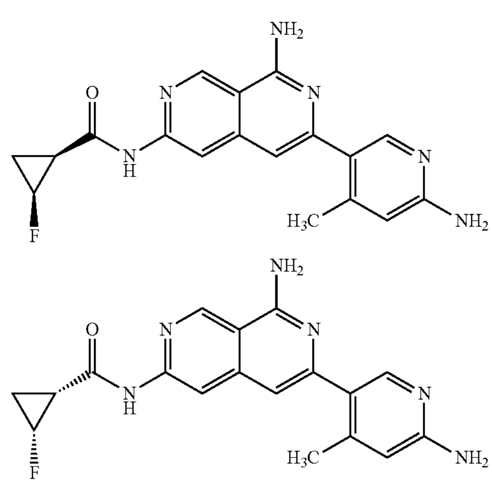 | cis-N-(8-amino-6-(6-amino-4-methylpyridin-3-yl)-2,7-naphthyridin-3-yl)-2-fluorocyclopropanecarboxamide |

TABLE 1-continued

| Cmpd No. | Structure | Name |
| --- | --- | --- |
| 17 | 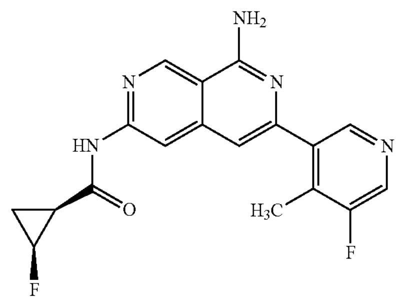 [SMILES: Cc1c(F)cncc1-c1cc2cc(NC(=O)[C@@H]3C[C@@H]3F)ncc2c(N)n1] | (1S,2S)-N-(8-amino-6-(5-fluoro-4-methylpyridin-3-yl)-2,7-naphthyridin-3-yl)-2-fluorocyclopropanecarboxamide |
| 18 | 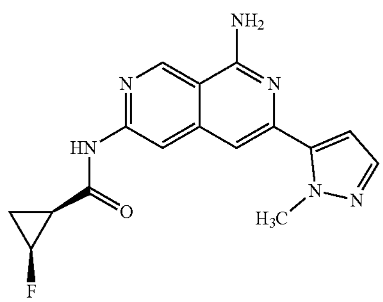 [SMILES: Cn1nccc1-c1cc2cc(NC(=O)[C@@H]3C[C@@H]3F)ncc2c(N)n1] | (1S,2S)-N-(8-amino-6-(1-methyl-1H-pyrazol-5-yl)-2,7-naphthyridin-3-yl)-2-fluorocyclopropanecarboxamide |
| 19 | | cis-N-(8-amino-6-(6-methyl-1H-benzo[d]imidazol-5-yl)-2,7-naphthyridin-3-yl)-2-fluorocyclopropanecarboxamide |
|  | |  |
| 20 | 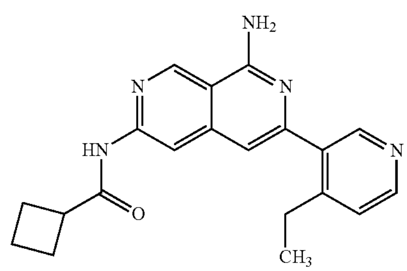 [SMILES: CCc1ccncc1-c1cc2cc(NC(=O)C3CCC3)ncc2c(N)n1] | N-[8-amino-6-(4-ethyl-3-pyridyl)-2,7-naphthyridin-3-yl]cyclobutanecarboxamide |

TABLE 1-continued
| Cmpd No. | Structure | Name |
|---|---|---|
| 21 | 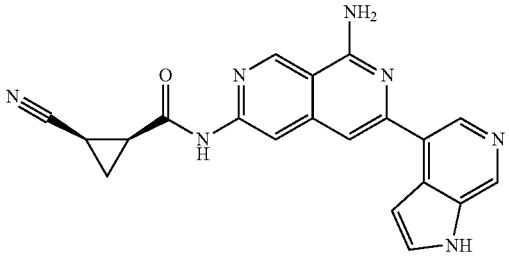 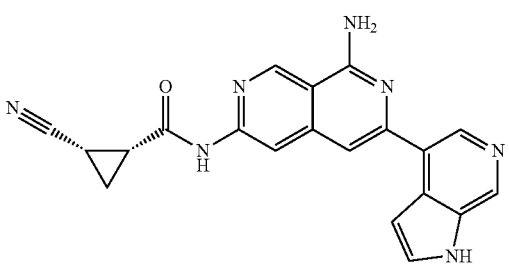 | cis-N-(8-amino-6-(1H-pyrrolo[2,3-c]pyridin-4-yl)-2,7-naphthyridin-3-yl)-2-cyanocyclopropanecarboxamide |
| 22 | 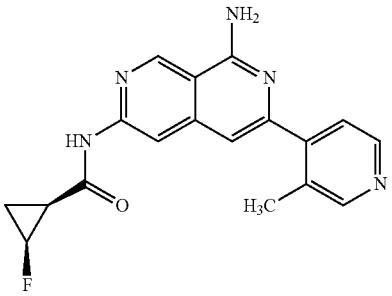 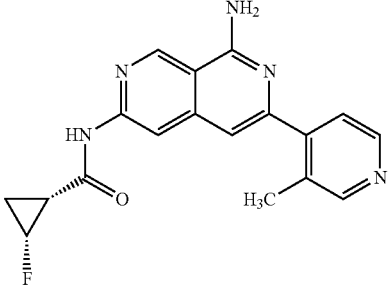 | cis-N-(8-amino-6-(3-methylpyridin-4-yl)-2,7-naphthyridin-3-yl)-2-fluorocyclopropanecarboxamide |
| 24 | 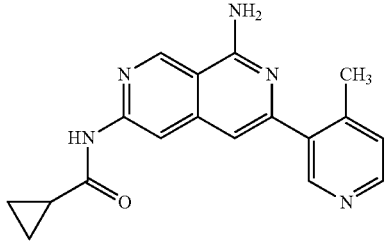 [SMILES: Cc1ccncc1-c1cc2cc(NC(=O)C3CC3)ncc2c(N)n1] | N-(8-amino-6-(4-methylpyridin-3-yl)-2,7-naphthyridin-3-yl)cyclopropanecarboxamide |

TABLE 1-continued

| Cmpd No. | Structure | Name |
|---|---|---|
| 25 | 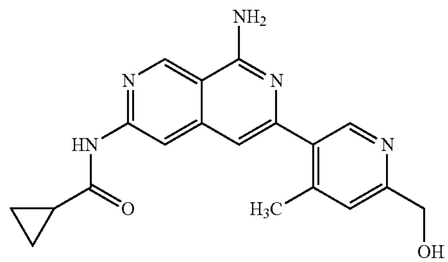 [SMILES: Cc1cc(CO)ncc1-c1cc2cc(NC(=O)C3CC3)ncc2c(N)n1] | N-(8-amino-6-(6-(hydroxymethyl)-4-methylpyridin-3-yl)-2,7-naphthyridin-3-yl)cyclopropanecarboxamide |
| 26 | 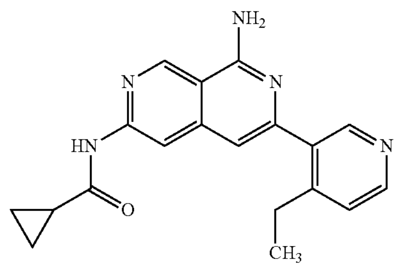 | N-(8-amino-6-(4-ethylpyridin-3-yl)-2,7-naphthyridin-3-yl)cyclopropanecarboxamide |
| 27 | 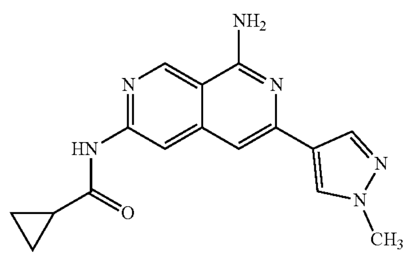 [SMILES: Cn1cc(-c2cc3cc(NC(=O)C4CC4)ncc3c(N)n2)cn1] | N-[8-amino-6-(1-methylpyrazol-4-yl)-2,7-naphthyridin-3-yl]cyclopropanecarboxamide |
| 28 | 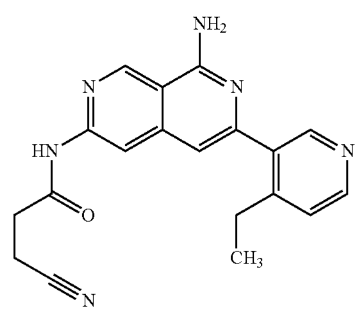 [SMILES: CCc1ccncc1-c1cc2cc(NC(=O)CCC#N)ncc2c(N)n1] | N-[8-amino-6-(4-ethyl-3-pyridyl)-2,7-naphthyridin-3-yl]-3-cyano-propanamide and N'-[8-amino-6-(4-ethyl-3-pyridyl)-2,7-naphthyridin-3-yl]butanediamide |
| 29 | 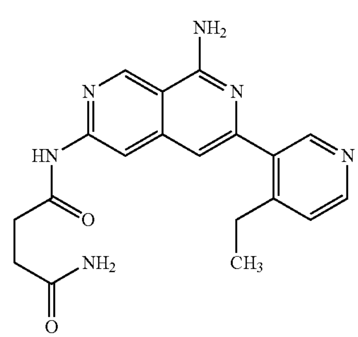 [SMILES: CCc1ccncc1-c1cc2cc(NC(=O)CCC(N)=O)ncc2c(N)n1] | N'-[8-amino-6-(4-ethyl-3-pyridyl)-2,7-naphthyridin-3-yl]butanediamide |

TABLE 1-continued

| Cmpd No. | Structure | Name |
|---|---|---|
| 30 | 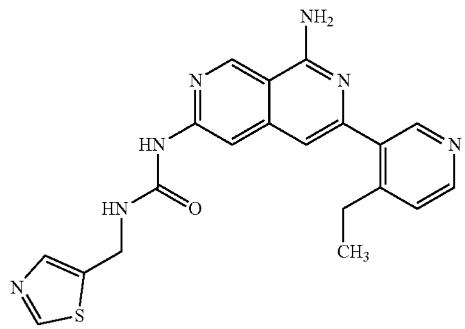 [SMILES: CCc1ccncc1-c1cc2cc(NC(=O)NCc3cncs3)ncc2c(N)n1] | 1-[8-amino-6-(4-ethyl-3-pyridyl)-2,7-naphthyridin-3-yl]-3-(thiazol-5-ylmethyl)urea |
| 31 | 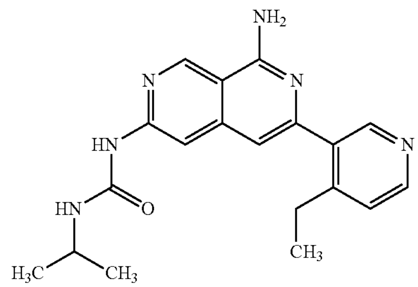 [SMILES: CCc1ccncc1-c1cc2cc(NC(=O)NC(C)C)ncc2c(N)n1] | 1-[8-amino-6-(4-ethyl-3-pyridyl)-2,7-naphthyridin-3-yl]-3-isopropyl-urea |
| 32 | 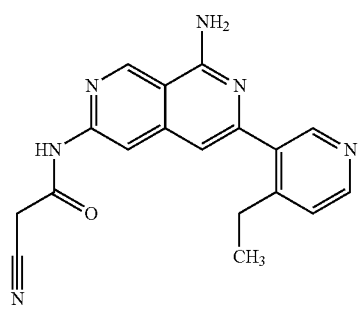 [SMILES: CCc1ccncc1-c1cc2cc(NC(=O)CC#N)ncc2c(N)n1] | N-[8-amino-6-(4-ethyl-3-pyridyl)-2,7-naphthyridin-3-yl]-2-cyano-acetamide |
| 33 | 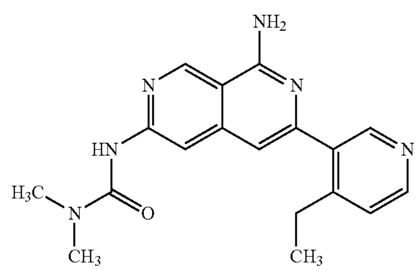 [SMILES: CCc1ccncc1-c1cc2cc(NC(=O)N(C)C)ncc2c(N)n1] | 3-[8-amino-6-(4-ethyl-3-pyridyl)-2,7-naphthyridin-3-yl]-1,1-dimethyl-urea |
| 34 | 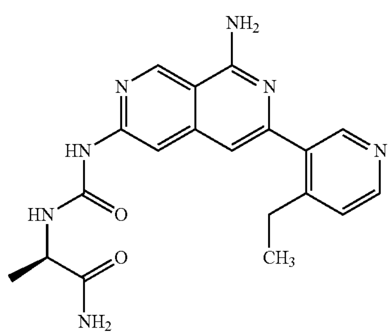 | 2-[[8-amino-6-(4-ethyl-3-pyridyl)-2,7-naphthyridin-3-yl]carbamoylamino]propanamide |

TABLE 1-continued

| Cmpd No. | Structure | Name |
|---|---|---|
| | (structure) | |
| 35 | (structure) | N-(8-amino-6-(4-methylpyridin-3-yl)-2,7-naphthyridin-3-yl)-2-cyano-2-methylpropanamide |
| 36 | (structure) | N-(8-amino-6-(4-methylpyridin-3-yl)-2,7-naphthyridin-3-yl)-2-methoxy-2-methylpropanamide |
| 37 | (structure) | N-(8-amino-6-(4-methylpyridin-3-yl)-2,7-naphthyridin-3-yl)isobutyramide |
| 38 | (structure) | N-(8-amino-6-(4-methylpyridin-3-yl)-2,7-naphthyridin-3-yl)-2-cyanopropanamide |

TABLE 1-continued

| Cmpd No. | Structure | Name |
|---|---|---|
| | | |
| 39 | 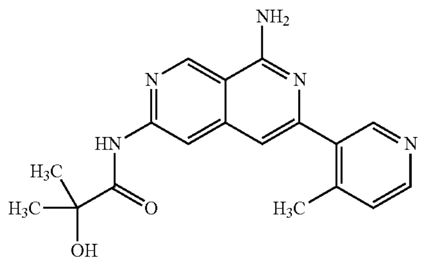 [SMILES: Cc1ccncc1-c1cc2cc(NC(=O)C(C)(C)O)ncc2c(N)n1] | N-(8-amino-6-(4-methylpyridin-3-yl)-2,7-naphthyridin-3-yl)-2-hydroxy-2-methylpropanamide |
| 40 | 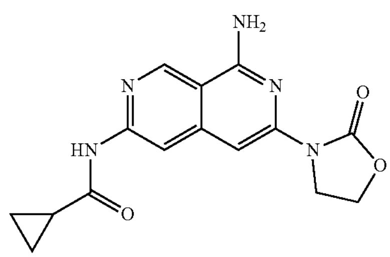 [SMILES: Nc1nc(N2CCOC2=O)cc2cc(NC(=O)C3CC3)ncc12] | N-(8-amino-6-(2-oxooxazolidin-3-yl)-2,7-naphthyridin-3-yl)cyclopropanecarboxamide |
| 42 | 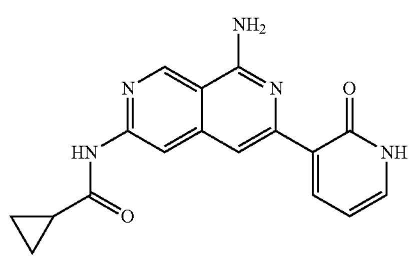 [SMILES: Nc1nc(-c2ccc[nH]c2=O)cc2cc(NC(=O)C3CC3)ncc12] | N-(8-amino-6-(2-oxo-1,2-dihydropyridin-3-yl)-2,7-naphthyridin-3-yl)cyclopropanecarboxamide |
| 43 | | trans-N-(8-amino-6-(4-methylpyridin-3-yl)-2,7-naphthyridin-3-yl)-2-cyanocyclopropanecarboxamide |

TABLE 1-continued

| Cmpd No. | Structure | Name |
|---|---|---|
| 44 | 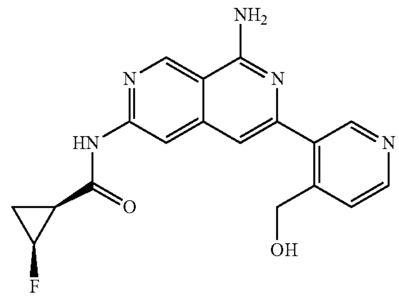 [SMILES: Nc1nc(-c2cnccc2CO)cc2cc(NC(=O)[C@@H]3C[C@@H]3F)ncc12] | (1S,2S)-N-(8-amino-6-(4-(hydroxymethyl)pyridin-3-yl)-2,7-naphthyridin-3-yl)-2-fluorocyclopropanecarboxamide |
| 45 | 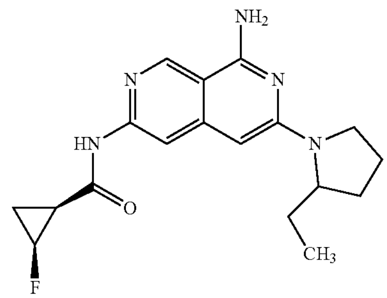 [SMILES: CCC1CCCN1c1cc2cc(NC(=O)[C@@H]3C[C@@H]3F)ncc2c(N)n1] | (1S,2S)-N-(8-amino-6-(2-ethylpyrrolidin-1-yl)-2,7-naphthyridin-3-yl)-2-fluorocyclopropanecarboxamide |
| 46 | | cis-N-(8-amino-6-(4-cyclopropylpyridin-3-yl)-2,7-naphthyridin-3-yl)-2-fluorocyclopropanecarboxamide |
| | | |
| 47 | 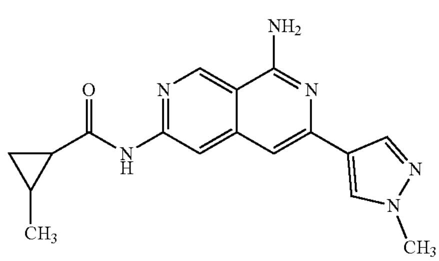 [SMILES: CC1CC1C(=O)Nc1cc2cc(-c3cnn(C)c3)nc(N)c2cn1] | N-(8-amino-6-(1-methyl-1H-pyrazol-4-yl)-2,7-naphthyridin-3-yl)-2-methylcyclopropanecarboxamide (3:1 ratio of trans/cis) |

TABLE 1-continued
| Cmpd No. | Structure | Name |
|---|---|---|
| 48 | 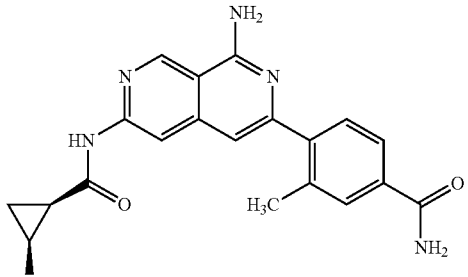 | 4-(1-amino-6-((cis)-2-fluorocyclopropanecarboxamido)-2,7-naphthyridin-3-yl)-3-methylbenzamide |
| 49 | 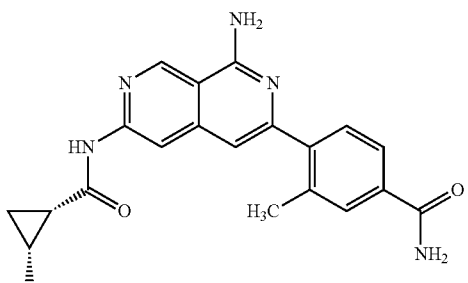 | 4-(1-amino-6-((cis)-2-fluorocyclopropanecarboxamido)-2,7-naphthyridin-3-yl)-N,3-dimethylbenzamide |
| 50 | 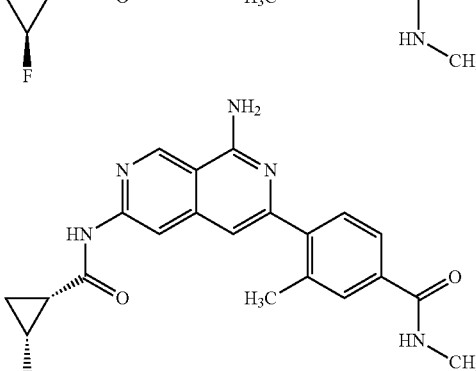 | trans-N-(8-amino-6-(4-isopropylpyridin-3-yl)-2,7-naphthyridin-3-yl)-2-cyanocyclopropanecarboxamide |

TABLE 1-continued

| Cmpd No. | Structure | Name |
|---|---|---|
| 51 | 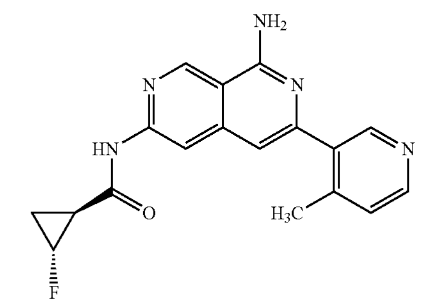 | trans-N-(8-amino-6-(4-methylpyridin-3-yl)-2,7-naphthyridin-3-yl)-2-fluorocyclopropanecarboxamide |
| 52 | 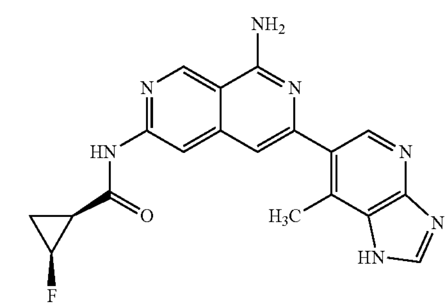 | cis-N-(8-amino-6-(7-methyl-1H-imidazo[4,5-b]pyridin-6-yl)-2,7-naphthyridin-3-yl)-2-fluorocyclopropanecarboxamide |

TABLE 1-continued

| Cmpd No. | Structure | Name |
|---|---|---|
| 53 | | trans-N-(8-amino-6-(4-ethylpyridin-3-yl)-2,7-naphthyridin-3-yl)-2-(methoxymethyl)cyclo propane carboxamide |
| 54 | | cis-N-(8-amino-6-(2-(2-hydroxyethyl)pyrrolidin-1-yl)-2,7-naphthyridin-3-yl)-2-fluorocyclopropanecarboxamide |
| 55 | 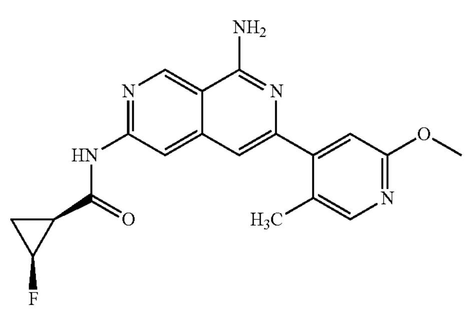 | cis-N-(8-amino-6-(2-methoxy-5-methylpyridin-4-yl)-2,7-naphthyridin-3-yl)-2-fluorocyclopropanecarboxamide |

TABLE 1-continued

| Cmpd No. | Structure | Name |
|---|---|---|
| | (structure) | |
| 56 | (structure) | cis-N-[8-amino-6-(5-methyl-2-oxo-1H-pyridin-4-yl)-2,7-naphthyridin-3-yl]-2-fluoro-cyclopropanecarboxamide |
| | (structure) | |
| 57 | (structure) | benzyl 8-amino-6-(4-ethylpyridin-3-yl)-2,7-naphthyridin-3-ylcarbamate |
| 58 | (structure) | cis-N-(8-amino-6-(6-methyl-2-oxoindolin-5-yl)-2,7-naphthyridin-3-yl)-2-fluorocyclopropanecarboxamide |

TABLE 1-continued

| Cmpd No. | Structure | Name |
|---|---|---|
| 59 | | cis-N-(8-amino-6-(6-methyl-2-oxoindolin-5-yl)-2,7-naphthyridin-3-yl)-2-fluorocyclopropanecarboxamide |
| 60 | | cis-N-(8-amino-6-(4-ethylpyridin-3-yl)-2,7-naphthyridin-3-yl)-2-cyanocyclopropanecarboxamide |

TABLE 1-continued

| Cmpd No. | Structure | Name |
|---|---|---|
| 61 | | cis-N1-(8-amino-6-(4-ethylpyridin-3-yl)-2,7-naphthyridin-3-yl)cyclopropane-1,2-dicarboxamide |
| | | |
| 62 | | cis-N-(8-amino-6-(2,4-dimethylpyridin-3-yl)-2,7-naphthyridin-3-yl)-2-fluorocyclopropanecarboxamide |
| | | |
| 63 | 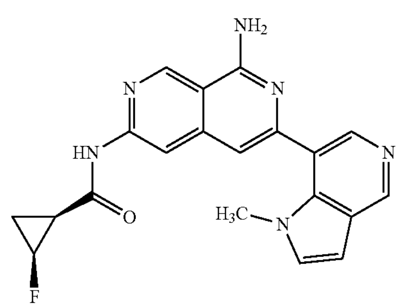 | cis-N-(8-amino-6-(1-methyl-1H-pyrrolo[3,2-c]pyridin-7-yl)-2,7-naphthyridin-3-yl)-2-fluorocyclopropanecarboxamide |

TABLE 1-continued

| Cmpd No. | Structure | Name |
|---|---|---|
| | (structure) | |
| 64 | (structure) | cis-N-[8-amino-6-(4-ethyl-1-methyl-6-oxo-3-pyridyl)-2,7-naphthyridin-3-yl]-2-fluoro-cyclopropanecarboxamide |
| | (structure) | |
| 65 | (structure) | (R)-1-(8-amino-6-(4-ethylpyridin-3-yl)-2,7-naphthyridin-3-yl)-3-(1-methyl-2-oxopyrrolidin-3-yl)urea |
| 66 | (structure) | cis-N-(8-amino-6-(4-ethyl-6-methoxypyridin-3-yl)-2,7-naphthyridin-3-yl)-2-fluorocyclopropanecarboxamide |

TABLE 1-continued

| Cmpd No. | Structure | Name |
|---|---|---|
| 67 | 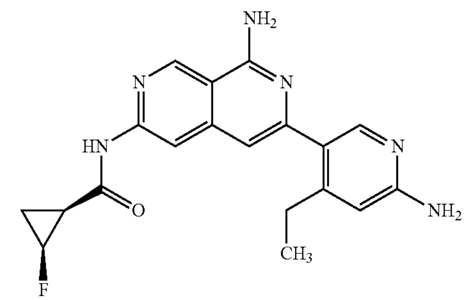 | cis-N-(8-amino-6-(6-amino-4-ethylpyridin-3-yl)-2,7-naphthyridin-3-yl)-2-fluorocyclopropanecarboxamide |
| 68 | 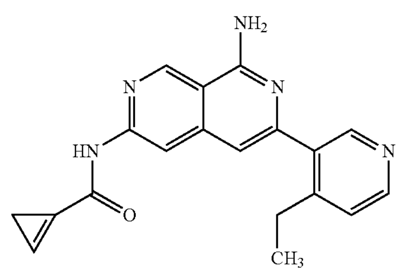 | N-[8-amino-6-(4-ethyl-3-pyridyl)-2,7-naphthyridin-3-yl]cyclopropene-1-carboxamide |
| 70 | 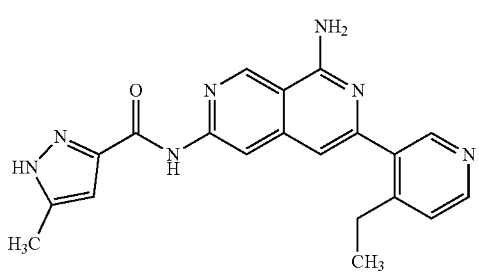 [SMILES: CCc1ccncc1-c1cc2cc(NC(=O)c3cc(C)[nH]n3)ncc2c(N)n1] | 5-Methyl-1H-pyrazole-3-carboxylic acid [8-amino-6-(4-ethylpyridin-3-yl)-[2,7]naphthyridin-3-yl]amide |

TABLE 1-continued

| Cmpd No. | Structure | Name |
|---|---|---|
| 71 | 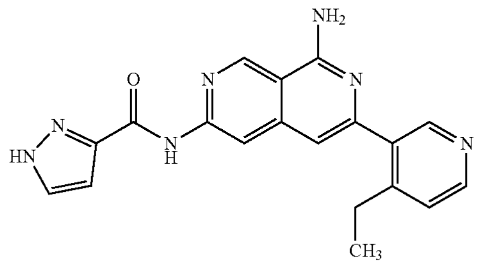 [SMILES: CCc1ccncc1-c1cc2cc(NC(=O)c3cc[nH]n3)ncc2c(N)n1] | 2H-Pyrazole-3-carboxylic acid [8-amino-6-(4-ethylpyridin-3-yl)-[2,7]naphthyridin-3-yl]amide |
| 72 | 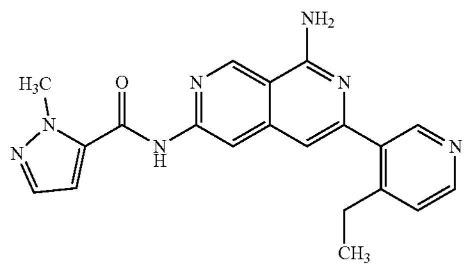 [SMILES: CCc1ccncc1-c1cc2cc(NC(=O)c3ccnn3C)ncc2c(N)n1] | 2-Methyl-2H-pyrazole-3-carboxylic acid [8-amino-6-(4-ethylpyridin-3-yl)-[2,7]naphthyridin-3-yl]amide |
| 73 | 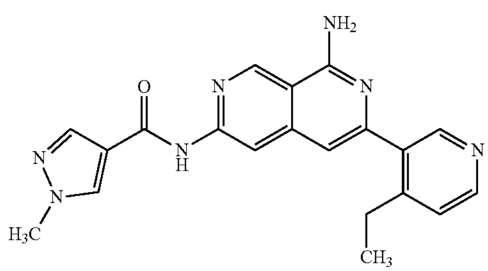 [SMILES: CCc1ccncc1-c1cc2cc(NC(=O)c3cnn(C)c3)ncc2c(N)n1] | 1-Methyl-1H-pyrazole-4-carboxylic acid [8-amino-6-(4-ethylpyridin-3-yl)-[2,7]naphthyridin-3-yl]amide |
| 74 | 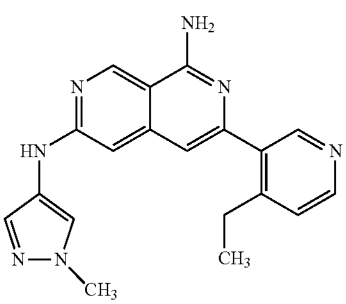 [SMILES: CCc1ccncc1-c1cc2cc(Nc3cnn(C)c3)ncc2c(N)n1] | 3-(4-Ethylpyridin-3-yl)-N6-(1-methyl-1H-pyrazol-4-yl)-[2,7]naphthyridine-1,6-diamine |
| 75 | 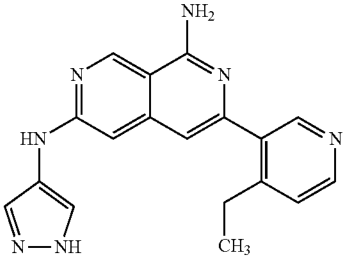 [SMILES: CCc1ccncc1-c1cc2cc(Nc3cn[nH]c3)ncc2c(N)n1] | 3-(4-Ethylpyridin-3-yl)-N6-(1H-pyrazol-4-yl)-[2,7]naphthyridine-1,6-diamine |

TABLE 1-continued

| Cmpd No. | Structure | Name |
|---|---|---|
| 76 | 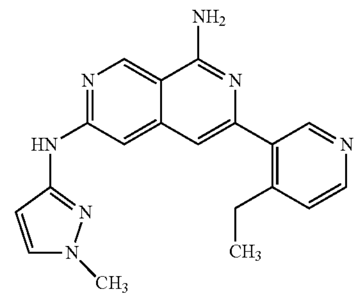 [SMILES: CCc1ccncc1-c1cc2cc(Nc3ccn(C)n3)ncc2c(N)n1] | 3-(4-Ethylpyridin-3-yl)-N6-(1-methyl-1H-pyrazol-3-yl)-[2,7]naphthyridine-1,6-diamine |
| 77 | 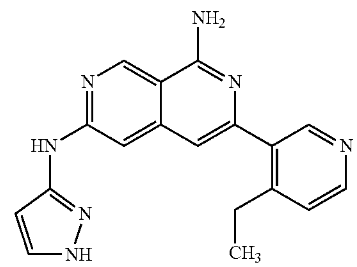 | 3-(4-Ethylpyridin-3-yl)-N6-(1H-pyrazol-3-yl)-[2,7]naphthyridine-1,6-diamine |
| 78 | 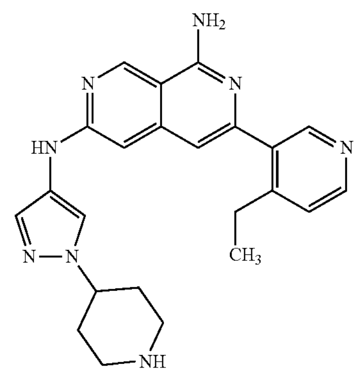 [SMILES: CCc1ccncc1-c1cc2cc(Nc3cnn(C4CCNCC4)c3)ncc2c(N)n1] | 3-(4-Ethylpyridin-3-yl)-N6-(1-piperidin-4-yl-1H-pyrazol-4-yl)-[2,7]naphthyridine-1,6-diamine |
| 79 | 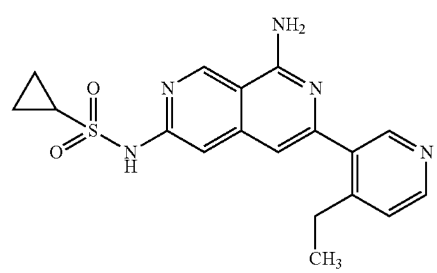 [SMILES: CCc1ccncc1-c1cc2cc(NS(=O)(=O)C3CC3)ncc2c(N)n1] | Cyclopropanesulfonic acid [8-amino-6-(4-ethylpyridin-3-yl)-[2,7]naphthyridin-3-yl]amide |
| 80 | 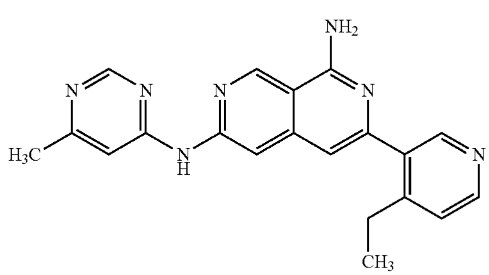 [SMILES: CCc1ccncc1-c1cc2cc(Nc3cc(C)ncn3)ncc2c(N)n1] | 3-(4-Ethylpyridin-3-yl)-N6-(6-methylpyrimidin-4-yl)-[2,7]naphthyridine-1,6-diamine |

TABLE 1-continued

| Cmpd No. | Structure | Name |
|---|---|---|
| 81 | 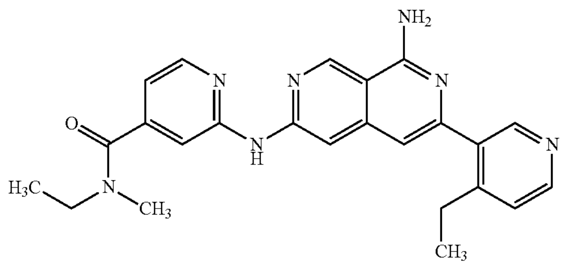 [SMILES: CCc1ccncc1-c1cc2cc(Nc3cc(C(=O)N(C)CC)ccn3)ncc2c(N)n1] | 2-[8-Amino-6-(4-ethylpyridin-3-yl)-[2,7]naphthyridin-3-ylamino]-N-ethyl-N-methylisonicotinamide |
| 82 | 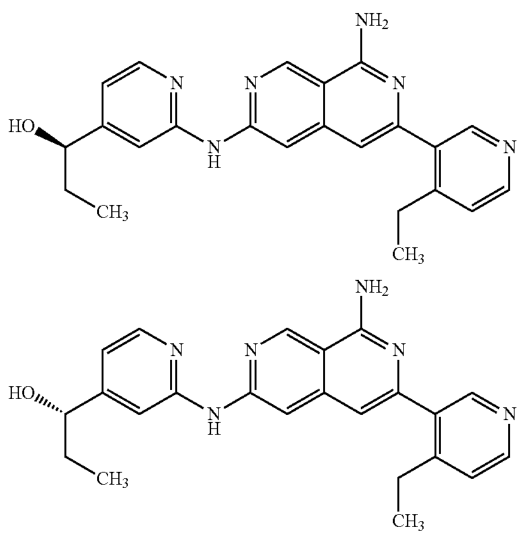 | 1-{2-[8-Amino-6-(4-ethylpyridin-3-yl)-[2,7]naphthyridin-3-ylamino]-pyridin-4-yl}propan-1-ol |
| 83 | 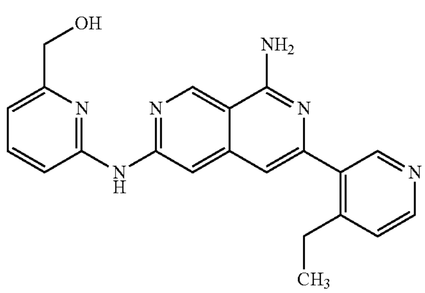 [SMILES: CCc1ccncc1-c1cc2cc(Nc3cccc(CO)n3)ncc2c(N)n1] | {6-[8-amino-6-(4-ethylpyridin-3-yl)-[2,7]naphthyridin-3-ylamino]pyridin-2-yl}methanol |
| 84 | 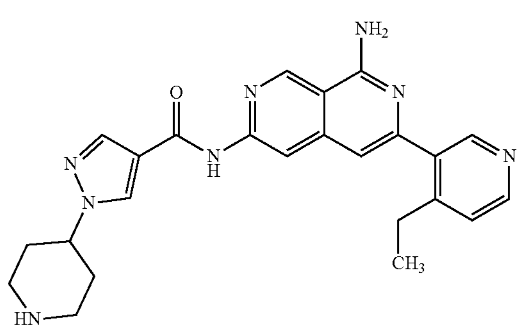 [SMILES: CCc1ccncc1-c1cc2cc(NC(=O)c3cnn(C4CCNCC4)c3)ncc2c(N)n1] | N-(8-amino-6-(4-ethylpyridin-3-yl)-2,7-naphthyridin-3-yl)-1-(piperidin-4-yl)-1H-pyrazole-4-carboxamide |

TABLE 1-continued

| Cmpd No. | Structure | Name |
|---|---|---|
| 85 | 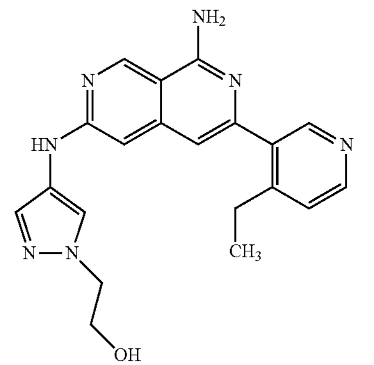 [SMILES: CCc1ccncc1-c1cc2cc(Nc3cnn(CCO)c3)ncc2c(N)n1] | 2-{4-[8-Amino-6-(4-ethylpyridin-3-yl)-[2,7]naphthyridin-3-ylamino]pyrazol-1-yl}ethanol |
| 86 | 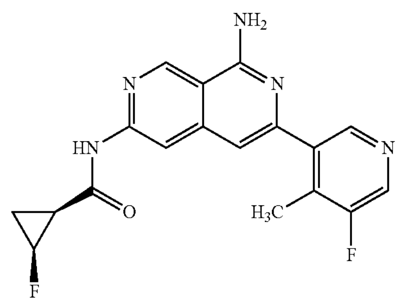 | (1S,2S)-N-(8-amino-6-(5-fluoro-4-methylpyridin-3-yl)-2,7-naphthyridin-3-yl)-2-fluorocyclopropane-1-carboxamide |
| 87, 88 | | cis-N-(8-amino-6-(2-ethylpyrrolidin-1-yl)-2,7-naphthyridin-3-yl)-2-fluorocyclopropane-1-carboxamide |

TABLE 1-continued

| Cmpd No. | Structure | Name |
|---|---|---|
| | | |
| | | |
| 89 | | cis-N-(8-amino-6-(4-ethyl-6-methoxypyridin-3-yl)-2,7-naphthyridin-3-yl)-2-fluorocyclopropane-1-carboxamide |
| | | |
| 90 | 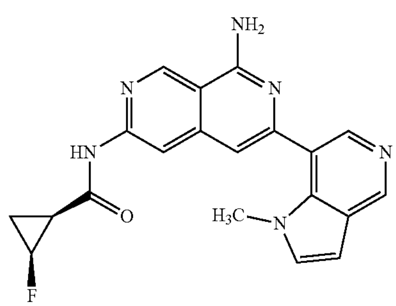 | cis-N-(8-amino-6-(1-methyl-1H-pyrrolo[3,2-c]pyridin-7-yl)-2,7-naphthyridin-3-yl)-2-fluorocyclopropane-1-carboxamide |

| Cmpd No. | Structure | Name |
|---|---|---|
| | | |
| 91, 92, 93, 94 | | N-(8-amino-6-(4-ethylpyridin-3-yl)-2,7-naphthyridin-3-yl)-2-cyanocyclopropane-1-carboxamide<br>trans-N-(8-amino-6-(4-ethylpyridin-3-yl)-2,7-naphthyridin-3-yl)-2-cyanocyclopropane-1-carboxamide<br>cis-N-(8-amino-6-(4-ethylpyridin-3-yl)-2,7-naphthyridin-3-yl)-2-cyanocyclopropane-1-carboxamide |

TABLE 1-continued

| Cmpd No. | Structure | Name |
| --- | --- | --- |
| 96, 97 | 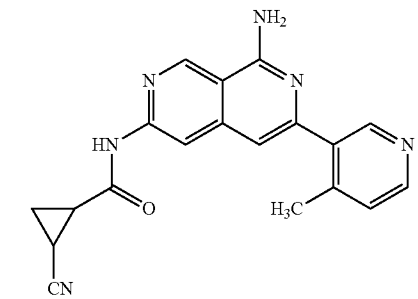 [SMILES: Cc1ccncc1-c1cc2cc(NC(=O)C3CC3C#N)ncc2c(N)n1] | trans-N-(8-amino-6-(4-methylpyridin-3-yl)-2,7-naphthyridin-3-yl)-2-cyanocyclopropane-1-carboxamide |
| 98 | | trans-N-(8-amino-6-(4-ethylpyridin-3-yl)-2,7-naphthyridin-3-yl)-2-(3-hydroxycyclobutane-1-carbonyl)cyclopropane-1-carboxamide |
| | | |
| 99 | 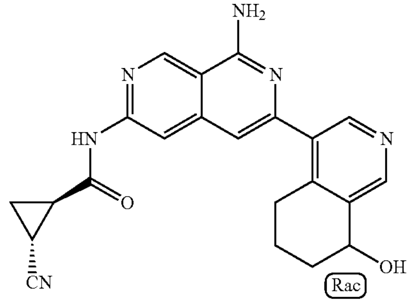 | trans-N-(8-amino-6-(8-hydroxy-5,6,7,8-tetrahydroisoquinolin-4-yl)-2,7-naphthyridin-3-yl)-2-cyanocyclopropane-1-carboxamide |

TABLE 1-continued

| Cmpd No. | Structure | Name |
|---|---|---|
| | (structure) | |
| 100 | (structure) | cis-N-(8-amino-6-(2-(hydroxymethyl)-5-methylpyridin-4-yl)-2,7-naphthyridin-3-yl)-2-fluorocyclopropane-1-carboxamide |
| | (structure) | |
| 101 | (structure) | cis-N-(8-amino-6-(2-cyano-5-methylpyridin-4-yl)-2,7-naphthyridin-3-yl)-2-fluorocyclopropane-1-carboxamide |
| | (structure) | |

TABLE 1-continued

| Cmpd No. | Structure | Name |
|---|---|---|
| 102 | 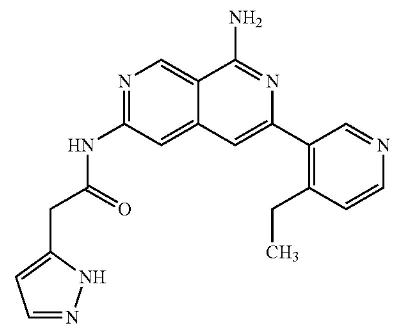 [SMILES: CCc1ccncc1-c1cc2cc(NC(=O)Cc3ccn[nH]3)ncc2c(N)n1] | N-(8-amino-6-(4-ethylpyridin-3-yl)-2,7-naphthyridin-3-yl)-2-(1H-pyrazol-5-yl)acetamide |
| 103 | | cis-N-(8-amino-6-(3,5-dimethyl-1H-pyrazol-4-yl)-2,7-naphthyridin-3-yl)-2-fluorocyclopropane-1-carboxamide |
| | | |
| 104 | | trans-N-(8-amino-6-(1,2-dimethyl-1H-imidazol-5-yl)-2,7-naphthyridin-3-yl)-2-cyanocyclopropane-1-carboxamide |
| | | |

TABLE 1-continued

| Cmpd No. | Structure | Name |
|---|---|---|
| 105 | 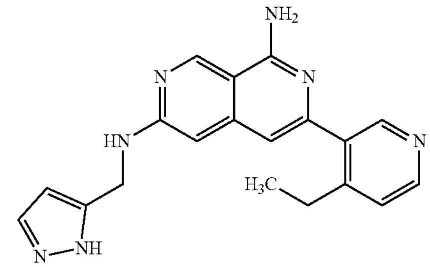 [SMILES: CCc1ccncc1-c1cc2cc(NCc3ccn[nH]3)ncc2c(N)n1] | N6-((1H-pyrazol-5-yl)methyl)-3-(4-ethylpyridin-3-yl)-2,7-naphthyridine-1,6-diamine |
| 106 | | cis-N-(8-amino-6-(pyridin-3-yl)-2,7-naphthyridin-3-yl)-2-fluorocyclopropane-1-carboxamide |
| 107, 108 | | trans-N-(8-amino-6-(4-methylpyridin-3-yl)-2,7-naphthyridin-3-yl)-2-fluorocyclopropane-1-carboxamide |

TABLE 1-continued

| Cmpd No. | Structure | Name |
|---|---|---|
| 109 | 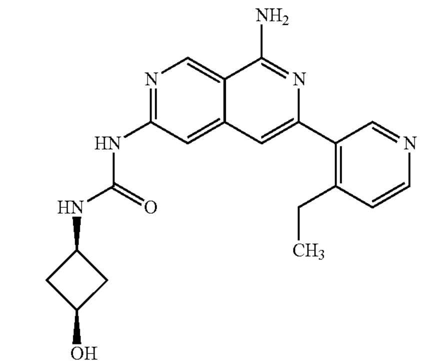 [SMILES: CCc1ccncc1-c1cc2cc(NC(=O)N[C@H]3C[C@@H](O)C3)ncc2c(N)n1] | 1-[8-amino-6-(4-ethyl-3-pyridyl)-2,7-naphthyridin-3-yl]-3-(cis-3-hydroxycyclobutyl)urea |
| 110 | 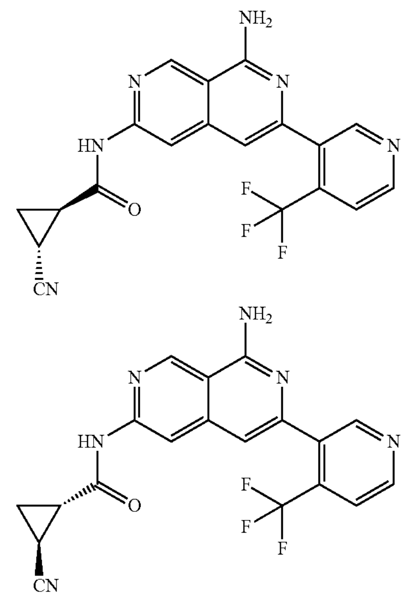 | trans-N-(8-amino-6-(4-(trifluoromethyl)pyridin-3-yl)-2,7-naphthyridin-3-yl)-2-cyanocyclopropane-1-carboxamide |
| 111 | 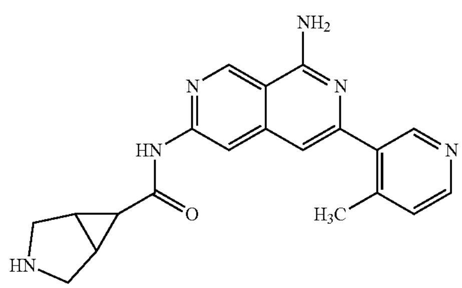 [SMILES: Cc1ccncc1-c1cc2cc(NC(=O)C3C4CNCC43)ncc2c(N)n1] | N-[8-amino-6-(4-methyl-3-pyridyl)-2,7-naphthyridin-3-yl]-3-azabicyclo[3.1.0]hexane-6-carboxamide |
| 112 | 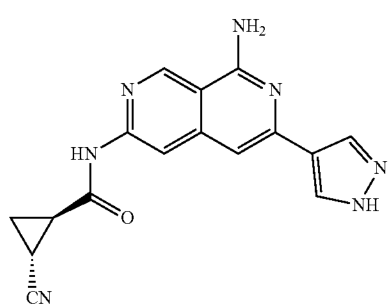 | trans-N-(8-amino-6-(1H-pyrazol-4-yl)-2,7-naphthyridin-3-yl)-2-cyanocyclopropane-1-carboxamide |

TABLE 1-continued

| Cmpd No. | Structure | Name |
|---|---|---|
| | | |
| 113 | 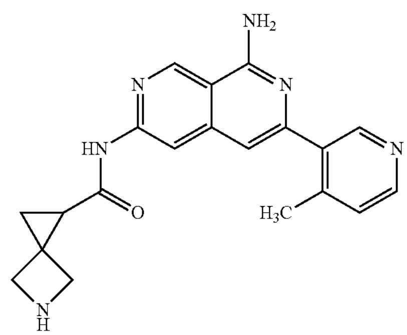 [SMILES: Cc1ccncc1-c1cc2cc(NC(=O)C3CC34CNC4)ncc2c(N)n1] | N-[8-amino-6-(4-methyl-3-pyridyl)-2,7-naphthyridin-3-yl]-5-azaspiro[2.3]hexane-2-carboxamide |
| 114 | 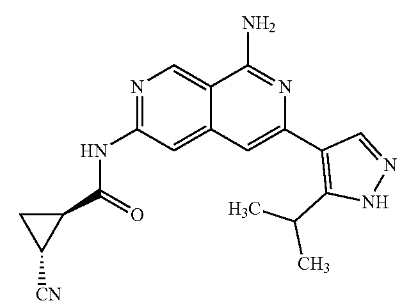 | trans-N-(8-amino-6-(5-isopropyl-1H-pyrazol-4-yl)-2,7-naphthyridin-3-yl)-2-cyanocyclopropane-1-carboxamide |
| | | |
| 115 | 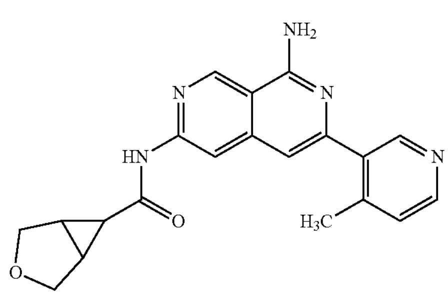 [SMILES: Cc1ccncc1-c1cc2cc(NC(=O)C3C4COCC43)ncc2c(N)n1] | rac-(1R,5S)-N-[8-amino-6-(4-methyl-3-pyridyl)-2,7-naphthyridin-3-yl]-3-oxabicyclo[3.1.0]hexane-6-carboxamide |

TABLE 1-continued

| Cmpd No. | Structure | Name |
|---|---|---|
| 116 | 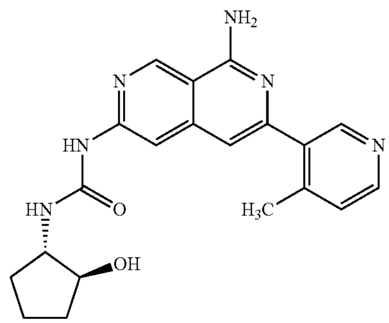 [SMILES: Cc1ccncc1-c1cc2cc(NC(=O)N[C@H]3CCC[C@@H]3O)ncc2c(N)n1] | 1-[8-amino-6-(4-methyl-3-pyridyl)-2,7-naphthyridin-3-yl]-3-[rac-(1S,2S)-2-hydroxycyclopentyl]urea |
| 117 | | 1-(8-amino-6-(4-methylpyridin-3-yl)-2,7-naphthyridin-3-yl)-3-(1-hydroxypropan-2-yl)urea |
| | | |
| 118 | | trans-N-(8-amino-6-(4-methylpyridin-3-yl)-2,7-naphthyridin-3-yl)-2-methylcyclopropane-1-carboxamide |

TABLE 1-continued
| Cmpd No. | Structure | Name |
|---|---|---|
| 119 | 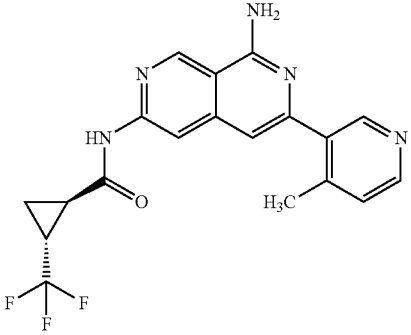 | trans-N-(8-amino-6-(4-methylpyridin-3-yl)-2,7-naphthyridin-3-yl)-2-(trifluoromethyl)cyclopropane-1-carboxamide |
| 120 | 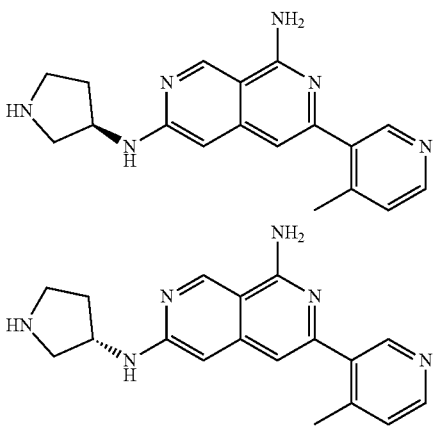 | 3-(4-methyl-3-pyridyl)-N6-pyrrolidin-3-yl-2,7-naphthyridine-1,6-diamine |
| 121 | 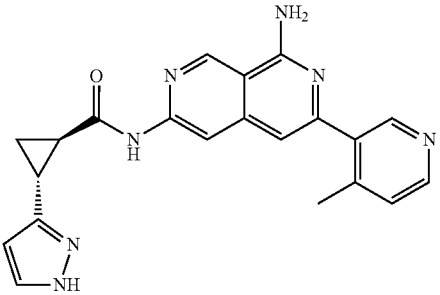 | trans-N-[8-amino-6-(4-methyl-3-pyridyl)-2,7-naphthyridin-3-yl]-2-(1H-pyrazol-3-yl)cyclopropanecarboxamide |

TABLE 1-continued
| Cmpd No. | Structure | Name |
|---|---|---|
| | 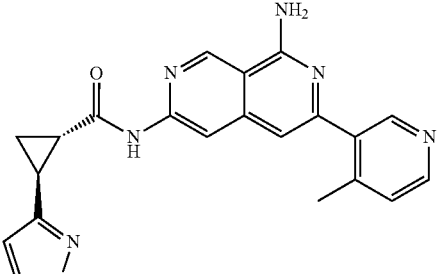 | |
| 122 | 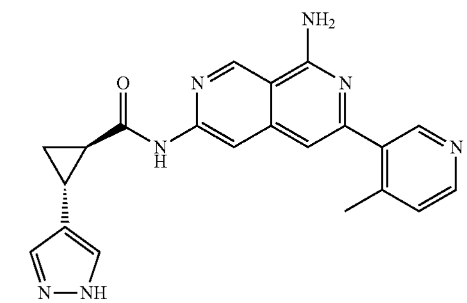 | trans-N-[8-amino-6-(4-methyl-3-pyridyl)-2,7-naphthyridin-3-yl]-2-(1H-pyrazol-4-yl)cyclopropanecarboxamide |
| |  | |
| 123 | 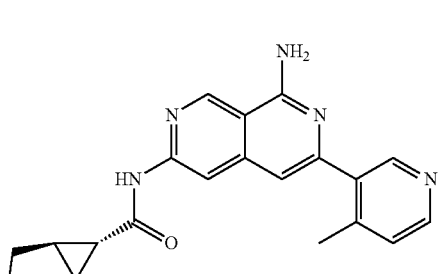 | (1R,5S,6R)-N-[8-amino-6-(4-methyl-3-pyridyl)-2,7-naphthyridin-3-yl]-3-oxabicyclo[3.1.0]hexane-6-carboxamide |

TABLE 1-continued

| Cmpd No. | Structure | Name |
|---|---|---|
| 124 | 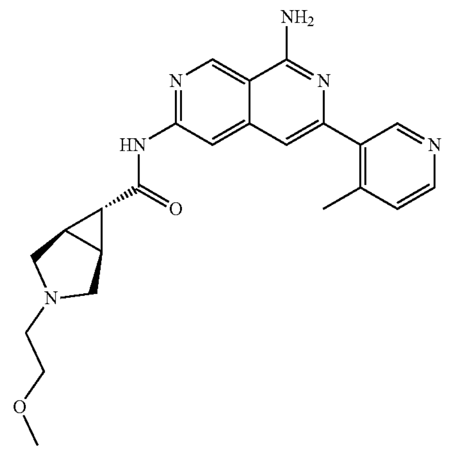 [SMILES: COCCN1C[C@@H]2[C@H](C1)[C@H]2C(=O)Nc1cc2cc(-c3cnccc3C)nc(N)c2cn1] | exo-N-[8-amino-6-(4-methyl-3-pyridyl)-2,7-naphthyridin-3-yl]-3-(2-methoxyethyl)-3-azabicyclo[3.1.0]hexane-6-carboxamide |
| 125 | | trans-N-(8-amino-6-(4-methylpyridin-3-yl)-2,7-naphthyridin-3-yl)-5-azaspiro[2.4]heptane-1-carboxamide |
| 126 | 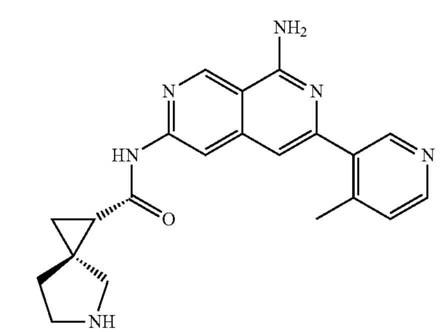 | cis-N-(8-amino-6-(4-methylpyridin-3-yl)-2,7-naphthyridin-3-yl)-5-azaspiro[2.4]heptane-1-carboxamide |

TABLE 1-continued

| Cmpd No. | Structure | Name |
|---|---|---|
| 127 | 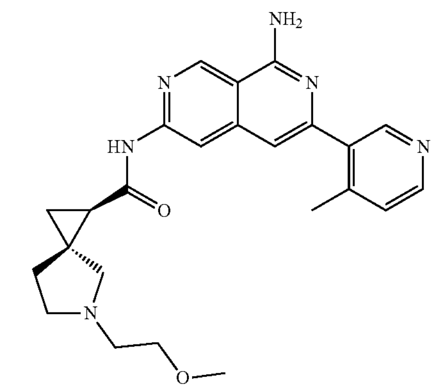 | trans-N-(8-amino-6-(4-methylpyridin-3-yl)-2,7-naphthyridin-3-yl)-5-(2-methoxyethyl)-5-azaspiro[2.4]heptane-1-carboxamide |
| 128 | 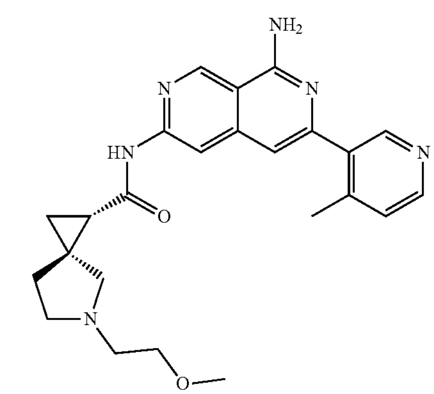 | cis-N-(8-amino-6-(4-methylpyridin-3-yl)-2,7-naphthyridin-3-yl)-5-(2-methoxyethyl)-5-azaspiro[2.4]heptane-1-carboxamide |

TABLE 1-continued

| Cmpd No. | Structure | Name |
|---|---|---|
| | | |
| 129 | 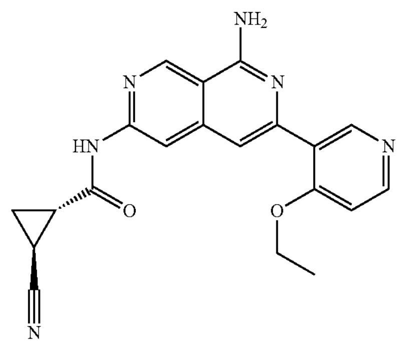 | trans-N-[8-amino-6-(4-ethoxy-3-pyridyl)-2,7-naphthyridin-3-yl]-2-cyano-cyclopropanecarboxamide |
| 130 | 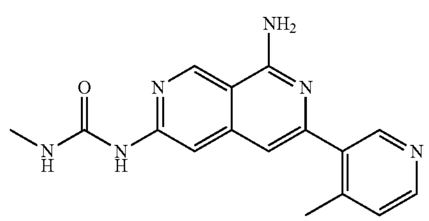 [SMILES: CNC(=O)Nc1cc2cc(-c3cnccc3C)nc(N)c2cn1] | 1-[8-amino-6-(4-methyl-3-pyridyl)-2,7-naphthyridin-3-yl]-3-methyl-urea |
| 131 | 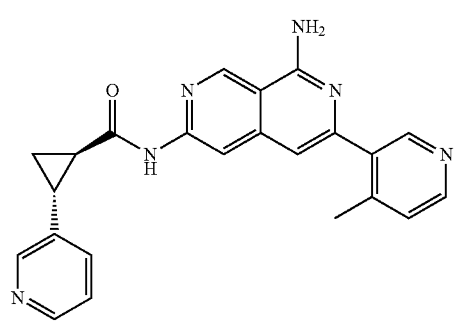 | trans-N-[8-amino-6-(4-methyl-3-pyridyl)-2,7-naphthyridin-3-yl]-2-(3-pyridy0cyclopropanecarboxamide |

TABLE 1-continued
| Cmpd No. | Structure | Name |
|---|---|---|
| | 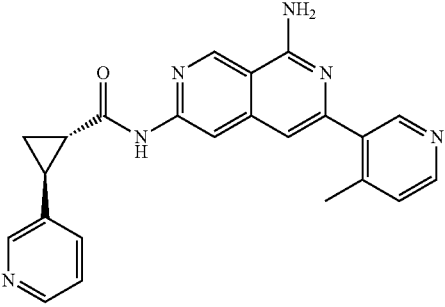 | |
| 132 | 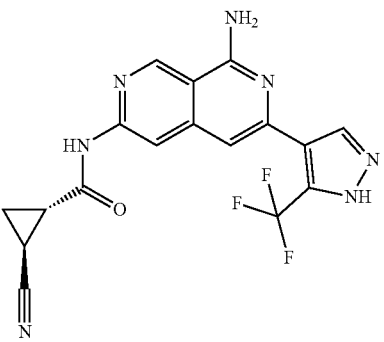 | trans-N-[8-amino-6-[5-(trifluoromethyl)-1H-pyrazol-4-yl]-2,7-naphthyridin-3-yl]-2-cyano-cyclopropanecarboxamide |
| 133 | 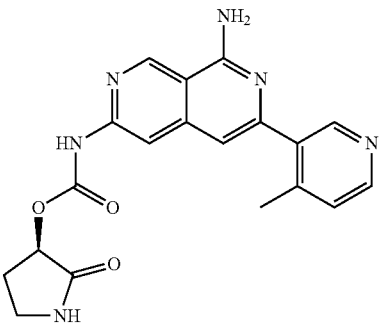 [SMILES: Cc1ccncc1-c1cc2cc(NC(=O)O[C@@H]3CCNC3=O)ncc2c(N)n1] | [(3R)-2-oxopyrrolidin-3-yl]N-[8-amino-6-(4-methyl-3-pyridyl)-2,7-naphthyridin-3-yl]carbamate |

TABLE 1-continued

| Cmpd No. | Structure | Name |
|---|---|---|
| 134 | 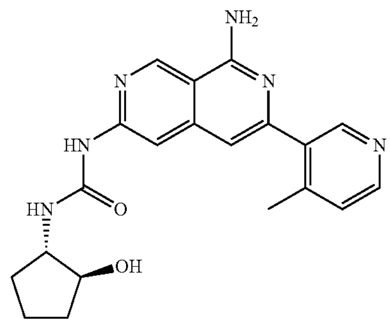 [SMILES: Cc1ccncc1-c1cc2cc(NC(=O)N[C@H]3CCC[C@@H]3O)ncc2c(N)n1] | 1-[8-amino-6-(4-methyl-3-pyridyl)-2,7-naphthyridin-3-yl]-3-[(1S,2S)-2-hydroxycyclopentyl]urea |
| 135 | 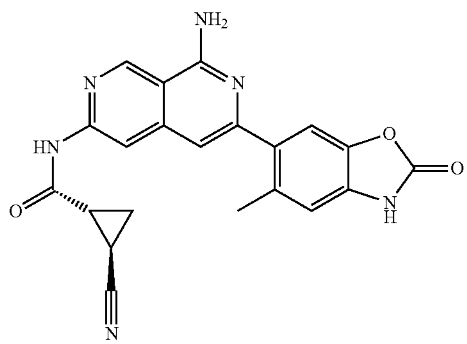 | trans-N-(8-amino-6-(5-methyl-2-oxo-2,3-dihydrobenzo[d]oxazol-6-yl)-2,7-naphthyridin-3-yl)-2-cyanocyclopropanecarboxamide |
| | | |
| 136 | 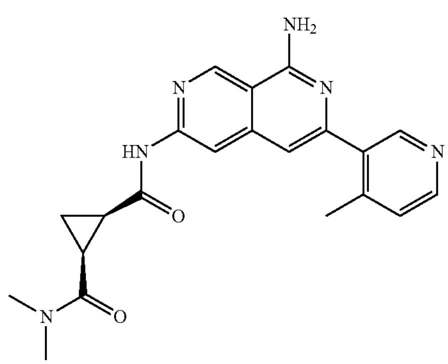 | cis-N1-(8-amino-6-(4-methylpyridin-3-yl)-2,7-naphthyridin-3-yl)-N2,N2-dimethylcyclopropane-1,2-dicarboxamide |

TABLE 1-continued

| Cmpd No. | Structure | Name |
|---|---|---|
| | | |
| 137 | 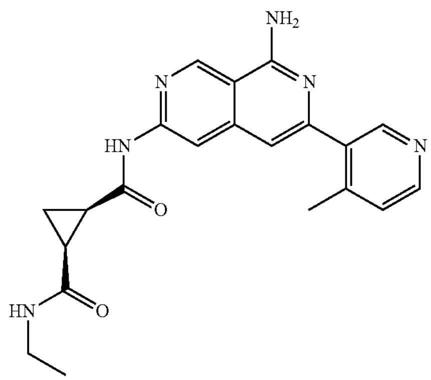 | cis-N1-(8-amino-6-(4-methylpyridin-3-yl)-2,7-naphthyridin-3-yl)-N2-ethylcyclopropane-1,2-dicarboxamide |
| 138 | 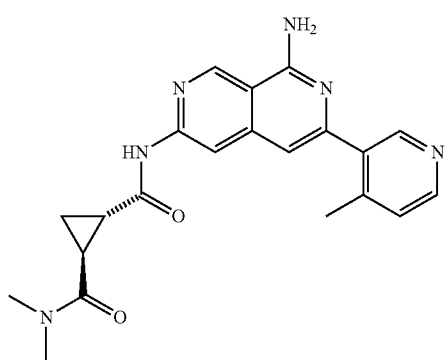 | trans-N1-(8-amino-6-(4-methylpyridin-3-yl)-2,7-naphthyridin-3-yl)-N2,N2-dimethylcyclopropane-1,2-dicarboxamide |

TABLE 1-continued

| Cmpd No. | Structure | Name |
|---|---|---|
| | (structure) | |
| 139 | (structure) | trans-N-(8-amino-6-(4-methylpyridin-3-yl)-2,7-naphthyridin-3-yl)-2-methylcyclopropanecarboxamide |
| | (structure) | |
| 140 | (structure) | trans-N-(8-amino-6-(4-methylpyridin-3-yl)-2,7-naphthyridin-3-yl)-2-(trifluoromethyl)cyclopropanecarboxamide |
| | (structure) | |

TABLE 1-continued
| Cmpd No. | Structure | Name |
|---|---|---|
| 141 | 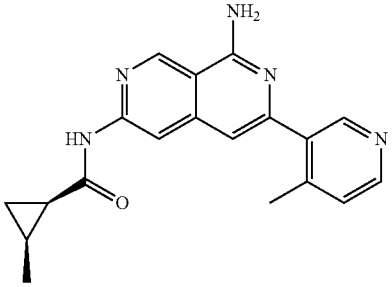 | cis-N-(8-amino-6-(4-methylpyridin-3-yl)-2,7-naphthyridin-3-yl)-2-methylcyclopropanecarboxamide |
| 142 | 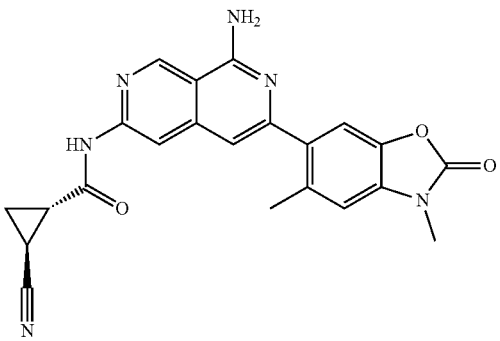 | trans-N-(8-amino-6-(3,5-dimethyl-2-oxo-2,3-dihydrobenzo[d]oxazol-6-yl)-2,7-naphthyridin-3-yl)-2-cyanocyclopropanecarboxamide |
| 143 | 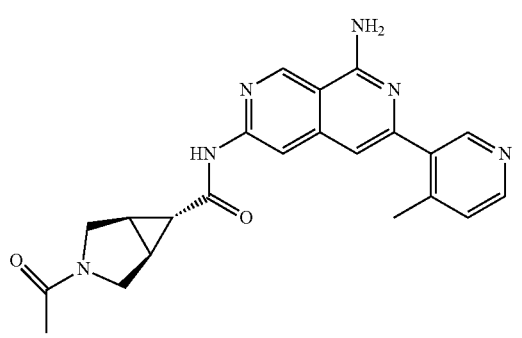 [SMILES: CC(=O)N1C[C@@H]2[C@H](C1)[C@H]2C(=O)Nc1cc2cc(-c3cnccc3C)nc(N)c2cn1] | exo-3-acetyl-N-[8-amino-6-(4-methyl-3-pyridyl)-2,7-naphthyridin-3-yl]-3-azabicyclo[3.1.0]hexane-6-carboxamide |

TABLE 1-continued
| Cmpd No. | Structure | Name |
|---|---|---|
| 144 | 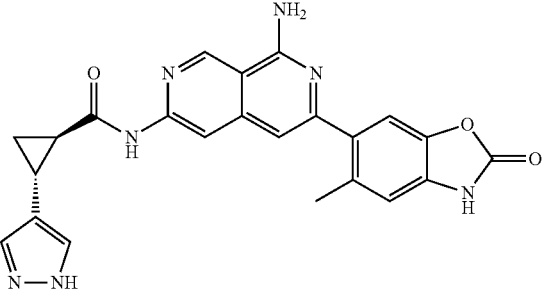 | trans-N-[8-amino-6-(5-methyl-2-oxo-3H-1,3-benzoxazol-6-yl)-2,7-naphthyridin-3-yl]-2-(1H-pyrazol-4-yl)cyclopropanecarboxamide |
| 145 | 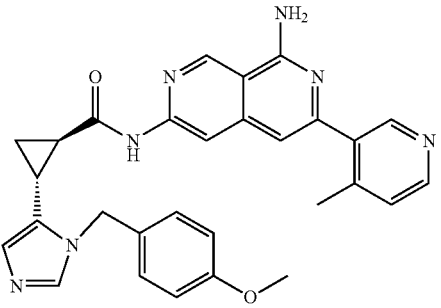 | trans-N-[8-amino-6-(4-methyl-3-pyridyl)-2,7-naphthyridin-3-yl]-2-[3-[(4-methoxyphenyl)methyl]imidazol-4-yl]cyclopropanecarboxamide |

TABLE 1-continued

| Cmpd No. | Structure | Name |
|---|---|---|
| 146 | 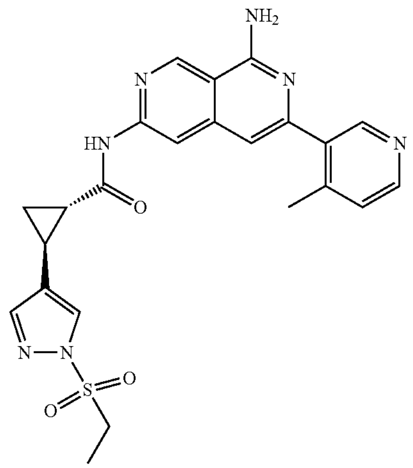 | trans-N-[8-amino-6-(4-methyl-3-pyridyl)-2,7-naphthyridin-3-yl]-2-(1-ethylsulfonylpyrazol-4-yl)cyclopropanecarboxamide |
| 147 | 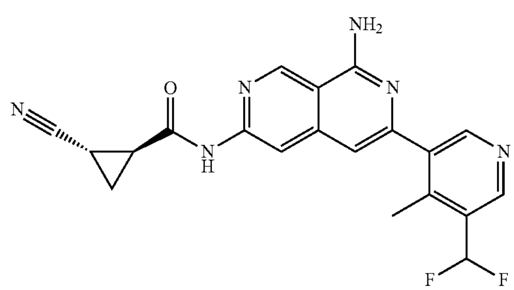 | trans-N-(8-amino-6-(5-(difluoromethyl)-4-methylpyridin-3-yl)-2,7-naphthyridin-3-yl)-2-cyanocyclopropanecarboxamide |

TABLE 1-continued

| Cmpd No. | Structure | Name |
| --- | --- | --- |
| 148 | 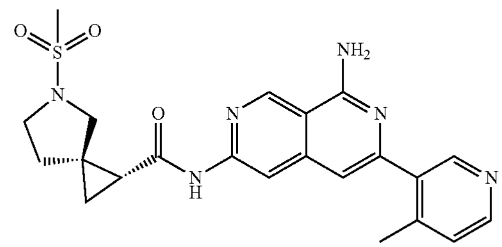 | trans-N-(8-amino-6-(4-methylpyridin-3-yl)-2,7-naphthyridin-3-yl)-5-(methylsulfonyl)-5-azaspiro[2.4]heptane-1-carboxamide |
| 149 | 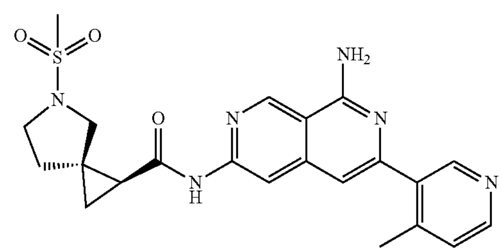 | cis-N-(8-amino-6-(4-methylpyridin-3-yl)-2,7-naphthyridin-3-yl)-5-(methylsulfonyl)-5-azaspiro[2.4]heptane-1-carboxamide |
| 150 | 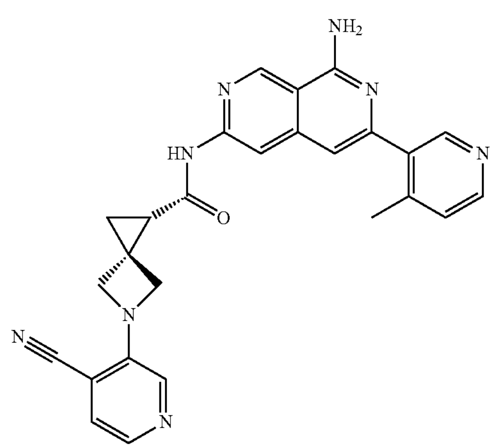 | N-(8-amino-6-(4-methylpyridin-3-yl)-2,7-naphthyridin-3-yl)-5-(3-cyanopyridin-2-yl)-5-azaspiro[2.3]hexane-1-carboxamide |

TABLE 1-continued

| Cmpd No. | Structure | Name |
|---|---|---|
| | | |
| 151 | 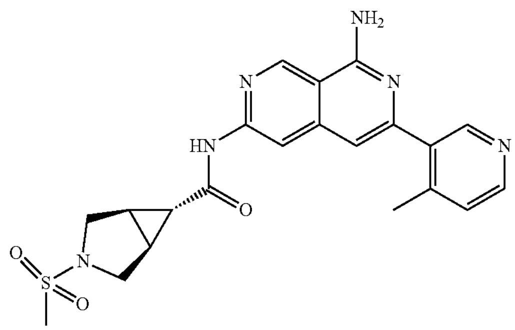 [SMILES: Cc1ccncc1-c1cc2cc(NC(=O)[C@H]3[C@@H]4CN(S(C)(=O)=O)C[C@@H]43)ncc2c(N)n1] | exo-N-[8-amino-6-(4-methyl-3-pyridyl)-2,7-naphthyridin-3-yl]-3-methylsulfonyl-3-azabicyclo[3.1.0]hexane-6-carboxamide |
| 152 | 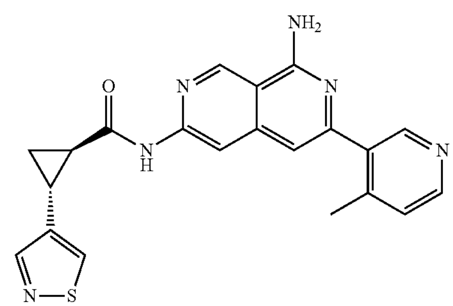 | trans-N-[8-amino-6-(4-methyl-3-pyridyl)-2,7-naphthyridin-3-yl]-2-isothiazol-4-yl-cyclopropanecarboxamide |
| 153 | 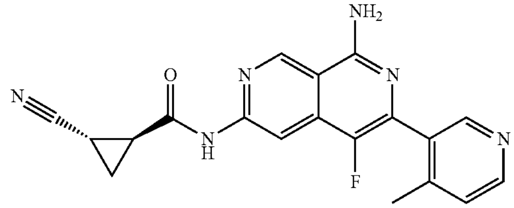 | trans-N-(8-amino-5-fluoro-6-(4-methylpyridin-3-yl)-2,7-naphthyridin-3-yl)-2-cyanocyclopropanecarboxamide |

TABLE 1-continued

| Cmpd No. | Structure | Name |
|---|---|---|
| | (cyanocyclopropane carboxamide structure with 8-amino-4-fluoro-6-(4-methylpyridin-3-yl)-2,7-naphthyridin-3-yl) | |
| 154 | (hydroxymethyl cyclopropane carboxamide structures, two stereoisomers) | trans-N-(8-amino-6-(4-methylpyridin-3-yl)-2,7-naphthyridin-3-yl)-2-(hydroxymethyl)cyclopropanecarboxamide |
| 155 | (aminomethyl cyclopropane carboxamide structures, two stereoisomers) | trans-N-(8-amino-6-(4-methylpyridin-3-yl)-2,7-naphthyridin-3-yl)-2-(aminomethyl)cyclopropanecarboxamide |
| 156 | (acetamide with 8-amino-5-fluoro-6-(4-methylpyridin-3-yl)-2,7-naphthyridin-3-yl) | N-(8-amino-5-fluoro-6-(4-methylpyridin-3-yl)-2,7-naphthyridin-3-yl)acetamide |

| Cmpd No. | Structure | Name |
|---|---|---|
| 157 | 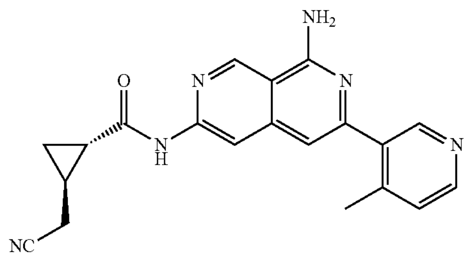 | trans-N-[8-amino-6-(4-methyl-3-pyridyl)-2,7-naphthyridin-3-yl]-2-(cyanomethyl)cyclopropanecarboxamide |
| 158 | 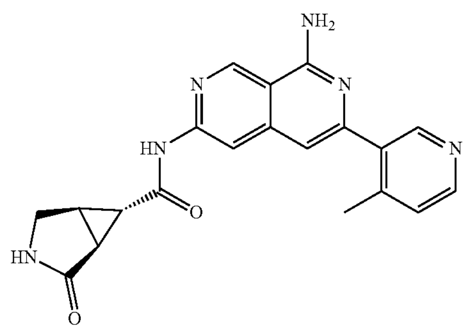 | exo-N-[8-amino-6-(4-methyl-3-pyridyl)-2,7-naphthyridin-3-yl]-4-oxo-3-azabicyclo[3.1.0]hexane-6-carboxamide |
| 159 | 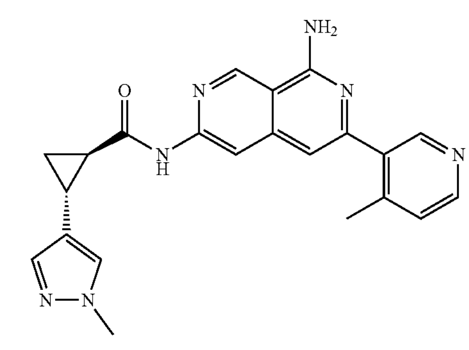 | trans-N-[8-amino-6-(4-methyl-3-pyridyl)-2,7-naphthyridin-3-yl]-2-(1-methylpyrazol-4-yl)cyclopropanecarboxamide |

TABLE 1-continued

| Cmpd No. | Structure | Name |
|---|---|---|
| | (structure) | |
| 160 | (structure) | trans-N-[8-amino-6-(3-hydroxy-6-methyl-2-oxo-indolin-5-yl)-2,7-naphthyridin-3-yl]-2-cyano-cyclopropanecarboxamide |
| 161 | (structure) | 1-[3-[4-[[8-amino-6-(4-methyl-3-pyridyl)-2,7-naphthyridin-3-yl]amino]pyrazol-1-yl]azetidin-1-yl]ethanone |
| 162 | (structure) | 1-[8-amino-5-fluoro-6-(4-methyl-3-pyridyl)-2,7-naphthyridin-3-yl]-3-(1-methylpyrazol-4-yl)urea |

TABLE 1-continued

| Cmpd No. | Structure | Name |
|---|---|---|
| 163 | 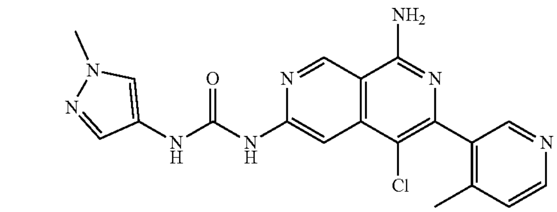 | 1-[8-amino-5-chloro-6-(4-methyl-3-pyridyl)-2,7-naphthyridin-3-yl]-3-(1-methylpyrazol-4-yl)urea |
| 164 | 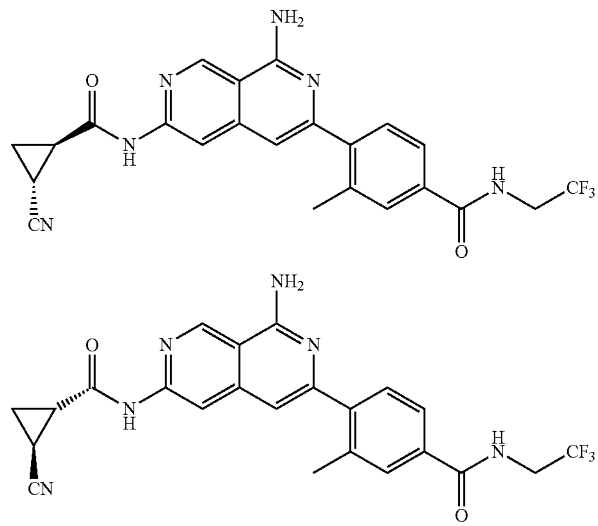 | trans-4-(1-amino-6-((trans)-2-cyanocyclopropanecarboxamido)-2,7-naphthyridin-3-yl)-3-methyl-N-(2,2,2-trifluoroethyl)benzamide) |
| | | |
| 165 | 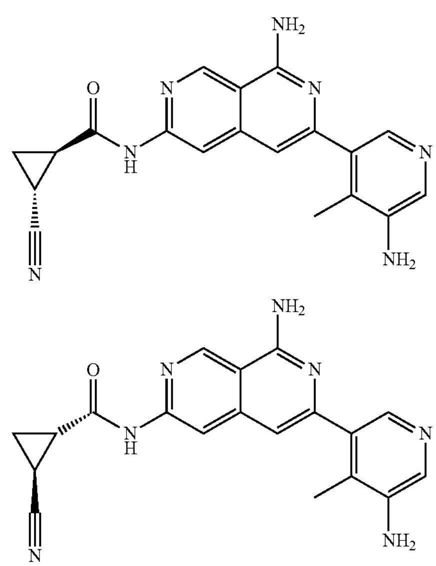 | trans-N-(8-amino-6-(5-amino-4-methylpyridin-3-yl)-2,7-naphthyridin-3-yl)-2-cyanocyclopropane carboxamide |
| | | |
| 166 | 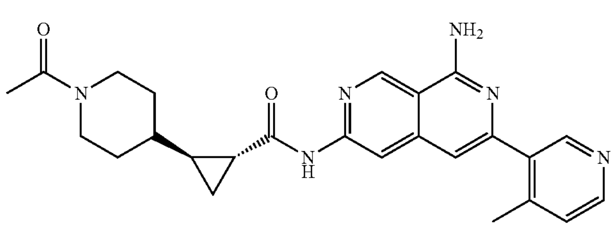 | trans-2-(1-acetylpiperidin-4-yl)-N-(8-amino-6-(4-methylpyridin-3-yl)-2,7-naphthyridin-3-yl)cyclopropanecarboxamide |

TABLE 1-continued

| Cmpd No. | Structure | Name |
|---|---|---|
| | | |
| 167 | 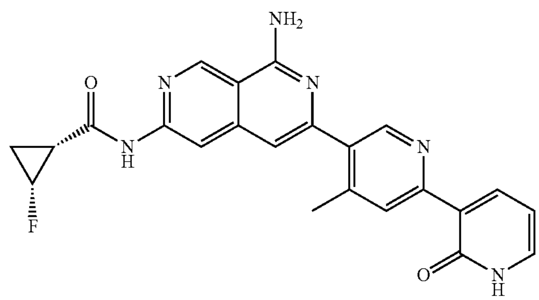 | cis-N-(8-amino-6-(4-methyl-6-(2-oxo-1,2-dihydropyridin-3-yl)pyridin-3-yl)-2,7-naphthyridin-3-yl)-2-fluorocyclopropanecarboxamide |
| 168 | 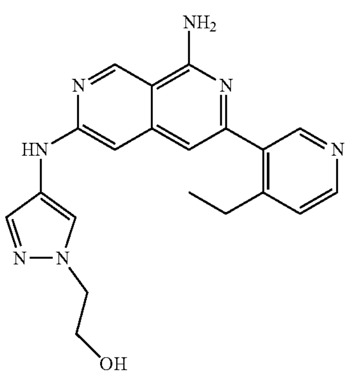 [SMILES: CCc1ccncc1-c1cc2cc(Nc3cnn(CCO)c3)ncc2c(N)n1] | 2-[4-[[8-amino-6-(4-ethyl-3-pyridyl)-2,7-naphthyridin-3-yl]amino]pyrazol-1-yl]ethanol |
| 169 | 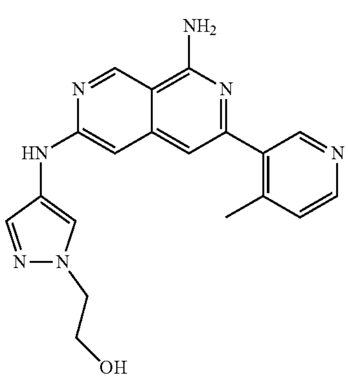 [SMILES: Cc1ccncc1-c1cc2cc(Nc3cnn(CCO)c3)ncc2c(N)n1] | 2-[4-[[8-amino-6-(4-methyl-3-pyridyl)-2,7-naphthyridin-3-yl]amino]pyrazol-1-yl]ethanol |

TABLE 1-continued

| Cmpd No. | Structure | Name |
|---|---|---|
| 170 | 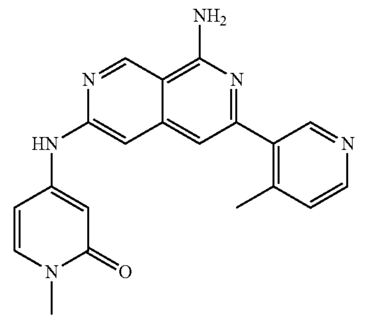 [SMILES: Cc1ccncc1-c1cc2cc(Nc3ccn(C)c(=O)c3)ncc2c(N)n1] | 4-[[8-amino-6-(4-methyl-3-pyridyl)-2,7-naphthyridin-3-yl]amino]-1-methyl-pyridin-2-one |
| 171 | 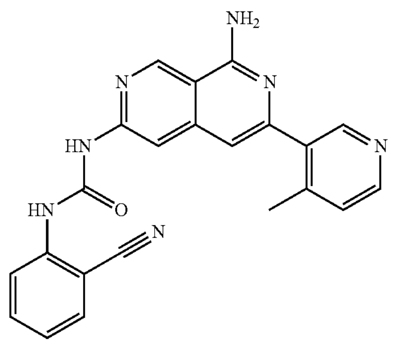 [SMILES: Cc1ccncc1-c1cc2cc(NC(=O)Nc3ccccc3C#N)ncc2c(N)n1] | 1-[8-amino-6-(4-methyl-3-pyridyl)-2,7-naphthyridin-3-yl]-3-(2-cyanophenyl)urea |
| 172 | | trans-N-(8-amino-5-fluoro-6-(4-methylpyridin-3-yl)-2,7-naphthyridin-3-yl)-2-(1H-pyrazol-4-yl)cyclopropanecarboxamide |
|  | | |
| 173 | 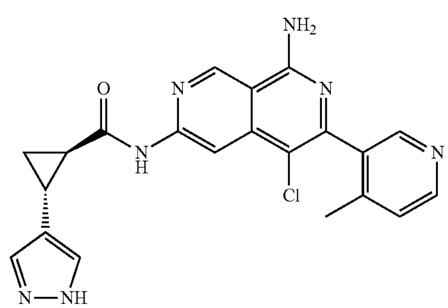 | trans-N-(8-amino-5-chloro-6-(4-methylpyridin-3-yl)-2,7-naphthyridin-3-yl)-2-(1H-pyrazol-4-yl)cyclopropanecarboxamide |

| Cmpd No. | Structure | Name |
|---|---|---|
| | (structure) | |
| 174 | (structure) | 1-(8-amino-6-(4-methylpyridin-3-yl)-2,7-naphthyridin-3-yl)-3-(1-(2-methoxyethyl)azetidin-3-yl)urea |
| 175 | (structure) | 1-(8-amino-6-(4-methylpyridin-3-yl)-2,7-naphthyridin-3-yl)-3-(azetidin-3-yl)urea |
| 176 | (structure) | (R)-1-(8-amino-6-(4-ethylpyridin-3-yl)-2,7-naphthyridin-3-yl)-3-(1-methyl-2-oxopyrrolidin-3-yl)urea |

TABLE 1-continued

| Cmpd No. | Structure | Name |
|---|---|---|
| 177 | 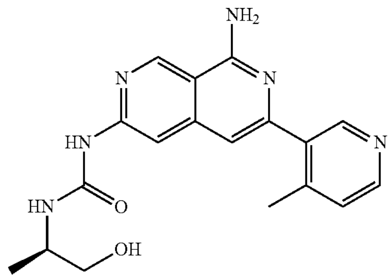 | 1-(8-amino-6-(4-methylpyridin-3-yl)-2,7-naphthyridin-3-yl)-3-(1-hydroxypropan-2-yl)urea |
| 178 | 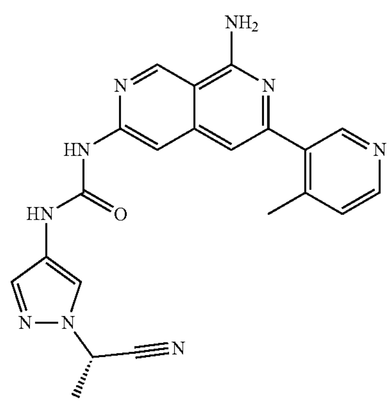 | 1-[8-amino-6-(4-methyl-3-pyridyl)-2,7-naphthyridin-3-yl]-3-[1-(1-cyanoethyl)pyrazol-4-yl]urea |

TABLE 1-continued

| Cmpd No. | Structure | Name |
|---|---|---|
| 179 | 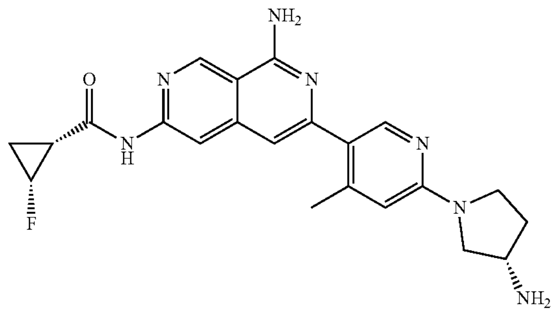 | cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide |
| | | cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide |
| 180 | 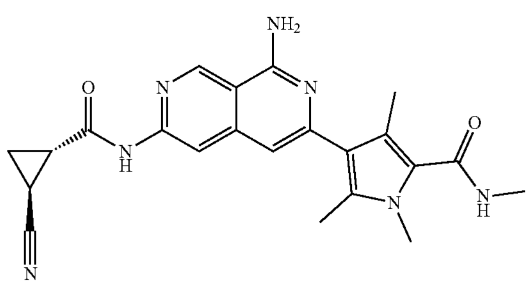 | trans-4-[1-amino-6-[[trans-2-cyanocyclopropanecarbonyl]amino]-2,7-naphthyridin-3-yl]-N,1,3,5-tetramethyl-pyrrole-2-carboxamide |
| | | trans-4-[1-amino-6-[[trans-2-cyanocyclopropanecarbonyl]amino]-2,7-naphthyridin-3-yl]-N,1,3,5-tetramethyl-pyrrole-2-carboxamide |
| 181 | 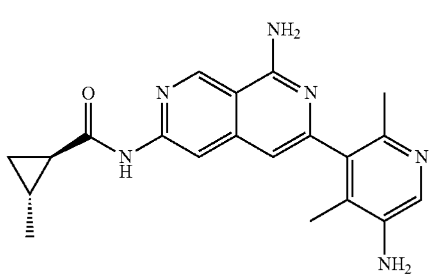 | trans-N-[8-amino-6-(5-amino-2,4-dimethyl-3-pyridyl)-2,7-naphthyridin-3-yl]-2-methyl-cyclopropanecarboxamide |

TABLE 1-continued

| Cmpd No. | Structure | Name |
|---|---|---|
| | | |
| 182 | 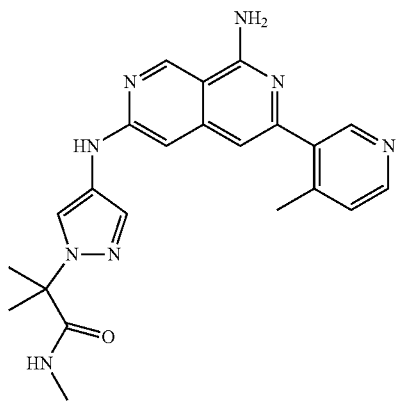 [SMILES: CNC(=O)C(C)(C)n1cc(Nc2cc3cc(-c4cnccc4C)nc(N)c3cn2)cn1] | 2-[4-[[8-amino-6-(4-methyl-3-pyridyl)-2,7-naphthyridin-3-yl]amino]pyrazol-1-yl]-N,2-dimethyl-propanamide |
| 183 | 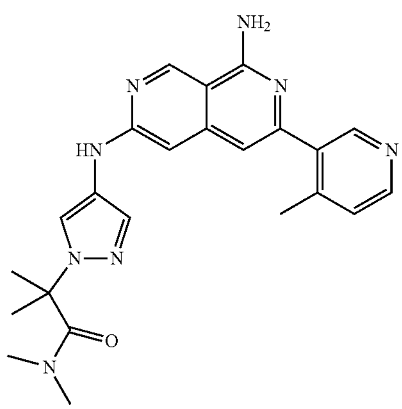 [SMILES: Cc1ccncc1-c1cc2cc(Nc3cnn(C(C)(C)C(=O)N(C)C)c3)ncc2c(N)n1] | 2-[4-[[8-amino-6-(4-methyl-3-pyridyl)-2,7-naphthyridin-3-yl]amino]pyrazol-1-yl]-N,N,2-trimethyl-propanamide |
| 184 | 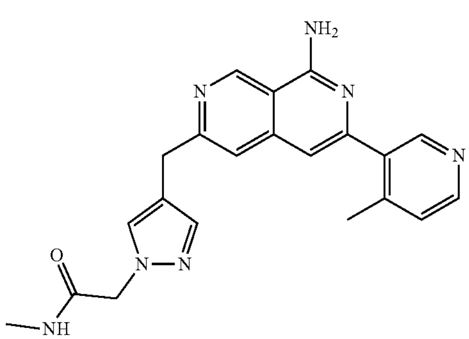 [SMILES: CNC(=O)Cn1cc(Cc2cc3cc(-c4cnccc4C)nc(N)c3cn2)cn1] | 2-[4-[[8-amino-6-(4-methyl-3-pyridyl)-2,7-naphthyridin-3-yl]amino]pyrazol-1-yl]-N-methyl-acetamide |

TABLE 1-continued
| Cmpd No. | Structure | Name |
| --- | --- | --- |
| 185 | 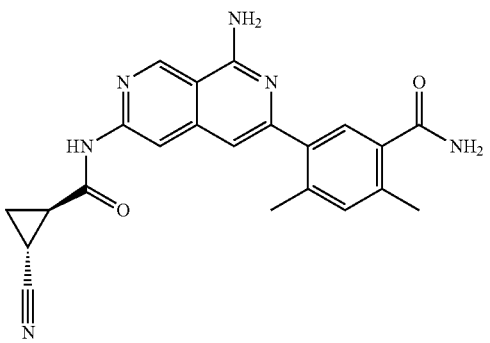 | trans-5-(1-amino-6-(trans-2-cyanocyclopropanecarboxamido)-2,7-naphthyridin-3-yl)-2,4-dimethylbenzamide |
| 186 | 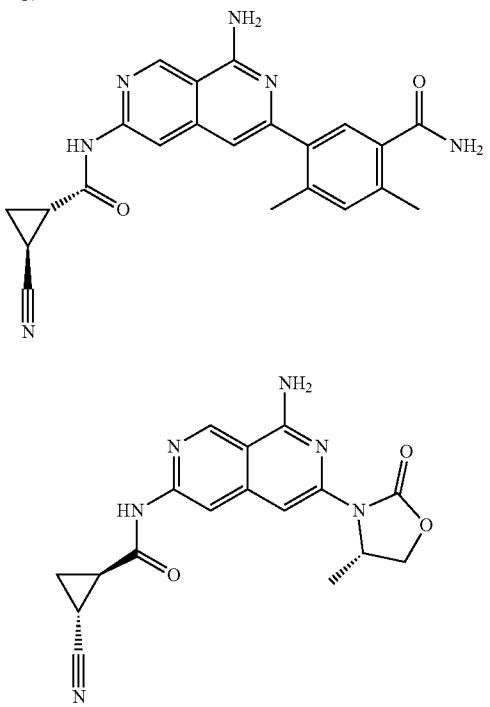 | trans-N-(8-amino-6-((S)-4-methyl-2-oxooxazolidin-3-yl)-2,7-naphthyridin-3-yl)-2-cyanocyclopropane carboxamide |
| 187 | 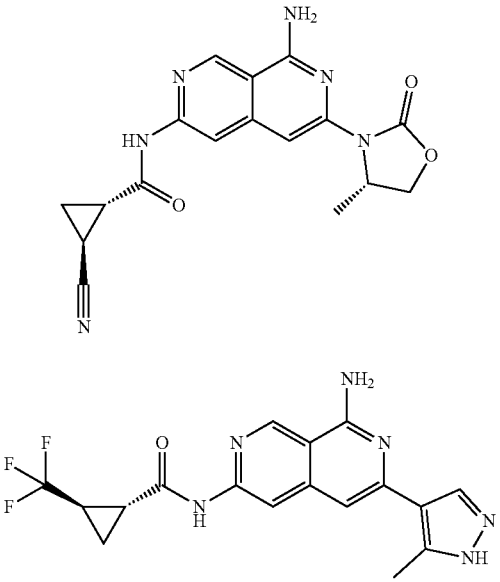 | trans-N-(8-amino-6-(5-methyl-1H-pyrazol-4-yl)-2,7-naphthyridin-3-yl)-2-(trifluoromethyl)cyclopropane carboxamide |

TABLE 1-continued

| Cmpd No. | Structure | Name |
|---|---|---|
| | | |
| 188 | | trans-N-(8-amino-6-(1,3,5-trimethyl-1H-pyrazol-4-yl)-2,7-naphthyridin-3-yl)-2-(trifluoromethyl)cyclopropanecarboxamide |
| 189 | | trans-N-(8-amino-6-(4-methylpyridin-3-yl)-2,7-naphthyridin-3-yl)-2-(pyrimidin-2-yl)cyclopropanecarboxamide |
| 190 | 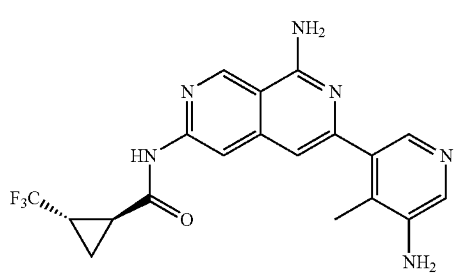 | trans-N-(8-amino-6-(5-amino-4-methylpyridin-3-yl)-2,7-naphthyridin-3-yl)-2-(trifluoromethyl)cyclopropanecarboxamide |

| Cmpd No. | Structure | Name |
|---|---|---|
| 191 | 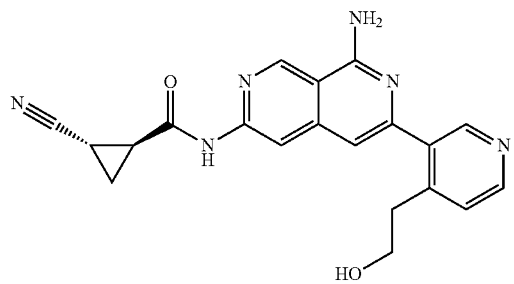 | trans-N-(8-amino-6-(4-(2-hydroxyethyl)pyridin-3-yl)-2,7-naphthyridin-3-yl)-2-cyanocyclopropanecarboxamide |
| 192 | 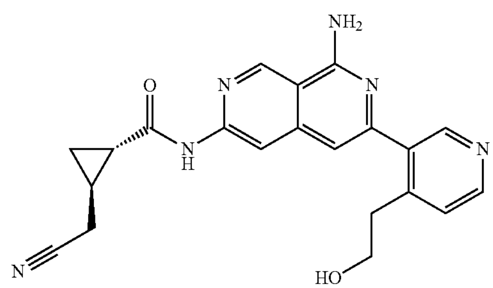 | trans-N-(8-amino-6-(4-(2-hydroxyethyl)pyridin-3-yl)-2,7-naphthyridin-3-yl)-2-(cyanomethyl)cyclopropanecarboxamide |

TABLE 1-continued

| Cmpd No. | Structure | Name |
|---|---|---|
| 193 | 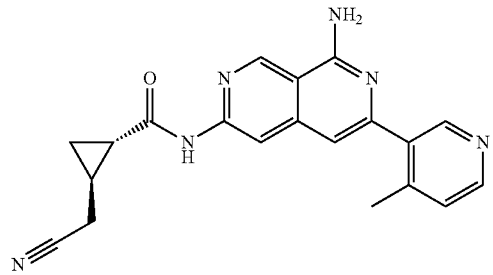 [SMILES: Cc1ccncc1-c1cc2cc(NC(=O)[C@H]3C[C@@H]3CC#N)ncc2c(N)n1] | (1S,2R)-N-(8-amino-6-(4-methylpyridin-3-yl)-2,7-naphthyridin-3-yl)-2-(cyanomethyl)cyclopropane-1-carboxamide |
| 194 | 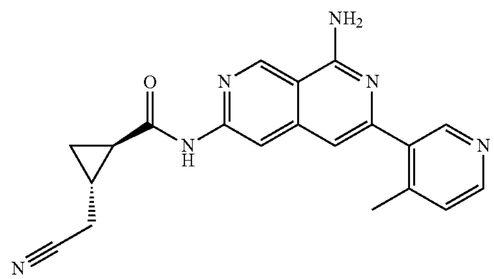 [SMILES: Cc1ccncc1-c1cc2cc(NC(=O)[C@@H]3C[C@H]3CC#N)ncc2c(N)n1] | (1R,2S)-N-(8-amino-6-(4-methylpyridin-3-yl)-2,7-naphthyridin-3-yl)-2-(cyanomethyl)cyclopropane-1-carboxamide |
| 195 | 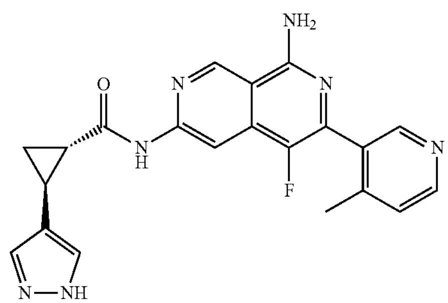 [SMILES: Cc1ccncc1-c1nc(N)c2cnc(NC(=O)[C@H]3C[C@@H]3c3cn[nH]c3)cc2c1F] | (1S,2S)-N-(8-amino-5-fluoro-6-(4-methylpyridin-3-yl)-2,7-naphthyridin-3-yl)-2-(1H-pyrazol-4-yl)cyclopropane-1-carboxamide |
| 196 | 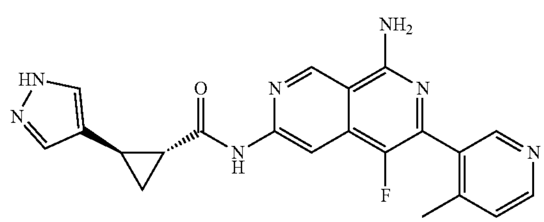 [SMILES: Cc1ccncc1-c1nc(N)c2cnc(NC(=O)[C@@H]3C[C@H]3c3cn[nH]c3)cc2c1F] | (1R,2R)-N-(8-amino-5-fluoro-6-(4-methylpyridin-3-yl)-2,7-naphthyridin-3-yl)-2-(1H-pyrazol-4-yl)cyclopropane-1-carboxamide |
| 197 | 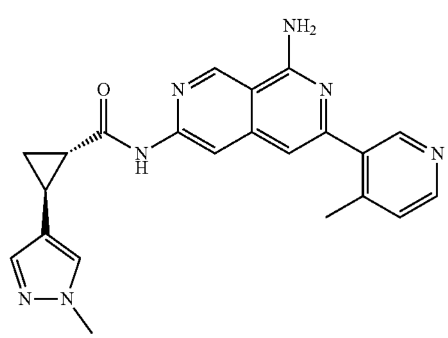 [SMILES: Cc1ccncc1-c1cc2cc(NC(=O)[C@H]3C[C@@H]3c3cnn(C)c3)ncc2c(N)n1] | (1S,2S)-N-(8-amino-6-(4-methylpyridin-3-yl)-2,7-naphthyridin-3-yl)-2-(1-methyl-1H-pyrazol-4-yl)cyclopropane-1-carboxamide |

TABLE 1-continued

| Cmpd No. | Structure | Name |
|---|---|---|
| 198 | 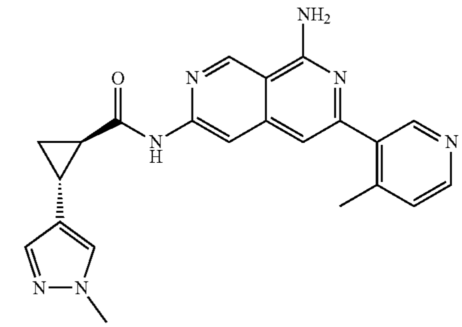 [SMILES: Cc1ccncc1-c1cc2cc(NC(=O)[C@@H]3C[C@H]3c3cnn(C)c3)ncc2c(N)n1] | (1R,2R)-N-(8-amino-6-(4-methylpyridin-3-yl)-2,7-naphthyridin-3-yl)-2-(1-methyl-1H-pyrazol-4-yl)cyclopropane-1-carboxamide |
| 199 | 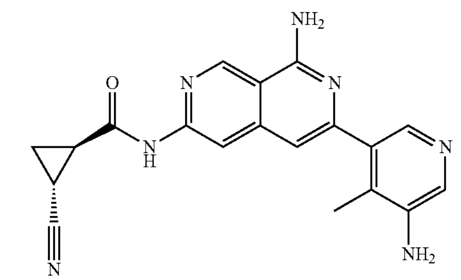 [SMILES: Cc1c(N)cncc1-c1cc2cc(NC(=O)[C@@H]3C[C@H]3C#N)ncc2c(N)n1] | (1R,2R)-N-(8-amino-6-(5-amino-4-methylpyridin-3-yl)-2,7-naphthyridin-3-yl)-2-cyanocyclopropane-1-carboxamide |
| 200 | 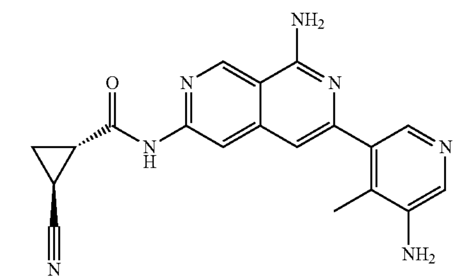 [SMILES: Cc1c(N)cncc1-c1cc2cc(NC(=O)[C@H]3C[C@@H]3C#N)ncc2c(N)n1] | (1S,2S)-N-(8-amino-6-(5-amino-4-methylpyridin-3-yl)-2,7-naphthyridin-3-yl)-2-cyanocyclopropane-1-carboxamide |
| 201 | | trans-N-(8-amino-6-(4-(trifluoromethyl)pyridin-3-yl)-2,7-naphthyridin-3-yl)-2-cyanocyclopropane-1-carboxamide |

TABLE 1-continued

| Cmpd No. | Structure | Name |
|---|---|---|
| 202 | 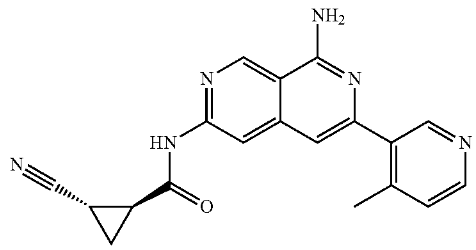 [SMILES: Cc1ccncc1-c1cc2cc(NC(=O)[C@H]3C[C@@H]3C#N)ncc2c(N)n1] | (1S,2S)-N-(8-amino-6-(4-methylpyridin-3-yl)-2,7-naphthyridin-3-yl)-2-cyanocyclopropane-1-carboxamide |
| 203 | 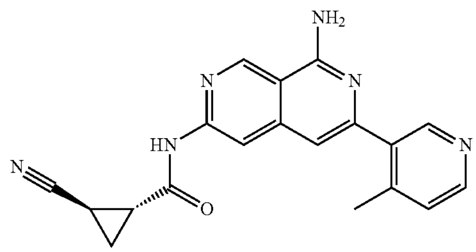 [SMILES: Cc1ccncc1-c1cc2cc(NC(=O)[C@@H]3C[C@H]3C#N)ncc2c(N)n1] | (1R,2R)-N-(8-amino-6-(4-methylpyridin-3-yl)-2,7-naphthyridin-3-yl)-2-cyanocyclopropane-1-carboxamide |
| 204 | | N-(8-amino-5-(3-hydroxycyclopent-1-enyl)-6-(4-methylpyridin-3-yl)-2,7-naphthyridin-3-yl)cyclopropanecarboxamide |
| | | |
| 205 | | trans-N-(8-amino-5-methyl-6-(4-methylpyridin-3-yl)-2,7-naphthyridin-3-yl)-2-(cyanomethyl)cyclopropanecarboxamide |

TABLE 1-continued
| Cmpd No. | Structure | Name |
|---|---|---|
| 206 | 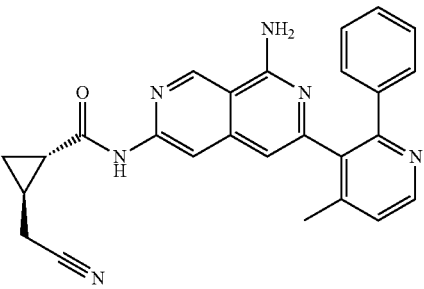 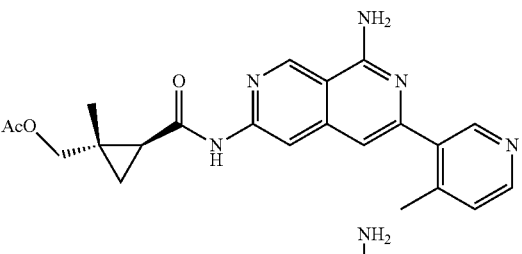 | trans-N-(8-amino-6-(4-methyl-2-phenylpyridin-3-yl)-2,7-naphthyridin-3-yl)-2-(cyanomethyl)cyclopropanecarboxamide |
| 207, 208 | 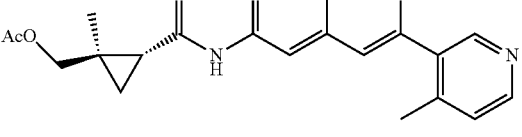 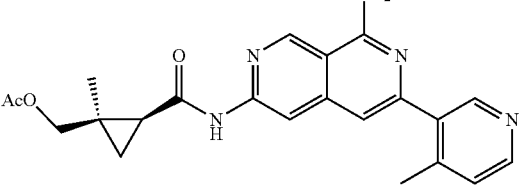 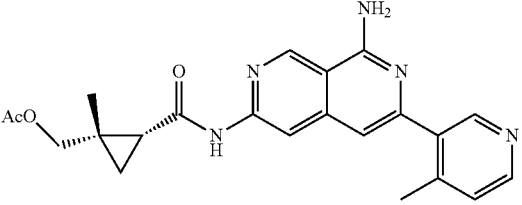 | 2-(8-amino-6-(4-methylpyridin-3-yl)-2,7-naphthyridin-3-ylcarbamoyl)-1-methylcyclopropyl)methyl acetate |

TABLE 1-continued

| Cmpd No. | Structure | Name |
|---|---|---|
| 209 | 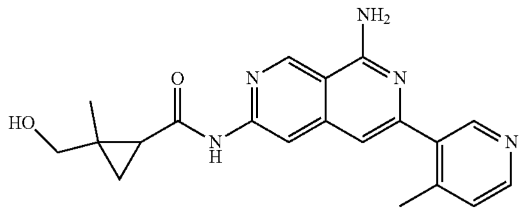 [SMILES: Cc1ccncc1-c1cc2cc(NC(=O)C3CC3(C)CO)ncc2c(N)n1] | N-(8-amino-6-(4-methylpyridin-3-yl)-2,7-naphthyridin-3-yl)-2-(hydroxymethyl)-2-methylcyclopropanecarboxamide |
| 210 | 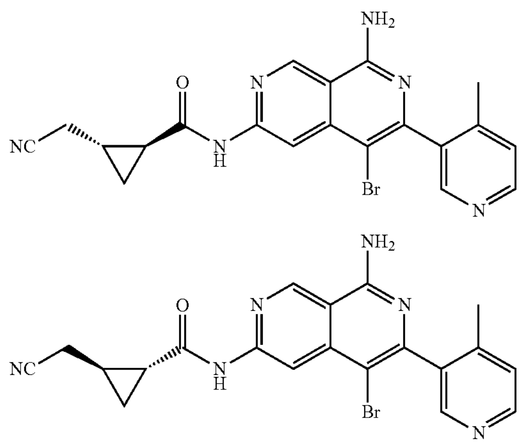 | trans-N-(8-amino-5-bromo-6-(4-methylpyridin-3-yl)-2,7-naphthyridin-3-yl)-2-(cyanomethyl)cyclopropanecarboxamide |
| 211 | 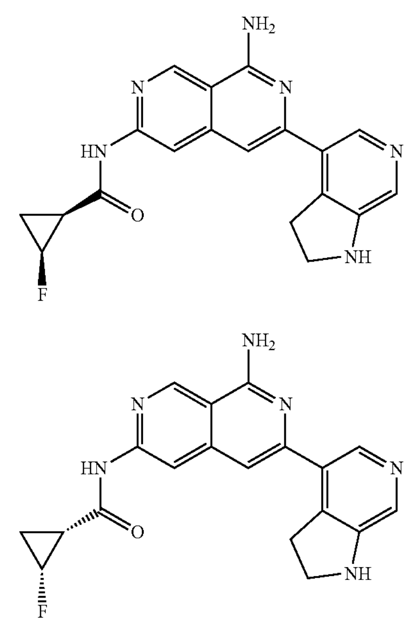 [SMILES: Nc1nc(-c2cncc3c2CCN3)cc2cc(NC(=O)[C@@H]3C[C@@H]3F)ncc12 ; Nc1nc(-c2cncc3c2CCN3)cc2cc(NC(=O)[C@H]3C[C@H]3F)ncc12] | cis-N-(8-amino-6-(2,3-dihydro-1H-pyrrolo[2,3-c]pyridin-4-yl)-2,7-naphthyridin-3-yl)-2-fluorocyclopropanecarboxamide |

TABLE 1-continued
| Cmpd No. | Structure | Name |
|---|---|---|
| 212 | 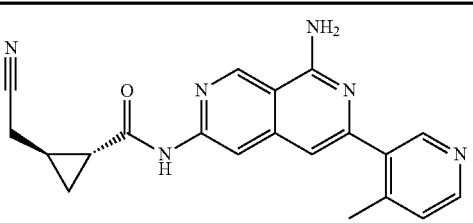<br>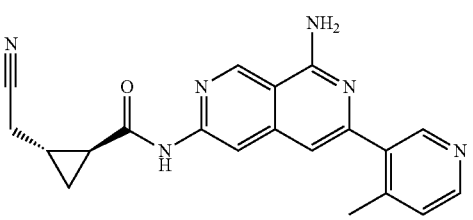 | trans-N-(8-amino-6-(4-methylpyridin-3-yl)-2,7-naphthyridin-3-yl)-2-(cyanomethyl)cyclopropanecarboxamide |
| 213 | 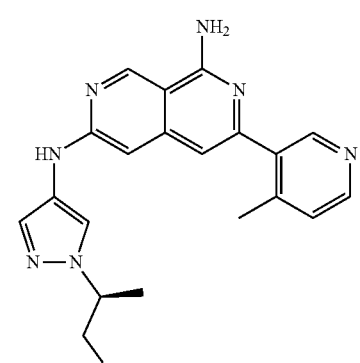<br>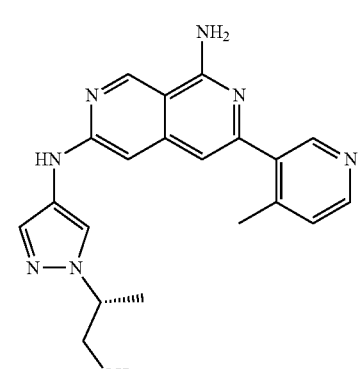 | 2-(4-(8-amino-6-(4-methylpyridin-3-yl)-2,7-naphthyridin-3-ylamino)-1H-pyrazol-1-yl)propan-1-ol |

TABLE 1-continued
| Cmpd No. | Structure | Name |
|---|---|---|
| 214, 215 | 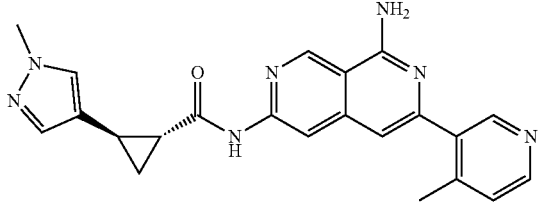 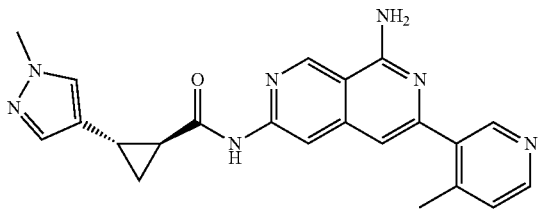 | trans-N-(8-amino-6-(4-(2-hydroxyethyl)pyridin-3-yl)-2,7-naphthyridin-3-yl)-2-(1-methyl-1H-pyrazol-4-yOcyclopropanecarboxamide |
| 216 | 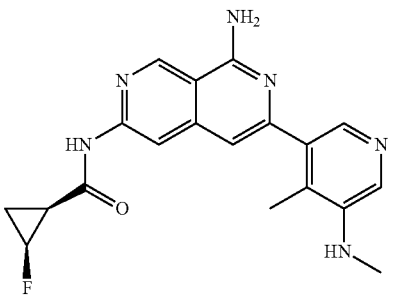 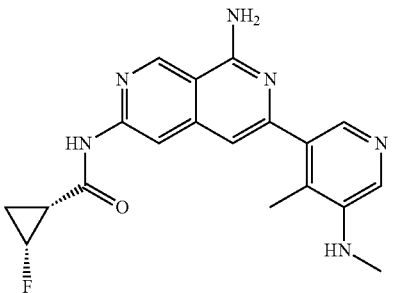 | cis-N-(8-amino-6-(4-methyl-5-(methylamino)pyridin-3-yl)-2,7-naphthyridin-3-yl)-2-fluorocyclopropanecarboxamide |

| Cmpd No. | Structure | Name |
|---|---|---|
| 217 | 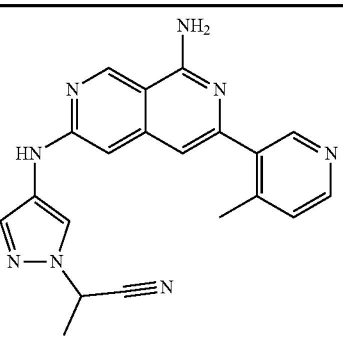 | 2-(4-(8-amino-6-(4-methylpyridin-3-yl)-2,7-naphthyridin-3-ylamino)-1H-pyrazol-1-yl)propanenitrile |
| 218 | | 1-(3-(4-(8-amino-6-(4-methylpyridin-3-yl)-2,7-naphthyridin-3-ylamino)-1H-pyrazol-1-yl)pyrrolidin-1-yl)ethanone |

| Cmpd No. | Structure | Name |
|---|---|---|
| 219 | | (trans)-3-(4-(8-amino-6-(4-methylpyridin-3-yl)-2,7-naphthyridin-3-ylamino)-1H-pyrazol-1-yl)-1-(oxetan-3-yl)piperidin-4-ol |
| | | (trans)-3-(4-(8-amino-6-(4-methylpyridin-3-yl)-2,7-naphthyridin-3-ylamino)-1H-pyrazol-1-yl)-1-(oxetan-3-yl)piperidin-4-ol |

TABLE 1-continued
| Cmpd No. | Structure | Name |
|---|---|---|
| 220 | 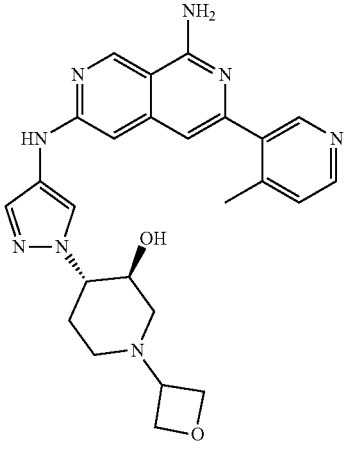 | (trans)-4-(4-(8-amino-6-(4-methylpyridin-3-yl)-2,7-naphthyridin-3-ylamino)-1H-pyrazol-1-yl)-1-(oxetan-3-yl)piperidin-3-ol |
| 221 | 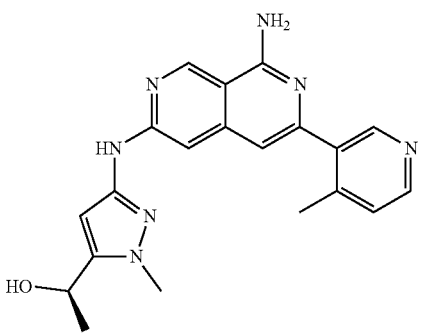 | 1-(3-(8-amino-6-(4-methylpyridin-3-yl)-2,7-naphthyridin-3-ylamino)-1-methyl-1H-pyrazol-5-yl)ethanol |

TABLE 1-continued

| Cmpd No. | Structure | Name |
|---|---|---|
| 222 | | cis-N-(8-amino-6-(3-oxo-3,4-dihydro-2H-pyrido[4,3-b][1,4]oxazin-8-yl)-2,7-naphthyridin-3-yl)-2-fluorocyclopropanecarboxamide |
| 223 | | cis-N-(8-amino-6-(3,4-dihydro-2H-pyrido[4,3-b][1,4]oxazin-8-yl)-2,7-naphthyridin-3-yl)-2-fluorocyclopropanecarboxamide |

TABLE 1-continued
| Cmpd No. | Structure | Name |
|---|---|---|
| 224 | 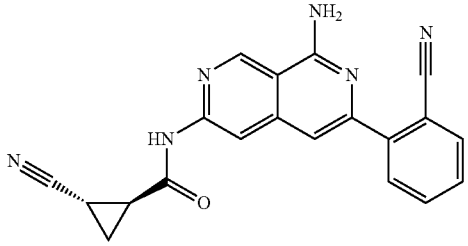 | trans-N-(8-amino-6-(2-cyanophenyl)-2,7-naphthyridin-3-yl)-2-cyanocyclopropanecarboxamide |
| 225 | 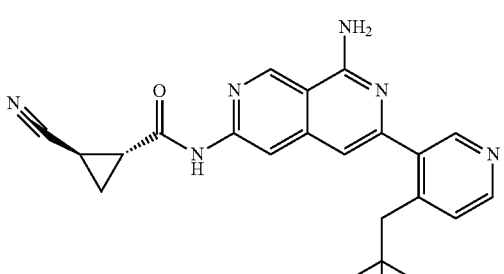 | trans-N-(8-amino-6-(4-(2-hydroxy-2-methylpropyl)pyridin-3-yl)-2,7-naphthyridin-3-yl)-2-cyanocyclopropanecarboxamide |

TABLE 1-continued
| Cmpd No. | Structure | Name |
|---|---|---|
| 226 | 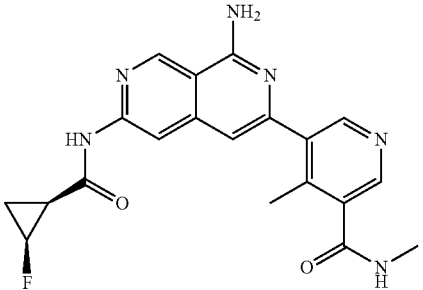<br>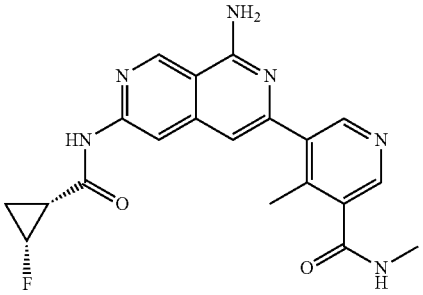 | cis-5-(1-amino-6-(-2-fluorocyclopropanecarboxamido)-2,7-naphthyridin-3-yl)-N,4-dimethylnicotinamide |
| 227 | 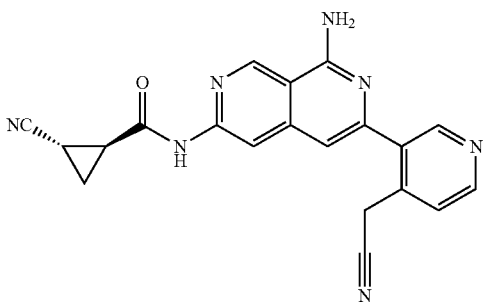<br>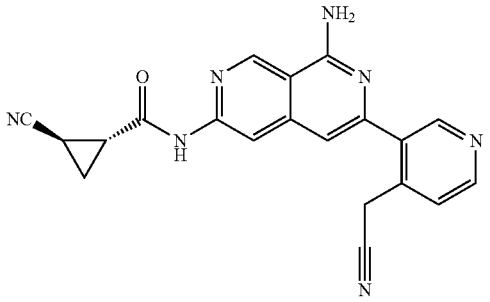 | trans-N-(8-amino-6-(4-(cyanomethyl)pyridin-3-yl)-2,7-naphthyridin-3-yl)-2-cyanocyclopropanecarboxamide |

TABLE 1-continued
| Cmpd No. | Structure | Name |
|---|---|---|
| 228 | 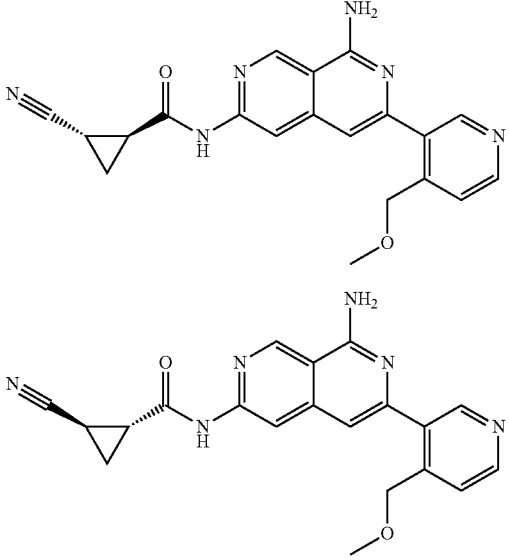 | trans-N-(8-amino-6-(4-(methoxymethyl)pyridin-3-yl)-2,7-naphthyridin-3-yl)-2-cyanocyclopropanecarboxamide |
| 229 | 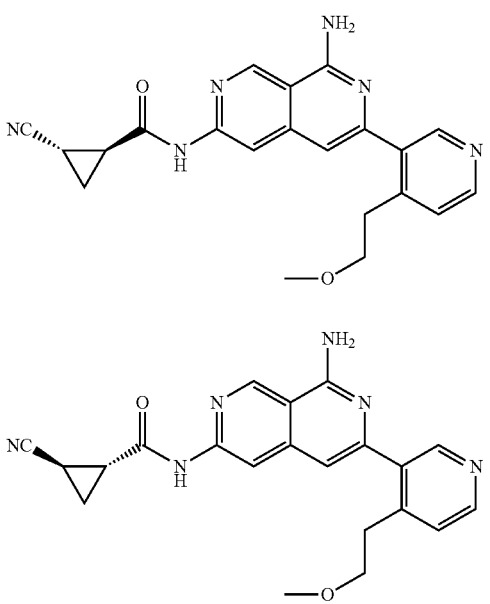 [SMILES: COCCc1ccncc1-c1cc2cc(NC(=O)[C@H]3C[C@@H]3C#N)ncc2c(N)n1 ; COCCc1ccncc1-c1cc2cc(NC(=O)[C@@H]3C[C@H]3C#N)ncc2c(N)n1] | trans-N-(8-amino-6-(4-(2-methoxyethyl)pyridin-3-yl)-2,7-naphthyridin-3-yl)-2-cyanocyclopropanecarboxamide |

TABLE 1-continued

| Cmpd No. | Structure | Name |
|---|---|---|
| 230 | 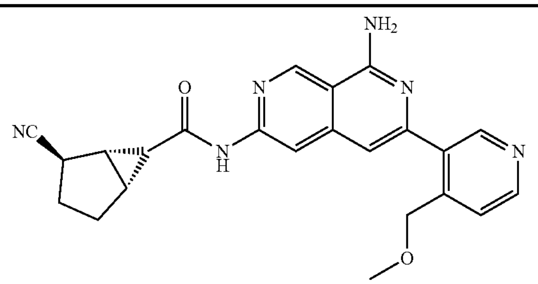 | (exo)-N-(8-amino-6-(4-methylpyridin-3-yl)-2,7-naphthyridin-3-yl)-2-cyanobicyclo[3.1.0]hexane-6-carboxamide |
| 231 | 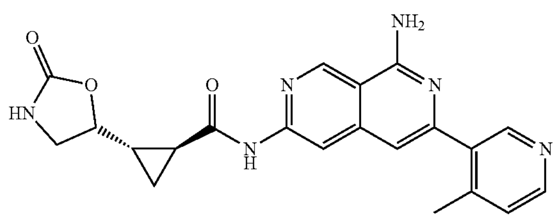 | trans-N-(8-amino-6-(4-methylpyridin-3-yl)-2,7-naphthyridin-3-yl-2-(2-oxooxazolidin-5-yl)cyclopropanecarboxamide |
| 232 | 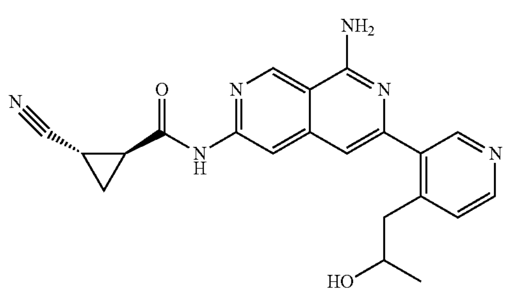 | trans-N-(8-amino-6-(4-(2-hydroxypropyl)pyridin-3-yl)-2,7-naphthyridin-3-yl)-2-cyanocyclopropanecarboxamide |

TABLE 1-continued

| Cmpd No. | Structure | Name |
|---|---|---|
| 233, 234 | | trans-N-(8-amino-5-chloro-6-(4-methylpyridin-3-yl)-2,7-naphthyridin-3-yl)-2-(1-methyl-1H-pyrazol-4-yl)cyclopropanecarboxamide |
| 235, 236 | | trans-N-(6-(4-(1H-pyrazol-4-yl)pyridin-3-yl)-8-amino-2,7-naphthyridin-3-yl)-2-cyanocyclopropanecarboxamide |
| 237, 238 | | trans-N-(8-amino-6-(4-methyl-6-(1-methyl-1H-pyrazol-4-yl)pyridin-3-yl)-2,7-naphthyridin-3-yl)-2-(cyanomethyl)cyclopropanecarboxamide |

TABLE 1-continued

| Cmpd No. | Structure | Name |
|---|---|---|
| 239, 240 | | trans-N-[8-amino-6-(4-methylpyridin-3-yl)-2,7-naphthyridin-3-yl]-2-(2-methoxypropan-2-yl)cyclopropane-1-carboxamide |
| 241, 242 | | trans-N-[8-amino-6-(4-methylpyridin-3-yl)-2,7-naphthyridin-3-yl]-2-(2-hydroxypropan-2-yl)cyclopropane-1-carboxamide |
| 243, 244 | | trans-N-(6-(4-(1H-pyrazol-3-yl)pyridin-3-yl)-8-amino-2,7-naphthyridin-3-yl)-2-cyanocyclopropanecarboxamide |

TABLE 1-continued
| Cmpd No. | Structure | Name |
|---|---|---|
| 245, 246 | 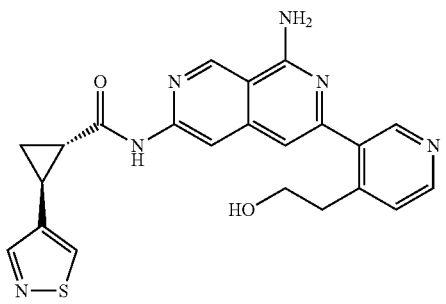 | trans-N-(8-amino-6-(4-(2-hydroxyethyl)pyridin-3-yl-2,7-naphthyridin-3-yl)-2-(isothiazol-4-yl)cyclopropanecarboxamide |
| 247, 248 | 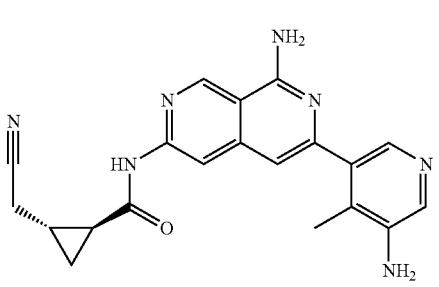 | trans-N-[8-amino-6-(5-amino-4-methylpyridin-3-yl)-2,7-naphthyridin-3-yl]-2-(cyanomethyl)cyclopropane-1-carboxamide |

TABLE 1-continued

| Cmpd No. | Structure | Name |
|---|---|---|
| 249, 250 | | 3-(4-[[8-amino-6-(4-methylpyridin-3-yl)-2,7-naphthyridin-3-yl]amino]-1H-pyrazol-1-yl)-1-methylpyrrolidin-2-one |
| 251, 252 | | 3-(4-[[8-amino-6-(4-methylpyridin-3-yl)-2,7-naphthyridin-3-yl]amino]-1H-pyrazol-1-yl)-1-methylpiperidin-2-one |

TABLE 1-continued

| Cmpd No. | Structure | Name |
|---|---|---|
| 253, 254 | 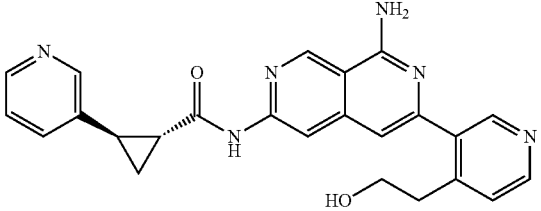 | trans-N-[8-amino-6-[4-(2-hydroxyethyl)pyridin-3-yl]-2,7-naphthyridin-3-yl]-2-(pyridin-3-yl)cyclopropane-1-carboxamide |
| 255 | 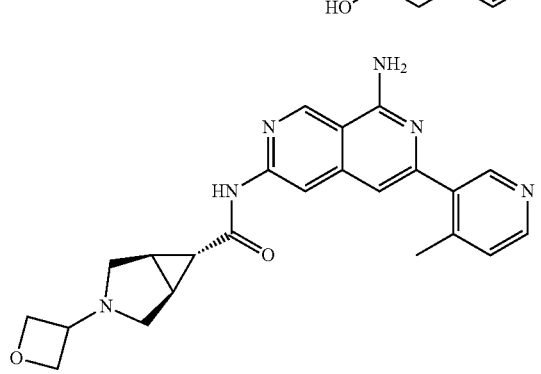 | Exo-N-[8-amino-6-(4-methylpyridin-3-yl)-2,7-naphthyridin-3-yl]-3-(oxetan-3-yl)-3-azabicyclo[3.1.0]hexane-6-carboxamide |
| 256 | 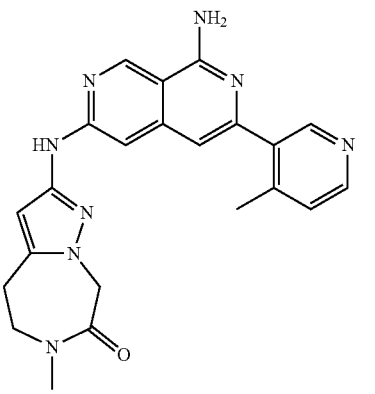 [SMILES: Cc1ccncc1-c1cc2cc(Nc3cc4n(n3)CC(=O)N(C)CC4)ncc2c(N)n1] | 2-[[8-amino-6-(4-methylpyridin-3-yl)-2,7-naphthyridin-3-yl]amino]-6-methyl-4H,5H,6H,7H,8H-pyrazolo[1,5-d][1,4]diazepin-7-one |
| 257 | 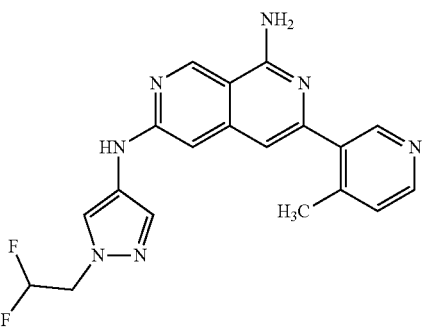 [SMILES: Cc1ccncc1-c1cc2cc(Nc3cnn(CC(F)F)c3)ncc2c(N)n1] | 6-N-[1-(2,2-difluoroethyl)-1H-pyrazol-4-yl]-3-(4-methylpyridin-3-yl)-2,7-naphthyridine-1,6-diamine |

TABLE 1-continued

| Cmpd No. | Structure | Name |
|---|---|---|
| 258 | 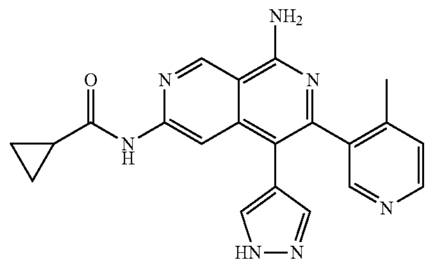 [SMILES: Cc1ccncc1-c1nc(N)c2cnc(NC(=O)C3CC3)cc2c1-c1cn[nH]c1] | N-(8-amino-6-(4-methylpyridin-3-yl)-5-(1H-pyrazol-4-yl-2,7-naphthyridin-3-yl)cyclopropanecarboxamide |
| 259 | 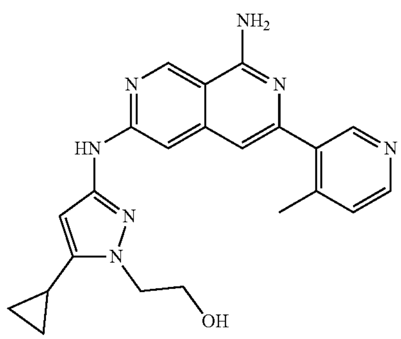 [SMILES: Cc1ccncc1-c1cc2cc(Nc3cc(C4CC4)n(CCO)n3)ncc2c(N)n1] | 2-(3-[[8-amino-6-(4-methylpyridin-3-yl)-2,7-naphthyridin-3-yl]amino]-5-cyclopropyl-1H-pyrazol-1-yl)ethan-1-ol |
| 260 | 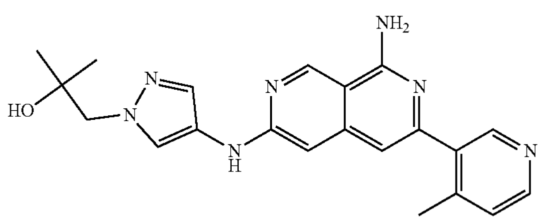 [SMILES: Cc1ccncc1-c1cc2cc(Nc3cnn(CC(C)(C)O)c3)ncc2c(N)n1] | 1-(4-[[8-amino-6-(4-methylpyridin-3-yl)-2,7-naphthyridin-3-yl]amino]-1H-pyrazol-1-yl)-2-methylpropan-2-ol |
| 261 | 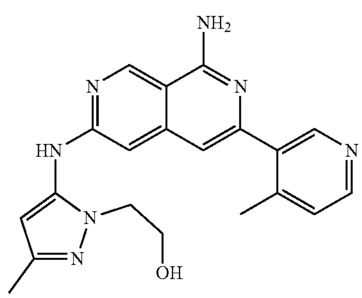 [SMILES: Cc1cc(Nc2cc3cc(-c4cnccc4C)nc(N)c3cn2)n(CCO)n1] | 2-(5-[[8-amino-6-(4-methylpyridin-3-yl)-2,7-naphthyridin-3-yl]amino]-3-methyl-1H-pyrazol-1-yl)ethan-1-ol |
| 262 | 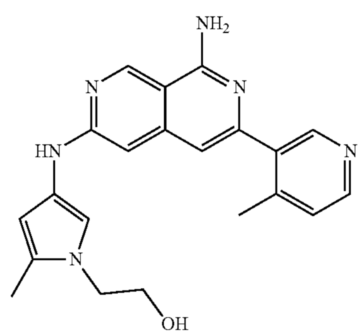 [SMILES: Cc1ccncc1-c1cc2cc(Nc3cc(C)n(CCO)c3)ncc2c(N)n1] | 2-(3-[[8-amino-6-(4-methylpyridin-3-yl)-2,7-naphthyridin-3-yl]amino]-5-methyl-1H-pyrazol-1-yl)ethan-1-ol |

TABLE 1-continued

| Cmpd No. | Structure | Name |
|---|---|---|
| 263 | 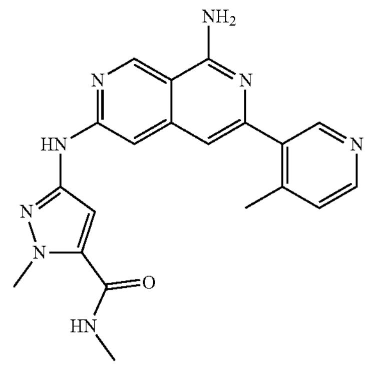 [SMILES: CNC(=O)c1cc(Nc2cc3cc(-c4cnccc4C)nc(N)c3cn2)nn1C] | 3-[[8-Amino-6-(4-methylpyridin-3-yl)-2,7-naphthyridin-3-yl]amino]-N,1-dimethyl-1H-pyrazole-5-carboxamide |
| 264 | 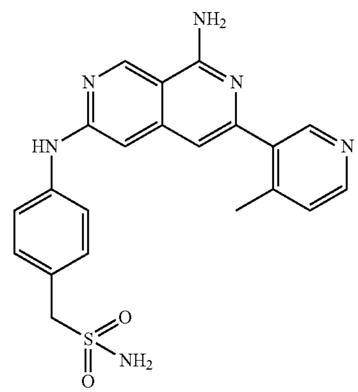 [SMILES: Cc1ccncc1-c1cc2cc(Nc3ccc(CS(N)(=O)=O)cc3)ncc2c(N)n1] | (4-[[8-Amino-6-(4-methylpyridin-3-yl-2,7-naphthyridin-3-yl]amino]phenyl)methanesulfonamide |
| 265 | 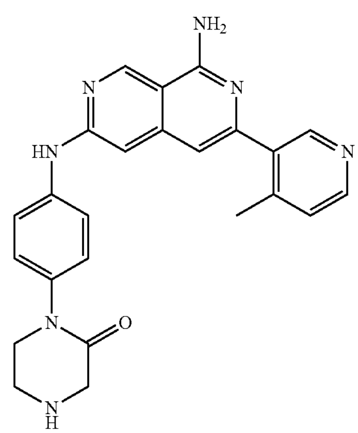 [SMILES: Cc1ccncc1-c1cc2cc(Nc3ccc(N4CCNCC4=O)cc3)ncc2c(N)n1] | 1-(4-[[8-amino-6-(4-methylpyridin-3-yl)-2,7-naphthyridin-3-yl]amino]phenyl)piperazin-2-one |
| 266 | 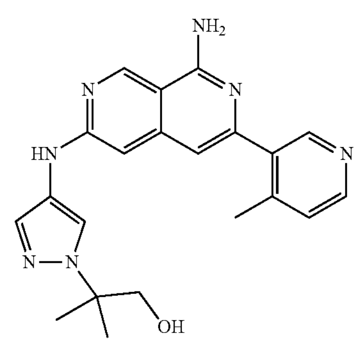 [SMILES: Cc1ccncc1-c1cc2cc(Nc3cnn(C(C)(C)CO)c3)ncc2c(N)n1] | 2-(4-[[8-amino-6-(4-methylpyridin-3-yl)-2,7-naphthyridin-3-yl]amino]-1H-pyrazol-1-yl)-2-methylpropan-1-ol |

TABLE 1-continued
| Cmpd No. | Structure | Name |
|---|---|---|
| 267 | 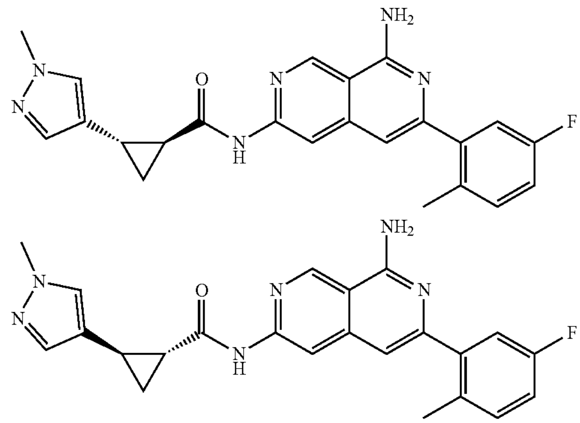 | trans-N-(8-amino-6-(5-fluoro-2-methylphenyl)-2,7-naphthyridin-3-yl)-2-(1-methyl-1H-pyrazol-4-yl)cyclopropanecarboxamide |
| 268 | 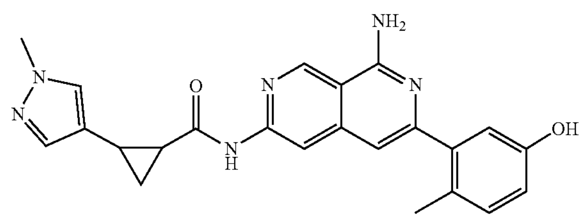 [SMILES: Cc1ccc(O)cc1-c1cc2cc(NC(=O)C3CC3c3cnn(C)c3)ncc2c(N)n1] | trans-N-[8-amino-6-(5-hydroxy-2-methylphenyl)-2,7-naphthyridin-3-yl]-2-(1-methyl-1H-pyrazol-4-yl)cyclopropane-1-carboxamide |
| 269, 270 | 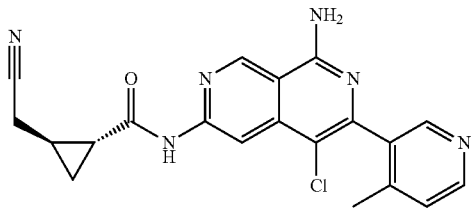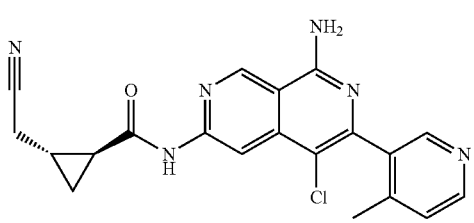 | trans-N-[8-amino-5-chloro-6-(4-methylpyridin-3-yl)-2,7-naphthyridin-3-yl]-2-(cyanomethyl)cyclopropane-1-carboxamide |

TABLE 1-continued
| Cmpd No. | Structure | Name |
|---|---|---|
| 271, 272 | 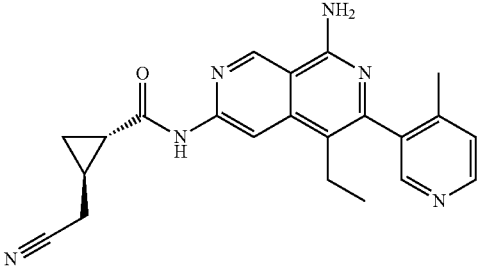 | trans-N-[8-amino-5-ethyl-6-(4-methylpyridin-3-yl)-2,7-naphthyridin-3-yl]-2-(cyanomethyl)cyclopropane-1-carboxamide |
| 273 | 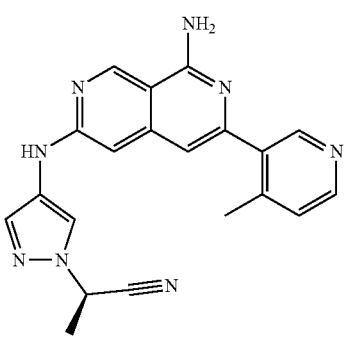 [SMILES: Cc1ccncc1-c1cc2cc(Nc3cnn([C@H](C)C#N)c3)ncc2c(N)n1] | (R)-2-(4-(8-amino-6-(4-methylpyridin-3-yl)-2,7-naphthyridin-3-ylamino)-1H-pyrazol-1-yl)propanenitrile |
| 274 | 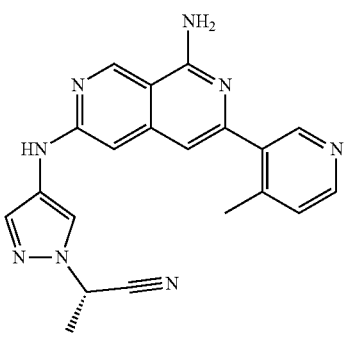 [SMILES: Cc1ccncc1-c1cc2cc(Nc3cnn([C@@H](C)C#N)c3)ncc2c(N)n1] | (S)-2-(4-(8-amino-6-(4-methylpyridin-3-yl)-2,7-naphthyridin-3-ylamino)-1H-pyrazol-1-yl)propanenitrile |

TABLE 1-continued

| Cmpd No. | Structure | Name |
|---|---|---|
| 275 | 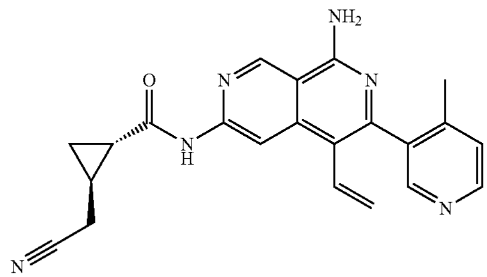 | trans-N-[8-amino-5-ethenyl-6-(4-methylpyridin-3-yl)-2,7-naphthyridin-3-yl]-2-(cyanomethyl)cyclopropane-1-carboxamide |
| 276, 277, 278, 279 | 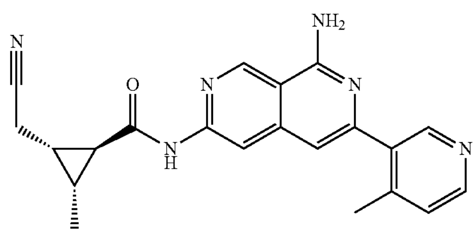 | (1,2)trans-N-[8-amino-6-(4-methylpyridin-3-yl-2,7-naphthyridin-3-yl]-2-(cyanomethyl)-3-methylcyclopropane-1-carboxamide |

TABLE 1-continued

| Cmpd No. | Structure | Name |
|---|---|---|
| 280, 281 | 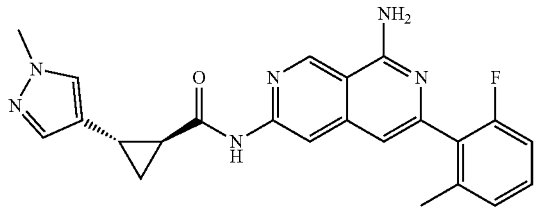 | trans-N-[8-amino-6-(2-fluoro-6-methylphenyl)-2,7-naphthyridin-3-yl]-2-(1-methyl-1H-pyrazol-4-yl)cyclopropane-1-carboxamide |
| 282, 283 | 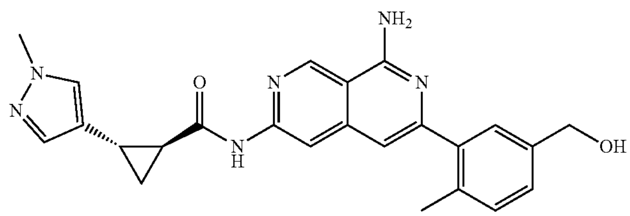 | trans-N-[8-amino-6-[5-(hydroxymethyl)-2-methylphenyl]-2,7-naphthyridin-3-yl]-2-(1-methyl-1H-pyrazol-4-yl)cyclopropane-1-carboxamide |
| 284, 285 | 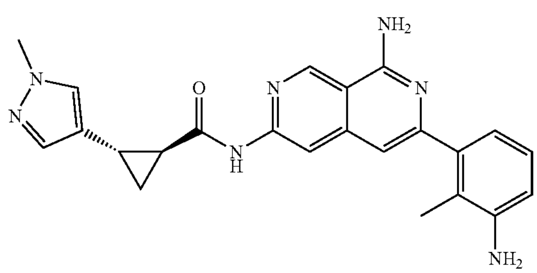 | trans-N-[8-amino-6-(3-amino-2-methylphenyl)-2,7-naphthyridin-3-yl]-2-(1-methyl-1H-pyrazol-4-yl)cyclopropane-1-carboxamide |

TABLE 1-continued

| Cmpd No. | Structure | Name |
|---|---|---|
| 286 | 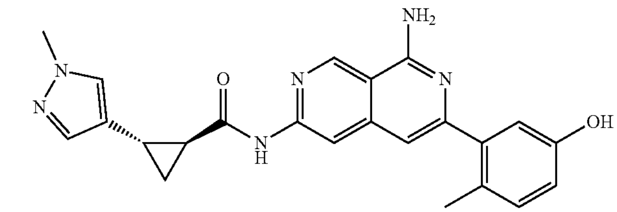 [SMILES: Cc1ccc(O)cc1-c1cc2cc(NC(=O)[C@H]3C[C@@H]3c3cnn(C)c3)ncc2c(N)n1] | (1S,2S)-N-[8-amino-6-(5-hydroxy-2-methylphenyl)-2,7-naphthyridin-3-yl]-2-(1-methyl-1H-pyrazol-4-yl)cyclopropane-1-carboxamide |
| 287 | 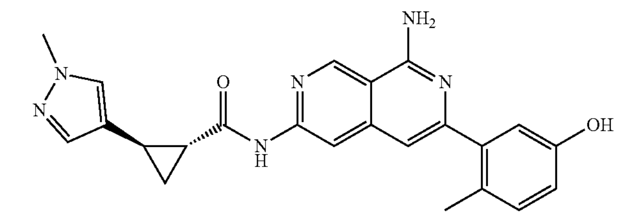 [SMILES: Cc1ccc(O)cc1-c1cc2cc(NC(=O)[C@@H]3C[C@H]3c3cnn(C)c3)ncc2c(N)n1] | (1R,2R)-N-[8-amino-6-(5-hydroxy-2-methylphenyl)-2,7-naphthyridin-3-yl]-2-(1-methyl-1H-pyrazol-4-yl)cyclopropane-1-carboxamide |
| 288, 289 | | trans-N-[8-amino-6-(5-methoxy-2-methylphenyl)-2,7-naphthyridin-3-yl]-2-(1-methyl-1H-pyrazol-4-yl)cyclopropane-1-carboxamide |
| 290, 291 | | trans-3-(1-amino-6-[[2-(1-methyl-1H-pyrazol-4-yl)cyclopropane]amido]-2,7-naphthyridin-3-yl)-N,N,4-trimethylbenzamide |

TABLE 1-continued

| Cmpd No. | Structure | Name |
| --- | --- | --- |
| 292, 293 | | trans-N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide |
| 294 | 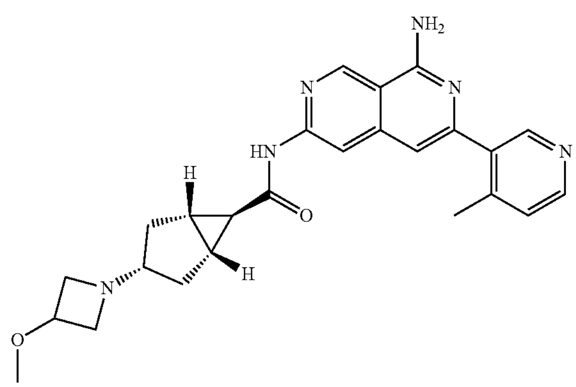 [SMILES: COC1CN([C@H]2C[C@@H]3[C@H](C2)[C@H]3C(=O)Nc2cc3cc(-c4cnccc4C)nc(N)c3cn2)C1] | (1R,3r,5S,6s)-N-[8-amino-6-(4-methylpyridin-3-yl)-2,7-naphthyridin-3-yl]-3-(3-methoxyazetidin-1-yl)bicyclo[3.1.0]hexane-6-carboxamide |
| 295, 296 | | trans-N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide |

TABLE 1-continued

| Cmpd No. | Structure | Name |
|---|---|---|
| 297 | 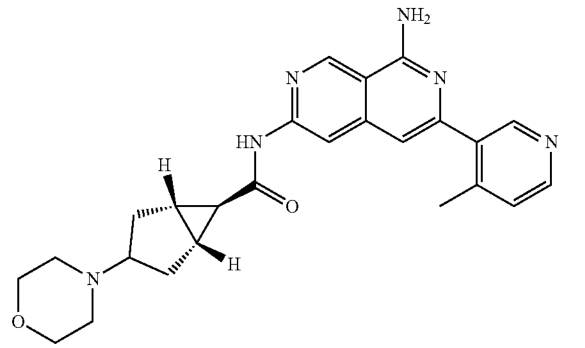 | exo-N-[8-amino-6-(4-methylpyridin-3-yl)-2,7-naphthyridin-3-yl]-3-(morpholin-4-yl)bicyclo[3.1.0]hexane-6-carboxamide |
| 298, 299 | | trans-N-[8-amino-6-(2-methylphenyl)-2,7-naphthyridin-3-yl]-2-(1-methyl-1H-pyrazol-4-yl)cyclopropane-1-carboxamide |
| 300, 301 | | trans-N-[8-amino-6-(5-cyano-2-methylphenyl)-2,7-naphthyridin-3-yl]-2-(1-methyl-1H-pyrazol-4-yl)cyclopropane-1-carboxamide |
| 302, 303 | 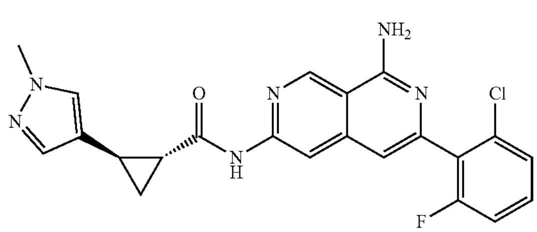 | trans-N-(8-amino-6-(2-chloro-6-fluorophenyl)-2,7-naphthyridin-3-yl]-2-(1-methyl-1H-pyrazol-4-yl)cyclopropanecarboxamide |

| Cmpd No. | Structure | Name |
|---|---|---|
| 304, 305 | | trans-N-[8-amino-6-(2-chlorophenyl)-2,7-naphthyridin-3-yl]-2-(1-methyl-1H-pyrazol-4-yl)cyclopropane-1-carboxamide |
| 306, 307 | | trans-N-[8-amino-6-(2,6-difluorophenyl)-2,7-naphthyridin-3-yl]-2-(1-methyl-1H-pyrazol-4-yl)cyclopropane-1-carboxamide |
| 308, 309 | | trans-N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide |

TABLE 1-continued

| Cmpd No. | Structure | Name |
|---|---|---|
| 310, 311 | | trans-N-(8-amino-6-(2,6-dichlorophenyl)-2,7-naphthyridin-3-yl)-2-(cyanomethyl)cyclopropane-1-carboxamide |
| 312, 313, 314, 315 | | N-[8-amino-6-(4-methylpyridin-3-yl)-2,7-naphthyridin-3-yl]-5-oxo-6-azaspiro[2.5]octane-1-carboxamide |
| 316, 317 | 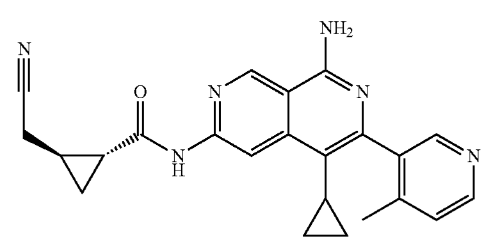 | trans-N-(8-amino-5-cyclopropyl-6-(4-methylpyridin-3-yl)-2,7-naphthyridin-3-yl)-2-(cyanomethyl)cyclopropane-1-carboxamide |

TABLE 1-continued

| Cmpd No. | Structure | Name |
|---|---|---|
| 318, 319 | 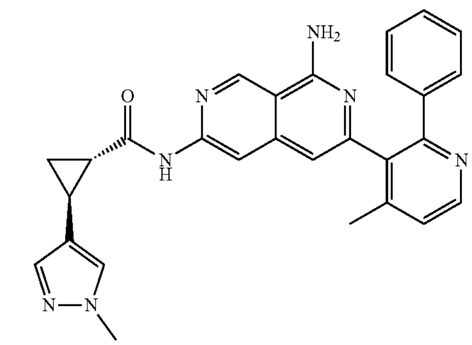 | trans-N-(8-amino-6-(4-methyl-2-phenylpyridin-3-yl)-2,7-naphthyridin-3-yl)-2-(1-methyl-1H-pyrazol-4-yl)cyclopropanecarboxamide |
| 320, 321, 322, 323 | 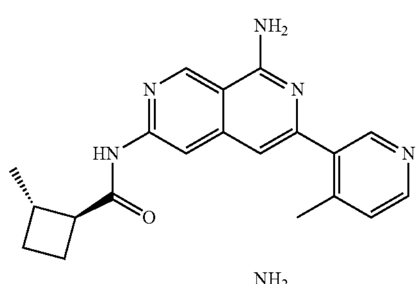 | N-(8-amino-6-(4-methylpyridin-3-yl)-2,7-naphthyridin-3-yl)-2-methylcyclobutanecarboxamide |

TABLE 1-continued

| Cmpd No. | Structure | Name |
|---|---|---|
| | (structure) | |
| | (structure) | |
| 324, 325 | (structure) | trans-N-[8-amino-6-(4-methylpyridin-3-yl)-2,7-naphthyridin-3-yl]-2-(oxan-4-yl)cyclopropane-1-carboxamide |
| | (structure) | |
| 326, 327, 328, 329 | (structure) | (1,3)trans-N-[8-amino-6-(4-methylpyridin-3-yl)-2,7-naphthyridin-3-yl]-2-methyl-3-(1-methyl-1H-pyrazol-4-yl)cyclopropane-1-carboxamide |
| | (structure) | |

TABLE 1-continued

| Cmpd No. | Structure | Name |
|---|---|---|
| 330 | 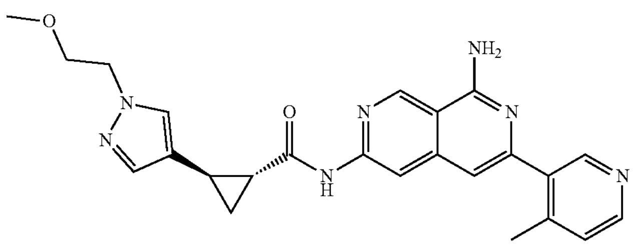 [SMILES: COCCn1cc([C@@H]2C[C@H]2C(=O)Nc2cc3cc(-c4cnccc4C)nc(N)c3cn2)cn1] | (1R,2R)-N-(8-amino-6-(4-methylpyridin-3-yl)-2,7-naphthyridin-3-yl)-2-(1-(2-methoxyethyl)-1H-pyrazol-4-yl)cyclopropanecarboxamide |
| 331 | 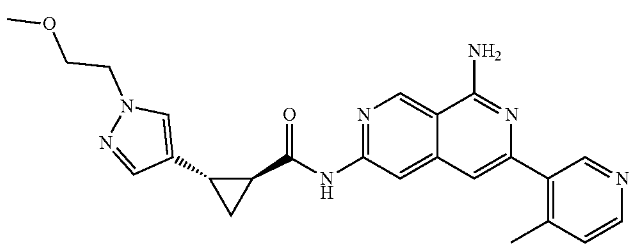 [SMILES: COCCn1cc([C@H]2C[C@@H]2C(=O)Nc2cc3cc(-c4cnccc4C)nc(N)c3cn2)cn1] | (1S,2S)-N-(8-amino-6-(4-methylpyridin-3-yl)-2,7-naphthyridin-3-yl)-2-(1-(2-methoxyethyl)-1H-pyrazol-4-yl)cyclopropanecarboxamide |
| 332 | 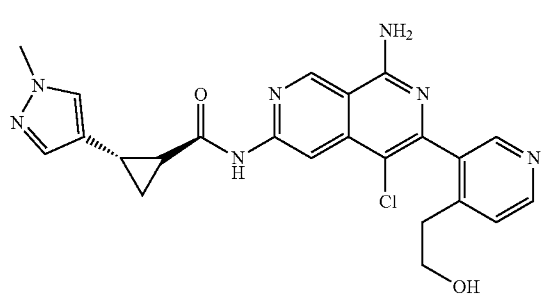 | (1S,2S)-N-(8-amino-5-chloro-6-(4-(2-hydroxyethyl)pyridin-3-yl)-2,7-naphthyridin-3-yl)-2-(1-methyl-1H-pyrazol-4-yl)cyclopropane-1-carboxamide |
| 333 | 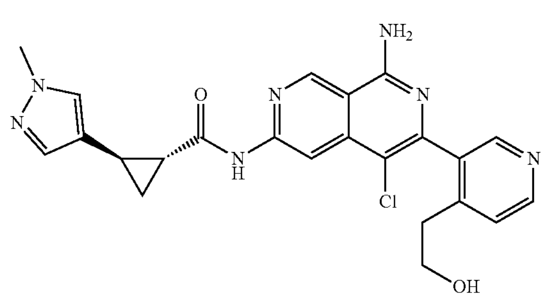 [SMILES: Cn1cc([C@@H]2C[C@H]2C(=O)Nc2cc3c(Cl)c(-c4cnccc4CCO)nc(N)c3cn2)cn1] | (1R,2R)-N-(8-amino-5-chloro-6-(4-(2-hydroxyethyl)pyridin-3-yl)-2,7-naphthyridin-3-yl)-2-(1-methyl-1H-pyrazol-4-yl)cyclopropane-1-carboxamide |

TABLE 1-continued

| Cmpd No. | Structure | Name |
| --- | --- | --- |
| 334, 335 | 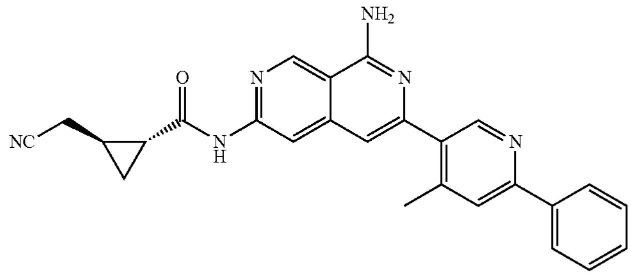 | trans-N-(8-amino-6-(4-methyl-6-phenylpyridin-3-yl)-2,7-naphthyridin-3-yl)-2-(cyanomethyl)cyclopropane-1-carboxamide |
| | | |
| 336 | 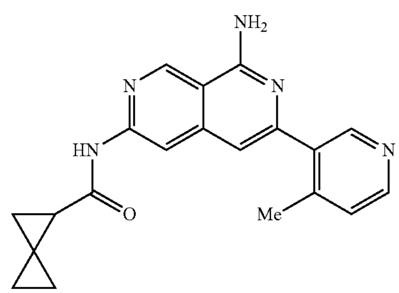 [SMILES: Cc1ccncc1-c1cc2cc(NC(=O)C3CC34CC4)ncc2c(N)n1] | N-(8-amino-6-(4-methylpyridin-3-yl)-2,7-naphthyridin-3-yl)spiro[2.2]pentane-1-carboxamide |
| 337 | 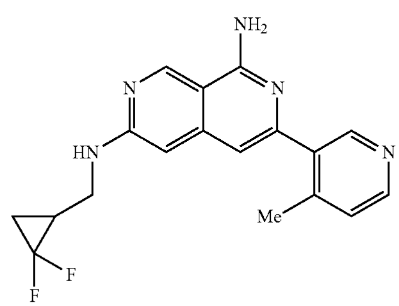 [SMILES: Cc1ccncc1-c1cc2cc(NCC3CC3(F)F)ncc2c(N)n1] | N6-((2,2-difluorocyclopropyl)methyl)-3-(4-methylpyridin-3-yl)-2,7-naphthyridine-1,6-diamine |
| 338 | 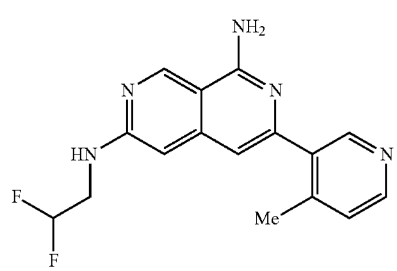 [SMILES: Cc1ccncc1-c1cc2cc(NCC(F)F)ncc2c(N)n1] | N6-(2,2-difluoroethyl)-3-(4-methylpyridin-3-yl)-2,7-naphthyridine-1,6-diamine |

TABLE 1-continued

| Cmpd No. | Structure | Name |
|---|---|---|
| 339 | 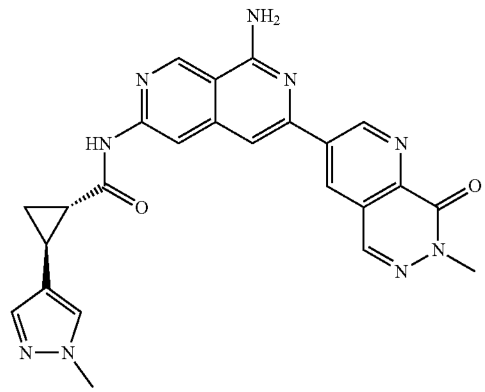 | trans-N-(8-amino-6-(7-methyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| | | |
| 340 | 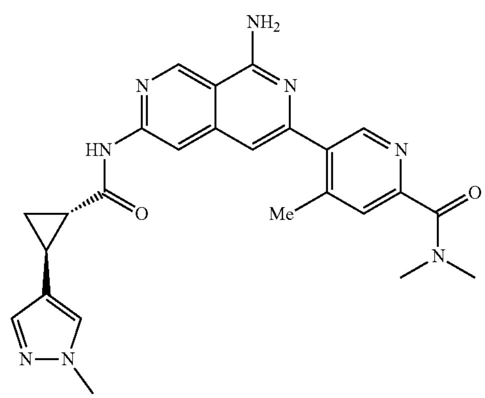 | 5-(1-amino-6-(trans-2-(1-methyl-1H-pyrazol-4-yl)cyclopropane-1-carboxamido)-2,7-naphthyridin-3-yl)-N,N,4-trimethylpicolinamide |

TABLE 1-continued
| Cmpd No. | Structure | Name |
|---|---|---|
| 341 | 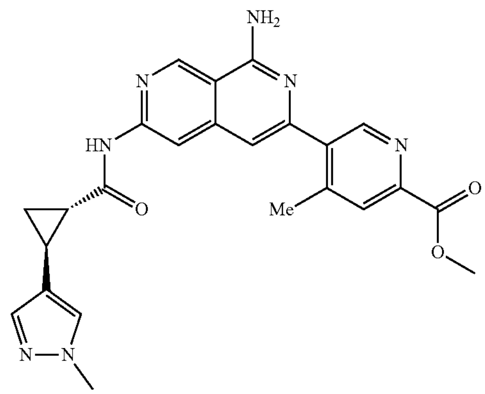 | methyl 5-(1-amino-6-(trans-2-(1-methyl-1H-pyrazol-4-yl)cyclopropane-1-carboxamido)-2,7-naphthyridin-3-yl)-4-methylpicolinate |
| 342 | 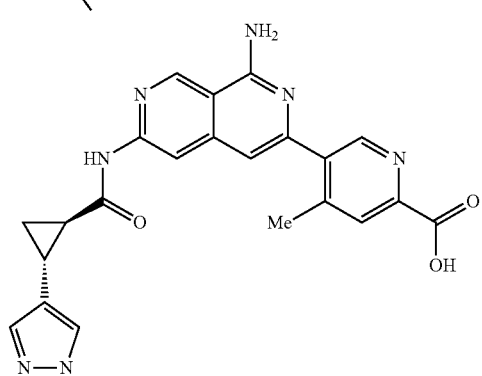 | 5-(1-amino-6-(trans-2-(1-methyl-1H-pyrazol-4-yl)cyclopropane-1-carboxamido)-2,7-naphthyridin-3-yl)-4-methylpicolinic acid |

TABLE 1-continued
| Cmpd No. | Structure | Name |
|---|---|---|
| 343 | 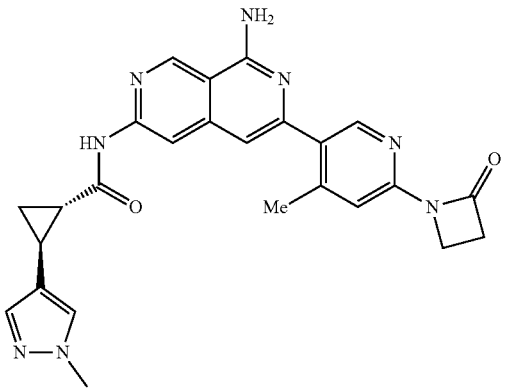 | trans-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide |
| 344 | 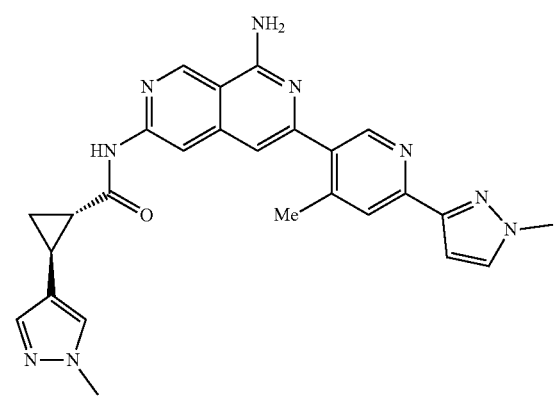 | trans-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide |

TABLE 1-continued

| Cmpd No. | Structure | Name |
|---|---|---|
| 345 | 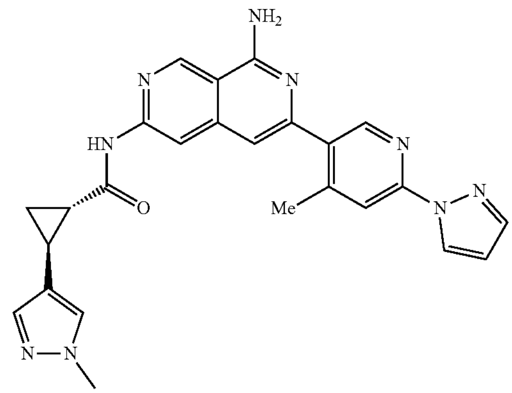 | trans-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide |
| 346 | 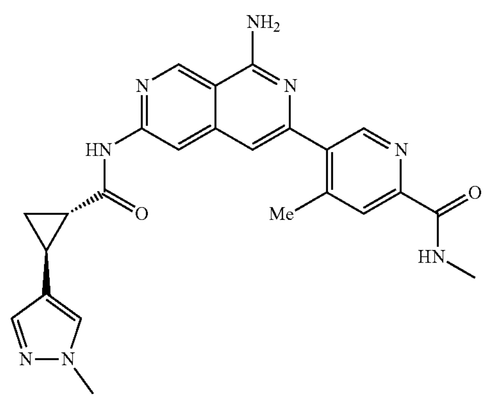 | 5-(1-amino-6-(trans-2-(1-methyl-1H-pyrazol-4-yl)cyclopropane-1-carboxamido)-2,7-naphthyridin-3-yl)-N,4-dimethylpicolinamide |

TABLE 1-continued

| Cmpd No. | Structure | Name |
|---|---|---|
| 347 | | trans-N-(8-amino-6-(6-amino-5-(trifluoromethyl)pyridin-3-yl)-2,7-naphthyridin-3-yl)-2-(1-methyl-1H-pyrazol-4-yl)cyclopropane-1-carboxamide |
| 348 | | 5-(1-amino-6-(trans-2-(1-methyl-1H-pyrazol-4-yl)cyclopropane-1-carboxamido)-2,7-naphthyridin-3-yl)-4-methylpicolinate |

TABLE 2

| Cmpd. No. | Structure | Name |
|---|---|---|
| 349 | 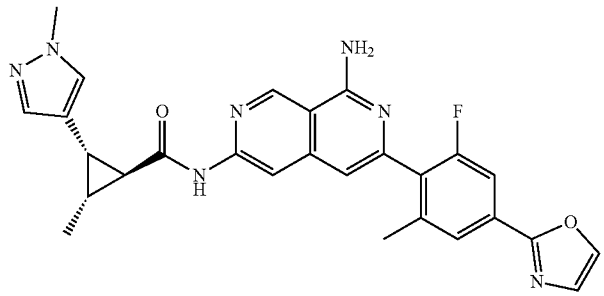 [SMILES: Cc1cc(-c2ncco2)cc(F)c1-c1cc2cc(NC(=O)[C@H]3[C@H](C)[C@@H]3c3cnn(C)c3)ncc2c(N)n1] | N-(8-amino-6-(2-fluoro-6-methyl-4-(oxazol-2-yl)phenyl)-2,7-naphthyridin-3-yl)-2-methyl-3-(1-methyl-1H-pyrazol-4-yl)cyclopropane-1-carboxamide |
| 350 | 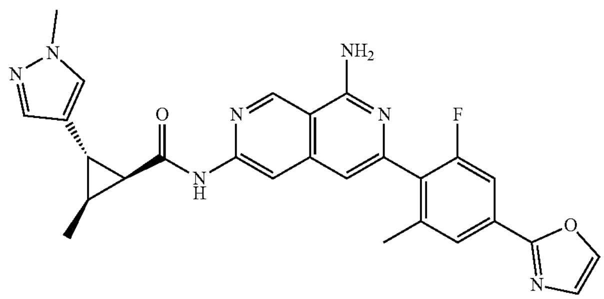 [SMILES: Cc1cc(-c2ncco2)cc(F)c1-c1cc2cc(NC(=O)[C@H]3[C@@H](C)[C@@H]3c3cnn(C)c3)ncc2c(N)n1] | (1S,2S,3S)-N-(8-amino-6-(2-fluoro-6-methyl-4-(oxazol-2-yl)phenyl)-2,7-naphthyridin-3-yl)-2-methyl-3-(1-methyl-1H-pyrazol-4-yl)cyclopropane-1-carboxamide |
| 351 | 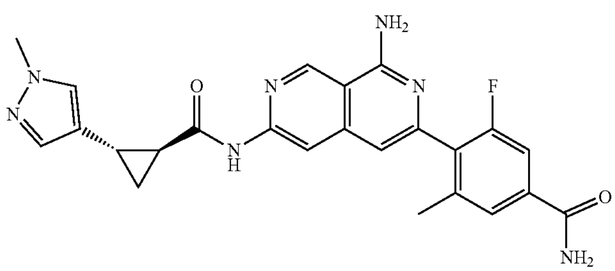 [SMILES: Cc1cc(C(N)=O)cc(F)c1-c1cc2cc(NC(=O)[C@H]3C[C@@H]3c3cnn(C)c3)ncc2c(N)n1] | 4-(1-amino-6-((1S,2S)-2-(1-methyl-1H-pyrazol-4-yl)cyclopropane-1-carboxamido)-2,7-naphthyridin-3-yl)-3-fluoro-5-methylbenzamide |
| 352 | 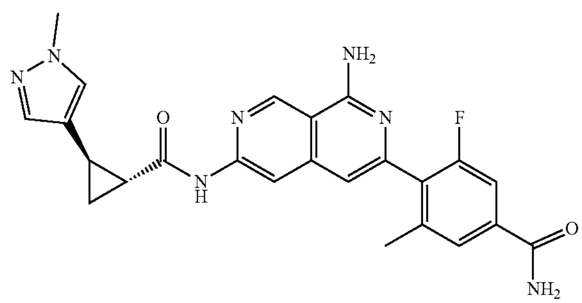 [SMILES: Cc1cc(C(N)=O)cc(F)c1-c1cc2cc(NC(=O)[C@@H]3C[C@H]3c3cnn(C)c3)ncc2c(N)n1] | 4-(1-amino-6-((1R,2R)-2-(1-methyl-1H-pyrazol-4-yl)cyclopropane-1-carboxamido)-2,7-naphthyridin-3-yl)-3-fluoro-5-methylbenzamide |
| 353 | 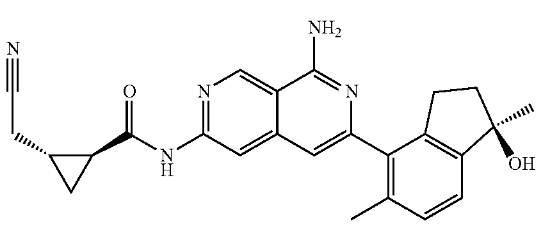 [SMILES: Cc1ccc2c(c1-c1cc3cc(NC(=O)[C@H]4C[C@@H]4CC#N)ncc3c(N)n1)CC[C@@]2(C)O] | (1S,2R)-N-(8-amino-6-((R)-1-hydroxy-1,5-dimethyl-2,3-dihydro-1H-inden-4-yl)-2,7-naphthyridin-3-yl)-2-(cyanomethyl)cyclopropane-1-carboxamide |

TABLE 2-continued

| Cmpd. No. | Structure | Name |
|---|---|---|
| 354 | 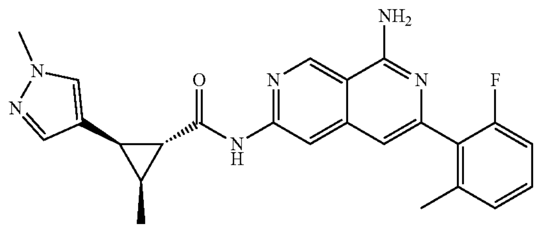 [SMILES: Cc1cccc(F)c1-c1cc2cc(NC(=O)[C@@H]3[C@@H](C)[C@H]3c3cnn(C)c3)ncc2c(N)n1] | (1R,2S,3R)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide |
| 355 | 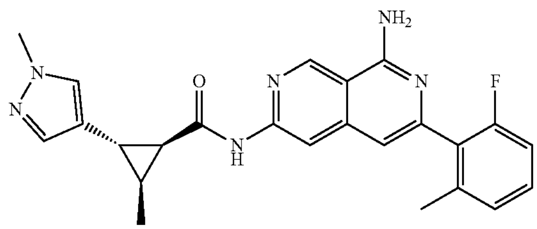 [SMILES: Cc1cccc(F)c1-c1cc2cc(NC(=O)[C@H]3[C@@H](C)[C@@H]3c3cnn(C)c3)ncc2c(N)n1] | (1S,2S,3S)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide |
| 356 | 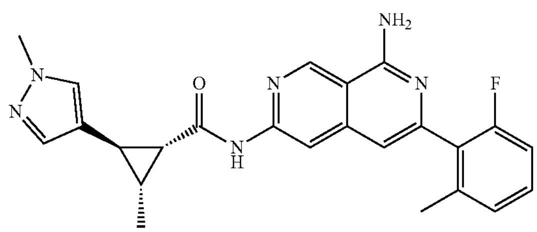 [SMILES: Cc1cccc(F)c1-c1cc2cc(NC(=O)[C@@H]3[C@H](C)[C@H]3c3cnn(C)c3)ncc2c(N)n1] | (1R,2R,3R)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide |
| 357 | 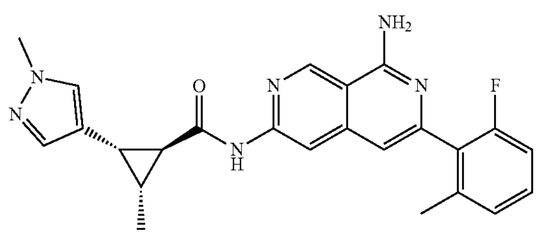 [SMILES: Cc1cccc(F)c1-c1cc2cc(NC(=O)[C@H]3[C@H](C)[C@@H]3c3cnn(C)c3)ncc2c(N)n1] | (1S,2R,3S)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide |
| 358 | 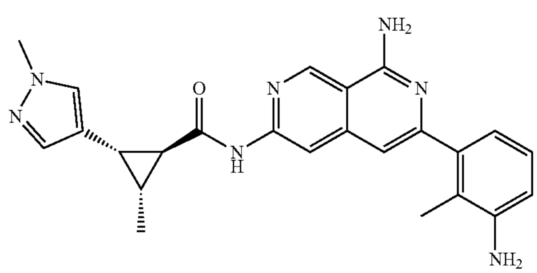 [SMILES: Cc1c(N)cccc1-c1cc2cc(NC(=O)[C@H]3[C@H](C)[C@@H]3c3cnn(C)c3)ncc2c(N)n1] | (1S,2R,3S)-N-(8-amino-6-(3-amino-2-methylphenyl)-2,7-naphthyridin-3-yl)-2-methyl-3-(1-methyl-1H-pyrazol-4-yl)cyclopropane-1-carboxamide |
| 359 | 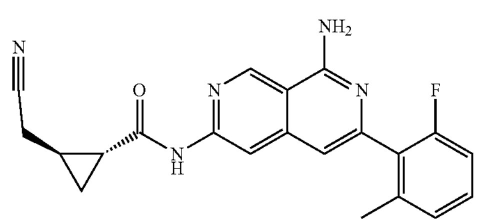 [SMILES: Cc1cccc(F)c1-c1cc2cc(NC(=O)[C@@H]3C[C@H]3CC#N)ncc2c(N)n1] | (1R,2S)-N-(8-amino-6-(2-fluoro-6-methylphenyl)-2,7-naphthyridin-3-yl)-2-(cyanomethyl)cyclopropane-1-carboxamide |

TABLE 2-continued

| Cmpd. No. | Structure | Name |
|---|---|---|
| 360 | 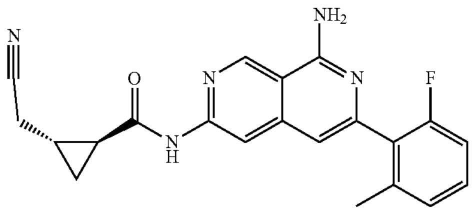 [SMILES: Cc1cccc(F)c1-c1cc2cc(NC(=O)[C@H]3C[C@@H]3CC#N)ncc2c(N)n1] | (1S,2R)-N-(8-amino-6-(2-fluoro-6-methylphenyl)-2,7-naphthyridin-3-yl)-2-(cyanomethyl)cyclopropane-1-carboxamide |
| 361 | 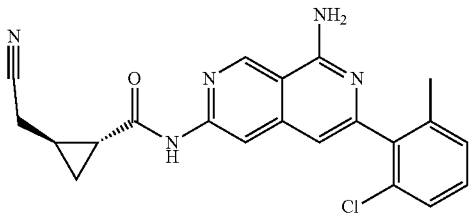 [SMILES: Cc1cccc(Cl)c1-c1cc2cc(NC(=O)[C@@H]3C[C@H]3CC#N)ncc2c(N)n1] | (1R,2S)-N-(8-amino-6-(2-chloro-6-methylphenyl)-2,7-naphthyridin-3-yl)-2-(cyanomethyl)cyclopropane-1-carboxamide |
| 362 | 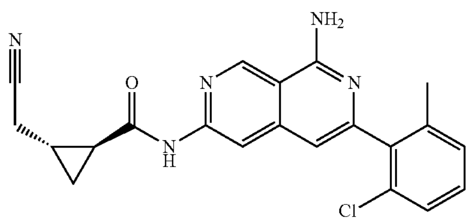 [SMILES: Cc1cccc(Cl)c1-c1cc2cc(NC(=O)[C@H]3C[C@@H]3CC#N)ncc2c(N)n1] | (1S,2R)-N-(8-amino-6-(2-chloro-6-methylphenyl)-2,7-naphthyridin-3-yl)-2-(cyanomethyl)cyclopropane-1-carboxamide |
| 363 | 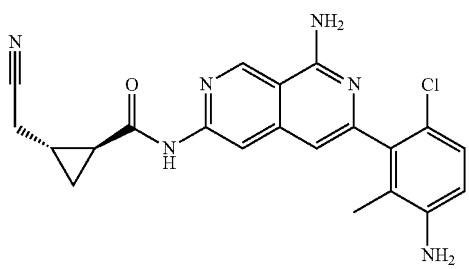 [SMILES: Cc1c(N)ccc(Cl)c1-c1cc2cc(NC(=O)[C@H]3C[C@@H]3CC#N)ncc2c(N)n1] | (1S,2R)-N-(8-amino-6-(3-amino-6-chloro-2-methylphenyl)-2,7-naphthyridin-3-yl)-2-(cyanomethyl)cyclopropane-1-carboxamide |
| 364 | 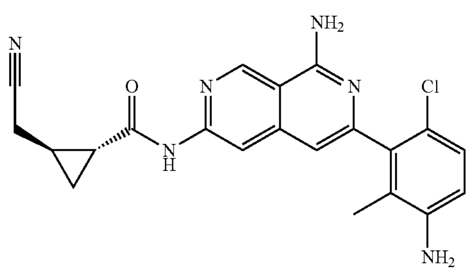 [SMILES: Cc1c(N)ccc(Cl)c1-c1cc2cc(NC(=O)[C@@H]3C[C@H]3CC#N)ncc2c(N)n1] | (1R,2S)-N-(8-amino-6-(3-amino-6-chloro-2-methylphenyl)-2,7-naphthyridin-3-yl)-2-(cyanomethyl)cyclopropane-1-carboxamide |
| 365 | 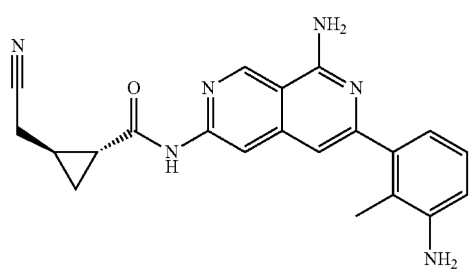 [SMILES: Cc1c(N)cccc1-c1cc2cc(NC(=O)[C@@H]3C[C@H]3CC#N)ncc2c(N)n1] | (1R,2S)-N-(8-amino-6-(3-amino-2-methylphenyl)-2,7-naphthyridin-3-yl)-2-(cyanomethyl)cyclopropane-1-carboxamide |

TABLE 2-continued

| Cmpd. No. | Structure | Name |
|---|---|---|
| 366 | 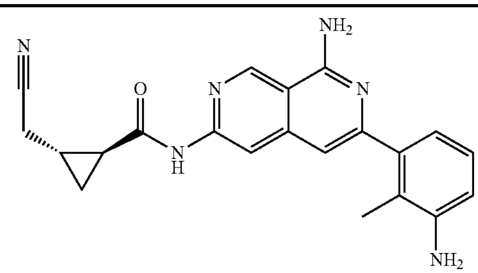 | (1S,2R)-N-(8-amino-6-(3-amino-2-methylphenyl)-2,7-naphthyridin-3-yl)-2-(cyanomethyl)cyclopropane-1-carboxamide |
| 367 | 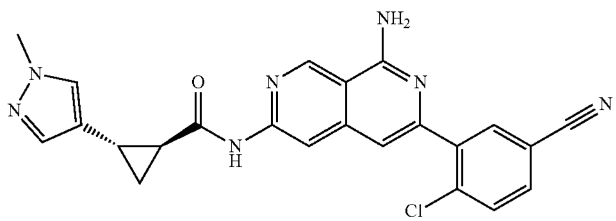 [SMILES: Cn1cc([C@H]2C[C@@H]2C(=O)Nc2cc3cc(-c4cc(C#N)ccc4Cl)nc(N)c3cn2)cn1] | (+/−)-trans-N-(8-amino-6-(2-chloro-5-cyanophenyl)-2,7-naphthyridin-3-yl)-2-(1-methyl-1H-pyrazol-4-yl)cyclopropane-1-carboxamide |
| 368 | 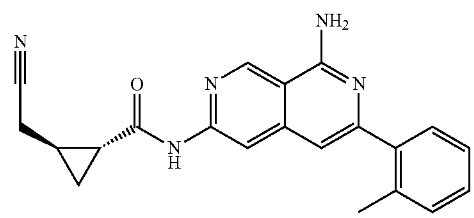 [SMILES: Cc1ccccc1-c1cc2cc(NC(=O)[C@@H]3C[C@H]3CC#N)ncc2c(N)n1] | (1R,2S)-N-(8-amino-6-(o-tolyl)-2,7-naphthyridin-3-yl)-2-(cyanomethyl)cyclopropane-1-carboxamide |
| 369 | 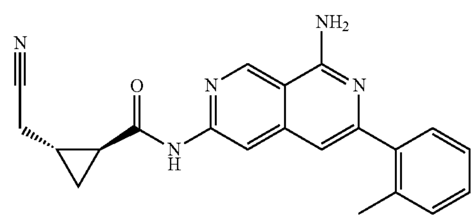 [SMILES: Cc1ccccc1-c1cc2cc(NC(=O)[C@H]3C[C@@H]3CC#N)ncc2c(N)n1] | (1S,2R)-N-(8-amino-6-(o-tolyl)-2,7-naphthyridin-3-yl)-2-(cyanomethyl)cyclopropane-1-carboxamide |
| 370 | 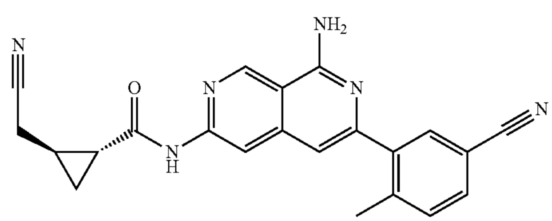 [SMILES: Cc1ccc(C#N)cc1-c1cc2cc(NC(=O)[C@@H]3C[C@H]3CC#N)ncc2c(N)n1] | (1R,2S)-N-(8-amino-6-(5-cyano-2-methylphenyl)-2,7-naphthyridin-3-yl)-2-(cyanomethyl)cyclopropane-1-carboxamide |
| 371 | 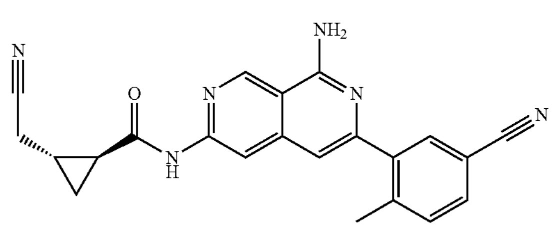 [SMILES: Cc1ccc(C#N)cc1-c1cc2cc(NC(=O)[C@H]3C[C@@H]3CC#N)ncc2c(N)n1] | (1S,2R)-N-(8-amino-6-(5-cyano-2-methylphenyl)-2,7-naphthyridin-3-yl)-2-(cyanomethyl)cyclopropane-1-carboxamide |
| 372 | 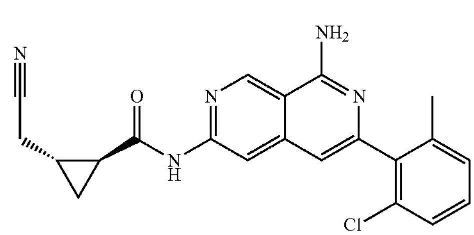 | trans-N-(8-amino-6-(2-chloro-6-methylphenyl)-2,7-naphthyridin-3-yl)-2-(cyanomethyl)cyclopropane-1-carboxamide |

TABLE 2-continued

| Cmpd. No. | Structure | Name |
|---|---|---|
| 373 | 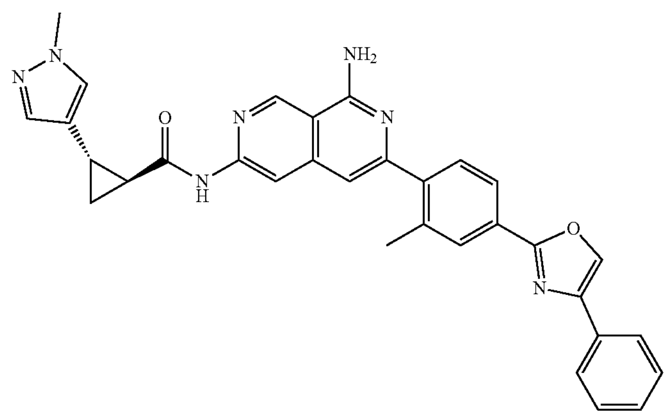 [SMILES: Cc1cc(-c2nc(-c3ccccc3)co2)ccc1-c1cc2cc(NC(=O)[C@H]3C[C@@H]3c3cnn(C)c3)ncc2c(N)n1] | (1S,2S)-N-(8-amino-6-(2-methyl-4-(4-phenyloxazol-2-yl)phenyl)-2,7-naphthyridin-3-yl)-2-(1-methyl-1H-pyrazol-4-yl)cyclopropane-1-carboxamide |
| 374 | 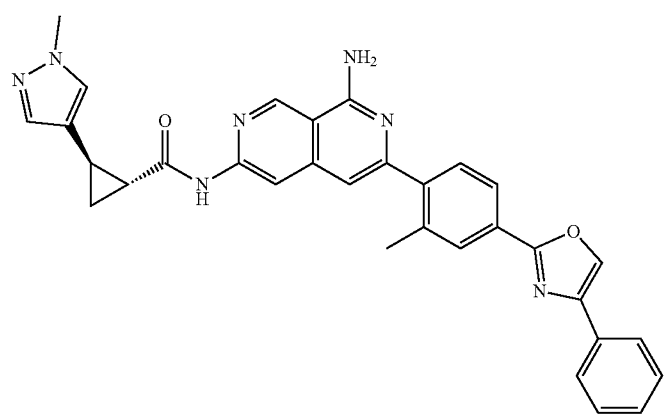 [SMILES: Cc1cc(-c2nc(-c3ccccc3)co2)ccc1-c1cc2cc(NC(=O)[C@@H]3C[C@H]3c3cnn(C)c3)ncc2c(N)n1] | (1R,2R)-N-(8-amino-6-(2-methyl-4-(4-phenyloxazol-2-yl)phenyl)-2,7-naphthyridin-3-yl)-2-(1-methyl-1H-pyrazol-4-yl)cyclopropane-1-carboxamide |
| 375 | 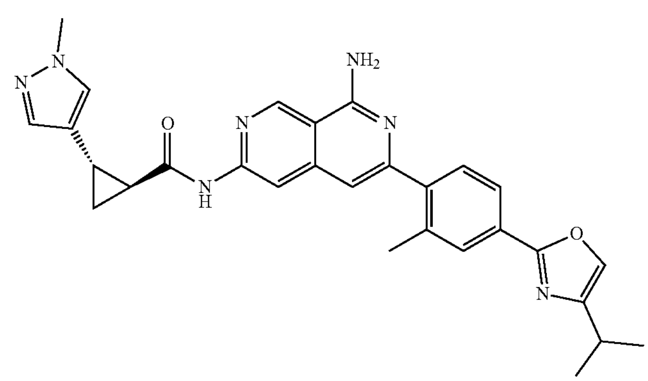 [SMILES: Cc1cc(-c2nc(C(C)C)co2)ccc1-c1cc2cc(NC(=O)[C@H]3C[C@@H]3c3cnn(C)c3)ncc2c(N)n1] | (1S,2S)-N-(8-amino-6-(4-(4-isopropyloxazol-2-yl)-2-methylphenyl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 376 | 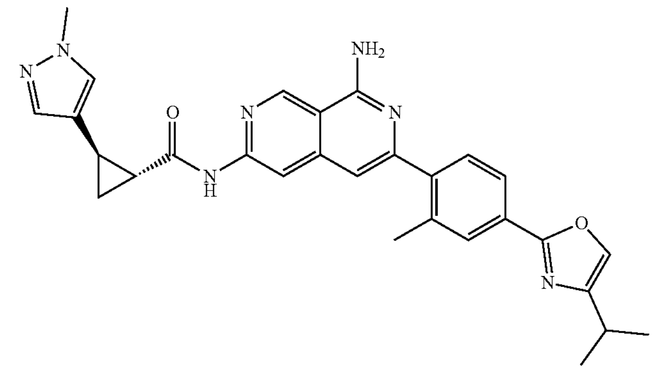 [SMILES: Cc1cc(-c2nc(C(C)C)co2)ccc1-c1cc2cc(NC(=O)[C@@H]3C[C@H]3c3cnn(C)c3)ncc2c(N)n1] | (1R,2R)-N-(8-amino-6-(4-(4-isopropyloxazol-2-yl)-2-methylphenyl)-2,7-naphthyridin-3-yl)-2-(1-methyl-1H-pyrazol-4-yl)cyclopropane-1-carboxamide |
| 377 | 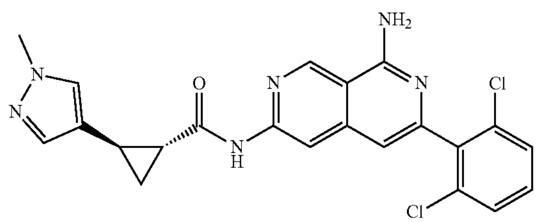 [SMILES: Cn1cc([C@@H]2C[C@H]2C(=O)Nc2cc3cc(-c4c(Cl)cccc4Cl)nc(N)c3cn2)cn1] | (1R,2R)-N-(8-amino-6-(2,6-dichlorophenyl)-2,7-naphthyridin-3-yl)-2-(1-methyl-1H-pyrazol-4-yl)cyclopropane-1-carboxamide |
| 378 | 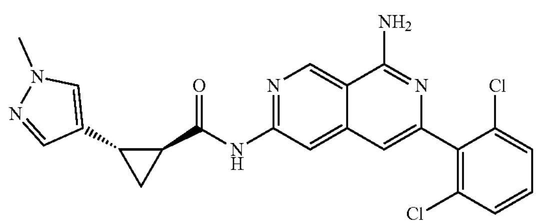 | (1S,2S)-N-(8-amino-6-(2,6-dichlorophenyl)-2,7-naphthyridin-3-yl)-2-(1-methyl-1H-pyrazol-4-yl)cyclopropane-1-carboxamide |
| 379 | 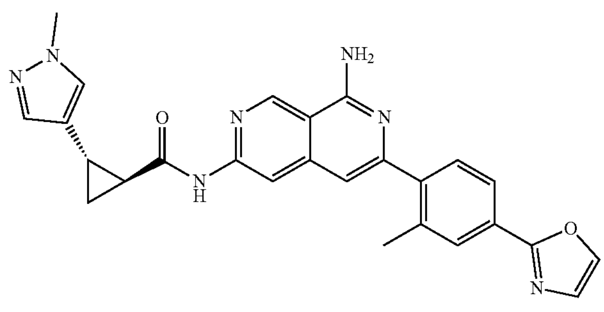 [SMILES: Cc1cc(-c2ncco2)ccc1-c1cc2cc(NC(=O)[C@H]3C[C@@H]3c3cnn(C)c3)ncc2c(N)n1] | (1S,2S)-N-(8-amino-6-(2-methyl-4-(oxazol-2-yl)phenyl)-2,7-naphthyridin-3-yl)-2-(1-methyl-1H-pyrazol-4-yl)cyclopropane-1-carboxamide |
| 380 | 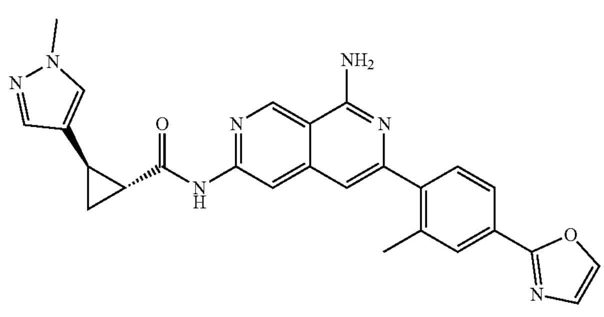 [SMILES: Cc1cc(-c2ncco2)ccc1-c1cc2cc(NC(=O)[C@@H]3C[C@H]3c3cnn(C)c3)ncc2c(N)n1] | (1R,2R)-N-(8-amino-6-(2-methyl-4-(oxazol-2-yl)phenyl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 381 | 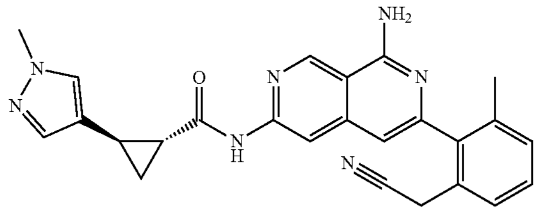 [SMILES: Cc1cccc(CC#N)c1-c1cc2cc(NC(=O)[C@@H]3C[C@H]3c3cnn(C)c3)ncc2c(N)n1] | (1R,2R)-N-(8-amino-6-(2-(cyanomethyl)-6-methylphenyl)-2,7-naphthyridin-3-yl)-2-(1-methyl-1H-pyrazol-4-yl)cyclopropane-1-carboxamide |
| 382 | 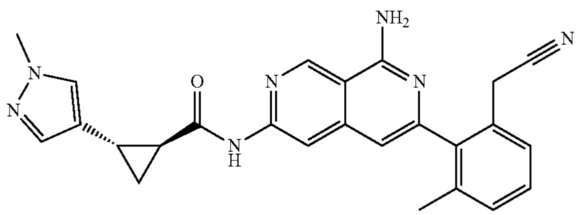 | trans-N-(8-amino-6-(2-(cyanomethyl)-6-methylphenyl)-2,7-naphthyridin-3-yl)-2-(1-methyl-1H-pyrazol-4-yl)cyclopropane-1-carboxamide |
| 383 | 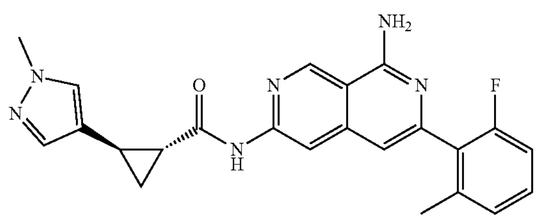 [SMILES: Cc1cccc(F)c1-c1cc2cc(NC(=O)[C@@H]3C[C@H]3c3cnn(C)c3)ncc2c(N)n1] | (1R,2R)-N-(8-amino-6-(2-fluoro-6-methylphenyl)-2,7-naphthyridin-3-yl)-2-(1-methyl-1H-pyrazol-4-yl)cyclopropane-1-carboxamide |
| 384 | 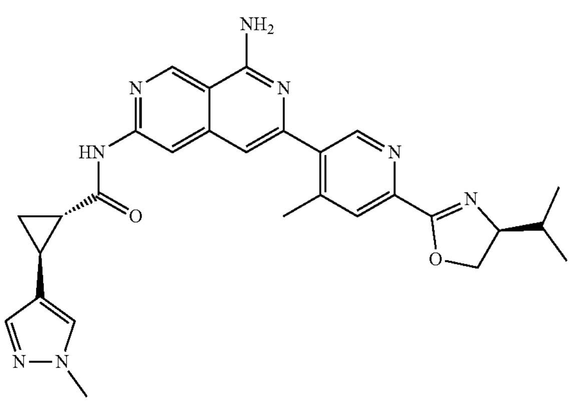 | trans-N-(8-amino-6-(6-((S)-4-isopropyl-4,5-dihydrooxazol-2-yl)-4-methylpyridin-3-yl)-2,7-naphthyridin-3-yl)-2-(1-methyl-1H-pyrazol-4-yl)cyclopropane-1-carboxamide |

| Cmpd. No. | Structure | Name |
|---|---|---|
| | | |
| 385 | 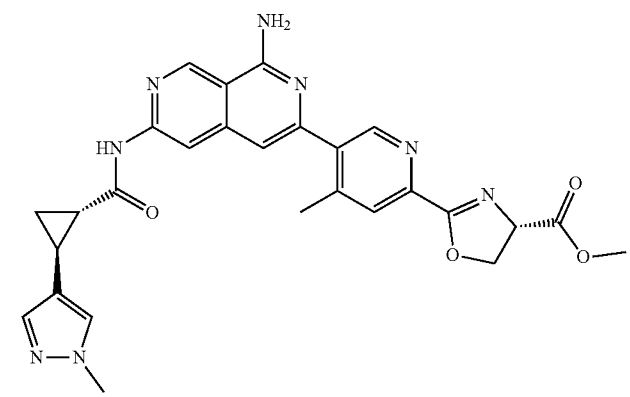 [SMILES: COC(=O)[C@@H]1COC(c2cc(C)c(-c3cc4cc(NC(=O)[C@H]5C[C@@H]5c5cnn(C)c5)ncc4c(N)n3)cn2)=N1] | methyl (S)-2-(5-(1-amino-6-((1S,2S)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate |
| 386 | 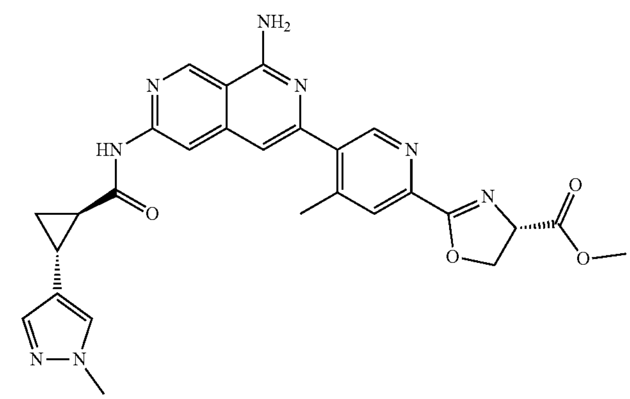 [SMILES: COC(=O)[C@@H]1COC(c2cc(C)c(-c3cc4cc(NC(=O)[C@@H]5C[C@H]5c5cnn(C)c5)ncc4c(N)n3)cn2)=N1] | methyl (S)-2-(5-(1-amino-6-((1R,2R)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate |
| 387 | 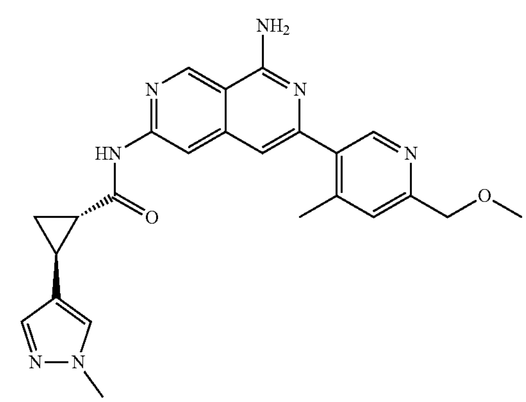 [SMILES: COCc1cc(C)c(-c2cc3cc(NC(=O)[C@H]4C[C@@H]4c4cnn(C)c4)ncc3c(N)n2)cn1] | (1S,2S)-N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 388 | 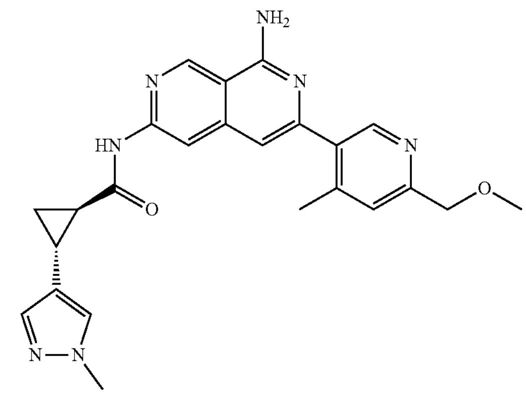 [SMILES: COCc1cc(C)c(-c2cc3cc(NC(=O)[C@@H]4C[C@H]4c4cnn(C)c4)ncc3c(N)n2)cn1] | (1R,2R)-N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide |
| 389 | 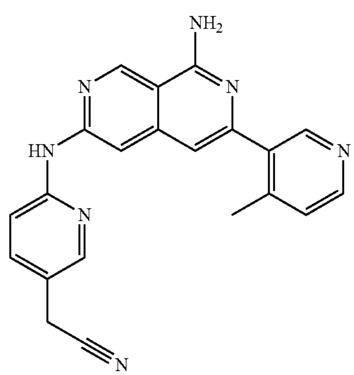 [SMILES: Cc1ccncc1-c1cc2cc(Nc3ccc(CC#N)cn3)ncc2c(N)n1] | 2-[6-[[8-amino-6-(4-methyl-3-pyridyl)-2,7-naphthyridin-3-yl]amino]-3-pyridyl]acetonitrile |
| 391 | 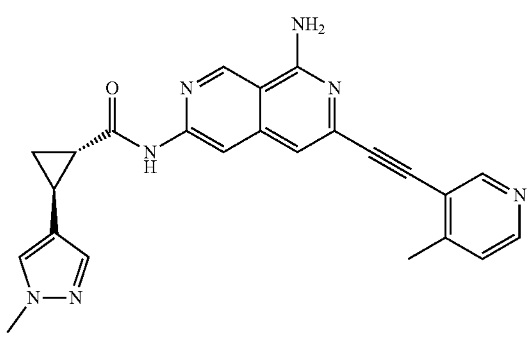 [SMILES: Cc1ccncc1C#Cc1cc2cc(NC(=O)[C@H]3C[C@@H]3c3cnn(C)c3)ncc2c(N)n1] | (1S,2S)-N-(8-amino-6-((4-methylpyridin-3-yl)ethynyl)-2,7-naphthyridin-3-yl)-2-(1-methyl-1H-pyrazol-4-yl)cyclopropane-1-carboxamide |
| 392 | 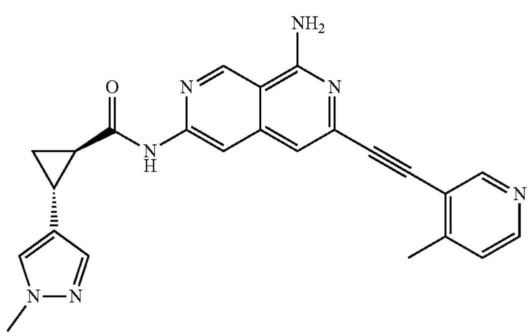 [SMILES: Cc1ccncc1C#Cc1cc2cc(NC(=O)[C@@H]3C[C@H]3c3cnn(C)c3)ncc2c(N)n1] | (1R,2R)-N-(8-amino-6-((4-methylpyridin-3-yl)ethynyl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 393 | 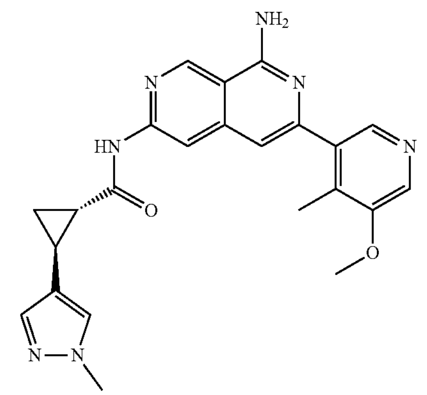 [SMILES: COc1cncc(-c2cc3cc(NC(=O)[C@H]4C[C@@H]4c4cnn(C)c4)ncc3c(N)n2)c1C] | (1S,2S)-N-(8-amino-6-(5-methoxy-4-methylpyridin-3-yl)-2,7-naphthyridin-3-yl)-2-(1-methyl-1H-pyrazol-4-yl)cyclopropane-1-carboxamide |
| 394 | 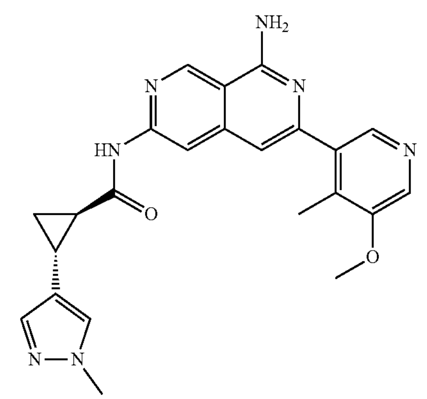 [SMILES: COc1cncc(-c2cc3cc(NC(=O)[C@@H]4C[C@H]4c4cnn(C)c4)ncc3c(N)n2)c1C] | (1R,2R)-N-(8-amino-6-(5-methoxy-4-methylpyridin-3-yl)-2,7-naphthyridin-3-yl)-2-(1-methyl-1H-pyrazol-4-yl)cyclopropane-1-carboxamide |
| 395 | 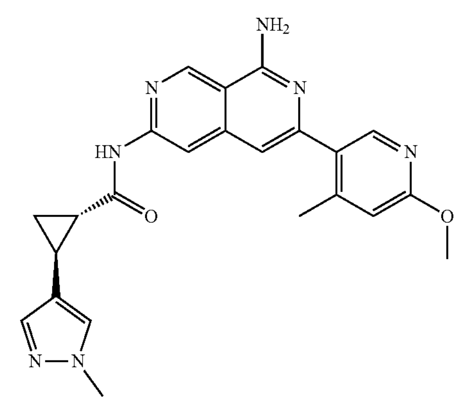 [SMILES: COc1cc(C)c(-c2cc3cc(NC(=O)[C@H]4C[C@@H]4c4cnn(C)c4)ncc3c(N)n2)cn1] | (1S,2S)-N-(8-amino-6-(6-methoxy-4-methylpyridin-3-yl)-2,7-naphthyridin-3-yl)-2-(1-methyl-1H-pyrazol-4-yl)cyclopropane-1-carboxamide |
| 396 | 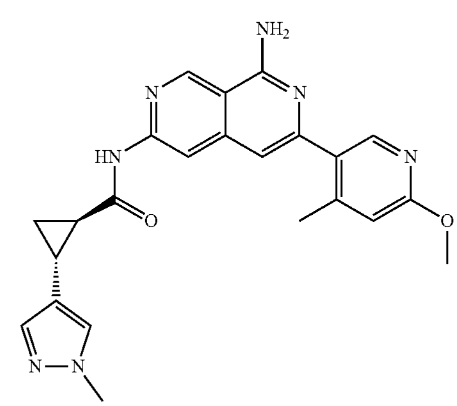 [SMILES: COc1cc(C)c(-c2cc3cc(NC(=O)[C@@H]4C[C@H]4c4cnn(C)c4)ncc3c(N)n2)cn1] | (1R,2R)-N-(8-amino-6-(6-methoxy-4-methylpyridin-3-yl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 397 | 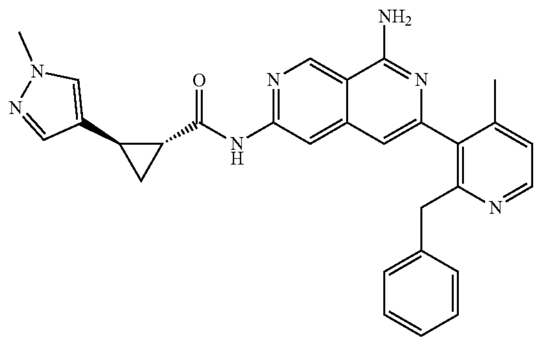 [SMILES: Cc1ccnc(Cc2ccccc2)c1-c1cc2cc(NC(=O)[C@@H]3C[C@H]3c3cnn(C)c3)ncc2c(N)n1] | (1R,2R)-N-(8-amino-6-(2-benzyl-4-methylpyridin-3-yl)-2,7-naphthyridin-3-yl)-2-(1-methyl-1H-pyrazol-4-yl)cyclopropane-1-carboxamide |
| 398 | 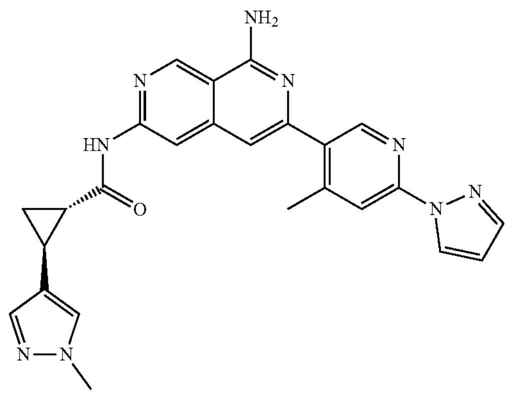 [SMILES: Cc1cc(-n2cccn2)ncc1-c1cc2cc(NC(=O)[C@H]3C[C@@H]3c3cnn(C)c3)ncc2c(N)n1] | (1S,2S)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide |
| 399 | 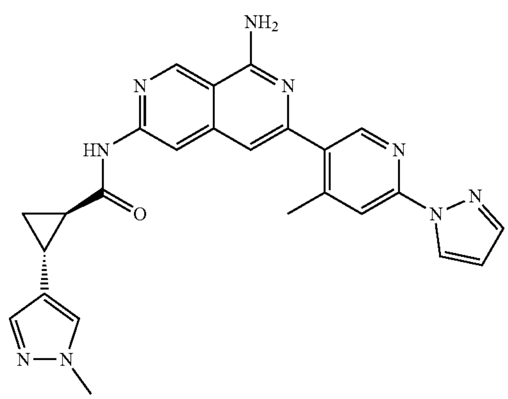 [SMILES: Cc1cc(-n2cccn2)ncc1-c1cc2cc(NC(=O)[C@@H]3C[C@H]3c3cnn(C)c3)ncc2c(N)n1] | (1R,2R)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide |
| 400 | 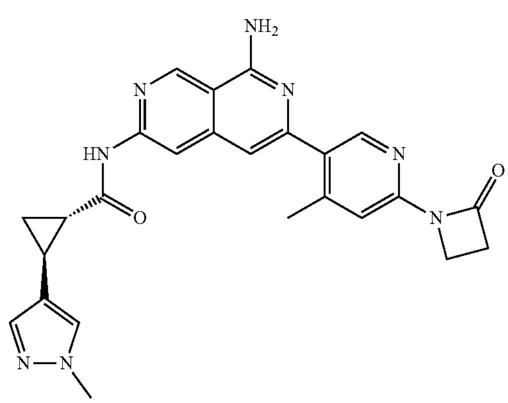 [SMILES: Cc1cc(N2CCC2=O)ncc1-c1cc2cc(NC(=O)[C@H]3C[C@@H]3c3cnn(C)c3)ncc2c(N)n1] | (1S,2S)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 401 | 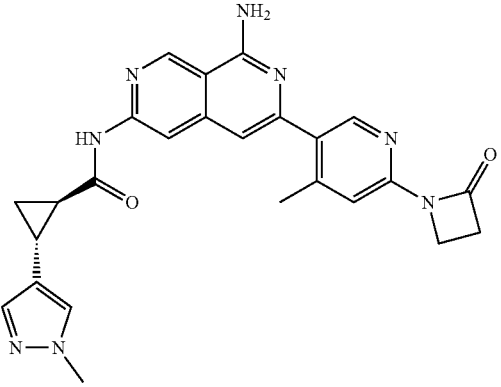 [SMILES: Cc1cc(N2CCC2=O)ncc1-c1cc2cc(NC(=O)[C@@H]3C[C@H]3c3cnn(C)c3)ncc2c(N)n1] | (1R,2R)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide |
| 402 | 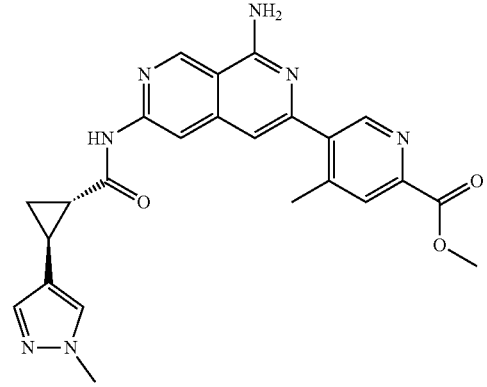 [SMILES: COC(=O)c1cc(C)c(-c2cc3cc(NC(=O)[C@H]4C[C@@H]4c4cnn(C)c4)ncc3c(N)n2)cn1] | methyl 5-(1-amino-6-((1S,2S)-2-(1-methyl-1H-pyrazol-4-yl)cyclopropane-1-carboxamido)-2,7-naphthyridin-3-yl)-4-methylpicolinate |
| 403 | 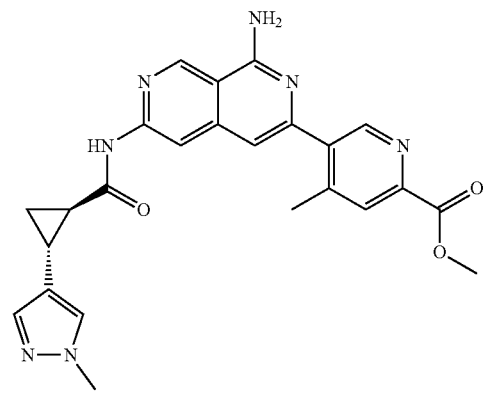 [SMILES: COC(=O)c1cc(C)c(-c2cc3cc(NC(=O)[C@@H]4C[C@H]4c4cnn(C)c4)ncc3c(N)n2)cn1] | methyl 5-(1-amino-6-((1R,2R)-2-(1-methyl-1H-pyrazol-4-yl)cyclopropane-1-carboxamido)-2,7-naphthyridin-3-yl)-4-methylpicolinate |
| 404 | 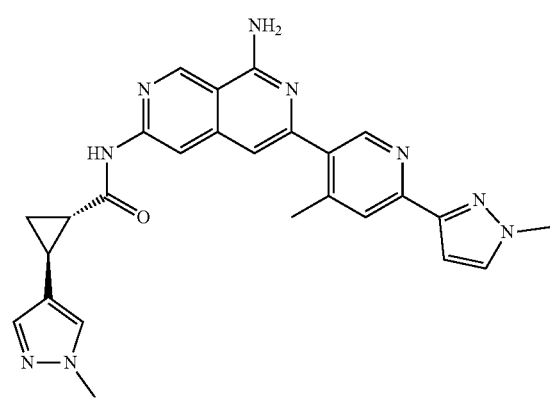 [SMILES: Cc1cc(-c2ccn(C)n2)ncc1-c1cc2cc(NC(=O)[C@H]3C[C@@H]3c3cnn(C)c3)ncc2c(N)n1] | (1S,2S)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 405 | 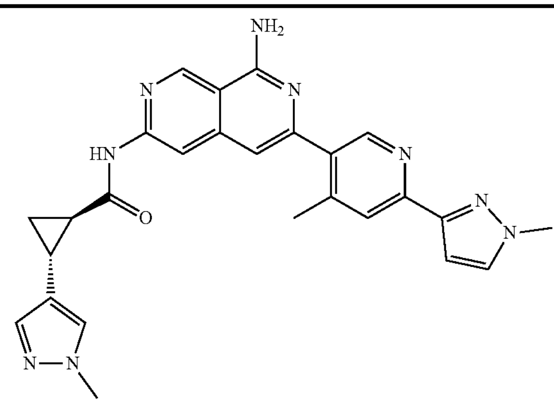 | (1R,2R)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide |
| 406 | 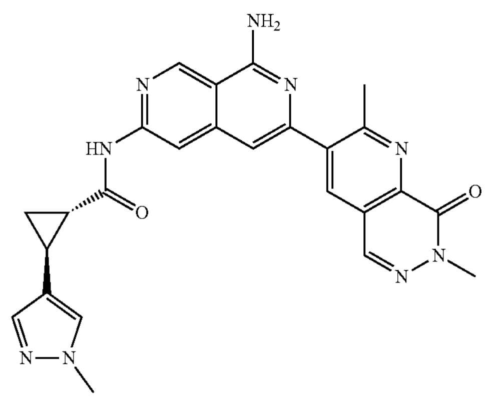 | (1S,2S)-N-(8-amino-6-(2,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| 407 | 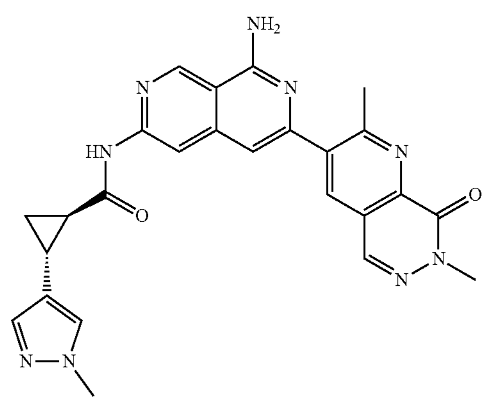 [SMILES: Cc1nc2c(=O)n(C)ncc2cc1-c1cc2cc(NC(=O)[C@@H]3C[C@H]3c3cnn(C)c3)ncc2c(N)n1] | (1R,2R)-N-(8-amino-6-(2,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| 408 | 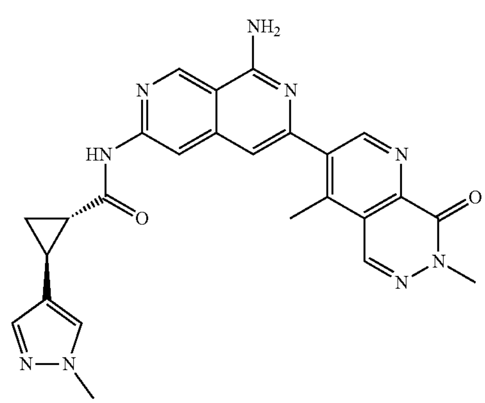 [SMILES: Cc1c(-c2cc3cc(NC(=O)[C@H]4C[C@@H]4c4cnn(C)c4)ncc3c(N)n2)cnc2c(=O)n(C)ncc12] | (1S,2S)-N-(8-amino-6-(4,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 409 | 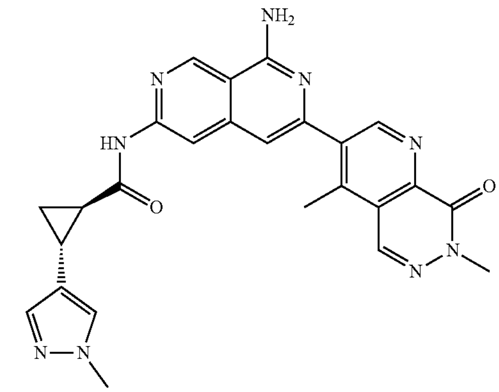 [SMILES: Cc1c(-c2cc3cc(NC(=O)[C@@H]4C[C@H]4c4cnn(C)c4)ncc3c(N)n2)cnc2c(=O)n(C)ncc12] | (1R,2R)-N-(8-amino-6-(4,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| 410 | 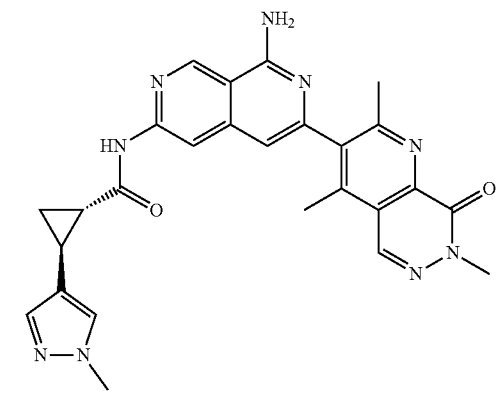 [SMILES: Cc1nc2c(=O)n(C)ncc2c(C)c1-c1cc2cc(NC(=O)[C@H]3C[C@@H]3c3cnn(C)c3)ncc2c(N)n1] | (1S,2S)-N-(8-amino-6-(2,4,7-trimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| 411 | 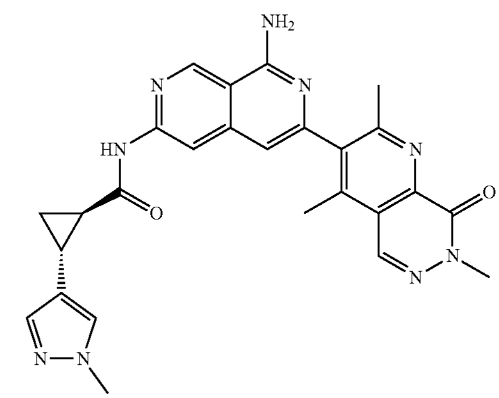 [SMILES: Cc1nc2c(=O)n(C)ncc2c(C)c1-c1cc2cc(NC(=O)[C@@H]3C[C@H]3c3cnn(C)c3)ncc2c(N)n1] | (1R,2R)-N-(8-amino-6-(2,4,7-trimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide |
| 412 | 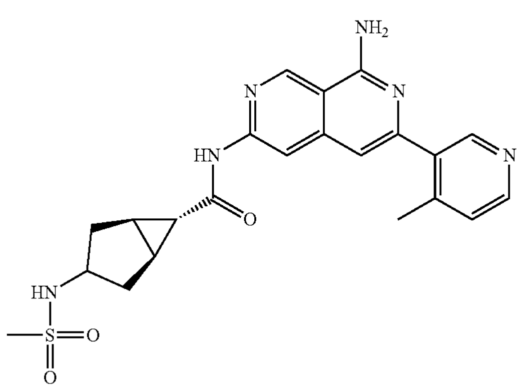 | N-(8-amino-6-(4-methylpyridin-3-yl)-2,7-naphthyridin-3-yl)-3-(methylsulfonamido)bicyclo[3.1.0]hexane-6-carboxamide |

TABLE 2-continued

| Cmpd. No. | Structure | Name |
|---|---|---|
| 413 | 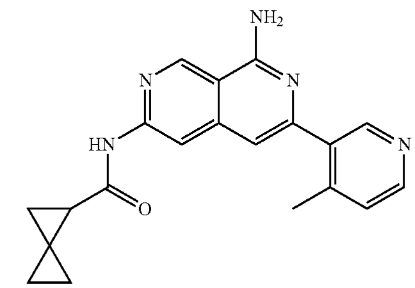 [SMILES: Cc1ccncc1-c1cc2cc(NC(=O)C3CC34CC4)ncc2c(N)n1] | N-(8-amino-6-(4-methylpyridin-3-yl)-2,7-naphthyridin-3-yl)spiro[2.2]pentane-1-carboxamide |
| 414 | 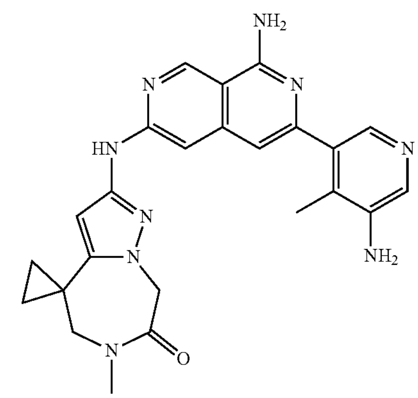 [SMILES: Cc1c(N)cncc1-c1cc2cc(Nc3cc4n(n3)CC(=O)N(C)CC43CC3)ncc2c(N)n1] | 2'-((8-amino-6-(5-amino-4-methylpyridin-3-yl)-2,7-naphthyridin-3-yl)amino)-6'-methyl-5',6'-dihydrospiro[cyclopropane-1,4'-pyrazolo[1,5-d][1,4]diazepin]-7'(8'H)-one |
| 415 | 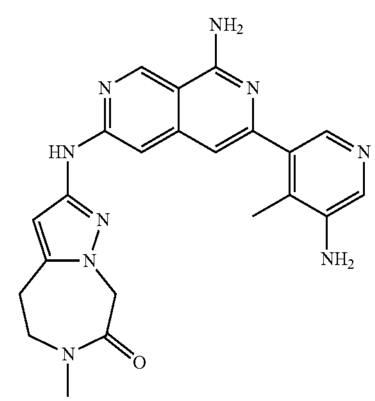 [SMILES: Cc1c(N)cncc1-c1cc2cc(Nc3cc4n(n3)CC(=O)N(C)CC4)ncc2c(N)n1] | 2-((8-amino-6-(5-amino-4-methylpyridin-3-yl)-2,7-naphthyridin-3-yl)amino)-6-methyl-5,6-dihydro-4H-pyrazolo[1,5-d][1,4]diazepin-7(8H)-one |
| 416 | 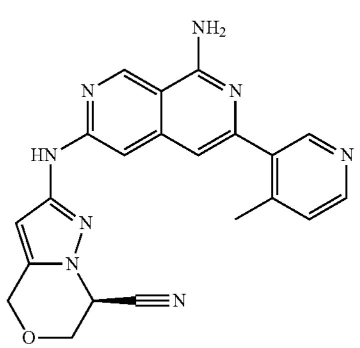 [SMILES: Cc1ccncc1-c1cc2cc(Nc3cc4n(n3)[C@@H](C#N)COC4)ncc2c(N)n1] | (S)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile |

TABLE 2-continued

| Cmpd. No. | Structure | Name |
|---|---|---|
| 417 | 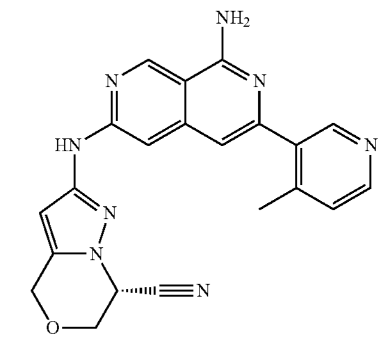 [SMILES: Cc1ccncc1-c1cc2cc(Nc3cc4n(n3)[C@H](C#N)COC4)ncc2c(N)n1] | (R)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile |
| 418 | 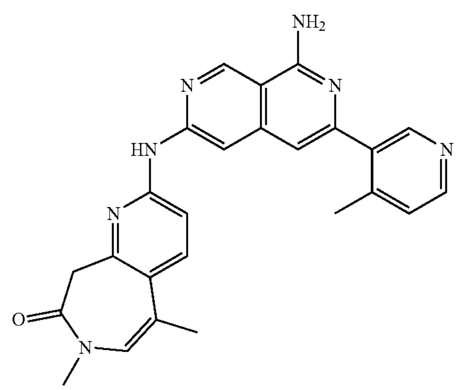 [SMILES: CC1=CN(C)C(=O)Cc2nc(Nc3cc4cc(-c5cnccc5C)nc(N)c4cn3)ccc21] | 2-((8-amino-6-(4-methylpyridin-3-yl)-2,7-naphthyridin-3-yl)amino)-5,7-dimethyl-7,9-dihydro-8H-pyrido[2,3-d]azepin-8-one |
| 419 | | 2-((8-amino-6-(1-(pyridin-2-yloxy)ethyl)-2,7-naphthyridin-3-yl)amino)-6-isopropyl-5,6-dihydro-4H-pyrazolo[1,5-d][1,4]diazepin-7(8H)-one |

TABLE 2-continued

| Cmpd. No. | Structure | Name |
|---|---|---|
| 420 | 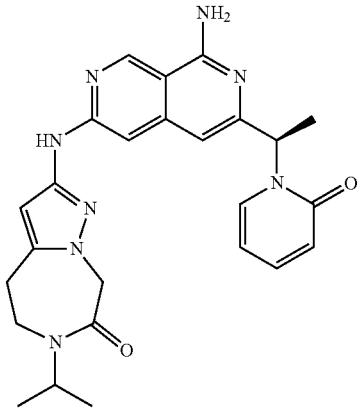 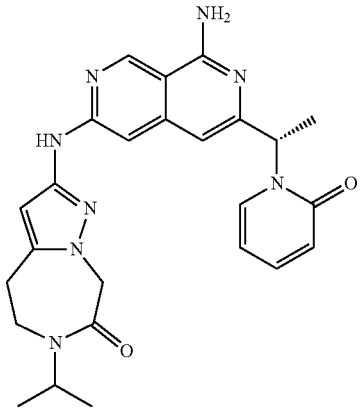 | 2-((8-amino-6-(1-(2-oxopyridin-1(2H)-yl)ethyl)-2,7-naphthyridin-3-yl)amino)-6-isopropyl-5,6-dihydro-4H-pyrazolo[1,5-d][1,4]diazepin-7(8H)-one |
| 421 | 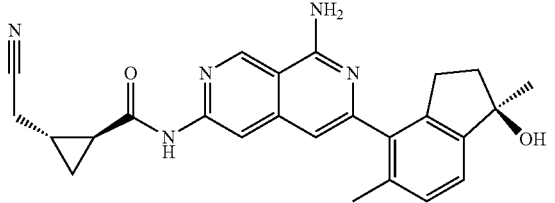 [SMILES: Cc1ccc2c(c1-c1cc3cc(NC(=O)[C@H]4C[C@@H]4CC#N)ncc3c(N)n1)CC[C@@]2(C)O] | (1S,2R)-N-(8-amino-6-((R)-1-hydroxy-1,5-dimethyl-2,3-dihydro-1H-inden-4-yl)-2,7-naphthyridin-3-yl)-2-(cyanomethyl)cyclopropane-1-carboxamide |
| 422 | 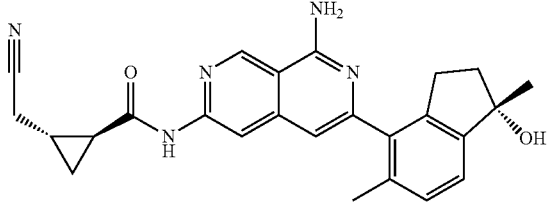 [SMILES: Cc1ccc2c(c1-c1cc3cc(NC(=O)[C@H]4C[C@@H]4CC#N)ncc3c(N)n1)CC[C@]2(C)O] | (1S,2R)-N-(8-amino-6-((S)-1-hydroxy-1,5-dimethyl-2,3-dihydro-1H-inden-4-yl)-2,7-naphthyridin-3-yl)-2-(cyanomethyl)cyclopropane-1-carboxamide |
| 423 | 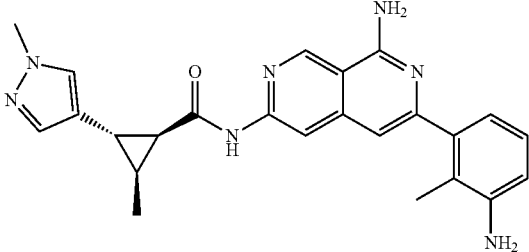 [SMILES: Cc1c(N)cccc1-c1cc2cc(NC(=O)[C@H]3[C@@H](C)[C@@H]3c3cnn(C)c3)ncc2c(N)n1] | (1S,2S,3S)-N-(8-amino-6-(3-amino-2-methylphenyl)-2,7-naphthyridin-3-yl)-2-methyl-3-(1-methyl-1H-pyrazol-4-yl)cyclopropane-1-carboxamide |

TABLE 2-continued

| Cmpd. No. | Structure | Name |
|---|---|---|
| 424 | 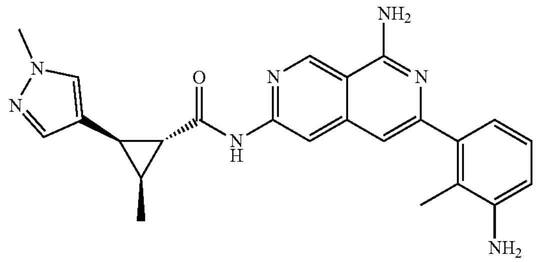 [SMILES: Cc1c(N)cccc1-c1cc2cc(NC(=O)[C@@H]3[C@@H](C)[C@H]3c3cnn(C)c3)ncc2c(N)n1] | (1R,2S,3R)-N-(8-amino-6-(3-amino-2-methylphenyl)-2,7-naphthyridin-3-yl)-2-methyl-3-(1-methyl-1H-pyrazol-4-yl)cyclopropane-1-carboxamide |
| 425 | 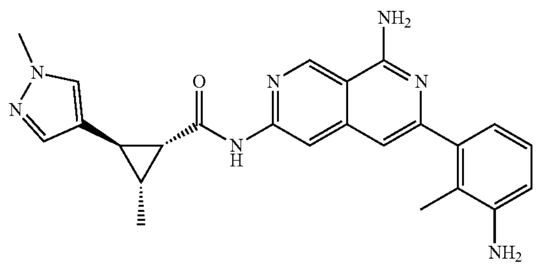 [SMILES: Cc1c(N)cccc1-c1cc2cc(NC(=O)[C@@H]3[C@H](C)[C@H]3c3cnn(C)c3)ncc2c(N)n1] | (1R,2R,3R)-N-(8-amino-6-(3-amino-2-methylphenyl)-2,7-naphthyridin-3-yl)-2-methyl-3-(1-methyl-1H-pyrazol-4-yl)cyclopropane-1-carboxamide |
| 426 | 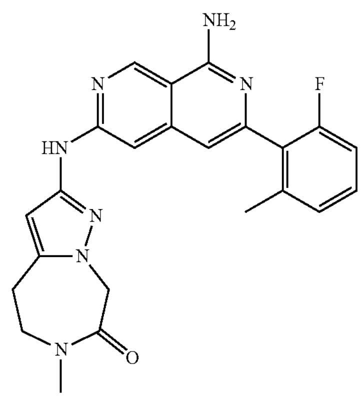 [SMILES: Cc1cccc(F)c1-c1cc2cc(Nc3cc4n(n3)CC(=O)N(C)CC4)ncc2c(N)n1] | 2-((8-amino-6-(2-fluoro-6-methylphenyl)-2,7-naphthyridin-3-yl)amino)-6-methyl-5,6-dihydro-4H-pyrazolo[1,5-d][1,4]diazepin-7(8H)-one |
| 427 | | trans-N-(8-amino-6-(2-benzyl-4-methylpyridin-3-yl)-2,7-naphthyridin-3-yl)-2-(1-methyl-1H-pyrazol-4-yl)cyclopropane-1-carboxamide |
| 428 | 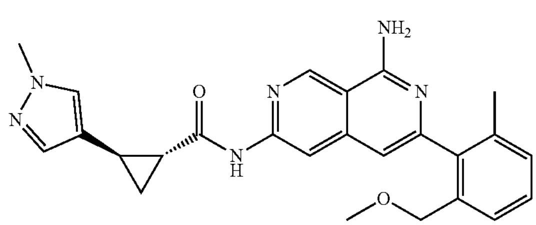 [SMILES: COCc1cccc(C)c1-c1cc2cc(NC(=O)[C@@H]3C[C@H]3c3cnn(C)c3)ncc2c(N)n1] | (1R,2R)-N-(8-amino-6-(2-(methoxymethyl)-6-methylphenyl)-2,7-naphthyridin-3-yl)-2-(1-methyl-1H-pyrazol-4-yl)cyclopropane-1-carboxamide |

TABLE 2-continued

| Cmpd. No. | Structure | Name |
|---|---|---|
| 429 | 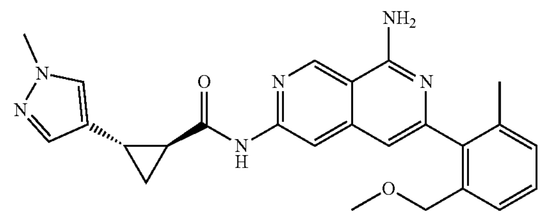 [SMILES: COCc1cccc(C)c1-c1cc2cc(NC(=O)[C@H]3C[C@@H]3c3cnn(C)c3)ncc2c(N)n1] | (1S,2S)-N-(8-amino-6-(2-(methoxymethyl)-6-methylphenyl)-2,7-naphthyridin-3-yl)-2-(1-methyl-1H-pyrazol-4-yl)cyclopropane-1-carboxamide |

TABLE 3

| Cmpd No. | Structure | Name |
|---|---|---|
| 430 | 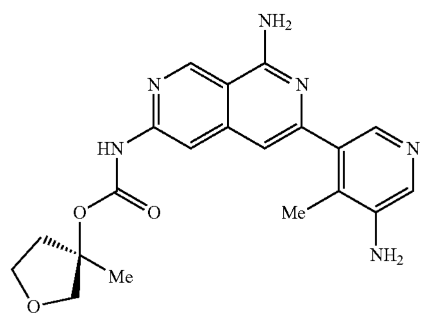 | 3-methyltetrahydrofuran-3-yl (8-amino-6-(5-amino-4-methylpyridin-3-yl)-2,7-naphthyridin-3-yl)carbamate |
| | | 3-methyltetrahydrofuran-3-yl (8-amino-6-(5-amino-4-methylpyridin-3-yl)-2,7-naphthyridin-3-yl)carbamate |
| 431 | 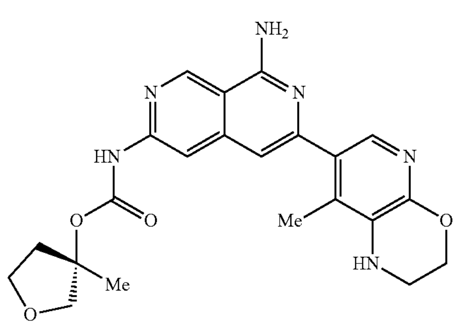 | 3-methyltetrahydrofuran-3-yl (8-amino-6-(8-methyl-2,3-dihydro-1H-pyrido[2,3-b][1,4]oxazin-7-yl)-2,7-naphthyridin-3-yl)carbamate |

TABLE 3-continued

| Cmpd No. | Structure | Name |
|---|---|---|
| | | |
| 432 | 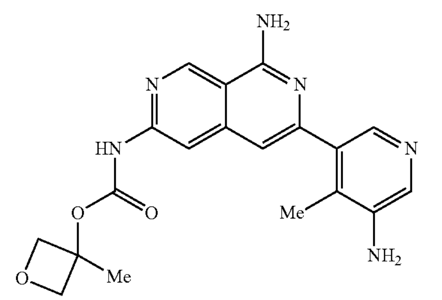 [SMILES: Cc1c(N)cncc1-c1cc2cc(NC(=O)OC3(C)COC3)ncc2c(N)n1] | 3-methyloxetan-3-yl (8-amino-6-(5-amino-4-methylpyridin-3-yl)-2,7-naphthyridin-3-yl)carbamate |
| 433 | 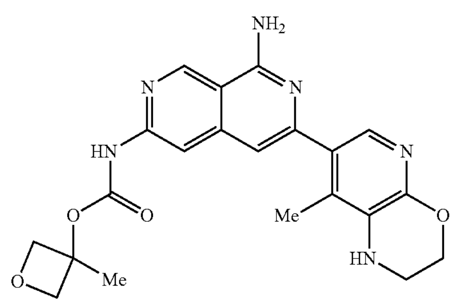 [SMILES: Cc1c(-c2cc3cc(NC(=O)OC4(C)COC4)ncc3c(N)n2)cnc2c1NCCO2] | 3-methyloxetan-3-yl (8-amino-6-(8-methyl-2,3-dihydro-1H-pyrido[2,3-b][1,4]oxazin-7-yl)-2,7-naphthyridin-3-yl)carbamate |
| 434 | 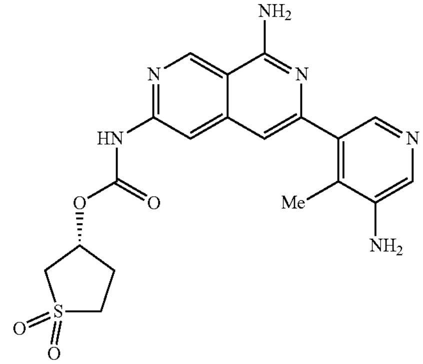 | 1,1-dioxidotetrahydrothiophen-3-yl (8-amino-6-(5-amino-4-methylpyridin-3-yl)-2,7-naphthyridin-3-yl)carbamate |

TABLE 3-continued

| Cmpd No. | Structure | Name |
|---|---|---|
| | | |
| 435 | 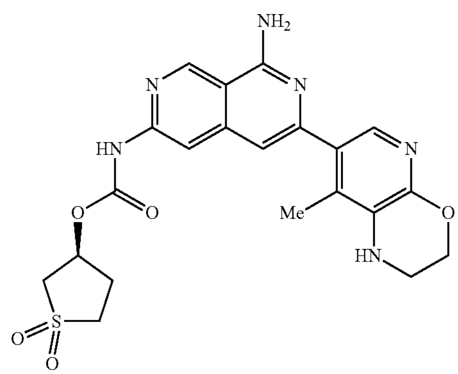 | 1,1-dioxidotetrahydrothiophen-3-yl (8-amino-6-(8-methyl-2,3-dihydro-1H-pyrido[2,3-b][1,4]oxazin-7-yl)-2,7-naphthyridin-3-yl)carbamate |
| | | |
| 436 | 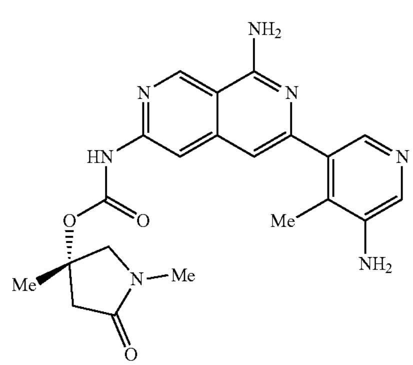 | 1,3-dimethyl-5-oxopyrrolidin-3-yl (8-amino-6-(5-amino-4-methylpyridin-3-yl)-2,7-naphthyridin-3-yl)carbamate |

TABLE 3-continued

| Cmpd No. | Structure | Name |
|---|---|---|
| | | |
| 437 | 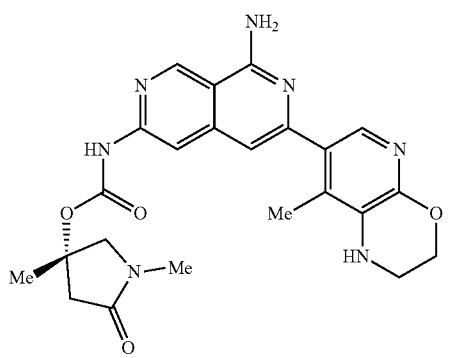 | 1,3-dimethyl-5-oxopyrrolidin-3-yl (8-amino-6-(8-methyl-2,3-dihydro-1H-pyrido[2,3-b][1,4]oxazin-7-yl)-2,7-naphthyridin-3-yl)carbamate |
| 438 | 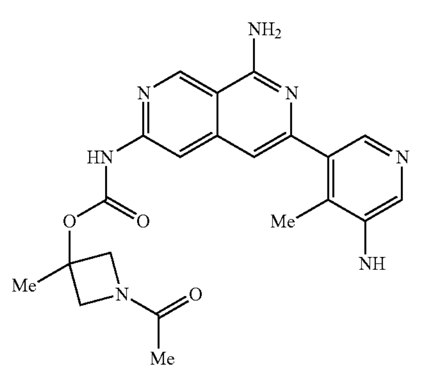 [SMILES: CC(=O)N1CC(C)(OC(=O)Nc2cc3cc(-c4cncc(N)c4C)nc(N)c3cn2)C1] | 1-acetyl-3-methylazetidin-3-yl (8-amino-6-(5-amino-4-methylpyridin-3-yl)-2,7-naphthyridin-3-yl)carbamate |

TABLE 3-continued

| Cmpd No. | Structure | Name |
|---|---|---|
| 439 | 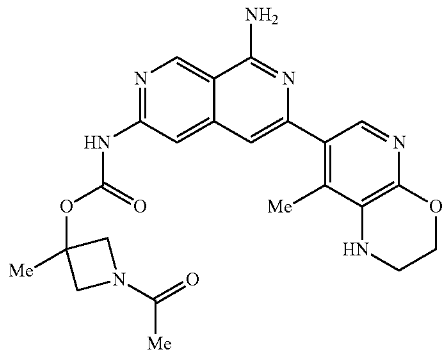 [SMILES: CC(=O)N1CC(C)(OC(=O)Nc2cc3cc(-c4cnc5c(c4C)NCCO5)nc(N)c3cn2)C1] | 1-acetyl-3-methylazetidin-3-yl (8-amino-6-(8-methyl-2,3-dihydro-1H-pyrido[2,3-b][1,4]oxazin-7-yl)-2,7-naphthyridin-3-yl)carbamate |
| 440 | 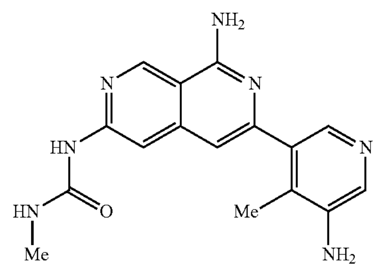 [SMILES: CNC(=O)Nc1cc2cc(-c3cncc(N)c3C)nc(N)c2cn1] | 1-(8-amino-6-(5-amino-4-methylpyridin-3-yl)-2,7-naphthyridin-3-yl)-3-methylurea |
| 441 | 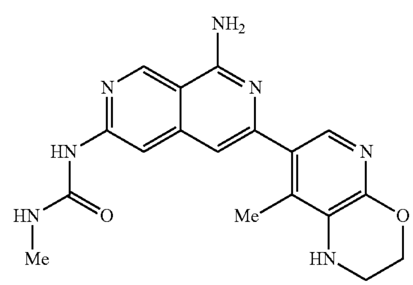 [SMILES: CNC(=O)Nc1cc2cc(-c3cnc4c(c3C)NCCO4)nc(N)c2cn1] | 1-(8-amino-6-(8-methyl-2,3-dihydro-1H-pyrido[2,3-b][1,4]oxazin-7-yl)-2,7-naphthyridin-3-yl)-3-methylurea |
| 442 | 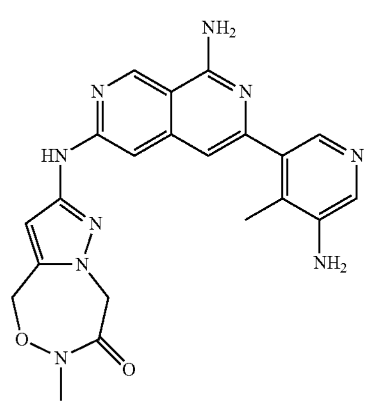 | 2-((8-amino-6-(5-amino-4-methylpyridin-3-yl)-2,7-naphthyridin-3-yl)amino)-6-methyl-4H,6H-pyrazolo[1,5-e][1,2,5]oxadiazepin-7(8H)-one |

TABLE 3-continued

| Cmpd No. | Structure | Name |
|---|---|---|
| 443 | 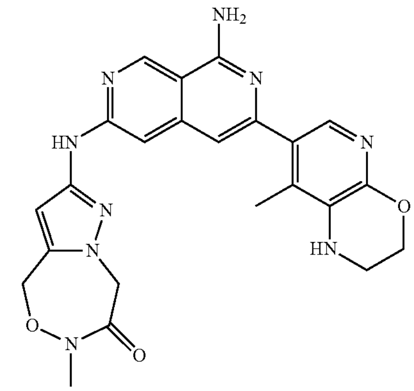 [SMILES: Cc1c(-c2cc3cc(Nc4cc5n(n4)CC(=O)N(C)OC5)ncc3c(N)n2)cnc2c1NCCO2] | 2-((8-amino-6-(8-methyl-2,3-dihydro-1H-pyrido[2,3-b][1,4]oxazin-7-yl)-2,7-naphthyridin-3-yl)amino)-6-methyl-4H,6H-pyrazolo[1,5-e][1,2,5]oxadiazepin-7(8H)-one |
| 444 | 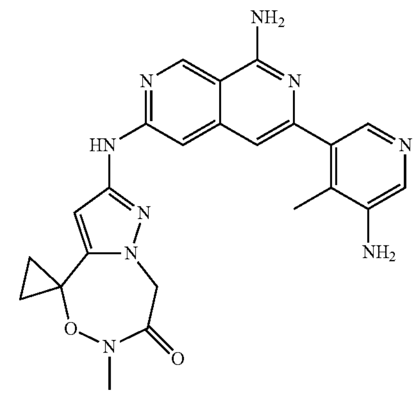 [SMILES: Cc1c(N)cncc1-c1cc2cc(Nc3cc4n(n3)CC(=O)N(C)OC43CC3)ncc2c(N)n1] | 2'-((8-amino-6-(5-amino-4-methylpyridin-3-yl)-2,7-naphthyridin-3-yl)amino)-6'-methyl-6'H-spiro[cyclopropane-1,4'-pyrazolo[1,5-e][1,2,5]oxadiazepin]-7'(8'H)-one |
| 445 | 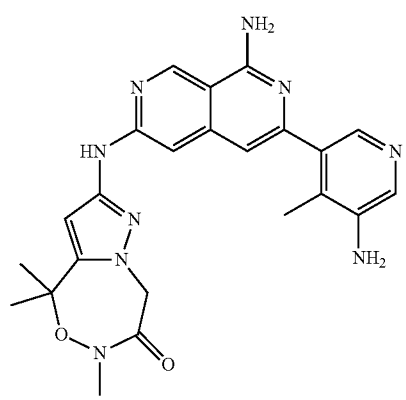 [SMILES: Cc1c(N)cncc1-c1cc2cc(Nc3cc4n(n3)CC(=O)N(C)OC4(C)C)ncc2c(N)n1] | 2-((8-amino-6-(5-amino-4-methylpyridin-3-yl)-2,7-naphthyridin-3-yl)amino)-4,4,6-trimethyl-4H,6H-pyrazolo[1,5-e][1,2,5]oxadiazepin-7(8H)-one |
| 446 | 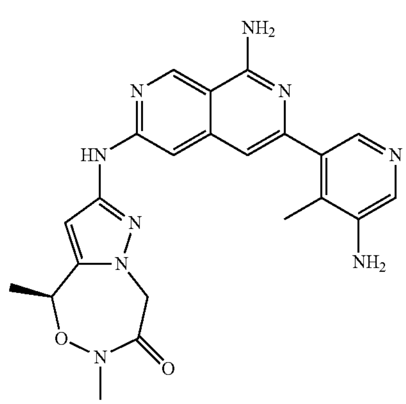 | 2-((8-amino-6-(5-amino-4-methylpyridin-3-yl)-2,7-naphthyridin-3-yl)amino)-4,6-dimethyl-4H,6H-pyrazolo[1,5-e][1,2,5]oxadiazepin-7(8H)-one |

| Cmpd No. | Structure | Name |
|---|---|---|
| | 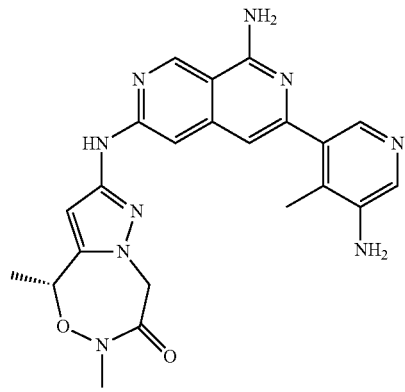 | |
| 447 | 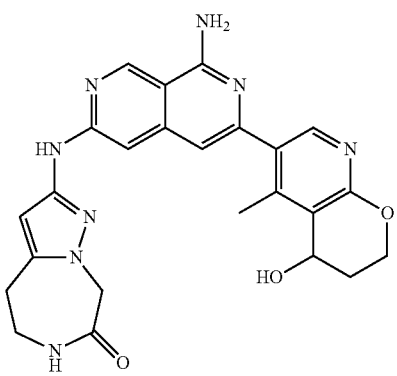 | 2-((8-amino-6-(4-hydroxy-5-methyl-3,4-dihydro-2H-pyrano[2,3-b]pyridin-6-yl)-2,7-naphthyridin-3-yl)amino)-5,6-dihydro-4H-pyrazolo[1,5-d][1,4]diazepin-7(8H)-one |
| | 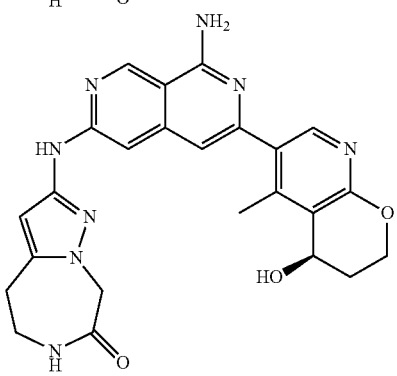 | |
| | 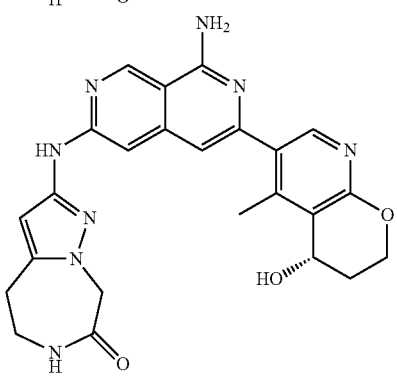 | |

US 11,034,692 B1
TABLE 3-continued
| Cmpd No. | Structure | Name |
|---|---|---|
| 448 | 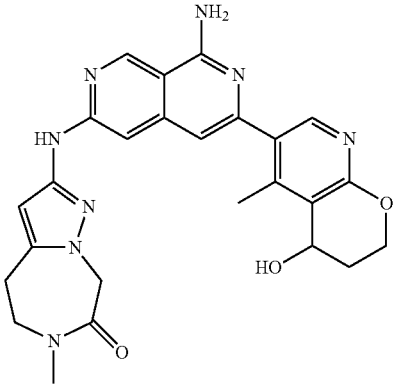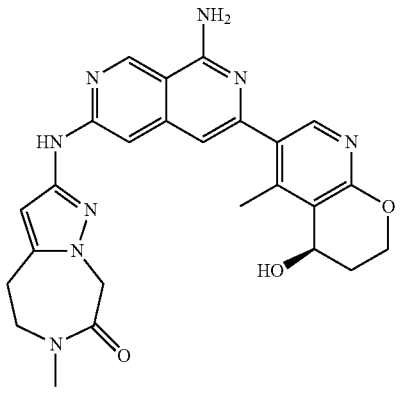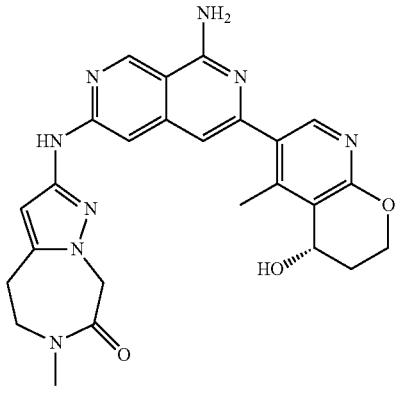 | 2-((8-amino-6-(4-hydroxy-5-methyl-3,4-dihydro-2H-pyrano[2,3-b]pyridin-6-yl)-2,7-naphthyridin-3-yl)amino)-6-methyl-5,6-dihydro-4H-pyrazolo[1,5-d][1,4]diazepin-7(8H)-one |
| 449 | 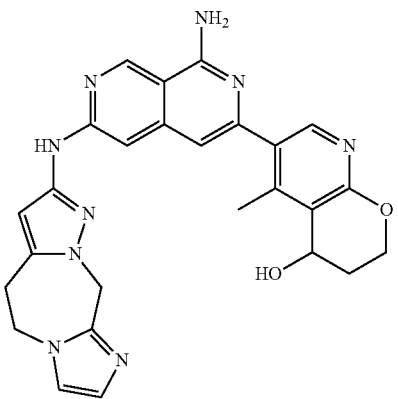 | 6-(1-amino-6-((5,6-dihydro-11H-imidazo[1,2-a]pyrazolo[1,5-d][1,4]diazepin-8-yl)amino)-2,7-naphthyridin-3-yl)-5-methyl-3,4-dihydro-2H-pyrano[2,3-b]pyridin-4-ol |

TABLE 3-continued

| Cmpd No. | Structure | Name |
|---|---|---|
| | | |
| | | |
| 450 | 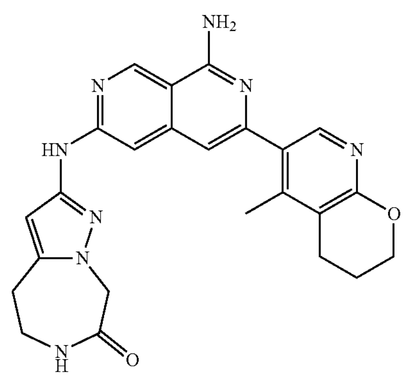 [SMILES: Cc1c(-c2cc3cc(Nc4cc5n(n4)CC(=O)NCC5)ncc3c(N)n2)cnc2c1CCCO2] | 2-((8-amino-6-(5-methyl-3,4-dihydro-2H-pyrano[2,3-b]pyridin-6-yl)-2,7-naphthyridin-3-yl)amino)-5,6-dihydro-4H-pyrazolo[1,5-d][1,4]diazepin-7(8H)-one |
| 451 | 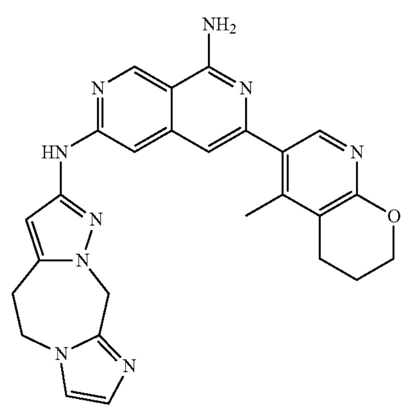 [SMILES: Cc1c(-c2cc3cc(Nc4cc5n(n4)Cc4nccn4CC5)ncc3c(N)n2)cnc2c1CCCO2] | N6-(5,6-dihydro-11H-imidazo[1,2-a]pyrazolo[1,5-d][1,4]diazepin-8-yl)-3-(5-methyl-3,4-dihydro-2H-pyrano[2,3-b]pyridin-6-yl)-2,7-naphthyridine-1,6-diamine |

TABLE 3-continued

| Cmpd No. | Structure | Name |
|---|---|---|
| 452 | 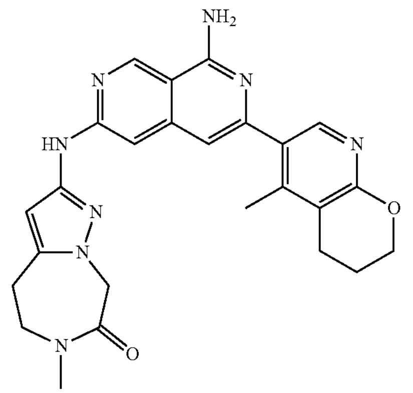 [SMILES: Cc1c(-c2cc3cc(Nc4cc5n(n4)CC(=O)N(C)CC5)ncc3c(N)n2)cnc2c1CCCO2] | 2-((8-amino-6-(5-methyl-3,4-dihydro-2H-pyrano[2,3-b]pyridin-6-yl)-2,7-naphthyridin-3-yl)amino)-6-methyl-5,6-dihydro-4H-pyrazolo[1,5-d][1,4]diazepin-7(8H)-one |
| 453 | | 2-((8-amino-6-(4-fluoro-5-methyl-3,4-dihydro-2H-pyrano[2,3-b]pyridin-6-yl)-2,7-naphthyridin-3-yl)amino)-5,6-dihydro-4H-pyrazolo[1,5-d][1,4]diazepin-7(8H)-one |

TABLE 3-continued
| Cmpd No. | Structure | Name |
|---|---|---|
| 454 | 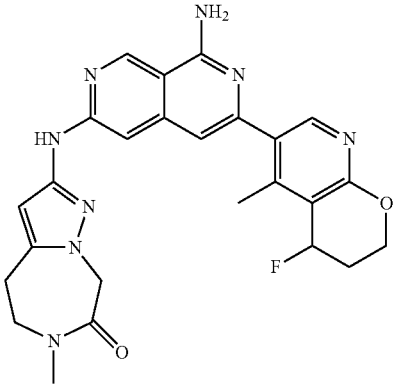 | 2-((8-amino-6-(4-fluoro-5-methyl-3,4-dihydro-2H-pyrano[2,3-b]pyridin-6-yl)-2,7-naphthyridin-3-yl)amino)-6-methyl-5,6-dihydro-4H-pyrazolo[1,5-d][1,4]diazepin-7(8H)-one |
|  | 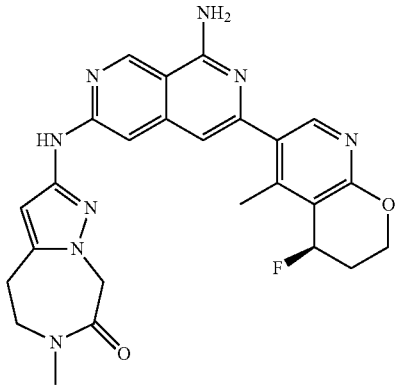 |  |
|  | 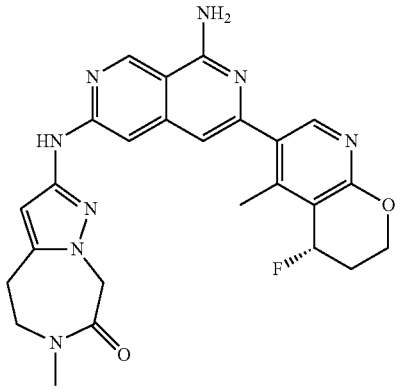 |  |
| 455 | 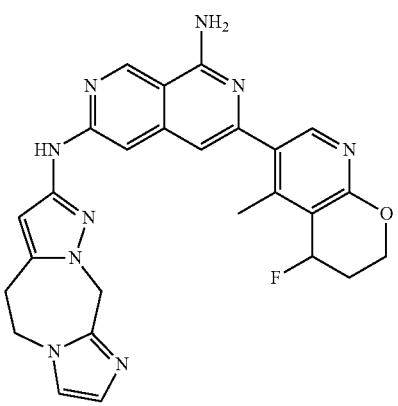 | N6-(5,6-dihydro-11H-imidazo[1,2-a]pyrazolo[1,5-d][1,4]diazepin-8-yl)-3-(4-fluoro-5-methyl-3,4-dihydro-2H-pyrano[2,3-b]pyridin-6-yl)-2,7-naphthyridine-1,6-diamine |

TABLE 3-continued

| Cmpd No. | Structure | Name |
|---|---|---|
| 456 | 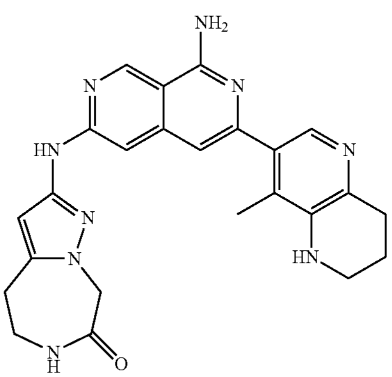 [SMILES: Cc1c(-c2cc3cc(Nc4cc5n(n4)CC(=O)NCC5)ncc3c(N)n2)cnc2c1NCCC2] | 2-((8-amino-6-(4-methyl-5,6,7,8-tetrahydro-1,5-naphthyridin-3-yl)-2,7-naphthyridin-3-yl)amino)-5,6-dihydro-4H-pyrazolo[1,5-d][1,4]diazepin-7(8H)-one |
| 457 | 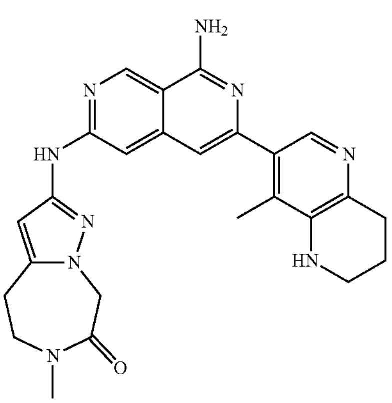 [SMILES: Cc1c(-c2cc3cc(Nc4cc5n(n4)CC(=O)N(C)CC5)ncc3c(N)n2)cnc2c1NCCC2] | 2-((8-amino-6-(4-methyl-5,6,7,8-tetrahydro-1,5-naphthyridin-3-yl)-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 458 | 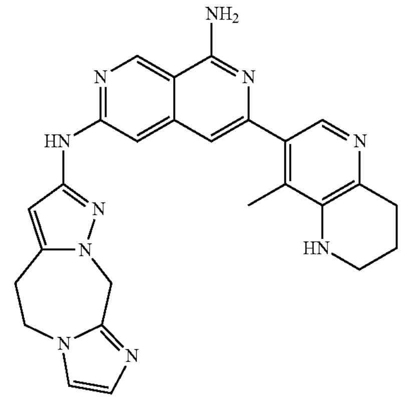 [SMILES: Cc1c(-c2cc3cc(Nc4cc5n(n4)Cc4nccn4CC5)ncc3c(N)n2)cnc2c1NCCC2] | N6-(5,6-dihydro-11H-imidazo[1,2-a]pyrazolo[1,5-d][1,4]diazepin-8-yl)-3-(4-methyl-5,6,7,8-tetrahydro-1,5-naphthyridin-3-yl)-2,7-naphthyridine-1,6-diamine |
| 459 | 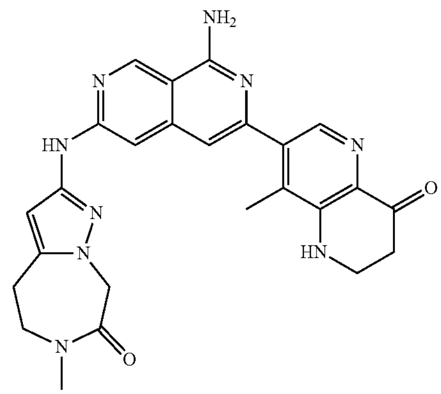 [SMILES: Cc1c(-c2cc3cc(Nc4cc5n(n4)CC(=O)N(C)CC5)ncc3c(N)n2)cnc2c1NCCC2=O] | 2-((8-amino-6-(4-methyl-8-oxo-5,6,7,8-tetrahydro-1,5-naphthyridin-3-yl)-2,7-naphthyridin-3-yl)amino)-6-methyl-5,6-dihydro-4H-pyrazolo[1,5-d][1,4]diazepin-7(8H)-one |
| 460 | 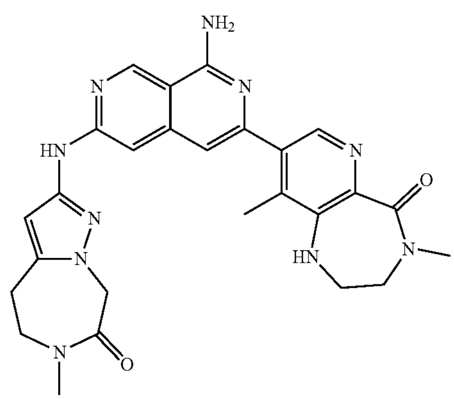 [SMILES: Cc1c(-c2cc3cc(Nc4cc5n(n4)CC(=O)N(C)CC5)ncc3c(N)n2)cnc2c1NCCN(C)C2=O] | 8-(1-amino-6-((6-methyl-7-oxo-5,6,7,8-tetrahydro-4H-pyrazolo[1,5-d][1,4]diazepin-2-yl)amino)-2,7-naphthyridin-3-yl)-4,9-dimethyl-1,2,3,4-tetrahydro-5H-pyrido[3,2-e][1,4]diazepin-5-one |
| 461 | 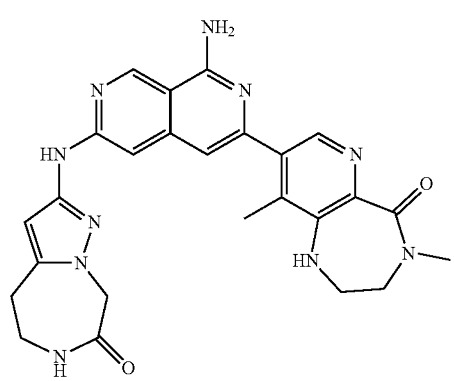 [SMILES: Cc1c(-c2cc3cc(Nc4cc5n(n4)CC(=O)NCC5)ncc3c(N)n2)cnc2c1NCCN(C)C2=O] | 8-(1-amino-6-((7-oxo-5,6,7,8-tetrahydro-4H-pyrazolo[1,5-d][1,4]diazepin-2-yl)amino)-2,7-naphthyridin-3-yl)-4,9-dimethyl-1,2,3,4-tetrahydro-5H-pyrido[3,2-e][1,4]diazepin-5-one |

TABLE 3-continued

| Cmpd No. | Structure | Name |
| --- | --- | --- |
| 462 | 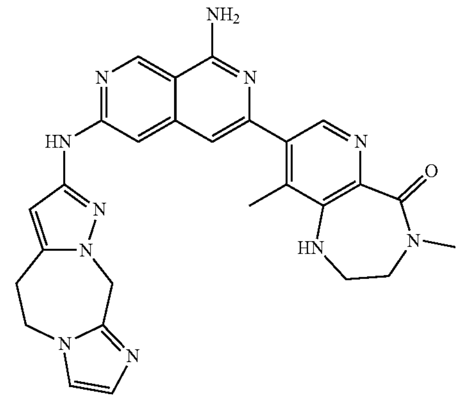 [SMILES: Cc1c(-c2cc3cc(Nc4cc5n(n4)Cc4nccn4CC5)ncc3c(N)n2)cnc2c1NCCN(C)C2=O] | 8-(1-amino-6-((5,6-dihydro-11H-imidazo[1,2-a]pyrazolo[1,5-d][1,4]diazepin-8-yl)amino)-2,7-naphthyridin-3-yl)-4,9-dimethyl-1,2,3,4-tetrahydro-5H-pyrido[3,2-e][1,4]diazepin-5-one |
| 463 | 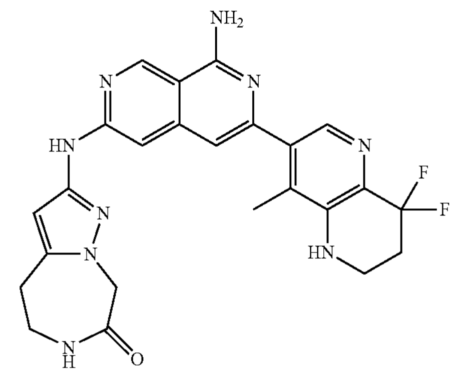 [SMILES: Cc1c(-c2cc3cc(Nc4cc5n(n4)CC(=O)NCC5)ncc3c(N)n2)cnc2c1NCCC2(F)F] | 2-((8-amino-6-(8,8-difluoro-4-methyl-5,6,7,8-tetrahydro-1,5-naphthyridin-3-yl)-2,7-naphthyridin-3-yl)amino)-5,6-dihydro-4H-pyrazolo[1,5-d][1,4]diazepin-7(8H)-one |
| 464 | 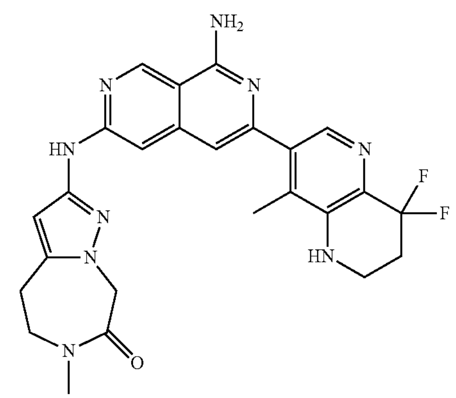 [SMILES: Cc1c(-c2cc3cc(Nc4cc5n(n4)CC(=O)N(C)CC5)ncc3c(N)n2)cnc2c1NCCC2(F)F] | 2-((8-amino-6-(8,8-difluoro-4-methyl-5,6,7,8-tetrahydro-1,5-naphthyridin-3-yl)-2,7-naphthyridin-3-yl)amino)-6-methyl-5,6-dihydro-4H-pyrazolo[1,5-d][1,4]diazepin-7(8H)-one |
| 465 | 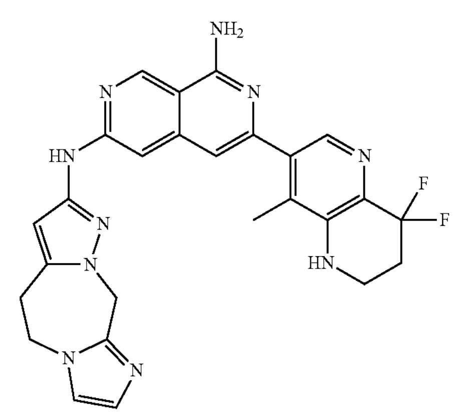 [SMILES: Cc1c(-c2cc3cc(Nc4cc5n(n4)Cc4nccn4CC5)ncc3c(N)n2)cnc2c1NCCC2(F)F] | 3-(8,8-difluoro-4-methyl-5,6,7,8-tetrahydro-1,5-naphthyridin-3-yl)-N6-(5,6-dihydro-11H-imidazo[1,2-a]pyrazolo[1,5-d][1,4]diazepin-8-yl)-2,7-naphthyridine-1,6-diamine |

TABLE 3-continued
| Cmpd No. | Structure | Name |
|---|---|---|
| 466 | 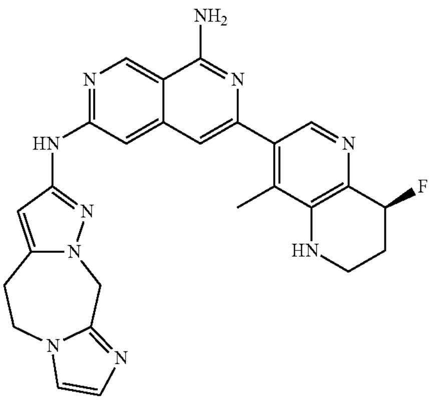 | N6-(5,6-dihydro-11H-imidazo[1,2-a]pyrazolo[1,5-d][1,4]diazepin-8-yl)-3-(8-fluoro-4-methyl-5,6,7,8-tetrahydro-1,5-naphthyridin-3-yl)-2,7-naphthyridine-1,6-diainine |
| 467 | 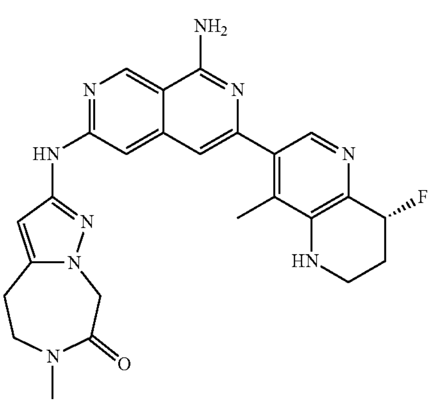 | 2-((8-amino-6-(8-fluoro-4-methyl-5,6,7,8-tetrahydro-1,5-naphthyridin-3-yl)-2,7-naphthyridin-3-yl)amino)-6-methyl-5,6-dihydro-4H-pyrazolo[1,5-d][1,4]diazepin-7(8H)-one |

| Cmpd No. | Structure | Name |
|---|---|---|
| | 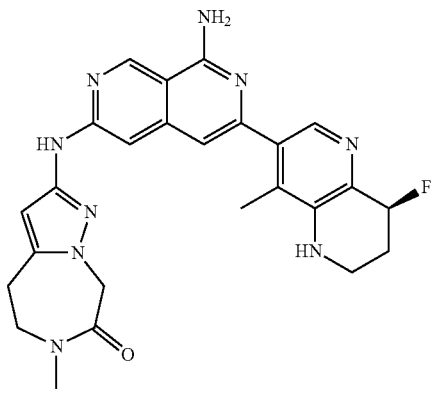 | |
| 468 | 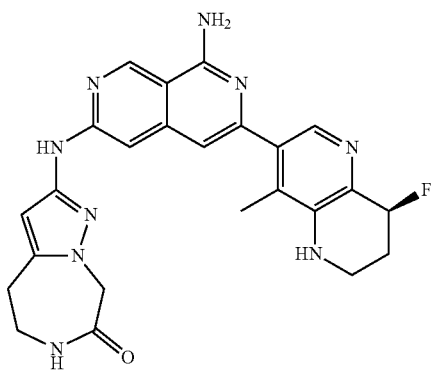<br>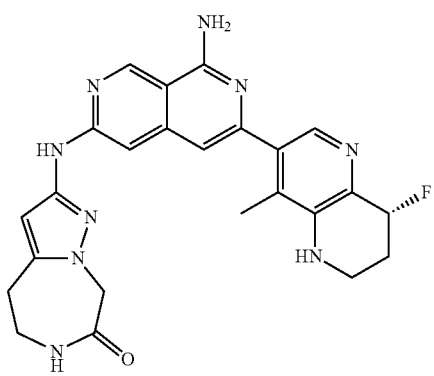 | 2-((8-amino-6-(8-fluoro-4-methyl-5,6,7,8-tetrahydro-1,5-naphthyridin-3-yl)-2,7-naphthyridin-3-yl)amino)-5,6-dihydro-4H-pyrazolo[1,5-d][1,4]diazepin-7(8H)-one |

TABLE 3-continued

| Cmpd No. | Structure | Name |
| --- | --- | --- |
| 469 | 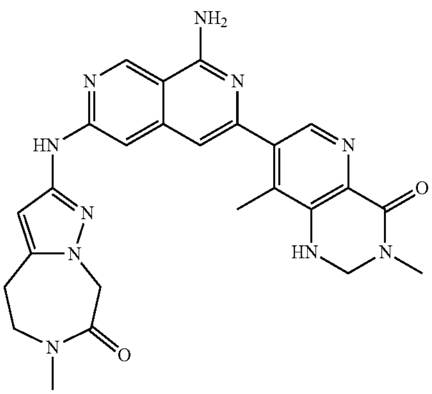 [SMILES: Cc1c(-c2cc3cc(Nc4cc5n(n4)CC(=O)N(C)CC5)ncc3c(N)n2)cnc2c1NCN(C)C2=O] | 7-(1-amino-6-((6-methyl-7-oxo-5,6,7,8-tetrahydro-4H-pyrazolo[1,5-d][1,4]diazepin-2-yl)amino)-2,7-naphthyridin-3-yl)-3,8-dimethyl-2,3-dihydropyrido[3,2-d]pyrimidin-4(1H)-one |
| 470 | 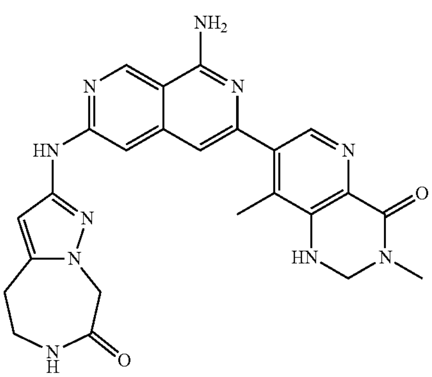 [SMILES: Cc1c(-c2cc3cc(Nc4cc5n(n4)CC(=O)NCC5)ncc3c(N)n2)cnc2c1NCN(C)C2=O] | 7-(1-amino-6-((7-oxo-5,6,7,8-tetrahydro-4H-pyrazolo[1,5-d][1,4]diazepin-2-yl)amino)-2,7-naphthyridin-3-yl)-3,8-dimethyl-2,3-dihydropyrido[3,2-d]pyrimidin-4(1H)-one |
| 471 | 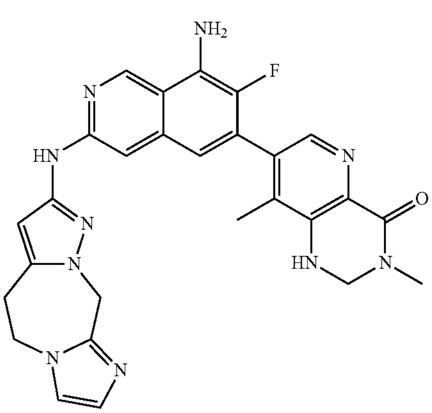 [SMILES: Cc1c(-c2cc3cc(Nc4cc5n(n4)Cc4nccn4CC5)ncc3c(N)c2F)cnc2c1NCN(C)C2=O] | 7-(8-amino-3-((5,6-dihydro-11H-imidazo[1,2-a]pyrazolo[1,5-d][1,4]diazepin-8-yl)amino)-7-fluoroisoquinolin-6-yl)-3,8-dimethyl-2,3-dihydropyrido[3,2-d]pyrimidin-4(1H)-one |

TABLE 3-continued

| Cmpd No. | Structure | Name |
|---|---|---|
| 472 | 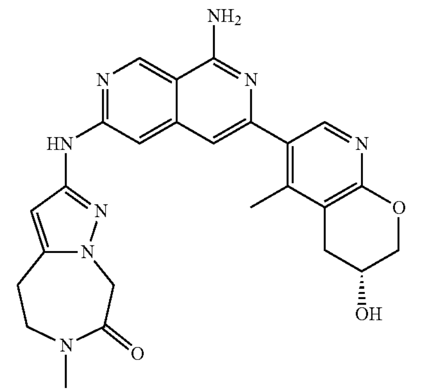 | 2-((8-amino-6-(3-hydroxy-5-methyl-3,4-dihydro-2H-pyrano[2,3-b]pyridin-6-yl)-2,7-naphthyridin-3-yl)amino)-6-methyl-5,6-dihydro-4H-pyrazolo[1,5-d][1,4]diazepin-7(8H)-one |
| 473 | 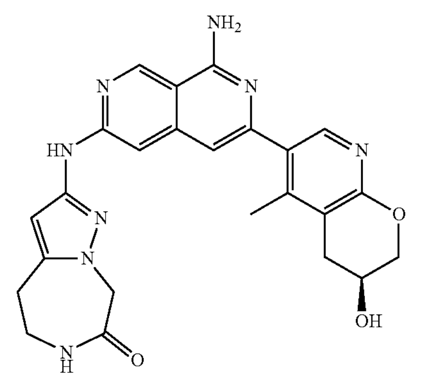 | 2-((8-amino-6-(3-hydroxy-5-methyl-3,4-dihydro-2H-pyrano[2,3-b]pyridin-6-yl)-2,7-naphthyridin-3-yl)amino)-5,6-dihydro-4H-pyrazolo[1,5-d][1,4]diazepin-7(8H)-one |

TABLE 3-continued
| Cmpd No. | Structure | Name |
|---|---|---|
| 474 | 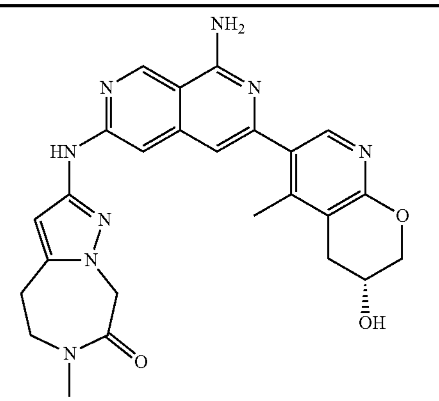 | 2-((8-amino-6-(3-hydroxy-5-methyl-3,4-dihydro-2H-pyrano[2,3-b]pyridin-6-yl)-2,7-naphthyridin-3-yl)amino)-6-methyl-5,6-dihydro-4H-pyrazolo[1,5-d][1,4]diazepin-7(8H)-one |
|  |  |  |
| 475 | 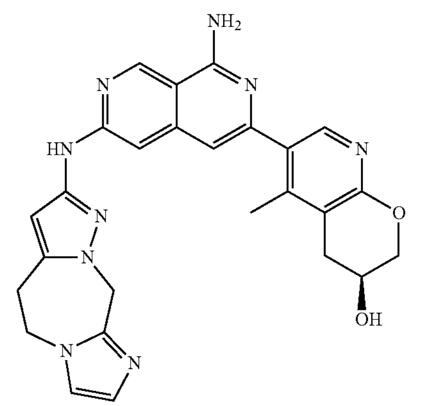 | 6-(1-amino-6-((5,6-dihydro-11H-imidazo[1,2-a]pyrazolo[1,5-d][1,4]diazepin-8-yl)amino)-2,7-naphthyridin-3-yl)-5-methyl-3,4-dihydro-2H-pyrano[2,3-b]pyridin-3-ol |

TABLE 3-continued
| Cmpd No. | Structure | Name |
|---|---|---|
| 476 | 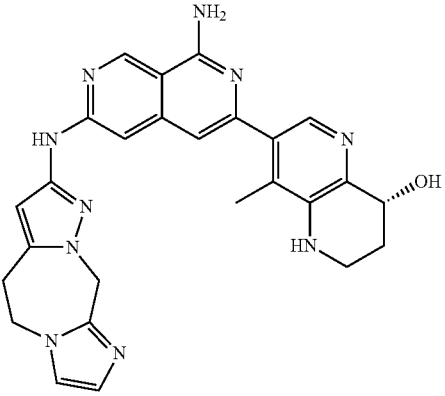 | 7-(1-amino-6-((5,6-dihydro-11H-imidazo[1,2-a]pyrazolo[1,5-d][1,4]diazepin-8-yl)amino)-2,7-naphthyridin-3-yl)-8-methyl-1,2,3,4-tetrahydro-1,5-naphthyridin-4-ol |
| |  | |
| 477 | 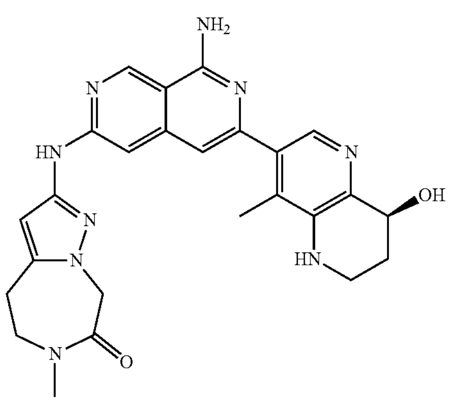 | 2-((8-amino-6-(8-hydroxy-4-methyl-5,6,7,8-tetrahydro-1,5-naphthyridin-3-yl)-2,7-naphthyridin-3-yl)amino)-6-methyl-5,6-dihydro-4H-pyrazolo[1,5-d][1,4]diazepin-7(8H)-one |
| |  | |

TABLE 3-continued
| Cmpd No. | Structure | Name |
|---|---|---|
| 478 | 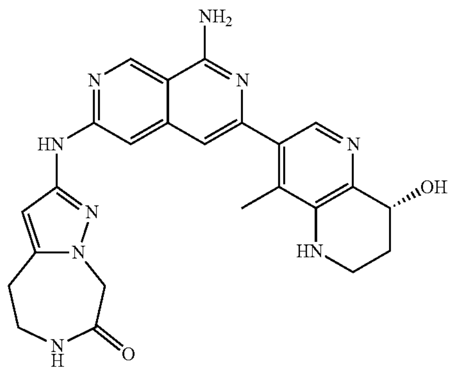 | 2-((8-amino-6-(8-hydroxy-4-methyl-5,6,7,8-tetrahydro-1,5-naphthyridin-3-yl)-2,7-naphthyridin-3-yl)amino)-5,6-dihydro-4H-pyrazolo[1,5-d][1,4]diazepin-7(8H)-one |
|  |  |  |
| 479 | 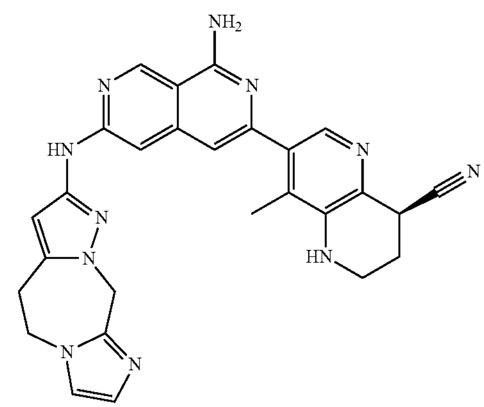 | 7-(1-amino-6-((5,6-dihydro-11H-imidazo[1,2-a]pyrazolo[1,5-d][1,4]diazepin-8-yl)amino)-2,7-naphthyridin-3-yl)-8-methyl-1,2,3,4-tetrahydro-1,5-naphthyridine-4-carbonitrile |
|  |  |  |

TABLE 3-continued

| Cmpd No. | Structure | Name |
|---|---|---|
| 480 | 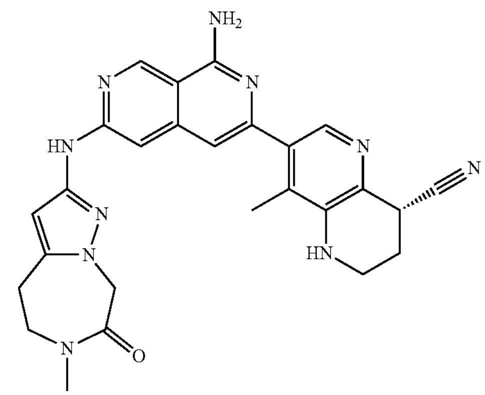 | 7-(1-amino-6-((6-methyl-7-oxo-5,6,7,8-tetrahydro-4H-pyrazolo[1,5-d][1,4]diazepin-2-yl)amino)-2,7-naphthyridin-3-yl)-8-methyl-1,2,3,4-tetrahydro-1,5-naphthyridine-4-carbonitrile |
| 481 | 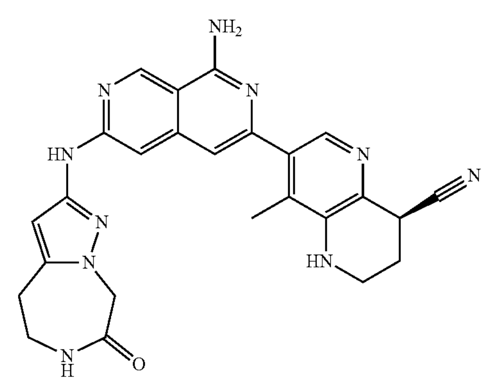 | 7-(1-amino-6-((7-oxo-5,6,7,8-tetrahydro-4H-pyrazolo[1,5-d][1,4]diazepin-2-yl)amino)-2,7-naphthyridin-3-yl)-8-methyl-1,2,3,4-tetrahydro-1,5-naphthyridine-4-carbonitrile |

TABLE 3-continued

| Cmpd No. | Structure | Name |
|---|---|---|
| 482 | 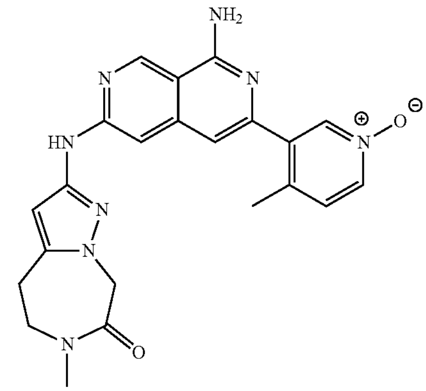 [SMILES: Cc1cc[n+]([O-])cc1-c1cc2cc(Nc3cc4n(n3)CC(=O)N(C)CC4)ncc2c(N)n1] | 3-(1-amino-6-((6-methyl-7-oxo-5,6,7,8-tetrahydro-4H-pyrazolo[1,5-d][1,4]diazepin-2-yl)amino)-2,7-naphthyridin-3-yl)-4-methylpyridine 1-oxide |
| 483 | 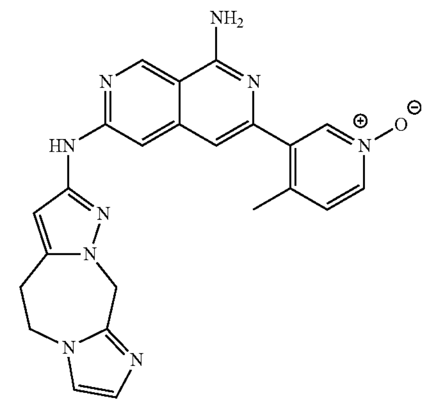 [SMILES: Cc1cc[n+]([O-])cc1-c1cc2cc(Nc3cc4n(n3)Cc3nccn3CC4)ncc2c(N)n1] | 3-(1-amino-6-((5,6-dihydro-11H-imidazo[1,2-a]pyrazolo[1,5-d][1,4]diazepin-8-yl)amino)-2,7-naphthyridin-3-yl)-4-methylpyridine 1-oxide |
| 484 | 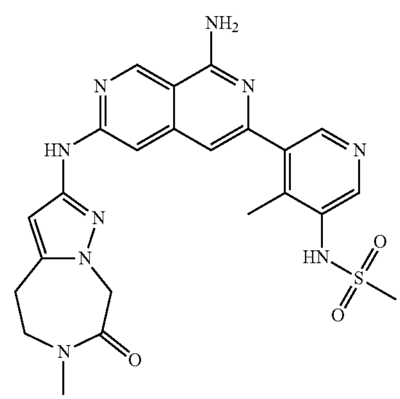 [SMILES: Cc1c(NS(C)(=O)=O)cncc1-c1cc2cc(Nc3cc4n(n3)CC(=O)N(C)CC4)ncc2c(N)n1] | N-(5-(1-amino-6-((6-methyl-7-oxo-5,6,7,8-tetrahydro-4H-pyrazolo[1,5-d][1,4]diazepin-2-yl)amino)-2,7-naphthyridin-3-yl)-4-methylpyridin-3-yl)methanesulfonamide |
| 485 | 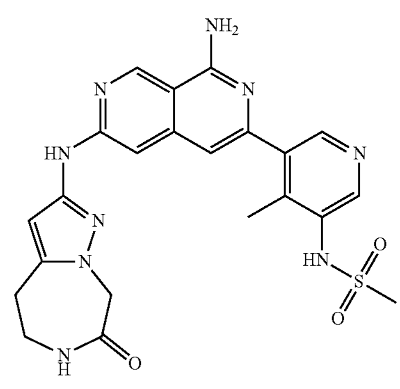 [SMILES: Cc1c(NS(C)(=O)=O)cncc1-c1cc2cc(Nc3cc4n(n3)CC(=O)NCC4)ncc2c(N)n1] | N-(5-(1-amino-6-((7-oxo-5,6,7,8-tetrahydro-4H-pyrazolo[1,5-d][1,4]diazepin-2-yl)amino)-2,7-naphthyridin-3-yl)-4-methylpyridin-3-yl)methanesulfonamide |

TABLE 3-continued

| Cmpd No. | Structure | Name |
|---|---|---|
| 486 | 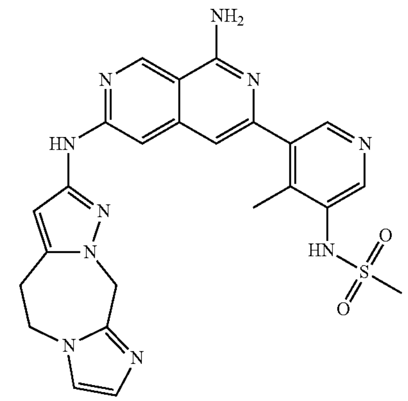 [SMILES: Cc1c(NS(C)(=O)=O)cncc1-c1cc2cc(Nc3cc4n(n3)Cc3nccn3CC4)ncc2c(N)n1] | N-(5-(1-amino-6-((5,6-dihydro-11H-imidazo[1,2-a]pyrazolo[1,5-d][1,4]diazepin-8-yl)amino)-2,7-naphthyridin-3-yl)-4-methylpyridin-3-yl)methanesulfonamide |
| 487 | 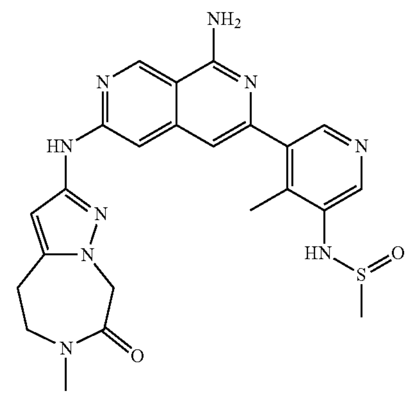 [SMILES: Cc1c(NS(C)=O)cncc1-c1cc2cc(Nc3cc4n(n3)CC(=O)N(C)CC4)ncc2c(N)n1] | N-(5-(1-amino-6-((6-methyl-7-oxo-5,6,7,8-tetrahydro-4H-pyrazolo[1,5-d][1,4]diazepin-2-yl)amino)-2,7-naphthyridin-3-yl)-4-methylpyridin-3-yl)methanesulfinamide |
| 488 | 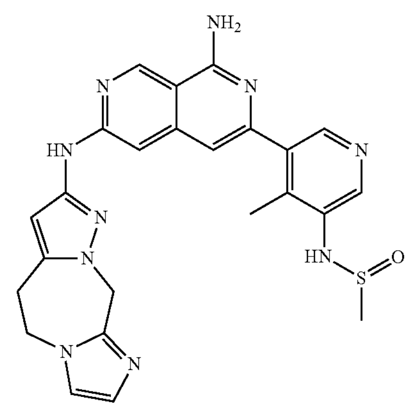 [SMILES: Cc1c(NS(C)=O)cncc1-c1cc2cc(Nc3cc4n(n3)Cc3nccn3CC4)ncc2c(N)n1] | N-(5-(1-amino-6-((5,6-dihydro-11H-imidazo[1,2-a]pyrazolo[1,5-d][1,4]diazepin-8-yl)amino)-2,7-naphthyridin-3-yl)-4-methylpyridin-3-yl)methanesulfinamide |
| 489 | 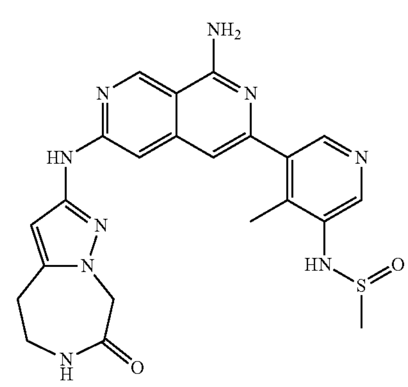 [SMILES: Cc1c(NS(C)=O)cncc1-c1cc2cc(Nc3cc4n(n3)CC(=O)NCC4)ncc2c(N)n1] | N-(5-(1-amino-6-((7-oxo-5,6,7,8-tetrahydro-4H-pyrazolo[1,5-d][1,4]diazepin-2-yl)amino)-2,7-naphthyridin-3-yl)-4-methylpyridin-3-yl)methanesulfinamide |

TABLE 3-continued

| Cmpd No. | Structure | Name |
|---|---|---|
| 490 | 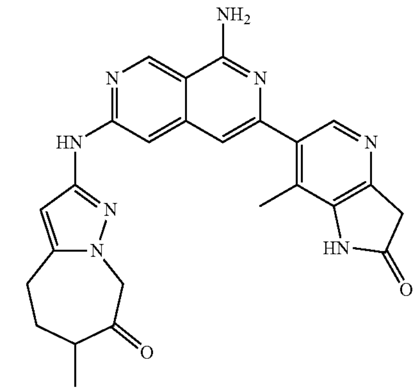 [SMILES: Cc1c(-c2cc3cc(Nc4cc5n(n4)CC(=O)C(C)CC5)ncc3c(N)n2)cnc2c1NC(=O)C2] | 2-((8-amino-6-(7-methyl-2-oxo-2,3-dihydro-1H-pyrrolo[3,2-b]pyridin-6-yl)-2,7-naphthyridin-3-yl)amino)-6-methyl-5,6-dihydro-4H-pyrazolo[1,5-d][1,4]diazepin-7(8H)-one |
| 491 | 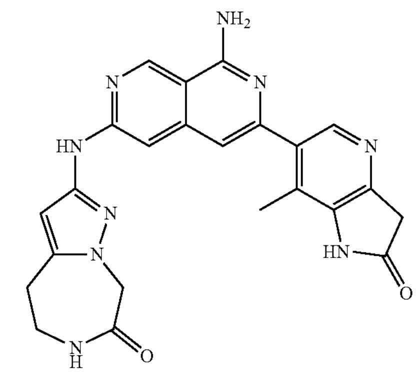 [SMILES: Cc1c(-c2cc3cc(Nc4cc5n(n4)CC(=O)NCC5)ncc3c(N)n2)cnc2c1NC(=O)C2] | 2-((8-amino-6-(7-methyl-2-oxo-2,3-dihydro-1H-pyrrolo[3,2-b]pyridin-6-yl)-2,7-naphthyridin-3-yl)amino)-5,6-dihydro-4H-pyrazolo[1,5-d][1,4]diazepin-7(8H)-one |
| 492 | 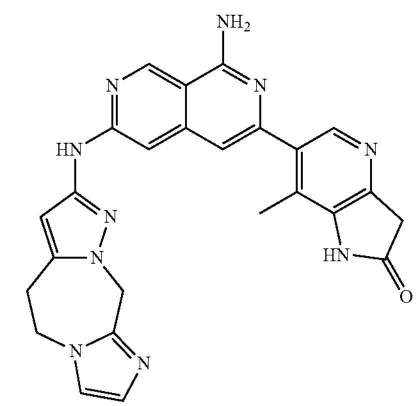 [SMILES: Cc1c(-c2cc3cc(Nc4cc5n(n4)Cc4nccn4CC5)ncc3c(N)n2)cnc2c1NC(=O)C2] | 6-(1-amino-6-((5,6-dihydro-11H-imidazo[1,2-a]pyrazolo[1,5-d][1,4]diazepin-8-yl)amino)-2,7-naphthyridin-3-yl)-7-methyl-1,3-dihydro-2H-pyrrolo[3,2-b]pyridin-2-one |
| 493 | 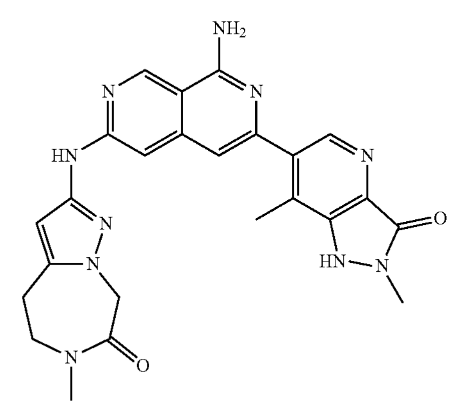 [SMILES: Cc1c(-c2cc3cc(Nc4cc5n(n4)CC(=O)N(C)CC5)ncc3c(N)n2)cnc2c(=O)n(C)[nH]c12] | 2-((8-amino-6-(2,7-dimethyl-3-oxo-2,3-dihydro-1H-pyrazolo[4,3-b]pyridin-6-yl)-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 494 | 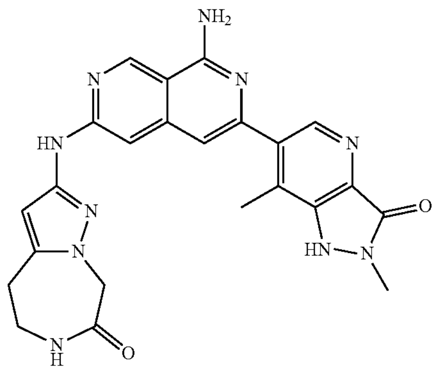 [SMILES: Cc1c(-c2cc3cc(Nc4cc5n(n4)CC(=O)NCC5)ncc3c(N)n2)cnc2c(=O)n(C)[nH]c12] | 2-((8-amino-6-(2,7-dimethyl-3-oxo-2,3-dihydro-1H-pyrazolo[4,3-b]pyridin-6-yl)-2,7-naphthyridin-3-yl)amino)-5,6-dihydro-4H-pyrazolo[1,5-d][1,4]diazepin-7(8H)-one |
| 495 | 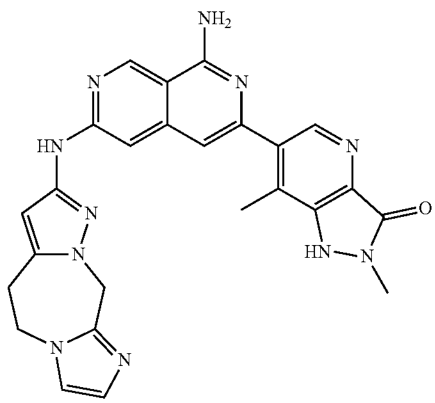 [SMILES: Cc1c(-c2cc3cc(Nc4cc5n(n4)Cc4nccn4CC5)ncc3c(N)n2)cnc2c(=O)n(C)[nH]c12] | 6-(1-amino-6-((5,6-dihydro-11H-imidazo[1,2-a]pyrazolo[1,5-d][1,4]diazepin-8-yl)amino)-2,7-naphthyridin-3-yl)-2,7-dimethyl-1,2-dihydro-3H-pyrazolo[4,3-b]pyridin-3-one |
| 496 | 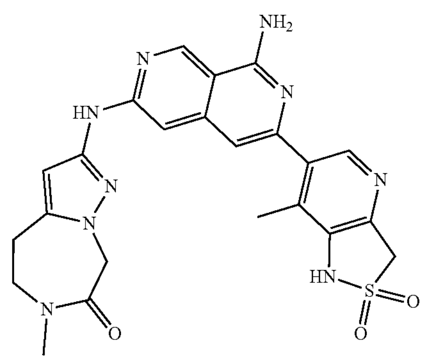 [SMILES: Cc1c(-c2cc3cc(Nc4cc5n(n4)CC(=O)N(C)CC5)ncc3c(N)n2)cnc2c1NS(=O)(=O)C2] | 2-((8-amino-6-(7-methyl-2,2-dioxido-1,3-dihydroisothiazolo[4,3-b]pyridini-6-yl)-2,7-naphthyridin-3-yl)amino)-6-methyl-5,6-dihydro-4H-pyrazolo[1,5-d][1,4]diazepin-7(8H)-one |
| 497 | 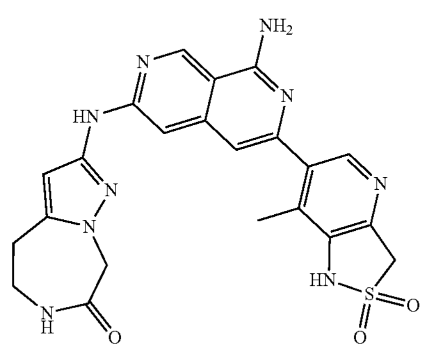 [SMILES: Cc1c(-c2cc3cc(Nc4cc5n(n4)CC(=O)NCC5)ncc3c(N)n2)cnc2c1NS(=O)(=O)C2] | 2-((8-amino-6-(7-methyl-2,2-dioxido-1,3-dihydroisothiazolo[4,3-b]pyridin-6-yl)-2,7-naphthyridin-3-yl)amino)-3,6-dihydro-4H-pyrazolo[1,5-d][1,4]diazepin-7(8H)-one |

TABLE 3-continued

| Cmpd No. | Structure | Name |
|---|---|---|
| 498 | 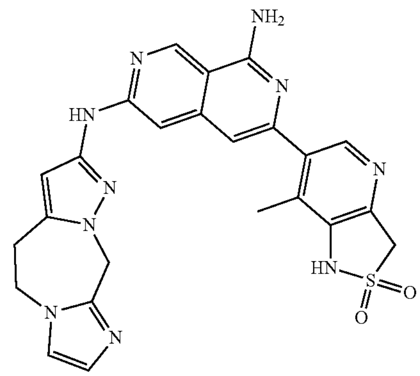 [SMILES: Cc1c(-c2cc3cc(Nc4cc5n(n4)Cc4nccn4CC5)ncc3c(N)n2)cnc2c1NS(=O)(=O)C2] | 6-(1-amino-6-((5,6-dihydro-11H-imidazo[1,2-a]pyrazolo[1,5-d][1,4]diazepin-8-yl)amino)-2,7-naphthyridin-3-yl)-7-methyl-1,3-dihydroisothiazolo[4,3-b]pyridine 2,2-dioxide |
| 499 | 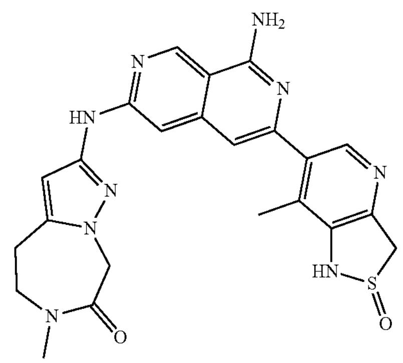 [SMILES: Cc1c(-c2cc3cc(Nc4cc5n(n4)CC(=O)N(C)CC5)ncc3c(N)n2)cnc2c1NS(=O)C2] | 2-((8-amino-6-(7-methyl-2-oxido-1,3-dihydroisothiazolo[4,3-b]pyridin-6-yl)-2,7-naphthyridin-3-yl)amino)-6-methyl-5,6-dihydro-4H-pyrazolo[1,5-d][1,4]diazepin-7(8H)-one |
| 500 | 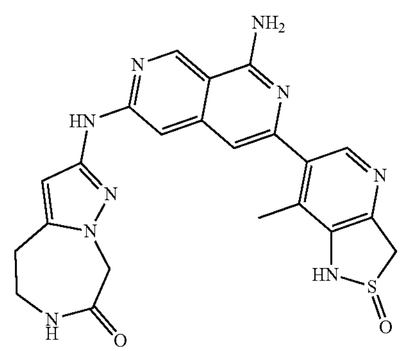 [SMILES: Cc1c(-c2cc3cc(Nc4cc5n(n4)CC(=O)NCC5)ncc3c(N)n2)cnc2c1NS(=O)C2] | 2-((8-amino-6-(7-methyl-2-oxido-1,3-dihydroisothiazolo[4,3-b]pyridin-6-yl)-2,7-naphthyridin-3-yl)amino)-5,6-dihydro-4H-pyrazolo[1,5-d][1,4]diazepin-7(8H)-one |
| 501 | 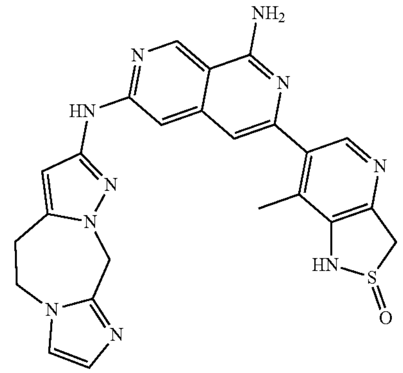 [SMILES: Cc1c(-c2cc3cc(Nc4cc5n(n4)Cc4nccn4CC5)ncc3c(N)n2)cnc2c1NS(=O)C2] | 6-(1-amino-6-((5,6-dihydro-11H-imidazo[1,2-a]pyrazolo[1,5-d][1,4]diazepin-8-yl)amino)-2,7-naphthyridin-3-yl)-7-methyl-1,3-dihydroisothiazolo[4,3-b]pyridine 2-oxide |

TABLE 3-continued

| Cmpd No. | Structure | Name |
|---|---|---|
| 502 | 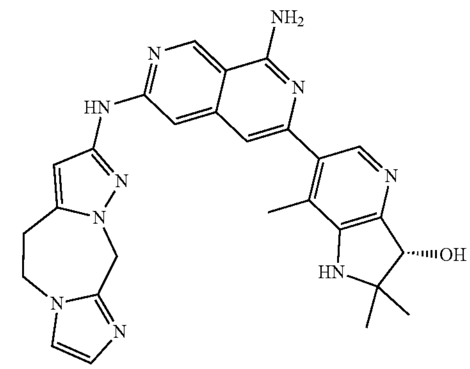 | 6-(1-amino-6-((5,6-dihydro-11H-imidazo[1,2-a]pyrazolo[1,5-d][1,4]diazepin-8-yl)amino)-2,7-naphthyridin-3-yl)-2,2,7-trimethyl-2,3-dihydro-1H-pyrrolo[3,2-b]pyridin-3-ol |
| 503 | 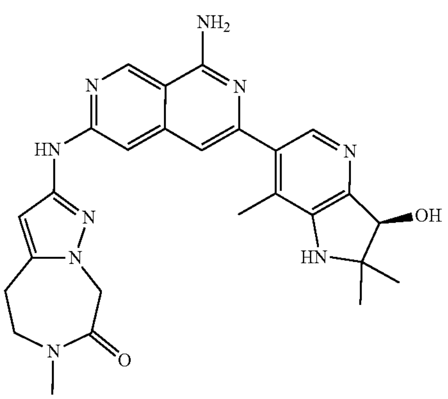 | 2-((8-amino-6-(3-hydroxy-2,2,7-trimethyl-2,3-dihydro-1H-pyrrolo[3,2-b]pyridin-6-yl)-2,7-naphthyridin-3-yl)amino)-6-methyl-5,6-dihydro-4H-pyrazolo[1,5-d][1,4]diazepin-7(8H)-one |

TABLE 3-continued
| Cmpd No. | Structure | Name |
|---|---|---|
| 504 | 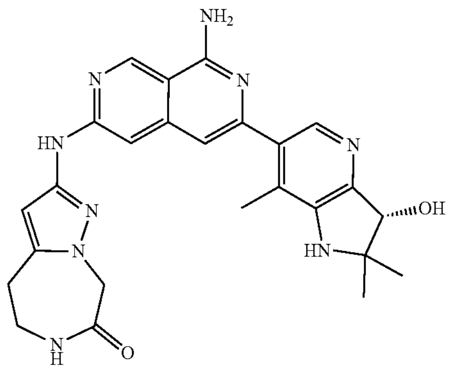 | 2-((8-amino-6-(3-hydroxy-2,2,7-trimethyl-23-dihydro-1H-pyrrolo[3,2-b]pyridin-6-yl)-2,7-naphthyridin-3-yl)amino)-5,6-dihydro-4H-pyrazolo[1,5-d][1,4]diazepin-7(8H)-one |
|  |  |  |
| 505 | 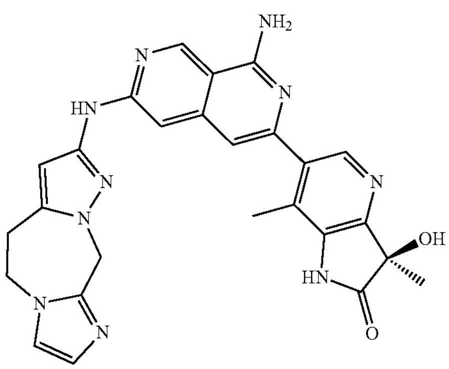 | 6-(1-amino-6-((5,6-dihydro-11H-imidazo[1,2-a]pyrazolo[1,5-d][1,4]diazepin-8-yl)amino)-2,7-naphthyridin-3-yl)-3-hydroxy-3,7-dimethyl-1,3-dihydro-2H-pyrrolo[3,2-b]pyridin-2-one |
|  |  |  |

TABLE 3-continued

| Cmpd No. | Structure | Name |
|---|---|---|
| 506 | 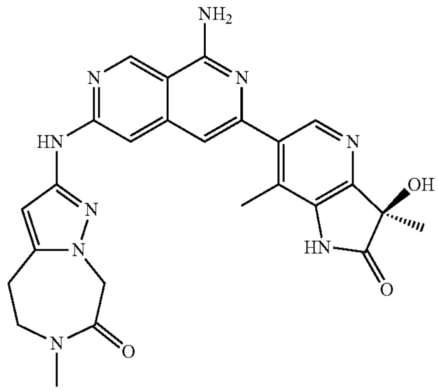 | 2-((8-amino-6-(3-hydroxy-3,7-dimethyl-2-oxo-2,3-dihydro-1H-pyrrolo[3,2-b]pyridin-6-yl)-2,7-naphthyridin-3-yl)amino)-6-methyl-5,6-dihydro-4H-pyrazolo[1,5-d][1,4]diazepin-7(8H)-one |
| 507 | 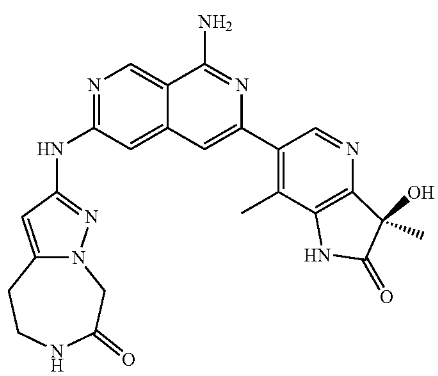 | 2-((8-amino-6-(3-hydroxy-3,7-dimethyl-2-oxo-2,3-dihydro-1H-pyrrolo[3,2-b]pyridin-6-yl)-2,7-naphthyridin-3-yl)amino)-5,6-dihydro-4H-pyrazolo[1,5-d][1,4]diazepin-7(8H)-one |

TABLE 3-continued

| Cmpd No. | Structure | Name |
|---|---|---|
| 508 | 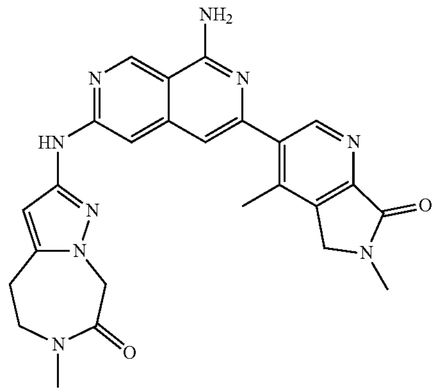 [SMILES: Cc1c(-c2cc3cc(Nc4cc5n(n4)CC(=O)N(C)CC5)ncc3c(N)n2)cnc2c1CN(C)C2=O] | 2-((8-amino-6-(4,6-dimethyl-7-oxo-6,7-dihydro-5H-pyrrolo[3,4-b]pyridin-3-yl)-2,7-naphthyridin-3-yl)amino)-6-methyl-5,6-dihydro-4H-pyrazolo[1,5-d][1,4]diazepin-7(8H)-one |
| 509 | 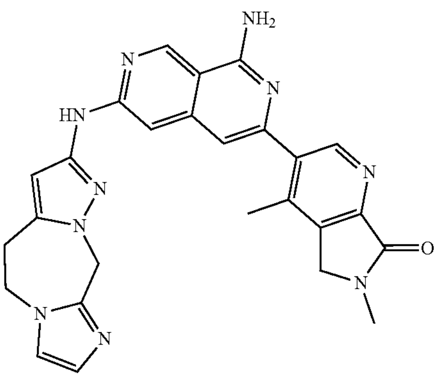 [SMILES: Cc1c(-c2cc3cc(Nc4cc5n(n4)Cc4nccn4CC5)ncc3c(N)n2)cnc2c1CN(C)C2=O] | 3-(1-amino-6-((5,6-dihydro-11H-imidazo[1,2-a]pyrazolo[1,5-d][1,4]diazepin-8-yl)amino)-2,7-naphthyridin-3-yl)-4,6-dimethyl-5,6-dihydro-7H-pyrrolo[3,4-b]pyridin-7-one |
| 510 | 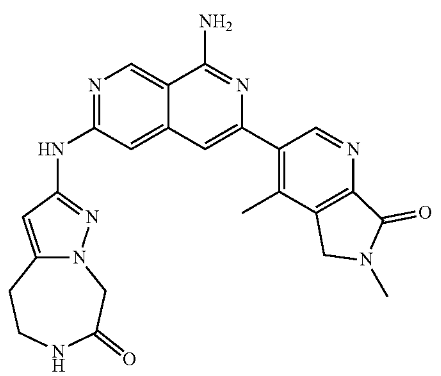 [SMILES: Cc1c(-c2cc3cc(Nc4cc5n(n4)CC(=O)NCC5)ncc3c(N)n2)cnc2c1CN(C)C2=O] | 2-((8-amino-6-(4,6-dimethyl-7-oxo-6,7-dihydro-5H-pyrrolo[3,4-b]pyridin-3-yl)-2,7-naphthyridin-3-yl)amino)-5,6-dihydro-4H-pyrazolo[1,5-d][1,4]diazepin-7(8H)-one |
| 511 | 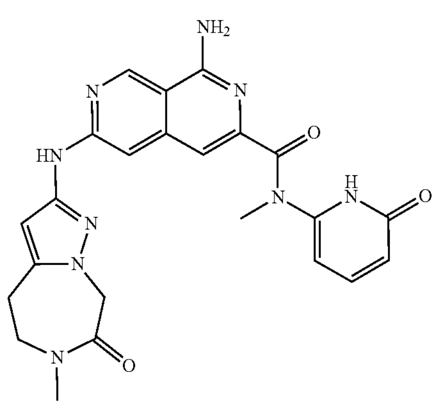 [SMILES: CN1CCc2cc(Nc3cc4cc(C(=O)N(C)c5cccc(=O)[nH]5)nc(N)c4cn3)nn2CC1=O] | 8-1-amino-N-methyl-6-((6-methyl-7-oxo-5,6,7,8-tetrahydro-4H-pyrazolo[1,5-d][1,4]diazepin-2-yl)amino)-N-(6-oxo-1,6-dihydropyridin-2-yl)-2,7-naphthyridine-3-carboxamide |

TABLE 3-continued

| Cmpd No. | Structure | Name |
|---|---|---|
| 512 | 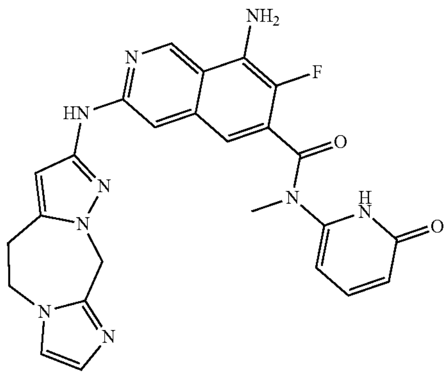 [SMILES: CN(C(=O)c1cc2cc(Nc3cc4n(n3)Cc3nccn3CC4)ncc2c(N)c1F)c1cccc(=O)[nH]1] | 8-amino-3-((5,6-dihydro-11H-imidazo[1,2-a]pyrazolo[1,5-d][1,4]diazepin-8-yl)amino)-7-fluoro-N-methyl-N-(6-oxo-1,6-diliydropyridin-2-yl)isoquinoline-6-carboxamide |
| 513 | 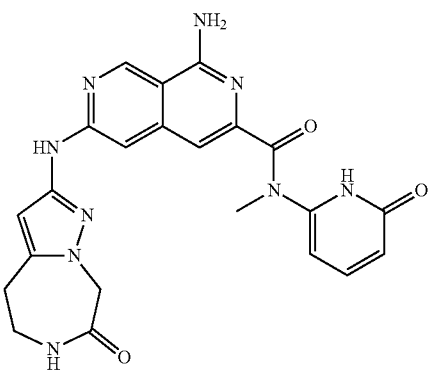 [SMILES: CN(C(=O)c1cc2cc(Nc3cc4n(n3)CC(=O)NCC4)ncc2c(N)n1)c1cccc(=O)[nH]1] | 1-amino-N-methyl-N-(6-oxo-1,6-dihydropyridin-2-yl)-6-((7-oxo-5,6,7,8-tetrahydro-4H-pyrazolo[1,5-d][1,4]diazepin-2-yl)amino)-2,7-naphthyridine-3-carboxamide |
| 514 | 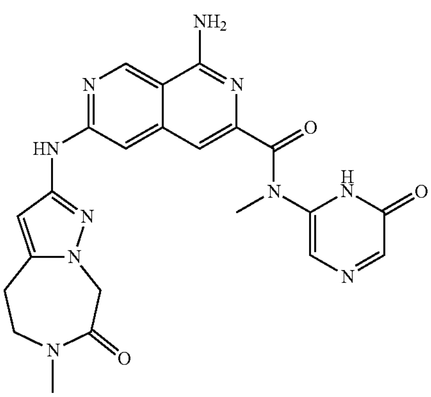 [SMILES: CN1CCc2cc(Nc3cc4cc(C(=O)N(C)c5cncc(=O)[nH]5)nc(N)c4cn3)nn2CC1=O] | 1-amino-N-methyl-6-((6-methyl-7-oxo-5,6,7,8-tetrahydro-4H-pyrazolo[1,5-d][1,4]diazepin-2-yl)amino)-N-(6-oxo-1,6-dihydropyrazin-2-yl)-2,7-naphthyridine-3-carboxamide |
| 515 | 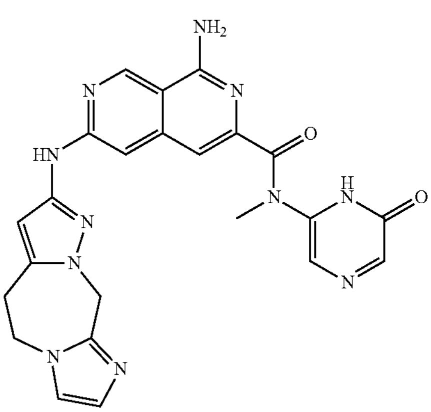 [SMILES: CN(C(=O)c1cc2cc(Nc3cc4n(n3)Cc3nccn3CC4)ncc2c(N)n1)c1cncc(=O)[nH]1] | 1-amino-6-((5,6-dihydro-11H-imidazo[1,2-a]pyrazolo[1,5-d][1,4]diazepin-8-yl)amino)-N-methyl-N-(6-oxo-1,6-dihydropyrazin-2-yl)-2,7-naphthyridine-3-carboxamide |

TABLE 3-continued

| Cmpd No. | Structure | Name |
|---|---|---|
| 516 | 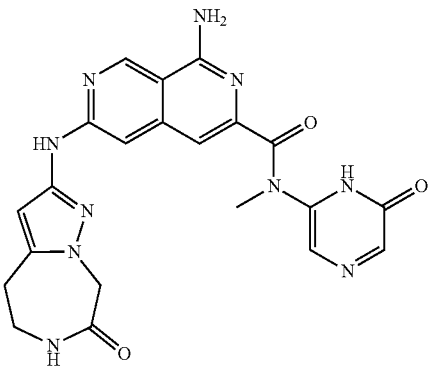 | 1-amino-N-methyl-N-(6-oxo-1,6-dihydropyrazin-2-yl)-6-((7-oxo-5,6,7,8-tetrahydro-4H-pyrazolo[1,5-d][1,4]diazepin-2-yl)amino)-2,7-naphthyridine-3-carboxamide |
| 517 | 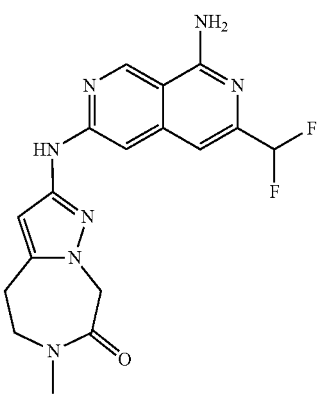 [SMILES: CN1CCc2cc(Nc3cc4cc(C(F)F)nc(N)c4cn3)nn2CC1=O] | 2-((8-amino-6-(difluoromethyl)-2,7-naphthyridin-3-yl)amino)-6-methyl-5,6-dihydro-4H-pyrazolo[1,5-d][1,4]diazepin-7(8H)-one |
| 518 | 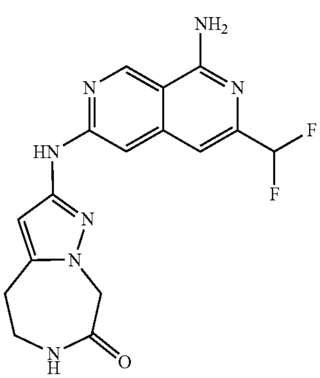 [SMILES: Nc1nc(C(F)F)cc2cc(Nc3cc4n(n3)CC(=O)NCC4)ncc12] | 2-((8-amino-6-(difluoromethyl)-2,7-naphthyridin-3-yl)amino)-5,6-dihydro-4H-pyrazolo[1,5-d][1,4]diazepin-7(8H)-one |
| 519 | 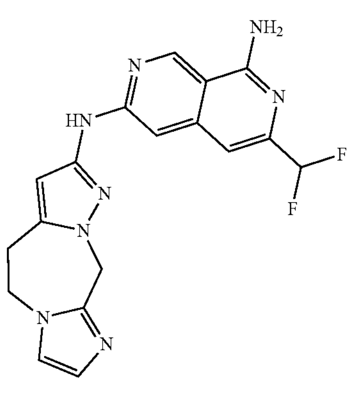 [SMILES: Nc1nc(C(F)F)cc2cc(Nc3cc4n(n3)Cc3nccn3CC4)ncc12] | 3-(difluoromethyl)-N6-(5,6-dihydro-11H-imidazo[1,2-a]pyrazolo[1,5-d][1,4]diazepin-8-yl)-2,7-naphthyridine-1,6-diamine |

TABLE 3-continued
| Cmpd No. | Structure | Name |
|---|---|---|
| 520 | 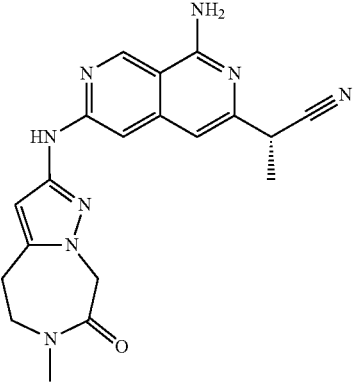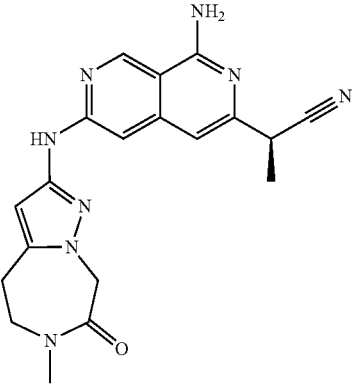 | 2-(1-amino-6-((6-methyl-7-oxo-5,6,7,8-tetrahydro-4H-pyrazolo[1,5-d][1,4]diazepin-2-yl)amino)-2,7-naphthyridin-3-yl)propanenitrile |
| 521 | 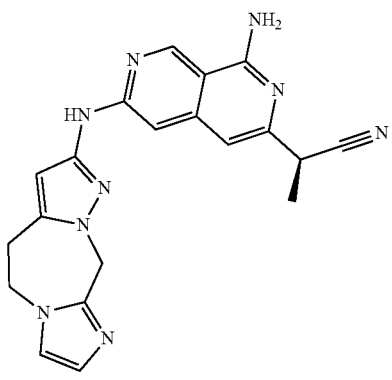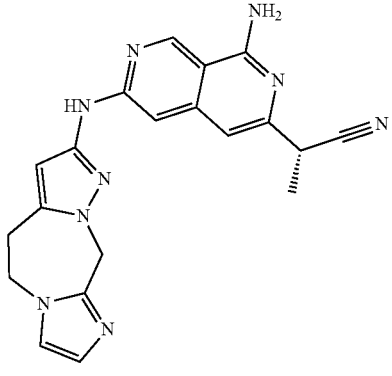 | 2-(1-amino-6-((5,6-dihydro-11H-imidazo[1,2-a]pyrazolo[1,5-d][1,4]diazepin-8-yl)amino)-2,7-naphthyridin-3-yl)propanenitrile |

TABLE 3-continued
| Cmpd No. | Structure | Name |
|---|---|---|
| 522 | 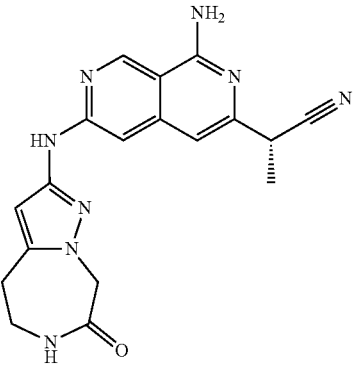 | 2-(1-amino-6-((7-oxo-5,6,7,8-tetrahydro-4H-pyrazolo[1,5-d][1,4]diazepin-2-yl)amino)-2,7-naphthyridin-3-yl)propanenitrile |
| 523 | 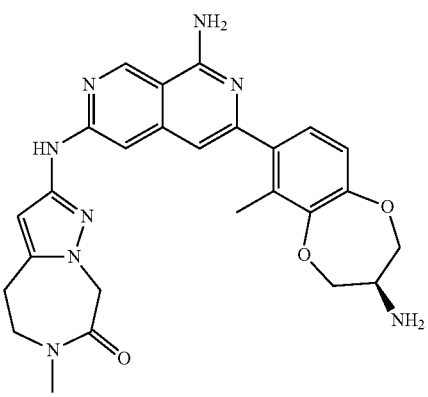 | 2-((8-amino-6-(3-amino-9-methyl-3,4-dihydro-2H-[1,4]dioxepino[2,3-b]pyridin-8-yl)-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 524 | 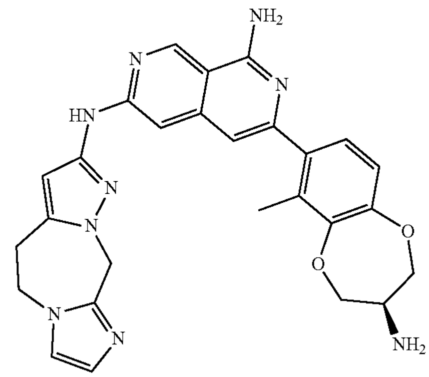 | 3-(3-amino-9-methyl-3,4-dihydro-2H-[1,4]dioxepino[2,3-b]pyridin-8-yl)-N6-(5,6-dihydro-11H-imidazo[1,2-a]pyrazolo[1,5-d][1,4]diazepin-8-yl)-2,7-naphthyridine-1,6-diamine |
| 525 | 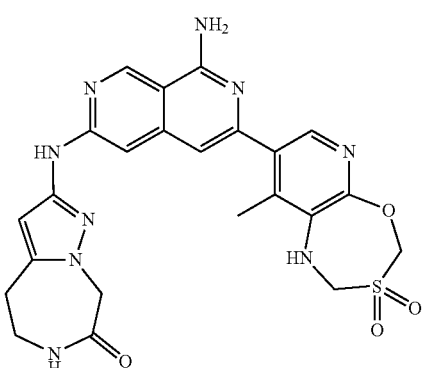 | 2-((8-amino-6-(9-methyl-3,3-dioxido-1,2-dihydro-4H-pyrido[3,2-f][1,3,5]oxathiazepin-8-yl)-2,7-naphthyndin-3-yl)amino)-5,6-dihydro-4H-pyrazolo[1,5-d][1,4]diazepin-7(8H)-one |
| 526 | 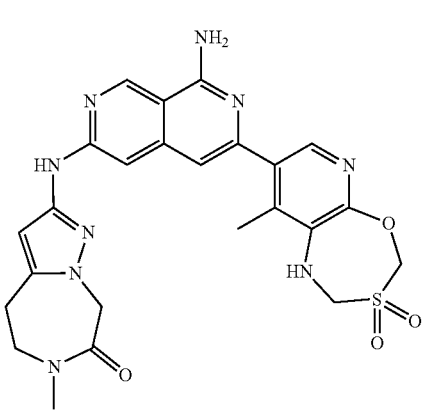 [SMILES: Cc1c(-c2cc3cc(Nc4cc5n(n4)CC(=O)N(C)CC5)ncc3c(N)n2)cnc2c1NCS(=O)(=O)CO2] | 2-((8-amino-6-(9-methyl-3,3-dioxido-1,2-dihydro-4H-pyrido[3,2-f][1,3,5]oxathiazepin-8-yl)-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 527 | 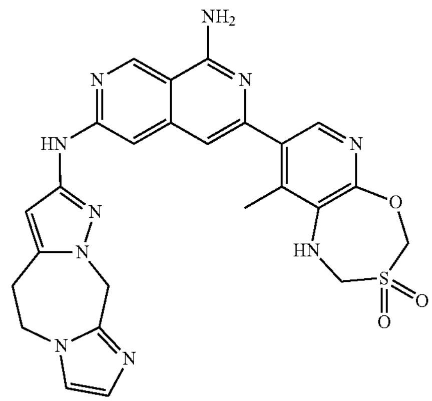 [SMILES: Cc1c(-c2cc3cc(Nc4cc5n(n4)Cc4nccn4CC5)ncc3c(N)n2)cnc2c1NCS(=O)(=O)CO2] | 8-(1-amino-6-((5,6-dihydro-11H-imidazo[1,2-a]pyrazolo[1,5-d][1,4]diazepin-8-yl)amino)-2,7-naphthyridin-3-yl)-9-methyl-1,2-dihydro-4H-pyrido[3,2-f][1,3,5]oxathiazepine 3,3-dioxide |
| 528 | 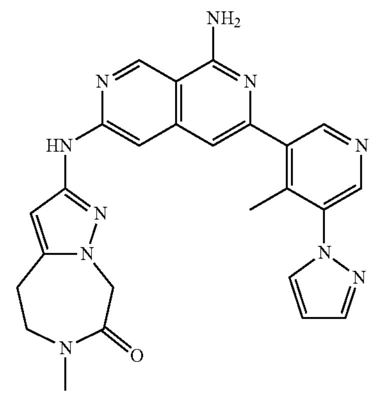 [SMILES: Cc1c(-c2cc3cc(Nc4cc5n(n4)CC(=O)N(C)CC5)ncc3c(N)n2)cncc1-n1cccn1] | 2-((8-amino-6-(4-methyl-5-(1H-pyrazol-1-yl)pyridin-3-yl)-2,7-naphthyridin-3-yl)amino)-6-methyl-5,6-dihydro-4H-pyrazolo[1,5-d][1,4]diazepin-7(8H)-one |
| 529 | 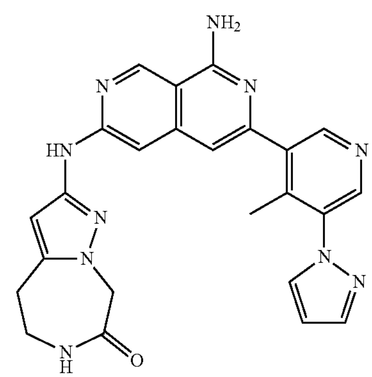 [SMILES: Cc1c(-c2cc3cc(Nc4cc5n(n4)CC(=O)NCC5)ncc3c(N)n2)cncc1-n1cccn1] | 2-((8-amino-6-(4-methyl-5-(1H-pyrazol-1-yl)pyridin-3-yl)-2,7-naphthyridin-3-yl)amino)-5,6-dihydro-4H-pyrazolo[1,5-d][1,4]diazepin-7(8H)-one |
| 530 | 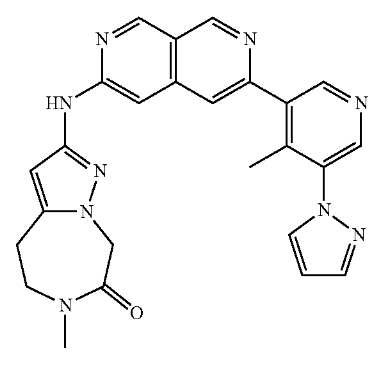 [SMILES: Cc1c(-c2cc3cc(Nc4cc5n(n4)CC(=O)N(C)CC5)ncc3cn2)cncc1-n1cccn1] | 2-((6-(5-(1H-imidazol-1-yl)-4-methylpyridin-3-yl)-2,7-naphthyridin-3-yl)amino)-6-methyl-5,6-dihydro-4H-pyrazolo[1-5-d][1,4]diazepin-7(8H)-one |

TABLE 3-continued

| Cmpd No. | Structure | Name |
| --- | --- | --- |
| 531 | 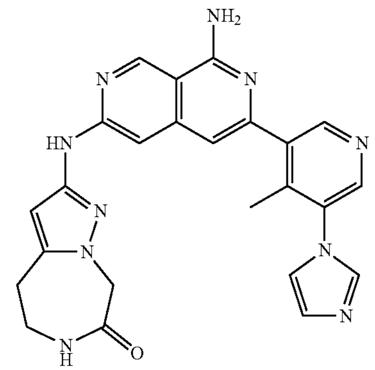 [SMILES: Cc1c(-c2cc3cc(Nc4cc5n(n4)CC(=O)NCC5)ncc3c(N)n2)cncc1-n1ccnc1] | 2-((6-(5-(1H-imidazol-1-yl)-4-methylpyridin-3-yl)-8-amino-2,7-naphthyridin-3-yl)amino)-5,6-dihydro-4H-pyrazolo[1,5-d][1,4]diazepin-7(8H)-one |
| 532 | 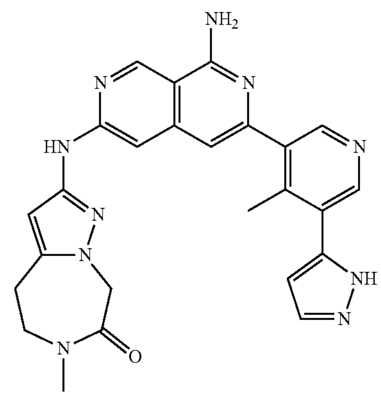 [SMILES: Cc1c(-c2cc3cc(Nc4cc5n(n4)CC(=O)N(C)CC5)ncc3c(N)n2)cncc1-c1ccn[nH]1] | 2-((8-amino-6-(4-methyl-5-(1H-pyrazol-5-yl)pyridin-3-yl)-2,7-naphthyridin-3-yl)amino)-6-methyl-5,6-dihydro-4H-pyrazolo[1,5-d][1,4]diazepin-7(8H)-one |
| 533 | 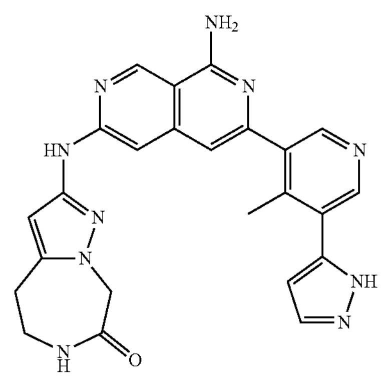 [SMILES: Cc1c(-c2cc3cc(Nc4cc5n(n4)CC(=O)NCC5)ncc3c(N)n2)cncc1-c1ccn[nH]1] | 2-((8-amino-6-(4-methyl-5-(1H-pyrazol-5-yl)pyridin-3-yl)-2,7-naphthyridin-3-yl)amino)-5,6-dihydro-4H-pyrazolo[1,5-d][1,4]diazepin-7(8H)-one |
| 534 | 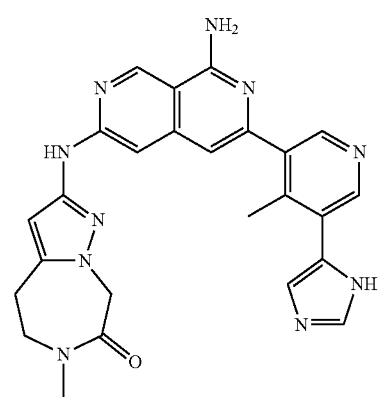 [SMILES: Cc1c(-c2cc3cc(Nc4cc5n(n4)CC(=O)N(C)CC5)ncc3c(N)n2)cncc1-c1cnc[nH]1] | 2-((6-(5-(1H-imidazol-5-yl)-4-methylpyridin-3-yl)-8-amino-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 535 | 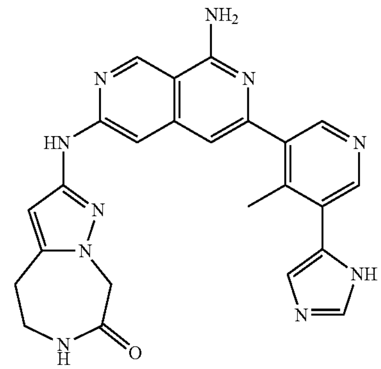 [SMILES: Cc1c(-c2cc3cc(Nc4cc5n(n4)CC(=O)NCC5)ncc3c(N)n2)cncc1-c1cnc[nH]1] | 2-((6-(5-(1H-imidazol-5-yl)-4-methylpyridin-3-yl)-8-amino-2,7-naphthyridin-3-yl)amino)-5,6-dihydro-4H-pyrazolo[1,5-d][1,4]diazepin-7(8H)-one |
| 536 | 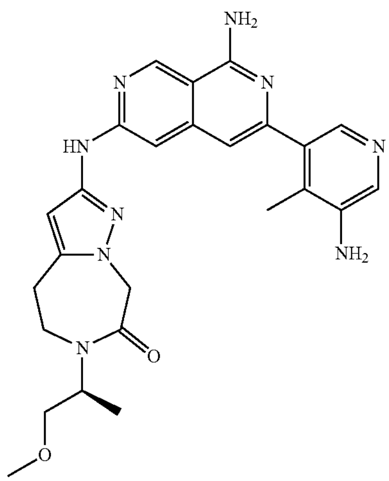 | 2-((8-amino-6-(5-amino-4-methylpyridin-3-yl)-2,7-naphthyridin-3-yl)amino)-6-(1-methoxypropan-2-yl)-5,6-dihydro-4H-pyrazolo[1,5-d][1,4]diazepin-7(8H)-one |

TABLE 3-continued
| Cmpd No. | Structure | Name |
|---|---|---|
| 537 | 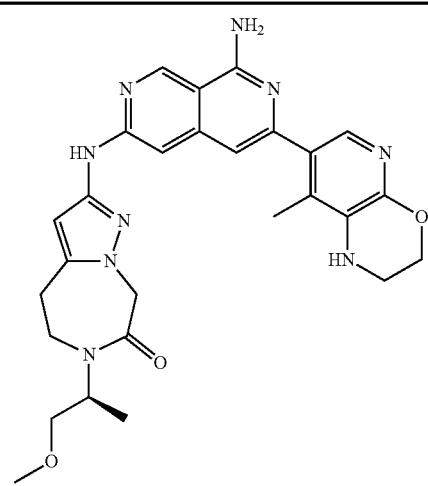 | 2-((8-amino-6-(8-methyl-2,3-dihydro-1H-pyrido[2,3-b][1,4]oxazin-7-yl)-2,7-naphthyridin-3-yl)amino)-6-(1-methoxypropan-2-yl)-5,6-dihydro-4H-pyrazolo[1,5-d][1,4]diazepin-7(8H)-one |
| 538 | 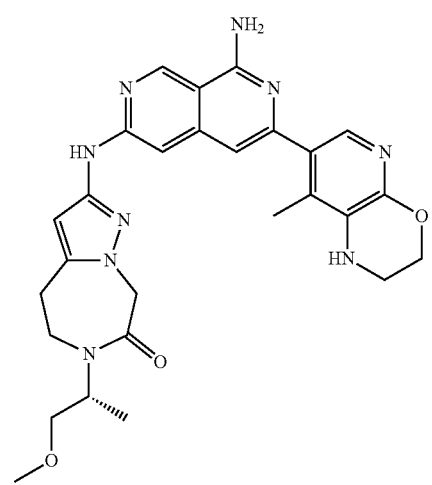 | 2-((8-amino-6-(8-methyl-2,3-dihydro-1H-pyrido[2,3-b][1,4]oxazin-7-yl)-2,7-naphthyridin-3-yl)amino)-6-(tetralndrofliran-3-yl)-5,6-dihydro-4H-pyrazolo[1,5-d][1,4]diazepin-7(8H)-one |

TABLE 3-continued

| Cmpd No. | Structure | Name |
|---|---|---|
| | | |
| 539 | 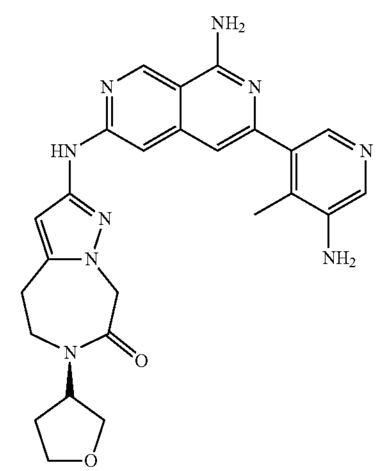 | 2-((8-amino-6-(5-amino-4-methylpyridin-3-yl)-2,7-naphthyridin-3-yl)amino)-6-(tetrahydrofuran-3-yl)-5,6-dihydro-4H-pyrazolo[1,5-d][1,4]diazepin-7(8H)-one |

TABLE 3-continued

| Cmpd No. | Structure | Name |
|---|---|---|
| 540 | 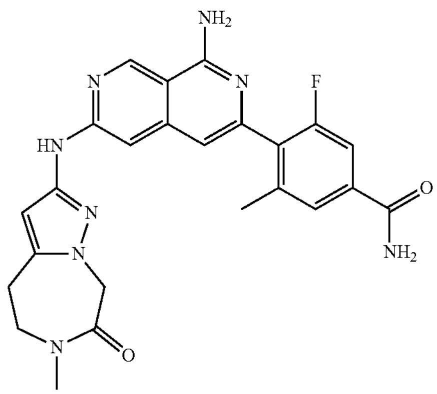 [SMILES: Cc1cc(C(N)=O)cc(F)c1-c1cc2cc(Nc3cc4n(n3)CC(=O)N(C)CC4)ncc2c(N)n1] | 4-(1-amino-6-((6-methyl-7-oxo-5,6,7,8-tetrahydro-4H-pyrazolo[1,5-d][1,4]diazepin-2-yl)amino)-2,7-naphthyridin-3-yl)-3-fluoro-5-methylbenzamide |
| 541 | 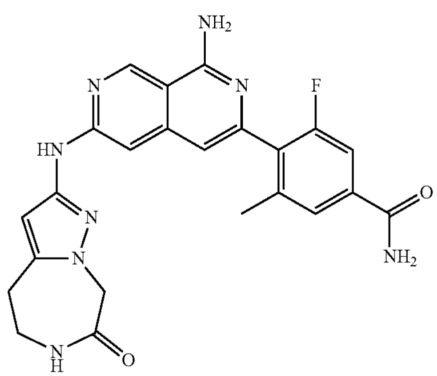 [SMILES: Cc1cc(C(N)=O)cc(F)c1-c1cc2cc(Nc3cc4n(n3)CC(=O)NCC4)ncc2c(N)n1] | 4-(1-amino-6-((7-oxo-5,6,7,8-tetrahydro-4H-pyrazolo[1,5-d][1,4]diazepin-2-yl)amino)-2,7-naphthyridin-3-yl)-3-fluoro-5-methylbenzamide |
| 542 | 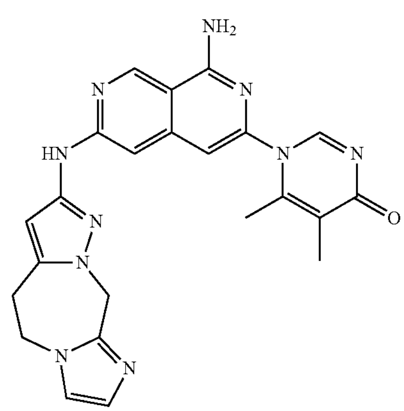 [SMILES: Cc1c(C)n(-c2cc3cc(Nc4cc5n(n4)Cc4nccn4CC5)ncc3c(N)n2)cnc1=O] | 1-(1-amino-6-((5,6-dihydro-11H-imidazo[1,2-a]pyrazolo[1,5-d][1,4]diazepin-8-yl)amino)-2,7-naphthyridin-3-yl)-5,6-dimethylpyrimidin-4(1H)-one |
| 543 | 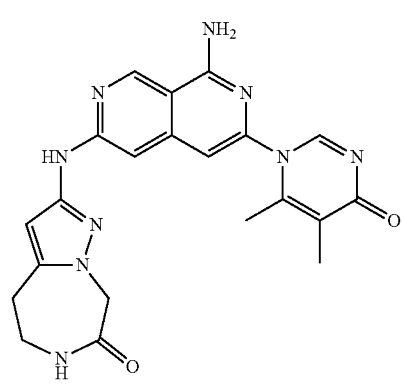 [SMILES: Cc1c(C)n(-c2cc3cc(Nc4cc5n(n4)CC(=O)NCC5)ncc3c(N)n2)cnc1=O] | 2-((8-amino-6-(5,6-dimethyl-4-oxopyrimidin-1(4H)-yl)-2,7-naphthyridin-3-yl)amino)-5,6-dihydro-4H-pyrazolo[1,5-d][1,4]diazepin-7(8H)-one |

TABLE 3-continued

| Cmpd No. | Structure | Name |
|---|---|---|
| 544 | 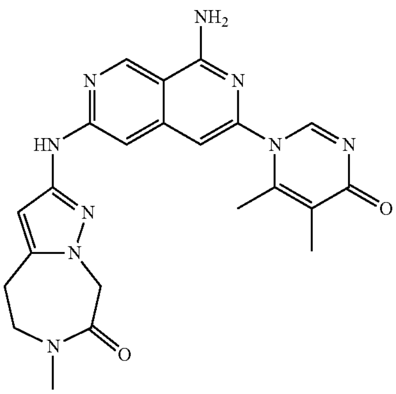 [SMILES: Cc1c(C)n(-c2cc3cc(Nc4cc5n(n4)CC(=O)N(C)CC5)ncc3c(N)n2)cnc1=O] | 2-((8-amino-6-(5,6-dimethyl-4-oxopyrimidin-1(4H)-yl)-2,7-naphthyridin-3-yl)amino)-6-methyl-5,6-dihydro-4H-pyrazolo[1,5-d][1,4]diazepin-7(8H)-one |
| 545 | 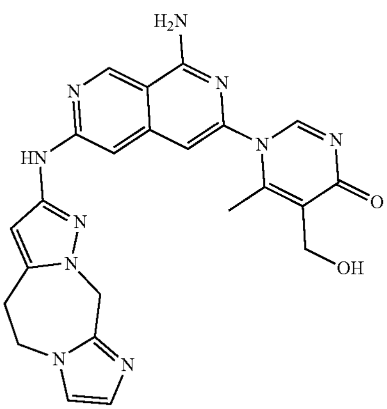 [SMILES: Cc1c(CO)c(=O)ncn1-c1cc2cc(Nc3cc4n(n3)Cc3nccn3CC4)ncc2c(N)n1] | 1-(1-amino-6-((5,6-dihydro-11H-imidazo[1,2-a]pyrazolo[1,5-d][1,4]diazepin-8-yl)amino)-2,7-naphthyridin-3-yl)-5-(hydroxymethyl)-6-methylpyrimidin-4(1H)-one |
| 546 | 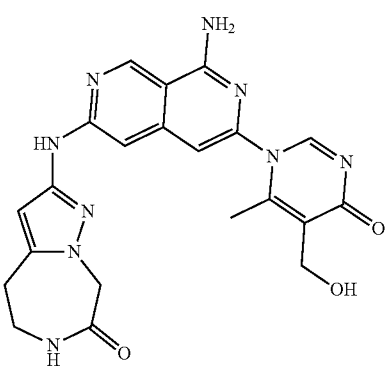 [SMILES: Cc1c(CO)c(=O)ncn1-c1cc2cc(Nc3cc4n(n3)CC(=O)NCC4)ncc2c(N)n1] | 2-((8-amino-6-(5-(hydroxymethyl)-6-methyl-4-oxopyrimidin-1(4H)-yl)-2,7-naphthyridin-3-yl)amino)-5,6-dihydro-4H-pyrazolo[1,5-d][1,4]diazepin-7(8H)-one |
| 547 | 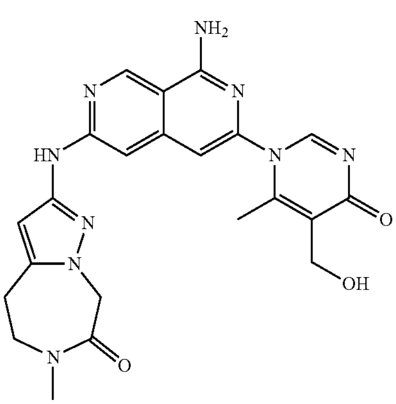 [SMILES: Cc1c(CO)c(=O)ncn1-c1cc2cc(Nc3cc4n(n3)CC(=O)N(C)CC4)ncc2c(N)n1] | 2-((8-amino-6-(5-(hydroxymethyl)-6-methyl-4-oxopyrimidin-1(4H)-yl)-2,7-naphthyridin-3-yl)amino)-6-methyl-5,6-dihydro-4H-pyrazolo[1,5-d][1,4]diazepin-7(8H)-one |

TABLE 3-continued

| Cmpd No. | Structure | Name |
|---|---|---|
| 548 | 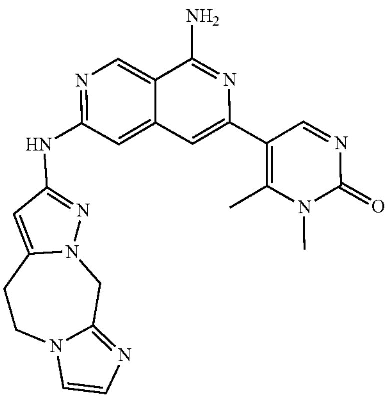 [SMILES: Cc1c(-c2cc3cc(Nc4cc5n(n4)Cc4nccn4CC5)ncc3c(N)n2)cnc(=O)n1C] | 5-(1-amino-6-((5,6-dihydro-11H-imidazo[1,2-a]pyrazolo[1,5-d][1,4]diazepin-8-yl)amino)-2,7-naphthyridin-3-yl)-1,6-dimethylpyrimidin-2(1H)-one |
| 549 | 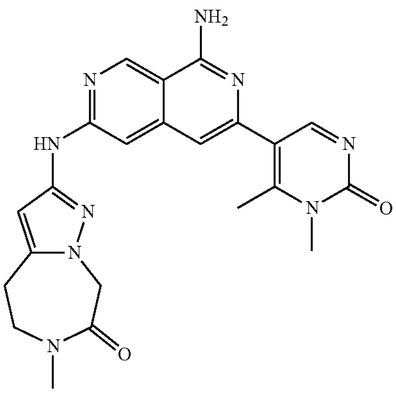 [SMILES: Cc1c(-c2cc3cc(Nc4cc5n(n4)CC(=O)N(C)CC5)ncc3c(N)n2)cnc(=O)n1C] | 2-((8-amino-6-(1,6-dimethyl-2-oxo-1,2-dihydropyrimidin-5-yl)-2,7-naphthyridin-3-yl)amino)-6-methyl-5,6-dihydro-4H-pyrazolo[1,5-d][1,4]diazepin-7(8H)-one |
| 550 | 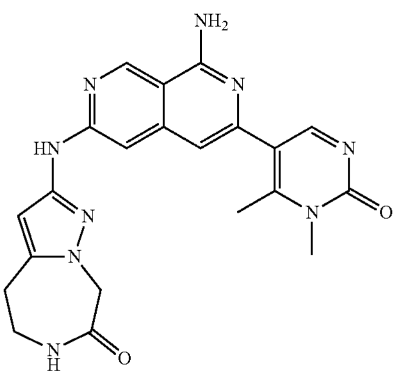 [SMILES: Cc1c(-c2cc3cc(Nc4cc5n(n4)CC(=O)NCC5)ncc3c(N)n2)cnc(=O)n1C] | 2-((8-amino-6-(1,6-dimethyl-2-oxo-1,2-dihydropyrimidin-5-yl)-2,7-naphthyridin-3-yl)amino)-5,6-dihydro-4H-pyrazolo[1,5-d][1,4]diazepin-7(8H)-one |
| 551 | 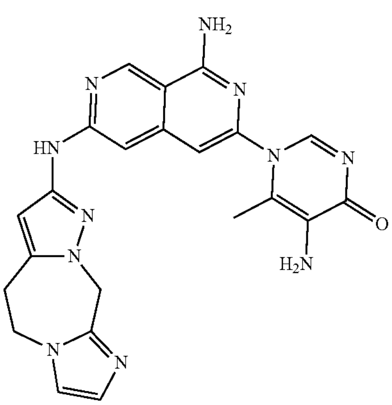 [SMILES: Cc1c(N)c(=O)ncn1-c1cc2cc(Nc3cc4n(n3)Cc3nccn3CC4)ncc2c(N)n1] | 5-amino-1-(1-amino-6-((5,6-dihydro-11H-imidazo[1,2-a]pyrazolo[1,5-d][1,4]diazepin-8-yl)amino)-2,7-naphthyridin-3-yl)-6-methylpyrimidin-4(1H)-one |

TABLE 3-continued

| Cmpd No. | Structure | Name |
|---|---|---|
| 552 | 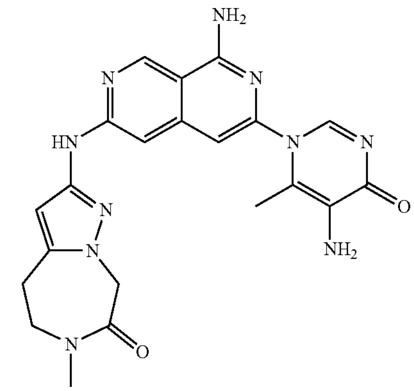 [SMILES: Cc1c(N)c(=O)ncn1-c1cc2cc(Nc3cc4n(n3)CC(=O)N(C)CC4)ncc2c(N)n1] | 2-((8-amino-6-(5-amino-6-methyl-4-oxopyrimidin-1(4H)-yl)-2,7-naphthyridin-3-yl)amino)-6-methyl-5,6-dihydro-4H-pyrazolo[1,5-d][1,4]diazepin-7(8H)-one |
| 553 | 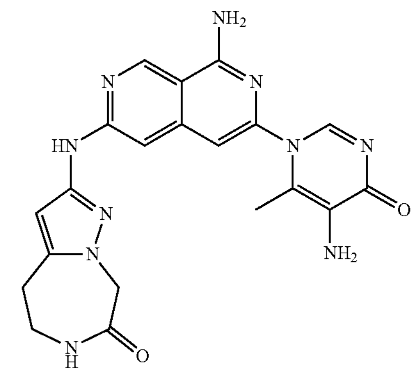 [SMILES: Cc1c(N)c(=O)ncn1-c1cc2cc(Nc3cc4n(n3)CC(=O)NCC4)ncc2c(N)n1] | 2-((8-amino-6-(5-amino-6-methyl-4-oxopyrimidin-1(4H)-yl)-2,7-naphthyridin-3-yl)amino)-5,6-dihydro-4H-pyrazolo[1,5-d][1,4]diazepin-7(8H)-one |
| 554 | | cis-N-(8-amino-6-(8-methyl-2,3-dihydro-1H-pyrido[2,3-b][1,4]oxazin-7-yl)-2,7-naphthyridin-3-yl)-2-(2-hydroxyethyl)cyclopropane-1-carboxamide |

TABLE 3-continued
| Cmpd No. | Structure | Name |
|---|---|---|
| 555 | 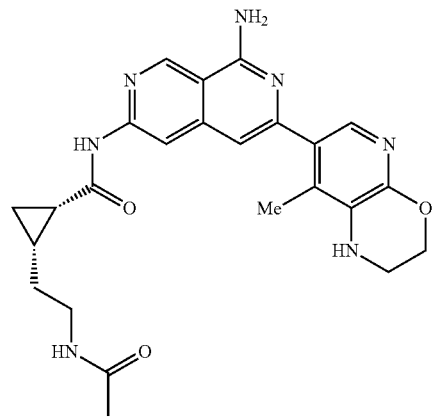 | cis-2-(2-acetamidoethyl)-N-(8-amino-6-(8-methyl-2,3-dihydro-1H-pyrido[2,3-b][1,4]oxazin-7-yl)-2,7-naphthyridin-3-yl)cyclopropane-1-carboxamide |
| 556 | 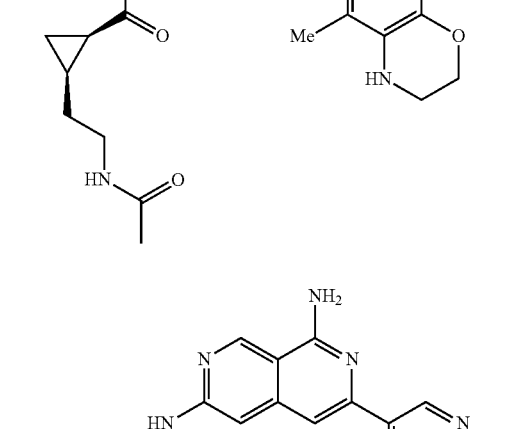 | (1R,3R,6S,7S)-3-acetamido-N-(8-amino-6-(8-methyl-2,3-dihydro-1H-pyrido[2,3-b][1,4]oxazin-7-yl)-2,7-naphthyridin-3-yl)bicyclo[4.1.0]heptane-7-carboxamide |
| 557 | 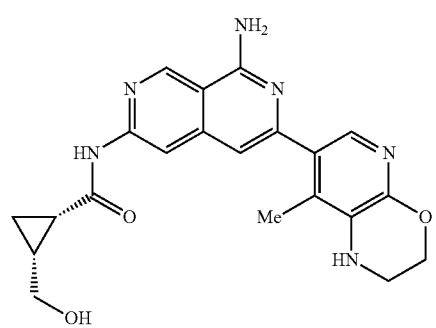 | cis-N-(8-amino-6-(8-methyl-2,3-dihydro-1H-pyrido[2,3-b][1,4]oxazin-7-yl)-2,7-naphthyridin-3-yl)-2-(hydroxymethyl)cyclopropane-1-carboxamide |

| Cmpd No. | Structure | Name |
|---|---|---|
| | | |
| 558 | 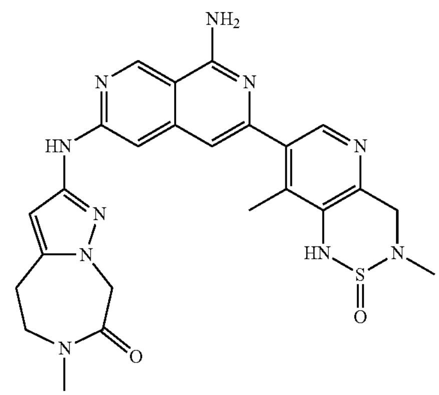 [SMILES: Cc1c(-c2cc3cc(Nc4cc5n(n4)CC(=O)N(C)CC5)ncc3c(N)n2)cnc2c1NS(=O)N(C)C2] | 7-(1-amino-6-((5,6-dihydro-11H-imidazo[1,2-a]pyrazolo[1,5-d][1,4]diazepin-8-yl)amino)-2,7-naphthyridin-3-yl)-3,8-dimethyl-3,4-dihydro-1H-pyrido[3,2-c][1,2,6]thiadiazine2-oxide |
| 559 | 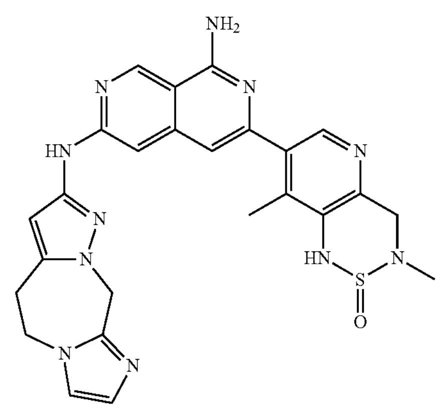 [SMILES: Cc1c(-c2cc3cc(Nc4cc5n(n4)Cc4nccn4CC5)ncc3c(N)n2)cnc2c1NS(=O)N(C)C2] | 2-((8-amino-6-(3,8-dimethyl-2-oxido-3,4-dihydro-1H-pyrido[3,2-c][1,2,6]thiadiazin-7-yl)-2,7-naphthyridin-3-yl)amino)-6-methyl-5,6-dihydro-4H-pyrazolo[1,5-d][1,4]diazepin-7(8H)-one |
| 560 | 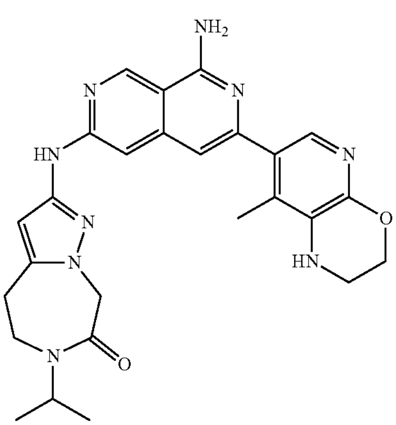 [SMILES: Cc1c(-c2cc3cc(Nc4cc5n(n4)CC(=O)N(C(C)C)CC5)ncc3c(N)n2)cnc2c1NCCO2] | 2-((8-amino-6-(8-methyl-2,3-dihydro-1H-pyrido[2,3-b][1,4]oxazin-7-yl)-2,7-naphthyridin-3-yl)amino)-6-isopropyl-5,6-dihydro-4H-pyrazolo[1,5-d][1,4]diazepin-7(8H)-one |

TABLE 3-continued

| Cmpd No. | Structure | Name |
|---|---|---|
| 561 | 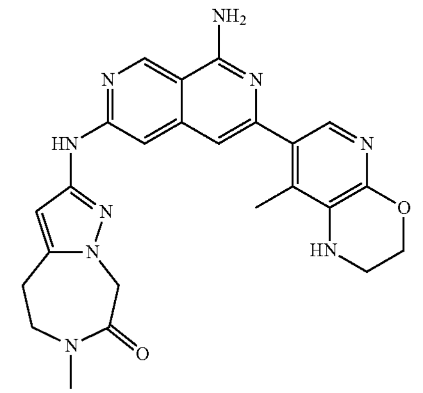 | 2-((8-amino-6-(8-methyl-2,3-dihydro-1H-pyrido[2,3-b][1,4]oxazin-7-yl)-2,7-naphthyridin-3-yl)amino)-6-methyl-5,6-dihydro-4H-pyrazolo[1,5-d][1,4]diazepin-7(8H)-one |
| 562 | 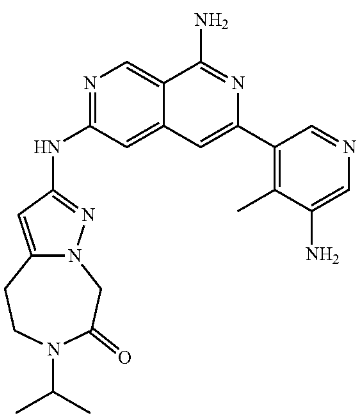 [SMILES: Cc1c(N)cncc1-c1cc2cc(Nc3cc4n(n3)CC(=O)N(C(C)C)CC4)ncc2c(N)n1] | 2-((8-amino-6-(5-amino-4-methylpyridin-3-yl)-2,7-naphthyridin-3-yl)amino)-6-isopropyl-5,6-dihydro-4H-pyrazolo[1,5-d][1,4]diazepin-7(8H)-one |
| 563 | 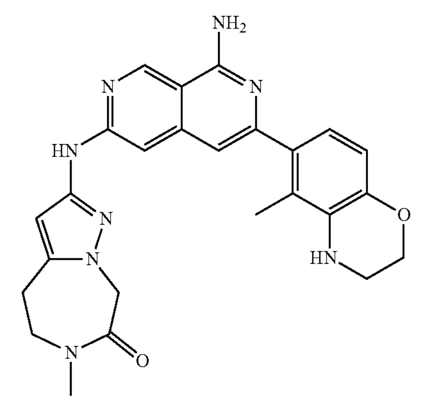 [SMILES: Cc1c(-c2cc3cc(Nc4cc5n(n4)CC(=O)N(C)CC5)ncc3c(N)n2)ccc2c1NCCO2] | 2-((8-amino-6-(5-methyl-3,4-dihydro-2H-benzo[b][1,4]oxazin-6-yl)-2,7-naphthyridin-3-yl)amino)-6-methyl-5,6-dihydro-4H-pyrazolo[1,5-d][1,4]diazepin-7(8H)-one |
| 564 | 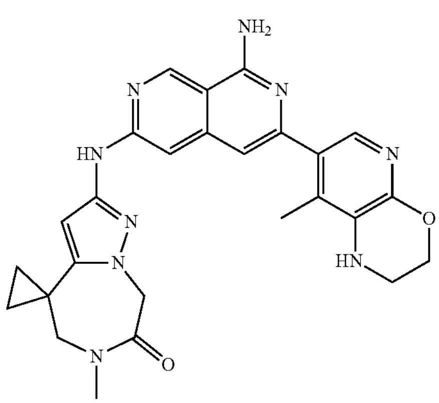 [SMILES: Cc1c(-c2cc3cc(Nc4cc5n(n4)CC(=O)N(C)CC54CC4)ncc3c(N)n2)cnc2c1NCCO2] | 2'-((8-amino-6-(8-methyl-2,3-dihydro-1H-pyrido[2,3-b][1,4]oxazin-7-yl)-2,7-naphthyridin-3-yl)amino)-6'-methyl-5',6'-dihydrospiro[cyclopropane-1,4'-pyrazolo[1,5-d][1,4]diazepin]-7'(8'H)-one |

TABLE 3-continued

| Cmpd No. | Structure | Name |
|---|---|---|
| 565 | 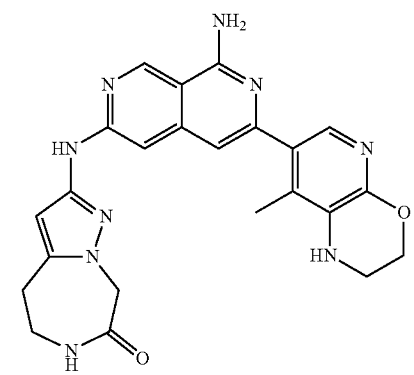 | 2-((8-amino-6-(8-methyl-2,3-dihydro-1H-pyrido[2,3-b][1,4]oxazin-7-yl)-2,7-naphthyridin-3-yl)amino)-5,6-dihydro-4H-pyrazolo[1,5-d][1,4]diazepin-7(8H)-one |
| 566 | 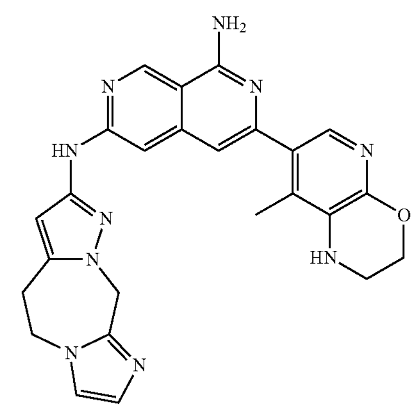 | N6-(5,6-dihydro-11H-imidazo[1,2-a]pyrazolo[1,5-d][1,4]diazepin-8-yl)-3-(8-methyl-2,3-dihydro-1H-pyrido[2,3-b][1,4]oxazin-7-yl)-2,7-naphthyridine-1,6-diamine |
| 567 | 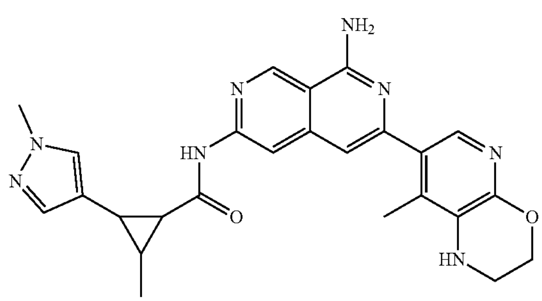 [SMILES: Cc1c(-c2cc3cc(NC(=O)C4C(C)C4c4cnn(C)c4)ncc3c(N)n2)cnc2c1NCCO2] | N-(8-amino-6-(8-methyl-2,3-dihydro-1H-pyrido[2,3-b][1,4]oxazin-7-yl)-2,7-naphthyridin-3-yl)-2-methyl-3-(1-methyl-1H-pyrazol-4-yl)cyclopropane-1-carboxamide |
| 568 | 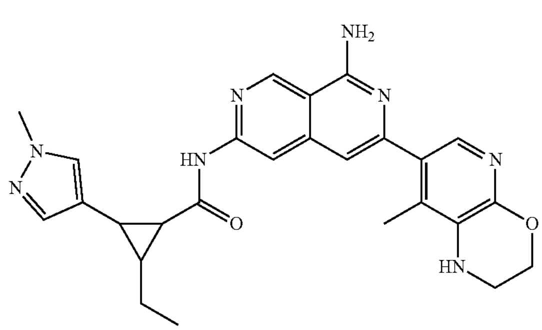 [SMILES: CCC1C(C(=O)Nc2cc3cc(-c4cnc5c(c4C)NCCO5)nc(N)c3cn2)C1c1cnn(C)c1] | N-(8-amino-6-(8-methyl-2,3-dihydro-1H-pyrido[2,3-b][1,4]oxazin-7-yl)-2,7-naphthyridin-3-yl)-2-ethyl-3-(1-methyl-1H-pyrazol-4-yl)cyclopropane-1-carboxamide |

TABLE 3-continued

| Cmpd No. | Structure | Name |
|---|---|---|
| 569 | 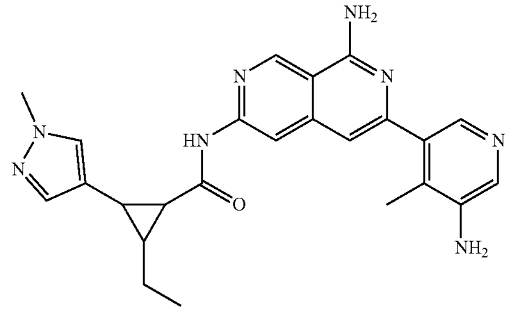 [SMILES: CCC1C(C(=O)Nc2cc3cc(-c4cncc(N)c4C)nc(N)c3cn2)C1c1cnn(C)c1] | N-(8-amino-6-(5-amino-4-methylpyridin-3-yl)-2,7-naphthyridin-3-yl)-2-ethyl-3-(1-methyl-1H-pyrazol-4-yl)cyclopropane-1-carboxamide |
| 570 | 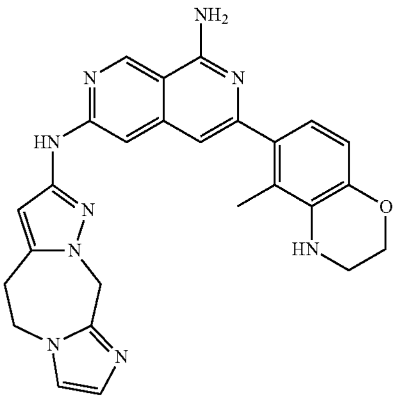 [SMILES: Cc1c(-c2cc3cc(Nc4cc5n(n4)Cc4nccn4CC5)ncc3c(N)n2)ccc2c1NCCO2] | N6-(5,6-dihydro-11H-imidazo[1,2-a]pyrazolo[1,5-d][1,4]diazepin-8-yl)-3-(5-methyl-3,4-dihydro-2H-benzo[b][1,4]oxazin-6-yl)-2,7-naphthyridine-1,6-diamine |
| 571 | 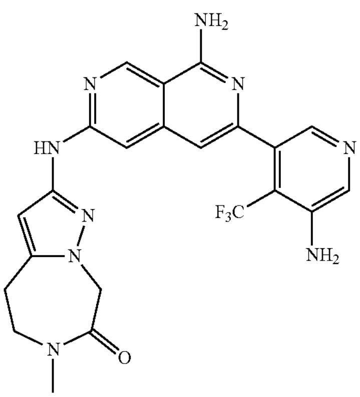 | 2-((8-amino-6-(5-amino-4-(trifluoromethyl)pyridin-3-yl)-2,7-naphthyridin-3-yl)amino)-6-methyl-5,6-dihydro-4H-pyrazolo[1,5-d][1,4]diazepin-7(8H)-one |
| 572 | 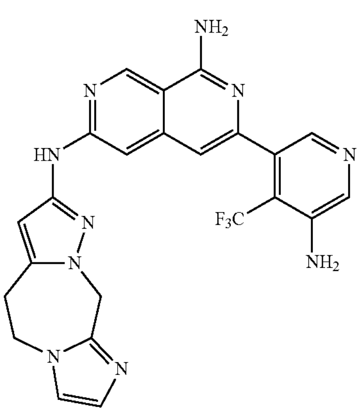 [SMILES: Nc1cncc(-c2cc3cc(Nc4cc5n(n4)Cc4nccn4CC5)ncc3c(N)n2)c1C(F)(F)F] | 3-(5-amino-4-(trifluoromethyl)pyridin-3-yl)-N6-(5,6-dihydro-11H-imidazo[1,2-a]pyrazolo[1,5-d][1,4]diazepin-8-yl)-2,7-naphthyridine-1,6-diamine |

In some embodiments, the compound is selected from the group consisting of Compound Nos. 1-348 in Table 1, or a pharmaceutically acceptable salt thereof. In some embodiments, the compound is selected from the group consisting of Compound Nos. 349-429 in Table 2, or a pharmaceutically acceptable salt thereof. In some embodiments, the compound is selected from the group consisting of Compound Nos. 430-572 in Table 3, or a pharmaceutically acceptable salt thereof.

Compounds of Formula I or Ia described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas I or Ia may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined herein.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

In embodiments, a pharmaceutical composition comprising a compound where all variables are as defined in any embodiment above, and a pharmaceutically acceptable carrier.

The subject matter disclosed herein includes prodrugs, metabolites, derivatives, and pharmaceutically acceptable salts of compounds of Formula I or Ia. Metabolites of the compounds of Formula I or Ia include compounds produced by a process comprising contacting a compound of Formula I or Ia with a mammal for a period of time sufficient to yield a metabolic product thereof.

If the compound of Formula I or Ia is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula I or Ia is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of Formula I or Ia can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

General Synthetic Schemes

Compounds of Formula I or Ia can be prepared by procedures in the Examples and generally by Schemes 1 and 2, where R groups are as described in Formula I or Ia, or precursors thereof.

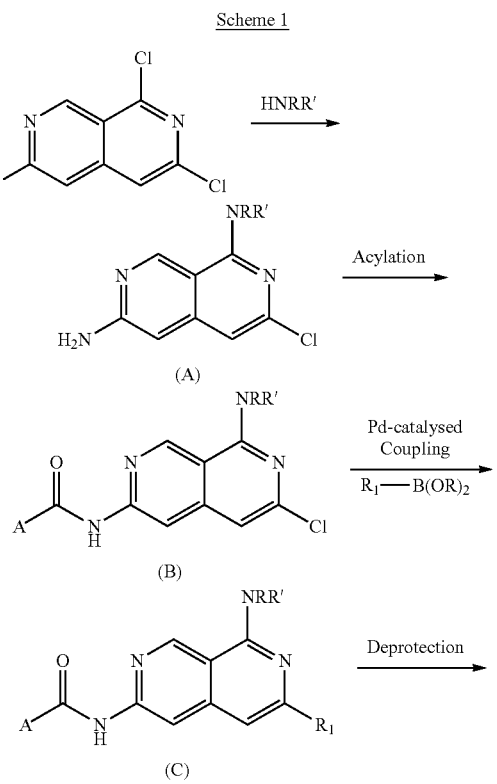

-continued

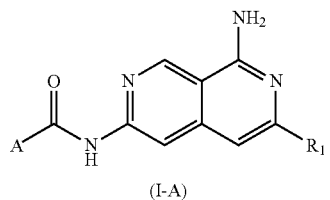

(I-A)

Scheme 1 shows a general synthetic method for preparing a compound of Formula I or Ia wherein $R_2$ is A-C(O)—. Reaction of 6,8-dichloro-2,7-naphthyridin-3-amine with an amine precursor HNRR' affords compound A, where R and R' are amine protecting groups (e.g., 4-methoxybenzyl or PMB). Acylation of the 3-amino group of compound A using an activated acyl compound (e.g., A-C(O)—X, where X is a leaving group such as Cl, Br or I) gives compound B. Pd-catalysed coupling of compound B with a boronic ester $R_1$—$B(OR)_2$ gives compound C. Deprotection of compound C yields the product of Formula (I-A), where A and $R_1$ are as defined for Formula I or Ia.

Provided is a method for making a compound of Formula (I-A) comprising reacting a compound B with a boronic ester $R_1$—$B(OR)_2$ (where R is an alkyl or aryl, or the two OR groups together with the boron atom to form a ring) and a Pd catalyst to form a compound C, and subjecting compound C to a condition for amine deprotection. The method may further comprise acylating a compound A (comprising reacting compound A with A-C(O)—X, where X is a leaving group such as Cl, Br or I) to form compound B

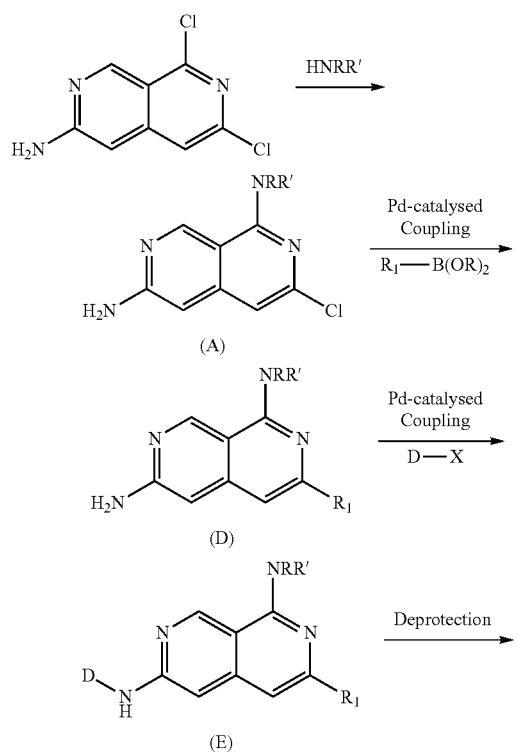

-continued

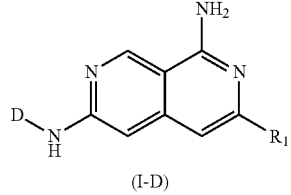

(I-D)

Scheme 2 shows a general synthetic method for preparing a compound of Formula I or Ia wherein $R_2$ is D. Reaction of 6,8-dichloro-2,7-naphthyridin-3-amine with an amine precursor HNRR' affords compound A, where R and R' are amine protecting groups (e.g., 4-methoxybenzyl). Pd-catalysed coupling of compound A with a boronic ester $R_1$—$B(OR)_2$ give compound D. Pd-catalysed coupling of compound D with a compound D-X gives compound E. Deprotection of compound C yields the product of Formula (I-D), where D and $R_1$ are as defined for Formula I or Ia.

Provided is a method for making a compound of Formula (I-D) comprising reacting a compound A with a boronic ester $R_1$—$B(OR)_2$ (where R is an alkyl or aryl, or the two OR groups together with the boron atom to form a ring) and a Pd catalyst to form a compound D; reacting a compound D with a compound D-X (where X is a leaving group such as Cl, Br or I) and a Pd catalyst to form a compound E, and subjecting compound E to a condition for amine deprotection.

Compositions

The presently disclosed compounds can be formulated into pharmaceutical compositions along with a pharmaceutically acceptable carrier.

Compounds of Formula I or Ia can be formulated in accordance with standard pharmaceutical practice as a pharmaceutical composition. According to this aspect, there is provided a pharmaceutical composition comprising a compound of Formula I or Ia in association with a pharmaceutically acceptable diluent or carrier.

A typical formulation is prepared by mixing a Formula I or Ia compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of Formula I or Ia is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of Formula I or Ia or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula I or Ia or stabilized form of the Formula I or Ia compound (e.g., complex with a cyclodextrin derivative or other known complexation agent) is dissolved in a suitable solvent in the presence of one or more of the excipients described above. The compound of Formula I or Ia is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations may be prepared for various routes and types of administration. For example, a compound of Formula I or Ia having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compounds of Formula I or Ia can be sterile. In particular, formulations to be used for in vivo administration should be sterile. Such sterilization is readily accomplished by filtration through sterile filtration membranes.

The compound ordinarily can be stored as a solid composition, a lyophilized formulation or as an aqueous solution.

The pharmaceutical compositions comprising a compound of Formula I or Ia can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences $16^{th}$ edition, Osol, A. Ed. (1980).

Sustained-release preparations of Formula I or Ia compounds may be prepared. Suitable examples of sustained-release preparations include semipermeable matrices of solid hydrophobic polymers containing a compound of Formula I or Ia, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or Ia suitable for oral administration may be prepared as discrete units such as pills, capsules, cachets or tablets each containing a predetermined amount of a compound of Formula I or Ia.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I or Ia intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400), and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise solely an emulsifier, it may also comprise a mixture of at least one emulsifier and a fat or oil, or both a fat and an oil. A hydrophilic emulsifier included together with a lipophilic emulsifier may act as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of Formula I or Ia compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I or Ia may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

In particular embodiments the pharmaceutical composition comprising the presently disclosed compounds further comprise a chemotherapeutic agent. In some of these embodiments, the chemotherapeutic agent is an immunotherapeutic agent.

Methods

The presently disclosed compounds find use in inhibiting the activity of the enzyme HPK1. HPK1, also referred to as mitogen activated protein kinase kinase kinase kinase 1 or MAP4K1, is a member of the germinal center kinase subfamily of Ste20-related serine/threonine kinases. HPK1 functions as a MAP4K by phosphorylating and activating MAP3K proteins, including MEKK1, MLK3 and TAK1, leading to the activation of the MAPK Jnk.

In an embodiment, the subject matter disclosed herein is directed to a method of inhibiting HPK1, the method comprising contacting HPK1 with an effective amount of a compound of Formula I or Ia or a pharmaceutical composition described herein.

In an embodiment, the subject matter disclosed herein is directed to a method for enhancing an immune response in a subject in need thereof, wherein the method comprises administering to the subject an effective amount of a compound of Formula I or Ia or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+CD8 T cells or enhanced levels of IL-2 or granzyme B production by T cells relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells.

In the methods described herein, a compound of Formula I or Ia or a pharmaceutical composition thereof is administered to a subject that has cancer as described elsewhere herein.

In an embodiment, the subject matter disclosed herein is directed to a method for treating a HPK1-dependent disorder, the method comprising administering to a subject in need thereof an effective amount of a compound of Formula I or Ia or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

HPK1 polynucleotides and polypeptides are known in the art (Hu et al. (1996) *Genes Dev.* 10: 2251-2264, which is herein incorporated by reference in its entirety). Non-limiting examples of HPK1 polynucleotides and polypeptides comprise the human HPK1 polynucleotide as set forth in SEQ ID NO: 1 (nucleotides 141-2642 of GenBank Accession No. NM_007181.5) and the encoded human HPK1 polypeptide (Accession No. NP_009112.1) as set forth in SEQ ID NO: 2. A shorter 821 amino acid isoform of HPK1 exists in humans, the coding sequence and amino acid sequence of which is set forth in SEQ ID NOs: 3 and 1, respectively (nucleotides 141-2606 of GenBank Accession No. NM_001042600.2 and GenBank Accession No. NP_001036065.1, respectively).

HPK1 polypeptides comprise a variety of conserved structural motifs. For ease of reference, such motifs will be discussed as they relate to the longer human HPK1 isoform, which is set forth in SEQ ID NO:2, comprises 833 amino acid residues. HPK1 polypeptides comprise an amino-terminal Ste20-like kinase domain that spans amino acid residues 17-293, which includes the ATP-binding site from amino acid residues 23-46. The kinase domain is followed by four proline-rich (PR) motifs that serve as binding sites for SH3-containing proteins, such as CrkL, Grb2, HIP-55, Gads, Nck, and Crk. The four PR motifs span amino acid residues 308-407, 394-402, 432-443, and 468-477, respectively. HPK1 becomes phosphorylated and activated in response to TCR or BCR stimulation. TCR- and BCR-induced phosphorylation of the tyrosine at position 381, located between PR1 and PR2, mediates binding to SLP-76 in T cells or BLNK in B cells via a SLP-76 or BLNK SH2 domain, and is required for activation of the kinase. A citron homology domain found in the C-terminus of HPK1, approximately spanning residues 495-800, may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a presently disclosed compound (i.e., compound of Formula I or Ia or a pharmaceutically acceptable salt, prodrug, metabolite, or derivative thereof).

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of Formula I or Ia or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of Formula I or Ia or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) *JEM* 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) *J Cell Biol* 195(5):839-853).

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

In some embodiments, administration of a compound of Formula I or Ia or a pharmaceutically acceptable salt, prodrug, metabolite, or derivative thereof to a subject results in an enhancement of T cell function.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

Accordingly, the presently disclosed compounds of Formula I or Ia or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

"Immunogenecity" refers to the ability of a particular substance to provoke an immune response. Tumors are immunogenic and enhancing tumor immunogenicity aids in the clearance of the tumor cells by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula I or Ia or a pharmaceutically acceptable salt, prodrug, metabolite, or derivative thereof. In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or at late state. In some embodiments, the subject has a hematological malignancy. The hematological malignancy may beat early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

The presently disclosed compounds may be administered in any suitable manner known in the art. In some embodiments, the compound of Formula I or Ia or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of Formula I or Ia or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In some embodiments, provided is a method for treating a cancer in a subject in need thereof comprising administering to the subject an effective amount of a compound of Formula I or Ia or a pharmaceutically acceptable salt, prodrug, metabolite, or derivative thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting the PI3K/AKT/mTOR pathway, HSP90 inhibitor, tubulin inhibitor, apoptosis inhibitor, and/or chemopreventative agent.

The additional therapy may be one or more of a chemotherapeutic agent. Thus, the method of treating cancer can comprise administering the presently disclosed HPK1 antagonists in conjunction with at least one chemotherapeutic agent.

As used herein, "in conjunction with" refers to administration of one treatment modality in addition to another treatment modality. As such, "in conjunction with" refers to administration of one treatment modality before, during, or after administration of the other treatment modality to the subject.

For example, the HPK1 antagonist and chemotherapeutic agent may be administered sequentially (at different times) or concurrently (at the same time). The HPK1 antagonist and chemotherapeutic agent may be administered by the same route of administration or by different routes of administration.

In certain embodiments, the HPK1 antagonist is administered in conjunction with another immunotherapy. For example, the HPK1 antagonist can be combined with a chemotherapeutic agent or biologic that targets the PDL1/PD1 pathway. A known inhibitory checkpoint pathway involves signaling through PD-1 receptors. The programmed-death 1 (PD-1) receptor and its ligands PD-L1 and PD-L2 are part of the same family of coregulatory molecules as CTLA-4.—See more at: http://www.onclive.com/web-exclusives/the-role-of-anti-pd-l1-immunotherapy-in-cancer/2#sthash.cGfYaT.dpuf Chemotherapeutic agents or biologics that block PD-L1 binding to PD-1 and CD80 can prevent PD-L1-mediated inhibition/suppression of T-cell activation. Programmed cell death ligand-1 (PD-L1) is widely expressed on antigen-presenting cells (APC) and other immune cells. It is upregulated on tumor cells from a broad range of human cancers, and has been implicated with inhibition of antitumor T-cell immunity. PD-L1 is a cell surface protein that binds to the receptors PD-1 and CD80 on activated T cells, B cells, and other myeloid cells. PD-L1 binding to PD-1 on activated T-cells has been found to interfere with T-cell proliferation and inhibit immune responses. Overexpression of PD-L1 on cancer cells may allow these cells to avoid immune detection and elimination. High levels of PD-L1 expression on tumor cells have been associated with increased tumor aggressiveness and a poor prognosis. Chemotherapeutic agents or biologics that block PD-L1 binding to PD-1 include anti-PD-L1 antibodies, such as durvalumab, nivolumab, pidlizumab, MPDL3280A, MK-3475 and BMS-936559, among others.

In another example, the HPK1 antagonist can be combined with a chemotherapeutic agent or biologic that targets OX40 and its ligand, OX40L, are members of the TNF superfamily. OX40 is expressed on activated CD4(+) and CD8(+) T cells as well as on a number of other lymphoid and non-lymphoid cells. Costimulatory signals from OX40 to a conventional T cell promote division and survival, augmenting the clonal expansion of effector and memory populations as they are being generated to antigen. OX40 additionally suppresses the differentiation and activity of T-regulatory cells, further amplifying this process. OX40 and OX40L also regulate cytokine production from T cells, antigen-presenting cells, natural killer cells, and natural killer T cells, and modulate cytokine receptor signaling. As one of the most prominent costimulatory molecules known to control T cells, stimulating OX40 has been shown be a target for therapeutic immunization strategies for cancer. Certain OX40 agonists include GBR 830, and those disclosed in Linch, et al., Frontiers in Oncology, v. 5, pp. 1-10 (2015), herein incorporated by reference in its entirety.

In some embodiments, the invention also provides compounds of Formula I or Ia described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of Formula I or Ia described herein or pharmaceutical compositions described herein for use in a method for inhibiting HPK1 as described herein.

In some embodiments, the invention also provides compounds of Formula I or Ia described herein or pharmaceutical compositions described herein for use in a method for enhancing an immune response in a subject in need thereof as described herein.

In some embodiments, the invention also provides compounds of Formula I or Ia described herein or pharmaceutical compositions described herein for use in a method for treating a HPK1-dependent disorder as described herein.

In some embodiments, the invention also provides the use of a compound of Formula I or Ia described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of Formula I or Ia described herein or a pharmaceutical composition described herein for the manufacture of a medicament for inhibiting HPK1.

In some embodiments, the invention also provides the use of a compound of Formula I or Ia described herein or a pharmaceutical composition described herein for the manufacture of a medicament for enhancing an immune response in a subject in need thereof.

In some embodiments, the invention also provides the use of a compound of Formula I or Ia described herein or a pharmaceutical composition described herein for the manufacture of a medicament treating a HPK1-dependent disorder.

In some embodiments, the invention also provides the use of compounds of Formula I or Ia described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of Formula I or Ia described herein or pharmaceutical compositions described herein in a method for inhibiting HPK1 as described herein.

In some embodiments, the invention also provides the use of compounds of Formula I or Ia described herein or pharmaceutical compositions described herein in a method for enhancing an immune response in a subject in need thereof as described herein.

In some embodiments, the invention also provides the use of compounds of Formula I or Ia described herein or pharmaceutical compositions described herein in a method for treating a HPK1-dependent disorder as described herein.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPK1 antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered a HPK1 antagonist is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for cancer may be a person demonstrating symptoms of cancer, one that has been diagnosed with cancer, a subject that is in remission from cancer, or a subject having an increased risk for developing cancer (e.g., a genetic predisposition, certain dietary or environmental exposures).

The following examples are offered by way of illustration and not by way of limitation.

EXAMPLES

Materials and Methods

Method A: Experiments performed on an Agilent 1100 HPLC with Agilent MSD mass spectrometer using ESI as ionization source using an Agilent SunFire-C18 3.5 μm, 4.6×50 column and a 2.0 ml/minute flow rate. The solvent system was a gradient starting with 95% water with 0.05% TFA (solvent A) and 5% acetonitrile with 0.05% TFA (solvent B), ramping up to 100% solvent B over 1.3 minutes. The final solvent system was held constant for a further 1.2 minutes.

Method B: Experiments performed on an Agilent 1200 HPLC with Agilent MSD mass spectrometer using ESI as ionization source using an Agilent SunFire-C18 3.5 μm, 4.6×50 column and a 2.0 ml/minute flow rate. The solvent system was a gradient starting with 95% water with 0.01% TFA (solvent A) and 5% acetonitrile with 0.01% TFA (solvent B), ramping up to 5% solvent A and 95% solvent B over 1.4 minutes. The final solvent system was held constant for a further 1.0 minute.

Method C: Experiments performed on an Agilent 1200 HPLC with Agilent MSD mass spectrometer using ESI as ionization source using an Agilent Xbridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.3 minutes. The final solvent system was held constant for a further 1.2 minutes.

Method D: Experiments performed on an Agilent 1200 HPLC with Agilent MSD mass spectrometer using ESI as ionization source using an Agilent Xbridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.6 minutes. The final solvent system was held constant for a further 1.0 minute.

Method E: Experiments performed on an Agilent 1200 HPLC with Agilent MSD mass spectrometer using ESI as ionization source using an Agilent SunFire-C18 3.5 μm, 4.6×50 column and a 2.0 ml/minute flow rate. The solvent system was a gradient starting with 95% water with 0.01% TFA (solvent A) and 5% acetonitrile with 0.01% TFA (solvent B), ramping up to 5% solvent A and 95% solvent B over 1.5 minutes. The final solvent system was held constant for a further 1.0 minute.

Method F: Experiments performed on an Agilent 1200 HPLC with Agilent MSD mass spectrometer using ESI as ionization source using an Agilent Xbridge-C18, 3.5 um, 4.6×50 mm column and a 1.8 ml/minute flow rate. The solvent system was a gradient starting with 90% water with 10 mM $NH_4HCO_3$ (solvent A) and 10% acetonitrile (solvent B), ramping up to 5% solvent A and 95% solvent B over 1.5 minutes. The final solvent system was held constant for a further 1.0 minute.

Method G: Experiments performed on an Agilent 1200 HPLC with Agilent MSD mass spectrometer using ESI as ionization source using an Agilent Xbridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.4 minutes. The final solvent system was held constant for a further 1.0 minute.

Method H: Experiments performed on an Agilent 1200 HPLC with Agilent MSD mass spectrometer using ESI as ionization source using Gemini-Nx 3μ, C18, 3 μm, 4.6×50 mm column and a 1.8 ml/minute flow rate. The solvent system was a gradient starting with 90% water with 10 mM $NH_4HCO_3$ (solvent A) and 10% acetonitrile (solvent B), ramping up to 5% solvent A and 95% solvent B over 1.5 minutes. The final solvent system was held constant for a further 1.0 minute.

Method I: Experiments performed on a Waters QDa mass spectrometer linked to a Waters Acquity H-Class UPLC system with a PDA detector. The spectrometer has an electrospray source operating in positive and negative ion mode. This system uses an Acquity BEH C18 1.7 μm, 50×2.1 mm column, maintained at 50° C. and a 1.0 mL/minute flow rate. The solvent system was a gradient from 97% water containing 0.1% formic acid (solvent A) and 3% acetonitrile containing 0.1% formic acid (solvent B) up to 1% solvent A and 99% solvent B over 1.5 minutes. This was maintained for 0.4 minutes before returning to 97% solvent A and 3% solvent B over the next 0.1 minutes. Total run time was 2.5 minutes.

Method I-1: Experiments performed on an Agilent 1200 HPLC with Agilent MSD mass spectrometer using ESI as ionization source using XBridge-C18, 3.5 μm, 4.6×50 mm column and a 1.8 ml/minute flow rate. The solvent system was a gradient starting with 95% water with 10 mM $NH_4HCO_3$ (solvent A) and 5% acetonitrile (solvent B), ramping up to 5% solvent A and 95% solvent B over 1.6 minutes. The final solvent system was held constant for a further 1.0 minute.

Method J: Experiments performed on a Waters Micromass ZQ mass spectrometer linked to a Waters Acquity UPLC system with a PDA detector. The spectrometer has an electrospray source operating in positive and negative ion mode. This system uses an Acquity BEH C18 1.7 μm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 0.2 minutes. Total run time was 8 minutes.

Method K: Experiments performed on a Waters Micromass ZQ mass spectrometer linked to an Agilent HP1100 HPLC system with a PDA detector. The spectrometer has an electrospray source operating in positive and negative ion mode. This system uses a Phenomenex Luna C18 3 μm, 30×4.6 mm column, and a 2.0 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 minutes. This was maintained for 1.0 minutes before returning to 95% solvent A and 5% solvent B over the next 0.5 minutes. Total run time was 6 minutes.

Method K-1: Experiments performed on a Shimadzu LC-20AD with LCMS-2020 mass spectrometer using ESI as ionization source using a Shim-Pack XR-ODS 2.2 μm, 3.0×50 column and a 1.2 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute.

Method L: Experiments performed on a Shimadzu LC-30AD with LCMS-2020 mass spectrometer using ESI as ionization source using an Ascentis Express C18 2.7 μm, 3.0×50 mm column and a 1.0 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute.

Method M: Experiments performed on a Shimadzu LC-20ADXR with LCMS-2020 mass spectrometer using ESI as ionization source using a poroshell HPH-C18, 2.7 um, 3.0×50 column and a 1.2 ml/minute flow rate. The solvent system was a gradient starting with 95% water with 5 mM $NH_4HCO_3$ (solvent A) and 5% acetonitrile (solvent B), ramping up to 95% solvent B over 2.0 minutes. The final solvent system was held constant for a further 0.7 minutes.

Method N: Experiments performed on a Shimadzu LC-30AD with LCMS-2020 mass spectrometer using ESI as ionization source using a CAPCELL CORE C18, 2.7 μm, 2.1×50 mm column and a 1.0 ml/minute flow rate. The solvent system was a gradient starting with 95% water with 0.1% FA (solvent A) and 5% acetonitrile with 0.1% FA (solvent B), ramping up to 5% solvent A and 95% solvent B over 2.0 minutes. The final solvent system was held constant for a further 0.7 minute.

Method O: Experiments performed on a Shimadzu LC-30AD with LCMS-2020 mass spectrometer using ESI as ionization source using a kinetex EVO C18, 2.7 μm, 2.1×50 column and a 1.2 ml/minute flow rate. The solvent system was a gradient starting with 95% water with 6.5 mM $NH_4HCO_3$ (solvent A) and 5% acetonitrile (solvent B), ramping up to 95% solvent B over 2.0 minutes. The final solvent system was held constant for a further 0.7 minutes.

Method P: Experiments performed on a Shimadzu LC-20AD with LCMS-2010 mass spectrometer using ESI as ionization source using a Shim-Pack XR-ODS 2.2 um, 3.0×50 column and a 1.2 ml/minute flow rate. The solvent system was a gradient starting with 95% water with 0.05% TFA (solvent A) and 5% acetonitrile with 0.05% TFA (solvent B), ramping up to 5% solvent A and 95% solvent B over 2.0 minutes. The final solvent system was held constant for a further 0.7 minute.

Method Q: Experiments performed on an Agilent 1290 UHPLC coupled with Agilent MSD (6140) mass spectrometer using ESI as ionization source. The LC separation was using a Phenomenex XB-C18, 1.7 μm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Preparation of Compounds

Example 1

Synthetic Intermediates

Example I.1

Intermediate 1: tert-butyl N-(6,8-dichloro-2,7-naphthyridin-3-yl)carbamate

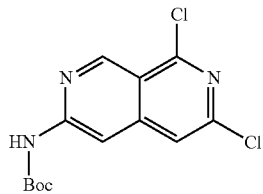 [SMILES: CC(C)(C)OC(=O)Nc1cc2cc(Cl)nc(Cl)c2cn1]

Step 1: 2,6-dichloro-4-iodonicotinic acid

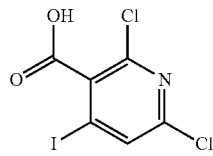 [SMILES: O=C(O)c1c(I)cc(Cl)nc1Cl]

To a solution of 2,6-dichloro-3-iodo-pyridine (13.69 g, 50 mmol) in dry THF (150 mL) was added dropwise LDA (2.0 M in THF, 27.5 mL, 55 mmol) at −78° C. under $N_2$. After the addition was completed, the reaction solution was stirred at −78° C. for 2 hours. After $CO_2$ was bubbled through for 5 min, the reaction mixture was stirred at room temperature for 2 hours. The reaction solution was quenched with conc. HCl and extracted with dichloromethane. The combined organic layer was dried over $Na_2SO_4$, filtered and concentrated to give 2,6-dichloro-4-iodo-pyridine-3-carboxylic acid (8.1 g, 51% yield) as a light yellow solid. LCMS (ESI) $[M+H]^+=317.8$.

Step 2: (2,6-dichloro-4-iodopyridin-3-yl)methanol

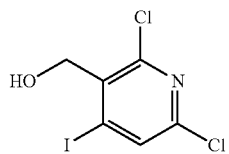 [SMILES: OCc1c(I)cc(Cl)nc1Cl]

A mixture of 2,6-dichloro-4-iodo-pyridine-3-carboxylic acid (6 g, 18.87 mmol) in THF (10 mL) was cooled to 0° C. $BH_3$-THF (1 M in THF, 94 mL, 94.37 mmol) was added slowly and then stirred at 85° C. for 16 hours. The mixture was poured into ice water and $K_2CO_3$ was added to adjust the pH to 8. The mixture was extracted with ethyl acetate (30 mL×2). The combined organic layer was dried over $Na_2SO_4$, filtered and concentrated. The crude product was purified by flash chromatography (petroleum ether/ethyl acetate=10/1) to give (2,6-dichloro-4-iodo-3-pyridyl)methanol (4 g, 69% yield) as a yellow solid. LCMS (ESI) $[M+H]^+=303.9$.

Step 3: 2,6-dichloro-4-iodonicotinaldehyde

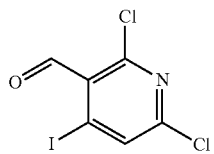 [SMILES: O=Cc1c(I)cc(Cl)nc1Cl]

To a solution of (2,6-dichloro-4-iodo-3-pyridyl)methanol (2.5 g, 8.23 mmol) in dichloromethane (100 mL) was added PCC (5 g, 23.26 mmol). The reaction mixture was stirred at 25° C. for 1 hour. The reaction mixture was filtered through a silica gel column and concentrated. The residue was purified by flash chromatography (petroleum ether/ethyl acetate=20/1) to give 2,6-dichloro-4-iodo-pyridine-3-carbaldehyde (1.6 g, 64% yield) as a yellow solid. $^1$H NMR (400 MHz, $CDCl_3$) δ 10.17 (s, 1H), 7.99 (s, 1H).

Step 4: (E)-N-tert-butyl-1-(2,6-dichloro-4-iodopyridin-3-yl)methanimine

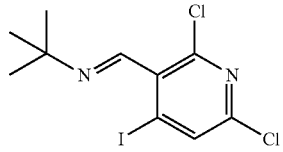

A mixture of 2,6-dichloro-4-iodo-pyridine-3-carbaldehyde (6.2 g, 20 mmol) and tert-butylamine (7.51 g, 103 mmol) in water (50 mL) was stirred at room temperature for 18 hours. The reaction mixture was extracted with ethyl acetate. The combined organic layer was dried over $Na_2SO_4$, filtered and concentrated to give N-tert-butyl-1-(2,6-dichloro-4-iodo-3-pyridyl) methanimine (7.2 g, 96% yield) as a white solid. LCMS (ESI) $[M+H]^+=356.9$.

Step 5: 6-((tert-butyldimethylsilyloxy)methyl)-1,3-dichloro-2,7-naphthyridine

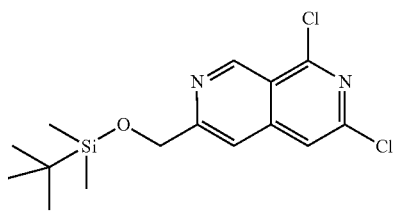 [SMILES: CC(C)(C)[Si](C)(C)OCc1cc2cc(Cl)nc(Cl)c2cn1]

A mixture of N-tert-butyl-1-(2,6-dichloro-4-iodo-3-pyridyl)methanimine (7.2 g, 20 mmol), tert-butyldimethyl(prop-2-ynyloxy)silane (3.78 g, 22 mmol), $NiCl_2$(DPPP) (546 mg, 1.01 mmol), Zn (196 mg, 3.03 mmol) in acetonitrile (40 mL) was heated to 85° C. for 18 hours under $N_2$. The reaction mixture was filtered. The filtrate was diluted with ethyl acetate, washed with water, dried over $Na_2SO_4$, filtered and concentrated. The crude was purified by flash chromatography (petroleum ether/ethyl acetate=15/1) to give tert-butyl-[(6,8-dichloro-2,7-naphthyridin-3-yl) methoxy]-dimethyl-silane (4 g, 44% yield) as a light yellow solid. LCMS (ESI) [M+H]$^+$=343.0.

Step 6: (6,8-dichloro-2,7-naphthyridin-3-yl)methanol

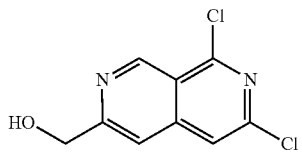 [SMILES: OCc1cc2cc(Cl)nc(Cl)c2cn1]

A solution of tert-butyl-[(6,8-dichloro-2,7-naphthyridin-3-yl)methoxy]-dimethyl-silane (4 g, 11.65 mmol) in a solution of HCl in ethanol (20 mL, 40 mmol) was stirred at 25° C. for 4 hours. The reaction mixture was filtered. The solid was collected, dissolved in aqueous NaHCO$_3$, and extracted with dichloromethane. The combined organic layers were dried over Na$_2$SO$_4$, filtered and concentrated to give (6,8-dichloro-2,7-naphthyridin-3-yl)methanol (2.5 g, 81% yield) as a yellow solid. LCMS (ESI) [M+H]$^+$=343.0.

Step 7: 6,8-dichloro-2,7-naphthyridine-3-carbaldehyde

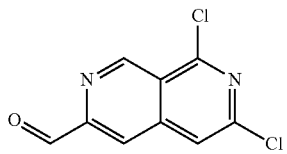 [SMILES: O=Cc1cc2cc(Cl)nc(Cl)c2cn1]

To a solution of (6,8-dichloro-2,7-naphthyridin-3-yl) methanol (2.8 g, 12 mmol) in dichloromethane (100 mL) and DMSO (25 mL) was added IBX (5.13 g, 18 mmol) at 0° C. The reaction solution was stirred at room temperature for 18 hours. The reaction mixture was diluted with dichloromethane, washed with 10% aqueous K$_2$CO$_3$ and brine, dried over MgSO$_4$, filtered and concentrated to give 6,8-dichloro-2,7-naphthyridine-3-carbaldehyde (2.2 g, 78% yield) as a white solid. LCMS (ESI) [M+H]$^+$=226.9.

Step 8: 6,8-dichloro-2,7-naphthyridine-3-carboxylic acid

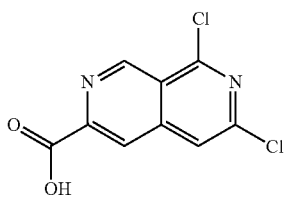 [SMILES: O=C(O)c1cc2cc(Cl)nc(Cl)c2cn1]

To a solution of 6,8-dichloro-2,7-naphthyridine-3-carbaldehyde (2.2 g, 9.69 mmol) in 1,4-dioxane (80 mL) and water (30 mL) was added NH$_2$SO$_3$H (1.13 g, 11.63 mmol) and NaClO$_2$ (1.05 g, 11.63 mmol) at room temperature. The reaction solution was stirred at room temperature for 18 hours. Water was then added. The precipitate was collected by filtration, washed with water and acetone to give 6,8-dichloro-2,7-naphthyridine-3-carboxylic acid (2.2 g, 74% yield) as a white solid. LCMS (ESI) [M+H]$^+$=242.9.

Step 9: tert-butyl N-(6,8-dichloro-2,7-naphthyridin-3-yl)carbamate

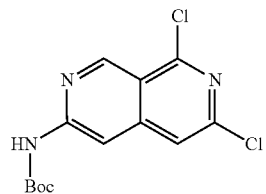 [SMILES: CC(C)(C)OC(=O)Nc1cc2cc(Cl)nc(Cl)c2cn1]

To a solution of 6,8-dichloro-2,7-naphthyridine-3-carboxylic acid (230 mg, 0.94 mmol), t-BuOH (1.4 g, 18.93 mmol) and DIPEA (158 mg, 1.23 mmol) in toluene (20 mL) was added a solution of DPPA (338 mg, 1.23 mmol) in toluene (2 mL) at 90° C. under N$_2$. The reaction solution was refluxed for 2 hours. The reaction solution was cooled to room temperature and methanol (40 mL) was added. The resulting solution was stirred at room temperature for 20 minutes, then concentrated. The residue was washed with methanol and dried to give tert-butyl N-(6,8-dichloro-2,7-naphthyridin-3-yl)carbamate (250 mg, 75% yield) as a white solid. LCMS (ESI) [M-55]$^+$=257.9. $^1$H NMR (400 MHz, DMSO-d$_6$) δ 10.56 (s, 1H), 9.37 (s, 1H), 8.23 (s, 1H), 8.10 (s, 1H), 1.52 (s, 9H).

Example I.2

Intermediate 2:6,8-dichloro-2,7-naphthyridin-3-amine

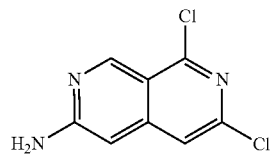 [SMILES: Nc1cc2cc(Cl)nc(Cl)c2cn1]

To a vial was added tert-butyl N-(6,8-dichloro-2,7-naphthyridin-3-yl)carbamate (1.05 g, 3.34 mmol), HCl in 1,4-dioxane (10 mL, 4 N, 40 mmol), and dichloromethane (5 mL). The mixture was stirred at 40° C. for 4 hours. The mixture was concentrated and dried under vacuum to give 6,8-dichloro-2,7-naphthyridin-3-amine hydrochloride (823 mg, 96% yield) as yellow solid. LCMS (ESI) [M+H]$^+$=214.1.

Example I.3

Intermediate 3: 3-chloro-N1,N1-bis(4-methoxybenzyl)-2,7-naphthyridine-1,6-diamine

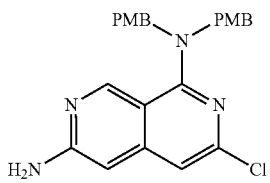

To a microwave tube was added 6,8-dichloro-2,7-naphthyridin-3-amine hydrochloride (800 mg, 3.19 mmol), 1-(4-methoxyphenyl)-N-[(4-methoxyphenyl)methyl]methanamine (2.47 g, 9.58 mmol), DIPEA (1.0 mL, 6.39 mmol), and 1,4-dioxane (4 mL). The mixture was stirred at 140° C. for 48 hours. The mixture was cooled, concentrated and purified by silica gel chromatography (dichloromethane/methanol/7N NH₃-methanol, 200/5/1) to afford 3-chloro-N1,N1-bis[(4-methoxyphenyl)methyl]-2,7-naphthyridine-1,6-diamine (1.02 g, 73% yield) as yellow solid. LCMS (ESI) [M+H]⁺=435.1.

Example I.4

Intermediate 4: (±)-cis-N-(6,8-dichloro-2,7-naphthyridin-3-yl)-2-fluorocyclopropanecarboxamide

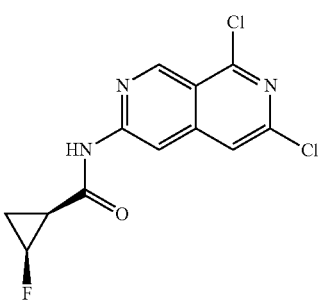 [SMILES: O=C(Nc1cc2cc(Cl)nc(Cl)c2cn1)[C@@H]1C[C@@H]1F]

To a solution of (±)-cis-2-fluorocyclopropanecarboxylic acid (200 mg, 1.92 mmol) in dichloromethane (10 mL) and DMF (0.10 mL) was added drop wise oxalyl dichloride (489 mg, 3.84 mmol). The mixture was stirred at 20° C. for 1 hour. The reaction mixture was then concentrated in vacuum to give a crude product of (±)-cis-2-fluorocyclopropanecarbonyl chloride as a yellow solid.

To a solution of 6,8-dichloro-2,7-naphthyridin-3-amine hydrochloride (400 mg, 1.6 mmol) in dichloromethane (15 mL) and pyridine (3 mL) was added (±)-cis-2-fluorocyclopropanecarbonyl chloride (220 mg, 1.8 mmol). The mixture was stirred at 20° C. for 2 hours. The reaction mixture was then washed with water (50 mL) and extracted with dichloromethane (100 mL×3). The organic extracts were combined and concentrated. The residue was purified by silica gel flash chromatography (petroleum ether/ethyl acetate=10:1 to 3:1) to afford (±)-cis-N-(6,8-dichloro-2,7-naphthyridin-3-yl)-2-fluoro-cyclopropanecarboxamide (350 mg, 66% yield) as a light yellow solid. LCMS (ESI) [M+H]⁺=300.2.

Example I.5

Intermediate 5: (±)-cis-N-(8-amino-6-chloro-2,7-naphthyridin-3-yl)-2-fluorocyclopropane carboxamide

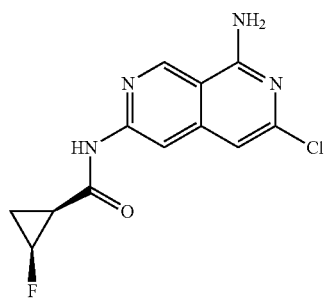 [SMILES: Nc1nc(Cl)cc2cc(NC(=O)[C@@H]3C[C@@H]3F)ncc12]

To a sealed tube was added N-(6,8-dichloro-2,7-naphthyridin-3-yl)-2-fluoro-cyclopropanecarboxamide (100 mg, 0.33 mmol), NH₄OH (1.0 mL) and 1,4-dioxane (2 mL). The mixture was stirred at 80° C. for 6 hours. The reaction mixture was then concentrated in vacuum and the residue was purified by silica gel flash chromatography (petroleum ether/ethyl acetate=3:1 to 1:5) to give N-(8-amino-6-chloro-2,7-naphthyridin-3-yl)-2-fluoro-cyclopropanecarboxamide (70 mg, 71% yield) as a white solid. LCMS (ESI) [M+H]⁺=281.1.

Example I.6

Intermediate 6: (±)-trans-2-cyano-N-(6,8-dichloro-2,7-naphthyridin-3-yl)cyclopropanecarboxamide

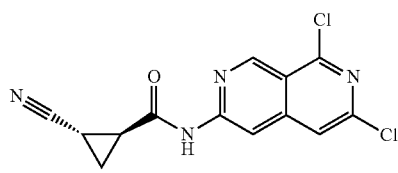 [SMILES: N#C[C@H]1C[C@@H]1C(=O)Nc1cc2cc(Cl)nc(Cl)c2cn1]

To a solution of 6,8-dichloro-2,7-naphthyridin-3-amine hydrochloride (250 mg, 1.0 mmol) in pyridine (5 mL) was added drop-wise a solution of (±)-trans-2-cyanocyclopropanecarbonyl chloride (200 mg, 1.8 mmol) in dichloromethane (5 mL) at 0° C. The mixture was stirred at 20° C. for 2 hours and then solvent was removed under reduced pressure. The resulting residue was purified by silica gel chromatography (petroleum ether/ethyl acetate from 10:1 to 1:2) to give (±)-trans-2-cyano-N-(6,8-dichloro-2,7-naphthyridin-3-yl)cyclopropanecarboxamide (255 mg, 79% yield) as a white solid. LCMS (ESI) [M+H]⁺=307.2.

Example I.7

Intermediate 7: (±)-trans-N-(8-amino-6-chloro-2,7-naphthyridin-3-yl)-2-cyanocyclopropane carboxamide

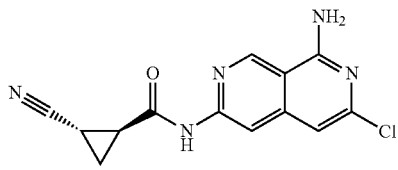

To a sealed tube was added (±)-trans-2-cyano-N-(6,8-dichloro-2,7-naphthyridin-3-yl) cyclopropane carboxamide (150 mg, 0.49 mmol), 1,4-dioxane (8 mL), and ammonium hydroxide (6 mL). The mixture was stirred at 100° C. for 4 hours and then concentrated to afford N-(8-amino-6-chloro-2,7-naphthyridin-3-yl)-2-cyano-cyclopropanecarboxamide (220 mg, 94% yield) as a white solid. LCMS (ESI) [M+H]$^+$=288.2.

Example I.8

Intermediate 8: (1S,2S)—N-(6,8-dichloro-2,7-naphthyridin-3-yl)-2-fluorocyclopropane carboxamide

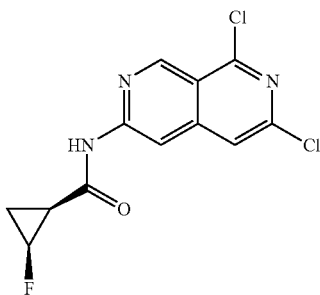 [SMILES: O=C(Nc1cc2cc(Cl)nc(Cl)c2cn1)[C@@H]1C[C@@H]1F]

To a solution of (1S,2S)-2-fluorocyclopropanecarboxylic acid (200 mg, 1.92 mmol) in dichloromethane (15 mL) and DMF (3 mL) was added dropwise oxalyl dichloride (0.24 mL, 2.88 mmol). The mixture was stirred at 20° C. for 2 hours. The reaction mixture was then concentrated under vacuum to give a yellow residue, which was then used in the next step directly.

To a solution of 6,8-dichloro-2,7-naphthyridin-3-amine hydrochloride (300 mg, 1.2 mmol) in dichloromethane (15 mL) and pyridine (3 mL) was added a solution of (1R,2S)-2-fluorocyclopropane carbonyl chloride (220 mg, 1.8 mmol) dissolved in dichloromethane (2 mL). The mixture was stirred at 20° C. for 2 hours. The reaction mixture was washed with water (50 mL) and extracted with dichloromethane (100 mL×3). The organic extracts were combined, concentrated in vacuum and the residue was purified by silica gel flash chromatography (petroleum ether/ethyl acetate=10:1 to 1:1) to give (1S,2S)—N-(6,8-dichloro-2,7-naphthyridin-3-yl)-2-fluoro-cyclopropanecarboxamide (330 mg, 71% yield) as a light yellow solid. LCMS (ESI) [M+H]$^+$=300.2.

Example I.9

Intermediate 9: (1S,2S)—N-(8-amino-6-chloro-2,7-naphthyridin-3-yl)-2-fluorocyclopropane carboxamide

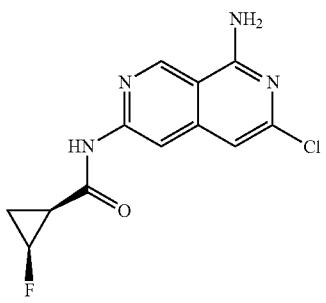 [SMILES: Nc1nc(Cl)cc2cc(NC(=O)[C@@H]3C[C@@H]3F)ncc12]

To a sealed tube was added (1S,2S)—N-(6,8-dichloro-2,7-naphthyridin-3-yl)-2-fluoro-cyclopropanecarboxamide (80 mg, 0.27 mmol), NH$_4$OH (1.0 mL) and 1,4-dioxane (2 mL). The mixture was stirred at 85° C. for 16 hours. The reaction mixture was then concentrated under vacuum. The residue was purified by silica gel flash chromatography (petroleum ether/ethyl acetate=3:1 to 1:5) to give (1S,2S)—N-(8-amino-6-chloro-2,7-naphthyridin-3-yl)-2-fluoro-cyclopropanecarboxamide (51 mg, 63% yield) as a white solid. LCMS (ESI) [M+H]$^+$=281.2.

Example I.10

Intermediate 10: Trans-N-(6,8-dichloro-2,7-naphthyridin-3-yl)-2-fluorocyclopropanecarboxamide

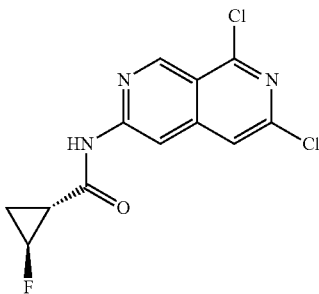 [SMILES: O=C(Nc1cc2cc(Cl)nc(Cl)c2cn1)[C@H]1C[C@@H]1F]

To a solution of (±)-trans-2-fluorocyclopropanecarboxylic acid (250 mg, 2.4 mmol) in dichloromethane (5 mL) and DMF (0.1 mL) was added dropwise oxalyl dichloride (375 mg, 2.95 mmol). The mixture was stirred at 20° C. for 2 hours. The reaction mixture was then concentrated under vacuum to give a yellow residue, which was then used in the next step directly.

To a solution of 6,8-dichloro-2,7-naphthyridin-3-amine hydrochloride (250 mg, 1.0 mmol) in pyridine (5 mL) was added a solution of (±)-trans-2-fluorocyclopropanecarbonyl chloride (240 mg, 1.96 mmol) dissolved in dichloromethane (2 mL). The mixture was stirred at 20° C. for 2 hours. The reaction was then concentrated under vacuum. The residue was purified by silica gel flash chromatography (petroleum ether/ethyl acetate=10:1 to 3:1) to give (±)-trans-N-(6,8- dichloro-2,7-naphthyridin-3-yl)-2-fluoro-cyclopropanecarboxamide (225 mg, 71% yield) as a light yellow solid. LCMS (ESI) [M+H]$^+$=300.0.

Example I.11

Intermediate 11: trans-N-(8-amino-6-chloro-2,7-naphthyridin-3-yl)-2-fluorocyclopropane carboxamide

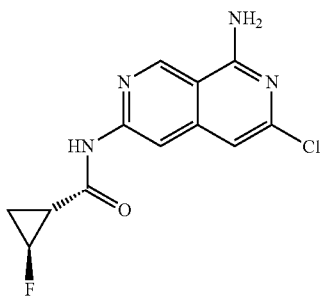

To a sealed tube was added (±)-trans-N-(6,8-dichloro-2,7-naphthyridin-3-yl)-2-fluoro-cyclopropanecarboxamide (125 mg, 0.42 mmol), NH$_4$OH (1.0 mL) and 1,4-dioxane (2 mL). The mixture was stirred at 90° C. for 16 hours. After 16 hours, the reaction mixture was concentrated under vacuum. The residue was purified by silica gel flash chromatography (petroleum ether/ethyl acetate=3:1 to 1:5) to give (1S,2R)—N-(8-amino-6-chloro-2,7-naphthyridin-3-yl)-2-fluoro-cyclopropanecarboxamide (75 mg, 64% yield) as a white solid. LCMS (ESI) [M+H]$^+$=281.2.

Example I.12

Intermediate 12: N-(6,8-dichloro-2,7-naphthyridin-3-yl)-2,2-difluorocyclopropanecarboxamide

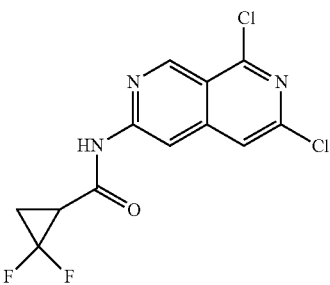 [SMILES: O=C(Nc1cc2cc(Cl)nc(Cl)c2cn1)C1CC1(F)F]

To a solution of 2,2-difluorocyclopropanecarboxylic acid (200 mg, 1.64 mmol) in dichloromethane (3 mL) and DMF (0.05 mL) was added dropwise oxalyl dichloride (0.21 mL, 2.46 mmol). The mixture was stirred at 20° C. for 2 hours. The reaction mixture was used in the next step directly without concentration.
To a solution of 6,8-dichloro-2,7-naphthyridin-3-amine hydrochloride (200 mg, 0.80 mmol) in pyridine (3 mL) was added 2,2-difluorocyclopropanecarbonyl chloride (200 mg, 1.42 mmol) dissolved in DMA (1 mL). The mixture was stirred at 20° C. for 2 hours. The reaction mixture was then concentrated. The residue was purified by silica gel flash chromatography (petroleum ether/ethyl acetate=20:1 to 3:1) to give N-(6,8-dichloro-2,7-naphthyridin-3-yl)-2,2-difluoro-cyclopropanecarboxamide (150 mg, 58% yield) as a yellow solid. LCMS (ESI) [M+H]$^+$=318.2.

Example I.13

Intermediate 13: N-(8-amino-6-chloro-2,7-naphthyridin-3-yl)-2,2-difluorocyclopropane carboxamide

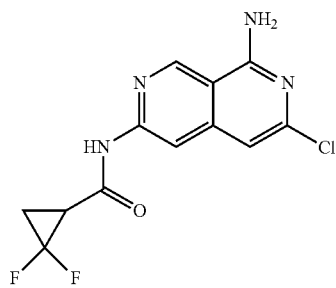 [SMILES: Nc1nc(Cl)cc2cc(NC(=O)C3CC3(F)F)ncc12]

To a sealed tube was added N-(6,8-dichloro-2,7-naphthyridin-3-yl)-2,2-difluoro-cyclopropanecarboxamide (100 mg, 0.31 mmol), NH$_4$OH (1.0 mL) and 1,4-dioxane (2 mL). The mixture was stirred at 95° C. for 6 hours. After 6 hours, the reaction mixture was concentrated in vacuum and the residue was purified by silica gel flash chromatography (petroleum ether/ethyl acetate=3:1 to 1:5) to give N-(8-amino-6-chloro-2,7-naphthyridin-3-yl)-2,2-difluoro-cyclopropanecarboxamide (55 mg, 59% yield) as a white solid. LCMS (ESI) [M+H]$^+$=299.2.

Example I.14

Intermediate 14: 4-ethylpyridin-3-ylboronic acid

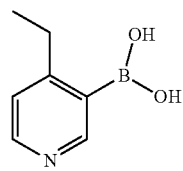

A solution of n-BuLi (2.5 M in hexane, 25 mL, 62.5 mmol) was added dropwise to a solution of 3-bromo-4-ethyl-pyridine (9.8 g, 52.69 mmol) and triisopropyl borate (12.0 g, 63.81 mmol) in THF (150 mL) at −78° C. over 0.5 h. The reaction mixture was stirred at −78° C. for another 0.5 h, then warmed slowly to room temperature and stirred for 0.5 hours. The reaction was quenched with water (120 mL). The aqueous layer was separated, washed with ethyl acetate (150 mL), and acidified with 3N HCl to pH 4-5. A light yellow solid precipitated. The precipitate was collected by filtration, and dried to give (4-ethyl-3-pyridyl)boronic acid (1.8 g, 23% yield) as a light yellow solid. LCMS (ESI) [M+H]$^+$=152.1.

Example I.15

Intermediate 15: 4-ethyl-3-(4,4,5,5-tetramethyl-1,3,2-dioxaborolan-2-yl)pyridine

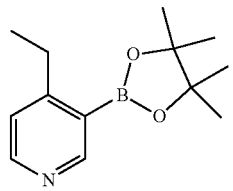 [SMILES: CCc1ccncc1B1OC(C)(C)C(C)(C)O1]

A mixture of 3-bromo-4-ethyl-pyridine (5.0 g, 26.88 mmol), bis(pinacolato)diboron (8.5 g, 33.47 mmol), PdCl$_2$dppf (1.0 g, 1.37 mmol), potassium acetate (8.0 g, 81.63 mmol) in 1,4-dioxane (150 mL) was stirred overnight at 90° C. under Ar. The reaction mixture was cooled to room temperature. Then bis(pinacolato)diboron (12.0 g, 47.26 mmol), PdCl$_2$dppf (1.0 g, 1.37 mmol) and 1,4-dioxane (150 mL) were added and the reaction mixture stirred overnight at 90° C. under Ar. The reaction mixture was cooled to room temperature and evaporated. The residue was purified with silica chromatography (petroleum ether/ethyl acetate=1/1) to afford 4-ethyl-3-(4,4,5,5-tetramethyl-1,3,2-dioxaborolan-2-yl)pyridine (4.3 g, 69% yield) as a black oil. LCMS (ESI) [M+H]$^+$=234.1.

Example I.16

Intermediate 16: 3-(4-ethylpyridin-3-yl)-N1,N1-bis(4-methoxybenzyl)-2,7-naphthyridine-1,6-diamine

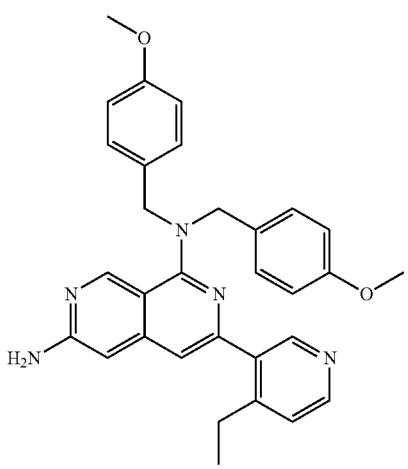 [SMILES: CCc1ccncc1-c1cc2cc(N)ncc2c(N(Cc2ccc(OC)cc2)Cc2ccc(OC)cc2)n1]

A mixture 3-chloro-N1,N1-bis[(4-methoxyphenyl)methyl]-2,7-naphthyridine-1,6-diamine (2.8 g, 6.44 mmol), 4-ethyl-3-(4,4,5,5-tetramethyl-1,3,2-dioxaborolan-2-yl)pyridine (2.5 g, 10.73 mol), XPhos Pd G2 (250 mg, 0.32 mmol), XPhos (250 mg, 0.53 mmol), K$_2$CO$_3$ (2 g, 14.49 mmol) in 1,4-dioxane (100 mL) and water (25 mL) was stirred at 100° C. under Ar for 2 hours. The reaction mixture was cooled to room temperature, diluted with ethyl acetate (200 mL), and washed with brine (100 mL). The organic layer was separated, dried over Na$_2$SO$_4$, filtered and concentrated. The residue was purified with silica gel chromatography (petroleum ether/ethyl acetate=1:2) to afford 3-(4-ethyl-3-pyridyl)-N1,N1-bis[(4-methoxyphenyl)methyl]-2,7-naphthyridine-1,6-diamine (1 g, 31% yield) as a brown solid. LCMS (ESI) [M+H]$^+$=506.2.

Example I.17

Intermediate 17: N1,N1-bis(4-methoxybenzyl)-3-(4-methylpyridin-3-yl)-2,7-naphthyridine-1,6-diamine

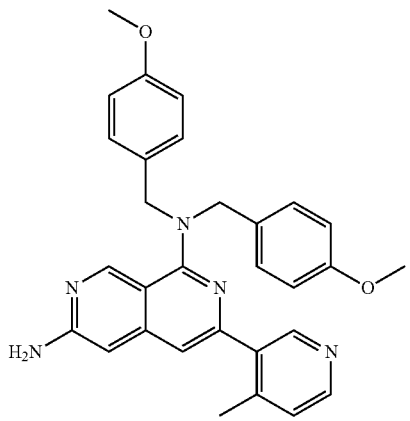 [SMILES: COc1ccc(CN(Cc2ccc(OC)cc2)c2nc(-c3cnccc3C)cc3cc(N)ncc23)cc1]

To a vial was added XPhos Pd G2 (120 mg, 0.15 mmol), X-phos (100 mg, 0.21 mmol), 3-chloro-N1,N1-bis[(4-methoxyphenyl)methyl]-2,7-naphthyridine-1,6-diamine (600 mg, 1.38 mmol), potassium acetate (300 mg, 3 mmol), 4-methyl-3-(4,4,5,5-tetramethyl-1,3,2-dioxaborolan-2-yl)pyridine (360 mg, 1.64 mmol), water (5 mL), and 1,4-dioxane (50 mL). The reaction mixture was bubbled with N$_2$ and stirred at 100° C. for 6 hours. The mixture was concentrated and purified by silica gel chromatography (dichloromethane/methanol from 30:1 to 10:1) to give N1,N1-bis[(4-methoxyphenyl)methyl]-3-(4-methyl-3-pyridyl)-2,7-naphthyridine-1,6-diamine (340 mg, 50% yield) as a yellow solid. LCMS (ESI) [M+H]$^+$=492.1.

Example I.18

Intermediate 18: N-(6-chloro-8-(diphenylmethyleneamino)-2,7-naphthyridin-3-yl) cyclopropane carboxamide

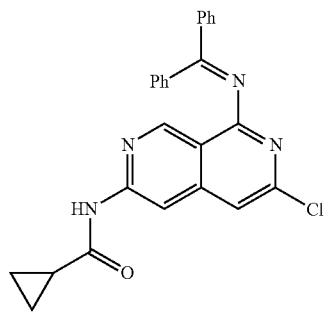 [SMILES: O=C(Nc1cc2cc(Cl)nc(N=C(c3ccccc3)c3ccccc3)c2cn1)C1CC1]

Step 1: N-(6,8-dichloro-2,7-naphthyridin-3-yl)cyclopropanecarboxamide

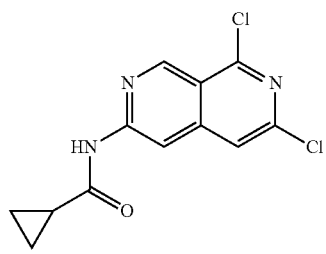 [SMILES: O=C(Nc1cc2cc(Cl)nc(Cl)c2cn1)C1CC1]

To a mixture of 6,8-dichloro-2,7-naphthyridin-3-amine (270 mg, 1.26 mmol) in pyridine (5 mL) was added cyclopropanecarbonyl chloride (197 mg, 1.89 mmol) at 0° C. The mixture was stirred at room temperature for 2 hours. Water (10 mL) was added and the mixture extracted with dichloromethane (10 mL×2). The organic layer was washed with water (20 mL×3), brine (20 mL×1), dried over $Na_2SO_4$, filtered and concentrated. The crude product was purified by flash chromatography (petroleum ether/ethyl acetate=3/1) to give N-(6,8-dichloro-2,7-naphthyridin-3-yl)cyclopropanecarboxamide (240 mg, 59% yield) as a yellow solid. LCMS (ESI) $[M-55]^+=282.0$.

Step 2: N-(6-chloro-8-(diphenylmethyleneamino)-2,7-naphthyridin-3-yl)cyclopropanecarboxamide

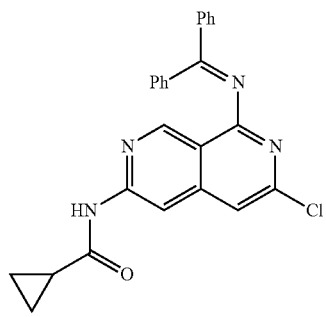 [SMILES: O=C(Nc1cc2cc(Cl)nc(N=C(c3ccccc3)c3ccccc3)c2cn1)C1CC1]

A mixture of N-(6,8-dichloro-2,7-naphthyridin-3-yl)cyclopropanecarboxamide (200 mg, 0.71 mmol), benzophenone imine (128 mg, 0.71 mmol), Pd(OAc)$_2$ (15 mg, 0.07 mmol), Xantphos (40 mg, 0.07 mmol), Cs$_2$CO$_3$ (462 mg, 1.42 mmol), DMF (1 mL) and toluene (1 mL) was heated to 145° C. for 1 hours in the microwave reactor. The reaction mixture was cooled to room temperature, diluted with ethyl acetate, and filtered through celite. The filtrate was washed with brine, dried over Na$_2$SO$_4$, filtered and concentrated. The residue was purified by prep-TLC (normal phase silica gel, dichloromethane/methanol=50/1) to give N-(6-chloro-8-(diphenylmethyleneamino)-2,7-naphthyridin-3-yl)cyclopropanecarboxamide (45 mg, 12% yield) as a yellow solid. LCMS (ESI) $[M-55]^+=427.1$.

Example I.19

Intermediate 19: 3-chloro-N1,N1-bis[(2,4-dimethoxyphenyl)methyl]-2,7-naphthyridine-1,6-diamine

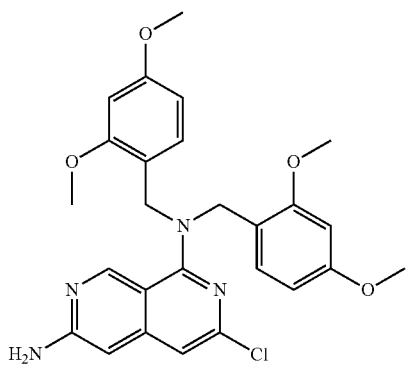 [SMILES: COc1ccc(CN(Cc2ccc(OC)cc2OC)c2nc(Cl)cc3cc(N)ncc23)c(OC)c1]

A mixture of 6,8-dichloro-2,7-naphthyridin-3-amine hydrochloride (2.5 g, 9.98 mmol), bis(2,4-dimethoxybenzyl)amine (12.67 g, 39.92 mmol) and Et$_3$N (5.04 g, 49.9 mmol) in 1,4-dioxane (100 mL) was stirred at 120° C. for 24 hours. The mixture was concentrated and purified by column chromatography (ethyl acetate/hexane=2:3) to afford 3-chloro-N1,N1-bis[(2,4-dimethoxyphenyl)methyl]-2,7-naphthyridine-1,6-diamine (3.8 g, 73% yield) as a white solid. LCMS (ESI) $[M+H]^+=495.1$.

Example I.20

Intermediate 20: N1,N1-bis[(2,4-dimethoxyphenyl)methyl]-3-(4-ethyl-3-pyridyl)-2,7-naphthyridine-1,6-diamine

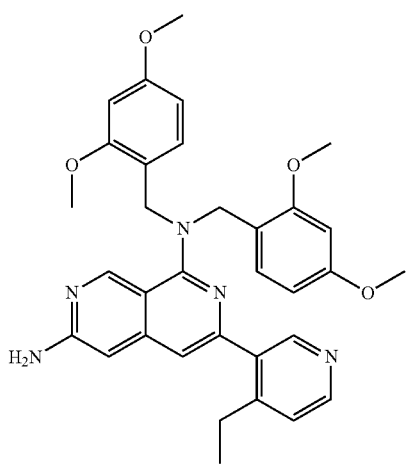 [SMILES: CCc1ccncc1-c1cc2cc(N)ncc2c(N(Cc2ccc(OC)cc2OC)Cc2ccc(OC)cc2OC)n1]

A mixture of 3-chloro-N1,N1-bis[(2,4-dimethoxyphenyl)methyl]-2,7-naphthyridine-1,6-diamine (2.6 g, 5.25 mmol), 4-ethyl-3-(4,4,5,5-tetramethyl-1,3,2-dioxaborolan-2-yl)pyridine (1.42 g, 5.78 mmol), XPhos Pd G2 (0.41 g, 0.53 mmol), potassium acetate (1.03 g, 10.51 mmol) and XPhos (0.5 g, 1.05 mmol) in 1,4-dioxane (100 mL) and water (10 mL) was stirred under Ar at 100° C. for 3 hours. The mixture was concentrated and purified by reverse phase preparative HPLC (C-18, acetonitrile/water+0.05% NH₄HCO₃) to give N1,N1-bis[(2,4-dimethoxyphenyl)methyl]-3-(4-ethyl-3-pyridyl)-2,7-naphthyridine-1,6-diamine (1.1 g, 27% yield) as a white solid. LCMS (ESI) [M+H]⁺=566.3.

Example I.21

Intermediate 21: 1-hydroxy-3H-oxaborolo[3,4-c]pyridine

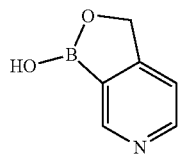

To a cooled (−78° C.) solution of (3-bromo-4-pyridyl) methanol (960 mg, 5.11 mmol) in THF (40 mL) was added n-BuLi (2.5 M in hexane, 7.5 mL, 12 mmol) drop wise. The mixture was stirred for 2 hours at −78° C. prior to the addition of triisopropyl borate (1.6 mL, 6.91 mmol). The mixture was stirred at −78° C. for 30 minutes, then allowed warm to room temperature slowly, and stirred for an additional 1 hours. The reaction was then re-cooled to −78° C. and quenched by the addition of water (10 mL). The mixture was acidified to pH=5 with 2 N HCl and washed with ethyl acetate (30 ml×2). The aqueous phase was concentrated in vacuo to get the crude 1-hydroxy-3H-oxaborolo[3,4-c]pyridine (1.8 g, 52% yield) as pale brown solid which was used for the next step directly. LCMS (ESI) [M+H]⁺=136.2.

Example I.22

Intermediate 22: (±)-cis-N-(8-amino-6-chloro-2,7-naphthyridin-3-yl)-2-cyanocyclopropanecarboxamide

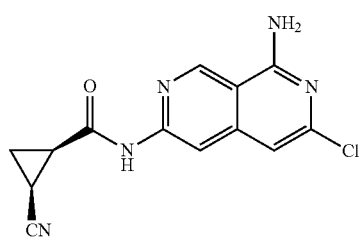 [SMILES: N#C[C@H]1C[C@H]1C(=O)Nc1cc2cc(Cl)nc(N)c2cn1]

Step 1: (±)-cis-2-cyano-N-(6, 8-dichloro-2,7-naphthyridin-3-yl)cyclopropanecarboxamide

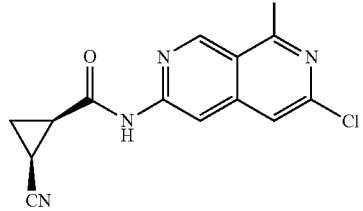

A mixture of (±)-cis-2-cyanocyclopropanecarboxylic acid (1500.0 mg, 13.5 mmol) and oxalyl dichloride (2.0 mL, 23.48 mmol) in dichloromethane (30 mL) was stirred at room temperature for 1 hours. The excess oxalyl dichloride was removed by rotary evaporation at room temperature. Then dichloromethane (30 mL), 6, 8-dichloro-2, 7-naphthyridin-3-amine (850.0 mg, 3.97 mmol), and pyridine (5.0 mL, 61.82 mmol) were added. The reaction mixture was stirred at 0° C. for 1 hour. The solvent was removed by rotary evaporation and the residue was washed with water and filtered to get the crude (±)-cis-2-cyano-N-(6,8-dichloro-2, 7-naphthyridin-3-yl)cyclopropanecarboxamide (1100 mg, 80% yield) as a yellow solid. LCMS (ESI): [M+H]⁺=307.0.

Step 2: (±)-cis-N-(6-chloro-8-(2,4-dimethoxybenzylamino)-2,7-naphthyridin-3-yl)-2-cyanocyclopropanecarboxamide

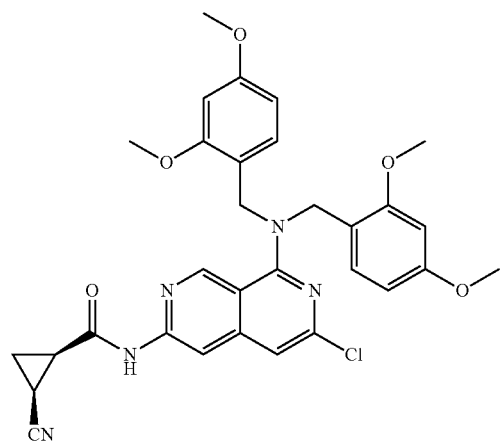 [SMILES: COc1ccc(CN(Cc2ccc(OC)cc2OC)c2nc(Cl)cc3cc(NC(=O)[C@@H]4C[C@@H]4C#N)ncc23)c(OC)c1]

A mixture of (±)-cis-2-cyano-N-(6, 8-dichloro-2, 7-naphthyridin-3-yl) cyclopropanecarboxamide (1.0 g, 3.26 mmol), 2,4-dimethoxybenzylamine (1.5 g, 8.97 mmol) in 1,4-dioxane (10 mL) was stirred at 80° C. for 4 hours. The reaction was concentrated to dryness. The crude product was purified by silica gel column chromatography (dichloromethane:methanol, 15:1) to afford crude (±)-cis-N-(6-chloro-8-(2, 4-dimethoxy benzylamino)-2, 7-naphthyridin-3-yl)-2-cyanocyclopropanecarboxamide (1.5 g) LCMS (ESI): [M+H]⁺=438.1.

Step 3: (±)-cis-N-(8-amino-6-chloro-2,7-naphthyridin-3-yl)-2-cyanocyclopropanecarboxamide

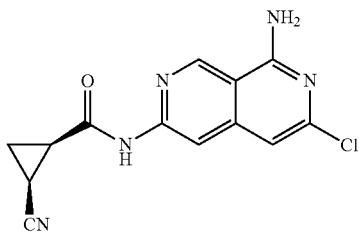 [SMILES: N#C[C@H]1C[C@H]1C(=O)Nc1cc2cc(Cl)nc(N)c2cn1]

A solution of (±)-cis-N-[6-chloro-8-[(2,4-dimethoxyphenyl)methylamino]-2,7-naphthyridin-3-yl]-2-cyano-cyclopropanecarboxamide (400 mg, 0.91 mmol) in trifluoroacetic acid (2.0 mL) was stirred at room temperature for 4 hours. The reaction was concentrated to dryness and the crude product was purified by silica gel column chromatography (ethyl acetate) to afford (±)-cis-N-(8-amino-6-chloro-2,7-naphthyridin-3-yl)-2-cyano-cyclopropanecarboxamide (170 mg, 58% yield) as yellow solid. LCMS (ESI): [M+H]⁺=288.1.

Examples I.23

Intermediate 23: tert-butyl 2-methyl-3-(1-methylpyrazol-4-Yl)cyclopropanecarboxylate

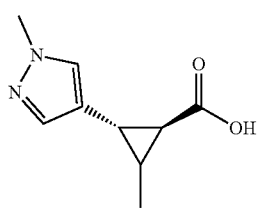

Step 1: ethyldiphenylsulfanium tetrafluoroboranuide

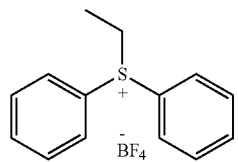

To a solution of AgBF₄ (37.48 g, 192.53 mmol) in dichloromethane (450 mL) was added iodoethane (30 g, 192.35 mmol) under nitrogen. The solution was stirred for 30 minutes at room temperature. Phenylsulfanyl)benzene (106.92 g, 573.99 mmol) was added and then stirred for 16 hours at 35° C. The mixture was filtered and the filtrate was concentrated under vacuum. The residue was washed with dichloromethane/ether (1/1) to afford ethyldiphenylsulfanium tetrafluoroboranuide (25 g, 116.28 mmol) as off-white solid. LCMS (ESI) [M+H]⁺=215.

Step 2: trans-tert-butyl 2-methyl-3-(1-methylpyrazol-4-yl)cyclopropanecarboxylate

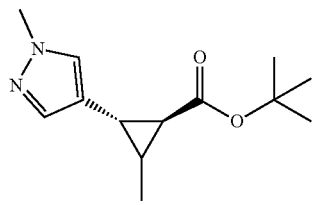 [SMILES: CC1[C@H](C(=O)OC(C)(C)C)[C@H]1c1cnn(C)c1]

To a solution of ethyl(diphenyl)sulfonium (1.55 g, 7.2 mmol) in dichloromethane (2 mL) and 1,2-dimethoxyethane (20 mL) was added lithium diisopropylamide (4.2 mL, 8.4 mmol) at −78° C. The resulting solution was stirred for 1 hour at −78° C. tert-Butyl (E)-3-(1-methylpyrazol-4-yl)prop-2-enoate (500 mg, 2.4 mmol) was added at −78° C. The mixture was stirred at 25° C. for 6 hours. The reaction was quenched with water and then extracted with dichloromethane. The organic layers were combined, dried over anhydrous sodium sulfate and concentrated under vacuum to afford trans-tert-butyl 2-methyl-3-(1-methylpyrazol-4-yl)cyclopropanecarboxylate (550 mg, crude) as a yellow oil. LCMS (ESI) [M+H]⁺=237.

Step 3: trans-tert-butyl 2-methyl-3-(1-methylpyrazol-4-yl)cyclopropanecarboxylate

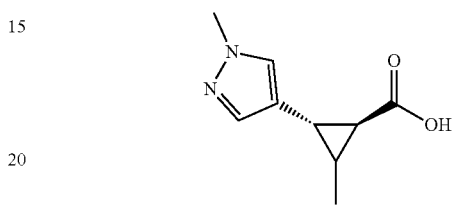

A solution of trans-tert-butyl 2-methyl-3-(1-methylpyrazol-4-yl)cyclopropanecarboxylate (500 mg, crude) in dichloromethane (3 mL) and 2,2,2-trifluoroacetic acid (4 mL) was stirred at 25° C. for 2 hours. The solvent was concentrated under vacuum. The reaction mixture was adjusted to pH 7 with ammonia in methanol (7 mol/L). The residue was purified by reverse phase chromatography (acetonitrile 0-40/0.1% HCl in water) to afford 4 stereoisomers of 2-methyl-3-(1-methylpyrazol-4-yl)cyclopropanecarboxylic acid (180 mg, 0.99 mmol) as a yellow oil. LCMS (ESI) [M+H]⁺=181. (Cyclopropane stereochemistry for isomers: pyrazole trans to carboxylic acid; All absolute stereochemistry arbitrarily assigned)

Examples I.24

Intermediate 24: 2-ethyl-3-(1-methylpyrazol-4-yl)cyclopropanecarboxylic acid

Step 1: Diphenyl(propyl)sulfonium tetrafluoroborate

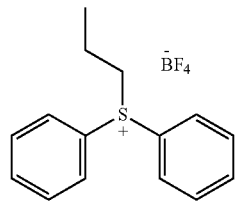

To a solution of silver tetrafluoroborate (2 g, 10.31 mmol) in dichloromethane (20 mL) was added 1-iodopropane (1.75 g, 10.31 mmol) and diphenyl sulfide (5.76 g, 30.93 mmol) at 0° C. The reaction was stirred at 35° C. for 15 hours. The mixture was filtered and the filtrate was concentrated under vacuum. The residue was washed with dichloromethane-ether to afford diphenyl(propyl)sulfonium tetrafluoroborate (2 g, 6.32 mmol) as a white solid. LCMS (ESI) [M+H]⁺=229.

Step 2: tert-butyl 2-ethyl-3-(1-methylpyrazol-4-yl)cyclopropanecarboxylate

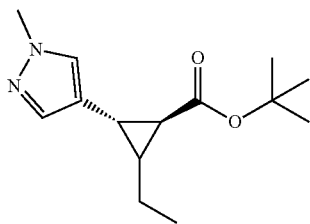 [SMILES: CCC1[C@H](C(=O)OC(C)(C)C)[C@H]1c1cnn(C)c1]

To a solution of diphenyl(propyl)sulfonium tetrafluoroborate (1.50 g, 4.75 mmol) in 1,2-dimethoxyethane (30 mL) and dichloromethane (3 mL) was added lithium diisopropylamide (5.54 ml, 11.09 mmol) at −78° C. The resulting mixture was stirred for 1 hour at −78° C. Then tert-butyl (Z)-3-(1-methylpyrazol-4-yl)prop-2-enoate (330 mg, 1.58 mmol) was added and stirred at −78° C. to 25° C. for 15 hours. The reaction was quenched with water. The resulting mixture was extracted with dichloromethane and dried with anhydrous sodium sulfate. After filtration, the filtrate was concentrated under vacuum to afford tert-butyl 2-ethyl-3-(1-methylpyrazol-4-yl)cyclopropanecarboxylate (350 mg, 1.40 mmol) as a brown oil. LCMS (ESI) [M+H]$^+$=251.

Step 3: 2-ethyl-3-(1-methylpyrazol-4-yl)cyclopropanecarboxylic acid

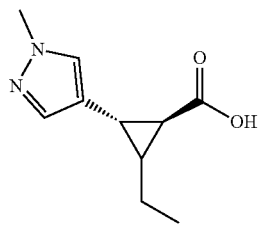

A solution of trans-tert-butyl 2-ethyl-3-(1-methylpyrazol-4-yl)cyclopropanecarboxylate (350 mg, 1.4 mmol) and 2,2,2-trifluoroacetic acid (8 mL) in dichloromethane (3 mL) was stirred at 25° C. for 1 hour. The mixture was concentrated under vacuum. The resulting residue was purified by reverse phase chromatography (acetonitrile 0-40/0.1% HCl in water) to afford 2-ethyl-3-(1-methylpyrazol-4-yl)cyclopropanecarboxylic acid (260 mg, 1.34 mmol) as a brown oil. Product mixture consists of 4 stereoisomers where pyrazole is trans to carboxylic acid and 2,2-dimethyl-3-(1-methyl-1H-pyrazol-4-yl)cyclopropane-1-carboxylic acid as a contaminant. LCMS (ESI) [M+H]$^+$=195.

Examples I.25

Intermediate 25: 2-bromo-6-isopropyl-5,6-dihydro-4H-pyrazolo[1,5-d][1,4]diazepin-7(8H)-one

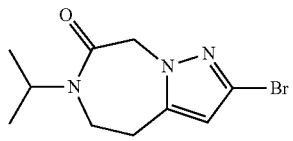

A solution of 2-bromo-4,5,6,8-tetrahydropyrazolo[1,5-d][1,4]diazepin-7-one (3.0 g, 13.04 mmol) and NaH (1.56 g, 39.12 mmol) in N,N-dimethylformamide (75 mL) was stirred at 0° C. for 10 min. Then 2-iodopropane (11.08 g, 65.2 mmol) was added. The mixture was stirred at 25° C. for 1 hour. The reaction was quenched with water. The mixture was concentrated under vacuum. The resulting residue was purified by reverse phase chromatography (acetonitrile 0-40/0.1% NH$_4$HCO$_3$ in water) to afford 2-bromo-6-isopropyl-5,8-dihydro-4H-pyrazolo[1,5-d][1,4]diazepin-7-one (2.1 g, 7.7166 mmol, 59.2% yield) as a white solid. LCMS (ESI) [M+H]$^+$=272.

Examples I.26

Intermediate 26: 2-bromo-5,5,6-trimethyl-4,8-dihydropyrazolo[1,5-d][1,4]diazepin-7-one

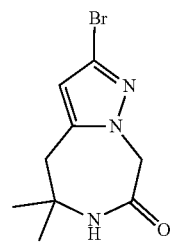

Step 1: 2-(3,5-dibromopyrazol-1-yl)acetonitrile

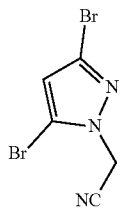

A mixture of 3,5-dibromo-1H-pyrazole (1.0 g, 4.43 mmol) and potassium carbonate (1.22 g, 8.85 mmol) in N,N-dimethylformamide (20 mL) was stirred at 25° C. for 10 min. Bromoacetonitrile (796.59 mg, 6.64 mmol) was added and the reaction was stirred at 25° C. for 2 h. After filtration, the filtrate was diluted with ethyl acetate (30 mL). The reaction was washed with water. The organic phase was dried with anhydrous sodium sulfate. After filtration, the filtrate was concentrated under vacuum. The residue was purified by flash chromatography on silica gel eluting with petroleum ether/dichloromethanol (1/1) to afford 2-(3,5-dibromopyrazol-1-yl)acetonitrile (950 mg, 3.59 mmol) as a white solid. LCMS (ESI) [M+H]⁺=264.

Step 2: 2-[3-bromo-5-(2-methylprop-1-enyl)pyrazol-1-yl]acetonitrile

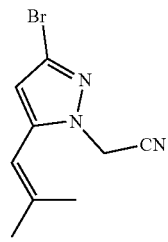

A mixture of 2-(3,5-dibromopyrazol-1-yl)acetonitrile (1.0 g, 3.77 mmol), 4,4,5,5-tetramethyl-2-(2-methylprop-1-en-1-yl)-1,3,2-dioxaborolane (687.29 mg, 3.77 mmol), Pd(dppf)Cl₂ (552.64 mg, 0.75 mmol), and potassium carbonate (1.56 g, 11.32 mmol) in 1,4-dioxane (20 mL) and water (2 mL) was stirred under nitrogen for 1 h at 100° C. After filtration, the filtrate was concentrated under vacuum. The residue was purified by silica gel flash chromatography eluting with ethyl acetate/petroleum ether (1/3) to afford 2-[3-bromo-5-(2-methylprop-1-enyl)pyrazol-1-yl]acetonitrile (700 mg, 2.92 mmol) as a white solid. LCMS (ESI) [M+H]⁺=240.

Step 3: 2-bromo-5,5-dimethyl-6,8-dihydro-4H-pyrazolo[1,5-d][1,4]diazepin-7-one

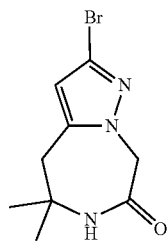

A mixture of 2-[3-bromo-5-(2-methylprop-1-enyl)pyrazol-1-yl]acetonitrile (700 mg, 2.92 mmol) in methylsulfonic acid (15 mL) was stirred at 65° C. for 3 d. The reaction was quenched with ice water. The reaction mixture was adjusted to pH 9-10 with an aqueous sodium hydroxide solution. The resulting solution was extracted with dichloromethane and dried with anhydrous sodium sulfate. After filtration, the filtrate was concentrated under vacuum. The residue was purified by reverse phase chromatography (acetonitrile 0-40/0.1% NH₄HCO₃ in water) to afford 2-bromo-5,5-dimethyl-6,8-dihydro-4H-pyrazolo[1,5-d][1,4]diazepin-7-one (300 mg, 1.16 mmol) as a white solid. LCMS (ESI) [M+H]⁺=258.

Step 4: 2-bromo-5,5,6-trimethyl-4,8-dihydropyrazolo[1,5-d][1,4]diazepin-7-one

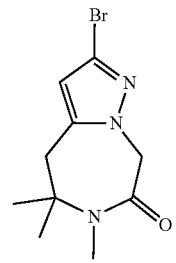

A mixture of 2-bromo-5,5-dimethyl-6,8-dihydro-4H-pyrazolo[1,5-d][1,4]diazepin-7-one (100 mg, 0.39 mmol) and potassium tert-butoxide (52.07 mg, 0.46 mmol) in tetrahydrofuran (10 mL) was stirred at 25° C. for 10 min. Iodomethane (82.52 mg, 0.58 mmol) was added. The reaction was stirred at 25° C. for 1 h. The reaction was concentrated under vacuum and purified by flash chromatography on silica gel eluting with dichloromethane/methanol (95/5) to afford 2-bromo-5,5,6-trimethyl-4,8-dihydropyrazolo[1,5-d][1,4]diazepin-7-one (80 mg, 0.29 mmol) as a white solid. LCMS (ESI) [M+H]⁺=272.

Examples I.27

Intermediate 27: 2-bromo-4-methylene-5,6-dihydro-4H-pyrazolo[1,5-d][1,4]diazepin-7(8H)-one

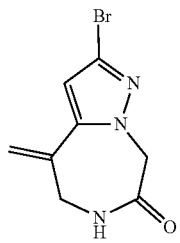

Step 1: 3,5-dibromo-1H-pyrazole

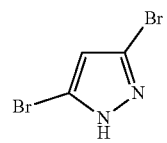

To a 3 L 3-necked round-bottom flask was added compound 1 (200 g, 656 mmol, 1.0 eq) in dimethyl tetrahydrofuran (1000 mL) under N₂ and then the solution was cooled to −78° C. n-BuLi (2.5 M, 525 mL, 2.0 eq) was added dropwise to the above solution for 1 hour at −78° C. and the mixture was stirred at −78° C. for 3 hours. TLC (Petroleum ether/Ethyl acetate=3/1, R$_f$=0.51) showed the reaction was completed and one main new spot formed. The two reactions were combined and the reaction mixture was poured into water (1000 mL) at 0° C. and the pH value of the solution was acidified to 4-5 with 2N HCl. The resulting solution was extracted with ethyl acetate (1000 mL, 800 mL, 400 mL). The combined organic phase was washed with brine (800 mL), dried with anhydrous Na$_2$SO$_4$ and concentrated under vacuum to give the title compound (284 g, 1.26 mol, 95.8% yield) as a yellow solid. The crude product was directly used to the next step without further purification.

Step 2: tert-butyl 2-(3,5-dibromo-1H-pyrazol-1-yl)acetate

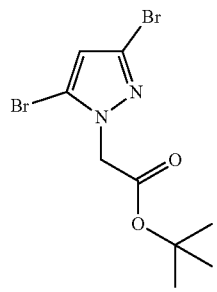

To the solution of 3,5-dibromo-1H-pyrazole (137 g, 607 mmol, 1.0 eq) in MeCN (959 mL) was added tert-butyl 2-chloroacetate (137 g, 910 mmol, 131 mL, 1.5 eq), K$_2$CO$_3$ (137 g, 989 mmol, 1.63 eq) and TBAI (11.0 g, 29.7 mmol, 0.049 eq). The resulting solution was stirred at 25° C. for 12 hours. TLC (Petroleum ether/Ethyl acetate=5/1, R$_f$=0.74) showed the reaction was complete and one main new spot formed. The reaction mixture was filtered, the filter cake was washed with EtOAc (500 mL×3, 300 mL, 200 mL). The combined filtrate was concentrated to give a residue. The residue was dissolved in EtOAc (2.0 L), washed with water (1.0 L), brine (1.0 L). The organic phase was dried with anhydrous Na$_2$SO$_4$, filtered and concentrated in vacuum to give the title compound (744 g, crude) as a brown oil. $^1$H NMR: (400 MHz, CDCl$_3$): δ 6.35 (s, 1H), 4.80 (s, 2H), 1.46 (s, 9H).

Step 3: 2-(3,5-dibromo-1H-pyrazol-1-yl)acetic acid

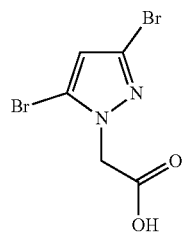

To the solution of compound tert-butyl 2-(3,5-dibromo-1H-pyrazol-1-yl)acetate (248 g, 729 mmol, 1.0 eq) in DCM (140 mL) was added TFA (2.08 kg, 18.2 mol, 1.35 L, 25 eq) and the resulting solution was heated to 80° C. and stirred for 2 hours. TLC (Petroleum ether/Ethyl acetate=5/1, R$_f$=0.03) showed the reaction was complete and one main new spot formed. The reaction was repeated twice. The combined reaction mixtures were concentrated under reduced pressure to give a crude product. The crude product was diluted with petroleum ether/ethyl acetate (4/1, 1.0 L) and the resulting suspension was stirred at 25° C. for 1 hour, then filtered. The filter cake was collected and dried in vacuum to give the title compound (471 g, 1.66 mol, 75.8% yield) as a creamy white solid. $^1$H NMR: (400 MHz, DMSO) δ 13.3 (br s, 1H), 6.70 (s, 1H), 4.96 (s, 2H).

Step 4: N-allyl-2-(3,5-dibromo-1H-pyrazol-1-yl)acetamide

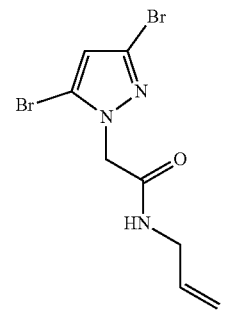

To the solution of 2-(3,5-dibromo-1H-pyrazol-1-yl)acetic acid (157 g, 553 mmol, 1.0 eq) in DMF (1.10 L) was added DIPEA (357 g, 2.77 mol, 482 mL, 5.0 eq) and EDCI (138 g, 719 mmol, 1.3 eq) at 0° C., the resulting solution was stirred at 0° C. for 30 min. Then HOBt (97.1 g, 719 mmol, 1.3 eq) was added and the mixture was stirred at 0° C. for another 30 min. Then prop-2-en-1-amine (47.4 g, 830 mmol, 62.2 mL, 1.5 eq) was added at 0° C. and the mixture was warmed to 25° C. and stirred for 16 hours. TLC (Petroleum ether/ Ethyl acetate=1/1, R$_f$=0.60) showed the reaction was completed and one main new spot formed. The reaction was repeated two more times. The three batches of reactions were combined and the reaction mixture was poured into ice water (12.0 L), extracted with ethyl acetate (2.00 L, 2.00 L, 1.00 L). The combined organic phase was washed with brine (2.0 L), and then concentrated in vacuum to give a crude product. The crude product was purified by column chromatography on silica gel (Petroleum ether/Ethyl acetate=3/ 1) to afford the title compound (340 g, 1.05 mol, 63.5% yield) as a white solid. $^1$H NMR: (400 MHz, CDCl$_3$) δ 6.41 (s, 1H), 5.89 (br s, 1H), 5.79 (m, 1H), 5.08-5.17 (m, 2H), 4.85 (s, 2H), 3.86-3.93 (m, 2H).

Step 5: N-allyl-2-(3,5-dibromo-1H-pyrazol-1-yl)-N-(4-methoxybenzyl)acetamide

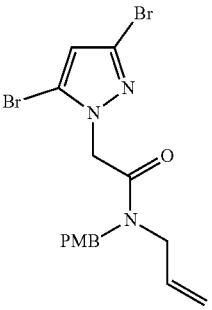

To a solution of N-allyl-2-(3,5-dibromo-1H-pyrazol-1-yl) acetamide (103 g, 319 mmol, 1.0 eq) in THF (721 mL) was added KOH (32.2 g, 574 mmol, 1.8 eq), 18-Crown-6 (3.37 g, 12.8 mmol, 0.04 eq) and 1-(chloromethyl)-4-methoxybenzene (64.9 g, 415 mmol, 56.5 mL, 1.3 eq), then the mixture was stirred at 25° C. for 64 h. TLC (Petroleum ether/Ethyl acetate=2/1, R$_f$=0.50) showed one main new spot formed. The reaction was repeated two more times. The three batches reactions were combined and the reaction mixture was added water (1.00 L), and the pH value was adjusted to 7-8 with 1M HCl, then extracted with EtOAc (1.00 L, 800 mL×3). The combined organic phase was washed with brine (800 mL), dried with anhydrous Na$_2$SO$_4$, filtered and concentrated in vacuum to give a crude product. The crude product was purified by column chromatography on silica gel (Petroleum ether/Ethyl acetate=2/1) to afford the title compound (320 g, 722 mmol, 75.5% yield) as a yellow oil.

Step 6: 2-bromo-6-(4-methoxybenzyl)-4-methylene-5,6-dihydro-4H-pyrazolo[1,5-d][1,4]diazepin-7(8H)-one

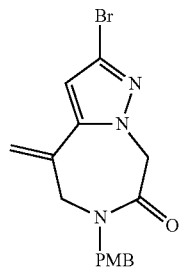

To a solution of N-allyl-2-(3,5-dibromo-1H-pyrazol-1-yl)-N-(4-methoxybenzyl)acetamide (50.0 g, 113 mmol, 1.0 eq) in DMF (1.0 L) was added K$_2$CO$_3$ (31.2 g, 226 mmol, 2.0 eq), Pd(PPh$_3$)$_4$ (17.0 g, 14.7 mmol, 0.13 eq) under Ar, then the mixture was stirred at 120° C. for 16 hours. The reaction was repeated six more times. The seven batches of reactions were combined and the reaction mixture was concentrated in vacuum to remove the solvent to give a residue. Then the residue was added water (2.0 L), extracted with ethyl acetate (2.0 L, 1.0 L, 1.0 L). The combined organic phase was washed with brine (1.0 L) and concentrated to give a crude product. The crude product was purified by column chromatography on silica gel (Petroleum ether/Ethyl acetate=2/1) to afford the title compound compound (74.1 g, 204 mmol, 25.9% yield, 98.7% purity) as a white solid. $^1$H NMR: (400 MHz, CDCl$_3$) δ 7.21 (d, J=8.8 Hz, 2H), 6.86-6.92 (m, 2H), 6.52 (s, 1H), 5.50 (s, 1H), 5.20 (s, 2H), 5.02 (s, 1H), 4.58 (s, 2H), 4.13 (s, 2H), 3.83 (s, 3H).

Step 7: 2-bromo-4-methylene-5,6-dihydro-4H-pyrazolo[1,5-d][1,4]diazepin-7(8H)-one

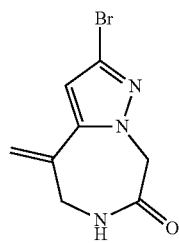

A solution of 2-bromo-6-(4-methoxybenzyl)-4-methylene-5,6-dihydro-4H-pyrazolo[1,5-d][1,4]diazepin-7(8H)-one_(3.90 g, 10.8 mmol, 1.0 eq), TFA (38.4 g, 336 mmol, 24.9 mL, 31.3 eq) and trifluoromethanesulfonic acid (16.2 g, 108 mmol, 9.5 mL, 10 eq) in DCM (28 mL) was stirred at 25° C. for 12 hours. The reaction mixture was concentrated to give a residue. To the residue was added water (100 mL), then the pH value was adjusted to 6-7 with saturated aqueous NaHCO$_3$ solution, extracted with EtOAc (100 mL×3, 60 mL×3). The combined organic phase was dried with anhydrous Na$_2$SO$_4$, filtered and concentrated in vacuum to give a crude product. The crude product was purified by column chromatography on silica gel (Petroleum ether/Ethyl acetate=1/1) to afford the title compound (1.90 g, 7.85 mmol, 72.9% yield) as a gray solid. $^1$H NMR: (400 MHz, CDCl$_3$) δ 6.88 (s, 1H), 6.54 (s, 1H), 5.55 (s, 1H), 5.21 (s, 1H), 5.08 (s, 2H), 4.15 (d, J=6.0 Hz, 2H).

Examples I.28

Intermediate 28: 2-Bromo-6-methyl-4-methylidene-4H,5H,6H,7H,8H-pyrazolo[1,5-d][1,4]diazepin-7-one Step 1: 2-(3,5-Dibromo-1H-pyrazol-1-yl)-N-methyl-N-(prop-2-en-1-yl)acetamide

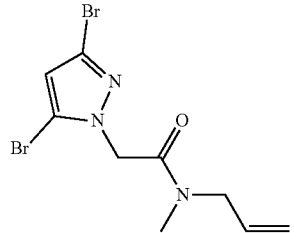

A solution of 2-(3,5-dibromo-1H-pyrazol-1-yl)acetic acid (15 g, 52.84 mmol), methyl(prop-2-en-1-yl)amine (5.7 g, 80.15 mmol), N,N-diisopropylethylamine (27 g, 208.9 mmol) and HATU (30 g, 78.9 mmol) in N,N-dimethylformamide (500 mL) was stirred for 16 hours at room temperature. The resulting mixture was diluted with ethyl acetate and then washed with sodium chloride solution. The organic phase was dried with anhydrous sodium sulfate. After filtration, the filtrate was concentrated under vacuum. The residue was purified by flash chromatography on silica gel eluting with ethyl acetate/petroleum ether (2/3) to afford 2-(3,5-dibromo-1H-pyrazol-1-yl)-N-methyl-N-(prop-2-en-1-yl)acetamide (16.3 g, 92%) as a yellow oil. LCMS (ESI) [M+H]$^+$=338.0.

Step 2: 2-Bromo-6-methyl-4-methylidene-4H,5H, 6H,7H,8H-pyrazolo[1,5-d][1,4]diazepin-7-one

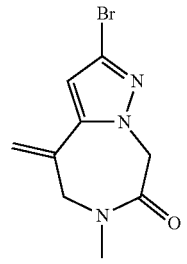

A mixture of 2-(3,5-dibromo-1H-pyrazol-1-yl)-N-methyl-N-(prop-2-en-1-yl)acetamide (5 g, 14.84 mmol), palladium acetate (166 mg, 0.74 mmol), triphenylphosphine (388 mg, 1.48 mmol), TBAB (4.8 g, 14.890 mmol) and potassium acetate (4.2 g, 42.80 mmol) in N,N-dimethylformamide (100 mL) was stirred for 10 h at 80° C. After filtration, the filtrate was concentrated under vacuum. The residue was purified on a silica gel column eluted with ethyl acetate/petroleum ether (2/1) to afford 2-bromo-6-methyl-4-methylidene-4H,5H,6H,7H,8H-pyrazolo[1,5-d][1,4]diazepin-7-one (3.2 g, 84%) as a brown oil. LCMS (ESI) [M+H]⁺=258.1.

Intermediate XX: 2'-bromo-6'-methyl-5',6'-dihydrospiro[cyclopropane-1,4'-pyrazolo[1,5-d][1,4]diazepin]-7'(8'H)-one

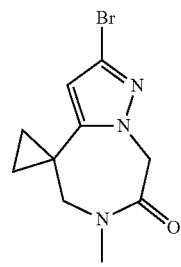

A mixture of trimethylsulfoxonium iodide (1.29 g, 5.86 mmol) and potassium tert-butoxide (656 mg, 5.85 mmol) in dimethyl sulfoxide (30 mL) was stirred for 30 min at room temperature. Then a solution of 2-bromo-6-methyl-4-methylidene-4H,5H,6H,7H,8H-pyrazolo[1,5-d][1,4]diazepin-7-one (500 mg, 1.95 mmol) in dimethyl sulfoxide (3 mL) was added. The mixture was then stirred for 12 h at 50° C. The reaction mixture was diluted with ethyl acetate and then washed with water. The organic layer was dried over anhydrous sodium sulfate, filtered and concentrated under vacuum. The residue was purified by silica gel column with dichloromethane/methanol (10/1) to afford 2'-bromo-6'-methyl-5',6'-dihydrospiro[cyclopropane-1,4'-pyrazolo[1,5-d][1,4]diazepin]-7'(8'H)-one (120 mg, 23%) as a white solid. LCMS (ESI) [M+H]⁺=270.

Examples I.29

Intermediate 29: 8-bromo-5,6-dihydro-11H-imidazo[1,2-a]pyrazolo[1,5-d][1,4]diazepine

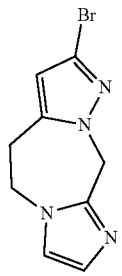

Step 1: 2-bromo-4,5,6,8-tetrahydropyrazolo[1,5-d][1,4]diazepine-7-thione

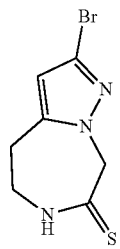 [SMILES: S=C1Cn2nc(Br)cc2CCN1]

A mixture of 2-bromo-4,5,6,8-tetrahydropyrazolo[1,5-d][1,4]diazepin-7-one (314 mg, 1.36 mmol) and Lawsson reagent (551.4 mg, 1.36 mmol) in 1,4-dioxane (10 mL) was stirred at 90° C. for 1 h. The reaction was concentrated under vacuum. The residue was purified by flash chromatography on silica gel eluting with dichloromethane/methanol (96/4) to afford 2-bromo-4,5,6,8-tetrahydropyrazolo[1,5-d][1,4]diazepine-7-thione (265 mg, 78.9%) as a white solid. LCMS (ESI) [M+H]⁺=246.0.

Step 2: 2-bromo-N-(2,2-diethoxyethyl)-5,8-dihydro-4H-pyrazolo[1,5-d][1,4]diazepin-7-Amine

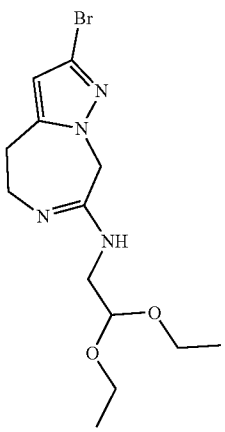 [SMILES: CCOC(CNC1=NCCc2cc(Br)nn2C1)OCC]

A mixture of 2-bromo-5,6-dihydro-4H-pyrazolo[1,5-d][1,4]diazepine-7(8H)-thione (265.0 mg, 1.07 mmol), 2,2-diethoxyethan-1-amine (1.42 g, 10.7 mmol) and silver carbonate (590 mg, 2.14 mmol) in tetrahydrofuran (10 mL) was stirred at 80° C. for 1 h. The solvent was concentrated under vacuum. The residue was purified by reverse-phase column eluting with water (0.05% TFA)/CH$_3$CN (85/15) to afford 2-bromo-N-(2,2-diethoxyethyl)-5,8-dihydro-4H-pyrazolo[1,5-d][1,4]diazepin-7-amine (295 mg, 80%) as a brown oil. LCMS (ESI) [M+H]$^+$=345.0.

Step 3: 8-bromo-5,6-dihydro-11H-imidazo[1,2-a]pyrazolo[1,5-d][1,4]diazepine

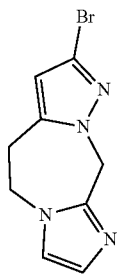 [SMILES: Brc1cc2n(n1)Cc1nccn1CC2]

A solution of 2-bromo-N-(2,2-diethoxyethyl)-5,8-dihydro-4H-pyrazolo[1,5-d][1,4]diazepin-7-amine (228 mg, 0.66 mmol) and concentrated hydrochloric acid (0.17 mL, 0.66 mmol) in acetic acid (5 mL) was stirred at 80° C. for 1 h. The reaction was concentrated under vacuum. The residue was purified by reverse-phase column eluting with water (0.05% TFA)/ACN (85/15) to afford 8-bromo-5,6-dihydro-11H-imidazo[1,2-a]pyrazolo[1,5-d][1,4]diazepine (150 mg, 89.7%) as a brown oil. LCMS (ESI) [M+H]$^+$=253.0.

Examples I.30

Intermediate 30: tert-butyl 8-methyl-7-(4,4,5,5-tetramethyl-1,3,2-dioxaborolan-2-yl)-2,3-dihydropyrido[2,3-b][1,4]oxazine-1-carboxylate

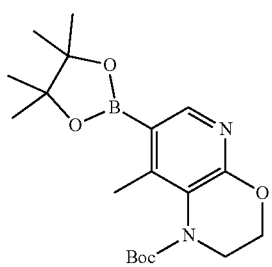 [SMILES: Cc1c(B2OC(C)(C)C(C)(C)O2)cnc2c1N(C(=O)OC(C)(C)C)CCO2]

Step 1: tert-butyl 7-bromo-8-methyl-2,3-dihydropyrido[2,3-b][1,4]oxazine-1-carboxylate

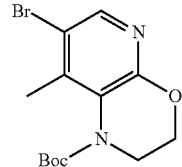 [SMILES: Cc1c(Br)cnc2c1N(C(=O)OC(C)(C)C)CCO2]

To a solution of 7-bromo-8-methyl-2,3-dihydro-1H-pyrido[2,3-b][1,4]oxazine (1 g, 4.37 mmol) in tetrahydrofuran (2 mL) was added dropwise LiHMDS (8.73 mL, 8.73 mmol, 1 mol/L) at 0° C. The resulting solution was stirred under nitrogen for 0.5 h at 0° C. Then di-tert-butyl dicarbonate (2.85 g, 13.07 mmol) was added and the reaction was stirred at room temperature for 2 h. The reaction was quenched by methanol (50 mL). The solvent was concentrated under vacuum. The residue was purified by silica gel flash chromatography (ethyl acetate/petroleum ether, 1/4) to afford tert-butyl 7-bromo-8-methyl-2,3-dihydropyrido[2,3-b][1,4]oxazine-1-carboxylate (800 mg, 2.43 mmol) as a yellow oil. LCMS (ESI) [M+H]$^+$=329.2.

Step 2: tert-butyl 8-methyl-7-(4,4,5,5-tetramethyl-1,3,2-dioxaborolan-2-yl)-2,3-dihydropyrido[2,3-b][1,4]oxazine-1-carboxylate

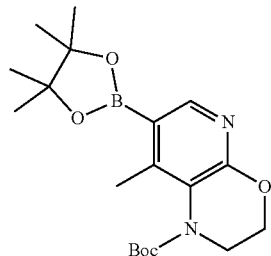 [SMILES: Cc1c(B2OC(C)(C)C(C)(C)O2)cnc2c1N(C(=O)OC(C)(C)C)CCO2]

A mixture of tert-butyl 7-bromo-8-methyl-2,3-dihydropyrido[2,3-b][1,4]oxazine-1-carboxylate (6.2 g, 18.83 mmol), dipinacoldiboron (23.93 g, 94.22 mmol), [1,1'-bis(diphenylphosphino)ferrocene]dichloropalladium(II) (2.76 g, 3.77 mmol) and potassium acetate (5.55 g, 56.62 mmol) in 1,4-dioxane (2 mL) was stirred under nitrogen for 2.5 h at 90° C. The solvent was concentrated under vacuum. The residue was purified by flash chromatography on silica gel eluting with ethyl acetate/petroleum ether (30%) to afford tert-butyl 8-methyl-7-(4,4,5,5-tetramethyl-1,3,2-dioxaborolan-2-yl)-2,3-dihydropyrido[2,3-b][1,4]oxazine-1-carboxylate (5 g, 13.29 mmol) as a yellow oil. LCMS (ESI) [M+H]$^+$=376.3.

Example 2

(±)-cis-N-(8-amino-6-(4-methylpyridin-3-yl)-2,7-naphthyridin-3-yl)-2-fluorocyclopropanecarboxamide (Compound 1)

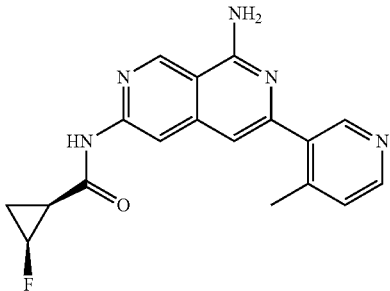 [SMILES: Cc1ccncc1-c1cc2cc(NC(=O)[C@@H]3C[C@@H]3F)ncc2c(N)n1]

To a sealed tube was added N-(8-amino-6-chloro-2,7-naphthyridin-3-yl)-2-fluoro-cyclopropanecarboxamide (50 mg, 0.18 mmol), 4-methyl-3-(4,4,5,5-tetramethyl-1,3,2-dioxaborolan-2-yl)pyridine (50 mg, 0.23 mmol), Xphos Pd G2 (14 mg, 0.02 mmol), Xphos (17 mg, 0.04 mmol), potassium acetate (52 mg, 0.53 mmol), 1,4-dioxane (1 mL) and water (0.2 mL). The mixture was stirred at 100° C. for 2 hours. The reaction mixture was then filtered. The filtrate was concentrated to give a yellow residue, which was purified by silica flash chromatography (dichloromethane/methanol, gradient from 20:1 to 10:1) to give N-[8-amino-6-(4-methyl-3-pyridyl)-2,7-naphthyridin-3-yl]-2-fluoro-cyclopropanecarboxamide (21 mg, 35% yield) as a white solid. LCMS (ESI): $R_T$ (min)=0.974, [M+H]$^+$=338.1, method=B; $^1$H NMR (400 MHz, CD$_3$OD) δ 9.30 (s, 1H), 8.54 (s, 1H), 8.43 (d, J=5.2 Hz, 1H), 8.33 (s, 1H), 7.40 (d, J=5.2 Hz, 1H), 6.70 (s, 1H), 4.99-4.80 (m, 1H), 2.46 (s, 3H), 2.19-2.15 (m, 1H), 1.87-1.80 (m, 1H), 1.26-1.21 (m, 1H).

Example 3

(±)-cis-N-(8-amino-6-(1,5-dimethyl-1H-pyrazol-4-yl)-2,7-naphthyridin-3-yl)-2-fluorocyclopropanecarboxamide (Compound 2)

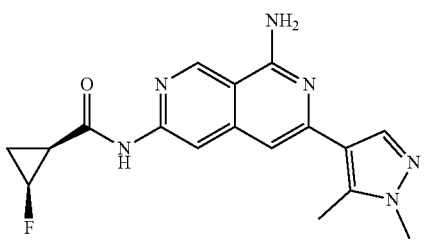 [SMILES: Cc1c(-c2cc3cc(NC(=O)[C@@H]4C[C@@H]4F)ncc3c(N)n2)cnn1C]

To a sealed tube was added N-(8-amino-6-chloro-2,7-naphthyridin-3-yl)-2-fluoro-cyclopropanecarboxamide (30 mg, 0.11 mmol), 1,5-dimethyl-1H-pyrazole-4-boronic acid pinacol ester (31 mg, 0.14 mmol), XphosPdG2 (8 mg, 0.01 mmol), Xphos (10 mg, 0.02 mmol), potassium acetate (31 mg, 0.32 mmol), 1,4-dioxane (1 mL) and water (0.4 mL). The mixture was stirred at 100° C. for 4 hours. The reaction mixture was concentrated and the residue was purified by silica gel flash chromatography (dichloromethane/methanol, gradient=20:1 to 10:1) to give cis-N-[8-amino-6-(1,5-dimethylpyrazol-4-yl)-2,7-naphthyridin-3-yl]-2-fluoro-cyclopropanecarboxamide (8 mg, 21% yield) as a light yellow solid. LCMS (ESI): $R_T$ (min)=1.051, [M+H]$^+$=341.2, method=B; $^1$H NMR (400 MHz, CD$_3$OD) δ 9.18 (s, 1H), 8.23 (s, 1H), 7.85 (s, 1H), 7.00 (s, 1H), 4.99-4.83 (m, 1H), 3.86 (s, 3H), 2.64 (s, 3H), 2.18-2.15 (m, 1H), 1.86-1.80 (m, 1H), 1.25-1.20 (m, 1H).

Example 4

(±)-cis-N-(8-amino-6-(1,3,5-trimethyl-1H-pyrazol-4-yl)-2,7-naphthyridin-3-yl)-2-fluorocyclopropanecarboxamide (Compound 3)

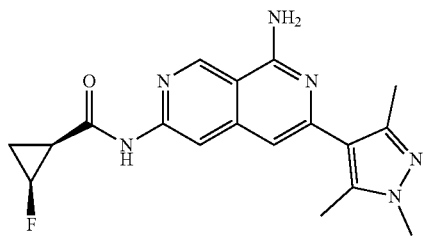 [SMILES: Cc1nn(C)c(C)c1-c1cc2cc(NC(=O)[C@@H]3C[C@@H]3F)ncc2c(N)n1]

To a sealed tube was added N-(8-amino-6-chloro-2,7-naphthyridin-3-yl)-2-fluoro-cyclopropanecarboxamide (20 mg, 0.07 mmol), 1,3,5-trimethyl-4-(4,4,5,5-tetramethyl-1,3,2-dioxaborolan-2-yl)-1H-pyrazole (22 mg, 0.09 mmol), Xphos Pd G2 (6 mg, 0.01 mmol), Xphos (7 mg, 0.01 mmol), potassium acetate (21 mg, 0.21 mmol), 1,4-dioxane (1 mL) and water (0.20 mL). The mixture was stirred at 100° C. for 5 hours. The reaction mixture was then filtered and concentrated to give a yellow residue which was purified by silica gel flash chromatography (dichloromethane/methanol, gradient=20:1 to 8:1) to give a yellow solid. The yellow solid was then purified by reverse phase flash chromatography (Biotage, ODS, 50 g column, uv 254 nm) eluting with methanol/water (+0.5% NH$_4$HCO$_3$) to give cis-N-[8-amino-6-(1,3,5-trimethylpyrazol-4-yl)-2,7-naphthyridin-3-yl]-2-fluoro-cyclopropanecarboxamide (9 mg, 35% yield) as a white solid. LCMS (ESI): $R_T$ (min)=1.055, [M+H]$^+$=355.2, method=B; $^1$H NMR (400 MHz, CD$_3$OD) δ 9.21 (s, 1H), 8.24 (s, 1H), 6.82 (s, 1H), 4.98-4.80 (m, 1H), 3.78 (s, 3H), 2.42 (s, 3H), 2.33 (s, 3H), 2.19-2.13 (m, 1H), 1.88-1.78 (m, 1H), 1.27-1.18 (m, 1H).

Example 5

N-(8-amino-6-(1-methyl-1H-pyrazol-4-yl)-2,7-naphthyridin-3-yl)-2-fluorocyclopropanecarboxamide (Compound 4)

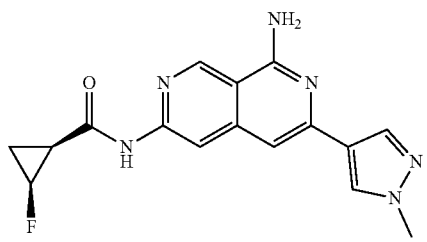 [SMILES: Cn1cc(-c2cc3cc(NC(=O)[C@@H]4C[C@@H]4F)ncc3c(N)n2)cn1]

To a sealed tube was added N-(8-amino-6-chloro-2,7-naphthyridin-3-yl)-2-fluoro-cyclopropanecarboxamide (20 mg, 0.07 mmol), 1-methyl-4-(4,4,5,5-tetramethyl-1,3,2-dioxaborolan-2-yl)-1H-pyrazole (19 mg, 0.09 mmol), Xphos Pd G2 (6 mg, 0.01 mmol), Xphos (7 mg, 0.01 mmol), potassium acetate (21 mg, 0.21 mmol), 1,4-dioxane (1 mL) and water (0.2 mL). The mixture was stirred at 100° C. for 4 hours. The reaction mixture was then filtered and concentrated to give a yellow residue, which was then purified by silica flash chromatography (dichloromethane/methanol, gradient=20:1 to 10:1) to give N-[8-amino-6-(1-methylpyrazol-4-yl)-2,7-naphthyridin-3-yl]-2-fluoro-cyclopropanecarboxamide (9 mg, 37% yield) as a white solid. LCMS (ESI): $R_T$ (min)=1.027, [M+H]$^+$=327.1, method=B; $^1$H NMR (400 MHz, CD$_3$OD) δ 9.16 (s, 1H), 8.22 (s, 1H), 8.14 (s, 1H), 8.03 (s, 1H), 7.13 (s, 1H), 4.99-4.82 (m, 1H), 3.96 (s, 3H), 2.18-2.15 (m, 1H), 1.86-1.80 (m, 1H), 1.26-1.21 (m, 1H).

Example 6

(±)-trans-N-(8-amino-6-(4-ethylpyridin-3-yl)-2,7-naphthyridin-3-yl)-2-cyanocyclopropanecarboxamide (Compound 5)

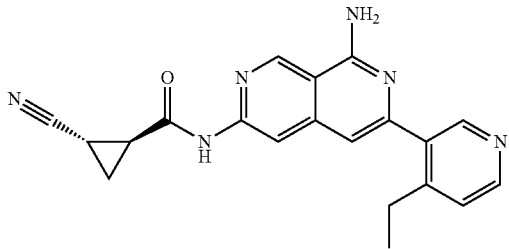 [SMILES: CCc1ccncc1-c1cc2cc(NC(=O)[C@H]3C[C@@H]3C#N)ncc2c(N)n1]

To a vial was added N-(8-amino-6-chloro-2,7-naphthyridin-3-yl)-2-cyano-cyclopropanecarboxamide (220 mg, 0.46 mmol), X-phos (43 mg, 0.09 mmol), XPhos Pd G2 (54 mg, 0.07 mmol), potassium acetate (135 mg, 1.38 mmol), (4-ethyl-3-pyridyl)boronic acid (69 mg, 0.46 mmol), water (1 mL) and 1,4-dioxane (10 mL). The reaction mixture was degassed by N$_2$ bubbling and then stirred at 100° C. for 6 hours. The mixture was concentrated and purified by silica gel chromatography (dichloromethane/methanol from 100:1 to 10:1) to afford (±)-trans-N-[8-amino-6-(4-ethyl-3-pyridyl)-2,7-naphthyridin-3-yl]-2-cyano-cyclopropanecarboxamide (102 mg, 64% yield) as a pale-yellow solid. LCMS (ESI): $R_T$ (min)=1.112, [M+H]$^+$=359.0, method=B; $^1$H-NMR (400 MHz, DMSO-d$_6$): δ 11.28 (s, 1H), 9.41 (s, 1H), 8.50 (s, 1H), 8.49 (d, J=5.2 Hz, 1H), 8.20 (s, 1H), 7.38-7.36 (m, 2H), 7.35 (d, J=5.2 Hz, 1H), 6.95 (s, 1H), 2.80-2.72 (m, 1H), 2.78 (q, J=7.6 Hz, 2H), 2.20-2.12 (m, 1H), 1.65-1.57 (m, 1H), 1.48-1.39 (m, 1H), 1.09 (t, J=7.6 Hz, 3H).

Example 7

(1S,2S)—N-(8-amino-6-(4-methylpyridin-3-yl)-2,7-naphthyridin-3-yl)-2-fluorocyclopropanecarboxamide (Compound 6)

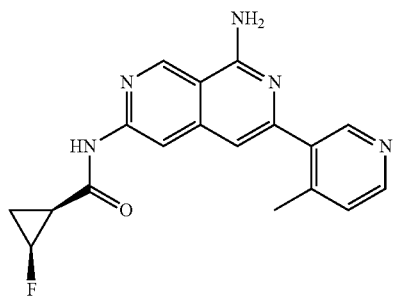 [SMILES: Cc1ccncc1-c1cc2cc(NC(=O)[C@@H]3C[C@@H]3F)ncc2c(N)n1]

To a sealed tube was added (1S,2S)—N-(8-amino-6-chloro-2,7-naphthyridin-3-yl)-2-fluoro-cyclopropanecarboxamide (50 mg, 0.18 mmol), 4-methyl-3-(4,4,5,5-tetramethyl-1,3,2-dioxaborolan-2-yl)pyridine (51 mg, 0.23 mmol), Xphos Pd G2 (14 mg, 0.02 mmol), Xphos (178 mg, 0.04 mmol), potassium acetate (52 mg, 0.53 mmol), 1,4-dioxane (1 mL) and water (0.20 mL). The mixture was stirred at 100° C. for 2 hours and then filtered. The filtrate was concentrated to give a yellow residue, which was then purified by silica gel flash chromatography (dichloromethane/methanol, gradient=20:1 to 10:1) to give a yellow solid. The yellow solid was then purified by reverse phase flash chromatography (Biotage, ODS, 40.0 g column, uv 254 nm) eluting with methanol/water (+0.5% NH$_4$HCO$_3$) to give (1S,2S)—N-[8-amino-6-(4-methyl-3-pyridyl)-2,7-naphthyridin-3-yl]-2-fluoro-cyclopropanecarboxamide (12 mg, 20% yield) as a white solid. LCMS (ESI): $R_T$ (min)=0.990, [M+H]$^+$=338.1, method=B; $^1$H NMR (400 MHz, CD$_3$OD) δ 9.30 (s, 1H), 8.54 (s, 1H), 8.44 (d, J=4.8 Hz, 1H), 8.34 (s, 1H), 7.40 (d, J=4.8 Hz, 1H), 7.00 (s, 1H), 4.98-4.80 (m, 1H), 2.46 (s, 3H), 2.19-2.16 (m, 1H), 1.87-1.80 (m, 1H), 1.26-1.21 (m, 1H).

Example 8

(1S,2S)—N-(8-amino-6-(1-methyl-1H-pyrazol-4-yl)-2,7-naphthyridin-3-yl)-2-fluorocyclopropanecarboxamide (Compound 7)

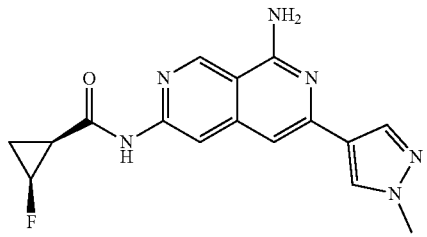 [SMILES: Cn1cc(-c2cc3cc(NC(=O)[C@@H]4C[C@@H]4F)ncc3c(N)n2)cn1]

To a sealed tube was added (1S,2S)—N-(8-amino-6-chloro-2,7-naphthyridin-3-yl)-2-fluoro-cyclopropanecarboxamide (50 mg, 0.18 mmol), 1-methyl-4-(4,4,5,5-tetramethyl-1,3,2-dioxaborolan-2-yl)-1H-pyrazole (48 mg, 0.23 mmol), Xphos Pd G2 (14 mg, 0.02 mmol), Xphos (17 mg, 0.04 mmol), potassium acetate (52 mg, 0.53 mmol), 1,4- dioxane (1 mL) and water (0.20 mL). The mixture was stirred at 100° C. for 4 hours. The reaction mixture was filtered and concentrated to give a yellow residue, which was then purified by silica gel flash chromatography (dichloromethane/methanol, gradient=20:1 to 10:1) to give a yellow solid. The yellow solid was then purified by reverse phase flash chromatography (Biotage, 40.0 g column, ODS, uv 254 nm) eluting with methanol/water (+0.5% NH₄HCO₃) to give (1S,2S)—N-[8-amino-6-(1-methylpyrazol-4-yl)-2,7-naphthyridin-3-yl]-2-fluoro-cyclopropanecarboxamide (29 mg, 50% yield) as a white solid. LCMS (ESI): $R_T$ (min)=1.038, [M+H]⁺=327.1, method=B; ¹H NMR (400 MHz, CD₃OD) δ 9.16 (s, 1H), 8.22 (s, 1H), 8.14 (s, 1H), 8.03 (s, 1H), 7.12 (s, 1H), 4.99-4.79 (m, 1H), 3.96 (s, 3H), 2.18-2.15 (m, 1H), 1.88-1.78 (m, 1H), 1.27-1.19 (m, 1H).

Example 9 trans-N-(8-amino-6-(1-methyl-1H-pyrazol-4-yl)-2,7-naphthyridin-3-yl)-2-fluorocyclopropanecarboxamide (Compound 8)

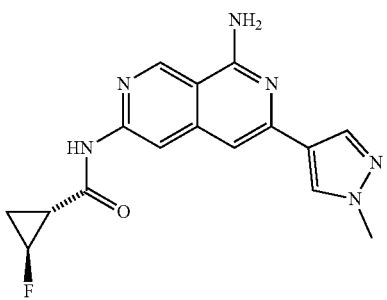 [SMILES: Cn1cc(-c2cc3cc(NC(=O)[C@H]4C[C@@H]4F)ncc3c(N)n2)cn1]

To a sealed tube was added (±)-trans-N-(8-amino-6-chloro-2,7-naphthyridin-3-yl)-2-fluoro-cyclopropanecarboxamide (75 mg, 0.27 mmol), 1-methyl-4-(4,4,5,5-tetramethyl-1,3,2-dioxaborolan-2-yl)-1H-pyrazole (72 mg, 0.35 mmol), Xphos Pd G2 (21 mg, 0.03 mmol), Xphos (25 mg, 0.05 mmol), potassium acetate (79 mg, 0.80 mmol), 1,4-dioxane (1 mL) and water (0.20 mL). The mixture was stirred at 100° C. for 4 hours. The reaction mixture was filtered and concentrated to give a yellow residue, which was then purified by silica gel flash chromatography (dichloromethane/methanol, gradient=20:1 to 10:1) to give a yellow solid. The yellow solid was purified by reverse phase flash chromatography (Biotage, 40.0 g column, ODS, uv 254 nm) eluting with methanol/water (+0.5% NH₄HCO₃) to give trans-N-[8-amino-6-(1-methylpyrazol-4-yl)-2,7-naphthyridin-3-yl]-2-fluoro-cyclopropanecarboxamide (32 mg, 37% yield) as a white solid. LCMS (ESI): $R_T$ (min)=1.063, [M+H]⁺=327.1, method=B; ¹H NMR (400 MHz, CD₃OD) δ 9.16 (s, 1H), 8.17 (s, 1H), 8.13 (s, 1H), 8.02 (s, 1H), 7.10 (s, 1H), 4.97-4.79 (m, 1H), 3.96 (s, 3H), 2.49-2.40 (m, 1H), 1.59-1.50 (m, 1H), 1.49-1.38 (m, 1H).

Example 10

1-(8-amino-6-(1-methyl-1H-pyrazol-4-yl)-2,7-naphthyridin-3-yl)-3-methylurea (Compound 9)

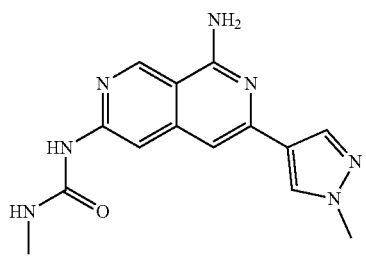 [SMILES: CNC(=O)Nc1cc2cc(-c3cnn(C)c3)nc(N)c2cn1]

Step 1: 1-(6,8-dichloro-2,7-naphthyridin-3-yl)-3-methylurea

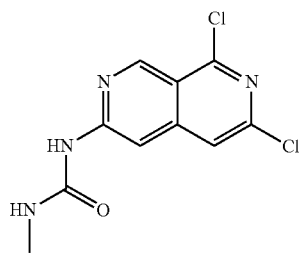 [SMILES: CNC(=O)Nc1cc2cc(Cl)nc(Cl)c2cn1]

To a solution of 6,8-dichloro-2,7-naphthyridin-3-amine hydrochloride (200 mg, 0.8 mmol) in THF (15 mL) was added Et₃N (403 mg, 3.99 mmol) and triphosgene (308 mg, 1.04 mmol). The mixture was stirred at 20° C. for 0.5 hour. Methylamine hydrochloride (108 mg, 1.6 mmol) was added. The resultant mixture was stirred at 20° C. for another 1 hour. The reaction mixture was quenched by water (10 mL) and extracted by dichloromethane (80 mL×3). The organic extracts were combined, concentrated and purified by silica gel flash chromatography (petroleum ether/ethyl acetate=5:1 to 1:2) to give 1-(6,8-dichloro-2,7-naphthyridin-3-yl)-3-methyl-urea (120 mg, 55% yield) as a light yellow solid. LCMS (ESI): [M+H]⁺=271.1.

Step 2: 1-(8-amino-6-chloro-2,7-naphthyridin-3-yl)-3-methylurea

To a sealed tube was added 1-(6,8-dichloro-2,7-naphthyridin-3-yl)-3-methyl-urea (120 mg, 0.44 mmol), NH₄OH (0.5 mL) and 1,4-dioxane (1.5 mL). The mixture was stirred at 80° C. for 6 hours. The reaction mixture was concentrated and purified by silica gel flash chromatography (petroleum ether/ethyl acetate=3:1 to 1:5) to give 1-(8-amino-6-chloro-2,7-naphthyridin-3-yl)-3-methyl-urea (80 mg, 62% yield) as a white solid. LCMS (ESI): [M+H]$^+$=252.2.

Step 3: 1-(8-amino-6-(1-methyl-1H-pyrazol-4-yl)-2,7-naphthyridin-3-yl)-3-methylurea, tert-butyl

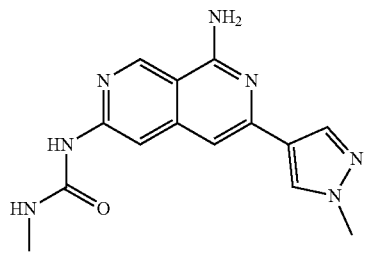 [SMILES: CNC(=O)Nc1cc2cc(-c3cnn(C)c3)nc(N)c2cn1]

To a sealed tube was added 1-(8-amino-6-chloro-2,7-naphthyridin-3-yl)-3-methyl-urea (50 mg, 0.20 mmol), 1-methyl-4-(4,4,5,5-tetramethyl-1,3,2-dioxaborolan-2-yl)-1H-pyrazole (54 mg, 0.26 mmol), Xphos Pd G2 (16 mg, 0.02 mmol), Xphos (19 mg, 0.04 mmol), potassium acetate (58 mg, 0.60 mmol), 1,4-dioxane (1 mL) and water (0.20 mL). The mixture was stirred at 100° C. for 4 hours. The reaction mixture was filtered and concentrated to give a yellow residue, which was purified by silica gel flash chromatography (dichloromethane/methanol, 20:1 to 8:1) to give a yellow solid. The yellow solid was purified by reverse phase flash chromatography (Biotage, 50 g column, ODS, uv 254 nm) eluting with methanol/water (+0.5% NH$_4$HCO$_3$) to give 1-[8-amino-6-(1-methylpyrazol-4-yl)-2,7-naphthyridin-3-yl]-3-methyl-urea (19 mg, 32% yield) as a light yellow solid. LCMS (ESI): R$_T$ (min)=0.934, [M+H]$^+$=298.2, method=B; $^1$H NMR (400 MHz, CD$_3$OD) δ 9.10 (s, 1H), 8.12 (s, 1H), 8.00 (s, 1H), 7.32 (s, 1H), 7.02 (s, 1H), 3.96 (s, 3H), 2.90 (s, 3H).

Example 11

(1S,2S)—N-(8-amino-6-(4-methoxypyridin-3-yl)-2,7-naphthyridin-3-yl)-2-fluorocyclopropanecarboxamide (Compound 10)

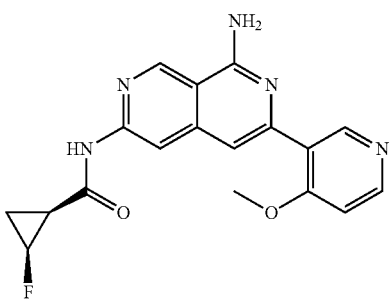 [SMILES: COc1ccncc1-c1cc2cc(NC(=O)[C@@H]3C[C@@H]3F)ncc2c(N)n1]

Step 1: 4-methoxypyridin-3-ylboronic acid

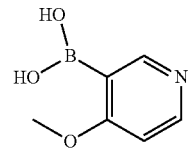

To a sealed tube was added 3-bromo-4-methoxy-pyridine (350 mg, 1.86 mmol), bis(pinacolato)diboron (709 mg, 2.79 mmol), Pd(dppf)Cl$_2$ (136 mg, 0.19 mmol), potassium acetate (548 mg, 5.58 mmol) and 1,4-dioxane (10 mL). The mixture was heated in a microwave reactor at 130° C. for 2 hours. The reaction mixture was used in the next step directly. LCMS (ESI): [M+H]$^+$=154.2.

Step 2: (1S,2S)—N-(8-amino-6-(4-methoxypyridin-3-yl)-2,7-naphthyridin-3-yl)-2-fluorocyclopropanecarboxamide

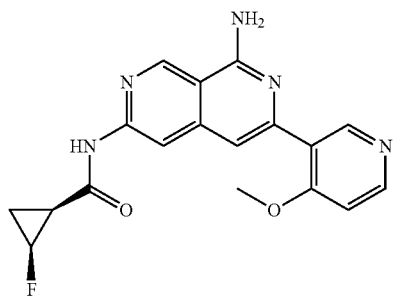 [SMILES: COc1ccncc1-c1cc2cc(NC(=O)[C@@H]3C[C@@H]3F)ncc2c(N)n1]

To a sealed tube was added (1S,2S)—N-(8-amino-6-chloro-2,7-naphthyridin-3-yl)-2-fluoro-cyclopropanecarboxamide (50 mg, 0.18 mmol), crude 4-methoxypyridin-3-ylboronic acid (35 mg, 0.23 mmol), Xphos Pd G2 (14 mg, 0.02 mmol), Xphos (17 mg, 0.04 mmol), potassium acetate (52 mg, 0.53 mmol), 1,4-dioxane (1.0 mL) and water (0.20 mL). The mixture was stirred at 95° C. for 5 hours. The reaction mixture was filtered and concentrated in vacuum to give a yellow residue, which was then purified by silica gel flash chromatography (dichloromethane/methanol, 20:1 to 10:1) to give a yellow solid. The yellow solid was then purified by reverse phase flash chromatography (Biotage, 40.0 g column, ODS, uv 254 nm) eluting with methanol/water (+0.5% NH$_4$HCO$_3$) to give (1S,2S)—N-[8-amino-6-(4-methoxy-3-pyridyl)-2,7-naphthyridin-3-yl]-2-fluoro-cyclopropanecarboxamide (4 mg, 6.4% yield) as an off-white solid. LCMS (ESI): R$_T$ (min)=0.790, [M+H]$^+$=354.1, method=B; $^1$H NMR (CD$_3$OD, 400 MHz) δ 9.24 (s, 1H), 8.78 (s, 1H), 8.43 (d, J=5.6 Hz, 1H), 7.35 (s, 1H), 7.19 (d, J=4.2 Hz, 1H), 4.97-4.77 (m, 1H), 4.00 (s, 3H), 2.17-2.15 (m, 1H), 1.90-1.78 (m, 1H), 1.28-1.18 (m, 1H).

Example 12

N-(8-amino-6-(4-methylpyridin-3-yl)-2,7-naphthyridin-3-yl)-2,2-difluorocyclopropanecarboxamide (Compound 11)

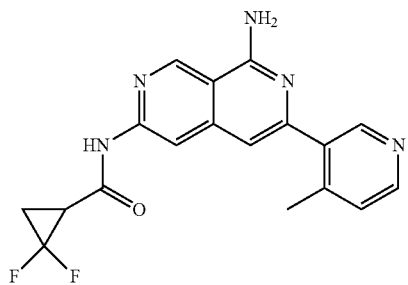 [SMILES: Cc1ccncc1-c1cc2cc(NC(=O)C3CC3(F)F)ncc2c(N)n1]

To a sealed tube was added N-(8-amino-6-chloro-2,7-naphthyridin-3-yl)-2,2-difluoro-cyclopropanecarboxamide (55 mg, 0.18 mmol), 4-methyl-3-(4,4,5,5-tetramethyl-1,3,2-dioxaborolan-2-yl)pyridine (52 mg, 0.24 mmol), Xphos-PdG$_2$ (14 mg, 0.02 mmol), Xphos (17 mg, 0.04 mmol), potassium acetate (54 mg, 0.55 mmol), 1,4-dioxane (1.0 mL) and water (0.20 mL). The reaction mixture was stirred at 95° C. for 4 hours. The reaction mixture was filtered and concentrated in vacuum to give a yellow residue, which was then purified by silica gel flash chromatography (dichloromethane/methanol, 20:1 to 10:1) to give a yellow solid. The yellow solid was then purified by reverse phase flash chromatography (Biotage, 40.0 g column, ODS, uv 254 nm) eluting with methanol/Water (+0.5% NH$_4$HCO$_3$) to give N-[8-amino-6-(4-methyl-3-pyridyl)-2,7-naphthyridin-3-yl]-2,2-difluoro-cyclopropanecarboxamide (23 mg, 34% yield) as a yellow solid. LCMS (ESI): R$_T$ (min)=1.074, [M+H]$^+$=356.1, method=B; $^1$H NMR (400 MHz, CD$_3$OD) δ 9.31 (s, 1H), 8.55 (s, 1H), 8.44 (d, J=5.2 Hz, 1H), 8.34 (s, 1H), 7.41 (d, J=5.2 Hz, 1H), 7.01 (s, 1H), 2.95-2.87 (m, 1H), 2.47 (s, 3H), 2.19-2.13 (m, 1H), 1.93-1.86 (m, 1H).

Example 13

(1S,2S)—N-(8-amino-6-(4-methylpyrimidin-5-yl)-2,7-naphthyridin-3-yl)-2-fluorocyclopropanecarboxamide (Compound 12)

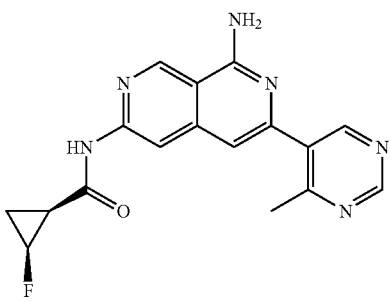

Step 1: 4-methylpyrimidin-5-ylboronic acid

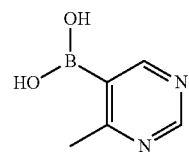

To a sealed tube was added bis(pinacolato)diboron (220 mg, 0.87 mmol), 5-bromo-4-methyl-pyrimidine (100 mg, 0.58 mmol), Pd(dppf)Cl$_2$ (42 mg, 0.06 mmol), potassium acetate (170 mg, 1.73 mmol) and 1,4-dioxane (1.5 mL). The mixture was stirred at 90° C. for 2 hours. LCMS showed the reaction was finished. The reaction mixture was used in the next step directly. LCMS (ESI): [M+H]$^+$=139.2.

Step 2: (1S,2S)—N-(8-amino-6-(4-methylpyrimidin-5-yl)-2,7-naphthyridin-3-yl)-2-fluorocyclopropanecarboxamide

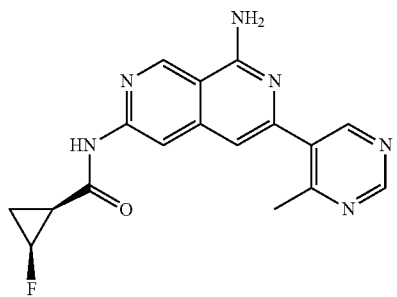 [SMILES: Cc1ncncc1-c1cc2cc(NC(=O)[C@@H]3C[C@@H]3F)ncc2c(N)n1]

To a sealed tube was added (1S,2S)—N-(8-amino-6-chloro-2,7-naphthyridin-3-yl)-2-fluoro-cyclopropanecarboxamide (70 mg, 0.25 mmol), (4-methylpyrimidin-5-yl)boronic acid (45 mg, 0.32 mmol) (the reaction mixture), Xphos Pd G2 (20 mg, 0.02 mmol), Xphos (24 mg, 0.05 mmol), potassium acetate (73 mg, 0.75 mmol), 1,4-dioxane (1.0 mL) and water (0.20 mL). The mixture was stirred at 95° C. for 2 hours. The reaction mixture was filtered and concentrated in vacuum to give a yellow residue, which was then purified by silica gel flash chromatography (dichloromethane/methanol, 20:1 to 10:1) to give a yellow solid. The solid was purified by reverse phase flash chromatography (Biotage, 40.0 g column, silica gel, uv 254 nm) eluting with methanol/water to give (1S,2S)—N-[8-amino-6-(4-methylpyrimidin-5-yl)-2,7-naphthyridin-3-yl]-2-fluoro-cyclopropane carboxamide (32 mg, 35% yield) as a white solid. LCMS (ESI): R$_T$ (min)=0.973, [M+H]$^+$=339.1, method=B; $^1$H NMR (400 MHz, CD$_3$OD) δ 9.31 (s, 1H), 9.05 (s, 1H), 8.80 (s, 1H), 9.36 (s, 1H), 7.09 (s, 1H), 4.97-4.81 (m, 1H), 2.63 (s, 3H), 2.19-2.16 (m, 1H), 1.87-1.80 (m, 1H), 1.26-1.21 (m, 1H).

Example 14

(1S,2S)—N-(8-amino-6-(4-ethylpyrimidin-5-yl)-2,7-naphthyridin-3-yl)-2-fluorocyclopropanecarboxamide (Compound 13)

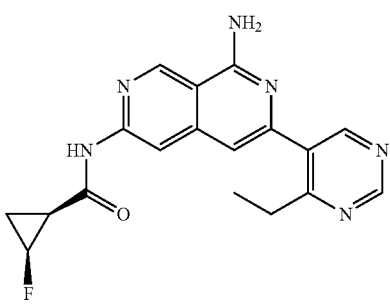 [SMILES: CCc1ncncc1-c1cc2cc(NC(=O)[C@@H]3C[C@@H]3F)ncc2c(N)n1]

Step 1: 4-ethylpyrimidin-5-ylboronic acid

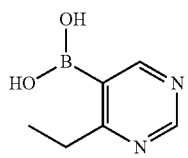

To a sealed tube was added bis(pinacolato)diboron (203 mg, 0.80 mmol), 5-bromo-4-ethyl-pyrimidine (100 mg, 0.53 mmol), Pd(dppf)Cl$_2$ (39 mg, 0.05 mmol), potassium acetate (157 mg, 1.6 mmol) and 1,4-dioxane (1.5 mL). The mixture was stirred at 100° C. for 2 hours. LCMS showed the reaction was finished. The reaction mixture was filtered and used in the next step directly. LCMS (ESI): [M+H]$^+$=153.1.

Step 2: (1S,2S)—N-(8-amino-6-(4-ethylpyrimidin-5-yl)-2,7-naphthyridin-3-yl)-2-fluorocyclopropanecarboxamide

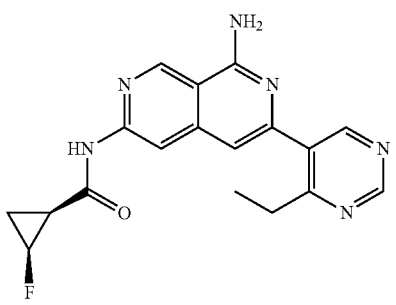

To a sealed tube was added (1S,2S)—N-(8-amino-6-chloro-2,7-naphthyridin-3-yl)-2-fluoro-cyclopropanecarboxamide (60 mg, 0.21 mmol), crude (4-ethylpyrimidin-5-yl)boronic acid (49 mg, 0.32 mmol), Xphos Pd G2 (17 mg, 0.02 mmol), Xphos (20 mg, 0.04 mmol), potassium acetate (63 mg, 0.64 mmol), 1,4-dioxane (1.0 mL) and water (0.20 mL). The mixture was stirred at 100° C. for 4 hours. The reaction mixture was filtered and concentrated in vacuum to give a yellow residue, which was then purified by silica gel flash chromatography (dichloromethane/methanol, 20:1 to 10:1) to give a yellow solid. The yellow solid was then purified by reverse phase flash chromatography (Biotage, 40.0 g column, ODS, uv 254 nm) eluting with methanol/water (+0.5% NH$_4$HCO$_3$) to give (1S,2S)—N-[8-amino-6-(4-ethylpyrimidin-5-yl)-2,7-naphthyridin-3-yl]-2-fluoro-cyclopropanecarboxamide (22 mg, 27% yield) as a white solid. LCMS (ESI): R$_T$ (min)=1.065, [M+H]$^+$=353.1, method=B; $^1$H NMR (400 MHz, CD$_3$OD) δ 9.31 (s, 1H), 9.09 (s, 1H), 8.76 (s, 1H), 8.35 (s, 1H), 7.05 (s, 1H), 4.98-4.81 (m, 1H), 2.98 (q, J=7.6 Hz, 2H), 2.19-2.16 (m, 1H), 1.87-1.80 (m, 1H), 1.29-1.21 (m, 4H).

Example 15

(1S,2S)—N-(8-amino-6-(4-(difluoromethyl)pyridin-3-yl)-2,7-naphthyridin-3-yl)-2-fluorocyclopropanecarboxamide (Compound 14)

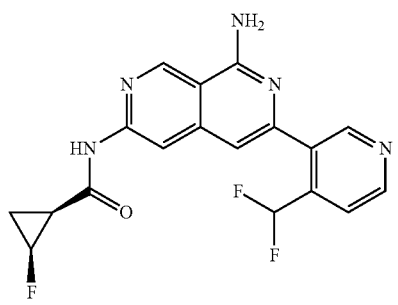

Step 1: 3-bromo-4-(difluoromethyl)pyridine

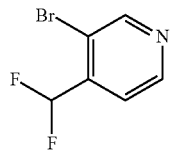

To a solution of 3-bromoisonicotinaldehyde (200 mg, 1.08 mmol) in dichloromethane (10 mL) was added dropwise DAST (693 mg, 4.3 mmol) at 0° C. The mixture was stirred at 0° C. for 2 hours. The reaction mixture was quenched with aqueous saturated NaHCO$_3$ (5 mL) and extracted with dichloromethane (50 mL×3). The organic extracts were combined, concentrated and purified by silica gel flash chromatography (petroleum ether/ethyl acetate=10:1 to 3:1) to give 3-bromo-4-(difluoromethyl)pyridine (150 mg, 67% yield) as a colorless oil. LCMS (ESI): [M+H]$^+$=208.2.

Step 2: 4-(difluoromethyl)pyridin-3-ylboronic acid

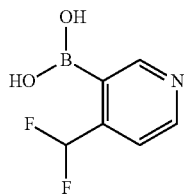 [SMILES: OB(O)c1cnccc1C(F)F]

To a sealed tube was added bis(pinacolato)diboron (183 mg, 0.72 mmol), 3-bromo-4-(difluoromethyl)pyridine (100 mg, 0.48 mmol), potassium acetate (141 mg, 1.44 mmol), Pd(dppf)Cl$_2$ (35 mg, 0.05 mmol) and 1,4-dioxane (1.5 mL). The mixture was stirred at 100° C. for 2 hours. The reaction mixture was filtered and the filtrate was used in the next step directly. LCMS (ESI): [M+H]$^+$=174.1.

Step 3: (1S,2S)—N-(8-amino-6-(4-(difluoromethyl)pyridin-3-yl)-2,7-naphthyridin-3-yl)-2-fluorocyclopropanecarboxamide

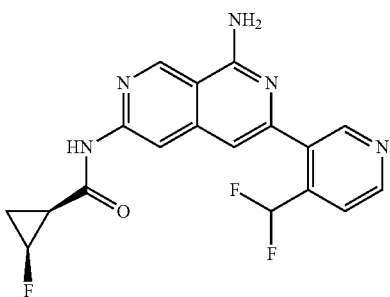 [SMILES: Nc1nc(-c2cnccc2C(F)F)cc2cc(NC(=O)[C@@H]3C[C@@H]3F)ncc12]

To a sealed tube was added (1S,2S)—N-(8-amino-6-chloro-2,7-naphthyridin-3-yl)-2-fluoro-cyclopropanecarboxamide (50 mg, 0.18 mmol), crude [4-(difluoromethyl)-3-pyridyl]boronic acid (46 mg, 0.27 mmol), Xphos Pd G2 (14 mg, 0.02 mmol), Xphos (17 mg, 0.04 mmol), potassium acetate (52 mg, 0.53 mmol), 1,4-dioxane (1.0 mL) and water (0.20 mL). The mixture was stirred at 100° C. for 4 hours. The reaction mixture was concentrated in vacuum and purified by silica gel flash chromatography (dichloromethane/methanol, 20:1 to 10:1) to give a yellow solid. The yellow solid was then purified by reverse phase flash chromatography (Biotage, 40.0 g column, ODS, uv 254 nm) eluting with methanol/water (+0.5% NH$_4$HCO$_3$) to give (1S,2S)—N-[8-amino-6-[4-(difluoromethyl)-3-pyridyl]-2,7-naphthyridin-3-yl]-2-fluoro-cyclopropanecarboxamide (18 mg, 26% yield) as a white solid. LCMS (ESI): R$_T$ (min)=1.142, [M+H]$^+$=374.1, method=B; $^1$H NMR (400 MHz, CD$_3$OD) δ 9.30 (s, 1H), 8.89 (s, 1H), 8.77 (d, J=5.2 Hz, 1H), 8.37 (s, 1H), 7.79 (d, J=5.2 Hz, 1H), 7.54 (t, J=14.8 Hz, 1H), 7.15 (s, 1H), 5.00-4.79 (m, 1H), 2.19-2.14 (m, 1H), 1.88-1.78 (m, 1H), 1.28-1.21 (m, 1H).

Example 16

(1S,2S)—N-(8-amino-6-(4-cyanopyridin-3-yl)-2,7-naphthyridin-3-yl)-2-fluorocyclopropanecarboxamide (Compound 15)

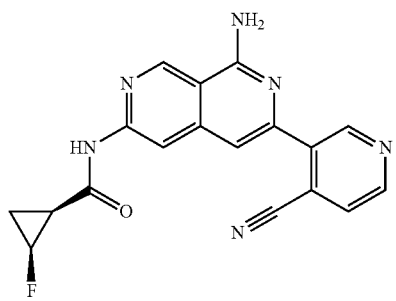 [SMILES: N#Cc1ccncc1-c1cc2cc(NC(=O)[C@@H]3C[C@@H]3F)ncc2c(N)n1]

To a sealed tube was added (1S,2S)—N-(8-amino-6-chloro-1,7-naphthyridin-3-yl)-2-fluoro-cyclopropanecarboxamide (60 mg, 0.21 mmol), 3-(4,4,5,5-tetramethyl-1,3,2-dioxaborolan-2-yl)pyridine-4-carbonitrile (59 mg, 0.26 mmol), Xphos Pd G2 (17 mg, 0.02 mmol), potassium acetate (63 mg, 0.64 mmol), Xphos (20 mg, 0.04 mmol), 1,4-dioxane (3.0 mL) and water (0.50 mL). The mixture was stirred at 100° C. for 2 hours. The reaction mixture was concentrated and purified by silica gel flash chromatography (dichloromethane/methanol, 20:1 to 10:1) to give (1S,2S)—N-(8-amino-6-(4-cyanopyridin-3-yl)-2,7-naphthyridin-3-yl)-2-fluorocyclopropanecarboxamide (8 mg, 10.7% yield) as a yellow solid. LCMS (ESI): R$_T$ (min)=1.603, [M+H]$^+$=349.1, method=C; $^1$H NMR (400 MHz, CD$_3$OD) δ 9.32 (s, 1H), 9.18 (s, 1H), 8.80 (d, J=5.2 Hz, 1H), 8.40 (s, 1H), 7.87 (d, J=4.8 Hz, 1H), 7.40 (s, 1H), 5.00-4.79 (m, 1H), 2.21-2.15 (m, 1H), 1.89-1.79 (m, 1H), 1.30-1.19 (m, 1H).

Example 17

(±)-cis-N-(8-amino-6-(6-amino-4-methylpyridin-3-yl)-2,7-naphthyridin-3-yl)-2-fluorocyclopropanecarboxamide (Compound 16)

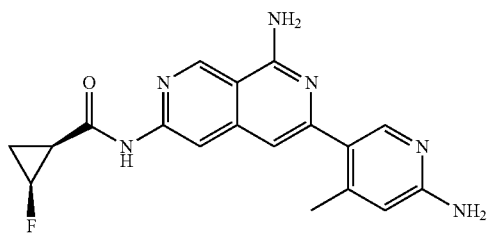 [SMILES: Cc1cc(N)ncc1-c1cc2cc(NC(=O)[C@@H]3C[C@@H]3F)ncc2c(N)n1]

Step 1: tert-butyl 5-bromo-4-methylpyridin-2-ylcarbamate

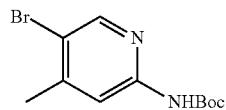

447

To a solution of 5-bromo-4-methyl-2-pyridinamine (2.0 g, 10.69 mmol) in dichloromethane (100 mL) was added Boc₂O (2.8 g, 12.83 mmol) and DMAP (3.26 g, 26.73 mmol). The mixture was stirred at 20° C. for 16 hours. The reaction mixture was concentrated in vacuum and the residue was purified by silica gel flash chromatography (petroleum ether/ethyl acetate, 20:1 to 5:1) to give tert-butyl N-(5-bromo-4-methyl-2-pyridyl)carbamate (1.6 g, 47% yield) as a white solid. LCMS (ESI): [M+H]⁺=289.1.

Step 2: tert-butyl 4-methyl-5-(4,4,5,5-tetramethyl-1,3,2-dioxaborolan-2-yl)pyridin-2-ylcarbamate

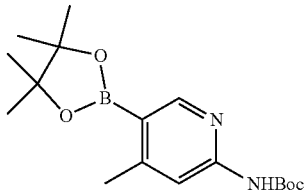 [SMILES: Cc1cc(NC(=O)OC(C)(C)C)ncc1B1OC(C)(C)C(C)(C)O1]

To a sealed tube was added tert-butyl N-(5-bromo-4-methyl-2-pyridyl)carbamate (1.0 g, 3.48 mmol), bis(pinacolato)diboron (1.06 g, 4.18 mmol), Pd(dppf)Cl₂ (254 mg, 0.35 mmol), potassium acetate (682 mg, 6.97 mmol) and 1,4-dioxane (10 mL). The mixture was stirred at 100° C. for 2 hours. The reaction mixture was concentrated and purified by silica gel flash chromatography (petroleum ether/ethyl acetate, 20:1 to 5:1) to give tert-butyl N-[4-methyl-5-(4,4,5,5-tetramethyl-1,3,2-dioxaborolan-2-yl)-2-pyridyl]carbamate (800 mg, 52% yield) as a white solid. LCMS (ESI): [M+H]⁺=335.2.

Step 3: (±)-tert-butyl 5-(1-amino-6-(cis-2-fluorocyclopropanecarboxamido)-2,7-naphthyridin-3-yl)-4-methylpyridin-2-ylcarbamate

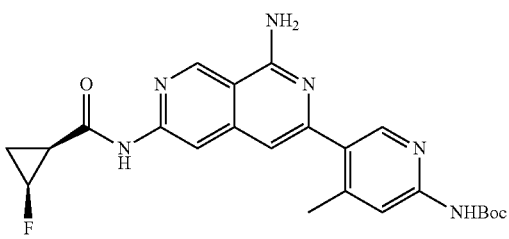 [SMILES: Cc1cc(NC(=O)OC(C)(C)C)ncc1-c1cc2cc(NC(=O)[C@@H]3C[C@@H]3F)ncc2c(N)n1]

To a sealed tube was added tert-butyl N-[4-methyl-5-(4,4,5,5-tetramethyl-1,3,2-dioxaborolan-2-yl)-2-pyridyl]carbamate (200 mg, 0.60 mmol), Pd(PPh₃)₄ (69 mg, 0.06 mmol), (±)-cis-N-(8-amino-6-chloro-2,7-naphthyridin-3-yl)-2-fluoro-cyclopropanecarboxamide (184 mg, 0.66 mmol), K₃PO₄ (117 mg, 1.2 mmol), water (0.2 mL) and 1,4-dioxane (2 mL). The mixture was stirred at 100° C. for 4 hours. The reaction mixture was concentrated was and purified by silica gel flash chromatography (dichloromethane/methanol, 50:1 to 10:1) to give (±)-tert-butyl N-[5-[1-amino-6-[[2-fluorocyclopropanecarbonyl]amino]-2,7-naphthyridin-3-yl]-4-methyl-2-pyridyl]carbamate (151 mg, 42% yield) as a yellow solid. LCMS (ESI): [M+H]⁺=453.0.

448

Step 4: (±)-cis-N-(8-amino-6-(6-amino-4-methylpyridin-3-yl)-2,7-naphthyridin-3-yl)-2-fluorocyclopropanecarboxamide

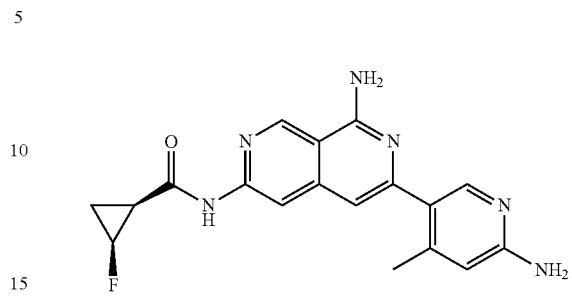

To a solution of (±)-tert-butyl N-[5-[1-amino-6-[[cis-2-fluorocyclopropanecarbonyl]amino]-2,7-naphthyridin-3-yl]-4-methyl-2-pyridyl]carbamate (150 mg, 0.33 mmol) in dichloromethane (5 mL) was added TFA (2.0 mL, 0.33 mmol). The mixture was stirred at 20° C. for 3 hours. The reaction mixture was concentrated in vacuum and the residue was adjusted to pH 8.0 by adding a solution of NH₃ (7 M in methanol). The resultant mixture was concentrated in vacuum and the residue was purified by silica gel flash chromatography (dichloromethane/methanol, 20:1 to 10:1) to give a yellow solid, which was then purified by reverse phase flash chromatography (Biotage, 40.0 g column, ODS, uv 254 nm) eluting with methanol/water (+0.5% NH₄HCO₃) to give cis-N-[8-amino-6-(6-amino-4-methyl-3-pyridyl)-2,7-naphthyridin-3-yl]-2-fluoro-cyclopropanecarboxamide (60 mg, 49% yield) as a white solid. LCMS (ESI): R$_T$ (min)=1.408, [M+H]⁺=353.2, method=G; ¹H NMR (400 MHz, DMSO-d₆) δ 10.94 (s, 1H), 9.31 (s, 1H), 8.18 (s, 1H), 8.02 (s, 1H), 7.17 (s, 2H), 6.84 (s, 1H), 6.31 (s, 1H), 5.96 (s, 2H), 5.03-4.86 (m, 1H), 2.30 (s, 3H), 2.28-2.24 (m, 1H), 1.70-1.63 (m, 1H), 1.21-1.14 (m, 1H).

Example 18

(1S,2S)—N-(8-amino-6-(5-fluoro-4-methylpyridin-3-yl)-2,7-naphthyridin-3-yl)-2-fluorocyclopropanecarboxamide (Compound 17)

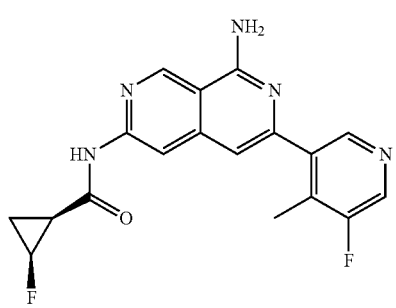 [SMILES: Cc1c(F)cncc1-c1cc2cc(NC(=O)[C@@H]3C[C@@H]3F)ncc2c(N)n1]

A mixture of (1S,2S)—N-(8-amino-6-chloro-2,7-naphthyridin-3-yl)-2-fluoro-cyclopropanecarboxamide (184 mg, 0.66 mmol), 3-fluoro-4-methyl-5-(4,4,5,5-tetramethyl-1,3,2-dioxaborolan-2-yl)pyridine (120 mg, 0.51 mmol), XPhos Pd G2 (40 mg, 0.05 mmol), X-phos (48 mg, 0.1 mmol) and acetoxypotassium (149 mg, 1.52 mmol) in 1,4-dioxane (5 mL) and water (0.5 mL) was stirred at 100° C. under the N₂ for 8 hours. The mixture was concentrated and the residue was purified by reversed phase flash chromatography (C18 gel, 0-30% acetonitrile in water with 0.1% formic acid) to give the (1S,2S)—N-[8-amino-6-(5-fluoro-4-methyl-3-pyridyl)-2,7-naphthyridin-3-yl]-2-fluoro-cyclopropanecarboxamide (42 mg, 23% yield) as a yellow solid. LCMS (ESI): $R_T$ (min)=1.099, [M+H]⁺=356.1, method=B; ¹H NMR (400 MHz, DMSO-$d_6$) δ 11.05 (s, 1H), 8.52 (s, 1H), 8.48 (s, 1H), 8.27 (s, 1H), 8.15 (s, 1H), 7.40 (s, 2H), 7.03 (s, 1H), 5.09-4.83 (m, 1H), 4.35 (d, J=2.0 Hz, 3H), 2.32-2.21 (m, 1H), 1.75-1.62 (m, 1H), 1.25-1.14 (m, 1H).

Example 19

(1S,2S)—N-(8-amino-6-(1-methyl-1H-pyrazol-5-yl)-2,7-naphthyridin-3-yl)-2-fluorocyclopropanecarboxamide (Compound 18)

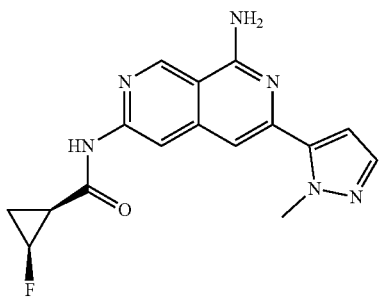 [SMILES: Cn1nccc1-c1cc2cc(NC(=O)[C@@H]3C[C@@H]3F)ncc2c(N)n1]

To a mixture of (1S,2S)—N-(8-amino-6-chloro-2,7-naphthyridin-3-yl)-2-fluoro-cyclopropanecarboxamide (150 mg, 0.53 mmol), 1-methyl-H-pyrazole-5-boronic acid pinacol ester (166 mg, 0.8 mmol), potassium acetate (157 mg, 1.6 mmol), X-phos (51 mg, 0.11 mmol) and XPhos Pd G2 (42 mg, 0.05 mmol) in 1,4-dioxane (5 mL) and water (0.5 mL) was stirred at 100° C. under the N₂ for 4 hours. The mixture was concentrated and the residue was purified by reverse phase preparative HPLC (C-18), eluting with 0-33% acetonitrile in water (with 0.1% formic acid) to give the desired product (1S,2S)—N-[8-amino-6-(2-methylpyrazol-3-yl)-2,7-naphthyridin-3-yl]-2-fluoro-cyclopropanecarboxamide (27 mg, 15% yield) as a yellow solid. LCMS (ESI): $R_T$ (min)=1.055, [M+H]⁺=327.1, method=B; ¹H NMR (400 MHz, DMSO-$d_6$) δ 11.02 (s, 1H), 8.24 (s, 1H), 8.15 (s, 1H), 7.45 (d, J=2.0 Hz, 1H), 7.40 (s, 2H), 7.21 (s, 1H), 6.73 (d, J=2.0 Hz, 1H), 5.07-4.84 (m, 1H), 4.19 (s, 3H), 2.32-2.21 (m, 1H), 1.75-1.62 (m, 1H), 1.25-1.14 (m, 1H).

Example 20

(±)-cis-N-(8-amino-6-(6-methyl-1H-benzo[d]imidazol-5-yl)-2,7-naphthyridin-3-yl)-2-fluorocyclopropanecarboxamide (Compound 19)

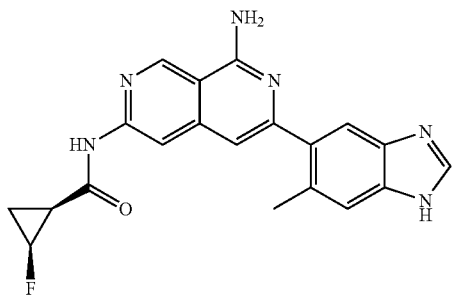 [SMILES: Cc1cc2[nH]cnc2cc1-c1cc2cc(NC(=O)[C@@H]3C[C@@H]3F)ncc2c(N)n1]

A mixture of cis-N-(8-amino-6-chloro-2,7-naphthyridin-3-yl)-2-fluoro-cyclopropanecarboxamide (50 mg, 0.18 mmol), tert-butyl 6-methyl-5-(4,4,5,5-tetramethyl-1,3,2-dioxaborolan-2-yl)benzimidazole-1-carboxylate (70 mg, 0.20 mmol), Pd(dppf)Cl₂ (13 mg, 0.02 mmol) and K₂CO₃ (73 mg, 0.53 mmol) in 1,4-dioxane (6 mL) and water (1 mL) was heated to 110° C. for 16 hours. The reaction mixture was concentrated. The residue was purified by prep-TLC (normal phase silica gel, dichloromethane/methanol, 10/1) to afford a yellow oil, which was further purified by prep-HPLC (Column Xbridge 21.2*250 mm c18, 10 μm Mobile Phase A: water (10 mmol/L NH₄HCO₃) B: acetonitrile) to give (±)-N-[8-amino-6-(6-methyl-1H-benzimidazol-5-yl)-2,7-naphthyridin-3-yl]-2-fluoro-cyclopropanecarboxamide (17 mg, 25% yield) as a white solid. LCMS (ESI): $R_T$ (min)=1.269, [M+H]⁺=377.1, method=A; ¹H NMR (400 MHz, CD₃OD) δ 9.29 (s, 1H), 8.32 (s, 1H), 8.18 (s, 1H), 7.66 (s, 1H), 7.53 (s, 1H), 6.95 (s, 1H), 4.95-4.84 (m, 1H), 2.45 (s, 3H), 2.22-2.14 (m, 1H), 1.88-1.78 (m, 1H), 1.26-1.18 (m, 1H).

Example 21

N-[8-amino-6-(4-ethyl-3-pyridyl)-2,7-naphthyridin-3-yl]cyclobutanecarboxamide (Compound 20)

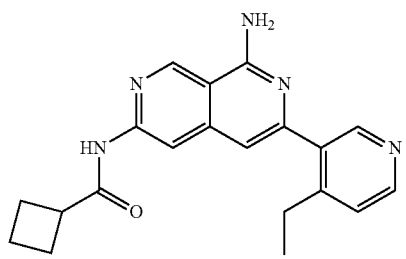 [SMILES: CCc1ccncc1-c1cc2cc(NC(=O)C3CCC3)ncc2c(N)n1]

Step 1: N-[8-[bis[(4-methoxyphenyl)methyl]amino]-6-(4-ethyl-3-pyridyl)-2,7-naphthyridin-3-yl]cyclobutanecarboxamide

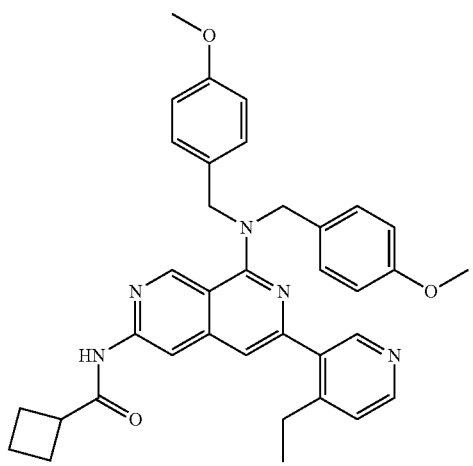 [SMILES: CCc1ccncc1-c1cc2cc(NC(=O)C3CCC3)ncc2c(N(Cc2ccc(OC)cc2)Cc2ccc(OC)cc2)n1]

A solution of cyclobutanecarbonyl chloride (60 mg, 0.51 mmol) in dichloromethane (0.3 mL) was added dropwise to a solution of 3-(4-ethyl-3-pyridyl)-N1,N1-bis[(4-methoxyphenyl) methyl]-2,7-naphthyridine-1,6-diamine (300 mg, 0.59 mmol), triethylamine (200.0 mg, 1.98 mmol) in dichloromethane (5 mL) at 0° C. and stirred at 0° C. for 1 hour. The reaction mixture was evaporated to give a residue that was purified with silica gel chromatography (petroleum ether/ethyl acetate=1:1 to 1:2) to afford N-[8-[bis[(4-methoxyphenyl)methyl]amino]-6-(4-ethyl-3-pyridyl)-2,7-naphthyridin-3-yl]cyclobutanecarboxamide (90 mg, 25% yield) as a brown solid. LCMS (ESI) [M+H]$^+$=588.3.

Step 2: N-[8-amino-6-(4-ethyl-3-pyridyl)-2,7-naphthyridin-3-yl]cyclobutanecarboxamide

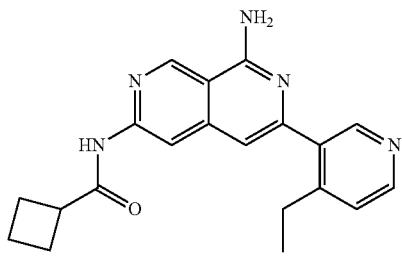 [SMILES: CCc1ccncc1-c1cc2cc(NC(=O)C3CCC3)ncc2c(N)n1]

A mixture of N-[8-[bis[(4-methoxyphenyl)methyl]amino]-6-(4-ethyl-3-pyridyl)-2,7-naphthyridin-3-yl]cyclobutanecarboxamide (90 mg, 0.15 mmol) in TFA (3 mL) was stirred at 25° C. for 1 hour and stirred at 80° C. for an additional 2 hours. The reaction mixture was evaporated. The residue was suspended in methanol (1 mL) and 7N NH$_3$-methanol was added until pH=10-11 (brown suspension). The solid was collected by filtration and the crude product purified by reverse phase flash chromatography (C18, methanol/water to formic acid/methanol/water) to give the formic acid salt of N-[8-amino-6-(4-ethyl-3-pyridyl)-2,7-naphthyridin-3-yl]cyclobutanecarboxamide (21 mg, 35% yield) as a brown solid. LCMS (ESI): R$_T$ (min)=1.752, [M+H]$^+$=348.2, method=C; $^1$H NMR (400 MHz, CD$_3$OD) δ 9.30 (s, 1H), 8.51-8.49 (m, 2H), 8.37 (s, 1H), 8.30 (brs, 1H), 7.46 (d, J=5.2 Hz, 1H), 7.00 (s, 1H), 3.45-3.41 (m, 1H), 2.85 (q, J=7.6 Hz, 2H), 2.43-2.36 (m, 2H), 2.31-2.23 (m, 2H), 2.12-2.05 (m, 1H), 1.98-1.93 (m, 1H), 1.20 (t, J=7.6 Hz, 3H).

Example 22

(±)-cis-N-(8-amino-6-(1H-pyrrolo[2,3-c]pyridin-4-yl)-2,7-naphthyridin-3-yl)-2-cyanocyclopropanecarboxamide (Compound 21)

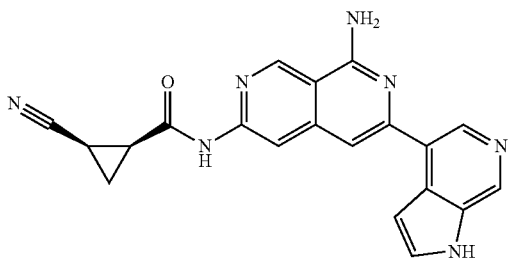 [SMILES: N#C[C@@H]1C[C@@H]1C(=O)Nc1cc2cc(-c3cncc4[nH]ccc34)nc(N)c2cn1]

Step 1: 1H-pyrrolo[2,3-c]pyridin-4-ylboronic acid

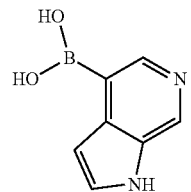 [SMILES: OB(O)c1cncc2[nH]ccc12]

A mixture of 4-bromo-1h-pyrrolo[2,3-c]pyridine (500 mg, 2.54 mmol), bis(pinacolato)diboron (6.4 g, 25.2 mmol), PdCl$_2$dppf (371 mg, 0.51 mmol), and potassium acetate (746 mg, 7.61 mmol) in 1,4-dioxane (20 mL) was heated at 120° C. for 16 hours under Ar. The reaction was filtered and concentrated to dryness. The residue was taken up in ethyl acetate (10 mL) and adjusted to pH 7-8 with NaOH. The water layer was adjusted pH to 3-4 with conc. HCl and ethyl acetate (20 mL) added. The water layer were then separated and concentrated to dryness. The residue was taken up in ethyl acetate:ethanol (1:1) and filtered. The resulting liquid was concentrated to dryness. This provided the title compound as a brown solid (350 mg, 85% yield). LCMS (ESI) [M+H]$^+$=163.1.

Step 2: (±)-cis-N-(8-amino-6-(1H-pyrrolo[2,3-c]pyridin-4-yl)-2,7-naphthyridin-3-yl)-2-cyanocyclopropanecarboxamide

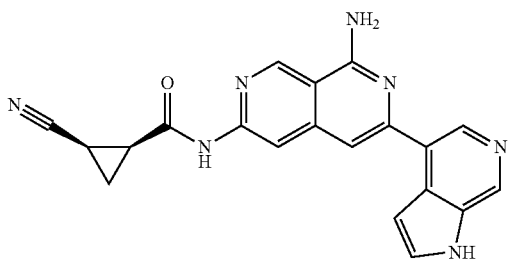 [SMILES: N#C[C@@H]1C[C@@H]1C(=O)Nc1cc2cc(-c3cncc4[nH]ccc34)nc(N)c2cn1]

A mixture of 1H-pyrrolo[2,3-c]pyridin-4-ylboronic acid (200 mg, 1.23 mmol), cis-N-(8-amino-6-chloro-2,7-naphthyridin-3-yl)-2-cyano-cyclopropanecarboxamide (100 mg, 0.35 mmol), Pd(PPh$_3$)$_4$ (40 mg, 0.03 mmol), K$_2$CO$_3$ (144 mg, 1.04 mmol) in 1,4-dioxane (4 mL) and water (1 mL) was heated at 100° C. for 3 hours under Ar. The reaction was concentrated to dryness. The residue was purified with silica chromatography (ethyl acetate to ethyl acetate/methanol=10:1) to give the title compound as a yellow solid (14.7 mg, 11.4% yield). LCMS (ESI): R$_T$(min)=1.035, [M+H]$^+$=370.1, method=B. $^1$H NMR (400 MHz, CD$_3$OD) δ 9.30 (s, 1H), 8.91 (s, 1H), 8.67 (s, 1H), 8.03 (s, 1H), 7.47 (s, 1H), 7.32 (s, 1H), 7.31 (s, 1H), 2.56-2.54 (m, 1H), 2.19-2.17 (m, 1H), 1.72-1.70 (m, 1H), 1.55-1.53 (m, 1H).

Example 23

(±)-cis-N-(8-amino-6-(3-methylpyridin-4-yl)-2,7-naphthyridin-3-yl)-2-fluorocyclopropanecarboxamide (Compound 22)

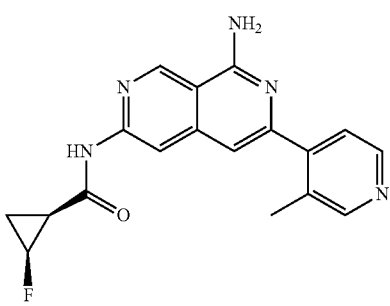 [SMILES: Cc1cnccc1-c1cc2cc(NC(=O)[C@@H]3C[C@@H]3F)ncc2c(N)n1]

Step 1: 3-methyl-4-(4,4,5,5-tetramethyl-1,3,2-dioxaborolan-2-yl)pyridine

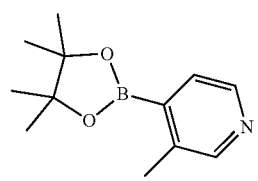 [SMILES: Cc1cnccc1B1OC(C)(C)C(C)(C)O1]

A mixture of 4-bromo-3-methyl-pyridine (5.0 g, 29.07 mmol), bis(pinacolato)diboron (7.38 g, 29.06 mmol), PdCl$_2$dppf (2.12 g, 2.9 mmol) and potassium acetate (8.54 g, 87.14 mmol) in 1,4-dioxane (100 mL) was heated at 110° C. for 3 hours under Ar. The reaction mixture was filtered and concentrated to dryness. The residue was taken up in water (40 mL) and adjusted pH to 11-12 with aqueous NaOH. The liquid was washed with ethyl acetate (100 ml). The aqueous layer was adjusted pH to 5-6 with HCl. The organics were then separated and dried (NaSO$_4$) before concentration to dryness. The product is brown solid (4 g, 60% yield) in the end. LCMS (ESI) [M+H]$^+$=220.2.

Step 2: (±)-cis-N-(8-amino-6-(3-methylpyridin-4-yl)-2,7-naphthyridin-3-yl)-2-fluorocyclopropanecarboxamide

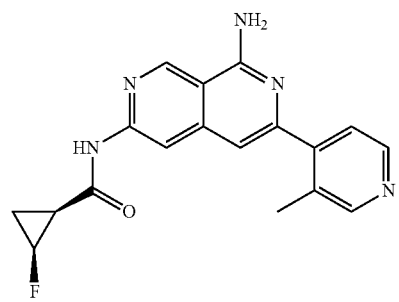 [SMILES: Cc1cnccc1-c1cc2cc(NC(=O)[C@@H]3C[C@@H]3F)ncc2c(N)n1]

A mixture of 3-methyl-4-(4,4,5,5-tetramethyl-1,3,2-dioxaborolan-2-yl)pyridine (100 mg, 0.46 mmol), (±)-cis-N-(8-amino-6-chloro-2,7-naphthyridin-3-yl)-2-fluoro-cyclopropanecarboxamide (128 mg, 0.46 mmol), XPhos Pd G2 (36 mg, 0.05 mmol), XPhos (22 mg, 0.05 mmol), and potassium acetate (134 mg, 1.37 mmol) in 1,4-dioxane (8 mL) and water (2 mL) was heated at 110° C. for 3 hours under Ar. The reaction was concentrated to dryness and the resulting residue was purified by silica gel chromatography (petroleum ether/ethyl acetate=1:1). This provided the title compound as a white solid (25.1 mg, 16% yield). LCMS (ESI): R$_T$(min)=1.059, [M+H]$^+$=338.1, method=B. $^1$H NMR (400 MHz, CD$_3$OD) δ 8.51 (s, 1H), 8.47 (s, 1H), 8.35 (s, 1H), 8.21 (s, 1H), 7.51 (d, J=4.8 Hz, 1H), 7.03 (s, 1H), 2.43 (s, 3H), 4.99-4.97 (m, 0.5H), 4.83-4.80 (m, 0.5H), 2.19-2.16 (m, 1H), 1.87-1.80 (m, 1H), 1.28-1.21 (m, 1H).

Example 24

N-(8-amino-6-(4-methylpyridin-3-yl)-2,7-naphthyridin-3-yl)cyclopropanecarboxamide (Compound 24)

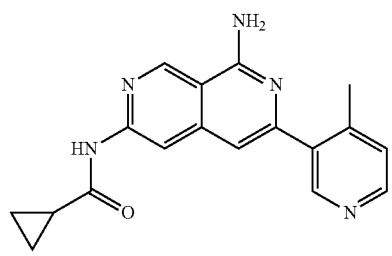 [SMILES: Cc1ccncc1-c1cc2cc(NC(=O)C3CC3)ncc2c(N)n1]

A mixture of N-(6-chloro-8-(diphenylmethyleneamino)-2,7-naphthyridin-3-yl)cyclopropanecarboxamide (45 mg, 0.11 mmol), 4-methyl-3-(4,4,5,5-tetramethyl-1,3,2-dioxaborolan-2-yl)pyridine (34 mg, 0.16 mmol), Pd(PPh$_3$)$_4$ (12 mg, 0.01 mmol) and Cs$_2$CO$_3$ (68 mg, 0.21 mmol) in 1,4-dioxane (10 mL) was heated to 100° C. for 18 hours in a glovebox. The reaction mixture was cooled to room temperature and filtered through celite. The filtrate was then concentrated and the resulting residue was dissolved in THF (5 mL). A HCl in dioxane solution (4 mL, 4 M, 16 mmol) was added and the reaction mixture was stirred at 25° C. for 2 hours. The reaction mixture was concentrated. The residue was diluted with ethyl acetate, adjusted pH to >7 with a 7N NH$_3$ in methanol solution and concentrated. The residue was extracted with dichloromethane/methanol (25/1) to give the crude product. The crude product was purified by prep-HPLC to give the product N-(8-amino-6-(4-methylpyridin-3-yl)-2,7-naphthyridin-3-yl)cyclopropanecarboxamide (12 mg, 30% yield) as a white solid. LCMS (ESI): R$_T$ (min)=1.580, [M+H]$^+$=320.1, method=F; $^1$H NMR (400 MHz, CD$_3$OD) δ 9.29 (s, 1H), 8.56 (s, 1H), 8.43 (d, 1H, J=5.2 Hz), 8.31 (s, 1H), 7.39 (d, 1H, J=5.2 Hz), 6.98 (s, 1H), 2.46 (s, 3H), 1.92-2.00 (m, 1H), 1.01-1.06 (m, 2H), 0.92-0.97 (m, 2H).

Example 25

N-(8-amino-6-(6-(hydroxymethyl)-4-methylpyridin-3-yl)-2,7-naphthyridin-3-yl)cyclopropanecarboxamide (Compound 25)

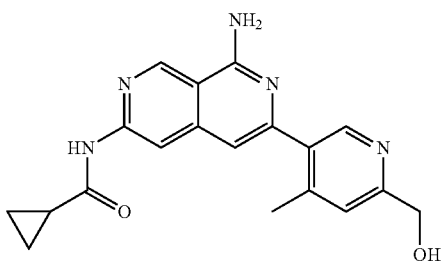 [SMILES: Cc1cc(CO)ncc1-c1cc2cc(NC(=O)C3CC3)ncc2c(N)n1]

Step 1: N-(8-(diphenylmethyleneamino)-6-(6-(hydroxymethyl)-4-methylpyridin-3-yl)-2,7-naphthyridin-3-yl)cyclopropanecarboxamide

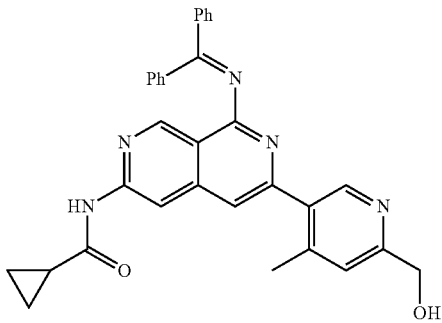 [SMILES: Cc1cc(CO)ncc1-c1cc2cc(NC(=O)C3CC3)ncc2c(N=C(c2ccccc2)c2ccccc2)n1]

A mixture of N-[8-(benzhydrylideneamino)-6-chloro-2,7-naphthyridin-3-yl]cyclopropanecarboxamide (78 mg, 0.18 mmol), [4-methyl-5-(4,4,5,5-tetramethyl-1,3,2-dioxaborolan-2-yl)-2-pyridyl]methanol (200 mg, 0.80 mmol), X-phos (8.7 mg, 0.02 mmol), Xphos Pd G2 (14 mg, 0.02 mmol) and potassium acetate (53 mg, 0.55 mmol) in 1,4-dioxane (10 mL) and water (1 mL) was heated to 100° C. under N$_2$ for 16 hours. The reaction mixture was then concentrated. The residue was purified by prep-TLC (normal phase silica gel, dichloromethane/methanol=25/1) to give the product N-[8-(benzhydrylideneamino)-6-[6-(hydroxymethyl)-4-methyl-3-pyridyl]-2,7-naphthyridin-3-yl]cyclopropanecarboxamide (30 mg, 23.3% yield) as a yellow solid. LCMS (ESI) [M+H]$^+$=514.2.

Step 2: N-(8-amino-6-(6-(hydroxymethyl)-4-methylpyridin-3-yl)-2,7-naphthyridin-3-yl)cyclopropanecarboxamide

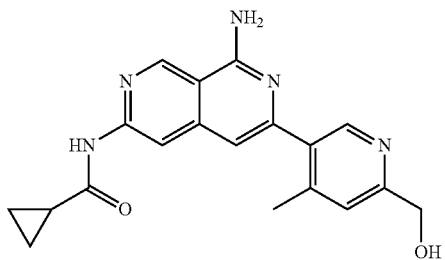 [SMILES: Cc1cc(CO)ncc1-c1cc2cc(NC(=O)C3CC3)ncc2c(N)n1]

A solution of N-[8-(benzhydrylideneamino)-6-[6-(hydroxymethyl)-4-methyl-3-pyridyl]-2,7-naphthyridin-3-yl] cyclopropanecarboxamide (30 mg, 0.06 mmol) in HCl/dioxane (4 mL, 4 M, 16 mmol) was stirred at room temperature for 2 h. The reaction mixture was concentrated. The pH of the residue was adjusted to >7 by adding 7N NH$_3$ in methanol, then concentrated. The residue was purified by reverse phase prep-HPLC to give the product N-[8-amino-6-[6-(hydroxymethyl)-4-methyl-3-pyridyl]-2,7-naphthyridin-3-yl]cyclopropanecarboxamide (6 mg, 27.6% yield) as a white solid. LCMS (ESI): R$_T$ (min)=1.627, [M+H]$^+$=350.1, method=G; $^1$H NMR (400 MHz, CD$_3$OD) δ 9.30 (s, 1H), 8.49 (s, 1H), 8.30 (s, 1H), 7.52 (s, 1H), 6.99 (s, 1H), 4.74 (s, 2H), 2.48 (s, 3H), 1.92-2.03 (m, 1H), 1.01-1.04 (m, 2H), 0.88-0.90 (m, 2H).

Example 26

N-(8-amino-6-(4-ethylpyridin-3-yl)-2,7-naphthyridin-3-yl)cyclopropanecarboxamide (Compound 26)

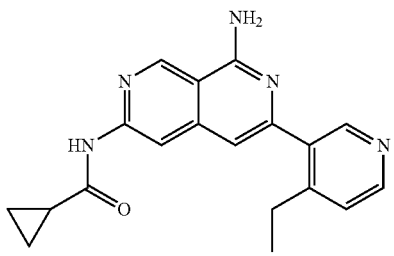

Step 1: N-(8-(diphenylmethyleneamino)-6-(4-ethylpyridin-3-yl)-2,7-naphthyridin-3-yl)cyclopropanecarboxamide

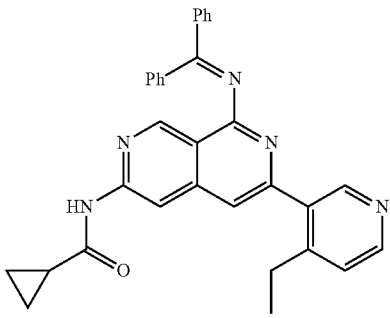 [SMILES: CCc1ccncc1-c1cc2cc(NC(=O)C3CC3)ncc2c(N=C(c2ccccc2)c2ccccc2)n1]

A mixture of N-[8-(benzhydrylideneamino)-6-chloro-2,7-naphthyridin-3-yl]cyclopropanecarboxamide (200 mg, 0.47 mmol), 4-ethyl-3-(4,4,5,5-tetramethyl-1,3,2-dioxaborolan-2-yl)pyridine (655 mg, 2.81 mmol), Pd(PPh$_3$)$_4$ (54 mg, 0.05 mmol) and Cs$_2$CO$_3$ (305 mg, 0.94 mmol) in 1,4-dioxane (1 mL) was heated at 100° C. in a glovebox for 18 hours. The reaction mixture was diluted with ethyl acetate, washed with water, dried over Na$_2$SO$_4$, filtered and concentrated to give the crude product, which was used in the next step without purification. LCMS (ESI) [M+H]$^+$=498.3.

Step 2: N-(8-amino-6-(4-ethylpyridin-3-yl)-2,7-naphthyridin-3-yl)cyclopropanecarboxamide

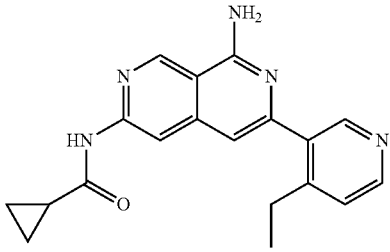 [SMILES: CCc1ccncc1-c1cc2cc(NC(=O)C3CC3)ncc2c(N)n1]

A solution of N-[8-(benzhydrylideneamino)-6-(4-ethyl-3-pyridyl)-2,7-naphthyridin-3-yl]cyclopropanecarboxamide (150 mg, 0.17 mmol) in HCl/dioxane (3.3 mL, 4 M, 13.2 mmol) was stirred at 25° C. for 2 hours, then concentrated. The pH of the residue was adjusted to >7 with 7 N NH$_3$ in methanol, then concentrated. The residue was purified by reverse phase prep-HPLC to give N-[8-amino-6-(4-ethyl-3-pyridyl)-2,7-naphthyridin-3-yl]cyclopropanecarboxamide (10 mg, 18.1% yield) as a white solid. LCMS (ESI): R$_T$ (min)=1.623, [M+H]$^+$=334.2, method=G; $^1$H NMR (400 MHz, CD$_3$OD) δ 9.18 (s, 1H), 8.39 (s, 1H), 8.37 (d, 1H, J=5.6 Hz), 8.17 (s, 1H), 7.33 (d, 1H, J=5.6 Hz), 6.81 (s, 1H), 2.72 (q, 2H, J=7.6 Hz), 1.78-1.88 (m, 1H), 1.07 (t, 3H, J=7.6 Hz), 0.87-0.95 (m, 2H), 0.74-0.82 (m, 2H).

Example 27

N-[8-amino-6-(1-methylpyrazol-4-yl)-2,7-naphthyridin-3-yl]cyclopropanecarboxamide (Compound 27)

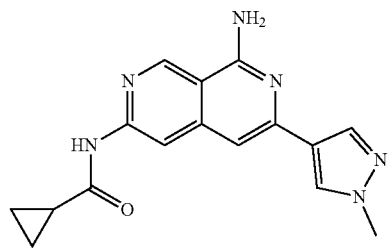 [SMILES: Cn1cc(-c2cc3cc(NC(=O)C4CC4)ncc3c(N)n2)cn1]

Step 1: N-(8-(diphenylmethyleneamino)-6-(1-methyl-1H-pyrazol-4-yl)-2,7-naphthyridin-3-yl)cyclopropanecarboxamide

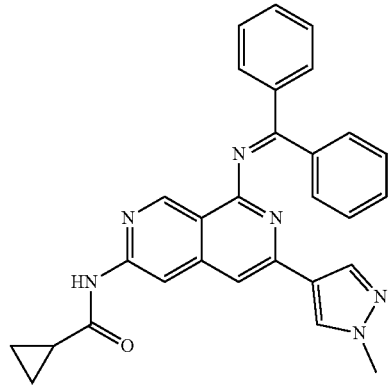 [SMILES: Cn1cc(-c2cc3cc(NC(=O)C4CC4)ncc3c(N=C(c3ccccc3)c3ccccc3)n2)cn1]

A mixture of N-[8-(benzhydrylideneamino)-6-chloro-2,7-naphthyridin-3-yl]cyclopropanecarboxamide (50 mg, 0.12 mmol), 1-methyl-4-(4,4,5,5-tetramethyl-1,3,2-dioxaborolan-2-yl)-1H-pyrazole (36 mg, 0.18 mmol), Pd(PPh$_3$)$_4$ (14 mg, 0.01 mmol) and Cs$_2$CO$_3$ (76 mg, 0.23 mmol) in 1,4-dioxane (5 mL) was heated to 100° C. for 4 hours in a glove-box. Ethyl acetate (50 mL) was added, the mixture was filtered and concentrated to give N-(8-(diphenylmethyleneamino)-6-(1-methyl-H-pyrazol-4-yl)-2,7-naphthyridin-3-yl)cyclopropanecarboxamide (68 mg, 59% yield) as yellow oil, which was used in the next step without further purification. LCMS (ESI) [M+H]$^+$=473.2.

459

Step 2: N-[8-amino-6-(1-methylpyrazol-4-yl)-2,7-naphthyridin-3-yl]cyclopropanecarboxamide

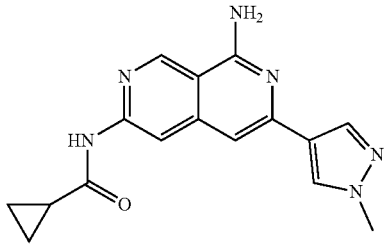 [SMILES: Cn1cc(-c2cc3cc(NC(=O)C4CC4)ncc3c(N)n2)cn1]

To a solution of N-[8-(benzhydrylideneamino)-6-(1-methylpyrazol-4-yl)-2,7-naphthyridin-3-yl]cyclopropanecarboxamide (68 mg, 0.10 mmol) in THF (5 mL) was added HCl in 1,4-dioxane (1 mL, 4 M, 4 mmol). The mixture was stirred for 1 hour. The reaction mixture was concentrated and purified by reverse phase prep-HPLC to afford N-[8-amino-6-(1-methylpyrazol-4-yl)-2,7-naphthyridin-3-yl]cyclopropanecarboxamide (18 mg, 59% yield) as white solid. LCMS (ESI): $R_T$ (min)=1.646, [M+H]$^+$=309.1, method=G; $^1$H NMR (400 MHz, CD$_3$OD-d$_4$) δ 9.15 (s, 1H), 8.19 (s, 1H), 8.14 (s, 1H), 8.02 (s, 1H), 7.11 (s, 1H), 3.96 (s, 3H), 1.98-1.92 (m, 1H), 1.05-1.02 (m, 2H), 0.96-0.91 (m, 2H).

Example 28

N-[8-amino-6-(4-ethyl-3-pyridyl)-2,7-naphthyridin-3-yl]-3-cyano-propanamide (Compound 28)

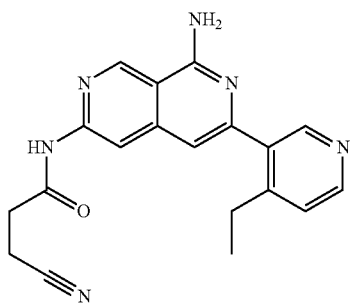

460

Step 1: N-[8-[bis[(4-methoxyphenyl)methyl]amino]-6-(4-ethyl-3-pyridyl)-2,7-naphthyridin-3-yl]-3-cyano-propanamide

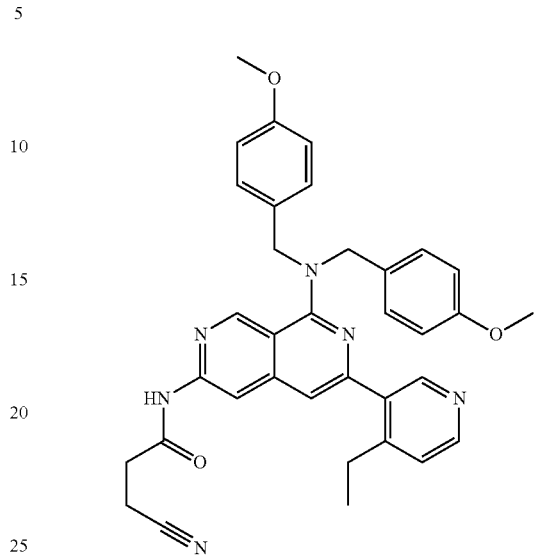

To a solution of 3-cyanopropanoic acid (64 mg, 0.64 mmol) and DMF (1 drop) in dichloromethane (6 mL) was added oxalyl chloride (125 mg, 0.98 mmol) at 0° C. and then stirred at room temperature for 1 hours. The mixture was concentrated and dissolved in dichloromethane (3 mL). The mixture was then added to a solution of 3-(4-ethyl-3-pyridyl)-N1,N1-bis[(4-methoxyphenyl)methyl]-2,7-naphthyridine-1,6-diamine (216 mg, 0.43 mmol) and Et$_3$N (216 mg, 2.14 mmol) in dichloromethane (5 mL) at 0° C., and stirred at room temperature for 1 hour. The mixture was concentrated and purified by column chromatography eluting with ethyl acetate/hexane (1:1) to afford N-[8-[bis[(4-methoxyphenyl)methyl]amino]-6-(4-ethyl-3-pyridyl)-2,7-naphthyridin-3-yl]-3-cyano-propanamide (160 mg, 29% yield) as a yellow solid. LCMS (ESI) [M+H]$^+$=587.3.

Step 2: N-[8-amino-6-(4-ethyl-3-pyridyl)-2,7-naphthyridin-3-yl]-3-cyano-propanamide and N'-[8-amino-6-(4-ethyl-3-pyridyl)-2,7-naphthyridin-3-yl]butanediamide

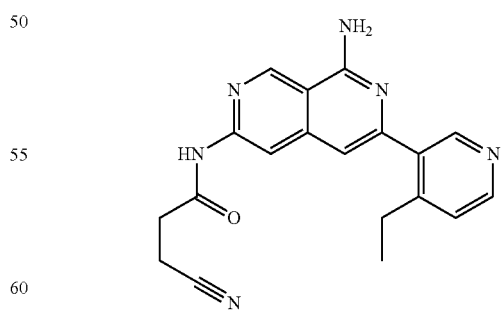

A mixture of N-[8-[bis[(4-methoxyphenyl)methyl]amino]-6-(4-ethyl-3-pyridyl)-2,7-naphthyridin-3-yl]-3-cyano-propanamide (160 mg, 0.13 mmol) in TFA (10 mL) was stirred at 80° C. for 1 hour. The reaction mixture was concentrated and neutralized with NH$_4$OH (37% yield) to pH=7-8. The mixture was concentrated and purified by preparative reverse phase HPLC (C-18), eluting with acetonitrile/water+0.05% NH$_4$HCO$_3$, to give N-[8-amino-6-(4-ethyl-3-pyridyl)-2,7-naphthyridin-3-yl]-3-cyano-propanamide (24 mg, 55% yield). LCMS (ESI) R$_T$ (min)=1.57, [M+H]$^+$=347.2, method=F. $^1$H NMR (400 MHz, DMSO-d$_6$) δ 10.85 (s, 1H), 9.39 (s, 1H), 8.51 (s, 1H), 8.49 (d, J=5.2 Hz, 1H), 8.26 (s, 1H), 7.36 (s, 1H), 7.34 (s, 2H), 6.98 (s, 1H), 2.86-2.74 (m, 6H), 1.10 (t, J=7.6 Hz, 3H).

Example 29

N'-[8-amino-6-(4-ethyl-3-pyridyl)-2,7-naphthyridin-3-yl]butanediamide (Compound 29)

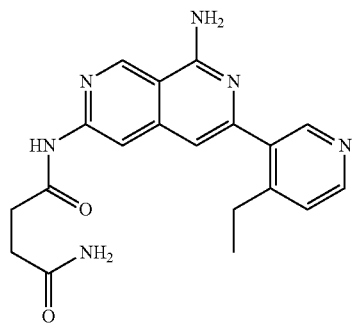 [SMILES: CCc1ccncc1-c1cc2cc(NC(=O)CCC(N)=O)ncc2c(N)n1]

A mixture of N-[8-[bis[(4-methoxyphenyl)methyl]amino]-6-(4-ethyl-3-pyridyl)-2,7-naphthyridin-3-yl]-3-cyano-propanamide (160 mg, 0.13 mmol) in TFA (10 mL) was stirred at 80° C. for 1 hour. The reaction mixture was concentrated and neutralized with NH$_4$OH (37% yield) to pH 7-8. The mixture was concentrated and purified by preparative reverse phase HPLC (C-18), eluting with acetonitrile/water+0.05% NH$_4$HCO$_3$, to afford N'-[8-amino-6-(4-ethyl-3-pyridyl)-2,7-naphthyridin-3-yl]butanediamide (11 mg, 22% yield) as a white solid. LCMS (ESI) R$_T$ (min)=1.372, [M+H]$^+$=365.2, method=G. $^1$H NMR (400 MHz, DMSO-d$_6$) δ 10.65 (s, 1H), 9.36 (s, 1H), 8.50 (s, 1H), 8.48 (d, J=4.8 Hz, 1H), 8.23 (s, 1H), 7.35 (s, 1H), 7.34 (d, J=5.2 Hz, 1H), 7.31 (s, 2H), 6.93 (s, 1H), 6.79 (s, 1H), 2.78 (q, J=7.6 Hz, 2H), 2.65 (t, J=7.0 Hz, 2H), 2.41 (t, J=7.0 Hz, 2H), 1.10 (t, J=7.6 Hz, 3H).

Example 30

1-[8-amino-6-(4-ethyl-3-pyridyl)-2,7-naphthyridin-3-yl]-3-(thiazol-5-ylmethyl)urea (Compound 30)

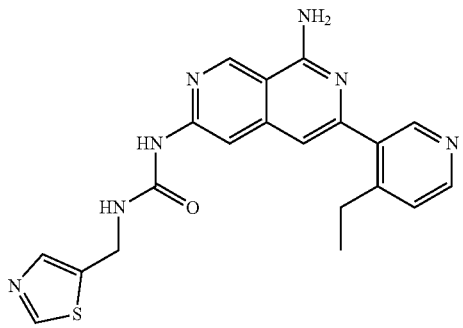 [SMILES: CCc1ccncc1-c1cc2cc(NC(=O)NCc3cncs3)ncc2c(N)n1]

Step 1: 1-[8-[bis[(4-methoxyphenyl)methyl]amino]-6-(4-ethyl-3-pyridyl)-2,7-naphthyridin-3-yl]-3-(thiazol-5-ylmethyl)urea

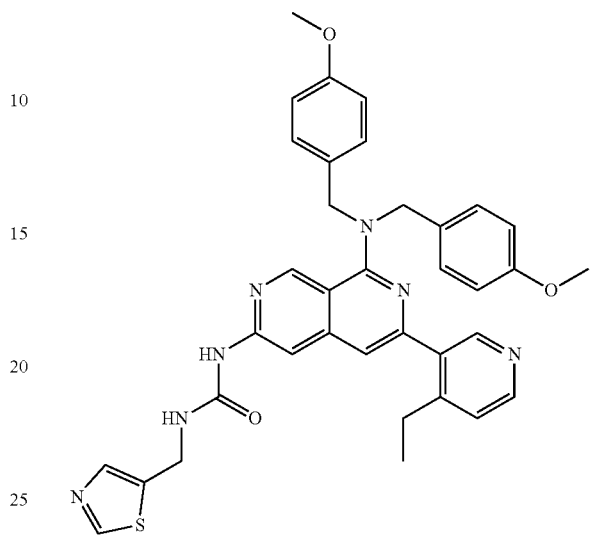

To a solution of triphosgene (183 mg, 0.62 mmol) in THF (8 mL) was added 3-(4-ethyl-3-pyridyl)-N1,N1-bis[(4-methoxyphenyl)methyl]-2,7-naphthyridine-1,6-diamine (260 mg, 0.31 mmol) and Et$_3$N (1.24 g, 12.34 mmol) in THF (3 ml). The mixture was stirred at 0° C. for 1 hour. Thiazol-5-ylmethanamine hydrochloride (930 mg, 6.17 mmol) was added and warmed to room temperature overnight. The mixture was concentrated and purified by silica gel chromatography eluting with dichloromethane/methanol (20:1) to afford 1-[8-[bis[(4-methoxyphenyl)methyl]amino]-6-(4-ethyl-3-pyridyl)-2,7-naphthyridin-3-yl]-3-(thiazol-5-ylmethyl)urea (35 mg, 15% yield) as a yellow solid. LCMS (ESI) [M+H]$^+$=646.3.

Step 2: 1-[8-amino-6-(4-ethyl-3-pyridyl)-2,7-naphthyridin-3-yl]-3-(thiazol-5-ylmethyl)urea

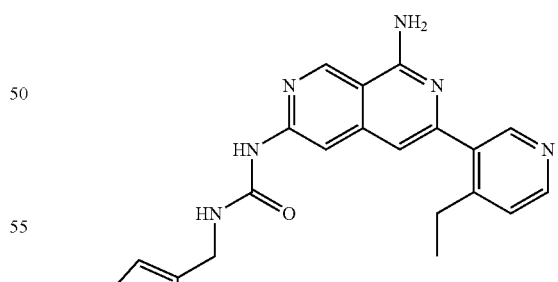

A mixture of 1-[8-[bis[(4-methoxyphenyl)methyl]amino]-6-(4-ethyl-3-pyridyl)-2,7-naphthyridin-3-yl]-3-(thiazol-5-ylmethyl)urea (35 mg, 0.05 mmol) in TFA (5 mL) was stirred at 80° C. for 3 hours. The mixture was concentrated and neutralized with NH$_4$OH (purity: 37% yield) to pH 7-8. The mixture was purified by preparative reverse phase HPLC (C-18), eluting with acetonitrile/water+0.05%

NH$_4$HCO$_3$, to give 1-[8-amino-6-(4-ethyl-3-pyridyl)-2,7-naphthyridin-3-yl]-3-(thiazol-5-ylmethyl)urea (13 mg, 59% yield) as a yellow solid. LCMS (ESI) R$_T$ (min)=1.56, [M+H]$^+$=406.1, method=C. $^1$H NMR (400 MHz, DMSO-d$_6$) δ 9.41 (s, 1H), 9.28 (s, 1H), 8.99 (d, J=0.8 Hz, 1H), 8.49 (s, 1H), 8.48 (d, J=5.2 Hz, 1H), 7.83 (s, 1H), 7.82 (s, 1H), 7.80 (s, 1H), 7.34 (d, J=5.2 Hz, 1H), 7.27 (s, 2H), 6.87 (s, 1H), 4.61 (d, J=6.0 Hz, 2H), 2.79 (q, J=7.6 Hz, 2H), 2.65 (t, J=7.6 Hz, 3H).

Example 31

1-[8-amino-6-(4-ethyl-3-pyridyl)-2,7-naphthyridin-3-yl]-3-isopropyl-urea (Compound 31)

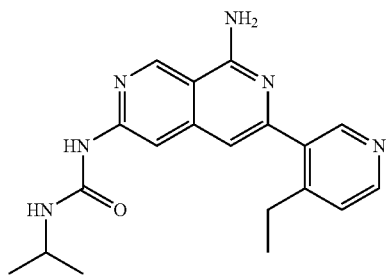 [SMILES: CCc1ccncc1-c1cc2cc(NC(=O)NC(C)C)ncc2c(N)n1]

Step 1: 1-[8-[bis[(4-methoxyphenyl)methyl]amino]-6-(4-ethyl-3-pyridyl)-2,7-naphthyridin-3-yl]-3-isopropyl-urea

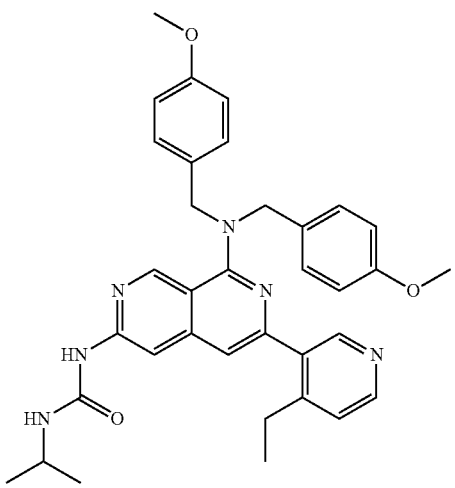 [SMILES: CCc1ccncc1-c1cc2cc(NC(=O)NC(C)C)ncc2c(N(Cc2ccc(OC)cc2)Cc2ccc(OC)cc2)n1]

A mixture of 3-(4-ethyl-3-pyridyl)-N1,N1-bis[(4-methoxyphenyl)methyl]-2,7-naphthyridine-1,6-diamine (150 mg, 0.15 mmol), isopropyl isocyanate (114 mg, 1.34 mmol) and DBU (113 mg, 0.74 mmol) in 1,4-dioxane (8 mL) was stirred at 110° C. for 16 hours. The mixture was concentrated and purified by reverse phase preparative HPLC (C-18), eluting with acetonitrile/water+0.05% NH$_4$HCO$_3$, to give 1-[8-[bis[(4-methoxyphenyl)methyl]amino]-6-(4-ethyl-3-pyridyl)-2,7-naphthyridin-3-yl]-3-isopropyl-urea (50 mg, 43% yield) as a yellow solid. LCMS (ESI) [M+H]$^+$=591.3.

Step 2: 1-[8-amino-6-(4-ethyl-3-pyridyl)-2,7-naphthyridin-3-yl]-3-isopropyl-urea

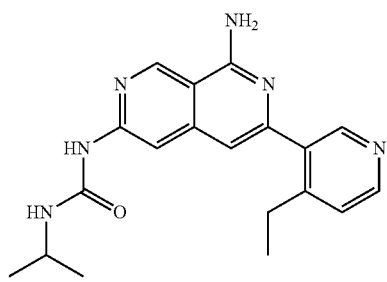 [SMILES: CCc1ccncc1-c1cc2cc(NC(=O)NC(C)C)ncc2c(N)n1]

A mixture of 1-[8-[bis[(4-methoxyphenyl)methyl]amino]-6-(4-ethyl-3-pyridyl)-2,7-naphthyridin-3-yl]-3-isopropyl-urea (50 mg, 0.08 mmol) in TFA (8 mL) was stirred at 80° C. for 3 hours. The reaction mixture was concentrated and neutralized with NH$_4$OH (37% yield) to pH 7-8. The mixture was concentrated and purified by preparative reverse phase HPLC (C-18), eluting with acetonitrile/water+0.05% NH$_4$HCO$_3$, to give 1-[8-amino-6-(4-ethyl-3-pyridyl)-2,7-naphthyridin-3-yl]-3-isopropyl-urea (17 mg, 57% yield) as a yellow solid. LCMS (ESI) R$_T$ (min)=1.581, [M+H]$^+$=351.2, method=G. $^1$H NMR (400 MHz, DMSO-d$_6$) δ 9.33 (s, 1H), 9.11 (s, 1H), 8.55 (s, 1H), 8.54 (d, J=5.2 Hz, 1H), 7.86 (s, 1H), 8.39 (d, J=5.2 Hz, 1H), 7.30 (s, 2H), 7.16 (d, J=6.8 Hz, 1H), 6.89 (s, 1H), 3.91-3.83 (m, 1H), 2.84 (q, J=7.6 Hz, 2H), 1.20 (d, J=6.4 Hz, 6H), 1.15 (t, J=7.6 Hz, 3H).

Example 32

N-[8-amino-6-(4-ethyl-3-pyridyl)-2,7-naphthyridin-3-yl]-2-cyano-acetamide (Compound 32)

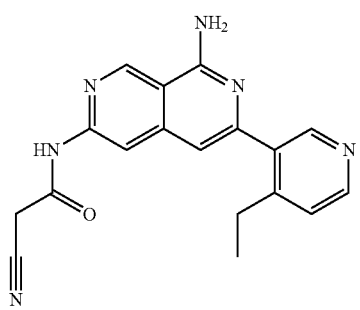 [SMILES: CCc1ccncc1-c1cc2cc(NC(=O)CC#N)ncc2c(N)n1]

465

Step 1: 2-cyano-N-(6,8-dichloro-2,7-naphthyridin-3-yl)acetamide

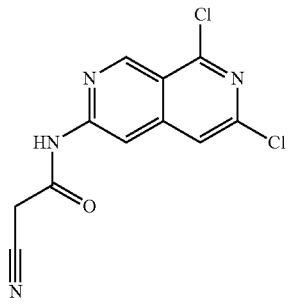 [SMILES: N#CCC(=O)Nc1cc2cc(Cl)nc(Cl)c2cn1]

To a solution of cyanoacetic acid (340 mg, 3.99 mmol) and DMF (1 drop) in dichloromethane (20 mL) at 0° C. was added oxalyl chloride (0.34 mL, 3.99 mmol) and stirred at room temperature for 2 h. The mixture was added to a solution of 6,8-dichloro-2,7-naphthyridin-3-amine hydrochloride (500 mg, 2 mmol) in pyridine (10 mL) and dichloromethane (20 mL) at 0° C. The reaction mixture was stirred at 0° C. for 1 hour. The mixture was concentrated and purified by silica gel chromatography, eluting with TH to afford 2-cyano-N-(6,8-dichloro-2,7-naphthyridin-3-yl)acetamide (600 mg, 60% yield) as a yellow solid. LCMS (ESI) [M+H]$^+$=281.0.

Step 2: N-(8-amino-6-chloro-2,7-naphthyridin-3-yl)-2-cyano-acetamide

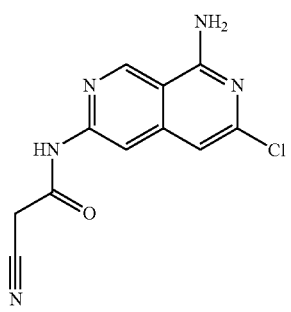 [SMILES: N#CCC(=O)Nc1cc2cc(Cl)nc(N)c2cn1]

A mixture of 2-cyano-N-(6,8-dichloro-2,7-naphthyridin-3-yl)acetamide (600 mg, 1.19 mmol) in 0.5 M NH$_3$ in dioxane (40 mL, 20 mmol) was stirred at 110° C. for 24 hours. The mixture was concentrated and purified by preparative reverse phase HPLC (C18), eluting with acetonitrile/water+0.05% NH$_4$HCO$_3$, to give N-(8-amino-6-chloro-2,7-naphthyridin-3-yl)-2-cyano-acetamide (130 mg, 32% yield) as a yellow solid. LCMS (ESI) [M+H]$^+$=262.3.

466

Step 3: N-[8-amino-6-(4-ethyl-3-pyridyl)-2,7-naphthyridin-3-yl]-2-cyano-acetamide


A mixture of N-(8-amino-6-chloro-2,7-naphthyridin-3-yl)-2-cyano-acetamide (100 mg, 0.38 mmol), 4-ethyl-3-(4,4,5,5-tetramethyl-1,3,2-dioxaborolan-2-yl)pyridine (216 mg, 0.76 mmol), XPhos Pd G2 (45 mg, 0.06 mmol), potassium acetate (75 mg, 0.76 mmol) and XPhos (55 mg, 0.11 mmol) in 1,4-dioxane (10 mL) and water (0.4 mL) under Ar was stirred at 100° C. for 8 hours. The mixture was concentrated and purified by preparative reverse phase HPLC (C-18), eluting with acetonitrile/water+0.05% NH$_4$HCO$_3$, to give N-[8-amino-6-(4-ethyl-3-pyridyl)-2,7-naphthyridin-3-yl]-2-cyano-acetamide (5 mg, 4% yield) as a yellow solid. LCMS (ESI) R$_T$(min)=1.568, [M+H]$^+$=333.1, method=C. $^1$H NMR (400 MHz, DMSO-d$_6$) δ 11.02 (s, 1H), 9.39 (s, 1H), 8.51 (s, 1H), 8.49 (d, J=5.2 Hz, 1H), 8.19 (s, 1H), 7.36 (s, 2H), 7.35 (s, 1H), 7.01 (s, 1H), 4.04 (s, 2H), 2.79 (q, J=7.6 Hz, 2H), 1.10 (t, J=7.6 Hz, 3H).

Example 33

3-[8-amino-6-(4-ethyl-3-pyridyl)-2,7-naphthyridin-3-yl]-1,1-dimethyl-urea (Compound 33)

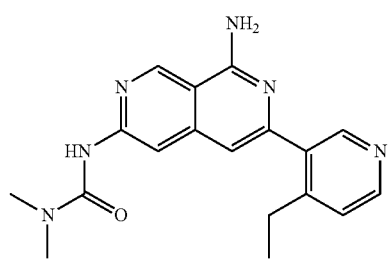 [SMILES: CCc1ccncc1-c1cc2cc(NC(=O)N(C)C)ncc2c(N)n1]

Step 1: 3-[8-[bis[(4-methoxyphenyl)methyl]amino]-6-(4-ethyl-3-pyridyl)-2,7-naphthyridin-3-yl]-1,1-dimethyl-urea

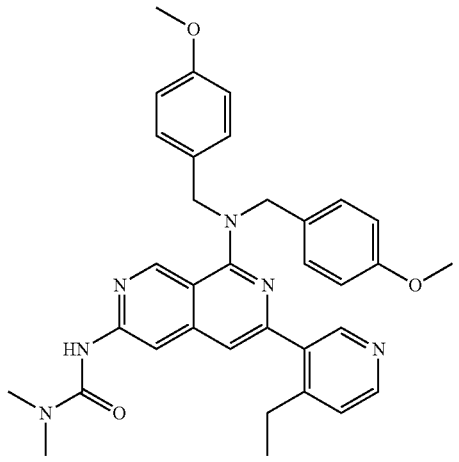

To a solution of triphosgene (293 mg, 0.99 mmol) in THF (6 mL) was added 3-(4-ethyl-3-pyridyl)-N1,N1-bis[(4-methoxyphenyl)methyl]-2,7-naphthyridine-1,6-diamine (500 mg, 0.49 mmol) and Et$_3$N (10.0 g, 9.89 mmol) in THF (10 ml). The mixture was stirred at 0° C. for 1 hour. N,N-dimethylamine (446 mg, 9.89 mmol) was added. The reaction was then stirred at room temperature for 2 hours. The mixture was concentrated and purified by silica gel chromatography (ethyl acetate/hexane, 9:1) to afford 3-[8-[bis[(4-methoxyphenyl)methyl]amino]-6-(4-ethyl-3-pyridyl)-2,7-naphthyridin-3-yl]-1,1-dimethyl-urea (42 mg, 13% yield) as a yellow solid. LCMS (ESI) [M+H]$^+$=577.3.

Step 2: 3-[8-amino-6-(4-ethyl-3-pyridyl)-2,7-naphthyridin-3-yl]-1,1-dimethyl-urea

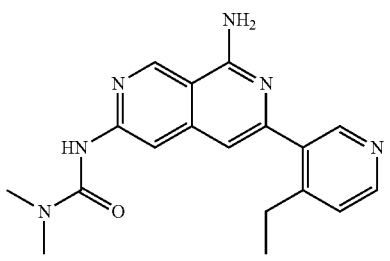 [SMILES: CCc1ccncc1-c1cc2cc(NC(=O)N(C)C)ncc2c(N)n1]

A mixture of 3-[8-[bis[(4-methoxyphenyl)methyl]amino]-6-(4-ethyl-3-pyridyl)-2,7-naphthyridin-3-yl]-1,1-dimethyl-urea (42 mg, 0.07 mmol) in TFA (8 mL) was stirred at 80° C. for 3 hours. The mixture was concentrated and neutralized with NH$_4$OH (37% yield) to pH 7-8. The mixture was concentrated and purified by preparative reverse phase HPLC (C-18), eluting with acetonitrile/water+0.05% NH$_4$HCO$_3$, to give 3-[8-amino-6-(4-ethyl-3-pyridyl)-2,7-naphthyridin-3-yl]-1,1-dimethyl-urea (15 mg, 57% yield) as a yellow solid. LCMS (ESI) R$_T$(min)=1.567, [M+H]$^+$=337.1, method=C. $^1$H NMR (400 MHz, DMSO-d$_6$) δ 9.33 (s, 1H), 8.98 (s, 1H), 8.49 (s, 1H), 8.48 (d, J=4.8 Hz, 1H), 7.96 (s, 1H), 7.34 (d, J=4.8 Hz, 1H), 7.25 (s, 2H), 6.87 (s, 1H), 2.98 (s, 6H), 2.78 (q, J=7.6 Hz, 2H), 1.10 (t, J=7.6 Hz, 3H).

Example 34

2-[[8-amino-6-(4-ethyl-3-pyridyl)-2,7-naphthyridin-3-yl]carbamoylamino]propanamide (Compound 34)

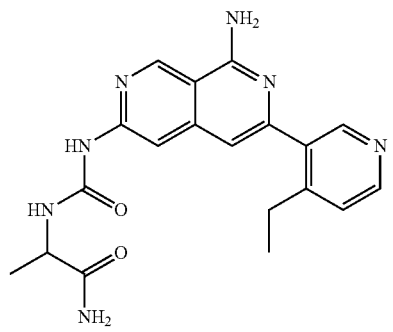 [SMILES: CCc1ccncc1-c1cc2cc(NC(=O)NC(C)C(N)=O)ncc2c(N)n1]

Step 1: 2-[[8-[bis[(2,4-dimethoxyphenyl)methyl]amino]-6-(4-ethyl-3-pyridyl)-2,7-naphthyridin-3-yl]carbamoylamino]propanamide

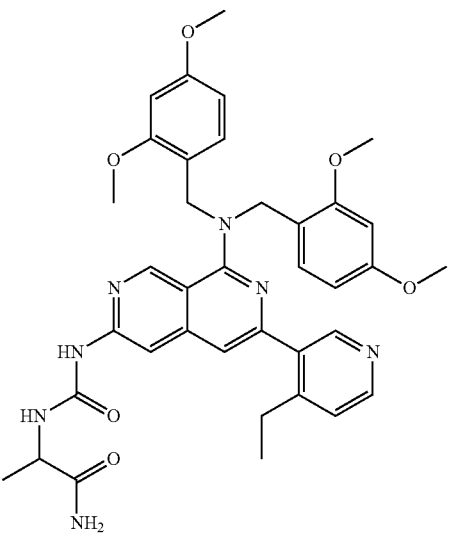 [SMILES: CCc1ccncc1-c1cc2cc(NC(=O)NC(C)C(N)=O)ncc2c(N(Cc2ccc(OC)cc2OC)Cc2ccc(OC)cc2OC)n1]

To a solution of triphosgene (210 mg, 0.71 mmol) in THF (6 mL) was added N1,N1-bis[(2,4-dimethoxyphenyl)methyl]-3-(4-ethyl-3-pyridyl)-2,7-naphthyridine-1,6-diamine (200 mg, 0.35 mmol) and Et$_3$N (714 mg, 7.07 mmol) in THF (10 ml). The mixture was stirred at 0° C. for 1 hour. 2-aminopropanamide hydrochloride (881 mg, 7.07 mmol) was added and stirred at room temperature for 2 hours. The mixture was concentrated and purified by silica gel chromatography eluting with ethyl acetate to afford 2-[[8-[bis[(2,4-dimethoxyphenyl)methyl]amino]-6-(4-ethyl-3-pyridyl)-2,7-naphthyridin-3-yl]carbamoylamino]propanamide (57 mg, 18% yield) as a yellow solid. LCMS (ESI) [M+H]$^+$=680.3.

Step 2: 2-[[8-amino-6-(4-ethyl-3-pyridyl)-2,7-naphthyridin-3-yl]carbamoylamino]propanamide

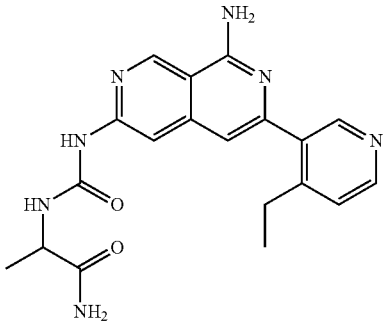 [SMILES: CCc1ccncc1-c1cc2cc(NC(=O)NC(C)C(N)=O)ncc2c(N)n1]

A mixture of 2-[[8-[bis[(2,4-dimethoxyphenyl)methyl]amino]-6-(4-ethyl-3-pyridyl)-2,7-naphthyridin-3-yl]carbamoylamino]propanamide (57 mg, 0.06 mmol) in TFA (5 mL) was stirred at 26° C. for 6 hours. The reaction mixture was concentrated and neutralized with NH$_4$OH (37% yield) to pH 7-8. The mixture was concentrated and purified by preparative reverse phase HPLC (C-18), eluting with acetonitrile/water+0.05% NH$_4$HCO$_3$, to give 2-[[8-amino-6-(4-ethyl-3-pyridyl)-2,7-naphthyridin-3-yl]carbamoylamino]propanamide (10 mg, 46% yield) as a yellow solid. LCMS (ESI) R$_T$ (min)=1.378, [M+H]$^+$=380.2, method=G. $^1$H NMR (400 MHz, DMSO-d$_6$) δ 9.33 (s, 1H), 9.28 (s, 1H), 8.49 (s, 1H), 8.48 (d, J=5.2 Hz, 1H), 7.78 (s, 1H), 7.58 (s, 1H), 7.53 (s, 1H), 7.30 (d, J=1.2 Hz, 1H), 7.25 (s, 2H), 7.06 (s, 1H), 6.84 (s, 1H), 4.29-4.22 (m, 1H), 2.78 (q, J=7.6 Hz, 2H), 1.28 (d, J=6.8 Hz, 3H), 1.10 (t, J=7.6 Hz, 3H).

Example 35

N-(8-amino-6-(4-methylpyridin-3-yl)-2,7-naphthyridin-3-yl)-2-cyano-2-methylpropanamide (Compound 35)

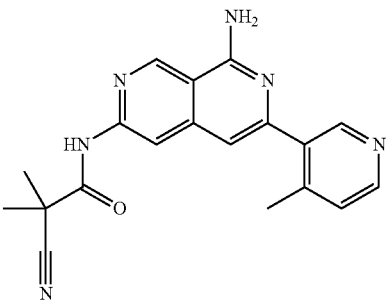 [SMILES: Cc1ccncc1-c1cc2cc(NC(=O)C(C)(C)C#N)ncc2c(N)n1]

Step 1: 2-cyano-2-methylpropanoic acid

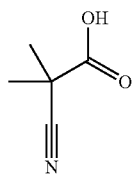

To a vial was added ethyl 2-cyano-2-methylpropanoate (1.0 g, 7.08 mmol), water (5 mL) and KOH (795 mg, 14.1 mmol). The mixture was stirred at 40° C. for 2 hours. The reaction mixture was concentrated to remove methanol, acidified to pH 5 with 1 N HCl and extracted with ethyl acetate (50 ml×2). The combined organic layers were washed with brine (10 mL), dried over Na$_2$SO$_4$, filtered and concentrated in vacuo to give 2-cyano-2-methyl-propanoic acid (600 mg, 73% yield) as a pale-yellow solid. $^1$H NMR (400 MHz, DMSO-d$_6$) δ 13.59 (br, 1H), 1.52 (s, 6H).

Step 2: 2-cyano-2-methylpropanoyl chloride

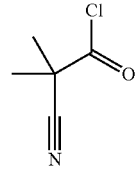

To a vial was added 2-cyano-2-methyl-propanoic acid (600 mg, 5.3 mmol) and dichloromethane (20 mL). Oxalyl chloride (1 mL, 11.72 mmol) was added drop-wise at 0° C. DMF (0.01 mL) was then added. The mixture was stirred at room temperature for 3 hours. The reaction mixture was concentrated in vacuo to get crude product and used for the next step directly.

Step 3: 2-cyano-N-(6,8-dichloro-2,7-naphthyridin-3-yl)-2-methylpropanamide

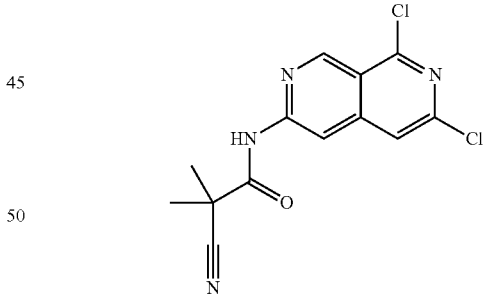

To a vial was added 6,8-dichloro-2,7-naphthyridin-3-amine hydrochloride (200 mg, 0.80 mmol), 2-cyano-2-methyl-propanoyl chloride (720 mg, 4.38 mmol) and pyridine (5 mL). The mixture was stirred at 20° C. for 2 hours. The mixture was poured into water (10 mL) and adjusted to pH=6 with 1N HCl, extracted with ethyl acetate (80 mL×2), dried over Na$_2$SO$_4$, filtered and concentrated. The residue was purified by silica gel chromatography (petroleum ether/ethyl acetate, 10:1 to 3:1) to give 2-cyano-N-(6,8-dichloro-2,7-naphthyridin-3-yl)-2-methyl-propanamide (230 mg, 93% yield) as a pale-yellow solid. LCMS (ESI) [M+H]$^+$=309.1.

Step 4: N-(8-amino-6-chloro-2,7-naphthyridin-3-yl)-2-cyano-2-methylpropanamide

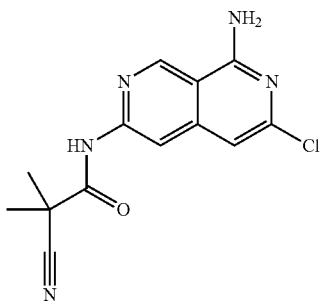 [SMILES: CC(C)(C#N)C(=O)Nc1cc2cc(Cl)nc(N)c2cn1]

To a microwave tube was added 2-cyano-N-(6,8-dichloro-2,7-naphthyridin-3-yl)-2-methyl-propanamide (130 mg, 0.42 mmol) and NH₃ (0.5 N in dioxane, 15 mL, 7.5 mmol). The mixture was stirred at 80° C. for 40 hours. The mixture was then concentrated in vacuo and purified by silica gel chromatography (petroleum ether/ethyl acetate, 1:1 to 0:100) to give N-(8-amino-6-chloro-2,7-naphthyridin-3-yl)-2-cyano-2-methyl-propanamide (86 mg, 70% yield) as a pale-yellow solid. LCMS (ESI) [M+H]⁺=290.1.

Step 5: N-(8-amino-6-(4-methylpyridin-3-yl)-2,7-naphthyridin-3-yl)-2-cyano-2-methylpropanamide

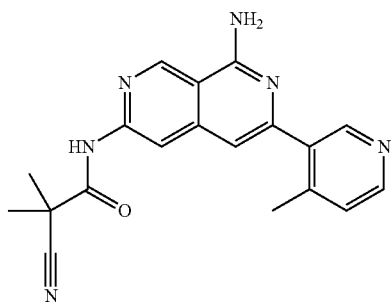 [SMILES: Cc1ccncc1-c1cc2cc(NC(=O)C(C)(C)C#N)ncc2c(N)n1]

To a vial was added N-(8-amino-6-chloro-2,7-naphthyridin-3-yl)-2-cyano-2-methyl-propanamide (86 mg, 0.3 mmol), 4-methyl-3-(4,4,5,5-tetramethyl-1,3,2-dioxaborolan-2-yl)pyridine (84 mg, 0.39 mmol), XPhos Pd G2 (35 mg, 0.04 mmol), X-phos (28 mg, 0.06 mmol), potassium acetate (87 mg, 0.89 mmol), water (0.5 mL) and 1,4-dioxane (20 mL). The reaction mixture was degassed by bubbling with nitrogen and then stirred at 100° C. for 6 hours. The reaction mixture was concentrated and purified by silica gel chromatography (dichloromethane/methanol, 20:1 to 10:1) to give N-[8-amino-6-(4-methyl-3-pyridyl)-2,7-naphthyridin-3-yl]-2-cyano-2-methyl-propanamide (73 mg, 71% yield) as a yellow solid. LCMS (ESI): $R_T$ (min)=1.041, [M+H]⁺=347.1, method=B; ¹H NMR (400 MHz, CD₃OD) δ 9.30 (s, 1H), 8.53, (s, 1H), 8.41 (d, J=5.2 Hz, 1H), 8.09 (s, 1H), 7.37 (d, J=5.2 Hz, 1H), 7.00 (s, 1H), 2.44 (s, 3H), 1.74 (s, 6H).

Example 36

N-(8-amino-6-(4-methylpyridin-3-yl)-2,7-naphthyridin-3-yl)-2-methoxy-2-methylpropanamide (Compound 36)

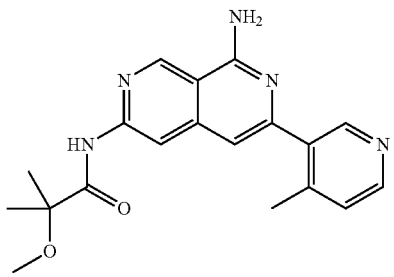 [SMILES: COC(C)(C)C(=O)Nc1cc2cc(-c3cnccc3C)nc(N)c2cn1]

Step 1: 2-methoxy-2-methylpropanoic acid

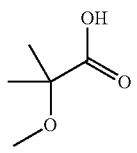

To a vial was added methyl 2-methoxy-2-methyl-propanoate (3.6 g, 27.24 mmol), methanol (5 mL), water (3 mL) and NaOH (1.28 g, 31.97 mmol). The mixture was stirred at 40° C. for 2 hours and concentrated in vacuo to remove the methanol. The mixture was then acidified to pH 4-5 with 2 N HCl, extracted with ethyl acetate (100 ml×2), washed with brine (30 ml), dried over Na₂SO₄, filtered and concentrated in vacuo to give 2-methoxy-2-methyl-propanoic acid (2.5 g, 77% yield) as a pale-yellow oil. ¹H NMR (400 MHz, CDCl₃) δ 3.35 (s, 3H), 1.47 (s, 6H).

Step 2: 2-methoxy-2-methylpropanoyl chloride

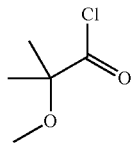

To a vial was added 2-methoxy-2-methyl-propanoic acid (300 mg, 2.54 mmol) and dichloromethane (10 mL). The mixture was then cooled to 0° C. and oxalyl chloride (0.5 mL, 5.61 mmol) was added drop-wise. DMF (0.01 mL, 0.07 mmol) was then added. The mixture was stirred at 40° C. for 1 hour. The reaction mixture was concentrated in vacuo to give a crude product which was used for the next step directly.

Step 3: N-(8-(bis(4-methoxybenzyl)amino)-6-(4-methylpyridin-3-yl)-2,7-naphthyridin-3-yl)-2-methoxy-2-methylpropanamide

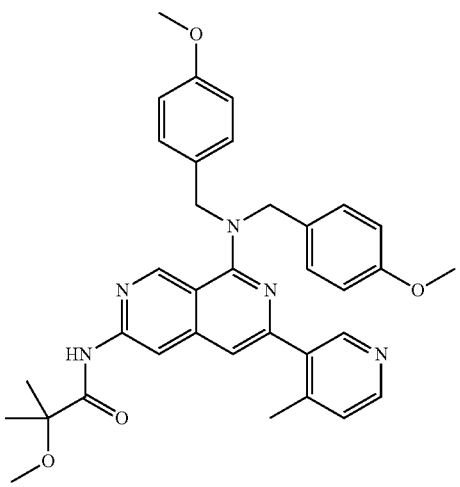 [SMILES: COc1ccc(CN(Cc2ccc(OC)cc2)c2nc(-c3cnccc3C)cc3cc(NC(=O)C(C)(C)OC)ncc23)cc1]

To vial was added N1,N1-bis[(4-methoxyphenyl)methyl]-3-(4-methyl-3-pyridyl)-2,7-naphthyridine-1,6-diamine (70 mg, 0.14 mmol), 2-methoxy-2-methyl-propanoyl chloride (300 mg, 2.2 mmol) and pyridine (5 mL). The mixture was stirred at 20° C. for 2 hours and then concentrated. The residue was purified by silica gel chromatography (petroleum ether/ethyl acetate, 10:1 to 3:1) to give N-[8-[bis[(4-methoxyphenyl)methyl]amino]-6-(4-methyl-3-pyridyl)-2,7-naphthyridin-3-yl]-2-methoxy-2-methyl-propanamide (300 mg, 71% yield) as a yellow solid. LCMS (ESI) [M+H]$^+$=592.1.

Step 4: N-(8-amino-6-(4-methylpyridin-3-yl)-2,7-naphthyridin-3-yl)-2-methoxy-2-methylpropanamide

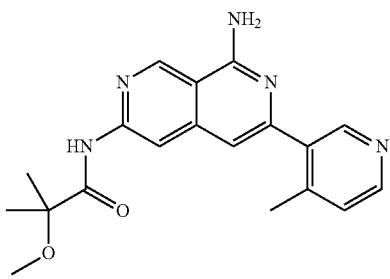 [SMILES: COC(C)(C)C(=O)Nc1cc2cc(-c3cnccc3C)nc(N)c2cn1]

To a vial was added N-[8-[bis[(4-methoxyphenyl)methyl]amino]-6-(4-methyl-3-pyridyl)-2,7-naphthyridin-3-yl]-2-methoxy-2-methyl-propanamide (300 mg, 0.10 mmol) and TFA (5 mL). The mixture was stirred at 80° C. for 2 hours. The mixture was then concentrated, and NH$_3$ (7 N in methanol, 5 mL) was added. The mixture was then concentrated and the residue was purified by silica gel chromatography (dichloromethane/methanol, 10:1) to give N-[8-amino-6-(4-methyl-3-pyridyl)-2,7-naphthyridin-3-yl]-2-methoxy-2-methyl-propanamide (26 mg, 73% yield) as a pale-yellow solid. LCMS (ESI): R$_T$ (min)=1.071, [M+H]$^+$=352.1, method=B; $^1$H NMR (400 MHz, CD$_3$OD) δ 9.30 (s, 1H), 8.54 (s, 1H), 8.43 (d, J=5.6 Hz, 1H), 8.37 (s, 1H), 7.28 (d, J=5.6 Hz, 1H), 6.99 (s, 1H), 3.41 (s, 3H), 2.45 (s, 3H), 1.49 (s, 6H).

Example 37

N-(8-amino-6-(4-methylpyridin-3-yl)-2,7-naphthyridin-3-yl)isobutyramide (Compound 37)

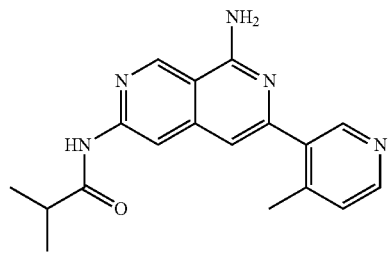 [SMILES: Cc1ccncc1-c1cc2cc(NC(=O)C(C)C)ncc2c(N)n1]

Step 1: N-(6,8-dichloro-2,7-naphthyridin-3-yl)isobutyramide

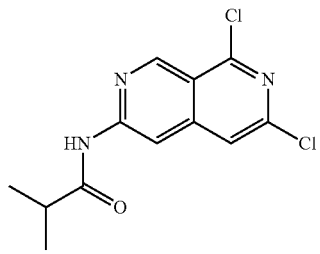 [SMILES: CC(C)C(=O)Nc1cc2cc(Cl)nc(Cl)c2cn1]

To a vial was added 6,8-dichloro-2,7-naphthyridin-3-amine hydrochloride (310.0 mg, 1.24 mmol), isobutyryl chloride (0.2 mL, 1.9 mmol), and pyridine (5 mL). The mixture was stirred at 20° C. for 2 hours. The mixture was then poured into water (10 mL) and pH adjusted to 6 with 1N HCl. The mixture was extracted with dichloromethane (50 mL×2), dried over Na$_2$SO$_4$, filtered and concentrated. The residue was purified by silica gel chromatography (petroleum ether/ethyl acetate, 10:1 to 3:1) to get N-(6,8-dichloro-2,7-naphthyridin-3-yl)-2-methyl-propanamide (345 mg, 98% yield) as a pale-yellow solid. LCMS (ESI) [M+H]$^+$=284.1.

Step 2: N-(8-amino-6-chloro-2,7-naphthyridin-3-yl)isobutyramide

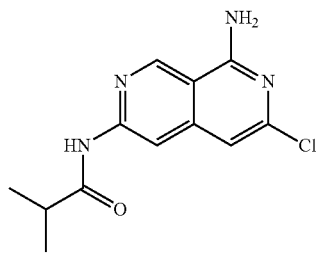 [SMILES: CC(C)C(=O)Nc1cc2cc(Cl)nc(N)c2cn1]

To a microwave tube was added N-(6,8-dichloro-2,7-naphthyridin-3-yl)-2-methyl-propanamide (150 mg, 0.53 mmol) and ammonium hydroxide (5 mL, 130 mmol). The mixture was stirred at 100° C. for 6 hours. The mixture was concentrated in vacuo to give N-(8-amino-6-chloro-2,7-naphthyridin-3-yl)-2-methyl-propanamide (180 mg, 96% yield) as a pale-yellow solid. LCMS (ESI) [M+H]$^+$=265.1.

Step 3: N-(8-amino-6-(4-methylpyridin-3-yl)-2,7-naphthyridin-3-yl)isobutyramide

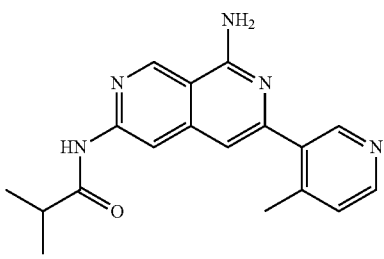 [SMILES: Cc1ccncc1-c1cc2cc(NC(=O)C(C)C)ncc2c(N)n1]

To a vial was added N-(8-amino-6-chloro-2,7-naphthyridin-3-yl)-2-methyl-propanamide (139 mg, 0.53 mmol), XPhos Pd G$_2$ (50 mg, 0.06 mmol), X-phos (45 mg, 0.1 mmol), potassium acetate (124 mg, 1.27 mmol), 4-methyl-3-(4,4,5,5-tetramethyl-1,3,2-dioxaborolan-2-yl)pyridine (172 mg, 0.79 mmol), 1,4-dioxane (5 mL), and water (0.3 mL). The reaction was stirred under N$_2$ at 110° C. for 16 hours. The mixture was concentrated and purified by silica gel chromatography (dichloromethane/methanol, 100:1 to 100:7) to give N-[8-amino-6-(4-methyl-3-pyridyl)-2,7-naphthyridin-3-yl]-2-methyl-propanamide (82 mg, 49% yield) as a pale-yellow solid. LCMS (ESI): R$_T$ (min)=1.221, [M+H]$^+$=322.1, method=B; $^1$H NMR (400 MHz, CDCl$_3$) δ 9.00 (s, 1H), 8.65 (s, 1H); 8.50 (d, J=5.2 Hz, 1H), 8.47 (s, 1H), 8.05 (br, 1H), 7.21 (d, J=5.2 Hz, 1H), 7.06 (s, 1H), 5.42 (br, 2H), 2.62 (heptet, J=6.8 Hz, 1H), 2.43 (s, 3H), 1.31 (d, J=6.8 Hz, 6H).

Example 38

N-(8-amino-6-(4-methylpyridin-3-yl)-2,7-naphthyridin-3-yl)-2-cyanopropanamide (Compound 38)

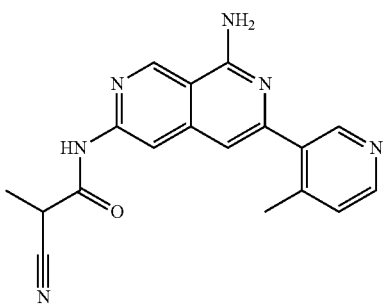 [SMILES: Cc1ccncc1-c1cc2cc(NC(=O)C(C)C#N)ncc2c(N)n1]

Step 1: 2-cyanopropanoic acid

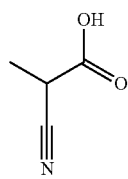

To a vial was added 2-cyanopropionic acid ethylester (1.0 g, 7.87 mmol), methanol (4 mL) and water (4 mL). The mixture was then cooled to 0° C. and KOH (882 mg, 16 mmol) was added. The mixture was stirred at 40° C. for 2 hours. The reaction mixture was concentrated to remove methanol, acidified to pH 5 with 1N HCl, and extracted with ethyl acetate (50 ml×2). The combined organic layers were washed with brine, dried over Na$_2$SO$_4$, filtered and concentrated in vacuo to give 2-cyanopropanoic acid (660 mg, 85% yield) as a violet oil. $^1$H NMR (400 MHz, DMSO-d$_6$) δ 13.59 (br, 1H), 4.03 (q, J=7.2 Hz, 1H), 1.41 (d, J=7.2 Hz, 3H).

Step 2: 2-cyanopropanoyl chloride

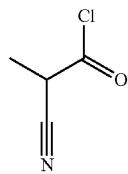

To a vial was added 2-cyanopropanoic acid (660 mg, 6.66 mmol) and dichloromethane (20 mL). The solution was cooled to 0° C. Oxalyl chloride (1.3 mL, 14.72 mmol) was added drop-wise and then DMF (0.01 mL) was added. The mixture was stirred at room temperature for 3 hours. The reaction mixture was concentrated in vacuo to get a crude product and used for the next step directly.

Step 3: 2-cyano-N-(6,8-dichloro-2,7-naphthyridin-3-yl)propanamide

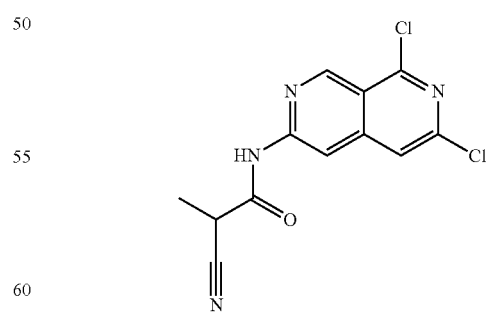

To a vial was added 6,8-dichloro-2,7-naphthyridin-3-amine hydrochloride (400 mg, 1.6 mmol), 2-cyanopropanoyl chloride (1.6 g, 10.89 mmol) and pyridine (5 mL). The mixture was stirred at 20° C. for 2 hours. The mixture was poured into water (10 mL), and pH adjusted to 6 with 1N HCl, extracted with ethyl acetate (50 ml×2), dried over Na₂SO₄, filtered and concentrated. The residue was purified by silica gel chromatography (petroleum ether/ethyl acetate, 10:1 to 3:1) to give 2-cyano-N-(6,8-dichloro-2,7-naphthyridin-3-yl)propanamide (450 mg, 96% yield) as pale-yellow solid. LCMS (ESI) [M+H]⁺=295.1.

Step 4: N-(8-amino-6-chloro-2,7-naphthyridin-3-yl)-2-cyanopropanamide

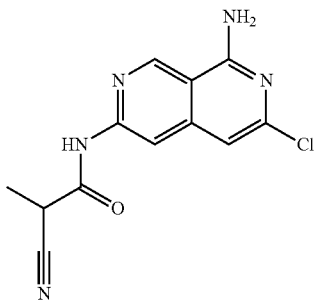 [SMILES: CC(C#N)C(=O)Nc1cc2cc(Cl)nc(N)c2cn1]

To a microwave tube was added 2-cyano-N-(6,8-dichloro-2,7-naphthyridin-3-yl)propanamide (150 mg, 0.51 mmol) and 0.5 N NH₃ in dioxane (12.5 mL, 6.25 mmol). The mixture was stirred at 80° C. for 40 hours. The mixture was concentrated and purified by silica gel chromatography (petroleum ether/ethyl acetate, 1:1 to 0:100) to give N-(8-amino-6-chloro-2,7-naphthyridin-3-yl)-2-cyano-propanamide (50 mg, 36% yield) as a yellow solid. LCMS (ESI) [M+H]⁺=276.1.

Step 5: N-(8-amino-6-(4-methylpyridin-3-yl)-2,7-naphthyridin-3-yl)-2-cyanopropanamide

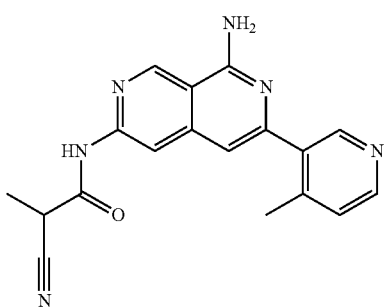 [SMILES: Cc1ccncc1-c1cc2cc(NC(=O)C(C)C#N)ncc2c(N)n1]

To a vial was added N-(8-amino-6-chloro-2,7-naphthyridin-3-yl)-2-cyano-propanamide (50 mg, 0.18 mmol), 4-methyl-3-(4,4,5,5-tetramethyl-1,3,2-dioxaborolan-2-yl)pyridine (52 mg, 0.24 mmol), XPhos Pd G2 (21 mg, 0.03 mmol), X-phos (17 mg, 0.04 mmol), potassium acetate (53 mg, 0.54 mmol), water (2 mL) and 1,4-dioxane (20 mL). The reaction mixture was bubbled through with nitrogen and then stirred at 100° C. for 6 hours. The mixture was concentrated and purified by silica gel chromatography (dichloromethane/methanol, 100:1 to 10:1) to give N-[8-amino-6-(4-methyl-3-pyridyl)-2,7-naphthyridin-3-yl]-2-cyano-propanamide (15 mg, 25% yield) as a pale-yellow solid. LCMS (ESI): R$_T$ (min)=1.541, [M+H]⁺=333.2, method=F; ¹H NMR (400 MHz, CD₃OD) δ 9.31 (s, 1H), 8.54 (s, 1H), 8.43 (d, J=5.2 Hz, 1H), 8.33 (s, 1H), 7.39 (d, J=5.2 Hz, 1H), 7.01 (s, 1H), 2.45 (s, 3H), 1.64 (s, 3H).

Example 39

N-(8-amino-6-(4-methylpyridin-3-yl)-2,7-naphthyridin-3-yl)-2-hydroxy-2-methylpropanamide (Compound 39)

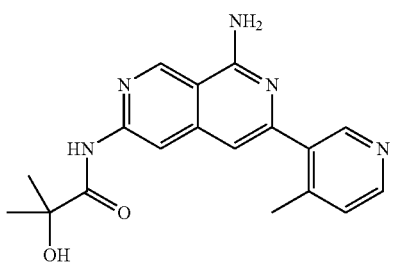 [SMILES: Cc1ccncc1-c1cc2cc(NC(=O)C(C)(C)O)ncc2c(N)n1]

Step 1: 1-chloro-2-methyl-1-oxopropan-2-yl formate

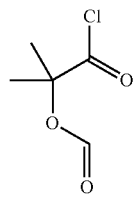

To a vial was added 2-hydroxy-2-methyl-propanoic acid (0.5 g, 4.8 mmol) and dichloromethane (20 mL) and the solution was cooled to 0° C. Oxalyl chloride (0.61 mL, 7.2 mmol) and DMF (0.1 mL, 1.30 mmol) were added dropwise. The mixture was stirred at room temperature for 3 hours. The reaction mixture was concentrated in high vacuo to get a crude product and used for the next step directly.

Step 2: 1-(6,8-dichloro-2,7-naphthyridin-3-ylamino)-2-methyl-1-oxopropan-2-yl formate

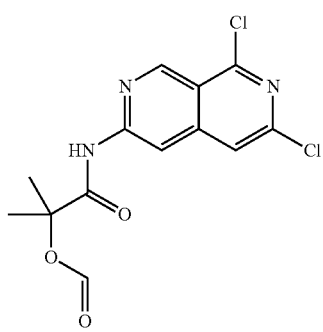 [SMILES: CC(C)(OC=O)C(=O)Nc1cc2cc(Cl)nc(Cl)c2cn1]

To a vial was added 6,8-dichloro-2,7-naphthyridin-3-amine hydrochloride (200 mg, 0.80 mmol), (2-chloro-1,1-dimethyl-2-oxo-ethyl) formate (1.3 mL, 2.16 mmol) and pyridine (5 mL). The mixture was stirred at 20° C. for 2 hours. The mixture was poured into water (10 mL), pH adjusted to 6 with 1N HCl, extracted with dichloromethane (50 ml×2), dried over Na$_2$SO$_4$, filtered and concentrated. The residue was purified by silica gel chromatography (petroleum ether/ethyl acetate, 10:1 to 3:1) to give [2-[(6, 8-dichloro-2,7-naphthyridin-3-yl)amino]-1,1-dimethyl-2-oxo-ethyl] formate (160 mg, 61% yield) as a pale-yellow solid. LCMS (ESI) [M+H]$^+$=328.0.

Step 3: N-(8-amino-6-chloro-2,7-naphthyridin-3-yl)-2-hydroxy-2-methylpropanamide

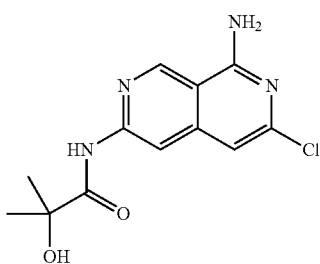 [SMILES: CC(C)(O)C(=O)Nc1cc2cc(Cl)nc(N)c2cn1]

To a microwave tube was added [2-[(6,8-dichloro-2,7-naphthyridin-3-yl)amino]-1,1-dimethyl-2-oxo-ethyl] formate (150 mg, 0.46 mmol) and ammonium hydroxide (17 mL, 112 mmol). The mixture was stirred at 80° C. for 6 hours. The mixture was then concentrated in vacuo to give crude product N-(8-amino-6-chloro-2,7-naphthyridin-3-yl)-2-hydroxy-2-methyl-propanamide (100 mg, 57% yield) as a pale-yellow solid. LCMS (ESI) [M+H]$^+$=281.1.

Step 4: N-(8-amino-6-(4-methylpyridin-3-yl)-2,7-naphthyridin-3-yl)-2-hydroxy-2-methylpropanamide

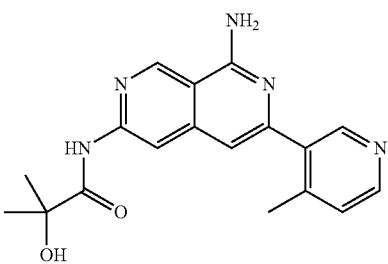 [SMILES: Cc1ccncc1-c1cc2cc(NC(=O)C(C)(C)O)ncc2c(N)n1]

To a vial was added N-(8-amino-6-chloro-2,7-naphthyridin-3-yl)-2-hydroxy-2-methyl-propanamide (150 mg, 0.53 mmol), XPhos Pd G2 (54 mg, 0.07 mmol), X-phos (49 mg, 0.1 mmol), potassium acetate (134 mg, 1.37 mmol), 4-methyl-3-(4,4,5,5-tetramethyl-1,3,2-dioxaborolan-2-yl) pyridine (175 mg, 0.80 mmol), 1,4-dioxane (5 mL), and water (0.3 mL). The reaction was then stirred at 110° C. for 16 hours under nitrogen. The reaction was then cooled to 0° C. and HCl in dioxane (10 mL, 4 M, 40 mmol) was added. The mixture was stirred at room temperature for 30 minutes. The mixture was concentrated and NH$_3$ (7N in methanol, 30 mL) was added. The mixture was then concentrated and purified by silica gel chromatography (dichloromethane/methanol, 100:1 to 10:1) to give N-[8-amino-6-(4-methyl-3-pyridyl)-2,7-naphthyridin-3-yl]-2-hydroxy-2-methyl-propanamide (7 mg, 4% yield) as a pale-yellow solid. LCMS (ESI): R$_T$ (min)=0.9660, [M+H]$^+$=338.1, method=B; $^1$H NMR (400 MHz, CD$_3$OD) δ 9.29 (s, 1H), 8.53 (s, 1H), 8.42 (d, J=5.2 Hz 1H), 8.38 (s, 1H), 7.37 (d, J=5.2 Hz, 1H), 6.99 (s, 1H), 2.45 (s, 3H), 1.50 (s, 6H).

Example 40

N-(8-amino-6-(2-oxooxazolidin-3-yl)-2,7-naphthyridin-3-yl)cyclopropanecarboxamide (Compound 40)

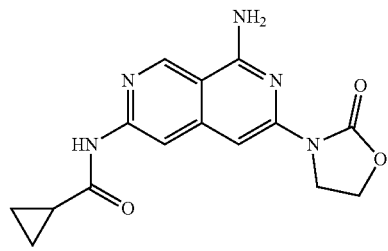 [SMILES: Nc1nc(N2CCOC2=O)cc2cc(NC(=O)C3CC3)ncc12]

To a vial was added N-[8-(benzhydrylideneamino)-6-chloro-2,7-naphthyridin-3-yl]cyclopropanecarboxamide (100 mg, 0.23 mmol), Pd$_2$(dba)$_3$ (21.45 mg, 0.0200 mmol), Xantphos (20 mg, 0.04 mmol), Cs$_2$CO$_3$ (152 mg, 0.47 mmol), 1,3-oxazolidin-2-one (30 mg, 0.35 mmol) and 1,4-dioxane (5 mL). The reaction was stirred at 110° C. for 8 hours under nitrogen. The reaction was concentrated and purified by silica gel chromatography (dichloromethane/methanol, 100:1 to 10:1) to give N-[8-amino-6-(2-oxooxazolidin-3-yl)-2,7-naphthyridin-3-yl]cyclopropanecarboxamide (45 mg, 60% yield) as a pale-yellow solid. LCMS (ESI): R$_T$ (min)=1.092, [M+H]$^+$=314.1, method=B; $^1$H NMR (400 MHz, DMSO-d$_6$) δ: 10.86 (s, 1H), 9.24 (s, 1H), 8.05 (s, 1H), 7.36-7.33 (m, 3H), 4.42 (t, J=8.0 Hz, 2H), 4.17 (t, J=8.0 Hz, 2H), 2.08-2.01 (m, 1H), 0.85-0.80 (m, 4H).

Example 41

N-(8-amino-6-(2-oxo-1,2-dihydropyridin-3-yl)-2,7-naphthyridin-3-yl) cyclopropanecarboxamide (Compound 42)

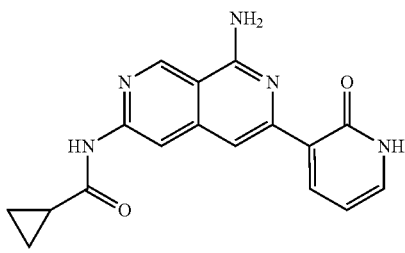 [SMILES: Nc1nc(-c2ccc[nH]c2=O)cc2cc(NC(=O)C3CC3)ncc12]

Step 1: 2-oxo-1,2-dihydropyridin-3-ylboronic acid

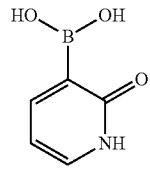

A mixture of 3-bromo-1H-pyridin-2-one (0.5 g, 2.87 mmol), bis(pinacolato)diboron (0.77 g, 3.02 mmol), potassium acetate (0.83 g, 8.49 mmol) and Pd(dppf)$_2$Cl$_2$ (0.23 g, 0.29 mmol) in 1,4-dioxane (10 mL) was stirred at 130° C. for 2 hours in a microwave reactor. The mixture was used for the next step directly. LCMS (ESI) [M+H]$^+$=140.1.

Step 2: N-(8-(bis(4-methoxybenzyl)amino)-6-chloro-2,7-naphthyridin-3-yl)cyclopropanecarboxamide

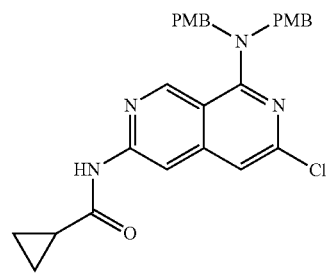

To a vial was added 3-chloro-N1,N1-bis[(4-methoxyphenyl)methyl]-2,7-naphthyridine-1,6-diamine (165 mg, 0.38 mmol), cyclopropanecarbonyl chloride (0.1 mL, 1.13 mmol) and pyridine (5 mL). The mixture was stirred at 20° C. for 2 hours. The mixture was concentrated. The residue was purified by silica chromatography (petroleum ether/ethyl acetate, 10:1 to 3:1) to get N-[8-[bis[(4-methoxyphenyl)methyl]amino]-6-chloro-2,7-naphthyridin-3-yl]cyclopropanecarboxamide (188 mg, 97% yield) as a pale-yellow solid. LCMS (ESI) [M+H]$^+$=503.1.

Step 3: N-(8-(bis(4-methoxybenzyl)amino)-6-(2-oxo-1,2-dihydropyridin-3-yl)-2,7-naphthyridin-3-yl)cyclopropanecarboxamide

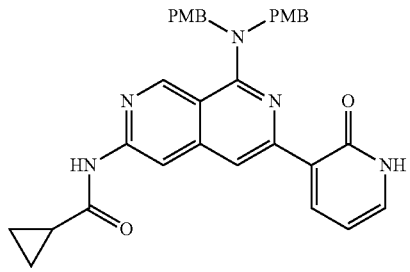

To a vial was added XPhos Pd G2 (24 mg, 0.03 mmol), X-phos (21 mg, 0.04 mmol), N-[8-[bis[(4-methoxyphenyl)methyl]amino]-6-chloro-2,7-naphthyridin-3-yl]cyclopropanecarboxamide (150 mg, 0.3 mmol), potassium acetate (150 mg, 1.53 mmol), (2-oxo-1H-pyridin-3-yl)boronic acid (300 mg, 1.08 mmol), water (2 mL) and 1,4-dioxane (20 mL). The reaction mixture was degassed by bubbling with nitrogen and then stirred at 100° C. for 16 hours. The mixture was then concentrated and purified by silica gel chromatography (ethyl acetate) to give N-[8-[bis[(4-methoxyphenyl)methyl]amino]-6-(2-oxo-1H-pyridin-3-yl)-2,7-naphthyridin-3-yl]cyclopropanecarboxamide (180 mg, 43% yield) as a yellow solid. LCMS (ESI) [M+H]$^+$=562.2.

Step 4: N-(8-amino-6-(2-oxo-1,2-dihydropyridin-3-yl)-2,7-naphthyridin-3-yl)cyclopropanecarboxamide

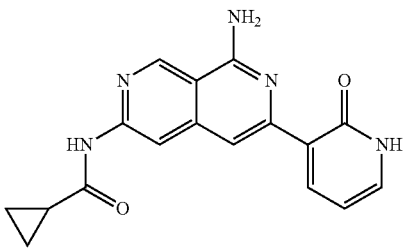 [SMILES: Nc1nc(-c2ccc[nH]c2=O)cc2cc(NC(=O)C3CC3)ncc12]

To a vial was added N-[8-[bis[(4-methoxyphenyl)methyl]amino]-6-(2-oxo-1H-pyridin-3-yl)-2,7-naphthyridin-3-yl]cyclopropanecarboxamide (180 mg, 0.1300 mmol) and TFA (5 mL). The mixture was stirred at 80° C. for 48 hours and then concentrated in vacuo. To this NH$_3$ (7 N in methanol, 3 mL) was added and the reaction mixture was concentrated in vacuo. The residue was purified by silica gel chromatography (dichloromethane/methanol/NH$_3$-water, 100:5:1) to give N-[8-amino-6-(2-oxo-1H-pyridin-3-yl)-2,7-naphthyridin-3-yl]cyclopropanecarboxamide (24 mg, 58% yield) as a yellow solid. LCMS (ESI): R$_T$(min)=1.034, [M+H]$^+$=322.1, method=B; $^1$H NMR (400 MHz, DMSO-d$_6$) δ 12.01 (br, 1H), 10.95 (s, 1H), 9.31 (s, 1H), 8.60 (d, J=6.4 Hz, 1H), 8.26 (s, 1H), 8.17 (s, 1H), 7.52 (br, 1H), 7.15 (br, 2H), 6.47-6.35 (m, 1H), 2.12-2.02 (m 1H), 0.91-076 (m, 4H).

Example 42 trans-N-(8-amino-6-(4-methylpyridin-3-yl)-2,7-naphthyridin-3-yl)-2-cyanocyclopropanecarboxamide (Compound 43)

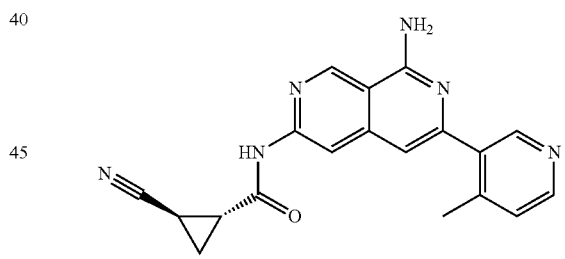

To a vial was added (±)-trans-N-(8-amino-6-chloro-2,7-naphthyridin-3-yl)-2-cyano-cyclopropanecarboxamide (78 mg, 0.27 mmol), K$_2$CO$_3$ (60 mg, 0.61 mmol), Pd(dppf)Cl$_2$ (30 mg, 0.04 mmol), 4-methyl-3-(4,4,5,5-tetramethyl-1,3,2-dioxaborolan-2-yl)pyridine (89 mg, 0.41 mmol), water (1 mL) and 1,4-dioxane (10 mL). The mixture was bubbled through with nitrogen for 20 min and then stirred at 100° C. for 2 hours. The mixture was concentrated and purified by silica gel chromatography (dichloromethane/methanol, 100:1 to 10:1) followed by reverse phase chromatography (Boston 40 g ODS column, eluted with NaHCO$_3$10 mmol/L:acetonitrile from 100:0 to 1:4, uv 254 nm, 214 nm) to give (±)-trans-N-[8-amino-6-(4-methyl-3-pyridyl)-2,7-naphthyridin-3-yl]-2-cyano-cyclopropanecarboxamide (25 mg, 29% yield) as a pale-yellow solid. LCMS (ESI): R$_T$(min)=1.094, [M+H]$^+$=345.2, method=B; $^1$H NMR (400 MHz, CD$_3$OD) δ 9.28 (s, 1H), 8.51 (s, 1H), 8.41 (d, J=5.2 Hz, 1H), 8.28 (s, 1H), 7.37 (d, J=5.2 Hz, 1H), 6.95 (s, 1H), 2.68-2.59 (m, 1H), 2.44 (s, 3H), 2.14-2.07 (m, 1H), 1.63-1.51 (m, 2H).

Example 43

(1S,2S)—N-(8-amino-6-(4-(hydroxymethyl)pyridin-3-yl)-2,7-naphthyridin-3-yl)-2-fluorocyclopropanecarboxamide (Compound 44)

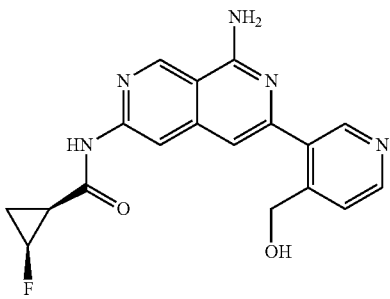 [SMILES: Nc1nc(-c2cnccc2CO)cc2cc(NC(=O)[C@@H]3C[C@@H]3F)ncc12]

Step 1: (3-(6-amino-1-(bis(4-methoxybenzyl)amino)-2,7-naphthyridin-3-yl)pyridin-4-yl)methanol

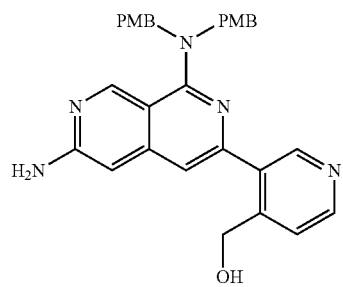

To a vial was added Pd(Ph₃P)₄ (80 mg, 0.07 mmol), Cs$_2$CO$_3$ (300 mg, 0.92 mmol), 3-chloro-N1,N1-bis[(4-methoxyphenyl)methyl]-2,7-naphthyridine-1,6-diamine (200 mg, 0.46 mmol), 1-hydroxy-3H-oxaborolo[3,4-c]pyridine (1.0 g, 2.22 mmol), water (1 mL) and 1,4-dioxane (10 mL). The reaction mixture was degassed by bubbled through with nitrogen for 20 min and then stirred at 100° C. for 16 hours. The mixture was concentrated and purified by silica gel chromatography (dichloromethane/methanol, 100:1 to 10:1) to give [3-[6-amino-1-[bis[(4-methoxyphenyl)methyl]amino]-2,7-naphthyridin-3-yl]-4-pyridyl]methanol (205 mg, 88% yield) as a yellow solid. LCMS (ESI) [M+H]⁺=508.2.

Step 2: (1S,2S)—N-(8-(bis(4-methoxybenzyl)amino)-6-(4-(hydroxymethyl)pyridin-3-yl)-2,7-naphthyridin-3-yl)-2-fluorocyclopropanecarboxamide

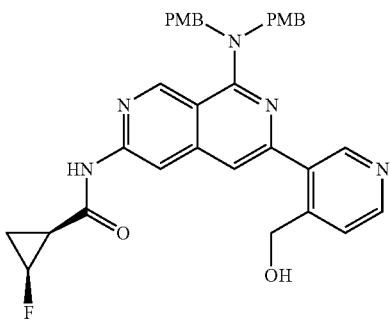

To a vial was added [3-[6-amino-1-[bis[(4-methoxyphenyl)methyl]amino]-2,7-naphthyridin-3-yl]-4-pyridyl]methanol (150 mg, 0.3 mmol), dichloromethane (3 mL), and pyridine (2 mL). A solution of (1S, 2S)-2-fluorocyclopropanecarbonyl chloride (181 mg, 1.48 mmol) was added drop wise. The mixture was stirred at room temperature for 2 h. The mixture was concentrated, dissolved in methanol (10 mL), and K$_2$CO$_3$ (300 mg, 2.17 mmol) was added. The mixture was stirred at 80° C. for 30 minutes. The mixture was then concentrated in vacuo to get a crude product, (1S,2S)—N-[8-[bis[(4-methoxyphenyl)methyl]amino]-6-[4-(hydroxymethyl)-3-pyridyl]-2,7-naphthyridin-3-yl]-2-fluoro-cyclopropanecarboxamide (560 mg, 96% yield) which was used for the next step directly. LCMS (ESI) [M+H]⁺=594.2.

Step 3: (1S,2S)—N-(8-amino-6-(4-(hydroxymethyl)pyridin-3-yl)-2,7-naphthyridin-3-yl)-2-fluorocyclopropanecarboxamide

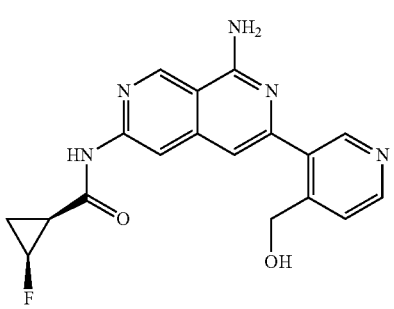 [SMILES: Nc1nc(-c2cnccc2CO)cc2cc(NC(=O)[C@@H]3C[C@@H]3F)ncc12]

To a vial was added (1S,2S)—N-[8-[bis[(4-methoxyphenyl)methyl]amino]-6-[4-(hydroxymethyl)-3-pyridyl]-2,7-naphthyridin-3-yl]-2-fluoro-cyclopropanecarboxamide (560 mg, 0.28 mmol) and TFA (5 mL). The mixture was stirred at 80° C. for 16 hours and then concentrated in vacuo. The residue was dissolved in NH$_3$ (7 N in methanol, 10 mL), concentrated and purified by prep-TLC (silica-gel, dichloromethane/methanol/NH$_3$-water, 100:10:1) to give (1S,2S)—N-[8-amino-6-[4-(hydroxymethyl)-3-pyridyl]-2,7-naphthyridin-3-yl]-2-fluoro-cyclopropanecarboxamide (95 mg, 90% yield) as a pale-yellow solid. LCMS (ESI): R$_T$ (min)=1.414, [M+H]⁺=354.2, method=F; ¹H NMR (400 MHz, DMSO-d$_6$) δ: 11.08 (s, 1H), 9.45 (s, 1H), 8.70 (s, 1H), 8.64 (d, J=5.2 Hz, 1H), 8.32 (s, 1H), 7.67 (d, J=5.2 Hz, 1H), 7.44 (br, 2H), 7.11 (s, 1H), 5.52 (t, J=5.6 Hz, 1H), 5.13-4.90 (m, 1H), 4.74 (d, J=5.6 Hz, 2H), 2.40-2.29 (m, 1H), 1.80-1.68 (m, 1H), 1.32-1.20 (m, 1H).

Example 44

(±)-(1S,2S)—N-(8-amino-6-(2-ethylpyrrolidin-1-yl)-2,7-naphthyridin-3-yl)-2-fluorocyclopropanecarboxamide (Compound 45)

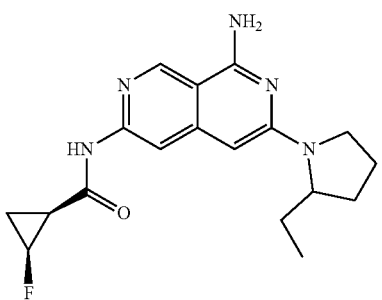 [SMILES: CCC1CCCN1c1cc2cc(NC(=O)[C@@H]3C[C@@H]3F)ncc2c(N)n1]

Step 1: 3-(2-ethylpyrrolidin-1-yl)-N1,N1-bis(4-methoxybenzyl)-2,7-naphthyridine-1,6-diamine

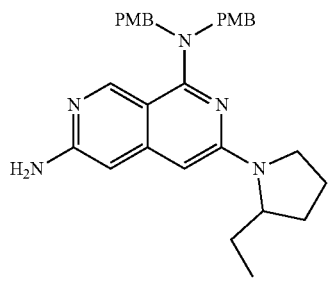

To a sealed tube was added 3-chloro-N1,N1-bis[(4-methoxyphenyl)methyl]-2,7-naphthyridine-1,6-diamine (200 mg, 0.46 mmol), 1-methyl-2-pyrrolidinone (3 mL) and (±)-2-ethylpyrrolidine (400 mg, 4 mmol). The reaction was heated to 200° C. in a microwave reactor for 8 hours. The reaction mixture was poured into water (30 mL) and extracted with ethyl acetate (50 mL×2). The combined organic extracts were washed with brine (30 ml), 1 N HCl (5 mL), brine (20 mL), dried over Na$_2$SO$_4$, filtered and concentrated in vacuo. The residue was purified by silica gel chromatography (dichloromethane/methanol, 100:1 to 20:1) to give (±)-3-(2-ethylpyrrolidin-1-yl)-N1,N1-bis[(4-methoxyphenyl)methyl]-2,7-naphthyridine-1,6-diamine (130 mg, 57% yield) as a yellow solid. LCMS (ESI) [M+H]$^+$=498.2.

Step 2: (1S,2S)—N-(8-(bis(4-methoxybenzyl)amino)-6-(2-ethylpyrrolidin-1-yl)-2,7-naphthyridin-3-yl)-2-fluorocyclopropanecarboxamide

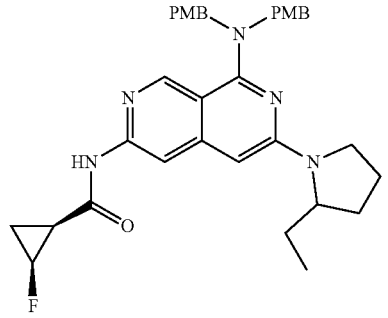

To a vial was added (±)-3-(2-ethylpyrrolidin-1-yl)-N1,N1-bis[(4-methoxyphenyl)methyl]-2,7-naphthyridine-1,6-diamine (130 mg, 0.24 mmol), pyridine (96 mg, 1.22 mmol) and dichloromethane (5 mL). A solution of (1S,2S)-2-fluorocyclopropanecarbonyl chloride (89 mg, 0.7300 mmol) in dichloromethane (5 mL) was added drop wise. The mixture was stirred at room temperature for 2 hours. The mixture was concentrated and purified by silica gel chromatography (dichloromethane/methanol/NH$_3$-water, 100:5:1) to give (1S,2S)—N-[8-[bis[(4-methoxyphenyl)methyl]amino]-6-(2-ethylpyrrolidin-1-yl)-2,7-naphthyridin-3-yl]-2-fluoro-cyclopropanecarboxamide (60 mg, 40% yield) as a yellow oil. LCMS (ESI) [M+H]$^+$=584.3.

Step 3: (±)-(1S,2S)—N-(8-amino-6-(2-ethylpyrrolidin-1-yl)-2,7-naphthyridin-3-yl)-2-fluorocyclopropanecarboxamide

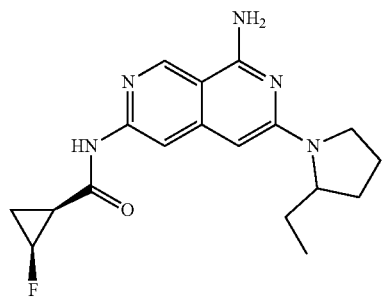 [SMILES: CCC1CCCN1c1cc2cc(NC(=O)[C@@H]3C[C@@H]3F)ncc2c(N)n1]

To a vial was added (1S,2S)—N-[8-[bis[(4-methoxyphenyl)methyl]amino]-6-(2-ethylpyrrolidin-1-yl)-2,7-naphthyridin-3-yl]-2-fluoro-cyclopropanecarboxamide (60 mg, 0.1 mmol) and TFA (5 mL). The mixture was stirred at 80° C. for 16 hours. The mixture was concentrated and NH$_3$ (7 N in methanol, 10 mL) was added. The reaction mixture was concentrated and purified by prep-TLC (silica, dichloromethane/methanol/NH$_3$.water=100:10:1, uv 254 nm) to give (±)-(1S,2S)—N-[8-amino-6-(2-ethylpyrrolidin-1-yl)-2,7-naphthyridin-3-yl]-2-fluoro-cyclopropanecarboxamide (20 mg, 60% yield) as a pale-yellow solid. LCMS (ESI): R$_T$ (min)=1.223, [M+H]$^+$=344.2, method=B; $^1$H NMR (400 MHz, CD3OD) δ: 8.68 (s, 1H), 7.69 (s, 1H), 5.57 (s, 1H), 4.87-4.63 (m, 1H), 3.93-3.84 (m, 1H), 3.45-3.37 (m, 1H), 3.35-3.27 (m, 1H), 2.03-1.81 (m, 4H), 1.80-1.60 (m, 3H), 1.36-1.23 (m, 1H), 1.14-1.03 (m, 1H), 0.84 (t, J=7.6 Hz, 3H).

Example 45

(±)-cis-N-(8-amino-6-(4-cyclopropylpyridin-3-yl)-2,7-naphthyridin-3-yl)-2-fluorocyclopropanecarboxamide (Compound 46)

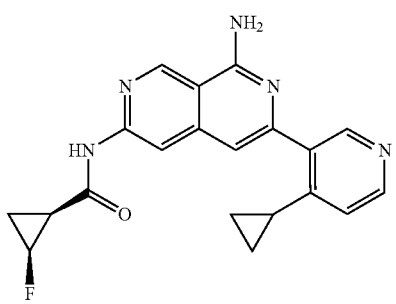 [SMILES: Nc1nc(-c2cnccc2C2CC2)cc2cc(NC(=O)[C@@H]3C[C@@H]3F)ncc12]

Step 1: 3-bromo-4-cyclopropylpyridine

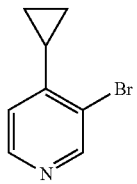

To a round bottom flask was added LiCi (644 mg, 15 mmol) and cyclopropylmagnesiumbromide (30 mL, 15 mmol). The mixture was stirred at room temperature for 30 min under nitrogen. In another flask, 3-bromopyridine (2.0 g, 12.66 mmol), THF (50 mL) and boron trifluoride diethyl etherate (1.8 mL, 14 mmol) was mixed at 0° C. The mixture was stirred at room temperature for 30 min. The solution was then re-cooled to −55° C. before the solution of cyclopropylmagnesiumbromide and LiCl complex was added drop wise. The mixture was stirred at −55° C. for 30 minutes, and then allow warmed to room temperature slowly. After stirring overnight at room temperature, the reaction was quenched with aqueous NaHCO₃ (10 mL) and water (20 mL). The mixture was extracted with ethyl acetate (50 ml×3), dried over Na₂SO₄, filtered and concentrated in vacuo. The residue was purified by silica gel chromatography (petroleum ether/ethyl acetate from 10:1 to 3:1) to give 3-bromo-4-cyclopropyl-pyridine (220 mg, 9% yield) as a colourless oil. LCMS (ESI) [M+H]⁺=198.0.

Step 2: 4-cyclopropylpyridin-3-ylboronic acid

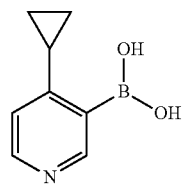

To a vial was added 3-bromo-4-cyclopropyl-pyridine (120 mg, 0.61 mmol), triisopropyl borate (230 mg, 1.22 mmol) and THF (5 mL). The mixture was then cooled to −78° C. before n-BuLi (2.5 M in hexane, 0.5 mL, 1.25 mmol) was added dropwise. The mixture was allowed to warm to room temperature slowly. After stirring for 2 h at room temperature, the mixture was quenched by water (10 mL), washed with ethyl acetate (20 mL×2), acified to pH 5 with 2N HCl, and concentrated in vacuo. The residue was re-suspended in ethanol (30 mL), filtered and concentrated in vacuo to give (4-cyclopropyl-3-pyridyl)boronic acid (120 mg, 97% yield) as a pale-yellow oil. LCMS (ESI) [M+H]⁺=164.2

Step 3: (±)-cis-N-(8-amino-6-(4-cyclopropylpyridin-3-yl)-2,7-naphthyridin-3-yl)-2-fluorocyclopropanecarboxamide

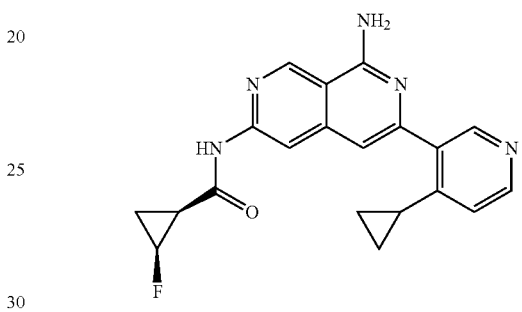

To a vial was added cis-N-(8-amino-6-chloro-2,7-naphthyridin-3-yl)-2-fluoro-cyclopropanecarboxamide (120 mg, 0.43 mmol), X-phos (40 mg, 0.09 mmol), XPhos Pd G2 (50 mg, 0.06 mmol), potassium acetate (126 mg, 1.28 mmol), (4-cyclopropyl-3-pyridyl)boronic acid (80 mg, 0.39 mmol), water (1 mL), and 1,4-dioxane (10 mL). The reaction mixture was degassed by bubbling with nitrogen for 20 min and then stirred at 100° C. for 6 hours. The mixture was concentrated and purified by silica gel chromatography (dichloromethane/methanol, 100:1 to 10:1) to give (±)-cis-N-[8-amino-6-(4-cyclopropyl-3-pyridyl)-2,7-naphthyridin-3-yl]-2-fluoro-cyclopropanecarboxamide (39 mg, 24% yield) as a pale-yellow solid. LCMS (ESI): R$_T$(min)=1.104, [M+H]⁺=364.1, method=B; ¹H NMR (400 MHz, CD₃OD) δ: 9.38 (s, 1H), 8.47 (s, 1H), 8.39 (d, J=5.6 Hz, 1H), 8.32 (s, 1H), 7.04 (s, 1H), 6.97 (d, J=5.6 Hz, 1H), 4.98-4.76 (m, 1H), 2.22-2.11 (m, 2H), 1.89-1.77 (m, 1H), 1.24-1.18 (m, 1H), 1.11-1.04 (m, 2H), 0.92-0.85 (m, 2H).

Example 46

(±)-trans-N-(8-amino-6-(1-methyl-1H-pyrazol-4-yl)-2,7-naphthyridin-3-yl)-2-methylcyclopropanecarboxamide (Compound 47)

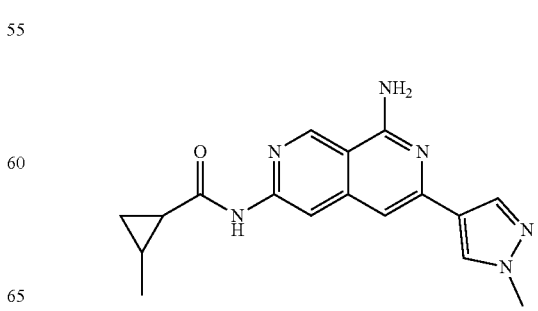

Step 1: (±)-trans-2-methylcyclopropanecarbonyl chloride

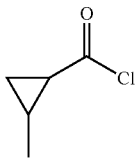

To a vial was added (±)-trans-2-methylcyclopropanecarboxylic acid (200 mg, 2.0 mmol) and dichloromethane (10 mL). The mixture was cooled to 0° C. before oxalyl chloride (0.3 mL, 4 mmol) and DMF (0.01 mL) were added drop wise. The mixture was stirred at 20° C. for 2 hours. The reaction mixture was concentrated in vacuo to get a crude product and used for the next step directly.

Step 2: (±)-trans-N-(6,8-dichloro-2,7-naphthyridin-3-yl)-2-methylcyclopropanecarboxamide

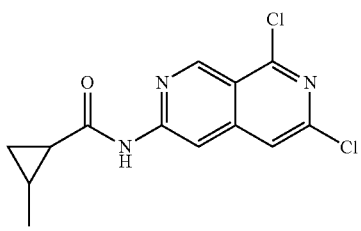 [SMILES: CC1CC1C(=O)Nc1cc2cc(Cl)nc(Cl)c2cn1]

To a vial was added 6,8-dichloro-2,7-naphthyridin-3-amine (60 mg, 0.28 mmol), pyridine (2 mL), and a solution of (±)-trans-2-methylcyclopropanecarbonyl chloride (166 mg, 1.4 mmol) in dichloromethane (3 mL). The reaction was stirred at room temperature for 2 hours. The mixture was concentrated in vacuo and purified by silica gel chromatography (dichloromethane/methanol, 20:1) to give (±)-trans-N-(6,8-dichloro-2,7-naphthyridin-3-yl)-2-methyl-cyclopropanecarboxamide (80 mg, 93% yield). LCMS (ESI) [M+H]$^+$=296.0.

Step 3: N-(8-amino-6-chloro-2,7-naphthyridin-3-yl)-2-methylcyclopropanecarboxamide

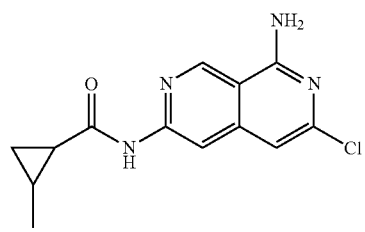 [SMILES: CC1CC1C(=O)Nc1cc2cc(Cl)nc(N)c2cn1]

To a 10 mL microwave tube was added (±)-trans-N-(6,8-dichloro-2,7-naphthyridin-3-yl)-2-methyl-cyclopropanecarboxamide (80 mg, 0.27 mmol), NH$_3$-water (2 mL, 13.51 mmol) and 1,4-dioxane (2 mL). The mixture was stirred at 80° C. for 16 hours. The mixture was concentrated in vacuo and purified by silica gel chromatography (dichloromethane/methanol/NH$_3$-water, 100:5:1) to get (±)-trans-N-(8-amino-6-chloro-2,7-naphthyridin-3-yl)-2-methyl-cyclopropanecarboxamide (80 mg, 99% yield) as a white solid. LCMS (ESI) [M+H]$^+$=277.1.

Step 4: (±)-trans-N-(8-amino-6-(1-methyl-1H-pyrazol-4-yl)-2,7-naphthyridin-3-yl)-2-methylcyclopropanecarboxamide

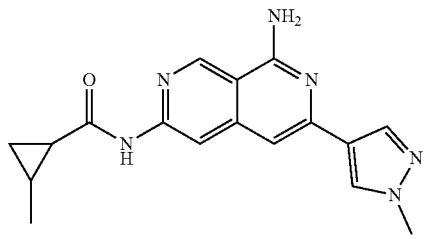 [SMILES: CC1CC1C(=O)Nc1cc2cc(-c3cnn(C)c3)nc(N)c2cn1]

To a vial was added XPhos Pd G2 (20 mg, 0.03 mmol), X-phos (18 mg, 0.04 mmol), N-(8-amino-6-chloro-2,7-naphthyridin-3-yl)-2-methyl-cyclopropanecarboxamide (80 mg, 0.26 mmol), potassium acetate (51 mg, 0.52 mmol), 1-methyl-4-(4,4,5,5-tetramethyl-1,3,2-dioxaborolan-2-yl)-1h-pyrazole (81 mg, 0.39 mmol), water (0.5 mL) and 1,4-dioxane (5 mL). The reaction was degassed by bubbling through with N$_2$ and then stirred at 100° C. for 16 hours. The mixture was concentrated and purified by silica gel chromatography (dichloromethane/methanol, 30:1 to 10:1) to give a mixture of the (±)-cis and (±)-trans-isomers of N-[8-amino-6-(1-methylpyrazol-4-yl)-2,7-naphthyridin-3-yl]-2-methyl-cyclopropanecarboxamide (42 mg, 50% yield, 1H NMR shows 3:1 trans:cis) as a yellow solid. LCMS (ESI): R$_T$ (min)=1.661, [M+H]$^+$=323.2, method=F; $^1$H NMR (400 MHz, DMSO-d$_6$) δ: 10.77 (s, 1H), 9.24 (s, 1H), 8.15 (s, 1H), 8.11 (s, 1H), 7.96 (s, 1H), 7.12 (br, 2H), 7.04 (s, 1H), 3.88 (s, 3H), 2.12-2.02 (m, 0.3H), 1.86-1.77 (m, 0.7H), 1.34-1.20 (m, 1H), 1.18-0.94 (m, 4H), 0.85-0.79 (m, 0.3H), 0.72-0.63 (m, 0.7H).

Example 47

(±)-4-(1-amino-6-((cis)-2-fluorocyclopropanecarboxamido)-2,7-naphthyridin-3-yl)-3-methylbenzamide (Compound 48)

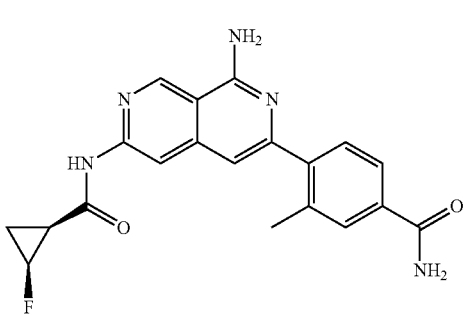 [SMILES: Cc1cc(C(N)=O)ccc1-c1cc2cc(NC(=O)[C@@H]3C[C@@H]3F)ncc2c(N)n1]

Step 1: 3-methyl-4-(4,4,5,5-tetramethyl-1,3,2-dioxa-borolan-2-yl)benzamide

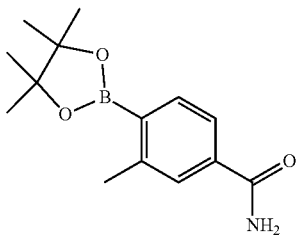 [SMILES: Cc1cc(C(N)=O)ccc1B1OC(C)(C)C(C)(C)O1]

To a sealed tube was added 4-bromo-3-methyl-benzamide (1.0 g, 4.67 mmol), bis(pinacolato)diboron (1.4 g, 5.61 mol), potassium acetate (1.4 g, 14.01 mmol), Pd(dppf)Cl$_2$ (341 mg, 0.47 mmol) and 1,4-dioxane (10 mL). The mixture was bubbled through with N$_2$ for 2 minutes and stirred at 100° C. for 3 hours. The mixture was concentrated in vacuo and purified by silica gel chromatography (petroleum ether/ethyl acetate, 1:1 to 0:100) to afford 3-methyl-4-(4,4,5,5-tetramethyl-1,3,2-dioxaborolan-2-yl)benzamide (920 mg, 71% yield) as a white solid. LCMS (ESI) [M+H]$^+$=262.2.

Step 2: (±)-4-(1-amino-6-((cis)-2-fluorocyclopropanecarboxamido)-2,7-naphthyridin-3-yl)-3-methyl-benzamide

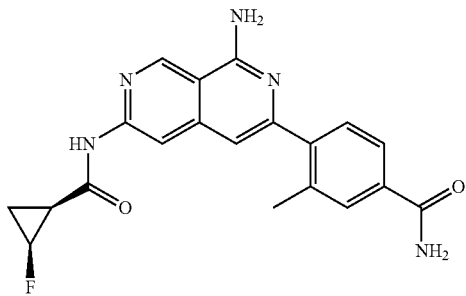 [SMILES: Cc1cc(C(N)=O)ccc1-c1cc2cc(NC(=O)[C@@H]3C[C@@H]3F)ncc2c(N)n1]

To a vial was added (±)-cis-N-(8-amino-6-chloro-2,7-naphthyridin-3-yl)-2-fluoro-cyclopropanecarboxamide (70 mg, 0.25 mmol), K$_2$CO$_3$ (49 mg, 0.5 mmol), Pd(dppf)Cl$_2$ (30 mg, 0.04 mmol), 3-methyl-4-(4,4,5,5-tetramethyl-1,3,2-dioxaborolan-2-yl)benzamide (98 mg, 0.37 mmol), water (0.5 mL) and 1,4-dioxane (5 mL). The reaction was bubbled through with N$_2$ for 20 minutes and then stirred at 90° C. for 5 hours. The mixture was then concentrated and purified by silica gel chromatography (dichloromethane/methanol, 100:1 to 10:1) and then reverse phase chromatography (Boston 40 g ODS column, eluted with NaHCO$_3$ 10 mmol/L:acetonitrile from 100:0 to 1:4, uv 254 nm, 214 nm) to give (±)-4-[1-amino-6-[[(cis)-2-fluorocyclopropanecarbonyl]amino]-2,7-naphthyridin-3-yl]-3-methyl-benzamide (35 mg, 37% yield) as a white solid. LCMS (ESI): R$_T$ (min)=1.086, [M+H]$^+$=380.2, method=B; $^1$H NMR (400 MHz, DMSO-d$_6$) δ: 10.99 (s, 1H), 9.37 (s, 1H), 8.24 (s, 1H), 7.97 (s, 1H), 7.79 (s, 1H), 7.75 (d, J=8.0 Hz, 1H), 7.48 (d, J=8.0 Hz, 1H), 7.35 (br, 1H), 7.28 (br, 2H), 6.92 (s, 1H), 5.07-4.83 (m, 1H), 2.41 (s, 3H), 2.32-2.22 (m, 1H), 1.74-1.61 (m, 1H), 1.24-1.14 (m 1H).

Example 48

4-(1-amino-6-((cis)-2-fluorocyclopropanecarboxamido)-2,7-naphthyridin-3-yl)-N,3-dimethylbenzamide (Compound 49)

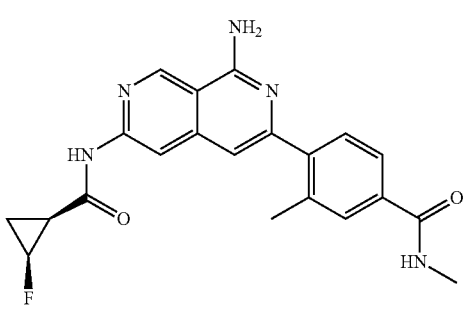 [SMILES: CNC(=O)c1ccc(-c2cc3cc(NC(=O)[C@@H]4C[C@@H]4F)ncc3c(N)n2)c(C)c1]

Step 1: 4-bromo-N,3-dimethylbenzamide

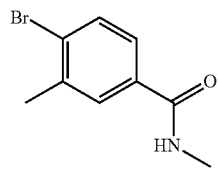

To a vial was added 4-bromo-3-methylbenzoic acid (1.0 g, 4.65 mmol), dichloromethane (10 mL) and DMF (0.1 mL, 4.65 mmol). Oxalyl chloride (1.2 mL, 13.95 mmol) was added drop-wise. The mixture was stirred at room temperature for 2 hours. The reaction was concentrated in vacuo and re-dissolved in dichloromethane (10 mL). Methylamine (30% in ethanol, 10 mL) was added and stirred at room temperature for 30 minutes. The mixture was concentrated in vacuo. The residue was purified by silica gel chromatography (petroleum ether/ethyl acetate, 1:1 to 0:100) to get 4-bromo-N,3-dimethyl-benzamide (1 g, 94% yield) as a white solid. LCMS (ESI) [M+H]$^+$=228.0.

Step 2. N,3-dimethyl-4-(4,4,5,5-tetramethyl-1,3,2-dioxaborolan-2-yl)benzamide

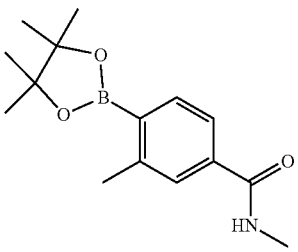

To a sealed tube was added 4-bromo-N,3-dimethyl-benzamide (0.99 g, 4.34 mmol), bis(pinacolato)diboron (1.32 g, 5.21 mmol), potassium acetate (1.28 g, 13 mmol) and Pd(dppf)Cl$_2$ (317 mg, 0.43 mmol) and 1,4-dioxane (100 mL). The mixture was degassed by bubbling through with N₂ for 2 minutes and stirred at 100° C. for 3 hours. The mixture was concentrated and purified by silica gel chromatography (petroleum ether/ethyl acetate, 3:1 to 1:1) to get N,3-dimethyl-4-(4,4,5,5-tetramethyl-1,3,2-dioxaborolan-2-yl)benzamide (1.05 g, 77% yield) as an off-white solid. LCMS (ESI) [M+H]⁺=276.2.

Step 3: (±)-4-(1-amino-6-((cis)-2-fluorocyclopropanecarboxamido)-2,7-naphthyridin-3-yl)-N,3-dimethylbenzamide

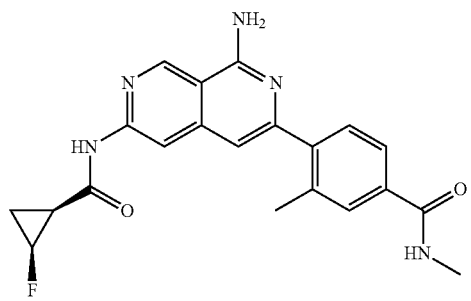 [SMILES: CNC(=O)c1ccc(-c2cc3cc(NC(=O)[C@@H]4C[C@@H]4F)ncc3c(N)n2)c(C)c1]

To a vial was added (±)-cis-N-(8-amino-6-chloro-2,7-naphthyridin-3-yl)-2-fluoro-cyclopropanecarboxamide (70 mg, 0.25 mmol), K₂CO₃ (50 mg, 0.51 mmol), Pd(dppf)Cl₂ (40 mg, 0.05 mmol), N,3-dimethyl-4-(4,4,5,5-tetramethyl-1,3,2-dioxaborolan-2-yl)benzamide (150 mg, 0.55 mmol), water (0.5 mL) and 1,4-dioxane (5 mL). The mixture was degassed by bubbling through with N₂ for 2 minutes and then stirred at 100° C. for 2 hours. The mixture was concentrated and purified by silica gel chromatography (dichloromethane/methanol, 100:1 to 10:1) and reverse phase chromatography (Boston 40 g ODS column, eluted with NaHCO₃ 10 mmol/L:acetonitrile from 2:1 to 1:2) to give 4-[1-amino-6-[[cis-2-fluorocyclopropanecarbonyl]amino]-2,7-naphthyridin-3-yl]-N,3-dimethyl-benzamide (35 mg, 35% yield) as white solid. LCMS (ESI): R$_T$ (min)=1.124, [M+H]⁺=394.1, method=B; ¹H NMR (400 MHz, DMSO-d₆) δ: 10.99 (s, 1H), 9.37 (s, 1H), 8.44 (q, J=4.4 Hz, 1H), 8.23 (s, 1H), 7.75 (s, 1H), 7.71 (d, J=8.0 Hz, 1H), 7.48 (d, J=8.0 Hz, 1H), 7.28 (br, 2H), 6.92 (s, 1H), 5.06-4.83 (m, 1H), 2.80 (d, J=4.4 Hz, 3H), 2.41 (s, 3H), 2.32-2.22 (m, 1H), 1.73-1.60 (m, 1H), 1.24-1.15 (m, 1H).

Example 49 trans-N-(8-amino-6-(4-isopropylpyridin-3-yl)-2,7-naphthyridin-3-yl)-2-cyanocyclopropanecarboxamide (Compound 50)

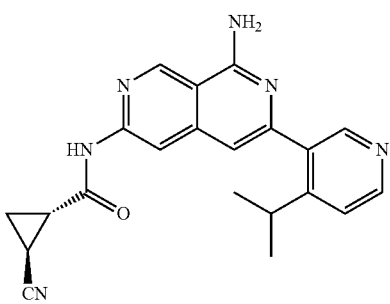 [SMILES: CC(C)c1ccncc1-c1cc2cc(NC(=O)[C@H]3C[C@@H]3C#N)ncc2c(N)n1]

Step 1: 3-bromo-4-isopropylpyridine

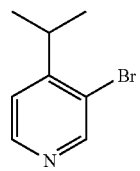

To a flask was added 3-bromopyridine (3.0 g, 18.99 mmol) and boron trifluoride diethyl etherate (3 mL, 23.55 mmol) was added dropwise. After stirring at room temperature for 30 min under N₂, the mixture was cooled to −55° C. and chloro(isopropyl)magnesium chlorolithium complex (18 mL, 23.4 mmol) was added dropwise. The mixture was stirred at −55° C. for 2 hours. The reaction was allowed to warm to room temperature and stirred at room temperature for 2 hours. The reaction was quenched with aqueous NaHCO₃ (10 mL), water (20 mL) added, extracted with ethyl acetate (50 mL×3), dried over Na₂SO₄, filtered and concentrated in vacuo. The residue was purified by silica gel chromatography (petroleum ether/ethyl acetate, 10:1 to 3:1) to get 3-bromo-4-isopropyl-pyridine (600 mg, 16% yield) as pale-yellow oil. LCMS (ESI) [M+H]⁺=200.0.

Step 2: 4-isopropylpyridin-3-ylboronic acid

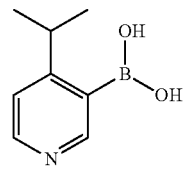

To a vial was added triisopropyl borate (1.2 g, 6.38 mmol), 3-bromo-4-isopropyl-pyridine (600 mg, 3 mmol) and THF (20 mL). The mixture was cooled to −78° C. A solution of n-BuLi (1.5 mL, 3.75 mmol, 2.5 M in hexane) was added dropwise. The mixture was allowed to warm to room temperature slowly, and stirred at room temperature for 2 hours. The mixture was quenched by water (10 mL), washed with ethyl acetate (20 mL×2), acidified to pH=5 with 2N HCl, and concentrated in vacuo. The residue was extracted with ethanol (30 mL), filtered and concentrated in vacuo to give (4-isopropyl-3-pyridyl)boronic acid (600 mg, 36% yield) as a pale-yellow solid, and used for the next step directly. LCMS (ESI) [M+H]⁺=166.1.

Step 3: (±)-trans-N-(8-amino-6-(4-isopropylpyridin-3-yl)-2,7-naphthyridin-3-yl)-2-cyanocyclopropanecarboxamide

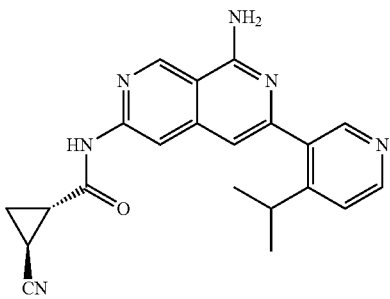 [SMILES: CC(C)c1ccncc1-c1cc2cc(NC(=O)[C@H]3C[C@@H]3C#N)ncc2c(N)n1]

To a vial was added (±)-trans-N-(8-amino-6-chloro-2,7-naphthyridin-3-yl)-2-cyano-cyclopropanecarboxamide (120 mg, 0.42 mmol), X-phos (40 mg, 0.08 mmol), XPhos Pd G2 (49 mg, 0.06 mmol), (4-isopropyl-3-pyridyl)boronic acid (70 mg, 0.42 mmol), water (1 mL) and 1,4-dioxane (10 mL). The reaction was degassed by bubbling with nitrogen for 2 min and then stirred at 100° C. for 6 hours. The mixture was concentrated and purified by silica gel chromatography (dichloromethane/methanol, 100:1 to 10:1) to give (±)-trans-N-[8-amino-6-(4-isopropyl-3-pyridyl)-2,7-naphthyridin-3-yl]-2-cyano-cyclopropanecarboxamide (17 mg, 11% yield) as a pale-yellow solid. LCMS (ESI): $R_T$ (min)=1.696, [M+H]$^+$=373.2, method=F; $^1$H NMR (400 MHz, CD$_3$OD) δ: 9.30 (s, 1H), 8.50 (d, J=5.6 Hz, 1H), 8.44 (s, 1H), 8.28 (s, 1H), 7.49 (d, J=5.6 Hz, 1H), 6.91 (s, 1H), 3.40-3.20 (m, 1H), 2.70-2.60 (m, 1H), 2.15-2.05 (m, 1H), 1.65-1.50 (m, 2H), 1.22 (d, J=6.8 Hz, 6H).

Example 50

(±)-trans-N-(8-amino-6-(4-methylpyridin-3-yl)-2,7-naphthyridin-3-yl)-2-fluorocyclopropanecarboxamide (Compound 51)

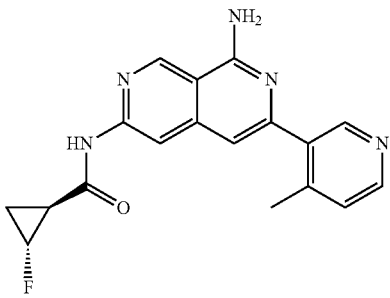 [SMILES: Cc1ccncc1-c1cc2cc(NC(=O)[C@@H]3C[C@H]3F)ncc2c(N)n1]

A mixture of (±)-trans-N-(8-amino-6-chloro-2,7-naphthyridin-3-yl)-2-fluoro-cyclopropane carboxamide (500 mg, 1.78 mmol), 4-methyl-3-(4,4,5,5-tetramethyl-1,3,2-dioxaborolan-2-yl)pyridine (450 mg, 2.05 mmol), X-Phos (90 mg, 0.19 mmol), X-Phos-Pd-G2 (90 mg, 0.11 mmol), K$_2$CO$_3$ (800 mg, 5.8 mmol) in 1,4-dioxane (6 mL) and water (1 mL) was stirred under inert Ar atmosphere at 110° C. for 2 hours. The reaction was concentrated and the resulting residue was purified by reverse phase chromatography (methyl alcohol 45-55/0.05% formic acid in water) to afford (±)-trans-N-[8-amino-6-(4-methyl-3-pyridyl)-2, 7-naphthyridin-3-yl]-2-fluoro-cyclopropanecarboxamide (57 mg, 9.5% yield) as a white solid. LCMS (ESI): $R_T$ (min)=1.440, [M+H]$^+$=338.1, method=E; $^1$H NMR (400 MHz, DMSO-d$_6$) δ 11.13 (s, 1H), 9.39 (s, 1H), 8.56 (s, 1H), 8.43 (d, J=4.8 Hz, 1H), 8.19 (s, 1H), 7.34 (s, 2H), 7.30 (d, J=5.2 Hz, 1H), 6.97 (s, 1H), 5.00-4.83 (m, 1H), 2.66-2.57 (m, 1H), 2.41 (s, 3H), 1.60-1.51 (m, 1H), 1.31-1.23 (m, 1H).

Example 51

(±)-cis-N-(8-amino-6-(7-methyl-1H-imidazo[4,5-b]pyridin-6-yl)-2,7-naphthyridin-3-yl)-2-fluorocyclopropanecarboxamide (Compound 52)

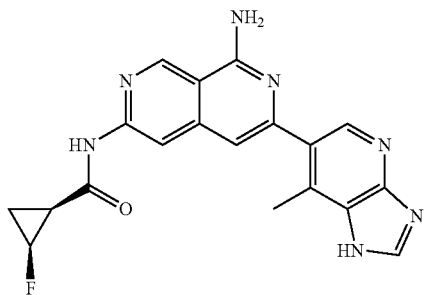 [SMILES: Cc1c(-c2cc3cc(NC(=O)[C@@H]4C[C@@H]4F)ncc3c(N)n2)cnc2nc[nH]c12]

Step 1: 7-methyl-6-(4, 4, 5, 5-tetramethyl-1,3,2-dioxaborolan-2-yl)-3H-imidazo[4,5-b]pyridine

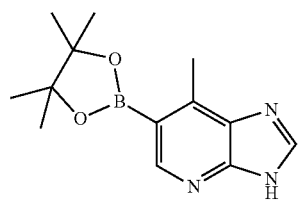 [SMILES: Cc1c(B2OC(C)(C)C(C)(C)O2)cnc2[nH]cnc12]

A mixture of 6-bromo-7-methyl-3H-imidazo[4,5-b]pyridine (320 mg, 1.51 mmol), Pd(dppf)Cl$_2$ (100 mg, 0.14 mmol), potassium acetate (600 mg, 6.12 mmol), and bis(pinacolato)diboron (3.8 g, 14.96 mmol) in DMF (10 mL) was stirred under a nitrogen atmosphere at 100° C. for 3 hours. To this brine (40 mL) was added and the mixture extracted with ethyl acetate (20 mL×3). The combined organic layers were dried with MgSO$_4$ and concentrated to dryness. The crude product was purified by column chromatography on silica gel eluting with ethyl acetate to afford 7-methyl-6-(4,4,5,5-tetramethyl-1,3,2-dioxaborolan-2-yl)-3H-imidazo[4,5-b]pyridine (180 mg, 35% yield) as a white solid. LCMS (ESI): [M+H]$^+$=260.2.

Step 2: (±)-cis-N-(8-amino-6-(7-methyl-1H-imidazo[4,5-b]pyridin-6-yl)-2,7-naphthyridin-3-yl)-2-fluorocyclopropanecarboxamide Step 1: (±)-trans-ethyl 2-(methoxymethyl)cyclopropanecarboxylate

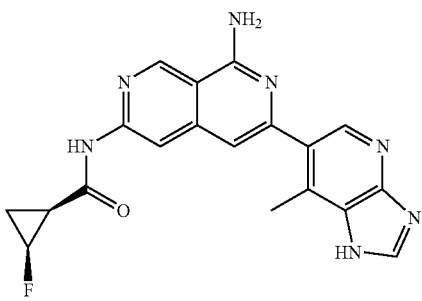 [SMILES: Cc1c(-c2cc3cc(NC(=O)[C@@H]4C[C@@H]4F)ncc3c(N)n2)cnc2nc[nH]c12]

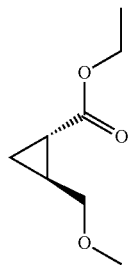

To a solution of (±)-trans-ethyl 2-(hydroxymethyl) cyclopropanecarboxylate (1.4 g, 9.71 mmol) in THF (10 mL) was added sodium hydride (60% in mine oil, 350 mg, 8.75 mmol) at room temperature. The reaction mixture was stirred at room temperature for 20 minutes. Then iodomethane (1.0 mL, 15.5 mmol) was added. The reaction mixture was stirred at room temperature for 3 h and monitored by LCMS. The reaction was quenched with a saturated NaCl solution. The reaction mixture was extracted with ethyl acetate (30 mL×3), dried over anhydrous sodium sulfate, and concentrated in vacuo to afford trans-ethyl 2-(methoxymethyl)cyclopropanecarboxylate (1.0 g, 91% yield) as a yellow liquid. LCMS: (ESI) [M+H]$^+$=159.1.

A mixture of 7-methyl-6-(4,4,5,5-tetramethyl-1,3,2-dioxaborolan-2-yl)-3H-imidazo[4,5-b]pyridine (60 mg, 0.23 mmol), (±)-cis-N-(8-amino-6-chloro-2,7-naphthyridin-3-yl)-2-fluorocyclopropanecarboxamide (60 mg, 0.21 mmol), Pd(dppf)Cl$_2$ (15 mg, 0.02 mmol), K$_2$CO$_3$ (100 mg, 0.72 mmol) in 1,4-dioxane (5 mL) and water (1 mL) was stirred under an Ar atmosphere at 110° C. for 3 hours. The reaction was concentrated to dryness. The resulting residue was purified by reverse phase chromatography (acetonitrile 0-45/0.1% NH$_4$HCO$_3$ in water) to afford (±)-cis-N-[8-amino-6-(7-methyl-1H-imidazo[4,5-b] pyridin-6-yl)-2,7-naphthyridin-3-yl]-2-fluoro-cyclopropanecarboxamide (10.6 mg, 13.1% yield) as a white solid. LCMS: (ESI): R$_T$(min)=1.03, [M+H]$^+$=378.1, method=B; $^1$H NMR (400 MHz, CD$_3$OD) δ 9.31 (s, 1H), 8.48 (s, 1H), 8.44 (s, 1H), 8.34 (s, 1H), 7.05 (s, 1H), 5.00-4.80 (m, 1H), 2.71 (s, 3H), 2.20-2.16 (m, 1H), 1.88-1.81 (m, 1H), 1.26-1.21 (m, 1H).

Step 2: (±)-trans-2-(methoxymethyl)cyclopropanecarboxylic acid

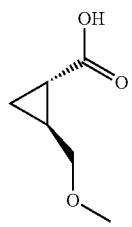

A mixture of (±)-trans-ethyl 2-(methoxymethyl)cyclopropanecarboxylate (1.0 g, 6.32 mmol), sodium hydroxide (800 mg, 20 mmol) in THF (20 mL) and water (5 mL) was stirred at 70° C. for 6 hours. THF was removed by rotary evaporation and the pH was adjusted to 1 with a 2 M HCl solution. The mixture was extracted with ethyl acetate (20×3 mL). The organic extracts were combined, dried over anhydrous sodium sulfate, and then concentrated in vacuo to afford (±)-trans-2-(methoxymethyl)cyclopropanecarboxylic acid (700 mg, 85% yield) as a colourless liquid.

Example 52

(±)-trans-N-(8-amino-6-(4-ethylpyridin-3-yl)-2,7-naphthyridin-3-yl)-2-(methoxymethyl) cyclopropane carboxamide (Compound 53)

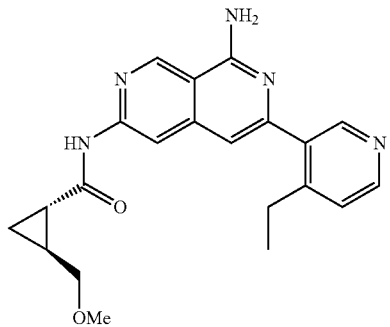 [SMILES: CCc1ccncc1-c1cc2cc(NC(=O)[C@H]3C[C@@H]3COC)ncc2c(N)n1]

Step 3: (±)-trans-N-(6,8-dichloro-2,7-naphthyridin-3-yl)-2-(methoxymethyl)cyclopropanecarboxamide

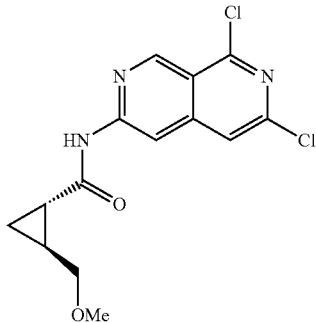 [SMILES: COC[C@H]1C[C@@H]1C(=O)Nc1cc2cc(Cl)nc(Cl)c2cn1]

To a solution of (±)-trans-2-(methoxymethyl)cyclopropanecarboxylic acid (700 mg, 5.38 mmol) and DMF (1 drop) in dichloromethane (20 mL) was added excess oxalyl chloride. The mixture was stirred at room temperature for 1 hour. The mixture was concentrated to remove excess oxalyl chloride and dichloromethane (10 mL) was added. The solution was added drop-wise to a solution of 6,8-dichloro-2,7-naphthyridin-3-amine (400 mg, 1.87 mmol), triethylamine (2.0 mL, 14.85 mmol) in dichloromethane (10 mL). The mixture was stirred at room temperature for 1 hour. The reaction mixture was then concentrated to afford the crude (±)-trans-N-(6,8-dichloro-2,7-naphthyridin-3-yl)-2-(methoxymethyl)cyclopropanecarboxamide (400 mg, 17.1% yield) as a yellow solid. LCMS (ESI): [M+H]⁺=326.0.

Step 4: (±)-trans-N-(8-amino-6-chloro-2,7-naphthyridin-3-yl)-2(methoxymethyl)cyclopropanecarboxamide

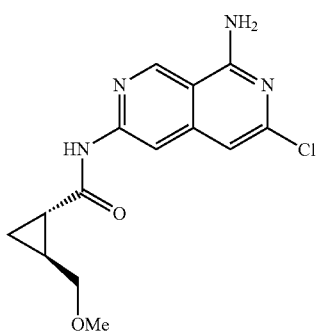 [SMILES: COC[C@H]1C[C@@H]1C(=O)Nc1cc2cc(Cl)nc(N)c2cn1]

A mixture of (±)-trans-N-(6, 8-dichloro-2, 7-naphthyridin-3-yl)-2-(methoxymethyl)cyclopropanecarboxamide (400.0 mg, 0.3200 mmol), and ammonia (25% in water) (2.0 mL, 105.88 mmol) in 1,4-dioxane (4 mL) was stirred at 110° C. for 2 hours. The reaction was concentrated to dryness. The crude product was then purified by column chromatography on silica gel eluting with dichloromethane/methanol (10:1) to afford N-(8-amino-6-chloro-2,7-naphthyridin-3-yl)-2-(methoxymethyl)cyclopropanecarboxamide (90 mg, 71% yield) as a yellow solid. LCMS (ESI): [M+H]⁺=307.1.

Step 5: (±)-trans-N-(8-amino-6-(4-ethylpyridin-3-yl)-2,7-naphthyridin-3-yl)-2-(methoxymethyl) cyclo propane carboxamide

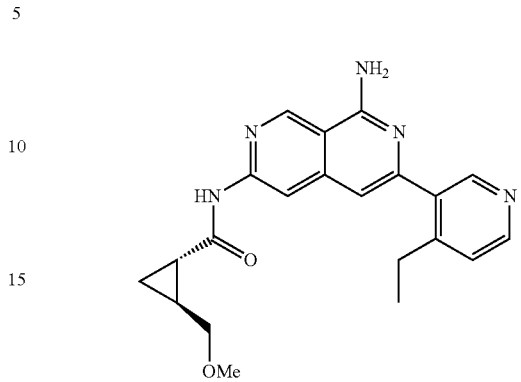

To a pressure reaction tube was added (±)-trans-N-(8-amino-6-chloro-2,7-naphthyridin-3-yl)-2-(methoxymethyl) cyclopropanecarboxamide (84 mg, 0.27 mmol), (4-ethyl-3-pyridyl)boronic acid (60 mg, 0.4 mmol), Pd(PPh$_3$)$_4$ (40 mg, 0.03 mmol), K$_2$CO$_3$ (120 mg, 0.87 mmol), 1,4-dioxane (5 mL) and water (1 mL). The reaction mixture was stirred under an Ar atmosphere at 110° C. for 6 hours and then concentrated to dryness. The resulting residue was purified by reverse phase chromatography (acetonitrile 0-40/0.1% NH$_4$HCO$_3$ in water) to afford (±)-trans-N-[8-amino-6-(4-ethyl-3-pyridyl)-2,7-naphthyridin-3-yl]-2-(methoxymethyl) cyclopropanecarboxamide (12 mg, 11.6% yield) as a white solid. LCMS (ESI): R$_T$ (min)=1.16, [M+H]⁺=378.2, method=B; ¹H NMR (400 MHz, CD$_3$OD) δ 9.18 (s, 1H), 8.38 (s, 1H), 8.36 (s, 1H), 8.17 (s, 1H), 7.32 (d, J=4.0 Hz, 1H), 6.83 (s, 1H), 3.42-3.39 (m, 1H), 3.22-3.18 (m, 4H), 2.72 (q, J=6.0 Hz, 2H), 1.80-1.79 (m, 1H), 1.64-1.60 (m, 1H), 1.17-1.13 (m, 1H), 1.06 (t, J=6.0 Hz, 3H), 0.86-0.82 (m, 1H).

Example 53

(±)-cis-N-(8-amino-6-(2-(2-hydroxyethyl)pyrrolidin-1-yl)-2,7-naphthyridin-3-yl)-2-fluorocyclopropanecarboxamide (Compound 54)

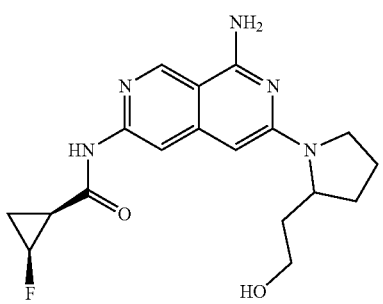 [SMILES: Nc1nc(N2CCCC2CCO)cc2cc(NC(=O)[C@@H]3C[C@@H]3F)ncc12]

501

Step 1: (±)-2-(1-(6-amino-1-(bis(4-methoxybenzyl)amino)-2,7-naphthyridin-3-yl)pyrrolidin-2-yl)ethanol

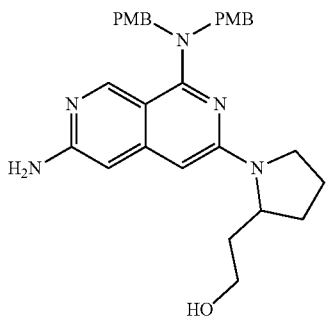

To a microwave tube was added 3-chloro-N1,N1-bis[(4-methoxyphenyl)methyl]-2,7-naphthyridine-1,6-diamine (200 mg, 0.46 mmol), (±)-2-pyrrolidin-2-ylethanol (450 mg, 3.91 mmol), and 1-methyl-2-pyrrolidinone (3 mL). The mixture was heated at 200° C. in a microwave reactor for 4 hours. The mixture was poured into water 20 mL and extracted with ethyl acetate (30 ml×2). The combined extracts were washed with 1 N HCl (10 mL), brine (20 ml×2), dried over Na$_2$SO$_4$, filtered and concentrated. The residue was purified by silica gel chromatography (dichloromethane/methanol/NH$_3$-water, 100:5:1) to give 2-[1-[6-amino-1-[bis[(4-methoxyphenyl)methyl]amino]-2,7-naphthyridin-3-yl]pyrrolidin-2-yl]ethanol (140 mg, 56% yield) as a pale-yellow solid. LCMS (ESI) [M+H]$^+$=514.2.

Step 2: (±)-2-[1-[6-[bis[cis-2-fluorocyclopropanecarbonyl]amino]-1-[bis[(4-methoxyphenyl)methyl]amino]-2,7-naphthyridin-3-yl]pyrrolidin-2-yl]ethyl cis-2-fluorocyclopropanecarboxylate

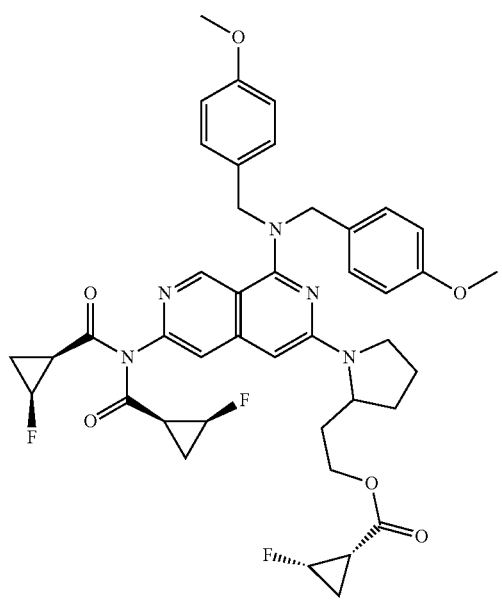 [SMILES: COc1ccc(CN(Cc2ccc(OC)cc2)c2nc(N3CCCC3CCOC(=O)[C@@H]3C[C@@H]3F)cc3cc(N(C(=O)[C@@H]4C[C@@H]4F)C(=O)[C@@H]4C[C@@H]4F)ncc23)cc1]

To a vial was added 2-[1-[6-amino-1-[bis[(4-methoxyphenyl)methyl]amino]-2,7-naphthyridin-3-yl]pyrrolidin-2-yl]ethanol (140 mg, 0.27 mmol), dichloromethane (5 mL) and pyridine (215 mg, 2.73 mmol). A solution of 2-[1-[6-amino-1-[bis[(4-methoxyphenyl)methyl]amino]-2,7-naphthyridin-3-yl]pyrrolidin-2-yl]ethanol (140 mg, 0.27 mmol) in dichloromethane (5 mL) was added dropwise. The mixture was stirred at room temperature for 2 hours. The mixture was concentrated in vacuo to get a crude product that was used directly for in next step. LCMS (ESI) [M+H]$^+$=772.2.

Step 3: (±)-cis-N-(8-(bis(4-methoxybenzyl)amino)-6-(2-(2-hydroxyethyl)pyrrolidin-1-yl)-2,7-naphthyridin-3-yl)-2-fluorocyclopropanecarboxamide

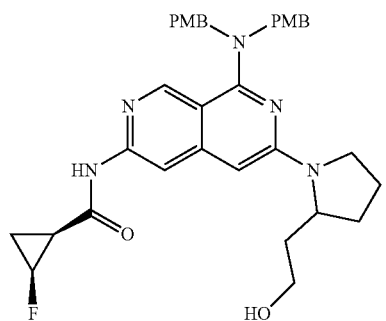

To a microwave tube was added 2-[I-[6-[bis[cis-2-fluorocyclopropanecarbonyl]amino]-1-[bis[(4-methoxyphenyl)methyl]amino]-2,7-naphthyridin-3-yl]pyrrolidin-2-yl]ethyl cis-2-fluorocyclopropanecarboxylate (300 mg, 0.27 mmol), 1,4-dioxane (4 mL), and ammonium hydroxide (3.6 mL, 47.62 mmol). The mixture was heated at 100° C. for 48 hours. The mixture was concentrated in vacuo, and purified by prep-TLC (silica-gel, dichloromethane/methanol, 10:1) to give (±)-cis-N-[8-[bis[(4-methoxyphenyl)methyl]amino]-6-[2-(2-hydroxyethyl)pyrrolidin-1-yl]-2,7-naphthyridin-3-yl]-2-fluoro-cyclopropanecarboxamide (180 mg, 55% yield) as a yellow oil. LCMS (ESI) [M+H]$^+$=600.3.

Step 4: (±)-cis-N-(8-amino-6-(2-(2-hydroxyethyl)pyrrolidin-1-yl)-2,7-naphthyridin-3-yl)-2-fluorocyclopropanecarboxamide

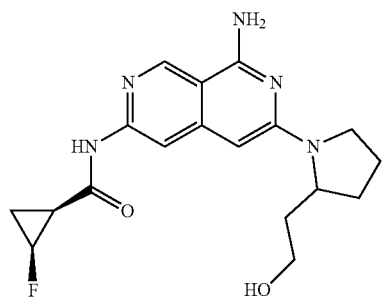 [SMILES: Nc1nc(N2CCCC2CCO)cc2cc(NC(=O)[C@@H]3C[C@@H]3F)ncc12]

To a vial was added (±)-cis-N-[8-[bis[(4-methoxyphenyl)methyl]amino]-6-[2-(2-hydroxyethyl)pyrrolidin-1-yl]-2,7-naphthyridin-3-yl]-2-fluoro-cyclopropanecarboxamide (180 mg, 0.15 mmol) and TFA (5 mL). The reaction was stirred at 90° C. for 16 hours. The mixture was concentrated and dissolved in a solution of NH$_3$ (7N in methanol, 10 mL).

K₂CO₃ (200 mg) was added. The reaction was stirred at 60° C. for 30 minutes, filtered and concentrated in vacuo. The residue was purified by prep-TLC (silica-gel, dichloromethane/methanol=10:1) to give (±)-cis-N-[8-amino-6-[2-(2-hydroxyethyl)pyrrolidin-1-yl]-2,7-naphthyridin-3-yl]-2-fluoro-cyclopropanecarboxamide (35 mg, 65% yield) as a yellow solid. LCMS (ESI): $R_T$(min)=1.100, [M+H]⁺=360.2, method=B; ¹H NMR (400 MHz, CD₃OD) δ: 8.80 (s, 1H), 7.84 (s, 1H), 5.75 (s, 1H), 4.96-4.73 (m, 1H), 4.45-4.35 (m, 1H), 3.65-3.55 (m, 2H), 3.53-3.45 (m, 1H), 3.39-3.31 (m, 1H), 2.16-1.93 (m, 4H), 1.93-1.73 (m, 3H), 1.70-1.58 (m, 1H), 1.24-1.12 (m, 1H).

Example 54 cis-N-(8-amino-6-(2-methoxy-5-methylpyridin-4-yl)-2,7-naphthyridin-3-yl)-2-fluorocyclopropanecarboxamide (Compound 55)

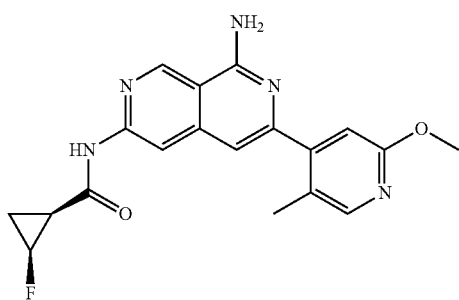

Step 1: 4-iodo-2-methoxy-5-methylpyridine

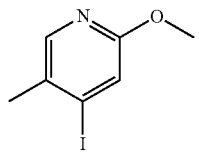

A mixture of 2-fluoro-4-iodo-5-methylpyridine (2.37 g, 10 mmol), sodium methoxide (1.0 g, 18.51 mmol) in dimethyl sulfoxide (10 mL) was stirred at room temperature for 2 hours. To this mixture was added saturated NaCl solution (20 mL) and then the mixture was extracted with ethyl acetate (15 mL×3). The organic extracts were combined, dried with MgSO₄, and concentrated to get the crude product. The crude product was purified by column chromatography on silica gel eluting with petroleum ether:ethyl acetate (10:1) to afford 4-iodo-2-methoxy-5-methyl-pyridine (2.3 g, 81% yield) as a colorless solid. LCMS (ESI): [M+H]⁺=249.9.

Step 2: 2-methoxy-5-methyl-4-(4,4,5,5-tetramethyl-1,3,2-dioxaborolan-2-yl)pyridine

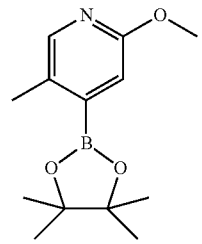

A mixture of 4-iodo-2-methoxy-5-methyl-pyridine (830 mg, 3.33 mmol), Pd(dppf)Cl₂ (200 mg, 0.27 mmol), potassium acetate (1.0 g, 10.2 mmol), and bis(pinacolato) diboron (6.0 g, 23.63 mmol) in anhydrous 1,4-dioxane (30 mL) was stirred under Ar at 100° C. for 5 hours. The reaction was concentrated to dryness. The crude product was purified by column chromatography on silica gel eluting with petroleum ether:ethyl acetate (10:1) to afford crude 2-methoxy-5-methyl-4-(4,4,5,5-tetramethyl-1,3,2-dioxaborolan-2-yl) pyridine (1.1 g) as a yellow liquid. LCMS (ESI): [M+H]⁺=250.1.

Step 3: (±)-cis-N-(8-amino-6-(2-methoxy-5-methylpyridin-4-yl)-2,7-naphthyridin-3-yl)-2-fluorocyclopropanecarboxamide

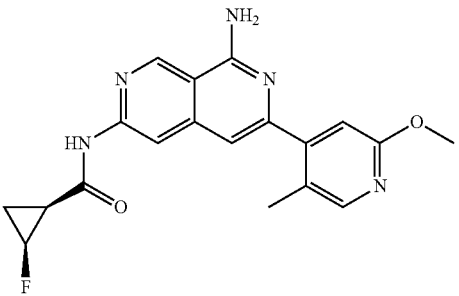 [SMILES: COc1cc(-c2cc3cc(NC(=O)[C@@H]4C[C@@H]4F)ncc3c(N)n2)c(C)cn1]

A mixture of 2-methoxy-5-methyl-4-(4,4,5,5-tetramethyl-1,3,2-dioxaborolan-2-yl)pyridine (600 mg, 2.41 mmol), (±)-cis-N-(8-amino-6-chloro-2,7-naphthyridin-3-yl)-2-fluoro-cyclopropanecarboxamide (280 mg, 1.0 mmol), Pd(dppf)Cl₂ (70 mg, 0.10 mmol), K₂CO₃ (420 mg, 3.04 mmol) in 1,4-dioxane (5 mL) and water (1 mL) was stirred under Ar at 110° C. for 3 hours. The reaction was concentrated to dryness. The resulting residue was purified by reverse phase chromatography (acetonitrile 0-45/0.1% NH₄HCO₃ in water) to afford (±)-cis-N-[8-amino-6-(2-methoxy-5-methyl-4-pyridyl)-2,7-naphthyridin-3-yl]-2-fluoro-cyclopropanecarboxamide (55 mg, 14.6% yield) as a white solid. LCMS (ESI): $R_T$ (min)=1.20, [M+H]⁺=368.2, method=B; ¹H NMR (400 MHz, DMSO-d₆) δ 11.02 (s, 1H), 9.38 (s, 1H), 8.25 (s, 1H), 8.05 (s, 1H), 7.34 (s, 2H), 6.98 (s, 1H), 6.85 (s, 1H), 5.04-4.86 (m, 1H), 3.85 (s, 3H), 2.30-2.23 (m, 4H), 1.70-1.64 (m, 1H), 1.22-1.17 (m, 1H).

Example 55

(±)-cis-N-[8-amino-6-(5-methyl-2-oxo-1H-pyridin-4-yl)-2,7-naphthyridin-3-yl]-2-fluoro-cyclopropanecarboxamide (Compound 56)

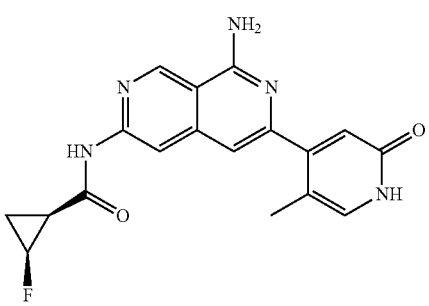 [SMILES: Cc1c[nH]c(=O)cc1-c1cc2cc(NC(=O)[C@@H]3C[C@@H]3F)ncc2c(N)n1]

To a solution of (±)-cis-N-[8-amino-6-(2-methoxy-5-methyl-4-pyridyl)-2,7-naphthyridin-3-yl]-2-fluoro-cyclopropanecarboxamide (45 mg, 0.12 mmol), iodotrimethylsilane (200 mg, 1.0 mmol) in acetonitrile (5 mL) was stirred at 80° C. for 2 hours. The reaction was concentrated and purified by reverse phase chromatography (acetonitrile 0-40/0.1% formic acid in water) to afford cis-N-[8-amino-6-(5-methyl-2-oxo-1H-pyridin-4-yl)-2,7-naphthyridin-3-yl]-2-fluoro-cyclopropanecarboxamide (13.3 mg, 30.7% yield) as a yellow solid, as the formic acid salt. LCMS (ESI): $R_T$ (min)=1.02, [M+H]$^+$=354.1, method=B; $^1$H NMR (400 MHz, CD$_3$OD) δ 9.30 (s, 1H), 8.34 (s, 1H), 7.35 (s, 1H), 6.98 (s, 1H), 6.63 (s, 1H), 5.00-4.79 (m, 1H), 2.19-2.16 (m, 1H), 2.114 (s, 3H), 1.87-1.80 (m, 1H), 1.28-1.19 (m, 1H).

Example 56

Benzyl 8-amino-6-(4-ethylpyridin-3-yl)-2,7-naphthyridin-3-ylcarbamate (Compound 57)

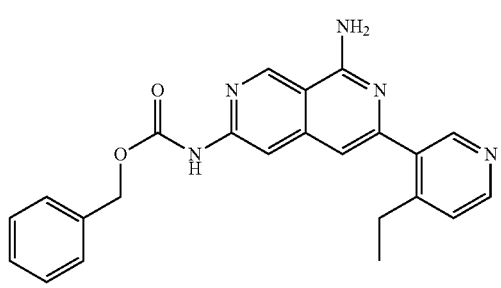 [SMILES: CCc1ccncc1-c1cc2cc(NC(=O)OCc3ccccc3)ncc2c(N)n1]

Step 1: Benzyl 6,8-dichloro-2,7-naphthyridin-3-ylcarbamate

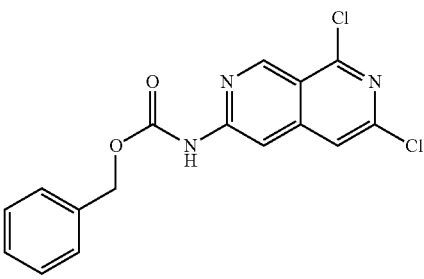 [SMILES: O=C(Nc1cc2cc(Cl)nc(Cl)c2cn1)OCc1ccccc1]

A mixture of 6,8-dichloro-2,7-naphthyridin-3-amine (100 mg, 0.47 mmol), benzyl chloroformate (1.0 mL, 7.33 mmol) and pyridine (1.0 mL, 12.36 mmol) in dichloromethane (10 mL) was stirred overnight at room temperature. The reaction was concentrated and the resulting residue was washed with water and filtered to afford benzyl N-(6,8-dichloro-2,7-naphthyridin-3-yl)carbamate (120 mg, 53% yield) as a yellow solid. LCMS (ESI): [M+H]$^+$=348.0.

Step 2: Benzyl 8-amino-6-chloro-2,7-naphthyridin-3-ylcarbamate

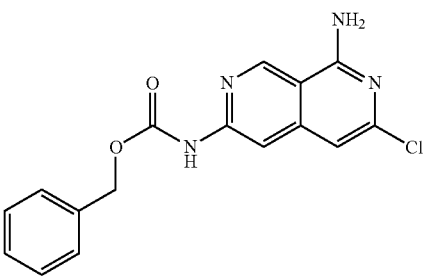 [SMILES: Nc1nc(Cl)cc2cc(NC(=O)OCc3ccccc3)ncc12]

A mixture of benzyl N-(6,8-dichloro-2,7-naphthyridin-3-yl)carbamate (120 mg, 0.34 mmol) and ammonia (25% in water, 2.0 mL, 105.88 mmol) in 1,4-dioxane (2 mL) was stirred at 110° C. for 2 hours. The reaction was concentrated to afford benzyl N-(8-amino-6-chloro-2,7-naphthyridin-3-yl)carbamate (110 mg, 89% yield) as a yellow solid. LCMS (ESI): [M+H]$^+$=329.1.

Step 3: Benzyl 8-amino-6-(4-ethylpyridin-3-yl)-2,7-naphthyridin-3-ylcarbamate

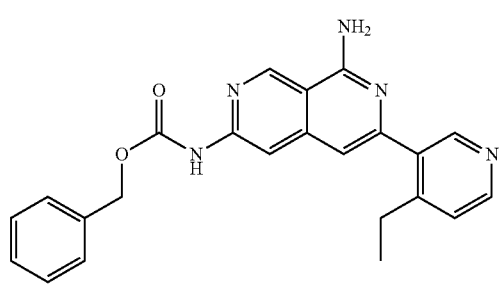 [SMILES: CCc1ccncc1-c1cc2cc(NC(=O)OCc3ccccc3)ncc2c(N)n1]

A mixture of benzyl N-(8-amino-6-chloro-2,7-naphthyridin-3-yl)carbamate (105 mg, 0.32 mmol), 4-ethyl-3-(4,4,5,5-tetramethyl-1,3,2-dioxaborolan-2-yl)pyridine (150 mg, 0.64 mmol), X-Phos (20 mg, 0.04 mmol), XPhos Pd G2 (20 mg, 0.03 mmol) and $K_2CO_3$ (150 mg, 1.09 mmol) in 1,4-dioxane (6 mL) and water (1 mL) was stirred under Ar at 110° C. for 2 hours. The reaction was concentrated and purified by reverse phase chromatography (methanol 45-55/0.05% formic acid in water) to afford benzyl N-[8-amino-6-(4-ethyl-3-pyridyl)-2,7-naphthyridin-3-yl]carbamate (9 mg, 7% yield) as a white solid (formic acid salt). LCMS (ESI): $R_T$ (min)=1.53, $[M+H]^+$=400.2, method=B; $^1$H NMR (400 MHz, $CD_3OD$) δ 9.26 (s, 1H), 8.48 (s, 1H), 8.50 (s, 1H), 8.10 (s, 1H), 7.48-7.34 (m, 6H), 6.97 (s, 1H), 5.27 (s, 2H), 2.83 (q, J=7.6 Hz, 2H), 1.19 (t, J=7.6 Hz, 3H).

Example 57

(±)-cis-N-(8-amino-6-(6-methyl-2-oxoindolin-5-yl)-2,7-naphthyridin-3-yl)-2-fluorocyclopropanecarboxamide (Compound 58)

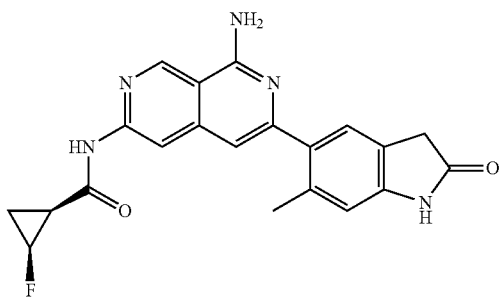 [SMILES: Cc1cc2c(cc1-c1cc3cc(NC(=O)[C@@H]4C[C@@H]4F)ncc3c(N)n1)CC(=O)N2]

Step 1: 5-bromo-6-methylindolin-2-one

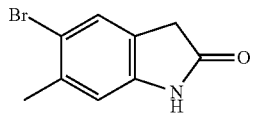

A mixture of 5-methyl-3H-1,3-benzoxazol-2-one (500 mg, 3.35 mmol) and 1-bromo-2,5-pyrrolidinedione (656 mg, 3.69 mmol) in acetic acid (10 mL) was stirred at 20° C. for 16 hours. The reaction mixture was diluted with water (25 mL) and stirred for further 15 minutes. The mixture was then filtered and washed with water (5 mL×2) to afford 6-bromo-5-methyl-3H-1,3-benzoxazol-2-one (600 mg, 77% yield) as a white solid. LCMS (ESI): $[M+H]^+$=228.2.

Step 2: 6-methyl-5-(4,4,5,5-tetramethyl-1,3,2-dioxaborolan-2-yl)indolin-2-one

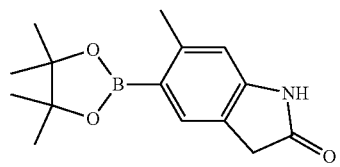 [SMILES: Cc1cc2c(cc1B1OC(C)(C)C(C)(C)O1)CC(=O)N2]

A mixture of 5-bromo-6-methyl-indolin-2-one (200 mg, 0.88 mmol), 4,4,4',4',5,5,5',5'-octamethyl-2,2'-bi(1,3,2-dioxaborolane) (336 mg, 1.33 mmol), Pd(dppf)Cl$_2$ (64 mg, 0.09 mmol), potassium acetate (86 mg, 0.88 mmol) and 1,4-dioxane (10 mL) was stirred at 100° C. under $N_2$ for 3 hours. The reaction mixture was concentrated and purified by silica gel chromatography eluting with 0-30% ethyl acetate in petroleum ether to give 6-methyl-5-(4,4,5,5-tetramethyl-1,3,2-dioxaborolan-2-yl)indolin-2-one (150 mg, 56% yield) as a yellow solid. LCMS (ESI): $[M+H]^+$=274.2.

Step 3: (±)-cis-N-(8-amino-6-(6-methyl-2-oxoindolin-5-yl)-2,7-naphthyridin-3-yl)-2-fluorocyclopropanecarboxamide

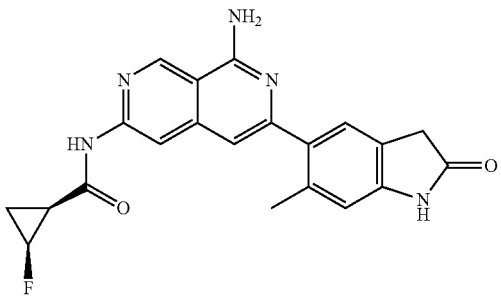 [SMILES: Cc1cc2c(cc1-c1cc3cc(NC(=O)[C@@H]4C[C@@H]4F)ncc3c(N)n1)CC(=O)N2]

A mixture of 6-methyl-5-(4,4,5,5-tetramethyl-1,3,2-dioxaborolan-2-yl)indolin-2-one (100 mg, 0.33 mmol), cis-N-(8-amino-6-chloro-2,7-naphthyridin-3-yl)-2-fluoro-cyclopropanecarboxamide (93 mg, 0.33 mmol), Pd(PPh$_3$)$_4$ (38 mg, 0.03 mmol), $K_2CO_3$ (91 mg, 0.67 mmol) in 1,4-dioxane (10 mL) and water (1 mL) was stirred at 105° C. under $N_2$ for 5 hours. The reaction mixture was concentrated and purified by silica gel chromatography eluting with 0-10% methanol in dichloromethane to give (±)-cis-N-[8-amino-6-(6-methyl-2-oxo-indolin-5-yl)-2,7-naphthyridin-3-yl]-2-fluoro-cyclopropanecarboxamide (20 mg 15% yield) as a white solid. LCMS (ESI): $R_T$ (min)=1.535, $[M+H]^+$=392.1, method=C; 1H NMR (400 MHz, DMSO-d$_6$) δ 10.95 (s, 1H), 10.42 (s, 1H), 9.33 (s, 1H), 8.19 (s, 1H), 7.28 (s, 1H), 7.20 (s, 2H), 6.82 (s, 1H), 6.70 (s, 1H), 5.05-4.83 (m, 1H), 3.46 (s 2H), 2.35 (s, 3H), 2.30-2.21 (m, 1H), 1.71-1.59 (m, 1H), 1.23-1.13 (m, 1H).

Example 58

(±)-cis-N-(8-amino-6-(6-(2-hydroxypropan-2-yl)-4-methylpyridin-3-yl)-2,7-naphthyridin-3-yl)-2-fluorocyclopropanecarboxamide (Compound 59)

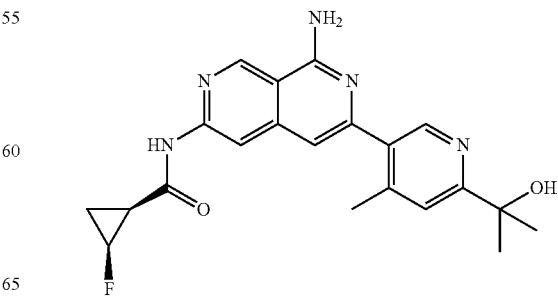

Step 1: 2-(5-bromo-4-methylpyridin-2-yl)propan-2-ol

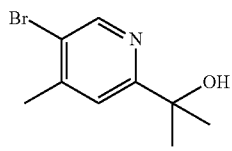

To a solution of 2,5-dibromo-4-methylpyridine (2 g, 7.97 mmol) in toluene (30 mL) was added a solution of n-BuLi (2.5 M in hexane, 4.8 mL, 11.96 mmol) at −78° C. under N$_2$. The mixture was stirred at −78° C. for 30 min. Acetone (1.85 g, 31.88 mmol) was added dropwise at −78° C. The mixture was stirred at 20° C. for 2 hours. The reaction mixture was washed with saturated NH$_4$Cl aqueous solution (100 mL) and the mixture was extracted with ethyl acetate (100 mL×3). The organic extracts were combined, concentrated under vacuum. The residue was purified by silica gel flash chromatography eluting with petroleum ether/ethyl acetate (20:1 to 3:1) to give 2-(5-bromo-4-methyl-2-pyridyl)propan-2-ol (1.5 g, 82% yield) as a white solid. LCMS (ESI): [M+H]$^+$=230.2.

Step 2: 2-(4-methyl-5-(4,4,5,5-tetramethyl-1,3,2-dioxaborolan-2-yl)pyridin-2-yl)propan-2-ol

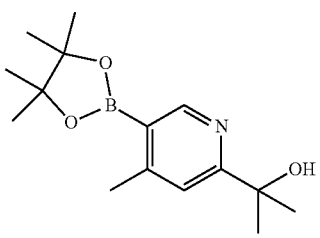 [SMILES: Cc1cc(C(C)(C)O)ncc1B1OC(C)(C)C(C)(C)O1]

To a pressure reaction tube was added 2-(5-bromo-4-methyl-2-pyridyl)propan-2-ol (200 mg, 0.87 mmol), bis(pinacolato)diboron (264 mg, 1.04 mmol), Pd(dppf)Cl$_2$ (63 mg, 0.09 mmol), potassium acetate (170 mg, 1.74 mmol), and 1,4-dioxane (8 mL). The mixture was stirred at 95° C. for 4 hours. The crude product was used in the next step without further purification. LCMS (ESI): [M+H]$^+$=278.2.

Step 3: (±)-cis-N-(8-amino-6-(6-methyl-2-oxoindolin-5-yl)-2,7-naphthyridin-3-yl)-2-fluorocyclopropanecarboxamide

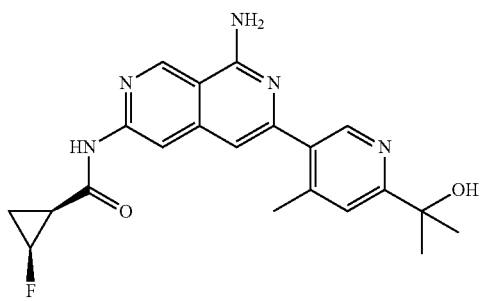 [SMILES: Cc1cc(C(C)(C)O)ncc1-c1cc2cc(NC(=O)[C@@H]3C[C@@H]3F)ncc2c(N)n1]

A mixture of 2-[4-methyl-5-(4,4,5,5-tetramethyl-1,3,2-dioxaborolan-2-yl)-2-pyridyl]propan-2-ol (100 mg, 0.36 mmol), Pd(t-Bu$_3$P)$_2$ (18 mg, 0.04 mmol), (±)-cis-N-(8-amino-6-chloro-2,7-naphthyridin-3-yl)-2-fluoro-cyclopropanecarboxamide (101 mg, 0.36 mmol) and K$_2$CO$_3$ (99 mg, 0.72 mmol) in 1,4-dioxane (10 mL) and water (1 mL) was stirred at 100° C. under nitrogen for 3 hours. The reaction mixture was concentrated and the residue was purified by silica gel chromatography eluting with 0-100% ethyl acetate in petroleum ether to give (±)-cis-N-[8-amino-6-[6-(1-hydroxy-1-methyl-ethyl)-4-methyl-3-pyridyl]-2,7-naphthyridin-3-yl]-2-fluoro-cyclopropanecarboxamide (61 mg, 43% yield) as a white solid. LCMS (ESI): R$_T$ (min)=1.309, [M+H]$^+$=396.1, method=A; $^1$H NMR (400 MHz, CD$_3$OD) δ 9.29 (s, 1H), 8.48 (s, 1H), 8.32 (s, 1H), 7.65 (s, 1H), 6.98 (s, 1H), 4.99-4.78 (m, 1H), 2.46 (s, 3H), 2.19-2.15 (m, 1H), 1.86-1.80 (m, 1H), 1.59 (s 6H), 1.26-1.20 (m, 1H).

Example 59 cis-N-(8-amino-6-(4-ethylpyridin-3-yl)-2,7-naphthyridin-3-yl)-2-cyanocyclopropanecarboxamide (Compound 60)

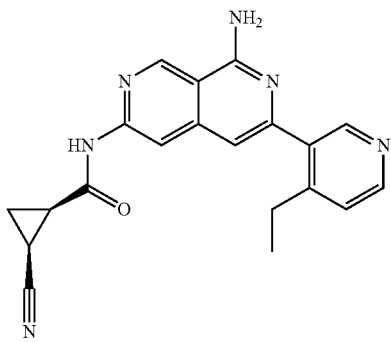 [SMILES: CCc1ccncc1-c1cc2cc(NC(=O)[C@@H]3C[C@@H]3C#N)ncc2c(N)n1]

Step 1: (±)-cis-N-(8-(bis(4-methoxybenzyl)amino)-6-(4-ethylpyridin-3-yl)-2,7-naphthyridin-3-yl)-2-cyanocyclopropanecarboxamide

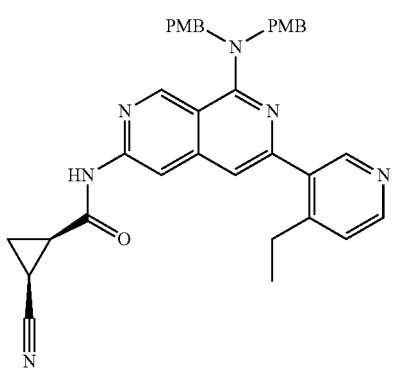

To a solution of (±)-cis-2-cyanocyclopropanecarboxylic acid (100 mg, 0.77 mmol) and DMF (0.01 mL) in dichloromethane (10 mL) was added ethanedioyl dichloride (0.09 mL, 0.93 mmol), the mixture was stirred at room temperature for 2 hours. The mixture was concentrated and the residue was added to a mixture of 3-(4-ethyl-3-pyridyl)-N1,N1-bis[(4-methoxyphenyl)methyl]-2,7-naphthyridine-1,6-diamine (390 mg, 0.77 mmol) and pyridine (2 mL) in dichloromethane (10 mL) at 0° C. drop-wise. The resulting mixture was stirred at room temperature for 2 hours, then diluted with dichloromethane (40 mL), and washed with water (10 mL×2). The combined organic layers were combined, concentrated and the residue purified by silica gel chromatography eluting with 0-100% ethyl acetate in petroleum ether to give (±)-trans-N-[8-[bis[(4-methoxyphenyl)methyl]amino]-6-(4-ethyl-3-pyridyl)-2,7-naphthyridin-3-yl]-2-cyano-cyclopropanecarboxamide (200 mg, 43% yield) as a brown solid. LCMS (ESI): [M+H]+=599.2.

Step 2: (±)-cis-N-(8-amino-6-(4-ethylpyridin-3-yl)-2,7-naphthyridin-3-yl)-2-cyanocyclopropanecarboxamide

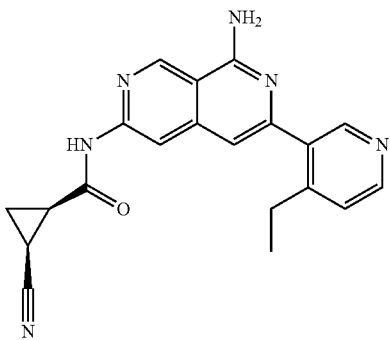 [SMILES: CCc1ccncc1-c1cc2cc(NC(=O)[C@@H]3C[C@@H]3C#N)ncc2c(N)n1]

A mixture of (±)-trans-N-[8-[bis[(4-methoxyphenyl)methyl]amino]-6-(4-ethyl-3-pyridyl)-2,7-naphthyridin-3-yl]-2-cyano-cyclopropanecarboxamide (200 mg, 0.33 mmol) and TFA (8 mL) was stirred at 80° C. for 1 hour. The mixture was concentrated and basified with NH₃ in methanol (7N). The residue was purified by silica gel chromatography eluting with 0-100% ethyl acetate in petroleum ether to give (±)-trans-N-[8-amino-6-(4-ethyl-3-pyridyl)-2,7-naphthyridin-3-yl]-2-cyano-cyclopropanecarboxamide (60 mg, 50% yield) as a white solid. LCMS (ESI): $R_T$ (min)=1.593, [M+H]⁺=359.1, method=C; ¹H NMR (400 MHz, CD₃OD) δ 9.32 (s, 1H), 8.50 (s, 1H), 8.48 (d, J=5.2 Hz, 1H), 8.37 (s, 1H), 7.44 (d, J=5.2 Hz, 1H), 7.00 (s, 1H), 2.83 (q, J=7.6 Hz, 2H), 2.56-2.50 (m, 1H), 2.18-2.12 (m, 1H), 1.71-1.67 (m, 1H), 1.55-1.50 (m, 1H), 1.19 (t, J=7.2 Hz, 3H).

Example 60

(±)-cis-N1-(8-amino-6-(4-ethylpyridin-3-yl)-2,7-naphthyridin-3-yl)cyclopropane-1,2-dicarboxamide (Compound 61)

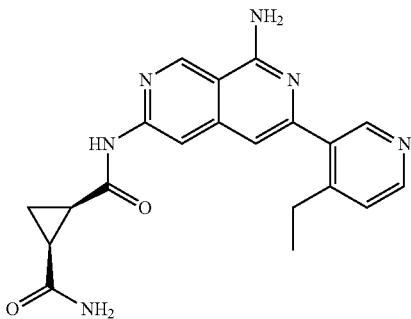 [SMILES: CCc1ccncc1-c1cc2cc(NC(=O)[C@@H]3C[C@@H]3C(N)=O)ncc2c(N)n1]

A mixture of (±)-cis-N-[8-[bis[(4-methoxyphenyl)methyl]amino]-6-(4-ethyl-3-pyridyl)-2,7-naphthyridin-3-yl]-2-cyano-cyclopropanecarboxamide (200 mg, 0.33 mmol) and TFA (8 mL) was stirred at 80° C. for 1 hour. The mixture was concentrated and basified with NH₃ in methanol (7N). The residue was purified by silica gel chromatography eluting with 0-100% ethyl acetate in petroleum ether to give (±)-cis-N1-(8-amino-6-(4-ethylpyridin-3-yl)-2,7-naphthyridin-3-yl)cyclopropane-1,2-dicarboxamide (23 mg, 18.4% yield) as a white solid. LCMS (ESI): RT (min)=1.449, [M+H]⁺=377.1, method=C; ¹H NMR (400 MHz, CD₃OD) δ 9.28 (s, 1H), 8.49 (s, 1H), 8.47 (d, J=5.2 Hz, 1H), 8.37 (s, 1H), 7.44 (d, J=5.2 Hz, 1H), 6.95 (s, 1H), 2.83 (q, J=7.6 Hz, 2H), 2.35-2.29 (m, 1H), 2.19-2.13 (m, 1H), 1.73-1.68 (m, 1H), 1.37-1.32 (m, 1H), 1.18 (t, J=7.2 Hz, 3H).

Example 61

(±)-cis-N-(8-amino-6-(2,4-dimethylpyridin-3-yl)-2,7-naphthyridin-3-yl)-2-fluorocyclopropanecarboxamide (Compound 62)

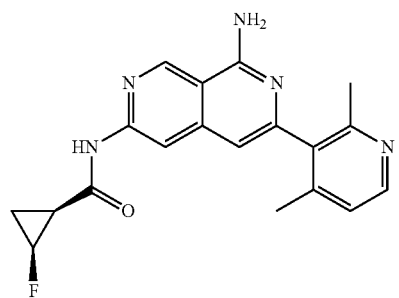 [SMILES: Cc1ccnc(C)c1-c1cc2cc(NC(=O)[C@@H]3C[C@@H]3F)ncc2c(N)n1]

513

Step 1: 2,4-dimethyl-3-(4,4,5,5-tetramethyl-1,3,2-dioxaborolan-2-yl)pyridine

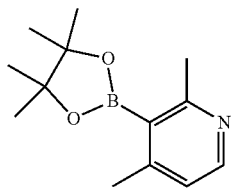 [SMILES: Cc1ccnc(C)c1B1OC(C)(C)C(C)(C)O1]

A mixture of 3-bromo-2,4-dimethyl-pyridine (500 mg, 2.69 mmol), 4,4,4',4',5,5,5',5'-octamethyl-2,2'-bi(1,3,2-dioxaborolane) (1023 mg, 4.03 mmol), Pd(dppf)Cl$_2$ (219 mg, 0.27 mmol), and potassium acetate (526 mg, 5.37 mmol) in 1,4-dioxane (15 mL) was stirred at 110° C. under N$_2$ for 5 hours. The mixture was used in the next step directly without any purification. LCMS (ESI): [M+H]$^+$=234.1.

Step 2: (±)-cis-N-(8-amino-6-(2,4-dimethylpyridin-3-yl)-2,7-naphthyridin-3-yl)-2-fluorocyclopropanecarboxamide

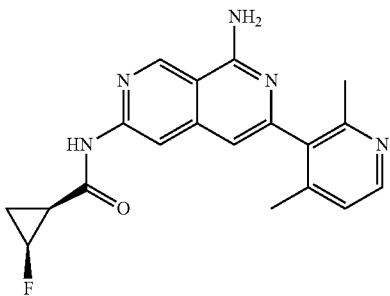 [SMILES: Cc1ccnc(C)c1-c1cc2cc(NC(=O)[C@@H]3C[C@@H]3F)ncc2c(N)n1]

A mixture of 2,4-dimethyl-3-(4,4,5,5-tetramethyl-1,3,2-dioxaborolan-2-yl)pyridine (100 mg, 0.43 mmol), (±)-cis-N-(8-amino-6-chloro-2,7-naphthyridin-3-yl)-2-fluoro-cyclopropanecarboxamide (120 mg, 0.43 mmol), Pd(PPh$_3$)$_4$ (49 mg, 0.04 mmol) and K$_2$CO$_3$ (118 mg, 0.86 mmol) in 1,4-dioxane (10 mL) containing water (1 mL) was stirred at 110° C. under N$_2$ for 5 hours. The reaction mixture was concentrated and the residue was purified by silica gel chromatography eluting with 0-15% methanol in dichloromethane to give (±)-cis-N-[8-amino-6-(2,4-dimethyl-3-pyridyl)-2,7-naphthyridin-3-yl]-2-fluoro-cyclopropanecarboxamide (25 mg, 16.6% yield) as a white solid. LCMS (ESI): RT (min)=1.556, [M+H]$^+$=352.1, method=C; $^1$H NMR (400 MHz, CD$_3$OD) δ 9.32 (s, 1H), 8.32 (d, J=5.2 Hz, 1H), 8.31 (s, 1H), 7.25 (d, J=5.2 Hz, 1H), 6.86 (s, 1H), 4.98-4.80 (m, 1H), 2.35 (s, 3H), 2.20 (s, 3H), 2.18-2.15 (m, 1H), 1.87-1.79 (m, 1H), 1.26-1.20 (m, 1H).

514

Example 62

(±)-cis-N-(8-amino-6-(1-methyl-1H-pyrrolo[3,2-c]pyridin-7-yl)-2,7-naphthyridin-3-yl)-2-fluorocyclopropanecarboxamide (Compound 63)

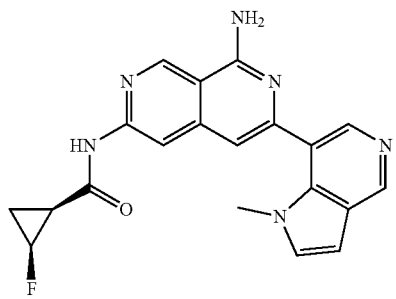 [SMILES: Cn1ccc2cncc(-c3cc4cc(NC(=O)[C@@H]5C[C@@H]5F)ncc4c(N)n3)c21]

Step 1: 7-bromo-1-methyl-1H-pyrrolo[3,2-c]pyridine

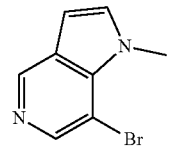

To a solution of 7-bromo-1H-pyrrolo[3,2-c]pyridine (700 mg, 3.55 mmol) in DMF (7 mL) was added sodium hydride (171 mg, 4.26 mmol). The resulting mixture was stirred for 0.5 hours at 25° C. Methyl iodide (656 mg, 4.62 mmol) was added and stirred for 1 hour. The reaction mixture was quenched with water (30 mL) and extracted with ethyl acetate (30 mL×2). The combined ethyl acetate layers were washed with water and brine, dried over Na$_2$SO$_4$, and concentrated in vacuo to give 7-bromo-1-methyl-pyrrolo[3,2-c]pyridine (640 mg, 81% yield) as a yellow solid. LCMS (ESI): [M+H]$^+$=211.0.

Step 2: 1-methyl-1H-pyrrolo[3,2-c]pyridin-7-ylboronic acid

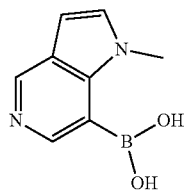

To a solution of 7-bromo-1-methyl-pyrrolo[3,2-c]pyridine (640 mg, 3.03 mmol) in THF (15 mL) was added n-BuLi (2.5 M in hexane) (1.8 mL, 4.55 mmol) at −78° C. The resulting mixture was stirred for 0.5 hour. Tri-isopropyl borate (855 mg, 4.55 mmol) was added and the reaction was slowly warmed to room temperature. The reaction mixture was quenched with water. The THF was removed in vacuo. The mixture was washed with ethyl acetate. The aqueous phase was adjusted to pH=5 with 1M HCl and filtered. The wet cake was washed with water and ethyl acetate and dried in vacuo to give (1-methylpyrrolo[3,2-c]pyridin-7-yl)boronic acid (520 mg, 97% yield) as a beige solid. LCMS (ESI): [M+H]$^+$=177.1.

Step 3: (±)-cis-N-(8-amino-6-(1-methyl-1H-pyrrolo[3,2-c]pyridin-7-yl)-2,7-naphthyridin-3-yl)-2-fluoro-cyclopropanecarboxamide

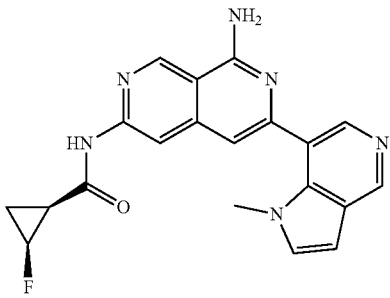 [SMILES: Cn1ccc2cncc(-c3cc4cc(NC(=O)[C@@H]5C[C@@H]5F)ncc4c(N)n3)c21]

A mixture of (±)-cis-N-(8-amino-6-chloro-2,7-naphthyridin-3-yl)-2-fluoro-cyclopropanecarboxamide (70 mg, 0.25 mmol), (1-methylpyrrolo[3,2-c]pyridin-7-yl)boronic acid (110 mg, 0.62 mmol), XPhos Pd G2 (10 mg, 0.01 mmol), X-phos (12 mg, 0.02 mmol) and potassium acetate (73 mg, 0.75 mmol) in 1,4-dioxane (2 mL) and water (0.2 mL) was stirred for 2 hours at 100° C. The reaction mixture was diluted with ethyl acetate (10 mL) and filtered. The filtrate was concentrated and the residue was purified by prep-TLC and reverse phase flash chromatography (ODS, acetonitrile/water+0.5% NH$_4$HCO$_3$, 0:1 to 1:1) to give (±)-cis-N-[8-amino-6-(1-methylpyrrolo[3,2-c]pyridin-7-yl)-2,7-naphthyridin-3-yl]-2-fluoro-cyclopropanecarboxamide (9 mg, 9.6% yield) as a yellow solid. LCMS (ESI): R$_T$ (min)=1.58, [M+H]$^+$=377.1, method=C; $^1$H NMR (400 MHz, CD$_3$OD): 9.28 (s, 1H), 8.84 (s, 1H), 8.35 (s, 1H), 8.25 (d, J=6.0 Hz, 1H), 7.55 (d, J=6.0 Hz, 1H), 7.32 (s, 1H), 7.06 (s, 1H), 4.99-4.82 (m, 1H), 4.07 (s, 3H), 2.20-2.16 (m, 1H), 1.88-1.81 (m, 1H), 1.27-1.23 (m, 1H).

Example 63

(±)-cis-N-[8-amino-6-(4-ethyl-1-methyl-6-oxo-3-pyridyl)-2,7-naphthyridin-3-yl]-2-fluoro-cyclopropanecarboxamide (Compound 64)

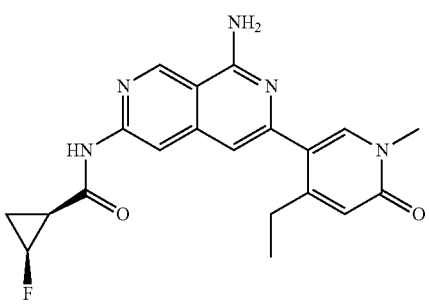 [SMILES: CCc1cc(=O)n(C)cc1-c1cc2cc(NC(=O)[C@@H]3C[C@@H]3F)ncc2c(N)n1]

Step 1: 5-bromo-4-ethyl-pyridin-2-amine

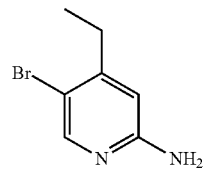

To a stirred solution of 2-amino-4-ethylpyridine (5.0 g, 40.9 mmol) in chloroform (200 mL) was added portionwise NBS (8.7 g, 48.9 mmol) at 0° C. over 15 minutes. After the reaction was complete, the mixture was directly purified by silica gel chromatography (ethyl acetate:petroleum ether=1:5 to 1:2) to give 5-bromo-4-ethyl-pyridin-2-amine (7 g, 72% yield) as a light yellow solid. LCMS (ESI): [M+H]$^+$=201.1.

Step 2: 5-bromo-4-ethyl-pyridin-2-ol

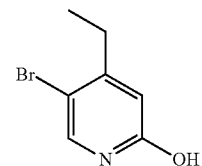

To a solution of 5-bromo-4-ethyl-pyridin-2-amine (7.0 g, 33.8 mmol) in concentrated hydrochloric acid (70 mL) at −20° C. was added portionwise an aqueous solution of NaNO$_2$ (4.8 g, 69.6 mmol) in water. After stirring for 1 hour, the reaction mixture was warmed to room temperature over a period of 3 hours. A 10 M aqueous NaOH solution (16 g of NaOH in 40 mL water) was added to adjust the pH to 12 while maintaining the temperature at 0° C. The reaction mixture was extracted with dichloromethane (3×25 mL). The combined extracts were then washed with water, dried and concentrated to afford 5-bromo-4-ethyl-pyridin-2-ol (2.0 g, 24% yield) as a white solid. LCMS (ESI): [M+H]$^+$=202.1.

Step 3: 5-bromo-4-ethyl-1-methyl-pyridin-2-one

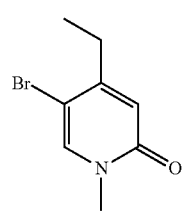

In a flask, K$_2$CO$_3$ (1.4 g, 10.1 mmol) and methyl iodide (1.1 g, 7.8 mmol) were added to a solution 5-bromo-4-ethyl-pyridin-2-ol (1.0 g, 4.9 mmol) in acetonitrile (20 mL). The reaction mixture was stirred at 25° C. overnight and then filtered. The filtrate was partitioned between H$_2$O (15 mL) and CH$_2$Cl$_2$ (2×10 mL). The combined organic layers were dried over Na$_2$SO$_4$ and concentrated. The residue was purified by silica gel chromatography (petroleum ether:ethyl acetate=9:1) to afford 5-bromo-4-ethyl-1-methyl-pyridin-2-one (754 mg, 71% yield) as a white solid. LCMS (ESI): [M+H]⁺=216.1.

Step 4: 4-ethyl-1-methyl-5-(4,4,5,5-tetramethyl-1,3,2-dioxaborolan-2-yl)pyridin-2-one

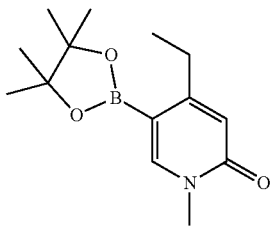 [SMILES: CCc1cc(=O)n(C)cc1B1OC(C)(C)C(C)(C)O1]

A solution of 5-bromo-4-ethyl-1-methyl-pyridin-2-one (700 mg, 3.2 mmol), bis(pinacolato)diboron (2060 mg, 8.1 mmol), Pd(dppf)Cl₂ (470 mg, 0.6 mmol) and potassium acetate (1270 mg, 13 mmol) in 1,4-dioxane (20 mL) was heated to 70° C. for 2 hours. The mixture was then filtered and purified by silica gel chromatography (ethyl acetate: petroleum ether=1:4) to give 4-ethyl-1-methyl-5-(4,4,5,5-tetramethyl-1,3,2-dioxaborolan-2-yl)pyridin-2-one (600 mg, 70% yield) as a white solid. LCMS (ESI): [M+H]⁺=264.1.

Step 5: (±)-cis-N-[8-amino-6-(4-ethyl-1-methyl-6-oxo-3-pyridyl)-2,7-naphthyridin-3-yl]-2-fluoro-cyclopropanecarboxamide

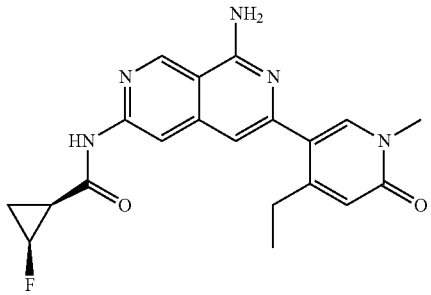 [SMILES: CCc1cc(=O)n(C)cc1-c1cc2cc(NC(=O)[C@@H]3C[C@@H]3F)ncc2c(N)n1]

(±)-cis-N-(8-amino-6-chloro-2,7-naphthyridin-3-yl)-2-fluoro-cyclopropanecarboxamide (100 mg, 0.4 mmol), Pd(PPh₃)₄ (41 mg, 0.04 mmol) and K₃PO₄ (151 mg, 0.7 mmol) were added sequentially to a solution of 4-ethyl-1-methyl-5-(4,4,5,5-tetramethyl-1,3,2-dioxaborolan-2-yl)pyridin-2-one (375 mg, 1.4 mmol) in 1,4-dioxane (8 mL) and water (1.5 mL). The reaction mixture was stirred at 100° C. for 2 hours. The reaction mixture was concentrated in vacuo and purified on silica gel chromatography (methanol/dichloromethane, 1:9) to afford (±)-cis-N-[8-amino-6-(4-ethyl-1-methyl-6-oxo-3-pyridyl)-2,7-naphthyridin-3-yl]-2-fluoro-cyclopropanecarboxamide (6 mg, 4.4% yield) as a white solid. LCMS (ESI): R_T (min)=1.43, [M+H]⁺=382.1, method=G; ¹H NMR (400 MHz, CD₃OD) δ 9.16 (s, 1H), 8.19 (s, 1H), 7.65 (s, 1H), 6.84 (s, 1H), 6.40 (s, 1H), 4.88-4.67 (m, 1H), 3.50 (s, 3H), 2.64 (q, J=7.6 Hz, 2H), 2.12-1.99 (m, 1H), 1.79-1.63 (m, 1H), 1.12-1.10 (m, 1H), 0.98 (t, J=7.6 Hz, 3H).

Example 64

(R)-1-(8-amino-6-(4-ethylpyridin-3-yl)-2,7-naphthyridin-3-yl)-3-(1-methyl-2-oxopyrrolidin-3-yl)urea
(Compound 65)

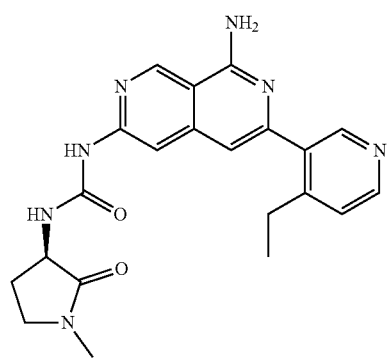 [SMILES: CCc1ccncc1-c1cc2cc(NC(=O)N[C@@H]3CCN(C)C3=O)ncc2c(N)n1]

Step 1: (R)-1-(8-(bis(4-methoxybenzyl)amino)-6-(4-ethylpyridin-3-yl)-2,7-naphthyridin-3-yl)-3-(1-methyl-2-oxopyrrolidin-3-yl)urea

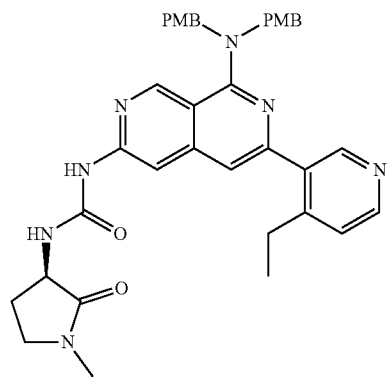

To a solution of triphosgene (108 mg, 0.36 mmol) in THF (4 mL) was added 3-(4-ethyl-3-pyridyl)-N1,N1-bis[(4-methoxyphenyl)methyl]-2,7-naphthyridine-1,6-diamine (180 mg, 0.18 mmol) and Et₃N (0.5 mL, 3.56 mmol) in THF (5 mL) at 0° C. The mixture was stirred at 0° C. for 1 hour. To this was added (3R)-3-amino-1-methyl-pyrrolidin-2-one (450 mg, 3.94 mmol). The mixture warmed to room temperature overnight. The mixture was directly purified by silica gel chromatography (dichloromethane/methanol, 20:1) to give 1-[8-[bis[(4-methoxyphenyl)methyl]amino]-6-(4-ethyl-3-pyridyl)-2,7-naphthyridin-3-yl]-3-[(3R)-1-methyl-2-oxo-pyrrolidin-3-yl]urea (32 mg, 28% yield) as a light yellow solid. LCMS (ESI): [M+H]⁺=646.3.

Step 2: (R)-1-(8-amino-6-(4-ethylpyridin-3-yl)-2,7-naphthyridin-3-yl)-3-(1-methyl-2-oxopyrrolidin-3-yl)urea

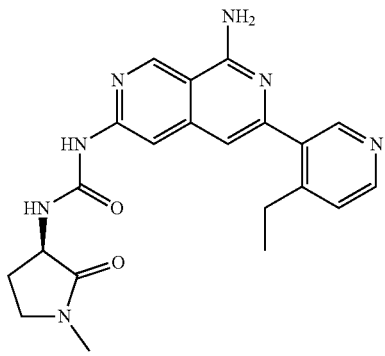 [SMILES: CCc1ccncc1-c1cc2cc(NC(=O)N[C@@H]3CCN(C)C3=O)ncc2c(N)n1]

A solution of 1-[8-[bis[(4-methoxyphenyl)methyl]amino]-6-(4-ethyl-3-pyridyl)-2,7-naphthyridin-3-yl]-3-[(3R)-1-methyl-2-oxo-pyrrolidin-3-yl]urea (27 mg, 0.04 mmol) in TFA (3 mL) was heated to reflux for 3 hours. The mixture was evaporated and neutralized by ammonium in methanol. The resulting residue was purified by reverse phase chromatography (acetonitrile 0-40/0.1% NH$_4$HCO$_3$ in water) to afford 1-[8-amino-6-(4-ethyl-3-pyridyl)-2,7-naphthyridin-3-yl]-3-[(3R)-1-methyl-2-oxo-pyrrolidin-3-yl]urea (5.5 mg, 33% yield) as a white solid. LCMS (ESI): R$_T$ (min)=1.501, [M+H]$^+$=406.2, Method=C; $^1$H NMR (400 MHz, CD$_3$OD): δ 9.29 (s, 1H), 8.50 (s, 2H), 7.52 (s, 1H), 7.45 (d, J=5.2 Hz, 1H), 6.89 (s, 1H), 4.49 (t, J=9.2 Hz, 1H), 3.47 (dd, J=4.0, 9.2 Hz, 2H), 2.93 (s, 3H), 2.83 (q, J=7.6 Hz, 2H), 2.62-2.57 (m, 1H), 2.09-2.04 (m, 1H), 1.19 (t, J=7.6 Hz, 3H).

Example 65

(±)-cis-N-(8-amino-6-(4-ethyl-6-methoxypyridin-3-yl)-2,7-naphthyridin-3-yl)-2-fluorocyclopropanecarboxamide (Compound 66)

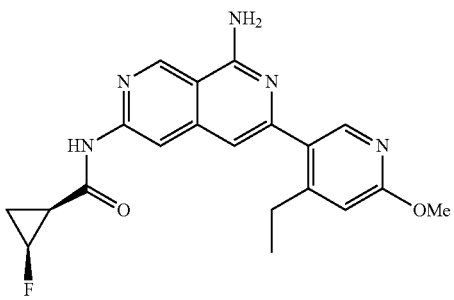 [SMILES: CCc1cc(OC)ncc1-c1cc2cc(NC(=O)[C@@H]3C[C@@H]3F)ncc2c(N)n1]

Step 1: 4-ethyl-5-(4,4,5,5-tetramethyl-1,3,2-dioxaborolan-2-yl)pyridin-2-amine

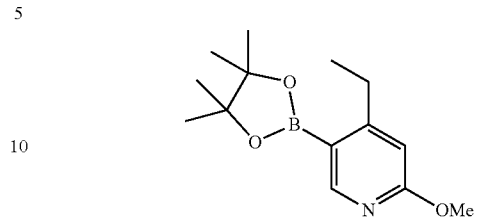

A solution of 5-bromo-4-ethyl-2-methoxy-pyridine (400 mg, 1.85 mmol), bis(pinacolato)diboron (940 mg, 3.7 mmol), Pd(dppf)Cl$_2$ (270 mg, 0.37 mmol) and potassium acetate (560 mg, 5.71 mmol) in 1,4-dioxane (30 mL) was heated to 70° C. for 2 hours. After the mixture was filtered and evaporated to give 4-ethyl-2-methoxy-5-(4,4,5,5-tetramethyl-1,3,2-dioxaborolan-2-yl)pyridine (400 mg, 82% yield) as a black solid, which was used directly in the next reaction. LCMS (ESI): [M+H]$^+$=264.2.

Step 2: (±)-cis-N-(8-amino-6-(4-ethyl-6-methoxypyridin-3-yl)-2,7-naphthyridin-3-yl)-2-fluorocyclopropanecarboxamide

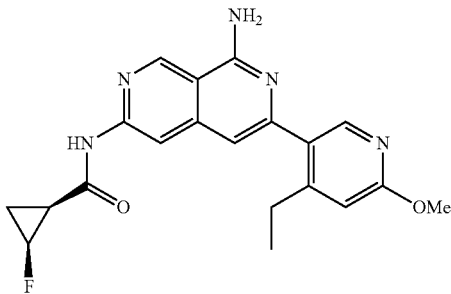 [SMILES: CCc1cc(OC)ncc1-c1cc2cc(NC(=O)[C@@H]3C[C@@H]3F)ncc2c(N)n1]

A solution of 4-ethyl-2-methoxy-5-(4,4,5,5-tetramethyl-1,3,2-dioxaborolan-2-yl)pyridine (380 mg, 1.44 mmol), (±)-cis-N-(8-amino-6-chloro-2,7-naphthyridin-3-yl)-2-fluorocyclopropanecarboxamide (100 mg, 0.36 mmol), K$_3$PO$_4$ (630 mg, 2.99 mmol), Pd$_2$(dba)$_3$ (140 mg, 0.15 mmol) and X-phos (76 mg, 0.16 mmol) in 1,4-dioxane (24 mL) and water (4 mL) was heated to 80° C. for 3 hours under an Ar atmosphere. The mixture was purified by reverse phase chromatography (acetonitrile 17-47/0.05% ammonium bicarbonate) to give (1S,2S)—N-[8-amino-6-(4-ethyl-6-methoxy-3-pyridyl)-2,7-naphthyridin-3-yl]-2-fluoro-cyclopropanecarboxamide (6 mg, 1.1% yield) as a white solid. LCMS (ESI): R$_T$ (min)=1.782, [M+H]$^+$=382.1, Method=C; $^1$H NMR (400 MHz, CD$_3$OD): δ 9.29 (s, 1H), 8.30 (s, 1H), 8.11 (s, 1H), 6.94 (s, 1H), 6.79 (s, 1H), 4.98-4.87 (m, 1H), 3.96 (s, 3H), 2.81 (q, J=6.0 Hz, 2H), 2.19-2.16 (m, 1H), 1.86-1.81 (m, 1H), 1.26-1.22 (m, 1H), 1.14 (t, J=6.0 Hz, 3H).

Example 66 cis-N-(8-amino-6-(6-amino-4-ethylpyridin-3-yl)-2,7-naphthyridin-3-yl)-2-fluorocyclopropanecarboxamide (Compound 67)

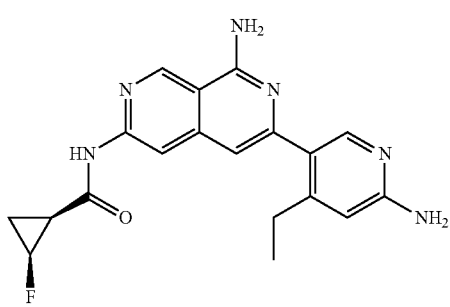 [SMILES: CCc1cc(N)ncc1-c1cc2cc(NC(=O)[C@@H]3C[C@@H]3F)ncc2c(N)n1]

Step 1: 4-ethyl-5-(4,4,5,5-tetramethyl-1,3,2-dioxaborolan-2-yl)pyridin-2-amine

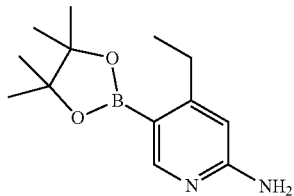 [SMILES: CCc1cc(N)ncc1B1OC(C)(C)C(C)(C)O1]

A solution of 5-bromo-4-ethyl-pyridin-2-amine (500 mg, 2.49 mmol), bis(pinacolato)diboron (750 mg, 2.95 mmol), Pd(dppf)Cl$_2$ (200 mg, 0.27 mmol) and potassium acetate (750 mg, 7.65 mmol) in 1,4-dioxane (30 mL) was heated to 120° C. for 2 hours. The mixture was filtered and evaporated to give 4-ethyl-5-(4,4,5,5-tetramethyl-1,3,2-dioxaborolan-2-yl)pyridin-2-amine (500 mg, 35% yield) as a black slurry, which was used directly in the next reaction. LCMS (ESI) [M+H]$^+$=249.1.

Step 2: (±)-cis-N-(8-amino-6-(6-amino-4-ethylpyridin-3-yl)-2,7-naphthyridin-3-yl)-2-fluorocyclopropanecarboxamide

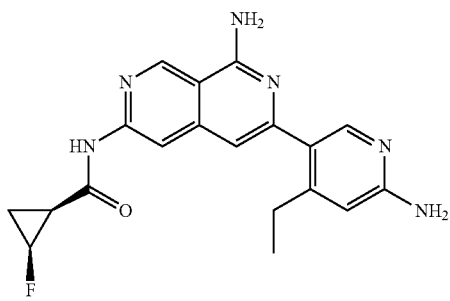 [SMILES: CCc1cc(N)ncc1-c1cc2cc(NC(=O)[C@@H]3C[C@@H]3F)ncc2c(N)n1]

A solution of 4-ethyl-5-(4,4,5,5-tetramethyl-1,3,2-dioxaborolan-2-yl)pyridin-2-amine (400 mg, 0.64 mmol), (±)-cis-N-(8-amino-6-chloro-2,7-naphthyridin-3-yl)-2-fluoro-cyclopropanecarboxamide (100 mg, 0.36 mmol), Pd(PPh$_3$)$_4$ (80 mg, 0.07 mmol) and K$_3$PO$_4$ (280 mg, 1.33 mmol) in 1,4-dioxane (24 mL) and water (4 mL) was heated to 100° C. for 3 hours. The mixture was purified by silica gel chromatography (dichloromethane:methanol, 10:1) to give (1S,2S)—N-[8-amino-6-(6-amino-4-ethyl-3-pyridyl)-2,7-naphthyridin-3-yl]-2-fluoro-cyclopropanecarboxamide (30 mg, 13% yield) as a white solid. LCMS (ESI): R$_T$ (min)=1.476, [M+H]$^+$=367.2, Method=G; $^1$H NMR (400 MHz, CD$_3$OD): δ 9.26 (s, 1H), 8.28 (s, 1H), 7.90 (s, 1H), 6.90 (s, 1H), 6.57 (s, 1H), 5.00-4.79 (m, 1H), 2.74 (q, J=7.6 Hz, 2H), 2.19-2.13 (m, 1H), 1.88-1.80 (m, 1H), 1.29-1.19 (m, 1H), 1.11 (t, J=7.6 Hz, 3H).

Example 67

N-[8-amino-6-(4-ethyl-3-pyridyl)-2,7-naphthyridin-3-yl]cyclopropene-1-carboxamide (Compound 68)

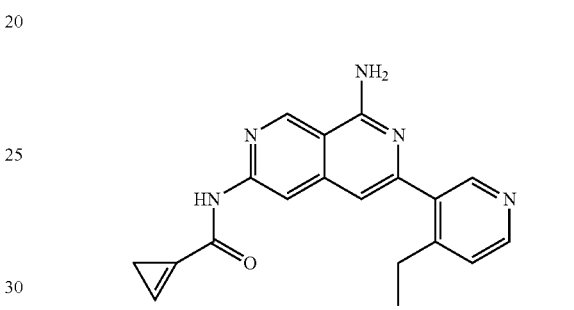

Step 1: N-[8-[bis[(4-methoxyphenyl)methyl]amino]-6-(4-ethyl-3-pyridyl)-2,7-naphthyridin-3-yl]-2-nitro-cyclopropanecarboxamide

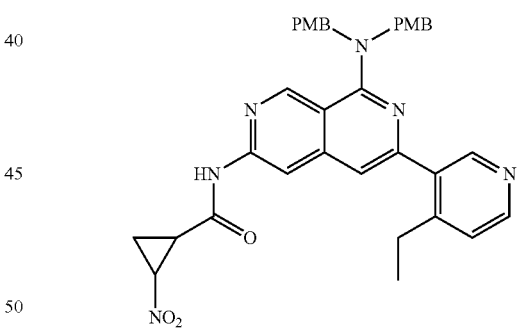

Oxalyl chloride (0.2 mL, 2.35 mmol) was added dropwise to a suspension of 2-nitrocyclopropanecarboxylic acid (200 mg, 1.53 mmol) and DMF (20 mg, 0.27 mmol) in dichloromethane (4 mL) at 25° C. and the mixture was stirred at 25° C. for 1 hour. The reaction mixture turned from a suspension to a solution. The mixture was concentrated at room temperature to remove the excess oxalyl chloride. The residue was dissolved in dichloromethane (1 mL) and added dropwise to a solution of 3-(4-ethyl-3-pyridyl)-N1,N1-bis[(4-methoxyphenyl)methyl]-2,7-naphthyridine-1,6-diamine (800 mg, 1.58 mmol) and triethylamine (700 mg, 6.93 mmol) in dichloromethane (8 mL) at 0° C. and stirred at 0° C. for 1 hour. The reaction mixture was evaporated and the resulting residue purified by silica gel chromatography (petroleum ether/ethyl acetate=1:1 to 1:2, Rf=0.8 at petroleum ether/ethyl acetate 1/2) to give N-[8-[bis[(4-methoxyphenyl)methyl]amino]-6-(4-ethyl-3-pyridyl)-2,7-naphthyridin-3-yl]-2-nitro-cyclopropanecarboxamide (240 mg, 25% yield) as brown solid. LCMS (ESI) [M+H]$^+$=619.2.

Step 2: N-[8-[bis[(4-methoxyphenyl)methyl]amino]-6-(4-ethyl-3-pyridyl)-2,7-naphthyridin-3-yl]-2-nitro-cyclopropanecarboxamide

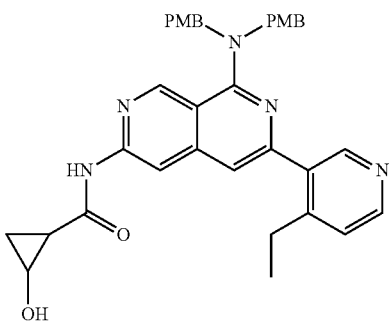

A mixture of N-[8-[bis[(4-methoxyphenyl)methyl]amino]-6-(4-ethyl-3-pyridyl)-2,7-naphthyridin-3-yl]-2-nitro-cyclopropanecarboxamide (230 mg, 0.37 mmol) and iron (400 mg, 7.14 mmol) in acetic acid (5 mL) was stirred at 50° C. for 1 hour. The reaction mixture was cooled to room temperature. A 5:1 mixture of ethyl acetate and/methanol (150 mL) was added. The mixture was then filtered and concentrated. To the residue was added water (20 mL), adjusted to pH 7-8 by saturated NaHCO$_3$ and extracted with ethyl acetate (50 mL×3). The ethyl acetate layers were combined, dried over Na$_2$SO$_4$, filtered and evaporated. The residue was purified with prep-TLC (petroleum ether/ethyl acetate 1/2, Rf=0.2 at petroleum ether/ethyl acetate 1/2) to give N-[8-[bis[(4-methoxyphenyl)methyl]amino]-6-(4-ethyl-3-pyridyl)-2,7-naphthyridin-3-yl]-2-hydroxy-cyclopropanecarboxamide (45 mg, 20% yield) as a brown solid. LCMS (ESI) [M+H]$^+$=590.2.

Step 3: N-[8-amino-6-(4-ethyl-3-pyridyl)-2,7-naphthyridin-3-yl]cyclopropene-1-carboxamide

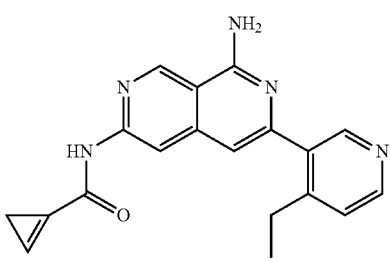 [SMILES: CCc1ccncc1-c1cc2cc(NC(=O)C3=CC3)ncc2c(N)n1]

A mixture of N-[8-[bis[(4-methoxyphenyl)methyl]amino]-6-(4-ethyl-3-pyridyl)-2,7-naphthyridin-3-yl]-2-hydroxy-cyclopropanecarboxamide (42 mg, 0.071 mmol) in TFA (4 mL) was stirred at 80° C. for 1.5 hours and then evaporated. The residue was suspended in methanol (1 mL). A 7N NH$_3$-methanol solution was added until the pH was between 9-10. The mixture was then purified with flash chromatography (C18, methanol/water to formic acid/methanol/water) to give the formic acid salt of N-[8-amino-6-(4-ethyl-3-pyridyl)-2,7-naphthyridin-3-yl]cyclopropene-1-carboxamide (15 mg, 56% yield) as a light brown solid. LCMS (ESI): R$_T$ (min)=1.336, [M+H]$^+$=332.1, method=A; $^1$H NMR (400 MHz, DMSO-d$_6$) δ 9.42 (s, 1H), 8.52-8.48 (m, 3H), 8.4 (brs, 1H), 7.58 (dd, J=1.6, 5.6 Hz, 1H), 7.39 (s, 2H), 7.35 (d, J=4.8 Hz, 1H), 7.01 (s, 1H), 6.34 (dd, J=1.6, 4.4 Hz, 1H), 4.79 (s, 2H), 2.80 (q, J=7.6 Hz, 2H), 1.10 (t, J=7.6 Hz, 3H).

Example 68

5-Methyl-1H-pyrazole-3-carboxylic acid [8-amino-6-(4-ethylpyridin-3-yl)-[2,7]naphthyridin-3-yl]amide (Compound 70)

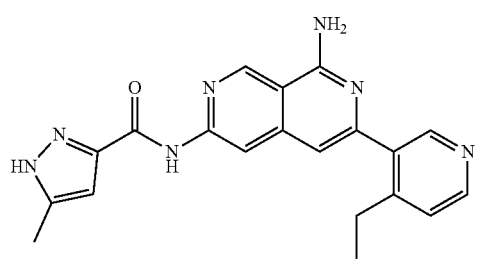

Step 1: 5-Methyl-1H-pyrazole-3-carboxylic acid [8-[bis-(4-methoxybenzyl)amino]-6-(4-ethylpyridin-3-yl)-[2,7]naphyridin-3-yl]amide

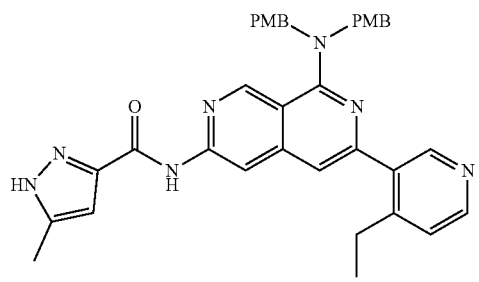

To a suspension of 5-methyl-1H-pyrazole-3-carboxylic acid (126 mg, 1 mmol) in anhydrous dichloromethane (5 mL) was added oxalyl chloride (0.423 mL, 5 mmol) and DMF (2 drops). The mixture was stirred at room temperature for 4.5 hour and then concentrated. The residue was azeotroped twice with dry chloroform then concentrated under vacuum to give crude acid chloride. This was dissolved in dry dichloromethane (2 mL). Half of this solution (0.5 mmol) was added to a solution of 3-(4-ethylpyridin-3-yl)-N1,N1-bis-(4-methoxybenzyl)-[2,7]naphthyridine-1,6-diamine (126 mg, 0.25 mmol) in dichloromethane (2 mL), followed by the addition of pyridine (0.1 mL, 1.24 mmol). The mixture was stirred at room temperature for 4.5 hours, then water (approx. 5 mL) was added and the phases separated. The aqueous phase was extracted with dichloromethane (3×). The combined organic extracts were dried (Na$_2$SO$_4$) and evaporated. The crude product was purified by silica gel chromatography (50-100% ethyl acetate/cyclohexane) to give the title compound (47 mg, 31% yield). LCMS (ESI): R$_T$ (min)=1.51, [M+H]$^+$=614, method=I.

Step 2: 5-Methyl-1H-pyrazole-3-carboxylic acid [8-amino-6-(4-ethylpyridin-3-yl)-[2,7]naphthyridin-3-yl]amide

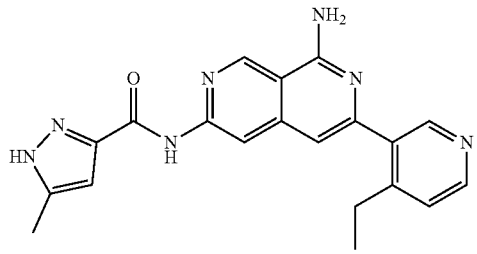

A solution of 5-methyl-1H-pyrazole-3-carboxylic acid [8-[bis-(4-methoxybenzyl)amino]-6-(4-ethylpyridin-3-yl)-[2,7]naphthyridin-3-yl]amide (47 mg, 0.077 mmol) in TFA (2 mL) was heated at 80° C. for 2.5 hours, then evaporated. The residue was slurried in a 2M ammonia/methanol solution. Addition methanol was added to dissolve all material. This solution was absorbed onto a Isolute® HM-N, loaded onto a silica gel column and eluted with 0-10% methanol/dichloromethane to give the title compound (27 mg, 94% yield). LCMS (ESI): $R_T$(min)=2.47, [M+H]$^+$=374, method=J; $^1$H NMR (400 MHz, DMSO-d$_6$) δ 13.28 (broad s, 1H), 9.65 (broad s, 1H), 9.43 (s, 1H), 8.54 (s, 1H), 8.52 (d, J=5.1 Hz, 1H), 8.35, (s, 1H), 7.49 (broad s, 2H), 7.38 (d, J=5.1 Hz, 1H), 7.04 (s, 1H), 6.62 (s, 1H), 2.80 (q, J=7.2 Hz, 2H), 2.31 (s, 3H), 1.11 (t, J=7.2 Hz, 3H).

Example 69

2H-Pyrazole-3-carboxylic acid [8-amino-6-(4-ethylpyridin-3-yl)-[2,7]naphthyridin-3-yl]amide (Compound 71)

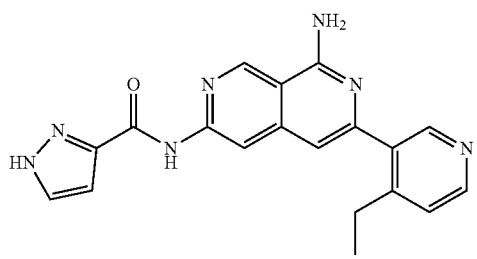

Step 1: 2H-Pyrazole-3-carboxylic acid [8-[bis-(4-methoxybenzyl)amino]-6-(4-ethylpyridin-3-yl)-[2,7]naphthyridin-3-yl]amide

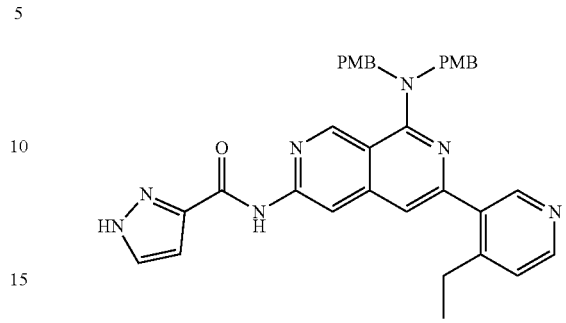

To a suspension of 1H-pyrazole-3-carboxylic acid (224 mg, 2 mmol) in dry dichloromethane (10 mL) was added oxalyl chloride (0.846 mL, 10 mmol) and DMF (2 drops). The mixture was stirred at room temperature for 4.5 hours and then evaporated. The residue was azeotroped twice with dry chloroform then dried under vacuum to give the crude acid chloride. To a mixture of this material (80 mg, 0.6 mmol) and 3-(4-ethylpyridin-3-yl)-N1,N1-bis-(4-methoxybenzyl)-[2,7]naphthyridine-1,6-diamine (150 mg, 0.29 mmol) in dichloromethane (2.5 mL) was added pyridine (0.12 mL, 1.44 mmol). The mixture was stirred at room temperature for 5 hour Water was then added and the phases separated. The aqueous phase was extracted three times with dichloromethane. The combined organic extracts were dried (Na$_2$SO$_4$) and evaporated. The crude product was chromatographed on silica gel (eluted with 50-100% ethyl acetate/cyclohexane) to give the title compound (66 mg, 38% yield). LCMS (ESI): $R_T$ (min)=3.10, [M+H]$^+$=600, method=K.

Step 2: 2H-Pyrazole-3-carboxylic acid [8-amino-6-(4-ethylpyridin-3-yl)-[2,7]naphthyridin-3-yl]amide

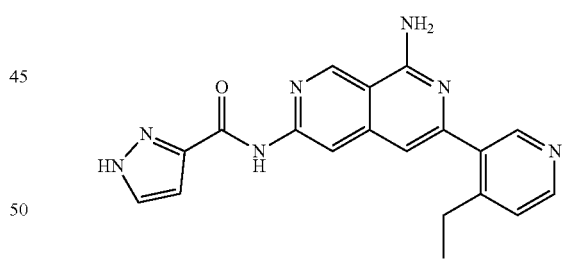

A solution of 2H-pyrazole-3-carboxylic acid [8-[bis-(4-methoxybenzyl)amino]-6-(4-ethylpyridin-3-yl)-[2,7]naphthyridin-3-yl]amide (66 mg, 0.11 mmol) in TFA (2 mL) was heated at 80° C. for 3.5 hours, then evaporated. The residue was slurried in a 2M solution of ammonia/methanol. Additional dichloromethane and methanol was added to dissolve all material. This solution was evaporated onto Isolute® HM-N, loaded onto a silica gel column and eluted with 0-10% methanol/dichloromethane. The product obtained was triturated with water and the solid was filtered off, washed with water and dried (vacuum, 60° C.) to give the title compound (17 mg, 43% yield). LCMS (ESI): $R_T$ (min)=2.28, [M+H]$^+$=360, method=J; $^1$H NMR (400 MHz, DMSO-d$_6$) δ 10.05 (broad, s, 1H), 9.59 (s, 1H), 8.65 (m, 2H), 8.47, (s, 1H), 8.31 (broad, s, 1H), 7.94 (s, 1H), 7.58 (d, J=5.2 Hz, 1H), 7.25 (s, 1H), 6.96 (s, 1H), 2.80 (q, J=7.2 Hz, 2H), 1.16 (t, J=7.2 Hz, 3H).

Example 70

2-Methyl-2H-pyrazole-3-carboxylic acid [8-amino-6-(4-ethylpyridin-3-yl)-[2,7]naphthyridin-3-yl]amide (Compound 72)

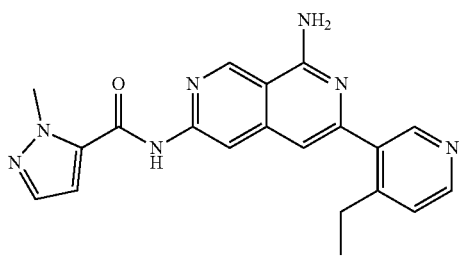 [SMILES: CCc1ccncc1-c1cc2cc(NC(=O)c3ccnn3C)ncc2c(N)n1]

Step 1: 2-Methyl-2H-pyrazole-3-carboxylic acid [8-[bis-(4-methoxybenzyl)amino]-6-(4-ethylpyridin-3-yl)-[2,7]naphthyridin-3-yl]amide

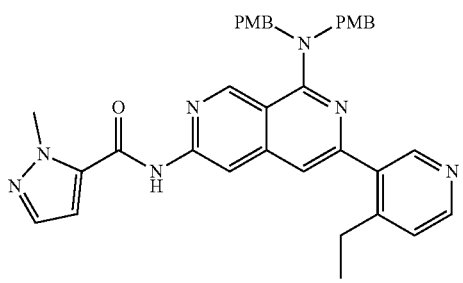

To a suspension of 2-methyl-1H-pyrazole-3-carboxylic acid (126 mg, 1 mmol) in dry dichloromethane (5 mL) was added oxalyl chloride (0.423 mL, 5 mmol) and DMF (2 drops). The mixture was stirred at room temperature for 4.5 hours and evaporated. The residue was azeotroped twice with dry chloroform then dried under vacuum to give crude acid chloride. This was dissolved in dry dichloromethane (2 mL). Half of this solution (0.5 mmol) was added to a solution of 3-(4-ethylpyridin-3-yl)-N1,N1-bis-(4-methoxybenzyl)-[2,7]naphthyridine-1,6-diamine (126 mg, 0.25 mmol) in dichloromethane (2 mL), followed by pyridine (0.1 mL, 1.24 mmol). The mixture was stirred at room temperature for 4.5 hours, then water (approx. 5 mL) was added and the phases separated. The aqueous phase was extracted with dichloromethane (3×). The combined organic fractions were dried (Na$_2$SO$_4$) and evaporated. The crude product was chromatographed on silica gel eluted with 50-100% ethyl acetate/cyclohexane to give the title compound (61 mg, 40% yield). LCMS (ESI): R$_T$ (min)=3.26, [M+H]$^+$=614, method=K.

Step 2: 2-Methyl-2H-pyrazole-3-carboxylic acid [8-amino-6-(4-ethylpyridin-3-yl)-[2,7]naphthyridin-3-yl]amide

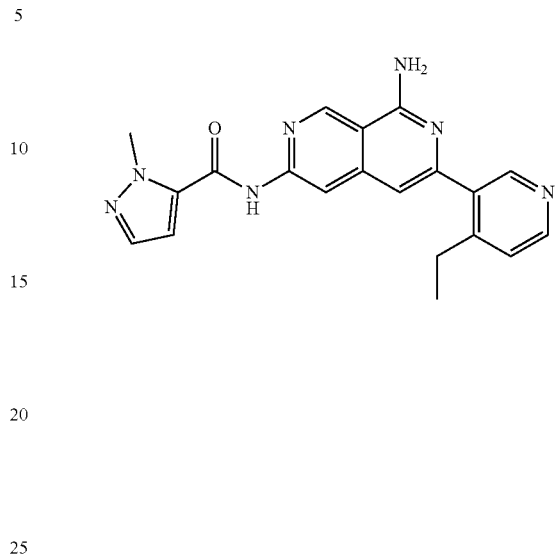

A solution of 2-methyl-1H-pyrazole-3-carboxylic acid [8-[bis-(4-methoxybenzyl)amino]-6-(4-ethylpyridin-3-yl)-[2,7]naphyridin-3-yl]amide (61 mg, 0.1 mmol) in TFA (2 mL) was heated at 80° C. for 2.5 hours, then evaporated. The residue was slurried with 2M ammonia/methanol. Additional methanol was added to dissolve all material. This solution was evaporated onto Isolute® HM-N, loaded onto a silica gel column and eluted with 0-7% methanol/dichloromethane to give the title compound (35 mg, 94% yield). LCMS (ESI): R$_T$(min)=2.44, [M+H]$^+$=374, method=J; $^1$H NMR (400 MHz, DMSO-d$_6$) δ 11.06 (s, 1H), 9.52 (s, 1H), 8.56 (s, 1H), 8.55 (d, J=5.4 Hz, 1H), 8.42 (s, 1H), 7.69 (broad s, 2H), 7.55 (d, J=2.1 Hz, 1H), 7.43 (d, J=5.4 Hz, 1H), 7.38 (d, J=2.1 Hz, 1H), 7.10 (s, 1H), 4.14 (s, 3H), 2.81 (q, J=7.5 Hz, 2H), 1.13 (t, J=7.5 Hz, 3H).

Example 71

1-Methyl-1H-pyrazole-4-carboxylic acid [8-amino-6-(4-ethylpyridin-3-yl)-[2,7]naphthyridin-3-yl]amide (Compound 73)

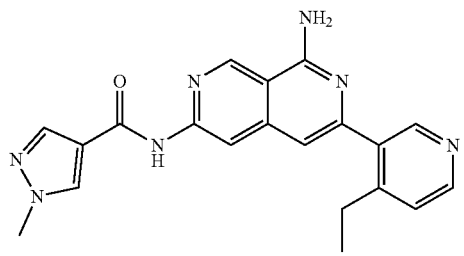 [SMILES: CCc1ccncc1-c1cc2cc(NC(=O)c3cnn(C)c3)ncc2c(N)n1]

Step 1: 1-Methyl-1H-pyrazole-4-carboxylic acid [8-bis-(4-methoxybenzyl)amino-6-(4-ethylpyridin-3-yl)-[2,7]naphthyridin-3-yl]amide

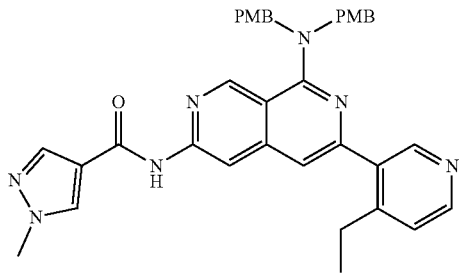

To a suspension of 1-methyl-1H-pyrazole-4-carboxylic acid (126 mg, 1 mmol) in dry dichloromethane (3 mL) was added oxalyl chloride (0.43 mL, 5 mmol) and DMF (2 drops). The mixture was stirred at room temperature for 16 hours and then evaporated. The residue was azeotroped twice with toluene to give crude acid chloride. This was dissolved in dry dichloromethane (1 mL). Half of this solution (0.5 mmol) was added to a solution of 3-(4-ethylpyridin-3-yl)-N1,N1-bis-(4-methoxybenzyl)-[2,7]naphthyridine-1,6-diamine (100 mg, 0.20 mmol) in dichloromethane (2 mL), followed by pyridine (0.1 mL, 1.24 mmol). The mixture was stirred at room temperature for 1 hour and then evaporated. The residue was re-dissolved in dichloromethane and washed with water. The organic phase was dried (PTFE cartridge) and evaporated. The crude product was chromatographed on silica gel (eluted with 0-100% ethyl acetate/dichloromethane) to give the title compound (100 mg, 80% yield). LCMS (ESI): $R_T$ (min)=1.57, $[M+H]^+$=614, method=I.

Step 2: 1-Methyl-1H-pyrazole-4-carboxylic acid [8-amino-6-(4-ethylpyridin-3-yl)-[2,7]naphthyridin-3-yl]amide

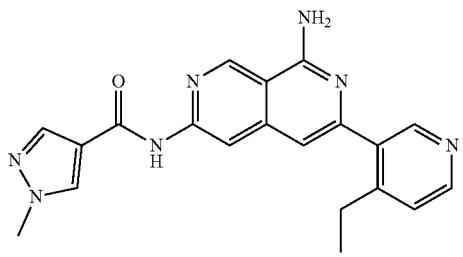 [SMILES: CCc1ccncc1-c1cc2cc(NC(=O)c3cnn(C)c3)ncc2c(N)n1]

A solution of 1-methyl-H-pyrazole-4-carboxylic acid [8-bis-(4-methoxybenzyl)amino-6-(4-ethylpyridin-3-yl)-[2,7]naphthyridin-3-yl]amide (98 mg, 0.155 mmol) in TFA (3 mL) was heated at 80° C. for 1 hour, then evaporated. The residue was taken up in 2M ammonia/methanol. The mixture was then evaporated. The residue was dissolved in hot chloroform/methanol and the solution was evaporated onto Isolute® HM-N, loaded onto a silica column and eluted with 0-10% methanol/dichloromethane to give the title compound which was recrystallized from ethyl acetate. LCMS (ESI): $R_T$ (min)=2.21, $[M+H]^+$=374, method=J; $^1$H NMR (400 MHz, DMSO-$d_6$) δ 10.64 (s, 1H), 9.43 (s, 1H), 8.51 (s, 1H), 8.49 (d, J=5.1 Hz, 1H), 8.47 (s, 1H), 8.36 (s, 1H), 8.18 (s, 1H), 7.35 (d, J=5.1 Hz, 1H), 7.33 (broad, 2H), 6.97 (s, 1H), 3.90 (s, 3H), 2.80 (q, J=7.3 Hz, 2H), 1.11 (t, J=7.3 Hz, 3H).

Example 72

3-(4-Ethylpyridin-3-yl)-N6-(1-methyl-1H-pyrazol-4-yl)-[2,7]naphthyridine-1,6-diamine (Compound 74)

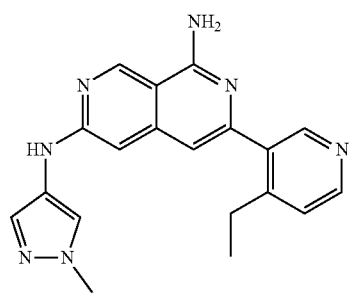 [SMILES: CCc1ccncc1-c1cc2cc(Nc3cnn(C)c3)ncc2c(N)n1]

Step 1: 3-(4-Ethylpyridin-3-yl)-N1,N1-bis-(4-methoxybenzyl)-N6-(1-methyl-H-pyrazol-4-yl)-[2,7]naphthyridine-1,6-diamine

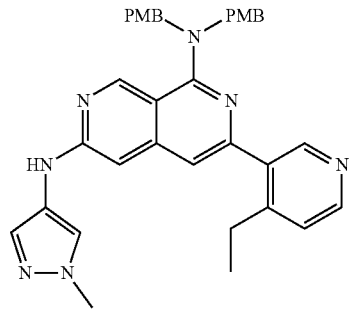

A mixture of 3-(4-ethylpyridin-3-yl)-N1,N1-bis-(4-methoxybenzyl)-[2,7]naphthyridine-1,6-diamine (126 mg, 0.25 mmol), 4-bromo-1-methyl-1H-pyrazole (56 mg, 0.35 mmol), 2-(di-tert-butylphosphino)-2',4',6'-triisopropyl-3,6-dimethoxybiphenyl (3.5 mg, 0.007 mmol) and t-BuBrettPhos Palladacycle Gen. 3 (6 mg, 0.007 mmol) in dry THF (3 mL) was purged with argon. Lithium bis(trimethylsilyl) amide (1 M in toluene, 0.77 mL, 0.77 mmol) was added and the mixture was heated at 80° C. for 18 hours. Further quantities of 4-bromo-1-methyl-1H-pyrazole (56 mg), 2-(di-tert-butylphosphino)-2',4',6'-triisopropyl-3,6-dimethoxybiphenyl (7 mg) and t-BuBrettPhos Palladacycle Gen. 3 (12 mg) were added and heating continued for 24 hours. The cooled mixture was diluted with water and extracted with ethyl acetate three times. The extracts were dried ($Na_2SO_4$) and evaporated. The crude product was chromatographed on silica eluted with 50-100% ethyl acetate/cyclohexane to give the title compound (27 mg, 18% yield). LCMS (ESI): $R_T$ (min)=2.88, $[M+H]^+$=586, method=K.

Step 2: 3-(4-Ethylpyridin-3-yl)-N6-(1-methyl-1H-pyrazol-4-yl)-[2,7]naphthyridine-1,6-diamine

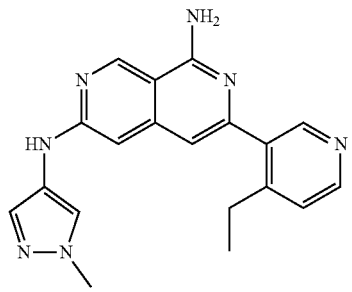 [SMILES: CCc1ccncc1-c1cc2cc(Nc3cnn(C)c3)ncc2c(N)n1]

A solution of 3-(4-ethylpyridin-3-yl)-N1,N1-bis-(4-methoxybenzyl)-N6-(1-methyl-1H-pyrazol-4-yl)-[2,7]naphthyridine-1,6-diamine (27 mg, 0.046 mmol) in TFA (1.5 mL) was heated at 80° C. for 4 hours, then evaporated. The residue was loaded onto a 2 g SCX-2 cartridge and eluted with methanol, then with 2M ammonia in methanol. Ammoniacal fractions were evaporated to give the title compound (14 mg, 88% yield). LCMS (ESI): $R_T$ (min)=2.10, $[M+H]^+$=346, method=J; $^1$H NMR (400 MHz, DMSO-$d_6$) δ 9.21 (s, 1H), 8.84 (s, 1H), 8.46 (s, 1H & d, J=5.0 Hz, 1H), 7.87 (s, 1H), 7.45 (s, 1H), 7.32 (d, J=5.0 Hz, 1H), 7.07 (broad, 2H), 6.72 (s, 1H), 6.62 (s, 1H), 3.83 (s, 3H), 2.78 (q, J=7.1 Hz, 2H), 1.10 (t, J=7.1 Hz, 3H).

Example 73

3-(4-Ethylpyridin-3-yl)-N6-(1H-pyrazol-4-yl)-[2,7]naphthyridine-1,6-diamine (Compound 75)

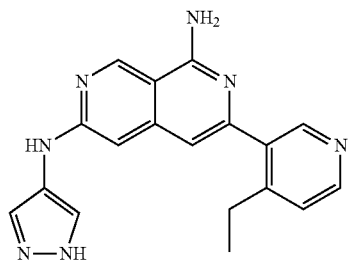 [SMILES: CCc1ccncc1-c1cc2cc(Nc3cn[nH]c3)ncc2c(N)n1]

Step 1: 3-(4-Ethylpyridin-3-yl)-N1,N1-bis-(4-methoxybenzyl)-N6-(1H-pyrazol-4-yl)-[2,7]naphthyridine-1,6-diamine

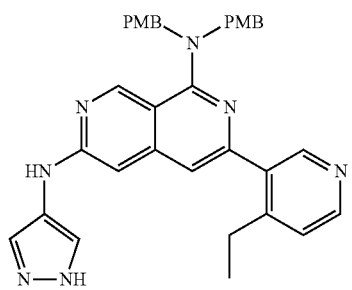

A mixture of 3-(4-ethylpyridin-3-yl)-N1,N1-bis-(4-methoxybenzyl)-[2,7]naphthyridine-1,6-diamine (126 mg, 0.25 mmol), 4-bromo-1H-pyrazole (74 mg, 0.50 mmol), 2-(di-tert-butylphosphino)-2',4',6'-triisopropyl-3,6-dimethoxybiphenyl (12 mg, 0.025 mmol) and t-BuBrettPhos Palladacycle Gen. 3 (21 mg, 0.025 mmol) in dry 1,4-dioxane (3 mL) was purged with argon. Lithium bis(trimethylsilyl)amide (1 M in toluene, 1.0 mL, 1.0 mmol) was added and the mixture was heated at 100° C. for 16 hours. The cooled mixture was diluted with water and extracted with ethyl acetate three times. The extracts were dried ($Na_2SO_4$) and evaporated. The crude product was chromatographed on silica (eluted with 0-5% methanol/ethyl acetate) to give the title compound (63 mg, 44% yield). LCMS (ESI): $R_T$ (min)=2.72, $[M+H]^+$=572, method=K.

Step 2: 3-(4-Ethylpyridin-3-yl)-N6-(1H-pyrazol-4-yl)-[2,7]naphthyridine-1,6-diamine

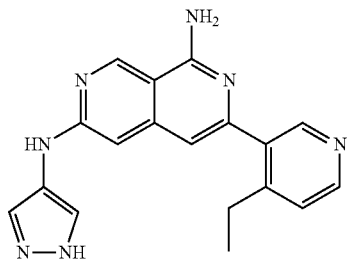 [SMILES: CCc1ccncc1-c1cc2cc(Nc3cn[nH]c3)ncc2c(N)n1]

A solution of 3-(4-ethylpyridin-3-yl)-N1,N1-bis-(4-methoxybenzyl)-N6-(1H-pyrazol-4-yl)-[2,7]naphthyridine-1,6-diamine (63 mg, 0.11 mmol) in TFA (2 mL) was heated at 80° C. for 3 hours, then evaporated. The residue was slurried with 2M ammonia in methanol. Additional methanol was added to dissolve all solid. The solution was evaporated onto Isolute® HM-N, loaded onto a silica column and eluted with 0-10% methanol/dichloromethane to give a solid which was triturated with water, filtered off and dried (vacuum, 50° C.) to give the title compound (23 mg, 63% yield). LCMS (ESI): $R_T$ (min)=1.92, $[M+H]^+$=332, method=J; $^1$H NMR (400 MHz, DMSO-$d_6$) δ 12.83 (v. broad, 1H), 9.66 (broad, 1H), 9.47 (s, 1H), 8.65 (d, J=5.3 Hz, 1H), 8.58 (s, 1H), 7.79 (broad, 2H), 7.50 (d, J=5.3 Hz, 1H), 6.99 (s, 1H), 6.78 (s, 1H), 2.68 (q, J=7.4 Hz, 2H), 1.14 (t, J=7.4 Hz, 3H).

Example 74

3-(4-Ethylpyridin-3-yl)-N6-(1-methyl-1H-pyrazol-3-yl)-[2,7]naphthyridine-1,6-diamine (Compound 76)

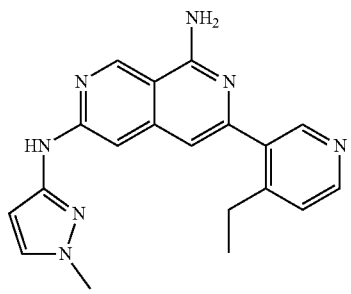 [SMILES: CCc1ccncc1-c1cc2cc(Nc3ccn(C)n3)ncc2c(N)n1]

Step 1: 3-(4-Ethylpyridin-3-yl)-N1,N1-bis-(4-methoxybenzyl)-N6-(1-methyl-1H-pyrazol-3-yl)-[2,7]naphthyridine-1,6-diamine

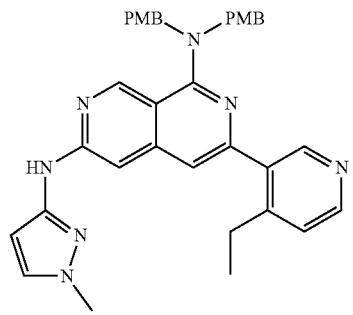

A mixture of 3-(4-ethylpyridin-3-yl)-N1,N1-bis-(4-methoxybenzyl)-[2,7]naphthyridine-1,6-diamine (126 mg, 0.25 mmol), 3-bromo-1-methyl-1H-pyrazole (81 mg, 0.50 mmol), 2-(di-tert-butylphosphino)-2',4',6'-triisopropyl-3,6-dimethoxybiphenyl (12 mg, 0.025 mmol) and t-BuBrettPhos Palladacycle Gen. 3 (21 mg, 0.025 mmol) in dry 1,4-dioxane (3 mL) was purged with argon. Lithium bis(trimethylsilyl)amide (1 M in toluene, 1.0 mL, 1.0 mmol) was added and the mixture was heated at 100° C. for 16 hours. The cooled mixture was diluted with water and extracted with ethyl acetate three times. The extracts were dried (Na$_2$SO$_4$) and evaporated. The crude product was chromatographed on silica (eluted with 0-5% methanol/ethyl acetate) to give the title compound (60 mg, 41% yield). LCMS (ESI): R$_T$ (min)=2.94, [M+H]$^+$=586, method=K.

Step 2: 3-(4-Ethylpyridin-3-yl)-N6-(1-methyl-1H-pyrazol-3-yl)-[2,7]naphthyridine-1,6-diamine

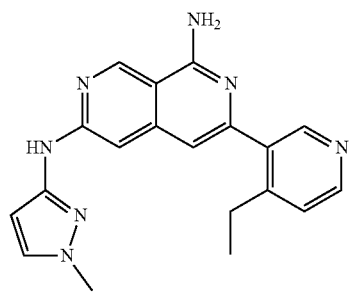 [SMILES: CCc1ccncc1-c1cc2cc(Nc3ccn(C)n3)ncc2c(N)n1]

A solution of 3-(4-ethylpyridin-3-yl)-N1,N1-bis-(4-methoxybenzyl)-N6-(1-methyl-H-pyrazol-3-yl)-[2,7]naphthyridine-1,6-diamine (60 mg, 0.10 mmol) in TFA (2 mL) was heated at 80° C. for 4.25 hours, then evaporated. The residue was loaded onto a 2 g SCX-2 cartridge and eluted with methanol, then with 2M ammonia in methanol. Ammoniacal fractions were evaporated to give the title compound (23 mg, 67% yield). LCMS (ESI): R$_T$ (min)=2.24, [M+H]$^+$=346, method=J; $^1$H NMR (400 MHz, DMSO-d$_6$) δ 9.37 (s, 1H), 9.22 (s, 1H), 8.48 (s, 1H), 8.47 (d, J=5.1 Hz, 1H), 7.55 (d, J=2.1 Hz, 1H), 7.49 (s, 1H), 7.32 (d, J=5.1 Hz, 1H), 7.07 (broad, 2H), 6.74 (s, 1H), 6.10 (d, J=2.1 Hz, 1H), 3.80 (s, 3H), 2.79 (q, J=7.0 Hz, 2H), 1.10 (t, J=7.0 Hz, 3H).

Example 75

3-(4-Ethylpyridin-3-yl)-N6-(1H-pyrazol-3-yl)-[2,7]naphthyridine-1,6-diamine (Compound 77)

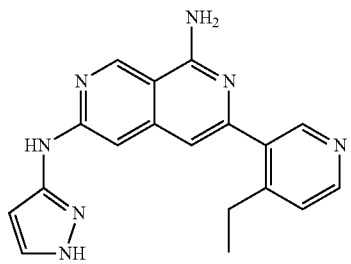 [SMILES: CCc1ccncc1-c1cc2cc(Nc3cc[nH]n3)ncc2c(N)n1]

Step 1: 3-(4-Ethylpyridin-3-yl)-N1,N1-bis-(4-methoxybenzyl)-N6-(1H-pyrazol-3-yl)-[2,7]naphthyridine-1,6-diamine

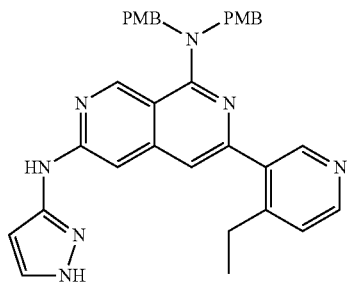

A mixture of 3-(4-ethylpyridin-3-yl)-N1,N1-bis-(4-methoxybenzyl)-[2,7]naphthyridine-1,6-diamine (140 mg, 0.28 mmol), 3-bromo-1-methyl-1H-pyrazole (82 mg, 0.56 mmol), 2-(di-tert-butylphosphino)-2',4',6'-triisopropyl-3,6-dimethoxybiphenyl (13 mg, 0.028 mmol) and t-BuBrettPhos Palladacycle Gen. 3 (24 mg, 0.028 mmol) in dry dioxane (3 mL) was purged with argon. Lithium bis(trimethylsilyl)amide (1 M in toluene, 1.16 mL, 1.16 mmol) was added and the mixture was heated at 100° C. for 16 hours. Further portions of 3-bromo-1-methyl-1H-pyrazole (82 mg, 0.56 mmol) and lithium bis(trimethylsilyl)amide (1.16 mL, 1.16 mmol) were added and the mixture was heated at 100° C. for 22 hours. The cooled mixture was diluted with water and the phases separated. The aqueous phase was extracted with ethyl acetate three times. The organic fractions were dried (Na$_2$SO$_4$) and evaporated. The crude product was chromatographed on silica (eluted with 0-5% methanol/ethyl acetate) to give a slightly impure product which was purified by mass-directed HPLC (C18 column, 10-95% acetonitrile/water+0.1% formic acid) to give the title compound (44 mg, 28% yield). LCMS (ESI): R$_T$ (min)=1.57, [M+H]$^+$=572, method=I.

Step 2: 3-(4-Ethylpyridin-3-yl)-N6-(1H-pyrazol-3-yl)-[2,7]naphthyridine-1,6-diamine

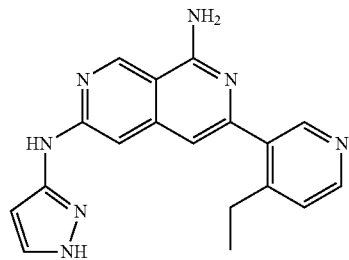 [SMILES: CCc1ccncc1-c1cc2cc(Nc3cc[nH]n3)ncc2c(N)n1]

A solution of 3-(4-ethylpyridin-3-yl)-N1,N1-bis-(4-methoxybenzyl)-N6-(1H-pyrazol-3-yl)-[2,7]naphthyridine-1,6-diamine (44 mg, 0.077 mmol) in TFA (0.5 mL) was heated at 80° C. for 1 hour. The cooled mixture, diluted with methanol and dichloromethane, was loaded onto a 2 g SCX-2 cartridge and eluted with methanol, then with 2M ammonia in methanol. Ammonia fractions were evaporated and the residue was triturated with diethyl ether to give the title compound (20 mg, 80% yield). LCMS (ESI): $R_T$ (min)=2.09, [M+H]$^+$=332, method=J; $^1$H NMR (400 MHz, DMSO-d$_6$) δ 12.17 (broad, 1H), 9.40 (s, 1H), 9.23 (s, 1H), 8.49 (s, 1H), 8.47 (d, J=5.2 Hz, 1H), 7.61 (broad, 2H), 7.33 (d, J=5.2 Hz, 1H), 7.10 (broad s, 2H), 6.74 (s, 1H), 6.12 (d, J=2.1 Hz, 1H), 2.79 (q, J=7.5 Hz, 2H), 1.10 (t, J=7.5 Hz, 3H).

Example 76

3-(4-Ethylpyridin-3-yl)-N6-(1-piperidin-4-yl-1H-pyrazol-4-yl)-[2,7] naphthyridine-1,6-diamine
(Compound 78)

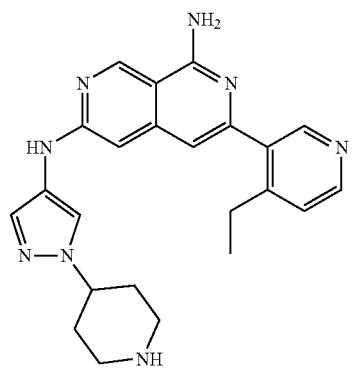 [SMILES: CCc1ccncc1-c1cc2cc(Nc3cnn(C4CCNCC4)c3)ncc2c(N)n1]

Step 1: 4-{4-[8-[Bis-(4-methoxybenzyl)amino]-6-(4-ethylpyridin-3-yl)-[2,7]naphthyridin-3-ylamino]pyrazol-1-yl}piperidine-1-carboxylic acid tert-butyl ester

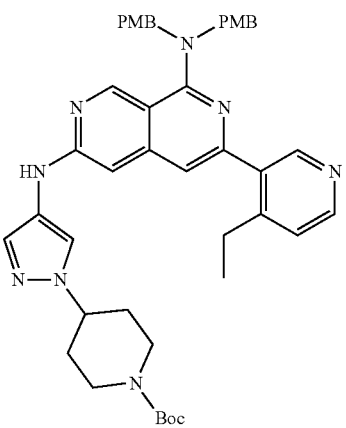

A mixture of 3-(4-ethylpyridin-3-yl)-N1,N1-bis-(4-methoxybenzyl)-[2,7]naphthyridine-1,6-diamine (150 mg, 0.29 mmol), 4-(4-bromopyrazol-1-yl)piperidine-1-carboxylic acid tert-butyl ester (195 mg, 0.59 mmol), 2-(di-tert-butylphosphino)-2',4',6'-triisopropyl-3,6-dimethoxybiphenyl (14 mg, 0.029 mmol) and t-BuBrettPhos Palladacycle Gen. 3 (24 mg, 0.029 mmol) in dry 1,4-dioxane (3 mL) was purged with argon. Lithium bis(trimethylsilyl)amide (1 M in toluene, 1.16 mL, 1.16 mmol) was added and the mixture was heated at 100° C. for 5.5 hours. The cooled mixture was diluted with water and extracted with ethyl acetate three times. The extracts were dried (Na$_2$SO$_4$) and evaporated. The crude product was chromatographed on silica eluted with 0-100% ethyl acetate/cyclohexane to give the title compound (89 mg, 41% yield). LCMS (ESI): $R_T$ (min)=3.50, [M+H]$^+$=755, method=K.

Step 2: 3-(4-Ethylpyridin-3-yl)-N6-(1-piperidin-4-yl-1H-pyrazol-4-yl)-[2,7] naphthyridine-1,6-diamine

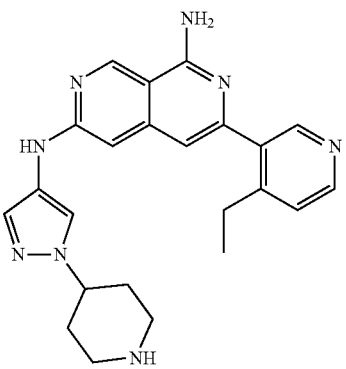 [SMILES: CCc1ccncc1-c1cc2cc(Nc3cnn(C4CCNCC4)c3)ncc2c(N)n1]

A solution of 4-{4-[8-[bis-(4-methoxybenzyl)amino]-6-(4-ethylpyridin-3-yl)-[2,7]naphthyridin-3-ylamino]pyrazol-1-yl}piperidine-1-carboxylic acid tert-butyl ester (89 mg, 0.118 mmol) in TFA (2 mL) was heated at 80° C. for 4 hours, then evaporated. The residue was loaded onto a 2 g SCX-2 cartridge and eluted with methanol, then with 2M ammonia in methanol. Ammonia fractions were evaporated to give the title compound (43 mg, 88% yield). LCMS (ESI): R$_T$ (min)=1.72, [M+H]$^+$=415, method=J; $^1$H NMR (400 MHz, DMSO-d$_6$) δ 9.21 (s, 1H), 8.87 & 8.82 (2×s*, 1H), 8.46 (m, 2H), 7.94 & 7.93 (2×s*, 1H), 7.52 & 7.49 (2×s*, 1H), 7.32 (d, J=5.1 Hz, 1H), 7.06 (broad, 2H), 6.72 (s, 1H), 6.64 (s, 1H), 4.32 & 4.13 (2×m*, 1H), 3.23 & 3.10 (2×m*, 2H), 2.84 (m, 2H), 2.79 (q, J=7.5 Hz, 2H), 2.08 (m, 2H), 1.97 (m, 2H) 1.09 (t, J=7.5 Hz, 3H). *=major & minor conformers.

Example 77

Cyclopropanesulfonic acid [8-amino-6-(4-ethylpyridin-3-yl)-[2,7]naphthyridin-3-yl]amide (Compound 79)

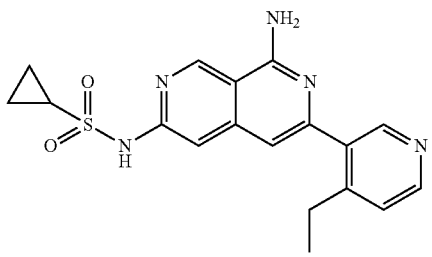 [SMILES: CCc1ccncc1-c1cc2cc(NS(=O)(=O)C3CC3)ncc2c(N)n1]

Step 1:
4-Bromo-1-cyclopropanesulfonyl-1H-pyrazole

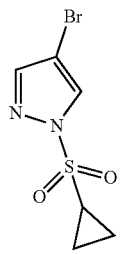 [SMILES: O=S(=O)(C1CC1)n1cc(Br)cn1]

Triethylamine (0.21 mL, 1.50 mmol) was added to a mixture of 4-bromo-H-pyrazole (200 mg, 1.36 mmol) and cyclopropanesulfonyl chloride (0.15 mL, 1.50 mmol) in dry dichloromethane (2 mL). The mixture was stirred at room temperature for 19 hours, then further portions of cyclopropanesulfonyl chloride (0.075 mL) and triethylamine (0.105 mL) were added and stirring was continued for 6.5 hours. Water was added and the phases were separated. The aqueous phase was extracted twice with dichloromethane. Organic fractions were dried (Na$_2$SO$_4$) and evaporated, and the crude product was chromatographed on silica gel (eluted with 0-20% ethyl acetate/cyclohexane) to give the title compound (226 mg, 66% yield). LCMS (ESI): R$_T$(min)=2.79, [M+H]$^+$=251/253, method=K.

Step 2: Cyclopropanesulfonic acid [8-bis-(4-methoxybenzyl)amino-6-(4-ethylpyridin-3-yl-[2,7]naphthyridin-3-yl]amide

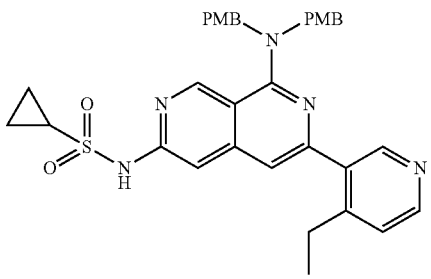

A mixture of 3-(4-ethylpyridin-3-yl)-N1,N1-bis-(4-methoxybenzyl)-[2,7]naphthyridine-1,6-diamine (150 mg, 0.29 mmol), 4-bromo-1-cyclopropanesulfonyl-1H-pyrazole (149 mg, 0.59 mmol), 2-(di-tert-butylphosphino)-2',4',6'-triisopropyl-3,6-dimethoxybiphenyl (14 mg, 0.029 mmol) and t-BuBrettPhos Palladacycle Gen. 3 (24 mg, 0.029 mmol) in dry dioxane (3 mL) was purged with argon. Lithium bis(trimethylsilyl)amide (1 M in toluene, 1.16 mL, 1.16 mmol) was added and the mixture was heated at 100° C. for 17.5 hours. The cooled mixture was diluted with water and extracted with ethyl acetate five times. The extracts were dried (Na$_2$SO$_4$) and evaporated. The crude product was chromatographed on silica gel (eluted with 50-100% ethyl acetate/cyclohexane) to give the title compound (45 mg, 25% yield). LCMS (ESI): R$_T$ (min)=2.75, [M+H]$^+$=572, method=K.

Step 3: Cyclopropanesulfonic acid [8-amino-6-(4-ethylpyridin-3-yl)-[2,7]naphthyridin-3-yl]amide

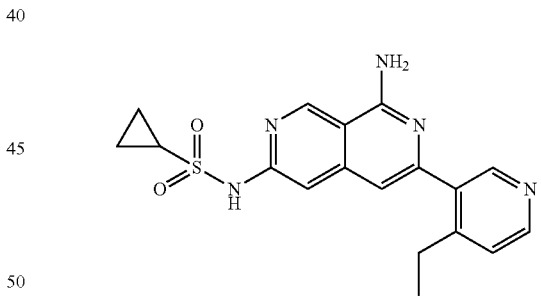

A solution of cyclopropanesulfonic acid [8-[bis-(4-methoxybenzyl)amino-6-(4-ethylpyridin-3-yl)-[2,7]naphthyridin-3-yl]amide (45 mg, 0.074 mmol) in TFA (2 mL) was heated at 80° C. for 4 hours, then evaporated. The residue was slurried with 2M ammonia in methanol, then methanol and dichloromethane added to dissolve all solid. The solution was evaporated onto Isolute® HM-N, loaded onto a silica column and eluted with 0-10% methanol/dichloromethane to give the title compound (26 mg, 95% yield). LCMS (ESI): R$_T$ (min)=2.23, [M+H]$^+$=370, method=J; $^1$H NMR (400 MHz, DMSO-d$_6$) δ 10.84 (broad s, 1H), 9.38 (s, 1H), 8.52 (s, 1H & d, J=5.1 Hz, 1H), 7.58 (broad, 2H), 7.38 (d, J=5.1 Hz, 1H), 7.23 (s, 1H), 6.97 (s, 1H), 3.08 (m, 1H), 2.78 (q, J=7.2 Hz, 2H), 1.10 (m, 5H), 1.03 (m, 2H).

Example 78

3-(4-Ethylpyridin-3-yl)-N6-(6-methylpyrimidin-4-yl)-[2,7]naphthyridine-1,6-diamine (Compound 80)

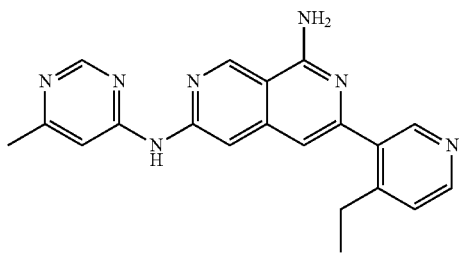 [SMILES: CCc1ccncc1-c1cc2cc(Nc3cc(C)ncn3)ncc2c(N)n1]

Step 1: 3-(4-Ethylpyridin-3-yl)-N1,N1-bis-(4-methoxybenzyl)-N6-(6-methylpyrimidin-4-yl)-[2,7]naphthyridine-1,6-diamine

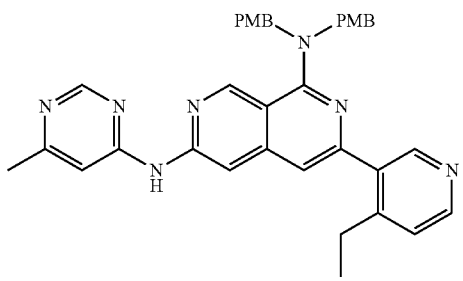

A mixture of 3-(4-ethylpyridin-3-yl)-N1,N1-bis-(4-methoxybenzyl)-[2,7]naphthyridine-1,6-diamine (150 mg, 0.29 mmol), 4-chloro-6-methylpyrimidine (58 mg, 0.45 mmol), tris(dibenzylideneacetone)dipalladium(0) (13 mg, 0.015 mmol), X-Phos (15 mg, 0.03 mmol) and cesium carbonate (189 mg, 0.58 mmol) in dry 1,4-dioxane (2 mL) was purged with argon and heated at 120° C. for 18 hours. The cooled mixture was diluted with water and extracted with ethyl acetate five times. The organic extracts were dried (Na$_2$SO$_4$) and evaporated. The crude product was purified by mass-directed HPLC (C18 column, 10-95% acetonitrile/water+0.1% ammonia) to give the title compound (40 mg, 23% yield). LCMS (ESI): R$_T$ (min)=2.64, [M+H]+=598, method=K.

Step 2: 3-(4-Ethylpyridin-3-yl)-N6-(6-methylpyrimidin-4-yl)-[2,7]naphthyridine-1,6-diamine

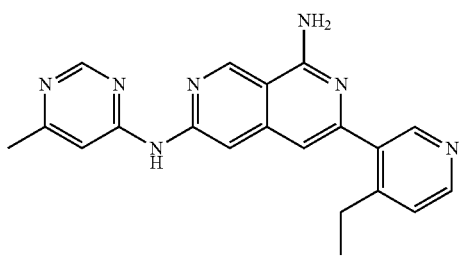 [SMILES: CCc1ccncc1-c1cc2cc(Nc3cc(C)ncn3)ncc2c(N)n1]

A solution of 3-(4-ethylpyridin-3-yl)-N1,N1-bis-(4-methoxybenzyl)-N6-(6-methylpyrimidin-4-yl)-[2,7]naphthyridine-1,6-diamine (40 mg, 0.067 mmol) in TFA (2 mL) was heated at 80° C. for 4.5 hours, then evaporated. The residue was loaded onto a 2 g SCX-2 cartridge and eluted with methanol, then with 2M ammonia in methanol. Ammonia fractions were evaporated to give the title compound (25 mg, 100% yield). LCMS (ESI): R$_T$ (min)=1.86, [M+H]$^+$=358, method=J; $^1$H NMR (400 MHz, DMSO-d$_6$) δ 10.33 (s, 1H), 9.39 (s, 1H), 8.65 (s, 1H), 8.51 (s, 1H), 8.49 (d, J=5.1 Hz, 1H), 8.19 (s, 1H), 7.35 (d, J=5.1 Hz, 1H), 7.31 (broad, 2H), 7.28 (s, 1H), 6.92 (s, 1H), 2.80 (q, J=7.5 Hz, 2H), 2.36 (s, 3H), 1.10 (t, 3H).

Example 79

2-[8-Amino-6-(4-ethylpyridin-3-yl)-[2,7]naphthyridin-3-ylamino]-N-ethyl-N-methylisonicotinamide (Compound 81)

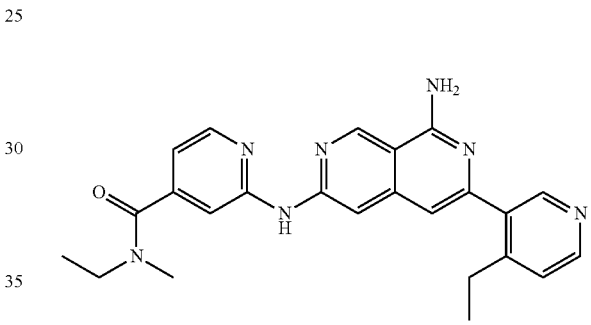

Step 1: 2-Chloro-N-ethyl-N-methylisonicotinamide

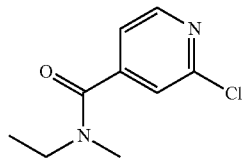

To a solution of 2-chloroisonicotinic acid (0.29 g, 1.85 mmol) in DMF (15 mL) was added O-(7-azabenzotriazol-1-yl)-N,N,N'N'-tetramethyluronium hexafluorophosphate (1.06 g, 2.78 mmol), N-ethylmethylamine (0.24 mL, 2.78 mmol), and N,N-diisopropylethylamine (1.25 mL, 7.4 mmol). The mixture was stirred at room temperature for 18 hours, then diluted with water and extracted with ethyl acetate four times. The extracts were washed with water and brine, dried (Na$_2$SO$_4$) and evaporated. The crude product was chromatographed on silica eluted with 0-50% ethyl acetate/cyclohexane to give the title compound (273 mg, 75% yield). LCMS (ESI): R$_T$ (min)=1.99, [M+H]$^+$=199, method=K.

Step 2: 2-[8-[Bis-(4-methoxybenzyl)amino]-6-(4-ethylpyridin-3-yl)-[2,7]naphthyridin-3-ylamino]-N-ethyl-N-methylisonicotinamide

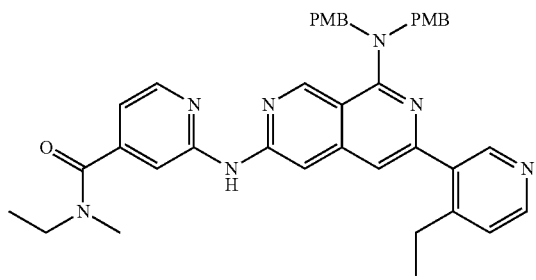

A mixture of 3-(4-ethylpyridin-3-yl)-N1,N1-bis-(4-methoxybenzyl)-[2,7]naphthyridine-1,6-diamine (150 mg, 0.29 mmol), 2-chloro-N-ethyl-N-methylisonicotinamide (115 mg, 0.58 mmol), tris(dibenzylideneacetone)dipalladium(0) (13 mg, 0.015 mmol), X-Phos (15 mg, 0.03 mmol) and cesium carbonate (189 mg, 0.58 mmol) in dry dioxane (2 mL) was purged with Argon and heated at 120° C. for 18 hours. The cooled mixture was diluted with water and extracted with ethyl acetate three times. The organic extracts were dried (Na$_2$SO$_4$) and evaporated. Crude product was chromatographed on silica (eluted with 50-100% ethyl acetate/cyclohexane) to give the title compound (85 mg, 44% yield). LCMS (ESI): R$_T$ (min)=2.67, [M+H]$^+$=668, method=K.

Step 3: 2-[8-Amino-6-(4-ethylpyridin-3-yl)-[2,7]naphthyridin-3-ylamino]-N-ethyl-N-methylisonicotinamide

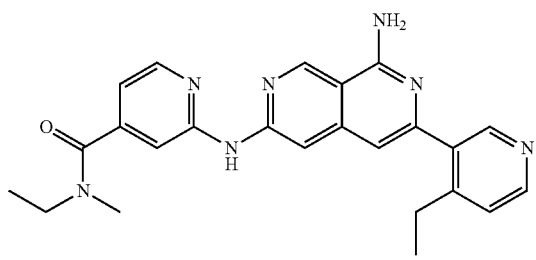 [SMILES: CCc1ccncc1-c1cc2cc(Nc3cc(C(=O)N(C)CC)ccn3)ncc2c(N)n1]

A solution of 2-[8-[bis-(4-methoxybenzyl)amino]-6-(4-ethylpyridin-3-yl)-[2,7]naphthyridin-3-ylamino]-N-ethyl-N-methylisonicotinamide (85 mg, 0.13 mmol) in TFA (2 mL) was heated at 80° C. for 4 hours, then evaporated. The residue was loaded onto a 2 g SCX-2 cartridge and eluted with methanol, then with 2M ammonia in methanol. Ammonia fractions were evaporated and the residue was chromatographed on silica (eluted with 0-7% methanol/dichloromethane) to give the title compound (46 mg, 83% yield). LCMS (ESI): R$_T$(min)=2.30, [M+H]$^+$=428, method=J; $^1$H NMR (400 MHz, DMSO-d$_6$, 80° C.) δ 9.73 (broad s, 1H), 9.32 (s, 1H), 8.50 (s, 1H), 8.46 (d, J=5.5 Hz, 1H), 8.31 (d, J=5.0 Hz, 1H), 8.07 (s, 1H), 7.43 (s, 1H), 7.29 (d, J=5.5 Hz, 1H), 6.91 (broad, 2H), 6.84 (s, 1H), 6.82 (d, J=5.1 Hz, 1H), 3.34 (broad, 2H), 2.93 (s, 3H), 2.80 (q, J=7.5 Hz, 2H), 1.12 (m, 6H).

Example 80

(±)-1-{2-[8-Amino-6-(4-ethylpyridin-3-yl)-[2,7]naphthyridin-3-ylamino]-pyridin-4-yl}propan-1-ol (Compound 82)

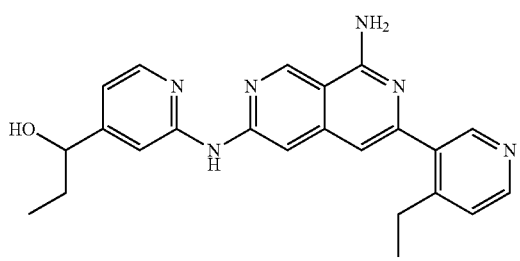 [SMILES: CCc1ccncc1-c1cc2cc(Nc3cc(C(O)CC)ccn3)ncc2c(N)n1]

Step 1: (±)-1-(2-Chloropyridin-4-yl)propan-1-ol

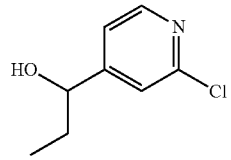

To a solution of 2-chloropyridine-4-carbaldehyde (0.71 g, 5.06 mmol) in anhydrous THF (16 mL) was added a solution of lanthanum(III) chloride bis(lithium chloride) complex (0.6M in THF, 16.7 mL, 10.03 mmol) and the mixture was stirred at room temperature for 0.75 hours, then cooled to 0° C. Ethyl magnesium bromide (3M in diethyl ether, 3.34 mL, 10.03 mmol) was added dropwise over 5-10 minutes. The mixture was stirred at 0° C. for 80 minutes, then quenched with aqueous ammonium chloride, diluted with water and extracted with ethyl acetate (3×). The organic extracts were dried (Na$_2$SO$_4$) and evaporated. The crude product was chromatographed on silica gel (eluted with 0-50% ethyl acetate/cyclohexane) to give the title compound (423 mg, 49% yield). LCMS (ESI): R$_T$ (min)=2.14, [M+H]$^+$=172, method=K. Further elution gave (2-chloropyridin-4-yl)methanol (191 mg, 26% yield). LCMS (ESI): R$_T$(min)=1.46, [M+H]$^+$=144, method=K.

Step 2: (±)-1-{2-[8-[Bis-(4-methoxybenzyl)amino]-6-(4-ethylpyridin-3-yl)-[2,7]naphthyridin-3-ylamino]pyridin-4-yl}propan-1-ol

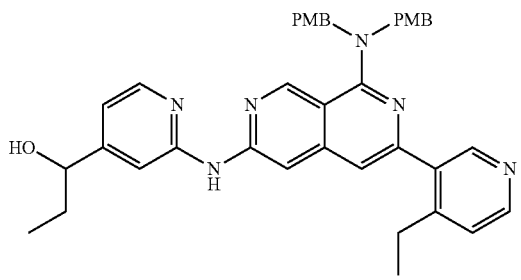

A mixture of 3-(4-ethylpyridin-3-yl)-N1,N1-bis-(4-methoxybenzyl)-[2,7]naphthyridine-1,6-diamine (150 mg, 0.29 mmol), (±)-1-(2-chloropyridin-4-yl)propan-1-ol (100 mg, 0.58 mmol), tris(dibenzylideneacetone)dipalladium(0) (13 mg, 0.015 mmol), X-Phos (15 mg, 0.03 mmol) and cesium carbonate (189 mg, 0.58 mmol) in dry dioxane (2 mL) was purged with argon and heated at 120° C. for 16 hours. The cooled mixture was diluted with water and extracted with ethyl acetate (5×). The organic extracts were dried (Na₂SO₄) and evaporated. The crude product was purified by mass-directed HPLC (C18 column, 10-95% acetonitrile/water+0.1% formic acid) to give the title compound (68 mg, 36% yield). LCMS (ESI): R$_T$ (min)=2.47, [M+H]⁺=641, method=K.

Step 3: (±)-1-{2-[8-Amino-6-(4-ethylpyridin-3-yl)-[2,7]naphthyridin-3-ylamino]-pyridin-4-yl}propan-1-ol

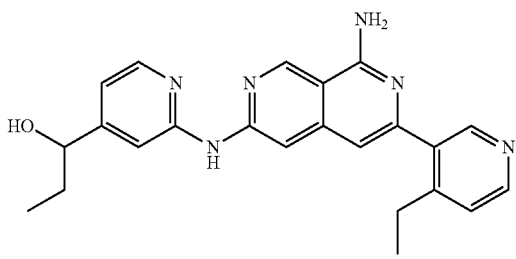 [SMILES: CCc1ccncc1-c1cc2cc(Nc3cc(C(O)CC)ccn3)ncc2c(N)n1]

A solution of (±)-1-{2-[8-[bis-(4-methoxybenzyl)amino]-6-(4-ethylpyridin-3-yl)-[2,7]naphthyridin-3-ylamino]pyridin-4-yl}propan-1-ol (68 mg, 0.106 mmol) in TFA (2 mL) was heated at 80° C. for 4.5 hours, then evaporated. The residue was loaded onto a 2 g SCX-2 cartridge and eluted with methanol, then with 2M ammonia in methanol. Ammonia fractions were evaporated and the residue was chromatographed on silica (eluted with 0-10% methanol/dichloromethane) to give the title compound (26 mg, 61% yield). LCMS (ESI): R$_T$(min)=2.04, [M+H]⁺=401, method=J; ¹H NMR (400 MHz, DMSO-d₆) δ 9.94 (broad s, 1H), 9.35 (s, 1H), 8.51 (s, 1H), 8.50 (d, J=5.1 Hz, 1H), 8.25 (s, 1H), 8.20 (d, J=5.1 Hz, 1H), 7.35 (broad m, 4H), 6.87 (broad m, 2H), 5.33 (d, J=4.2 Hz, 1H), 4.43 (m, 1H), 2.79 (q, J=7.5 Hz, 2H), 1.61 (m, 2H), 1.11 (t, J=7.5 Hz, 3H), 0.87 (t, J=7.3 Hz, 3H)

Example 81

{6-[8-amino-6-(4-ethylpyridin-3-yl)-[2,7]naphthyridin-3-ylamino]pyridin-2-yl}methanol (Compound 83)

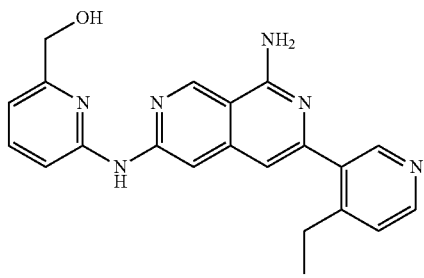 [SMILES: CCc1ccncc1-c1cc2cc(Nc3cccc(CO)n3)ncc2c(N)n1]

Step 1: {6-[8-[Bis-(4-methoxybenzyl)amino]-6-(4-ethylpyridin-3-yl)-[2,7]naphthyridin-3-ylamino]pyridin-2-yl}methanol

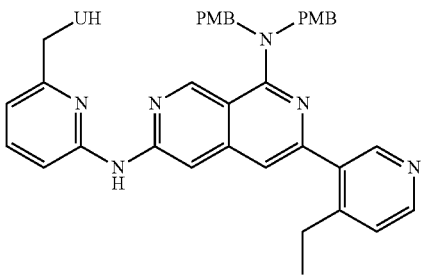

A mixture of 3-(4-ethylpyridin-3-yl)-N1,N1-bis-(4-methoxybenzyl)-[2,7]naphthyridine-1,6-diamine (150 mg, 0.29 mmol), (6-chloropyridin-2-yl)methanol (83 mg, 0.58 mmol), tris(dibenzylideneacetone)dipalladium(0) (13 mg, 0.015 mmol), X-Phos (15 mg, 0.03 mmol) and cesium carbonate (189 mg, 0.58 mmol) in dry dioxane (2 mL) was purged with argon and heated at 120° C. for 16 hours. The cooled mixture was diluted with water and extracted with ethyl acetate four times. The organic extracts were dried (Na₂SO₄) and evaporated. The crude product was chromatographed on silica (eluted with 50-100% ethyl acetate/cyclohexane) to give the title compound (56 mg, 32% yield). LCMS (ESI): R$_T$ (min)=2.36, [M+H]⁺=613, method=K.

Step 2: {6-[8-amino-6-(4-ethylpyridin-3-yl)-[2,7]naphthyridin-3-ylamino]pyridin-2-yl}methanol

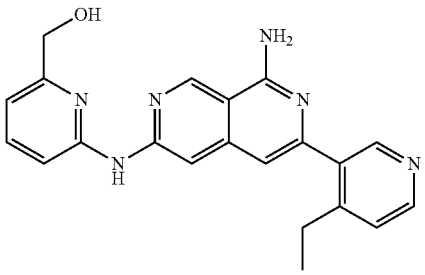 [SMILES: CCc1ccncc1-c1cc2cc(Nc3cccc(CO)n3)ncc2c(N)n1]

A solution of {6-[8-[bis-(4-methoxybenzyl)amino]-6-(4-ethylpyridin-3-yl)-[2,7]naphthyridin-3-ylamino]pyridin-2-yl}methanol (56 mg, 0.092 mmol) in TFA (2 mL) was heated at 80° C. for 4 hours, then evaporated. The residue was loaded onto a 2 g SCX-2 cartridge and eluted with methanol, then with 2M ammonia in methanol. Ammonia fractions were evaporated and the residue was chromatographed on silica (eluted with 0-10% methanol/dichloromethane) to give the title compound (25 mg, 73% yield). LCMS (ESI): R$_T$(min)=1.81, [M+H]⁺=373, method=J; ¹H NMR (400 MHz, DMSO-d₆) δ 9.86 (s, 1H), 9.31 (s, 1H), 8.50 (s, 1H), 8.48 (d, J=5.1 Hz, 1H), 8.27 (s, 1H), 7.66 (t, J=7.7 Hz, 1H), 7.34 (d, J=5.1 Hz, 1H), 7.25 (d, J=7.7 Hz, 1H), 7.16 (broad, 2H), 6.97 (d, J=5.1 Hz, 1H)), 6.86 (s, 1H), 5.34 (t, J=6.0 Hz, 1H), 4.55 (d, J=6.0 Hz, 2H), 2.80 (q, J=7.5 Hz, 2H), 1.11 (t, J=7.5 Hz, 3H).

Example 82

1-Piperidin-4-yl-1H-pyrazole-4-carboxylic acid [8-amino-6-(4-ethylpyridin-3-yl)-[2,7]naphthyridin-3-yl]amide (Compound 84)

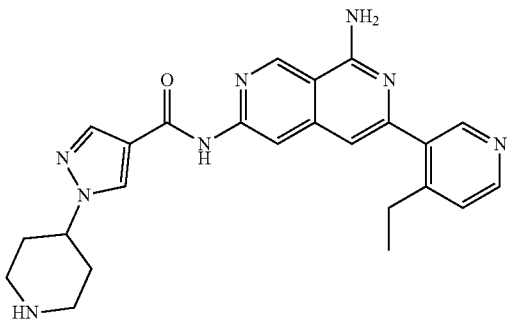 [SMILES: CCc1ccncc1-c1cc2cc(NC(=O)c3cnn(C4CCNCC4)c3)ncc2c(N)n1]

Step 1: 4-(4-Ethoxycarbonylpyrazol-1-yl)piperidine-1-carboxylic acid tert-butyl ester

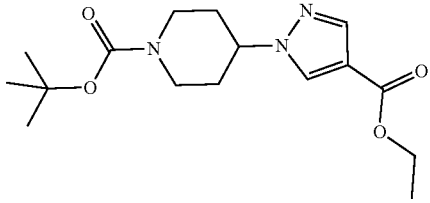 [SMILES: CCOC(=O)c1cnn(C2CCN(C(=O)OC(C)(C)C)CC2)c1]

A mixture of ethyl 1H-pyrazole-4-carboxylate (0.20 g, 1.40 mmol) and 4-methanesulfonyloxypiperidine-1-carboxylic acid tert-butyl ester (0.36 g, 1.30 mmol) in dry DMF (5 mL) was cooled to 0° C. Sodium hydride (60% in mineral oil, 78 mg, 1.95 mmol) was added and the mixture was stirred at 0° C. for 0.5 hours, then heated at 50° C. for 16 hours. The cooled mixture was diluted with diethyl ether and water and the phases separated. The aqueous phase was extracted again with ether. The combined organic fractions were washed with water (4×) and brine, dried (Na$_2$SO$_4$) and evaporated. The crude product was chromatographed on silica (eluted with 0-40% ethyl acetate/cyclohexane) to give the title compound (0.183 g, 44% yield). LCMS (ESI): R$_T$ (min)=3.27, [M+H]$^+$—C$_4$H$_8$-ethanol=222, method=K.

Step 2: 4-(4-Carboxypyrazol-1-yl)piperidine-1-carboxylic acid tert-butyl ester

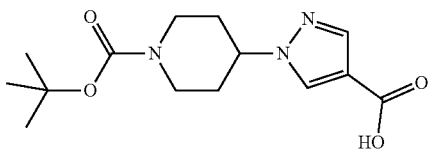 [SMILES: CC(C)(C)OC(=O)N1CCC(n2cc(C(=O)O)cn2)CC1]

A mixture of 4-(4-ethoxycarbonylpyrazol-1-yl)piperidine-1-carboxylic acid tert-butyl ester (0.183 g, 0.57 mmol) and potassium hydroxide (0.127 g, 2.27 mmol) in methanol (2 mL) and water (0.5 mL) was stirred at room temperature for 16 hours. The solvent was removed under vacuum and the residue was treated with 5% aqueous potassium hydrogensulfate to acidify, then extracted with ethyl acetate (5×). The extracts were dried (Na$_2$SO$_4$) and evaporated to give the title compound (0.158 g, 94% yield). LCMS (ESI): R$_T$ (min)=2.58, [M+H]$^+$—C$_4$H$_8$=240, [M−H]$^−$=294, method=K.

Step 3: 4-{4-[8-[Bis-(4-methoxybenzyl)amino]-6-(4-ethylpyridin-3-yl)-[2,7]naphthyridin-3-ylcarbamoyl]pyrazol-1-yl}piperidine-1-carboxylic acid tert-butyl ester

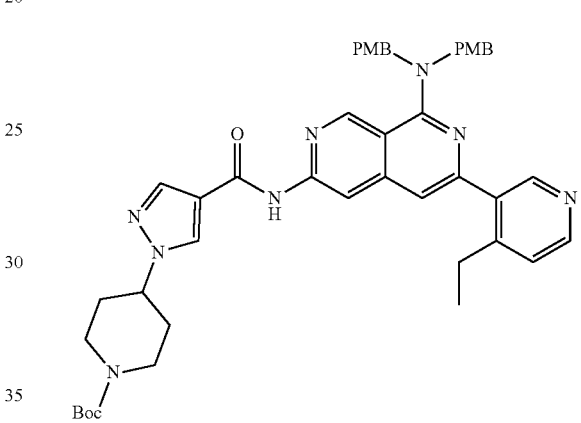

To a solution of 4-(4-carboxypyrazol-1-yl)piperidine-1-carboxylic acid tert-butyl ester (158 mg, 0.54 mmol) in dry dichloromethane (10 mL) was added oxalyl chloride (0.091 mL, 1.07 mmol) and DMF (2 drops). The mixture was stirred at room temperature for 3 hours. A further portion of oxalyl chloride (0.09 mL) was added and stirring continued for 2 hours. The mixture was then evaporated. The residue was azeotroped twice with dry chloroform then dried under vacuum to give crude acid chloride. A mixture of this material (0.54 mmol crude), 3-(4-ethylpyridin-3-yl)-N1,N1-bis-(4-methoxybenzyl)-[2,7]naphthyridine-1,6-diamine (150 mg, 0.29 mmol) and pyridine (0.12 mL, 1.44 mmol) in dry dichloromethane (2.5 mL) was stirred at room temperature for 22 hours, then water was added and the phases separated. The aqueous phase was extracted with dichloromethane (4×). The combined organic fractions were treated with methanol, dried (Na$_2$SO$_4$) and evaporated. The crude product was purified by mass-directed HPLC (C18 column, 10-95% acetonitrile/water+0.1% formic acid) to give the title compound (34 mg, 8% yield). LCMS (ESI): R$_T$ (min)=3.69, [M+H]$^+$=783, method=K.

Step 4: 1-Piperidin-4-yl-1H-pyrazole-4-carboxylic acid [8-amino-6-(4-ethylpyridin-3-yl)-[2,7]naphthyridin-3-yl]amide

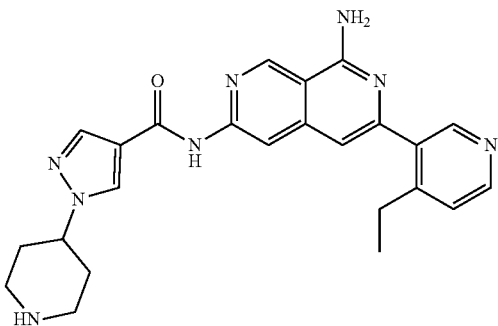 [SMILES: CCc1ccncc1-c1cc2cc(NC(=O)c3cnn(C4CCNCC4)c3)ncc2c(N)n1]

A solution of 4-{4-[8-[bis-(4-methoxybenzyl)amino]-6-(4-ethylpyridin-3-yl)-[2,7]naphthyridin-3-ylcarbamoyl]pyrazol-1-yl}piperidine-1-carboxylic acid tert-butyl ester (34 mg, 0.043 mmol) in TFA (2 mL) was heated at 80° C. for 2.5 hours, then evaporated. The residue was loaded onto a 2 g SCX-2 cartridge and eluted with methanol, then with 2M ammonia in methanol. Ammonia fractions were evaporated and the residue was triturated with dichloromethane and dried under vacuum to give the title compound (12 mg, 63% yield). LCMS (ESI): $R_T$ (min)=1.81, $[M+H]^+$=443, method=J; $^1$H NMR (400 MHz, DMSO-$d_6$) δ 10.28 (broad s, 1H), 9.40 (s, 1H), 8.55 (s, 1H), 8.51 (s, 1H), 8.47 (d, J=5.1 Hz, 1H), 8.32 (s, 1H), 8.11 (s, 1H), 7.30 (d, J=5.1 Hz, 1H), 7.04 (broad, 2H), 6.95 (s, 1H), 4.25 (m, 1H), 3.07 (m, 2H, masked by water), 2.80 (q, J=7.5 Hz, 2H), 2.64 (m, 2H), 2.02 (m, 2H), 1.80 (m, 2H), 1.11 (t, J=7.5 Hz, 3H).

Example 83

2-{4-[8-Amino-6-(4-ethylpyridin-3-yl)-[2,7]naphthyridin-3-ylamino]pyrazol-1-yl}ethanol (Compound 85)

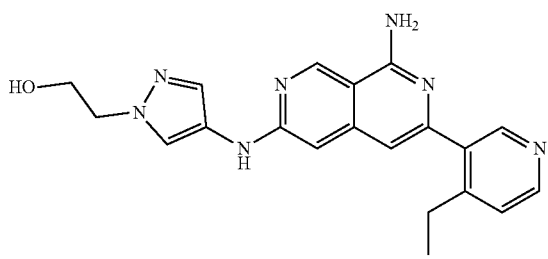 [SMILES: CCc1ccncc1-c1cc2cc(Nc3cnn(CCO)c3)ncc2c(N)n1]

Step 1: 4-Bromo-1-[2-(tetrahydropyran-2-yloxy)ethyl]-1H-pyrazole

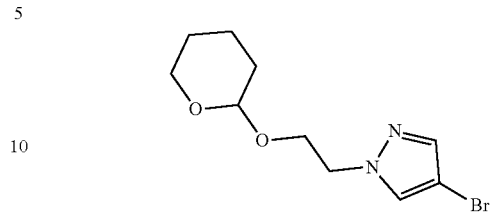

Sodium hydride (60% in mineral oil, 0.65 g, 16.3 mmol) was added to a solution of 4-bromo-1H-pyrazole (0.80 g, 5.44 mmol) in dry DMF (20 mL) at 0° C. The mixture was stirred at 0° C. for 0.5 hours, then 2-(2-bromoethoxy)tetrahydropyran (1.71 g, 8.16 mmol) was added dropwise. The mixture was stirred at 0° C. for another 1 hours, then allowed to warm to room temperature overnight. Water was added cautiously, followed by ethyl acetate and more water. The phases were separated and the aqueous phase was extracted with ethyl acetate (2×). The combined organic fractions were washed with brine, dried ($Na_2SO_4$) and evaporated. The residue was chromatographed on silica (eluted with 0-50% ethyl acetate/cyclohexane) to give the title compound (1.40 g, 94% yield). LCMS (ESI): $R_T$ (min)=2.96, $[M+H-THP]^+$=191/193, method=K.

Step 2: 3-(4-Ethylpyridin-3-yl)-N1,N1-bis-(4-methoxybenzyl)-N6-{1-[2-(tetrahydropyran-2-yloxy)ethyl]-1H-pyrazol-4-yl}-[2,7]naphthyridine-1,6-diamine

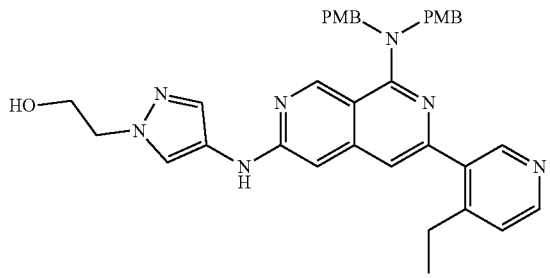

A mixture of 3-(4-ethylpyridin-3-yl)-N1,N1-bis-(4-methoxybenzyl)-[2,7]naphthyridine-1,6-diamine (160 mg, 0.32 mmol), 4-bromo-1-[2-(tetrahydropyran-2-yloxy)ethyl]-1H-pyrazole (176 mg, 0.64 mmol), 2-(di-tert-butylphosphino)-2',4',6'-triisopropyl-3,6-dimethoxybiphenyl (15 mg, 0.03 mmol) and t-BuBrettPhos Palladacycle Gen. 3 (27 mg, 0.03 mmol) in dry 1,4-dioxane (3 mL) was purged with argon. Lithium bis(trimethylsilyl)amide (1 M in toluene, 1.32 mL, 1.32 mmol) was added and the mixture was heated at 100° C. for 16 hours. The cooled mixture was diluted with water and extracted with ethyl acetate (5×). The extracts were dried ($Na_2SO_4$) and evaporated. The crude product was chromatographed on silica (eluted with 0-100% ethyl acetate/cyclohexane) to give the title compound (70 mg, 31% yield). LCMS (ESI): $R_T$ (min)=3.14, $[M+H]^+$=700, method=K.

Step 3: 2-{4-[8-Amino-6-(4-ethylpyridin-3-yl)-[2,7]naphthyridin-3-ylamino]pyrazol-1-yl}ethanol

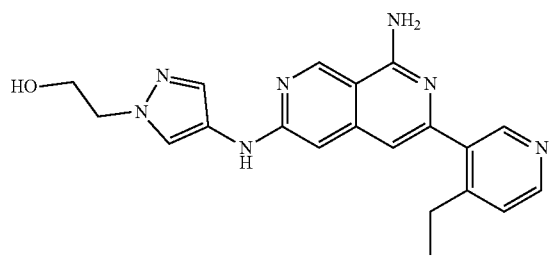 [SMILES: CCc1ccncc1-c1cc2cc(Nc3cnn(CCO)c3)ncc2c(N)n1]

A solution of 3-(4-ethylpyridin-3-yl)-N1,N1-bis-(4-methoxybenzyl)-N6-{1-[2-(tetrahydropyran-2-yloxy)ethyl]-1H-pyrazol-4-yl}-[2,7]naphthyridine-1,6-diamine (70 mg, 0.10 mmol) in TFA (2 mL) was heated at 80° C. for 4 hours, then evaporated. The residue was loaded onto a 2 g SCX-2 cartridge and eluted with methanol, then with 2M ammonia in methanol. Ammonia fractions were evaporated and the residue was chromatographed on silica (eluted with 0-10% methanol/dichloromethane) to give the title compound (22 mg, 59% yield). LCMS (ESI): $R_T$ (min)=1.93, $[M+H]^+$=376, method=J; $^1$H NMR (400 MHz, DMSO-$d_6$) δ 9.21 (s, 1H), 8.84 (s, 1H), 8.46 (s, 1H & d, J=5.1 Hz, 1H), 7.91 (s, 1H), 7.49 (s, 1H), 7.32 (d, J=5.1 Hz, 1H), 7.04 (broad, 2H), 6.71 (s, 1H), 6.63 (s, 1H), 4.89 (t, J=5.5 Hz, 1H), 4.12 (t, J=5.8 Hz, 2H), 3.74 (q, J=5.8 Hz, 2H), 2.78 (q, J=7.5 Hz, 2H), 1.09 (t, J=7.5 Hz, 3H).

Example 84

(±)-3-(4-methyl-3-pyridyl)-N6-pyrrolidin-3-yl-2,7-naphthyridine-1,6-diamine (Compound 120)

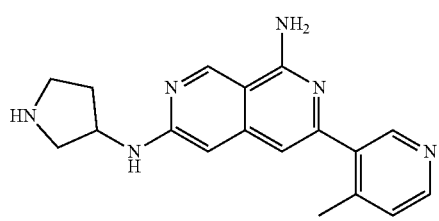 [SMILES: Cc1ccncc1-c1cc2cc(NC3CCNC3)ncc2c(N)n1]

Step 1: tert-butyl 3-hydroxypyrrolidine-1-carboxylate

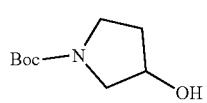 [SMILES: CC(C)(C)OC(=O)N1CCC(O)C1]

NaBH$_4$ (0.3 g, 7.9 mmol) was added portionwise to a solution of N-Boc-3-pyrrolidinone (1.2 g, 6.48 mmol) in methyl alcohol (15 mL). The resultant mixture was stirred at 25° C. for 1 h. To the reaction mixture was added H$_2$O (3 mL) and the mixture was concentrated. The residue was purified with silica-gel chromatography (PE:EA=1:1 to EA) to give (±)-tert-butyl 3-hydroxypyrrolidine-1-carboxylate (1.1 g, 91% yield) as a colorless oil. LCMS (ESI) $[M+23]^+$=210.1.

Step 2: (±)-tert-butyl 3-[tert-butoxycarbonyl-(6,8-dichloro-2,7-naphthyridin-3-yl)amino]pyrrolidine-1-carboxylate

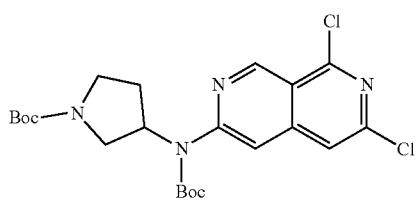 [SMILES: CC(C)(C)OC(=O)N1CCC(N(C(=O)OC(C)(C)C)c2cc3cc(Cl)nc(Cl)c3cn2)C1]

DIAD (550 mg, 2.72 mmol) was added to a mixture of tert-butyl N-(6,8-dichloro-2,7-naphthyridin-3-yl)carbamate (300 mg, 0.95 mmol), (±)-tert-butyl 3-hydroxypyrrolidine-1-carboxylate (400 mg, 2.14 mmol), and PPh$_3$ (550 mg, 2.1 mmol) in tetrahydrofuran (15 mL). The resultant mixture was stirred at 50° C. under Ar for 18 h. The reaction mixture was concentrated and the residue was purified by silica-gel chromatography (PE:EA=4:1) to give (±)-tert-butyl 3-[tert-butoxycarbonyl-(6,8-dichloro-2,7-naphthyridin-3-yl)amino]pyrrolidine-1-carboxylate (crude, 600 mg, mixed with some DIAD+2) as a yellow oil. LCMS (ESI) $[M-Boc]^+$=383.1.

Step 3: (±)-tert-butyl 3-[(8-amino-6-chloro-2,7-naphthyridin-3-yl)-tert-butoxycarbonyl-amino]pyrrolidine-1-carboxylate

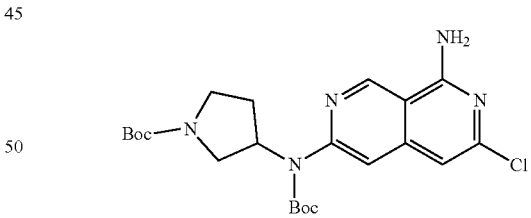

A mixture of (±)-tert-butyl 3-[tert-butoxycarbonyl-(6,8-dichloro-2,7-naphthyridin-3-yl)amino]pyrrolidine-1-carboxylate (600 mg, crude) in ammonium hydroxide (10 mL), 1,4-dioxane (10 mL) was stirred at 90° C. in sealed tube for 3 h. The reaction mixture was cooled to room temperature and evaporated. The residue was purified with silica-gel chromatography (PE:EA=1:2 to 1:3) to give (±)-tert-butyl 3-[(8-amino-6-chloro-2,7-naphthyridin-3-yl)-tert-butoxycarbonyl-amino]pyrrolidine-1-carboxylate (310 mg, 70% yield for two steps) as a colorless oil. LCMS (ESI) $[M+H]^+$=464.2.

Step 4: (±)-tert-butyl 3-[[8-amino-6-(4-methyl-3-pyridyl)-2,7-naphthyridin-3-yl]-tert-butoxycarbonyl-amino]pyrrolidine-1-carboxylate

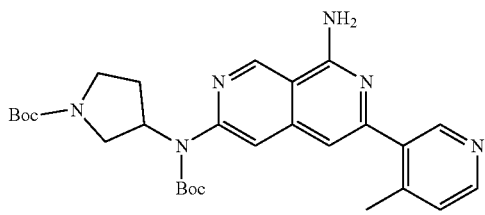 [SMILES: Cc1ccncc1-c1cc2cc(N(C(=O)OC(C)(C)C)C3CCN(C(=O)OC(C)(C)C)C3)ncc2c(N)n1]

A mixture of (±)-tert-butyl 3-[(8-amino-6-chloro-2,7-naphthyridin-3-yl)-tert-butoxycarbonyl-amino]pyrrolidine-1-carboxylate (310 mg, 0.67 mmol), 4-methyl-3-(4,4,5,5-tetramethyl-1,3,2-dioxaborolan-2-yl)pyridine (170 mg, 0.78 mmol), XPhos Pd G2 (70 mg, 0.09 mmol), XPhos (70 mg, 0.15 mmol) and K$_2$CO$_3$ (310 mg, 2.25 mmol) in 1,4-dioxane (16 mL) and water (4 mL) was stirred at 100° C. under Ar for 2 h. The reaction mixture was cooled to room temperature and diluted with ethyl acetate (100 mL) and washed with brine (30 mL). The organic layer was separated, dried over Na$_2$SO$_4$, filtered and evaporated. The residue was purified with silica-gel chromatography (EA to EA:MeOH=20:1) to give (±)-tert-butyl 3-[[8-amino-6-(4-methyl-3-pyridyl)-2,7-naphthyridin-3-yl]-tert-butoxycarbonyl-amino]pyrrolidine-1-carboxylate (250 mg, 72% yield) as a brown solid. LCMS (ESI) [M+H]$^+$=521.3.

Step 5: (±)-3-(4-methyl-3-pyridyl)-N6-pyrrolidin-3-yl-2,7-naphthyridine-1,6-diamine

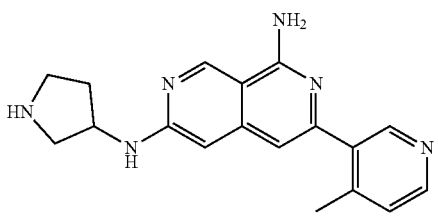 [SMILES: Cc1ccncc1-c1cc2cc(NC3CCNC3)ncc2c(N)n1]

A mixture of (±)-tert-butyl 3-[[8-amino-6-(4-methyl-3-pyridyl)-2,7-naphthyridin-3-yl]-tert-butoxycarbonyl-amino]pyrrolidine-1-carboxylate (250 mg, 0.48 mmol) in 2,2,2-trifluoroacetic acid (4 mL), dichloromethane (12 mL) was stirred at 25° C. for 1 h. The reaction mixture was evaporated. The residue was dissolved in MeOH (2 mL) and pH adjusted to 9-10 by adding 7N NH$_3$/MeOH. The mixture was purified by flash chromatography (C18, HCOOH/MeOH/H$_2$O) to give the bis-formate salt of (±)-3-(4-methyl-3-pyridyl)-N6-pyrrolidin-3-yl-2,7-naphthyridine-1,6-diamine (140 mg, 71% yield) as a yellow solid. LCMS (ESI): R$_T$ (min)=1.34, [M+H]$^+$=321.1, method=C; $^1$H NMR (400 MHz, CD$_3$OD): δ 9.20 (s, 1H), 8.52 (s, 1H), 8.47 (d, J=5.2 Hz, 1H), 8.41 (brs, 2H), 7.42 (d, J=5.2 Hz, 1H), 6.78 (s, 1H), 6.65 (s, 1H), 4.69-4.66 (m, 1H), 3.66-3.54 (m, 2H), 3.48-3.37 (m, 2H), 2.48-2.41 (m, 1H), 2.44 (s, 3H), 2.20-2.15 (m, 1H).

Example 85

(±)-trans-N-[8-amino-6-(4-methyl-3-pyridyl)-2,7-naphthyridin-3-yl]-2-(1H-pyrazol-3-yl)cyclopropanecarboxamide (Compound 121)

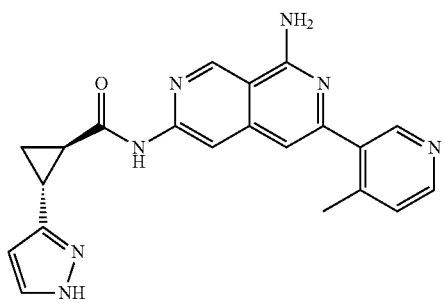 [SMILES: Cc1ccncc1-c1cc2cc(NC(=O)[C@@H]3C[C@H]3c3cc[nH]n3)ncc2c(N)n1]

Step 1: 3-iodo-1-tetrahydropyran-2-yl-pyrazole

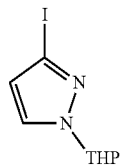

A mixture of 3-iodo-1H-pyrazole (5 g, 25.78 mmol), 3,4-dihydro-2H-pyran (10 g, 118.88 mmol), p-TsOH (900 mg, 5.23 mmol) in tetrahydrofuran (100 mL) was refluxed overnight. The reaction mixture was cooled to room temperature and washed with sat. NaHCO$_3$ (20 mL). The organic layer was separated, dried over Na$_2$SO$_4$, filtered and evaporated. The residue was purified with silica-gel column chromatography (PE:EA=20:1 to 10:1) to give 3-iodo-1-tetrahydropyran-2-yl-pyrazole (7 g, 98% yield) as a light yellow oil. LCMS (ESI) [M+Na]$^+$=300.9. $^1$H NMR (400 MHz, CDCl$_3$) δ 7.45 (d, J=2.4 Hz, 1H), 6.46 (d, J=2.4 Hz, 1H), 5.39-5.36 (m, 1H), 4.08-4.04 (m, 1H), 3.72-3.66 (m, 1H), 2.10-2.01 (m, 2H), 1.73-1.54 (m, 4H).

Step 2: methyl (E)-3-(1-tetrahydropyran-2-ylpyrazol-3-yl)prop-2-enoate

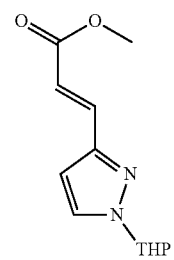

A mixture of 3-iodo-1-tetrahydropyran-2-yl-pyrazole (6.6 g, 23.73 mmol), methyl acrylate (7.5 mL, 83.29 mmol), Pd(OAc)$_2$ (660 mg, 2.95 mmol), tris-(o-tolyl)phosphine (2 g, 6.58 mmol), TEA (7 g, 69.31 mmol) in acetonitrile (80 mL) was refluxed vigorously under Ar at 110° C. for 2 h. The reaction mixture was cooled to room temperature and evaporated. The residue was purified with silica-gel column chromatography (PE:EA=8:1 to 6:1 to 4:1) to give methyl (E)-3-(1-tetrahydropyran-2-ylpyrazol-3-yl)prop-2-enoate (4.6 g, 82% yield) as a brown oil. LCMS (ESI) [M+H]+=237.1. 1H NMR (400 MHz, CDCl3) δ 7.71 (d, J=16.0 Hz, 1H), 7.61 (d, J=2.4 Hz, 1H), 6.55 (d, J=2.4 Hz, 1H), 6.44 (d, J=16.0 Hz, 1H), 5.42-5.38 (m, 1H), 4.10-4.07 (m, 1H), 3.76-3.69 (m, 1H), 2.15-2.04 (m, 2H), 1.74-1.62 (m, 4H).

Step 3: (±)-methyl trans-2-(1-tetrahydropyran-2-ylpyrazol-3-yl)cyclopropanecarboxylate

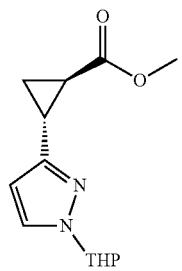

t-BuOK (3.87 g, 34.55 mmol) was added portionwise to a solution of trimethyl sulfoxoniumiodide (7.74 g, 35.17 mmol) in dimethyl sulfoxide (50 mL) at 25°. The mixture was stirred at 25° C. for 0.5 h. Then a solution of methyl (E)-3-(1-tetrahydropyran-2-ylpyrazol-3-yl)prop-2-enoate (3.87 g, 16.38 mmol) in dimethyl sulfoxide (10 mL) was added dropwise to the reaction mixture at 25° C. The mixture was stirred at 25° C. for 2 h. The reaction mixture was neutralized with sat. NH4Cl (150 mL) and extracted with EA (50 mL×3). The combined EA layers were combined, dried over Na2SO4, filtered and evaporated. The residue was purified with silica-gel column chromatography (PE:EA=4:1) to give methyl trans-2-(1-tetrahydropyran-2-ylpyrazol-3-yl)cyclopropanecarboxylate (1.1 g, 27% yield) as a light yellow oil. LCMS (ESI) [M+H]+=251.1.

Step 4: (±)-trans-2-(1-tetrahydropyran-2-ylpyrazol-3-yl)cyclopropanecarboxylic acid

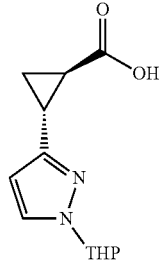

A mixture of methyl (±)-trans-2-(1-tetrahydropyran-2-ylpyrazol-3-yl)cyclopropanecarboxylate (1.07 g, 4.28 mmol) and LiOH H2O (1.07 g, 25.48 mmol) in tetrahydrofuran (20 mL) and water (20 mL) was stirred at 20° C. for 3 h. The reaction mixture was evaporated to remove the organic solvent. The residue aqueous layer was acidified with conc. HCl to pH=4 and extracted with EA (50 mL×3). The combined EA layers were combined, dried over Na2SO4, filtered and evaporated to give crude (±)-trans-2-(1-tetrahydropyran-2-ylpyrazol-3-yl)cyclopropanecarboxylic acid (1 g, 99% yield) as a light yellow oil. LCMS (ESI) [M+Na]+=259.1.

Step 5: (±)-trans-N-(6,8-dichloro-2,7-naphthyridin-3-yl)-2-(1-tetrahydropyran-2-ylpyrazol-3-yl)cyclopropanecarboxamide

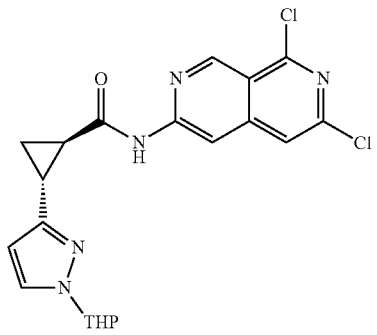

POCl3 (500 mg, 3.27 mmol) was added dropwise to a mixture of (±)-trans-2-(1-tetrahydropyran-2-ylpyrazol-3-yl)cyclopropanecarboxylic acid (350 mg, 1.48 mmol), 6,8-dichloro-2,7-naphthyridin-3-amine hydrochloride (250 mg, 1 mmol) and pyridine (2 mL, 24.73 mmol) in dichloromethane (40 mL) at 0° C. The mixture was stirred at 20° C. for 1 h. The reaction mixture diluted with H2O (15 mL). The organic layer was separated, dried over Na2SO4, filtered and concentrated. The residue was purified by silica-gel column chromatography (PE:EA:DCM=4:2:1 to 2:2:1) to give (±)-trans-N-(6,8-dichloro-2,7-naphthyridin-3-yl)-2-(1-tetrahydropyran-2-ylpyrazol-3-yl)cyclopropanecarboxamide (340 mg, 79% yield) as a white solid. LCMS (ESI) [M+Na]+=454.0.

Step 6: (±)-trans-N-(8-amino-6-chloro-2,7-naphthyridin-3-yl)-2-(1-tetrahydropyran-2-ylpyrazol-3-yl)cyclopropanecarboxamide

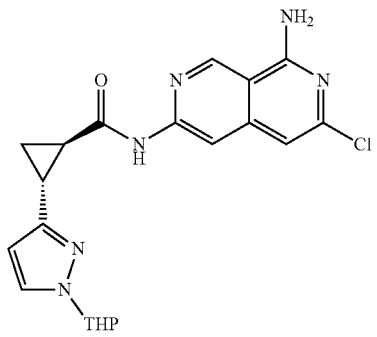

A mixture of (±)-trans-N-(6,8-dichloro-2,7-naphthyridin-3-yl)-2-(1-tetrahydropyran-2-ylpyrazol-3-yl)cyclopropanecarboxamide (340 mg, 0.79 mmol) and ammonium hydroxide (10 mL) in 1,4-dioxane (10 mL) was stirred at 90° C. in sealed tube for 3.5 h. The reaction mixture was cooled to room temperature and evaporated to yield crude (±)-trans- N-(8-amino-6-chloro-2,7-naphthyridin-3-yl)-2-(1-tetrahydropyran-2-ylpyrazol-3-yl)cyclopropanecarboxamide (320 mg, 99% yield) as a light yellow solid. The crude product was used directly in next step. LCMS (ESI) [M+H]$^+$=413.1.

Step 7: (±)-trans-N-[8-amino-6-(4-methyl-3-pyridyl)-2,7-naphthyridin-3-yl]-2-(1-tetrahydropyran-2-ylpyrazol-3-yl)cyclopropanecarboxamide

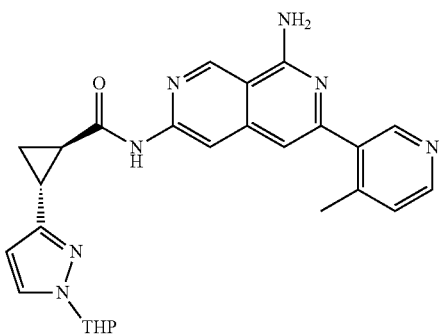

A mixture of (±)-trans-N-(8-amino-6-chloro-2,7-naphthyridin-3-yl)-2-(1-tetrahydropyran-2-ylpyrazol-3-yl)cyclopropanecarboxamide (320 mg, 0.78 mmol), 4-methyl-3-(4,4,5,5-tetramethyl-1,3,2-dioxaborolan-2-yl)pyridine (200 mg, 0.91 mmol), XPhos Pd G2 (50 mg, 0.06 mmol), XPhos (60 mg, 0.13 mmol) and K$_2$CO$_3$ (350 mg, 2.54 mmol) in 1,4-dioxane (16 mL), water (4 mL) was stirred under Ar at 100° C. for 2 h. The reaction mixture was cooled to room temperature and diluted with EA (50 mL). The mixture was washed with brine (20 mL), dried over Na$_2$SO$_4$, filtered and evaporated. The residue was purified by silica-gel column chromatography (EA to EA:MeOH=10:1) to give (±)-trans-N-[8-amino-6-(4-methyl-3-pyridyl)-2,7-naphthyridin-3-yl]-2-(1-tetrahydropyran-2-ylpyrazol-3-yl)cyclopropanecarboxamide (340 mg, 93% yield) as a brown solid. LCMS (ESI) [M+H]$^+$=470.2.

Step 8: (±)-trans-N-[8-amino-6-(4-methyl-3-pyridyl)-2,7-naphthyridin-3-yl]-2-(1H-pyrazol-3-yl)cyclopropanecarboxamide

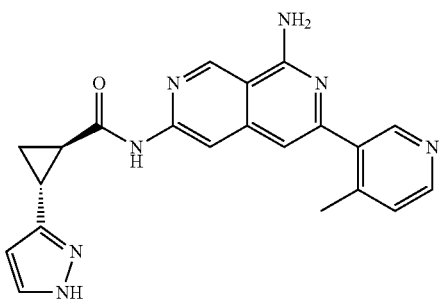

A mixture of (±)-trans-N-[8-amino-6-(4-methyl-3-pyridyl)-2,7-naphthyridin-3-yl]-2-(1-tetrahydropyran-2-ylpyrazol-3-yl)cyclopropanecarboxamide (340 mg, 0.72 mmol) and 2,2,2-trifluoroacetic acid (2 mL) in dichloromethane (10 mL) was stirred at 20° C. for 3 h. The reaction mixture was concentrated. The residue was re-dissolved in MeOH (3 mL). A 7N NH$_3$ in MeOH solution was added until pH=9-10. The mixture was purified with flash chromatography (C18, NH$_4$HCO$_3$/MeOH/H$_2$O) to give (±)-trans-N-[8-amino-6-(4-methyl-3-pyridyl)-2,7-naphthyridin-3-yl]-2-(1H-pyrazol-3-yl)cyclopropane carboxamide (110 mg, 39% yield) as a light yellow solid. LCMS (ESI): R$_T$ (min)=1.54, [M+H]$^+$=386.1, method=C; $^1$H NMR (400 MHz, CD$_3$OD): δ 9.29 (s, 1H), 8.54 (s, 1H), 8.43 (d, J=5.2 Hz, 1H), 8.34 (s, 1H), 7.54 (s, 1H), 7.40 (d, J=5.2 Hz, 1H), 6.99 (s, 1H), 6.16 (d, J=1.6 Hz, 1H), 2.62-2.57 (m, 1H), 2.46 (s, 3H), 2.31-2.27 (m, 1H), 1.67-1.62 (m, 1H), 1.46-1.41 (m, 1H).

Example 86

(±)-trans-N-[8-amino-6-(4-methyl-3-pyridyl)-2,7-naphthyridin-3-yl]-2-(1-tetrahydropyran-2-ylpyrazol-4-yl)cyclopropanecarboxamide (Compound 122)

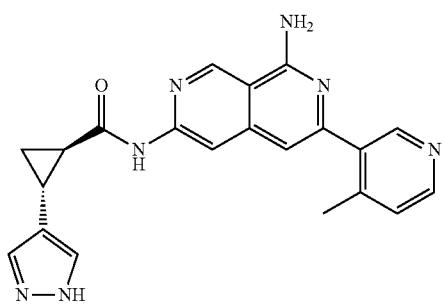 [SMILES: Cc1ccncc1-c1cc2cc(NC(=O)[C@@H]3C[C@H]3c3cn[nH]c3)ncc2c(N)n1]

Step 1: 4-iodo-1-tetrahydropyran-2-yl-pyrazole

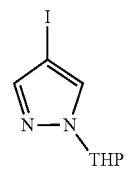

To a stirred solution of 4-iodopyrazole (5.0 g, 25.8 mmol) in dichloromethane (10 mL) was added TsOH H2O (0.5 g, 2.9 mmol) and 3,4-dihydro-2h-pyran (4.5 g, 53.5 mmol). The resulting mixture was stirred at room temperature for 2 h. The reaction mixture was concentrated in vacuo. The residue was purified by silica gel column eluted ethyl acetate/petroleum ether (1:3) to afford desired product 4-iodo-1-tetrahydropyran-2-yl-pyrazole (7 g, 93% yield) as a colorless oil. LCMS (ESI): [M−84+H]+=195.1.

Step 2: methyl (E)-3-(1-tetrahydropyran-2-ylpyrazol-4-yl)prop-2-enoate

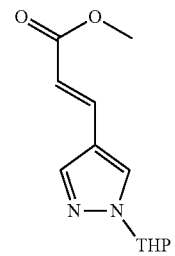

A solution of 4-iodo-1-tetrahydropyran-2-yl-pyrazole (6.7 g, 24.1 mmol), methyl acrylate (7.0 g, 81.3 mmol), TEA (4 mL, 28.8 mmol), Pd(OAc)$_2$ (550 mg, 2.5 mmol) and trimethyl phosphite (600 mg, 4.8 mmol) in N,N-dimethylformamide (50 mL) was stirred under N$_2$ at 110° C. for 3 h. The reaction was filtered and concentrated. The reaction mixture was diluted with H$_2$O (50 mL) and EtOAc (100 ml). The organic layer was then washed with water and brine solution, dried (MgSO$_4$) and concentrated. The crude was then purified by flash column chromatography eluting with 50% EtOAc in isohexane to give methyl (E)-3-(1-tetrahydropyran-2-ylpyrazol-4-yl)prop-2-enoate (4 g, 70% yield) as a yellow oil. LCMS (ESI): [M+23]$^+$=259.1.

Step 3: (±)-trans-methyl 2-(1-tetrahydropyran-2-ylpyrazol-4-yl)cyclopropanecarboxylate

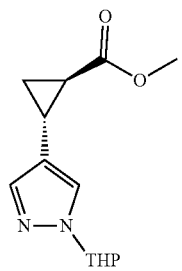

A mixture of trimethyloxosulfonium iodide (2.7 g, 12.3 mmol), NaH (500 mg, 12.5 mmol, 60% in oil) in dimethyl sulfoxide (25 mL) was stirred under N$_2$ at rt for 0.5 h. Methyl (E)-3-(1-tetrahydropyran-2-ylpyrazol-4-yl)prop-2-enoate (2.5 g, 10.6 mmol) in dimethyl sulfoxide (50 ml) was added. The mixture was stirred under N$_2$ under complete disappearance of the starting olefin. Saturated aqueous ammonium chloride solution and water were added and the product was extracted with ethyl acetate. The organic layer was washed with water and brine, dried over anhydrous magnesium sulfate, and filtrated, and concentrated. The residue was purified by silica gel column chromatography (hexane-ethyl acetate 100:0-60:40) to give methyl 2-(1-tetrahydropyran-2-ylpyrazol-4-yl)cyclopropanecarboxylate (750 mg, 25.5% yield) as a colorless oil. LCMS (ESI): [M+23]$^+$=273.1.

Step 4: (±)-trans-2-(1-tetrahydropyran-2-ylpyrazol-4-yl)cyclopropanecarboxylic acid

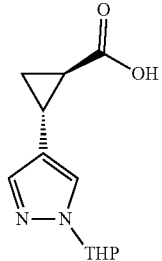

To a solution of methyl 2-(1-tetrahydropyran-2-ylpyrazol-4-yl)cyclopropanecarboxylate (300 mg, 1.2 mmol) in tetrahydrofuran (27 mL) and water (9 mL) was added lithium hydroxide monohydrate (300 mg, 7.2 mmol) at rt and the reaction mixture was stirred for 8 h. The resulting reaction mixture was concentrated to dryness, diluted with water (10 mL) and washed with EtOAc (3×80 mL). The aqueous phase was acidified to pH=4 with concentrated aqueous HCl and extracted with DCM (3×20 mL). The DCM extracts were combined and dried under reduced pressure to give the title compound (270 mg, 95% yield) as a colorless oil. LCMS (ESI): [M+H]$^+$=237.2.

Step 5: (±)-trans-N-(6,8-dichloro-2,7-naphthyridin-3-yl)-2-(1-tetrahydropyran-2-ylpyrazol-4-yl)cyclopropanecarboxamide

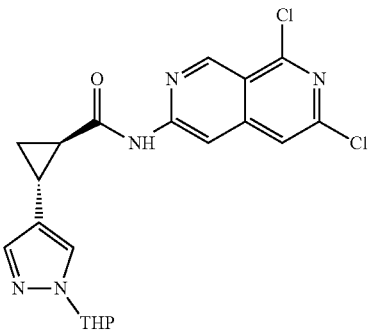

To a mixture of 6,8-dichloro-2,7-naphthyridin-3-amine (270 mg, 1.3 mmol) and (±)-trans-2-(1-tetrahydropyran-2-ylpyrazol-4-yl)cyclopropanecarboxylic acid (270 mg, 1.1 mmol) in pyridine (10 mL) was added phosphorus oxychloride (270 mg, 1.8 mmol) at 0° C. The resulting mixture was stirred for 1 h at 0° C. The reaction was then quenched with saturated aq.NaHCO$_3$ and extracted with EA (20 mL×2). The combined EA extracts were concentrated in vacuo. The residue was purified by flash column chromatography (PE: EA=3:1-1:3) to give (±)-trans-N-(6,8-dichloro-2,7-naphthyridin-3-yl)-2-(1-tetrahydropyran-2-ylpyrazol-4-yl)cyclopropanecarboxamide (300 mg, 61% yield) as a colorless oil. LCMS (ESI): [M+H]+=432.1.

Step 6: (±)-trans-N-(8-amino-6-chloro-2,7-naphthyridin-3-yl)-2-(1-tetrahydropyran-2-ylpyrazol-4-yl)cyclopropanecarboxamide

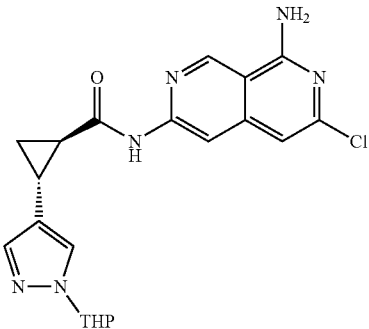

A mixture of (±)-trans-N-(6,8-dichloro-2,7-naphthyridin-3-yl)-2-(1-tetrahydropyran-2-ylpyrazol-4-yl)cyclopropanecarboxamide (300 mg, 0.69 mmol) and NH$_4$OH (8 mL, 0.69 mmol) in 1,4-dioxane (8 mL) was heated at 90° C. for 4 h under Ar. The reaction was concentrated to dryness. The crude material was used directly without further purification. LCMS (ESI): [M+H]⁺=413.1.

Step 7: (±)-trans-N-[8-amino-6-(4-methyl-3-pyridyl)-2,7-naphthyridin-3-yl]-2-(1-tetrahydropyran-2-ylpyrazol-4-yl)cyclopropanecarboxamide

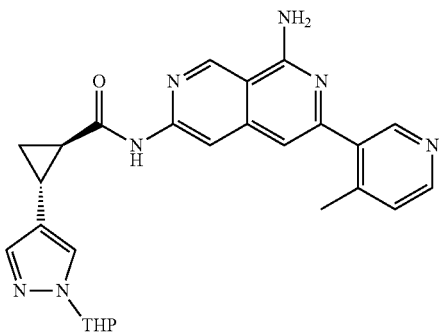

A mixture of (±)-trans-N-(8-amino-6-chloro-2,7-naphthyridin-3-yl)-2-(1-tetrahydropyran-2-ylpyrazol-4-yl)cyclopropanecarboxamide (240 mg, 0.58 mmol), 4-methyl-3-(4,4,5,5-tetramethyl-1,3,2-dioxaborolan-2-yl)pyridine (160 mg, 0.73 mmol), Pd(dppf)Cl₂ (80 mg, 0.11 mmol) and Na₂CO₃ (200 mg, 1.89 mmol) in 1,4-dioxane (8 mL) and water (1 mL) was heated at 100° C. for 1 h under Ar. The crude (±)-trans-N-[8-amino-6-(4-methyl-3-pyridyl)-2,7-naphthyridin-3-yl]-2-(1-tetrahydropyran-2-ylpyrazol-4-yl)cyclopropanecarboxamide (300 mg, 88% yield) was used directly in the next step without further purification. LCMS (ESI): [M+H]⁺=470.2.

Step 8: (±)-trans-N-[8-amino-6-(4-methyl-3-pyridyl)-2,7-naphthyridin-3-yl]-2-(1H-pyrazol-4-yl)cyclopropanecarboxamide

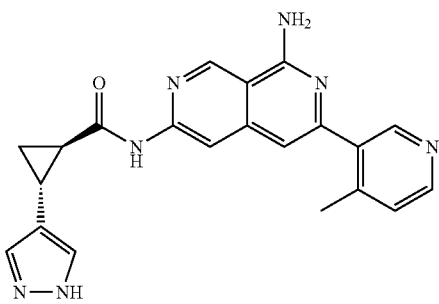

The mixture of (±)-trans-N-[8-amino-6-(4-methyl-3-pyridyl)-2,7-naphthyridin-3-yl]-2-(1-tetrahydropyran-2-ylpyrazol-4-yl)cyclopropanecarboxamide (300 mg, 0.64 mmol) and TFA (10 mL, 134.6 mmol) in dichloromethane (20 mL) was stirred at rt for 1 h. The mixture was neutralized by NH₃ in MeOH and concentrated. The residue was purified by prep-HPLC to give (±)-trans-N-[8-amino-6-(4-methyl-3-pyridyl)-2,7-naphthyridin-3-yl]-2-(1H-pyrazol-4-yl)cyclopropanecarboxamide (68 mg, 28% yield) as a white solid. LCMS (ESI): RT (min)=1.240, [M+H]⁺=386.1, method=G; 1H NMR (400 MHz, DMSO-d₆) δ 12.62 (s, 1H), 10.94 (s, 1H), 9.37 (s, 1H), 8.57 (s, 1H), 8.44 (d, J=5.2 Hz, 1H), 8.26 (s, 1H), 7.62 (s, 1H), 7.37 (s, 1H), 7.32-7.31 (m, 3H), 6.97 (s, 1H), 2.41 (s, 3H), 2.27-2.19 (m, 2H), 1.50-1.36 (m, 1H), 1.27-1.11 (m, 1H).

Example 87 exo-N-[8-amino-6-(4-methyl-3-pyridyl)-2,7-naphthyridin-3-yl]-3-(2-methoxyethyl)-3-azabicyclo[3.1.0]hexane-6-carboxamide (Compound 124)

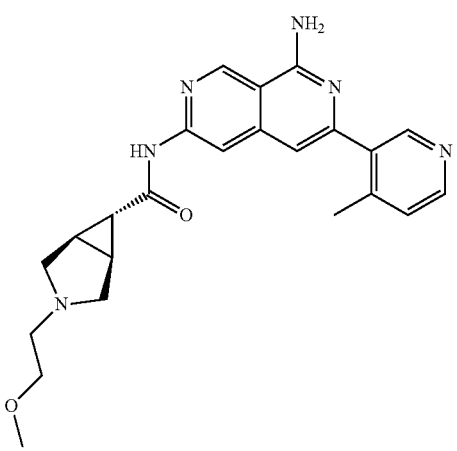 [SMILES: COCCN1C[C@@H]2[C@H](C1)[C@H]2C(=O)Nc1cc2cc(-c3cnccc3C)nc(N)c2cn1]

To a mixture of exo-N-[8-amino-6-(4-methyl-3-pyridyl)-2,7-naphthyridin-3-yl]-3-azabicyclo[3.1.0]hexane-6-carboxamide (100 mg, 0.28 mmol) in N,N-dimethylformamide (1 mL) was added 2-bromoethyl methyl ether (50 mg, 0.36 mmol) and DIPEA (107 mg, 0.83 mmol). The mixture was stirred at 25° C. for 3 d. The mixture was purified by prep-HPLC to give exo-N-[8-amino-6-(4-methyl-3-pyridyl)-2,7-naphthyridin-3-yl]-3-(2-methoxyethyl)-3-azabicyclo[3.1.0]hexane-6-carboxamide (39 mg, 34% yield) as a yellow solid. LCMS (ESI): R_T(min)=1.775, [M+H]⁺=419.2, method=I-1; ¹H NMR (400 MHz, CD₃OD) δ 9.28 (s, 1H), 8.53 (s, 1H), 8.43 (d, J=5.2 Hz, 1H), 8.27 (s, 1H), 7.39 (d, J=5.2 Hz, 1H), 6.96 (s, 1H), 3.51 (t, J=5.6 Hz, 2H), 3.37 (s, 3H), 3.20-3.18 (m, 2H), 2.70 (t, J=5.6 Hz, 2H), 2.56-2.63 (m, 2H), 2.45 (s, 3H), 2.24-2.22 (m, 1H), 2.05 (s, 2H).

Example 88

(±)-trans-N-(8-amino-6-(4-methylpyridin-3-yl)-2,7-naphthyridin-3-yl)-5-azaspiro[2.4]heptane-1-carboxamide (Compound 125)

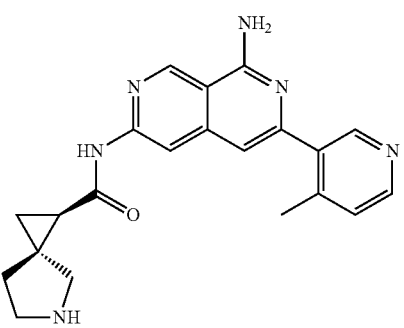 [SMILES: Cc1ccncc1-c1cc2cc(NC(=O)[C@@H]3C[C@]34CCNC4)ncc2c(N)n1]

Step 1: (±)-trans-tert-butyl 1-(6,8-dichloro-2,7-naphthyridin-3-ylcarbamoyl)-5-azaspiro[2.4]heptane-5-carboxylate

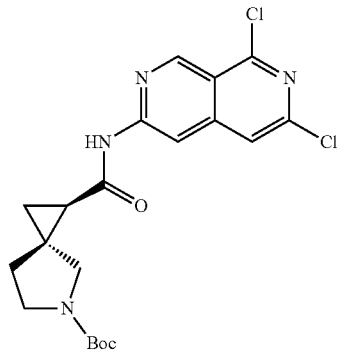 [SMILES: CC(C)(C)OC(=O)N1CC[C@]2(C[C@H]2C(=O)Nc2cc3cc(Cl)nc(Cl)c3cn2)C1]

To a mixture of 6,8-dichloro-2,7-naphthyridin-3-amine (270 mg, 1.26 mmol), 5-tert-butoxycarbonyl-5-azaspiro[2.4]heptane-2-carboxylic acid (365 mg, 1.51 mmol) and pyridine (1.0 mL, 12.61 mmol) in DCM (5 mL) was added POCl$_3$ (212 mg, 1.39 mmol) at 0° C. After the addition was completed, the reaction solution was stirred for 1 h at rt. The reaction was concentrated to dryness and purified by flash column chromatography eluting 20% EA in PE to give (±)-trans-tert-butyl 1-(6,8-dichloro-2,7-naphthyridin-3-ylcarbamoyl)-5-azaspiro[2.4]heptane-5-carboxylate (290 mg, 52% yield) as a white solid. LCMS (ESI): [M−56]$^+$=381.1.

Step 2: (±)-trans-tert-butyl 1-(8-amino-6-chloro-2,7-naphthyridin-3-ylcarbamoyl)-5-azaspiro[2.4]heptane-5-carboxylate

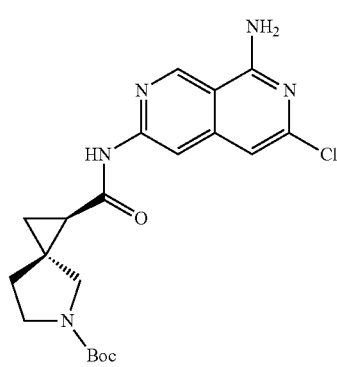 [SMILES: CC(C)(C)OC(=O)N1CC[C@]2(C[C@H]2C(=O)Nc2cc3cc(Cl)nc(N)c3cn2)C1]

A mixture of (±)-trans-tert-butyl 1-(6,8-dichloro-2,7-naphthyridin-3-ylcarbamoyl)-5-azaspiro[2.4]heptane-5-carboxylate (290 mg, 0.66 mmol) and NH$_4$OH (2 mL) in 1,4-dioxane (5 mL) was heated in a sealed tube at 80° C. for 3 h. The mixture was concentrated and the crude product was washed with water and PE to give trans-tert-butyl 1-(8-amino-6-chloro-2,7-naphthyridin-3-ylcarbamoyl)-5-azaspiro[2.4]heptane-5-carboxylate (213 mg, 77% yield) as a white solid. LCMS (ESI): [M+H]$^+$=418.2.

Step 3: (±)-trans-N-(8-amino-6-(4-methylpyridin-3-yl)-2,7-naphthyridin-3-yl)-5-azaspiro[2.4]heptane-1-carboxamide

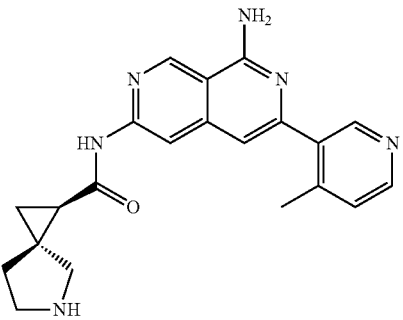 [SMILES: Cc1ccncc1-c1cc2cc(NC(=O)[C@@H]3C[C@]34CCNC4)ncc2c(N)n1]

To a sealed tube was added (±)-trans-tert-butyl 1-(8-amino-6-chloro-2,7-naphthyridin-3-ylcarbamoyl)-5-azaspiro[2.4]heptane-5-carboxylate (340 mg), K$_2$CO$_3$ (3 eq), Pd(dppf)Cl$_2$ (0.2 eq), 4-methyl-3-(4,4,5,5-tetramethyl-1,3,2-dioxaborolan-2-yl)pyridine (1.3 eq), 1,4-dioxane (20 mL) and water (1 mL). The mixture was bubbled with N$_2$ for 2 min and stirred at 110° C. for 3 h. The reaction was concentrated and to the resulting residue was added DCM (3 mL) and TFA (0.5 mL). The mixture was stirred at rt for 2 h. The mixture was concentrated and purified by prep-HPLC to give (±)-trans-N-(8-amino-6-(4-methylpyridin-3-yl)-2,7-naphthyridin-3-yl)-5-azaspiro[2.4]heptane-1-carboxamide (47 mg, 37% yield) as a white solid. LCMS (ESI): R$_T$ (min)=1.390, [M+H]$^+$=375.2, method=G; $^1$H NMR (400 MHz, CD$_3$OD) δ 9.29 (s, 1H), 8.53 (s, 1H), 8.43 (d, J=4.8 Hz, 1H), 8.33 (s, 1H), 7.40 (d, J=4.8 Hz, 1H), 6.97 (s, 1H), 3.29-3.20 (m, 4H), 2.45 (s, 3H), 2.25-2.22 (m, 1H), 2.11-2.04 (m, 1H), 2.00-1.1.94 (m, 1H), 1.45-1.43 (m, 1H), 1.34-1.31 (m, 1H).

Example 89

(±)-cis-N-(8-amino-6-(4-methylpyridin-3-yl)-2,7-naphthyridin-3-yl)-5-azaspiro[2.4]heptane-1-carboxamide (Compound 126)

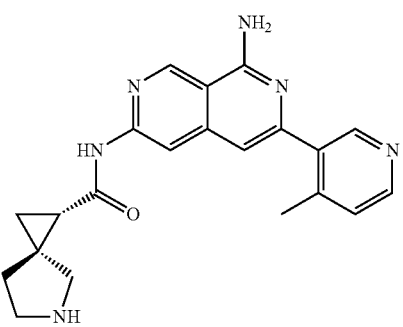

Step 1: (±)-cis-tert-butyl 1-(6,8-dichloro-2,7-naph-thyridin-3-ylcarbamoyl)-5-azaspiro[2.4]heptane-5-carboxylate

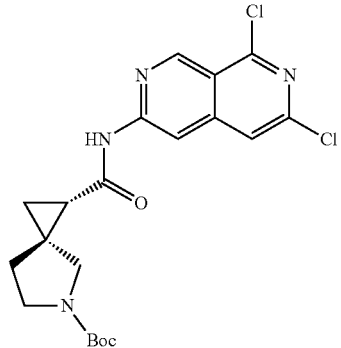 [SMILES: CC(C)(C)OC(=O)N1CC[C@]2(C[C@@H]2C(=O)Nc2cc3cc(Cl)nc(Cl)c3cn2)C1]

To a mixture of 6,8-dichloro-2,7-naphthyridin-3-amine (270 mg, 1.26 mmol), 5-tert-butoxycarbonyl-5-azaspiro[2.4]heptane-2-carboxylic acid (365 mg, 1.51 mmol) and pyridine (1.0 mL, 12.61 mmol) in DCM (5 mL) was added POCl$_3$ (212 mg, 1.39 mmol) at 0° C. The reaction solution was stirred for 1 h at rt. The reaction was concentrated to dryness and purified by flash column chromatography eluting with 20% EA in PE to give (±)-cis-tert-butyl 1-(6,8-dichloro-2,7-naphthyridin-3-ylcarbamoyl)-5-azaspiro[2.4]heptane-5-carboxylate (210 mg, 38% yield) as a white solid. LCMS (ESI): [M−56]$^+$=381.1.

Step 2: (±)-cis-tert-butyl 1-(8-amino-6-chloro-2,7-naphthyridin-3-ylcarbamoyl)-5-azaspiro[2.4]heptane-5-carboxylate

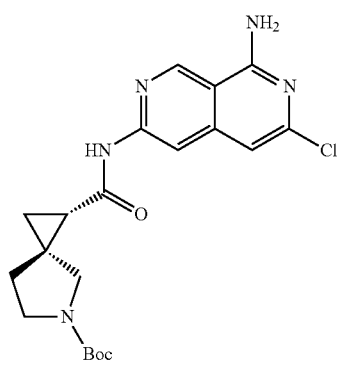 [SMILES: CC(C)(C)OC(=O)N1CC[C@]2(C[C@@H]2C(=O)Nc2cc3cc(Cl)nc(N)c3cn2)C1]

A mixture of (±)-cis-tert-butyl 1-(6,8-dichloro-2,7-naphthyridin-3-ylcarbamoyl)-5-azaspiro[2.4]heptane-5-carboxylate (210 mg, 0.48 m(±)-mol) and NH$_4$OH (2 mL) in 1,4-dioxane (5 mL) was heated to 80° C. for 3 h in a sealed tube. The mixture was concentrated and the crude product was washed with water and PE to give (±)-cis-tert-butyl 1-(8-amino-6-chloro-2,7-naphthyridin-3-ylcarbamoyl)-5-azaspiro[2.4]heptane-5-carboxylate (155 mg, 77% yield) as a white solid. LCMS (ESI): [M+H]$^+$=418.2.

Step 3: (±)-cis-N-(8-amino-6-(4-methylpyridin-3-yl)-2,7-naphthyridin-3-yl)-5-azaspiro[2.4]heptane-1-carboxamide

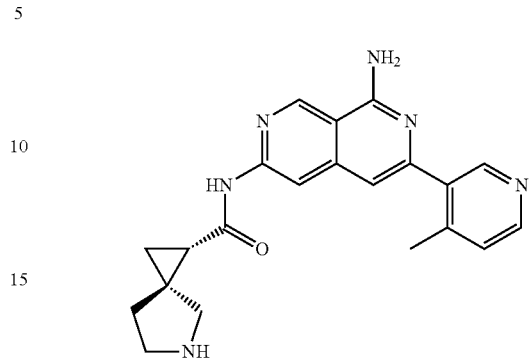

To a sealed tube was added (±)-cis-tert-butyl 1-(8-amino-6-chloro-2,7-naphthyridin-3-ylcarbamoyl)-5-azaspiro[2.4]heptane-5-carboxylate (340 mg), K$_2$CO$_3$ (3 eq), Pd(dppf)Cl$_2$ (0.2 eq), and 4-methyl-3-(4,4,5,5-tetramethyl-1,3,2-dioxaborolan-2-yl)pyridine (1.3 eq), 1,4-dioxane (20 mL) and water (1 mL). The mixture was bubbled with N$_2$ for 2 min and stirred at 110° C. for 3 h. The reaction mixture was concentrated and to the residue was added DCM (3 mL) and TFA (0.5 mL). The mixture was stirred at rt for 2 h. The mixture was concentrated and purified by prep-HPLC to give (±)-cis-N-(8-amino-6-(4-methylpyridin-3-yl)-2,7-naphthyridin-3-yl)-5-azaspiro[2.4]heptane-1-carboxamide (44 mg, 31% yield) as a white solid. LCMS (ESI): R$_T$(min)=1.413, [M+H]$^+$=375.2, method=G; $^1$H NMR (400 MHz, CD$_3$OD) δ 9.30 (s, 1H), 8.54 (s, 1H), 8.43 (d, J=5.2 Hz, 1H), 8.33 (s, 1H), 7.40 (d, J=5.2 Hz, 1H), 6.98 (s, 1H), 3.15-3.08 (m, 2H), 3.03-2.91 (m, 2H), 2.46 (s, 3H), 2.16-2.13 (m, 1H), 2.03-1.98 (m, 2H), 1.48-1.45 (m, 1H), 1.26-1.24 (m, 1H).

Example 90

(±)-trans-N-(8-amino-6-(4-methylpyridin-3-yl)-2,7-naphthyridin-3-yl)-5-(2-methoxyethyl)-5-azaspiro[2.4]heptane-1-carboxamide (Compound 127)

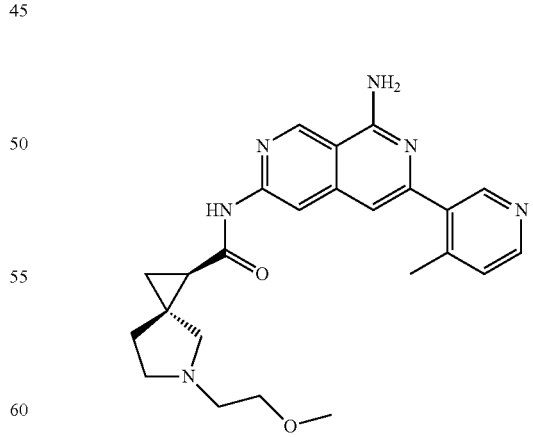

A mixture of (±)-trans-N-(8-amino-6-(4-methylpyridin-3-yl)-2,7-naphthyridin-3-yl)-5-azaspiro[2.4]heptane-1-carboxamide (30 mg, 0.08 mmol) in N,N-dimethylformamide (1 mL) was added 2-bromoethyl methyl ether (14 mg, 0.10 mmol) and DIPEA (31 mg, 0.24 mmol). The mixture was stirred at 25° C. for 3 days. The mixture was concentrated and purified by prep-HPLC to give (±)-trans-N-(8-amino-6-(4-methylpyridin-3-yl)-2,7-naphthyridin-3-yl)-5-(2-methoxyethyl)-5-azaspiro[2.4]heptane-1-carboxamide (13 mg, 38% yield) as a white solid. LCMS (ESI): $R_T$ (min)= 1.723, [M+H]$^+$=433.2, method=I-1; $^1$H NMR (400 MHz, CD$_3$OD) δ 9.29 (s, 1H), 8.54 (s, 1H), 8.43 (d, J=5.2 Hz, 1H), 8.32 (s, 1H), 7.40 (d, J=5.2 Hz, 1H), 6.98 (s, 1H), 3.53-3.50 (m, 2H), 3.33 (s, 3H), 2.87-2.69 (m, 6H), 2.45 (s, 3H), 2.13-1.92 (m, 3H), 1.43-1.41 (m, 1H), 1.22-1.19 (m, 1H).

Example 91

(±)-cis-N-(8-amino-6-(4-methylpyridin-3-yl)-2,7-naphthyridin-3-yl)-5-(2-methoxyethyl)-5-azaspiro[2.4]heptane-1-carboxamide (Compound 128)

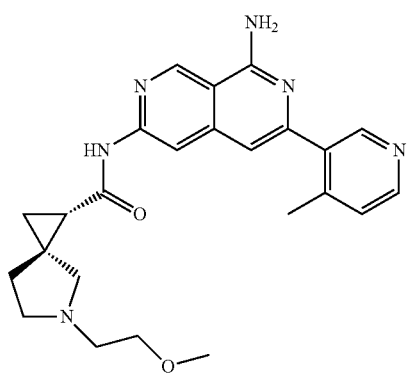 [SMILES: COCCN1CC[C@]2(C[C@@H]2C(=O)Nc2cc3cc(-c4cnccc4C)nc(N)c3cn2)C1]

To a mixture of (±)-cis-N-(8-amino-6-(4-methylpyridin-3-yl)-2,7-naphthyridin-3-yl)-5-azaspiro[2.4]heptane-1-carboxamide (30 mg, 0.08 mmol) in N,N-dimethylformamide (1 mL) was added 2-bromoethyl methyl ether (14 mg, 0.10 mmol) and DIPEA (31 mg, 0.24 mmol). The mixture was stirred at 25° C. for 3 days. The mixture was concentrated and purified by prep-HPLC to give (±)-cis-N-(8-amino-6-(4-methylpyridin-3-yl)-2,7-naphthyridin-3-yl)-5-(2-methoxyethyl)-5-azaspiro[2.4]heptane-1-carboxamide (22 mg, 64% yield) as a white solid. LCMS (ESI): $R_T$ (min)= 1.763, [M+H]$^+$=433.3, method=I-1; $^1$H NMR (400 MHz, CD$_3$OD) δ 9.29 (s, 1H), 8.54 (s, 1H), 8.43 (d, J=5.2 Hz, 1H), 8.32 (s, 1H), 7.39 (d, J=5.2 Hz, 1H), 6.97 (s, 1H), 3.56-3.53 (m, 2H), 3.36 (s, 3H), 2.91-2.60 (m, 6H), 2.45 (s, 3H), 2.12-1.96 (m, 3H), 1.40-1.37 (m, 1H), 1.21-1.18 (m, 1H).

Example 92

(±)-trans-N-[8-amino-6-(4-ethoxy-3-pyridyl)-2,7-naphthyridin-3-yl]-2-cyano-cyclopropanecarboxamide (Compound 129)

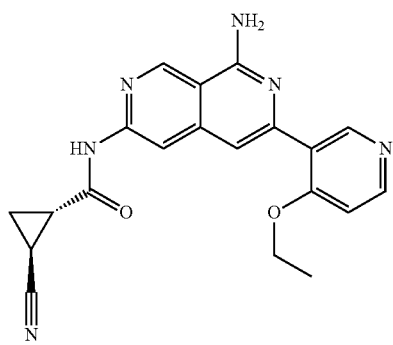 [SMILES: CCOc1ccncc1-c1cc2cc(NC(=O)[C@H]3C[C@@H]3C#N)ncc2c(N)n1]

Step 1: (4-ethoxy-3-pyridyl)boronic acid

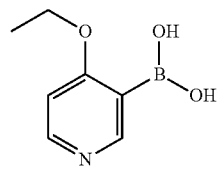

A solution of n-BuLi (2.5 M in hexane, 1.1 mL, 2.75 mmol) was added dropwise to a solution of 3-bromo-4-ethoxy-pyridine (500 mg, 2.47 mmol), triisopropyl borate (930 mg, 4.94 mmol) in tetrahydrofuran (5 mL) at −78° C. The mixture was stirred at −78° C. for 0.5 h then warmed to 20° C. and stirred for 0.5 h. The reaction mixture was quenched with H$_2$O (5 mL) and the aqueous layer separated and washed with EA (10 mL). The aqueous layer was acidified to pH 4-5 by conc. HCl and washed with EA (10 mL×3). The aqueous layer was separated and evaporated and the residue was purified with flash chromatography (C18, HCOOH/MeOH/H$_2$O) to give (4-ethoxy-3-pyridyl)boronic acid (110 mg, 27% yield) as a white solid. LCMS (ESI) [M+H]$^+$=168.1.

Step 2: (±)-trans-N-[8-amino-6-(4-ethoxy-3-pyridyl)-2,7-naphthyridin-3-yl]-2-cyano-cyclopropanecarboxamide

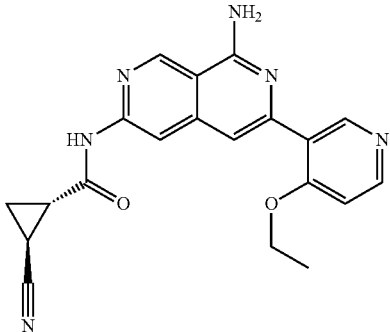 [SMILES: CCOc1ccncc1-c1cc2cc(NC(=O)[C@H]3C[C@@H]3C#N)ncc2c(N)n1]

A mixture of (±)-trans-N-(8-amino-6-chloro-2,7-naphthyridin-3-yl)-2-cyano-cyclopropanecarboxamide (100 mg, 0.35 mmol), (4-ethoxy-3-pyridyl)boronic acid (110 mg, 0.66 mmol), XPhos Pd G2 (30 mg, 0.04 mmol), XPhos (40 mg, 0.08 mmol) and K$_2$CO$_3$ (150 mg, 1.09 mmol) in 1,4-dioxane (16 mL) and water (4 mL) was stirred at 100° C. under Ar for 2 h. The reaction mixture was cooled to room temperature and diluted with EA (100 mL). The mixture was washed with brine (20 mL). The organic layer was separated, dried over Na$_2$SO$_4$, filtered and evaporated. The residue was purified by silica-gel column chromatography (EA to EA:MeOH=10:1) to give (±)-trans-N-[8-amino-6-(4-ethoxy-3-pyridyl)-2,7-naphthyridin-3-yl]-2-cyano-cyclopropane carboxamide (75 mg, 58% yield) as a light yellow solid. LCMS (ESI): R$_T$(min)=1.639, [M+H]$^+$=375.1, method=C; $^1$H NMR (400 MHz, DMSO-d$_6$): δ11.28 (brs, 1H), 9.37 (s, 1H), 8.95 (s, 1H), 8.42 (d, J=5.6 Hz, 1H), 8.15 (s, 1H), 7.42 (s, 1H), 7.31 (brs, 2H), 7.14 (d, J=5.6 Hz, 1H), 4.23 (q, J=7.2 Hz, 2H), 2.78-2.74 (m, 1H), 2.19-2.15 (m, 1H), 1.64-1.59 (m, 1H), 1.47-1.42 (m, 1H), 1.39 (t, J=7.2 Hz, 3H).

Example 93

1-[8-amino-6-(4-methyl-3-pyridyl)-2,7-naphthyridin-3-yl]-3-methyl-urea (Compound 130)

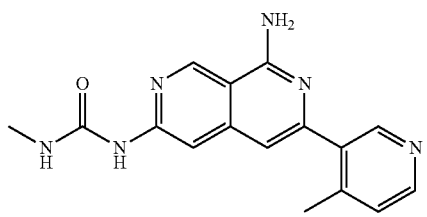 [SMILES: CNC(=O)Nc1cc2cc(-c3cnccc3C)nc(N)c2cn1]

Step 1: 1-(6,8-dichloro-2,7-naphthyridin-3-yl)-3-methyl-urea

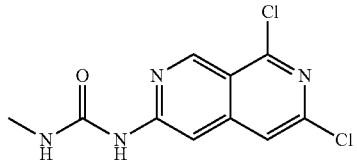 [SMILES: CNC(=O)Nc1cc2cc(Cl)nc(Cl)c2cn1]

To a mixture of 6,8-dichloro-2,7-naphthyridin-3-amine hydrochloride (500 mg, 2.0 mmol) in tetrahydrofuran (30 mL) was added in triethylamine (8 mL, 57.4 mmol) and triphosgene (600 mg, 2.02 mmol). The mixture was stirred at room temperature for 10 min before methanamine hydrochloride (1400 mg, 20.73 mmol) was added. The reaction mixture was stirred at room temperature for 1 h. The reaction mixture was concentrated to dryness and purified by column chromatography eluting with ethyl acetate/petroleum ether (1/1) to afford 1-(6,8-dichloro-2,7-naphthyridin-3-yl)-3-methyl-urea (190 mg, 31% yield) as a yellow solid. LCMS (ESI): [M+H]$^+$=271.0.

Step 2: 1-(8-amino-6-chloro-2,7-naphthyridin-3-yl)-3-methyl-urea

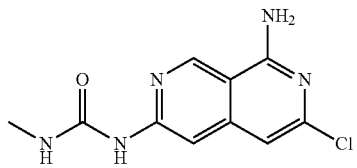 [SMILES: CNC(=O)Nc1cc2cc(Cl)nc(N)c2cn1]

A mixture of 1-(6,8-dichloro-2,7-naphthyridin-3-yl)-3-methyl-urea (170 mg, 0.63 mmol) in 1,4-dioxane (4 mL) and ammonium hydroxide (25%, 4 mL, 212.71 mmol) was stirred at 90° C. for 4 h. The mixture was concentrated to dryness to afford crude 1-(8-amino-6-chloro-2,7-naphthyridin-3-yl)-3-methyl-urea (220 mg) as a yellow solid. LCMS (ESI): [M+H]$^+$=252.1.

Step 3: 1-[8-amino-6-(4-methyl-3-pyridyl)-2,7-naphthyridin-3-yl]-3-methyl-urea

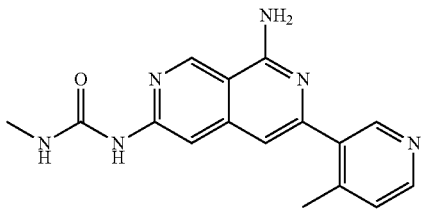 [SMILES: CNC(=O)Nc1cc2cc(-c3cnccc3C)nc(N)c2cn1]

A mixture of 1-(8-amino-6-chloro-2,7-naphthyridin-3-yl)-3-methyl-urea (220 mg, 0.87 mmol), 4-methyl-3-(4,4,5,5-tetramethyl-1,3,2-dioxaborolan-2-yl)pyridine (176 mg, 0.80 mmol), X-Phos-Pd-G2 (48 mg, 0.06 mmol), X-Phos (56 mg, 0.12 mmol) and K$_2$CO$_3$ (180 mg, 1.3 mmol) in 1,4-dioxane (6 mL) and water (1 mL) was stirred under Ar at 90° C. for 1 h. The reaction was concentrated to dryness and purified by column chromatography on silica gel eluting with ethyl methanol/dichloromethane (1/10-1/7) to afford 1-[8-amino-6-(4-methyl-3-pyridyl)-2, 7-naphthyridin-3-yl]-3-methyl-urea (64 mg, 24% yield) as a yellow solid. LCMS (ESI): [M+H]$^+$=309.2, R$_7$(min)=1.35, Method=E; $^1$H NMR (400 MHz, DMSO-d$_6$) δ 9.26 (s, 2H), 8.56 (s, 1H), 8.43 (d, J=4.8 Hz, 1H), 7.76 (s, 1H), 7.30 (d, J=4.8 Hz, 1H), 7.26 (s, 2H), 7.13 (d, J=4.4 Hz, 1H), 6.88 (s, 1H), 2.72 (d, J=4.8 Hz, 3H), 2.41 (s, 3H).

Example 94

(±)-trans-N-[8-amino-6-(4-methyl-3-pyridyl)-2,7-naphthyridin-3-yl]-2-(3-pyridyl)cyclopropane carboxamide (Compound 131)

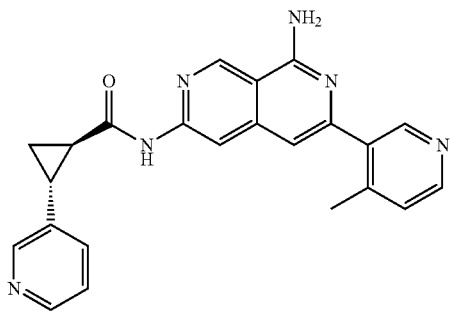 [SMILES: Cc1ccncc1-c1cc2cc(NC(=O)[C@@H]3C[C@H]3c3cccnc3)ncc2c(N)n1]

Step 1: tert-butyl (E)-3-(3-pyridyl)prop-2-enoate

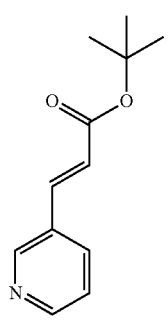

A mixture of tert-butyl acrylate (12 mL, 81.92 mmol), 3-iodopyridine (6.15 g, 30 mmol), tris-(o-tolyl)phosphine (2.1 g, 6.91 mmol), Pd(OAc)$_2$ (767 mg, 3.42 mmol) and triethylamine (12 mL, 86.1 mmol) in acetonitrile (50 mL) was stirred under Ar at 95° C. for 2 h. The mixture was concentrated and purified by column chromatography (ethyl acetate/petroleum 1/3 to 1/1) to afford tert-butyl (E)-3-(3-pyridyl)prop-2-enoate (5.55 g, 90% yield) as a yellow solid. LCMS(ESI): [M+H]$^+$=206.1.

Step 2: (±)-tert-butyl (trans)-2-(3-pyridyl)cyclopropanecarboxylate

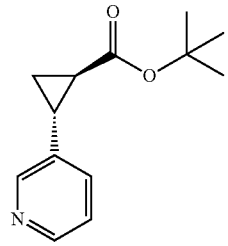 [SMILES: CC(C)(C)OC(=O)[C@@H]1C[C@H]1c1cccnc1]

Sodium tert-butoxide (520 mg, 5.41 mmol) was added to a solution of trimethyl sulfoxoniumiodide (1.1 g, 5 mmol) in dimethyl sulfoxide (10 mL) at room temperature. The mixture was stirred under Ar at room temperature for 20 min. The reaction mixture was added slowly dropwise to a solution of tert-butyl (E)-3-(3-pyridyl)prop-2-enoate (1.0 g, 4.87 mmol) in dimethyl sulfoxide (10 mL). The mixture was stirred under Ar at room temperature for 1 h. The reaction mixture was diluted with sat. NH$_4$Cl and extracted with ethyl acetate. The organic layer was concentrated and purified by silica gel column chromatography (ethyl acetate/petroleum ether) to afford (±)-tert-butyl (trans)-2-(3-pyridyl)cyclopropanecarboxylate (550 mg, 43% yield) as a yellow liquid. LCMS(ESI): [M+H]$^+$=220.2.

Step 3: (±)-trans-2-(3-pyridyl)cyclopropanecarboxylic acid

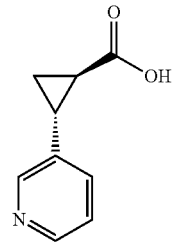

A solution of (±)-tert-butyl (trans)-2-(3-pyridyl)cyclopropanecarboxylate (550 mg, 2.51 mmol) in trifluoroacetic acid (2 mL, 25.96 mmol) was stirred at room temperature for 1 h. The solution was concentrated to dryness to afford (±)-crude trans-2-(3-pyridyl)cyclopropanecarboxylic acid (300 mg) as a colorless liquid. LCMS(ESI): [M+H]$^+$=164.1.

Step 4: (±)-trans-N-(6,8-dichloro-2,7-naphthyridin-3-yl)-2-(3-pyridyl)cyclopropanecarboxamide

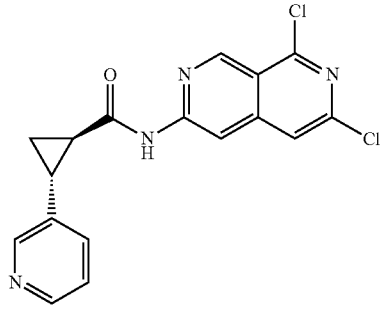

A mixture of (±)-trans-2-(3-pyridyl)cyclopropanecarboxylic acid (300 mg, 1.84 mmol), 6,8-dichloro-2,7-naphthyridin-3-amine (400 mg, 1.87 mmol) and pyridine (3 mL, 37.09 mmol) in dichloromethane (10 mL) was stirred at room temperature. POCl$_3$ (0.5 mL, 5.36 mmol) was added dropwise to the mixture at room temperature. The mixture was stirred at room temperature for 1 h and then diluted with 1 ml of water. The mixture was concentrated and purified by column chromatography (ethyl acetate/petroleum ether 30-100%) to afford (±)-trans-N-(6,8-dichloro-2,7-naphthyridin-3-yl)-2-(3-pyridyl)cyclopropanecarboxamide (220 mg, 31% yield) as a yellow solid. LCMS(ESI): [M+H]$^+$=359.0.

Step 5: (±)-trans-N-(8-amino-6-chloro-2,7-naphthyridin-3-yl)-2-(3-pyridyl)cyclopropanecarboxamide

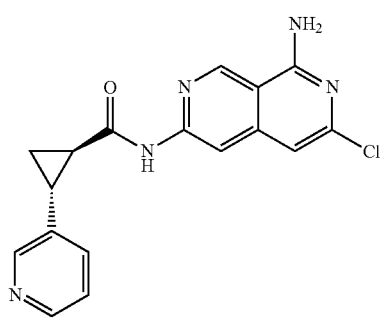 [SMILES: Nc1nc(Cl)cc2cc(NC(=O)[C@@H]3C[C@H]3c3cccnc3)ncc12]

A mixture of (±)-trans-N-(6,8-dichloro-2,7-naphthyridin-3-yl)-2-(3-pyridyl)cyclopropane carboxamide (220 mg, 0.61 mmol) in 1,4-dioxane (4 mL) and ammonium hydroxide (25%, 3 mL, 159.53 mmol) was stirred at 95° C. for 3 h. The mixture was concentrated to dryness to afford (±)-trans-N-(8-amino-6-chloro-2,7-naphthyridin-3-yl)-2-(3-pyridyl)cyclopropanecarboxamide (250 mg) as a yellow solid. LCMS (ESI): [M+H]$^+$=340.1.

Step 6: (±)-trans-N-[8-amino-6-(4-methyl-3-pyridyl)-2,7-naphthyridin-3-yl]-2-(3-pyridyl)cyclopropanecarboxamide

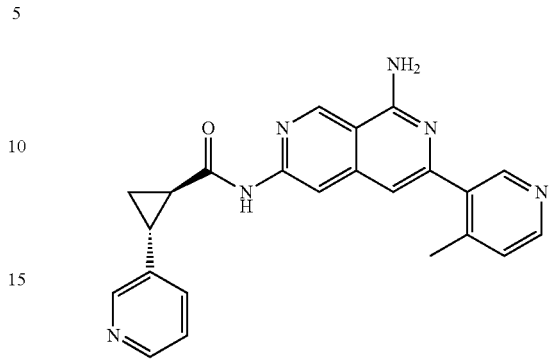

A mixture of (±)-trans-N-(8-amino-6-chloro-2,7-naphthyridin-3-yl)-2-(3-pyridyl) cyclopropanecarboxamide (250 mg, 0.74 mmol), 4-methyl-3-(4,4,5,5-tetramethyl-1,3,2-dioxaborolan-2-yl)pyridine (180 mg, 0.82 mmol), X-Phos-Pd-G2 (46 mg, 0.06 mmol), X-Phos (68 mg, 0.14 mmol) and K$_2$CO$_3$ (266 mg, 1.93 mmol) in 1,4-dioxane (7 mL) and water (1 mL) was stirred under Ar at 100° C. for 1 h. The reaction was concentrated and purified by column chromatography (ethyl methanol/dichloromethane, 1/10-1/7) to afford (±)-trans-N-[8-amino-6-(4-methyl-3-pyridyl)-2,7-naphthyridin-3-yl]-2-(3-pyridyl) cyclopropanecarboxamide (130 mg, 45% yield) as a yellow solid. LCMS(ESI): [M+H]$^+$=397.2, R$_T$(min)=1.27, Method=B; $^1$H NMR (400 MHz, DMSO-d$_6$) δ 11.00 (s, 1H), 9.37 (s, 1H), 8.57 (s, 1H), 8.51 (d, J=2.0 Hz, 1H), 8.45-8.42 (m, 2H), 8.28 (s, 1H), 7.57 (d, J=8.0 Hz, 1H), 7.35-7.31 (m, 4H), 6.99 (s, 1H), 2.48-2.46 (m, 1H), 2.46-2.45 (m, 1H), 2.42 (s, 3H), 1.59-1.54 (m, 1H), 1.50-1.46 (m, 1H).

Example 95

(±)-trans-N-[8-amino-6-[5-(trifluoromethyl)-1H-pyrazol-4-yl]-2, 7-naphthyridin-3-yl]-2-cyano-cyclopropanecarboxamide (Compound 132)

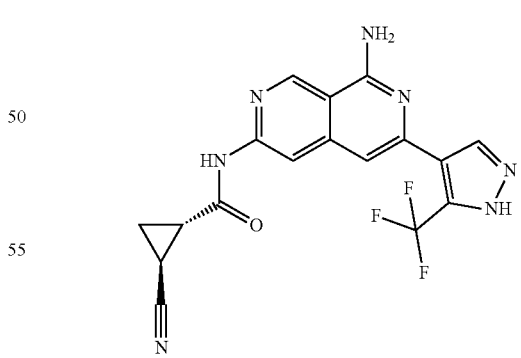

A sealed tube containing (±)-trans-N-(8-amino-6-chloro-2,7-naphthyridin-3-yl)-2-cyano-cyclopropanecarboxamide (120 mg, 0.42 mmol), 4-(4,4,5,5-tetramethyl-1,3,2-dioxaborolan-2-yl)-5-(trifluoromethyl)-1H-pyrazole (130 mg, 0.50 mmol), X-Phos-Pd-G2 (22 mg, 0.03 mmol), X-Phos (27 mg, 0.06 mmol) and potassium acetate (100 mg, 1.02 mmol) was heated to 130° C. in a microwave reactor for 1 h. The reaction was concentrated to dryness and purified by reverse phase chromatography (methanol 0-60/0.1% ammonia in water) to afford (±)-trans-N-[8-amino-6-[5-(trifluoromethyl)-1H-pyrazol-4-yl]-2,7-naphthyridin-3-yl]-2-cyano-cyclopropanecarboxamide (28 mg, 17% yield) as a yellow solid. LCMS (ESI): [M+H]$^+$=388.0, R$_f$(min)=1.76, method=E; $^1$H NMR (400 MHz, CD$_3$OD) δ 9.11 (s, 1H), 8.09 (s, 2H), 6.93 (s, 1H), 2.55-2.50 (m, 1H), 2.06-2.01 (m, 1H), 1.52-1.42 (m, 2H).

Example 96

1-[8-amino-6-(4-methyl-3-pyridyl)-2,7-naphthyridin-3-yl]-3-[(1R,2R)-2-hydroxycyclopentyl]urea (Compound 133)

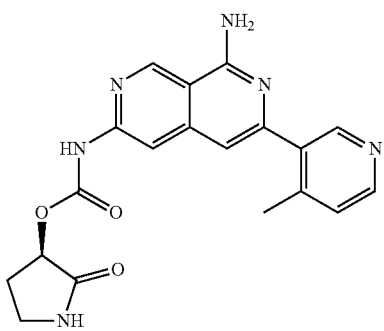 [SMILES: Cc1ccncc1-c1cc2cc(NC(=O)O[C@@H]3CCNC3=O)ncc2c(N)n1]

Step 1: 1-[8-[bis[(2,4-dimethoxyphenyl)methyl]amino]-6-chloro-2,7-naphthyridin-3-yl]-3-[(1S,2S)-2-hydroxycyclopentyl]urea

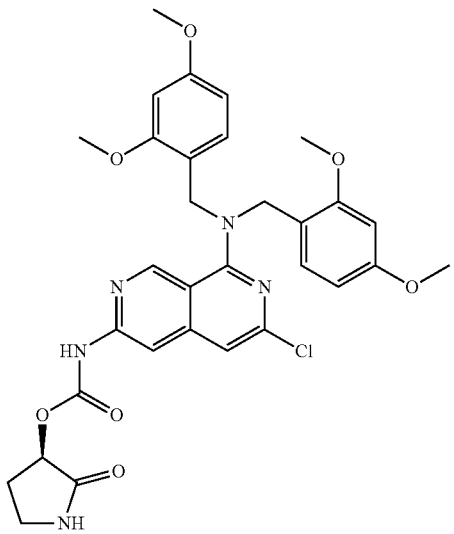 [SMILES: COc1ccc(CN(Cc2ccc(OC)cc2OC)c2nc(Cl)cc3cc(NC(=O)O[C@@H]4CCNC4=O)ncc23)c(OC)c1]

A solution of triphosgene (110 mg, 0.37 mmol) in tetrahydrofuran (5 mL) was added to a mixture of 3-chloro-N1,N1-bis[(2,4-dimethoxyphenyl)methyl]-2,7-naphthyridine-1,6-diamine (100 mg, 0.2 mmol) and triethylamine (0.5 mL, 3.59 mmol). The mixture was stirred at room temperature for 10 min before (3R)-3-hydroxypyrrolidin-2-one (200 mg, 1.98 mmol) was added. The reaction mixture was stirred at room temperature for 1 h. The reaction mixture was concentrated to dryness and purified by column chromatography (ethyl acetate then methanol/dichloromethane, 1/15) to afford [(3R)-2-oxopyrrolidin-3-yl] N-[8-[bis[(2,4-dimethoxyphenyl)methyl]amino]-6-chloro-2,7-naphthyridin-3-yl]carbamate (52 mg, 31% yield) as a yellow solid. LCMS (ESI): [M+H]$^+$=622.2.

Step 2: [(3R)-2-oxopyrrolidin-3-yl]N-[8-[bis[(2,4-dimethoxyphenyl)methyl]amino]-6-(4-methyl-3-pyridyl)-2,7-naphthyridin-3-yl]carbamate

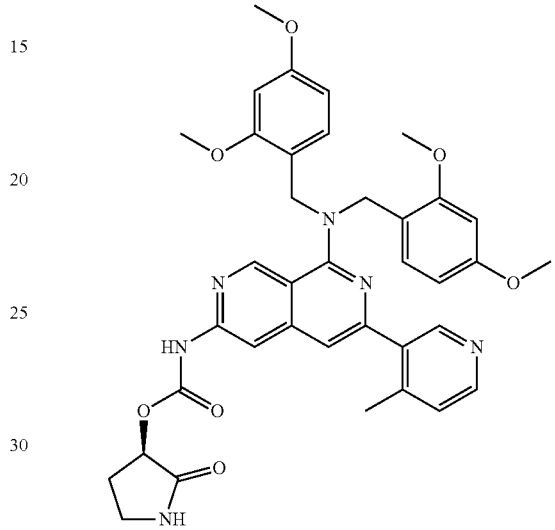

A sealed tube containing [(3R)-2-oxopyrrolidin-3-yl] N-[8-[bis[(2,4-dimethoxyphenyl) methyl]amino]-6-chloro-2,7-naphthyridin-3-yl]carbamate (52 mg, 0.08 mmol), 4-methyl-3-(4,4,5,5-tetramethyl-1,3,2-dioxaborolan-2-yl)pyridine (30 mg, 0.14 mmol), X-Phos-Pd-G2 (8.0 mg, 0.01 mmol), X-Phos (10.0 mg, 0.02 mmol) and potassium acetate (30 mg, 0.31 mmol) was stirred under Ar at 100° C. for 1 h. The reaction was concentrated to dryness and purified by column chromatography (methanol/dichloromethane 1/15) to afford [(3R)-2-oxopyrrolidin-3-yl]N-[8-[bis[(2,4-dimethoxyphenyl)methyl]amino]-6-(4-methyl-3-pyridyl)-2,7-naphthyridin-3-yl]carbamate (47 mg, 44.5% yield) as a yellow solid. LCMS (ESI): [M+H]$^+$=679.3.

Step 3: [(3R)-2-oxopyrrolidin-3-yl]N-[8-amino-6-(4-methyl-3-pyridyl)-2,7-naphthyridin-3-yl]carbamate

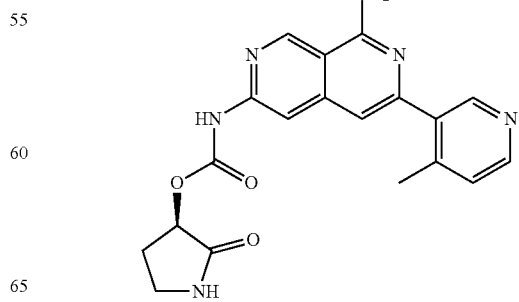

A solution of [(3R)-2-oxopyrrolidin-3-yl] N-[8-[bis[(2,4-dimethoxyphenyl)methyl]amino]-6-(4-methyl-3-pyridyl)-2,7-naphthyridin-3-yl]carbamate (47 mg, 0.07 mmol) in trifluoroacetic acid (3.0 mL, 38.94 mmol) was stirred at 55° C. for 1 h. The reaction was concentrated to dryness and purified by reverse phase chromatography (methanol 50% in 0.05% ammonia in water) to afford [(3R)-2-oxopyrrolidin-3-yl] N-[8-amino-6-(4-methyl-3-pyridyl)-2,7-naphthyridin-3-yl]carbamate (8 mg, 30% yield) as a white solid. LCMS (ESI): [M+H]$^+$=379.2, R$_T$(min)=1.45, method=F; $^1$H NMR (400 MHz, DMSO-d$_6$) δ 10.50 (s, 1H), 9.33 (s, 1H), 8.57 (s, 1H), 8.44 (d, J=4.8 Hz, 1H), 8.09 (s, 1H), 7.97 (s, 1H), 7.32-7.27 (m, 3H), 6.99 (s, 1H), 5.24 (t, J=4.4 Hz, 1H), 3.29-3.24 (m, 2H), 2.42 (s, 3H), 2.06-1.88 (m, 2H).

Example 97

1-[8-amino-6-(4-methyl-3-pyridyl)-2,7-naphthyridin-3-yl]-3-[(1S,2S)-2-hydroxycyclopentyl]urea (Compound 134)

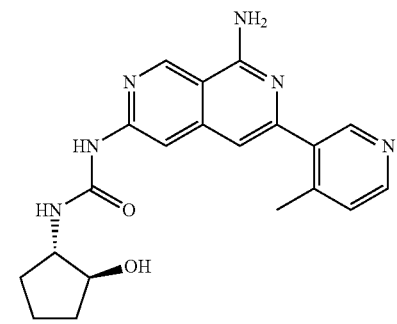 [SMILES: Cc1ccncc1-c1cc2cc(NC(=O)N[C@H]3CCC[C@@H]3O)ncc2c(N)n1]

Step 1: 1-[8-[bis[(2,4-dimethoxyphenyl)methyl]amino]-6-chloro-2,7-naphthyridin-3-yl]-3-[(1S,2S)-2-hydroxycyclopentyl]urea

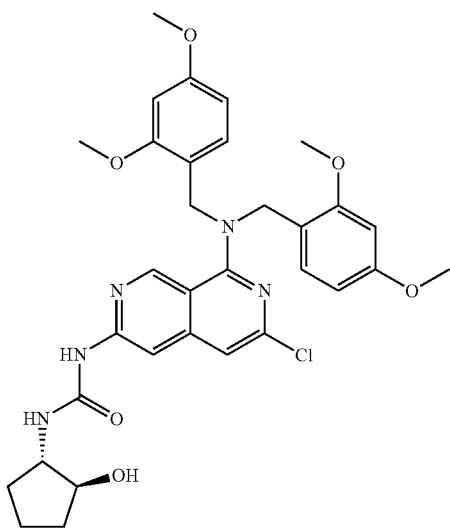 [SMILES: COc1ccc(CN(Cc2ccc(OC)cc2OC)c2nc(Cl)cc3cc(NC(=O)N[C@H]4CCC[C@@H]4O)ncc23)c(OC)c1]

A solution of phenyl N-[8-[bis[(2,4-dimethoxyphenyl)methyl]amino]-6-chloro-2,7-naphthyridin-3-yl]carbamate (500 mg, 0.81 mmol), (1S,2S)-2-aminocyclopentanol (300 mg, 2.97 mmol) and triethylamine (1.0 mL) in N,N-dimethylformamide (5 mL) was stirred at 90° C. for 2 h. To the reaction mixture 20 mL of brine was added and the mixture was extracted with ethyl acetate (20 mL). The organics were then separated, concentrated to dryness, and the resulting residue purified by column chromatography (ethyl ethyl acetate) to afford 1-[8-[bis[(2,4-dimethoxyphenyl)methyl]amino]-6-chloro-2,7-naphthyridin-3-yl]-3-[(1S,2S)-2-hydroxycyclopentyl]urea (148 mg, 25% yield) as a white solid. LCMS(ESI): [M+H]$^+$=622.2.

Step 2: 1-[8-[bis[(2,4-dimethoxyphenyl)methyl]amino]-6-(4-methyl-3-pyridyl)-2,7-naphthyridin-3-yl]-3-[(1S,2S)-2-hydroxycyclopentyl]urea

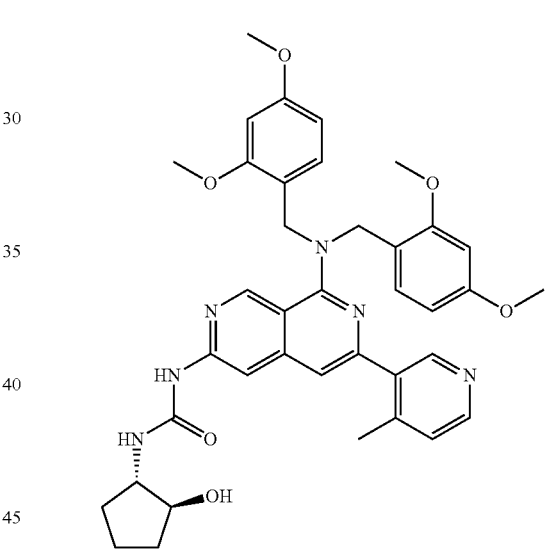

A sealed tube containing 1-[8-[bis[(2,4-dimethoxyphenyl)methyl]amino]-6-chloro-2,7-naphthyridin-3-yl]-3-[(1S,2S)-2-hydroxycyclopentyl]urea (148 mg, 0.24 mmol), 4-methyl-3-(4,4,5,5-tetramethyl-1,3,2-dioxaborolan-2-yl)pyridine (70 mg, 0.32 mmol), X-Phos-Pd-G2 (20 mg, 0.03 mmol), X-Phos (24 mg, 0.05 mmol) and K$_2$CO$_3$ (100.0 mg, 0.72 mmol) was stirred under Ar at 100° C. for 1 h. The reaction was concentrated to dryness and purified by column chromatography (methanol/dichloromethane, 1/10) to afford 1-[8-[bis[(2,4-dimethoxyphenyl)methyl]amino]-6-(4-methyl-3-pyridyl)-2,7-naphthyridin-3-yl]-3-[(1S,2S)-2-hydroxycyclopentyl]urea (140 mg, 59% yield) as a yellow solid. LCMS(ESI): [M+H]+=679.3.

577

Step 3: 1-[8-amino-6-(4-methyl-3-pyridyl)-2,7-naphthyridin-3-yl]-3-[(1S,2S)-2-hydroxycyclopentyl]urea

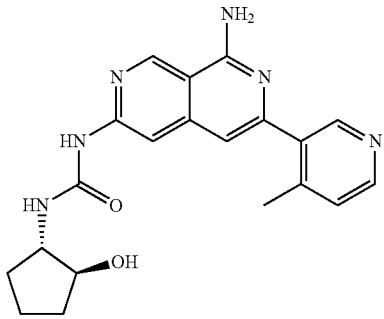 [SMILES: Cc1ccncc1-c1cc2cc(NC(=O)N[C@H]3CCC[C@@H]3O)ncc2c(N)n1]

A solution of 1-[8-[bis [(2, 4-dimethoxyphenyl) methyl] amino]-6-(4-methyl-3-pyridyl)-2,7-naphthyridin-3-yl]-3-[(1S,2S)-2-hydroxycyclopentyl]urea (140 mg, 0.21 mmol) in trifluoroacetic acid (3.0 mL, 38.94 mmol) was stirred at 55° C. for 1 h. The reaction was concentrated to dryness and purified by prep-HPLC (acetonitrile/0.1% HCOOH in water) to afford the formate salt of 1-[8-amino-6-(4-methyl-3-pyridyl)-2,7-naphthyridin-3-yl]-3-[(1S,2S)-2-hydroxycyclopentyl]urea (14 mg, 18% yield) as a white solid. LCMS (ESI): [M+H]$^+$=379.1, R$_T$(min)=1.64, method=E; $^1$H NMR (400 MHz, DMSO-d$_6$) δ 9.26 (s, 1H), 9.09 (s, 1H), 8.56 (s, 1H), 8.43 (d, J=4.8 Hz, 1H), 8.20 (s, 1H), 7.79 (s, 1H), 7.30 (d, J=4.8 Hz, 1H), 7.24 (s, 3H), 3.87-3.83 (m, 1H), 3.78-3.72 (m, 1H), 2.41 (s, 3H), 2.05-2.00 (m, 1H), 1.85-1.78 (m, 1H), 1.71-1.60 (m, 2H), 1.53-1.46 (m, 1H), 1.42-1.35 (m, 1H).

Example 98

(±)-((trans-)-N-(8-amino-6-(5-methyl-2-oxo-2,3-dihydrobenzo[d]oxazol-6-yl)-2,7-naphthyridin-3-yl)-2-cyanocyclopropanecarboxamide (Compound 135)

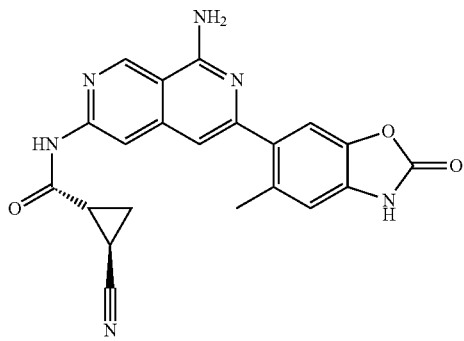

578

Step 1: (±)-(trans-)-N-(8-amino-6-(3-(4-methoxybenzyl)-5-methyl-2-oxo-2,3-dihydrobenzo[d]oxazol-6-yl)-2,7-naphthyridin-3-yl)-2-cyanocyclopropanecarboxamide

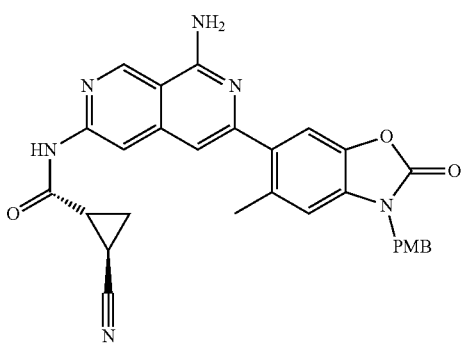

A mixture of (±)-trans-N-(8-amino-6-chloro-2,7-naphthyridin-3-yl)-2-cyano-cyclopropanecarboxamide (130 mg, 0.45 mmol), 3-[(4-methoxyphenyl)methyl]-5-methyl-6-(4,4,5,5-tetramethyl-1,3,2-dioxaborolan-2-yl)-1,3-benzoxazol-2-one (178 mg, 0.45 mmol), K$_2$CO$_3$ (146 mg, 0.45 mmol) and Pd(dppf)Cl$_2$ (33 mg, 0.045 mmol) in 1,4-dioxane (10 mL) and water (1 mL) was stirred at 100° C. for 2 h. The mixture was concentrated and purified by flash column chromatography (0-100% EA in PE) to give (±)-trans-N-[8-amino-6-[3-[(4-methoxyphenyl)methyl]-5-methyl-2-oxo-1,3-benzoxazol-6-yl]-2,7-naphthyridin-3-yl]-2-cyano-cyclopropanecarboxamide (120 mg, 51% yield) as a brown solid. LCMS (ESI): [M+H]$^+$=521.2

Step 2: (±)-(trans-)-N-(8-amino-6-(5-methyl-2-oxo-2,3-dihydrobenzo[d]oxazol-6-yl)-2,7-naphthyridin-3-yl)-2-cyanocyclopropanecarboxamide

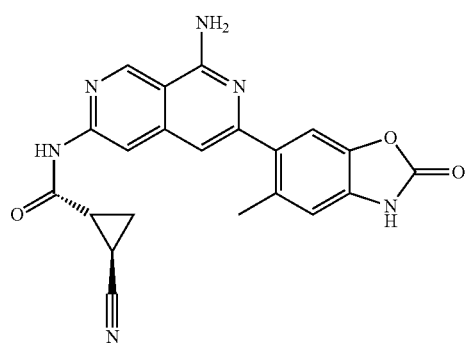

A mixture of (±)-trans-N-[8-amino-6-[3-[(4-methoxyphenyl)methyl]-5-methyl-2-oxo-1,3-benzoxazol-6-yl]-2,7-naphthyridin-3-yl]-2-cyano-cyclopropanecarboxamide (100 mg, 0.19 mmol), TFA (1 mL) and TfOH (1 mL) was stirred at 25° C. for 2 hours. The mixture was concentrated and basified with NH$_3$ in methanol (7M). The resulting residue was purified by reverse phase chromatography (acetonitrile 17-47% in 0.05% HCOOH in water) to give (±)-trans-N-[8-amino-6-(5-methyl-2-oxo-3H-1,3-benzoxazol-6-yl]-2,7-naphthyridin-3-yl]-2-cyano-cyclopropanecarboxamide (18 mg, 24% yield) as a white solid. LCMS (ESI): R$_T$ (min)=1.419, [M+H]$^+$=401.1, method=B; $^1$H NMR (400

MHz, DMSO-d$_6$) δ 11.24 (s, 1H), 9.37 (s, 1H), 8.17 (s, 1H), 8.15 (s, 1H), 7.31 (s, 1H), 7.27 (s, 2H), 6.98 (s, 1H), 6.88 (s, 1H), 2.78-2.73 (m, 1H), 2.37 (s, 3H), 2.17-2.12 (m, 1H), 1.63-1.58 (m, 1H), 1.45-1.41 (m, 1H).

Example 99

(±)-cis-N1-(8-amino-6-(4-methylpyridin-3-yl)-2,7-naphthyridin-3-yl)-N2,N2-dimethylcyclopropane-1,2-dicarboxamide (Compound 136)

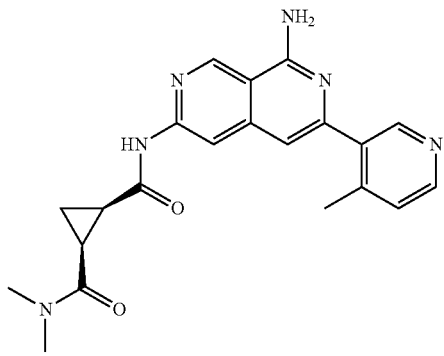 [SMILES: Cc1ccncc1-c1cc2cc(NC(=O)[C@@H]3C[C@@H]3C(=O)N(C)C)ncc2c(N)n1]

Step 1: (±)-cis-methyl 2-(8-(bis(4-methoxybenzyl)amino)-6-(4-methylpyridin-3-yl)-2,7-naphthyridin-3-ylcarbamoyl)cyclopropanecarboxylate

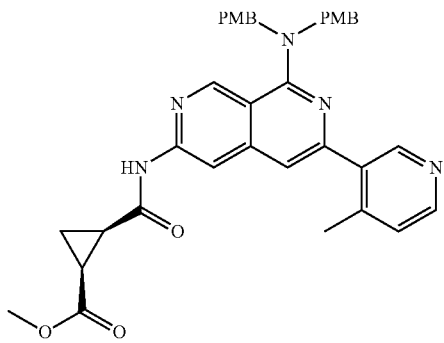

To a solution of (±)-cis-2-(methoxycarbonyl)cyclopropanecarboxylic acid (263 mg, 1.83 mmol) and DMF (10 mg) in dichloromethane (10 mL) was added ethanedioyl dichloride (278 mg, 2.2 mmol). The mixture was stirred at 25° C. for 1 h. The mixture was concentrated and added to a solution of N1,N1-bis[(4-methoxyphenyl)methyl]-3-(4-methyl-3-pyridyl)-2,7-naphthyridine-1,6-diamine (900 mg, 1.83 mmol) and pyridine (2 mL) in dichloromethane (10 mL). The mixture was stirred at 25° C. for 1 h. The mixture was concentrated and purified by flash column chromatography (0-100% EA in PE) to give N1,N1-bis[(4-methoxyphenyl)methyl]-3-(4-methyl-3-pyridyl)-2,7-naphthyridine-1,6-diamine (700 mg, 75% yield) as a brown solid. LCMS (ESI): [M+H]$^+$=618.2

Step 2: (±)-cis-2-(8-(bis(4-methoxybenzyl)amino)-6-(4-methylpyridin-3-yl)-2,7-naphthyridin-3-ylcarbamoyl)cyclopropanecarboxylic acid

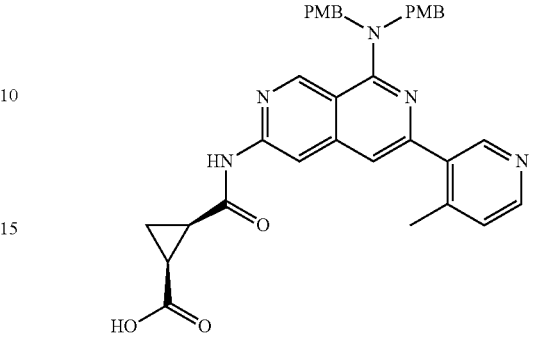

To a solution of methyl (±)-cis-2-[[8-[bis[(4-methoxyphenyl)methyl]amino]-6-(4-methyl-3-pyridyl)-2,7-naphthyridin-3-yl]carbamoyl]cyclopropanecarboxylate (100 mg, 0.16 mmol) in THF (10 mL) was added 1N NaOH (0.32 mL). The mixture was stirred at 25° C. for 16 hours. The mixture was acidified with 2 N HCl, extracted with EA (30 mL×2), dried over Na$_2$SO$_4$ and concentrated to afford crude (±)-cis-2-[[8-[bis[(4-methoxyphenyl)methyl]amino]-6-(4-methyl-3-pyridyl)-2,7-naphthyridin-3-yl]carbamoyl]cyclopropanecarboxylic acid (70 mg, 72% yield) as a brown solid. LCMS (ESI): [M+H]$^+$=604.2

Step 3: (±)-(cis)-N1-(8-(bis(4-methoxybenzyl)amino)-6-(4-methylpyridin-3-yl)-2,7-naphthyridin-3-yl)-N2,N2-dimethylcyclopropane-1,2-dicarboxamide

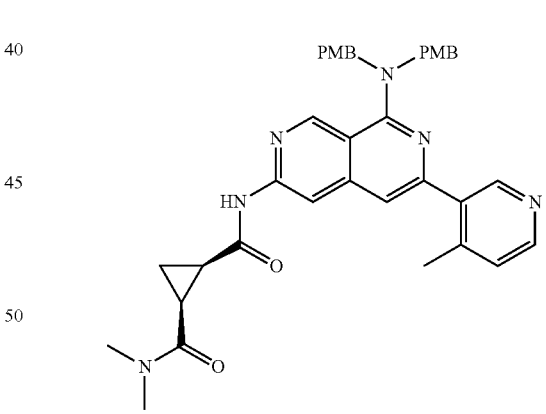

To a solution of (±)-cis-2-[[8-[bis[(4-methoxyphenyl)methyl]amino]-6-(4-methyl-3-pyridyl)-2,7-naphthyridin-3-yl]carbamoyl]cyclopropanecarboxylic acid (200 mg, 0.33 mmol), HATU (125 mg, 0.33 mmol) and DIPEA (128 mg, 0.99 mmol) in dichloromethane (10 mL) was added N,N-dimethylamine hydrochloride (135 mg, 1.66 mmol). The mixture was stirred at 25° C. for 16 hours. The mixture was washed with water (5 mL) and concentrated to give the crude (±)-cis-N2-[8-[bis[(4-methoxyphenyl)methyl]amino]-6-(4-methyl-3-pyridyl)-2,7-naphthyridin-3-yl]-N1,N1-dimethyl-cyclopropane-1,2-dicarboxamide (160 mg, 51% yield) as a brown solid. LCMS (ESI): [M+H]$^+$=631.3

Step 4: (±)-(cis)-N1-(8-amino-6-(4-methylpyridin-3-yl)-2,7-naphthyridin-3-yl)-N2,N2-dimethylcyclopropane-1,2-dicarboxamide

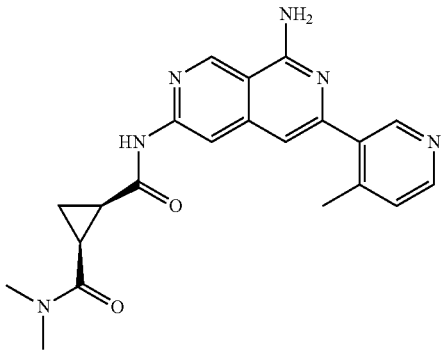 [SMILES: Cc1ccncc1-c1cc2cc(NC(=O)[C@@H]3C[C@@H]3C(=O)N(C)C)ncc2c(N)n1]

A mixture of (±)-cis-N2-[8-[bis[(4-methoxyphenyl)methyl]amino]-6-(4-methyl-3-pyridyl)-2,7-naphthyridin-3-yl]-N1,N1-dimethyl-cyclopropane-1,2-dicarboxamide (80 mg, 0.13 mmol) in TFA (3 mL) was stirred at 25° C. for 4 hours. The mixture was concentrated and basified with NH$_3$ in methanol (7M). The resulting residue was purified by reverse phase chromatography (acetonitrile 0-70 in 0.05% NH$_4$HCO$_3$ in water) to afford (±)-cis-N2-[8-amino-6-(4-methyl-3-pyridyl)-2,7-naphthyridin-3-yl]-N1,N1-dimethyl-cyclopropane-1,2-dicarboxamide (3 mg, 6.1% yield) as a white solid. LCMS (ESI): R$_T$ (min)=1.402, [M+H]$^+$=391.2, method=C; $^1$H NMR (400 MHz, CD$_3$OD) δ 9.26 (s, 1H), 8.53 (s, 1H), 8.43 (d, J=4.8 Hz, 1H), 8.28 (s, 1H), 7.40 (d, J=4.8 Hz, 1H), 6.98 (s, 1H), 3.18 (s, 3H), 2.93 (s, 3H), 2.45 (s, 3H), 2.43-2.41 (m, 1H), 2.35-2.29 (m, 1H), 1.73-1.69 (m, 1H), 1.38-1.33 (m, 1H).

Example 100

(±)-(cis)-N1-(8-amino-6-(4-methylpyridin-3-yl)-2,7-naphthyridin-3-yl)-N2-ethylcyclopropane-1,2-dicarboxamide (Compound 137)

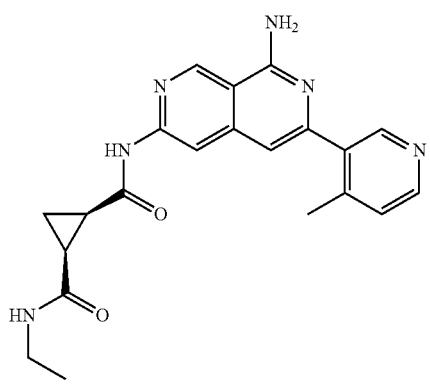 [SMILES: CCNC(=O)[C@H]1C[C@H]1C(=O)Nc1cc2cc(-c3cnccc3C)nc(N)c2cn1]

Step 1: (±)-cis-N1-(8-(bis(4-methoxybenzyl)amino)-6-(4-methylpyridin-3-yl)-2,7-naphthyridin-3-yl)-N2-ethylcyclopropane-1,2-dicarboxamide

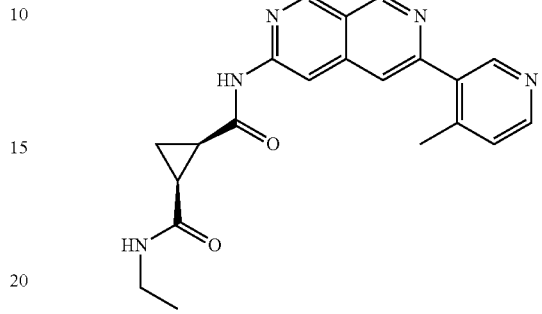

To a solution of (±)-cis-2-[[8-[bis[(4-methoxyphenyl)methyl]amino]-6-(4-methyl-3-pyridyl)-2,7-naphthyridin-3-yl]carbamoyl]cyclopropanecarboxylic acid (200 mg, 0.33 mmol), HATU (125 mg, 0.33 mmol) and DIPEA (128 mg, 0.99 mmol) in dichloromethane (10 mL) was added ethanamine hydrochloride (135 mg, 1.66 mmol). The mixture was stirred at 25° C. for 16 hours. The mixture was washed with water and extracted with DCM (15 mL×2). The organics were concentrated to give crude (±)-cis-N1-[8-[bis[(4-methoxyphenyl)methyl]amino]-6-(4-methyl-3-pyridyl)-2,7-naphthyridin-3-yl]-N2-ethyl-cyclopropane-1,2-dicarboxamide (150 mg, 72% yield) as a brown solid. LCMS (ESI): [M+H]$^+$=631.2

Step 2: (±)-cis-N1-(8-amino-6-(4-methylpyridin-3-yl)-2,7-naphthyridin-3-yl)-N2-ethylcyclopropane-1,2-dicarboxamide

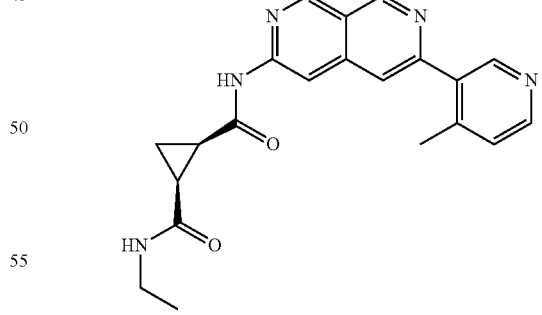

A mixture of (±)-cis-N1-[8-[bis[(4-methoxyphenyl)methyl]amino]-6-(4-methyl-3-pyridyl)-2,7-naphthyridin-3-yl]-N2-ethyl-cyclopropane-1,2-dicarboxamide (80 mg, 0.13 mmol) and TFA (2 mL) was stirred at 60° C. for 2 hours. The mixture was concentrated and basified with NH$_3$ in methanol (7M). The resulting residue was purified by reverse phase chromatography (acetonitrile 0-70% in 0.05% NH$_4$HCO$_3$ in water) to obtain (±)-cis-N1-[8-amino-6-(4-methyl-3-pyridyl)-2,7-naphthyridin-3-yl]-N2-ethyl-cyclopropane-1, 2-dicarboxamide (6 mg, 12.1% yield) as a white solid. LCMS (ESI): $R_T$ (min)=1.428, [M+H]⁺=391.1, method=C; ¹H NMR (400 MHz, CD₃OD) δ 9.28 (s, 1H), 8.54 (s, 1H), 8.43 (d, J=5.2 Hz, 1H), 8.31 (s, 1H), 7.40 (d, J=5.2 Hz, 1H), 6.98 (s, 1H), 3.24-3.18 (m, 2H), 2.45 (s, 3H), 2.30-2.26 (m, 1H), 2.14-2.12 (m, 1H), 1.72-1.69 (m, 1H), 1.34-1.30 (m, 1H), 1.11 (t, J=7.2 Hz, 3H).

Example 101

(±)-trans-N1-(8-amino-6-(4-methylpyridin-3-yl)-2,7-naphthyridin-3-yl)-N2,N2-dimethylcyclopropane-1,2-dicarboxamide (Compound 138)

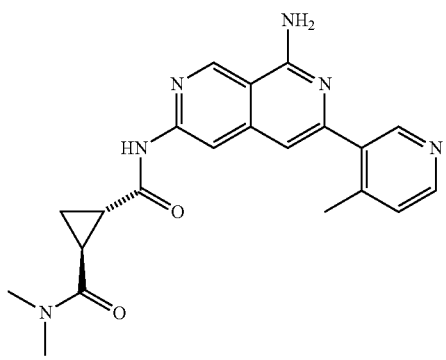

Step 1: (±)-trans-methyl 2-(8-(bis(2,4-dimethoxybenzyl)amino)-6-(4-methylpyridin-3-yl)-2,7-naphthyridin-3-ylcarbamoyl)cyclopropanecarboxylate

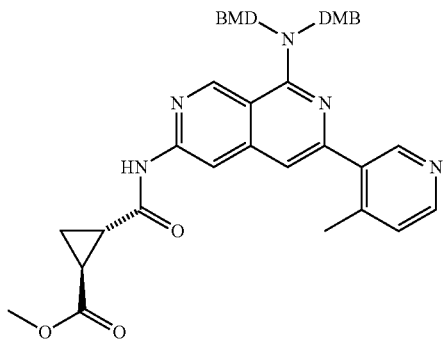

To a solution of (±)-trans-2-methoxycarbonylcyclopropanecarboxylic acid (109 mg, 0.76 mmol) and DMF (10 mg) in dichloromethane (15 mL) was added ethanedioyl dichloride (120 mg, 0.95 mmol). The mixture was stirred at 25° C. for 1 hour and then concentrated. The residue was added to a solution of N1,N1-bis[(2,4-dimethoxyphenyl)methyl]-3-(4-methyl-3-pyridyl)-2,7-naphthyridine-1,6-diamine (350 mg, 0.63 mmol) and pyridine (0.5 mL) in dichloromethane (15 mL). The mixture was stirred at 25° C. for another 1 h. The mixture was concentrated to give methyl (±)-trans-2-[[8-[bis[(2,4-dimethoxyphenyl)methyl]amino]-6-(4-methyl-3-pyridyl)-2,7-naphthyridin-3-yl]carbamoyl] cyclopropanecarboxylate (560 mg, 29% yield). LCMS (ESI): [M+H]⁺=678.3.

Step 2: (±)-trans-2-(8-(bis(2,4-dimethoxybenzyl)amino)-6-(4-methylpyridin-3-yl)-2,7-naphthyridin-3-ylcarbamoyl)cyclopropanecarboxylic acid

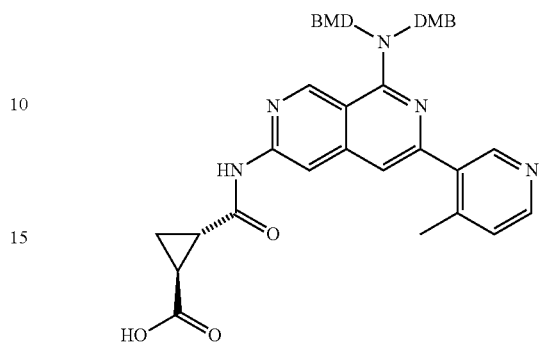

A mixture of methyl (trans)-2-[[8-[bis[(2,4-dimethoxyphenyl)methyl]amino]-6-(4-methyl-3-pyridyl)-2,7-naphthyridin-3-yl]carbamoyl]cyclopropanecarboxylate (560 mg, 0.18 mmol) and 1N LiOH (0.73 mL) in tetrahydrofuran (10 mL) was stirred at 25° C. for 16 hours. The mixture was diluted with ethyl acetate (10 mL). The aqueous layer was acidified with 1 N HCl and extracted with ethyl acetate (15 mL×2). The organic layer was concentrated to give (±)-(trans-)-2-[[8-[bis[(2,4-dimethoxyphenyl)methyl]amino]-6-(4-methyl-3-pyridyl)-2,7-naphthyridin-3-yl]carbamoyl]cyclopropanecarboxylic acid (120 mg, 40% yield) as a brown solid. LCMS (ESI): [M+H]⁺=664.3.

Step 3: (±)-trans-N1-(8-(bis(2,4-dimethoxybenzyl)amino)-6-(4-methylpyridin-3-yl)-2,7-naphthyridin-3-yl)-N2,N2-dimethylcyclopropane-1,2-dicarboxamide

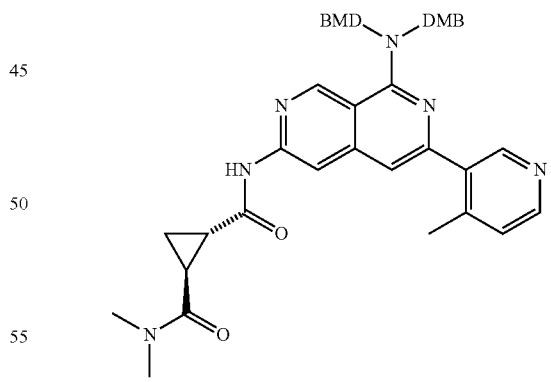

A mixture of (±)-trans-2-[[8-[bis[(2,4-dimethoxyphenyl)methyl]amino]-6-(4-methyl-3-pyridyl)-2,7-naphthyridin-3-yl]carbamoyl]cyclopropanecarboxylic acid (120 mg, 0.07 mmol), N,N-dimethylamine hydrochloride (29 mg, 0.36 mmol), HATU (27 mg, 0.07 mmol) and DIPEA (27 mg, 0.22 mmol) in dichloromethane (10 mL) was stirred at 25° C. for 16 h. The mixture was washed with H₂O (10 mL), concentrated and the residue was used for next step directly without further purification. LCMS (ESI): [M+H]⁺=691.3

Step 4: (±)-trans-N1-(8-amino-6-(4-methylpyridin-3-yl)-2,7-naphthyridin-3-yl)-N2,N2-dimethylcyclopropane-1,2-dicarboxamide

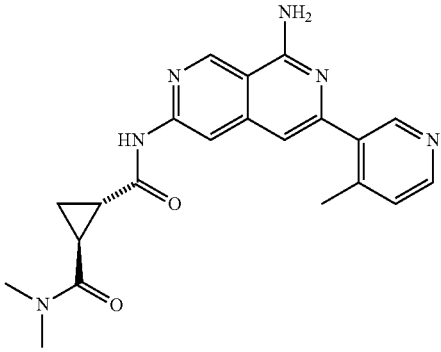

A mixture of (±)-trans-N2-[8-[bis[(2,4-dimethoxyphenyl)methyl]amino]-6-(4-methyl-3-pyridyl)-2,7-naphthyridin-3-yl]-N1,N1-dimethyl-cyclopropane-1,2-dicarboxamide (150 mg, 0.22 mmol) in TFA (8 mL) was stirred at 50° C. for 3 hours. The mixture was concentrated and basified with NH$_3$ in methanol (7M). The resulting residue was purified by reverse phase chromatography (acetonitrile 0-70/0.5% NH$_4$HCO$_3$ in water) to afford (±)-trans-N2-[8-amino-6-(4-methyl-3-pyridyl)-2,7-naphthyridin-3-yl]-N1,N1-dimethyl-cyclopropane-1,2-dicarboxamide (40 mg, 47% yield) as a white solid. LCMS (ESI): R$_T$ (min)=1.522, [M+H]$^+$=391.2, method=C; $^1$H NMR (400 MHz, DMSO-d$_6$) δ 11.05 (s, 1H), 9.37 (s, 1H), 8.56 (s, 1H), 8.44 (d, J=4.8 Hz, 1H), 8.25 (s, 1H), 7.32 (d, J=4.8 Hz, 1H), 7.30 (s, 2H), 6.97 (s, 1H), 3.12 (s, 3H), 2.86 (s, 3H), 2.48-2.45 (m, 1H), 2.41 (s, 3H), 2.39-2.35 (m, 1H), 1.28-1.25 (m, 1H).

Example 102

(±)-trans-N-(8-amino-6-(4-methylpyridin-3-yl)-2,7-naphthyridin-3-yl)-2-methylcyclopropane carboxamide (Compound 139)

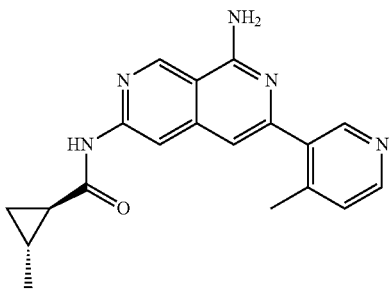 [SMILES: Cc1ccncc1-c1cc2cc(NC(=O)[C@@H]3C[C@H]3C)ncc2c(N)n1]

Step 1: (±)-trans-N-(6,8-dichloro-2,7-naphthyridin-3-yl)-2-methylcyclopropanecarboxamide

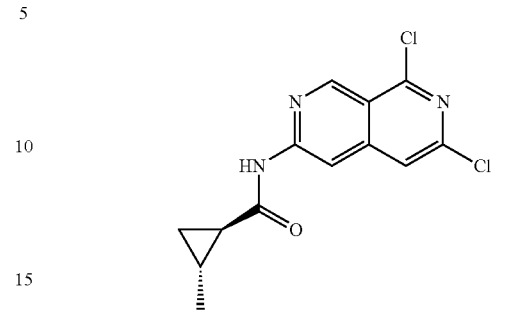

A mixture of 6,8-dichloro-2,7-naphthyridin-3-amine (200 mg, 0.93 mmol), (±)-(trans)-2-methylcyclopropanecarboxylic acid (113 mg, 1.13 mmol) in pyridine (0.5 mL) and dichloromethane (4 mL) was stirred at 0° C. for 0.5 h. POCl$_3$ (0.1 mL, 1.07 mmol) was added in portions. The mixture stirred for 1 h at room temperature. The reaction was diluted with EtOAc (10 mL) and the pH adjusted to 7-8 with sat NaHCO$_3$. The organics were then separated, dried (NaSO$_4$) and concentrated to dryness. The residue was purified with silica gel column chromatography (PE:EA=10:1 to PE:EA=4:1) to give the title compound as a solid (200 mg, 70% yield). LCMS (ESI) [M+H]$^+$=296.1.

Step 2: (±)-trans-N-(8-amino-6-chloro-2,7-naphthyridin-3-yl)-2-methylcyclopropanecarboxamide

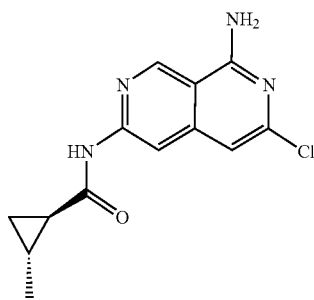 [SMILES: C[C@@H]1C[C@H]1C(=O)Nc1cc2cc(Cl)nc(N)c2cn1]

A mixture of (±)-trans-N-(6,8-dichloro-2,7-naphthyridin-3-yl)-2-methyl-cyclopropanecarboxamide (195 mg, 0.66 mmol), NH$_4$OH (2 mL, 0.66 mmol) in 1,4-dioxane (2 mL) was heated at 90° C. for 3 h under Ar. The reaction was concentrated and purified by silica gel chromatography (PE:EA=2:1 to PE:EA=1:1) to give the title compound as a white solid (150 mg, 82% yield). LCMS (ESI) [M+H]$^+$=277.1.

Step 3: (±)-trans-N-(8-amino-6-(4-methylpyridin-3-yl)-2,7-naphthyridin-3-yl)-2-methylcyclopropanecarboxamide

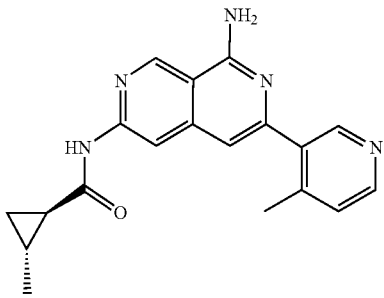 [SMILES: Cc1ccncc1-c1cc2cc(NC(=O)[C@@H]3C[C@H]3C)ncc2c(N)n1]

A mixture of (±)-trans-N-(8-amino-6-chloro-2,7-naphthyridin-3-yl)-2-methyl-cyclopropanecarboxamide (80 mg, 0.29 mmol), 4-methyl-3-(4,4,5,5-tetramethyl-1,3,2-dioxaborolan-2-yl)pyridine (76 mg, 0.35 mmol), XPhos Pd G2 (23 mg, 0.03 mmol), XPhos (14 mg, 0.03 mmol) and $K_2CO_3$ (120 mg, 0.87 mmol) in 1,4-dioxane (4 mL) and water (1 mL) was heated at 100° C. for 3 h under Ar. The reaction was concentrated to dryness and purified by silica gel chromatography (PE:EA=1:1 to EA) to give the title compound as a white solid (67.3 mg, 70% yield). LCMS (ESI): $R_T$(min)= 1.39, $[M+H]^+$=334.2, method=B. $^1H$ NMR (400 MHz, DMSO-$d_6$) δ 10.87 (s, 1H), 9.36 (s, 1H), 8.56 (s, 1H), 8.43 (d, J=4.8 Hz, 1H), 8.22 (s, 1H), 7.31-7.30 (m, 3H), 6.95 (s, 1H), 2.40 (s, 3H), 1.85-1.81 (m, 1H), 1.29-1.24 (m, 1H), 1.10 (d, J=6.0 Hz, 3H), 1.07-1.02 (m, 1H), 0.71-0.66 (m, 1H).

Example 103

(±)-trans-N-(8-amino-6-(4-methylpyridin-3-yl)-2,7-naphthyridin-3-yl)-2-(trifluoromethyl) cyclopropane carboxamide (Compound 140)

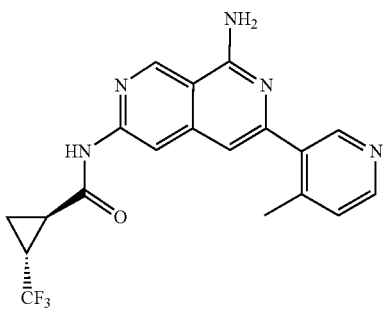 [SMILES: Cc1ccncc1-c1cc2cc(NC(=O)[C@@H]3C[C@H]3C(F)(F)F)ncc2c(N)n1]

Step 1: (±)-trans-N-(6,8-dichloro-2,7-naphthyridin-3-yl)-2-(trifluoromethyl)cyclopropanecarboxamide

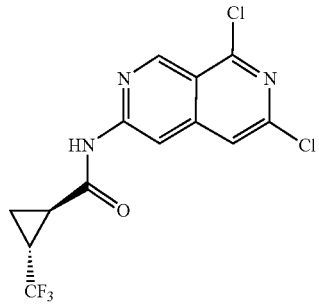 [SMILES: O=C(Nc1cc2cc(Cl)nc(Cl)c2cn1)[C@@H]1C[C@H]1C(F)(F)F]

A mixture of 6,8-dichloro-2,7-naphthyridin-3-amine (200 mg, 0.93 mmol), (±)-trans-2-(trifluoromethyl)cyclopropane carboxylic acid (173 mg, 1.12 mmol) in pyridine (0.5 mL) and dichloromethane (4 mL) was stirred at 0° C. for 0.5 h. $POCl_3$ (0.1 mL, 1.07 mmol) was then added to the reaction mixture and the mixture stirred at room temperature for 1 h. The reaction mixture was diluted with EtOAc (20 mL) and adjusted pH to 7-8 with sat $NaHCO_3$. The organics were separated, dried ($NaSO_4$) and concentrated to dryness. The residue was purified with silica column chromatography (PE:EA=10:1 to PE:EA=4:1) to give the title compound as a white solid (220 mg, 65% yield). LCMS (ESI) $[M+H]^+$=350.0.

Step 2: (±)-trans-N-(8-amino-6-chloro-2,7-naphthyridin-3-yl)-2-(trifluoromethyl)cyclopropanecarboxamide

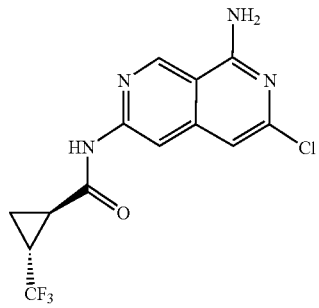

A mixture of (±)-trans-N-(6,8-dichloro-2,7-naphthyridin-3-yl)-2-(trifluoromethyl)cyclopropanecarboxamide (215 mg, 0.61 mmol) and $NH_4OH$ (2 mL, 0.61 mmol) in 1,4-dioxane (2 mL) was heated at 90° C. for 3 h under Ar. The reaction was concentrated and purified with silica column chromatography (PE:EA=4:1 PE:EA=2:1) to give the title compound as a white solid (180 mg, 88% yield). LCMS (ESI) $[M+H]^+$=331.1.

589

Step 3: (±)-trans-N-(8-amino-6-(4-methylpyridin-3-yl)-2,7-naphthyridin-3-yl)-2-(trifluoromethyl)cyclopropane carboxamide

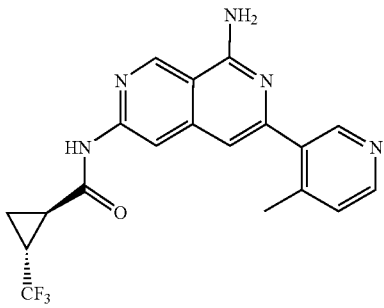 [SMILES: Cc1ccncc1-c1cc2cc(NC(=O)[C@@H]3C[C@H]3C(F)(F)F)ncc2c(N)n1]

A mixture of 4-methyl-3-(4,4,5,5-tetramethyl-1,3,2-dioxaborolan-2-yl)pyridine (64 mg, 0.29 mmol), (trans)-N-(8-amino-6-chloro-2,7-naphthyridin-3-yl)-2-(trifluoromethyl)cyclopropanecarboxamide (80 mg, 0.24 mmol), XPhos Pd G2 (19 mg, 0.02 mmol), XPhos (12 mg, 0.03 mmol) and K$_2$CO$_3$ (101 mg, 0.73 mmol) in 1,4-dioxane (4 mL) and water (1 mL) was heated at 100° C. for 3 h under Ar. The reaction was concentrated and purified by silica gel chromatography (PE:EA=3:1) to give the title compound as a white solid (50.3 mg, 54% yield). LCMS (ESI): R$_T$(min)=1.46, [M+H]$^+$=388.2, method=B. $^1$H NMR (400 MHz, DMSO-d$_6$) δ 11.20 (s, 1H), 9.39 (s, 1H), 8.56 (s, 1H), 8.43 (d, J=4.8 Hz, 1H), 8.23 (s, 1H), 7.35 (s, 2H), 7.31 (d, J=4.8 Hz, 1H), 6.99 (s, 1H), 2.32-2.59 (m, 1H), 2.41 (s, 3H), 2.33-2.30 (m, 1H), 1.35-1.31 (m, 2H).

Example 104

(±)-cis-N-(8-amino-6-(4-methylpyridin-3-yl)-2,7-naphthyridin-3-yl)-2-methylcyclopropanecarboxamide (Compound 141)

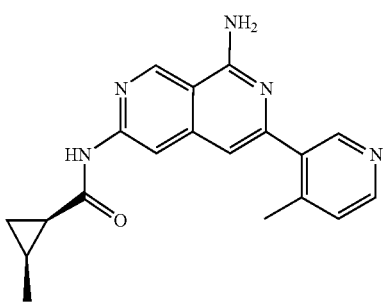 [SMILES: Cc1ccncc1-c1cc2cc(NC(=O)[C@@H]3C[C@@H]3C)ncc2c(N)n1]

590

Step 1: (±)-cis-N-(6,8-dichloro-2,7-naphthyridin-3-yl)-2-methylcyclopropanecarboxamide

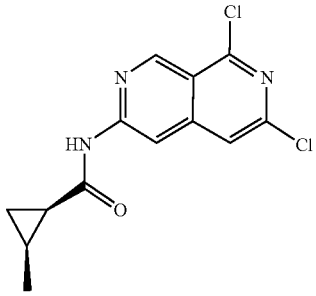 [SMILES: C[C@H]1C[C@H]1C(=O)Nc1cc2cc(Cl)nc(Cl)c2cn1]

A mixture of 6,8-dichloro-2,7-naphthyridin-3-amine (200 mg, 0.93 mmol), (±)-cis-2-methylcyclopropanecarboxylic acid (113 mg, 1.13 mmol) in pyridine (0.5 mL) and dichloromethane (4 mL) was stirred at 0° C. for 0.5 h. POCl$_3$ (0.1 mL, 1.07 mmol) was then added in portions. The mixture was stirred for 1 h at room temperature. The reaction mixture was diluted with EtOAc (10 ml) and adjusted pH to 7-8 with sat NaHCO$_3$. The organics were then separated, dried (Na$_2$SO$_4$), concentrated and purified by silica gel chromatography (PE:EA=10:1 to PE:EA=4:1) to give (±)-cis-N-(6,8-dichloro-2,7-naphthyridin-3-yl)-2-methyl-cyclopropanecarboxamide (200 mg, 72% yield) as a white solid. LCMS (ESI) [M+H]$^+$=296.1.

Step 2: (±)-cis-N-(8-amino-6-chloro-2,7-naphthyridin-3-yl)-2-methylcyclopropanecarboxamide

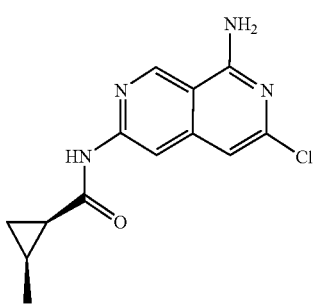 [SMILES: C[C@H]1C[C@H]1C(=O)Nc1cc2cc(Cl)nc(N)c2cn1]

A mixture of (±)-cis-N-(6,8-dichloro-2,7-naphthyridin-3-yl)-2-methyl-cyclopropanecarboxamide (180 mg, 0.61 mmol), NH$_4$OH (4 mL, 0.61 mmol) in 1,4-dioxane (4 mL) was heated at 90° C. for 3 h under Ar. The reaction was concentrated and purified by silica gel chromatography (PE:EA=2:1 to PE:EA=1:1) to give (±)-cis-N-(8-amino-6-chloro-2,7-naphthyridin-3-yl)-2-methyl-cyclopropanecarboxamide (150 mg, 89% yield) as a white solid. LCMS (ESI) [M+H]$^+$=277.1.

Step 3: (±)-cis-N-(8-amino-6-(4-methylpyridin-3-yl)-2,7-naphthyridin-3-yl)-2-methylcyclopropane carboxamide

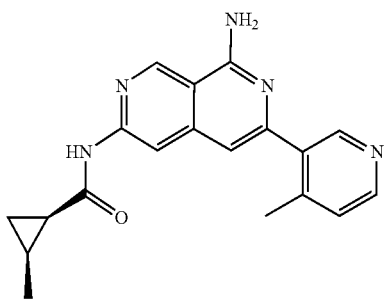 [SMILES: Cc1ccncc1-c1cc2cc(NC(=O)[C@@H]3C[C@@H]3C)ncc2c(N)n1]

A mixture of (±)-cis-N-(8-amino-6-chloro-2,7-naphthyridin-3-yl)-2-methyl-cyclopropanecarboxamide (130 mg, 0.47 mmol), 4-methyl-3-(4,4,5,5-tetramethyl-1,3,2-dioxaborolan-2-yl)pyridine (124 mg, 0.57 mmol), XPhos Pd G$_2$ (74 mg, 0.09 mmol), XPhos (90 mg, 0.19 mmol) and K$_2$CO$_3$ (195 mg, 1.41 mmol) in 1,4-dioxane (15 mL) and water (3 mL) was heated at 100° C. for 3 h under Ar. The reaction was concentrated and purified by silica gel chromatography (PE:EA=1:1 to EA to DCM:MeOH=20)) to give (±)-cis-N-[8-amino-6-(4-methyl-3-pyridyl)-2,7-naphthyridin-3-yl]-2-methyl-cyclopropanecarboxamide (71 mg, 46% yield) as a white solid. LCMS (ESI): R$_T$ (min)=1.72, [M+H]$^+$=334.1, method=C; $^1$H NMR (CD$_3$OD, 400 MHz): δ 9.29 (s, 1H), 8.54 (s, 1H), 8.43 (d, J=5.2 Hz, 1H), 8.32 (s, 1H), 7.41 (d, J=5.2 Hz, 1H), 7.00 (s, 1H), 2.46 (s, 3H), 2.03-1.98 (m, 1H), 1.45-1.38 (m, 1H), 1.22 (d, J=6.0 Hz, 3H), 1.10-1.05 (m, 1H), 1.02-0.98 (m, 1H).

Example 105

(±)-trans-N-(8-amino-6-(3,5-dimethyl-2-oxo-2,3-dihydrobenzo[d]oxazol-6-yl)-2,7-naphthyridin-3-yl)-2-cyanocyclopropanecarboxamide (Compound 142)

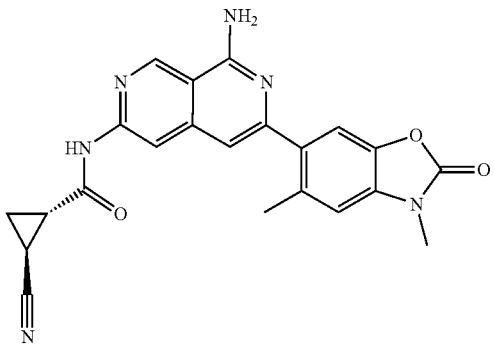 [SMILES: Cc1cc2c(cc1-c1cc3cc(NC(=O)[C@H]4C[C@@H]4C#N)ncc3c(N)n1)oc(=O)n2C]

Step 1: 6-bromo-5-methylbenzo[d]oxazol-2(3H)-one

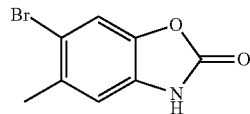

A mixture of 5-methyl-3H-1,3-benzoxazol-2-one (1.0 g, 6.70 mmol) and 1-bromo-2,5-pyrrolidinedione (1.3 g, 7.30 mmol) in acetic acid (15 mL) was stirred at 20° C. for 16 hours. The mixture was diluted with water (50 mL) and stirred for an additional 15 minutes. The mixture was then filtered and washed with water (10 mL) to gave 6-bromo-5-methyl-3H-1,3-benzoxazol-2-one (1.2 g, 79% yield) as a white solid. LCMS (ESI) [M+H]$^+$=228.1.

Step 2: 6-bromo-3,5-dimethylbenzo[d]oxazol-2(3H)-one

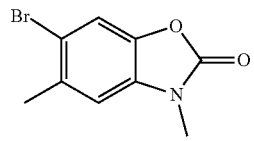

To a solution of 6-bromo-5-methyl-3H-1,3-benzoxazol-2-one (200 mg, 0.88 mmol) in N,N-dimethylformamide (4 mL) was added in sodium hydride (60% in mine oil, 50 mg, 1.25 mmol) at 0° C. The mixture was stirred at 0° C. for 15 min. Iodomethane (0.1 mL, 1.61 mmol) was added. The reaction mixture was stirred at 0° C. for 1 h before diluting with 20 mL of brine. The mixture was extracted with ethyl acetate (10 mL) and the organics were washed with brine. The organics were separated, concentrated and purified by silica gel column chromatography (EA:PE=1:4) to give 6-bromo-3,5-dimethyl-1,3-benzoxazol-2-one (190 mg, 0.78 mmol, 89.5% yield) as a white solid. LCMS (ESI) [M+H]$^+$=242.1.

Step 3: 3,5-dimethyl-6-(4,4,5,5-tetramethyl-1,3,2-dioxaborolan-2-yl)benzo[d]oxazol-2(3H)-one

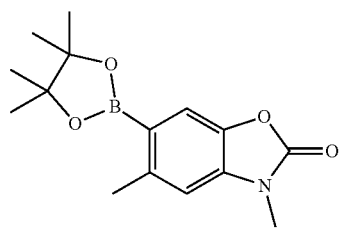 [SMILES: Cc1cc2c(cc1B1OC(C)(C)C(C)(C)O1)oc(=O)n2C]

To a sealed tube was added 6-bromo-3,5-dimethyl-1,3-benzoxazol-2-one (180 mg, 0.74 mmol), bis(pinacolato)diboron (220 mg, 0.87 mmol), Pd(dppf)Cl$_2$ (52 mg, 0.07 mmol), acetoxypotassium (220 mg, 2.24 mmol) and 1,4-dioxane (10 mL). The mixture was bubbled with N$_2$ for 2 min, and stirred at 100° C. for 3 h. The mixture was then directly purified by silica gel column chromatography (EA:PE=1:4) to give 3,5-dimethyl-6-(4,4,5,5-tetramethyl-1,3,2- dioxaborolan-2-yl)-1,3-benzoxazol-2-one (180 mg, 84% yield) as a white solid. LCMS (ESI) [M+H]⁺=290.1.

Step 4: (±)-trans-N-(8-amino-6-(3,5-dimethyl-2-oxo-2,3-dihydrobenzo[d]oxazol-6-yl)-2,7-naphthyridin-3-yl)-2-cyanocyclopropanecarboxamide

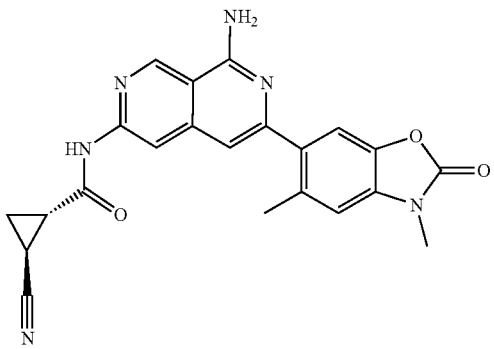 [SMILES: Cc1cc2c(cc1-c1cc3cc(NC(=O)[C@H]4C[C@@H]4C#N)ncc3c(N)n1)oc(=O)n2C]

A mixture of (±)-trans-N-(8-amino-6-chloro-2,7-naphthyridin-3-yl)-2-cyano-cyclopropanecarboxamide (100 mg, 0.35 mmol), 3,5-dimethyl-6-(4,4,5,5-tetramethyl-1,3,2-dioxaborolan-2-yl)-1,3-benzoxazol-2-one (207.0 mg, 0.72 mmol), XPhos Pd G$_2$ (60 mg, 0.08 mmol), AcOK (80 mg, 0.82 mmol) and XPhos (70 mg, 0.15 mmol) in 1,4-dioxane (15 mL) and water (3 mL) was stirred under Ar at 100° C. for 2 h. The mixture was directly purified by silica gel column chromatography (EA:PE=1:1 to EA to DCM:MeOH=20:1) followed by reverse phase chromatography (acetonitrile 0-50/0.1% NH$_4$HCO$_3$ in water) to afford (±)-trans-N-[8-amino-6-(3,5-dimethyl-2-oxo-1,3-benzoxazol-6-yl)-2,7-naphthyridin-3-yl]-2-cyano-cyclopropanecarboxamide (7.7 mg, 5.3% yield) as a white solid. LCMS (ESI): R$_T$ (min)=1.76, [M+H]⁺=415.1, method=C; ¹HNMR (400 MHz, DMSO-d$_6$): δ 11.24 (s, 1H), 9.37 (s, 1H), 8.18 (s, 1H), 7.36 (s, 1H), 7.29 (s, 2H), 7.17 (s, 1H), 6.89 (s, 1H), 3.36 (s, 3H), 2.79-2.73 (m, 1H), 2.42 (s, 3H), 2.18-2.13 (m, 1H), 1.63-1.59 (m, 1H), 1.46-1.41 (m, 1H).

Example 106 exo-3-acetyl-N-[8-amino-6-(4-methyl-3-pyridyl)-2,7-naphthyridin-3-yl]-3-azabicyclo[3.1.0]hexane-6-carboxamide (Compound 143)

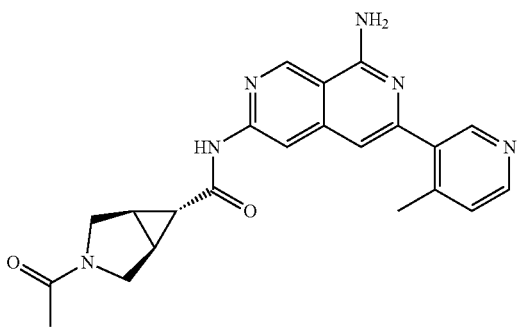 [SMILES: CC(=O)N1C[C@@H]2[C@H](C1)[C@H]2C(=O)Nc1cc2cc(-c3cnccc3C)nc(N)c2cn1]

A mixture of exo-N-[8-amino-6-(4-methyl-3-pyridyl)-2,7-naphthyridin-3-yl]-3-azabicyclo[3.1.0]hexane-6-carboxamide (80 mg, 0.22 mmol), TEA (67 mg, 0.66 mmol) and CH$_3$COCl (22 mg, 0.28 mmol) in dichloromethane (6 mL) was stirred at 25° C. for 2 h. The reaction mixture was concentrated and purified by prep-HPLC (Column Xbridge 21.2×250 mm C18, 10 um, Mobile Phase A: water (10 mmol/L NH$_4$HCO$_3$) B: ACN) to give exo-3-acetyl-N-[8-amino-6-(4-methyl-3-pyridyl)-2,7-naphthyridin-3-yl]-3-azabicyclo[3.1.0]hexane-6-carboxamide (4 mg, 4.5% yield) as a white solid. LCMS (ESI): RT (min)=1.436, [M+H]⁺=403.1, method=H; ¹H NMR (400 MHz, DMSO-d$_6$) δ 10.82 (s, 1H), 9.36 (s, 1H), 8.56 (s, 1H), 8.43 (d, J=5.2 Hz, 1H), 8.22 (s, 1H), 7.32-7.31 (m, 3H), 6.95 (s, 1H), 3.70-3.66 (m, 2H), 3.38-3.33 (m, 2H), 2.41 (s, 3H), 2.14-2.12 (m, 1H), 2.07-2.05 (m, 1H), 1.95-1.93 (m, 4H).

Example 107

(±)-trans-N-[8-amino-6-(5-methyl-2-oxo-3H-1,3-benzoxazol-6-yl)-2,7-naphthyridin-3-yl]-2-(1H-pyrazol-4-yl)cyclopropanecarboxamide (Compound 144)

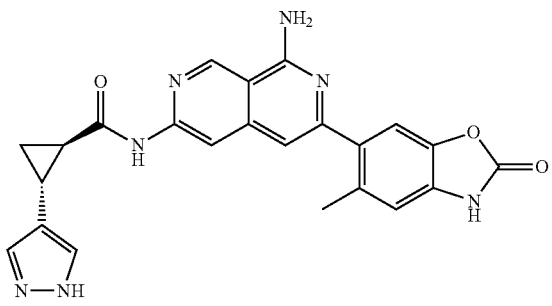 [SMILES: Cc1cc2[nH]c(=O)oc2cc1-c1cc2cc(NC(=O)[C@@H]3C[C@H]3c3cn[nH]c3)ncc2c(N)n1]

Step 1: (±)-trans-N-[8-amino-6-[3-[(4-methoxyphenyl)methyl]-5-methyl-2-oxo-1,3-benzoxazol-6-yl]-2,7-naphthyridin-3-yl]-2-(1-tetrahydropyran-2-ylpyrazol-4-yl)cyclopropanecarboxamide

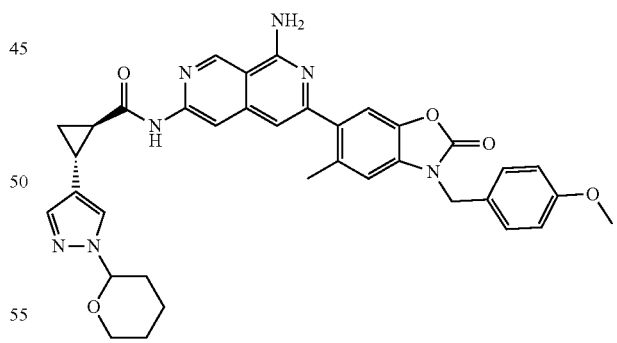

A mixture of (±)-trans-N-(8-amino-6-chloro-2,7-naphthyridin-3-yl)-2-(1-tetrahydropyran-2-ylpyrazol-4-yl)cyclopropanecarboxamide (280 mg, 0.7 mmol), X-phos-Pd-G2 (98 mg, 0.12 mmol), K$_2$CO$_3$ (280 mg, 2 mmol) and 3-[(4-methoxyphenyl)methyl]-5-methyl-6-(4,4,5,5-tetramethyl-1,3,2-dioxaborolan-2-yl)-1,3-benzoxazol-2-one (280 mg, 0.7 mmol) in 1,4-dioxane (2 mL) and water (0.5 mL) was heated at 100° C. for 3 h under Ar. The reaction was concentrated and purified by flash column chromatography to give (±)-trans-N-[8-amino-6-[3-[(4-methoxyphenyl)methyl]-5- methyl-2-oxo-1,3-benzoxazol-6-yl]-2,7-naphthyridin-3-yl]-2-(1-tetrahydropyran-2-ylpyrazol-4-yl)cyclopropanecarboxamide (180 mg, 33% yield) as a yellow solid. LCMS (ESI): [M+H]$^+$=645.1.

Step 2: (±)-trans-N-[8-amino-6-(5-methyl-2-oxo-3H-1,3-benzoxazol-6-yl)-2,7-naphthyridin-3-yl]-2-(1H-pyrazol-4-yl)cyclopropanecarboxamide

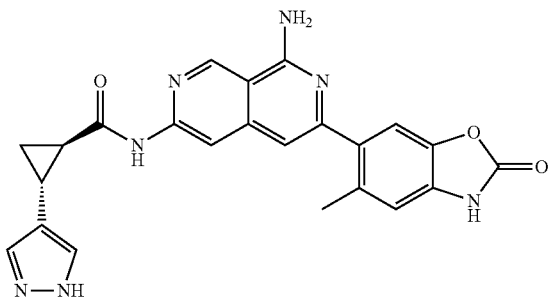 [SMILES: Cc1cc2[nH]c(=O)oc2cc1-c1cc2cc(NC(=O)[C@@H]3C[C@H]3c3cn[nH]c3)ncc2c(N)n1]

A mixture of (±)-trans-N-[8-amino-6-[3-[(4-methoxyphenyl)methyl]-5-methyl-2-oxo-1,3-benzoxazol-6-yl]-2,7-naphthyridin-3-yl]-2-(1-tetrahydropyran-2-ylpyrazol-4-yl)cyclopropanecarboxamide (140 mg, 0.2 mmol), TFA (3 mL, 0.2 mmol) and TfOH (3 mL, 0.2 mmol) was stirred at 25° C. for 2 h. The mixture was neutralized by NH$_3$ in MeOH, concentrated and purified by prep-HPLC to give (±)-trans-N-[8-amino-6-(5-methyl-2-oxo-3H-1,3-benzoxazol-6-yl)-2,7-naphthyridin-3-yl]-2-(1H-pyrazol-4-yl)cyclopropanecarboxamide (7 mg, 7.3% yield) as a yellow solid. LCMS (ESI): RT (min)=1.504, [M+H]$^+$=442.1, method=E; $^1$H NMR (400 MHz, DMSO-d$_6$) δ 9.27 (s, 1H), 8.30 (s, 1H), 7.27 (s, 1H), 7.03 (s, 1H), 6.91 (s, 1H), 2.46-2.41 (m, 1H), 2.38 (s, 3H), 2.15-2.13 (m, 1H), 1.63-1.56 (m, 1H), 1.31-1.28 (m, 1H).

Example 108

(±)-trans-N-[8-amino-6-(4-methyl-3-pyridyl)-2,7-naphthyridin-3-yl]-2-[3-[(4-methoxyphenyl)methyl]imidazol-4-yl]cyclopropanecarboxamide (Compound 145)

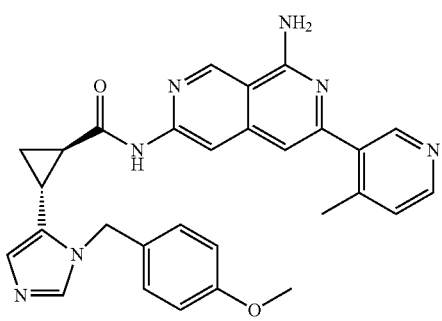 [SMILES: COc1ccc(Cn2cncc2[C@@H]2C[C@H]2C(=O)Nc2cc3cc(-c4cnccc4C)nc(N)c3cn2)cc1]

Step 1: methyl (E)-3-(1H-imidazol-5-yl)prop-2-enoate

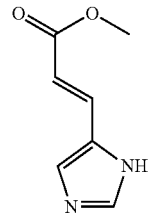

To a solution of (E)-3-(1H-imidazol-5-yl)prop-2-enoic acid (5 g, 36 mmol) in methanol (50 mL) was added thionyl chloride (5.5 mL, 75 mmol) at 0° C. The mixture was allowed to heat to 70° C. and refluxed overnight. The mixture was then concentrated and the resulting residue dissolved in ethyl acetate and washed with water. The organic layer was concentrated to afford methyl (E)-3-(1H-imidazol-5-yl)prop-2-enoate (6 g, 98% yield) as a white solid. LCMS (ESI): [M+H]$^+$=153.1.

Step 2: methyl (E)-3-[3-[(4-methoxyphenyl)methyl]imidazol-4-yl]prop-2-enoate

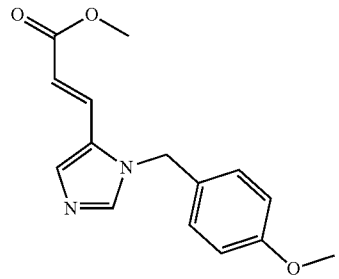 [SMILES: COC(=O)/C=C/c1cncn1Cc1ccc(OC)cc1]

To the mixture of methyl (E)-3-(1H-imidazol-5-yl)prop-2-enoate (6 g, 39 mmol) in N,N-dimethylformamide (50 mL) was added NaH (1.6 g, 40 mmol) at 0° C. The reaction was stirred for 0.5 h before the addition of 4-methoxybenzyl chloride (6.2 g, 39 mmol). The reaction was stirred overnight at 25° C. The mixture was diluted with ethyl acetate (200 mL), washed with brine (10 mL×3), and the organics were dried and concentrated. The resulting residue was purified by flash column chromatography (10% EtOAc in PE) to give methyl (E)-3-[3-[(4-methoxyphenyl)methyl]imidazol-4-yl]prop-2-enoate (10 g, 74% yield) as a white solid. LCMS (ESI): [M+H]$^+$=273.1.

Step 3: (±)-methyl 2-[3-[(4-methoxyphenyl)methyl]imidazol-4-yl]cyclopropanecarboxylate

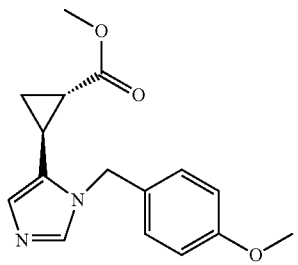 [SMILES: COC(=O)[C@H]1C[C@@H]1c1cncn1Cc1ccc(OC)cc1]

To a mixture of trimethyloxosulfonium iodide (10.5 g, 47 mmol) in dimethyl sulfoxide (100 mL) was added NaH (2 g, 50 mmol). The mixture was stirred under $N_2$ at rt for 0.5 h before the addition of methyl (E)-3-[3-[(4-methoxyphenyl)methyl] imidazol-4-yl]prop-2-enoate (10 g, 36 mmol) in dimethyl sulfoxide (150 mL). The mixture was stirred under N2 at rt for 1 h. A saturated aqueous ammonium chloride solution and water were added to the reaction mixture and the mixture was extracted with ethyl acetate. The organic layer was washed with water and saturated brine, dried over anhydrous magnesium sulfate, filtrated, and concentrated. The residue was purified by silica gel column chromatography (hexane-ethyl acetate 100:0-60:40, v/v) to give methyl 2-[3-[(4-methoxyphenyl)methyl] imidazol-4-yl]cyclopropanecarboxylate (1.8 g, 10% yield) as a colorless oil. LCMS (ESI): $[M+H]^+$=287.1.

Step 4: (±)-trans-2-[3-[(4-methoxyphenyl)methyl]imidazol-4-yl]cyclopropanecarboxylic acid

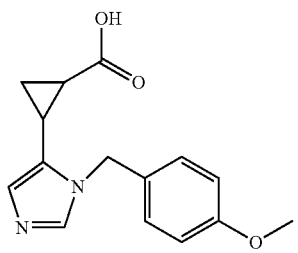 [SMILES: COc1ccc(Cn2cncc2C2CC2C(=O)O)cc1]

To a solution of methyl 2-[3-[(4-methoxyphenyl)methyl]imidazol-4-yl]cyclopropanecarboxylate (2 g, 7 mmol) in tetrahydrofuran (60 mL) and water (20 mL) was added lithium hydroxide monohydrate (2 g, 47 mmol) at rt. The reaction was stirred for 3 h. The resulting reaction was concentrated to dryness. The residue was diluted with water (10 mL) and then extracted with EtOAc (3×80 mL). The aqueous phase was acidified to pH=4 with concentrated aqueous HCl and dried under reduced pressure to give the title compound 2-[3-[(4-methoxyphenyl)methyl]imidazol-4-yl]cyclopropanecarboxylic acid (1.6 g, 73% yield) as a white solid. LCMS (ESI): $[M+H]^+$=272.2,

Step 5: (±)-trans-N-(6,8-dichloro-2,7-naphthyridin-3-yl)-2-[3-[(4-methoxyphenyl)methyl]imidazol-4-yl]cyclopropanecarboxamide

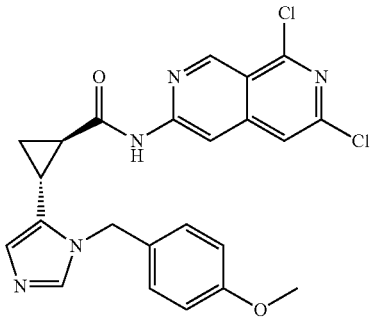 [SMILES: COc1ccc(Cn2cncc2[C@@H]2C[C@H]2C(=O)Nc2cc3cc(Cl)nc(Cl)c3cn2)cc1]

To a mixture of 6,8-dichloro-2,7-naphthyridin-3-amine (200 mg, 0.9 mmol) and phosphorus oxychloride (120 mg, 0.8 mmol) in pyridine (8 mL) was added (±)-trans-2-[3-[(4-methoxyphenyl)methyl]imidazol-4-yl]cyclopropanecarboxylic acid (200 mg, 0.7 mmol) at 0° C. The resulting mixture was stirred for 1 h at 0° C. The reaction was then diluted with saturated aq.NaHCO$_3$ and extracted with ethyl acetate (20 mL×2). The combined ethyl acetate layers were concentrated and purified by flash column chromatography (PE: EA=3:1-1:3) to give (±)-trans-N-(6,8-dichloro-2,7-naphthyridin-3-yl)-2-[3-[(4-methoxyphenyl)methyl]imidazol-4-yl] cyclopropanecarboxamide (400 mg, 81% yield) as a light yellow solid. LCMS (ESI): $[M+H]^+$=467.1.

Step 6: (±)-trans-N-(8-amino-6-chloro-2,7-naphthyridin-3-yl)-2-[3-[(4-methoxyphenyl)methyl]imidazol-4-yl]cyclopropanecarboxamide

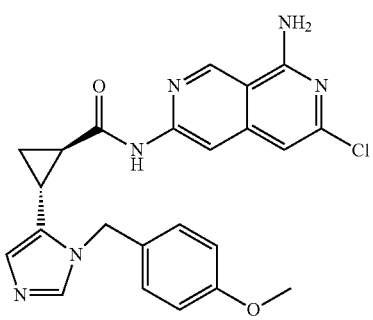 [SMILES: COc1ccc(Cn2cncc2[C@@H]2C[C@H]2C(=O)Nc2cc3cc(Cl)nc(N)c3cn2)cc1]

A mixture of (±)-trans-N-(6,8-dichloro-2,7-naphthyridin-3-yl)-2-(1-tetrahydropyran-2-ylpyrazol-4-yl)cyclopropanecarboxamide (300 mg, 0.69 mmol), NH$_4$OH (8 mL, 0.69 mmol) in 1,4-dioxane (8 mL) was heated at 90° C. for 4 h under Ar. The reaction was concentrated to dryness. The crude was used directly without further purification. LCMS (ESI): $[M+H]^+$=449.1

Step 7: (±)-trans-N-[8-amino-6-(4-methyl-3-pyridyl)-2,7-naphthyridin-3-yl]-2-[3-[(4-methoxyphenyl)methyl]imidazol-4-yl]cyclopropanecarboxamide

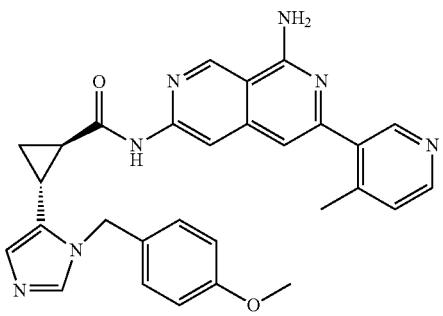 [SMILES: COc1ccc(Cn2cncc2[C@@H]2C[C@H]2C(=O)Nc2cc3cc(-c4cnccc4C)nc(N)c3cn2)cc1]

A mixture of 4-methyl-3-(4,4,5,5-tetramethyl-1,3,2-dioxaborolan-2-yl)pyridine (175 mg, 0.8 mmol), (±)-trans-N-(8-amino-6-chloro-2,7-naphthyridin-3-yl)-2-[3-[(4-methoxyphenyl)methyl]imidazol-4-yl]cyclopropanecarboxamide (250 mg, 0.5 mmol), XPhos Pd G2 (50 mg, 0.06 mmol), XPhos (60 mg, 0.1 mmol) and K$_2$CO$_3$ (250 mg, 1.8 mmol) in 1,4-dioxane (10 mL) and water (2 mL) was heated at 100° C. for 3 h under Ar. The reaction mixture was concentrated and purified on silica gel column (ethyl acetate/petroleum ether, 1:1) to afford (±)-trans-N-[8-amino-6-(4-methyl-3-pyridyl)-2,7-naphthyridin-3-yl]-2-[3-[(4-methoxyphenyl)methyl]imidazol-4-yl]cyclopropane carboxamide (69 mg, 24.5% yield) as a light yellow solid. LCMS (ESI): RT (min)=1.40, [M+H]$^+$=506.1, method=B; $^1$H NMR (400 MHz, DMSO-d$_6$) δ 9.28 (s, 1H), 8.54 (s, 1H), 8.43 (d, J=5.2 Hz, 1H), 8.32 (s, 1H), 7.63 (s, 1H), 7.40 (d, J=5.2 Hz, 1H), 7.23 (d, J=8.5 Hz, 2H), 7.01-6.89 (m, 4H), 5.09 (s, 2H), 3.80 (s, 3H), 2.54-2.39 (m, 4H), 2.26-2.15 (m, 1H), 1.57-1.52 (m, 1H), 1.42-1.38 (m, 1H).

Example 109

(±)-trans-N-[8-amino-6-(4-methyl-3-pyridyl)-2,7-naphthyridin-3-yl]-2-(1-ethylsulfonylpyrazol-4-yl)cyclopropanecarboxamide (Compound 146)

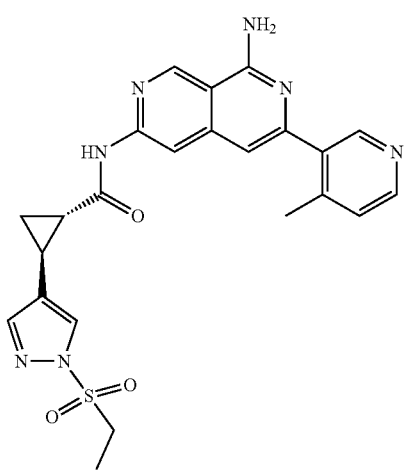 [SMILES: CCS(=O)(=O)n1cc([C@H]2C[C@@H]2C(=O)Nc2cc3cc(-c4cnccc4C)nc(N)c3cn2)cn1]

Step 1: (±)-trans-N-(6,8-dichloro-2,7-naphthyridin-3-yl)-2-(1H-pyrazol-4-yl)cyclopropanecarboxamide

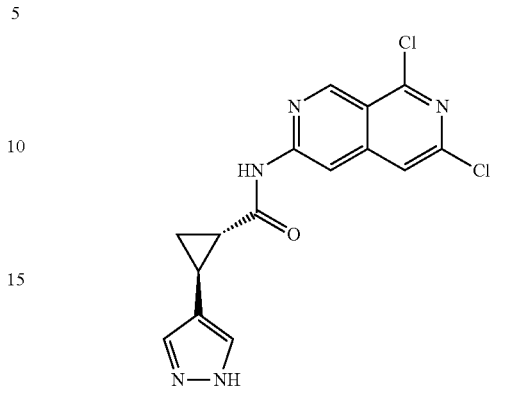

To a mixture of (±)-trans-N-(6,8-dichloro-2,7-naphthyridin-3-yl)-2-(1-tetrahydropyran-2-ylpyrazol-4-yl)cyclopropanecarboxamide (290 mg, 0.6 mmol) in dichloromethane (5 mL) was added TFA (5 mL, 67.3 mmol). The mixture was stirred at rt for 1 h. The crude was used directly without further purification. LCMS (ESI): [M+H]$^+$=348.1.

Step 2: (±)-trans-N-(6,8-dichloro-2,7-naphthyridin-3-yl)-2-(1-ethylsulfonylpyrazol-4-yl)cyclopropanecarboxamide

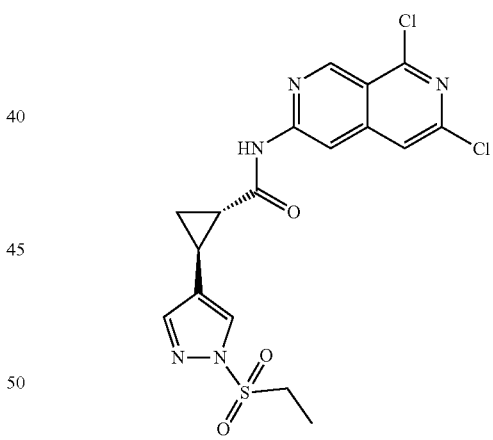

To a solution of ethanesulfonyl chloride (2 mL) and (±)-trans-N-(6,8-dichloro-2,7-naphthyridin-3-yl)-2-(1H-pyrazol-4-yl)cyclopropanecarboxamide (190 mg, 0.5 mmol) in dichloromethane (10 mL) was added NEt$_3$ (2 mL, 0.5 mmol). The mixture was stirred at 20° C. for 2 h. The reaction mixture was concentrated and purified on silica gel column chromatography eluted with ethyl acetate/petroleum ether (1:1) to afford (±)-trans-N-(6,8-dichloro-2,7-naphthyridin-3-yl)-2-(1-ethylsulfonylpyrazol-4-yl)cyclopropanecarboxamide (150 mg, 56% yield) as a light yellow solid. LCMS (ESI): [M+H]+=440.1.

601

Step 3: (±)-trans-N-(8-amino-6-chloro-2,7-naphthyridin-3-yl)-2-(1H-pyrazol-4-yl)cyclopropanecarboxamide

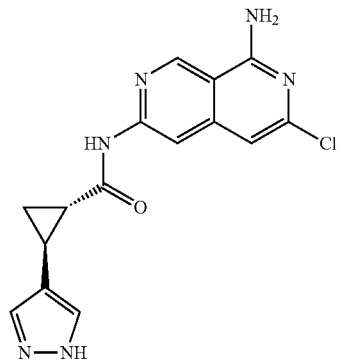 [SMILES: Nc1nc(Cl)cc2cc(NC(=O)[C@H]3C[C@@H]3c3cn[nH]c3)ncc12]

A mixture of NH₄OH (8 mL, 0.6 mmol), (±)-trans-N-(6,8-dichloro-2,7-naphthyridin-3-yl)-2-(1-ethylsulfonylpyrazol-4-yl)cyclopropanecarboxamide (290 mg, 0.6 mmol) in 1,4-dioxane (8 mL) was heated at 90° C. for 4 h under Ar. The reaction was concentrated and used directly without further purification. LCMS (ESI): [M+H]+=329.1.

Step 4: (±)-trans-N-(8-amino-6-chloro-2,7-naphthyridin-3-yl)-2-(1-ethylsulfonylpyrazol-4-yl)cyclopropanecarboxamide

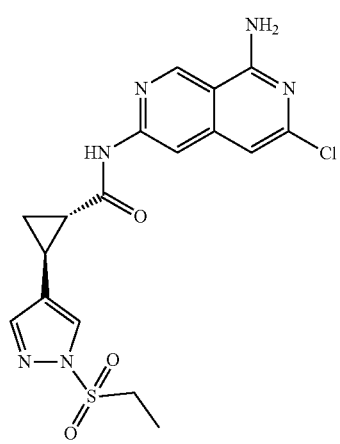 [SMILES: CCS(=O)(=O)n1cc([C@H]2C[C@@H]2C(=O)Nc2cc3cc(Cl)nc(N)c3cn2)cn1]

To a solution of ethanesulfonyl chloride (2 mL) and (±)-trans-N-(8-amino-6-chloro-2,7-naphthyridin-3-yl)-2-(1H-pyrazol-4-yl)cyclopropanecarboxamide (140 mg, 0.4 mmol) in dichloromethane (2 mL) was added NEt₃ (2 mL, 0.5 mmol). The mixture was stirred at 20° C. for 2 h. The reaction mixture concentrated and purified by flash chromatography to give (±)-trans-N-(8-amino-6-chloro-2,7-naphthyridin-3-yl)-2-(1-ethylsulfonylpyrazol-4-yl)cyclopropanecarboxamide (100 mg, 50% yield) as a white solid. LCMS (ESI): [M+H]+=420.1.

602

Step 5: (±)-trans-N-[8-amino-6-(4-methyl-3-pyridyl)-2,7-naphthyridin-3-yl]-2-(1-ethylsulfonylpyrazol-4-yl)cyclopropanecarboxamide

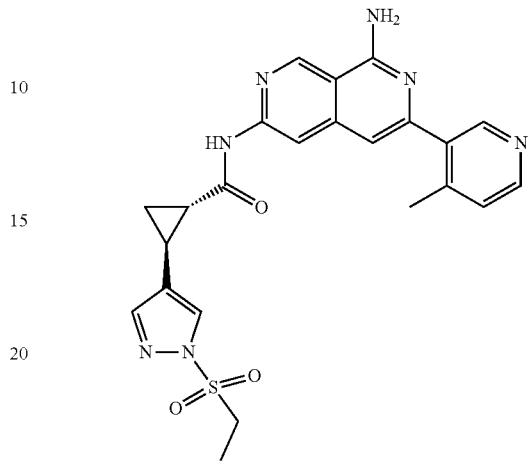

A mixture of 4-methyl-3-(4,4,5,5-tetramethyl-1,3,2-dioxaborolan-2-yl)pyridine (80 mg, 0.3 mmol), XPhos Pd G2 (20 mg, 0.03 mmol), XPhos (30 mg, 0.06 mmol), K₂CO₃ (110 mg, 0.8 mmol) and (±)-trans-N-(8-amino-6-chloro-2,7-naphthyridin-3-yl)-2-(1-ethylsulfonylpyrazol-4-yl)cyclopropanecarboxamide (100 mg, 0.2 mmol) in 1,4-dioxane (10 mL) and water (2 mL) was heated at 100° C. for 3 h under Ar. The reaction mixture was concentrated and purified by prep-HPLC to afford (±)-trans-N-[8-amino-6-(4-methyl-3-pyridyl)-2,7-naphthyridin-3-yl]-2-(1-ethylsulfonylpyrazol-4-yl)cyclopropanecarboxamide (40 mg, 35% yield) as a white solid. LCMS (ESI): RT (min)=1.560, [M+H]+=478.1, method=B; ¹H NMR (400 MHz, CD₃OD) δ 9.30 (s, 1H), 8.55 (s, 1H), 8.44 (d, J=5.2 Hz, 1H), 8.34 (s, 1H), 8.12 (s, 1H), 7.85 (s, 1H), 7.41 (d, J=5.2 Hz, 1H), 7.00 (s, 1H), 3.56 (q, J=7.6 Hz, 2H), 2.48-2.47 (m, 4H), 2.28-2.13 (m, 1H), 1.67-1.62 (m, 1H), 1.39-1.34 (m, 1H), 1.21 (t, J=7.6 Hz, 3H).

Example 110

(±)-trans-N-(8-amino-6-(5-(difluoromethyl)-4-methylpyridin-3-yl)-2,7-naphthyridin-3-yl)-2-cyanocyclopropanecarboxamide (Compound 147)

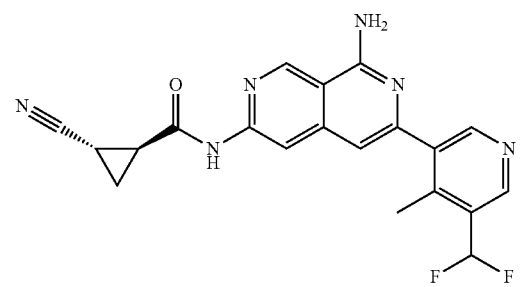 [SMILES: Cc1c(-c2cc3cc(NC(=O)[C@H]4C[C@@H]4C#N)ncc3c(N)n2)cncc1C(F)F]

Step 1: 3-bromo-5-(difluoromethyl)-4-methylpyridine

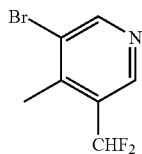

To a solution of 5-bromo-4-methyl-pyridine-3-carbaldehyde (300 mg, 1.50 mmol) in dichloromethane (20 mL) was added diethylaminosulfur trifluoride (290 mg, 1.80 mmol) under argon, the reaction mixture was stirred for 16 h under argon. The mixture was quenched with sat NaHCO₃ (5 mL) and the phases were separated. The organic layer was collected, washed with brine (5 mL×3), dried over $Na_2SO_4$, filtered and concentrated in vacuo. The residue was purified by prep-TLC (EtOAc/PE=1:5) to give 3-bromo-5-(difluoromethyl)-4-methyl-pyridine (220 mg, 63% yield) as a yellow oil. LCMS (ESI) [M+H]⁺=221.7.

Step 2: 3-(difluoromethyl)-4-methyl-5-(4,4,5,5-tetramethyl-1,3,2-dioxaborolan-2-yl)pyridine

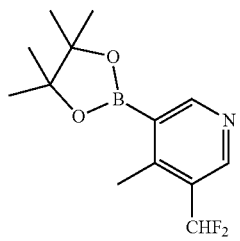 [SMILES: Cc1c(B2OC(C)(C)C(C)(C)O2)cncc1C(F)F]

To a reaction tube was added 3-bromo-5-(difluoromethyl)-4-methyl-pyridine (80 mg, 0.36 mmol), KOAc (70 mg, 0.72 mmol), Pd(dppf)Cl₂ (13 mg, 0.02 mmol), bis(pinacolato)diboron (183 mg, 0.72 mmol) and 1,4-dioxane (10 mL). The mixture was stirred at 100° C. for 16 h under N₂. The reaction mixture was filtered and concentrated in vacuo. The crude material was be used directly in the next step without further purification. LCMS (ESI) [M+H]⁺=187.7.

Step 3: (±)-trans-N-(8-amino-6-(5-(difluoromethyl)-4-methylpyridin-3-yl)-2,7-naphthyridin-3-yl)-2-cyanocyclopropanecarboxamide

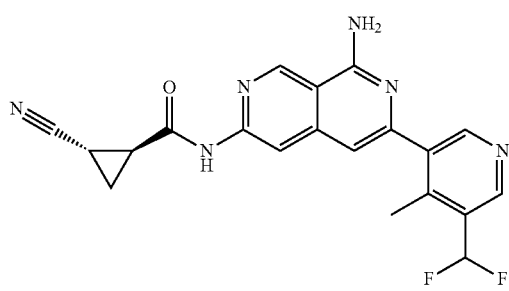 [SMILES: Cc1c(-c2cc3cc(NC(=O)[C@H]4C[C@@H]4C#N)ncc3c(N)n2)cncc1C(F)F]

To a mixture of 3-(difluoromethyl)-4-methyl-5-(4,4,5,5-tetramethyl-1,3,2-dioxaborolan-2-yl)pyridine (84 mg, 0.31 mmol) in 1,4-dioxane (10 mL) and water (2 mL) were added (+)-trans-N-(8-amino-6-chloro-2,7-naphthyridin-3-yl)-2-cyano-cyclopropanecarboxamide (60 mg, 0.21 mmol), XphosPdG2 (16 mg, 0.02 mmol), Xphos (20 mg, 0.04 mmol) and KOAc (61 mg, 0.63 mmol). The mixture was heated to 100° C. for 2 h. This reaction mixture was concentrated in vacuo and purified by prep-TLC (DCM/MeOH=20/1) followed by prep-HPLC to give (±)-trans-N-[8-amino-6-[5-(difluoromethyl)-4-methyl-3-pyridyl]-2,7-naphthyridin-3-yl]-2-cyano-cyclopropanecarboxamide (14 mg, 16.8% yield) as a white solid. LCMS (ESI) [M+H]⁺=394.7, $R_T$(min)=1.591, Method=G; ¹H NMR (400 MHz, DMSO-d₆) δ 11.29 (s, 1H), 9.42 (s, 1H), 8.69 (s, 1H), 8.68 (s, 1H), 8.22 (s, 1H), 7.21-7.48 (m, 3H), 7.00 (s, 1H), 2.74-2.79 (m, 1H), 2.40 (s, 3H), 2.13-2.18 (m, 1H), 1.59-1.64 (m, 1H), 1.41-1.46 (m, 1H).

Example 111

(±)-trans-N-(8-amino-6-(4-methylpyridin-3-yl)-2,7-naphthyridin-3-yl)-5-(methylsulfonyl)-5-azaspiro[2.4]heptane-1-carboxamide (Compound 148)

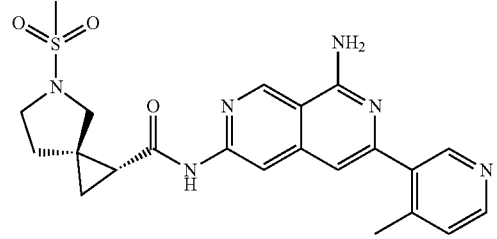 [SMILES: Cc1ccncc1-c1cc2cc(NC(=O)[C@@H]3C[C@]34CCN(S(C)(=O)=O)C4)ncc2c(N)n1]

To a suspension of N,N-diethylamine (0.50 mL, 4.65 mmol) in dichloromethane (15 mL) was added methanesulfonyl chloride (0.17 mL, 2.20 mmol) and (±)-trans-N-[8-amino-6-(4-methyl-3-pyridyl)-2,7-naphthyridin-3-yl]-5-azaspiro[2.4]heptane-2-carboxamide hydrochloride (50 mg, 0.12 mmol) at 0° C. The mixture was stirred for 30 min at 0° C. Methanesulfonyl chloride (84 mg) was added to the mixture at 0° C. The reaction mixture was stirred for another 30 min and then diluted with water (3 mL). The mixture was concentrated and purified by Prep-HPLC to give (±)-trans-N-[8-amino-6-(4-methyl-3-pyridyl)-2,7-naphthyridin-3-yl]-5-methylsulfonyl-5-azaspiro[2.4]heptane-2-carboxamide (29 mg, 51% yield) as a white solid. LCMS (ESI) [M+H]⁺=452.7, $R_T$(min)=1.494, Method=G. ¹H NMR (400 MHz, DMSO-d₆) δ 11.00 (s, 1H), 9.37 (s, 1H), 8.56 (s, 1H), 8.43 (d, J=4.8 Hz, 1H), 8.27 (s, 1H), 7.30-7.32 (m, 3H), 6.99 (s, 1H), 3.33-3.39 (m, 4H), 2.84 (s, 3H), 2.41 (s, 3H), 2.26-2.30 (m, 1H), 1.88-2.01 (m, 2H), 1.22-1.29 (m, 2H).

Example 112

(±)-cis-N-(8-amino-6-(4-methylpyridin-3-yl)-2,7-naphthyridin-3-yl)-5-(methylsulfonyl)-5-azaspiro[2.4]heptane-1-carboxamide (Compound 149)

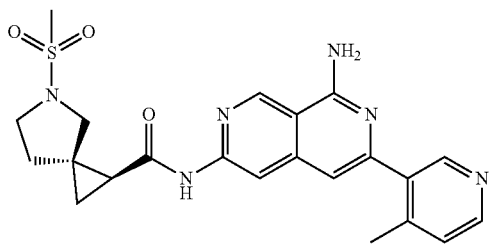 [SMILES: Cc1ccncc1-c1cc2cc(NC(=O)[C@H]3C[C@]34CCN(S(C)(=O)=O)C4)ncc2c(N)n1]

To a suspension of (±)-cis-N-[8-amino-6-(4-methyl-3-pyridyl)-2,7-naphthyridin-3-yl]-5-azaspiro[2.4]heptane-2-carboxamide hydrochloride (25 mg, 0.06 mmol) in dichloromethane (10 mL) was added N,N-diethylamine (0.29 mL, 2.79 mmol) and methanesulfonyl chloride (140 mg) at 0° C. The mixture was stirred for 30 min at 0° C. Methanesulfonyl chloride (84 mg) was added to the mixture at 0° C. and the reaction mixture was stirred for another 30 min at 0° C. The reaction mixture was diluted with water (3 mL) and concentrated. The crude material was purified by Prep-HPLC to give (±)-cis-N-[8-amino-6-(4-methyl-3-pyridyl)-2,7-naphthyridin-3-yl]-5-methylsulfonyl-5-azaspiro[2.4]heptane-2-carboxamide (9 mg, 33% yield) as a white solid. LCMS (ESI) [M+H]$^+$=452.7, R$_T$(min)=1.504, Method=G. $^1$HNMR (400 MHz, CD$_3$OD) δ 9.30 (s, 1H), 8.54 (s, 1H), 8.43 (d, J=5.2 Hz, 1H), 8.34 (s, 1H), 7.40 (d, J=4.8 Hz, 1H), 6.99 (s, 1H), 3.35-3.54 (m, 4H), 2.94 (s, 3H), 2.46 (s, 3H), 2.12-2.23 (m, 3H), 1.45-1.48 (m, 1H), 1.28-1.32 (m, 1H).

Example 113

N-(8-amino-6-(4-methylpyridin-3-yl)-2,7-naphthyridin-3-yl)-5-(3-cyanopyridin-2-yl)-5-azaspiro[2.3]hexane-1-carboxamide (Compound 150)

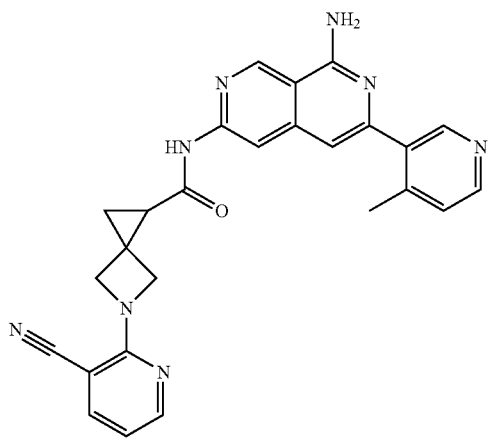 [SMILES: Cc1ccncc1-c1cc2cc(NC(=O)C3CC34CN(c3ncccc3C#N)C4)ncc2c(N)n1]

Step 1: 5-azaspiro[2.3]hexane-1-carboxylic acid hydrochloride

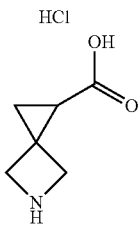

A solution of 5-tert-butoxycarbonyl-5-azaspiro[2.3]hexane-2-carboxylic acid (590 mg, 2.6 mmol) in HCl/dioxane (5 mL, 20 mmol) was stirred for 1 h at 25° C. The mixture was concentrated in vacuo and the residue was dissolved in MeOH. The product was precipitated by the addition of EtOA and collected by filtration to give 5-azaspiro[2.3]hexane-2-carboxylic acid hydrochloride as a white solid (420 mg, 99%): $^1$H NMR (400 MHz, DMSO-d$_6$) δ 12.60 (bs, 1H), 4.09-3.96 (m, 4H), 1.94-1.92 (m, 1H), 1.37-1.29 (m, 1H), 1.09-1.05 (m, 1H).

Step 2: 5-(3-cyanopyridin-2-yl)-5-azaspiro[2.3]hexane-1-carboxylic acid

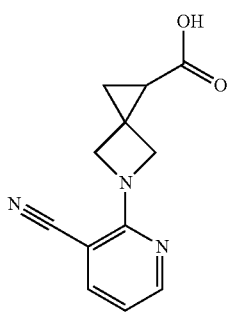 [SMILES: N#Cc1cccnc1N1CC2(CC2C(=O)O)C1]

To a mixture of 5-azaspiro[2.3]hexane-2-carboxylic acid (400 mg, 3.15 mmol), 3-cyano-2-fluoropyridine (640 mg, 5.24 mmol) in N,N-dimethylformamide (3 ml) was added K$_2$CO$_3$ (1.6 g, 11.59 mmol). The mixture was stirred for 15 h at 85° C. The pH was adjusted to around 6 by adding 1N HCl solution. The product was extracted with ethyl acetate (20 ml×3). The organic layer was dried, concentrated, and purified by prep-TLC (DCM/MeOH=20/1) to give 5-(3-cyano-2-pyridyl)-5-azaspiro[2.3]hexane-2-carboxylic acid as a yellow solid (400 mg, 55% yield): LCMS (ESI) [M+H]$^+$=230.1

Step 3: 5-(3-cyanopyridin-2-yl)-N-(6,8-dichloro-2,7-naphthyridin-3-yl)-5-azaspiro[2.3]hexane-1-carboxamide

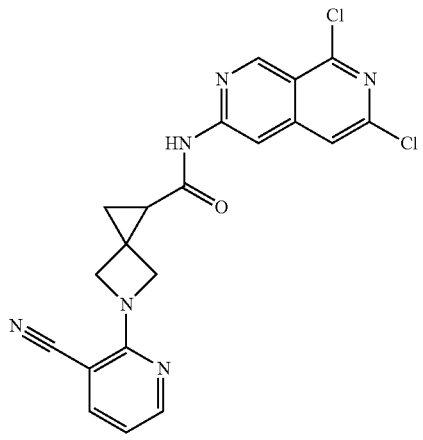 [SMILES: N#Cc1cccnc1N1CC2(CC2C(=O)Nc2cc3cc(Cl)nc(Cl)c3cn2)C1]

To a mixture of pyridine (0.76 mL, 9.34 mmol), 6,8-dichloro-2,7-naphthyridin-3-amine (200 mg, 0.93 mmol) and 5-(3-cyano-2-pyridyl)-5-azaspiro[2.3]hexane-2-carboxylic acid (350 mg, 1.53 mmol) in dichloromethane (5 mL) at 0° C. was added POCl₃ (186 mg, 1.21 mmol). The mixture was stirred for 1 h at rt, quenched with aq. NaHCO₃, and extracted with DCM (50 mL×3). The combined organics were dried, concentrated, and the resulting crude residue purified by prep-TLC (EA/PE=1/1) to give 5-(3-cyano-2-pyridyl)-N-(6,8-dichloro-2,7-naphthyridin-3-yl)-5-azaspiro[2.3]hexane-2-carboxamide as a yellow solid (200 mg, 50% yield). LCMS (ESI) [M+H]⁺=425.2. ¹H NMR (400 MHz, CDCl₃) δ 9.39 (s, 1H), 8.50-8.46 (m, 2H), 8.28 (d, J=4.8 Hz, 1H), 7.69-7.59 (m, 2H), 6.66-6.63 (m, 1H), 4.58-4.48 (m, 4H), 3.19-3.18 (m, 1H), 1.42-1.26 (m, 2H).

Step 4: N-(8-amino-6-chloro-2,7-naphthyridin-3-yl)-5-(3-cyanopyridin-2-yl)-5-azaspiro[2.3]hexane-1-carboxamide

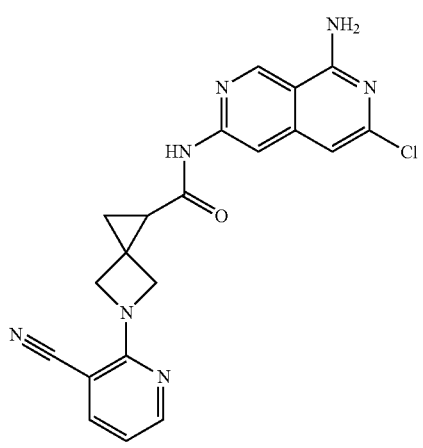 [SMILES: N#Cc1cccnc1N1CC2(CC2C(=O)Nc2cc3cc(Cl)nc(N)c3cn2)C1]

A solution of 5-(3-cyano-2-pyridyl)-N-(6,8-dichloro-2,7-naphthyridin-3-yl)-5-azaspiro[2.3]hexane-2-carboxamide (180 mg, 0.42 mmol) in NH₃.H₂O (5 mL, 18 mmol) and 1,4-dioxane (5 mL) was stirred at 90° C. for 3 h. The solution was concentrated. The crude mixture was washed with a mixture of ethyl acetate (3 mL) and PE (10 mL) to give crude N-(8-amino-6-chloro-2,7-naphthyridin-3-yl)-5-(3-cyano-2-pyridyl)-5-azaspiro[2.3]hexane-2-carboxamide (200 mg, 37% yield) as a yellow solid. LCMS (ESI) [M+H]⁺=406.2

Step 5: N-(8-amino-6-(4-methylpyridin-3-yl)-2,7-naphthyridin-3-yl)-5-(3-cyanopyridin-2-yl)-5-azaspiro[2.3]hexane-1-carboxamide

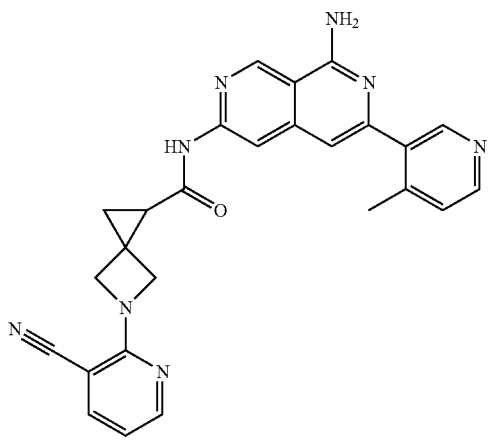 [SMILES: Cc1ccncc1-c1cc2cc(NC(=O)C3CC34CN(c3ncccc3C#N)C4)ncc2c(N)n1]

To a sealed tube was added Na₂CO₃ (50 mg, 0.47 mmol), Pd(dppf)Cl₂ (23 mg, 0.03 mmol), 4-methyl-3-(4,4,5,5-tetramethyl-1,3,2-dioxaborolan-2-yl)pyridine (69 mg, 0.32 mmol) and N-(8-amino-6-chloro-2,7-naphthyridin-3-yl)-5-(3-cyano-2-pyridyl)-5-azaspiro[2.3]hexane-2-carboxamide (200 mg, 0.16 mmol) in 1,4-dioxane (20 mL) and water (4 mL). The mixture was bubbled with N₂ for 2 min, and stirred at 100° C. for 4 h. The reaction was concentrated to dryness and purified by Prep-HPLC (C18) to give N-[8-amino-6-(4-methyl-3-pyridyl)-2,7-naphthyridin-3-yl]-5-(3-cyano-2-pyridyl)-5-azaspiro[2.3]hexane-2-carboxamide as a yellow solid (15 mg, 21% yield). (ESI): $R_T$ (min)=1.641, [M+H]⁺=463.2, method=G; ¹H NMR (400 MHz, DMSO-d₆) δ 11.05 (s, 1H), 9.38 (s, 1H), 8.57 (s, 1H), 8.43 (d, J=4.8 Hz, 1H), 8.32 (dd, J=2.0, 4.8 Hz, 1H), 8.28 (s, 1H), 7.96 (dd, J=1.6, 7.6 Hz, 1H), 7.32-7.31 (m, 3H), 7.00 (s, 1H), 6.78 (dd, J=4.8, 7.6 Hz, 1H), 4.39-4.30 (m, 4H), 2.41-2.36 (m, 4H), 1.39-1.27 (m, 2H).

Example 114 exo-N-[8-amino-6-(4-methyl-3-pyridyl)-2,7-naphthyridin-3-yl]-3-methylsulfonyl-3-azabicyclo [3.1.0] hexane-6-carboxamide (Compound 151)

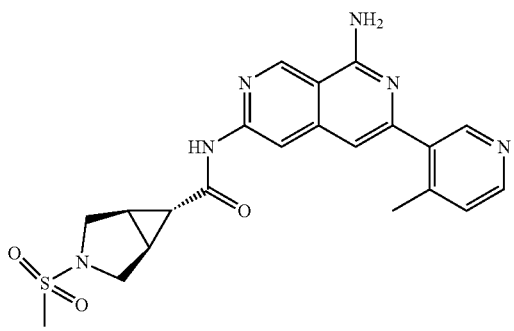 [SMILES: Cc1ccncc1-c1cc2cc(NC(=O)[C@H]3[C@@H]4CN(S(C)(=O)=O)C[C@@H]43)ncc2c(N)n1]

A mixture of exo-N-[8-amino-6-(4-methyl-3-pyridyl)-2,7-naphthyridin-3-yl]-3-azabicyclo[3.1.0]hexane-6-carboxamide (78 mg, 0.22 mmol), TEA (110 mg, 1.09 mmol) and MsCl (28 mg, 0.25 mmol) in dichloromethane (10 mL) was stirred at 25° C. for 2 h. The reaction mixture was concentrated and the residue purified by Prep-HPLC (C18) to give exo-N-[8-amino-6-(4-methyl-3-pyridyl)-2,7-naphthyridin-3-yl]-3-methylsulfonyl-3-azabicyclo[3.1.0]hexane-6-carboxamide (27 mg, 29% yield) as a white solid. LCMS (ESI): RT (min)=1.467, [M+H]$^+$=439.1, method=H; $^1$H NMR (400 MHz, DMSO-d$_6$) δ 10.95 (s, 1H), 9.37 (s, 1H), 8.56 (s, 1H), 8.43 (d, J=5.2 Hz, 1H), 8.22 (s, 1H), 7.32-7.30 (m, 3H), 6.96 (s, 1H), 3.45-3.43 (m, 4H), 2.95 (s, 3H), 2.41 (s, 3H), 2.19-2.17 (m, 1H), 2.11-2.09 (m, 2H).

Example 115

(±)-trans-N-(8-amino-6-(4-methylpyridin-3-yl)-2,7-naphthyridin-3-yl)-2-(isothiazol-4-yl)cyclopropanecarboxamide (Compound 152)

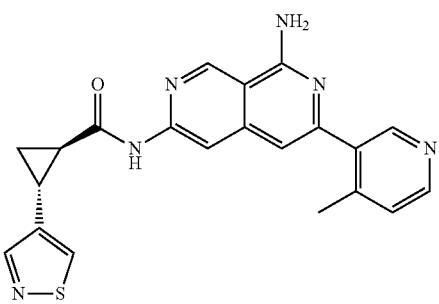 [SMILES: Cc1ccncc1-c1cc2cc(NC(=O)[C@@H]3C[C@H]3c3cnsc3)ncc2c(N)n1]

Step 1: tert-butyl (E)-3-isothiazol-4-ylprop-2-enoate

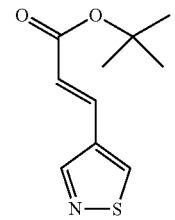

A mixture of 4-bromo-isothiazole (4.7 g, 28.66 mmol), tert-butyl acrylate (13 mL, 96.96 mmol), Pd(OAc)$_2$ (700 mg, 3.13 mmol), tris-(o-tolyl)phosphine (2.1 g, 6.91 mmol), and TEA (10 g, 99.01 mmol) in 1,4-dioxane (100 mL) was refluxed vigorously under Ar at 125° C. for 2 h. The reaction mixture was cooled to room temperature and concentrated. The residue was purified by silica gel chromatography (PE:EA=15:1 to 10:1) to give tert-butyl (E)-3-isothiazol-4-ylprop-2-enoate (2.7 g, 44.6% yield) as a light yellow solid. LCMS (ESI) [M+Na]$^+$=212.1. $^1$H NMR (400 MHz, CDCl$_3$): δ 8.72 (s, 1H), 8.69 (s, 1H), 7.63 (d, J=16.0 Hz, 1H), 6.36 (d, J=16.0 Hz, 1H), 1.55 (s, 9H).

Step 2: (±)-tert-butyl trans-2-isothiazol-4-ylcyclopropanecarboxylate

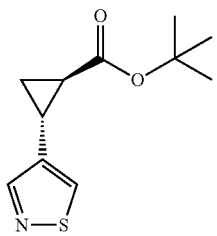

t-BuOK (3 g, 26.79 mmol) was added portionwise to a solution of trimethylsulfoxoniumiodide (6.1 g, 27.72 mmol) in dimethyl sulfoxide (30 mL) at 25° C. and the mixture was stirred at 25° C. for 0.5 h. A solution of tert-butyl (E)-3-isothiazol-4-ylprop-2-enoate (2.7 g, 12.78 mmol) in dimethyl sulfoxide (10 mL) was added dropwise to the reaction mixture at 25° C. The mixture was stirred at 25° C. for 1 h. The reaction mixture was diluted with sat. NH$_4$Cl (150 mL) and extracted with EA (50 mL×3). The ethyl acetate layers were combined, dried over Na$_2$SO$_4$, filtered and evaporated. The residue was purified with silica gel chromatography (PE:EA=10:1) to give tert-butyl trans-2-isothiazol-4-ylcyclopropanecarboxylate (1.94 g, 67.4% yield) as a light yellow oil. LCMS (ESI) [M+H]$^+$=226.1.

611

Step 3: (±)-trans-2-isothiazol-4-ylcyclopropanecarboxylic acid

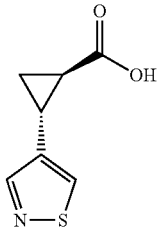 [SMILES: O=C(O)[C@@H]1C[C@H]1c1cnsc1]

A mixture of tert-butyl (±)-trans-2-isothiazol-4-ylcyclopropanecarboxylate (1.94 g, 8.61 mmol) in 2,2,2-trifluoroacetic acid (15 mL) was stirred at 20° C. for 1 h. The reaction mixture was evaporated and the resulting residue purified by silica gel chromatography (PE:EA=1:1 to 1:2) to give (±)-trans-2-isothiazol-4-ylcyclopropanecarboxylic acid (1.37 g, 94% yield) as a light brown oil. LCMS (ESI) [M+H]$^+$=170.0.

Step 4: (±)-trans-N-(6,8-dichloro-2,7-naphthyridin-3-yl)-2-isothiazol-4-yl-cyclopropanecarboxamide

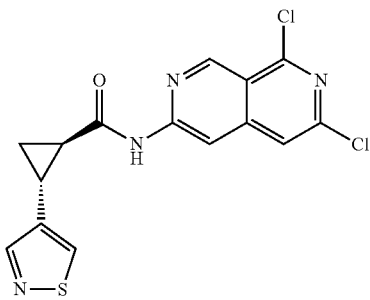

POCl$_3$ (150 mg, 0.98 mmol) was added dropwise to a mixture of 6,8-dichloro-2,7-naphthyridin-3-amine hydrochloride (200 mg, 0.80 mmol), (±)-trans-2-isothiazol-4-ylcyclopropanecarboxylic acid (250 mg, 1.48 mmol) and pyridine (1 mL, 12.36 mmol) in dichloromethane (10 mL) at 0° C. Then the reaction mixture was warmed to 20° C. and stirred for 1 h. To the reaction mixture was added DCM (20 mL) and the mixture washed with H$_2$O (10 mL). The DCM layer was separated, dried over Na$_2$SO$_4$, filtered and evaporated. The residue was purified by silica gel chromatography (PE:EA=3:1 PE:EA:THF=3:1:1) to give (±)-trans-N-(6,8-dichloro-2,7-naphthyridin-3-yl)-2-isothiazol-4-yl-cyclopropanecarboxamide (220 mg, 75% yield) as a light yellow solid. LCMS (ESI) [M+Na]$^+$=365.0.

612

Step 5: (±)-trans-N-(8-amino-6-chloro-2,7-naphthyridin-3-yl)-2-isothiazol-4-yl-cyclopropanecarboxamide

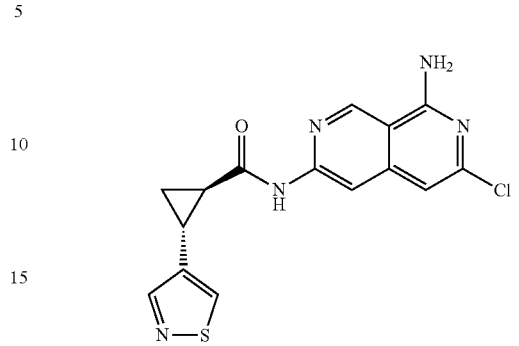

A mixture of (±)-trans-N-(6,8-dichloro-2,7-naphthyridin-3-yl)-2-isothiazol-4-yl-cyclopropanecarboxamide (220 mg, 0.60 mmol) in ammonium hydroxide (10 mL) in 1,4-dioxane (10 mL) was stirred at 90° C. in sealed tube for 3 h. The reaction mixture was cooled to room temperature and evaporated to give trans-N-(8-amino-6-chloro-2,7-naphthyridin-3-yl)-2-isothiazol-4-yl-cyclopropanecarboxamide (230 mg) as a brown solid. The crude product was used directly in next step. LCMS (ESI) [M+Na]$^+$=346.1/348.1.

Step 6: (±)-trans-N-[8-amino-6-(4-methyl-3-pyridyl)-2,7-naphthyridin-3-yl]-2-isothiazol-4-yl-cyclopropanecarboxamide

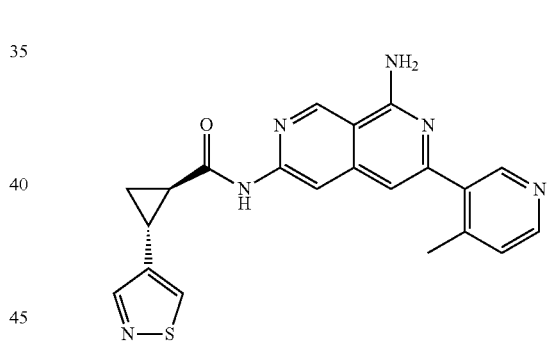

A mixture of (±)-trans-N-(8-amino-6-chloro-2,7-naphthyridin-3-yl)-2-isothiazol-4-yl-cyclopropanecarboxamide (crude 230 mg, about 0.60 mmol), 4-methyl-3-(4,4,5,5-tetramethyl-1,3,2-dioxaborolan-2-yl)pyridine (250 mg, 1.14 mmol), XPhos Pd G2 (50 mg, 0.06 mmol), XPhos (60 mg, 0.13 mmol) and K$_2$CO$_3$ (250 mg, 1.81 mmol) in 1,4-dioxane (16 mL) and water (4 mL) was stirred at 100° C. under Ar for 2 h. The reaction mixture was cooled to room temperature and diluted with ethyl acetate (100 mL). The organic layer was washed with brine (30 mL). Organic layer was separated, dried over Na$_2$SO$_4$, filtered and evaporated. The residue was purified with silica gel chromatography (PE:THF=1:3) followed by flash chromatography (C18, NH$_4$HCO$_3$/MeOH/H$_2$O) to give (±)-trans-N-[8-amino-6-(4-methyl-3-pyridyl)-2,7-naphthyridin-3-yl]-2-isothiazol-4-yl-cyclopropanecarboxamide (45 mg, 18.6% yield of two steps) as a light yellow solid. LCMS (ESI): R$_T$ (min)=1.67, [M+H]$^+$=403.1, method=C; $^1$H NMR (400 MHz, DMSO-d$_6$): δ 11.00 (brs, 1H), 9.37 (s, 1H), 8.77 (s, 1H), 8.57 (s, 1H), 8.53 (s, 1H), 8.44 (d, J=4.8 Hz, 1H), 8.27 (s, 1H), 7.32 (brs, 2H), 7.31 (s, 1H), 6.98 (s, 1H), 2.60-2.55 (m, 1H), 2.41 (s, 3H), 2.44-2.40 (m, 1H), 1.56-1.51 (m, 1H), 1.47-1.44 (m, 1H).

Example 116

(±)-trans-N-(8-amino-5-fluoro-6-(4-methylpyridin-3-yl)-2,7-naphthyridin-3-yl)-2-cyanocyclopropanecarboxamide (Compound 153)

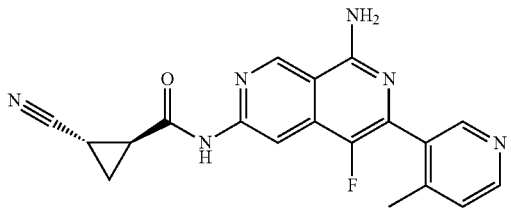 [SMILES: Cc1ccncc1-c1nc(N)c2cnc(NC(=O)[C@H]3C[C@@H]3C#N)cc2c1F]

To a sealed tube was added (±)-trans-N-[8-amino-6-(4-methyl-3-pyridyl)-2,7-naphthyridin-3-yl]-2-cyano-cyclopropanecarboxamide (160 mg, 0.46 mmol), acetonitrile (20 mL) and Selectfluor (105 mg, 0.28 mmol). The mixture was stirred at 75° C. for 2 hours. The mixture was filtered, concentrated and purified by silica-gel column chromatography (eluted with DCM/MeOH=30:1 to 10:1) followed by prep-HPLC (acetonitrile 30-80%/0.1% NH$_4$HCO$_3$ in water) to give (±)-trans-N-[8-amino-5-fluoro-6-(4-methyl-3-pyridyl)-2,7-naphthyridin-3-yl]-2-cyano-cyclopropanecarboxamide (25 mg, 15% yield) as a white solid. LCMS (ESI): R$_T$ (min)=1.546, [M+H]$^+$=363.2, method=G; $^1$H NMR (400 MHz, CD$_3$OD) δ 9.32 (s, 1H), 8.51 (s, 1H), 8.47 (s, 1H), 8.45 (d, J=5.2 Hz, 1H), 7.41 (d, J=5.2 Hz, 1H), 2.70-2.62 (m, 1H), 2.37 (s, 3H), 2.15-2.09 (m, 1H), 1.65-1.52 (m, 2H).

Example 117

(±)-trans-N-(8-amino-6-(4-methylpyridin-3-yl)-2,7-naphthyridin-3-yl)-2-(hydroxymethyl)cyclopropanecarboxamide (Compound 154)

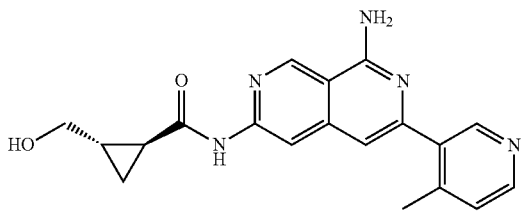 [SMILES: Cc1ccncc1-c1cc2cc(NC(=O)[C@H]3C[C@@H]3CO)ncc2c(N)n1]

Step 1: (±)-trans-2-(hydroxymethyl)cyclopropanecarboxylic acid

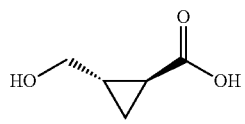

To a vial was added methyl (trans)-2-(hydroxymethyl)cyclopropanecarboxylate (520 mg, 4 mmol), water (5 mL), tetrahydrofuran (5 mL), methyl alcohol (5 mL) and NaOH (728 mg, 18.2 mmol). The mixture was stirred at 40° C. for 2 hours. The reaction was concentrated to remove the organic solvent, and acidified to pH=3-4 with 2 N HCl. The product was extracted with ethyl acetateA (50 mL×2) The combined extracts were washed with brine (20 mL), dried over Na$_2$SO$_4$, filtered and concentrated in vacuo to give (±)-trans-2-(hydroxymethyl)cyclopropanecarboxylic acid (320 mg, 69% yield) as a pale-yellow oil.

Step 2: (±)-trans-2-(acetoxymethyl)cyclopropanecarboxylic acid

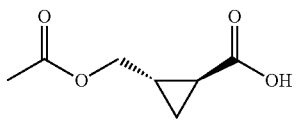

To a vial was added (±)-trans-2-(hydroxymethyl)cyclopropanecarboxylic acid (320 mg, 2.76 mmol), dichloromethane (20 mL) and acetyl chloride (1.5 mL, 21 mmol). The mixture was stirred at 40° C. for 2 hours. The mixture was concentrated in vacuo to give the crude title compound as a pale-yellow oil.

Step 3: (±)-trans-2-(chlorocarbonyl)cyclopropyl)methyl acetate

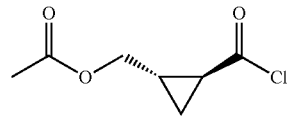

To a vial was added (±)-trans-2-(acetoxymethyl)cyclopropanecarboxylic acid (430 mg, 2.7 mmol) and DCM (30 mL). Oxalyl chloride (0.5 mL, 5.4 mmol) was added dropwise at 0° C. N,N-Dimethylformamide (0.01 mL) was added. The mixture was stirred at 20° C. for 2 hours. The reaction mixture was concentrated to give the title compound.

Step 4: (±)-trans-2-(6,8-dichloro-2,7-naphthyridin-3-ylcarbamoyl)cyclopropyl)methyl acetate

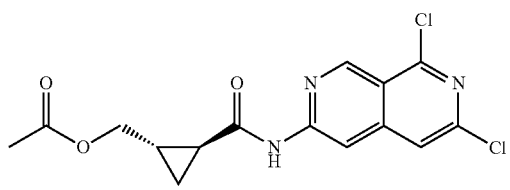 [SMILES: CC(=O)OC[C@H]1C[C@@H]1C(=O)Nc1cc2cc(Cl)nc(Cl)c2cn1]

To a vial was added 6,8-dichloro-2,7-naphthyridin-3-amine hydrochloride (300 mg, 1.2 mmol), pyridine (1 mL, 12 mmol) and DCM (5 mL). A solution of (±)-[trans-2-chlorocarbonylcyclopropyl]methyl acetate (430 mg, 2.43 mmol) in DCM (5 mL) was added dropwise. The mixture was stirred at rt for 2 hours. The mixture was concentrated and purified by silica-gel chromatography (eluted with PE/EA from 1:1 to 0:100) to give (±)-[trans-2-[(6,8-dichloro-2,7-naphthyridin-3-yl)carbamoyl]cyclopropyl]methyl acetate (430 mg, 61% yield) as a yellow solid. LCMS (ESI) [M+H]⁺=354.0.

Step 5: (±)-trans-2-(8-amino-6-chloro-2,7-naphthyridin-3-ylcarbamoyl)cyclopropyl)methyl acetate

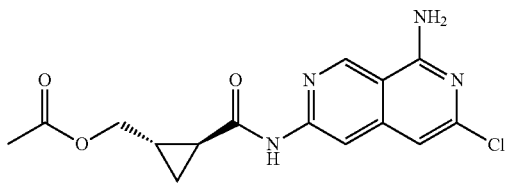 [SMILES: CC(=O)OC[C@H]1C[C@@H]1C(=O)Nc1cc2cc(Cl)nc(N)c2cn1]

To a sealed tube was added (±)-[trans-2-[(6,8-dichloro-2,7-naphthyridin-3-yl)carbamoyl]cyclopropyl]methyl acetate (430 mg, 0.73 mmol), NH₃ (0.5 N in dioxane, 18 mL, 9 mmol) and ammonium hydroxide (14 mL). The mixture was stirred at 90° C. for 4 hours. The mixture was concentrated to get crude (±)-[trans-2-[(8-amino-6-chloro-2,7-naphthyridin-3-yl)carbamoyl]cyclopropyl]methyl acetate (440 mg, 90% yield) as a yellow solid. LCMS (ESI) [M+H]⁺=335.1.

Step 6: (±)-trans-2-(8-amino-6-(4-methylpyridin-3-yl)-2,7-naphthyridin-3-ylcarbamoyl)cyclopropyl) methyl acetate

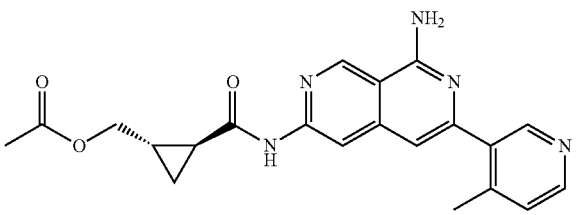 [SMILES: CC(=O)OC[C@H]1C[C@@H]1C(=O)Nc1cc2cc(-c3cnccc3C)nc(N)c2cn1]

To a sealed tube was added Na₂CO₃ (215 mg, 2.0 mmol), Pd(dppf)Cl₂ (112 mg, 0.15 mmol), (±)-[trans-2-[(8-amino-6-chloro-2,7-naphthyridin-3-yl)carbamoyl]cyclopropyl] methyl acetate (440 mg, 0.66 mmol) and 4-methyl-3-(4,4,5,5-tetramethyl-1,3,2-dioxaborolan-2-yl)pyridine (292 mg, 1.33 mmol), 1,4-dioxane (10 mL) and water (1 mL). The mixture was bubbled with N₂ for 2 min, and stirred at 100° C. for 4 h. The mixture filtered and concentrated to give crude (±)-[trans-2-[[8-amino-6-(4-methyl-3-pyridyl)-2,7-naphthyridin-3-yl]carbamoyl]cyclopropyl]methyl acetate (500 mg, 58% yield) as a brown solid. The crude product was used for the next step directly. LCMS (ESI) [M+H]⁺=392.2.

Step 7: (±)-trans-N-(8-amino-6-(4-methylpyridin-3-yl)-2,7-naphthyridin-3-yl)-2-(hydroxymethyl)cyclopropanecarboxamide

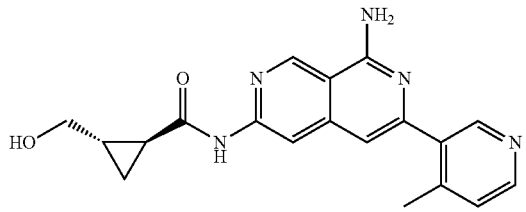 [SMILES: Cc1ccncc1-c1cc2cc(NC(=O)[C@H]3C[C@@H]3CO)ncc2c(N)n1]

To a vial was added (±)-[trans-2-[[8-amino-6-(4-methyl-3-pyridyl)-2,7-naphthyridin-3-yl]carbamoyl]cyclopropyl] methyl acetate (500 mg, 0.38 mmol), Na₂CO₃ (500 mg, 4.7 mmol) and MeOH (10 mL). The mixture was stirred at rt for 2 hours. The mixture was filtered and concentrated. The residue was purified by silica-gel column chromatography (DCM/MeOH from 50:1 to 10:1) followed by prep-HPLC (Mobile Phase: A: Water (10 mmol NH₄HCO₃), B: Acetonitrile) to give (±)-trans-N-[8-amino-6-(4-methyl-3-pyridyl)-2,7-naphthyridin-3-yl]-2-(hydroxymethyl)cyclopropanecarboxamide (21 mg, 16% yield) as a white solid. LCMS (ESI): R$_T$(min)=1.285, [M+H]⁺=350.2, method=B; ¹H NMR (400 MHz, CD₃OD) δ 9.27 (s, 1H), 8.52 (s, 1H), 8.41 (d, J=5.2 Hz, 1H), 8.28 (s, 1H), 7.37 (d, J=5.2 Hz, 1H), 6.94 (s, 1H), 3.64 (dd, J=6.0, 11.6 Hz, 1H), 3.46 (dd, J=6.4, 11.6 Hz, 1H), 2.44 (s, 3H), 1.90-1.84 (m, 1H), 1.76-1.68 (m, 1H), 1.29-1.21 (m, 1H), 0.97-0.91 (m, 1H).

Example 118

(±)-trans-N-(8-amino-6-(4-methylpyridin-3-yl)-2,7-naphthyridin-3-yl)-2-(aminomethyl)cyclopropanecarboxamide (Compound 155)

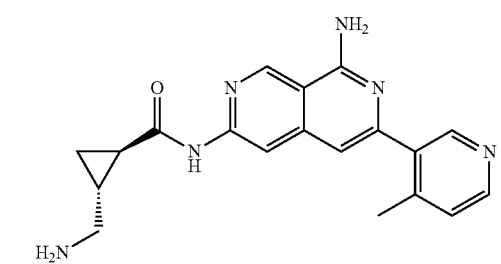 [SMILES: Cc1ccncc1-c1cc2cc(NC(=O)[C@@H]3C[C@H]3CN)ncc2c(N)n1]

Step 1: (±)-trans-N-(8-amino-6-(4-methylpyridin-3-yl)-2,7-naphthyridin-3-yl)-2-formylcyclopropanecarboxamide

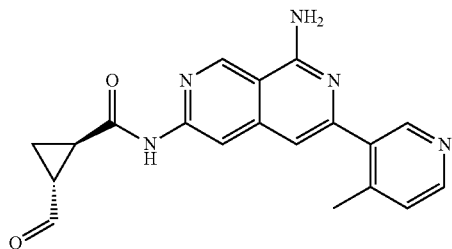 [SMILES: Cc1ccncc1-c1cc2cc(NC(=O)[C@@H]3C[C@H]3C=O)ncc2c(N)n1]

To a vial was added (±)-trans-N-[8-amino-6-(4-methyl-3-pyridyl)-2,7-naphthyridin-3-yl]-2-cyano-cyclopropanecarboxamide (230 mg, 0.67 mmol) and dichloromethane (20 mL). The mixture was cooled to −30° C. before adding DIBAL-H (1 N in toluene, 4 mL, 4 mmol) dropwise. The mixture was stirred at −30° C. for 2 hours. The reaction was quenched by adding saturated NH$_4$Cl aq. (2 mL) at −30° C. and then concentrated. The solid was re-dissolved in DCM/MeOH=10:1 (50 mL), filtered and concentrated to give crude (±)-trans-N-[8-amino-6-(4-methyl-3-pyridyl)-2,7-naphthyridin-3-yl]-2-formyl-cyclopropanecarboxamide (300 mg, 26% yield). LCMS (ESI) [M+H]$^+$=348.1.

Step 2: (±)-trans-N-(8-amino-6-(4-methylpyridin-3-yl)-2,7-naphthyridin-3-yl)-2-(aminomethyl)cyclopropanecarboxamide

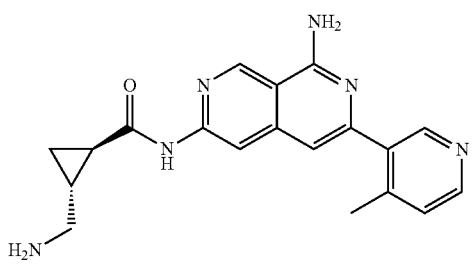 [SMILES: Cc1ccncc1-c1cc2cc(NC(=O)[C@@H]3C[C@H]3CN)ncc2c(N)n1]

To a vial was added (±)-trans-N-[8-amino-6-(4-methyl-3-pyridyl)-2,7-naphthyridin-3-yl]-2-formyl-cyclopropanecarboxamide (300 mg, 0.17 mmol) and NH$_3$ (7N in MeOH, 10 mL, 70 mmol). The mixture was stirred at rt for 60 min. After cooling to 0° C., NaBH$_4$ (200 mg, 5.29 mmol) was added in portions and stirred for 10 min. The mixture was quenched by adding saturated NH$_4$Cl aq. (1 mL). Na$_2$SO$_4$ (5 g) was added, the reaction mixture was stirred at rt for 5 min, filtered and concentrated in vacuo. The residue was purified by prep-TLC (DCM/MeOH/NH$_4$OH=100:10:1) to give (±)-trans-2-(aminomethyl)-N-[8-amino-6-(4-methyl-3-pyridyl)-2,7-naphthyridin-3-yl]cyclopropanecarboxamide (23 mg, 36% yield) as a brown solid. LCMS (ESI): R$_T$(min)=1.373, [M+H]$^+$=349.2, method=G; $^1$H NMR (400 MHz, CD$_3$OD) δ: 9.18 (s, 1H), 8.42 (s, 1H), 8.31 (d, J=5.2 Hz, 1H), 8.17 (s, 1H), 7.28 (d, J=5.2 Hz, 1H), 6.86 (s, 1H), 2.66 (dd, J=6.8, 13.2 Hz, 1H), 2.55 (dd, J=7.2, 13.2 Hz, 1H), 2.34 (s, 3H), 1.77-1.71 (m, 1H), 1.56-1.51 (m, 1H), 1.20-1.15 (m, 1H), 0.86-0.79 (m, 1H).

Example 119

N-(8-amino-5-fluoro-6-(4-methylpyridin-3-yl)-2,7-naphthyridin-3-yl)acetamide (Compound 156)

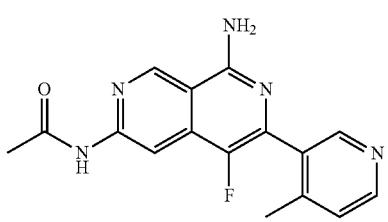 [SMILES: CC(=O)Nc1cc2c(F)c(-c3cnccc3C)nc(N)c2cn1]

Step 1:
N-(6,8-dichloro-2,7-naphthyridin-3-yl)acetamide

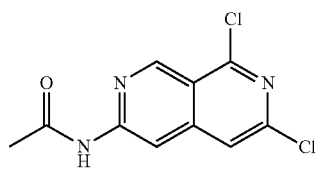 [SMILES: CC(=O)Nc1cc2cc(Cl)nc(Cl)c2cn1]

To a vial was added 6,8-dichloro-2,7-naphthyridin-3-amine hydrochloride (615 mg, 2.45 mmol), 1,2-dichloroethane (30 mL), pyridine (2 mL, 24.93 mmol) and acetyl chloride (1 mL, 14.18 mmol) The mixture was stirred at rt for 2 hours. The mixture was concentrated and purified by silica gel column chromatography (PE/EA from 1:1 to 0:100) to give N-(6,8-dichloro-2,7-naphthyridin-3-yl)acetamide (780 mg, 99% yield) as a yellow solid. LCMS (ESI) [M+H]$^+$=256.0.

Step 2: N-(8-amino-6-chloro-2,7-naphthyridin-3-yl)acetamide

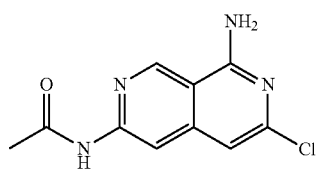 [SMILES: CC(=O)Nc1cc2cc(Cl)nc(N)c2cn1]

To a sealed tube was added NH$_3$ (0.5 N in dioxane, 6 mL, 3 mmol), NH$_3$·H$_2$O (6 mL, 39 mmol) and N-(6,8-dichloro-2,7-naphthyridin-3-yl)acetamide (780 mg, 2.44 mmol). The mixture was stirred at 90° C. for 4 hours. The mixture was concentrated to give crude N-(8-amino-6-chloro-2,7-naphthyridin-3-yl)acetamide (810 mg, 98% yield) as a yellow solid. LCMS (ESI) [M+H]$^+$=237.1.

619

Step 3: N-(8-amino-6-(4-methylpyridin-3-yl)-2,7-naphthyridin-3-yl)acetamide

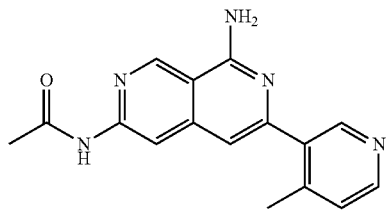 [SMILES: CC(=O)Nc1cc2cc(-c3cnccc3C)nc(N)c2cn1]

To a vial was added Pd(dppf)Cl₂ (120 mg, 0.17 mmol), 4-methyl-3-(4,4,5,5-tetramethyl-1,3,2-dioxaborolan-2-yl)pyridine (606 mg, 2.77 mmol), Na₂CO₃ (746 mg, 7 mmol), N-(8-amino-6-chloro-2,7-naphthyridin-3-yl)acetamide (810 mg, 2.4 mmol), 1,4-dioxane (50 mL) and water (5 mL) The mixture was stirred at 100° C. for 1.5 h under N₂. The mixture was concentrated and purified by silica-gel column chromatography (DCM/MeOH from 100:1 to 10:1) to give N-[8-amino-6-(4-methyl-3-pyridyl)-2,7-naphthyridin-3-yl]acetamide (665 mg, 85% yield) as a yellow solid. LCMS (ESI) [M+H]⁺=294.1.

Step 4: N-(8-amino-5-fluoro-6-(4-methylpyridin-3-yl)-2,7-naphthyridin-3-yl)acetamide

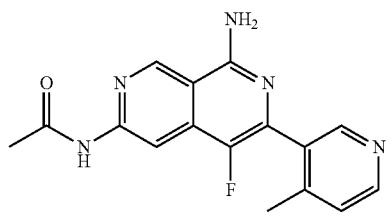 [SMILES: CC(=O)Nc1cc2c(F)c(-c3cnccc3C)nc(N)c2cn1]

To a vial was added N-[8-amino-6-(4-methyl-3-pyridyl)-2,7-naphthyridin-3-yl]acetamide (600 mg, 2.05 mmol), acetonitrile (70 mL) and Selectfluor (600 mg, 1.61 mmol). The mixture was stirred at 60° C. for 16 hours. The mixture was filtered and concentrated. The residue was purified by prep-HPLC (acetonitrile 30-70%/0.1% NH₄OH in water) to give N-[8-amino-5-fluoro-6-(4-methyl-3-pyridyl)-2,7-naphthyridin-3-yl]acetamide (120 mg, 17% yield) as a white solid. LCMS (ESI): $R_T$ (min)=1.489, [M+H]⁺=312.0, method=C; ¹H NMR (400 MHz, DMSO-d₆) δ 10.88 (s, 1H), 9.42 (s, 1H), 8.52 (s, 1H), 8.49 (d, J=4.8 Hz, 1H), 8.37 (s, 1H), 7.37 (d, J=4.8 Hz, 1H), 7.30 (br, 2H), 2.28 (s, 3H), 2.17 (s, 3H).

Example 120

(±)-trans-N-[8-amino-6-(4-methyl-3-pyridyl)-2,7-naphthyridin-3-yl]-2-(cyanomethyl)cyclopropanecarboxamide (Compound 157)

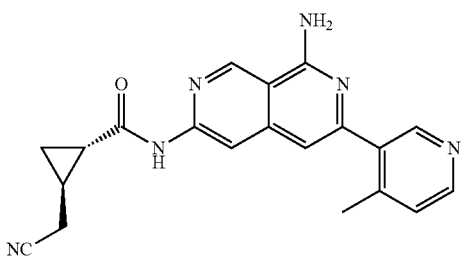 [SMILES: Cc1ccncc1-c1cc2cc(NC(=O)[C@H]3C[C@@H]3CC#N)ncc2c(N)n1]

Step 1: (±)-trans-2-(cyanomethyl)cyclopropanecarboxylic acid

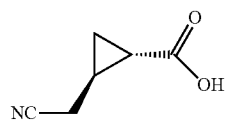

To a solution of ethyl trans-2-(cyanomethyl)cyclopropanecarboxylate (500 mg, 3.26 mmol) in tetrahydrofuran (8 mL), water (8 mL) was added LiOH H₂O (268 mg, 6.53 mmol). The reaction mixture was stirred at 25° C. for overnight. The solution was concentrated and the residue was diluted with H₂O (20 mL) and washed with ethyl acetate (20 mL). The aqueous layer was acidified with 4N HCl to pH=3 and extracted with ethyl acetate (30 mL×3). The combined organic layers were washed with brine, dried over Na₂SO₄ and concentrated under reduced pressure to give (±)-trans-2-(cyanomethyl)cyclopropane carboxylic acid (380 mg, 3.04 mmol, 95% yield) as a colorless oil. ¹H NMR (400 MHz, DMSO-d₆) δ 12.28 (s, 1H), 2.67-2.64 (m, 2H), 1.59-1.50 (m, 2H), 1.07-1.03 (m, 1H), 0.91-0.88 (m, 1H).

Step 2: (±)-trans-2-(cyanomethyl)-N-(6,8-dichloro-2,7-naphthyridin-3-yl)cyclopropanecarboxamide

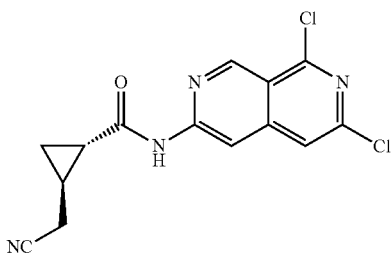 [SMILES: N#CC[C@H]1C[C@@H]1C(=O)Nc1cc2cc(Cl)nc(Cl)c2cn1]

To a mixture of (±)-trans-2-(cyanomethyl)cyclopropanecarboxylic acid (342 mg, 2.73 mmol), 6,8-dichloro-2,7-naphthyridin-3-amine (450 mg, 2.1 mmol) and pyridine (1.7 mL, 21.02 mmol) in dichloromethane (20 mL) was added POCl₃ (419 mg, 2.73 mmol) 0° C. The mixture was stirred for 1 h at rt. The mixture was concentrated and purified by flash column chromatography (EtOAc/PE=1/1) to give (±)-trans-2-(cyanomethyl)-N-(6,8-dichloro-2,7-naphthyridin-3-yl)cyclopropanecarboxamide (536 mg, 79% yield) as a yellow solid. LCMS (ESI): [M+H−100]⁺=321.0;

Step 3: (±)-trans-N-(8-amino-6-chloro-2,7-naphthyridin-3-yl)-2-(cyanomethyl)cyclopropanecarboxamide

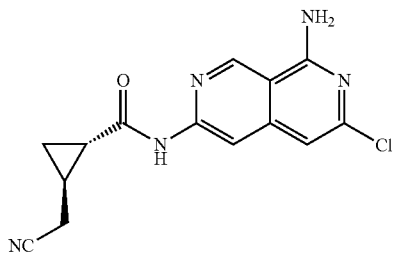 [SMILES: N#CC[C@H]1C[C@@H]1C(=O)Nc1cc2cc(Cl)nc(N)c2cn1]

A mixture of (±)-trans-2-(cyanomethyl)-N-(6,8-dichloro-2,7-naphthyridin-3-yl)cyclopropanecarboxamide (486 mg, 1.51 mmol) and NH$_3$H$_2$O (5 mL, 1.51 mmol) in 1,4-dioxane (20 mL) was heated to 80° C. for 5 h in a sealed tube. The solution was concentrated and the crude product was washed with EA/PE=1:1 to give (±)-trans-N-(8-amino-6-chloro-2,7-naphthyridin-3-yl)-2-(cyanomethyl) cyclopropanecarboxamide (435 mg, 95% yield) as a yellow solid. LCMS (ESI): [M+H]⁺=302.0.

Step 4: (±)-trans-N-[8-amino-6-(4-methyl-3-pyridyl)-2,7-naphthyridin-3-yl]-2-(cyanomethyl) cyclopropane carboxamide

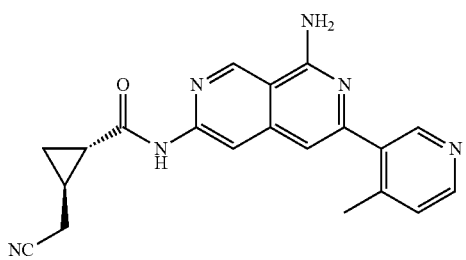 [SMILES: Cc1ccncc1-c1cc2cc(NC(=O)[C@H]3C[C@@H]3CC#N)ncc2c(N)n1]

A mixture of (±)-trans-N-(8-amino-6-chloro-2,7-naphthyridin-3-yl)-2-(cyanomethyl) cyclopropanecarboxamide (250 mg, 0.83 mmol), 4-methyl-3-(4,4,5,5-tetramethyl-1,3,2-dioxaborolan-2-yl)pyridine (236 mg, 1.08 mmol), Pd(dppf)Cl$_2$ (61 mg, 0.08 mmol) and Na$_2$CO$_3$ (263 mg, 2.49 mmol) in 1,4-dioxane (12 mL) and water (3 mL) was stirred at 110° C. for 2 h. The mixture was diluted with water (20 ml) and extracted with EA (30 mL×3). The organics were washed with a saturated NaCl solution (50 ml), dried with anhydrous Na$_2$SO$_4$, filtered and concentrated. The crude product was purified by Prep-HPLC (Mobile phase: A water (0.01% NH$_3$)+10 mm (NH$_4$HCO$_3$), B Acetonitrile) to give (±)-trans-N-[8-amino-6-(4-methyl-3-pyridyl)-2,7-naphthyridin-3-yl]-2-(cyanomethyl)cyclopropanecarboxamide (62 mg, 20.9% yield) as a white solid. LCMS (ESI): R$_T$ (min)=1.543, [M+H]⁺=359.1, method=C; ¹H NMR (400 MHz, DMSO-d$_6$) δ 9.45 (s, 1H), 8.58 (s, 1H), 8.44 (d, J=5.2 Hz, 1H), 8.38 (s, 1H), 7.45 (s, 2H), 7.32 (d, J=4.8 Hz, 1H), 7.08 (s, 1H), 5.04 (d, J=3.6 Hz, 1H), 3.14-3.11 (m, 2H), 2.91-2.86 (m, 1H), 2.59-2.55 (m, 1H), 2.47-2.45 (m, 4H), 2.01-2.00 (m, 1H).

Example 121

Exo-N-(8-amino-6-(4-methylpyridin-3-yl)-2,7-naphthyridin-3-yl)-2-oxo-3-azabicyclo[3.1.0]hexane-6-carboxamide (Compound 158)

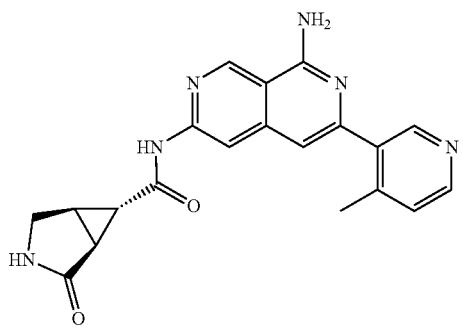 [SMILES: Cc1ccncc1-c1cc2cc(NC(=O)[C@H]3[C@@H]4CNC(=O)[C@@H]43)ncc2c(N)n1]

Step 1: exo-3-(tert-butoxycarbonyl)-2-oxo-3-azabicyclo[3.1.0]hexane-6-carboxylic acid

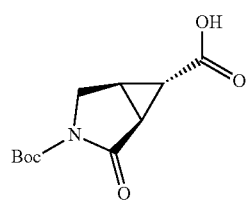 [SMILES: CC(C)(C)OC(=O)N1C[C@H]2[C@H](C(=O)O)[C@H]2C1=O]

A mixture of exo-3-tert-butoxycarbonyl-3-azabicyclo[3.1.0]hexane-6-carboxylic acid (360 mg, 1.58 mmol), NaIO$_4$ (847 mg, 3.96 mmol) and RuCl$_3$.3H$_2$O (36 mg, 0.17 mmol) in ethyl acetate (10 mL) and water (10 mL) was stirred at 25° C. overnight. Then the mixture was filtered, ethyl acetate (30 mL) was added. The mixture was washed with water (30 mL×1), brine (30 mL×1), dried over anhydrous Na$_2$SO$_4$, filtered and concentrated by rotavap to give crude exo-3-tert-butoxycarbonyl-4-oxo-3-azabicyclo[3.1.0]hexane-6-carboxylic acid (287 mg, 75% yield) as a yellow oil. LCMS (ESI): [M+H−56]⁺=186.1.

Step 2: exo-tert-butyl 6-(6,8-dichloro-2,7-naphthyridin-3-ylcarbamoyl)-2-oxo-3-azabicyclo[3.1.0]hexane-3-carboxylate

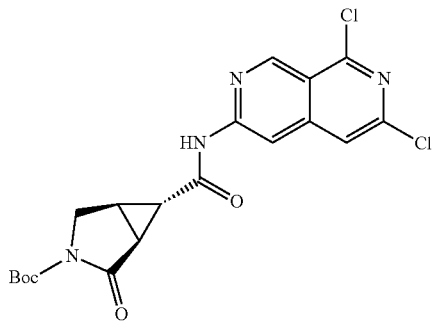 [SMILES: CC(C)(C)OC(=O)N1C[C@H]2[C@H](C(=O)Nc3cc4cc(Cl)nc(Cl)c4cn3)[C@H]2C1=O]

To a mixture of 6,8-dichloro-2,7-naphthyridin-3-amine (45 mg, 0.21 mmol), exo-3-tert-butoxycarbonyl-4-oxo-3-azabicyclo[3.1.0]hexane-6-carboxylic acid (80 mg, 0.33 mmol) and pyridine (0.34 mL, 4.2 mmol) in dichloromethane (10 mL) being cooled to 0° C. was added the POCl$_3$ (97 mg, 0.63 mmol). The mixture was stirred for 1 h at rt. Then the mixture was concentrated and purity by flash column chromatography (eluting EtOAc/PE=1/1) to give exo-tert-butyl 6-(6,8-dichloro-2,7-naphthyridin-3-ylcarbamoyl)-2-oxo-3-azabicyclo[3.1.0]hexane-3-carboxylate (90 mg, 98% yield) as a yellow solid. LCMS (ESI): [M+H−100]$^+$=337.0.

Step 3: exo-N-(8-amino-6-chloro-2,7-naphthyridin-3-yl)-2-oxo-3-azabicyclo[3.1.0]hexane-6-carboxamide

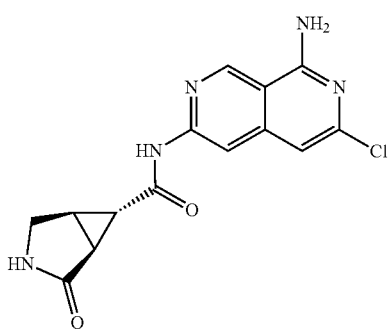 [SMILES: Nc1nc(Cl)cc2cc(NC(=O)[C@H]3[C@@H]4CNC(=O)[C@@H]43)ncc12]

A mixture of tert-butyl exo-6-[(6,8-dichloro-2,7-naphthyridin-3-yl)carbamoyl]-4-oxo-3-azabicyclo[3.1.0] hexane-3-carboxylate (52 mg, 0.12 mmol) and NH$_3$H$_2$O (2.0 mL, 0.12 mmol) in 1,4-dioxane (6 mL) was heated to 80° C. overnight in a sealed tube. The mixture was concentrated. The residue was taken up in EtOAc (20 mL) and washed with water (10 mL×2), saturated NaCl solution (10 mL), dried with anhydrous Na$_2$SO$_4$, filtered and concentrated. The crude product exo-N-(8-amino-6-chloro-2,7-naphthyridin-3-yl)-4-oxo-3-azabicyclo[3.1.]hexane-6-carboxamide (35 mg, 94% yield) was used in the next step without purification. LCMS (ESI): [M+H]$^+$=318.0.

Step 4: exo-N-[8-amino-6-(4-methyl-3-pyridyl)-2,7-naphthyridin-3-yl]-4-oxo-3-azabicyclo[3.1.0]hexane-6-carboxamide

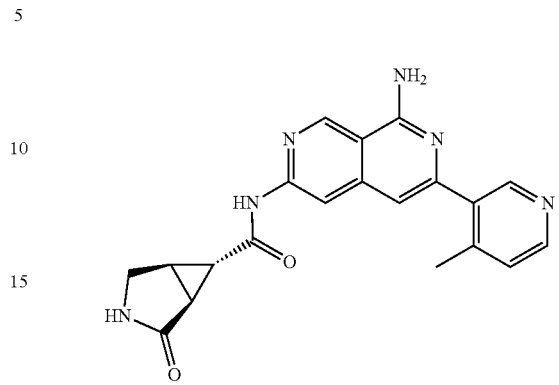

A mixture of exo-N-(8-amino-6-chloro-2,7-naphthyridin-3-yl)-4-oxo-3-azabicyclo[3.1.0] hexane-6-carboxamide (35 mg, 0.11 mmol), 4-methyl-3-(4,4,5,5-tetramethyl-1,3,2-dioxaborolan-2-yl)pyridine (31 mg, 0.14 mmol), Pd(dppf)Cl$_2$ (8.0 mg, 0.011 mmol), K$_2$CO$_3$ (46 mg, 0.33 mmol) in 1,4-dioxane (4.0 mL) and water (0.8 mL) was stirred at 110° C. for 2 hours. The reaction was filtered through a pad of silica gel, and the filtrate was concentrated in vacuo. The crude product was further purified by Prep-HPLC (Mobile phase: A water (0.01% NH$_3$)+10 mm (NH$_4$HCO$_3$), B Acetonitrile) to give exo-N-[8-amino-6-(4-methyl-3-pyridyl)-2,7-naphthyridin-3-yl]-4-oxo-3-azabicyclo[3.1.0] hexane-6-carboxamide (6 mg, 14.6% yield) as a white solid. LCMS (ESI): R$_T$ (min)=1.326, [M+H]$^+$=375.1, method=G; $^1$H NMR (400 MHz, DMSO-d$_6$) δ 11.08 (s, 1H), 9.38 (s, 1H), 8.56 (s, 1H), 8.43 (d, J=4.8 Hz, 1H), 8.21 (s, 1H), 7.43 (s, 1H), 7.34-7.31 (m, 3H), 6.98 (s, 1H), 3.51-3.48 (m, 2H), 2.41-2.40 (m, 4H), 2.18-2.16 (m, 1H), 2.09-2.08 (m, 1H).

Example 122

(±)-trans-N-[8-amino-6-(4-methyl-3-pyridyl)-2,7-naphthyridin-3-yl]-2-(1-methylpyrazol-4-yl) cyclopropanecarboxamide (Compound 159)

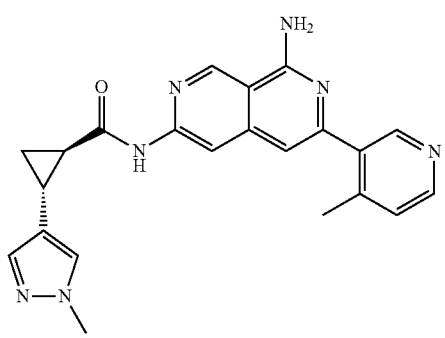 [SMILES: Cc1ccncc1-c1cc2cc(NC(=O)[C@@H]3C[C@H]3c3cnn(C)c3)ncc2c(N)n1]

625

Step 1: tert-butyl (E)-3-(1-methylpyrazol-4-yl)prop-2-enoate

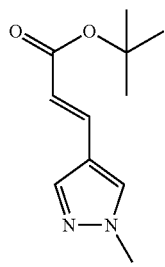

A mixture of 1-methyl-4-iodo-1h-pyrazole (12 g, 57.69 mmol), tert-butyl acrylate (30 g, 234.06 mmol), Pd(OAc)$_2$ (0.9 g, 4.02 mmol), tri-p-tolylphosphine (3.45 g, 11.35 mmol) and TEA (58 g, 574.26 mmol) in acetonitrile (100 mL) under Ar was stirred at 110° C. for 3 h. The mixture was concentrated and purified by column chromatography eluting with EtOAc/hexane=1:2 to afford tert-butyl (E)-3-(1-methylpyrazol-4-yl)prop-2-enoate (4.6 g, 21.87 mmol, 38% yield) as a brown oil. LCMS (ESI) [M+H]$^+$=209.2.

Step 2: (±)-tert-butyl trans-2-(1-methylpyrazol-4-yl)cyclopropanecarboxylate

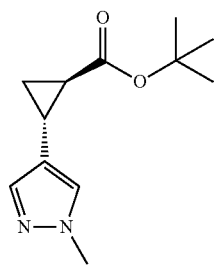 [SMILES: Cn1cc([C@@H]2C[C@H]2C(=O)OC(C)(C)C)cn1]

To a solution of trimethylsulfoxoniumiodide (5.96 g, 27.08 mmol) in dimethyl sulfoxide (60 mL) was added sodium tert-butoxide (2.71 g, 28.23 mmol). The mixture was stirred at 25° C. for 0.5 h. tert-butyl (E)-3-(1-methylpyrazol-4-yl)prop-2-enoate (4.7 g, 22.57 mmol) in DMSO (40 mL) was added to the mixture and stirred at rt overnight. Saturated NH$_4$Cl (80 mL) was added. The mixture was extracted with EtOAc (3×200 mL). The combined extracts were washed with brine (3×100 mL), dried with Na$_2$SO$_4$, filtered and concentrated to give crude (±)-tert-butyl trans-2-(1-methylpyrazol-4-yl)cyclopropanecarboxylate (3.2 g, 13.25 mmol, 59% yield) as a brown oil. LCMS (ESI) [M+H]$^+$=223.1.

626

Step 3: (±)-trans-2-(1-methylpyrazol-4-yl)cyclopropanecarboxylic acid

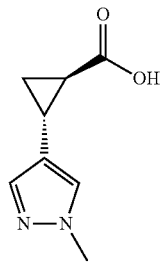

A mixture of (±)-tert-butyl trans-2-(1-methylpyrazol-4-yl)cyclopropanecarboxylate (3.2 g, 14.4 mmol) in 2,2,2-trifluoroacetic acid (30 mL) was stirred at 25° C. for 1 h. The reaction mixture was neutralized with sat NaHCO$_3$ (aq.) to pH=8. The mixture was the re-adjusted to pH 4. The mixture was concentrated and purified by preparative HPLC Reverse phase (C-18), eluting with Acetonitrile/Water+0.05% NH$_4$HCO$_3$, to give (±)-trans-2-(1-methylpyrazol-4-yl)cyclopropanecarboxylic acid (1.7 g, 10.23 mmol, 71% yield) as a white solid. LCMS (ESI) [M+H]$^+$=167.1.

Step 4: (±)-trans-N-(6,8-dichloro-2,7-naphthyridin-3-yl)-2-(1-methylpyrazol-4-yl)cyclopropanecarboxamide

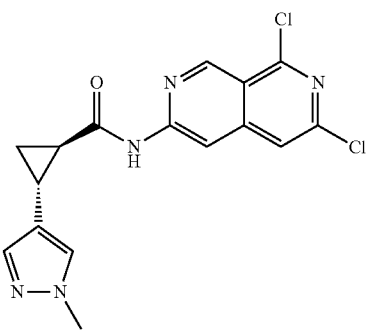 [SMILES: Cn1cc([C@@H]2C[C@H]2C(=O)Nc2cc3cc(Cl)nc(Cl)c3cn2)cn1]

To a solution of (±)-trans-2-(1-methylpyrazol-4-yl)cyclopropanecarboxylic acid (300 mg, 1.81 mmol), pyridine (3 mL, 37.09 mmol) and 6,8-dichloro-2,7-naphthyridin-3-amine hydrochloride (452 mg, 1.8 mmol) in dichloromethane (25 mL) at 0° C. was added POCl$_3$ (900 mg, 5.88 mmol). The mixture was warmed up to rt and stirred at rt for 2 h. H$_2$O (100 mL) was added and the mixture extracted with DCM (3×150 mL). The combined extracts were washed with brine (150 mL), dried with Na$_2$SO$_4$, filtered and concentrated to give crude (±)-(trans)-N-(6,8-dichloro-2,7-naphthyridin-3-yl)-2-(1-methylpyrazol-4-yl)cyclopropanecarboxamide (700 mg, 1.39 mmol, 77% yield) as a yellow solid. LCMS (ESI) [M+H]$^+$=362.1.

Step 5: (±)-trans-N-(8-amino-6-chloro-2,7-naphthyridin-3-yl)-2-(1-methylpyrazol-4-yl)cyclopropanecarboxamide

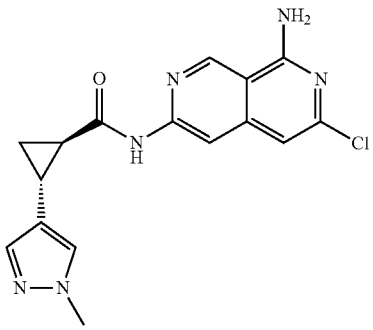 [SMILES: Cn1cc([C@@H]2C[C@H]2C(=O)Nc2cc3cc(Cl)nc(N)c3cn2)cn1]

A mixture of (±)-trans-N-(6,8-dichloro-2,7-naphthyridin-3-yl)-2-(1-methylpyrazol-4-yl)cyclopropanecarboxamide (500 mg, 1.38 mmol) and NH₄OH (12 mL, 1.38 mmol) in 1,4-dioxane (12 mL) was stirred at 90° C. for 3 h. The mixture was concentrated and purified by column chromatography eluting with EtOAc to afford (±)-trans-N-(6,8-dichloro-2,7-naphthyridin-3-yl)-2-(1-methylpyrazol-4-yl)cyclopropanecarboxamide (500 mg, 1.38 mmol) as a yellow solid. LCMS (ESI) [M+H]⁺=343.1.

Step 6: (±)-trans-N-[8-amino-6-(4-methyl-3-pyridyl)-2,7-naphthyridin-3-yl]-2-(1-methylpyrazol-4-yl)cyclopropane carboxamide

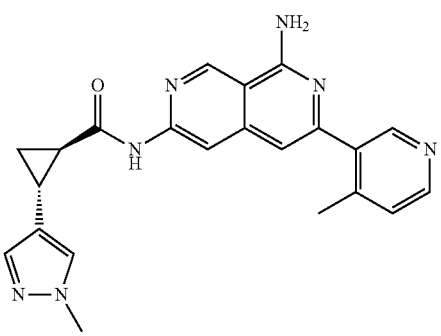 [SMILES: Cc1ccncc1-c1cc2cc(NC(=O)[C@@H]3C[C@H]3c3cnn(C)c3)ncc2c(N)n1]

A mixture of (±)-trans-N-(8-amino-6-chloro-2,7-naphthyridin-3-yl)-2-(1-methylpyrazol-4-yl)cyclopropanecarboxamide (180 mg, 0.53 mmol), 4-methyl-3-(4,4,5,5-tetramethyl-1,3,2-dioxaborolan-2-yl)pyridine (138 mg, 0.63 mmol), x-Phos-Pd-G2 (83 mg, 0.11 mmol), X-Phos (100 mg, 0.21 mmol) and K₂CO₃ (145 mg, 1.05 mmol) in 1,4-dioxane (7 mL) and water (1 mL) under Ar was stirred at 100° C. for 1 h. The mixture was concentrated and purified by column chromatography eluting with DCM/MeOH=10:1 to afford (±)-trans-N-[8-amino-6-(4-methyl-3-pyridyl)-2,7-naphthyridin-3-yl]-2-(1-methylpyrazol-4-yl)cyclopropanecarboxamide (105 mg, 0.26 mmol, 50% yield) as a yellow solid. LCMS (ESI) R_T(min)=1.497, [M+H]⁺=400.2, method=G. ¹H NMR (400 MHz, DMSO-d₆) δ 10.95 (s, 1H), 9.37 (s, 1H), 8.57 (s, 1H), 8.44 (d, J=5.2 Hz, 1H), 8.26 (s, 1H), 7.56 (s, 1H), 7.32 (s, 2H), 7.31 (d, J=5.2 Hz, 1H), 7.30 (s, 1H), 6.97 (s, 1H), 3.77 (s, 3H), 2.41 (s, 3H), 2.23-2.19 (m, 2H), 1.40-1.38 (m, 1H), 1.23-1.18 (m, 1H).

Example 123 trans-N-[8-amino-6-(3-hydroxy-6-methyl-2-oxo-indolin-5-yl)-2,7-naphthyridin-3-yl]-2-cyano-cyclopropanecarboxamide (Compound 160)

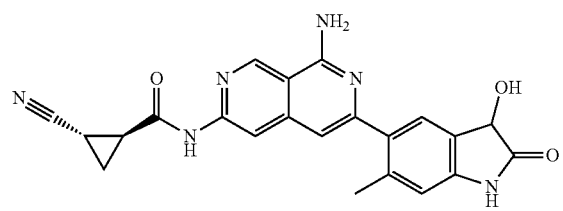 [SMILES: Cc1cc2c(cc1-c1cc3cc(NC(=O)[C@H]4C[C@@H]4C#N)ncc3c(N)n1)C(O)C(=O)N2]

Step 1: 5-bromo-3-hydroxy-6-methyl-indolin-2-one

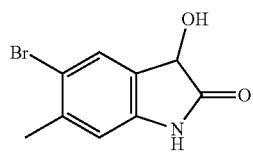

To a solution of 5-bromo-6-methyl-indoline-2,3-dione (980 mg, 4.08 mmol) in tetrahydrofuran (50 mL) at 0° C. was added NaBH₄ (124 mg, 3.26 mmol). The mixture was stirred at 0° C. for 10 min. H₂O (50 mL) was added and the mixture extracted with EtOAc (3×200 mL). The combined extracts were washed with brine (100 mL), dried with Na₂SO₄, filtered and concentrated to give crude 5-bromo-3-hydroxy-6-methyl-indolin-2-one (650 mg, 2.5 mmol, 61% yield) as a brown solid. LCMS (ESI) [M+Na]⁺=265.9.

Step 2: 6-methyl-5-(4,4,5,5-tetramethyl-1,3,2-dioxaborolan-2-yl)indoline-2,3-dione

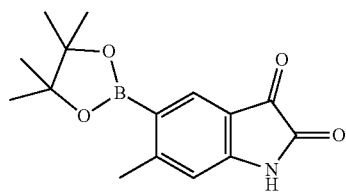 [SMILES: Cc1cc2c(cc1B1OC(C)(C)C(C)(C)O1)C(=O)C(=O)N2]

A mixture of 5-bromo-3-hydroxy-6-methyl-indolin-2-one (630 mg, 2.6 mmol), bis(pinacolato)diboron (331 mg, 13.01 mmol), Pd(dppf)Cl₂ (380 mg, 0.52 mmol) and AcOK (510 mg, 5.2 mmol) in 1,4-dioxane (12 mL) under Ar was stirred at 95° C. for 2 h. The mixture was concentrated and purified by column chromatography eluting with EtOAc/hexane=5:1 to afford 6-methyl-5-(4,4,5,5-tetramethyl-1,3,2-dioxaborolan-2-yl)indoline-2,3-dione (650 mg, 1.45 mmol, 56% yield) as a brown solid. LCMS (ESI) [M+H]⁺=288.1.

Step 3: (±)-trans-N-[8-amino-6-(6-methyl-2,3-di-oxo-indolin-5-yl)-2,7-naphthyridin-3-yl]-2-cyano-cyclopropane carboxamide

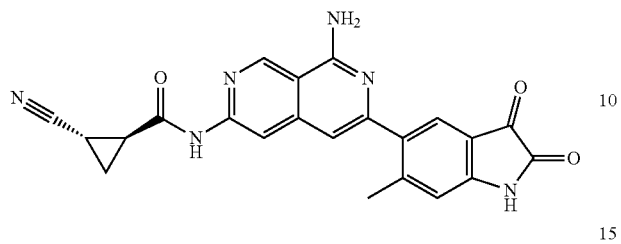

A mixture of (±)-trans-N-(8-amino-6-chloro-2,7-naphthyridin-3-yl)-2-cyano-cyclopropanecarboxamide (300 mg, 1.04 mmol), 6-methyl-5-(4,4,5,5-tetramethyl-1,3,2-dioxaborolan-2-yl)indoline-2,3-dione (449 mg, 1.56 mmol), X-Phos (199 mg, 0.42 mmol), X-Phos-Pd-G2 (164 mg, 0.21 mmol) and $K_2CO_3$ (288 mg, 2.09 mmol) in 1,4-dioxane (12 mL) and water (1 mL) under Ar atmosphere was stirred at 100° C. for 1 h. The mixture was concentrated and purified by column chromatography eluting with DCM/MeOH=10:1 to afford trans-N-[8-amino-6-(6-methyl-2,3-dioxo-indolin-5-yl)-2,7-naphthyridin-3-yl]-2-cyano-cyclopropanecarboxamide (300 mg, 0.27 mmol, 26% yield) as a brown solid. LCMS (ESI) [M+H]$^+$=413.2.

Step 4: trans-N-[8-amino-6-(3-hydroxy-6-methyl-2-oxo-indolin-5-yl)-2,7-naphthyridin-3-yl]-2-cyano-cyclopropane carboxamide

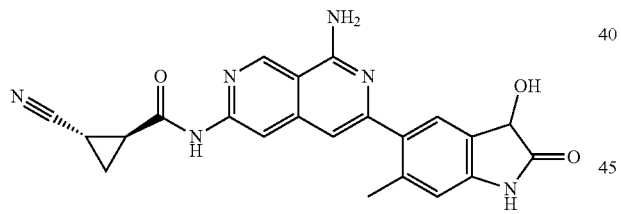

To a solution of trans-N-[8-amino-6-(6-methyl-2,3-dioxo-indolin-5-yl)-2,7-naphthyridin-3-yl]-2-cyano-cyclopropanecarboxamide (300 mg, 0.27 mmol) in tetrahydrofuran (15 mL) at 0° C. was added $NaBH_4$ (4 mg, 0.11 mmol). The mixture was stirred at 0° C. for 10 min. The mixture was concentrated and purified by column chromatography eluting with DCM/MeOH=10:1 to afford trans-N-[8-amino-6-(3-hydroxy-6-methyl-2-oxo-indolin-5-yl)-2,7-naphthyridin-3-yl]-2-cyano-cyclopropanecarboxamide (38 mg, 0.085 mmol, 32% yield) as a yellow solid. LCMS (ESI) $R_T$ (min)=1.437, [M+H]$^+$=415.1, method=C. $^1$H NMR (400 MHz, DMSO-d$_6$) δ 11.23 (s, 1H), 10.3 (s, 1H), 9.35 (s, 1H), 8.16 (s, 1H), 7.37 (s, 1H), 7.26 (s, 2H), 6.84 (s, 1H), 6.68 (s, 1H), 6.16 (d, J=7.6 Hz, 1H), 4.84 (d, J=7.6 Hz, 1H), 2.78-2.74 (m, 1H), 2.36 (s, 3H), 2.17-2.13 (m, 1H), 1.63-1.59 (m, 1H), 1.46-1.41 (m, 1H).

Example 124

1-[3-[4-[[8-amino-6-(4-methyl-3-pyridyl)-2,7-naphthyridin-3-yl]amino]pyrazol-1-yl]azetidin-1-yl]ethanone (Compound 161)

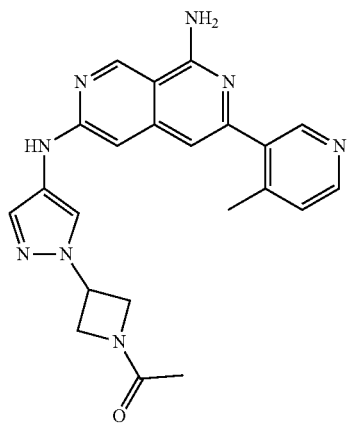 [SMILES: CC(=O)N1CC(n2cc(Nc3cc4cc(-c5cnccc5C)nc(N)c4cn3)cn2)C1]

Step 1: tert-butyl 3-(4-bromopyrazol-1-yl)azetidine-1-carboxylate

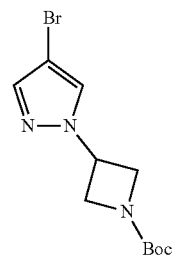 [SMILES: CC(C)(C)OC(=O)N1CC(n2cc(Br)cn2)C1]

To a solution of 4-bromo-1H-pyrazole (2.0 g, 13.61 mmol) in N,N-dimethylformamide (40 mL) at 0° C. was added NaH (1.63 g, 40.75 mmol). The mixture was stirred at 0° C. for 0.5 h. 1-Boc-3-iodoazetidine (5.0 g, 17.66 mmol) was added and stirred at 0° C. for 1 h. The mixture was warmed up to ambient temperature and stirred overnight. $H_2O$ (100 mL) was added. The mixture was extracted with EtOAc (3×200 mL). The combined extracts were washed with brine (3×100 mL), dried with $Na_2SO_4$, filtered and evaporated under reduced pressure. The residue was purified by column chromatography eluting with EtOAc/hexane=1:5 to afford tert-butyl 3-(4-bromopyrazol-1-yl)azetidine-1-carboxylate (1.8 g, 4.38 mmol, 32% yield) as a colourless oil. LCMS (ESI) [M+H−56]$^+$=247.9.

631

Step 2: 1-(azetidin-3-yl)-4-bromo-pyrazole

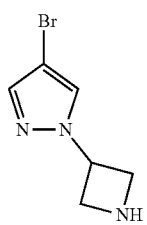

A mixture of tert-butyl 3-(4-bromopyrazol-1-yl)azetidine-1-carboxylate (1.8 g, 4.35 mmol) and 2,2,2-trifluoroacetic acid (8 mL) in dichloromethane (15 mL) was stirred at 25° C. for 2 h. The reaction mixture was neutralized with sat. NaHCO$_3$ (aq.) to pH=7-8. The mixture was concentrated and purified by preparative HPLC Reverse phase (C-18), eluting with acetonitrile/water+0.05% NH$_4$HCO$_3$, to give 1-(azetidin-3-yl)-4-bromo-pyrazole (875 mg, 3.55 mmol, 82% yield) as a white solid. LCMS (ESI) [M+H]$^+$=202.0.

Step 3: 1-[3-(4-bromopyrazol-1-yl)azetidin-1-yl]ethanone

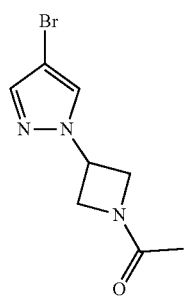

To a solution of 1-(azetidin-3-yl)-4-bromo-pyrazole (400 mg, 1.98 mmol) and pyridine (1.61 mL, 19.85 mmol) in dichloromethane (20 mL) at 0° C. was added acetyl chloride (466 mg, 5.94 mmol). The mixture was stirred at 0° C. for 3 h, The mixture was concentrated and purified by column chromatography eluting with DCM/MeOH=20:1 to afford 1-[3-(4-bromopyrazol-1-yl)azetidin-1-yl]ethanone (400 mg, 1.27 mmol, 64% yield) as a brown solid. LCM (ESI) [M+H]$^+$=244.0.

632

Step 4: 1-[3-[4-[[8-[bis[2,4-dimethoxybenzyl]amino]-6-(4-methyl-3-pyridyl)-2,7-naphthyridin-3-yl]amino]pyrazol-1-yl]azetidin-1-yl]ethanone

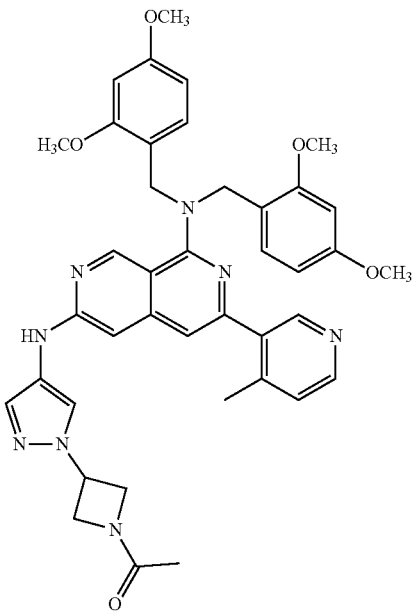 [SMILES: COc1ccc(CN(Cc2ccc(OC)cc2OC)c2nc(-c3cnccc3C)cc3cc(Nc4cnn(C5CN(C(C)=O)C5)c4)ncc23)c(OC)c1]

A mixture of N1,N1-bis[(2,4-dimethoxybenzyl)]-3-(4-methyl-3-pyridyl)-2,7-naphthyridine-1,6-diamine (250 mg, 0.45 mmol), 1-[3-(4-bromopyrazol-1-yl)azetidin-1-yl]ethanone (359 mg, 1.13 mmol), t-BuBrettPhos Palladacycle Gen. 3 (82 mg, 0.09 mmol), t-BuBrettPhos (44 mg, 0.09 mmol) and LiHMDS (1.8 mL, 1.8 mmol) in 1,4-dioxane (10 mL) was stirred under Ar at 100° C. for 20 h. The mixture was concentrated and purified by column chromatography eluting with MeOH/DCM=1:25 to afford 1-[3-[4-[[8-[bis[(2,4-dimethoxybenzyl)]amino]-6-(4-methyl-3-pyridyl)-2,7-naphthyridin-3-yl]amino]pyrazol-1-yl]azetidin-1-yl]ethanone (120 mg, 0.12 mmol, 26% yield) as a yellow solid. LCMS (ESI) [M+H]$^+$=715.4.

Step 5: 1-[3-[4-[[8-amino-6-(4-methyl-3-pyridyl)-2,7-naphthyridin-3-yl]amino]pyrazol-1-yl]azetidin-1-yl]ethanone

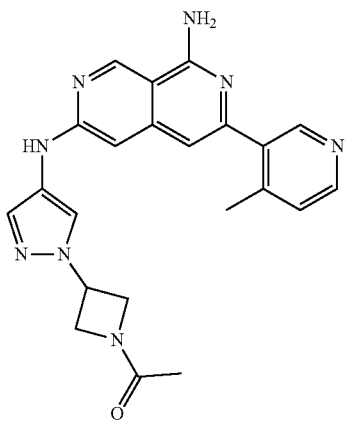 [SMILES: CC(=O)N1CC(n2cc(Nc3cc4cc(-c5cnccc5C)nc(N)c4cn3)cn2)C1]

A mixture of 1-[3-[4-[[8-[bis[(2,4-dimethoxybenzyl)]amino]-6-(4-methyl-3-pyridyl)-2,7-naphthyridin-3-yl]amino]pyrazol-1-yl]azetidin-1-yl]ethanone (120 mg, 0.12 mmol) in 2,2,2-trifluoroacetic acid (5 mL) was stirred at 50° C. for 1 h. The reaction mixture was concentrated and neutralized with 7 N NH$_3$ in MeOH to pH=7-8. The mixture was concentrated and purified by preparative HPLC reverse phase (C-18), eluting with Acetonitrile/Water+0.05% NH$_4$HCO$_3$, to give 1-[3-[4-[[8-amino-6-(4-methyl-3-pyridyl)-2,7-naphthyridin-3-yl]amino]pyrazol-1-yl]azetidin-1-yl]ethanone (35 mg, 0.084 mmol, 73% yield) as a yellow solid. LC-MS (ESI) R$_T$(min)=1.413, [M+H]$^+$=415.2, method=C. $^1$H NMR (400 MHz, DMSO-d$_6$) δ 9.23 (s, 1H), 8.98 (s, 1H), 8.53 (s, 1H), 8.42 (d, J=4.8 Hz, 1H), 8.09 (s, 1H), 7.63 (s, 1H), 7.29 (d, J=5.2 Hz, 1H), 7.10 (s, 2H), 6.77 (s, 1H), 6.68 (s, 1H), 5.27-5.21 (m, 1H), 4.55 (t, J=13.8 Hz, 1H), 4.41 (q, J=4.8 Hz, 1H), 4.29 (t, J=9.0 Hz, 1H), 4.14-4.09 (m, 1H), 2.40 (s, 3H), 1.83 (s, 3H).

Example 125

1-[8-amino-5-fluoro-6-(4-methyl-3-pyridyl)-2,7-naphthyridin-3-yl]-3-(1-methylpyrazol-4-yl)urea
(Compound 162)

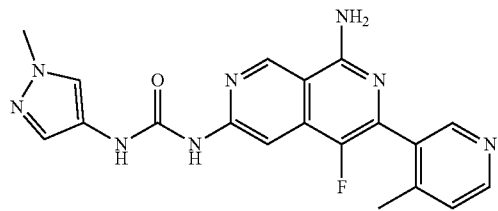 [SMILES: Cc1ccncc1-c1nc(N)c2cnc(NC(=O)Nc3cnn(C)c3)cc2c1F]

Step 1: phenyl N-[8-[bis[(2,4-dimethoxybenzyl)]amino]-6-chloro-2,7-naphthyridin-3-yl]carbamate

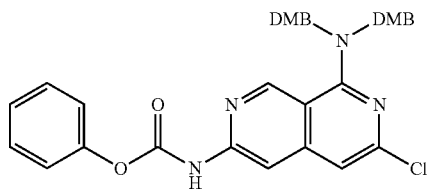

To a solution of 3-chloro-N1,N1-bis[(2,4-dimethoxybenzyl)]-2,7-naphthyridine-1,6-diamine (2.0 g, 4.04 mmol) and pyridine (10 mL, 123.64 mmol) in dichloromethane (40 mL) at 0° C. was added phenyl chloroformate (0.65 mL, 5.18 mmol). The mixture was stirred 0° C. ° C. for 2 h. The mixture was concentrated and purified by column chromatography eluting with EtOAc/hexane=1:2 to afford phenyl N-[8-[bis[(2,4-dimethoxybenzyl)]amino]-6-chloro-2,7-naphthyridin-3-yl]carbamate (1.8 g, 2.9 mmol, 72% yield) as a yellow solid. LCMS (ESI) [M+H]$^+$=615.2.

Step 2: 1-[8-[bis[(2,4-dimethoxybenzyl)]amino]-6-chloro-2,7-naphthyridin-3-yl]-3-(1-methylpyrazol-4-yl)urea

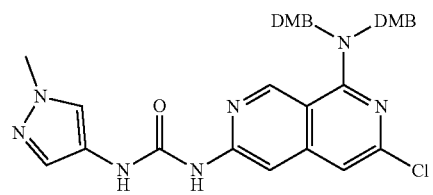

A mixture of phenyl N-[8-[bis[(2,4-dimethoxybenzyl)]amino]-6-chloro-2,7-naphthyridin-3-yl]carbamate (1.8 g, 2.93 mmol), 1-methyl-1h-pyrazol-4-amine (1.42 g, 14.62 mmol) and Et$_3$N (3.0 g, 29.7 mmol) in 1,4-dioxane (80 mL) was stirred at 90° C. for 2 h. The mixture was concentrated and purified by column chromatography eluting with EtOAc/hexane=4:1 to afford 1-[8-[bis[(2,4-dimethoxybenzyl)]amino]-6-chloro-2,7-naphthyridin-3-yl]-3-(1-methylpyrazol-4-yl)urea (1.6 g, 2.59 mmol, 89% yield) as a white solid. LCMS (ESI) [M+H]$^+$=618.1.

Step 3: 1-[8-[bis[(2,4-dimethoxybenzyl)]amino]-6-(4-methyl-3-pyridyl)-2,7-naphthyridin-3-yl]-3-(1-methyl pyrazol-4-yl)urea

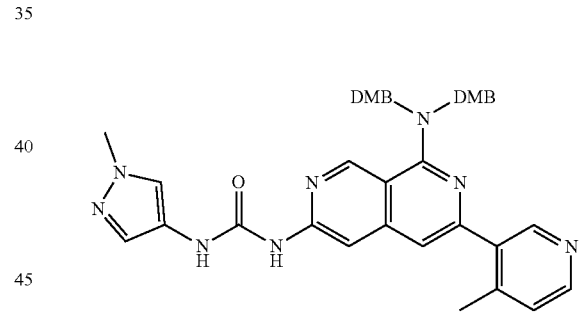

A mixture of 1-[8-[bis[(2,4-dimethoxybenzyl)]amino]-6-chloro-2,7-naphthyridin-3-yl]-3-(1-methylpyrazol-4-yl)urea (1.6 g, 2.59 mmol), 4-methyl-3-(4,4,5,5-tetramethyl-1,3,2-dioxaborolan-2-yl)pyridine (0.68 g, 3.1 mmol), x-Phos-Pd-G2 (407 mg, 0.52 mmol), x-Phos (493 mg, 1.04 mmol) and K$_2$CO$_3$ (0.74 g, 5.36 mmol) in 1,4-dioxane (80 mL) and water (10 mL) was stirred under Ar at 100° C. for 1.5 h. The mixture was concentrated and purified by column chromatography eluting with DCM/MeOH=20:1 to afford 1-[8-[bis[(2,4-dimethoxybenzyl)]amino]-6-(4-methyl-3-pyridyl)-2,7-naphthyridin-3-yl]-3-(1-methylpyrazol-4-yl)urea (1.7 g, 2.29 mmol, 89% yield) as a yellow solid. LCMS (ESI) [M+H]$^+$=675.3.

635

Step 4: 1-[8-amino-6-(4-methyl-3-pyridyl)-2,7-naphthyridin-3-yl]-3-(1-methylpyrazol-4-yl)urea

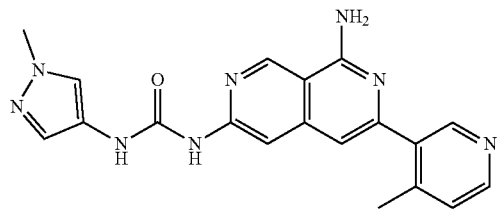 [SMILES: Cc1ccncc1-c1cc2cc(NC(=O)Nc3cnn(C)c3)ncc2c(N)n1]

A mixture of 1-[8-[bis[(2,4-dimethoxybenzyl)]amino]-6-(4-methyl-3-pyridyl)-2,7-naphthyridin-3-yl]-3-(1-methylpyrazol-4-yl)urea (1.7 g, 2.29 mmol) in 2,2,2-trifluoroacetic acid (30 mL) was stirred at 50° C. for 1 h. The mixture was concentrated and neutralized with 7N NH$_3$ in MeOH to pH=9-10. The mixture was concentrated, filtered, washed with DCM (200 ml) and H$_2$O (100 ml), and dried to give crude 1-[8-amino-6-(4-methyl-3-pyridyl)-2,7-naphthyridin-3-yl]-3-(1-methylpyrazol-4-yl)urea (1.7 g) as a yellow solid. LCMS (ESI) [M+H]$^+$=375.2.

Step 5: 1-[8-amino-5-fluoro-6-(4-methyl-3-pyridyl)-2,7-naphthyridin-3-yl]-3-(1-methylpyrazol-4-yl)urea

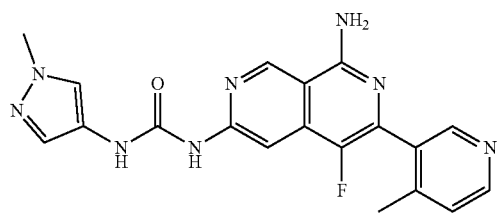 [SMILES: Cc1ccncc1-c1nc(N)c2cnc(NC(=O)Nc3cnn(C)c3)cc2c1Cl]

To a solution of 1-[8-amino-6-(4-methyl-3-pyridyl)-2,7-naphthyridin-3-yl]-3-(1-methylpyrazol-4-yl)urea (300 mg, 0.8 mmol) in N,N-dimethylformamide (20 mL) was added Selectfluor (149 mg, 0.4 mmol). The mixture was stirred at 50° C. for 3 h. The mixture was concentrated and purified by preparative HPLC (C-18), eluting with acetonitrile/Water+0.05% NH$_4$HCO$_3$, to give 1-[8-amino-5-fluoro-6-(4-methyl-3-pyridyl)-2,7-naphthyridin-3-yl]-3-(1-methylpyrazol-4-yl)urea (2.7 mg, 0.0063 mmol, 0.8% yield) as a yellow solid. LC-MS (ESI) R$_T$(min)=1.713, [M+H]+=393.2, method=G. $^1$H NMR (400 MHz, DMSO-d$_6$) δ 9.48 (s, 1H), 9.27 (s, 1H), 9.19 (s, 1H), 8.43 (s, 1H), 8.40 (d, J=5.2 Hz, 1H), 7.97 (s, 1H), 7.77 (s, 1H), 7.34 (s, 1H), 7.29 (d, J=4.8 Hz, 1H), 7.19 (s, 2H), 3.71 (s, 3H), 2.20 (s, 3H).

Example 126

1-[8-amino-5-chloro-6-(4-methyl-3-pyridyl)-2,7-naphthyridin-3-yl]-3-(1-methylpyrazol-4-yl)urea (Compound 163)

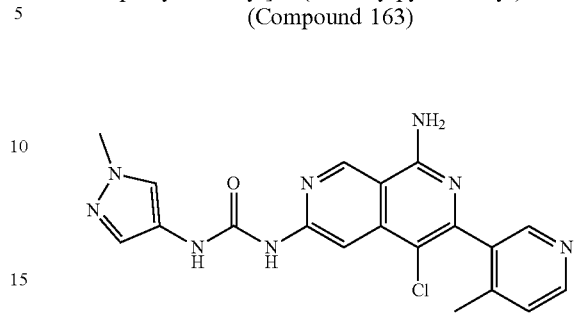

To a solution of 1-[8-amino-6-(4-methyl-3-pyridyl)-2,7-naphthyridin-3-yl]-3-(1-methylpyrazol-4-yl)urea (100 mg, 0.27 mmol) in N,N-dimethylformamide (10 mL) was added NCS (178 mg, 1.34 mmol). The mixture was stirred at 25° C. overnight. The mixture was purified by preparative HPLC (C-18), eluting with acetonitrile/Water+0.05% NH$_4$HCO$_3$, to give 1-[8-amino-5-chloro-6-(4-methyl-3-pyridyl)-2,7-naphthyridin-3-yl]-3-(1-methylpyrazol-4-yl)urea (44 mg, 0.11 mmol, 40% yield) as a yellow solid. LC-MS (ESI) R$_T$(min)=1.765, [M+H]+=409.2, method=G. $^1$H NMR (400 MHz, DMSO-d$_6$) δ 9.57 (s, 1H), 9.38 (s, 1H), 9.26 (s, 1H), 8.49 (d, J=4.8 Hz, 1H), 8.42 (s, 1H), 8.26 (s, 1H), 7.90 (s, 1H), 7.56 (s, 2H), 7.44 (s, 1H), 7.37 (d, J=5.2 Hz, 1H), 3.81 (s, 3H), 2.19 (s, 3H).

Example 127

(±)-trans-4-(1-amino-6-((trans)-2-cyanocyclopropanecarboxamido)-2,7-naphthyridin-3-yl)-3-methyl-N-(2,2,2-trifluoroethyl)benzamide) (Compound 164)

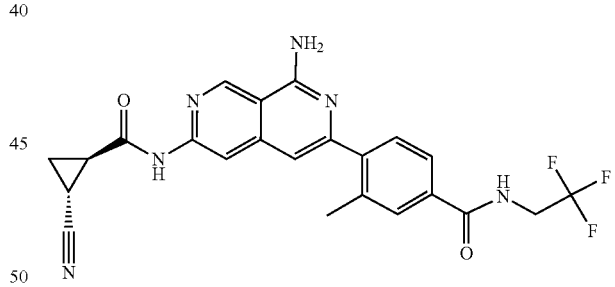

Step 1: 4-bromo-3-methyl-N-(2,2,2-trifluoroethyl)benzamide

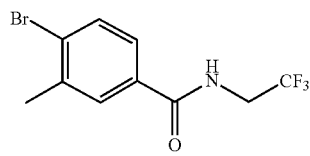 [SMILES: Cc1cc(C(=O)NCC(F)(F)F)ccc1Br]

To a solution of 4-bromo-3-methylbenzoic acid (500.0 mg, 2.33 mmol) and 2,2,2-trifluoroethylamine (210.0 mg, 2.12 mmol) in pyridine (5 mL) was added phosphorus oxychloride (1300 mg, 8.48 mmol) at 0° C. The resulting mixture was stirred for 1 h. The reaction was quenched with sat. NaHCO₃ (aq) and extracted with ethyl acetate (40 mL×2). The combined ethyl acetate extracts were concentrated in vacuo and purified by flash column chromatography (PE:EA=3:1-1:3) to give 4-bromo-3-methyl-N-(2,2,2-trifluoroethyl)benzamide (490 mg, 72.7% yield) as a yellow solid. LCMS (ESI): [M+H]⁺=296.0.

Step 2: 3-methyl-4-(4,4,5,5-tetramethyl-1,3,2-dioxaborolan-2-yl)-N-(2,2,2-trifluoroethyl)benzamide

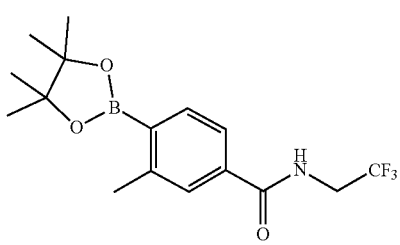 [SMILES: Cc1cc(C(=O)NCC(F)(F)F)ccc1B1OC(C)(C)C(C)(C)O1]

A mixture of 4-bromo-3-methyl-N-(2,2,2-trifluoroethyl) benzamide (200 mg, 0.680 mmol), KOAc (133 mg, 1.35 mmol), bis(pinacolato)diboron (206 mg, 0.810 mmol) and Pd(dppf)Cl₂ (49 mg, 0.07 mmol) in 1,4-dioxane (5 mL) was stirred for 3 hr at 80° C. Mixture was concentrated and purified by flash column chromatography (PE/EA=10%-50%) to give 3-methyl-4-(4,4,5,5-tetramethyl-1,3,2-dioxaborolan-2-yl)-N-(2,2,2-trifluoroethyl)benzamide (200 mg, 86% yield) as a white solid. LCMS (ESI): [M+H]⁺=344.1.

Step 3: 4-(1-amino-6-((trans)-2-cyanocyclopropanecarboxamido)-2,7-naphthyridin-3-yl)-3-methyl-N-(2,2,2-trifluoroethyl)benzamide)

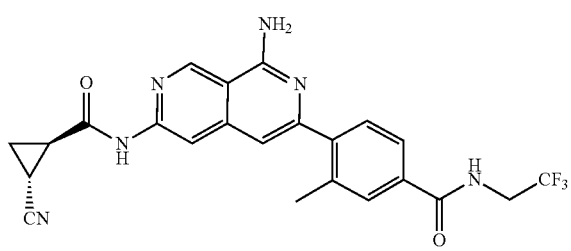 [SMILES: Cc1cc(C(=O)NCC(F)(F)F)ccc1-c1cc2cc(NC(=O)[C@@H]3C[C@H]3C#N)ncc2c(N)n1]

A mixture of (±)-trans-N-(8-amino-6-chloro-2,7-naphthyridin-3-yl)-2-cyano-cyclopropanecarboxamide (168 mg, 0.58 mmol), 3-methyl-4-(4,4,5,5-tetramethyl-1,3,2-dioxaborolan-2-yl)-N-(2,2,2-trifluoroethyl)benzamide (100 mg, 0.29 mmol), acetoxypotassium (86 mg, 0.87 mmol), Xphos-PdG₂ (23 mg, 0.03 mmol) and Xphos (28 mg, 0.06 mmol) in 1,4-dioxane (4 mL) and H₂O (0.4 mL) was stirred for 48 h at 100° C. The mixture was concentrated and purified by by reverse phase chromatography (acetonitrile 10-45% in 0.05% NH₄HCO₃ in water) to give 4-[1-amino-6-[[(trans)-2-cyanocyclopropanecarbonyl]amino]-2,7-naphthyridin-3-yl]-3-methyl-N-(2,2,2-trifluoroethyl)benzamide (6.2 mg, 4.5% yield) as a yellow solid. LCMS (ESI): R_T (min)=1.75, [M+H]⁺=469.1, method=C; ¹H NMR (400 MHz, CD₃OD): 9.30 (s, 1H), 8.29 (s, 2H), 7.31 (s, 1H), 7.79 (dd, J=1.2, 8.0 Hz, 1H), 7.53 (d, J=8.0 Hz, 1H), 4.16 (q, J=9.2 Hz, 2H), 2.66-2.64 (m, 1H), 2.16-2.11 (m, 1H), 1.62-1.55 (m, 2H).

Example 128

(±)-trans-N-(8-amino-6-(5-amino-4-methylpyridin-3-yl)-2,7-naphthyridin-3-yl)-2-cyanocyclopropanecarboxamide (Compound 165)

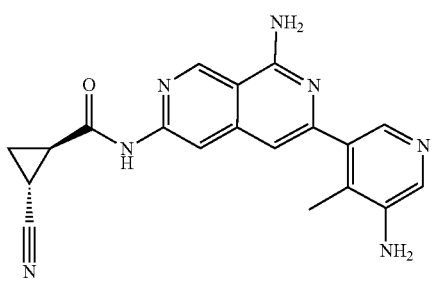 [SMILES: Cc1c(N)cncc1-c1cc2cc(NC(=O)[C@@H]3C[C@H]3C#N)ncc2c(N)n1]

Step 1: 5-bromo-4-methylpyridin-3-amine

A mixture of iron (3.1 g, 55.3 mmol) and 3-bromo-4-methyl-5-nitropyridine (2.0 g, 9.22 mmol) in ethanol (20 mL) and sat. NH₄Cl (4 mL) was stirred for 4 h at 70° C. The reaction was cooled to rt and diluted with ethyl acetate (200 mL). Na₂SO₄ was added and the reaction was stirred for 0.5 h before being filtered. The filtrate was concentrated to give 5-bromo-4-methyl-pyridin-3-amine (1.4 g, 74.5% yield) as a yellow solid. LCMS (ESI): [M+H]⁺=187.1.

Step 2: (tert-butyl 5-bromo-4-methylpyridin-3-ylcarbamate

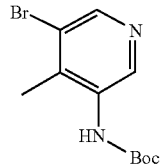

To a solution of 5-bromo-4-methyl-pyridin-3-amine (600 mg, 3.21 mmol) in tetrahydrofuran (10 mL) was added NaHMDS (6.5 mL, 6.5 mmol) and stirred for 0.5 h at 0° C. Di-tert-butyldicarbonate (770 mg, 3.53 mmol) was added. The mixture was stirred for 2 hr at rt. The reaction was then diluted with water (0.5 mL) and concentrated. The residue was purified by flash column chromatography (PE/EA=20%) to give tert-butyl N-(5-bromo-4-methyl-3-pyridyl)carbamate (710 mg, 66.7% yield) as a white solid. LCMS (ESI): [M+H]⁺=287.0.

Step 3: tert-butyl 4-methyl-5-(4,4,5,5-tetramethyl-1,3,2-dioxaborolan-2-yl)pyridin-3-ylcarbamate

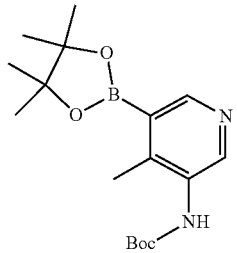 [SMILES: Cc1c(NC(=O)OC(C)(C)C)cncc1B1OC(C)(C)C(C)(C)O1]

A mixture of tert-butyl N-(5-bromo-4-methyl-3-pyridyl)carbamate (710 mg, 2.47 mmol), acetoxypotassium (486 mg, 4.95 mmol) and bis(pinacolato)diboron (756 mg, 2.98 mmol) and Pd(dppf)Cl$_2$ (91 mg, 0.12 mmol) in 1,4-dioxane (10 mL) was stirred for 18 h at 90° C. The mixture was concentrated and purified by flash column chromatography (PE/EA=30%-70%) to give tert-butyl N-[4-methyl-5-(4,4,5,5-tetramethyl-1,3,2-dioxaborolan-2-yl)-3-pyridyl]carbamate (510 mg, 56.9% yield) as a yellow solid. LCMS (ESI): [M+H]$^+$=335.2.

Step 4: (±)-tert-butyl 5-(1-amino-6-((trans)-2-cyanocyclopropanecarboxamido)-2,7-naphthyridin-3-yl)-4-methylpyridin-3-ylcarbamate

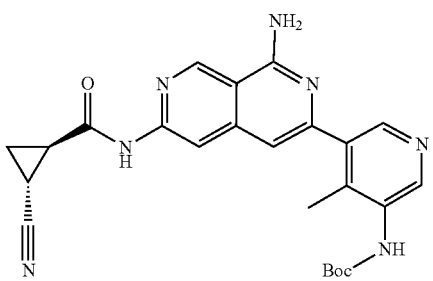 [SMILES: Cc1c(NC(=O)OC(C)(C)C)cncc1-c1cc2cc(NC(=O)[C@@H]3C[C@H]3C#N)ncc2c(N)n1]

A mixture of tert-butyl N-[4-methyl-5-(4,4,5,5-tetramethyl-1,3,2-dioxaborolan-2-yl)-3-pyridyl]carbamate (140 mg, 0.42 mmol), (±)-trans-N-(8-amino-6-chloro-2,7-naphthyridin-3-yl)-2-cyano-cyclopropane carboxamide (100 mg, 0.35 mmol), Pd(dppf)Cl$_2$ (13 mg, 0.02 mmol) and Na$_2$CO$_3$ (74.0 mg, 0.7 mmol) in 1,4-dioxane (4 mL) and H$_2$O (0.4 mL) was stirred for 18 h at 100° C. The mixture was cooled to rt and diluted with water (10 mL). The mixture was then extracted with ethyl acetate (30 mL×2). The combined ethyl acetate extracts were dried over Na$_2$SO$_4$ and concentrated in vacuo to give (±)-tert-butyl N-[5-[1-amino-6-[[(trans)-2-cyanocyclopropanecarbonyl]amino]-2,7-naphthyridin-3-yl]-4-methyl-3-pyridyl]carbamate (160 mg, 41.6% yield) as a brown oil. LCMS (ESI): [M+H]$^+$=460.2.

Step 5: (±)-trans-N-(8-amino-6-(5-amino-4-methylpyridin-3-yl)-2,7-naphthyridin-3-yl)-2-cyanocyclopropanecarboxamide

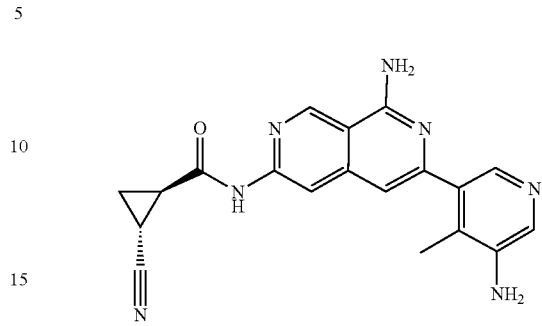

A solution of (±)-tert-butyl N-[5-[1-amino-6-[[(trans)-2-cyanocyclopropanecarbonyl]amino]-2,7-naphthyridin-3-yl]-4-methyl-3-pyridyl]carbamate (160 mg, 0.14 mmol) in dichloromethane (1 mL) and 2,2,2-trifluoroacetic acid (1 mL) was stirred for 4 h at 25° C. The mixture was concentrated and the purified by prep-HPLC (acetonitrile 5-40% in 0.05% NH$_4$HCO$_3$ in water) to give (±)-trans-N-[8-amino-6-(5-amino-4-methyl-3-pyridyl)-2,7-naphthyridin-3-yl]-2-cyano-cyclopropanecarboxamide (34.5 mg, 66.4% yield) as a yellow solid. LCMS (ESI): R$_T$ (min)=1.43, [M+H]$^+$=360.1, method=C; $^1$H NMR (400 MHz, CD$_3$OD): 9.30 (s, 1H), 8.23 (s, 1H), 8.00 (s, 1H), 7.85 (s, 1H), 6.95 (s, 1H), 2.66-2.64 (m, 1H), 2.17 (s, 3H), 2.15-2.11 (m, 1H), 1.62-1.55 (m, 2H).

Example 129

(±)-trans-2-(1-acetylpiperidin-4-yl)-N-(8-amino-6-(4-methylpyridin-3-yl)-2,7-naphthyridin-3-yl)cyclopropanecarboxamide (Compound 166)

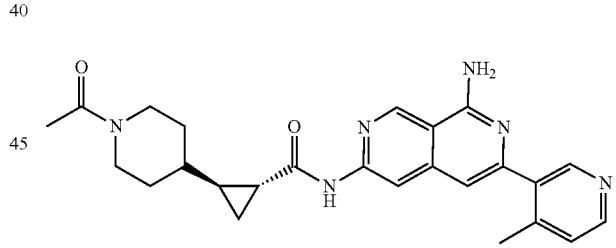

Step 1: (E)-tert-butyl 4-(3-tert-butoxy-3-oxoprop-1-enyl)piperidine-1-carboxylate

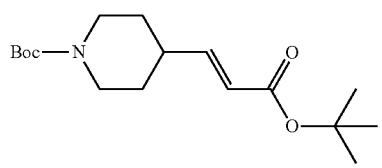 [SMILES: CC(C)(C)OC(=O)/C=C/C1CCN(C(=O)OC(C)(C)C)CC1]

To a solution of tert-butyl diethylphosphonoacetate (2.6 g, 10.32 mmol) in tetrahydrofuran (20 mL) was added methylmagnesiumbromide (3.44 mL, 10.32 mmol) at 0° C. The mixture was stirred for 0.5 h. To the reaction solution was then added tert-butyl 4-formyl-1-piperidinecarboxylate (2.0 g, 9.38 mmol). The mixture was stirred for 5 h at 25° C. The mixture was diluted with sat. NH₄Cl, and concentrated. The residue was purified by flash column chromatography (PE/EA=1%-10%) to give tert-butyl 4-[(E)-3-tert-butoxy-3-oxo-prop-1-enyl]piperidine-1-carboxylate (2.4 g, 82.2% yield) as a yellow solid. LCMS (ESI): [M+H]⁺=334.2.

Step 2: (±)-tert-butyl 4-((trans)-2-(tert-butoxycarbonyl)cyclopropyl)piperidine-1-carboxylate

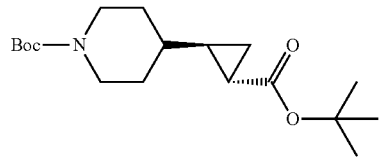 [SMILES: CC(C)(C)OC(=O)[C@H]1C[C@@H]1C1CCN(C(=O)OC(C)(C)C)CC1]

To solution of trimethylsulfoxonium iodide (1979 mg, 8.99 mmol) in dimethyl sulfoxide (10 mL) was added tert-butoxypotassium (1009 mg, 8.99 mmol). The mixture was stirred for 0.5 h. tert-Butyl 4-[(E)-3-tert-butoxy-3-oxo-prop-1-enyl]piperidine-1-carboxylate (1.4 g, 4.5 mmol) was added and the mixture was stirred for 4 h at 25° C. The mixture was diluted with water (50 mL) and extracted with PE (50 mL×3). The combined PE was dried over Na₂SO₄ and concentrated in vacuo to give tert-butyl 4-[(trans)-2-tert-butoxycarbonylcyclopropyl]piperidine-1-carboxylate (830 mg, 56.7% yield) as a colorless oil.

Step 3: (±)-trans-2-(piperidin-4-yl)cyclopropanecarboxylic acid

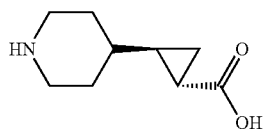 [SMILES: O=C(O)[C@H]1C[C@@H]1C1CCNCC1]

A mixture of (±)-tert-butyl 4-[(trans)-2-tert-butoxycarbonylcyclopropyl]piperidine-1-carboxylate (830 mg, 1.99 mmol) in 5 mL of 4M HCl in dioxane was stirred for 18 h at 25° C. The reaction was concentrated to give (±)-trans-2-(4-piperidyl)cyclopropanecarboxylic acid (640 mg, 90% yield) as a white solid. LCMS (ESI): [M+H]⁺=170.1

Step 4: (±)-trans-2-(1-acetylpiperidin-4-yl)cyclopropanecarboxylic acid

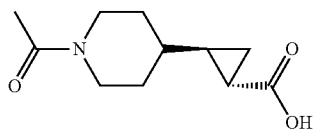

A mixture of (±)-trans-2-(4-piperidyl)cyclopropanecarboxylic acid (640 mg, 3.78 mmol), Ac₂O (1158.0 mg, 11.35 mmol) and TEA (574 mg, 5.67 mmol) in methyl alcohol (5 mL) was stirred for 18 h at 25° C. The mixture was then concentrated and purified by flash column chromatography (MeOH 5%-40%/0.02% HCOOH in water) to give (±)-trans-2-(1-acetyl-4-piperidyl)cyclopropanecarboxylic acid (450 mg, 56.3% yield) as whit solid. LCMS (ESI): [M+H]⁺=212.2

Step 5: (±)-trans-2-(1-acetylpiperidin-4-yl)-N-(6,8-dichloro-2,7-naphthyridin-3-yl)cyclopropanecarboxamide

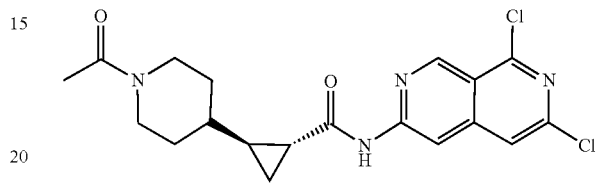

To a mixture of (±)-trans-2-(1-acetyl-4-piperidyl)cyclopropanecarboxylic acid (430 mg, 2.04 mmol), 6,8-dichloro-2,7-naphthyridin-3-amine (436 mg, 2.04 mmol), pyridine (644 mg, 8.14 mmol) in dichloromethane (4 mL) was added POCl₃ (1248 mg, 8.14 mmol). The reaction was stirred for 1 h at 25° C. The mixture was diluted with sat. NaHCO₃ and extracted with ethyl acetate (30 mL×2). The combined ethyl acetate extracts were dried over Na₂SO₄ and concentrated in vacuo to give (±)-trans-2-(1-acetyl-4-piperidyl)-N-(6,8-dichloro-2,7-naphthyridin-3-yl)cyclopropanecarboxamide (720 mg, 54.3% yield) as a crude yellow solid. LCMS (ESI): [M+H]⁺=407.1.

Step 6: (±)-trans-2-(1-acetylpiperidin-4-yl)-N-(8-amino-6-chloro-2,7-naphthyridin-3-yl)cyclopropanecarboxamide

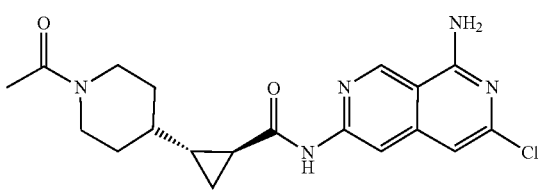 [SMILES: CC(=O)N1CCC([C@H]2C[C@@H]2C(=O)Nc2cc3cc(Cl)nc(N)c3cn2)CC1]

A mixture of (±)-trans-2-(1-acetyl-4-piperidyl)-N-(6,8-dichloro-2,7-naphthyridin-3-yl)cyclopropane carboxamide (700 mg, 1.72 mmol) in 1,4-dioxane (5 mL) and ammonium hydroxide (25%, 10 mL) was stirred at 90° C. for 2 h. The mixture was diluted with 2 mL MeOH and ethyl acetate (20 mL). The suspension was stirred for 0.5 h at rt. The suspension was then filtered. The wet cake was washed with ethyl acetate and dried in vacuo to give at (±)-trans-2-(1-acetyl-4-piperidyl)-N-(8-amino-6-chloro-2,7-naphthyridin-3-yl)cyclopropanecarboxamide (580 mg, 82.7% yield) as a yellow solid. LCMS (ESI): [M+H]⁺=288.2.

Step 7: (±)-trans-2-(1-acetylpiperidin-4-yl)-N-(8-amino-6-(4-methylpyridin-3-yl)-2,7-naphthyridin-3-yl)cyclopropanecarboxamide

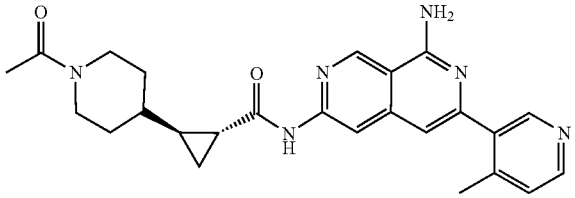 [SMILES: CC(=O)N1CCC([C@@H]2C[C@H]2C(=O)Nc2cc3cc(-c4cnccc4C)nc(N)c3cn2)CC1]

A mixture of (±)-trans-2-(1-acetyl-4-piperidyl)-N-(8-amino-6-chloro-2,7-naphthyridin-3-yl)cyclopropanecarboxamide (380 mg, 0.98 mmol), 4-methyl-3-(4,4,5,5-tetramethyl-1,3,2-dioxaborolan-2-yl)pyridine (322 mg, 1.47 mmol), Pd(dppf)Cl$_2$ (36 mg, 0.05 mmol) and Na$_2$CO$_3$ (312 mg, 2.94 mmol) in 1,4-dioxane (15 mL) and water (2 mL) was stirred for 5 h at 100° C. The mixture was then cooled to rt and filtered. The filtrate was concentrated and purified by prep-HPLC (acetonitrile 10-60%/0.1% NH$_4$HCO$_3$ in water) to give (±)-trans-2-(1-acetyl-4-piperidyl)-N-[8-amino-6-(4-methyl-3-pyridyl)-2,7-naphthyridin-3-yl]cyclopropanecarboxamide (169 mg, 38.8% yield) as a white solid. LCMS (ESI): R$_T$ (min)=1.49, [M+H]$^+$=445.3, method=C; $^1$H NMR (400 MHz, CD$_3$OD): 9.29 (s, 1H), 8.54 (s, 1H), 8.44 (d, J=4.8 Hz, 1H), 8.29 (s, 1H), 7.40 (d, J=4.8 Hz, 1H), 6.97 (s, 1H), 6.26 (s, 1H), 4.54-4.52 (m, 1H), 3.96-3.94 (m, 1H), 3.09-3.07 (m, 1H), 2.63-2.61 (m, 1H), 2.45 (s, 3H), 2.12 (s, 3H), 1.90-1.86 (m, 3H), 1.31-1.14 (m, 5H), 1.01-0.99 (s, 1H).

Example 130

(±)-cis-N-(8-amino-6-(4-methyl-6-(2-oxo-1,2-dihydropyridin-3-yl)pyridin-3-yl)-2,7-naphthyridin-3-yl)-2-fluorocyclopropanecarboxamide (Compound 167)

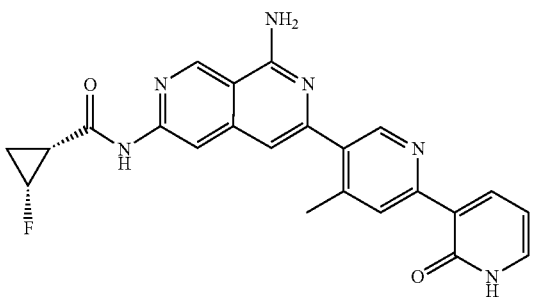 [SMILES: Cc1cc(-c2ccc[nH]c2=O)ncc1-c1cc2cc(NC(=O)[C@H]3C[C@H]3F)ncc2c(N)n1]

Step 1: (3-(5-bromo-4-methylpyridin-2-yl)pyridin-2(1H)-one

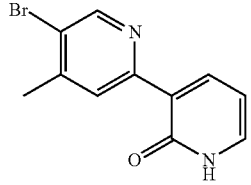

A mixture of 2,5-dibromo-4-methylpyridine (500 mg, 1.99 mmol), (2-oxo-1H-pyridin-3-yl)boronic acid (415 mg, 2.99 mmol), Na$_2$CO$_3$ (422 mg, 3.99 mmol) and Pd(dppf)Cl$_2$ (73 mg, 0.10 mmol) in 1,4-dioxane (10 mL) and water (0.4 mL) was stirred at 90° C. for 18 h. The mixture was cooled to rt and diluted with water. The product was extracted with ethyl acetate (50 mL×3). The combined ethyl acetate was dried over Na$_2$SO$_4$ and concentrated in vacuo. The residue was purified by flash column chromatography (PE/EA=50%-80%) to give 3-(5-bromo-4-methyl-2-pyridyl)-1H-pyridin-2-one (320 mg, 60.6% yield) as a white solid. LCMS (ESI): [M+H]$^+$=267.0.

Step 2: 3-(4-methyl-5-(4,4,5,5-tetramethyl-1,3,2-dioxaborolan-2-yl)pyridin-2-yl)pyridin-2(1H)-one

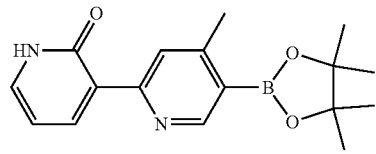 [SMILES: Cc1cc(-c2ccc[nH]c2=O)ncc1B1OC(C)(C)C(C)(C)O1]

A mixture of 3-(5-bromo-4-methyl-2-pyridyl)-1H-pyridin-2-one (350 mg, 1.32 mmol), bis(pinacolato)diboron (402 mg, 1.58 mmol), acetoxypotassium (259 mg, 2.64 mmol) and Pd(dppf)Cl$_2$ (48 mg, 0.070 mmol) in 1,4-dioxane (10 mL) was stirred for 18 h at 110° C. The reaction was cooled to rt and diluted with water. The mixture was extracted with ethyl acetate (50 mL×3). The combined ethyl acetate layers were dried over Na$_2$SO$_4$ and concentrated in vacuo. The residue was washed with PE (20 mL) and filtered. The collected solid cake was dried in vacuo to give 3-[4-methyl-5-(4,4,5,5-tetramethyl-1,3,2-dioxaborolan-2-yl)-2-pyridyl]-1H-pyridin-2-one (620 mg, 48.3% yield) as a black solid. This crude material was used in the next step without purification. LCMS (ESI): [M+H]$^+$=313.2

645

Step 3: (±)-cis-N-(8-amino-6-(4-methyl-6-(2-oxo-1,2-dihydropyridin-3-yl)pyridin-3-yl)-2,7-naphthyridin-3-yl)-2-fluorocyclopropanecarboxamide

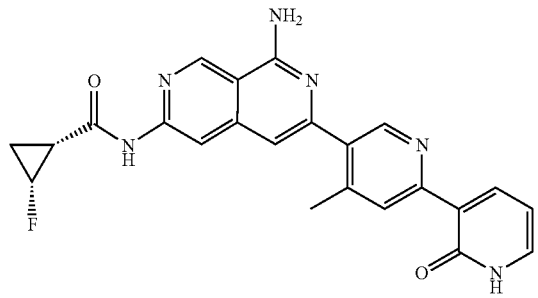 [SMILES: Cc1cc(-c2ccc[nH]c2=O)ncc1-c1cc2cc(NC(=O)[C@H]3C[C@H]3F)ncc2c(N)n1]

A mixture of 3-[4-methyl-5-(4,4,5,5-tetramethyl-1,3,2-dioxaborolan-2-yl)-2-pyridyl]-1H-pyridin-2-one (620 mg, 0.87 mmol), (±)-cis-N-(8-amino-6-chloro-2,7-naphthyridin-3-yl)-2-fluoro-cyclopropane carboxamide (180 mg, 0.64 mmol), Na$_2$CO$_3$ (170 mg, 1.6 mmol) and Pd(dppf)Cl$_2$ (23 mg, 0.030 mmol) in 1,4-dioxane (2 mL) and H$_2$O (0.2 mL) was stirred for 4 h at 100° C. The reaction was cooled to rt and filtered. The filtrate was concentrated purified by prep-HPLC (acetonitrile 10-70%/0.1% NH$_4$HCO$_3$ in water) to give (±)-cis-N-[8-amino-6-[4-methyl-6-(2-oxo-1H-pyridin-3-yl)-3-pyridyl]-2,7-naphthyridin-3-yl]-2-fluoro-cyclopropanecarboxamide (42.5 mg, 14.7% yield) as a yellow solid. LCMS (ESI): R$_T$ (min)=1.43, [M+H]$^+$=431.2, method=C; $^1$H NMR (400 MHz, DMSO-d$_6$): 11.99 (s, 1H), 10.02 (s, 1H), 9.39 (s, 1H), 8.65 (s, 1H), 8.56 (s, 1H), 8.51 (d, J=5.2 Hz, 1H), 8.26 (s, 1H), 7.54 (d, J=5.2 Hz, 1H), 7.34 (s, 1H), 7.03 (s, 2H), 6.43-6.40 (m, 0.5H), 5.05-4.87 (m, 0.5H), 2.40 (s, 3H), 2.28-2.45 (m, 1H), 1.71-1.64 (m, 1H), 1.23-1.18 (m, 1H).

Example 131

2-[4-[[8-amino-6-(4-ethyl-3-pyridyl)-2,7-naphthyridin-3-yl]amino]pyrazol-1-yl]ethanol (Compound 168)

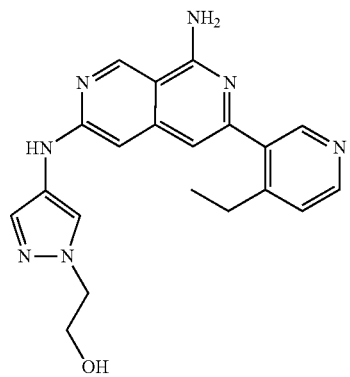 [SMILES: CCc1ccncc1-c1cc2cc(Nc3cnn(CCO)c3)ncc2c(N)n1]

646

Step 1: N1,N1-bis[(2,4-dimethoxyphenyl)methyl]-3-(4-ethyl-3-pyridyl)-N6-[1-(2-tetrahydropyran-2-yloxyethyl)pyrazol-4-yl]-2,7-naphthyridine-1,6-diamine

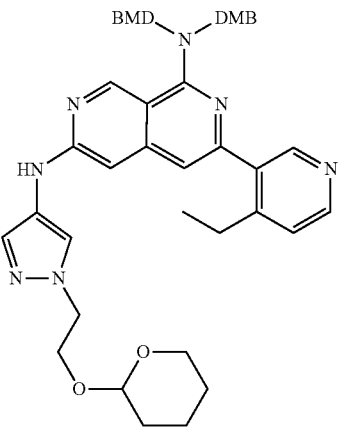

A mixture of N1,N1-bis[(2,4-dimethoxyphenyl)methyl]-3-(4-ethyl-3-pyridyl)-2,7-naphthyridine-1,6-diamine (600 mg, 1.06 mmol), 4-bromo-1-(2-tetrahydropyran-2-yloxyethyl)pyrazole (1200 mg, 4.36 mmol), t-BuBrettPhos Pd G3 (150 mg, 0.18 mmol), t-BuBrettPhos (120 mg, 0.25 mmol), t-BuONa (400 mg, 4.17 mmol) in toluene (20 mL) was stirred under Ar in sealed tube at 100° C. for 24 h. The reaction mixture was cooled to room temperature and diluted with ethyl acetate (100 mL). The mixture was washed with sat. NH$_4$Cl (20 mL). The organic layer was separated, dried over Na$_2$SO$_4$, filtered and evaporated. The residue was purified with silica chromatography (PE:EA=1:3) to give N1,N1-bis[(2,4-dimethoxyphenyl)methyl]-3-(4-ethyl-3-pyridyl)-N6-[1-(2-tetrahydropyran-2-yloxyethyl)pyrazol-4-yl]-2,7-naphthyridine-1,6-diamine (470 mg, 58.3% yield) as a brown solid. LCMS (ESI) [M+H]$^+$=760.3.

Step 2: 2-[4-[[8-amino-6-(4-ethyl-3-pyridyl)-2,7-naphthyridin-3-yl]amino]pyrazol-1-yl]ethanol

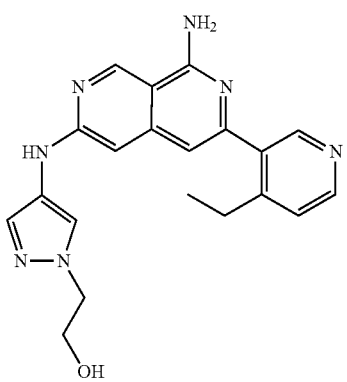 [SMILES: CCc1ccncc1-c1cc2cc(Nc3cnn(CCO)c3)ncc2c(N)n1]

A mixture of N1,N1-bis[(2,4-dimethoxyphenyl)methyl]-3-(4-ethyl-3-pyridyl)-N6-[1-(2-tetrahydropyran-2-yloxyethyl)pyrazol-4-yl]-2,7-naphthyridine-1,6-diamine (470 mg, 0.62 mmol) in 2,2,2-trifluoroacetic acid (5 mL) was stirred at 80° C. for 1 h. The reaction mixture was concentrated. The residue was re-dissolved in MeOH (3 mL) and basified with 7N NH₃/MeOH to pH 9-10. The material was purified with flash chromatography (C18, NH₄HCO₃/MeOH/H₂O) to give 2-[4-[[8-amino-6-(4-ethyl-3-pyridyl)-2,7-naphthyridin-3-yl]amino]pyrazol-1-yl]ethanol (125 mg, 53.8% yield) as a yellow solid. LCMS (ESI): $R_T$ (min)=1.45, $[M+H]^+$=376.1, method=C; ¹H NMR (400 MHz, DMSO-d₆): δ 9.22 (s, 1H), 8.85 (brs, 1H), 8.47-8.46 (m, 2H), 7.91 (s, 1H), 7.49 (s, 1H), 7.32 (d, J=5.2 Hz, 1H), 7.06 (brs, 2H), 6.71 (s, 1H), 6.64 (s, 1H), 4.92-4.89 (m, 1H), 4.14-4.09 (m, 2H), 3.76-3.72 (m, 2H), 2.79 (q, J=7.6 Hz, 2H), 1.10 (t, J=7.6 Hz, 3H).

Example 132

2-[4-[[8-amino-6-(4-methyl-3-pyridyl)-2,7-naphthyridin-3-yl]amino]pyrazol-1-yl]ethanol (Compound 169)

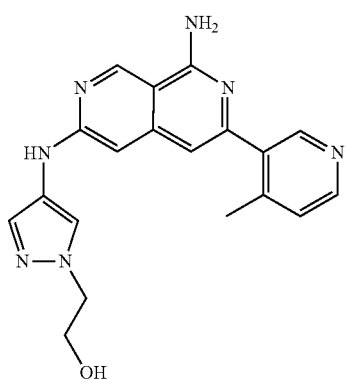 [SMILES: Cc1ccncc1-c1cc2cc(Nc3cnn(CCO)c3)ncc2c(N)n1]

Step 1:
4-bromo-1-(2-tetrahydropyran-2-yloxyethyl)pyrazole

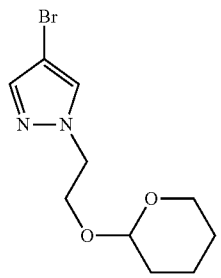 [SMILES: Brc1cnn(CCOC2CCCCO2)c1]

NaH (60% in oil, 580 mg, 14.5 mmol) was added portionwise to a solution of 4-bromo-1H-pyrazole (2 g, 13.61 mmol) in N,N-Dimethylformamide (25 mL) at 0° C. The mixture was stirred at 0° C. for 2 h. 2-(2-bromoethoxy)tetrahydro-2h-pyran (3 g, 14.35 mmol) was added to the reaction mixture. The resulting mixture was stirred at 15° C. for 2 h. The reaction mixture was diluted with water (20 mL) and NH₄Cl (50 mL). The product was extracted with ethyl acetate (100 mL×3). The ethyl acetate layers were combined, washed with brine (100 mL×2), dried over Na₂SO₄, filtered and evaporated. The residue was purified with silica chromatography (PE:EA=4:1) to give 4-bromo-1-(2-tetrahydropyran-2-yloxyethyl)pyrazole (3 g, 80.1% yield) as a colorless oil. LCMS (ESI) $[M+23]^+$=297.0.

Step 2: N1,N1-bis[(2,4-dimethoxyphenyl)methyl]-3-(4-methyl-3-pyridyl)-N6-[1-(2-tetrahydropyran-2-yloxyethyl)pyrazol-4-yl]-2,7-naphthyridine-1,6-diamine

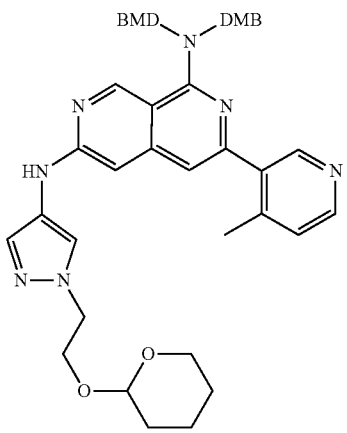

A mixture of N1,N1-bis[(2,4-dimethoxyphenyl)methyl]-3-(4-methyl-3-pyridyl)-2,7-naphthyridine-1,6-diamine (200 mg, 0.36 mmol), 4-bromo-1-(2-tetrahydropyran-2-yloxyethyl)pyrazole (400 mg, 1.45 mmol), t-BuBrettPhos Pd G3 (40 mg, 0.05 mmol), t-BuBrettPhos (40 mg, 0.08 mmol), t-BuONa (120 mg, 1.25 mmol) in toluene (10 mL) was stirred at 100° C. under Ar in sealed tube for 16 h. The reaction mixture was cooled to room temperature and diluted with ethyl acetate (30 mL). The mixture was washed with sat. NH₄Cl (10 mL). The organic layer was separated, dried over Na₂SO₄, filtered and evaporated. The residue was purified by silica chromatography (PE:EA=1:3 to EA) to give N1,N1-bis[(2,4-dimethoxyphenyl)methyl]-3-(4-methyl-3-pyridyl)-N6-[1-(2-tetrahydropyran-2-yloxyethyl)pyrazol-4-yl]-2,7-naphthyridine-1,6-diamine (90 mg, 33.3% yield) as a brown solid. LCMS (ESI) $[M+H]^+$=746.4.

Step 3: 2-[4-[[8-amino-6-(4-methyl-3-pyridyl)-2,7-naphthyridin-3-yl]amino]pyrazol-1-yl]ethanol

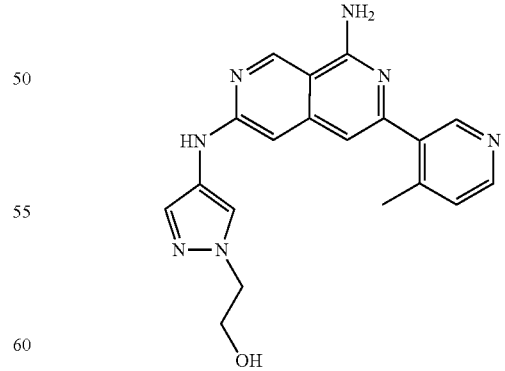

A mixture of N1,N1-bis[(2,4-dimethoxyphenyl)methyl]-3-(4-methyl-3-pyridyl)-N6-[1-(2-tetrahydropyran-2-yloxyethyl)pyrazol-4-yl]-2,7-naphthyridine-1,6-diamine (90 mg, 0.12 mmol) in 2,2,2-trifluoroacetic acid (5 mL) was stirred at 80° C. for 1 h. The reaction mixture was evaporated. The residue was diluted with CH$_3$CN (1 mL) and DMF (1 mL) before being purified by prep-HPLC to give 2-[4-[[8-amino-6-(4-methyl-3-pyridyl)-2,7-naphthyridin-3-yl]amino]pyrazol-1-yl]ethanol (23.4 mg, 53.7% yield) as a light yellow solid. LCMS (ESI): R$_T$(min)=1.39, [M+H]$^+$=362.1, method=C; $^1$H NMR (400 MHz, CD$_3$OD): δ 9.14 (s, 1H), 8.50 (s, 1H), 8.42 (d, J=5.2 Hz, 1H), 7.93 (s, 1H), 7.60 (s, 1H), 7.39 (d, J=5.2 Hz, 1H), 6.75 (s, 1H), 6.71 (s, 1H), 4.24 (t, J=5.2 Hz, 2H), 3.93 (t, J=5.2 Hz, 2H), 2.44 (s, 3H).

Example 133

4-[[8-amino-6-(4-methyl-3-pyridyl)-2,7-naphthyridin-3-yl]amino]-1-methyl-pyridin-2-one (Compound 170)

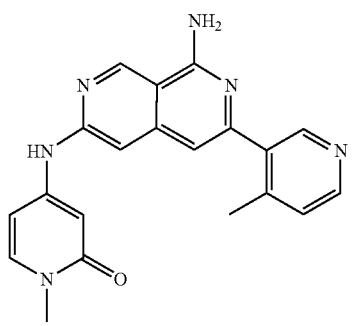 [SMILES: Cc1ccncc1-c1cc2cc(Nc3ccn(C)c(=O)c3)ncc2c(N)n1]

Step 1: 4-[[8-[bis[(2,4-dimethoxyphenyl)methyl]amino]-6-(4-methyl-3-pyridyl)-2,7-naphthyridin-3-yl]amino]-1-methyl-pyridin-2-one

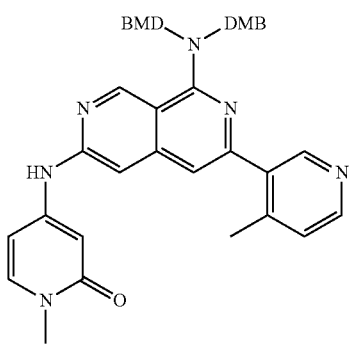

A mixture of N1,N1-bis[(2,4-dimethoxyphenyl)methyl]-3-(4-methyl-3-pyridyl)-2,7-naphthyridine-1,6-diamine (300 mg, 0.54 mmol), 4-bromo-1-methyl-pyridin-2-one (300 mg, 1.6 mmol), Pd$_2$dba$_3$ (100 mg, 0.11 mmol), t-BuBrettPhos (140 mg, 0.29 mmol), and Cs$_2$CO$_3$ (300 mg, 0.92 mmol) in 1,4-dioxane (15 mL) was stirred at 100° C. under Ar in sealed tube for 16 h. The reaction mixture was cooled to room temperature and diluted with ethyl acetate (50 mL). The mixture was washed with brine (20 mL), dried over Na$_2$SO$_4$, filtered and evaporated. The residue was purified with silica gel chromatography (EA to EA:MeOH=10:1) to give 4-[[8-[bis[(2,4-dimethoxyphenyl)methyl]amino]-6-(4-methyl-3-pyridyl)-2,7-naphthyridin-3-yl]amino]-1-methyl-pyridin-2-one (140 mg, 39.1% yield) as a brown solid. LCMS (ESI) [M+H]$^+$=659.3.

Step 2: 4-[[8-amino-6-(4-methyl-3-pyridyl)-2,7-naphthyridin-3-yl]amino]-1-methyl-pyridin-2-one

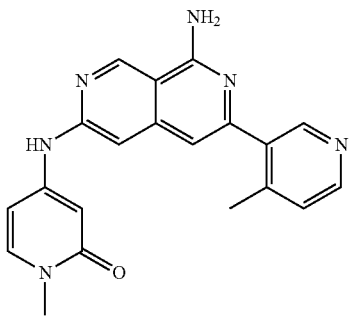 [SMILES: Cc1ccncc1-c1cc2cc(Nc3ccn(C)c(=O)c3)ncc2c(N)n1]

A mixture of 4-[[8-[bis[(2,4-dimethoxyphenyl)methyl]amino]-6-(4-methyl-3-pyridyl)-2,7-naphthyridin-3-yl]amino]-1-methyl-pyridin-2-one (140 mg, 0.21 mmol) in 2,2,2-trifluoroacetic acid (5 mL) was stirred at 80° C. for h. The reaction mixture was concentrated and purified by flash chromatography (C18, NH$_4$HCO$_3$/MeOH/H$_2$O) to yield 4-[[8-amino-6-(4-methyl-3-pyridyl)-2,7-naphthyridin-3-yl]amino]-1-methyl-pyridin-2-one (48 mg, 63% yield) as a white solid. LCMS (ESI): R$_T$ (min)=1.36, [M+H]$^+$=359.2, method=G; $^1$H NMR (400 MHz, DMSO-d$_6$+D$_2$O): δ 9.34 (s, 1H), 8.54 (s, 1H), 8.42 (d, J=4.8 Hz, 1H), 7.52 (d, J=7.6 Hz, 1H), 7.32 (d, J=4.8 Hz, 1H), 7.05 (s, 1H), 6.91 (s, 1H), 6.89 (d, J=2.0 Hz, 1H), 6.38 (dd, J=2.0, 7.6 Hz, 1H), 3.34 (s, 3H), 2.40 (s, 3H).

Example 134

1-[8-amino-6-(4-methyl-3-pyridyl)-2,7-naphthyridin-3-yl]-3-(2-cyanophenyl)urea (Compound 171)

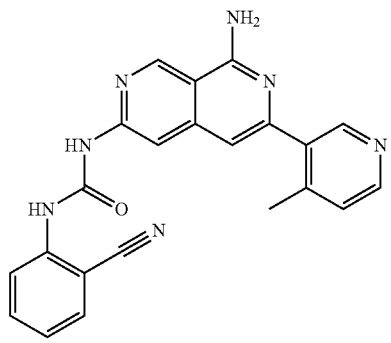 [SMILES: Cc1ccncc1-c1cc2cc(NC(=O)Nc3ccccc3C#N)ncc2c(N)n1]

Step 1: 1-[8-[bis[(2,4-dimethoxyphenyl)methyl]amino]-6-chloro-2,7-naphthyridin-3-yl]-3-(2-cyanophenyl)urea

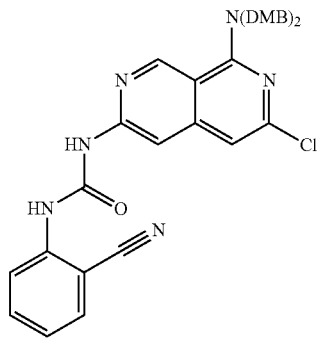

Me₃Al (2 M in toluene, 0.8 mL, 1.6 mmol) was added dropwise to a solution of 2-aminobenzonitrile (200 mg, 1.69 mmol) in toluene (10 mL) at 15° C. The mixture was stirred at 15° C. for 1 h. Phenyl N-[8-[bis[(2,4-dimethoxyphenyl)methyl]amino]-6-chloro-2,7-naphthyridin-3-yl]carbamate (170 mg, 0.28 mmol) was added to the reaction mixture in one portion The mixture was stirred at 15° C. for 1 h. The reaction mixture was diluted with H₂O (1 mL) and ethyl acetate (100 mL). The organic layer was washed with sat. NH₄Cl (30 mL), dried over Na₂SO₄, filtered and evaporated. The residue was purified with silica gel chromatography (PE:EA=2:1 to EA) to give 1-[8-[bis[(2,4-dimethoxyphenyl)methyl]amino]-6-chloro-2,7-naphthyridin-3-yl]-3-(2-cyanophenyl)urea (130 mg, 73.6% yield) as a light yellow solid. LCMS (ESI) [M+H]⁺=639.3.

Step 2: 1-[8-[bis[(2,4-dimethoxyphenyl)methyl]amino]-6-(4-methyl-3-pyridyl)-2,7-naphthyridin-3-yl]-3-(2-cyanophenyl)urea

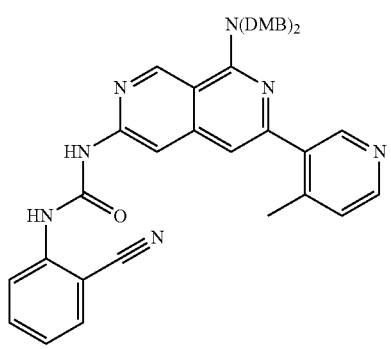

A mixture of 1-[8-[bis[(2,4-dimethoxyphenyl)methyl]amino]-6-chloro-2,7-naphthyridin-3-yl]-3-(2-cyanophenyl)urea (110 mg, 0.17 mmol), 4-methyl-3-(4,4,5,5-tetramethyl-1,3,2-dioxaborolan-2-yl)pyridine (110 mg, 0.50 mmol), XPhos Pd G2 (40 mg, 0.05 mmol), XPhos (40 mg, 0.08 mmol) and K₂CO₃ (110 mg, 0.80 mmol) in 1,4-dioxane (16 mL) and water (4 mL) was stirred at 100° C. under Ar in sealed tube for 3 h. The reaction mixture was cooled to room temperature and diluted with ethyl acetate (100 mL). The organic layer was washed with brine (20 mL), dried over Na₂SO₄, filtered and evaporated. The residue was purified by silica gel chromatography (PE:EA=1:2 to EA to EA:MeOH=10:1) to give 1-[8-[bis[(2,4-dimethoxyphenyl)methyl]amino]-6-(4-methyl-3-pyridyl)-2,7-naphthyridin-3-yl]-3-(2-cyanophenyl)urea (80 mg, 66.8% yield) as a brown solid. LCMS (ESI) [M+H]⁺=696.3.

Step 3: 1-[8-amino-6-(4-methyl-3-pyridyl)-2,7-naphthyridin-3-yl]-3-(2-cyanophenyl)urea

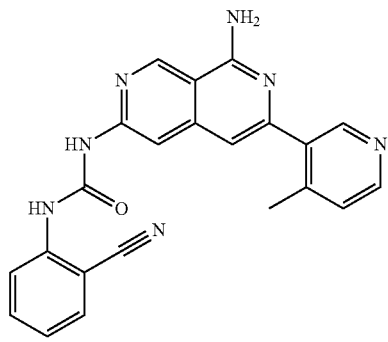 [SMILES: Cc1ccncc1-c1cc2cc(NC(=O)Nc3ccccc3C#N)ncc2c(N)n1]

A mixture of 1-[8-[bis[(2,4-dimethoxyphenyl)methyl]amino]-6-(4-methyl-3-pyridyl)-2,7-naphthyridin-3-yl]-3-(2-cyanophenyl)urea (80 mg, 0.11 mmol) in 2,2,2-trifluoroacetic acid (5 mL) was stirred at 50° C. for 1 h. The reaction mixture was concentrated and purified by prep-HPLC (NH₄HCO₃/CH₃CN/H₂O) to give 1-[8-amino-6-(4-methyl-3-pyridyl)-2,7-naphthyridin-3-yl]-3-(2-cyanophenyl)urea (12.4 mg, 27.3% yield) as a white solid. LCMS (ESI): $R_T$ (min)=1.43, [M+H]⁺=396.1, method=C; ¹H NMR (400 MHz, CD₃OD): δ 9.60 (s, 1H), 8.60 (s, 1H), 8.45 (d, J=4.0 Hz, 1H), 8.13 (s, 1H), 7.84 (s, 1H), 7.65-7.61 (m, 1H), 7.42 (d, J=4.0 Hz, 1H), 7.28-7.19 (m, 3H), 2.50 (s, 3H).

Example 135

(±)-trans-N-(8-amino-5-fluoro-6-(4-methylpyridin-3-yl)-2,7-naphthyridin-3-yl)-2-(1H-pyrazol-4-yl)cyclopropanecarboxamide (Compound 172)

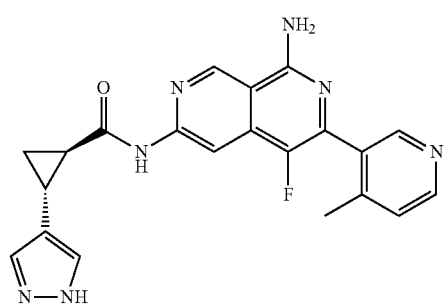 [SMILES: Cc1ccncc1-c1nc(N)c2cnc(NC(=O)[C@@H]3C[C@H]3c3cn[nH]c3)cc2c1F]

To a solution of (±)-trans-N-[8-amino-6-(4-methyl-3-pyridyl)-2,7-naphthyridin-3-yl]-2-(1H-pyrazol-4-yl)cyclopropanecarboxamide (190 mg, 0.49 mmol) in N,N-dimethylformamide (10 mL) was added Selectfluor (95 mg, 0.25 mmol). The mixture was stirred at 50° C. for 3 h. The mixture was directly purified by reverse phase chromatography (acetonitrile 17-47% in 0.05% ammonia in water) to give (±)-trans-N-[8-amino-5-fluoro-6-(4-methyl-3-pyridyl)-2,7-naphthyridin-3-yl]-2-(1H-pyrazol-4-yl)cyclopropanecarboxamide (33 mg, 16.6% yield). LCMS (ESI): $R_T$ (min)=1.538, [M+H]$^+$=404.1, method=C; $^1$H NMR (400 MHz, DMSO-d$_6$): δ 12.64 (s, 1H), 11.19 (s, 1H), 9.43 (s, 1H), 8.52 (s, 1H), 8.49 (d, J=5.2 Hz, 1H), 8.41 (s, 1H), 7.63 (s, 1H), 7.38 (s, 1H), 7.37 (d, J=5.2 Hz, 1H), 7.32 (s, 2H), 2.28 (s, 3H), 2.25-2.21 (m, 2H), 1.45-1.40 (m, 1H), 1.29-1.24 (m, 1H).

Example 136

(±)-trans-N-(8-amino-5-chloro-6-(4-methylpyridin-3-yl)-2,7-naphthyridin-3-yl)-2-(1H-pyrazol-4-yl)cyclopropanecarboxamide (Compound 173)

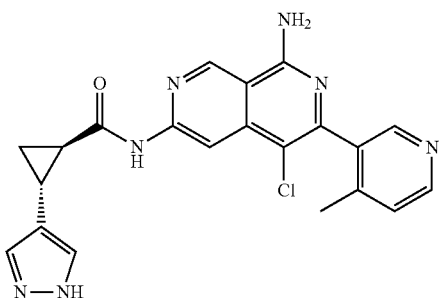 [SMILES: Cc1ccncc1-c1nc(N)c2cnc(NC(=O)[C@@H]3C[C@H]3c3cn[nH]c3)cc2c1Cl]

To a stirred solution of (±)-trans-N-[8-amino-6-(4-methyl-3-pyridyl)-2,7-naphthyridin-3-yl]-2-(1H-pyrazol-4-yl)cyclopropanecarboxamide (100 mg, 0.26 mmol) in N,N-dimethylformamide (8 mL) was added N-chlorosuccinimide (180 mg, 1.35 mmol). The resulting mixture was stirred overnight at room temperature. The mixture was directly purified by reverse phase chromatography (acetonitrile 17-47% in 0.05% ammonia in water) to give (±)-trans-N-[8-amino-5-chloro-6-(4-methyl-3-pyridyl)-2,7-naphthyridin-3-yl]-2-(1H-pyrazol-4-yl)cyclopropanecarboxamide (38 mg, 35% yield) as a white solid. LCMS (ESI): $R_T$ (min)=1.486, [M+H]$^+$=420.1, method=G; 1H NMR (400 MHz, DMSO-d$_6$): δ 12.65 (s, 1H), 11.19 (s, 1H), 9.44 (s, 1H), 8.61 (s, 1H), 8.48 (d, J=5.2 Hz, 1H), 8.41 (s, 1H), 7.60 (br, 4H), 7.36 (d, J=5.2 Hz, 1H), 2.30-2.21 (m, 2H), 2.17 (s, 3H), 1.45-1.42 (m, 1H), 1.29-1.26 (m, 1H).

Example 137

1-(8-amino-6-(4-methylpyridin-3-yl)-2,7-naphthyridin-3-yl)-3-(1-(2-methoxyethyl)azetidin-3-yl)urea (Compound 174)

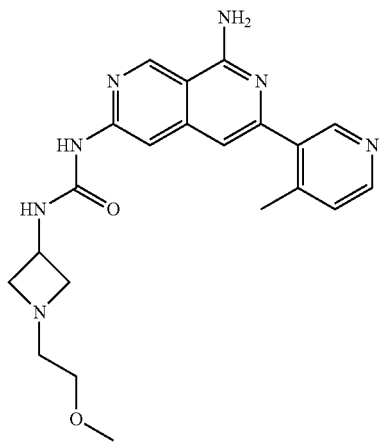 [SMILES: COCCN1CC(NC(=O)Nc2cc3cc(-c4cnccc4C)nc(N)c3cn2)C1]

Step 1: tert-butyl 1-(2-methoxyethyl)azetidin-3-ylcarbamate

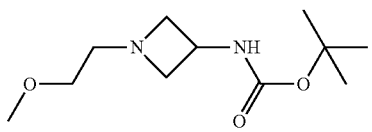

A solution of 3-boc-aminoazetidinehydrochloride (900 mg, 4.31 mmol), 2-bromoethyl methyl ether (1.26 g, 9.07 mmol) and potassium carbonate (1.26 g, 9.13 mmol) in acetonitrile (50 mL) was heated to 80° C. for 24 h. The mixture was filtered and concentrated in vacuo to give tert-butyl N-[1-(2-methoxyethyl)azetidin-3-yl]carbamate (800 mg, 81% yield) as an orange solid. LCMS (ESI) [M+H]$^+$=231.1.

Step 2: 1-(2-methoxyethyl)azetidin-3-amine hydrochloride

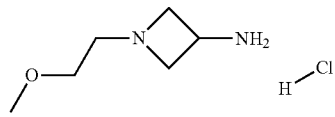

A solution of tert-butyl N-[1-(2-methoxyethyl)azetidin-3-yl]carbamate (800 mg, 3.47 mmol) in HCl/dioxane (4M, 16. mL, 64 mmol) was stirred for 1 h at room temperature. The mixture was evaporated and the resulting solid was washed with (EA:PE=1:1) to give 1-(2-methoxyethyl)azetidin-3-amine hydrochloride (600 mg, 51.8% yield) as a yellow solid. LCMS (ESI) [M+H]$^+$=261.2.

Step 3: 1-(8-(bis(2,4-dimethoxybenzyl)amino)-6-chloro-2,7-naphthyridin-3-yl)-3-(1-(2-methoxyethyl)azetidin-3-yl)urea

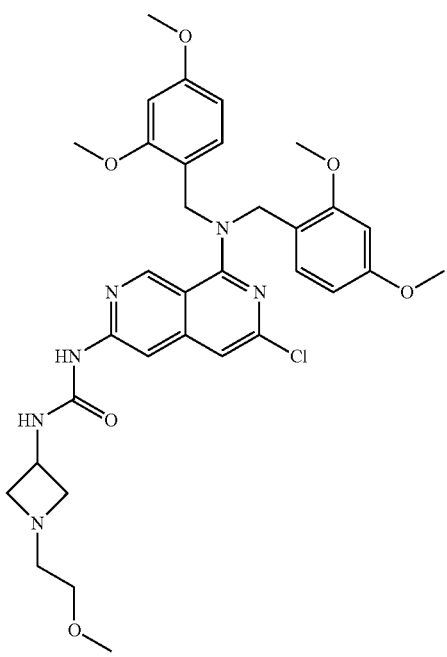 [SMILES: COCCN1CC(NC(=O)Nc2cc3cc(Cl)nc(N(Cc4ccc(OC)cc4OC)Cc4ccc(OC)cc4OC)c3cn2)C1]

A mixture of phenyl N-[8-[bis[(2,4-dimethoxyphenyl)methyl]amino]-6-chloro-2,7-naphthyridin-3-yl]carbamate (800 mg, 30% purity, 0.39 mmol), 1-(2-methoxyethyl)azetidin-3-amine hydrochloride (600 mg, 1.8 mmol) and Et$_3$N (0.8 g, 7.92 mmol) in N,N-dimethylformamide (15 mL) was stirred at 90° C. for 3 h. The mixture was diluted with ethyl acetate (50 mL), washed with water (30 mL×3) and brine (30 mL×2). The organic layer was dried over sodium sulfate, filtered and concentrated in vacuo. The residue was purified by silica gel column (EA:PE=1:1 to DCM:MeOH=20:1) to give 1-[8-[bis[(2,4-dimethoxyphenyl)methyl]amino]-6-chloro-2,7-naphthyridin-3-yl]-3-[1-(2-methoxyethyl)azetidin-3-yl]urea (150 mg, 39.6% yield) as a white solid. LCMS (ESI) [M+H]$^+$=651.3.

Step 4: 1-(8-bis(2,4-dimethoxybenzyl)amino)-6-(4-methylpyridin-3-yl)-2,7-naphthyridin-3-yl)-3-(1-(2-methoxyethyl)azetidin-3-yl)urea

A solution of 1-[8-[bis[(2,4-dimethoxyphenyl)methyl]amino]-6-chloro-2,7-naphthyridin-3-yl]-3-[1-(2-methoxyethyl)azetidin-3-yl]urea (140 mg, 0.14 mmol), 4-methyl-3-(4,4,5,5-tetramethyl-1,3,2-dioxaborolan-2-yl)pyridine (60 mg, 0.27 mmol), Pd(dppf)Cl$_2$ (25 mg, 0.03 mmol) and K$_2$CO$_3$ (50 mg, 0.36 mmol) in 1,4-dioxane (10 mL) and water (2 mL) was heated to 105° C. for 3 h. The mixture was directly purified by silica gel column (EA to DCM:MeOH=10:1) to give 1-[8-[bis[(2,4-dimethoxyphenyl)methyl]amino]-6-(4-methyl-3-pyridyl)-2,7-naphthyridin-3-yl]-3-[1-(2-methoxyethyl)azetidin-3-yl]urea (80 mg, 75% yield) as a grey solid. LCMS (ESI) [M+H]$^+$=708.3.

Step 5: 1-(8-amino-6-(4-methylpyridin-3-yl)-2,7-naphthyridin-3-yl)-3-(1-(2-methoxyethyl)azetidin-3-yl)urea

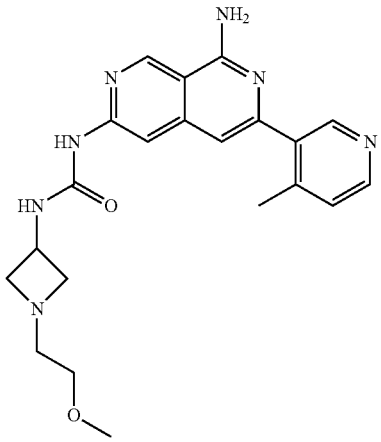 [SMILES: COCCN1CC(NC(=O)Nc2cc3cc(-c4cnccc4C)nc(N)c3cn2)C1]

A solution of 1-[8-[bis[(4-methoxyphenyl)methyl]amino]-6-(4-methyl-3-pyridyl)-2,7-naphthyridin-3-yl]-3-[1-(2-methoxyethyl)azetidin-3-yl]urea (80 mg, 0.12 mmol) in 2,2,2-trifluoroacetic acid (5 mL) was heated to 45° C. for 1 h. After the solvent was evaporated, the residue was neutralized by ammonia in MeOH. The resulting mixture was purified by reverse phase chromatography (acetonitrile 17-47% in 0.05% ammonia in water) to give 1-[8-amino-6-(4-methyl-3-pyridyl)-2,7-naphthyridin-3-yl]-3-[1-(2-methoxyethyl)azetidin-3-yl]urea (23.1 mg, 46% yield) as a white solid. LCMS (ESI): R$_T$ (min)=1.473, [M+H]$^+$=408.3, method=F; $^1$HNMR (400 MHz, CD3OD): δ 9.24 (s, 1H), 8.52 (s, 1H), 8.42 (d, J=5.2 Hz, 1H), 7.54 (s, 1H), 7.39 (d, J=5.2 Hz, 1H), 6.89 (s, 1H), 4.50 (t, J=6.8 Hz, 1H), 3.79 (dt, J=2.0, 6.8 Hz, 2H), 3.45 (t, J=5.6 Hz, 2H), 3.35 (s, 3H), 3.15 (dt, J=2.0, 6.8 Hz, 2H), 2.74 (t, J=5.6 Hz, 2H), 2.45 (s, 3H).

Example 138

1-(8-amino-6-(4-methylpyridin-3-yl)-2,7-naphthyridin-3-yl)-3-(azetidin-3-yl)urea (Compound 175)

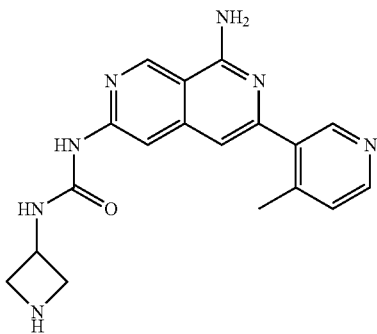 [SMILES: Cc1ccncc1-c1cc2cc(NC(=O)NC3CNC3)ncc2c(N)n1]

Step 1: tert-butyl 3-(3-(8-(bis(2,4-dimethoxybenzyl)amino)-6-chloro-2,7-naphthyridin-3-yl)ureido)azetidine-1-carboxylate

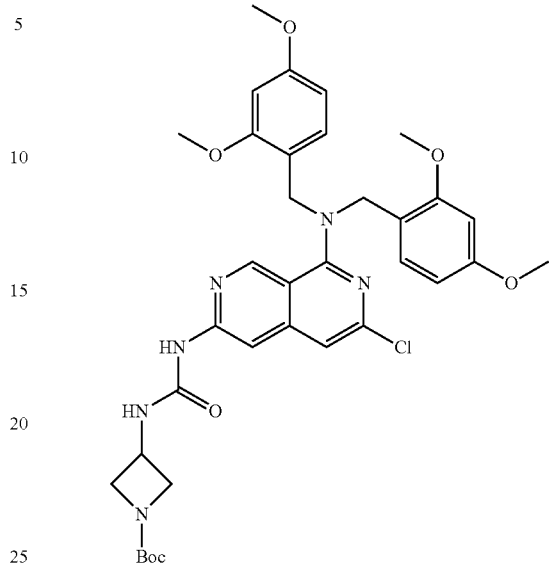

A mixture of phenyl N-[8-[bis[(2,4-dimethoxyphenyl)methyl]amino]-6-chloro-2,7-naphthyridin-3-yl]carbamate (240 mg, 0.39 mmol), 1-Boc-3-(amino)azetidine (400 mg, 2.32 mmol) and Et$_3$N (0.8 g, 7.92 mmol) in N,N-dimethylformamide (15 mL) was stirred at 90° C. for 3 h. The mixture was diluted with ethyl acetate (50 mL), washed with water (30 mL×3) and brine (30 mL×2). The organic layer was dried over sodium sulfate, filtered and concentrated in vacuo. The residue was purified by silica gel column (EA:PE=1:2 to 1:1) to give tert-butyl 3-[[8-[bis[(2,4-dimethoxyphenyl)methyl]amino]-6-chloro-2,7-naphthyridin-3-yl]carbamoylamino]azetidine-1-carboxylate (110 mg, 27% yield) as a white solid. LCMS (ESI) [M+H]$^+$=693.3.

Step 2: tert-butyl 3-(3-(8-(bis(2,4-dimethoxybenzyl)amino)-6-(4-methylpyridin-3-yl)-2,7-naphthyridin-3-yl)ureido)azetidine-1-carboxylate

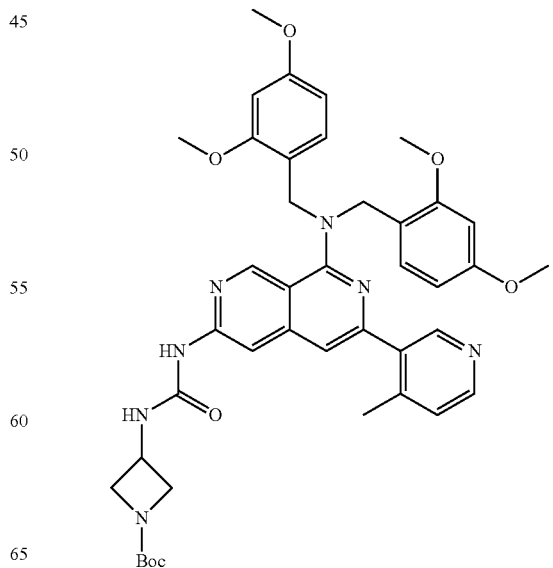

A mixture of tert-butyl 3-[[8-[bis[(2,4-dimethoxyphenyl)methyl]amino]-6-chloro-2,7-naphthyridin-3-yl]carbamoylamino]azetidine-1-carboxylate (100 mg, 0.10 mmol), 4-methyl-3-(4,4,5,5-tetramethyl-1,3,2-dioxaborolan-2-yl)pyridine (28 mg, 0.13 mmol), XPhos Pd G2 (12 mg, 0.02 mmol), AcOK (23 mg, 0.23 mmol) and XPhos (18 mg, 0.04 mmol) in 1,4-dioxane (10 mL) and water (2 mL) was stirred under Ar at 100° C. for 2 h. The mixture was concentrated and purified by silica gel column (EA:PE=1:1 to 100% EA to DCM:MeOH=10:1) to give tert-butyl 3-[[8-[bis[(2,4-dimethoxyphenyl)methyl]amino]-6-(4-methyl-3-pyridyl)-2,7-naphthyridin-3-yl]carbamoylamino]azetidine-1-carboxylate (80 mg, 88% yield) as a light yellow solid. LCMS (ESI) [M+H]$^+$=750.3.

Step 3: 1-(8-amino-6-(4-methylpyridin-3-yl)-2,7-naphthyridin-3-yl)-3-(azetidin-3-yl)urea

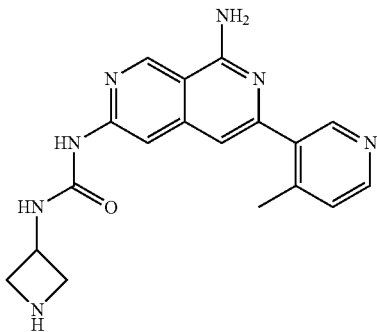 [SMILES: Cc1ccncc1-c1cc2cc(NC(=O)NC3CNC3)ncc2c(N)n1]

A solution of tert-butyl 3-[[8-[bis[(2,4-dimethoxyphenyl)methyl]amino]-6-(4-methyl-3-pyridyl)-2,7-naphthyridin-3-yl]carbamoylamino]azetidine-1-carboxylate (75 mg, 0.08 mmol) in 2,2,2-trifluoroacetic acid (5 mL) was heated to 45° C. for 1 h. After the solvent was evaporated, the mixture was neutralized by ammonia in MeOH. The resulting residue was purified by reverse phase chromatography (acetonitrile 17-47% in 0.05% ammonia bicarbonate in water) to give 1-[8-amino-6-(4-methyl-3-pyridyl)-2,7-naphthyridin-3-yl]-3-(azetidin-3-yl)urea (14.3 mg, 51% yield) as a white solid. LCMS (ESI): R$_T$ (min)=1.366, [M+H]$^+$=350.1, method=C; $^1$HNMR (400 MHz, DMSO-d$_6$) δ 9.26 (s, 1H), 9.17 (s, 1H), 8.56 (s, 1H), 8.42 (d, J=5.2 Hz, 1H), 7.80 (s, 1H), 7.67 (d, J=5.2 Hz, 1H), 7.30 (d, J=5.2 Hz, 1H), 7.26 (s, 2H), 6.88 (s, 1H), 4.5-4.47 (m, 1H), 3.63-3.59 (m, 2H), 3.40-3.32 (m, 2H), 2.41 (s, 3H).

Example 139

(R)-1-(8-amino-6-(4-ethylpyridin-3-yl)-2,7-naphthyridin-3-yl)-3-(1-methyl-2-oxopyrrolidin-3-yl)urea
(Compound 176)

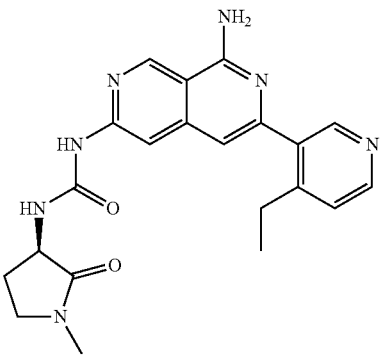 [SMILES: CCc1ccncc1-c1cc2cc(NC(=O)N[C@@H]3CCN(C)C3=O)ncc2c(N)n1]

Step 1: (R)-1-(8-(bis(4-methoxybenzyl)amino)-6-(4-ethylpyridin-3-yl)-2,7-naphthyridin-3-yl)-3-(1-methyl-2-oxopyrrolidin-3-yl)urea

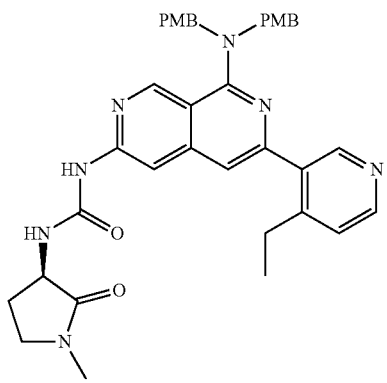

To a solution of triphosgene (108 mg, 0.36 mmol) in tetrahydrofuran (4 mL) was added 3-(4-ethyl-3-pyridyl)-N1,N1-bis[(4-methoxyphenyl)methyl]-2,7-naphthyridine-1,6-diamine (180 mg, 0.18 mmol) and Et$_3$N (0.5 mL, 3.56 mmol) in tetrahydrofuran (5 mL) at 0° C. The mixture was stirred at 0° C. for 1 h. (3R)-3-amino-1-methyl-pyrrolidin-2-one (450 mg, 3.94 mmol) was added. The mixture was warmed up to rt overnight. The mixture was directly purified by silica gel column chromatography (DCM:MeOH=20:1) to give 1-[8-[bis[(4-methoxyphenyl)methyl]amino]-6-(4-ethyl-3-pyridyl)-2,7-naphthyridin-3-yl]-3-[(3R)-1-methyl-2-oxo-pyrrolidin-3-yl]urea (32 mg, 28% yield) as a light yellow solid. LCMS (ESI) [M+H]$^+$=646.3.

Step 2: (R)-1-(8-amino-6-(4-ethylpyridin-3-yl)-2,7-naphthyridin-3-yl)-3-(1-methyl-2-oxopyrrolidin-3-yl)urea

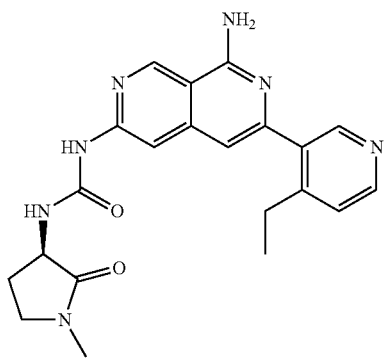 [SMILES: CCc1ccncc1-c1cc2cc(NC(=O)N[C@@H]3CCN(C)C3=O)ncc2c(N)n1]

A solution of 1-[8-[bis[(4-methoxyphenyl)methyl]amino]-6-(4-ethyl-3-pyridyl)-2,7-naphthyridin-3-yl]-3-[(3R)-1-methyl-2-oxo-pyrrolidin-3-yl]urea (27 mg, 0.0400 mmol) in 2,2,2-trifluoroacetic acid (3 mL) was heated to reflux for 3 h. The mixture was evaporated and neutralized by ammonia in MeOH. The resulting residue was purified by reverse phase chromatography (acetonitrile 0-40/0.1% NH$_4$HCO$_3$ in water) to afford 1-[8-amino-6-(4-ethyl-3-pyridyl)-2,7-naphthyridin-3-yl]-3-[(3R)-1-methyl-2-oxo-pyrrolidin-3-yl]urea (5.5 mg, 33% yield) as a white solid. LCMS (ESI): R$_T$ (min)=1.50, [M+H]$^+$=406.2, method=C;

$^1$HNMR (400 MHz, CD$_3$OD) δ 9.29 (s, 1H), 8.50 (s, 2H), 7.52 (s, 1H), 7.45 (d, J=5.2 Hz, 1H), 6.89 (s, 1H), 4.49 (t, J=9.2 Hz, 1H), 3.47 (dd, J=4.0, 9.2 Hz, 2H), 2.93 (s, 3H), 2.83 (q, J=7.6 Hz, 2H), 2.62-2.57 (m, 1H), 2.09-2.04 (m, 1H), 1.19 (t, J=7.6 Hz, 3H).

Example 140

1-(8-amino-6-(4-methylpyridin-3-yl)-2,7-naphthyridin-3-yl)-3-(1-hydroxypropan-2-yl)urea (Compound 177)

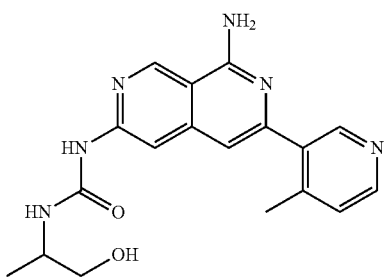 [SMILES: Cc1ccncc1-c1cc2cc(NC(=O)NC(C)CO)ncc2c(N)n1]

Step 1: 1-(8-(bis(2,4-dimethoxybenzyl)amino)-6-chloro-2,7-naphthyridin-3-yl)-3-(1-hydroxypropan-2-yl)urea

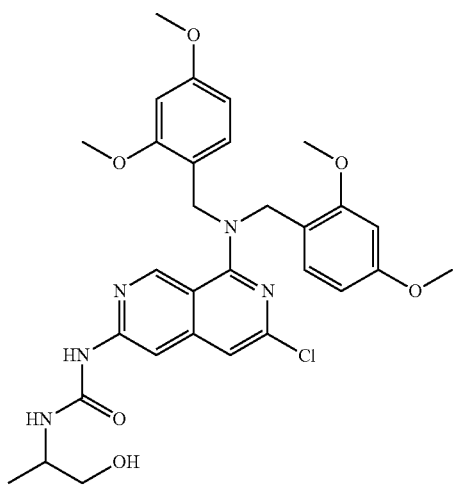 [SMILES: COc1ccc(CN(Cc2ccc(OC)cc2OC)c2nc(Cl)cc3cc(NC(=O)NC(C)CO)ncc23)c(OC)c1]

A mixture of phenyl N-[8-[bis[(2,4-dimethoxyphenyl)methyl]amino]-6-chloro-2,7-naphthyridin-3-yl]carbamate (150 mg, 0.24 mmol), DL-alaninol (75 mg, 1 mmol) and Et$_3$N (500 mg, 4.95 mmol) in N,N-dimethylformamide (10 mL) was stirred at 90° C. for 2 h. The mixture was diluted with ethyl acetate (80 mL), washed with water (30 mL×3) and brine (30 mL×2). The organic layer was dried over sodium sulfate, filtered and concentrated in vacuo. The residue was purified by silica gel column (EA:PE=1:1 to 4:1) to give 1-[8-[bis[(2,4-dimethoxyphenyl)methyl]amino]-6-chloro-2,7-naphthyridin-3-yl]-3-(2-hydroxy-1-methyl-ethyl)urea (110 mg, 0.18 mmol, 76% yield) as a white solid. LCMS (ESI) [M+H]$^+$=596.2.

Step 2: 1-(8-(bis(2,4-dimethoxybenzyl)amino)-6-(4-methylpyridin-3-yl)-2,7-naphthyridin-3-yl)-3-(1-hydroxypropan-2-yl)urea

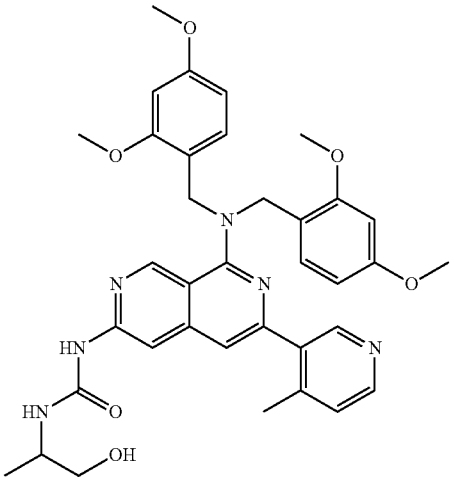 [SMILES: COc1ccc(CN(Cc2ccc(OC)cc2OC)c2nc(-c3cnccc3C)cc3cc(NC(=O)NC(C)CO)ncc23)c(OC)c1]

A mixture of 1-[8-[bis[(2,4-dimethoxyphenyl)methyl]amino]-6-chloro-2,7-naphthyridin-3-yl]-3-(2-hydroxy-1-methyl-ethyl)urea (100 mg, 0.17 mmol), 4-methyl-3-(4,4,5,5-tetramethyl-1,3,2-dioxaborolan-2-yl)pyridine (50 mg, 0.23 mmol), XPhos Pd G2 (20 mg, 0.03 mmol), AcOK (40 mg, 0.41 mmol) and XPhos (30 mg, 0.06 mmol) in 1,4-dioxane (10 mL) and water (2 mL) was stirred under Ar at 100° C. for 2 h. The mixture was concentrated and purified by silica gel column chromatography (DCM:MeOH=10:1) to give 1-[8-[bis[(2,4-dimethoxyphenyl)methyl]amino]-6-(4-methyl-3-pyridyl)-2,7-naphthyridin-3-yl]-3-(2-hydroxy-1-methyl-ethyl)urea (85 mg, 78% yield) as a light yellow solid. LCMS (ESI) [M+H]$^+$=653.3.

Step 3: 1-(8-amino-6-(4-methylpyridin-3-yl)-2,7-naphthyridin-3-yl)-3-(1-hydroxypropan-2-yl)urea

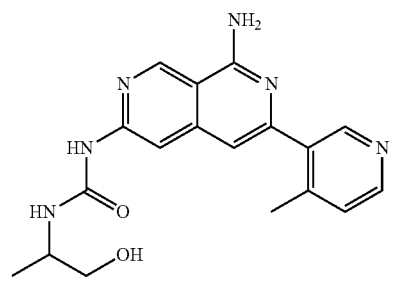 [SMILES: Cc1ccncc1-c1cc2cc(NC(=O)NC(C)CO)ncc2c(N)n1]

A solution of 1-[8-[bis[(2,4-dimethoxyphenyl)methyl]amino]-6-(4-methyl-3-pyridyl)-2,7-naphthyridin-3-yl]-3-(2-hydroxy-1-methyl-ethyl)urea (80 mg, 0.12 mmol) in 2,2,2-trifluoroacetic acid (5 mL) was heated to 45° C. for 1 h. After the solvent was evaporated, the residue was neutralized by ammonia in methanol. The mixture was directly purified by reverse phase HPLC (acetonitrile 17-47% in 0.05% ammonia bicarbonate in water) to give 1-[8-amino-6-(4-methyl-3-pyridyl)-2,7-naphthyridin-3-yl]-3-(2-hydroxy-1-methyl-ethyl)urea (28.9 mg, 67% yield) as a white solid. LCMS (ESI): R$_T$(min)=1.432, [M+H]$^+$=353.1, method=C; $^1$HNMR (400 MHz, DMSO-d$_6$) δ 9.26 (s, 1H), 9.16 (s, 1H), 8.56 (s, 1H), 8.42 (d, J=5.2 Hz, 1H), 7.78 (s, 1H), 7.29 (d, J=5.2 Hz, 1H), 7.23-7.21 (m, 3H), 6.87 (s, 1H), 4.83 (t, J=5.2 Hz, 1H), 3.79-3.70 (m, 1H), 3.43-3.32 (m, 2H), 2.41 (s, 3H), 1.11 (d, J=6.8 Hz, 3H).

Example 141

1-[8-amino-6-(4-methyl-3-pyridyl)-2,7-naphthyridin-3-yl]-3-[1-(1-cyanoethyl)pyrazol-4-yl]urea (Compound 178)

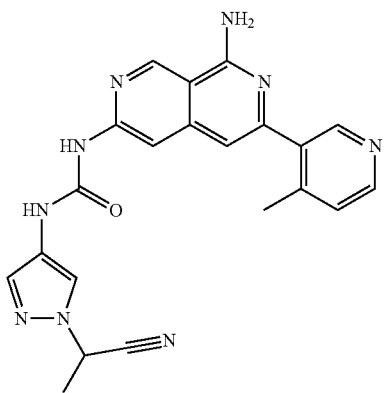 [SMILES: Cc1ccncc1-c1cc2cc(NC(=O)Nc3cnn(C(C)C#N)c3)ncc2c(N)n1]

Step 1: (±)-2-(4-nitropyrazol-1-yl)propanenitrile

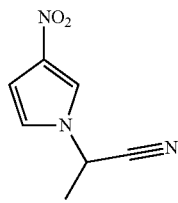

A mixture of 4-nitro-1H-pyrazole (500 mg, 4.42 mmol), 2-bromopropionitrile (1185 mg, 8.85 mmol) and potassium carbonate (610 mg, 4.42 mmol) in N,N-dimethylformamide (15 mL) was stirred at 80° C. for 2 h. The reaction mixture was concentrated and the residue was purified by flash column chromatography eluting with PE/EA (5/1) to give (±)-2-(4-nitropyrazol-1-yl)propanenitrile (720 mg, 4.334 mmol, 98% yield) as a yellow solid. LCMS (ESI): [M+H]$^+$=167.1.

Step 2: (±)-2-(4-aminopyrazol-1-yl)propanenitrile

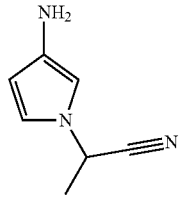

A mixture of (±)-2-(4-nitropyrazol-1-yl)propanenitrile (720 mg, 4.33 mmol) andiron (1230 mg, 21.96 mmol) in acetic acid (20 mL) was stirred at 25° C. overnight. The reaction mixture was filtered and concentrated. The residue was purified by flash column chromatography eluting with DCM/MeOH (20/1) to give (±)-2-(4-aminopyrazol-1-yl)propanenitrile (200 mg, 33.9% yield) as a yellow solid. LCMS (ESI): [M+H]$^+$=137.1.

Step 3: (±)-1-[8-[bis[(2,4-dimethoxyphenyl)methyl]amino]-6-chloro-2,7-naphthyridin-3-yl]-3-[1-(1-cyanoethyl)pyrazol-4-yl]urea

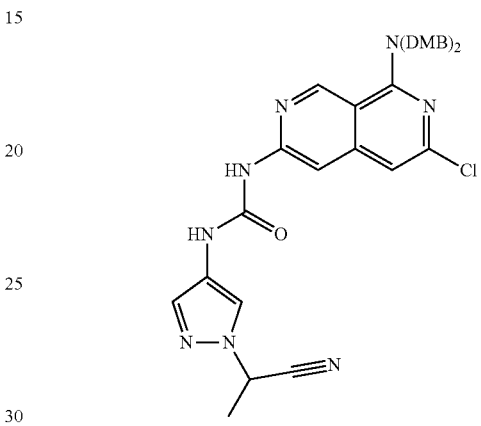

A mixture of (±)-2-(4-aminopyrazol-1-yl)propanenitrile (176 mg, 1.29 mmol), phenyl N-[8-[bis[(2,4-dimethoxyphenyl)methyl]amino]-6-chloro-2,7-naphthyridin-3-yl]carbamate (160 mg, 0.26 mmol) and triethylamine (100 mg, 0.99 mmol) in 1,4-dioxane (5 mL) was stirred at 110° C. overnight. The reaction mixture was concentrated and purified by prep-TLC (DCM/MeOH=10/1) to give 1-[8-[bis[(2,4-dimethoxyphenyl)methyl]amino]-6-chloro-2,7-naphthyridin-3-yl]-3-[1-(1-cyanoethyl)pyrazol-4-yl]urea (165 mg, 96.5% yield) as a yellow solid. LCMS (ESI): [M+H]$^+$=657.1.

Step 4: (±)-1-[8-[bis[(2,4-dimethoxyphenyl)methyl]amino]-6-(4-methyl-3-pyridyl)-2,7-naphthyridin-3-yl]-3-[i-(1-cyanoethyl)pyrazol-4-yl]urea

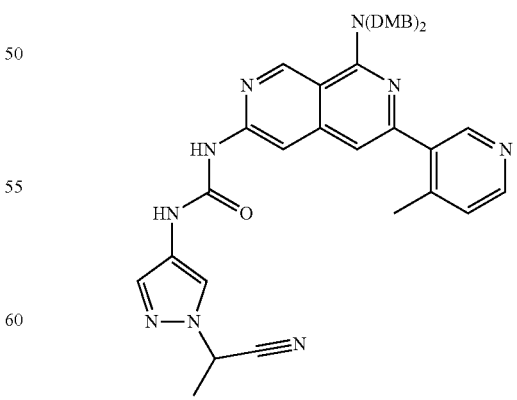

A mixture of (±)-1-[8-[bis[(2,4-dimethoxyphenyl)methyl]amino]-6-chloro-2,7-naphthyridin-3-yl]-3-[1-(1-cyanoethyl)pyrazol-4-yl]urea (200 mg, 0.3 mmol), 4-methyl-3-(4, 4,5,5-tetramethyl-1,3,2-dioxaborolan-2-yl)pyridine (80 mg, 0.37 mmol), Xphos-Pd-G2 (24 mg, 0.030 mmol), Xphos (28 mg, 0.06 mmol) and potassium carbonate (84 mg, 0.61 mmol) in 1,4-dioxane (8 mL) and water (0.8 mL) was stirred at 100° C. for 2 h. The reaction mixture was concentrated and purified by prep-TLC (DCM/MeOH=10/1) to give (±)-1-[8-[bis[(2,4-dimethoxyphenyl)methyl]amino]-6-(4-methyl-3-pyridyl)-2,7-naphthyridin-3-yl]-3-[1-(1-cyanoethyl)pyrazol-4-yl]urea (200 mg, 92.1% yield) as a yellow solid. LCMS (ESI): [M+H]$^+$=714.1.

Step 5: (±)-1-[8-amino-6-(4-methyl-3-pyridyl)-2,7-naphthyridin-3-yl]-3-[1-(1-cyanoethyl)pyrazol-4-yl]urea

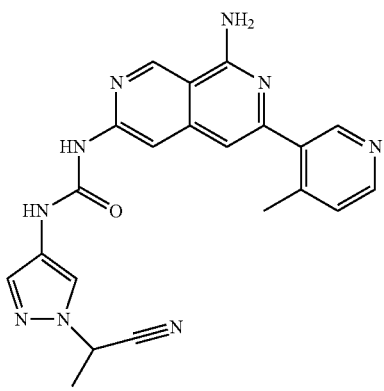 [SMILES: Cc1ccncc1-c1cc2cc(NC(=O)Nc3cnn(C(C)C#N)c3)ncc2c(N)n1]

A solution of (±)-1-[8-[bis[(2,4-dimethoxyphenyl)methyl]amino]-6-(4-methyl-3-pyridyl)-2,7-naphthyridin-3-yl]-3-[1-(1-cyanoethyl)pyrazol-4-yl]urea (220 mg, 0.31 mmol) in 2,2,2-trifluoroacetic acid (10 mL) was stirred at 50° C. for 3 h. The reaction mixture was concentrated and was purified by prep-HPLC (Mobile Phase A: water (10 mmol/L NH$_4$HCO$_3$) B: ACN) to give (±)-1-[8-amino-6-(4-methyl-3-pyridyl)-2,7-naphthyridin-3-yl]-3-[1-(1-cyanoethyl)pyrazol-4-yl]urea (60 mg, 47.1% yield) as a white solid. LCMS (ESI): RT (min)=1.532, [M+H]$^+$=414.1, method=H; $^1$H NMR (400 MHz, DMSO-d$_6$) δ 9.44 (s, 2H), 9.32 (s, 1H), 8.56 (s, 1H), 8.43 (d, J=5.2 Hz, 1H), 8.07 (s, 1H), 7.87 (s, 1H), 7.65 (s, 1H), 7.32-7.31 (m, 2H), 6.94 (s, 1H), 5.82-5.83 (m, 1H), 2.42 (s, 3H), 1.78 (d, J=6.8 Hz, 3H).

Example 142

(±)-cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide (Compound 179)

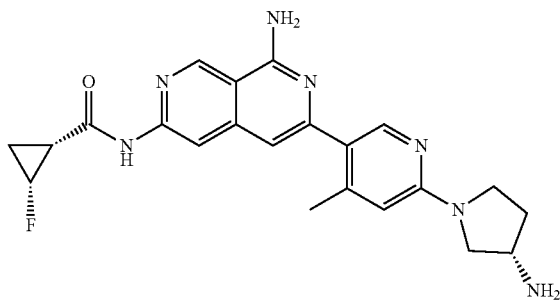 [SMILES: Cc1cc(N2CC[C@H](N)C2)ncc1-c1cc2cc(NC(=O)[C@H]3C[C@H]3F)ncc2c(N)n1]

Step 1: tert-Butyl N-[(3S)-1-(5-bromo-4-methyl-2-pyridyl)pyrrolidin-3-yl]carbamate

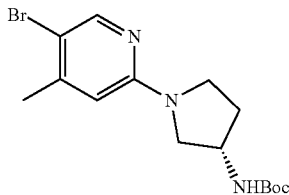 [SMILES: Cc1cc(N2CC[C@H](NC(=O)OC(C)(C)C)C2)ncc1Br]

A mixture of 5-bromo-2-fluoro-4-methyl-pyridine (1000 mg, 5.26 mmol), tert-butyl (3S)-3-pyrrolidinylcarbamate (1200 mg, 6.44 mmol) and potassium carbonate (2200 mg, 15.94 mmol) in dimethyl sulfoxide (15 mL) was stirred at 100° C. overnight. The reaction mixture was diluted with water (30 mL) and extracted with ethyl acetate (3×20 mL). The combined organic layers was washed with brine, dried over sodium sulfate and concentrated. The residue was purified by flash column chromatography eluting with PE/EA (10/1) to give tert-butyl N-[(3S)-1-(5-bromo-4-methyl-2-pyridyl)pyrrolidin-3-yl]carbamate (1700 mg, 90.7% yield) as a white solid. LCMS (ESI): [M+H]$^+$=356.1.

Step 2: tert-Butyl N-[(3S)-1-[4-methyl-5-(4,4,5,5-tetramethyl-1,3,2-dioxaborolan-2-yl)-2-pyridyl]pyrrolidin-3-yl]carbamate

A mixture of tert-butyl N-[(3S)-1-(5-bromo-4-methyl-2-pyridyl)pyrrolidin-3-yl]carbamate (1000 mg, 2.81 mmol), bis(pinacolato)diboron (3500 mg, 13.78 mmol), [1,1'-bis(diphenylphosphino)ferrocene]dichloropalladium(II) (229 mg, 0.28 mmol) and potassium acetate (835 mg, 8.52 mmol) in 1,4-dioxane (20 mL) was stirred at 90° C. overnight. The reaction mixture was concentrated and purified by prep-TLC (PE/EA=1/1) to give tert-butyl N-[(3S)-1-[4-methyl-5-(4,4,5,5-tetramethyl-1,3,2-dioxaborolan-2-yl)-2-pyridyl]pyrrolidin-3-yl]carbamate (1000 mg, 1.24 mmol, 44.2% yield) as a yellow oil. LCMS (ESI): [M+H]$^+$=404.1.

Step 3: (±)-tert-Butyl N-[(3S)-1-[5-[1-amino-6-[[cis-2-fluorocyclopropanecarbonyl]amino]-2,7-naphthyridin-3-yl]-4-methyl-2-pyridyl]pyrrolidin-3-yl]carbamate

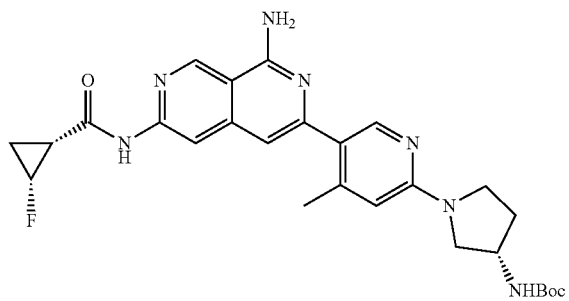 [SMILES: Cc1cc(N2CC[C@H](NC(=O)OC(C)(C)C)C2)ncc1-c1cc2cc(NC(=O)[C@H]3C[C@H]3F)ncc2c(N)n1]

A mixture of (±)-cis-N-(8-amino-6-chloro-2,7-naphthyridin-3-yl)-2-fluoro-cyclopropanecarboxamide (70 mg, 0.25 mmol), tert-butyl N-[(3S)-1-[4-methyl-5-(4,4,5,5-tetramethyl-1,3,2-dioxaborolan-2-yl)-2-pyridyl]pyrrolidin-3-yl]carbamate (100 mg, 0.25 mmol), Xphos-Pd-G2 (19 mg, 0.02 mmol), Xphos (24 mg, 0.05 mmol) and potassium carbonate (68 mg, 0.49 mmol) in 1,4-dioxane (8 mL) and water (2 mL) was stirred at 100° C. for 2 h. The reaction mixture was concentrated and purified by Prep-TLC (PE/EA=1/1) to give tert-butyl N-[(3S)-1-[5-[1-amino-6-[[(1R,2R)-2-fluorocyclopropanecarbonyl]amino]-2,7-naphthyridin-3-yl]-4-methyl-2-pyridyl]pyrrolidin-3-yl]carbamate (100 mg, 77.3% yield) as a yellow oil. LCMS (ESI): [M+H]$^+$=522.1.

Step 4: (±)-cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide

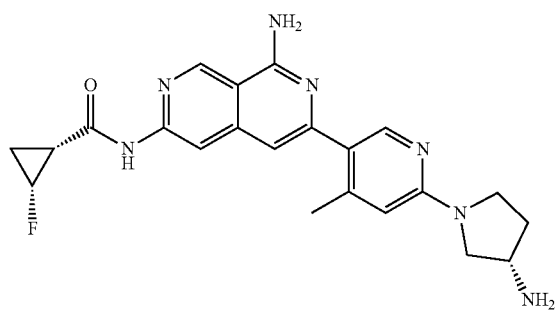 [SMILES: Cc1cc(N2CC[C@H](N)C2)ncc1-c1cc2cc(NC(=O)[C@H]3C[C@H]3F)ncc2c(N)n1]

A solution of tert-butyl N-[(3S)-1-[5-[1-amino-6-[[cis-2-fluorocyclopropanecarbonyl]amino]-2,7-naphthyridin-3-yl]-4-methyl-2-pyridyl]pyrrolidin-3-yl]carbamate (100 mg, 0.19 mmol) and hydrogen chloride in 1,4-dioxane (4N, 0.5 mL, 1.9 mmol) in 1,4-dioxane (5 mL) was stirred at 25° C. for 1 h. The reaction mixture was concentrated before ammonia in methanol was added. The solution was concentrated and purified by prep-HPLC (Mobile Phase A: water (10 mmol/L NH$_4$HCO$_3$) B: ACN) to give (±)-cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide (45 mg, 55.7% yield) as a yellow solid. LCMS (ESI): RT (min)=1.407, [M+H]$^+$=422.1, method=H; $^1$HNMR (400 MHz, CD$_3$OD) δ 9.24 (s, 1H), 8.26 (s, 1H), 8.07 (s, 1H), 6.88 (s, 1H), 6.41 (s, 1H), 4.98-4.95 (m, 1H), 4.81-4.79 (m, 1H), 3.72-3.63 (m, 3H), 3.54-3.48 (m, 1H), 3.27-3.25 (m, 1H), 2.38 (s, 3H), 2.30-2.25 (m, 1H), 2.18-2.15 (m, 1H), 1.96-1.80 (m, 2H), 1.26-1.20 (m, 1H).

Example 143

(±)-trans-4-[1-amino-6-[[trans-2-cyanocyclopropanecarbonyl]amino]-2,7-naphthyridin-3-yl]-N,1,3,5-tetramethyl-pyrrole-2-carboxamide (Compound 180)

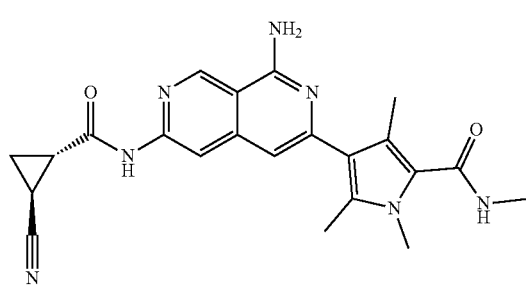 [SMILES: CNC(=O)c1c(C)c(-c2cc3cc(NC(=O)[C@H]4C[C@@H]4C#N)ncc3c(N)n2)c(C)n1C]

Step 1: ethyl 4-bromo-3,5-dimethyl-1H-pyrrole-2-carboxylate

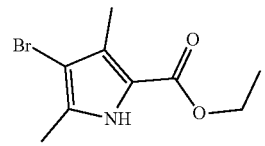

N-Bromosuccinimide (385 mg, 2.16 mmol) was added in portions to a mixture of ethyl-3,5-dimethyl-1H-pyrrole-2-carboxylate (350 mg, 2.09 mmol) and potassium carbonate (307 mg, 2.22 mmol) in acetonitrile (20 mL) at 0° C. The mixture was warmed to room temperature, diluted with water and then stirred for 30 mins. The precipitate was collected by vacuum filtration, washed with ethanol:water (1:2) and dried to give ethyl 4-bromo-3,5-dimethyl-1H-pyrrole-2-carboxylate (450 mg, 1.8285 mmol, 87.4% yield) as a white solid. LCMS (ESI): [M+H]$^+$=246.1.

Step 2: ethyl 4-bromo-1,3,5-trimethyl-pyrrole-2-carboxylate

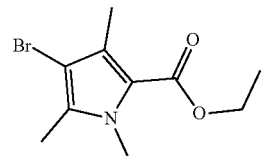

A mixture of ethyl 4-bromo-3,5-dimethyl-1H-pyrrole-2-carboxylate (450 mg, 1.83 mmol) in tetrahydrofuran (20 mL) was stirred at 0° C. for 10 min. Sodium hydride (60 mg, 2.5 mmol) was added at 0° C. The reaction mixture was stirred at 0° C. for 10 min. Iodomethane (312 mg, 2.2 mmol)

was then added. The reaction mixture was warmed to 25° C. and stirred for 2 h. The reaction mixture was concentrated and purified by flash column chromatography (PE/EA=20/1) to give ethyl 4-bromo-1,3,5-trimethyl-pyrrole-2-carboxylate (320 mg, 1.23 mmol, 67.3% yield) as a yellow solid. LCMS (ESI): [M+H]⁺=260.1.

Step 3:
4-bromo-1,3,5-trimethyl-pyrrole-2-carboxylic acid

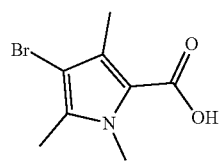

A mixture of ethyl 4-bromo-1,3,5-trimethyl-pyrrole-2-carboxylate (320 mg, 1.23 mmol) and potassium hydroxide (138 mg, 2.46 mmol) in ethanol (10 mL) and water (5 mL) was stirred at 100° C. for 4 h. The reaction was concentrated and then diluted with water (20 mL). The mixture was washed with ethyl acetate (2×20 mL). The water phase was adjusted to pH 4 and extracted with ethyl acetate (2×20 mL). The organic layer was dried over sodium sulfate, filtered and concentrated to 4-bromo-1,3,5-trimethyl-pyrrole-2-carboxylic acid (270 mg, 1.1634 mmol, 94.6% yield) as a white solid. LCMS (ESI): [M+H]⁺=232.1.

Step 4:
4-bromo-N,1,3,5-tetramethyl-pyrrole-2-carboxamide

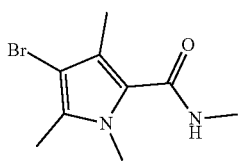

A mixture of 4-bromo-1,3,5-trimethyl-pyrrole-2-carboxylic acid (260 mg, 1.12 mmol), 2-(7-Aza-1H-benzotriazole-1-yl)-1,1,3,3-tetramethyluronium hexafluorophosphate (0.64 g, 1.68 mmol), potassium carbonate (462.0 mg, 3.35 mmol) and methanamine (105.0 mg, 3.38 mmol) in dichloromethane (10 mL) was stirred at 25° C. for 1 h. The reaction mixture was concentrated and purified by flash column chromatography (50% ethyl acetate in petroleum ether) to give 4-bromo-N,1,3,5-tetramethyl-pyrrole-2-carboxamide (250 mg, 1.02 mmol, 91% yield) as a white solid. LCMS (ESI): [M+H]⁺=245.1.

Step 5: N,1,3,5-tetramethyl-4-(4,4,5,5-tetramethyl-1,3,2-dioxaborolan-2-yl)pyrrole-2-carboxamide

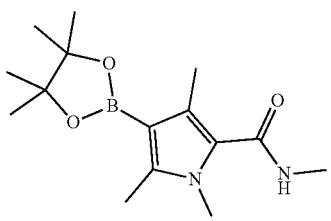

A mixture of 4-bromo-N,1,3,5-tetramethyl-pyrrole-2-carboxamide (100 mg, 0.41 mmol), bis(pinacolato)diboron (510 mg, 2.01 mmol), [1,1'-bis(diphenylphosphino)ferrocene]dichloropalladium(II) (34 mg, 0.04 mmol) and potassium phosphate (260 mg, 1.23 mmol) in 1,4-dioxane (10 mL) was stirred at 85° C. overnight. The reaction mixture was concentrated and purified by prep-TLC (PE/EA, 1/1) to give N,1,3,5-tetramethyl-4-(4,4,5,5-tetramethyl-1,3,2-dioxaborolan-2-yl)pyrrole-2-carboxamide (120 mg, 49.3% yield) as a yellow solid. LCMS (ESI): [M+H]⁺=245.1.

Step 6: (±)-trans-4-[1-amino-6-[[trans-2-cyanocyclopropanecarbonyl]amino]-2,7-naphthyridin-3-yl]-N,1,3,5-tetramethyl-pyrrole-2-carboxamide

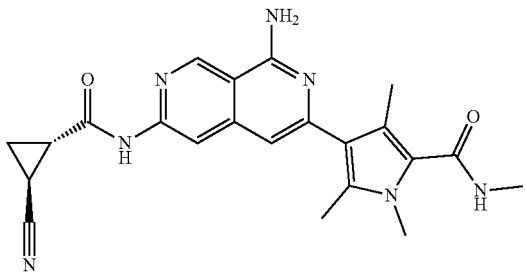 [SMILES: CNC(=O)c1c(C)c(-c2cc3cc(NC(=O)[C@H]4C[C@@H]4C#N)ncc3c(N)n2)c(C)n1C]

A solution of (±)-trans-N-(8-amino-6-chloro-2,7-naphthyridin-3-yl)-2-cyano-cyclopropanecarboxamide (95 mg, 0.33 mmol), N,1,3,5-tetramethyl-4-(4,4,5,5-tetramethyl-1,3,2-dioxaborolan-2-yl)pyrrole-2-carboxamide (100 mg, 0.34 mmol), Xphos-Pd-G2 (27 mg, 0.03 mmol), Xphos (32 mg, 0.07 mmol) and potassium carbonate (95 mg, 0.69 mmol) in 1,4-dioxane (5 mL) and water (1 mL) was stirred at 82° C. overnight. The reaction mixture was as concentrated and purified by prep-HPLC (Mobile Phase A: water (10 mmol/L NH₄HCO₃) B: ACN) to give 4-[1-amino-6-[[(1S,2S)-2-cyanocyclopropanecarbonyl]amino]-2,7-naphthyridin-3-yl]-N,1,3,5-tetramethyl-pyrrole-2-carboxamide (11 mg, 0.0250 mmol, 7.3% yield) as a yellow solid. LCMS (ESI): RT (min)=1.47, [M+H]+=418.1, method=H; ¹H NMR (400 MHz, CD₃OD) δ 9.23 (s, 1H), 8.21 (s, 1H), 6.75 (s, 1H), 6.41 (s, 2H), 3.68 (s, 3H), 2.93 (s, 3H), 2.63-2.62 (m, 1H), 2.31 (s, 3H), 2.22 (s, 3H), 2.16-2.11 (m, 1H), 1.62-1.54 (m, 2H).

Example 144

(±)-trans-N-[8-amino-6-(5-amino-2,4-dimethyl-3-pyridyl)-2,7-naphthyridin-3-yl]-2-methyl-cyclopropane carboxamide (Compound 181)

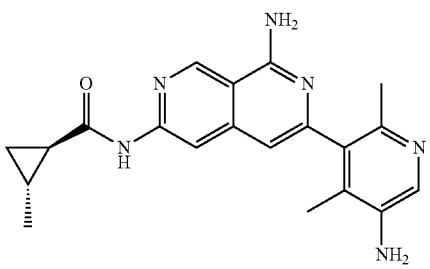

Step 1: tert-butyl N-(5-bromo-4,6-dimethyl-3-pyridyl)carbamate

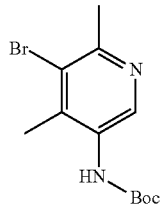

A mixture of 3,5-dibromo-2,4-dimethyl-pyridine (670 mg, 2.53 mmol), tert-butyl carbamate (300 mg, 2.56 mmol), Pd$_2$(dba)$_3$ (183 mg, 0.2 mmol), xantphos (235 mg, 0.41 mmol), Cs$_2$CO$_3$ (1500 mg, 4.62 mmol) in 1,4-dioxane (10 mL) was stirred under Ar at 90° C. for 16 hr. The reaction mixture was concentrated and purified by column chromatography on silica gel (ethyl acetate/petroleum ether, 1/5) to afford tert-butyl N-(5-bromo-4,6-dimethyl-3-pyridyl)carbamate (470 mg, 60.4% yield) as a yellow solid. LCMS (ESI): [M+H]$^+$=303.0.

Step 2: tert-butyl N-[4,6-dimethyl-5-(4,4,5,5-tetramethyl-1,3,2-dioxaborolan-2-yl)-3-pyridyl]carbamate

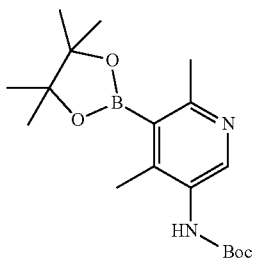 [SMILES: Cc1ncc(NC(=O)OC(C)(C)C)c(C)c1B1OC(C)(C)C(C)(C)O1]

A mixture of tert-butyl N-(5-bromo-4,6-dimethyl-3-pyridyl)carbamate (600 mg, 1.99 mmol), bis(pinacolato)diboron (1000 mg, 3.94 mmol), potassium acetate (400 mg, 4.08 mmol), Pd(dppf)Cl$_2$ (150 mg, 0.2 mmol) in 1,4-dioxane (10 mL) was stirred under Ar at 100° C. for 2 h. The reaction mixture was concentrated and purified by column chromatography on silica gel (ethyl acetate/petroleum ether 20=50%) to afford tert-butyl N-[4,6-dimethyl-5-(4,4,5,5-tetramethyl-1,3,2-dioxaborolan-2-yl)-3-pyridyl]carbamate (620 mg, 63.6% yield) as a yellow solid. LCMS(ESI): [M+H]$^+$=349.2.

Step 3: (±)-trans-N-(6,8-dichloro-2,7-naphthyridin-3-yl)-2-methyl-cyclopropanecarboxamide

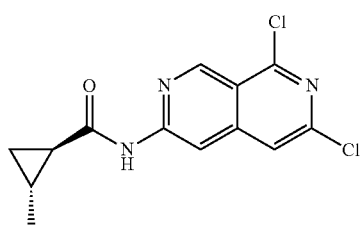

A mixture of 6,8-dichloro-2,7-naphthyridin-3-amine (320 mg, 1.49 mmol), pyridine (2 mL, 24.73 mmol) and POCl$_3$ (0.4 mL, 5.87 mmol) was stirred at room temperature. (±)-trans-2-methylcyclopropanecarboxylic acid (160 mg, 1.6 mmol) was then added. The reaction mixture was stirred at room temperature for 1 h. The reaction mixture was concentrated purified by reverse phase chromatography (methanol 0-80% in 0.05% ammonia in water) to afford (±)-trans-N-(6,8-dichloro-2,7-naphthyridin-3-yl)-2-methyl-cyclopropanecarboxamide (270 mg, 59% yield) as a yellow solid. LCMS(ESI): [M+H]$^+$=296.0.

Step 4: (±)-trans-N-(8-amino-6-chloro-2,7-naphthyridin-3-yl)-2-methyl-cyclopropanecarboxamide

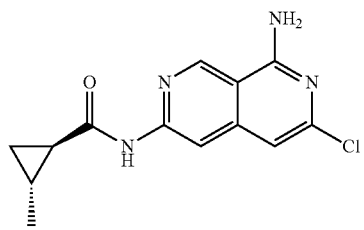 [SMILES: C[C@@H]1C[C@H]1C(=O)Nc1cc2cc(Cl)nc(N)c2cn1]

A mixture of (±)-trans-N-(6,8-dichloro-2,7-naphthyridin-3-yl)-2-methyl-cyclopropanecarboxamide (270 mg, 0.91 mmol) in ammonium hydroxide (25%, 4 mL) and 1,4-dioxane (4 mL) was stirred at 90° C. for 4 h. The mixture was concentrated to dryness to afford crude (±)-trans-N-(8-amino-6-chloro-2,7-naphthyridin-3-yl)-2-methyl-cyclopropanecarboxamide (310 mg) as a yellow liquid. LCMS(ESI): [M+H]$^+$=277.1.

Step 5: (±)-trans-tert-butyl N-[5-[1-amino-6-[[(trans)-2-methylcyclopropanecarbonyl]amino]-2,7-naphthyridin-3-yl]-4,6-dimethyl-3-pyridyl]carbamate

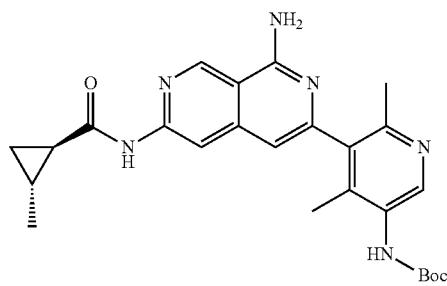 [SMILES: Cc1ncc(NC(=O)OC(C)(C)C)c(C)c1-c1cc2cc(NC(=O)[C@@H]3C[C@H]3C)ncc2c(N)n1]

A mixture of X-Phos-Pd-G2 (40 mg, 0.05 mmol), K$_2$CO$_3$ (200 mg, 1.45 mmol), X-Phos (50 mg, 0.11 mmol), tert-butyl N-[4,6-dimethyl-5-(4,4,5,5-tetramethyl-1,3,2-dioxaborolan-2-yl)-3-pyridyl]carbamate (300 mg, 0.86 mmol), and (±)-trans-N-(8-amino-6-chloro-2,7-naphthyridin-3-yl)-2-methyl-cyclopropanecarboxamide (150 mg, 0.54 mmol) in 1,4-dioxane (6 mL) and water (1 mL) was stirred under Ar at 100° C. for 1 h. The reaction was concentrated and purified by column chromatography on (methanol/dichloromethane, 1/10) to afford (±)-tert-butyl N-[5-[1-amino-6-[[(trans)-2-methylcyclopropanecarbonyl]amino]-2,7-naphthyridin-3-yl]-4,6-dimethyl-3-pyridyl]carbamate (80 mg, 21.8% yield) as a yellow solid. LCMS(ESI): [M+H]⁺=463.3.

Step 6: (±)-trans-N-[8-amino-6-(5-amino-2,4-dimethyl-3-pyridyl)-2,7-naphthyridin-3-yl]-2-methyl-cyclopropanecarboxamide

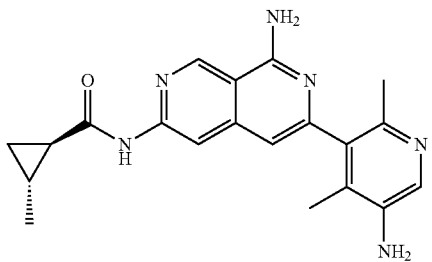 [SMILES: Cc1ncc(N)c(C)c1-c1cc2cc(NC(=O)[C@@H]3C[C@H]3C)ncc2c(N)n1]

A solution of (±)-tert-butyl N-[5-[1-amino-6-[[(trans)-2-methylcyclopropanecarbonyl]amino]-2,7-naphthyridin-3-yl]-4,6-dimethyl-3-pyridyl]carbamate (80 mg, 0.17 mmol) in HCl in dioxane (4M, 2 mL, 8 mmol) was stirred at room temperature for 1 h. The reaction solution was concentrated and purified by reverse phase chromatography (methanol 0-30%% in 0.05% ammonia in water) to afford (±)-trans-N-[8-amino-6-(5-amino-2,4-dimethyl-3-pyridyl)-2,7-naphthyridin-3-yl]-2-methyl-cyclopropanecarboxamide (27 mg, 42.6% yield) as a yellow solid. LCMS(ESI): [M+H]⁺=363.2, R$_T$(min)=1.56, Method=F; ¹H NMR (400 MHz, CD₃OD) δ 9.30 (s, 1H), 8.25 (s, 1H), 7.92 (s, 1H), 6.78 (s, 1H), 2.19 (s, 3H), 1.97 (s, 3H), 1.72-1.67 (m, 1H), 1.48-1.45 (m, 1H), 1.25-1.22 (m, 1H), 1.19 (d, J=6.0 Hz, 3H), 0.79-0.75 (m, 1H).

Example 145

2-[4-[[8-amino-6-(4-methyl-3-pyridyl)-2,7-naphthyridin-3-yl]amino]pyrazol-1-yl]-N,2-dimethyl-propanamide (Compound 182)

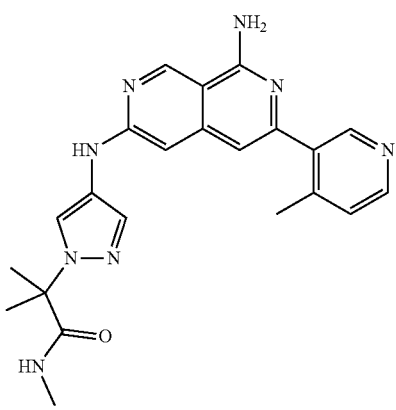 [SMILES: CNC(=O)C(C)(C)n1cc(Nc2cc3cc(-c4cnccc4C)nc(N)c3cn2)cn1]

Step 1: 2-bromo-N,2-dimethyl-propanamide

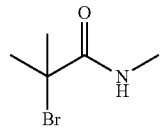

To a solution of methanamine (2M in THF, 10. mL, 20 mmol) 0° C. was added 2-bromo-2-methylpropionyl bromide (1 mL, 8.09 mmol). The mixture was warmed to room temperature for 30 min. The reaction was concentrated and washed with 1 N sodium bicarbonate. The aqueous layer was extracted with dichloromethane (15 mL×2) and separated. The organics was dried over sodium sulfate, filtered and concentrated to afforded 2-bromo-N,2-dimethyl-propanamide (1.2 g, 82.4% yield) as colorless crystals. LCMS (ESI): [M+H]⁺=182.0.

Step 2: 2-(4-bromopyrazol-1-yl)-N,2-dimethyl-propanamide

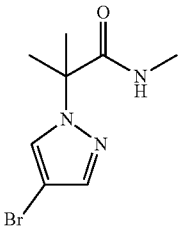

A mixture of 4-bromo-1H-pyrazole (735 mg, 5 mmol), NaH (60% in mine oil, 310 mg, 7.75 mmol) in N,N-dimethylformamide (5 mL) was stirred at room temperature for 10 min. A solution of 2-bromo-N,2-dimethyl-propanamide (1130 mg, 6.28 mmol) in N,N-dimethyl formamide (5 mL) was added. The reaction mixture was stirred at room temperature for 1 h. The reaction was diluted with saturated NH₄Cl aqueous (5 mL) and 50 mL of brine. The mixture was extracted with ethyl acetate (20 mL×3). The organics was separated and dried with Na₂SO₄, concentrated and purified by column chromatography (ethyl acetate/petroleum ether 1/1) to afford 2-(4-bromopyrazol-1-yl)-N,2-dimethyl-propanamide (1400 mg, 92.9% yield) as a colorless liquid. LCMS (ESI): [M+H]⁺=246.0.

Step 3: 2-[4-[[8-[bis [(2,4-dimethoxyphenyl)methyl]
amino]-6-(4-methyl-3-pyridyl)-2,7-naphthyridin-3-
yl]amino]pyrazol-1-yl]-N,2-dimethyl-propanamide

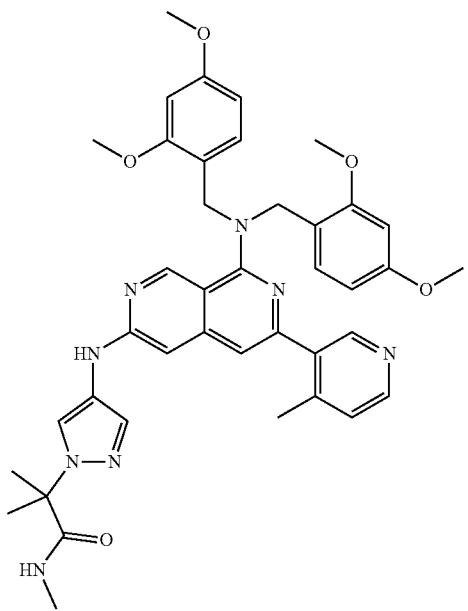 [SMILES: CNC(=O)C(C)(C)n1cc(Nc2cc3cc(-c4cnccc4C)nc(N(Cc4ccc(OC)cc4OC)Cc4ccc(OC)cc4OC)c3cn2)cn1]

A mixture of N1,N1-bis[(2,4-dimethoxyphenyl)methyl]-3-(4-methyl-3-pyridyl)-2,7-naphthyridine-1,6-diamine (220 mg, 0.4 mmol), t-BuONa (250 mg, 2.6 mmol), t-BuXPhos (200 mg, 0.42 mmol), Pd$_2$(dba)$_3$ (183 mg, 0.2 mmol), 2-(4-bromopyrazol-1-yl)-N,2-dimethyl-propanamide (600 mg, 2.44 mmol) in 1,4-dioxane (10 mL) was stirred under Ar at 130° C. for 16 hr. The reaction mixture was concentrated and purified by column chromatography (methanol/dichloromethane, 1/10) to afford 2-[4-[[8-[bis[(2,4-dimethoxyphenyl)methyl]amino]-6-(4-methyl-3-pyridyl)-2,7-naphthyridin-3-yl]amino]pyrazol-1-yl]-N,2-dimethyl-propanamide (130 mg, 41.7% yield) as a yellow solid. LCMS(ESI): [M+H]$^+$=717.4.

Step 4: 2-[4-[[8-amino-6-(4-methyl-3-pyridyl)-2,7-naphthyridin-3-yl]amino]pyrazol-1-yl]-N,2-dimethyl-propanamide

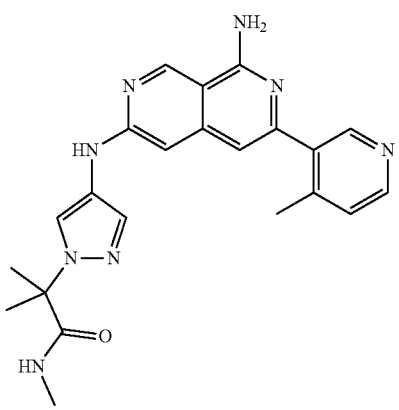 [SMILES: CNC(=O)C(C)(C)n1cc(Nc2cc3cc(-c4cnccc4C)nc(N)c3cn2)cn1]

A solution of 2-[4-[[8-[bis[(2,4-dimethoxyphenyl)methyl]amino]-6-(4-methyl-3-pyridyl)-2,7-naphthyridin-3-yl]amino]pyrazol-1-yl]-N,2-dimethyl-propanamide (130 mg, 0.18 mmol) in trifluoroacetic acid (2 mL) was stirred at 80° C. for 1 h. The reaction was concentrated and purified by reverse phase chromatography (acetonitrile 26-35% in 0.05% ammonia in water) to afford 2-[4-[[8-amino-6-(4-methyl-3-pyridyl)-2,7-naphthyridin-3-yl]amino]pyrazol-1-yl]-N,2-dimethyl-propanamide (40 mg, 48.7% yield) as a yellow solid. LCMS(ESI): [M+H]$^+$=417.2, R$_T$(min)=1.40, Method=F; $^1$H NMR (400 MHz, CD$_3$OD) δ 9.16 (s, 1H), 8.51 (s, 1H), 8.43 (d, J=5.2 Hz, 1H), 8.05 (s, 1H), 7.68 (s, 1H), 7.39 (d, J=5.2 Hz, 1H), 6.77 (s, 1H), 6.75 (s, 1H), 2.74 (s, 3H), 2.45 (s, 3H), 1.83 (s, 6H).

Example 146

2-[4-[[8-amino-6-(4-methyl-3-pyridyl)-2,7-naphthyridin-3-yl]amino]pyrazol-1-yl]-N,N,2-trimethyl-propanamide (Compound 183)

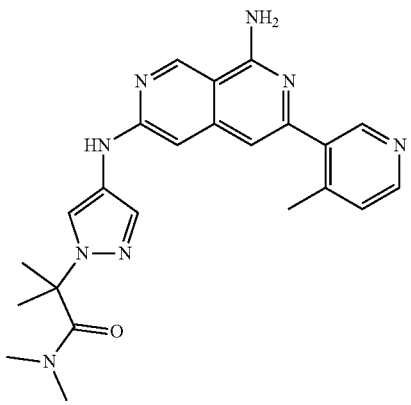 [SMILES: Cc1ccncc1-c1cc2cc(Nc3cnn(C(C)(C)C(=O)N(C)C)c3)ncc2c(N)n1]

Step 1: methyl 2-(4-bromopyrazol-1-yl)-2-methyl-propanoate

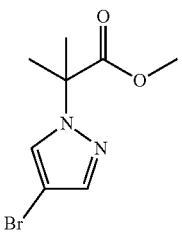

To a solution of 4-bromo-1H-pyrazole (3.0 g, 20.4 mmol) in N,N-dimethylformamide (10 mL) was added NaH (60% in mineral oil, 1.0 g, 25 mmol) at 0° C. The reaction mixture was stirred at 0° C. for 10 min. Methyl 2-bromo-2-methyl-propanoate (5 mL, 38.67 mmol) was added. The reaction mixture was stirred at room temperature for 1 h before 50 mL of brine was added. The mixture was extracted with ethyl acetate (20 mL×3). The organics were dried with Na$_2$SO$_4$, concentrated and purified by column chromatography (ethyl acetate/petroleum ether, 1:3) to afford methyl 2-(4-bromopyrazol-1-yl)-2-methyl-propanoate (4.7 g, 93.2% yield) as a colorless liquid. LCMS(ESI): [M+H]⁺=249.0.

Step 2:
2-(4-bromopyrazol-1-yl)-2-methyl-propanoic acid

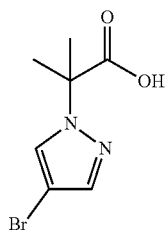

A mixture of methyl 2-(4-bromopyrazol-1-yl)-2-methyl-propanoate (2.0 g, 8.09 mmol), NaOH (600 mg, 15 mmol) in methyl alcohol (10 mL) and water (1 mL) was stirred at room temperature for 4 h. The reaction was neutralized with a solution of HCl (3 mL, 36 mmol). The reaction was concentrated to dryness and purified by column chromatography (ethyl acetate/petroleum ether 30-50%) to afford 2-(4-bromopyrazol-1-yl)-2-methyl-propanoic acid (1.42 g, 75.3% yield) as a white solid. LCMS(ESI): [M+H]⁺=233.1.

Step 3: 2-(4-bromopyrazol-1-yl)-N,N,2-trimethyl-propanamide

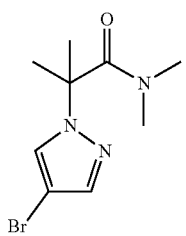

A solution of 2-(4-bromopyrazol-1-yl)-2-methyl-propanoic acid (700 mg, 3 mmol), N,N-dimethylamine (2M in THF, 6 mL, 12 mmol) in dichloromethane (20 mL) was stirred at 0° C. POCl₃ (0.5 mL, 5.38 mmol) was added dropwise and the reaction mixture stirred at room temperature overnight. The reaction mixture was diluted with 20 mL water. The organics were then separated, concentrated and purified by column chromatography (ethyl acetate/petroleum ether, 30-50%) to afford 2-(4-bromopyrazol-1-yl)-N,N,2-trimethyl-propanamide (400 mg, 51.2% yield) as a white solid. LCMS (ESI): [M+H]⁺=262.0.

Step 4: 2-[4-[[8-[bis[(2,4-dimethoxyphenyl)methyl]amino]-6-(4-methyl-3-pyridyl)-2,7-naphthyridin-3-yl]amino]pyrazol-1-yl]-N,N,2-trimethyl-propanamide

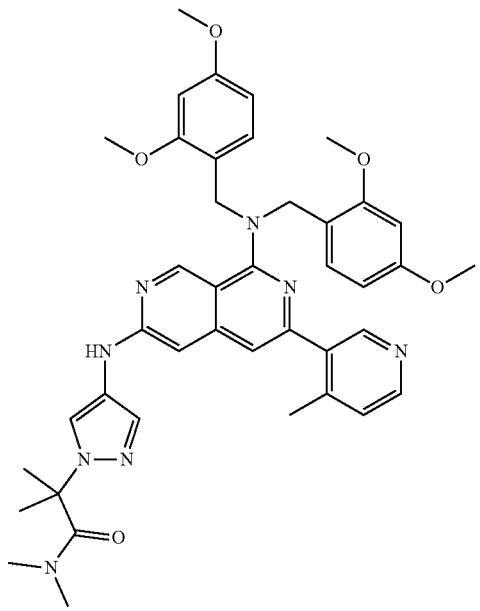

A mixture of N1,N1-bis[(2,4-dimethoxyphenyl)methyl]-3-(4-methyl-3-pyridyl)-2,7-naphthyridine-1,6-diamine (200 mg, 0.36 mmol), t-BuONa (150 mg, 1.56 mmol), t-BuXPhos (150 mg, 0.31 mmol), Pd₂(dba)₃ (140 mg, 0.15 mmol), and 2-(4-bromopyrazol-1-yl)-N,N,2-trimethyl-propanamide (370 mg, 1.42 mmol) in 1,4-dioxane (10 mL) was stirred under Ar at 130° C. for 7 h. The reaction was concentrated to dryness and purified by column chromatography (ethyl acetate to 5% methanol/dichloromethane) to afford 2-[4-[[8-[bis[(2,4-dimethoxyphenyl)methyl]amino]-6-(4-methyl-3-pyridyl)-2,7-naphthyridin-3-yl]amino]pyrazol-1-yl]-N,N,2-trimethyl-propanamide (220 mg, 70.5% yield) as a yellow solid. LCMS (ESI): [M+H]⁺=731.4.

Step 5: 2-[4-[[8-amino-6-(4-methyl-3-pyridyl)-2,7-naphthyridin-3-yl]amino]pyrazol-1-yl]-N,N,2-trimethyl-propanamide

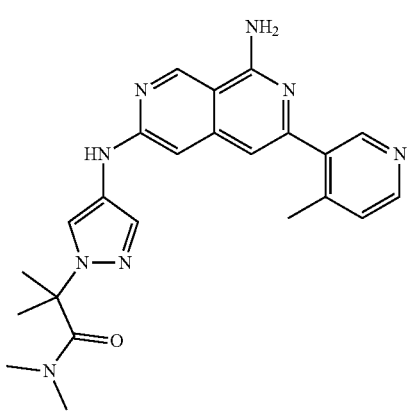 [SMILES: Cc1ccncc1-c1cc2cc(Nc3cnn(C(C)(C)C(=O)N(C)C)c3)ncc2c(N)n1]

A solution of 2-[4-[[8-[bis[(2,4-dimethoxyphenyl)methyl]amino]-6-(4-methyl-3-pyridyl)-2,7-naphthyridin-3-yl]amino]pyrazol-1-yl]-N,N,2-trimethyl-propanamide (220 mg, 0.3 mmol) in trifluoroacetic acid (2 mL) was stirred at 80° C. for h. The reaction was concentrated to dryness and purified by reverse phase chromatography (methanol 45-55%% in 0.05% ammonia in water) to afford 2-[4-[[8-amino-6-(4-methyl-3-pyridyl)-2,7-naphthyridin-3-yl]amino]pyrazol-1-yl]-N,N,2-trimethyl-propanamide (73 mg, 56.3% yield) as a yellow solid. LCMS(ESI): [M+H]$^+$=431.2, R$_T$(min)=1.29, Method=A; $^1$H NMR (400 MHz, CD$_3$OD) δ 9.18 (s, 1H), 8.50 (s, 1H), 8.42 (d, J=5.2 Hz, 1H), 8.06 (s, 1H), 7.67 (s, 1H), 7.39 (d, J=5.2 Hz, 1H), 6.77 (s, 1H), 6.72 (s, 1H), 2.99 (s, 3H), 2.54 (s, 3H), 2.45 (s, 3H), 1.82 (s, 6H).

Example 147

2-[4-[[8-amino-6-(4-methyl-3-pyridyl)-2,7-naphthyridin-3-yl]amino]pyrazol-1-yl]-N-methyl-acetamide (Compound 184)

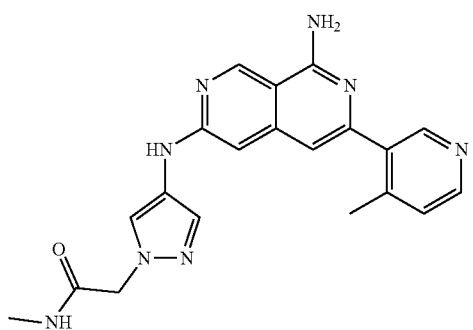 [SMILES: CNC(=O)Cn1cc(Nc2cc3cc(-c4cnccc4C)nc(N)c3cn2)cn1]

Step 1 2-(4-bromopyrazol-1-yl)-N-methyl-acetamide

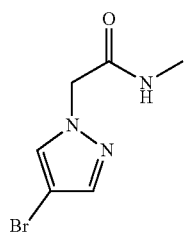

A mixture of 4-bromo-1H-pyrazole (735 mg, 5 mmol), NaH (60% in mine oil, 330 mg, 8.25 mmol) in N,N-dimethylformamide (5 mL) was stirred at room temperature for 10 min. A solution of 2-bromo-N-methyl-acetamide (910 mg, 5.99 mmol) in N,N-dimethylformamide (5 mL) was then added. The reaction mixture was stirred at room temperature for 1 h. The reaction was diluted with saturated NH$_4$Cl solution (5 ml) and brine (50 mL). The mixture was extracted with ethyl acetate (20 mL×3). The organics was separated and dried with Na$_2$SO$_4$. The organics was concentrated to dryness and purified by column chromatography (methanol/DCM, 1:10) to afford 2-(4-bromopyrazol-1-yl)-N-methyl-acetamide (870 mg, 79.8% yield) as a white solid. LCMS(ESI): [M+H]$^+$=220.0.

Step 2: 2-[4-[[8-[bis[(2,4-dimethoxyphenyl)methyl]amino]-6-(4-methyl-3-pyridyl)-2,7-naphthyridin-3-yl]amino]pyrazol-1-yl]-N-methyl-acetamide

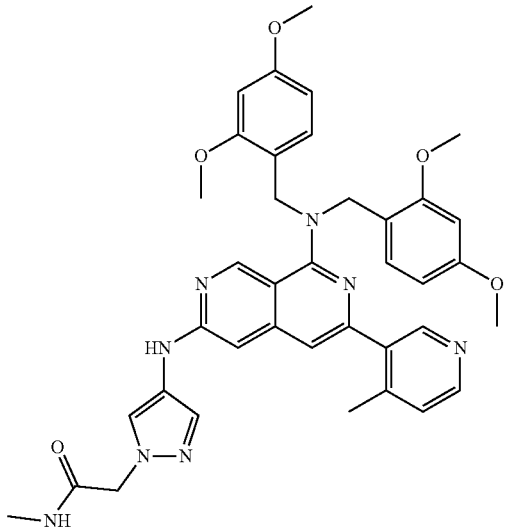

A mixture t-BuONa (500 mg, 5.2 mmol), t-BuXPhos (180 mg, 0.37 mmol), Pd$_2$(dba)$_3$ (183.0 mg, 0.2 mmol), 2-(4-bromopyrazol-1-yl)-N-methyl-acetamide (440 mg, 2.02 mmol), and N1,N1-bis[(2,4-dimethoxyphenyl)methyl]-3-(4-methyl-3-pyridyl)-2,7-naphthyridine-1,6-diamine (220 mg, 0.4 mmol) in 1,4-dioxane (10 mL) was stirred under an Ar atmosphere at 130° C. for 7 h. The reaction was concentrated to dryness and the crude residue was then purified by column chromatography on silica gel eluting with ethyl acetate/methanol 1/10 to afford 2-[4-[[8-[bis[(2,4-dimethoxyphenyl) methyl] amino]-6-(4-methyl-3-pyridyl)-2,7-naphthyridin-3-yl]amino]pyrazol-1-yl]-N-methyl-acetamide (40 mg, 10.7% yield) as a yellow solid. LCMS(ESI): [M+H]$^+$=689.4.

Step 3: 2-[4-[[8-amino-6-(4-methyl-3-pyridyl)-2,7-naphthyridin-3-yl]amino]pyrazol-1-yl]-N-methyl-acetamide

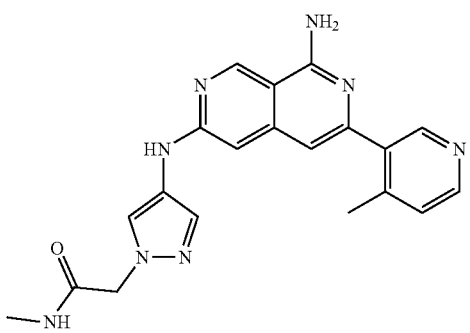

A solution of 2-[4-[[8-[bis[(2,4-dimethoxyphenyl)methyl]amino]-6-(4-methyl-3-pyridyl)-2,7-naphthyridin-3-yl]amino]pyrazol-1-yl]-N-methyl-acetamide (40 mg, 0.06 mmol) in trifluoroacetic acid (1 mL) was stirred at 80° C. for 1 h. The reaction was concentrated to dryness and purified by reverse phase chromatography (methanol 45-55%% in 0.05% ammonia in water) to afford 2-[4-[[8-amino-6-(4-methyl-3-pyridyl)-2,7-naphthyridin-3-yl]amino]pyrazol-1-yl]-N-methyl-acetamide (8 mg, 35.5% yield) as a yellow solid. LCMS(ESI): [M+H]$^+$=389.2, R$_T$(min)=1.18, Method=A; $^1$H NMR (400 MHz, CD$_3$OD) S 9.15 (s, 1H), 8.50 (s, 1H), 8.42 (d, J=5.2 Hz, 1H), 7.98 (s, 1H), 7.64 (s, 1H), 7.39 (d, J=5.2 Hz, 1H), 6.76 (s, 1H), 6.75 (s, 1H), 4.86 (s, 2H), 2.80 (s, 3H), 2.44 (s, 3H).

Example 148

(±)-trans-2-cyano-N-(6-((S)-4-methyl-2-oxooxazolidin-3-yl)isoquinolin-3-yl)cyclopropanecarboxamide (Compound 185)

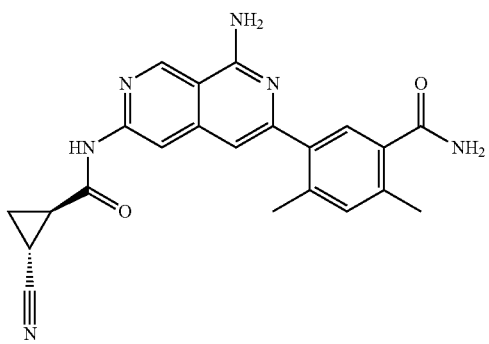 [SMILES: Cc1cc(C)c(-c2cc3cc(NC(=O)[C@@H]4C[C@H]4C#N)ncc3c(N)n2)cc1C(N)=O]

Step 1: 5-bromo-2,4-dimethylbenzoic acid

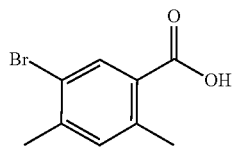

A mixture of methyl 5-bromo-2,4-dimethyl-benzoate (400 mg, 1.65 mmol), LiOH (197 mg, 8.21 mmol) in tetrahydrofuran (3 mL) and water (3 mL) was stirred under N$_2$ at 70° C. for 3 h. The reaction was then diluted with 30 mL of water and 20 mL of EtOAc. The mixture was then adjusted pH to 4-5 with 1N HCl. The organic layer was concentrated to dryness to give the title compound as a white solid (350 mg, 92.9% yield). LCMS (ESI) [M+H]+=230.9.

Step 2: 5-bromo-2,4-dimethylbenzamide

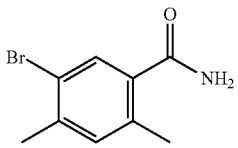

A mixture of 5-bromo-2,4-dimethyl-benzoic acid (350 mg, 1.53 mmol), ammoniumchloride (162 mg, 3.03 mmol), DIEA (798 mg, 6.19 mmol), HATU (754 mg, 1.98 mmol) in dichloromethane (20 mL) was stirred at room temperature for 2 h. The reaction was concentrated to dryness. The residue was taken up in EtOAc (10 mL), washed with 150 mL of brine, dried (NaSO$_4$) and concentrated. The residue was purified with column chromatography (PE:EA=5:1 to PE:EA=1:1) to afford the title compound as a white solid (340 mg, 92% yield). LCMS (ESI) [M+H]+=230.1.

Step 3: 2,4-dimethyl-5-(4,4,5,5-tetramethyl-1,3,2-dioxaborolan-2-yl)benzamide

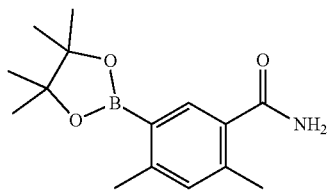 [SMILES: Cc1cc(C)c(C(N)=O)cc1B1OC(C)(C)C(C)(C)O1]

A mixture of 5-bromo-2,4-dimethyl-benzamide (340 mg, 1.49 mmol), bis(pinacolato)diboron (567 mg, 2.23 mmol), PdCl$_2$dppf (218 mg, 0.3 mmol), KOAc (438 mg, 4.47 mmol) in 1,4-dioxane (15 mL) was stirred under Ar at 100° C. for 3 h. The reaction was concentrated and purified by silica chromatography (PE:EA=4:1 to PE:EA=2:1) to give the title compound as a white solid (370 mg, 62.1% yield). LCMS (ESI) [M+H]+=276.2.

Step 4: (±)-5-(1-amino-6-(trans-2-cyanocyclopropanecarboxamido)-2,7-naphthyridin-3-yl)-2,4-dimethylbenzamide

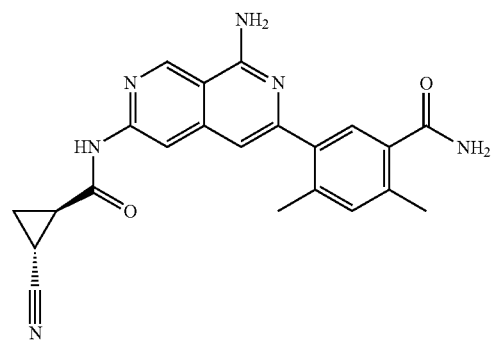 [SMILES: Cc1cc(C)c(-c2cc3cc(NC(=O)[C@@H]4C[C@H]4C#N)ncc3c(N)n2)cc1C(N)=O]

A mixture of 2,4-dimethyl-5-(4,4,5,5-tetramethyl-1,3,2-dioxaborolan-2-yl)benzamide (300 mg, 1.09 mmol), trans-N-(8-amino-6-chloro-2,7-naphthyridin-3-yl)-2-cyano-cyclopropanecarboxamide (100 mg, 0.35 mmol), PdCl$_2$dppf (80 mg, 0.11 mmol), K$_2$CO$_3$ (450 mg, 3.26 mmol) in 1,4-dioxane (10 mL) was heated at 100° C. for 3 h under Ar gas. The reaction was concentrated to dryness. The residue was purified with silica chromatography (PE:EA=4:1 to PE:EA=1:1, Rf=0.4 at PE/EA 1/1). The product is a white solid (50.9 mg, 11.7% yield). LCMS (ESI): RT(min)=1.45, [M+H]$^+$=401.2, method=B. $^1$HNMR (400 MHz, DMSO-d$_6$) δ 11.25 (s, 1H), 9.37 (s, 1H), 8.18 (s, 1H), 7.69 (s, 1H), 7.50 (s, 1H), 7.28-7.26 (m, 3H), 7.12 (s, 1H), 6.94 (s, 1H), 2.77-2.75 (m, 1H), 2.38 (s, 6H), 2.15-2.13 (m, 1H), 1.61-1.57 (m, 1H), 1.43-1.41 (m, 1H).

Example 149 trans-N-(8-amino-6-((S)-4-methyl-2-oxooxazolidin-3-yl)-2,7-naphthyridin-3-yl)-2-cyanocyclopropanecarboxamide (Compound 186)

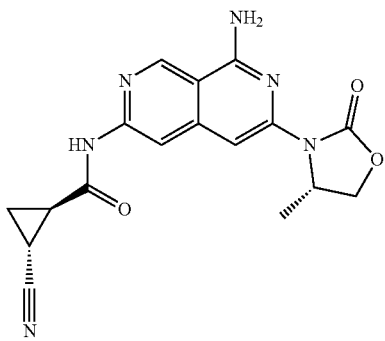 [SMILES: C[C@H]1COC(=O)N1c1cc2cc(NC(=O)[C@@H]3C[C@H]3C#N)ncc2c(N)n1]

Step 1: (±)-trans-N-[8-[bis[(2,4-dimethoxybenzyl)methyl]amino]-6-chloro-2,7-naphthyridin-3-yl]-2-cyano-cyclopropanecarboxamide

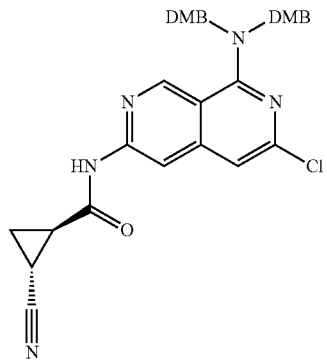

A mixture of at (±)-trans-2-cyano-N-(6,8-dichloro-2,7-naphthyridin-3-yl)cyclopropanecarboxamide (1 g, 3.26 mmol), bis(2,4-dimethoxybenzyl)amine (5 g, 15.75 mmol), TEA (2.5 mL, 18.07 mmol) in 1,4-dioxane (40 mL) was stirred under Ar at 120° C. for 16 h. The reaction was concentrated to dryness and purified by silica gel chromatography (PE:EA=4:1 to PE:EA=2:1) to give the title compound as a yellow solid (520 mg, 21.8% yield). LCMS (ESI) [M+H]+=588.2.

Step 2: trans-N-[8-[bis[(2,4-dimethoxybenzyl)methyl]amino]-6-[(4S)-4-methyl-2-oxo-oxazolidin-3-yl]-2,7-naphthyridin-3-yl]-2-cyano-cyclopropanecarboxamide

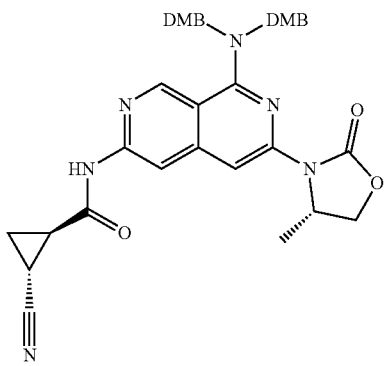

A mixture of (±)-trans-N-[8-[bis[(2,4-dimethoxybenzyl)methyl]amino]-6-chloro-2,7-naphthyridin-3-yl]-2-cyano-cyclopropanecarboxamide (470 mg, 0.8 mmol), (4S)-4-methyloxazolidin-2-one (300 mg, 2.97 mmol), Xantphos (200 mg, 0.35 mmol), Pd$_2$(dba)$_3$ (300 mg, 0.33 mmol) and K$_2$CO$_3$ (330 mg, 2.39 mmol) in 1,4-dioxane (40 mL) was stirred under Ar at 100° C. for 3 h. The reaction was concentrated and purified by silica gel chromatography (PE:EA=4:1) followed by prep-HPLC (eluent: 5%-95% methanol and 0.1 mL/L % TFA in water) to give the title compound as a yellow solid (190 mg, 24.3% yield). LCMS (ESI) [M+H]+=653.3.

Step 3: trans-N-(8-amino-6-((S)-4-methyl-2-oxooxazolidin-3-yl)-2,7-naphthyridin-3-yl)-2-cyanocyclopropane carboxamide

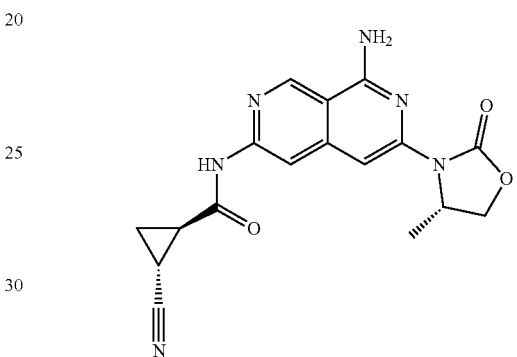

A mixture of trans-N-[8-[bis[(2,4-dimethoxybenzyl)]amino]-6-[(4S)-4-methyl-2-oxo-oxazolidin-3-yl]-2,7-naphthyridin-3-yl]-2-cyano-cyclopropanecarboxamide (180 mg, 0.28 mmol) in TFA (4 mL, 0.28 mmol) was heated under Ar at 70° C. for 4 h. The reaction was concentrated and purified by prep-HPLC (eluent: 5%-95% methanol and 0.8 g/L NH$_4$HCO$_3$ in water) to give the title compound as a white solid (43.3 mg, 42.6% yield). LCMS (ESI): RT(min)=1.60, [M+H]+=353.2, method=B. $^1$HNMR (400 MHz, DMSO-d$_6$) δ 11.17 (s, 1H), 9.26 (s, 1H), 8.01 (s, 1H), 7.38 (s, 2H), 7.30 (s, 1H), 4.85-4.81 (m, 1H), 4.50 (t, J=8.4 Hz, 1H), 4.06-4.03 (m, 1H), 2.76-2.71 (m, 1H), 2.17-2.13 (m, 1H), 1.61-1.57 (m, 1H), 1.45-1.40 (m, 1H), 1.38 (d, J=6.4 Hz, 3H).

Example 150

(±)-trans-N-(8-amino-6-(5-methyl-1H-pyrazol-4-yl)-2,7-naphthyridin-3-yl)-2-(trifluoromethyl)cyclopropanecarboxamide (Compound 187)

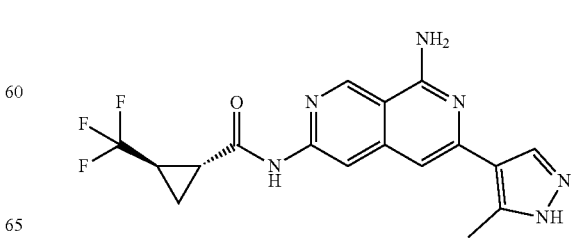

Step 1: (±)-trans-N-(6,8-dichloro-2,7-naphthyridin-3-yl)-2-(trifluoromethyl)cyclopropanecarboxamide

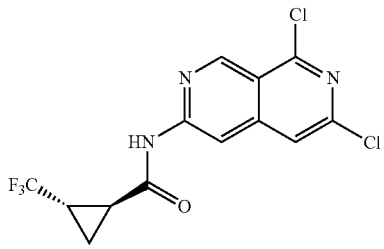 [SMILES: O=C(Nc1cc2cc(Cl)nc(Cl)c2cn1)[C@H]1C[C@@H]1C(F)(F)F]

A mixture of (±)-trans-2-(trifluoromethyl)cyclopropanecarboxylic acid (734 mg, 4.76 mmol), 6,8-dichloro-2,7-naphthyridin-3-amine (850 mg, 3.97 mmol) in pyridine (1 mL) and dichloromethane (20 mL) was stirred at room temperature for 0.5 h. POCl$_3$ (0.4 mL, 4.29 mmol) was added in portions at room temperature. The mixture was stirred for 1 h. The reaction was neutralized with sat NaHCO$_3$. The organics were then separated and dried (NaSO$_4$) before concentration and purified by silica gel chromatography (PE:EA=10:1 to PE:EA=4:1) to give the title compound as a white solid (1.1 g, 76.7% yield). LCMS (ESI) [M+H]+=350.0.

Step 2: (±)-trans-N-(8-amino-6-chloro-2,7-naphthyridin-3-yl)-2-(trifluoromethyl)cyclopropanecarboxamide

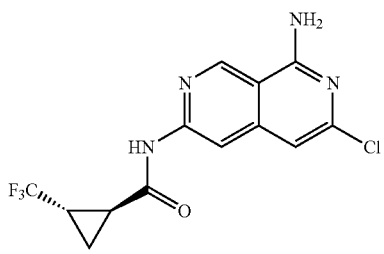 [SMILES: Nc1nc(Cl)cc2cc(NC(=O)[C@H]3C[C@@H]3C(F)(F)F)ncc12]

A mixture of (±)-trans-N-(6,8-dichloro-2,7-naphthyridin-3-yl)-2-(trifluoromethyl)cyclopropanecarboxamide (1.1 g, 3.14 mmol), NH$_4$OH (10 mL, 3.14 mmol) in 1,4-dioxane (10 mL) was stirred under Ar at 90° C. for 3 h. The reaction was concentrated and purified by silica gel chromatography (PE:EA=4:1) to give the title compound as a white solid (0.9 g, 85.3% yield). LCMS (ESI) [M+H]+=331.1.

Step 3: (±)-trans-N-(8-amino-6-(5-methyl-1H-pyrazol-4-yl)-2,7-naphthyridin-3-yl)-2-(trifluoromethyl) cyclopropane carboxamide

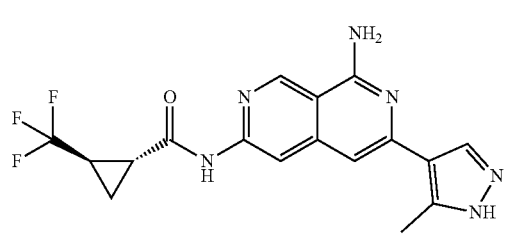 [SMILES: Cc1[nH]ncc1-c1cc2cc(NC(=O)[C@@H]3C[C@H]3C(F)(F)F)ncc2c(N)n1]

A mixture of (±)-trans-N-(8-amino-6-chloro-2,7-naphthyridin-3-yl)-2-(trifluoromethyl)cyclopropanecarboxamide (150 mg, 0.45 mmol), 5-methyl-4-(4,4,5,5-tetramethyl-1,3,2-dioxaborolan-2-yl)-1H-pyrazole (113 mg, 0.54 mmol), XPhos (22 mg, 0.05 mmol), XPhos Pd G2 (36 mg, 0.05 mmol) and K$_2$CO$_3$ (187 mg, 1.36 mmol) in 1,4-dioxane (8 mL) and water (2 mL) was stirred under Ar at 120° C. for 3 h. The reaction was concentrated and purified by silica gel chromatography (PE:EA=1:1) to give the title compound as a white solid (58.1 mg, 33.8% yield). LCMS (ESI): RT(min)=1.56, [M+H]+=377.2, method=B. $^1$HNMR (400 MHz, DMSO-d$_6$) δ 12.64 (s, 1H), 11.09 (s, 1H), 9.26 (s, 1H), 8.12 (s, 1H), 7.96 (d, J=8.4 Hz, 1H), 7.12 (s, 2H), 6.98 (s, 1H), 2.62-2.56 (m, 4H), 2.33-2.27 (m, 1H), 1.32-1.30 (m, 2H).

Example 151

(±)-trans-N-(8-amino-6-(1,3,5-trimethyl-1H-pyrazol-4-yl)-2,7-naphthyridin-3-yl)-2-(trifluoromethyl)cyclopropanecarboxamide (Compound 188)

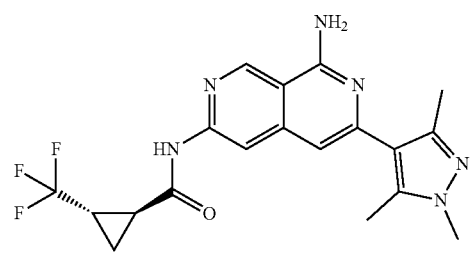 [SMILES: Cc1nn(C)c(C)c1-c1cc2cc(NC(=O)[C@H]3C[C@@H]3C(F)(F)F)ncc2c(N)n1]

A mixture of 1,3,5-trimethyl-4-(4,4,5,5-tetramethyl-1,3,2-dioxaborolan-2-yl)-1h-pyrazole (161 mg, 0.68 mmol), (±)-trans-N-(8-amino-6-chloro-2,7-naphthyridin-3-yl)-2-(trifluoromethyl)cyclopropanecarboxamide (150 mg, 0.45 mmol), Pd(PPh$_3$)$_4$ (104 mg, 0.09 mmol) and K$_2$CO$_3$ (186 mg, 1.35 mmol) in 1,4-dioxane (8 mL) and water (2 mL) was stirred under Ar at 100° C. for 3 h. The reaction was concentrated and purified by silica gel chromatography (PE:EA=1:1 to EA:DCM=4:1) to give the title compound as a white solid (72.3 mg, 39.1% yield). LCMS (ESI): RT(min)=1.57, [M+H]+=405.2, method=B. $^1$HNMR (400 MHz, CD$_3$OD) δ 9.21 (s, 1H), 8.23 (s, 1H), 6.81 (s, 1H), 3.77 (s, 3H), 2.46-2.43 (m, 1H), 2.41 (s, 3H), 2.33 (s, 3H), 2.30-2.26 (m, 1H), 1.45-1.41 (m, 1H), 1.37-1.32 (m, 1H).

Example 152

(±)-trans-N-(8-amino-6-(4-methylpyridin-3-yl)-2,7-naphthyridin-3-yl)-2-(pyrimidin-2-yl)cyclopropanecarboxamide (Compound 189)

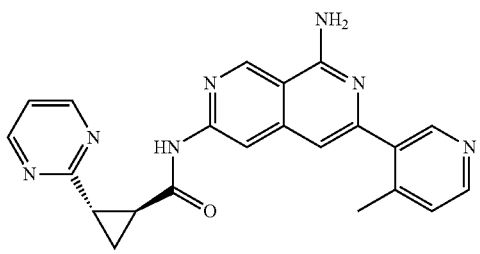 [SMILES: Cc1ccncc1-c1cc2cc(NC(=O)[C@H]3C[C@@H]3c3ncccn3)ncc2c(N)n1]

Step 1: (E)-tert-butyl 3-(pyrimidin-2-yl)acrylate

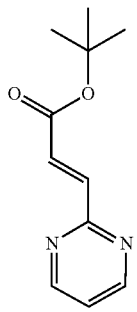

A mixture of tert-butyl diethylphosphonoacetate (4.5 g, 17.84 mmol), NaH (0.84 g, 35 mmol) in tetrahydrofuran (50 mL) was stirred at 0° C. for 0.5 h. 2-pyrimidinecarboxaldehyde (1.9 g, 17.58 mmol) was added at room temperature. The mixture was stirred for 2 h. The reaction diluted with EtOAc (50 mL) and the pH adjusted to 7-8 with sat. NH$_4$Cl. The organics were then separated, dried (NaSO$_4$) and concentrated to dryness. The residue was purified by silica gel chromatography (PE:EA=2:1) to give the title compound as a colorless oil (2.5 g, 67.9% yield). LCMS (ESI) [M+H]$^+$=207.1. $^1$H NMR (400 MHz, DMSO-d$_6$) δ 8.88 (s, 1H), 8.87 (s, 1H), 7.48 (t, J=4.8 Hz, 1H), 7.41 (d, J=15.6 Hz, 1H), 6.94 (d, J=15.6 Hz, 1H), 1.48 (s, 9H).

Step 2: (±)-trans-tert-butyl 2-(pyrimidin-2-yl)cyclopropanecarboxylate

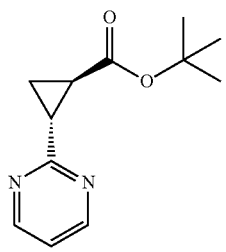 [SMILES: CC(C)(C)OC(=O)[C@@H]1C[C@H]1c1ncccn1]

A mixture of trimethyloxosulfonium iodide (2.7 g, 11.64 mmol) and tBuOK (1.3 g, 11.61 mmol) in dimethyl sulfoxide (50 mL) was stirred at room temperature for 0.5 h. tert-Butyl (E)-3-pyrimidin-2-ylprop-2-enoate (2.4 g, 11.64 mmol) was then added. The mixture was stirred for 2 h. The reaction was diluted with EtOAc (50 mL) and adjusted pH to 7-8 with sat NH$_4$Cl. The organics were then separated, dried (NaSO$_4$) and concentrated to dryness. The residue was purified with silica gel chromatography (PE:EA=10:1 to PE:EA=4:1) to give the title compound as a colorless oil (370 mg, 14.4% yield). LCMS (ESI) [M+H]+=165.2.

Step 3: (±)-trans-2-(pyrimidin-2-yl)cyclopropanecarboxylic acid

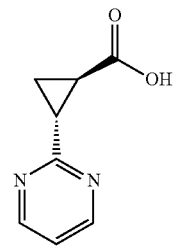

A mixture of tert-butyl (±)-trans-2-pyrimidin-2-ylcyclopropanecarboxylate (370 mg, 1.68 mmol) in a solution of HCl in dioxane (4 mL, 1.68 mmol) and one drop of water was stirred at room temperature for 1 h. The reaction was concentrated to give the title compound as a white solid (380 mg, crude). LCMS (ESI) [M+H]+=165.1.

Step 4: (±)-trans-N-(6,8-dichloro-2,7-naphthyridin-3-yl)-2-(pyrimidin-2-yl)cyclopropanecarboxamide

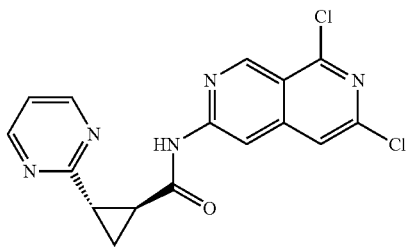

A mixture of (±)-trans-2-pyrimidin-2-ylcyclopropanecarboxylic acid (370 mg, 2.25 mmol), 6,8-dichloro-2,7-naphthyridin-3-amine (200 mg, 0.93 mmol) in pyridine (1.5 mL) in dichloromethane (20 mL) was stirred at room temperature for 0.5 h. POCl$_3$ (0.3 mL, 2.25 mmol) was added to the reaction in portions at room temperature. The mixture was stirred for 1 h at rt. The reaction was diluted with EtOAc (50 mL) and adjusted pH to 7-8 with sat NaHCO$_3$. The organics were then separated, dried (Na$_2$SO$_4$) and concentrated to dryness. The residue was purified by silica gel chromatography (PE:EA=2:1 to PE:EA=1:1) to give the title compound a white solid (330 mg, 39.8% yield). LCMS (ESI) [M+H]+=360.0.

Step 5: (±)-trans-N-(8-amino-6-chloro-2,7-naphthyridin-3-yl)-2-(pyrimidin-2-yl)cyclopropanecarboxamide

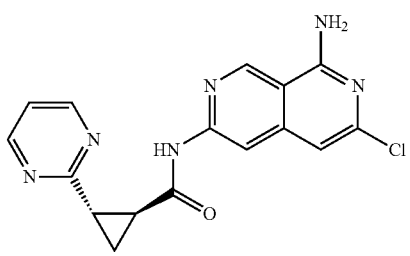 [SMILES: Nc1nc(Cl)cc2cc(NC(=O)[C@H]3C[C@@H]3c3ncccn3)ncc12]

A mixture of (±)-trans-N-(6,8-dichloro-2,7-naphthyridin-3-yl)-2-pyrimidin-2-yl-cyclopropanecarboxamide (330 mg, 0.92 mmol) and NH₄OH (5 mL, 0.92 mmol) in 1,4-dioxane (5 mL) was heated under Ar at 90° C. for 3 h. The reaction was concentrated to dryness to give the title compound as a yellow solid (380 mg, crude). LCMS (ESI) [M+H]+=341.1.

Step 6: (±)-trans-N-(8-amino-6-(4-methylpyridin-3-yl)-2,7-naphthyridin-3-yl)-2-(pyrimidin-2-yl)cyclopropanecarboxamide

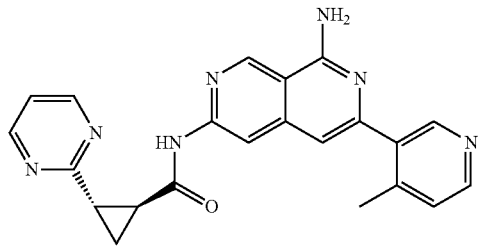 [SMILES: Cc1ccncc1-c1cc2cc(NC(=O)[C@H]3C[C@@H]3c3ncccn3)ncc2c(N)n1]

A mixture of (±)-trans-N-(8-amino-6-chloro-2,7-naphthyridin-3-yl)-2-pyrimidin-2-yl-cyclopropanecarboxamide (187 mg, 0.55 mmol), 4-methyl-3-(4,4,5,5-tetramethyl-1,3,2-dioxaborolan-2-yl)pyridine (144 mg, 0.66 mmol), XPhos Pd G2 (45 mg, 0.06 mmol), XPhos (27 mg, 0.06 mmol) and K₂CO₃ (228 mg, 1.65 mmol) in 1,4-dioxane (8 mL) and water (2 mL) was stirred under Ar at 100° C. for 3 h. The reaction was concentrated and purified by silica gel chromatography (PE:EA=2:1 to PE:EA=1:2) to give the title compound as a white solid (92.1 mg, 42.2% yield). LCMS (ESI): RT(min)=1.38, [M+H]⁺=398.2, method=B. ¹HNMR (400 MHz, DMSO-d₆) δ 11.09 (s, 1H), 9.36 (s, 1H), 8.72 (s, 1H), 8.71 (s, 1H), 8.57 (s, 1H), 8.44 (d, J=4.8 Hz, 1H), 8.27 (s, 1H), 7.37-7.31 (m, 4H), 6.99 (s, 1H), 2.76-2.71 (m, 1H), 2.65-2.61 (m, 1H), 2.41 (s, 3H), 1.59-1.57 (m, 2H).

Example 153

(±)-trans-N-(8-amino-6-(5-amino-4-methylpyridin-3-yl)-2,7-naphthyridin-3-yl)-2-(trifluoromethyl)cyclopropanecarboxamide (Compound 190)

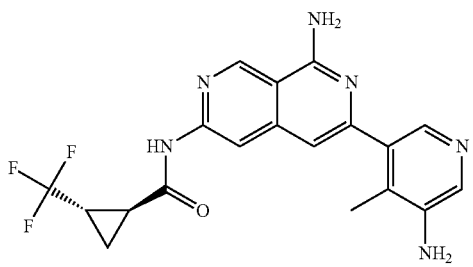 [SMILES: Cc1c(N)cncc1-c1cc2cc(NC(=O)[C@H]3C[C@@H]3C(F)(F)F)ncc2c(N)n1]

Step 1: tert-butyl 4-methyl-5-(4,4,5,5-tetramethyl-1,3,2-dioxaborolan-2-yl)pyridin-3-ylcarbamate

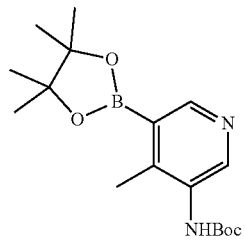 [SMILES: Cc1c(NC(=O)OC(C)(C)C)cncc1B1OC(C)(C)C(C)(C)O1]

A mixture of bis(pinacolato)diboron (2.2 g, 8.66 mmol), tert-butyl N-(5-bromo-4-methyl-3-pyridyl)carbamate (500 mg, 1.74 mmol), PdCl₂dppf (254 mg, 0.35 mmol) and KOAc (340 mg, 3.47 mmol) in 1,4-dioxane (15 mL) was heated under Ar at 85° C. for 16 h. The reaction was filtered and concentrated to give the title compound as a black solid (3.2 g, crude). LCMS (ESI) [M+H]+=335.2.

Step 2: (±)-trans-tert-butyl 5-(1-amino-6-((trans)-2-(trifluoromethyl)cyclopropanecarboxamido)-2,7-naphthyridin-3-yl)-4-methylpyridin-3-ylcarbamate

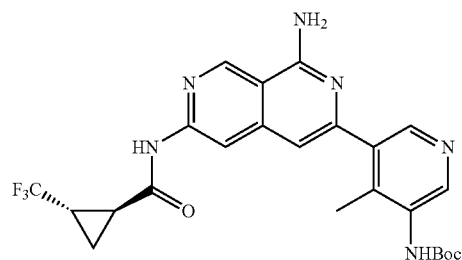 [SMILES: Cc1c(NC(=O)OC(C)(C)C)cncc1-c1cc2cc(NC(=O)[C@H]3C[C@@H]3C(F)(F)F)ncc2c(N)n1]

A mixture of (±)-trans-N-(8-amino-6-chloro-2,7-naphthyridin-3-yl)-2-(trifluoromethyl)cyclopropanecarboxamide (200 mg, 0.6 mmol), tert-butyl N-[4-methyl-5-(4,4,5,5-tetramethyl-1,3,2-dioxaborolan-2-yl)-3-pyridyl]carbamate (1.5 g, 4.49 mmol), Pd(PPh₃)₄ (140 mg, 0.12 mmol) and K₂CO₃ (250 mg, 1.81 mmol) in 1,4-dioxane (16 mL) and water (4 mL) was heated under Ar at 100° C. for 3 h. The reaction was concentrated and purified by silica gel chromatography (PE:EA=1:1 to EA:MeOH=20:1) to give the title compound as a white solid (190 mg, 40.8% yield). LCMS (ESI) [M+H]+=503.2.

Step 3: (±)-trans-N-(8-amino-6-(5-amino-4-methylpyridin-3-yl)-2,7-naphthyridin-3-yl)-2-(trifluoromethyl)cyclopropanecarboxamide

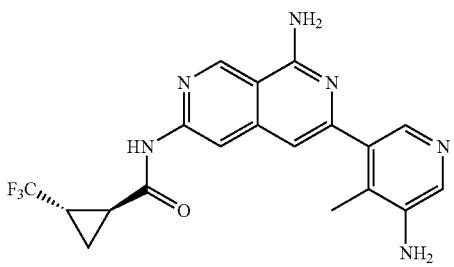 [SMILES: Cc1c(N)cncc1-c1cc2cc(NC(=O)[C@H]3C[C@@H]3C(F)(F)F)ncc2c(N)n1]

A mixture of (±)-trans-tert-butyl N-[5-[1-amino-6-[[(trans)-2-(trifluoromethyl)cyclopropanecarbonyl]amino]-2,7-naphthyridin-3-yl]-4-methyl-3-pyridyl]carbamate (190 mg, 0.38 mmol), TFA (1 mL, 0.38 mmol) in dichloromethane (4 mL) was stirred at room temperature for 2 h. The reaction was concentrated to dryness. The residue was taken up in MeOH (2 mL) and adjusted pH to 7-8 with sat NaHCO$_3$. The mixture was purified by prep-HPLC (eluent: 5%-95% methanol and 0.8 g/L NH$_4$HCO$_3$ in water) to give the title compound as a white solid (92.8 mg, 57.4% yield). LCMS (ESI): RT(min)=1.57, [M+H]$^+$=403.2, method=G. $^1$HNMR (400 MHz, DMSO-d$_6$) δ 11.19 (s, 1H), 9.37 (s, 1H), 8.19 (s, 1H), 7.93 (s, 1H), 7.77 (s, 1H), 7.30 (s, 2H), 6.85 (s, 1H), 5.16 (s, 2H), 2.60-2.58 (m, 1H), 2.32-2.30 (m, 1H), 2.06 (s, 3H), 1.33-1.30 (m, 2H).

Example 154

(±)-trans-N-(8-amino-6-(4-(2-hydroxyethyl)pyridin-3-yl)-2,7-naphthyridin-3-yl)-2-cyanocyclopropanecarboxamide (Compound 191)

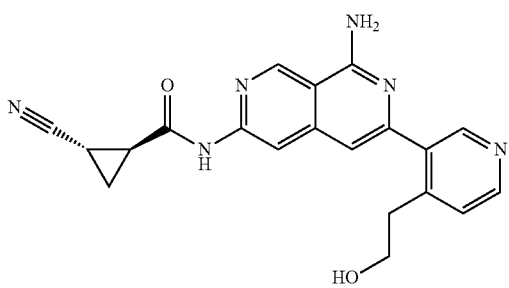 [SMILES: N#C[C@H]1C[C@@H]1C(=O)Nc1cc2cc(-c3cnccc3CCO)nc(N)c2cn1]

Step 1: 3,4-dihydro-1H-[1,2]oxaborinino[3,4-c]pyridin-1-ol

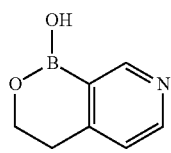 [SMILES: OB1OCCc2ccncc21]

To a stirred solution of 2-(3-bromo-4-pyridyl)ethanol (1.0 g, 4.95 mmol) and triisopropyl borate (1.1 g, 5.85 mmol) in tetrahydrofuran (30 mL) was added dropwise n-BuLi (4 mL, 10 mmol) at −78° C. The resulting mixture was stirred at −78° C. for 0.5 h. The mixture was warmed slowly to room temperature and stirred for 1 h. The reaction mixture was then diluted with water (10 mL) and washed with EA (10 mL×2). The aqueous layer was acidified to pH 4-5 by adding 6 N HCl and concentrated to dryness. The residue was suspended in a 1:1 solution of ethyl acetate and EtOH (10 mL) and filtered. The filtrate was concentrated to give 1-hydroxy-3,4-dihydrooxaborinino[3,4-c]pyridine (700 mg, 95% yield) as a yellow oil. LCMS (ESI) [M+H]$^+$=150.1.

Step 2: (±)-trans-N-(8-amino-6-(4-(2-hydroxyethyl)pyridin-3-yl)-2,7-naphthyridin-3-yl)-2-cyanocyclopropanecarboxamide

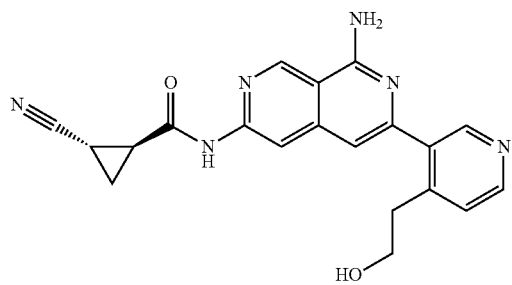 [SMILES: N#C[C@H]1C[C@@H]1C(=O)Nc1cc2cc(-c3cnccc3CCO)nc(N)c2cn1]

A mixture of 1-hydroxy-3,4-dihydrooxaborinino[3,4-c]pyridine (700 mg, 4.7 mmol), (±)-trans-N-(8-amino-6-chloro-2,7-naphthyridin-3-yl)-2-cyano-cyclopropanecarboxamide (140 mg, 0.49 mmol), XPhos Pd G2 (56 mg, 0.07 mmol), XPhos (65 mg, 0.14 mmol) and K$_2$CO$_3$ (140 mg, 1.01 mmol) in 1,4-dioxane (10 mL) and water (2 mL) was heated under Ar to 100° C. for 3 h. The mixture was directly purified by reverse phase HPLC (acetonitrile 0-40/0.1% NH$_4$HCO$_3$ in water) to afford (±)-trans-N-[8-amino-6-[4-(2-hydroxyethyl)-3-pyridyl]-2,7-naphthyridin-3-yl]-2-cyano-cyclopropanecarboxamide (72 mg, 39.5% yield) as a white solid. LCMS (ESI): RT(min)=1.169, [M+H]$^+$=375.1, method=A. $^1$HNMR (400 MHz, DMSO-d$_6$) δ 11.29 (s, 1H), 9.41 (s, 1H), 8.51 (s, 1H), 8.47 (d, J=5.2 Hz, 1H), 8.20 (s, 1H), 7.36 (d, J=5.2 Hz, 1H), 7.34 (s, 2H), 6.98 (s, 1H), 4.77 (t, J=4.8 Hz, 1H), 3.57-3.55 (m, 2H), 2.93 (t, J=6.8 Hz, 2H), 2.78-2.74 (m, 1H), 2.18-2.14 (m, 1H), 1.64-1.59 (m, 1H), 1.46-1.41 (m, 1H).

Example 155

(±)-trans-N-(8-amino-6-(4-(2-hydroxyethyl)pyridin-3-yl)-2,7-naphthyridin-3-yl)-2-(cyanomethyl)cyclopropanecarboxamide (Compound 192)

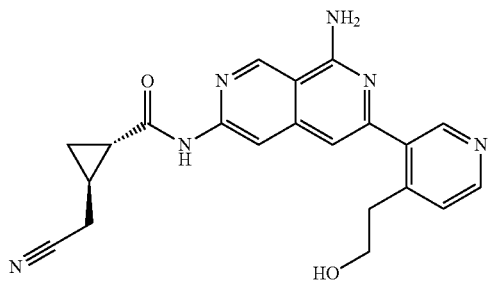 [SMILES: N#CC[C@H]1C[C@@H]1C(=O)Nc1cc2cc(-c3cnccc3CCO)nc(N)c2cn1]

A solution of (±)-trans-N-(8-amino-6-chloro-2,7-naphthyridin-3-yl)-2-(cyanomethyl) cyclopropanecarboxamide (140 mg, 0.46 mmol), 1-hydroxy-3,4-dihydro-2H-borinino[2,3-c]pyridine (800 mg, 5.44 mmol), XPhos (56 mg, 0.12 mmol), XPhos Pd G2 (56 mg, 0.07 mmol) and $K_2CO_3$ (140 mg, 1.01 mmol) in water (2 mL) and 1,4-dioxane (10 mL) was heated under Ar at 100° C. for 3 h. The mixture was directly purified by silica gel column chromatography (DCM:MeOH=10:1) and reverse phase HPLC (acetonitrile 17-47% in 0.05% ammonia in water) to give the title compound (36 mg, 20% yield) as a white solid. LCMS (ESI): RT(min)=1.404, [M+H]$^+$=389.0, method=C. $^1$HNMR (400 MHz, DMSO-d$_6$) δ 11.08 (s, 1H), 9.39 (s, 1H), 8.52 (s, 1H), 8.47 (d, J=5.2 Hz, 1H), 8.23 (s, 1H), 7.36 (d, J=5.2 Hz, 1H), 7.34 (s, 2H), 6.97 (s, 1H), 4.80 (t, J=4.8 Hz, 1H), 3.60-3.56 (m, 2H), 2.93 (t, J=6.8 Hz, 2H), 2.76-2.73 (m, 2H), 2.12-2.09 (m, 1H), 1.59-1.58 (m, 1H), 1.16-1.13 (m, 1H), 0.99-0.96 (m, 1H).

Example 156

(1S,2R)—N-(8-amino-6-(4-methylpyridin-3-yl)-2,7-naphthyridin-3-yl)-2-(cyanomethyl)cyclopropane-1-carboxamide (Compound 193) and (1R,2S)—N-(8-amino-6-(4-methylpyridin-3-yl)-2,7-naphthyridin-3-yl)-2-(cyanomethyl)cyclopropane-1-carboxamide (Compound 194)

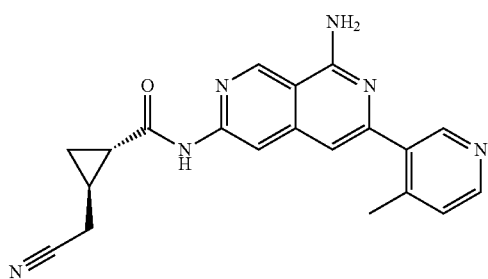

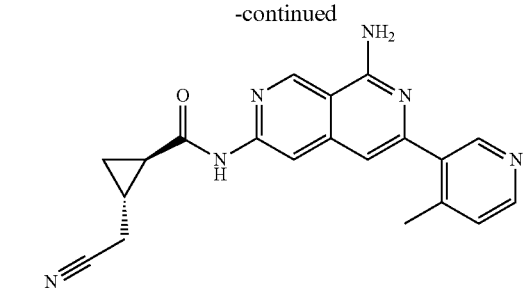

The title compounds were prepared according to the procedure described for (±)-trans-N-[8-amino-6-(4-methyl-3-pyridyl)-2,7-naphthyridin-3-yl]-2-(cyanomethyl)cyclopropane carboxamide (Compound 157). The single stereoisomers were isolated by chiral SFC. (Compound 193): $^1$HNMR (400 MHz, DMSO-d$_6$) δ 11.04 (s, 1H), 9.37 (s, 1H), 8.56 (s, 1H), 8.43 (d, J=5.0 Hz, 1H), 8.22 (s, 1H), 7.30-7.31 (m, 3H), 6.97 (s, 1H), 3.74 (m, 2H), 2.41 (s, 3H), 2.11 (m, 1H), 1.58 (m, 1H), 1.13 (m, 1H), 0.96 (m, 1H). (Compound 194): $^1$HNMR (400 MHz, DMSO-d$_6$) δ 11.04 (s, 1H), 9.37 (s, 1H), 8.56 (s, 1H), 8.43 (d, J=5.0 Hz, 1H), 8.22 (s, 1H), 7.30-7.31 (m, 3H), 6.97 (s, 1H), 3.74 (m, 2H), 2.41 (s, 3H), 2.11 (m, 1H), 1.58 (m, 1H), 1.13 (m, 1H), 0.96 (m, 1H).

Example 157

(1S,2S)—N-(8-amino-5-fluoro-6-(4-methylpyridin-3-yl)-2,7-naphthyridin-3-yl)-2-(1H-pyrazol-4-yl)cyclopropane-1-carboxamide (Compound 195) and (1R,2R)—N-(8-amino-5-fluoro-6-(4-methylpyridin-3-yl)-2,7-naphthyridin-3-yl)-2-(1H-pyrazol-4-yl)cyclopropane-1-carboxamide (Compound 196)

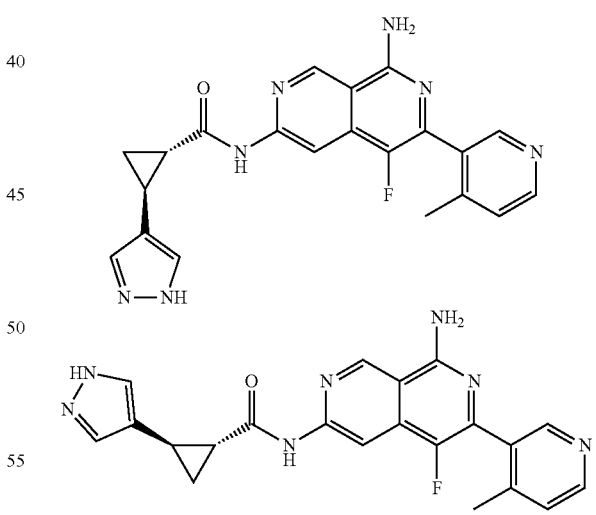

The title compounds were prepared according to procedure described for (±)-trans-N-(8-amino-5-fluoro-6-(4-methylpyridin-3-yl)-2,7-naphthyridin-3-yl)-2-(1H-pyrazol-4-yl)cyclopropanecarboxamide (Compound 172). The single stereoisomers were isolated by chiral SFC. (Compound 195): $^1$HNMR (400 MHz, DMSO-d$_6$) δ 12.63 (br s, 1H), 11.19 (s, 1H), 9.42 (s, 1H), 8.51 (s, 1H), 8.48 (d, J=5.1 Hz, 1H), 8.40 (s, 1H), 7.61 (br s, 1H), 7.38 (d, J=5.1 Hz, 2H), 7.32 (br s, 2H), 2.27 (s, 3H), 2.19-2.26 (m, 2H), 1.41 (m, 1H), 1.26 (m, 1H). (Compound 196): ¹HNMR (400 MHz, DMSO-d₆) δ 12.63 (br s, 1H), 11.19 (s, 1H), 9.42 (s, 1H), 8.51 (s, 1H), 8.48 (d, J=5.1 Hz, 1H), 8.40 (s, 1H), 7.61 (br s, 1H), 7.38 (d, J=5.1 Hz, 2H), 7.32 (br s, 2H), 2.27 (s, 3H), 2.19-2.26 (m, 2H), 1.41 (m, 1H), 1.26 (m, 1H).

Example 158

(1S,2S)—N-(8-amino-6-(4-methylpyridin-3-yl)-2,7-naphthyridin-3-yl)-2-(1-methyl-1H-pyrazol-4-yl)cyclopropane-1-carboxamide (Compound 197) and (1R,2R)—N-(8-amino-6-(4-methylpyridin-3-yl)-2,7-naphthyridin-3-yl)-2-(1-methyl-H-pyrazol-4-yl)cyclopropane-1-carboxamide (Compound 198)

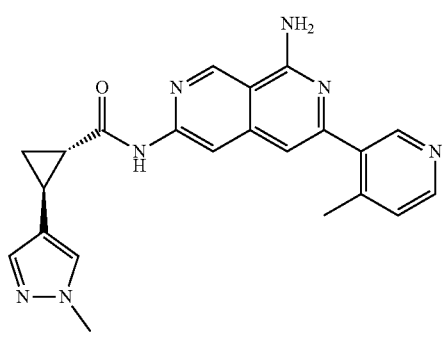

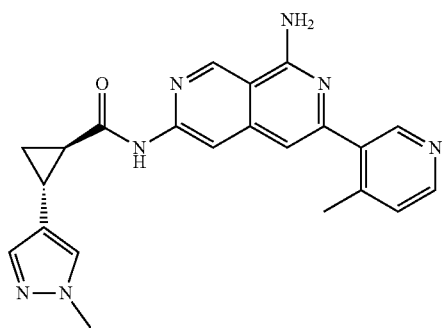

The title compounds were prepared according to the procedure described for (±)-trans-N-[8-amino-6-(4-methyl-3-pyridyl)-2,7-naphthyridin-3-yl]-2-(1-methylpyrazol-4-yl)cyclopropane carboxamide (Compound 159). The single stereoisomers were isolated by chiral SFC. (Compound 197): ¹HNMR (400 MHz, DMSO-d₆) δ 10.93 (s, 1H), 9.36 (s, 1H), 8.57 (br s, 1H), 8.43 (br s, 1H), 8.25 (s, 1H), 7.56 (s, 1H), 7.29-7.32 (m, 4H), 6.97 (s, 1H), 3.77 (s, 3H), 2.41 (s, 3H), 2.19-2.22 (m, 2H), 1.39 (m, 1H), 1.19 (m, 1H). (Compound 198): ¹HNMR (400 MHz, DMSO-d₆) δ 10.93 (s, 1H), 9.36 (s, 1H), 8.57 (br s, 1H), 8.43 (br s, 1H), 8.25 (s, 1H), 7.56 (s, 1H), 7.29-7.32 (m, 4H), 6.97 (s, 1H), 3.77 (s, 3H), 2.41 (s, 3H), 2.19-2.22 (m, 2H), 1.39 (m, 1H), 1.19 (m, 1H).

Example 159

(1R,2R)—N-(8-amino-6-(5-amino-4-methylpyridin-3-yl)-2,7-naphthyridin-3-yl)-2-cyanocyclopropane-1-carboxamide (Compound 199) and (1S,2S)—N-(8-amino-6-(5-amino-4-methylpyridin-3-yl)-2,7-naphthyridin-3-yl)-2-cyanocyclopropane-1-carboxamide (Compound 200)

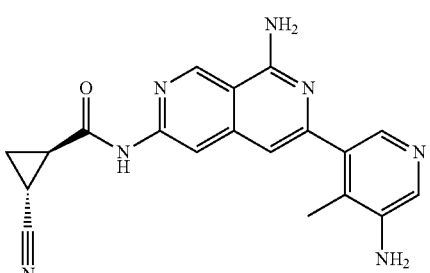

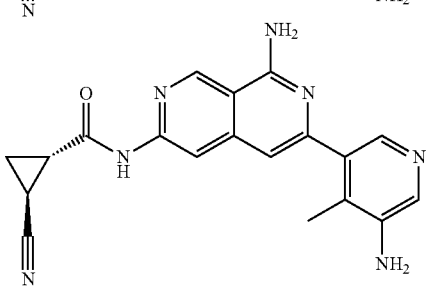

The title compounds were prepared according to the procedure described for (±)-(trans)-N-(8-amino-6-(5-amino-4-methylpyridin-3-yl)-2,7-naphthyridin-3-yl)-2-cyanocyclopropane carboxamide (Compound 165). The single stereoisomers were isolated by chiral SFC. (Compound 199): ¹HNMR (400 MHz, DMSO-d₆) δ 11.24 (s, 1H), 9.38 (s, 1H), 8.17 (s, 1H), 7.93 (s, 1H), 7.76 (s, 1H), 7.29 (s, 2H), 6.84 (s, 1H), 5.13 (br s, 2H), 2.76 (m, 1H), 2.15 (m, 1H), 2.06 (s, 3H), 1.61 (m, 1H), 1.43 (m, 1H). (Compound 200): ¹HNMR (400 MHz, DMSO-d₆) δ 11.24 (s, 1H), 9.38 (s, 1H), 8.17 (s, 1H), 7.93 (s, 1H), 7.76 (s, 1H), 7.29 (s, 2H), 6.84 (s, 1H), 5.13 (br s, 2H), 2.76 (m, 1H), 2.15 (m, 1H), 2.06 (s, 3H), 1.61 (m, 1H), 1.43 (m, 1H).

Example 160

(±)-trans-N-(8-amino-6-(4-(trifluoromethyl)pyridin-3-yl)-2,7-naphthyridin-3-yl)-2-cyanocyclopropane-1-carboxamide (Compound 201)

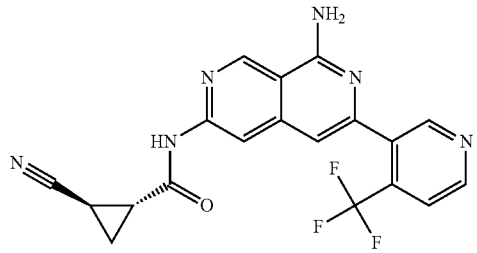 [SMILES: N#C[C@@H]1C[C@H]1C(=O)Nc1cc2cc(-c3cnccc3C(F)(F)F)nc(N)c2cn1]

The title compound was prepared in a fashion that is analoguous to (±)-trans-N-[8-amino-6-(4-ethoxy-3-pyridyl)-2,7-naphthyridin-3-yl]-2-cyano-cyclopropanecarboxamide (Compound 129). LCMS (ESI): RT(min)=1.55, [M+H]⁺=399.1, method=B. ¹HNMR (400 MHz, DMSO-d₆) δ 11.3 (s, 1H), 9.43 (s, 1H), 8.89 (d, 1H), 8.83 (s, 1H), 8.20 (s, 1H), 7.85 (d, 1H), 7.42 (s, 2H), 6.97 (s, 1H), 2.74-2.79 (m, 1H), 2.13-2.18 (m, 1H), 1.59-1.64 (m, 1H), 1.41-1.46 (m, 1H).

Example 161

(1S,2S)—N-(8-amino-6-(4-methylpyridin-3-yl)-2,7-naphthyridin-3-yl)-2-cyanocyclopropane-1-carboxamide (Compound 202) and (1R,2R)—N-(8-amino-6-(4-methylpyridin-3-yl)-2,7-naphthyridin-3-yl)-2-cyanocyclopropane-1-carboxamide (Compound 203)

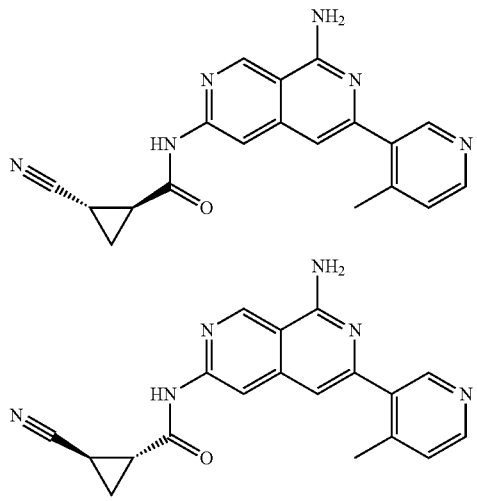

The title compounds were prepared according to the procedure described for (±)-trans-N-(8-amino-6-(4-methylpyridin-3-yl)-2,7-naphthyridin-3-yl)-2-cyanocyclopropane-1-carboxamide. (Compound 43). The single stereoisomers were isolated by chiral SFC. (Compound 202): ¹HNMR (400 MHz, DMSO-d₆) δ 11.26 (s, 1H), 9.39 (s, 1H), 8.56 (s, 1H), 8.43 (d, J=5.0 Hz, 1H), 8.20 (s, 1H), 7.34 (br s, 2H), 7.30 (d, J=5.0 Hz, 1H), 6.98 (s, 1H), 2.76 (m, 1H), 2.40 (s, 3H), 2.15 (m, 1H), 1.61 (m, 1H), 1.44 (m, 1H). (Compound 203): ¹HNMR (400 MHz, DMSO-d₆) δ 11.26 (s, 1H), 9.39 (s, 1H), 8.56 (s, 1H), 8.43 (d, J=5.0 Hz, 1H), 8.20 (s, 1H), 7.34 (br s, 2H), 7.30 (d, J=5.0 Hz, 1H), 6.98 (s, 1H), 2.76 (m, 1H), 2.40 (s, 3H), 2.15 (m, 1H), 1.61 (m, 1H), 1.44 (m, 1H).

Example 162

N-(8-amino-5-(3-hydroxycyclopent-1-enyl)-6-(4-methylpyridin-3-yl)-2,7-naphthyridin-3-yl)cyclopropanecarboxamide (Compound 204)

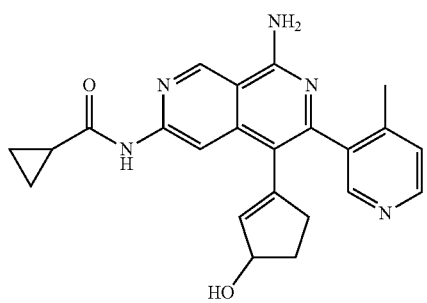 [SMILES: Cc1ccncc1-c1nc(N)c2cnc(NC(=O)C3CC3)cc2c1C1=CC(O)CC1]

Step 1: 3-oxocyclopent-1-enyl trifluoromethanesulfonate

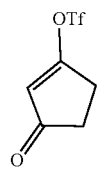 [SMILES: O=C1C=C(OS(=O)(=O)C(F)(F)F)CC1]

A solution of cyclopentane-1,3-dione (3 g, 30.58 mmol), Tf₂O (8.6 g, 30.48 mmol) and TEA (9.3 g, 91.90 mmol) in dichloromethane (30 mL) was stirred for 1 h at 0° C. The reaction was diluted with water and extracted with DCM. The collected organic was dried over Na₂SO₄, filtered, and concentrated under vacuum. The residue was purified by silica-gel chromatography eluted with PE/EA (10:1) to afford 3-oxocyclopent-1-en-1-yl trifluoromethanesulfonate (2.8 g, 40%) as a yellowish oil. LCMS (ESI): [M+H]⁺= 231.1.

Step 2: 3-(4,4,5,5-tetramethyl-1,3,2-dioxaborolan-2-yl)cyclopent-2-enone

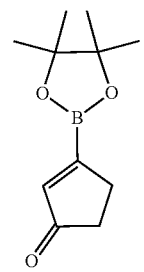

A solution of 3-oxocyclopent-1-en-1-yl trifluoromethanesulfonate (2.5 g, 10.86 mmol) in dioxane (50 mL) was added 4,4,5,5-tetramethyl-2-(tetramethyl-1,3,2-dioxaborolan-2-yl)-1,3,2-dioxaborolane (5.5 g, 21.65 mmol), Pd(dppf)Cl₂ (720 mg, 0.98 mmol), KOAc (2.1 g, 21.39 mmol). The resultant solution was stirred for 1 h at 100° C. under nitrogen. The solution was cooled to room temperature, diluted with water and extracted with dichloromethane. The collected organic was dried over Na₂SO₄, filtered, and concentrated under vacuum. The residue was purified by a silica-gel column eluted with PE/EA (10/1) to afford 3-(4,4,5,5-tetramethyl-1,3,2-dioxaborolan-2-yl)cyclopent-2-enone (2 g, crude product) as a yellow oil. LCMS (ESI): [M+H]⁺=127.1.

Step 3: N-(8-amino-6-(4-methylpyridin-3-yl)-5-(3-oxocyclopent-1-enyl)-2,7-naphthyridin-3-yl)cyclopropanecarboxamide

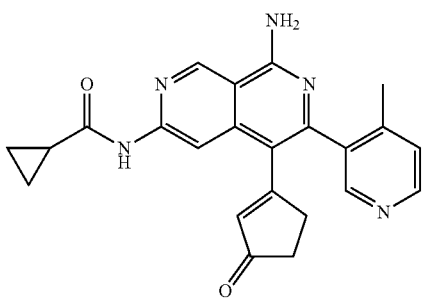 [SMILES: Cc1ccncc1-c1nc(N)c2cnc(NC(=O)C3CC3)cc2c1C1=CC(=O)CC1]

A solution of N-[8-amino-5-bromo-6-(4-methylpyridin-3-yl)-2,7-naphthyridin-3-yl]cyclopropanecarboxamide (500 mg, 1.25 mmol) in dioxane (10 mL)/water (2 mL) was added to a mixture of 3-(4,4,5,5-tetramethyl-1,3,2-dioxaborolan-2-yl)cyclopent-2-enone (320 mg, 2.54 mmol), Pd(dppf)Cl₂ (280 mg, 0.38 mmol), and sodium bicarbonate (220 mg, 2.61 mmol). The mixture was stirred 100° C. under nitrogen. After 6 h, the reaction mixture was concentrated. The residue was purified with silica gel chromatography eluted with DCM/MeOH (10:1). This resulted in N-[8-amino-6-(4-methylpyridin-3-yl)-5-(3-oxocyclopent-1-en-1-yl)-2,7-naphthyridin-3-yl]cyclopropanecarboxamide (200 mg, 40%) as a yellow solid. LCMS (ESI): [M+H]⁺=400.1.

Step 4: N-(8-amino-5-(3-hydroxycyclopent-1-enyl)-6-(4-methylpyridin-3-yl)-2,7-naphthyridin-3-yl)cyclopropanecarboxamide

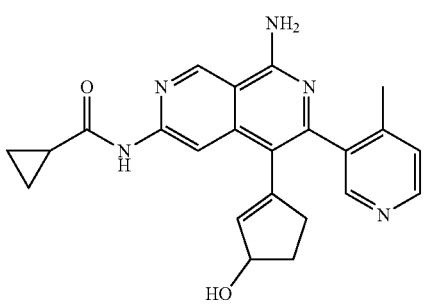 [SMILES: Cc1ccncc1-c1nc(N)c2cnc(NC(=O)C3CC3)cc2c1C1=CC(O)CC1]

NaBH₄ (50 mg, 1.32 mmol) was added to a solution of N-[8-amino-6-(4-methylpyridin-3-yl)-5-(3-oxocyclopent-1-en-1-yl)-2,7-naphthyridin-3-yl]cyclopropanecarboxamide (50 mg, 0.12 mmol) in methanol (10 mL) at room temperature. After 1 h, the reaction mixture was concentrated. The residue was purified by silica gel chromatography eluted with DCM/MeOH (10:1) to provide N-[8-amino-5-(3-hydroxycyclopent-1-en-1-yl)-6-(4-methylpyridin-3-yl)-2,7-naphthyridin-3-yl]cyclopropanecarboxamide (2.8 mg, 6%) as a yellow solid. LCMS (ESI): R$_T$(min)=1.52, [M+H]⁺=402.1, method=M; ¹H NMR (300 MHz, DMSO-d₆) δ 10.96 (s, 1H), 9.38 (s, 1H), 8.37 (d, J=4.8 Hz, 1H), 8.31 (s, 1H), 8.24 (s, 1H), 7.30 (s, 2H), 7.25 (d, J=4.8 Hz, 1H), 5.49 (s, 1H), 4.71 (d, J=4.5 Hz, 1H), 4.65 (s, 1H), 2.30 (s, 1H), 2.14 (s, 3H), 2.07-2.03 (m, 3H), 1.48-1.45 (m, 1H), 0.85-0.80 (m, 4H).

Example 163

(+/−)-trans-N-(8-amino-5-methyl-6-(4-methylpyridin-3-yl)-2,7-naphthyridin-3-yl)-2-(cyanomethyl)cyclopropanecarboxamide (Compound 205)

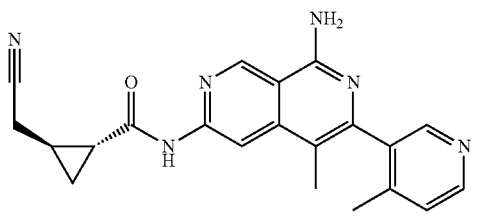

Step 1: trans-N-(8-amino-5-methyl-6-(4-methylpyridin-3-yl)-2,7-naphthyridin-3-yl)-2-(cyanomethyl)cyclopropanecarboxamide

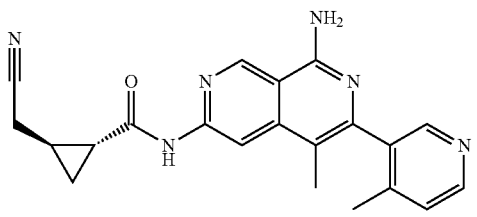 [SMILES: Cc1ccncc1-c1nc(N)c2cnc(NC(=O)[C@@H]3C[C@H]3CC#N)cc2c1C]

A mixture of trans-N-[8-amino-5-bromo-6-(4-methylpyridin-3-yl)-2,7-naphthyridin-3-yl]-2-(cyanomethyl)cyclopropane-1-carboxamide (120 mg, 0.27 mmol), trimethyl-1,3,5,2,4,6-trioxatriborinane (52 mg, 0.41 mmol), Pd(PPh₃)₄ (32 mg, 0.03 mmol), and K₃PO₄ (175 mg, 0.82 mmol) in dioxane (5 mL)/water (1 mL) was stirred for 15 h at 100° C. under nitrogen. The reaction mixture was concentrated, and the residue was purified by Prep-HPLC to afford trans-N-(8-amino-5-methyl-6-(4-methylpyridin-3-yl)-2,7-naphthyridin-3-yl)-2-(cyanomethyl)cyclopropanecarboxamide (3.0 mg, 3%) as a white solid. LCMS (ESI): R$_T$ (min)=1.69, [M+H]⁺=373.3, method=K-1-1; ¹H NMR (400 MHz, CD₃OD) δ 9.32 (s, 1H), 8.48 (s, 1H), 8.46 (d, J=5.2 Hz, 1H), 8.37 (s, 1H), 7.45 (d, J=5.2 Hz, 1H), 2.78-2.65 (m, 2H), 2.23 (s, 3H), 2.14 (s, 3H), 2.06-2.00 (m, 1H), 1.81-1.70 (m, 1H), 1.41-1.30 (m, 1H), 1.12-1.02 (m, 1H).

Example 164

(+/−)-N-(8-amino-6-(4-methyl-2-phenylpyridin-3-yl)-2,7-naphthyridin-3-yl)-2-(cyanomethyl)cyclopropanecarboxamide (Compound 206)

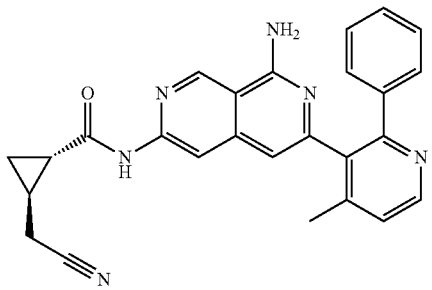 [SMILES: Cc1ccnc(-c2ccccc2)c1-c1cc2cc(NC(=O)[C@H]3C[C@@H]3CC#N)ncc2c(N)n1]

A mixture of trans-N-(8-amino-6-chloro-2,7-naphthyridin-3-yl)-2-(cyanomethyl)cyclopropane-1-carboxamide (10 mg, 0.03 mmol), 4-methyl-2-phenyl-3-(tetramethyl-1,3,2-dioxaborolan-2-yl)pyridine (20 mg, 0.07 mmol), Pd(amphos)Cl$_2$ (3 mg, 0.01 mmol), K$_3$PO$_4$ (21 mg, 0.10 mmol) in dioxane (0.9 mL)/water (0.3 mL) was stirred for 20 min at 100° C. under nitrogen. The solids were filtered, and the filtrate was concentrated. The residue was purified by silica gel chromatography eluted with dichloromethane/methanol (15:1). The collected fractions were combined and concentrated. The product was further purified by Prep-HPLC to afford trans-N-[8-amino-6-(4-methyl-2-phenylpyridin-3-yl)-2,7-naphthyridin-3-yl]-2-(cyanomethyl)cyclopropane-1-carboxamide (3 mg, 21%) as a green solid. LCMS (ESI): R$_T$ (min)=1.14, [M+H]$^+$=435.3, method=K-1-1; 1H NMR (400 MHz, DMSO-d$_6$) δ 11.01 (s, 1H), 9.33 (s, 1H), 8.54 (d, J=4.7 Hz, 1H), 7.96 (s, 1H), 7.48-7.28 (m, 5H), 7.23-7.10 (m, 3H), 6.48 (s, 1H), 2.81-2.71 (m, 2H), 2.17 (s, 3H), 2.11-2.03 (m, 1H), 1.61-1.51 (m, 1H), 1.10-1.06 (m, 1H), 1.03-0.93 (m, 1H).

Example 165

((1S,2S)-2-(8-amino-6-(4-methylpyridin-3-yl)-2,7-naphthyridin-3-ylcarbamoyl)-1-methylcyclopropyl)methyl acetate (Compound 207)

((1R,2S)-2-(8-amino-6-(4-methylpyridin-3-yl)-2,7-naphthyridin-3-ylcarbamoyl)-1-methylcyclopropyl)methyl acetate (Compound 208)

N-(8-amino-6-(4-methylpyridin-3-yl)-2,7-naphthyridin-3-yl)-2-(hydroxymethyl)-2-methylcyclopropanecarboxamide (Compound 209)

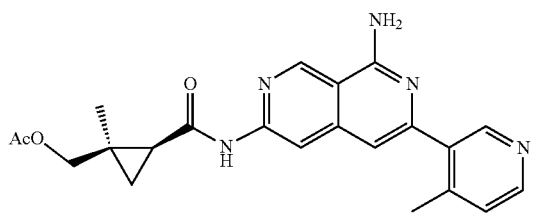

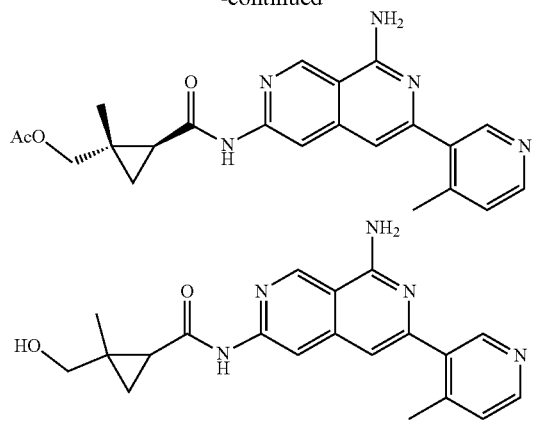

Step 1: Tert-butyl 2-[(acetyloxy)methyl]-2-methylcyclopropane-1-carboxylate

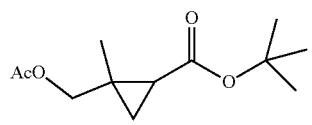 [SMILES: CC(=O)OCC1(C)CC1C(=O)OC(C)(C)C]

A mixture of 2-methylprop-2-en-1-yl acetate (10 g, 87.61 mmol), Cu(OAc)$_2$ (950 mg, 5.23 mmol), and tert-butyl 2-diazoacetate (20 g, 140.69 mmol) in toluene (300 mL) was stirred for 3 h at 95° C. The solids were filtered, and the filtrate was concentrated to afford tert-butyl 2-[(acetyloxy)methyl]-2-methylcyclopropane-1-carboxylate (18 g, crude) as a brown oil.

Step 2: 2-[(Acetyloxy)methyl]-2-methylcyclopropane-1-carboxylic acid

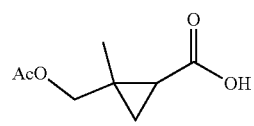

A solution of tert-butyl 2-[(acetyloxy)methyl]-2-methylcyclopropane-1-carboxylate (18 g, 78.85 mmol) in dichloromethane (80 mL)/trifluoroacetic acid (150 mL) was stirred for 16 hours. The resulting mixture was concentrated. The residue was dissolved in water, and the pH of the solution was adjusted to 11 with 20% aqueous sodium hydroxide solution. The resulting mixture was extracted with ethyl acetate. The pH of the aqueous layer was adjusted to 3 with hydrochloric acid (2 M). The resulting solution was extracted with ethyl acetate, and the organic layer dried over Na$_2$SO$_4$ and concentrated under vacuum to afford 2-[(acetyloxy)methyl]-2-methylcyclopropane-1-carboxylic acid (10 g, 74%) as a red oil. LCMS (ESI): [M–H]$^+$=171.1.

Step 3 (2-(6,8-dichloro-2,7-naphthyridin-3-ylcarbamoyl)-1-methylcyclopropyl)methyl acetate

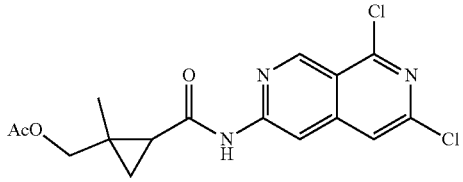 [SMILES: CC(=O)OCC1(C)CC1C(=O)Nc1cc2cc(Cl)nc(Cl)c2cn1]

POCl$_3$ (4 g, 26.09 mmol) was added dropwise to a solution of 6,8-dichloro-2,7-naphthyridin-3-amine (2 g, 9.34 mmol), 2-[(acetyloxy)methyl]-2-methylcyclopropane-1-carboxylic acid (4 g, 23.23 mmol) in pyridine (5 mL)/dichloromethane (50 mL) at room temperature under nitrogen. After, 30 min, the reaction was diluted with iced water, and the resulting solution was extracted with dichloromethane. The collected organic extract was dried over Na$_2$SO$_4$, filtered and concentrated under vacuum. The residue was purified by silica gel chromatography eluted with ethyl acetate/petroleum ether (1:3) to afford [2-[(6,8-dichloro-2,7-naphthyridin-3-yl)carbamoyl]-1-methylcyclopropyl] methyl acetate (2.2 g, 64%) as a red oil. LCMS (ESI): [M+H]$^+$=368.1.

Step 4: (2-(8-amino-6-chloro-2,7-naphthyridin-3-ylcarbamoyl)-1-methylcyclopropyl)methyl acetate

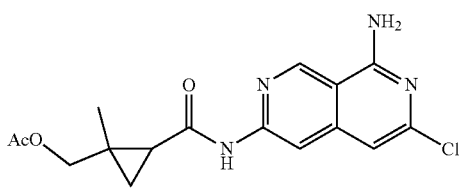 [SMILES: CC(=O)OCC1(C)CC1C(=O)Nc1cc2cc(Cl)nc(N)c2cn1]

A solution of [2-[(6,8-dichloro-2,7-naphthyridin-3-yl)carbamoyl]-1-methylcyclopropyl]methyl acetate (2.2 g, 5.98 mmol) in ammonium hydroxide (20 mL), and 1,4-dioxane (27 mL) was heated at 90° C. After 3 h, the reaction mixture was concentrated under vacuum to afford (2-(8-amino-6-chloro-2,7-naphthyridin-3-ylcarbamoyl)-1-methylcyclopropyl)methyl acetate (2.4 g, crude) as a yellow solid. LCMS (ESI): [M+H]$^+$=349.1.

Step 5: (±)-((1S,2S)-2-(8-amino-6-(4-methylpyridin-3-yl)-2,7-naphthyridin-3-ylcarbamoyl)-1-methylcyclopropyl)methyl acetate (Compound 207)

(±)-((1R,2S)-2-(8-amino-6-(4-methylpyridin-3-yl)-2,7-naphthyridin-3-ylcarbamoyl)-1-methylcyclopropyl)methyl acetate (Compound 208)

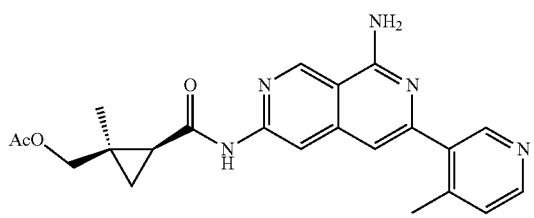

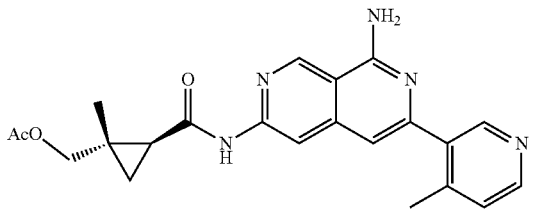

A mixture of [2-[(8-amino-6-chloro-2,7-naphthyridin-3-yl)carbamoyl]-1-methylcyclopropyl]methyl acetate (2.4 g, 6.88 mmol), (4-methylpyridin-3-yl)boronic acid (1.8 g, 13.14 mmol), Pd(dppf)Cl$_2$ (600 mg, 0.82 mmol) and sodium carbonate (1.6 g, 15.10 mmol) in 1,4-dioxane (80 mL)/water (13 mL) was heated at 100° C. under nitrogen. After 2 h, the solids were filtered, and the filtrate was concentrated under vacuum. The resulting residue was purified by Prep-HPLC and chiral SFC to afford two diastereoisomers. (Compound 207): LCMS (ESI): R$_T$ (min)=1.13, [M+H]$^+$=406.2, method=K-1; $^1$H NMR (300 MHz, CD$_3$OD) δ 9.29 (s, 1H), 8.54 (s, 1H), 8.43 (d, J=5.1 Hz, 1H), 8.33 (s, 1H), 7.40 (d, J=5.1 Hz, 1H), 6.99 (s, 1H), 4.07-3.95 (m, 2H), 2.46 (s, 3H), 2.11 (s, 3H), 2.09-2.04 (m, 1H), 1.31 (s, 3H), 1.27-1.24 (m, 1H), 1.06-1.01 (m, 1H). (Compound 208): LCMS (ESI): R$_T$ (min)=1.28, [M+H]$^+$=406.2, method=M; $^1$H NMR (300 MHz, CD$_3$OD) δ $^1$H NMR (300 MHz, CD$_3$OD) δ 9.29 (s, 1H), 8.54 (s, 1H), 8.43 (d, J=5.1 Hz, 1H), 8.29 (s, 1H), 7.40 (d, J=5.1 Hz, 1H), 6.99 (s, 1H), 4.38 (d, J=11.4 Hz, 1H), 4.19 (d, J=11.4 Hz, 1H), 2.46 (s, 3H), 2.03-1.99 (m, 1H), 1.94 (s, 3H), 1.42-1.39 (m, 1H), 1.32 (s, 3H), 1.06-1.01 (m, 1H).

Step 6: N-(8-amino-6-(4-methylpyridin-3-yl)-2,7-naphthyridin-3-yl)-2-(hydroxymethyl)-2-methylcyclopropanecarboxamide (Compound 209)

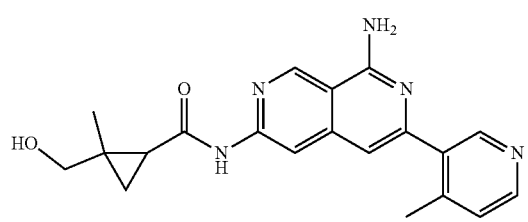 [SMILES: Cc1ccncc1-c1cc2cc(NC(=O)C3CC3(C)CO)ncc2c(N)n1]

LiOH.H$_2$O (930 mg, 22.16 mmol) in water (50 mL) was added dropwise to a solution of (2-[[8-amino-6-(4-methylpyridin-3-yl)-2,7-naphthyridin-3-yl]carbamoyl]-1-methylcyclopropyl)methyl acetate (3 g, 7.40 mmol) in tetrahydrofuran (150 mL) at room temperature. After 4 h, the reaction was filtered, and the filtrate was concentrated under vacuum. The resulting residue was purified by Prep-HPLC to afford N-[8-amino-6-(4-methylpyridin-3-yl)-2,7-naphthyridin-3-yl]-2-(hydroxymethyl)-2-methylcyclopropane-1-carboxamide (282.5 mg, 11%) as a white solid. LCMS (ESI): R$_T$ (min)=1.13, [M+H]+=364.2, method=M; $^1$H NMR (300 MHz, DMSO-d$_6$) δ 10.69 (s, 1H), 9.35 (s, 1H), 8.56 (s, 1H), 8.43 (d, J=5.1 Hz, 1H), 8.25 (s, 1H), 7.31 (d, J=5.1 Hz, 1H), 7.30 (s, 2H), 6.97 (s, 1H), 4.65 (t, J=9.0 Hz, 1H), 3.31-3.29 (m, 2H), 2.41 (s, 3H), 2.06-1.95 (m, 1H), 1.18 (s, 3H), 0.99-0.91 (m, 2H).

Example 166

(+/−)-N-(8-amino-5-bromo-6-(4-methylpyridin-3-yl)-2,7-naphthyridin-3-yl)-2-(cyanomethyl)cyclopropanecarboxamide (Compound 210)

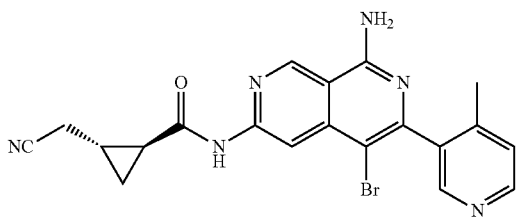 [SMILES: Cc1ccncc1-c1nc(N)c2cnc(NC(=O)[C@H]3C[C@@H]3CC#N)cc2c1Br]

A mixture of trans-N-[8-amino-6-(4-methylpyridin-3-yl)-2,7-naphthyridin-3-yl]-2-(cyanomethyl)cyclopropane-1-carboxamide (160 mg, 0.44 mmol) and NBS (210 mg, 1.18 mmol) in dichloromethane (10 mL) was stirred for 2 h at room temperature under nitrogen. The reaction solution was concentrated under vacuum. The resulting residue was purified by Flash-Prep-HPLC to afford trans-N-[8-amino-5-bromo-6-(4-methylpyridin-3-yl)-2,7-naphthyridin-3-yl]-2-(cyanomethyl)cyclopropane-1-carboxamide (31 mg, 16%) as a brown solid. LCMS (ESI): $R_T$ (min)=1.54, [M+H]+=437.1, method=K-1; $^1$H NMR (400 MHz, DMSO-$d_6$) δ 11.25 (s, 1H), 9.40 (s, 1H), 8.58 (s, 1H), 8.47 (d, J=6.0 Hz, 1H), 8.36 (s, 1H), 7.59 (s, 2H), 7.35 (d, J=6.0 Hz, 1H), 2.76-2.73 (m, 2H), 2.14-2.10 (m, 4H), 1.64-1.58 (m, 1H), 1.19-1.14 (m, 1H), 1.02-0.95 (m, 1H).

Example 167

(+/−)-cis-N-(8-amino-6-(2,3-dihydro-1H-pyrrolo[2,3-c]pyridin-4-yl)-2,7-naphthyridin-3-yl)-2-fluorocyclopropanecarboxamide (Compound 211)

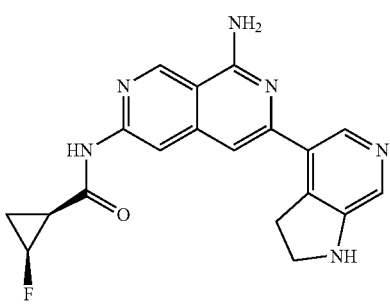 [SMILES: Nc1nc(-c2cncc3c2CCN3)cc2cc(NC(=O)[C@@H]3C[C@@H]3F)ncc12]

Step 1: 1-(tert-butoxycarbonyl)-2,3-dihydro-1H-pyrrolo[2,3-c]pyridin-4-ylboronic acid

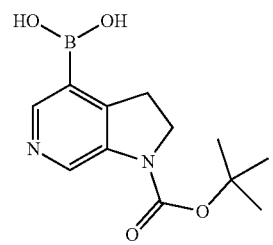 [SMILES: CC(C)(C)OC(=O)N1CCc2c(B(O)O)cncc21]

To a solution of tert-butyl 4-[(trifluoromethane)sulfonyloxy]-1H,2H,3H-pyrrolo[2,3-c]pyridine-1-carboxylate (1 g, 2.71 mmol ((J. Med. Chem. 2014, 57, 2462) in dioxane (40 mL) was added 4,4,5,5-tetramethyl-2-(tetramethyl-1,3,2-dioxaborolan-2-yl)-1,3,2-dioxaborolane (2 g, 7.87 mmol), Pd(dppf)Cl$_2$ (400 mg, 0.54 mmol) and KOAc (800 mg, 8.15 mmol). The reaction was stirred for 3 h at 100° C. under nitrogen and then cooled to room temperature. The pH of the resulting mixture was adjusted to 14 with sodium hydroxide. The resulting solution was washed with ethyl acetate and the aqueous layer was collected. The pH of the aqueous layer was adjusted to 1 with 2 N HCl. The resulting solution was extracted with ethyl acetate. The collected organic was dried over Na$_2$SO$_4$, filtered, and concentrated under vacuum to afford [1-[(tert-butoxy)carbonyl]-1H,2H,3H-pyrrolo[2,3-c]pyridin-4-yl]boronic acid (500 mg, 70%) as a yellow solid. LCMS (ESI): [M+H]+=265.1.

Step 2: cis-tert-butyl 4-(1-amino-6-((1S,2S)-2-fluorocyclopropanecarboxamido)-2,7-naphthyridin-3-yl)-2,3-dihydropyrrolo[2,3-c]pyridine-1-carboxylate

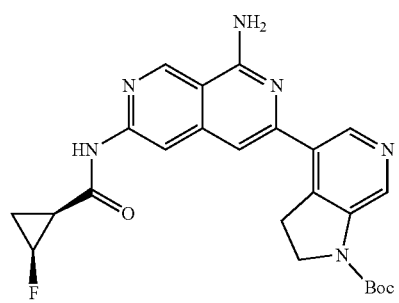

A suspension of cis-N-(8-amino-6-chloro-2,7-naphthyridin-3-yl)-2-fluorocyclopropane-1-carboxamide (200 mg, 0.71 mmol), 1-[(tert-butoxy)carbonyl]-1H,2H,3H-pyrrolo[2,3-c]pyridin-4-ylboronic acid (200 mg, 0.75 mmol), Pd(PPh$_3$)$_4$ (164 mg, 0.14 mmol) and Cs$_2$CO$_3$ (464 mg, 1.42 mmol) in dioxane (10 mL)/water (1 mL) was stirred at 100° C. After 3 h, the reaction mixture was concentrated under vacuum to afford crude cis-tert-butyl 4-(1-amino-6-[[(1S,2S)-2-fluorocyclopropane]amido]-2,7-naphthyridin-3-yl)-1H,2H,3H-pyrrolo[2,3-c]pyridine-1-carboxylate (200 mg) as a white solid. LCMS (ESI): [M+H]+=253.1.

Step 3: cis-N-(8-amino-6-(2,3-dihydro-1H-pyrrolo[2,3-c]pyridin-4-yl)-2,7-naphthyridin-3-yl)-2-fluorocyclopropanecarboxamide

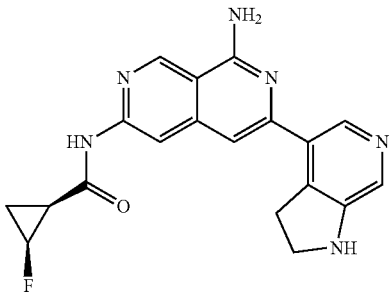 [SMILES: Nc1nc(-c2cncc3c2CCN3)cc2cc(NC(=O)[C@@H]3C[C@@H]3F)ncc12]

A solution of cis-tert-butyl 4-(1-amino-6-[[(1S,2S)-2-fluorocyclopropane]amido]-2,7-naphthyridin-3-yl)-1H,2H,3H-pyrrolo[2,3-c]pyridine-1-carboxylate (200 mg, 0.43 mmol) and trifluoroacetic acid (10 mL) in dichloromethane (50 mL) was stirred for 3 h at room temperature. The reaction mixture was then concentrated under vacuum, and the resulting residue was purified by Prep-HPLC to afford cis-N-(8-amino-6-[1H,2H,3H-pyrrolo[2,3-c]pyridin-4-yl]-2,7-naphthyridin-3-yl)-2-fluorocyclopropane-1-carboxamide formic acid salt (9.1 mg, 5%) as a yellow solid. LCMS (ESI): $R_T$ (min)=1.68, $[M+H]^+$=365.1, method=K-1; $^1$H NMR (300 MHz, DMSO-$d_6$) δ 11.07 (s, 1H), 9.41 (s, 1H), 8.41 (s, 1H), 8.35 (s, 1H), 7.83 (s, 1H), 7.48 (s, 2H), 7.31 (s, 1H), 6.54 (s, 1H), 5.08-5.11 (m, 1H), 4.86-4.89 (m, 1H), 3.66-3.49 (m, 4H), 2.32 (s, 1H), 1.76-1.62 (m, 1H), 1.21-1.26 (m, 1H).

Example 168

(+/−)-trans-N-(8-amino-6-(4-methylpyridin-3-yl)-2,7-naphthyridin-3-yl)-2-(cyanomethyl)cyclopropanecarboxamide (Compound 212)

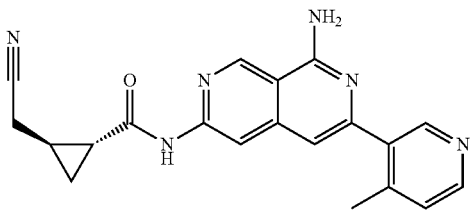 [SMILES: Cc1ccncc1-c1cc2cc(NC(=O)[C@@H]3C[C@H]3CC#N)ncc2c(N)n1]

A suspension of trans-N-(8-amino-6-chloro-2,7-naphthyridin-3-yl)-2-(cyanomethyl)cyclopropane-1-carboxamide (250 mg, 0.83 mmol), (4-methylpyridin-3-yl)boronic acid (170 mg, 1.24 mmol), Pd(dppf)Cl$_2$ (61 mg, 0.08 mmol) and potassium carbonate (343 mg, 2.48 mmol) in dioxane (8 mL)/water (2 mL) was stirred for 2 h at 110° C. under nitrogen. The solids were filtered, and the filtrate was concentrated under vacuum. The resulting residue was purified by Prep-HPLC to afford trans-N-(8-amino-6-(4-methylpyridin-3-yl)-2,7-naphthyridin-3-yl)-2-(cyanomethyl)cyclopropanecarboxamide (101 mg, 34%) as a white solid. LCMS (ESI): $R_T$(min)=0.96, $[M+H]^+$=359.2, method=K-1; $^1$H NMR (400 MHz, CD$_3$OD) δ 9.30 (s, 1H), 8.54 (s, 1H), 8.43 (d, J=5.1 Hz, 1H), 8.30 (s, 1H), 7.40 (d, J=5.1 Hz, 1H), 6.99 (s, 1H), 2.80-2.63 (m, 2H), 2.46 (s, 3H), 2.02-1.98 (m, 1H), 1.81-1.69 (m, 1H), 1.35-1.20 (m, 1H), 1.10-0.98 (m, 1H).

Example 169

(+/−)-2-(4-(8-amino-6-(4-methylpyridin-3-yl)-2,7-naphthyridin-3-ylamino)-1H-pyrazol-1-yl)propan-1-ol (Compound 213)

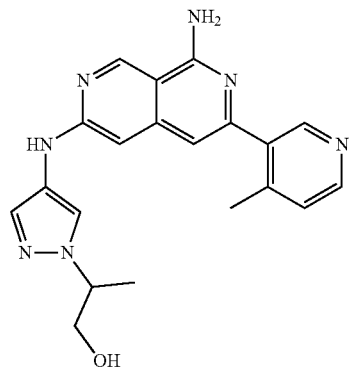 [SMILES: Cc1ccncc1-c1cc2cc(Nc3cnn(C(C)CO)c3)ncc2c(N)n1]

Step 1: methyl 2-(4-bromo-1H-pyrazol-1-yl)propanoate

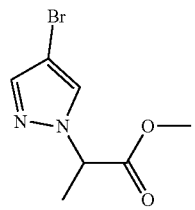

A suspension of 4-bromo-1H-pyrazole (5 g, 34.02 mmol), methyl 2-bromopropanoate (6.82 g, 40.85 mmol), and potassium carbonate (9.43 g, 68.30 mmol) in N,N-dimethylformamide (10 mL) was stirred for 5 h at 80° C. The reaction was quenched by water (30 mL), and the resulting solution was extracted with ethyl acetate. The combined organic extracts were dried over Na$_2$SO$_4$, filtered, and concentrated under vacuum to provide methyl 2-(4-bromo-1H-pyrazol-1-yl)propanoate (7.1 g, 90%) as a colorless oil. LCMS(ESI): $[M+H]^+$=233.1.

Step 2: 2-(4-bromo-1H-pyrazol-1-yl)propan-1-ol

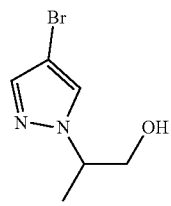

NaBH₄ (489 mg, 12.92 mmol) was added portionwise to a stirred solution of methyl 2-(4-bromo-1H-pyrazol-1-yl)propanoate (1 g, 4.29 mmol) in methanol (10 mL) at 25° C. After 3 h, the reaction was quenched by water (30 mL), and the resulting solution was extracted with ethyl acetate (100 mL). The collected organic was dried over Na₂SO₄, filtered, and concentrated under vacuum to afford 2-(4-bromo-1H-pyrazol-1-yl)propan-1-ol (716 mg, 81%) as a colorless oil. LCMS (ESI): [M+H]⁺=205.2.

Step 3: 2-(4-(8-(bis(2,4-dimethoxybenzyl)amino)-6-(4-methylpyridin-3-yl)-2,7-naphthyridin-3-ylamino)-1H-pyrazol-1-yl)propan-1-ol

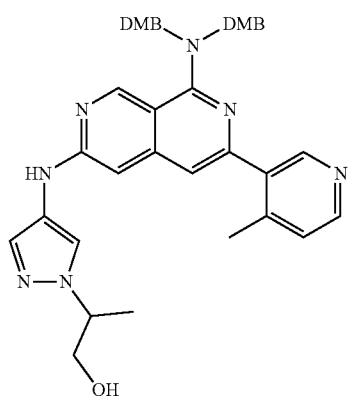

A suspension of 1-N,1-N-bis[(2,4-dimethoxyphenyl)methyl]-3-(4-methylpyridin-3-yl)-2,7-naphthyridine-1,6-diamine (300 mg, 0.54 mmol), 2-(4-bromo-1H-pyrazol-1-yl)propan-1-ol (223 mg, 1.09 mmol), Cs₂CO₃ (1.062 g, 3.26 mmol), t-BuBrettPhos (131 mg, 0.27 mmol) and 3rd Generation t-BuBrettPhos precatalyst (232 mg, 0.27 mmol) in dioxane (5 mL) was stirred for 2 h at 120° C. under nitrogen. The solids were filtered, and the filtrate was concentrated under vacuum. The resulting residue was purified by silica gel chromatography (20:1 dichloromethane/methanol) to provide 2-[4-[(8-[bis[(2,4-dimethoxyphenyl)methyl]amino]-6-(4-methylpyridin-3-yl)-2,7-naphthyridin-3-yl)amino]-1H-pyrazol-1-yl]propan-1-ol (288 mg, 8%) as a brown solid. LCMS (ESI): [M+H]⁺=676.2.

Step 4: 2-(4-(8-amino-6-(4-methylpyridin-3-yl)-2,7-naphthyridin-3-ylamino)-1H-pyrazol-1-yl)propan-1-ol

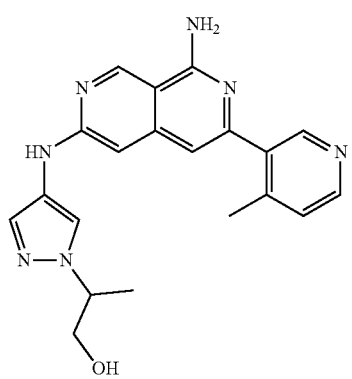 [SMILES: Cc1ccncc1-c1cc2cc(Nc3cnn(C(C)CO)c3)ncc2c(N)n1]

A solution of 2-[4-[(8-[bis[(2,4-dimethoxyphenyl)methyl]amino]-6-(4-methylpyridin-3-yl)-2,7-naphthyridin-3-yl)amino]-1H-pyrazol-1-yl]propan-1-ol (278 mg, 0.41 mmol) in trifluoroacetic acid (8 mL) was heated at 50° C. After 2 h, the reaction was concentrated under vacuum. The residue was diluted with ammonium hydroxide to pH=13, and the resulting solution was purified by Prep-HPLC to afford 2-(4-(8-amino-6-(4-methylpyridin-3-yl)-2,7-naphthyridin-3-ylamino)-1H-pyrazol-1-yl)propan-1-ol (3 mg, 2%) as a white solid. LCMS (ESI): R$_T$ (min)=1.58, [M+H]⁺=376.4, method=N; ¹H NMR (400 MHz, DMSO-d₆) δ 9.22 (s, 1H), 8.83 (s, 1H), 8.53 (s, 1H), 8.42 (d, J=5.0 Hz, 1H), 7.90 (s, 1H), 7.50 (s, 1H), 7.29 (d, J=5.0 Hz, 1H), 7.06 (s, 2H), 6.75 (s, 1H), 6.64 (s, 1H), 4.92 (t, J=5.5 Hz, 1H), 4.45-4.32 (m, 1H), 3.73-3.55 (m, 2H), 2.40 (s, 3H), 1.40 (d, J=6.8 Hz, 3H).

Example 170

(1R,2R)—N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Compound 214) and (1S,2S)—N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Compound 215)

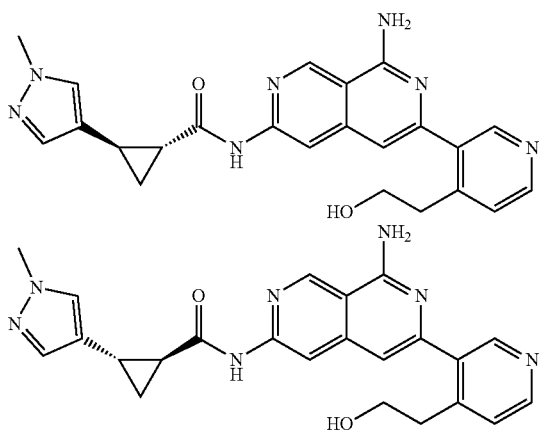

Step 1: trans-N-(6,8-dichloro-2,7-naphthyridin-3-yl)-2-(1-methyl-1H-pyrazol-4-yl)cyclopropane-1-carboxamide

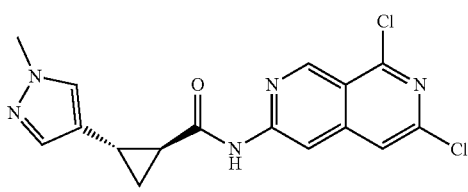 [SMILES: Cn1cc([C@H]2C[C@@H]2C(=O)Nc2cc3cc(Cl)nc(Cl)c3cn2)cn1]

Oxalyl chloride (1.16 g, 9.14 mmol) was added dropwise to a solution of trans-2-(1-methyl-1H-pyrazol-4-yl)cyclopropane-1-carboxylic acid (1.00 g, 6.01 mmol) and N,N-dimethylformamide (3 drop, cat) in 2:1 dichloromethane/pyridine (30 mL) at 0° C. The reaction was stirred for 30 mins at room temperature. The reaction solution was then added dropwise to a stirred solution of 6,8-dichloro-2,7-naphthyridin-3-amine hydrochloride (1.25 g, 4.99 mmol) in dichloromethane (50 mL) at 0° C. The mixture was warmed to room temperature for 2 h under nitrogen. The reaction was diluted with water (30 mL), and the resulting solution was extracted with dichloromethane (100 mL). The organic extract was dried over Na$_2$SO$_4$, filtered, and concentrated under vacuum. Purified by silica-gel column chromatography (20:1 DCM/MeOH) afforded trans-N-(6,8-dichloro-2,7-naphthyridin-3-yl)-2-(1-methyl-1H-pyrazol-4-yl)cyclopropane-1-carboxamide (800 mg, 40%) as an off-white solid. LCMS (ESI): [M+H]$^+$=362.0.

Step 2: trans-N-(8-amino-6-chloro-2,7-naphthyridin-3-yl)-2-(1-methyl-1H-pyrazol-4-yl)cyclopropane-1-carboxamide

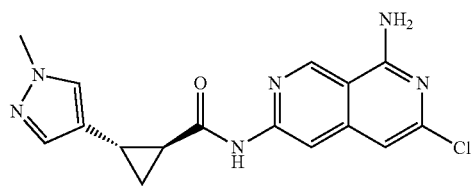 [SMILES: Cn1cc([C@H]2C[C@@H]2C(=O)Nc2cc3cc(Cl)nc(N)c3cn2)cn1]

A solution of trans-N-(6,8-dichloro-2,7-naphthyridin-3-yl)-2-(1-methyl-1H-pyrazol-4-yl)cyclopropane-1-carboxamide (300 mg, 0.83 mmol) and ammonium hydroxide (8 mL) in dioxane (8 mL) was heated at 100° C. under nitrogen. After 16 h, the reaction mixture was concentrated under vacuum, and the resulting residue was purified by silica-gel column chromatography (10:1 DCM/MeOH) to provide trans-N-(8-amino-6-chloro-2,7-naphthyridin-3-yl)-2-(1-methyl-1H-pyrazol-4-yl)cyclopropane-1-carboxamide (250 mg, 88%) as an off-white solid. LCMS (ESI): [M+H]$^+$=343.0.

Step 3: trans-N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Compound 214) and trans-N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Compound 215)

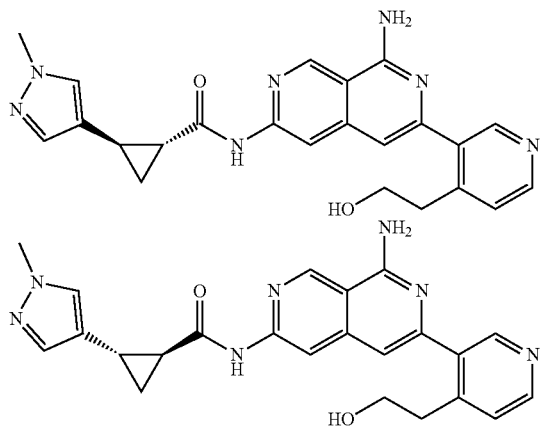

A suspension of trans-N-(8-amino-6-chloro-2,7-naphthyridin-3-yl)-2-(1-methyl-1H-pyrazol-4-yl)cyclopropane-1-carboxamide (300 mg, 0.87 mmol), 1H,3H,4H-[1,2]oxaborinino[3,4-c]pyridin-1-ol (390.05 mg, 2.61 mmol), XPhos (83.86 mg, 0.17 mmol), XPhos-PdCl-2nd G (71.81 mg, 0.09 mmol), and KOAc (258.02 mg, 2.62 mmol) in 10:1 dioxane/water (16.5 mL) was stirred for 2 h at 100° C. under nitrogen. The reaction was concentrated under vacuum, and the resulting residue was purified by silica-gel column chromatography (15:1 dichloromethane/methanol) to afford trans-N-[8-amino-6-[4-(2-hydroxyethyl)pyridin-3-yl]-2,7-naphthyridin-3-yl]-2-(1-methyl-1H-pyrazol-4-yl)cyclopropane-1-carboxamide (70 mg, 18%) as a white solid. The enantiomers were separated by chiral SFC. Compound 214: LCMS (ESI): R$_T$(min)=1.04, [M+H]$^+$=430.0, method=M; $^1$H NMR (400 MHz, DMSO-d$_6$) δ 10.95 (s, 1H), 9.38 (s, 1H), 8.52 (s, 1H), 8.48 (d, J=4.8 Hz, 1H), 8.25 (s, 1H), 7.56 (s, 1H), 7.37 (d, J=4.8 Hz, 1H), 7.32 (s, 2H), 7.29 (s, 1H), 6.97 (s, 1H), 4.78 (t, J=5.2 Hz, 1H), 3.77 (s, 3H), 3.60-3.55 (m, 2H), 2.95-2.91 (m, 2H), 2.23-2.19 (m, 2H), 1.41-1.37 (m, 1H), 1.22-1.19 (m, 1H). Compound 215: LCMS (ESI): R$_T$(min)=1.04, [M+H]$^+$=430.0, method=M; $^1$H NMR (400 MHz, CD$_3$OD) δ10.95 (s, 1H), 9.38 (s, 1H), 8.52 (s, 1H), 8.48 (d, J=4.8 Hz, 1H), 8.25 (s, 1H), 7.56 (s, 1H), 7.37 (d, J=4.8 Hz, 1H), 7.32 (s, 2H), 7.29 (s, 1H), 6.97 (s, 1H), 4.78 (t, J=5.2 Hz, 1H), 3.77 (s, 3H), 3.60-3.55 (m, 2H), 2.95-2.91 (m, 2H), 2.23-2.19 (m, 2H), 1.41-1.37 (m, 1H), 1.22-1.19 (m, 1H).

Example 171

(+/−)-cis-N-(8-amino-6-(4-methyl-5-(methylamino)pyridin-3-yl)-2,7-naphthyridin-3-yl)-2-fluorocyclopropanecarboxamide (Compound 216)

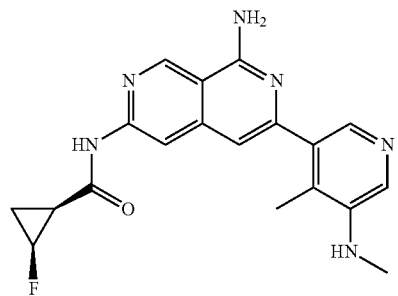 [SMILES: CNc1cncc(-c2cc3cc(NC(=O)[C@@H]4C[C@@H]4F)ncc3c(N)n2)c1C]

Step 1: 5-bromo-N,4-dimethylpyridin-3-amine

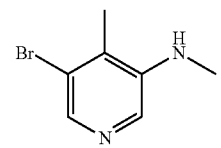

A mixture of 3,5-dibromo-4-methylpyridine (1 g, 3.98 mmol), Cu (52 mg, 0.81 mmol) and CH$_3$NH$_2$ (8 mL) in dioxane (5 mL) was heated at 100° C. After 5 h, the mixture was concentrated under vacuum, and the resulting residue was purified by silica gel chromatography (10:1 dichloromethane/methanol) to afford 5-bromo-N,4-dimethylpyridin-3-amine (400 mg, 50%) as a light yellow solid. LCMS (ESI): M+H⁺=201.0.

Step 2: [4-methyl-5-(methylamino)pyridin-3-yl]boronic acid

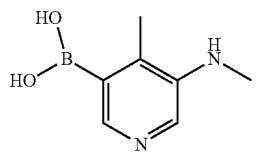

A suspension of 5-bromo-N,4-dimethylpyridin-3-amine (1.648 g, 8.19 mmol), 4,4,5,5-tetramethyl-2-(tetramethyl-1,3,2-dioxaborolan-2-yl)-1,3,2-dioxaborolane (8.3 g, 32.68 mmol), Pd(dppf)Cl$_2$ (599 mg, 0.81 mmol), KOAc (2.41 g, 24.55 mmol) in dioxane (80 mL) was stirred for 3 h at 100° C. under nitrogen. The solid were filtered, and the filtrate was concentrated under vacuum. The resulting residue was diluted with water (30 mL) and the pH of the solution was adjusted to 10 with aqueous NaOH. The basic solution was washed with ethyl acetate. The aqueous layer was collected and acidified to pH=3 with HCl. The acidic solution was extracted with ethyl acetate, and the collected extracts were dried over Na$_2$SO$_4$, filtered, and concentrated under vacuum. The resulting residue was dissolved in 1:1 ethyl acetate/ethanol and filtered. The filtrate was concentrated under vacuum to afford [4-methyl-5-(methylamino)pyridin-3-yl]boronic acid (595 mg, 44%) as a brown oil. LCMS (ESI): [M+H]⁺=167.1.

Step 3: cis-N-[8-amino-6-[4-methyl-5-(methylamino)pyridin-3-yl]-2,7-naphthyridin-3-yl]-2-fluorocyclopropane-1-carboxamide

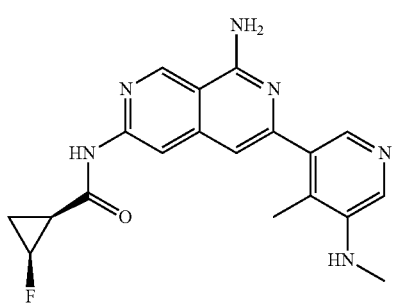 [SMILES: CNc1cncc(-c2cc3cc(NC(=O)[C@@H]4C[C@@H]4F)ncc3c(N)n2)c1C]

A suspension of cis-N-(8-amino-6-chloro-2,7-naphthyridin-3-yl)-2-fluorocyclopropane-1-carboxamide (506 mg, 1.80 mmol), [4-methyl-5-(methylamino)pyridin-3-yl]boronic acid (1.09 g, 6.56 mmol), X-Phos (86 mg, 0.18 mmol), XPhos palladium(II) biphenyl-2-amine chloride (142 mg, 0.18 mmol) and potassium carbonate (745 mg, 5.39 mmol) in 4:1 dioxane/water (25 mL) was stirred for 2 h at 100° C. under nitrogen. The solids were filtered, and the filtrate was concentrated under vacuum. The crude product was purified by Flash-Prep-HPLC to afford cis-N-[8-amino-6-[4-methyl-5-(methylamino)pyridin-3-yl]-2,7-naphthyridin-3-yl]-2-fluorocyclopropane-1-carboxamide (60 mg, 9%) as a light brown solid. LCMS (ESI): R$_T$ (min)=1.46, [M+H]⁺=367.2, method=M; ¹H NMR (400 MHz, DMSO-d$_6$) δ 10.99 (s, 1H), 9.37 (s, 1H), 8.21 (s, 1H), 7.87 (s, 1H), 7.83 (s, 1H), 7.28 (s, 2H), 6.85 (s, 1H), 5.33-5.03 (m, 1H), 5.09-4.82 (m, 1H), 2.82 (d, J=6.0 Hz, 3H), 2.30-2.23 (m, 1H), 2.09 (s, 3H), 1.76-1.61 (m, 1H), 1.25-1.14 (m, 1H).

Example 172

(+/−)-2-(4-(8-amino-6-(4-methylpyridin-3-yl)-2,7-naphthyridin-3-ylamino)-1H-pyrazol-1-yl)propanenitrile (Compound 217)

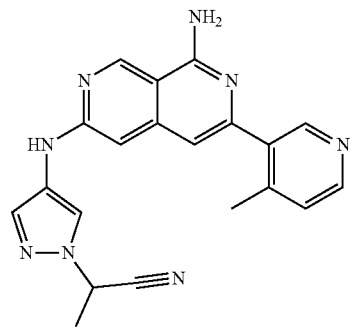 [SMILES: Cc1ccncc1-c1cc2cc(Nc3cnn(C(C)C#N)c3)ncc2c(N)n1]

Step 1: 2-(4-bromo-1H-pyrazol-1-yl)propanenitrile

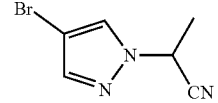

A suspension of 4-bromo-1H-pyrazole (1 g, 6.80 mmol), 2-chloropropanenitrile (612 mg, 6.83 mmol), Cs$_2$CO$_3$ (2.43 g, 7.45 mmol) in tetrahydrofuran (10 mL) was heated at 100° C. After 2 h, the solids were filtered, and the filtrate was concentrated under vacuum. Purification by silica gel chromatography (10:1 dichloromethane/methanol) afforded 2-(4-bromo-1H-pyrazol-1-yl)propanenitrile (952 mg, 70%) as a white solid. LCMS (ESI): [M+H]⁺=200.0.

Step 2: 2-(4-(8-(bis(2,4-dimethoxybenzyl)amino)-6-(4-methylpyridin-3-yl)-2,7-naphthyridin-3-ylamino)-1H-pyrazol-1-yl)propanenitrile

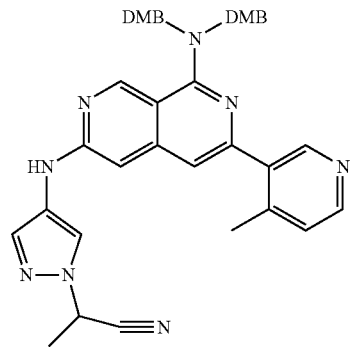

A suspension of 1-N,1-N-bis[(2,4-dimethoxyphenyl)methyl]-3-(4-methylpyridin-3-yl)-2,7-naphthyridine-1,6-diamine (552 mg, 1.00 mmol), 2-(4-bromo-1H-pyrazol-1-yl)propanenitrile (800 mg, 3.99 mmol), t-BuBrettPhos (97 mg, 0.20 mmol), 3rd Generation t-BuBrettPhos precatalyst (171 mg, 0.20 mmol), and potassium carbonate (828 mg, 5.99 mmol) in dioxane (15 mL) was heated at 120° C. After 5 h, the reaction was concentrated under vacuum. The resulting residue was purified by silica gel chromatography (10:1 dichloromethane/methanol) to yield 2-[4-[(8-[bis[(2,4-dimethoxyphenyl)methyl]amino]-6-(4-methylpyridin-3-yl)-2,7-naphthyridin-3-yl)amino]-1H-pyrazol-1-yl]propanenitrile (302 mg, 45%) as a brown oil. LCMS (ESI): [M+H]$^+$=671.3.

Step 3: 2-(4-(8-amino-6-(4-methylpyridin-3-yl)-2,7-naphthyridin-3-ylamino)-1H-pyrazol-1-yl)propanenitrile

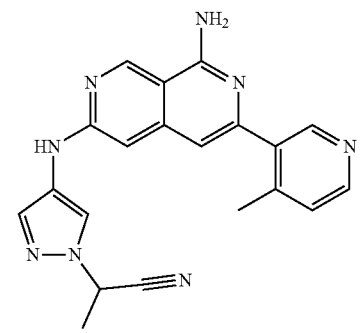

A solution of 2-[4-[(8-[bis[(2,4-dimethoxyphenyl)methyl]amino]-6-(4-methylpyridin-3-yl)-2,7-naphthyridin-3-yl)amino]-1H-pyrazol-1-yl]propanenitrile (248 mg, 0.37 mmol) in TFA (20 mL) was heded at 80° C. After 45 min, the reaction was concentrated under vacuum, and the residue was diluted with methanol. The solution was basified to pH=8 with ammonium hydroxide and purified by Prep-HPLC to provide 2-(4-[[8-amino-6-(4-methylpyridin-3-yl)-2,7-naphthyridin-3-yl]amino]-1H-pyrazol-1-yl)propanenitrile (65.4 mg, 48%) as a yellow solid. LCMS (ESI): R$_T$ (min)=2.00, [M+H]$^+$=371.2, method=M; $^1$H NMR (400 MHz, CD$_3$OD) δ 9.19 (s, 1H), 8.50 (s, 1H), 8.42 (d, J=6.0 Hz, 1H), 8.13 (s, 1H), 7.70 (s, 1H), 7.39 (d, J=6.0 Hz, 1H), 6.78 (s, 1H), 6.74 (s, 1H), 5.64 (q, J=6.0 Hz, 1H), 2.44 (s, 3H), 1.91 (d, J=6.0 Hz, 3H).

Example 173

(+/−)-1-(3-(4-(8-amino-6-(4-methylpyridin-3-yl)-2,7-naphthyridin-3-ylamino)-1H-pyrazol-1-yl)pyrrolidin-1-yl)ethanone (Compound 218)

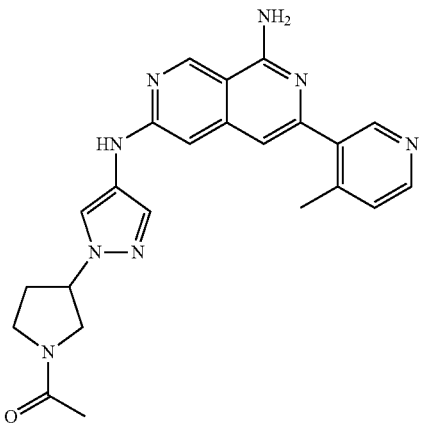 [SMILES: CC(=O)N1CCC(n2cc(Nc3cc4cc(-c5cnccc5C)nc(N)c4cn3)cn2)C1]

Step 1: tert-butyl 3-(4-bromo-1H-pyrazol-1-yl)pyrrolidine-1-carboxylate

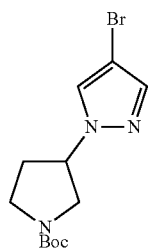 [SMILES: Brc1cnn(C2CCNC2)c1]

A suspension of 4-bromo-1H-pyrazole (200 mg, 1.36 mmol), tert-butyl 3-bromopyrrolidine-1-carboxylate (409 mg, 1.64 mmol), and potassium carbonate (567 mg, 4.10 mmol) in N,N-dimethylformamide (4 mL) was heated at 100° C. After 12 h, the reaction mixture was concentrated under vacuum, and the resulting residue was purified by silica gel chromatography (100:1 dichloromethane/methanol) to afford tert-butyl 3-(4-bromo-1H-pyrazol-1-yl)pyrrolidine-1-carboxylate (310 mg, 72%) as a yellow oil. LCMS (ESI): [M+H]$^+$=316.2

Step 2: 4-bromo-1-(pyrrolidin-3-yl)-1H-pyrazole

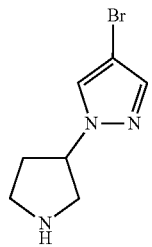

A solution of tert-butyl 3-(4-bromo-1H-pyrazol-1-yl)pyrrolidine-1-carboxylate (3.0 g, 9.49 mmol) in trifluoroacetic acid (5 mL) and dichloromethane (15 mL) was stirred for 2 h at 25° C. The resulting mixture was concentrated under vacuum to afford crude 4-bromo-1-(pyrrolidin-3-yl)-1H-pyrazole (2.6 g). LCMS (ESI): [M+H]$^+$=216.1.

Step 3: 1-(3-(4-bromo-1H-pyrazol-1-yl)pyrrolidin-1-yl)ethanone

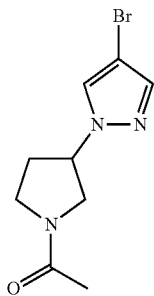

To an ice-cooled solution of 4-bromo-1-(pyrrolidin-3-yl)-1H-pyrazole (2 g, 9.25 mmol) and triethylamine (5 mL, 35.97 mmol) in dichloromethane (15 mL) was added acetyl chloride (1.1 g, 14.01 mmol) dropwise. The reaction was warmed to 25° C. After 1 h, the reaction was diluted with water (30 mL), and the solution was extracted with ethyl acetate. The organic extract was dried over Na$_2$SO$_4$, filtered, and concentrated under vacuum. Purification by silica gel chromatography (98:1 dichloromethane/methanol) provided 1-[3-(4-bromo-1H-pyrazol-1-yl)pyrrolidin-1-yl]ethan-1-one (1.2 g, 50%) as a yellow oil. LCMS (ESI): [M+H]$^+$=258.2.

Step 4: 1-(3-(4-(8-(bis(2,4-dimethoxybenzyl)amino)-6-(4-methylpyridin-3-yl)-2,7-naphthyridin-3-ylamino)-1H-pyrazol-1-yl)pyrrolidin-1-yl)ethanone

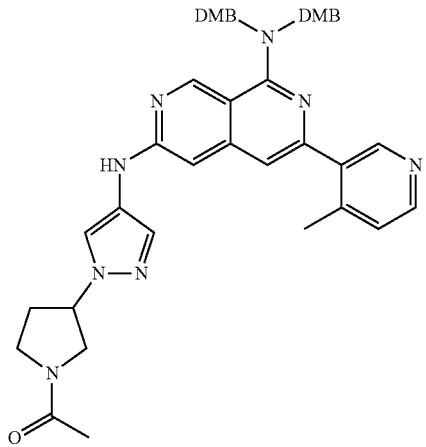

A suspension of 1-N,1-N-bis[(2,4-dimethoxyphenyl)methyl]-3-(4-methylpyridin-3-yl)-2,7-naphthyridine-1,6-diamine (350 mg, 0.63 mmol), 1-[3-(4-bromo-1H-pyrazol-1-yl)pyrrolidin-1-yl]ethan-1-one (409 mg, 1.58 mmol), potassium carbonate (525 mg, 3.79 mmol), t-BuBrettPhos (154 mg, 0.32 mmol) and 3rd generation t-BuBrettPhos precatalyst (271 mg, 0.32 mmol) in dioxane (5 mL) was heated at 120° C. After 2 h, the reaction was cooled to room temperature and filtered. The filtrate was concentrated under vacuum, and the resulting residue was purified by silica gel chromatography (25:1 dichloromethane/methanol) to provide 1-(3-[4-[(8-[bis[(2,4-dimethoxyphenyl)methyl]amino]-6-(4-methylpyridin-3-yl)-2,7-naphthyridin-3-yl)amino]-1H-pyrazol-1-yl]pyrrolidin-1-yl)ethan-1-one (349 mg, 30%) as a brown solid. LCMS (ESI): [M+H]$^+$=729.8.

Step 5: 1-(3-(4-(8-amino-6-(4-methylpyridin-3-yl)-2,7-naphthyridin-3-ylamino)-1H-pyrazol-1-yl)pyrrolidin-1-yl)ethanone

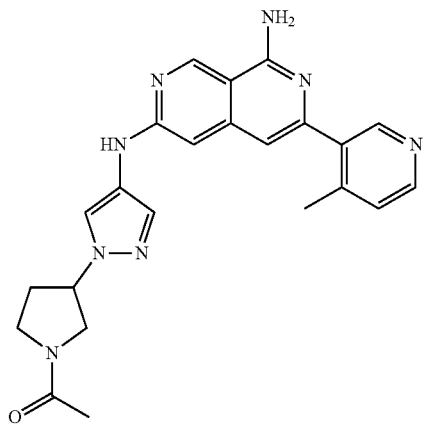 [SMILES: CC(=O)N1CCC(n2cc(Nc3cc4cc(-c5cnccc5C)nc(N)c4cn3)cn2)C1]

A solution of 1-(3-[4-[(8-[bis[(2,4-dimethoxyphenyl)methyl]amino]-6-(4-methylpyridin-3-yl)-2,7-naphthyridin-3-yl)amino]-1H-pyrazol-1-yl]pyrrolidin-1-yl)ethan-1-one (299 mg, 0.41 mmol) in trifluoroacetic acid (6 ml) was heated at 50° C. After 2 h, the reaction solution was concentrated under vacuum. The resulting residue was dissolved in methanol, and the solution was basified to pH=9 with aqueous ammonium hydroxide. Purification by Prep-HPLC afforded 1-(3-(4-(8-amino-6-(4-methylpyridin-3-yl)-2,7-naphthyridin-3-ylamino)-1H-pyrazol-1-yl)pyrrolidin-1-yl)ethanone (40 mg, 23%) as a white solid. LCMS (ESI): R$_T$ (min)=1.51, [M+H]$^+$=429.2, method=K-1; $^1$H NMR (400 MHz, DMSO-d$_6$) δ 9.22 (s, 1H), 8.91 (d, J=6.6 Hz, 1H), 8.53 (s, 1H), 8.42 (d, J=5.0 Hz, 1H), 8.00 (d, J=11.7 Hz, 1H), 7.55 (d, J=5.0 Hz, 1H), 7.29 (d, J=6.6 Hz, 1H), 7.08 (s, 2H), 6.76 (s, 1H), 6.66 (s, 1H), 5.10-4.90 (m, 0.5H), 3.98-3.90 (m, 1H), 3.81-3.71 (m, 1H), 3.71-3.58 (m, 1.5H), 3.54-3.40 (m, 1H), 2.40 (s, 4H), 2.34-2.26 (m, 1H), 1.97 (d, J=5.3 Hz, 3H).

Example 174

(+/−)-trans-3-(4-(8-amino-6-(4-methylpyridin-3-yl)-2,7-naphthyridin-3-ylamino)-1H-pyrazol-1-yl)-1-(oxetan-3-yl)piperidin-4-ol (Compound 219) and (+/−)-trans-4-(4-(8-amino-6-(4-methylpyridin-3-yl)-2,7-naphthyridin-3-ylamino)-1H-pyrazol-1-yl)-1-(oxetan-3-yl)piperidin-3-ol (Compound 220)

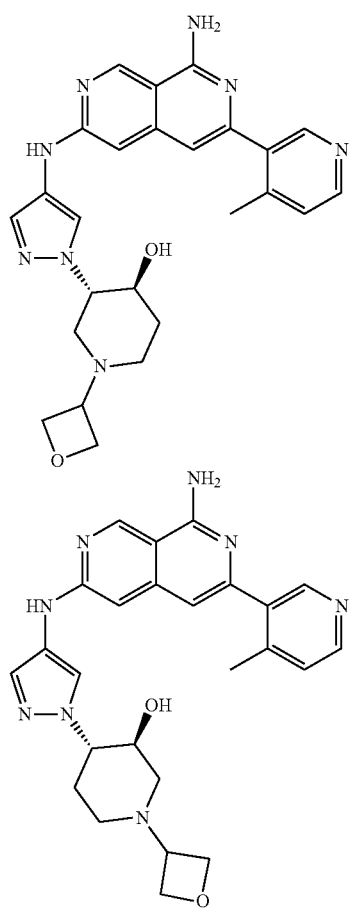

Step 1: tert-Butyl trans-4-(4-bromo-1H-pyrazol-1-yl)-3-hydroxypiperidine-1-carboxylate and tert-butyl trans-3-(4-bromo-1H-pyrazol-1-yl)-4-hydroxypiperidine-1-carboxylate

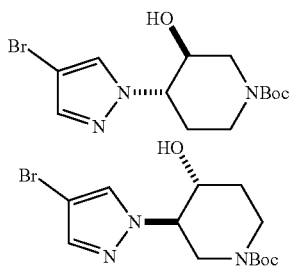

To an ice-cooled a solution of 4-bromo-1H-pyrazole (10.0 g, 68.04 mmol) in tetrahydrofuran (100 mL) was added sodium hydride (2.28 g, 95.01 mmol) portionwise. The reaction was warmed to room temperature. After 1 h, tert-butyl 7-oxa-3-azabicyclo[4.1.0]heptane-3-carboxylate (20.0 g, 100.38 mmol) was added to the reaction, and the resulting solution was heated at 70° C. for 16 h. The reaction was diluted with water, and the mixture was extracted with dichloromethane. The organic extract was dried over Na$_2$SO$_4$, filtered, and concentrated under vacuum. Purification by silica gel chromatography (1:2 ethyl acetate/petroleum ether) afforded a mixture of tert-butyl trans-4-(4-bromo-1H-pyrazol-1-yl)-3-hydroxypiperidine-1-carboxylate and tert-butyl trans-3-(4-bromo-1H-pyrazol-1-yl)-4-hydroxypiperidine-1-carboxylate (1.4 g, 6%) as a white solid. LCMS (ESI): [M+H]$^+$=346.1.

Step 2: trans-4-(4-Bromo-1H-pyrazol-1-yl)piperidin-3-ol and trans-3-(4-bromo-1H-pyrazol-1-yl)piperidin-4-ol

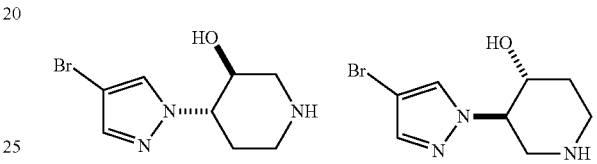

A solution of 4 M hydrogen chloride in 1,4-dioxane (20 mL) was added dropwise to a solution of tert-butyl 4-(4-bromo-1H-pyrazol-1-yl)-3-hydroxypiperidine-1-carboxylate and tert-butyl trans-3-(4-bromo-1H-pyrazol-1-yl)-4-hydroxypiperidine-1-carboxylate (650 mg, 1.88 mmol) in dichloromethane (10 mL) at room temperature. After 2 h, the reaction was concentrated under vacuum to afford a mixture of 4-(4-bromo-1H-pyrazol-1-yl)piperidin-3-ol hydrochloride and 3-(4-bromo-1H-pyrazol-1-yl)piperidin-4-ol hydrochloride (670 mg) as a white solid. LCMS (ESI): [M+H]$^+$=248.0.

Step 3: trans-4-(4-Bromo-1H-pyrazol-1-yl)-1-(oxetan-3-yl)piperidin-3-ol and trans-3-(4-bromo-1H-pyrazol-1-yl)-1-(oxetan-3-yl)piperidin-4-ol

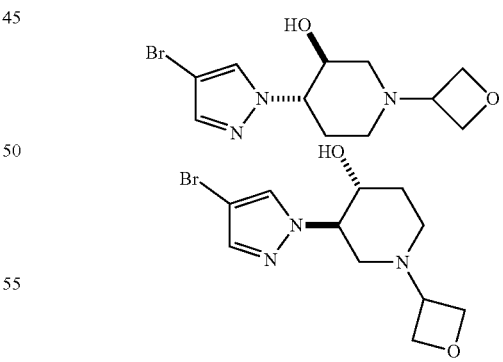

NaBH$_3$CN (250 mg, 3.98 mmol) was added to a solution of the above mixture of 4-(4-bromo-1H-pyrazol-1-yl)piperidin-3-ol and 3-(4-bromo-1H-pyrazol-1-yl)piperidin-4-ol (650 mg, 2.64 mmol) and oxetan-3-one (250 mg, 3.47 mmol) in methanol (20 mL) at room temperature. After 16 h, the reaction was diluted with water and concentrated under vacuum. The resulting residue was purified by silica gel chromatography (10:1 dichloromethane/methanol) to

721 provide a mixture of 4-(4-bromo-1H-pyrazol-1-yl)-1-(oxetan-3-yl)piperidin-3-ol and 3-(4-bromo-1H-pyrazol-1-yl)-1-(oxetan-3-yl)piperidin-4-ol (600 mg, 75%) as a light yellow oil. LCMS (ESI): [M+H]$^+$=302.2.

Step 4: 4-[4-[(8-[Bis[(2,4-dimethoxybenzyl)]amino]-6-(4-methylpyridin-3-yl)-2,7-naphthyridin-3-yl)amino]-1H-pyrazol-1-yl]-1-(oxetan-3-yl)piperidin-3-ol and 3-(4-((8-(bis(3,4-dimethylbenzyl)amino)-6-(4-methylpyridin-3-yl)-2,7-naphthyridin-3-yl)amino)-1H-pyrazol-1-yl)-1-(oxetan-3-yl)piperidin-4-ol

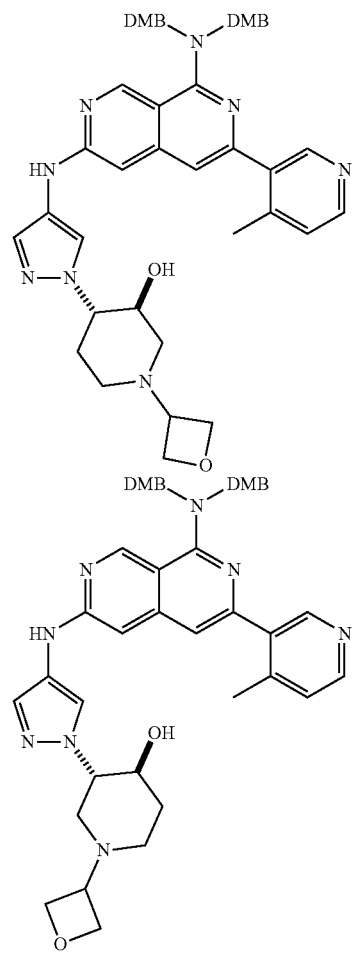

A mixture of 1-N,1-N-bis[(2,4-dimethoxyphenyl)methyl]-3-(4-methylpyridin-3-yl)-2,7-naphthyridine-1,6-diamine (100 mg, 0.18 mmol), 4-(4-bromo-1H-pyrazol-1-yl)-1-(oxetan-3-yl)piperidin-3-ol/3-(4-bromo-1H-pyrazol-1-yl)-1-(oxetan-3-yl)piperidin-4-ol (218 mg, 0.72 mmol), LiHMDS (226 mg, 1.35 mmol), 3rd generation t-BuBrett Phos precatalyst (80 mg, 0.09 mmol) and t-BuBrettPhos (43 mg, 0.09 mmol) in 1,4-dioxane (3.5 mL) was heated with microwave radiation for 2 h at 135° C. The solids were filtered, and the filtrate was concentrated. The resulting residue was purified by silica gel chromatography (10:1 dichloromethane/methanol) to afford 4-[4-[(8-[bis[(2,4-dimethoxyphenyl)methyl]amino]-6-(4-methylpyridin-3-yl)-2,7-naphthyridin-3-yl)amino]-1H-pyrazol-1-yl]-1-(oxetan-3-yl)piperidin-3-ol and 3-(4-((8-(bis(3,4-dimethylbenzyl)

722 amino)-6-(4-methylpyridin-3-yl)-2,7-naphthyridin-3-yl)amino)-1H-pyrazol-1-yl)-1-(oxetan-3-yl)piperidin-4-ol (72.5 mg, 52%) as a yellow solid. LCMS (ESI): [M+H]$^+$=773.0.

Step 5: (±)-trans-4-(4-(8-amino-6-(4-methylpyridin-3-yl)-2,7-naphthyridin-3-ylamino)-1H-pyrazol-1-yl)-1-(oxetan-3-yl)piperidin-3-ol and (±)-trans-3-(4-(8-amino-6-(4-methylpyridin-3-yl)-2,7-naphthyridin-3-ylamino)-1H-pyrazol-1-yl)-1-(oxetan-3-yl)piperidin-4-ol

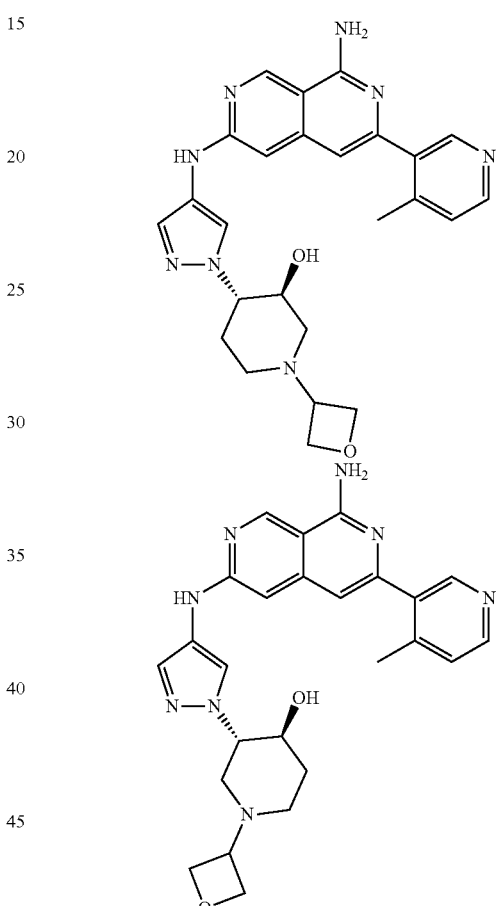

A solution of 4-[4-[(8-[bis[(2,4-dimethoxyphenyl)methyl]amino]-6-(4-methylpyridin-3-yl)-2,7-naphthyridin-3-yl)amino]-1H-pyrazol-1-yl]-1-(oxetan-3-yl)piperidin-3-ol/3-(4-(8-amino-6-(4-methylpyridin-3-yl)-2,7-naphthyridin-3-ylamino)-1H-pyrazol-1-yl)-1-(oxetan-3-yl)piperidin-4-ol (300 mg, 0.39 mmol) in trifluoroacetic acid (15 mL) was heated at 80° C. After 2 h, the reaction solution was concentrated under vacuum. The resulting residue was dissolved in methanol, and the pH of the solution was adjusted to 9 with ammonium hydroxide. Purification by Prep-HPLC provided a mixture of regioisomers (32 mg). The regioisomers were separated by chiral-Prep-HPLC. Compound 219: LCMS (ESI): R$_T$ (min)=2.12, [M+H]$^+$=473.2, method=M; $^1$H NMR (300 MHz, CD$_3$OD) δ 9.15 (s, 1H), 8.50 (s, 1H), 8.43 (d, J=5.1 Hz, 1H), 8.00 (s, 1H), 7.61 (s, 1H), 7.40 (d, J=5.1 Hz, 1H), 6.80 (s, 1H), 6.70 (s, 1H), 4.88-4.60 (m, 4H), 4.18-4.11 (m, 1H), 4.05-3.96 (m, 1H), 3.66-3.55 (m, 1H), 3.04-3.00 (m, 1H), 2.87-2.84 (m, 1H), 2.44-2.38 (m, 4H), 2.14-2.07 (m, 2H), 1.78-1.73 (m, 1H). Compound 220: LCMS (ESI): $R_T$(min)=0.92, [M+H]$^+$=473.2, method=K-1; $^1$H NMR (300 MHz, CD$_3$OD) δ 9.15 (s, 1H), 8.51 (s, 1H), 8.45 (d, J=5.1 Hz, 1H), 7.96 (s, 1H), 7.62 (s, 1H), 7.41 (d, J=5.1 Hz, 1H), 6.80 (s, 1H), 6.70 (s, 1H), 4.88-4.60 (m, 4H), 4.07-4.00 (m, 1H), 3.98-3.94 (m, 1H), 3.65-3.55 (m, 1H), 3.09-3.03 (m, 1H), 2.92-2.89 (m, 1H), 2.44 (s, 3H), 2.23-2.20 (m, 1H), 2.13-2.06 (m, 2H), 1.95-1.88 (m, 1H).

Example 175

(+/−)-1-(3-(8-amino-6-(4-methylpyridin-3-yl)-2,7-naphthyridin-3-ylamino)-1-methyl-1H-pyrazol-5-yl)ethanol (Compound 221)

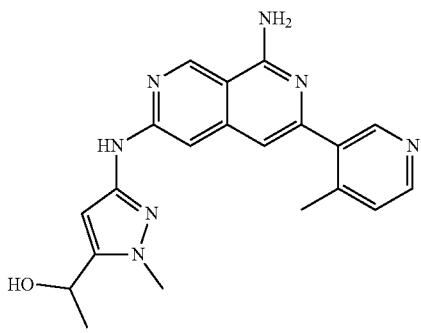

Step 1: 1-(3-Bromo-1-methyl-1H-pyrazol-5-yl)ethan-1-ol

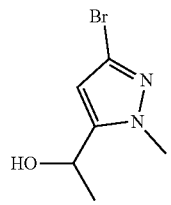

n-BuLi (3.1 mL, 2.5M in hexane) was added dropwise to a solution of 3,5-dibromo-1-methyl-1H-pyrazole (1.70 g, 7.09 mmol) in tetrahydrofuran (30 mL) at −70° C. under nitrogen. After 1 h, acetaldehyde (374 mg, 8.49 mmol) was added. The temperature of the reaction was slowly raised to room temperature. After 1 h, the reaction was diluted with water, and the resulting mixture was extracted with ethyl acetate. The collected organic was concentrated under vacuum. Purification by silica gel chromatography (1:1 dichloromethane/ethyl acetate) afforded 1-(3-bromo-1-methyl-1H-pyrazol-5-yl)ethan-1-ol (370 mg, 25%) as a yellow oil. $^1$H NMR (300 MHz, DMSO-d$_6$) δ 6.25 (s, 1H), 5.38 (d, J=5.7 Hz, 1H), 4.82-4.74 (m, 1H), 3.77 (s, 3H), 1.38 (d, J=6.6 Hz, 3H).

Step 2: 1-[3-[(8-[bis[(2,4-dimethoxyphenyl)methyl]amino]-6-(4-methylpyridin-3-yl)-2,7-naphthyridin-3-yl)amino]-1-methyl-1H-pyrazol-5-yl]ethan-1-ol

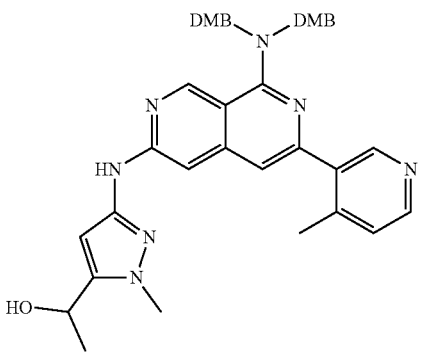

A mixture of 1-N,1-N-bis[(2,4-dimethoxyphenyl)methyl]-3-(4-methylpyridin-3-yl)-2,7-naphthyridine-1,6-diamine (200 mg, 0.36 mmol), 1-(3-bromo-1-methyl-1H-pyrazol-5-yl)ethan-1-ol (185 mg, 0.90 mmol), LiHMDS (450 mg, 2.69 mmol), 3rd generation t-BuBrettPhos precatalyst (155 mg, 0.18 mmol) and t-BuBrettPhos (87 mg, 0.18 mmol) in 1,4-dioxane (10 mL) was heated with microwave radiation for 2 h at 130° C. The solids were filtered, and the filtrate was concentrated under vacuum. The resulting residue was purified by silica gel chromatography (10:1 dichloromethane/methanol) to provide 1-[3-[(8-[bis[(2,4-dimethoxyphenyl)methyl]amino]-6-(4-methylpyridin-3-yl)-2,7-naphthyridin-3-yl)amino]-1-methyl-1H-pyrazol-5-yl]ethan-1-ol (170 mg, 69%) as a yellow solid. LCMS (ESI): [M+H]$^+$=676.3.

Step 3: 1-(3-(8-amino-6-(4-methylpyridin-3-yl)-2,7-naphthyridin-3-ylamino)-1-methyl-1H-pyrazol-5-yl)ethanol

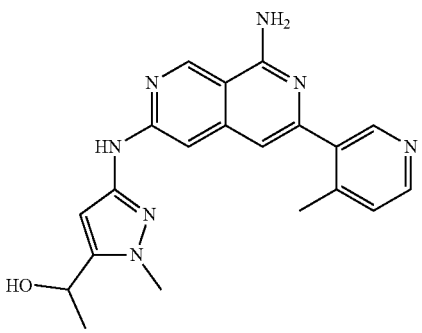 [SMILES: Cc1ccncc1-c1cc2cc(Nc3cc(C(C)O)n(C)n3)ncc2c(N)n1]

A solution of 1-[3-[(8-[bis[(2,4-dimethoxyphenyl)methyl]amino]-6-(4-methylpyridin-3-yl)-2,7-naphthyridin-3-yl)amino]-1-methyl-1H-pyrazol-5-yl]ethan-1-ol (250 mg, 0.37 mmol) in trifluoroacetic acid (12 mL) was stirred for 2 h at 80° C. The reaction solution was then concentrated under vacuum. The resulting residue was dissolved in methanol, and the pH of the solution was adjust to 9 with ammonium hydroxide. Purification by Prep-HPLC provided 1-(3-(8-amino-6-(4-methylpyridin-3-yl)-2,7-naphthyridin-3-ylamino)-1-methyl-1H-pyrazol-5-yl)ethanol (32.5 mg, 23%) as a yellow solid. LCMS (ESI): $R_T$ (min)=1.72,

[M+H]⁺=376.2, method=M; ¹H NMR (300 MHz, DMSO-d₆) δ 9.34 (s, 1H), 9.21 (s, 1H), 8.54 (s, 1H), 8.41 (d, J=4.8 Hz, 1H), 7.48 (s, 1H), 7.29 (d, J=4.8 Hz, 1H), 7.08 (s, 2H), 6.76 (s, 1H), 6.06 (s, 1H), 5.30 (d, J=6.6 Hz, 1H), 4.82-4.74 (m, 1H), 3.74 (s, 3H), 2.40 (s, 3H), 1.41 (d, J=6.6 Hz, 3H).

Example 176

(+/−)-cis-N-(8-amino-6-(3-oxo-3,4-dihydro-2H-pyrido[4,3-b][1,4]oxazin-8-yl)-2,7-naphthyridin-3-yl)-2-fluorocyclopropanecarboxamide (Compound 222)

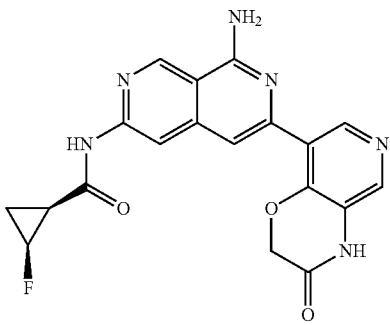 [SMILES: Nc1nc(-c2cncc3c2OCC(=O)N3)cc2cc(NC(=O)[C@@H]3C[C@@H]3F)ncc12]

Step 1: 3-oxo-3,4-dihydro-2H-pyrido[4,3-b][1,4]oxazin-8-ylboronic acid

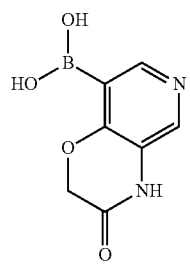 [SMILES: O=C1COc2c(cncc2B(O)O)N1]

A mixture of 8-bromo-2H,3H,4H-pyrido[4,3-b][1,4]oxazin-3-one (500 mg, 2.18 mmol), 4,4,5,5-tetramethyl-2-(tetramethyl-1,3,2-dioxaborolan-2-yl)-1,3,2-dioxaborolane (1.7 g, 6.69 mmol), Pd(dppf)Cl₂ (320 mg, 0.43 mmol), and KOAc (640 mg, 6.52 mmol) in 1,4-dioxane (15 mL) was heated at 100° C. for 12 h under nitrogen. The solids were filtered, and the pH of the filtrate was adjusted to ~9 with NaOH. The resulting solution was washed with ethyl acetate. The aqueous layer was acidified to pH value ~3 with diluted aqueous HCl. The resulting solution was extracted with ethyl acetate. The collected organic was dried over Na₂SO₄, filtered, and concentrated under vacuum to provide [3-oxo-2H,3H,4H-pyrido[4,3-b][1,4]oxazin-8-yl]boronic acid (300 mg, 71%) as a yellow oil.

Step 2 cis-N-(8-amino-6-(3-oxo-3,4-dihydro-2H-pyrido[4,3-b][1,4]oxazin-8-yl)-2,7-naphthyridin-3-yl)-2-fluorocyclopropanecarboxamide

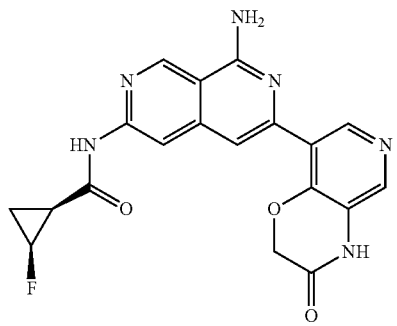 [SMILES: Nc1nc(-c2cncc3c2OCC(=O)N3)cc2cc(NC(=O)[C@@H]3C[C@@H]3F)ncc12]

A mixture of cis-N-(8-amino-6-chloro-2,7-naphthyridin-3-yl)-2-fluorocyclopropane-1-carboxamide (200 mg, 0.71 mmol), [3-oxo-2H,3H,4H-pyrido[4,3-b][1,4]oxazin-8-yl]boronic acid (277 mg, 1.42 mmol), Pd(dppf)Cl₂ (104 mg, 0.14 mmol), and potassium carbonate (197 mg, 1.42 mmol) in dioxane (10 mL) and water (1 mL) was heated at 100° C. for 2 h under nitrogen. The solids were filtered, and the filtrate was concentrated under vacuum. The resulting residue was sequentially purified by flash column chromatography and Prep-HPLC to afford cis-N-(8-amino-6-[3-oxo-2H,3H,4H-pyrido[4,3-b][1,4]oxazin-8-yl]-2,7-naphthyridin-3-yl)-2-fluorocyclopropane-1-carboxamide (4.9 mg, 2%) as a yellow solid. LCMS (ESI): R$_T$(min)=1.08, [M+H]⁺=395.1, method=K-1; ¹H NMR (400 MHz, DMSO-d₆) δ 11.02 (s, 1H), 10.99 (s, 1H), 9.37 (s, 1H), 8.72 (s, 1H), 8.23 (s, 1H), 8.09 (s, 1H), 7.42 (s, 1H), 7.33 (s, 2H), 4.86 (s, 3H), 2.36-2.17 (m, 1H), 1.79-1.59 (m, 1H), 1.32-1.11 (m, 1H).

Example 177

(+/−)-cis-N-(8-amino-6-(3,4-dihydro-2H-pyrido[4,3-b][1,4]oxazin-8-yl)-2,7-naphthyridin-3-yl)-2-fluorocyclopropanecarboxamide (Compound 223)

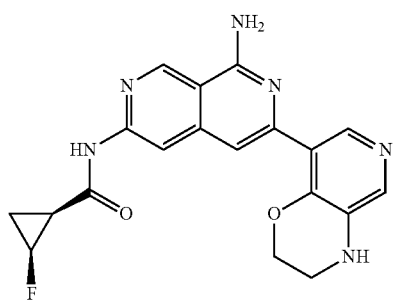 [SMILES: Nc1nc(-c2cncc3c2OCCN3)cc2cc(NC(=O)[C@@H]3C[C@@H]3F)ncc12]

Step 1: 8-bromo-2H-pyrido[4,3-b][1,4]oxazin-3 (4H)-one

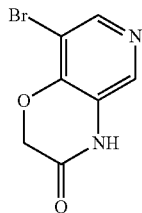 [SMILES: O=C1COc2c(Br)cncc2N1]

A mixture of 3-amino-5-bromopyridin-4-ol (1 g, 5.29 mmol), 2-chloroacetyl chloride (658 mg, 5.82 mmol), potassium carbonate (1.82 g, 13.16 mmol) in N,N-dimethylformamide (25 mL) was stirred overnight at room temperature under nitrogen. The reaction was diluted with water, and the resulting solution was extracted with ethyl acetate. The collected organic was dried over $Na_2SO_4$, filtered, and concentrated under vacuum to afford 8-bromo-2H-pyrido[4,3-b][1,4]oxazin-3 (4H)-one (500 mg, 39%) as a white solid. LCMS (ESI): $[M+H]^+$=230.0, 232.0.

Step 2: 8-bromo-3,4-dihydro-2H-pyrido[4,3-b][1,4]oxazine

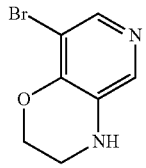

1 M Borane-tetrahydrofuran solution (19.6 mL, 19.6 mmol) was added dropwise to a solution of 8-bromo-2H,3H,4H-pyrido[4,3-b][1,4]oxazin-3-one (1.5 g, 6.54 mmol) in tetrahydrofuran (30 mL) and methanol (10 mL). The reaction mixture was stirred for 1 h at room temperature and another 1 h at 65° C. The reaction mixture was concentrated under vacuum. The resulting residue was dissolved in water and the pH of the solution was adjust to 8-9 with aqueous NaOH (1 mol/L). The basic solution was extracted with ethyl acetate. The collected organic was dried over $Na_2SO_4$, filtered, and concentrated under vacuum to provide 8-bromo-2H,3H,4H-pyrido[4,3-b][1,4]oxazine (900 mg, 64%) as a white solid. LCMS (ESI): $[M+H]^+$=215.0, 217.0.

Step 3: 3,4-dihydro-2H-pyrido[4,3-b][1,4]oxazin-8-ylboronic acid

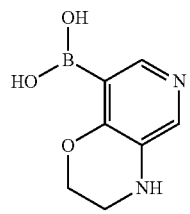 [SMILES: OB(O)c1cncc2c1OCCN2]

A mixture of 8-bromo-2H,3H,4H-pyrido[4,3-b][1,4]oxazine (400 mg, 1.86 mmol), Pd(dppf)Cl$_2$ (272 mg, 0.37 mmol), KOAc (547 mg, 5.57 mmol) and 4,4,5,5-tetramethyl-2-(tetramethyl-1,3,2-dioxaborolan-2-yl)-1,3,2-dioxaborolane (1.42 g, 5.59 mmol) in dioxane (10 mL) was stirred for 12 h at 100° C. under nitrogen. The solids were filtered, and the pH of the filtrate was adjusted to 9-10 with aqueous NaOH. The resulting solution was washed with ethyl acetate. The pH of the aqueous layer was adjusted to 3-4 with aqueous HCl. The acidic solution was then extracted with ethyl acetate. The collected organic was dried over $Na_2SO_4$, filtered, and concentrated under vacuum to afford 3,4-dihydro-2H-pyrido[4,3-b][1,4]oxazin-8-ylboronic acid (350 mg) as a brown solid. LCMS (ESI): $[M+H]^+$=181.0, 183.0.

Step 4: cis-N-(6,8-dichloro-2,7-naphthyridin-3-yl)-2-fluorocyclopropanecarboxamide

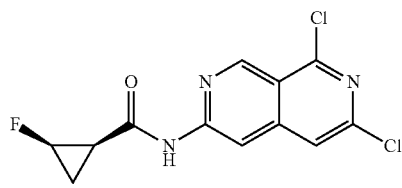

Oxalyl chloride (414 mg, 3.26 mmol) was added dropwise to an ice-cooled solution of cis-2-fluorocyclopropane-1-carboxylic acid (228 mg, 2.19 mmol), pyridine (3 mL), and N,N-dimethylformamide (0.05 mL) in dichloromethane (15 mL) under nitrogen. After 30 mins the reaction was added to a solution of 6,8-dichloro-2,7-naphthyridin-3-amine hydrochloride (500 mg, 2.33 mmol) in dichloromethane (20 mL) at room temperature. After 2 h, the reaction was then diluted by water, and the resulting mixture was extracted with dichloromethane. The collected organic was dried over $Na_2SO_4$, filtered, and concentrated under vacuum. Purification by flash column chromatography (15:1 dichloromethane/methanol) afforded cis-N-(6,8-dichloro-2,7-naphthyridin-3-yl)-2-fluorocyclopropane-1-carboxamide (300 mg, 39%) as a light yellow solid. LCMS (ESI): $[M+H]^+$=301.1.

Step 5: cis-N-(8-amino-6-chloro-2,7-naphthyridin-3-yl)-2-fluorocyclopropanecarboxamide

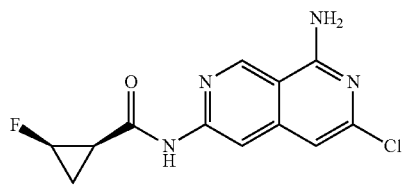 [SMILES: Nc1nc(Cl)cc2cc(NC(=O)[C@H]3C[C@H]3F)ncc12]

A solution of cis-N-(6,8-dichloro-2,7-naphthyridin-3-yl)-2-fluorocyclopropane-1-carboxamide (100 mg, 0.33 mmol) and ammonium hydroxide (2 mL) in 1,4-dioxane (4 mL) was heated at 90° C. for 16 h. The reaction mixture was concentrated under vacuum. Purification of the resulting residue by flash column chromatography (8:1 dichloromethane/methanol) provided cis-N-(8-amino-6-chloro-2,7-naphthyridin-3-yl)-2-fluorocyclopropane-1-carboxamide (60 mg, 58%) as a light yellow solid. LCMS (ESI): [M+H]⁺=281.6.

Step 6: cis-N-(8-amino-6-(3,4-dihydro-2H-pyrido[4,3-b][1,4]oxazin-8-yl)-2,7-naphthyridin-3-yl)-2-fluorocyclopropanecarboxamide

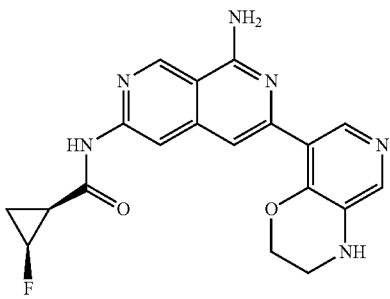 [SMILES: Nc1nc(-c2cncc3c2OCCN3)cc2cc(NC(=O)[C@@H]3C[C@@H]3F)ncc12]

A suspension of cis-N-(8-amino-6-chloro-2,7-naphthyridin-3-yl)-2-fluorocyclopropane-1-carboxamide (200 mg, 0.71 mmol), [2H,3H,4H-pyrido[4,3-b][1,4]oxazin-8-yl]boronic acid (258 mg, 1.43 mmol), Pd(PPh₃)₄ (165 mg, 0.14 mmol), and Cs₂CO₃ (466 mg, 1.43 mmol) in 10:1 1,4-dioxane/water (11 mL) was heated at 100° C. for 12 h under nitrogen. The solids were filtered, and the filtrate was concentrated under vacuum. The resulting residue was purified by flash column chromatography (10:1 dichloromethane/methanol) to afford cis-N-(8-amino-6-[2H,3H,4H-pyrido[4,3-b][1,4]oxazin-8-yl]-2,7-naphthyridin-3-yl)-2-fluorocyclopropane-1-carboxamide (18.4 mg, 7%) as a yellow solid. LCMS (ESI): R_T (min)=1.16, [M+H]⁺=381.1, method=M; ¹H NMR (300 MHz, CD₃OD) δ 9.24 (s, 1H), 8.32-8.22 (s, 1H), 8.16 (s, 1H), 7.83 (s, 1H), 7.34 (s, 1H), 5.02-4.97 (m, 1H), 4.80-4.75 (m, 1H), 4.45-4.33 (m, 2H), 3.51-3.41 (m, 2H), 2.21-2.11 (m, 1H), 1.90-1.76 (m, 1H), 1.28-1.17 (m, 1H).

Example 178

(+/−)-trans-N-(8-amino-6-(2-cyanophenyl)-2,7-naphthyridin-3-yl)-2-cyanocyclopropanecarboxamide (Compound 224)

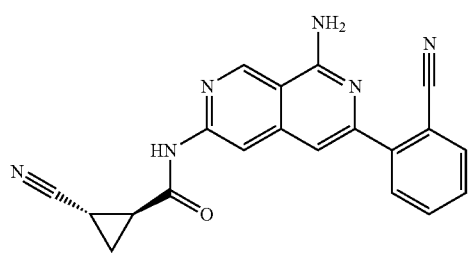 [SMILES: N#Cc1ccccc1-c1cc2cc(NC(=O)[C@H]3C[C@@H]3C#N)ncc2c(N)n1]

Step 1: trans-N-(8-amino-6-chloro-2,7-naphthyridin-3-yl)-2-cyanocyclopropane-1-carboxamide

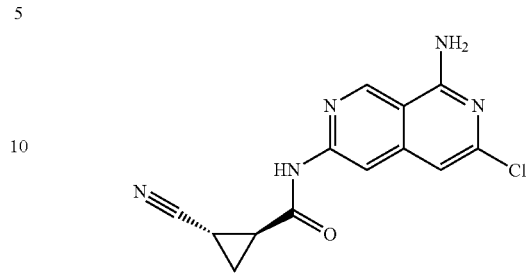

A solution of trans-2-cyano-N-(6,8-dichloro-2,7-naphthyridin-3-yl)cyclopropane-1-carboxamide (200 mg, 0.65 mmol) in 1,4-dioxane (8 mL) and ammonium hydroxide (6 mL) was heated at 100° C. for 1 h under nitrogen. The reaction solution was concentrated under vacuum to afford crude trans-N-(8-amino-6-chloro-2,7-naphthyridin-3-yl)-2-cyanocyclopropane-1-carboxamide (208 mg) as a yellow solid. LCMS (ESI): [M+H]⁺=288.1.

Step 2: trans-N-(8-amino-6-(2-cyanophenyl)-2,7-naphthyridin-3-yl)-2-cyanocyclopropanecarboxamide

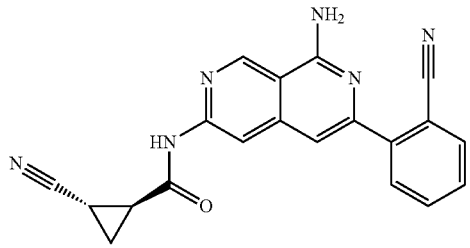 [SMILES: N#Cc1ccccc1-c1cc2cc(NC(=O)[C@H]3C[C@@H]3C#N)ncc2c(N)n1]

A mixture of trans-N-(8-amino-6-chloro-2,7-naphthyridin-3-yl)-2-cyanocyclopropane-1-carboxamide (200 mg, 0.70 mmol), (2-cyanophenyl)boronic acid (256 mg, 1.74 mmol), 2nd generation XPhos precatalyst (82 mg, 0.11 mmol), XPhos (66 mg, 0.14 mmol) and KOAc (204 mg, 2.08 mmol) in 5:1 1,4-dioxane/water (12 mL) was heated at 100° C. for 6 h under nitrogen. The solids were filtered, and the filtrate was concentrated under vacuum. The resulting residue was purified by Prep-HPLC to afford trans-N-[8-amino-6-(2-cyanophenyl)-2,7-naphthyridin-3-yl]-2-cyanocyclopropane-1-carboxamide (40.5 mg, 16%) as a yellow solid. LCMS (ESI): R_T(min)=2.32, [M+H]⁺=355.1, method=M; ¹H NMR (300 MHz, DMSO-d₆) δ 11.32 (s, 1H), 9.43 (s, 1H), 8.24 (s, 1H), 7.94-7.89 (m, 2H), 7.87-7.81 (m, 1H), 7.63-7.58 (m, 1H), 7.43 (s, 2H), 7.22 (s, 1H), 2.79-2.72 (m, 1H), 2.20-2.13 (m, 1H), 1.65-1.61 (m, 1H), 1.60-1.47 (m, 1H).

Example 179

(+/−)-trans-N-(8-amino-6-(4-(2-hydroxy-2-methyl-propyl)pyridin-3-yl)-2,7-naphthyridin-3-yl)-2-cyano-cyclopropanecarboxamide (Compound 225)

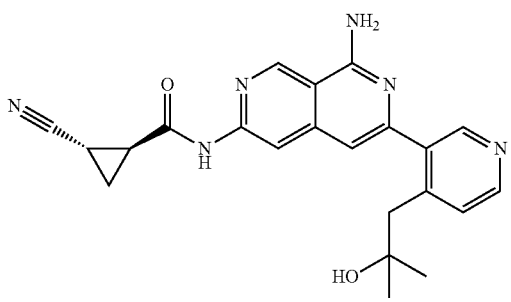 [SMILES: CC(C)(O)Cc1ccncc1-c1cc2cc(NC(=O)[C@H]3C[C@@H]3C#N)ncc2c(N)n1]

Step 1:
1-(3-bromopyridin-4-yl)-2-methylpropan-2-ol

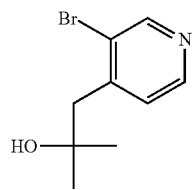

LDA in tetrahydrofuran (4.3 mL, 31.71 mmol) was added dropwise to a solution of 3-bromo-4-methylpyridine (1 g, 5.81 mmol) in tetrahydrofuran (30 mL) at −78° C. After 30 min, acetone (405 mg, 6.973 mmol) was added at −78° C., and the reaction mixture was stirred for another 2 hour under nitrogen. The reaction was diluted with water, and the resulting mixture was extracted with ethyl acetate. The collected organic was dried over Na$_2$SO$_4$, filtered, and concentrated under vacuum. Purification by flash column chromatography (10:1 ethyl acetate/petroleum ether) provided 1-(3-bromopyridin-4-yl)-2-methylpropan-2-ol (1.0 g, 74% yield) as a yellow solid. LCMS (ESI): [M+H]$^+$=230.1.

Step 2: 3,3-dimethyl-3,4-dihydro-[1,2]oxaborinino[3,4-c]pyridin-1-ol

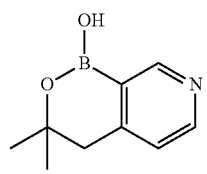

A mixture of 1-(3-bromopyridin-4-yl)-2-methylpropan-2-ol (500 mg, 2.17 mmol), 4,4,5,5-tetramethyl-2-(tetramethyl-1,3,2-dioxaborolan-2-yl)-1,3,2-dioxaborolane, Pd(dppf)Cl$_2$ (360 mg, 0.44 mmol) and KOAc (660 mg, 6.72 mmol) in dioxane (10 mL) was heated at 100° C. for 4 h under nitrogen. The reaction mixture was concentrated under vacuum, and the residue was dissolved in water. The pH of the solution was adjusted to ~10 with aqueous sodium hydroxide (1 mol/L). The resulting solution was then washed with ethyl acetate. The basic aqueous layer was acidified to pH=4 with aqueous HCl (1 mol/L). The resulting acidic solution was extracted with ethyl acetate. The collected organic was dried over Na$_2$SO$_4$, filtered, and concentrated under vacuum to afford 3,3-dimethyl-1H,3H,4H-[1,2]oxaborinino[3,4-c]pyridin-1-ol (260 mg, 68%) as a yellow solid. LCMS (ESI): [M+H]$^+$=178.1.

Step 3: trans-N-(8-amino-6-(4-(2-hydroxy-2-methyl-propyl)pyridin-3-yl)-2,7-naphthyridin-3-yl)-2-cyano-cyclopropanecarboxamide

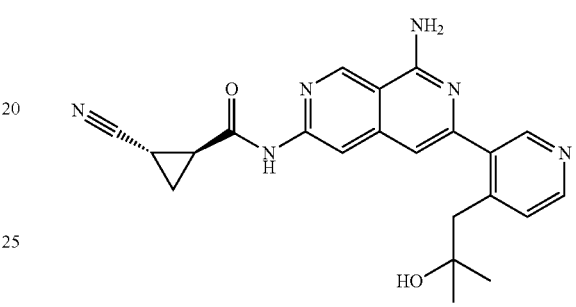

A suspension of trans-N-(8-amino-6-chloro-2,7-naphthyridin-3-yl)-2-cyanocyclopropane-1-carboxamide (200 mg, 0.69 mmol), 3,3-dimethyl-1H,3H,4H-[1,2]oxaborinino[3,4-c]pyridin-1-ol (600 mg, 3.39 mmol), Pd(PPh$_3$)$_4$ (120 mg, 0.10 mmol) and Cs$_2$CO$_3$ (452 mg, 1.38 mmol) in 10:1 dioxane/water (11 mL) was heated at 100° C. for 4 h under nitrogen. The reaction mixture was concentrated under vacuum. Purification by silica gel chromatography (10:1 dichloromethane/methanol) provided trans-N-[8-amino-6-[4-(2-hydroxy-2-methylpropyl)pyridin-3-yl]-2,7-naphthyridin-3-yl]-2-cyanocyclopropane-1-carboxamide (13.3 mg 5%) as a yellow solid. LCMS (ESI): R$_T$ (min)=1.85, [M+H]$^+$=403.1, method=K-1; $^1$H NMR (300 MHz, DMSO-d$_6$) δ 9.34 (s, 1H), 8.56 (s, 1H), 8.50 (d, J=1.8 Hz, 1H), 8.30 (s, 1H), 7.46 (d, J=1.8 Hz, 1H), 7.00 (s, 1H), 3.02 (s, 2H), 2.70-2.59 (m, 1H), 2.14-2.12 (m, 1H), 1.67-1.53 (m, 2H), 1.26 (s, 6H).

Example 180 cis-5-(1-amino-6-(-2-fluorocyclopropanecarbox-amido)-2,7-naphthyridin-3-yl)-N,4-dimethylnicoti-namide (Compound 226)

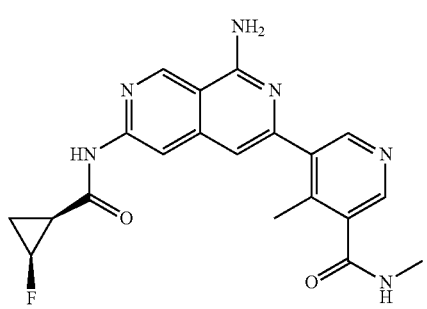 [SMILES: CNC(=O)c1cncc(-c2cc3cc(NC(=O)[C@@H]4C[C@@H]4F)ncc3c(N)n2)c1C]

Step 1: 5-bromo-4-methylnicotinic acid

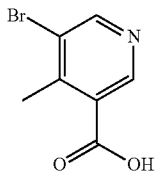

n-BuLi (0.72 mL, 7.64 mmol, 11M in hexanes) was added dropwise to a solution of 3,5-dibromo-4-methylpyridine (500 mg, 1.99 mmol) in tetrahydrofuran (10 mL) at −78° C. under nitrogen. After 1 h, $CO_2$ (g) was introduced in the solution at −78° C., and the resulting solution was warmed to room temperature. After 1 h, the reaction was diluted with 1M aqueous HCl. The resulting solution was extracted with ethyl acetate. The combined organic extract was dried over $Na_2SO_4$, filtered, and concentrated under vacuum to provide 5-bromo-4-methylpyridine-3-carboxylic acid (0.23 g, 53%) as a white solid.

Step 2: 5-bromo-N,4-dimethylnicotinamide

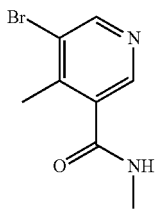

A solution of 5-bromo-4-methylpyridine-3-carboxylic acid (1 g, 4.62 mmol), HATU (2.64 g, 6.94 mmol), triethylamine (1.4 g, 13.83 mmol), and methylamine (2.6 mL, 167.43 mmol) in dichloromethane (50 mL) was stirred for 8 h at room temperature. The reaction was diluted with water, and the resulting mixture was extracted with dichloromethane. The collected organic was dried over $Na_2SO_4$, filtered, and concentrated under vacuum. Purification by silica-gel column chromatography (10:1 dichloromethane/methanol) provided 5-bromo-N,4-dimethylpyridine-3-carboxamide (0.6 g, 57%) as a white solid.

Step 3: 4-methyl-5-(methylcarbamoyl)pyridin-3-ylboronic acid

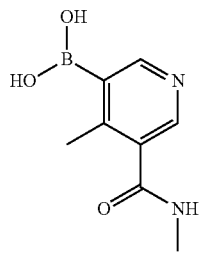

A mixture of 5-bromo-N,4-dimethylpyridine-3-carboxamide (400 mg, 1.74 mmol), Pd(dppf)Cl$_2$ (255 mg, 0.34 mmol), KOAc (513 mg, 5.22 mmol) and 4,4,5,5-tetramethyl-2-(tetramethyl-1,3,2-dioxaborolan-2-yl)-1,3,2-dioxaborolane (2.22 g, 8.74 mmol) in 1,4-dioxane (15 mL) was heated at 100° C. for 5 h under nitrogen. The solids were filtered, and the filtrate was acidified to pH=3-4 with aqueous HCl. The acidic solution was extracted with ethyl acetate. The organic extract was dried over $Na_2SO_4$, filtered, and concentrated under vacuum to afford [4-methyl-5-(methylcarbamoyl)pyridin-3-yl]boronic acid (280 mg, crude) as a white solid.

Step 4: cis-5-(1-amino-6 (2-fluorocyclopropanecarboxamido)-2,7-naphthyridin-3-yl)-N,4-dimethylnicotinamide

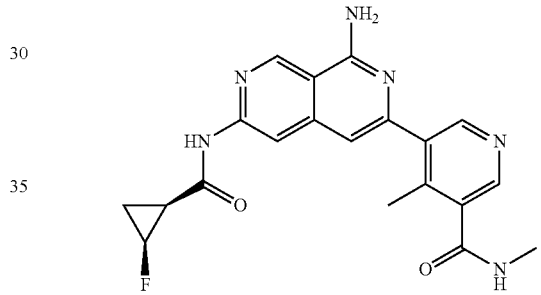

A mixture of cis-N-(8-amino-6-chloro-2,7-naphthyridin-3-yl)-2-fluorocyclopropane-1-carboxamide (200 mg, 0.71 mmol), [4-methyl-5-(methylcarbamoyl)pyridin-3-yl]boronic acid (277 mg, 1.42 mmol), Pd(dppf)Cl$_2$ (104 mg, 0.14 mmol), and potassium carbonate (197 mg, 1.42 mmol) in 10:1 1,4-dioxane/water (16.5 mL) was heated at 100° C. for 2 h under nitrogen. The solids were filtered, and the filtrate was concentrated under vacuum. Purification by silica-gel column chromatography (10:1 dichloromethane/methanol) yielded cis-5-(1-amino-6-[[-2-fluorocyclopropane]amido]-2,7-naphthyridin-3-yl)-N,4-dimethylpyridine-3-carboxamide (35.6 mg, 13%) as a white solid. LCMS (ESI): $R_T$ (min)=0.95, [M+H]$^+$=395.2, method=M; $^1$H NMR (300 MHz, CD$_3$OD) δ 9.38 (s, 1H), 8.58 (s, 1H), 8.50 (s, 1H), 8.33 (s, 1H), 6.98 (s, 1H), 5.02-4.97 (m, 1H), 4.80-4.75 (m, 1H), 2.96 (s, 3H), 2.44 (s, 3H), 2.21-2.12 (m, 1H), 1.89-1.76 (m, 1H), 1.30-1.17 (m, 1H).

Example 181

(+/−)-trans-N-(8-amino-6-(4-(cyanomethyl)pyridin-3-yl)-2,7-naphthyridin-3-yl)-2-cyanocyclopropan-ecarboxamide (Compound 227)

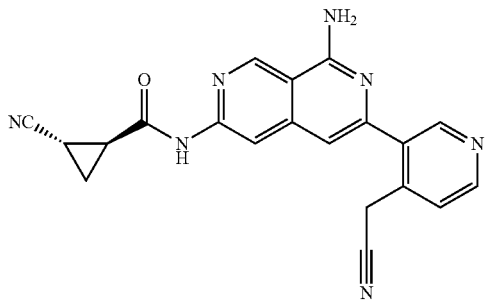 [SMILES: N#CCc1ccncc1-c1cc2cc(NC(=O)[C@H]3C[C@@H]3C#N)ncc2c(N)n1]

Step 1: 3-Bromo-4-(chloromethyl)pyridine hydrochloride

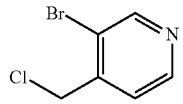

A mixture of (3-bromopyridin-4-yl)methanol (3.0 g, 15.95 mmol) and thionyl chloride (3.8 g, 31.94 mmol) in dichloromethane (80 mL) was stirred for 2 h at room temperature. The reaction mixture was concentrated under vacuum to afford crude 3-bromo-4-(chloromethyl)pyridine hydrochloride (3.7 g, 95%) as a white solid. LCMS (ESI): [M+H]$^+$=206.0.

Step 2: 2-(3-bromopyridin-4-yl)acetonitrile

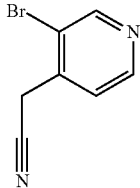

A mixture of 3-bromo-4-(chloromethyl)pyridine hydrochloride (4.1 g, 16.88 mmol), KCN (2.2 g, 33.79 mmol) in 1:1 ethanol/water (100 mL) was heated at 100° C. for 3 h. The reaction was concentrated under vacuum, and the resulting residue was dissolved with H$_2$O (50 mL). The aqueous solution was extracted with ethyl acetate. The organic extract was dried over Na$_2$SO$_4$, filtered, and concentrated under vacuum. Purification by silica gel chromatography (1:2 ethyl acetate/petroleum ether) afforded 2-(3-bromopyridin-4-yl)acetonitrile (2.4 g, 72%) as a light yellow solid. LCMS (ESI): [M+H]$^+$=197.0.

Step 3: [4-(cyanomethyl)pyridin-3-yl]boronic acid

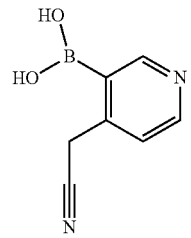 [SMILES: N#CCc1ccncc1B(O)O]

A mixture of 2-(3-bromopyridin-4-yl)acetonitrile (1 g, 5.08 mmol), 4,4,5,5-tetramethyl-2-(tetramethyl-1,3,2-dioxaborolan-2-yl)-1,3,2-dioxaborolane (1.93 g, 7.6 mmol), Pd(dppf)Cl$_2$ (371 mg, 0.51 mmol) and KOAc (1.49 g, 15.18 mmol) in dioxane (30 mL) was heated at 100° C. for 3 h under nitrogen. The solids were filtered, and the filtrate was concentrated under vacuum. The resulting residue was dissolved in H$_2$O, and the solution was basified to pH=10 with aqueous NaOH. The basic solution was washed with ethyl acetate. The aqueous layer was acidified to pH=5-6 with aqueous HCl and concentrated under high vacuum. The resulting residue was suspended in 1:1 ethyl acetate/ethanol and filtered. The filtrate was concentrated under vacuum to afford [4-(cyanomethyl)pyridin-3-yl]boronic acid (658 mg, 80%) as a brown solid. LCMS (ESI): [M+H]$^+$=163.1.

Step 4: trans-N-[8-amino-6-[4-(cyanomethyl)pyridin-3-yl]-2,7-naphthyridin-3-yl]-2-cyanocyclopropane-1-carboxamide

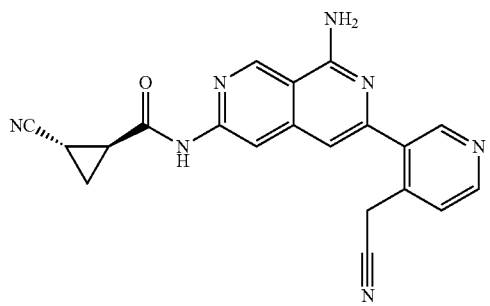 [SMILES: N#CCc1ccncc1-c1cc2cc(NC(=O)[C@H]3C[C@@H]3C#N)ncc2c(N)n1]

A mixture of trans-N-(8-amino-6-chloro-2,7-naphthyridin-3-yl)-2-cyanocyclopropane-1-carboxamide (440 mg, 1.53 mmol), [4-(cyanomethyl)pyridin-3-yl]boronic acid (495 mg, 3.06 mmol), XPhos (73 mg, 0.15), XPhos palladium(II) biphenyl-2-amine chloride (121 mg, 0.15), potassium carbonate (633 mg, 4.58), and 5:1 dioxane/water (12 mL) was heated at 100° C. for 1 h under nitrogen. The reaction was concentrated, and the crude product was purified by Flash-Prep-HPLC to afford trans-N-[8-amino-6-[4-(cyanomethyl)pyridin-3-yl]-2,7-naphthyridin-3-yl]-2-cyanocyclopropane-1-carboxamide (160, 28%) as a brown solid. LCMS (ESI): R$_T$ (min)=1.12, [M+H]$^+$=370.1, method=M; $^1$H NMR (300 MHz, DMSO-d$_6$) δ 11.31 (s, 1H), 9.41 (s, 1H), 8.77 (s, 1H), 8.64 (d, J=6.0 Hz, 1H), 8.25 (s, 1H), 7.54 (d, J=6.0 Hz, 1H), 7.44 (s, 2H), 7.16 (s, 1H), 4.48 (s, 2H), 2.80-2.74 (m, 1H), 2.21-2.14 (m, 1H), 1.66-1.59 (m, 1H), 1.48-1.42 (m, 1H).

Example 182

(+/−)-trans-N-(8-amino-6-(4-(methoxymethyl)pyridin-3-yl)-2,7-naphthyridin-3-yl)-2-cyanocyclopropanecarboxamide (Compound 228)

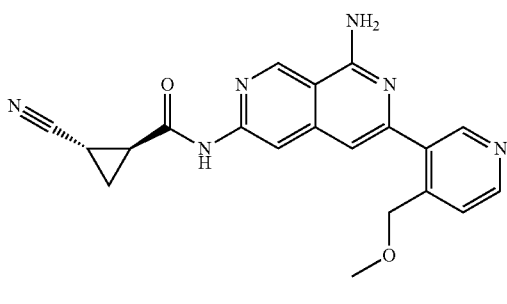 [SMILES: COCc1ccncc1-c1cc2cc(NC(=O)[C@H]3C[C@@H]3C#N)ncc2c(N)n1]

Step 1: 3-bromo-4-(methoxymethyl)pyridine

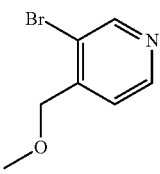

To an ice-cooled solution of sodium hydride (255 mg, 10.62 mmol) in tetrahydrofuran (30 mL) was added (3-bromopyridin-4-yl)methanol (1 g, 5.31 mmol). After 30 min, CH$_3$I (0.336 mL, 5.39 mmol) was added at 0° C., and the reaction temperature was maintained at 0° C. for another 30 min before warming to room temperature. After 12 h, the reaction was diluted with water, and the resulting solution was extracted with dichloromethane. The organic extract was dried over Na$_2$SO$_4$, filtered, and concentrated under vacuum. Purification by silica gel chromatography (5:1 ethyl acetate/petroleum ether) provided 3-bromo-4-(methoxymethyl)pyridine (500 mg, 47%) as a yellow oil. LCMS (ESI): [M+H]$^+$=202.1.

Step 2: 4-(methoxymethyl)pyridin-3-ylboronic acid

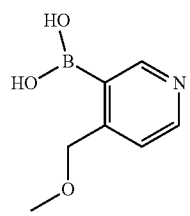

A mixture of 3-bromo-4-(methoxymethyl)pyridine (500 mg, 2.47 mmol), 4,4,5,5-tetramethyl-2-(tetramethyl-1,3,2-dioxaborolan-2-yl)-1,3,2-dioxaborolane (1.8 g, 7.08 mmol), Pd(dppf)Cl$_2$ (406 mg, 0.49 mmol) and KOAc (731 mg, 7.44 mmol) in dioxane (10 mL) was heated at 100° C. for 4 h under nitrogen. The reaction was concentrated under vacuum, and the resulting residue was dissolve in H$_2$O. The pH of the solution was adjusted to 10 with aqueous NaOH, and the basic solution was washed with ethyl acetate. The aqueous layer was then acidified to pH=5-6 with aqueous HCl and concentrated under vacuum. The residue was suspended in 1:1 ethyl acetate/ethanol and filtered. The filtrate was concentrated under vacuum to afford crude [4-(methoxymethyl)pyridin-3-yl]boronic acid (400, mg 97%) as a yellow solid. LCMS (ESI): [M+H]$^+$=168.1.

Step 3: trans-N-(8-amino-6-chloro-2,7-naphthyridin-3-yl)-2-cyanocyclopropanecarboxamide

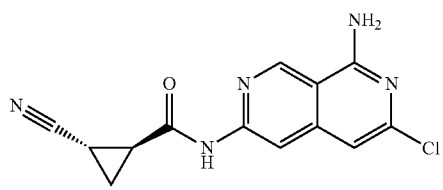 [SMILES: N#C[C@H]1C[C@@H]1C(=O)Nc1cc2cc(Cl)nc(N)c2cn1]

A solution of trans-2-cyano-N-(6,8-dichloro-2,7-naphthyridin-3-yl)cyclopropane-1-carboxamide (200 mg, 0.65 mmol) and ammonium hydroxide (6 mL) in dioxane (8 mL) was heated at 100° C. for 1 h. The reaction mixture was concentrated to afford crude trans-N-(8-amino-6-chloro-2,7-naphthyridin-3-yl)-2-cyanocyclopropane-1-carboxamide (200 mg) as a white solid. LCMS (ESI): [M+H]$^+$=288.1.

Step 4: trans-N-(8-amino-6-(4-(methoxymethyl)pyridin-3-yl)-2,7-naphthyridin-3-yl)-2-cyanocyclopropanecarboxamide

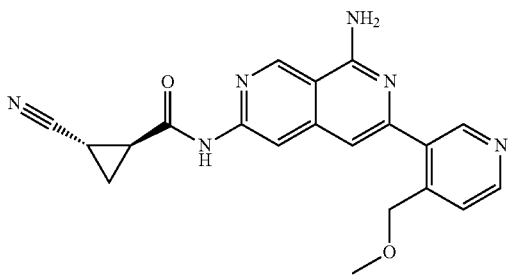 [SMILES: COCc1ccncc1-c1cc2cc(NC(=O)[C@H]3C[C@@H]3C#N)ncc2c(N)n1]

A suspension of trans-N-(8-amino-6-chloro-2,7-naphthyridin-3-yl)-2-cyanocyclopropane-1-carboxamide (200 mg, 0.69 mmol), [4-(methoxymethyl)pyridin-3-yl]boronic acid (139 mg, 0.83 mmol), XPhos-PdCl-2nd generation (55 mg, 0.07 mmol), XPhos (32 mg, 0.06 mmol) and potassium carbonate (200 mg, 1.44 mmol) in 10:1 dioxane/water (11 mL) was heated at 100° C. for 4 h under nitrogen. The reaction mixture was concentrated under vacuum, and the resulting residue was purified by flash column chromatography (10:1 dichloromethane/methanol) to provide trans-N-[8-amino-6-[4-(methoxymethyl)pyridin-3-yl]-2,7-naphthyridin-3-yl]-2-cyanocyclopropane-1-carboxamide (54.7 mg, 18%) as a yellow solid. LCMS (ESI): R$_T$ (min)=1.02, [M+H]$^+$=375.1, method=K-1; $^1$H NMR (300 MHz, DMSO-d$_6$) δ 11.31 (s, 1H), 9.41 (s, 1H), 8.69 (s, 1H), 8.59 (d, J=5.1 Hz, 1H), 8.23 (s, 1H), 7.54 (d, J=5.2 Hz, 1H), 7.40 (s, 2H), 7.06 (d, J=2.2 Hz, 1H), 4.69 (s, 2H), 3.31 (s, 3H), 2.78-2.75 (m, 1H), 2.22-2.13 (m, 1H), 1.68-1.55 (m, 1H), 1.52-1.34 (m, 1H).

Example 183

(+/−)-trans-N-(8-amino-6-(4-(2-methoxyethyl)pyridin-3-yl)-2,7-naphthyridin-3-yl)-2-cyanocyclopropanecarboxamide (Compound 229)

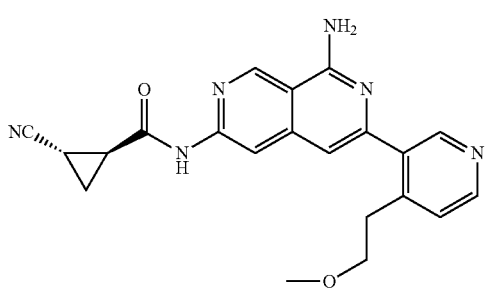 [SMILES: COCCc1ccncc1-c1cc2cc(NC(=O)[C@H]3C[C@@H]3C#N)ncc2c(N)n1]

Step 1: 3-bromo-4-(2-methoxyethyl)pyridine

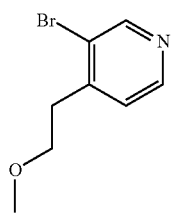

To an ice-cooled solution of 2-(3-bromopyridin-4-yl)ethan-1-ol (4.83 g, 23.91 mmol) in tetrahydrofuran (100 mL) was added sodium hydride (1.44 g, 60.0 mmol). The reaction was warmed to room temperature. After 4 h, CH$_3$I (5.11 g, 36.0) was added, and the reaction was maintained at room temperature for 12 h. Excess sodium hydride was quenched with methanol, and the reaction mixture was concentrated. Purification by flash column chromatography (1:5 ethyl acetate/petroleum ether) provided 3-bromo-4-(2-methoxyethyl)pyridine (2.3 g, 45%) as a light yellow oil. LCMS: (ESI) [M+H]$^+$=216.0

Step 2: [4-(2-methoxyethyl)pyridin-3-yl]boronic acid

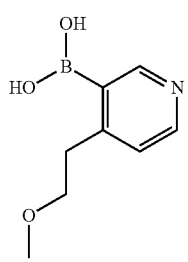

A mixture of 3-bromo-4-(2-methoxyethyl)pyridine (2.11 g, 9.77 mmol), 4,4,5,5-tetramethyl-2-(tetramethyl-1,3,2-dioxaborolan-2-yl)-1,3,2-dioxaborolane (7.44 g, 29.29), Pd(dppf)Cl$_2$ (715 mg, 0.98 mmol) and KOAc (2.87 g, 29.24 mmol) in dioxane (50 mL) was heated at 100° C. for 12 h. The solids were filtered, and the filtrate was concentrated under vacuum. The resulting residue was dissolved in H$_2$O and the solution was basified to pH=7-8 with aqueous NaOH. The basic solution was washed with ethyl acetate. The aqueous was then acidified to pH=3-4 with HCl. The acidic solution was concentrated under vacuum. The resulting residue was suspended in 1:1 ethyl acetate/ethanol and filtered. The filtrate was concentrated under vacuum to afford [4-(2-methoxyethyl)pyridin-3-yl]boronic acid (1.6 g, 91%) as a light yellow solid. LCMS: (ESI) [M+H]$^+$=182.1.

Step 3: trans-N-[8-amino-6-[4-(2-methoxyethyl)pyridin-3-yl]-2,7-naphthyridin-3-yl]-2-cyanocyclopropane-1-carboxamide

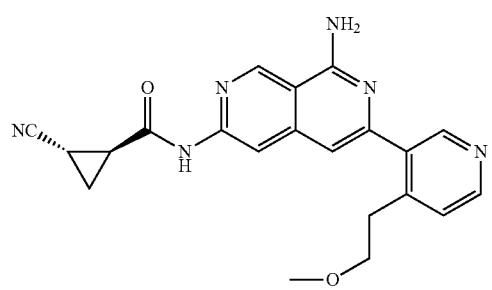 [SMILES: COCCc1ccncc1-c1cc2cc(NC(=O)[C@H]3C[C@@H]3C#N)ncc2c(N)n1]

A mixture of trans-N-(8-amino-6-chloro-2,7-naphthyridin-3-yl)-2-cyanocyclopropane-1-carboxamide (205 mg, 0.71 mmol), [4-(2-methoxyethyl)pyridin-3-yl]boronic acid (155 mg, 0.86 mmol), XPhos (34 mg, 0.07 mmol), potassium carbonate (209 mg, 1.51 mmol) and XPhos palladium (II) biphenyl-2-amine chloride (56 mg, 0.07 mmol) in 4:1 dioxane/water (5 mL) was heated at 100° C. for 3 h under nitrogen. The solids were filtered, and the filtrate was concentrated under vacuum. The resulting residue was purified by Flash-Prep-HPLC to afford trans-N-[8-amino-6-[4-(2-methoxyethyl)pyridin-3-yl]-2,7-naphthyridin-3-yl]-2-cyanocyclopropane-1-carboxamide (70.9 mg, 26%) as a white solid. LCMS (ESI): R$_T$ (min)=1.14, [M+H]$^+$=389.2, method=M; $^1$H NMR (300 MHz, DMSO-d$_6$) δ 11.29 (s, 1H), 9.41 (s, 1H), 8.53 (s, 1H), 8.48 (d, J=6.0 Hz, 1H), 8.20 (s, 1H), 7.37-7.36 (m, 3H), 6.98 (s, 1H), 3.50 (t, J=6.0 Hz, 2H), 3.15 (s, 3H), 3.03 (t, J=6.0 Hz, 2H), 2.80-2.74 (m, 1H), 2.20-2.13 (m, 1H), 1.65-1.59 (m, 1H), 1.48-1.41 (m, 1H).

Example 184

(1R,5R,6S)—N-(8-amino-6-(4-methylpyridin-3-yl)-2,7-naphthyridin-3-yl)-2-cyanobicyclo[3.1.0]hexane-6-carboxamide (Compound 230)

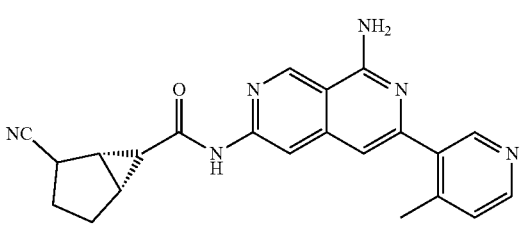

Step 1: (exo)-N-(8-(bis(2,4-dimethoxybenzyl)amino)-6-chloro-2,7-naphthyridin-3-yl)-2-hydroxybicyclo[3.1.0]hexane-6-carboxamide

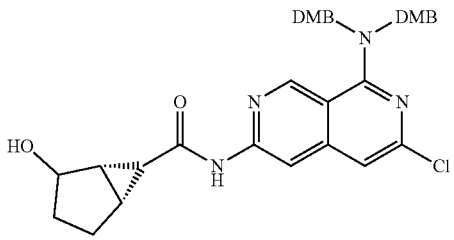

NaBH₄ (550 mg, 14.54 mmol) was added portionwise to a solution of (exo)-N-(8-[bis [(2,4-dimethoxyphenyl) methyl]amino]-6-chloro-2,7-naphthyridin-3-yl)-2-oxobicyclo[3.1.]hexane-6-carboxamide (1.5 g, 2.43 mmol) in methanol (20 mL), dichloromethane (10 mL), and tetrahydrofuran (5 mL) at room temperature. After 1 h, excess sodium borohydride was quenched with H₂O, and the suspension was concentrated under vacuum. Purification of the residue by silica-gel chromatography (10:1 dichloromethane/methanol) provided (exo)-N-(8-[bis[(2,4-dimethoxyphenyl)methyl]amino]-6-chloro-2,7-naphthyridin-3-yl)-2-hydroxybicyclo[3.1.0]hexane-6-carboxamide (1.3 g, 86%) as a yellow solid. LCMS (ESI) [M+H]⁺=619.3.

Step 2: (exo)-N-(8-(bis(2,4-dimethoxybenzyl)amino)-6-chloro-2,7-naphthyridin-3-yl)-2-cyanobicyclo[3.1.0]hexane-6-carboxamide

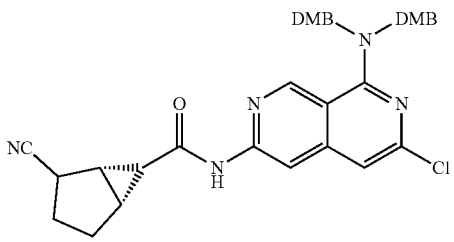

To a solution of (exo)-N-(8-[bis[(2,4-dimethoxyphenyl)methyl]amino]-6-chloro-2,7-naphthyridin-3-yl)-2-hydroxybicyclo[3.1.0]hexane-6-carboxamide (600 mg, 0.96 mmol), triethylamine (980 mg, 9.691 mmol) in dichloromethane (5 mL) was added MsCl (555 mg, 4.84 mmol) at room temperature. After 30 min, the reaction was diluted with water, and the solution was extracted with dichloromethane. The organic extract was dried over Na₂SO₄, filtered, and concentrated under vacuum. To a solution of the crude mesylate in tetrahydrofuran (5 mL) was added KCN (504 mg, 7.75 mmol) and 18-crown-6 (256 mg, 0.96 mmol). The reaction was heated at 60° C. for 16 h before concentration. Purification of the resulting residue by silica-gel chromatography (1:3 petroleum ether/ethyl acetate) afforded (exo)-N-(8-[bis[(2,4-dimethoxyphenyl) methyl]amino]-6-chloro-2,7-naphthyridin-3-yl)-2-cyanobicyclo[3.1.0] hexane-6-carboxamide (100 mg, 16%) as a brown solid. LCMS: (ESI) [M+H]⁺=628.3.

Step 3: (exo)-N-(8-(bis(2,4-dimethoxybenzyl)amino)-6-(4-methylpyridin-3-yl)-2,7-naphthyridin-3-yl)-2-cyanobicyclo[3.1.0]hexane-6-carboxamide

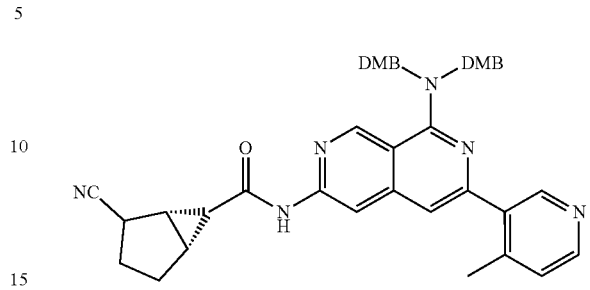

A mixture of (exo)-N-(8-[bis[(2,4-dimethoxyphenyl)methyl]amino]-6-chloro-2,7-naphthyridin-3-yl)-2-cyanobicyclo[3.1.0]hexane-6-carboxamide (100 mg, 0.16 mmol), 4-methylpyridin-3-yl) boronic acid (65 mg, 0.47 mmol), X-phos G2 Pd(25 mg, 0.03 mmol), X-phos (22 mg, 0.05 mmol), and KOAc (78 mg, 0.79 mmol) in 9:1 1,4-dioxane/water (2 mL) was heated at 100° C. After 2.5 h, the reaction was concentrated under vacuum, and the resulting residue was purified by silica-gel chromatography (10:1 dichloromethane/methanol) to afford (exo)-N-(8-[bis [(2,4-dimethoxyphenyl)methyl]amino]-6-(4-methylpyridin-3-yl)-2,7-naphthyridin-3-yl)-2-cyanobicyclo[3.1.0]hexane-6-carboxamide (80 mg, 73%) as a brown solid. LCMS: (ESI) [M+H]⁺=685.4.

Step 4: (exo)-N-(8-amino-6-(4-methylpyridin-3-yl)-2,7-naphthyridin-3-yl)-2-cyanobicyclo[3.1.0]hexane-6-carboxamide

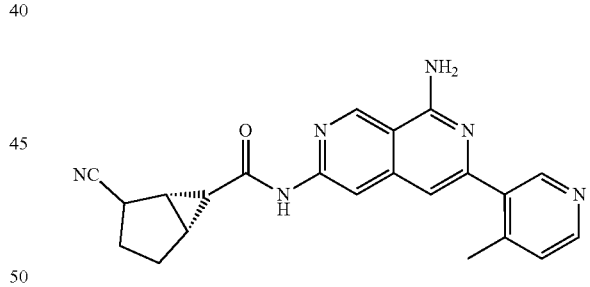

A solution of (exo)-N-(8-[bis[(2,4-dimethoxyphenyl)methyl]amino]-6-(4-methylpyridin-3-yl)-2,7-naphthyridin-3-yl)-2-cyanobicyclo[3.1.0]hexane-6-carboxamide (60 mg, 0.08 mmol) in dichloromethane (2 mL) was added trifluoroacetic acid (4 mL) at room temperature. After 4 h, the reaction was concentrated under vacuum. Purification by flash column chromatography (10:1 dichloromethane/methanol) followed by Prep-HPLC afforded (exo)-N-[8-amino-6-(4-methyl pyridin-3-yl)-2,7-naphthyridin-3-yl]-2-cyanobicyclo[3.1.0]hexane-6-carboxamide (6 mg, 18%) as an off-white solid. LCMS (ESI): $R_T$ (min)=2.34, [M+H]⁺=385.2, method=K-1; ¹H NMR (300 MHz, DMSO-$d_6$) δ 10.80 (s, 1H), 9.35 (s, 1H), 8.55 (s, 1H), 8.43 (d, J=5.0 Hz, 1H), 8.20 (s, 1H), 7.40-7.22 (m, 3H), 6.97 (s, 1H), 3.36 (d, J=5.0 Hz, 1H), 2.40 (s, 3H), 2.14-2.02 (m, 2H), 2.02-1.80 (m, 4H), 1.55-1.45 (m, 1H).

Example 185 trans-N-(8-amino-6-(4-methylpyridin-3-yl)-2,7-naphthyridin-3-yl)-2-((S)-2-oxooxazolidin-5-yl)cyclopropanecarboxamide (Compound 231)

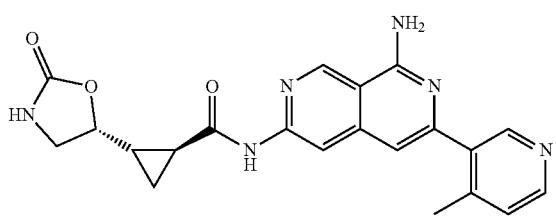

Step 1: 5-[[(tert-butyldimethylsilyl)oxy]methyl]-1,3-oxazolidin-2-one

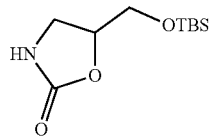

A mixture of 5-(hydroxymethyl)-1,3-oxazolidin-2-one (3 g, 25.61 mmol), imidazole (3.49 g, 51.26 mmol), and TBSCl (4.65 g, 30.85 mmol) in N,N-dimethylformamide (120 mL) was stirred for 4 h at room temperature. The reaction was diluted with H$_2$O, and the resulting mixture was extracted with ethyl acetate. The collected organic extract was dried over Na$_2$SO$_4$, filtered, and concentrated under vacuum to provide 5-[[(tert-butyldimethylsilyl)oxy]methyl]-1,3-oxazolidin-2-one (5.03 g, 85%) as a light yellow oil. LCMS(ESI): [M+H]$^+$=232.1.

Step 2: 5-[[(tert-butyldimethylsilyl)oxy]methyl]-3-[(4-methoxyphenyl)methyl]-1,3-oxazolidin-2-one

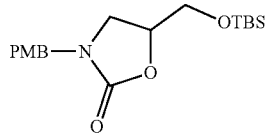

Sodium hydride (2.4 g, 100.01 mmol) was added to a solution of 5-[[(tert-butyldimethylsilyl)oxy]methyl]-1,3-oxazolidin-2-one (4.6 g, 19.88 mmol) in N,N-dimethylformamide (100 mL) at room temperature under nitrogen for 30 min. para-Methoxybenzyl chloride (PMBCl) (3.1 g, 19.79 mmol) was added to the reaction, and the mixture was stirred for 2 h at room temperature. Excess sodium hydride was quenched by water, and the resulting solution was extracted with ethyl acetate. The collected organic was dried over Na$_2$SO$_4$, filtered, and concentrated under vacuum. Purification by flash column chromatography (10:1 dichloromethane/methanol) afforded 5-[[(tert-butyldimethylsilyl)oxy]methyl]-3-[(4-methoxyphenyl)methyl]-1,3-oxazolidin-2-one (6.3 g, 90%) as a light yellow oil. LCMS(ESI): [M+H]$^+$=352.2.

Step 3: 5-(hydroxymethyl)-3-[(4-methoxyphenyl)methyl]-1,3-oxazolidin-2-one

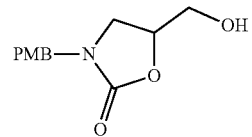

A mixture of 5-[[(tert-butyldimethylsilyl)oxy]methyl]-3-[(4-methoxyphenyl)methyl]-1,3-oxazolidin-2-one (6.2 g, 17.63 mmol) and TBAF (9.12 g, 34.88 mmol) in tetrahydrofuran (100 mL) was stirred for 3 h at room temperature. The reaction was diluted with H$_2$O, and the resulting mixture was extracted with dichloromethane. The organic extract was dried over Na$_2$SO$_4$, filtered, and concentrated under vacuum. Purification by flash column chromatography (10:1 dichloromethane/methanol) afforded 5-(hydroxymethyl)-3-[(4-methoxyphenyl)methyl]-1,3-oxazolidin-2-one (93.7 g, 88%) as a light yellow oil. LCMS(ESI): [M+H]$^+$=238.1.

Step 4: 3-[(4-methoxyphenyl)methyl]-2-oxo-1,3-oxazolidine-5-carbaldehyde

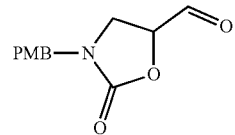

A solution of DMSO (1.56 g, 19.96 mmol) in dichloromethane (20 mL) was added dropwise to oxalyl chloride (1.27 g, 10.00 mmol) in dichloromethane (20 mL) at −78° C. After 30 min 5-(hydroxymethyl)-3-[(4-methoxyphenyl)methyl]-1,3-oxazolidin-2-one (1.98 g, 8.34 mmol) was added to the reaction at −78° C. After 1 h, triethylamine (1.69 g, 16.70 mmol) was added, and the reaction mixture was warmed to room temperature for 16 h. The mixture was concentrated under vacuum to afford 3-[(4-methoxyphenyl)methyl]-2-oxo-1,3-oxazolidine-5-carbaldehyde (1.2 g, crude) as a light yellow solid.

Step 5: ethyl (2E)-3-[3-[(4-methoxyphenyl)methyl]-2-oxo-1,3-oxazolidin-5-yl]prop-2-enoate

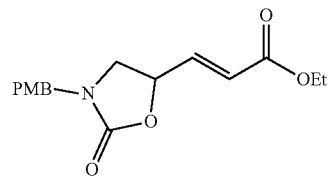

A mixture of 3-[(4-methoxyphenyl)methyl]-2-oxo-1,3-oxazolidine-5-carbaldehyde (1.2 g, 5.10 mmol) and ethyl 2-(triphenylphosphanylidene)acetate (2.67 g, 7.66 mmol) in tetrahydrofuran (50 mL) was stirred for 12 h at room temperature. The reaction mixture was concentrated under vacuum. The residue was purified by flash column chromatography (1:1 ethyl acetate/petroleum ether) to provide ethyl (2E)-3-[3-[(4-methoxyphenyl)methyl]-2-oxo-1,3-oxazolidin-5-yl]prop-2-enoate (1.14 g, 73%) as a light yellow solid. LCMS (ESI): [M+H]⁺=306.1.

Step 6: ethyl trans-2-[3-[(4-methoxyphenyl)methyl]-2-oxo-1,3-oxazolidin-5-yl]cyclopropane-1-carboxylate

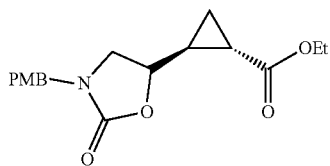

A mixture of trimethylsulfoxonium iodide (1.5 g, 6.81 mmol) and t-BuOK (762 mg, 6.79 mmol) in DMSO (15 mL) was stirred for 30 min at room temperature. Ethyl (2E)-3-[3-[(4-methoxyphenyl)methyl]-2-oxo-1,3-oxazolidin-5-yl]prop-2-enoate (1.04 g, 3.40 mmol) was added. The mixture was allowed to react for 12 h at room temperature before dilution with water. The solution was extracted with ethyl acetate, and the extracts were combined and concentrated. Purification by silica gel chromatography (1:1 ethyl acetate/petroleum ether) afforded ethyl trans-2-[3-[(4-methoxyphenyl)methyl]-2-oxo-1,3-oxazolidin-5-yl]cyclopropane-1-carboxylate (278 mg, 26%) as a colorless oil. LCMS (ESI): [M+H]⁺=320.1;

Step 7: trans-2-[3-[(4-methoxyphenyl)methyl]-2-oxo-1,3-oxazolidin-5-yl]cyclopropane-1-carboxylic acid

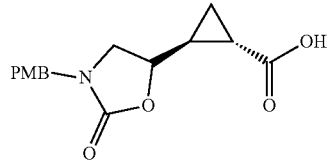

A mixture of ethyl trans-2-[3-[(4-methoxyphenyl)methyl]-2-oxo-1,3-oxazolidin-5-yl]cyclopropane-1-carboxylate (241 mg, 0.75 mmol) and LiOH (55 mg, 2.29 mmol) in 1:1 tetrahydrofuran/water (10 mL) was stirred for 1 h at room temperature. The reaction solution was diluted with water and acidified to pH 5 with 2 M aqueous hydrogen chloride. The solution was extracted with DCM. The extracts were dried with Na₂SO₄, filtered, and concentrated under vacuum to afford crude trans-2-[3-[(4-methoxyphenyl)methyl]-2-oxo-1,3-oxazolidin-5-yl]cyclopropane-1-carboxylic acid (260 mg) as a light yellow solid.

Step 8: trans-N-(8-[bis[(2,4-dimethoxyphenyl)methyl]amino]-6-(4-methylpyridin-3-yl)-2,7-naphthyridin-3-yl)-2-[3-[(4-methoxyphenyl)methyl]-2-oxo-1,3-oxazolidin-5-yl]cyclopropane-1-carboxamide

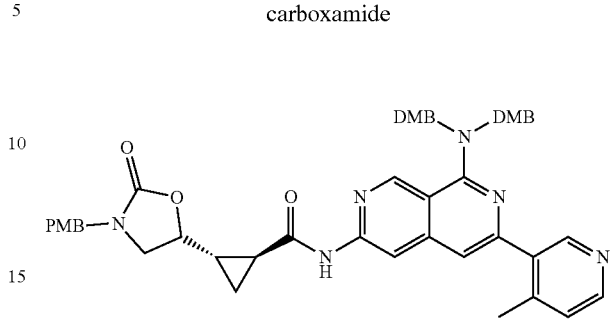

To an ice-cooled solution of trans-2-[3-[(4-methoxyphenyl)methyl]-2-oxo-1,3-oxazolidin-5-yl]cyclopropane-1-carboxylic acid (216 mg, 0.74 mmol), 1-N,1-N-bis[(2,4-dimethoxyphenyl)methyl]-3-(4-methylpyridin-3-yl)-2,7-naphthyridine-1,6-diamine (341 mg, 0.62 mmol) and pyridine (1 mL) in dichloromethane (5 mL) was added POCl₃ (285 mg, 1.85 mmol) dropwise. After 1 h the reaction mixture was diluted with water, and the solution was extracted with dichloromethane. The collected organic was dried over Na₂SO₄, filtered and concentrated under vacuum to provide crude trans-N-(8-[bis[(2,4-dimethoxyphenyl)methyl]amino]-6-(4-methylpyridin-3-yl)-2,7-naphthyridin-3-yl)-2-[3-[(4-methoxyphenyl)methyl]-2-oxo-1,3-oxazolidin-5-yl]cyclopropane-1-carboxamide (200 mg) as a brown solid. LCMS (ESI): [M+H]⁺=825.4.

Step 9: trans-N-[8-amino-6-(4-methylpyridin-3-yl)-2,7-naphthyridin-3-yl]-2-(2-oxo-1,3-oxazolidin-5-yl)cyclopropane-1-carboxamide

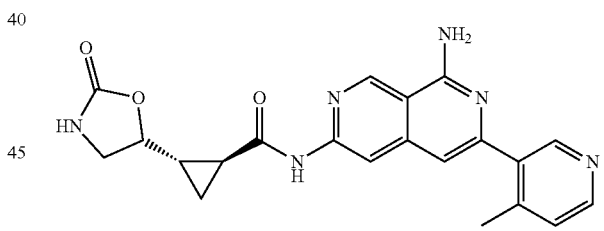

A mixture of trans-N-(8-[bis[(2,4-dimethoxyphenyl)methyl]amino]-6-(4-methylpyridin-3-yl)-2,7-naphthyridin-3-yl)-2-[3-[(4-methoxyphenyl)methyl]-2-oxo-1,3-oxazolidin-5-yl]cyclopropane-1-carboxamide (241 mg, 0.29 mmol) in trifluoroacetic acid (5 mL) was heated at 80° C. for 1 h. The solution was then cooled to room temperature. CF₃SO₃H (3 mL) was added, and the reaction mixture was stirred for an additional hour at room temperature. The mixture was concentrated under vacuum to provide a residue that was dissolved in MeOH. The solution was basified to pH 8-9 with ammonium hydroxide and purified by Prep-HPLC to afford trans-N-[8-amino-6-(4-methylpyridin-3-yl)-2,7-naphthyridin-3-yl]-2-(2-oxo-1,3-oxazolidin-5-yl)cyclopropane-1-carboxamide (7.7 mg, 7%) as a light yellow solid. LCMS (ESI): R$_T$ (min)=1.40, [M+H]⁺=405.2, method=M; ¹H NMR (300 MHz, DMSO-d₆) δ 11.07-11.0 (m, 1H), 9.38 (s, 1H), 8.57 (s, 1H), 8.44 (d, J=6.0 Hz, 1H), 8.23 (s, 1H), 7.55 (s, 1H), 7.34 (s, 2H), 7.30 (d, J=6.0 Hz, 1H), 6.98 (s, 1H), 4.42-4.18 (m, 1H), 3.64-3.58 (m, 1H), 3.32-3.23 (m, 1H), 2.41 (s, 3H), 2.25-2.12 (m, 1H), 1.67-1.62 (m, 1H), 1.17-0.96 (m, 2H).

Example 186

(+/−)-trans-N-(8-amino-6-(4-(2-hydroxypropyl)pyridin-3-yl)-2,7-naphthyridin-3-yl)-2-cyanocyclopropanecarboxamide (Compound 232)

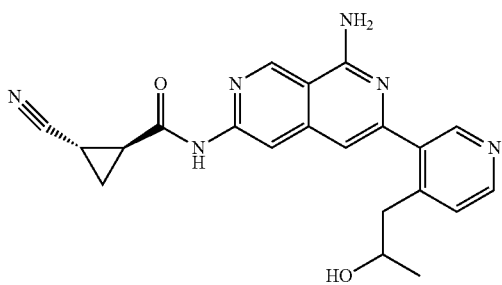 [SMILES: CC(O)Cc1ccncc1-c1cc2cc(NC(=O)[C@H]3C[C@@H]3C#N)ncc2c(N)n1]

Step 1: 1-(3-bromopyridin-4-yl)propan-2-ol

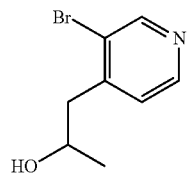

LDA (4.4 mL, 32.44 mmol) was added dropwise to a solution of 3-bromo-4-methylpyridine (1 g, 5.81 mmol) in tetrahydrofuran (30 mL) at −78° C. After 1 h, acetaldehyde (386 mg, 8.762 mmol) was added and the reaction solution was stirred for an additional 2 h at −78° C. The reaction was then diluted with water, and the resulting solution was extracted with ethyl acetate. The collected organic was dried over Na$_2$SO$_4$, filtered, and concentrated under vacuum. The residue was purified by flash column chromatography (10:1 dichloromethane/methanol) to provide 1-(3-bromopyridin-4-yl)propan-2-ol (100 mg, 8%) as a yellow oil. LCMS (ESI): [M+H]$^+$=216.1.

Step 2: 3-methyl-3,4-dihydro-[1,2]oxaborinino[3,4-c]pyridin-1-ol

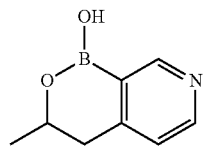

A mixture of 1-(3-bromopyridin-4-yl)propan-2-ol (500 mg, 2.31 mmol), 4,4,5,5-tetramethyl-2-(tetramethyl-1,3,2-dioxaborolan-2-yl)-1,3,2-dioxaborolane (2.9 g, 10.74 mmol), Pd(dppf)Cl$_2$ (380 mg, 0.46 mmol), KOAc (684 mg, 6.96 mmol) in dioxane (10 mL) was heated at 100° C. for 4 h under nitrogen. The reaction mixture was concentrated under vacuum, and the resulting residue was dissolved in H$_2$O. The aqueous solution was basified to pH ~10 with aqueous NaOH and then washed with ethyl acetate. The aqueous layer was acidified to pH 5-6 with HCl and concentrated in vacuo. The residue was suspended in 1:1 ethyl acetate/ethanol and filtered. The filtrate was concentrated under vacuum to afford crude 3-methyl-1H,3H,4H-[1,2]oxaborinino[3,4-c]pyridin-1-ol (300 mg, 80%) as a yellow solid. LCMS (ESI): [M+H]$^+$=164.1.

Step 3: trans-N-(8-amino-6-chloro-2,7-naphthyridin-3-yl)-2-cyanocyclopropanecarboxamide

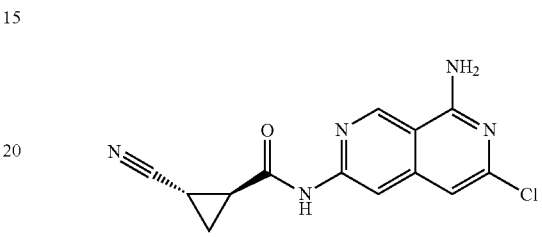

A mixture of trans-2-cyano-N-(6,8-dichloro-2,7-naphthyridin-3-yl)cyclopropane-1-carboxamide (200 mg, 0.65 mmol) and ammonium hydroxide (0.17 mmol) in dioxane (8 mL) was heated at 100° C. for 1 h under nitrogen. The reaction mixture was concentrated under vacuum to afford crude trans-N-(8-amino-6-chloro-2,7-naphthyridin-3-yl)-2-cyanocyclopropane-1-carboxamide (200 mg) as a white solid. LCMS (ESI): [M+H]$^+$=288.1.

Step 4: trans-N-(8-amino-6-(4-(2-hydroxypropyl)pyridin-3-yl)-2,7-naphthyridin-3-yl)-2-cyanocyclopropanecarboxamide

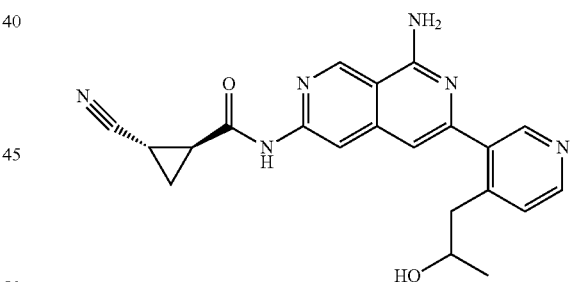

A mixture of trans-N-(8-amino-6-chloro-2,7-naphthyridin-3-yl)-2-cyanocyclopropane-1-carboxamide (200 mg, 0.69 mmol), 3-methyl-1H,3H,4H-[1,2]oxaborinino[3,4-c]pyridin-1-ol (546 mg, 3.35 mmol), Pd(PPh$_3$)$_4$ (120 mg, 0.10 mmol), and Cs$_2$CO$_3$ (452 mg, 1.38 mmol) in 10:1 dioxane/water (11 mL) was heated at 100° C. for 4 h under nitrogen. The reaction mixture was concentrated under vacuum, and the resulting residue was purified by flash column chromatography (10:1 dichloromethane/methanol) to provide trans-N-[8-amino-6-[4-(2-hydroxypropyl)pyridin-3-yl]-2,7-naphthyridin-3-yl]-2-cyanocyclopropane-1-carboxamide (80.1 mg 30%) as a yellow solid. LCMS (ESI): R$_T$ (min)=1.71, [M+H]$^+$=389.1, method=K-1; $^1$H NMR (300 MHz, DMSO-d$_6$) δ 11.31 (s, 1H), 9.41 (s, 1H), 8.69 (s, 1H), 8.59 (d, J=2.2 Hz, 1H), 8.23 (s, 1H), 7.54 (d, J=2.2 Hz, 1H), 7.40 (s, 2H), 7.06 (s, 1H), 4.82-4.80 (m, 1H), 3.81-3.79 (m, 1H), 2.92-

2.77 (m, 3H), 2.22-2.13 (m, 1H), 1.68-1.55 (m, 1H), 1.52-1.34 (m, 1H), 0.98 (d, J=4.8 Hz, 3H).

Example 187

(1S,2S)—N-(8-amino-5-chloro-6-(4-methylpyridin-3-yl)-2,7-naphthyridin-3-yl)-2-(1-methyl-1H-pyrazol-4-yl)cyclopropanecarboxamide (Compound 233) and (1R,2R)—N-(8-amino-5-chloro-6-(4-methylpyridin-3-yl)-2,7-naphthyridin-3-yl)-2-(1-methyl-1H-pyrazol-4-yl)cyclopropanecarboxamide (Compound 234)

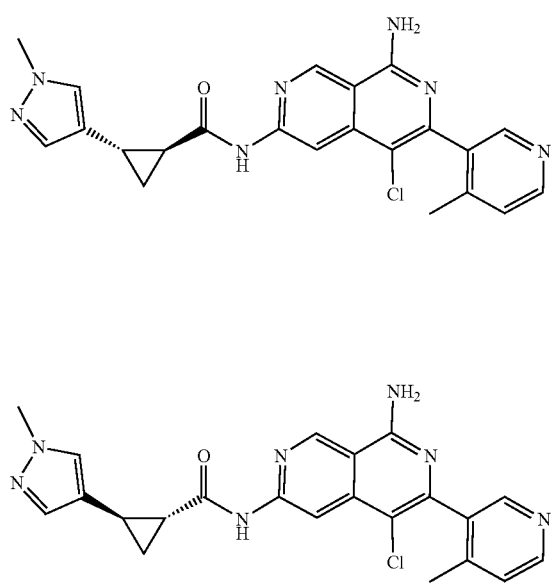

Step 1: trans-N-(8-amino-6-chloro-2,7-naphthyridin-3-yl)-2-(1-methyl-1H-pyrazol-4-yl)cyclopropanecarboxamide

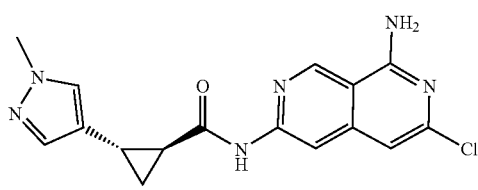 [SMILES: Cn1cc([C@H]2C[C@@H]2C(=O)Nc2cc3cc(Cl)nc(N)c3cn2)cn1]

A mixture of trans-N-(6,8-dichloro-2,7-naphthyridin-3-yl)-2-(1-methyl-H-pyrazol-4-yl)cyclopropane-1-carboxamide (1.8 g, 4.97 mmol) and ammonium hydroxide (36 mL) in 1,4-dioxane (36 mL) was heated at 100° C. for 15 h. The resulting mixture was concentrated under vacuum to afford crude trans-N-(8-amino-6-chloro-2,7-naphthyridin-3-yl)-2-(1-methyl-1H-pyrazol-4-yl)cyclopropanecarboxamide as a white solid (1.7 g, crude). LCMS (ESI)[M+H]⁺=343.1.

Step 2: trans-N-(8-amino-6-(4-methylpyridin-3-yl)-2,7-naphthyridin-3-yl)-2-(1-methyl-1H-pyrazol-4-yl)cyclopropanecarboxamide

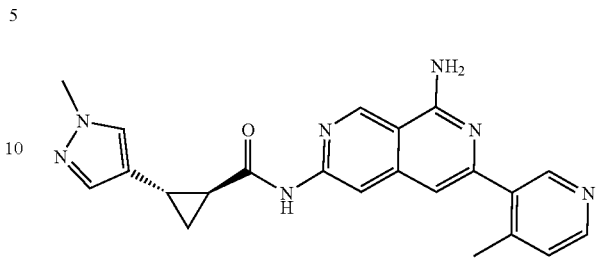

A mixture of trans-N-(8-amino-6-chloro-2,7-naphthyridin-3-yl)-2-(1-methyl-1H-pyrazol-4-yl)cyclopropane-1-carboxamide (280 mg, 0.82 mmol), (4-methylpyridin-3-yl)boronic acid (168 mg, 1.23 mmol), XPhos (78 mg, 0.16 mmol), XPhos-PdCl-2nd G (62 mg, 0.08 mmol) and potassium carbonate (339 mg, 2.45 mmol) in 10:1 1,4-dioxane/water (11 mL) was heated at 100° C. for 1 h under nitrogen. The solids were filtered, and the filtrate was concentrated. Purification by flash column chromatography (15:1 dichloromethane/methanol) afforded trans-N-[8-amino-6-(4-methylpyridin-3-yl)-2,7-naphthyridin-3-yl]-2-(1-methyl-H-pyrazol-4-yl)cyclopropane-1-carboxamide (122 mg, 37% yield) as a yellow solid. LCMS(ESI)[M+H]⁺=400.2.

Step 3: (1S,2S)—N-(8-amino-5-chloro-6-(4-methylpyridin-3-yl)-2,7-naphthyridin-3-yl)-2-(1-methyl-1H-pyrazol-4-yl)cyclopropanecarboxamide and (1R,2R)—N-(8-amino-5-chloro-6-(4-methylpyridin-3-yl)-2,7-naphthyridin-3-yl)-2-(1-methyl-1H-pyrazol-4-yl)cyclopropanecarboxamide

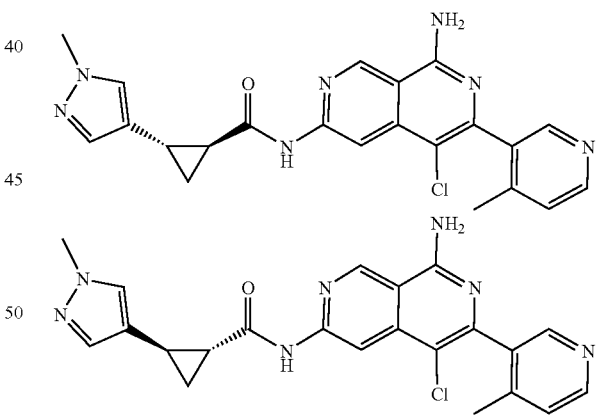

To a solution of trans-N-[8-amino-6-(4-methylpyridin-3-yl)-2,7-naphthyridin-3-yl]-2-(1-methyl-1H-pyrazol-4-yl)cyclopropane-1-carboxamide (50 mg, 0.125 mmol) in N,N-dimethylformamide (10 mL) was added NCS (20.06 mg, 0.150 mmol) in 2 portions at room temperature. After 5 h, the reaction was concentrated under vacuum, and the residue was purified by flash column chromatography (20:1 dichloromethane/methanol) to afford racemic product (15 mg, 26% yield) as a light yellow solid. The enantiomers were isolated by chiral SFC. Compound 233: LCMS (ESI): $R_T$(min)=1.15, [M+H]⁺=434.1, method=K-1; ¹H NMR (300 MHz, CD₃OD) δ 9.34 (d, J=0.9 Hz, 1H), 8.72 (d, J=0.9 Hz, 1H), 8.48 (d, J=5.2 Hz, 1H), 8.41 (s, 1H), 7.51 (s, 1H), 7.44 (d, J=5.3 Hz, 1H), 7.38 (d, J=0.8 Hz, 1H), 3.86 (s, 3H), 2.41-2.39 (m, 1H), 2.29 (s, 3H), 2.14-2.11 (m, 1H), 1.60-1.58 (m, 1H), 1.29-1.26 (m, 1H). Compound 234: LCMS (ESI): R$_T$(min)=1.16, [M+H]$^+$=434.1, method=K-1; $^1$H NMR (400 MHz, CD$_3$OD) δ 9.34 (d, J=0.9 Hz, 1H), 8.72 (d, J=0.9 Hz, 1H), 8.48 (d, J=5.2 Hz, 1H), 8.41 (s, 1H), 7.51 (s, 1H), 7.44 (d, J=5.3 Hz, 1H), 7.38 (d, J=0.8 Hz, 1H), 3.86 (s, 3H), 2.41-2.39 (m, 1H), 2.29 (s, 3H), 2.14-2.11 (m, 1H), 1.60-1.58 (m, 1H), 1.29-1.26 (m, 1H).

Example 188

(1R,2R)—N-(6-(4-(1H-pyrazol-4-yl)pyridin-3-yl)-8-amino-2,7-naphthyridin-3-yl)-2-cyanocyclopropanecarboxamide (Compound 235) and (1S,2S)—N-(6-(4-(1H-pyrazol-4-yl)pyridin-3-yl)-8-amino-2,7-naphthyridin-3-yl)-2-cyanocyclopropanecarboxamide (Compound 236)

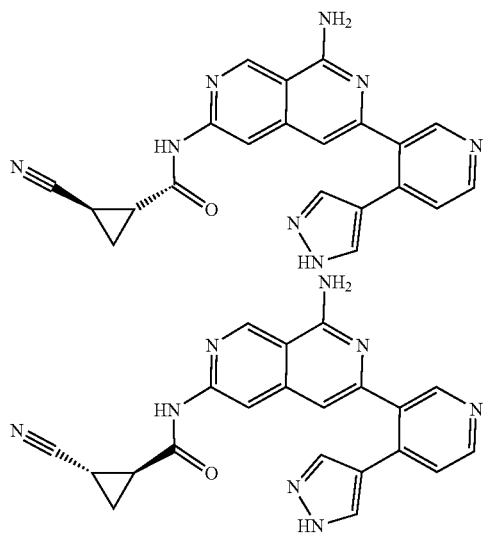

Step 1: 3-bromo-4-(1-(tetrahydro-2H-pyran-2-yl)-1H-pyrazol-4-yl)pyridine

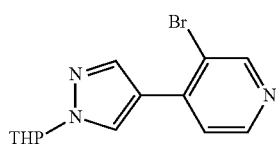

A mixture of 1-(oxan-2-yl)-4-(tetramethyl-1,3,2-dioxaborolan-2-yl)-1H-pyrazole (2.94 g, 10.57 mmol), 3-bromo-4-iodopyridine (2.00 g, 7.05 mmol), potassium carbonate (2.92 g, 21.12 mmol) and Pd(dppf)Cl$_2$·CH$_2$Cl$_2$ (580 mg, 0.710 mmol) in N,N-dimethylformamide (20 mL)/water (4 mL) was heated at 80° C. for 6 h under nitrogen. The resulting solution was extracted with ethyl acetate, and the combined extracts were dried over Na$_2$SO$_4$, filtered, and concentrated under vacuum. Purification by silica gel chromatography (7:3 ethyl acetate/petroleum ether) provided 3-bromo-4-[1-(oxan-2-yl)-1H-pyrazol-4-yl]pyridine (2.75 g) as a yellow oil. LCMS (ESI): [M+H]$^+$=308.2.

Step 2: 4-(1-(tetrahydro-2H-pyran-2-yl)-1H-pyrazol-4-yl)pyridin-3-ylboronic acid

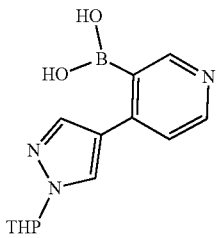

A mixture of 3-bromo-4-[1-(oxan-2-yl)-1H-pyrazol-4-yl]pyridine (2.70 g, 8.76 mmol), 4,4,5,5-tetramethyl-2-(tetramethyl-1,3,2-dioxaborolan-2-yl)-1,3,2-dioxaborolane (8.90 g, 35.04 mmol), Pd(dppf)Cl$_2$ dichloromethane (720 mg, 0.88 mmol) and KOAc (3.44 g, 35.05 mmol) in 1,4-dioxane (40 mL) was heated at 100° C. for 4 h under nitrogen. The mixture was concentrated under vacuum, and the resulting residue was purified by silica gel chromatography (9:1 dichloromethane/methanol) to afford [4-[1-(oxan-2-yl)-1H-pyrazol-4-yl]-1,3-azaborinin-5-yl]boronic acid (1.5 g, 63% yield) as a black solid. LCMS (ESI): [M+H]$^+$=274.1.

Step 3: trans-N-(8-amino-6-(4-(1-(tetrahydro-2H-pyran-2-yl)-1H-pyrazol-4-yl)pyridin-3-yl)-2,7-naphthyridin-3-yl)-2-cyanocyclopropanecarboxamide

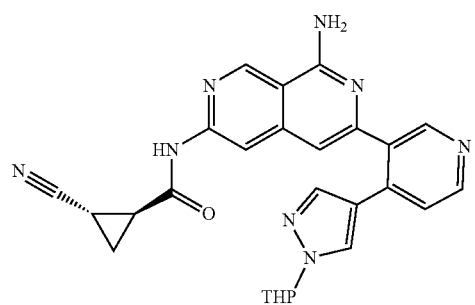

A mixture of trans-N-(8-amino-6-chloro-2,7-naphthyridin-3-yl)-2-cyanocyclopropane-1-carboxamide (400 mg, 1.39 mmol), [4-[1-(oxan-2-yl)-1H-pyrazol-4-yl]pyridin-3-yl]boronic acid (1139.07 mg, 4.17 mmol), X-Phos (66.28 mg, 0.13 mmol), XPhos-PdOMs (111.14 mg, 0.13 mmol), and potassium carbonate (576 mg, 4.17 mmol) in 5:1 dioxane/water (36 mL) was heated at 100° C. for 6 h under nitrogen. The reaction was concentrated under vacuum, and the resulting residue was purified by silica gel chromatography (9:1 dichloromethane/methanol) to afford trans-N-(8-amino-6-[4-[1-(oxan-2-yl)-1H-pyrazol-4-yl]pyridin-3-yl]-2,7-naphthyridin-3-yl)-2-cyanocyclopropane-1-carboxamide (510 mg, 76% yield) as a brown oil. LCMS53 (ESI): [M+H]$^+$=481.1

Step 4: (1R,2R)—N-(6-(4-(1H-pyrazol-4-yl)pyridin-3-yl)-8-amino-2,7-naphthyridin-3-yl)-2-cyanocyclopropanecarboxamide and (1S,2S)—N-(6-(4-(1H-pyrazol-4-yl)pyridin-3-yl)-8-amino-2,7-naphthyridin-3-yl)-2-cyanocyclopropanecarboxamide

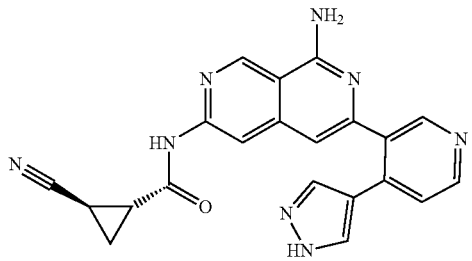

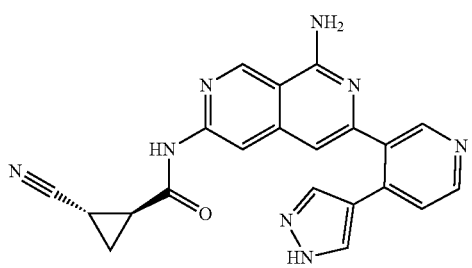

A mixture of (1S,2S)—N-(8-amino-6-[4-[1-(oxan-2-yl)-1H-pyrazol-4-yl]pyridin-3-yl]-2,7-naphthyridin-3-yl)-2-cyanocyclopropane-1-carboxamide (510 mg, 1.06 mmol) and trifluoroacetic acid (4 mL) in dichloromethane (10 mL) was stirred for 5 h at 25° C. The resulting mixture was concentrated under vacuum. The crude product was purified by Prep-HPLC and chiral SFC to afford two enantiomers. Compound 235: LCMS (ESI): [M+H]$^+$=397.15, R$_T$ (min)=1.46, method=K-1; $^1$H NMR (300 MHz, DMSO-d$_6$) δ 12.91 (s, 1H), 11.28 (s, 1H), 9.41 (s, 1H), 8.52 (d, J=5.3 Hz, 1H), 8.46 (s, 1H), 8.12 (s, 1H), 7.61-7.58 (m, 3H), 7.40 (s, 2H), 6.83 (s, 1H), 2.81-2.69 (m, 1H), 2.14-2.12 (m, 1H), 1.60-1.58 (m, 1H), 1.42-1.40 (m, 1H). Compound 236: LCMS (ESI): [M+H]$^+$=397.15, R$_T$ (min)=0.92, method=K-1; $^1$H NMR (300 MHz, DMSO-d$_6$) δ 12.91 (s, 1H), 11.28 (s, 1H), 9.41 (s, 1H), 8.52 (d, J=5.3 Hz, 1H), 8.46 (s, 1H), 8.12 (s, 1H), 7.61-7.58 (m, 3H), 7.40 (s, 2H), 6.83 (s, 1H), 2.81-2.69 (m, 1H), 2.14-2.12 (m, 1H), 1.60-1.58 (m, 1H), 1.42-1.40 (m, 1H).

Example 189

(1R,2S)—N-(8-amino-6-(4-methyl-6-(1-methyl-1H-pyrazol-4-yl)pyridin-3-yl)-2,7-naphthyridin-3-yl)-2-(cyanomethyl)cyclopropanecarboxamide (Compound 237) and (1S,2R)—N-(8-amino-6-(4-methyl-6-(i-methyl-H-pyrazol-4-yl)pyridin-3-yl)-2,7-naphthyridin-3-yl)-2-(cyanomethyl)cyclopropanecarboxamide (Compound 238)

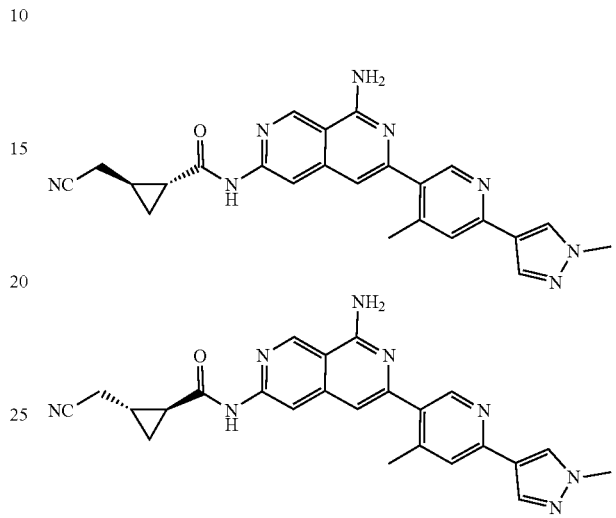

The title compound was prepared using a procedure as described for (1R,2R)—N-(6-(4-(1H-pyrazol-4-yl)pyridin-3-yl)-8-amino-2,7-naphthyridin-3-yl)-2-cyanocyclopropanecarboxamide (Compound 235). The enantiomers were isolated by chiral SFC. Compound 237: LCMS (ESI): R$_T$(min)=1.09, [M+H]$^+$=439.2, method=M; $^1$H NMR (400 MHz, DMSO-d$_6$) δ 11.05 (s, 1H), 9.37 (s, 1H), 8.51 (s, 1H), 8.30 (s, 1H), 8.23 (s, 1H), 8.02 (s, 1H), 7.59 (s, 1H), 7.31 (s, 1H), 6.98 (s, 2H), 3.97 (s, 3H), 2.74 (d, J=9.0 Hz, 2H), 2.45 (s, 3H), 2.14-2.09 (m, 1H), 1.62-1.55 (m, 1H), 1.17-1.11 (m, 1H), 1.00-0.94 (m, 1H). Compound 238: LCMS (ESI): R$_T$ (min)=1.09, [M+H]$^+$=439.2, method=M; $^1$H NMR (400 MHz, DMSO-d$_6$) δ 11.05 (s, 1H), 9.37 (s, 1H), 8.51 (s, 1H), 8.30 (s, 1H), 8.23 (s, 1H), 8.02 (s, 1H), 7.59 (s, 1H), 7.31 (s, 1H), 6.98 (s, 2H), 3.97 (s, 3H), 2.74 (d, J=9.0 Hz, 2H), 2.45 (s, 3H), 2.14-2.09 (m, 1H), 1.62-1.55 (m, 1H), 1.17-1.11 (m, 1H), 1.00-0.94 (m, 1H).

Example 190

(1R,2R)—N-[8-amino-6-(4-methylpyridin-3-yl)-2,7-naphthyridin-3-yl]-2-(2-methoxypropan-2-yl)cyclopropane-1-carboxamide (Compound 239) and (1S,2S)—N-[8-amino-6-(4-methylpyridin-3-yl)-2,7-naphthyridin-3-yl]-2-(2-methoxypropan-2-yl)cyclopropane-1-carboxamide (Compound 240)

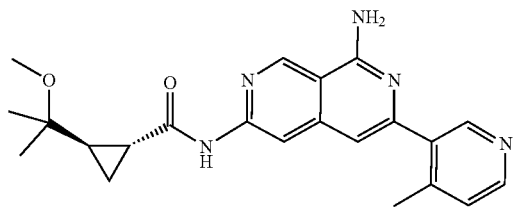

755
-continued

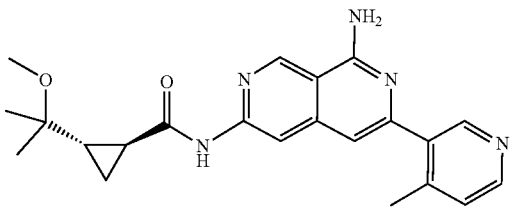

The title compounds were prepared using a procedure as described for (1R,2R)—N-[8-amino-6-(4-methylpyridin-3-yl)-2,7-naphthyridin-3-yl]-2-(2-hydroxypropan-2-yl)cyclopropane-1-carboxamide (Compound 241). Compound 239): LCMS (ESI): $R_T$ (min)=1.08, [M+H]$^+$=392.2, method=K-1; $^1$H NMR (300 MHz, CD$_3$OD) δ 9.30 (s, 1H), 8.54 (s, 1H), 8.43 (d, J=5.1 Hz, 1H), 8.31 (s, 1H), 7.40 (d, J=5.1 Hz, 1H), 6.98 (s, 1H), 3.28 (s, 3H), 2.46 (s, 3H), 2.10-2.02 (m, 1H), 1.67-1.58 (m, 1H), 1.24 (s, 3H), 1.21 (s, 3H), 1.24-1.15 (m, 1H), 1.10-1.01 (m, 1H). Compound 240: LCMS (ESI): $R_T$ (min)=1.08, [M+H]$^+$=392.2, method=K-1; $^1$H NMR (300 MHz, CD$_3$OD) δ 9.30 (s, 1H), 8.54 (s, 1H), 8.43 (d, J=5.1 Hz, 1H), 8.31 (s, 1H), 7.40 (d, J=5.1 Hz, 1H), 6.98 (s, 1H), 3.28 (s, 3H), 2.46 (s, 3H), 2.10-2.02 (m, 1H), 1.67-1.58 (m, 1H), 1.24 (s, 3H), 1.21 (s, 3H), 1.24-1.15 (m, 1H), 1.10-1.01 (m, 1H).

Example 191

(1R,2R)—N-[8-amino-6-(4-methylpyridin-3-yl)-2,7-naphthyridin-3-yl]-2-(2-hydroxypropan-2-yl)cyclopropane-1-carboxamide (Compound 241) and (1S,2S)—N-[8-amino-6-(4-methylpyridin-3-yl)-2,7-naphthyridin-3-yl]-2-(2-hydroxypropan-2-yl)cyclopropane-1-carboxamide (Compound 242)

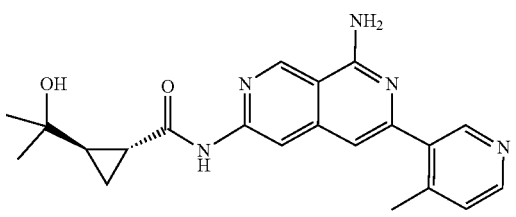

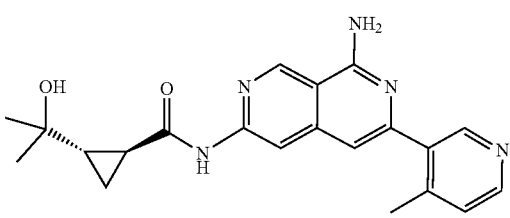

756

Step 1: Methyl-2-[(8-[bis[(2,4-dimethoxyphenyl)methyl]amino]-6-(4-methylpyridin-3-yl)-2,7-naphthyridin-3-yl)carbamoyl]cyclopropane-1-carboxylate

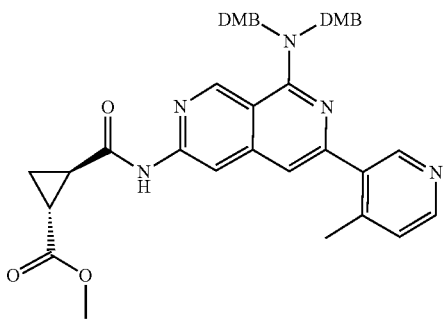

To an ice-cooled solution of trans-2-(methoxycarbonyl)cyclopropane-1-carboxylic acid (210 mg, 1.46 mmol), pyridine (3 mL, 37.271 mmol), and N,N-dimethylformamide (0.05 mL) in dichloromethane (6 mL) was added oxalyl chloride (320 mg, 2.521 mmol). The reaction mixture was warmed to room temperature for 30 min. 1-N,1-N-bis[(2,4-dimethoxyphenyl)methyl]-3-(4-methylpyridin-3-yl)-2,7-naphthyridine-1,6-diamine (0.5 g, 0.906 mmol) was added. After 1.5 h, the reaction mixture was concentrated under vacuum, and the resulting residue was purified by silica gel chromatography (1:6 ethyl acetate/petroleum ether) to afford methyl 2-[(8-[bis[(2,4-dimethoxyphenyl)methyl]amino]-6-(4-methylpyridin-3-yl)-2,7-naphthyridin-3-yl)carbamoyl]cyclopropane-1-carboxylate (0.56 g, 91%) as a yellow solid. LCMS (ESI) [M+H]$^+$ 402.1.

Step 2: N-(8-[[(2,4-dimethoxyphenyl)methyl][(2-methoxyphenyl)methyl]amino]-6-(4-methylpyridin-3-yl)-2,7-naphthyridin-3-yl)-2-(2-hydroxypropan-2-yl)cyclopropane-1-carboxamide

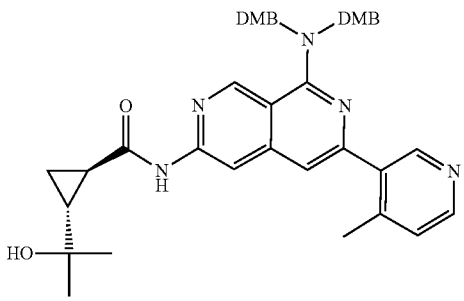

To an ice-cooled solution of methyl 2-[(8-[bis[(2,4-dimethoxyphenyl)methyl]amino]-6-(4-methylpyridin-3-yl)-2,7-naphthyridin-3-yl)carbamoyl]cyclopropane-1-carboxylate (650 mg, 0.959 mmol) in tetrahydrofuran (15.00 mL) was added methyllithium (1.51 mL, 2.405 mmol). The reaction was warmed to 25° C. for 3 h and then concentrated in vacuo. Purification by silica gel chromatography (15:1 dichloromethane/methanol) afforded N-(8-[[(2,4-dimethoxyphenyl)methyl][(2-methoxyphenyl)methyl]amino]-6-(4-methylpyridin-3-yl)-2,7-naphthyridin-3-yl)-2-(2-hydroxypropan-2-yl)cyclopropane-1-carboxamide (0.36 g, 58%) as a yellow solid. LCMS (ESI) [M+H]$^+$ 402.2.

Step 3: (1R,2R)—N-[8-amino-6-(4-methylpyridin-3-yl)-2,7-naphthyridin-3-yl]-2-(2-hydroxypropan-2-yl)cyclopropane-1-carboxamide and (1S,2S)—N-[8-amino-6-(4-methylpyridin-3-yl)-2,7-naphthyridin-3-yl]-2-(2-hydroxypropan-2-yl)cyclopropane-1-carboxamide

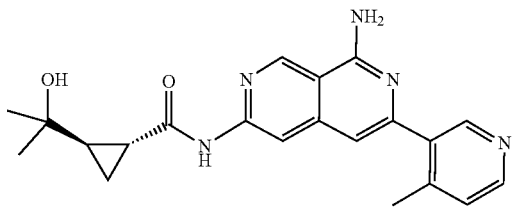

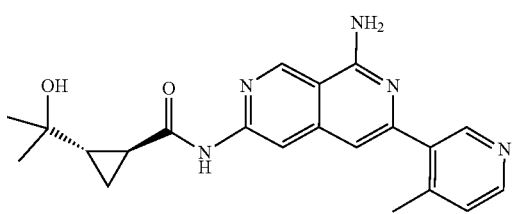

A solution of N-(8-[bis[(2,4-dimethoxyphenyl)methyl]amino]-6-(4-methylpyridin-3-yl)-2,7-naphthyridin-3-yl)-2-(2-hydroxypropan-2-yl)cyclopropane-1-carboxamide (100 mg, 0.148 mmol) in trifluoroacetic acid (4 mL) was heated at 50° C. After 1 h, the reaction was concentrated under vacuum, and the crude product (70 mg) was separated by Chiral-Prep-HPLC to afford (1S,2S)—N-[8-amino-6-(4-methylpyridin-3-yl)-2,7-naphthyridin-3-yl]-2-(2-hydroxypropan-2-yl)cyclopropane-1-carboxamide (18.7 mg, 27%) as a white solid and (1R,2R)—N-[8-amino-6-(4-methylpyridin-3-yl)-2,7-naphthyridin-3-yl]-2-(2-hydroxypropan-2-yl)cyclopropane-1-carboxamide (19.6 mg, 28%) as a white solid. Compound 241: LCMS (ESI): $R_T$ (min)=0.98, [M+H]$^+$=378, method=K-1; $^1$H NMR (300 MHz, CD$_3$OD) δ 9.29 (s, 1H), 8.53 (s, 1H), 8.42 (d, J=5.1 Hz, 1H), 8.29 (s, 1H), 7.39 (d, J=5.1 Hz, 1H), 6.97 (s, 1H), 2.45 (s, 3H), 2.04-1.95 (m, 1H), 1.65-1.55 (m, 1H), 1.28 (d, J=3.0 Hz, 6H), 1.17-1.06 (m, 2H). Compound 242: LCMS (ESI): $R_T$ (min)=0.98, [M+H]$^+$=378, method=K-1; $^1$H NMR (300 MHz, CD$_3$OD) δ 9.29 (s, 1H), 8.53 (s, 1H), 8.42 (d, J=5.1 Hz, 1H), 8.29 (s, 1H), 7.39 (d, J=5.1 Hz, 1H), 6.97 (s, 1H), 2.45 (s, 3H), 2.04-1.95 (m, 1H), 1.65-1.55 (m, 1H), 1.28 (d, J=3.0 Hz, 6H), 1.17-1.06 (m, 2H).

Example 192

(1R,2R)—N-(6-(4-(1H-pyrazol-3-yl)pyridin-3-yl)-8-amino-2,7-naphthyridin-3-yl)-2-cyanocyclopropanecarboxamide (Compound 243) and (1S,2S)—N-(6-(4-(1H-pyrazol-3-yl)pyridin-3-yl)-8-amino-2,7-naphthyridin-3-yl)-2-cyanocyclopropanecarboxamide (Compound 244)

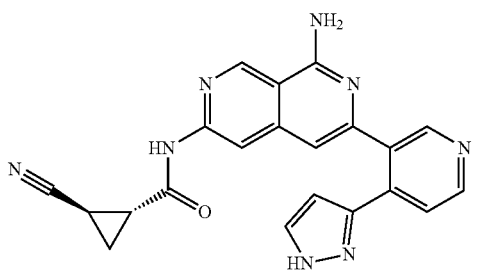

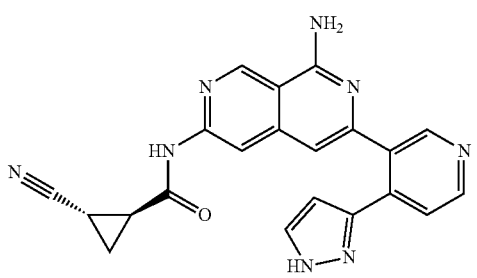

The title compounds were prepared using a procedure as described for (1R,2R)—N-(6-(4-(1H-pyrazol-4-yl)pyridin-3-yl)-8-amino-2,7-naphthyridin-3-yl)-2-cyanocyclopropanecarboxamide (Compound 235). The enantiomers were separated by chiral SFC. Compound 243: LCMS (ESI): $R_T$ (min)=1.01, [M+H]$^+$=397.2, method=K-1; $^1$H NMR (300 MHz, DMSO-d$_6$) δ 13.02 (s, 1H), 11.26 (s, 1H), 9.39 (s, 1H), 8.73-8.45 (m, 2H), 8.08 (s, 1H), 7.81 (d, J=5.2 Hz, 1H), 7.59 (s, 1H), 7.35 (s, 2H), 6.77 (s, 1H), 5.80 (d, J=2.5 Hz, 1H), 2.75-2.73 (m, 1H), 2.14-2.12 (m, 1H), 1.60-1.58 (m, 1H), 1.49-1.32 (m, 1H). Compound 244: LCMS (ESI): $R_T$(min)=1.01, [M+H]$^+$=397.2, method=K-1; $^1$H NMR (300 MHz, DMSO-d$_6$) δ 13.02 (s, 1H), 11.26 (s, 1H), 9.39 (s, 1H), 8.73-8.45 (m, 2H), 8.08 (s, 1H), 7.81 (d, J=5.2 Hz, 1H), 7.59 (s, 1H), 7.35 (s, 2H), 6.77 (s, 1H), 5.80 (d, J=2.5 Hz, 1H), 2.75-2.73 (m, 1H), 2.14-2.12 (m, 1H), 1.60-1.58 (m, 1H), 1.49-1.32 (m, 1H).

Example 193

(1S,2S)—N-(8-amino-6-(4-(2-hydroxyethyl)pyridin-3-yl)-2,7-naphthyridin-3-yl)-2-(isothiazol-4-yl)cyclopropanecarboxamide (Compound 245) and (1R,2R)—N-(8-amino-6-(4-(2-hydroxyethyl)pyridin-3-yl)-2,7-naphthyridin-3-yl)-2-(isothiazol-4-yl)cyclopropanecarboxamide (Compound 246)

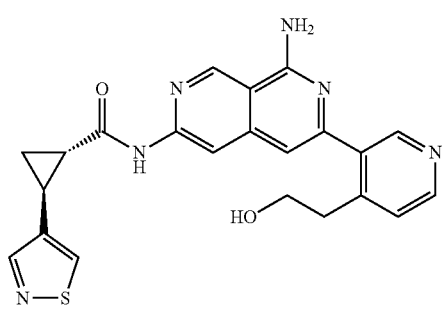

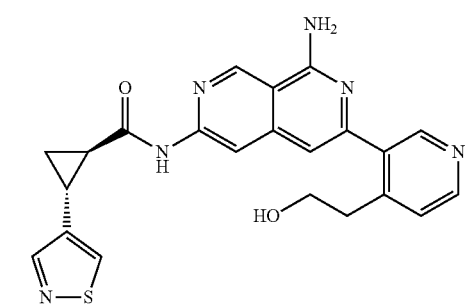

Step 1: tert-butyl (2E)-3-(1,2-thiazol-4-yl)prop-2-enoate

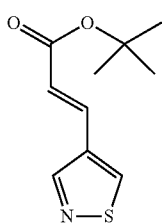

To a solution of 4-bromo-1,2-thiazole (5.0 g, 30.5 mmol) in dioxane (100 mL) was added tert-butyl prop-2-enoate (13.7 g, 107 mmol), Pd(OAc)$_2$ (67 mg, 0.298 mmol), P(o-Tol)$_3$ (2.3 g, 7.6 mmol) and triethylamine (9.3 g, 91.9 mmol). The reaction was heated at 125° C. for 2 h and then concentrated under vacuum. Purified by flash column chromatography (10:1 ethyl acetate/petroleum ether) afforded tert-butyl (2E)-3-(1,2-thiazol-4-yl)prop-2-enoate (2.7 g, 42%) as a yellow solid. LCMS (ESI): [M+H]$^+$=212.1.

Step 2: trans-tert-butyl-2-(1,2-thiazol-4-yl)cyclopropane-1-carboxylate

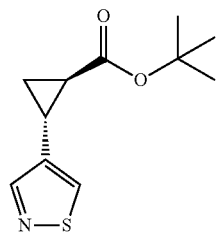

To a solution of tert-butyl (2E)-3-(1,2-thiazol-4-yl)prop-2-enoate (1.3 g, 6.2 mmol) in DMSO (10 mL) was added trimethyloxosulfonium iodide (3 g, 13.6 mmol) and t-BuOK (1.5 g, 13.368 mmol) at 25° C. After 1 h, the resulting solution was extracted with ethyl acetate, and the extracts were concentrated under vacuum. Purification by flash column chromatography (10:ethyl acetate/petroleum ether) afforded trans-tert-butyl-2-(1,2-thiazol-4-yl)cyclopropane-1-carboxylate (510 mg, 37%) as a yellow oil. LCMS (ESI): [M+H]$^+$=226.1.

Step 3: trans-2-(1,2-thiazol-4-yl)cyclopropane-1-carboxylic acid

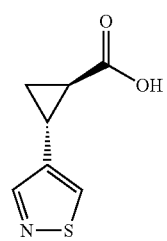 [SMILES: O=C(O)[C@@H]1C[C@H]1c1cnsc1]

A solution of trans-tert-butyl-2-(1,2-thiazol-4-yl)cyclopropane-1-carboxylate (0.50 g, 2.22 mmol) in trifluoroacetic acid (4 mL) was stirred for 1 h at 25° C. The resulting mixture was concentrated, and the residue was purified by flash column chromatography (1:1 ethyl acetate/petroleum ether) to provide trans-2-(1,2-thiazol-4-yl)cyclopropane-1-carboxylic acid (346 mg, 92%) as a brown oil. LCMS (ESI): [M+H]$^+$=170.1

Step 4: trans-N-(6,8-dichloro-2,7-naphthyridin-3-yl)-2-(1,2-thiazol-4-yl)cyclopropane-1-carboxamide

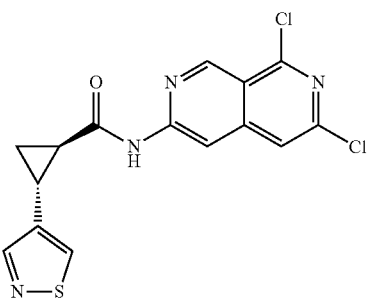 [SMILES: O=C(Nc1cc2cc(Cl)nc(Cl)c2cn1)[C@@H]1C[C@H]1c1cnsc1]

761

To a solution of 6,8-dichloro-2,7-naphthyridin-3-amine (232 mg, 1.08 mmol) in dichloromethane (10 mL) was added (1R,2R)-2-(1,2-thiazol-4-yl)cyclopropane-1-carboxylic acid (290 mg, 1.71 mmol), POCl$_3$ (174 mg, 1.14 mmol) and pyridine (1 mL, 12 mmol) at 25° C. After 1 h, the reaction was concentrated under vacuum. Purified by flash column chromatography (1:1 ethyl acetate/petroleum ether) yielded (trans)-N-(6,8-dichloro-2,7-naphthyridin-3-yl)-2-(1,2-thiazol-4-yl)cyclopropane-1-carboxamide (330 mg, 83%) as a yellow solid. LCMS (ESI): [M+H]$^+$=365.1.

Step 5: trans-N-(8-amino-6-chloro-2,7-naphthyridin-3-yl)-2-(1,2-thiazol-4-yl)cyclopropane-1-carboxamide

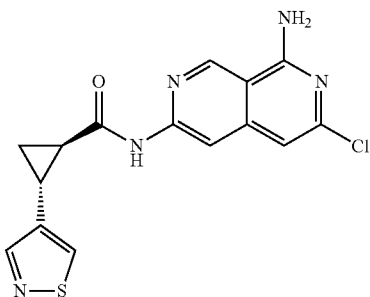

A mixture of trans-N-(6,8-dichloro-2,7-naphthyridin-3-yl)-2-(1,2-thiazol-4-yl)cyclopropane-1-carboxamide (110 mg, 0.301 mmol) and ammonium hydroxide (5 mL) in 1,4-dioxane (5 mL) was heated at 90° C. for 3 h. The mixture was concentrated under vacuum to afford crude trans-N-(8-amino-6-chloro-2,7-naphthyridin-3-yl)-2-(1,2-thiazol-4-yl)cyclopropane-1-carboxamide (120 mg) as a yellow solid. LCMS (ESI): [M+H]$^+$=346.1.

Step 6: (1S,2S)—N-(8-amino-6-(4-(2-hydroxyethyl)pyridin-3-yl)-2,7-naphthyridin-3-yl)-2-(isothiazol-4-yl)cyclopropanecarboxamide and (1R,2R)—N-(8-amino-6-(4-(2-hydroxyethyl)pyridin-3-yl)-2,7-naphthyridin-3-yl)-2-(isothiazol-4-yl)cyclopropanecarboxamide

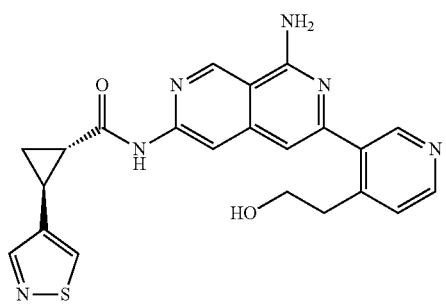

762

-continued

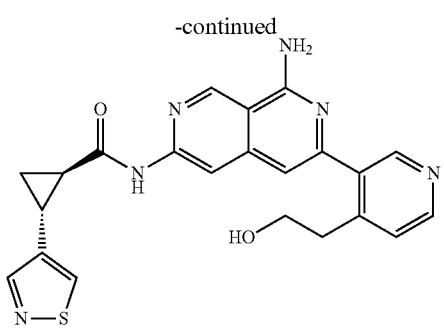

To a solution of trans-N-(8-amino-6-chloro-2,7-naphthyridin-3-yl)-2-(1,2-thiazol-4-yl)cyclopropane-1-carboxamide (350 mg, 1.01 mmol) in 10:1 dioxane/water (11 mL) was added 1H,3H,4H-[1,2]oxaborinino[3,4-c]pyridin-1-ol (605 mg, 4.06 mmol), 2nd Generation XPhos precatalyst (84 mg, 0.107 mmol), XPhos (50 mg, 0.105 mmol) and potassium carbonate (420 mg, 3.039 mmol). The resulting suspension was heated at 100° C. After 1 h, the reaction was concentrated under vacuum. Purification by flash column chromatography (10:1 dichloromethane/methanol) afforded racemic product. The enantiomers were separated by chiral SFC. Compound 245: LCMS (ESI): R$_T$ (min)=1.17, [M+H]$^+$=433.1, method=K-1; $^1$H NMR (300 MHz, DMSO-d$_6$) δ 11.00 (s, 1H), 9.37 (s, 1H), 8.76 (s, 1H), 8.49 (d, J=18.5 Hz, 3H), 8.26 (s, 1H), 7.40-7.28 (m, 3H), 6.97 (s, 1H), 4.77-4.66 (m, 1H), 3.58-3.52 (m, 2H), 2.93-2.85 (m, 2H), 2.57-2.50 (m, 1H), 2.48-2.35 (m, 1H), 1.59-1.39 (m, 2H). Compound 246: LCMS (ESI): R$_T$ (min)=1.17, [M+H]$^+$=433.1, method=K-1; $^1$H NMR (300 MHz, DMSO-d$_6$) δ 11.00 (s, 1H), 9.37 (s, 1H), 8.76 (s, 1H), 8.49 (d, J=18.5 Hz, 3H), 8.26 (s, 1H), 7.40-7.28 (m, 3H), 6.97 (s, 1H), 4.77-4.66 (m, 1H), 3.58-3.52 (m, 2H), 2.93-2.85 (m, 2H), 2.57-2.50 (m, 1H), 2.48-2.35 (m, 1H), 1.59-1.39 (m, 2H).

Example 194

(1S,2R)—N-[8-amino-6-(5-amino-4-methylpyridin-3-yl)-2,7-naphthyridin-3-yl]-2-(cyanomethyl)cyclopropane-1-carboxamide (Compound 247) and (1R,2S)—N-[8-amino-6-(5-amino-4-methylpyridin-3-yl)-2,7-naphthyridin-3-yl]-2-(cyanomethyl)cyclopropane-1-carboxamide (Compound 248)

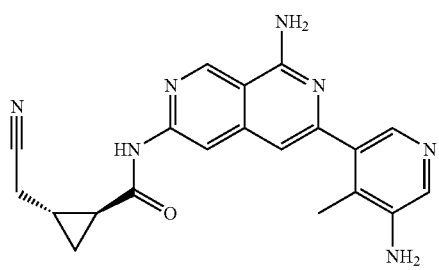

-continued

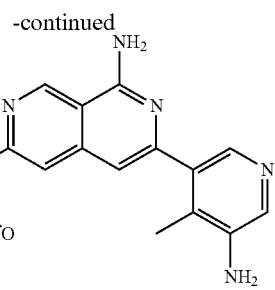

Step 1: Tert-butyl
N-(5-bromo-4-methylpyridin-3-yl)carbamate

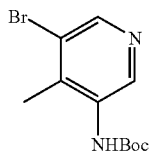

To an ice-cooled solution of 5-bromo-4-methylpyridin-3-amine (8.10 g, 43.31 mmol) in tetrahydrofuran (165 mL) was added NaHMDS (94.5 mL, 1M in tetrahydrofuran). After 30 min, Boc$_2$O (12.2 g, 55.90 mmol) was added, and the reaction was warmed to room temperature for 3.5 h. The reaction was then diluted with methanol and concentrated under vacuum. Purification by silica gel chromatography (3:1 dichloromethane/ethyl acetate) provided tert-butyl N-(5-bromo-4-methylpyridin-3-yl)carbamate (8.0 g, 64%) as a light yellow solid. LCMS (ESI): [M+H]$^+$=287.0.

Step 2: (5-[[(Tert-butoxy)carbonyl]amino]-4-methylpyridin-3-yl)boronic acid

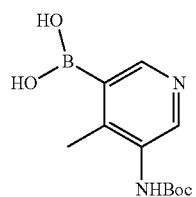

To a solution of tert-butyl N-(5-bromo-4-methylpyridin-3-yl)carbamate (5 g, 17.41 mmol) in 1,4-dioxane (200 mL) was added 4,4,5,5-tetramethyl-2-(tetramethyl-1,3,2-dioxaborolan-2-yl)-1,3,2-dioxaborolane (39 g, 153.58 mmol), Pd(dppf)Cl$_2$ (3.77 g, 5.15 mmol) and KOAc (5.1 g, 51.97 mmol). The resulting solution was heated at 100° C. After 6 h, the reaction was filtered, and the filtrate was concentrated under vacuum. The residue was dissolved in water, and the aqueous solution was basified to pH 10 with aqueous NaOH. The basic solution was washed with ethyl acetate. The aqueous was acidified to pH=4 with 1N HCl. The aqueous solution was concentrated under vacuum, and the resulting residue was suspended in 1:1 ethyl acetate/ethanol. The solids were filtered, and the filtrate was concentrated under vacuum to afford (5-[[(tert-butoxy)carbonyl]amino]-4-methylpyridin-3-yl)boronic acid (2.5 g, 57%) as a reddish oil. LCMS (ESI): [M+H]$^+$=253.2.

Step 3: (1S,2R)—N-[8-amino-6-(5-amino-4-methylpyridin-3-yl)-2,7-naphthyridin-3-yl]-2-(cyanomethyl)cyclopropane-1-carboxamide and (1R,2S)—N-[8-amino-6-(5-amino-4-methylpyridin-3-yl)-2,7-naphthyridin-3-yl]-2-(cyanomethyl)cyclopropane-1-carboxamide

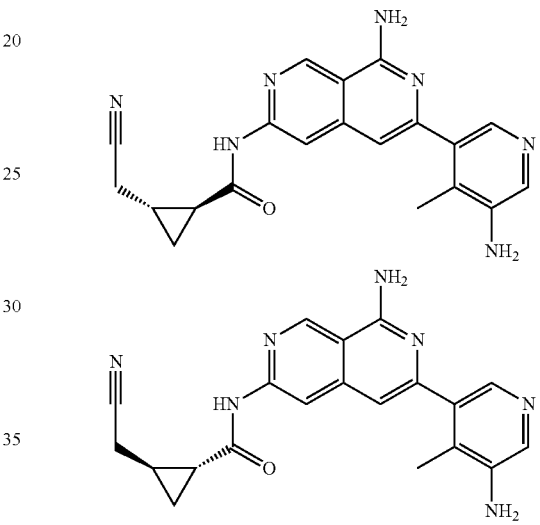

To a solution of trans-N-(8-amino-6-chloro-2,7-naphthyridin-3-yl)-2-(cyanomethyl)cyclopropane-1-carboxamide (200 mg, 0.66 mmol) in 1,4-dioxane (12 mL)/water (2 mL) was added (5-[[(tert-butoxy)carbonyl]amino]-4-methylpyridin-3-yl)boronic acid (834 mg, 3.31 mmol), potassium carbonate (320 mg, 2.32 mmol) and Pd(dppf)Cl$_2$ (120 mg, 0.16 mmol). The resulting solution was stirred for 3 h at 120° C. The reaction was filtered, and the filtrate was concentrated under vacuum. Purification by Prep-HPLC followed by chiral SFC provided enantiomerically pure products. Compound 247: LCMS (ESI): R$_T$ (min)=0.99, [M+H]$^+$=374.1, method=M; $^1$H NMR (300 MHz, DMSO-d$_6$) δ 11.03 (s, 1H), 9.35 (s, 1H), 8.20 (s, 1H), 7.93 (s, 1H), 7.76 (s, 1H), 7.26 (s, 2H), 6.82 (s, 1H), 5.14 (s, 2H), 2.73 (d, J=6.9 Hz, 2H), 2.13-2.06 (m, 4H), 1.60-1.54 (m, 1H), 1.15-1.11 (m, 1H), 0.98-0.95 (m, 1H). Compound 248: LCMS (ESI): R$_T$ (min)=1.58, [M+H]$^+$=374.1, method=M; $^1$H NMR (300 MHz, DMSO-d$_6$) δ 11.03 (s, 1H), 9.35 (s, 1H), 8.20 (s, 1H), 7.93 (s, 1H), 7.76 (s, 1H), 7.26 (s, 2H), 6.82 (s, 1H), 5.14 (s, 2H), 2.73 (d, J=6.9 Hz, 2H), 2.13-2.06 (m, 4H), 1.60-1.54 (m, 1H), 1.15-1.11 (m, 1H), 0.98-0.95 (m, 1H).

Example 195

(3R)-3-(4-[[8-amino-6-(4-methylpyridin-3-yl)-2,7-naphthyridin-3-yl]amino]-1H-pyrazol-1-yl)-1-methylpyrrolidin-2-one (Compound 249) and (3S)-3-(4-[[8-amino-6-(4-methylpyridin-3-yl)-2,7-naphthyridin-3-yl]amino]-1H-pyrazol-1-yl)-1-methylpyrrolidin-2-one (Compound 250)

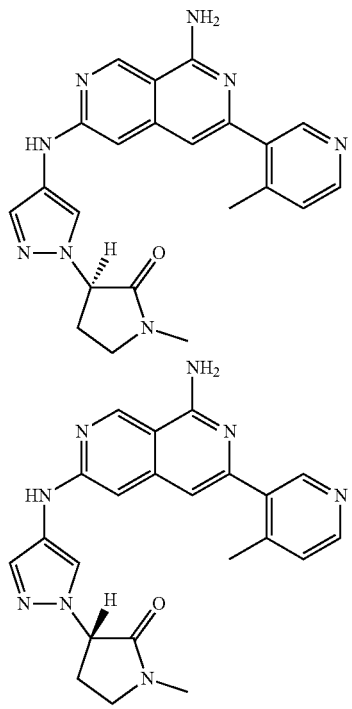

Step 1: 3-(4-bromo-1H-pyrazol-1-yl)-1-methylpyrrolidin-2-one

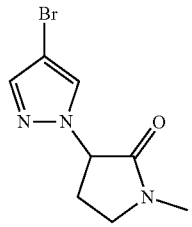

A suspension of 4-bromo-1H-pyrazole (1.00 g, 6.80 mmol), 3-bromo-1-methylpyrrolidin-2-one (1.33 g, 7.47 mmol), and potassium carbonate (1.88 g, 13.60 mmol) in N,N-dimethylformamide (12 mL) was heated at 60° C. After 1 h, the reaction was diluted with water (35 mL), and the solution was extracted with ethyl acetate (3×70 mL). The combined extracts were dried over $Na_2SO_4$, filtered, and concentrated under vacuum to afford 3-(4-bromo-1H-pyrazol-1-yl)-1-methylpyrrolidin-2-one as an off-white solid (930 mg, 56%). LCMS (ESI)[M+H]$^+$ 244, 246.

Step 2: 3-[4-[(8-[bis[(2,4-dimethoxyphenyl)methyl]amino]-6-(4-methylpyridin-3-yl)-2,7-naphthyridin-3-yl)amino]-1H-pyrazol-1-yl]-1-methylpyrrolidin-2-one

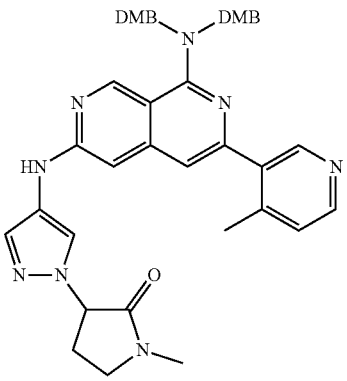

A solution of 1-N,1-N-bis[(2,4-dimethoxyphenyl)methyl]-3-(4-methylpyridin-3-yl)-2,7-naphthyridine-1,6-diamine (0.40 g, 0.725 mmol), 3-(4-bromo-1H-pyrazol-1-yl)-1-methylpyrrolidin-2-one (360 mg, 1.47 mmol), $Cs_2CO_3$ (1.42 g, 4.36 mmol), t-BuBrettPhos (179.95 mg, 0.37 mmol) and 3rd generation t-BuBrettPhos precatalyst (300 mg, 0.35 mmol) in dioxane (16.00 mL, 188.86 mmol) was heated at 100° C. After 2 h, the reaction was concentrated under vacuum, and the resulting residue was purified by silica gel chromatography (15:1 dichloromethane/methanol) to afford 3-[4-[(8-[bis[(2,4-dimethoxyphenyl)methyl]amino]-6-(4-methylpyridin-3-yl)-2,7-naphthyridin-3-yl)amino]-1H-pyrazol-1-yl]-1-methylpyrrolidin-2-one as a yellow solid (470 mg, 45%). LCMS (ESI) [M+H]$^+$=715.

Step 3: 3-(4-[[8-amino-6-(4-methylpyridin-3-yl)-2,7-naphthyridin-3-yl]amino]-1H-pyrazol-1-yl)-1-methylpyrrolidin-2-one

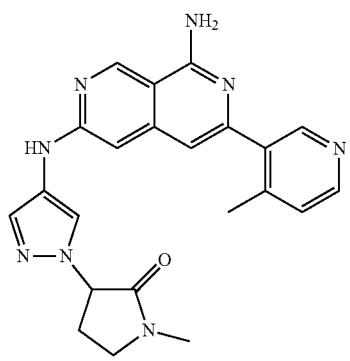 [SMILES: Cc1ccncc1-c1cc2cc(Nc3cnn(C4CCN(C)C4=O)c3)ncc2c(N)n1]

A solution of 3-[4-[(8-[[(3,4-dimethoxyphenyl)methyl][(3,5-dimethoxyphenyl)methyl]amino]-6-(4-methylpyridin-3-yl)-2,7-naphthyridin-3-yl)amino]-1H-pyrazol-1-yl]-1-methylpyrrolidin-2-one (250 mg, 0.35 mmol) in trifluoroacetic acid (25 mL) was heated at 70° C. for 2 h. The reaction was concentrated, and the resulting residue was purified by silica gel chromatography (15:1 dichloromethane/methanol) to afford the titled compound (110 mg, 74%) as a yellow solid. LCMS (ESI)[M+H]$^+$ 415.2.

Step 4: (3R)-3-(4-[[8-amino-6-(4-methylpyridin-3-yl)-2,7-naphthyridin-3-yl]amino]-1H-pyrazol-1-yl)-1-methylpyrrolidin-2-one and (3S)-3-(4-[[8-amino-6-(4-methylpyridin-3-yl)-2,7-naphthyridin-3-yl]amino]-1H-pyrazol-1-yl)-1-methylpyrrolidin-2-one

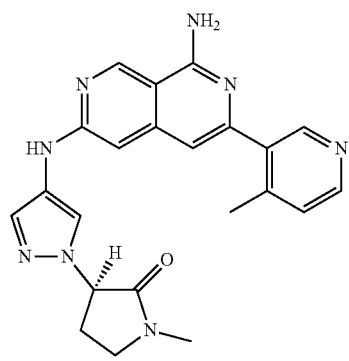

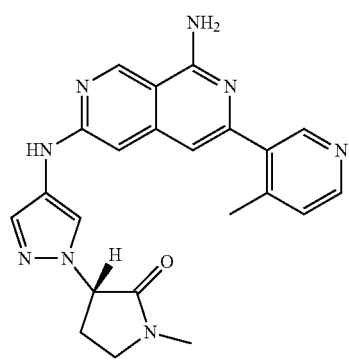

Racemic 3-(4-[[8-amino-6-(4-methylpyridin-3-yl)-2,7-naphthyridin-3-yl]amino]-1H-pyrazol-1-yl)-1-methylpyrrolidin-2-one was separated by chiral SFC. Compound 249: LCMS (ESI): $R_T$ (min)=1.01, [M+H]$^+$=415.2, method=K-1; $^1$H NMR (300 MHz, DMSO-d$_6$) δ 9.23 (s, 1H), 8.94 (s, 1H), 8.53 (s, 1H), 8.42 (d, J=5.2 Hz, 1H), 7.99 (s, 1H), 7.54 (s, 1H), 7.29 (d, J=5.2 Hz, 1H), 6.76 (s, 2H), 6.76 (s, 1H), 6.66 (s, 1H), 5.11-5.07 (m, 1H), 3.53-3.47 (m, 1H), 3.44-3.38 (m, 1H), 2.82 (s, 3H), 2.60-2.57 (m, 1H), 2.50-2.43 (m, 1H), 3.40 (m, 3H). Compound 250: LCMS (ESI): $R_T$(min)=1.01, [M+H]$^+$=415.2, method=K-1; $^1$H NMR (300 MHz, DMSO-d$_6$) δ 9.23 (s, 1H), 8.94 (s, 1H), 8.53 (s, 1H), 8.42 (d, J=5.2 Hz, 1H), 7.99 (s, 1H), 7.54 (s, 1H), 7.29 (d, J=5.2 Hz, 1H), 6.76 (s, 2H), 6.76 (s, 1H), 6.66 (s, 1H), 5.11-5.07 (m, 1H), 3.53-3.47 (m, 1H), 3.44-3.38 (m, 1H), 2.82 (s, 3H), 2.60-2.57 (m, 1H), 2.50-2.43 (m, 1H), 3.40 (m, 3H).

Example 196

(3R)-3-(4-[[8-amino-6-(4-methylpyridin-3-yl)-2,7-naphthyridin-3-yl]amino]-1H-pyrazol-1-yl)-1-methylpiperidin-2-one (Compound 251) and (3S)-3-(4-[[8-amino-6-(4-methylpyridin-3-yl)-2,7-naphthyridin-3-yl]amino]-1H-pyrazol-1-yl)-1-methylpiperidin-2-one (Compound 252)

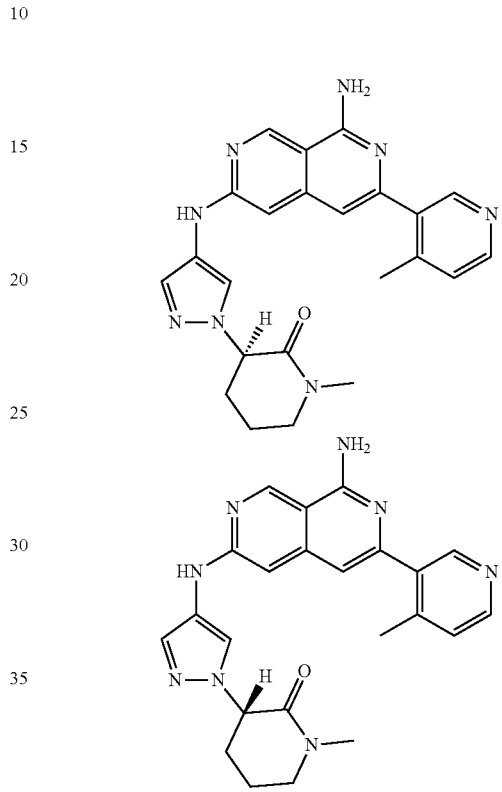

The title compounds were prepared using a procedure as described for (3R)-3-(4-[[8-amino-6-(4-methylpyridin-3-yl)-2,7-naphthyridin-3-yl]amino]-1H-pyrazol-1-yl)-1-methylpyrrolidin-2-one (Compound 249). The enantiomers were isolated by chiral SFC. Compound 251: LCMS (ESI): [M+H]$^+$=429.3, $R_T$ (min)=1.04, Method=K-1; $^1$H NMR (400 MHz, DMSO-d$_6$) δ 9.22 (s, 1H), 8.92 (s, 1H), 8.54 (s, 1H), 8.42 (d, J=5.0 Hz, 1H), 7.91 (s, 1H), 7.49 (s, 1H), 7.29 (d, J=5.0 Hz, 1H), 7.10 (s, 2H), 6.76 (s, 1H), 6.65 (s, 1H), 4.95-4.92 (m, 1H), 3.44-3.42 (m, 1H), 3.32 (s, 1H), 2.87 (s, 3H), 2.41 (s, 3H), 2.37-2.27 (m, 1H), 2.25-2.13 (m, 1H), 2.02-2.00 (m, 1H), 1.92-1.90 (m, 1H). Compound 252: LCMS (ESI): [M+H]$^+$=429.2, $R_T$(min)=1.05, Method=K-1; $^1$H NMR (400 MHz, DMSO-d$_6$) δ 9.22 (s, 1H), 8.92 (s, 1H), 8.54 (s, 1H), 8.42 (d, J=5.0 Hz, 1H), 7.91 (s, 1H), 7.49 (s, 1H), 7.29 (d, J=5.0 Hz, 1H), 7.10 (s, 2H), 6.76 (s, 1H), 6.65 (s, 1H), 4.95-4.92 (m, 1H), 3.44-3.42 (m, 1H), 3.32 (s, 1H), 2.87 (s, 3H), 2.41 (s, 3H), 2.37-2.27 (m, 1H), 2.25-2.13 (m, 1H), 2.02-2.00 (m, 1H), 1.92-1.90 (m, 1H).

Example 197

(1R,2R)—N-[8-amino-6-[4-(2-hydroxyethyl)pyridin-3-yl]-2,7-naphthyridin-3-yl]-2-(pyridin-3-yl)cyclopropane-1-carboxamide (Compound 253) and (1S,2S)—N-[8-amino-6-[4-(2-hydroxyethyl)pyridin-3-yl]-2,7-naphthyridin-3-yl]-2-(pyridin-3-yl)cyclopropane-1-carboxamide (Compound 254)

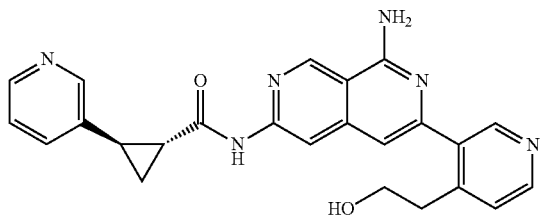

Step 1: 1H,3H,4H-[1,2]oxaborinino[3,4-c]pyridin-1-ol

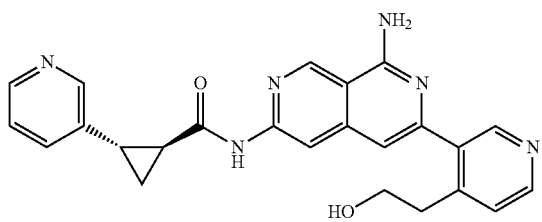

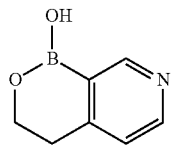 [SMILES: OB1OCCc2ccncc21]

A mixture of 2-(2-bromopyridin-3-yl)ethan-1-ol (5.0 g, 24.7 mmol), 4,4,5,5-tetramethyl-2-(tetramethyl-1,3,2-dioxaborolan-2-yl)-1,3,2-dioxaborolane (25.1 g, 98.8 mmol), KOAc (7.28 g, 74.17 mmol), Pd(dppf)Cl$_2$ (1.8 g, 2.46 mmol) in dioxane (120 mL) was heated at 100° C. After 1 h, the reaction was filtered, and the filtrate was concentrated under vacuum. The resulting residue was dissolved in water and the pH of the solution was adjusted to 7-8 with aqueous NaOH. The basic solution was washed with ethyl acetate. The aqueous layer was then acidified to pH 5-6 with HCl. The acidic solution was concentrated under vacuum. The resulting residue was suspended in 1:1 ethyl acetate/ethanol and filtered. The filtrate was concentrated under vacuum to afford crude 1H,3H,4H-[1,2]oxaborinino[3,4-c]pyridin-1-ol (3.34 g, 91%) as a brown oil. LCMS (ESI): [M+H]$^+$=150.1

Step 2: (1R,2R)—N-[8-amino-6-[4-(2-hydroxyethyl)pyridin-3-yl]-2,7-naphthyridin-3-yl]-2-(pyridin-3-yl)cyclopropane-1-carboxamide and (1S,2S)—N-[8-amino-6-[4-(2-hydroxyethyl)pyridin-3-yl]-2,7-naphthyridin-3-yl]-2-(pyridin-3-yl)cyclopropane-1-carboxamide

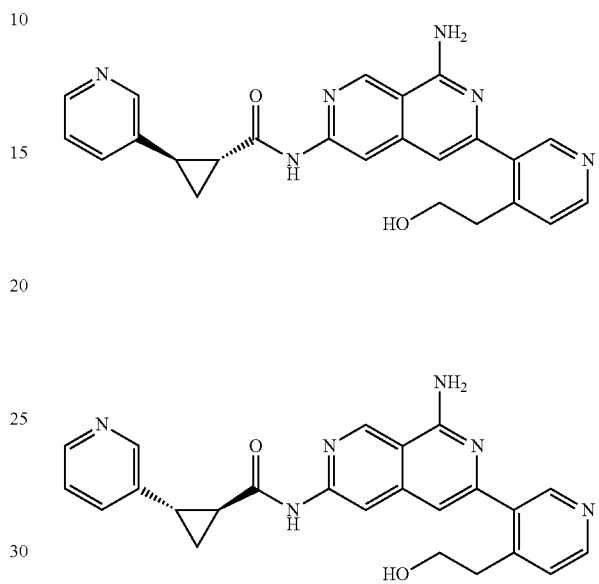

A mixture of trans-N-(8-amino-6-chloro-2,7-naphthyridin-3-yl)-2-(pyridin-3-yl)cyclopropane-1-carboxamide (0.40 g, 1.17 mmol), 1H,3H,4H-[1,2]oxaborinino[3,4-c]pyridin-1-ol (701 mg, 4.70 mmol), XPhos palladium(II) biphenyl-2-amine chloride (93 mg, 0.11 mmol), X-Phos (56 mg, 0.11 mmol), and potassium carbonate (489 mg, 3.53 mmol) in 5:1 dioxane/water (12 mL) was heated at 100° C. for 1 h. The reaction mixture was concentrated under vacuum, and the crude material was purified by Flash-Prep-HPLC to afford racemic product. The enantiomers were separated by chiral SFC. Compound 253: LCMS (ESI): [M+H]$^+$=427.2, R$_T$ (min)=1.88, Method=M; $^1$H NMR (400 MHz, DMSO-d$_6$) δ 11.03 (s, 1H), 9.38 (s, 1H), 8.53 (s, 1H), 8.52-8.51 (m, 1H), 8.48 (d, J=6 Hz, 1H), 8.45-8.42 (m, 1H), 8.28 (s, 1H), 7.59-7.55 (m, 1H), 7.43-7.32 (m, 4H), 6.99 (s, 1H), 4.79 (t, J=6 Hz, 1H), 3.62-3.55 (m, 2H), 2.94 (t, J=6 Hz, 2H), 2.55-2.45 (m, 2H), 1.60-1.46 (m, 2H). Compound 254: LCMS (ESI): [M+H]$^+$=427.2, R$_T$ (min)=1.24, Method=M; $^1$H NMR (400 MHz, DMSO-d$_6$) δ 11.03 (s, 1H), 9.38 (s, 1H), 8.53 (s, 1H), 8.52-8.51 (m, 1H), 8.48 (d, J=6 Hz, 1H), 8.45-8.42 (m, 1H), 8.28 (s, 1H), 7.59-7.55 (m, 1H), 7.43-7.32 (m, 4H), 6.99 (s, 1H), 4.79 (t, J=6 Hz, 1H), 3.62-3.55 (m, 2H), 2.94 (t, J=6 Hz, 2H), 2.55-2.45 (m, 2H), 1.60-1.46 (m, 2H).

Example 198

(exo)-N-[8-amino-6-(4-methylpyridin-3-yl)-2,7-naphthyridin-3-yl]-3-(oxetan-3-yl)-3-azabicyclo[3.1.0]hexane-6-carboxamide (Compound 255)

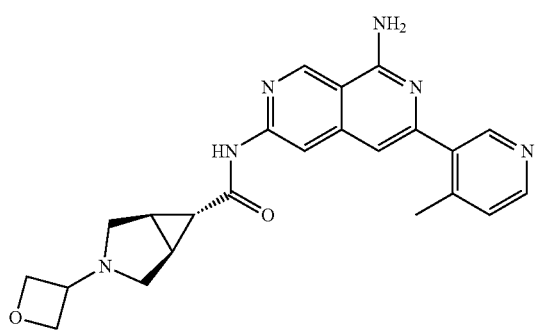 [SMILES: Cc1ccncc1-c1cc2cc(NC(=O)[C@H]3[C@@H]4CN(C5COC5)C[C@@H]43)ncc2c(N)n1]

Step 1: tert-butyl (exo)-6-[(6,8-dichloro-2,7-naphthyridin-3-yl)carbamoyl]-3-azabicyclo[3.1.0]hexane-3-carboxylate

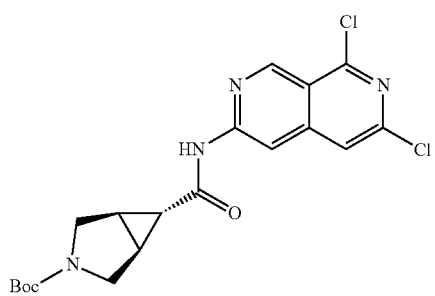 [SMILES: CC(C)(C)OC(=O)N1C[C@@H]2[C@H](C1)[C@H]2C(=O)Nc1cc2cc(Cl)nc(Cl)c2cn1]

A mixture of (exo)-3-[(tert-butoxy)carbonyl]-3-azabicyclo[3.1.0]hexane-6-carboxylic acid (2.0 g, 8.8 mmol), 6,8-dichloro-2,7-naphthyridin-3-amine hydrochloride (1.8 g, 7.2 mmol), pyridine (10 mL), and POCl₃ (1.67 g, 10.891 mmol) in dichloromethane (100 mL) was stirred for 1 h at room temperature. The reaction was quenched by the slow addition of saturated aqueous sodium bicarbonate solution. The resulting solution was extracted with dichloromethane, and the combined organic was concentrated under vacuum. Purification by flash column chromatography (10:1 dichloromethane/methanol) afforded tert-butyl (exo)-6-[(6,8-dichloro-2,7-naphthyridin-3-yl)carbamoyl]-3-azabicyclo[3.1.0]hexane-3-carboxylate (2 g, 66%) as a yellow solid. LCMS (ESI): [M+H]⁺=423.1.

Step 2: tert-butyl(1R,5S,6R)-6-[(8-amino-6-chloro-2,7-naphthyridin-3-yl)carbamoyl]-3-azabicyclo[3.1.0]hexane-3-carboxylate

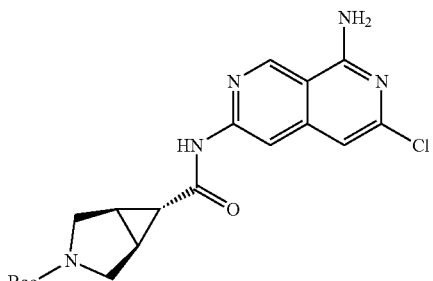

A mixture of tert-butyl (1R,5S,6R)-6-[(6,8-dichloro-2,7-naphthyridin-3-yl)carbamoyl]-3-azabicyclo[3.1.0]hexane-3-carboxylate (2 g, 4.725 mmol) and ammonium hydroxide (20 mL) in dioxane (20 mL) was heated at 90° C. for 3 h. The reaction was concentrated to afford crude tert-butyl (exo)-6-[(8-amino-6-chloro-2,7-naphthyridin-3-yl)carbamoyl]-3-azabicyclo[3.1.]hexane-3-carboxylate (2 g) as a yellow solid. LCMS (ESI): [M+H]⁺=404.1.

Step 3: tert-butyl (exo)-6-[[8-amino-6-(4-methylpyridin-3-yl)-2,7-naphthyridin-3-yl]carbamoyl]-3-azabicyclo[3.1.0]hexane-3-carboxylate

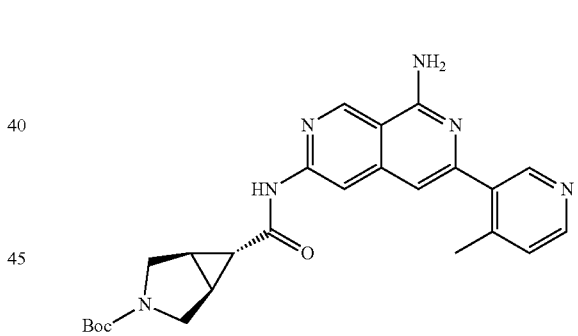

A mixture of (4-methylpyridin-3-yl)boronic acid (510 mg, 3.72 mmol), tert-butyl (exo)-6-[(8-amino-6-chloro-2,7-naphthyridin-3-yl)carbamoyl]-3-azabicyclo[3.1.0]hexane-3-carboxylate (0.50 g, 1.24 mmol), Pd(dppf)Cl₂ (90 mg, 0.12 mmol) and sodium carbonate (400 mg, 3.77 mmol) in 10:1 dioxane/water (16.5 mL) heated at 100° C. for 12 h under nitrogen. The reaction was filtered, and the filtrate was concentrated. Purification by flash column chromatography (10:1 dichloromethane/methanol) yielded tert-butyl (exo)-6-[[8-amino-6-(4-methylpyridin-3-yl)-2,7-naphthyridin-3-yl]carbamoyl]-3-azabicyclo[3.1.0]hexane-3-carboxylate (380 mg, 67%) as a yellow solid. LCMS (ESI): [M+H]=461.2.

Step 4: (exo)-N-[8-amino-6-(4-methylpyridin-3-yl)-2,7-naphthyridin-3-yl]-3-azabicyclo[3.1.0]hexane-6-carboxamide

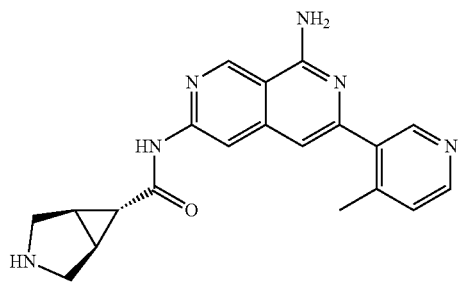 [SMILES: Cc1ccncc1-c1cc2cc(NC(=O)[C@H]3[C@@H]4CNC[C@@H]43)ncc2c(N)n1]

A solution of tert-butyl(exo)-6-[[8-amino-6-(4-methylpyridin-3-yl)-2,7-naphthyridin-3-yl]carbamoyl]-3-azabicyclo[3.1.0]hexane-3-carboxylate (380 mg, 0.825 mmol) and CF$_3$COOH (4 mL) in dichloromethane (20 mL) was stirred for 1 h at room temperature. The reaction was concentrated to afford crude (exo)-N-[8-amino-6-(4-methylpyridin-3-yl)-2,7-naphthyridin-3-yl]-3-azabicyclo[3.1.0]hexane-6-carboxamide (0.3 g) as a yellow oil. LCMS (ESI): [M+H]$^+$=361.2.

Step 5: (exo)-N-[8-amino-6-(4-methylpyridin-3-yl)-2,7-naphthyridin-3-yl]-3-(oxetan-3-yl)-3-azabicyclo[3.1.0]hexane-6-carboxamide

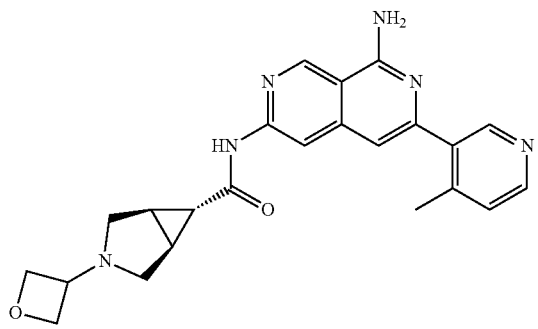 [SMILES: Cc1ccncc1-c1cc2cc(NC(=O)[C@H]3[C@@H]4CN(C5COC5)C[C@@H]43)ncc2c(N)n1]

To a solution of (exo)-N-[8-amino-6-(4-methylpyridin-3-yl)-2,7-naphthyridin-3-yl]-3-azabicyclo[3.1.0]hexane-6-carboxamide (0.30 g, 0.83 mmol), oxetan-3-one (180 mg, 2.5 mmol) in methanol (20 mL) was added NaBH$_3$CN (157 mg, 2.5 mmol) at room temperature. After 2 h, the reaction was concentrated under vacuum, and the resulting residue was purified by Prep-HPLC to afford (exo)-N-[8-amino-6-(4-methylpyridin-3-yl)-2,7-naphthyridin-3-yl]-3-(oxetan-3-yl)-3-azabicyclo[3.1.0]hexane-6-carboxamide (125 mg, 36%) as a white solid. LCMS (ESI): R$_T$(min)=1.25, [M+H]$^+$=417.2, method=K-1; $^1$H NMR (300 MHz, DMSO-d$_6$) δ 10.79 (s, 1H), 9.35 (s, 1H), 8.57 (s, 1H), 8.44 (d, J=5.0 Hz, 1H), 8.23 (s, 1H), 7.48-7.21 (m, 3H), 6.96 (s, 1H), 4.56 (t, J=6.6 Hz, 2H), 4.44 (t, J=6.0 Hz, 2H), 3.73 (m, 1H), 3.05 (d, J=8.9 Hz, 2H), 2.47-2.42 (m, 3H), 2.41 (s, 3H), 1.95 (t, J=2.2 Hz, 2H).

Example 199

2-[[8-amino-6-(4-methylpyridin-3-yl)-2,7-naphthyridin-3-yl]amino]-6-methyl-4H,5H,6H,7H,8H-pyrazolo[1,5-d][1,4]diazepin-7-one (Compound 256)

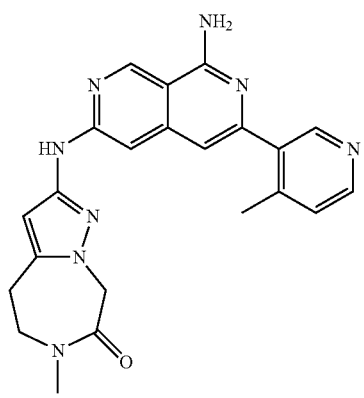 [SMILES: Cc1ccncc1-c1cc2cc(Nc3cc4n(n3)CC(=O)N(C)CC4)ncc2c(N)n1]

Step 1: methyl 3-bromo-1-(oxan-2-yl)-1H-pyrazole-5-carboxylate

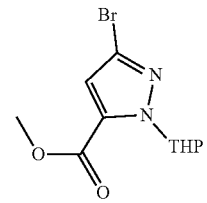

A mixture of methyl 3-bromo-1H-pyrazole-5-carboxylate (10.0 g, 48.8 mmol), TsOH (830 mg, 4.82 mmol), 3,4-dihydro-2H-pyran (12.2 g, 145 mmol) in ethyl acetate (150 mL) was refluxed for 4 h. The reaction mixture was concentrated, and the resulting residue was purified by flash chromatography (1:3 ethyl acetate/petroleum ether) to afford methyl 3-bromo-1-(oxan-2-yl)-1H-pyrazole-5-carboxylate (8 g, 57%) as an oil. LCMS (ESI): [M+H]$^+$=289.0.

Step 2: [3-bromo-1-(oxan-2-yl)-1H-pyrazol-5-yl]methanol

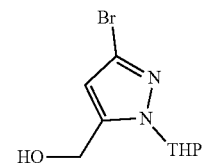

To an ice-cooled solution of methyl 3-bromo-1-(oxan-2-yl)-1H-pyrazole-5-carboxylate (7.4 g, 25.6 mmol) in dichloromethane (100 mL) was added diisobutylaluminum hydride (102 mL, 608 mmol) dropwise under nitrogen. After 1 h, the reaction was diluted with H$_2$O (100 mL), and the resulting solution was extracted with dichloromethane. The combined organic was dried over Na$_2$SO$_4$, filtered, and concentrated under vacuum to provide crude [3-bromo-1-(oxan-2-yl)-1H-pyrazol-5-yl]methanol (5.2 g) as a light yellow oil. LCMS (ESI): [M+H]⁺=261.0.

Step 3: [3-bromo-1-(oxan-2-yl)-1H-pyrazol-5-yl] methyl methanesulfonate

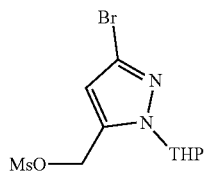

To an ice-cooled solution of [3-bromo-1-(oxan-2-yl)-1H-pyrazol-5-yl]methanol (5.5 g, 21 mmol), triethylamine (6.38 g, 63.0 mmol) in dichloromethane (100 mL) was added MsCl (5.3 g, 46 mmol). After 15 min, the reaction was diluted with water, and resulting solution was extracted with dichloromethane. The collected organic was dried over Na₂SO₄, filtered, and concentrated under vacuum to yield crude [3-bromo-1-(oxan-2-yl)-1H-pyrazol-5-yl]methyl methanesulfonate (6.3 g) as a colorless oil. LCMS (ESI): [M+H]⁺=339.0.

Step 4: 2-[3-bromo-1-(oxan-2-yl)-1H-pyrazol-5-yl] acetonitrile

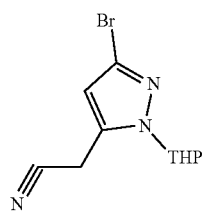

A mixture of [3-bromo-1-(oxan-2-yl)-1H-pyrazol-5-yl] methyl methanesulfonate (4.0 g, 11.8 mmol) and KCN (2.3 g, 35 mmol) in DMSO (100 mL) was heated at 50° C. After 2 h, the reaction was diluted with H₂O (500 mL), and the resulting solution was extracted with ethyl acetate. The combined extract was dried over Na₂SO₄, filtered, and concentrated under vacuum. Purification by flash column chromatography (10:1 dichloromethane/methanol) afforded 2-[3-bromo-1-(oxan-2-yl)-1H-pyrazol-5-yl]acetonitrile (2.1 g, 66%) as colorless oil. LCMS (ESI): [M+H]⁺=270.0.

Step 5: 2-(3-bromo-1H-pyrazol-5-yl)acetonitrile

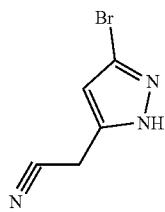

A solution of 2-[3-bromo-1-(oxan-2-yl)-1H-pyrazol-5-yl] acetonitrile (2.2 g, 8.1 mmol) in dichloromethane (30 mL) was added trifluoroacetic acid (6 mL) at room temperature. After 2 h, the reaction was concentrated, and the resulting residue was diluted with dichloromethane (20 mL). The solution was basified to pH=8 with 7 M NH₃ in methanol. The solution was concentrated under vacuum, and the crude product was purified by flash column chromatography (10:1 dichloromethane/methanol) to afford 2-(3-bromo-1H-pyrazol-5-yl)acetonitrile (1.44 g, 95%) as a light yellow oil. LCMS (ESI): [M+H]⁺=186.0.

Step 6: methyl 2-[3-bromo-5-(cyanomethyl)-1H-pyrazol-1-yl]acetate

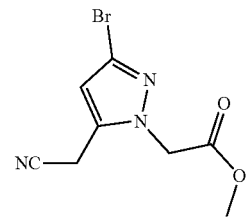

To a suspension of 2-(3-bromo-1H-pyrazol-5-yl)acetonitrile (1.66 g, 8.92 mmol), tetrabutylammonium iodide (328 mg, 0.88 mmol), potassium carbonate (1.2 g, 8.68 mmol) in N,N-dimethylformamide (80 mL) was added methyl 2-chloroacetate (961 mg, 8.85 mmol) at room temperature. After 1 h, the reaction mixture was diluted with H₂O (100 mL), and the resulting solution was extracted with ethyl acetate. The combined organics were concentrated. Purification by Flash-Prep-HPLC afforded methyl 2-[3-bromo-5-(cyanomethyl)-1H-pyrazol-1-yl]acetate (760 mg, 33%) as a colorless oil. LCMS (ESI): [M+H]⁺=258.0.

Step 7: 2-bromo-4H,5H,6H,7H,8H-pyrazolo[1,5-d][1,4]diazepin-7-one

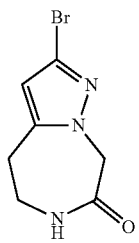 [SMILES: O=C1Cn2nc(Br)cc2CCN1]

A mixture of methyl 2-[3-bromo-5-(cyanomethyl)-1H-pyrazol-1-yl]acetate (394 mg, 1.52 mmol) and PtO₂ (173 mg, 0.762 mmol) in methanol (20 mL) was stirred for 2 h at room temperature under hydrogen (2 atm). The reaction was filtered, and the filtrate was concentrated. Purification by flash column chromatography (10:1 dichloromethane/methanol) to give 2-bromo-4H,5H,6H,7H,8H-pyrazolo[1,5-d][1,4]diazepin-7-one (155 mg, 44%) as a white solid. LCMS (ESI): [M+H]⁺=230.0.

Step 8: 2-bromo-6-methyl-4H,5H,6H,7H,8H-pyrazolo[1,5-d][1,4]diazepin-7-one

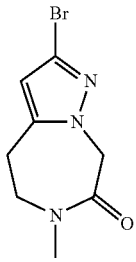

To a mixture of 2-bromo-4H-pyrazolo[1,5-d][1,4]diazepin-7-one (105 mg, 0.45 mmol) and t-BuOK (56 mg, 0.50 mmol) in tetrahydrofuran (5 mL) was added CH₃I (98 mg, 0.69 mmol) at room temperature. After 2 h, the solution was concentrated under vacuum. Purification by flash column chromatography (10:1 dichloromethane/methanol) afforded 2-bromo-6-methyl-4H-pyrazolo[1,5-d][1,4]diazepin-7-one (90 mg, 81%) as a white solid. LCMS (ESI): [M+H]⁺=244.0

Step 9: 2-[(8-[bis[(2,4-dimethoxyphenyl)methyl]amino]-6-(4-methylpyridin-3-yl)-2,7-naphthyridin-3-yl)amino]-6-methyl-4H-pyrazolo[1,5-d][1,4]diazepin-7-one

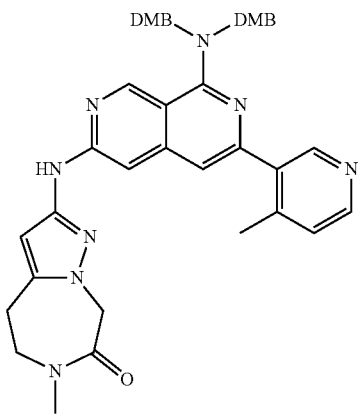

A suspension of 1-N,1-N-bis[(2,4-dimethoxyphenyl)methyl]-3-(4-methylpyridin-3-yl)-2,7-naphthyridine-1,6-diamine (380 mg, 0.68 mmol), 2-bromo-6-methyl-4H-pyrazolo[1,5-d][1,4]diazepin-7-one (112 mg, 0.45 mmol), 3rd generation t-BuBrettPhos precatalyst (157 mg, 0.18 mmol), t-BuBrettPhos (87 mg, 0.17 mmol) and Cs₂CO₃ (747 mg, 2.29 mmol) in dioxane (8 mL) was heated at 130° C. for 4 h. The reaction mixture was concentrated under vacuum, and the crude product was purified by flash column chromatography (10:1 dichloromethane/methanol) to afford 2-[(8-[bis[(2,4-dimethoxyphenyl)methyl]amino]-6-(4-methylpyridin-3-yl)-2,7-naphthyridin-3-yl)amino]-6-methyl-4H-pyrazolo[1,5-d][1,4]diazepin-7-one (0.20 g, 41%) as a light yellow oil. LCMS (ESI): [M+H]⁺=715.3.

Step 10: 2-[[8-amino-6-(4-methylpyridin-3-yl)-2,7-naphthyridin-3-yl]amino]-6-methyl-4H-pyrazolo[1,5-d][1,4]diazepin-7-one

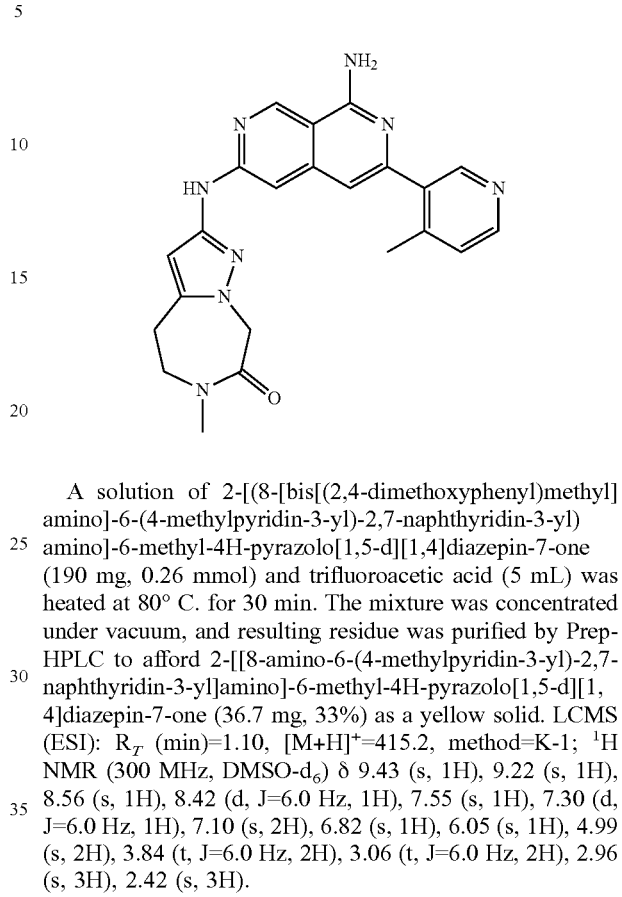

A solution of 2-[(8-[bis[(2,4-dimethoxyphenyl)methyl]amino]-6-(4-methylpyridin-3-yl)-2,7-naphthyridin-3-yl)amino]-6-methyl-4H-pyrazolo[1,5-d][1,4]diazepin-7-one (190 mg, 0.26 mmol) and trifluoroacetic acid (5 mL) was heated at 80° C. for 30 min. The mixture was concentrated under vacuum, and resulting residue was purified by Prep-HPLC to afford 2-[[8-amino-6-(4-methylpyridin-3-yl)-2,7-naphthyridin-3-yl]amino]-6-methyl-4H-pyrazolo[1,5-d][1,4]diazepin-7-one (36.7 mg, 33%) as a yellow solid. LCMS (ESI): R$_T$ (min)=1.10, [M+H]⁺=415.2, method=K-1; ¹H NMR (300 MHz, DMSO-d₆) δ 9.43 (s, 1H), 9.22 (s, 1H), 8.56 (s, 1H), 8.42 (d, J=6.0 Hz, 1H), 7.55 (s, 1H), 7.30 (d, J=6.0 Hz, 1H), 7.10 (s, 2H), 6.82 (s, 1H), 6.05 (s, 1H), 4.99 (s, 2H), 3.84 (t, J=6.0 Hz, 2H), 3.06 (t, J=6.0 Hz, 2H), 2.96 (s, 3H), 2.42 (s, 3H).

Example 200

6-N-[1-(2,2-difluoroethyl)-1H-pyrazol-4-yl]-3-(4-methylpyridin-3-yl)-2,7-naphthyridine-1,6-diamine (Compound 257)

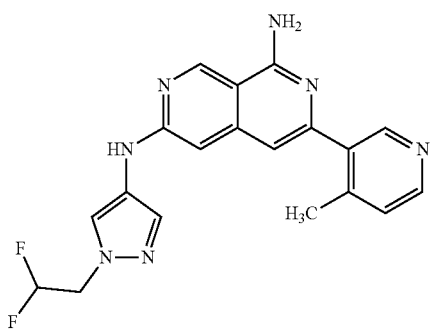 [SMILES: Cc1ccncc1-c1cc2cc(Nc3cnn(CC(F)F)c3)ncc2c(N)n1]

The title compound was prepared using a procedure as described for (3R)-3-(4-[[8-amino-6-(4-methylpyridin-3-yl)-2,7-naphthyridin-3-yl]amino]-1H-pyrazol-1-yl)-1-methylpyrrolidin-2-one (Compound 249) LCMS (ESI): R$_T$ (min)=1.05, [M+H]⁺=382.2, method=M; ¹H NMR (300 MHz, CD₃OD) δ 9.22-9.15 (m, 1H), 8.51 (s, 1H), 8.43 (d, J=5.1 Hz, 1H), 8.04 (s, 1H), 7.67 (d, J=0.8 Hz, 1H), 7.44-7.36 (m, 1H), 6.75 (dd, J=13.6, 0.9 Hz, 2H), 6.49-5.95 (m, 1H), 4.58 (td, J=14.4, 3.9 Hz, 2H), 2.45 (s, 3H).

Example 201

N-(8-amino-6-(4-methylpyridin-3-yl)-5-(1H-pyrazol-4-yl)-2,7-naphthyridin-3-yl)cyclopropanecarboxamide (Compound 258)

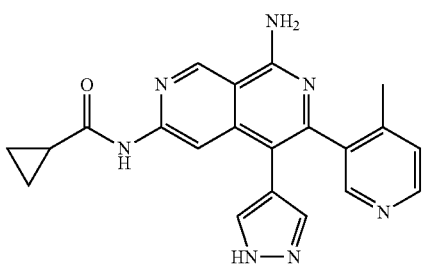 [SMILES: Cc1ccncc1-c1nc(N)c2cnc(NC(=O)C3CC3)cc2c1-c1cn[nH]c1]

Step 1: N-(8-amino-6-(4-methylpyridin-3-yl)-2,7-naphthyridin-3-yl)cyclopropanecarboxamide

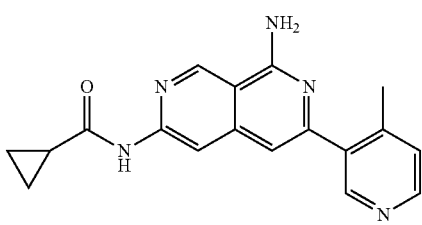 [SMILES: Cc1ccncc1-c1cc2cc(NC(=O)C3CC3)ncc2c(N)n1]

A mixture of N-(8-amino-6-chloro-2,7-naphthyridin-3-yl)cyclopropanecarboxamide (0.50 g, 1.9 mmol), (4-methylpyridin-3-yl)boronic acid (391 mg, 2.86 mmol), XPhos (181 mg, 0.38 mmol), XPhos-PdCl-2nd G (144 mg, 0.19 mmol) and potassium carbonate (787 mg, 5.69 mmol) in 10:1 1,4-dioxane/water (11 mL) was heated at 100° C. for 1 h. The reaction was filtered, and the filtrate was concentrated under vacuum. Purification by silica gel chromatography (20:1 dichloromethane/methanol) afforded N-[8-amino-6-(4-methylpyridin-3-yl)-2,7-naphthyridin-3-yl]cyclopropanecarboxamide (534 mg, 88%) as a brown solid. LCMS (ESI): [M+H]$^+$=320.1.

Step 2: N-(8-amino-5-bromo-6-(4-methylpyridin-3-yl)-2,7-naphthyridin-3-yl)cyclopropanecarboxamide

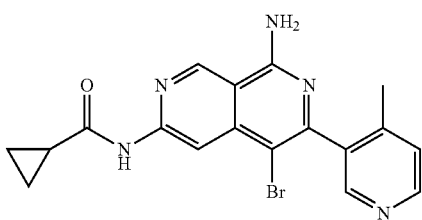 [SMILES: Cc1ccncc1-c1nc(N)c2cnc(NC(=O)C3CC3)cc2c1Br]

A mixture of N-[8-amino-6-(4-methylpyridin-3-yl)-2,7-naphthyridin-3-yl]cyclopropanecarboxamide (524 mg, 1.64 mmol), NBS (350 mg, 1.97 mmol) and dichloromethane (20 mL) was stirred for 30 min at 25° C. The reaction mixture was extracted with dichloromethane, the combined extracts were dried over anhydrous sodium sulfate, filtered, and concentrated under vacuum. Purification by silica gel chromatography (20:1 dichloromethane/methanol) afforded N-[8-amino-5-bromo-6-(4-methylpyridin-3-yl)-2,7-naphthyridin-3-yl]cyclopropanecarboxamide (427 mg, 65%) as a brown solid. LCMS (ESI): [M+H]$^+$=398.2.

Step 3: N-(8-amino-6-(4-methylpyridin-3-yl)-5-(1H-pyrazol-4-yl)-2,7-naphthyridin-3-yl)cyclopropanecarboxamide

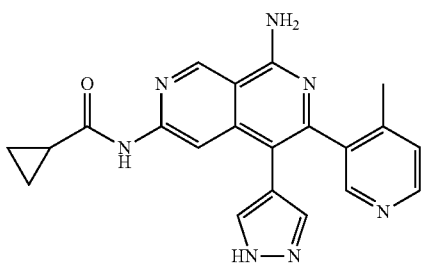 [SMILES: Cc1ccncc1-c1nc(N)c2cnc(NC(=O)C3CC3)cc2c1-c1cn[nH]c1]

A mixture of N-[8-amino-5-bromo-6-(4-methylpyridin-3-yl)-2,7-naphthyridin-3-yl]cyclopropanecarboxamide (0.10 g, 0.25 mmol), (1H-pyrazol-4-yl)boronic acid (42 mg, 0.38 mmol), Pd(dppf)Cl$_2$ (19 mg, 0.03 mmol), and potassium carbonate (104 mg, 0.75 mmol) in 4:1 dioxane/water (10 mL) was heated at 100° C. After 15 h, the reaction was filtered, and the filtrate was concentrated under vacuum. Purification by Prep-HPLC afforded N-[8-amino-6-(4-methylpyridin-3-yl)-5-(1H-pyrazol-4-yl)-2,7-naphthyridin-3-yl]cyclopropanecarboxamide (27.6 mg, 29%) as a green solid. LCMS (ESI): R$_T$(min)=0.91, [M+H]$^+$=386.2, method=K-1; $^1$H NMR (400 MHz, DMSO-d$_6$) δ 12.72 (s, 1H), 10.95 (s, 1H), 9.41 (d, J=0.9 Hz, 1H), 8.39-8.22 (m, 2H), 8.20 (s, 1H), 7.45 (s, 1H), 7.33 (s, 2H), 7.14 (d, J=4.4 Hz, 2H), 2.03 (s, 4H), 1.01-0.51 (m, 4H).

Example 202

2-(3-[[8-amino-6-(4-methylpyridin-3-yl)-2,7-naphthyridin-3-yl]amino]-5-cyclopropyl-1H-pyrazol-1-yl)ethan-1-ol (Compound 259)

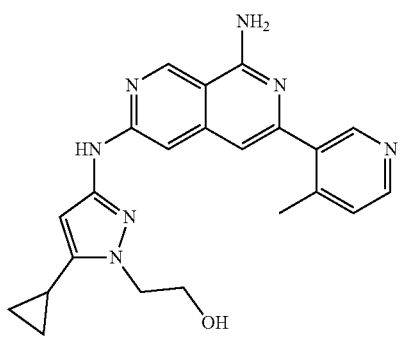 [SMILES: Cc1ccncc1-c1cc2cc(Nc3cc(C4CC4)n(CCO)n3)ncc2c(N)n1]

Step 1: 3-Cyclopropyl-5-iodo-1-[2-(oxan-2-yloxy)ethyl]-1H-pyrazole

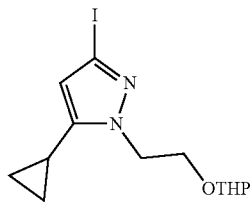

To an ice-cooled solution of 3-cyclopropyl-5-iodo-1H-pyrazole (950 mg, 4.06 mmol) in N,N-dimethylformamide (10 mL) was added sodium hydride (292 mg, 12.168 mmol). After 2 h, 2-(2-bromoethoxy)oxane (1.242 g, 5.940 mmol) was added to the reaction, and the reaction mixture was warmed to 25° C. for 3 h. The reaction was diluted with water, and the resulting solution was extracted with ethyl acetate. The combined organic extracts were dried over Na$_2$SO$_4$, filtered, and concentrated under vacuum. Purification by silica gel chromatography (1:4 ethyl acetate/petroleum ether) afforded 3-cyclopropyl-5-iodo-1-[2-(oxan-2-yloxy)ethyl]-1H-pyrazole (1.30 g, 89%) as a yellow oil. LCMS (ESI): [M+H]$^+$=363.0.

Step 2: 6-N-[5-cyclopropyl-1-[2-(oxan-2-yloxy)ethyl]-1H-pyrazol-3-yl]-1-N,1-N-bis[(2,4-dimethoxyphenyl)methyl]-3-(4-methylpyridin-3-yl)-2,7-naphthyridine-1,6-diamine

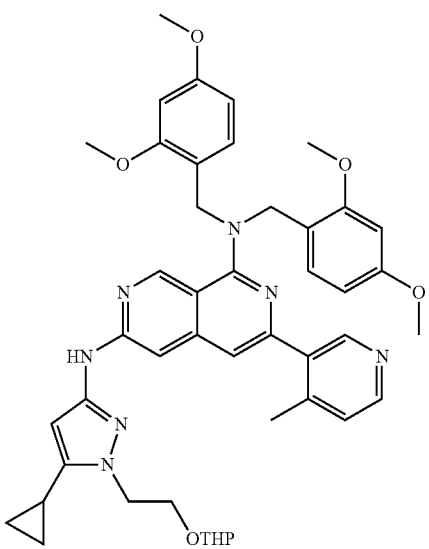

A suspension of 1-N,1-N-bis[(2,4-dimethoxyphenyl)methyl]-3-(4-methylpyridin-3-yl)-2,7-naphthyridine-1,6-diamine (0.30 g, 0.54 mmol), 5-cyclopropyl-3-iodo-1-[2-(oxan-2-yloxy)ethyl]-1H-pyrazole (394 mg, 1.09 mmol), Cs$_2$CO$_3$ (1.06 g, 3.25 mmol), 3rd generation t-BuBrettPhos precatalyst (93 mg, 0.11 mmol), and t-BuBrettPhos (132 mg, 0.27 mmol) in dioxane (8 mL) was heated at 110° C. under nitrogen for 12 h. The reaction mixture was cooled to room temperature and concentrated under vacuum. Purification by silica gel chromatography (25:1 dichloromethane/methanol) afforded 6-N-[5-cyclopropyl-1-[2-(oxan-2-yloxy)ethyl]-1H-pyrazol-3-yl]-1-N,1-N-bis[(2,4-dimethoxyphenyl)methyl]-3-(4-methylpyridin-3-yl)-2,7-naphthyridine-1,6-diamine (0.24 g, 56%) as a yellow solid. LCMS (ESI): [M+H]$^+$=786.4.

Step 3: 2-(3-[[8-amino-6-(4-methylpyridin-3-yl)-2,7-naphthyridin-3-yl]amino]-5-cyclopropyl-1H-pyrazol-1-yl)ethan-1-ol

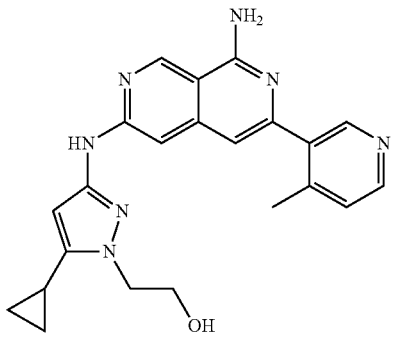 [SMILES: Cc1ccncc1-c1cc2cc(Nc3cc(C4CC4)n(CCO)n3)ncc2c(N)n1]

A solution of 6-N-[5-cyclopropyl-1-[2-(oxan-2-yloxy)ethyl]-1H-pyrazol-3-yl]-1-N,1-N-bis[(2,4-dimethoxyphenyl)methyl]-3-(4-methylpyridin-3-yl)-2,7-naphthyridine-1,6-diamine (320 mg, 0.41 mmol) in trifluoroacetic acid (10 mL) was heated at 50° C. After 1 h, the reaction was concentrated under vacuum, and the resulting residue was purified by silica gel chromatography (15:1 dichloromethane/methanol) to afford 2-(3-[[8-amino-6-(4-methylpyridin-3-yl)-2,7-naphthyridin-3-yl]amino]-5-cyclopropyl-1H-pyrazol-1-yl)ethan-1-ol (0.136 g, 83%) as a yellow solid. LCMS (ESI): R$_T$ (min)=1.07, [M+H]$^+$=402.2, method=K-1; $^1$H NMR (300 MHz, CD$_3$OD) δ 9.32 (s, 1H), 8.56 (s, 1H), 8.54 (d, J=5.4 Hz, 1H), 7.78 (s, 1H), 7.47 (d, J=5.4 Hz, 1H), 6.85 (s, 1H), 6.71 (s, 1H), 4.15 (t, J=5.2 Hz, 2H), 3.87 (t, J=5.2 Hz, 2H), 2.44 (s, 3H), 1.84-1.75 (m, 1H), 0.85-0.83 (m, 4H).

Example 203

1-(4-[[8-amino-6-(4-methylpyridin-3-yl)-2,7-naphthyridin-3-yl]amino]-1H-pyrazol-1-yl)-2-methylpropan-2-ol (Compound 260)

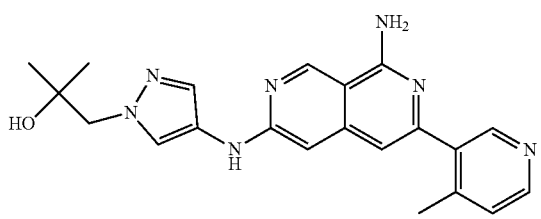 [SMILES: Cc1ccncc1-c1cc2cc(Nc3cnn(CC(C)(C)O)c3)ncc2c(N)n1]

The title compound was prepared using a procedure as described for 2-(3-[[8-amino-6-(4-methylpyridin-3-yl)-2,7-naphthyridin-3-yl]amino]-5-cyclopropyl-1H-pyrazol-1-yl)ethan-1-ol (Compound 259) LCMS (ESI): R$_T$ (min)=1.50, [M+H]$^+$=390.1, method=K-1; $^1$H NMR (300 MHz, DMSO-d$_6$) δ 9.20 (s, 1H), 8.86 (s, 1H), 8.52 (s, 1H), 8.40 (d, J=5.0 Hz, 1H), 7.88 (s, 1H), 7.48 (s, 1H), 7.28 (d, J=5.0 Hz, 1H), 7.06 (s, 2H), 6.73 (s, 1H), 6.62 (s, 1H), 4.69 (s, 1H), 3.98 (s, 2H), 2.39 (s, 3H), 1.07 (s, 6H).

Example 204

2-(5-[[8-amino-6-(4-methylpyridin-3-yl)-2,7-naphthyridin-3-yl]amino]-3-methyl-1H-pyrazol-1-yl)ethan-1-ol (Compound 261)

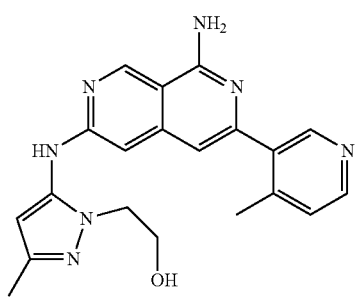 [SMILES: Cc1cc(Nc2cc3cc(-c4cnccc4C)nc(N)c3cn2)n(CCO)n1]

The title compound was prepared using a procedure as described for: 2-(3-[[8-amino-6-(4-methylpyridin-3-yl)-2,7-naphthyridin-3-yl]amino]-5-cyclopropyl-1H-pyrazol-1-yl)ethan-1-ol (Compound 259) LCMS (ESI): $R_T$ (min)=1.01, [M+H]$^+$=376.1, method=K-1; $^1$H NMR (300 MHz, CD$_3$OD) δ 9.17 (t, J=0.9 Hz, 1H), 8.51 (s, 1H), 8.42 (d, J=5.1 Hz, 1H), 7.49-7.30 (m, 1H), 6.84 (dd, J=7.3, 0.9 Hz, 2H), 6.16 (d, J=0.6 Hz, 1H), 4.16 (t, J=5.4 Hz, 2H), 3.89 (dd, J=5.7, 5.0 Hz, 2H), 2.44 (d, J=0.6 Hz, 3H), 2.27 (d, J=0.5 Hz, 3H).

Example 205

2-(3-[[8-amino-6-(4-methylpyridin-3-yl)-2,7-naphthyridin-3-yl]amino]-5-methyl-1H-pyrazol-1-yl)ethan-1-ol (Compound 262)

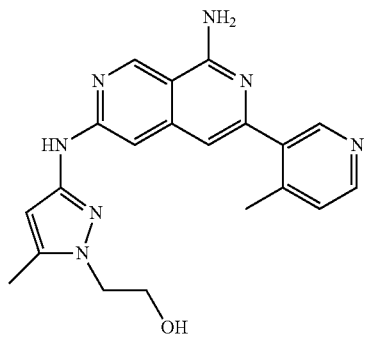 [SMILES: Cc1ccncc1-c1cc2cc(Nc3cc(C)n(CCO)n3)ncc2c(N)n1]

The title compound was prepared using a procedure as described for: 2-(3-[[8-amino-6-(4-methylpyridin-3-yl)-2,7-naphthyridin-3-yl]amino]-5-cyclopropyl-1H-pyrazol-1-yl)ethan-1-ol (Compound 259) LCMS (ESI): $R_T$ (min)=1.01, [M+H]$^+$=376.1, method=K-1; $^1$H NMR (300 MHz, CD$_3$OD) δ 9.16 (t, J=0.8 Hz, 1H), 8.52 (s, 1H), 8.43 (d, J=5.1 Hz, 1H), 7.48-7.34 (m, 2H), 6.89-6.78 (m, 1H), 6.03 (d, J=0.8 Hz, 1H), 4.13 (t, J=5.4 Hz, 2H), 3.93 (t, J=5.4 Hz, 2H), 2.46 (s, 3H), 2.36 (d, J=0.8 Hz, 3H).

Example 206

3-[[8-Amino-6-(4-methylpyridin-3-yl)-2,7-naphthyridin-3-yl]amino]-N,1-dimethyl-1H-pyrazole-5-carboxamide (Compound 263)

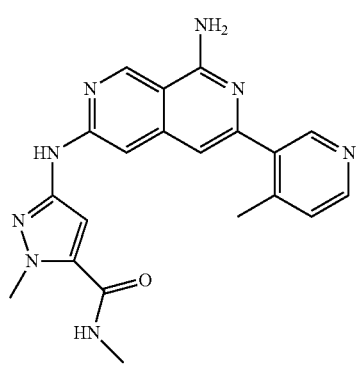 [SMILES: CNC(=O)c1cc(Nc2cc3cc(-c4cnccc4C)nc(N)c3cn2)nn1C]

Step 1:
3-Bromo-N,1-dimethyl-1H-pyrazole-5-carboxamide

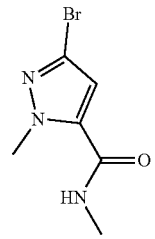

To a solution of 3-bromo-1-methyl-1H-pyrazole-5-carboxylic acid (0.50 g, 2.44 mmol) in N,N-dimethylformamide (8 mL) at 25° C. was sequentially added methylamine hydrochloride (0.30 g, 4.44 mmol), diisopropylethylamine (2.5 mL, 15 mmol), and HATU (1.1 g, 2.9 mmol). After 12 h, the reaction mixture was concentrated, and the resulting residue was purified by silica gel chromatography (1:3 ethyl acetate/petroleum ether) to afford 3-bromo-N,1-dimethyl-1H-pyrazole-5-carboxamide (480 mg, 90%) as a white solid. LCMS (ESI): [M+H]$^+$=218.1.

Step 2: 3-[(8-[Bis[(2,4-dimethoxyphenyl)methyl]amino]-6-(4-methylpyridin-3-yl)-2,7-naphthyridin-3-yl)amino]-N,1-dimethyl-1H-pyrazole-5-carboxamide

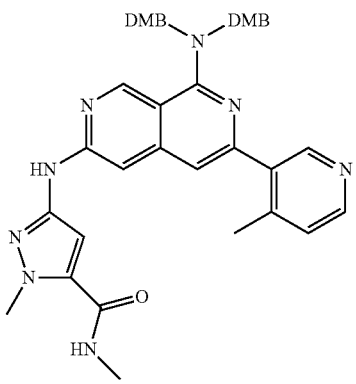

A suspension of 1-N,1-N-bis[(2,4-dimethoxyphenyl)methyl]-3-(4-methylpyridin-3-yl)-2,7-naphthyridine-1,6-diamine (0.50 g, 0.906 mmol), 3-bromo-N,1-dimethyl-1H-pyrazole-5-carboxamide (0.50 g, 2.293 mmol), t-BuBrettPhos (225 mg, 0.464 mmol), 3rd generation t-BuBrettPhos precatalyst (120 mg, 0.140 mmol) and $Cs_2CO_3$ (1.78 g, 5.463 mmol) in dioxane (12 mL) was heated at 110° C. for 2 h under nitrogen. The reaction was filtered, and the filtrate was concentrated under vacuum to afford crude 3-[(8-[bis[(2,4-dimethoxyphenyl)methyl]amino]-6-(4-methylpyridin-3-yl)-2,7-naphthyridin-3-yl)amino]-N,1-dimethyl-1H-pyrazole-5-carboxamide (0.58 g, 93%) as a yellow solid. LCMS (ESI): $[M+H]^+$=689.3.

Step 3: 3-[[8-Amino-6-(4-methylpyridin-3-yl)-2,7-naphthyridin-3-yl]amino]-N,1-dimethyl-1H-pyrazole-5-carboxamide

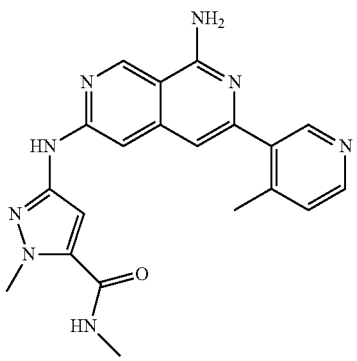 [SMILES: CNC(=O)c1cc(Nc2cc3cc(-c4cnccc4C)nc(N)c3cn2)nn1C]

A solution of 3-[(8-[bis[(2,4-dimethoxyphenyl)methyl]amino]-6-(4-methylpyridin-3-yl)-2,7-naphthyridin-3-yl)amino]-N,1-dimethyl-1H-pyrazole-5-carboxamide (0.50 g, 0.73 mmol) in trifluoroacetic acid (8 mL) was heated at 50° C. After 2 h, the reaction was concentrated under vacuum, and the resulting residue was purified by Prep-HPLC to afford 3-[[8-amino-6-(4-methylpyridin-3-yl)-2,7-naphthyridin-3-yl]amino]-N,1-dimethyl-1H-pyrazole-5-carboxamide (75.1 mg, 27%) as a yellow solid. LCMS (ESI): $R_T$ (min) =0.91, $[M+H]^+$=389.2, method=K-1; $^1$H NMR (300 MHz, $CD_3OD$) δ 9.19 (s, 1H), 8.52 (s, 1H), 8.43 (d, J=5.1 Hz, 1H), 7.42 (s, 1H), 7.39 (d, J=5.1 Hz, 1H), 6.85 (s, 1H), 6.72 (s, 1H), 4.07 (s, 3H), 2.89 (s, 3H), 2.45 (s, 3H).

Example 207

(4-[[8-Amino-6-(4-methylpyridin-3-yl)-2,7-naphthyridin-3-yl]amino]phenyl)methanesulfonamide (Compound 264)

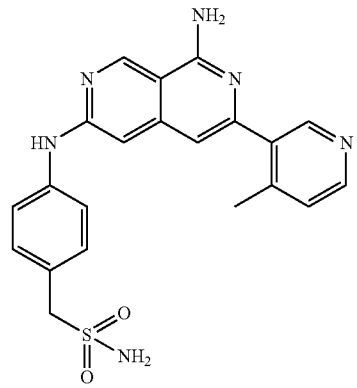 [SMILES: Cc1ccncc1-c1cc2cc(Nc3ccc(CS(N)(=O)=O)cc3)ncc2c(N)n1]

Step 1: (4-Bromophenyl)methanesulfonamide

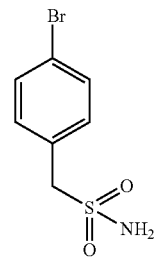 [SMILES: NS(=O)(=O)Cc1ccc(Br)cc1]

A solution of $NH_3$ in 1,4-dioxane (80 mL, 0.5 M) was added dropwise to an ice-cooled solution of (4-bromophenyl)methanesulfonyl chloride (2.00 g, 7.42 mmol) in dichloromethane (20 mL). The resulting mixture was warmed to room temperature for 30 min. The reaction was concentrated under vacuum, and the resulting residue was suspended with 10:1 dichloromethane/ethyl acetate (20 mL), and the solids were collected by filtration to afford (4-bromophenyl)methanesulfonamide (1.6 g, 86%) as a white solid. $^1$H NMR (300 MHz, DMSO-$d_6$) δ 7.58 (d, J=8.4 Hz, 2H), 7.32 (d, J=8.4 Hz, 2H), 6.85 (s, 2H), 4.25 (s, 2H).

Step 2: [4-[(8-[Bis[(2,4-dimethoxyphenyl)methyl]amino]-6-(4-methylpyridin-3-yl)-2,7-naphthyridin-3-yl)amino]phenyl]methanesulfonamide

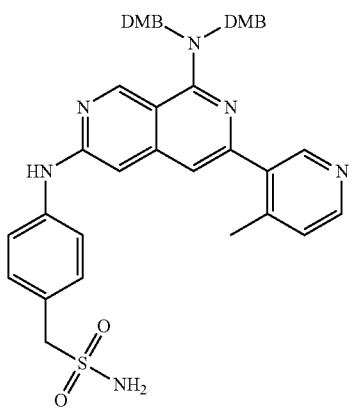

To a solution of 1-N,1-N-bis[(2,4-dimethoxyphenyl)methyl]-3-(4-methylpyridin-3-yl)-2,7-naphthyridine-1,6-diamine (0.25 g, 0.45 mmol) in 1,4-dioxane (12.5 mL) was sequentially added (4-bromophenyl)methanesulfonamide (453 mg, 1.81 mmol), Pd$_2$(dba)$_3$ (41.5 mg, 0.045 mmol), XPhos (43 mg, 0.091 mmol) and t-BuONa (261 mg, 2.72 mmol). The reaction mixture was heated with microwave radiation at 110° C. for 1 h. The reaction was filtered, and the filtrate was concentrated under vacuum. Purification by silica gel chromatography (15:1 dichloromethane/methanol) afforded [4-[(8-[bis[(2,4-dimethoxyphenyl)methyl]amino]-6-(4-methylpyridin-3-yl)-2,7-naphthyridin-3-yl)amino]phenyl]methanesulfonamide (160 mg, 49%) as a yellow solid. LCMS (ESI): [M+H]$^+$=721.0.

Step 3: (4-[[8-Amino-6-(4-methylpyridin-3-yl)-2,7-naphthyridin-3-yl]amino]phenyl)methanesulfonamide

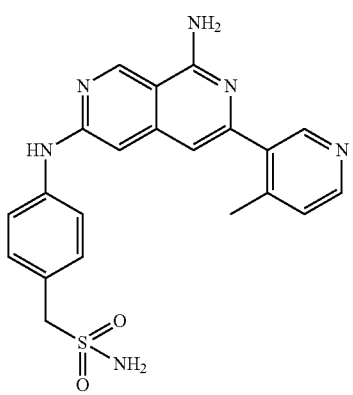 [SMILES: Cc1ccncc1-c1cc2cc(Nc3ccc(CS(N)(=O)=O)cc3)ncc2c(N)n1]

A solution of [4-[(8-[bis[(2,4-dimethoxyphenyl)methyl]amino]-6-(4-methylpyridin-3-yl)-2,7-naphthyridin-3-yl)amino]phenyl]methanesulfonamide (130 mg, 0.18 mmol) in trifluoroacetic acid (10 mL) was heated at 45° C. for 5 h. The reaction mixture was concentrated under vacuum, and the resulting residue was purified by Prep-HPLC to afford (4-[[8-amino-6-(4-methylpyridin-3-yl)-2,7-naphthyridin-3-yl]amino]phenyl)methanesulfonamide (36.6 mg, 48%) as a yellow solid. LCMS (ESI): R$_T$ (min)=1.07, [M+H]$^+$=421.1, method=M; $^1$H NMR (300 MHz, DMSO-d$_6$) δ 13.07-12.83 (m, 1H), 9.97 (s, 1H), 9.58 (s, 1H), 8.98-8.42 (m, 3H), 7.60 (d, J=8.4 Hz, 2H), 7.54 (s, 1H), 7.48 (d, J=4.8 Hz, 2H), 7.07 (s, 1H), 7.01 (s, 1H), 6.82 (s, 2H), 4.24 (s, 2H), 2.38 (s, 3H).

Example 208

1-(4-[[8-amino-6-(4-methylpyridin-3-yl)-2,7-naphthyridin-3-yl]amino]phenyl)piperazin-2-one (Compound 265)

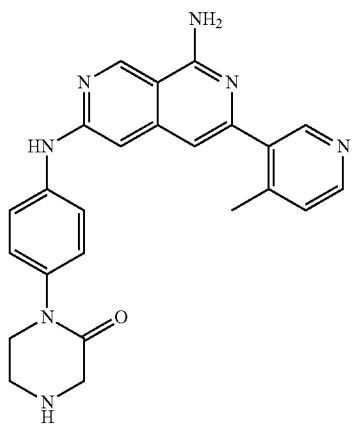 [SMILES: Cc1ccncc1-c1cc2cc(Nc3ccc(N4CCNCC4=O)cc3)ncc2c(N)n1]

Step 1: tert-butyl 4-(4-bromophenyl)-3-oxopiperazine-1-carboxylate

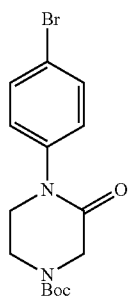 [SMILES: CC(C)(C)OC(=O)N1CCN(c2ccc(Br)cc2)C(=O)C1]

A suspension of 1-bromo-4-iodobenzene (5.0 g, 17.7 mmol), tert-butyl 3-oxopiperazine-1-carboxylate (3.53 g, 17.6 mmol), methyl[2-(methylamino)ethyl]amine (310 mg, 3.52 mmol), CuI (670 mg, 3.52 mmol), and K$_3$PO$_4$ (11.2 g, 52.8 mmol) in N,N-dimethylformamide (100 mL) was heated at 100° C. After 3 h, the reaction was cooled to room temperature and diluted with water. The resulting solution was extracted with ethyl acetate, and the combined organic extracts were concentrated under vacuum. Purification by silica gel chromatography (1:1 ethyl acetate/petroleum ether) afforded tert-butyl 4-(4-bromophenyl)-3-oxopiperazine-1-carboxylate (2.8 g, 45%) as a white solid. LCMS (ESI): [M+H]$^+$=355.1.

Step 2: tert-butyl 4-[4-[(8-[bis[(2,4-dimethoxyphenyl)methyl]amino]-6-(4-methylpyridin-3-yl)-2,7-naphthyridin-3-yl)amino]phenyl]-3-oxopiperazine-1-carboxylate

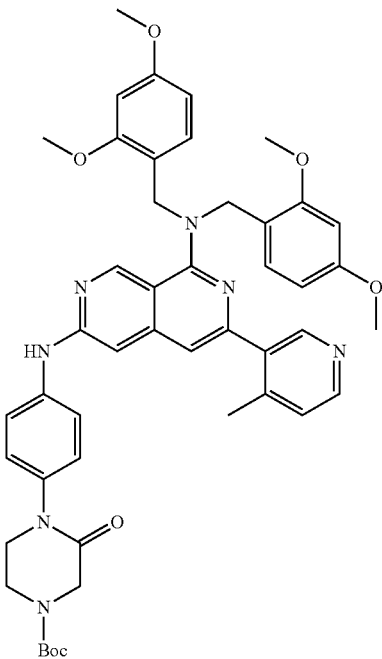 [SMILES: COc1ccc(CN(Cc2ccc(OC)cc2OC)c2nc(-c3cnccc3C)cc3cc(Nc4ccc(N5CCN(C(=O)OC(C)(C)C)CC5=O)cc4)ncc23)c(OC)c1]

A mixture of 1-N,1-N-bis[(2,4-dimethoxyphenyl)methyl]-3-(4-methylpyridin-3-yl)-2,7-naphthyridine-1,6-diamine (20 mg, 0.036 mmol), tert-butyl 4-(4-bromophenyl)-3-oxopiperazine-1-carboxylate (32 mg, 0.090 mmol), Pd$_2$(dba)$_3$ (1.6 mg, 0.002 mmol), XPhos (1.7 mg, 0.004 mmol), and Cs$_2$CO$_3$ (23.6 mg, 0.072 mmol) in dioxane (2 mL) was heated at 100° C. for 12 h. The reaction was filtered, and the filtrate was concentrated under vacuum. Purification by silica gel chromatography (15:1 dichloromethane/methanol) yielded 4-[4-[(8-[bis[(2,4-dimethoxyphenyl)methyl]amino]-6-(4-methylpyridin-3-yl)-2,7-naphthyridin-3-yl)amino]phenyl]-3-oxopiperazine-1-carboxylate (10 mg, 34%) as a yellow solid. LCMS (ESI): [M+H]$^+$=826.9.

Step 3: 1-(4-[[8-amino-6-(4-methylpyridin-3-yl)-2,7-naphthyridin-3-yl]amino]phenyl)piperazin-2-one

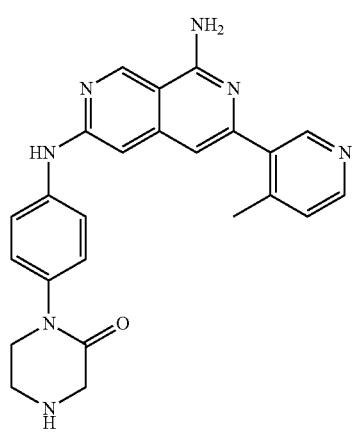 [SMILES: Cc1ccncc1-c1cc2cc(Nc3ccc(N4CCNCC4=O)cc3)ncc2c(N)n1]

A solution of tert-butyl 4-[4-[(8-[bis[(2,4-dimethoxyphenyl)methyl]amino]-6-(4-methylpyridin-3-yl)-2,7-naphthyridin-3-yl)amino]phenyl]-3-oxopiperazine-1-carboxylate (0.20 g, 0.242 mmol) in trifluoroacetic acid (5 mL) was heated at 80° C. for 2 h. The mixture was concentrated under vacuum, and the resulting residue was purified by Prep-HPLC to afford 1-(4-[[8-amino-6-(4-methylpyridin-3-yl)-2,7-naphthyridin-3-yl]amino]phenyl)piperazin-2-one (57.1 mg, 55%) as a white solid. LCMS (ESI): R$_T$ (min)=1.67, [M+H]$^+$=426.2, method=M; $^1$H NMR (300 MHz, CD$_3$OD) δ 9.19 (t, J=0.9 Hz, 1H), 8.50 (s, 1H), 8.41 (d, J=5.1 Hz, 1H), 7.65-7.55 (m, 2H), 7.38 (d, J=5.2 Hz, 1H), 7.31-7.23 (m, 2H), 6.95 (d, J=0.9 Hz, 1H), 6.79 (d, J=0.8 Hz, 1H), 3.72 (t, J=5.5 Hz, 2H), 3.57 (s, 2H), 3.19 (t, J=5.5 Hz, 2H), 2.44 (s, 3H).

Example 209

2-(4-[[8-amino-6-(4-methylpyridin-3-yl)-2,7-naphthyridin-3-yl]amino]-1H-pyrazol-1-yl)-2-methylpropan-1-ol (Compound 266)

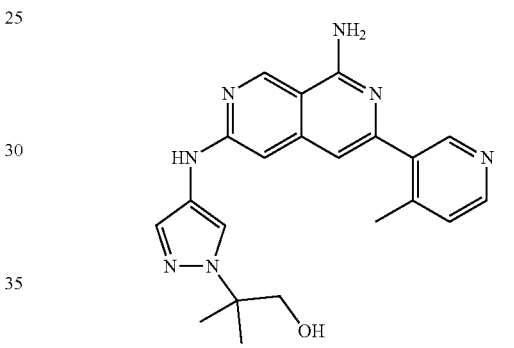

The title compound was prepared using a procedure as described for (3R)-3-(4-[[8-amino-6-(4-methylpyridin-3-yl)-2,7-naphthyridin-3-yl]amino]-1H-pyrazol-1-yl)-1-methylpyrrolidin-2-one (Compound 249) LCMS (ESI): R$_T$ (min)=1.83, [M+H]$^+$=390.2, method=M; $^1$H NMR (400 MHz, DMSO-d$_6$) δ 9.21 (s, 1H), 8.78 (s, 1H), 8.52 (s, 1H), 8.42-8.40 (m, 1H), 7.91 (s, 1H), 7.51 (s, 1H), 7.29-7.27 (m, 1H), 7.04 (m, 2H), 6.74 (s, 1H), 6.62 (s, 1H), 4.97 (t, J=5.7 Hz, 1H), 5.58 (d, J=5.7 Hz, 2H), 2.39 (s, 3H), 1.47 (s, 6H).

Example 210

(+/−)-trans-N-(8-amino-6-(5-fluoro-2-methylphenyl)-2,7-naphthyridin-3-yl)-2-(1-methyl-1H-pyrazol-4-yl)cyclopropanecarboxamide (Compound 267)

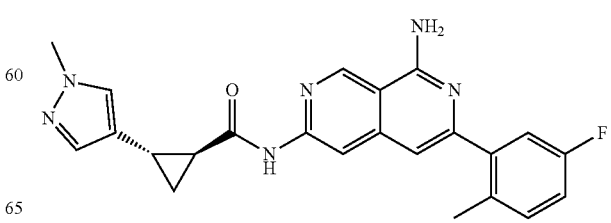

Step 1: trans-N-(8-amino-6-(5-fluoro-2-methylphenyl)-2,7-naphthyridin-3-yl)-2-(1-methyl-1H-pyrazol-4-yl)cyclopropanecarboxamide

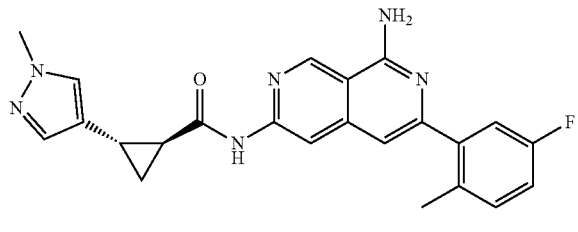 [SMILES: Cc1ccc(F)cc1-c1cc2cc(NC(=O)[C@H]3C[C@@H]3c3cnn(C)c3)ncc2c(N)n1]

A mixture of trans-N-(8-amino-6-(5-fluoro-2-methylphenyl)-2,7-naphthyridin-3-yl)-2-(1-methyl-1H-pyrazol-4-yl)cyclopropanecarboxamide (0.20 g, 0.58 mmol), 5-fluoro-2-methylphenylboronic acid (269 mg, 1.75 mmol), Pd(PPh$_3$)$_4$ (135 mg, 0.11 mmol) and K$_3$PO$_4$ (372 mg, 1.75 mmol) in 4:1 1,4-dioxane/water (10 mL) was heated at 100° C. for 6 h. The resulting mixture was concentrated under vacuum, and the resulting residue was purified by silica gel chromatography (ethyl acetate) followed by Prep-HPLC to afford trans-N-(8-amino-6-(5-fluoro-2-methylphenyl)-2,7-naphthyridin-3-yl)-2-(1-methyl-1H-pyrazol-4-yl) cyclopropanecarboxamide (3 mg) as a white solid. LCMS (ESI): R$_T$ (min)=1.67, [M+H]$^+$=417.2, method=K-1; $^1$H NMR (300 MHz, CD$_3$OD) δ 9.27 (t, J=0.9 Hz, 1H), 8.32-8.26 (m, 1H), 7.50 (s, 1H), 7.36 (d, J=0.8 Hz, 1H), 7.30-7.28 (m, 1H), 7.14-7.11 (m, 1H), 7.05-7.03 (m, 1H), 6.90 (d, J=0.8 Hz, 1H), 3.84 (s, 3H), 2.37-2.35 (m, 1H), 2.32 (s, 3H), 2.15-2.03 (m, 1H), 1.56-1.53 (m, 1H), 1.25-1.22 (m, 1H).

Example 211

(+/−)-trans-N-[8-amino-6-(5-hydroxy-2-methylphenyl)-2,7-naphthyridin-3-yl]-2-(1-methyl-1H-pyrazol-4-yl)cyclopropane-1-carboxamide (Compound 268)

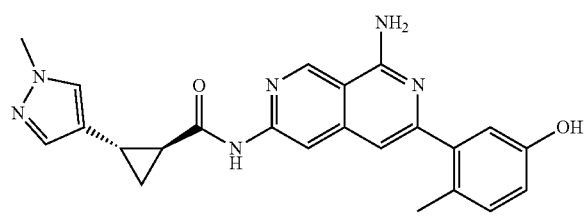 [SMILES: Cc1ccc(O)cc1-c1cc2cc(NC(=O)[C@H]3C[C@@H]3c3cnn(C)c3)ncc2c(N)n1]

To a solution of trans-N-(8-amino-6-chloro-2,7-naphthyridin-3-yl)-2-(1-methyl-1H-pyrazol-4-yl)cyclopropane-1-carboxamide (0.20 g, 0.58 mmol) in 5:1 1,4-dioxane/water (12 mL) was sequentially added (5-hydroxy-2-methylphenyl)boronic acid (134 mg, 0.88 mmol), Pd(PPh$_3$)$_4$ (135 mg, 0.12 mmol) and K$_3$PO$_4$ (372 mg, 1.75 mmol). The resulting solution was heated at 100° C. After 5 h, the reaction was filtered, and the filtrate was concentrated under vacuum. Purification by Prep-HPLC provided trans-N-[8-amino-6-(5-hydroxy-2-methylphenyl)-2,7-naphthyridin-3-yl]-2-(1-methyl-1H-pyrazol-4-yl)cyclopropane-1-carboxamide (120 mg, 50%) as a white solid. LCMS (ESI): R$_T$ (min)=1.26, [M+H]$^+$=415.2, method=K-1; $^1$H NMR (400 MHz, CD$_3$OD) δ 9.26 (s, 1H), 8.27 (s, 1H), 7.50 (s, 1H), 7.37 (s, 1H), 7.10 (d, J=8.0 Hz, 1H), 6.84 (d, J=8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H).

Example 212

(1R,2S)—N-[8-amino-5-chloro-6-(4-methylpyridin-3-yl)-2,7-naphthyridin-3-yl]-2-(cyanomethyl)cyclopropane-1-carboxamide (Compound 269) and (1S,2R)—N-[8-amino-5-chloro-6-(4-methylpyridin-3-yl)-2,7-naphthyridin-3-yl]-2-(cyanomethyl)cyclopropane-1-carboxamide (Compound 270)

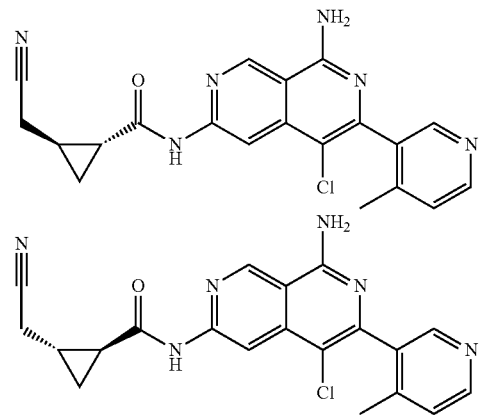

To a solution of trans-N-[8-amino-6-(4-methylpyridin-3-yl)-2,7-naphthyridin-3-yl]-2-(cyanomethyl)cyclopropane-1-carboxamide (210 mg, 0.59 mmol) in N,N-dimethylformamide (7 mL) at 25° C. was added NCS (156 mg, 1.17 mmol). After 15 h, the reaction was concentrated and purified by Prep-HPLC to afford racemic product (0.10 g, 43%) as a white solid. The enantiomers were separated by chiral SFC. Compound 269: LCMS (ESI): R$_T$ (min)=2.06, [M+H]+=393, method=K-1; $^1$H NMR (400 MHz, CD$_3$OD) δ 9.34 (s, 1H), 8.69 (s, 1H), 8.48 (d, J=5.2 Hz, 1H), 8.41 (s, 1H), 7.44 (d, J=5.2 Hz, 1H), 2.81-2.62 (m, 2H), 2.29 (s, 3H), 2.07-2.02 (m, 1H), 1.79-1.75 (m, 1H), 1.39-1.33 (m, 1H), 1.09-1.05 (m, 1H). Compound 270: LCMS (ESI): R$_T$ (min)=1.14, [M+H]+=393, method=K-1; $^1$H NMR (400 MHz, CD$_3$OD) δ 9.34 (s, 1H), 8.69 (s, 1H), 8.48 (d, J=5.2 Hz, 1H), 8.41 (s, 1H), 7.44 (d, J=5.2 Hz, 1H), 2.81-2.62 (m, 2H), 2.29 (s, 3H), 2.07-2.02 (m, 1H), 1.79-1.75 (m, 1H), 1.39-1.35 (m, 1H), 1.10-1.05 (m, 1H).

Example 213

(1R,2S)—N-[8-amino-5-ethyl-6-(4-methylpyridin-3-yl)-2,7-naphthyridin-3-yl]-2-(cyanomethyl)cyclopropane-1-carboxamide (Compound 271) and (1R,2S)—N-[8-amino-5-ethyl-6-(4-methylpyridin-3-yl)-2,7-naphthyridin-3-yl]-2-(cyanomethyl)cyclopropane-1-carboxamide (Compound 272)

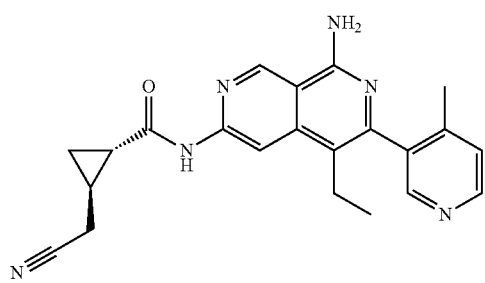

A suspension of trans-N-[8-amino-5-ethenyl-6-(4-methylpyridin-3-yl)-2,7-naphthyridin-3-yl]-2-(cyanomethyl)cyclopropane-1-carboxamide (68 mg, 0.18 mmol) (Compound 275) and palladium on carbon (50 mg, 0.47 mmol) in methanol (6 mL) was stirred for 30 min at 25° C. under hydrogen (1 atm). The reaction mixture was filtered, and the filtrate was concentrated under vacuum. Purification by Prep-HPLC afforded racemic product (11 mg, 16%) as a yellow solid. The enantiomers were separated by chiral SFC. Compound 271: LCMS (ESI): $R_T$ (min)=1.06, [M+H]$^+$=387, method=K-1; $^1$H NMR (400 MHz, CD$_3$OD) δ 9.34 (s, 1H), 8.57 (s, 1H), 8.49 (d, J=5.2 Hz, 1H), 8.38 (s, 1H), 7.46 (d, J=5.2 Hz, 1H), 2.78-2.68 (m, 3H), 2.52-2.39 (m, 1H), 2.22 (s, 3H), 2.07-2.02 (m, 1H), 1.79-1.74 (m, 1H), 1.39-1.36 (m, 1H), 1.12-1.02 (m, 4H). Compound 272: LCMS (ESI): $R_T$ (min)=1.05, [M+H]+=387, method=K-1; $^1$H NMR (300 MHz, CD$_3$OD) δ 9.34 (s, 1H), 8.58 (s, 1H), 8.49 (d, J=5.2 Hz, 1H), 8.38 (s, 1H), 7.46 (d, J=5.2 Hz, 1H), 2.78-2.68 (m, 3H), 2.52-2.39 (m, 1H), 2.22 (s, 3H), 2.07-2.02 (m, 1H), 1.79-1.74 (m, 1H), 1.39-1.36 (m, 1H), 1.12-1.02 (m, 4H).

Example 214

(R)-2-(4-(8-amino-6-(4-methylpyridin-3-yl)-2,7-naphthyridin-3-ylamino)-1H-pyrazol-1-yl)propanenitrile (Compound 273) and (S)-2-(4-(8-amino-6-(4-methylpyridin-3-yl)-2,7-naphthyridin-3-ylamino)-1H-pyrazol-1-yl)propanenitrile (Compound 274)

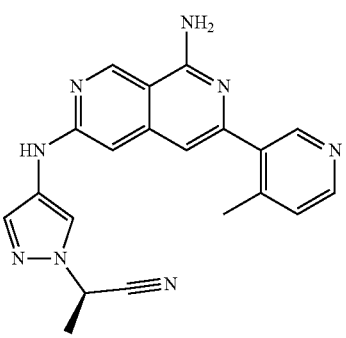

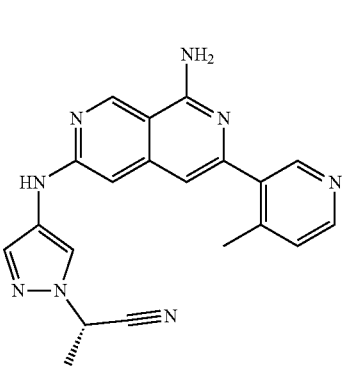

Step 1: 2-(4-bromo-1H-pyrazol-1-yl)propanenitrile

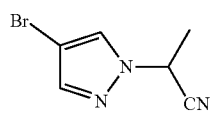

A suspension of 4-bromo-1H-pyrazole (1 g, 6.80 mmol), 2-chloropropanenitrile (612 mg, 6.83 mmol), Cs$_2$CO$_3$ (2.43 g, 7.45 mmol) in tetrahydrofuran (10 mL) was heated at 100° C. After 2 h, the reaction was filtered, and the filtrate was concentrated under vacuum. Purification by silica gel chromatography (10:1 dichloromethane/methanol) afforded 2-(4-bromo-1H-pyrazol-1-yl)propanenitrile (952 mg, 70%) as a white solid. LCMS (ESI): [M+H]$^+$=200.0.

Step 2: 2-[4-[(8-[bis[(2,4-dimethoxyphenyl)methyl] amino]-6-(4-methylpyridin-3-yl)-2,7-naphthyridin-3-yl)amino]-1H-pyrazol-1-yl]propanenitrile

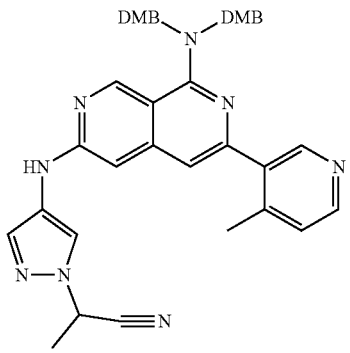

A mixture of 1-N,1-N-bis[(2,4-dimethoxyphenyl) methyl]-3-(4-methylpyridin-3-yl)-2,7-naphthyridine-1,6-diamine (552 mg, 1.00 mmol), 2-(4-bromo-1H-pyrazol-1-yl) propanenitrile (800 mg, 3.99 mmol), t-BuBrettPhos (97 mg, 0.20 mmol), 3rd generation t-BuBrettPhos precatalyst (171 mg, 0.20 mmol), and potassium carbonate (828 mg, 5.99 mmol) in dioxane (15 mL) was heated at 120° C. under nitrogen. After 5 h, the mixture was concentrated under vacuum. Purification by silica gel chromatography (10:1 dichloromethane/methanol) afforded 2-[4-[(8-[bis[(2,4-dimethoxyphenyl)methyl]amino]-6-(4-methylpyridin-3-yl)-2,7-naphthyridin-3-yl)amino]-1H-pyrazol-1-yl]propanenitrile (302 mg, 45%) as a brown oil. LCMS (ESI): [M+H]$^+$=671.3.

Step 3: (R)-2-(4-(8-amino-6-(4-methylpyridin-3-yl)-2,7-naphthyridin-3-ylamino)-1H-pyrazol-1-yl)propanenitrile and (S)-2-(4-(8-amino-6-(4-methylpyridin-3-yl)-2,7-naphthyridin-3-ylamino)-1H-pyrazol-1-yl) propanenitrile

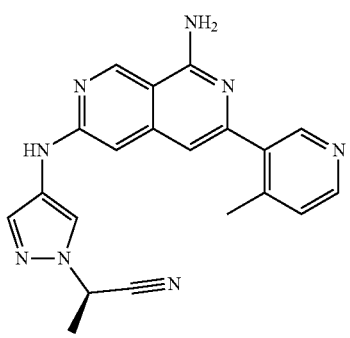

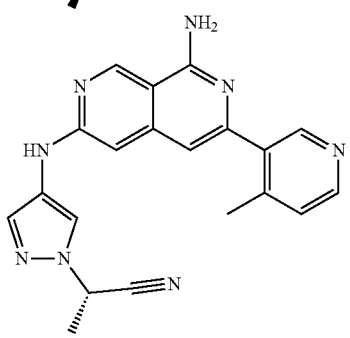

A solution of 2-[4-[(8-[bis[(2,4-dimethoxyphenyl) methyl]amino]-6-(4-methylpyridin-3-yl)-2,7-naphthyridin-3-yl)amino]-1H-pyrazol-1-yl]propanenitrile (248 mg, 0.37 mmol) and CF$_3$COOH (20 mL) was heated at 80° C. for 45 min. The mixture was concentrated under vacuum, and the resulting residue was dissolved with DCM (10 mL). The solution was adjusted to pH=8 with NH$_3$ in methanol. Purification by Prep-HPLC to afford racemic product (65.4 mg, 48%) as a yellow solid. The enantiomers were separated by chiral SFC. Compound 273: LCMS (ESI): R$_T$ (min)= 1.62, [M+H]$^+$=371, method=K-1; $^1$H NMR (300 MHz, CD$_3$OD) δ 9.19 (s, 1H), 8.50 (s, 1H), 8.42 (d, J=6.0 Hz, 1H), 8.13 (s, 1H), 7.70 (s, 1H), 7.39 (d, J=6.0 Hz, 1H), 6.78 (s, 1H), 6.74 (s, 1H), 5.64 (q, J=6.0 Hz, 1H), 2.44 (s, 3H), 1.91 (d, J=6.0 Hz, 3H). Compound 274: LCMS (ESI): R$_T$(min)=1.61, [M+H]$^+$=371, method=K-1; $^1$H NMR (300 MHz, CD$_3$OD) δ 9.19 (s, 1H), 8.50 (s, 1H), 8.42 (d, J=6.0 Hz, 1H), 8.13 (s, 1H), 7.70 (s, 1H), 7.39 (d, J=6.0 Hz, 1H), 6.78 (s, 1H), 6.74 (s, 1H), 5.64 (q, J=6 Hz, 1H), 2.44 (s, 3H), 1.91 (d, J=6 Hz, 3H).

Example 215

(+/−)-trans-N-[8-amino-5-ethenyl-6-(4-methylpyridin-3-yl)-2,7-naphthyridin-3-yl]-2-(cyanomethyl) cyclopropane-1-carboxamide (Compound 275)

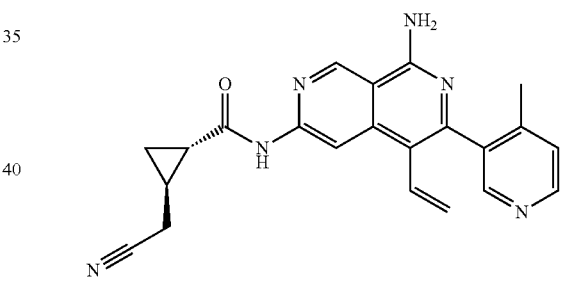

To a solution of trans-N-[8-amino-5-bromo-6-(4-methylpyridin-3-yl)-2,7-naphthyridin-3-yl]-2-(cyanomethyl)cyclopropane-1-carboxamide (0.050 g, 0.11 mmol) in dioxane (2 mL) and water (0.1 mL) was sequentially added potassium vinyltrifluoroborate (23 mg, 0.17 mmol), Pd(PPh$_3$)$_4$ (13 mg, 0.01 mmol), and sodium carbonate (37 mg, 0.35 mmol). The resulting mixture was heated at 85° C. for 15 h. The reaction was filtered and concentrated under vacuum. Purification by silica gel (15:1 dichloromethane/methanol) followed by Prep-HPLC afforded racemic product (2.5 mg, 6%) as a white solid. Compound 275: LCMS (ESI): R$_T$ (min)=1.86 min [M+H]$^+$=385.2, method=K-1; $^1$H NMR (300 MHz, CD$_3$OD) δ 9.34 (s, 1H), 8.71 (s, 1H), 8.44 (d, J=5.2 Hz, 1H), 8.35 (s, 1H), 7.40 (d, J=5.2 Hz, 1H), 6.59-6.52 (m, 1H), 5.40-5.37 (m, 1H), 5.25-5.21 (m, 1H), 2.82-2.63 (m, 2H), 2.23 (s, 3H), 2.05-2.01 (m, 1H), 1.77-1.72 (m, 1H), 1.37-1.34 (m, 1H), 1.08-1.03 (m, 1H).

Example 216

(1S,2S,3R)—N-[8-amino-6-(4-methylpyridin-3-yl)-2,7-naphthyridin-3-yl]-2-(cyanomethyl)-3-methylcyclopropane-1-carboxamide (Compound 276), (1R,2R,3S)—N-[8-amino-6-(4-methylpyridin-3-yl)-2,7-naphthyridin-3-yl]-2-(cyanomethyl)-3-methylcyclopropane-1-carboxamide (Compound 277) (1S,2S,3S)—N-[8-amino-6-(4-methylpyridin-3-yl)-2,7-naphthyridin-3-yl]-2-(cyanomethyl)-3-methylcyclopropane-1-carboxamide (Compound 278), and (1R,2R,3R)—N-[8-amino-6-(4-methylpyridin-3-yl)-2,7-naphthyridin-3-yl]-2-(cyanomethyl)-3-methylcyclopropane-1-carboxamide (Compound 279)

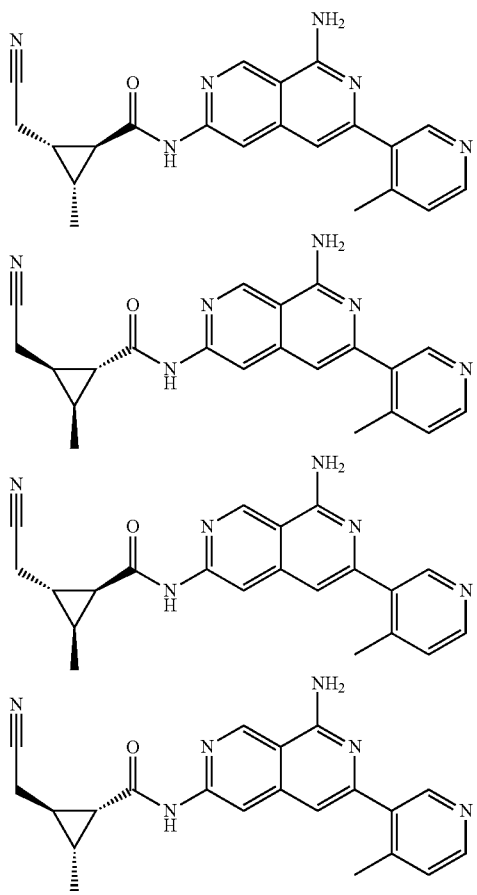

Step 1: tert-butyl (2E)-4-(benzyloxy)but-2-enoate

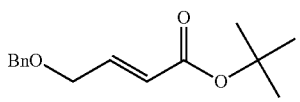 [SMILES: CC(C)(C)OC(=O)/C=C/COCc1ccccc1]

A mixture of 2-(benzyloxy)acetaldehyde (10.0 g, 66.6 mmol), tert-butyl 2-(diethoxyphosphoryl)acetate (16.8 g, 66.6 mmol), LiCi (16.7 g, 394 mmol), THF (200 mL) and diisopropylethylamine (8.5 g, 66 mmol) was stirred for 1 day at room temperature. The reaction was diluted with water (10 mL) and concentrated under vacuum. Purification by silica gel chromatography (100:1→10:1 petroleum ether/ethyl acetate) afforded tert-butyl (2E)-4-(benzyloxy)but-2-enoate (3.5 g, 21%) as a light yellow solid. LCMS (ESI): $[M+H]^+$=249.3.

Step 2: tert-butyl-2-[(benzyloxy)methyl]-3-methyl-cyclopropane-1-carboxylate

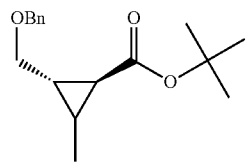 [SMILES: CC1[C@H](COCc2ccccc2)[C@H]1C(=O)OC(C)(C)C]

To a solution of ethyldiphenylsulfonium tetrafluoroborate (10.5 g, 34.75 mmol) in 1,2-dimethoxyethane (250 mL) and dichloromethane (25 mL) at −30° C. was added LDA (41 mL, 2M in THF). After 1 h, tert-butyl (2E)-4-(benzyloxy)but-2-enoate (2.9 g, 11.68 mmol) was added, and the reaction was warmed to room temperature for 16 h. The reaction was diluted with water (100 mL), and the resulting solution was extracted with ethyl acetate. The collected organic was concentrated. Purification by silica gel chromatography (100:1→10:1 petroleum ether/ethyl acetate) afforded tert-butyl-2-[(benzyloxy)methyl]-3-methylcyclopropane-1-carboxylate (1.5 g, 46%) as alight yellow solid. LCMS (ESI): $[M+H]^+$=277.0.

Step 3: 2-[(benzyloxy)methyl]-3-methylcyclopropane-1-carboxylic acid

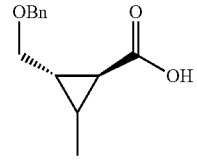 [SMILES: CC1[C@H](COCc2ccccc2)[C@H]1C(=O)O]

A solution of tert-butyl-2-[(benzyloxy)methyl]-3-methyl-cyclopropane-1-carboxylate (1.2 g, 4.34 mmol) in dichloromethane (5 mL) and trifluoroacetic acid (5 mL) was stirred for 16 h at room temperature. The mixture was concentrated under vacuum, and the resulting residue was purified by silica gel chromatography to afford 2-[(benzyloxy)methyl]-3-methylcyclopropane-1-carboxylic acid (700 mg, 73%) as light yellow oil.

Step 4: 2-[(benzyloxy)methyl]-N-(8-[bis[(3,4-dimethoxyphenyl)methyl]amino]-6-(4-methylpyridin-3-yl)-2,7-naphthyridin-3-yl)-3-methylcyclopropane-1-carboxamide

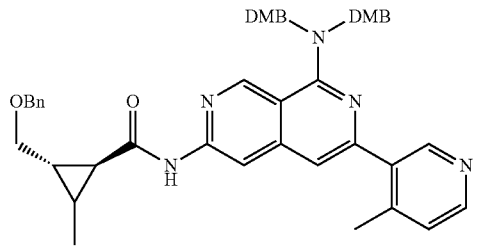

A mixture of 2-[(benzyloxy)methyl]-3-methylcyclopropane-1-carboxylic acid (1.1 g, 4.99 mmol), 1-N,1-N-bis[(3,4-dimethoxyphenyl)methyl]-3-(4-methylpyridin-3-yl)-2,7-naphthyridine-1,6-diamine (0.390 g, 0.71 mmol), pyridine (2 mL) and POCl$_3$ (2 mL) in dichloromethane (20 mL) was stirred for 1 h at room temperature. The reaction was diluted with water, and the resulting solution was extracted with ethyl acetate. The organic layers were combined and concentrated under vacuum. Purification by silica gel chromatography eluted with (100:1→1:1 petroleum ether/ethyl acetate) provided 2-[(benzyloxy)methyl]-N-(8-[bis[(3,4-dimethoxyphenyl)methyl]amino]-6-(4-methylpyridin-3-yl)-2,7-naphthyridin-3-yl)-3-methylcyclopropane-1-carboxamide (700 mg) as a light yellow solid. LCMS (ESI): [M+H]$^+$=754.4.

Step 5: N-(8-[bis[(2,4-dimethoxyphenyl)methyl]amino]-6-(4-methylpyridin-3-yl)-2,7-naphthyridin-3-yl)-2-(hydroxymethyl)-3-methylcyclopropane-1-carboxamide

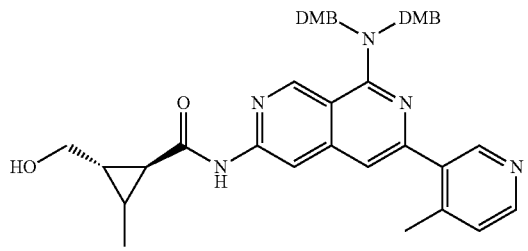

A suspension of 2-[(benzyloxy)methyl]-N-(8-[bis[(2,4-dimethoxyphenyl)methyl]amino]-6-(4-methylpyridin-3-yl)-2,7-naphthyridin-3-yl)-3-methylcyclopropane-1-carboxamide (0.60 g, 0.80 mmol) and palladium on carbon (3 g, 28.19 mmol) in methanol (30 mL) was stirred at room temperature under hydrogen (2 atm). After 16 h, the reaction was filtered, and the filtrate was concentrated under vacuum. Purification by silica gel chromatography 100:1 petroleum ether/ethyl acetate→ethyl acetate afforded N-(8-[bis[(2,4-dimethoxyphenyl)methyl]amino]-6-(4-methylpyridin-3-yl)-2,7-naphthyridin-3-yl)-2-(hydroxymethyl)-3-methylcyclopropane-1-carboxamide (0.50 g, 95%) as a light yellow solid. LCMS (ESI): [M+H]$^+$=664.8.

Step 6: [trans-2-[(8-[bis[(3,4-dimethoxyphenyl)methyl]amino]-6-(4-methylpyridin-3-yl)-2,7-naphthyridin-3-yl)carbamoyl]-3-methylcyclopropyl]methyl methanesulfonate

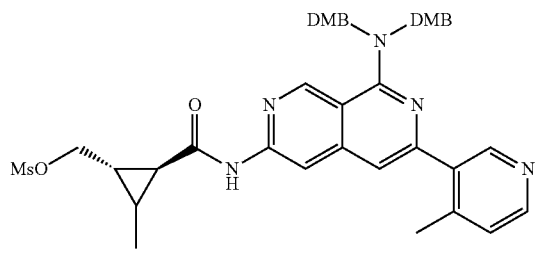

To an ice-cooled solution of N-(8-[bis[(3,4-dimethoxyphenyl)methyl]amino]-6-(4-methylpyridin-3-yl)-2,7-naphthyridin-3-yl)-2-(hydroxymethyl)-3-methylcyclopropane-1-carboxamide (0.10 g, 0.15 mmol) and triethylamine (45 mg, 0.45 mmol) in dichloromethane (10 mL) was added MsCl (34 mg, 0.30 mmol). The resulting solution was warmed to room temperature. After 1 h, the reaction was diluted with water, and the solution was extracted with ethyl acetate. The collected organic layers concentrated under vacuum to yield crude [2-[(8-[bis[(3,4-dimethoxyphenyl)methyl]amino]-6-(4-methylpyridin-3-yl)-2,7-naphthyridin-3-yl)carbamoyl]-3-methylcyclopropyl]methyl methanesulfonate (90 mg, 81%) as light yellow oil.

Step 7: trans-N-(8-[bis[(2,4-dimethoxyphenyl)methyl]amino]-6-(4-methylpyridin-3-yl)-2,7-naphthyridin-3-yl)-2-(cyanomethyl)-3-methylcyclopropane-1-carboxamide

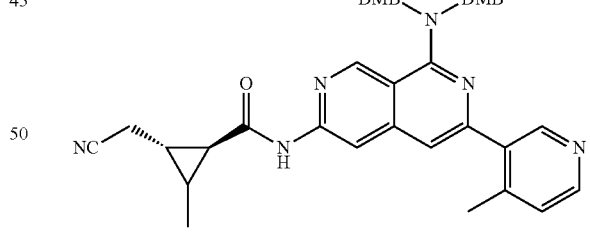

A mixture of N-(8-[bis[(2,4-dimethoxyphenyl)methyl]amino]-6-(4-methylpyridin-3-yl)-2,7-naphthyridin-3-yl)-2-(hydroxymethyl)-3-methylcyclopropane-1-carboxamide (550 mg, 0.83 mmol) and and KCN (234 mg, 3.59 mmol) in DMSO (15 mL) was heated at 50° C. for 3 h. The reaction was diluted with H$_2$O, and the resulting solution was extracted with ethyl acetate. The combined organic layers were dried over Na$_2$SO$_4$, filtered, and concentrated under vacuum to provide N-(8-[bis[(2,4-dimethoxyphenyl)methyl]amino]-6-(4-methylpyridin-3-yl)-2,7-naphthyridin-3-yl)-2-(cyanomethyl)-3-methylcyclopropane-1-carboxamide (0.50 g, 90%) as a light yellow solid.

Step 8: (1S,2S,3R)—N-[8-amino-6-(4-methylpyridin-3-yl)-2,7-naphthyridin-3-yl]-2-(cyanomethyl)-3-methylcyclopropane-1-carboxamide, (1R,2R,3S)—N-[8-amino-6-(4-methylpyridin-3-yl)-2,7-naphthyridin-3-yl]-2-(cyanomethyl)-3-methylcyclopropane-1-carboxamide, (1S,2S,3S)—N-[8-amino-6-(4-methylpyridin-3-yl)-2,7-naphthyridin-3-yl]-2-(cyanomethyl)-3-methylcyclopropane-1-carboxamide, (1R,2R,3R)—N-[8-amino-6-(4-methylpyridin-3-yl)-2,7-naphthyridin-3-yl]-2-(cyanomethyl)-3-methylcyclopropane-1-carboxamide

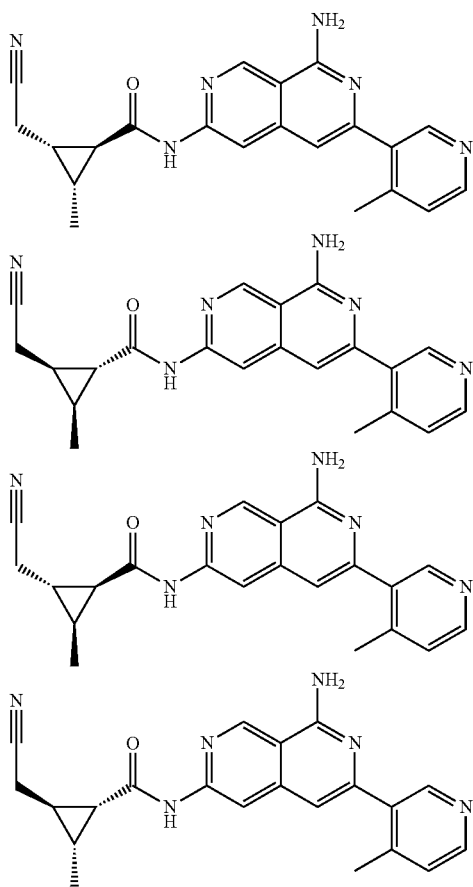

A solution of N-[8-[1,3-bis(2,4-dimethoxyphenyl)propan-2-yl]-6-(4-methylpyridin-3-yl)-2,7-naphthyridin-3-yl]-2-(cyanomethyl)-3-methylcyclopropane-1-carboxamide (0.20 g, 0.30 mmol) in trifluoroacetic acid (10 mL) was stirred for 16 h at room temperature. The reaction mixture was concentrated under vacuum. Sequential purification by Prep-HPLC followed by chiral SFC afforded 4 compounds. Compound 276: LCMS (ESI): R$_T$ (min)=3.24, [M+H]$^+$=372, method=M; $^1$H NMR (300 MHz, CD$_3$OD) δ 9.32 (s, 1H), 8.55 (s, 1H), 8.42 (d, J=5.2 Hz, 1H), 8.34 (s, 1H), 7.42 (d, J=5.2 Hz, 1H), 7.01 (s, 1H), 2.74-2.68 (m, 2H), 2.46 (s, 3H), 2.07-2.03 (m, 1H), 1.73-1.68 (m, 1H), 1.51-1.44 (m, 1H), 1.27 (d, J=8.0 Hz, 3H). Compound 277: LCMS (ESI): R$_T$ (min)=0.85, [M+H]$^+$=372, method=K-1; $^1$H NMR (300 MHz, CD$_3$OD) δ 9.32 (s, 1H), 8.55 (s, 1H), 8.42 (d, J=5.2 Hz, 1H), 8.34 (s, 1H), 7.42 (d, J=5.2 Hz, 1H), 7.01 (s, 1H), 2.74-2.68 (m, 2H), 2.46 (s, 3H), 2.07-2.03 (m, 1H), 1.73-1.68 (m, 1H), 1.51-1.44 (m, 1H), 1.27 (d, J=8.0 Hz, 3H). Compound 278: LCMS (ESI): R$_T$ (min)=0.99, [M+H]$^+$=372, method=K-1; $^1$H NMR (300 MHz, CD$_3$OD) δ 9.30 (s, 1H), 8.54 (s, 1H), 8.43 (d, J=5.2 Hz, 1H), 8.30 (s, 1H), 7.41 (d, J=5.2 Hz, 1H), 6.98 (s, 1H), 2.74-2.67 (m, 2H), 2.46 (s, 3H), 1.88-1.81 (m, 1H), 1.73-1.68 (m, 2H), 1.28 (d, J=8.0 Hz, 3H). Compound 279: LCMS (ESI): R$_T$(min)=1.79, [M+H]$^+$=372, method=M; $^1$H NMR (300 MHz, CD$_3$OD) δ 9.30 (s, 1H), 8.54 (s, 1H), 8.43 (d, J=5.2 Hz, 1H), 8.30 (s, 1H), 7.41 (d, J=5.2 Hz, 1H), 6.98 (s, 1H), 2.74-2.67 (m, 2H), 2.46 (s, 3H), 1.88-1.81 (m, 1H), 1.73-1.68 (m, 2H), 1.28 (d, J=8.0 Hz, 3H).

Example 217

(1S,2S)—N-[8-amino-6-(2-fluoro-6-methylphenyl)-2,7-naphthyridin-3-yl]-2-(1-methyl-1H-pyrazol-4-yl)cyclopropane-1-carboxamide (Compound 280) and (1R,2R)—N-[8-amino-6-(2-fluoro-6-methylphenyl)-2,7-naphthyridin-3-yl]-2-(1-methyl-1H-pyrazol-4-yl)cyclopropane-1-carboxamide (Compound 281)

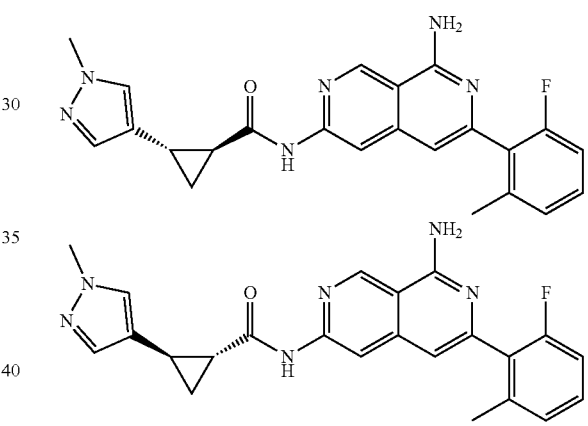

To a solution of trans-N-(8-amino-6-chloro-2,7-naphthyridin-3-yl)-2-(1-methyl-1H-pyrazol-4-yl)cyclopropane-1-carboxamide (0.20 g, 0.58 mmol) in 4:1 dioxane/water (10 mL) was sequentially added (2-fluoro-6-methylphenyl)boronic acid (0.270 g, 1.75 mmol), Pd(PPh$_3$)$_4$ (135 mg, 0.117 mmol) and K$_3$PO$_4$ (371.55 mg, 1.75 mmol). The resulting solution was heated at 100° C. for 16 h under nitrogen. The reaction was concentrated, and the resulting residue was purified by silica gel chromatography (ethyl acetate). The product was further purified by Prep-HPLC followed by chiral SFC to afford the titled compounds. Compound 280: LCMS (ESI): R$_T$(min)=2.89, [M+H]$^+$=417.2, method=K-1; $^1$H NMR (300 MHz, CD$_3$OD) δ 9.28 (s, 1H), 8.28 (s, 1H), 7.48 (s, 1H), 7.35-7.27 (m, 2H), 7.12 (d, J=7.8 Hz, 1H), 7.01 (t, J=9.0 Hz, 1H), 6.85 (s, 1H), 3.83 (s, 3H), 2.39-2.32 (m, 1H), 2.22 (s, 3H), 2.12-2.06 (m, 1H), 1.58-1.52 (m, 1H), 1.27-1.20 (m, 1H). Compound 281: LCMS (ESI): R$_T$ (min)=1.67, [M+H]+=417.20, method=K-1; $^1$H NMR (300 MHz, CD$_3$OD) δ 9.28 (s, 1H), 8.28 (s, 1H), 7.48 (s, 1H), 7.35-7.27 (m, 2H), 7.12 (d, J=7.8 Hz, 1H), 7.01 (t, J=9.0 Hz, 1H), 6.85 (s, 1H), 3.83 (s, 3H), 2.39-2.32 (m, 1H), 2.22 (s, 3H), 2.12-2.06 (m, 1H), 1.58-1.52 (m, 1H), 1.27-1.20 (m, 1H).

Example 218

(1S,2S)—N-[8-amino-6-[5-(hydroxymethyl)-2-methylphenyl]-2,7-naphthyridin-3-yl]-2-(1-methyl-1H-pyrazol-4-yl)cyclopropane-1-carboxamide (Compound 282) and (1R,2R)—N-[8-amino-6-[5-(hydroxymethyl)-2-methylphenyl]-2,7-naphthyridin-3-yl]-2-(1-methyl-H-pyrazol-4-yl)cyclopropane-1-carboxamide (Compound 283)

Example 219

(1S,2S)—N-[8-amino-6-(3-amino-2-methylphenyl)-2,7-naphthyridin-3-yl]-2-(1-methyl-1H-pyrazol-4-yl)cyclopropane-1-carboxamide (Compound 284) and (1R,2R)—N-[8-amino-6-(3-amino-2-methylphenyl)-2,7-naphthyridin-3-yl]-2-(1-methyl-1H-pyrazol-4-yl)cyclopropane-1-carboxamide (Compound 285)

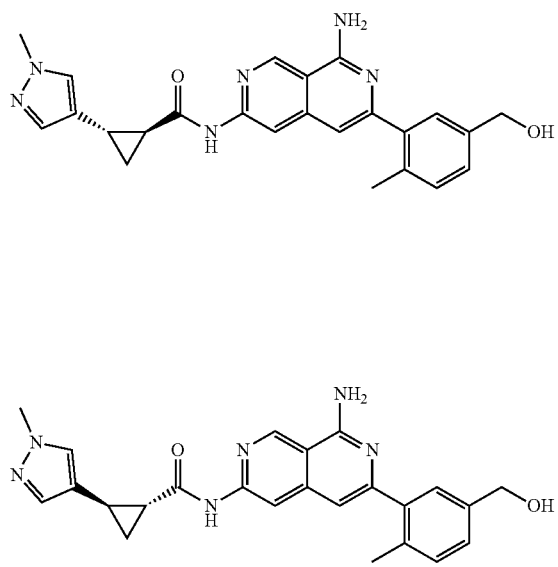 [SMILES: Cc1ccc(CO)cc1-c1cc2cc(NC(=O)[C@H]3C[C@@H]3c3cnn(C)c3)ncc2c(N)n1 ; Cc1ccc(CO)cc1-c1cc2cc(NC(=O)[C@@H]3C[C@H]3c3cnn(C)c3)ncc2c(N)n1]

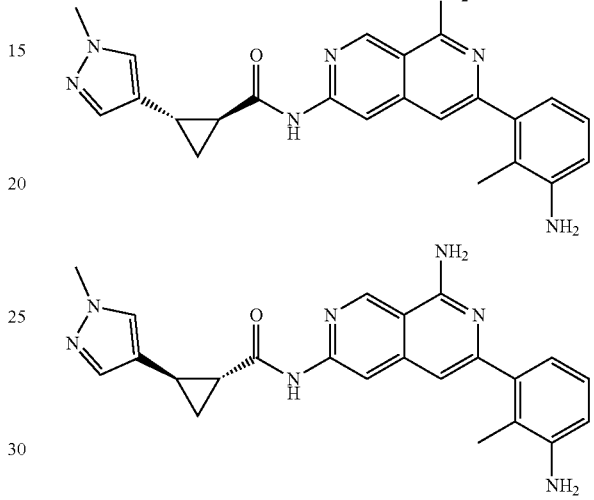

To a solution of trans-N-(8-amino-6-chloro-2,7-naphthyridin-3-yl)-2-(1-methyl-1H-pyrazol-4-yl)cyclopropane-1-carboxamide (150 mg, 0.44 mmol) in 5:1 dioxane/water (12 mL) was sequentially added [4-methyl-3-(tetramethyl-1,3,2-dioxaborolan-2-yl)phenyl]methanol (162.87 mg, 0.66 mmol), $K_3PO_4$ (278.66 mg, 1.31 mmol) and $Pd(PPh_3)_4$ (101.13 mg, 0.09 mmol). The resulting solution was heated at 100° C. for 2 h under nitrogen. The reaction was concentrated, and the resulting residue was sequentially purified by silica gel chromatography (15:1 dichloromethane/methanol), Prep-HPLC, and chiral SFC to afford the titled compounds. Compound 282: LCMS (ESI): $R_T$ (min)=1.59, [M+H]$^+$=429.2, method=K-1; $^1$H NMR (400 MHz, CD$_3$OD) δ 9.30 (s, 1H), 8.28 (s, 1H), 7.50 (s, 1H), 7.38-7.37 (m, 2H), 7.34-7.27 (m, 2H), 6.89 (s, 1H), 4.64 (s, 2H), 3.85 (s, 3H), 2.41-2.37 (m, 1H), 2.35 (s, 3H), 2.13-2.09 (m, 1H), 1.60-1.55 (m, 1H), 1.29-1.24 (m, 1H). Compound 283: LCMS (ESI): $R_T$ (min)=1.52, [M+H]$^+$=429.3, method=K-1; $^1$H NMR (400 MHz, CD$_3$OD) δ 9.30 (s, 1H), 8.28 (s, 1H), 7.50 (s, 1H), 7.38-7.37 (m, 2H), 7.34-7.27 (m, 2H), 6.89 (s, 1H), 4.64 (s, 2H), 3.85 (s, 3H), 2.41-2.37 (m, 1H), 2.35 (s, 3H), 2.13-2.09 (m, 1H), 1.60-1.55 (m, 1H), 1.29-1.24 (m, 1H).

To a solution of trans-N-(8-amino-6-chloro-2,7-naphthyridin-3-yl)-2-(1-methyl-1H-pyrazol-4-yl)cyclopropane-1-carboxamide (250 mg, 0.729 mmol) in 5:1 dioxane/water (12 mL) was sequentially added 2-methyl-3-(tetramethyl-1,3,2-dioxaborolan-2-yl)aniline (425 mg, 1.82 mmol), $Pd(PPh_3)_4$ (170 mg, 0.147 mmol) and $K_3PO_4$ (465 mg, 2.19 mmol). The resulting solution was heated at 100° C. for 12 h under nitrogen. The reaction was concentrated, and the resulting residue was sequentially purified by flash column chromatography (30:1 dichloromethane/methanol), Prep-HPLC, and chiral SFC to afford the titled compounds. Compound 284: LCMS (ESI): $R_T$ (min)=2.09, [M+H]$^+$=414.3, method=K-1; $^1$H NMR (300 MHz, DMSO-d$_6$) δ 10.89 (s, 1H), 9.32 (s, 1H), 8.18 (s, 1H), 7.56 (s, 1H), 7.29 (s, 1H), 7.17 (s, 2H), 6.92 (t, J=7.8 Hz, 1H), 6.72 (s, 1H), 6.65 (d, J=7.2 Hz, 1H), 6.57 (t, J=7.2 Hz, 1H), 4.87 (s, 2H), 3.76 (s, 3H), 2.22-2.17 (m, 2H), 2.00 (s, 3H), 1.41-1.35 (m, 1H), 1.23-1.16 (m, 1H). Compound 285: LCMS (ESI): $R_T$ (min)=2.09, [M+H]$^+$=414.3, method=K-1; $^1$H NMR (300 MHz, DMSO-d$_6$) δ 10.89 (s, 1H), 9.32 (s, 1H), 8.18 (s, 1H), 7.56 (s, 1H), 7.29 (s, 1H), 7.17 (s, 2H), 6.92 (t, J=7.8 Hz, 1H), 6.72 (s, 1H), 6.65 (d, J=7.2 Hz, 1H), 6.57 (t, J=7.2 Hz, 1H), 4.87 (s, 2H), 3.76 (s, 3H), 2.22-2.17 (m, 2H), 2.00 (s, 3H), 1.41-1.35 (m, 1H), 1.23-1.16 (m, 1H).

Example 220

(1S,2S)—N-[8-amino-6-(5-hydroxy-2-methylphenyl)-2,7-naphthyridin-3-yl]-2-(1-methyl-1H-pyrazol-4-yl)cyclopropane-1-carboxamide (Compound 286) and (1R,2R)—N-[8-amino-6-(5-hydroxy-2-methylphenyl)-2,7-naphthyridin-3-yl]-2-(1-methyl-1H-pyrazol-4-yl)cyclopropane-1-carboxamide (Compound 287)

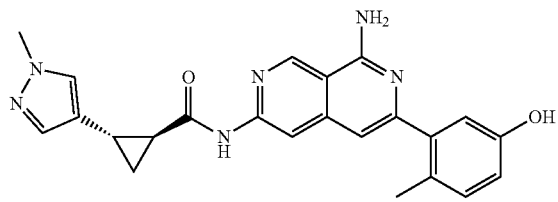

To a solution of trans-N-(8-amino-6-chloro-2,7-naphthyridin-3-yl)-2-(1-methyl-1H-pyrazol-4-yl)cyclopropane-1-carboxamide (0.20 g, 0.58 mmol) in 5:1 1,4-dioxane/water (12 mL) was sequentially added (5-hydroxy-2-methylphenyl)boronic acid (134 mg, 0.88 mmol), Pd(PPh$_3$)$_4$ (135 mg, 0.12 mmol) and K$_3$PO$_4$ (372 mg, 1.75 mmol). The resulting solution was heated at 100° C. for 5 h under nitrogen. The reaction was filtered, and the filtrate was concentrated under vacuum. Purification by Prep-HPLC followed by chiral SFC afforded the titled compounds. Compound 286: LCMS (ESI): R$_T$ (min)=2.22, [M+H]+=415.3, method=K-1; $^1$H NMR (300 MHz, CD$_3$OD) δ 9.26 (s, 1H), 8.27 (s, 1H), 7.50 (s, 1H), 7.37 (s, 1H), 7.10 (d, J=8.0 Hz, 1H), 6.84 (d, J=8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H). Compound 287: LCMS (ESI): R$_T$ (min)=1.26, [M+H]+=415.3, method=K-1; $^1$H NMR (300 MHz, CD$_3$OD) δ 9.26 (s, 1H), 8.27 (s, 1H), 7.50 (s, 1H), 7.37 (s, 1H), 7.10 (d, J=8.0 Hz, 1H), 6.84 (d, J=8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H).

Example 221

(1S,2S)—N-[8-amino-6-(5-methoxy-2-methylphenyl)-2,7-naphthyridin-3-yl]-2-(1-methyl-1H-pyrazol-4-yl)cyclopropane-1-carboxamide (Compound 288) and (1R,2R)—N-[8-amino-6-(5-methoxy-2-methylphenyl)-2,7-naphthyridin-3-yl]-2-(1-methyl-H-pyrazol-4-yl)cyclopropane-1-carboxamide (Compound 289)



To a solution of trans-N-(8-amino-6-chloro-2,7-naphthyridin-3-yl)-2-(1-methyl-1H-pyrazol-4-yl)cyclopropane-1-carboxamide (216 mg, 0.63 mmol) in 5:1 1,4-dioxane/water (12 mL) was added 2-(5-methoxy-2-methylphenyl)-4,4,5,5-tetramethyl-1,3,2-dioxaborolane (0.20 g, 0.81 mmol), Pd(PPh$_3$)$_4$ (136 mg, 0.12 mmol) and K$_3$PO$_4$ (372 mg, 1.75 mmol). The resulting solution was heated at 100° C. for 12 h under nitrogen. The reaction was filtered, and the filtrate was concentrated under vacuum. Purification by Prep-HPLC followed by chiral SFC afforded the titled compounds. Compound 288: LCMS (ESI): R$_T$ (min)=2.29, [M+H]$^+$=429.3, method=K-1; $^1$H NMR (300 MHz, DMSO-d$_6$) δ 10.93 (s, 1H), 9.34 (s, 1H), 8.22 (s, 1H), 7.56 (s, 1H), 7.29-7.16 (m, 4H), 6.96 (d, J=2.7 Hz, 1H), 6.88-6.85 (m, 2H), 3.76 (d, J=3.9 Hz, 6H), 2.27 (s, 3H), 2.22-2.17 (m, 2H), 1.40-1.38 (m, 1H), 1.19-1.18 (m, 1H). Compound 289: LCMS (ESI): R$_T$ (min)=2.30, [M+H]$^+$=429.3, method=K-1; $^1$H NMR (300 MHz, DMSO-d$_6$) δ 10.93 (s, 1H), 9.34 (s, 1H), 8.22 (s, 1H), 7.56 (s, 1H), 7.29-7.16 (m, 4H), 6.96 (d, J=2.7 Hz, 1H), 6.88-6.85 (m, 2H), 3.76 (d, J=3.9 Hz, 6H), 2.27 (s, 3H), 2.22-2.17 (m, 2H), 1.40-1.38 (m, 1H), 1.19-1.18 (m, 1H).

Example 222

3-(1-amino-6-[[(1S,2S)-2-(1-methyl-1H-pyrazol-4-yl)cyclopropane]amido]-2,7-naphthyridin-3-yl)-N,N,4-trimethylbenzamide (Compound 290) and 3-(1-amino-6-[[(1R,2R)-2-(1-methyl-1H-pyrazol-4-yl)cyclopropane]amido]-2,7-naphthyridin-3-yl)-N,N,4-trimethylbenzamide (Compound 291)

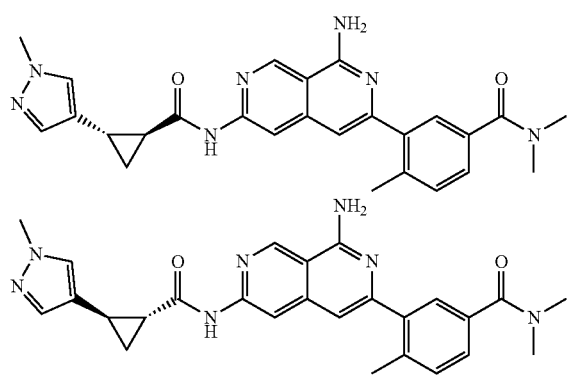

Step 1: 3-bromo-N,N,4-trimethylbenzamide

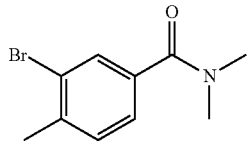

To a solution of 3-bromo-4-methylbenzoic acid (5.00 g, 23.2 mmol) in dichloromethane (100 mL) was added diisopropylethylamine (12.02 g, 93.00 mmol), HATU (13.26 g, 34.87 mmol) and dimethylamine (2.10 g, 46.6 mmol) at room temperature. After 16 h, the reaction was concentrated under vacuum, and the resulting residue was purified by silica gel chromatography (1:1 ethyl acetate/petroleum ether) to afford 3-bromo-N,N,4-trimethylbenzamide (4.7 g, 83%) as a white solid. LCMS (ESI): [M+H]$^+$=242.1

Step 2: N,N,4-trimethyl-3-(tetramethyl-1,3,2-dioxaborolan-2-yl)benzamide

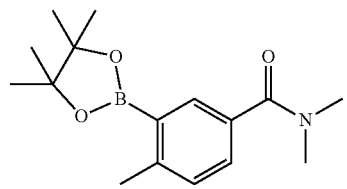

To a solution of 3-bromo-N,N,4-trimethylbenzamide (2.50 g, 10.3 mmol) in dioxane (100 mL) was added 4,4,5,5-tetramethyl-2-(tetramethyl-1,3,2-dioxaborolan-2-yl)-1,3,2-dioxaborolane (5.24 g, 20.6 mmol), KOAc (3.04 g, 30.97 mmol) and Pd(dppf)Cl$_2$ (755.54 mg, 1.03 mmol). The resulting solution was heated at 100° C. under nitrogen. After 16 h, the reaction was concentrated under vacuum, and the resulting residue was purified by silica gel chromatography (10:1 dichloromethane/methanol) to afford N,N,4-trimethyl-3-(tetramethyl-1,3,2-dioxaborolan-2-yl)benzamide (1.1 g, 37%) as a orange oil. LCMS (ESI): [M+H]$^+$=290.2.

Step 3: 3-(1-amino-6-[[(1S,2S)-2-(1-methyl-1H-pyrazol-4-yl)cyclopropane]amido]-2,7-naphthyridin-3-yl)-N,N,4-trimethylbenzamide and 3-(1-amino-6-[[(1R,2R)-2-(1-methyl-1H-pyrazol-4-yl)cyclopropane]amido]-2,7-naphthyridin-3-yl)-N,N,4-trimethylbenzamide

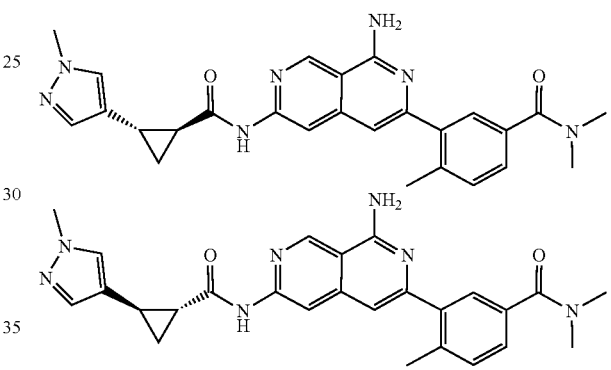

To a solution of trans-N-(8-amino-6-chloro-2,7-naphthyridin-3-yl)-2-(1-methyl-1H-pyrazol-4-yl)cyclopropane-1-carboxamide (0.20 g, 0.58 mmol) in 5:1 dioxane/water (12 mL) was added K$_3$PO$_4$ (372 mg, 1.75 mmol), N,N,4-trimethyl-3-(tetramethyl-1,3,2-dioxaborolan-2-yl)benzamide (506 mg, 1.75 mmol) and Pd(PPh$_3$)$_4$ (134.84 mg, 0.11 mmol). The resulting solution was heated at 100° C. for 2 h under nitrogen. The reaction was concentrated, and the resulting residue was sequentially purified by silica gel chromatography (20:1 dichloromethane/methanol and chiral SFC to afford the titled compounds. Compound 290: LCMS (ESI): R$_T$ (min)=1.25, [M+H]+=470.3, method=K-1; $^1$H NMR (300 MHz, CD$_3$OD) δ 9.30 (s, 1H), 8.33 (s, 1H), 7.55-7.47 (m, 2H), 7.46-7.36 (m, 3H), 6.95 (s, 1H), 3.86 (s, 3H), 3.12 (d, J=10.1 Hz, 6H), 2.43-2.30 (m, 4H), 2.18-2.05 (m, 1H), 1.65-1.50 (m, 1H), 1.35-1.20 (m, 1H). Compound 291: LCMS (ESI): R$_T$ (min)=1.25, [M+H]$^+$=470.3, method=K-1; $^1$H NMR (300 MHz, CD$_3$OD) δ 9.30 (s, 1H), 8.33 (s, 1H), 7.55-7.47 (m, 2H), 7.46-7.36 (m, 3H), 6.95 (s, 1H), 3.86 (s, 3H), 3.12 (d, J=10.1 Hz, 6H), 2.43-2.30 (m, 4H), 2.18-2.05 (m, 1H), 1.65-1.50 (m, 1H), 1.35-1.20 (m, 1H).

Example 223

(1S,2S)—N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide (Compound 292) and (1R,2R)—N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide (Compound 293)

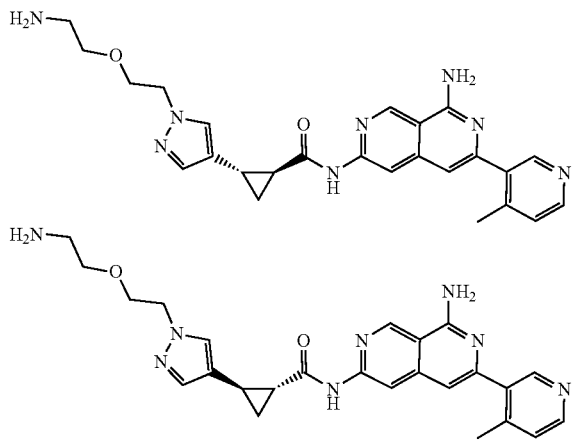

Step 1: 4-iodo-1-(oxan-2-yl)-1H-pyrazole

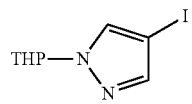

To a solution of 4-iodo-1H-pyrazole (50.0 g, 258 mmol), 3,4-dihydro-2H-pyran (65.05 g, 773.3 mmol), and p-toluenesulfonic acid (3.11 g, 18.1 mmol) in ethyl acetate (300 mL) was heated at 90° C. After 2 h, the reaction was concentrated, and the residue was purified by silica gel chromatography (95:5 petroleum ether/ethyl acetate) to afford 4-iodo-1-(oxan-2-yl)-1H-pyrazole (65 g, 91%) as a yellow oil. LCMS (ESI): [M+H]$^+$=279.1.

Step 2: ethyl (2E)-3-[1-(oxan-2-yl)-1H-pyrazol-4-yl]prop-2-enoate

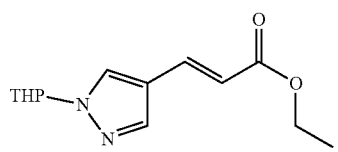

A mixture of 4-iodo-1-(oxan-2-yl)-1H-pyrazole (50.0 g, 180 mmol), ethyl prop-2-enoate (72 g, 720 mmol), Pd(OAc)$_2$ (6.05 g, 27.0 mmol), P(o-Tol)$_3$ (16.4 g, 54 mmol) and triethylamine (109 g, 1.08 mol) in CH$_3$CN (250 mL) was heated at 110° C. for 3 h under nitrogen. The reaction was concentrated, and the resulting residue was purified by silica gel chromatography (9:1 petroleum ether/ethyl acetate) to afford ethyl (2E)-3-[1-(oxan-2-yl)-1H-pyrazol-4-yl]prop-2-enoate (35 g, 78%) as a yellow oil. LCMS (ESI): [M+H]$^+$=251.3.

Step 3: trans-ethyl 2-(1-(tetrahydro-2H-pyran-2-yl)-1H-pyrazol-4-yl)cyclopropanecarboxylate

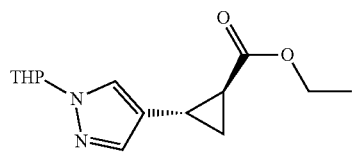

To a solution of trimethylsulfoxonium iodide (21 g, 95 mmol) in DMSO (300 mL) at room temperature was added sodium hydride (3.68 g, 153.35 mmol). After 30 min, ethyl (2E)-3-[1-(oxan-2-yl)-1H-pyrazol-4-yl]prop-2-enoate (20.0 g, 79.9 mmol) was added, and the resulting solution was maintained at 25° C. for 16 h. The reaction was diluted with H$_2$O, and the solution was extracted with ethyl acetate. The collected organic layer was concentrated. Purification by flash column chromatography (99:1 dichloromethane/methanol) provided trans-ethyl 2-(1-(tetrahydro-2H-pyran-2-yl)-1H-pyrazol-4-yl)cyclopropanecarboxylate (5.7 g, 27%) as a yellow oil. LCMS (ESI): [M+H]$^+$=265.3.

Step 4: (1S,2S)-ethyl 2-(1H-pyrazol-4-yl)cyclopropanecarboxylate

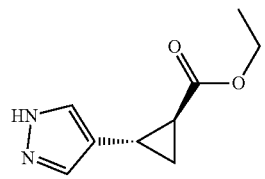

A solution of trans-ethyl 2-(1-(tetrahydro-2H-pyran-2-yl)-1H-pyrazol-4-yl)cyclopropanecarboxylate (5.7 g, 21.6 mmol) in trifluoroacetic acid (10 mL) and dichloromethane (50 mL) was stirred for 3 h at 25° C. The reaction was concentrated, and the resulting residue was purified by flash column chromatography (97:3 dichloromethane/methanol) to afford trans-ethyl 2-(1H-pyrazol-4-yl)cyclopropanecarboxylate (2.4 g, 62%) as a yellow oil. LCMS (ESI): [M+H]$^+$=181.2

Step 5: tert-butyl N-[2-[2-(methanesulfonyloxy)ethoxy]ethyl]carbamate

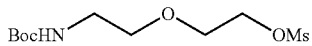

To an ice-cooled solution of tert-butyl N-[2-(2-hydroxyethoxy)ethyl]carbamate (12.0 g, 58.5 mmol) and triethylamine (17.8 g, 175 mmol) in dichloromethane (100 mL) was added MsCl (10.05 g, 87.73 mmol). After 15 min, the reaction mixture was washed with H$_2$O. The aqueous layer was extracted with dichloromethane. The combined organic

811 layers were concentrated under vacuum to afford crude tert-butyl N-[2-[2-(methanesulfonyloxy)ethoxy]ethyl]carbamate (20 g) as a yellow oil.

Step 6: trans-ethyl-2-[1-[2-(2-[[(tert-butoxy)carbonyl]amino]ethoxy)ethyl]-1H-pyrazol-4-yl]cyclopropane-1-carboxylate

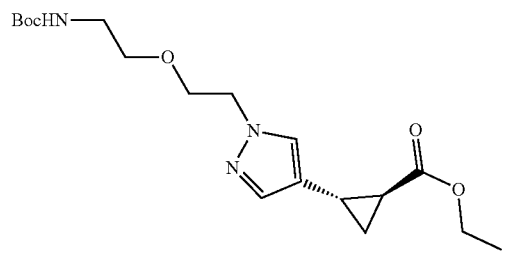 [SMILES: CCOC(=O)[C@H]1C[C@@H]1c1cnn(CCOCCNC(=O)OC(C)(C)C)c1]

A suspension of tert-butyl N-[2-[2-(methanesulfonyloxy)ethoxy]ethyl]carbamate (16.04 g, 56.61 mmol), trans-ethyl-2-(1H-pyrazol-4-yl)cyclopropane-1-carboxylate (6.80 g, 37.7 mmol), $Cs_2CO_3$ (12.29 g, 37.72 mmol) and N,N-dimethylformamide (120 mL) was heated at 80° C. After 4 h, the resulting mixture was diluted with $H_2O$. The aqueous solution was extracted with ethyl acetate, and the combined organic extracts were concentrated. Purification by flash column chromatography (96:4 dichloromethane/methanol) provided trans-ethyl-2-[1-[2-(2-[[(tert-butoxy)carbonyl]amino]ethoxy)ethyl]-1H-pyrazol-4-yl]cyclopropane-1-carboxylate (12.2 g, 88%) as a yellow oil. LCMS (ESI): $[M+H]^+$=368.4.

Step 7: trans-2-[1-[2-(2-[[(tert-butoxy)carbonyl]amino]ethoxy)ethyl]-1H-pyrazol-4-yl]cyclopropane-1-carboxylic acid

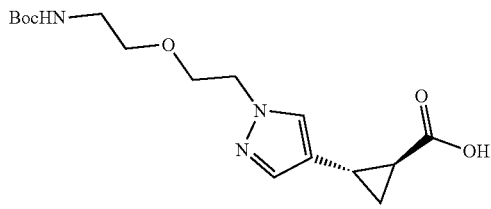 [SMILES: CC(C)(C)OC(=O)NCCOCCn1cc([C@H]2C[C@@H]2C(=O)O)cn1]

To a solution of trans-ethyl-2-[1-[2-(2-[[(tert-butoxy)carbonyl]amino]ethoxy)ethyl]-1H-pyrazol-4-yl]cyclopropane-1-carboxylate (12.2 g, 33.2 mmol) in tetrahydrofuran (100 mL)/ethanol (100 mL)/water (40 mL) was added $LiOH·H_2O$ (9.75 g, 232 mmol) at 25° C. After 16 h, the reaction mixture was washed with $H_2O$. The aqueous solution was washed with dichloromethane. The aqueous was acidified to pH=5 with 12% hydrogen chloride aqueous solution. The acidic solution was extracted with ethyl acetate, and the extract was concentrated to afford crude trans-2-[1-[2-(2-[[(tert-butoxy)carbonyl]amino]ethoxy)ethyl]-1H-pyrazol-4-yl]cyclopropane-1-carboxylic acid (4 g, 35%) as a yellow oil. LCMS (ESI): $[M-H]^-$=338.1.

812

Step 8: tert-butyl 2-(2-(4-((1S,2S)-2-(8-(bis(2,4-dimethoxybenzyl)amino)-6-(4-methylpyridin-3-yl)-2,7-naphthyridin-3-ylcarbamoyl)cyclopropyl)-1H-pyrazol-1-yl)ethoxy)ethylcarbamate

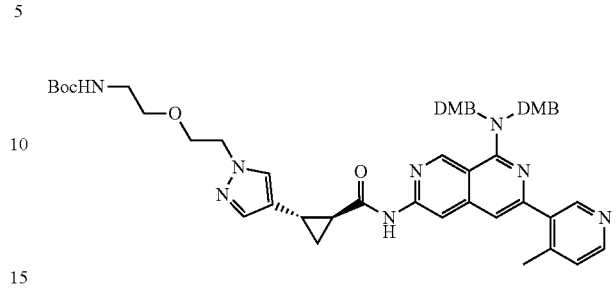

A mixture of 1-N,1-N-bis[(2,4-dimethoxyphenyl)methyl]-3-(4-methylpyridin-3-yl)-2,7-naphthyridine-1,6-diamine (55 mg, 0.10 mmol), trans-2-[1-[2-(2-[[(tert-butoxy)carbonyl]amino]ethoxy)ethyl]-1H-pyrazol-4-yl]cyclopropane-1-carboxylic acid (0.040 g, 0.12 mmol), pyridine (1 mL) and $POCl_3$ (30 mg, 0.196 mmol) in dichloromethane (5 mL) was stirred for 30 min at room temperature. The reaction was then diluted with water, and the resulting solution was extracted with ethyl acetate. The combined organic was concentrated and purified by flash column chromatography (10:1 dichloromethane/methanol) afforded trans-tert-butyl 2-(2-(4-(2-(8-(bis(2,4-dimethoxybenzyl)amino)-6-(4-methylpyridin-3-yl)-2,7-naphthyridin-3-ylcarbamoyl)cyclopropyl)-1H-pyrazol-1-yl)ethoxy)ethylcarbamate (60 mg) as a yellow solid. LCMS (ESI): $[M-H]^-$=873.6

Step 9: (1S,2S)—N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide and (1R,2R)—N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide

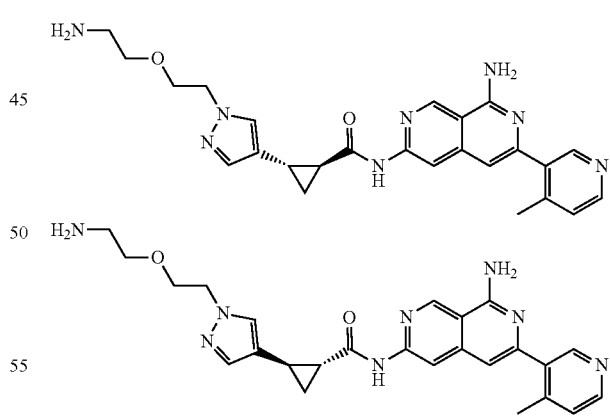

A solution of tert-butyl N-[2-(2-[4-[(1S,2S)-2-[(8-[bis[(2,4-dimethoxyphenyl)methyl]amino]-6-(4-methylpyridin-3-yl)-2,7-naphthyridin-3-yl)carbamoyl]cyclopropyl]-1H-pyrazol-1-yl]ethoxy)ethyl]carbamate (0.20 g, 0.23 mmol) in trifluoroacetic acid (4 mL) and dichloromethane (4 mL) was stirred for 6 h at 25° C. The resulting mixture was concentrated under vacuum, and the crude product was purified by Prep-HPLC followed by chiral SFC to afford the titled compounds. Compound 292: LCMS (ESI): $R_t$(min)=1.94,

[M+H]⁺=473.3, method=K-1; ¹H NMR (400 MHz, CD₃OD) δ 9.30 (s, 1H), 8.54 (s, 1H), 8.44 (d, J=5.1 Hz, 1H), 8.33 (s, 1H), 7.61 (s, 1H), 7.48-7.36 (m, 2H), 6.99 (m, 1H), 4.30-4.28 (m, 2H), 3.82-3.80 (m, 2H), 3.66-3.49 (m, 2H), 2.85-2.82 (m, 2H), 2.46 (s, 3H), 2.42-2.37 (m, 1H), 2.14-2.10 (m, 1H), 1.61-1.56 (m, 1H), 1.29-1.26 (m, 1H). Compound 293: LCMS (ESI): R_T (min)=1.94, [M+H]+=473.2, method=K-1; ¹H NMR (400 MHz, CD₃OD) δ 9.30 (s, 1H), 8.54 (s, 1H), 8.44 (d, J=5.1 Hz, 1H), 8.33 (s, 1H), 7.61 (s, 1H), 7.48-7.36 (m, 2H), 6.99 (m, 1H), 4.30-4.28 (m, 2H), 3.82-3.80 (m, 2H), 3.66-3.49 (m, 2H), 2.85-2.82 (m, 2H), 2.46 (s, 3H), 2.42-2.37 (m, 1H), 2.14-2.10 (m, 1H), 1.61-1.56 (m, 1H), 1.29-1.26 (m, 1H).

Example 224

(1S,3r,5R,6r)-N-(8-amino-6-(4-methylpyridin-3-yl)-2,7-naphthyridin-3-yl)-3-(3-methoxyazetidin-1-yl)bicyclo[3.1.0]hexane-6-carboxamide (Compound 294)

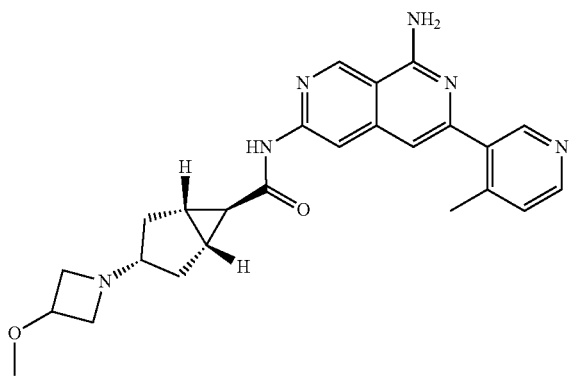 [SMILES: COC1CN([C@H]2C[C@@H]3[C@H](C2)[C@H]3C(=O)Nc2cc3cc(-c4cnccc4C)nc(N)c3cn2)C1]

Step 1: (1S,3r,5R,6r)-N-(8-(2,4-dimethoxybenzylamino)-6-(4-methylpyridin-3-yl)-2,7-naphthyridin-3-yl)-3-(3-methoxyazetidin-1-yl)bicyclo[3.1.0]hexane-6-carboxamide

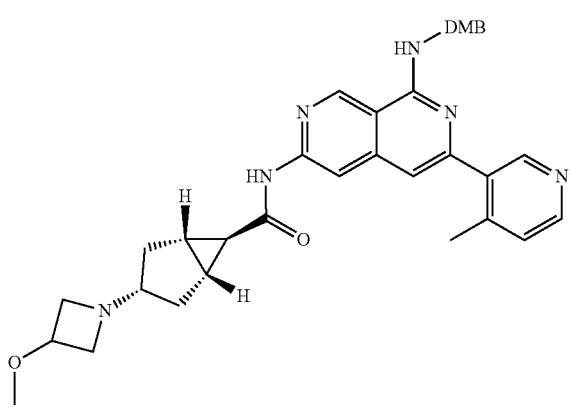

A mixture of (1R,5S,6R)—N-(8-[bis[(2,4-dimethoxyphenyl)methyl]amino]-6-(4-methylpyridin-3-yl)-2,7-naphthyridin-3-yl)-3-oxobicyclo[3.1.0]hexane-6-carboxamide (0.20 g, 0.29 mmol) (see Example 226), 3-methoxyazetidine hydrochloride (183 mg, 1.48 mmol), NaBH₃CN (55.96 mg, 0.89 mmol), and AcOH (0.89 mg, 0.01 mmol) in methanol (10 mL) was heated at 60° C. After 16 h, the reaction mixture was concentrated, and the resulting residue was purified by silica gel chromatography (92:8 dichloromethane/methanol) to provide (1R,3r,5S,6S)—N-[8-[(2,4-dimethoxyphenyl)amino]-6-(4-methylpyridin-3-yl)-2,7-naphthyridin-3-yl]-3-(3-methoxyazetidin-1-yl)bicyclo[3.1.0]hexane-6-carboxamide (0.20 g) as a yellow solid. LCMS (ESI): [M+H]⁺=595.4.

Step 2: (1S,3r,5R,6r)-N-(8-amino-6-(4-methylpyridin-3-yl)-2,7-naphthyridin-3-yl)-3-(3-methoxyazetidin-1-yl)bicyclo[3.1.0]hexane-6-carboxamide

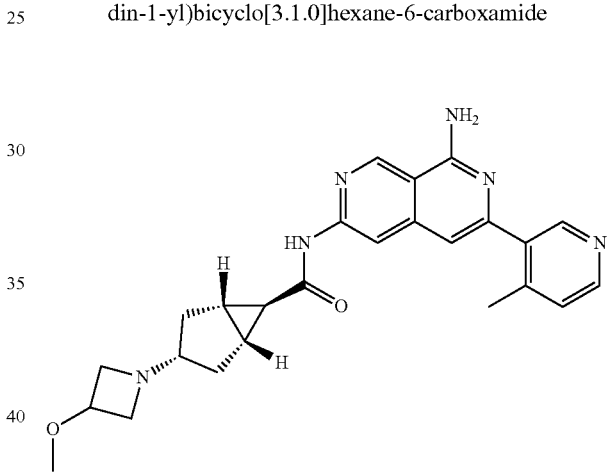

A solution of (1R,3r,5S,6S)—N-(8-[[(2,4-dimethoxyphenyl)methyl]amino]-6-(4-methylpyridin-3-yl)-2,7-naphthyridin-3-yl)-3-(3-methoxyazetidin-1-yl)bicyclo[3.1.0]hexane-6-carboxamide (0.20 g, 0.33 mmol) in trifluoroacetic acid (10 mL)/dichloromethane (5 mL) was stirred for 6 h at 25° C. The reaction mixture was concentrated, and the crude product was purified by Prep-HPLC to afford (1R,3r,5S,6S)—N-[8-amino-6-(4-methylpyridin-3-yl)-2,7-naphthyridin-3-yl]-3-(3-methoxyazetidin-1-yl)bicyclo[3.1.0]hexane-6-carboxamide formic acid salt (4.4 mg, 3%) as an off-white solid. LCMS (ESI): R_T (min)=1.91, [M+H]⁺=445.2, method=K-1; ¹H NMR (400 MHz, CD₃OD) δ 9.29 (s, 1H), 8.53 (s, 1H), 8.44 (d, J=5.1 Hz, 1H), 8.26 (s, 1H), 7.40 (d, J=5.1 Hz, 1H), 6.97 (s, 1H), 4.08-4.02 (m, 1H), 3.69-3.49 (m, 2H), 3.32 (s, 3H), 3.24 (s, 1H), 3.18-3.07 (m, 2H), 2.46 (s, 3H), 2.30 (t, J=3.0 Hz, 1H), 2.18-2.16 (m, 2H), 2.01-1.92 (m, 2H), 1.73-1.69 (m, 2H).

Example 225

(1S,2S)—N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide (Compound 295) and (1R,2R)—N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide (Compound 296)

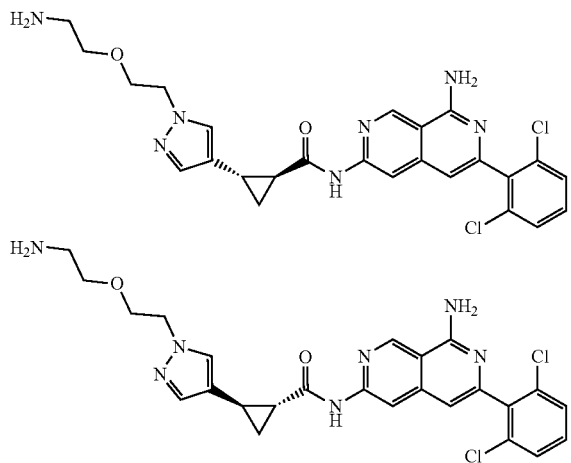

Step 1: 2-hydroxypropan-2-yl N-[2-(2-[4-[(1S,2S)-2-[(6,8-dichloro-2,7-naphthyridin-3-yl)carbamoyl]cyclopropyl]-1H-pyrazol-1-yl]ethoxy)ethyl]carbamate

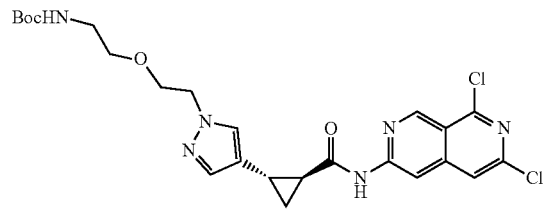 [SMILES: CC(C)(C)OC(=O)NCCOCCn1cc([C@H]2C[C@@H]2C(=O)Nc2cc3cc(Cl)nc(Cl)c3cn2)cn1]

To an ice-cooled solution of trans-2-[1-[2-(2-[[(tert-butoxy)carbonyl]amino]ethoxy)ethyl]-1H-pyrazol-4-yl]cyclopropane-1-carboxylic acid (1.73 g, 5.09 mmol), 6,8-dichloro-2,7-naphthyridin-3-amine (1.28 g, 5.98 mmol), and pyridine (5 mL) in dichloromethane (25 mL) was added POCl$_3$ (2.34 g, 15.26 mmol). The resulting solution was warmed to room temperature for 30 min. The reaction was slowly diluted with water, and the aqueous solution was extracted with ethyl acetate. The collected organic was concentrated under vacuum, and the residue was purified by silica gel chromatography (10:1 dichloromethane/methanol) to afford 2-hydroxypropan-2-yl trans-N-[2-(2-[4-[2-[(6,8-dichloro-2,7-naphthyridin-3-yl)carbamoyl]cyclopropyl]-1H-pyrazol-1-yl]ethoxy)ethyl]carbamate (2.0 g, 73%) as a light yellow solid. LCMS (ESI): [M+H]$^+$=535.4.

Step 2: trans-tert-butyl N-[2-(2-[4-[2-[(8-[bis[(2,4-dimethoxyphenyl)methyl]amino]-6-chloro-2,7-naphthyridin-3-yl)carbamoyl]cyclopropyl]-1H-pyrazol-1-yl]ethoxy)ethyl]carbamate

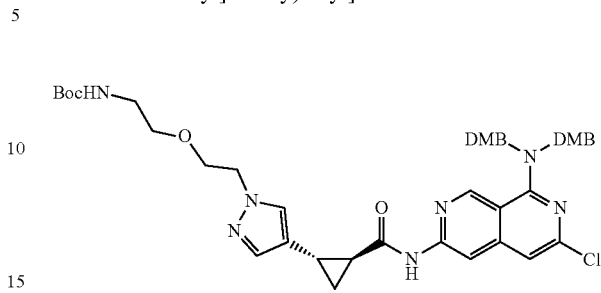

A mixture of trans-tert-butyl N-[2-(2-[4-[2-[(6,8-dichloro-2,7-naphthyridin-3-yl)carbamoyl]cyclopropyl]-1H-pyrazol-1-yl]ethoxy)ethyl]carbamate (2.0 g, 3.73 mmol), bis[(2,4-dimethoxyphenyl)methyl]amine (4.74 g, 14.9 mmol) and triethylamine (1.89 g, 18.7 mmol) in dioxane (40 mL) was heated at 110° C. After 12 h, the reaction was concentrated, and the resulting residue was purified by silica gel chromatography (10:1 dichloromethane/methanol) to provide trans-tert-butyl N-[2-(2-[4-[2-[(8-[bis[(2,4-dimethoxyphenyl)methyl]amino]-6-chloro-2,7-naphthyridin-3-yl)carbamoyl]cyclopropyl]-1H-pyrazol-1-yl]ethoxy)ethyl]carbamate (2.5 g, 82%) as a light yellow solid. LCMS (ESI): [M+H]$^+$=816.3.

Step 3: trans-tert-butyl 2-(2-(4-(2-(8-(bis(2,4-dimethoxybenzyl)amino)-6-(2,6-dichlorophenyl)-2,7-naphthyridin-3-ylcarbamoyl)cyclopropyl)-1H-pyrazol-1-yl)ethoxy)ethylcarbamate

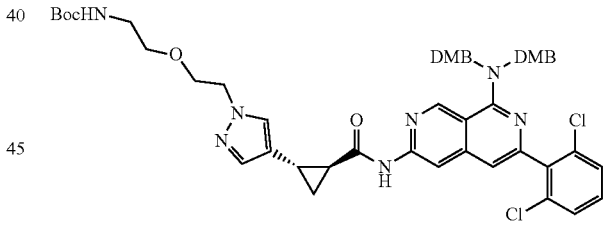

A mixture of trans-tert-butyl N-[2-(2-[4-[2-[(8-[bis[(2,4-dimethoxyphenyl)methyl]amino]-6-chloro-2,7-naphthyridin-3-yl)carbamoyl]cyclopropyl]-1H-pyrazol-1-yl]ethoxy)ethyl]carbamate (2.28 g, 2.79 mmol), (2,6-dichlorophenyl)boronic acid (6.39 g, 33.48 mmol), Pd(PPh$_3$)$_4$ (645 mg, 0.55 mmol), and sodium bicarbonate (2.81 g, 33.45 mmol) in ethanol (60 mL)/water (6 mL)/toluene (60 mL) was heated at 100° C. under nitrogen. After 12 h, the reaction was concentrated, and the resulting residue was purified by silica gel chromatography (10:1 dichloromethane/methanol) to yield tert-butyl 2-(2-(4-((1S,2S)-2-(8-(bis(2,4-dimethoxybenzyl)amino)-6-(2,6-dichlorophenyl)-2,7-naphthyridin-3-ylcarbamoyl)cyclopropyl)-1H-pyrazol-1-yl)ethoxy)ethylcarbamate (2.0 g, 77%) as a brown oil. LCMS (ESI): [M+H]$^+$=926.9.

Step 4: (1S,2S)—N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide and (1R,2R)—N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide

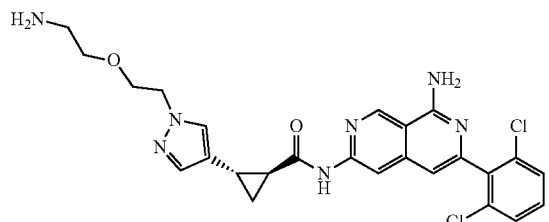

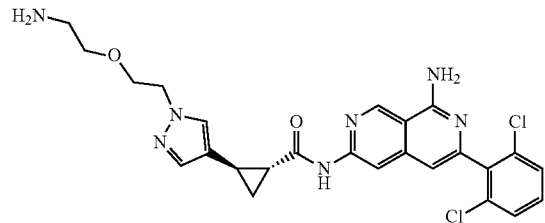

A solution of trans-tert-butyl N-[2-(2-[4-[2-[(8-[bis[(2,4-dimethoxyphenyl)methyl]amino]-6-(2,6-dichlorophenyl)-2,7-naphthyridin-3-yl)carbamoyl]cyclopropyl]-1H-pyrazol-1-yl]ethoxy)ethyl]carbamate (2.55 g, 2.75 mmol) in trifluoroacetic acid (10 mL) was heated at 80° C. After 20 min, the mixture was concentrated under vacuum, and the resulting residue was diluted with dichloromethane. The solution was basified to pH=8 with 7M NH₃/methanol and concentrated. Purification by Prep-HPLC followed by chiral SFC afforded the titled compounds. Compound 295: LCMS (ESI): $R_T$ (min)=1.43, [M+H]$^+$=526.1, method=K-1; $^1$H NMR (300 MHz, DMSO-d₆) δ 10.98 (s, 1H), 9.38 (s, 1H), 8.23 (s, 1H), 7.62 (s, 1H), 7.58-7.55 (m, 2H), 7.48-7.42 (m, 3H), 7.32 (s, 1H), 6.80 (s, 1H), 4.19 (t, J=6.0 Hz, 2H), 3.71 (t, J=6.0 Hz, 2H), 3.35-3.26 (m, 2H), 2.62 (t, J=6.0 Hz, 2H), 2.22 (t, J=6.0 Hz, 2H), 2.00-1.80 (m, 2H), 1.42-1.36 (m, 1H), 1.24-1.17 (m, 1H). Compound 296: LCMS (ESI): $R_T$ (min)=1.43, [M+H]+=526.1, method=K-1; $^1$H NMR (300 MHz, DMSO-d₆) δ 10.98 (s, 1H), 9.38 (s, 1H), 8.23 (s, 1H), 7.62 (s, 1H), 7.58-7.55 (m, 2H), 7.48-7.42 (m, 3H), 7.32 (s, 1H), 6.80 (s, 1H), 4.19 (t, J=6.0 Hz, 2H), 3.71 (t, J=6.0 Hz, 2H), 3.35-3.26 (m, 2H), 2.62 (t, J=6.0 Hz, 2H), 2.22 (t, J=6.0 Hz, 2H), 2.00-1.80 (m, 2H), 1.42-1.36 (m, 1H), 1.24-1.17 (m, 1H).

Example 226

(exo)-N-[8-amino-6-(4-methylpyridin-3-yl)-2,7-naphthyridin-3-yl]-3-(morpholin-4-yl)bicyclo[3.1.0]hexane-6-carboxamide (Compound 297)

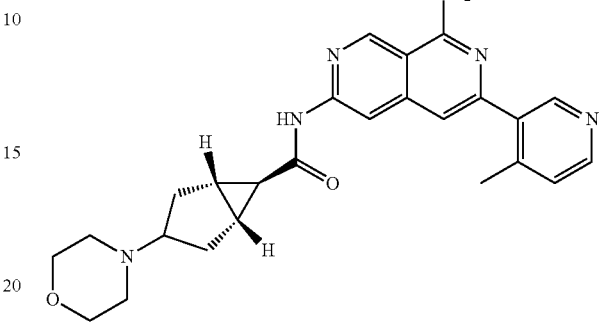

Step 1: (exo)-3-[(tert-butyldiphenylsilyl)oxy]bicyclo[3.1.0]hexane-6-carboxylic acid

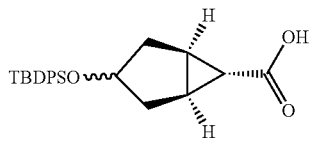

To a solution of ethyl (exo)-3-[(tert-butyldiphenylsilyl)oxy]bicyclo[3.1.0]hexane-6-carboxylate (3.20 g, 7.83 mmol) in ethanol (30 mL) and water (30 mL) was added sodium hydroxide (1.88 g, 47.0 mmol) at 25° C. After 6 h, the organic removed under vacuum. The remaining aqueous solution was washed with ethyl acetate. The aqueous solution was acidified to pH=3 with concentrated hydrochloric acid and concentrated under vacuum to afford crude (exo)-3-[(tert-butyldiphenylsilyl)oxy]bicyclo[3.1.0]hexane-6-carboxylic acid (3 g) as a white solid. LCMS (ESI): [M+H]$^+$=379.2.

Step 2: (exo)-3-[(tert-butyldiphenylsilyl)oxy]-N-(6,8-dichloro-2,7-naphthyridin-3-yl)bicyclo[3.1.0]hexane-6-carboxamide

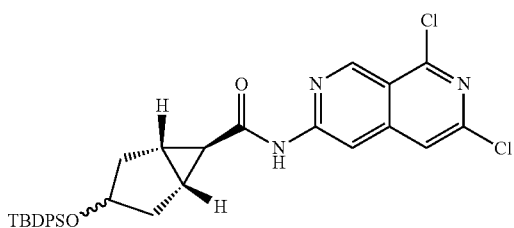

A mixture of (exo)-3-[(tert-butyldiphenylsilyl)oxy]bicyclo[3.1.0]hexane-6-carboxylic acid (3.00 g, 7.88 mmol), 6,8-dichloro-2,7-naphthyridin-3-amine (1.69 g, 7.90 mmol), POCl₃ (3.63 g, 23.67 mmol), and pyridine (4 mL) in dichloromethane (40 mL) was stirred for 30 min at 25° C. The reaction was slowly diluted with water, and the resulting mixture was extracted with dichloromethane. The organic extracts were concentrated, and the resulting residue was purified by silica gel chromatography (1:9 ethyl acetate/petroleum ether) to afford (1R,5S,6R)-3-[(tert-butyldiphenylsilyl)oxy]-N-(6,8-dichloro-2,7-naphthyridin-3-yl)bicyclo[3.1.0]hexane-6-carboxamide (3.7 g, 81%) as a yellow oil. LCMS (ESI): [M+H]$^+$=576.3.

Step 3: (exo)-N-(8-[bis[(2,4-dimethoxyphenyl)methyl]amino]-6-chloro-2,7-naphthyridin-3-yl)-3-[(tert-butyldiphenylsilyl)oxy]bicyclo[3.1.0]hexane-6-carboxamide

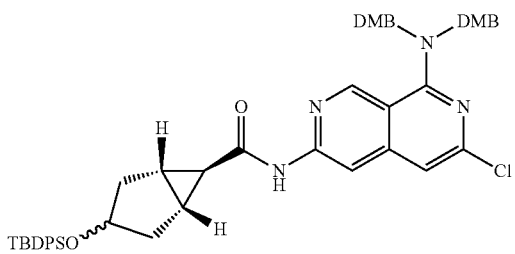

A mixture of (exo)-3-[(tert-butyldiphenylsilyl)oxy]-N-(6,8-dichloro-2,7-naphthyridin-3-yl)bicyclo[3.1.0]hexane-6-carboxamide (3.60 g, 6.24 mmol), bis[(2,4-dimethoxyphenyl)methyl]amine (7.93 g, 25.0 mmol), triethylamine (3.16 g, 31.2 mmol) and dioxane (100 mL) was heated at 110° C. After 16 h, the reaction was concentrated, and the resulting residue was purified by silica gel chromatography (3:7 ethyl acetate/petroleum ether) to provide (exo)-N-(8-[bis[(2,4-dimethoxyphenyl)methyl]amino]-6-chloro-2,7-naphthyridin-3-yl)-3-[(tert-butyldiphenylsilyl)oxy]bicyclo[3.1.0]hexane-6-carboxamide (4.0 g, 75%) as a yellow oil. LCMS (ESI): [M+H]$^+$=857.5.

Step 4: (exo)-N-(8-[bis[(2,4-dimethoxyphenyl)methyl]amino]-6-(4-methylpyridin-3-yl)-2,7-naphthyridin-3-yl)-3-[(tert-butyldiphenylsilyl)oxy]bicyclo[3.1.0]hexane-6-carboxamide

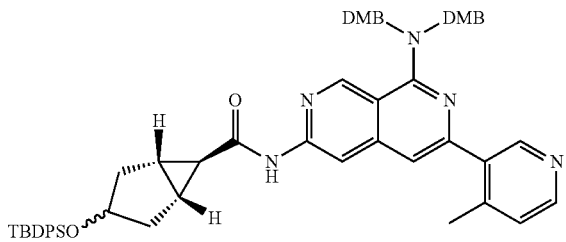

To a solution of (exo)-N-(8-[bis[(2,4-dimethoxyphenyl)methyl]amino]-6-chloro-2,7-naphthyridin-3-yl)-3-[(tert-butyldiphenylsilyl)oxy]bicyclo[3.1.0]hexane-6-carboxamide (4.0 g, 4.7 mmol) in dioxane (50 mL)/water (8 mL) was added (4-methylpyridin-3-yl)boronic acid (1.15 g, 8.40 mmol), XPhos palladium(II) biphenyl-2-amine chloride (730 mg, 0.93 mmol), XPhos (670 mg, 1.41 mmol) and KOAc (1.60 g, 16.3 mmol). The resulting solution was heated at 100° C. under nitrogen. After 2 h, the reaction was filtered, and the filtrate was concentrated under vacuum. Purification by silica gel chromatography (20:1 dichloromethane/methanol) provided (exo)-N-(8-[bis[(2,4-dimethoxyphenyl)methyl]amino]-6-(4-methylpyridin-3-yl)-2,7-naphthyridin-3-yl)-3-[(tert-butyldiphenylsilyl)oxy]bicyclo[3.1.0]hexane-6-carboxamide (4 g, 94%) as a yellow oil. LCMS (ESI): [M+H]$^+$=913.5.

Step 5: (exo)-N-(8-[bis[(2,4-dimethoxyphenyl)methyl]amino]-6-(4-methylpyridin-3-yl)-2,7-naphthyridin-3-yl)-3-hydroxybicyclo[3.1.0]hexane-6-carboxamide

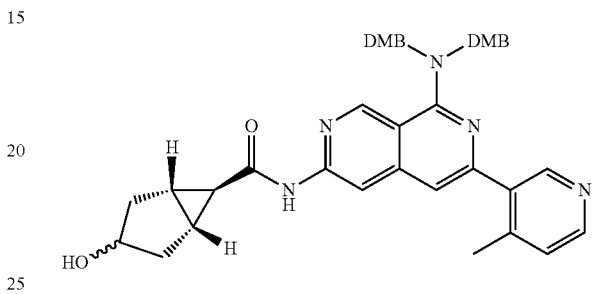

To a solution of (exo)-N-(8-[bis[(2,4-dimethoxyphenyl)methyl]amino]-6-(4-methylpyridin-3-yl)-2,7-naphthyridin-3-yl)-3-[(tert-butyldiphenylsilyl)oxy]bicyclo[3.1.0]hexane-6-carboxamide (3.2 g, 3.5 mmol) in tetrahydrofuran (40 mL) was added TBAF trihydrate (5.5 g, 17.5 mmol) at 25° C. After 4 h, the reaction was diluted with water, and the resulting solution was extracted with dichloromethane. The combined organic was washed with saturated aqueous sodium chloride solution, dried over Na$_2$SO$_4$, filtered, and concentrated under vacuum. Purification by silica gel (10:1 dichloromethane/methanol) afforded (1R,5S,6R)—N-(8-[bis[(2,4-dimethoxyphenyl)methyl]amino]-6-(4-methylpyridin-3-yl)-2,7-naphthyridin-3-yl)-3-hydroxybicyclo[3.1.0]hexane-6-carboxamide (2.1 g, 89%) as a light yellow solid. LCMS (ESI): [M+H]$^+$=676.4.

Step 6: (exo)-N-(8-[bis[(2,4-dimethoxyphenyl)methyl]amino]-6-(4-methylpyridin-3-yl)-2,7-naphthyridin-3-yl)-3-oxobicyclo[3.1.0]hexane-6-carboxamide

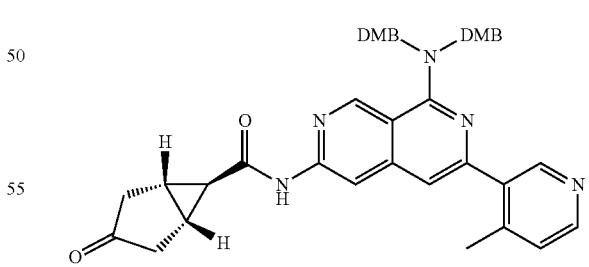

To a solution of (exo)-N-(8-[bis[(2,4-dimethoxyphenyl)methyl]amino]-6-(4-methylpyridin-3-yl)-2,7-naphthyridin-3-yl)-3-hydroxybicyclo[3.1.0]hexane-6-carboxamide (0.80 g, 1.18 mmol) in dichloromethane (20 mL) was added Dess-Martin Periodinane (3.51 g, 8.29 mmol) at room temperature. The resulting solution was warmed to 45° C. After 3 h, the reaction was concentrated under vacuum, and the resulting residue was purified by silica gel chromatography (95:5 dichloromethane/methanol) to provide (exo)-N-(8-[bis[(2,4-dimethoxyphenyl)methyl]amino]-6-(4-methylpyridin-3-yl)-2,7-naphthyridin-3-yl)-3-oxobicyclo[3.1.0]hexane-6-carboxamide (0.80 g) as a yellow solid. LCMS (ESI): [M+H]+=674.4.

Step 7: (exo)-N-(8-[bis[(2,4-dimethoxyphenyl)methyl]amino]-6-(4-methylpyridin-3-yl)-2,7-naphthyridin-3-yl)-3-(morpholin-4-yl)bicyclo[3.1.0]hexane-6-carboxamide

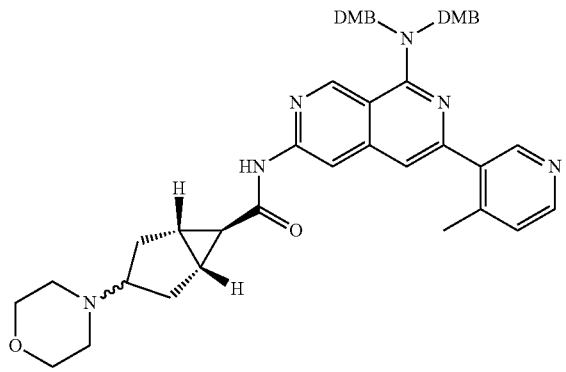

A mixture of (exo)-N-(8-[bis[(2,4-dimethoxyphenyl)methyl]amino]-6-(4-methylpyridin-3-yl)-2,7-naphthyridin-3-yl)-3-oxobicyclo[3.1.0]hexane-6-carboxamide (0.20 g, 0.30 mmol), morpholine (129 mg, 1.48 mmol), NaBH$_3$CN (56 mg, 0.89 mmol), and AcOH (0.89 mg, 0.02 mmol) in methanol (10 mL) was heated at 60° C. After 6 h, the reaction was concentrated under vacuum, and the resulting residue was purified by silica gel chromatography (95:5 dichloromethane/methanol) to give (exo)-N-(8-[bis[(2,4-dimethoxyphenyl)methyl]amino]-6-(4-methylpyridin-3-yl)-2,7-naphthyridin-3-yl)-3-(morpholin-4-yl)bicyclo[3.1.0]hexane-6-carboxamide (0.20 g, 90%) as a yellow oil. LCMS (ESI): [M+H]+=745.5.

Step 8: (exo)-N-[8-amino-6-(4-methylpyridin-3-yl)-2,7-naphthyridin-3-yl]-3-(morpholin-4-yl)bicyclo[3.1.0]hexane-6-carboxamide

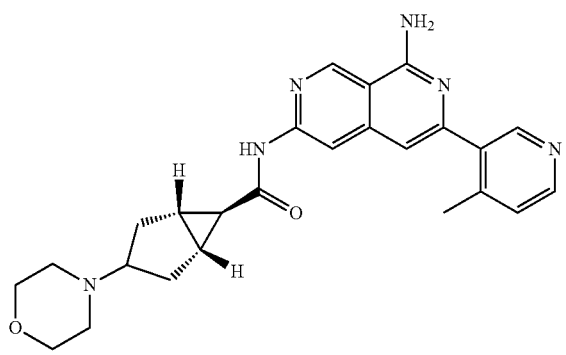

A solution of (exo)-N-(8-[bis[(2,4-dimethoxyphenyl)methyl]amino]-6-(4-methylpyridin-3-yl)-2,7-naphthyridin-3-yl)-3-(morpholin-4-yl)bicyclo[3.1.0]hexane-6-carboxamide (0.20 g, 0.27 mmol) in trifluoroacetic acid (10 mL) and dichloromethane (10 mL) was stirred for 6 h at 25° C. The resulting mixture was concentrated under vacuum. The crude product was purified by Prep-HPLC to afford (exo)-N-[8-amino-6-(4-methylpyridin-3-yl)-2,7-naphthyridin-3-yl]-3-(morpholin-4-yl)bicyclo[3.1.0]hexane-6-carboxamide (17.2 mg, 14%) as an off-white solid. LCMS (ESI): R$_T$ (min)=1.75, [M+H]+=445.2, method=K-1; $^1$H NMR (400 MHz, DMSO-d$_6$) δ 10.87 (s, 1H), 9.37 (s, 1H), 8.56 (s, 1H), 8.43 (d, J=5.1 Hz, 1H), 8.21 (s, 1H), 7.31 (d, J=5.3 Hz, 3H), 6.95 (s, 1H), 3.59-3.57 (m, 4H), 2.89-2.72 (m, 1H), 2.41 (s, 3H), 2.32 (d, J=5.5 Hz, 4H), 2.16-2.06 (m, 3H), 1.77-1.74 (m, 2H), 1.59-1.56 (m, 2H).

Example 227

(1R,2R)—N-[8-amino-6-(2-methylphenyl)-2,7-naphthyridin-3-yl]-2-(1-methyl-1H-pyrazol-4-yl)cyclopropane-1-carboxamide (Compound 298) and (1S,2S)—N-[8-amino-6-(2-methylphenyl)-2,7-naphthyridin-3-yl]-2-(1-methyl-1H-pyrazol-4-yl)cyclopropane-1-carboxamide (Compound 299)

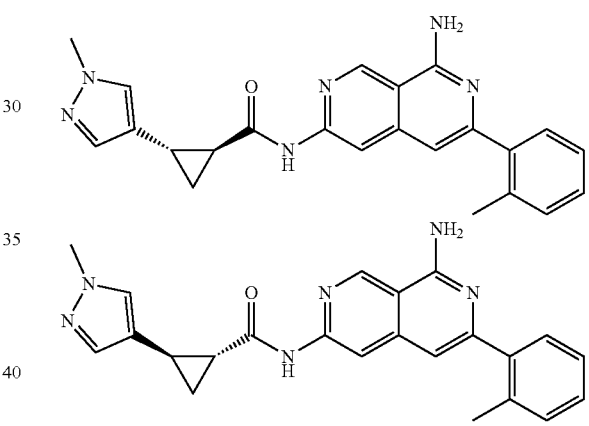

To a solution of trans-N-(8-amino-6-chloro-2,7-naphthyridin-3-yl)-2-(1-methyl-1H-pyrazol-4-yl)cyclopropane-1-carboxamide (0.10 g, 0.29 mmol) in dioxane (5 mL) and water (1 mL) was added (2-methylphenyl)boronic acid (0.060 g, 0.44 mmol), Pd(PPh$_3$)$_4$ (68 mg, 0.06 mmol) and K$_3$PO$_4$ (186 mg, 0.87 mmol). The solution was stirred was heated at 100° C. under nitrogen. After 12 h, the reaction was concentrated under vacuum, and the crude product was purified by Prep-HPLC to afford trans-N-[8-amino-6-(2-methylphenyl)-2,7-naphthyridin-3-yl]-2-(1-methyl-1H-pyrazol-4-yl)cyclopropane-1-carboxamide (50 mg, 43%) as a white solid. The enantiomers were separated by chiral SFC. Compound 298: LCMS (ESI): R$_T$ (min)=1.33 [M+H]+= 399.1, method=K-1; $^1$H NMR (400 MHz, CD$_3$OD) δ 9.28 (s, 1H), 8.29 (s, 1H), 7.51 (s, 1H), 7.41-7.35 (m, 2H), 7.35-7.25 (m, 3H), 6.89 (d, J=0.9 Hz, 1H), 3.86 (s, 3H), 2.41-2.37 (m, 1H), 2.36 (s, 3H), 2.14-2.09 (m, 1H), 1.60-1.55 (m, 1H), 1.33-1.23 (m, 1H). Compound 299: LCMS (ESI): R$_T$ (min)=1.84 [M+H]+=399.1, method=K; $^1$H NMR (400 MHz, CD$_3$OD) δ 9.28 (s, 1H), 8.29 (s, 1H), 7.51 (s, 1H), 7.41-7.35 (m, 2H), 7.35-7.25 (m, 3H), 6.89 (d, J=0.9 Hz, 1H), 3.86 (s, 3H), 2.41-2.37 (m, 1H), 2.36 (s, 3H), 2.14-2.09 (m, 1H), 1.60-1.55 (m, 1H), 1.33-1.23 (m, 1H).

Example 228

(1R,2R)—N-[8-amino-6-(5-cyano-2-methylphenyl)-2,7-naphthyridin-3-yl]-2-(1-methyl-1H-pyrazol-4-yl)cyclopropane-1-carboxamide (Compound 300) and (1S,2S)—N-[8-amino-6-(5-cyano-2-methylphenyl)-2,7-naphthyridin-3-yl]-2-(1-methyl-1H-pyrazol-4-yl)cyclopropane-1-carboxamide (Compound 301)

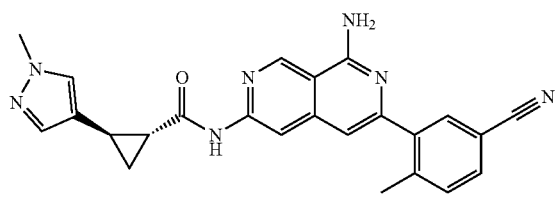

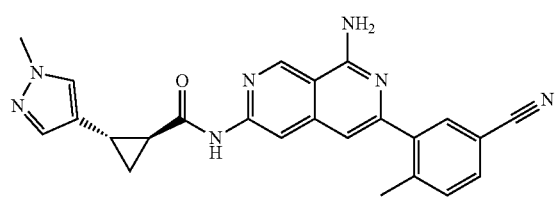

To a solution of trans-N-(8-amino-6-chloro-2,7-naphthyridin-3-yl)-2-(1-methyl-1H-pyrazol-4-yl)cyclopropane-1-carboxamide (0.15 g, 0.44 mmol) in dioxane (5 mL) and water (1 mL) was added 4-methyl-3-(tetramethyl-1,3,2-dioxaborolan-2-yl)benzonitrile (532 mg, 2.19 mmol), $Cs_2CO_3$ (428 mg, 1.31 mmol), XPhos (21 mg, 0.04 mmol), and XPhos-PdCl-2nd G (33 mg, 0.04 mmol). The mixture was heated at 100° C. under nitrogen. After 12 h, the solution was concentrated under vacuum, and the crude product was purified by Prep-HPLC to afford trans-N-[8-amino-6-(5-cyano-2-methylphenyl)-2,7-naphthyridin-3-yl]-2-(1-methyl-1H-pyrazol-4-yl)cyclopropane-1-carboxamide (68 mg, 37%) as a yellow solid. The enantiomers were separated by chiral SFC. Compound 300: LCMS (ESI): $R_T$ (min)=1.33 [M+H]$^+$=424.2, method=K-1; $^1$H NMR (300 MHz, DMSO-$d_6$) δ 10.97 (s, 1H), 9.38 (s, 1H), 8.27 (s, 1H), 7.87 (s, 1H), 7.77 (d, J=9.0 Hz, 1H), 7.58 (s, 1H), 7.52 (d, J=9.0 Hz, 1H), 7.35 (s, 2H), 7.31 (s, 1H), 6.99 (s, 1H), 3.77 (s, 3H), 2.46 (s, 3H), 2.24-2.20 (m, 2H), 1.43-1.37 (m, 1H), 1.23-1.18 (m, 1H). Compound 301: LCMS (ESI): RT (min)=1.33, [M+H]$^+$=424.2, method=K; $^1$H NMR (300 MHz, DMSO-$d_6$) δ 10.97 (s, 1H), 9.38 (s, 1H), 8.27 (s, 1H), 7.87 (s, 1H), 7.77 (d, J=9.0 Hz, 1H), 7.58 (s, 1H), 7.52 (d, J=9.0 Hz, 1H), 7.35 (s, 2H), 7.31 (s, 1H), 6.99 (s, 1H), 3.77 (s, 3H), 2.46 (s, 3H), 2.24-2.20 (m, 2H), 1.43-1.37 (m, 1H), 1.23-1.18 (m, 1H).

Example 229

(1R,2R)—N-(8-amino-6-(2-chloro-6-fluorophenyl)-2,7-naphthyridin-3-yl)-2-(1-methyl-1H-pyrazol-4-yl)cyclopropanecarboxamide (Compound 302) and (1S,2S)—N-(8-amino-6-(2-chloro-6-fluorophenyl)-2,7-naphthyridin-3-yl)-2-(1-methyl-H-pyrazol-4-yl)cyclopropanecarboxamide (Compound 303)

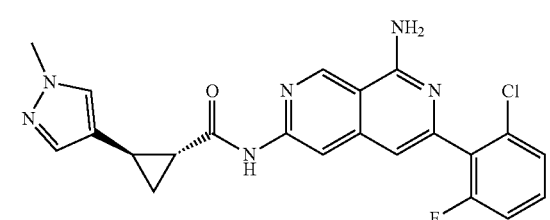

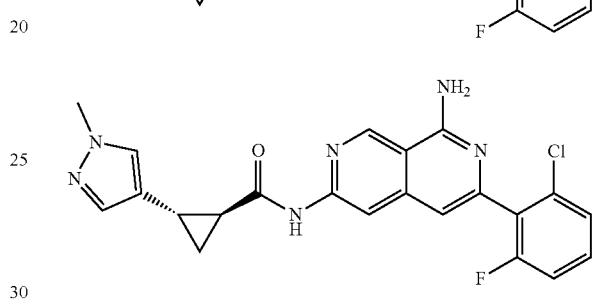

A mixture of $KHF_2$ (91 mg, 1.17 mmol), (2-chloro-6-fluorophenyl)boronic acid (122 mg, 0.70 mmol) in water (1.5 mL) and tert-butanol (6 mL) was stirred for 15 min at 25° C. under nitrogen. A mixture of trans-N-(8-amino-6-chloro-2,7-naphthyridin-3-yl)-2-(1-methyl-1H-pyrazol-4-yl)cyclopropane-1-carboxamide (0.20 g, 0.58 mmol), Pd(PPh$_3$)$_4$ (68 mg, 0.06 mmol), and $K_3PO_4$ (149 mg, 0.70 mmol) was added to the above solution, and the combined mixture was heated to 120° C. under nitrogen. After 45 min, the reaction was concentrated under vacuum, and the crude product was purified by Prep-HPLC to afford trans-N-[8-amino-6-(2-chloro-6-fluorophenyl)-2,7-naphthyridin-3-yl]-2-(1-methyl-1H-pyrazol-4-yl)cyclopropane-1-carboxamide (50 mg, 20%) as a white solid. The enantiomers were separated by chiral SFC. Compound 302: LCMS (ESI): $R_T$ (min)=1.34, [M+H]$^+$=437.2, method=K-1; $^1$H NMR (400 MHz, CD$_3$OD) δ 9.55 (s, 1H), 8.55 (s, 1H), 7.68-7.62 (m, 1H), 7.55-7.51 (m, 2H), 7.40-7.33 (m, 2H), 7.24 (s, 1H), 3.86 (s, 3H), 2.45-2.39 (m, 1H), 2.18-2.12 (m, 1H), 1.63-1.58 (m, 1H), 1.34-1.27 (m, 1H). Compound 303: LCMS (ESI): $R_T$ (min)=1.35, [M+H]$^+$=437.2, method=K-1; $^1$H NMR (400 MHz, CD$_3$OD) δ 9.55 (s, 1H), 8.55 (s, 1H), 7.68-7.62 (m, 1H), 7.55-7.51 (m, 2H), 7.40-7.33 (m, 2H), 7.24 (s, 1H), 3.86 (s, 3H), 2.45-2.39 (m, 1H), 2.18-2.12 (m, 1H), 1.63-1.58 (m, 1H), 1.34-1.27 (m, 1H).

Example 230

(1S,2S)—N-[8-amino-6-(2-chlorophenyl)-2,7-naph-thyridin-3-yl]-2-(1-methyl-1H-pyrazol-4-yl)cyclo-propane-1-carboxamide (Compound 304) and (1R,2R)—N-[8-amino-6-(2-chlorophenyl)-2,7-naphthyridin-3-yl]-2-(1-methyl-H-pyrazol-4-yl)cyclopropane-1-carboxamide (Compound 305)

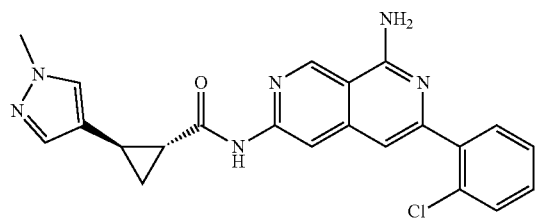

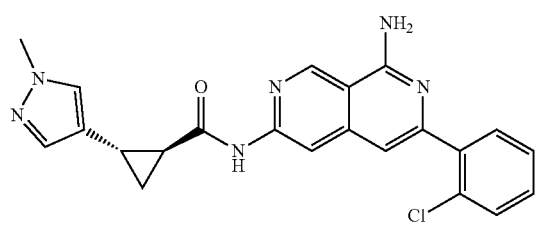

A suspension of trans-N-(8-amino-6-chloro-2,7-naphthy-ridin-3-yl)-2-(1-methyl-1H-pyrazol-4-yl)cyclopropane-1-carboxamide (190 mg, 0.55 mmol), (2-chlorophenyl)bo-ronic acid (433 mg, 2.76 mmol), Pd(PPh$_3$)$_4$ (63 mg, 0.06 mmol), and potassium carbonate (117 mg, 0.84 mmol) in dioxane (3 mL)/water (0.3 mL) was heated at 100° C. under nitrogen. After 3 h, the reaction was concentrated under vacuum, and the resulting residue was purified by Prep-HPLC to give trans-N-[8-amino-6-(2-chlorophenyl)-2,7-naphthyridin-3-yl]-2-(1-methyl-1H-pyrazol-4-yl)cyclopro-pane-1-carboxamide (60 mg, 23%) as a light yellow solid. The enantiomers were separated by chiral SFC. Compound 304: LCMS (ESI): R$_T$ (min)=0.95, [M+H]$^+$=419, method=K-1; $^1$H NMR (400 MHz, DMSO-d$_6$) δ 10.98 (s, 1H), 9.39 (s, 1H), 8.25 (s, 1H), 7.61-7.54 (m, 3H), 7.45-7.42 (m, 2H), 7.35 (s, 2H), 7.31 (s, 1H), 7.00 (s, 1H), 3.78 (s, 3H), 2.24-2.18 (m, 2H), 1.14-1.37 (m, 1H), 1.24-1.17 (m, 1H). Compound 305: LCMS (ESI): R$_T$ (min)=1.31 [M+H]$^+$=419, method=K-1; $^1$H NMR (400 MHz, DMSO-d$_6$) δ 10.98 (s, 1H), 9.39 (s, 1H), 8.25 (s, 1H), 7.61-7.54 (m, 3H), 7.45-7.42 (m, 2H), 7.35 (s, 2H), 7.31 (s, 1H), 7.00 (s, 1H), 3.78 (s, 3H), 2.24-2.18 (m, 2H), 1.14-1.37 (m, 1H), 1.24-1.17 (m, 1H).

Example 231

(1S,2S)—N-[8-amino-6-(2,6-difluorophenyl)-2,7-naphthyridin-3-yl]-2-(1-methyl-1H-pyrazol-4-yl)cyclopropane-1-carboxamide (Compound 306) and (1R,2R)—N-[8-amino-6-(2,6-difluorophenyl)-2,7-naphthyridin-3-yl]-2-(1-methyl-1H-pyrazol-4-yl)cyclopropane-1-carboxamide (Compound 307)

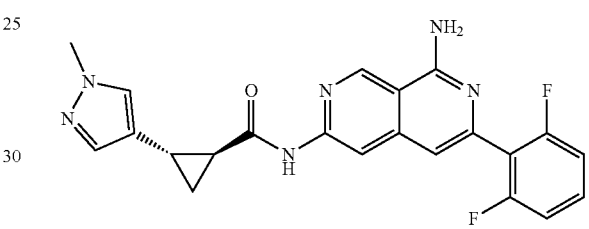

A mixture of trans-N-(8-amino-6-chloro-2,7-naphthyri-din-3-yl)-2-(1-methyl-1H-pyrazol-4-yl)cyclopropane-1-car-boxamide (455 mg, 1.32 mmol), (2,6-difluorophenyl)bo-ronic acid (0.20 g, 1.26 mmol), X-Phos (27 mg, 0.08 mmol), XPhos palladium(II) biphenyl-2-amine chloride (45 mg, 0.05 mmol), and AcOK (171 mg, 1.74 mmol) in dioxane (5 mL)/water (0.5 mL) was heated at 110° C. under nitrogen. After 3 h, the reaction was concentrated under vacuum, and the resulting residue was purified by Prep-HPLC to give racemic (trans)-N-[8-amino-6-(2,6-difluorophenyl)-2,7-naphthyridin-3-yl]-2-(1-methyl-1H-pyrazol-4-yl)cyclopro-pane-1-carboxamide (60 mg, 11%) as a light yellow solid. The enantiomers were separated by chiral SFC. Compound 306: LCMS (ESI): R$_T$ (min)=1.280, [M+H]$^+$=421, method=K-1; $^1$H NMR (400 MHz, CD$_3$OD) δ 9.30 (s, 1H), 8.31 (s, 1H), 7.52-7.44 (m, 2H), 7.37 (s, 1H), 7.13-7.05 (m, 2H), 6.99 (s, 1H), 3.02 (s, 3H), 2.41-2.34 (m, 1H), 2.13-2.10 (m, 1H), 1.61-1.56 (m, 1H), 1.29-1.25 (m, 1H). Compound 307: LCMS (ESI): R$_T$ (min)=1.272, [M+H]$^+$=421, method=K-1; $^1$H NMR (400 MHz, CD$_3$OD) δ 9.30 (s, 1H), 8.31 (s, 1H), 7.52-7.44 (m, 2H), 7.37 (s, 1H), 7.13-7.05 (m, 2H), 6.99 (s, 1H), 3.02 (s, 3H), 2.41-2.34 (m, 1H), 2.13-2.10 (m, 1H), 1.61-1.56 (m, 1H), 1.29-1.25 (m, 1H).

Example 232

(1S,2S)—N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide (Compound 308) and (1R,2R)—N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide (Compound 309)

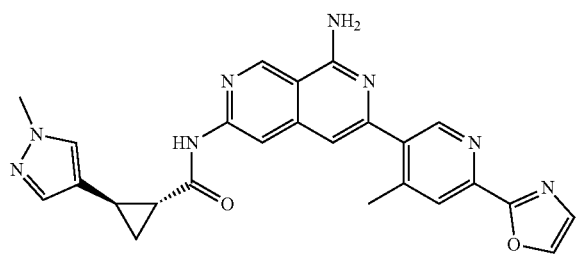

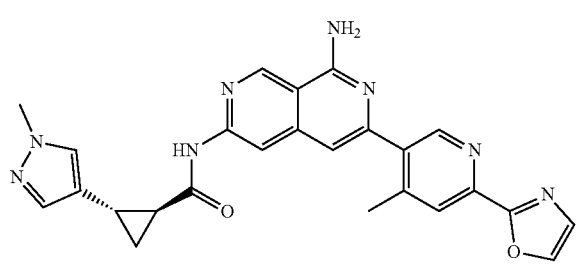

Step 1: 5-bromo-4-methyl-2-(1,3-oxazol-2-yl)pyridine

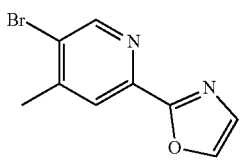

A mixture of 2,5-dibromo-4-methylpyridine (0.60 g, 2.39 mmol), 2-(tributylstannyl)-1,3-oxazole (1.02 g, 2.86 mmol), and Pd(PPh$_3$)$_4$ (276.32 mg, 0.23 mmol) in dioxane (15 mL) was heated at 90° C. under nitrogen. After 16 h, the mixture was concentrated under vacuum, and the resulting residue was purified by flash column chromatography (1:3 ethyl acetate/petroleum ether) to afford 5-bromo-4-methyl-2-(1,3-oxazol-2-yl)pyridine (0.20 g, 35%) as a light yellow solid. LCMS (ESI) [M+H]$^+$=239.0.

Step 2: 4-methyl-2-(1,3-oxazol-2-yl)-5-(tetramethyl-1,3,2-dioxaborolan-2-yl)pyridine

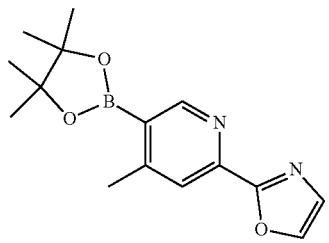 [SMILES: Cc1cc(-c2ncco2)ncc1B1OC(C)(C)C(C)(C)O1]

A mixture of 5-bromo-4-methyl-2-(1,3-oxazol-2-yl)pyridine (0.10 g, 0.41 mmol), 4,4,5,5-tetramethyl-2-(tetramethyl-1,3,2-dioxaborolan-2-yl)-1,3,2-dioxaborolane (1.06 g, 4.18 mmol), Pd(dppf)Cl$_2$ (31 mg, 0.04 mmol), and KOAc (103 mg, 1.05 mmol) in dioxane (5 mL) was heated at 90° C. under nitrogen. After 2 h, the solids were filtered, and the filtrate was concentrated under vacuum to afford crude 4-methyl-2-(1,3-oxazol-2-yl)-5-(tetramethyl-1,3,2-dioxaborolan-2-yl)pyridine (0.10 g) as a white solid. LCMS (ESI) [M+H]$^+$=287.0.

Step 3: (1R,2R)—N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide and (1S,2S)—N-[8-amino-6-[4-methyl-6-(1,3-oxazol-2-yl)pyridin-3-yl]-2,7-naphthyridin-3-yl]2-(1-methyl-1H-pyrazol-4-yl)cyclopropane-1-carboxamide

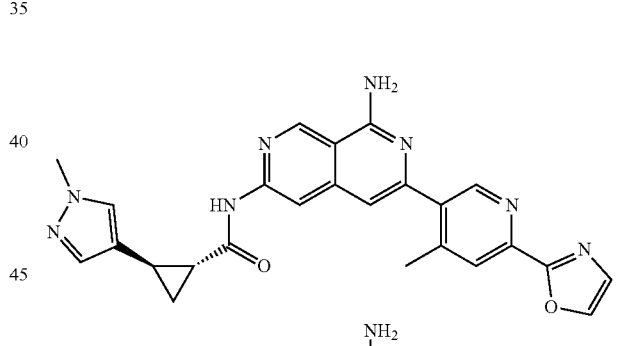

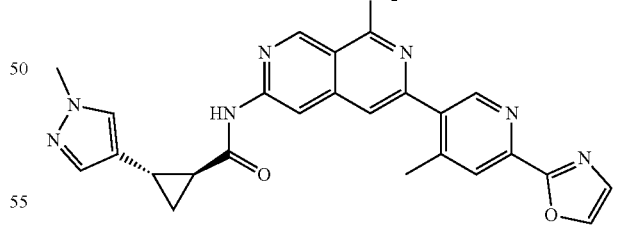

A mixture of 4-methyl-2-(1,3-oxazol-2-yl)-5-(tetramethyl-1,3,2-dioxaborolan-2-yl)pyridine (167 mg, 0.58 mmol), trans-N-(8-amino-6-chloro-2,7-naphthyridin-3-yl)-2-(1-methyl-1H-pyrazol-4-yl)cyclopropane-1-carboxamide (0.10 g, 0.29 mmol), 2nd generation XPhos precatalyst (22 mg, 0.028 mmol), X-Phos (13 mg, 0.03 mmol), and potassium carbonate (80 mg, 0.57 mmol) in water (1 mL)/dioxane (5 mL) was heated at 90° C. under nitrogen. After 2 h, the mixture was concentrated under vacuum, and the crude product was purified by Prep-HPLC to give racemic (trans)-

N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide (45 mg, 17%) as a brown solid. The enantiomers were separated by chiral-Prep-HPLC. Compound 308: LCMS (ESI): [M+H]⁺=467, R$_T$ (min)=1.272, method=K-1; ¹H NMR (400 MHz, CD$_3$OD) δ 9.33 (s, 1H), 8.70 (s, 1H), 8.38 (s, 1H), 8.15-8.14 (m, 2H), 7.51 (s, 1H), 7.45-7.44 (m, 1H), 7.38 (s, 1H), 7.09 (s, 1H), 3.86 (s, 3H), 2.57 (s, 3H), 2.42-2.37 (m, 1H), 2.14-2.10 (m, 1H), 1.61-1.56 (m, 1H), 1.34-1.25 (m, 1H). Compound 309: LCMS (ESI): [M+H]⁺=467, R$_T$ (min)=1.280, method=K-1; ¹H NMR (400 MHz, CD$_3$OD) δ 9.33 (s, 1H), 8.70 (s, 1H), 8.38 (s, 1H), 8.15-8.14 (m, 2H), 7.51 (s, 1H), 7.45-7.44 (m, 1H), 7.38 (s, 1H), 7.09 (s, 1H), 3.86 (s, 3H), 2.57 (s, 3H), 2.42-2.37 (m, 1H), 2.14-2.10 (m, 1H), 1.61-1.56 (m, 1H), 1.34-1.25 (m, 1H).

Example 233

(1S,2R)—N-(8-amino-6-(2,6-dichlorophenyl)-2,7-naphthyridin-3-yl)-2-(cyanomethyl)cyclopropanecarboxamide (Compound 310) and (1R,2S)—N-(8-amino-6-(2,6-dichlorophenyl)-2,7-naphthyridin-3-yl)-2-(cyanomethyl)cyclopropanecarboxamide (Compound 311)

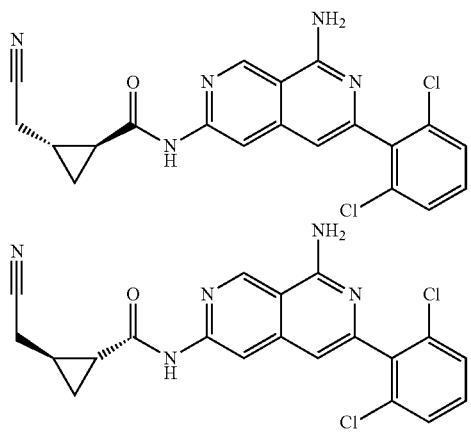

A mixture of trans-N-(8-amino-6-chloro-2,7-naphthyridin-3-yl)-2-(cyanomethyl)cyclopropane-1-carboxamide (160 mg, 2.7 mmol), (2,6-dichlorophenyl)boronic acid (2.52 g, 13.2 mmol), Pd(PPh$_3$)$_4$ (310 mg, 0.23 mmol), and sodium bicarbonate (1.12 g, 13.30 mmol) in water (2 mL)/ethanol (20 mL)/toluene (20 mL) was heated at 110° C. under nitrogen. After 15 h, the solids were filtered, and the filtrate was concentrated under vacuum. The crude product was purified by Prep-HPLC to give racemic product (110 mg, 10%) as a white solid. The enantiomers were separated by chiral SFC. Compound 310: LCMS (ESI): R$_T$=2.46 min, [M+H]⁺=412.1, method=K-1; ¹H NMR (400 MHz, CD$_3$OD) δ 9.33 (s, 1H), 8.29 (s, 1H), 7.56-7.48 (m, 2H), 7.42 (dd, J=8.0, 8.0 Hz, 1H), 6.86 (s, 1H), 2.79-2.64 (m, 2H), 2.03 (m, 1H), 1.81-1.70 (m, 1H), 1.35 (m, 1H), 1.06 (m, 1H). Compound 311: LCMS (ESI): R$_T$=1.37 min, [M+H]⁺=412.1, method=K-1; ¹H NMR (400 MHz, CD$_3$OD) δ 9.33 (s, 1H), 8.29 (s, 1H), 7.56-7.48 (m, 2H), 7.42 (dd, J=8.0, 8.0 Hz, 1H), 6.86 (s, 1H), 2.79-2.64 (m, 2H), 2.03 (m, 1H), 1.81-1.70 (m, 1H), 1.35 (m, 1H), 1.06 (m, 1H).

Example 234

(1R,3R)—N-[8-amino-6-(4-methylpyridin-3-yl)-2,7-naphthyridin-3-yl]-5-oxo-6-azaspiro[2.5]octane-1-carboxamide (Compound 315), (1S,3S)—N-[8-amino-6-(4-methylpyridin-3-yl)-2,7-naphthyridin-3-yl]-5-oxo-6-azaspiro[2.5]octane-1-carboxamide (Compound 314), (1S,3R)—N-[8-amino-6-(4-methylpyridin-3-yl)-2,7-naphthyridin-3-yl]-5-oxo-6-azaspiro[2.5]octane-1-carboxamide (Compound 313) and (1R,3S)—N-[8-amino-6-(4-methylpyridin-3-yl)-2,7-naphthyridin-3-yl]-5-oxo-6-azaspiro[2.5]octane-1-carboxamide (Compound 312)

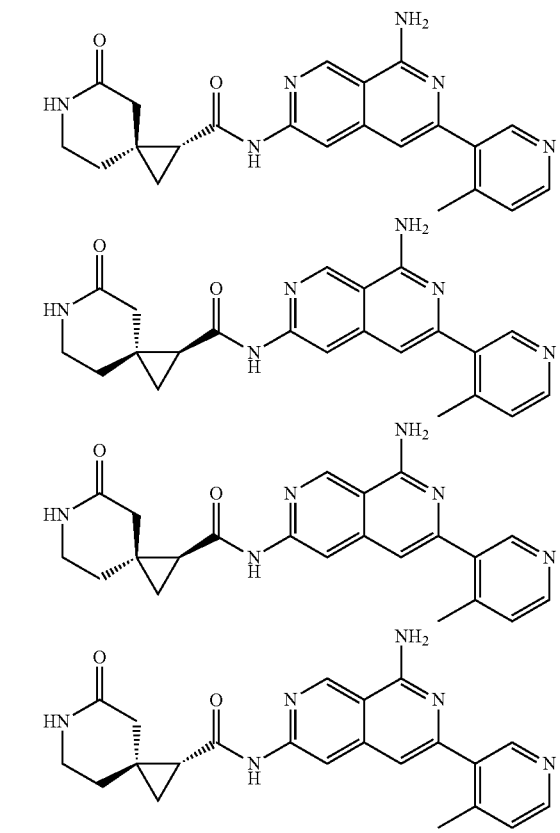

Step 1: tert-butyl 1-[(8-[bis[(2,4-dimethoxyphenyl)methyl]amino]-6-(4-methylpyridin-3-yl)-2,7-naphthyridin-3-yl)carbamoyl]-5-oxo-6-azaspiro[2.5]octane-6-carboxylate

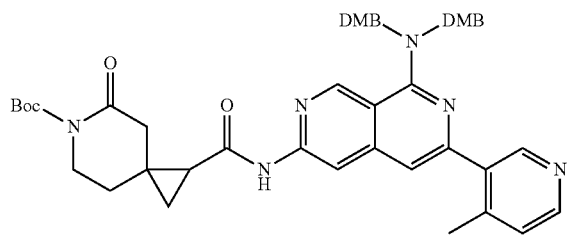

To an ice-cooled solution of 6-[(tert-butoxy)carbonyl]-5-oxo-6-azaspiro[2.5]octane-1-carboxylic acid (740 mg, 2.74 mmol) and 1-N,1-N-bis[(2,4-dimethoxyphenyl)methyl]-3-(4-methylpyridin-3-yl)-2,7-naphthyridine-1,6-diamine (1.16 g, 2.10 mmol) in pyridine (3 mL)/dichloromethane (15 mL) was added POCl$_3$ (643 mg, 4.19 mmol). After 30 min, excess POCl$_3$ was quenched with water. The resulting mixture was concentrated under vacuum to afford crude tert-butyl 1-[(8-[bis[(2,4-dimethoxyphenyl)methyl]amino]-6-(4-methylpyridin-3-yl)-2,7-naphthyridin-3-yl)carbamoyl]-5-oxo-6-azaspiro[2.5]octane-6-carboxylate (660 mg) as a brown solid. LCMS (ESI): [M+H]$^+$=803.4.

Step 2: (1R,3R)—N-[8-amino-6-(4-methylpyridin-3-yl)-2,7-naphthyridin-3-yl]-5-oxo-6-azaspiro[2.5]octane-1-carboxamide, (1S,3S)—N-[8-amino-6-(4-methylpyridin-3-yl)-2,7-naphthyridin-3-yl]-5-oxo-6-azaspiro[2.5]octane-1-carboxamide, (1S,3R)—N-[8-amino-6-(4-methylpyridin-3-yl)-2,7-naphthyridin-3-yl]-5-oxo-6-azaspiro[2.5]octane-1-carboxamide and (1R,3S)—N-[8-amino-6-(4-methylpyridin-3-yl)-2,7-naphthyridin-3-yl]-5-oxo-6-azaspiro[2.5]octane-1-carboxamide

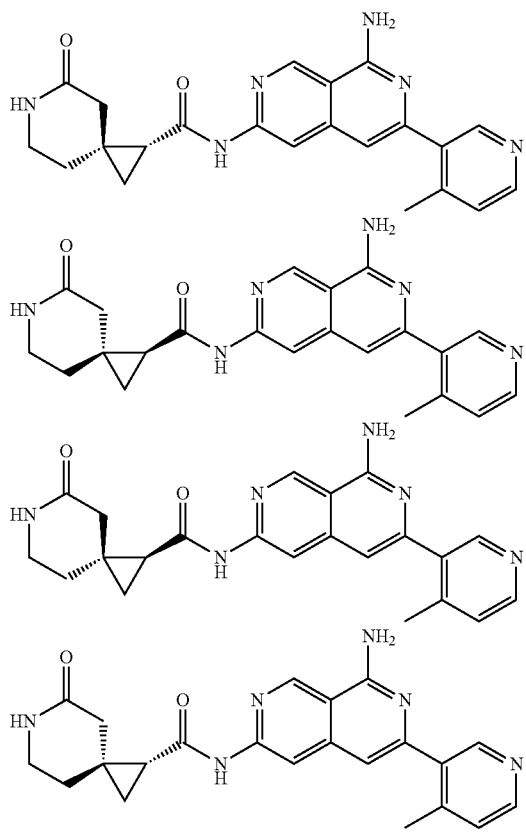

A mixture of tert-butyl 1-[(8-[bis[(2,4-dimethoxyphenyl)methyl]amino]-6-(4-methylpyridin-3-yl)-2,7-naphthyridin-3-yl)carbamoyl]-5-oxo-6-azaspiro[2.5]octane-6-carboxylate (660 mg, 0.82 mmol) and trifluoroacetic acid (10 mL) was heated at 80° C. After 40 min, the mixture was concentrated, and the resulting residue was diluted with MeOH (10 mL). The solution was basified to pH=8 with an NH$_3$ methanol solution (7 mol/L). The crude product was purified by Prep-HPLC followed by chiral SFC. Compound 315: LCMS (ESI): R$_T$ (min)=1.007, [M+H]$^+$=403.2, method=K-1; $^1$H NMR (300 MHz, CD$_3$OD) δ 9.30 (s, 1H), 8.54 (s, 1H), 8.44 (d, J=6.0 Hz, 1H), 8.32 (s, 1H), 7.41 (d, J=6.0 Hz, 1H), 6.99 (s, 1H), 3.27-3.21 (m, 2H), 2.46-2.30 (m, 5H), 2.06-1.99 (m, 3H), 1.47-1.39 (m, 1H), 1.11-1.07 (m, 1H). Compound 314: LCMS (ESI): R$_T$=1.014 min, [M+H]$^+$=403.2, method=K-1; $^1$H NMR (300 MHz, DMSO-d$_6$) δ 10.96 (s, 1H), 9.37 (s, 1H), 8.57 (s, 1H), 8.43 (d, J=6.0 Hz, 1H), 8.25 (s, 1H), 7.58 (s, 1H), 7.32-7.30 (m, 3H), 6.97 (s, 1H), 3.15-3.12 (m, 1H), 3.02-2.99 (m, 1H), 2.41 (s, 3H), 2.31-2.25 (m, 1H), 2.11-2.04 (m, 2H), 1.92-1.78 (m, 2H), 1.19-1.16 (m, 1H), 1.10-0.96 (m, 1H). Compound 313: LCMS (ESI): R$_T$ (min)=0.903, [M+H]$^+$=403.2, method=K-1; $^1$H NMR (300 MHz, DMSO-d$_6$) δ 10.97 (s, 1H), 9.39 (s, 1H), 8.58 (s, 1H), 8.45 (d, J=6.0 Hz, 1H), 8.27 (s, 1H), 7.53 (s, 1H), 7.41 (s, 2H), 7.33 (d, J=6.0 Hz, 1H), 7.01 (s, 1H), 3.21-3.16 (m, 2H), 2.42 (s, 3H), 2.38-2.36 (m, 2H), 2.12-2.08 (m, 1H), 1.97-1.70 (m, 1H), 1.53-1.45 (m, 1H), 1.12-1.05 (m, 2H). Compound 312: LCMS (ESI): R$_T$ (min)=0.903, [M+H]$^+$=403.2, method=K-1; $^1$H NMR (300 MHz, DMSO-d$_6$) δ 10.95 (s, 1H), 9.37 (s, 1H), 8.57 (s, 1H), 8.43 (d, J=6.0 Hz, 1H), 8.25 (s, 1H), 7.53 (s, 1H), 7.32-7.31 (m, 3H), 6.99 (s, 1H), 3.22-3.20 (m, 2H), 2.42 (s, 3H), 2.38-2.36 (m, 2H), 2.12-2.08 (m, 1H), 1.76-1.74 (m, 1H), 1.52-1.49 (m, 1H), 1.10-1.06 (m, 2H).

Example 235

(1R,2S)—N-(8-amino-5-cyclopropyl-6-(4-methylpyridin-3-yl)-2,7-naphthyridin-3-yl)-2-(cyanomethyl)cyclopropanecarboxamide (Compound 316) and (1S,2R)—N-(8-amino-5-cyclopropyl-6-(4-methylpyridin-3-yl)-2,7-naphthyridin-3-yl)-2-(cyanomethyl)cyclopropanecarboxamide (Compound 317)

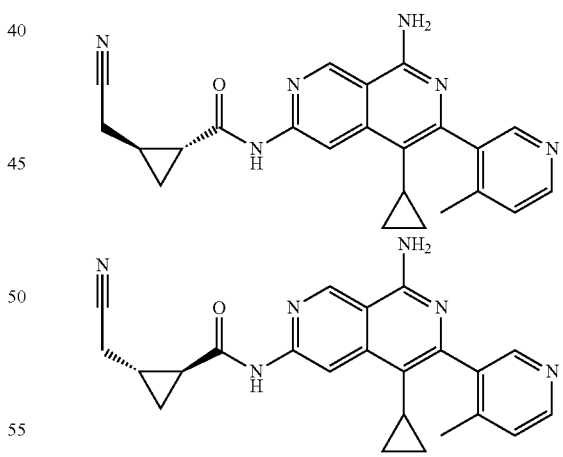

A mixture of trans-N-[8-amino-5-bromo-6-(4-methylpyridin-3-yl)-2,7-naphthyridin-3-yl]-2-(cyanomethyl)cyclopropane-1-carboxamide (0.30 g, 0.69 mmol), potassium cyclopropyl trifluoroborate (153 mg, 1.03 mmol), Pd(OAc)$_2$ (15 mg, 0.07 mmol), PCy$_3$ (39 mg, 0.14 mmol), and potassium carbonate (285 mg, 2.06 mmol) in water (0.5 mL)/toluene (5 mL) was heated at 90° C. under nitrogen. After 15 h, the solids were filtered, and the filtrate was concentrated under vacuum. The crude product was purified by Prep-HPLC to afford N-[8-amino-5-cyclopropyl-6-(4-methylpyridin-3-yl)-2,7-naphthyridin-3-yl]-2-(cyanomethyl)cyclopropane-1-carboxamide formic acid (20 mg, 7%) as a white solid. The enantiomers were separated by chiral SFC. Compound 316: LCMS (ESI): $R_T$ (min)=2.182, [M+H]$^+$=399.2, method=K-1; $^1$H NMR (400 MHz, CD$_3$OD) δ 9.39 (s, 1H), 9.04 (s, 1H), 8.51 (d, J=4 Hz, 1H), 8.50 (s, 1H), 8.51 (d, J=4 Hz, 1H), 2.81-2.66 (m, 2H), 2.34 (s, 3H), 2.09-2.03 (m, 1H), 1.90-1.75 (m, 2H), 1.41-1.36 (m, 1H), 1.11-1.07 (m, 1H), 0.88-0.77 (s, 2H), 0.17-0.07 (m, 2H). Compound 317: LCMS (ESI): $R_T$ (min)=1.079, [M+H]$^+$=399.2, method=K-1; $^1$H NMR (400 MHz, CD$_3$OD) δ 9.39 (s, 1H), 9.04 (s, 1H), 8.51 (d, J=4 Hz, 1H), 8.50 (s, 1H), 8.51 (d, J=4 Hz, 1H), 2.81-2.66 (m, 2H), 2.34 (s, 3H), 2.09-2.03 (m, 1H), 1.90-1.75 (m, 2H), 1.41-1.36 (m, 1H), 1.11-1.07 (m, 1H), 0.88-0.77 (s, 2H), 0.17-0.07 (m, 2H).

were separated by chiral SFC. Compound 318; LCMS (ESI): $R_T$ (min)=1.196, [M+H]$^+$=476.3, method=K-1; $^1$H NMR (400 MHz, CD$_3$OD) δ 9.22 (s, 1H), 8.52 (d, J=4 Hz, 1H), 8.05 (s, 1H), 7.48 (s, 1H), 7.42 (d, J=4.0 Hz, 1H), 7.40-7.38 (m, 2H), 7.35 (s, 1H), 7.23-7.20 (m, 3H), 6.57 (s, 1H), 3.85 (s, 3H), 2.37-2.33 (m, 1H), 2.31 (s, 3H), 2.09-2.058 (m, 1H), 1.56-1.51 (m, 1H), 1.26-1.21 (m, 1H). Compound 319: LCMS (ESI): [M+H]$^+$=476.3, $R_T$ (min)=1.197, method=K-1; $^1$H NMR (400 MHz, CD$_3$OD) δ 9.22 (s, 1H), 8.52 (d, J=4 Hz, 1H), 8.05 (s, 1H), 7.48 (s, 1H), 7.42 (d, J=4.0 Hz, 1H), 7.40-7.38 (m, 2H), 7.35 (s, 1H), 7.23-7.20 (m, 3H), 6.57 (s, 1H), 3.85 (s, 3H), 2.37-2.33 (m, 1H), 2.31 (s, 3H), 2.09-2.06 (m, 1H), 1.56-1.51 (m, 1H), 1.26-1.21 (m, 1H).

Example 236

(1S,2S)—N-(8-amino-6-(4-methyl-2-phenylpyridin-3-yl)-2,7-naphthyridin-3-yl)-2-(1-methyl-1H-pyrazol-4-yl)cyclopropanecarboxamide (Compound 318) and (1R,2R)—N-(8-amino-6-(4-methyl-2-phenylpyridin-3-yl)-2,7-naphthyridin-3-yl)-2-(1-methyl-1H-pyrazol-4-yl)cyclopropanecarboxamide (Compound 319)

Example 237

(1S,2S)—N-(8-amino-6-(4-methylpyridin-3-yl)-2,7-naphthyridin-3-yl)-2-methylcyclobutanecarboxamide (Compound 320), (1S,2R)—N-(8-amino-6-(4-methylpyridin-3-yl)-2,7-naphthyridin-3-yl)-2-methylcyclobutanecarboxamide (Compound 321), (1R,2R)—N-(8-amino-6-(4-methylpyridin-3-yl)-2,7-naphthyridin-3-yl)-2-methylcyclobutanecarboxamide (Compound 322), (1R,2S)—N-(8-amino-6-(4-methylpyridin-3-yl)-2,7-naphthyridin-3-yl)-2-methylcyclobutanecarboxamide (Compound 323)

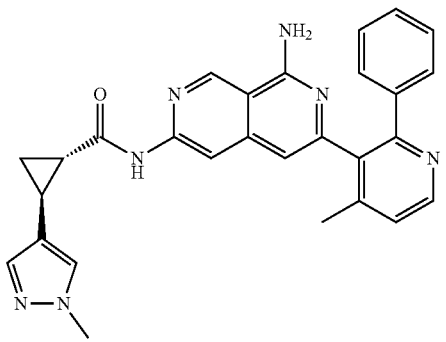

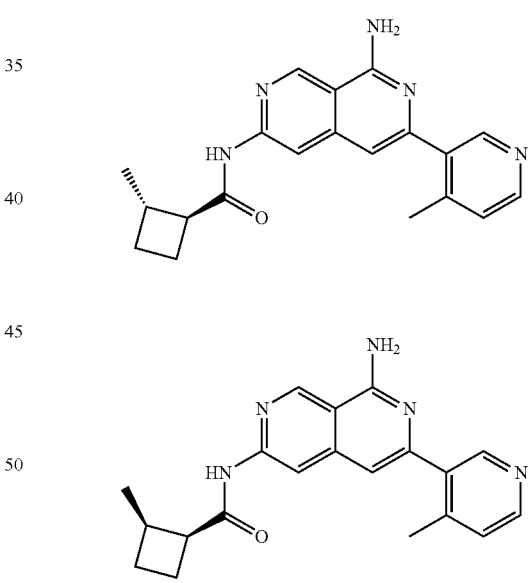

A mixture of trans-N-(8-amino-6-chloro-2,7-naphthyridin-3-yl)-2-(1-methyl-1H-pyrazol-4-yl)cyclopropane-1-carboxamide (311 mg, 0.91 mmol), 4-methyl-2-phenyl-3-(tetramethyl-1,3,2-dioxaborolan-2-yl)pyridine (402 mg, 1.36 mmol), Pd-AMPHOS (64 mg, 0.09 mmol), and K$_3$PO$_4$ (577 mg, 2.72 mmol) in water (2 mL)/dioxane (6 mL) was heated at 100° C. under nitrogen. After 20 min, the solids were filtered, and the filtrate was concentrated under vacuum. The crude product was purified by Prep-HPLC to give N-[8-amino-6-(4-methyl-2-phenylpyridin-3-yl)-2,7-naphthyridin-3-yl]-2-(1-methyl-1H-pyrazol-4-yl)cyclopropane-1-carboxamide (2.4 mg, 1%) as a white solid. The enantiomers

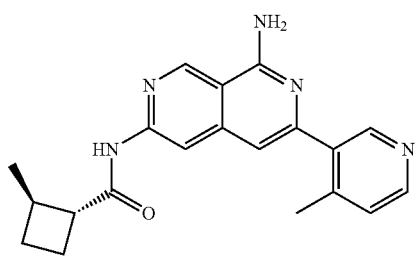

-continued

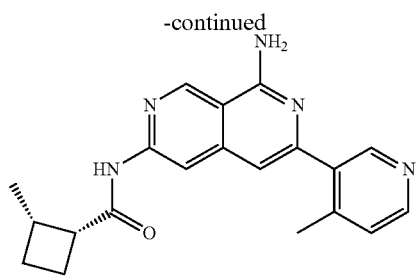

Step 1: N-(6,8-dichloro-2,7-naphthyridin-3-yl)-2-methylcyclobutanecarboxamide

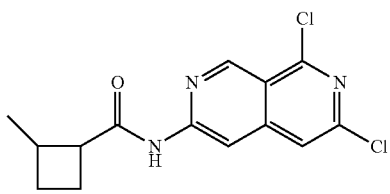 [SMILES: CC1CCC1C(=O)Nc1cc2cc(Cl)nc(Cl)c2cn1]

To a mixture of 6,8-dichloro-2,7-naphthyridin-3-amine hydrochloride (847 mg, 3.38 mmol) and 2-methylcyclobutane-1-carboxylic acid (0.50 g, 4.38 mmol) in pyridine (8 mL)/dichloromethane (40 mL) was added POCl₃ (1.03 g, 6.72 mmol) at 0° C. The reaction was stirred for 30 min at room temperature and diluted with water. The solution was extracted with dichloromethane. The combined organic was dried over anhydrous sodium sulfate, filtered, and concentrated under vacuum to afford N-(6,8-dichloro-2,7-naphthyridin-3-yl)-2-methylcyclobutane-1-carboxamide (890 mg, 85%) as a yellow solid. LCMS (ESI): [M+H]⁺=310.2.

Step 2: N-(8-amino-6-chloro-2,7-naphthyridin-3-yl)-2-methylcyclobutanecarboxamide

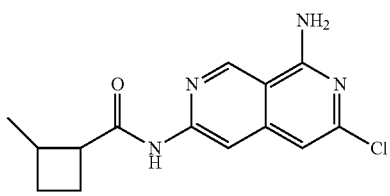 [SMILES: CC1CCC1C(=O)Nc1cc2cc(Cl)nc(N)c2cn1]

A mixture of N-(6,8-dichloro-2,7-naphthyridin-3-yl)-2-methylcyclobutane-1-carboxamide (490 mg, 1.58 mmol) in ammonium hydroxide (10 mL, 257 mmol) and dioxane (10 mL) was heated at 80° C. for 2 h. The reaction was concentrated under vacuum to afford crude N-(8-amino-6-chloro-2,7-naphthyridin-3-yl)-2-methylcyclobutane-1-carboxamide (910 mg) as a yellow solid. LCMS (ESI): [M+H]⁺=291.1

Step 3: (1S,2S)—N-(8-amino-6-(4-methylpyridin-3-yl)-2,7-naphthyridin-3-yl)-2-methylcyclobutanecarboxamide, (1S,2R)—N-(8-amino-6-(4-methylpyridin-3-yl)-2,7-naphthyridin-3-yl)-2-methylcyclobutanecarboxamide, (1R,2R)—N-(8-amino-6-(4-methylpyridin-3-yl)-2,7-naphthyridin-3-yl)-2-methylcyclobutanecarboxamide, (1R,2S)—N-(8-amino-6-(4-methylpyridin-3-yl)-2,7-naphthyridin-3-yl)-2-methylcyclobutanecarboxamide

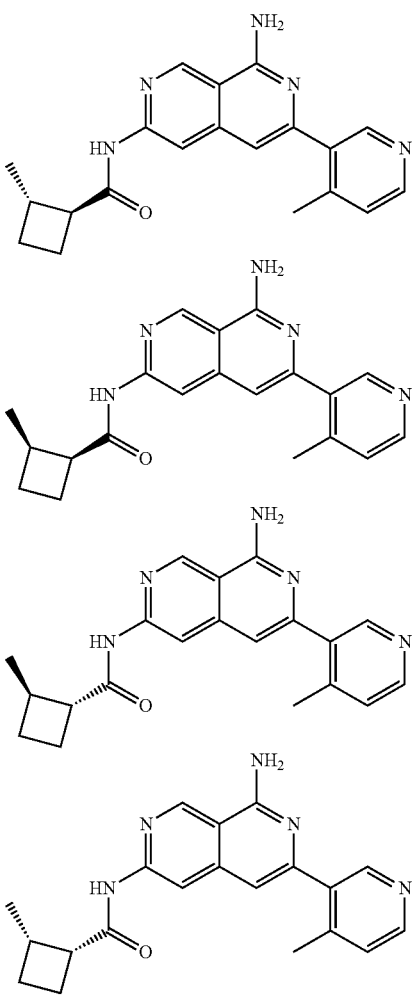

A mixture of N-(8-amino-6-chloro-2,7-naphthyridin-3-yl)-2-methylcyclobutane-1-carboxamide (440 mg, 1.51 mmol), (4-methylpyridin-3-yl)boronic acid (311 mg, 2.27 mmol), XPhos (144 mg, 0.30 mmol), XPhos-PdCl-2nd G (115 mg, 0.15 mmol), and potassium carbonate (626 mg, 4.53 mmol) in 10:1 dioxane water (11 mL) was heated at 100° C. under nitrogen. After 1 h, the solids were filtered, and the filtrate was concentrated under vacuum. The crude product was purified by chiral-Prep-HPLC followed by chiral SFC. Compound 320: LCMS (ESI): R$_T$(min)=1.29, [M+H]⁺=348.1, method=K-1; ¹H NMR (400 MHz, CD₃OD) δ 9.29 (s, 1H), 8.55 (s, 1H), 8.44 (d, J=4.0 Hz, 1H), 8.37 (s, 1H), 7.41 (d, J=4 Hz, 1H), 7.01 (s, 1H), 2.99-2.92 (m, 1H), 2.76-2.68 (m, 1H), 2.47 (s, 3H), 2.25-2.05 (m, 3H), 1.69-1.60 (m, 1H), 1.19 (d, J=8.0 Hz, 3H). Compound 321: LCMS (ESI): R$_T$(min)=1.42, [M+H]⁺=348.1, method=K-1;

¹H NMR (400 MHz, CD₃OD) δ 9.29 (s, 1H), 8.56 (s, 1H), 8.44 (d, J=4.0 Hz, 1H), 8.39 (s, 1H), 7.41 (d, J=4.0 Hz, 1H), 7.01 (s, 1H), 3.51-3.45 (m, 1H), 2.96-2.89 (m, 1H), 2.55-2.48 (m, 1H), 2.47 (s, 3H), 2.27-2.18 (m, 1H), 2.09-2.00 (m, 1H), 1.73-1.65 (m, 1H), 1.11 (d, J=8.0 Hz, 3H). Compound 322: LCMS (ESI): [M+H]⁺=348.1, R_T (min)=0.98, method=K-1; ¹H NMR (400 MHz, CD₃OD) δ 9.29 (s, 1H), 8.55 (s, 1H), 8.44 (d, J=4.0 Hz, 1H), 8.37 (s, 1H), 7.41 (d, J=4.0 Hz, 1H), 7.01 (s, 1H), 2.99-2.92 (m, 1H), 2.76-2.68 (m, 1H), 2.47 (s, 3H), 2.25-2.05 (m, 3H), 1.69-1.60 (m, 1H), 1.19 (d, J=8.0 Hz, 3H). Compound 323: LCMS (ESI): [M+H]⁺=348.1, R_T(min)=0.98, method=K-1; ¹H NMR (400 MHz, CD₃OD) δ 9.29 (s, 1H), 8.56 (s, 1H), 8.44 (d, J=4.0 Hz, 1H), 8.39 (s, 1H), 7.41 (d, J=4.0 Hz, 1H), 7.01 (s, 1H), 3.51-3.45 (m, 1H), 2.96-2.89 (m, 1H), 2.55-2.48 (m, 1H), 2.47 (s, 3H), 2.27-2.18 (m, 1H), 2.09-2.00 (m, 1H), 1.73-1.65 (m, 1H), 1.11 (d, J=8.0 Hz, 3H).

Example 238

(1S,2R)—N-[8-amino-6-(4-methylpyridin-3-yl)-2,7-naphthyridin-3-yl]-2-(oxan-4-yl)cyclopropane-1-carboxamide (Compound 324) and (1R,2S)—N-[8-amino-6-(4-methylpyridin-3-yl)-2,7-naphthyridin-3-yl]-2-(oxan-4-yl)cyclopropane-1-carboxamide (Compound 325)

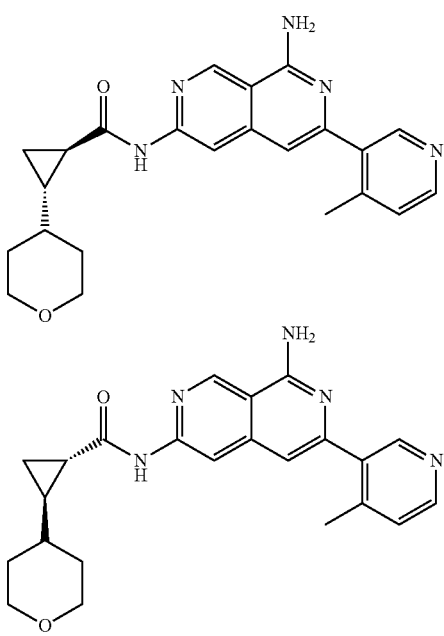

Step 1: (E)-tert-butyl 3-(tetrahydro-2H-pyran-4-yl)acrylate

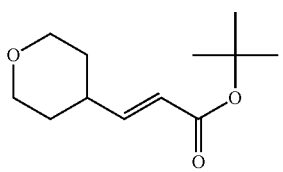

A solution of oxane-4-carbaldehyde (2.0 g, 17.5 mmol) and tert-butyl 2-(triphenylphosphoranylidene)acetate (7.2 g, 19 mmol) in tetrahydrofuran (100 mL) was stirred for 6 h at room temperature. The resulting mixture was concentrated under vacuum, and the resulting residue was purified by silica gel chromatography (3:1 petroleum ether/ethyl acetate) to afford tert-butyl (2E)-3-(oxan-4-yl)prop-2-enoate (3 g, 81%) as a white solid.

Step 2: trans-tert-butyl 2-(tetrahydro-2H-pyran-4-yl)cyclopropanecarboxylate

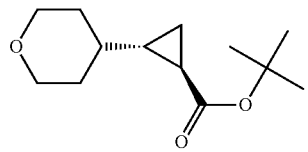 [SMILES: CC(C)(C)OC(=O)[C@@H]1C[C@H]1C1CCOCC1]

A mixture of trimethylsulfonium iodide (5.5 g, 24.99 mmol), t-BuOK (2.78 g, 24.77 mmol), tert-butyl (2E)-3-(oxan-4-yl)prop-2-enoate (2.5 g, 11.77 mmol) in DMSO (30 mL) was stirred for 3 h at room temperature under N₂. The reaction was diluted with water, and the aqueous layer was extracted with ethyl acetate. The combined organic layers were dried over Na₂SO₄, filtered, and concentrated under vacuum to afford trans-tert-butyl 2-(tetrahydro-2H-pyran-4-yl)cyclopropanecarboxylate (1.5 g, 56%) as a white solid.

Step 3: trans-2-(tetrahydro-2H-pyran-4-yl)cyclopropanecarboxylic acid

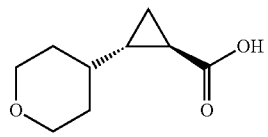 [SMILES: O=C(O)[C@@H]1C[C@H]1C1CCOCC1]

A solution of trans-tert-butyl-2-(oxan-4-yl)cyclopropane-1-carboxylate (1.5 g, 6.62 mmol) in dichloromethane (20 mL)/trifluoroacetic acid (20 mL) was stirred for 6 h at room temperature. The reaction solution was basified to pH 8 with 1M aqueous NaOH. The aqueous solution was washed with ethyl acetate and acidified to pH 2-3 with aqueous HCl. The acidic solution was extracted with ethyl acetate. The collected extracts were dried over Na₂SO₄, filtered, and concentrated under vacuum to yield crude trans-2-(tetrahydro-2H-pyran-4-yl)cyclopropanecarboxylic acid (1 g, 89%) as an oil.

Step 4: trans-N-(6,8-dichloro-2,7-naphthyridin-3-yl)-2-(tetrahydro-2H-pyran-4-yl)cyclopropanecarboxamide

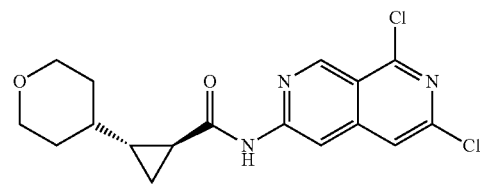 [SMILES: O=C(Nc1cc2cc(Cl)nc(Cl)c2cn1)[C@H]1C[C@@H]1C1CCOCC1]

POCl₃ (1.49 g, 9.71 mmol) was added dropwise to an ice-cooled solution of trans-2-(oxan-4-yl)cyclopropane-1-carboxylic acid (1.0 g, 5.87 mmol) and 6,8-dichloro-2,7-naphthyridin-3-amine hydrochloride (1.23 g, 4.91 mmol) and pyridine (2 mL, 24.84 mmol) in dichloromethane (20 mL). The reaction mixture was warmed to room temperature for 1 h. The reaction was washed with H₂O (15 mL), and the organic layer was dried over Na₂SO₄, filtered, and concentrated under vacuum. Purification by flash column chromatography (1:1 petroleum ether/ethyl acetate) afforded trans-N-(6,8-dichloro-2,7-naphthyridin-3-yl)-2-(oxan-4-yl)cyclopropane-1-carboxamide (0.60 g, 28%) as a yellow solid. LCMS (ESI): [M+H]⁺=367.2.

Step 5: trans-N-(8-amino-6-chloro-2,7-naphthyridin-3-yl)-2-(tetrahydro-2H-pyran-4-yl)cyclopropanecarboxamide

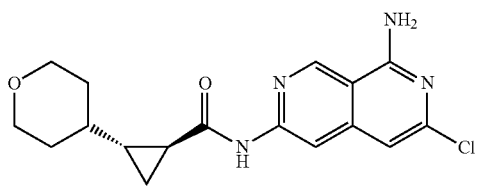 [SMILES: Nc1nc(Cl)cc2cc(NC(=O)[C@H]3C[C@@H]3C3CCOCC3)ncc12]

A solution of trans-N-(6,8-dichloro-2,7-naphthyridin-3-yl)-2-(oxan-4-yl)cyclopropane-1-carboxamide (500 mg, 1.36 mmol) in ammonium hydroxide (6 mL) and dioxane (6 mL) was heated at 100° C. After 1 h, the reaction mixture was concentrated under vacuum to afford trans-N-(8-amino-6-chloro-2,7-naphthyridin-3-yl)-2-(oxan-4-yl)cyclopropane-1-carboxamide (550 mg, 93%) as a yellow solid.

Step 6: (1S,2R)—N-[8-amino-6-(4-methylpyridin-3-yl)-2,7-naphthyridin-3-yl]-2-(oxan-4-yl)cyclopropane-1-carboxamide and (1R,2S)—N-[8-amino-6-(4-methylpyridin-3-yl)-2,7-naphthyridin-3-yl]-2-(oxan-4-yl)cyclopropane-1-carboxamide

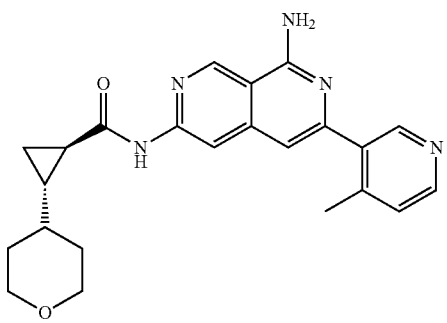

-continued

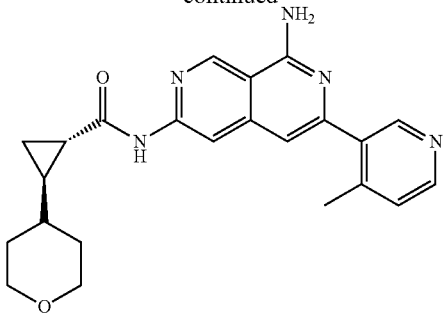

A mixture of trans-N-(8-amino-6-chloro-2,7-naphthyridin-3-yl)-2-(oxan-4-yl)cyclopropane-1-carboxamide (0.50 g, 1.44 mmol), (4-methylpyridin-3-yl)boronic acid (590 mg, 4.30 mmol), Pd(dppf)Cl₂ (110 mg, 0.15 mmol), and sodium carbonate (460 mg, 4.34 mmol) in 10:1 dioxane/water (16.5 mL) was heated at 100° C. under nitrogen. After 4 h, the reaction mixture was concentrated under vacuum, and the residue was purified by flash column chromatography (10:1 dichloromethane/methanol) to afford trans-N-[8-amino-6-(4-methylpyridin-3-yl)-2,7-naphthyridin-3-yl]-2-(oxan-4-yl)cyclopropane-1-carboxamide (200 mg, 34%) as a white solid. The enantiomers were separated by chiral-Prep-HPLC. Compound 324: LCMS (ESI): [M+H]⁺=404.2, $R_T$ (min)=1.10, method=K-1; ¹H NMR (400 MHz, CD₃OD) δ 9.32 (s, 1H), 8.55 (s, 1H), 8.46 (d, J=5.1 Hz, 1H), 8.32 (s, 1H), 7.43 (d, J=5.1 Hz, 1H), 7.01 (s, 1H), 4.03-3.92 (m, 2H), 3.47-3.37 (m, 2H), 2.47 (s, 3H), 1.87-1.83 (m, 1H), 1.76 (t, J=14.6 Hz, 2H), 1.57-1.42 (m, 2H), 1.38-1.31 (m, 1H), 1.25-1.21 (m, 1H), 1.19-1.07 (m, 1H), 0.93-0.89 (m, 1H). Compound 325: LCMS (ESI): [M+H]⁺=404.2, $R_T$ (min)=1.08 min, method=K-1; ¹H NMR (400 MHz, CD₃OD) δ 9.32 (s, 1H), 8.55 (s, 1H), 8.46 (d, J=5.1 Hz, 1H), 8.32 (s, 1H), 7.43 (d, J=5.1 Hz, 1H), 7.01 (s, 1H), 4.03-3.92 (m, 2H), 3.47-3.37 (m, 2H), 2.47 (s, 3H), 1.87-1.83 (m, 1H), 1.76 (t, J=14.6 Hz, 2H), 1.57-1.42 (m, 2H), 1.38-1.31 (m, 1H), 1.25-1.21 (m, 1H), 1.19-1.07 (m, 1H), 0.93-0.89 (m, 1H).

Example 239

(1R,2S,3R)—N-[8-amino-6-(4-methylpyridin-3-yl)-2,7-naphthyridin-3-yl]-2-methyl-3-(1-methyl-1H-pyrazol-4-yl)cyclopropane-1-carboxamide (Compound 326), (1S,2R,3S)—N-[8-amino-6-(4-methylpyridin-3-yl)-2,7-naphthyridin-3-yl]-2-methyl-3-(1-methyl-1H-pyrazol-4-yl)cyclopropane-1-carboxamide (Compound 327), (1S,2S,3S)—N-[8-amino-6-(4-methylpyridin-3-yl)-2,7-naphthyridin-3-yl]-2-methyl-3-(1-methyl-1H-pyrazol-4-yl)cyclopropane-1-carboxamide (Compound 328) and (1R,2R,3R)—N-[8-amino-6-(4-methylpyridin-3-yl)-2,7-naphthyridin-3-yl]-2-methyl-3-(1-methyl-1H-pyrazol-4-yl)cyclopropane-1-carboxamide (Compound 329)

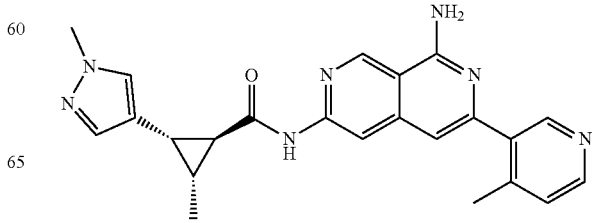

-continued

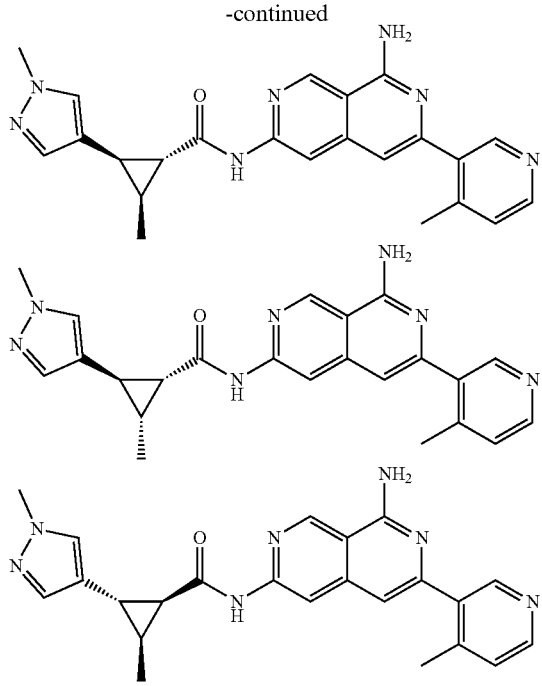

Step 1: Ethyldiphenylsulfonium tetrafluoroborate

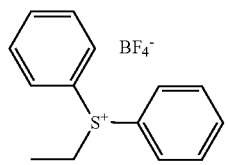

To a solution of iodoethane (3.00 g, 19.23 mmol) in dichloromethane (45 mL) was added diphenyl sulfide (10.69 g, 57.39 mmol) and AgBF$_4$ (3.75 g, 19.26 mmol). The resulting solution was stirred for 30 min at room temperature and overnight at 35° C. The solids were filtered, and the filtrate was concentrated under vacuum. The resulting residue were triturated with dichloromethane/ether (3×50 mL) to afford ethyldiphenylsulfanium tetrafluoroboranuide as an off-white solid (2.5 g, 34%). LCMS (ESI): [M+H]$^+$=215.0;

Step 2: Tert-butyl (2E)-3-(1-methyl-1H-pyrazol-4-yl)prop-2-enoate

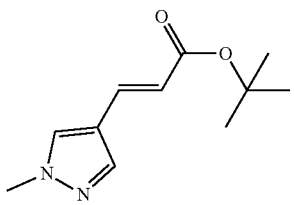

To a solution of 4-iodo-1-methyl-1H-pyrazole (5.0 g, 24 mmol) in N,N-dimethylformamide (20 mL) was added tert-butyl prop-2-enoate (9.23 g, 72.0 mmol), triethylamine (2.91 g, 28.8 mmol), Pd(OAc)$_2$ (538 mg, 2.40 mmol) and P(o-Tol)$_3$ (1.46 g, 4.80 mmol). The resulting mixture was heated overnight at 110° C. under nitrogen. The reaction was concentrated, and the resulting residue was purified by flash column chromatography (1:3 ethyl acetate/petroleum ether) to provide tert-butyl (2E)-3-(1-methyl-H-pyrazol-4-yl)prop-2-enoate as a light yellow oil (3.9 g, 74%). LCMS (ESI): [M+H]$^+$=209.0.

Step 3: tert-butyl-2-methyl-3-(1-methyl-1H-pyrazol-4-yl)cyclopropane-1-carboxylate

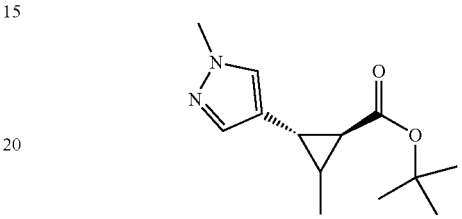

To a solution of diphenylehylsulfonium tetrafluoroborate (1.45 g, 4.80 mmol) in 1,2-dimethoxyethane (75 mL) and dichloromethane (12.5 mL) at −78° C. was added dropwise LDA (1.06 mL, 19.79 mmol). After 30 min, tert-butyl (2E)-3-(1-methyl-1H-pyrazol-4-yl)prop-2-enoate (0.50 g, 2.4 mmol) was added, and the resulting solution was stirred overnight at room temperature. The reaction was diluted with water and extracted with dichloromethane. The combined organic layers were dried over Na$_2$SO$_4$, filtered, and concentrated under vacuum to provide crude tert-butyl-2-methyl-3-(1-methyl-1H-pyrazol-4-yl)cyclopropane-1-carboxylate as a yellow solid (0.60 g). LCMS (ESI): [M+H]$^+$=237.0.

Step 4: 2-methyl-3-(i-methyl-1H-pyrazol-4-yl)cyclopropane-1-carboxylic acid

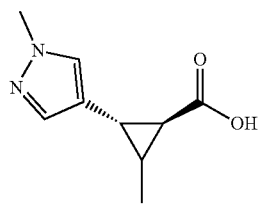

To a solution of tert-butyl-2-methyl-3-(1-methyl-H-pyrazol-4-yl)cyclopropane-1-carboxylate (0.60 g, 2.5 mmol) in dichloromethane (10 mL) was added trifluoroacetic acid (10 mL). The resulting solution was stirred for 5 h at room temperature. The reaction was concentrated under vacuum, and the resulting residue was dissolved in water (45 mL). The aqueous solution was basified to pH=9-10 with 10 M aqueous sodium hydroxide. The basic solution was washed with ether. The aqueous was then acidified to pH=3-4 with 1M aqueous hydrochloric acid. The acidic solution was extracted with ethyl acetate, and the organic was a concentrated under vacuum to provide crude 2-methyl-3-(1-methyl-H-pyrazol-4-yl)cyclopropane-1-carboxylic acid as an off-white solid (0.50 g). LCMS [M+H]$^+$=181.0.

Step 5: N-(6,8-dichloro-2,7-naphthyridin-3-yl)-2-methyl-3-(i-methyl-1H-pyrazol-4-yl)cyclopropane-1-carboxamide

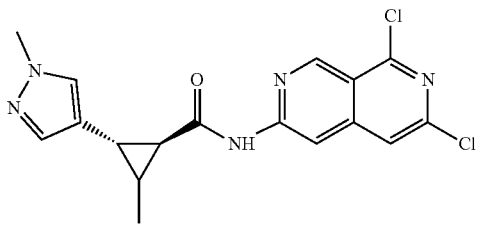 [SMILES: CC1[C@H](C(=O)Nc2cc3cc(Cl)nc(Cl)c3cn2)[C@H]1c1cnn(C)c1]

To an ice-cooled solution of 6,8-dichloro-2,7-naphthyridin-3-amine hydrochloride (0.50 g, 2.0 mmol) and trans-2-methyl-3-(1-methyl-1H-pyrazol-4-yl)cyclopropane-1-carboxylic acid (432 mg, 2.39 mmol) in pyridine (8.00 mL)/dichloromethane (45 mL) was added $POCl_3$ (612 mg, 3.99 mmol). The reaction was warmed to room temperature. After 30 min, the reaction was diluted with water (30 mL), and the resulting solution was extracted with dichloromethane (3×70 mL). The combined organic layers were dried over anhydrous sodium sulfate, filtered, and concentrated. Purification by flash column chromatography (1:2 ethyl acetate/petroleum ether) provided N-(6,8-dichloro-2,7-naphthyridin-3-yl)-2-methyl-3-(1-methyl-1H-pyrazol-4-yl)cyclopropane-1-carboxamide as a light yellow solid (350 mg, 42%). LCMS (ESI) $[M+H]^+=376.0$.

Step 6: N-(8-amino-6-chloro-2,7-naphthyridin-3-yl)-2-methyl-3-(i-methyl-1H-pyrazol-4-yl)cyclopropane-1-carboxamide

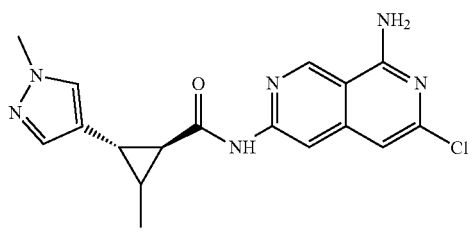 [SMILES: CC1[C@H](C(=O)Nc2cc3cc(Cl)nc(N)c3cn2)[C@H]1c1cnn(C)c1]

To a solution of N-(6,8-dichloro-2,7-naphthyridin-3-yl)-2-methyl-3-(1-methyl-1H-pyrazol-4-yl)cyclopropane-1-carboxamide (0.60 g, 1.59 mmol) in dioxane (10 mL) was added ammonium hydroxide (10 mL). The solution was heated at 100° C. After 2 h, the mixture was concentrated under vacuum to afford crude N-(8-amino-6-chloro-2,7-naphthyridin-3-yl)-2-methyl-3-(1-methyl-1H-pyrazol-4-yl)cyclopropane-1-carboxamide as an off-white solid (550 mg, 77%). LCMS (ESI) $[M+H]^+=357.0$.

Step 7: (1R,2S,3R)—N-[8-amino-6-(4-methylpyridin-3-yl)-2,7-naphthyridin-3-yl]-2-methyl-3-(1-methyl-1H-pyrazol-4-yl)cyclopropane-1-carboxamide, (1S,2R,3S)—N-[8-amino-6-(4-methylpyridin-3-yl)-2,7-naphthyridin-3-yl]-2-methyl-3-(1-methyl-1H-pyrazol-4-yl)cyclopropane-1-carboxamide, (1S,2S,3S)—N-[8-amino-6-(4-methylpyridin-3-yl)-2,7-naphthyridin-3-yl]-2-methyl-3-(1-methyl-1H-pyrazol-4-yl)cyclopropane-1-carboxamide and (1R,2R,3R)—N-[8-amino-6-(4-methylpyridin-3-yl)-2,7-naphthyridin-3-yl]-2-methyl-3-(1-methyl-1H-pyrazol-4-yl)cyclopropane-1-carboxamide

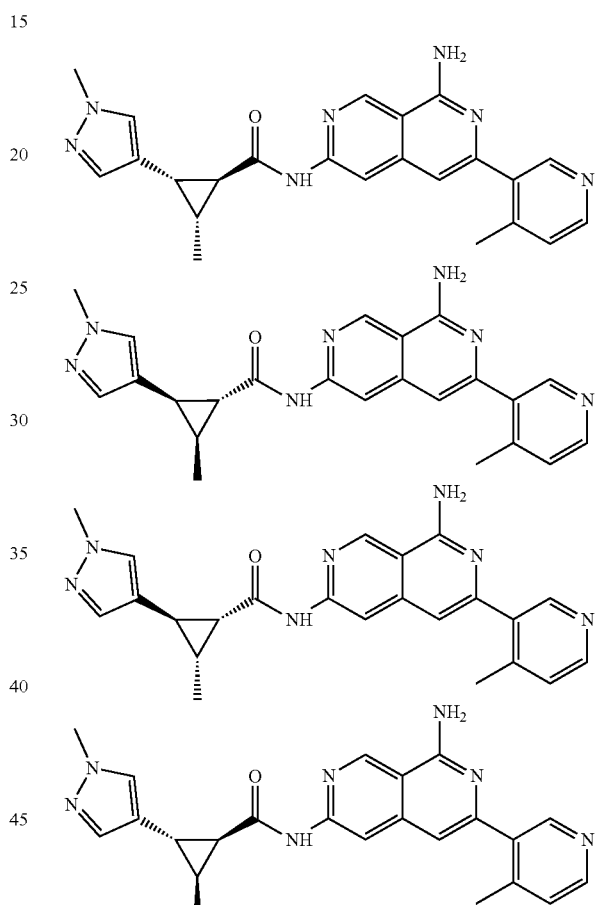

To a solution of N-(8-amino-6-chloro-2,7-naphthyridin-3-yl)-2-methyl-3-(1-methyl-1H-pyrazol-4-yl)cyclopropane-1-carboxamide (550 mg, 1.54 mmol) in dioxane (16 mL)/water (4 mL) was added (4-methylpyridin-3-yl)boronic acid (422 mg, 3.08 mmol), KOAc (454 mg, 4.62 mmol), 2nd generation XPhos precatalyst (121 mg, 0.15 mmol) and XPhos (147 mg, 0.31 mmol). The resulting solution was heated at 100° C. under nitrogen. After 2 h, the reaction was concentrated under vacuum, and the resulting residue was purified by silica gel chromatography (15:1 dichloromethane/methanol) followed by chiral-Prep-HPLC.

Compound 326: LCMS (ESI): $R_T$ (min)=1.98, $[M+H]^+=414.2$, method=K-1; $^1H$ NMR (400 MHz, $CD_3OD$) δ 9.29 (s, 1H), 8.53 (s, 1H), 8.43-8.41 (m, 1H), 8.32 (s, 1H), 7.50 (s, 1H), 7.40-7.38 (m, 1H), 7.33 (s, 1H), 6.98 (s, 1H), 3.87 (s, 3H), 2.54-2.49 (m, 1H), 2.45 (s, 3H), 2.00-1.97 (m, 1H), 1.79-1.72 (m, 1H), 1.06-1.04 (m, 3H). (Pyrazole trans to amide; methyl relative stereochemistry arbitrarily assigned; Absolute stereochemistry arbitrarily assigned).
Compound 327: LCMS (ESI): [M+H]⁺=414.2; $R_T$ (min)= 1.09 min, method=K-1; ¹H NMR (400 MHz, CD₃OD) δ 9.28 (s, 1H), 8.54 (s, 1H), 8.43-8.41 (m, 1H), 8.34 (s, 1H), 7.45 (s, 1H), 7.40-7.38 (m, 1H), 7.33 (s, 1H), 6.99 (s, 1H), 3.84 (s, 3H), 2.45 (s, 3H), 2.31-2.35 (m, 1H), 2.14-2.18 (m, 1H), 1.63-1.67 (m, 1H), 1.33-1.35 (m, 3H). (Pyrazole trans to amide; methyl relative stereochemistry arbitrarily assigned; Absolute stereochemistry arbitrarily assigned).
Compound 328: LCMS (ESI): [M+H]⁺=414.2; $R_T$ (min)= 1.08, method=K-1; ¹H NMR (400 MHz, CD₃OD) δ 9.29 (s, 1H), 8.53 (s, 1H), 8.43-8.41 (m, 1H), 8.32 (s, 1H), 7.50 (s, 1H), 7.40-7.38 (m, 1H), 7.33 (s, 1H), 6.98 (s, 1H), 3.93 (s, 3H), 2.54-2.49 (m, 1H), 2.45 (s, 3H), 2.00-1.97 (m, 1H), 1.79-1.72 (m, 1H), 1.06-1.04 (m, 3H). (Pyrazole trans to amide; methyl relative stereochemistry arbitrarily assigned; Absolute stereochemistry arbitrarily assigned).
Compound 329: LCMS (ESI): [M+H]⁺=414.2; $R_T$ (min)= 1.07, method=K-1; ¹H NMR (400 MHz, CD₃OD) δ 9.29 (s, 1H), 8.53 (s, 1H), 8.43-8.41 (m, 1H), 8.34 (s, 1H), 7.45 (s, 1H), 7.40-7.38 (m, 1H), 7.33 (s, 1H), 6.98 (s, 1H), 3.84 (s, 3H), 2.45 (s, 3H), 2.31-2.35 (m, 1H), 2.14-2.18 (m, 1H), 1.63-1.67 (m, 1H), 1.33-1.35 (m, 3H). (Pyrazole trans to amide; methyl relative stereochemistry arbitrarily assigned; Absolute stereochemistry arbitrarily assigned).

Example 240

(1R,2R)—N-(8-amino-6-(4-methylpyridin-3-yl)-2,7-naphthyridin-3-yl)-2-(1-(2-methoxyethyl)-1H-pyrazol-4-yl)cyclopropanecarboxamide (Compound 330) and (1S,2S)—N-(8-amino-6-(4-methylpyridin-3-yl)-2,7-naphthyridin-3-yl)-2-(1-(2-methoxyethyl)-1H-pyrazol-4-yl)cyclopropanecarboxamide (Compound 331)

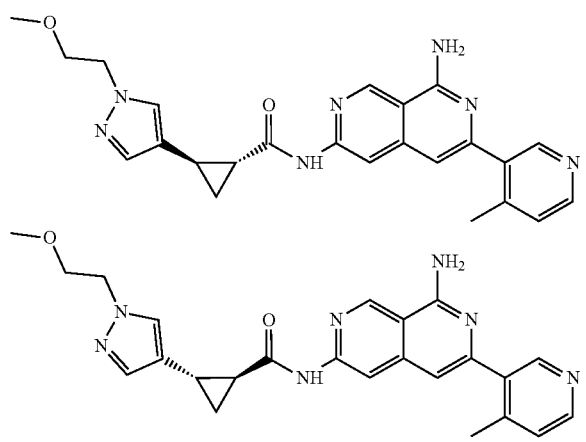

Step 1: 4-iodo-1-(2-methoxyethyl)-1H-pyrazole

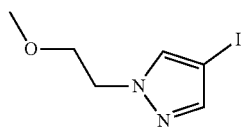

A mixture of 4-iodo-1H-pyrazole (10.00 g, 51.553 mmol), 1-chloro-2-methoxyethane (14.62 g, 154.64 mmol), potassium hydroxide (5.78 g, 103.02 mmol), and KBr (610 mg, 5.12 mmol) in ethanol (200 mL) was heated at 100° C. After 16 h, the mixture was concentrated under vacuum, and the resulting residue was purified by silica gel chromatography (95:5 dichloromethane/methanol) to afford 4-iodo-1-(2-methoxyethyl)-1H-pyrazole (12 g, 92%) as a yellow oil. LCMS (ESI): [M+H]⁺=292.95.

Step 2: (E)-methyl 3-(1-(2-methoxyethyl)-1H-pyrazol-4-yl)acrylate

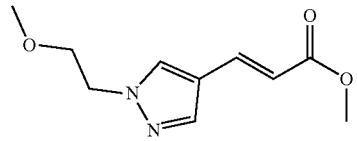

A mixture of 4-iodo-1-(2-methoxyethyl)-1H-pyrazole (11.0 g, 43.6 mmol), methyl prop-2-enoate (15.03 g, 174.5 mmol), Pd(OAc)₂ (1.47 g, 6.54 mmol), P(p-Tol)₃ (3.98 g, 13.1 mmol), and triethylamine (26.5 g, 262 mmol) in CH₃CN (200 mL) was heated at 110° C. under nitrogen. After 2 h, the reaction was concentrated under vacuum, and the residue was purified by silica gel chromatography 3:2 ethyl acetate/petroleum ether) to provide methyl (2E)-3-[1-(2-methoxyethyl)-1H-pyrazol-4-yl]prop-2-enoate (6.95 g, 76%) as a yellow oil. LCMS (ESI): [M+H]⁺=211.15.

Step 3: trans-methyl 2-(1-(2-methoxyethyl)-1H-pyrazol-4-yl)cyclopropanecarboxylate

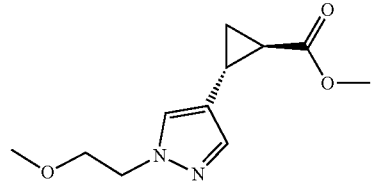

A freshly prepared solution of diazomethane in ether was added to an ice-cooled mixture of (2E)-3-[1-(2-methoxyethyl)-1H-pyrazol-4-yl]prop-2-enoate (0.50 g, 2.37 mmol), Pd(OAc)₂ (53 mg, 0.23 mmol) in dichloromethane (40 mL). After 30 min, the reaction was quenched with acetic acid (1 mL) and concentrated. The resulting residue was diluted with water, and the aqueous solution was extracted with ethyl acetate. The collected organic was washed with saturated aqueous NaHCO₃ solution, dried over Na₂SO₄, filtered, and concentrated to afford crude trans-methyl 2-[1-(2-methoxyethyl)-1H-pyrazol-4-yl]cyclopropane-1-carboxylate (230 mg) as a light brown oil. LCMS (ESI): [M+H]⁺=225.2.

847

Step 4: trans-2-(1-(2-methoxyethyl)-1H-pyrazol-4-yl)cyclopropanecarboxylic acid

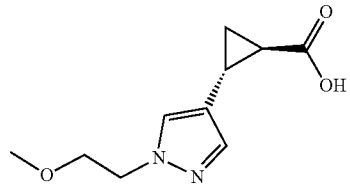

A mixture of trans-2-[1-(2-methoxyethyl)-1H-pyrazol-4-yl]cyclopropane-1-carboxylate (1.3 g, 5.8 mmol), LiOH.H$_2$O (1.46 g, 34.8 mmol) in tetrahydrofuran (5 mL)/water (5 mL) was stirred for 3 h at 25° C. The reaction was concentrated under vacuum, and the residue was dissolved with water. The aqueous solution was acidified to pH=3 with hydrochloric acid. The acidic solution was extracted with ethyl acetate. The combined organic layers were concentrated under vacuum to afford crude trans-2-[1-(2-methoxyethyl)-1H-pyrazol-4-yl]cyclopropane-1-carboxylic acid (1.0 g, 82%) as a yellow solid. LCMS (ESI): [M+H]$^+$=211.10.

Step 5: trans-N-(6,8-dichloro-2,7-naphthyridin-3-yl)-2-(1-(2-methoxyethyl)-1H-pyrazol-4-yl)cyclopropanecarboxamide

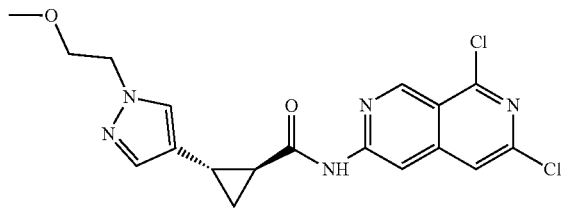 [SMILES: COCCn1cc([C@H]2C[C@@H]2C(=O)Nc2cc3cc(Cl)nc(Cl)c3cn2)cn1]

To an ice-cooled solution of trans-2-[1-(2-methoxyethyl)-1H-pyrazol-4-yl]cyclopropane-1-carboxylic acid (0.90 g, 4.28 mmol), 6,8-dichloro-2,7-naphthyridin-3-amine hydrochloride (896 mg, 3.58 mmol) and pyridine (4 mL) in dichloromethane (20 mL) was added POCl$_3$ (2.73 g, 17.8 mmol). The solution was warmed to 25° C. After 1 h, saturated aqueous sodium bicarbonate solution (100 mL) was added to the reaction, and the mixture was extracted with dichloromethane. The combined organic layers were dried over Na$_2$SO$_4$, filtered, and concentrated under vacuum. Purification by flash column chromatography (97:3 dichloromethane/methanol) to afford trans-N-(6,8-dichloro-2,7-naphthyridin-3-yl)-2-[1-(2-methoxyethyl)-1H-pyrazol-4-yl]cyclopropane-1-carboxamide (0.70 g, 48%) as a yellow solid. LCMS (ESI): [M+H]$^+$=405.9.

848

Step 6: trans-N-(8-amino-6-chloro-2,7-naphthyridin-3-yl)-2-(1-(2-methoxyethyl)-1H-pyrazol-4-yl)cyclopropanecarboxamide

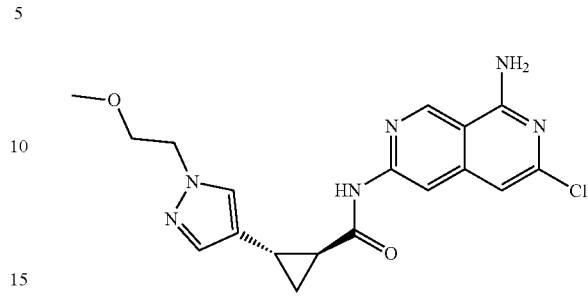

A mixture of N-(6,8-dichloro-2,7-naphthyridin-3-yl)-2-[1-(2-methoxyethyl)-1H-pyrazol-4-yl]cyclopropane-1-carboxamide (0.60 g, 1.47 mmol) and NH$_4$OH (18 mL) in dioxane (18 mL) was heated at 100° C. After 4 h, the mixture was concentrated under vacuum to afford crude trans-N-(8-amino-6-chloro-2,7-naphthyridin-3-yl)-2-[1-(2-methoxyethyl)-1H-pyrazol-4-yl]cyclopropane-1-carboxamide (0.60 g) as a light yellow solid, LCMS (ESI): [M+H]$^+$=387.10.

Step 7: (1S,2S)—N-(8-amino-6-(4-methylpyridin-3-yl)-2,7-naphthyridin-3-yl)-2-(1-(2-methoxyethyl)-1H-pyrazol-4-yl)cyclopropanecarboxamide and (1R,2R)—N-(8-amino-6-(4-methylpyridin-3-yl)-2,7-naphthyridin-3-yl)-2-(1-(2-methoxyethyl)-1H-pyrazol-4-yl)cyclopropanecarboxamide

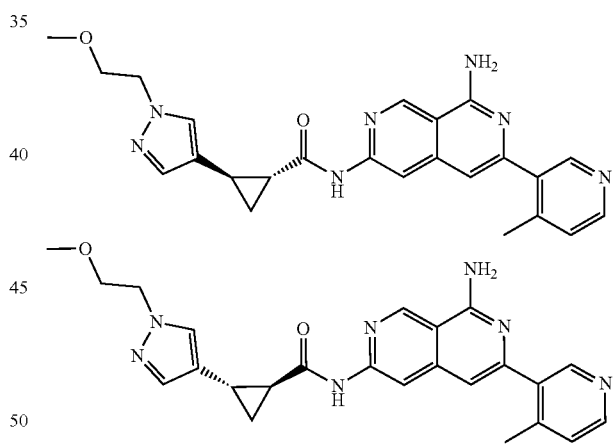

A mixture of trans-N-(8-amino-6-chloro-2,7-naphthyridin-3-yl)-2-[1-(2-methoxyethyl)-1H-pyrazol-4-yl]cyclopropane-1-carboxamide (550 mg, 1.42 mmol), (4-methylpyridin-3-yl)boronic acid (389 mg, 2.84 mmol), potassium carbonate (786 mg, 5.68 mmol), Pd(dppf)Cl$_2$ (116 mg, 0.14 mmol) in dioxane (20 mL)/water (4 mL) was heated at 100° C. under nitrogen. After 3 h, the mixture was concentrated under vacuum. Purification by Prep-HPLC afforded trans-N-[8-amino-6-(4-methylpyridin-3-yl)-2,7-naphthyridin-3-yl]-2-[1-(2-methoxyethyl)-1H-pyrazol-4-yl]cyclopropane-1-carboxamide (270 mg) as a white solid. The enantiomers were separated by chiral-Prep-HPLC. Compound 330: LCMS (ESI): [M+H]$^+$=444.2; R$_T$ (min)=1.06, method=K-1; $^1$H NMR (300 MHz, DMSO-d$_6$) δ 10.97 (s, 1H), 9.38 (s, 1H), 8.57 (s, 1H), 8.45 (d, J=6.0 Hz, 1H), 8.26 (s, 1H), 7.59

(s, 1H), 7.41 (s, 2H), 7.38-7.22 (m, 2H), 6.99 (s, 1H), 4.17 (t, J=6.0 Hz, 2H), 3.64 (t, J=6.0 Hz, 2H), 3.22 (s, 3H), 2.41 (s, 3H), 2.22 (t, J=6.0 Hz, 2H), 1.52-1.33 (m, 1H), 1.23-1.27 (m, 1H). Compound 331: LCMS (ESI): [M+H]$^+$=444.2; R$_T$ (min)=1.05, method=K-1; $^1$H NMR (300 MHz, DMSO-d$_6$) δ 10.97 (s, 1H), 9.38 (s, 1H), 8.57 (s, 1H), 8.45 (d, J=6.0 Hz, 1H), 8.26 (s, 1H), 7.59 (s, 1H), 7.41 (s, 2H), 7.38-7.22 (m, 2H), 6.99 (s, 1H), 4.17 (t, J=6.0 Hz, 2H), 3.64 (t, J=6.0 Hz, 2H), 3.22 (s, 3H), 2.41 (s, 3H), 2.22 (t, J=6.0 Hz, 2H), 1.52-1.33 (m, 1H), 1.23-1.27 (m, 1H).

Example 241

(1S,2S)—N-(8-amino-5-chloro-6-(4-(2-hydroxy-ethyl)pyridin-3-yl)-2,7-naphthyridin-3-yl)-2-(1-methyl-1H-pyrazol-4-yl)cyclopropanecarboxamide (Compound 332) and (1R,2R)—N-(8-amino-5-chloro-6-(4-(2-hydroxyethyl)pyridin-3-yl)-2,7-naphthyridin-3-yl)-2-(1-methyl-1H-pyrazol-4-yl)cyclopropanecarboxamide (Compound 333)

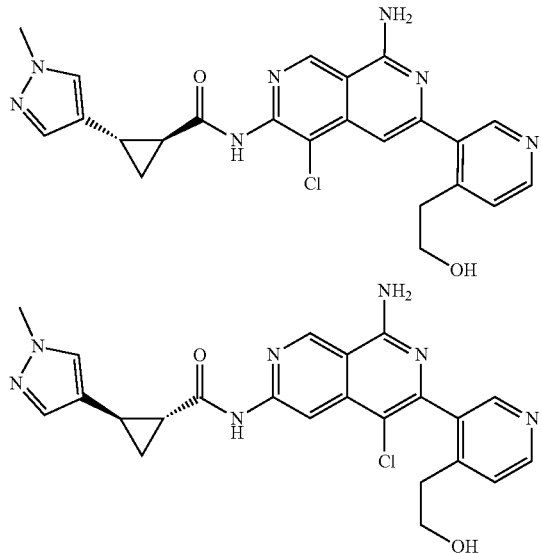

Step 1: trans-N-(8-amino-6-(4-(2-hydroxyethyl)pyridin-3-yl)-2,7-naphthyridin-3-yl)-2-(1-methyl-1H-pyrazol-4-yl)cyclopropanecarboxamide

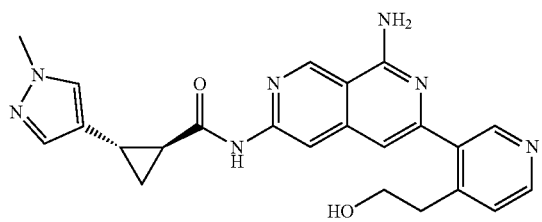 [SMILES: Cn1cc([C@H]2C[C@@H]2C(=O)Nc2cc3cc(-c4cnccc4CCO)nc(N)c3cn2)cn1]

A mixture of trans-N-(8-amino-6-chloro-2,7-naphthyridin-3-yl)-2-(1-methyl-1H-pyrazol-4-yl)cyclopropane-1-carboxamide (280 mg, 0.82 mmol), 1H,3H,4H-[1,2]oxaborinino[3,4-c]pyridin-1-ol (183 mg, 1.23 mmol), XPhos (78 mg, 0.16 mmol), XPhos-PdCl-2nd G (63 mg, 0.08 mmol), and KOAc (241 mg, 2.46 mmol) in dioxane (10 mL)/water (1 mL) was heated at 110° C. under nitrogen. After 15 h, the solids were filtered, and the filtrate was concentrated under vacuum. Purification by silica gel chromatography (15:1 dichloromethane/methanol) afforded trans-N-[8-amino-6-[4-(2-hydroxyethyl)pyridin-3-yl]-2,7-naphthyridin-3-yl]-2-(1-methyl-1H-pyrazol-4-yl)cyclopropane-1-carboxamide (61 mg, 17%) as a yellow solid. LCMS (ESI): [M+H]$^+$=430.3.

Step 3: (1S,2S)—N-(8-amino-5-chloro-6-(4-(2-hydroxyethyl)pyridin-3-yl)-2,7-naphthyridin-3-yl)-2-(1-methyl-H-pyrazol-4-yl)cyclopropanecarboxamide and (1R,2R)—N-(8-amino-5-chloro-6-(4-(2-hydroxyethyl)pyridin-3-yl)-2,7-naphthyridin-3-yl)-2-(1-methyl-1H-pyrazol-4-yl)cyclopropanecarboxamide

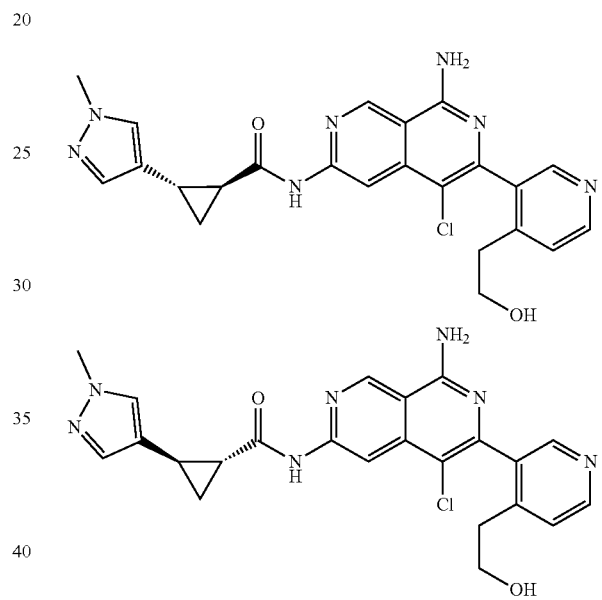

A mixture of trans-N-[8-amino-6-[4-(2-hydroxyethyl)pyridin-3-yl]-2,7-naphthyridin-3-yl]-2-(1-methyl-1H-pyrazol-4-yl)cyclopropane-1-carboxamide (79 mg, 0.18 mmol) and NCS (49 mg, 0.37 mmol) in N,N-dimethylformamide (6 mL) was stirred for 5 h at 25° C. The reaction was concentrated, and the crude product was purified by Prep-HPLC to afford trans-N-[8-amino-5-chloro-6-[4-(2-hydroxyethyl)pyridin-3-yl]-2,7-naphthyridin-3-yl]-2-(1-methyl-H-pyrazol-4-yl)cyclopropane-1-carboxamide (3 mg, 4%) as a yellow solid. The enantiomers were separated by chiral-Prep-HPLC. Compound 332: LCMS (ESI): [M+H]$^+$=464.2, R$_T$ (min)=1.09, method=K-1; $^1$H NMR (400 MHz, CD$_3$OD) δ 9.36 (s, 1H), 8.74 (s, 1H), 8.59 (d, J=8.0 Hz, 1H), 8.53 (s, 1H), 7.65 (d, J=8.0 Hz, 1H), 7.51 (s, 1H), 7.38 (s, 1H), 3.86 (s, 3H), 3.75 (t, J=8.0 Hz, 2H), 2.89 (t, J=8.0 Hz, 2H), 2.44-2.39 (m, 1H), 2.16-2.12 (m, 1H), 1.62-1.58 (m, 1H), 1.32-1.27 (m, 1H). Compound 333: LCMS (ESI): [M+H]$^+$=464.2, R$_T$ (min)=1.09, method=K-1. $^1$H NMR (400 MHz, CD$_3$OD) δ 9.36 (s, 1H), 8.74 (s, 1H), 8.59 (d, J=8.0 Hz, 1H), 8.53 (s, 1H), 7.65 (d, J=8.0 Hz, 1H), 7.51 (s, 1H), 7.38 (s, 1H), 3.86 (s, 3H), 3.75 (t, J=8.0 Hz, 2H), 2.89 (t, J=8.0 Hz, 2H), 2.44-2.39 (m, 1H), 2.16-2.12 (m, 1H), 1.62-1.58 (m, 1H), 1.32-1.27 (m, 1H).

Example 242

(1R,2S)—N-[8-amino-6-(4-methyl-6-phenylpyridin-3-yl)-2,7-naphthyridin-3-yl]-2-(cyanomethyl)cyclopropane-1-carboxamide (Compound 334) and (1S,2R)—N-[8-amino-6-(4-methyl-6-phenylpyridin-3-yl)-2,7-naphthyridin-3-yl]-2-(cyanomethyl)cyclopropane-1-carboxamide (Compound 335)

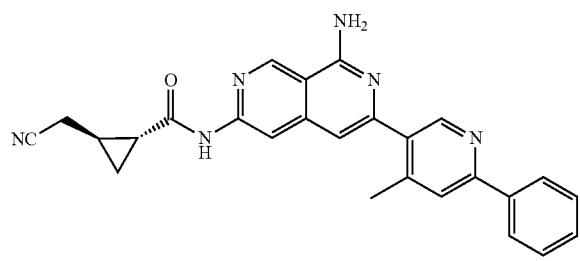

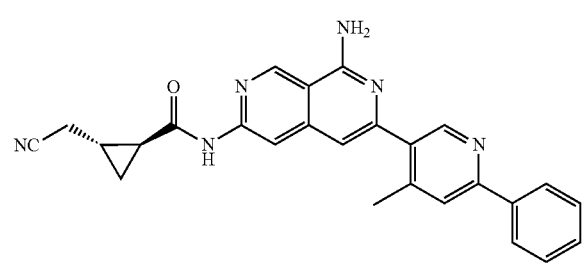

Step 1: 5-bromo-4-methyl-2-phenylpyridine

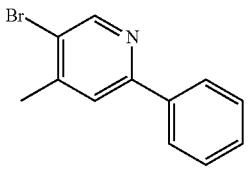

A mixture of 2,5-dibromo-4-methylpyridine (2.0 g, 8.0 mmol), phenylboronic acid (1.069 g, 8.77 mmol), Pd(PPh₃)₄ (921 mg, 0.79 mmol), and potassium carbonate (3.3 g, 23.87 mmol) in water (10 mL)/1,2-dimethoxyethane (40 mL) was heated at 90° C. under nitrogen. After 12 h, the reaction mixture was diluted with H₂O, and the resulting solution was extracted with ethyl acetate. The combined extracts were dried over Na₂SO₄, filtered, and concentrated under vacuum. Purification by flash column chromatography (1% ethyl acetate in petroleum ether) provided 5-bromo-4-methyl-2-phenylpyridine (1.78 g, 90%) as a colorless oil. LCMS (ESI): [M+H]⁺=248.0.

Step 2: (4-methyl-6-phenylpyridin-3-yl)boronic acid

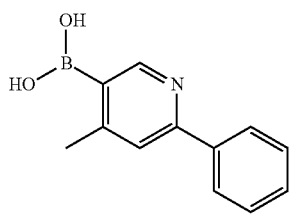 [SMILES: Cc1cc(-c2ccccc2)ncc1B(O)O]

A mixture of 5-bromo-4-methyl-2-phenylpyridine (1.68 g, 6.77 mmol), 4,4,5,5-tetramethyl-2-(tetramethyl-1,3,2-dioxaborolan-2-yl)-1,3,2-dioxaborolane (5.16 g, 20.3 mmol), Pd(dppf)Cl₂ (494 g, 675 mmol), and KOAc (1.99 g, 20.3 mmol) in dioxane (30 mL) was heated at 100° C. under nitrogen. After 3 h, the solids were filtered, and the filtrate was concentrated under vacuum. Purification by flash column chromatography (1:5 ethyl acetate/petroleum ether) gave (4-methyl-6-phenylpyridin-3-yl)boronic acid (1.25 g, 87%) as a light brown solid. LCMS (ESI): M+H⁺=214.1.

Step 3: (1R,2S)—N-[8-amino-6-(4-methyl-6-phenylpyridin-3-yl)-2,7-naphthyridin-3-yl]-2-(cyanomethyl)cyclopropane-1-carboxamide and (1S,2R)—N-[8-amino-6-(4-methyl-6-phenylpyridin-3-yl)-2,7-naphthyridin-3-yl]-2-(cyanomethyl)cyclopropane-1-carboxamide

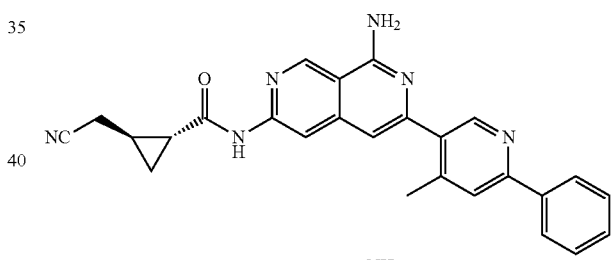

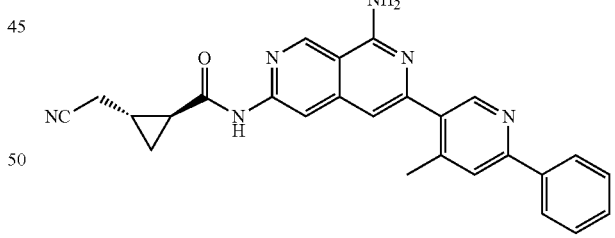

A mixture of trans-N-(8-amino-6-chloro-2,7-naphthyridin-3-yl)-2-(cyanomethyl)cyclopropane-1-carboxamide (0.30 g, 0.99 mmol), (4-methyl-6-phenylpyridin-3-yl)boronic acid (852 mg, 3.99 mmol), XPhos palladium(II) biphenyl-2-amine chloride (79 mg, 0.10 mmol), X-Phos (48 mg, 0.10 mmol), and potassium carbonate (414 mg, 2.99 mmol) in water (2 mL)/dioxane (10 mL) was heated at 100° C. under nitrogen. After 1 h, the solids were filtered, and the filtrate was concentrated under vacuum. Purification by Prep-HPLC gave trans-N-[8-amino-6-(4-methyl-6-phenylpyridin-3-yl)-2,7-naphthyridin-3-yl]-2-(cyanomethyl)cyclopropane-1-carboxamide (50 mg, 12%) as a white solid. The enantiomers were separated by chiral-Prep-HPLC.

Compound 334: LCMS (ESI): [M+H]$^+$=435.2; R$_T$ (min)=1.37, method=K-1; $^1$H NMR (300 MHz, CD$_3$OD) δ 9.31 (s, 1H), 8.62 (s, 1H), 8.32 (s, 1H), 8.02-7.98 (m, 2H), 7.82 (s, 1H), 7.56-7.54 (m, 3H), 7.03 (s, 1H), 2.79-2.69 (m, 2H), 2.54 (s, 3H), 2.06-2.00 (m, 1H), 1.97-1.72 (m, 1H), 1.39-1.31 (m, 1H), 1.09-1.02 (m, 1H). Compound 335: LCMS (ESI): [M+H]$^+$=435.2; R$_T$ (min)=1.37, method=K-1; $^1$H NMR (300 MHz, CD$_3$OD) δ 9.31 (s, 1H), 8.62 (s, 1H), 8.32 (s, 1H), 8.02-7.98 (m, 2H), 7.82 (s, 1H), 7.56-7.54 (m, 3H), 7.03 (s, 1H), 2.79-2.69 (m, 2H), 2.54 (s, 3H), 2.06-2.00 (m, 1H), 1.97-1.72 (m, 1H), 1.39-1.31 (m, 1H), 1.09-1.02 (m, 1H).

Example 243

(±)-N-(8-amino-6-(4-methylpyridin-3-yl)-2,7-naphthyridin-3-yl)spiro[2.2]pentane-1-carboxamide (Compound 336)

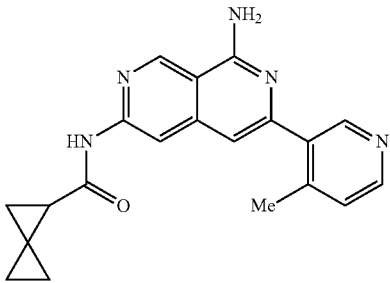 [SMILES: Cc1ccncc1-c1cc2cc(NC(=O)C3CC34CC4)ncc2c(N)n1]

To a solution of spiro[2.2]pentane-1-carboxylic acid (32 mg, 0.0272 mmol), N1,N1-bis(2,4-dimethoxybenzyl)-3-(4-methylpyridin-3-yl)-2,7-naphthyridine-1,6-diamine (150 mg, 0.272 mmol) in pyridine (2.7 mL) was added POCl$_3$ (0.050 mL, 0.54 mmol). After 2 days, saturated aqueous sodium bicarbonate solution was added to the reaction, and the mixture was extracted with dichloromethane. The combined organic was dried over MgSO$_4$, filtered, and concentrated under vacuum. Purification by flash column chromatography (100:0-95:5 dichloromethane/methanol) to afford the intermediate compound, which was dissolved in a mixture of dichloromethane (3 mL) and TFA (0.2 mL). The reaction was stirred for 20 h, neutralized with ammonia in methanol (7 M), the solvent removed and the residue purified by HPLC to afford the target compound as a white solid (7.9 mg, 5% over 2 steps); $^1$H NMR (400 MHz, DMSO-d$_6$) δ 10.75 (s, 1H), 9.35 (s, 1H), 8.56 (s, 1H), 8.43 (d, J=5.0 Hz, 1H), 8.26 (s, 1H), 7.28 (br s, 2H), 7.33-7.21 (m, 1H), 6.95 (s, 1H), 2.43-2.40 (m, 1H), 2.41 (s, 3H), 1.42 (t, J=3.8 Hz, 1H), 1.35 (dd, J=7.4, 3.4 Hz, 1H), 0.95-0.73 (m, 4H).

Example 244

(±)-N6-((2,2-difluorocyclopropyl)methyl)-3-(4-methylpyridin-3-yl)-2,7-naphthyridine-1,6-diamine (Compound 337)

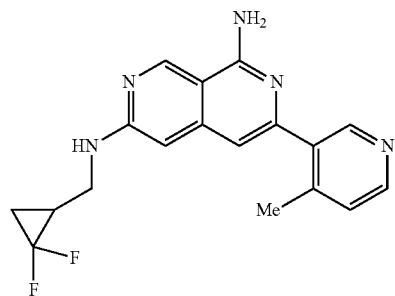 [SMILES: Cc1ccncc1-c1cc2cc(NCC3CC3(F)F)ncc2c(N)n1]

Step 1: (±)-tert-butyl (8-(bis(2,4-dimethoxybenzyl)amino)-6-(4-methylpyridin-3-yl)-2,7-naphthyridin-3-yl)((2,2-difluorocyclopropyl)methyl)carbamate

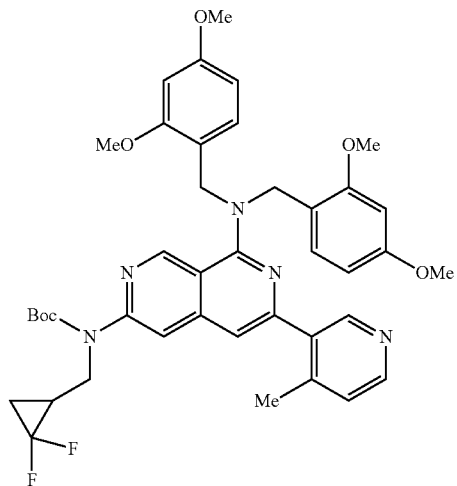 [SMILES: COc1ccc(CN(Cc2ccc(OC)cc2OC)c2nc(-c3cnccc3C)cc3cc(N(CC4CC4(F)F)C(=O)OC(C)(C)C)ncc23)c(OC)c1]

To a solution of tert-butyl (8-(bis(2,4-dimethoxybenzyl)amino)-6-chloro-2,7-naphthyridin-3-yl)carbamate (200 mg, 0.336 mmol) in DMF (1.7 mL) was added 1-bromomethyl-2,2-difluorocyclopropane (182 mg, 1.01 mmol). The reaction mixture was stirred under nitrogen at 80° C. for 3 h. The reaction mixture was diluted with dichloromethane and filtered. After concentration, onto the crude intermediate residue was weighed 4-methyl-3-(4,4,5,5-tetramethyl-1,3,2-dioxaborolan-2-yl)pyridine (81.0 mg, 0.370 mmol), chloro(2-dicyclohexylphosphino-2',4',6'-triisopropyl-1,1'-biphenyl)[2-(2'-amino-1,1'-biphenyl)]palladium(II) (14.2 mg, 0.0168 mmol), 2-dicyclohexylphosphino-2',4',6'-triisopropylbiphenyl (8.2 mg, 0.018 mmol), and potassium carbonate (139 mg, 1.01 mmol). The vial was purged with nitrogen gas, charged with degassed tetrahydrofuran (1.7 mL) and distilled water (0.3 mL), then sealed, and the reaction mixture was stirred at 80° C. for 1 h. After cooling to rt, the mixture was concentrated to dryness. The reaction residue thus obtained was purified by flash column chromatography (heptane/iPrOAc, 100:0-0:100) to afford the title compound as a yellow foam (175 mg, 70% over 2 steps); $^1$H NMR (400 MHz, Chloroform-d) δ 9.25 (s, 1H), 8.57 (s, 1H), 8.43 (d, J=5.0 Hz, 1H), 7.88 (s, 1H), 7.24-7.19 (m, 2H), 7.11 (d, J=5.1 Hz, 1H), 7.08 (s, 1H), 6.45-6.37 (m, 4H), 4.78 (s, 4H), 4.24-4.11 (m, 2H), 3.79 (s, 6H), 3.64 (s, 6H), 2.21 (s, 3H), 2.15-2.04 (m, 1H), 1.56 (s, 9H), 1.44-1.26 (m, 2H).

Step 2: (±)-N6-((2,2-difluorocyclopropyl)methyl)-3-(4-methylpyridin-3-yl)-2,7-naphthyridine-1,6-diamine

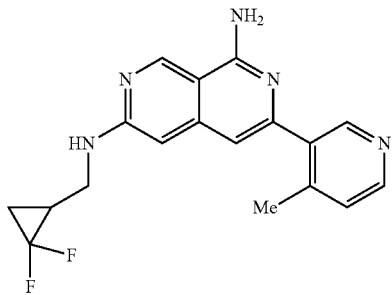 [SMILES: Cc1ccncc1-c1cc2cc(NCC3CC3(F)F)ncc2c(N)n1]

To a solution of (±)-tert-butyl (8-(bis(2,4-dimethoxybenzyl)amino)-6-(4-methylpyridin-3-yl)-2,7-naphthyridin-3-yl)((2,2-difluorocyclopropyl)methyl)carbamate (175 mg, 0.236 mmol) in dichloromethane (0.7 mL) was added trifluoroacetic acid (0.7 mL) and the mixture was stirred at rt for 22 h. Then, 0.4 mL trifluoroacetic acid was added and the mixture stirred at 40° C. for 22 h. The mixture was concentrated to dryness and then purified by HPLC to afford the target compound as a yellow solid (60.3 mg, 75%); $^1$H NMR (400 MHz, DMSO-d$_6$) δ 9.20 (s, 1H), 8.54 (s, 1H), 8.46 (d, J=5.0 Hz, 1H), 7.33 (d, J=5.0 Hz, 1H), 7.25 (br s, 2H), 6.75 (s, 1H), 6.51 (s, 1H), 3.53-3.39 (m, 2H), 2.38 (s, 3H), 2.14-1.98 (m, 1H), 1.66-1.52 (m, 1H), 1.39-1.28 (m, 1H).

Example 245

N6-(2,2-difluoroethyl)-3-(4-methylpyridin-3-yl)-2,7-naphthyridine-1,6-diamine (Compound 338)

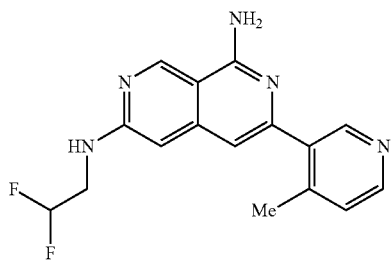 [SMILES: Cc1ccncc1-c1cc2cc(NCC(F)F)ncc2c(N)n1]

Procedure was the same as for (±)-N6-((2,2-difluorocyclopropyl)methyl)-3-(4-methylpyridin-3-yl)-2,7-naphthyridine-1,6-diamine (Compound 337), except that 1,1-difluoro-2-iodoethane was used as alkylating agent, and the reaction was carried directly forward into the Suzuki reaction and deprotection. Thus, reaction of tert-butyl (8-(bis(2,4-dimethoxybenzyl)amino)-6-chloro-2,7-naphthyridin-3-yl)carbamate (162 mg, 0.272 mmol) afforded the target compound as a white solid (58.9 mg, 68% over 3 steps); $^1$H NMR (400 MHz, DMSO-d$_6$) δ 9.14 (s, 1H), 8.52 (s, 1H), 8.41 (d, J=5.0 Hz, 1H), 7.28 (d, J=5.0 Hz, 1H), 7.14 (t, J=6.4 Hz, 1H), 7.04 (br s, 2H), 6.69 (s, 1H), 6.56 (s, 1H), 6.13 (tt, J=56.3, 4.0 Hz, 1H), 3.84-3.69 (m, 2H), 2.39 (s, 3H).

Example 246

(±)-(trans)-N-(8-amino-6-(7-methyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Compound 339)

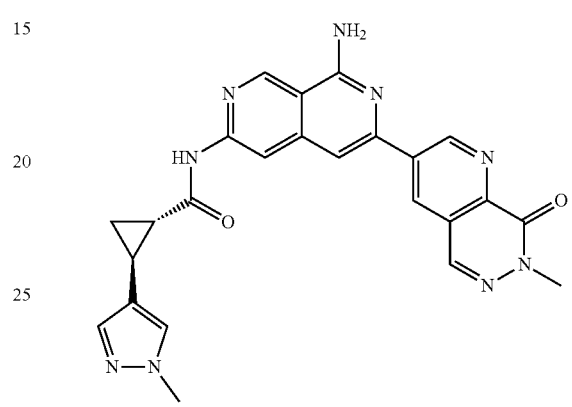

Step 1: methyl 5-bromo-3-(dibromomethyl)pyridine-2-carboxylate

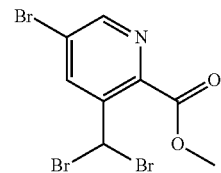

To a solution of N-bromosuccinimide (20.89 g, 117.4 mmol) and benzoylperoxide (2.84 g, 11.74 mmol) in carbon tetrachloride (150 mL) was added methyl 5-bromo-3-methyl-pyridine-2-carboxylate (9.0 g, 39 mmol). The mixture was stirred at 80 C for 16 h under nitrogen. The solution was then concentrated and the residue was purified by flash chromatography (5%-10%-20% ethyl acetate in petroleum ether) to afford methyl 5-bromo-3-(dibromomethyl)pyridine-2-carboxylate as a yellow oil (12 g, 79% yield); LCMS (ESI) [M+H]$^+$=385.8.

Step 2: 3-bromo-7H-pyrido[2,3-d]pyridazin-8-one

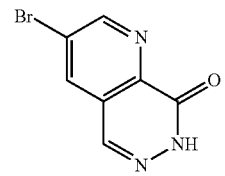 [SMILES: O=c1[nH]ncc2cc(Br)cnc12]

To a solution of methyl 5-bromo-3-(dibromomethyl) pyridine-2-carboxylate (1.0 g, 2.58 mmol) in ethanol (15 mL) was added of hydrazine hydrate (0.77 mL, 15.47 mmol). The reaction mixture was stirred at 80° C. for 1.5 h and then cooled to 15° C. The solids were filtered, washed with MeOH and dried to give one batch of desired product. The filtrate was concentrated and triturated with MeOH. The solids were filtered, rinsed with MeOH and dried to give another batch desired product. The two batches were combined to give 3-bromo-7H-pyrido[2,3-d]pyridazin-8-one as a yellow solid (500 mg, 2.2121 mmol, 86% yield); LCMS (ESI) [M+H]⁺=226.0.

Step 3: 3-bromo-7-methyl-pyrido[2,3-d]pyridazin-8-one

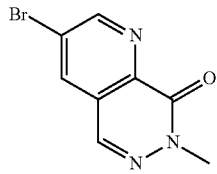

To a suspension of 3-bromo-7H-pyrido[2,3-d]pyridazin-8-one (500 mg, 2.21 mmol) and cesium carbonate (2.52 g, 7.74 mmol) in N,N-Dimethylformamide (5 mL) at 0° C. was added iodomethane (0.59 mL, 9.51 mmol). The reaction mixture was stirred at 15° C. for 16 h. The solvent was removed and the residue was diluted with water (15 mL). The suspension was extracted with ethyl acetate (15 mL×4). The organic layers were washed with brine, dried over sodium sulfate, filtered and concentrated to afford 3-bromo-7-methyl-pyrido[2,3-d]pyridazin-8-one as a yellow solid (140 mg, 26% yield); LCMS (ESI) [M+H]⁺=240.0.

Step 4: (±)-(trans)-N-(8-amino-6-(7-methyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide

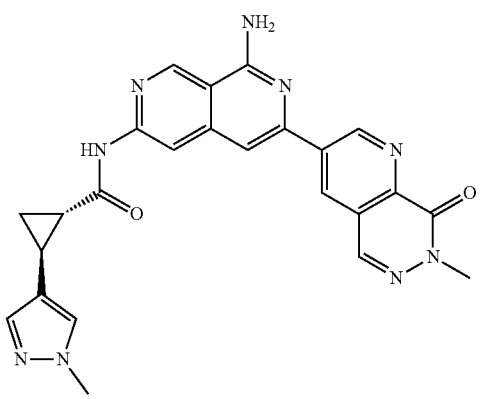 [SMILES: Cn1cc([C@H]2C[C@@H]2C(=O)Nc2cc3cc(-c4cnc5c(=O)n(C)ncc5c4)nc(N)c3cn2)cn1]

Into a vial was weighed 3-bromo-7-methylpyrido[2,3-d]pyridazin-8 (7H)-one (80.0 mg, 0.333 mmol), [1,1'-bis(diphenylphosphino)ferrocene]dichloropalladium(II)-dichloromethane complex (13.9 mg, 0.0167 mmol), bis(pinacolato)diboron (102 mg, 0.400 mmol), and potassium acetate (98.1 mg, 1.00 mmol). Under nitrogen, anhydrous 1,4-dioxane (1.7 mL) was added and the vial was sealed. The reaction mixture was stirred at 100° C. for 3 days. After cooling to rt, under nitrogen, to the reaction vessel was added (±)-(trans)-N-(8-(bis(2,4-dimethoxybenzyl)amino)-6-chloro-2,7-naphthyridin-3-yl)-2-(1-methyl-1H-pyrazol-4-yl)cyclopropane-1-carboxamide (214 mg, 0.333 mmol), chloro(2-dicyclohexylphosphino-2',4',6'-triisopropyl-1,1'-biphenyl)[2-(2'-amino-1,1'-biphenyl)]palladium(II) (14.1 mg, 0.0168 mmol), 2-dicyclohexylphosphino-2',4',6'-triisopropylbiphenyl (8.1 mg, 0.0168 mmol), and potassium phosphate tribasic monohydrate (237 mg, 1.00 mmol), and water (0.3 mL). The vial was sealed and stirred at 100° C. for 2 h. The reaction mixture was concentrated to dryness and residue purified by flash column chromatography (CH₂Cl₂/MeOH, 100:0-90:10). The crude compound thus obtained was then dissolved in thioanisole (0.4 mL) and trifluoroacetic acid added (1.7 mL). After stirring for 18 h, the mixture was concentrated and purified by HPLC to afford the target compound as a yellow solid (68.0 mg, 44% over 2 steps); ¹H NMR (400 MHz, DMSO-d₆) δ 11.01 (s, 1H), 9.77 (d, J=2.3 Hz, 1H), 9.41 (s, 1H), 9.00 (d, J=2.3 Hz, 1H), 8.50 (s, 1H), 8.37 (s, 1H), 7.75 (s, 1H), 7.57 (s, 1H), 7.50 (s, 2H), 7.30 (s, 1H), 3.78 (s, 3H), 3.77 (s, 3H), 2.28-2.18 (m, 2H), 1.46-1.36 (m, 1H), 1.28-1.15 (m, 1H).

Example 247

(±)-5-(1-amino-6-((trans)-2-(1-methyl-1H-pyrazol-4-yl)cyclopropane-1-carboxamido)-2,7-naphthyridin-3-yl)-N,N,4-trimethylpicolinamide (Compound 340)

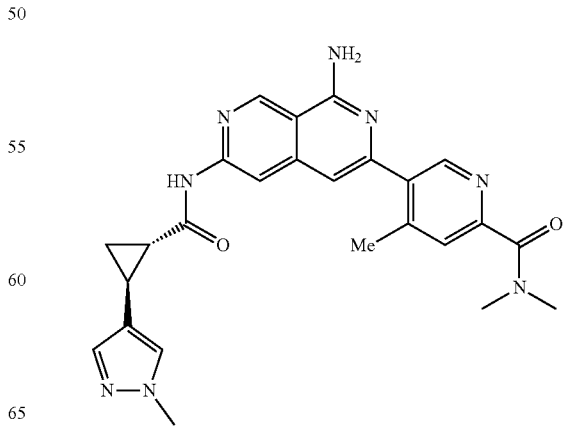

Step 1: (±)-5-(1-(bis(2,4-dimethoxybenzyl)amino)-6-((trans)-2-(1-methyl-1H-pyrazol-4-yl)cyclopropane-1-carboxamido)-2,7-naphthyridin-3-yl)-4-methylpicolinic acid Step 2: (±)-5-(1-amino-6-((trans)-2-(1-methyl-1H-pyrazol-4-yl)cyclopropane-1-carboxamido)-2,7-naphthyridin-3-yl)-N,N,4-trimethylpicolinamide

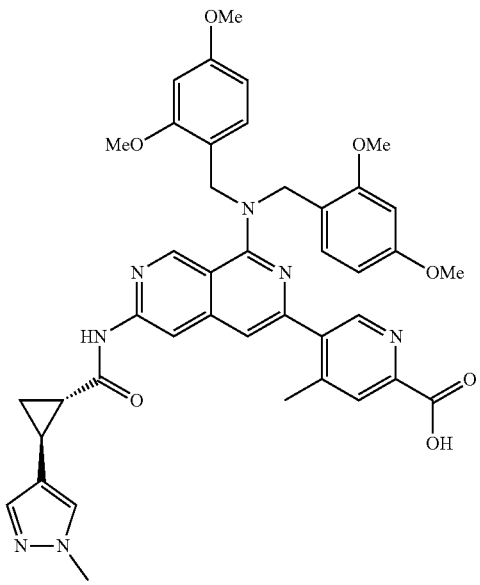 [SMILES: COc1ccc(CN(Cc2ccc(OC)cc2OC)c2nc(-c3cnc(C(=O)O)cc3C)cc3cc(NC(=O)[C@H]4C[C@@H]4c4cnn(C)c4)ncc23)c(OC)c1]

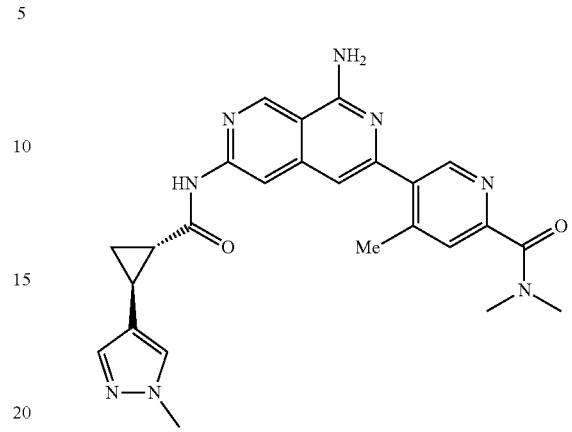

Into a vial was weighed methyl 5-bromo-4-methylpicolinate (1.00 g, 4.35 mmol), [1,1'-bis(diphenylphosphino)ferrocene]dichloropalladium(II)-dichloromethane complex (181 mg, 0.217 mmol), bis(pinacolato)diboron (1.21 g, 4.78 mmol), and potassium acetate (1.28 g, 13.0 mmol). Under nitrogen, anhydrous 1,4-dioxane (11 mL) was added and the vial was sealed. The reaction mixture was stirred at 100° C. for 18 h. After cooling to rt, the reaction mixture was concentrated and the residue purified by flash column chromatography ($CH_2Cl_2$/MeOH, 100:0-90:10) to afford 756 mg of crude aryl pinacolboranate intermediate (contaminated with pinacolborane by 1H NMR). Combining this intermediate (323 mg, ~1.17 mmol) with (±)-(1S,2S)—N-(8-(bis(2,4-dimethoxybenzyl)amino)-6-chloro-2,7-naphthyridin-3-yl)-2-(1-methyl-1H-pyrazol-4-yl)cyclopropane-1-carboxamide (500 mg, 0.777 mmol), chloro(2-dicyclohexylphosphino-2',4',6'-triisopropyl-1,1'-biphenyl)[2-(2'-amino-1,1'-biphenyl)]palladium(II) (32.8 mg, 0.0389 mmol), 2-dicyclohexylphosphino-2',4',6'-triisopropylbiphenyl (18.9 mg, 0.0389 mmol), and potassium phosphate tribasic monohydrate (554 mg, 2.33 mmol) in a vial, tetrahydrofuran (3.9 mL) and water (0.7 mL) were added under nitrogen and the vial was sealed and stirred at 80° C. for 19 h. The reaction mixture still contained starting material and so an equal aliquot of catalyst, ligand and water, as well as potassium phosphate tribasic monohydrate (184 mg, 0.777 mmol) and crude aryl pinacolboranate (215 mg, ~0.77 mmol) were added and stirred at 80° C. for 3 days. The mixture was concentrated to dryness and residue purified by flash column chromatography ($CH_2Cl_2$/MeOH, 100:0-90:10). The crude compound thus obtained was a yellow oil that contained the product according to HPLC-MS.

To a solution of crude (±)-5-(1-(bis(2,4-dimethoxybenzyl)amino)-6-((trans)-2-(1-methyl-1H-pyrazol-4-yl)cyclopropane-1-carboxamido)-2,7-naphthyridin-3-yl)-4-methylpicolinic acid (100 mg, ~0.13 mmol) and HATU (104 mg, 0.269 mmol) in DMF (0.5 mL) was added dimethylamine hydrochloride (16.4 mg, 0.201 mmol) and triethylamine (0.094 mL, 0.672 mmol). The reaction mixture was stirred for 18 h before being diluted with iPrOAc, washed with sat. $NaHCO_3$ and dried over $MgSO_4$. After concentration, the reaction residue obtained was purified by flash column chromatography ($CH_2Cl_2$/MeOH, 100:0-90:10) to afford 44 mg of crude amide, which was then dissolved in thioanisole (0.033 mL). To that solution was added TFA (0.300 mL), and stirred for 22 h, before being concentrated and purified by HPLC to afford the target compound as a white solid (9.6 mg, 36% over 2 steps); $^1$H NMR (400 MHz, DMSO-$d_6$) δ 10.96 (s, 1H), 9.38 (s, 1H), 8.58 (s, 1H), 8.25 (s, 1H), 7.56 (s, 1H), 7.48 (s, 1H), 7.34 (br s, 2H), 7.29 (s, 1H), 7.03 (s, 1H), 3.76 (s, 3H), 3.02 (s, 3H), 2.99 (s, 3H), 2.46 (s, 3H), 2.24-2.16 (m, 2H), 1.44-1.33 (m, 1H), 1.24-1.12 (m, 1H).

Example 248

(±)-methyl 5-(1-amino-6-((trans)-2-(1-methyl-1H-pyrazol-4-yl)cyclopropane-1-carboxamido)-2,7-naphthyridin-3-yl)-4-methylpicolinate (Compound 341)

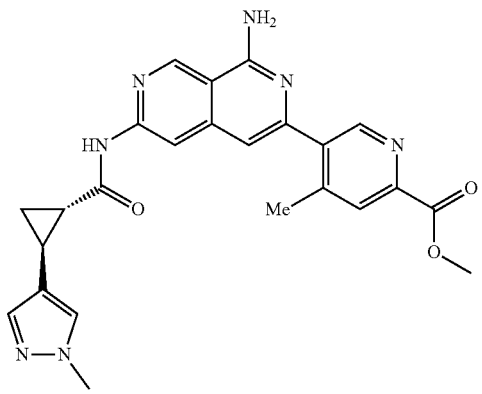

Into a vial was weighed methyl 5-bromo-4-methylpicolinate (300 mg, 1.30 mmol), [1,1'-bis(diphenylphosphino)ferrocene]dichloropalladium(II)-dichloromethane complex (54.3 mg, 0.0652 mmol), bis(pinacolato)diboron (364 mg, 1.43 mmol), and potassium acetate (384 mg, 3.91 mmol). Under nitrogen, anhydrous 1,4-dioxane (6.5 mL) was added and the vial was sealed. The reaction mixture was stirred at 120° C. for 18 h. After cooling to rt, under nitrogen, to the reaction vessel was added (±)-(trans)-N-(8-amino-6-chloro-2,7-naphthyridin-3-yl)-2-(1-methyl-1H-pyrazol-4-yl)cyclopropane-1-carboxamide (447 mg, 1.30 mmol), [1,1'-bis(diphenylphosphino)ferrocene]dichloropalladium(II)-dichloromethane complex (54.3 mg, 0.0652 mmol), and potassium carbonate (540 mg, 3.91 mmol), and water (1.3 mL). The vial was sealed and stirred at 100° C. for 23 h. The reaction mixture was concentrated to dryness and residue purified by flash column chromatography ($CH_2Cl_2$/MeOH, 100:0-85:15) to afford the target compound as a brown solid (126 mg, 21% over 2 steps); $^1$H NMR (400 MHz, DMSO-$d_6$) δ 10.95 (s, 1H), 9.38 (s, 1H), 8.71 (s, 1H), 8.28 (s, 1H), 8.01 (s, 1H), 7.56 (s, 1H), 7.37 (br s, 2H), 7.29 (s, 1H), 7.05 (s, 1H), 3.91 (s, 3H), 3.77 (s, 3H), 2.25-2.16 (m, 2H), 1.90 (s, 3H), 1.43-1.34 (m, 1H), 1.24-1.14 (m, 1H).

Example 249

(±)-trans-5-(1-amino-6-((1S,2S)-2-(1-methyl-1H-pyrazol-4-yl)cyclopropane-1-carboxamido)-2,7-naphthyridin-3-yl)-4-methylpicolinic acid (Compound 342)

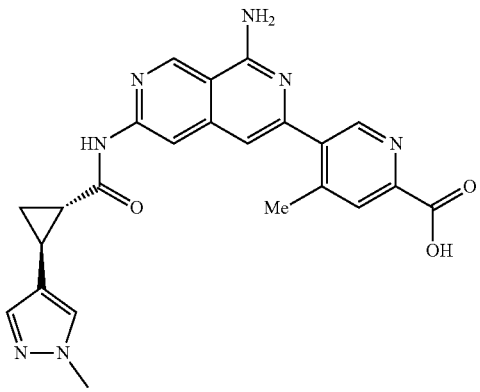 [SMILES: Cc1cc(C(=O)O)ncc1-c1cc2cc(NC(=O)[C@H]3C[C@@H]3c3cnn(C)c3)ncc2c(N)n1]

A solution of (±)-methyl 5-(1-amino-6-((1S,2S)-2-(1-methyl-1H-pyrazol-4-yl)cyclopropane-1-carboxamido)-2,7-naphthyridin-3-yl)-4-methylpicolinate (95.6 mg, 0.209 mmol) and lithium hydroxide hydrate (29.4 mg, 0.700 mmol) in tetrahydrofuran (2.1 mL) and water (0.7 mL) was stirred for 2 days. Hydrochloric acid in dioxane (0.162 mL, 0.648 mmol, 4.0 M) was added and the product precipitated from the reaction mixture and was collected by filtration, rinsing with iPrOAc and 1,4-dioxane to afford a grey solid (92.5 mg, 99%); $^1$H NMR (400 MHz, DMSO-$d_6$) δ 10.94 (s, 1H), 9.37 (s, 1H), 8.59 (s, 1H), 8.27 (s, 1H), 7.90 (s, 1H), 7.56 (s, 1H), 7.34 (br s, 2H), 7.29 (s, 1H), 7.01 (s, 1H), 3.77 (s, 3H), 2.46 (s, 3H), 2.25-2.16 (m, 2H), 1.43-1.34 (m, 1H), 1.23-1.13 (m, 1H).

Example 250

(±)-(trans)-N-(8-amino-6-(4-methyl-6-(2-oxoazetidin-1-yl)pyridin-3-yl)-2,7-naphthyridin-3-yl)-2-(1-methyl-H-pyrazol-4-yl)cyclopropane-1-carboxamide (Compound 343)

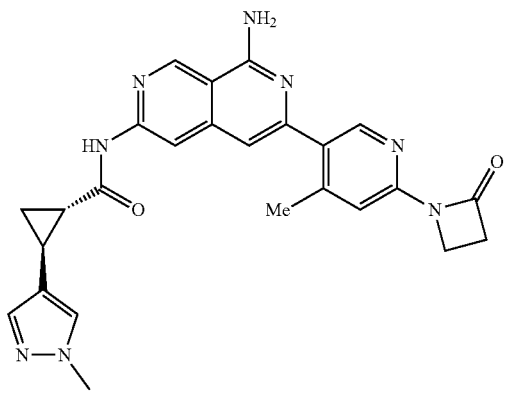 [SMILES: Cc1cc(N2CCC2=O)ncc1-c1cc2cc(NC(=O)[C@H]3C[C@@H]3c3cnn(C)c3)ncc2c(N)n1]

Step 1:
1-(5-bromo-4-methylpyridin-2-yl)azetidin-2-one

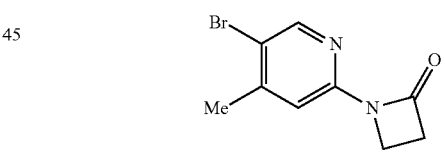

Into a vial was weighed 2,5-dibromo-4-methylpyridine (1.22 g, 4.84 mmol), 2-azetidinone (421 mg, 5.81 mmol), tris(dibenzylideneacetone)dipalladium(0) (111 mg, 0.121 mmol), 4,5-bis(diphenylphosphino)-9,9-dimethylxanthene (140 mg, 0.242 mmol), 3 Å molecular sieves (600 mg), and cesium carbonate (3.16 g, 9.69 mmol). Under a stream of nitrogen gas, the vessel was charged with anhydrous toluene (16 mL) and the vial was sealed. The reaction mixture was stirred at 120° C. for 19.5 h before cooling to rt. The reaction mixture was filtered through Celite rinsing with dichloromethane. After concentration, the crude residue was purified by flash chromatography (100:0-70:30 heptanes/iPrOAc) to afford the title compound as a white solid (828 mg, 71%); $^1$H NMR (400 MHz, Chloroform-d) δ 8.31 (s, 1H), 7.66 (s, 1H), 3.77 (dd, J=4.7, 4.7 Hz, 2H), 3.12 (dd, J=4.7, 4.7 Hz, 2H), 2.39 (s, 3H).

863

Step 2: (±)-(trans)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide

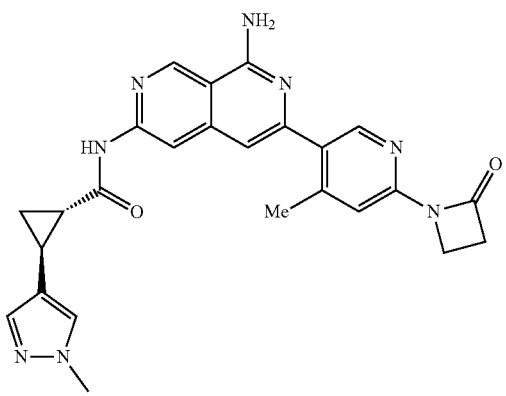 [SMILES: Cc1cc(N2CCC2=O)ncc1-c1cc2cc(NC(=O)[C@H]3C[C@@H]3c3cnn(C)c3)ncc2c(N)n1]

Into a vial was weighed 1-(5-bromo-4-methylpyridin-2-yl)azetidin-2-one (50 mg, 0.207 mmol), [1,1'-bis(diphenylphosphino)ferrocene]dichloropalladium(II)-dichloromethane complex (8.6 mg, 0.0103 mmol), bis(pinacolato)diboron (52.7 mg, 0.207 mmol), and potassium acetate (61.1 mg, 0.622 mmol). Under nitrogen, anhydrous 1,4-dioxane (1.0 mL) was added and the vial was sealed. The reaction mixture was stirred at 100° C. for 17 h. After cooling to rt, under nitrogen, to the reaction vessel was added (±)-(1S, 2S)—N-(8-amino-6-chloro-2,7-naphthyridin-3-yl)-2-(1-methyl-1H-pyrazol-4-yl)cyclopropane-1-carboxamide (71.1 mg, 0.207 mmol), chloro(2-dicyclohexylphosphino-2',4',6'-triisopropyl-1,1'-biphenyl)[2-(2'-amino-1,1'-biphenyl)]palladium(II) (8.8 mg, 0.0104 mmol), 2-dicyclohexylphosphino-2',4',6'-triisopropylbiphenyl (5.0 mg, 0.0104 mmol), potassium carbonate (86 mg, 0.622 mmol), and water (0.2 mL). The vial was sealed and stirred at 100° C. for 19 h. The reaction mixture was concentrated to dryness and residue purified by flash column chromatography (CH$_2$Cl$_2$/MeOH, 100:0-85:15) and then by HPLC to afford the target compound as a white solid (29.6 mg, 31% over 2 steps); $^1$H NMR (400 MHz, DMSO-d$_6$) δ 10.92 (s, 1H), 9.35 (s, 1H), 8.34 (s, 1H), 8.24 (s, 1H), 7.56 (s, 1H), 7.52 (s, 1H), 7.29 (s, 1H), 7.28 (br s, 2H), 6.93 (s, 1H), 3.77 (s, 3H), 3.73 (dd, J=4.7, 4.7 Hz, 2H), 3.12 (dd, J=4.7, 4.7 Hz, 2H), 2.44 (s, 3H), 2.24-2.17 (m, 2H), 1.43-1.33 (m, 1H), 1.23-1.14 (m, 1H).

864

Example 251

(±)-(trans)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide (Compound 344)

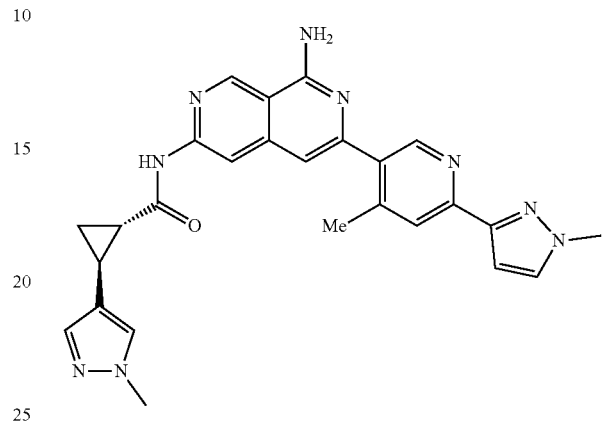

Step 1: 5-bromo-4-methyl-2-(1-methyl-1H-pyrazol-3-yl)pyridine

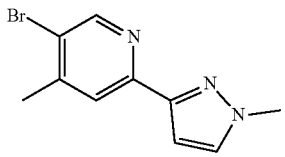

Into a vial was weighed 2,5-dibromo-4-methylpyridine (300 mg, 1.20 mmol), 1-Methyl-1H-pyrazole-3-boronic acid pinacol ester (251 mg, 1.20 mmol), [1,1'-bis(diphenylphosphino)ferrocene]dichloropalladium(II)-dichloromethane complex (49.3 mg, 0.0600 mmol), and sodium carbonate (380 mg, 3.59 mmol). Under nitrogen, anhydrous 1,4-dioxane (6.0 mL) and water (1.2 mL) was added and the vial was sealed. The reaction mixture was stirred at 100° C. for 18 h. After cooling to rt, the reaction mixture was concentrated and the residue purified by flash column chromatography (100:0-40:60 heptanes/iPrOAc) to afford the target compound as a white solid (144 mg, 48%); $^1$H NMR (400 MHz, Chloroform-d) δ 8.62 (s, 1H), 7.81 (s, 1H), 7.40 (d, J=2.4 Hz, 1H), 6.84 (d, J=2.4 Hz, 1H), 3.97 (s, 3H), 2.43 (s, 3H).

865

Step 2: (±)-(trans)-N-(8-amino-6-(4-methyl-6-(1-methyl-H-pyrazol-3-yl)pyridin-3-yl)-2,7-naphthyridin-3-yl)-2-(1-methyl-H-pyrazol-4-yl)cyclopropane-1-carboxamide

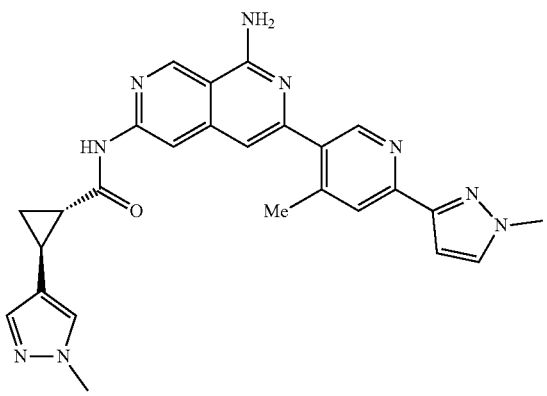 [SMILES: Cc1cc(-c2ccn(C)n2)ncc1-c1cc2cc(NC(=O)[C@H]3C[C@@H]3c3cnn(C)c3)ncc2c(N)n1]

Procedure was the same as for (±)-(trans)-N-(8-amino-6-(4-methyl-6-(2-oxoazetidin-1-yl)pyridin-3-yl)-2,7-naphthyridin-3-yl)-2-(1-methyl-H-pyrazol-4-yl)cyclopropane-1-carboxamide (Compound 343) except that 5-bromo-4-methyl-2-(1-methyl-1H-pyrazol-3-yl)pyridine (53 mg, 0.210 mmol) was used as starting material, affording the target compound as a white solid (27.3 mg, 27% over 2 steps); $^1$H NMR (400 MHz, DMSO-d$_6$) δ 10.93 (s, 1H), 9.36 (s, 1H), 8.56 (s, 1H), 8.26 (s, 1H), 7.83 (s, 1H), 7.78 (d, J=2.1 Hz, 1H), 7.56 (s, 1H), 7.30 (br s, 2H), 7.29 (d, J=2.1 Hz, 1H), 7.00 (s, 1H), 6.81 (s, 1H), 3.93 (s, 3H), 3.77 (s, 3H), 2.47 (s, 3H), 2.26-2.14 (m, 2H), 1.45-1.32 (m, 1H), 1.28-1.15 (m, 1H).

Example 252

(±)-(trans)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide (Compound 345)

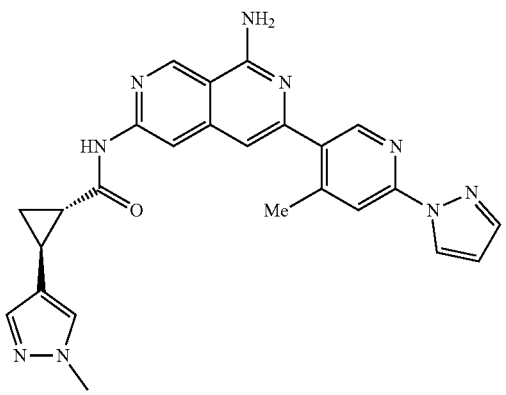 [SMILES: Cc1cc(-n2cccn2)ncc1-c1cc2cc(NC(=O)[C@H]3C[C@@H]3c3cnn(C)c3)ncc2c(N)n1]

866

Step 1:
5-bromo-4-methyl-2-(1H-pyrazol-1-yl)pyridine

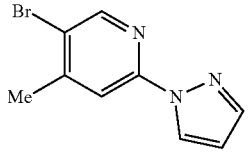 [SMILES: Cc1cc(-n2cccn2)ncc1Br]

To a stirring solution of pyrazole (81.4 mg, 1.20 mmol) in anhydrous DMF (2.4 mL) was added sodium hydride (71.7 mg, 1.79 mmol, [60% in mineral oil]). After 20 min, 2,5-dibromo-4-methylpyridine (300 mg, 1.19 mmol) was added and the vial sealed. The reaction mixture was stirred at 100° C. for 20.5 h and then cooled to rt, diluted with isopropyl acetate, washed with water (ix), brine (x), and dried over magnesium sulfate. Following concentration, the crude residue was subjected to flash column chromatography (100:0-95:5 heptanes/iPrOAc) to afford the title compound as a white solid (141 mg, 49%); $^1$H NMR (400 MHz, Chloroform-d) δ 8.51 (d, J=2.7 Hz, 1H), 8.42 (s, 1H), 7.90 (s, 1H), 7.73 (d, J=1.8 Hz, 1H), 6.46 (dd, J=2.7, 1.8 Hz 1H), 2.47 (s, 3H).

Step 2: (±)-(trans)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide

Procedure was the same as for (±)-(trans)-N-(8-amino-6-(4-methyl-6-(2-oxoazetidin-1-yl)pyridin-3-yl)-2,7-naphthyridin-3-yl)-2-(1-methyl-H-pyrazol-4-yl)cyclopropane-1-carboxamide (Compound 343) except that 5-bromo-4-methyl-2-(1H-pyrazol-1-yl)pyridine (50 mg, 0.210 mmol) was used as starting material, affording the target compound as a white solid (32.4 mg, 33% over 2 steps); $^1$H NMR (400 MHz, DMSO-d$_6$) δ 10.94 (s, 1H), 9.37 (s, 1H), 8.65 (d, J=3.0 Hz, 1H), 8.48 (s, 1H), 8.27 (s, 1H), 7.88 (s, 1H), 7.85 (d, J=3.0 Hz, 1H), 7.56 (s, 1H), 7.33 (br s, 2H), 7.29 (s, 1H), 7.03 (s, 1H), 6.60 (s, 1H), 3.77 (s, 3H), 2.54 (s, 3H), 2.25-2.16 (m, 2H), 1.43-1.34 (m, 1H), 1.23-1.16 (m, 1H).

Example 253

(±)-5-(1-amino-6-((trans)-2-(1-methyl-1H-pyrazol-4-yl)cyclopropane-1-carboxamido)-2,7-naphthyridin-3-yl)-N,4-dimethylpicolinamide (Compound 346)

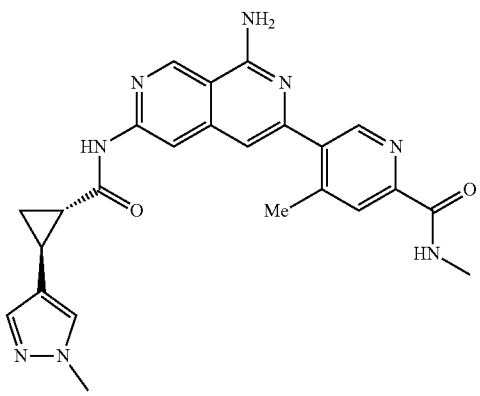

To a solution of (±)-5-(1-amino-6-((1S,2S)-2-(1-methyl-1H-pyrazol-4-yl)cyclopropane-1-carboxamido)-2,7-naphthyridin-3-yl)-4-methylpicolinic acid (37.1 mg, 0.0837 mmol) and HATU (64.9 mg, 0.167 mmol) in DMF (0.8 mL) was added methylamine hydrochloride (11.3 mg, 0.167 mmol) and triethylamine (0.070 mL, 0.50 mmol). The reaction mixture was stirred for 18 h before being diluted with dichloromethane, washed with sat. NaHCO$_3$ and dried over MgSO$_4$. After concentration, the reaction residue obtained was purified by flash column chromatography (CH$_2$Cl$_2$/MeOH, 100:0-85:15) and HPLC to afford the target compound as a white solid (10.2 mg, 27%); $^1$H NMR (400 MHz, DMSO-d$_6$) δ 10.95 (s, 1H), 9.38 (s, 1H), 8.79 (q, J=4.9 Hz, 1H), 8.61 (s, 1H), 8.27 (s, 1H), 7.96 (s, 1H), 7.56 (s, 1H), 7.36 (br s, 2H), 7.29 (s, 1H), 7.04 (s, 1H), 3.77 (s, 3H), 2.84 (d, J=4.9 Hz, 3H), 2.26-2.16 (m, 2H), 1.43-1.32 (m, 1H), 1.23-1.15 (m, 1H).

Example 254

(±)-(trans)-N-(8-amino-6-(6-amino-5-(trifluoromethyl)pyridin-3-yl)-2,7-naphthyridin-3-yl)-2-(1-methyl-1H-pyrazol-4-yl)cyclopropane-1-carboxamide (Compound 347)

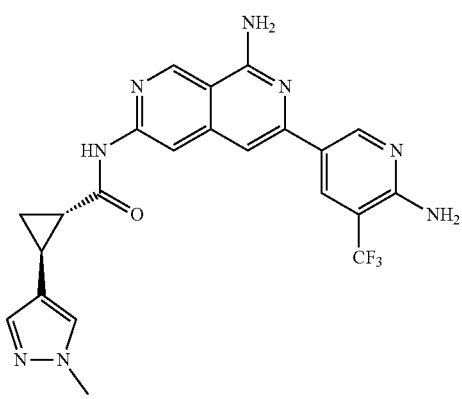 [SMILES: Cn1cc([C@H]2C[C@@H]2C(=O)Nc2cc3cc(-c4cnc(N)c(C(F)(F)F)c4)nc(N)c3cn2)cn1]

Into a vial was weighed (±)-(1S,2S)—N-(8-amino-6-chloro-2,7-naphthyridin-3-yl)-2-(1-methyl-1H-pyrazol-4-yl)cyclopropane-1-carboxamide (60.0 mg, 0.175 mmol), 5-(4,4,5,5-tetramethyl-1,3,2-dioxaborolan-2-yl)-3-(trifluoromethyl)pyridin-2-amine (50.4 mg, 0.175 mmol), chloro(2-dicyclohexylphosphino-2',4',6'-triisopropyl-1,1'-biphenyl)[2-(2'-amino-1,1'-biphenyl)]palladium(II) (7.4 mg, 0.0088 mmol), 2-dicyclohexylphosphino-2',4',6'-triisopropylbiphenyl (4.3 mg, 0.0088 mmol), and potassium carbonate (73 mg, 0.53 mmol). Under nitrogen, anhydrous tetrahydrofuran (0.9 mL) and water (0.2 mL) were added and the vial was sealed. The reaction mixture was stirred at 80° C. for 17 h. After cooling to rt, the reaction mixture was filtered through celite, rinsing with dichloromethane and methanol. After concentrating to dryness, the residue was purified by HPLC to afford the target compound as a white solid (17.2 mg, 21%); $^1$H NMR (400 MHz, DMSO-d$_6$) δ 10.87 (s, 1H), 9.28 (s, 1H), 8.98 (d, J=2.3 Hz, 1H), 8.47 (d, J=2.3 Hz, 1H), 8.24 (s, 1H), 7.56 (s, 1H), 7.42 (s, 1H), 7.29 (s, 1H), 7.28 (br s, 2H), 6.75 (br s, 2H), 3.77 (s, 3H), 2.26-2.15 (m, 2H), 1.44-1.30 (m, 1H), 1.24-1.16 (m, 1H).

Example 255

(±)-benzyl 5-(1-amino-6-((trans)-2-(1-methyl-1H-pyrazol-4-yl)cyclopropane-1-carboxamido)-2,7-naphthyridin-3-yl)-4-methylpicolinate (Compound 348)

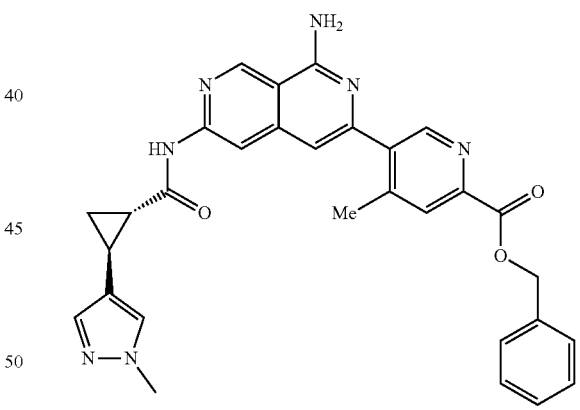

To a suspension of (±)-5-(1-amino-6-((1S,2S)-2-(1-methyl-1H-pyrazol-4-yl)cyclopropane-1-carboxamido)-2,7-naphthyridin-3-yl)-4-methylpicolinic acid (33.3 mg, 0.0751 mmol) in anhydrous dimethylsulfoxide (0.8 mL) was added potassium carbonate (21 mg, 0.11 mmol) and benzyl bromide (0.013 mL, 0.11 mmol). The reaction vessel was sealed and stirred at 80° C. for 24 h. The mixture was filtered and concentrated. Purification of the residue obtained by HPLC afforded the target compound as a yellow solid (8.3 mg, 21%); $^1$H NMR (400 MHz, DMSO-d$_6$) δ 10.95 (s, 1H), 9.38 (s, 1H), 8.71 (s, 1H), 8.27 (s, 1H), 8.04 (s, 1H), 7.56 (s, 1H), 7.53-7.47 (m, 2H), 7.45-7.34 (m, 5H), 7.29 (s, 1H), 7.04 (s, 1H), 5.41 (s, 2H), 3.77 (s, 3H), 2.25-2.16 (m, 2H), 1.45-1.33 (m, 1H), 1.26-1.16 (m, 1H).

Example 256

(1S,2R,3S)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 357) (1R,2R,3R)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 356) (1S,2S,3S)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 355) and (1R,2S,3R)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 354)

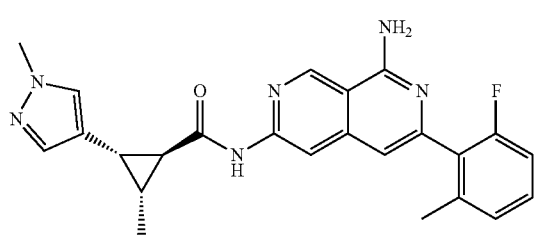

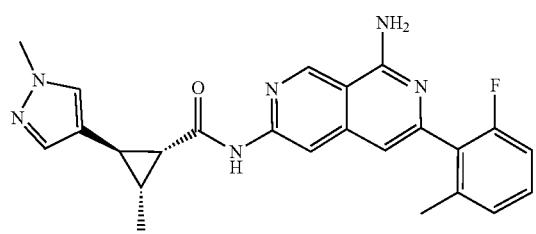

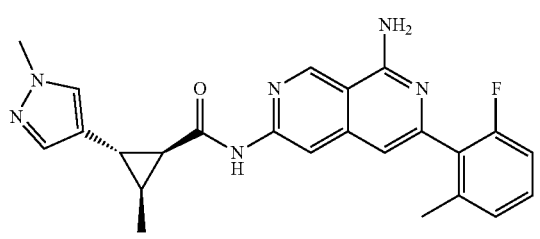

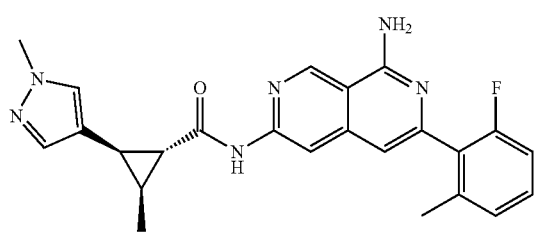

Step 1: tert-butyl (2E)-3-(1-methyl-1H-pyrazol-4-yl)prop-2-enoate

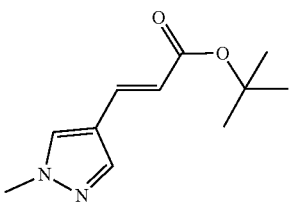

To a solution of 4-iodo-1-methyl-1H-pyrazole (20 g, 96.15 mmol) in N,N-dimethylformamide (100 mL) was added tert-butyl prop-2-enoate (40.6 g, 316.77 mmol), triethylamine (13.6 g, 134.40 mmol), palladium diacetate (3.23 g, 14.39 mmol) and tri(2-methylphenyl)phosphine (5.85 g, 19.22 mmol). The reaction was stirred for 16 h at 110° C. The resulting mixture was cooled to room temperature and then concentrated under vacuum. The residue was purified on a silica gel column eluted with ethyl acetate/petroleum ether (1/2) to afford tert-butyl (2E)-3-(1-methyl-1H-pyrazol-4-yl)prop-2-enoate (14.5 g, 69.38 mmol) as a red oil. LCMS (ESI) [M+H]$^+$=209.1.

Step 2: trans-tert-butyl-2-methyl-3-(1-methyl-1H-pyrazol-4-yl)cyclopropane-1-carboxylate

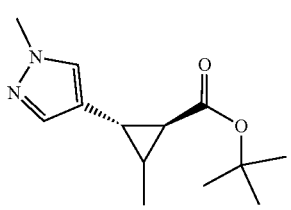 [SMILES: CC1[C@H](C(=O)OC(C)(C)C)[C@H]1c1cnn(C)c1]

To a solution of ethyldiphenylsulfanium tetrafluoroboranuide (13.7 g, 45.34 mmol) in ethylene glycol dimethyl ether (150 mL) and dichloromethane (10 mL) was added LDA (23 ml, 2 mmol in THF) dropwise over 10 min at −65° C. The reaction was stirred for 1 h at −65° C. A solution of tert-butyl (2E)-3-(1-methyl-1H-pyrazol-4-yl)prop-2-enoate (3 g, 14.41 mmol) in ethylene glycol dimethyl ether (5 mL) was added dropwised for 5 mins at −65° C. The resulting solution was stirred for 5 h at room temperature. The reaction was quenched by the addition of water. The resulting mixture was extracted with dichloromethane and dried with anhydrous sodium sulfate. After filtration, the filtrate was concentrated under vacuum to afford trans-tert-butyl-2-methyl-3-(1-methyl-1H-pyrazol-4-yl)cyclopropane-1-carboxylate (4.5 g, crude) as a brown oil. LCMS (ESI) [M+H]$^+$=237.1.

Step 3: trans-2-methyl-3-(1-methyl-1H-pyrazol-4-yl)cyclopropane-1-carboxylic acid

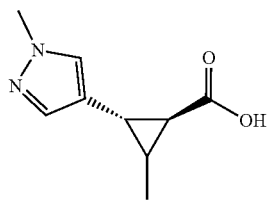

A solution of trans-tert-butyl-2-methyl-3-(1-methyl-1H-pyrazol-4-yl)cyclopropane-1-carboxylate (4.5 g, 19.04 mmol) in trifluoroacetic acid (10 mL) and dichloromethane (10 mL) was stirred for 3 h at room temperature. The resulting mixture was concentrated under vacuum. The pH value of the solution was adjusted to pH 11 with 12% aqueous sodium hydroxide solution. The resulting solution was extracted with dichloromethane, and the aqueous layer was adjusted to pH 3 with 12% aqueous hydrogen chloride. The resulting solution was extracted with ethyl acetate, dried with anhydrous sodium sulfate. After filtration, the filtrate was concentrated under vacuum to afford trans-2-methyl-3-(1-methyl-1H-pyrazol-4-yl)cyclopropane-1-carboxylic acid (3 g, 16.57 mmol) as a light yellow oil. LCMS (ESI) [M+H]$^+$=181.1.

Step 3: trans-N-(8-[bis[(2,4-dimethoxyphenyl)methyl]amino]-6-(2-fluoro-6-methylphenyl)-2,7-naphthyridin-3-yl)-2-methyl-3-(1-methyl-1H-pyrazol-4-yl)cyclopropane-1-carboxamide

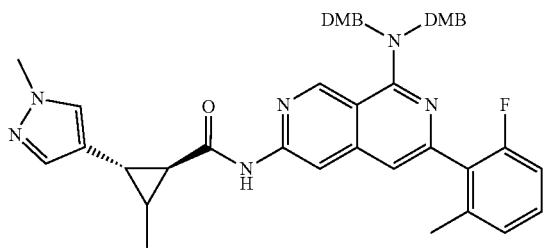

To a solution of 1-N,1-N-bis[(2,4-dimethoxyphenyl)methyl]-3-(2-fluoro-6-methylphenyl)-2,7-naphthyridine-1,6-diamine (600 mg, 1.05 mmol), trans-2-methyl-3-(1-methyl-1H-pyrazol-4-yl)cyclopropane-1-carboxylic acid (247 mg, 1.37 mmol) in dichloromethane (20 mL) and pyridine (4 mL) was added POCl$_3$ (323 mg, 2.10 mmol) over 5 mins at 0° C. The reaction was stirred for 30 min at 25° C. The reaction was then quenched by the addition of water. The resulting solution was extracted with 3×100 mL of dichloromethane and the organic layers combined and dried over anhydrous sodium sulfate and concentrated under vacuum to afford trans-N-(8-[bis[(2,4-dimethoxyphenyl)methyl]amino]-6-(2-fluoro-6-methylphenyl)-2,7-naphthyridin-3-yl)-2-methyl-3-(1-methyl-1H-pyrazol-4-yl)cyclopropane-1-carboxamide (700 mg, 0.96 mmol) as a brown solid. LCMS (ESI) [M+H]$^+$=731.

Step 4: (1S,2R,3S)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 357) (1R,2R,3R)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 356) (1S,2S,3S)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 355) and (1R,2S,3R)—N-[8-amino-6-(2-fluoro-6-methylphenyl)-2,7-naphthyridin-3-yl]-2-methyl-3-(1-methyl-1H-pyrazol-4-yl)cyclopropane-1-carboxamide (Compound 354)

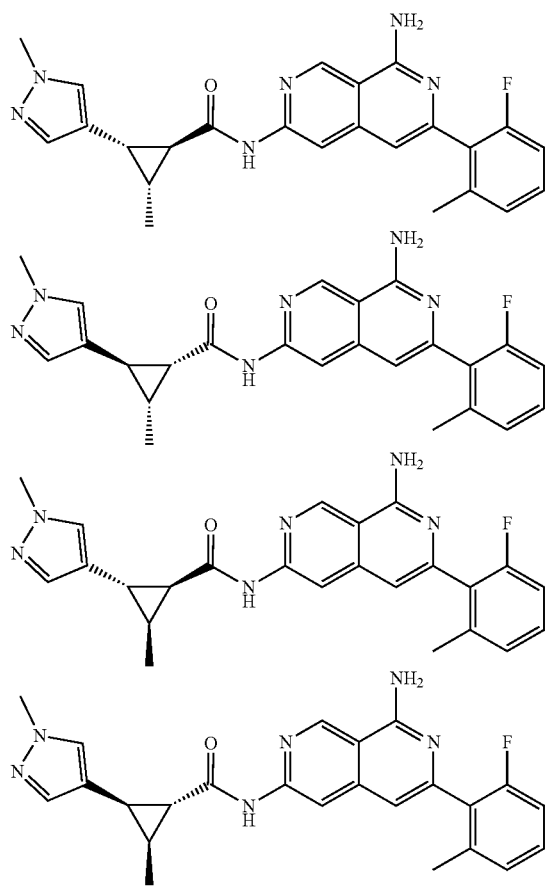

A mixture of trans-N-(8-[[(2,4-dimethoxyphenyl)methyl][(3,5-dimethoxyphenyl)methyl]amino]-6-(2-fluoro-6-methylphenyl)-2,7-naphthyridin-3-yl)-2-methyl-3-(1-methyl-1H-pyrazol-4-yl)cyclopropane-1-carboxamide (700 mg, 0.96 mmol) in trifluoroacetic acid (10 mL) was stirred for 1 h at 25° C. The mixture was concentrated under vacuum. The reaction mixture was adjusted to pH 10 with ammonia in methanol (7 mol/L). The crude product was purified by Prep-HPLC (C18 OBD Column; 0.5% NH$_4$HCO$_3$ in water: ACN=30%-60% in 9 min) to afford trans-N-[8-amino-6-(2-fluoro-6-methylphenyl)-2,7-naphthyridin-3-yl]-2-methyl-3-(1-methyl-1H-pyrazol-4-yl)cyclopropane-1-carboxamide (400 mg, 0.93 mmol) as a white solid. The racemate was separated by chiral SFC to afford four isomers: (Cyclopropane stereochemistry for the isomers: pyrazole trans to amide; methyl relative stereochemistry arbitrarily assigned; All absolute stereochemistry arbitrarily assigned) Isomer 1: (109.1 mg, 0.25 mmol) as a white solid. Retention time: 1.823 min (Lux 3u Cellulose-3 100*4.6 mm, 2 um; MeOH (20 nM NH$_3$); 4 mL/min); LCMS(ESI) [M+H]$^+$=431; $^1$H NMR (400 MHz, CD$_3$OD) δ 9.31 (s, 1H), 8.29 (s, 1H), 7.51 (s, 1H), 7.40 (s, 1H), 7.33-7.31 (m, 1H), 7.13 (d, J=7.6 Hz, 1H), 7.03 (t, J=8.9 Hz, 1H), 6.86 (s, 1H), 3.88 (s, 3H), 2.53-2.50 (m, 1H), 2.23 (s, 3H), 2.01-2.00 (m, 1H), 1.82-1.71 (m, 1H), 1.06 (d, J=6.3 Hz, 3H); Isomer 2: (19.4 mg, 0.045 mmol) as a white solid. Retention time: 2.833 min (CHIRALPAK AD-3, 3*100 mm, 3 um; ACN:EtOH=1:1 (0.1% DEA); 2 mL/min); LCMS(ESI) [M+H]$^+$=431; $^1$HNMR (400 MHz, CD$_3$OD) δ 9.30 (s, 1H), 8.31 (s, 1H), 7.47 (s, 1H), 7.35-7.30 (m, 2H), 7.14 (d, J=7.6 Hz, 1H), 7.04 (t, J=8.8 Hz, 1H), 6.87 (s, 1H), 3.85 (s, 3H), 2.35-2.32 (m, 1H), 2.24 (s, 3H), 2.18-2.15 (m, 1H), 1.69-1.63 (m, 1H), 1.35 (d, J=6.2 Hz, 3H); Isomer 3: (26.5 mg, 0.061 mmol) as a white solid. Retention time: 2.031 min (Lux 3u Cellulose-3 100*4.6 mm, 2 um; MeOH (20 nM NH$_3$); 4 mL/min); LCMS(ESI) [M+H]$^+$=431; $^1$H NMR (400 MHz, CD$_3$OD) δ 9.30 (s, 1H), 8.31 (s, 1H), 7.47 (s, 1H), 7.35-7.30 (m, 2H), 7.14 (d, J=7.6 Hz, 1H), 7.04 (t, J=8.8 Hz, 1H), 6.87 (s, 1H), 3.85 (s, 3H), 2.35-2.32 (m, 1H), 2.24 (s, 3H), 2.18-2.15 (m, 1H), 1.69-1.63 (m, 1H), 1.35 (d, J=6.2 Hz, 3H); Isomer 4: (93.7 mg, 0.22 mmol) as a white solid. Retention time: 3.994 min (CHIRALPAK AD-3, 3*100 mm, 3 um; ACN: EtOH=1:1 (0.1% DEA); 2 mL/min); LCMS(ESI) [M+H]$^+$=431; $^1$H NMR (400 MHz, CD$_3$OD) δ 9.31 (s, 1H), 8.29 (s, 1H), 7.51 (s, 1H), 7.40 (s, 1H), 7.33-7.31 (m, 1H), 7.13 (d, J=7.6 Hz, 1H), 7.03 (t, J=8.9 Hz, 1H), 6.86 (s, 1H), 3.88 (s, 3H), 2.53-2.50 (m, 1H), 2.23 (s, 3H), 2.01-2.00 (m, 1H), 1.82-1.71 (m, 1H), 1.06 (d, J=6.3 Hz, 3H).

Example 257

Compound Nos. 349, 350, 351, 352, 353, 358, 359, 360, 361, 362, 363, 364, 365, 366, 367, 368, 369, 370, 371, 372, 373, 374, 375, 376, 377, 378, 379, 380, 381, 382, 383, 421, 422, 423, 424, 425, 428, and 429 were prepared in a fashion analogous to Example 256.

Example 258

(1R,2R)—N-(8-amino-6-((4-methylpyridin-3-yl)ethynyl)-2,7-naphthyridin-3-yl)-2-(1-methyl-1H-pyrazol-4-yl)cyclopropanecarboxamide (Compound 392) and (1S,2S)—N-(8-amino-6-((4-methylpyridin-3-yl)ethynyl)-2,7-naphthyridin-3-yl)-2-(1-methyl-1H-pyrazol-4-yl)cyclopropanecarboxamide (Compound 391)

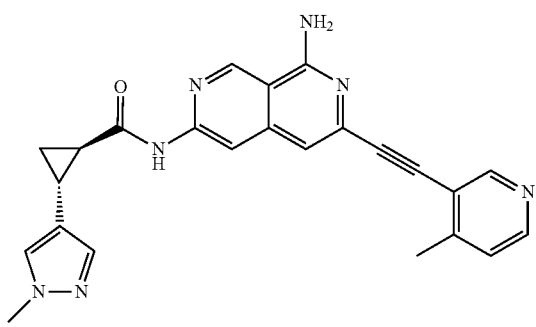

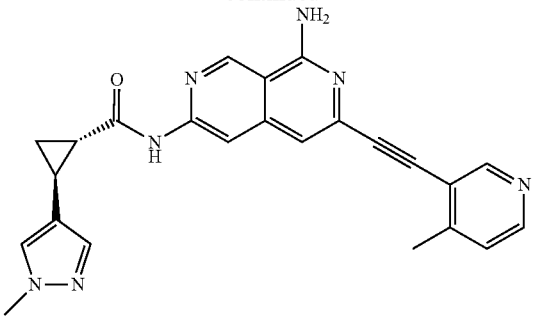

Step 1: 4-methyl-3-((trimethylsilyl)ethynyl)pyridine

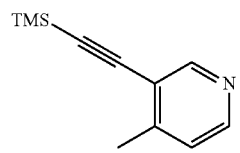

A mixture of 3-bromo-4-methylpyridine (3 g, 17.44 mmol), ethynyltrimethylsilane (2.56 g, 26.06 mmol), Pd(PPh$_3$)$_2$Cl$_2$ (612 mg, 0.87 mmol), CuI (165 mg, 0.86 mmol), TEA (7 g, 69.17 mmol) in N,N-dimethylformamide (200 mL) was stirred for 12 h at 100° C. under nitrogen. The resulting solution was diluted with ethyl acetate (300 mL) and then washed with water. The resulting mixture was concentrated under vacuum. The residue was purified by flash chromatography on a silica gel column eluted with petroleum ether/ethyl acetate (10/1) to afford 4-methyl-3-[2-(trimethylsilyl)ethynyl]pyridine (1 g, 5.26 mmol) as a colorless oil. LCMS (ESI) [M+H]$^+$=190.

Step 2: 3-ethynyl-4-methylpyridine

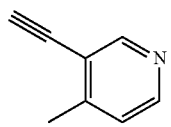

A mixture of 4-methyl-3-[2-(trimethylsilyl)ethynyl]pyridine (1 g, 5.28 mmol) and potassium carbonate (2.2 g, 15.91 mmol) in methanol (30 mL) was stirred for 3 h at room temperature. After filtration the filtrate was concentrated under vacuum. The residue was purified by flash chromatography on a silica gel column eluted with petroleum ether/ethyl acetate (10/1) to afford 3-ethynyl-4-methylpyridine (500 mg, 4.23 mmol) as colorless oil. LCMS (ESI) [M+H]$^+$=118.

Step 3: (1R,2R)—N-(8-amino-6-((4-methylpyridin-3-yl)ethynyl)-2,7-naphthyridin-3-yl)-2-(1-methyl-1H-pyrazol-4-yl)cyclopropanecarboxamide and (1S,2S)—N-(8-amino-6-((4-methylpyridin-3-yl)ethynyl)-2,7-naphthyridin-3-yl)-2-(1-methyl-1H-pyrazol-4-yl)cyclopropanecarboxamide

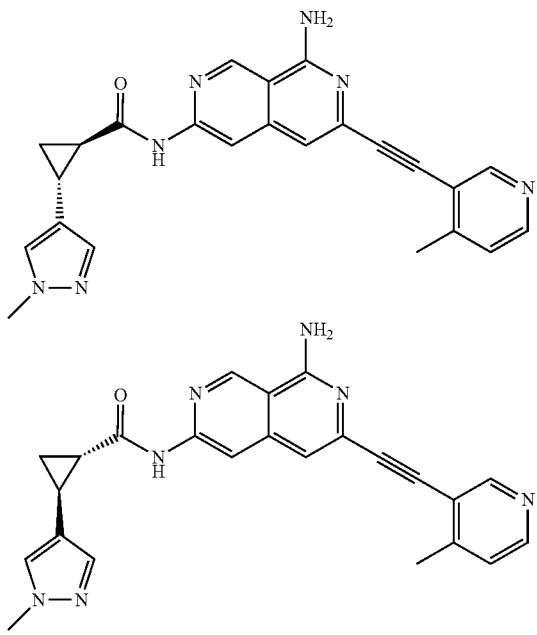

A mixture of 3-ethynyl-4-methylpyridine (855 mg, 7.30 mmol), (1R,2R)—N-(8-amino-6-chloro-2,7-naphthyridin-3-yl)-2-(1-methyl-1H-pyrazol-4-yl)cyclopropane-1-carboxamide (500 mg, 1.46 mmol), potassium carbonate (404 mg, 2.92 mmol), Pd(AcO)$_2$ (33 mg, 0.15 mmol) and PPh$_3$ (77 mg, 0.29 mmol) in N,N-dimethylformamide (10 mL) was stirred for 12 h at 110° C. under nitrogen. After filtration the filtrate was concentrated under vacuum. The residue was purified by Prep-HPLC (XBridge Prep C18 OBD, 19×150 mm 5um; water (0.05% NH$_3$H$_2$O):ACN=0% ACN up to 50% in 7 min) to afford the racemic product (40 mg). The racemic product was separated by Chiral-HPLC to afford two isomers: (Cyclopropane stereochemistry for isomers: pyrazole trans to amide; All absolute stereochemistry arbitrarily assigned) Isomer 1: (51.4 mg, 0.1215 mmol, 8% yield) (assumed) as a yellow solid. Retention time: 2.527 min (CHIRALPAK IC-3. 0.46*5 cm; 3 um; Hex (0.1% DEA):EtOH=50:50; 1.0 ml/min); LCMS (53) [M+H]+= 424.3, $^1$H NMR (400 MHz, DMSO-d$_6$) δ 11.01 (s, 1H), 9.34 (s, 1H), 8.67 (s, 1H), 8.47 (d, J=5.0 Hz, 1H), 8.23 (s, 1H), 7.57 (s, 1H), 7.48-7.37 (m, 3H), 7.30 (s, 1H), 7.20 (s, 1H), 3.77 (s, 3H), 2.49 (s, 3H), 2.28-2.12 (m, 2H), 1.50-1.36 (m, 1H), 1.26-1.12 (m, 1H); Isomer 2: (51.2 mg, 0.1210 mmol, 8% yield) (assumed) as a yellow solid. Retention time: 3.588 min (CHIRALPAK IC-3. 0.46*5 cm; 3 um; Hex (0.1% DEA):EtOH=50:50; 1.0 ml/min); LCMS (53) [M+H]+= 424.2, $^1$H NMR (400 MHz, DMSO-d$_6$) δ 11.01 (s, 1H), 9.34 (s, 1H), 8.67 (s, 1H), 8.47 (d, J=5.0 Hz, 1H), 8.23 (s, 1H), 7.57 (s, 1H), 7.48-7.37 (m, 3H), 7.30 (s, 1H), 7.20 (s, 1H), 3.77 (s, 3H), 2.49 (s, 3H), 2.28-2.12 (m, 2H), 1.50-1.36 (m, 1H), 1.26-1.12 (m, 1H).

Example 259

N-(8-amino-6-(4-methylpyridin-3-yl)-2,7-naphthyridin-3-yl)-3-(methylsulfonamido)bicyclo[3.1.0]hexane-6-carboxamide (Compound 412)

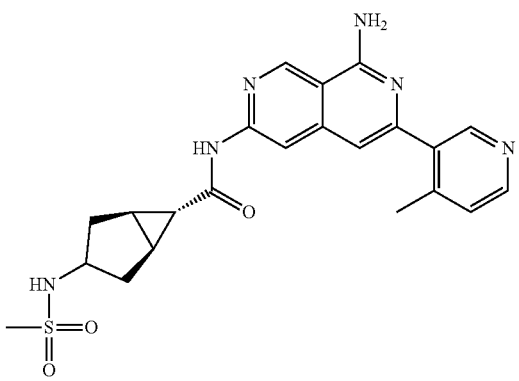

Step 1: 3-amino-N-(8-(bis(2,4-dimethoxybenzyl)amino)-6-(4-methylpyridin-3-yl)-2,7-naphthyridin-3-yl)bicyclo[3.1.0]hexane-6-carboxamide

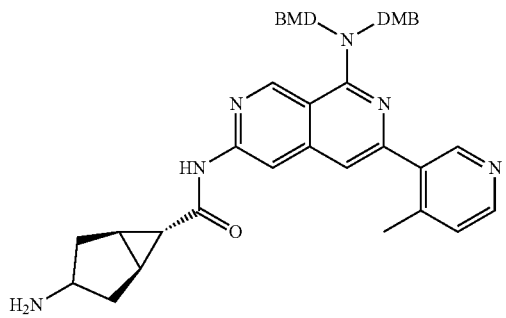

A mixture of N-(8-[bis[(2,4-dimethoxyphenyl)methyl]amino]-6-(4-methylpyridin-3-yl)-2,7-naphthyridin-3-yl)-3-oxobicyclo[3.1.0]hexane-6-carboxamide (200.00 mg, 0.29 mmol), NH$_4$OAc (228.81 mg, 2.96 mmol), NaBH$_3$CN (27.98 mg, 0.44 mmol) in methanol (5 mL) was stirred for 2 h at 60° C. The reaction mixture was concentrated under vacuum. The residue was purified with silica-gel chromatography (DCM:MeOH=10:1) to give 3-amino-N-(8-(bis(2,4-dimethoxybenzyl)amino)-6-(4-methylpyridin-3-yl)-2,7-naphthyridin-3-yl)bicyclo[3.1.0]hexane-6-carboxamide was got (80 mg, 40%) as brown oil, LCMS (ESI) [M+H]+=675.3

Step 2N-(8-(bis(2,4-dimethoxybenzyl)amino)-6-(4-methylpyridin-3-yl)-2,7-naphthyridin-3-yl)-3-(methylsulfonamido)bicyclo[3.1.0]hexane-6-carboxamide

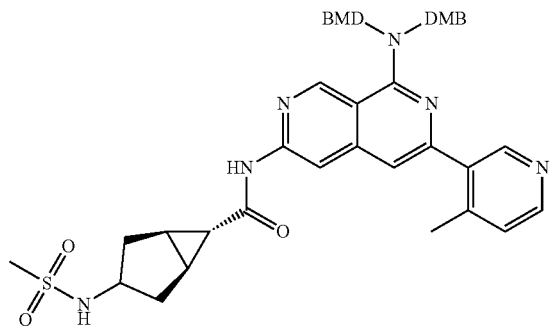

To a mixture of 3-amino-N-(8-[bis[(2,4-dimethoxyphenyl)methyl]amino]-6-(4-methylpyridin-3-yl)-2,7-naphthyridin-3-yl)bicyclo[3.1.0]hexane-6-carboxamide (80.00 mg, 0.12 mmol) and TEA (59.98 mg, 0.59 mmol) in dichloromethane was added Ms$_2$O at 0° C. The reaction solution was stirred for 10 min at 0° C. The reaction was quenched by the addition of water, extracted with dichloromethane and the organic layers combined and dried in an oven under reduced pressure as yellow solid. This solid was used in the next step. LCMS (ESI) [M+H]$^+$=753.3.

Step 3: N-(8-amino-6-(4-methylpyridin-3-yl)-2,7-naphthyridin-3-yl)-3-(methylsulfonamido)bicyclo[3.1.0]hexane-6-carboxamide

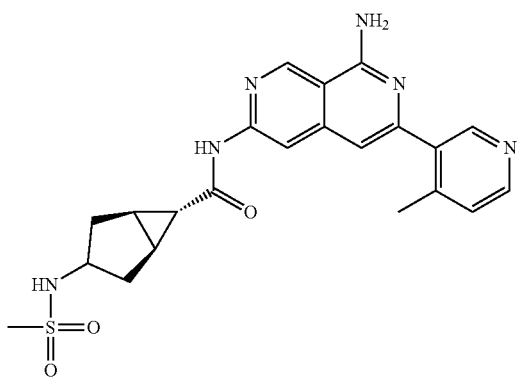

Exo, sterochemistry for NHMs unknown

To a solution of N-(8-[bis[(2,4-dimethoxyphenyl)methyl]amino]-6-(4-methylpyridin-3-yl)-2,7-naphthyridin-3-yl)-3-methanesulfonamidobicyclo[3.1.0]hexane-6-carboxamide (60 mg, 0.08 mmol) in dichloromethane was added trifluoroacetic acid (2.5 mL). The reaction solution was stirred for 4 h at 25° C., then concentrated under vacuum. The residue was purified by Prep-HPLC (XBridge Prep C18 OBD, 19×150 mm 5um; water (0.05% NH$_3$H$_2$O):CH$_3$CN=0% ACN up to 50% in 7 min) to afford (1R,5S,6R)—N-(8-amino-6-(4-methylpyridin-3-yl)-2,7-naphthyridin-3-yl)-3-(methylsulfonamido)bicyclo[3.1.0]hexane-6-carboxamide as a white solid. LCMS (ESI) [M+H]$^+$=453.3, $^1$H NMR (300 MHz, CD$_3$OD) δ 9.35 (s, 1H), 8.52 (s, 1H), 8.46-8.40 (m, 2H), 7.38 (d, J=5.1 Hz, 1H), 7.01 (s, 1H), 5.32-5.00 (m, 1H), 3.98-3.72 (m, 1H), 3.22-3.02 (m, 1H), 3.01-2.94 (m, 1H), 2.92 (s, 3H), 2.90-2.71 (m, 1H), 2.62-2.49 (m, 1H), 2.41 (s, 3H), 2.19-1.98 (m, 1H), 1.70-1.50 (m, 1H).

Example 260

(1S,2S)—N-(8-amino-6-(2,4,7-trimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide, (Compound 410), (1R,2R)—N-(8-amino-6-(2,4,7-trimethyl-8-oxo-7,8-dihydropyrido[2,3-d]pyridazin-3-yl)-2,7-naphthyridin-3-yl)-2-(1-methyl-H-pyrazol-4-yl)cyclopropane-1-carboxamide, (Compound 411); (1S,2S)—N-(8-amino-6-(4,7-dimethyl-8-oxo-7,8-dihydropyrido[2,3-d]pyridazin-3-yl)-2,7-naphthyridin-3-yl)-2-(1-methyl-H-pyrazol-4-yl)cyclopropane-1-carboxamide (Compound 408), (1R,2R)—N-(8-amino-6-(4,7-dimethyl-8-oxo-7,8-dihydropyrido[2,3-d]pyridazin-3-yl)-2,7-naphthyridin-3-yl)-2-(1-methyl-H-pyrazol-4-yl)cyclopropane-1-carboxamide (Compound 409); (1S,2S)—N-(8-amino-6-(2,7-dimethyl-8-oxo-7,8-dihydropyrido[2,3-d]pyridazin-3-yl)-2,7-naphthyridin-3-yl)-2-(1-methyl-H-pyrazol-4-yl)cyclopropane-1-carboxamide (Compound 406), and (1R,2R)—N-(8-amino-6-(2,7-dimethyl-8-oxo-7,8-dihydropyrido[2,3-d]pyridazin-3-yl)-2,7-naphthyridin-3-yl)-2-(1-methyl-H-pyrazol-4-yl)cyclopropane-1-carboxamide (Compound 407)

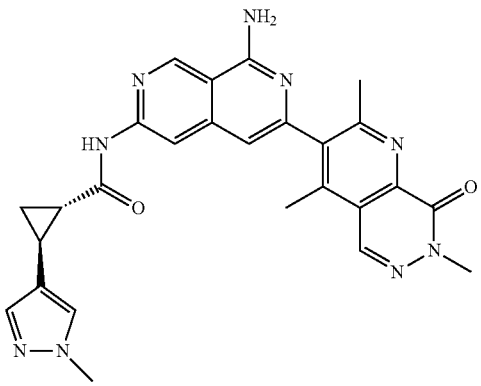

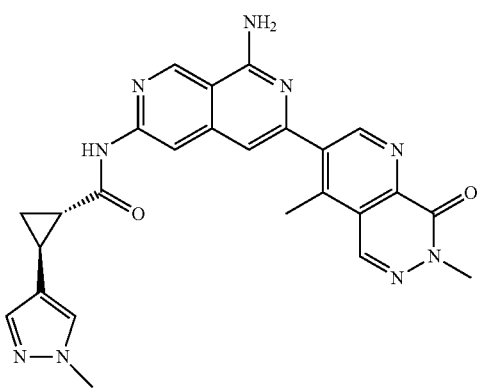

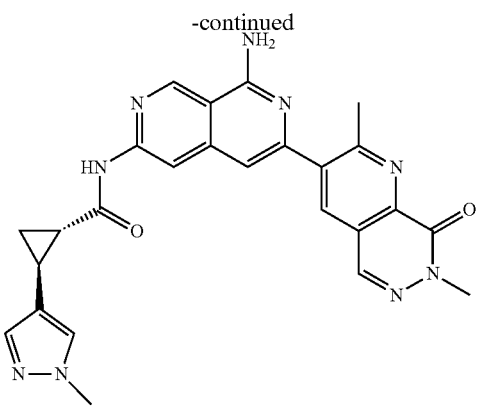

Into a pressure flask was weighed 3-bromo-7-methylpyrido[2,3-d]pyridazin-8-one (400 mg, 1.67 mmol) and (4,4'-di-tert-butyl-2,2'-bipyridine)bis[(2-pyridinyl)phenyl]iridium(III) hexafluorophosphate [Ir(ppy)2(dtbpy)]PF6 (27.7 mg, 2 mol %). Under a stream of nitrogen gas was added acetonitrile (8.3 mL), trifluoroacetic acid (8.3 mL) and tert-butyl peroxyacetate (0.640 mL, 2.00 mmol) and the flask was sealed. The reaction mixture was stirred for 20 h while irradiating with a Kessil H150B blue LED light with a fan directed at the airspace between the light and the mixture. The mixture was diluted with dichloromethane and washed with sat. aq. sodium bicarbonate, then organics dried (MgSO$_4$) and concentrated. The residue was purified by flash column chromatography (CH$_2$Cl$_2$/MeOH, 100:0-95:5) to afford a mixture of mono- and dimethylated products (410 mg crude). Onto this mixture in a vial was weighed [1,1'-bis(diphenylphosphino)ferrocene]dichloropalladium(II)-dichloromethane complex (63.7 mg, 0.0764 mmol), bis(pinacolato)diboron (388 mg, 1.53 mmol), and potassium acetate (450 mg, 4.59 mmol). Under nitrogen, anhydrous 1,4-dioxane (5.1 mL) was added and the vial was sealed. The reaction mixture was stirred at 100° C. for 25 h. After cooling to rt, under nitrogen, to the reaction vessel was added (±)-(1R,2R)—N-(8-amino-6-chloro-2,7-naphthyridin-3-yl)-2-(1-methyl-1H-pyrazol-4-yl)cyclopropane-1-carboxamide (524 mg, 1.53 mmol), chloro(2-dicyclohexylphosphino-2',4',6'-triisopropyl-1,1'-biphenyl)[2-(2'-amino-1,1'-biphenyl)]palladium(II) (61.4 mg, 0.0765 mmol), 2-dicyclohexylphosphino-2',4',6'-triisopropylbiphenyl (37.2 mg, 0.0765 mmol), and potassium carbonate (634 mg, 4.59 mmol), and water (1.5 mL). The vial was sealed and stirred at 80° C. for 69 h. The reaction mixture was concentrated to dryness and residue purified by flash column chromatography (CH$_2$Cl$_2$/MeOH, 100:0-85:15) and by enantiodiscriminatory SFC to afford the dimethyl target compounds as red solids (3.1 mg, 0.4% over 3 steps and 3.4 mg, 0.4% over 3 steps), and the C5- and C7-monomethylated products as white and red solids (8.0 mg, 1.0% over 3 steps; 8.8 mg, 1.0% over 3 steps; 6.9 mg, 0.8% over 3 steps; 6.6 mg, 0.8% over 3 steps). The 5- and 7-assignment was not determined and is assigned arbitrarily (Cyclopropane stereochemistry for isomers: pyrazole trans to amide; All absolute stereochemistry arbitrarily assigned.) Data for dimethyl: $^1$H NMR (400 MHz, DMSO-d$_6$) δ 10.97 (s, 1H), 9.40 (s, 1H), 8.57 (s, 1H), 8.24 (s, 1H), 7.56 (s, 1H), 7.45 (br s, 2H), 7.29 (s, 1H), 6.85 (s, 1H), 3.77 (s, 3H), 3.77 (s, 3H), 2.45 (s, 3H), 2.41 (s, 3H), 2.20 (dd, J=6.9, 6.9 Hz, 2H), 1.42-1.33 (m, 1H), 1.22-1.15 (m, 1H). Data for 5-methyl (assignment arbitrary): $^1$H NMR (400 MHz, DMSO-d$_6$) δ 10.98 (s, 1H), 9.41 (s, 1H), 8.45 (s, 1H), 8.40 (s, 1H), 8.29 (s, 1H), 7.56 (s, 1H), 7.44 (br s, 2H), 7.29 (s, 1H), 7.12 (s, 1H), 3.77 (s, 6H), 2.78 (s, 3H), 2.26-2.17 (m, 2H), 1.45-1.34 (m, 1H), 1.27-1.13 (m, 1H). Data for 7-methyl (assignment arbitrary): $^1$H NMR (400 MHz, DMSO-d$_6$) δ 10.98 (s, 1H), 9.41 (s, 1H), 9.03 (s, 1H), 8.67 (s, 1H), 8.30 (s, 1H), 7.56 (s, 1H), 7.45 (br s, 2H), 7.29 (s, 1H), 7.08 (s, 1H), 3.79 (s, 3H), 3.77 (s, 3H), 2.71 (s, 3H), 2.21 (dd, J=7.2, 7.2 Hz, 2H), 1.44-1.36 (m, 1H), 1.23-1.14 (m, 1H).

Example 261

(1S,2S)—N-(8-amino-6-(6-methoxy-4-methylpyridin-3-yl)-2,7-naphthyridin-3-yl)-2-(1-methyl-1H-pyrazol-4-yl)cyclopropane-1-carboxamide ((Compound 395), (1R,2R)—N-(8-amino-6-(6-methoxy-4-methylpyridin-3-yl)-2,7-naphthyridin-3-yl)-2-(1-methyl-1H-pyrazol-4-yl)cyclopropane-1-carboxamide (Compound 396)

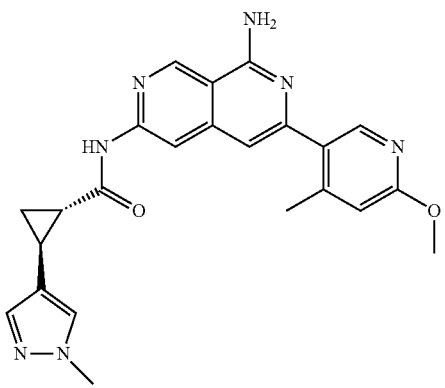

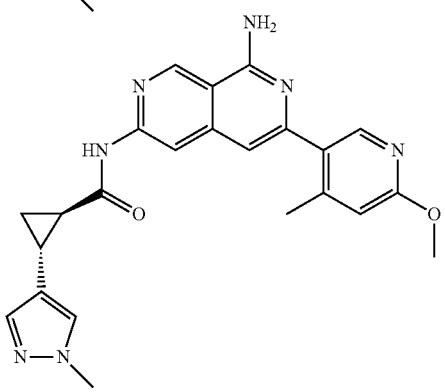

Into a vial was weighed (±)-(1S,2S)—N-(8-amino-6-chloro-2,7-naphthyridin-3-yl)-2-(1-methyl-1H-pyrazol-4-yl)cyclopropane-1-carboxamide (100.0 mg, 0.292 mmol), (6-methoxy-4-methylpyridin-3-yl)boronic acid (51.3 mg, 0.292 mmol), chloro(2-dicyclohexylphosphino-2',4',6'-triisopropyl-1,1'-biphenyl)[2-(2'-amino-1,1'-biphenyl)]palladium(II) (12.3 mg, 0.0146 mmol), 2-dicyclohexylphosphino-2',4',6'-triisopropylbiphenyl (7.1 mg, 0.0146 mmol), and potassium carbonate (121 mg, 0.875 mmol). Under nitrogen, anhydrous tetrahydrofuran (1.5 mL) and water (0.3 mL) were added and the vial was sealed. The reaction mixture was stirred at 100° C. for 17 h. After cooling to rt, the reaction mixture was filtered through celite, rinsing with dichloromethane and methanol. After concentrating to dryness, the residue was purified by HPLC and chiral SFC to afford the target compounds as white solids (23.9 mg, 19% and 29.4 mg, 24%); $^1$H NMR (400 MHz, DMSO-d$_6$) δ 10.91 (s, 1H), 9.34 (s, 1H), 8.23 (s, 1H), 8.19 (s, 1H), 7.56 (s, 1H), 7.29 (s, 1H), 7.24 (br s, 2H), 6.91 (s, 1H), 6.74 (s, 1H), 3.87 (s, 3H), 3.77 (s, 3H), 2.38 (s, 3H), 2.26-2.14 (m, 2H), 1.46-1.32 (m, 1H), 1.27-1.05 (m, 1H). (Cyclopropane stereochemistry for isomers: pyrazole trans to amide; All absolute stereochemistry arbitrarily assigned.)

Example 262

(1S,2S)—N-(8-amino-6-(5-methoxy-4-methylpyridin-3-yl)-2,7-naphthyridin-3-yl)-2-(1-methyl-1H-pyrazol-4-yl)cyclopropane-1-carboxamide ((Compound 393), (1R,2R)—N-(8-amino-6-(5-methoxy-4-methylpyridin-3-yl)-2,7-naphthyridin-3-yl)-2-(1-methyl-1H-pyrazol-4-yl)cyclopropane-1-carboxamide (Compound 394)

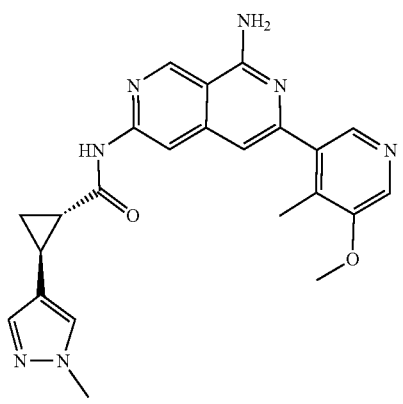

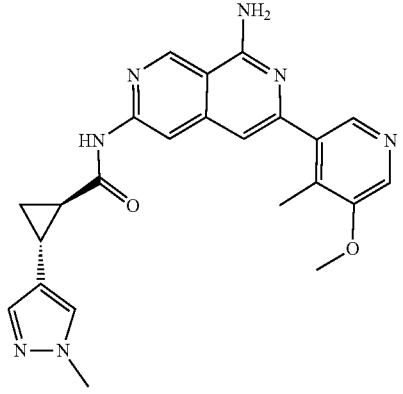

Into a vial was weighed 3-bromo-5-methoxy-4-methylpyridine (120 mg, 0.594 mmol), [1,1'-bis(diphenylphosphino)ferrocene]dichloropalladium(II)-dichloromethane complex (24.7 mg, 0.0297 mmol), bis(pinacolato)diboron (151 mg, 0.594 mmol), and potassium acetate (175 mg, 1.78 mmol). Under nitrogen, anhydrous 1,4-dioxane (3.0 mL) was added and the vial was sealed. The reaction mixture was stirred at 100° C. for 40.5 h. After cooling to rt, under nitrogen, to the reaction vessel was added (±)-(1S,2S)—N-(8-amino-6-chloro-2,7-naphthyridin-3-yl)-2-(1-methyl-1H-pyrazol-4-yl)cyclopropane-1-carboxamide (447 mg, 1.30 mmol), [1,1'-bis(diphenylphosphino)ferrocene]dichloropalladium(II)-dichloromethane complex (24.7 mg, 0.0297 mmol), and potassium carbonate (246 mg, 1.78 mmol), and water (0.6 mL). The vial was sealed and stirred at 80° C. for 4.5 days. The reaction mixture was concentrated to dryness and residue purified by flash column chromatography (CH$_2$Cl$_2$/MeOH, 100:0-85:15) to afford the target compound as a brown solid (85 mg, 33% over 2 steps). Further separation of the enantiomers by chiral SFC afforded the target compounds as white solids; $^1$H NMR (400 MHz, DMSO-d$_6$) δ 10.93 (s, 1H), 9.36 (s, 1H), 8.29 (s, 1H), 8.24 (s, 1H), 8.23 (s, 1H), 7.56 (s, 1H), 7.31 (br s, 2H), 7.29 (s, 1H), 6.91 (s, 1H), 3.94 (s, 3H), 3.77 (s, 3H), 2.25-2.14 (m, 2H), 2.21 (s, 3H), 1.45-1.33 (m, 1H), 1.23-1.12 (m, 1H). (Cyclopropane stereochemistry for isomers: pyrazole trans to amide; All absolute stereochemistry arbitrarily assigned.)

Example 263

(1S,2S)—N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide ((Compound 387), (1R,2R)—N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide (Compound 388)

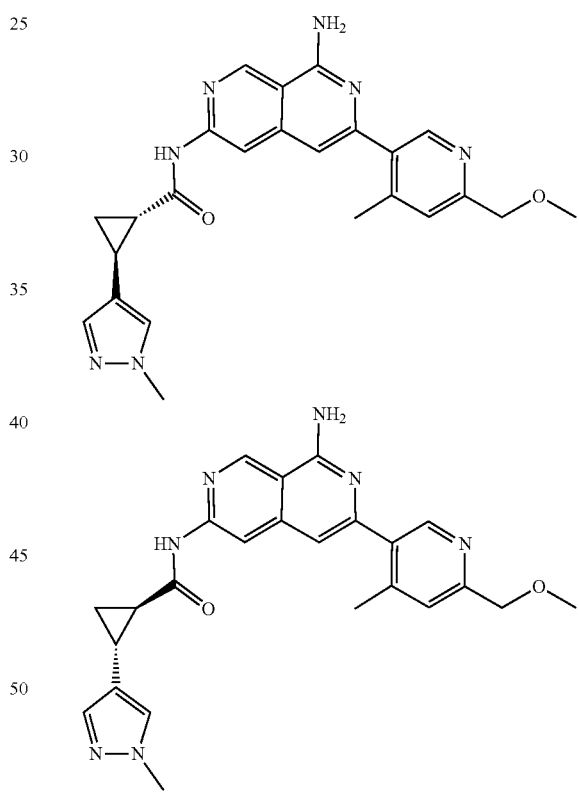

Procedure was the same as for (±)-(1S,2S)—N-(8-amino-6-(4-methyl-6-(2-oxoazetidin-1-yl)pyridin-3-yl)-2,7-naphthyridin-3-yl)-2-(1-methyl-H-pyrazol-4-yl)cyclopropane-1-carboxamide ((Compound 343)) except that methyl 5-bromo-4-methyl-pyridine-2-carboxylate (140 mg, 0.648 mmol) was used as starting material, affording the target compounds as white solids after column chromatography (CH$_2$Cl$_2$/MeOH, 100:0-85:15) and chiral SFC separation (28.0 mg, 10% over 2 steps and 24.5 mg, 9% over 2 steps); $^1$H NMR (400 MHz, DMSO-d$_6$) δ 10.93 (s, 1H), 9.36 (s, 1H), 8.51 (s, 1H), 8.25 (s, 1H), 7.56 (s, 1H), 7.35-7.21 (m, 4H), 6.96 (s, 1H), 4.51 (s, 2H), 3.77 (s, 3H), 3.39 (s, 3H), 2.43 (s, 3H), 2.24-2.13 (m, 2H), 1.44-1.32 (m, 1H), 1.24-1.13 (m, 1H). (Cyclopropane stereochemistry for isomers: pyrazole trans to amide; All absolute stereochemistry arbitrarily assigned.)

Example 264

Methyl (S)-2-(5-(1-amino-6-((1S,2S)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate (Compound 385), Methyl (S)-2-(5-(1-amino-6-((1R,2R)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate (Compound 386)

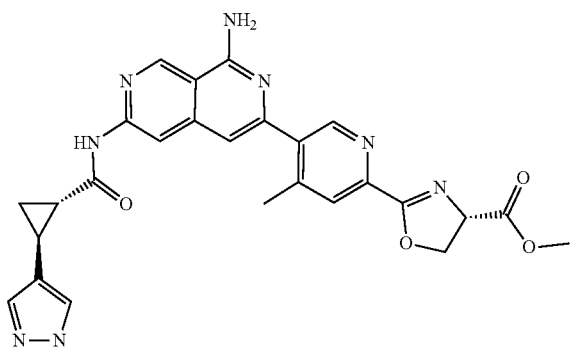

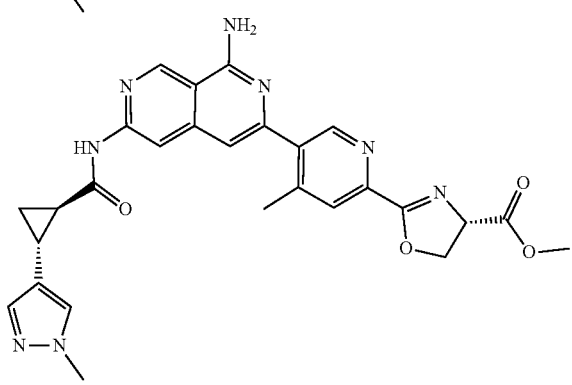

Step 1: methyl (5-bromo-4-methylpicolinoyl)-L-serinate

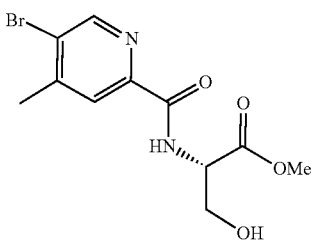 [SMILES: COC(=O)[C@H](CO)NC(=O)c1cc(C)c(Br)cn1]

To a solution of 5-bromo-4-methylpicolinic acid (3.00 g, 13.9 mmol) in anhydrous tetrahydrofuran (46 mL) under nitrogen and at 0° C., was added anhydrous DMF (0.10 mL, 1.4 mmol) followed by dropwise addition of oxalyl chloride over 10 min (1.80 mL, 20.8 mmol). After 5 minutes of stirring, the ice bath was removed, allowing the mixture to come to rt. After 19 h, the mixture was concentrated to dryness. In a separate flask, a solution of L-serine methyl ester hydrochloride (2.38 g, 15.3 mmol) in anhydrous tetrahydrofuran (25 mL) was charged with triethylamine (2.3 mL, 17 mmol) and stirred for 1 h before being poured onto the dried acyl chloride prepared above. The combined reaction mixture was stirred for a further 1.5 h and then poured into sat. aq. sodium bicarbonate and extracted with isopropyl acetate. The organics were washed with brine, dried over magnesium sulfate and then concentrated to dryness. The residue thus obtained was purified by flash column chromatography ($CH_2Cl_2$/MeOH, 100:0-95:5) to afford the title compound as a yellow solid (1.457 g, 33%); $^1$H NMR (400 MHz, Chloroform-d) δ 8.69 (br d, J=7.9 Hz, 1H), 8.60 (s, 1H), 8.04 (s, 1H), 4.85 (dt, J=7.9, 3.9 Hz, 1H), 4.17-3.98 (m, 2H), 3.83 (s, 3H), 2.57 (t, J=6.1 Hz, 1H), 2.47 (s, 3H).

Step 2: methyl (S)-2-(5-(1-amino-6-(trans-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate To a solution of methyl (5-bromo-4-methylpicolinoyl)-L-serinate (400 mg, 1.26 mmol) in anhydrous dichloromethane (6.3 mL) under nitrogen and at −78° C., was added anhydrous diethylaminosulfur trifluoride (0.33 mL, 2.5 mmol) and allowed to warm to rt. After stirring for 1 h, the reaction was carefully quenched by the addition of sat. aq. sodium bicarbonate and extracted with dichloromethane. The organics were dried over magnesium sulfate and concentrated to a crude orange solid. Onto this crude solid in a vial was weighed [1,1'-bis(diphenylphosphino)ferrocene]dichloropalladium(II)-dichloromethane complex (52.5 mg, 0.0630 mmol), bis(pinacolato)diboron (320 mg, 1.26 mmol), and potassium acetate (371 mg, 3.78 mmol). Under nitrogen, anhydrous 1,4-dioxane (6.3 mL) was added and the vial was sealed. The reaction mixture was stirred at 100° C. for 22 h. After cooling to rt, under nitrogen, to the reaction vessel was added (±)-(1R,2R)—N-(8-amino-6-chloro-2,7-naphthyridin-3-yl)-2-(1-methyl-1H-pyrazol-4-yl)cyclopropane-1-carboxamide (432 mg, 1.26 mmol), chloro(2-dicyclohexylphosphino-2',4',6'-triisopropyl-1,1'-biphenyl)[2-(2'-amino-1,1'-biphenyl)]palladium(II) (53.2 mg, 0.0630 mmol), 2-dicyclohexylphosphino-2',4',6'-triisopropylbiphenyl (30.7 mg, 0.0630 mmol), and potassium carbonate (523 mg, 3.78 mmol), and water (1.3 mL). The vial was sealed and stirred at 100° C. for 18.5 h. The reaction mixture was concentrated to dryness and residue purified by flash column chromatography ($CH_2Cl_2$/MeOH, 100:0-85:15) to afford the racemic compound as a white solid (62.2 mg, 9% over 3 steps). Further separation of the enantiomers by chiral SFC afforded the target compounds as white solids; $^1$H NMR (400 MHz, DMSO-$d_6$) δ 10.96 (s, 1H), 10.36 (s, 1H), 9.39 (s, 1H), 8.71 (s, 1H), 8.28 (s, 1H), 8.08 (s, 1H), 7.56 (s, 1H), 7.37 (br s, 2H), 7.29 (s, 1H), 7.07 (s, 1H), 6.63 (s, 1H), 5.90 (d, J=1.5 Hz, 1H), 3.86 (s, 3H), 3.77 (s, 3H), 2.54 (s, 3H), 2.24-2.17 (m, 2H), 1.44-1.34 (m, 1H), 1.29-1.06 (m, 1H). (Pyrazole trans to amide; All absolute stereochemistry arbitrarily assigned).

Example 265 trans-N-(8-amino-6-(6-((S)-4-isopropyl-4,5-dihydrooxazol-2-yl)-4-methylpyridin-3-yl)-2,7-naphthyridin-3-yl)-2-(1-methyl-1H-pyrazol-4-yl)cyclopropane-1-carboxamide (Compound 384)

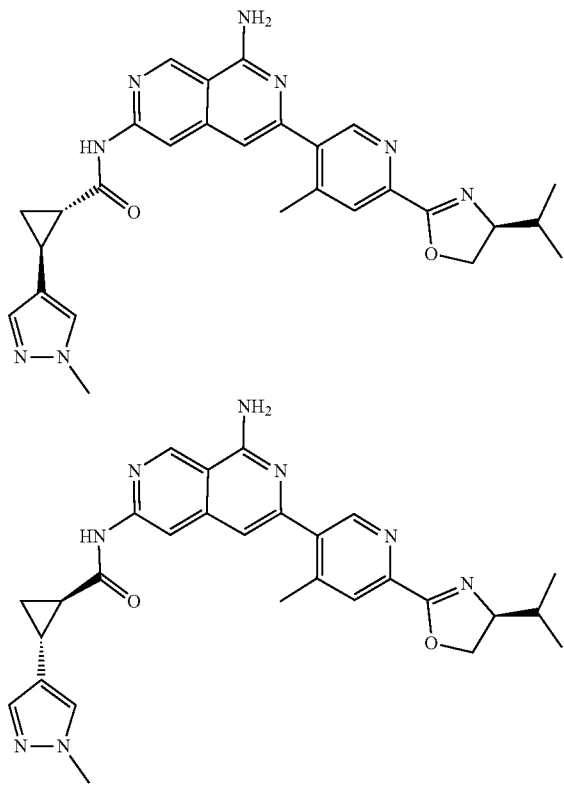

Step 1: (S)-5-bromo-N-(1-hydroxy-3-methylbutan-2-yl)-4-methylpicolinamide

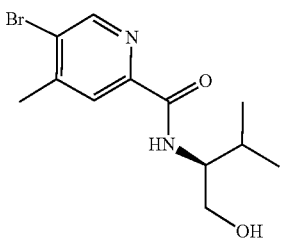 [SMILES: Cc1cc(C(=O)N[C@H](CO)C(C)C)ncc1Br]

To a solution of 5-bromo-4-methylpicolinic acid (2.00 g, 9.26 mmol) and anhydrous DMF (0.14 mL, 1.9 mmol) in anhydrous tetrahydrofuran (31 mL) under nitrogen and at 0° C., was added oxalyl chloride over 10 min (1.61 mL, 18.5 mmol). The ice bath was removed, allowing the mixture to come to rt. After 42 h, the mixture was concentrated to dryness. The crude acid chloride was then dissolved in anhydrous tetrahydrofuran (31 mL) and L-valinol (1.1 mL, 9.3 mmol) was added. The reaction mixture was stirred for 7 days and then poured into sat. aq. sodium bicarbonate and extracted with isopropyl acetate. The organics were washed with brine, dried over magnesium sulfate and then concentrated to dryness. The residue thus obtained was purified by flash column chromatography (heptane/iPrOAc, 100:0-0:100) to afford the title compound as a yellow liquid (1.08 g, 39%); $^1$H NMR (400 MHz, DMSO-$d_6$) δ 8.73 (s, 1H), 8.24 (br d, J=9.7 Hz, 1H), 8.03 (s, 1H), 4.73 (t, J=5.4 Hz, 1H), 3.78-3.70 (m, 1H), 3.63-3.54 (m, 1H), 3.54-3.44 (m, 1H), 2.46 (s, 3H), 1.96-1.87 (m, 1H), 0.91 (d, J=6.6 Hz, 3H), 0.86 (d, J=6.9 Hz, 3H).

Step 2: trans-N-(8-amino-6-(6-((S)-4-isopropyl-4,5-dihydrooxazol-2-yl)-4-methylpyridin-3-yl)-2,7-naphthyridin-3-yl)-2-(1-methyl-1H-pyrazol-4-yl)cyclopropane-1-carboxamide Procedure was the same as for Example 264, except that (S)-5-bromo-N-(1-hydroxy-3-methylbutan-2-yl)-4-methylpicolinamide (118 mg, 0.417 mmol) was used as starting material, affording the target compound as a white solid after column chromatography (CH$_2$Cl$_2$/MeOH, 100:0-85:15) and HPLC purification (10.8 mg, 5% over 2 steps); $^1$H NMR (400 MHz, DMSO-$d_6$) δ 10.95 (s, 1H), 9.38 (s, 1H), 8.65 (s, 1H), 8.27 (s, 1H), 7.93 (s, 1H), 7.56 (s, 1H), 7.36 (br s, 2H), 7.29 (s, 1H), 7.03 (s, 1H), 4.54-4.37 (m, 1H), 4.22-4.05 (m, 2H), 3.77 (s, 3H), 2.25-2.13 (m, 2H), 1.87-1.71 (m, 1H), 1.45-1.30 (m, 1H), 1.24-1.10 (m, 1H), 0.98 (d, J=6.7 Hz, 3H), 0.91 (d, J=6.7 Hz, 3H). (Cyclopropane stereochemistry for isomers: pyrazole trans to amide; absolute stereochemistry arbitrarily assigned.)

Example 266

Compound Nos. 397, 398, 399, 400, 401, 402, 403, 404, 405, 413, 419, 420, and 427 were prepared in a fashion analogous to the procedures in Example 263 or Example 265.

Example 267

2'-((8-amino-6-(5-amino-4-methylpyridin-3-yl)-2,7-naphthyridin-3-yl)amino)-6'-methyl-5',6'-dihydrospiro[cyclopropane-1,4'-pyrazolo[1,5-d][1,4]diazepin]-7'(8'H)-one (Compound 414)

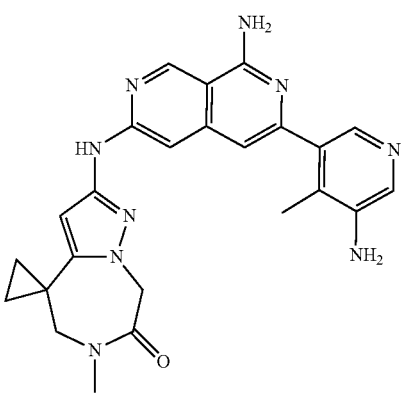 [SMILES: Cc1c(N)cncc1-c1cc2cc(Nc3cc4n(n3)CC(=O)N(C)CC43CC3)ncc2c(N)n1]

887

Step 1: 2-(3,5-Dibromo-1H-pyrazol-1-yl)-N-methyl-N-(prop-2-en-1-yl)acetamide

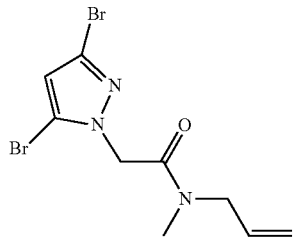

A solution of 2-(3,5-dibromo-1H-pyrazol-1-yl)acetic acid (15 g, 52.84 mmol), methyl(prop-2-en-1-yl)amine (5.7 g, 80.15 mmol), N,N-diisopropylethylamine (27 g, 208.9 mmol) and HATU (30 g, 78.9 mmol) in N,N-dimethylformamide (500 mL) was stirred for 16 hours at room temperature. The resulting mixture was diluted with ethyl acetate and. The organic layer was washed with sodium chloride solution, dried with anhydrous sodium sulfate, filtered and concentrated under vacuum. The residue was purified by flash chromatography on silica gel eluting with ethyl acetate/petroleum ether (2/3) to afford 2-(3,5-dibromo-1H-pyrazol-1-yl)-N-methyl-N-(prop-2-en-1-yl)acetamide (16.3 g, 92%) as a yellow oil. LCMS (ESI) [M+H]$^+$=338.0.

Step 2: 2-Bromo-6-methyl-4-methylidene-4H,5H,6H,7H,8H-pyrazolo[1,5-d][1,4]diazepin-7-one

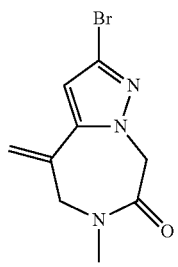

A mixture of 2-(3,5-dibromo-1H-pyrazol-1-yl)-N-methyl-N-(prop-2-en-1-yl)acetamide (5 g, 14.84 mmol), palladium acetate (166 mg, 0.74 mmol), triphenylphosphine (388 mg, 1.48 mmol), TBAB (4.8 g, 14.890 mmol) and potassium acetate (4.2 g, 42.80 mmol) in N,N-dimethylformamide (100 mL) was stirred for 10 h at 80° C. After filtration, the filtrate was concentrated under vacuum. The residue was purified on a silica gel column eluted with ethyl acetate/petroleum ether (2/1) to afford 2-bromo-6-methyl-4-methylidene-4H,5H,6H,7H,8H-pyrazolo[1,5-d][1,4]diazepin-7-one (3.2 g, 84%) as a brown oil. LCMS (ESI) [M+H]$^+$=258.1.

888

Step 3: 2'-bromo-6'-methyl-5',6'-dihydrospiro[cyclopropane-1,4'-pyrazolo[1,5-d][1,4]diazepin]-7'(8'H)-one

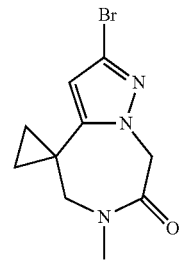

A mixture of trimethylsulfoxonium iodide (1.29 g, 5.86 mmol) and potassium tert-butoxide (656 mg, 5.85 mmol) in dimethyl sulfoxide (30 mL) was stirred for 30 min at room temperature. Then a solution of 2-bromo-6-methyl-4-methylidene-4H,5H,6H,7H,8H-pyrazolo[1,5-d][1,4]diazepin-7-one (500 mg, 1.95 mmol) in dimethyl sulfoxide (3 mL) was added. The mixture was then stirred for 12 h at 50° C. The reaction mixture was diluted with ethyl acetate and then washed with water. The organic layer was dried over anhydrous sodium sulfate, filtered and concentrated under vacuum. The residue was purified by silica gel column with dichloromethane/methanol (10/1) to afford 2'-bromo-6'-methyl-5',6'-dihydrospiro[cyclopropane-1,4'-pyrazolo[1,5-d][1,4]diazepin]-7'(8'H)-one (120 mg, 23%) as a white solid. LCMS (ESI) [M+H]$^+$=270.

Step 4: tert-butyl N-[5-[6-amino-1-[bis[(2,4-dimethoxyphenyl)methyl]amino]-2,7-naphthyridin-3-yl]-4-methyl-3-pyridyl]-N-tert-butoxycarbonyl-carbamate

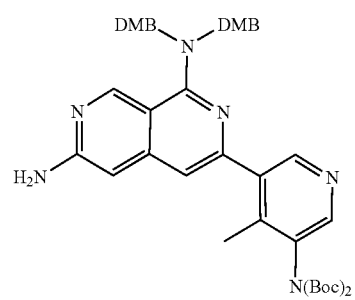

A mixture of 3-chloro-N1,N1-bis[(2,4-dimethoxyphenyl)methyl]-2,7-naphthyridine-1,6-diamine (560 mg, 1.13 mmol), tert-butyl N-tert-butoxycarbonyl-N-[4-methyl-5-(4,4,5,5-tetramethyl-1,3,2-dioxaborolan-2-yl)-3-pyridyl]carbamate (737 mg, 1.7 mmol), XPhosPdG2 (171 mg, 0.23 mmol), XPhos (215 mg, 0.45 mmol) and KOAc (332 mg, 3.39 mmol) in 1,4-dioxane (15 mL) and water (1.5 mL) was stirred at 100° C. for 1 hour. The mixture was concentrated under vacuum. The residue was purified by reverse phase chromatography with water/CH$_3$CN (15/85) to afford tert-butyl N-[5-[6-amino-1-[bis[(2,4-dimethoxyphenyl)methyl]amino]-2,7-naphthyridin-3-yl]-4-methyl-3-pyridyl]-N-tert-butoxycarbonyl-carbamate (220 mg, 0.28 mmol) as a brown solid. LCMS (ESI) [M+H]$^+$=767.

Step 5: tert-butyl N-[5-[1-[bis[(2,4-dimethoxyphenyl)methyl]amino]-6-[(6-methyl-7-oxo-spiro[5,8-dihydropyrazolo[1,5-d][1,4]diazepine-4,1'-cyclopropane]-2-yl)amino]-2,7-naphthyridin-3-yl]-4-methyl-3-pyridyl]-N-tert-butoxycarbonyl-carbamate

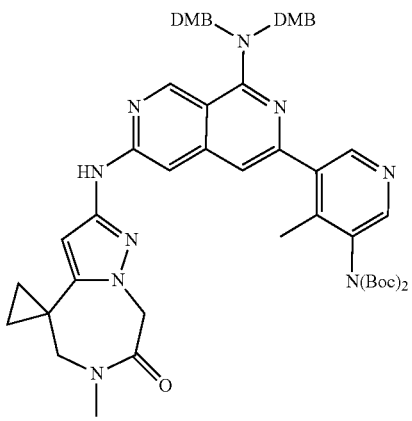

A mixture of tert-butyl N-[5-[6-amino-1-[bis[(2,4-dimethoxyphenyl)methyl]amino]-2,7-naphthyridin-3-yl]-4-methyl-3-pyridyl]-N-tert-butoxycarbonyl-carbamate (215.0 mg, 0.2800 mmol), 2-bromo-6-methyl-spiro[5,8-dihydropyrazolo[1,5-d][1,4]diazepine-4,1'-cyclopropane]-7-one (90 mg, 0.34 mmol), t-BuBrettphos Pd G3 (95 mg, 0.11 mmol), t-BuBrettphos (54 mg, 0.11 mmol) and $Cs_2CO_3$ (456 mg, 1.4 mmol) in 1,4-dioxane (15 mL) was stirred at 130° C. for 2 hours. The reaction was concentrated under vacuum. The residue was purified by flash chromatography on silica gel eluting with DCM/MeOH (97/3) to afford tert-butyl N-[5-[1-[bis[(2,4-dimethoxyphenyl)methyl]amino]-6-[(6-methyl-7-oxo-spiro[5,8-dihydropyrazolo[1,5-d][1,4]diazepine-4,1'-cyclopropane]-2-yl)amino]-2,7-naphthyridin-3-yl]-4-methyl-3-pyridyl]-N-tert-butoxycarbonyl-carbamate (140 mg, 0.14 mmol) as a brown solid. LCMS (ESI) [M+H]$^+$=956.

Step 6: 2-[[8-amino-6-(5-amino-4-methyl-3-pyridyl)-2,7-naphthyridin-3-yl]amino]-6-methyl-spiro[5,8-dihydropyrazolo[1,5-d][1,4]diazepine-4,1'-cyclopropane]-7-one

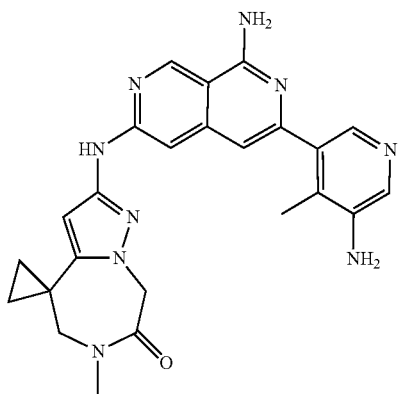 [SMILES: Cc1c(N)cncc1-c1cc2cc(Nc3cc4n(n3)CC(=O)N(C)CC43CC3)ncc2c(N)n1]

A solution of tert-butyl N-[5-[1-[bis[(2,4-dimethoxyphenyl)methyl]amino]-6-[(6-methyl-7-oxo-spiro[5,8-dihydropyrazolo[1,5-d][1,4]diazepine-4,1'-cyclopropane]-2-yl)amino]-2,7-naphthyridin-3-yl]-4-methyl-3-pyridyl]-N-tert-butoxycarbonyl-carbamate (140 mg, 0.15 mmol) and TFA (5 mL) in dichloromethane (0.5 mL) was stirred at 80° C. for 0.5 hour. The mixture was concentrated under vacuum. The reaction mixture was adjusted to pH 10 with $NH_3.H_2O$. The crude product was purified by Prep-HPLC with the following conditions: Column: XBridge Shield RP18 OBD Column 30*150 mm, 5 um; mobile phase A: Water (10 mmol/L $NH_4HCO_3$), Mobile Phase B: ACN; Flow rate: 60 mL/min; Gradient: 20% B to 27% B in 7 min; 254 nm; Rt: 5.9 min to afford 2-[[8-amino-6-(5-amino-4-methyl-3-pyridyl)-2,7-naphthyridin-3-yl]amino]-6-methyl-spiro[5,8-dihydropyrazolo[1,5-d][1,4]diazepine-4,1'-cyclopropane]-7-one (20.4 mg, 0.044 mmol) as a white solid. LCMS (ESI) [M+H]$^+$=456.3; $^1$H NMR (300 MHz, DMSO-d$_6$) δ 9.31 (s, 1H), 9.19 (s, 1H), 7.92 (s, 1H), 7.75 (s, 1H), 7.45 (s, 1H), 7.02 (s, 2H), 6.68 (s, 1H), 5.67 (s, 1H), 5.10-5.06 (m, 4H), 3.72 (s, 2H), 2.99 (s, 3H), 2.06 (s, 3H), 1.23-1.16 (m, 2H), 0.96-0.92 (m, 2H).

Example 268

2-((8-amino-6-(5-amino-4-methylpyridin-3-yl)-2,7-naphthyridin-3-yl)amino)-6-methyl-5,6-dihydro-4H-pyrazolo[1,5-d][1,4]diazepin-7(8H)-one (Compound 415)

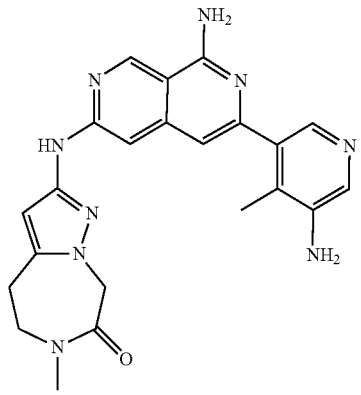 [SMILES: Cc1c(N)cncc1-c1cc2cc(Nc3cc4n(n3)CC(=O)N(C)CC4)ncc2c(N)n1]

Step 1: Methyl 2-(3-bromo-5-methyl-pyrazol-1-yl)acetate

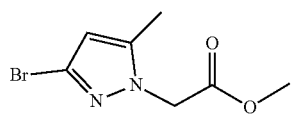

A solution of 3-bromo-5-methyl-1H-pyrazole (100 g, 621.12 mmol), methyl 2-chloroacetate (101.11 g, 931.68 mmol) and $K_2CO_3$ (154.29 g, 1118 mmol) in N,N-dimethylformamide (1 L) was added TBAI (11.46 g, 31.06 mmol). The resulting solution was stirred for 12 h at 20° C. The reaction mixture was diluted with EA (5000 mL). The solution was washed with water (300 mL×3) and the organic

891 layers were combined. The organic layer was dried over anhydrous sodium sulfate and concentrated under vacuum. The residue was purified by flash chromatography on silica gel eluting with PE/DCM (60/40) to afford methyl 2-(3-bromo-5-methyl-pyrazol-1-yl)acetate (120 g, 82.9% yield) as a white solid.

Step 2: Methyl 2-[3-bromo-5-(bromomethyl)pyrazol-1-yl]acetate

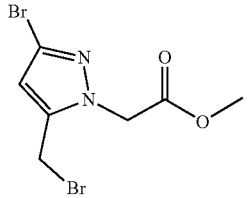

A solution of methyl 2-(3-bromo-5-methyl-pyrazol-1-yl)acetate (50.0 g, 214.54 mmol) and AIBN (3.52 g, 21.45 mmol) in carbon tetrachloride (1500 mL) was stirred at RT for 5 mins. 1-Bromo-2,5-pyrrolidinedione (40.09 g, 225.26 mmol) was added. The mixture was stirred at 80° C. for 1 hour. The reaction mixture was concentrated under vacuum. The residue was purified by flash chromatography on silica gel eluting with PE/EA (92/8) to afford methyl 2-[3-bromo-5-(bromomethyl)pyrazol-1-yl]acetate (35.5 g, 53% yield) as a white solid.

Step 3: Methyl 2-(3-bromo-5-(cyanomethyl)-1H-pyrazol-1-yl)acetate

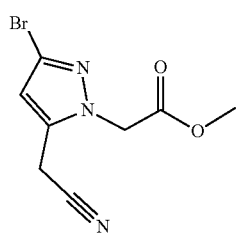

A solution of methyl 2-[3-bromo-5-(bromomethyl)pyrazol-1-yl]acetate (35.4 g, 113.48 mmol) and sodium cyanide (8.87 g, 181.02 mmol) in dimethyl sulfoxide (550 mL) was stirred at RT for 1 hour. The reaction solution was diluted with EA (2.5 L). The solution was washed with water (200 mL×5) and the organic layers were combined. The organic layer was dried over anhydrous sodium sulfate, filtered and concentrated under vacuum. The residue was purified by flash chromatography on silica gel eluting with DCM/MeOH (99/1) to afford methyl 2-(3-bromo-5-(cyanomethyl)-1H-pyrazol-1-yl)acetate (17.6 g, 60% yield) as a white solid.

892

Step 4: Methyl 2-(5-(2-aminoethyl)-3-bromo-1H-pyrazol-1-yl)acetate

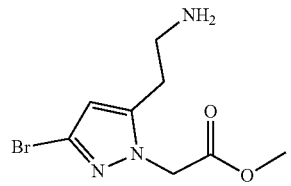

To a solution of methyl 2-[3-bromo-5-(cyanomethyl) pyrazol-1-yl]acetate (3.0 g, 11.62 mmol) in methanol (600 mL) was added PtO$_2$ (600 mg, 2.64 mmol). The mixture was stirred under 10 atm of hydrogen gas at 25° C. for 15 hours. The mixture was filtrated. The filtrate would be directly used in the next step without purification.

Step 5: 2-bromo-4,5,6,8-tetrahydropyrazolo[1,5-d][1,4]diazepin-7-one

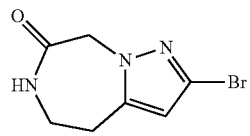 [SMILES: O=C1Cn2nc(Br)cc2CCN1]

To a solution (600 mL) of methyl 2-[5-(2-aminoethyl)-3-bromo-pyrazol-1-yl]acetate was added TEA (70 mL). The mixture was stirred at 25° C. for 15 hours. The resulting solution was concentrated under vacuum. The residue was purified by flash chromatography on silica gel eluting with DCM/MeOH (98/2) to afford 2-bromo-4,5,6,8-tetrahydropyrazolo[1,5-d][1,4]diazepin-7-one (1.12 g, 41.9% yield in two steps) as a white solid.

Step 6: 2-bromo-6-methyl-5,6-dihydro-4H-pyrazolo[1,5-d][1,4]diazepin-7(8H)-one

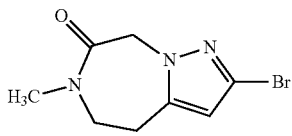

To a mixture of 2-bromo-5,6,7,8-tetrahydro-4H-pyrazolo[1,5-d][1,4]diazepine (469.53 mg, 2.17 mmol) and potassium tert-butoxide (365.74 mg, 3.26 mmol) in tetrahydrofuran (20 mL) was added iodomethane (616.86 mg, 4.35 mmol) at 20° C. The resulting solution was stirred at 20° C. for 1 h. The mixture was concentrated under vacuum. The residue was purified by flash chromatography on silica gel eluting with dichloromethane/methanol (20/1) to afford 2-bromo-6-methyl-4,5,7,8-tetrahydropyrazolo[1,5-d][1,4]diazepine (400 mg, 1.74 mmol, 80% yield). LCMS (ESI) [M+H]$^+$=244.

Step 7: tert-butyl N-[5-[1-[bis[(2,6-dimethoxyphenyl)methyl]amino]-6-[(6-methyl-7-oxo-5,8-dihydro-4H-pyrazolo[1,5-d][1,4]diazepin-2-yl)amino]-2,7-naphthyridin-3-yl]-4-methyl-3-pyridyl]-N-tert-butoxycarbonyl-carbamate

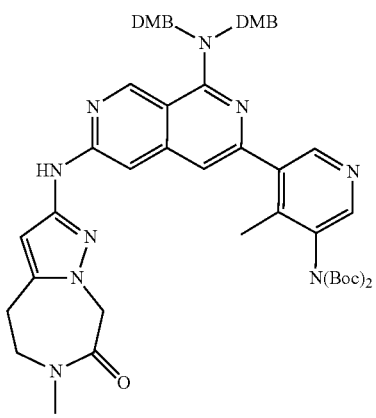

A mixture of tert-butyl N-[5-[6-amino-1-[bis[(2,6-dimethoxyphenyl)methyl]amino]-2,7-naphthyridin-3-yl]-4-methyl-3-pyridyl]-N-tert-butoxycarbonyl-carbamate (130 mg, 0.17 mmol), 2-bromo-6-methyl-5,8-dihydro-4H-pyrazolo[1,5-d][1,4]diazepin-7-one (67 mg, 0.26 mmol), tBuBrettphos Pd G3 (60 mg, 0.07 mmol), tBuBrettphos (41 mg, 0.09 mmol) and Cs$_2$CO$_3$ (166 mg, 0.51 mmol) in 1,4-dioxane (10 mL) was stirred at 120° C. for 1 hour. The mixture was concentrated under vacuum. The residue was purified by flash chromatography on silica gel eluting with MeOH/DCM (1/10) to afford tert-butyl N-[5-[1-[bis[(2,6-dimethoxyphenyl)methyl]amino]-6-[(6-methyl-7-oxo-5,8-dihydro-4H-pyrazolo[1,5-d][1,4]diazepin-2-yl)amino]-2,7-naphthyridin-3-yl]-4-methyl-3-pyridyl]-N-tert-butoxycarbonyl-carbamate (50 mg, 0.05 mmol) as a yellow solid. LCMS (ESI) [M+H]$^+$=931.

Step 8: 2-[[8-amino-6-(5-amino-4-methyl-3-pyridyl)-2,7-naphthyridin-3-yl]amino]-6-methyl-5,8-dihydro-4H-pyrazolo[1,5-d][1,4]diazepin-7-one

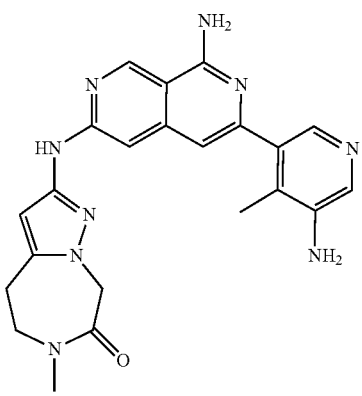 [SMILES: Cc1c(N)cncc1-c1cc2cc(Nc3cc4n(n3)CC(=O)N(C)CC4)ncc2c(N)n1]

A mixture of tert-butyl N-[5-[1-[bis[(2,6-dimethoxyphenyl)methyl]amino]-6-[(6-methyl-7-oxo-5,8-dihydro-4H-pyrazolo[1,5-d][1,4]diazepin-2-yl)amino]-2,7-naphthyridin-3-yl]-4-methyl-3-pyridyl]-N-tert-butoxycarbonyl-carbamate (50.0 mg, 0.05 mmol) in CF$_3$COOH (1.0 mL) was stirred at 80° C. for 30 min. The mixture was concentrated under vacuum. The reaction mixture was adjusted to pH=8 with a solution of NH$_3$ in methanol. The crude product was purified by Prep-HPLC with the following conditions: Column, XBridge Prep C18 OBD Column 19×150 mm; mobile phase: water (0.05% NH$_3$H$_2$O) and ACN (10%-50%); Detector, UV 254 nm. R$_T$:[7 min] to afford 2-[[8-amino-6-(5-amino-4-methyl-3-pyridyl)-2,7-naphthyridin-3-yl]amino]-6-methyl-5,8-dihydro-4H-pyrazolo[1,5-d][1,4]diazepin-7-one (10 mg, 0.023 mmol) as a yellow solid. LCMS (ESI) [M+H]$^+$=430.2. $^1$HNMR (400 MHz, DMSO-d$_6$) δ 9.37 (s, 1H), 9.20 (s, 1H), 7.93 (s, 1H), 7.77 (s, 1H), 7.51 (s, 1H), 7.03 (s, 2H), 6.68 (s, 1H), 6.06 (s, 1H), 5.11 (s, 2H), 4.99 (s, 2H), 3.84 (t, J=6 Hz, 2H), 3.06 (t, J=6 Hz, 2H), 2.96 (s, 3H), 2.08 (s, 3H).

Example 269

(S)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile (Compound 416) and (R)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile (Compound 417)

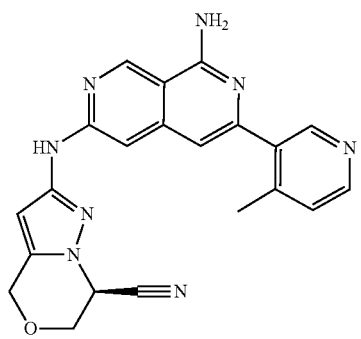

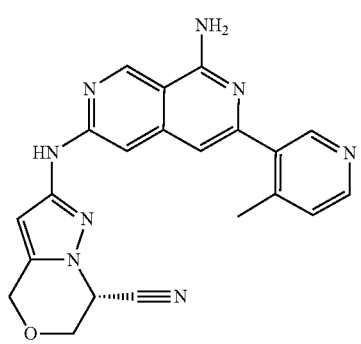

Step 1: methyl 3-bromo-1-(oxan-2-yl)-1H-pyrazole-5-carboxylate

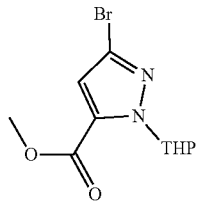

A mixture of methyl 3-bromo-1H-pyrazole-5-carboxylate (10 g, 48.77 mmol), 4-methylbenzene-1-sulfonic acid (500 mg, 2.90 mmol) and 3,4-dihydro-2H-pyran (12.2 g, 145.03 mmol) in ethyl acetate (150 mL) was stirred for 4 h at 80° C. The reaction was concentrated under vacuum. The residue was purified by silica gel column with dichloromethane/methanol (10/1) to afford methyl 3-bromo-1-(oxan-2-yl)-1H-pyrazole-5-carboxylate (9 g, 31.14 mmol) as yellow oil. LCMS (ESI) [M+H]$^+$=289.

Step 2: [3-bromo-1-(oxan-2-yl)-1H-pyrazol-5-yl]methanol

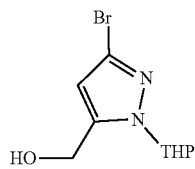

To a solution of methyl 3-bromo-1-(oxan-2-yl)-1H-pyrazole-5-carboxylate (7.5 g, 25.94 mmol) in dichloromethane (200 mL) was added DIBALH (103 mL, 51.88 mmol) at 0° C. The resulting solution was stirred for 1 h at 0° C. in a water/ice bath. The reaction was quenched with ice water. After filtration, the resulting solution was extracted with dichloromethane and the organic layers combined and dried over anhydrous sodium sulfate. The solids were filtered out. The resulting mixture was concentrated under vacuum to afford [3-bromo-1-(oxan-2-yl)-1H-pyrazol-5-yl]methanol (6 g, 23.07 mmol) as colorless oil. LCMS (ESI) [M+H]$^+$=261.

Step 3: 3-[[3-bromo-1-(oxan-2-yl)-1H-pyrazol-5-yl]methoxy]-2-hydroxypropanoic acid

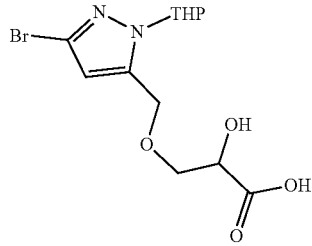

A mixture of [3-bromo-1-(oxan-2-yl)-1H-pyrazol-5-yl]methanol (200 mg, 0.76 mmol), sodium hydride (62 mg, 2.58 mmol), ethyl oxirane-2-carboxylate (134 mg, 1.15 mmol) in tetrahydrofuran (10 mL) was stirred for 12 h at room temperature under nitrogen. The reaction was then quenched with water. The reaction mixture was adjusted to pH 4 with hydrogen chloride. The resulting solution was extracted with ethyl acetate and dried with anhydrous sodium sulfate. After filtration, the filtrate was concentrated under vacuum. The residue was purified by reverse phase chromatography (acetonitrile 0-40/0.1% HCl in water) to afford 3-[[3-bromo-1-(oxan-2-yl)-1H-pyrazol-5-yl]methoxy]-2-hydroxypropanoic acid (130 mg, 0.37 mmol) as a white solid. LCMS (ESI) [M+H]$^+$=349.

Step 4: methyl 3-[[3-bromo-1-(oxan-2-yl)-1H-pyrazol-5-yl]methoxy]-2-hydroxypropanoate

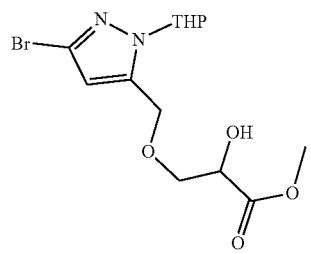

To a solution of 3-[[3-bromo-1-(oxan-2-yl)-1H-pyrazol-5-yl]methoxy]-2-hydroxypropanoic acid (130 mg, 0.37 mmol) in tetrahydrofuran (10 mL) and methanol (2 mL) was added TMSCHN$_2$ (0.22 mL, 3.852 mmol). The resulting solution was stirred for 2 h at room temperature. The resulting mixture was concentrated under vacuum to afford methyl 3-[[3-bromo-1-(oxan-2-yl)-1H-pyrazol-5-yl]methoxy]-2-hydroxypropanoate (140 mg, crude) as a white solid. LCMS (ESI) [M+H]$^+$=363.

Step 5: methyl 3-[(3-bromo-1H-pyrazol-5-yl)methoxy]-2-hydroxypropanoate

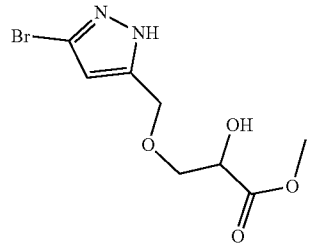

A mixture of methyl 3-[[3-bromo-1-(oxan-2-yl)-1H-pyrazol-5-yl]methoxy]-2-hydroxypropanoate (130 mg, 0.35 mmol) in dichloromethane (4 mL) and trifluoroacetic acid (2 mL) was stirred for 3 h at room temperature. The resulting mixture was concentrated under vacuum to afford methyl 3-[(3-bromo-1H-pyrazol-5-yl)methoxy]-2-hydroxypropanoate (50 mg, 0.18 mmol) as a white solid. LCMS (ESI) [M+H]$^+$=279.

Step 6: methyl 3-[(3-bromo-1H-pyrazol-5-yl)methoxy]-2-chloropropanoate

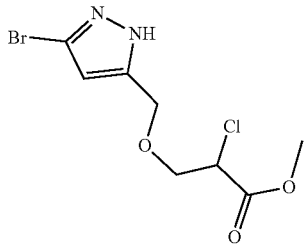

A mixture of methyl 3-[(3-bromo-1H-pyrazol-5-yl)methoxy]-2-hydroxypropanoate (100 mg, 0.35 mmol) and thionyl chloride (1 mL) in dichloromethane (10 mL) was stirred for 5 h at 70° C. The resulting mixture was concentrated under vacuum to afford methyl 3-[(3-bromo-1H-pyrazol-5-yl)methoxy]-2-chloropropanoate (80 mg, 0.27 mmol) as a white solid. LCMS (ESI) [M+H]$^+$=297.

Step 7: methyl 2-bromo-4H,6H,7H-pyrazolo[3,2-c][1,4]oxazine-7-carboxylate

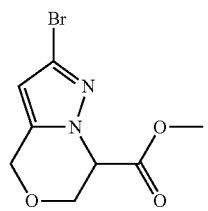

A mixture of methyl 3-[(3-bromo-1H-pyrazol-5-yl)methoxy]-2-chloropropanoate (650 mg, 2.18 mmol) and potassium carbonate (909 mg, 6.57 mmol) in N,N-dimethylformamide (10 mL) was stirred for 12 h at room temperature. The resulting solution was diluted with H$_2$O and extracted with ethyl acetate and the organic layers combined and concentrated under vacuum. The residue was purified by flash chromatography on silica gel eluting with dichloromethane/methanol (10/1) to afford methyl 2-bromo-4H,6H,7H-pyrazolo[3,2-c][1,4]oxazine-7-carboxylate (300 mg, 1.15 mmol) as a gray solid. LCMS (ESI) [M+H]$^+$=261.

Step 8: 2-bromo-4H,6H,7H-pyrazolo[3,2-c][1,4]oxazine-7-carboxamide

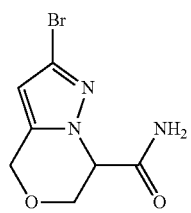 [SMILES: NC(=O)C1COCc2cc(Br)nn21]

A mixture of methyl 2-bromo-4H,6H,7H-pyrazolo[3,2-c][1,4]oxazine-7-carboxylate (300 mg, 1.15 mmol) and NH$_3$ in methanol (10 mL, 7M) was stirred for 6 h at 90° C. The resulting mixture was concentrated under vacuum to afford 2-bromo-4H,6H,7H-pyrazolo[3,2-c][1,4]oxazine-7-carboxamide (200 mg, 0.81 mmol) as a white solid. LCMS (ESI) [M+H]$^+$=246.

Step 9: 2-bromo-4H,6H,7H-pyrazolo[3,2-c][1,4]oxazine-7-carbonitrile

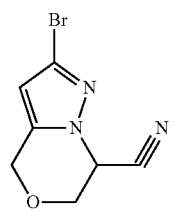 [SMILES: N#CC1COCc2cc(Br)nn21]

To a solution of 2-bromo-4H,6H,7H-pyrazolo[3,2-c][1,4]oxazine-7-carboxamide (200 mg, 0.81 mmol) and TEA (247 mg, 2.44 mmol) in dichloromethane (10 mL) was added TFAA (343 mg, 1.63 mmol) at 0° C. and then was stirred for 2 h at room temperature. The resulting mixture was concentrated under vacuum. The residue was purified by silica gel column with dichloromethane/methanol (98/2) to afford 2-bromo-4H,6H,7H-pyrazolo[3,2-c][1,4]oxazine-7-carbonitrile (100 mg, 0.44 mmol) as a white solid. LCMS (ESI) [M+H]$^+$=228.

Step 10: 2-[(8-[bis[(3,4-dimethoxyphenyl)methyl]amino]-6-(4-methylpyridin-3-yl)-2,7-naphthyridin-3-yl)amino]-4H,6H,7H-pyrazolo[3,2-c][1,4]oxazine-7-carbonitrile

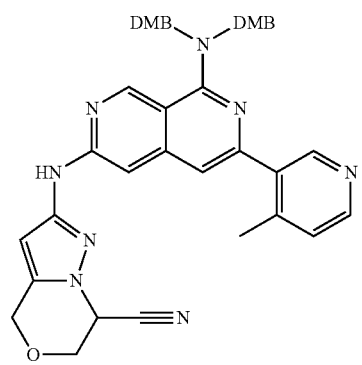

A mixture of 1-N,1-N-bis[(3,4-dimethoxyphenyl)methyl]-3-(4-methylpyridin-3-yl)-2,7-naphthyridine-1,6-diamine (242 mg, 0.44 mmol), 2-bromo-4H,6H,7H-pyrazolo[3,2-c][1,4]oxazine-7-carbonitrile (100 mg, 0.44 mmol), BrettPhos Pd G3 (75 mg, 0.08 mmol), t-BuBrettPhos (85 mg, 0.17 mmol) and Cs$_2$CO$_3$ (575 mg, 1.76 mmol) in dioxane (10 mL) was stirred for 0.5 h at 120° C. After filtration, the filtrate was concentrated under vacuum. The residue was purified by flash chromatography on silica gel eluting with dichloromethane/methanol (10/1) to afford 2-[(8-[bis[(3,4-dimethoxyphenyl)methyl]amino]-6-(4-methylpyridin-3-yl)-2,7-naphthyridin-3-yl)amino]-4H,6H,7H-pyrazolo[3,2-c][1,4]oxazine-7-carbonitrile (100 mg, 0.25 mmol) as a white solid. LCMS (ESI) [M+H]$^+$=699.

Step 11: (7S)-2-[[8-amino-6-(4-methylpyridin-3-yl)-2,7-naphthyridin-3-yl]amino]-4H,6H,7H-pyrazolo[3,2-c][1,4]oxazine-7-carbonitrile and (7R)-2-[[8-amino-6-(4-methylpyridin-3-yl)-2,7-naphthyridin-3-yl]amino]-4H,6H,7H-pyrazolo[3,2-c][1,4]oxazine-7-carbonitrile

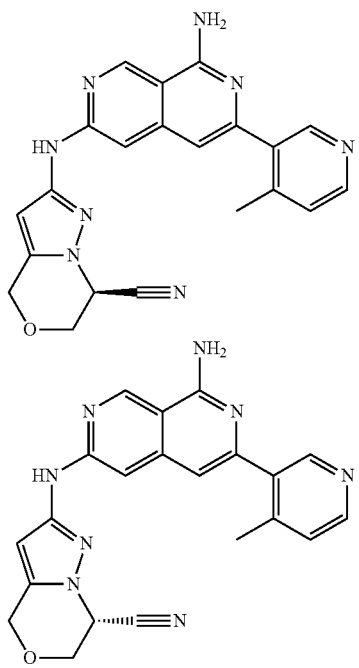

A mixture of 2-[(8-[bis[(3,4-dimethoxyphenyl)methyl]amino]-6-(4-methylpyridin-3-yl)-2,7-naphthyridin-3-yl)amino]-4H,6H,7H-pyrazolo[3,2-c][1,4]oxazine-7-carbonitrile (100 mg, 0.14 mmol) in trifluoroacetic acid (5 mL) was stirred for 30 min at 80° C. The resulting mixture was concentrated under vacuum. The residue was purified by reverse phase chromatography (acetonitrile 0-50/0.1% NH$_4$HCO$_3$ in water) to afford 2-[[8-amino-6-(4-methylpyridin-3-yl)-2,7-naphthyridin-3-yl]amino]-4H,6H,7H-pyrazolo[3,2-c][1,4]oxazine-7-carbonitrile (50 mg, 0.12 mmol) as a yellow solid. The racemate was separated by Chiral-HPLC to afford two isomers: Isomer 1: Retention time:3.37 min(CHIRAL Cellulose-SB, 0.46*15 cm; 5 um; 100% MeOH (0.1% DEA); 1 ml/min); LCMS (ESI) [M+H]$^+$=399; $^1$H NMR (400 MHz, CD$_3$OD) δ 9.17 (s, 1H), 8.51 (s, 1H), 8.41 (d, J=4 Hz, 1H), 7.67 (s, 1H), 7.37 (d, J=8 Hz, 1H), 6.85 (s, 1H), 6.14 (s, 1H), 5.33-5.32 (m, 1H), 4.98 (d, J=12 Hz, 1H), 4.77 (s, 1H), 4.45 (d, J=4 Hz, 1H), 4.29-4.25 (m, 1H), 2.44 (s, 3H); Isomer 2: Retention time:4.13 min(CHIRAL Cellulose-SB, 0.46*15 cm; 5 um; 100% MeOH (0.1% DEA); 1 ml/min); LCMS (ESI) [M+H]$^+$=399; $^1$H NMR (400 MHz, CD$_3$OD) δ 9.17 (s, 1H), 8.51 (s, 1H), 8.41 (d, J=4 Hz, 1H), 7.67 (s, 1H), 7.37 (d, J=8 Hz, 1H), 6.85 (s, 1H), 6.14 (s, 1H), 5.33-5.32 (m, 1H), 4.98 (d, J=12 Hz, 1H), 4.77 (s, 1H), 4.45 (d, J=4 Hz, 1H), 4.29-4.25 (m, 1H), 2.44 (s, 3H).

Example 270

Compound Nos. 418 and 426 were prepared in a fashion analogous to the procedures in Example 166.

Example 271

Compound Nos. 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, and 572 are prepared using procedures similar to those described herein or methods known in the art.

Example 272

Compound Nos. 86, 87, 88, 89, 90, 91, 92, 93, 94, 96, 97, 98, 99, 100, 101, 102, 103, 104, 105, 106, 107, 108, 109, 110, 111, 112, 113, 114, 115, 116, 117, 118, 119, 123, 160, and 389 were prepared using procedures similar to those described herein or methods known in the art.

Evaluation of Compounds

Chemical Analysis

Exemplary compounds of Formula I or Ia. Tables A-1 and A-2 include preparation and characterization of certain compounds.

TABLE A-1

| Compd No. | Structure/Name | LCMS R$_T$(min) M + H$^+$, Method | $^1$H NMR (ppm) |
|---|---|---|---|
| 1 | ![structure] (±)-cis-N-(8-amino-6-(4-methyl-3-pyridyl)-2,7-naphthyridin-3-yl)-2-fluoro-cyclopropanecarboxamide | 0.974 338.1 B | $^1$H NMR (400 MHz, CD$_3$OD) δ 9.30 (s, 1H), 8.54 (s, 1H), 8.43 (d, J = 5.2 Hz, 1H), 8.33 (s, 1H), 7.40 (d, J = 5.2 Hz, 1H), 6.70 (s, 1H), 4.99-4.80 (m, 1H), 2.46 (s, 3H), 2.19-2.15 (m, 1H), 1.87-1.80 (m, 1H), 1.26-1.21 (m, 1H). |

TABLE A-1-continued

| Compd No. | Structure/Name | LCMS R_T(min) M + H⁺, Method | ¹H NMR (ppm) |
|---|---|---|---|
| 2 | 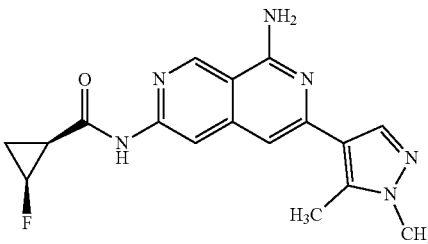<br>(±)-cis-N-(8-amino-6-(1,5-dimethyl-1H-pyrazol-4-yl)-2,7-naphthyridin-3-yl)-2-fluorocyclopropanecarboxamide | 1.051<br>341.2<br>B | ¹H NMR (400 MHz, CD₃OD) δ 9.18 (s, 1H), 8.23 (s, 1H), 7.85 (s, 1H), 7.00 (s, 1H), 4.99-4.83 (m, 1H), 3.86 (s, 3H), 2.64 (s, 3H), 2.18-2.15 (m, 1H), 1.86-1.80 (m, 1H), 1.25-1.20 (m, 1H). |
| 3 | 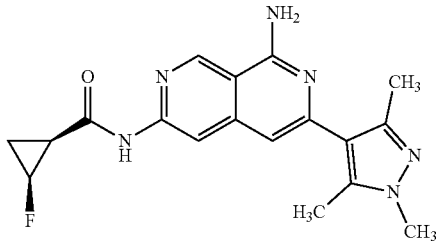 [SMILES: Cc1nn(C)c(C)c1-c1cc2cc(NC(=O)[C@@H]3C[C@@H]3F)ncc2c(N)n1]<br>(±)-cis-N-(8-amino-6-(1,3,5-trimethyl-1H-pyrazol-4-yl)-2,7-naphthyridin-3-yl)-2-fluorocyclopropanecarboxamide | 1.055<br>355.2<br>B | ¹H NMR (400 MHz, CD₃OD) δ 9.21 (s, 1H), 8.24 (s, 1H), 6.82 (s, 1H), 4.98-4.80 (m, 1H), 3.78 (s, 3H), 2.42 (s, 3H), 2.33 (s, 3H), 2.19-2.13 (m, 1H), 1.88-1.78 (m, 1H), 1.27-1.18 (m, 1H). |
| 4 | 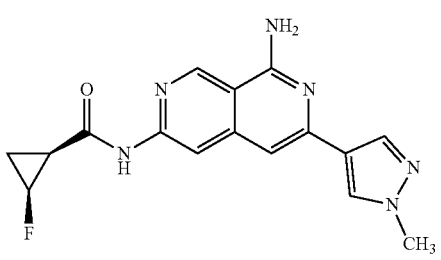 [SMILES: Cn1cc(-c2cc3cc(NC(=O)[C@@H]4C[C@@H]4F)ncc3c(N)n2)cn1]<br>(±)-cis-N-(8-amino-6-(1-methyl-1H-pyrazol-4-yl)-2,7-naphthyridin-3-yl)-2-fluorocyclopropanecarboxamide | 1.027<br>327.1<br>B | ¹H NMR (400 MHz, CD₃OD) δ 9.16 (s, 1H), 8.22 (s, 1H), 8.14 (s, 1H), 8.03 (s, 1H), 7.13 (s, 1H), 4.99-4.82 (m, 1H), 3.96 (s, 3H), 2.18-2.15 (m, 1H), 1.86-1.80 (m, 1H), 1.26-1.21 (m, 1H). |
| 5 | 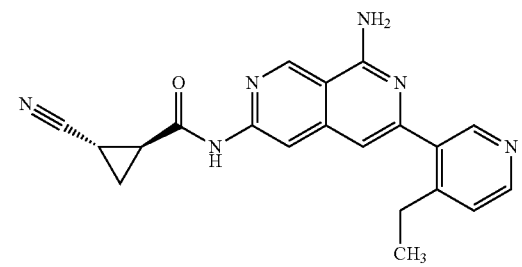 [SMILES: CCc1ccncc1-c1cc2cc(NC(=O)[C@H]3C[C@@H]3C#N)ncc2c(N)n1]<br>(±)-trans-N-(8-amino-6-(4-ethylpyridin-3-yl)-2,7-naphthyridin-3-yl)-2-cyanocyclopropanecarboxamide | 1.112<br>359.0<br>B | ¹H NMR (400 MHz, DMSO-d₆): δ 11.28 (s, 1H), 9.41 (s, 1H), 8.50 (s, 1H), 8.49 (d, J = 5.2 Hz, 1H), 8.20 (s, 1H), 7.38-7.36 (m, 2H), 7.35 (d, J = 5.2 Hz, 1H), 6.95 (s, 1H), 2.80-2.72 (m, 1H), 2.78 (q, J = 7.6 Hz, 2H), 2.20-2.12 (m, 1H), 1.65-1.57 (m, 1H), 1.48-1.39 (m, 1H), 1.09 (t, J = 7.6 Hz, 3H). |

TABLE A-1-continued

| Compd No. | Structure/Name | LCMS R$_T$(min) M + H$^+$, Method | $^1$H NMR (ppm) |
|---|---|---|---|
| 6 | 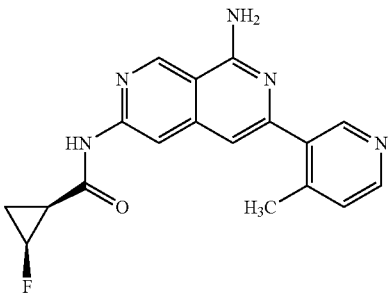 [SMILES: Cc1ccncc1-c1cc2cc(NC(=O)[C@@H]3C[C@@H]3F)ncc2c(N)n1]<br>(1S,2S)-N-(8-amino-6-(4-methylpyridin-3-yl)-2,7-naphthyridin-3-yl)-2-fluorocyclopropanecarboxamide | 0.990<br>338.1<br>B | $^1$H NMR (400 MHz, CD$_3$OD) δ 9.30 (s, 1H), 8.54 (s, 1H), 8.44 (d, J = 4.8 Hz, 1H), 8.34 (s, 1H), 7.40 (d, J = 4.8 Hz, 1H), 7.00 (s, 1H), 4.98–4.80 (m, 1H), 2.46 (s, 3H), 2.19-2.16 (m, 1H), 1.87-1.80 (m, 1H), 1.26-1.21 (m, 1H). |
| 7 | 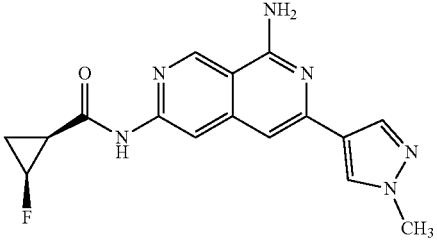 [SMILES: Cn1cc(-c2cc3cc(NC(=O)[C@@H]4C[C@@H]4F)ncc3c(N)n2)cn1]<br>(1S,2S)-N-(8-amino-6-(1-methyl-1H-pyrazol-4-yl)-2,7-naphthyridin-3-yl)-2-fluorocyclopropanecarboxamide | 1.038<br>327.1<br>B | $^1$H NMR (400 MHz, CD$_3$OD) δ 9.16 (s, 1H), 8.22 (s, 1H), 8.14 (s, 1H), 8.03 (s, 1H), 7.12 (s, 1H), 4.99-4.79 (m, 1H), 3.96 (s, 3H), 2.18-2.15 (m, 1H), 1.88-1.78 (m, 1H), 1.27-1.19 (m, 1H). |
| 8 | 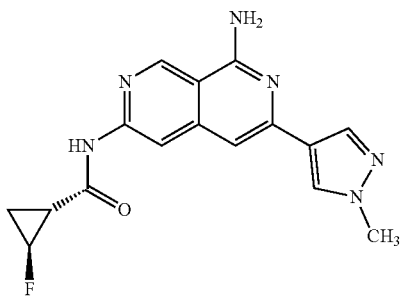<br>(±)-trans-N-(8-amino-6-(1-methyl-1H-pyrazol-4-yl)-2,7-naphthyridin-3-yl)-2-fluorocyclopropanecarboxamide | 1.063<br>327.1<br>B | $^1$H NMR (400 MHz, CD$_3$OD) δ 9.16 (s, 1H), 8.17 (s, 1H), 8.13 (s, 1H), 8.02 (s, 1H), 7.10 (s, 1H), 4.97-4.79 (m, 1H), 3.96 (s, 3H), 2.49-2.40 (m, 1H), 1.59-1.50 (m, 1H), 1.49-1.38 (m, 1H). |
| 9 | 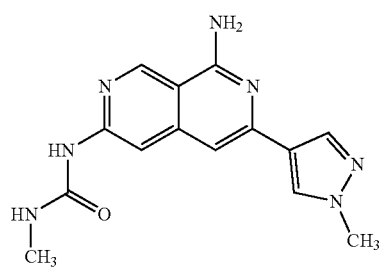 [SMILES: CNC(=O)Nc1cc2cc(-c3cnn(C)c3)nc(N)c2cn1]<br>1-(8-amino-6-(1-methyl-1H-pyrazol-4-yl)-2,7-naphthyridin-3-yl)-3-methylurea | 0.934<br>298.2<br>B | $^1$H NMR (400 MHz, CD$_3$OD) δ 9.10 (s, 1H), 8.12 (s, 1H), 8.00 (s, 1H), 7.32 (s, 1H), 7.02 (s, 1H), 3.96 (s, 3H), 2.90 (s, 3H). |

TABLE A-1-continued

| Compd No. | Structure/Name | LCMS R_T(min) M + H+, Method | 1H NMR (ppm) |
|---|---|---|---|
| 10 | 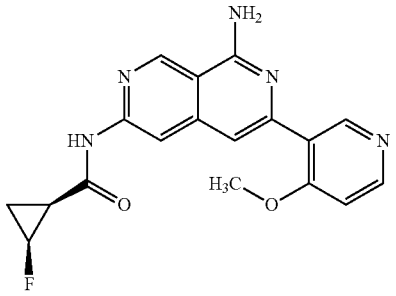 [SMILES: COc1ccncc1-c1cc2cc(NC(=O)[C@@H]3C[C@@H]3F)ncc2c(N)n1]<br>(1S,2S)-N-(8-amino-6-(4-methoxypyridin-3-yl)-2,7-naphthyridin-3-yl)-2-fluorocyclopropanecarboxamide | 0.790<br>354.1<br>B | $^1$H NMR (CD$_3$OD, 400 MHz) δ 9.24 (s, 1H), 8.78 (s, 1H), 8.43 (d, J = 5.6 Hz, 1H), 7.35 (s, 1H), 7.19 (d, J = 4.2 Hz, 1H), 4.97-4.77 (m, 1H), 4.00 (s, 3H), 2.17-2.15 (m, 1H), 1.90-1.78 (m, 1H), 1.28-1.18 (m, 1H). |
| 11 | 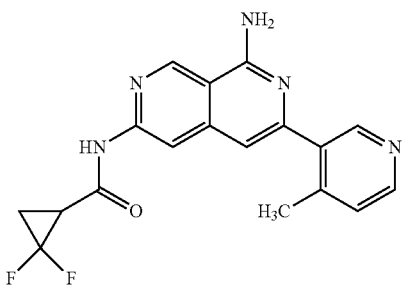 [SMILES: Cc1ccncc1-c1cc2cc(NC(=O)C3CC3(F)F)ncc2c(N)n1]<br>N-(8-amino-6-(4-methylpyridin-3-yl)-2,7-naphthyridin-3-yl)-2,2-difluorocyclopropanecarboxamide | 1.074<br>356.1<br>B | $^1$H NMR (400 MHz, CD$_3$OD) δ 9.31 (s, 1H), 8.55 (s, 1H), 8.44 (d, J = 5.2 Hz, 1H), 8.34 (s, 1H), 7.41 (d, J = 5.2 Hz, 1H), 7.01 (s, 1H), 2.95-2.87 (m, 1H), 2.47 (s, 3H), 2.19-2.13 (m, 1H), 1.93-1.86 (m, 1H). |
| 12 | 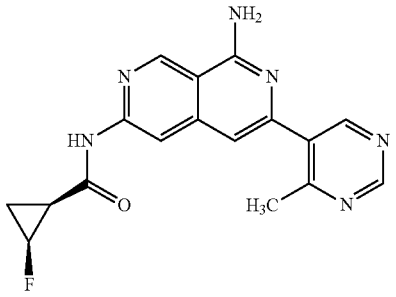 [SMILES: Cc1ncncc1-c1cc2cc(NC(=O)[C@@H]3C[C@@H]3F)ncc2c(N)n1]<br>(1S,2S)-N-(8-amino-6-(4-methylpyrimidin-5-yl)-2,7-naphthyridin-3-yl)-2-fluorocyclopropanecarboxamide | 0.973<br>339.1<br>B | $^1$H NMR (400 MHz, CD$_3$OD) δ 9.31 (s, 1H), 9.05 (s, 1H), 8.80 (s, 1H), 9.36 (s, 1H), 7.09 (s, 1H), 4.97-4.81 (m, 1H), 2.63 (s, 3H), 2.19-2.16 (m, 1H), 1.87-1.80 (m, 1H), 1.26-1.21 (m, 1H). |
| 13 | 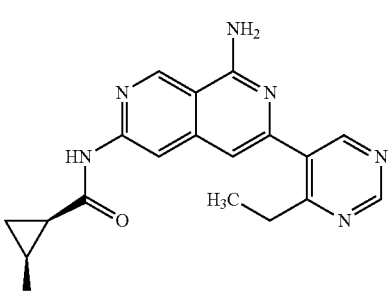<br>(1S,2S)-N-(8-amino-6-(4-ethylpyrimidin-5-yl)-2,7-naphthyridin-3-yl)-2-fluorocyclopropanecarboxamide | 1.065<br>353.1<br>B | $^1$H NMR (400 MHz, CD$_3$OD) δ 9.31 (s, 1H), 9.09 (s, 1H), 8.76 (s, 1H), 8.35 (s, 1H), 7.05 (s, 1H), 4.984.81 (m, 1H), 2.98 (q, J = 7.6 Hz, 2H), 2.19-2.16 (m, 1H), 1.87-1.80 (m, 1H), 1.29-1.21 (m, 4H). |

TABLE A-1-continued

| Compd No. | Structure/Name | LCMS R_T(min) M + H+, Method | 1H NMR (ppm) |
|---|---|---|---|
| 14 | 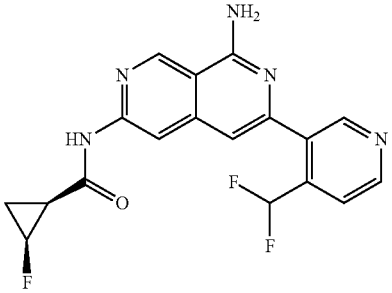 [SMILES: Nc1nc(-c2cnccc2C(F)F)cc2cc(NC(=O)[C@@H]3C[C@@H]3F)ncc12]<br>(1S,2S)-N-(8-amino-6-(4-(difluoromethyl)pyridin-3-yl)-2,7-naphthyridin-3-yl)-2-fluorocyclopropanecarboxamide | 1.142<br>374.1<br>B | $^1$H NMR (400 MHz, CD$_3$OD) δ 9.30 (s, 1H), 8.89 (s, 1H), 8.77 (d, J = 5.2 Hz, 1H), 8.37 (s, 1H), 7.79 (d, J = 5.2 Hz, 1H), 7.54 (t, J = 14.8 Hz, 1H), 7.15 (s, 1H), 5.00-4.79 (m, 1H), 2.19-2.14 (m, 1H), 1.88-1.78 (m, 1H), 1.28-1.21 (m, 1H). |
| 15 | 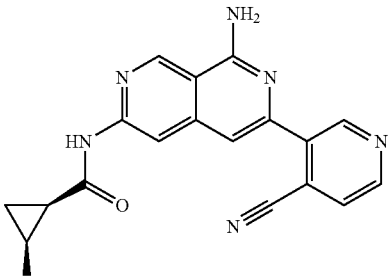<br>(1S,2S)-N-(8-amino-6-(4-cyanopyridin-3-yl)-2,7-naphthyridin-3-yl)-2-fluorocyclopropanecarboxamide | 1.603<br>349.1<br>C | $^1$H NMR (400 MHz, CD$_3$OD) δ 9.32 (s, 1H), 9.18 (s, 1H), 8.80 (d, J = 5.2 Hz, 1H), 8.40 (s, 1H), 7.87 (d, J = 4.8 Hz, 1H), 7.40 (s, 1H), 5.00-4.79 (m, 1H), 2.21-2.15 (m, 1H), 1.89-1.79 (m, 1H), 1.30-1.19 (m, 1H). |
| 16 | 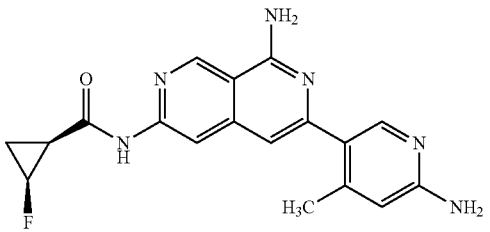 [SMILES: Cc1cc(N)ncc1-c1cc2cc(NC(=O)[C@@H]3C[C@@H]3F)ncc2c(N)n1]<br>(±)-cis-N-(8-amino-6-(6-amino-4-methylpyridin-3-yl)-2,7-naphthyridin-3-yl)-2-fluorocyclopropanecarboxamide | 1.408<br>353.2<br>G | $^1$H NMR (400 MHz, DMSO-d$_6$) δ 10.94 (s, 1H), 9.31 (s, 1H), 8.18 (s, 1H), 8.02 (s, 1H), 7.17 (s, 2H), 6.84 (s, 1H), 6.31 (s, 1H), 5.96 (s, 2H), 5.03-4.86 (m, 1H), 2.30 (s, 3H), 2.28-2.24 (m, 1H), 1.70-1.63 (m, 1H), 1.21-1.14 (m, 1H). |
| 17 | 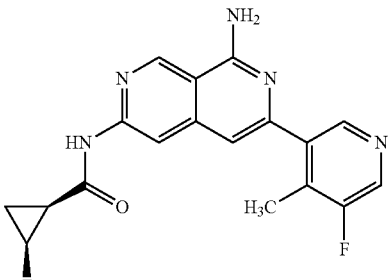<br>(1S,2S)-N-(8-amino-6-(5-fluoro-4-methylpyridin-3-yl)-2,7-naphthyridin-3-yl)-2-fluorocyclopropanecarboxamide | 1.099<br>356.1<br>B | $^1$H NMR (400 MHz, DMSO-d$_6$) δ 11.05 (s, 1H), 9.40 (s, 1H), 8.52 (s, 1H), 8.48 (s, 1H), 8.27 (s, 1H), 8.15 (s, 1H), 7.40 (s, 2H), 7.03 (s, 1H), 5.09-4.83 (m, 1H), 4.35 (d, J = 2.0 Hz, 3H), 2.32-2.21 (m, 1H), 1.75-1.62 (m, 1H), 1.25-1.14 (m, 1H). |

TABLE A-1-continued

| Compd No. | Structure/Name | LCMS R$_T$(min) M + H$^+$, Method | $^1$H NMR (ppm) |
|---|---|---|---|
| 18 | 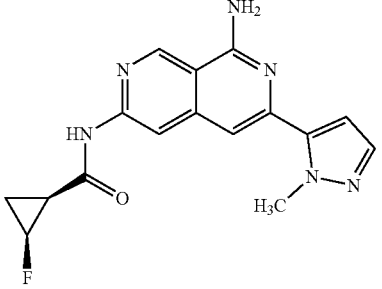 [SMILES: Cn1nccc1-c1cc2cc(NC(=O)[C@@H]3C[C@@H]3F)ncc2c(N)n1]<br>(1S,2S)-N-(8-amino-6-(1-methyl-1H-pyrazol-5-yl)-2,7-naphthyridin-3-yl)-2-fluorocyclopropanecarboxamide | 1.055<br>327.1<br>B | $^1$H NMR (400 MHz, DMSO-d$_6$) δ 11.02 (s, 1H), 8.24 (s, 1H), 8.15 (s, 1H), 7.45 (d, J = 2.0 Hz, 1H), 7.40 (s, 2H), 7.21 (s, 1H), 6.73 (d, J = 2.0 Hz, 1H), 5.07-4.84 (m, 1H), 4.19 (s, 3H), 2.32-2.21(m, 1H), 1.75-1.62 (m, 1H), 1.25-1.14 (m, 1H). |
| 19 | 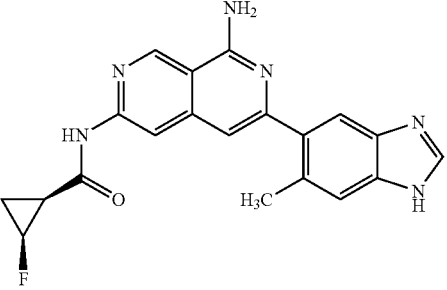 [SMILES: Cc1cc2[nH]cnc2cc1-c1cc2cc(NC(=O)[C@@H]3C[C@@H]3F)ncc2c(N)n1]<br>(±)-cis-N-(8-amino-6-(6-methyl-1H-benzo[d]imidazol-5-yl)-2,7-naphthyridin-3-yl)-2-fluorocyclopropanecarboxamide | 1.269<br>377.1<br>A | $^1$H NMR (400 MHz, CD$_3$OD) δ 9.29 (s, 1H), 8.32 (s, 1H), 8.18 (s, 1H), 7.66 (s, 1H), 7.53 (s, 1H), 6.95 (s, 1H), 4.95-4.84 (m, 1H), 2.45 (s, 3H), 2.22-2.14 (m, 1H), 1.88-1.78 (m, 1H), 1.26-1.18 (m, 1H). |
| 20 | 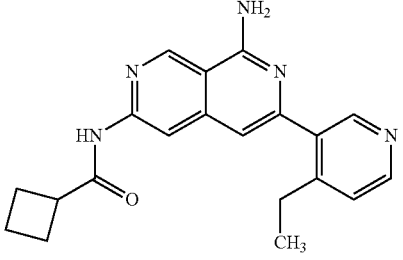<br>N-[8-amino-6-(4-ethyl-3-pyridyl)-2,7-naphthyridin-3-yl]cyclobutanecarboxamide | 1.752<br>348.2<br>C | $^1$H NMR (400 MHz, CD$_3$OD) δ 9.30 (s, 1H), 8.51-8.49 (m, 2H), 8.37 (s, 1H), 8.30 (brs, 1H), 7.46 (d, J = 5.2 Hz, 1H), 7.00 (s, 1H), 3.45-3.41 (m, 1H), 2.85 (q, J = 7.6 Hz, 2H), 2.43-2.36 (m, 2H), 2.31-2.23 (m, 2H), 2.12-2.05 (m, 1H), 1.98-1.93 (m, 1H), 1.20 (t, J = 7.6 Hz, 3H). |
| 21 | 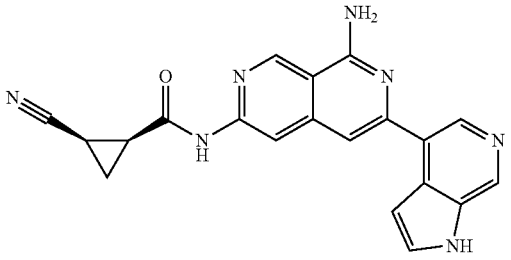 [SMILES: N#C[C@@H]1C[C@@H]1C(=O)Nc1cc2cc(-c3cncc4[nH]ccc34)nc(N)c2cn1]<br>(±)-cis-N-(8-amino-6-(1H-pyrrolo[2,3-c]pyridin-4-yl)-2,7-naphthyridin-3-yl)-2-cyanocyclopropanecarboxamide | 1.035<br>370.1<br>B | $^1$H NMR (400 MHz, CD$_3$OD) δ 9.30 (s, 1H), 8.91 (s, 1H), 8.67 (s, 1H), 8.03 (s, 1H), 7.47 (s, 1H), 7.32 (s, 1H), 7.31 (s, 1H), 2.56-2.54 (m, 1H), 2.19-2.17 (m, 1H), 1.72-1.70 (m, 1H), 1.55-1.53 (m, 1H). |

TABLE A-1-continued

| Compd No. | Structure/Name | LCMS R_T(min) M + H+, Method | 1H NMR (ppm) |
|---|---|---|---|
| 22 | 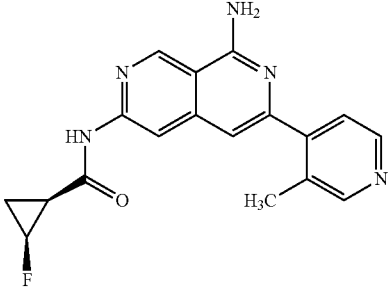 [SMILES: Cc1cnccc1-c1cc2cc(NC(=O)[C@@H]3C[C@@H]3F)ncc2c(N)n1]<br>(±)-cis-N-(8-amino-6-(3-methylpyridin-4-yl)-2,7-naphthyridin-3-yl)-2-fluorocyclopropanecarboxamide | 1.059<br>338.1<br>B | 1H NMR (400 MHz, CD$_3$OD) δ 8.51 (s, 1H), 8.47 (s, 1H), 8.35 (s, 1H), 8.21 (s, 1H), 7.51 (d, J = 4.8 Hz, 1H), 7.03 (s, 1H), 2.43 (s, 3H), 4.99-4.80 (m, 1H), 2.19-2.16 (m, 1H), 1.87-1.80 (m, 1H), 1.28-1.21 (m, 1H). |
| 24 | 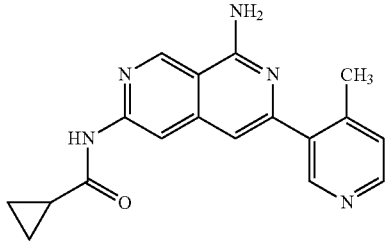 [SMILES: Cc1ccncc1-c1cc2cc(NC(=O)C3CC3)ncc2c(N)n1]<br>N-(8-amino-6-(4-methylpyridin-3-yl)-2,7-naphthyridin-3-yl)cyclopropanecarboxamide | 1.580<br>320.1<br>F | 1H NMR (400 MHz, CD$_3$OD) δ 9.29 (s, 1H), 8.56 (s, 1H), 8.43 (d, J = 5.2 Hz, 1H), 8.31 (s, 1H), 7.39 (d, J = 5.2 Hz, 1H), 6.98 (s, 1H), 2.46 (s, 3H), 1.92-2.00 (m, 1H), 1.01-1.06 (m, 2H), 0.92-0.97 (m, 2H). |
| 25 | 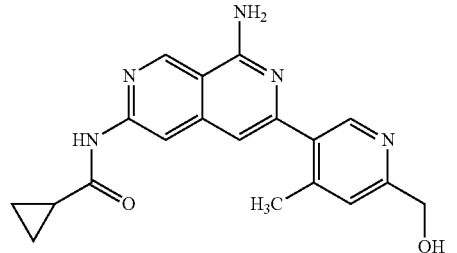 [SMILES: Cc1cc(CO)ncc1-c1cc2cc(NC(=O)C3CC3)ncc2c(N)n1]<br>N-(8-amino-6-(6-(hydroymethyl)-4-methylpyridin-3-yl)-2,7-naphthyridin-3-yl)cyclopropanecarboxamide | 1.627<br>350.1<br>G | 1H NMR (400 MHz, CD$_3$OD) δ 9.30 (s, 1H), 8.49 (s, 1H), 8.30 (s, 1H), 7.52 (s, 1H), 6.99 (s, 1H), 4.74 (s, 2H), 2.48 (s, 3H), 1.92-2.03 (m, 1H), 1.01-1.04 (m, 2H), 0.88-0.90 (m, 2H). |
| 26 | 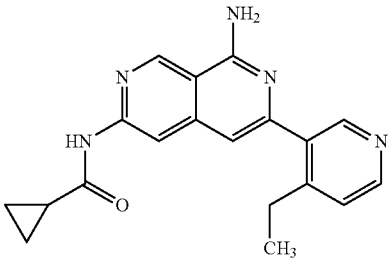 [SMILES: CCc1ccncc1-c1cc2cc(NC(=O)C3CC3)ncc2c(N)n1]<br>N-(8-amino-6-(4-ethylpyridin-3-yl)-2,7-naphthyridin-3-yl)cyclopropanecarboxamide | 1.623<br>334.2<br>G | 1H NMR (400 MHz, CD$_3$OD) δ 9.18 (s, 1H), 8.39 (s, 1H), 8.37 (d, J = 5.6 Hz, 1H), 8.17 (s, 1H), 7.33 (d, J = 5.6 Hz, 1H), 6.81 (s, 1H), 2.72 (q, J = 7.6 Hz, 2 H), 1.88-1.78 (m, 1H), 1.07 (t, J = 7.6 Hz, 3H), 0.95-0.87 (m, 2H), 0.82-0.74 (m, 2H). |

| Compd No. | Structure/Name | LCMS R$_T$(min) M + H$^+$, Method | $^1$H NMR (ppm) |
|---|---|---|---|
| 27 | 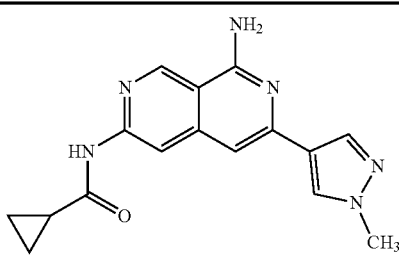<br>N-[8-amino-6-(1-methylpyrazol-4-yl)-2,7-naphthyridin-3-yl]cyclopropanecarboxamide | 1.646<br>309.1<br>G | $^1$H NMR (400 MHz, CD$_3$OD) δ 9.15(s, 1H), 8.19(s, 1H), 8.14(s, 1H), 8.02(s, 1H), 7.11(s, 1H), 3.96 (s, 3H), 1.98-1.92(m, 1H), 1.05-1.02(m, 2H), 0.96-0.91(m, 2H). |
| 28 | 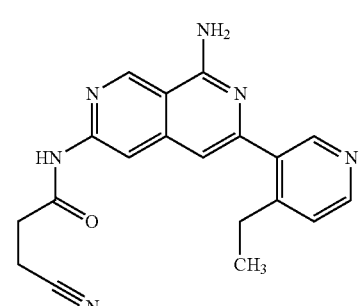<br>N-[8-amino-6-(4-ethyl-3-pyridyl)-2,7-naphthyridin-3-yl]-3-cyano-propanamide and N'-[8-amino-6-(4-ethyl-3-pyridyl)-2,7-naphthyridin-3-yl]butanediamide | 1.57<br>347.2<br>F | $^1$H NMR (400 MHz, DMSO-d$_6$) δ 10.85 (s, 1H), 9.39 (s, 1H), 8.51 (s, 1H), 8.49 (d, J = 5.2 Hz, 1H), 8.26 (s, 1H), 7.36 (s, 1H), 7.34 (s, 2H), 6.98 (s, 1H), 2.86-2.74 (m, 6H), 1.10 (t, J = 7.6 Hz, 3H). |
| 29 | 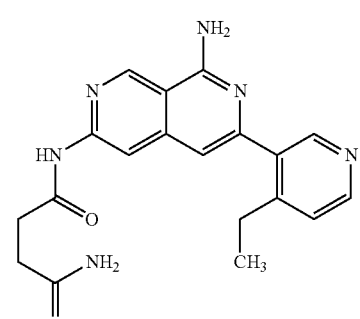<br>N'-[8-amino-6-(4-ethyl-3-pyridyl)-2,7-naphthyridin-3-yl]butanediamide | 1.372<br>365.2<br>G | $^1$H NMR (400 MHz, DMSO-d$_6$) δ 10.65 (s, 1H), 9.36 (s, 1H), 8.50 (s, 1H), 8.48 (d, J = 4.8 Hz, 1H), 8.23 (s, 1H), 7.35 (s, 1H), 7.34 (d, J = 5.2 Hz, 1H), 7.31 (s, 2H), 6.93 (s, 1H), 6.79 (s, 1H), 2.78 (q, J = 7.6 Hz, 2H), 2.65 (t, J = 7.0 Hz, 2H), 2.41 (t, J = 7.0 Hz, 2H), 1.10 (t, J = 7.6 Hz, 3H). |
| 30 | 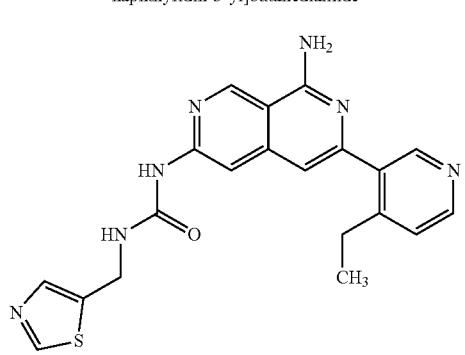<br>1-[8-amino-6-(4-ethyl-3-pyridyl)-2,7-naphthyridin-3-yl]-3-(thiazol-5-ylmethyl)urea | 1.56<br>406.1<br>C | $^1$H NMR (400 MHz, DMSO-d$_6$) δ 9.41 (s, 1H), 9.28 (s, 1H), 8.99 (d, J = 0.8 Hz, 1H), 8.49 (s, 1H), 8.48 (d, J = 5.2 Hz, 1H), 7.83 (s, 1H), 7.82 (s, 1H), 7.80 (s, 1H), 7.34 (d, J = 5.2 Hz, 1H), 7.27 (s, 2H), 6.87 (s, 1H), 4.61 (d, J = 6.0 Hz, 2H), 2.79 (q, J = 7.6 Hz, 2H), 2.65 (t, J = 7.6 Hz, 3H). |

TABLE A-1-continued

| Compd No. | Structure/Name | LCMS R_T(min) M + H+, Method | 1H NMR (ppm) |
|---|---|---|---|
| 31 | 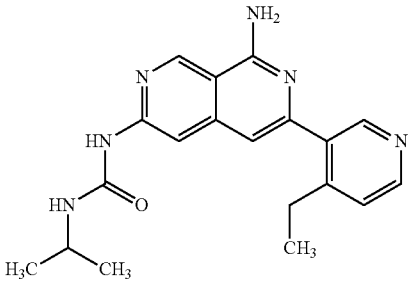<br>1-[8-amino-6-(4-ethyl-3-pyridyl)-2,7-naphthyridin-3-yl]-3-isopropyl-urea | 1.581<br>351.2<br>G | $^1$H NMR (400 MHz, DMSO-$d_6$) δ 9.33 (s, 1H), 9.11 (s, 1H), 8.55 (s, 1H), 8.54 (d, J = 5.2 Hz, 1H), 7.86 (s, 1H), 8.39 (d, J = 5.2 Hz, 1H), 7.30 (s, 2H), 7.16 (d, J = 6.8 Hz, 1H), 6.89 (s, 1H), 3.91-3.83 (m, 1H), 2.84 (q, J = 7.6 Hz, 2H), 1.20 (d, J = 6.4 Hz, 6H), 1.15 (t, J = 7.6 Hz, 3H). |
| 32 | 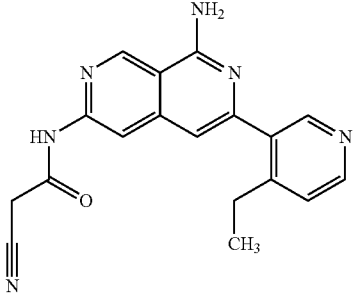 [SMILES: CCc1ccncc1-c1cc2cc(NC(=O)CC#N)ncc2c(N)n1]<br>N-[8-amino-6-(4-ethyl-3-pyridyl)-2,7-naphthyridin-3-yl]-2-cyano-acetamide | 1.568<br>333.1<br>C | $^1$H NMR (400 MHz, DMSO-$d_6$) δ 11.02 (s, 1H), 9.39 (s, 1H), 8.51 (s, 1H), 8.49 (d, J = 5.2 Hz, 1H), 8.19 (s, 1H), 7.36 (s, 2H), 7.35 (s, 1H), 7.01 (s, 1H), 4.04 (s, 2H), 2.79 (q, J = 7.6 Hz, 2H), 1.10 (t, J = 7.6 Hz, 3H). |
| 33 | 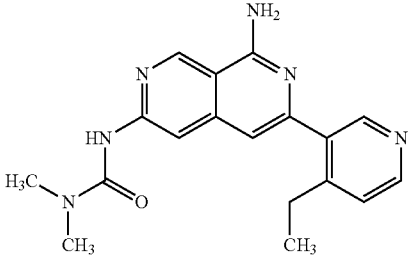<br>3-[8-amino-6-(4-ethyl-3-pyridyl)-2,7-naphthyridin-3-yl]-1,1-dimethyl-urea | 1.567<br>337.1<br>C | $^1$H NMR (400 MHz, DMSO-$d_6$) δ 9.33 (s, 1H), 8.98 (s, 1H), 8.49 (s, 1H), 8.48 (d, J = 4.8 Hz, 1H), 7.96 (s, 1H), 7.34 (d, J = 4.8 Hz, 1H), 7.25 (s, 2H), 6.87 (s, 1H), 2.98 (s, 6H), 2.78 (q, J = 7.6 Hz, 2H), 1.10 (t, J = 7.6 Hz, 3H). |
| 34 | 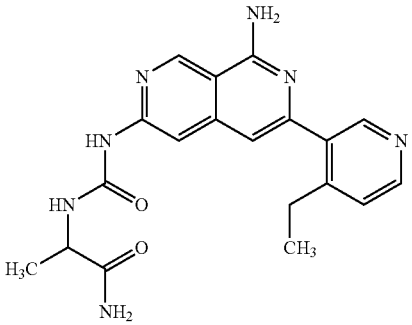 [SMILES: CCc1ccncc1-c1cc2cc(NC(=O)NC(C)C(N)=O)ncc2c(N)n1]<br>(±)-2-[[8-amino-6-(4-ethyl-3-pyridyl)-2,7-naphthyridin-3-yl]carbamoylamino]propanamide | 1.378<br>380.2<br>G | $^1$H NMR (400 MHz, DMSO-$d_6$) δ 9.33 (s, 1H), 9.28 (s, 1H), 8.49 (s, 1H), 8.48 (d, J = 5.2 Hz, 1H), 7.78 (s, 1H), 7.58 (s, 1H), 7.53 (s, 1H), 7.30 (d, J = 1.2 Hz, 1H), 7.25 (s, 2H), 7.06 (s, 1H), 6.84 (s, 1H), 4.29-4.22 (m, 1H), 2.78 (q, J = 7.6 Hz, 2H), 1.28 (d, J = 6.8 Hz, 3H), 1.10 (t, J = 7.6 Hz, 3H). |

TABLE A-1-continued

| Compd No. | Structure/Name | LCMS R$_T$(min) M + H$^+$, Method | $^1$H NMR (ppm) |
|---|---|---|---|
| 35 | 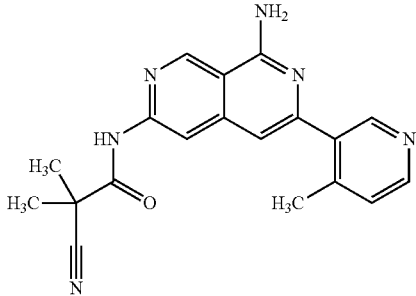 [SMILES: Cc1ccncc1-c1cc2cc(NC(=O)C(C)(C)C#N)ncc2c(N)n1]<br>N-(8-amino-6-(4-methylpyridin-3-yl)-2,7-naphthyridin-3-yl)-2-cyano-2-methylpropanamide | 1.041<br>347.1<br>B | $^1$H NMR (400 MHz, CD$_3$OD) δ 9.30 (s, 1H), 8.53, (s, 1H), 8.41 (d, J = 5.2 Hz, 1H), 8.09 (s, 1H), 7.37 (d, J = 5.2 Hz, 1H), 7.00 (s, 1H), 2.44 (s, 3H), 1.74 (s, 6H). |
| 36 | 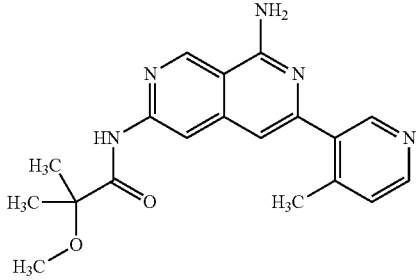 [SMILES: COC(C)(C)C(=O)Nc1cc2cc(-c3cnccc3C)nc(N)c2cn1]<br>N-(8-amino-6-(4-methylpyridin-3-yl)-2,7-naphthyridin-3-yl)-2-methoxy-2-methylpropanamide | 1.071<br>352.1<br>B | $^1$H NMR (400 MHz, CD$_3$OD) δ 9.30 (s, 1H), 8.54 (s, 1H), 8.43 (d, J = 5.6 Hz, 1H), 8.37 (s, 1H), 7.28 (d, J = 5.6 Hz, 1H), 6.99 (s, 1H), 3.41(s, 3H), 2.45 (s, 3H), 1.49 (s, 6H). |
| 37 | 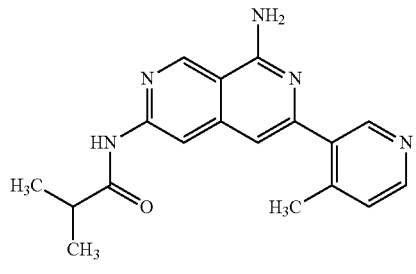 [SMILES: Cc1ccncc1-c1cc2cc(NC(=O)C(C)C)ncc2c(N)n1]<br>N-(8-amino-6-(4-methylpyridin-3-yl)-2,7-naphthyridin-3-yl)isobutyramide | 1.221<br>332.1<br>B | $^1$H NMR (400 MHz, CDCl$_3$) δ 9.00 (s, 1H), 8.65 (s, 1H), 8.50 (d, J = 5.2 Hz, 1H), 8.47 (s, 1H), 8.05 (br, 1H), 7.21 (d, J = 5.2 Hz, 1H), 7.06 (s, 1H), 5.42 (br, 2H), 2.62 (heptet, J = 6.8 Hz, 1H), 2.43 (s, 3H), 1.31 (d, J = 6.8 Hz, 6H). |
| 38 | 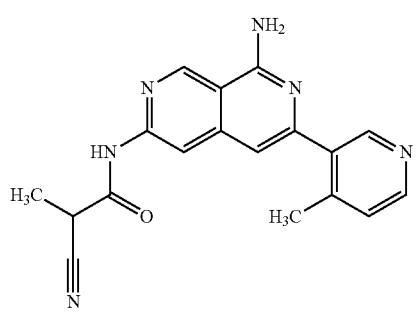 [SMILES: Cc1ccncc1-c1cc2cc(NC(=O)C(C)C#N)ncc2c(N)n1]<br>(±)-N-(8-amino-6-(4-methylpyridin-3-yl)-2,7-naphthyridin-3-yl)-2-cyanopropanamide | 1.541<br>333.1<br>F | $^1$H NMR (400 MHz, CD$_3$OD) δ 9.31 (s, 1H), 8.54 (s, 1H), 8.43 (d, J = 5.2 Hz, 1H), 8.33 (s, 1H), 7.39 (d, J = 5.2 Hz, 1H), 7.01 (s, 1H), 2.45 (s, 3H), 1.64 (s, 3H). |

| Compd No. | Structure/Name | LCMS R_T(min) M + H+, Method | $^1$H NMR (ppm) |
|---|---|---|---|
| 39 | 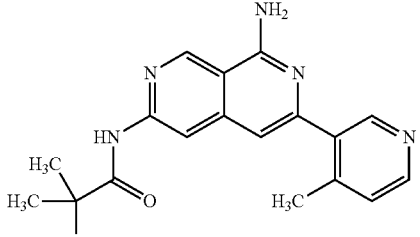<br>N-(8-amino-6-(4-methylpyridin-3-yl)-2,7-naphthyridin-3-yl)-2-hydroxy-2-methylpropanamide | 0.996<br>338.1<br>B | $^1$H NMR (400 MHz, CD$_3$OD) δ 9.29 (s, 1H), 8.53 (s, 1H), 8.42 (d, J = 5.2 Hz, 1H), 8.38 (s, 1H), 7.37 (d, J = 5.2 Hz, 1H), 6.99 (s, 1H), 2.45 (s, 3H), 1.50(s, 6H). |
| 40 | 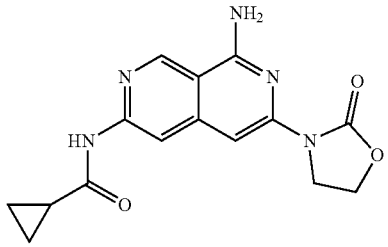 [SMILES: Nc1nc(N2CCOC2=O)cc2cc(NC(=O)C3CC3)ncc12]<br>N-(8-amino-6-(2-oxooxazolidin-3-yl)-2,7-naphthyridin-3-yl)cyclopropanecarboxamide | 1.092<br>314.2<br>B | $^1$H NMR (400 MHz, DMSO-d$_6$) δ: 10.86 (s, 1H), 9.24 (s, 1H), 8.05 (s, 1H), 7.36-7.33 (m, 3H), 4.42 (t, J = 8.0 Hz, 2H), 4.17 (t, J = 8.0 Hz, 2H), 2.08-2.01 (m, 1H), 0.85-0.80 (m, 4H). |
| 42 | 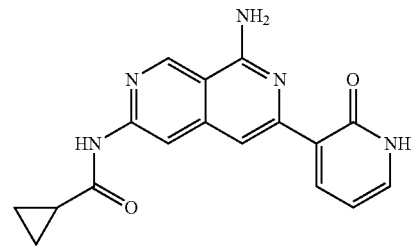 [SMILES: Nc1nc(-c2ccc[nH]c2=O)cc2cc(NC(=O)C3CC3)ncc12]<br>N-(8-amino-6-(2-oxo-1,2-dihydropyridin-3-yl)-2,7-naphthyridin-3-yl)cyclopropanecarboxamide | 1.034<br>322.1<br>B | $^1$H NMR (400 MHz, DMSO-d$_6$) δ 12.01 (br, 1H), 10.95 (s, 1H), 9.31 (s, 1H), 8.60 (d, J = 6.4 Hz, 1H), 8.26 (s, 1H), 8.17 (s, 1H), 7.52 (br, 1H), 7.15 (br, 2H), 6.47-6.35 (m, 1H), 2.12-2.02 (m 1H), 0.91-076 (m, 4H). |
| 43 | 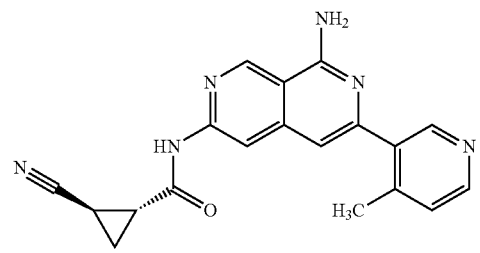 [SMILES: Cc1ccncc1-c1cc2cc(NC(=O)[C@@H]3C[C@H]3C#N)ncc2c(N)n1]<br>(±)-trans-N-(8-amino-6-(4-methylpyridin-3-yl)-2,7-naphthyridin-3-yl)-2-cyanocyclopropanecarboxamide | 1.094<br>345.2<br>B | $^1$H NMR (400 MHz, CD$_3$OD) δ 9.28 (s, 1H), 8.51 (s, 1H), 8.41 (d, J = 5.2 Hz, 1H), 8.28 (s, 1H), 7.37 (d, J = 5.2 Hz, 1H), 6.95 (s, 1H), 2.68-2.59 (m, 1H), 2.44 (s, 3H), 2.14-2.07 (m, 1H), 1.63-1.51 (m, 2H). |

TABLE A-1-continued

| Compd No. | Structure/Name | LCMS R_T(min) M + H+, Method | 1H NMR (ppm) |
|---|---|---|---|
| 44 | 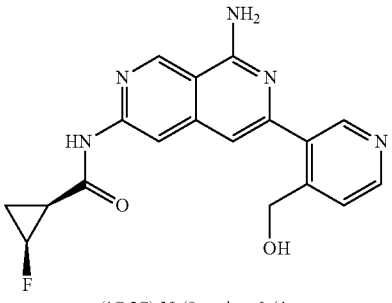<br>(1S,2S)-N-(8-amino-6-(4-(hydroxymethyl)pyridin-3-yl)-2,7-naphthyridin-3-yl)-2-fluorocyclopropanecarboxamide | 1.414<br>354.2<br>F | 1H NMR (400 MHz, DMSO-d_6) δ: 9.45 (s, 1H), 8.70 (s, 1H), 8.64 (d, J = 5.2 Hz, 1H), 8.32 (s, 1H), 7.67 (d, J = 5.2 Hz, 1H), 7.44 (br, 2H), 7.11 (s, 1H), 5.52 (t, J = 5.6 Hz, 1H), 5.13-4.90 (m, 1H), 4.74 (d, J = 5.6 Hz, 2H), 2.40-2.29 (m, 1H), 1.80-1.68 (m, 1H), 1.32-1.20 (m, 1H). |
| 45 | 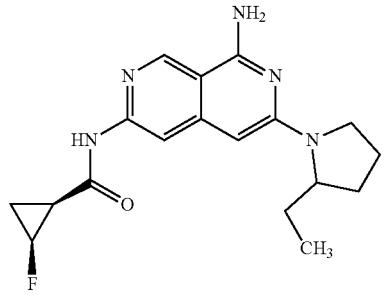 [SMILES: CCC1CCCN1c1cc2cc(NC(=O)[C@@H]3C[C@@H]3F)ncc2c(N)n1]<br>(1S,2S)-N-(8-amino-6-(2-ethylpyrrolidin-1-yl)-2,7-naphthyridin-3-yl)-2-fluorocyclopropanecarboxamide | 1.223<br>344.2<br>B | 1H NMR (400 MHz, CD_3OD) δ: 8.68 (s, 1H), 7.69 (s, 1H), 5.57 (s, 1H), 4.87-4.63 (m, 1H), 3.93-3.84 (m, 1H), 3.45-3.37 (m, 1H), 3.35-3.27 (m, 1H), 2.03-1.81 (m, 4H), 1.80-1.60 (m, 3H), 1.36-1.23 (m, 1H), 1.14-1.03 (m, 1H), 0.84 (t, J = 7.6 Hz, 3H). |
| 46 | 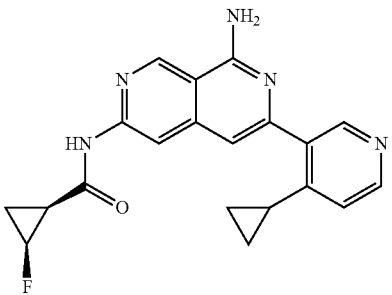 [SMILES: Nc1nc(-c2cnccc2C2CC2)cc2cc(NC(=O)[C@@H]3C[C@@H]3F)ncc12]<br>(±)-cis-N-(8-amino-6-(4-cyclopropylpyridin-3-yl)-2,7-naphthyridin-3-yl)-2-fluorocyclopropanecarboxamide | 1.104<br>346.1<br>B | 1H NMR (400 MHz, CD_3OD) δ: 9.38 (s, 1H), 8.47 (s, 1H), 8.39 (d, J = 5.6 Hz, 1H), 8.32 (s, 1H), 7.04 (s, 1H), 6.97 (d, J = 5.6 Hz, 1H), 4.98-4.76 (m, 1H), 2.22-2.11 (m, 2H), 1.89-1.77 (m, 1H), 1.24-1.18 (m, 1H), 1.11-1.04 (m, 2H), 0.92-0.85 (m, 2H). |
| 47 | 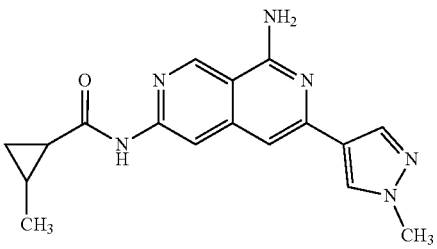 [SMILES: CC1CC1C(=O)Nc1cc2cc(-c3cnn(C)c3)nc(N)c2cn1]<br>N-(8-amino-6-(1-methyl-1H-pyrazol-4-yl)-2,7-naphthyridin-3-yl)-2-methylcyclopropanecarboxamide (3:1 ratio of trans/cis) | 1.661<br>323.2<br>F | 1H NMR of mixture of isomers (400 MHz, DMSO-d_6) δ: 10.77 (s, 1H), 9.24 (s, 1H), 8.15 (s, 1H), 8.11 (s, 1H), 7.96 (s, 1H), 7.12 (br, 2H), 7.04 (s, 1H), 3.88 (s, 3H), 2.12-2.02 (m, 0.3H), 1.86-1.77 (m, 0.7H), 1.34-1.20 (m, 1H), 1.18-0.94 (m, 4H), 0.85-0.79 (m, 0.3H), 0.72-0.63 (m, 0.7H). |

TABLE A-1-continued

| Compd No. | Structure/Name | LCMS R_T(min) M + H+, Method | $^1$H NMR (ppm) |
|---|---|---|---|
| 48 | 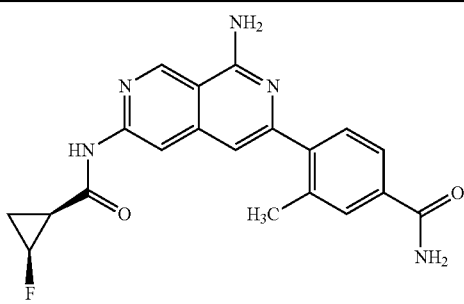<br>(±)-4-(1-amino-6-((cis)-2-fluorocyclopropanecarboxamido)-2,7-naphthyridin-3-yl)-3-methylbenzamide | 1.086<br>380.2<br>B | $^1$H NMR (400 MHz, DMSO-d$_6$) δ: 10.99 (s, 1H), 9.37 (s, 1H), 8.24 (s, 1H), 7.97 (s, 1H), 7.79 (s, 1H), 7.75 (d, J = 8.0 Hz, 1H), 7.48 (d, J = 8.0 Hz, 1H), 7.35 (br, 1H), 7.28 (br, 2H), 6.92 (s, 1H), 5.07-5.00 (m, 0.5 H), 4.90-4.83 (m, 0.5 H), 2.41 (s, 3H), 2.32-2.22 (m, 1H), 1.74-1.61 (m, 1H), 1.24-1.14 (m 1H). |
| 49 | 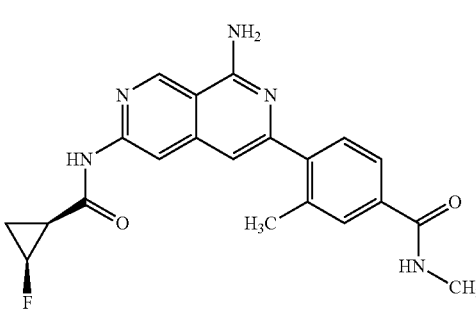<br>(±)-4-(1-amino-6-((cis)-2-fluorocyclopropanecarboxamido)-2,7-naphthyridin-3-yl)-N,3-dimethylbenzamide | 1.124<br>394.1<br>B | $^1$H NMR (400 MHz, DMSO-d$_6$) δ: 10.99 (s, 1H), 9.37 (s, 1H), 8.44 (q, J = 4.4 Hz, 1H), 8.23 (s, 1H), 7.75 (s, 1H), 7.71 (d, J = 8.0 Hz, 1H), 7.48 (d, J = 8.0 Hz, 1H), 7.28 (br, 2H), 6.92 (s, 1H), 5.06-4.99 (m, 0.5H), 4.90-4.83 (m, 0.5H), 2.80 (d, J = 4.4 Hz, 3H), 2.41 (s, 3H), 2.32-2.22 (m, 1H), 1.73-1.60 (m, 1H), 1.24-1.15 (m, 1H). |
| 50 | 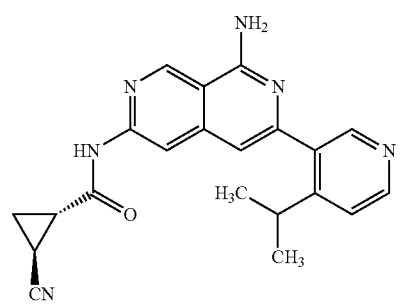 [SMILES: CC(C)c1ccncc1-c1cc2cc(NC(=O)[C@H]3C[C@@H]3C#N)ncc2c(N)n1]<br>(±)-trans-N-(8-amino-6-(4-ispropylpyridin-3-yl)-2,7-naphthyridin-3-yl)-2-cyanocyclopropanecarboxamide | 1.696<br>373.2<br>F | $^1$H NMR (400 MHz, CD$_3$OD) δ: 9.30 (s, 1H), 8.50 (d, J = 5.6 Hz, 1H), 8.44 (s, 1H), 8.28 (s, 1H), 7.49 (d, J = 5.6 Hz, 1H), 6.91 (s, 1H), 3.40-3.20 (m, 1H), 2.70-2.60 (m, 1H), 2.15-2.05 (m, 1H), 1.65-1.50 (m, 2H), 1.22 (d, J = 6.8 Hz, 6 H). |
| 51 | 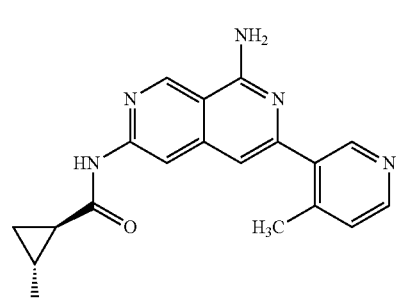<br>(±)-trans-N-(8-amino-6-(4-methylpyridin-3-yl)-2,7-naphthyridin-3-yl)-2-fluorocyclopropanecarboxamide | 1.440<br>338.1<br>E | $^1$H NMR (400 MHz, DMSO-d$_6$) δ 11.13 (s, 1H), 9.39 (s, 1H), 8.56 (s, 1H), 8.43 (d, J = 4.8 Hz, 1H), 8.19 (s, 1H), 7.34 (s, 2H), 7.30 (d, J = 5.2 Hz, 1H), 6.97 (s, 1H), 5.00 (s, 0.5 H), 4.83 (m, 0.5 H), 2.66-2.57 (m, 1H), 2.41 (s, 3H), 1.60-1.51 (m, 1H), 1.31-1.23 (m, 1H). |

TABLE A-1-continued

| Compd No. | Structure/Name | LCMS R$_T$(min) M + H$^+$, Method | $^1$H NMR (ppm) |
|---|---|---|---|
| 52 | 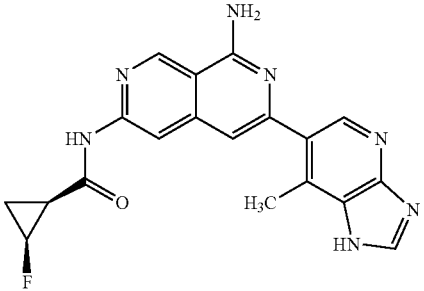 [SMILES: Cc1c(-c2cc3cc(NC(=O)[C@@H]4C[C@@H]4F)ncc3c(N)n2)cnc2nc[nH]c12]<br>(±)-cis-N-(8-amino-6-(7-methyl-1H-imidazo (4,5-b]pyridin-6-yl)-2,7-naphthyridin-3-yl)-2-fluorocyclopropanecarboxamide | 1.03<br>378.1<br>B | $^1$H NMR (400 MHz, CD$_3$OD) δ 9.31 (s, 1H), 8.48 (s, 1H), 8.44 (s, 1H), 8.34 (s, 1H), 7.05 (s, 1H), 5.00-4.80 (m, 1H), 2.71 (s, 3H), 2.20-2.16 (m, 1H), 1.88-1.81 (m, 1H), 1.26-1.21 (m, 1H). |
| 53 | 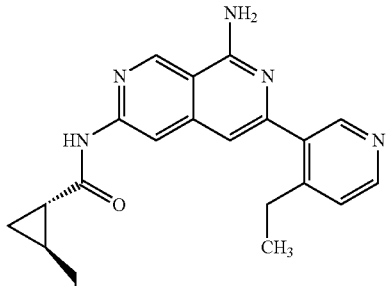<br>(±)-trans-N-(8-amino-6-(4-ethylpyridin-3-yl)-2,7-naphthyridin-3-yl)-2-(methoxymethyl)cyclopropane carboxamide | 1.16<br>378.2<br>B | $^1$H NMR (400 MHz, CD$_3$OD) δ 9.18 (s, 1H), 8.38 (s, 1H), 8.36 (s, 1H), 8.17 (s, 1H), 7.32 (d, J = 4.0 Hz, 1H), 6.83 (s, 1H), 3.42-3.39 (m, 1H), 3.22-3.18 (m, 4H), 2.72 (q, J = 6.0 Hz, 2H), 1.80-1.79 (m, 1H), 1.64-1.60 (m, 1H), 1.17-1.13 (m, 1H), 1.06 (t, J = 6.0 Hz, 3H), 0.86-0.82 (m, 1H). |
| 54 | 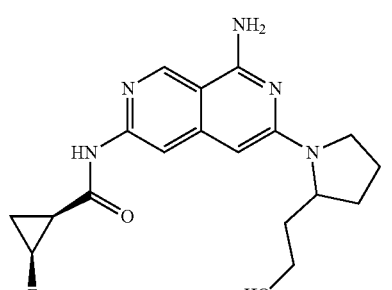<br>(±)-cis-N-(8-amino-6-(2-(2-hydroxyethyl)pyrrolidin-1-yl)-2,7-naphthyridin-3-yl)-2-fluorocyclopropanecarboxamide | 1.100<br>360.2<br>B | $^1$H NMR (400 MHz, CD$_3$OD) δ: 8.80 (s, 1H), 7.84 (s, 1H), 5.75 (s, 1H), 4.96-4.73 (m, 1H), 4.45-4.35 (m, 1H), 3.65-3.55 (m, 2H), 3.53-3.45 (m, 1H), 3.39-3.31 (m, 1H), 2.16-1.93 (m, 4H), 1.93-1.73 (m, 3H), 1.70-1.58 (m, 1H), 1.24-1.12 (m, 1H). |
| 55 | 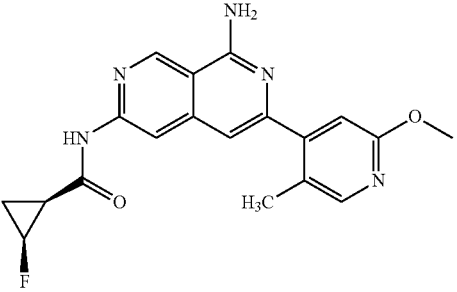 [SMILES: COc1cc(-c2cc3cc(NC(=O)[C@@H]4C[C@@H]4F)ncc3c(N)n2)c(C)cn1]<br>(±)-cis-N-(8-amino-6-(2-methoxy-5-methylpyridin-4-yl)-2,7-naphthyridin-3-yl)-2-fluorocyclopropanecarboxamide | 1.20<br>368.2<br>B | $^1$H NMR (400 MHz, DMSO-d$_6$) δ 11.02 (s, 1H), 9.38 (s, 1H), 8.25 (s, 1H), 8.05 (s, 1H), 7.34 (s, 2H), 6.98 (s, 1H), 6.85 (s, 1H), 5.04-4.86 (m, 1H), 3.85 (s, 3H), 2.30-2.23 (m, 4H), 1.70-1.64 (m, 1H), 1.22-1.17 (m, 1H). |

TABLE A-1-continued

| Compd No. | Structure/Name | LCMS R_T(min) M + H+, Method | 1H NMR (ppm) |
|---|---|---|---|
| 56 | 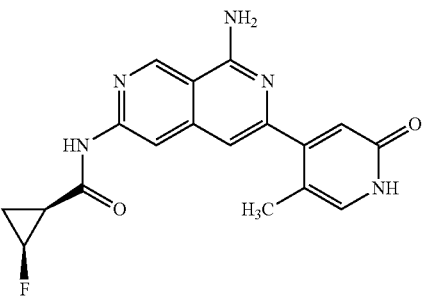 [SMILES: Cc1c[nH]c(=O)cc1-c1cc2cc(NC(=O)[C@@H]3C[C@@H]3F)ncc2c(N)n1]<br>(±)-cis-N-[8-amino-6-(5-methyl-2-oxo-1H-pyridin-4-yl)-2,7-naphthyridin-3-yl]-2-fluoro-cyclopropanecarboxamide | 1.02<br>354.1<br>B | $^1$H NMR (400 MHz, CD$_3$OD) δ 9.30 (s, 1H), 8.34 (s, 1H), 7.35 (s, 1H), 6.98 (s, 1H), 6.63 (s, 1H), 5.00-4.79 (m, 1H), 2.19-2.16 (m, 1H), 2.114 (s, 3H), 1.87-1.80 (m, 1H), 1.28-1.19 (m, 1H). |
| 57 | 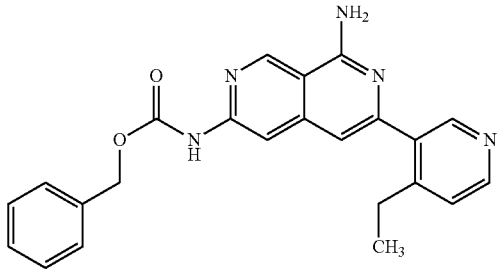 [SMILES: CCc1ccncc1-c1cc2cc(NC(=O)OCc3ccccc3)ncc2c(N)n1]<br>benzyl 8-amino-6-(4-ethylpyridin-3-yl)-2,7-naphthyridin-3-ylcarbamate | 1.53<br>400.2<br>B | $^1$H NMR (400 MHz, CD$_3$OD) δ 9.26 (s, 1H), 8.48 (s, 1H), 8.50 (s, 1H), 8.10 (s, 1H), 7.48-7.34 (m, 6 H), 6.97 (s, 1H), 5.27 (s, 2H), 2.83 (q, J = 7.6 Hz, 2H), 1.19 (t, J = 7.6 Hz, 3H). |
| 58 | 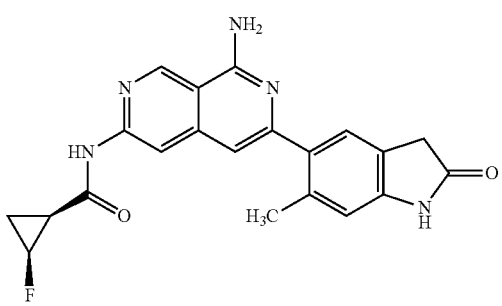 [SMILES: Cc1cc2c(cc1-c1cc3cc(NC(=O)[C@@H]4C[C@@H]4F)ncc3c(N)n1)CC(=O)N2]<br>(±)-cis-N-(8-amino-6-(6-methyl-2-oxoindolin-5-yl)-2,7-naphthyridin-3-yl)-2-fluorocyclopropanecarboxamide | 1.535<br>392.1<br>C | 1H NMR (400 MHz, DMSO-d$_6$) δ 10.95(s, 1H), 10.42 (s, 1H), 9.33 (s, 1H), 8.19(s, 1H), 7.28 (s, 1H), 7.20 (s, 2H), 6.82(s, 1H), 6.70(s, 1H), 5.05-4.83 (m, 1H), 3.46 (s, 2H), 2.35 (s, 3H), 2.30-2.21 (m, 1H), 1.71-1.59(m, 1H), 1.23-1.13(m, 1H). |
| 59 | 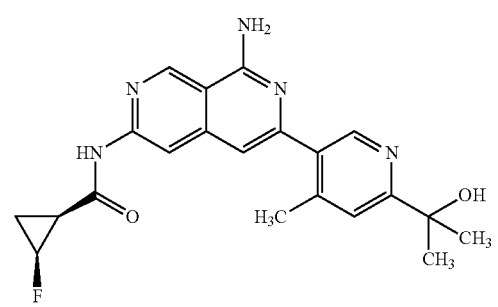 [SMILES: Cc1cc(C(C)(C)O)ncc1-c1cc2cc(NC(=O)[C@@H]3C[C@@H]3F)ncc2c(N)n1]<br>(±)-cis-N-(8-amino-6-(6-methyl-2-oxoindolin-5-yl)-2,7-naphthyridin-3-yl)-2-fluorocyclopropanecarboxamide | 1.309<br>396.1<br>A | $^1$H NMR (400 MHz, CD$_3$OD) δ 9.29 (s, 1H), 8.48 (s, 1H), 8.32 (s, 1H), 7.65 (s, 1H), 6.98 (s, 1H), 4.99-4.78 (m, 1H), 2.46 (s, 3H), 2.19-2.15 (m, 1H), 1.86-1.80 (m, 1H), 1.59 (s, 6H), 1.26-1.20 (m, 1H). |

| Compd No. | Structure/Name | LCMS R$_T$(min) M + H$^+$, Method | $^1$H NMR (ppm) |
|---|---|---|---|
| 60 | 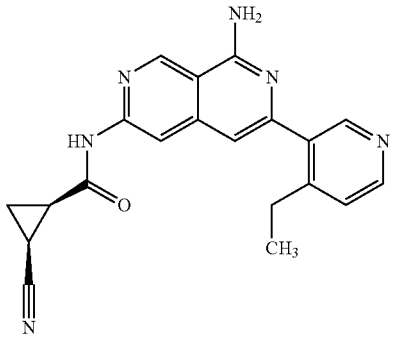 [SMILES: CCc1ccncc1-c1cc2cc(NC(=O)[C@@H]3C[C@@H]3C#N)ncc2c(N)n1]<br>(±)-cis-N-(8-amino-6-(4-ethylpyridin-3-yl)-2,7-naphthyridin-3-yl)-2-cyanocyclopropanecarboxamide | 1.593<br>359.1<br>C | $^1$H NMR (400 MHz, CD$_3$OD) δ 9.32(s, 1H), 8.50 (s, 1H), 8.48 (d, J = 5.2 Hz, 1H), 8.37(s, 1H), 7.44 (d, J = 5.2 Hz, 1H), 7.00 (s, 1H), 2.83(q, J = 7.6 Hz, 2H), 2.56-2.50 (m, 1H), 2.18-2.12 (m, 1H), 1.71-1.67 (m, 1H), 1.55-1.50 (m, 1H), 1.19 (t, J = 7.2 Hz, 3H). |
| 61 | 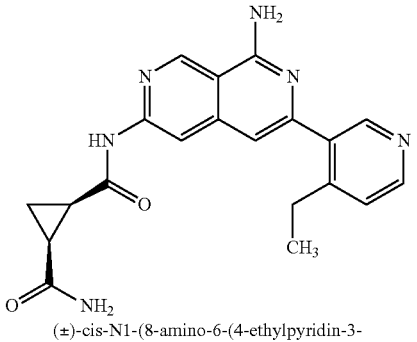<br>(±)-cis-N1-(8-amino-6-(4-ethylpyridin-3-yl)-2,7-naphthyridin-3-yl)cyclopropane-1,2-dicarboxamide | 1.449<br>377.1<br>C | $^1$H NMR (400 MHz, CD$_3$OD) δ 9.28(s, 1H), 8.49 (s, 1H), 8.47 (d, J = 5.2 Hz, 1H), 8.37(s, 1H), 7.44 (d, J = 5.2 Hz, 1H), 6.95 (s, 1H), 2.83 (q, J = 7.6 Hz, 2H), 2.35-2.29 (m, 1H), 2.19-2.13 (m, 1H), 1.73-1.68 (m, 1H), 1.37-1.32 (m, 1H), 1.18 (t, J = 7.2 Hz, 3H). |
| 62 | 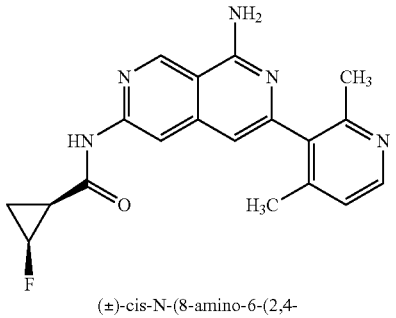<br>(±)-cis-N-(8-amino-6-(2,4-dimethylpyridin-3-yl)-2,7-naphthyridin-3-yl)-2-fluorocyclopropanecarboxamide | 1.556<br>352.1<br>C | $^1$H NMR (400 MHz, CD$_3$OD) δ 9.32(s, 1H), 8.32 (d, J = 5.2 Hz, 1H), 8.31 (s, 1H), 7.25 (d, J = 5.2 Hz, 1H), 6.86 (s, 1H), 4.98-4.80 (m, 1H), 2.35(s, 3H), 2.20(s, 3H), 2.18-2.15 (m, 1H), 1.87-1.79(m, 1H), 1.26-1.20 (m, 1H). |
| 63 | 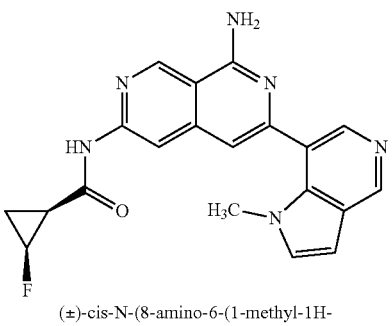<br>(±)-cis-N-(8-amino-6-(1-methyl-1H-pyrrolo[3,2-c]pyridin-7-yl)-2,7-naphthyridin-3-yl)-2-fluorocyclopropanecarboxamide | 1.58<br>377.1<br>C | $^1$H NMR (400 MHz, CD$_3$OD): 9.28 (s, 1H), 8.84 (s, 1H), 8.35 (s, 1H), 8.25 (d, J = 6.0 Hz, 1H), 7.55 (d, J = 6.0 Hz, 1H), 7.32 (s, 1H), 7.06 (s, 1H), 4.99-4.82 (m, 1H), 4.07 (s, 3H), 2.20-2.16 (m, 1H), 1.88-1.81 (m, 1H), 1.27-1.23 (m, 1H). |

TABLE A-1-continued

| Compd No. | Structure/Name | LCMS $R_T$(min) M + H+, Method | 1H NMR (ppm) |
|---|---|---|---|
| 64 | 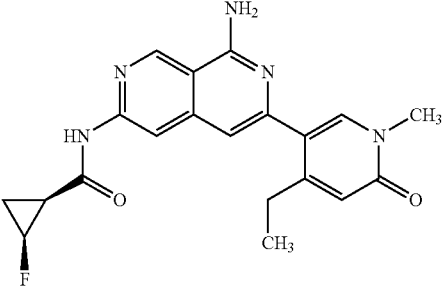 [SMILES: CCc1cc(=O)n(C)cc1-c1cc2cc(NC(=O)[C@@H]3C[C@@H]3F)ncc2c(N)n1]<br>(±)-cis-N-[8-amino-6-(4-ethyl-1-methyl-6-oxo-3-pyridyl)-2,7-naphthyridin-3-yl]-2-fluoro-cyclopropanecarboxamide | 1.43<br>382.1<br>G | 1H NMR (400 MHz, CD3OD) δ 9.16 (s, 1H), 8.19 (s, 1H), 7.65 (s, 1H), 6.84 (s, 1H), 6.40 (s, 1H), 4.88-4.67 (m, 1H), 3.50 (s, 3H), 2.64 (q, J = 7.6 Hz, 2H), 2.12-1.99 (m, 1H), 1.79-1.63 (m, 1H), 1.12-1.10 (m, 1H), 0.98 (t, J = 7.6 Hz, 3H). |
| 65 | 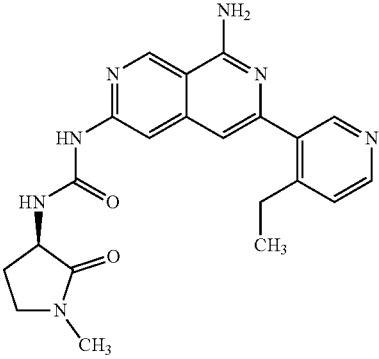 [SMILES: CCc1ccncc1-c1cc2cc(NC(=O)N[C@@H]3CCN(C)C3=O)ncc2c(N)n1]<br>(R)-1-(8-amino-6-(4-ethylpyridin-3-yl)-2,7-naphthyridin-3-yl)-3-(1-methyl-2-oxopyrrolidin-3-yl)urea | 1.501<br>406.2<br>C | 1H NMR (400 MHz, CD3OD): δ 9.29 (s, 1H), 8.50 (s, 2H), 7.52 (s, 1H), 7.45 (d, J = 5.2 Hz, 1H), 6.89 (s, 1H), 4.49 (t, J = 9.2 Hz, 1H), 3.47 (dd, J = 4.0, 9.2 Hz, 2H), 2.93 (s, 3H), 2.83 (q, J = 7.6 Hz, 2H), 2.62-2.57 (m, 1H), 2.09-2.04 (m, 1H), 1.19 (t, J = 7.6 Hz, 3H). |
| 66 | 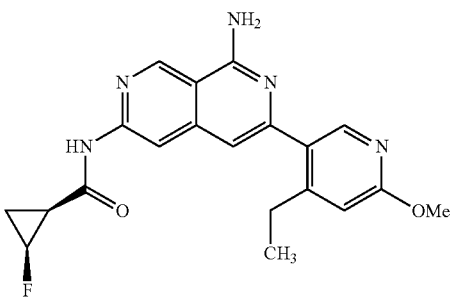 [SMILES: CCc1cc(OC)ncc1-c1cc2cc(NC(=O)[C@@H]3C[C@@H]3F)ncc2c(N)n1]<br>(±)-cis-N-(8-amino-6-(4-ethyl-6-methoxypyridin-3-yl)-2,7-naphthyridin-3-yl)-2-fluorocyclopropanecarboxamide | 1.782<br>382.1<br>C | 1H NMR (400 MHz, CD3OD): δ 9.29 (s, 1H), 8.30 (s, 1H), 8.11 (s, 1H), 6.94 (s, 1H), 6.79 (s, 1H), 4.98-4.87 (m, 1H), 3.96 (s, 3H), 2.81 (q, J = 6.0 Hz, 2H), 2.19-2.16 (m, 1H), 1.86-1.81 (m, 1H), 1.26-1.22 (m, 1H), 1.14 (t, J = 6.0 Hz, 3H). |
| 67 | 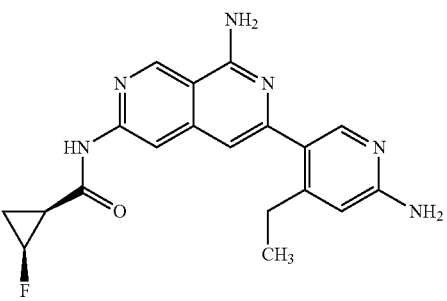 [SMILES: CCc1cc(N)ncc1-c1cc2cc(NC(=O)[C@@H]3C[C@@H]3F)ncc2c(N)n1]<br>(±)-cis-N-(8-amino-6-(6-amino-4-ethylpyridin-3-yl)-2,7-naphthyridin-3-yl)-2-fluorocyclopropanecarboxamide | 1.476<br>367.2<br>G | 1H NMR (400 MHz, CD3OD): δ 9.26 (s, 1H), 8.28 (s, 1H), 7.90 (s, 1H), 6.90 (s, 1H), 6.57 (s, 1H), 5.00-4.79 (m, 1H), 2.74 (q, J = 7.6 Hz, 2H), 2.19-2.13 (m, 1H), 1.88-1.80 (m, 1H), 1.29-1.19 (m, 1H), 1.11 (t, J = 7.6 Hz, 3H). |

TABLE A-1-continued

| Compd No. | Structure/Name | LCMS R$_T$(min) M + H$^+$, Method | $^1$H NMR (ppm) |
|---|---|---|---|
| 68 | N-[8-amino-6-(4-ethyl-3-pyridyl)-2,7-naphthyridin-3-yl]cyclopropene-1-carboxamide | 1.336 332.1 A | $^1$H NMR (400 MHz, DMSO-d$_6$) δ 9.42 (s, 1H), 8.52-8.48 (m, 3H), 8.4 (brs, 1H), 7.58 (dd, J = 1.6, 5.6 Hz, 1H), 7.39 (s, 2H), 7.35 (d, J = 4.8 Hz, 1H), 7.01 (s, 1H), 6.34 (dd, J = 1.6, 4.4 Hz, 1H), 4.79 (s, 2H), 2.80 (q, J = 7.6 Hz, 2H), 1.10 (t, J = 7.6 Hz, 3H). |
| 70 | 5-Methyl-1H-pyrazole-3-carboxylic acid [8-amino-6-(4-ethylpyridin-3-yl)-[2,7]naphthyridin-3-yl]amide | 2.47 374 J | $^1$H NMR (400 MHz, DMSO-d$_6$) δ 13.28 (broad s, 1H), 9.65 (broad s, 1H), 9.43 (s, 1H), 8.54 (s, 1H), 8.52 (d, J = 5.1Hz, 1H), 8.35, (s, 1H), 7.49 (broad s, 2H), 7.38 (d, J = 5.1Hz, 1H), 7.04 (s, 1H), 6.62 (s, 1H), 2.80 (q, J = 7.2 Hz, 2H), 2.31 (s, 3H), 1.11 (t, J = 7.2 Hz, 3H). |
| 71 | 2H-Pyrazole-3-carboxylic acid[8-amino-6-(4-ethylpyridin-3-yl)-[2,7]naphthyridin-3-yl]amide | 2.28 360 J | $^1$H NMR (400 MHz, DMSO-d$_6$) δ 10.05 (v. broad), 9.59 (s, 1H), 8.65 (s, 1H & d, J = 5.2 Hz, 1H), 8.47, (s, 1H), 8.31 (v.broad), 7.94 (s, 1H), 7.58 (d, J = 5.2 Hz, 1H), 7.25 (s, 1H), 6.96 (s, 1H), 2.80 (q, J = 7.2 Hz, 2H), 1.16 (t, J = 7.2 Hz, 3H). |
| 72 | 2-Methyl-2H-pyrazole-3-carboxylic acid [8-amino-6-(4-ethylpyridin-3-yl)-[2,7]naphthyridin-3-yl]amide | 2.44 374 J | $^1$H NMR (400 MHz, DMSO-d$_6$) δ 11.06 (s, 1H), 9.52 (s, 1H), 8.56 (s, 1H), 8.55 (d, J = 5.4 Hz, 1H), 8.42 (s, 1H), 7.69 (broad, 2H), 7.55 (d, J = 2.1Hz, 1H), 7.43 (d, J = 5.4 Hz, 1H), 7.38 (d, J = 2.1Hz, 1H), 7.10 (s, 1H), 4.14 (s, 3H), 2.81 (q, J = 7.5 Hz, 2H), 1.13 (t, J = 7.5 Hz, 3H). |

TABLE A-1-continued

| Compd No. | Structure/Name | LCMS R_T(min) M + H+, Method | $^1$H NMR (ppm) |
|---|---|---|---|
| 73 | 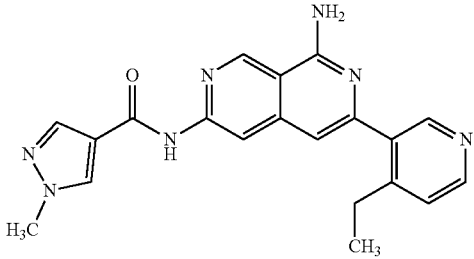 [SMILES: CCc1ccncc1-c1cc2cc(NC(=O)c3cnn(C)c3)ncc2c(N)n1]<br>1-Methyl-1H-pyrazole-4-carboxylic acid [8-amino-6-(4-ethylpyridin-3-yl)-[2,7]naphthyridin-3-yl]amide | 2.21<br>374<br>J | $^1$H NMR (400 MHz, DMSO-d$_6$) δ 10.64 (s, 1H), 9.43 (s, 1H), 8.51 (s, 1H), 8.49 (d, J = 5.1Hz, 1H), 8.47 (s, 1H), 8.36 (s 1H), 8.18 (s, 1H), 7.35 (d, J = 5.1Hz, 1H), 7.33 (broad, 2H), 6.97 (s, 1H), 3.90 (s, 3H), 2.80 (q, J = 7.3 Hz, 2H), 1.11 (t, J = 7.3 Hz, 3H). |
| 74 | 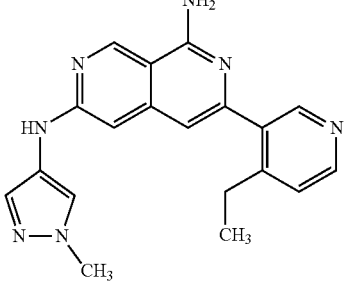<br>3-(4-Ethylpyridin-3-yl)-N6-(1-methyl-1H-pyrazol-4-yl)-[2,7]naphthyridine-1,6-diamine | 2.10<br>346<br>J | $^1$H NMR (400 MHz, DMSO-d$_6$) δ 9.21 (s, 1H), 8.84 (s, 1H), 8.46 (s, 1H) & d, J = 5.0 Hz, 1H), 7.87 (s, 1H), 7.45 (s, 1H), 7.32 (d, J = 5.0 Hz, 1H), 7.07 (broad, 2H), 6.72 (s, 1H), 6.62 (s, 1H), 3.83 (s, 3H), 2.78 (q, J = 7.1Hz, 2H), 1.10 (t, J = 7.1Hz, 3H). |
| 75 | 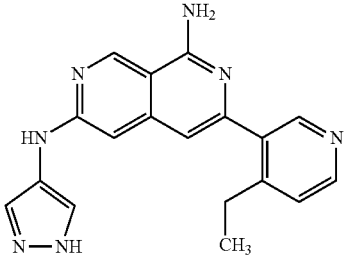 [SMILES: CCc1ccncc1-c1cc2cc(Nc3cn[nH]c3)ncc2c(N)n1]<br>3-(4-Ethylpyridin-3-yl)-N6-(1H-pyrazol-4-yl)-[2,7]naphthyridine-1,6-diamine | 1.92<br>332<br>J | $^1$H NMR (400 MHz, DMSO-d$_6$) δ 12.83 (v. broad, 1H), 9.66 (broad, 1H), 9.47 (s, 1H), 8.65 (d, J = 5.3 Hz, 1H), 8.58 (s, 1H), 7.79 (broad, 2H), 7.50 (d, J = 5.3 Hz, 1H), 6.99 (s, 1H), 6.78 (s, 1H), 2.68 (q, J = 7.4 Hz, 2H), 1.14 (t, J = 7.4 Hz, 3H). |
| 76 | 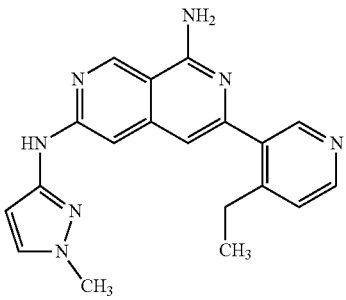 [SMILES: CCc1ccncc1-c1cc2cc(Nc3ccn(C)n3)ncc2c(N)n1]<br>3-(4-Ethylpyridin-3-yl)-N6-(1-methyl-1H-pyrazol-3-yl)-[2,7]naphthyridine-1,6-diamine | 2.24<br>346<br>J | $^1$H NMR (400 MHz, DMSO-d$_6$) δ 9.37 (s, 1H), 9.22 (s, 1H), 8.48 (s, 1H), 8.47 (d, J = 5.1Hz, 1H), 7.55 (d, J = 2.1Hz, 1H), 7.49 (s, 1H), 7.32 (d, J = 5.1Hz, 1H), 7.07 (broad, 2H), 6.74 (s, 1H), 6.10 (d, J = 2.1Hz, 1H), 3.80 (s, 3H), 2.79 (q, J = 7.0 Hz, 2H), 1.10 (t, J = 7.0 Hz, 3H). |

TABLE A-1-continued

| Compd No. | Structure/Name | LCMS R_T(min) M + H+, Method | ¹H NMR (ppm) |
|---|---|---|---|
| 77 | 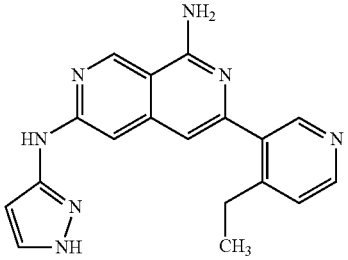 [SMILES: CCc1ccncc1-c1cc2cc(Nc3cc[nH]n3)ncc2c(N)n1]<br>3-(4-Ethylpyridin-3-yl)-N6-(1H-pyrazol-3-yl)-[2,7]naphthyridine-1,6-diamine | 2.09<br>332<br>J | ¹H NMR (400 MHz, DMSO-d₆) δ 12.17 (broad, 1H), 9.40 (s, 1H), 9.23 (s, 1H), 8.49 (s, 1H), 8.47 (d, J = 5.2 Hz, 1H), 7.61 (broad, 2H), 7.33 (d, J = 5.2 Hz, 1H), 7.10 (broad s, 2H), 6.74 (s, 1H), 6.12 (d, J = 2.1Hz, 1H), 2.79 (q, J = 7.5 Hz, 2H), 1.10 (t, J = 7.5 Hz, 3H). |
| 78 | 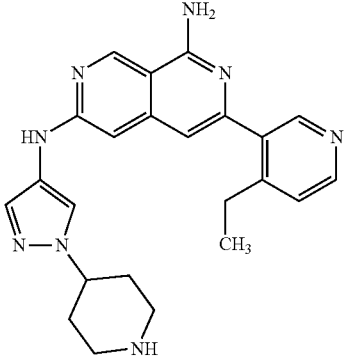 [SMILES: CCc1ccncc1-c1cc2cc(Nc3cnn(C4CCNCC4)c3)ncc2c(N)n1]<br>3-(4-Ethylpyridin-3-yl)-N6-(1-piperidin-4-yl-1H-pyrazol-4-yl)-[2,7]naphthyridine-1,6-diamine | 1.72<br>415<br>J | ¹H NMR (400 MHz, DMSO-d₆) δ 9.21 (s, 1H), 8.87 & 8.82 (2x s*, 1H), 8.46 (m, 2H), 7.94 & 7.93 (2x s*, 1H), 7.52 & 7.49 (2x s*, 1H), 7.32 (d, J = 5.1Hz, 1H), 7.06 (broad, 2H), 6.72 (s, 1H), 6.64 (s, 1H), 4.32 & 4.13 (2x m*, 1H), 3.23 & 3.10 (2x m*, 2H), 2.84 (m, 2H), 2.79 (q, J = 7.5 Hz, 2H), 2.08 (m, 2H), 1.97 (m, 2H), 1.09 (t, J = 7.5 Hz, 3H).<br>*Major & minor conformers |
| 79 | 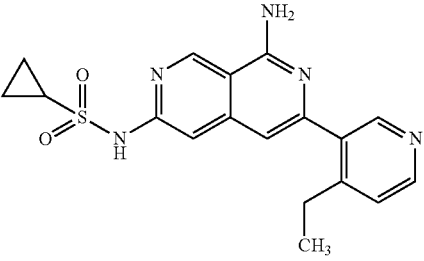 [SMILES: CCc1ccncc1-c1cc2cc(NS(=O)(=O)C3CC3)ncc2c(N)n1]<br>Cyclopropanesulfonic acid [8-amino-6-(4-ethylpyridin-3-yl)-[2,7]naphthyridin-3-yl]amide | 2.23<br>370<br>J | ¹H NMR (400 MHz, DMSO-d₆) δ 10.84 (broad s, 1H), 9.38 (s, 1H), 8.52 (s, 1H & d, J = 5.1Hz, 1H), 7.58 (broad, 2H), 7.38 (d, J = 5.1 Hz, 1H), 7.23 (s, 1H), 6.97 (s, 1H), 3.08 (m, 1H), 2.78 (q, J = 7.2 Hz, 2H), 1.10 (m, 5H), 1.03 (m, 2H). |
| 80 | 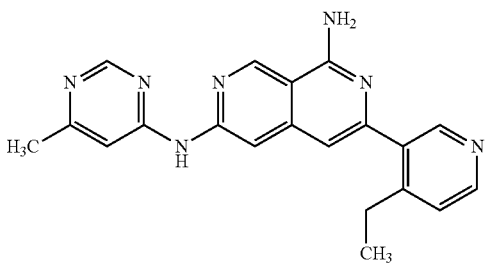 [SMILES: CCc1ccncc1-c1cc2cc(Nc3cc(C)ncn3)ncc2c(N)n1]<br>3-(4-Ethylpyridin-3-yl)-N6-(6-methylpyrimidin-4-yl)-[2,7]naphthyridine-1,6-diamine | 1.86<br>358<br>J | ¹H NMR (400 MHz, DMSO-d₆) δ 10.33 (s, 1H), 9.39 (s, 1H), 8.65 (s, 1H), 8.51 (s, 1H), 8.49 (d, J = 5.1 Hz, 1H), 8.19 (s, 1H), 7.35 (d, J = 5.1Hz, 1H), 7.31 (broad, 2H), 7.28 (s, 1H), 6.92 (s, 1H), 2.80 (q, J = 7.5 Hz, 2H), 2.36 (s, 3H), 1.10 (t, 3H). |

TABLE A-1-continued

| Compd No. | Structure/Name | LCMS $R_T$(min) M + H+, Method | $^1$H NMR (ppm) |
|---|---|---|---|
| 81 | 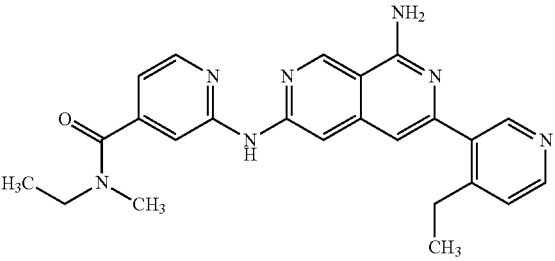 [SMILES: CCc1ccncc1-c1cc2cc(Nc3cc(C(=O)N(C)CC)ccn3)ncc2c(N)n1] 2-[8-Amino-6-(4-ethylpyridin-3-yl)-[2,7]naphthyridin-3-ylaminol-N-ethyl-N-methylisonicotinamide | 2.30 428 J | $^1$H NMR (400 MHz, DMSO-d$_6$, 80° C.) δ 9.73 (broad s, 1H), 9.32 (s, 1H), 8.50 (s, 1H), 8.46 (d, J = 5.5 Hz, 1H), 8.31 (d, J = 5.0 Hz, 1H), 8.07 (s, 1H), 7.43 (s, 1H), 7.29 (d, J = 5.5 Hz, 1H), 6.91 (broad, 2H), 6.84 (s, 1H), 6.82 (d, J = 5.1Hz, 1H), 3.34 (broad, 2H), 2.93 (s, 3H), 2.80 (q, J = 7.5 Hz, 2H), 1.12 (m, 6H). |
| 82 | 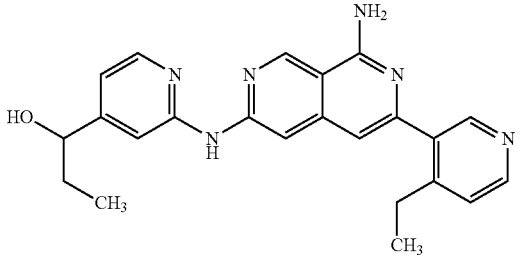 [SMILES: CCc1ccncc1-c1cc2cc(Nc3cc(C(O)CC)ccn3)ncc2c(N)n1] (±)-1-{2-[8-Amino-6-(4-ethylpyridin-3-yl)-[2,7]naphthyridin-3-ylamino]-pyridin-4-yl}propan-1-ol | 2.04 401 J | $^1$H NMR (400 MHz, DMSO-d$_6$) δ 9.94 (broad s, 1H), 9.35 (s, 1H), 8.51 (s, 1H), 8.50 (d, J = 5.1Hz, 1H), 8.25 (s, 1H), 8.20 (d, J = 5.1 Hz, 1H), 7.35 (broad m, 4H), 6.87 (broad m, 2H), 5.33 (d, J = 4.2 Hz, 1H), 4.43 (m, 1H), 2.79 (q, J = 7.5 Hz, 2H), 1.61 (m, 2H), 1.11 (t, J = 7.5 Hz, 3H), 0.87 (t, J = 7.3 Hz, 3H). |
| 83 | 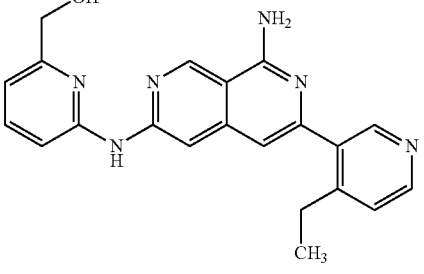 {6-[8-amino-6-(4-ethylpyridin-3-yl)-[2,7]naphthyridin-3-ylamino]pyridin-2-yl}methanol | 1.81 373 J | $^1$H NMR (400 MHz, DMSO-d$_6$) δ 9.86 (s, 1H), 9.31 (s, 1H), 8.50 (s, 1H), 8.48 (d, J = 5.1Hz, 1H), 8.27 (s, 1H), 7.66 (t, J = 7.7 Hz, 1H), 7.34 (d, J = 5.1Hz, 1H), 7.25 (d, J = 7.7 Hz, 1H), 7.16 (broad, 2H), 6.97 (d, J = 5.1Hz, 1H)), 6.86 (s, 1H), 5.34 (t, J = 6.0 Hz, 1H), 4.55 (d, J = 6.0 Hz, 2H), 2.80 (q, J = 7.5 Hz, 2H), 1.11 (t, J = 7.5 Hz, 3H). |
| 84 | 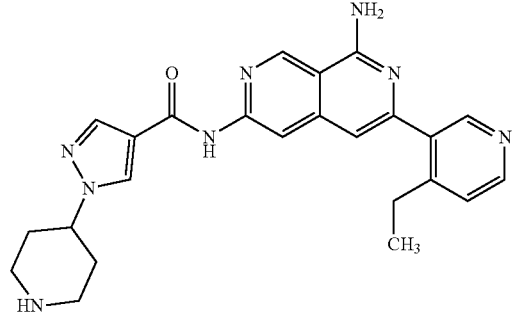 [SMILES: CCc1ccncc1-c1cc2cc(NC(=O)c3cnn(C4CCNCC4)c3)ncc2c(N)n1] N-(8-amino-6-(4-ethylpyridin-3-yl)-2,7-naphthyridin-3-yl)-1-(piperidin-4-yl)-1H-pyrazole-4-carboxamide | 1.81 443 J | $^1$H NMR (400 MHz, DMSO-d$_6$) δ 10.28 (broad s, 1H), 9.40 (s, 1H), 8.55 (s, 1H), 8.51 (s, 1H), 8.47 (d, J = 5.1Hz, 1H), 8.32 (s, 1H), 8.11 (s, 1H), 7.30 (d, J = 5.1Hz, 1H), 7.04 (broad, 2H), 6.95 (s, 1H), 4.25 (m, 1H), 3.07 (m, 2H, masked by water), 2.80 (q, J = 7.5 Hz, 2H), 2.64 (m, 2H), 2.02 (m, 2H), 1.80 (m, 2H), 1.11 (t, J = 7.5 Hz, 3H). |

TABLE A-1-continued

| Compd No. | Structure/Name | LCMS R_T(min) M + H+, Method | $^1$H NMR (ppm) |
|---|---|---|---|
| 85 | 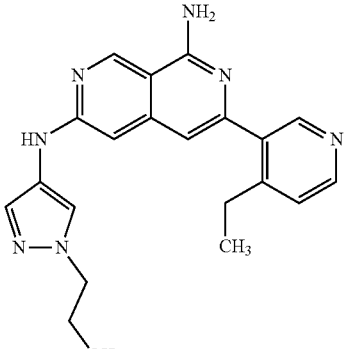<br>2-{4-[8-Amino-6-(4-ethylpyridin-3-yl)-[2,7]naphthyridin-3-ylamino]pyrazol-1-yl}ethanol | 1.93<br>376<br>J | $^1$H NMR (400 MHz, DMSO-d$_6$) δ 9.21 (s, 1H), 8.84 (s, 1H), 8.46 (s, 1H & d, J = 5.1Hz, 1H), 7.91 (s, 1H), 7.49 (s, 1H), 7.32 (d, J = 5.1 Hz, 1H), 7.04 (broad, 2H), 6.71 (s, 1H), 6.63 (s, 1H), 4.89 (t, J = 5.5 Hz, 1H), 4.12 (t, J = 5.8 Hz, 2H), 3.74 (q, J = 5.8 Hz, 2H), 2.78 (q, J = 7.5 Hz, 2H), 1.09 (t, J = 7.5 Hz, 3H). |
| 86 | 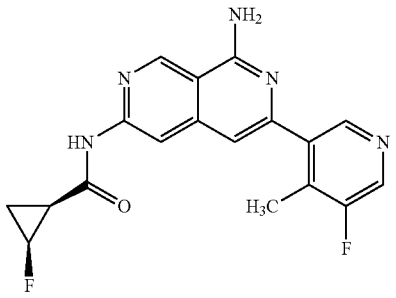 [SMILES: Cc1c(F)cncc1-c1cc2cc(NC(=O)[C@@H]3C[C@@H]3F)ncc2c(N)n1]<br>(1S,2S)-N-(8-amino-6-(5-fluoro-4-methylpyridin-3-yl)-2,7-naphthyridin-3-yl)-2-fluorocyclopropane-1-carboxamide | 1.10<br>356.1<br>P | — |
| 87 | 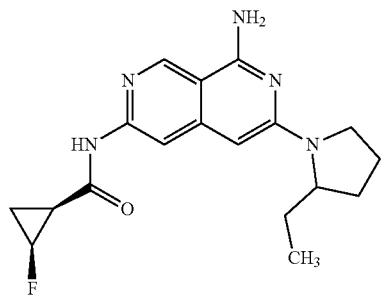 [SMILES: CCC1CCCN1c1cc2cc(NC(=O)[C@@H]3C[C@@H]3F)ncc2c(N)n1]<br>(±)-cis-N-(8-amino-6-(2-ethylpyrrolidin-1-yl)-2,7-naphthyridin-3-yl)-2-fluorocyclopropane-1-carboxamide | 3.47,<br>344.2<br>Q | — |
| 88 | 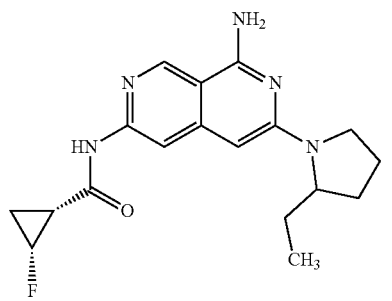 [SMILES: CCC1CCCN1c1cc2cc(NC(=O)[C@H]3C[C@H]3F)ncc2c(N)n1]<br>(±)-cis-N-(8-amino-6-(2-ethylpyrrolidin-1-yl)-2,7-naphthyridin-3-yl)-2-fluorocyclopropane-1-carboxamide | 3.45,<br>344.2<br>Q | — |

| Compd No. | Structure/Name | LCMS R$_T$(min) M + H$^+$, Method | $^1$H NMR (ppm) |
|---|---|---|---|
| 89 | 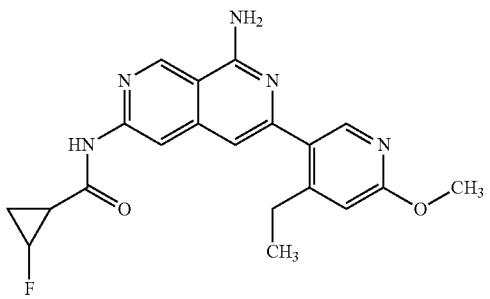<br>(±)-cis-N-(8-amino-6-(4-ethyl-6-methoxypyridin-3-yl)-2,7-naphthyridin-3-yl)-2-fluorocyclopropane-1-carboxamide | n/a | — |
| 90 | 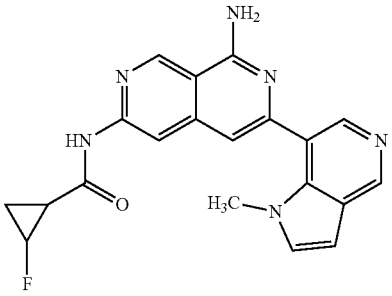<br>(±)-cis-N-(8-amino-6-(1-methyl-1H-pyrrolo[3,2-c]pyridin-7-yl)-2,7-naphthyridin-3-yl)-2-fluorocyclopropane-1-carboxamide | 1.48, 377.1 C | — |

TABLE A-1-continued

| Compd No. | Structure/Name | LCMS R_T(min) M + H+, Method | ¹H NMR (ppm) |
|---|---|---|---|
| 91 | 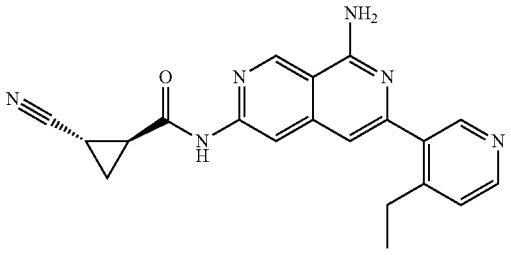 [SMILES: CCc1ccncc1-c1cc2cc(NC(=O)[C@H]3C[C@@H]3C#N)ncc2c(N)n1]<br>(1S,2S)-N-(8-amino-6-(4-ethylpyridin-3-yl)-2,7-naphthyridin-3-yl)-2-cyanocyclopropane-1-carboxamide (Absolute stereochemistry arbitrarily assigned) | 2.68, 360.1 Q | — |
| 92 | 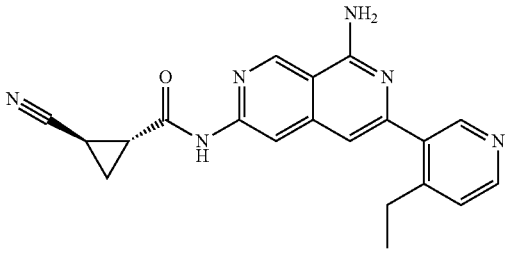 [SMILES: CCc1ccncc1-c1cc2cc(NC(=O)[C@@H]3C[C@H]3C#N)ncc2c(N)n1]<br>(1R,2R)-N-(8-amino-6-(4-ethylpyridin-3-yl)-2,7-naphthyridin-3-yl)-2-cyanocyclopropane-1-carboxamide (Absolute stereochemistry arbitrarily assigned) | 2.68, 360.1 Q | — |
| 93 | 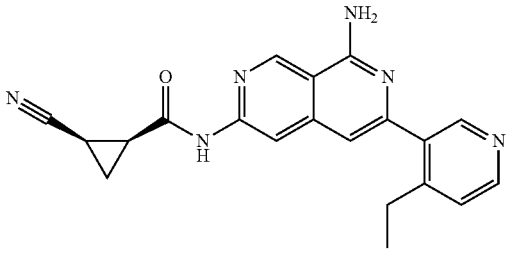 [SMILES: CCc1ccncc1-c1cc2cc(NC(=O)[C@H]3C[C@H]3C#N)ncc2c(N)n1]<br>(1S,2R)-N-(8-amino-6-(4-ethylpyridin-3-yl)-2,7-naphthyridin-3-yl)-2-cyanocyclopropane-1-carboxamide (Absolute stereochemistry arbitrarily assigned) | 2.68, 360.1 Q | — |
| 94 | 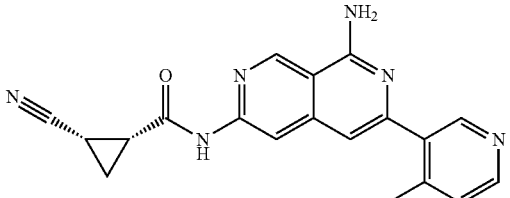<br>(1R,2S)-N-(8-amino-6-(4-ethylpyridin-3-yl)-2,7-naphthyridin-3-yl)-2-cyanocyclopropane-1-carboxamide (Absolute stereochemistry arbitrarily assigned) | 2.68, 360.1 Q | — |

TABLE A-1-continued

| Compd No. | Structure/Name | LCMS $R_T$(min) M + H$^+$, Method | $^1$H NMR (ppm) |
|---|---|---|---|
| 96 | 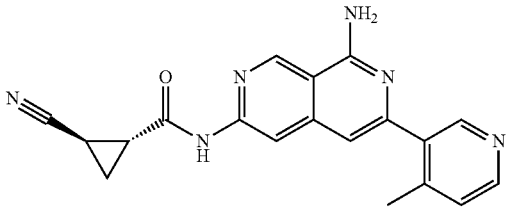 [SMILES: Cc1ccncc1-c1cc2cc(NC(=O)[C@@H]3C[C@H]3C#N)ncc2c(N)n1]<br>(1R,2R)-N-(8-amino-6-(4-methylpyridin-3-yl)-2,7-naphthyridin-3-yl)-2-cyanocyclopropane-1-carboxamide<br>(Absolute stereochemistry arbitrarily assigned) | 2.52, 345.1 Q | — |
| 97 | 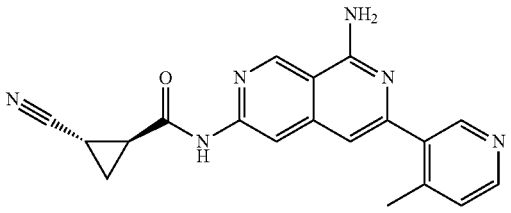 [SMILES: Cc1ccncc1-c1cc2cc(NC(=O)[C@H]3C[C@@H]3C#N)ncc2c(N)n1]<br>(1S,2S)-N-(8-amino-6-(4-methylpyridin-3-yl)-2,7-naphthyridin-3-yl)-2-cyanocyclopropane-1-carboxamide<br>(Absolute stereochemistry arbitrarily assigned) | 2.52, 345.1 Q | — |
| 98 | 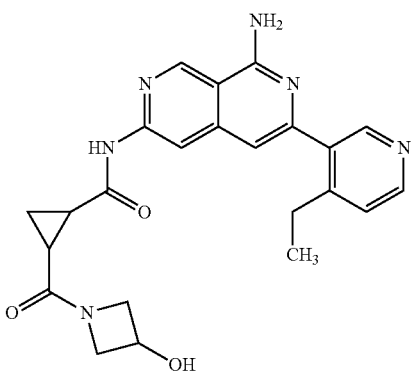 | 1.43, 433.2 C | — |
| | 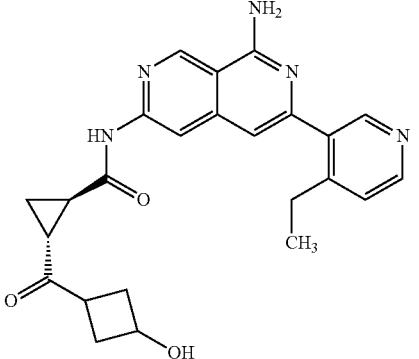<br>(±)-trans-N-(8-amino-6-(4-ethylpyridin-3-yl)-2,7-naphthyridin-3-yl)-2-(3-hydroxycyclobutane-1-carbonyl)cyclopropane-1-carboxamide<br>(Absolute stereochemistry arbitrarily assigned) | | |

TABLE A-1-continued
| Compd No. | Structure/Name | LCMS R_T(min) M + H+, Method | ¹H NMR (ppm) |
|---|---|---|---|
| 99 | 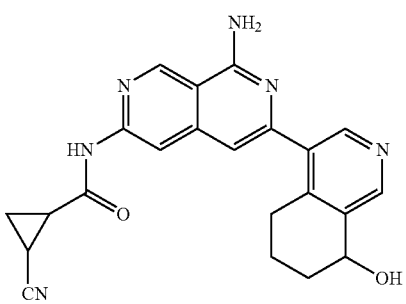 (±)-trans-N-(8-amino-6-(8-hydroxy-5,6,7,8-tetrahydroisoquinolin-4-yl)-2,7-naphthyridin-3-yl)-2-cyanocyclopropane-1-carboxamide (Absolute stereochemistry arbitrarily assigned) | 1.30 401.1 A | — |
| 100 | 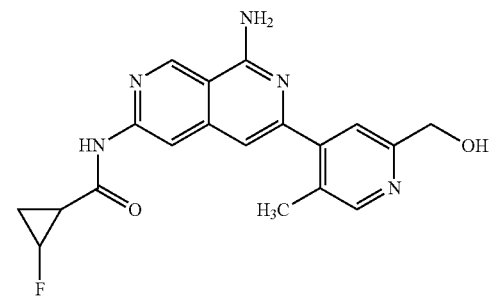 (±)-cis-N-(8-amino-6-(2-(hydroxymethyl)-5-methylpyridin-4-yl)-2,7-naphthyridin-3-yl)-2-fluorocyclopropane-1-carboxamide | 1.48 368.2 F | — |

TABLE A-1-continued
| Compd No. | Structure/Name | LCMS R_T(min) M + H+, Method | $^1$H NMR (ppm) |
|---|---|---|---|
| 101 | 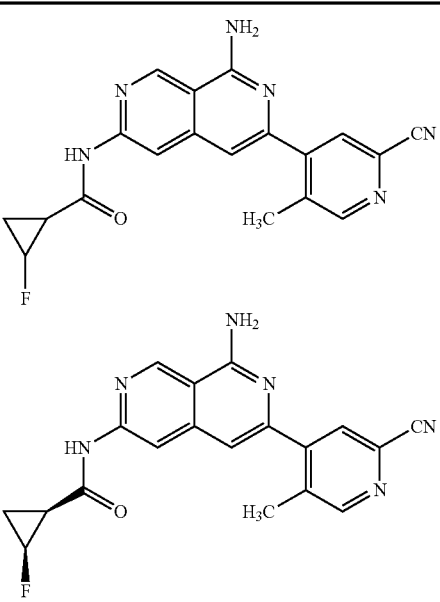<br>(±)-cis-N-(8-amino-6-(2-cyano-5-methylpyridin-4-yl)-2,7-naphthyridin-3-yl)-2-fluorocyclopropane-1-carboxamide | 1.52<br>363.2<br>B | — |
| 102 | 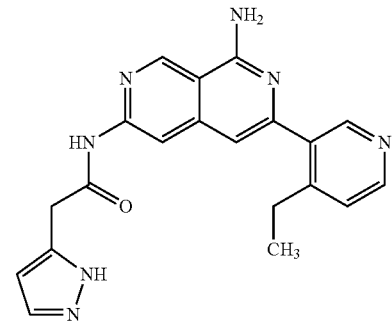 [SMILES: CCc1ccncc1-c1cc2cc(NC(=O)Cc3ccn[nH]3)ncc2c(N)n1] | 1.54<br>374.2<br>C | — |
| 103 | 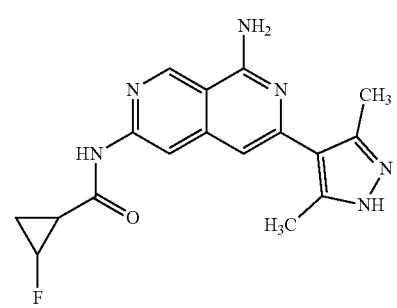 | 1.31,<br>341.1<br>B | — |

TABLE A-1-continued

| Compd No. | Structure/Name | LCMS R_T(min) M + H+, Method | ¹H NMR (ppm) |
|---|---|---|---|
| | (±)-cis-N-(8-amino-6-{3,5-dimethyl-1H-pyrazol-4-yl)-2,7-naphthyridin-3-yl)-2-fluorocyclopropane-1-carboxamide | | |
| 104 | (±)-trans-N-(8-amino-6-(1.2-dimethyl-1H-imidazol-5-yl)-2,7-naphthyridin-3-yl)-2-cyanocyclopropane-1-carboxamide | 1.50 348.2 F | — |
| 105 | | 1.53, 346.1 F | — |

TABLE A-1-continued

| Compd No. | Structure/Name | LCMS R_T(min) M + H+, Method | ¹H NMR (ppm) |
|---|---|---|---|
| 106 | (±)-cis-N-(8-amino-6-(pyridin-3-yl)-2,7-naphthyridin-3-yl)-2-fluorocyclopropane-1-carboxamide | 324.1 | — |
| 107 | Enantiomer 1 of (trans)-N-(8-amino-6-(4-methylpyridin-3-yl)-2,7-naphthyridin-3-yl)-2-fluorocyclopropane-1-carboxamide | 2.69, 338.1 Q | — |

TABLE A-1-continued
| Compd No. | Structure/Name | LCMS R_T(min) M + H+, Method | ¹H NMR (ppm) |
|---|---|---|---|
| 108 | 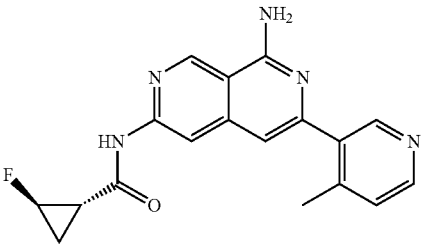 [SMILES: Cc1ccncc1-c1cc2cc(NC(=O)[C@@H]3C[C@H]3F)ncc2c(N)n1]  Enantiomer 2 of (trans)-N-(8-amino-6-(4-methylpyridin-3-yl)-2,7-naphthyridin-3-yl)-2-fluorocyclopropane-1-carboxamide | 2.69, 338.1 Q | — |
| 109 | 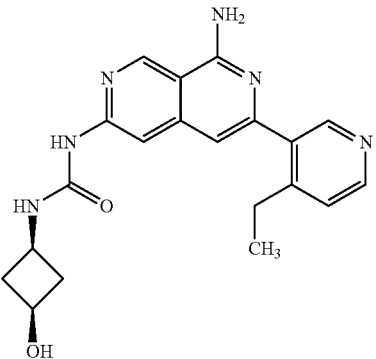 [SMILES: CCc1ccncc1-c1cc2cc(NC(=O)N[C@H]3C[C@@H](O)C3)ncc2c(N)n1]  1-[8-amino-6-(4-ethyl-3-pyridyl)-2,7-naphthyridin-3-yl]-3-(cis-3-hydroxycyclobutyl)urea | 1.48 379.2 F | — |
| 110 | 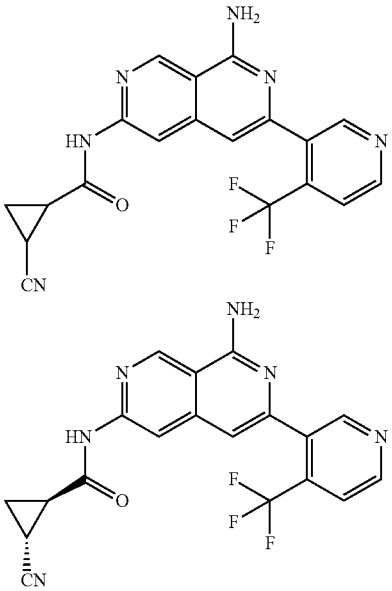  (±)-trans-N-(8-amino-6-(4-(trifluoromethyl)pyridin-3-yl)-2,7-naphthyridin-3-yl)-2-cyanocyclopropane-1-carboxamide | 1.55 399.1 E | — |

TABLE A-1-continued
| Compd No. | Structure/Name | LCMS R_T(min) M + H+, Method | ¹H NMR (ppm) |
|---|---|---|---|
| 111 | 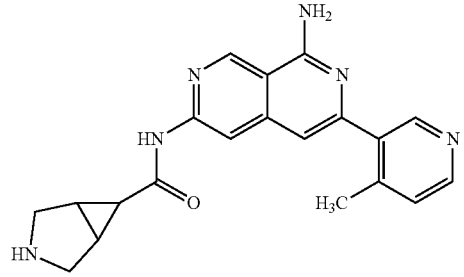 [SMILES: Cc1ccncc1-c1cc2cc(NC(=O)C3C4CNCC43)ncc2c(N)n1]<br>N-[8-amino-6-(4-methyl-3-pyridyl)-2,7-naphthyridin-3-yl]-3-azabicyclo[3.1.0]hexane-6-carboxamide | 1.17 361.1 E | — |
| 112 | 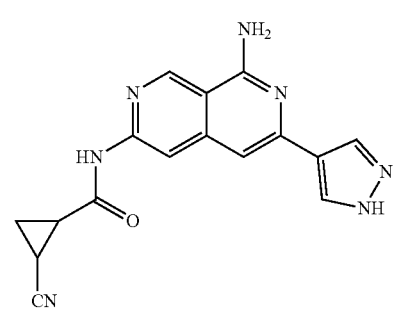<br>(±)-trans-N-(8-amino-6-(1H-pyrazol-4-yl)-2,7-naphthyridin-3-yl)-2-cyanocyclopropane-1-carboxamide | 1.32, 320.1 E | — |
| 113 | 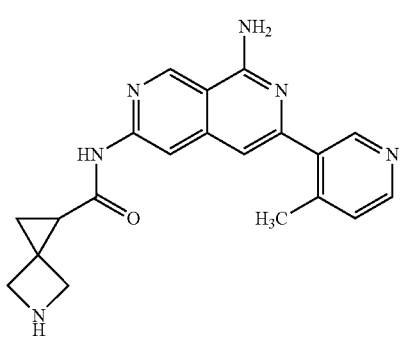 [SMILES: Cc1ccncc1-c1cc2cc(NC(=O)C3CC34CNC4)ncc2c(N)n1]<br>N-[8-amino-6-(4-methyl-3-pyridyl)-2,7-naphthyridin-3-yl]-5-azaspiro[2.3]hexane-2-carboxamide | 1.38, 361.1 F | — |

TABLE A-1-continued
| Compd No. | Structure/Name | LCMS R_T(min) M + H+, Method | ¹H NMR (ppm) |
|---|---|---|---|
| 114 | 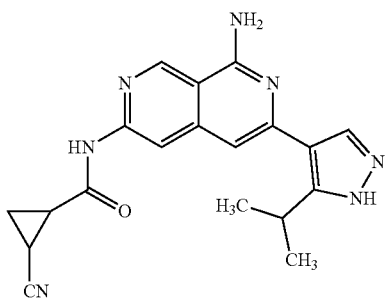 | n/a | — |
| | 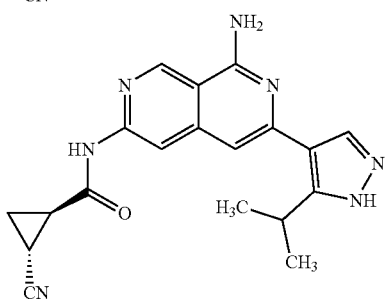<br>(±)-trans-N-(8-amino-6-(5-isopropyl-1H-pyrazol-4-yl)-2,7-naphthyridin-3-yl)-2-cyanocyclopropane-1-carboxamide | | |
| 115 | 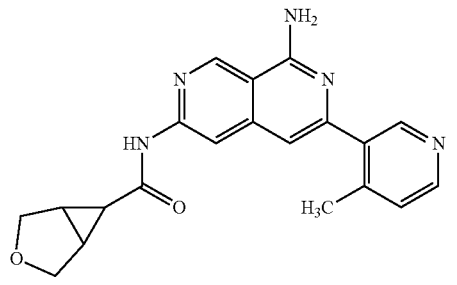 [SMILES: Cc1ccncc1-c1cc2cc(NC(=O)C3C4COCC43)ncc2c(N)n1]<br>amino-6-(4-methyl-3-pyridyl)-2,7-naphthyridin-3-yl]-3-oxabicyclo[3.1.0]hexane-6-carboxamide | n/a | — |
| 116 | 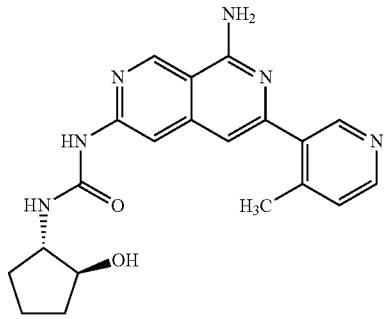 [SMILES: Cc1ccncc1-c1cc2cc(NC(=O)N[C@H]3CCC[C@@H]3O)ncc2c(N)n1]<br>1-[8-amino-6-(4-methyl-3-pyridyl)-2,7-naphthyridin-3-yl]-3-[rac-(1S,2S)-2-hydroxycyclopentyl]urea | n/a | — |

| Compd No. | Structure/Name | LCMS R_T(min) M + H+, Method | 1H NMR (ppm) |
|---|---|---|---|
| 117 | 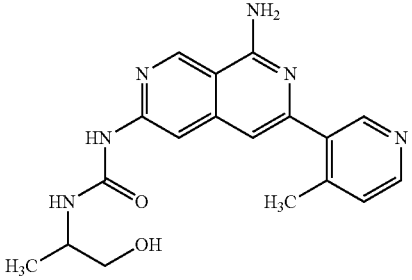 [SMILES: Cc1ccncc1-c1cc2cc(NC(=O)NC(C)CO)ncc2c(N)n1]<br>1-(8-amino-6-(4-methylpyridin-3-yl)-2,7-naphthyridin-3-yl)-3-(1-hydroxypropan-2-yl)urea | n/a | — |
| 118 | 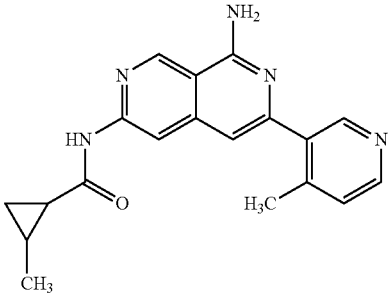<br>(±)-trans-N-(8-amino-6-(4-methylpyridin-3-yl)-2,7-naphthyridin-3-yl)-2-methylcyclopropane-1-carboxamide | n/a | — |
| 119 | 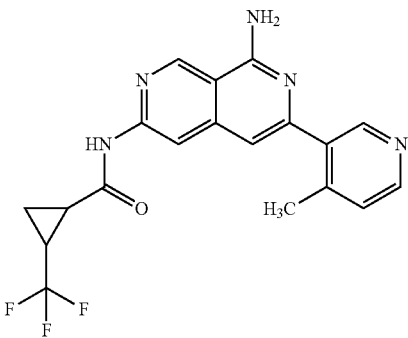 | n/a | — |

| Compd No. | Structure/Name | LCMS R$_T$(min) M + H$^+$, Method | $^1$H NMR (ppm) |
|---|---|---|---|
|  | (±)-trans-N-(8-amino-6-(4-methylpyridin-3-yl)-2,7-naphthyridin-3-yl)-2-(trifluoromethyl)cyclopropane-1-carboxamide | | |
| 120 | (±)-3-(4-methyl-3-pyridyl)-N6-pyrrolidin-3-yl-2,7-naphthyridine-1,6-diamine | 1.34 321.1 C | $^1$H NMR (400 MHz, CD$_3$OD): 9.20 (s, 1H), 8.52 (s, 1H), 8.47 (d, J = 5.2 Hz, 1H), 8.41 (brs, 2H), 7.42 (d, J = 5.2 Hz, 1H), 6.78 (s, 1H), 6.65 (s, 1H), 4.69-4.66 (m, 1H), 3.66-3.54 (m, 2H), 3.48-3.37 (m, 2H), 2.48-2.41 (m, 1H), 2.44 (s, 3H), 2.20-2.15 (m, 1H). |
| 121 | (±)-trans-N-[8-amino-6-(4-methyl-3-pyridyl)-2,7-naphthyridin-3-yl]-2-(1H-pyrazol-3-yl)cyclopropanecarboxamide | 1.54 386.1 C | $^1$H NMR (400 MHz, CD$_3$OD): δ 9.29 (s, 1H), 8.54 (s, 1H), 8.43 (d, J = 5.2 Hz, 1H), 8.34 (s, 1H), 7.54 (s, 1H), 7.40 (d, J = 5.2 Hz, 1H), 6.99 (s, 1H), 6.16 (d, J = 1.6 Hz, 1H), 2.62-2.57 (m, 1H), 2.46 (s, 3H), 2.31-2.27 (m, 1H), 1.67-1.62 (m, 1H), 1.46-1.41 (m, 1H). |
| 122 | (±)-trans-N-[8-amino-6-(4-methyl-3-pyridyl)-2,7-naphthyridin-3-yl]-2-(1H-pyrazol-4-yl)cyclopropanecarboxamide | 1.240 386.1 G | 1H NMR (400 MHz, DMSO-d$_6$) δ 12.62 (s, 1H), 10.94 (s, 1H), 9.37 (s, 1H), 8.57 (s, 1H), 8.26 (s, 1H), 8.44 (d, J = 5.2 Hz, 1H), 7.62 (s, 1H), 7.37 (s, 1H), 7.32-7.31 (m, 3H), 6.97 (s, 1H), 2.41 (s, 3H), 2.27-2.19 (m, 2H), 1.50-1.36 (m, 1H), 1.27-1.11 (m, 1H). |

TABLE A-1-continued

| Compd No. | Structure/Name | LCMS R<sub>T</sub>(min) M + H<sup>+</sup>, Method | ¹H NMR (ppm) |
|---|---|---|---|
| 123 | 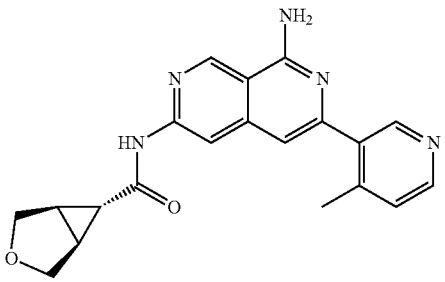 [SMILES: Cc1ccncc1-c1cc2cc(NC(=O)[C@H]3[C@@H]4COC[C@@H]43)ncc2c(N)n1]<br>(1R,5S,6R)-N-[8-amino-6-(4-methyl-3-pyridyl)-2,7-naphthyridin-3-yl]-3-oxabicyclo[3.1.0]hexane-6-carboxamide<br>(Absolute stereochemistry arbitrarily assigned) | 1.262<br>362.1<br>A | $^{1}$H NMR (400 MHz, CD$_3$OD) δ 9.28 (s, 1H), 8.53 (s, 1H), 8.43 (d, J = 5.2 Hz, 1H), 8.28 (s, 1H), 7.40 (d, J = 5.2 Hz, 1H), 6.97 (s, 1H), 3.98 (d, J = 8.8 Hz, 2H), 3.81 (d, J = 8.8 Hz, 2H), 2.45 (s, 3H), 2.26-2.26 (m, 2H), 1.91-1.89 (m, 1H). |
| 124 | 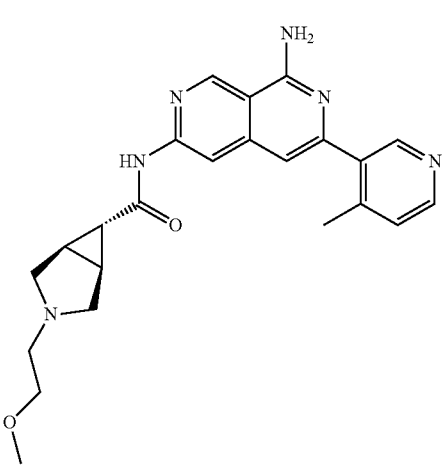 [SMILES: COCCN1C[C@@H]2[C@H](C1)[C@H]2C(=O)Nc1cc2cc(-c3cnccc3C)nc(N)c2cn1]<br>exo-N-[8-amino-6-(4-methyl-3-pyridyl)-2,7-naphthyridin-3-yl]-3-(2-methoxyethyl)-3-azabicyclo[3.1.0]hexane-6-carboxamide<br>(Absolute stereochemistry arbitrarily assigned) | 1.775<br>419.2<br>I-1 | $^{1}$H NMR (400 MHz, CD$_3$OD) δ 9.28 (s, 1H), 8.53 (s, 1H), 8.43 (d, J = 5.2 Hz, 1H), 8.27 (s, 1H), 7.39 (d, J = 5.2 Hz, 1H), 6.96 (s, 1H), 3.51 (t, J = 5.6 Hz, 2H), 3.37 (s, 3H), 3.20-3.18 (m, 2H), 2.70 (t, J = 5.6 Hz, 2H), 2.56-2.63 (m, 2H), 2.45 (s, 3H), 2.24-2.22 (m, 1H), 2.05 (s, 2H). |
| 125 | 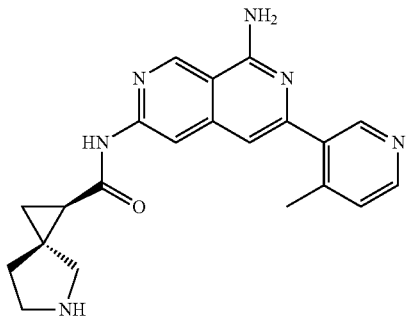 [SMILES: Cc1ccncc1-c1cc2cc(NC(=O)[C@@H]3C[C@]34CCNC4)ncc2c(N)n1]<br>(±)-trans-N-(8-amino-6-(4-methylpyridin-3-yl)-2,7-naphthyridin-3-yl)-5-azaspiro[2.4]heptane-1-carboxamide | 1.390<br>375.2<br>G | $^{1}$H NMR (400 MHz, CD$_3$OD) δ 9.29 (s, 1H), 8.53 (s, 1H), 8.43 (d, J = 4.8 Hz, 1H), 8.33 (s, 1H), 7.40 (d, J = 4.8 Hz, 1H), 6.97 (s, 1H), 3.29-3.20 (m, 4H), 2.45 (s, 3H), 2.25-2.22 (m, 1H), 2.11-2.04 (m, 1H), 2.00-1.1.94 (m, 1H), 1.45-1.43 (m, 1H), 1.34-1.31 (m, 1H). |

| Compd No. | Structure/Name | LCMS R$_T$(min) M + H$^+$, Method | $^1$H NMR (ppm) |
|---|---|---|---|
| 126 | 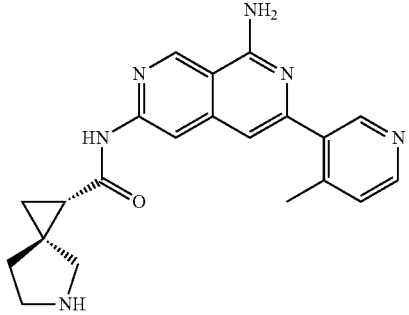 [SMILES: Cc1ccncc1-c1cc2cc(NC(=O)[C@H]3C[C@]34CCNC4)ncc2c(N)n1]<br>(±)-cis-N-(8-amino-6-(4-methylpyridin-3-yl)-2,7-naphthyridin-3-yl)-5-azaspiro[2.4]heptane-1-carboxamide | 1.413<br>375.2<br>G | $^1$H NMR (400 MHz, CD$_3$OD) δ 9.30 (s, 1H), 8.54 (s, 1H), 8.43 (d, J = 5.2 Hz, 1H), 8.33 (s, 1H), 7.40 (d, J = 5.2 Hz, 1H), 6.98 (s, 1H), 3.15-3.08 (m, 2H), 3.03-2.91 (m, 2H), 2.46 (s, 3H), 2.16-2.13 (m, 1H), 2.03-1.98 (m, 2H), 1.48-1.45 (m, 1H), 1.26-1.24 (m, 1H). |
| 127 | 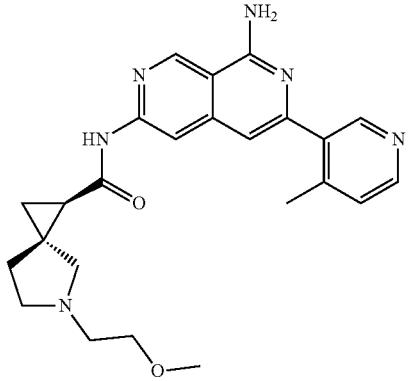 [SMILES: COCCN1CC[C@]2(C[C@H]2C(=O)Nc2cc3cc(-c4cnccc4C)nc(N)c3cn2)C1]<br>(±)-trans-N-(8-amino-6-(4-methylpyridin-3-yl)-2,7-naphthyridin-3-yl)-5-(2-methoxyethyl)-5-azaspiro[2.4]heptane-1-carboxamide | 1.723<br>433.2<br>I-1 | $^1$H NMR (400 MHz, CD$_3$OD) δ 9.29 (s, 1H), 8.54 (s, 1H), 8.43 (d, J = 5.2 Hz, 1H), 8.32 (s, 1H), 7.40 (d, J = 5.2 Hz, 1H), 6.98 (s, 1H), 3.53-3.50 (m, 2H), 3.33 (s, 3H), 2.87-2.69 (m, 6H), 2.45 (s, 3H), 2.13-1.92 (m, 3H), 1.43-1.41 (m, 1H), 1.22-1.19 (m, 1H). |
| 128 | 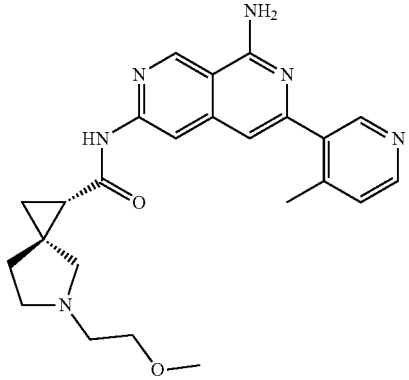 [SMILES: COCCN1CC[C@]2(C[C@@H]2C(=O)Nc2cc3cc(-c4cnccc4C)nc(N)c3cn2)C1]<br>(±)-cis-N-(8-amino-6-(4-methylpyridin-3-yl)-2,7-naphthyridin-3-yl)-5-(2-methoxyethyl)-5-azaspiro[2.4]heptane-1-carboxamide | 1.763<br>433.3<br>I-1 | $^1$H NMR (400 MHz, CD$_3$OD) δ 9.29 (s, 1H), 8.54 (s, 1H), 8.43 (d, J = 5.2 Hz, 1H), 8.32 (s, 1H), 7.39 (d, J = 5.2 Hz, 1H), 6.97 (s, 1H), 3.56-3.53 (m, 2H), 3.36 (s, 3H), 2.91-2.60 (m, 6H), 2.45 (s, 3H), 2.12-1.96 (m, 3H), 1.40-1.37 (m, 1H), 1.21-1.18 (m, 1H). |

TABLE A-1-continued

| Compd No. | Structure/Name | LCMS R$_T$(min) M + H$^+$, Method | $^1$H NMR (ppm) |
|---|---|---|---|
| 129 | 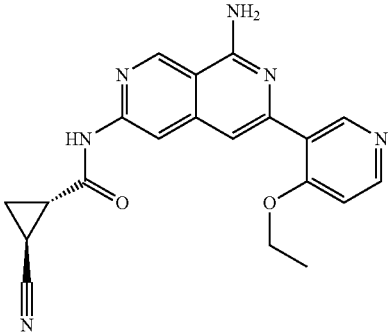 [SMILES: CCOc1ccncc1-c1cc2cc(NC(=O)[C@H]3C[C@@H]3C#N)ncc2c(N)n1]  (±)-trans-N-[8-amino-6-(4-ethoxy-3-pyridyl)-2,7-naphthyridin-3-yl]-2-cyano-cyclopropanecarboxamide | 1.639 375.1 C | $^1$H NMR (400 MHz, DMSO-d$_6$): δ11.28 (brs, 1H), 9.37 (s, 1H), 8.95 (s, 1H), 8.42 (d, J = 5.6 Hz, 1H), 8.15 (s, 1H), 7.42 (s, 1H), 7.31 (brs, 2H), 7.14 (d, J = 5.6 Hz, 1H), 4.23 (q, J = 7.2 Hz, 2H), 2.78-2.74 (m, 1H), 2.19-2.15 (m, 1H), 1.64-1.59 (m, 1H), 1.47-1.42 (m, 1H), 1.39 (t, J = 7.2 Hz, 3H). |
| 130 | 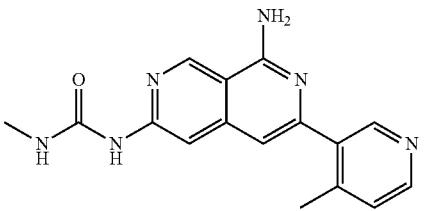 [SMILES: CNC(=O)Nc1cc2cc(-c3cnccc3C)nc(N)c2cn1]  1-[8-amino-6-(4-methyl-3-pyridyl)-2,7-naphthyridin-3-yl]-3-methyl-urea | 1.35 309.2 E | $^1$H NMR (400 MHz, DMSO-d$_6$) δ 9.26 (s, 2H), 8.56 (s, 1H), 8.43 (d, J = 4.8 Hz, 1H), 7.76 (s, 1H), 7.30 (d, J = 4.8 Hz, 1H), 7.26 (s, 2H), 7.13 (d, J = 4.4 Hz, 1H), 6.88 (s, 1H), 2.72 (d, J = 4.8 Hz, 3H), 2.41 (s, 3H). |
| 131 | 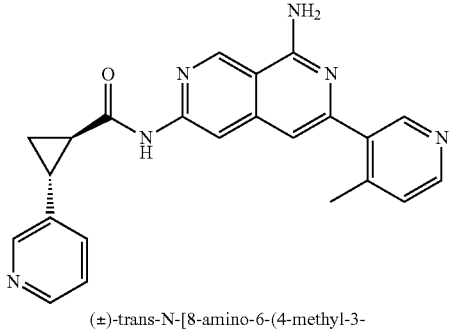  (±)-trans-N-[8-amino-6-(4-methyl-3-pyridyl)-2,7-naphthyridin-3-yl]-2-(3-pyridyl)cyclopropanecarboxamide | 1.27 397.2 B | $^1$H NMR (400 MHz, DMSO-d$_6$) δ 11.00 (s, 1H), 9.37 (s, 1H), 8.57 (s, 1H), 8.51 (d, J = 2.0 Hz, 1H), 8.45-8.42 (m, 2H), 8.28 (s, 1H), 7.57 (d, J = 8.0 Hz, 1H), 7.35-7.31 (m, 4H), 6.99 (s, 1H), 2.48-2.46 (m, 1H), 2.46-2.45 (m, 1H), 2.42 (s, 3H), 1.59-1.54 (m, 1H), 1.50-1.46 (m, 1H). |
| 132 | 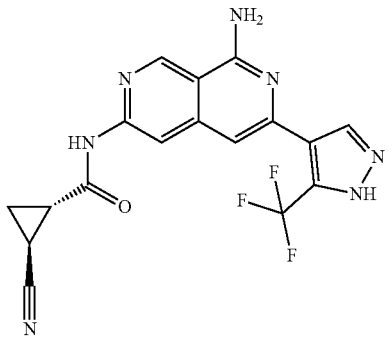 [SMILES: N#C[C@H]1C[C@@H]1C(=O)Nc1cc2cc(-c3cn[nH]c3C(F)(F)F)nc(N)c2cn1]  (±)-trans-N-[8-amino-6-[5-(trifluoromethyl)-1H-pyrazol-4-yl]-2,7-naphthyridin-3-yl]-2-cyano-cyclopropanecarboxamide | 1.76 388.0 E | $^1$H NMR (400 MHz, CD$_3$OD) δ 9.11 (s, 1H), 8.09 (s, 2H), 6.93 (s, 1H), 2.55-2.50 (m, 1H), 2.06-2.01 (m, 1H), 1.52-1.42 (m, 2H). |

TABLE A-1-continued

| Compd No. | Structure/Name | LCMS R$_T$(min) M + H$^+$, Method | $^1$H NMR (ppm) |
|---|---|---|---|
| 133 | 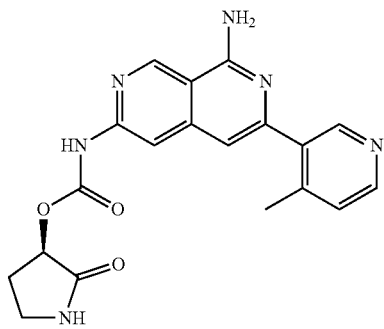 [SMILES: Cc1ccncc1-c1cc2cc(NC(=O)O[C@@H]3CCNC3=O)ncc2c(N)n1]<br>[(3R)-2-oxopyrrolidin-3-yl] N-[8-amino-6-(4-methyl-3-pyridyl)-2,7-naphthyridin-3-yl]carbamate | 1.45<br>379.2<br>F | $^1$H NMR (400 MHz, DMSO-d$_6$) δ 10.50 (s, 1H), 9.33 (s, 1H), 8.57 (s, 1H), 8.44 (d, J = 4.8 Hz, 1H), 8.09 (s, 1H), 7.97 (s, 1H), 7.32-7.27 (m, 3H), 6.99(s, 1H), 5.24 (t, J = 4.4 Hz, 1H), 3.29-3.24 (m, 2H), 2.42 (s, 3H), 2.06-1.88 (m, 2H). |
| 134 | 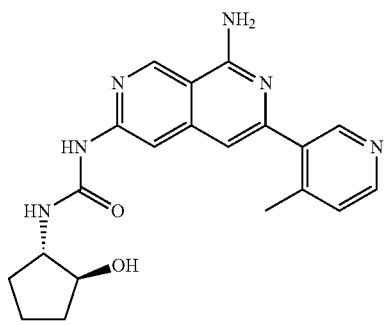 [SMILES: Cc1ccncc1-c1cc2cc(NC(=O)N[C@H]3CCC[C@@H]3O)ncc2c(N)n1]<br>1-[8-amino-6-(4-methyl-3-pyridyl)-2,7-naphthyridin-3-yl]-3-[(1S,2S)-2-hydroxycyclopentyl]urea<br>(Absolute stereochemistry arbitrarily assigned) | 1.64<br>379.1<br>E | $^1$H NMR (400 MHz, DMSO-d$_6$) δ 9.26 (s, 1H), 9.09 (s, 1H), 8.56 (s, 1H), 8.43 (d, J = 4.8 Hz, 1H), 8.20 (s, 1H), 7.79 (s, 1H), 7.30 (d, J = 4.8 Hz, 1H), 7.24 (s, 3H), 3.87-3.83 (m, 1H), 3.78-3.72 (m, 1H), 2.41 (s, 3H), 2.05-2.00 (m, 1H), 1.85-1.78 (m, 1H), 1.71-1.60 (m, 2H), 1.53-1.46 (m, 1H), 1.42-1.35 (m, 1H). |
| 135 | 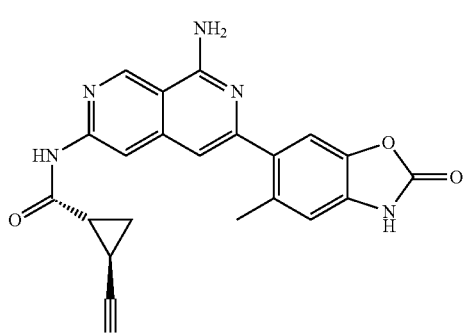<br>(±)-trans-N-(8-amino-6-(5-methyl-2-oxo-2,3-dihydrobenzo[d]oxazol-6-yl)-2,7-naphthyridin-3-yl)-2-cyanocyclopropanecarboxamide | 1.419<br>401.1<br>B | $^1$H NMR (400 MHz, DMSO-d$_6$) δ 11.24 (s, 1H), 9.37 (s, 1H), 8.17 (s, 1H), 8.15 (s, 1H), 7.31 (s, 1H), 7.27 (s, 2H), 6.98 (s, 1H), 6.88 (s, 1H), 2.78-2.73 (m, 1H), 2.37 (s, 3H), 2.17-2.12 (m, 1H), 1.63-1.58 (m, 1H), 1.45-1.41 (m, 1H). |

TABLE A-1-continued

| Compd No. | Structure/Name | LCMS R_T(min) M + H+, Method | ¹H NMR (ppm) |
|---|---|---|---|
| 136 | 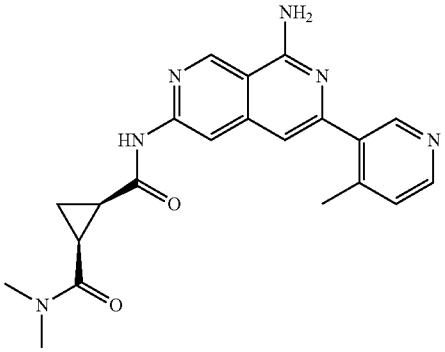 [SMILES: Cc1ccncc1-c1cc2cc(NC(=O)[C@@H]3C[C@@H]3C(=O)N(C)C)ncc2c(N)n1]<br>(±)-cis-N1-{8-amino-6-(4-methyl)pyridin-3-yl)-2,7-naphthyridin-3-yl)-N2,N2-dimethylcyclopropane-1,2-dicarboxamide | 1.402<br>391.2<br>C | ¹H NMR (400 MHz, CD₃OD) δ 9.26 (s, 1H), 8.53 (s, 1H), 8.43 (d, J = 4.8 Hz, 1H), 8.28 (s, 1H), 7.40 (d, J = 4.8 Hz, 1H), 6.98 (s, 1H), 3.18(s, 3H), 2.93 (s, 3H), 2.453 (s, 3H), 2.432-2.411(m, 1H), 2.357-2.296(m, 1H), 1.738-1.694(m, 1H), 1.383-1.330(m, 1H). |
| 137 | 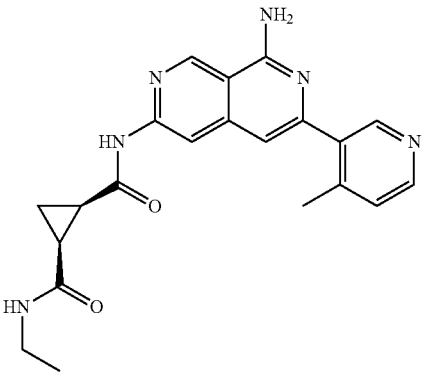 [SMILES: CCNC(=O)[C@H]1C[C@H]1C(=O)Nc1cc2cc(-c3cnccc3C)nc(N)c2cn1]<br>(±)-cis-N1-(8-amino-6-(4-methylpyridin-3-yl)-2,7-naphthyridin-3-yl)-N2-ethylcyclopropane-1,2-dicarboxamide | 1.428<br>391.1<br>C | ¹H NMR (400 MHz, CD₃OD) δ 9.28 (s, 1H), 8.54 (s, 1H), 8.43 (d, J = 5.2 Hz, 1H), 8.31(s, 1H), 7.40 (d, J = 5.2 Hz, 1H), 6.98(s, 1H), 3.24-3.18 (m, 2H), 2.45 (s, 3H), 2.30-2.26 (m, 1H), 2.14-2.12 (m, 1H), 1.72-1.69(m, 1H), 1.34-1.30 (m, 1H), 1.11(t, J = 7.2 Hz, 3H). |
| 138 | 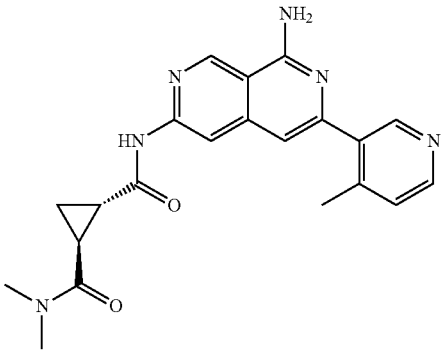 [SMILES: Cc1ccncc1-c1cc2cc(NC(=O)[C@H]3C[C@@H]3C(=O)N(C)C)ncc2c(N)n1]<br>(±)-trans-N1-(8-amino-6-(4-methylpyridin-3-yl)-2,7-naphthyridin-3-yl)-N2,N2-dimethylcyclopropane-1,2-dicarboxamide | 1.522<br>391.2<br>C | ¹H NMR (400 MHz, DMSO-d₆) δ 11.05 (s, 1H), 9.37 (s, 1H), 8.56 (s, 1H), 8.44 (d, J = 4.8 Hz, 1H), 8.25 (s, 1H), 7.32 (d, J = 4.8 Hz, 1H), 7.30 (s, 2H), 6.97 (s, 1H), 3.12 (s, 3H), 2.86 (s, 3H), 2.48-2.45 (m, 1H), 2.41 (s, 3H), 2.39-2.35 (m, 1H), 1.28-1.25(m, 1H). |

TABLE A-1-continued

| Compd No. | Structure/Name | LCMS R$_T$(min) M + H$^+$, Method | $^1$H NMR (ppm) |
|---|---|---|---|
| 139 | (±)-trans-N-(8-amino-6-(4-methylpyridin-3-yl)-2,7-naphthyridin-3-yl)-2-methylcyclopropanecarboxamide | 1.39 334.2 B | $^1$H NMR (400 MHz, DMSO-d$_6$) δ 10.87 (s, 1H), 9.36 (s, 1H), 8.56 (s, 1H), 8.43 (d, J = 4.8 Hz, 1H), 8.22 (s, 1H), 7.31-7.30 (m, 3H), 6.95 (s, 1H), 2.40 (s, 3H), 1.85-1.81 (m, 1H), 1.29-1.24 (m, 1H), 1.10 (d, J = 6.0 Hz, 3H), 1.07-1.02 (m, 1H), 0.71-0.66 (m, 1H). |
| 140 | (±)-trans-N-(8-amino-6-(4-methylpyridin-3-yl)-2,7-naphthyridin-3-yl)-2-(trifluoromethyl)cyclopropanecarboxamide | 1.46 388.2 B | $^1$H NMR (400 MHz, DMSO-d$_6$) δ 11.20 (s, 1H), 9.39 (s, 1H), 8.56 (s, 1H), 8.43 (d, J = 4.8 Hz, 1H), 8.23 (s, 1H), 7.35 (s, 2H), 7.31 (d, J = 4.8 Hz, 1H), 6.99 (s, 1H), 2.32-2.59 (m, 1H), 2.41 (s, 3H), 2.33-2.30 (m, 1H), 1.35-1.31 (m, 2H). |
| 141 | (±)-cis-N-(8-amino-6-(4-methylpyridin-3-yl)-2,7-naphthyridin-3-yl)-2-methylcyclopropanecarboxamide | 1.72 334.1 C | 1.72, [M + H]$^+$ = 334.1, method = C; $^1$H NMR (CD$_3$OD, 400 MHz): δ 9.29 (s, 1H), 8.54 (s, 1H), 8.43 (d, J = 5.2 Hz, 1H), 8.32 (s, 1H), 7.41 (d, J = 5.2 Hz, 1H), 7.00 (s, 1H), 2.46 (s, 3H), 2.03-1.98 (m, 1H), 1.45-1.38 (m, 1H), 1.22 (d, J = 6.0 Hz, 3H), 1.10-1.05 (m, 1H), 1.02-0.98 (m, 1H). |
| 142 | (±)-trans-N-(8-amino-6-(3,5-dimethyl-2-oxo-2,3-dihydrobenzo[d]oxazol-6-yl)-2,7-naphthyridin-3-yl)-2-cyanocyclopropanecarboxamide | 1.76 415.1 C | $^1$HNMR (400 MHz, DMSO-d$_6$): δ 11.24 (s, 1H), 9.37 (s, 1H), 8.18 (s, 1H), 7.36 (s, 1H), 7.29 (s, 2H), 7.17 (s, 1H), 6.89 (s, 1H), 3.36 (s, 3H), 2.79-2.73 (m, 1H), 2.42 (s, 3H), 2.18-2.13 (m, 1H), 1.63-1.59 (m, 1H), 1.46-1.41 (m, 1H). |

TABLE A-1-continued

| Compd No. | Structure/Name | LCMS R$_T$(min) M + H$^+$, Method | $^1$H NMR (ppm) |
|---|---|---|---|
| 143 | 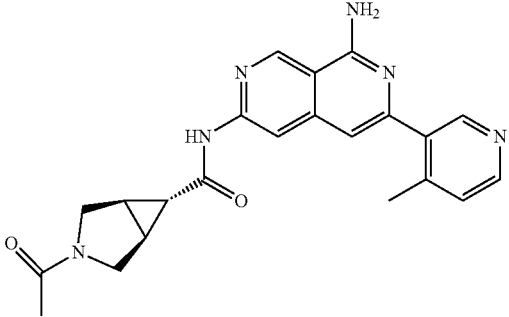 [SMILES: CC(=O)N1C[C@@H]2[C@H](C1)[C@H]2C(=O)Nc1cc2cc(-c3cnccc3C)nc(N)c2cn1]<br>exo-3-acetyl-N-[8-amino-6-(4-methyl-3-pyridyl)-2,7-naphthyridin-3-yl]-3-azabicyclo[3.1.0]hexane-6-carboxamide | 1.436<br>403.1<br>H | 1H NMR (400 MHz, DMSO-d$_6$) δ 10.82 (s, 1H), 9.36 (s, 1H), 8.56 (s, 1H), 8.43 (d, J = 5.2 Hz, 1H), 8.22 (s, 1H), 7.32-7.31 (m, 3H), 6.95 (s, 1H), 3.70-3.66 (m, 2H), 3.38-3.33 (m, 2H), 2.41 (s, 3H), 2.14-2.12 (m, 1H), 2.07-2.05 (m, 1H), 1.95-1.93 (m, 4H). |
| 144 | 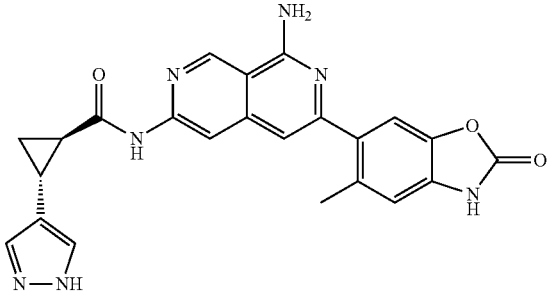 [SMILES: Cc1cc2[nH]c(=O)oc2cc1-c1cc2cc(NC(=O)[C@@H]3C[C@H]3c3cn[nH]c3)ncc2c(N)n1]<br>(±)-trans-N-[8-amino-6-(5-methyl-2-oxo-3H-1,3-benzoxazol-6-yl)-2,7-naphthyridin-3-yl]-2-(1H-pyrazol-4-yl)cyclopropanecarboxamide | 1.504<br>442.1<br>E | $^1$H NMR (400 MHz, DMSO-d$_6$) δ 9.27 (s, 1H), 8.30 (s, 1H), 7.27 (s, 1H), 7.03 (s, 1H), 6.91 (s, 1H), 2.46-2.41 (m, 1H), 2.38 (s, 3H), 2.15-2.13 (m, 1H), 1.63-1.56 (m, 1H), 1.31-1.28 (m, 1H). |
| 145 | 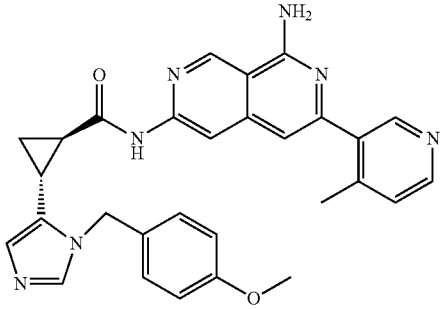 [SMILES: COc1ccc(Cn2cncc2[C@@H]2C[C@H]2C(=O)Nc2cc3cc(-c4cnccc4C)nc(N)c3cn2)cc1]<br>(±)-trans-N-[8-amino-6-(4-methyl-3-pyridyl)-2,7-naphthyridin-3-yl]-2-[3-[(4-methoxyphenyl)methyl]imidazol-4-yl]cyclopropanecarboxamide | 1.40<br>506.1<br>B | $^1$H NMR (400 MHz, DMSO-d$_6$) δ 9.28 (s, 1H), 8.54 (s, 1H), 8.43 (d, J = 5.2 Hz, 1H), 8.32 (s, 1H), 7.63 (s, 1H), 7.40 (d, J = 5.2 Hz, 1H), 7.23 (d, J = 8.5 Hz, 2H), 7.01-6.89 (m, 4H), 5.09 (s, 2H), 3.80 (s, 3H), 2.54-2.39 (m, 4H), 2.26-2.15 (m, 1H), 1.57-1.52 (m, 1H), 1.42-1.38 (m, 1H). |

TABLE A-1-continued

| Compd No. | Structure/Name | LCMS $R_T$(min) M + H+, Method | $^1$H NMR (ppm) |
|---|---|---|---|
| 146 | 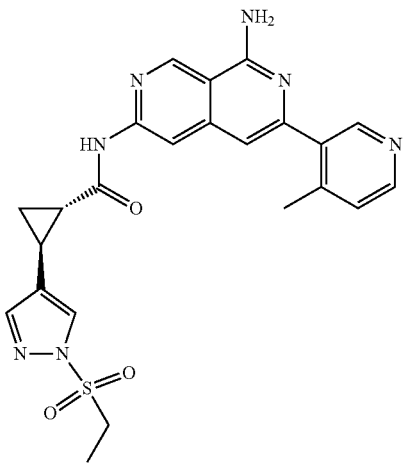 [SMILES: CCS(=O)(=O)n1cc([C@H]2C[C@@H]2C(=O)Nc2cc3cc(-c4cnccc4C)nc(N)c3cn2)cn1]<br>(±)-trans-N-[8-amino-6-(4-methyl-3-pyridyl)-2,7-naphthyridin-3-yl]-2-(1-ethylsulfonylpyrazol-4-yl)cyclopropanecarboxamide | 1.560<br>478.1<br>B | $^1$H NMR (400 MHz, CD$_3$OD) δ 9.30 (s, 1H), 8.55 (s, 1H), 8.44 (d, J = 5.2 Hz, 1H), 8.34 (s, 1H), 8.12 (s, 1H), 7.85 (s, 1H), 7.41 (d, J = 5.2 Hz, 1H), 7.00 (s, 1H), 3.56 (q, J = 7.6 Hz, 2H), 2.48-2.47 (m, 4H), 2.28-2.13 (m, 1H), 1.67-1.62 (m, 1H), 1.39-1.34 (m, 1H), 1.21 (t, J = 7.6 Hz, 3H). |
| 147 | 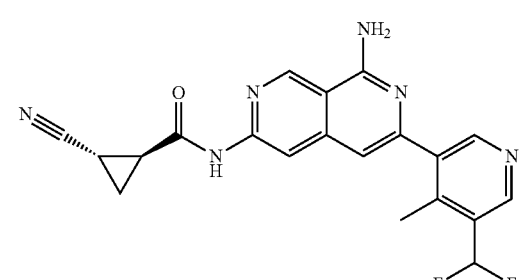<br>(±)-trans-N-(8-amino-6-(5-(difluoromethyl)-4-methylpyridin-3-yl)-2,7-naphthyridin-3-yl)-2-cyanocyclopropanecarboxamide | 1.591<br>394.7<br>G | $^1$H NMR (400 MHz, DMSO-d$_6$) δ 11.29 (s, 1H), 9.42 (s, 1H), 8.69 (s, 1H), 8.68 (s, 1H), 8.22 (s, 1H), 7.21-7.48 (m, 3H), 7.00 (s, 1H), 2.74-2.79 (m, 1H), 2.40 (s, 3H), 2.13-2.18 (m, 1H), 1.59-1.64 (m, 1H), 1.41-1.46 (m, 1H). |
| 148 | 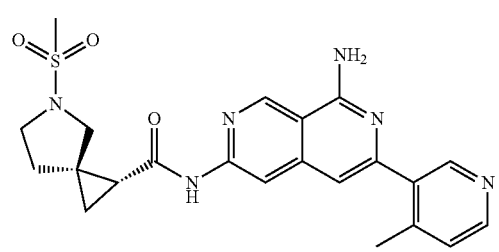 [SMILES: Cc1ccncc1-c1cc2cc(NC(=O)[C@@H]3C[C@]34CCN(S(C)(=O)=O)C4)ncc2c(N)n1]<br>trans-N-8-amino-6-(4-methylpyridin-3-yl)-2,7-naphthyridin-3-yl)-5-(methylsulfonyl)-5-azaspiro[2.4]heptane-1-carboxamide | 1.494<br>452.7<br>G | $^1$H NMR (400 MHz, DMSO-d$_6$) δ 11.00 (s, 1H), 9.37 (s, 1H), 8.56 (s, 1H), 8.43 (d, J = 4.8 Hz, 1H), 8.27 (s, 1H), 7.30-7.32 (m, 3H), 6.99 (s, 1H), 3.33-3.39 (m, 4H), 2.84 (s, 3H), 2.41 (s, 3H), 2.26-2.30 (m, 1H), 1.88-2.01 (m, 2H), 1.22-1.29 (m, 2H). |

TABLE A-1-continued

| Compd No. | Structure/Name | LCMS R_T(min) M + H+, Method | ¹H NMR (ppm) |
|---|---|---|---|
| 149 | 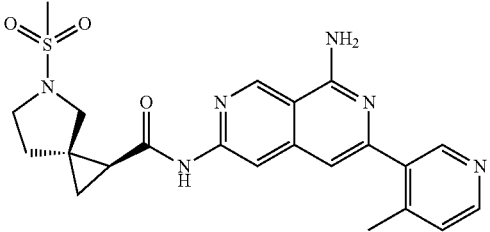 [SMILES: Cc1ccncc1-c1cc2cc(NC(=O)[C@H]3C[C@]34CCN(S(C)(=O)=O)C4)ncc2c(N)n1]<br>cis-N-(8-amino-6-(4-methylpyridin-3-yl)-2,7-naphthyridin-3-yl)-5-(methylsulfonyl)-5-azaspiro[2.4]heptane-1-carboxamide | 1.504<br>452.7<br>G | ¹HNMR (400 MHz, CD₃OD) δ 9.30 (s, 1H), 8.54 (s, 1H), 8.43 (d, J = 5.2 Hz, 1H), 8.34 (s, 1H), 7.40 (d, J = 4.8 Hz, 1H), 6.99 (s, 1H), 3.35-3.54 (m, 4H), 2.94 (s, 3H), 2.46 (s, 3H), 2.12-2.23 (m, 3H), 1.45-1.48 (m, 1H), 1.28-1.32 (m, 1H). |
| 150 | 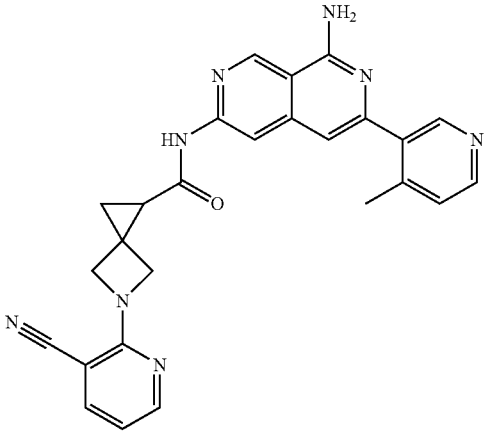 [SMILES: Cc1ccncc1-c1cc2cc(NC(=O)C3CC34CN(c3ncccc3C#N)C4)ncc2c(N)n1]<br>(±)-N-(8-amino-6-(4-methylpyridin-3-yl)-2,7-naphthyridin-3-yl)-5-(3-cyanopyridin-2-yl)-5-azaspiro[2.3]hexane-1-carboxamide | 1.641<br>463.2<br>G | ¹H NMR (400 MHz, DMSO-d₆) δ 11.05 (s, 1H), 9.38 (s, 1H), 8.57 (s, 1H), 8.43 (d, J = 4.8 Hz, 1H), 8.32 (dd, J = 2.0, 4.8 Hz, 1H), 8.28 (s, 1H), 7.96 (dd, J = 1.6, 7.6 Hz, 1H), 7.32-7.31 (m, 3H), 7.00 (s, 1H), 6.78 (dd, J = 4.8, 7.6 Hz, 1H), 4.39-4.30 (m, 4H), 2.41-2.36 (m, 4H), 1.39-1.27 (m, 2H). |
| 151 | 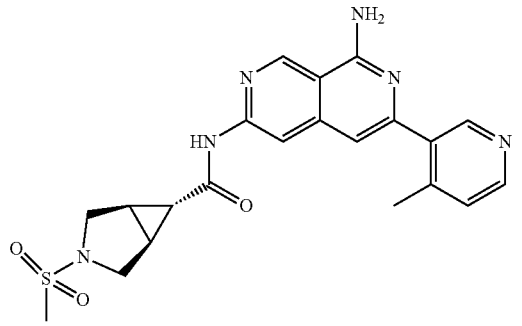 [SMILES: Cc1ccncc1-c1cc2cc(NC(=O)[C@H]3[C@@H]4CN(S(C)(=O)=O)C[C@@H]43)ncc2c(N)n1]<br>exo-N-[8-amino-6-(4-methyl-3-pyridyl)-2,7-naphthyridin-3-yl]-3-methylsulfonyl-3-azabicyclo[3.1.0]hexane-6-carboxamide | 1.467<br>439.1<br>H | ¹H NMR (400 MHz, DMSO-d₆) δ 10.95 (s, 1H), 9.37 (s, 1H), 8.56 (s, 1H), 8.43 (d, J = 5.2 Hz, 1H), 8.22 (s, 1H), 7.32-7.30 (m, 3 H), 6.96 (s, 1H), 3.45-3.43 (m, 4 H), 2.95 (s, 3 H), 2.41 (s, 3 H), 2.19-2.17 (m, 1H), 2.11-2.09 (m, 2H). |

TABLE A-1-continued

| Compd No. | Structure/Name | LCMS R_T(min) M + H+, Method | $^1$H NMR (ppm) |
|---|---|---|---|
| 152 | 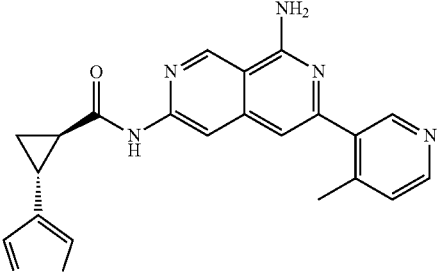<br>(±)-trans-N-[8-amino-6-(4-methyl-3-pyridyl)-2,7-naphthyridin-3-yl]-2-isothiazol-4-yl-cyclopropanecarboxamide | 1.67<br>403.1<br>C | $^1$H NMR (400 MHz, DMSO-d$_6$): δ 11.00 (brs, 1H), 9.37 (s, 1H), 8.77 (s, 1H), 8.57 (s, 1H), 8.53 (s, 1H), 8.44 (d, J = 4.8 Hz, 1H), 8.27 (s, 1H), 7.32 (brs, 2H), 7.31 (s, 1H), 6.98 (s, 1H), 2.60-2.55 (m, 1H), 2.41 (s, 3H), 2.44-2.40 (m, 1H), 1.56-1.51 (m, 1H), 1.47-1.44 (m, 1H). |
| 153 | 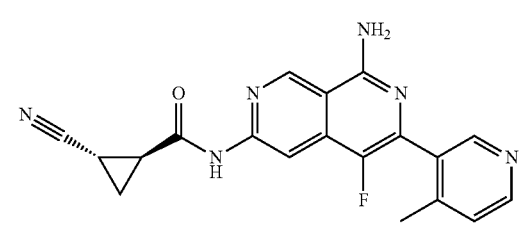 [SMILES: Cc1ccncc1-c1nc(N)c2cnc(NC(=O)[C@H]3C[C@@H]3C#N)cc2c1F]<br>(±)-trans-N-(8-amino-5-fluoro-6-(4-methylpyridin-3-yl)-2,7-naphthyridin-3-yl)-2-cyanocyclopropanecarboxamide | 1.546<br>363.2<br>G | $^1$H NMR (400 MHz, CD$_3$OD) δ 9.32 (s, 1H), 8.51 (s, 1H), 8.47 (s, 1H), 8.45 (d, J = 5.2 Hz, 1H), 7.41 (d, J = 5.2 Hz, 1H), 2.70-2.62 (m, 1H), 2.37 (s, 3H), 2.15-2.09 (m, 1H), 1.65-1.52 (m, 2H). |
| 154 | 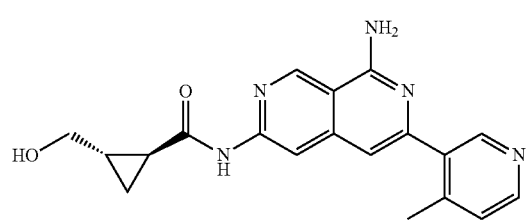 [SMILES: Cc1ccncc1-c1cc2cc(NC(=O)[C@H]3C[C@@H]3CO)ncc2c(N)n1]<br>(±)-trans-N-(8-amino-6-(4-methylpyridin-3-yl)-2,7-naphthyridin-3-yl)-2-(hydroxymethyl)cyclopropanecarboxamide | 1.285<br>350.2<br>B | Racemate: $^1$H NMR (400 MHz, CD$_3$OD) δ 9.27 (s, 1H), 8.52 (s, 1H), 8.41 (d, J = 5.2 Hz, 1H), 8.28 (s, 1H), 7.37 (d, J = 5.2 Hz, 1H), 6.94 (s, 1H), 3.64 (dd, J = 6.0, 11.6 Hz, 1H), 3.46 (dd, J = 6.4, 11.6 Hz, 1H), 2.44 (s, 3H), 1.90-1.84 (m, 1H), 1.76-1.68 (m, 1H), 1.29-1.21 (m, 1H), 0.97-0.91 (m, 1H). |
| 155 | 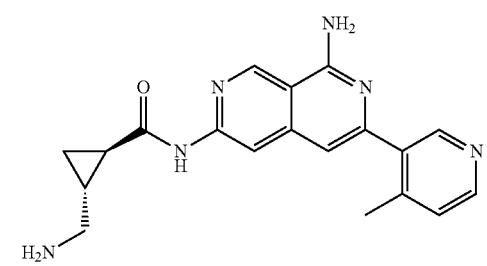 [SMILES: Cc1ccncc1-c1cc2cc(NC(=O)[C@@H]3C[C@H]3CN)ncc2c(N)n1]<br>(±)-trans-N-(8-amino-6-(4-methylpyridin-3-yl)-2,7-naphthyridin-3-yl)-2-(aminomethyl)cyclopropanecarboxamide | 1.373<br>349.2<br>G | $^1$H NMR (400 MHz, CD$_3$OD) δ: 9.18 (s, 1H), 8.42 (s, 1H), 8.31 (d, J = 5.2 Hz, 1H), 8.17 (s, 1H), 7.28 (d, J = 5.2 Hz, 1H), 6.86 (s, 1H), 2.66 (dd, J = 6.8, 13.2 Hz, 1H), 2.55 (dd, J = 7.2, 13.2 Hz, 1H), 2.34 (s, 3H), 1.77-1.71 (m, 1H), 1.56-1.51 (m, 1H), 1.20-1.15 (m, 1H), 0.86-0.79 (m, 1H). |
| 156 | 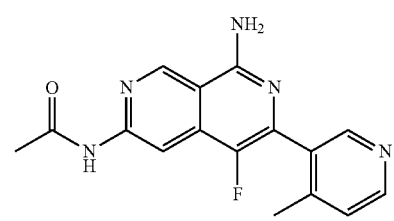 [SMILES: CC(=O)Nc1cc2c(F)c(-c3cnccc3C)nc(N)c2cn1]<br>N-(8-amino-5-fluoro-6-(4-methylpyridin-3-yl)-2,7-naphthyridin-3-yl)acetamide | 1.489<br>312.0<br>C | $^1$H NMR (400 MHz, DMSO-d$_6$) δ 10.88 (s, 1H), 9.42 (s, 1H), 8.52 (s, 1H), 8.49 (d, J = 4.8 Hz, 1H), 8.37 (s, 1H), 7.37 (d, J = 4.8 Hz, 1H), 7.30 (br, 2H), 2.28 (s, 3H), 2.17 (s, 3H). |

TABLE A-1-continued

| Compd No. | Structure/Name | LCMS R$_T$(min) M + H$^+$, Method | $^1$H NMR (ppm) |
|---|---|---|---|
| 157 | 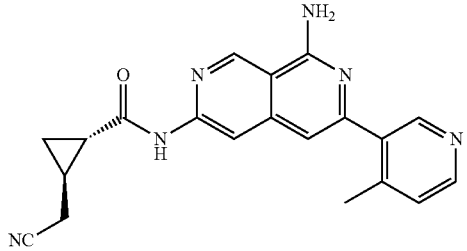 [SMILES: Cc1ccncc1-c1cc2cc(NC(=O)[C@H]3C[C@@H]3CC#N)ncc2c(N)n1]<br>(±)-trans-N-[8-amino-6-(4-methyl-3-pyridyl)-2,7-naphthyridin-3-yl]-2-(cyanomethyl)cyclopropanocarboxamide | 1.543<br>359.1<br>C | $^1$H NMR (400 MHz, DMSO-d$_6$) δ 9.45 (s, 1H), 8.58 (s, 1H), 8.44 (d, J = 5.2 Hz, 1H), 8.38 (s, 1H), 7.45 (s, 2H), 7.32 (d, J = 4.8 Hz, 1H), 7.08 (s, 1H), 5.04 (d, J = 3.6 Hz, 1H), 3.14-3.11 (m, 2H), 2.91-2.86 (m, 1H), 2.59-2.55 (m, 1H), 2.47-2.45 (m, 4H), 2.01-2.00 (m, 1H). |
| 158 | 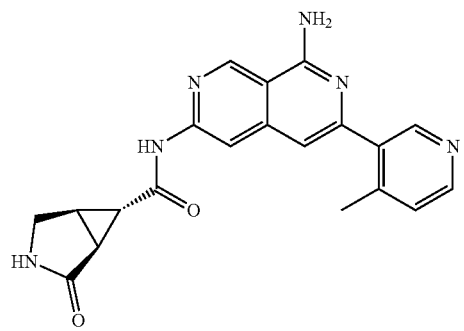 [SMILES: Cc1ccncc1-c1cc2cc(NC(=O)[C@H]3[C@@H]4CNC(=O)[C@@H]43)ncc2c(N)n1]<br>(±)-exo-N-[8-amino-6-(4-methyl-3-pyridyl)-2,7-naphthyridin-3-yl]-4-oxo-3-azabicyclo[3.1.0]hexane-6-carboxamide | 1.326<br>375.1<br>G | $^1$H NMR (400 MHz, DMSO-d$_6$) δ 11.08 (s, 1H), 9.38 (s, 1H), 8.56 (s, 1H), 8.43 (d, J = 4.8 Hz, 1H), 8.21 (s, 1H), 7.43 (s, 1H), 7.43-7.31 (m, 3H), 6.98 (s, 1H), 3.51-3.48 (m, 2H), 2.41-2.40 (m, 4H), 2.18-2.16 (m, 1H), 2.09-2.08 (m, 1H). |
| 159 | 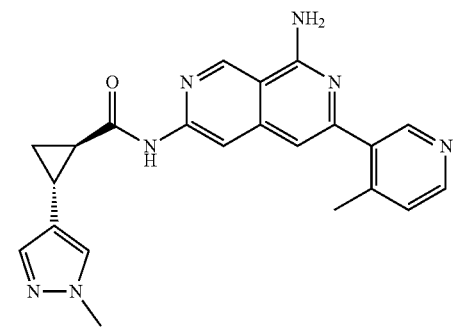 [SMILES: Cc1ccncc1-c1cc2cc(NC(=O)[C@@H]3C[C@H]3c3cnn(C)c3)ncc2c(N)n1]<br>(±)-trans-N-[8-amino-6-(4-methyl-3-pyridyl)-2,7-naphthyridin-3-yl]-2-(1-methylpyrazol-4-yl)cyclopropane carboxamide | 1.497<br>400.2<br>G | $^1$H NMR (400 MHz, DMSO-d$_6$) δ 10.95 (s, 1H), 9.37 (s, 1H), 8.57 (s, 1H), 8.44 (d, J = 5.2 Hz, 1H), 8.26 (s, 1H), 7.56 (s, 1H), 7.32 (s, 2H), 7.31 (d, J = 5.2 Hz, 1H), 7.30 (s, 1H), 6.97 (s, 1H), 3.77 (s, 3H), 2.41 (s, 3H), 2.23-2.19 (m, 2H), 1.40-1.38 (m, 1H), 1.23-1.18 (m, 1H). |
| 160 | 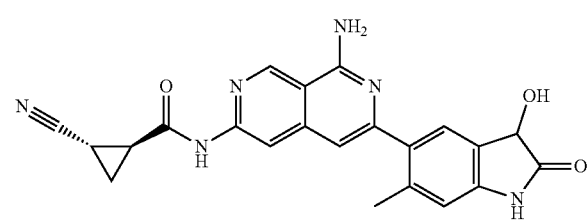 [SMILES: Cc1cc2c(cc1-c1cc3cc(NC(=O)[C@H]4C[C@@H]4C#N)ncc3c(N)n1)C(O)C(=O)N2]<br>trans-N-[8-amino-6-(3-hydroxy-6-methyl-2-oxo-indolin-5-yl)-2,7-naphthyridin-3-yl]-2-cyano-cyclopropane carboxamide | 1.437<br>415.1<br>C | $^1$H NMR (400 MHz, DMSO-d$_6$) δ 11.23 (s, 1H), 10.3 (s, 1H), 9.35 (s, 1H), 8.16 (s, 1H), 7.37 (s, 1H), 7.26 (s, 2H), 6.84 (s, 1H), 6.68 (s, 1H), 6.16 (d, J = 7.6 Hz, 1H), 4.84 (d, J = 7.6 Hz, 1H), 2.78-2.74 (m, 1H), 2.36 (s, 3H), 2.17-2.13 (m, 1H), 1.63-1.59 (m, 1H), 1.46-1.41 (m, 1H). |

TABLE A-1-continued

| Compd No. | Structure/Name | LCMS R_T(min) M + H⁺, Method | ¹H NMR (ppm) |
|---|---|---|---|
| 161 | 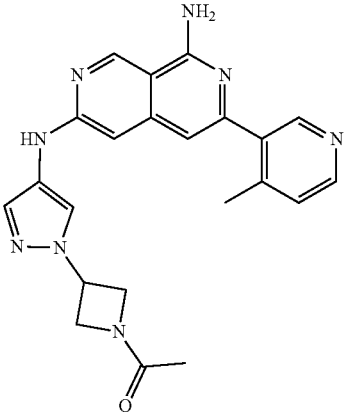 [SMILES: CC(=O)N1CC(n2cc(Nc3cc4cc(-c5cnccc5C)nc(N)c4cn3)cn2)C1]<br>1-[3-[4-[[8-amino-6-(4-methyl-3-pyridyl)-2,7-naphthyridin-3-yl]amino]pyrazol-1-yl]azetidin-1-yl]ethanone | 1.413<br>415.2<br>C | ¹H NMR (400 MHz, DMSO-d₆) δ 9.23 (s, 1H), 8.98 (s, 1H), 8.53 (s, 1H), 8.42 (d, J = 4.8 Hz, 1H), 8.09 (s, 1H), 7.63 (s, 1H), 7.29 (d, J = 5.2 Hz, 1H), 7.10 (s, 2H), 6.77 (s, 1H), 6.68 (s, 1H), 5.27-5.21 (m, 1H), 4.55 (t, J = 13.8 Hz, 1H), 4.41 (q, J = 4.8 Hz, 1H), 4.29 (t, J = 9.0 Hz, 1H), 4.14-4.09 (m, 1H), 2.40 (s, 3H), 1.83 (s, 3H). |
| 162 | 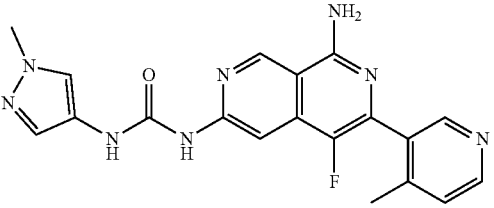 [SMILES: Cc1ccncc1-c1nc(N)c2cnc(NC(=O)Nc3cnn(C)c3)cc2c1F]<br>1-[8-amino-5-fluoro-6-(4-methyl-3-pyridyl)-2,7-naphthyridin-3-yl]-3-(1-methylpyrazol-4-yl)urea | 1.713<br>393.2<br>G | ¹H NMR (400 MHz, DMSO-d₆) δ 9.48 (s, 1H), 9.27 (s, 1H), 9.19 (s, 1H), 8.43 (s, 1H), 8.40 (d, J = 5.2 Hz, 1H), 7.97 (s, 1H), 7.77 (s, 1H), 7.34 (s, 1H), 7.29 (d, J = 4.8 Hz, 1H), 7.19 (s, 2H), 3.71 (s, 3H), 2.20 (s, 3H). |
| 163 | 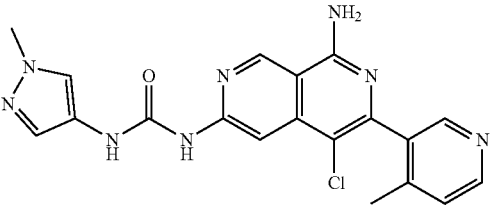<br>1-[8-amino-5-chloro-6-(4-methyl-3-pyridyl)-2,7-naphthyridin-3-yl]-3-(1-methylpyrazol-4-yl)urea | 1.765<br>409.2<br>G | ¹H NMR (400 MHz, DMSO-d₆) δ 9.57 (s, 1H), 9.38 (s, 1H), 9.26 (s, 1H), 8.49 (d, J = 4.8 Hz, 1H), 8.42 (s, 1H), 8.26 (s, 1H), 7.90 (s, 1H), 7.56 (s, 2H), 7.44 (s, 1H), 7.37 (d, J = 5.2 Hz, 1H), 3.81 (s, 3H), 2.19 (s, 3H). |
| 164 | 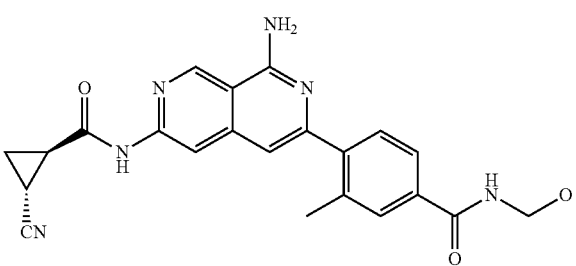 [SMILES: Cc1cc(C(=O)NCO)ccc1-c1cc2cc(NC(=O)[C@@H]3C[C@H]3C#N)ncc2c(N)n1]<br>(±)-trans-4-(1-amino-6-((trans)-2-cyanocyclopropanecarboxamido)-2,7-naphthyridin-3-yl)-3-methyl-N-(2,2,2-trifluoroethyl)benzamide) | 1.75<br>469.1<br>C | ¹H NMR (400 MHz, CD₃OD): 9.30 (s, 1H), 8.29 (s, 2H), 7.31(s, 1H), 7.79 (dd, J = 1.2, 8.0 Hz, 1H), 7.53 (d, J = 8.0 Hz, 1H), 4.16 (q, J = 9.2 Hz, 2H), 2.66-2.64 (m, 1H), 2.16-2.11(m, 1H), 1.62-1.55 (m, 2H). |

| Compd No. | Structure/Name | LCMS $R_T$(min) M + H+, Method | ¹H NMR (ppm) |
|---|---|---|---|
| 165 | 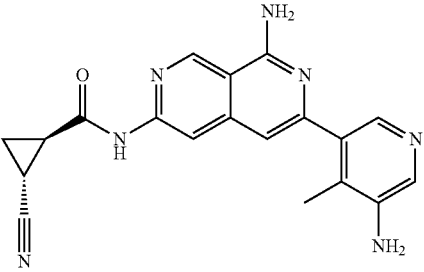 [SMILES: Cc1c(N)cncc1-c1cc2cc(NC(=O)[C@@H]3C[C@H]3C#N)ncc2c(N)n1]<br>(±)-trans-N-(8-amino-6-(5-amino-4-methylpyridin-3-yl)-2,7-naphthyridin-3-yl)-2-cyanocyclopropane carboxamide | 1.43<br>360.1<br>C | ¹H NMR (400 MHz, CD₃OD): 9.30 (s, 1H), 8.23 (s, 1H), 8.00 (s, 1H), 7.85 (s, 1H), 6.95 (s, 1H), 2.66-2.64 (m, 1H), 2.17 (s, 3H), 2.15-2.11 (m, 1H), 1.62-1.55 (m, 2H). |
| 166 | 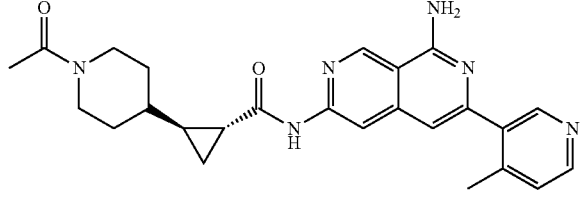 [SMILES: CC(=O)N1CCC([C@@H]2C[C@H]2C(=O)Nc2cc3cc(-c4cnccc4C)nc(N)c3cn2)CC1]<br>(±)-trans-2-(1-acetylpiperidin-4-yl)-N-(8-amino-6-(4-methylpyridin-3-yl)-2,7-naphthyridin-3-yl)cyclopropanecarboxamide | 1.49<br>445.3<br>C | ¹H NMR (400 MHz, CD₃OD): 9.29 (s, 1H), 8.54 (s, 1H), 8.44 (d, J = 4.8 Hz, 1H), 8.29 (s, 1H), 7.40 (d, J = 4.8 Hz, 1H), 6.97 (s, 1H), 6.26 (s, 1H), 4.54-4.52 (m, 1H), 3.96-3.94 (m, 1H), 3.09-3.07 (m, 1H), 2.63-2.61 (m, 1H), 2.45 (s, 3H), 2.12 (s, 3H), 1.90-1.86 (m, 3H), 1.31-1.14 (m, 5H), 1.01-0.99 (s, 1H). |
| 167 | 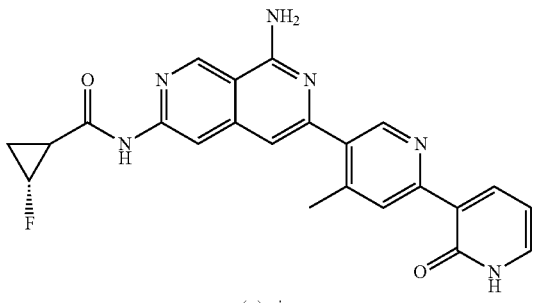<br>(±)-cis-N-(8-amino-6-(4-methyl-6-(2-oxo-1,2-dihydropyridin-3-yl)pyridin-3-yl)-2,7-naphthyridin-3-yl)-2-fluorocyclopropanecarboxamide | 1.43<br>431.2<br>C | ¹H NMR (400 MHz, DMSO-d₆): 11.99 (s, 1H), 10.02 (s, 1H), 9.39 (s, 1H), 8.65 (s, 1H), 8.56 (s, 1H), 8.51 (d, J = 5.2 Hz, 1H), 8.26 (s, 1H), 7.54 (d, J = 5.2 Hz, 1H), 7.34 (s, 1H), 7.03 (s, 2H), 6.43-6.40 (m, 0.5H), 5.05-4.87 (m, 0.5H), 2.40 (s, 3H), 2.28-2.45 (m, 1H), 1.71-1.64 (m, 1H), 1.23-1.18 (m, 1H) |
| 168 | 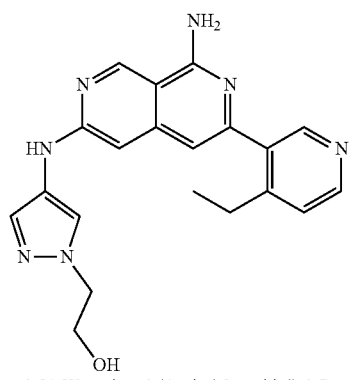<br>2-[4-[[8-amino-6-(4-ethyl-3-pyridyl)-2,7-naphthyridin-3-yl]amino]pyrazol-1-yl]ethanol | 1.45<br>376.1<br>C | ¹H NMR (400 MHz, DMSO-d₆): δ 9.22 (s, 1H), 8.85 (brs, 1H), 8.47-8.46 (m, 2H), 7.91 (s, 1H), 7.49 (s, 1H), 7.32 (d, J = 5.2 Hz, 1H), 7.06 (brs, 2H), 6.71 (s, 1H), 6.64 (s, 1H), 4.92-4.89 (m, 1H), 4.14-4.09 (m, 2H), 3.76-3.72 (m, 2H), 2.79 (q, J = 7.6 Hz, 2H), 1.10 (t, J = 7.6 Hz, 3H). |

TABLE A-1-continued

| Compd No. | Structure/Name | LCMS R_T(min) M + H+, Method | $^1$H NMR (ppm) |
|---|---|---|---|
| 169 | 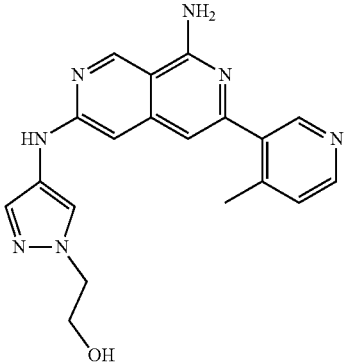 [SMILES: Cc1ccncc1-c1cc2cc(Nc3cnn(CCO)c3)ncc2c(N)n1]<br>2-[4-[[8-amino-6-(4-methyl-3-pyridyl)-2,7-naphthyridin-3-yl]amino]pyrazol-1-yl]ethanol | 1.39<br>362.1<br>C | $^1$H NMR (400 MHz, CD$_3$OD): δ 9.14 (s, 1H), 8.50 (s, 1H), 8.42 (d, J = 5.2 Hz, 1H), 7.93 (s, 1H), 7.60 (s, 1H), 7.39 (d, J = 5.2 Hz, 1H), 6.75 (s, 1H), 6.71 (s, 1H), 4.24 (t, J = 5.2 Hz, 2H), 3.93 (t, J = 5.2 Hz, 2H), 2.44 (s, 3H). |
| 170 | 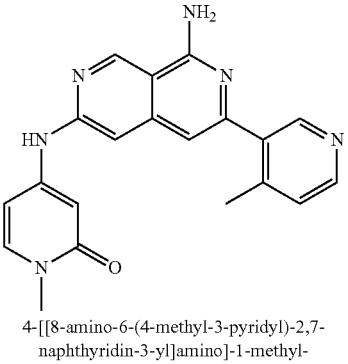<br>4-[[8-amino-6-(4-methyl-3-pyridyl)-2,7-naphthyridin-3-yl]amino]-1-methyl-pyridin-2-one | 1.36<br>359.2<br>G | $^1$H NMR (400 MHz, DMSO-d$_6$ + D$_2$O): δ 9.34 (s, 1H), 8.54 (s, 1H), 8.42 (d, J = 4.8 Hz, 1H), 7.52 (d, J = 7.6 Hz, 1H), 7.32 (d, J = 4.8 Hz, 1H), 7.05 (s, 1H), 6.91 (s, 1H), 6.89 (d, J = 2.0 Hz, 1H), 6.38 (dd, J = 2.0, 7.6 Hz, 1H), 3.34 (s, 3H), 2.40 (s, 3H). |
| 171 | 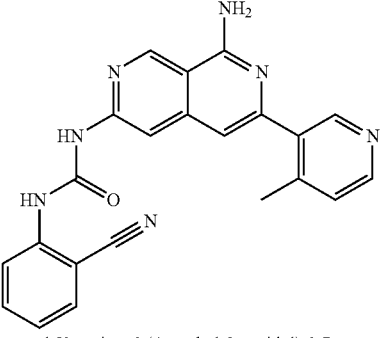<br>1-[8-amino-6-(4-methyl-3-pyridyl)-2,7-naphthyridin-3-yl]-3-(2-cyanophenyl)urea | 1.43<br>396.1<br>C | $^1$H NMR (400 MHz, CD$_3$OD): δ 9.60 (s, 1H), 8.60 (s, 1H), 8.45 (d, J = 4.0 Hz, 1H), 8.13 (s, 1H), 7.84 (s, 1H), 7.65-7.61 (m, 1H), 7.42 (d, J = 4.0 Hz, 1H), 7.28-7.19 (m, 3H), 2.50 (s, 3H). |

| Compd No. | Structure/Name | LCMS R$_T$(min) M + H$^+$, Method | $^1$H NMR (ppm) |
|---|---|---|---|
| 172 | 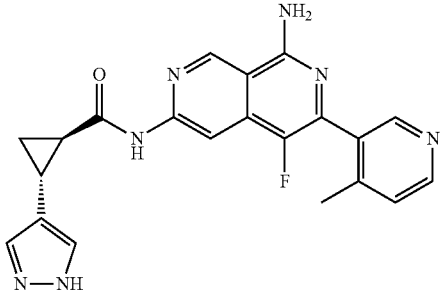 [SMILES: Cc1ccncc1-c1nc(N)c2cnc(NC(=O)[C@@H]3C[C@H]3c3cn[nH]c3)cc2c1F]<br>(±)-trans-N-(8-amino-5-fluoro-6-(4-methylpyridin-3-yl)-2,7-naphthyridin-3-yl)-2-(1H-pyrazo-4-yl)cyclopropanecarboxamide | 1.538<br>404.1<br>C | $^1$H NMR (400 MHz, DMSO-d$_6$): δ 12.64 (s, 1H), 11.19 (s, 1H), 9.43 (s, 1H), 8.52 (s, 1H), 8.49 (d, J = 5.2 Hz, 1H), 8.41 (s, 1H), 7.63 (s, 1H), 7.38 (s, 1H), 7.37 (d, J = 5.2 Hz, 1H), 7.32 (s, 2H), 2.28 (s, 3H), 2.25-2.21 (m, 2H), 1.45-1.40 (m, 1H), 1.29-1.24 (m, 1H). |
| 173 | 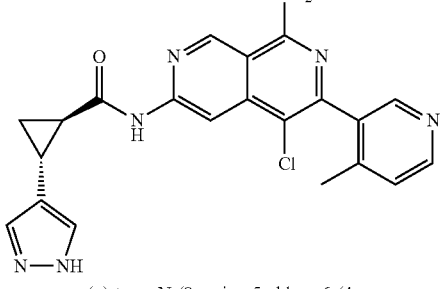<br>(±)-trans-N-(8-amino-5-chloro-6-(4-methylpyridin-3-yl)-2,7-naphthyridin-3-yl)-2-(1H-pyrazol-4-yl)cyclopropanecarboxamide | 1.486<br>420.1<br>G | 1H NMR (400 MHz, DMSO-d$_6$): δ 12.65 (s, 1H), 11.19 (s, 1H), 9.44 (s, 1H), 8.61 (s, 1H), 8.48 (d, J = 5.2 Hz, 1H), 8.41 (s, 1H), 7.60 (br, 4H), 7.36 (d, J = 5.2 Hz, 1H), 2.30-2.21 (m, 2H), 2.17 (s, 3H), 1.45-1.42 (m, 1H), 1.29-1.26 (m, 1H). |
| 174 | 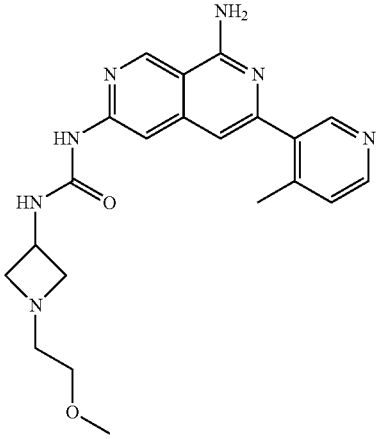 [SMILES: COCCN1CC(NC(=O)Nc2cc3cc(-c4cnccc4C)nc(N)c3cn2)C1]<br>1-(8-amino-6-(4-methylpyridin-3-yl)-2,7-naphthyridin-3-yl)-3-(1-(2-methoxyethyl)azetidin-3-yl)urea | 1.473<br>408.3<br>F | $^1$HNMR (400 MHz, CD3OD): δ 9.24 (s, 1H), 8.52 (s, 1H), 8.42 (d, J = 5.2 Hz, 1H), 7.54 (s, 1H), 7.39 (d, J = 5.2 Hz, 1H), 6.89 (s, 1H), 4.50 (t, J = 6.8 Hz, 1H), 3.79 (dt, J = 2.0, 6.8 Hz, 2H), 3.45 (t, J = 5.6 Hz, 2H), 3.35 (s, 3H), 3.15 (dt, J = 2.0, 6.8 Hz, 2H), 2.74 (t, J = 5.6 Hz, 2H), 2.45 (s, 3H). |

TABLE A-1-continued

| Compd No. | Structure/Name | LCMS R_T(min) M + H+, Method | 1H NMR (ppm) |
|---|---|---|---|
| 175 | 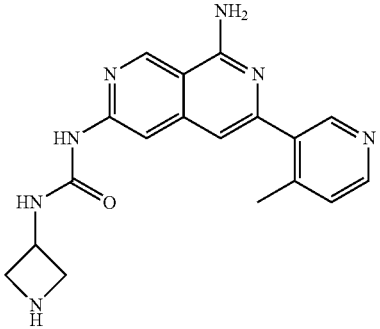 [SMILES: Cc1ccncc1-c1cc2cc(NC(=O)NC3CNC3)ncc2c(N)n1]<br>1-(8-amino-6-(4-methylpyridin-3-yl)-2,7-naphthyridin-3-yl)-3-(azetidin-3-yl)urea | 1.366<br>350.1<br>C | 1HNMR (400 MHz, DMSO-d$_6$) δ 9.26 (s, 1H), 9.17 (s, 1H), 8.56 (s, 1H), 8.42 (d, J = 5.2 Hz, 1H), 7.80 (s, 1H), 7.67(d, J = 5.2 Hz, 1H), 7.30 (d, J = 5.2 Hz, 1H), 7.26 (s, 2H), 6.88 (s, 1H), 4.5-4.47 (m, 1H), 3.63-3.59 (m, 2H), 3.40-3.32 (m, 2H), 2.41 (s, 3H). |
| 176 | 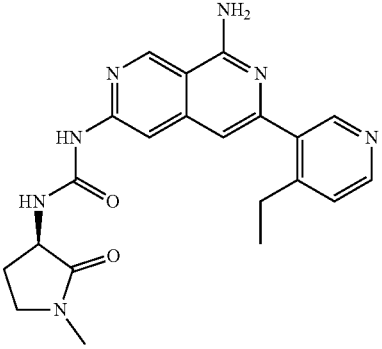 [SMILES: CCc1ccncc1-c1cc2cc(NC(=O)N[C@@H]3CCN(C)C3=O)ncc2c(N)n1]<br>(R)-1-(8-amino-6-(4-ethylpyridin-3-yl)-2,7-naphthyridin-3-yl)-3-(1-methyl-2-oxopyrrolidin-3-yl)urea | 1.50<br>406.2<br>C | 1HNMR (400 MHz, CD$_3$OD) δ 9.29 (s, 1H), 8.50 (s, 2H), 7.52 (s, 1H), 7.45 (d, J = 5.2 Hz, 1H), 6.89 (s, 1H), 4.49 (t, J = 9.2 Hz, 1H), 3.47 (dd, J = 4.0, 9.2 Hz, 2H), 2.93 (s, 3H), 2.83 (q, J = 7.6 Hz, 2H), 2.62-2.57 (m, 1H), 2.09-2.04 (m, 1H), 1.19 (t, J = 7.6 Hz, 3H). |
| 177 | 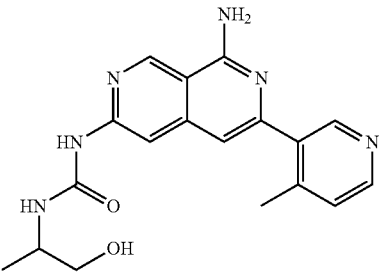 [SMILES: Cc1ccncc1-c1cc2cc(NC(=O)NC(C)CO)ncc2c(N)n1]<br>(±)-1-(8-amino-6-{4-methylpyridin-3-yl)-2,7-naphthyridin-3-yl)-3-(1-hydroxypropan-2-yl)urea | 1.432<br>353.1<br>C | 1HNMR (400 MHz, DMSO-d$_6$) δ 9.26 (s, 1H), 9.16 (s, 1H), 8.56 (s, 1H), 8.42 (d, J = 5.2 Hz, 1H), 7.78 (s, 1H), 7.29 (d, J = 5.2 Hz, 1H), 7.23-7.21 (m, 3H), 6.87 (s, 1H), 4.83 (t, J = 5.2 Hz, 1H), 3.79-3.70 (m, 1H), 3.43-3.32 (m, 2H), 2.41 (s, 3H), 1.11 (d, J = 6.8 Hz, 3H). |

TABLE A-1-continued

| Compd No. | Structure/Name | LCMS R$_T$(min) M + H$^+$, Method | $^1$H NMR (ppm) |
|---|---|---|---|
| 178 | 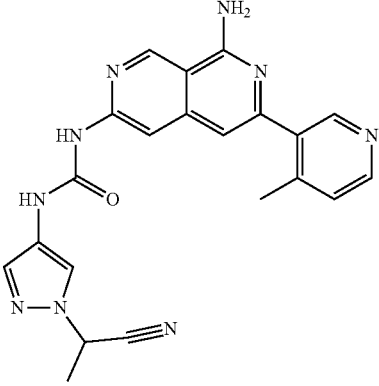 [SMILES: Cc1ccncc1-c1cc2cc(NC(=O)Nc3cnn(C(C)C#N)c3)ncc2c(N)n1]<br>(±)-1-[8-amino-6-(4-methyl-3-pyridyl)-2,7-naphthyridin-3-yl]-3-[1-(1-cyanoethyl)pyrazol-4-yl]urea | 1.532<br>414.2<br>H | $^1$H NMR (400 MHz, DMSO-d$_6$) δ 9.44 (s, 2H), 9.32 (s, 1H), 8.56 (s, 1H), 8.43 (d, J = 5.2 Hz, 1H), 8.07 (s, 1H), 7.87 (s, 1H), 7.65 (s, 1H), 7.32-7.31 (m, 2H), 6.94 (s, 1H), 5.82-5.83 (m, 1H), 2.42 (s, 3H), 1.78 (d, J = 6.8 Hz, 3H). |
| 179 | 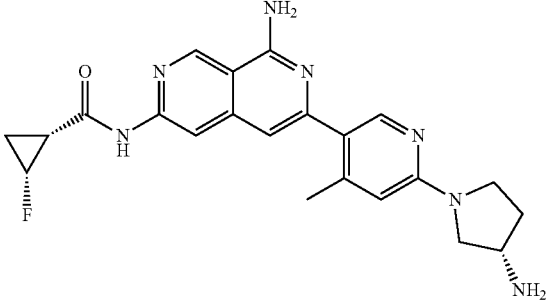 [SMILES: Cc1cc(N2CC[C@H](N)C2)ncc1-c1cc2cc(NC(=O)[C@H]3C[C@H]3F)ncc2c(N)n1]<br>(±)-cis-N-[8-amino-6-[6-[(3S)-3-aminopyrrolidin-1-yl]-4-methyl-3-pyridyl]-2,7-naphthyridin-3-yl]-2-fluoro-cyclopropanecarboxamide | 1.407<br>422.1<br>H | $^1$HNMR (400 MHz, CD$_3$OD) δ 9.24 (s, 1H), 8.26 (s, 1H), 8.07 (s, 1H), 6.88 (s, 1H), 6.41 (s, 1H), 4.98-4.95 (m, 1H), 4.81-4.79 (m, 1H), 3.72-3.63 (m, 3H), 3.54-3.48 (m, 1H), 3.27-3.25 (m, 1H), 2.38 (s, 3H), 2.30-2.25 (m, 1H), 2.18-2.15 (m, 1H), 1.96-1.80 (m, 2H), 1.26-1.20 (m, 1H). |
| 180 | 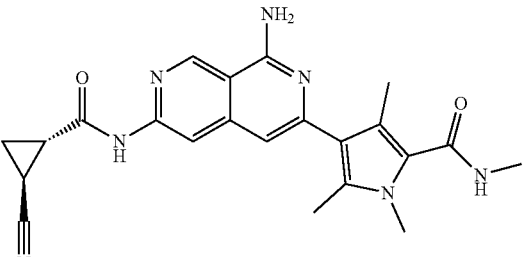<br>(±)-trans-4-[1-amino-6-[[trans-2-cyanocyclopropanecarbonyl]amino]-2,7-naphthyridin-3-yl]-N-1,3,5-tetramethyl-pyrrole-2-carboxamide | 1.47<br>418.1<br>H | $^1$H NMR (400 MHz, CD$_3$OD) δ 9.23 (s, 1H), 8.21 (s, 1H), 6.75 (s, 1H), 6.41 (s, 2H), 3.68 (s, 3H), 2.93 (s, 3H), 2.63-2.62 (m, 1H), 2.31 (s, 3 H), 2.22 (s, 3H), 2.16-2.11 (m, 1H), 1.62-1.54 (m, 2H). |

TABLE A-1-continued

| Compd No. | Structure/Name | LCMS R_T(min) M + H+, Method | ¹H NMR (ppm) |
|---|---|---|---|
| 181 | 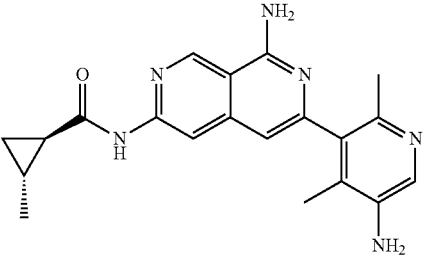<br>(±)-trans-N-[8-amino-6-(5-amino-2,4-dimethyl-3-pyridyl)-2,7-naphthyridin-3-yl]-2-methyl-cyclopropanecarboxamide | 1.56<br>363.2<br>F | ¹H NMR (400 MHz, CD₃OD) δ 9.30 (s, 1H), 8.25 (s, 1H), 7.92 (s, 1H), 6.78 (s, 1H), 2.19 (s, 3H), 1.97 (s, 3H), 1.72-1.67 (m, 1H), 1.48-1.45 (m, 1H), 1.25-1.22 (m, 1H), 1.19(d, J = 6.0 Hz, 3H), 0.79-0.75 (m, 1H). |
| 182 | 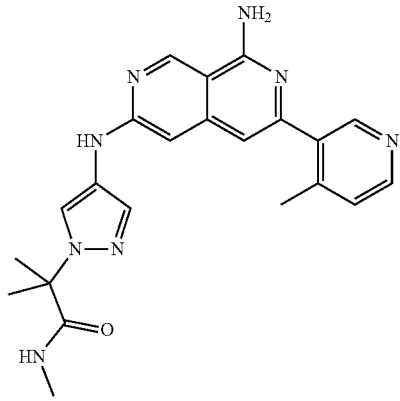 [SMILES: CNC(=O)C(C)(C)n1cc(Nc2cc3cc(-c4cnccc4C)nc(N)c3cn2)cn1]<br>2-[4-[[8-amino-6-(4-methyl-3-pyridyl)-2,7-naphthyridin-3-yl]amino]pyrazol-1-yl]-N,2-dimethyl-propanamide | 1.40<br>417.2<br>F | 417.2, R_T(min) = 1.40, Method = F; ¹H NMR (400 MHz, CD₃OD) δ 9.16 (s, 1H), 8.51 (s, 1H), 8.43 (d, J = 5.2 Hz, 1H), 8.05 (s, 1H), 7.68 (s, 1H), 7.39 (d, J = 5.2 Hz, 1H), 6.77 (s, 1H), 6.75 (s, 1H), 2.74 (s, 3H), 2.45 (s, 3H), 1.83 (s, 6H). |
| 183 | 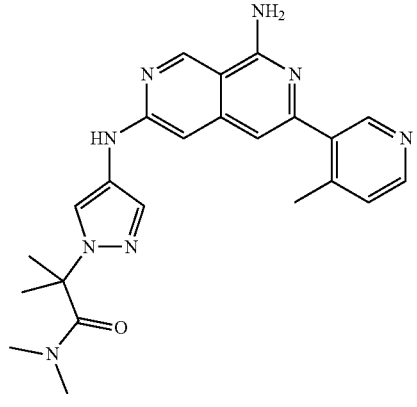 [SMILES: Cc1ccncc1-c1cc2cc(Nc3cnn(C(C)(C)C(=O)N(C)C)c3)ncc2c(N)n1]<br>2-[4-[[8-amino-6-(4-methyl-3-pyridyl)-2,7-naphthyridin-3-yl]amino]pyrazol-1-yl]-N,N,2-trimethyl-propanamide | 1.29<br>431.2<br>A | ¹H NMR (400 MHz, CD₃OD) δ 9.18 (s, 1H), 8.50 (s, 1H), 8.42 (d, J = 5.2 Hz, 1H), 8.06 (s, 1H), 7.67 (s, 1H), 7.39 (d, J = 5.2 Hz, 1H), 6.77 (s, 1H), 6.72 (s, 1H), 2.99 (s, 3H), 2.54 (s, 3H), 2.45 (s, 3H), 1.82 (s, 6H). |

TABLE A-1-continued

| Compd No. | Structure/Name | LCMS R$_T$(min) M + H$^+$, Method | $^1$H NMR (ppm) |
|---|---|---|---|
| 184 | 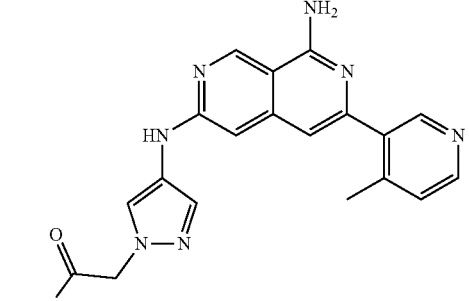<br>2-[4-[[8-amino-6-(4-methyl-3-pyridyl)-2,7-naphthyridin-3-yl]amino]pyrazol-1-yl]-N-methyl-acetamide | 1.18<br>389.2<br>A | $^1$H NMR (400 MHz, CD$_3$OD) δ 9.15 (s, 1H), 8.50 (s, 1H), 8.42 (d, J = 5.2 Hz, 1H), 7.98 (s, 1H), 7.64 (s, 1H), 7.39 (d, J = 5.2 Hz, 1H), 6.76 (s, 1H), 6.75 (s, 1H), 4.86 (s, 2H), 2.80 (s, 3H), 2.44 (s, 3H). |
| 185 | 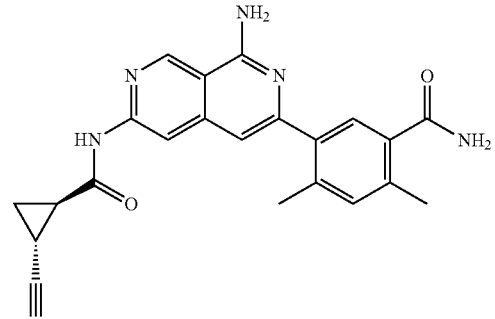<br>(±)-trans-5-(1-amino-6-(trans-2-cyanocyclopropanecarboxamido)-2,7-naphthyridin-3-yl)-2,4-dimethylbenzamide | 1.45<br>401.2<br>B | $^1$HNMR (400 MHz, DMSO-d$_6$) δ 11.25 (s, 1H), 9.37 (s, 1H), 8.18 (s, 1H), 7.69 (s, 1H), 7.50 (s, 1H), 7.28-7.26 (m, 3H), 7.12 (s, 1H), 6.94 (s, 1H), 2.77-2.75 (m, 1H), 2.38 (s, 6H), 2.15-2.13 (m, 1H), 1.61-1.57 (m, 1H), 1.43-1.41 (m, 1H). |
| 186 | 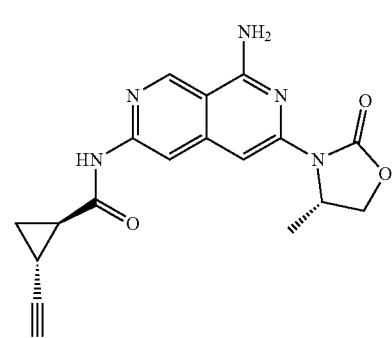<br>trans-N-(8-amino-6-((S)-4-methyl-2-oxooxazolidin-3-yl)-2,7-naphthyridin-3-yl)-2-cyanocyclopropane carboxamide | 1.60<br>353.2<br>B | $^1$HNMR (400 MHz, DMSO-d$_6$) δ 11.17 (s, 1H), 9.26 (s, 1H), 8.01 (s, 1H), 7.38 (s, 2H), 7.30 (s, 1H), 4.85-4.81 (m, 1H), 4.50 (t, J = 8.4 Hz, 1H), 4.06-4.03 (m, 1H), 2.76-2.71 (m, 1H), 2.17-2.13 (m, 1H), 1.61-1.57 (m, 1H), 1.45-1.40 (m, 1H), 1.38 (d, J = 6.4 Hz, 3H). |
| 187 | 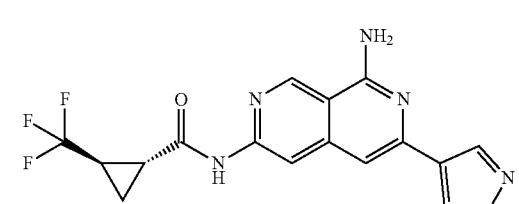<br>(±)-trans-N-(8-amino-6-(5-methyl-1H-pyrazol-4-yl)-2,7-naphthyridin-3-yl)-2-(trifluoromethyl)cyclopropane carboxamide | 1.56<br>377.2<br>B | $^1$HNMR (400 MHz, DMSO-d$_6$) δ 12.64 (s, 1H), 11.09 (s, 1H), 9.26 (s, 1H), 8.12 (s, 1H), 7.96 (d, J = 8.4 Hz, 1H), 7.12 (s, 2H), 6.98 (s, 1H), 2.62-2.56 (m, 4H), 2.33-2.27 (m, 1H), 1.32-1.30 (m, 2H). |

| Compd No. | Structure/Name | LCMS $R_T$(min) M + H+, Method | 1H NMR (ppm) |
|---|---|---|---|
| 188 | 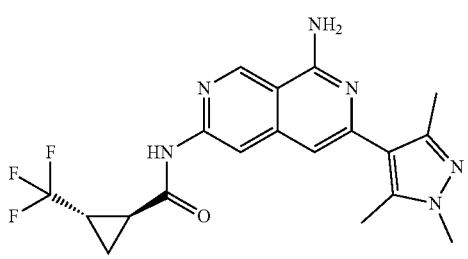 [SMILES: Cc1nn(C)c(C)c1-c1cc2cc(NC(=O)[C@H]3C[C@@H]3C(F)(F)F)ncc2c(N)n1]<br>(±)-trans-N-(8-amino-6-(1,3,5-trimethyl-1H-pyrazol-4-yl)-2,7-naphthyridin-3-yl)-(trifluoromethyl)cyclopropanecarboxamide | 1.57<br>405.2<br>B | 1HNMR (400 MHz, CD3OD) δ 9.21 (s, 1H), 8.23 (s, 1H), 6.81 (s, 1H), 3.77 (s, 3H), 2.46--2.43 (m, 1H), 2.41 (s, 3H), 2.33 (s, 3H), 2.30-2.26 (m, 1H), 1.45-1.41 (m, 1H), 1.37-1.32 (m, 1H). |
| 189 | 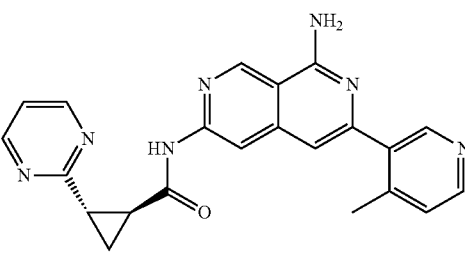<br>(±)-trans-N-(8-amino-6-(4-methylpyridin-3-yl)-2,7-naphthyridin-3-yl)-2-(pyrimidin-2-yl)cyclopropanecarboxamide | 1.38<br>398.2<br>B | 1HNMR (400 MHz, DMSO-d6) δ 11.09 (s, 1H), 9.36 (s, 1H), 8.72 (s, 1H), 8.71 (s, 1H), 8.57 (s, 1H), 8.44 (d, J = 4.8 Hz, 1H), 8.27 (s, 1H), 7.37-7.31 (m, 4H), 6.99 (s, 1H), 2.76-2.71 (m, 1H), 2.65-2.61 (m, 1H), 2.41 (s, 3H), 1.59-1.57 (m, 2H). |
| 190 | 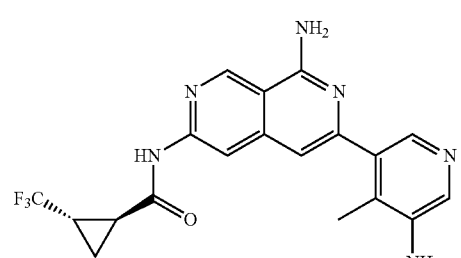<br>(±)-trans-N-(8-amino-6-(5-amino-4-methylpyridin-3-yl)-2,7-naphthyridin-3-yl)-2-(trifluoromethyl)cyclopropanecarboxamide | 1.57<br>403.2<br>G | 1HNMR (400 MHz, DMSO-d6) δ 11.19 (s, 1H), 9.37 (s, 1H), 8.19 (s, 1H), 7.93 (s, 1H), 7.77 (s, 1H), 7.30 (s, 2H), 6.85 (s, 1H), 5.16 (s, 2H), 2.60-2.58 (m, 1H), 2.32-2.30 (m, 1H), 2.06 (s, 3H), 1.33-1.30 (m, 2H). |
| 191 | 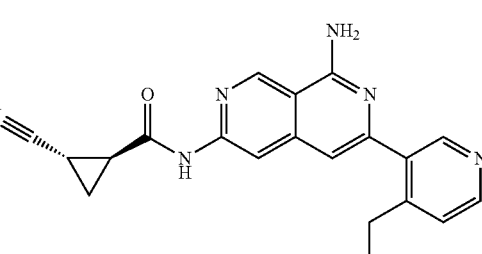<br>(±)-trans-N-(8-amino-6-(4-(2-hydroxyethyl)pyridin-3-yl)-2,7-naphthyridin-3-yl)-2-cyanocyclopropanecarboxamide | 1.169<br>375.1<br>A | 1HNMR (400 MHz, DMSO-d6) δ 11.29 (s, 1H), 9.41 (s, 1H), 8.51 (s, 1H), 8.47 (d, J = 5.2 Hz, 1H), 8.20 (s, 1H), 7.36 (d, J = 5.2 Hz, 1H), 7.34 (s, 2H), 6.98 (s, 1H), 4.77 (t, J = 4.8 Hz, 1H), 3.57-3.55 (m, 2H), 2.93 (t, J = 6.8 Hz, 2H), 2.78-2.74 (m, 1H), 2.18-2.14(m, 1H), 1.64-1.59 (m, 1H), 1.46-1.41(m, 1H). |

| Compd No. | Structure/Name | LCMS R_T(min) M + H+, Method | ¹H NMR (ppm) |
|---|---|---|---|
| 192 | 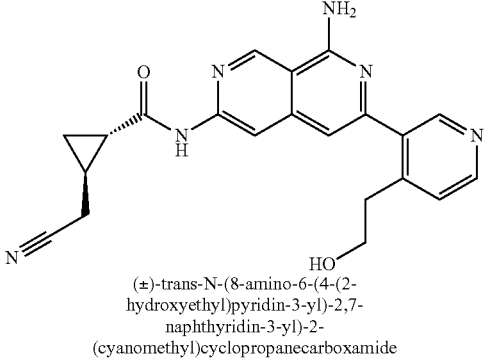<br>(±)-trans-N-(8-amino-6-(4-(2-hydroxyethyl)pyridin-3-yl)-2,7-naphthyridin-3-yl)-2-(cyanomethyl)cyclopropanecarboxamide | 1.404<br>389.0<br>C | ¹HNMR (400 MHz, DMSO-d₆) δ 11.08 (s, 1H), 9.39 (s, 1H), 8.52 (s, 1H), 8.47 (d, J = 5.2 Hz, 1H), 8.23 (s, 1H), 7.36 (d, J = 5.2 Hz, 1H), 7.34 (s, 2H), 6.97 (s, 1H), 4.80 (t, J = 4.8 Hz, 1H), 3.60-3.56 (m, 2H), 2.93 (t, J = 6.8 Hz, 2H), 2.76-2.73 (m, 2H), 2.12-2.09 (m, 1H), 1.59-1.58 (m, 1H), 1.16-1.13 (m, 1H), 0.99-0.96 (m, 1H). |
| 193 | 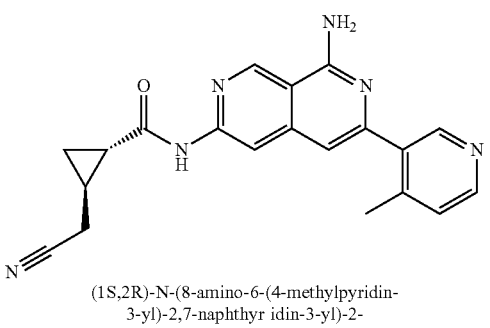<br>(1S,2R)-N-(8-amino-6-(4-methylpyridin-3-yl)-2,7-naphthyridin-3-yl)-2-(cyanomethyl)cyclopropane-1-carboxamide (Absolute stereochemistry arbitrarily assigned) | 2.62<br>359.1<br>J | ¹HNMR (400 MHz, DMSO-d₆) δ 11.04 (s, 1H), 9.37 (s, 1H), 8.56 (s, 1H), 8.43 (d, J = 5.0 Hz, 1H), 8.22 (s, 1H), 7.30-7.31 (m, 3H), 6.97 (s, 1H), 3.74 (m, 2 H), 2.41 (s, 3H), 2.11 (m, 1H), 1.58 (m, 1H), 1.13 (m, 1H), 0.96 (m, 1H). |
| 194 | 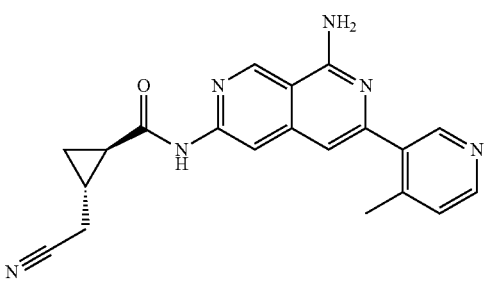 [SMILES: Cc1ccncc1-c1cc2cc(NC(=O)[C@@H]3C[C@H]3CC#N)ncc2c(N)n1]<br>(1R,2S)-N-(8-amino-6-(4-methylpyridin-3-yl)-2,7-naphthyridin-3-yl)-2-(cyanomethyl)cyclopropane-1-carboxamide (Absolute stereochemistry arbitrarily assigned) | 2.66<br>359.1<br>J | ¹HNMR (400 MHz, DMSO-d₆) δ 11.04 (s, 1H), 9.37 (s, 1H), 8.56 (s, 1H), 8.43 (d, J = 5.0 Hz, 1H), 8.22 (s, 1H), 7.30-7.31 (m, 3H), 6.97 (s, 1H), 3.74 (m, 2 H), 2.41 (s, 3H), 2.11 (m, 1H), 1.58 (m, 1H), 1.13 (m, 1H), 0.96 (m, 1H). |
| 195 | 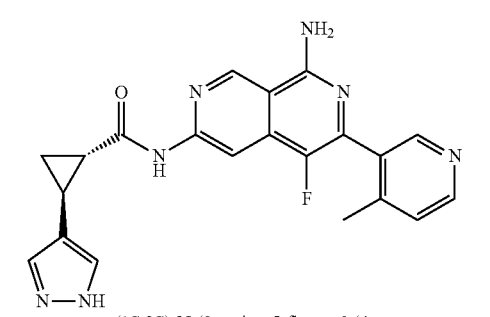<br>(1S,2S)-N-(8-amino-5-fluoro-6-(4-methylpyridin-3-yl)-2,7-naphthyridin-3-yl)-2-(1H-pyrazol-4-yl)cyclopropane-1-carboxamide (Absolute stereochemistry arbitrarily assigned) | 3.05<br>404.1<br>J | ¹HNMR (400 MHz, DMSO-d₆) δ 12.63 (br s, 1H), 11.19 (s, 1H), 9.42 (s, 1H), 8.51 (s, 1H), 8.48 (d, J = 5.1Hz, 1H), 8.40 (s, 1H), 7.61 (br s, 1H), 7.38 (d, J = 5.1Hz, 2H), 7.32 (br s, 2H), 2.27 (s, 3H), 2.19-2.26 (m, 2H), 1.41 (m, 1H), 1.26 (m, 1H). |

TABLE A-1-continued

| Compd No. | Structure/Name | LCMS R*T*(min) M + H⁺, Method | ¹H NMR (ppm) |
|---|---|---|---|
| 196 | (1R,2R)-N-(8-amino-5-fluoro-6-(4-methylpyridin-3-yl)-2,7-naphthyridin-3-yl)-2-(1H-pyrazol-4-yl)cyclopropane-1-carboxamide (Absolute stereochemistry arbitrarily assigned) | 3.06 404.1 J | ¹HNMR (400 MHz, DMSO-d₆) δ 12.63 (br s, 1H), 11.19 (s 1H), 9.42 (s, 1H), 8.51 (s, 1H), 8.48 (d, J = 5.1Hz, 1H), 8.40 (s, 1H), 7.61 (br s, 1H), 7.38 (d, J = 5.1Hz, 2H), 7.32 (br s, 2H), 2.27 (s, 3H), 2.19-2.26 (m, 2H), 1.41 (m, 1H), 1.26 (m, 1H). |
| 197 | (1S,2S)-N-(8-amino-6-(4-methylpyridin-3-yl)-2,7-naphthyridin-3-yl)-2-(1-methyl-1H-pyrazol-4-yl)cyclopropane-1-carboxamide (Absolute stereochemistry arbitrarily assigned) | 2.86 400.2 J | ¹HNMR (400 MHz, DMSO-d₆) δ 10.93 (s, 1H), 9.36 (s, 1H), 8.57 (br s, 1H), 8.43 (br s, 1H), 8.25 (s, 1H), 7.56 (s, 1H), 7.29-7.32 (m, 4H), 6.97 (s, 1H), 3.77 (s, 3H), 2.41 (s, 3H), 2.19-2.22 (m, 2H), 1.39 (m, 1H), 1.19 (m, 1H). |
| 198 | (1R,2R)-N-(8-amino-6-(4-methylpyridin-3-yl)-2,7-naphthyridin-3-yl)-2-(1-methyl-1H-pyrazol-4-yl)cyclopropane-1-carboxamide (Absolute stereochemistry arbitrarily assigned) | 2.87 400.2 J | ¹HNMR (400 MHz, DMSO-d₆) δ 10.93 (s, 1H), 9.36 (s, 1H), 8.57 (br s, 1H), 8.43 (br s, 1H), 8.25 (s, 1H), 7.56 (s, 1H), 7.29-7.32 (m, 4H), 6.97 (s, 1H), 3.77 (s, 3H), 2.41 (s, 3H), 2.19-2.22 (m, 2H), 1.39 (m, 1H), 1.19 (m, 1H). |

TABLE A-1-continued

| Compd No. | Structure/Name | LCMS R_T(min) M + H+, Method | $^1$H NMR (ppm) |
|---|---|---|---|
| 199 | 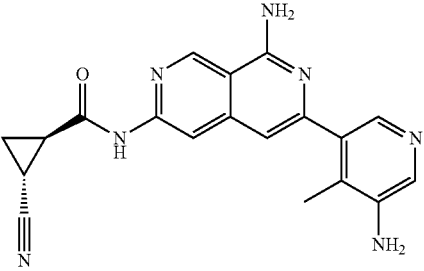 [SMILES: Cc1c(N)cncc1-c1cc2cc(NC(=O)[C@@H]3C[C@H]3C#N)ncc2c(N)n1]<br>(1R,2R)-N-(8-amino-6-(5-amino-4-methylpyridin-3-yl)-2,7-naphthyridin-3-yl)-2-cyanocyclopropane-1-carboxamide<br>(Absolute stereochemistry arbitrarily assigned) | 2.20<br>360.2<br>J | $^1$HNMR (400 MHz, DMSO-d$_6$) δ 11.24 (s, 1H), 9.38 (s, 1H), 8.17 (s, 1H), 7.93 (s, 1H), 7.76 (s, 1H), 7.29 (s, 2H), 6.84 (s, 1H), 5.13 (br s, 2H), 2.76 (m, 1H), 2.15 (m, 1H), 2.06 (s, 3H), 1.61 (m, 1H), 1.43 (m, 1H). |
| 200 | 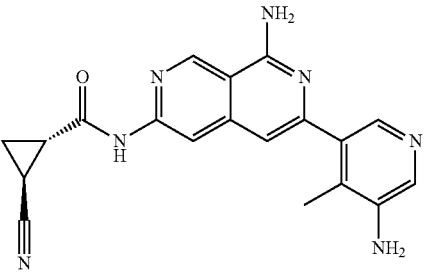 [SMILES: Cc1c(N)cncc1-c1cc2cc(NC(=O)[C@H]3C[C@@H]3C#N)ncc2c(N)n1]<br>(1S,2S)-N-(8-amino-6-(5-amino-4-methylpyridin-3-yl)-2,7-naphthyridin-3-yl)-2-cyanocyclopropane-1-carboxamide<br>(Absolute stereochemistry arbitrarily assigned) | 2.21<br>360.2<br>J | $^1$HNMR (400 MHz, DMSO-d$_6$) δ 11.24 (s, 1H), 9.38 (s, 1H), 8.17 (s, 1H), 7.93 (s, 1H), 7.76 (s, 1H), 7.29 (s, 2H), 6.84 (s, 1H), 5.13 (br s, 2H), 2.76 (m, 1H), 2.15 (m, 1H), 2.06 (s, 3H), 1.61 (m, 1H), 1.43 (m, 1H). |
| 201 | 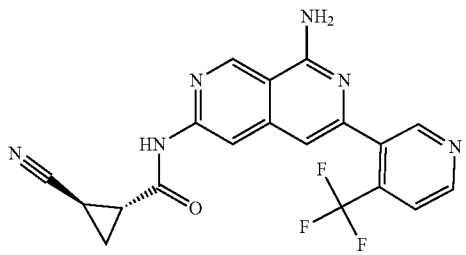 [SMILES: N#C[C@@H]1C[C@H]1C(=O)Nc1cc2cc(-c3cnccc3C(F)(F)F)nc(N)c2cn1]<br>(±)-trans-N-(8-amino-6-(4-(trifluoromethyl)pyridin-3-yl)-2,7-naphthyridin-3-yl)-2-cyanocyclopropane-1-carboxamide | 1.55<br>399.1<br>B | $^1$HNMR (400 MHz, DMSO-d$_6$) δ 11.3 (s, 1H), 9.43 (s, 1H), 8.89 (d, 1H), 8.83 (s, 1H), 8.20 (s, 1H), 7.85 (d, 1H), 7.42 (s, 2H), 6.97 (s, 1H), 2.74-2.79 (m, 1H), 2.13-2.18 (m, 1H), 1.59-1.64 (m, 1H), 1.41-1.46 (m, 1H). |
| 202 | 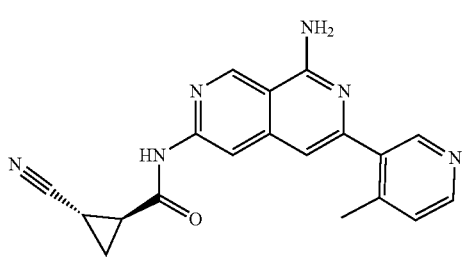 [SMILES: Cc1ccncc1-c1cc2cc(NC(=O)[C@H]3C[C@@H]3C#N)ncc2c(N)n1]<br>(1S,2S)-N-(8-amino-6-(4-methylpyridin-3-yl)-2,7-naphthyridin-3-yl)-2-cyanocyclopropane-1-carboxamide<br>(Absolute stereochemistry arbitrarily assigned) | 2.50<br>345.1<br>J | $^1$HNMR (400 MHz, DMSO-d$_6$) δ 11.26 (s, 1H), 9.39 (s, 1H), 8.56 (s, 1H), 8.43 (d, J = 5.0 Hz, 1H), 8.20 (s, 1H), 7.34 (br s, 2H), 7.30 (d, J = 5.0 Hz, 1H), 6.98 (s, 1H), 2.76 (m, 1H), 2.40 (s, 3H), 2.15 (m, 1H), 1.61 (m, 1H), 1.44 (m, 1H). |

TABLE A-1-continued

| Compd No. | Structure/Name | LCMS R$_T$(min) M + H$^+$, Method | $^1$H NMR (ppm) |
|---|---|---|---|
| 203 | 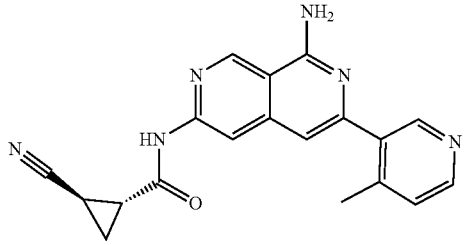 [SMILES: Cc1ccncc1-c1cc2cc(NC(=O)[C@@H]3C[C@H]3C#N)ncc2c(N)n1]<br>(1R,2R)-N-(8-amino-6-(4-methylpyridin-3-yl)-2,7-naphthyridin-3-yl)-2-cyanocyclopropane-1-carboxamide<br>(Absolute stereochemistry arbitrarily assigned) | 2.50<br>345.1<br>J | $^1$HNMR (400 MHz, DMSO-d$_6$) δ 11.26 (s, 1H), 9.39 (s, 1H), 8.56 (s, 1H), 8.43 (d, J = 5.0 Hz, 1H), 8.20 (s, 1H), 7.34 (br s, 2H), 7.30 (d, J = 5.0 Hz, 1H), 6.98 (s, 1H), 2.76 (m, 1H), 2.40 (s, 3H), 2.15 (m, 1H), 1.61 (m, 1H), 1.44 (m, 1H). |
| 204 | 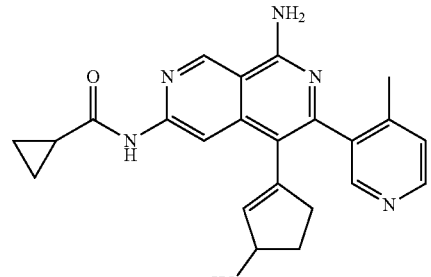<br>(±)-N-(8-amino-5-(3-hydroxycyclopent-1-enyl)-6-(4-methylpyridin-3-yl)-2,7-naphthyridin-3-yl)cyclopropanecarboxamide | 1.52<br>402<br>M | $^1$H NMR (300 MHz, DMSO-d$_6$) δ 10.96 (s, 1H), 9.38 (s, 1H), 8.37 (d, J = 4.8 Hz, 1H), 8.31 (s, 1H), 8.24 (s, 1H), 7.30 (s, 2H), 7.25 (d, J = 4.8 Hz, 1H), 5.49 (s, 1H), 4.71 (d, J = 4.5 Hz, 1H), 4.65 (s, 1H), 2.30 (s, 1H), 2.14 (s, 3H), 2.07-2.03 (m, 3H), 1.48-1.45 (m, 1H), 0.85-0.80 (m, 4H). |
| 205 | 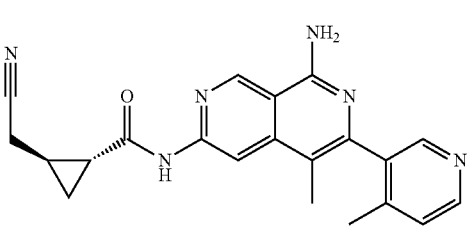 [SMILES: Cc1ccncc1-c1nc(N)c2cnc(NC(=O)[C@@H]3C[C@H]3CC#N)cc2c1C]<br>(±)-trans-N-(8-amino-5-methyl-6-(4-methylpyridin-3-yl)-2,7-naphthyridin-3-yl)-2-(cyanomethyl)cyclopropanecarboxamide | 1.69<br>373<br>K-1 | $^1$H NMR (400 MHz, CD$_3$OD) δ 9.32 (s, 1H), 8.48 (s, 1H), 8.46 (d, J = 5.2 Hz, 1H), 8.37 (s, 1H), 7.45 (d, J = 5.2 Hz, 1H), 2.78-2.65 (m, 2H), 2.23 (s, 3H), 2.14 (s, 3H), 2.06-2.00 (m, 1H), 1.81-1.70 (m, 1H), 1.41-1.30 (m, 1H), 1.12-1.02 (m, 1H). |
| 206 | 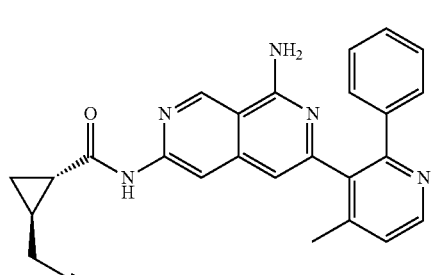<br>(±)-trans-N-(8-amino-6-(4-methyl-2-phenylpyridin-3-yl)-2,7-naphthyridin-3-yl)-2-(cyanomethyl)cyclopropanecarboxamide | 1.14<br>435<br>K-1 | $^1$H NMR (400 MHz, DMSO-d$_6$) δ 11.01 (s, 1H), 9.33 (s, 1H), 8.54 (d, J = 4.7 Hz, 1H), 7.96 (s, 1H), 7.48-7.28 (m, 5H), 7.23-7.10 (m, 3H), 6.48 (s, 1H), 2.81-2.71(m, 2H), 2.17 (s, 3H), 2.11-2.03 (m, 1H), 1.61-1.51 (m, 1H), 1.10-1.06 (m, 1H), 1.03-0.93 (m, 1H). |

TABLE A-1-continued

| Compd No. | Structure/Name | LCMS R_T(min) M + H+, Method | 1H NMR (ppm) |
|---|---|---|---|
| 207 | 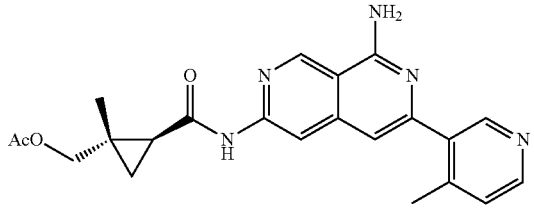 [SMILES: CC(=O)OC[C@@]1(C)C[C@@H]1C(=O)Nc1cc2cc(-c3cnccc3C)nc(N)c2cn1](±)-((1S,2S)-2-(8-amino-6-(4-methylpyridin-3-yl)-2,7-naphthyridin-3-ylcarbamoyl)-1-methylcyclopropyl)methyl acetate (Absolute stereochemistry arbitrarily assigned) | 1.13 406 K-1 | $^1$H NMR (300 MHz, CD$_3$OD) δ 9.29 (s, 1H), 8.54 (s, 1H), 8.43 (d, J = 5.1Hz, 1H), 8.33 (s, 1H), 7.40 (d, J = 5.1Hz, 1H), 6.99 (s, 1H), 4.07-3.95 (m, 2H), 2.46 (s, 3H), 2.11 (s, 3H), 2.09-2.04 (m, 1H), 1.31 (s, 3H), 1.27-1.24 (m, 1H), 1.06-1.01 (m, 1H). |
| 208 | 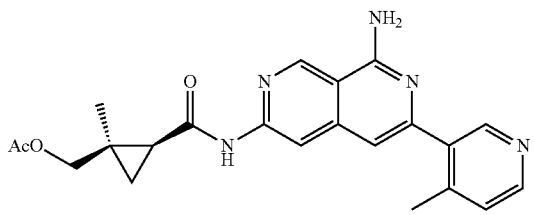 [SMILES: CC(=O)OC[C@]1(C)C[C@@H]1C(=O)Nc1cc2cc(-c3cnccc3C)nc(N)c2cn1](±)-((1R,2S)-2-(8-amino-6-(4-methylpyridin-3-yl)-2,7-naphthyridin-3-ylcarbamoyl)-1-methylcyclopropyl)methyl acetate (Absolute stereochemistry arbitrarily assigned) | 1.28 406 M | $^1$H NMR (300 MHz, CD$_3$OD) δ 9.29 (s, 1H), 8.54 (s, 1H), 8.43 (d, J = 5.1Hz, 1H), 8.29 (s, 1H), 7.40 (d, J = 5.1Hz, 1H), 6.99 (s, 1H), 4.38 (d, J = 11.4 Hz, 1H), 4.19 (d, J = 11.4 Hz, 1H), 2.46 (s, 3H), 2.03-1.99 (m, 1H), 1.94 (s, 3H), 1.42-1.39 (m, 1H), 1.32 (s, 3H), 1.06-1.01 (m, 1H). |
| 209 | 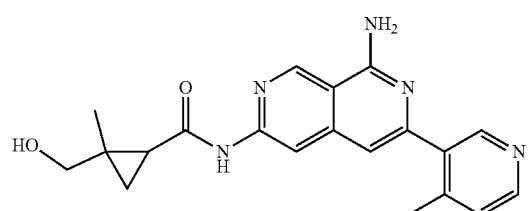(±)-N-(8-amino-6-(4-methylpyridin-3-yl)-2,7-naphthyridin-3-yl)-2-(hydroxymethyl)-2-methylcyclopropanecarboxamide | 1.13 364 M | $^1$H NMR (300 MHz, DMSO-d$_6$) δ 10.69 (s, 1H), 9.35 (s, 1H), 8.56 (s, 1H), 8.43 (d, J = 5.1Hz, 1H), 8.25 (s, 1H), 7.31 (d, J = 5.1Hz, 1H), 7.30 (s, 2H), 6.97 (s, 1H), 4.65 (t, J = 9.0 Hz, 1H), 3.31-3.29 (m, 2H), 2.41 (s, 3H), 2.06-1.95 (m, 1H), 1.18 (s, 3H), 0.99-0.91 (m, 2H). |
| 210 | 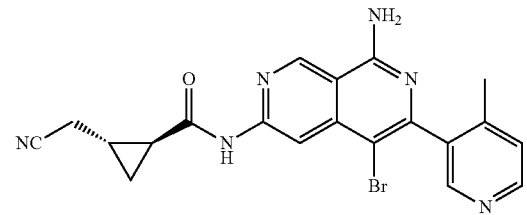 [SMILES: Cc1ccncc1-c1nc(N)c2cnc(NC(=O)[C@H]3C[C@@H]3CC#N)cc2c1Br](±)-trans-N-(8-amino-5-bromo-6-(4-methylpyridin-3-yl)-2,7-naphthyridin-3-yl)-2-(cyanoniethyl)cyclopropanecarboxamide | 1.54 437 K-1 | $^1$H NMR (400 MHz, DMSO-d$_6$): δ 11.25 (s, 1H), 9.40 (s, 1H), 8.58 (s, 1H), 8.47 (d, J = 6.0 Hz, 1H), 8.36 (s, 1H), 7.59 (s, 2H), 7.35 (d, J = 6.0 Hz, 1H), 2.76-2.73 (m, 2H), 2.14-2.10 (m, 4H), 1.64-1.58 (m, 1H), 1.19-1.14 (m, 1H), 1.02-0.95 (m, 1H). |

TABLE A-1-continued

| Compd No. | Structure/Name | LCMS R_T(min) M + H+, Method | $^1$H NMR (ppm) |
|---|---|---|---|
| 211 | 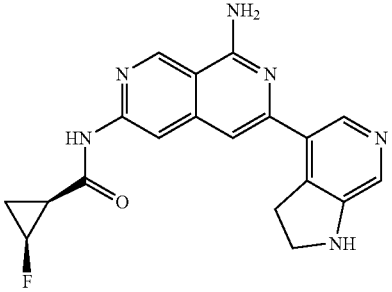 [SMILES: Nc1nc(-c2cncc3c2CCN3)cc2cc(NC(=O)[C@@H]3C[C@@H]3F)ncc12]<br>(±)-cis-N-(8-amino-6-(2,3-dihydro-1H-pyrrolo[2,3-c]pyridin-4-yl)-2,7-naphthyridin-3-yl)-2-fluorocyclopropanecarboxamide | 1.68<br>365<br>K-1 | $^1$H NMR (300 MHz, DMSO-d$_6$): δ 11.07 (s, 1H), 9.41 (s, 1H), 8.41 (s, 1H), 8.35 (s, 1H), 7.83 (s, 1H), 7.48 (s, 2H), 7.31 (s, 1H), 6.54 (s, 1H), 5.08-5.11 (m, 1H), 4.86-4.89 (m, 1H), 3.66-3.49 (m, 4H), 2.32 (s, 1H), 1.76-1.62 (m, 1H), 1.21-1.26 (m, 1H). |
| 212 | 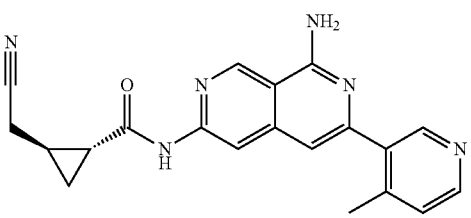 [SMILES: Cc1ccncc1-c1cc2cc(NC(=O)[C@@H]3C[C@H]3CC#N)ncc2c(N)n1]<br>(±)-trans-N-(8-amino-6-(4-methylpyridin-3-yl)-2,7-naphthyridin-3-yl)-2-(cyanomethyl)cyclopropanecarboxamide | 0.96<br>359<br>K-1 | $^1$H NMR (400 MHz, CD$_3$OD) δ 9.30 (s, 1H), 8.54 (s, 1H), 8.43 (d, J = 5.1Hz, 1H), 8.30 (s, 1H), 7.40 (d, J = 5.1Hz, 1H), 6.99 (s, 1H), 2.80-2.63 (m, 2H), 2.46 (s, 3H), 2.02-1.98 (m, 1H), 1.81-1.69 (m, 1H), 1.35-1.20 (m, 1H), 1.10-0.98 (m, 1H). |
| 213 | 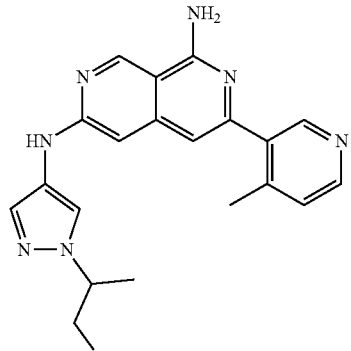<br>(±)-2-(4-(8-amino-6-(4-methylpyridin-3-yl)-2,7-naphthyridin-3-ylamino)-1H-pyrazol-1-yl)propan-1-ol | 1.58<br>376<br>N | $^1$H NMR (400 MHz, DMSO-d$_6$) δ 9.22 (s, 1H), 8.83 (s, 1H), 8.53 (s, 1H), 8.42 (d, J = 5.0 Hz, 1H), 7.90 (s, 1H), 7.50 (s, 1H), 7.29 (d, J = 5.0 Hz, 1H), 7.06 (s, 2H), 6.75 (s, 1H), 6.64 (s, 1H), 4.92 (t, J = 5.5 Hz, 1H), 4.45-4.32 (m, 1H), 3.73-3.55 (m, 2H), 2.40 (s, 3H), 1.40 (d, J = 6.8 Hz, 3H). |
| 214 | 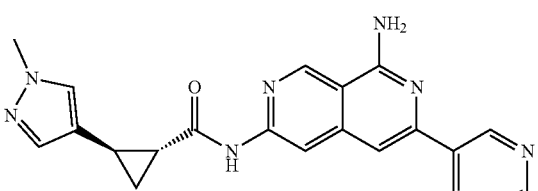<br>(1R,2R)-N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Absolute stereochemistry arbitrarily assigned) | 1.04<br>430<br>M | $^1$H NMR (400 MHz, DMSO-d$_6$) δ 10.95 (s, 1H), 9.38 (s, 1H), 8.52 (s, 1H), 8.48 (d, J = 4.8 Hz, 1H), 8.25 (s, 1H), 7.56 (s, 1H), 7.37 (d, J = 4.8 Hz, 1H), 7.32(s, 2H), 7.29 (s, 1H), 6.97 (s, 1H), 4.78 (t, J = 5.2 Hz, 1H), 3.77 (s, 3H), 3.60-3.55 (m, 2H), 2.95-2.91 (m, 2H), 2.23-2.19 (m, 2H), 1.41-1.37 (m, 1H), 1.22-1.19 (m, 1H). |

TABLE A-1-continued

| Compd No. | Structure/Name | LCMS R_T(min) M + H+, Method | $^1$H NMR (ppm) |
|---|---|---|---|
| 215 | 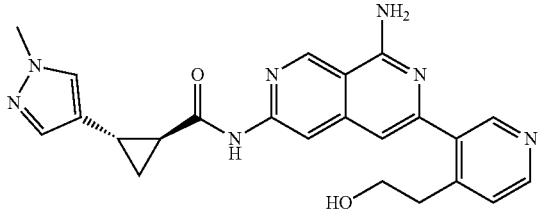 [SMILES: Cn1cc([C@H]2C[C@@H]2C(=O)Nc2cc3cc(-c4cnccc4CCO)nc(N)c3cn2)cn1]<br>(1S,2S)-N-(8-amino-6-(4-(2-hydroxyethyl)pyridin-3-yl)-2,7-naphthyridin-3-yl)-2-(1-methyl-1H-pyrazol-4-yl)cyclopropanecarboxamide (Absolute stereochemistry arbitrarily assigned) | 1.04<br>430<br>M | $^1$H NMR (400 MHz, CD$_3$OD) δ 10.95 (s, 1H), 9.38 (s, 1H), 8.52 (s, 1H), 8.48 (d, J = 4.8 Hz, 1H), 8.25 (s, 1H), 7.56 (s, 1H), 7.37 (d, J = 4.8 Hz, 1H), 7.32(s, 2H), 7.29 (s, 1H), 6.97 (s, 1H), 4.78 (t, J = 5.2 Hz, 1H), 3.77 (s, 3H), 3.60-3.55 (m, 2H), 2.95-2.91 (m, 2H), 2.23-2.19 (m, 2H), 1.41-1.37 (m, 1H), 1.22-1.19 (m, 1H). |
| 216 | 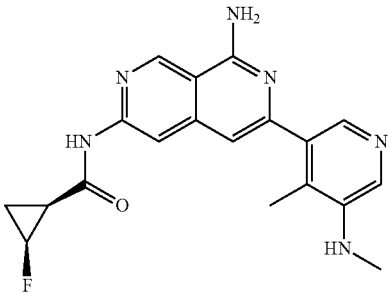 [SMILES: CNc1cncc(-c2cc3cc(NC(=O)[C@@H]4C[C@@H]4F)ncc3c(N)n2)c1C]<br>(±)-cis-N-(8-amino-6-(4-methyl-5-(methylamino)pyridin-3-yl)-2,7-naphthyridin-3-yl)-2-fluorocyclopropanecarboxamide | 1.46<br>367<br>M | $^1$H NMR (400 MHz, DMSO-d$_6$) δ 10.99 (s, 1H), 9.37 (s, 1H), 8.21 (s, 1H), 7.87 (s, 1H), 7.83 (s, 1H), 7.28 (s, 2H), 6.85 (s, 1H), 5.33-5.03 (m, 1H), 5.09-4.82 (m, 1H), 2.82 (d, J = 6.0 Hz, 3H), 2.30-2.23 (m, 1H), 2.09(s, 3H), 1.76-1.61 (m, 1H), 1.25-1.14 (m, 1H). |
| 217 | 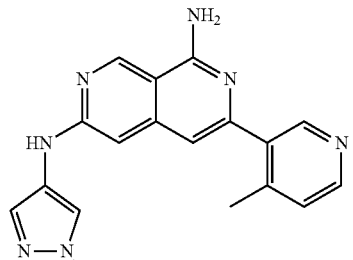<br>(±)-2-(4-(8-amino-6-(4-methylpyridin-3-yl)-2,7-naphthyridin-3-ylamino)-1H-pyrazol-1-yl)propanenitrile | 2.00<br>371<br>M | $^1$H NMR (400 MHz, CD$_3$OD) δ 9.19 (s, 1H), 8.50 (s, 1H), 8.42 (d, J = 6.0 Hz, 1H), 8.13 (s, 1H), 7.70 (s, 1H), 7.39 (d, J = 6.0 Hz, 1H), 6.78 (s, 1H), 6.74 (s, 1H), 5.64 (q, J = 6.0 Hz, 1H), 2.44 (s, 3H), 1.91 (d, J = 6.0 Hz, 3H). |

TABLE A-1-continued

| Compd No. | Structure/Name | LCMS R_T(min) M + H+, Method | $^1$H NMR (ppm) |
|---|---|---|---|
| 218 | 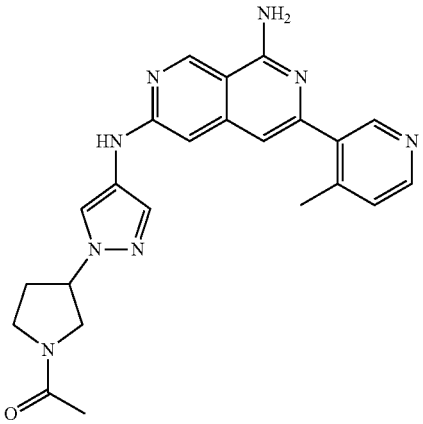 [SMILES: CC(=O)N1CCC(n2cc(Nc3cc4cc(-c5cnccc5C)nc(N)c4cn3)cn2)C1]<br>(±)-1-(3-(4-(8-amino-6-(4-methylpyridin-3-yl)-2,7-naphthyridin-3-ylamino)-1H-pyrazol-1-yl)pyrrolidin-1-yl)ethanone | 1.51<br>492<br>K-1 | $^1$H NMR (400 MHz, DMSO-d$_6$) δ 9.22 (s, 1H), 8.91(d, J = 6.6 Hz, 1H), 8.53 (s, 1H), 8.42 (d, J = 5.0 Hz, 1H), 8.00 (d, J = 11.7 Hz, 1H), 7.55 (d, J = 5.0 Hz, 1H), 7.29 (d, J = 6.6 Hz, 1H), 7.08 (s, 2H), 6.76 (s, 1H), 6.66 (s, 1H), 5.10-4.90 (m, 0.5H), 3.98-3.90 (m, 1H), 3.81-3.71 (m, 1H), 3.71-3.58 (m, 1.5H), 3.54-3.40 (m, 1H), 2.40 (s, 4H), 2.34-2.26 (m, 1H), 1.97 (d, J = 5.3 Hz, 3H). |
| 219 | 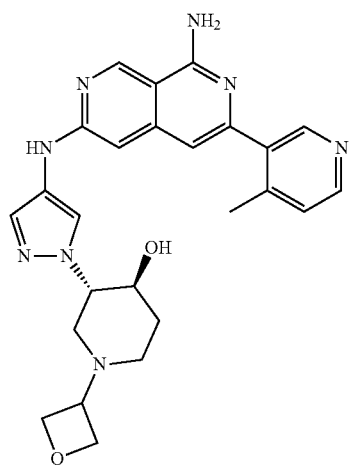 [SMILES: Cc1ccncc1-c1cc2cc(Nc3cnn([C@H]4CN(C5COC5)CC[C@@H]4O)c3)ncc2c(N)n1]<br>(±)-(trans)-3-(4-(8-amino-6-(4-methylpyridin-3-yl)-2,7-naphthyridin-3-ylamino)-1H-pyrazol-1-yl)-1-(oxetan-3-yl)piperidin-4-ol | 0.92<br>473<br>K-1 | $^1$H NMR (300 MHz, CD$_3$OD) δ 9.15 (s, 1H), 8.51 (s, 1H), 8.45 (d, J = 5.1Hz, 1H), 7.96 (s, 1H), 7.62 (s, 1H), 7.41 (d, J = 5.1Hz, 1H), 6.80 (s, 1H), 6.70 (s, 1H), 4.88-4.60 (m, 4H), 4.07-4.00 (m, 1H), 3.98-3.94 (m, 1H), 3.65-3.55 (m, 1H), 3.09-3.03 (m, 1H), 2.92-2.89 (m, 1H), 2.44 (s, 3H), 2.23-2.20 (m, 1H), 2.13-2.06 (m, 2H), 1.95-1.88 (m, 1H). |

| Compd No. | Structure/Name | LCMS R_T(min) M + H+, Method | $^1$H NMR (ppm) |
|---|---|---|---|
| 220 | 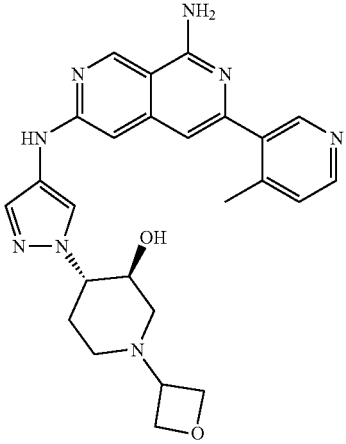 [SMILES: Cc1ccncc1-c1cc2cc(Nc3cnn([C@H]4CCN(C5COC5)C[C@@H]4O)c3)ncc2c(N)n1]<br>(±)-(trans)-4-(4-(8-amino-6-(4-methylpyridin-3-yl)-2,7-naphthyridin-3-ylamino)-1H-pyrazol-1-yl)-1-(oxetan-3-yl)piperidin-3-ol | 2.12<br>473<br>M | $^1$H NMR (300 MHz, CD$_3$OD) δ 9.15 (s, 1H), 8.50 (s, 1H), 8.43 (d, J = 5.1Hz, 1H), 8.00 (s, 1H), 7.61 (s, 1H), 7.40 (d, J = 5.1Hz, 1H), 6.80 (s, 1H), 6.70 (s, 1H), 4.88-4.60 (m, 4H), 4.18-4.11 (m, 1H), 4.05-3.96 (m, 1H), 3.66-3.55 (m, 1H), 3.04-3.00 (m, 1H), 2.87-2.84 (m, 1H), 2.44-2.38 (m, 4H), 2.14-2.07 (m, 2H), 1.78-1.73 (m, 1H). |
| 221 | 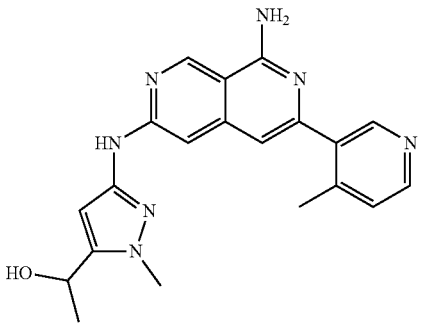 [SMILES: Cc1ccncc1-c1cc2cc(Nc3cc(C(C)O)n(C)n3)ncc2c(N)n1]<br>(±)-1-(3-(8-amino-6-(4-methylpyridin-3-yl)-2,7-naphthyridin-3-ylamino)-1-methyl-1H-pyrazol-5-yl)ethanol | 1.72<br>376<br>M | $^1$H NMR (300 MHz, DMSO-d$_6$) δ 9.34 (s, 1H), 9.21 (s, 1H), 8.54 (s, 1H), 8.41 (d, J = 4.8 Hz, 1H), 7.48 (s, 1H), 7.29 (d, J = 4.8 Hz, 1H), 7.08 (s, 2H), 6.76 (s, 1H), 6.06 (s, 1H), 5.30 (d, J = 6.6 Hz, 1H), 4.82-4.74 (m, 1H), 3.74 (s, 3H), 2.40 (s, 3H), 1.41 (d, J = 6.6 Hz, 3H). |
| 222 | 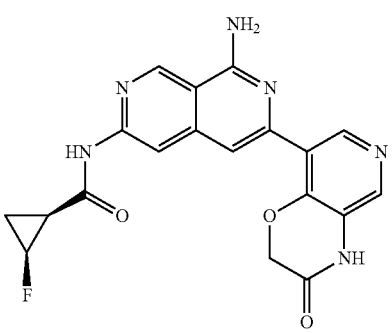 [SMILES: Nc1nc(-c2cncc3c2OCC(=O)N3)cc2cc(NC(=O)[C@@H]3C[C@@H]3F)ncc12]<br>(±)-cis-N-(8-amino-6-(3-oxo-3,4-dihydro-2H-pyrido[4,3-b][1,4]oxazin-8-yl)-2,7-naphthyridin-3-yl)-2-fluorocyclopropanecarboxamide | 1.08<br>395<br>K-1 | $^1$H NMR (400 MHz, DMSO-d$_6$) δ 11.02 (s, 1H), 10.99 (s, 1H), 9.37 (s, 1H), 8.72 (s, 1H), 8.23 (s, 1H), 8.09 (s, 1H), 7.42 (s, 1H), 7.33 (s, 2H), 4.86 (s, 3H), 2.36-2.17 (m, 1H), 1.79-1.59 (m, 1H), 1.32-1.11 (m, 1H). |

TABLE A-1-continued

| Compd No. | Structure/Name | LCMS R_T(min) M + H+, Method | 1H NMR (ppm) |
|---|---|---|---|
| 223 | 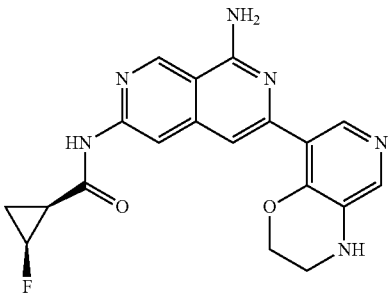 [SMILES: Nc1nc(-c2cncc3c2OCCN3)cc2cc(NC(=O)[C@@H]3C[C@@H]3F)ncc12]<br>(±)-cis-N-(8-amino-6-(3,4-dihydro-2H-pyrido[4,3-b][1,4]oxazin-8-yl)-2,7-naphthyridin-3-yl)-2-fluorocyclopropanecarboxamide | 1.16<br>381<br>M | 1H NMR (300 MHz, CD$_3$OD) δ 9.24 (s, 1H), 8.32-8.22 (s, 1H), 8.16 (s, 1H), 7.83 (s, 1H), 7.34 (s, 1H), 5.02-4.97 (m, 1H), 4.80-4.75 (m, 1H), 4.45-4.33 (m, 2H), 3.51-3.41 (m, 2H), 2.21-2.11 (m, 1H), 1.90-1.76 (m, 1H), 1.28-1.17 (m, 1H). |
| 224 | 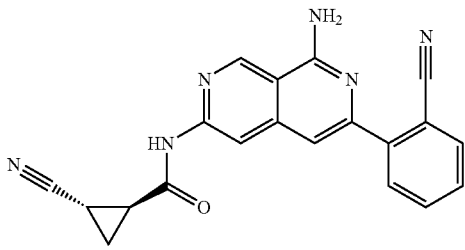 [SMILES: N#Cc1ccccc1-c1cc2cc(NC(=O)[C@H]3C[C@@H]3C#N)ncc2c(N)n1]<br>(±)-trans-N-(8-amino-6-(2-cyanophenyl)-2,7-naphthyridin-3-yl)-2-cyanocyclopropanecarboxamide | 2.32<br>355<br>M | 1H NMR (300 MHz, DMSO-d$_6$) δ 11.32 (s, 1H), 9.43 (s, 1H), 8.24 (s, 1H), 7.94-7.89 (m, 2H), 7.87-7.81 (m, 1H), 7.63-7.58 (m, 1H), 7.43 (s, 2H), 7.22 (s, 1H), 2.79-2.72 (m, 1H), 2.20-2.13 (m, 1H), 1.65-1.61 (m, 1H), 1.60-1.47 (m, 1H) |
| 225 | 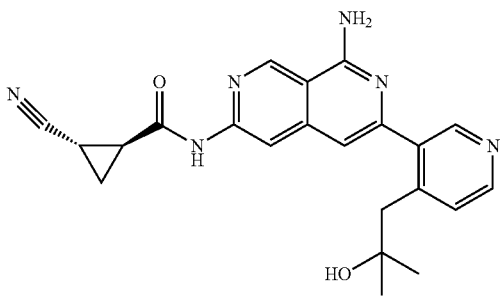 [SMILES: CC(C)(O)Cc1ccncc1-c1cc2cc(NC(=O)[C@H]3C[C@@H]3C#N)ncc2c(N)n1]<br>(±)-trans-N-(8-amino-6-(4-(2-hydroxy-2-methylpropyl)pyridin-3-yl)-2,7-naphthyridin-3-yl)-2-cyanocyclopropanecarboxamide | 1.85<br>403<br>K-1 | 1H NMR (300 MHz, DMSO-d$_6$) δ 9.34 (s, 1H), 8.56 (s, 1H), 8.50 (d, J = 1.8 Hz, 1H), 8.30(s, 1H), 7.46 (d, J = 1.8 Hz, 1H), 7.00(s, 1H), 3.02 (s, 2H), 2.70-2.59 (m, 1H), 2.14-2.12 (m, 1H), 1.67-1.53 (m, 2H), 1.26 (s, 6H). |
| 226 | 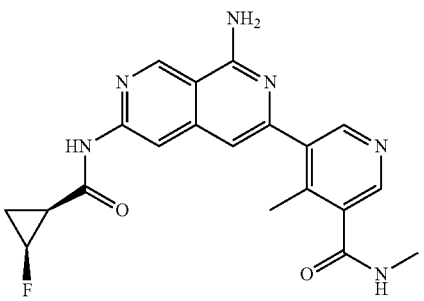 [SMILES: CNC(=O)c1cncc(-c2cc3cc(NC(=O)[C@@H]4C[C@@H]4F)ncc3c(N)n2)c1C]<br>(±)-cis-5-(1-amino-6-(-2-fluorocyclopropanecarboxamido)-2,7-naphthyridin-3-yl)-N,4-dimethylnicotinamide | 0.95<br>395<br>M | 1H NMR (300 MHz, CD$_3$OD): δ 9.38 (s, 1H), 8.58 (s, 1H), 8.50 (s, 1H), 8.33(s, 1H), 6.98 (s, 1H), 5.02-4.97 (m, 1H), 4.80-4.75 (m, 1H), 2.96 (s, 3H), 2.44 (s, 3H), 2.21-2.12 (m, 1H), 1.89-1.76 (m, 1H), 1.30-1.17 (m, 1H). |

TABLE A-1-continued

| Compd No. | Structure/Name | LCMS $R_T$(min) M + H$^+$, Method | $^1$H NMR (ppm) |
|---|---|---|---|
| 227 | 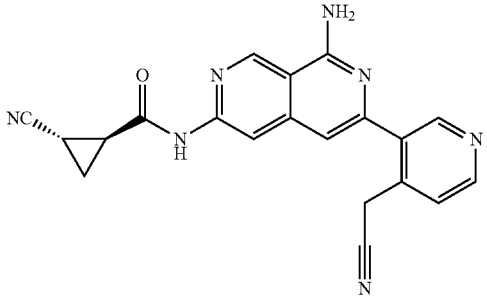 [SMILES: N#CCc1ccncc1-c1cc2cc(NC(=O)[C@H]3C[C@@H]3C#N)ncc2c(N)n1]<br>(±)-trans-N-(8-amino-6-(4-(cyanomethyl)pyridin-3-yl)-2,7-naphthyridin-3-yl)-2-cyanocyclopropanecarboxamide | 1.12<br>370<br>M | $^1$H NMR (300 MHz, DMSO-d$_6$) δ 11.31 (s, 1H), 9.41 (s, 1H), 8.77 (s, 1H), 8.64 (d, J = 6.0 Hz, 1H), 8.25 (s, 1H), 7.54 (d, J = 6.0 Hz, 1H), 7.44 (s, 2H), 7.16 (s, 1H), 4.48 (s, 2H), 2.80-2.74 (m, 1H), 2.21-2.14 (m, 1H), 1.66-1.59 (m, 1H), 1.48-1.42 (m, 1H). |
| 228 | 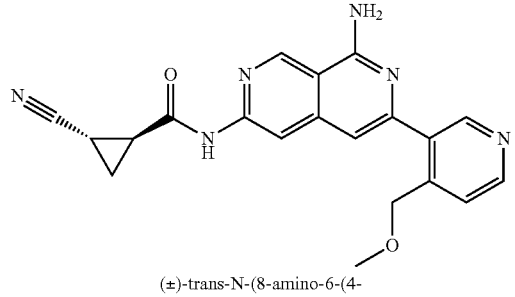<br>(±)-trans-N-(8-amino-6-(4-(methoxymethyl)pyridin-3-yl)-2,7-naphthyridin-3-yl)-2-cyanocyclopropanecarboxamide | 1.02<br>375<br>K-1 | $^1$H NMR (300 MHz, DMSO-d$_6$): δ 11.31 (s, 1H), 9.41 (s, 1H), 8.69 (s, 1H), 8.59 (d, J = 5.1Hz, 1H), 8.23 (s, 1H), 7.54 (d, J = 5.2 Hz, 1H), 7.40 (s, 2H), 7.06 (d, J = 2.2 Hz, 1H), 4.69 (s, 2H), 3.31 (s, 3H), 2.78-2.75 (m, 1H), 2.22-2.13 (m, 1H), 1.68-1.55 (m, 1H), 1.52-1.34 (m, 1H). |
| 229 | 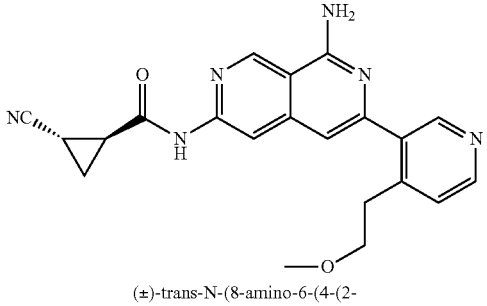<br>(±)-trans-N-(8-amino-6-(4-(2-methoxyethyl)pyridin-3-yl)-2,7-naphthyridin-3-yl)-2-cyanocyclopropanecarboxamide | 1.14<br>389<br>M | $^1$H NMR (300 MHz, DMSO-d$_6$) δ 11.29 (s, 1H), 9.41 (s, 1H), 8.53 (s, 1H), 8.48 (d, J = 6.0 Hz, 1H), 8.20 (s, 1H), 7.37-7.36 (m, 3H), 6.98 (s, 1H), 3.50 (t, J = 6.0 Hz, 2H), 3.15 (s, 3H), 3.03 (t, J = 6.0 Hz, 2H), 2.80-2.74 (m, 1H), 2.20-2.13 (m, 1H), 1.65-1.59 (m, 1H), 1.48-1.41 (m, 1H). |
| 230 | 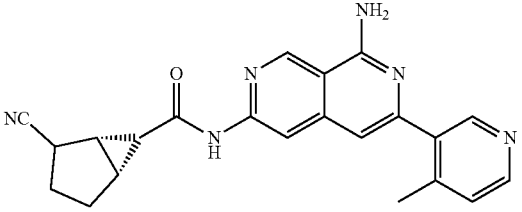<br>(exo)-N-(8-amino-6-(4-methylpyridin-3-yl)-2,7-naphthyridin-3-yl)-2-cyanobicyclo[3.1.0]hexane-6-carboxamide | 2.34<br>385<br>K-1 | $^1$H NMR (300 MHz, DMSO-d$_6$) δ 10.80 (s, 1H), 9.35 (s, 1H), 8.55 (s, 1H), 8.43 (d, J = 5.0 Hz, 1H), 8.20 (s, 1H), 7.40-7.22 (m, 3H), 6.97 (s, 1H), 3.36 (d, J = 5.0 Hz, 1H), 2.40 (s, 3H), 2.14-2.02 (m, 2H), 2.02-1.80 (m, 4H), 1.55-1.45 (m, 1H). |

TABLE A-1-continued

| Compd No. | Structure/Name | LCMS R_T(min) M + H+, Method | 1H NMR (ppm) |
|---|---|---|---|
| 231 | 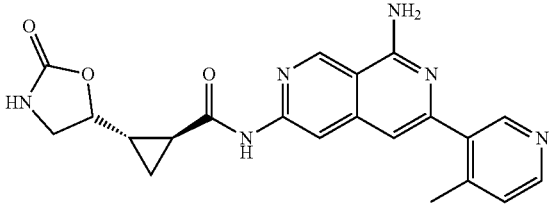 [SMILES: Cc1ccncc1-c1cc2cc(NC(=O)[C@H]3C[C@@H]3C3CNC(=O)O3)ncc2c(N)n1]<br>trans-N-(8-amino-6-(4-methylpyridin-3-yl)-2,7-naphthyridin-3-yl)-2-(2-oxooxazolidin-5-yl)cyclopropanecarboxamide | 1.40<br>405<br>M | $^1$H NMR (300 MHz, DMSO-d$_6$) δ 11.07-11.0 (m, 1H), 9.38 (s, 1H), 8.57 (s, 1H), 8.44 (d, J = 6.0 Hz, 1H), 8.23 (s, 1H), 7.55 (s, 1H), 7.34 (s, 2H), 7.30 (d, J = 6.0 Hz, 1H), 6.98 (s, 1H), 4.42-4.18 (m, 1H), 3.64-3.58 (m, 1H), 3.32-3.23 (m, 1H), 2.41 (s, 3H), 2.25-2.12 (m, 1H), 1.67-1.62 (m, 1H), 1.17-0.96 (m, 2H). |
| 232 | 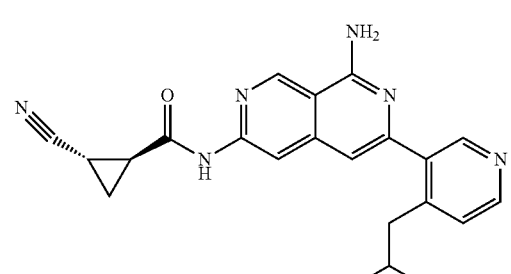<br>trans-N-(8-amino-6-(4-(2-hydroxypropyl)pyridin-3-yl)-2,7-naphthyridin-3-yl)-2-cyanocyclopropanecarboxamide | 1.71<br>389<br>K-1 | $^1$H NMR (300 MHz, DMSO-d$_6$) δ 11.31 (s, 1H), 9.41 (s, 1H), 8.69 (s, 1H), 8.59 (d, J = 2.2 Hz, 1H), 8.23 (s, 1H), 7.54 (d, J = 2.2 Hz, 1H), 7.40 (s, 2H), 7.06 (s, 1H), 4.82-4.80 (m, 1H), 3.81-3.79 (m, 1H), 2.92-2.77 (m, 3H), 2.22-2.13 (m, 1H), 1.68-1.55 (m, 1H), 1.52-1.34 (m, 1H), 0.98 (d, J = 4.8 Hz, 3H). |
| 233 | 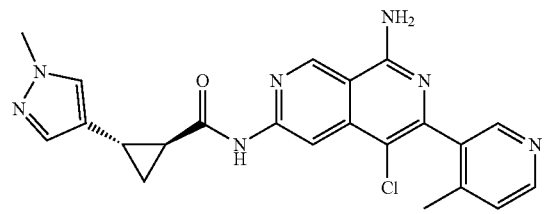 [SMILES: Cc1ccncc1-c1nc(N)c2cnc(NC(=O)[C@H]3C[C@@H]3c3cnn(C)c3)cc2c1Cl]<br>(1S,2S)-N-(8-amino-5-chloro-6-(4-methylpyridin-3-yl)-2,7-naphthyridin-3-yl)-2-(1-methyl-1H-pyrazol-4-yl)cyclopropanecarboxamide (Absolute stereochemistry-arbitrarily assigned) | 1.15<br>434.1<br>K-1 | $^1$H NMR (300 MHz, CD$_3$OD) δ 9.34 (d, J = 0.9 Hz, 1H), 8.72 (d, J = 0.9 Hz, 1H), 8.48 (d, J = 5.2 Hz, 1H), 8.41 (s, 1H), 7.51 (s, 1H), 7.44 (d, J = 5.3 Hz, 1H), 7.38 (d, J = 0.8 Hz, 1H), 3.86 (s, 3H), 2.41-2.39 (m, 1H), 2.29 (s, 3H), 2.14-2.11 (m, 1H), 1.60-1.58 (m, 1H), 1.29-1.26 (m, 1H). |

TABLE A-1-continued

| Compd No. | Structure/Name | LCMS R$_T$(min) M + H$^+$, Method | $^1$H NMR (ppm) |
|---|---|---|---|
| 234 | 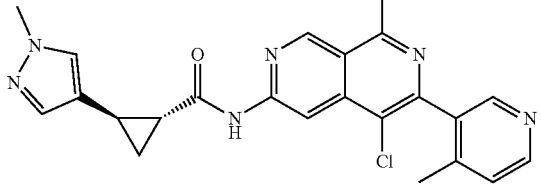<br>(1R,2R)-N-(8-amino-5-chloro-6-(4-methylpyridin-3-yl)-2,7-naphthyridin-3-yl)-2-(1-methyl-1H-pyrazol-4-yl)cyclopropanecarboxamide (Absolute stereochemistry arbitrarily assigned) | 1.16<br>434.1<br>K-1 | $^1$H NMR (300 MHz, CD$_3$OD) δ 9.34 (d, J = 0.9 Hz, 1H), 8.72 (d, J = 0.9 Hz, 1H), 8.48 (d, J = 5.2 Hz, 1H), 8.41 (s, 1H), 7.51 (s, 1H), 7.44 (d, J = 5.3 Hz, 1H), 7.38 (d, J = 0.8 Hz, 1H), 3.86 (s, 3H), 2.41-2.39 (m, 1H), 2.29 (s, 3H), 2.14-2.11 (m, 1H), 1.60-1.58 (m, 1H), 1.29-1.26 (m, 1H). |
| 235 | 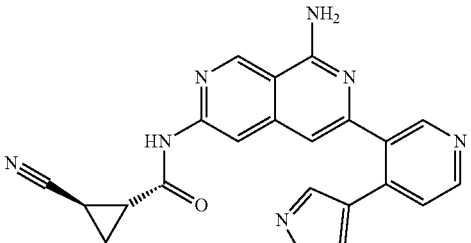<br>(1R,2R)-N-(6-(4-(1H-pyrazol-4-yl)pyridin-3-yl)-8-amino-2,7-naphthyridin-3-yl)-2-cyanocyclopropanecarboxamide (Absolute stereochemistry arbitrarily assigned) | 1.46<br>397.15<br>K-1 | $^1$H NMR (300 MHz, DMSO-d$_6$) δ 12.91 (s, 1H), 11.28 (s, 1H), 9.41 (s, 1H), 8.52 (d, J = 5.3 Hz, 1H), 8.46 (s, 1H), 8.12 (s, 1H), 7.61-7.58 (m, 3H), 7.40 (s, 2H), 6.83 (s, 1H), 2.81-2.69 (m, 1H), 2.14-2.12 (m, 1H), 1.60-1.58 (m, 1H), 1.42-1.40 (m, 1H). |
| 236 | 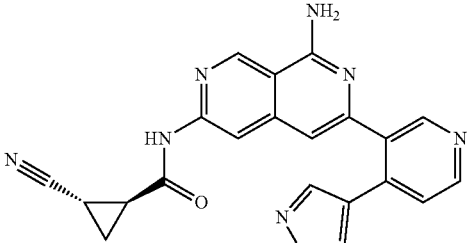<br>(1S,2S)-N-(6-(4-(1H-pyrazol-4-yl)pyridin-3-yl)-8-amino-2,7-naphthyridin-3-yl)-2-cyanocyclopropanecarboxamide (Absolute stereochemistry arbitrarily assigned) | 0.92<br>397.15<br>K-1 | $^1$H NMR (300 MHz, DMSO-d$_6$) δ 12.91 (s, 1H), 11.28 (s, 1H), 9.41 (s, 1H), 8.52 (d, J = 5.3 Hz, 1H), 8.46 (s, 1H), 8.12 (s, 1H), 7.61-7.58 (m, 3H), 7.40 (s, 2H), 6.83 (s, 1H), 2.81-2.69 (m, 1H), 2.14-2.12 (m, 1H), 1.60-1.58 (m, 1H), 1.42-1.40 (m, 1H). |
| 237 | 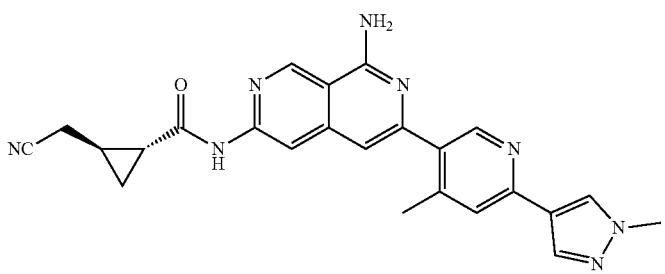 [SMILES: Cc1cc(-c2cnn(C)c2)ncc1-c1cc2cc(NC(=O)[C@@H]3C[C@H]3CC#N)ncc2c(N)n1]<br>(1R,2S)-N-(8-amino-6-(4-methyl-6-(1-methyl-1H-pyrazol-4-yl)pyridin-3-yl)-2,7-naphthyridin-3-yl)-2-(cyanomethyl)cyclopropanecarboxamide (Absolute stereochemistry arbitrarily assigned) | 1.09<br>439.2<br>M | $^1$H NMR (400 MHz, DMSO-d$_6$) δ 11.05 (s, 1H), 9.37 (s, 1H), 8.51 (s, 1H), 8.30 (s, 1H), 8.23 (s, 1H), 8.02 (s, 1H), 7.59 (s, 1H), 7.31 (s, 1H), 6.98 (s, 2H), 3.97 (s, 3H), 2.74 (d, J = 9.0 Hz, 2H), 2.45 (s, 3H), 2.14-2.09 (m, 1H), 1.62-1.55 (m, 1H), 1.17-1.11 (m, 1H), 1.00-0.94 (m, 1H). |

TABLE A-1-continued

| Compd No. | Structure/Name | LCMS R$_T$(min) M + H$^+$, Method | $^1$H NMR (ppm) |
|---|---|---|---|
| 238 | (1S,2R)-N-(8-amino-6-(4-methyl-6-(1-methyl-1H-pyrazol-4-yl)pyridin-3-yl)-2,7-naphthyridin-3-yl)-2-(cyanomethyl)cyclopropanecarboxamide (Absolute stereochemistry arbitrarily assigned) | 1.09 439.2 M | $^1$H NMR (400 MHz, DMSO-d$_6$) δ 11.05 (s, 1H), 9.37 (s, 1H), 8.51 (s, 1H), 8.30 (s, 1H), 8.23 (s, 1H), 8.02 (s, 1H), 7.59 (s, 1H), 7.31 (s, 1H), 6.98 (s, 2H), 3.97 (s, 3H), 2.74 (d, J = 9.0 Hz, 2H), 2.45 (s, 3H), 2.14-2.09 (m, 1H), 1.62-1.55 (m, 1H), 1.17-1.11 (m, 1H), 1.00-0.94 (m, 1H). |
| 239 | (1R,2R)-N-[8-amino-6-(4-methylpyridin-3-yl)-2,7-naphthyridin-3-yl]-2-(2-methoxypropan-2-yl)cyclopropane-1-carboxamide (Absolute stereochemistry arbitrarily assigned) | 1.08 392.2 K-1 | $^1$H NMR (300 MHz, CD$_3$OD) δ 9.30 (s, 1H), 8.54 (s, 1H), 8.43 (d, J = 5.1Hz, 1H), 8.31 (s, 1H), 7.40 (d, J = 5.1Hz, 1H), 6.98 (s, 1H), 3.28 (s, 3H), 2.46 (s, 3H), 2.10-2.02 (m, 1H), 1.67-1.58 (m, 1H), 1.24 (s, 3H), 1.21 (s, 3H), 1.24-1.15 (m, 1H), 1.10-1.01 (m, 1H). |
| 240 | (1S,2S)-N-[8-amino-6-(4-methylpyridin-3-yl)-2,7-naphthyridin-3-yl]-2-(2-methoxypropan-2-yl)cyclopropane-1-carboxamide (Absolute stereochemistry arbitrarily assigned) | 1.08 392.2 K-1 | $^1$H NMR (300 MHz, CD$_3$OD) δ 9.30 (s, 1H), 8.54 (s, 1H), 8.43 (d, J = 5.1Hz, 1H), 8.31 (s, 1H), 7.40 (d, J = 5.1Hz, 1H), 6.98 (s, 1H), 3.28 (s, 3H), 2.46 (s, 3H), 2.10-2.02 (m, 1H), 1.67-1.58 (m, 1H), 1.24 (s, 3H), 1.21 (s, 3H), 1.24-1.15 (m, 1H), 1.10-1.01 (m, 1H). |
| 241 | (1R,2R)-N-[8-amino-6-(4-methylpyridin-3-yl)-2,7-naphthyridin-3-yl]-2-(2-hydroxypropan-2-yl)cyclopropane-1-carboxamide (Absolute stereochemistry arbitrarily assigned) | 0.98 378 K-1 | $^1$H NMR (300 MHz, CD$_3$OD) δ 9.29 (s, 1H), 8.53 (s, 1H), 8.42 (d, J = 5.1Hz, 1H), 8.29 (s, 1H), 7.39 (d, J = 5.1Hz, 1H), 6.97 (s, 1H), 2.45 (s, 3H), 2.04-1.95 (m, 1H), 1.65-1.55 (m, 1H), 1.28 (d, J = 3.0 Hz, 6H), 1.17-1.06 (m, 2H). |

TABLE A-1-continued

| Compd No. | Structure/Name | LCMS R_T(min) M + H+, Method | $^1$H NMR (ppm) |
|---|---|---|---|
| 242 | 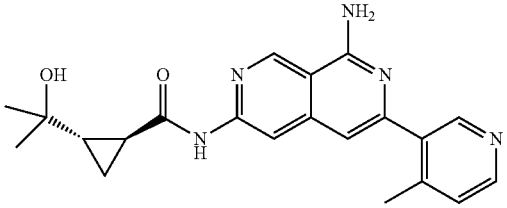 [SMILES: Cc1ccncc1-c1cc2cc(NC(=O)[C@H]3C[C@@H]3C(C)(C)O)ncc2c(N)n1]<br>(1S,2S)-N-[8-amino-6-(4-methylpyridin-3-yl)-2,7-naphthyridin-3-yl]-2-(2-hydroxypropan-2-yl)cyclopropane-1-carboxamide (Absolute stereochemistry arbitrarily assigned) | 0.98<br>378<br>K-1 | $^1$H NMR (300 MHz, CD$_3$OD) δ 9.29 (s, 1H), 8.53 (s, 1H), 8.42 (d, J = 5.1Hz, 1H), 8.29 (s, 1H), 7.39 (d, J = 5.1Hz, 1H), 6.97 (s, 1H), 2.45 (s, 3H), 2.04-1.95 (m, 1H), 1.65-1.55 (m, 1H), 1.28 (d, J = 3.0 Hz, 6H), 1.17-1.06 (m, 2H). |
| 243 | 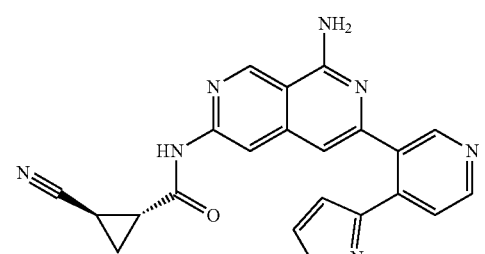<br>(1R,2R)-N-(6-(4-(1H-pyrazol-3-yl)pyridin-3-yl)-8-amino-2,7-naphthyridin-3-yl)-2-cyanocyclopropanecarboxamide (Absolute stereochemistry arbitrarily assigned) | 1.01<br>397.2<br>K-1 | $^1$H NMR (300 MHz, DMSO-d$_6$) δ 13.02 (s, 1H), 11.26 (s, 1H), 9.39 (s, 1H), 8.73-8.45 (m, 2H), 8.08 (s, 1H), 7.81 (d, J = 5.2 Hz, 1H), 7.59 (s, 1H), 7.35 (s, 2H), 6.77 (s, 1H), 5.80 (d, J = 2.5 Hz, 1H), 2.75-2.73 (m, 1H), 2.14-2.12 (m, 1H), 1.60-1.58 (m, 1H), 1.49-1.32 (m, 1H). |
| 244 | 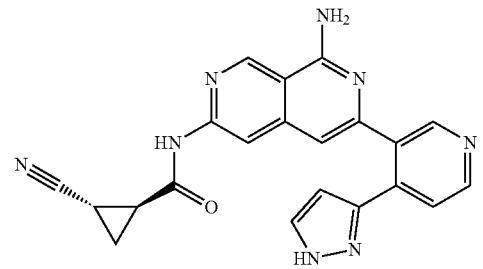<br>(1S,2S)-N-(6-(4-(1H-pyrazol-3-yl)pyridin-3-yl)-8-amino-2,7-naphthyridin-3-yl)-2-cyanocyclopropanecarboxamide (Absolute stereochemistry-arbitrarily assigned) | 1.01<br>397.2<br>K-1 | $^1$H NMR (300 MHz, DMSO-d$_6$) δ 13.02 (s, 1H), 11.26 (s, 1H), 9.39 (s, 1H), 8.73-8.45 (m, 2H), 8.08 (s, 1H), 7.81 (d, J = 5.2 Hz, 1H), 7.59 (s, 1H), 7.35 (s, 2H), 6.77 (s, 1H), 5.80 (d, J = 2.5 Hz, 1H), 2.75-2.73 (m, 1H), 2.14-2.12 (m, 1H), 1.60-1.58 (m, 1H), 1.49-1.32 (m, 1H). |
| 245 | 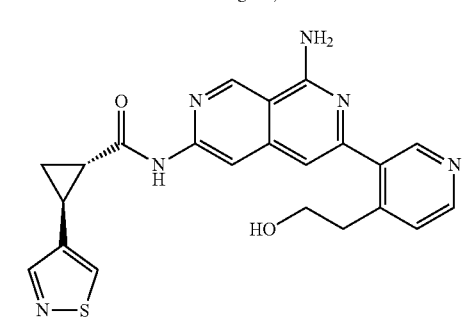<br>(1S,2S)-N-(8-amino-6-(4-(2-hydroxyethyl)pyridin-3-yl)-2,7-naphthyridin-3-yl)-2-(isothiazol-4-yl)cyclopropanecarboxamide (Absolute stereochemistry arbitrarily assigned) | 1.17<br>433.1<br>K-1 | $^1$H NMR (300 MHz, DMSO-d$_6$) δ 11.00 (s, 1H), 9.37 (s, 1H), 8.76 (s, 1H), 8.49 (d, J = 18.5 Hz, 3H), 8.26 (s, 1H), 7.40-7.28 (m, 3H), 6.97 (s, 1H), 4.77-4.66 (m, 1H), 3.58-3.52 (m, 2H), 2.93-2.85 (m, 2H), 2.57-2.50 (m, 1H), 2.48-2.35 (m, 1H), 1.59-1.39 (m, 2H). |

TABLE A-1-continued

| Compd No. | Structure/Name | LCMS R$_T$(min) M + H$^+$, Method | $^1$H NMR (ppm) |
|---|---|---|---|
| 246 | 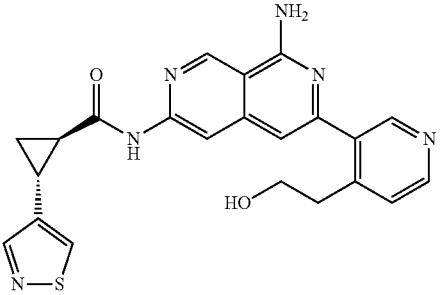 [SMILES: Nc1nc(-c2cnccc2CCO)cc2cc(NC(=O)[C@@H]3C[C@H]3c3cnsc3)ncc12]<br>(1R,2R)-N-(8-amino-6-(4-(2-hydroxyethyl)pyridin-3-yl)-2,7-naphthyridin-3-yl)-2-(isothiazol-4-yl)cyclopropanecarboxamide (Absolute stereochemistry arbitrarily assigned) | 1.17<br>433.1<br>K-1 | $^1$H NMR (300 MHz, DMSO-d$_6$) δ 11.00 (s, 1H), 9.37 (s, 1H), 8.76 (s, 1H), 8.49 (d, J = 18.5 Hz, 3H), 8.26 (s, 1H), 7.40-7.28 (m, 3H), 6.97 (s, 1H), 4.77-4.66 (m, 1H), 3.58-3.52 (m, 2H), 2.93-2.85 (m, 2H), 2.57-2.50 (m, 1H), 2.48-2.35 (m, 1H), 1.59-1.39 (m, 2H). |
| 247 | 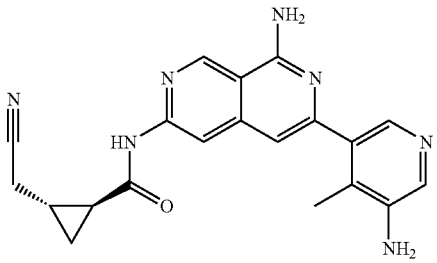 [SMILES: Cc1c(N)cncc1-c1cc2cc(NC(=O)[C@H]3C[C@@H]3CC#N)ncc2c(N)n1]<br>(1S,2R)-N-[8-amino-6-(5-amino-4-methylpyridin-3-yl)-2,7-naphthyridin-3-yl]-2-(cyanomethyl)cyclopropane-1-carboxamide (Absolute stereochemistry arbitrarily assigned) | 0.99<br>374.1<br>M | $^1$H NMR (300 MHz, DMSO-d$_6$) δ 11.03 (s, 1H), 9.35 (s, 1H), 8.20 (s, 1H), 7.93 (s, 1H), 7.76 (s, 1H), 7.26 (s, 2H), 6.82 (s, 1H), 5.14 (s, 2H), 2.73 (d, J = 6.9 Hz, 2H), 2.13-2.06 (m, 4H), 1.60-1.54 (m, 1H), 1.15-1.11 (m, 1H), 0.98-0.95 (m, 1H). |
| 248 | 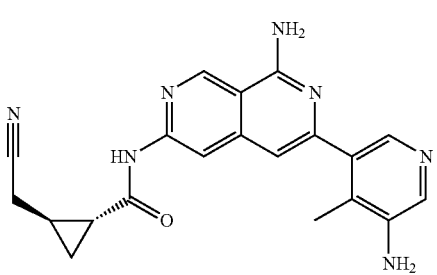 [SMILES: Cc1c(N)cncc1-c1cc2cc(NC(=O)[C@@H]3C[C@H]3CC#N)ncc2c(N)n1]<br>(1R,2S)-N-[8-amino-6-(5-amino-4-methylpyridin-3-yl)-2,7-naphthyridin-3-yl]-2-(cyanomethyl)cyclopropane-1-carboxamide (Absolute stereochemistry arbitrarily assigned) | 1.48<br>374.1<br>M | $^1$H NMR (300 MHz, DMSO-d$_6$) δ 11.03 (s, 1H), 9.35 (s, 1H), 8.20 (s, 1H), 7.93 (s, 1H), 7.76 (s, 1H), 7.26 (s, 2H), 6.82 (s, 1H), 5.14 (s, 2H), 2.73 (d, J = 6.9 Hz, 2H), 2.13-2.06 (m, 4H), 1.60-1.54 (m, 1H), 1.15-1.11 (m, 1H), 0.98-0.95 (m, 1H). |

TABLE A-1-continued

| Compd No. | Structure/Name | LCMS R_T(min) M + H+, Method | 1H NMR (ppm) |
|---|---|---|---|
| 249 | 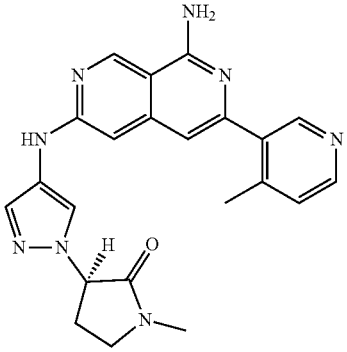 [SMILES: Cc1ccncc1-c1cc2cc(Nc3cnn([C@@H]4CCN(C)C4=O)c3)ncc2c(N)n1]<br>(3R)-3-(4-[[8-amino-6-(4-methylpyridin-3-yl)-2,7-naphthyridin-3-yl]amino]-1H-pyrazol-1-yl)-1-methylpyrrolidin-2-one<br>(Absolute stereochemistry arbitrarily assigned) | 1.01<br>415.2<br>K-1 | $^1$H NMR (300 MHz, DMSO-$d_6$) δ 9.23 (s, 1H), 8.94 (s, 1H), 8.53 (s, 1H), 8.42 (d, J = 5.2 Hz, 1H), 7.99 (s, 1H), 7.54 (s, 1H), 7.29 (d, J = 5.2 Hz, 1H), 6.76 (s, 2H), 6.76 (s, 1H), 6.66 (s, 1H), 5.11-5.07 (m, 1H), 3.53-3.47 (m, 1H), 3.44-3.38 (m, 1H), 2.82 (s, 3H), 2.60-2.57 (m, 1H), 2.50-2.43 (m, 1H), 3.40 (m, 3H). |
| 250 | 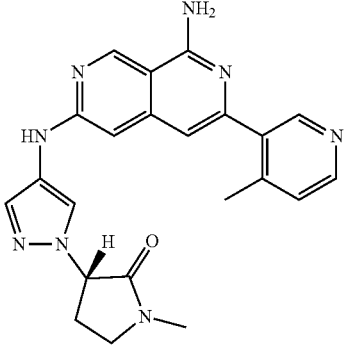 [SMILES: Cc1ccncc1-c1cc2cc(Nc3cnn([C@H]4CCN(C)C4=O)c3)ncc2c(N)n1]<br>(3S)-3-(4-[[8-amino-6-(4-methylpyridin-3-yl)-2,7-naphthyridin-3-yl]amino]-1H-pyrazol-1-yl)-1-methylpyrrolidin-2-one<br>(Absolute stereochemistry arbitrarily assigned) | 1.01<br>415.2<br>K-1 | $^1$H NMR (300 MHz, DMSO-$d_6$) δ 9.23 (s, 1H), 8.94 (s, 1H), 8.53 (s, 1H), 8.42 (d, J = 5.2 Hz, 1H), 7.99 (s, 1H), 7.54 (s, 1H), 7.29 (d, J = 5.2 Hz, 1H), 6.76 (s, 2H), 6.76 (s, 1H), 6.66 (s, 1H), 5.11-5.07 (m, 1H), 3.53-3.47 (m, 1H), 3.44-3.38 (m, 1H), 2.82 (s, 3H), 2.60-2.57 (m, 1H), 2.50-2.43 (m, 1H), 3.40 (m, 3H). |
| 251 | 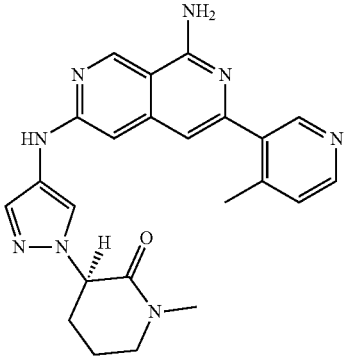 [SMILES: Cc1ccncc1-c1cc2cc(Nc3cnn([C@@H]4CCCN(C)C4=O)c3)ncc2c(N)n1]<br>(3R)-3-(4-[[8-amino-6-(4-methylpyridin-3-yl)-2,7-naphthyridin-3-yl]amino]-1H-pyrazol-1-yl)-1-methylpiperidin-2-one<br>(Absolute stereochemistry arbitrarily assigned) | 1.04<br>429.3<br>K-1 | $^1$H NMR (400 MHz, DMSO-$d_6$) δ 9.22 (s, 1H), 8.92 (s, 1H), 8.54 (s, 1H), 8.42 (d, J = 5.0 Hz, 1H), 7.91 (s, 1H), 7.49 (s, 1H), 7.29 (d, J = 5.0 Hz, 1H), 7.10 (s, 2H), 6.76 (s, 1H), 6.65 (s, 1H), 4.95-4.92 (m, 1H), 3.44-3.42 (m, 1H), 3.32 (s, 1H), 2.87 (s, 3H), 2.41 (s, 3H), 2.37-2.27 (m, 1H), 2.25-2.13 (m, 1H), 2.02-2.00 (m, 1H), 1.92-1.90 (m, 1H). |

TABLE A-1-continued

| Compd No. | Structure/Name | LCMS R_T(min) M + H+, Method | $^1$H NMR (ppm) |
|---|---|---|---|
| 252 | (3S)-3-(4-[[8-amino-6-(4-methylpyridin-3-yl)-2,7-naphthyridin-3-yl]amino]-1H-pyrazol-1-yl)-1-methylpiperidin-2-one (Absolute stereochemistry arbitrarily assigned) | 1.05 429.2 K-1 | $^1$H NMR (400 MHz, DMSO-d$_6$) δ 9.22 (s, 1H), 8.92 (s, 1H), 8.54 (s, 1H), 8.42 (d, J = 5.0 Hz, 1H), 7.91 (s, 1H), 7.49 (s, 1H), 7.29 (d, J = 5.0 Hz, 1H), 7.10 (s, 2H), 6.76 (s, 1H), 6.65 (s, 1H), 4.95-4.92 (m, 1H), 3.44-3.42 (m, 1H), 3.32 (s, 1H), 2.87 (s, 3H), 2.41(s, 3H), 2.37-2.27 (m, 1H), 2.25-2.13 (m, 1H), 2.02-2.00 (m, 1H), 1.92-1.90 (m, 1H). |
| 253 | (1R,2R)-N-[8-amino-6-[4-(2-hydroxyethyl)pyridin-3-yl]-2,7-naphthyridin-3-yl]-2-(pyridin-3-yl)cyclopropane-1-carboxamide (Absolute stereochemistry arbitrarily assigned) | 1.88 427.2 M | $^1$H NMR (400 MHz, DMSO-d$_6$) δ 11.03 (s, 1H), 9.38 (s, 1H), 8.53 (s, 1H), 8.52-8.51 (m, 1H), 8.48 (d, J = 6 Hz, 1H), 8.45-8.42 (m, 1H), 8.28 (s, 1H), 7.59-7.55 (m, 1H), 7.43-7.32 (m, 4H), 6.99 (s, 1H), 4.79 (t, J = 6 Hz, 1H), 3.62-3.55 (m, 2H), 2.94 (t, J = 6 Hz, 2H), 2.55-2.45 (m, 2H), 1.60-1.46 (m, 2H). |
| 254 | (1S,2S)-N-[8-amino-6-[4-(2-hydroxyethyl)pyridin-3-yl]-2,7-naphthyridin-3-yl]-2-(pyridin-3-yl)cyclopropane-1-carboxamide (Absolute stereochemistry-arbitrarily assigned) | 1.24 427.2 M | $^1$H NMR (400 MHz, DMSO-d$_6$) δ 11.03 (s, 1H), 9.38 (s, 1H), 8.53 (s, 1H), 8.52-8.51 (m, 1H), 8.48 (d, J = 6 Hz, 1H), 8.45-8.42 (m, 1H), 8.28 (s, 1H), 7.59-7.55 (m, 1H), 7.43-7.32 (m, 4H), 6.99 (s, 1H), 4.79 (t J = 6 Hz, 1H), 3.62-3.55 (m, 2H), 2.94 (t, J = 6 Hz, 2H), 2.55-2.45 (m, 2H), 1.60-1.46 (m, 2H). |

TABLE A-1-continued

| Compd No. | Structure/Name | LCMS R_T(min) M + H+, Method | 1H NMR (ppm) |
|---|---|---|---|
| 255 | 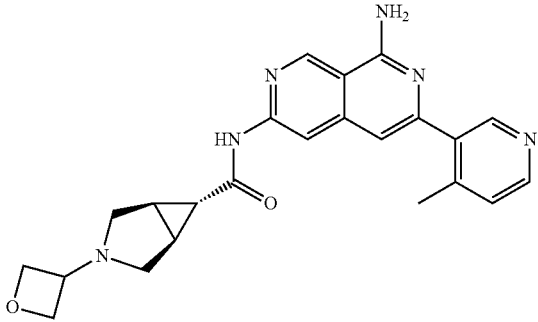 [SMILES: Cc1ccncc1-c1cc2cc(NC(=O)[C@H]3[C@@H]4CN(C5COC5)C[C@@H]43)ncc2c(N)n1]<br>Exo-N-[8-amino-6-(4-methylpyridin-3-yl)-2,7-naphthyridin-3-yl]-3-(oxetan-3-yl)-3-azabicyclo[3.1.0]hexane-6-carboxamide | 1.25<br>417.2<br>K-1 | $^1$H NMR (300 MHz, DMSO-$d_6$) δ 10.79 (s, 1H), 9.35 (s, 1H), 8.57 (s, 1H), 8.44 (d, J = 5.0 Hz, 1H), 8.23 (s, 1H), 7.48-7.21 (m, 3H), 6.96 (s, 1H), 4.56 (t, J = 6.6 Hz, 2H), 4.44 (t, J = 6.0 Hz, 2H), 3.73 (m, 1H), 3.05 (d, J = 8.9 Hz, 2H), 2.47-2.42 (m, 3H), 2.41 (s, 3H), 1.95 (t, J = 2.2 Hz, 2H). |
| 256 | 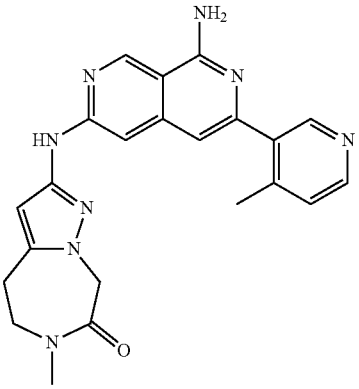 [SMILES: Cc1ccncc1-c1cc2cc(Nc3cc4n(n3)CC(=O)N(C)CC4)ncc2c(N)n1]<br>2-[[8-amino-6-(4-methylpyridin-3-yl)-2,7-naphthyridin-3-yl]amino]-6-methyl-4H,5H,6H,7H,8H-pyrazolo[1,5-d][1,4]diazepin-7-one | 1.10<br>415.2<br>K-1 | $^1$H NMR (300 MHz, DMSO-$d_6$) δ 9.43 (s, 1H), 9.22 (s, 1H), 8.56 (s, 1H), 8.42 (d, J = 6.0 Hz, 1H), 7.55 (s, 1H), 7.30 (d, J = 6.0 Hz, 1H), 7.10 (s, 2H), 6.82 (s, 1H), 6.05 (s, 1H), 4.99 (s, 2H), 3.84(t, J = 6.0 Hz, 2H), 3.06 (t, J = 6.0 Hz, 2H), 2.96 (s, 3H), 2.42 (s, 3H). |
| 257 | 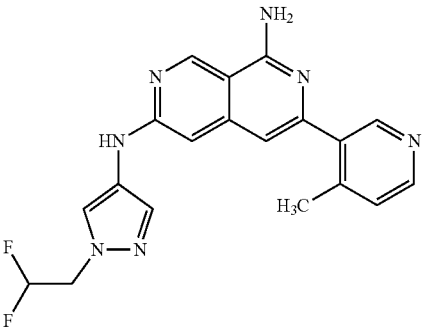 [SMILES: Cc1ccncc1-c1cc2cc(Nc3cnn(CC(F)F)c3)ncc2c(N)n1]<br>6-N-[1-(2,2-difluoroethyl)-1H-pyrazol-4-yl]-3-(4-methylpyridin-3-yl)-2,7-naphthyridine-1,6-diamine | 1.05<br>382.2<br>M | $^1$H NMR (300 MHz, CD$_3$OD) δ 9.22-9.15 (m, 1H), 8.51 (s, 1H), 8.43 (d, J = 5.1Hz, 1H), 8.04 (s, 1H), 7.67 (d, J = 0.8 Hz, 1H), 7.44-7.36 (m, 1H), 6.76 (dd, J = 13.6, 0.9 Hz, 2H), 6.49-5.95 (m, 1H), 4.58 (td, J = 14.4, 3.9 Hz, 2H), 2.45 (s, 3H). |

TABLE A-1-continued

| Compd No. | Structure/Name | LCMS R$_T$(min) M + H$^+$, Method | $^1$H NMR (ppm) |
|---|---|---|---|
| 258 | 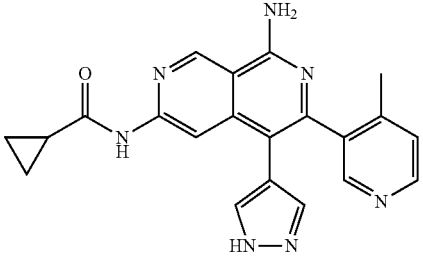 [SMILES: Cc1ccncc1-c1nc(N)c2cnc(NC(=O)C3CC3)cc2c1-c1cn[nH]c1]<br>N-(8-amino-6-(4-methylpyridin-3-yl)-5-(1H-pyrazol-4-yl)-2,7-naphthyridin-3-yl)cyclopropanecarboxamide | 0.91<br>386.2<br>K-1 | $^1$H NMR (400 MHz, DMSO-d$_6$) δ 12.72 (s, 1H), 10.95 (s, 1H), 9.41 (d, J = 0.9 Hz, 1H), 8.39-8.22 (m, 2H), 8.20 (s, 1H), 7.45 (s, 1H), 7.33 (s, 2H), 7.14 (d, J = 4.4 Hz, 2H), 2.03 (s, 4H), 1.01-0.51 (m, 4H). |
| 259 | 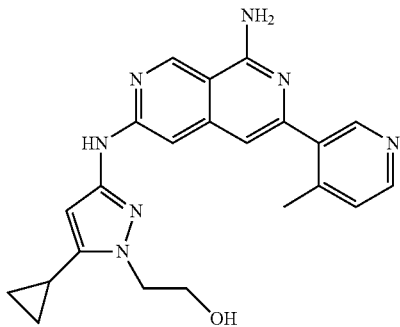 [SMILES: Cc1ccncc1-c1cc2cc(Nc3cc(C4CC4)n(CCO)n3)ncc2c(N)n1]<br>2-(3-[[8-amino-6-(4-methylpyridin-3-yl)-2,7-naphthyridin-3-yl]amino]-5-cyclopropyl-1H-pyrazol-1-yl)ethan-1-ol | 1.07<br>402.2<br>K-1 | $^1$H NMR (300 MHz, CD$_3$OD) δ 9.32 (s, 1H), 8.56 (s, 1H), 8.54 (d, J = 5.4 Hz, 1H), 7.78 (s, 1H), 7.47 (d, J = 5.4 Hz, 1H), 6.85 (s, 1H), 6.71 (s, 1H), 4.15 (t, J = 5.2 Hz, 2H), 3.87 (t, J = 5.2 Hz, 2H), 2.44 (s, 3H), 1.84-1.75 (m, 1H), 0.85-0.83 (m, 4H). |
| 260 | 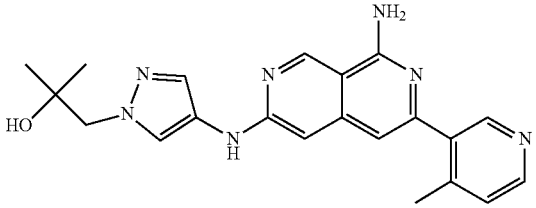 [SMILES: Cc1ccncc1-c1cc2cc(Nc3cnn(CC(C)(C)O)c3)ncc2c(N)n1]<br>1-(4-[[8-amino-6-(4-methylpyridin-3-yl)-2,7-naphthyridin-3-yl]amino]-1H-pyrazol-1-yl)-2-methylpropan-2-ol | 1.05<br>390.1<br>K-1 | $^1$H NMR (300 MHz, DMSO-d$_6$) δ 9.20 (s, 1H), 8.86 (s, 1H), 8.52 (s, 1H), 8.40 (d, J = 5.0 Hz, 1H), 7.88 (s, 1H), 7.48 (s, 1H), 7.28 (d, J = 5.0 Hz, 1H), 7.06 (s, 2H), 6.73 (s, 1H), 6.62 (s, 1H), 4.69 (s, 1H), 3.98 (s, 2H), 2.39 (s, 3H), 1.07 (s, 6H). |
| 261 | 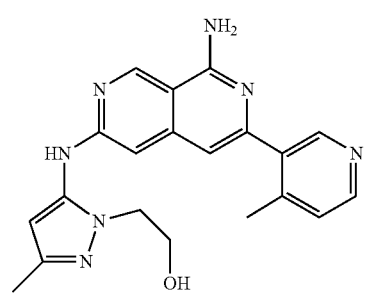 [SMILES: Cc1cc(Nc2cc3cc(-c4cnccc4C)nc(N)c3cn2)n(CCO)n1]<br>2-(5-[[8-amino-6-(4-methylpyridin-3-yl)-2,7-naphthyridin-3-yl]amino]-3-methyl-1H-pyrazol-1-yl)ethan-1-ol | 1.01<br>376.1<br>K-1 | $^1$H NMR (300 MHz, CD$_3$OD) δ 9.17 (t, J = 0.9 Hz, 1H), 8.51 (s, 1H), 8.42 (d, J = 5.1 Hz, 1H), 7.49-7.30 (m, 1H), 6.84 (dd, J = 7.3, 0.9 Hz, 2H), 6.16 (d, J = 0.6 Hz, 1H), 4.16 (t, J = 5.4 Hz, 2H), 3.89 (dd, J = 5.7, 5.0 Hz, 2H), 2.44 (d, J = 0.6 Hz, 3H), 2.27 (d, J = 0.5 Hz, 3H). |

| Compd No. | Structure/Name | LCMS R_T(min) M + H+, Method | 1H NMR (ppm) |
|---|---|---|---|
| 262 | 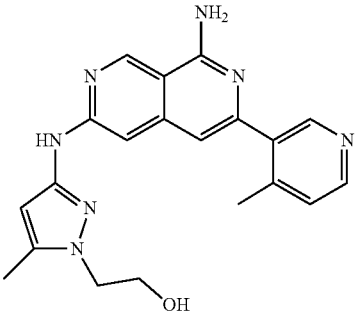 [SMILES: Cc1ccncc1-c1cc2cc(Nc3cc(C)n(CCO)n3)ncc2c(N)n1]<br>2-(3-[[8-amino-6-(4-methylpyridin-3-yl)-2,7-naphthyridin-3-yl]amino]-5-methyl-1H-pyrazol-1-yl)ethan-1-ol | 1.01<br>376.1<br>K-1 | 1H NMR (300 MHz, CD3OD) δ 9.16 (t, J = 0.8 Hz, 1H), 8.52 (s, 1H), 8.43 (d, J = 5.1Hz, 1H), 7.48-7.34 (m, 2H), 6.89-6.78 (m, 1H), 6.03 (d, J = 0.8 Hz, 1H), 4.13 (t, J = 5.4 Hz, 2H), 3.93 (t, J = 5.4 Hz, 2H), 2.46 (s, 3H), 2.36 (d, J = 0.8 Hz, 3H). |
| 263 | 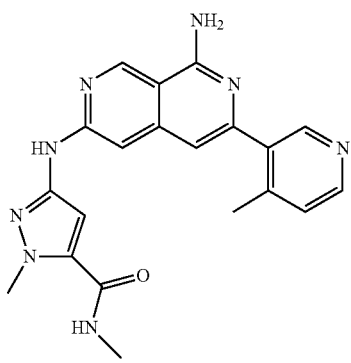 [SMILES: CNC(=O)c1cc(Nc2cc3cc(-c4cnccc4C)nc(N)c3cn2)nn1C]<br>3-[[8-Amino-6-(4-methylpyridin-3-yl)-2,7-naphthyridin-3-yl]amino]-N,1-dimethyl-1H-pyrazole-5-carboxamide | 0.91<br>389.2<br>K-1 | 1H NMR (300 MHz, CD3OD) δ 9.19 (s, 1H), 8.52 (s, 1H), 8.43 (d, J = 5.1Hz, 1H), 7.42 (s, 1H), 7.39 (d, J = 5.1Hz, 1H), 6.85 (s, 1H), 6.72 (s, 1H), 4.07 (s, 3H), 2.89 (s, 3H), 2.45 (s, 3H). |
| 264 | 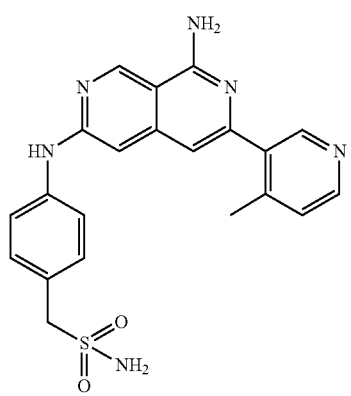<br>(4-[[8-Amino-6-(4-methylpyridin-3-yl)-2,7-naphthyridin-3-yl]amino]phenyl)methanesulfonamide | 1.07<br>421.1<br>M | 1H NMR (300 MHz, DMSO-d6) δ 13.07-12.83 (m, 1H), 9.97 (s, 1H), 9.58 (s, 1H), 8.98-8.42 (m, 3H), 7.60 (d, J = 8.4 Hz, 2H), 7.54 (s, 1H), 7.48 (d, J = 4.8 Hz, 2H), 7.07 (s, 1H), 7.01 (s, 1H), 6.82 (s, 2H), 4.24 (s, 2H), 2.38 (s, 3H). |

| Compd No. | Structure/Name | LCMS R$_T$(min) M + H$^+$, Method | $^1$H NMR (ppm) |
|---|---|---|---|
| 265 | 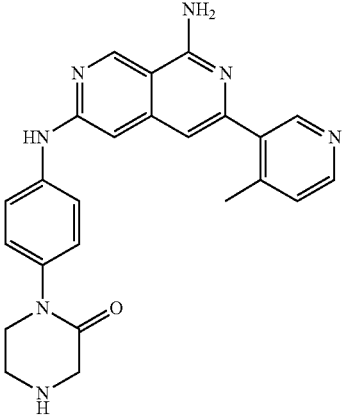 [SMILES: Cc1ccncc1-c1cc2cc(Nc3ccc(N4CCNCC4=O)cc3)ncc2c(N)n1]<br>1-(4-[[8-amino-6-(4-methylpyridin-3-yl)-2,7-naphthyridin-3-yl]amino]phenyl)piperazin-2-one | 1.67<br>426.2<br>M | $^1$H NMR (300 MHz, CD$_3$OD) δ 9.19 (t, J = 0.9 Hz, 1H), 8.50 (s, 1H), 8.41 (d, J = 5.1Hz, 1H), 7.65-7.55 (m, 2H), 7.38 (d, J = 5.2 Hz, 1H), 7.31-7.23 (m, 2H), 6.95 (d, J = 0.9 Hz, 1H), 6.79 (d, J = 0.8 Hz, 1H), 3.72 (t, J = 5.5 Hz, 2H), 3.57 (s, 2H), 3.19 (t, J = 5.5 Hz, 2H), 2.44 (s, 3H). |
| 266 | 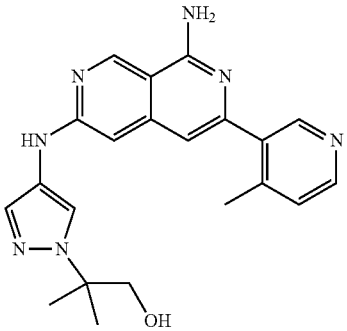 [SMILES: Cc1ccncc1-c1cc2cc(Nc3cnn(C(C)(C)CO)c3)ncc2c(N)n1]<br>2-(4-[[8-amino-6-(4-methylpyridin-3-yl)-2,7-naphthyridin-3-yl]amino]-1H-pyrazol-1-yl)-2-methylpropan-1-ol | 1.83<br>390.2<br>M | $^1$H NMR (400 MHz, DMSO-d$_6$) δ 9.21 (s, 1H), 8.78 (s, 1H), 8.52 (s, 1H), 8.42-8.40 (m, 1H), 7.91 (s, 1H), 7.51 (s, 1H), 7.29-7.27 (m, 1H), 7.04 (m, 2H), 6.74 (s, 1H), 6.62 (s, 1H), 4.97 (t, J = 5.7 Hz, 1H), 5.58 (d, J = 5.7 Hz, 2H), 2.39 (s, 3H), 1.47 (s, 6H). |
| 267 | 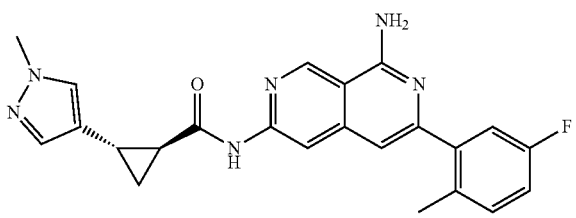 [SMILES: Cc1ccc(F)cc1-c1cc2cc(NC(=O)[C@H]3C[C@@H]3c3cnn(C)c3)ncc2c(N)n1]<br>trans-N-(8-amino-6-(5-fluoro-2-methylphenyl)-2,7-naphthyridin-3-yl)-2-(1-methyl-1H-pyrazol-4-yl)cyclopropanecarboxamide | 1.67<br>417.2<br>K-1 | $^1$H NMR (300 MHz, CD$_3$OD) δ 9.27 (t, J = 0.9 Hz, 1H), 8.32-8.26 (m, 1H), 7.50 (s, 1H), 7.36 (d, J = 0.8 Hz, 1H), 7.30-7.28 (m, 1H), 7.14-7.11 (m, 1H), 7.05-7.03 (m, 1H), 6.90 (d, J = 0.8 Hz, 1H), 3.84 (s, 3H), 2.37-2.35 (m, 1H), 2.32 (s, 3H), 2.15-2.03 (m, 1H), 1.56-1.53 (m, 1H), 1.25-1.22 (m, 1H). |

TABLE A-1-continued

| Compd No. | Structure/Name | LCMS R_T(min) M + H+, Method | ¹H NMR (ppm) |
|---|---|---|---|
| 268 | trans-N-[8-amino-6-(5-hydroxy-2-methylphenyl)-2,7-naphthyridin-3-yl]-2-(1-methyl-1H-pyrazol-4-yl)cyclopropane-1-carboxamide | 1.26<br>415.2<br>K-1 | ¹H NMR (400 MHz, CD₃OD) δ 9.26 (s, 1H), 8.27 (s, 1H), 7.50 (s, 1H), 7.37 (s, 1H), 7.10 (d, J = 8.0 Hz, 1H), 6.84 (d, J = 8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H). |
| 269 | (1R,2S)-N-[8-amino-5-chloro-6-(4-methylpyridin-3-yl)-2,7-naphthyridin-3-yl]-2-(cyanomethyl)cyclopropane-1-carboxamide (Absolute stereochemistry arbitrarily assigned) | 2.06<br>393,<br>K-1 | ¹H NMR (400 MHz, CD₃OD) δ 9.34 (s, 1H), 8.69 (s, 1H), 8.48 (d, J = 5.2 Hz, 1H), 8.41 (s, 1H), 7.44 (d, J = 5.2 Hz, 1H), 2.81-2.62 (m, 2H), 2.29 (s, 3H), 2.07-2.02 (m, 1H), 1.79-1.75 (m, 1H), 1.39-1.33 (m, 1H), 1.09-1.05 (m, 1H). |
| 270 | (1S,2R)-N-[8-amino-5-chloro-6-(4-methylpyridin-3-yl)-2,7-naphthyridin-3-yl]-2-(cyanomethyl)cyclopropane-1-carboxamide (Absolute stereochemistry arbitrarily assigned) | 1.14<br>393,<br>K-1 | ¹H NMR (400 MHz, CD₃OD) δ 9.34 (s, 1H), 8.69 (s, 1H), 8.48 (d, J = 5.2 Hz, 1H), 8.41 (s, 1H), 7.44 (d, J = 5.2 Hz, 1H), 2.81-2.62 (m, 2H), 2.29 (s, 3H), 2.07-2.02 (m, 1H), 1.79-1.75 (m, 1H), 1.39-1.35 (m, 1H), 1.10-1.05 (m, 1H). |
| 271 | (1S,2R)-N-[8-amino-5-ethyl-6-(4-methylpyridin-3-yl)-2,7-naphthyridin-3-yl]-2-(cyanomethyl)cyclopropane-1-carboxamide (Absolute stereochemistiy arbitrarily assigned) | 1.06<br>387,<br>K-1 | ¹H NMR (400 MHz, CD₃OD) δ 9.34 (s, 1H), 8.57 (s, 1H), 8.49 (d, J = 5.2 Hz, 1H), 8.38 (s, 1H), 7.46 (d, J = 5.2 Hz, 1H), 2.78-2.68 (m, 3H), 2.52-2.39 (m, 1H), 2.22 (s, 3H), 2.07-2.02 (m, 1H), 1.79-1.74 (m, 1H), 1.39-1.36 (m, 1H), 1.12-1.02 (m, 4H). |

TABLE A-1-continued

| Compd No. | Structure/Name | LCMS R$_T$(min) M + H$^+$, Method | $^1$H NMR (ppm) |
|---|---|---|---|
| 272 | (1R,2S)-N-[8-amino-5-ethyl-6-(4-methylpyridin-3-yl)-2,7-naphthyridin-3-yl]-2-(cyanomethyl)cyclopropane-1-carboxamide (Absolute stereochemistry arbitrarily assigned) | 1.05 387, K-1 | $^1$H NMR (300 MHz, CD$_3$OD) δ 9.34 (s, 1H), 8.58 (s, 1H), 8.49 (d, J = 5.2 Hz, 1H), 8.38 (s, 1H), 7.46 (d, J = 5.2 Hz, 1H), 2.78-2.68 (m, 3H), 2.52-2.39 (m, 1H), 2.22 (s, 3H), 2.07-2.02 (m, 1H), 1.79-1.74 (m, 1H), 1.39-1.36 (m, 1H), 1.12-1.02 (m, 4H). |
| 273 | (R)-2-(4-(8-amino-6-(4-methylpyridin-3-yl)-2,7-naphthyridin-3-ylamino)-1H-pyrazol-1-yl)propanenitrile (Absolute stereochemistry arbitrarily assigned) | 1.62 371, K-1 | $^1$H NMR (300 MHz, CD$_3$OD) δ 9.19 (s, 1H), 8.50 (s, 1H), 8.42 (d, J = 6.0 Hz, 1H), 8.13 (s, 1H), 7.70 (s, 1H), 7.39 (d, J = 6.0 Hz, 1H), 6.78 (s, 1H), 6.74 (s, 1H), 5.64 (q, J = 6.0 Hz, 1H), 2.44(s, 3H), 1.91 (d, J = 6.0 Hz, 3H). |
| 274 | (S)-2-(4-(8-amino-6-(4-methylpyridin-3-yl)-2,7-naphthyridin-3-ylamino)-1H-pyrazol-1-yl)propanenitrile (Absolute stereochemistry arbitrarily assigned) | 1.61 371, K-1 | $^1$H NMR (300 MHz, CD$_3$OD) δ 9.19 (s, 1H), 8.50 (s, 1H), 8.42 (d, J = 6.0 Hz, 1H), 8.13(s, 1H), 7.70(s, 1H), 7.39(d, J = 6.0 Hz, 1H), 6.78 (s, 1H), 6.74 (s, 1H), 5.64 (q, J = 6 Hz, 1H), 2.44 (s, 3H), 1.91(d, J = 6 Hz, 3H). |

TABLE A-1-continued

| Compd No. | Structure/Name | LCMS R$_T$(min) M + H$^+$, Method | $^1$H NMR (ppm) |
|---|---|---|---|
| 275 | 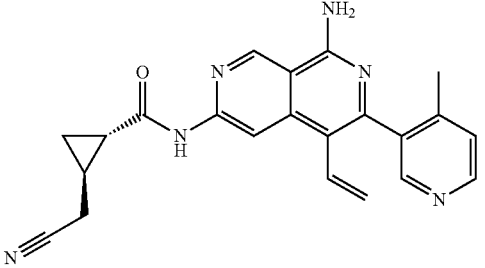 [SMILES: C=Cc1c(-c2cnccc2C)nc(N)c2cnc(NC(=O)[C@H]3C[C@@H]3CC#N)cc12]<br>trans-N-[8-amino-5-ethenyl-6-(4-methylpyridin-3-yl)-2,7-naphthyridin-3-yl]-2-(cyanomethyl)cyclopropane-1-carboxamide | 1.86<br>385.2<br>K-1 | $^1$H NMR (300 MHz, CD$_3$OD) δ 9.34 (s, 1H), 8.71 (s, 1H), 8.44 (d, J = 5.2 Hz, 1H), 8.35 (s, 1H), 7.40 (d, J = 5.2 Hz, 1H), 6.59-6.52 (m, 1H), 5.40-5.37 (m, 1H), 5.25-5.21 (m, 1H), 2.82-2.63 (m, 2H), 2.23 (s, 3H), 2.05-2.01 (m, 1H), 1.77-1.72 (m, 1H), 1.37-1.34 (m, 1H), 1.08-1.03 (m, 1H). |
| 276 | 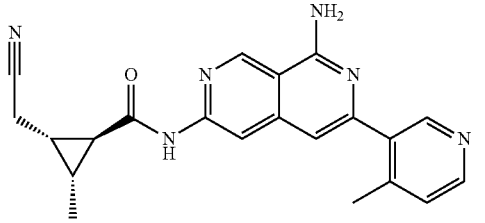 [SMILES: Cc1ccncc1-c1cc2cc(NC(=O)[C@H]3[C@H](C)[C@@H]3CC#N)ncc2c(N)n1]<br>(1S,2S,3R)-N-[8-amino-6-(4-methylpyridin-3-yl)-2,7-naphthyridin-3-yl]-2-(cyanomethyl)-3-methylcyclopropane-1-carboxamide<br>(Absolute stereochemistry arbitrarily assigned) | 3.24<br>372<br>M | $^1$H NMR (300 MHz, CD$_3$OD) δ 9.32 (s, 1H), 8.55 (s, 1H), 8.42 (d, J = 5.2 Hz, 1H), 8.34 (s, 1H), 7.42 (d, J = 5.2 Hz, 1H), 7.01 (s, 1H), 2.74-2.68 (m, 2H), 2.46 (s, 3H), 2.07-2.03 (m, 1H), 1.73-1.68 (m, 1H), 1.51-1.44 (m, 1H), 1.27 (d, J = 8.0 Hz, 3H). |
| 277 | 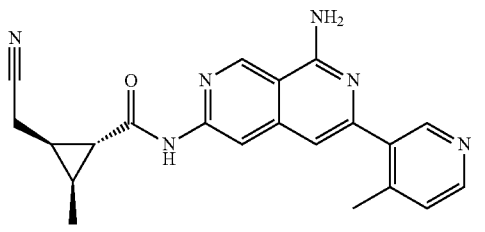<br>(1R,2R,3S)-N-[8-amino-6-(4-methylpyridin-3-yl)-2,7-naphthyridin-3-yl]-2-(cyanomethyl)-3-methylcyclopropane-1-carboxamide<br>(Absolute stereochemistry arbitrarily assigned) | 0.85<br>372<br>K-1 | $^1$H NMR (300 MHz, CD$_3$OD) δ 9.32 (s, 1H), 8.55 (s, 1H), 8.42 (d, J = 5.2 Hz, 1H), 8.34 (s, 1H), 7.42 (d, J = 5.2 Hz, 1H), 7.01 (s, 1H), 2.74-2.68 (m, 2H), 2.46 (s, 3H), 2.07-2.03 (m, 1H), 1.73-1.68 (m, 1H), 1.51-1.44 (m, 1H), 1.27 (d, J = 8.0 Hz, 3H). |
| 278 | 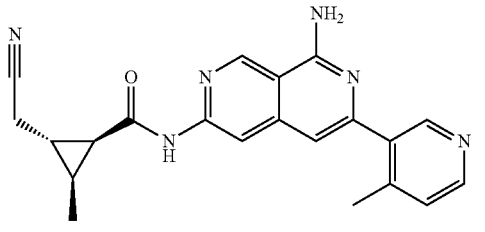 [SMILES: Cc1ccncc1-c1cc2cc(NC(=O)[C@H]3[C@@H](C)[C@@H]3CC#N)ncc2c(N)n1]<br>(1S,2S,3S)-N-[8-amino-6-(4-methylpyridin-3-yl)-2,7-naphthyridin-3-yl]-2-(cyanomethyl)-3-methylcyclopropane-1-carboxamide<br>(Absolute stereochemistry arbitrarily assigned) | 0.99<br>372<br>K-1 | $^1$H NMR (300 MHz, CD$_3$OD) δ 9.30 (s, 1H), 8.54 (s, 1H), 8.43 (d, J = 5.2 Hz, 1H), 8.30 (s, 1H), 7.41 (d, J = 5.2 Hz, 1H), 6.98 (s, 1H), 2.74-2.67 (m, 2H), 2.46 (s, 3H), 1.88-1.81 (m, 1H), 1.73-1.68 (m, 2H), 1.28 (d, J = 8.0 Hz, 3H). |

TABLE A-1-continued

| Compd No. | Structure/Name | LCMS R$_T$(min) M + H$^+$, Method | $^1$H NMR (ppm) |
|---|---|---|---|
| 279 | 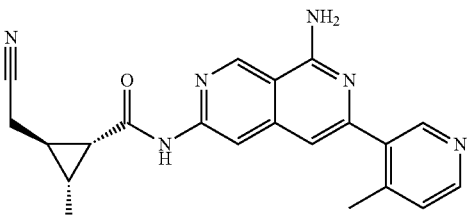<br>(1R,2R,3R)-N-[8-amino-6-(4-methylpyridin-3-yl)-2,7-naphthyridin-3-yl]-2-(cyanomethyl)-3-methylcyclopropane-1-carboxamide (Absolute stereochemistry arbitrarily assigned) | 1.79<br>372<br>K-1 | $^1$H NMR (300 MHz, CD$_3$OD) δ 9.30 (s, 1H), 8.54 (s, 1H), 8.43 (d, J = 5.2 Hz, 1H), 8.30 (s, 1H), 7.41 (d, J = 5.2 Hz, 1H), 6.98 (s, 1H), 2.74-2.67 (m, 2H), 2.46 (s, 3H), 1.88-1.81 (m, 1H), 1.73-1.68 (m, 2H), 1.28 (d, J = 8.0 Hz, 3H). |
| 280 | 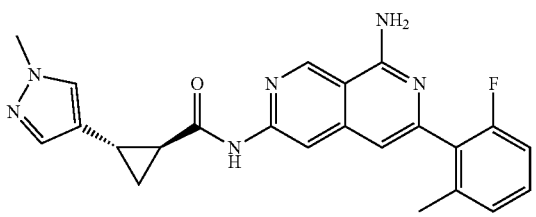 [SMILES: Cc1cccc(F)c1-c1cc2cc(NC(=O)[C@H]3C[C@@H]3c3cnn(C)c3)ncc2c(N)n1]<br>(1S,2S)-N-[8-amino-6-(2-fluoro-6-methylphenyl)-2,7-naphthyridin-3-yl]-2-(1-methyl-1H-pyrazol-4-yl)cyclopropane-1-carboxamide (Absolute stereochemistry arbitrarily assigned) | 2.89<br>417.2<br>K-1 | $^1$H NMR (300 MHz, CD$_3$OD) δ 9.28 (s, 1H), 8.28 (s, 1H), 7.48 (s, 1H), 7.35-7.27 (m, 2H), 7.12 (d, J = 7.8 Hz, 1H), 7.01 (t, J = 9.0 Hz, 1H), 6.85 (s, 1H), 3.83 (s, 3H), 2.39-2.32 (m, 1H), 2.22 (s, 3H), 2.12-2.06 (m, 1H), 1.58-1.52 (m, 1H), 1.27-1.20 (m, 1H). |
| 281 | 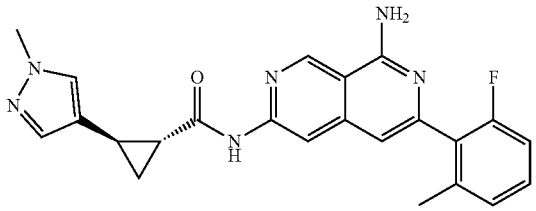 [SMILES: Cc1cccc(F)c1-c1cc2cc(NC(=O)[C@@H]3C[C@H]3c3cnn(C)c3)ncc2c(N)n1]<br>(1R,2R)-N-[8-amino-6-(2-fluoro-6-methylphenyl)-2,7-naphthyridin-3-yl]-2-(1-methyl-1H-pyrazol-4-yl)cyclopropane-1-carboxamide (Absolute stereochemistry arbitrarily assigned) | 1.67<br>417.2<br>K-1 | $^1$H NMR (300 MHz, CD$_3$OD) δ 9.28 (s, 1H), 8.28 (s, 1H), 7.48 (s, 1H), 7.35-7.27 (m, 2H), 7.12 (d, J = 7.8 Hz, 1H), 7.01 (t, J = 9.0 Hz, 1H), 6.85 (s, 1H), 3.83 (s, 3H), 2.39-2.32 (m, 1H), 2.22 (s, 3H), 2.12-2.06 (m, 1H), 1.58-1.52 (m, 1H), 1.27-1.20 (m, 1H). |
| 282 | 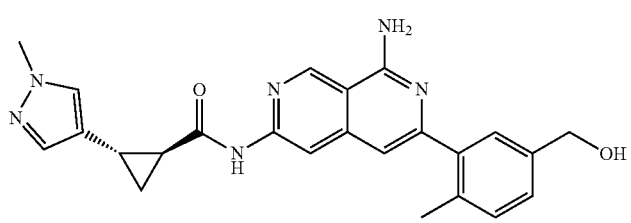 [SMILES: Cc1ccc(CO)cc1-c1cc2cc(NC(=O)[C@H]3C[C@@H]3c3cnn(C)c3)ncc2c(N)n1]<br>(1S,2S)-N-[8-amino-6-[5-(hydroxymethyl)-2-methylphenyl]-2,7-naphthyridin-3-yl]-2-(1-methyl-1H-pyrazol-4-yl)cyclopropane-1-carboxamide (Absolute stereochemistry arbitrarily assigned) | 1.59<br>429.2<br>K-1 | $^1$H NMR (400 MHz, CD$_3$OD) δ 9.30 (s, 1H), 8.28 (s, 1H), 7.50 (s, 1H), 7.38-7.37 (m, 2H), 7.34-7.27 (m, 2H), 6.89 (s, 1H), 4.64 (s, 2H), 3.85 (s, 3H), 2.41-2.37 (m, 1H), 2.35 (s, 3H), 2.13-2.09 (m, 1H), 1.60-1.55 (m, 1H), 1.29-1.24 (m, 1H). |

TABLE A-1-continued

| Compd No. | Structure/Name | LCMS R_T(min) M + H+, Method | $^1$H NMR (ppm) |
|---|---|---|---|
| 283 | 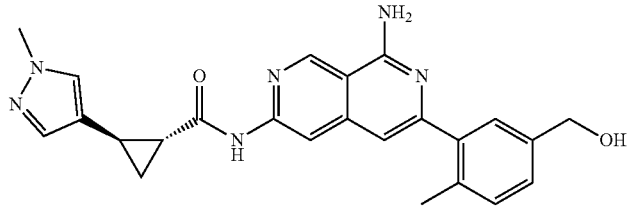 [SMILES: Cc1ccc(CO)cc1-c1cc2cc(NC(=O)[C@@H]3C[C@H]3c3cnn(C)c3)ncc2c(N)n1]<br>(1R,2R)-N-[8-amino-6-[5-(hydroxymethyl)-2-methylphenyl]-2,7-naphthyridin-3-yl]-2-(1-methyl-1H-pyrazol-4-yl)cyclopropane-1-carboxamide (Absolute stereochemistry arbitrarily assigned) | 1.52<br>429.3<br>K-1 | $^1$H NMR (400 MHz, CD$_3$OD) δ 9.30 (s, 1H), 8.28 (s, 1H), 7.50 (s, 1H), 7.38-7.37 (m, 2H), 7.34-7.27 (m, 2H), 6.89 (s, 1H), 4.64 (s, 2H), 3.85 (s, 3H), 2.41-2.37 (m, 1H), 2.35 (s, 3H), 2.13-2.09 (m, 1H), 1.60-1.55 (m, 1H), 1.29-1.24 (m, 1H). |
| 284 | 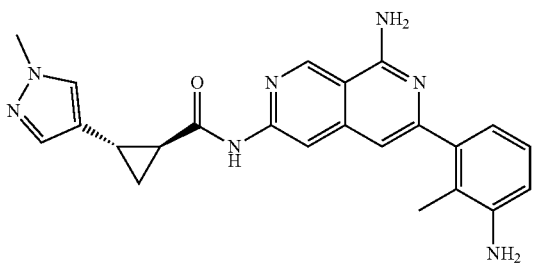<br>(1S,2S)-N-[8-amino-6-(3-amino-2-methylphenyl)-2,7-naphthyridin-3-yl]-2-(1-methyl-1H-pyrazol-4-yl)cyclopropane-1-carboxamide (Absolute stereochemistry arbitrarily assigned) | 2.09<br>414.3<br>K-1 | $^1$H NMR (300 MHz, DMSO-d$_6$) δ 10.89 (s, 1H), 9.32 (s, 1H), 8.18 (s, 1H), 7.56 (s, 1H), 7.29 (s, 1H), 7.17 (s, 2H), 6.92 (t, J = 7.8 Hz, 1H), 6.72 (s, 1H), 6.65 (d, J = 7.2 Hz, 1H), 6.57 (t, J = 7.2 Hz, 1H), 4.87 (s, 2H), 3.76 (s, 3H), 2.22-2.17 (m, 2H), 2.00 (s, 3H), 1.41-1.35 (m, 1H), 1.23-1.16 (m, 1H). |
| 285 | 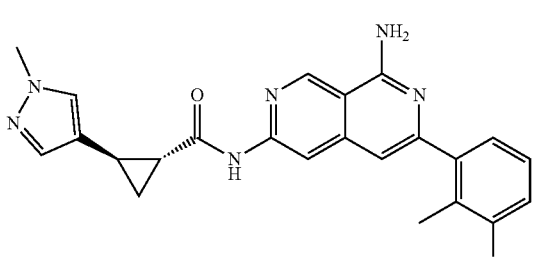<br>(1R,2R)-N-[8-amino-6-(3-amino-2-methylphenyl)-2,7-naphthyridin-3-yl]-2-(1-methyl-1H-pyrazol-4-yl)cyclopropane-1-carboxamide (Absolute stereochemistry arbitrarily assigned) | 2.09<br>414.3<br>K-1 | $^1$H NMR (300 MHz, DMSO-d$_6$) δ 10.89 (s, 1H), 9.32 (s, 1H), 8.18 (s, 1H), 7.56 (s, 1H), 7.29 (s, 1H), 7.17 (s, 2H), 6.92 (t, J = 7.8 Hz, 1H), 6.72 (s, 1H), 6.65 (d, J = 7.2 Hz, 1H), 6.57 (t, J = 7.2 Hz, 1H), 4.87 (s, 2H), 3.76 (s, 3H), 2.22-2.17 (m, 2H), 2.00 (s, 3H), 1.41-1.35 (m, 1H), 1.23-1.16 (m, 1H). |
| 286 | 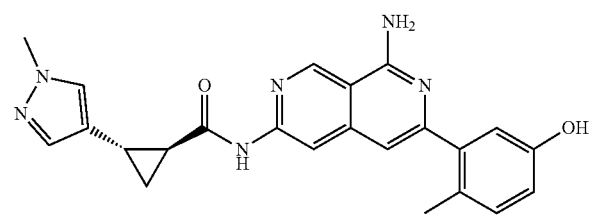 [SMILES: Cc1ccc(O)cc1-c1cc2cc(NC(=O)[C@H]3C[C@@H]3c3cnn(C)c3)ncc2c(N)n1]<br>(1S,2S)-N-[8-amino-6-(5-hydroxy-2-methylphenyl)-2,7-naphthyridin-3-yl]-2-(1-methyl-1H-pyrazol-4-yl)cyclopropane-1-carboxamide (Absolute stereochemistry arbitrarily assigned) | 2.22<br>415.3<br>K-1 | $^1$H NMR (300 MHz, CD$_3$OD) δ 9.26 (s, 1H), 8.27 (s, 1H), 7.50 (s, 1H), 7.37 (s, 1H), 7.10 (d, J = 8.0 Hz, 1H), 6.84 (d, J = 8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H). |

| Compd No. | Structure/Name | LCMS $R_T$(min) M + H+, Method | 1H NMR (ppm) |
|---|---|---|---|
| 287 | 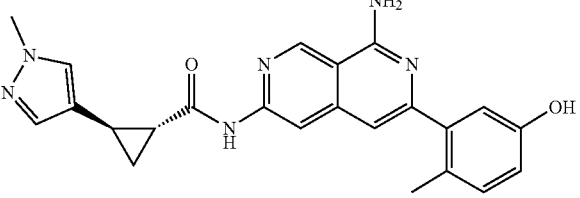<br>(1R,2R)-N-[8-amino-6-(5-hydroxy-2-methylphenyl)-2,7-naphthyridin-3-yl]-2-(1-methyl-1H-pyrazol-4-yl)cyclopropane-1-carboxamide (Absolute stereochemistry arbitrarily assigned) | 1.26<br>415.3<br>K-1 | 1H NMR (300 MHz, CD3OD) δ 9.26 (s, 1H), 8.27 (s, 1H), 7.50 (s, 1H), 7.37 (s, 1H), 7.10 (d, J = 8.0 Hz, 1H), 6.84 (d, J = 8.0 Hz, 2H), 6.77-6.75 (m, 1H), 3.85 (s, 3H), 2.40-2.35 (m, 1H), 2.24 (s, 3H), 2.13-2.08 (m, 1H), 1.59-1.55 (m, 1H), 1.28-1.26 (m, 1H). |
| 288 | 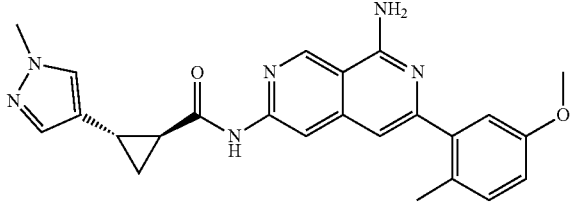 [SMILES: COc1ccc(C)c(-c2cc3cc(NC(=O)[C@H]4C[C@@H]4c4cnn(C)c4)ncc3c(N)n2)c1]<br>(1S,2S)-N-[8-amino-6-(5-methoxy-2-methylphenyl)-2,7-naphthyridin-3-yl]-2-(1-methyl-1H-pyrazol-4-yl)cyclopropane-1-carboxamide (Absolute stereochemistry arbitrarily assigned) | 2.29<br>429.3<br>K-1 | 1H NMR (300 MHz, DMSO-d6) δ 10.93 (s, 1H), 9.34 (s, 1H), 8.22 (s, 1H), 7.56 (s, 1H), 7.29-7.16 (m, 4H), 6.96 (d, J = 2.7 Hz, 1H), 6.88-6.85 (m, 2H), 3.76 (d, J = 3.9 Hz, 6H), 2.27 (s, 3H), 2.22-2.17 (m, 2H), 1.40-1.38 (m, 1H), 1.19-1.18 (m, 1H). |
| 289 | 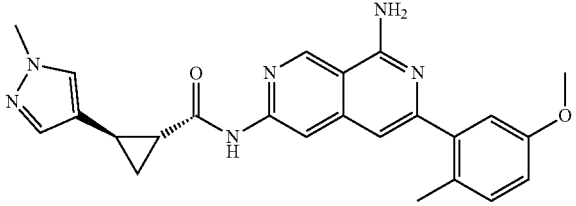<br>(1R,2R)-N-[8-amino-6-(5-methoxy-2-methylphenyl)-2,7-naphthyridin-3-yl]-2-(1-methyl-1H-pyrazol-4-yl)cyclopropane-1-carboxamide (Absolute stereochemistry arbitrarily assigned) | 2.30<br>429.3<br>K-1 | 1H NMR (300 MHz, DMSO-d6) δ 10.93 (s, 1H), 9.34 (s, 1H), 8.22 (s, 1H), 7.56 (s, 1H), 7.29-7.16 (m, 4H), 6.96 (d, J = 2.7 Hz, 1H), 6.88-6.85 (m, 2H), 3.76 (d, J = 3.9 Hz, 6H), 2.27 (s, 3H), 2.22-2.17 (m, 2H), 1.40-1.38 (m, 1H), 1.19-1.18 (m, 1H). |
| 290 | 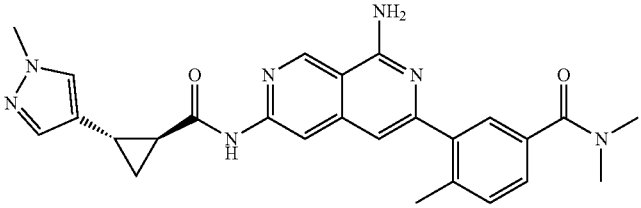 [SMILES: Cc1ccc(C(=O)N(C)C)cc1-c1cc2cc(NC(=O)[C@H]3C[C@@H]3c3cnn(C)c3)ncc2c(N)n1]<br>3-(1-amino-6-[[(1S,2S)-2-(1-methyl-1H-pyrazol-4-yl)cyclopropane]amido]-2,7-naphthyridin-3-yl)-N,N,4-trimethylbenzamide (Absolute stereochemistry arbitrarily assigned) | 1.25<br>470.3<br>K-1 | 1H NMR (300 MHz, CD3OD) δ 9.30 (s, 1H), 8.33 (s, 1H), 7.55-7.47 (m, 2H), 7.46-7.36 (m, 3H), 6.95 (s, 1H), 3.86 (s, 3H), 3.12 (d, J = 10.1Hz, 6H), 2.43-2.30 (m, 4H), 2.18-2.05 (m, 1H), 1.65-1.50 (m, 1H), 1.35-1.20 (m, 1H). |

TABLE A-1-continued

| Compd No. | Structure/Name | LCMS R_T(min) M + H⁺, Method | ¹H NMR (ppm) |
|---|---|---|---|
| 291 | 3-(1-amino-6-[[(1R,2R)-2-(1-methyl-1H-pyrazol-4-yl)cyclopropane]amido]-2,7-naphthyridin-3-yl)-N,N,4-trimethylbenzamide (Absolute stereochemistry arbitrarily assigned) | 1.25 470.3 K-1 | ¹H NMR (300 MHz, CD₃OD) δ 9.30 (s, 1H), 8.33 (s, 1H), 7.55-7.47 (m, 2H), 7.46-7.36 (m, 3H), 6.95 (s, 1H), 3.86 (s, 3H), 3.12 (d, J = 10.1Hz, 6H), 2.43-2.30 (m, 4H), 2.18-2.05 (m, 1H), 1.65-1.50 (m, 1H), 1.35-1.20 (m, 1H). |
| 292 | (1S,2S)-N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide (Absolute stereochemistry arbitrarily assigned) | 1.94 473.3 K-1 | ¹H NMR (400 MHz, CD₃OD) δ 9.30 (s, 1H), 8.54 (s, 1H), 8.44 (d, J = 5.1Hz, 1H), 8.33 (s, 1H), 7.61(s, 1H), 7.48-7.36 (m, 2H), 6.99 (m, 1H), 4.30-4.28 (m, 2H), 3.82-3.80 (m, 2H), 3.66-3.49 (m, 2H), 2.85-2.82 (m, 2H), 2.46 (s, 3H), 2.42-2.37 (m, 1H), 2.14-2.10 (m, 1H), 1.61-1.56 (m, 1H), 1.29-1.26 (m, 1H). |
| 293 | (1R,2R)-N-[8-amino-6-(4-methylpyridin-3-yl)-2,7-naphthyridin-3-yl]-2-[1-[2-(2-aminoethoxy)ethyl]-1H-pyrazol-4-yl]cyclopropane-1-carboxamide (Absolute stereochemistry arbitrarily assigned) | 1.94 473.2 K-1 | ¹H NMR (400 MHz, CD₃OD) δ 9.30 (s, 1H), 8.54 (s, 1H), 8.44 (d, J = 5.1Hz, 1H), 8.33 (s, 1H), 7.61(s, 1H), 7.48-7.36 (m, 2H), 6.99 (m, 1H), 4.30-4.28 (m, 2H), 3.82-3.80 (m, 2H), 3.66-3.49 (m, 2H), 2.85-2.82 (m, 2H), 2.46 (s, 3H), 2.42-2.37 (m, 1H), 2.14-2.10 (m, 1H), 1.61-1.56 (m, 1H), 1.29-1.26 (m, 1H). |

TABLE A-1-continued

| Compd No. | Structure/Name | LCMS $R_T$(min) $M + H^+$, Method | $^1$H NMR (ppm) |
|---|---|---|---|
| 294 | 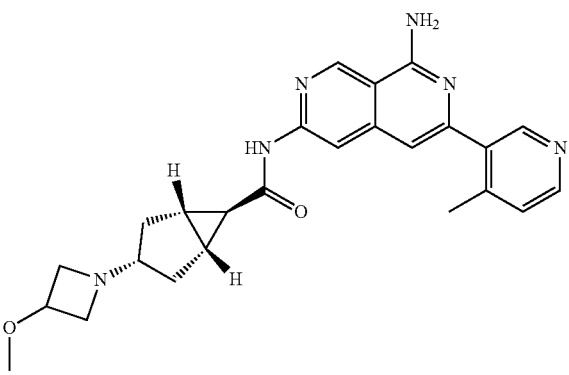 [SMILES: COC1CN([C@@H](C)C[C@H]2[C@@H](C)[C@@H]2C(=O)Nc2cc3cc(-c4cnccc4C)nc(N)c3cn2)C1](1R,3r,5S,6S)-N-[8-amino-6-(4-methylpyridin-3-yl)-2,7-naphthyridin-3-yl]-3-(3-methoxyazetidin-1-yl)bicyclo[3.1.0]hexane-6-carboxamide | 1.91 445.2 K-1 | $^1$H NMR (400 MHz, CD$_3$OD) δ 9.29 (s, 1H), 8.53 (s, 1H), 8.44 (d, J = 5.1Hz, 1H), 6.97 (s, 1H), 4.08-4.02 (m, 1H), 3.69-3.49 (m, 2H), 3.32 (s, 3H), 3.24 (s, 1H), 3.18-3.07 (m, 2H), 2.46 (s, 3H), 2.30 (t, J = 3.0 Hz, 1H), 2.18-2.16 (m, 2H), 2.01-1.92 (m, 2H), 1.73-1.69 (m, 2H) |
| 295 | 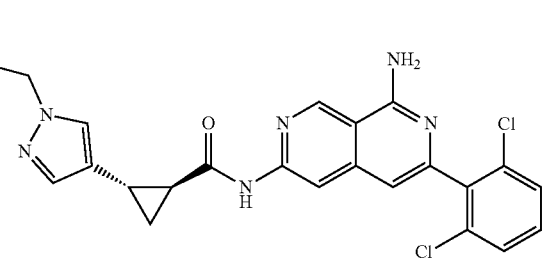(1S,2S)-N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide (Absolute stereochemistry arbitrarily assigned) | 1.43 526.1 K-1 | $^1$H NMR (300 MHz, DMSO-d$_6$) δ 10.98 (s, 1H), 9.38 (s, 1H), 8.23 (s, 1H), 7.62 (s, 1H), 7.58-7.55 (m, 2H), 7.48-7.42 (m, 3H), 7.32 (s, 1H), 6.80 (s, 1H), 4.19 (t, J = 6.0 Hz, 2H), 3.71 (t, J = 6.0 Hz, 2H), 3.35-3.26 (m, 2H), 2.62 (t, J = 6.0 Hz, 2H), 2.22 (t, J = 6.0 Hz, 2H), 2.00-1.80 (m, 2H), 1.42-1.36 (m, 1H), 1.24-1.17 (m, 1H). |
| 296 | 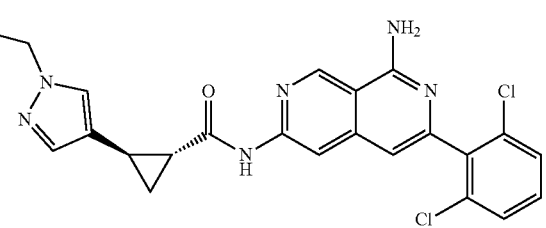(1R,2R)-N-[8-amino-6-(2,6-dichlorophenyl)-2,7-naphthyridin-3-yl]-2-[1-[2-(2-aminoethoxy)ethyl]-1H-pyrazol-4-yl]cyclopropane-1-carboxamide (Absolute stereochemistry arbitrarily assigned) | 1.43 526.1 K-1 | $^1$H NMR (300 MHz, DMSO-d$_6$) δ 10.98 (s, 1H), 9.38 (s, 1H), 8.23 (s, 1H), 7.62 (s, 1H), 7.58-7.55 (m, 2H), 7.48-7.42 (m, 3H), 7.32 (s, 1H), 6.80 (s, 1H), 4.19 (t, J = 6.0 Hz, 2H), 3.71 (t, J = 6.0 Hz, 2H), 3.35-3.26 (m, 2H), 2.62 (t, J = 6.0 Hz, 2H), 2.22 (t, J = 6.0 Hz, 2H), 2.00-1.80 (m, 2H), 1.42-1.36 (m, 1H), 1.24-1.17 (m, 1H). |

TABLE A-1-continued

| Compd No. | Structure/Name | LCMS R_T (min) M + H+, Method | 1H NMR (ppm) |
|---|---|---|---|
| 297 | 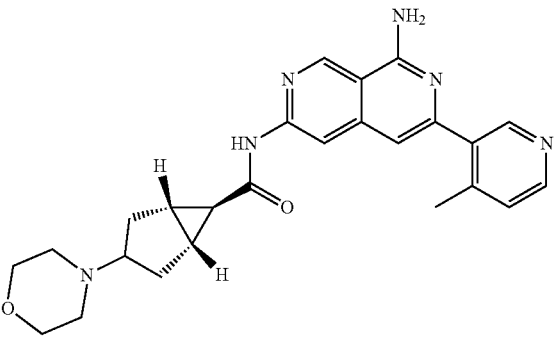 [SMILES: Cc1ccncc1-c1cc2cc(NC(=O)[C@H]3[C@H](C)[C@@H]3CC(C)N3CCOCC3)ncc2c(N)n1]<br>(1R,5S,6R)-N-[8-amino-6-(4-methylpyridin-3-yl)-2,7-naphthyridin-3-yl]-3-(morpholin-4-yl)bicyclo[3.1.0]hexane-6-carboxamide (Absolute stereochemistry arbitrarily assigned) | 1.75<br>445.2<br>K-1 | $^1$H NMR (400 MHz, DMSO-$d_6$) δ 10.87 (s, 1H), 9.37 (s, 1H), 8.56 (s, 1H), 8.43 (d, J = 5.1Hz, 1H), 8.21 (s, 1H), 7.31 (d, J = 5.3 Hz, 3H), 6.95 (s, 1H), 3.59-3.57 (m, 4H), 2.89-2.72 (m, 1H), 2.41 (s, 3H), 2.32 (d, J = 5.5 Hz, 4H), 2.16-2.06 (m, 3H), 1.77-1.74 (m, 2H), 1.59-1.56 (m, 2H). |
| 298 | 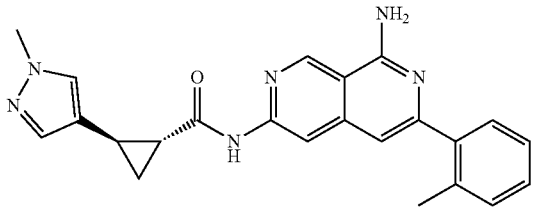 [SMILES: Cc1ccccc1-c1cc2cc(NC(=O)[C@@H]3C[C@H]3c3cnn(C)c3)ncc2c(N)n1]<br>(1R,2R)-N-[8-amino-6-(2-methylphenyl)-2,7-naphthyridin-3-yl]-2-(1-methyl-1H-pyrazol-4-yl)cyclopropane-1-carboxamide (Absolute stereochemistry arbitrarily assigned) | 1.330<br>399<br>K-1 | $^1$H NMR (400 MHz, CD$_3$OD) δ 9.28 (s, 1H), 8.29 (s, 1H), 7.51 (s, 1H), 7.41-7.35 (m, 2H), 7.35-7.25 (m, 3H), 6.89 (d, J = 0.9 Hz, 1H), 3.86 (s, 3H), 2.41-2.37 (m, 1H), 2.36 (s, 3H), 2.14-2.09 (m, 1H), 1.60-1.55 (m, 1H), 1.33-1.23 (m, 1H). |
| 299 | 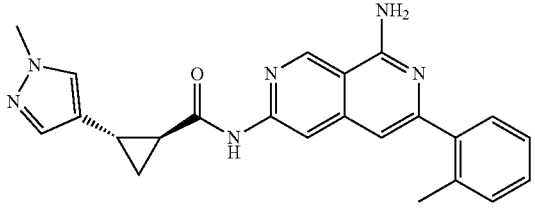 [SMILES: Cc1ccccc1-c1cc2cc(NC(=O)[C@H]3C[C@@H]3c3cnn(C)c3)ncc2c(N)n1]<br>(1S,2S)-N-[8-amino-6-(2-methylphenyl)-2,7-naphthyridin-3-yl]-2-(1-methyl-1H-pyrazol-4-yl)cyclopropane-1-carboxamide (Absolute stereochemistry arbitrarily assigned) | 1.840<br>399<br>K-1 | $^1$H NMR (400 MHz, CD$_3$OD) δ 9.28 (s, 1H), 8.29 (s, 1H), 7.51 (s, 1H), 7.41-7.35 (m, 2H), 7.35-7.25 (m, 3H), 6.89 (d, J = 0.9 Hz, 1H), 3.86 (s, 3H), 2.41-2.37 (m, 1H), 2.36 (s, 3H), 2.14-2.09 (m, 1H), 1.60-1.55 (m, 1H), 1.33-1.23 (m, 1H). |
| 300 | 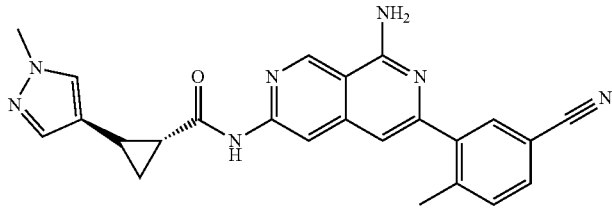<br>(1R,2R)-N-[8-amino-6-(5-cyano-2-methylphenyl)-2,7-naphthyridin-3-yl]-2-(1-methyl-1H-pyrazol-4-yl)cyclopropane-1-carboxamide (Absolute stereochemistry arbitrarily assigned) | 1.330<br>424<br>K-1 | $^1$H NMR (300 MHz, DMSO-$d_6$) δ 10.97 (s, 1H), 9.38 (s, 1H), 8.27 (s, 1H), 7.87 (s, 1H), 7.77 (d, J = 9.0 Hz, 1H), 7.58 (s, 1H), 7.52 (d, J = 9.0 Hz, 1H), 7.35 (s, 2H), 7.31 (s, 1H), 6.99 (s, 1H), 3.77 (s, 3H), 2.46 (s, 3H), 2.24-2.20 (m, 2H), 1.43-1.37 (m, 1H), 1.23-1.18 (m, 1H). |

TABLE A-1-continued

| Compd No. | Structure/Name | LCMS R_T(min) M + H+, Method | ¹H NMR (ppm) |
|---|---|---|---|
| 301 | (1S,2S)-N-[8-amino-6-(5-cyano-2-methylphenyl)-2,1-naphthyridin-3-yl]-2-(1-methyl-1H-pyrazol-4-yl)cyclopropane-1-carboxamide (Absolute stereochemistry arbitrarily assigned) | 1.330 424 K-1 | ¹H NMR (300 MHz, DMSO-d$_6$) δ10.97 (s, 1H), 9.38 (s, 1H), 8.27 (s, 1H), 7.87 (s, 1H), 7.77 (d, J = 9.0 Hz, 1H), 7.58 (s, 1H), 7.52 (d, J = 9.0 Hz, 1H), 7.35 (s, 2H), 7.31 (s, 1H), 6.99 (s, 1H), 3.77 (s, 3H), 2.46 (s, 3H), 2.24-2.20 (m, 2H), 1.43-1.37 (m, 1H), 1.23-1.18 (m, 1H). |
| 302 | (1R,2R)-N-(8-amino-6-(2-chloro-6-fluorophenyl)-2,7-naphthyridin-3-yl)-2-(1-methyl-1H-pyrazol-4-yl)cyclopropanecarboxamide (Absolute stereochemistry arbitrarily assigned) | 1.340 437 K-1 | ¹H NMR (400 MHz, CD$_3$OD) δ 9.55 (s, 1H), 8.55 (s, 1H), 7.68-7.62 (m, 1H), 7.55-7.51 (m, 2H), 7.40-7.33 (m, 2H), 7.24 (s, 1H), 3.86 (s, 3H), 2.45-2.39 (m, 1H), 2.18-2.12 (m, 1H), 1.63-1.58 (m, 1H), 1.34-1.27 (m, 1H). |
| 303 | (1S,2S)-N-(8-amino-6-(2-chloro-6-fluorophenyl)-2,7-naphthyridin-3-yl)-2-(1-methyl-1H-pyrazol-4-yl)cyclopropanecarboxamide (Absolute stereochemistry arbitrarily assigned) | 1.350 437 K-1 | ¹H NMR (400 MHz, CD$_3$OD) δ 9.55 (s, 1H), 8.55 (s, 1H), 7.68-7.62 (m, 1H), 7.55-7.51 (m, 2H), 7.40-7.33 (m, 2H), 7.24 (s, 1H), 3.86 (s, 3H), 2.45-2.39 (m, 1H), 2.18-2.12 (m, 1H), 1.63-1.58 (m, 1H), 1.34-1.27 (m, 1H). |
| 304 | (1S,2S)-N-[8-amino-6-(2-chlorophenyl)-2,7-naphthyridin-3-yl]-2-(1-methyl-1H-pyrazol-4-yl)cyclopropane-1-carboxamide (Absolute stereochemistry arbitrarily assigned) | 0.95 419 K-1 | ¹H NMR (400 MHz, DMSO-d$_6$) δ 10.98 (s, 1H), 9.39 (s, 1H), 8.25 (s, 1H), 7.61-7.54 (m, 3H), 7.45-7.42 (m, 2H), 7.35 (s, 2H), 7.31 (s, 1H), 7.00 (s, 1H), 3.78 (s, 3H), 2.24-2.18 (m, 2H), 1.14-1.37 (m, 1H), 1.24-1.17 (m, 1H) |

TABLE A-1-continued

| Compd No. | Structure/Name | LCMS R$_T$(min) M + H+, Method | $^1$H NMR (ppm) |
|---|---|---|---|
| 305 | 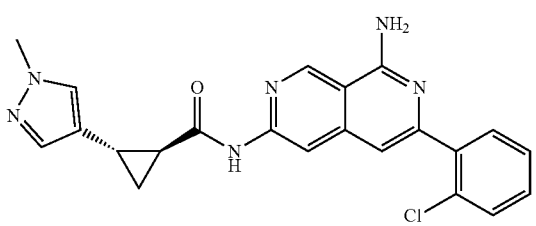 [SMILES: Cn1cc([C@H]2C[C@@H]2C(=O)Nc2cc3cc(-c4ccccc4Cl)nc(N)c3cn2)cn1]<br>(1R,2R)-N-[8-amino-6-(2-chlorophenyl)-2,7-naphthyridin-3-yl]-2-(1-methyl-1H-pyrazol-4-yl)cyclopropane-1-carboxamide (Absolute stereochemistry arbitrarily assigned) | 1.31<br>419<br>K-1 | $^1$H NMR (400 MHz, DMSO-d$_6$) δ 10.98 (s, 1H), 9.39 (s, 1H), 8.25 (s, 1H), 7.61-7.54 (m, 3H), 7.45-7.42 (m, 2H), 7.35 (s, 2H), 7.31 (s, 1H), 7.00 (s, 1H), 3.78 (s, 3H), 2.24-2.18 (m, 2H), 1.14-1.37 (m, 1H), 1.24-1.17 (m, 1H) |
| 306 | 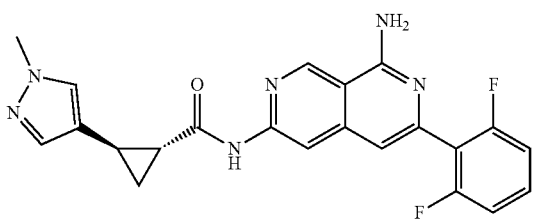 [SMILES: Cn1cc([C@@H]2C[C@H]2C(=O)Nc2cc3cc(-c4c(F)cccc4F)nc(N)c3cn2)cn1]<br>(1S,2S)-N-[8-amino-6-(2,6-difluorophenyl)-2,7-naphthyridin-3-yl]-2-(1-methyl-1H-pyrazol-4-yl)cyclopropane-1-carboxamide (Absolute stereochemistry arbitrarily assigned) | 2.332<br>421<br>K-1 | $^1$H NMR (400 MHz, CD$_3$OD) δ9.30 (s, 1H), 8.31 (s, 1H), 7.52-7.44 (m, 2H), 7.37 (s, 1H), 7.13-7.05 (m, 2H), 6.99 (s, 1H), 3.02 (s, 3H), 2.41-2.34 (m, 1H), 2.13-2.10 (m, 1H), 1.61-1.56 (m, 1H), 1.29-1.25 (m, 1H). |
| 307 | 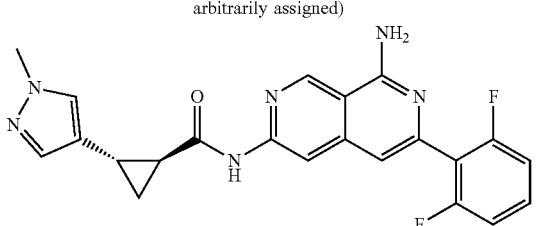<br>(1R,2R)-N-[8-amino-6-(2,6-difluorophenyl)-2,7-naphthyridin-3-yl]-2-(1-methyl-1H-pyrazol-4-yl)cyclopropane-1-carboxamide (Absolute stereochemistry arbitrarily assigned) | 1.310<br>421<br>K-1 | $^1$H NMR (400 MHz, CD$_3$OD) δ 9.30 (s, 1H), 8.31 (s, 1H), 7.52-7.44 (m, 2H), 7.37 (s, 1H), 7.13-7.05 (m, 2H), 6.99 (s, 1H), 3.02 (s, 3H), 2.41-2.34 (m, 1H), 2.13-2.10 (m, 1H), 1.61-1.56 (m, 1H), 1.29-1.25 (m, 1H). |
| 308 | 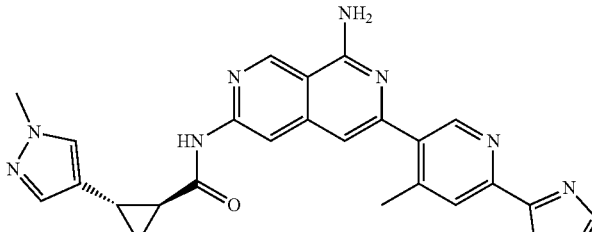<br>(1S,2S)-N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide (Absolute stereochemistry arbitrarily assigned) | 1.272<br>467<br>K-1 | $^1$H NMR (400 MHz, CD$_3$OD) δ 9.33 (s, 1H), 8.70 (s, 1H), 8.38 (s, 1H), 8.15-8.14 (m, 2H), 7.51 (s, 1H), 7.45-7.44 (m, 1H), 7.38 (s, 1H), 7.09 (s, 1H), 3.86 (s, 3H), 2.57 (s, 3H), 2.42-2.37 (m, 1H), 2.14-2.10 (m, 1H), 1.61-1.56 (m, 1H), 1.34-1.25 (m, 1H). |

TABLE A-1-continued

| Compd No. | Structure/Name | LCMS R$_T$(min) M + H$^+$, Method | $^1$H NMR (ppm) |
|---|---|---|---|
| 309 | 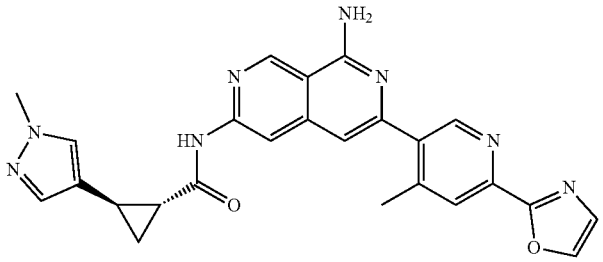 [SMILES: Cc1cc(-c2ncco2)ncc1-c1cc2cc(NC(=O)[C@@H]3C[C@H]3c3cnn(C)c3)ncc2c(N)n1]<br>(1R,2R)-N-[8-amino-6-[4-methyl-6-(1,3-oxazol-2-yl)pyridin-3-yl]-2,7-naphthyridin-3-yl]-2-(1-methyl-1H-pyrazol-4-yl)cyclopropane-1-carboxamide (Absolute stereochemistry arbitrarily assigned) | 1.280<br>467<br>K-1 | $^1$H NMR (400 MHz, CD$_3$OD) δ 9.33 (s, 1H), 8.70 (s, 1H), 8.38 (s, 1H), 8.15-8.14 (m, 2H), 7.51 (s, 1H), 7.45-7.44 (m, 1H), 7.38 (s, 1H), 7.09 (s, 1H), 3.86 (s, 3H), 2.57 (s, 3H), 2.42-2.37 (m, 1H), 2.14-2.10 (m, 1H), 1.61-1.56 (m, 1H), 1.34-1.25 (m, 1H). |
| 310 | 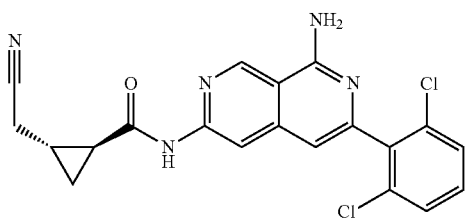<br>(1S,2R)-N-(8-amino-6-(2,6-dichlorophenyl)-2,7-naphthyridin-3-yl)-2-(cyanomethyl)cyclopropanecarboxamide (Absolute stereochemistry arbitrarily assigned) | 2.46<br>412<br>K-1 | $^1$H NMR (400 MHz, CD$_3$OD) δ 9.33 (s, 1H), 8.29 (s, 1H), 7.56-7.48 (m, 2H), 7.42 (dd, J = 8.0, 8.0 Hz, 1H), 6.86 (s, 1H), 2.79-2.64 (m, 2H), 2.03 (m, 1H), 1.81-1.70 (m, 1H), 1.35 (m, 1H), 1.06 (m, 1H). |
| 311 | 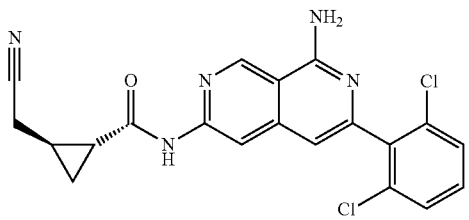<br>(1R,2S)-N-(8-amino-6-(2,6-dichlorophenyl)-2,7-naphthyridin-3-yl)-2-(cyanomethyl)cyclopropanecarboxamide (Absolute stereochemistry arbitrarily assigned) | 1.370<br>412<br>K-1 | $^1$H NMR (400 MHz, CD$_3$OD) δ 9.33 (s, 1H), 8.29 (s, 1H), 7.56-7.48 (m, 2H), 7.42 (dd, J = 8.0, 8.0 Hz, 1H), 6.86 (s, 1H), 2.79-2.64 (m, 2H), 2.03 (m, 1H), 1.81-1.70 (m, 1H), 1.35 (m, 1H), 1.06 (m, 1H). |
| 312 | 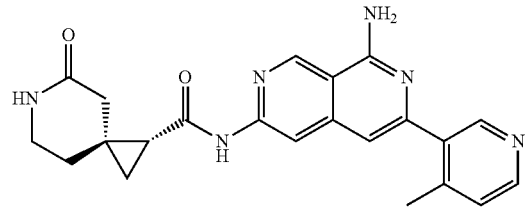 [SMILES: Cc1ccncc1-c1cc2cc(NC(=O)[C@@H]3C[C@@]34CCNC(=O)C4)ncc2c(N)n1]<br>(1R,3S)-N-[8-amino-6-(4-methylpyridin-3-yl)-2,7-naphthyridin-3-yl]-5-oxo-6-azaspiro[2.5]octane-1-carboxamide (Absolute stereochemistry arbitrarily assigned) | 0.903<br>403<br>K-1 | $^1$H NMR (300 MHz, DMSO-d$_6$) δ 10.95 (s, 1H), 9.37 (s, 1H), 8.57 (s, 1H), 8.43 (d, J = 6.0 Hz, 1H), 8.25 (s, 1H), 7.53 (s, 1H), 7.32-7.31 (m, 3H), 6.99 (s, 1H), 3.22-3.20 (m, 2H), 2.42 (s, 3H), 2.38-2.36 (m, 2H), 2.12-2.08 (m, 1H), 1.76-1.74 (m, 1H), 1.52-1.49 (m, 1H), 1.10-1.06 (m, 2H). |

TABLE A-1-continued

| Compd No. | Structure/Name | LCMS R_T(min) M + H+, Method | $^1$H NMR (ppm) |
|---|---|---|---|
| 313 | 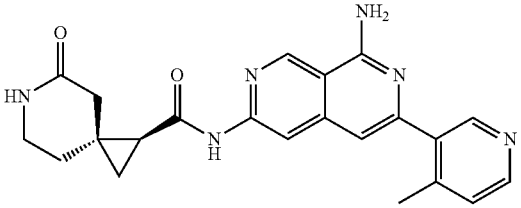 [SMILES: Cc1ccncc1-c1cc2cc(NC(=O)[C@H]3C[C@]34CCNC(=O)C4)ncc2c(N)n1]<br>(1S,3R)-N-[8-amino-6-(4-methylpyridin-3-yl)-2,7-naphthyridin-3-yl]-5-oxo-6-azaspiro[2.5]octane-1-carboxamide (Absolute stereochemistry arbitrarily assigned) | 0.903<br>403<br>K-1 | $^1$H NMR (300 MHz, DMSO-d$_6$) δ 10.97 (s, 1H), 9.39 (s, 1H), 8.58 (s, 1H), 8.45 (d, J = 6.0 Hz, 1H), 8.27 (s, 1H), 7.53 (s, 1H), 7.41 (s, 2H), 7.33 (d, J = 6.0 Hz, 1H), 7.01 (s, 1H), 3.21-3.16 (m, 2H), 2.42 (s, 3H), 2.38-2.36 (m, 2H), 2.12-2.08 (m, 1H), 1.97-1.70 (m, 1H), 1.53-1.45(m, 1H), 1.12-1.05 (m, 2H). |
| 314 | 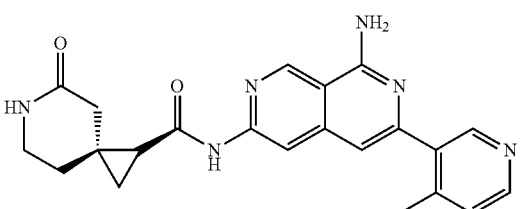<br>(1S,3S)-N-[8-amino-6-(4-methylpyridin-3-yl)-2,7-naphthyridin-3-yl]-5-oxo-6-azaspiro[2.5]octane-1-carboxamide (Absolute stereochemistry arbitrarily assigned) | 1.014<br>403<br>K-1 | $^1$H NMR (300 MHz, DMSO-d$_6$) 10.96 (s, 1H), 9.37(s, 1H), 8.57 (s, 1H), 8.43 (d, J = 6.0 Hz, 1H), 8.25 (s, 1H), 7.58 (s, 1H), 7.32-7.30 (m, 3H), 6.97 (s, 1H), 3.15-3.12 (m, 1H), 3.02-2.99 (m, 1H), 2.41 (s, 3H), 2.31-2.25 (m, 1H), 2.11-2.04 (m, 2H), 1.92-1.78(m, 2H), 1.19-1.16 (m, 1H), 1.10-0.96 (m, 1H). |
| 315 | 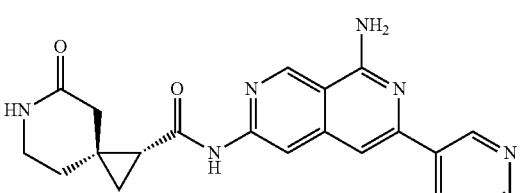<br>(1R,3R)-N-[8-amino-6-(4-methylpyridin-3-yl)-2,7-naphthyridin-3-yl]-5-oxo-6-azaspiro[2.5]octane-1-carboxamide (Absolute stereochemistry arbitrarily assigned) | 1.007<br>403<br>K-1 | $^1$H NMR (300 MHz, CD$_3$OD) 9.30 (s, 1H), 8.54 (s, 1H), 8.44 (d, J = 6.0 Hz, 1H), 8.32 (s, 1H), 7.41 (d, J = 6.0 Hz, 1H), 6.99 (s, 1H), 3.27-3.21 (m, 2H), 2.46-2.30 (m, 5H), 2.06-1.99 (m, 3H), 1.47-1.39 (m, 1H), 1.11-1.07 (m, 1H). |
| 316 | 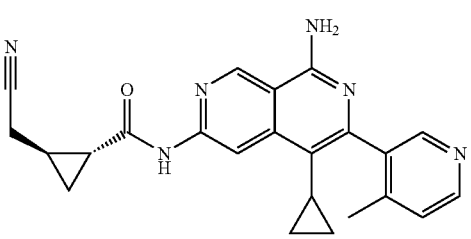 [SMILES: Cc1ccncc1-c1nc(N)c2cnc(NC(=O)[C@@H]3C[C@H]3CC#N)cc2c1C1CC1]<br>(1R,2S)-N-(8-amino-5-cyclopropyl-6-(4-methylpyridin-3-yl)-2,7-naphthyridin-3-yl)-2-(cyanomethyl)cyclopropane-1-carboxamide (Absolute stereochemistiy arbitrarily assigned) | 2.182<br>399<br>K-1 | $^1$H NMR (400 MHz, CD$_3$OD) δ 9.39 (s, 1H), 9.04 (s, 1H), 8.51 (d, J = 4 Hz, 1H), 8.50 (s, 1H), 8.51 (d, J = 4 Hz, 1H), 2.81-2.66 (m, 2H), 2.34 (s, 3H), 2.09-2.03 (m, 1H), 1.90-1.75 (m, 2H), 1.41-1.36 (m, 1H), 1.11-1.07 (m, 1H), 0.88-0.77 (s, 2H), 0.17-0.07 (m, 2H). |

TABLE A-1-continued

| Compd No. | Structure/Name | LCMS R_T(min) M + H+, Method | 1H NMR (ppm) |
|---|---|---|---|
| 317 | 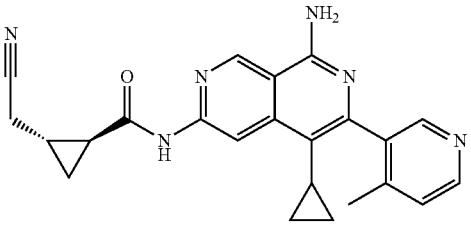 [SMILES: Cc1ccncc1-c1nc(N)c2cnc(NC(=O)[C@H]3C[C@@H]3CC#N)cc2c1C1CC1]<br>(1S,2R)-N-(8-amino-5-cyclopropyl-6-(4-methylpyridin-3-yl)-2,7-naphthyridin-3-yl)-2-(cyanomethyl)cyclopropane-1-carboxamide (Absolute stereochemistry arbitrarily assigned) | 1.079<br>399<br>K-1 | 1H NMR (400 MHz, CD3OD) δ 9.39 (s, 1H), 9.04 (s, 1H), 8.51 (d, J = 4 Hz, 1H), 8.50 (s, 1H), 8.51 (d, J = 4 Hz, 1H), 2.81-2.66 (m, 2H), 2.34 (s, 3H), 2.09-2.03 (m, 1H), 1.90-1.75 (m, 2H), 1.41-1.36 (m, 1H), 1.11-1.07 (m, 1H), 0.88-0.77 (s, 2H), 0.17-0.07 (m, 2H). |
| 318 | 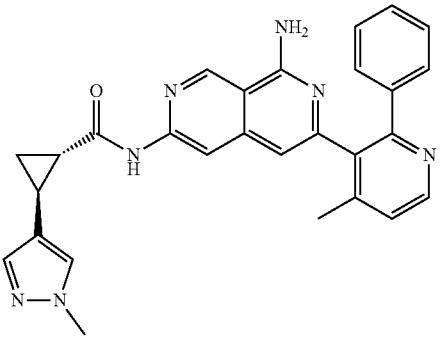 [SMILES: Cc1ccnc(-c2ccccc2)c1-c1cc2cc(NC(=O)[C@H]3C[C@@H]3c3cnn(C)c3)ncc2c(N)n1]<br>(1S,2S)-N-(8-amino-6-(4-methyl-2-phenylpyridin-3-yl)-2,7-naphthyridin-3-yl)-2-(1-methyl-1H-pyrazol-4-yl)cyclopropanecarboxamide (Absolute stereochemistry arbitrarily assigned) | 1.196<br>476<br>K-1 | 1H NMR (400 MHz, CD3OD) δ 9.22 (s, 1H), 8.52 (d, J = 4 Hz, 1H), 8.05 (s, 1H), 7.48 (s, 1H), 7.42 (d, J = 4.0 Hz, 1H), 7.40-7.38 (m, 2H), 7.35 (s, 1H), 7.23-7.20 (m, 3H), 6.57 (s, 1H), 3.85 (s, 3H), 2.37-2.33 (m, 1H), 2.31 (s, 3H), 2.09-2.058 (m, 1H), 1.56-1.51 (m, 1H), 1.26-1.21 (m, 1H). |
| 319 | 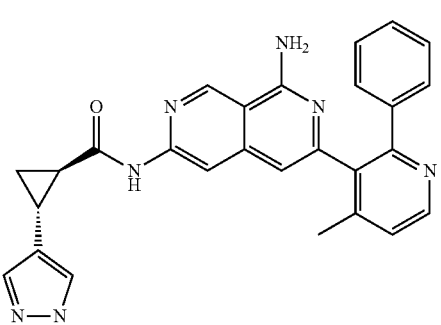<br>(1R,2R)-N-(8-amino-6-(4-methyl-2-phenylpyridin-3-yl)-2,7-naphthyridin-3-yl)-2-(1-methyl-1H-pyrazol-4-yl)cyclopropanecarboxamide (Absolute stereochemistry arbitrarily assigned) | 1.197<br>476<br>K-1 | 1H NMR (400 MHz, CD3OD) δ 9.22 (s, 1H), 8.52 (d, J = 4 Hz, 1H), 8.05(s, 1H), 7.48 (s, 1H), 7.42 (d, J = 4.0 Hz, 1H), 7.40-7.38 (m, 2H), 7.35 (s, 1H), 7.23-7.20 (m, 3H), 6.57 (s, 1H), 3.85 (s, 3H), 2.37-2.33 (m, 1H), 2.31 (s, 3H), 2.09-2.06 (m, 1H), 1.56-1.51 (m, 1H), 1.26-1.21 (m, 1H). |

TABLE A-1-continued

| Compd No. | Structure/Name | LCMS R_T(min) M + H+, Method | 1H NMR (ppm) |
|---|---|---|---|
| 320 | 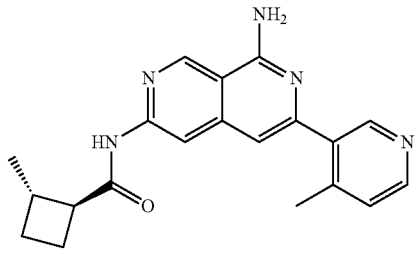 [SMILES: Cc1ccncc1-c1cc2cc(NC(=O)[C@H]3CC[C@@H]3C)ncc2c(N)n1]<br>(1S,2S)-N-(8-amino-6-(4-methylpyridin-3-yl)-2,7-naphthyridin-3-yl)-2-methylcyclobutanecarboxamide (Absolute stereochemistry arbitrarily assigned) | 1.290<br>348<br>K-1 | $^1$H NMR (400 MHz, CD$_3$OD) δ 9.29 (s, 1H), 8.55 (s, 1H), 8.44 (d, J = 4.0 Hz, 1H), 8.37 (s, 1H), 7.41 (d, J = 4 Hz, 1H), 7.01 (s, 1H), 2.99-2.92 (m, 1H), 2.76-2.68 (m, 1H), 2.47 (s, 3H), 2.25-2.05 (m, 3H), 1.69-1.60 (m, 1H), 1.19 (d, J = 8.0 Hz, 3H). |
| 321 | 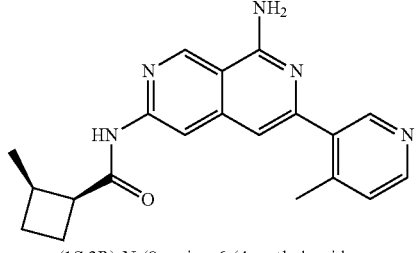<br>(1S,2R)-N-(8-amino-6-(4-methylpyridm-3-yl)-2,7-naphthyridin-3-yl)-2-methylcyclobutanecarboxamide (Absolute stereochemistry arbitrarily assigned) | 1.420<br>348<br>K-1 | $^1$H NMR (400 MHz, CD$_3$OD) δ 9.29 (s, 1H), 8.56 (s, 1H), 8.44 (d, J = 4.0 Hz, 1H), 8.39 (s, 1H), 7.41 (d, J = 4.0 Hz, 1H), 7.01 (s, 1H), 3.51-3.45 (m, 1H), 2.96-2.89 (m, 1H), 2.55-2.48 (m, 1H), 2.47 (s, 3H), 2.27-2.18 (m, 1H), 2.09-2.00 (m, 1H), 1.73-1.65 (m, 1H), 1.11 (d, J = 8.0 Hz, 3H). |
| 322 | 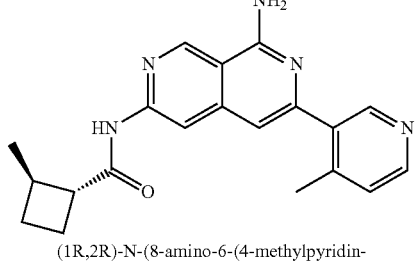<br>(1R,2R)-N-(8-amino-6-(4-methylpyridin-3-yl)-2,7-naphthyridin-3-yl)-2-methylcyclobutanecarboxamide (Absolute stereochemistry-arbitrarily assigned) | 0.980<br>348<br>K-1 | $^1$H NMR (400 MHz, CD$_3$OD) δ 9.29 (s, 1H), 8.55 (s, 1H), 8.44 (d, J = 4.0 Hz, 1H), 8.37 (s, 1H), 7.41 (d, J = 4.0 Hz, 1H), 7.01 (s, 1H), 2.99-2.92 (m, 1H), 2.76-2.68 (m, 1H), 2.47 (s, 3H), 2.25-2.05 (m, 3H), 1.69-1.60 (m, 1H), 1.19 (d, J = 8.0 Hz, 3H). |
| 323 | 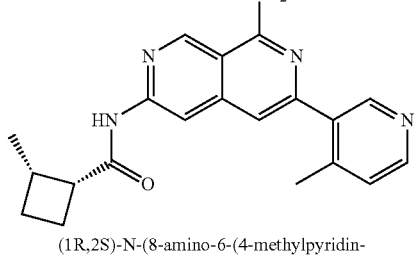<br>(1R,2S)-N-(8-amino-6-(4-methylpyridin-3-yl)-2,7-naphthyridin-3-yl)-2-methylcyclobutanecarboxamide (Absolute stereochemistry arbitrarily assigned) | 0.980<br>348<br>K-1 | $^1$H NMR (400 MHz, CD$_3$OD) δ 9.29 (s, 1H), 8.56 (s, 1H), 8.44 (d, J = 4.0 Hz, 1H), 8.39 (s, 1H), 7.41 (d, J = 4.0 Hz, 1H), 7.01 (s, 1H), 3.51-3.45 (m, 1H), 2.96-2.89 (m, 1H), 2.55-2.48 (m, 1H), 2.47 (s, 3H), 2.27-2.18 (m, 1H), 2.09-2.00 (m, 1H), 1.73-1.65 (m, 1H), 1.11 (d, J = 8.0 Hz, 3H). |

TABLE A-1-continued

| Compd No. | Structure/Name | LCMS R_T(min) M + H+, Method | ¹H NMR (ppm) |
|---|---|---|---|
| 324 | 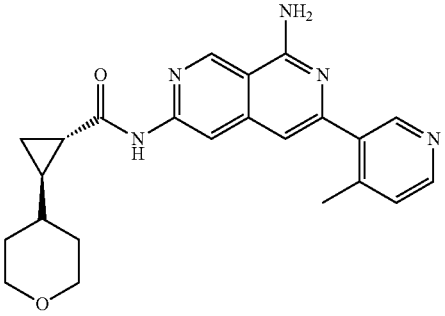 [SMILES: Cc1ccncc1-c1cc2cc(NC(=O)[C@H]3C[C@@H]3C3CCOCC3)ncc2c(N)n1]<br>(1S,2R)-N-[8-amino-6-(4-methylpyridin-3-yl)-2,7-naphthyridin-3-yl]-2-(oxan-4-yl)cyclopropane-1-carboxamide<br>(Absolute stereochemistry arbitrarily assigned) | 1.100<br>404<br>K-1 | ¹H NMR (400 MHz, CD₃OD) δ 9.32 (s, 1H), 8.55 (s, 1H), 8.46 (d, J = 5.1Hz, 1H), 8.32 (s, 1H), 7.43 (d, J = 5.1Hz, 1H), 7.01 (s, 1H), 4.03-3.92 (m, 2H), 3.47-3.37 (m, 2H), 2.47 (s, 3H), 1.87-1.83 (m, 1H), 1.76 (t, J = 14.6 Hz, 2H), 1.57-1.42 (m, 2H), 1.38-1.31 (m, 1H), 1.25-1.21 (m, 1H), 1.19-1.07 (m, 1H), 0.93-0.89 (m, 1H). |
| 325 | 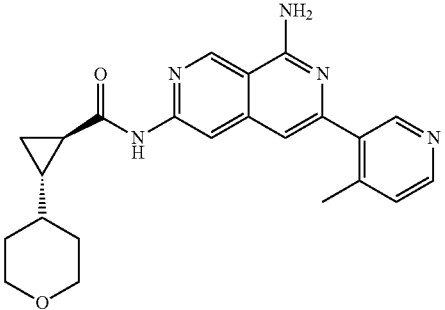 [SMILES: Cc1ccncc1-c1cc2cc(NC(=O)[C@@H]3C[C@H]3C3CCOCC3)ncc2c(N)n1]<br>(1R,2S)-N-[8-amino-6-(4-methylpyridin-3-yl)-2,7-naphthyridin-3-yl]-2-(oxan-4-yl)cyclopropane-1-carboxamide<br>(Absolute stereochemistry arbitrarily assigned) | 1.080<br>404<br>K-1 | ¹H NMR (400 MHz, CD₃OD) δ 9.32 (s, 1H), 8.55 (s, 1H), 8.46 (d, J = 5.1Hz, 1H), 8.32 (s, 1H), 7.43 (d, J = 5.1Hz, 1H), 7.01 (s, 1H), 4.03-3.92 (m, 2H), 3.47-3.37 (m, 2H), 2.47 (s, 3H), 1.87-1.83 (m, 1H), 1.76 (t, J = 14.6 Hz, 2H), 1.57-1.42 (m, 2H), 1.38-1.31 (m, 1H), 1.25-1.21 (m, 1H), 1.19-1.07 (m, 1H), 0.93-0.89 (m, 1H). |
| 326 | 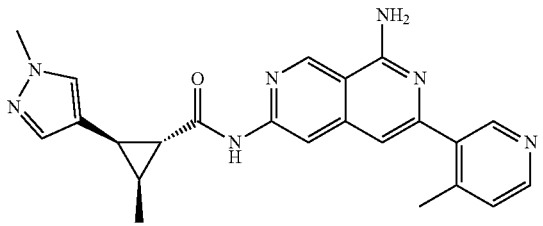 [SMILES: Cc1ccncc1-c1cc2cc(NC(=O)[C@@H]3[C@@H](C)[C@H]3c3cnn(C)c3)ncc2c(N)n1]<br>(1R,2S,3R)-N-[8-amino-6-(4-methylpyridin-3-yl)-2,7-naphthyridin-3-yl]-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | 1.980<br>414<br>K-1 | ¹H NMR (400 MHz, CD₃OD) δ 9.29 (s, 1H), 8.53 (s, 1H), 8.43-8.41 (m, 1H), 8.32 (s, 1H), 7.50 (s, 1H), 7.40-7.38 (m, 1H), 7.33 (s, 1H), 6.98 (s, 1H), 3.87 (s, 3H), 2.54-2.49 (m, 1H), 2.45 (s, 3H), 2.00-1.97 (m, 1H), 1.79-1.72 (m, 1H), 1.06-1.04 (m, 3H). |

TABLE A-1-continued

| Compd No. | Structure/Name | LCMS R_T(min) M + H+, Method | 1H NMR (ppm) |
| --- | --- | --- | --- |
| 327 | (1S,2R,3S)-N-[8-amino-6-(4-methylpyridin-3-yl)-2,7-naphthyridin-3-yl]-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | 1.090 414 K-1 | 1H NMR (400 MHz, CD3OD) δ 9.28 (s, 1H), 8.54 (s, 1H), 8.43-8.41 (m, 1H), 8.34 (s, 1H), 7.45 (s, 1H), 7.40-7.38 (m, 1H), 7.33 (s, 1H), 6.99 (s, 1H), 3.84 (s, 3H), 2.45 (s, 3H), 2.31-2.35 (m, 1H), 2.14-2.18 (m, 1H), 1.63-1.67(m, 1H), 1.33-1.35 (m, 3H). |
| 328 | (1S,2S,3S)-N-[8-amino-6-(4-methylpyridin-3-yl)-2,7-naphthyridin-3-yl]-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | 1.076 414 K-1 | 1H NMR (400 MHz, CD3OD) δ 9.29 (s, 1H), 8.53 (s, 1H), 8.43-8.41 (m, 1H), 8.32 (s, 1H), 7.50 (s, 1H), 7.40-7.38 (m, 1H), 7.33 (s, 1H), 6.98 (s, 1H), 3.93 (s, 3H), 2.54-2.49 (m, 1H), 2.45 (s, 3H), 2.00-1.97 (m, 1H), 1.79-1.72 (m, 1H), 1.06-1.04 (m, 3H). |
| 329 | (1R,2R,3R)-N-[8-amino-6-(4-methylpyridin-3-yl)-2,7-naphthyridin-3-yl]-2-methyl-3-(1-methyl-1H-pyrazol-4-yl)cyclopropane-1-carboxamide (Pyrazole trans to amide; methyl relative stereochemistry arbitrarily assigned; Absolute stereochemistry7 arbitrarily assigned) | 1.070 414 K-1 | 1H NMR (400 MHz, CD3OD) δ 9.29 (s, 1H), 8.53 (s, 1H), 8.43-8.41 (m, 1H), 8.34 (s, 1H), 7.45 (s, 1H), 7.40-7.38 (m, 1H), 7.33 (s, 1H), 6.98 (s, 1H), 3.84 (s, 3H), 2.45 (s, 3H), 2.31-2.35 (m, 1H), 2.14-2.18 (m, 1H), 1.63-1.67(m, 1H), 1.33-1.35 (m, 3H). |

TABLE A-1-continued

| Compd No. | Structure/Name | LCMS R$_T$(min) M + H$^+$, Method | $^1$H NMR (ppm) |
|---|---|---|---|
| 330 | (1R,2R)-N-(8-amino-6-(4-methylpyridin-3-yl)-2,7-naphthyridin-3-yl)-2-(1-(2-methoxyethyl)-1H-pyrazol-4-yl)cyclopropanecarboxamide (Absolute stereochemistry arbitrarily assigned) | 1.060 444 K-1 | $^1$H NMR (300 MHz, DMSO-d$_6$) δ 10.97 (s, 1H), 9.38 (s, 1H), 8.57 (s, 1H), 8.45 (d, J = 6.0 Hz, 1H), 8.26 (s, 1H), 7.59 (s, 1H), 7.41 (s, 2H), 7.38-7.22 (m, 2H), 6.99 (s, 1H), 4.17 (t, J = 6.0 Hz, 2H), 3.64 (t, J = 6.0 Hz, 2H), 3.22 (s, 3H), 2.41 (s, 3H), 2.22 (t, J = 6.0 Hz, 2H), 1.52-1.33 (m, 1H), 1.23-1.27 (m, 1H). |
| 331 | (1S,2S)-N-(8-amino-6-(4-methylpyridin-3-yl)-2,7-naphthyridin-3-yl)-2-(1-(2-methoxyethyl)-1H-pyrazol-4-yl)cyclopropanecarboxamide (Absolute stereochemistry arbitrarily assigned) | 1.050 444 K-1 | $^1$H NMR (300 MHz, DMSO-d$_6$) δ 10.97 (s, 1H), 9.38 (s, 1H), 8.57 (s, 1H), 8.45 (d, J = 6.0 Hz, 1H), 8.26 (s, 1H), 7.59 (s, 1H), 7.41 (s, 2H), 7.38-7.22 (m, 2H), 6.99 (s, 1H), 4.17 (t, J = 6.0 Hz, 2H), 3.64 (t, J = 6.0 Hz, 2H), 3.22 (s, 3H), 2.41 (s, 3H), 2.22 (t, J = 6.0 Hz, 2H), 1.52-1.33 (m, 1H), 1.23-1.27 (m, 1H). |
| 332 | (1S,2S)-N-(8-amino-5-chloro-6-(4-(2-hydroxyethyl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 1.090 464 K-1 | $^1$H NMR (400 MHz, CD$_3$OD) δ 9.36 (s, 1H), 8.74 (s, 1H), 8.59 (d, J = 8.0 Hz, 1H), 8.53 (s, 1H), 7.65 (d, J = 8.0 Hz, 1H), 7.51 (s, 1H), 7.38 (s, 1H), 3.86 (s, 3H), 3.75 (t, J = 8.0 Hz, 2H), 2.89 (t, J = 8.0 Hz, 2H), 2.44-2.39 (m, 1H), 2.16-2.12 (m, 1H), 1.62-1.58 (m, 1H), 1.32-1.27 (m, 1H). |
| 333 | (1R,2R)-N-(8-amino-5-chloro-6-(4-(2-hydroxyethyl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 1.090 464 K-1 | $^1$H NMR (400 MHz, CD$_3$OD) δ 9.36 (s, 1H), 8.74 (s, 1H), 8.59 (d, J = 8.0 Hz, 1H), 8.53 (s, 1H), 7.65 (d, J = 8.0 Hz, 1H), 7.51 (s, 1H), 7.38 (s, 1H), 3.86 (s, 3H), 3.75 (t, J = 8.0 Hz, 2H), 2.89 (t, J = 8.0 Hz, 2H), 2.44-2.39 (m, 1H), 2.16-2.12 (m, 1H), 1.62-1.58 (m, 1H), 1.32-1.27 (m, 1H). |

TABLE A-1-continued

| Com- pd No. | Structure/Name | LCMS R$_T$(min) M + H$^+$, Method | $^1$H NMR (ppm) |
|---|---|---|---|
| 334 | (1R,2S)-N-(8-amino-6-(4-methyl-6-phenylpyridin-3-yl)-2,7-naphthyridin-3-yl)-2-(cyanomethyl)cyclopropane-1-carboxamide (Absolute stereochemistry arbitrarily assigned) | 1.370 435 K-1 | $^1$H NMR (300 MHz, CD$_3$OD) δ 9.31 (s, 1H), 8.62 (s, 1H), 8.32 (s, 1H), 8.02-7.98 (m, 2H), 7.82 (s, 1H), 7.56-7.54 (m, 2H), 7.03 (s, 1H), 2.79-2.69 (m, 2H), 2.54 (s, 3H), 2.06-2.00 (m, 1H), 1.97-1.72 (m, 1H), 1.39-1.31 (m, 1H), 1.09-1.02 (m, 1H). |
| 335 | (1S,2R)-N-(8-amino-6-(4-methyl-6-phenylpyridin-3-yl)-2,7-naphthyridin-3-yl)-2-(cyanomethyl)cyclopropane-1-carboxamide (Absolute stereochemistry arbitrarily assigned) | 1.370 435 K-1 | $^1$H NMR (300 MHz, CD$_3$OD) δ 9.31 (s, 1H), 8.62 (s, 1H), 8.32 (s, 1H), 8.02-7.98 (m, 2H), 7.82 (s, 1H), 7.56-7.54 (m, 3H), 7.03 (s, 1H), 2.79-2.69 (m, 2H), 2.54 (s, 3H), 2.06-2.00 (m, 1H), 1.97-1.72 (m, 1H), 1.39-1.31 (m, 1H), 1.09-1.02 (m, 1H). |
| 336 | N-(8-amino-6-(4-methylpyridin-3-yl)-2,7-naphthyridin-3-yl)spiro[2.2]pentane-1-carboxamide | 2.82 346.1 Q | $^1$H NMR (400 MHz, DMSO-d$_6$) δ 10.75 (s, 1H), 9.35 (s, 1H), 8.56 (s, 1H), 8.43 (d, J = 5.0 Hz, 1H), 8.26 (s, 1H), 7.28 (br s, 2H), 7.33-7.21 (m, 1H), 6.95 (s, 1H), 2.43-2.40 (m, 1H), 2.41 (s, 3H), 1.42 (t, J = 3.8 Hz, 1H), 1.35 (dd, J = 7.4, 3.4 Hz, 1H), 0.95-0.73 (m, 4H). |
| 337 | N6-((2,2-difluorocyclopropyl)methyl)-3-(4-methylpyridin-3-yl)-2,7-naphthyridine-1,6-diamine | 2.69 342.1 Q | $^1$H NMR (400 MHz, DMSO-d$_6$) δ 9.20 (s, 1H), 8.54 (s, 1H), 8.46 (d, J = 5.0 Hz, 1H), 7.33 (d, J = 5.0 Hz, 1H), 7.25 (br s, 2H), 6.75 (s, 1H), 6.51 (s, 3H), 3.53-3.39 (m, 2H), 2.38 (s, 3H), 2.14-1.98 (m, 1H), 1.66-1.52 (m, 1H), 1.39-1.28 (m, 1H). |

TABLE A-1-continued

| Compd No. | Structure/Name | LCMS R_T(min) M + H+, Method | ¹H NMR (ppm) |
|---|---|---|---|
| 338 | 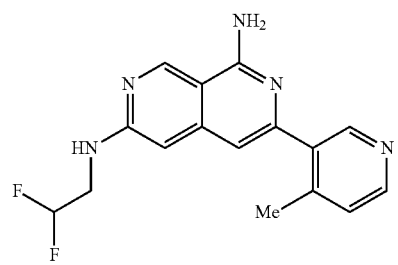 [SMILES: Cc1ccncc1-c1cc2cc(NCC(F)F)ncc2c(N)n1]<br>N6-(2,2-difluoroethyl)-3-(4-methylpyridin-3-yl)-2,7-naphthyridine-1,6-diamine | 2.23<br>316.1<br>Q | ¹H NMR (400 MHz, DMSO-d$_6$) δ 9.14 (s, 1H), 8.52 (s, 1H), 8.41 (d, J = 5.0 Hz, 1H), 7.28 (d, J = 5.0 Hz, 1H), 7.14 (t, J = 6.4 Hz, 1H), 7.04 (br s, 2H), 6.69 (s, 1H), 6.56 (s, 1H), 6.13 (tt, J = 56.3, 4.0 Hz, 1H), 3.84-3.69 (m, 2H), 2.39 (s, 3H). |
| 339 | 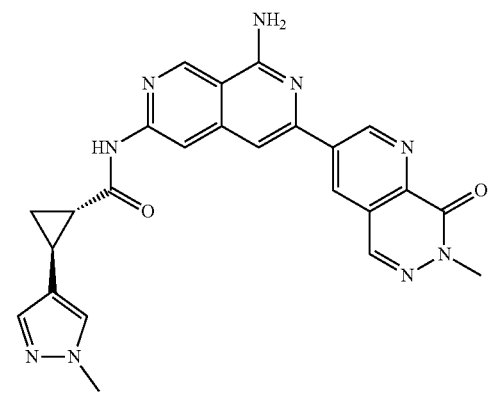 [SMILES: Cn1cc([C@H]2C[C@@H]2C(=O)Nc2cc3cc(-c4cnc5c(=O)n(C)ncc5c4)nc(N)c3cn2)cn1]<br>(1S,2S)-N-(8-amino-6-(7-methyl-8-oxo-7,8-dihydropyrido[2,3-d]pyridazin-3-yl)-2,7-naphthyndin-3-yl)-2-(1-methyl-1H-pyrazol-4-yl)cyclopropane-1-carboxamide (Absolute stereochemistry arbitrarily assigned) | 3.33<br>468.2<br>Q | ¹H NMR (400 MHz, DMSO-d$_6$) δ 11.01 (s, 1H), 9.77 (d, J = 2.3 Hz, 1H), 9.41 (s, 1H), 9.00 (d, J = 2.3 Hz, 1H), 8.50 (s, 1H), 8.37 (s, 1H), 7.75 (s, 1H), 7.57 (s, 1H), 7.50 (s, 2H), 7.30 (s, 1H), 3.78 (s, 3H), 3.77 (s, 3H), 2.28-2.18 (m, 2H), 1.46-1.36 (m, 1H), 1.28-1.15 (m, 1H). |
| 340 | 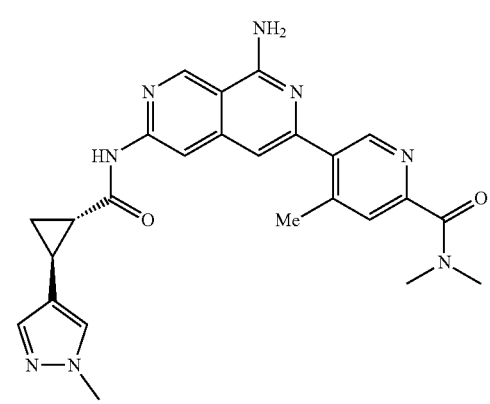 [SMILES: Cc1cc(C(=O)N(C)C)ncc1-c1cc2cc(NC(=O)[C@H]3C[C@@H]3c3cnn(C)c3)ncc2c(N)n1]<br>5-(1-amino-6-((1S,2S)-2-(1-methyl-1H-pyrazol-4-yl)cyclopropane-1-carboxamido)-2,7-naphthyridin-3-yl)-N,N,4-trimethylpicolinamide (Absolute stereochemistry arbitrarily assigned) | 3.23<br>471.2<br>Q | ¹H NMR (400 MHz, DMSO-d$_6$) δ 10.96 (s, 1H), 9.38 (s, 1H), 8.58 (s, 1H), 8.25 (s, 1H), 7.56 (s, 1H), 7.48 (s, 1H), 7.34 (br s, 2H), 7.29 (s, 1H), 7.03 (s, 1H), 3.76 (s, 3H), 3.02 (s, 3H), 2.99 (s, 3H), 2.46 (s, 3H), 2.24-2.16 (m, 2H), 1.44-1.33 (m, 1H), 1.24-1.12 (m, 1H). |

TABLE A-1-continued

| Compd No. | Structure/Name | LCMS R$_T$(min) M + H$^+$, Method | $^1$H NMR (ppm) |
|---|---|---|---|
| 341 | 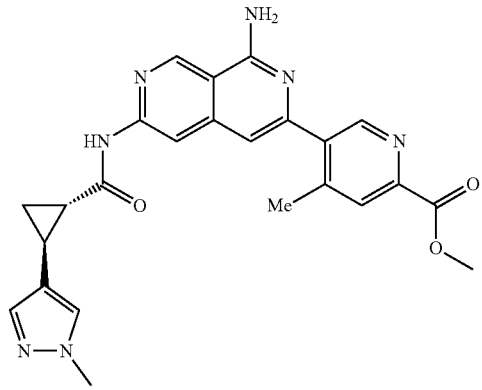 [SMILES: COC(=O)c1cc(C)c(-c2cc3cc(NC(=O)[C@H]4C[C@@H]4c4cnn(C)c4)ncc3c(N)n2)cn1]<br>methyl 5-(1-amino-6-((1S,2S)-2-(1-methyl-1H-pyrazol-4-yl)cyclopropane-1-carboxamido)-2,7-naphthyridin-3-yl)-4-methylpicolinate (Absolute stereochemistry arbitrarily assigned) | 3.43<br>458.1<br>Q | $^1$H NMR (400 MHz, DMSO-d$_6$) δ 10.95 (s, 1H), 9.38 (s, 1H), 8.71 (s, 1H), 8.28 (s, 1H), 8.01 (s, 1H), 7.56 (s, 1H), 7.37 (br s, 2H), 7.29 (s, 1H), 7.05 (s, 1H), 3.91 (s, 3H), 3.77 (s, 3H), 2.25-2.16 (m, 2H), 1.90 (s, 3H), 1.43-1.34 (m, 1H), 1.24-1.14 (m, 1H). |
| 342 | 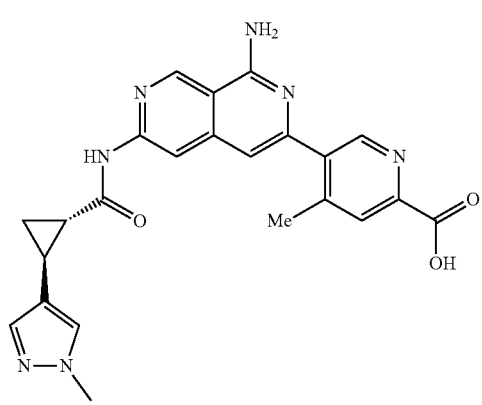 [SMILES: Cc1cc(C(=O)O)ncc1-c1cc2cc(NC(=O)[C@H]3C[C@@H]3c3cnn(C)c3)ncc2c(N)n1]<br>5-(1-amino-6-((1S,2S)-2-(1-methyl-1H-pyrazol-4-yl)cyclopropane-1-carboxamido)-2,7-naphthyridin-3-yl)-4-methylpicolinic acid (Absolute stereochemistry arbitrarily assigned) | 2.91<br>444.1<br>Q | $^1$H NMR (400 MHz, DMSO-d$_6$) δ 10.94 (s, 1H), 9.37 (s, 1H), 8.59 (s, 1H), 8.27 (s, 1H), 7.90 (s, 1H), 7.56 (s, 1H), 7.34 (br s, 2H), 7.29 (s, 1H), 7.01 (s, 1H), 3.77 (s, 3H), 2.46 (s, 3H), 2.25-2.16 (m, 2H), 1.43-1.34 (m, 1H), 1.23-1.13 (m, 1H). |
| 343 | 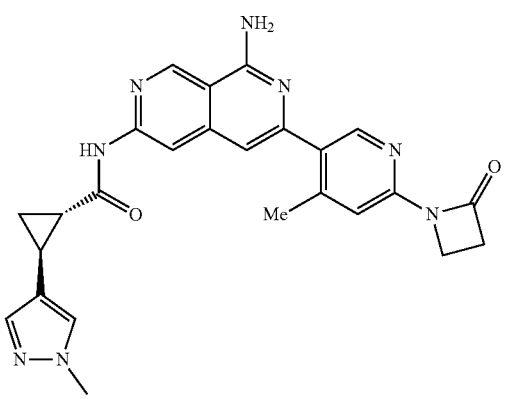 [SMILES: Cc1cc(N2CCC2=O)ncc1-c1cc2cc(NC(=O)[C@H]3C[C@@H]3c3cnn(C)c3)ncc2c(N)n1]<br>(1S,2S)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 3.29<br>469.2<br>Q | $^1$H NMR (400 MHz, DMSO-d$_6$) δ 10.92 (s, 1H), 9.35 (s, 1H), 8.34 (s, 1H), 8.24 (s, 1H), 7.56 (s, 1H), 7.52 (s, 1H), 7.29 (s, 1H), 7.28 (br s, 2H), 6.93 (s, 1H), 3.77 (s, 3H), 3.73 (dd, J = 4.7, 4.7 Hz, 2H), 3.12 (dd, J = 4.7, 4.7 Hz, 2H), 2.44 (s, 3H), 2.24-2.17 (m, 2H), 1.43-1.33 (m, 1H), 1.23-1.14 (m, 1H). |

TABLE A-1-continued

| Compd No. | Structure/Name | LCMS R$_T$(min) M + H$^+$, Method | $^1$H NMR (ppm) |
|---|---|---|---|
| 344 | 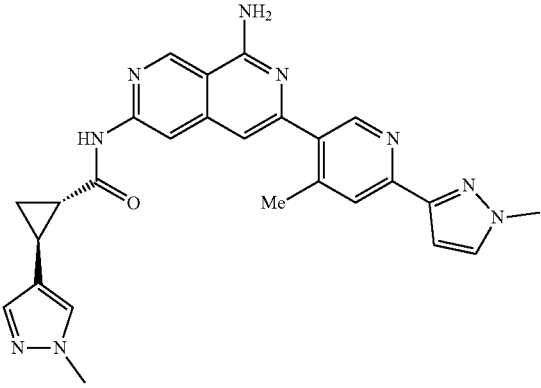 [SMILES: Cc1cc(-c2ccn(C)n2)ncc1-c1cc2cc(NC(=O)[C@H]3C[C@@H]3c3cnn(C)c3)ncc2c(N)n1]<br>(1S,2S)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 3.79<br>480.2<br>Q | $^1$H NMR (400 MHz, DMSO-d$_6$) δ 10.93 (s, 1H), 9.36 (s, 1H), 8.56 (s, 1H), 8.26 (s, 1H), 7.83 (s, 1H), 7.78 (d, J = 2.1Hz, 1H), 7.56 (s, 1H), 7.30 (br s, 2H), 7.29 (d, J = 2.1Hz, 1H), 7.00 (s, 1H), 6.81 (s, 1H), 3.93 (s, 3H), 3.77 (s, 3H), 2.47 (s, 3H), 2.26-2.14 (m, 2H), 1.45-1.32 (m, 1H), 1.28-1.15 (m, 1H). |
| 345 | 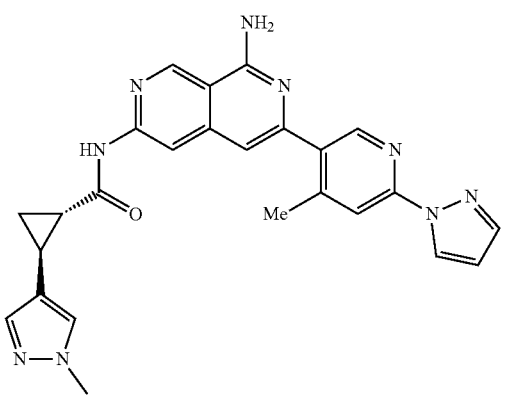 [SMILES: Cc1cc(-n2cccn2)ncc1-c1cc2cc(NC(=O)[C@H]3C[C@@H]3c3cnn(C)c3)ncc2c(N)n1]<br>(1S,2S)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 4.10<br>466.2<br>Q | $^1$H NMR (400 MHz, DMSO-d$_6$) δ 10.94 (s, 1H), 9.37 (s, 1H), 8.65 (d, J = 3.0 Hz, 1H), 8.48 (s, 1H), 8.27 (s, 1H), 7.88 (s, 1H), 7.85 (d, J = 3.0 Hz, 1H), 7.56 (s, 1H), 7.33 (br s, 2H), 7.29 (s, 1H), 7.03 (s, 1H), 6.60 (s, 1H), 3.77 (s, 3H), 2.54 (s, 3H), 2.25-2.16 (m, 2H), 1.43-1.34 (m, 1H), 1.23-1.16 (m, 1H). |
| 346 | 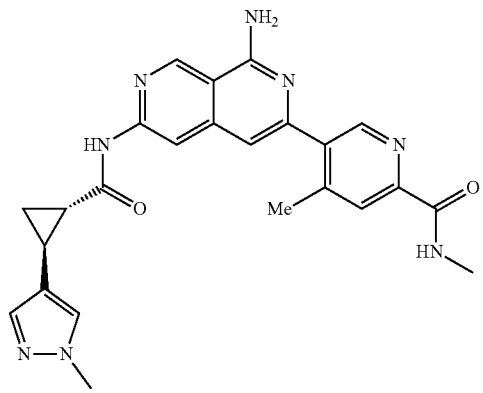 [SMILES: CNC(=O)c1cc(C)c(-c2cc3cc(NC(=O)[C@H]4C[C@@H]4c4cnn(C)c4)ncc3c(N)n2)cn1]<br>5-(1-amino-6-((1S,2S)-2-(1-methyl-1H-pyrazol-4-yl)cyclopropane-1-carboxamido)-2,7-naphthyridin-3-yl)-N,4-dimethylpicolinamide (Absolute stereochemistry arbitrarily assigned) | 3.40<br>427.1<br>Q | $^1$H NMR (400 MHz, DMSO-d$_6$) δ 10.95 (s, 1H), 9.38 (s, 1H), 8.79 (q, J = 4.9 Hz, 1H), 8.61 (s, 1H), 8.27 (s, 1H), 7.96 (s, 1H), 7.56 (s, 1H), 7.36 (br s, 2H), 7.29 (s, 1H), 7.04 (s, 1H), 3.77 (s, 3H), 2.84 (d, J = 4.9 Hz, 3H), 2.26-2.16 (m, 2H), 1.43-1.32 (m, 1H), 1.23-1.15 (m, 1H). |

TABLE A-1-continued

| Compd No. | Structure/Name | LCMS R_T(min) M + H+, Method | $^1$H NMR (ppm) |
|---|---|---|---|
| 347 | 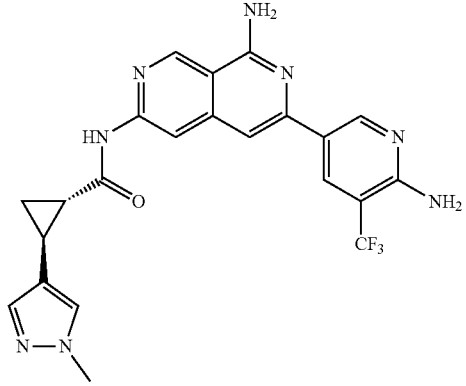 [SMILES: Cn1cc([C@H]2C[C@@H]2C(=O)Nc2cc3cc(-c4cnc(N)c(C(F)(F)F)c4)nc(N)c3cn2)cn1]<br>(1S,2S)-N-(8-amino-6-(6-amino-5-(trifluoromethyl)pyridin-3-yl)-2,7-naphthyridin-3-yl)-2-(1-methyl-1H-pyrazol-4-yl)cyclopropane-1-carboxamide (Absolute stereochemistry arbitrarily assigned) | 3.78<br>469.1<br>Q | $^1$H NMR (400 MHz, DMSO-d$_6$) δ 10.87 (s, 1H), 9.28 (s, 1H), 8.98 (d, J = 2.3 Hz, 1H), 8.47 (d, J = 2.3 Hz, 1H), 8.24 (s, 1H), 7.56 (s, 1H), 7.42 (s, 1H), 7.29 (s, 1H), 7.28 (br s, 2H), 6.75 (br s, 2H), 3.77 (s, 3H), 2.26-2.15 (m, 2H), 1.44-1.30 (m, 1H), 1.24-1.16 (m, 1H). |
| 348 | 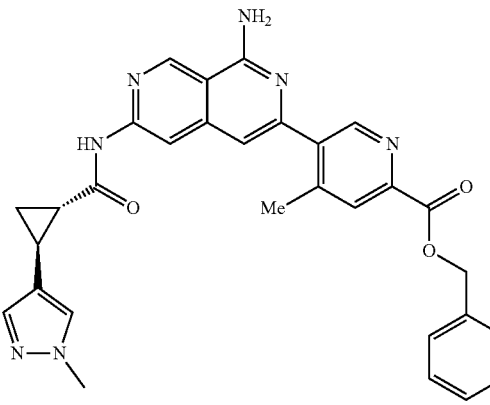<br>benzyl 5-(1-amino-6-((1S,2S)-2-(1-methyl-1H-pyrazol-4-yl)cyclopropane-1-carboxamido)-2,7-naphthyridin-3-yl)-4-methylpicolinate (Absolute stereochemistry arbitrarily assigned) | 4.39<br>534.2<br>Q | $^1$H NMR (400 MHz, DMSO-d$_6$) δ 10.95 (s, 1H), 9.38 (s, 1H), 8.71 (s, 1H), 8.27 (s, 1H), 8.04 (s, 1H), 7.56 (s, 1H), 7.53-7.47 (m, 2H), 7.45-7.34 (m, 5H), 7.29 (s, 1H), 7.04 (s, 1H), 5.41 (s, 2H), 3.77 (s, 3H), 2.25-2.16 (m, 2H), 1.45-1.33 (m, 1H), 1.26-1.16 (m, 1H). |

TABLE A-2

| Cmpd No. | Structure/Name | LCMS R_T (min) M + H+ Method | $^1$H NMR (ppm) |
|---|---|---|---|
| 349 | 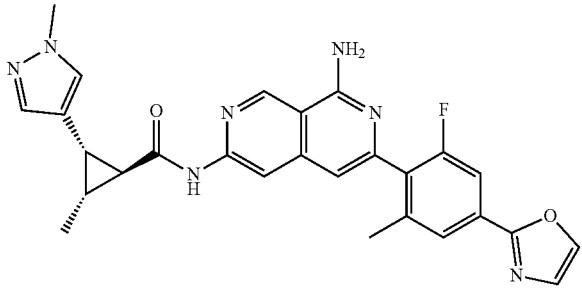 [SMILES: Cc1cc(-c2ncco2)cc(F)c1-c1cc2cc(NC(=O)[C@H]3[C@H](C)[C@@H]3c3cnn(C)c3)ncc2c(N)n1]<br>N-(8-amino-6-(2-fluoro-6-methyl-4-(oxazol-2-yl)phenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | 3.9<br>498.1<br>N | — |
| 350 | 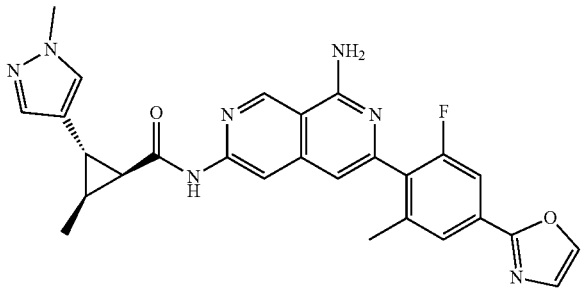 [SMILES: Cc1cc(-c2ncco2)cc(F)c1-c1cc2cc(NC(=O)[C@H]3[C@@H](C)[C@@H]3c3cnn(C)c3)ncc2c(N)n1]<br>(1S,2S,3S)-N-(8-amino-6-(2-fluoro-6-methyl-4-(oxazol-2-yl)phenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; All absolute stereochemistry arbitrarily assigned) | 3.9<br>498.1<br>N | — |
| 351 | 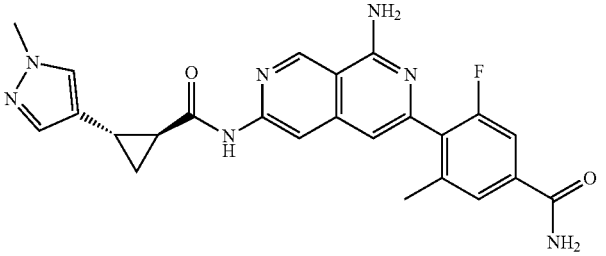 [SMILES: Cc1cc(C(N)=O)cc(F)c1-c1cc2cc(NC(=O)[C@H]3C[C@@H]3c3cnn(C)c3)ncc2c(N)n1]<br>4-(1-amino-6-((1S,2S)-2-(1-methyl-1H-pyrazol-4-yl)cyclopropane-1-carboxamido)-2,7-naphthyridin-3-yl)-3-fluoro-5-methylbenzamide<br>(Pyrazole trans to amide; Absolute stereochemistry arbitrarily assigned) | 3.1<br>460.1<br>N | $^1$H NMR (400 MHz, DMSO-d$_6$) δ 10.94 (s, 1H), 9.37 (d, J = 1.0 Hz, 1H), 8.22 (d, J = 0.8 Hz, 1H), 8.04 (s, 1H), 7.67 (d, J = 1.5 Hz, 1H), 7.57 (m, 2H), 7.49 (br s, 1H), 7.33 (br s, 2H), 7.29 (d, J = 0.8 Hz, 1H), 6.84 (s, 1H), 3.77 (s, 3H), 2.25-2.16 (m, 5H), 1.43-1.34 (m, 1H), 1.26-1.12 (m, 2H). |

TABLE A-2-continued

| Cmpd No. | Structure/Name | LCMS R_T (min) M + H⁺ Method | ¹H NMR (ppm) |
|---|---|---|---|
| 352 | 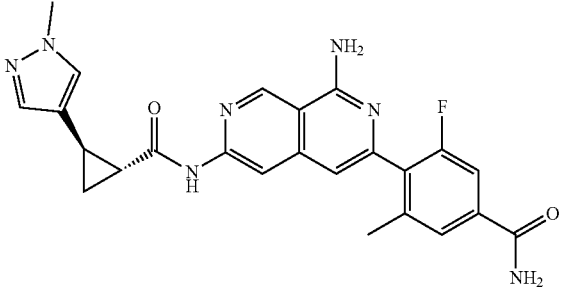 [SMILES: Cc1cc(C(N)=O)cc(F)c1-c1cc2cc(NC(=O)[C@@H]3C[C@H]3c3cnn(C)c3)ncc2c(N)n1]<br>4-(1-amino-6-((1R,2R)-2-(1-methyl-1H-pyrazol-4-yl)cyclopropane-1-carboxamido)-2,7-naphthyridin-3-yl)-3-fluoro-5-methylbenzamide<br>(Pyrazole trans to amide; Absolute stereochemistry arbitrarily assigned) | 3.0 460.1 N | ¹H NMR (400 MHz, DMSO-d$_6$) δ 10.94 (s, 1H), 9.37 (s, 1H), 8.22 (s, 1H), 8.04 (s, 1H), 7.67 (d, J = 1.6 Hz, 1H), 7.58 (d, J = 1.7 Hz, 1H), 7.56 (s, H), 7.49 (s, 1H), 7.31 (d, J = 14.8 Hz, 3H), 6.84 (s, 1H), 3.77 (s, 3H), 3.42-3.31 (m, 0H), 3.29 (s, 0H), 2.21 (d, J = 9.2 Hz, 5H), 1.43-1.34 (m, 1H), 1.26-1.12 (m, 2H). |
| 353 | 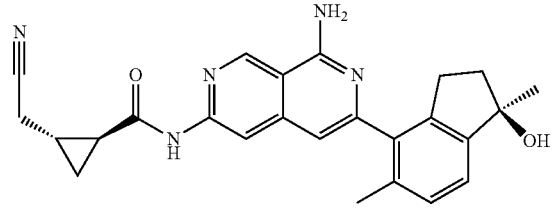 [SMILES: Cc1ccc2c(c1-c1cc3cc(NC(=O)[C@H]4C[C@@H]4CC#N)ncc3c(N)n1)CC[C@@]2(C)O]<br>(1S,2R)-N-(8-amino-6-((R)-1-hydroxy-1,5-dimethyl-2,3-dihydro-1H-inden-4-yl)-2,7-naphthyridin-3-yl)-2-(cyanomethyl)cyclopropane-1-carboxamide<br>(Cyanomethyl trans to amide; All absolute stereochemistry arbitrarily assigned) | 1.278 428.3 K | ¹H NMR (400 MHz, CD$_3$OD) δ 9.29 (s, 1H), 8.25 (s, 1H), 7.30 (d, J = 7.8 Hz, 1H), 7.20 (d, J = 7.8 Hz, 1 H), 6.80 (s, 1H), 2.87-2.58 (m, 4H), 2.22 (s, 3H), 2.14 (t, J = 7.0 Hz, 2H), 2.02-1.97 (m, 1H), 1.83-1.70 (m, 1H), 1.54 (s, 3H), 1.37-1.34 (m, 1H), 1.07-1.03 (m, 1H). |
| 354 | 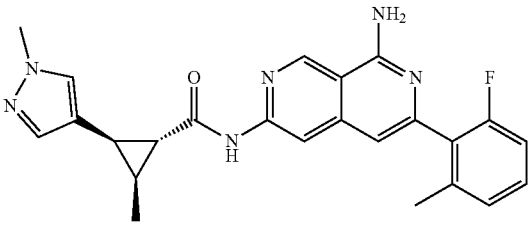 [SMILES: Cc1cccc(F)c1-c1cc2cc(NC(=O)[C@@H]3[C@@H](C)[C@H]3c3cnn(C)c3)ncc2c(N)n1]<br>(1R,2S,3R)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | 1.414 431.3 J | ¹H NMR (400 MHz, CD$_3$OD) δ 9.31 (s, 1H), 8.29 (s, 1H), 7.51 (s, 1H), 7.40 (s, 1H), 7.33-7.31 (m, 1H), 7.13 (d, J = 7.6 Hz, 1H), 7.03 (t, J = 8.9 Hz, 1H), 6.86 (s, 1H), 3.88 (s, 3H), 2.53-2.50 (m, 1H), 2.23 (s, 3H), 2.01-2.00 (m, 1H), 1.82-1.71 (m, 1H), 1.06 (d, J = 6.3 Hz, 3H). |

TABLE A-2-continued

| Cmpd No.. | Structure/Name | LCMS R$_T$ (min) M + H$^+$ Method | $^1$H NMR (ppm) |
|---|---|---|---|
| 355 | 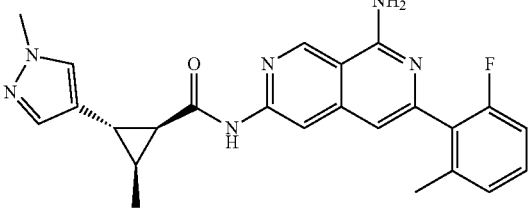<br>(1S,2S,3S)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | 1.422<br>431.3<br>J | $^1$H NMR (400 MHz, CD$_3$OD) δ 9.30 (s, 1H), 8.31 (s, 1H), 7.47 (s, 1H), 7.35-7.30 (m, 2H), 7.14 (d, J = 7.6 Hz, 1H), 7.04 (t, J = 8.8 Hz, 1H), 6.87 (s, 1H), 3.85 (s, 3H), 2.35-2.32 (m, 1H), 2.24 (s, 3H), 2.18-2.15 (m, 1H), 1.69-1.63 (m, 1H), 1.35 (d, J = 6.2 Hz, 3H). |
| 356 | 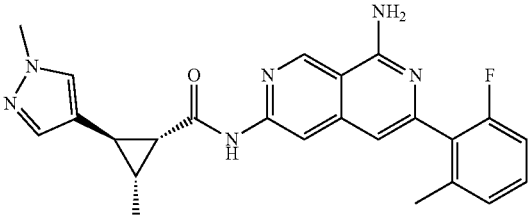<br>(1R,2R,3R)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | 1.423<br>431.3<br>J | $^1$H NMR (400 MHz, CD$_3$OD) δ 9.30 (s, 1H), 8.31 (s, 1H), 7.47 (s, 1H), 7.35-7.30 (m, 2H), 7.14 (d, J = 7.6 Hz, 1H), 7.04 (t, J = 8.8 Hz, 1H), 6.87 (s, 1H), 3.85 (s, 3H), 2.35-2.32 (m, 1H), 2.24 (s, 3H), 2.18-2.15 (m, 1H), 1.69-1.63 (m, 1H), 1.35 (d, J = 6.2 Hz, 3H). |
| 357 | 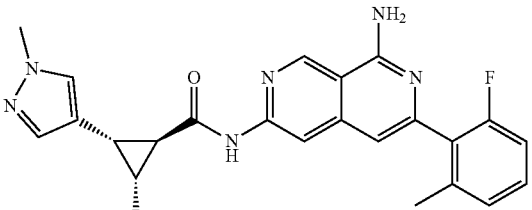<br>(1S,2R,3S)-N-(8-amino-6-(2-fluoro-6-methylphenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned; Absolute stereochemistry arbitrarily assigned) | 1.413<br>431.3<br>J | $^1$H NMR (400 MHz, CD$_3$OD) δ 9.31 (s, 1H), 8.29 (s, 1H), 7.51 (s, 1H), 7.40 (s, 1H), 7.33-7.31 (m, 1H), 7.13 (d, J = 7.6 Hz, 1H), 7.03 (t, J = 8.9 Hz, 1H), 6.86 (s, 1H), 3.88 (s, 3H), 2.53-2.50 (m, 1H), 2.23 (s, 3H), 2.01-2.00 (m, 1H), 1.82-1.71 (m, 1H), 1.06 (d, J = 6.3 Hz, 3H). |

TABLE A-2-continued

| Cmpd No. | Structure/Name | LCMS R_T (min) M + H+ Method | ¹H NMR (ppm) |
|---|---|---|---|
| 358 | (1S,2R,3S)-N-(8-amino-6-(3-amino-2-methylphenyl)-2,7-naphthyridin-3-yl)-2-methyl-3-(1-methyl-1H-pyrazol-4-yl)cyclopropane-1-carboxamide (Pyrazole trans to amide; methyl relative stereochemistry arbitrarily assigned; Absolute stereochemistry arbitrarily assigned) | 1.18 428.30 J | ¹H NMR (400 MHz, DMSO-$d_6$) δ 10.83 (s, 1H), 9.33 (s, 1H), 8.17 (s, 1H), 7.53 (s, 1H), 7.28 (s, 1H), 7.23-7.10 (m, 2H), 6.91 (t, J = 7.7 Hz, 1H), 6.72 (s, 1H), 6.65 (dd, J = 8.0, 1.3 Hz, 1H), 6.56 (dd, J = 7.6, 1.3 Hz, 1H), 4.85 (s, 2H), 3.79 (s, 3H), 2.32-2.25 (m, 1H), 2.12 (t, J = 4.7 Hz, 1H), 2.00 (s, 3H), 1.69-1.49 (m, 1H), 0.95 (d, J = 6.2 Hz, 3H). |
| 359 | (1R,2S)-N-(8-amino-6-(2-fluoro-6-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.341 376.2 K | ¹H NMR (400 MHz, CD$_3$OD) δ 9.28 (s, 1H), 8.24 (s, 1H), 7.33-7.31 (m, 1H), 7.11 (d, J = 7.6 Hz, 1H), 7.01 (t, J = 8.9 Hz, 1H), 6.84 (s, 1H), 2.79-2.64 (m, 2H), 2.21 (s, 3H), 2.02-1.97 (m, 1H), 1.75-1.70 (m, 1H), 1.34-1.28 (m, 1H), 1.05-1.00 (m, 1H). |
| 360 | (1S,2R)-N-(8-amino-6-(2-fluoro-6-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.336 376.2 K | ¹H NMR (400 MHz, CD$_3$OD) δ 9.28 (s, 1H), 8.24 (s, 1H), 7.33-7.31 (m, 1H), 7.11 (d, J = 7.6 Hz, 1H), 7.01 (t, J = 8.9 Hz, 1H), 6.84 (s, 1H), 2.79-2.64 (m, 2H), 2.21 (s, 3H), 2.02-1.97 (m, 1H), 1.75-1.70 (m, 1H), 1.34-1.28 (m, 1H), 1.05-1.00 (m, 1H). |

TABLE A-2-continued

| Cmpd No.. | Structure/Name | LCMS $R_T$ (min) M + H⁺ Method | ¹H NMR (ppm) |
|---|---|---|---|
| 361 | 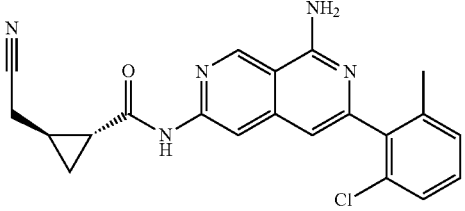 [SMILES: Cc1cccc(Cl)c1-c1cc2cc(NC(=O)[C@@H]3C[C@H]3CC#N)ncc2c(N)n1]<br>(1R,2S)-N-(8-amino-6-(2-chloro-6-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.526<br>392.2<br>M | ¹H NMR (400 MHz, DMSO-d₆) δ 11.08 (s, 1H), 9.39 (s, 1H), 8.19 (s, 1H), 7.37-7.26 (m, 5H), 6.74 (s, 1H), 2.75 (d, J = 2.0 Hz, 2H), 2.11 (s, 4H), 1.61-1.59 (m, 1H), 1.19-1.09 (m, 1H), 1.01-0.90 (m, 1H). |
| 362 | 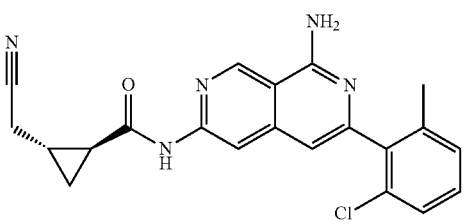 [SMILES: Cc1cccc(Cl)c1-c1cc2cc(NC(=O)[C@H]3C[C@@H]3CC#N)ncc2c(N)n1]<br>(1S,2R)-N-(8-amino-6-(2-chloro-6-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.523<br>392.2<br>M | ¹H NMR (400 MHz, DMSO-d₆) δ 11.08 (s, 1H), 9.39 (s, 1H), 8.19 (s, 1H), 7.37-7.26 (m, 5H), 6.74 (s, 1H), 2.75 (d, J = 2.0 Hz, 2H), 2.11 (s, 4H), 1.61-1.59 (m, 1H), 1.19-1.09 (m, 1H), 1.01-0.90 (m, 1H) |
| 363 | 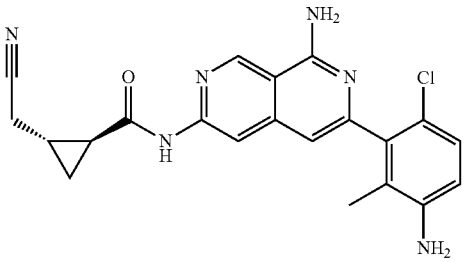 [SMILES: Cc1c(N)ccc(Cl)c1-c1cc2cc(NC(=O)[C@H]3C[C@@H]3CC#N)ncc2c(N)n1]<br>(1S,2R)-N-(8-amino-6-(3-amino-6-chloro-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.232<br>407.2<br>K | ¹H NMR (300 MHz, DMSO-d₆) δ 11.01 (s, 1H), 9.36 (s, 1H), 8.15 (s, 1H), 7.25 (s, 2H), 7.00 (d, J = 8.5 Hz, 1H), 6.67-6.64 (m, 2H), 5.02 (s, 2H), 2.73 (d, J = 6.2 Hz, 2H), 2.10-2.09 (m, 1H), 1.78 (s, 3H), 1.57-1.53 (m, 1H), 1.20-1.06 (m, 1H), 0.98-0.95 (m, 1H). |
| 364 | 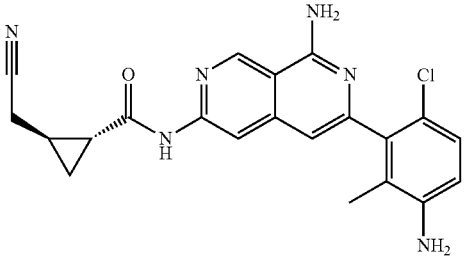<br>(1R,2S)-N-(8-amino-6-(3-amino-6-chloro-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 2.112<br>407.2<br>K | ¹H NMR (300 MHz, DMSO-d₆) δ 11.01 (s, 1H), 9.35 (s, 1H), 8.14 (s, 1H), 7.24 (s, 2H), 6.99 (d, J = 8.5 Hz, 1H), 6.67-6.64 (m, 2H), 5.01 (s, 2H), 2.73 (d, J = 6.2 Hz, 2H), 2.10-2.09 (m, 1H), 1.78 (s, 3H), 1.57-1.53 (m, 1H), 1.20-1.06 (m, 1H), 0.98-0.95 (m, 1H). |

TABLE A-2-continued

| Cmpd No.. | Structure/Name | LCMS R$_T$ (min) M + H$^+$ Method | $^1$H NMR (ppm) |
|---|---|---|---|
| 365 | (1R,2S)-N-(8-amino-6-(3-amino-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.07 373 K | $^1$H NMR (300 MHz, DMSO-d$_6$) δ 11.04 (s, 1H), 9.38 (s, 1H), 8.19 (s, 1H), 7.24-6.92 (m, 3H), 6.85-6.51 (m, 3H), 4.92 (s, 2H), 2.75-2.72 (m, 2H), 2.14-2.11 (m, 1H), 2.01 (s, 3H), 1.65-1.53 (m, 1H), 1.24-1.16 (m, 1H), 1.02-0.91 (m, 1H). |
| 366 | (1S,2R)-N-(8-amino-6-(3-amino-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.07 373 K | $^1$H NMR (400 MHz, CD$_3$OD) δ 9.27 (s, 1H), 8.24 (s, 1H), 7.05 (t, J = 7.7 Hz. 1H), 6.87-6.71 (m, 3H), 2.82-2.60 (m, 2H), 2.11 (s, 3H), 2.05-1.99 (m,1H), 1.82-1.69 (m, 1H), 1.41-1.27 (m, 1H), 1.08-1.03 (m, 1H). |
| 367 | (+/−)-trans-N-(8-amino-6-(2-chloro-5-cyanophenyl)-2,7-naphthyridin-3-yl)-2-(1-methyl-1H-pyrazol-4-yl)cyclopropane-1-carboxamide (Pyrazole trans to amide; Absolute stereochemistiy arbitrarily assigned) | 1.332 444.2 J | $^1$H NMR (300 MHz, DMSO-d$_6$) δ 10.97 (s, 1H), 9.38 (s, 1H), 8.25 (s, 1H), 8.07 (d, J = 3 Hz, 1H), 7.92-7.91 (m, 1H), 7.81 (d, J = 8.3 Hz, 1H), 7.55 (s, 1H), 7.40 (s, 2H), 7.29 (s, 1H), 7.08 (s, 1H), 3.76 (s, 3H), 2.22-2.18 (m, 2H), 1.42-1.36 (m, 1H), 1.22-1.16 (m, 1H). |
| 368 | (1R,2S)-N-(8-amino-6-(o-tolyl)-2,7-naphthyridin-3-yl)-2-(cyanomethyl)cyclopropane-1-carboxamide (Cyanomethyl trans to amide; Absolute stereochemistry arbitrarily assigned) | 1.350 358.2 K | $^1$H NMR (400 MHz, DMSO-d$_6$) δ 11.01 (s, 1H), 9.36 (s, 1H), 8.20 (s, 1H), 7.40 (d, J = 6.8 Hz, 1H), 7.30-7.22 (m, 5H), 6.85 (s, 1H), 2.83-2.63 (m, 2H), 2.36 (s, 3H), 2.11-2.08 (m, 1H), 1.60-1.55 (m, 1H), 1.14-1.11 (m, 1H), 0.98-0.96 (m, 1H). |

TABLE A-2-continued

| Cmpd No. | Structure/Name | LCMS R$_T$ (min) M + H$^+$ Method | $^1$H NMR (ppm) |
|---|---|---|---|
| 369 | 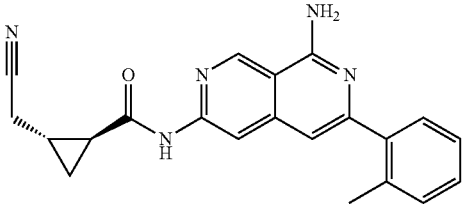 [SMILES: Cc1ccccc1-c1cc2cc(NC(=O)[C@H]3C[C@@H]3CC#N)ncc2c(N)n1]<br>(1S,2R)-N-(8-amino-6-(o-tolyl)-2,7-naphthyridin-3-yl)-2-(cyanomethyl)cyclopropane-1-carboxamide (Cyanomethyl trans to amide; Absolute stereochemistry arbitrarily assigned) | 1.344<br>358.2<br>K | $^1$H NMR (400 MHz, DMSO-d$_6$) δ 11.00 (s, 1H), 9.36 (s, 1H), 8.19 (s, 1H), 7.40 (d, J = 6.8 Hz, 1H), 7.32-7.12 (m, 5H), 6.85 (s, 1H), 2.74-2.67 (m, 2H), 2.36 (s, 3H), 2.13-2.09 (m, 1H), 1.60-1.55 (m, 1H), 1.15-1.11 (m, 1H), 0.98-0.96 (m, 1H). |
| 370 | 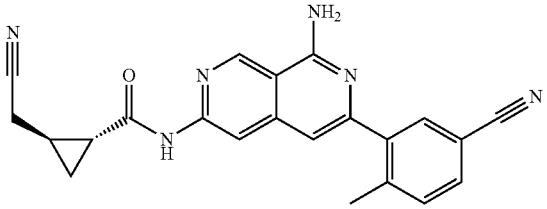 [SMILES: Cc1ccc(C#N)cc1-c1cc2cc(NC(=O)[C@@H]3C[C@H]3CC#N)ncc2c(N)n1]<br>(1R,2S)-N-(8-amino-6-(5-cyano-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 2.468<br>383.2<br>M | $^1$H NMR (400 MHz, DMSO-d$_6$) δ 11.04 (s, 1H), 9.38 (s, 1H), 8.23 (s, 1H), 7.85 (s, 1H), 7.75 (d, J = 8 Hz, 1H), 7.51 (d, J = 7.9 Hz, 1H), 7.32 (s, 2H), 6.98 (s, 1H), 2.74-2.72 (m, 2H), 2.45 (s, 3H), 2.12-2.08 (m, 1H), 1.65-1.52 (m, 1H), 1.14-1.10 (m, 1H), 1.01-0.92 (m, 1H). |
| 371 | 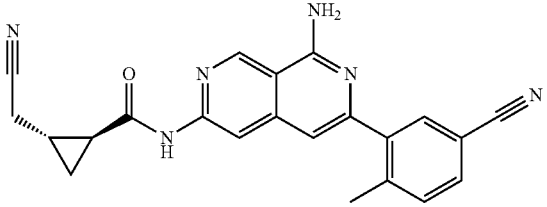 [SMILES: Cc1ccc(C#N)cc1-c1cc2cc(NC(=O)[C@H]3C[C@@H]3CC#N)ncc2c(N)n1]<br>(1S,2R)-N-(8-amino-6-(5-cyano-2-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.295<br>383.2<br>K | $^1$H NMR (400 MHz, DMSO-d$_6$) δ 11.04 (s, 1H), 9.38 (s, 1H), 8.23 (s, 1H), 7.85 (s, 1H), 7.75 (d, J = 8 Hz, 1H), 7.51 (d, J = 7.9 Hz, 1H), 7.32 (s, 2H), 6.98 (s, 1H), 2.74-2.72 (m, 2H), 2.45 (s, 3H), 2.12-2.08 (m, 1H), 1.65-1.52 (m, 1H), 1.14-1.10 (m, 1H), 1.01-0.92 (m, 1H). |
| 372 | 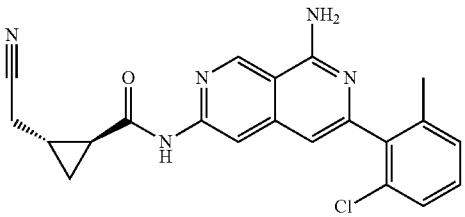 [SMILES: Cc1cccc(Cl)c1-c1cc2cc(NC(=O)[C@H]3C[C@@H]3CC#N)ncc2c(N)n1]<br>(+/−)-trans-N-(8-amino-6-(2-chloro-6-methylphenyl)-2,7-naphthyridin-3-yl)-2-(cyanomethyl)cyclopropane-1-carboxamide (Cyanomethyl trans to amide; Absolute stereochemistry arbitrarily assigned) | 1.533<br>392.2<br>M | $^1$H NMR (400 MHz, DMSO-d$_6$) δ 11.05 (s, 1H), 9.38 (s, 1H), 8.18 (s, 1H), 7.36-7.25 (m, 5H), 6.73 (s, 1H), 2.74 (d, J = 8.4 Hz, 2 H), 2.13-2.09 (m, 4 H), 1 76-1.51 (m, 1H), 1.15-1.10 (m, 1H), 0.98-0.94 (m, 1H). |

TABLE A-2-continued

| Cmpd No.. | Structure/Name | LCMS R_T (min) M + H+ Method | ¹H NMR (ppm) |
|---|---|---|---|
| 373 | 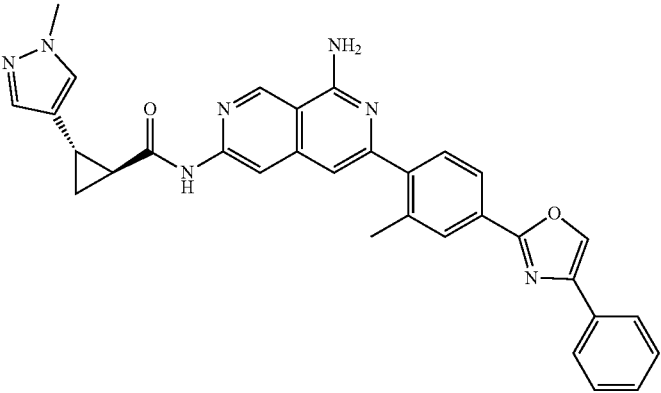 [SMILES: Cc1cc(-c2nc(-c3ccccc3)co2)ccc1-c1cc2cc(NC(=O)[C@H]3C[C@@H]3c3cnn(C)c3)ncc2c(N)n1]<br>(1S,2S)-N-(8-amino-6-(2-methyl-4-(4-phenyloxazol-2-yl)phenyl)-2,7-naphthyridin-3-yl)-2-(1-methyl-1H-pyrazol-4-yl)cyclopropane-1-carboxamide (Pyrazole trans to amide; Absolute stereochemistry arbitrarily assigned) | 4.6<br>542.2<br>N | ¹H NMR (400 MHz, DMSO-d$_6$) δ 10.93 (s, 1H), 9.37 (s, 1H), 8.75 (s, 1H), 8.26 (s, 1H), 8.02-7.86 (m, 4H), 7.62 (d, J = 8.0 Hz, 1H), 7.56 (s, 1H), 7.48 (dd, J = 8.3, 7.0 Hz, 2H), 7.42-7.29 (m, 1H), 7.29 (s, 3H), 6.97 (s, 1H), 3.77 (s, 3H), 3.30 (s, 1H), 3.32-3.20 (m, 0H), 2.27-2.17 (m, 2H), 1.39 (ddd, J = 9.1, 5.9, 3.7 Hz, 1H), 1.26-1.14 (m, 2H). |
| 374 | 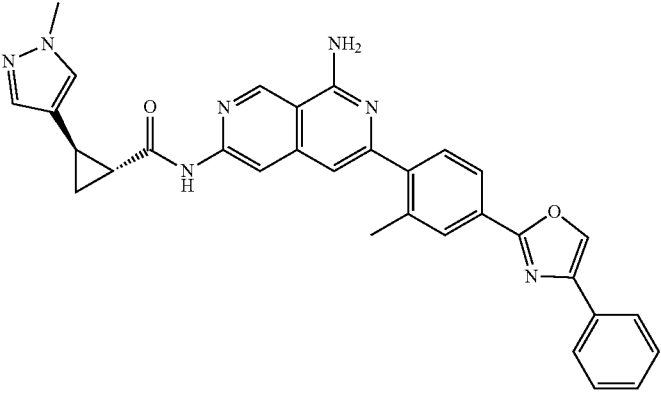 [SMILES: Cc1cc(-c2nc(-c3ccccc3)co2)ccc1-c1cc2cc(NC(=O)[C@@H]3C[C@H]3c3cnn(C)c3)ncc2c(N)n1]<br>(1R,2R)-N-(8-amino-6-(2-methyl-4-(4-phenyloxazol-2-yl)phenyl)-2,7-naphthyridin-3-yl)-2-(1-methyl-1H-pyrazol-4-yl)cyclopropane-1-carboxamide (Pyrazole trans to amide; Absolute stereochemistry arbitrarily assigned) | 4.6<br>542.2<br>N | ¹H NMR (400 MHz, DMSO-d$_6$) δ 10.93 (s, 1H), 9.37 (s, 0H), 8.75 (s, 0H), 8.26 (s, 0H), 8.02-7.91 (m, 1H), 7.93-7.86 (m, 1H), 7.62 (d, J = 8.0 Hz, 0H), 7.56 (s, 0H), 7.48 (t, J = 7.7 Hz, 1H), 7.42-7.32 (m, 1H), 7.32-7.27 (m, 1H), 6.97 (s, 0H), 3.77 (s, 2H), 3.45-3.22 (m, 1H), 2.26-2.17 (m, 1H), 1.39 (ddd, J = 8.0, 5.9, 3.8 Hz, 1H), 1.26-1.14 (m, 1H). |

TABLE A-2-continued

| Cmpd No.. | Structure/Name | LCMS R$_T$ (min) M + H$^+$ Method | $^1$H NMR (ppm) |
|---|---|---|---|
| 375 | (1S,2S)-N-(8-amino-6-(4-(4-isopropyloxazol-2-yl)-2-methylphenyl)-2,7-naphthyridin-3-yl)-2-(1-methyl-1H-pyrazol-4-yl)cyclopropane-1-carboxamide (Pyrazole trans to amide; Absolute stereochemistry arbitrarily assigned) | 4.3 508.2 N | — |
| 376 | (1R,2R)-N-(8-amino-6-(4-(4-isopropyloxazol-2-yl)-2-methylphenyl)-2,7-naphthyridin-3-yl)-2-(1-methyl-1H-pyrazol-4-yl)cyclopropane-1-carboxamide (Pyrazole trans to amide; Absolute stereochemistry arbitrarily assigned) | 4.3 508.2 N | — |
| 377 | (1R,2R)-N-(8-amino-6-(2,6-dichlorophenyl)-2,7-naphthyridin-3-yl)-2-(1-methyl-1H-pyrazol-4-yl)cyclopropane-1-carboxamide (Pyrazole trans to amide; Absolute stereochemistry arbitrarily assigned) | 1.387 453.2 K | $^1$HNMR (400 MHz, DMSO-d$_6$) δ 10.95 (s, 1H), 9.39 (s, 1H), 8.23 (s, 1H), 7.56 (t, J = 4.1 Hz, 3H), 7.50-7.31 (m, 3H), 7.29 (s, 1H), 6.81 (s, 1H), 3.77 (s, 3H), 2.21 (t, J = 7.0 Hz, 2H), 1.54-1.32 (m, 1H), 1.23-1.13 (m, 1H). |

TABLE A-2-continued

| Cmpd No.. | Structure/Name | LCMS $R_T$ (min) M + H+ Method | $^1$H NMR (ppm) |
|---|---|---|---|
| 378 | 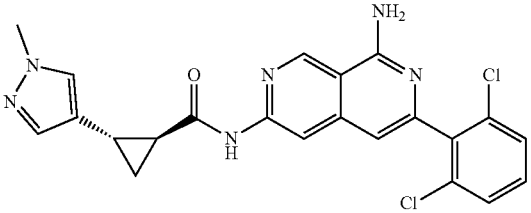 [SMILES: Cn1cc([C@H]2C[C@@H]2C(=O)Nc2cc3cc(-c4c(Cl)cccc4Cl)nc(N)c3cn2)cn1]<br>(1S,2S)-N-(8-amino-6-(2,6-dichlorophenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 1.388<br>453.2<br>K | $^1$HNMR (400 MHz, DMSO-d$_6$) δ 10.95 (s, 1H), 9.39 (s, 1H), 8.23 (s, 1H), 7.56 (t, J = 4.1 Hz, 3H), 7.50-7.31 (m, 3H), 7.29 (s, 1H), 6.81 (s, 1H), 3.77 (s, 3H), 2.21 (t, J = 7.0 Hz, 2H), 1.54-1.32 (m, 1H), 1.23-1.13 (m, 1H). |
| 379 | 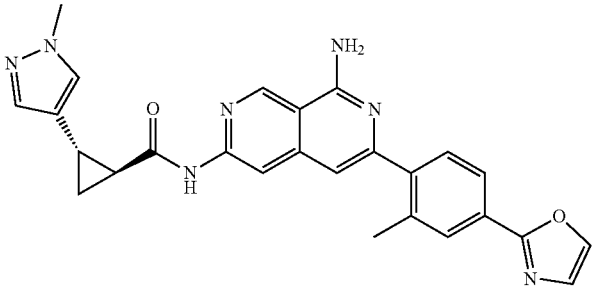 [SMILES: Cc1cc(-c2ncco2)ccc1-c1cc2cc(NC(=O)[C@H]3C[C@@H]3c3cnn(C)c3)ncc2c(N)n1]<br>(1S,2S)-N-(8-amino-6-(2-methyl-4-(oxazol-2-yl)phenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 3.6<br>466.2<br>N | — |
| 380 | 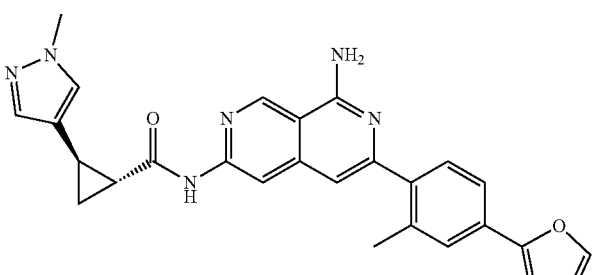<br>(1R,2R)-N-(8-amino-6-(2-methyl-4-(oxazol-2-yl)phenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 3.6<br>466.2<br>N | — |

TABLE A-2-continued

| Cmpd No.. | Structure/Name | LCMS R$_T$ (min) M + H$^+$ Method | $^1$H NMR (ppm) |
|---|---|---|---|
| 381 | 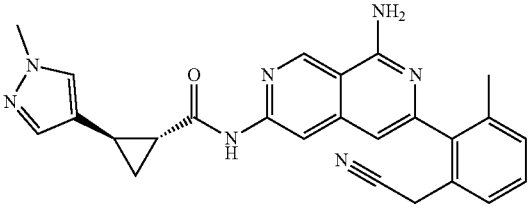 [SMILES: Cc1cccc(CC#N)c1-c1cc2cc(NC(=O)[C@@H]3C[C@H]3c3cnn(C)c3)ncc2c(N)n1]<br>(1R,2R)-N-(8-amino-6-(2-(cyanomethyl)-6-methylphenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 1.328<br>438.3<br>K | $^1$H NMR (300 MHz, DMSO-d$_6$) δ 10.95 (s, 1H), 9.37 (s, 1H), 8.22 (s, 1H), 7.56 (s, 1H), 7.47-7.21 (m, 6H), 6.75 (s, 1H), 3.77 (s, 3H), 7.75 (s, 2H), 2.20 (t, J = 7.2 Hz, 2H), 2.12 (s, 3H) 1.39-1.36 (m, 1H), 1.22-1.17 (m, 1H). |
| 382 | 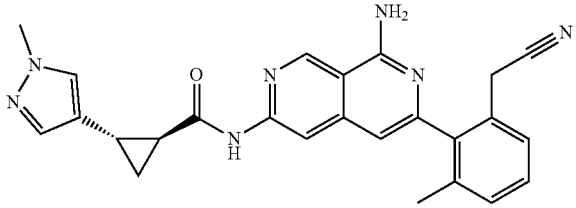 [SMILES: Cc1cccc(CC#N)c1-c1cc2cc(NC(=O)[C@H]3C[C@@H]3c3cnn(C)c3)ncc2c(N)n1]<br>(+/−)-trans-N-(8-amino-6-(2-(cyanomethyl)-6-methylphenyl)-2,7-naphthyridin-3-yl)-2-(1-methyl-1H-pyrazol-4-yl)cyclopropane-1-carboxamide | 1.335<br>438.3<br>J | $^1$H NMR (300 MHz, DMSO-d$_6$) δ 10.95 (s, 1H), 9.37 (s, 1H), 8.22 (s, 1H), 7.56 (s, 1H), 7.47-7.21 (m, 6H), 6.75 (s, 1H), 3.77 (s, 3H), 7.75 (s, 2H), 2.20 (t, J = 7.2 Hz, 2H), 2.12 (s, 3H) 1.39-1.36 (m, 1H), 1.22-1.17 (m, 1H). |
| 383 | 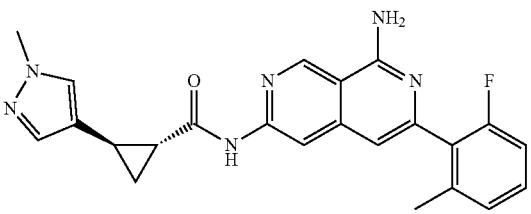 [SMILES: Cc1cccc(F)c1-c1cc2cc(NC(=O)[C@@H]3C[C@H]3c3cnn(C)c3)ncc2c(N)n1]<br>(1R,2R)-N-(8-amino-6-(2-fluoro-6-methylphenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 1.676<br>417.2<br>J | $^1$H NMR (400 MHz, CD$_3$OD) δ 9.30 (s, 1H), 8.30 (s, 1H), 7.49 (s, 1H), 7.40-7.27 (m, 2H), 7.14 (d, J = 7.6 Hz, 1H), 7.04 (t, J = 8.9 Hz, 1H), 6.88 (s, 1H), 3.84 (s, 3H), 2.38-2.34 (m, 1H), 2.24 (s, 3H), 2.13-2.07 (m, 1H), 1.59-1.53 (m, 1H), 1.33-1.19 (m, 1H). |

TABLE A-2-continued

| Cmpd No.. | Structure/Name | LCMS $R_T$ (min) M + H⁺ Method | ¹H NMR (ppm) |
|---|---|---|---|
| 384 | 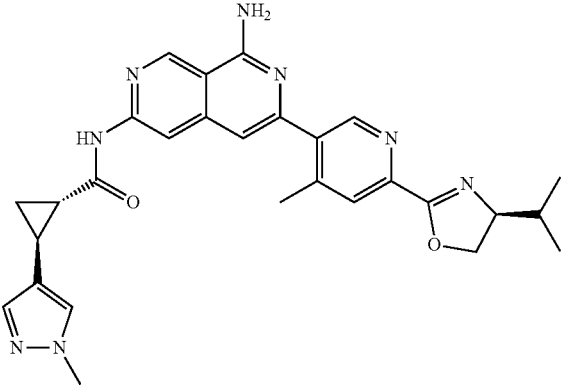 [SMILES: Cc1cc(C2=N[C@@H](C(C)C)CO2)ncc1-c1cc2cc(NC(=O)[C@H]3C[C@@H]3c3cnn(C)c3)ncc2c(N)n1]<br>(+/−)-trans-N-(8-amino-6-(6-((S)-4-isopropyl-4,5-dihydrooxazol-2-yl)-4-methylpyridin-3-yl)-2,7-naphthyridin-3-yl)-2-(1-methyl-1H-pyrazol-4-yl)cyclopropane-1-carboxamide | 511.2 | 1H NMR (400 MHz, DMSO-d₆) δ 10.95 (s, 1H), 9.38 (s, 1H), 8.65 (s, 1H), 8.27 (s, 1H), 7.93 (s, 1H), 7.56 (s, 1H), 7.36 (br s, 2H), 7.29 (s, 1H), 7.03 (s, 1H), 4.54-4.37 (m, 1H), 4.22-4.05 (m, 2H), 3.77 (s, 3H), 2.25-2.13 (m, 2H), 1.87-1.71 (m, 1H), 1.45-1.30 (m, 1H), 1.24-1.10 (m, 1H), 0.98 (d, J = 6.7 Hz, 3H), 0.91 (d, J = 6.7 Hz, 3H). |
| 385 | 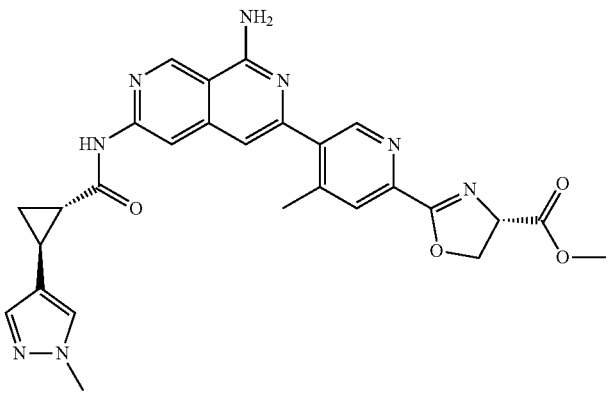 [SMILES: COC(=O)[C@@H]1COC(c2cc(C)c(-c3cc4cc(NC(=O)[C@H]5C[C@@H]5c5cnn(C)c5)ncc4c(N)n3)cn2)=N1]<br>methyl (S)-2-(5-(1-amino-6-((1S,2S)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate<br>(Pyrazole trans to amide; absolute stereochemistry arbitrarily assigned) | 527.2 | 1H NMR (400 MHz, DMSO-d₆) δ 10.96 (s, 1H), 10.36 (s, 1H), 9.39 (s, 1H), 8.71 (s, 1H), 8,28 (s, 1H), 8.08 (s, 1H), 7.56 (s, 1H), 7.37 (br s, 2H), 7.29 (s, 1H), 7.07 (s, 1H), 6.63 (s, 1H), 5.90 (d, J = 1.5 Hz, 1H), 3.86 (s, 3H), 3.77 (s, 3H), 2.54 (s, 3H), 2.24-2.17 (m, 2H), 1.44-1.34 (m, 1H), 1.29-1.06 (m, 1H). |

TABLE A-2-continued

| Cmpd No.. | Structure/Name | LCMS $R_T$ (min) M + H+ Method | $^1$H NMR (ppm) |
|---|---|---|---|
| 386 | 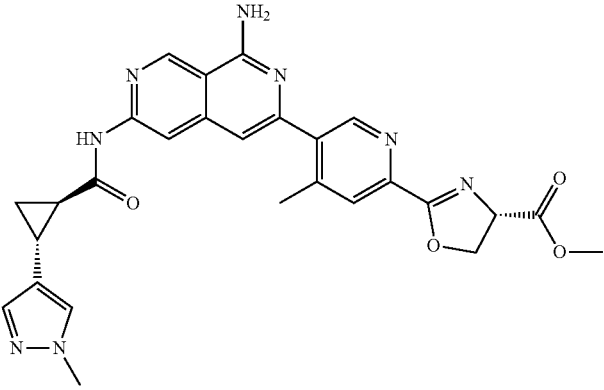 [SMILES: COC(=O)[C@@H]1COC(c2cc(C)c(-c3cc4cc(NC(=O)[C@@H]5C[C@H]5c5cnn(C)c5)ncc4c(N)n3)cn2)=N1]<br>methyl (S)-2-(5-(1-amino-6-((1R,2R)-2-(1-methyl-1H-pyrazol-4-yl)cyclopropane-1-carboxamido)-2,7-naphthyridin-3-yl)-4-methylpyridin-2-yl)-4,5-dihydrooxazole-4-carboxylate<br>(Pyrazole trans to amide; absolute stereochemistry arbitrarily assigned) | 527.2 | 1H NMR (400 MHz, DMSO-d$_6$) δ 10.96 (s, 1H), 10.36 (s, 1H), 9.39 (s, 1H), 8.71 (s, 1H), 8.28 (s, 1H), 8.08 (s, 1H), 7.56 (s, 1H), 7.37 (br s, 2H), 7.29 (s, 1H), 7.07 (s, 1H), 6.63 (s, 1H), 5.90 (d, J = 1.5 Hz, 1H), 3.86 (s, 3H), 3.77 (s, 3H), 2.54 (s, 3H), 2.24-2.17 (m, 2H), 1.44-1.34 (m, 1H), 1.29-1.06 (m, 1H). |
| 387 | 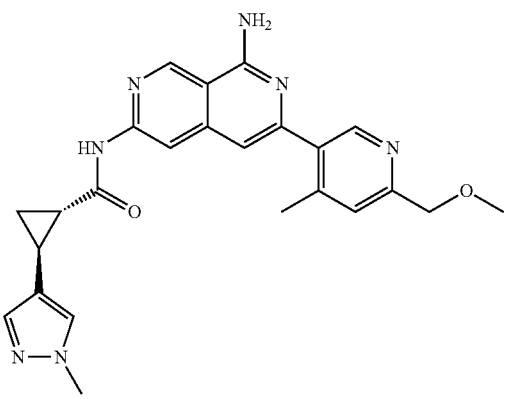 [SMILES: COCc1cc(C)c(-c2cc3cc(NC(=O)[C@H]4C[C@@H]4c4cnn(C)c4)ncc3c(N)n2)cn1]<br>(1S,2S)-N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 444.2 | 1H NMR (400 MHz, DMSO-d$_6$) δ 10.93 (s, 1H), 9.36 (s, 1H), 8.51 (s, 1H), 8.25 (s, 1H), 7.56 (s, 1H), 7.35-7.21 (m, 4H), 6.96 (s, 1H), 4.51 (s, 2H), 3.77 (s, 3H), 3.39 (s, 3H), 2.43 (s, 3H), 2.24-2.13 (m, 2H), 1.44-1.32 (m, 1H), 1.24-1.13 (m, 1H). |

TABLE A-2-continued

| Cmpd No. | Structure/Name | LCMS R$_T$ (min) M + H$^+$ Method | $^1$H NMR (ppm) |
|---|---|---|---|
| 388 | 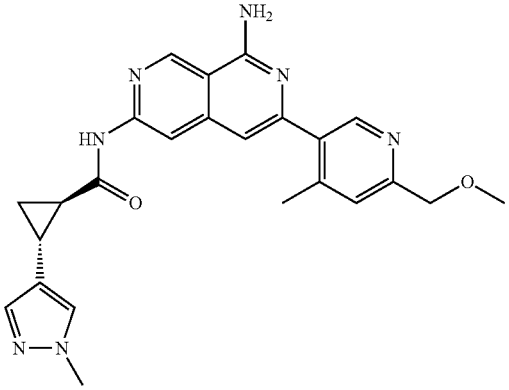 [SMILES: COCc1cc(C)c(-c2cc3cc(NC(=O)[C@@H]4C[C@H]4c4cnn(C)c4)ncc3c(N)n2)cn1]<br>(1R,2R)-N-(8-amino-6-(6-(methoxymethyl)-4-methylpyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 444.2 | 1H NMR (400 MHz, DMSO-d$_6$) δ 10.93 (s, 1H), 9.36 (s, 1H), 8.51 (s, 1H), 8.25 (s, 1H), 7.56 (s, 1H), 7.35-7.21 (m, 4H), 6.96 (s, 1H), 4.51 (s, 2H), 3.77 (s, 3H), 3.39 (s, 3H), 2.43 (s, 3H), 2.24-2.13 (m, 2H), 1.44-1.32 (m, 1H), 1.24-1.13 (m, 1H). |
| 391 | 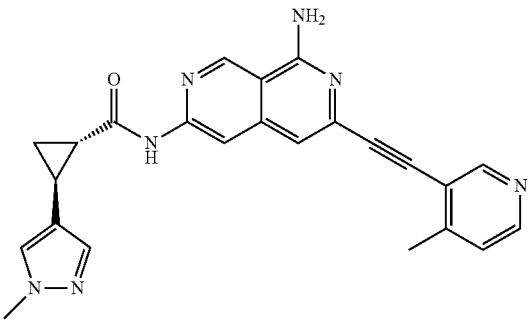 [SMILES: Cc1ccncc1C#Cc1cc2cc(NC(=O)[C@H]3C[C@@H]3c3cnn(C)c3)ncc2c(N)n1]<br>(1S,2S)-N-(8-amino-6-((4-methylpyridin-3-yl)ethynyl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 1.160 424.2 K | 1H NMR (400 MHz, DMSO-d$_6$) δ 11.01 (s, 1H), 9.34 (s, 1H), 8.67 (s, 1H), 8.47 (d, J = 5.0 Hz, 1H), 8.23 (s, 1H), 7.57 (s, 1H), 7.48-7.37 (m, 3H), 7.30 (s, 1H), 7.20 (s, 1H), 3.77 (s, 3H), 2.49 (s, 3H), 2.28-2.12 (m, 2H), 1.50-1.36 (m, 1H), 1.26-1.12 (m, 1H). |
| 392 | 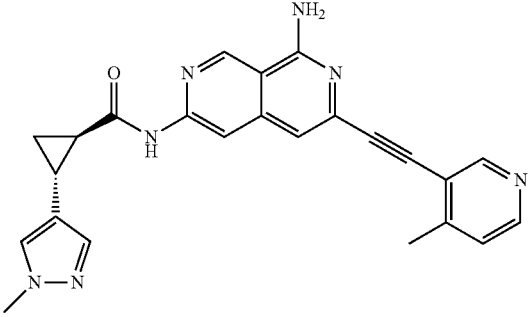 [SMILES: Cc1ccncc1C#Cc1cc2cc(NC(=O)[C@@H]3C[C@H]3c3cnn(C)c3)ncc2c(N)n1]<br>(1R,2R)-N-(8-amino-6-((4-methylpyridin-3-yl)ethynyl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 1.159 424.2 K | 1H NMR (400 MHz, DMSO-d$_6$) δ 11.01 (s, 1H), 9.34 (s, 1H), 8.67 (s, 1H), 8.47 (d, J = 5.0 Hz, 1H), 8.23 (s, 1H), 7.57 (s, 1H), 7.48-7.37 (m, 3H), 7.30 (s, 1H), 7.20 (s, 1H), 3.77 (s, 3H), 2.49 (s, 3H), 2.28-2.12 (m, 2H), 1.50-1.36 (m, 1H), 1.26-1.12 (m, 1H). |

TABLE A-2-continued

| Cmpd No. | Structure/Name | LCMS R$_T$ (min) M + H$^+$ Method | $^1$H NMR (ppm) |
|---|---|---|---|
| 393 | (1S,2S)-N-(8-amino-6-(5-methoxy-4-methylpyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 430.2 | 1H NMR (400 MHz, DMSO-d$_6$) δ 10.93 (s, 1H), 9.36 (s, 1H), 8.29 (s, 1H), 8.24 (s, 1H), 8.23 (s, 1H), 7.56 (s, 1H), 7.31 (br s, 2H), 7.29 (s, 1H), 6.91 (s, 1H), 3.94 (s, 3H), 3.77 (s, 3H), 2.25-2.14 (m, 2H), 2.21 (s, 3H), 1.45-1.33 (m, 1H), 1.23-1.12 (m, 1H). |
| 394 | (1R,2R)-N-(8-amino-6-(5-methoxy-4-methylpyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 430.2 | 1H NMR (400 MHz, DMSO-d$_6$) δ 10.93 (s, 1H), 9.36 (s, 1H), 8.29 (s, 1H), 8.24 (s, 1H), 8.23 (s, 1H), 7.56 (s, 1H), 7.31 (br s, 2H), 7.29 (s, 1H), 6.91 (s, 1H), 3.94 (s, 3H), 3.77 (s, 3H), 2.25-2.14 (m, 2H), 2.21 (s, 3H), 1.45-1.33 (m, 1H), 1.23-1.12 (m, 1H). |

TABLE A-2-continued

| Cmpd No. | Structure/Name | LCMS R$_T$ (min) M + H$^+$ Method | $^1$H NMR (ppm) |
|---|---|---|---|
| 395 | (1S,2S)-N-(8-amino-6-(6-methoxy-4-methylpyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 430.2 | 1H NMR (400 MHz, DMSO-d$_6$) δ 10.91 (s, 1H), 9.34 (s, 1H), 8.23 (s, 1H), 8.19 (s, 1H), 7.56 (s, 1H), 7.29 (s, 1H), 7.24 (br s, 2H), 6.91 (s, 1H), 6.74 (s, 1H), 3.87 (s, 3H), 3.77 (s, 3H), 2.38 (s, 3H), 2.26-2.14 (m, 2H), 1.46-1.32 (m, 1H), 1.27-1.05 (m, 1H). |
| 396 | (1R,2R)-N-(8-amino-6-(6-methoxy-4-methylpyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 430.1 | 1H NMR (400 MHz, DMSO-d$_6$) δ 10.91 (s, 1H), 9.34 (s, 1H), 8.23 (s, 1H), 8.19 (s, 1H), 7.56 (s, 1H), 7.29 (s, 1H), 7.24 (br s, 2H), 6.91 (s, 1H), 6.74 (s, 1H), 3.87 (s, 3H), 3.77 (s, 3H), 2.38 (s, 3H), 2.26-2.14 (m, 2H), 1.46-1.32 (m, 1H), 1.27-1.05 (m, 1H). |

TABLE A-2-continued

| Cmpd No.. | Structure/Name | LCMS R$_T$ (min) M + H$^+$ Method | $^1$H NMR (ppm) |
|---|---|---|---|
| 397 | 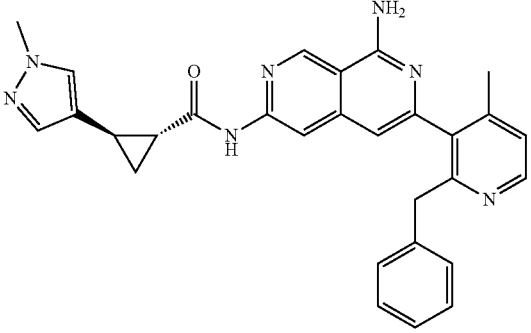 [SMILES: Cc1ccnc(Cc2ccccc2)c1-c1cc2cc(NC(=O)[C@@H]3C[C@H]3c3cnn(C)c3)ncc2c(N)n1]<br>(1R,2R)-N-(8-amino-6-(2-benzyl-4-methylpyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 1.156 490.3 K | 1H NMR (400 MHz, DMSO-d$_6$) δ 10.96 (s, 1H), 9.38 (s, 1H), 8.37 (d, J = 5.0 Hz, 1H), 8.15 (s, 1H), 7.56 (s, 1H), 7.37 (s, 2H), 7.30 (s, 1H), 7.18-7.07 (m, 4H), 7.02-6.98 (m, 2H), 6.66 (s, 1H), 3.91 (s, 2H), 3.77 (s, 3H), 2.20 (t, J = 7.1 Hz, 2H), 2.10 (s, 3H), 1.40-1.36 (m, 1H), 1.22-1.17 (s, 1H). |
| 398 | 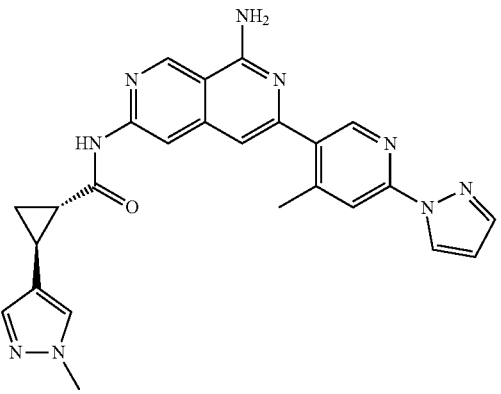 [SMILES: Cc1cc(-n2cccn2)ncc1-c1cc2cc(NC(=O)[C@H]3C[C@@H]3c3cnn(C)c3)ncc2c(N)n1]<br>(1S,2S)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 466.2 | 1H NMR (400 MHz, DMSO-d$_6$) δ 10.94 (s, 1H), 9.37 (s, 1H), 8.65 (d, J = 3.0 Hz, 1H), 8.48 (s, 1H), 8.27 (s, 1H), 7.88 (s, 1H), 7.85 (d, J = 3.0 Hz, 1H), 7.56 (s, 1H), 7.33 (br s, 2H), 7.29 (s, 1H), 7.03 (s, 1H), 6.60 (s, 1H), 3.77 (s, 3H), 2.54 (s, 3H), 2.25-2.16 (m, 2H), 1.43-1.34 (m, 1H), 1.23-1.16 (m, 1H). |
| 399 | 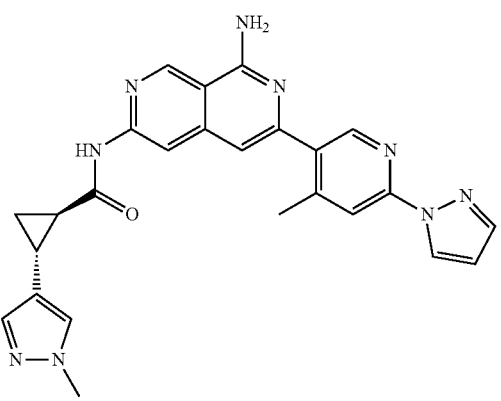 [SMILES: Cc1cc(-n2cccn2)ncc1-c1cc2cc(NC(=O)[C@@H]3C[C@H]3c3cnn(C)c3)ncc2c(N)n1]<br>(1R,2R)-N-(8-amino-6-(4-methyl-6-(1H-pyrazol-1-yl)pyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 466.2 | 1H NMR (400 MHz, DMSO-d$_6$) δ 10.94 (s, 1H), 9.37 (s, 1H), 8.65 (d, J = 3.0 Hz, 1H), 8.48 (s, 1H), 8.27 (s, 1H), 7.88 (s, 1H), 7.85 (d, J = 3.0 Hz, 1H), 7.56 (s, 1H), 7.33 (br s, 2H), 7.29 (s, 1H), 7.03 (s, 1H), 6.60 (s, 1H), 3.77 (s, 3H), 2.54 (s, 3H), 2.25-2.16 (m, 2H), 1.43-1.34 (m, 1H), 1.23-1.16 (m, 1H). |

| Cmpd No.. | Structure/Name | LCMS $R_T$ (min) M + H$^+$ Method | $^1$H NMR (ppm) |
|---|---|---|---|
| 400 | 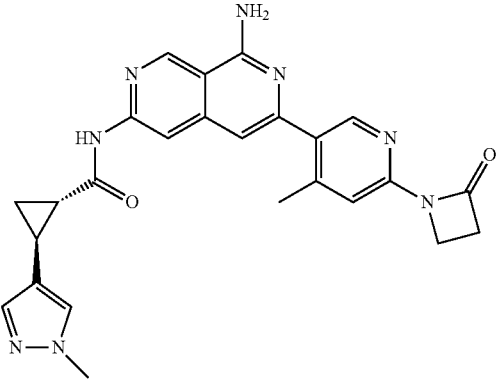 [SMILES: Cc1cc(N2CCC2=O)ncc1-c1cc2cc(NC(=O)[C@H]3C[C@@H]3c3cnn(C)c3)ncc2c(N)n1]<br>(1S,2S)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 469.2 | 1H NMR (400 MHz, DMSO-d$_6$) δ 10.92 (s, 1H), 9.35 (s, 1H), 8.34 (s, 1H), 8.24 (s, 1H), 7.56 (s, 1H), 7.52 (s, 1H), 7.29 (s, 1H), 7.28 (br s, 2H), 6.93 (s, 1H), 3.77 (s, 3H), 3.73 (dd, J = 4.7, 4.7 Hz, 2H), 3.12 (dd, J = 4.7, 4.7 Hz, 2H), 2.44 (s, 3H), 2.24-2.17 (m, 2H), 1.43-1.33 (m, 1H), 1.23-1.14 (m, 1H). |
| 401 | 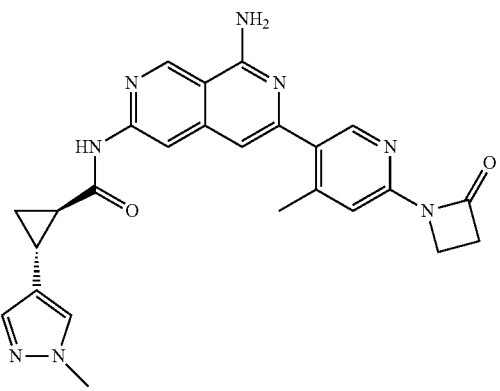 [SMILES: Cc1cc(N2CCC2=O)ncc1-c1cc2cc(NC(=O)[C@@H]3C[C@H]3c3cnn(C)c3)ncc2c(N)n1]<br>(1R,2R)-N-(8-amino-6-(4-methyl-6-(2-oxoazetidin-1-yl)pyridin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 469.2 | 1H NMR (400 MHz, DMSO-d$_6$) δ 10.92 (s, 1H), 9.35 (s, 1H), 8.34 (s, 1H), 8.24 (s, 1H), 7.56 (s, 1H), 7.52 (s, 1H), 7.29 (s, 1H), 7.28 (br s, 2H), 6.93 (s, 1H), 3.77 (s, 3H), 3.73 (dd, J = 4.7, 4.7 Hz, 2H), 3.12 (dd, J = 4.7, 4.7 Hz, 2H), 2.44 (s, 3H), 2.24-2.17 (m, 2H), 1.43-1.33 (m, 1H), 1.23-1.14 (m, 1H). |

TABLE A-2-continued

| Cmpd No.. | Structure/Name | LCMS R$_T$ (min) M + H$^+$ Method | $^1$H NMR (ppm) |
|---|---|---|---|
| 402 | 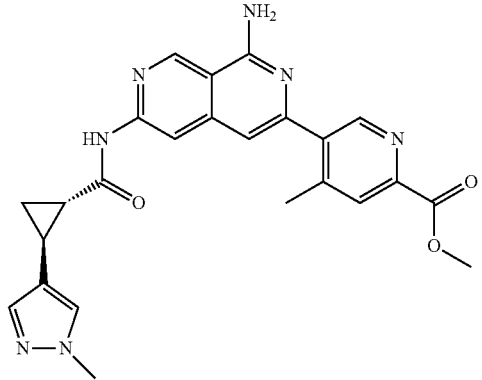 [SMILES: COC(=O)c1cc(C)c(-c2cc3cc(NC(=O)[C@H]4C[C@@H]4c4cnn(C)c4)ncc3c(N)n2)cn1]<br>methyl 5-(1-amino-6-(((1S,2S)-2-(1-methyl-1H-pyrazol-4-yl)cyclopropane-1-carboxamido)-2,7-naphthyridin-3-yl)-4-methylpicolinate<br>(Pyrazole trans to amide; All absolute stereochemistry arbitrarily assigned) | 458.1 | 1H NMR (400 MHz, DMSO-d$_6$) δ 10.95 (s, 1H), 9.38 (s, 1H), 8.71 (s, 1H), 8.28 (s, 1H), 8.01 (s, 1H), 7.56 (s, 1H), 7.37 (br s, 2H), 7.29 (s, 1H), 7.05 (s, 1H), 3.91 (s, 3H), 3.77 (s, 3H), 2.25-2.16 (m, 2H), 1.90 (s, 3H), 1.43-1.34 (m, 1H), 1.24-1.14 (m, 1H). |
| 403 | 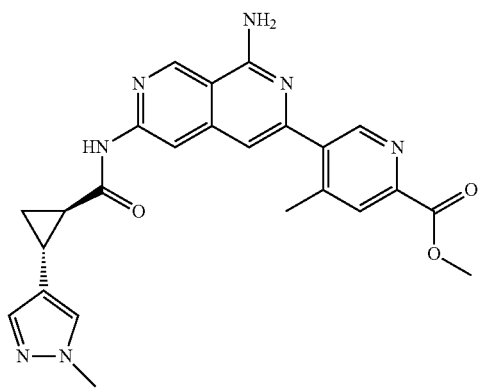 [SMILES: COC(=O)c1cc(C)c(-c2cc3cc(NC(=O)[C@@H]4C[C@H]4c4cnn(C)c4)ncc3c(N)n2)cn1]<br>methyl 5-(1-amino-6-(((1R,2R)-2-(1-methyl-1H-pyrazol-4-yl)cyclopropane-1-carboxamido)-2,7-naphthyridin-3-yl)-4-methylpicolinate<br>(Pyrazole trans to amide; All absolute stereochemistry arbitrarily assigned) | 458.1 | 1H NMR (400 MHz, DMSO-d$_6$) δ 10.95 (s, 1H), 9.38 (s, 1H), 8.71 (s, 1H), 8.28 (s, 1H), 8.01 (s, 1H), 7.56 (s, 1H), 7.37 (br s, 2H), 7.29 (s, 1H), 7.05 (s, 1H), 3.91 (s, 3H), 3.77 (s, 3H), 2.25-2.16 (m, 2H), 1.90 (s, 3H), 1.43-1.34 (m, 1H), 1.24-1.14 (m, 1H). |

TABLE A-2-continued

| Cmpd No.. | Structure/Name | LCMS $R_T$ (min) M + H$^+$ Method | $^1$H NMR (ppm) |
| --- | --- | --- | --- |
| 404 | 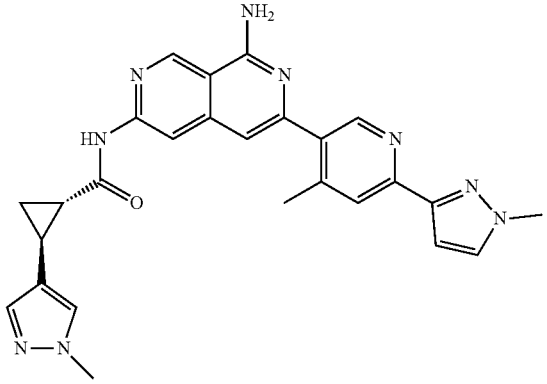 [SMILES: Cc1cc(-c2ccn(C)n2)ncc1-c1cc2cc(NC(=O)[C@H]3C[C@@H]3c3cnn(C)c3)ncc2c(N)n1]<br>(1S,2S)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 480.2 | 1H NMR (400 MHz, DMSO-d$_6$) δ 10.93 (s, 1H), 9.36 (s, 1H), 8.56 (s, 1H), 8.26 (s, 1H), 7.83 (s, 1H), 7.78 (d, J = 2.1 Hz, 1H), 7.56 (s, 1H), 7.30 (br s, 2H), 7.29 (d, J = 2.1 Hz, 1H), 7.00 (s, 1H), 6.81 (s, 1H), 3.93 (s, 3H), 3.77 (s, 3H), 2.47 (s, 3H), 2.26-2.14 (m, 2H), 1.45-1.32 (m, 1H), 1.28-1.15 (m, 1H). |
| 405 | 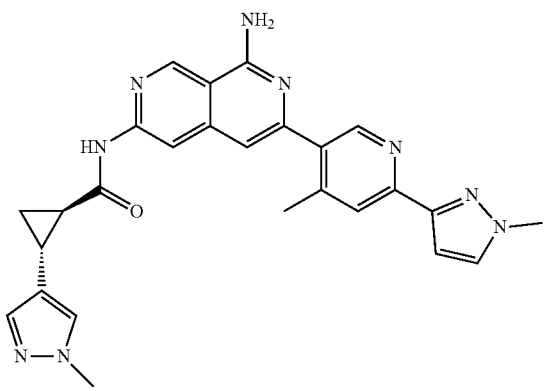 [SMILES: Cc1cc(-c2ccn(C)n2)ncc1-c1cc2cc(NC(=O)[C@@H]3C[C@H]3c3cnn(C)c3)ncc2c(N)n1]<br>(1R,2R)-N-(8-amino-6-(4-methyl-6-(1-methyl-1H-pyrazol-3-yl)pyridin-3-yl)-2,7-naphthyridin-3-yl)-2-(1-methyl-1H-pyrazol-4-yl)cyclopropane-1-carboxamide<br>(Pyrazole trans to amide; All absolute stereochemistry arbitrarily assigned) | 480.2 | 1H NMR (400 MHz, DMSO-d$_6$) δ 10.93 (s, 1H), 9.36 (s, 1H), 8.56 (s, 1H), 8.26 (s, 1H), 7.83 (s, 1H), 7.78 (d, J = 2.1 Hz, 1H), 7.56 (s, 1H), 7.30 (br s, 2H), 7.29 (d, J = 2.1 Hz, 1H), 7.00 (s, 1H), 6.81 (s, 1H), 3.93 (s, 3H), 3.77 (s, 3H), 2.47 (s, 3H), 2.26-2.14 (m, 2H), 1.45-1.32 (m, 1H), 1.28-1.15 (m, 1H). |

TABLE A-2-continued

| Cmpd No.. | Structure/Name | LCMS R$_T$ (min) M + H$^+$ Method | $^1$H NMR (ppm) |
|---|---|---|---|
| 406 | 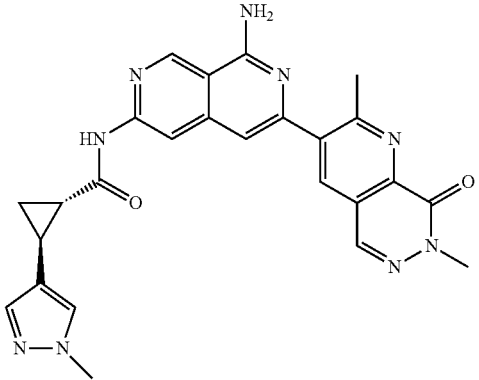 [SMILES: Cc1nc2c(=O)n(C)ncc2cc1-c1cc2cc(NC(=O)[C@H]3C[C@@H]3c3cnn(C)c3)ncc2c(N)n1]<br>(1S,2S)-N-(8-amino-6-(2,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 482.2 | 1H NMR (400 MHz, DMSO-d$_6$) δ 10.98 (s, 1H), 9.41 (s, 1H), 9.03 (s, 1H), 8.67 (s, 1H), 8.30 (s, 1H), 7.56 (s, 1H), 7.45 (br s, 2H), 7.29 (s, 1H), 7.08 (s, 1H), 3.79 (s, 3H), 3.77 (s, 3H), 2.71 (s, 3H), 2.21 (dd, J = 7.2, 7.2 Hz, 2H), 1.44-1.36 (m, 1H), 1.23-1.14 (m, 1H). |
| 407 | 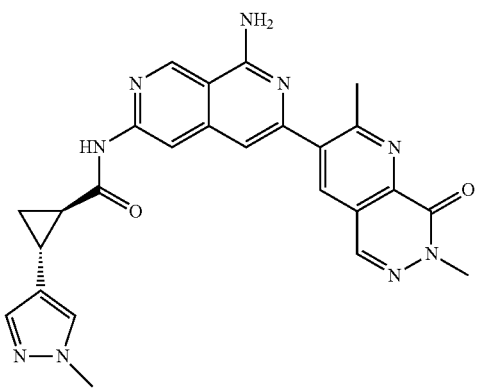 [SMILES: Cc1nc2c(=O)n(C)ncc2cc1-c1cc2cc(NC(=O)[C@@H]3C[C@H]3c3cnn(C)c3)ncc2c(N)n1]<br>(1R,2R)-N-(8-amino-6-(2,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 482.2 | 1H NMR (400 MHz, DMSO-d$_6$) δ 10.98 (s, 1H), 9.41 (s, 1H), 9.03 (s, 1H), 8.67 (s, 1H), 8.30 (s, 1H), 7.56 (s, 1H), 7.45 (br s, 2H), 7.29 (s, 1H), 7.08 (s, 1H), 3.79 (s, 3H), 3.77 (s, 3H), 2.71 (s, 3H), 2.21 (dd, J = 7.2, 7.2 Hz, 2H), 1.44-1.36 (m, 1H), 1.23-1.14 (m, 1H). |

TABLE A-2-continued

| Cmpd No.. | Structure/Name | LCMS R$_T$ (min) M + H$^+$ Method | $^1$H NMR (ppm) |
|---|---|---|---|
| 408 | 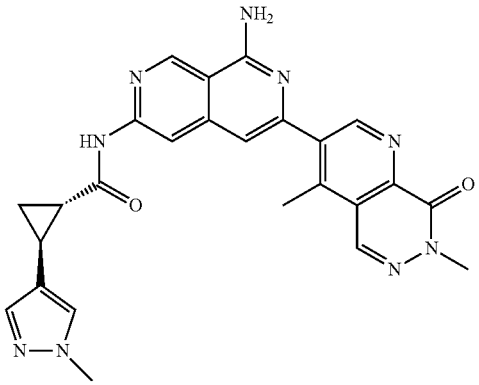 [SMILES: Cc1c(-c2cc3cc(NC(=O)[C@H]4C[C@@H]4c4cnn(C)c4)ncc3c(N)n2)cnc2c(=O)n(C)ncc12]<br>(1S,2S)-N-(8-amino-6-(4,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 482.1 | 1H NMR (400 MHz, DMSO-d$_6$) δ 10.98 (s, 1H), 9.41 (s, 1H), 8.45 (s, 1H), 8.40 (s, 1H), 8.29 (s, 1H), 7.56 (s, 1H), 7.44 (br s, 2H), 7.29 (s, 1H), 7.12 (s, 1H), 3.77 (s, 6H), 2.78 (s, 3H), 2.26-2.17 (m, 2H), 1.45-1.34 (m, 1H), 1.27-1.13 (m, 1H). |
| 409 | 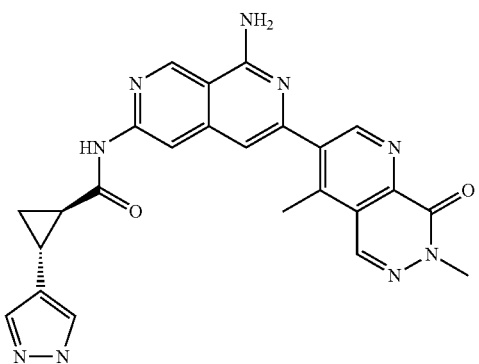<br>(1R,2R)-N-(8-amino-6-(4,7-dimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 482.2 | 1H NMR (400 MHz, DMSO-d$_6$) δ 10.98 (s, 1H), 9.41 (s, 1H), 8.45 (s, 1H), 8.40 (s, 1H), 8.29 (s, 1H), 7.56 (s, 1H), 7.44 (br s, 2H), 7.29 (s, 1H), 7.12 (s, 1H), 3.77 (s, 6H), 2.78 (s, 3H), 2.26-2.17 (m, 2H), 1.45-1.34 (m, 1H), 1.27-1.13 (m, 1H). |

TABLE A-2-continued

| Cmpd No.. | Structure/Name | LCMS R_T (min) M + H+ Method | $^1$H NMR (ppm) |
|---|---|---|---|
| 410 | 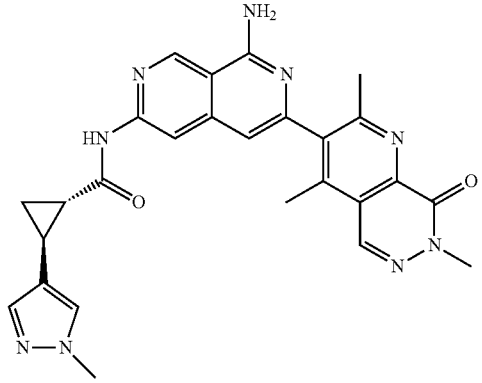 [SMILES: Cc1nc2c(=O)n(C)ncc2c(C)c1-c1cc2cc(NC(=O)[C@H]3C[C@@H]3c3cnn(C)c3)ncc2c(N)n1]<br>(1S,2S)-N-(8-amino-6-(2,4,7-trimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 496.2 | 1H NMR (400 MHz, DMSO-d$_6$) δ 10.97 (s, 1H), 9.40 (s, 1H), 8.57 (s, 1H), 8.24 (s, 1H), 7.56 (s, 1H), 7.45 (br s, 2H), 7.29 (s, 1H), 6.85 (s, 1H), 3.77 (s, 3H), 3.77 (s, 3H), 2.45 (s, 3H), 2.41 (s, 3H), 2.20 (dd, J = 6.9, 6.9 Hz, 2H), 1.42-1.33 (m, 1H), 1.22-1.15 (m, 1H). |
| 411 | 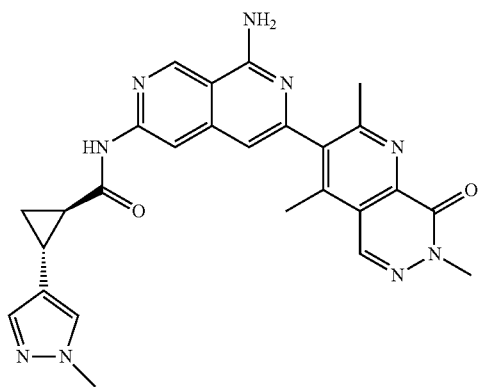 [SMILES: Cc1nc2c(=O)n(C)ncc2c(C)c1-c1cc2cc(NC(=O)[C@@H]3C[C@H]3c3cnn(C)c3)ncc2c(N)n1]<br>(1R,2R)-N-(8-amino-6-(2,4,7-trimethyl-8-oxo-7,8-dihydropyrido[2,3-d]pyridazin-3-yl)-2,7-naphthyridin-3-yl)-2-(1-methyl-1H-pyrazol-4-yl)cyclopropane-1-carboxamide (Pyrazole trans to amide; All absolute stereochemistry arbitrarily assigned) | 496.2 | 1H NMR (400 MHz, DMSO-d$_6$) δ 10.97 (s, 1H), 9.40 (s, 1H), 8.57 (s, 1H), 8.24 (s, 1H), 7.56 (s, 1H), 7.45 (br s, 2H), 7.29 (s, 1H), 6.85 (s, 1H), 3.77 (s, 3H), 3.77 (s, 3H), 2.45 (s, 3H), 2.41 (s, 3H), 2.20 (dd, J = 6.9, 6.9 Hz, 2H), 1.42-1.33 (m, 1H), 1.22-1.15 (m, 1H). |
| 412 | 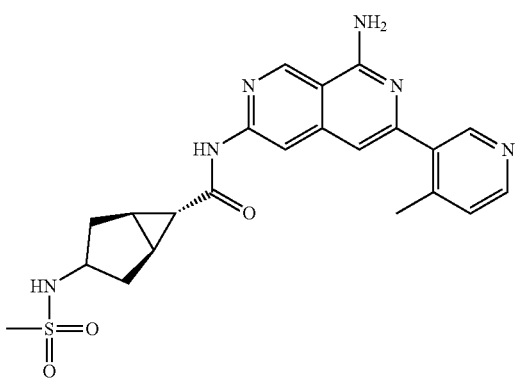<br>N-(8-amino-6-(4-methylpyridin-3-yl)-2,7-naphthyridin-3-yl)-3-(methylsulfonamido)bicyclo[3.1.0]hexane-6-carboxamide | 1.391<br>453.3<br>J | 1H NMR (300 MHz, CD3OD) δ 9.35 (s, 1H), 8.52 (s, 1H), 8.46-8.40 (m, 2H), 7.38 (d, J = 5.1 Hz, 1H), 7.01 (s, 1H), 5.32-5.00 (m, 1H), 3.98-3.72 (m, 1H), 3.22-3.02 (m, 1H), 3.01-2.94 (m, 1H), 2.92 (s, 3H), 2.90-2.71 (m, 1H), 2.62-2.49 (m, 1H), 2.41 (s, 3H), 2.19-1.98 (m, 1H), 1.70-1.50 (m, 1H) |

TABLE A-2-continued

| Cmpd No. | Structure/Name | LCMS R_T (min) M + H+ Method | ¹H NMR (ppm) |
|---|---|---|---|
| 413 | 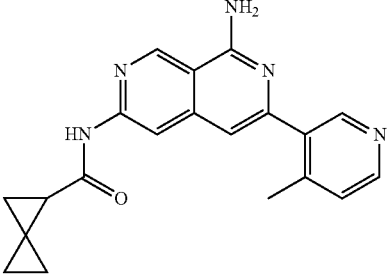 [SMILES: Cc1ccncc1-c1cc2cc(NC(=O)C3CC34CC4)ncc2c(N)n1]<br>N-(8-amino-6-(4-methylpyridin-3-yl)-2,7-naphthyridin-3-yl)spiro[2.2]pentane-1-carboxamide | 346.1 | 1H NMR (400 MHz, DMSO-d₆) δ 10.75 (s, 1H), 9.35 (s, 1H), 8.56 (s, 1H), 8.43 (d, J = 5.0 Hz, 1H), 8.26 (s, 1H), 7.28 (br s, 2H), 7.33-7.21 (m, 1H), 6.95 (s, 1H), 2.43-2.40 (m, 1H), 2.41 (s, 3H), 1.42 (t, J = 3.8 Hz, 1H), 1.35 (dd, J = 7.4, 3.4 Hz, 1H), 0.95-0.73 (m, 4H). |
| 414 | 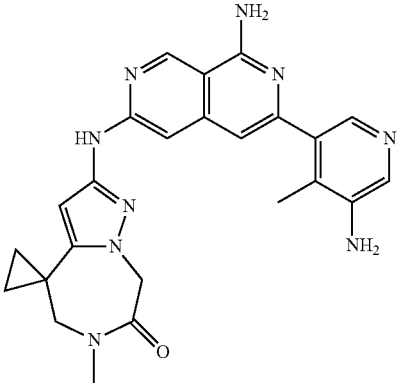 [SMILES: Cc1c(N)cncc1-c1cc2cc(Nc3cc4n(n3)CC(=O)N(C)CC43CC3)ncc2c(N)n1]<br>2'-((8-amino-6-(5-amino-4-methylpyridin-3-yl)-2,7-naphthyridin-3-yl)amino)-6'-methyl-5',6'-dihydrospiro[cyclopropane-1,4'-pyrazolo[1,5-d][1,4]diazepin]-7'(8'H)-one | 0.962<br>456.3<br>J | 1H NMR (300 MHz, DMSO-d₆) δ 9.31 (s, 1H), 9.19 (s, 1H), 7.92 (s, 1H), 7.75 (s, 1H), 7.45 (s, 1H), 7.02 (s, 2H), 6.68 (s, 1H), 5.67 (s, 1H), 5.10-5.06 (m, 4H), 3.72 (s, 2H), 2.99 (s, 3H), 2.06 (s, 3H), 1.23-1.16 (m, 2H), 0.96-0.92 (m, 2H) |
| 415 | 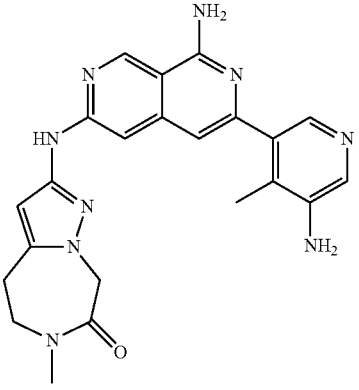 [SMILES: Cc1c(N)cncc1-c1cc2cc(Nc3cc4n(n3)CC(=O)N(C)CC4)ncc2c(N)n1]<br>2-((8-amino-6-(5-amino-4-methylpyridin-3-yl)-2,7-naphthyridin-3-yl)amino)-6-methyl-5,6-dihydro-4H-pyrazolo[1,5-d][1,4]diazepin-7(8H)-one | 1.407<br>430.2<br>J | 1H NMR (400 MHz, DMSO-d₆) δ 9.37 (s, 1H), 9.20 (s, 1H), 7.93 (s, 1H), 7.77 (s, 1H), 7.51 (s, 1H), 7.03 (s, 2H), 6.68 (s, 1H), 6.06 (s, 1H), 5.11 (s, 2H), 4.99 (s, 2H), 3.84 (t, J = 6Hz, 2H), 3.06 (t, J = 6 Hz, 2H), 2.96 (s, 3H), 2.08 (s, 3H) |

TABLE A-2-continued

| Cmpd No.. | Structure/Name | LCMS R$_T$ (min) M + H$^+$ Method | $^1$H NMR (ppm) |
|---|---|---|---|
| 416 | 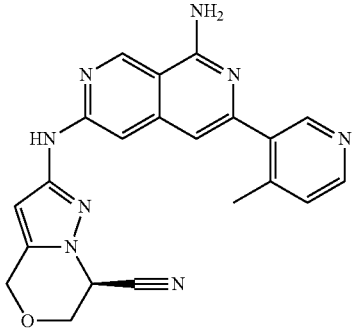<br>(S)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile (Absolute stereochemistry arbitrarily assigned) | 0.965<br>399.3<br>J | 1H NMR (400 MHz, CD3OD) δ 9.17 (s, 1H), 8.51 (s, 1H), 8.41 (d, J = 4 Hz, 1H), 7.67 (s, 1H), 7.37 (d, J = 8 Hz, 1H), 6.85 (s, 1H), 6.14 (s, 1H), 5.33-5.32 (m, 1H), 4.98 (d, J = 12 Hz, 1H), 4.77 (s, 1H), 4.45 (d, J = 4 Hz, 1H), 4.29-4.25 (m, 1H), 2.44 (s, 3H) |
| 417 | 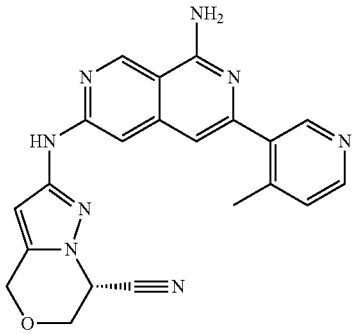<br>(R)-2-((8-amino-6-(4-methylpyridin-3-yl)-2,7-naphthyridin-3-yl)amino)-6,7-dihydro-4H-pyrazolo[5,1-c][1,4]oxazine-7-carbonitrile (Absolute stereochemistry arbitrarily assigned) | 1.554<br>399.3<br>J | 1H NMR (400 MHz, CD3OD) δ 9.17 (s, 1H), 8.51 (s, 1H), 8.41 (d, J = 4 Hz, 1H), 7.67 (s, 1H), 7.37 (d, J = 8 Hz, 1H), 6.85 (s, 1H), 6.14 (s, 1H), 5.33-5.32 (m, 1H), 4.98 (d, J = 12 Hz, 1H), 4.77 (s, 1H), 4.45 (d, J = 4 Hz, 1H), 4.29-4.25 (m, 1H), 2.44 (s, 3H). |
| 418 | 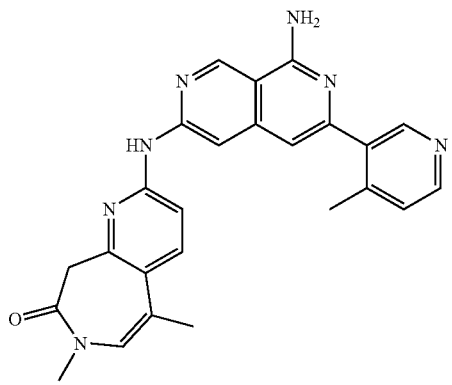 [SMILES: CC1=CN(C)C(=O)Cc2nc(Nc3cc4cc(-c5cnccc5C)nc(N)c4cn3)ccc21]<br>2-((8-amino-6-(4-methylpyridin-3-yl)-2,7-naphthyridin-3-yl)amino)-5,7-dimethyl-7,9-dihydro-8H-pyrido[2,3-d]azepin-8-one | 3.03<br>438.1<br>N | — |

TABLE A-2-continued

| Cmpd No.. | Structure/Name | LCMS R$_T$ (min) M + H$^+$ Method | $^1$H NMR (ppm) |
|---|---|---|---|
| 419 | 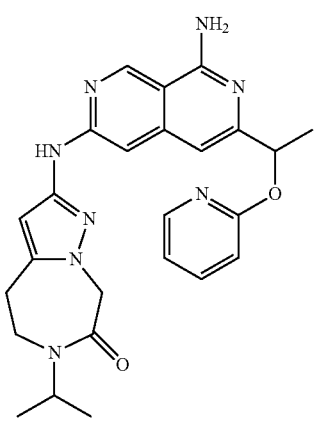 [SMILES: CC(Oc1ccccn1)c1cc2cc(Nc3cc4n(n3)CC(=O)N(C(C)C)CC4)ncc2c(N)n1]<br>(+/−)-2-((8-amino-6-(1-(pyridin-2-yloxy)ethyl)-2,7-naphthyridin-3-yl)amino)-6-isopropyl-5,6-dihydro-4H-pyrazolo[1,5-d][1,4]diazepin-7(8H)-one | 2.411<br>473.2<br>J | 1H NMR (400 MHz, DMSO-d$_6$) δ 9.33 (s, 1H), 9.12 (s, 1H), 8.11-8.08 (m, 1H), 7.76-7.69 (m, 1H), 7.40 (s, 1H), 7.05 (s, 2H), 6.94-6.92 (m, 2H), 6.62 (s, 1H), 6.00 (s, 1H), 5.96-5.90 (m, 1H), 4.96 (s, 2H), 4.64-4.55 (m, 1H), 3.79 (t, J = 6 Hz, 2H), 2.99 (t, J = 6 Hz, 2H), 1.57 (d, J = 9 Hz, 3H), 1.12 (d, J = 9 Hz, 6H). |
| 420 | 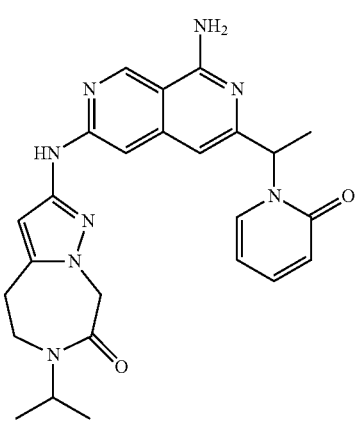 [SMILES: CC(C)N1CCc2cc(Nc3cc4cc(C(C)n5ccccc5=O)nc(N)c4cn3)nn2CC1=O]<br>(+/−)-2-((8-amino-6-(1-(2-oxopyridin-1(2H)-yl)ethyl)-2,7-naphthyridin-3-yl)amino)-6-isopropyl-5,6-dihydro-4H-pyrazolo[1,5-d][1,4]diazepin-7(8H)-one | 1.967<br>473.2<br>J | 1H NMR (400 MHz, DMSO-d$_6$) δ 9.43 (s, 1H), 9.14 (s, 1H), 7.60-7.58 (m, 1H), 7.48 (s, 1H), 7.42-7.36 (m, 1H), 7.08 (s, 2H), 6.64 (s, 1H), 6.41 (d, J = 9 Hz, 1H), 6.24-6.19 (m, 1H), 6.03 (s, 1H), 5.99-5.92 (m, 1H), 4.98 (s, 2H), 4.64-4.55 (m, 1H), 3.79 (t, J = 6 Hz, 2H), 2.99 (t, J = 6 Hz, 2H), 1.63 (d, J = 9 Hz, 3H), 1.12 (d, J = 9 Hz, 6H) |
| 421 | 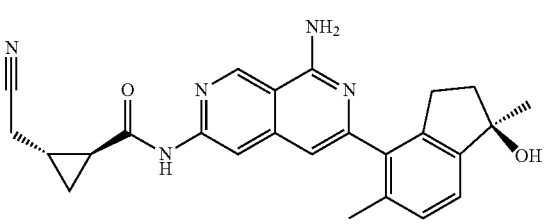 [SMILES: Cc1ccc2c(c1-c1cc3cc(NC(=O)[C@H]4C[C@@H]4CC#N)ncc3c(N)n1)CC[C@@]2(C)O]<br>(1S,2R)-N-(8-amino-6-((R)-1-hydroxy-1,5-dimethyl-2,3-dihydro-1H-inden-4-yl)-2,7-naphthyridin-3-yl)-2-(cyanomethyl)cyclopropane-1-carboxamide (Cyanomethyl trans to amide; Absolute stereochemistry arbitrarily assigned) | 1.28<br>428.3<br>P | — |

TABLE A-2-continued

| Cmpd No.. | Structure/Name | LCMS $R_T$ (min) M + H⁺ Method | ¹H NMR (ppm) |
|---|---|---|---|
| 422 | (1S,2R)-N-(8-amino-6-((S)-1-hydroxy-1,5-dimethyl-2,3-dihydro-1H-inden-4-yl)-2,7-naphthyridin-3-yl)-2-(cyanomethyl)cyclopropane-1-carboxamide (Cyanomethyl trans to amide; Absolute stereochemistry arbitrarily assigned) | 1.27 428.3 P | — |
| 423 | (1S,2S,3S)-N-(8-amino-6-(3-amino-2-methylphenyl)-2,7-naphthyridin-3-yl)-2-methyl-3-(1-methyl-1H-pyrazol-4-yl)cyclopropane-1-carboxamide (Pyrazole trans to amide; methyl relative stereochemistry arbitrarily assigned; All absolute stereochemistry arbitrarily assigned) | 1.179 428.3 P | — |
| 424 | (1R,2S,3R)-N-(8-amino-6-(3-amino-2-methylphenyl)-2,7-naphthyridin-3-yl)-2-methyl-3-(1-methyl-1H-pyrazol-4-yl)cyclopropane-1-carboxamide (Pyrazole trans to amide; methyl relative stereochemistry arbitrarily assigned; All absolute stereochemistry arbitrarily assigned) | 1.19 428.3 P | — |

TABLE A-2-continued

| Cmpd No.. | Structure/Name | LCMS $R_T$ (min) M + H$^+$ Method | $^1$H NMR (ppm) |
|---|---|---|---|
| 425 | 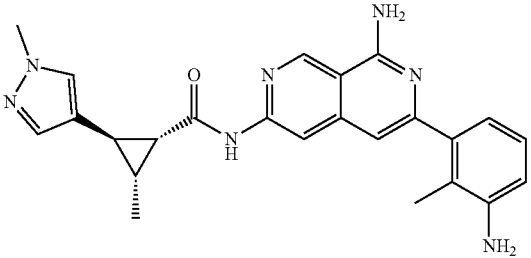<br>(1R,2R,3R)-N-(8-amino-6-(3-amino-2-methylphenyl)-2,7-naphthyridin-3-yl)-2-methyl-3-(1-methyl-1H-pyrazol-4-yl)cyclopropane-1-carboxamide<br>(Pyrazole trans to amide; methyl relative stereochemistry arbitrarily assigned: All absolute stereochemistry arbitrarily-assigned) | 1.19<br>428.3<br>P | — |
| 426 | 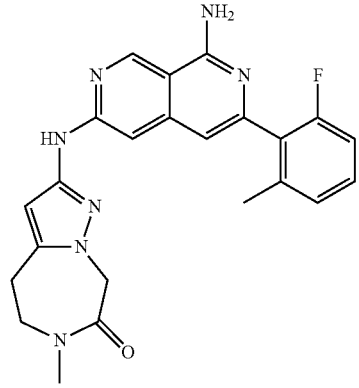 [SMILES: Cc1cccc(F)c1-c1cc2cc(Nc3cc4n(n3)CC(=O)N(C)CC4)ncc2c(N)n1]<br>2-((8-amino-6-(2-fluoro-6-methylphenyl)-2,7-naphthyridin-3-yl)amino)-6-methyl-5,6-dihydro-4H-pyrazolo[1,5-d][1,4]diazepin-7(8H)-one | 1.122<br>432.3<br>P | — |
| 427 | 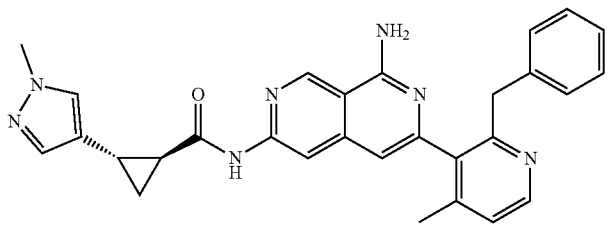 [SMILES: Cc1ccnc(Cc2ccccc2)c1-c1cc2cc(NC(=O)[C@H]3C[C@@H]3c3cnn(C)c3)ncc2c(N)n1]<br>(+/−)-trans-N-(8-amino-6-(2-benzyl-4-methylpyridin-3-yl)-2,7-naphthyridin-3-yl)-2-(1-methyl-1H-pyrazol-4-yl)cyclopropane-1-carboxamide | 1.96<br>490.3<br>P | — |

TABLE A-2-continued

| Cmpd No. | Structure/Name | LCMS $R_T$ (min) M + H⁺ Method | ¹H NMR (ppm) |
|---|---|---|---|
| 428 | 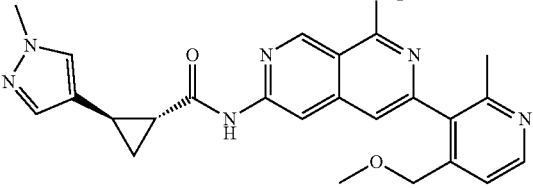<br>(1R,2R)-N-(8-amino-6-(2-(methoxymethyl)-6-methylphenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 1.37<br>443.3<br>P | — |
| 429 | 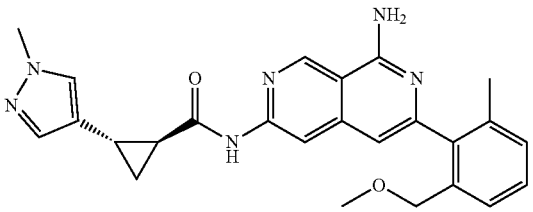 [SMILES: COCc1cccc(C)c1-c1cc2cc(NC(=O)[C@H]3C[C@@H]3c3cnn(C)c3)ncc2c(N)n1]<br>(1R,2R)-N-(8-amino-6-(2-(methoxymethyl)-6-methylphenyl)-2,7-naphthyridin-3-yl)-2-(1-methyl-1H-pyrazol-4-yl)cyclopropane-1-carboxamide<br>(Pyrazole trans to amide; Absolute stereochemistry arbitrarily assigned) | 1.36<br>443.3<br>P | — |

"—" refers to unreported data.

Biological Evaluation

Exemplary compounds of Formula I or Ia were tested to assess compound inhibition of HPK-1. The $K_i$ for each exemplary compound was determined Example B1

HPK1 Ki Determination

Example B1A

HPK1-FL HTRF Enzymatic Assay ("HTRF")

Assay Principle:

HPK-FL enzyme phosphorylates Biotin-SLP-76 substrate in the presence of ATP at 1 mM and varying concentrations of test compound. Product is detected by FRET using Eu-anti-pSLP76 Ab and SA-XL665. See www.cisbio.com/HTRF for additional HTRF technology information.

Instrumentation:
Echo555 compound dispenser
Agilent Bravo
Perkin Elmer Envision

| Final Assay Conditions: | |
|---|---|
| HPK full length, T165E S171E: | 0.125 nM |
| Biotin-SLP76: | 100 nM |
| ATP: | 1 mM |
| | (ATP Km = 20 uM) |
| Eu-anti-pSLP76: | 2 nM |
| SA-XL665: | 8.3 nM |
| Preincubation time: | 30 min |
| Kinase reaction time: | 60 min |
| Temperature: | ambient |
| Total volume: | 12 ul |
| ATP$^{app}$ Km: | 17.7 uM |

Materials:
Assay plate: White ProxiPlate 384 F (PerkinElmer cat #6008289)
Kinase: HPK full length double mutant
Substrate: Biotin-SLP76
ATP: 100 mM ATP
BSG: 2% BSG
DMSO: DMSO (Sigma cat #34869-100ML)
Reaction Buffer: H₂O/50 mM HEPES, pH 7.5/10 mM MgCl₂/2 mM TCEP/0.01% Brij-35/0.01% BSG
Detection mix: Eu-anti-pSLP76/SA-XL665 (Cisbio, #610SAXAC)

Assay Procedure Ki Determination:

To a 384 well Proxiplate with 80 nL compound or DMSO spotted on was added 4 μl/well kinase mix. The mixture was preincubated for 30 minutes and then 4 μl/well substrate mix was added. The solution was incubated for 60 min and then 4 μl/well detection mix was added. The solution was incubated for another 60 min. The plates were then loaded onto a Perkin Elmer Envision and the TR-FRET signal was measured at 615 and 665 nm. A ratio of 665/620 was used to calculate the % activity at each concentration of compound.

Example B1B

HPK1 Lantha Binding Assay ("Lanth")

| Materials: | |
|---|---|
| Reagent | Vender-Cat# |
| white ProxiPlate 384 F(assay plate) | PerkinElmer-6008289 |
| 384-well Microplate(compound plate) | Labcyte-LP-0200 |
| HPK1 enzyme | Signalchem-M23-11G |
| Tracer-222 | Invitrogen-PV6121 |
| Eu-Anti-GST Ab | Invitrogen-PV5594 |
| Assay Buffer | 2 mM DTT(Sigma-43815), 0.01% BRIJ-35(Sigma-B4184), 10 mM MgCl$_2$, 50 mM HEPES (Invitrogen-15630130 ) |

Procedure:

I. Compound Dilution:

The compounds to be tested were diluted by preparing 12.5 uL/well of 5 mM compound (100×) in columns 2 and 13 and 10 ul/well of DMSO in columns 3-12, 14-23, and wells A1-H1 and I24-P24 of the compound plate using a Bravo liquid handling platform. For the reference compound, the top concentration was 1 mM. To the plate was added 10 ul 2 mM staurosporine in wells J1-P1 and A24-H24. A 11 point 5-fold compound serial dilution was performed using the Bravo liquid handling platform. From the plate were transferred 2.5 ul of the solutions from column 2 and column 13 to the 10 ul of DMSO in columns 3 and 14 & so on. The compound plate was centrifuged at 2500 rpm for 1 min. From the compound plate was transferred 80 nl of the compounds into an assay plate using the Echo liquid handler system. One compound plate makes two assay plates. Each assay plate is sealed and stored in an N$_2$ cabinet.

II. Assay Condition:

The following assay concentrations and times were used: 2 nM HPK1, 2 nM Eu-Anti-GST Ab, and 15 nM Tracer222, with 60 min incubation time.

III. HPK Lantha Binding Assay:

For the binding assay, 4 ul 2×HPK1 and Eu-anti-GST antibody were added to each well of the assay plate using a Multidrop reagent dispenser. The solutions were incubated in a 23 C incubator for 1 h. To each well of the assay plate was added 4 ul 2× Tracer-222 using a Multidrop reagent dispenser. The solutions were again incubated in a 23 C incubator for 1 h. The results of the assay were read using an Envision plate reader with the following parameters: TR_FRET, 340ex/615 and 665em; 100 usec Delay; and 200 usec integration.

IV. Analysis:

Compound Ki was analyzed using Morrison ki fit model in XL-fit a. fit=$(1-((((E+x)+(Ki*(1+(S/Kd))))-(((((E+x)+(Ki*(1+(S/Kd))))^{\wedge})-((4*E)*x))^{\wedge}0.5))/(2*E)))$
   res=(y-fit)

b. Parameters:
   E=enzyme concentration
   S=Tracer222 concentration, Kd=Tracer222 Kd
   All measurements reported using the same units (uM)

Exemplary compounds of Formula I or Ia were tested in the binding assays. The Ki values determined are listed in Tables B1-1 and B1-2. The Ki data in Table B1-1 are based on the "Lanth" assay.

TABLE B1-1

| Compound No. | HPK1 $K_i$ (μM) (Lanth) |
|---|---|
| 1 | 0.00038 |
| 2 | 0.00156 |
| 3 | 0.00514 |
| 4 | 0.00287 |
| 5 | 0.00131 |
| 6 | 0.000793 |
| 7 | 0.00289 |
| 8 | 0.00164 |
| 9 | 0.00716 |
| 10 | 0.00173 |
| 11 | 0.00365 |
| 12 | 0.0493 |
| 13 | 0.0156 |
| 14 | 0.00946 |
| 15 | 0.0226 |
| 16 | 0.00721 |
| 17 | 0.0161 |
| 18 | 0.0475 |
| 19 | 0.0079 |
| 20 | 0.00322 |
| 21 | 0.00276 |
| 22 | 0.00491 |
| 23 | 0.0492 |
| 24 | 0.00068 |
| 25 | 0.00154 |
| 26 | 0.00021 |
| 27 | 0.00108 |
| 28 | 0.0149 |
| 29 | 0.014 |
| 30 | 0.00175 |
| 31 | 0.0039 |
| 32 | 0.0264 |
| 33 | 0.0341 |
| 34 | 0.034 |
| 35 | 5.54 |
| 36 | 4.08 |
| 37 | 0.0298 |
| 38 | 0.0484 |
| 39 | 2.03 |
| 40 | 0.098 |
| 41 | 5.8 |
| 42 | 0.0405 |
| 43 | 0.00205 |
| 44 | 0.048 |
| 45 | 0.0117 |
| 46 | 0.00152 |
| 47 | 0.00185 |
| 48 | 0.0103 |
| 49 | 0.00682 |
| 50 | 0.0059 |
| 51 | 0.0013 |
| 52 | 0.00298 |
| 53 | 0.000736 |
| 54 | 0.0489 |
| 55 | 0.0064 |
| 56 | 0.0065 |
| 57 | 0.00524 |
| 58 | 0.00281 |
| 59 | 0.0417 |

TABLE B1-1-continued

| Compound No. | HPK1 $K_i$ (μM) (Lanth) |
|---|---|
| 60 | 0.0106 |
| 61 | 0.0258 |
| 62 | 0.00503 |
| 63 | 0.101 |
| 64 | 0.44 |
| 65 | 0.00547 |
| 66 | 0.00488 |
| 67 | 0.00576 |
| 68 | 0.545 |
| 70 | 0.0276 |
| 71 | 0.010 |
| 72 | 0.0141 |
| 73 | 0.0134 |
| 74 | 0.0013 |
| 75 | 0.0008 |
| 76 | 0.0013 |
| 77 | 0.0006 |
| 78 | 0.0001 |
| 79 | 0.839 |
| 80 | 0.0003 |
| 81 | 0.0003 |
| 82 | 0.0004 |
| 83 | 0.0003 |
| 84 | 0.0018 |
| 85 | 0.00198 |
| 86 | 0.0161 |
| 87 | 0.0103 |
| 88 | 0.172 |
| 89 | 0.00488 |
| 90 | 0.101 |
| 91 | 0.000583 |
| 92 | 0.00736 |
| 93 | 0.00364 |
| 94 | 0.00321 |
| 96 | 0.00406 |
| 97 | 0.00040 |
| 98 | 0.163 |
| 99 | 0.0707 |
| 100 | 0.0183 |
| 101 | 0.0225 |
| 102 | 0.0215 |
| 103 | 0.00382 |
| 104 | 0.0189 |
| 105 | 0.0402 |
| 106 | 0.00497 |
| 107 | 0.000654 |
| 108 | 0.0028 |
| 109 | 0.0013 |
| 110 | 0.00649 |
| 111 | 0.00238 |
| 112 | 0.00187 |
| 113 | 0.00353 |
| 114 | 0.00224 |
| 115 | 0.00489 |
| 116 | 0.00557 |
| 117 | 0.00847 |
| 118 | 0.000476 |
| 119 | 0.00142 |
| 120 | 2.4 |
| 121 | 0.00058 |
| 122 | 0.0000629 |
| 123 | 0.0049 |
| 124 | 0.0011 |
| 125 | 0.0068 |
| 126 | 0.007 |
| 127 | 0.0053 |
| 128 | 0.0025 |
| 129 | 0.00098 |
| 130 | 0.0026 |
| 131 | 0.00031 |
| 132 | 0.0065 |
| 133 | 0.015 |
| 134 | 0.0056 |
| 135 | 0.00025 |
| 136 | 0.13 |
| 137 | 0.11 |
| 138 | 0.032 |

TABLE B1-1-continued

| Compound No. | HPK1 $K_i$ (μM) (Lanth) |
|---|---|
| 139 | 0.00048 |
| 140 | 0.0014 |
| 141 | 0.0023 |
| 142 | 0.0014 |
| 143 | 0.0059 |
| 144 | 0.0011 |
| 145 | 0.002 |
| 146 | 0.000020 |
| 147 | 0.039 |
| 148 | 0.0028 |
| 149 | 0.00078 |
| 150 | 0.00077 |
| 151 | 0.015 |
| 152 | 0.00015 |
| 153 | 0.0044 |
| 154 | 0.0011 |
| 155 | 0.0024 |
| 156 | 0.021 |
| 157 | 0.00057 |
| 158 | 0.0036 |
| 159 | 0.00023 |
| 160 | 0.0012 |
| 161 | 0.000020 |
| 162 | 0.0032 |
| 163 | 0.0012 |
| 164 | 0.0081 |
| 165 | 0.00095 |
| 166 | 0.0015 |
| 167 | 0.0094 |
| 168 | 0.002 |
| 169 | 0.00048 |
| 170 | 0.003 |
| 171 | 1.5 |
| 172 | 0.00019 |
| 173 | 0.000047 |
| 174 | 0.0025 |
| 175 | 0.0034 |
| 176 | 0.0055 |
| 177 | 0.0085 |
| 178 | 0.00025 |
| 179 | 0.0029 |
| 180 | 0.044 |
| 181 | 0.0032 |
| 182 | 0.0012 |
| 183 | 0.00098 |
| 184 | 0.0025 |
| 185 | 0.089 |
| 186 | 0.004 |
| 187 | 0.016 |
| 188 | 0.012 |
| 189 | 0.01 |
| 190 | 0.0011 |
| 191 | 0.0027 |
| 192 | 0.000501 |
| 193 | 0.000135 |
| 194 | 0.000967 |
| 195 | 0.00002 |
| 196 | 0.00601 |
| 197 | 0.000027 |
| 198 | 0.00055 |
| 199 | 0.00339 |
| 200 | 0.000343 |
| 201 | 0.00649 |
| 202 | 0.0004 |
| 203 | 0.0004 |
| 204 | 0.00099 |
| 205 | 0.0000881 |
| 206 | 0.0000509 |
| 207 | 0.0171 |
| 208 | 0.0146 |
| 209 | 0.0307 |
| 210 | 0.000258 |
| 211 | 0.000154 |
| 212 | 0.000685 |
| 213 | 0.000957 |
| 214 | 0.000039 |
| 215 | 0.00119 |

TABLE B1-1-continued

| Compound No. | HPK1 $K_i$ (μM) (Lanth) |
|---|---|
| 216 | 0.00353 |
| 217 | 0.0000614 |
| 218 | 0.000020 |
| 219 | 0.000567 |
| 220 | 0.000592 |
| 221 | 0.000026 |
| 222 | 0.00177 |
| 223 | 0.000135 |
| 224 | 0.0152 |
| 225 | 0.0842 |
| 226 | 0.0586 |
| 227 | 0.0387 |
| 228 | 0.011 |
| 229 | 0.0212 |
| 230 | 0.000295 |
| 231 | 0.000173 |
| 232 | 0.00728 |
| 233 | 0.000694 |
| 234 | 0.000078 |
| 235 | 0.000706 |
| 236 | 0.0233 |
| 237 | 0.0102 |
| 238 | 0.00194 |
| 239 | 0.00528 |
| 240 | 0.047 |
| 241 | 0.00219 |
| 242 | 0.0312 |
| 243 | 0.00137 |
| 244 | 0.00356 |
| 245 | 0.00542 |
| 246 | 0.0000455 |
| 247 | 0.0000219 |
| 248 | 0.00103 |
| 249 | 0.000433 |
| 250 | 0.000184 |
| 251 | 0.000512 |
| 252 | 0.000569 |
| 253 | 0.0000892 |
| 254 | 0.00455 |
| 255 | 0.0339 |
| 256 | 0.00002 |
| 257 | 0.00101 |
| 258 | 0.000695 |
| 259 | 0.146 |
| 260 | 0.00073 |
| 261 | 0.0367 |
| 262 | 0.000439 |
| 263 | 0.000021 |
| 264 | 0.000134 |
| 265 | 0.000249 |
| 266 | 0.000118 |
| 267 | 0.000113 |
| 268 | 0.000147 |
| 269 | 0.0023 |
| 270 | 0.000116 |
| 271 | 0.000768 |
| 272 | 0.000139 |
| 273 | 0.0000675 |
| 274 | 0.000297 |
| 275 | 0.000225 |
| 276 | 0.00601 |
| 277 | 0.000837 |
| 278 | 0.000763 |
| 279 | 0.000188 |
| 280 | |
| 281 | |
| 282 | |
| 283 | |
| 284 | |
| 285 | |
| 286 | 0.00182 |
| 287 | 0.000078 |
| 288 | 0.00619 |
| 289 | 0.00739 |
| 290 | 0.00336 |
| 291 | 0.0638 |
| 292 | 0.0000417 |
| 293 | 0.000668 |
| 294 | 0.00214 |
| 295 | 0.000287 |
| 296 | 0.000026 |
| 297 | 0.000972 |
| 298 | 0.000932 |
| 299 | 0.0000359 |
| 300 | 0.00136 |
| 301 | 0.0000692 |
| 302 | 0.00065 |
| 303 | 0.000027 |
| 304 | 0.00302 |
| 305 | 0.000152 |
| 306 | 0.00325 |
| 307 | 0.000112 |
| 308 | 0.00304 |
| 309 | 0.000184 |
| 310 | 0.0000675 |
| 311 | 0.00115 |
| 312 | 0.00577 |
| 313 | 0.00002 |
| 314 | 0.0131 |
| 315 | 0.0122 |
| 316 | 0.000522 |
| 317 | 0.000020 |
| 318 | 0.000032 |
| 319 | 0.000020 |
| 320 | 0.00782 |
| 321 | 0.0574 |
| 322 | 0.0148 |
| 323 | 0.0763 |
| 324 | 0.00048 |
| 325 | 0.00343 |
| 326 | 0.000074 |
| 327 | 0.00143 |
| 328 | 0.000114 |
| 329 | 0.00265 |
| 330 | <0.000020 |
| 331 | 0.00112 |
| 332 | 0.00562 |
| 333 | 0.000432 |
| 334 | 0.0204 |
| 335 | 0.00441 |
| 336 | 0.00135 |
| 337 | 0.0613 |
| 338 | 0.345 |
| 339 | 0.00314 |
| 340 | 0.00614 |
| 341 | 0.000509 |
| 342 | 0.00143 |
| 343 | 0.00173 |
| 344 | 0.00226 |
| 345 | 0.0033 |
| 346 | 0.00244 |
| 347 | 0.0118 |
| 348 | 0.00117 |

TABLE B1-2

| Compound No. | HPK1 Ki L = Lanth H = HTRF |
|---|---|
| 349 | 6.2 nM (H) |
| 350 | 39.7 nM (H) |
| 351 | 0.33 nM (H) |
| 352 | 5 nM (H) |
| 353 | 29 nM (L) |
| 354 | 0.083 nM (L) |
| 355 | 1.8 nM (L) |
| 356 | 0.30 nM (L) |
| 357 | 2.7 nM (L) |
| 358 | 0.52 nM (L) |
| 359 | 1.1 nM (L) |

TABLE B1-2-continued

| Compound No. | HPK1 Ki<br>L = Lanth<br>H = HTRF |
|---|---|
| 360 | 0.099 nM (L) |
| 361 | 2.3 nM (L) |
| 362 | 0.22 nM (L) |
| 363 | 0.17 nM (L) |
| 364 | 2.1 nM (L) |
| 365 | 7.3 nM (L) |
| 366 | 0.53 nM (L) |
| 367 | 1.4 nM (L) |
| 368 | 3.7 nM (L) |
| 369 | 0.22 nM (L) |
| 370 | 1.8 nM (L) |
| 371 | 0.46 nM (L) |
| 372 | 0.41 nM (L) |
| 373 | 75 nM (L) |
| 374 | 12 nM (L) |
| 375 | 96 nM (L) |
| 376 | 15 nM (L) |
| 377 | 0.66 nM (L) |
| 378 | 0.049 nM (L) |
| 379 | 0.69 nM (L) |
| 380 | 22 nM (L) |
| 381 | 8.1 nM (L) |
| 382 | 14 nM (L) |
| 383 | 0.47 nM (L) |
| 384 | 1.8 nM (L) |
| 385 | 2.9 nM (L) |
| 386 | 20 nM (L) |
| 387 | 19 nM (L) |
| 388 | 1.6 nM (L) |
| 389 | 0.033 nM (L) |
| 391 | 170 nM (L) |
| 392 | 9.3 nM (L) |
| 393 | 1.7 nM (L) |
| 394 | 34 nM (L) |
| 395 | 0.29 nM (L) |
| 396 | 5.6 nM (L) |
| 397 | 0.25 nM (L) |
| 398 | 30 nM (L) |
| 399 | 3.6 nM (L) |
| 400 | 1.2 nM (L) |
| 401 | 21 nM (L) |
| 402 | 0.26 nM (L) |
| 403 | 7.6 nM (L) |
| 404 | 1.9 nM (L) |
| 405 | 20 nM (L) |
| 406 | 0.74 nM (L) |
| 407 | 6.3 nM (L) |
| 408 | 9.9 nM (L) |
| 409 | 20 nM (L) |
| 410 | 33 nM (L) |
| 411 | 6.3 nM (L) |
| 412 | 96 nM (L) |
| 413 | 15 nM (L) |
| 414 | 0.013 nM (H) |
| 415 | 0.21 nM (H) |
| 416 | 0.97 nM (L) |
| 417 | 0.27 nM (L) |
| 418 | 1.4 nM (L) |
| 419 | 511 nM (H) |
| 420 | 1644 nM (H) |
| 421 | 190 nM, L |
| 422 | 8 nM, L |
| 423 | 9.4 nM, L |
| 424 | 8 nM, L |
| 425 | 1 nM, L |
| 426 | 0.02 nM, L |
| 427 | 0.78 nM, L |
| 428 | 8 nM, L |
| 429 | 51 nM, L |

Example B2

Human T-Cell IL2 Induction Assay

Assay Principle:

Anti-CD3 and anti-CD28 activates TCR signaling in primary human pan T cells leading to IL-2 promoter induction. Secreted IL-2 in cell culture supernatant is detected by electrochemiluminescence using a capture antibody against IL-2 and an anti-IL-2 antibody labeled with SULFO-tag.

Literature:

See www.mesoscale.com for additional electrochemiluminescence technology information.

Assay Procedure:

Incubate primary human pan T cells with varying concentrations of test compounds for 30 minutes in a humidified incubator at 37° C. and 5% $CO_2$. Transfer cells to a plate pre-coated with a fixed concentration of anti-human CD3 (determined separately for each donor lot) and add soluble anti-human CD28 (final concentration=1 µg/ml). Stimulate cells in a humidified incubator at 37° C. and 5% $CO_2$ for 4 hours. Transfer 25 µl of supernatant to a MSD single spot plate pre-coated with an anti-human IL-2 antibody. Incubate MSD plate overnight at 4° C. with gentle shaking. Wash MSD plate 4× with wash buffer. Add SULFO-tagged detection antibody at a 1:50 dilution and incubate at room temperature shaking for 2 hours. Wash MSD plate 4× with wash buffer and add 150 µl 2×MSD read buffer. Read on an MSD instrument. Normalize data to stimulated/untreated controls to calculate % activity at each concentration of compound.

Materials:

Frozen Primary Human Pan-T Cells (StemCell Technologies #70024)

anti-human CD3 (OKT3 clone) (eBioscience #16-0037-81)

anti-human CD28 (CD28.2 clone) (BD #555725)

96-well Human IL-2 tissue culture kit (MSD #K151AHB-4)

Instrumentation:

Biomek FX for liquid handling (Beckman Coulter)

MSD SECTOR S 600 (Meso Scale Discovery)

Exemplary compounds of Formula I or Ia were tested in the human T-cell IL-2 induction assays. The % increase measured for IL-2 in cells treated by the test compounds relative to untreated cells are provided in Table B2 for certain compounds (structures as shown with the HPK1 Ki values).

TABLE B2

| Cmpound No. | HPK1 Ki (nM)<br>H = HTRF<br>L = Lanth | % IL-2 increase relative to untreated cells | Assayed concentration (µM) |
|---|---|---|---|
| 24 | 0.68, L | 513% | 0.93 |
| 103 | 3.8, L | 94% | 0.31 |
| 130 | 2.6, L | 274% | 0.93 |
| 256 | 0.59, H | 699% | 0.31 |
| 273 | 0.06, L | 830% | 0.93 |
| 328 | 0.11, L | 936% | 0.93 |
| 356 | 0.3, L | 732% | 2.8 |
| 379 | 0.69, L | 547% | 2.8 |
| 389 | 0.033, L | 265% | 0.10 |

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Further Embodiments

Embodiment 1. A compound of Formula I:

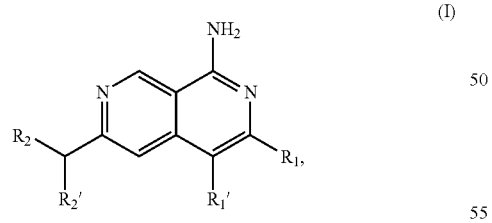

(I)

or a pharmaceutically acceptable salt thereof, wherein,
$R_1$ is:
$C_{2-9}$ heteroaryl, $C_{2-9}$ heterocyclyl, or $C_{6-10}$ aryl, wherein said heteroaryl or heterocyclyl has 1-4 heteroatoms selected from O, S and N; and wherein said aryl, heteroaryl and heterocyclyl can be optionally substituted with one, two, three or four substituents, $R_6$, $R_7 R_8$ and $R_{8'}$, each of which is independently selected from the group consisting of:
 i. branched or linear $C_{1-6}$ alkyl, $C_{1-6}$ alkenyl, $C_{1-6}$ alkenylene, and $C_{3-9}$ cycloalkyl, wherein said alkyl, alkenyl, alkenylene, and cycloalkyl can be optionally substituted with hydroxyl, halogen, —$CF_2$, —$CF_3$, amino, di($C_{1-6}$)alkylamino, mono($C_{1-6}$)alkylamino, cyano, $C_{3-7}$ cycloalkyl, $C_{1-6}$ alkoxy, —$SO_2R'$, —$SO_2NR'R''$, —(CO)NR'R'', or —NR'(CO)R'', wherein R' and R'' are independently H or $C_{1-6}$ alkyl;
 ii. $NR^aR^b$—C(O)—,
  wherein, $R^a$ and $R^b$ are each independently hydrogen or $C_{1-6}$ alkyl, wherein said alkyl can optionally be substituted with hydroxyl, halogen, —$CF_2$, or —$CF_3$;
 iii. $C_{1-6}$ alkoxy;
 iv. halogen;
 v. cyano;
 vi. hydroxyl;
 vii. amino;
 viii. di($C_{1-6}$)alkylamino;
 ix. mono($C_{1-6}$)alkylamino;
 x. —$NR^c(CO)R^d$, wherein $R^c$ and $R^d$ are independently H or $C_{1-6}$ alkyl;
 xi. —$CF_3$;
 xii. —$CF_2$;
 xiii. —$SO_2R'$, wherein R' is as described above;
 xiv. —$SO_2NR'R''$, wherein R' and R'' are as described above;
 xv. —(CO)$NR^cR^d$; wherein $R^c$ and $R^d$ are as described above;
 xvi. —(CO)$OR^e$; wherein $R^e$ is H, $C_{1-6}$ alkyl, or $CH_2$-aryl;
 xvii. substituted or unsubstituted $C_{6-10}$ aryl or $C_{3-5}$ heterocyclyl; and
wherein a carbon embedded in said aryl, heteroaryl or heterocyclyl taken together with an oxygen to which it is bound can form a carbonyl;
$R_1$ is:
$C_{1-6}$ alkyl, $C_{2-6}$ alkenyl, $C_{3-6}$ cycloalkyl, $C_{2-9}$ heteroaryl, or halogen, wherein said alkyl, alkenyl, cycloalkyl, and heteroaryl can be optionally substituted with hydroxyl, halogen, or amino; $R_2$ is A-C(O)—, wherein, A is:
 i. $C_{3-7}$ cycloalkyl($C_{1-6}$)$_j$alkyl- or $C_{2-9}$ heterocyclyl ($C_{1-6}$)$_j$alkyl-, wherein, j is 1 or 0; and wherein said cycloalkyl or heterocyclyl can be optionally substituted with one, two, three or four of $R_5$, wherein $R_5$, in each instance, is independently selected from the group consisting of branched or linear $C_{1-6}$ alkyl, halogen, cyano, cyano($C_{1-6}$)alkyl-, —$CF_3$, —$CF_2$, hydroxy($C_{1-6}$)alkyl, halo($C_{1-6}$)alkyl, hydroxyl, ($C_{1-6}$ alkyl)-O—($C_{1-6}$ alkyl)-, amino, di($C_{1-6}$)alkylamino, mono($C_{1-6}$)alkylamino, amino($C_{1-6}$)alkyl, $C_{1-6}$ alkoxy, $CH_3CO_2$—($C_{1-6}$ alkyl)-, —$SO_2R'$, —$SO_2NR'R''$, —(CO)NR'R'', —NR'(CO)R'', wherein, in each instance, R' and R'' are as described above, optionally substituted $C_{2-9}$ heteroaryl, optionally substituted $C_{2-9}$ heterocyclyl, optionally substituted $C_{6-10}$ aryl and $NR^eR^f$—C(O)—($C_{1-6}$ alkyl)$_k$-, wherein $R^e$ and $R^f$ are each independently selected from the group consisting of hydrogen and branched or linear $C_{1-6}$ alkyl, or $R^e$ and $R^f$ together with the nitrogen to which each is bound can form a $C_{3-7}$ cycloalkyl, which can be optionally substituted with branched or linear $C_{1-6}$ alkyl, $C_{3-4}$ cycloalkyl, halogen, cyano, —$CF_3$, —$CF_2$, or hydroxyl;
  and k is 1 or 0;
 or, said cycloalkyl or heterocyclyl together with two of $R_5$ form a bicyclic or spiro ring, wherein two of $R_5$ attached to different carbons are taken together with the carbon to which each is attached to form a bicyclic, or two of $R_5$ attached to the same carbon are taken together with the carbon to which each is attached to form a spiro ring;

ii. —$NR^gR^h$, wherein $R^g$ is H or branched or linear $C_{1-6}$ alkyl, wherein said alkyl can be optionally substituted with hydroxyl, halogen, cyano, amino, di($C_{1-6}$)alkylamino, mono ($C_{1-6}$)alkylamino; —$CF_2$, or —$CF_3$;

$R^h$ is selected from the group consisting of:
  a. branched or linear $C_{1-6}$ alkyl, wherein said alkyl can be optionally substituted with hydroxyl, halogen, cyano, amino, di($C_{1-6}$)alkylamino, mono($C_{1-6}$)alkylamino, —$CF_2$, —$CF_3$, or $NR^{e'}R^{f'}$—C(O)—, wherein $R^{e'}$ and $R^{f'}$ are each independently hydrogen or branched or linear $C_{1-6}$ alkyl;

and,
  b. $C_{3-7}$ cycloalkyl($C_{1-6}$ alkyl)$_m$-, $C_{2-9}$ heteroaryl ($C_{1-6}$ alkyl)$_m$-$C_{6-10}$ aryl($C_{1-6}$ alkyl)$_m$- or $C_{2-9}$ heterocyclyl($C_{1-6}$ alkyl)$_m$-, wherein, m is 1 or 0; and wherein said cycloalkyl, heteroaryl, aryl or heterocyclyl can be optionally substituted with one or two of $R_{5'}$,
  wherein $R_{5'}$, in each instance, is independently selected from the group consisting of branched or linear $C_{1-6}$ alkyl, halogen, cyano, —$CF_3$, —$CF_2$, hydroxy($C_{1-6}$)alkyl, halo($C_{1-6}$)alkyl, hydroxyl, $C_{1-6}$ alkoxy, amino, amino($C_{1-6}$)alkyl, and $NR^iR^j$—C(O)—($C_{1-6}$ alkyl)$_{k'}$-,
  wherein $R^i$ and $R^j$ are independently selected from the group consisting of hydrogen and branched or linear $C_{1-6}$ alkyl, and k' is 1 or 0;

iii. $R_9$—($C_{1-6}$ alkyl)-, wherein $R_9$ is selected from the group consisting of hydroxyl, halogen, —$CF_2$, —$CF_3$, cyano, $C_{1-6}$ alkoxy, —$NR^oR^p$, wherein $R^o$ and $R^p$ are each independently H or branched or linear $C_{1-6}$ alkyl, $NR^{o'}R^{p'}$—CO—, wherein $R^{o'}$ and $R^{p'}$ are each independently hydrogen or branched or linear $C_{1-6}$ alkyl;

iv. B—($C_{1-6}$ alkyl)$_t$-, wherein, B is $C_{3-9}$ heteroaryl or $C_{3-7}$ heterocyclyl, wherein, said heteroaryl or heterocyclyl has 1-3 heteroatoms selected from O, S and N; and wherein said heteroaryl or heterocyclyl can be optionally substituted with one, two or three of $R^{10}$, $R^{10'}$ and $R^{10''}$, each of which is independently selected from the group consisting of:
  a. branched or linear $C_{1-6}$ alkyl or $C_{3-4}$ cycloalkyl, wherein said alkyl or cycloalkyl can be optionally substituted with hydroxyl, halogen, —$CF_2$, —$CF_3$, amino, di($C_{1-6}$)alkylamino, mono($C_{1-6}$)alkylamino, cyano, —(CO)$NR^qR^r$ or —$NR^q$(CO)$R^r$, wherein $R^q$ and $R^r$ are independently H or $C_{1-6}$ alkyl;
  b. $C_{3-7}$ cycloalkyl; and
  c. $C_{3-7}$ heterocyclyl;
  d. hydroxyl;
  e. halogen;
  f. —$CF_2$;
  g. —$CF_3$;
  h. amino;
  i. di($C_{1-6}$)alkylamino;
  j. mono($C_{1-6}$)alkylamino;
  k. cyano;
  l. —(CO)$NR^sR^t$, wherein $R^s$ and $R^t$ are independently H or $C_{1-6}$ alkyl; and
  m. —$NR^s$(CO)$R^t$, wherein $R^s$ and $R^t$ are independently H or $C_{1-6}$ alkyl;
  and, t is 1 or 0;

v. $(C_{6-10}$ aryl)$_{q'}$-($C_{1-6}$ alkyl)$_n$-O— or pyrrolidinyl-O—, wherein, said aryl can be optionally substituted with one, two or three of $R^{11}$, $R^{12}$ and $R^{13}$, each of which is selected from the group consisting of branched or linear $C_{1-6}$ alkyl, hydroxyl, halogen, —$CF_2$, —$CF_3$, cyano, $C_{1-6}$ alkoxy, and $NR^uR^v$—, wherein $R^u$ and $R^v$ are each independently H or branched or linear $C_{1-6}$ alkyl,
  and, n is 1 or 0, q' is 1 or 0, provided that one of n and q' is 1;

vi. branched or linear $C_{1-6}$ alkyl, $C_{1-6}$ alkenyl, $C_{1-6}$ alkenylene, wherein said alkyl, alkenyl, and alkenylene, can be optionally substituted with hydroxyl, halogen, —$CF_2$, —$CF_3$, amino, di($C_{1-6}$)alkylamino, mono($C_{1-6}$)alkylamino, cyano, $C_{3-7}$ cycloalkyl, $C_{1-6}$ alkoxy, —$SO_2R'$, —$SO_2NR'R''$, —(CO)NR'R'', or —NR'(CO)R'', wherein R' and R'' are independently H or $C_{1-6}$ alkyl;

or, $R_2$ is D, wherein D is:
i. $C_{6-10}$ aryl-($C_{1-6}$ alkyl)$_z$-, or $C_{3-9}$ heteroaryl-($C_{1-6}$ alkyl)$_z$-, wherein, said heteroaryl has 1-4 heteroatoms selected from O, S and N; and wherein said aryl or heteroaryl can be optionally substituted with one, two, three or four of $R^{14}$, $R^1$, $R^{16'}$ and $R^{16}$, each of which is independently selected from the group consisting of:
  a. branched or linear $C_{1-6}$ alkyl, wherein said alkyl can be optionally substituted with hydroxyl, halogen, —$CF_2$, —$CF_3$, amino, di($C_{1-6}$)alkylamino, mono ($C_{1-6}$)alkylamino, cyano $C_{1-6}$ alkoxy, —$SO_2R'$, —$SO_2NR'R''$, —(CO)$NR^wR^x$, or —$NR^w$(CO)$R^x$, wherein $R^w$ and $R^x$ are independently H or $C_{1-6}$ alkyl, wherein two of $R^{14}$, $R^{15}$, $R^{16'}$ and $R^{16}$ attached to different atoms are taken together with the atom to which each is attached to form a bicyclic;
  b. $C_{3-7}$ cycloalkyl;
  c. $C_{3-7}$ heterocyclyl;
  d. hydroxyl;
  e. halogen;
  f. —$CF_2$;
  g. —$CF_3$;
  h. amino;
  i. di($C_{1-6}$)alkylamino;
  j. mono($C_{1-6}$)alkylamino;
  k. cyano;
  l. —$NR^y$(CO)$R^z$, wherein $R^y$ and $R^z$ are independently H or $C_{1-6}$ alkyl;
  m. —(CO)$NR^yR^z$, wherein $R^y$ and $R^z$ are independently H or $C_{1-6}$ alkyl;
  n. —$SO_2NR^yR^z$, wherein $R^y$ and $R^z$ are independently H or $C_{1-6}$ alkyl; and
  o. —(CO)$OR^y$, wherein $R^y$ is H or $C_{1-6}$ alkyl; and, z is 1 or 0;

ii. $C_{3-7}$ cycloalkyl-($SO_2$)—, wherein said cycloalkyl can be optionally substituted with one or two of $R^{6'}$, wherein $R^{6'}$, in each instance, is independently selected from the group consisting of branched or linear $C_{1-6}$ alkyl, halogen, cyano, —$CF_3$, —$CF_2$, hydroxy($C_{1-6}$) alkyl, halo($C_{1-6}$)alkyl, hydroxyl, ($C_{1-6}$ alkyl)-O—($C_{1-6}$ alkyl)-, $C_{1-6}$ alkoxy, amino, di($C_{1-6}$)alkylamino, mono ($C_{1-6}$)alkylamino, amino($C_{1-6}$)alkyl, and $NR^{e'}R^{f'}$—C (O)—($C_{1-6}$ alkyl)$_n$-, wherein $R^{e'}$ and $R^{f'}$ are independently selected from the group consisting of hydrogen and branched or linear $C_{1-6}$ alkyl, and n is 1 or 0; and iii. $C_{1-6}$ alkyl or pyrrolidine, wherein said alkyl is optionally substituted with halogen;

and, $R_2$, is H or branched or linear $C_{1-6}$ alkyl.

Embodiment 2. The compound of embodiment 1, wherein $R_1$ is an optionally substituted $C_{2-9}$ heteroaryl or $C_{3-7}$ heterocyclyl.

Embodiment 3. The compound of embodiment 2, wherein $R_1$ is selected from the group consisting of:

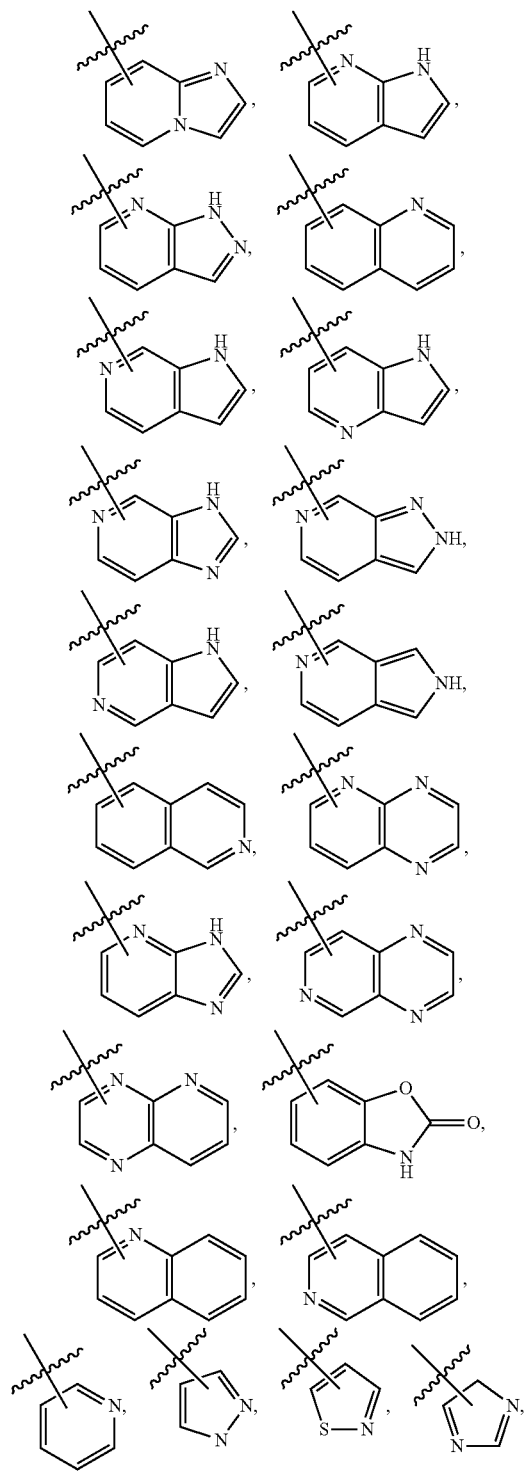

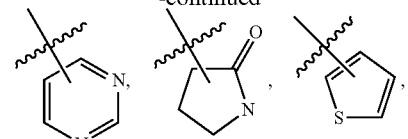

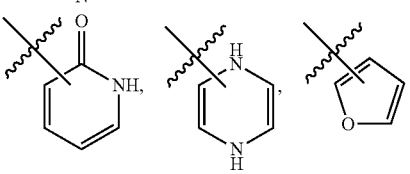

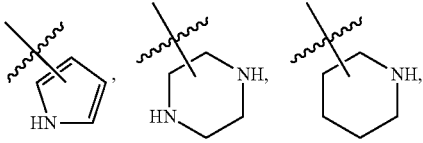

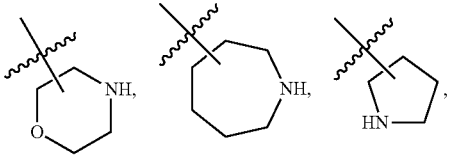

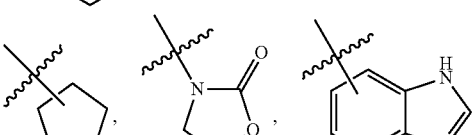

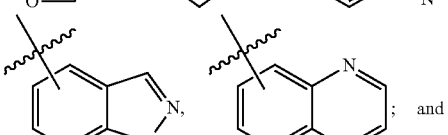

; and

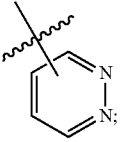

each of which can be optionally substituted with one, two or three substituents, $R_6$, $R_7$ and $R_8$.

Embodiment 4. The compound of embodiment 3, wherein $R_1$ is selected from the group consisting of:

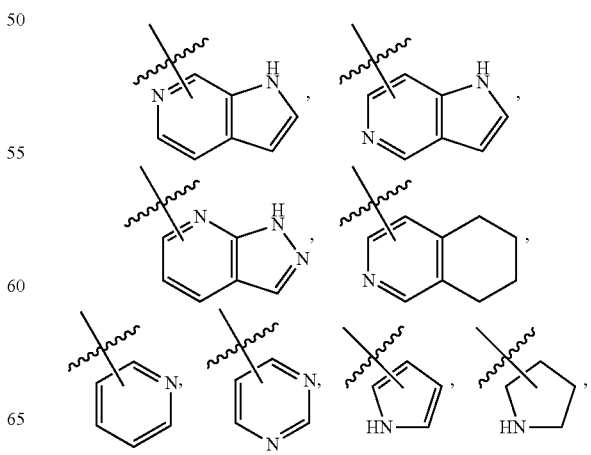

-continued

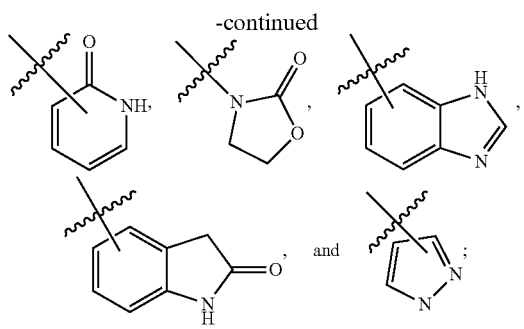

each of which can be optionally substituted with one, two or three substituents, $R_6$, $R_7$ and $R_8$.

Embodiment 5. The compound of embodiment 4, wherein $R_1$ is:

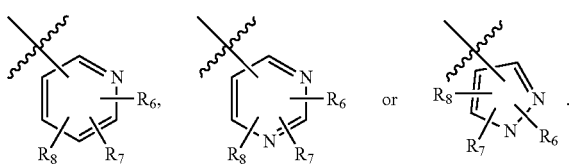

Embodiment 6. The compound of embodiment 5, wherein $R_1$ is

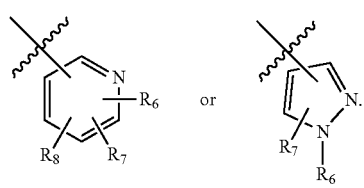

Embodiment 7. The compound of embodiment 6, wherein $R_1$ is:

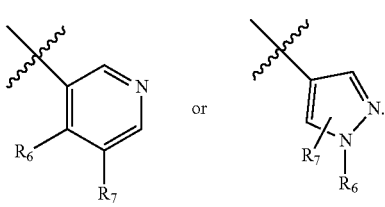

Embodiment 8. The compound of embodiment 7, wherein $R_1$ is:

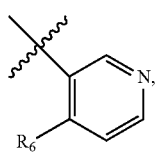

wherein, $R_6$ is $C_{1-6}$ alkyl, optionally substituted with hydroxyl, —$CF_2$, —$CF_3$, or halogen.

Embodiment 9. The compound of embodiment 7, wherein $R_6$ is methyl.

Embodiment 10. The compound of embodiment 2, wherein A is i.

Embodiment 11. The compound of embodiment 10, wherein A is optionally substituted $C_{3-7}$ cycloalkyl($C_{1-6}$)$_j$alkyl-.

Embodiment 12. The compound of embodiment 11, wherein j is 0.

Embodiment 13. The compound of embodiment 12, wherein $R_2$ is:

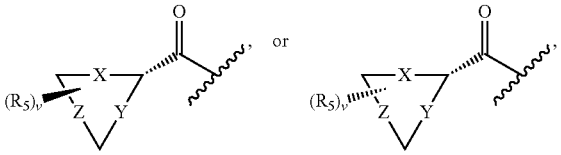

wherein, v is zero, one, two, three or four; X, Y and Z are each independently absent or —$CH_2$—, and wherein, if present, zero, one or two of H on each of X, Y and Z can be $R_5$.

Embodiment 14. The compound of embodiment 12, wherein $R_2$ is:

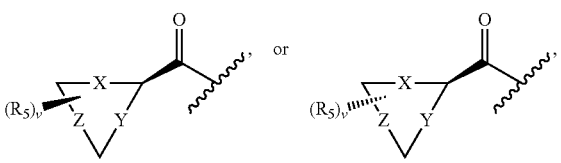

wherein, v is zero, one, two, three or four; X, Y and Z are each independently absent or —$CH_2$—, and wherein, if present, zero, one or two of H on each of X, Y and Z can be $R_5$.

Embodiment 15. The compound of embodiment 12, wherein $R_2$ is:

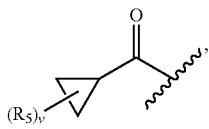

wherein, v is zero, one or two.

Embodiment 16. The compound of embodiment 15, wherein $R_2$ is:

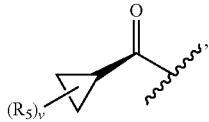

wherein, v is zero, one or two.

Embodiment 17. The compound of embodiment 16, wherein $R_5$ is other than hydrogen and $R_2$ is:

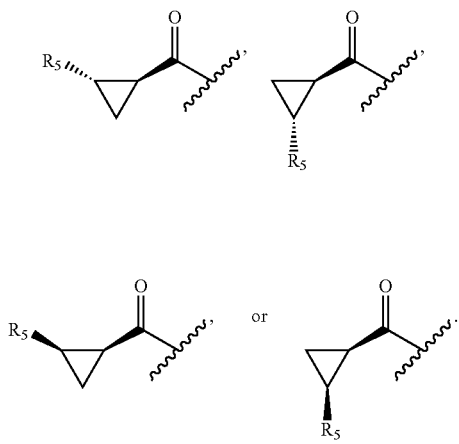

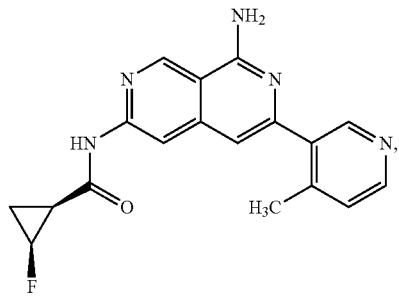
1

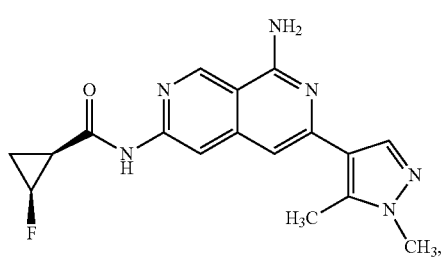
2

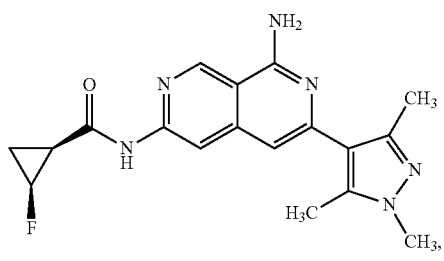
3

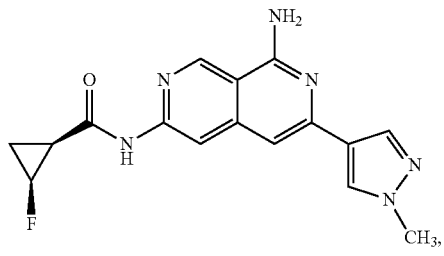
4

Embodiment 18. The compound of embodiment 15, wherein $R_2$ is

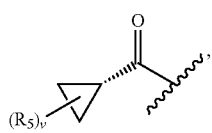

wherein, v is zero, one or two.

Embodiment 19. The compound of embodiment 18, wherein $R_5$ is other than hydrogen and $R_2$ is:

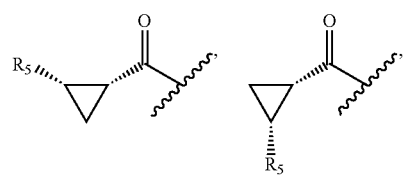

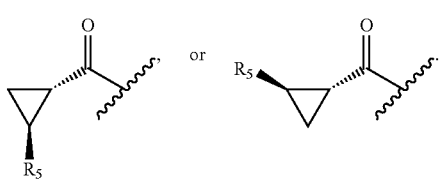

Embodiment 20. The compound of embodiment 11, wherein said cycloalkyl is bicyclic, spiro or unsaturated.

Embodiment 21. The compound of embodiment 13, wherein $R_5$ is selected from the group consisting of hydrogen, fluorine, cyano, $NH_2$—C(O)—, alkyl-($C_{1-6}$)alkoxy-, optionally substituted $C_{2-9}$ heteroaryl, and cyano($C_{1-6}$)alkyl.

Embodiment 22. The compound of embodiment 21, wherein $R_5$ is fluoro or cyano.

Embodiment 23. The compound of embodiment 21, wherein $R_5$ is hydrogen.

Embodiment 24. The compound of embodiment 12, having one of the following structures:

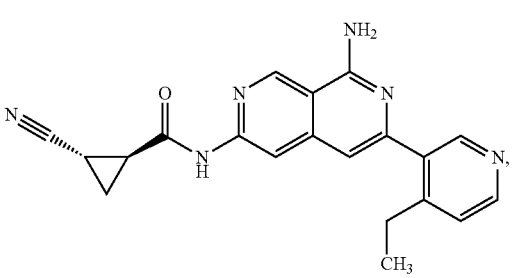
5

-continued
6
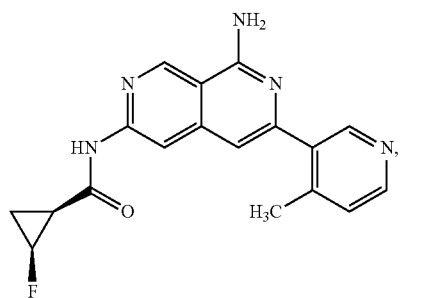
7
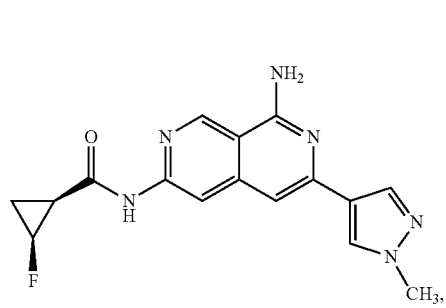
8
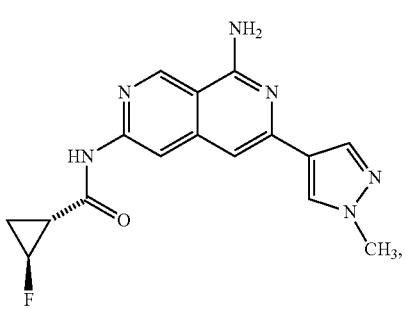
10
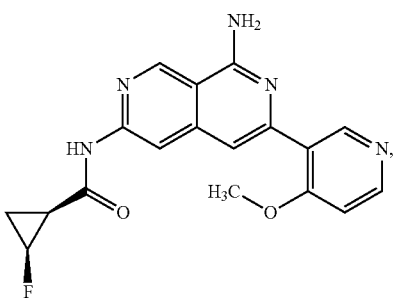
11
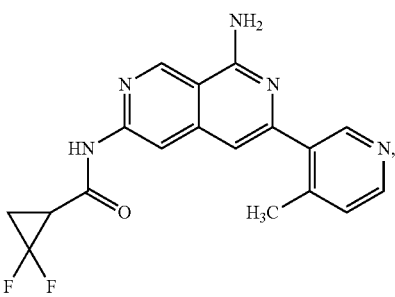
-continued
12
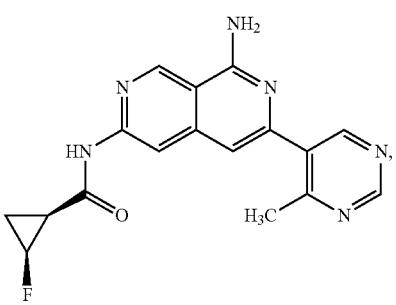
13
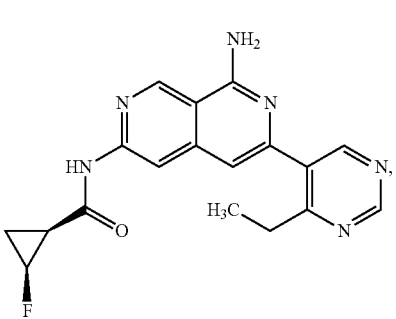
14
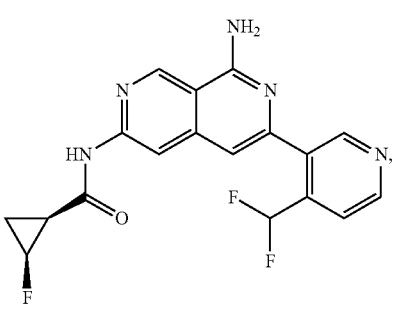
15
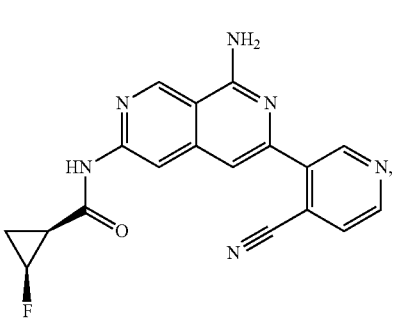
16
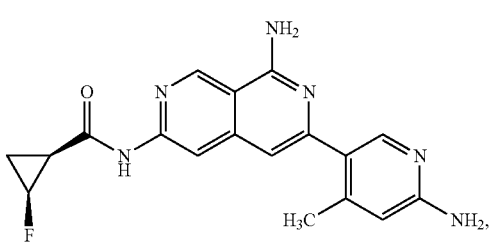

-continued
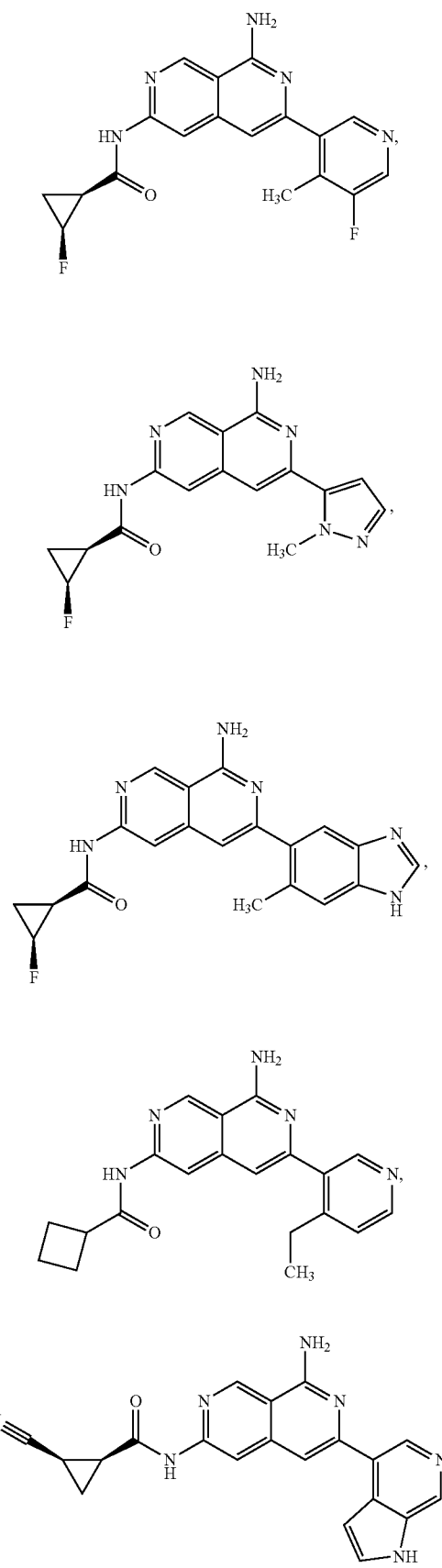
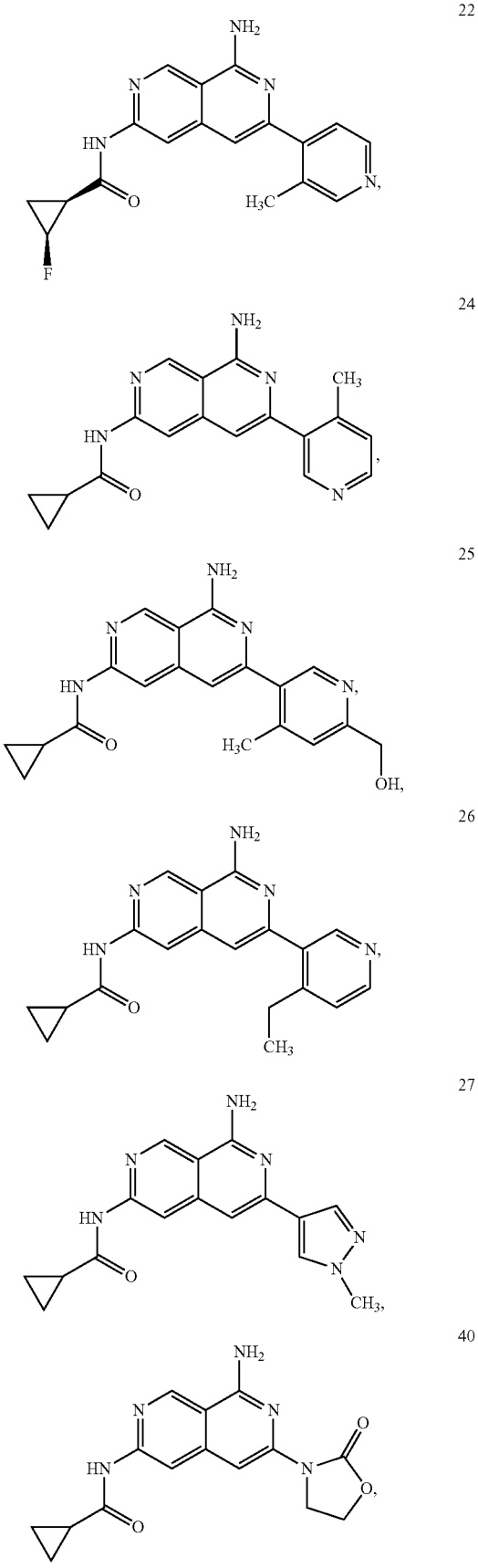

1177
-continued
42
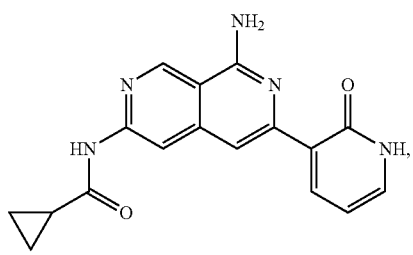
43
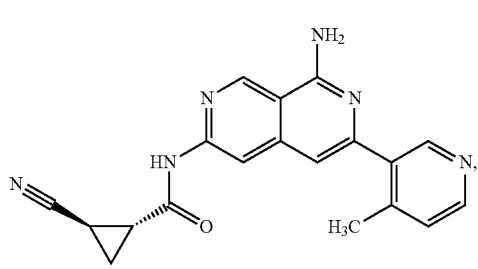
44
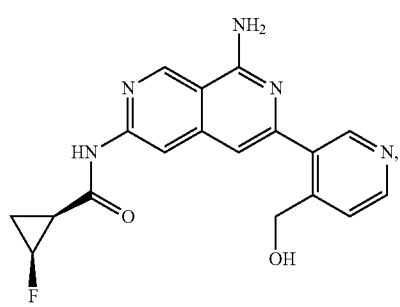
45
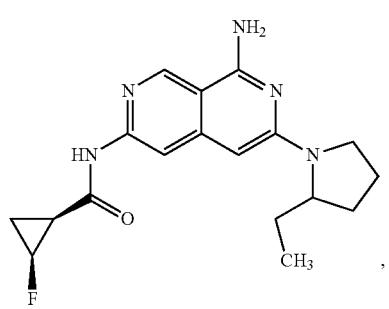
46
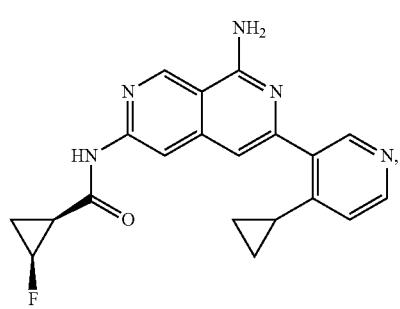
1178
-continued
47
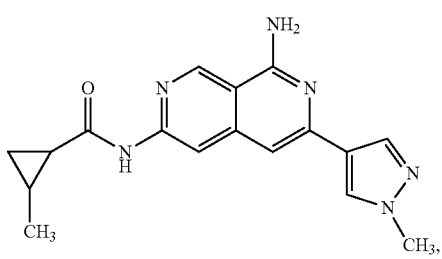
50
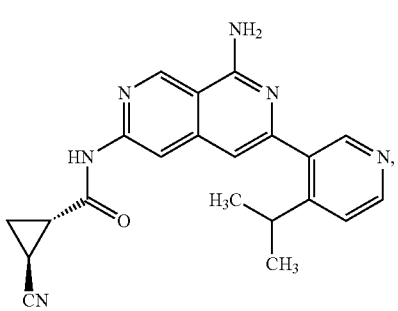
51
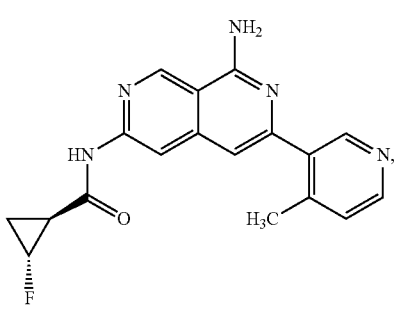
52
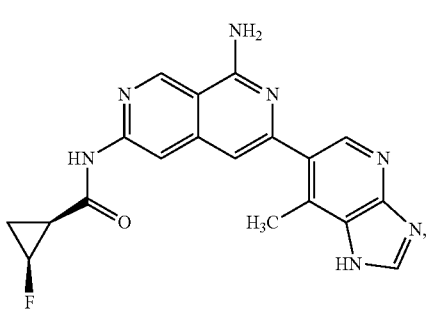
53
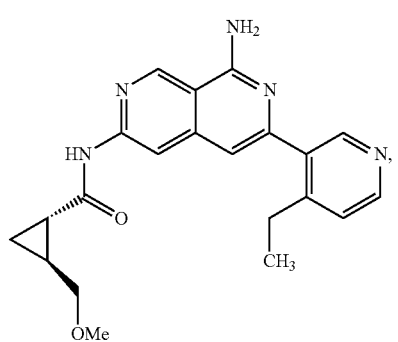

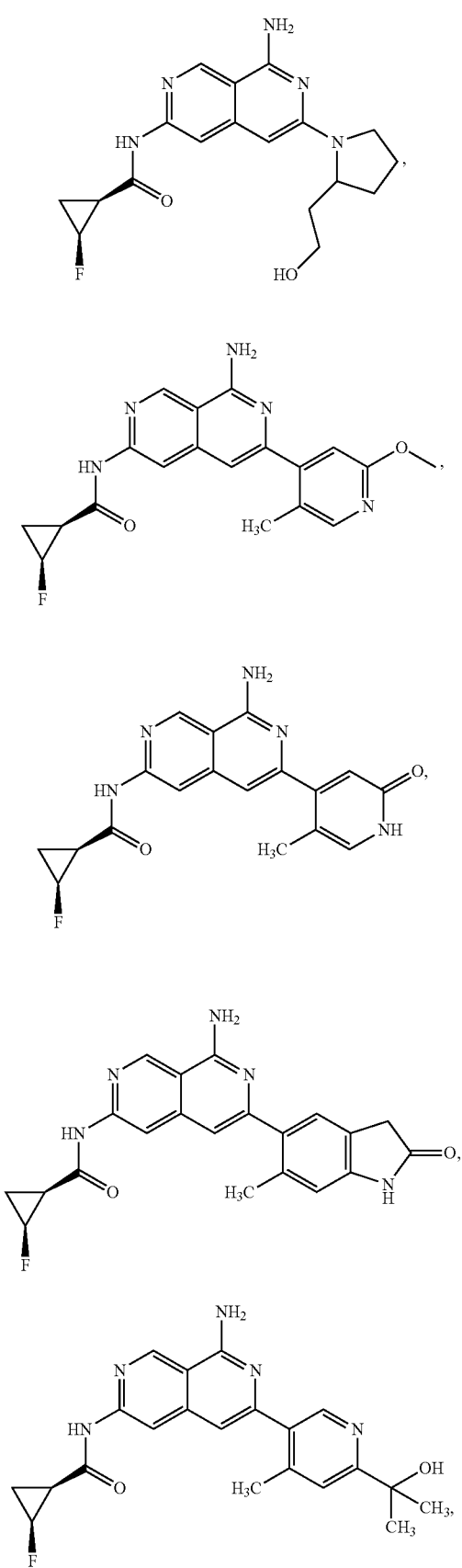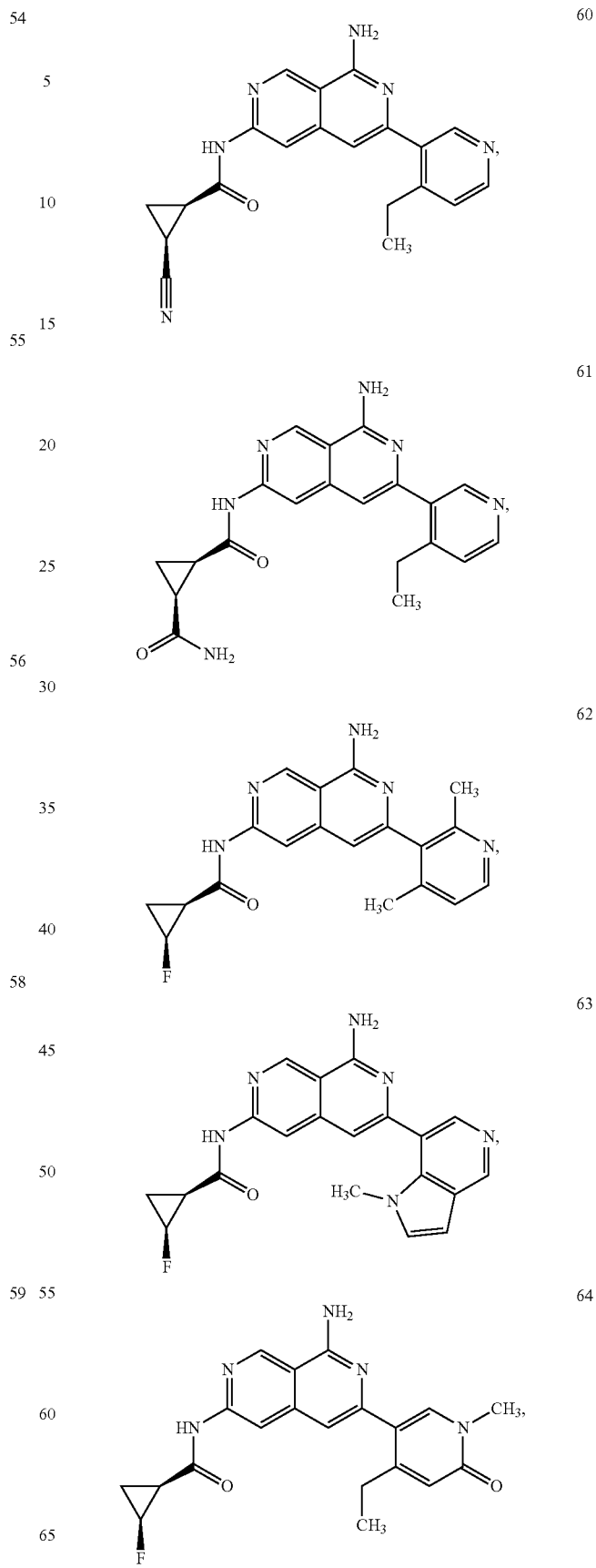

66
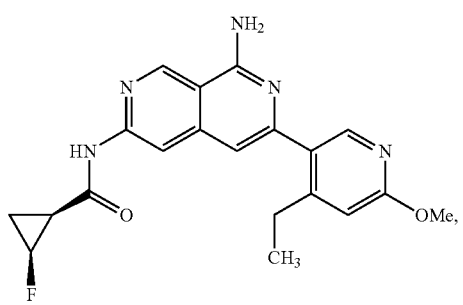
67
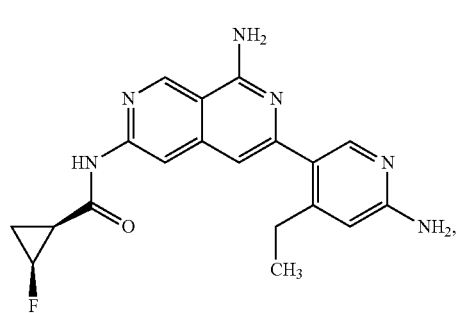
68
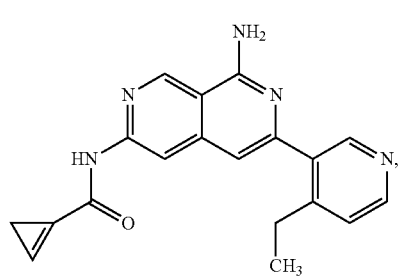
86
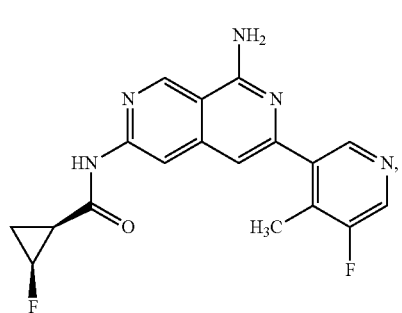
87, 88
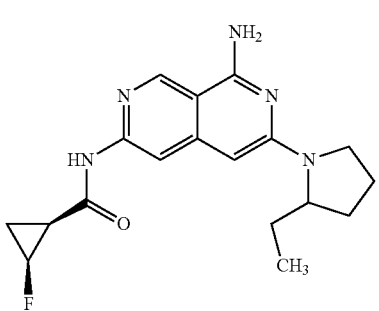
89
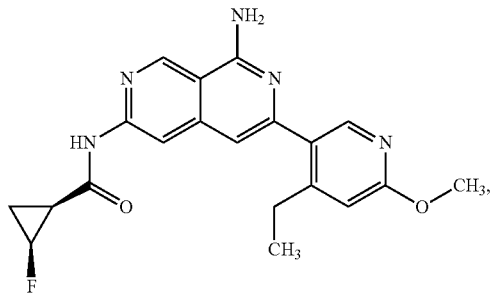
90
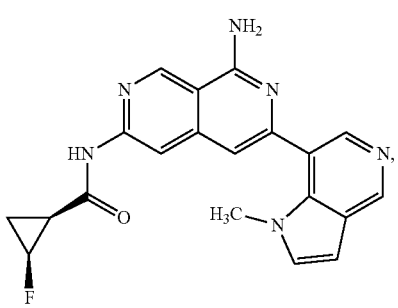
91
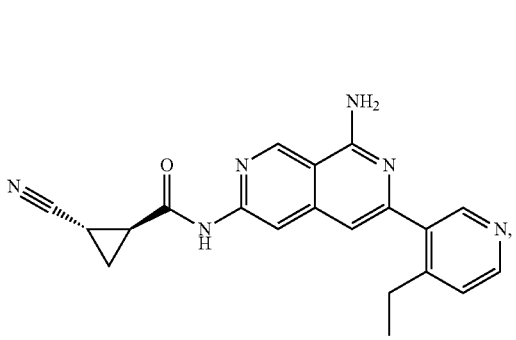
92
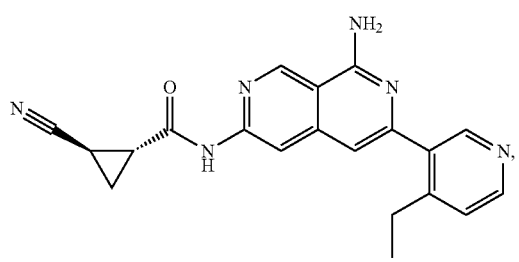
93
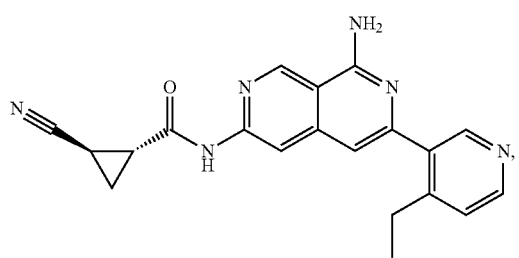

94
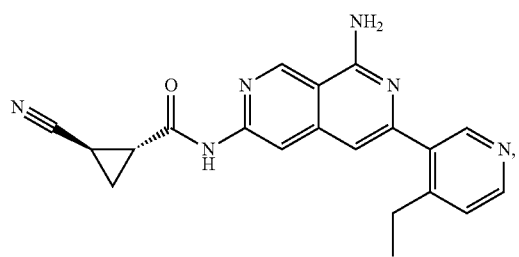
96
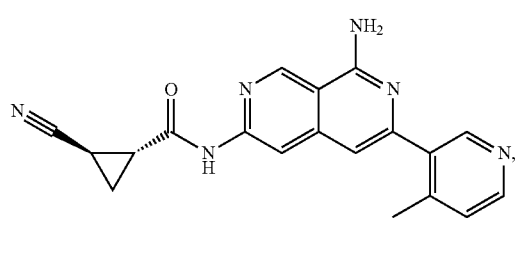
97
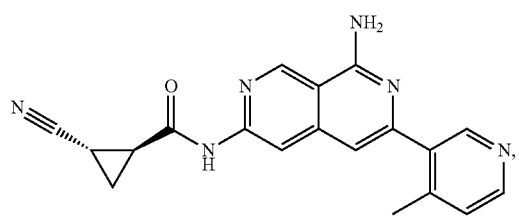
98
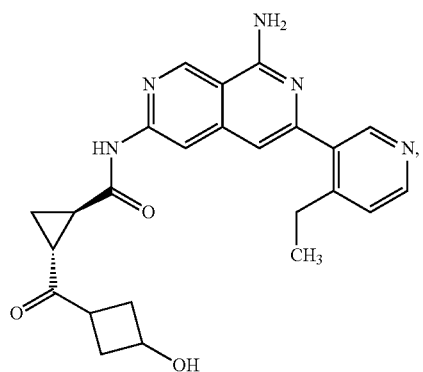
99
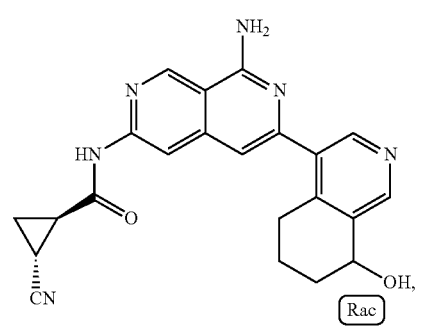
100
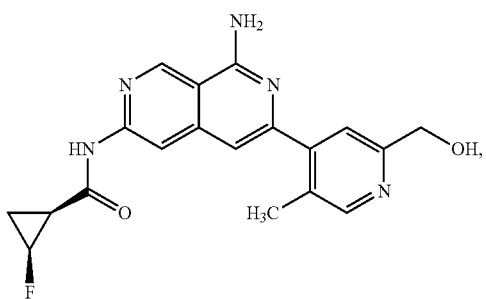
101
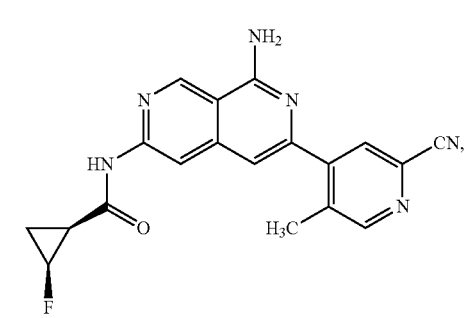
103
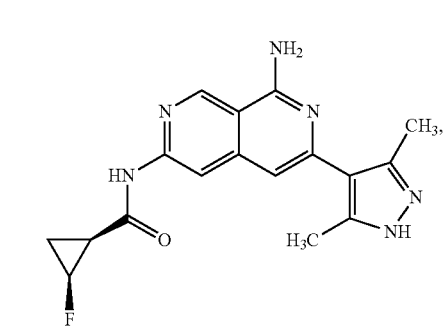
104
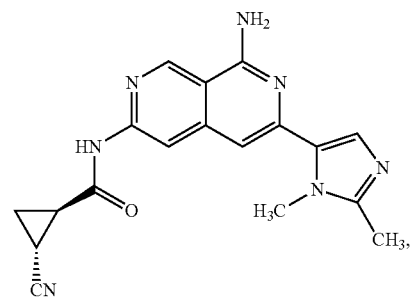
106
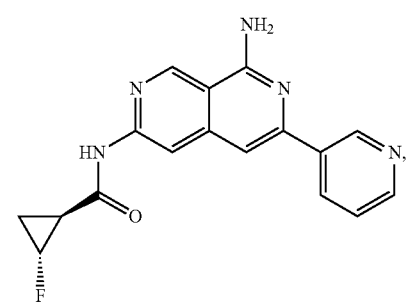

1185
107
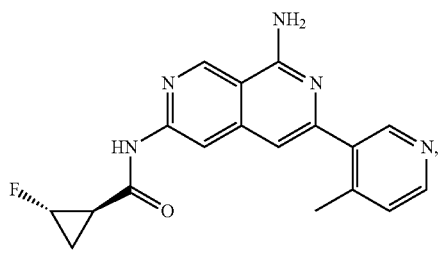
108
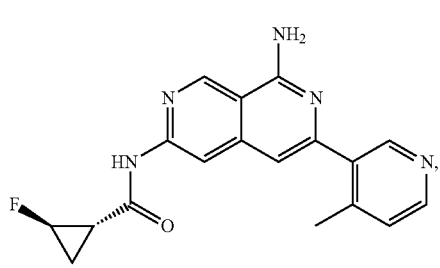
110
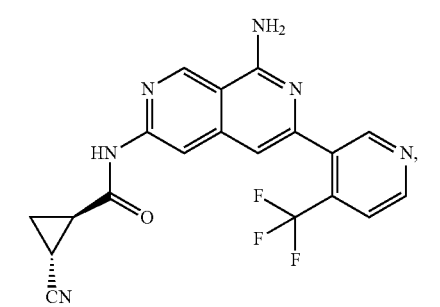
111
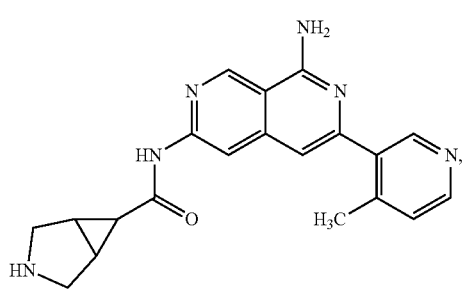
112
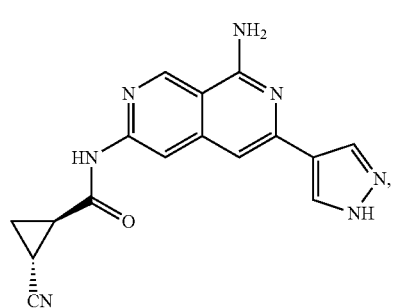
1186
113
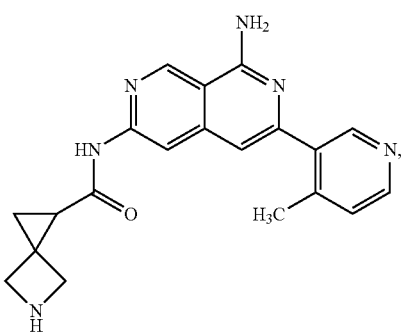
114
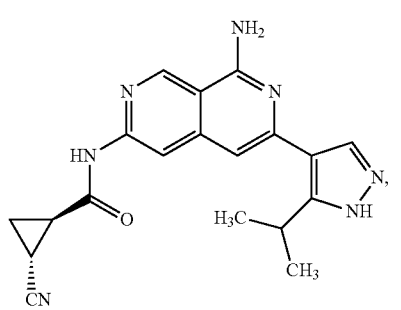
115
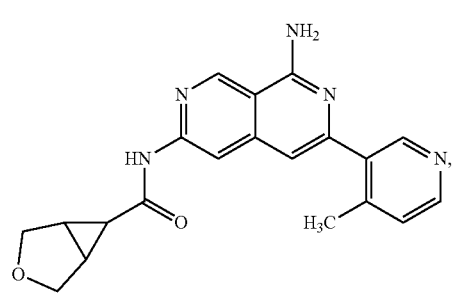
118
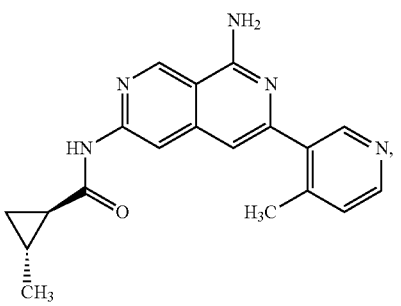
119
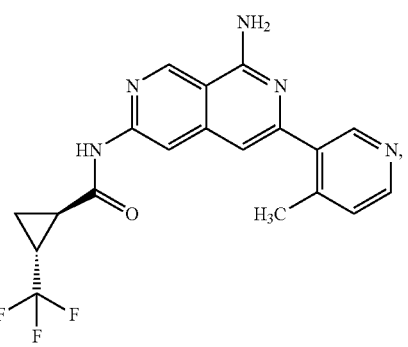

| 1187 | 1188 |
|---|---|
| 121 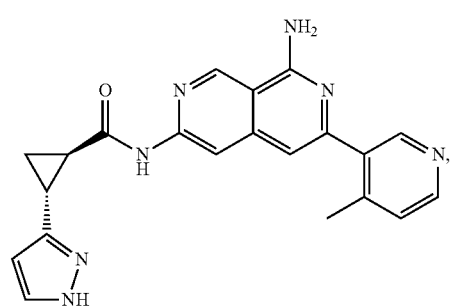 | 126 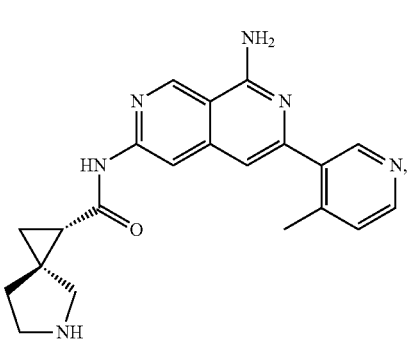 |
| 122 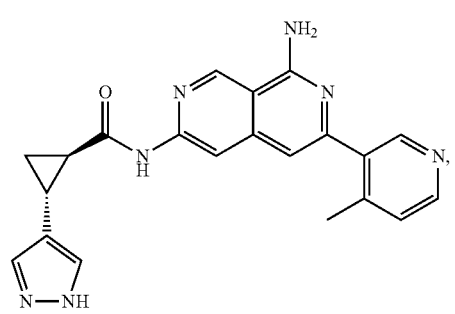 | 127 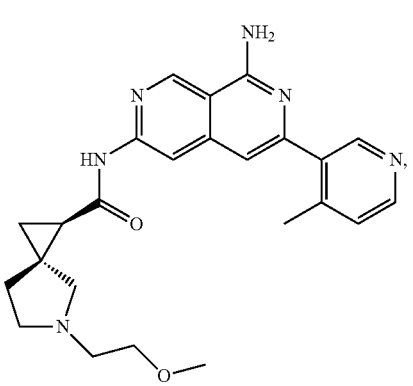 |
| 123 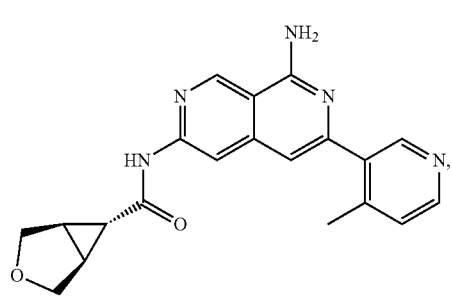 | 128 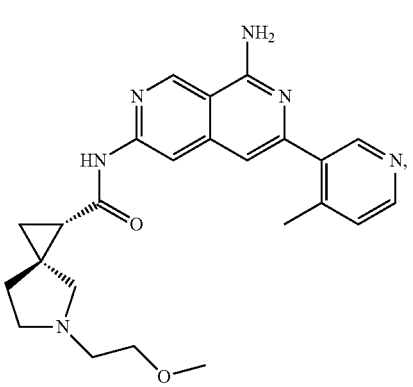 |
| 124 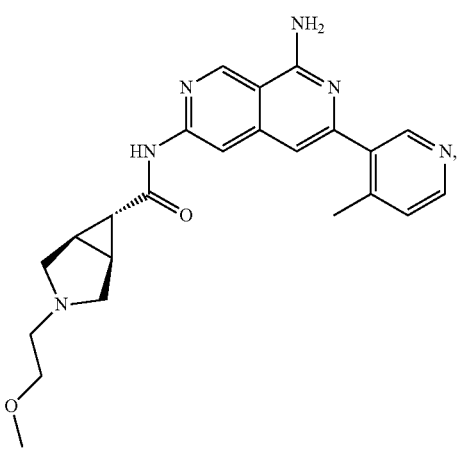 | 129 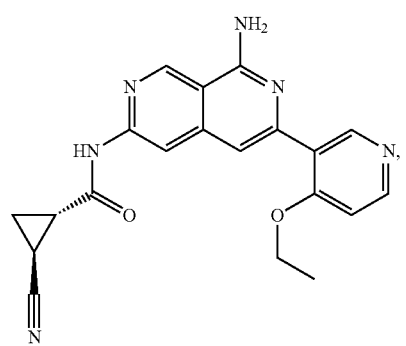 |
| 125 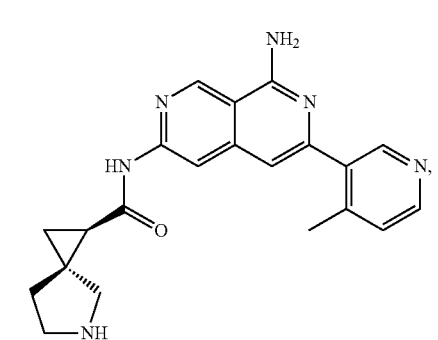 | |

1189
-continued
| | |
|---|---|
| 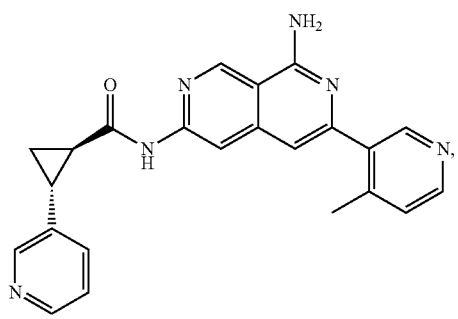 | 131 |
| 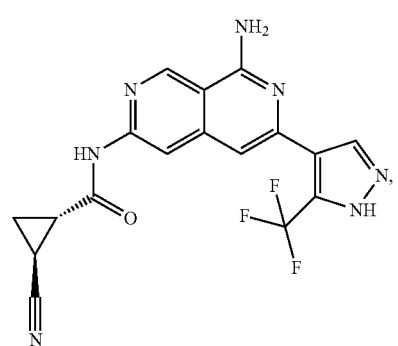 | 132 |
| 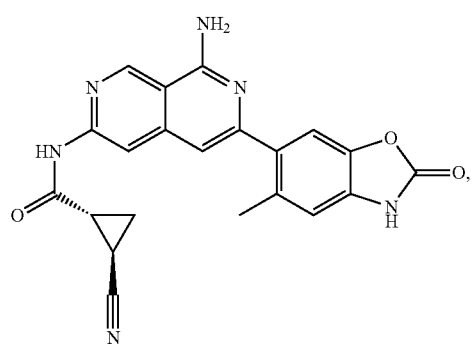 | 135 |
| 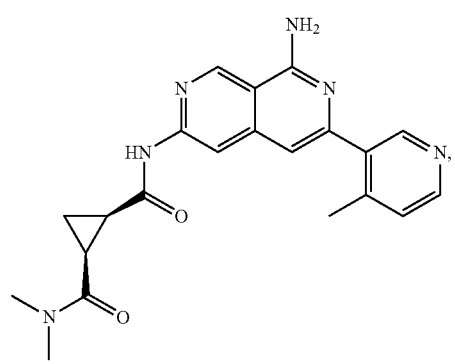 | 136 |
1190
-continued
| | |
|---|---|
| 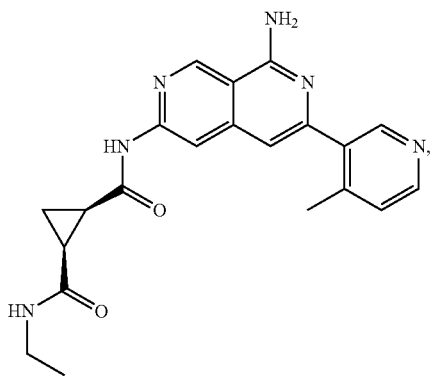 | 137 |
| 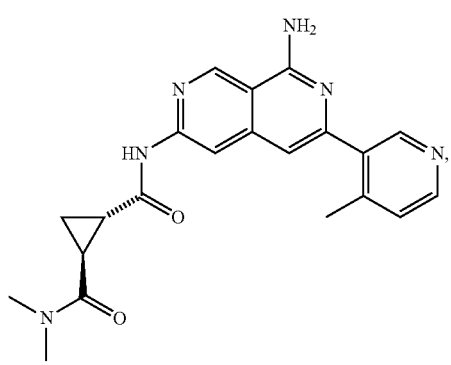 | 138 |
| | 139 |
| 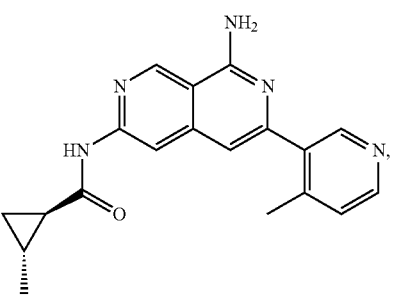 | 140 |
| 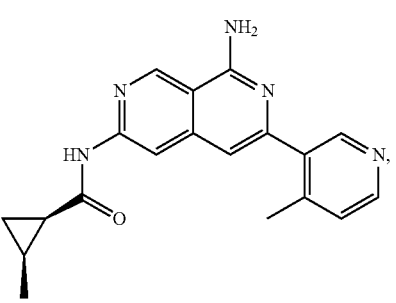 | 141 |

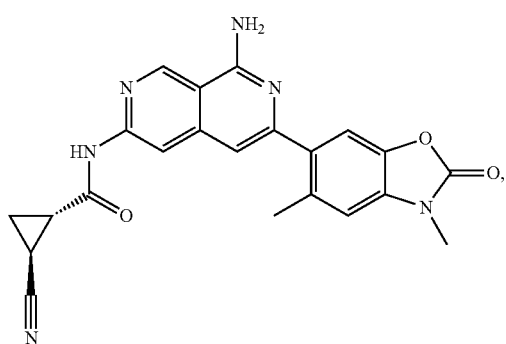
142
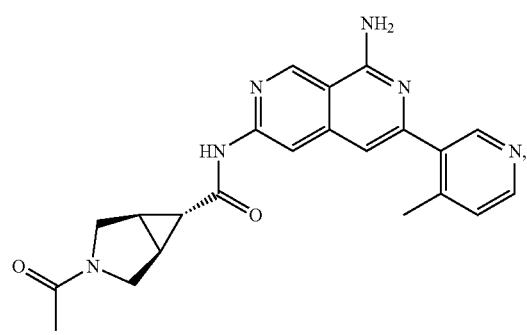
143
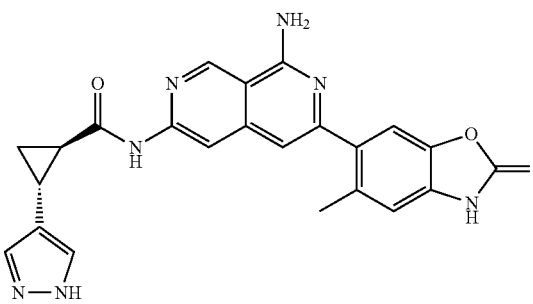
144
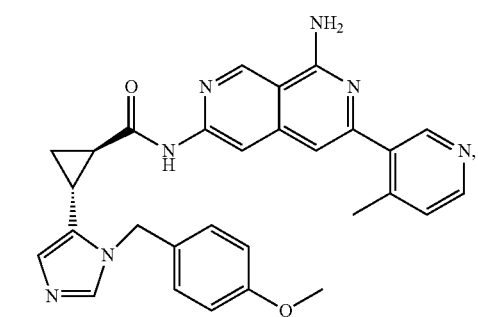
145

146
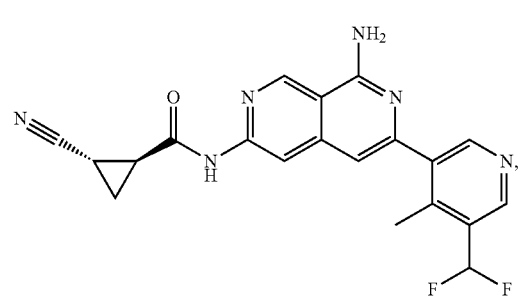
147
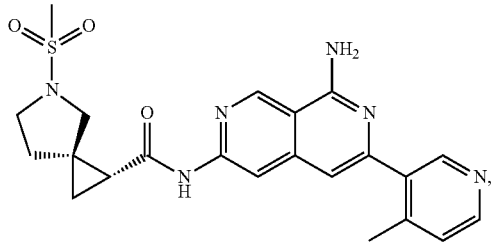
148
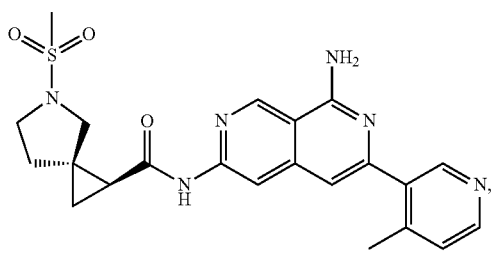
149

1193 -continued
150 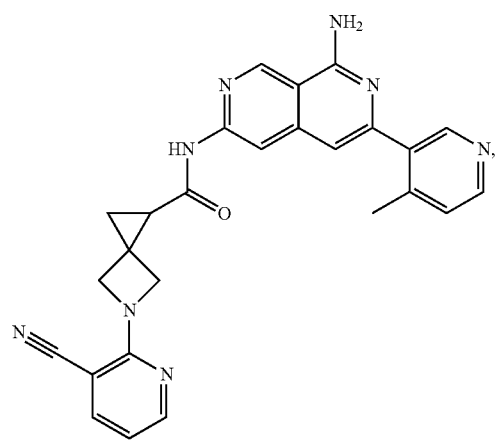
151 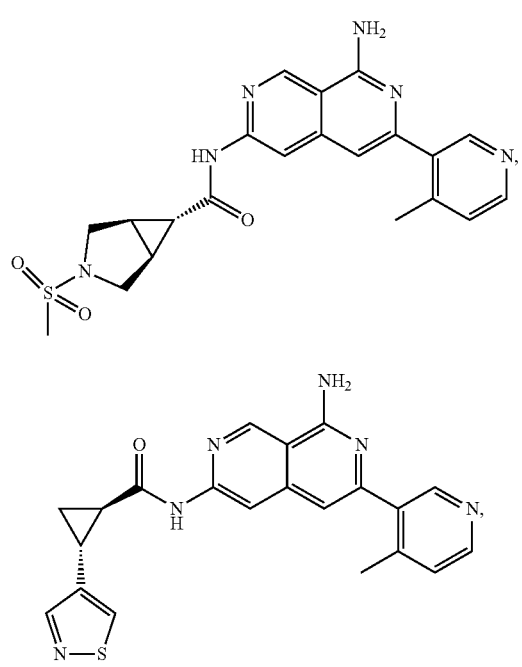
152 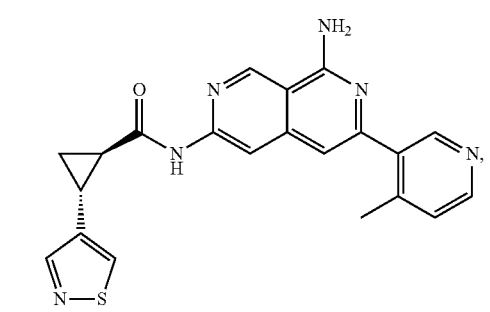
154 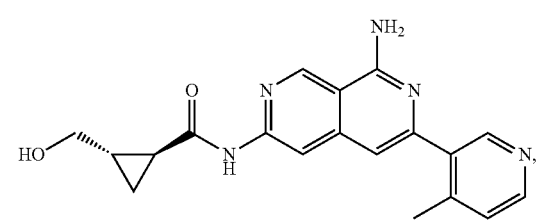
155 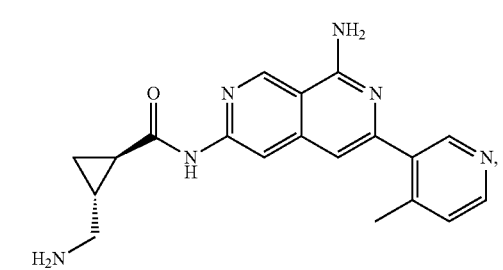
1194 -continued
157 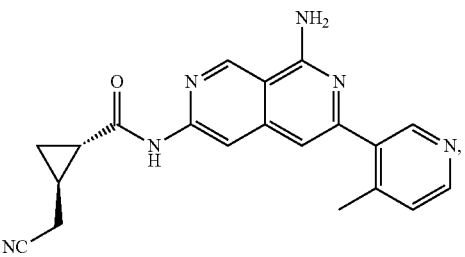
158 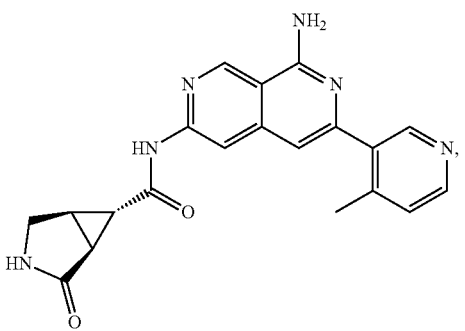
159 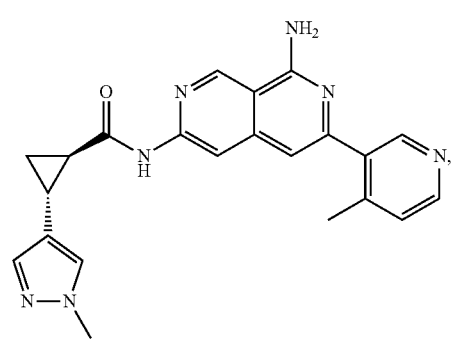
160 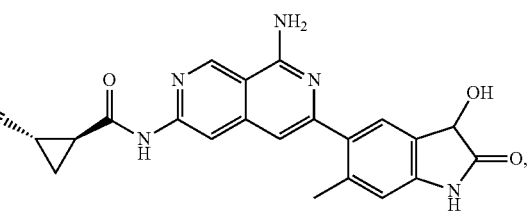
165 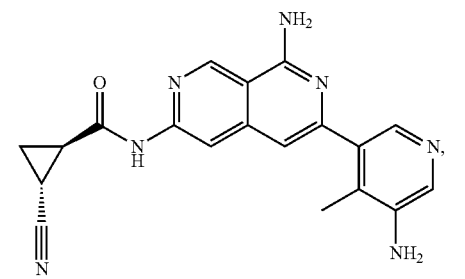

166
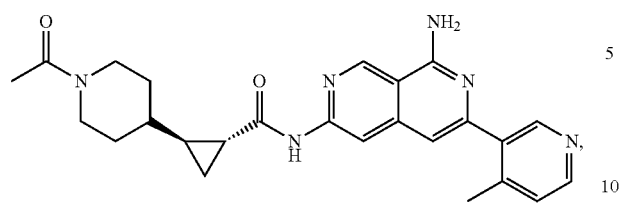
167
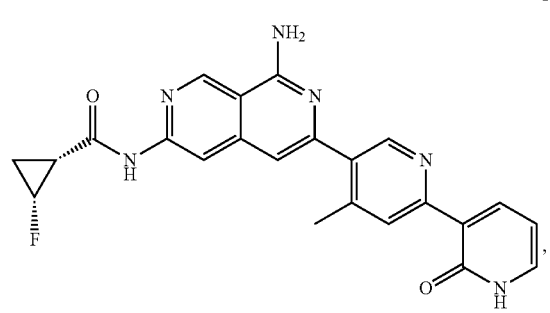
179
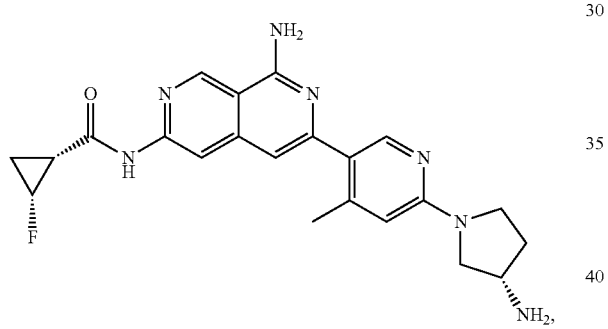
180
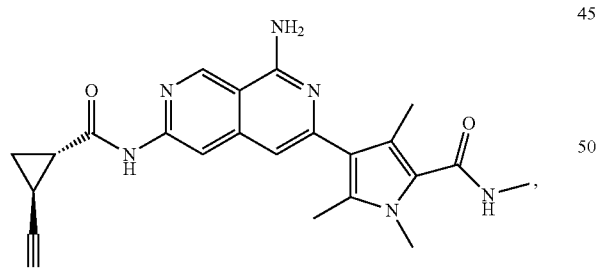
181
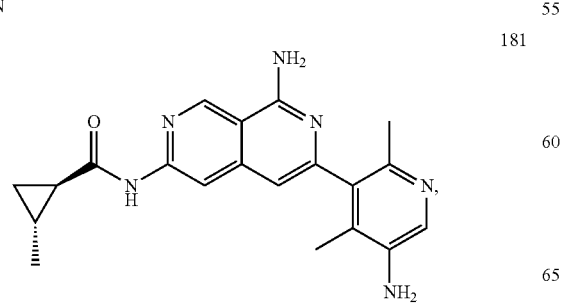
186
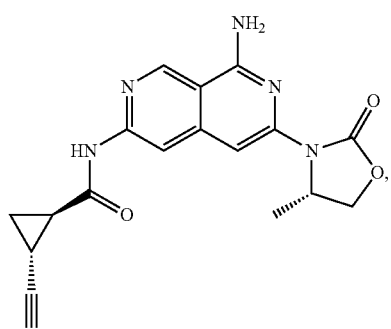
187
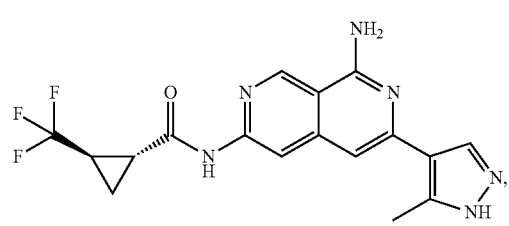
188
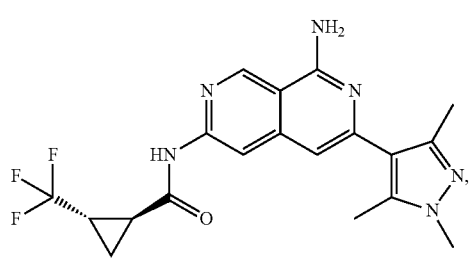
189
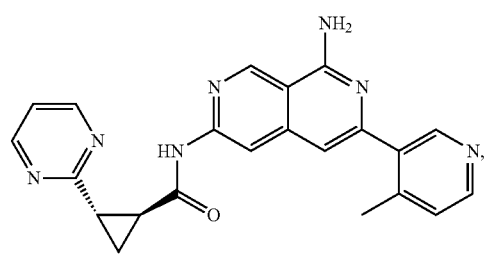
190
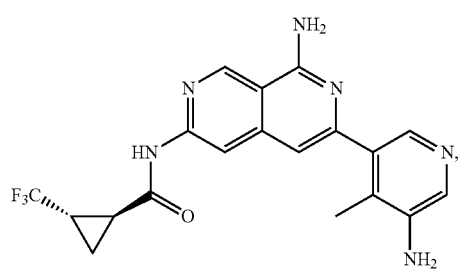

1197 -continued
191
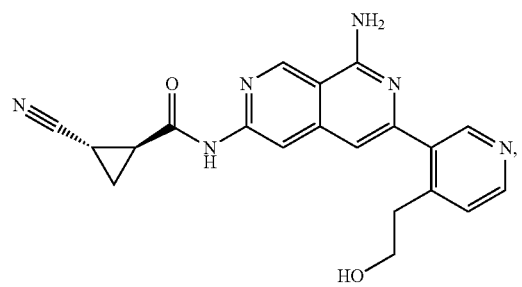
192
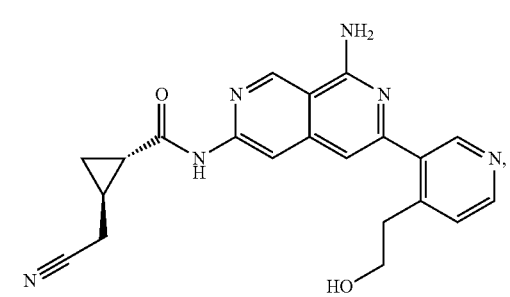
193
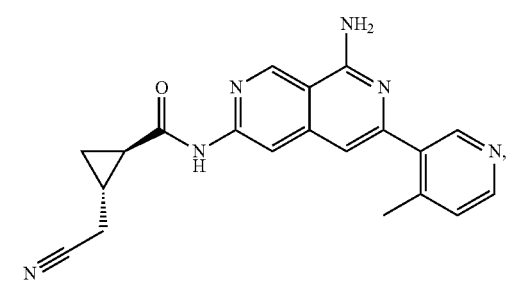
194
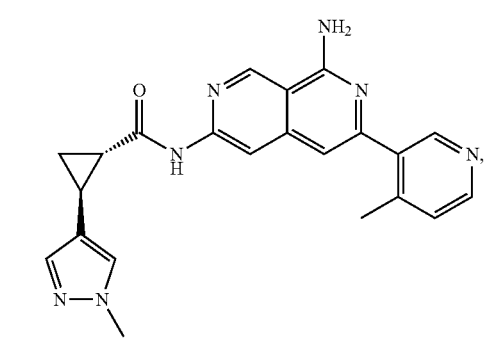
197
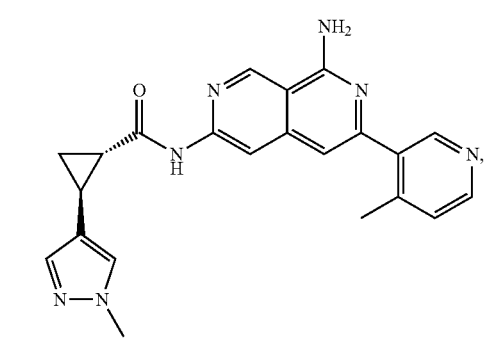
1198 -continued
198
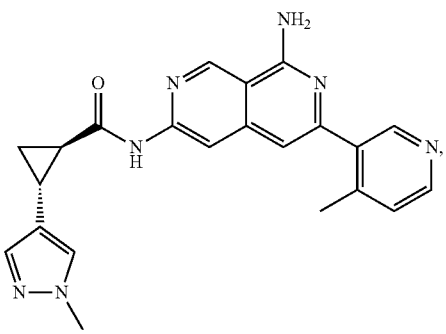
199
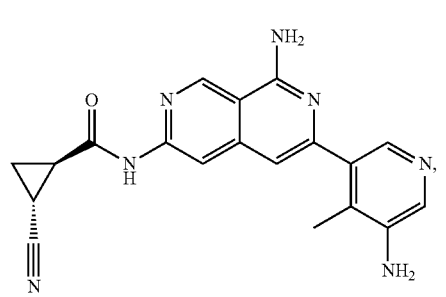
200
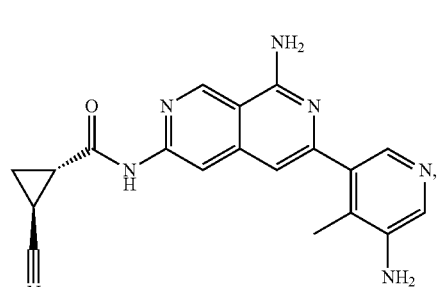
201
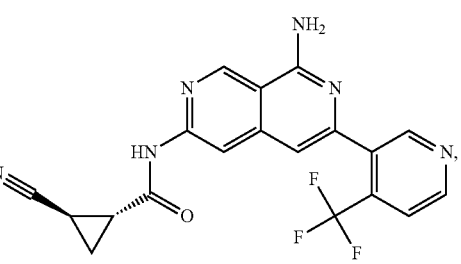
202
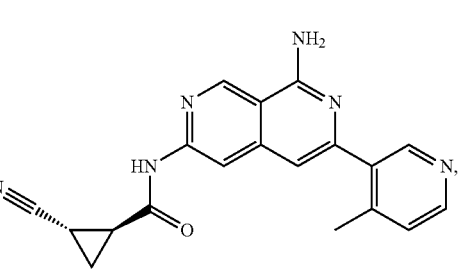

1199
-continued
203
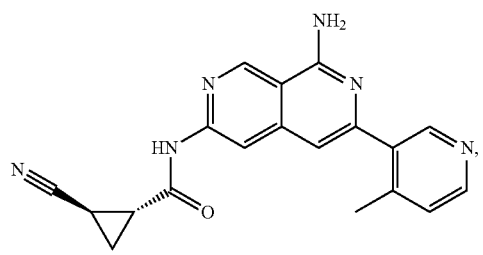
206
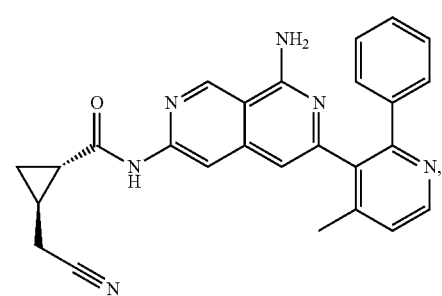
207
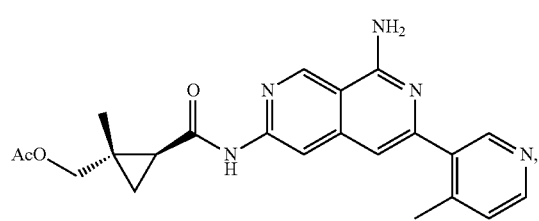
208
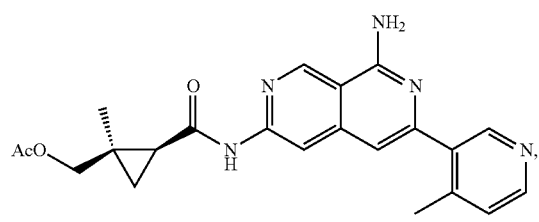
209
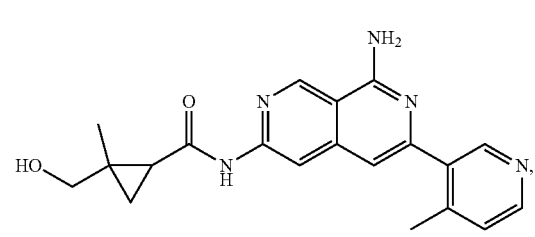
211
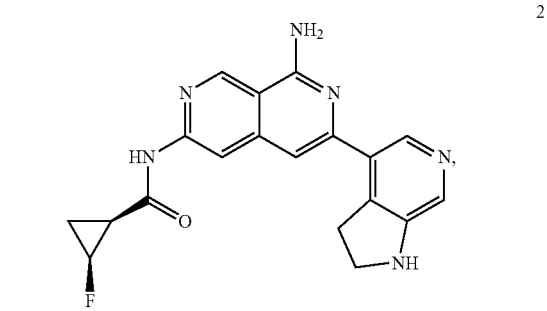
1200
-continued
212
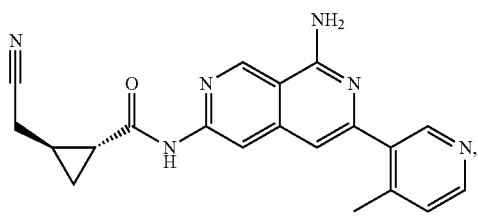
214
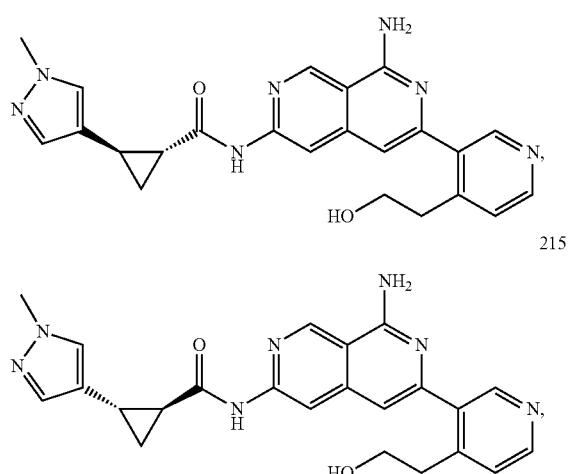
215
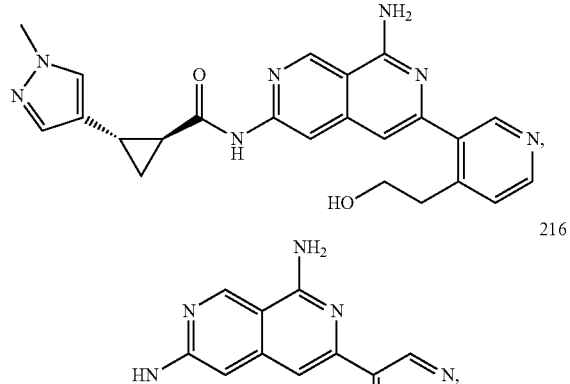
216
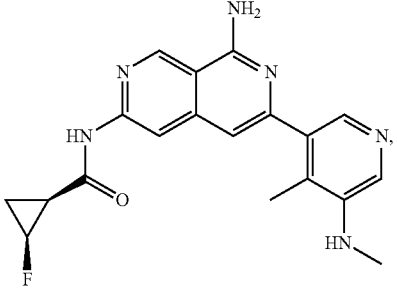
222
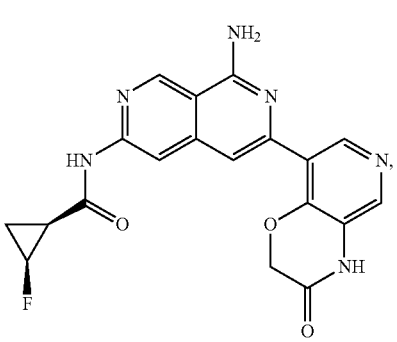
223
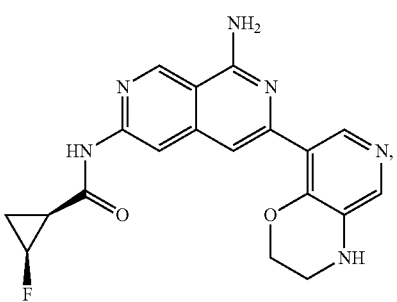

225
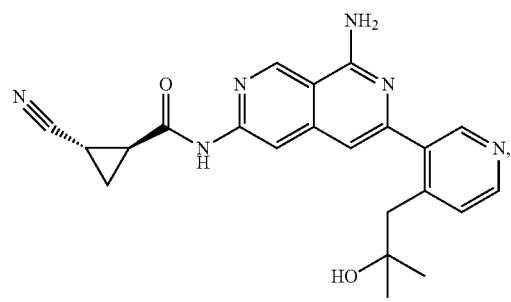
226
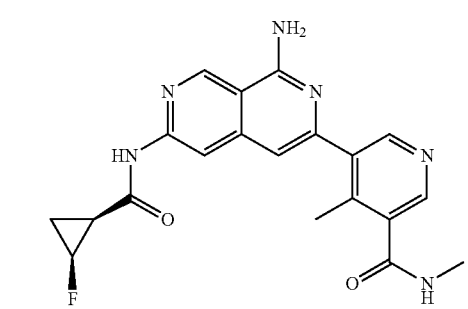
227
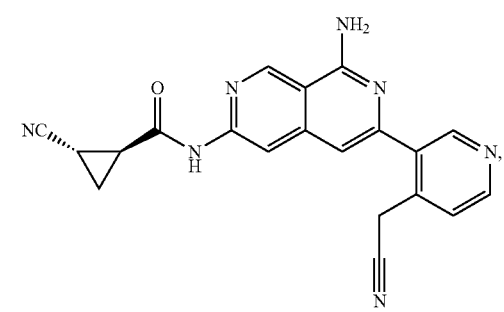
228
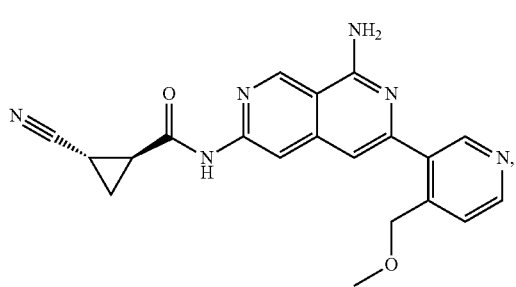
229
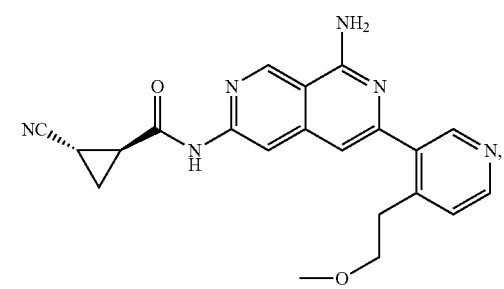
230
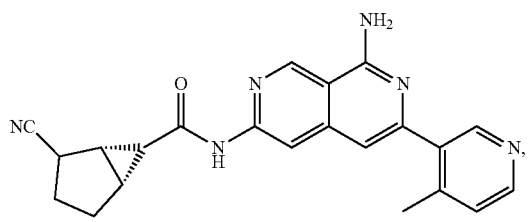
231
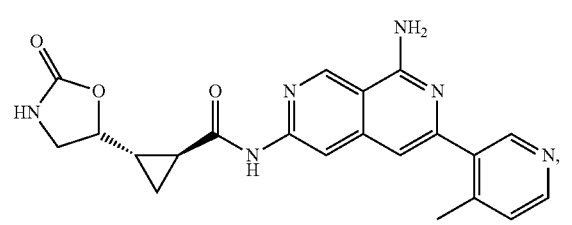
232
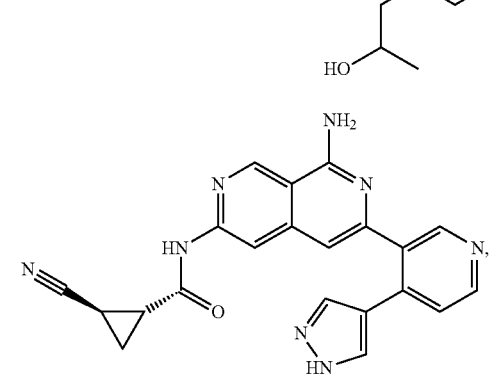
235
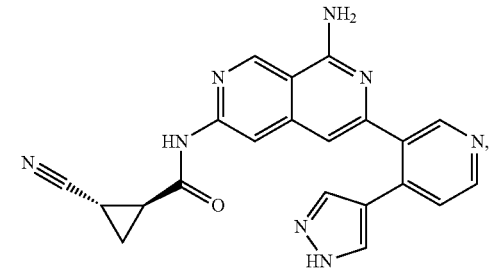
236
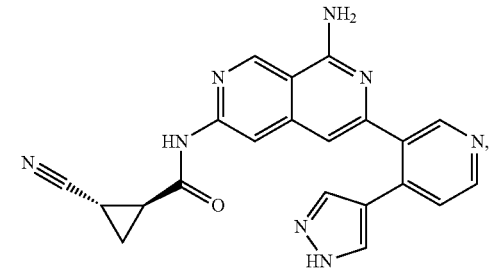
237
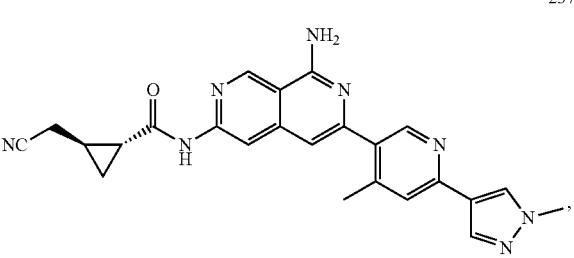

1203
-continued
238
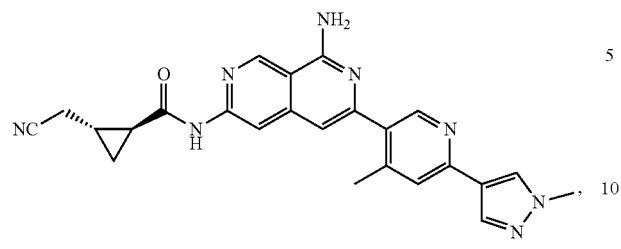
239
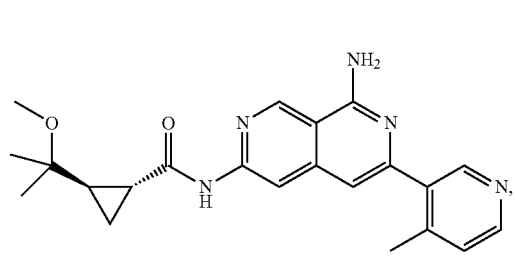
240
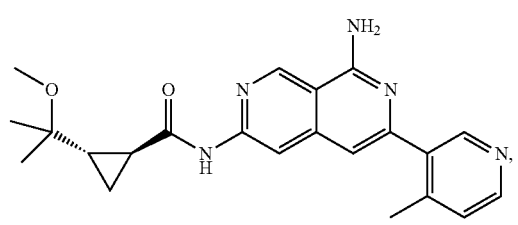
241
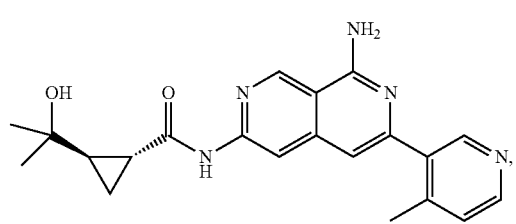
242
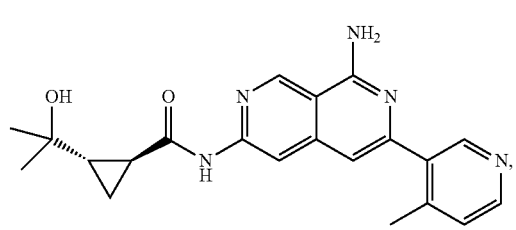
243
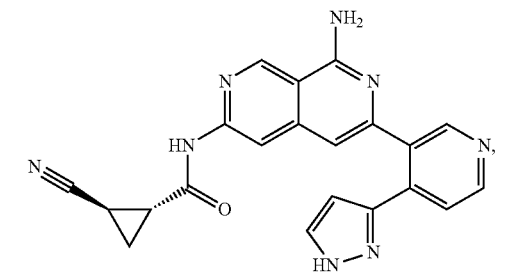
1204
-continued
244
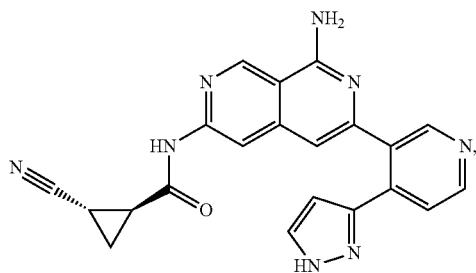
245
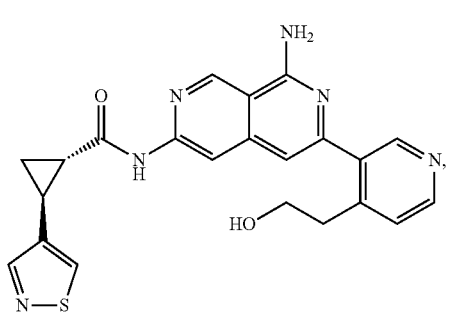
246
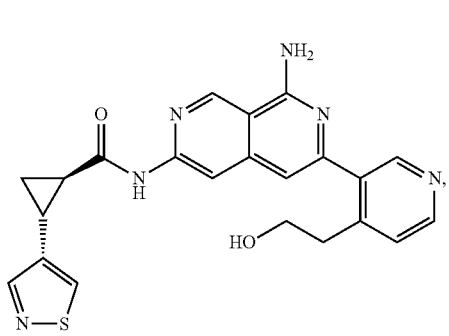
247
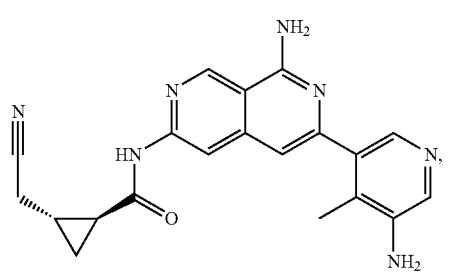
248
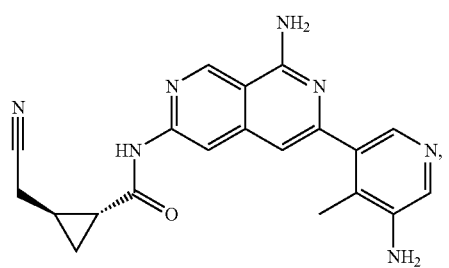

1205 -continued
253
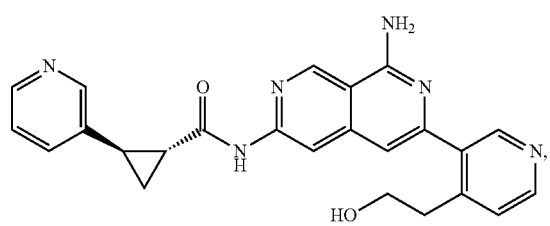
254
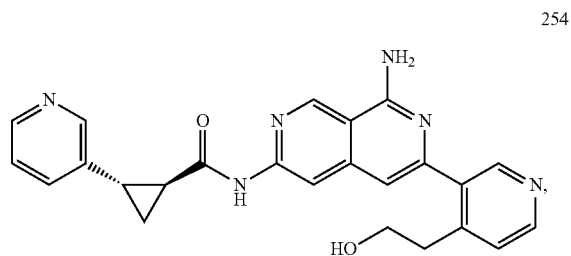
255
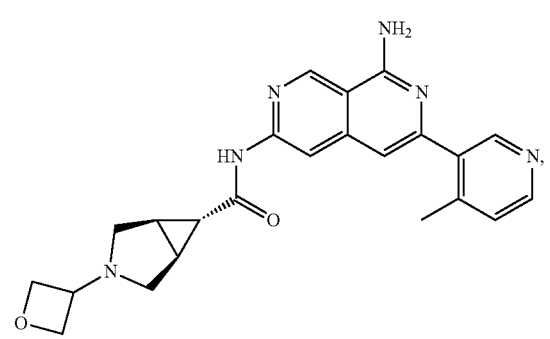
276
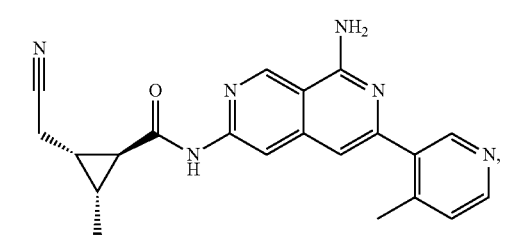
277
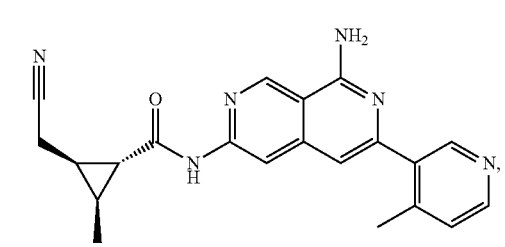
278
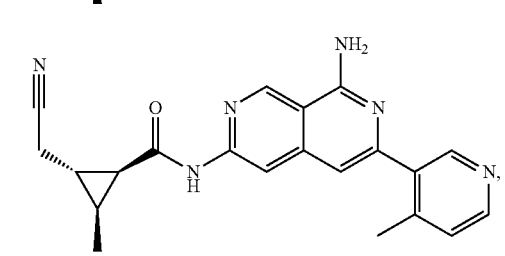
1206 -continued
279
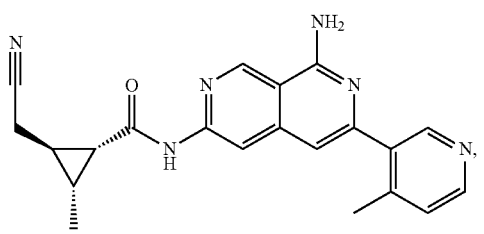
292
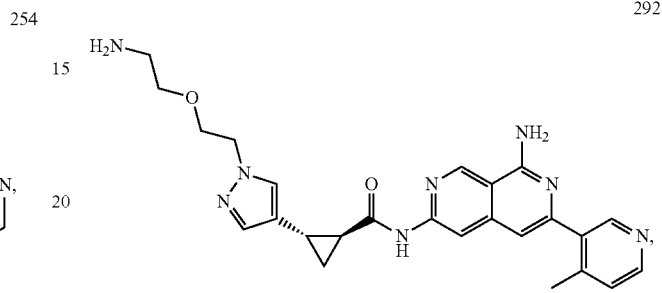
293
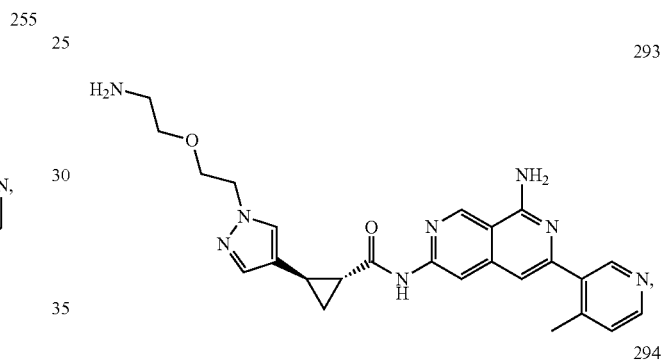
294
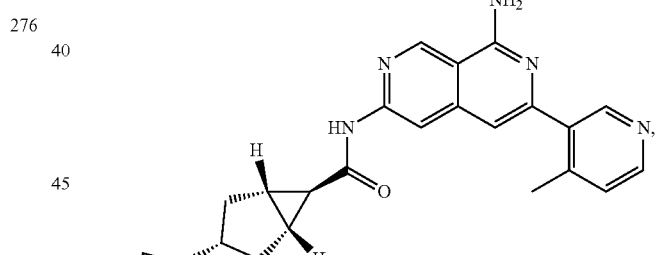
297
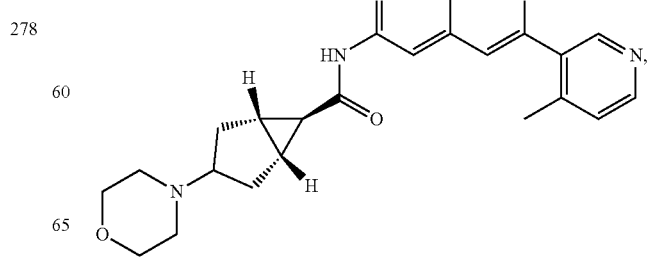
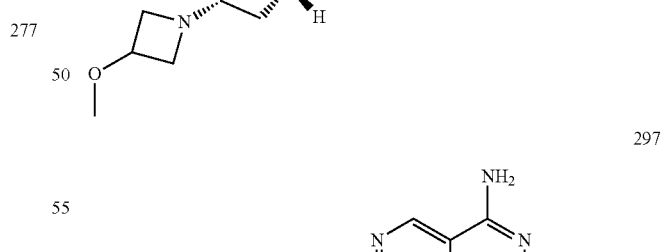

308
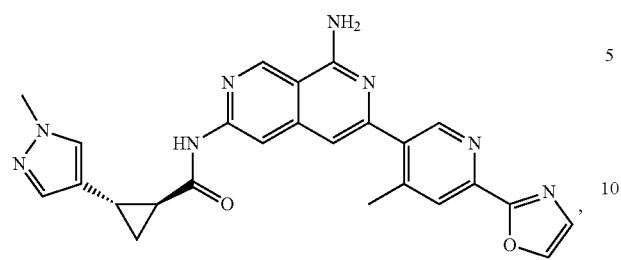
309
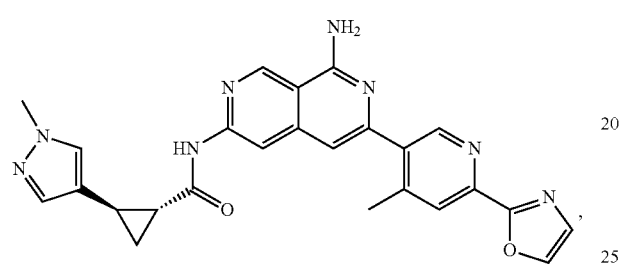
312
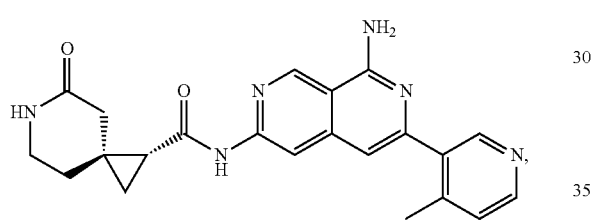
313
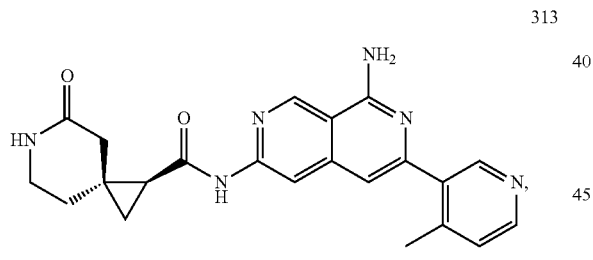
314
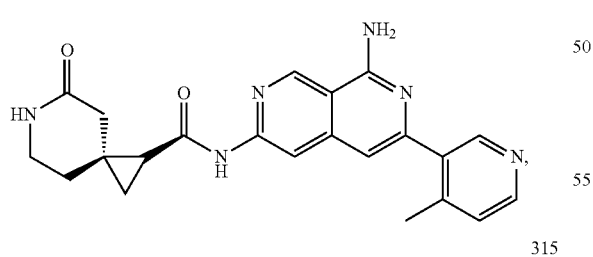
315
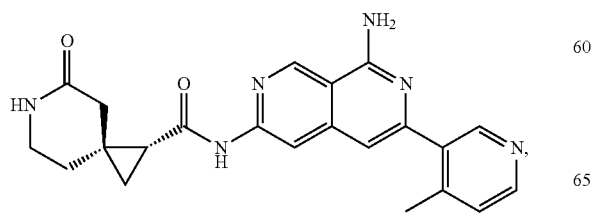
318
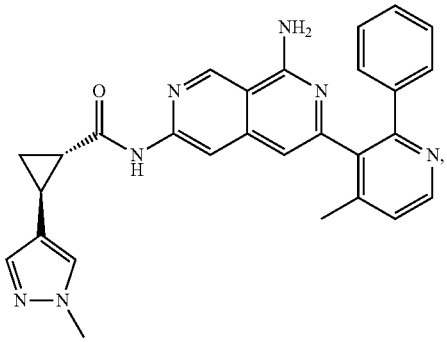
319
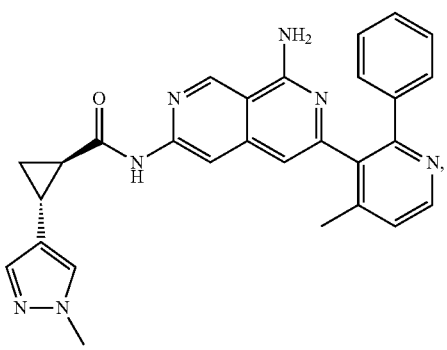
320
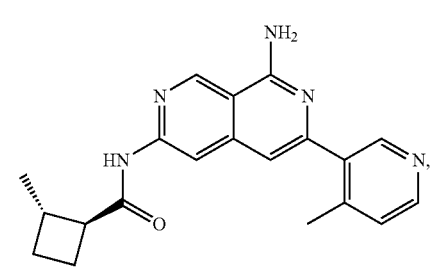
321
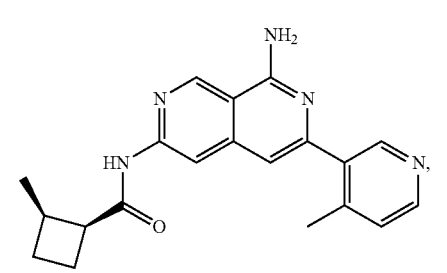
322
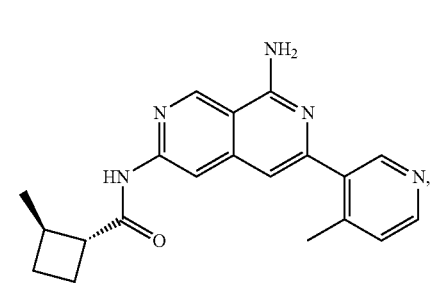

1209
-continued
323
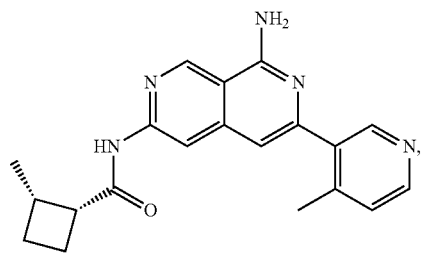
324
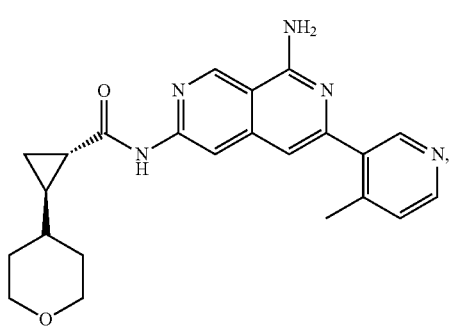
325
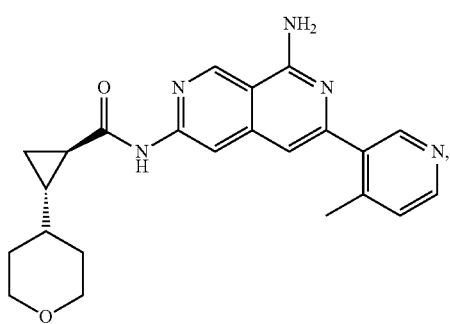
326
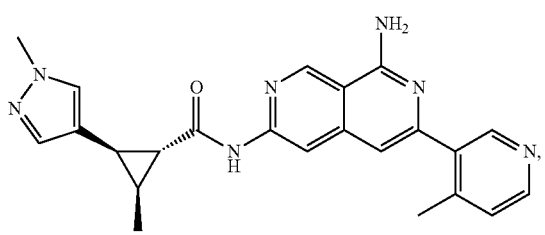
327
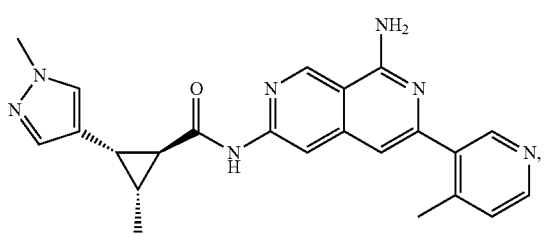
1210
-continued
328
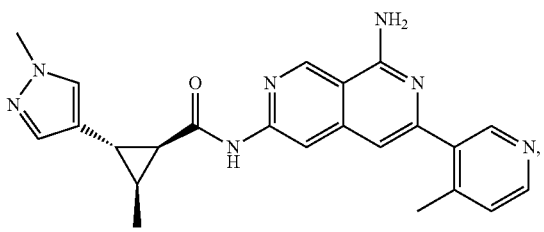
329
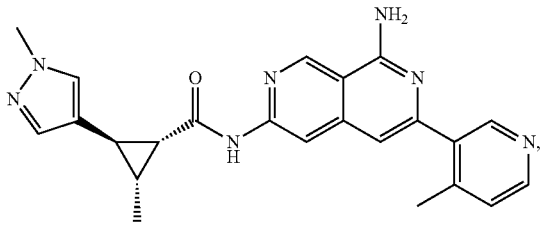
330
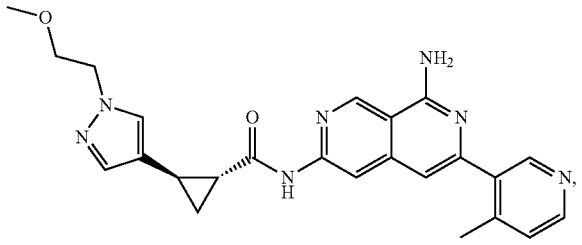
331
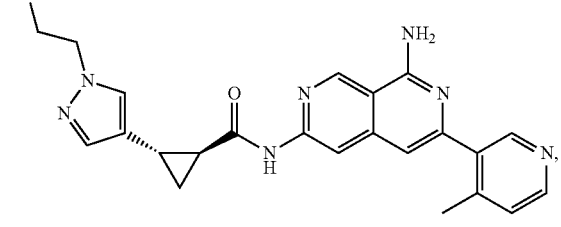
334
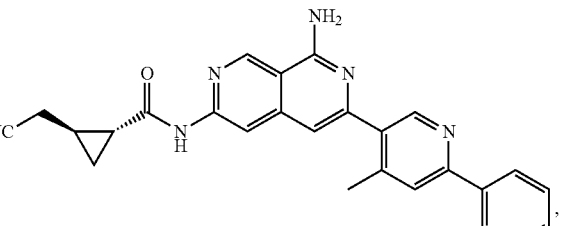
335
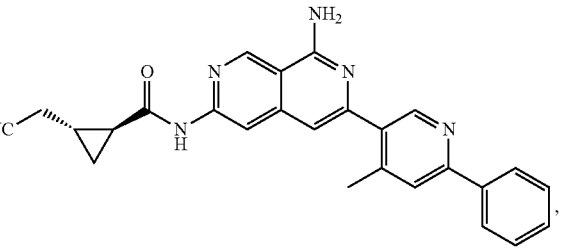

| 336 | 342 |
|---|---|
| 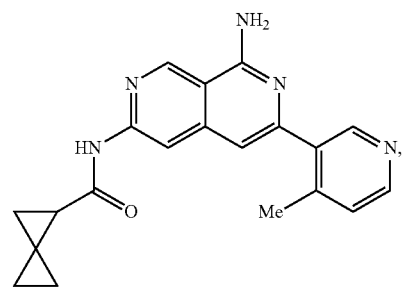 | 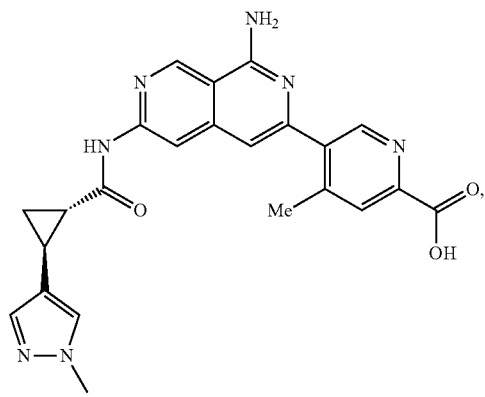 |
| 339 | 343 |
| 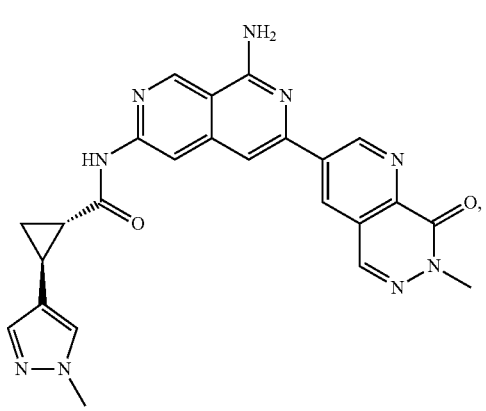 | 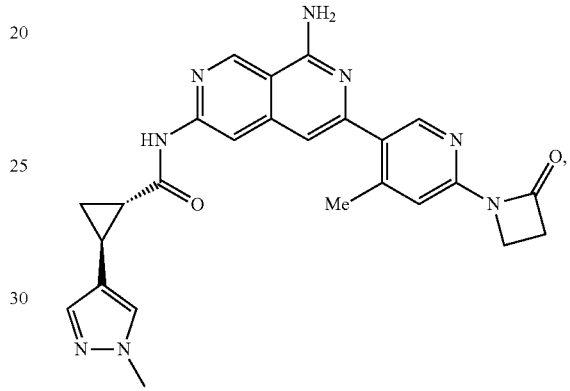 |
| 340 | 344 |
| 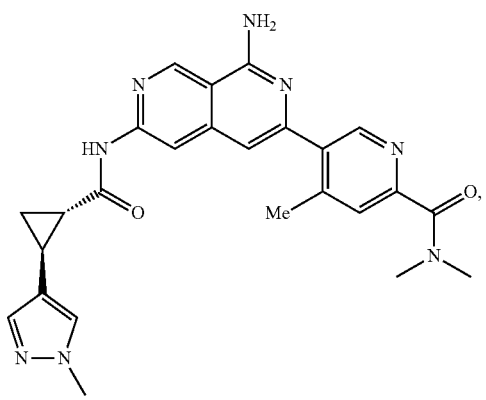 | 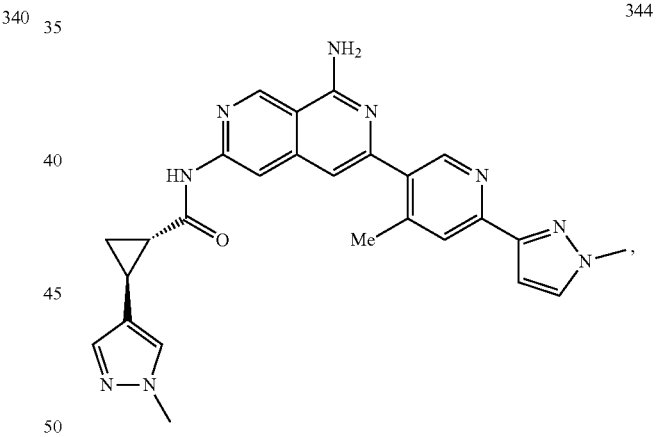 |
| 341 | 345 |
| 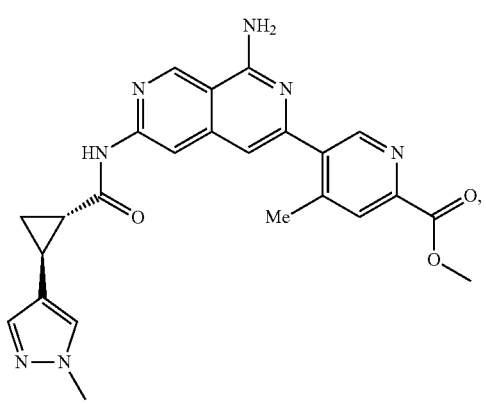 | 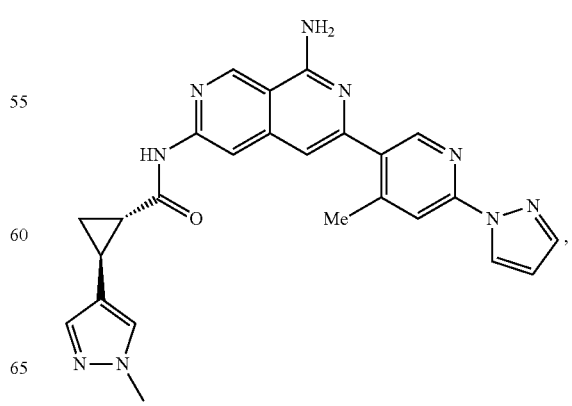 |

346

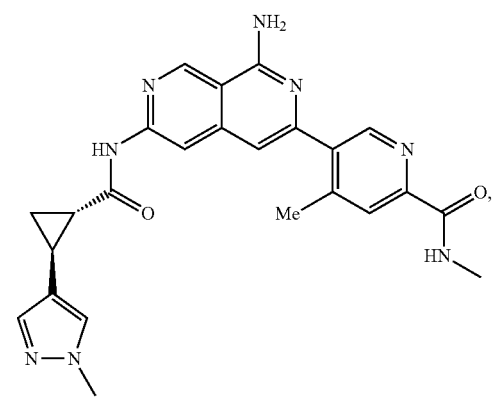

347

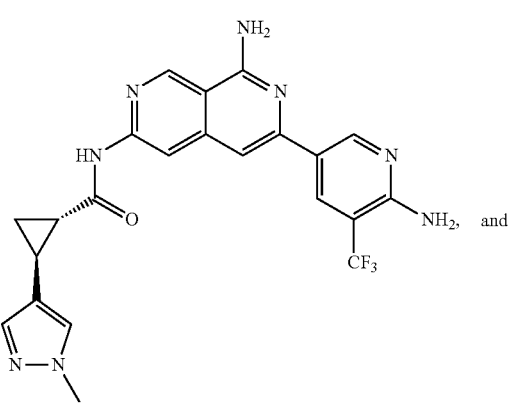
and

348

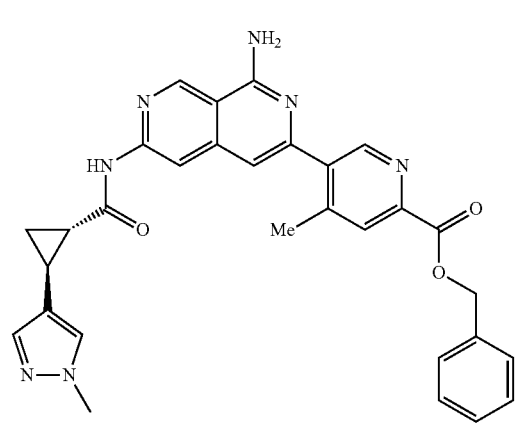

157

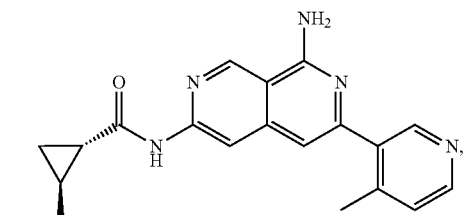

192

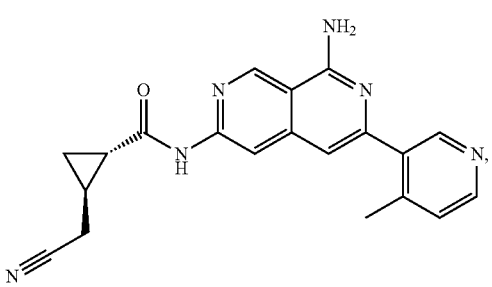

193

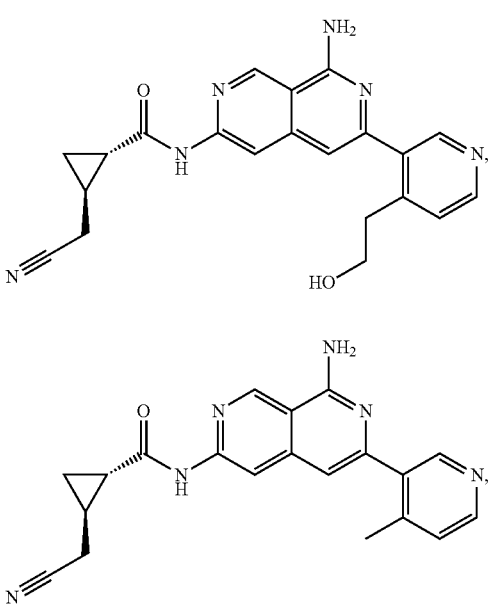

194

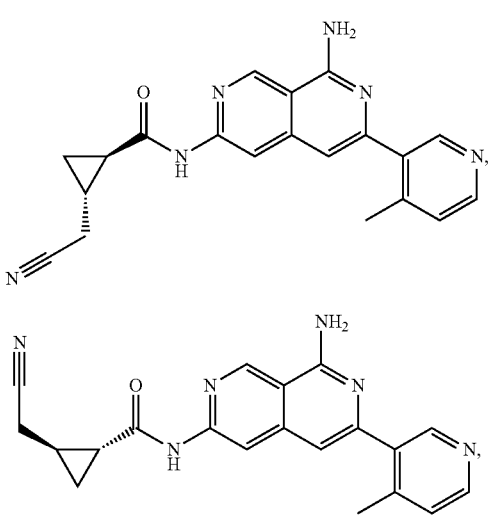

212

237

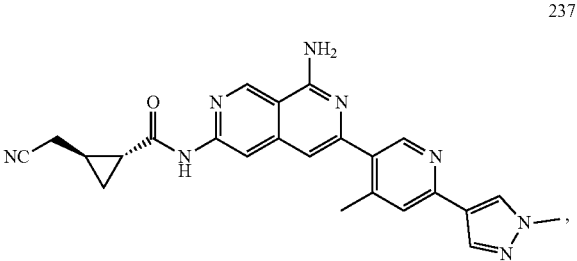,

Embodiment 25. The compound of embodiment 21, wherein at least one $R_5$ is optionally substituted $C_{2-9}$ heteroaryl or cyano($C_{1-6}$)alkyl.

Embodiment 26. The compound of embodiment 25, wherein at least one $R_5$ is cyano($C_{1-6}$)alkyl.

Embodiment 27. The compound of embodiment 26, wherein at least one $R_5$ is cyano-$CH_2$—.

Embodiment 28. The compound of embodiment 27, having one of the following structures:

238

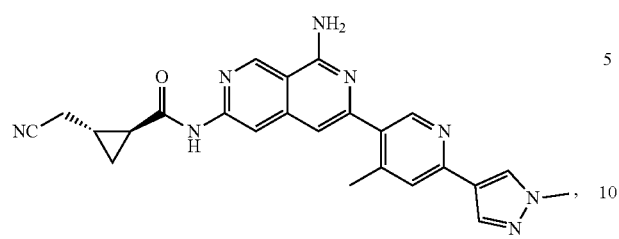

247

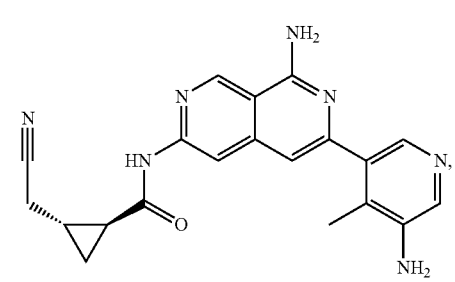

248

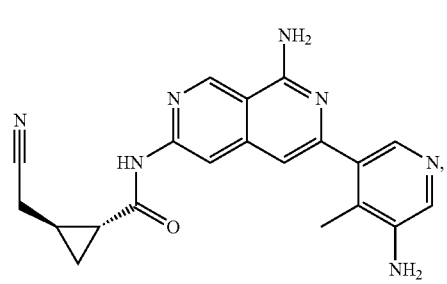

276

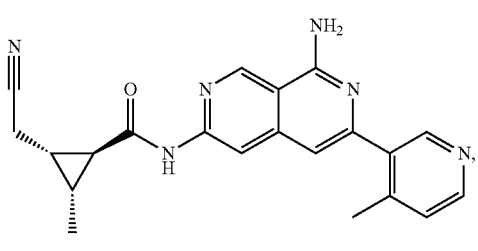

277

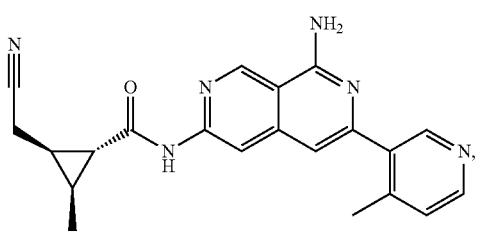

278

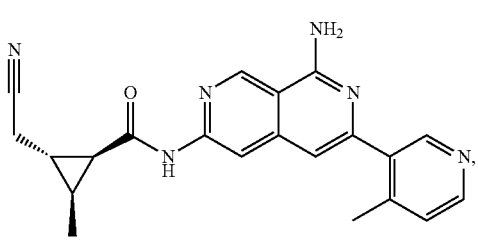

279

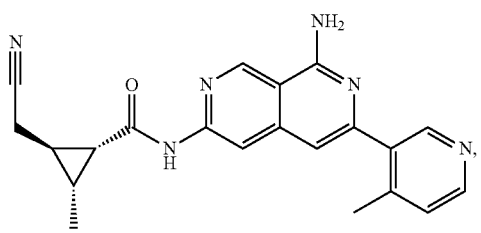

310

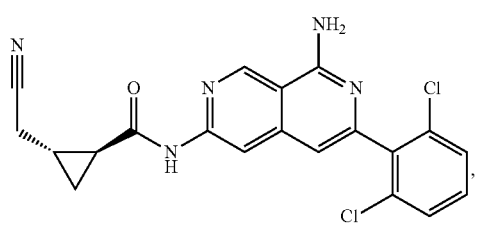

311

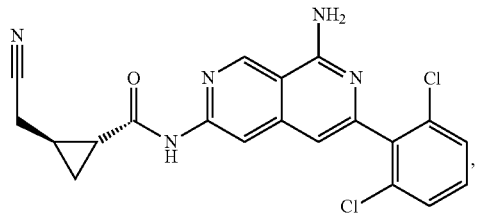

334

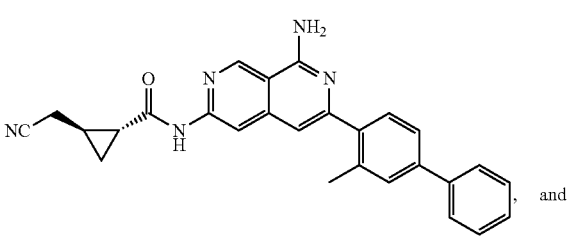

, and

335

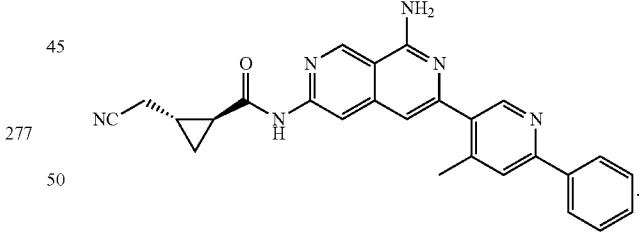

.

Embodiment 29. The compound of embodiment 21, wherein at least one $R_5$ is optionally substituted $C_{2-9}$ heteroaryl.

Embodiment 30. The compound of embodiment 29, wherein said optionally substituted $C_{2-9}$ heteroaryl is an optionally substituted 5-member heteroaryl containing 1 or 2 nitrogen atoms.

Embodiment 31. The compound of embodiment 30, wherein said optionally substituted 5-member heteroaryl is an optionally substituted pyrazole.

Embodiment 32. The compound of embodiment 31, wherein said optionally substituted pyrazole is

1217

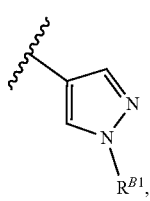

wherein the wavy line denotes the point of attachment to the cyclopropyl ring; and wherein $R^B$ is:

i. branched or linear $C_{1-6}$ alkyl, wherein said alkyl can be optionally substituted with one to four hydroxyl, halogen, nitrile, amino, —O—$(C_{1-6})$alkyl, —O—$(C_{1-6})$alkylamino-, di$(C_{1-6})$alkylamino-, or —NR$^y$(CO)R$^z$, wherein R$^y$ and R$^z$, in each instance, is independently hydrogen or $C_{1-6}$ alkyl;

ii. or —SO$_2$R', wherein R' is $C_{1-6}$ alkyl.

Embodiment 33. The compound of embodiment 32, wherein $R^{B1}$ is optionally substituted linear $C_{1-6}$ alkyl.

Embodiment 34. The compound of embodiment 33, wherein said optionally substituted linear $C_{1-6}$ alkyl is methyl.

Embodiment 35. The compound of embodiment 32, having one of the following structures:

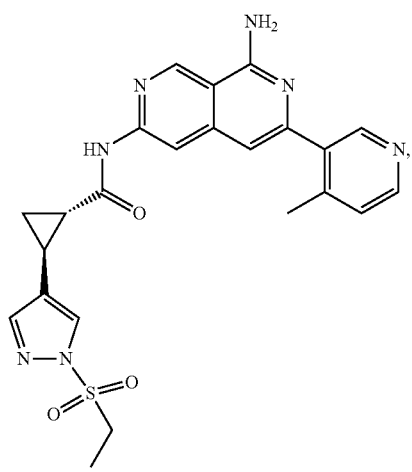

146

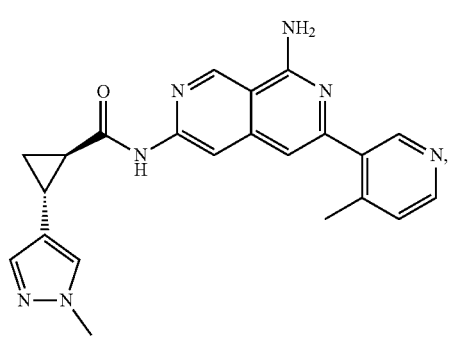

159

-continued

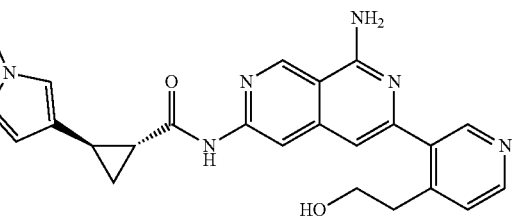

197

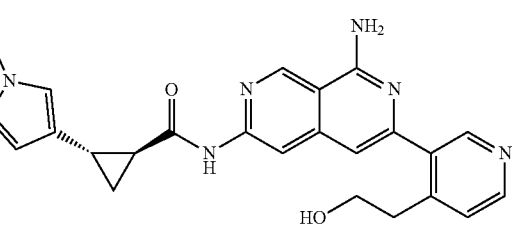

198

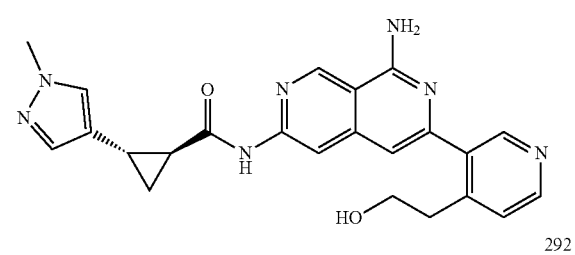

214

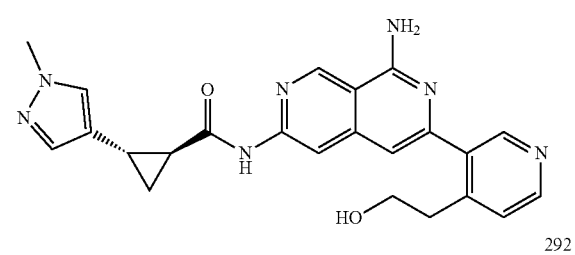

215

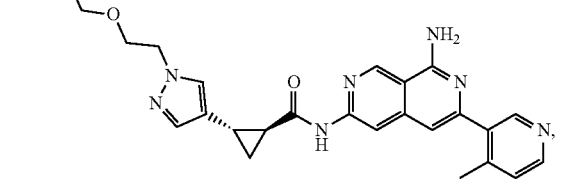

292

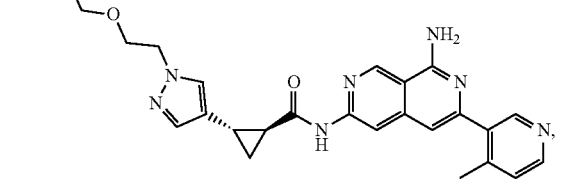

293

1219 -continued
308
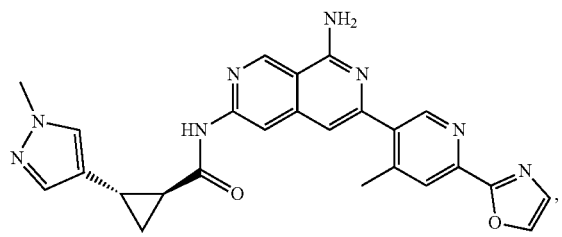
309
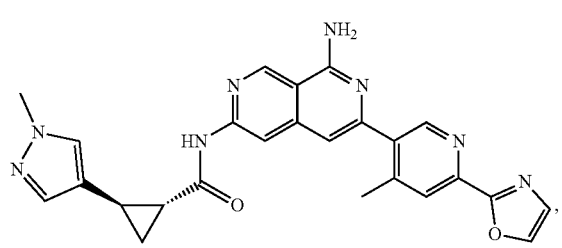
318
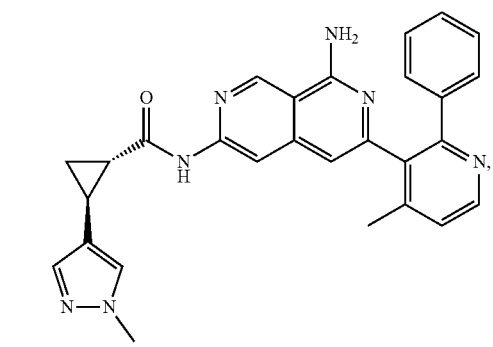
319
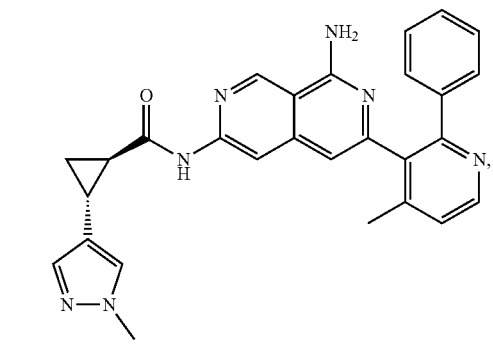
326
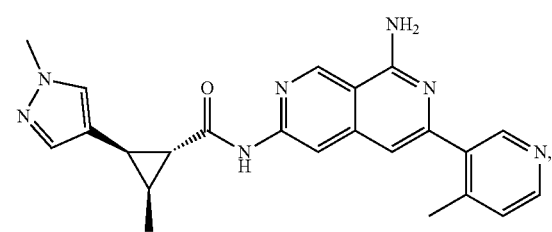
1220 -continued
327
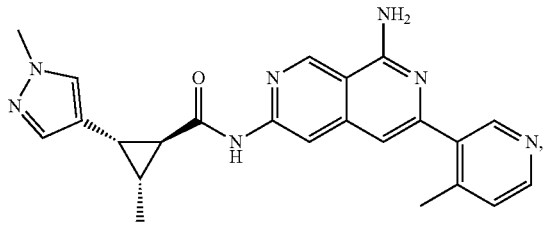
328
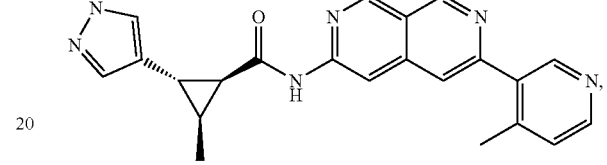
329
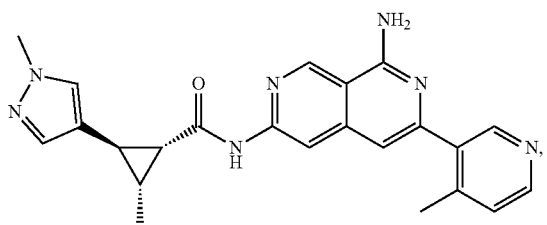
330
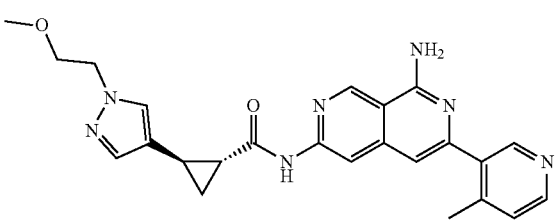
331
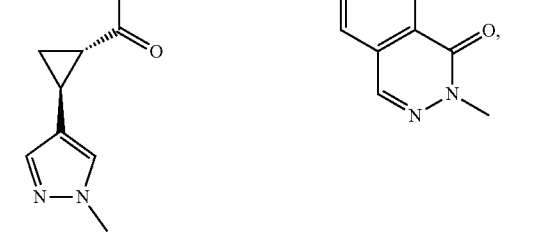
339
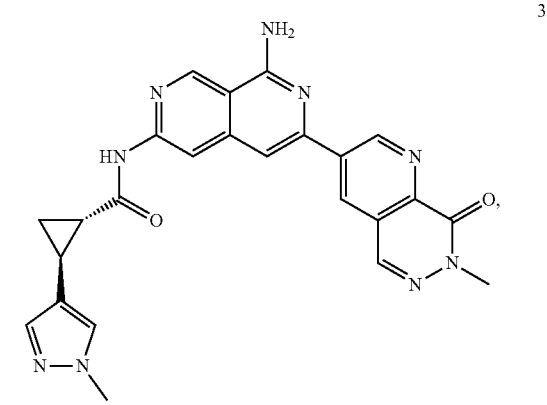

1221
-continued
340 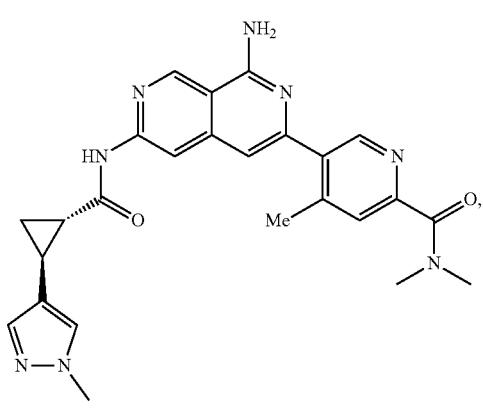
341 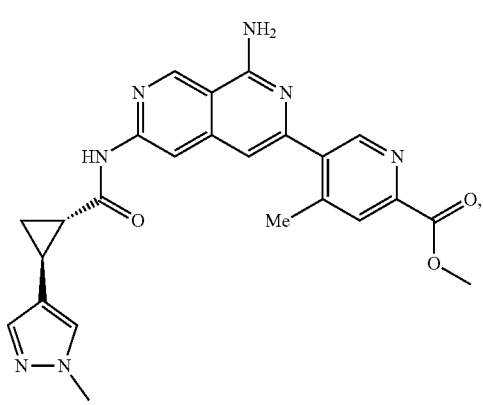
342 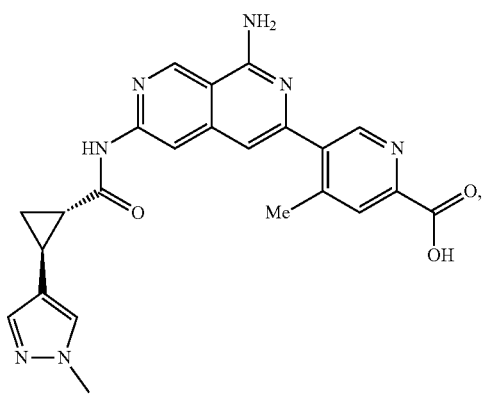
343 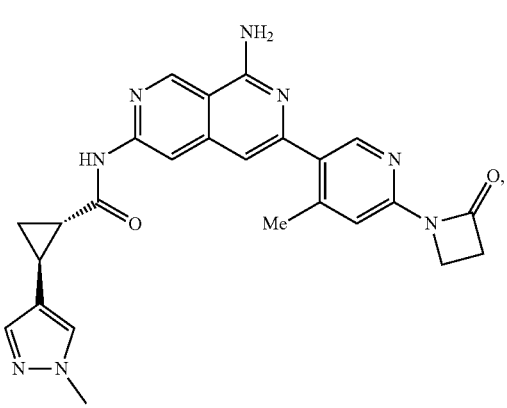
1222
-continued
344 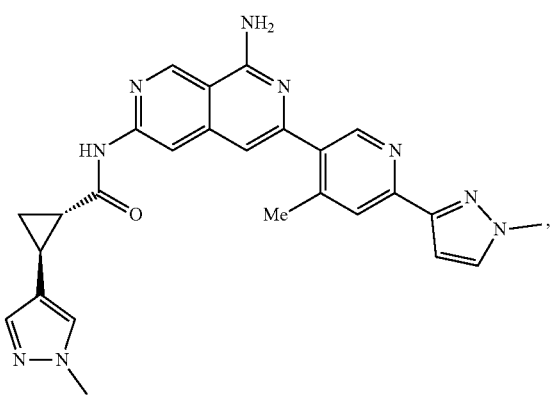
345 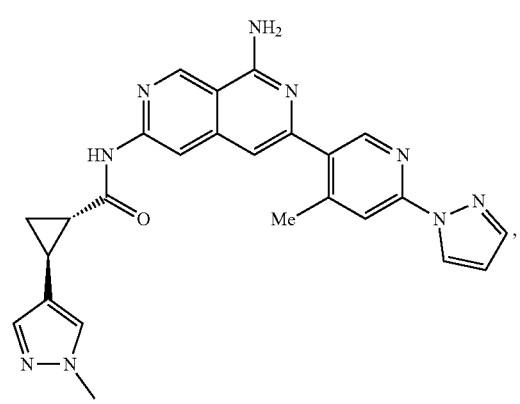
346 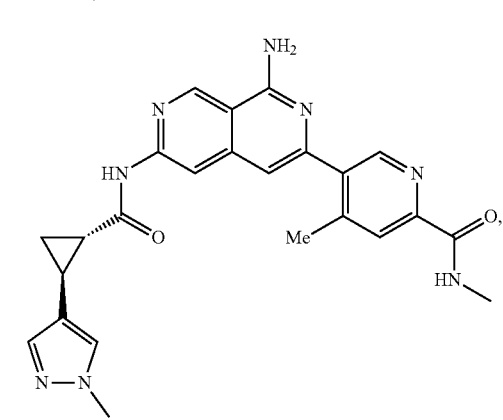
347 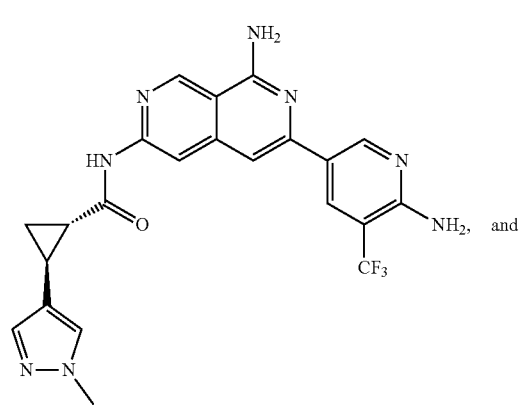

348
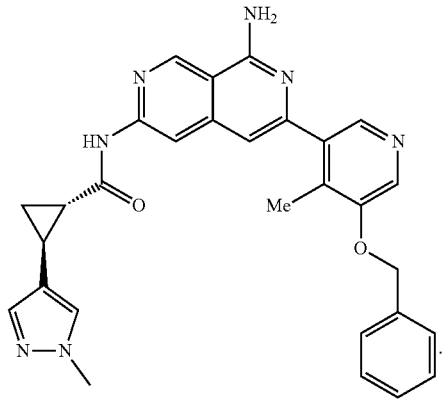
Embodiment 36. The compound of embodiment 2, wherein A is —NR$^g$R$^h$.
Embodiment 37. The compound of embodiment 36, wherein R$^g$ is H or methyl.
Embodiment 38. The compound of embodiment 37, wherein R$^g$ is H.
Embodiment 39. The compound of embodiment 38, wherein m is 0.
Embodiment 40. The compound of embodiment 39, having one of the following structures:
9
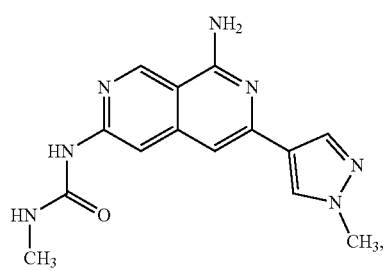
31
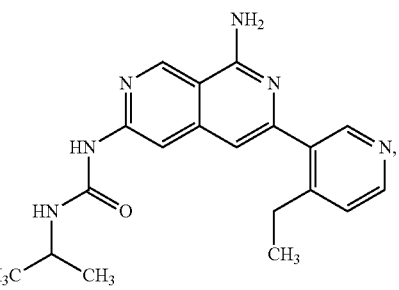
34
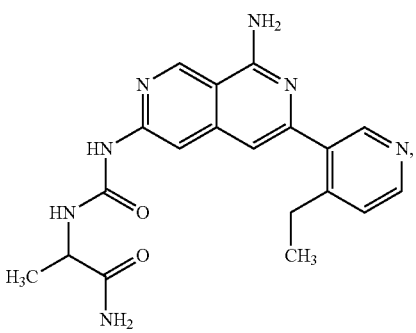
65
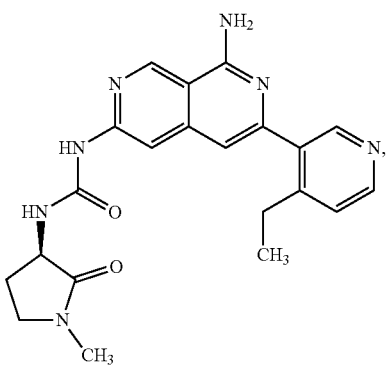
109
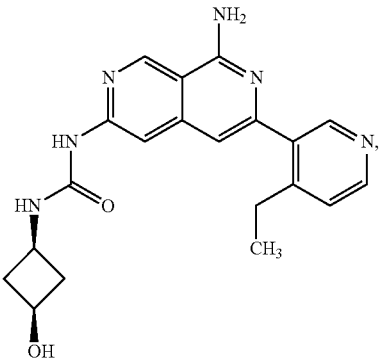
116
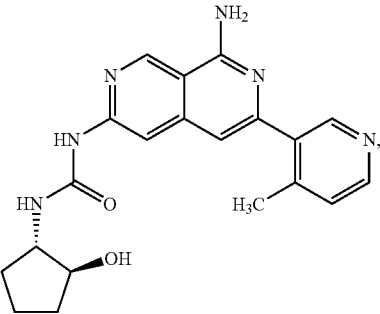
117
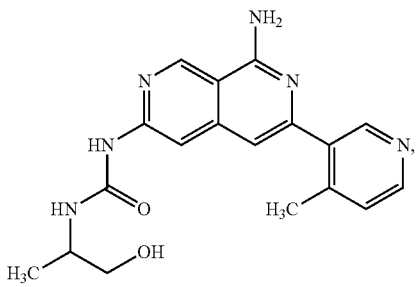
130
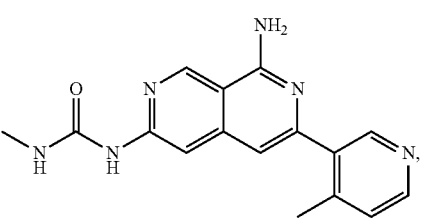

134 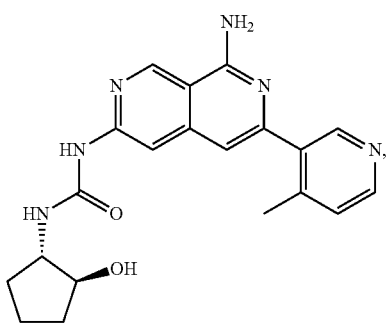
171 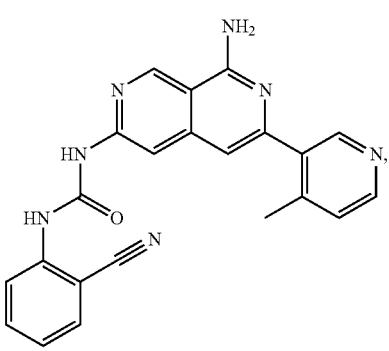
174 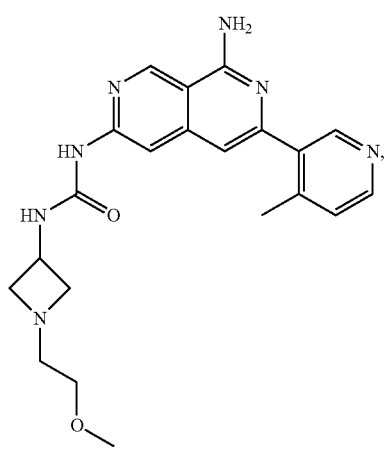
175 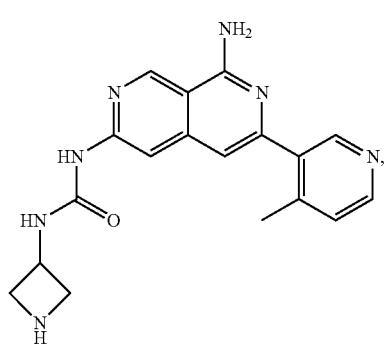
176 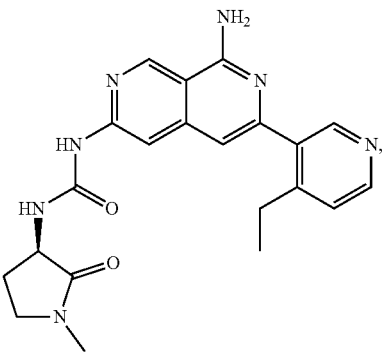
177 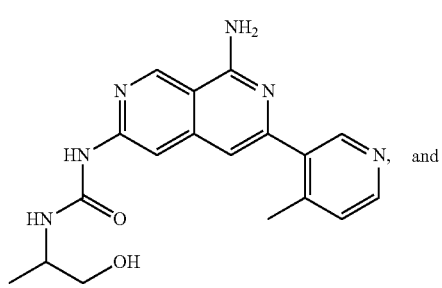
178 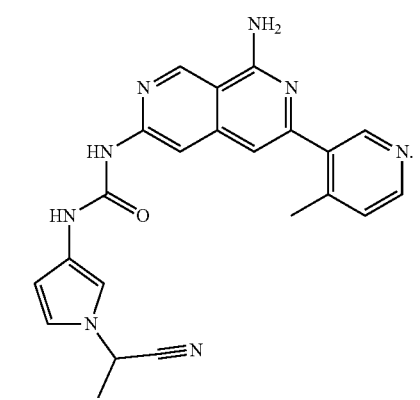
Embodiment 41. The compound of embodiment 37, having one of the following structures:
30 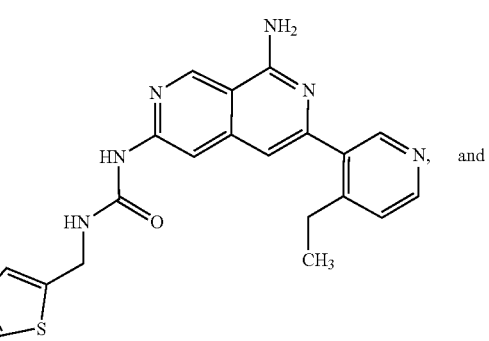

Embodiment 42. The compound of embodiment 2, wherein A is R$_9$—(C$_{1-6}$ alkyl)-.

Embodiment 43. The compound of embodiment 42, wherein said R$_9$—(C$_{1-6}$ alkyl)- is R$_9$—(C$_{1-4}$ alkyl)-, wherein said alkyl is linear or branched and can be optionally substituted.

Embodiment 44. The compound of embodiment 43, having one of the following structures:

Embodiment 45. The compound of embodiment 2, wherein A is B—(C$_{1-6}$ alkyl)$_t$-.

Embodiment 46. The compound of embodiment 45, wherein t is 0.

Embodiment 47. The compound of embodiment 46, wherein B is C$_{3-9}$ heteroaryl.

Embodiment 48. The compound of embodiment 47, wherein said heteroaryl is selected from the group consisting of:

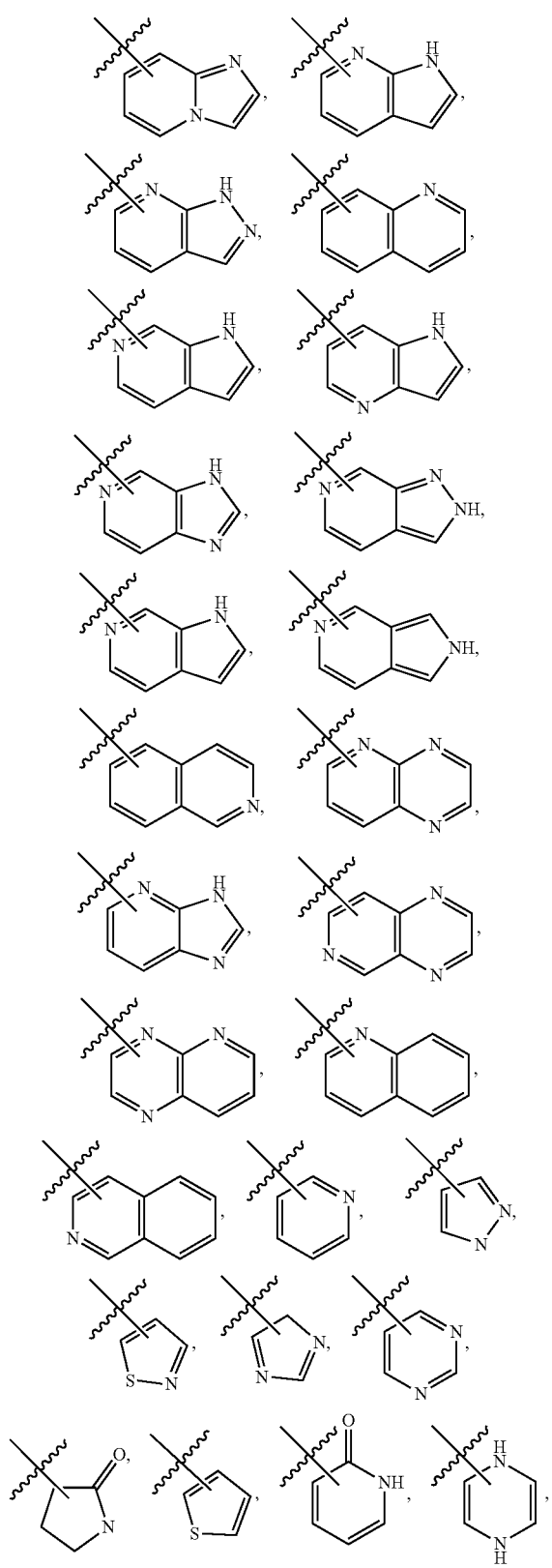

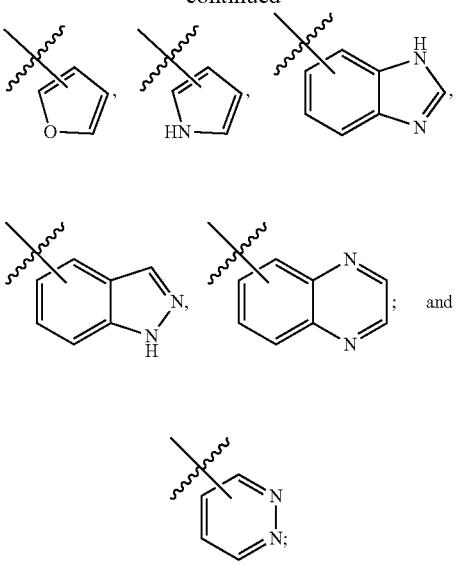

each of which can be optionally substituted with one, two or three substituents, $R^{10}$, $R^{10'}$ and $R^{10''}$.

Embodiment 49. The compound of embodiment 48, wherein said heteroaryl is:

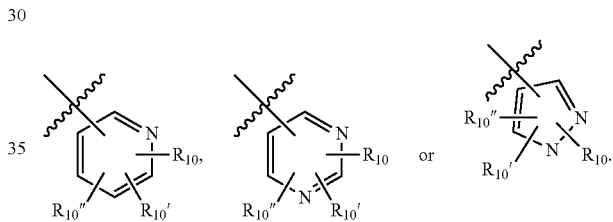

Embodiment 50. The compound of embodiment 49, wherein said heteroaryl is:

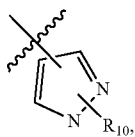

wherein, $R_{10}$ is $C_{1-6}$ alkyl.

Embodiment 51. The compound of embodiment 50, having one of the following structures:

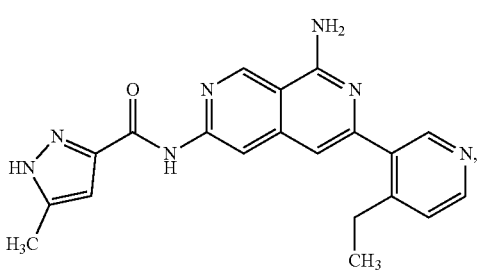

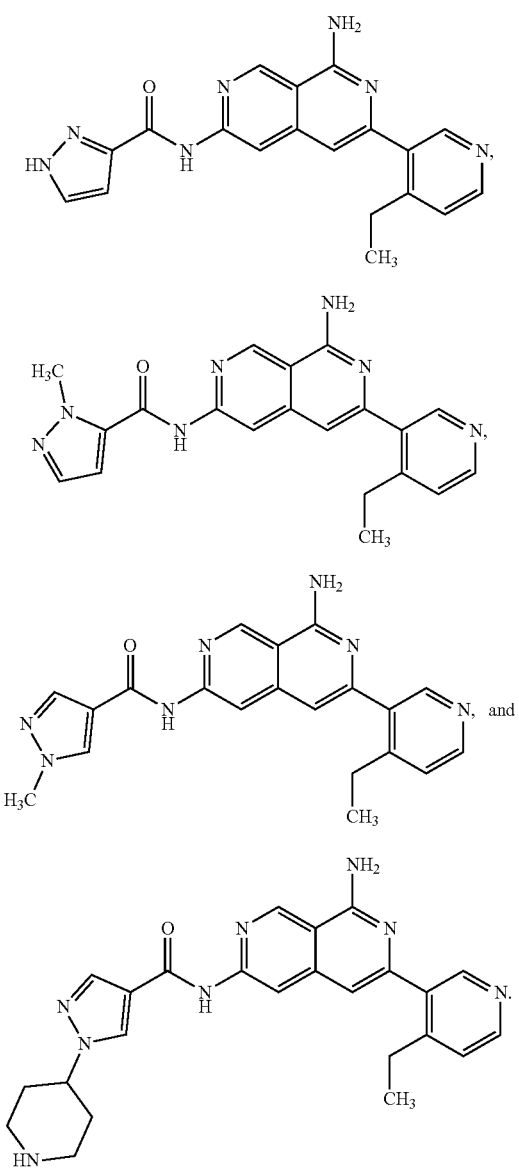
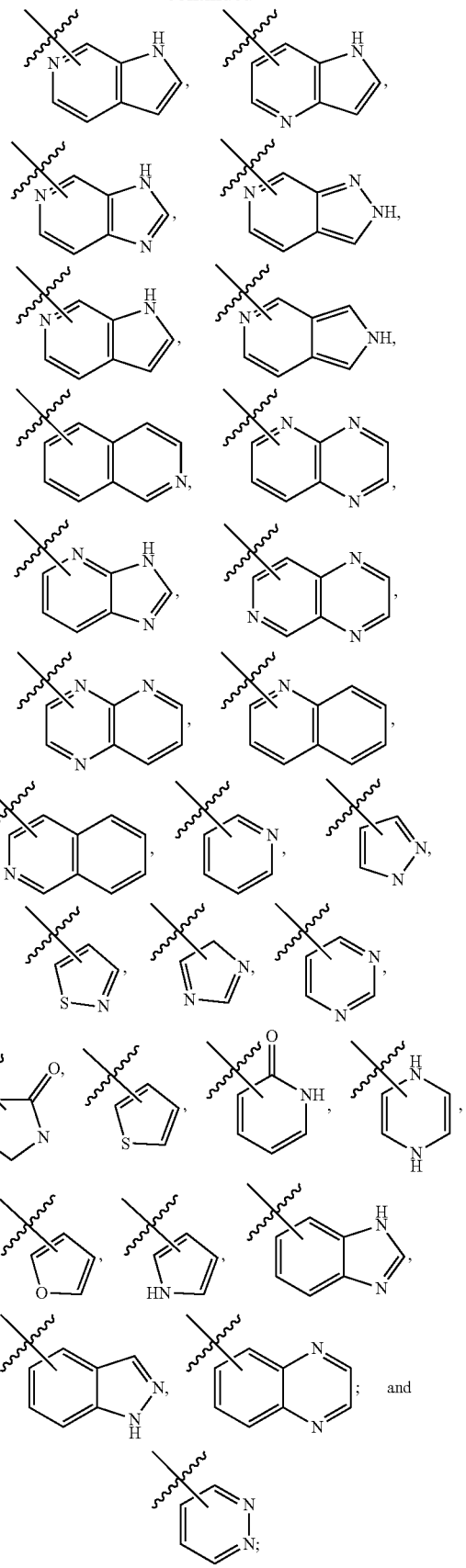
Embodiment 52. The compound of embodiment 2, wherein $R_2$ is D.
Embodiment 53. The compound of embodiment 52, wherein z is 0.
Embodiment 54. The compound of embodiment 53, wherein said heteroaryl is selected from the group consisting of:
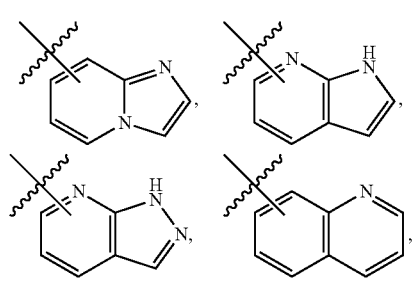

each of which can be optionally substituted with one, two or three substituents, $R^{14}$, $R^{15}$ and $R^{16}$.
Embodiment 55. The compound of embodiment 54, wherein said heteroaryl is:
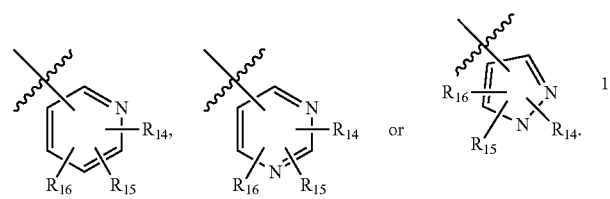
Embodiment 56. The compound of embodiment 55, wherein said heteroaryl is:
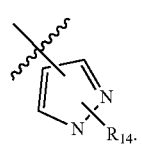
Embodiment 57. The compound of embodiment 56, having one of the following structures:
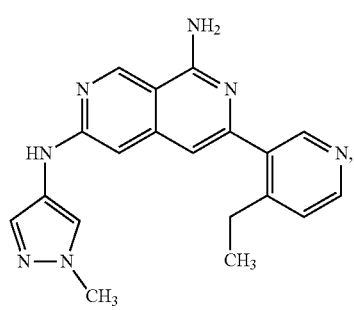
74
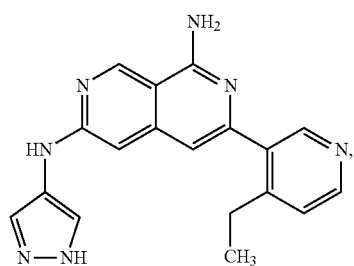
75
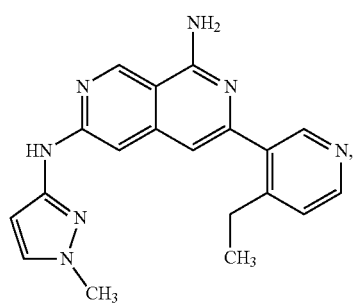
76
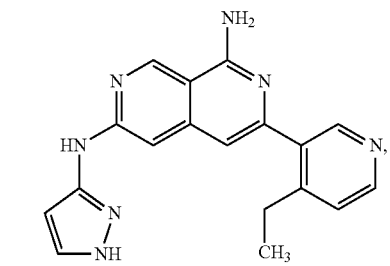
77
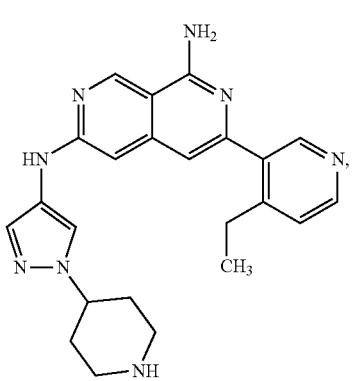
78
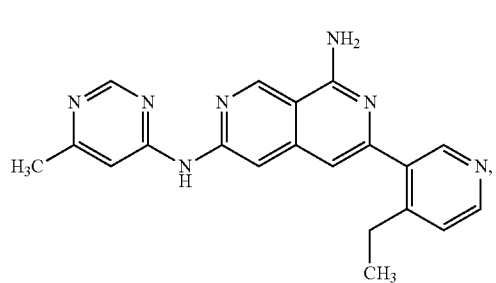
80
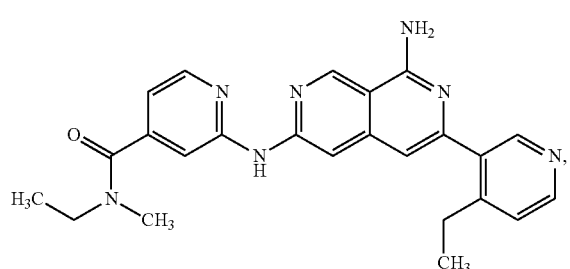
81
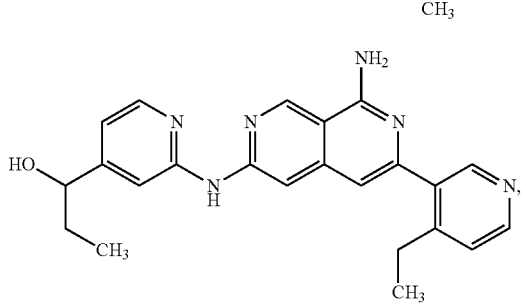
82

1235
-continued
83
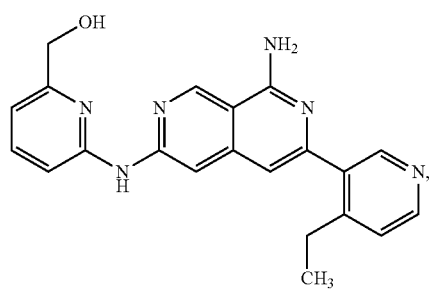
85
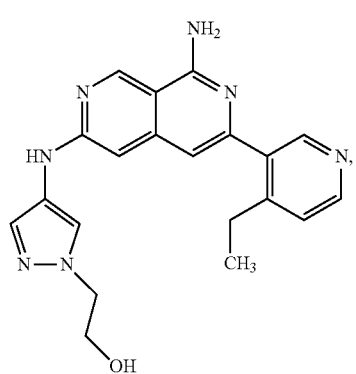
161
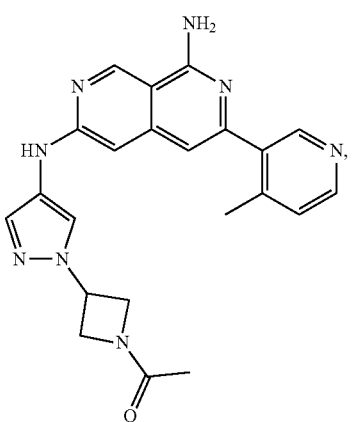
168
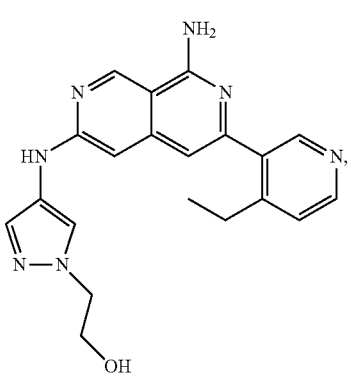
1236
-continued
170
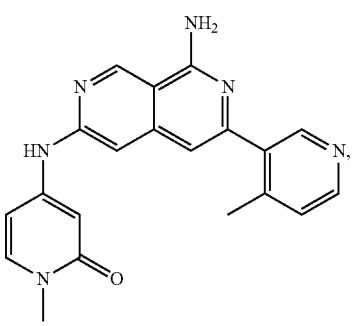
169
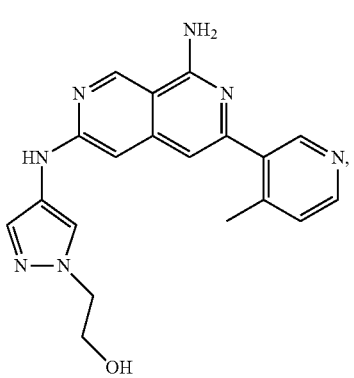
182
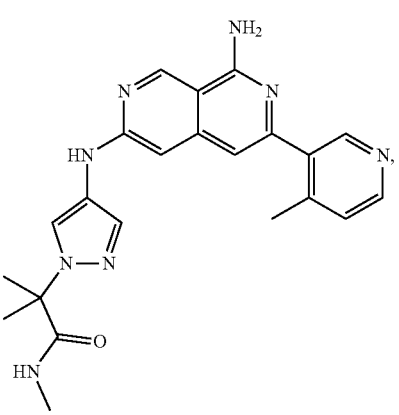
183
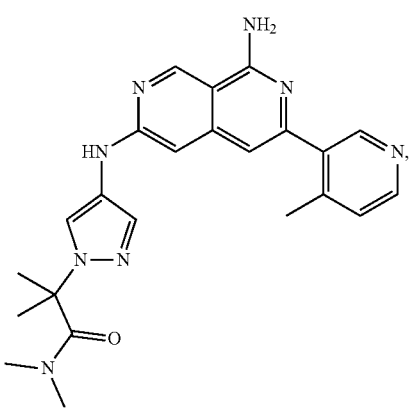

1237
-continued
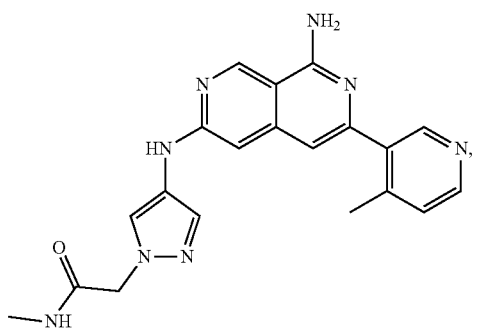
184
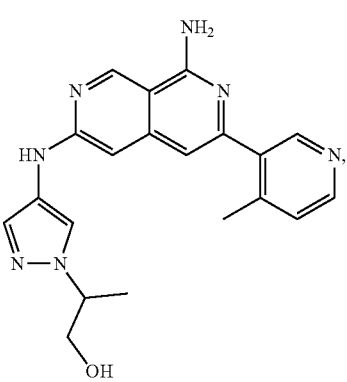
213
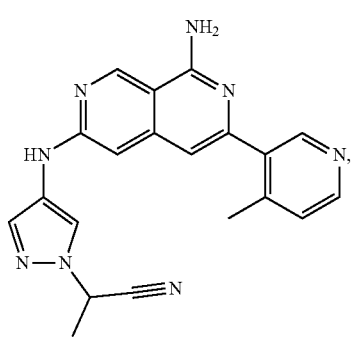
217
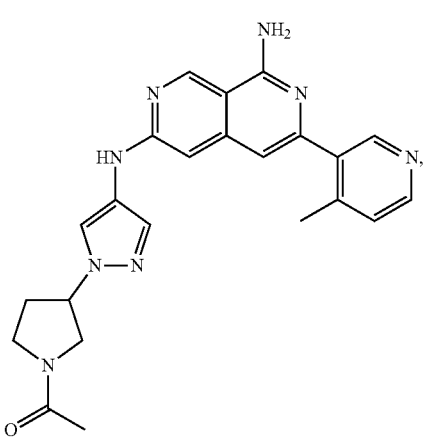
218
1238
-continued
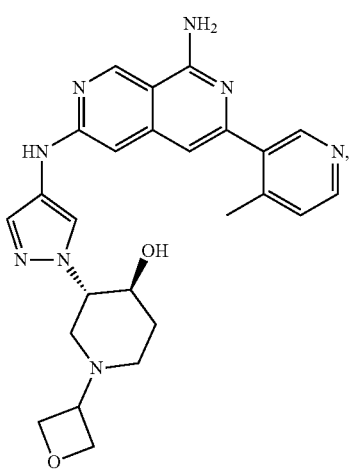
219
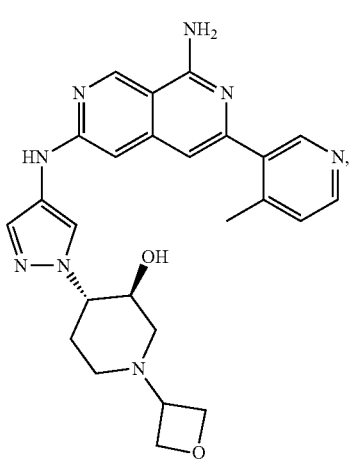
220
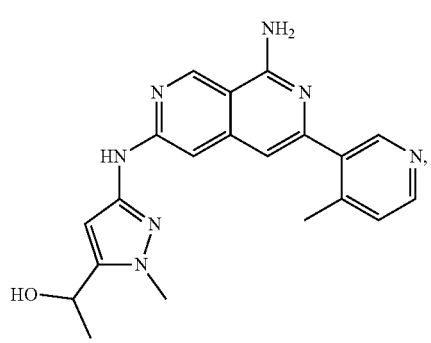
221
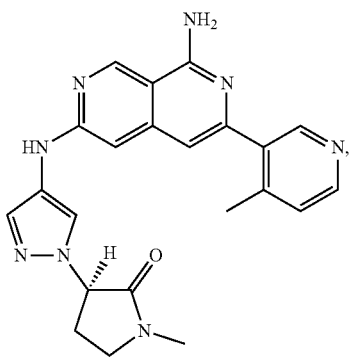
249

| 1239 | 1240 |
|---|---|
| -continued | -continued |
| 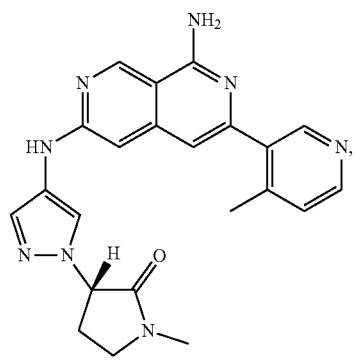 | 250 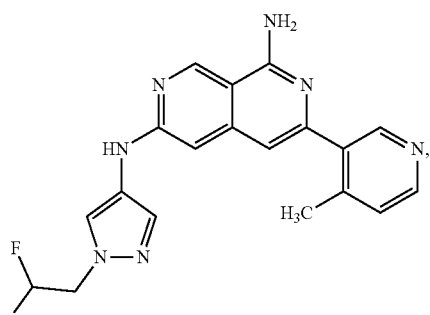 257 |
| 251 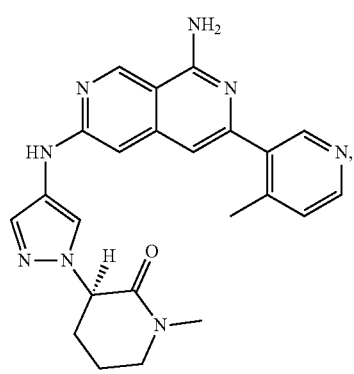 | 259 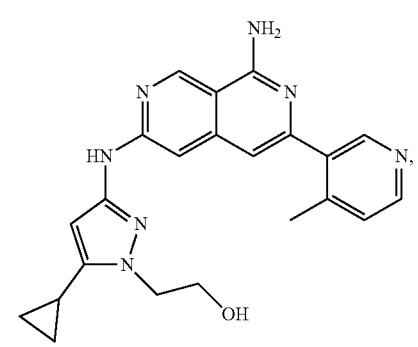 |
| 252 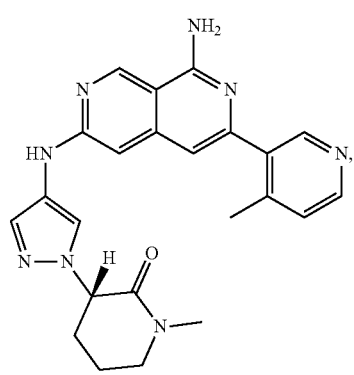 | 260 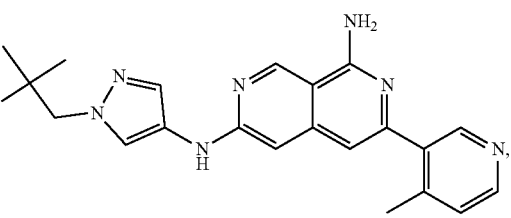 |
| 256 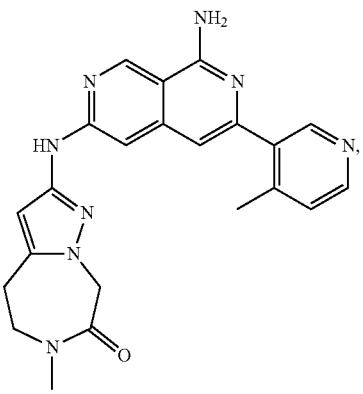 | 261 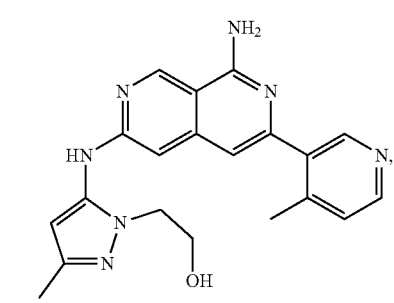 |
| | 262 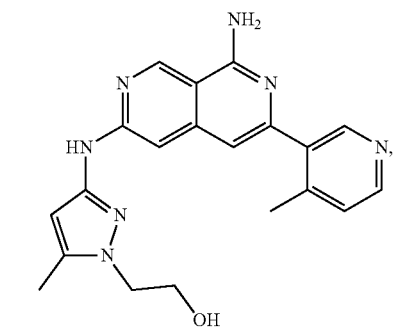 |

Embodiment 58. The compound of embodiment 53, wherein D is optionally substituted $C_{6-10}$ aryl.

Embodiment 59. The compound of embodiment 58, wherein said optionally substituted $C_{6-10}$ aryl is an optionally substituted phenyl.

Embodiment 60. The compound of embodiment 59, wherein said optionally substituted phenyl is substituted with an optionally substituted branched or linear $C_{1-6}$ alkyl or a $C_{3-7}$ heterocyclyl.

Embodiment 61. The compound of embodiment 60, having one of the following structures:

Embodiment 62. The compound of embodiment 2, wherein $R_{1'}$ is optionally substituted $C_{2-9}$ heteroaryl.

Embodiment 63. The compound of embodiment 62, wherein said optionally substituted $C_{2-9}$ heteroaryl is an optionally substituted 5-member heteroaryl containing 1 or 2 nitrogen atoms.

Embodiment 64. The compound of embodiment 63, wherein said 5-member heteroaryl is a pyrazole.

Embodiment 65. The compound of embodiment 2, wherein $R_{1'}$ is halogen.

Embodiment 66. The compound of embodiment 65, wherein said halogen is fluoro or chloro.

Embodiment 67. The compound of embodiment 2, wherein $R_{1'}$ is optionally substituted $C_{1-6}$ alkyl, $C_{2-6}$ alkenyl, or $C_{3-6}$ cycloalkyl.

Embodiment 68. The compound of embodiment 67, wherein $R_{1'}$ is optionally substituted $C_{1-6}$ alkyl.

Embodiment 69. The compound of embodiment 68, wherein $R_{1'}$ is optionally substituted methyl or ethyl.

Embodiment 70. The compound of embodiment 69, wherein $R_{1'}$ is methyl.

Embodiment 71. The compound of of any one of embodiments 64, 66, or 67 having one of the following structures:

153
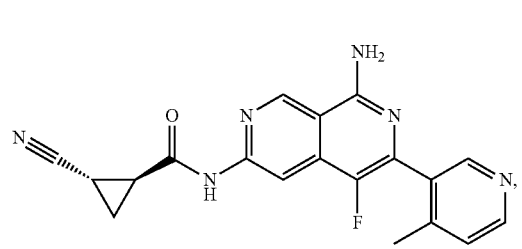
156
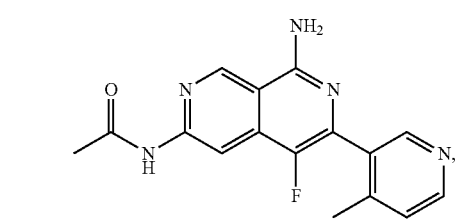
162
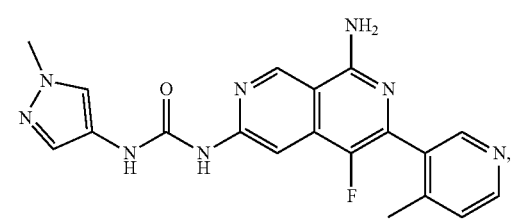
163
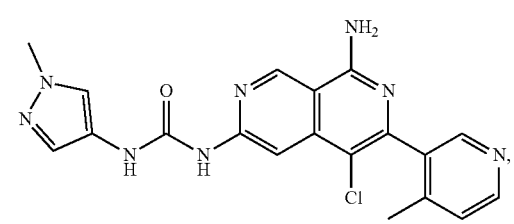
172
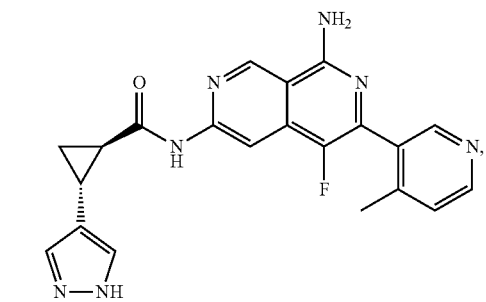
173
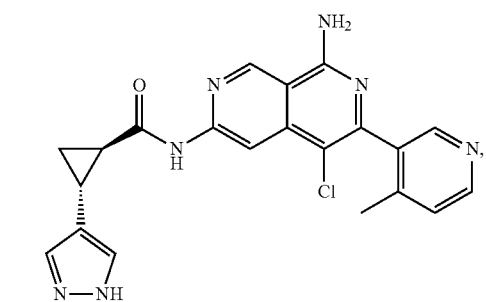
195
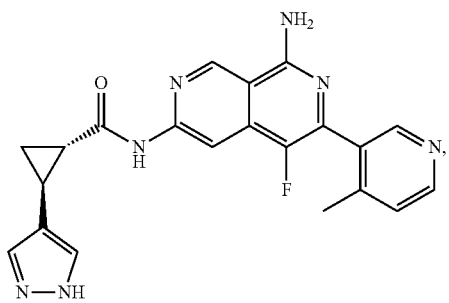
196
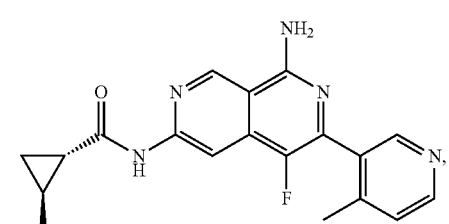
204
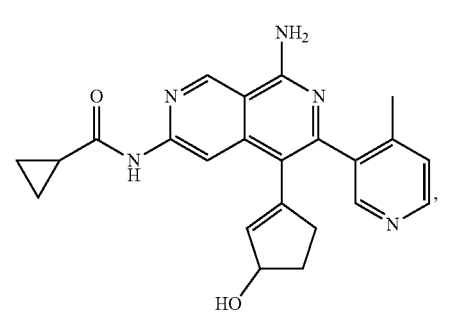
205
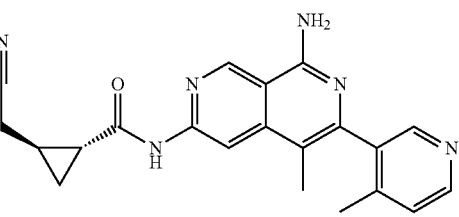
210
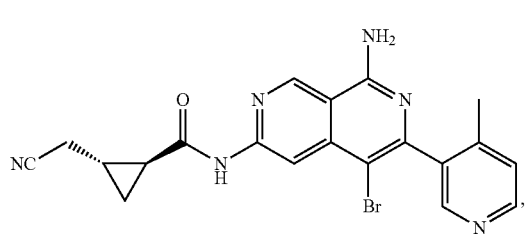
233
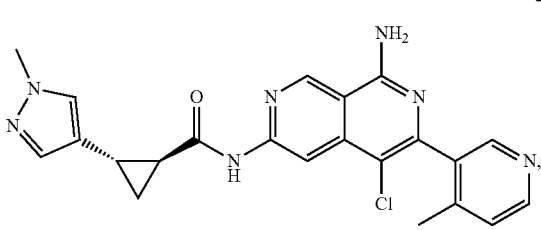

1245
-continued

234
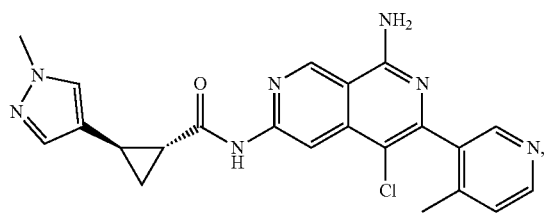

258
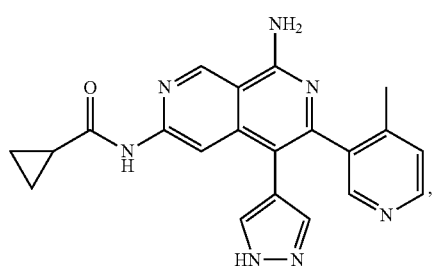

269
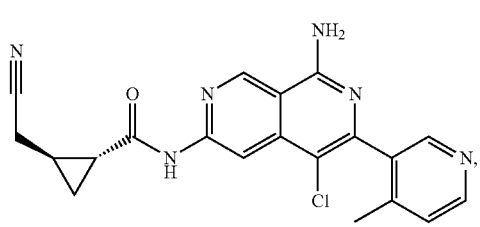

270
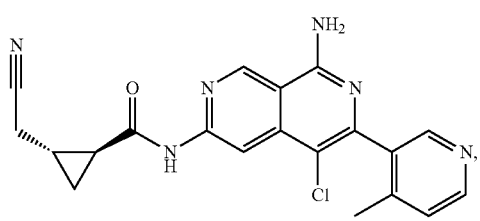

271
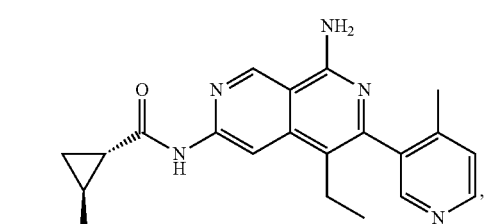

272
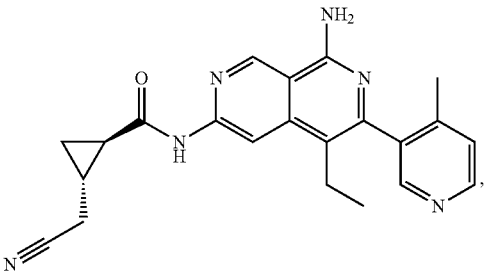

1246
-continued

275
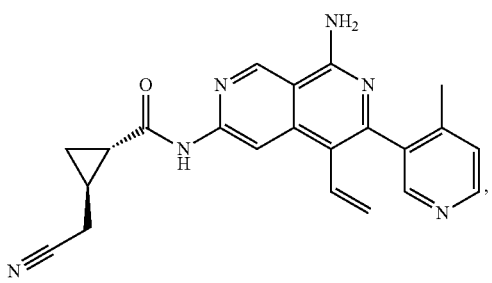

316
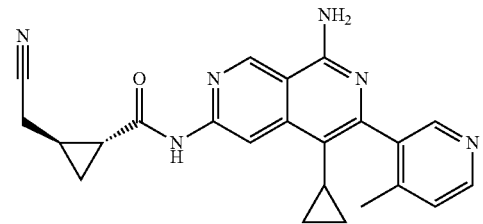

317
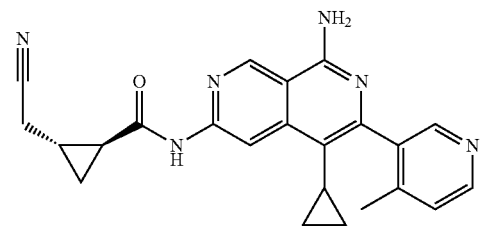

332
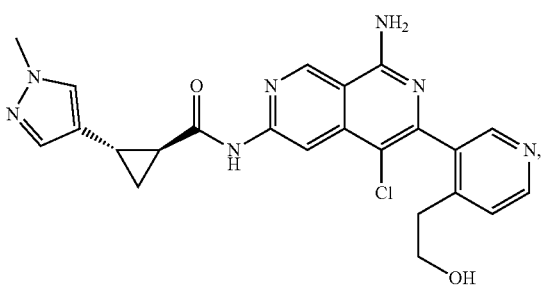

and

333
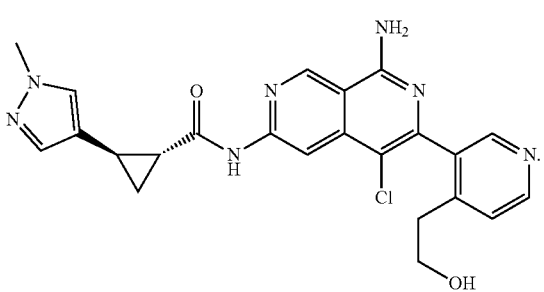

Embodiment 72. The compound of embodiment 1, wherein $R_1$ is optionally substituted $C_{6-10}$ aryl.

Embodiment 73. The compound of embodiment 72, wherein said optionally substituted $C_{6-10}$ aryl is optionally substituted phenyl.

Embodiment 74. The compound of embodiment 73, wherein said optionally substituted phenyl is substituted with optionally substituted branched or linear $C_{1-6}$ alkyl, $C_{1-6}$ alkoxy, halogen, cyano, hydroxyl, amino, —$CF_3$, or —(CO)$NR^cR^d$; wherein $R^c$ and $R^d$ are as described above.

Embodiment 75. The compound of embodiment 74, having one of the following structures:
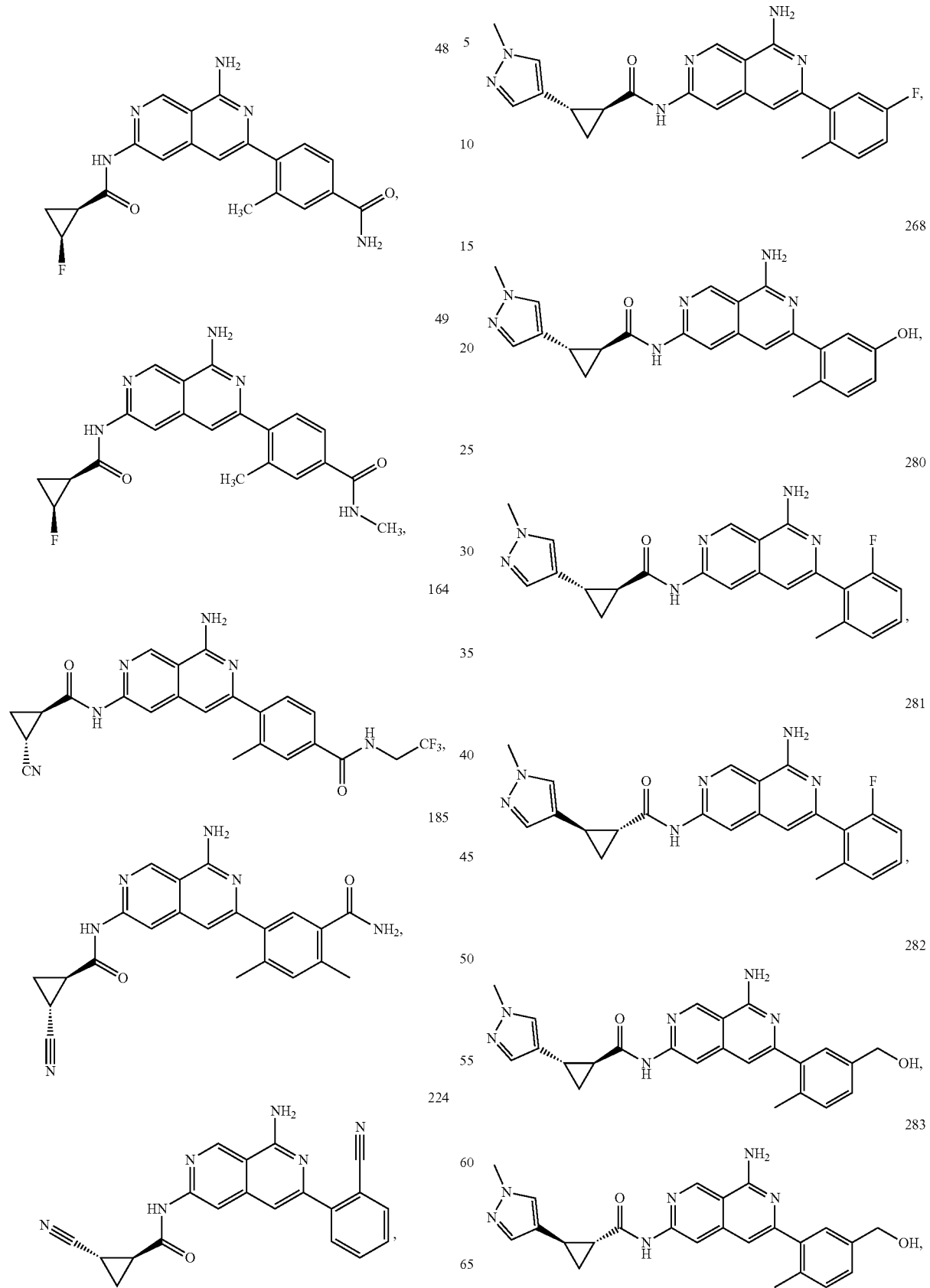

300

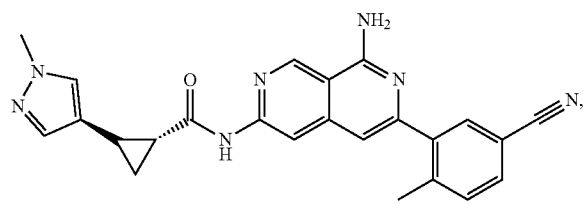

301

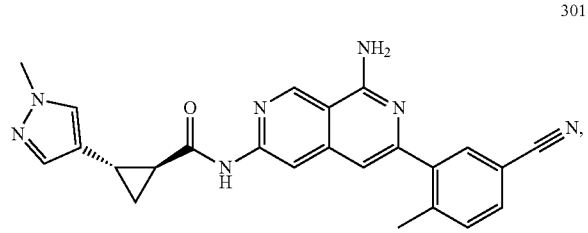

302

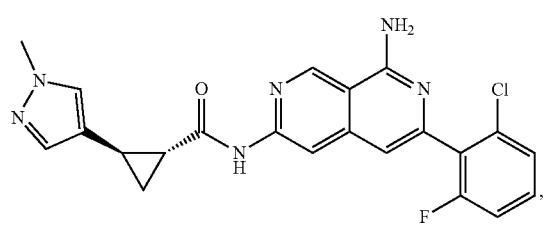

303

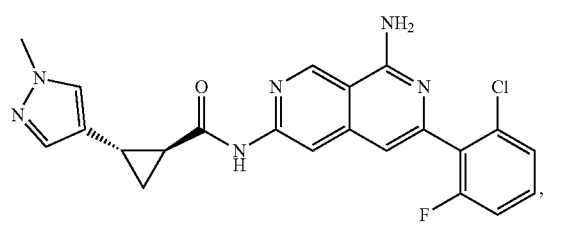

304

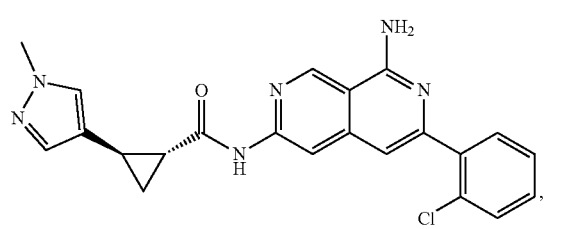

305

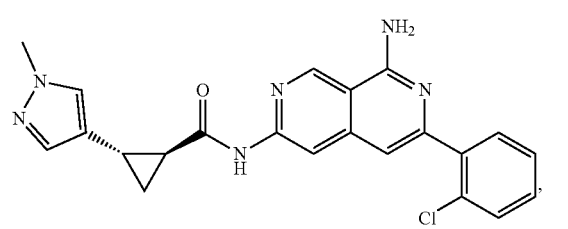

306

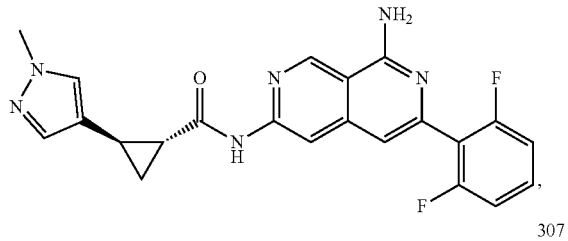

307

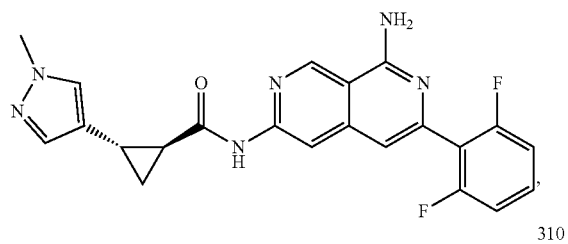

310

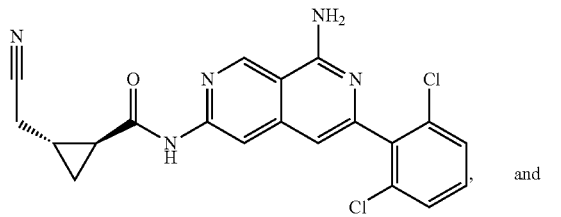

and

311

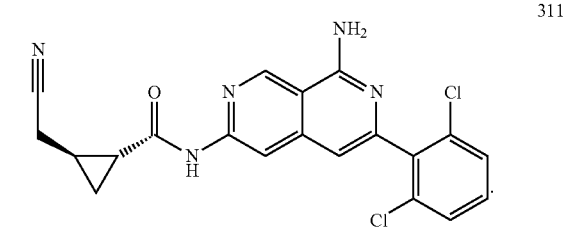

Embodiment 76. A pharmaceutical composition comprising a compound of any one of embodiments 1-75 and a pharmaceutically acceptable carrier.

Embodiment 77. The pharmaceutical composition of embodiment 76, wherein said composition further comprises a chemotherapeutic agent.

Embodiment 78. The pharmaceutical composition of embodiment 77, wherein said chemotherapeutic agent is an immunotherapeutic agent.

Embodiment 79. A method for inhibiting HPK1, said method comprising contacting HPK1 with an effective amount of a compound of any one of embodiments 1-75 or a pharmaceutical composition of any one of embodiments 76-78.

Embodiment 80. A method for enhancing an immune response in a subject in need thereof, wherein the method comprises administering to said subject an effective amount of a compound of any one of embodiments 1-75 or a pharmaceutical composition of any one of embodiments 76-78.

Embodiment 81. The method of embodiment 80, wherein T cells in the subject have at least one of enhanced priming, enhanced activation, enhanced migration, enhanced proliferation, enhanced survival, and enhanced cytolytic activity relative to prior to the administration of the compound or pharmaceutical composition.

Embodiment 82. The method of embodiment 81, wherein the T cell activation is characterized by an elevated frequency of γ-IFN$^+$ CD8 T cells or enhanced levels of IL-2 or granzyme B production by T cells relative to prior to administration of the compound or pharmaceutical composition.

Embodiment 83. The method of embodiment 81, wherein the number of T cells is elevated relative to prior to administration of the compound or pharmaceutical composition.

Embodiment 84. The method of any one of embodiments 81-83, wherein the T cell is an antigen-specific CD8 T cell.

Embodiment 85. The method of embodiment 84, wherein the antigen presenting cells in the subject have enhanced maturation and activation relative prior to the administration of the compound or pharmaceutical composition.

Embodiment 86. The method of embodiment 85, wherein the antigen presenting cells are dendritic cells.

Embodiment 87. The method of embodiment 85, wherein the maturation of the antigen presenting cells is characterized by increased frequency of CD83$^+$ dendritic cells.

Embodiment 88. The method of embodiment 85, wherein the activation of the antigen presenting cells is characterized by elevated expression of CD80 and CD86 on dendritic cells.

Embodiment 89. The method of any one of embodiments 79-88, wherein said subject has cancer.

Embodiment 90. A method for treating a HPK1-dependent disorder, said method comprising administering to a subject in need thereof an effective amount of a compound of any one of embodiments 1-75 or a pharmaceutical composition of any one of embodiments 76-78.

Embodiment 91. The method of embodiment 90, wherein said HPK1-dependent disorder is a cancer.

Embodiment 92. The method of embodiment 89 or 91, wherein the cancer comprises at least one cancer selected from the group consisting of colorectal cancer, melanoma, non-small cell lung cancer, ovarian cancer, breast cancer, pancreatic cancer, a hematological malignancy, and a renal cell carcinoma.

Embodiment 93. The method of any one of embodiments 89, 91, or 92, wherein the cancer has elevated levels of T-cell infiltration.

Embodiment 94. The method of any one of embodiments 89, 91, 92, or 93, wherein the cancer cells in the subject selectively have elevated expression of MHC class I antigen expression relative to prior to the administration of the compound or composition.

Embodiment 95. The method of any one of embodiments 89, 91, 92, 93, or 94, wherein said method further comprises administering a chemotherapeutic agent to said subject.

Embodiment 96. The method of embodiment 95, wherein said chemotherapeutic agent is administered to said subject simultaneously with said compound or said composition.

Embodiment 97. The method of embodiment 95, wherein said chemotherapeutic agent is administered to said subject prior to administration of said compound or said composition.

Embodiment 98. The method of embodiment 95, wherein said chemotherapeutic agent is administered to said subject after administration of said compound or said composition.

The invention claimed is:

1. A method for enhancing an immune response in a subject in need thereof comprising administering to said subject an effective amount a compound of Formula I:

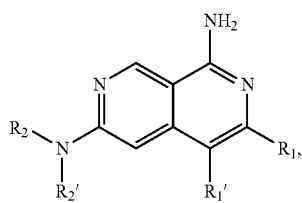

or a pharmaceutically acceptable salt thereof, wherein, $R_1$ is $C_{2-9}$ heteroaryl, $C_{2-9}$ heterocyclyl, $C_{6-10}$ aryl, $C_{3-9}$ cycloalkyl, $C_{1-6}$ alkyl, $C_{2-6}$ alkenyl, $C_{2-6}$ alkynyl, —C≡C—($C_{2-9}$ heteroaryl), —C≡C—($C_{6-10}$ aryl), —CH(R$^{j'}$)—O—($C_{2-9}$ heteroaryl), —CH(R$^{j'}$)—O—($C_{2-9}$) heterocyclyl), —CH(R$^{j'}$)—O—($C_{6-10}$ aryl), —CH(R$^{j'}$)—O—($C_{3-9}$ cycloalkyl), —CH(R$^{j'}$)—O—($C_{1-6}$ alkyl), —C(O)N(R$^{j'}$)($C_{2-9}$ heteroaryl), —C(O)N(R$^{j'}$)($C_{2-9}$ heterocyclyl), —C(O)NR$^{24}$R$^{25}$, —C(O)OR$^{26}$, —C(=NR$^{29}$)R$^{27}$, —C(=NR$^{29}$)NR$^{24}$R$^{25}$, —C(=NOR$^{29}$)R$^{27}$, cyano, hydrogen, halogen, —NR$^{24}$R$^{25}$, —NR$^{28}$C(O)R$^{27}$, —NR$^{28}$C(O)NR$^{24}$R$^{25}$, —NR$^{28}$C(O)OR$^{26}$, —NR$^{28}$S(O)R$^{29}$; —NR$^{28}$SO$_2$R$^{29}$, —NR$^{28}$SO$_2$NR$^{24}$R$^{25}$, —OR$^{26}$, —OC(O)R$^{27}$, —OC(O)NR$^{24}$R$^{25}$, —S(O)R$^{29}$; —SO$_2$R$^{29}$, or —SO$_2$NR$^{24}$R$^{25}$;

wherein the $C_{2-9}$ heteroaryl and $C_{2-9}$ heterocyclyl of $R_1$ independently have 1-4 heteroatoms selected from O, S and N; and wherein the $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl and $C_{2-9}$ heterocyclyl of $R_1$ are optionally substituted independently with one, two, three, four or live substituents;

wherein the $C_{3-9}$ cycloalkyl, $C_{6-10}$ aryl, $C_{2-9}$ heteroaryl or $C_{2-9}$ heterocyclyl of $R_1$ together with two of said substituents can form a bicyclic which is optionally substituted;

wherein a carbon embedded in said cycloalkyl, aryl, heteroaryl or heterocyclyl taken together with an oxygen to which it is bound can form a carbonyl;

each R$^{j'}$ is independently hydrogen or optionally substituted $C_{1-6}$ alkyl;

each R$^{24}$ and R$^{25}$ is independently hydrogen or optionally substituted $C_{1-6}$ alkyl; or R$^{24}$ and R$^{25}$ are taken together with the nitrogen atom to which they are attached to form a $C_{3-7}$ heterocyclyl optionally substituted with one to four substituents;

each R$^{26}$, R$^{27}$ and R$^{28}$ is independently hydrogen or optionally substituted $C_{1-6}$ alkyl;

each R$^{29}$ is independently optionally substituted $C_{1-6}$ alkyl;

$R_{1'}$ is hydrogen, $C_{1-6}$ alkyl, alkenyl, $C_{3-6}$ cycloalkyl, $C_{6-10}$ aryl, $C_{2-9}$ heteroaryl, or halogen, wherein said alkyl, alkenyl, cycloalkyl, aryl and heteroaryl can be optionally substituted with one, two, three, four or five substituents; provided at least one of $R_1$ and $R_{1'}$ is other than hydrogen;

$R_2$ is A-C(O)— or D;

A is $C_{1-6}$ alkyl, $C_{2-6}$ alkenyl, $C_{2-6}$ alkynyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{1-6}$ alkylene)-, —NR$^g$R$^h$ or —OR$^h$;

wherein the $C_{1-6}$ alkyl, $C_{3-9}$ cycloalkyl, $C_{6-10}$ aryl, $C_{2-9}$ heteroaryl and $C_{2-9}$ heterocyclyl of A are optionally substituted independently with one, two, three, four or five substituents;

R$^g$ is H or $C_{1-6}$ alkyl optionally substituted with one to four substituents independently selected from the group consisting of hydroxyl, halogen, cyano, amino, di($C_{1-6}$ alkyl)amino, mono($C_{1-6}$ alkyl)amino; —CHF$_2$, and —CF$_3$;

R$^h$ is $C_{1-6}$ alkyl, $C_{3-7}$ cycloalkyl, $C_{6-10}$ aryl $C_{2-9}$ heteroaryl, €2-9 heterocyclyl ($C_{3-7}$ cycloalkyl)-($C_{1-6}$ alkylene)-, ($C_{6-10}$ aryl)-($C_{1-6}$ alkylene)-, ($C_{2-9}$ heteroaryl)($C_{1-6}$ alkylene)-, or ($C_{2-9}$ heterocyclyl)-($C_{1-6}$ alkylene)-;

wherein the $C_{1-6}$ alkyl, $C_{3-7}$ cycloalkyl, $C_{6-10}$ aryl, $C_{2-9}$ heteroaryl and $C_{2-9}$ heterocyclyl of R$^h$ are optionally substituted independently with one, two, three, four or five substituents;

D is H, $C_{1-6}$ alkyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{1-6}$ alkylene)-, or ($C_{3-7}$ cycloalkyl)-S(O)$_2$—;

wherein the $C_{2-9}$ heteroaryl and $C_{2-9}$ heterocyclyl of D independently have 1-4 heteroatoms selected from O, S and N; and wherein the $C_{1-6}$ alkyl, $C_{3-7}$ cycloalkyl, $C_{6-10}$ aryl, $C_{2-9}$ heteroaryl and $C_{2-9}$ heterocyclyl of D are optionally substituted independently with one, two, three, four or five substituents, wherein two of the substituents attached to different atoms are taken together with the atoms to which they attached to form a bicyclic or tricyclic, wherein said bicyclic or tricyclic is optionally substituted, and wherein a carbon embedded in said heteroaryl or heterocyclyl taken together with an oxygen to which it is bound can form a carbonyl;

and $R_{2'}$ is H or optionally substituted $C_{1-6}$ alkyl.

2. The method of claim 1, wherein said subject has cancer.

3. A method for treating a HPK1-dependent disorder comprising administering to a subject in need thereof an effective amount of a compound of Formula I:

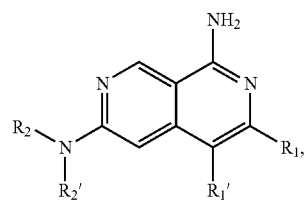

(I)

or a pharmaceutically acceptable salt thereof, wherein, $R_1$ is $C_{2-9}$ heteroaryl, $C_{2-9}$ heterocyclyl, $C_{6-10}$ aryl, $C_{3-9}$ cycloalkyl, $C_{1-6}$ alkyl, $C_{2-6}$ alkenyl, $C_{2-6}$ alkynyl, —C≡C—($C_{2-9}$ heteroaryl), —C≡C—($C_{6-10}$ aryl), —CH($R^{j'}$)—O—($C_{2-9}$ heteroaryl), —CH($R^{j'}$)—O—($C_{2-9}$ heterocyclyl), —CH($R^{j'}$)—O—($C_{6-10}$ aryl), —CH($R_1$)—O—($C_{3-9}$ cycloalkyl), —CH($R^{j'}$)—(O)—($C_{1-6}$ alkyl), —C(O)N($R^{j'}$)($C_{2-9}$ heteroaryl), —C(O)N($R^{j'}$)($C_{2-9}$ heterocyclyl), —C(O)N$R^{24}R^{25}$, —C(O)O$R^{26}$, —C(=N$R^{29}$)$R^{27}$, —C(=N$R^{29}$)N$R^{24}R^{25}$, —C(=NO$R^{29}$)$R^{27}$, cyano, hydrogen, halogen, —N$R^{24}R^{25}$, —N$R^{28}$C(O)$R^{27}$, —N$R^{28}$C(O)N$R^{24}R^{25}$, —N$R^{28}$C(O)O$R^{26}$, —N$R^{28}$S(O)$R^{29}$, —N$R^{28}$SO$_2R^{29}$, —N$R^{28}$SO$_2$N$R^{24}R^{25}$, —O$R^{26}$, —OC(O)$R^{27}$, —OC(O)N$R^{24}R^{25}$, —S(O)$R^{29}$, —SO$_2R^{29}$, or —SO$_2$N$R^{24}R^{25}$;

wherein the $C_{2-9}$ heteroaryl and $C_{2-9}$ heterocyclyl of $R_1$ independently have 1-4 heteroatoms selected from O, S and N; and wherein the $C_{1-6}$ alkyl, $C_{2-6}$ alkenyl, $C_{2-6}$ alkynyl, $C_{3-9}$ cycloalkyl, $C_{6-10}$ aryl, $C_{2-9}$ heteroaryl and $C_{2-9}$ heterocyclyl of $R_1$ are optionally substituted independently with one, two, three, four or five substituents;

wherein the $C_{3-9}$ cycloalkyl, $C_{6-10}$ aryl, $C_{2-9}$ heteroaryl or $C_{2-9}$ heterocyclyl of $R_1$ together with two of said substituents can form a bicyclic which is optionally substituted;

wherein a carbon embedded in said cycloalkyl, aryl, heteroaryl or heterocyclyl taken together with an oxygen to winch it is bound can form a carbonyl;

each $R^{j'}$ is independently hydrogen or optionally substituted $C_{1-6}$ alkyl;

each $R^{24}$ and $R^{25}$ is independently hydrogen or optionally substituted $C_{1-6}$ alkyl; or $R^{24}$ and $R^{25}$ are taken together with the nitrogen atom to which they are attached to form a $C_{3-7}$ heterocyclyl optionally substituted with one to four substituents;

each $R^{26}$, $R^{27}$ and $R^{28}$ is independently hydrogen or optionally substituted $C_{1-6}$ alkyl;

each $R^{29}$ is independently optionally substituted $C_{1-6}$ alkyl;

$R_{1'}$ is hydrogen, $C_{1-6}$ alkyl, $C_{2-6}$ alkenyl, $C_{3-6}$ cycloalkyl, $C_{6-10}$ aryl, $C_{2-9}$ heteroaryl, or halogen, wherein said alkyl, alkenyl, cycloalkyl, aryl and heteroaryl can be optionally substituted with one, two, three, four or five substituents; provided at least one of $R_1$ and $R_{1'}$ is other than hydrogen;

$R_2$ is A-C(O)— or D;

A is $C_{1-6}$ alkyl, $C_{2-6}$ alkenyl, $C_{2-6}$ alkynyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{1-6}$ alkylene)-, —N$R^gR^h$ or —O$R^h$;

wherein the $C_{1-6}$ alkyl, $C_{3-9}$ cycloalkyl, $C_{6-10}$ aryl, $C_{2-9}$ heteroaryl and $C_{2-9}$ heterocyclyl of A are optionally substituted independently with one, two, three, four or five substituents;

$R^g$ is H or CM, alkyl optionally substituted with one to four substituents independently selected from the group consisting of hydroxyl, halogen, cyano, amino, di($C_{1-6}$ alkyl)amino, mono($C_{1-6}$ alkyl)amino; —CHF$_2$, and CF$_3$;

$R^h$ is $C_{1-6}$ alkyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, or heterocyclyl)-($C_{1-6}$ alkylene)-;

wherein the $C_{1-6}$ alkyl, $C_{3-7}$ cycloalkyl, $C_{6-10}$ aryl, $C_{2-9}$ heteroaryl and $C_{2-9}$ heterocyclyl of $R^h$ are optionally substituted independently with one, two, three, four or five substituents;

D is H, $C_{1-6}$ alkyl, $C_{3-7}$ cycloalkyl, $C_{6-10}$ aryl, $C_{2-9}$ heteroaryl, $C_{2-9}$ heterocyclyl, ($C_{3-7}$ cycloalkyl)-($C_{1-6}$ alkylene)-, ($C_{6-10}$ aryl)-($C_{1-6}$ alkylene)-, ($C_{2-9}$ heteroaryl)-($C_{1-6}$ alkylene)-, ($C_{2-9}$ heterocyclyl)-($C_{3-6}$ alkylene)-, or ($C_{3-7}$ cycloalkyl)-S(O)$_2$—;

wherein the $C_{2-9}$ heteroaryl and $C_{2-9}$ heterocyclyl of D independently have 1-4 heteroatoms selected from O, S and N; and wherein the $C_{1-6}$ alkyl, $C_{3-7}$ cycloalkyl, $C_{6-10}$ aryl, $C_{2-9}$ heteroaryl and $C_{2-9}$ heterocyclyl of D are optionally substituted independently with one, two, three, four or five substituents;

wherein two of the substituents attached to different atoms are taken together with the atoms to which they attached to form a bicyclic or tricyclic, wherein said bicyclic or tricyclic is optionally substituted; and wherein a carbon embedded in said heteroaryl or heterocyclyl taken together with an oxygen to which it is bound can form a carbonyl;

and $R_{2'}$ is H or optionally substituted $C_{1-6}$ alkyl;

wherein the HPK1-dependent disorder is a cancer selected from the group consisting of colorectal cancer, melanoma, non-small cell lung cancer, ovarian cancer, breast cancer, pancreatic cancer, a hematological malignancy, and a renal cell carcinoma.

4. The method of claim 3, further comprising administering a chemotherapeutic agent to the subject.

5. The method of claim 3, wherein $R_1$ is:

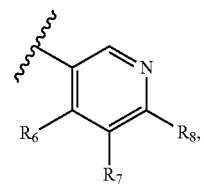

wherein $R_6$, $R_7$, and $R_8$ are each independently selected from the group consisting of hydrogen, hydroxyl amino, $C_{1-6}$ alkyl, $C_{1-6}$alkoxy, and mono($C_{1-6}$ alkyl)amino; or two of $R_6$, $R_7$, and $R_8$ can form a bicyclic.

6. The method of claim 5, wherein $R_1$ is

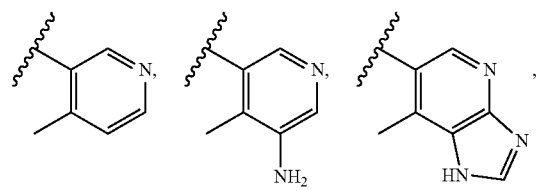

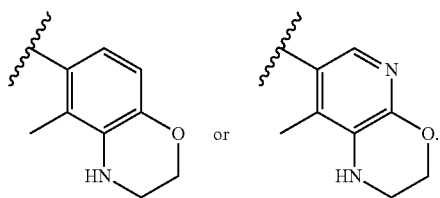

7. The method of claim 3, wherein $R_2$ is A-C(O)—.

8. The method of claim 7, wherein A is $(C_{3-7}$ cycloalkyl)$(C_{1-6}$ alkyl$)_j$-, $(C_{2-9}$ heterocyclyl$)(C_{1-6}$alkyl$)_j$-, $(C_{6-10}$ aryl$)_{q'}$-$(C_{1-6}$ alkyl$)_n$-O—, or $(C_{2-7}$ heterocyclyl$)$-O—, wherein said cycloalkyl, alkyl, aryl or heterocylyl can be optionally substituted; j is 1 or 0; and n is 1 or 0 and q' is 1 or 0, provided that one of n and q' is 1.

9. The method of claim 3, wherein $R_2$ is:

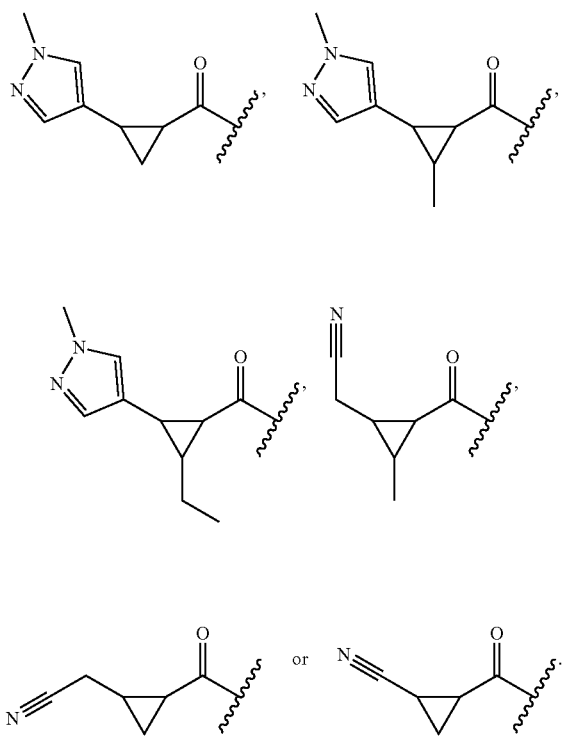

10. The method of claim 3, wherein $R_2$ is D.

11. The method of claim 10, wherein D is optionally substituted $(C_{3-9}$ heteroaryl$)(C_{1-6}$ alkyl$)_z$-, and z is 0 or 1.

12. The method of claim 10, wherein D is a 5-membered heteroaryl having the formula

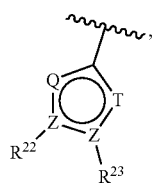

or a 6-membered heteroaryl having the formula

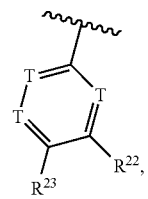

wherein:
Q is $NR^{20}$, $CR^{20}$, O or S;
each T is independently N or $CR^{21}$;
each Z is independently N or C, provided that only one Z is N;
each $R^{20}$ and $R^{21}$ is independently hydrogen, alkyl, haloalkyl, alkoxy, halogen, hydroxy, or cyano; and
$R^{22}$ and $R^{23}$ are taken together with the atoms to which they are attached to form a bicyclic; wherein the bicyclic may contain one more heteroatoms selected from N, S and O; and wherein the bicyclic is optionally substituted with one, two, three, four or five $R^{30}$;
wherein each $R^{30}$ is independently $C_{1-6}$ alkyl, $C_{2-6}$ alkenyl, $C_{3-7}$ cycloalkyl, $C_{3-7}$ heterocyclyl, halogen, cyano, oxo, $-NR^{31}R^{32}$, $-SO_2NR^{31}R^{32}$, $-C(O)NR^{31}R^{32}$, $-C(O)OR^{33}$, $-OR^{33}$, $-NR^{33}C(O)R^{34}$, $-NR^{33}SO_2R^{35}$ or $-SO_2R^{35}$; wherein the $C_{1-6}$ alkyl, $C_{2-6}$ alkenyl, $C_{3-7}$ cycloalkyl and $C_{3-7}$ heterocyclyl of $R^{30}$ are optionally substituted with one to four $R^{40}$; or two $R^{30}$ groups are taken together with the parent moiety to with they are attached to form a ring which is optionally substituted with one to four $R^{40}$;
each $R^{31}$ and $R^{32}$ is independently hydrogen or $C_{1-6}$ alkyl; or $R^{31}$ and $R^{32}$ are taken together with the nitrogen atom to which they are attached to form a $C_{3-7}$ heterocyclyl optionally substituted with one to four $R^{40}$;
each $R^{33}$ and $R^{34}$ are independently hydrogen or $C_{1-6}$ alkyl;
$R^{35}$ is $C_{1-6}$ alkyl,
each $R^{40}$ is independently halogen, cyano, oxo, $-NR^{41}R^{42}$, $-SO_2NR^{41}R^{42}$, $-C(O)NR^{43}R^{42}$, $-C(O)OR^{43}$, $-OR^{43}$, $-NR^{43}C(O)R^{44}$, $-NR^{43}SO_2R^{45}$, $-SO_2R^{45}$, $C_{1-6}$ alkyl, $C_{1-6}$ haloalkyl, $C_{2-9}$ heteroaryl, $C_{6-10}$ aryl, or oxo; or two $R^{40}$ groups are taken together with the parent moiety to with they are attached to form a ring which is optionally substituted with one to three substituents selected from $C_{1-6}$ alkyl, $C_{1-6}$ haloalkyl, hydroxyl and oxo,
each $R^{41}$ and $R^{42}$ is independently hydrogen or $C_{1-6}$ alkyl; or $R^{41}$ and $R^{42}$ are taken together with the nitrogen atom to which they are attached to form a $C_{3-7}$ heterocyclyl optionally substituted with one to three substituents selected from $C_{1-6}$ alkyl, $C_{1-6}$ haloalkyl, hydroxyl and oxo;
each $R^{43}$ and $R^{44}$ are independently hydrogen or $C_{1-6}$ alkyl; and
$R^{45}$ is $C_{1-6}$ alkyl.

13. The method of claim 3, wherein $R^{1'}$ is hydrogen.

14. The method of claim 3, wherein $R^{2'}$ is hydrogen.

15. The method of claim 3, wherein the compound is selected from the group consisting of Compound Nos. 1-348 in Table 1, having the structures:

1273
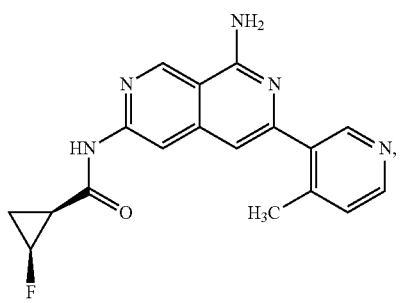
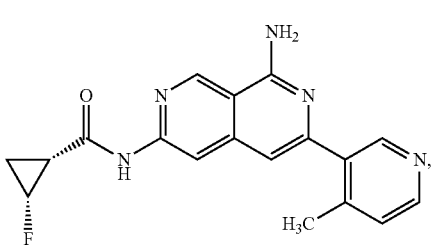
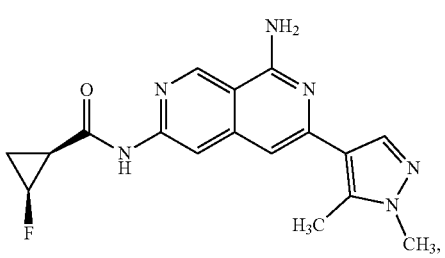
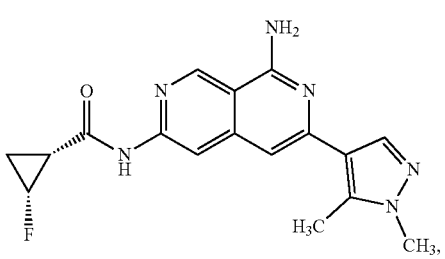
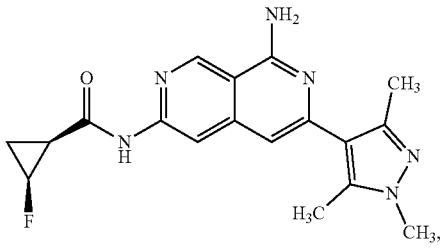
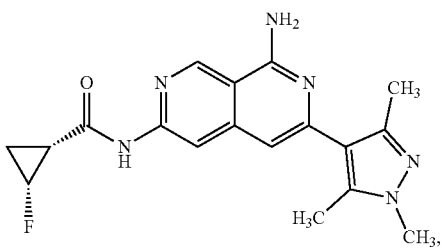
1274
-continued
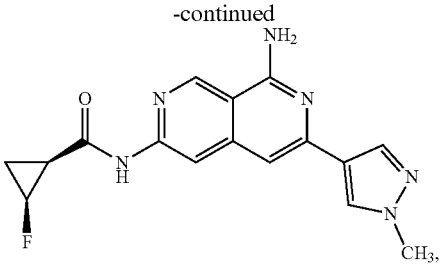
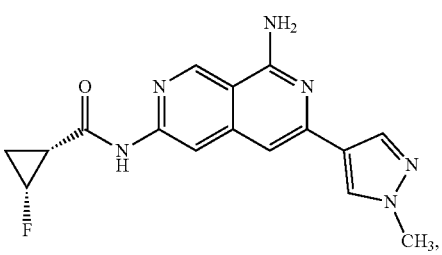
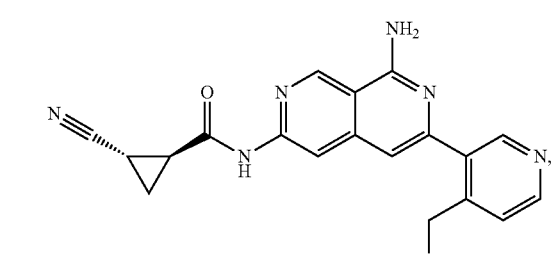
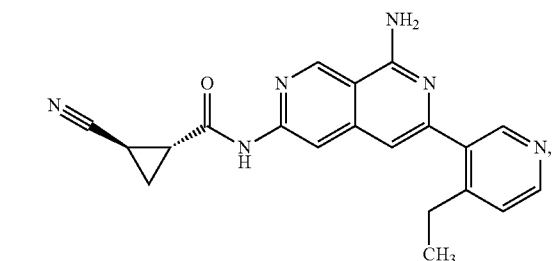
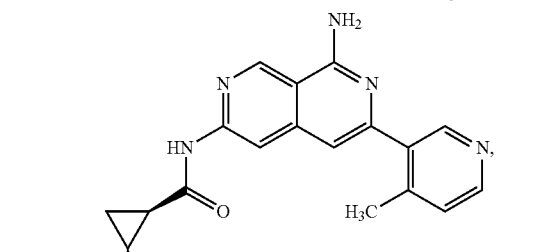
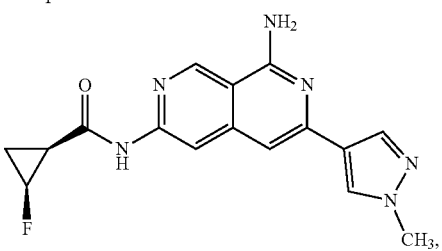

1275
-continued
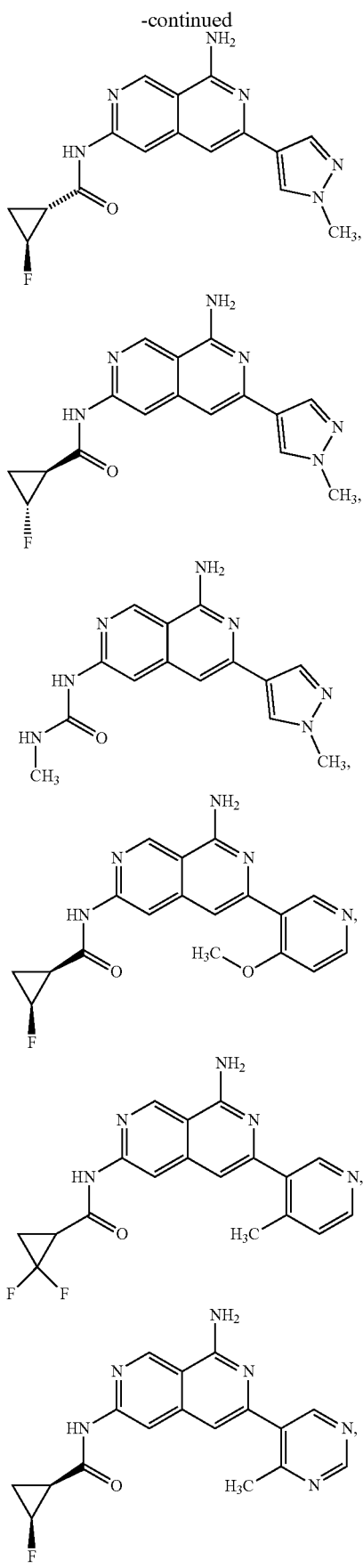
1276
-continued
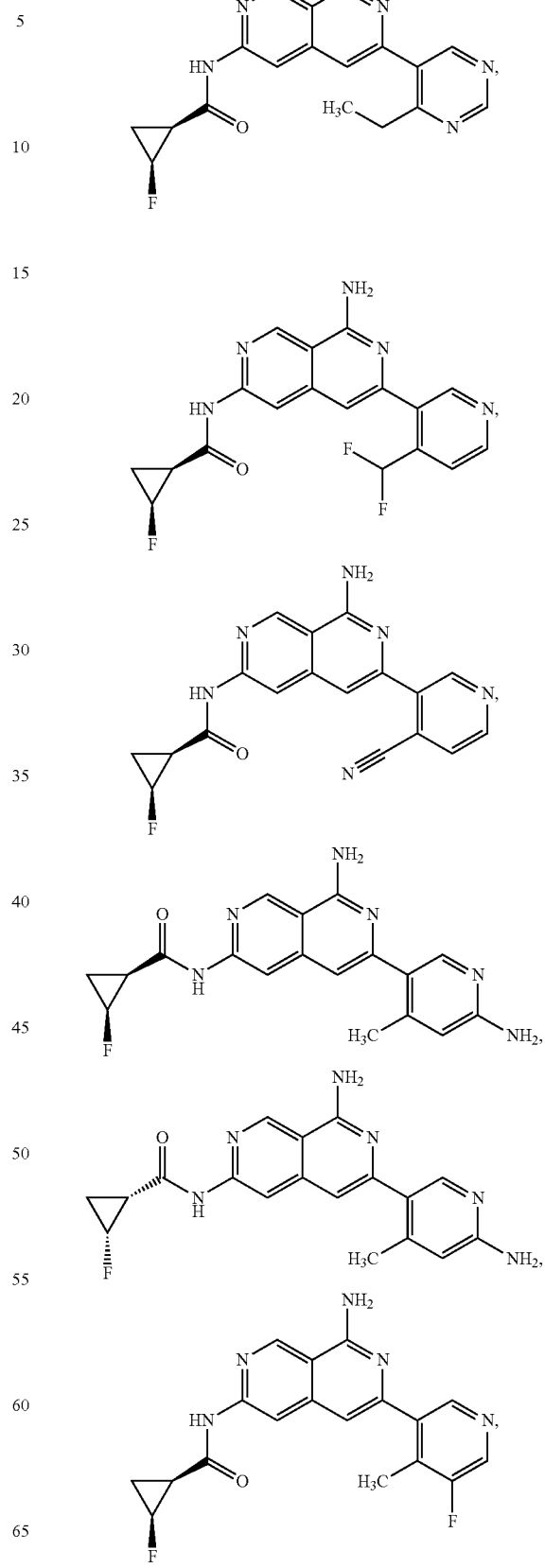

1277
-continued
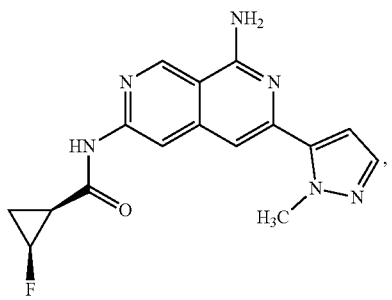
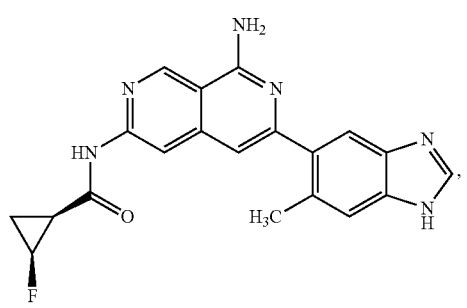
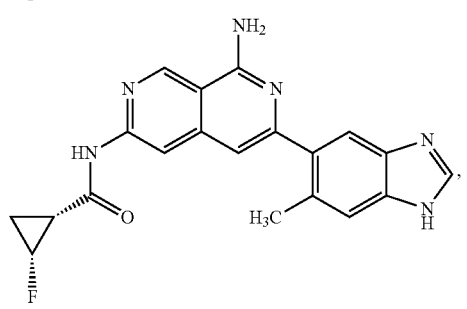
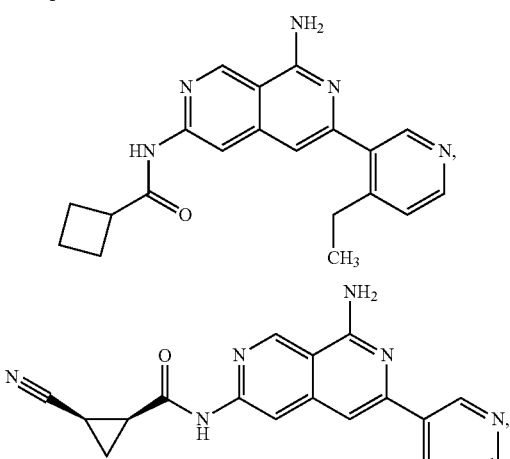
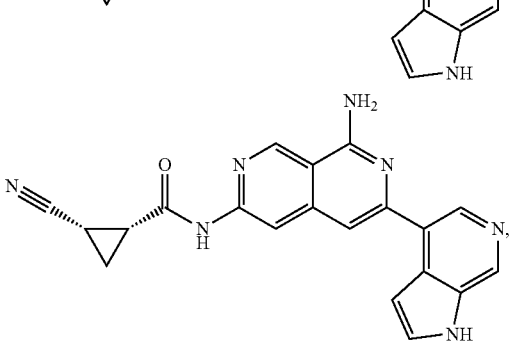
1278
-continued
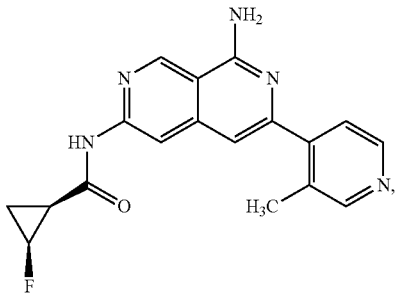
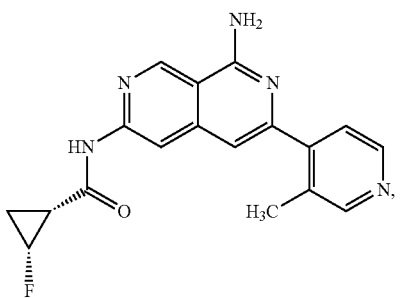
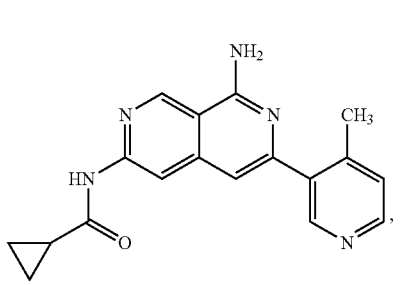
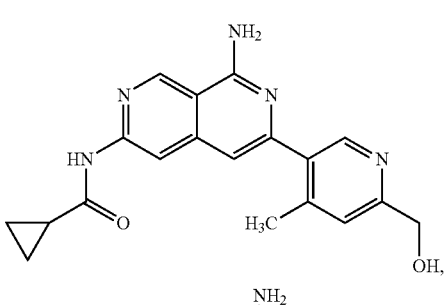
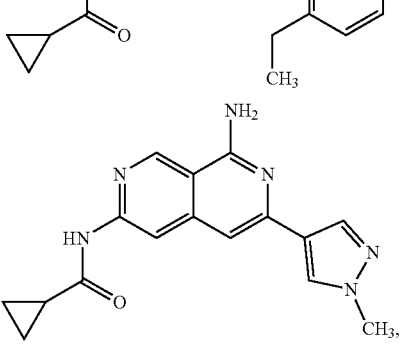

1279
-continued

1280
-continued

1281
-continued
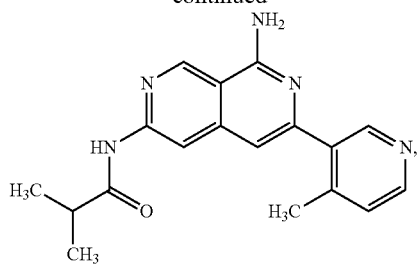
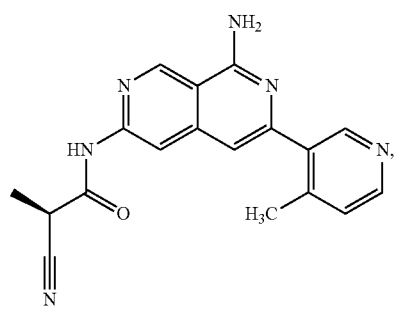
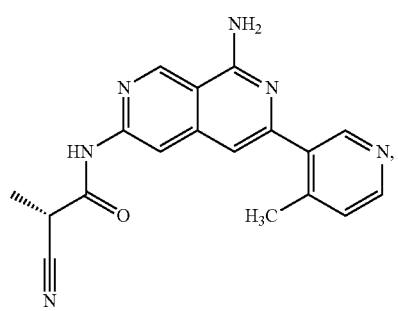
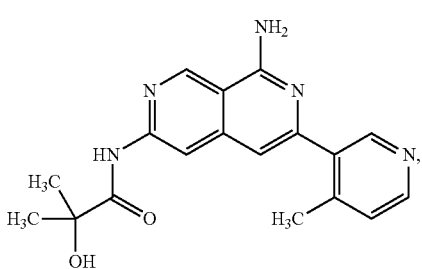
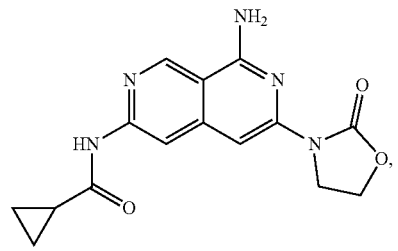
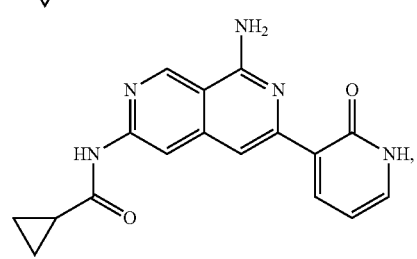
1282
-continued
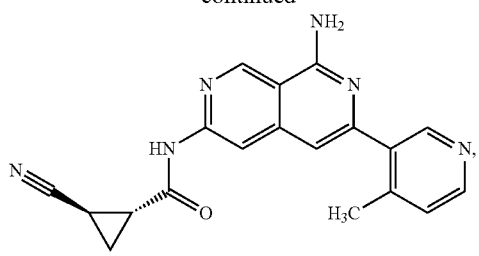
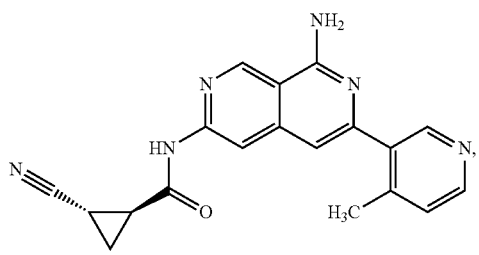
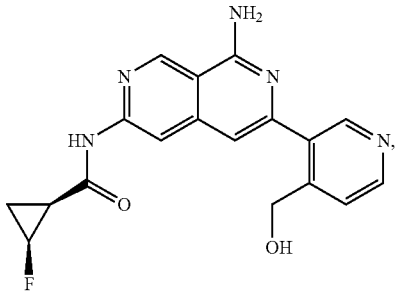
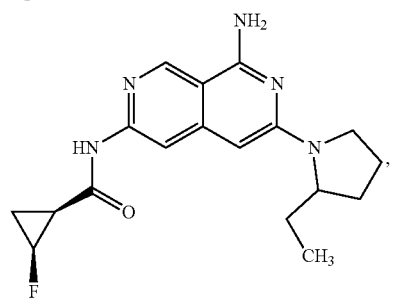
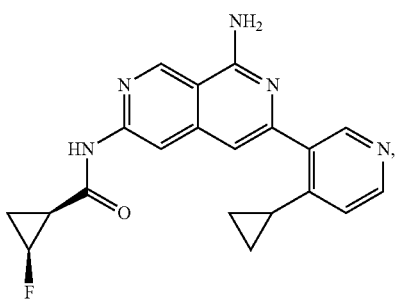
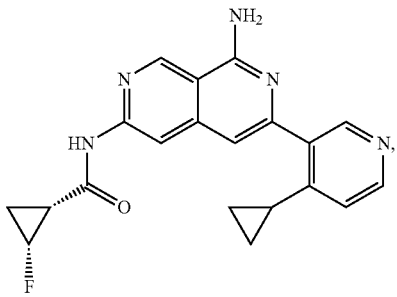

1283
-continued
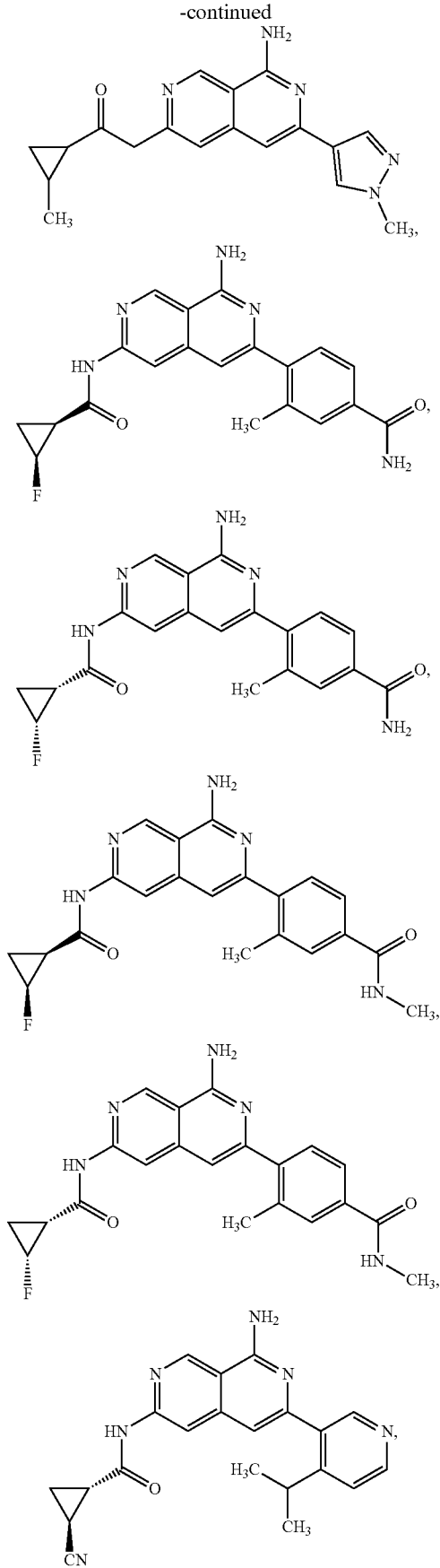
1284
-continued
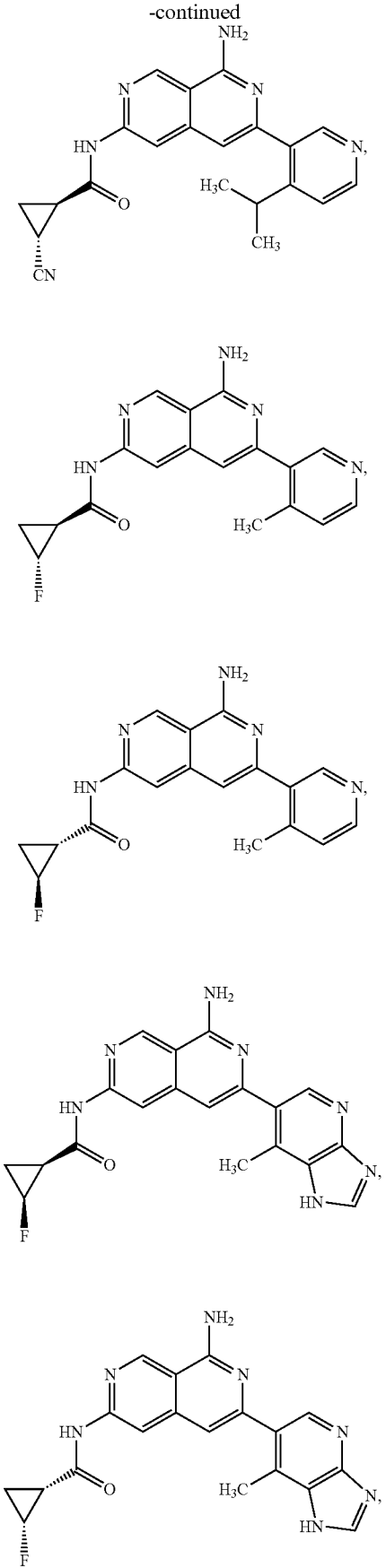

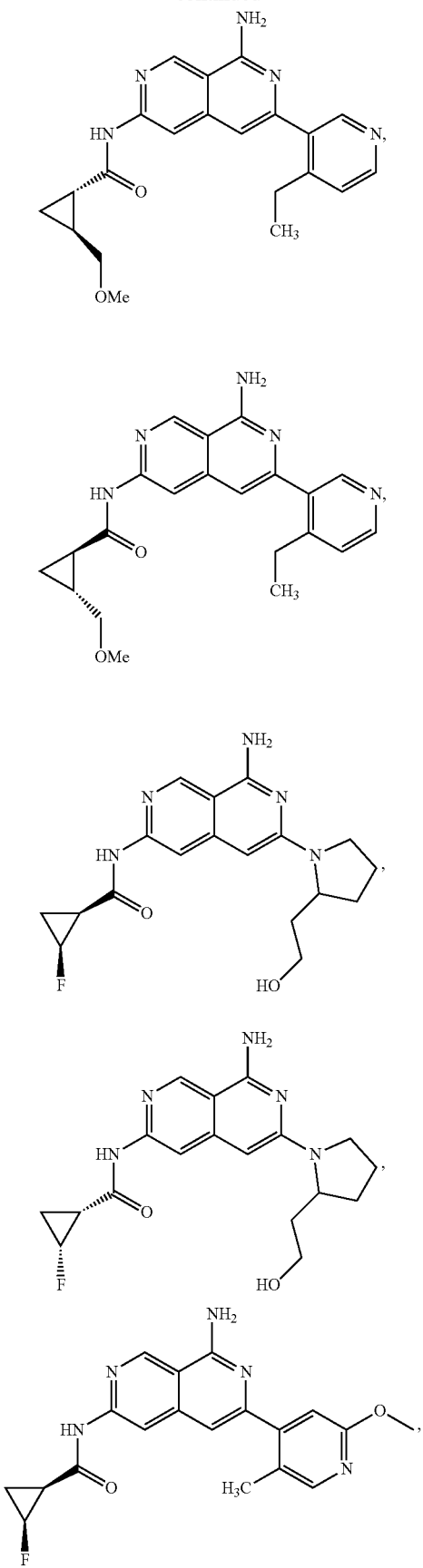
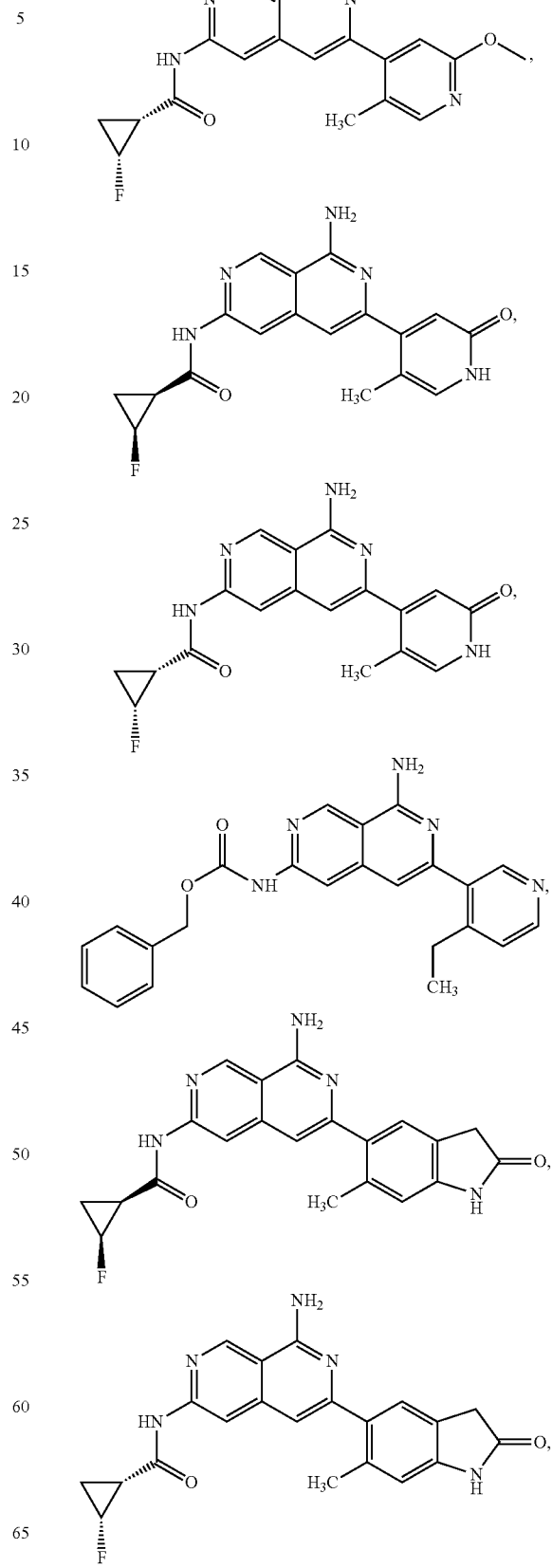

1287
-continued
1288
-continued
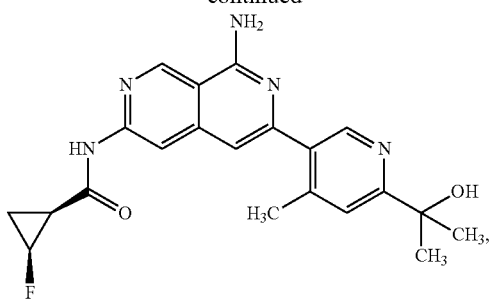
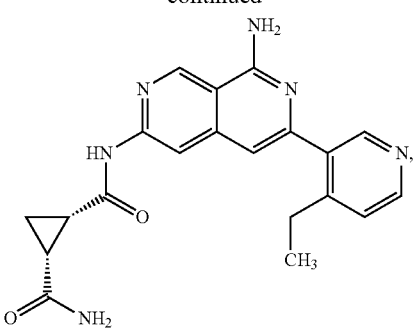

1289
-continued
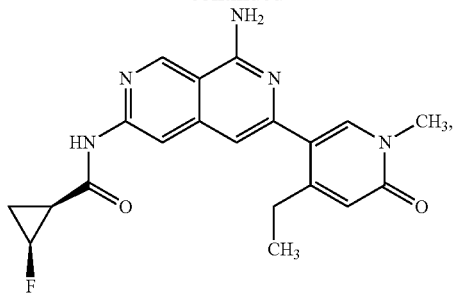
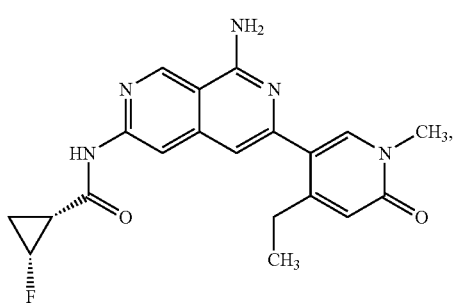
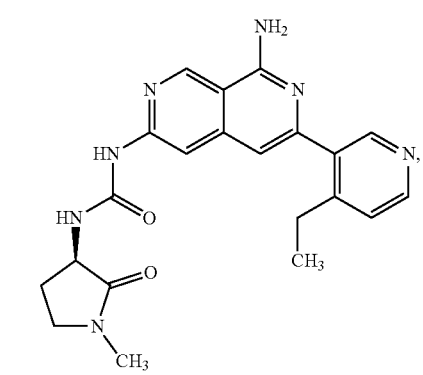
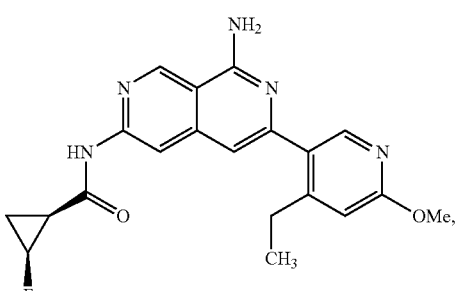
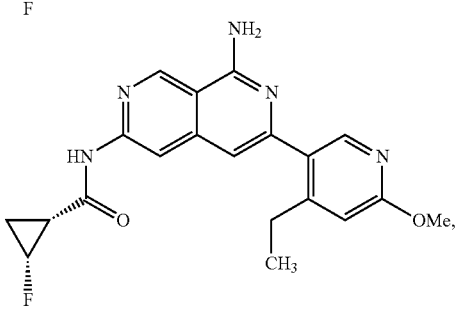
1290
-continued
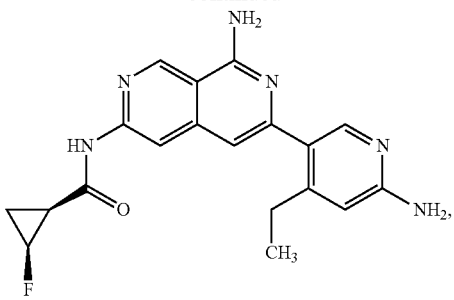
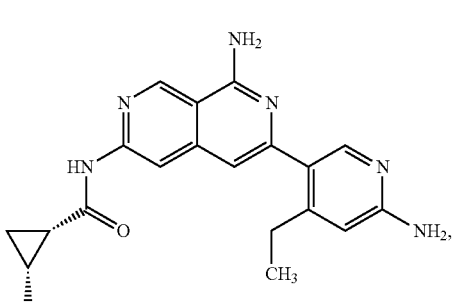
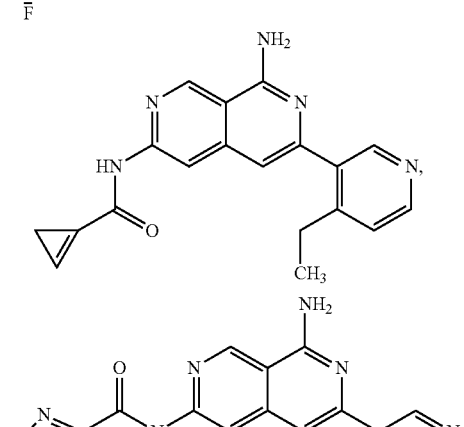
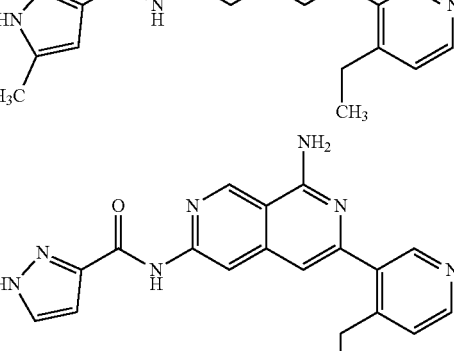
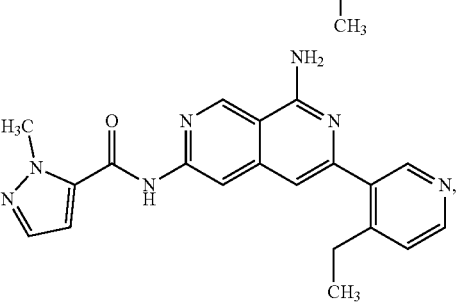

-continued
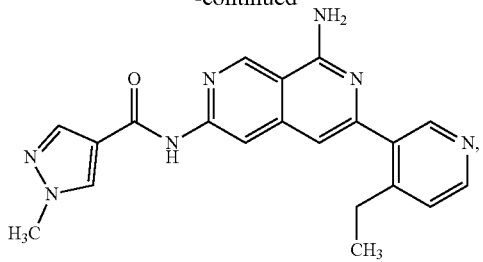
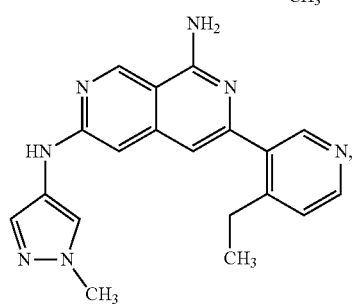
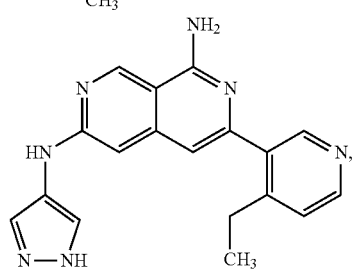
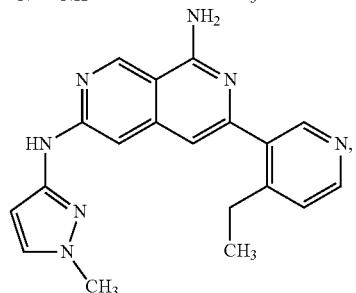
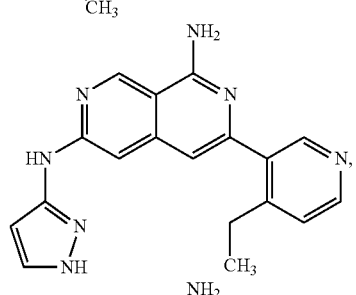
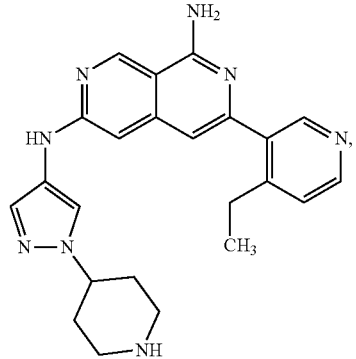
-continued
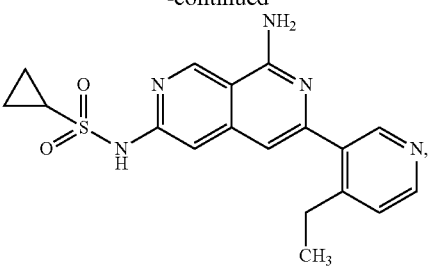
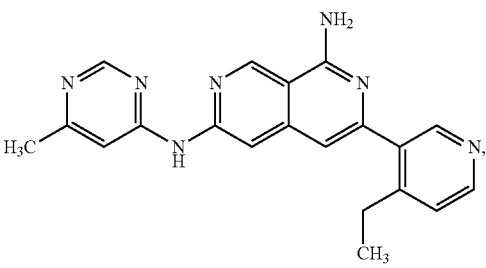
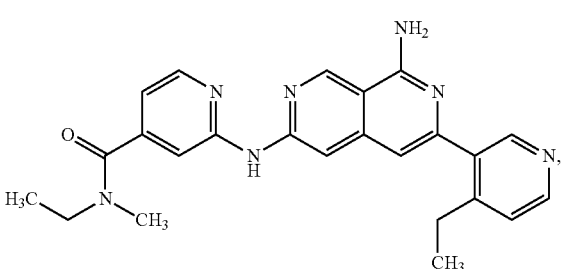
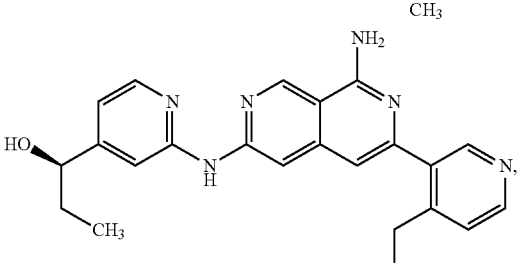
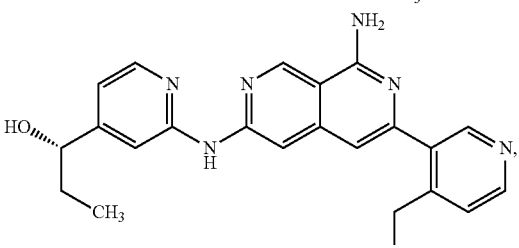
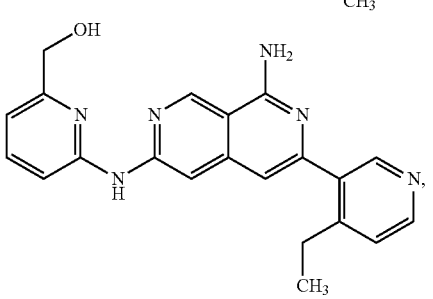

1293
1294

1295
-continued
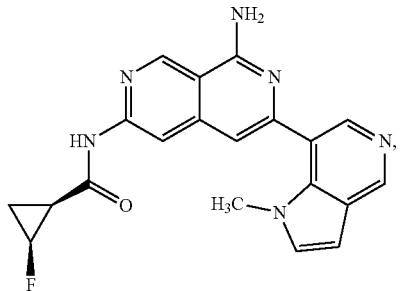
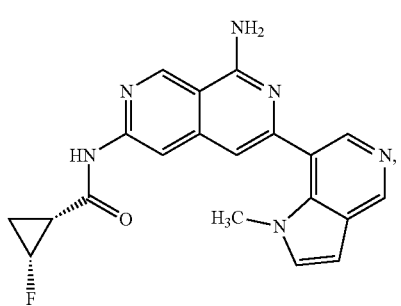
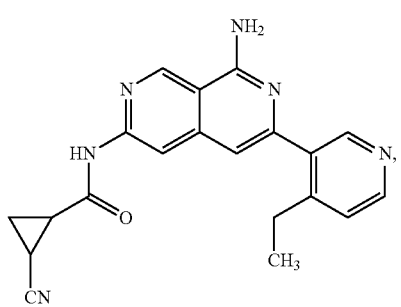
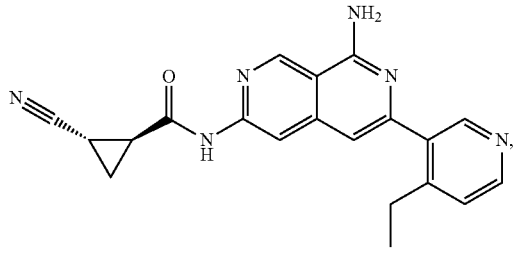
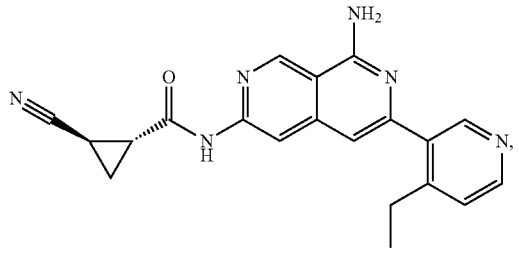
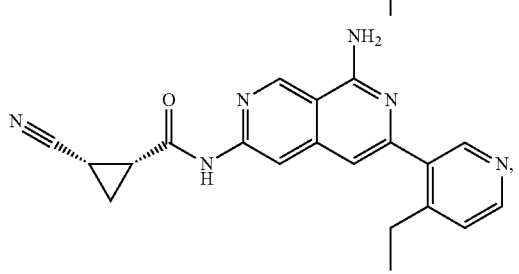
1296
-continued
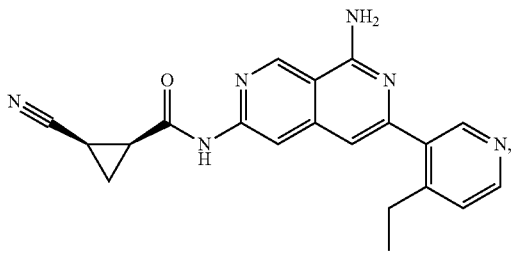
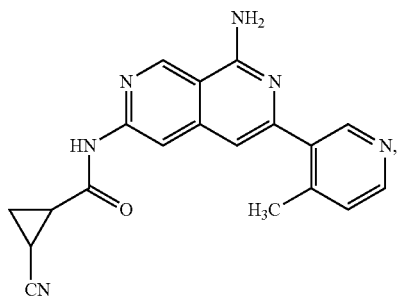
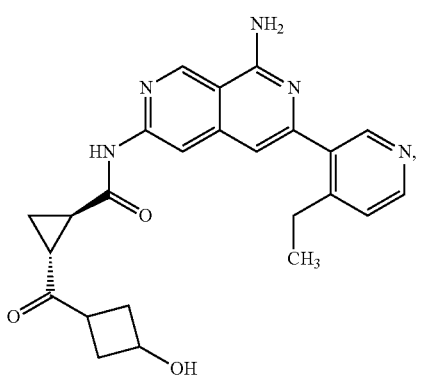
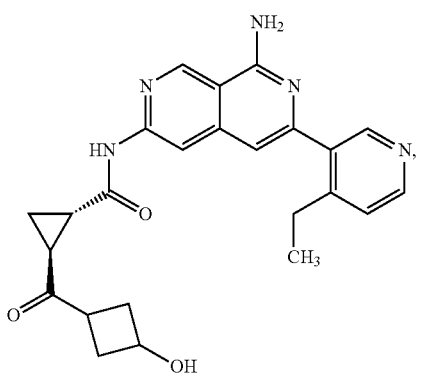
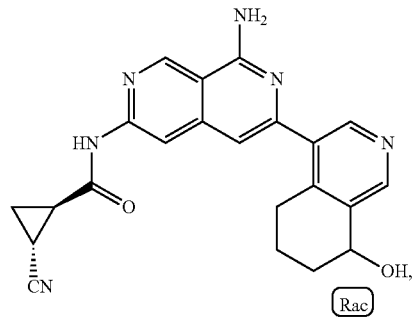

1297
-continued
1298
-continued
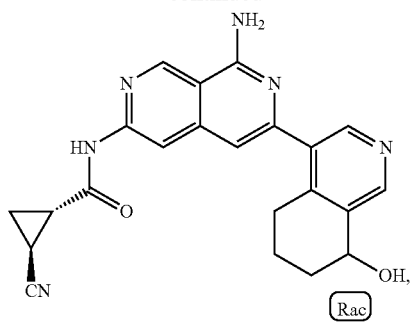
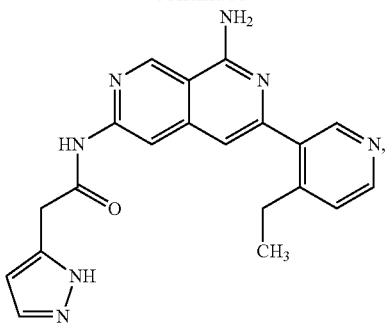

| 1299 | 1300 |
|---|---|
| -continued | -continued |
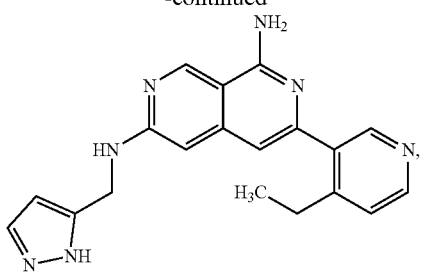
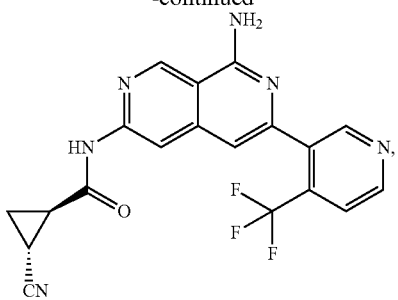
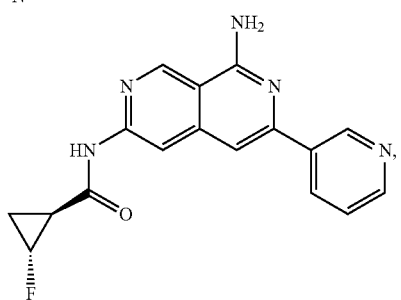
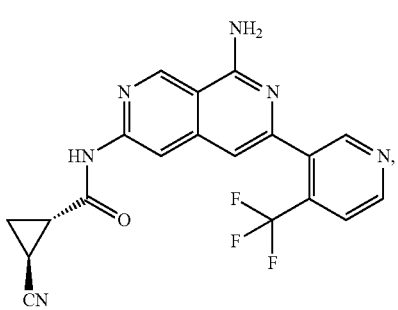
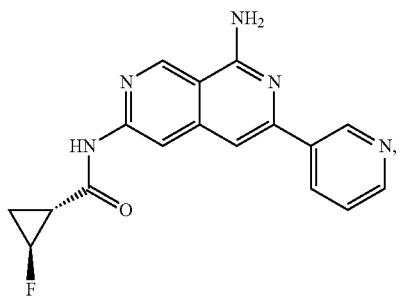
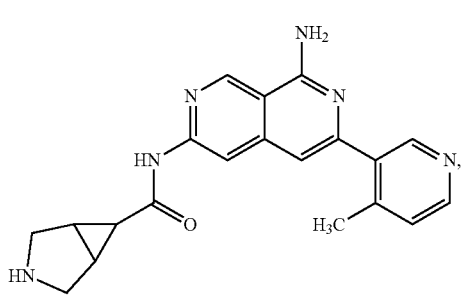
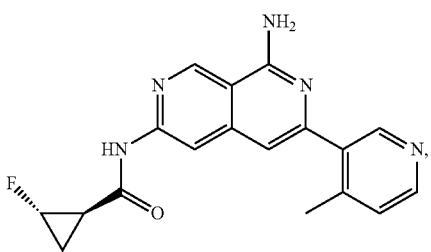
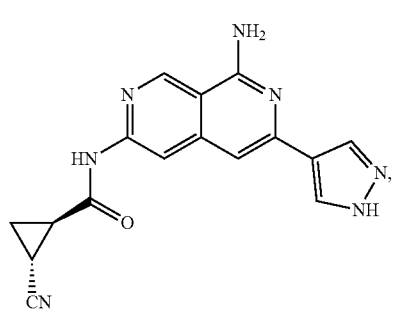
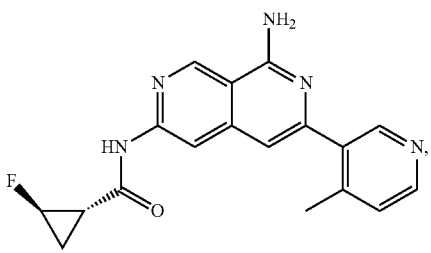
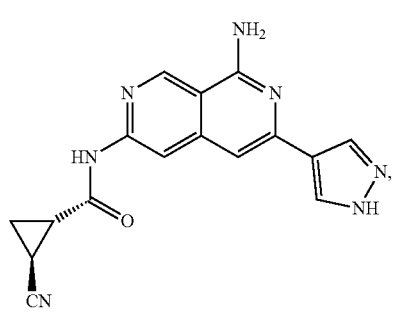
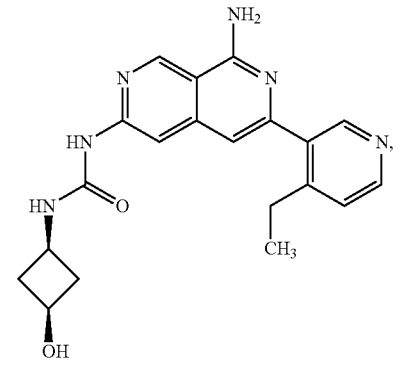

| 1301 | 1302 |
|---|---|
| -continued | -continued |
| 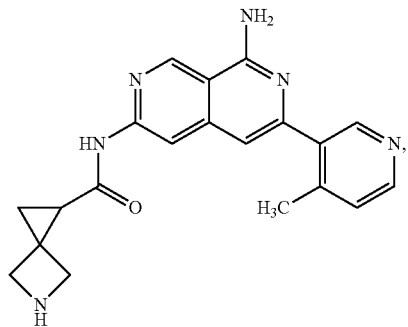 | 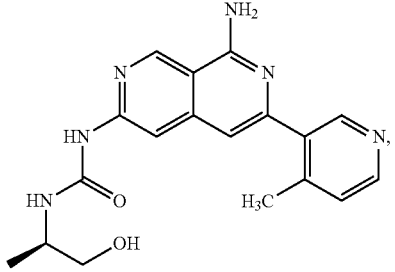 |
| 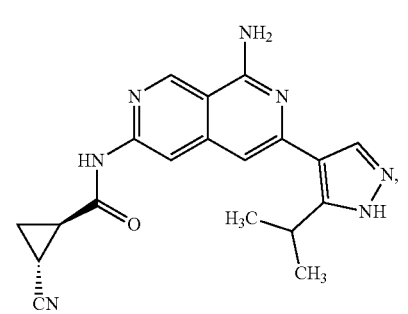 | 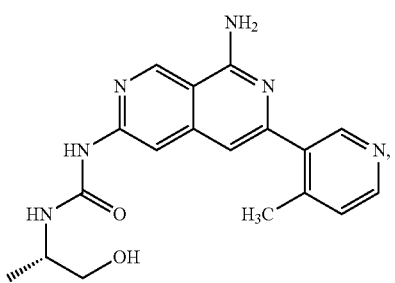 |
| 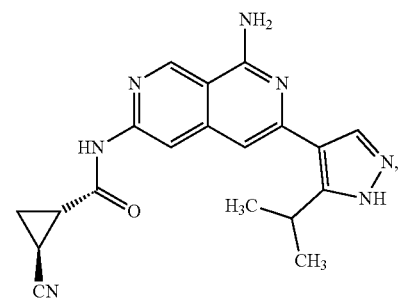 | 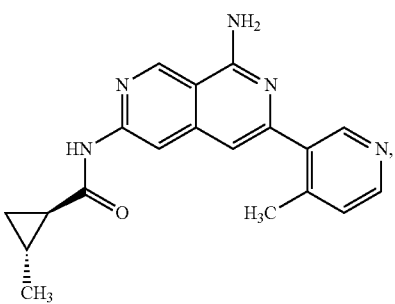 |
| 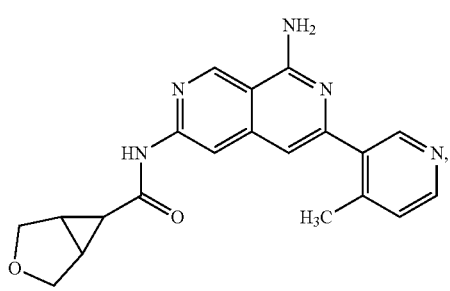 | 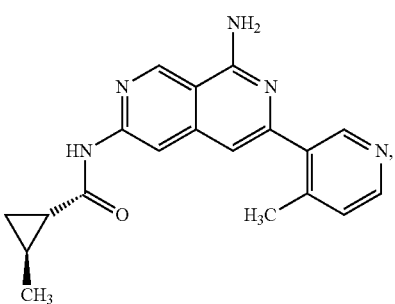 |
| 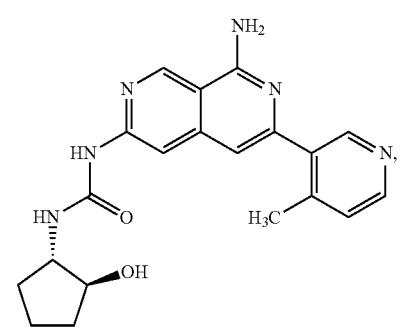 | 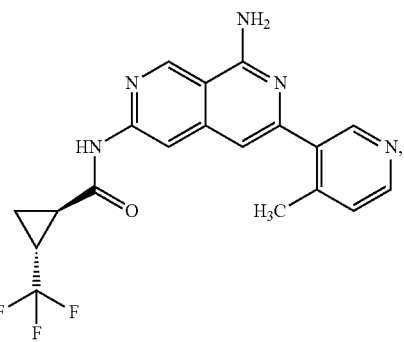 |

1303
-continued
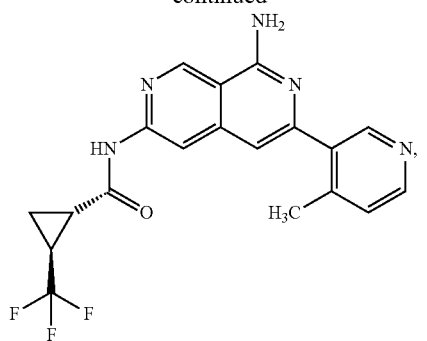
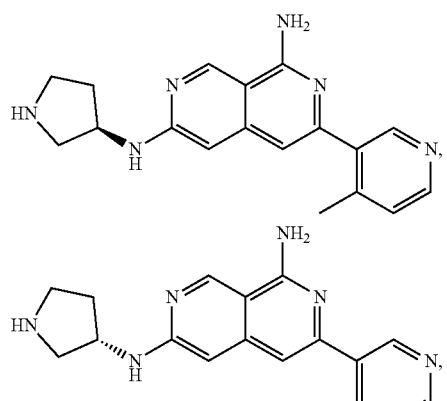
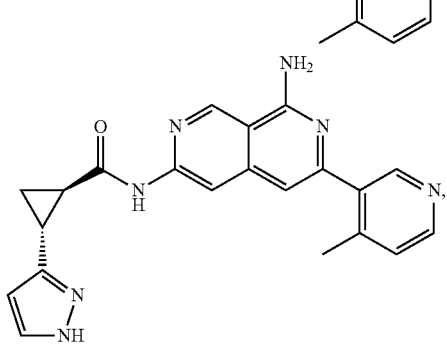
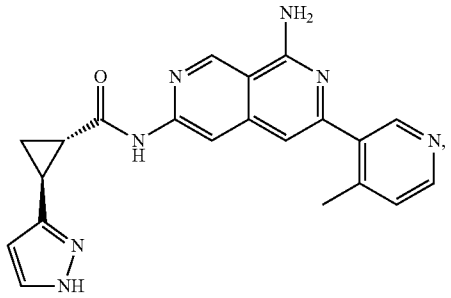
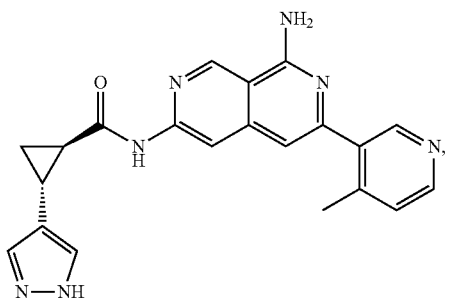
1304
-continued
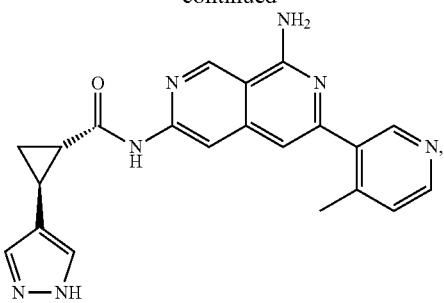
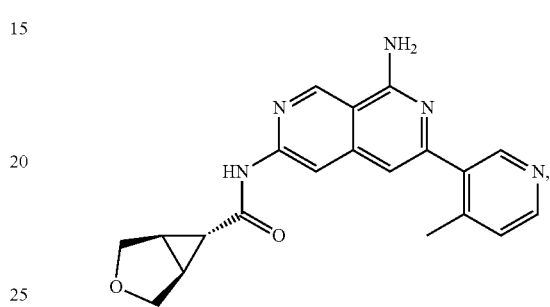
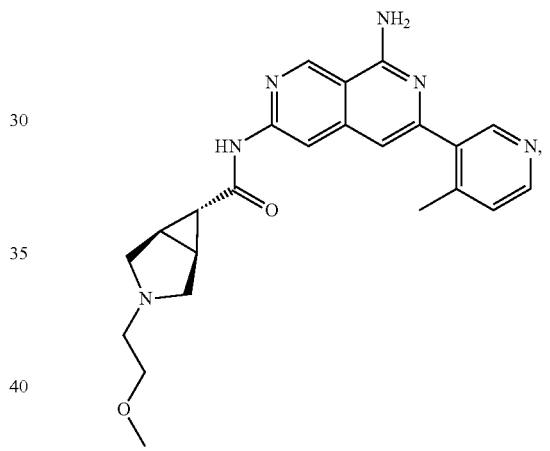
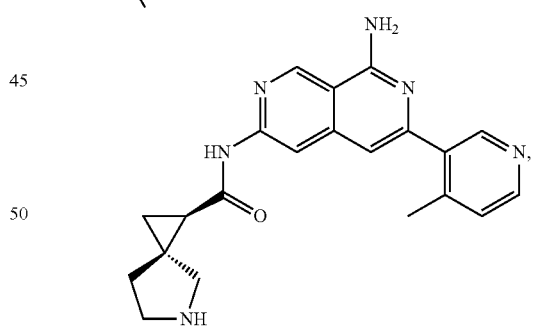
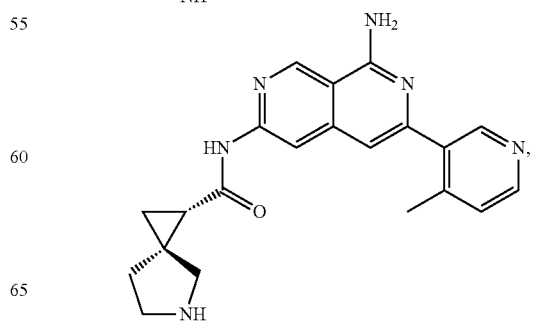

-continued
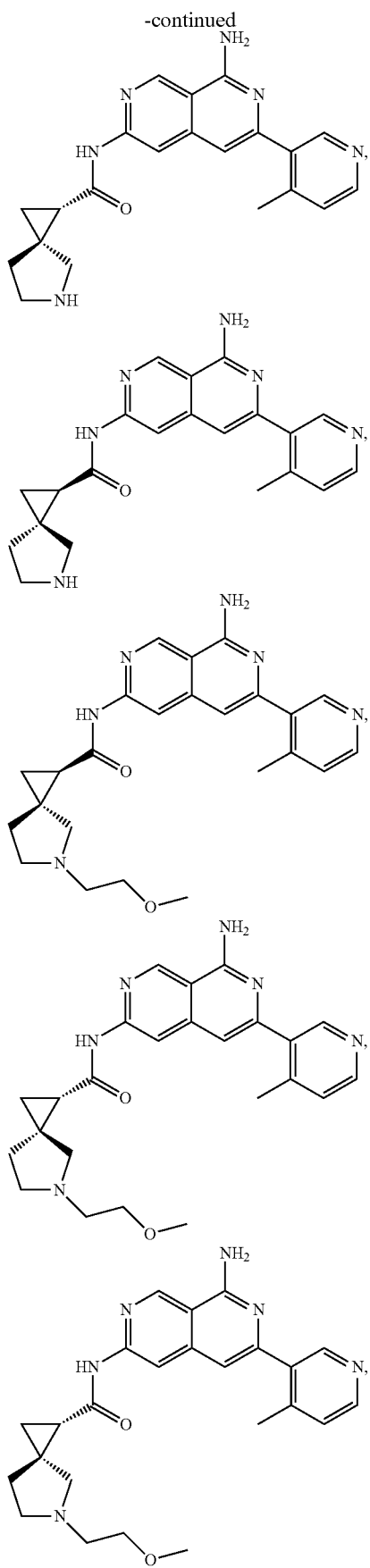
-continued
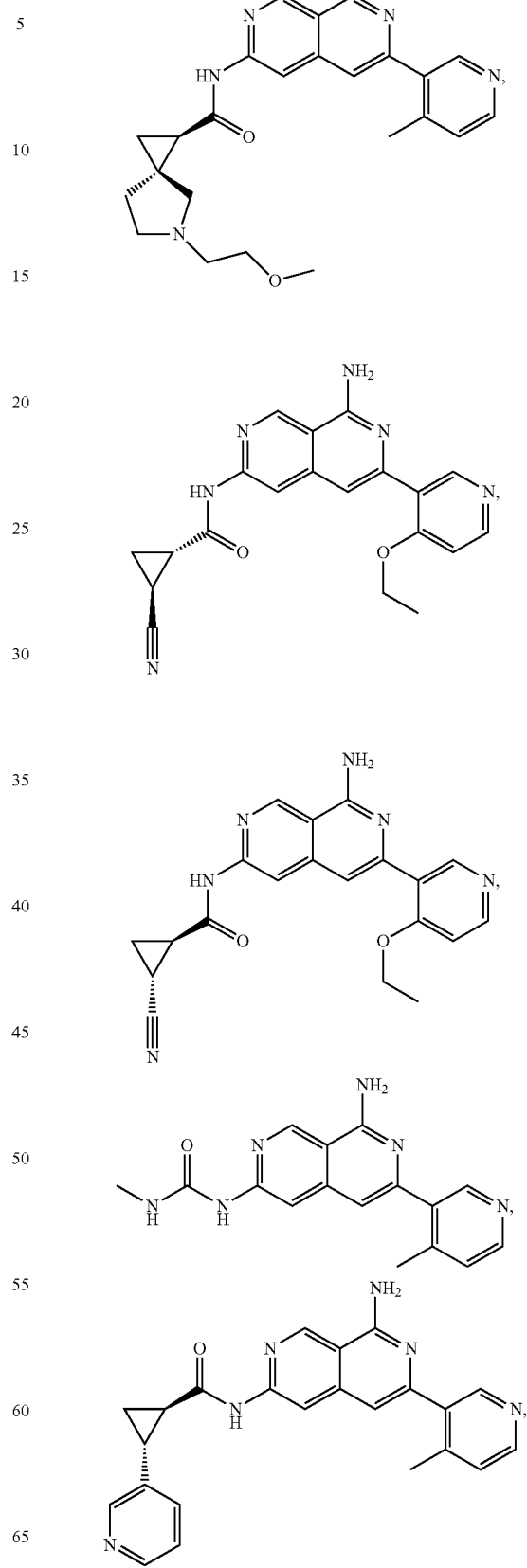

1307
-continued
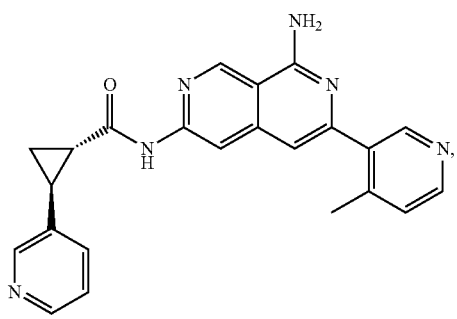
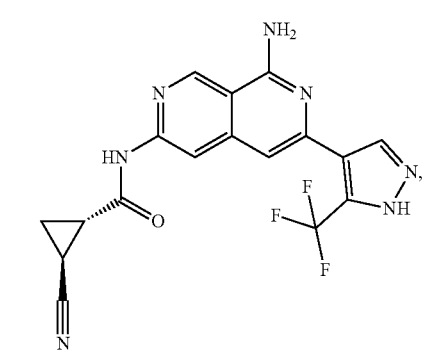
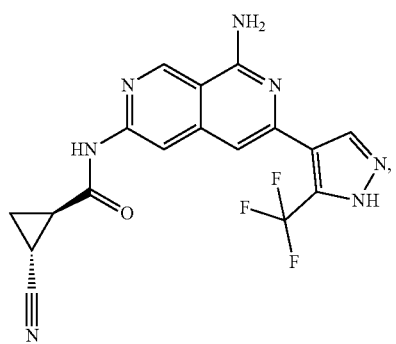
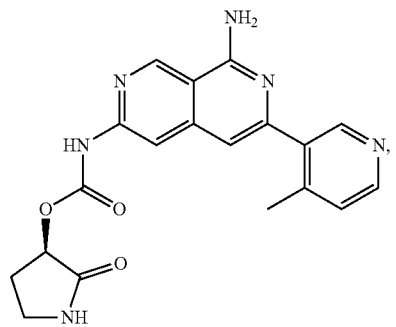
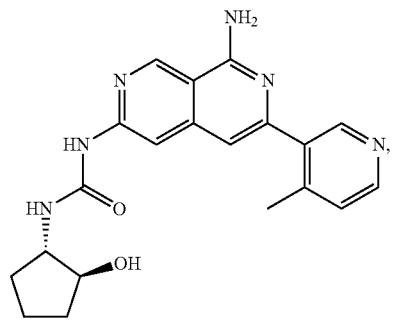
1308
-continued
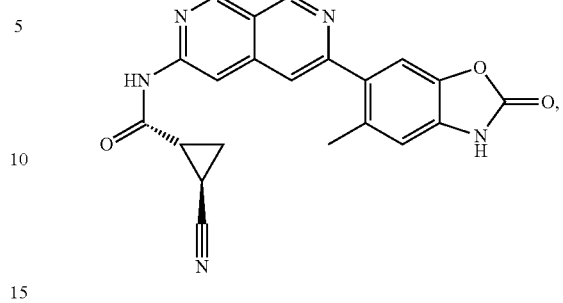
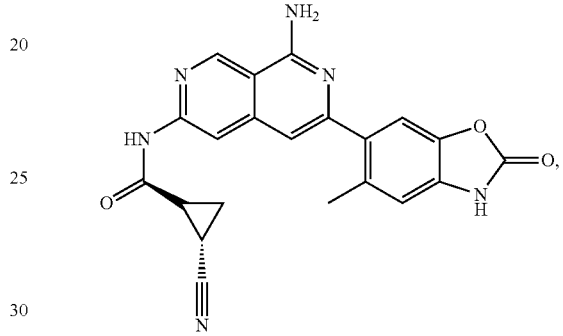
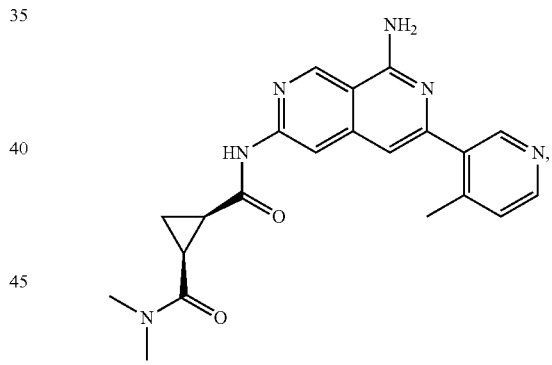
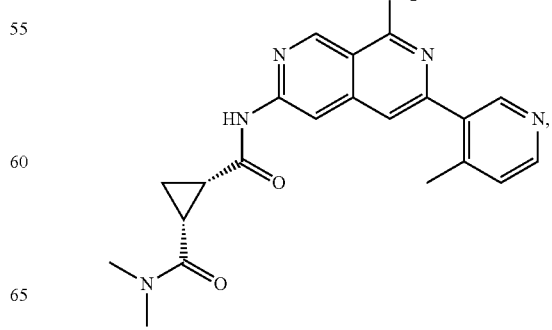

1309
-continued
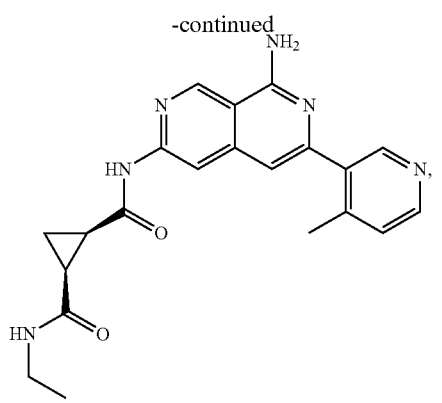
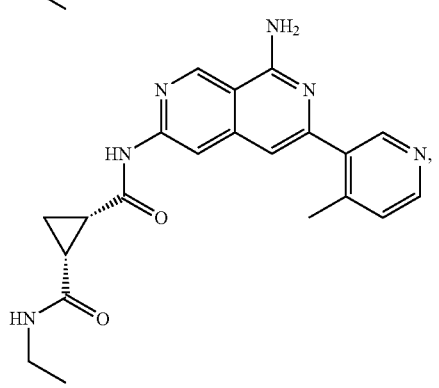
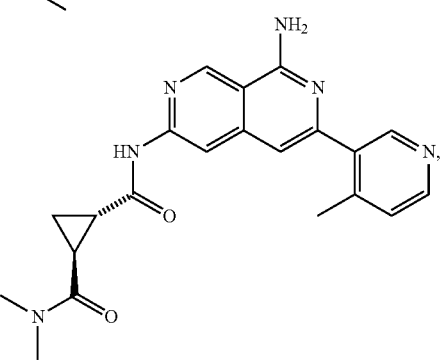
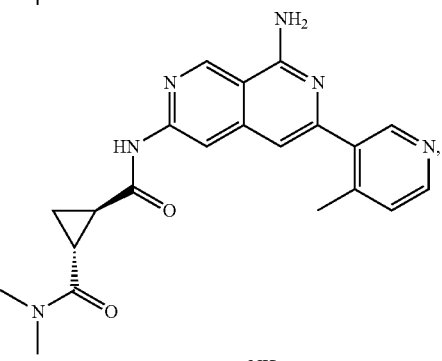
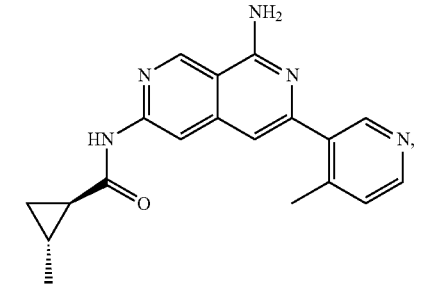
1310
-continued
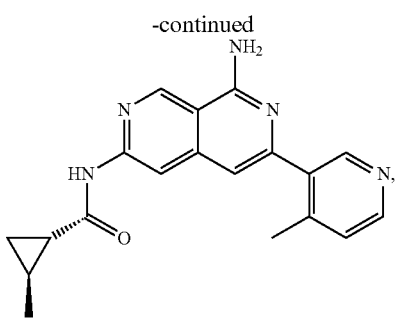
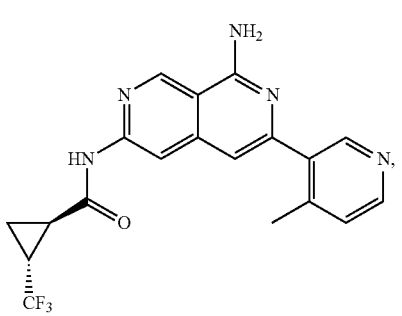
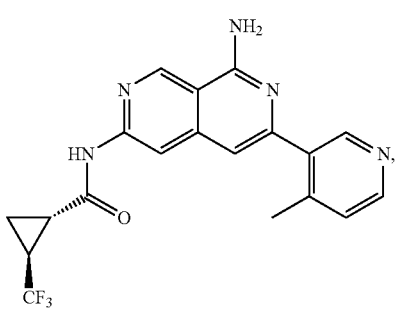
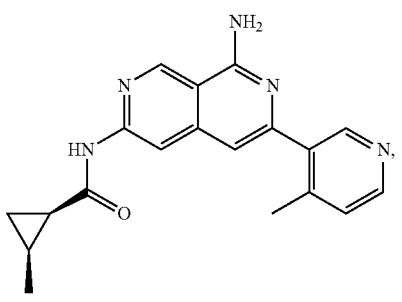
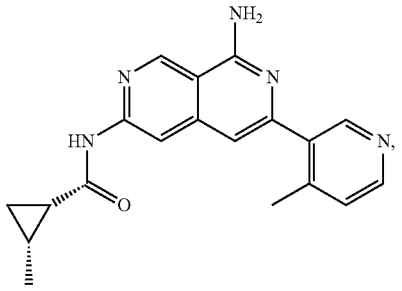

1311
-continued
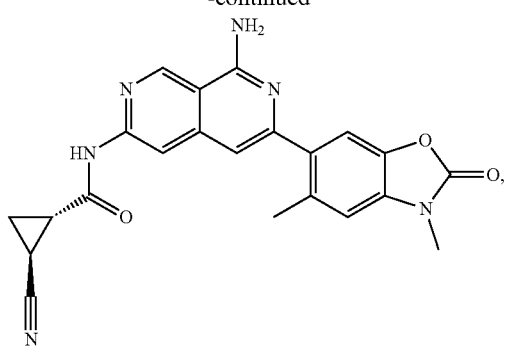
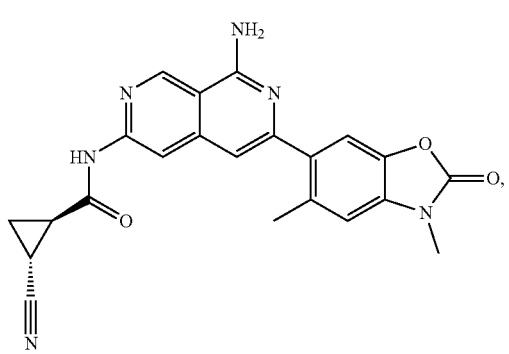
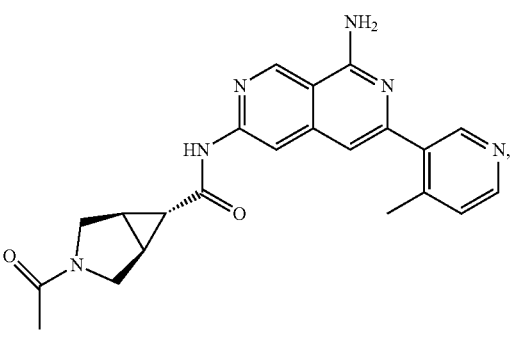
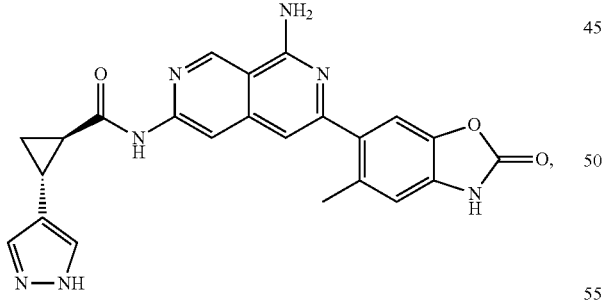
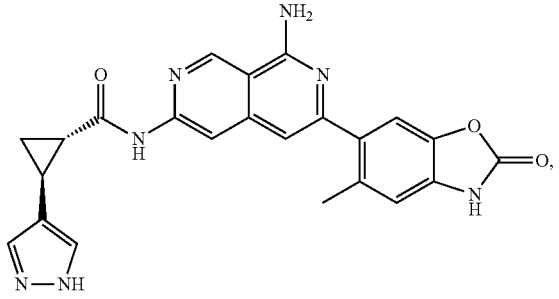
1312
-continued
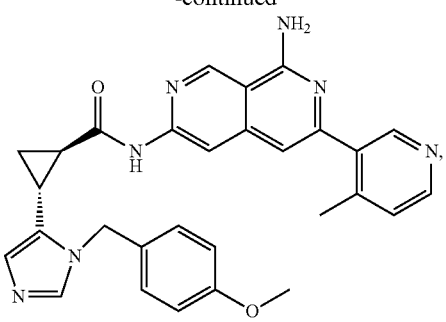
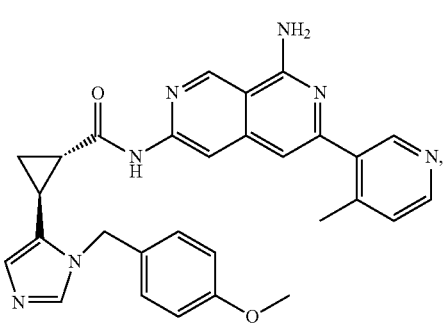
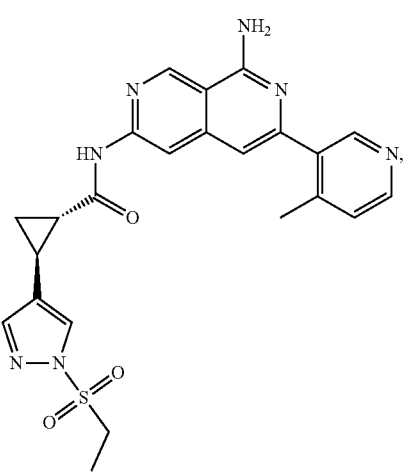
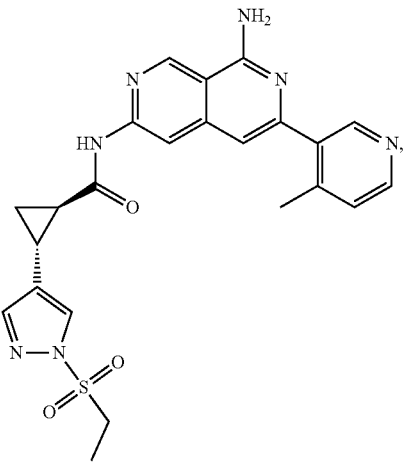

1313
-continued
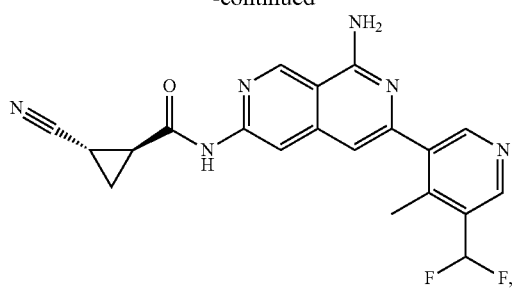
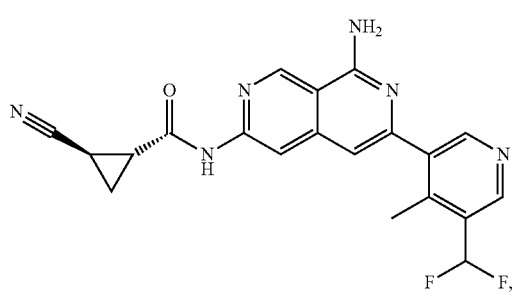
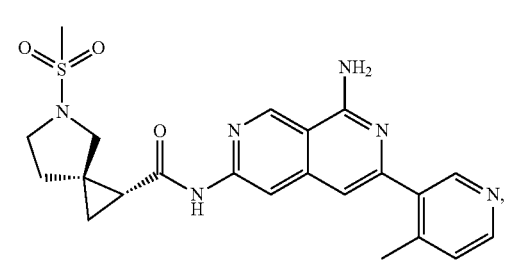
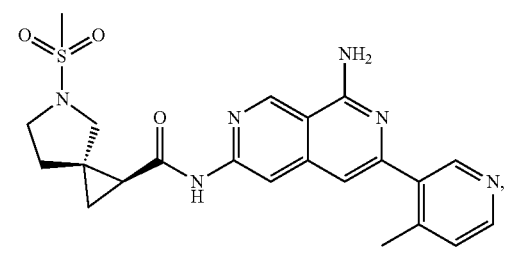
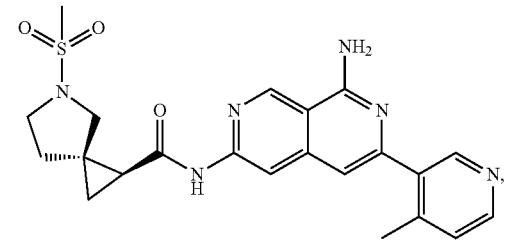
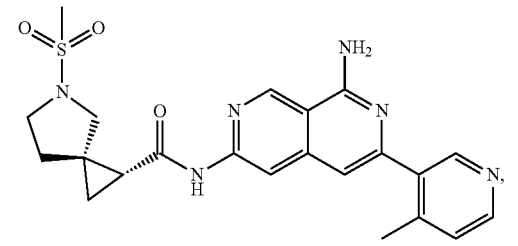
1314
-continued
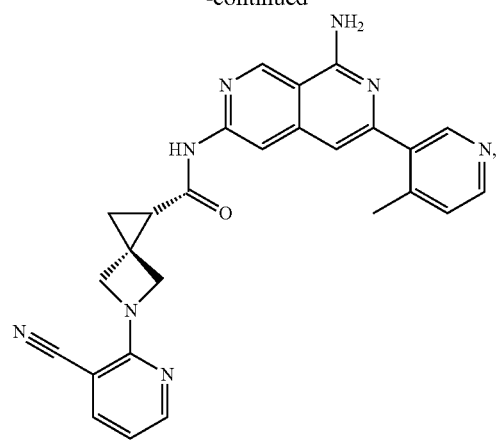
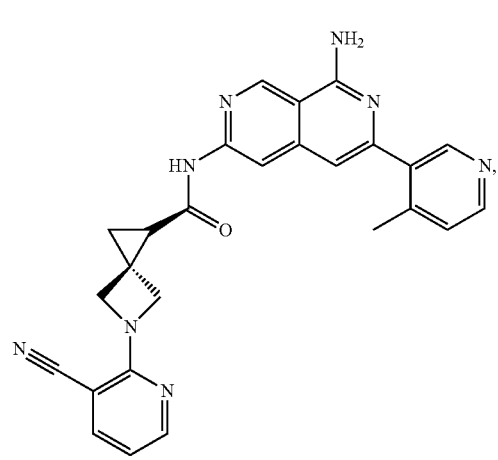
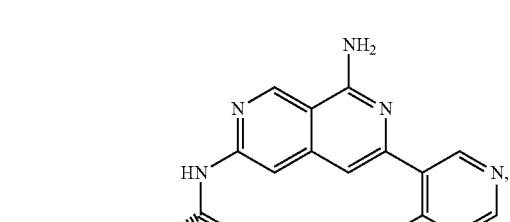
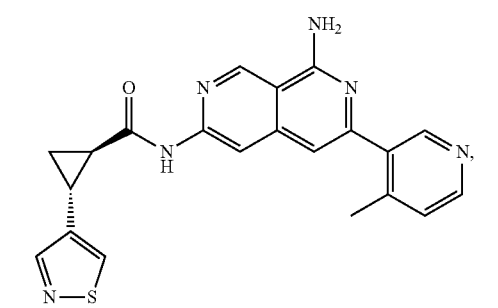

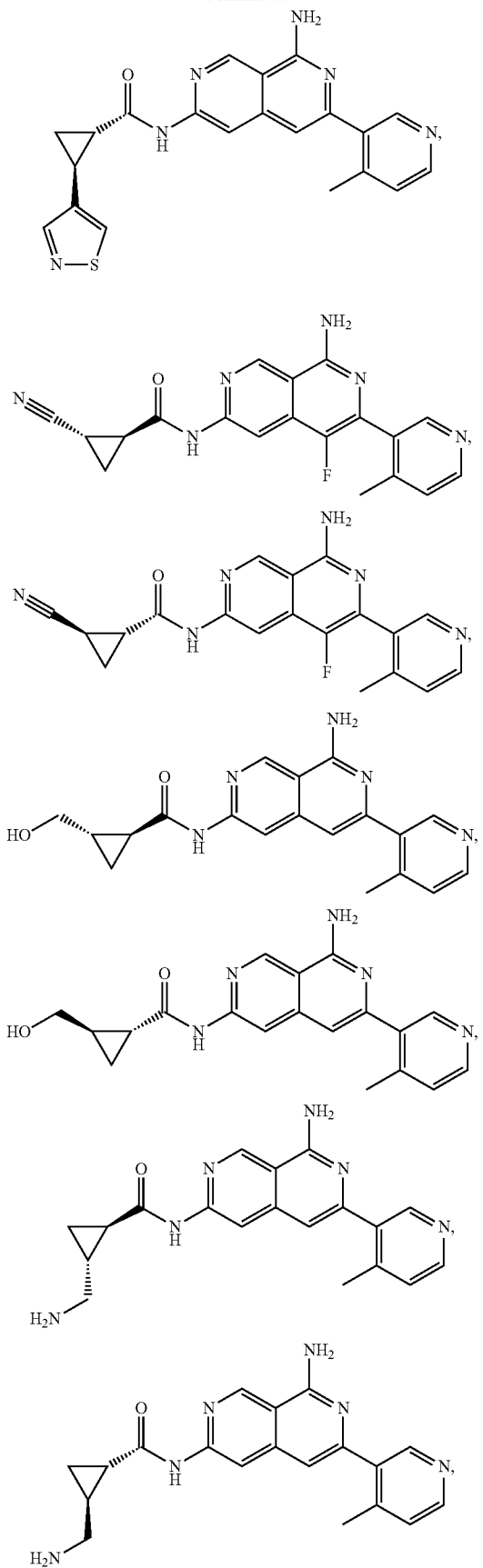
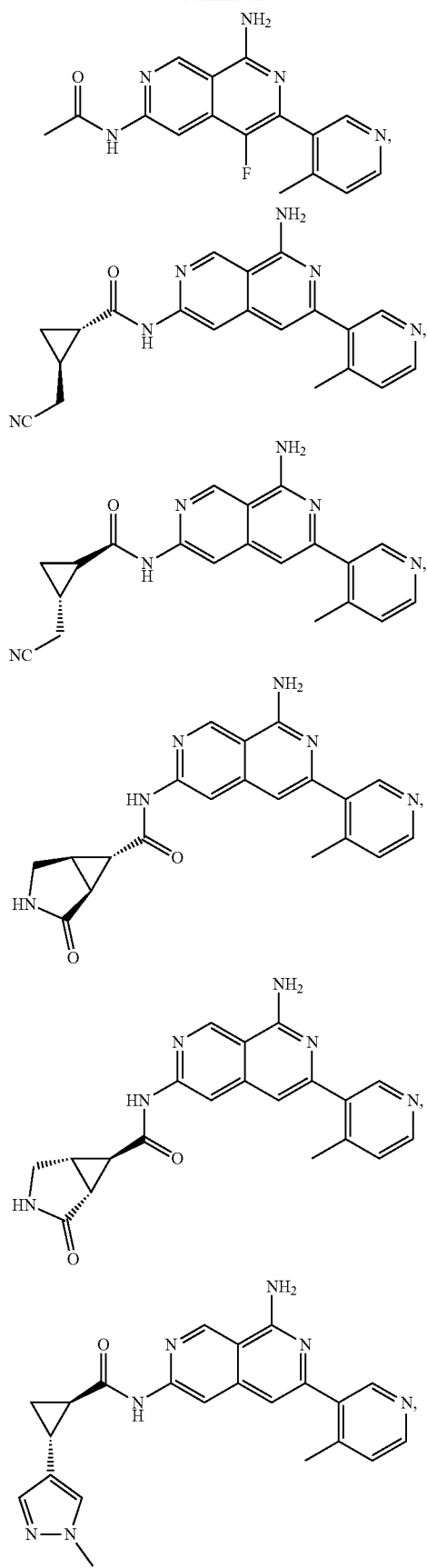

1317
-continued
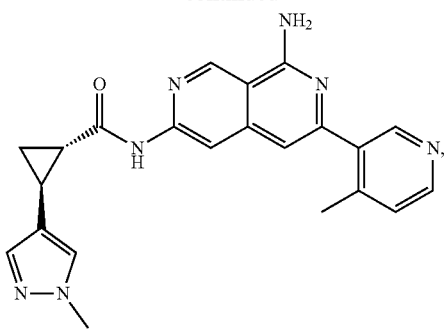
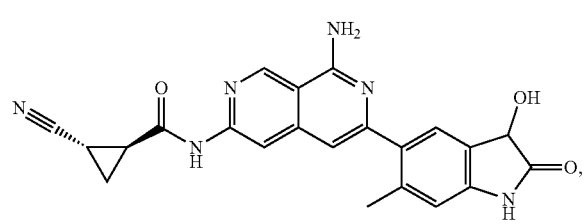
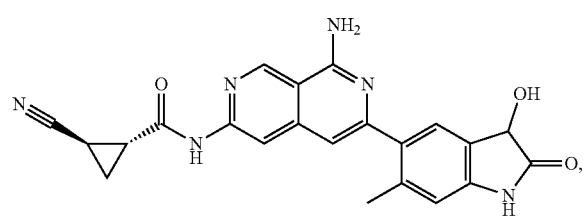
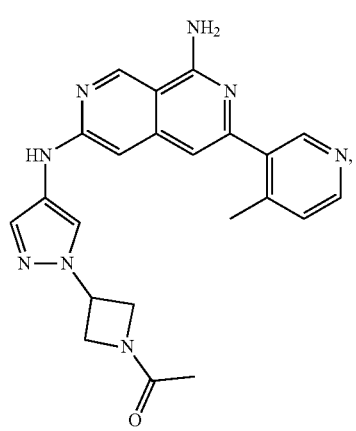
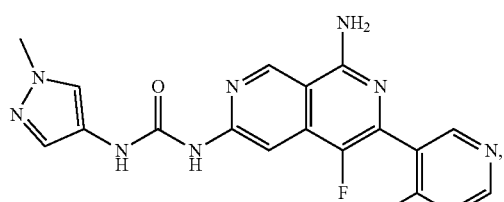
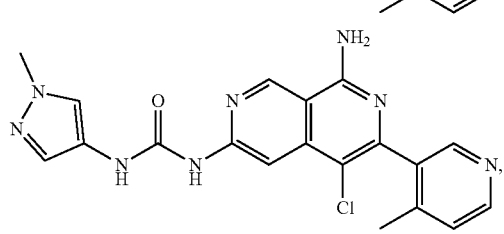
1318
-continued
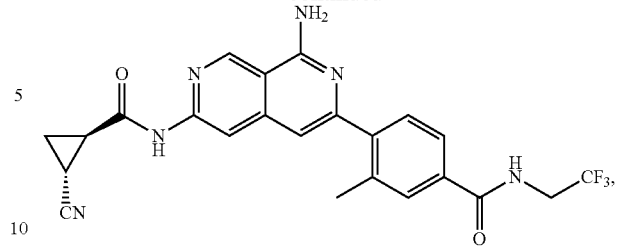
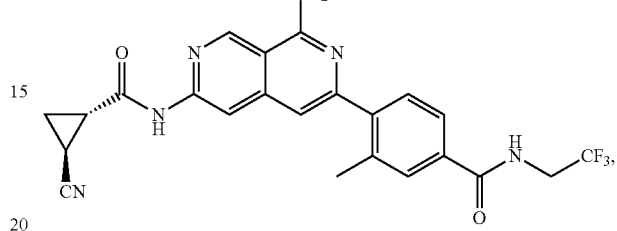
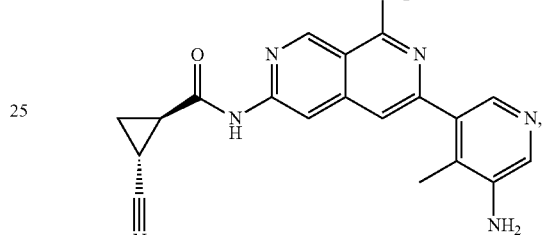
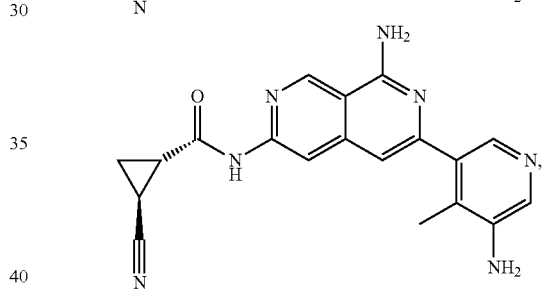
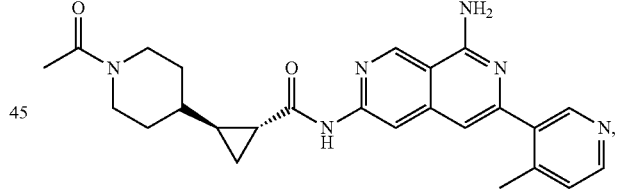
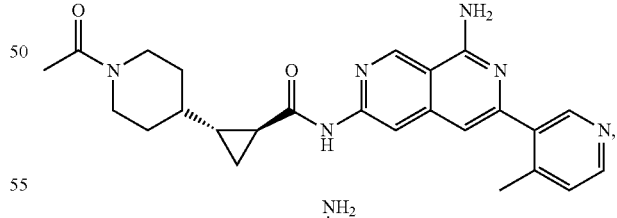
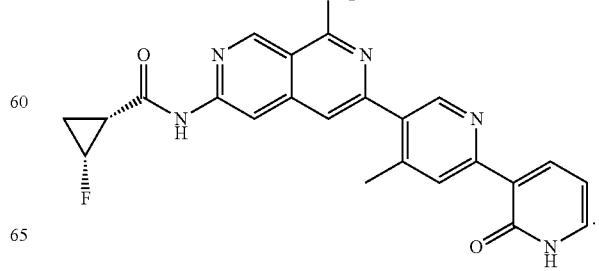

1319
-continued
1320
-continued
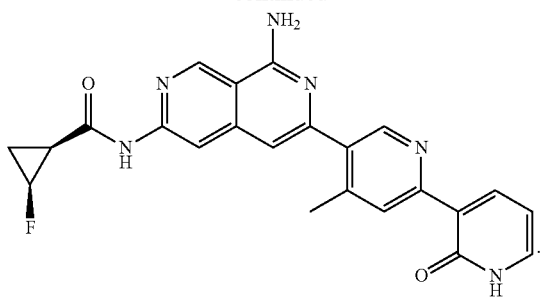
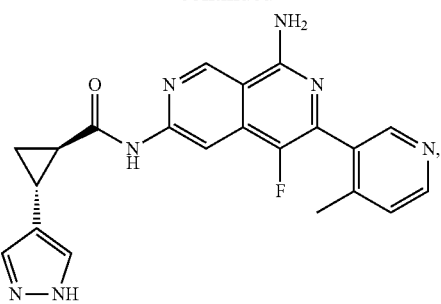

1321
-continued
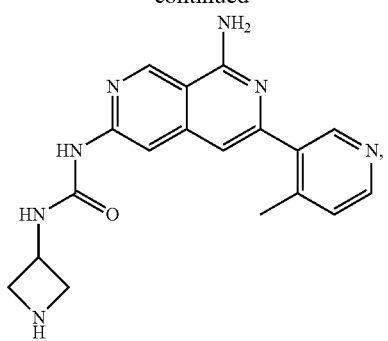
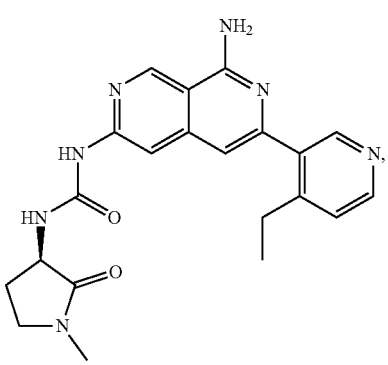
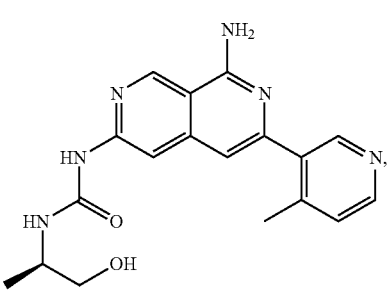
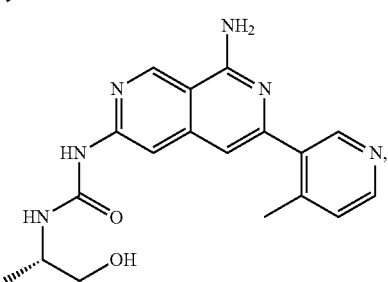
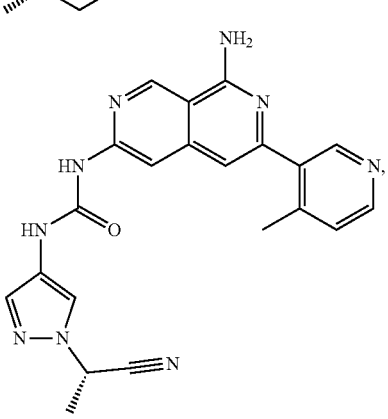
1322
-continued
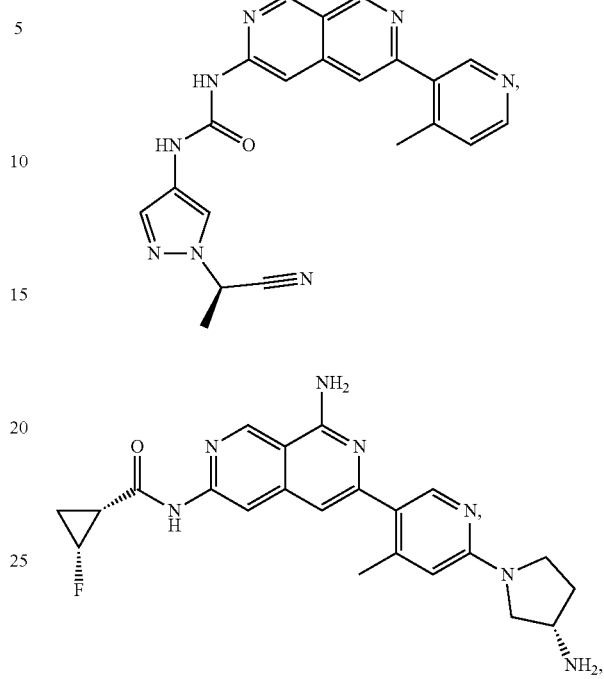
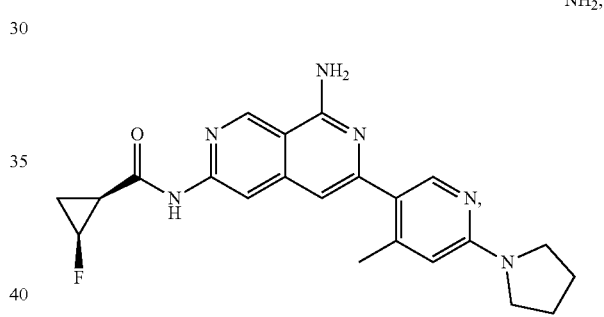
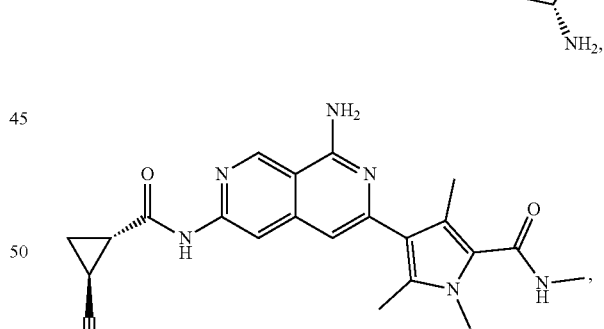
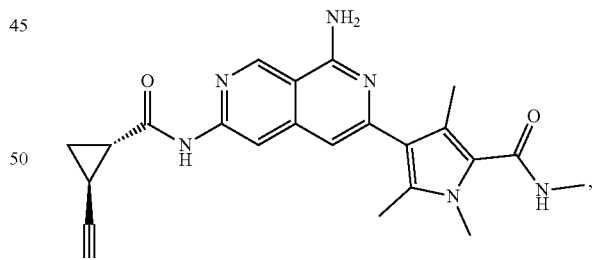
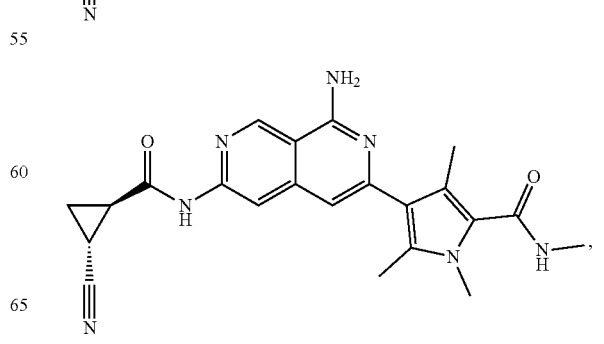

1323
-continued
1324
-continued
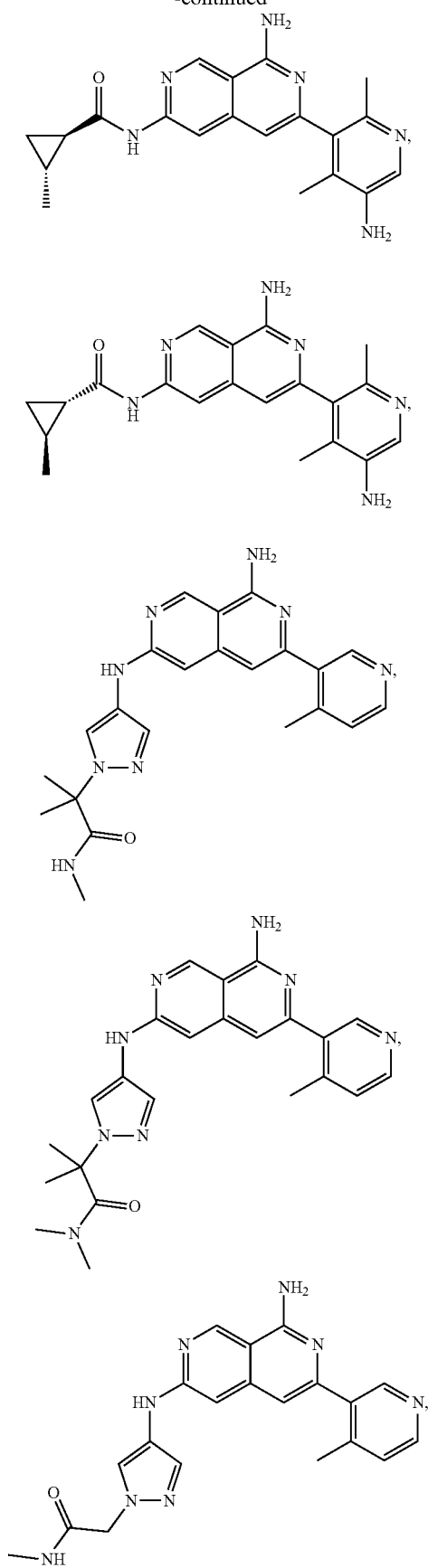
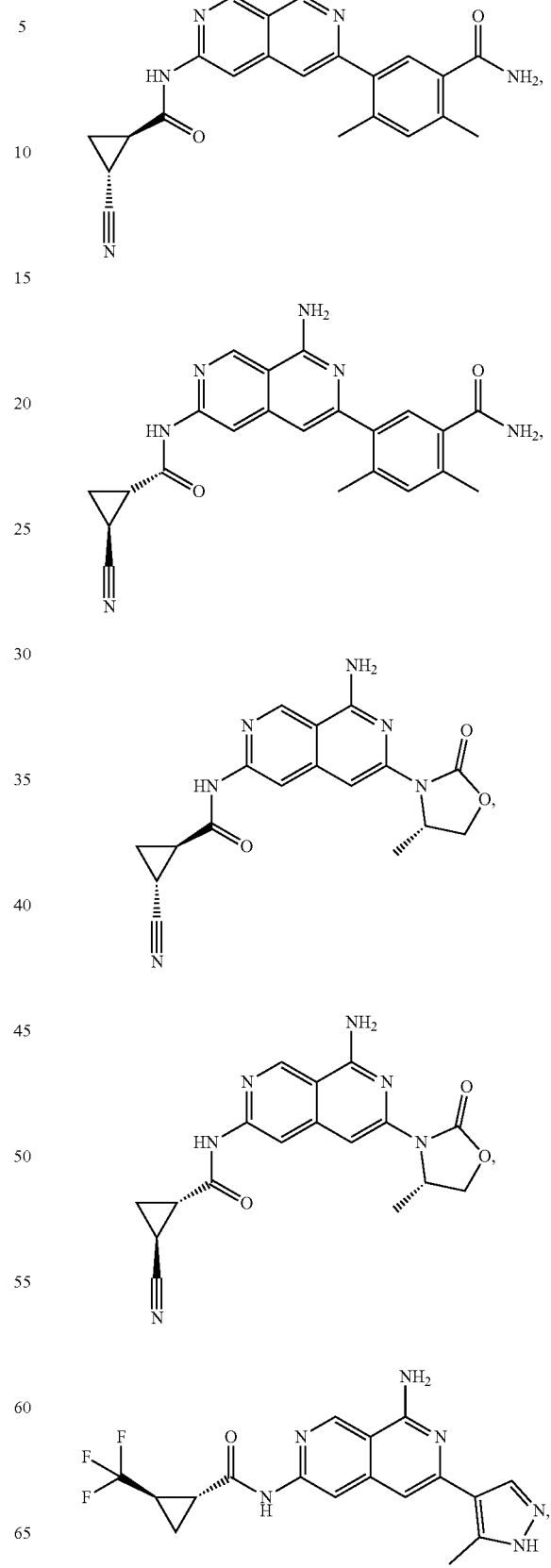

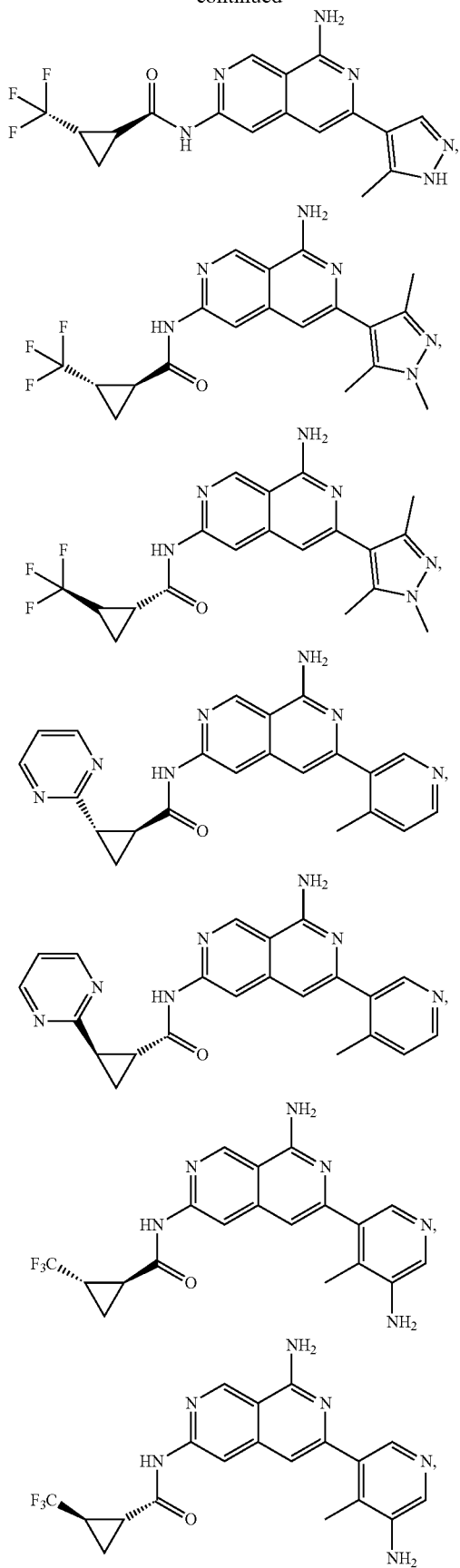
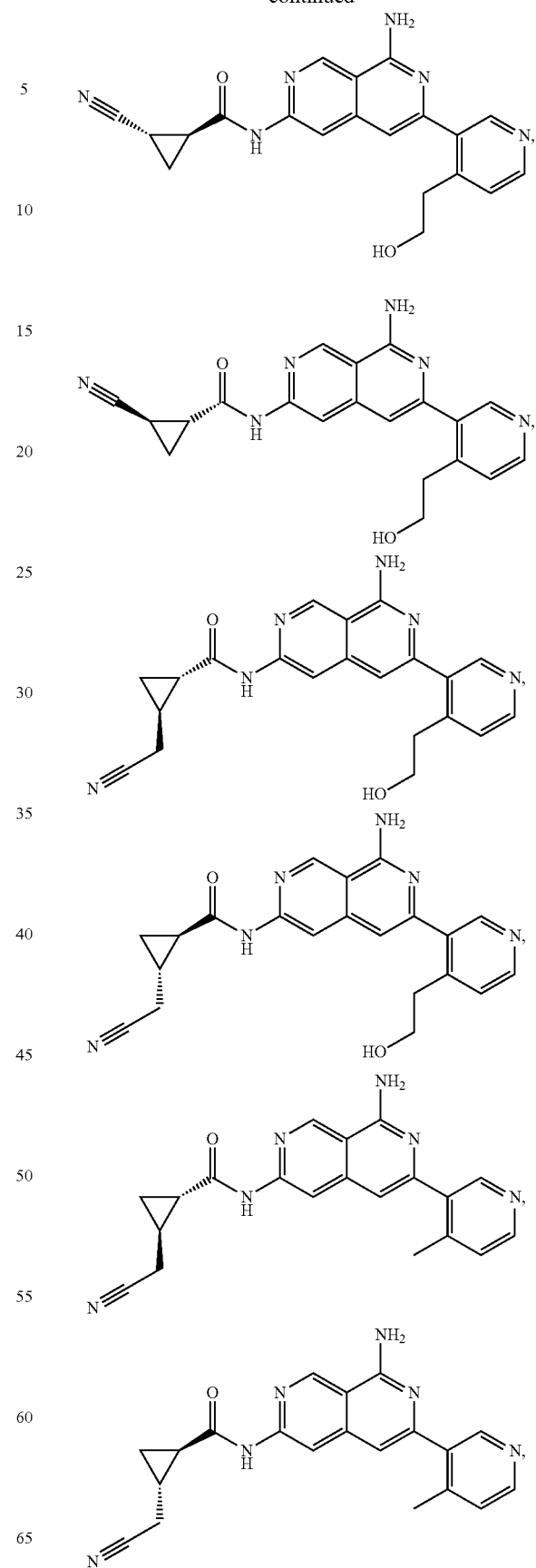

1327
-continued
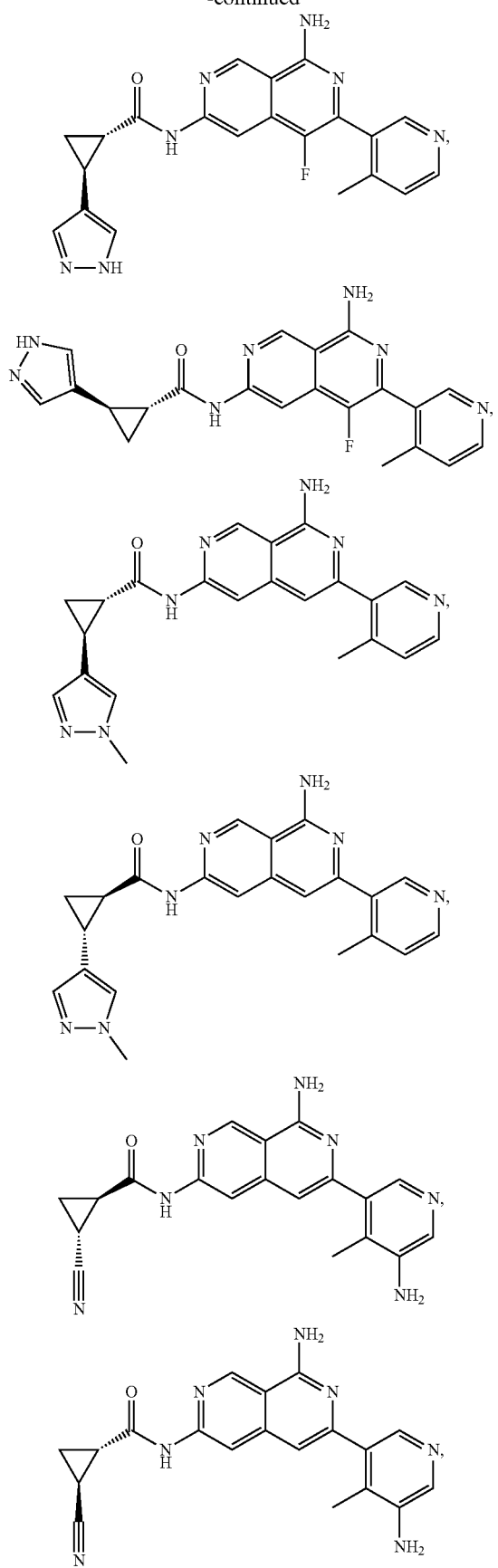
1328
-continued
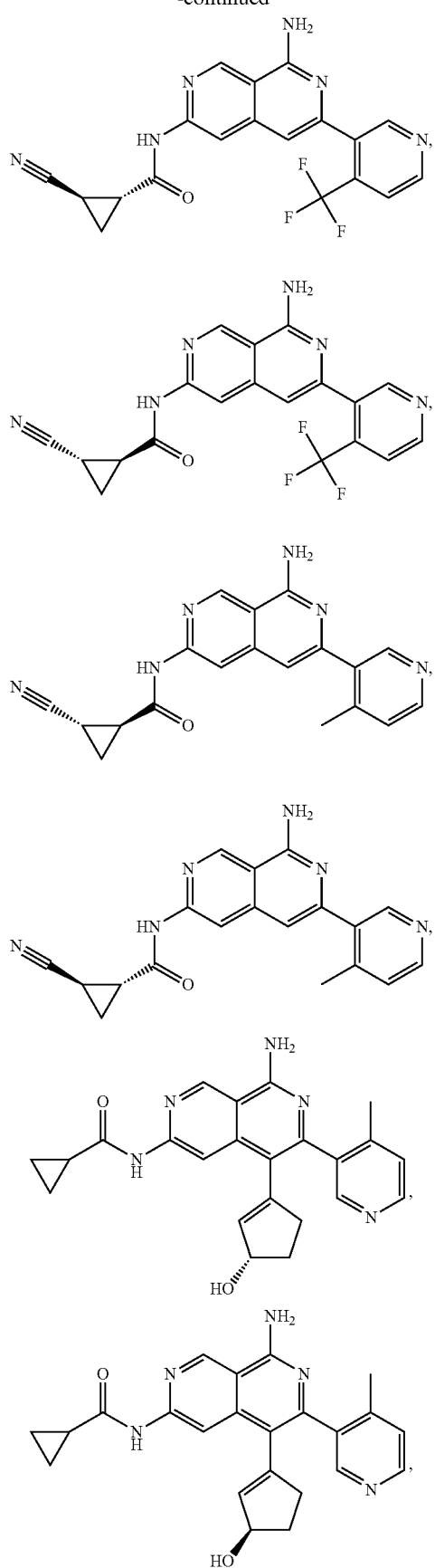

1329
-continued
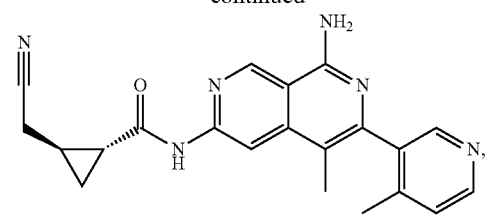
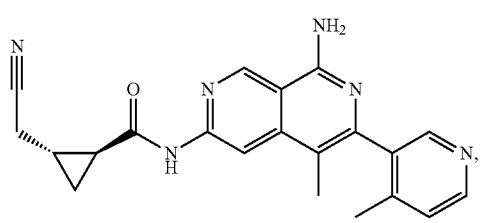
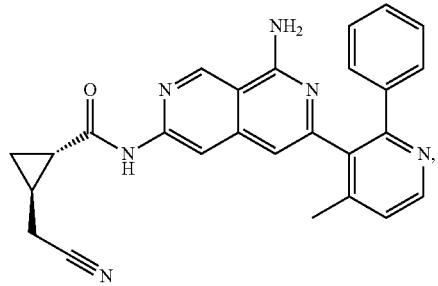
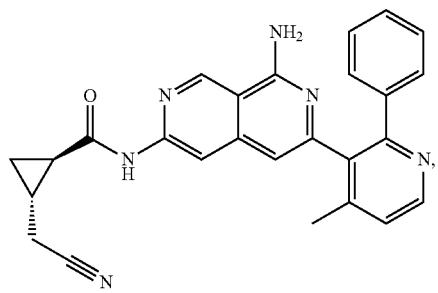
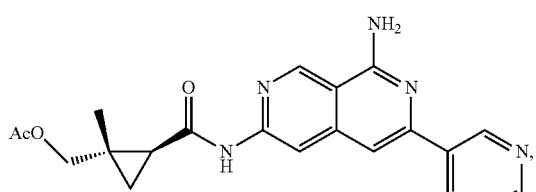
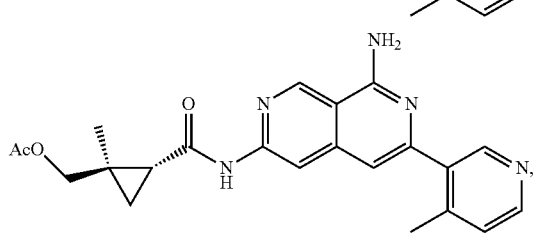
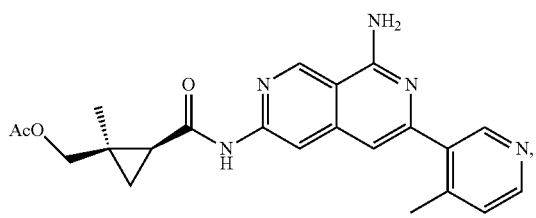
1330
-continued
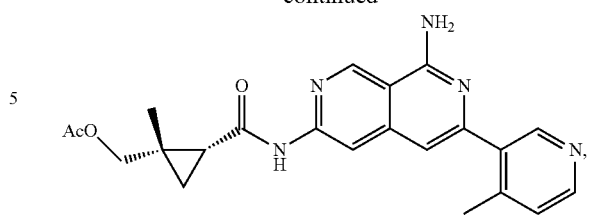

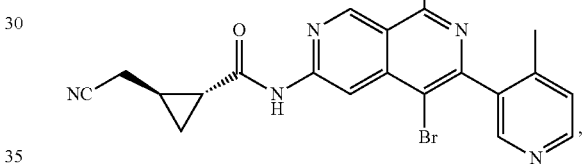
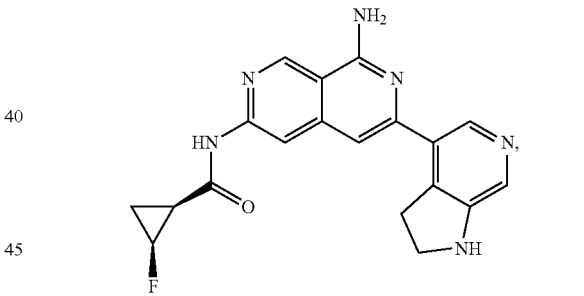
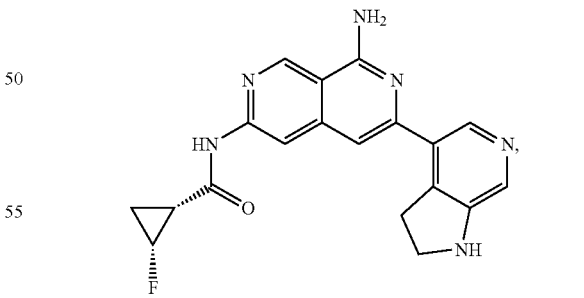
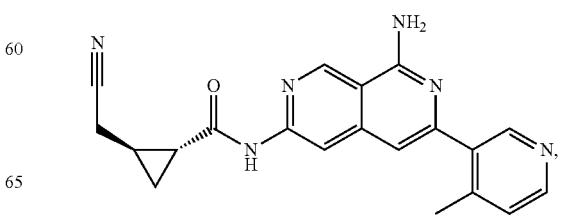

1331
-continued
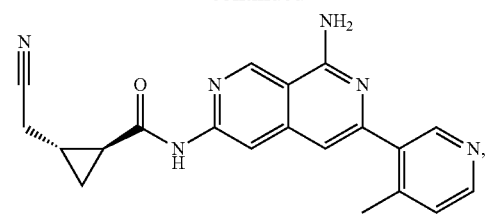
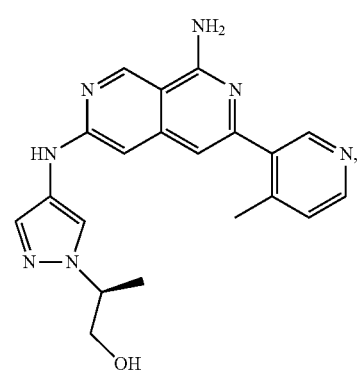
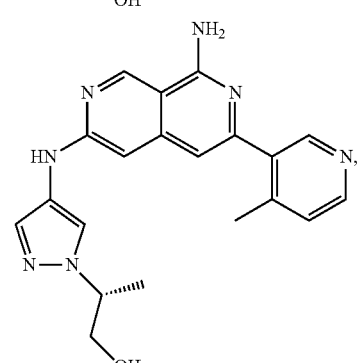
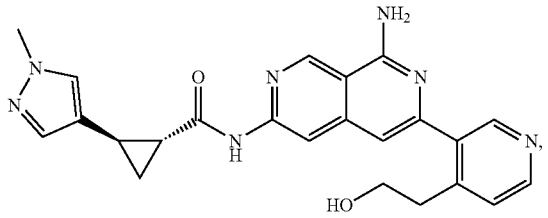
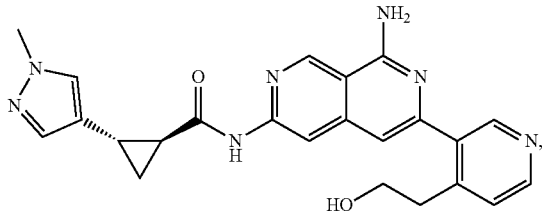
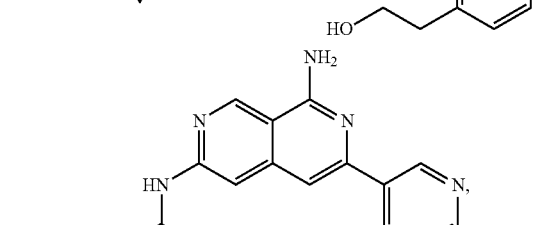
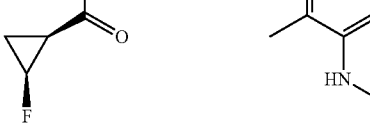
1332
-continued
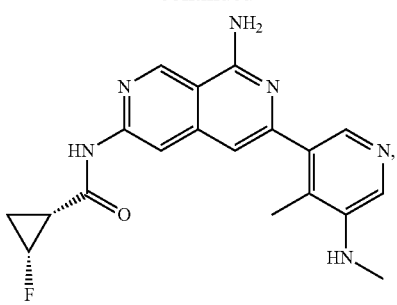
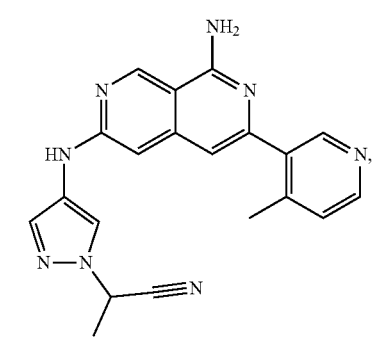
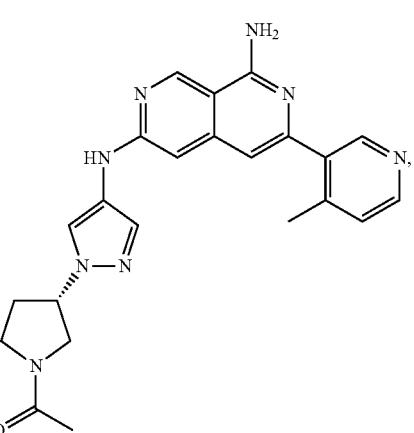
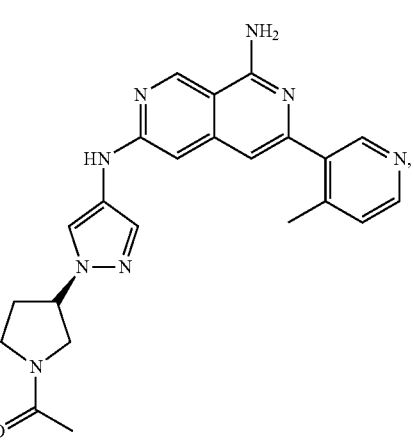

1333
-continued
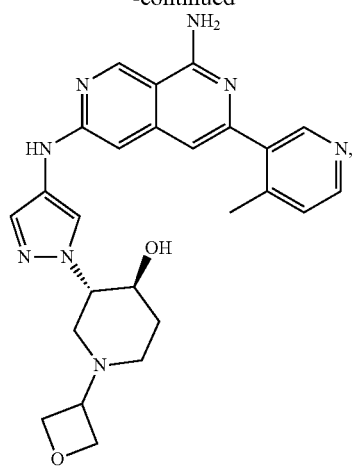
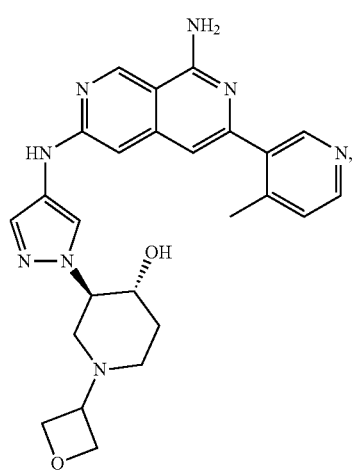
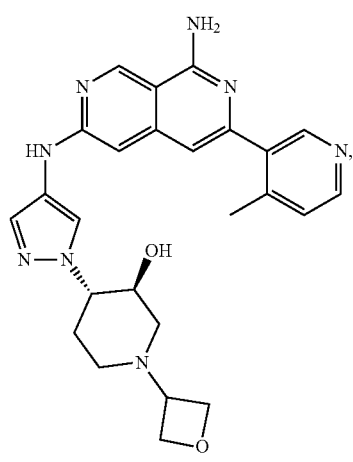
1334
-continued
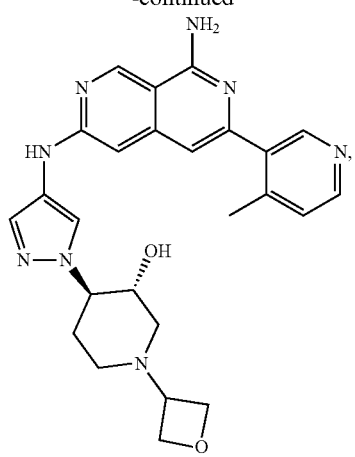
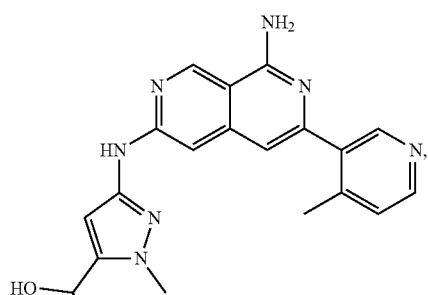
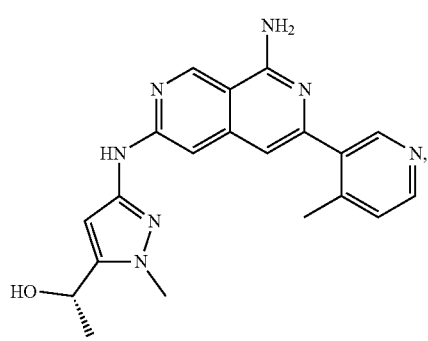
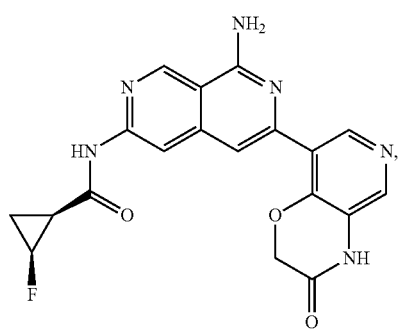

1335 -continued
1336 -continued
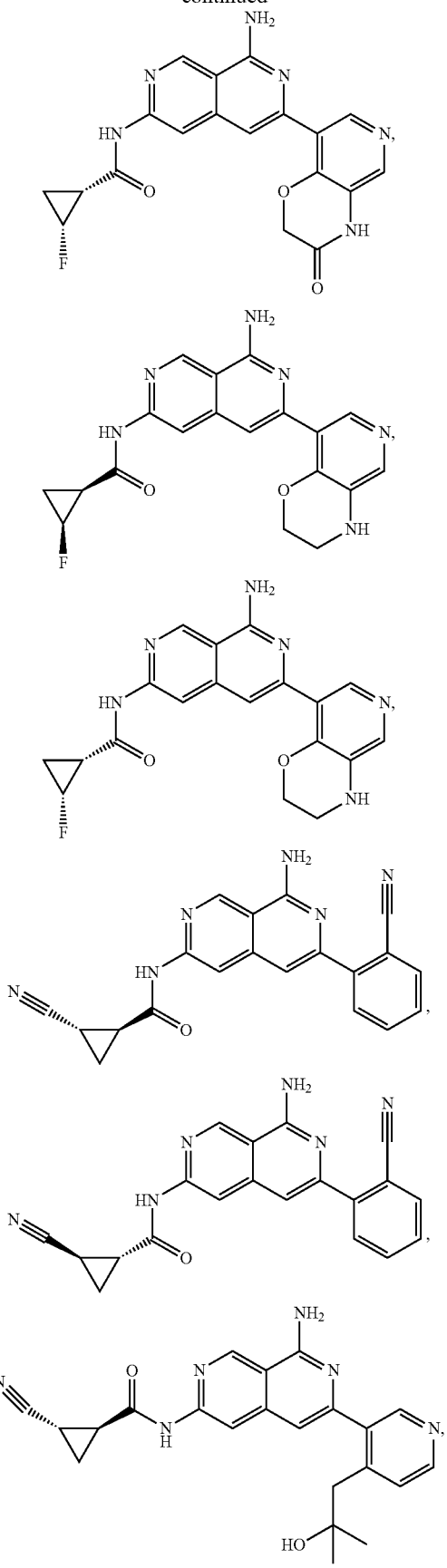

1337
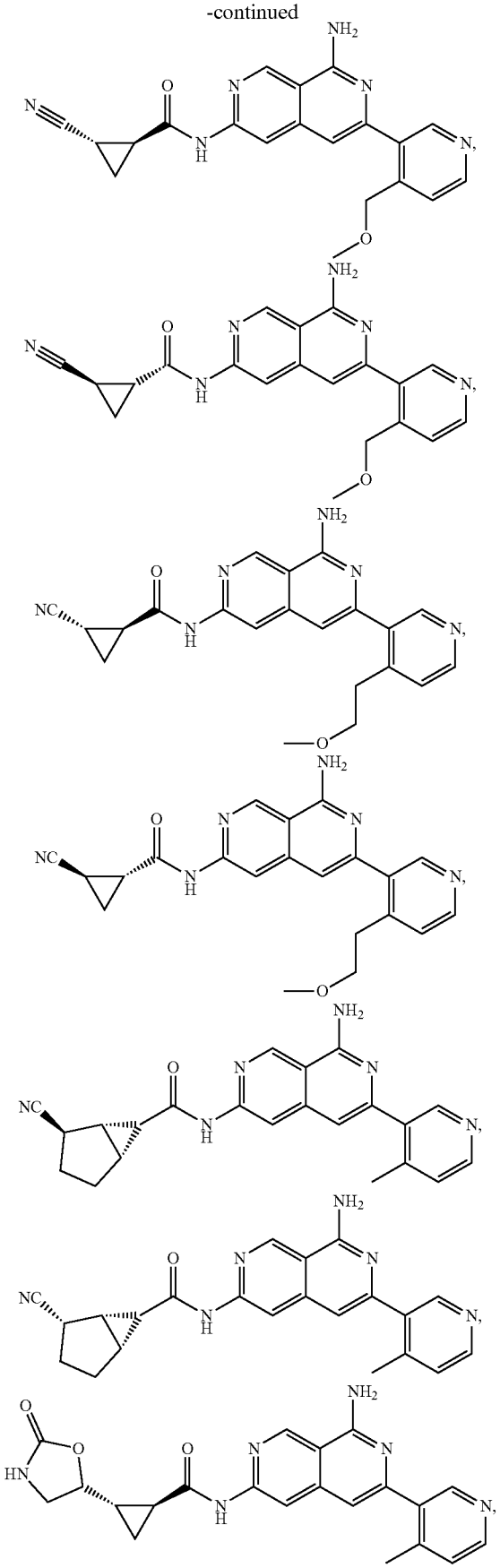
1338
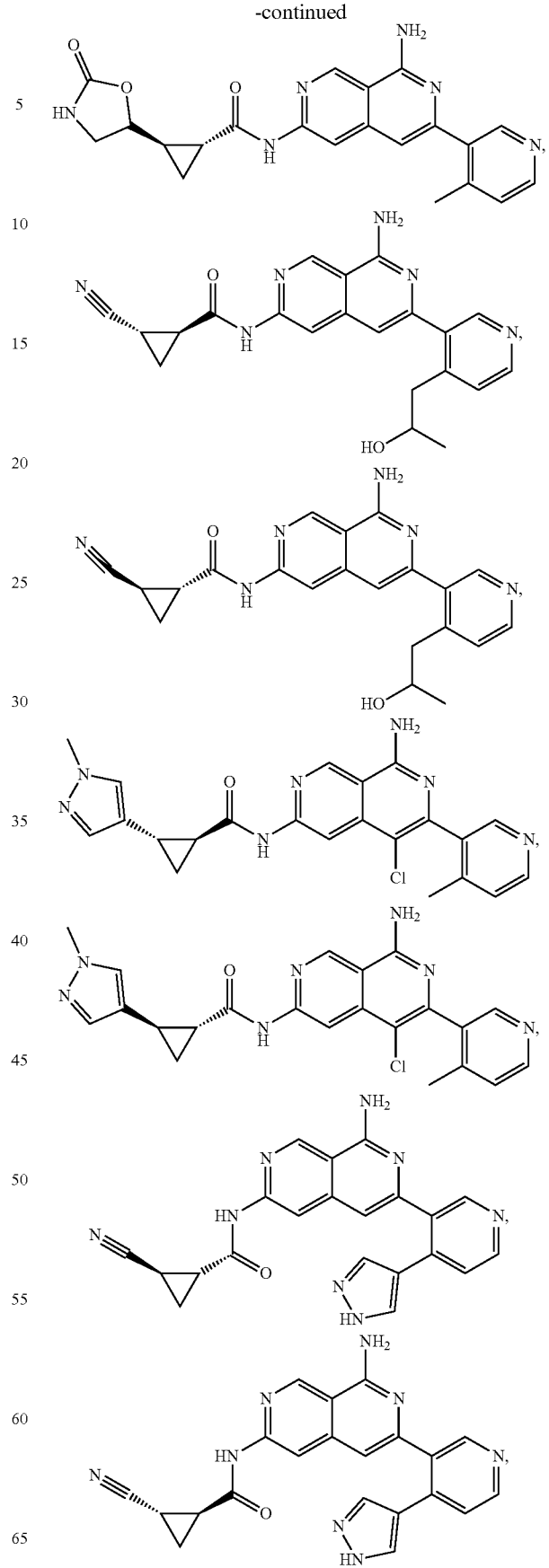

1339
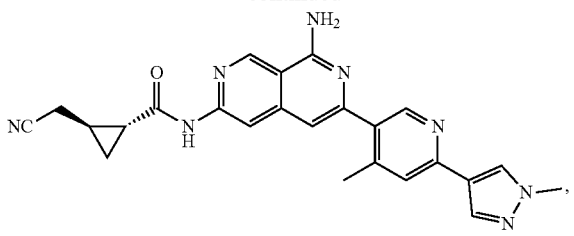
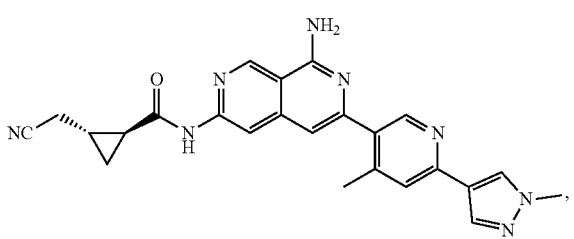
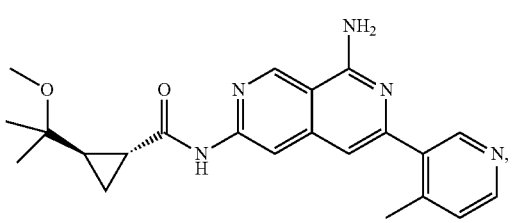
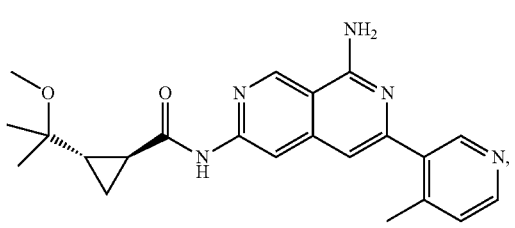
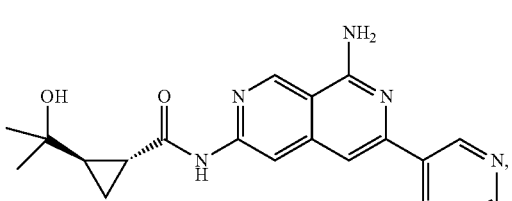
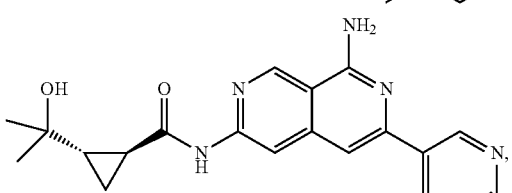
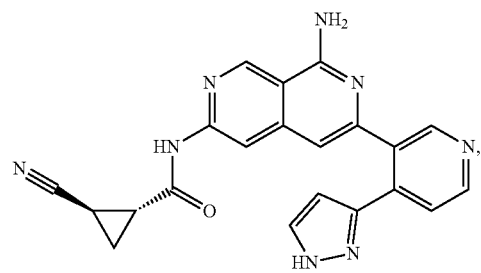
1340
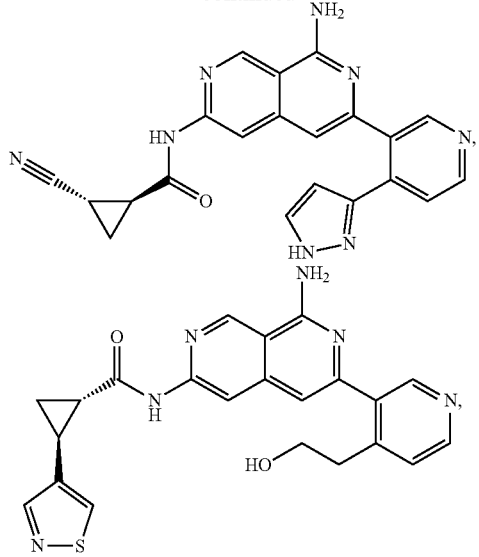
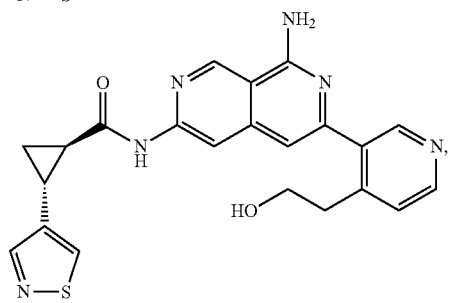
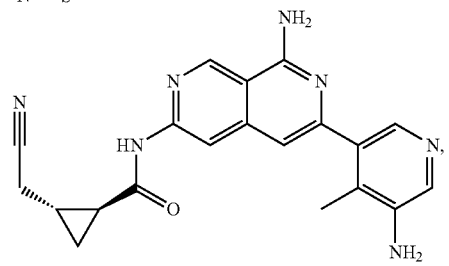
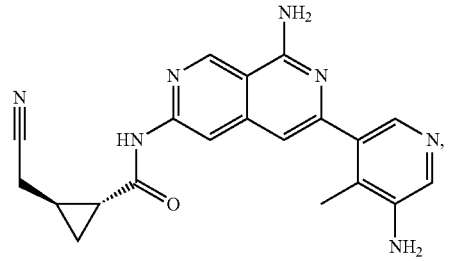
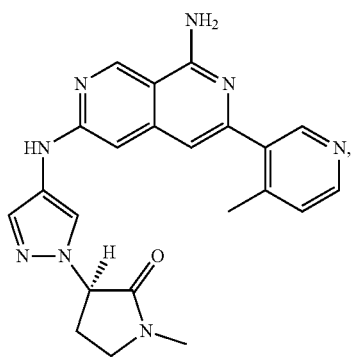

1341
-continued
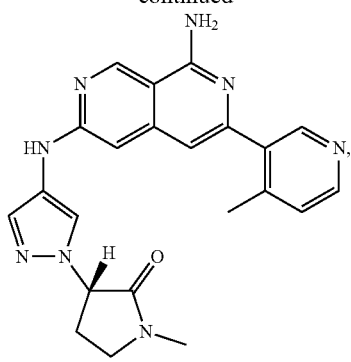
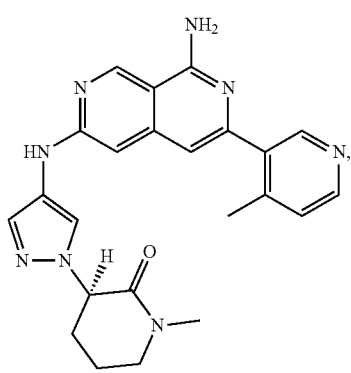
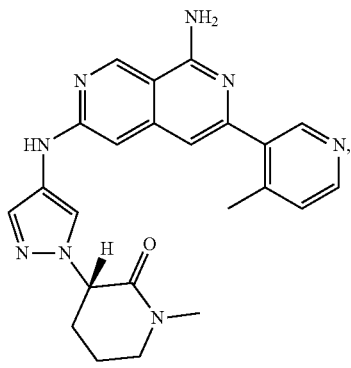
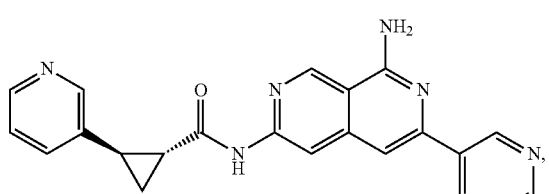
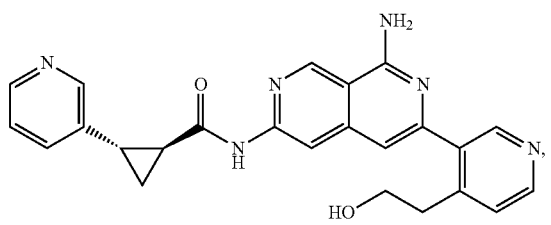
1342
-continued
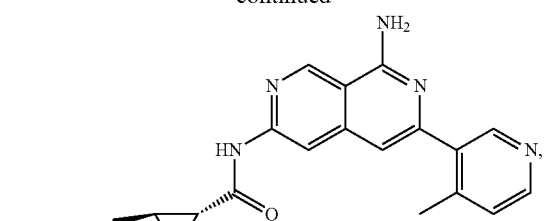
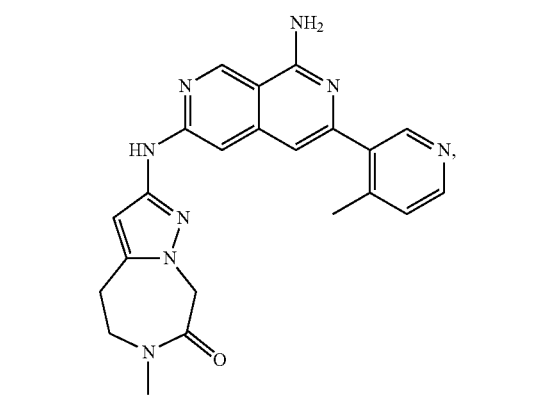
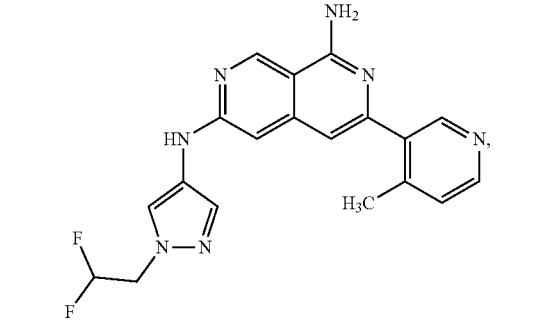
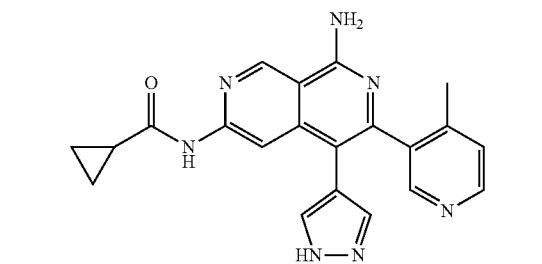
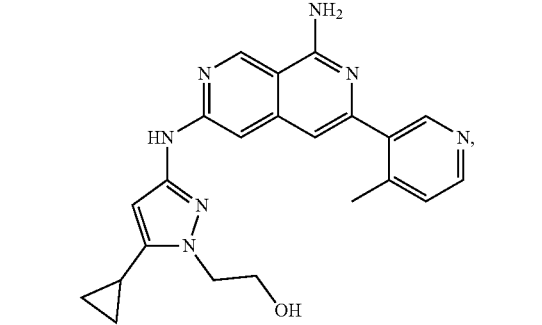

1343
-continued
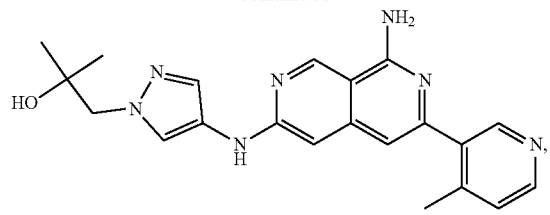
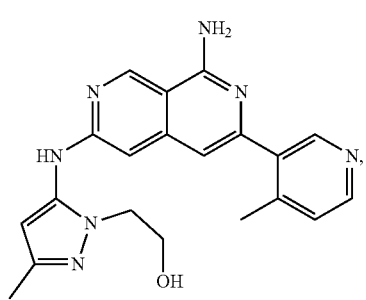
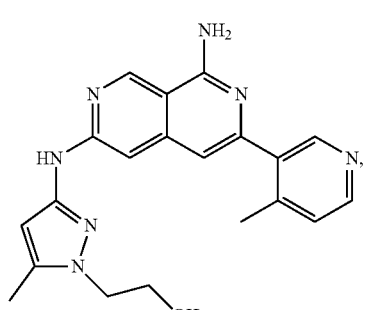
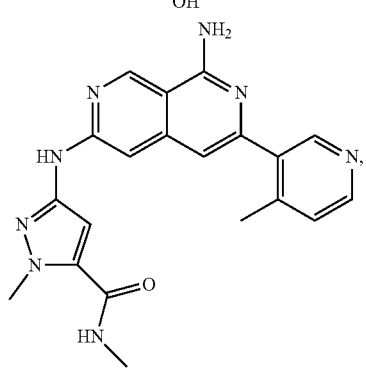
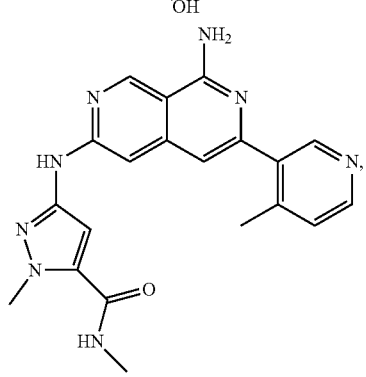
1344
-continued
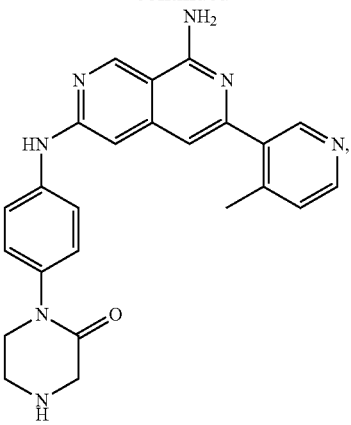
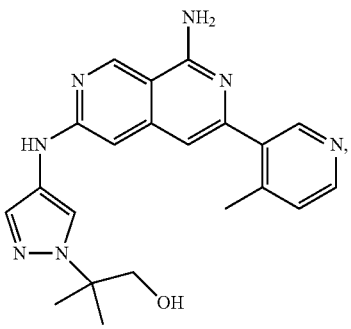
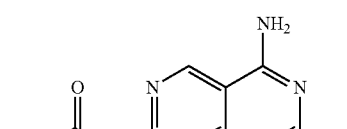
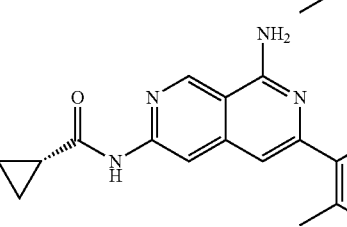

1345
-continued
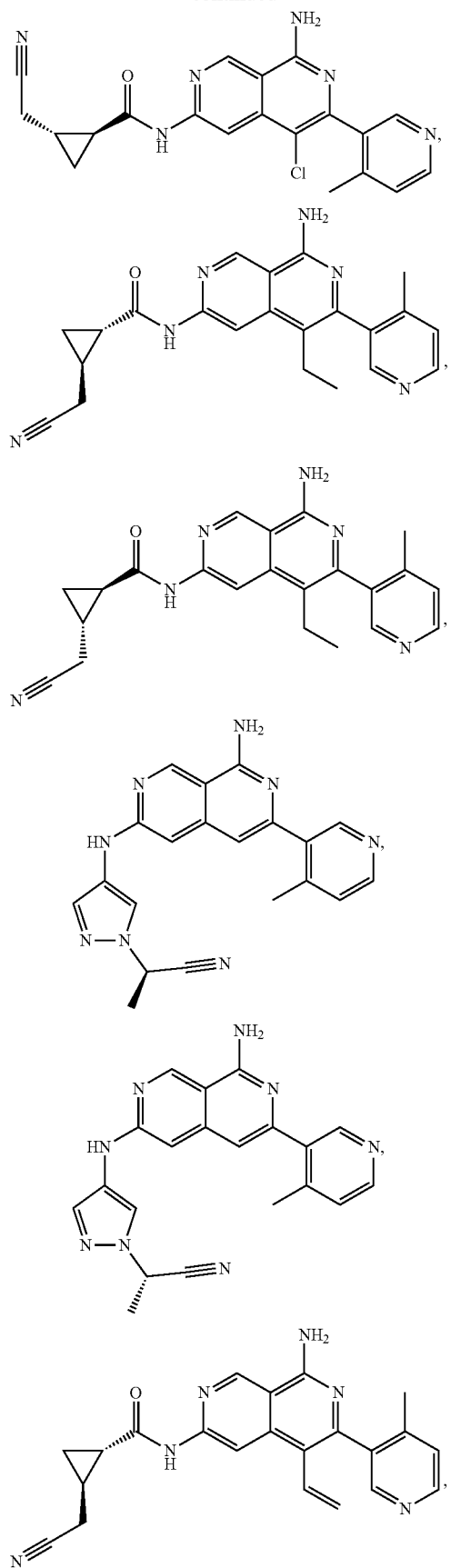
1346
-continued
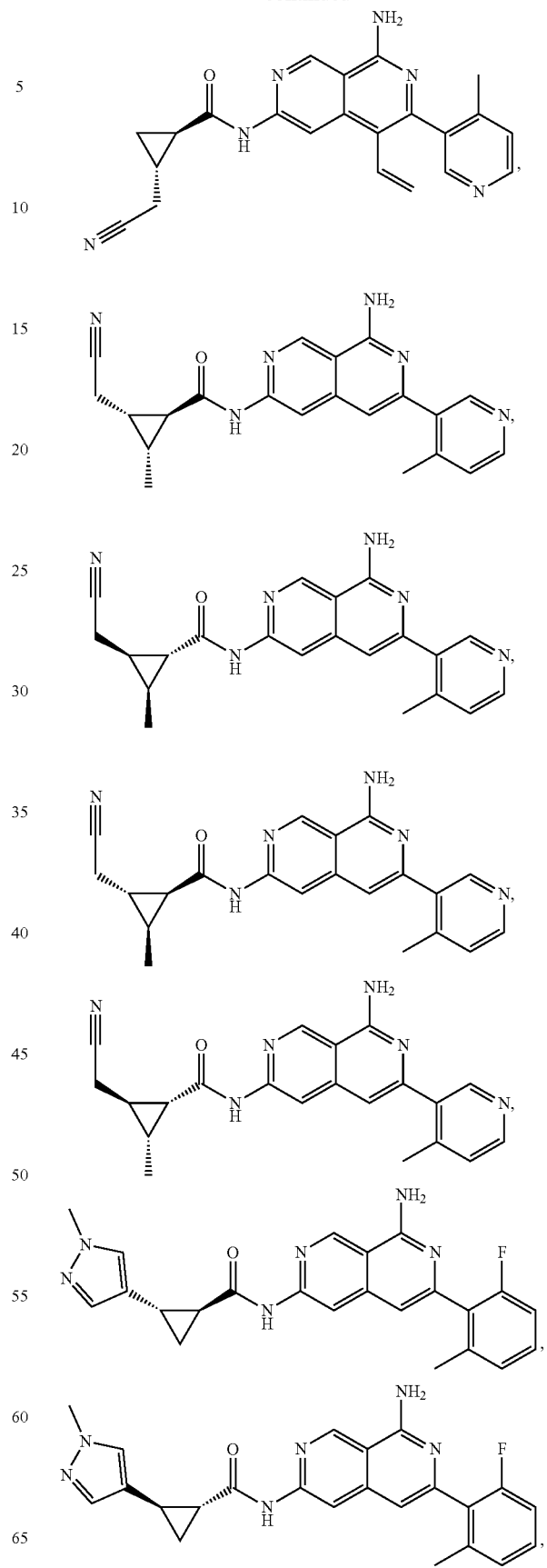

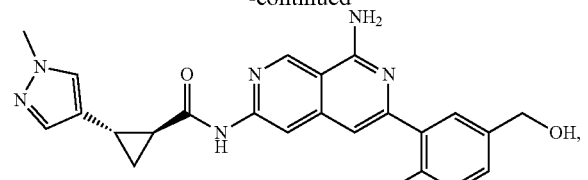
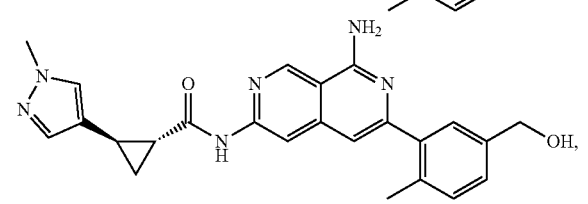

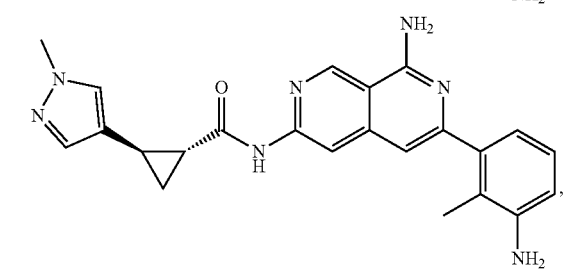
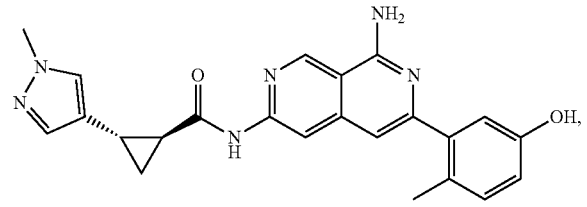
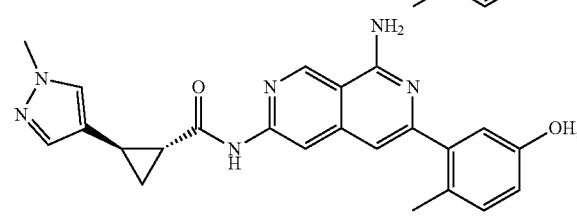

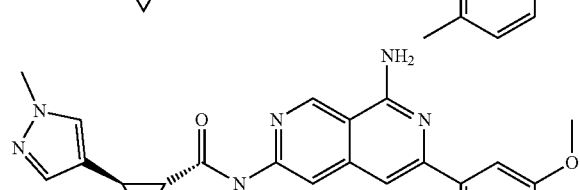
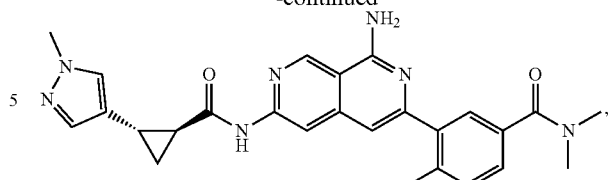
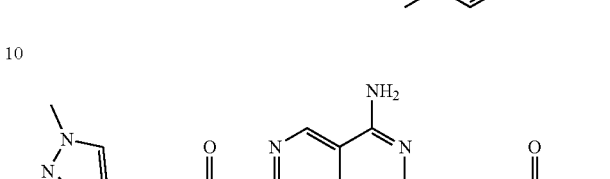
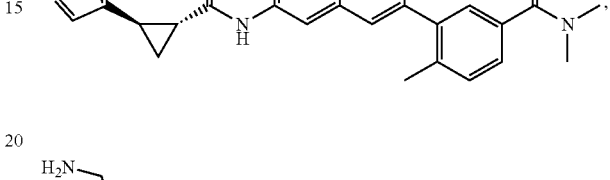
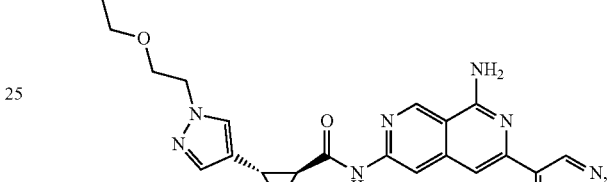
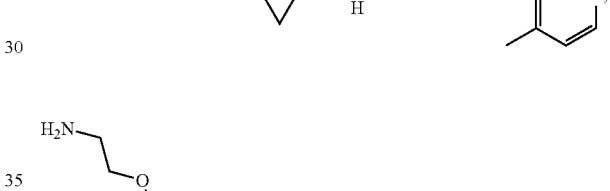
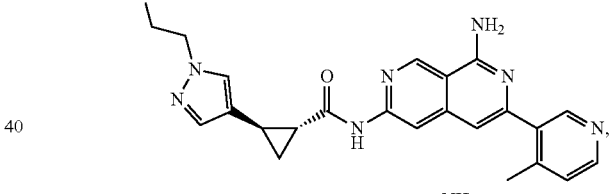
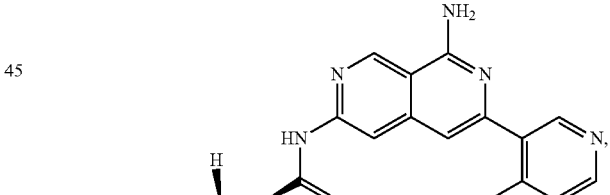
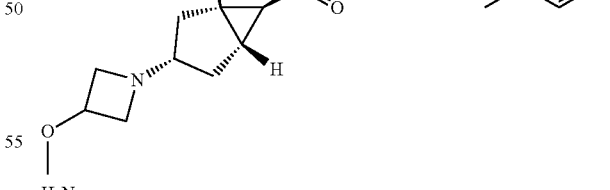
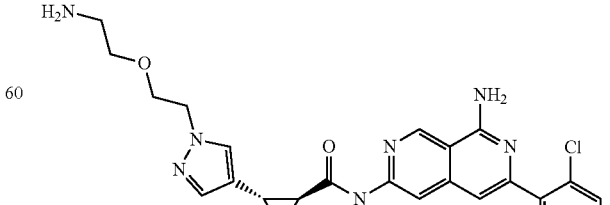

1349
-continued
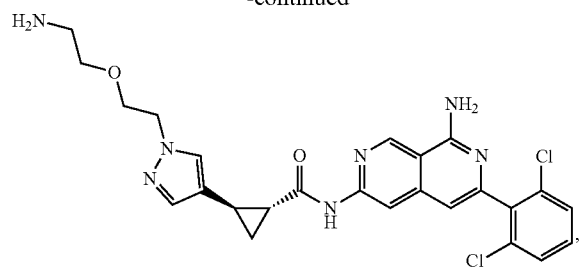
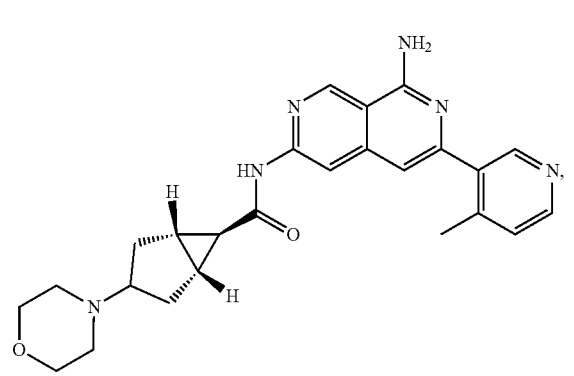
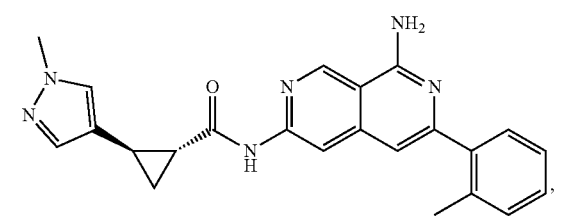
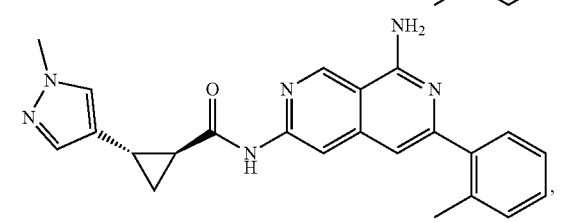
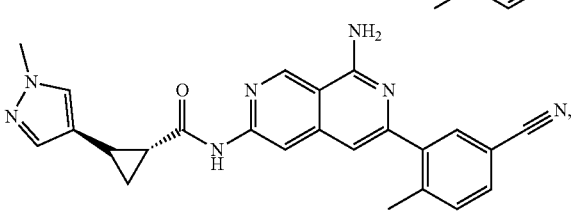
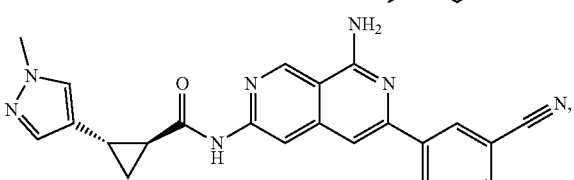
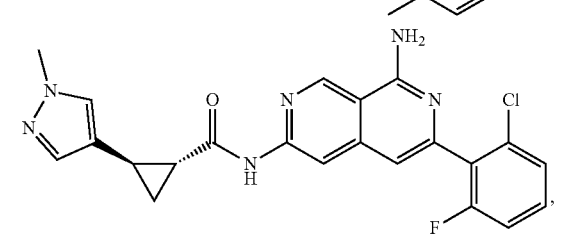
1350
-continued
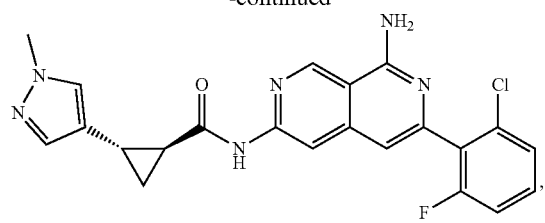
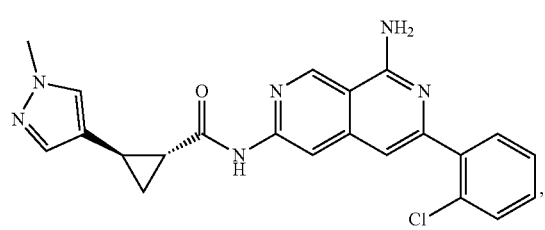
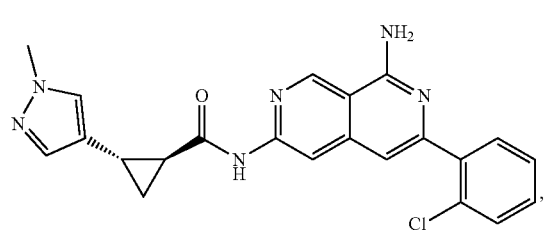
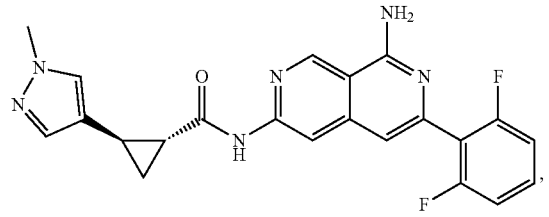
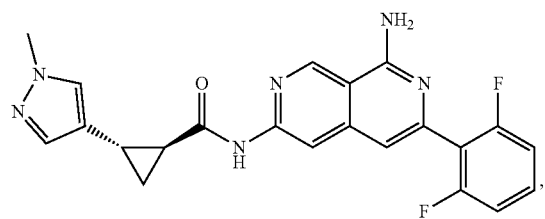
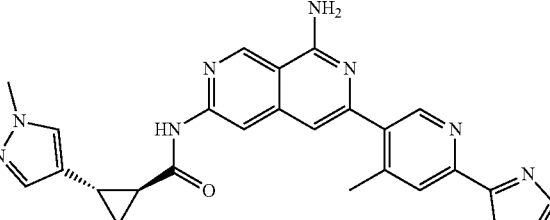
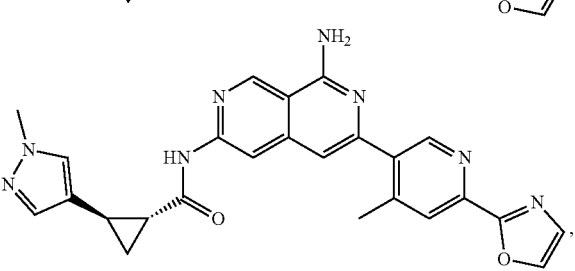

1351
-continued
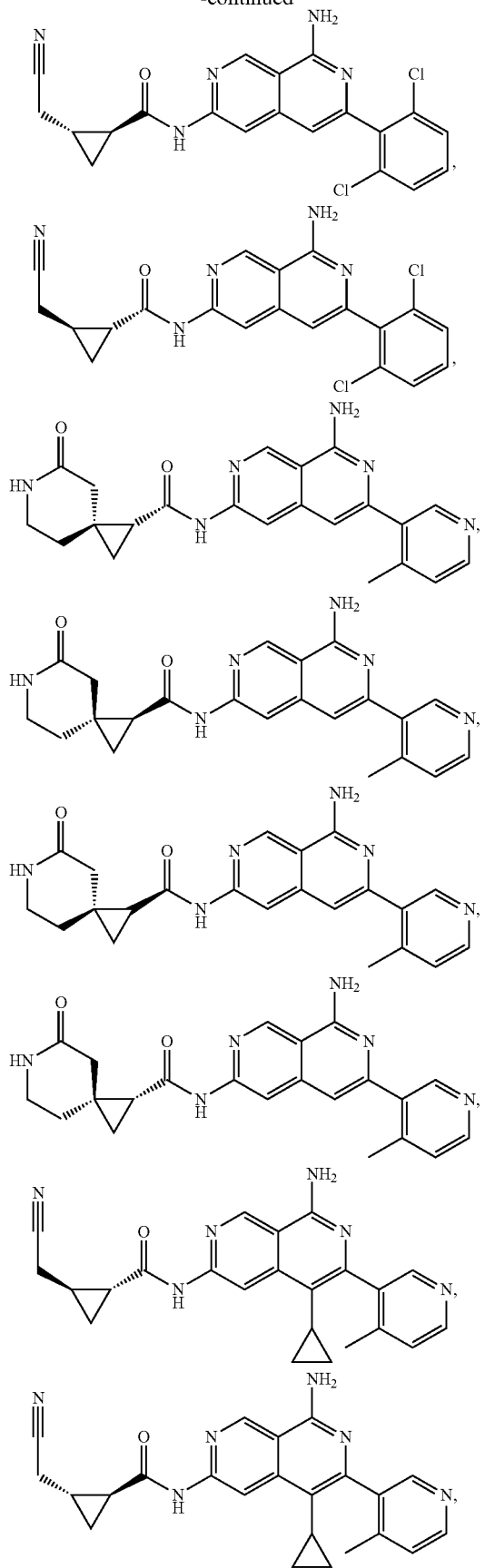
1352
-continued
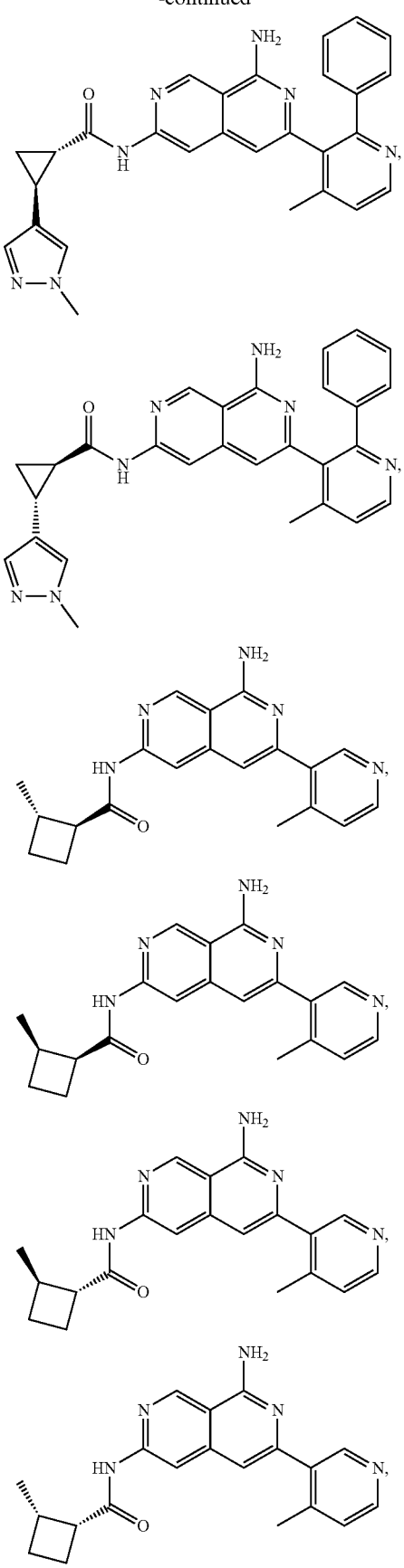

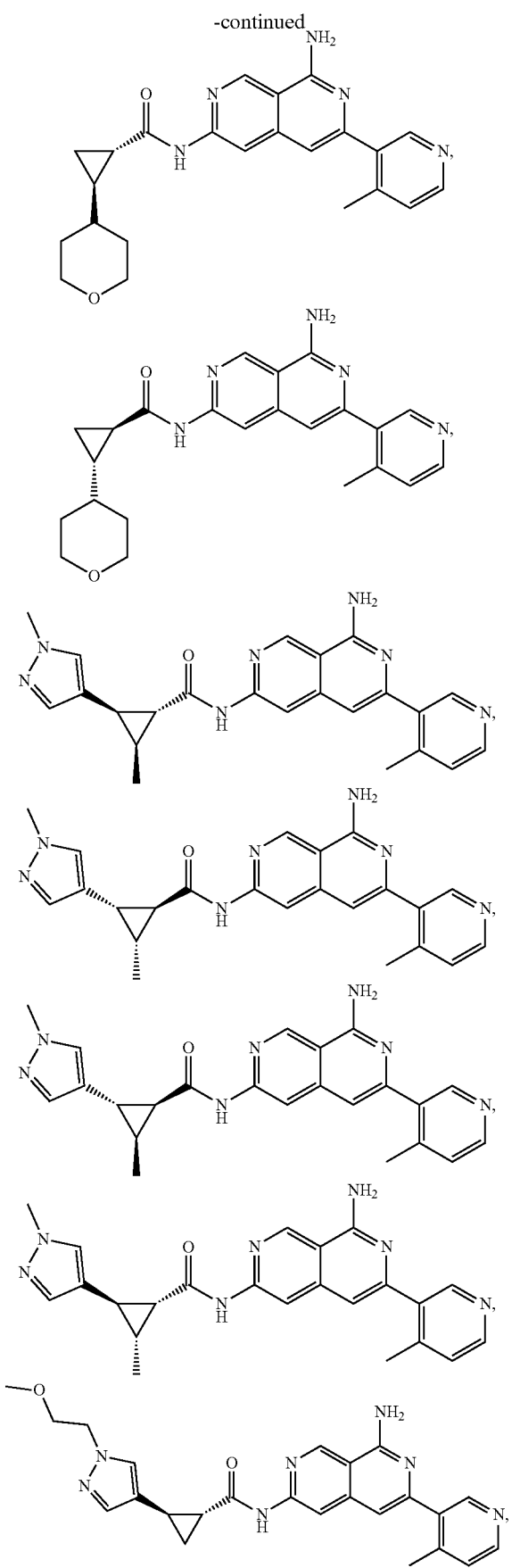
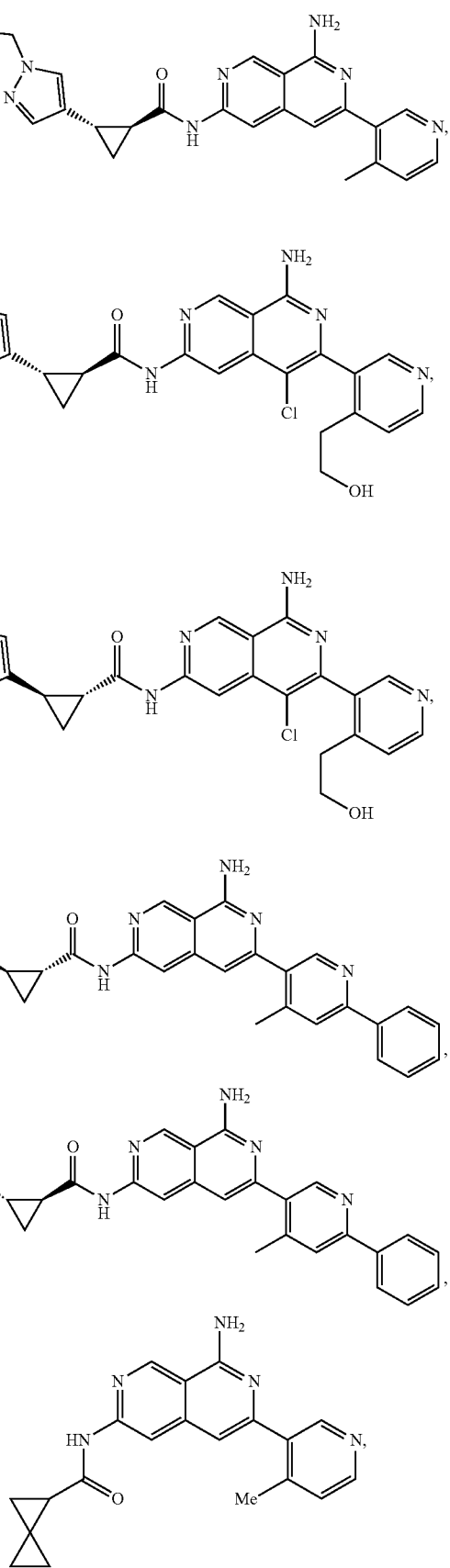

1355
-continued
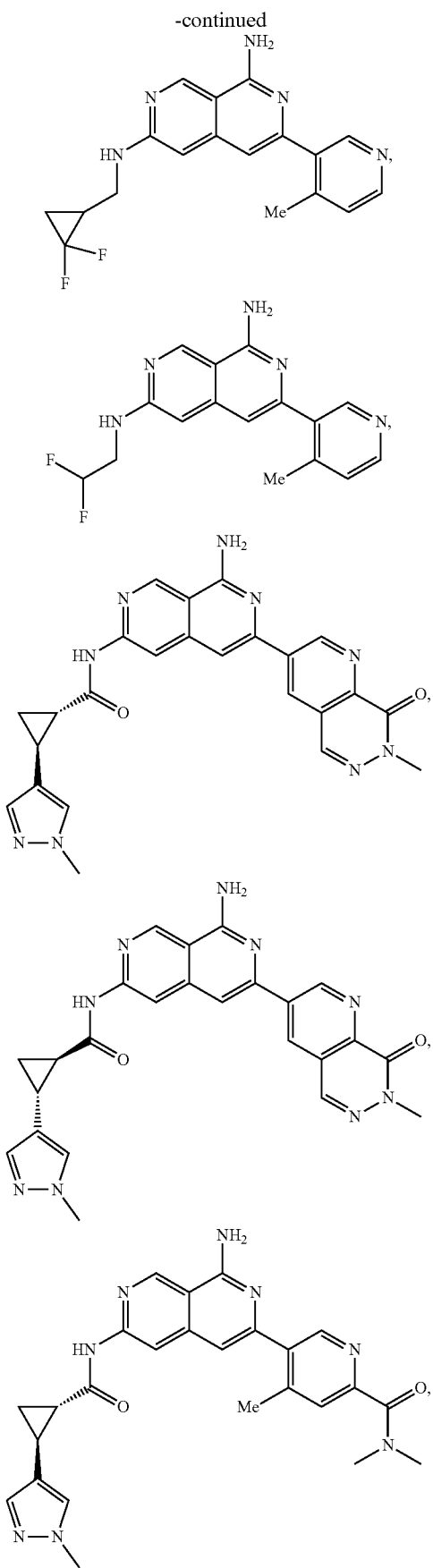
1356
-continued
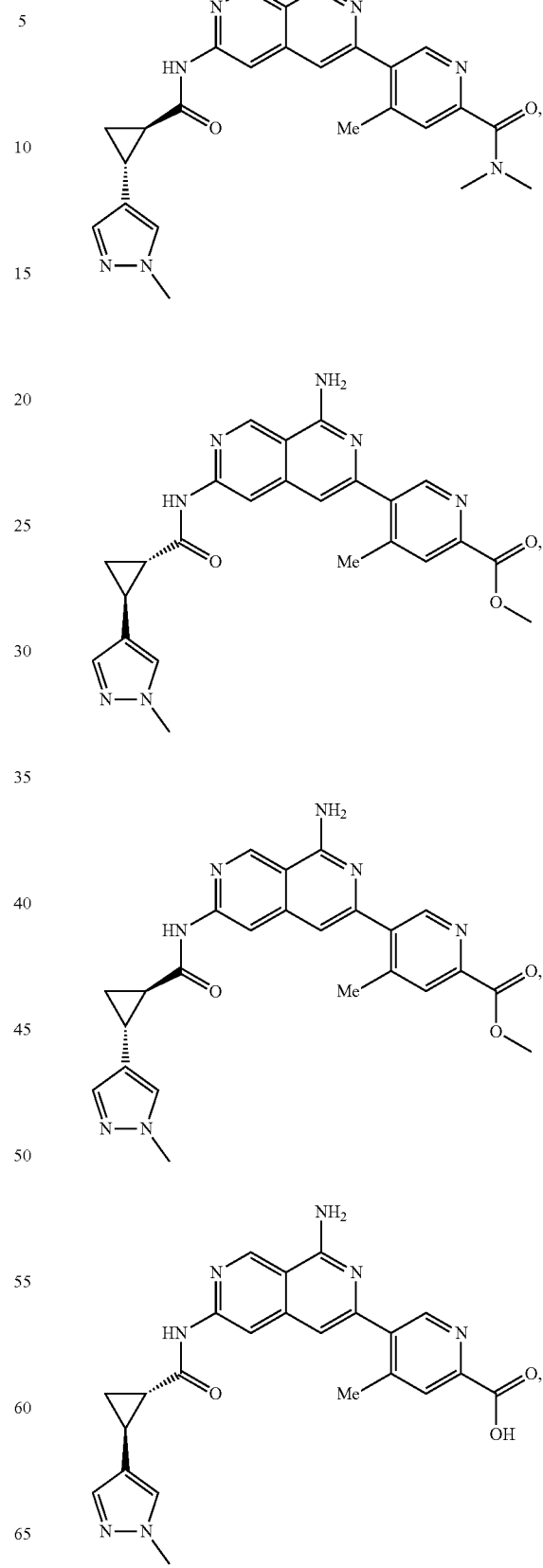

1357
-continued
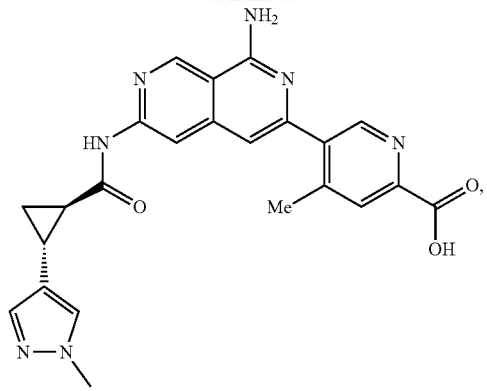
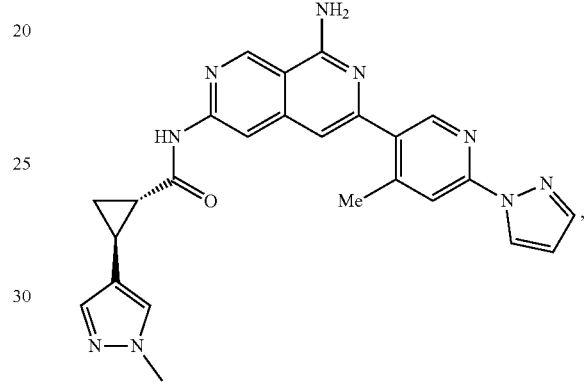
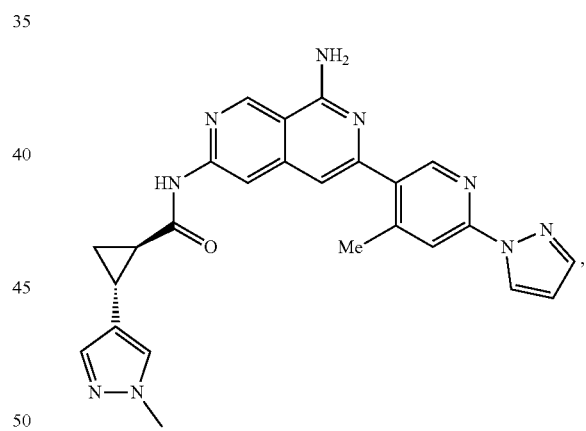
1358
-continued
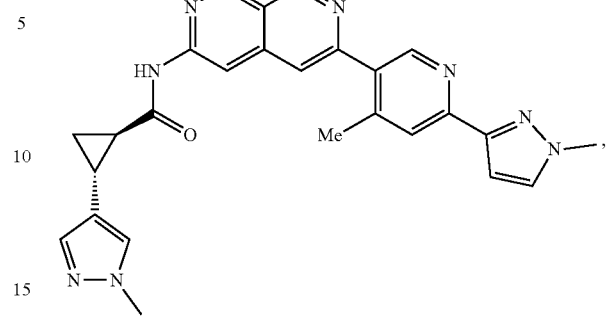
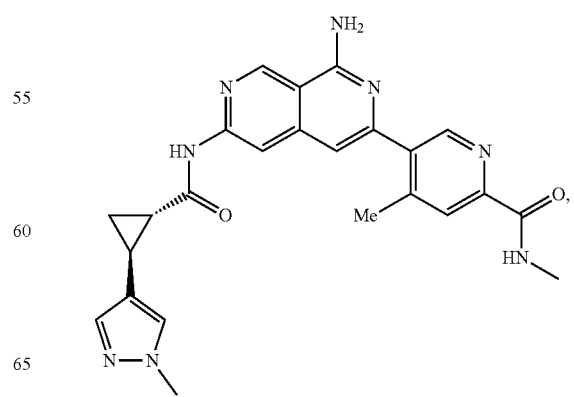

1359
-continued
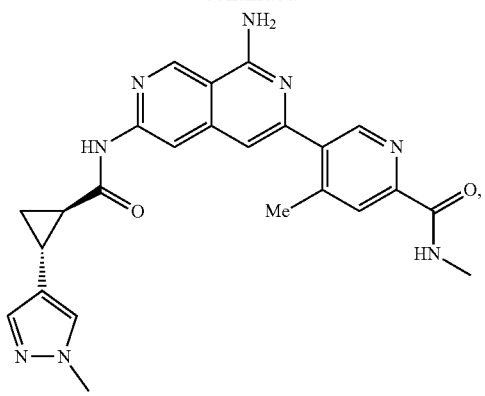
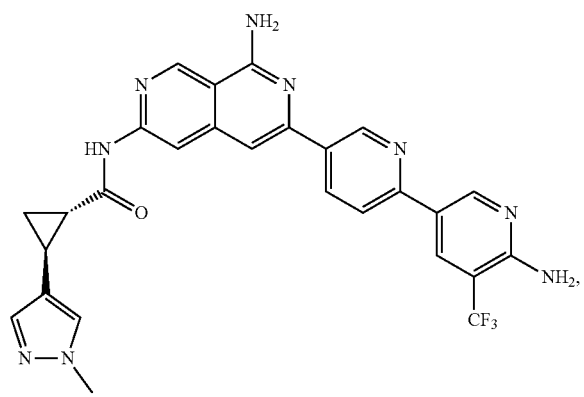
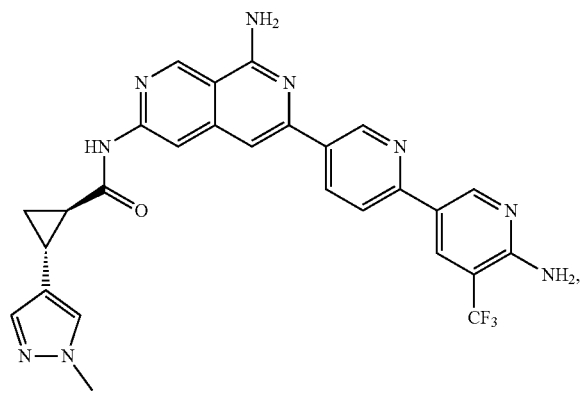
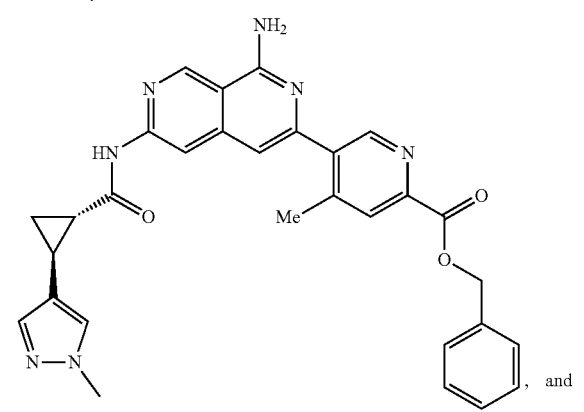
, and
1360
-continued
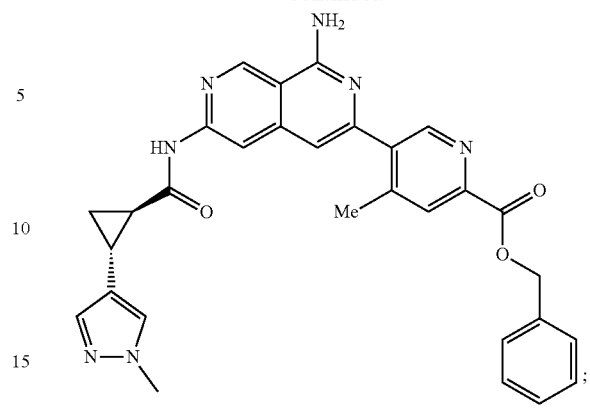
or a pharmaceutically acceptable salt thereof.
16. The method of claim 3, wherein the compound is selected from the group consisting of Compound Nos. 349-429 in Table 2, having the structures:
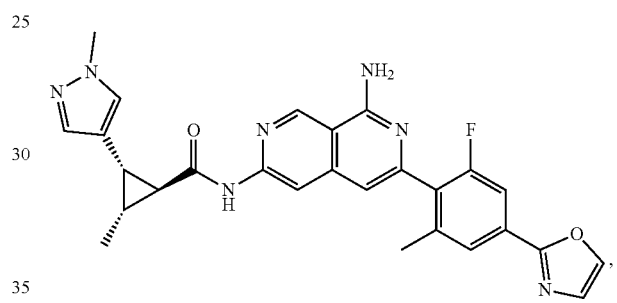
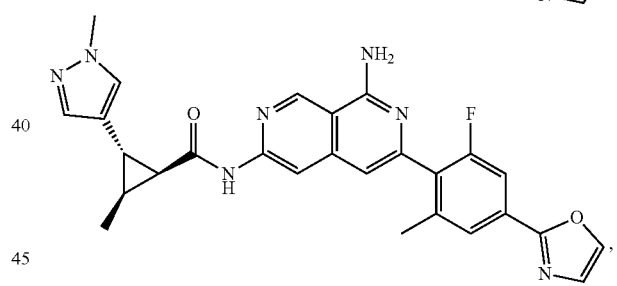
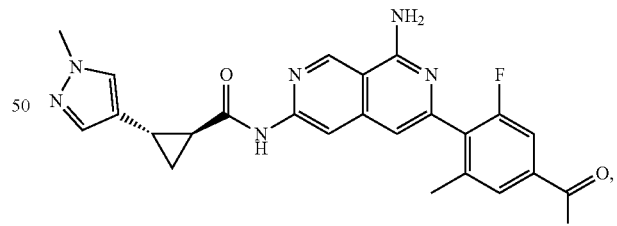
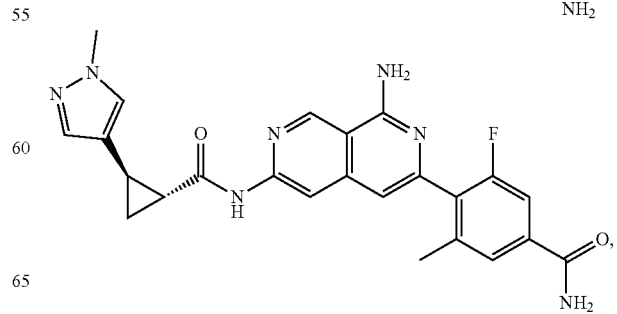

1361
-continued
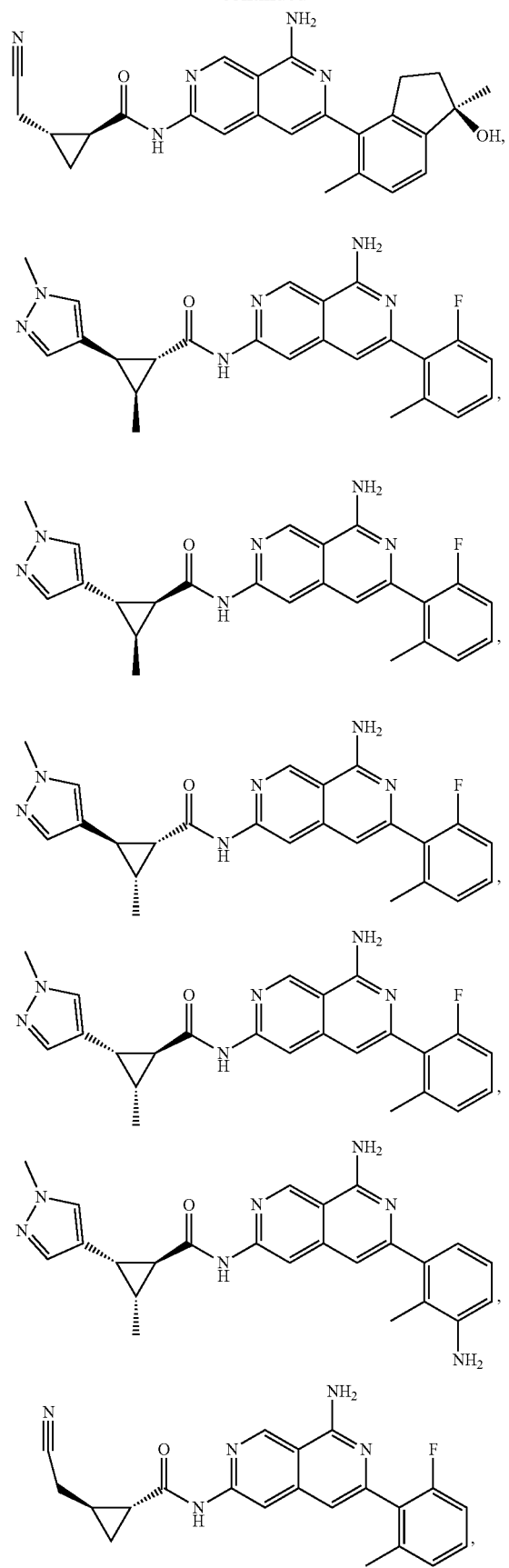
1362
-continued
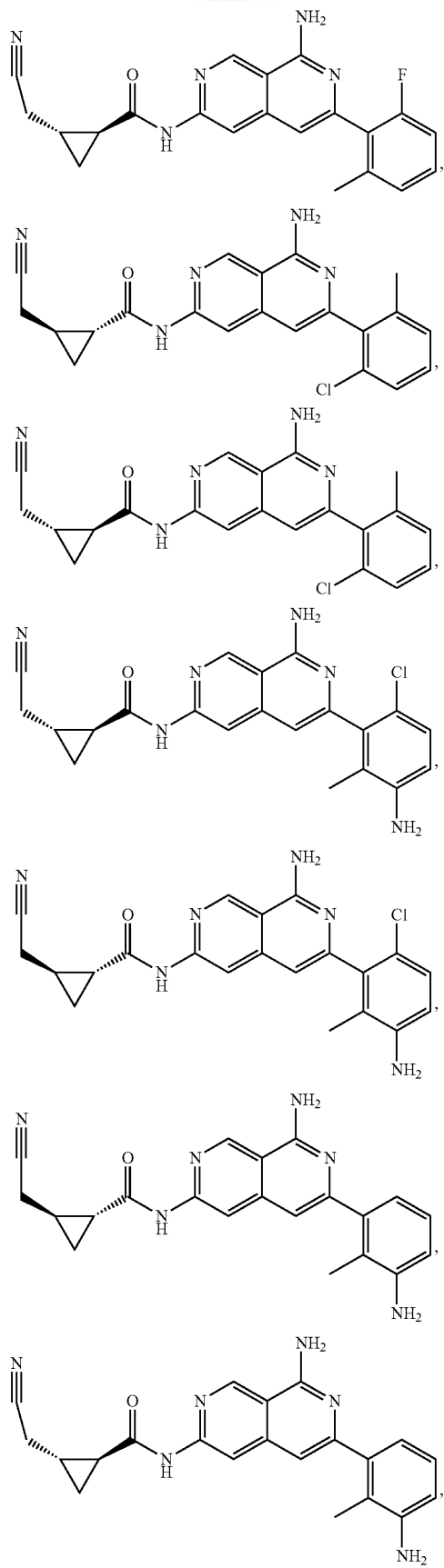

1363
-continued
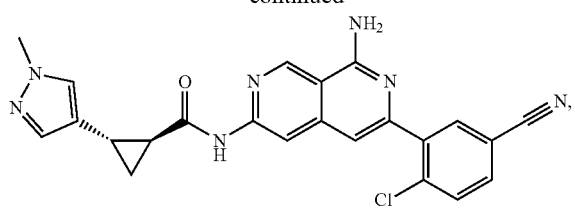
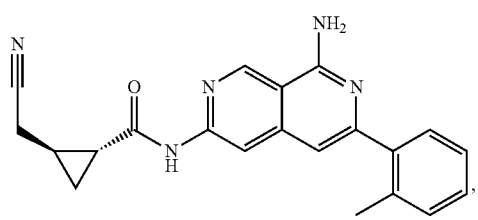
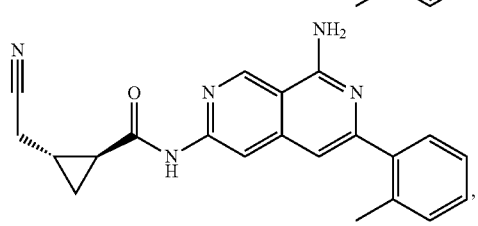
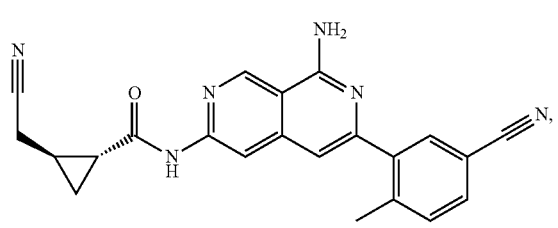
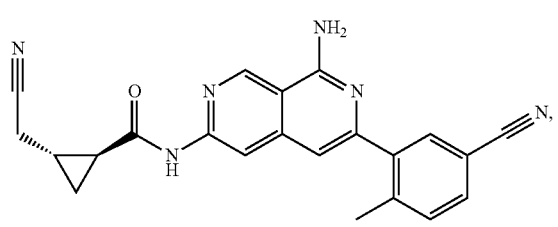
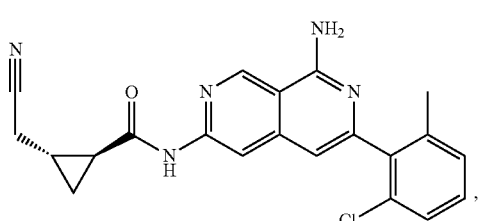
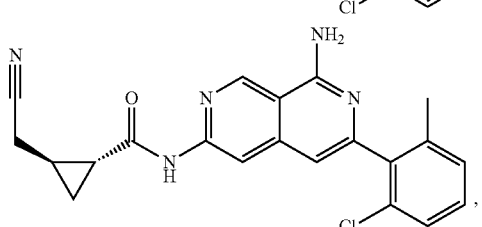
1364
-continued
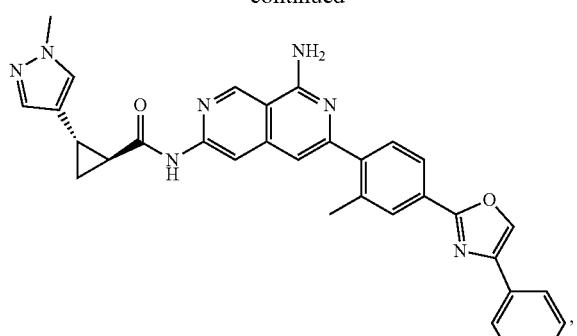
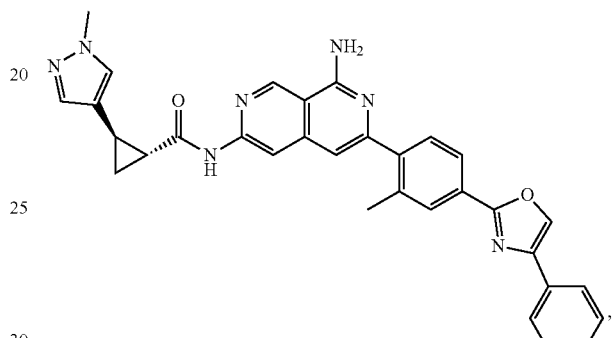
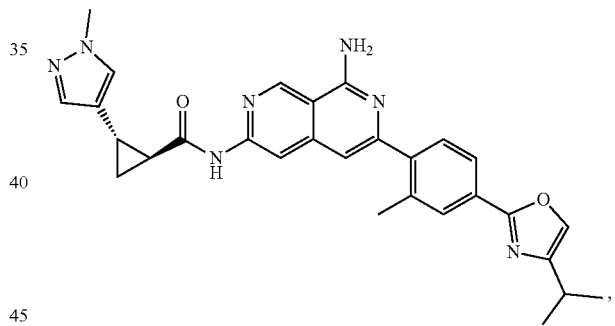
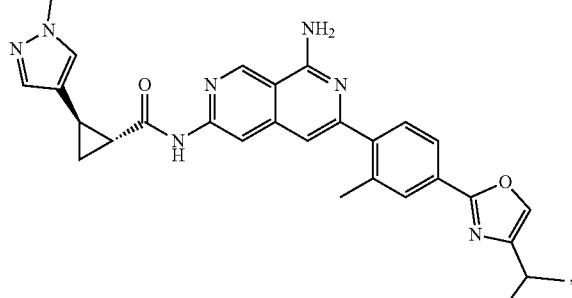
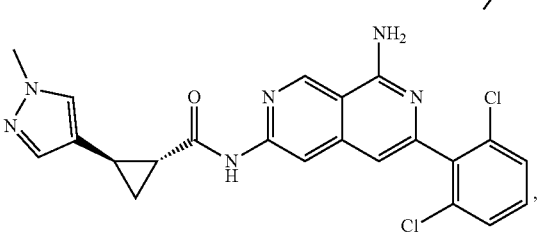

1365
-continued
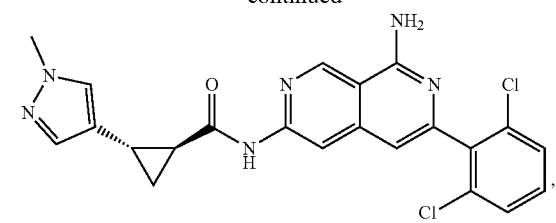
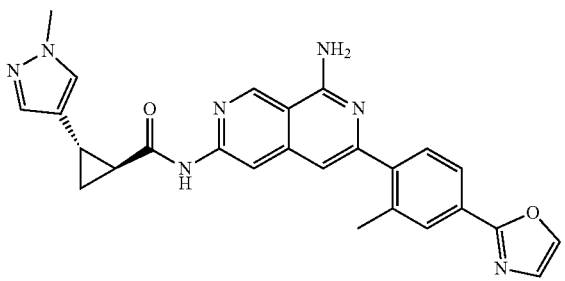
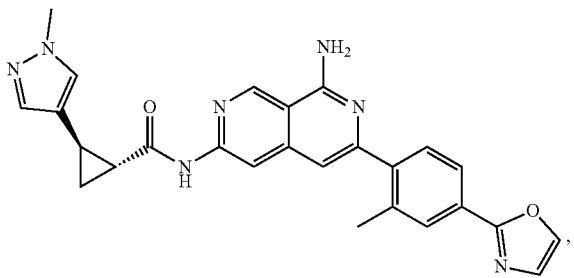
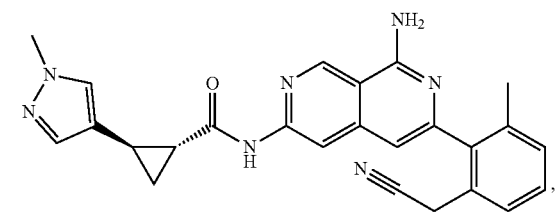
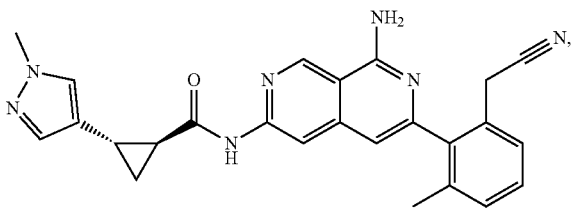
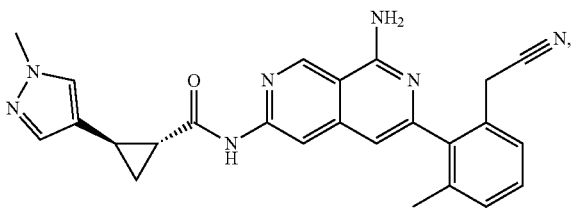
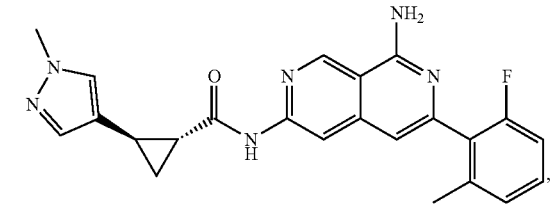
1366
-continued
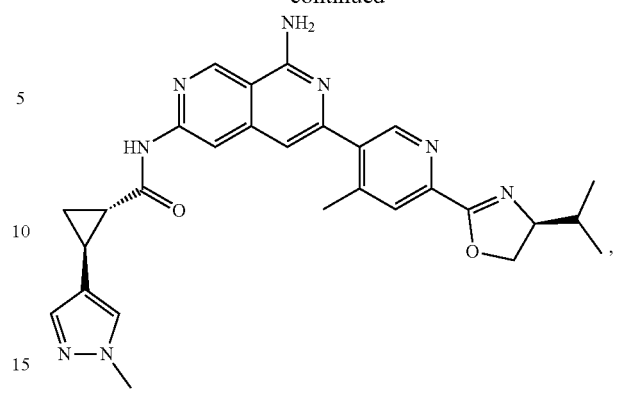
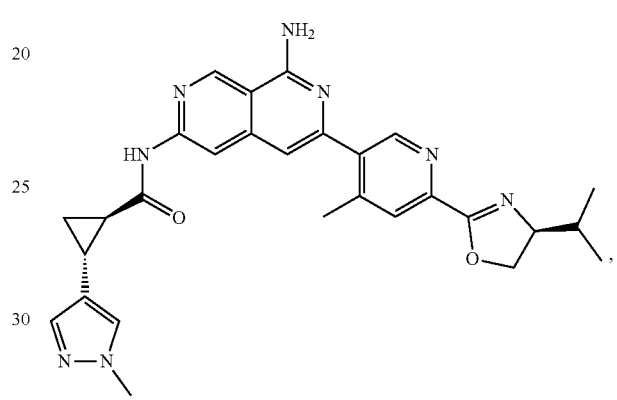
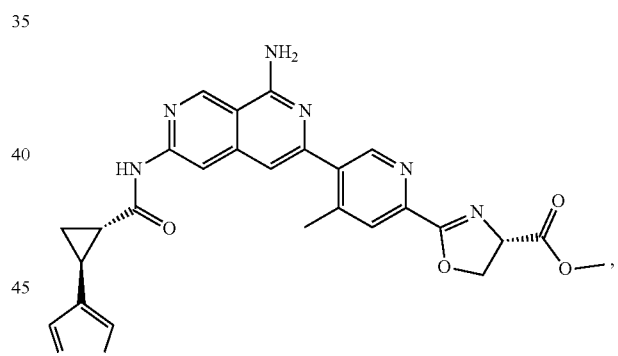
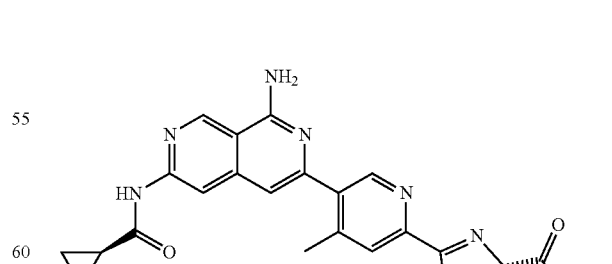
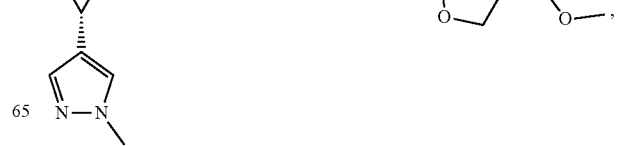

1367
-continued
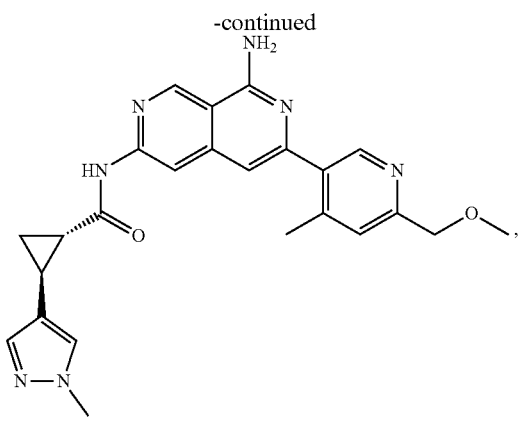
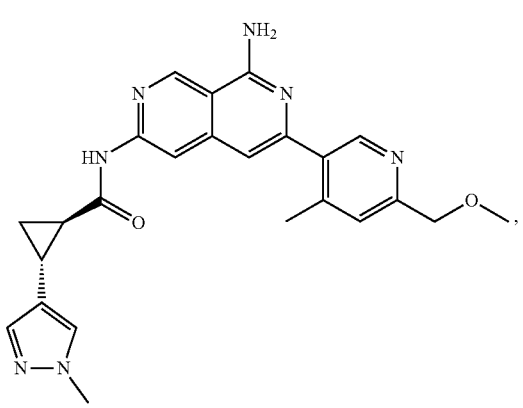
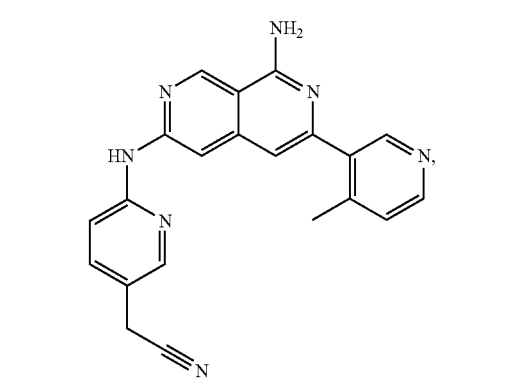
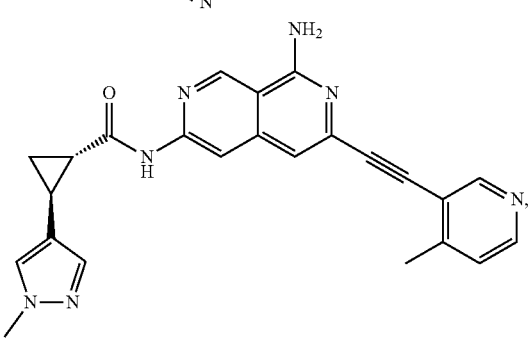
1368
-continued
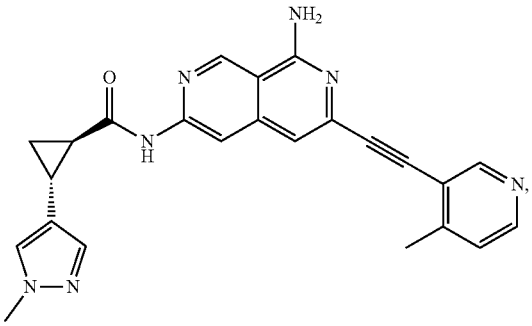
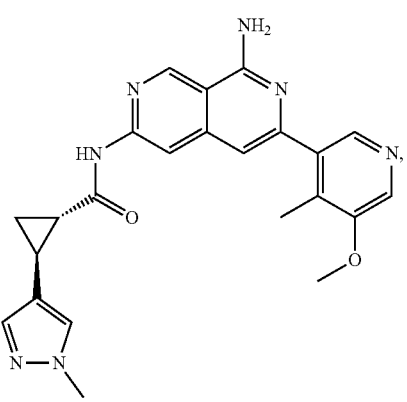
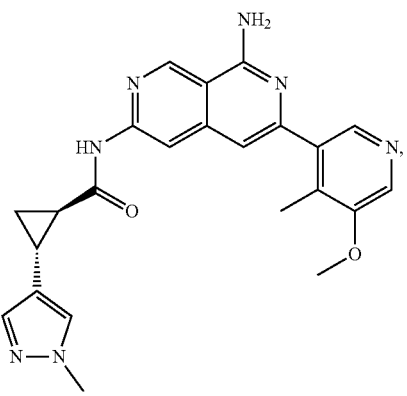

1369
-continued
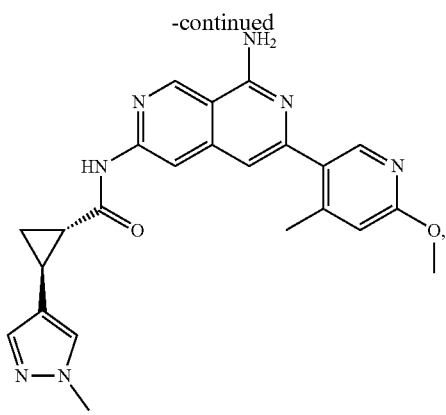
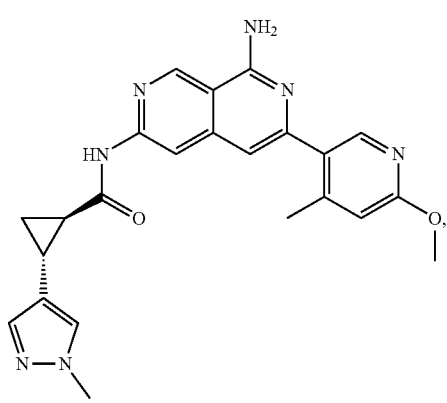
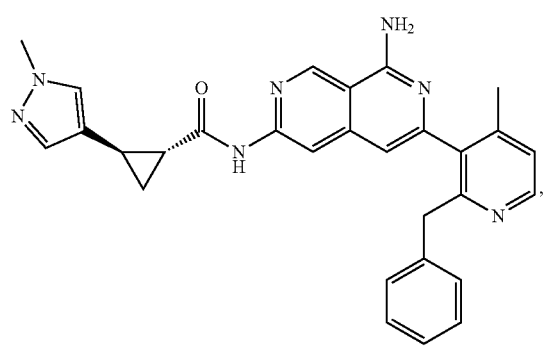
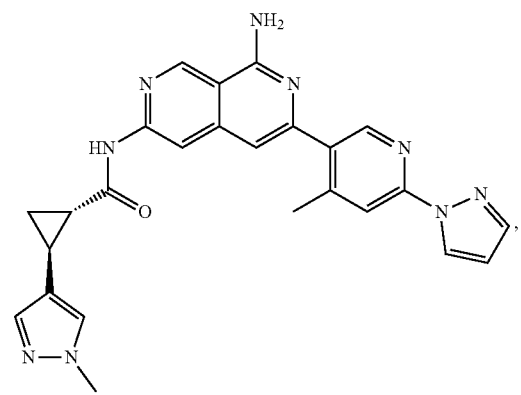
1370
-continued
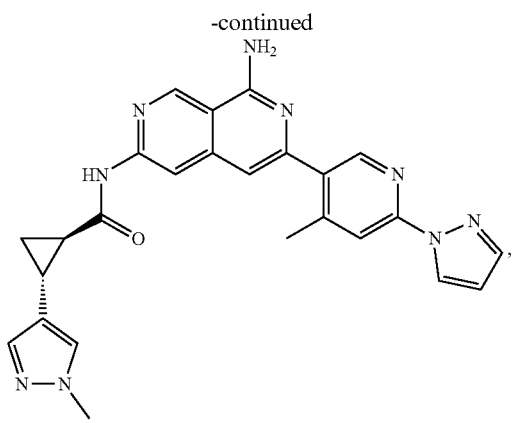
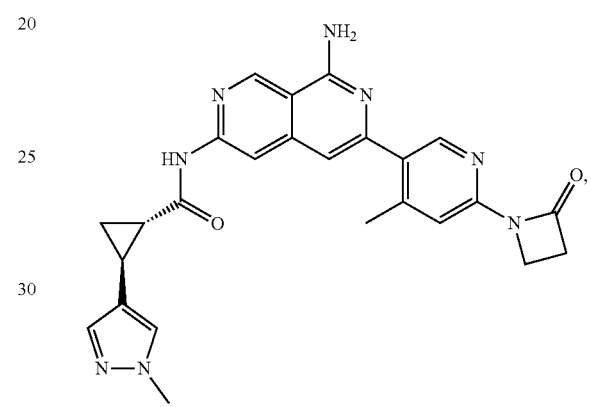
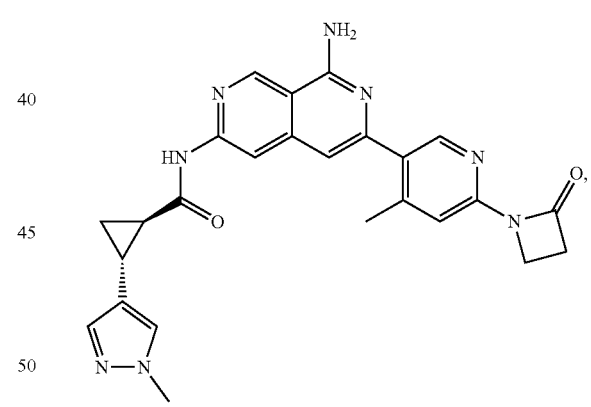
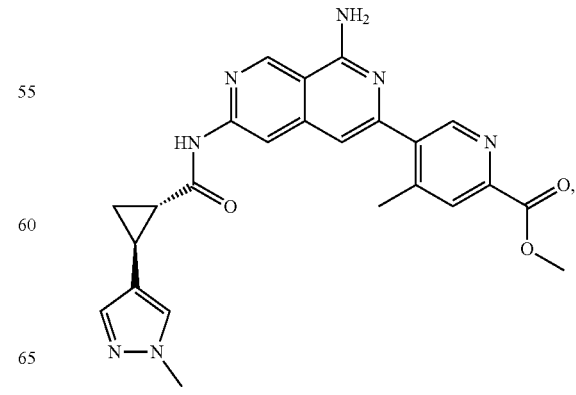

1371
-continued
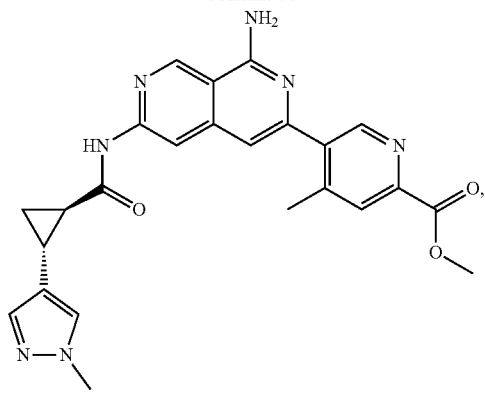
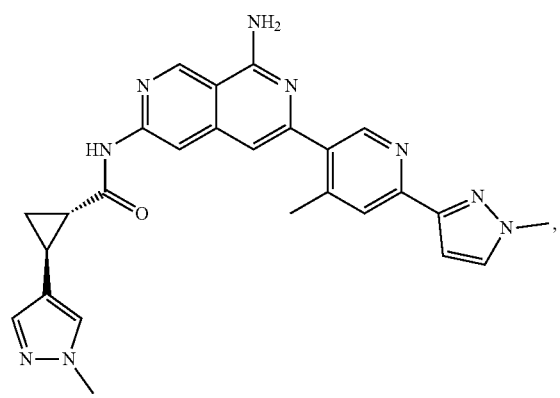
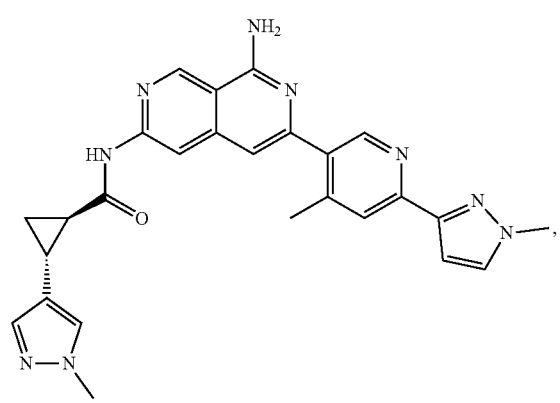
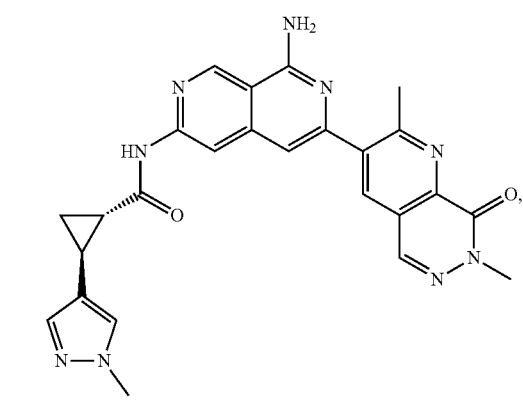
1372
-continued
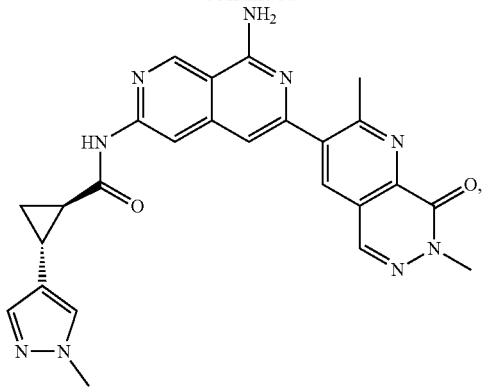
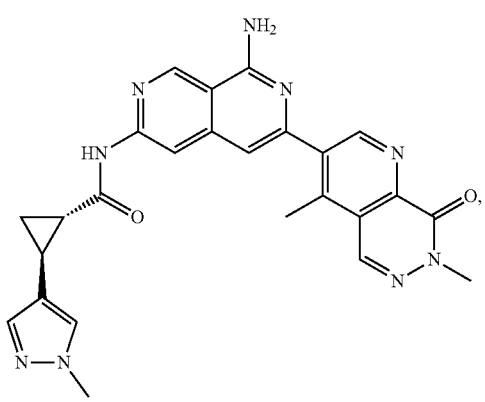
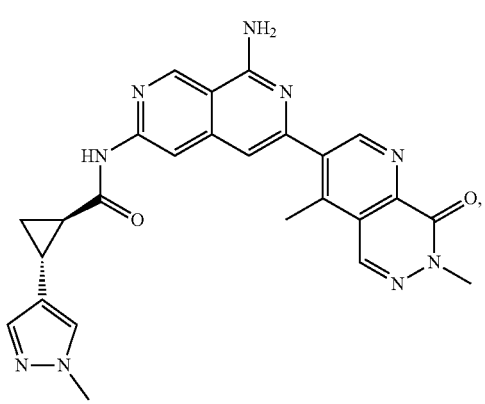
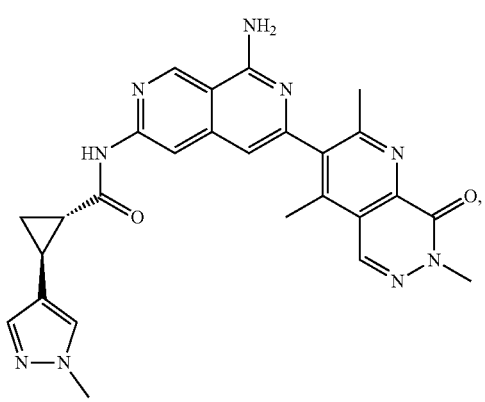

1373
-continued
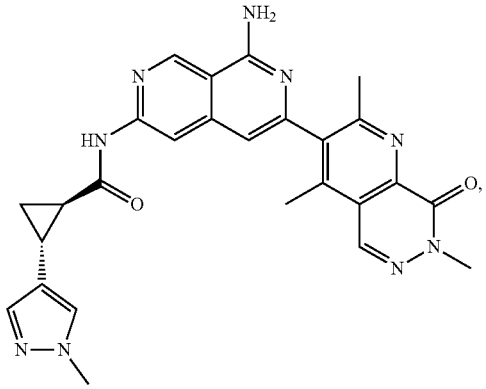
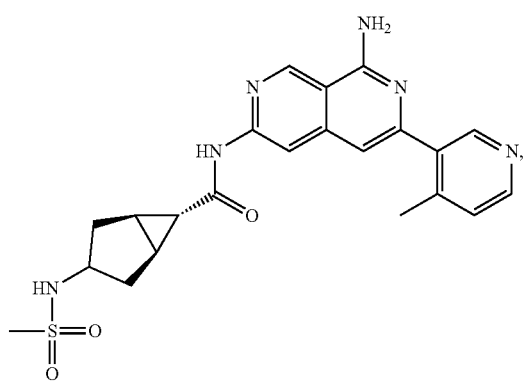
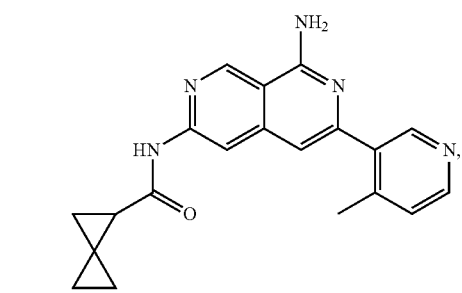
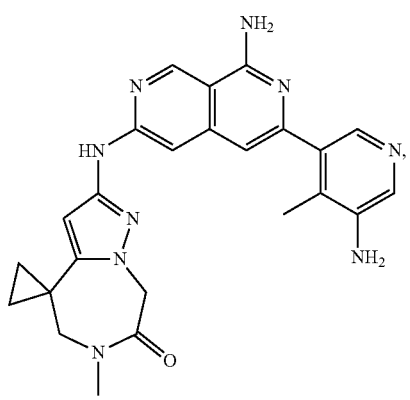
1374
-continued
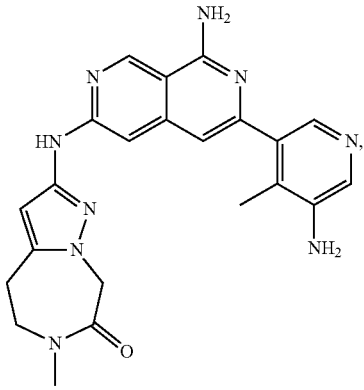
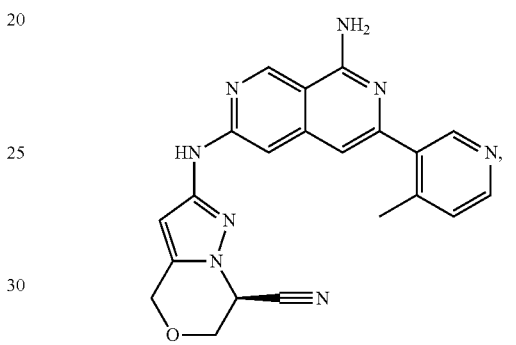
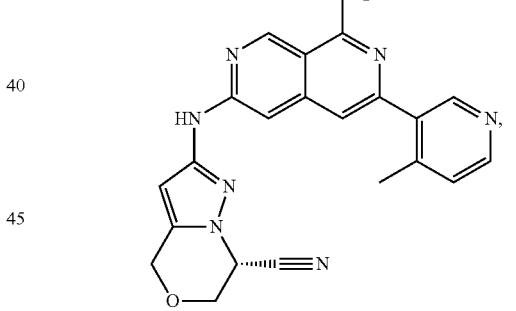
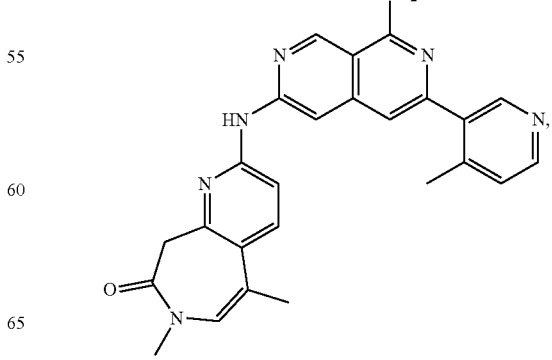

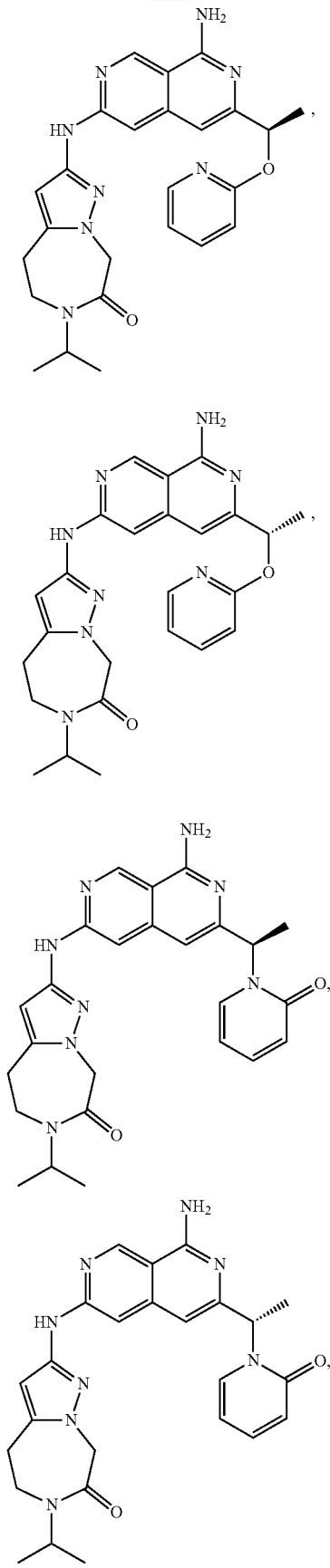
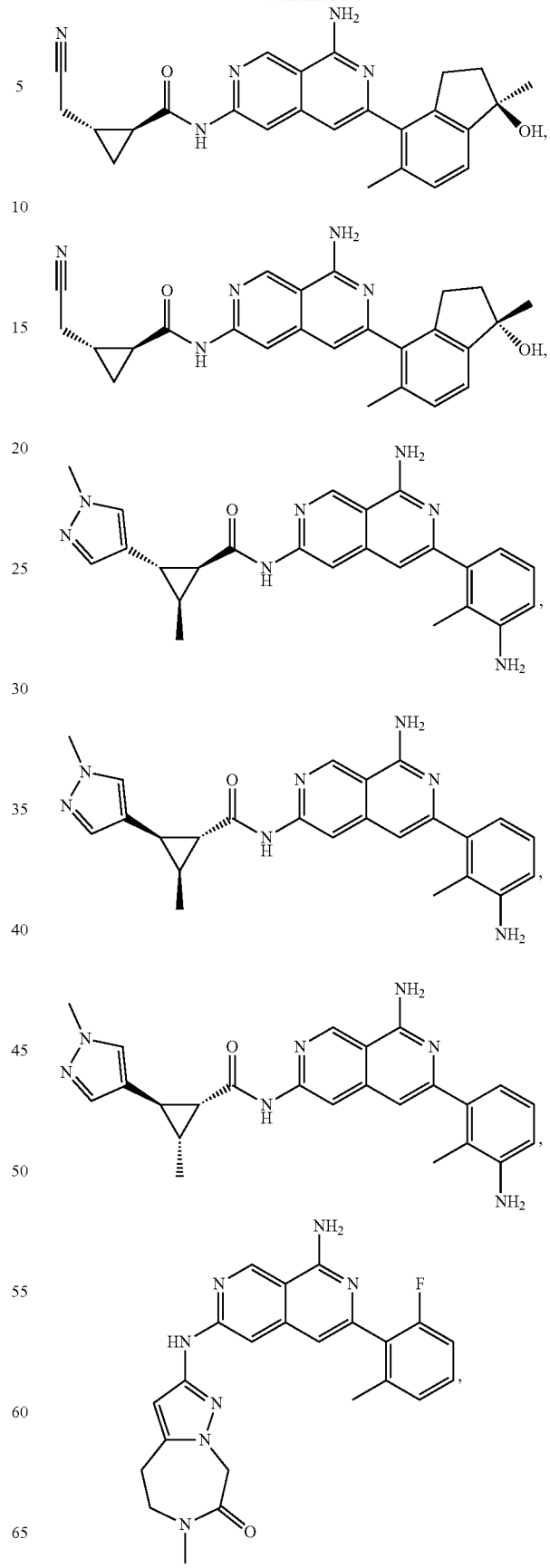

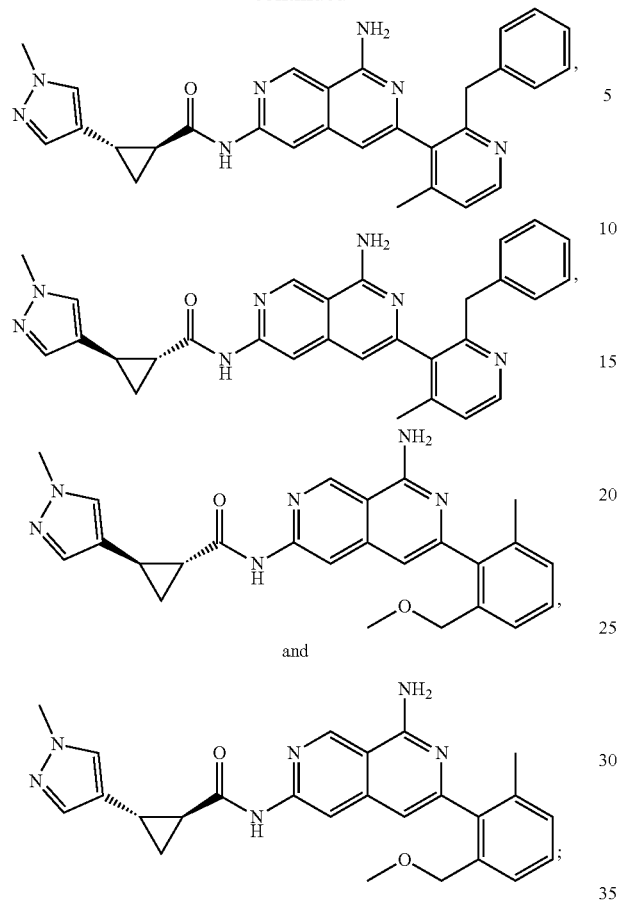
or a pharmaceutically acceptable salt thereof.
17. The method of claim 3, wherein the compound is selected from the group consisting of Compound Nos. 430-572 in Table 3, having the structures:
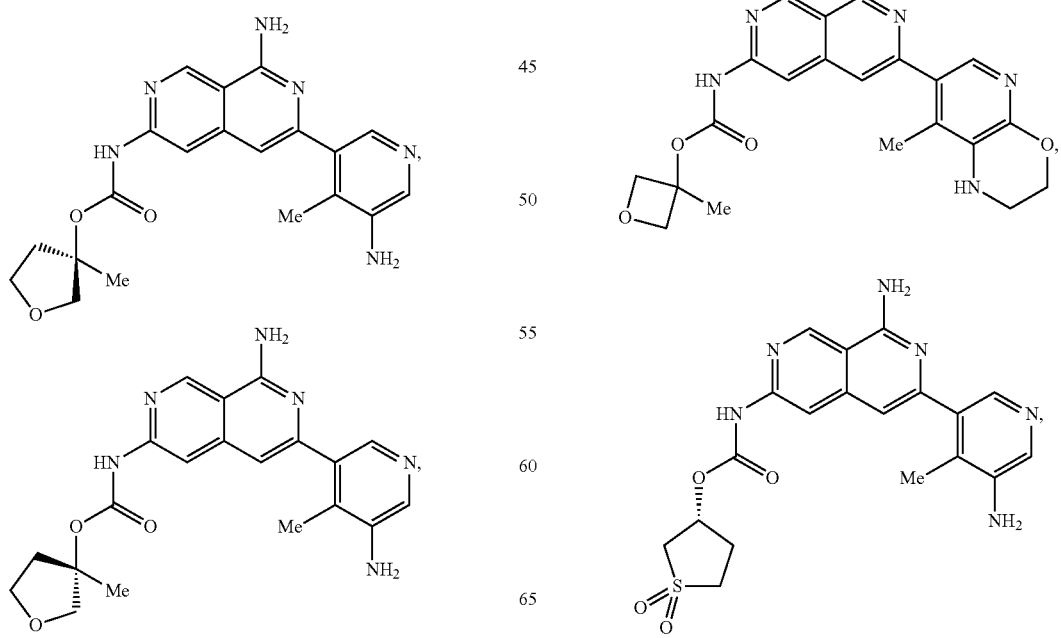

1379
-continued
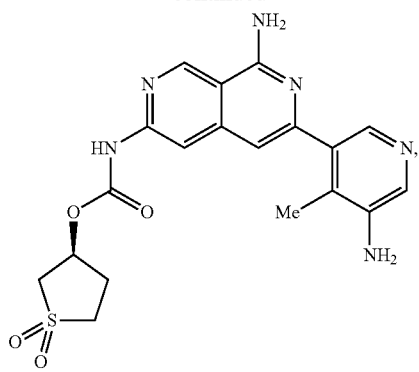
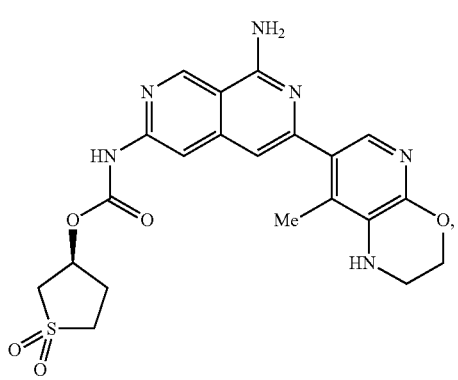
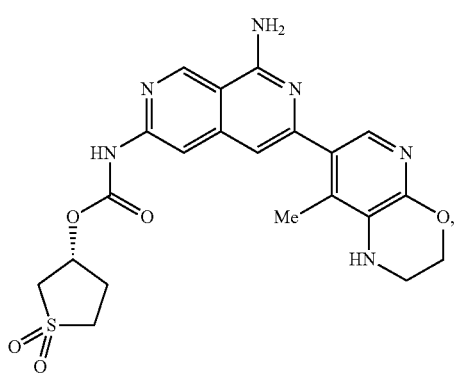
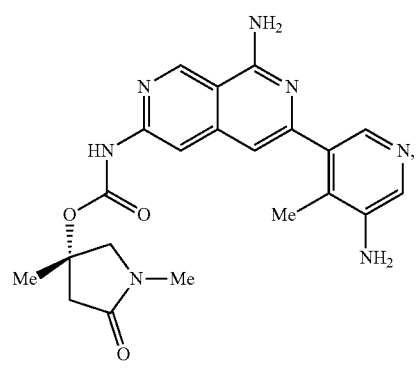
1380
-continued
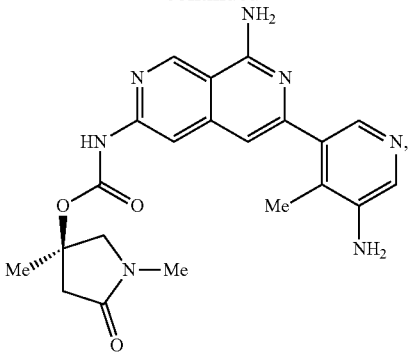
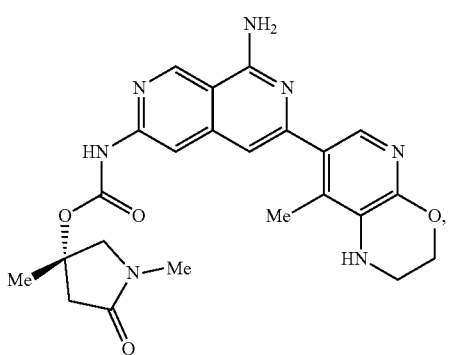
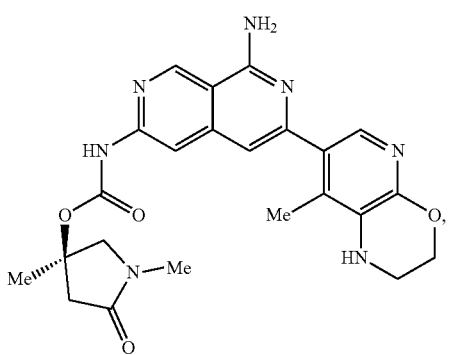
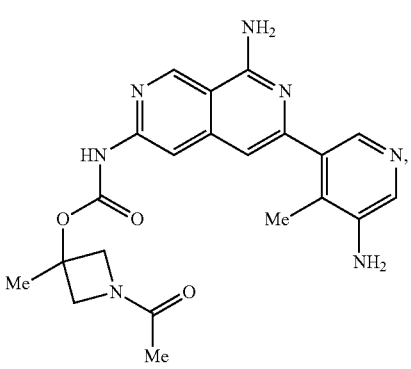

1381
-continued
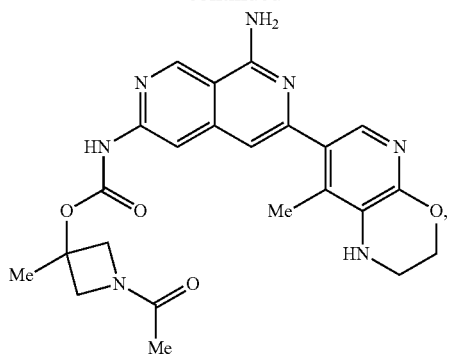
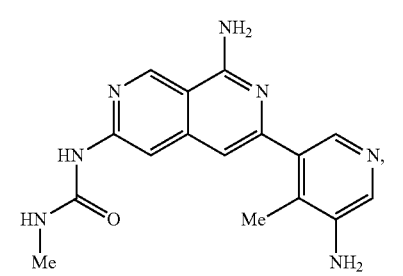
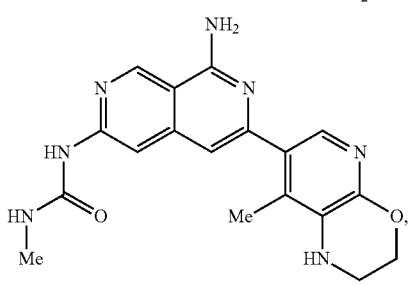
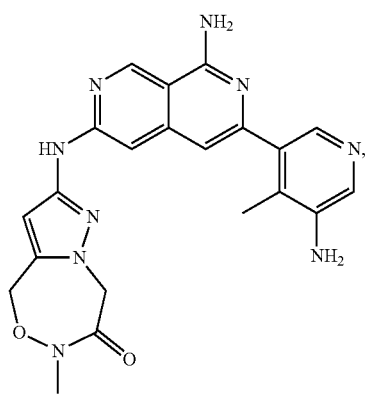
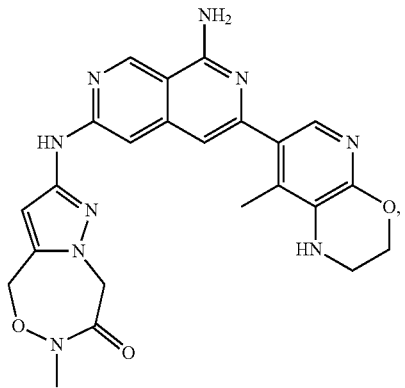
1382
-continued
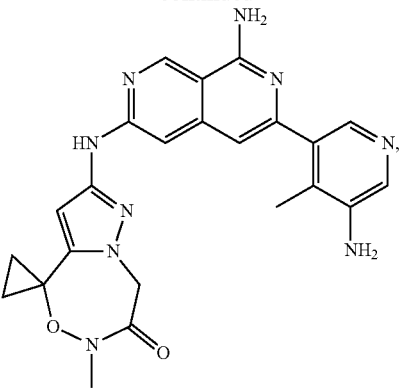
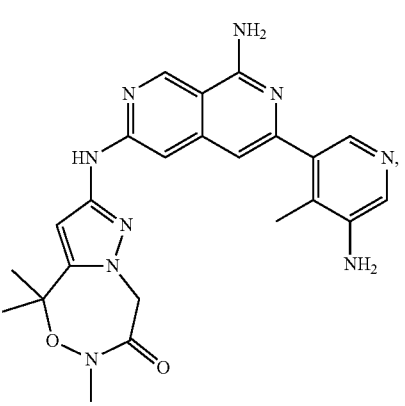
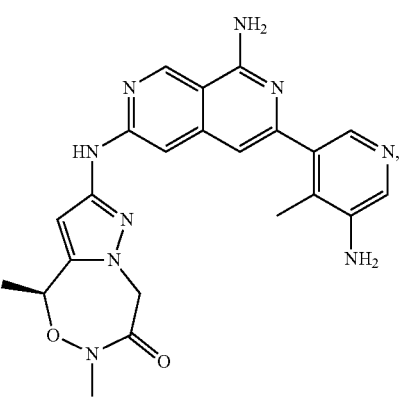
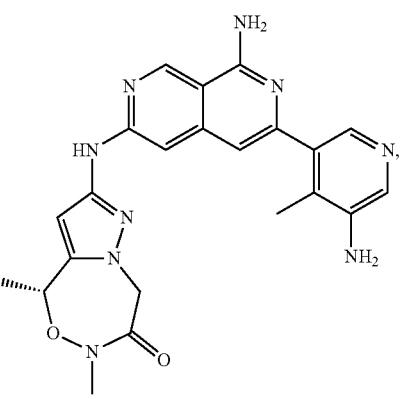

1383
-continued
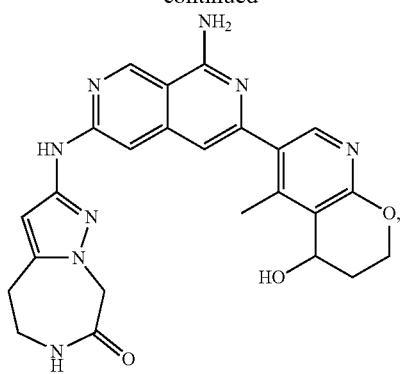
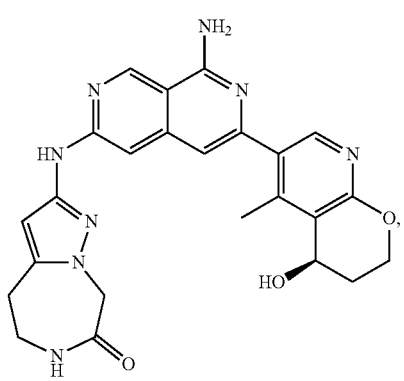
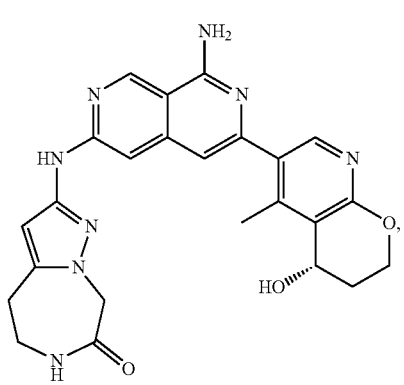
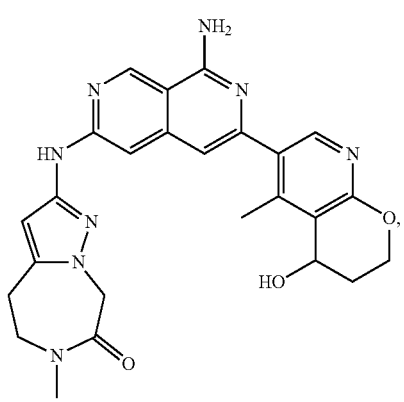
1384
-continued
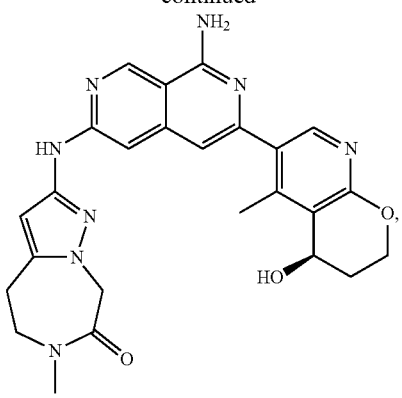
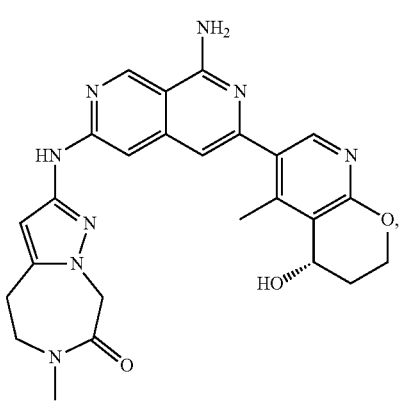
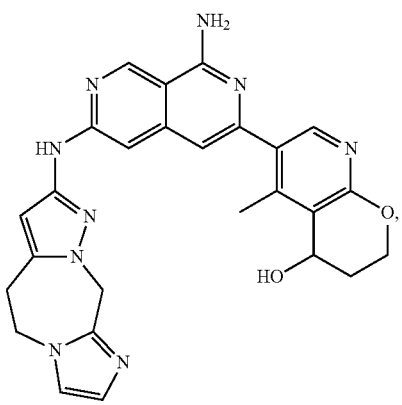
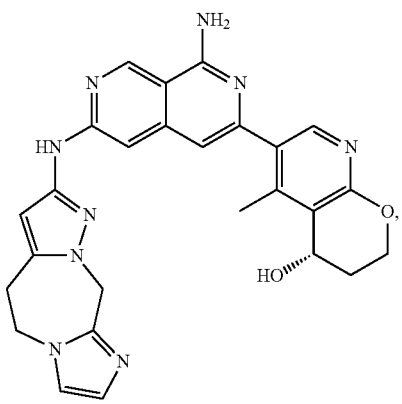

1385
-continued
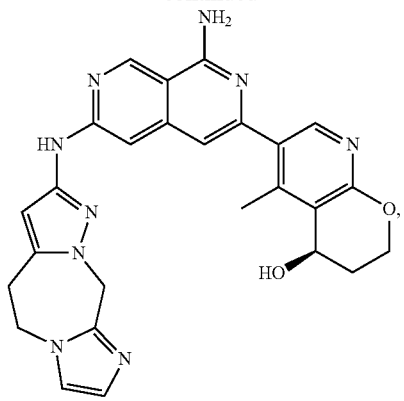
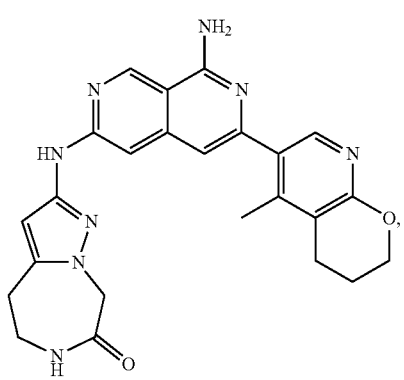
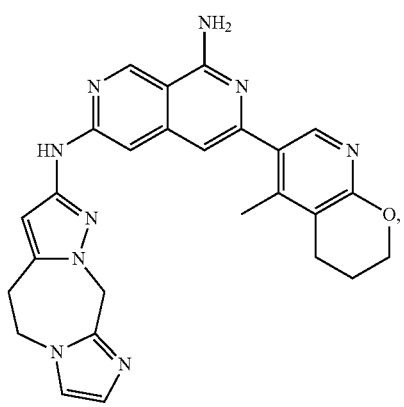
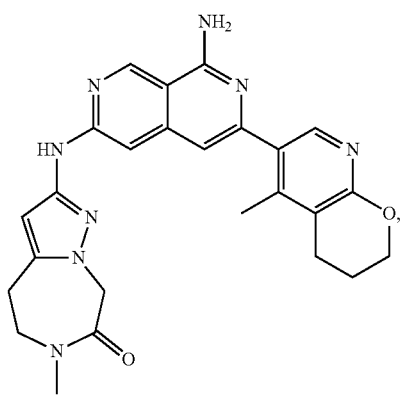
1386
-continued
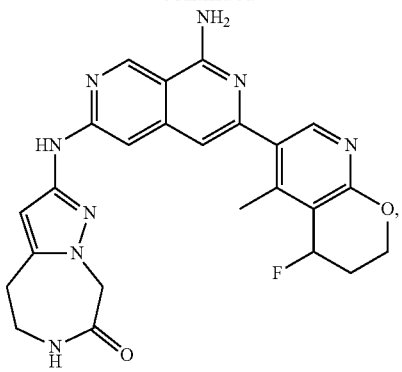
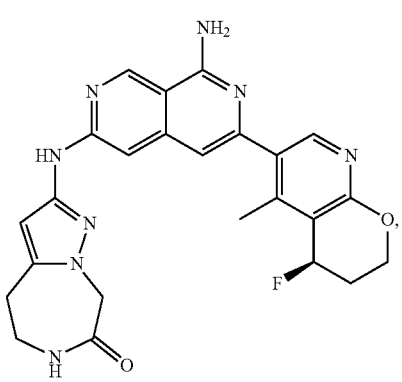
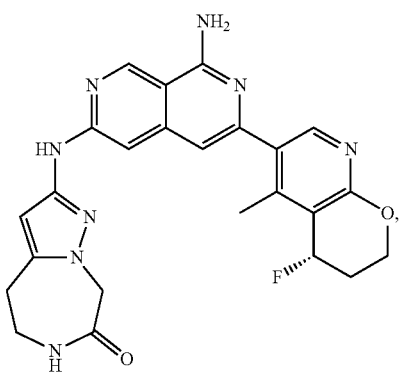
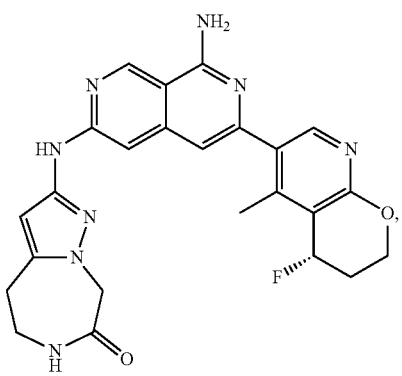

1387
-continued
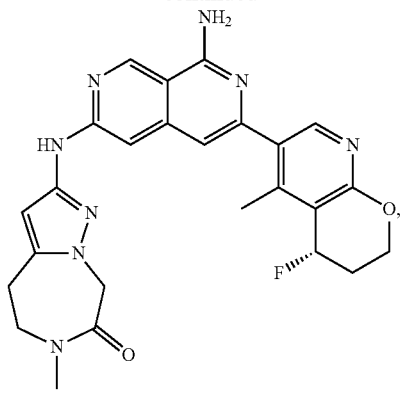
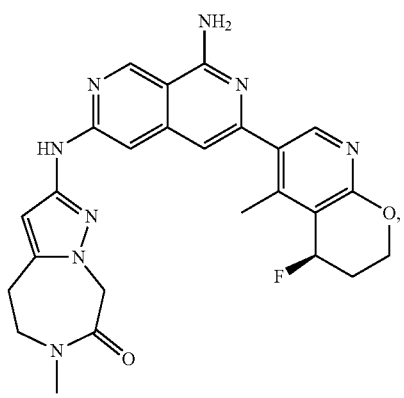
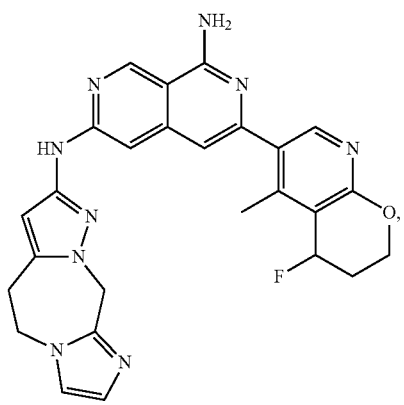
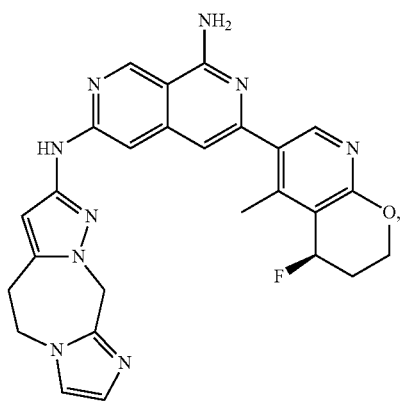
1388
-continued
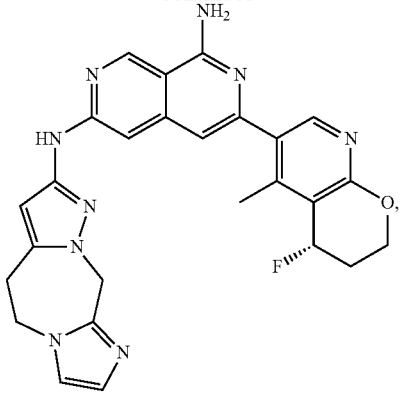
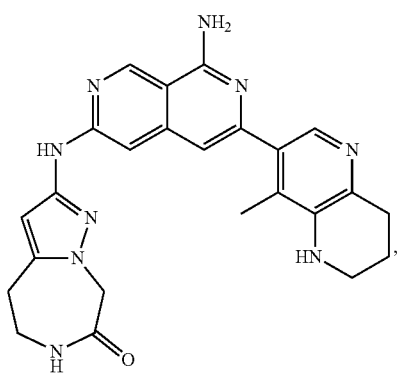
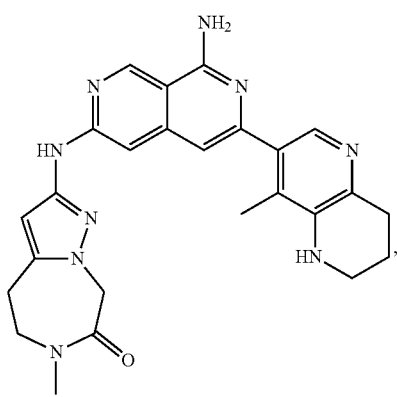
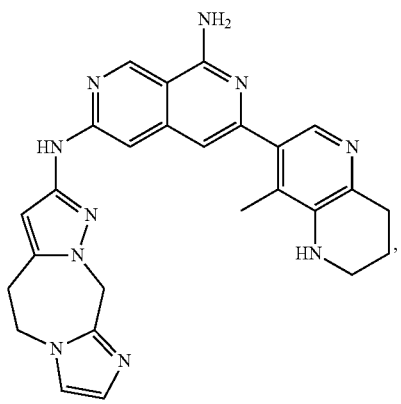

1389
-continued
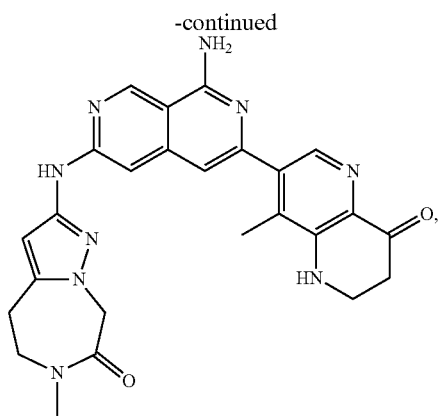
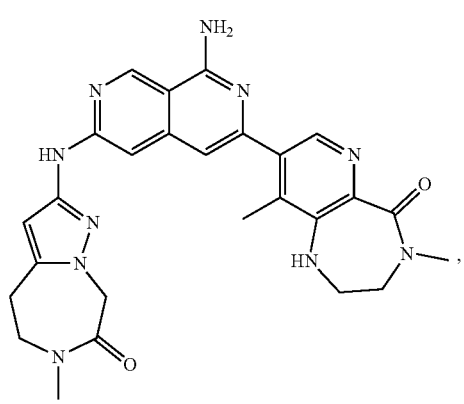
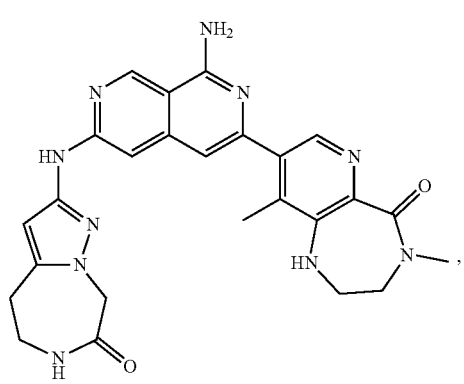
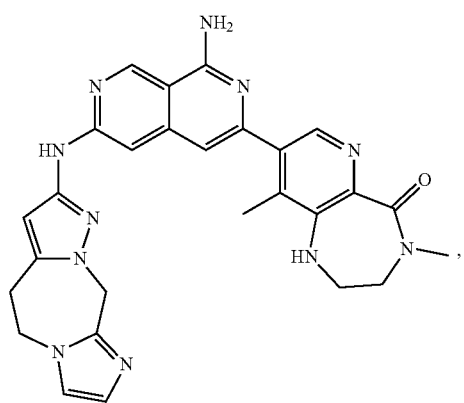
1390
-continued
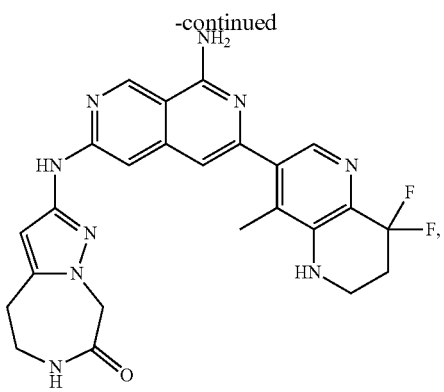
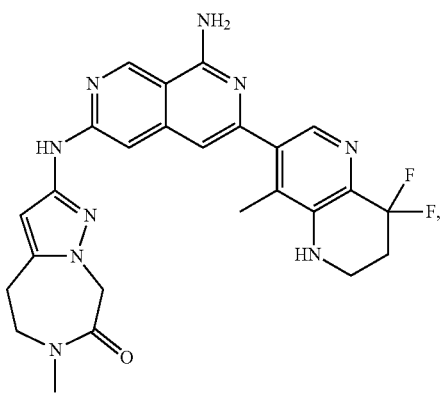
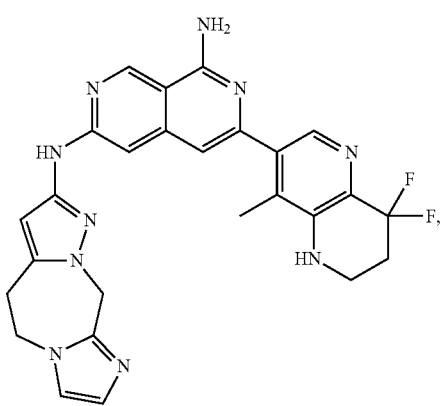
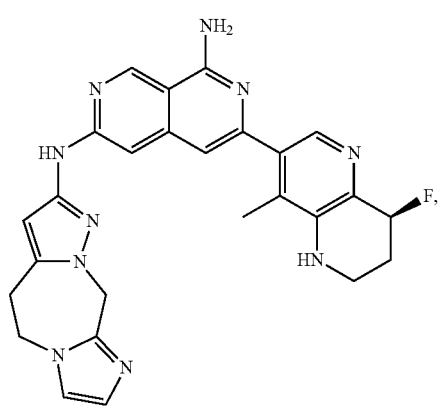

1391
-continued
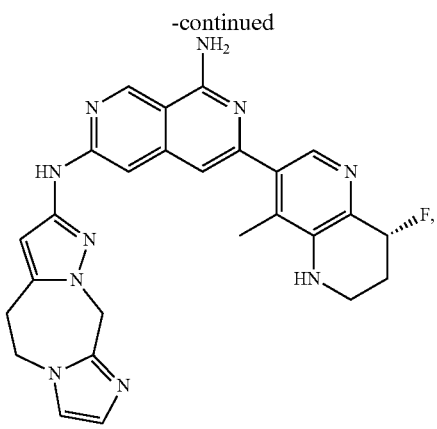
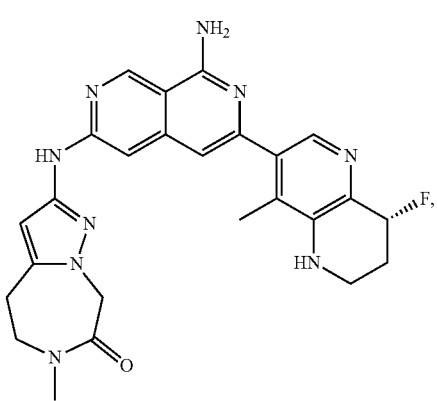
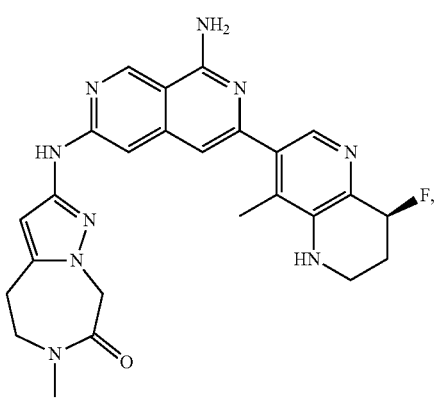
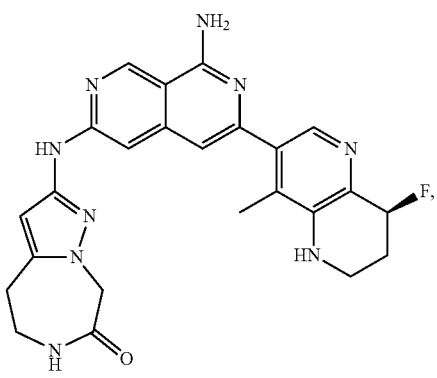
1392
-continued
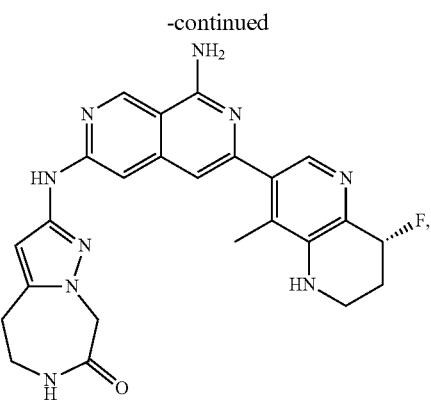
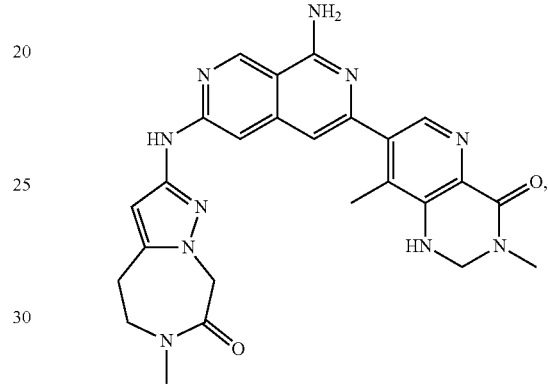
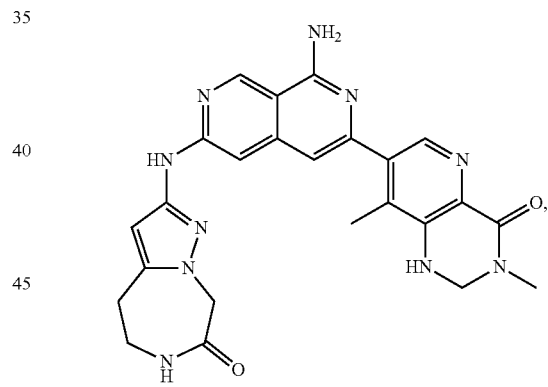
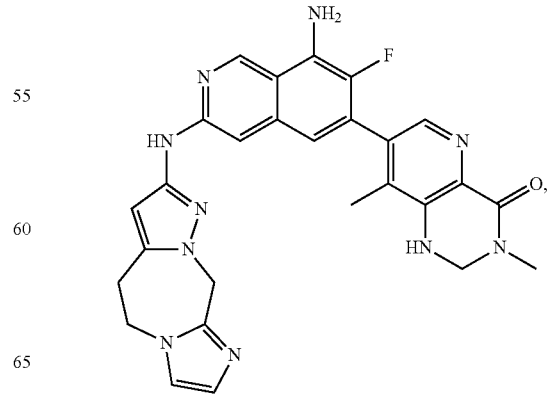

1393
-continued
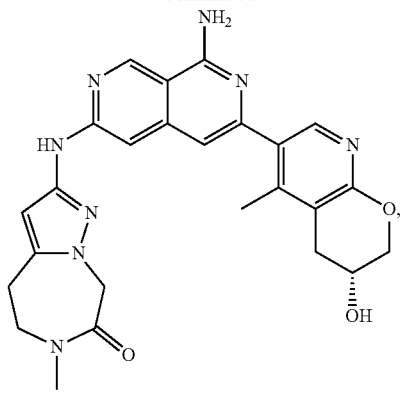
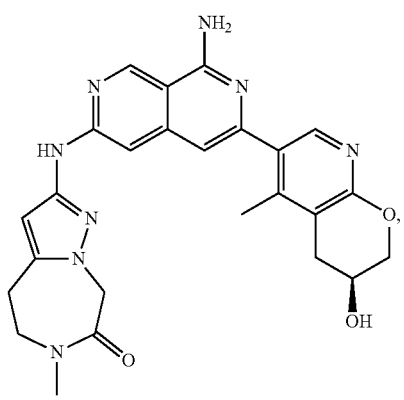
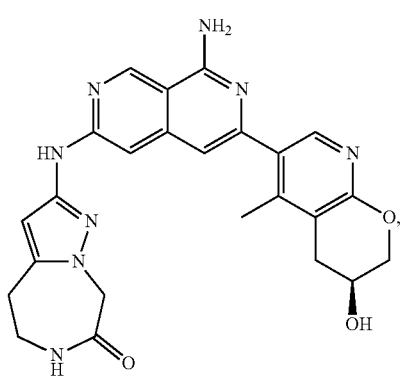
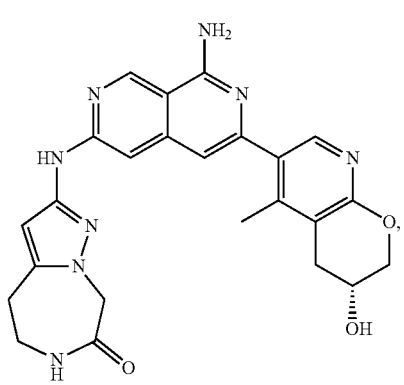
1394
-continued
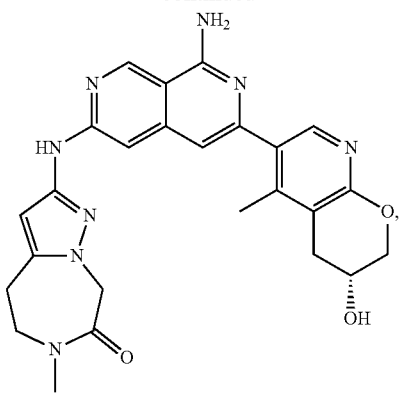
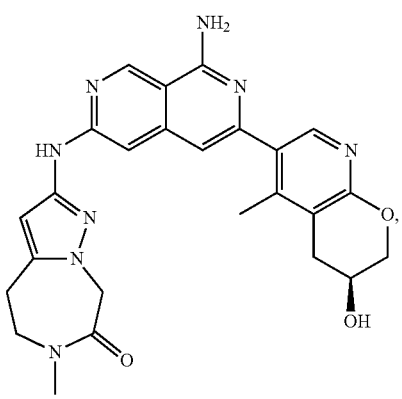
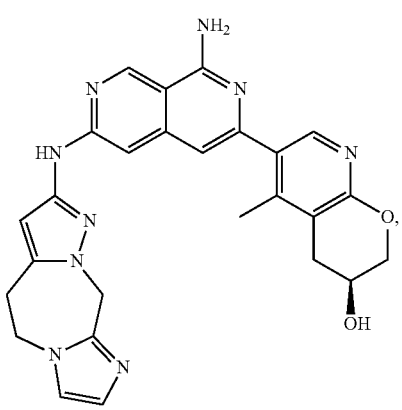
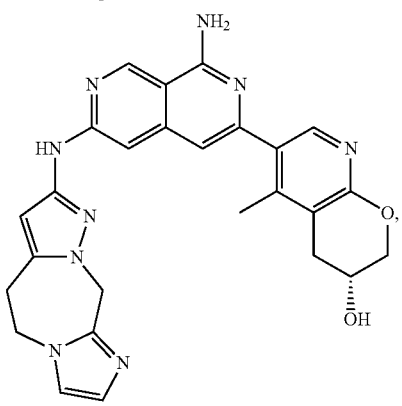

1395
-continued
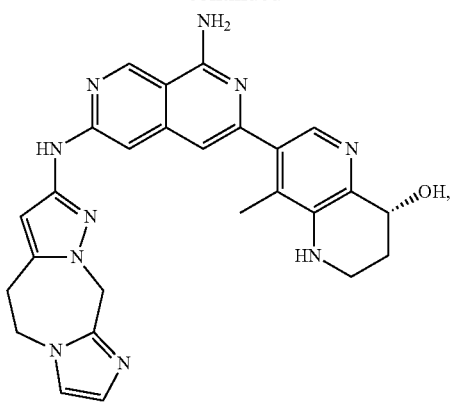
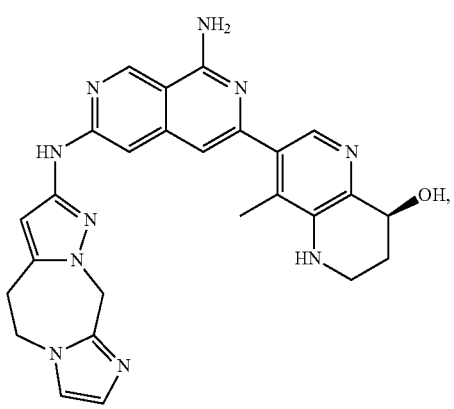
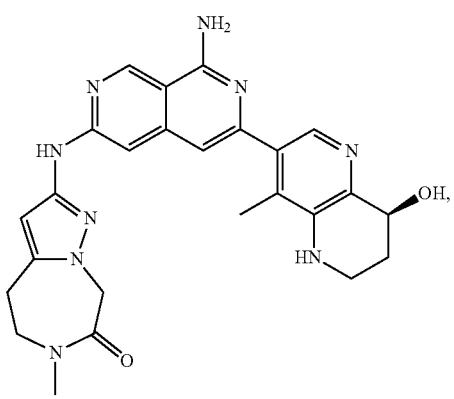
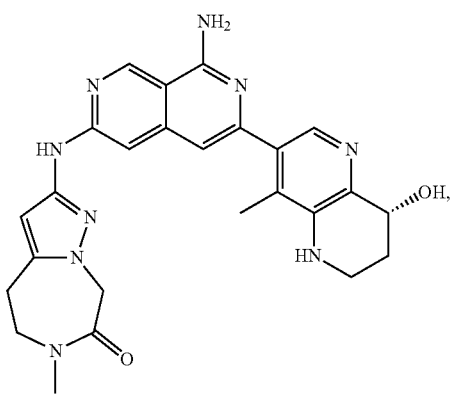
1396
-continued
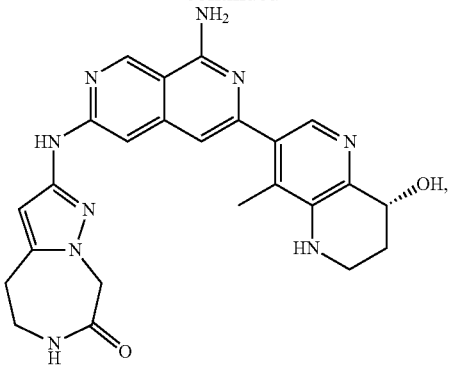
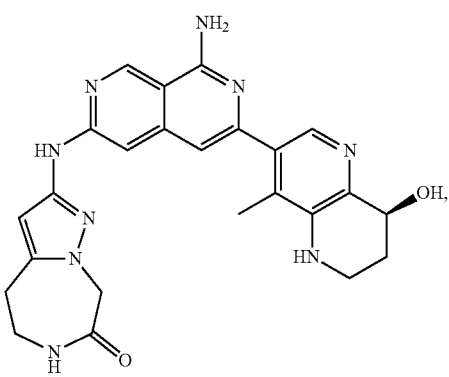
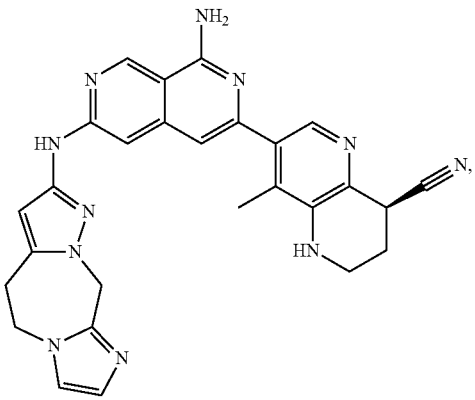
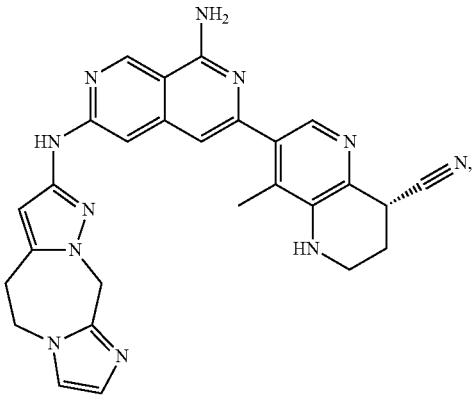

1397
-continued
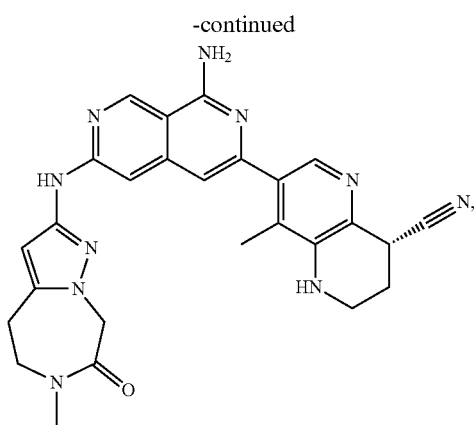
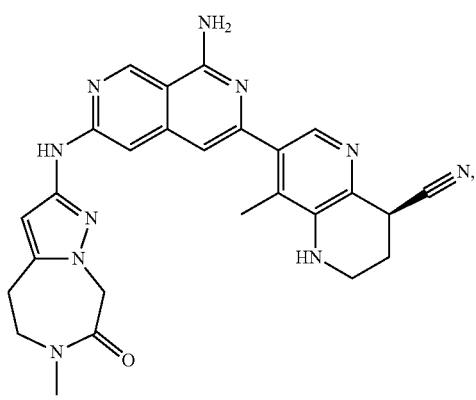
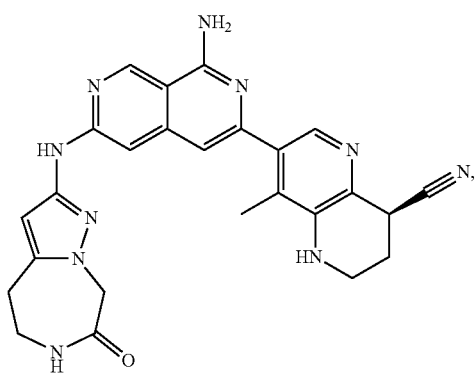
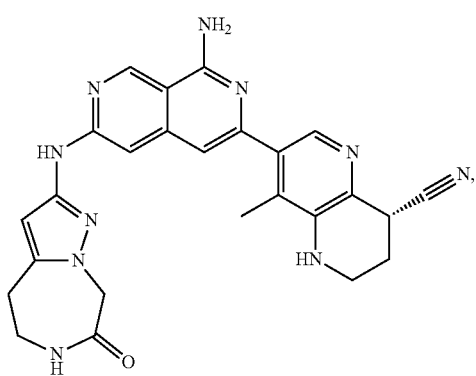
1398
-continued
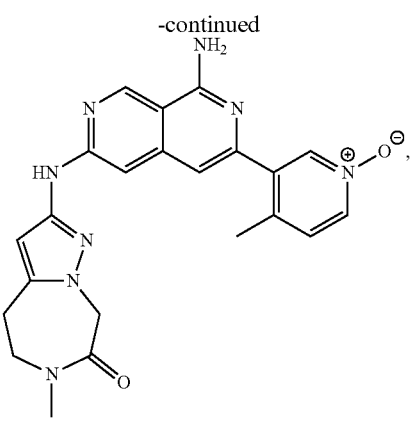
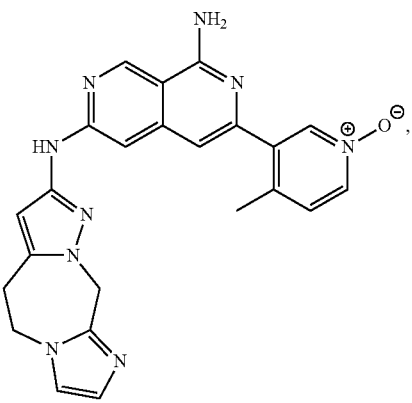
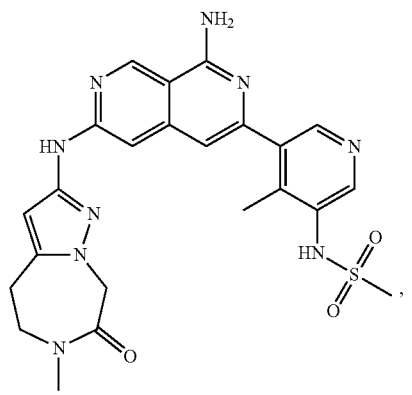
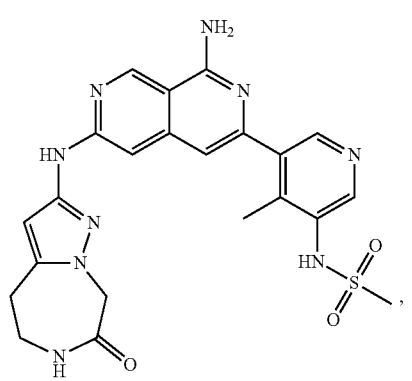

1399
-continued
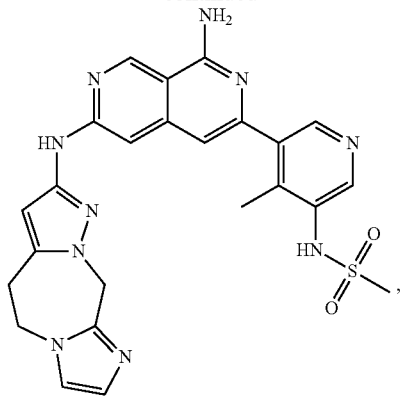
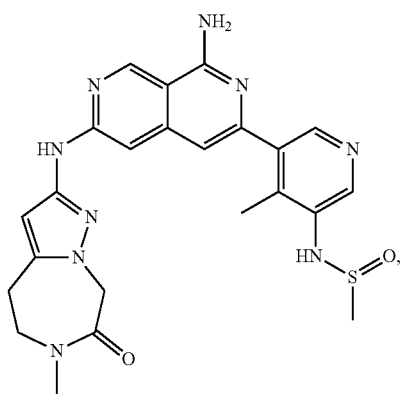
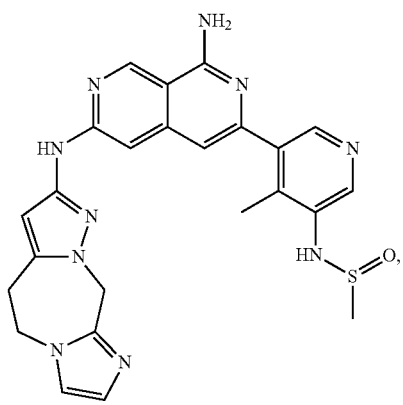
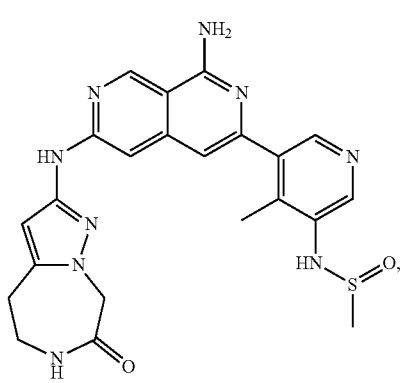
1400
-continued
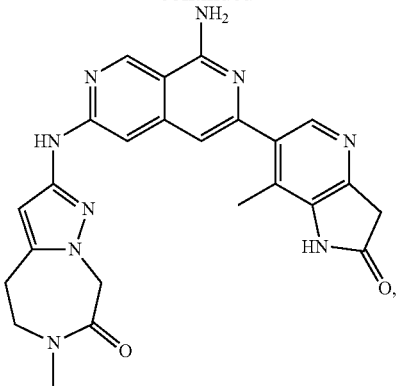
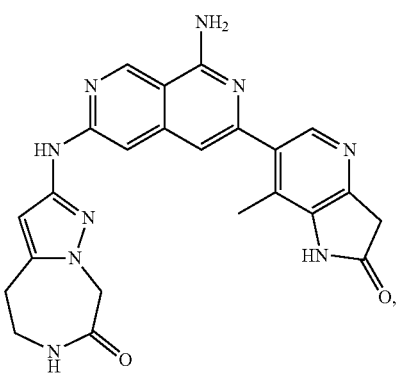
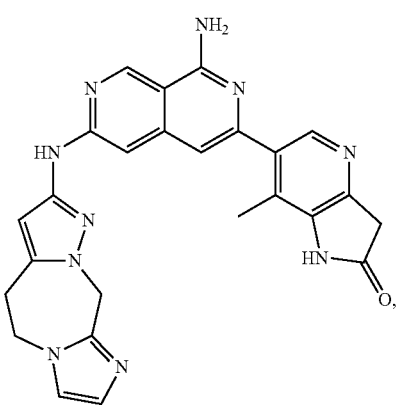
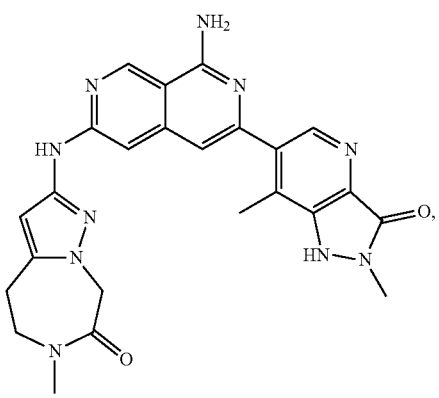

1401
-continued
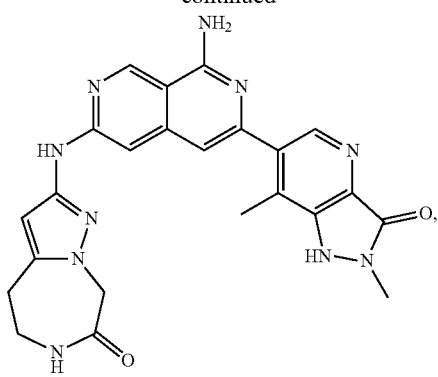
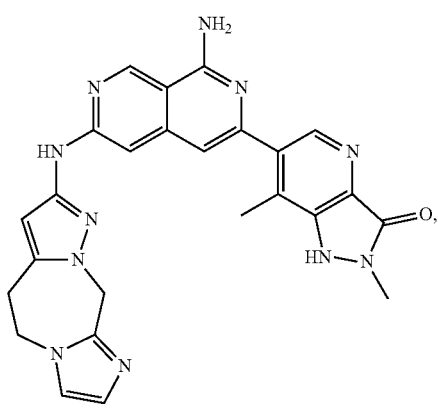
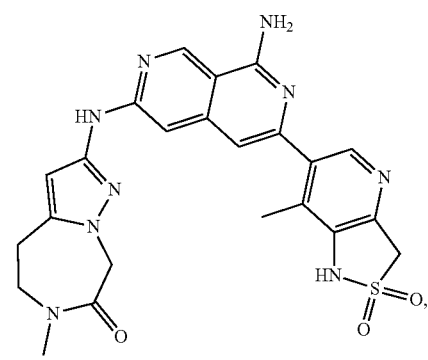
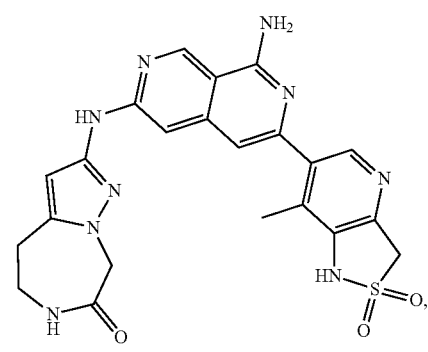
1402
-continued
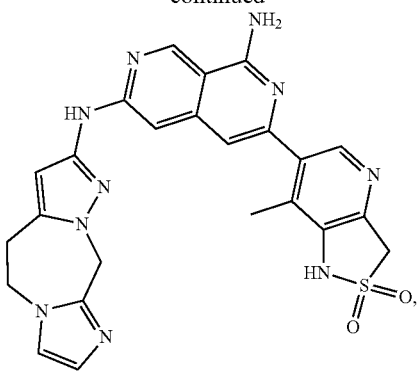
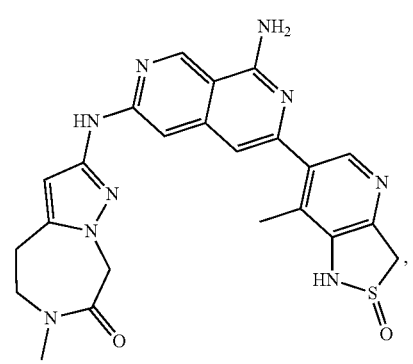
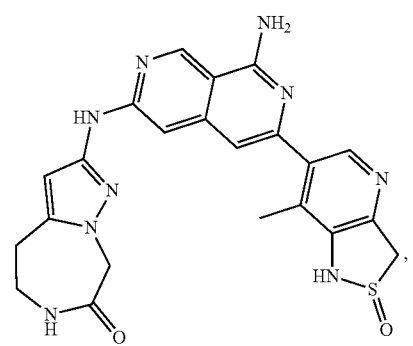
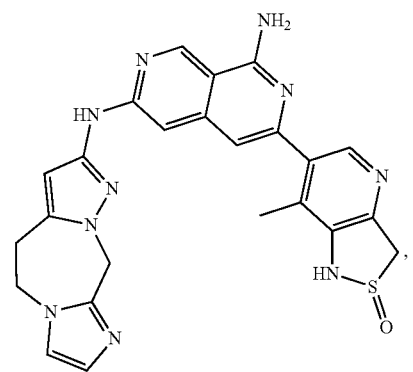

1403
-continued
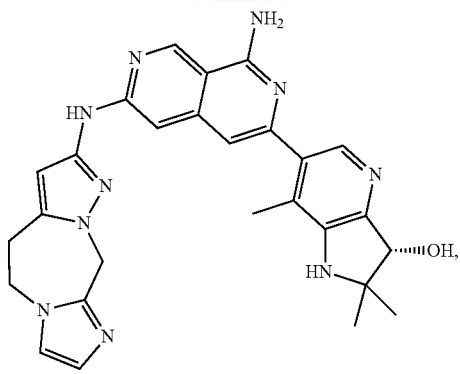
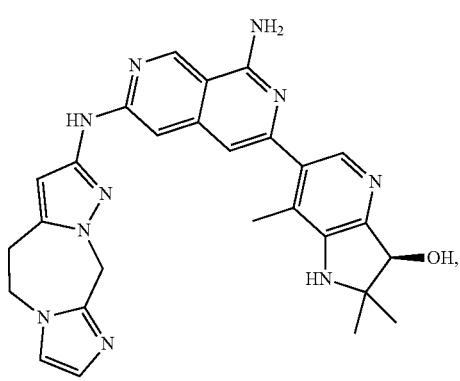
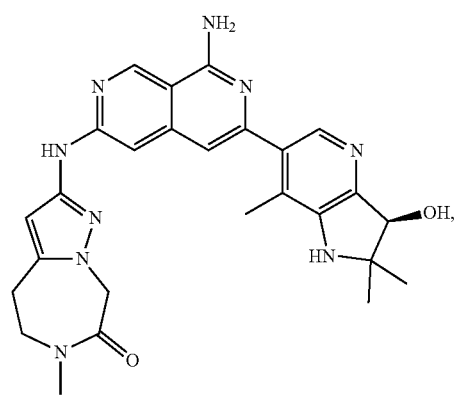
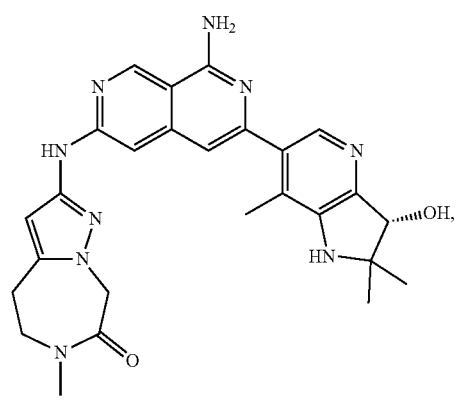
1404
-continued
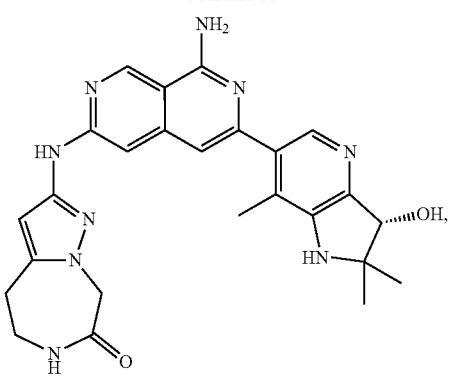
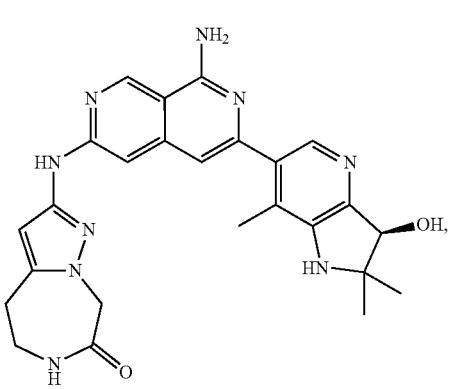
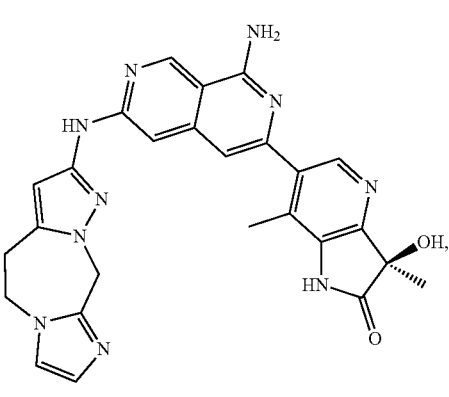
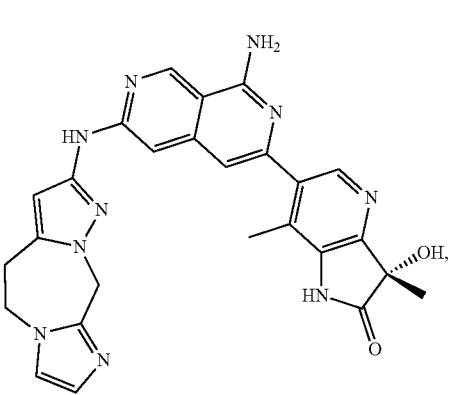

1405
-continued
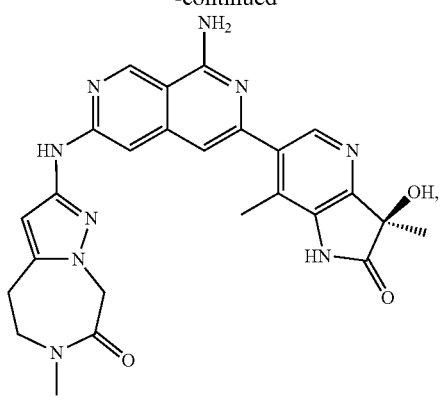
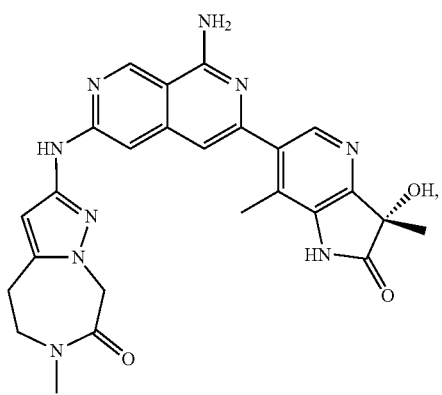
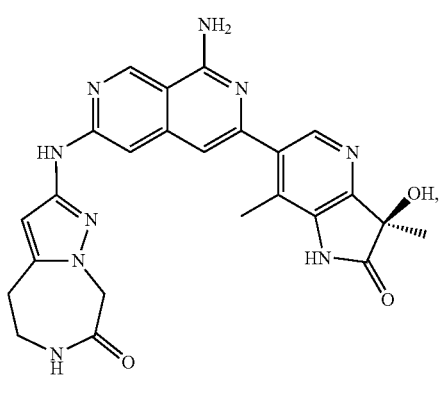
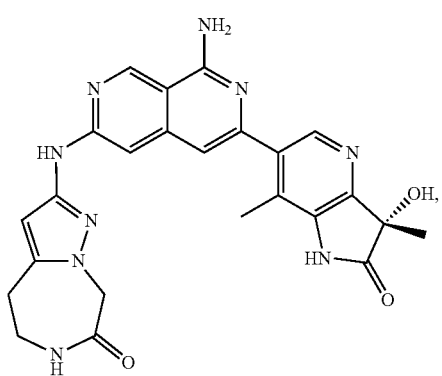
1406
-continued
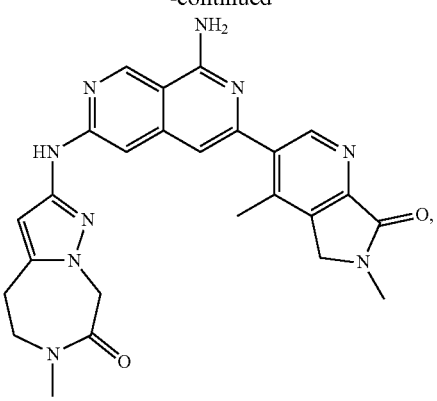
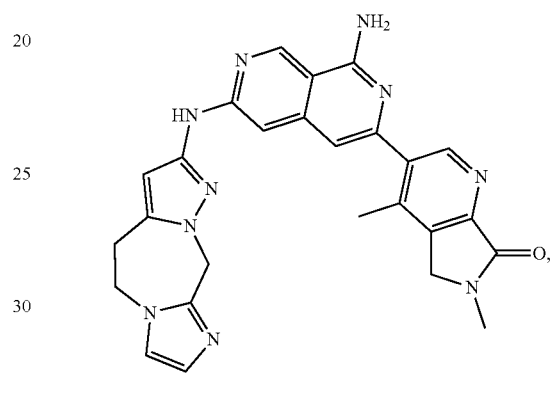
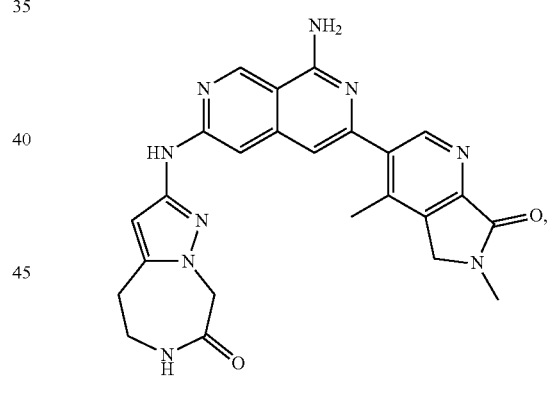
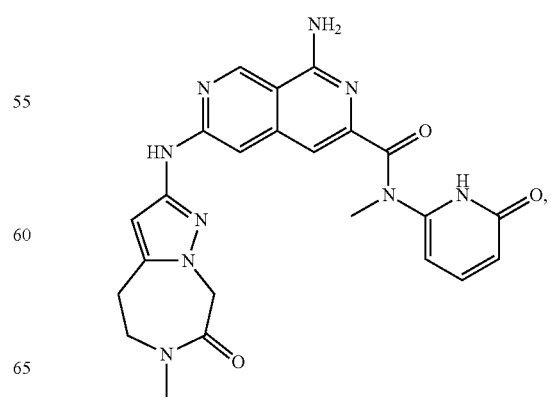

1407
-continued
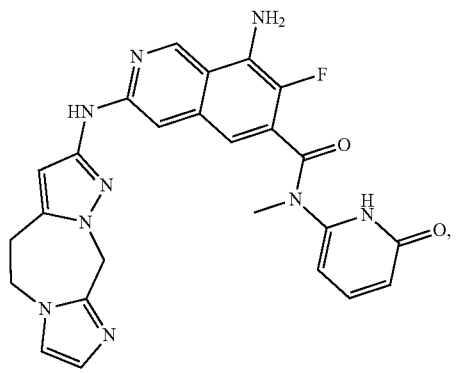
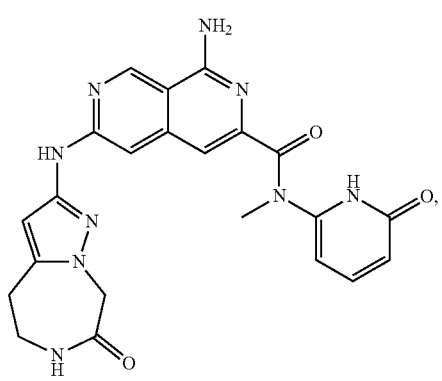
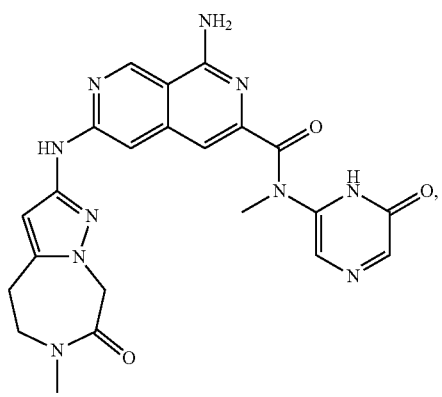
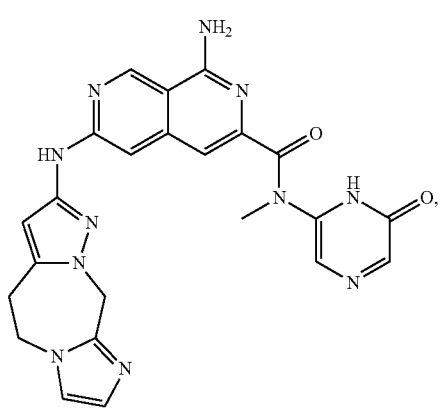
1408
-continued
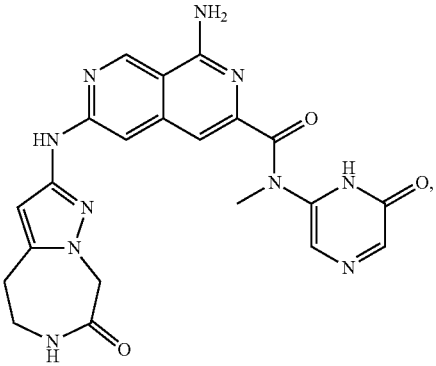
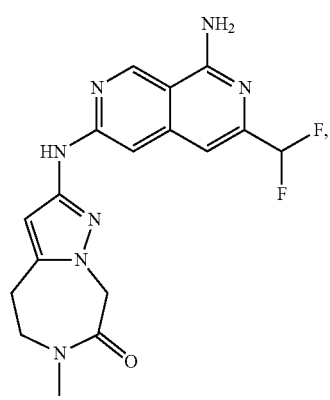
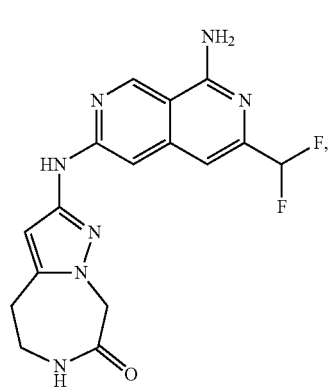
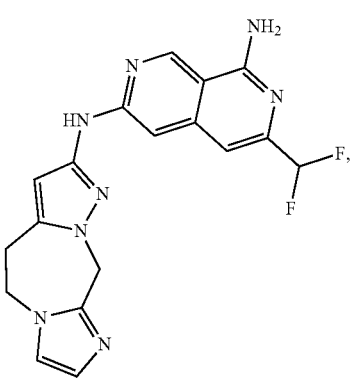

1409
-continued
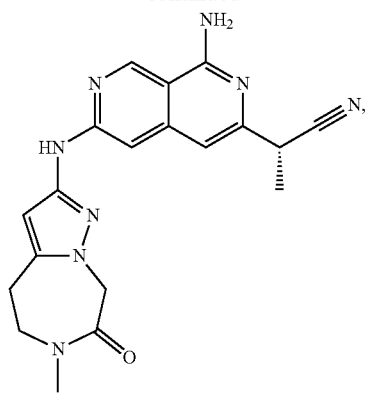
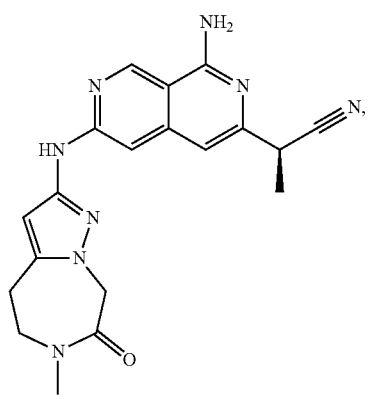
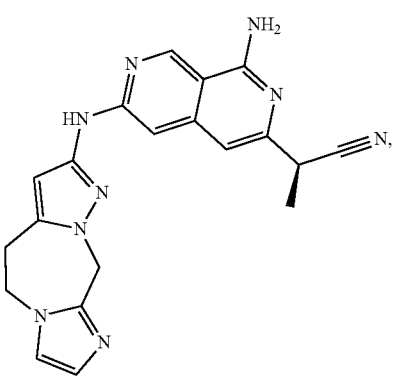
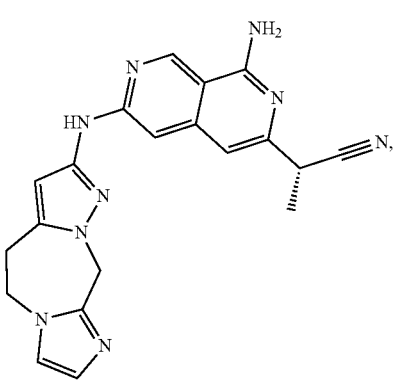
1410
-continued
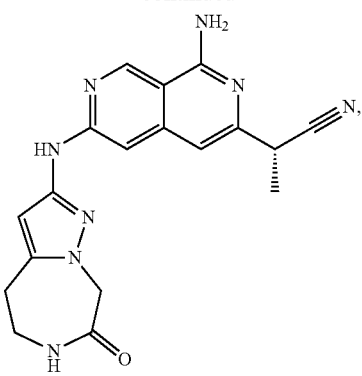
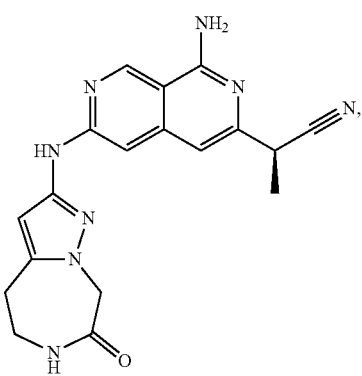
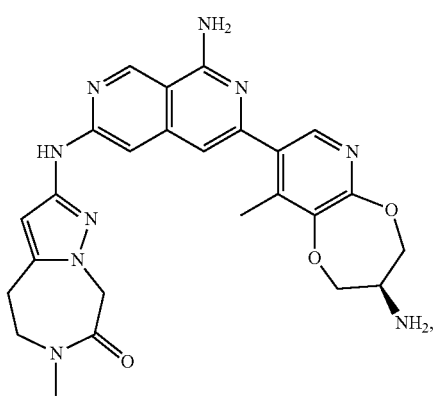
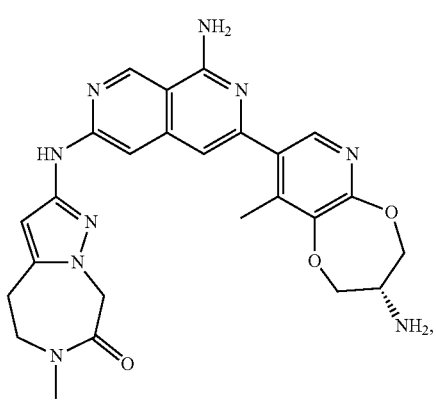

1411
-continued
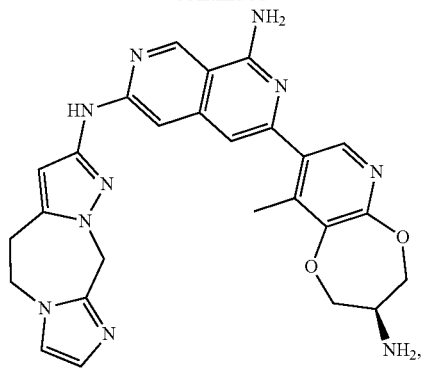
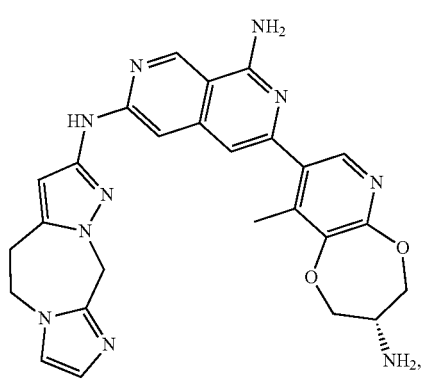
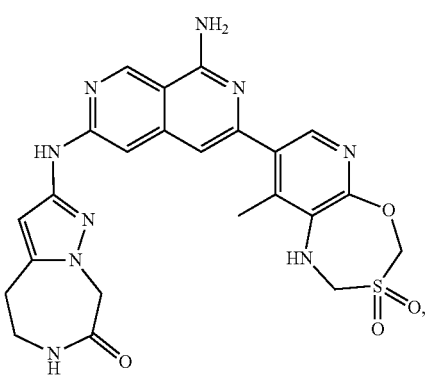
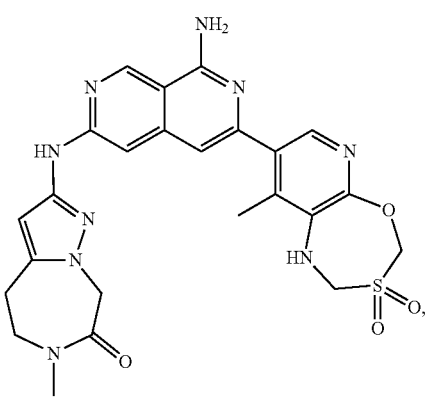
1412
-continued
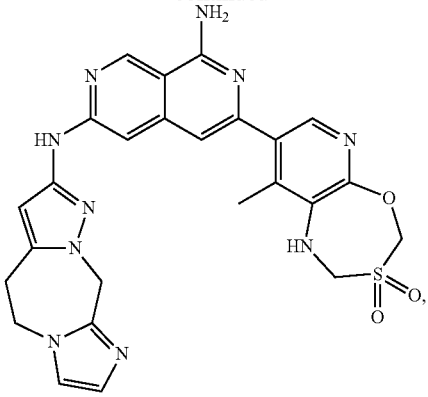
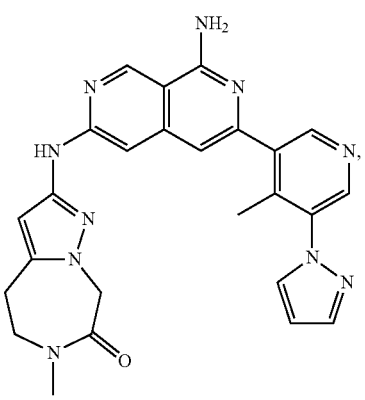
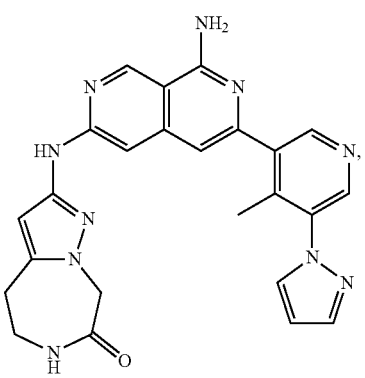
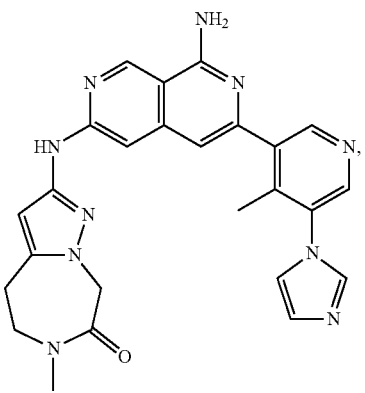

1413
-continued
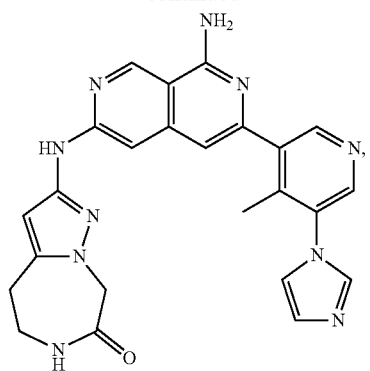
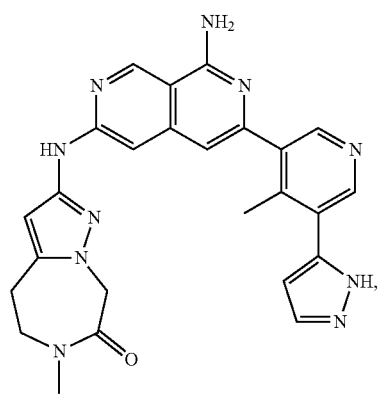
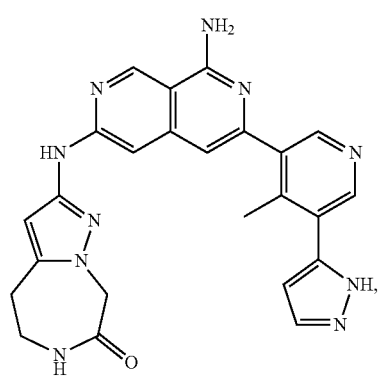
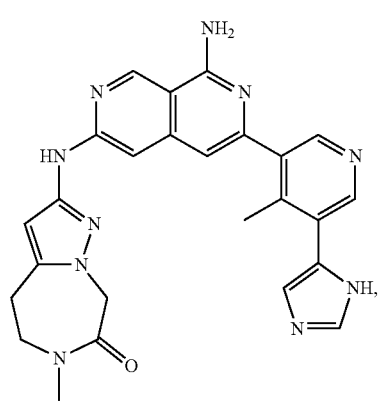
1414
-continued
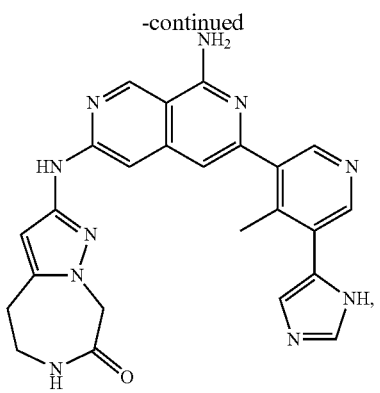
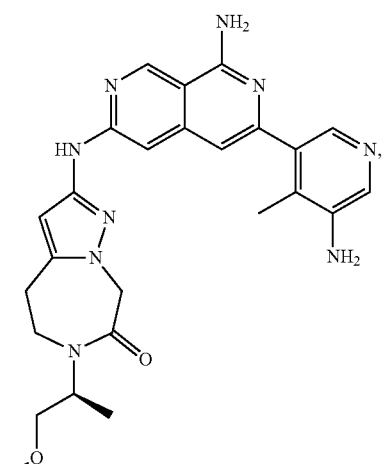
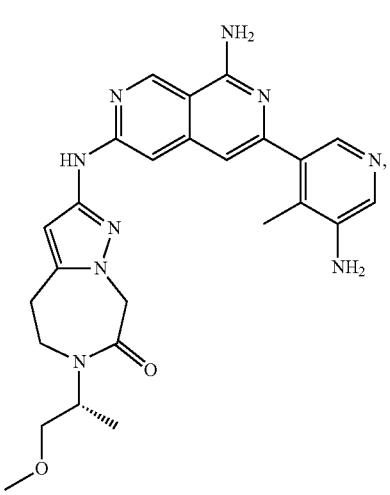

1415
-continued
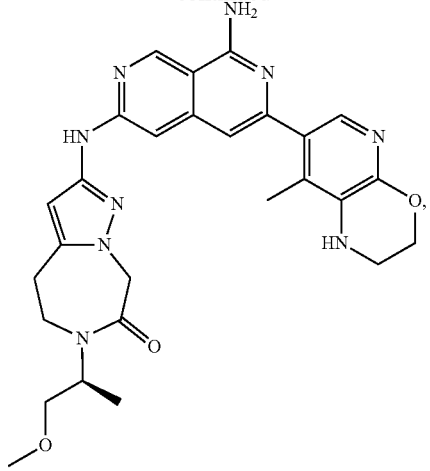
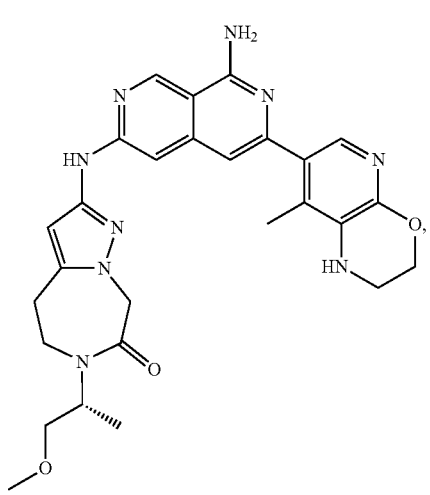
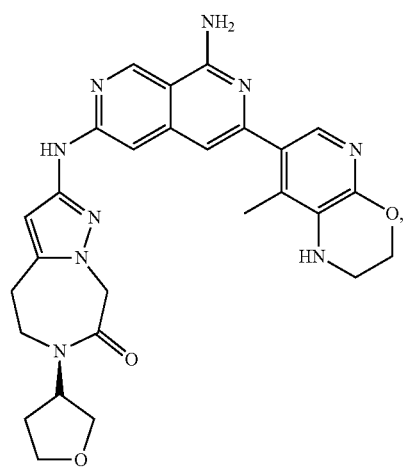
1416
-continued
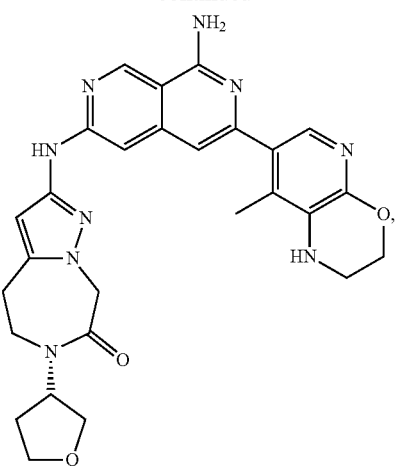
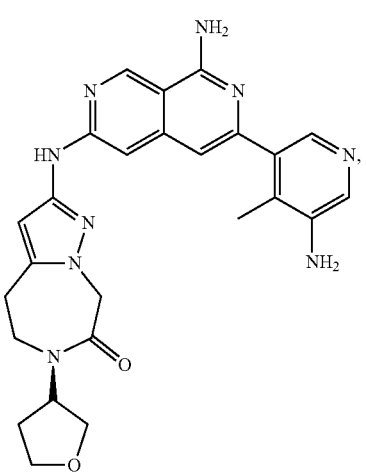
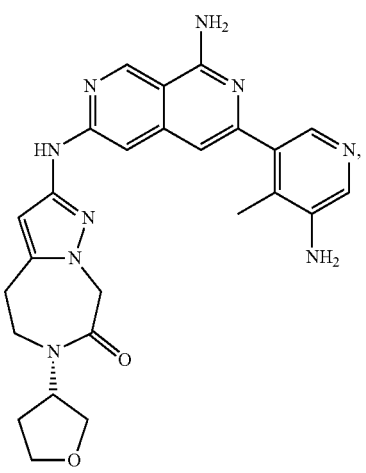

1417
-continued
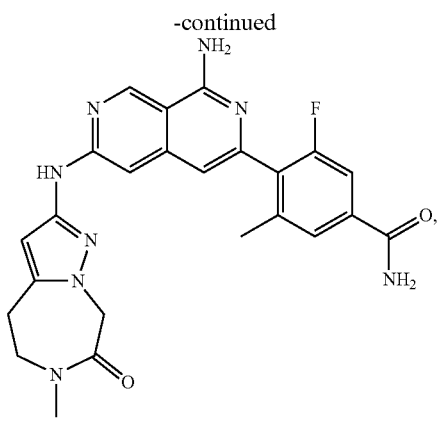
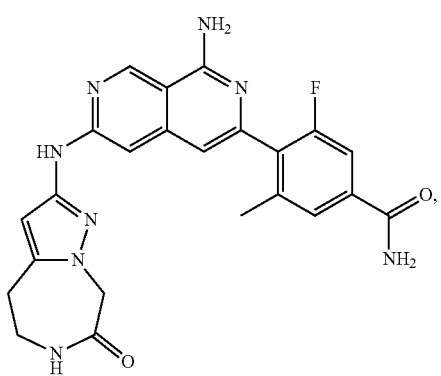
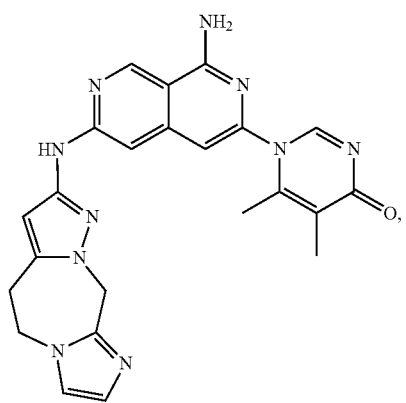
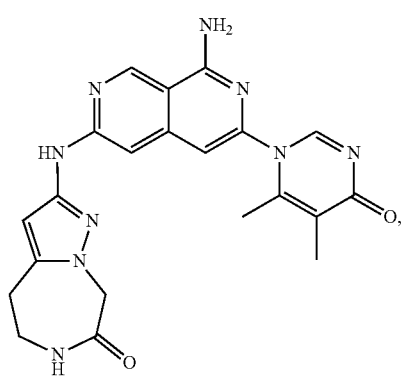
1418
-continued
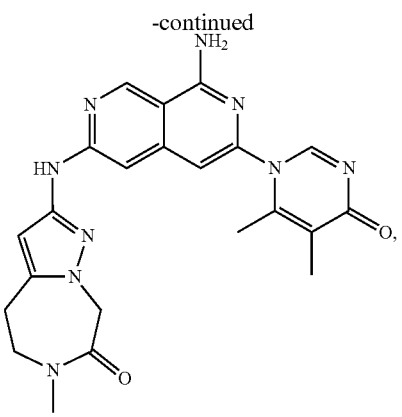
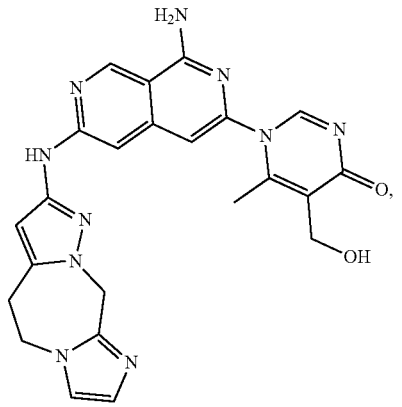
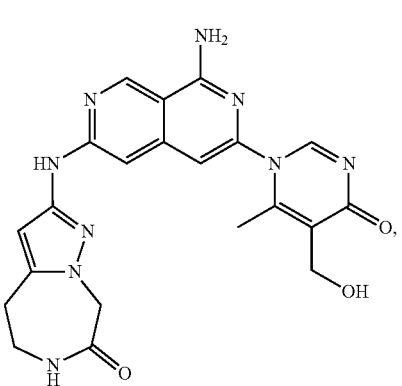
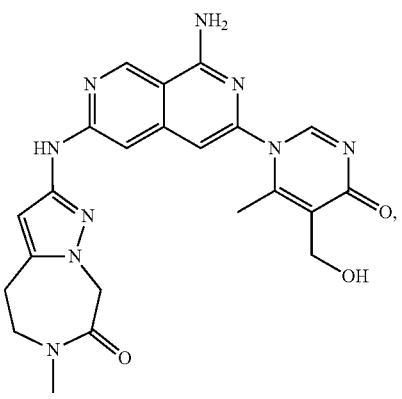

1419
-continued
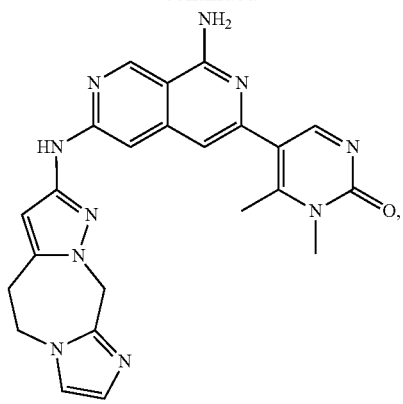
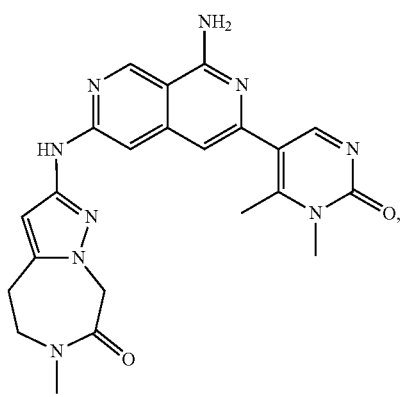
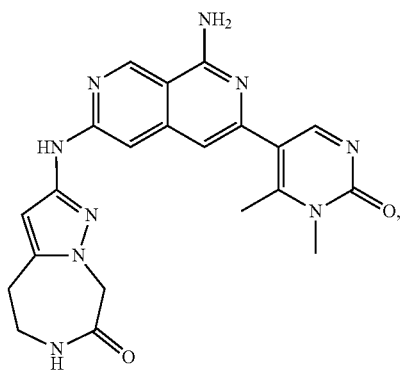
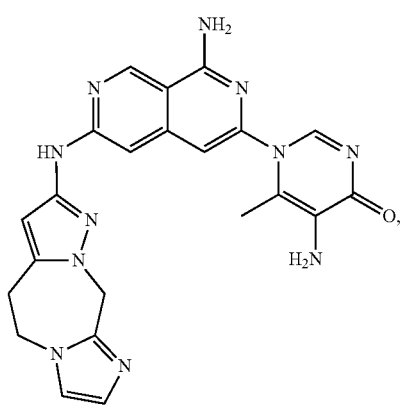
1420
-continued
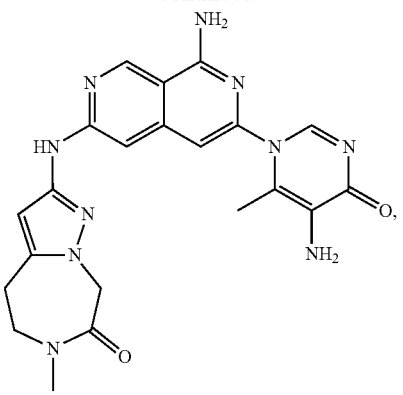
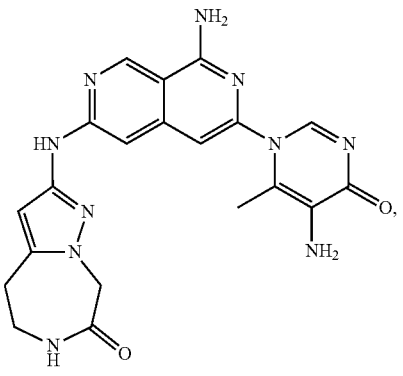
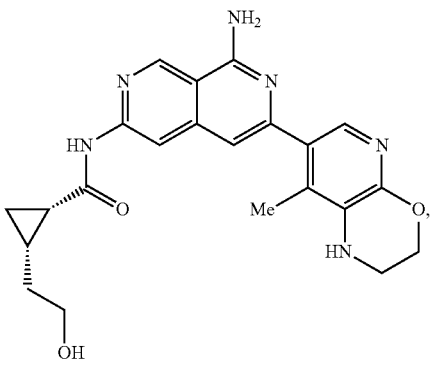
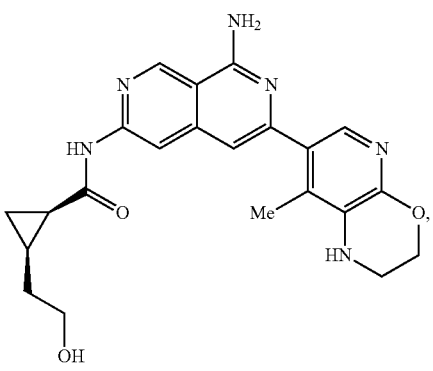

1421
-continued
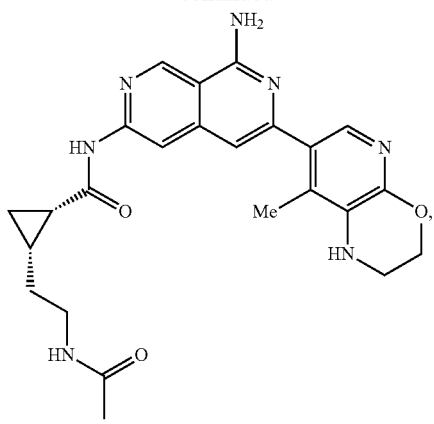
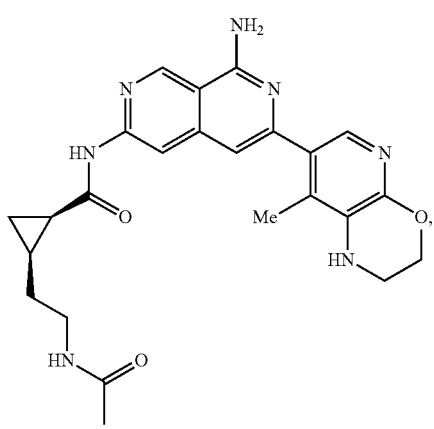
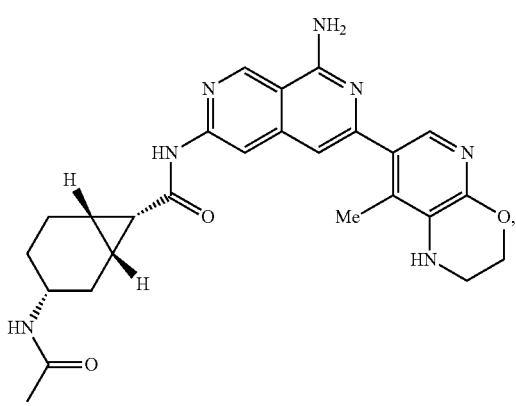
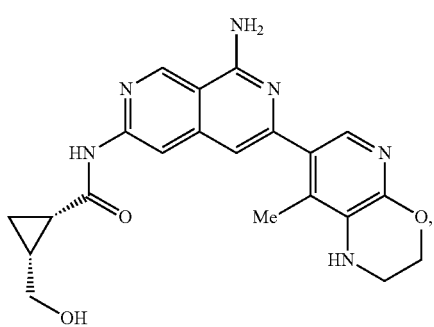
1422
-continued
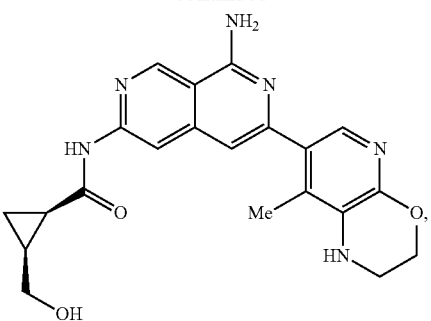
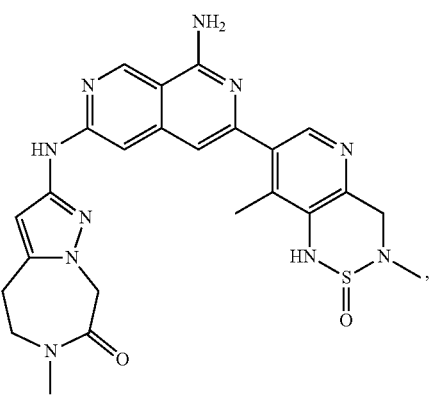
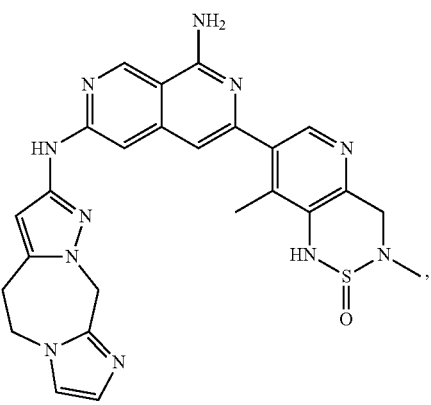
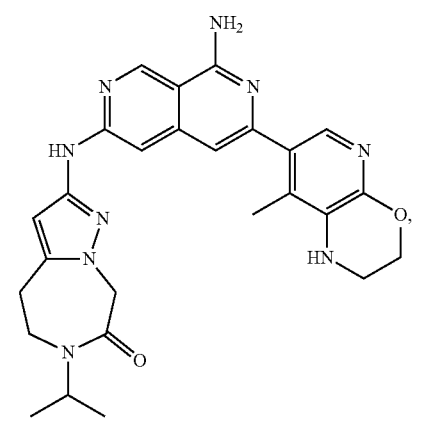

1423
-continued
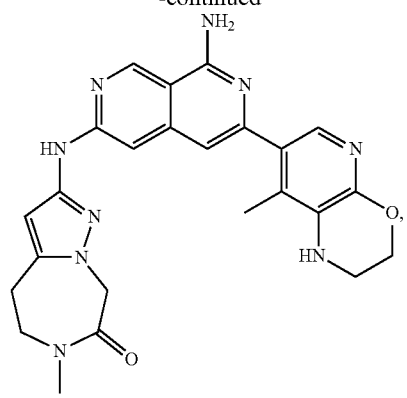
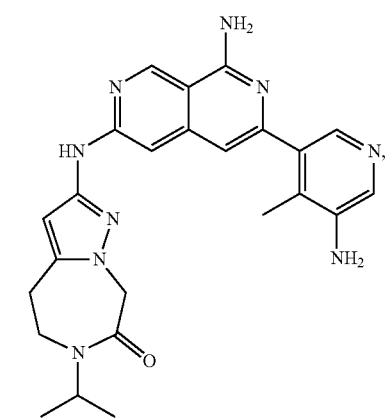
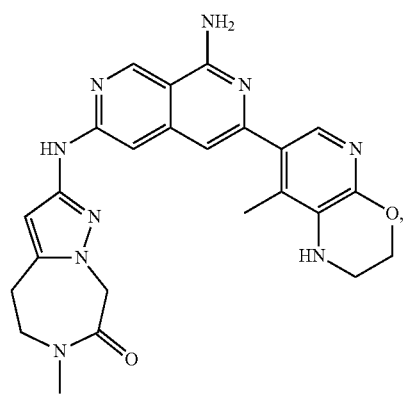
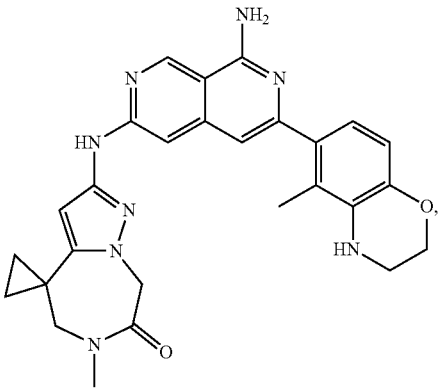
1424
-continued
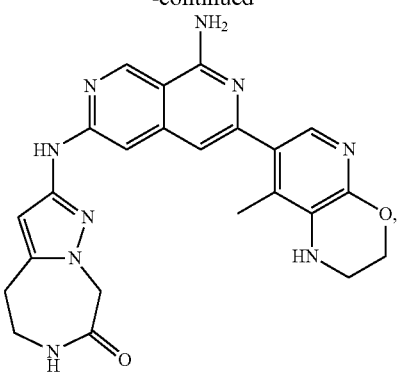
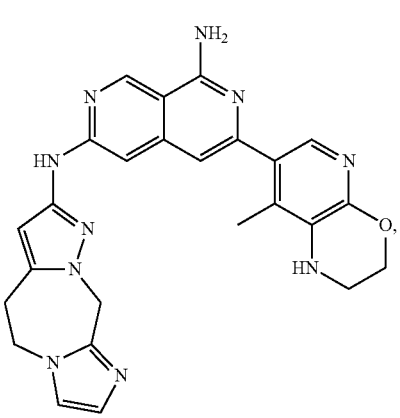
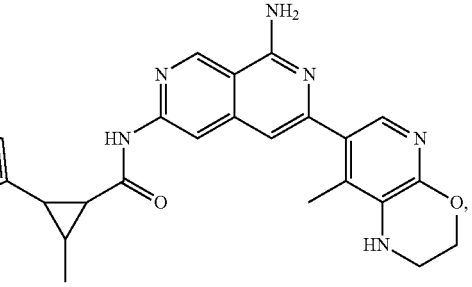
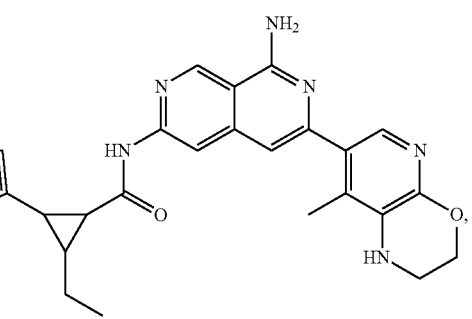
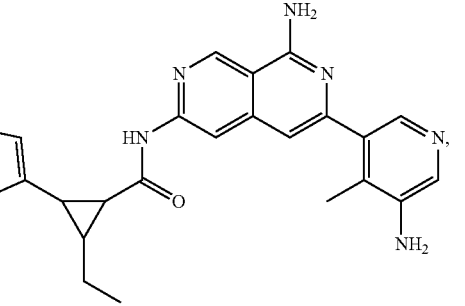

1425
-continued
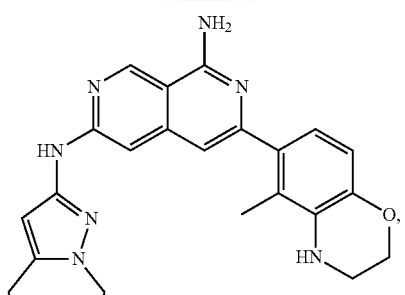
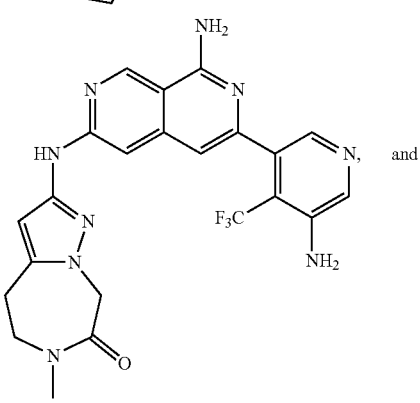
and
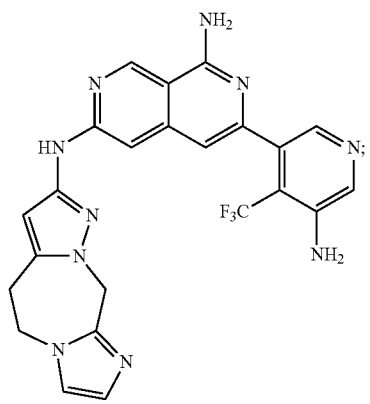
or a pharmaceutically acceptable salt, thereof.
18. The method of claim 1, wherein the compound is selected from the group consisting of Compound Nos. 1-348 in Table 1, having the structures:
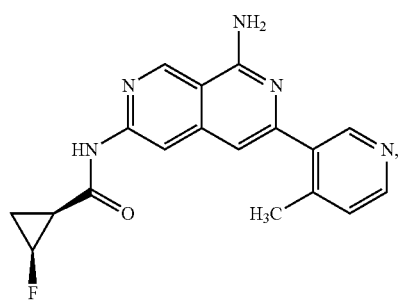
1426
-continued
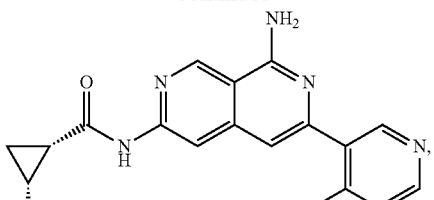
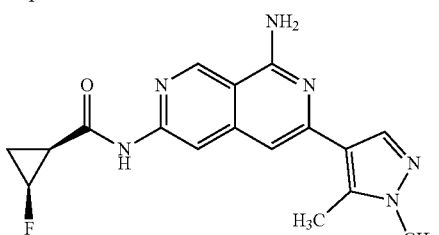
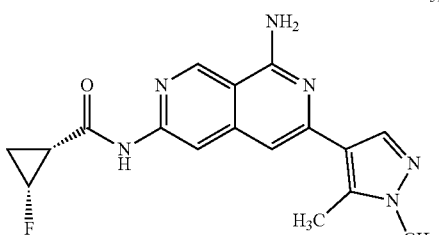
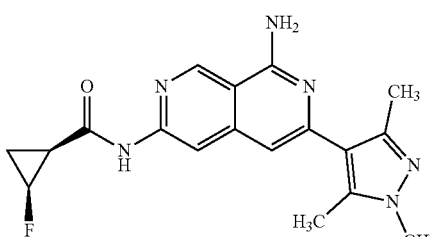
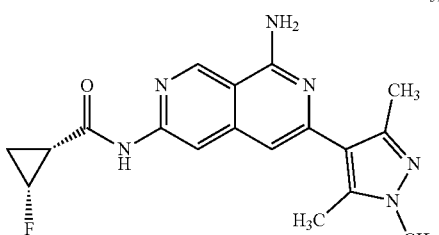
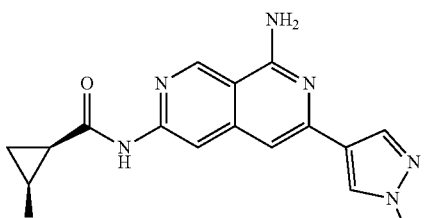
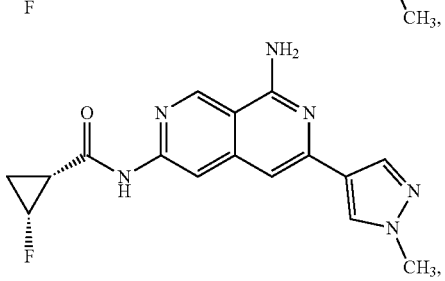

1427
-continued
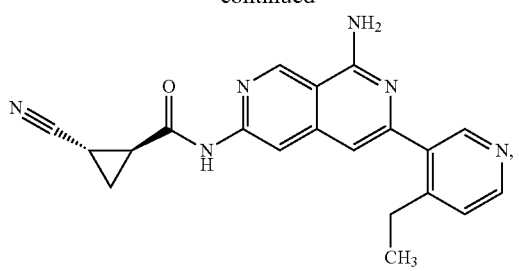
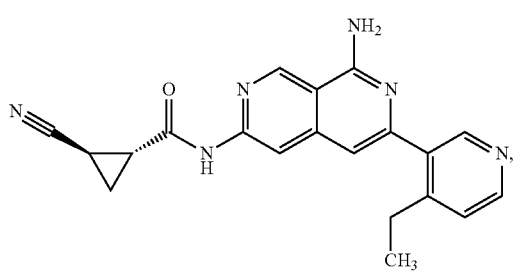
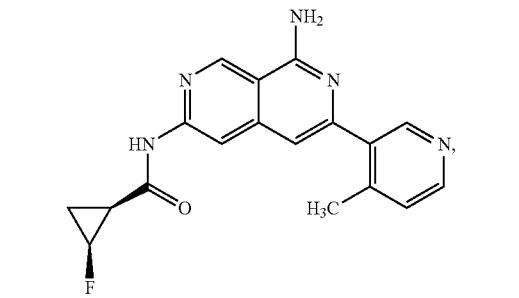
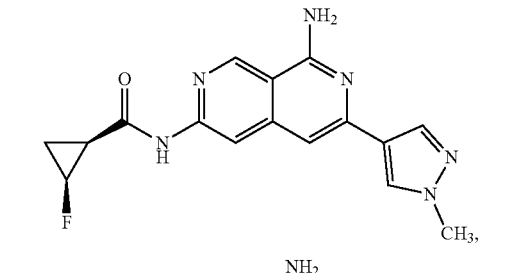
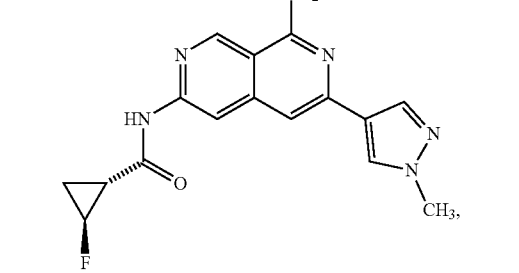
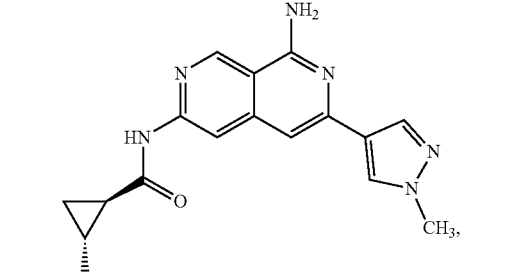
1428
-continued
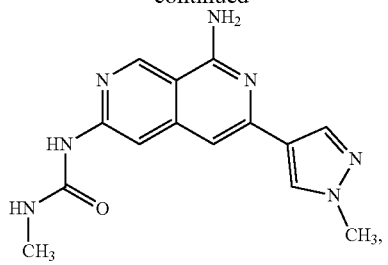
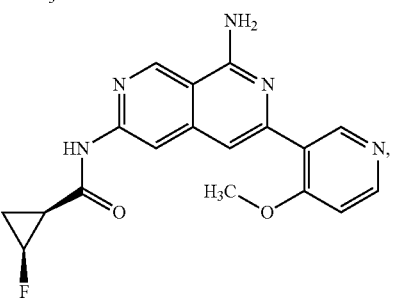
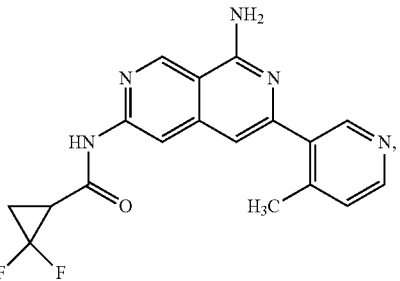
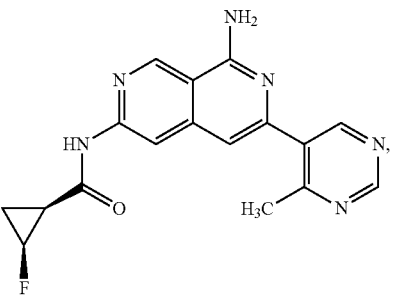
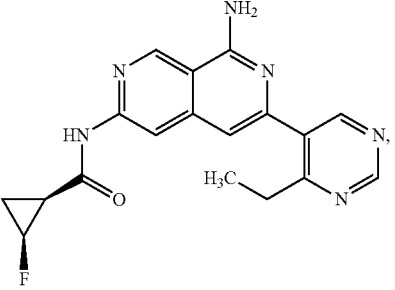
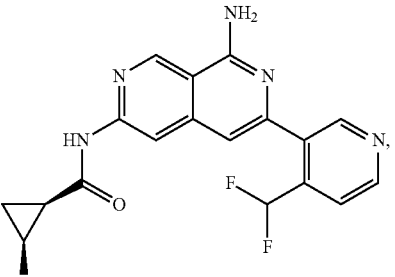

1429
-continued
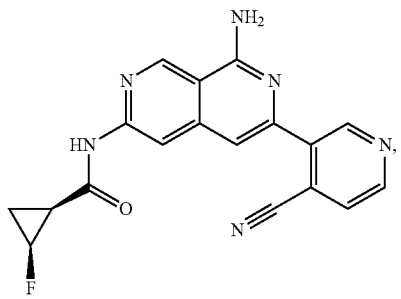
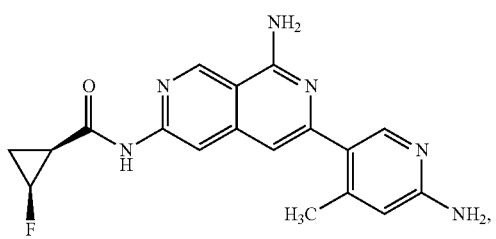
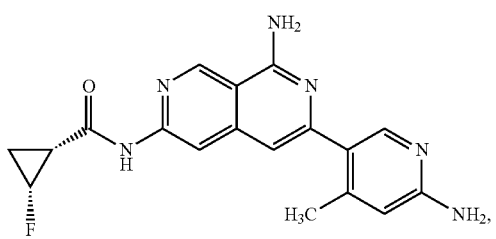
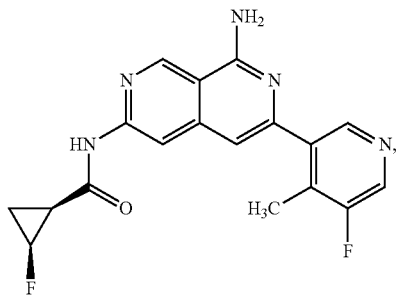
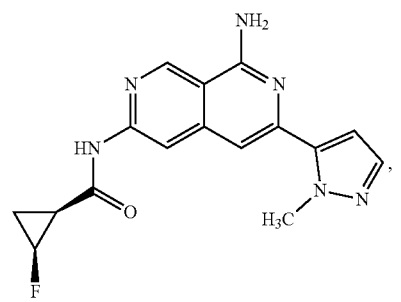
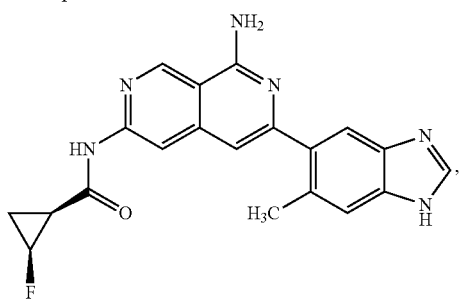
1430
-continued
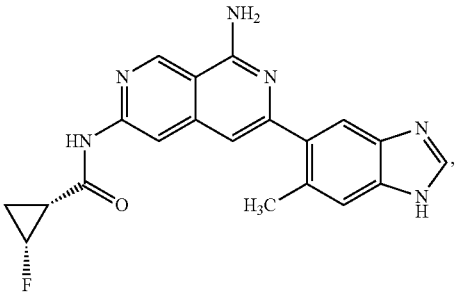
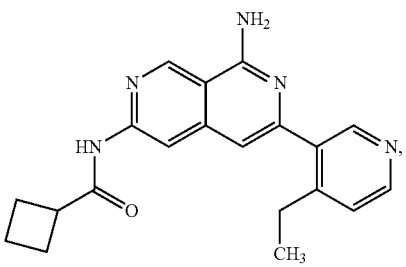
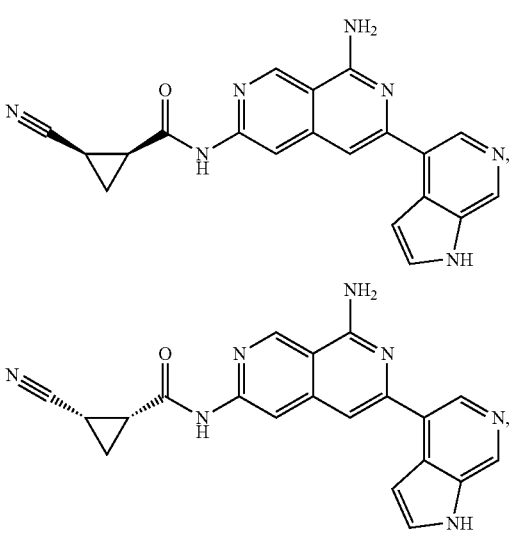
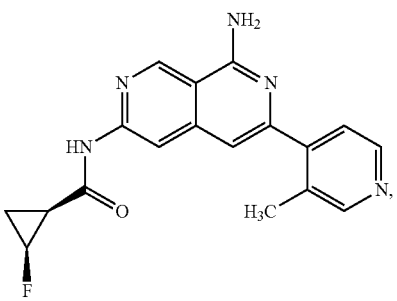
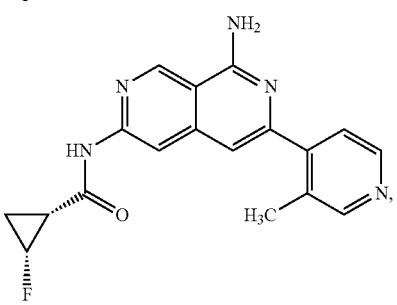

1431
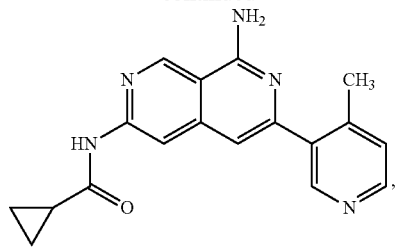
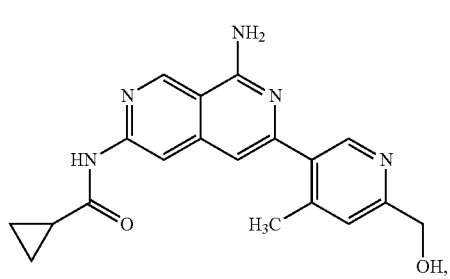
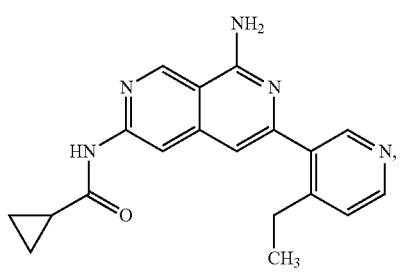
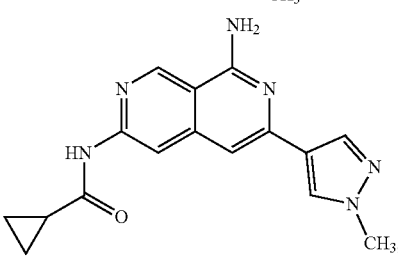
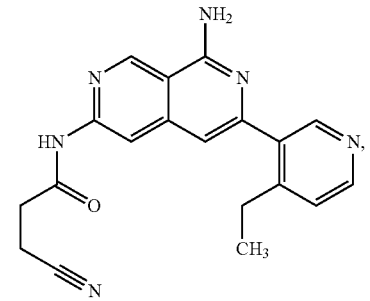
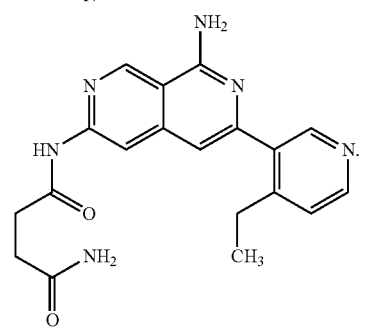
1432
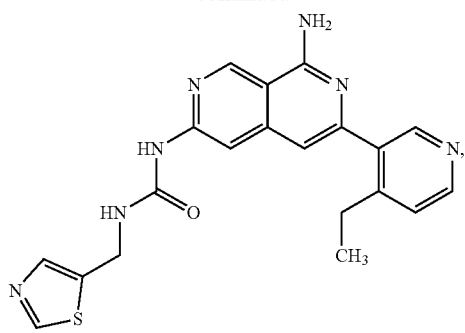
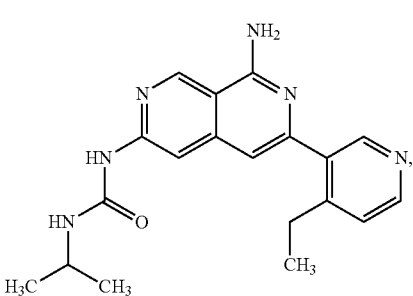
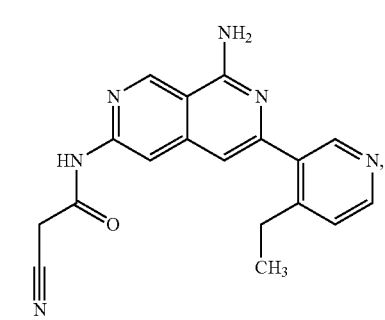
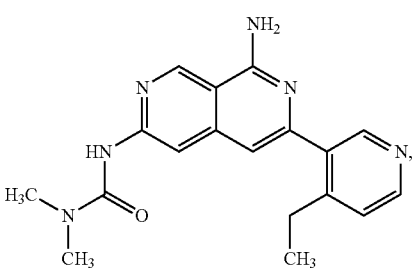
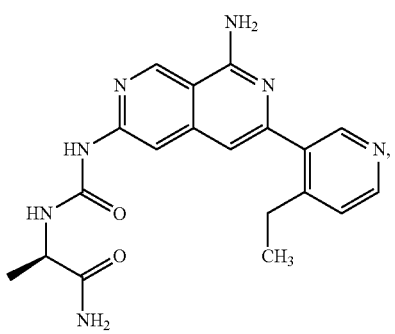

1433
-continued
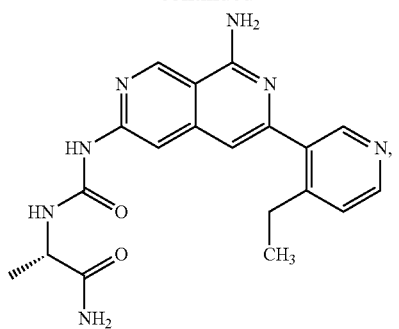
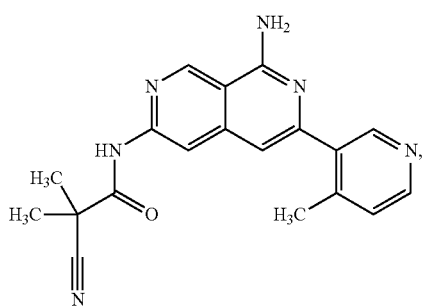
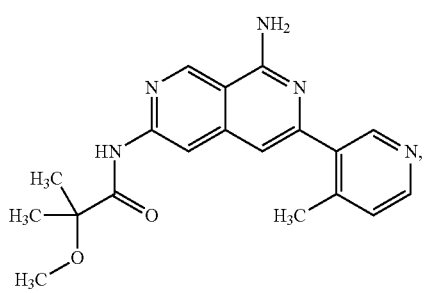
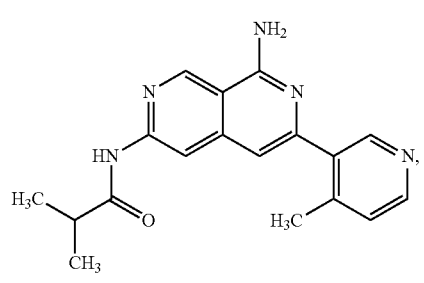
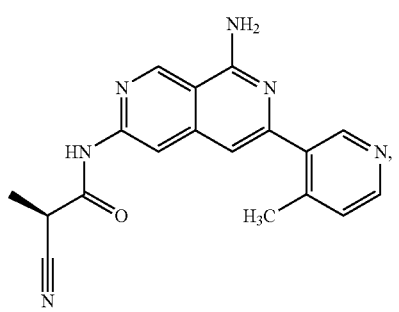
1434
-continued
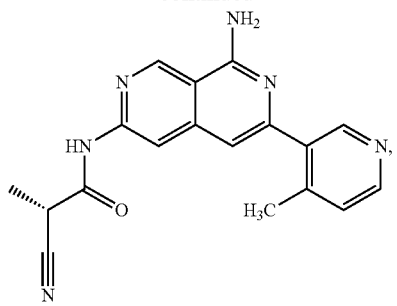
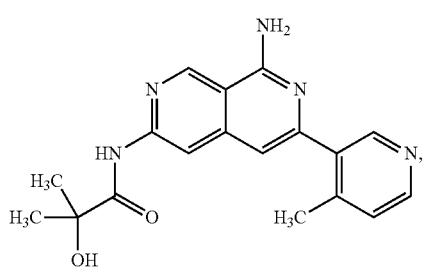
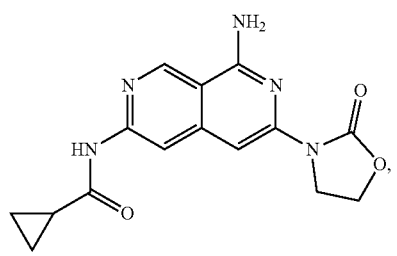
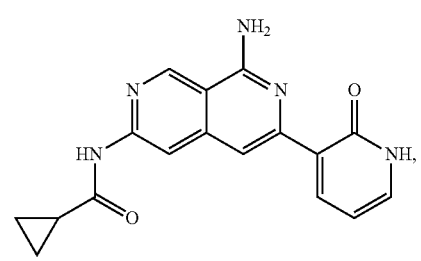
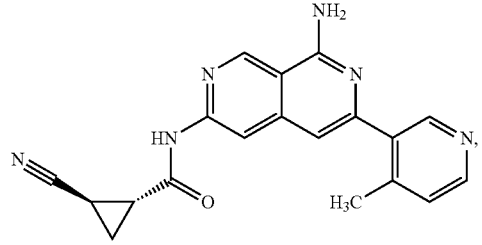
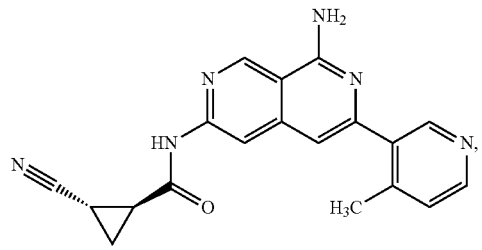

1435
-continued
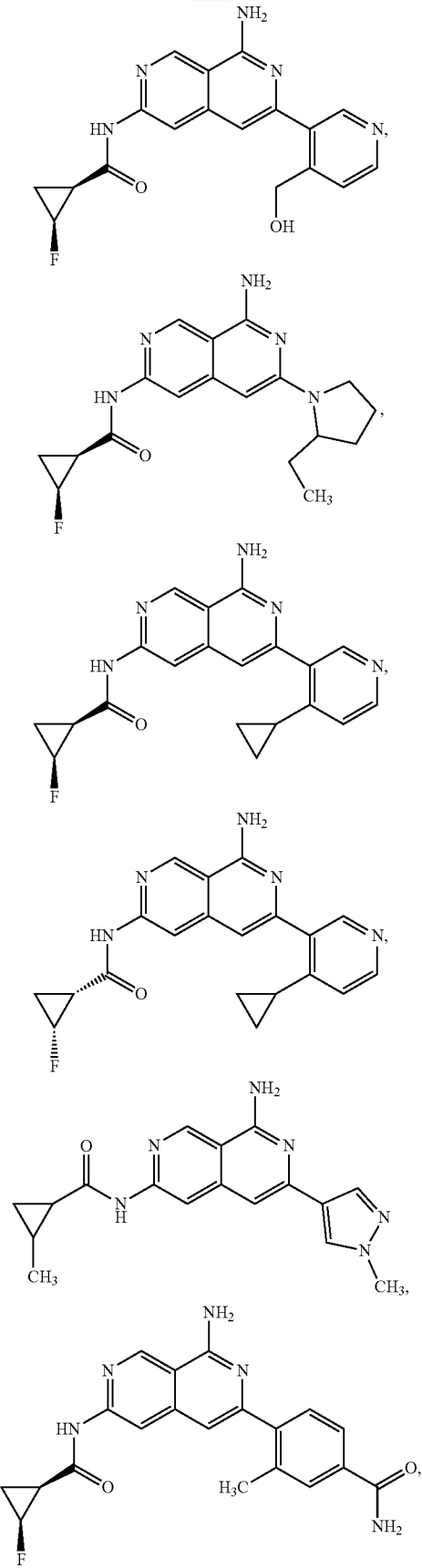
1436
-continued
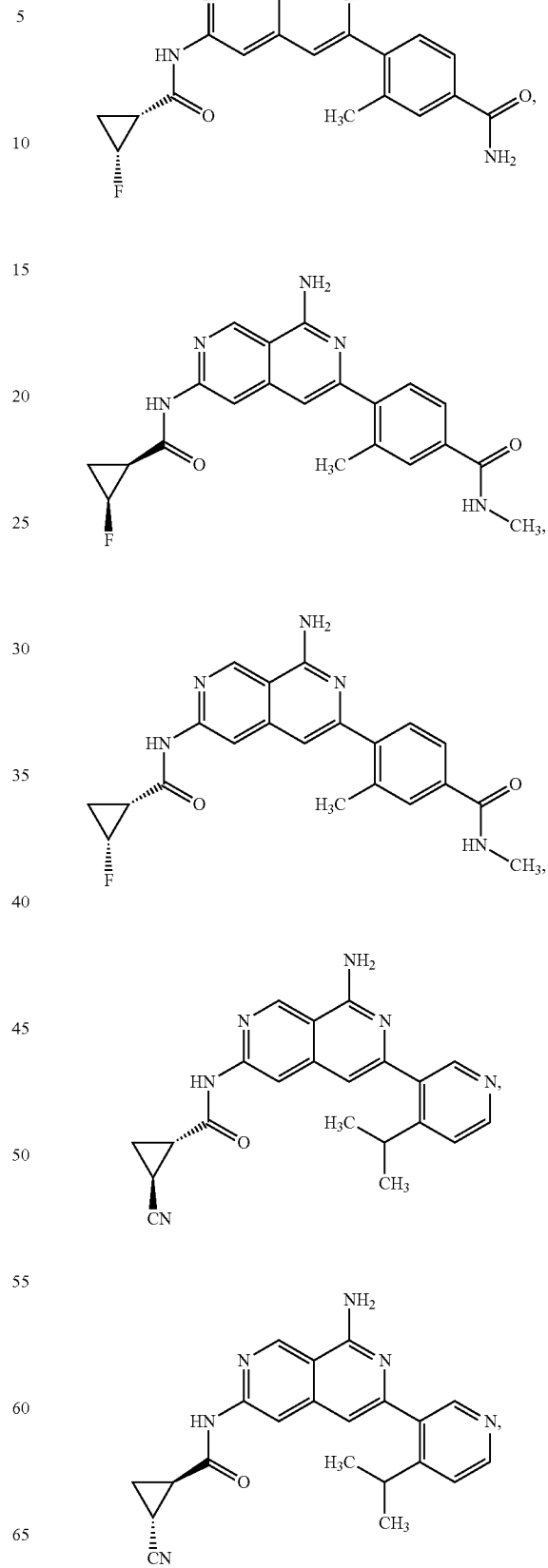

1437
-continued
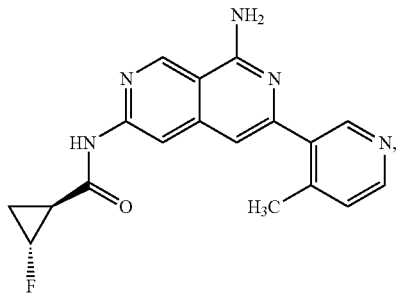
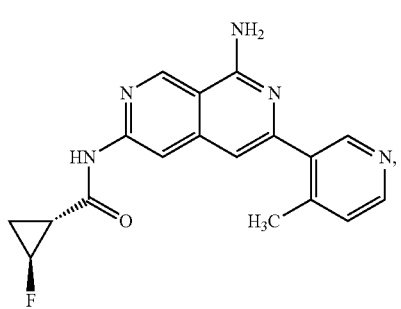
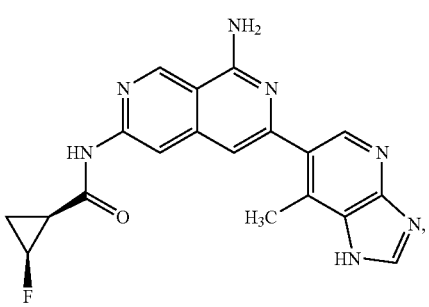
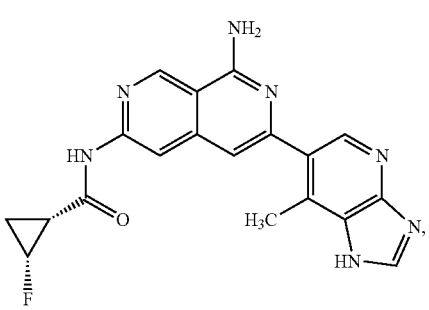
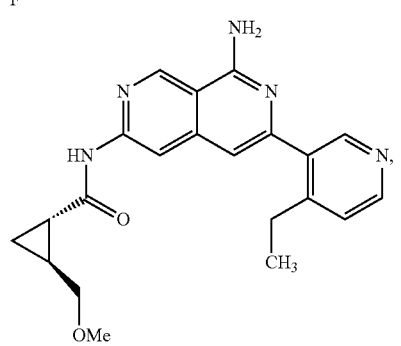
1438
-continued
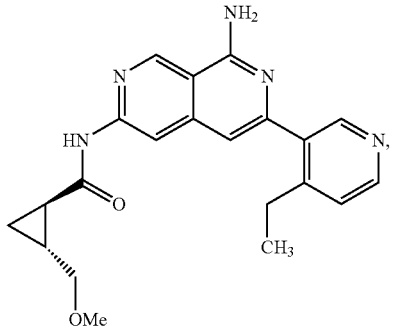
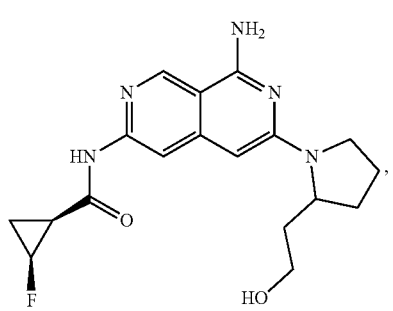
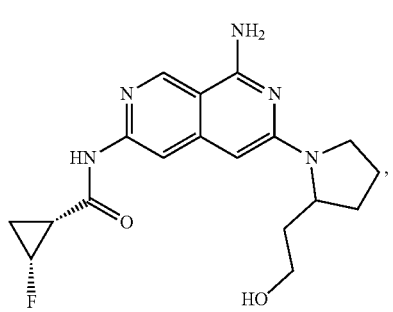
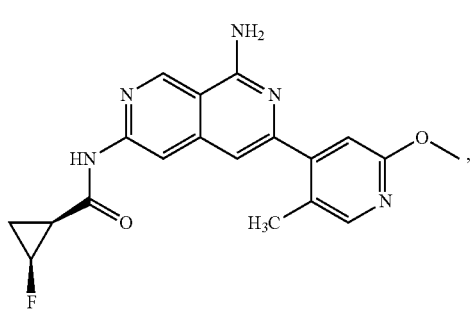
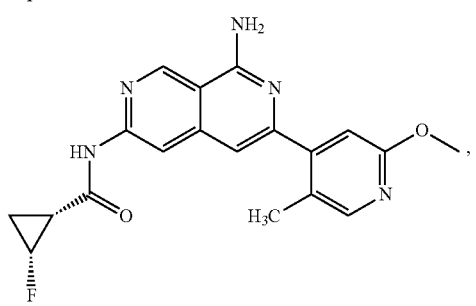

1439
-continued
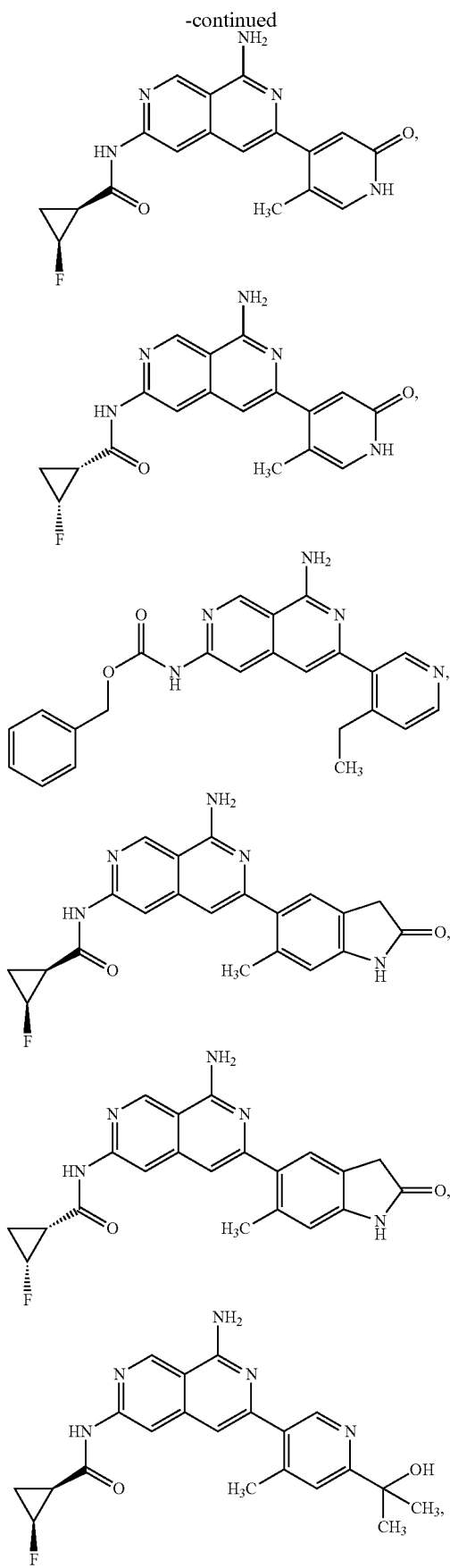
1440
-continued
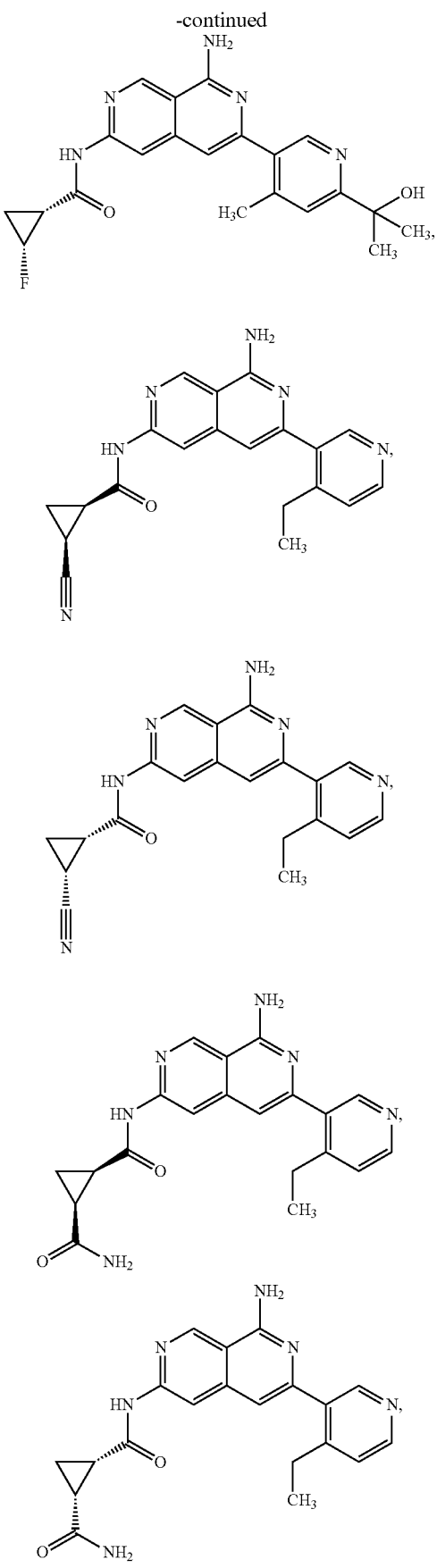

1441
-continued
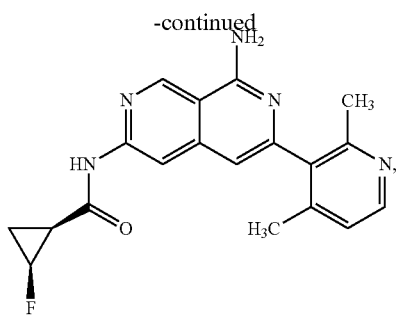
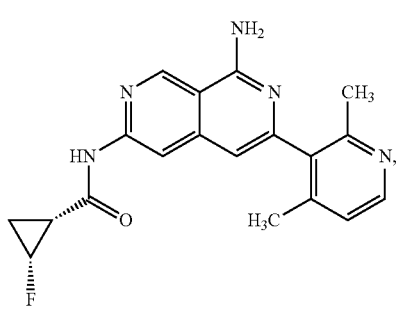
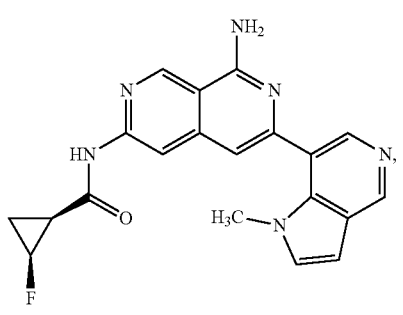
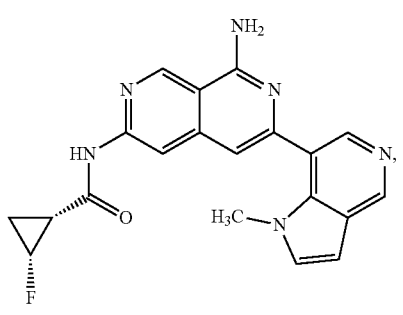
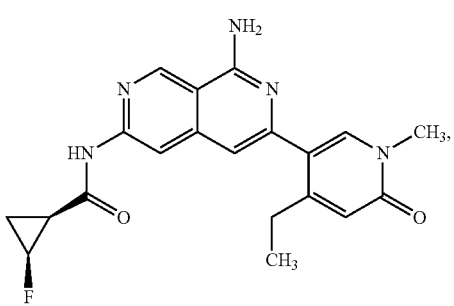
1442
-continued
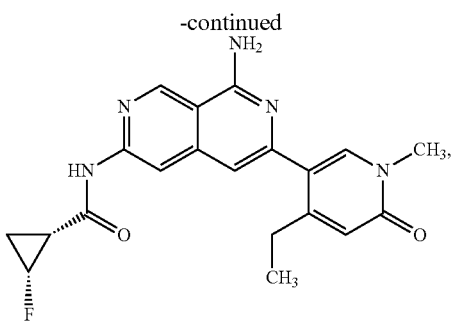
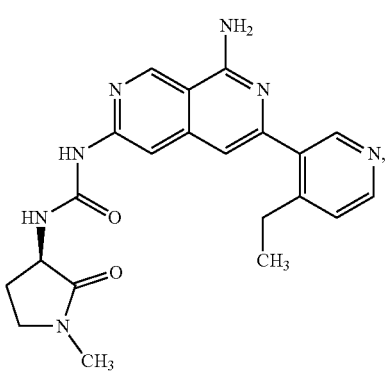
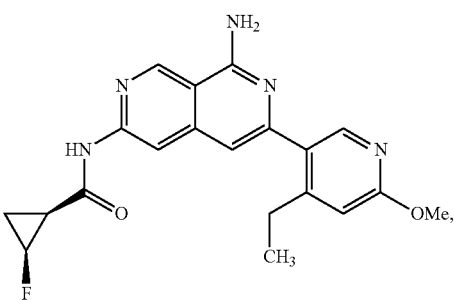
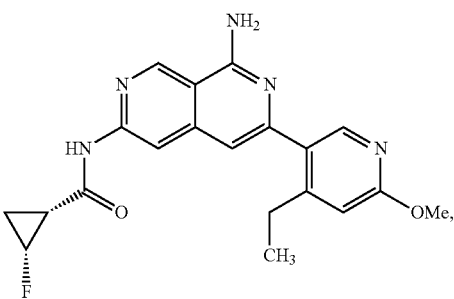
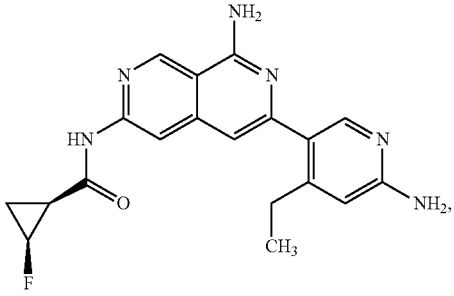

1443
-continued
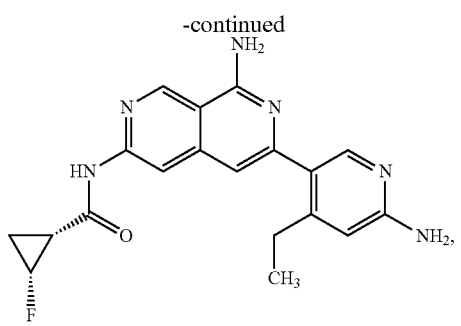
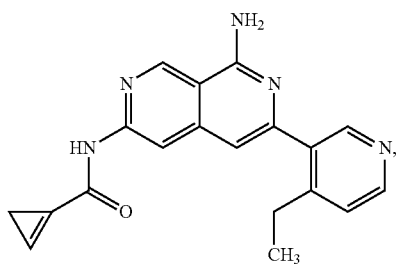
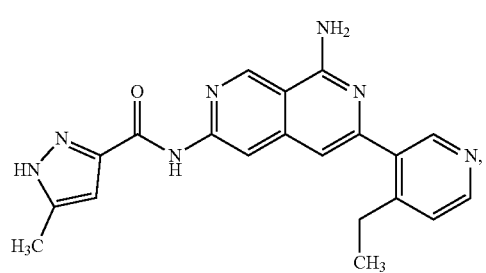
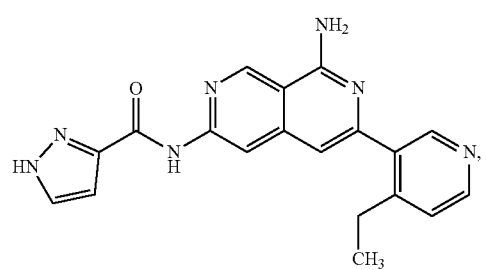
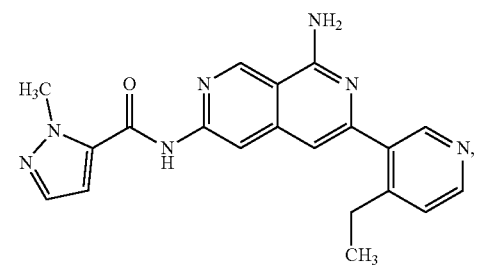
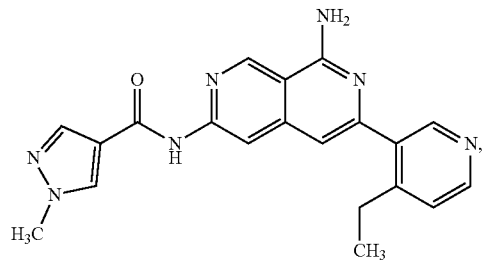
1444
-continued
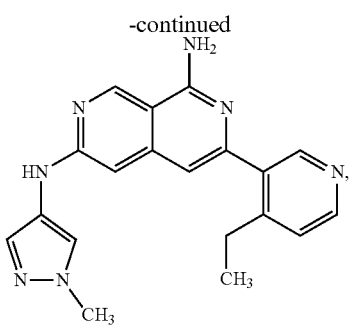
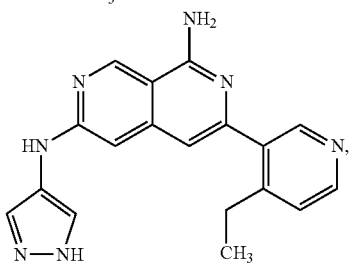
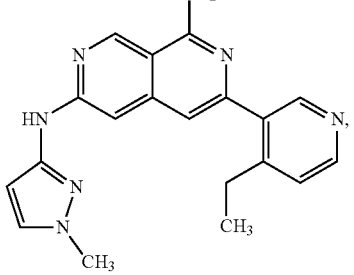
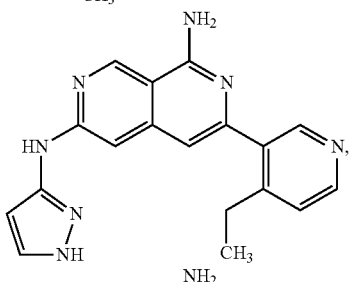
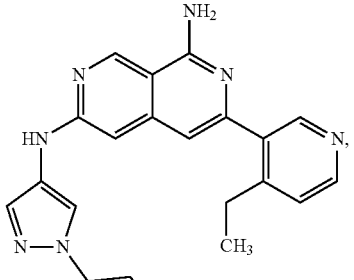
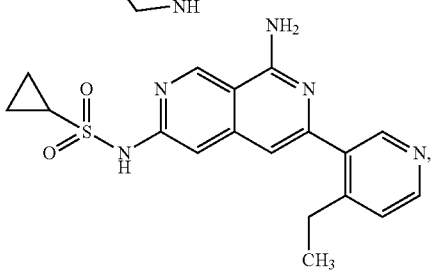

1445
-continued
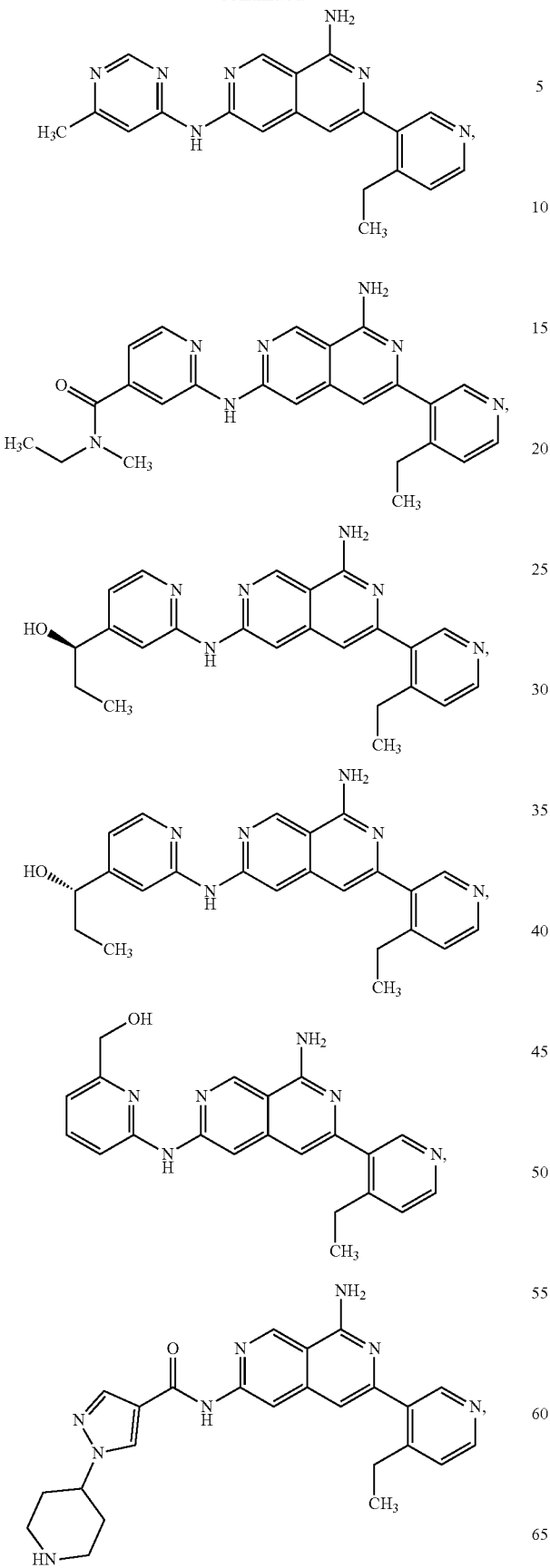
1446
-continued
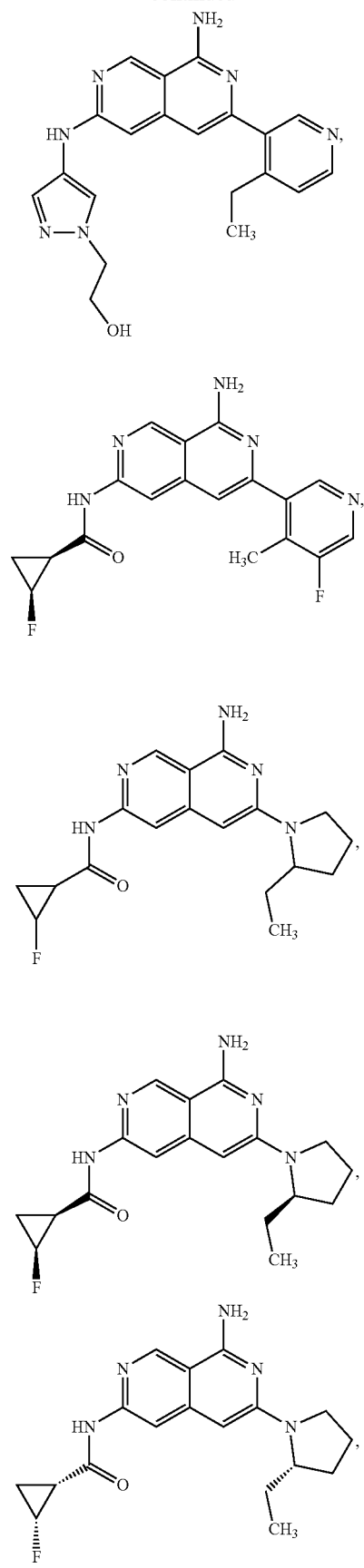

1447
-continued
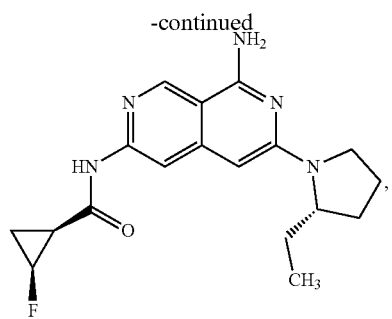
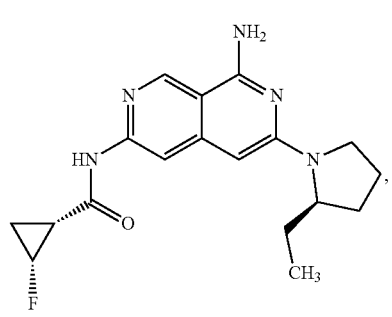
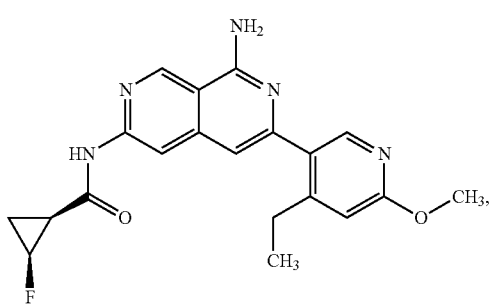
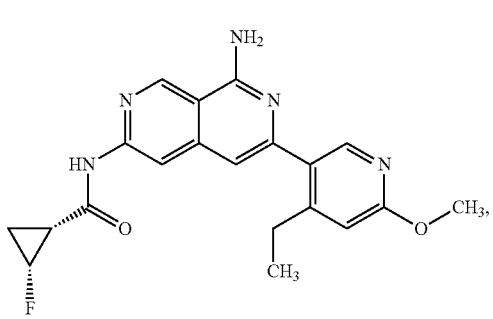
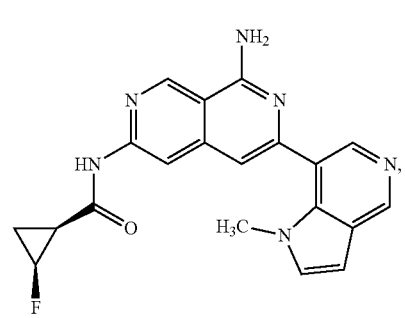
1448
-continued
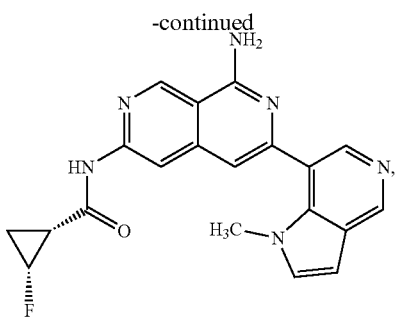
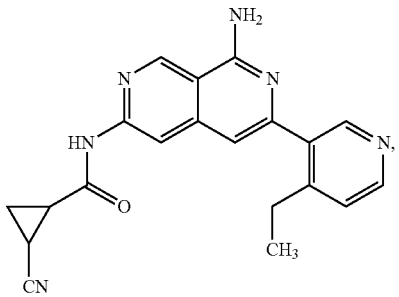
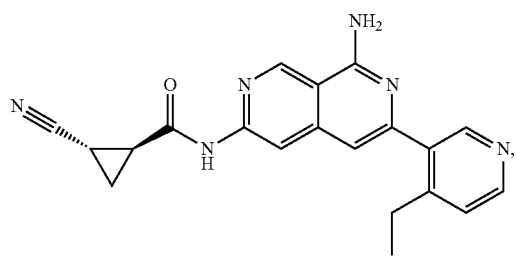
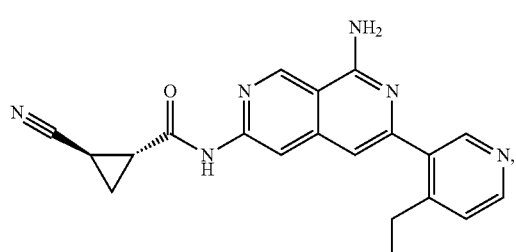
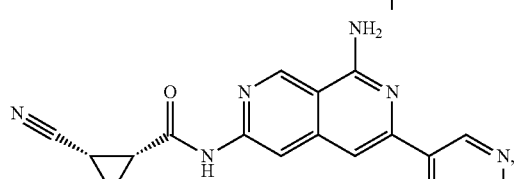
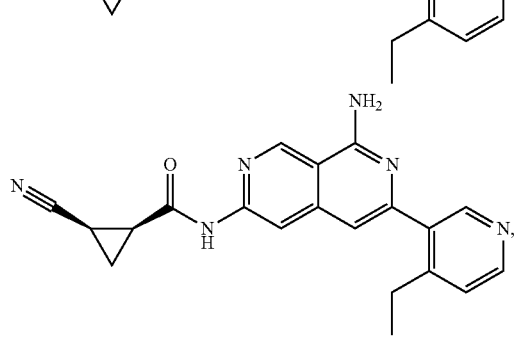

1449
-continued
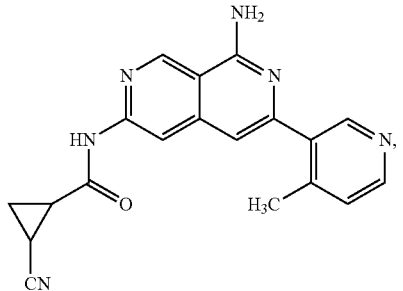
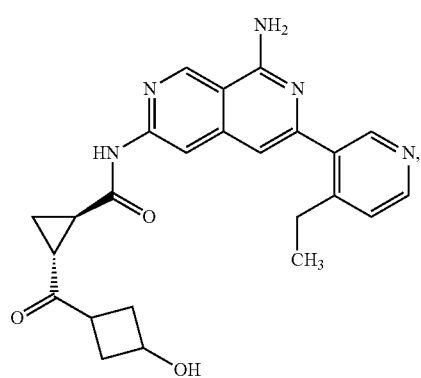
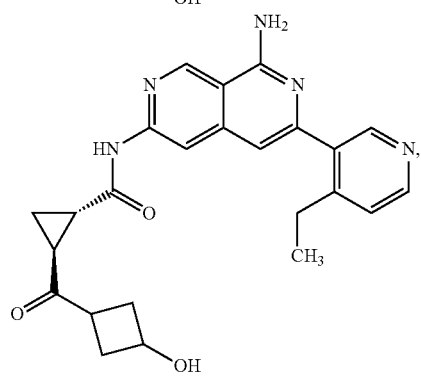
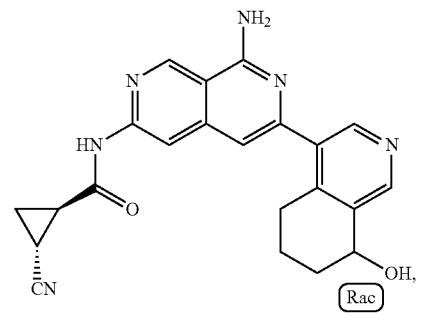
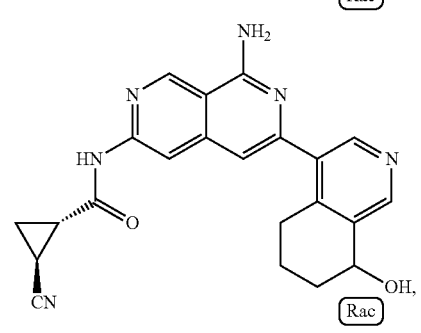
1450
-continued
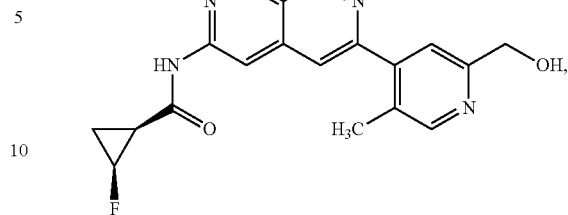
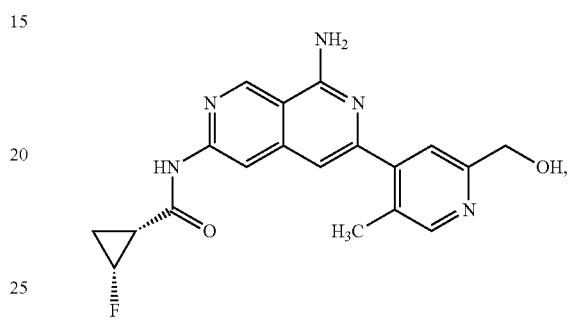
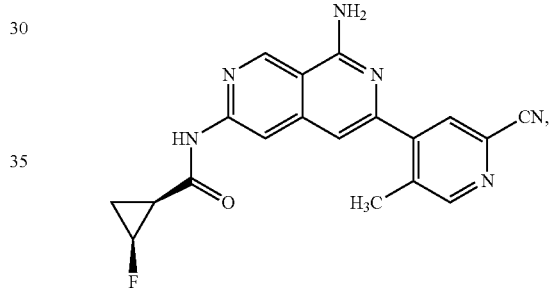
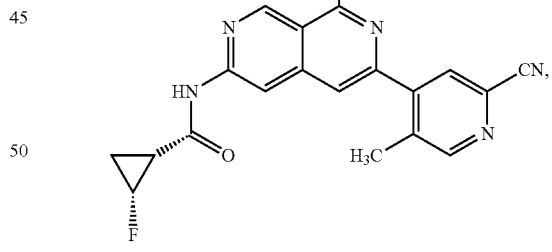
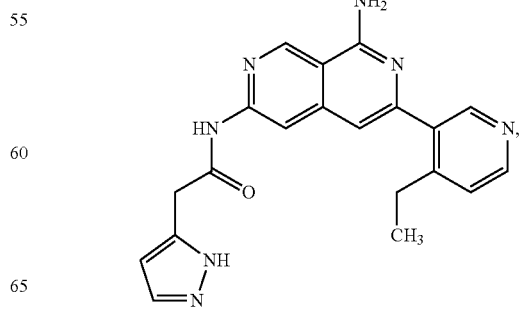

1451
-continued
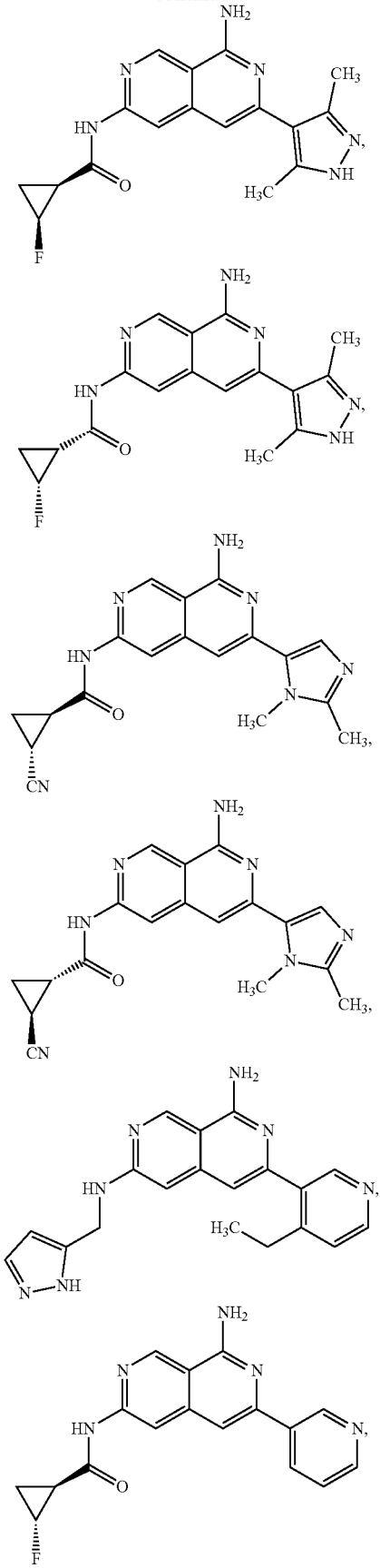
1452
-continued
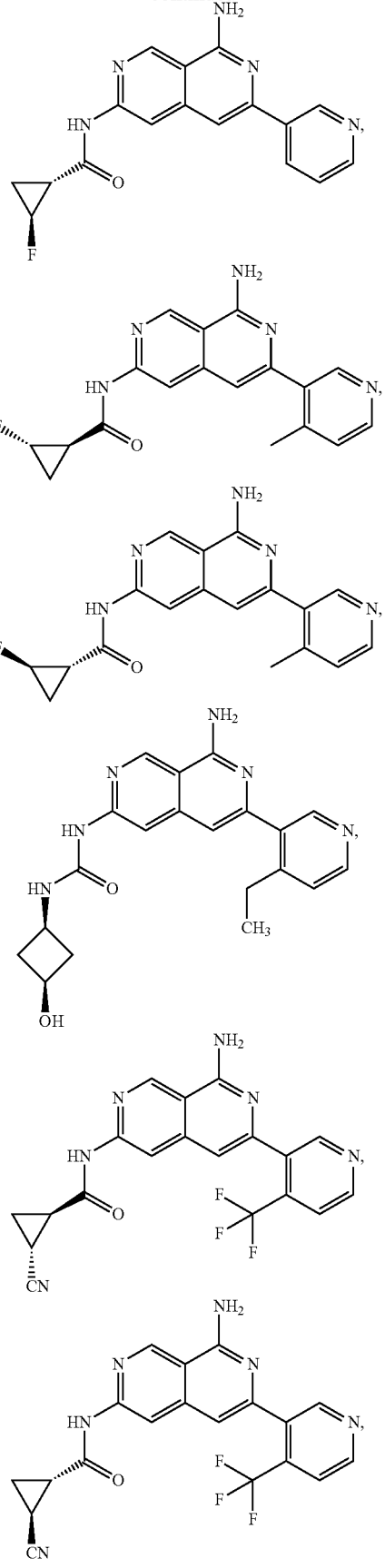

1453
-continued
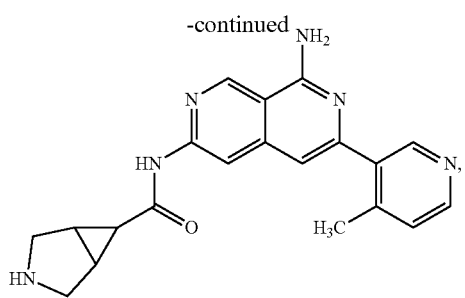
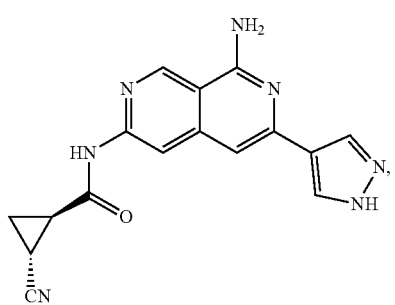
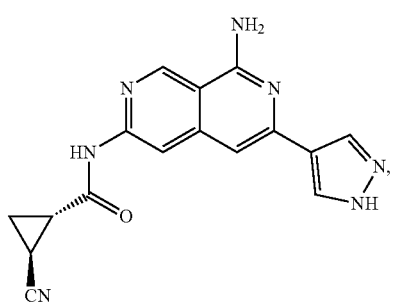
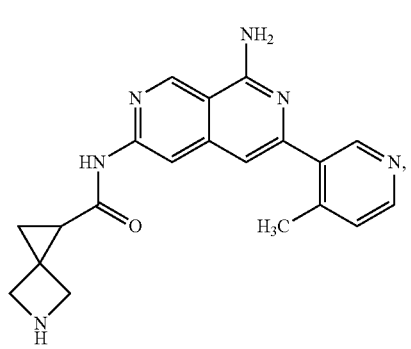
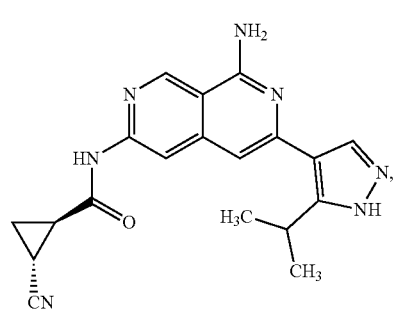
1454
-continued
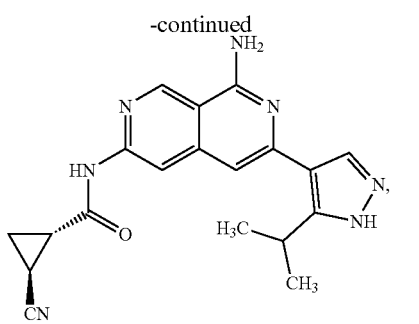
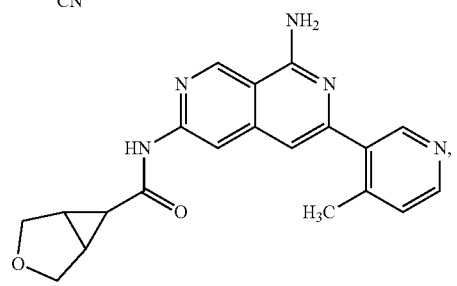
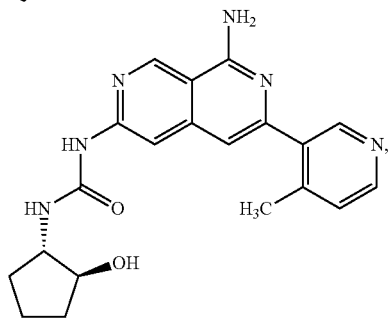
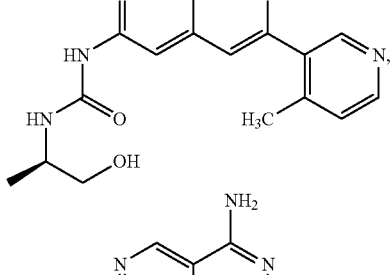
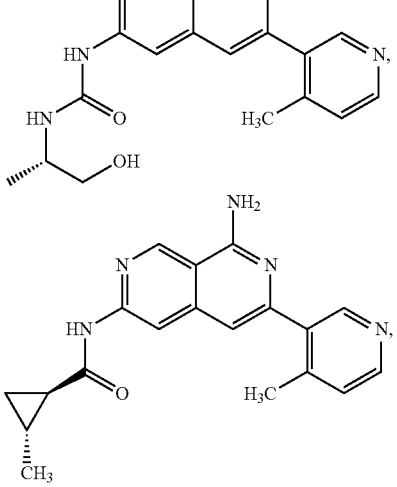

1455
-continued
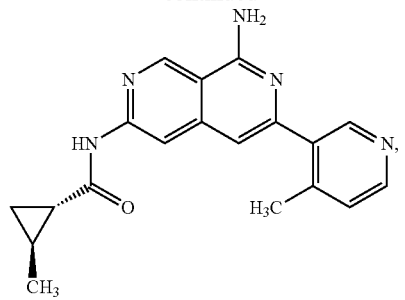
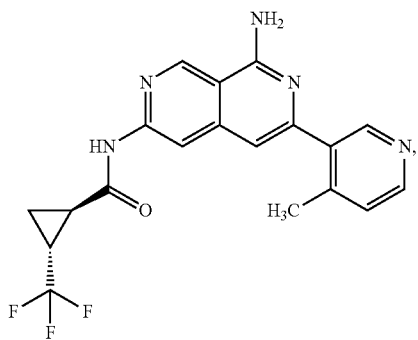
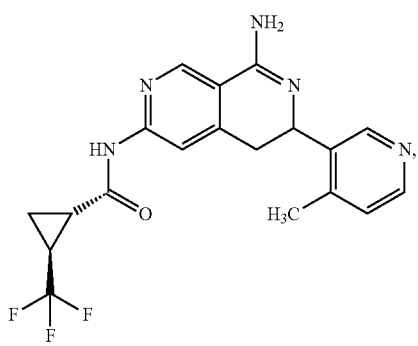
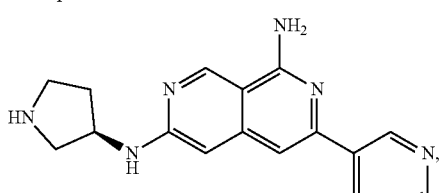
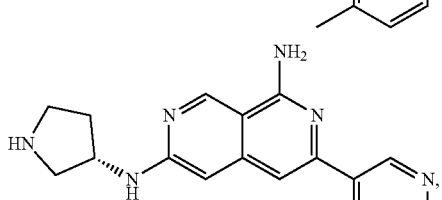
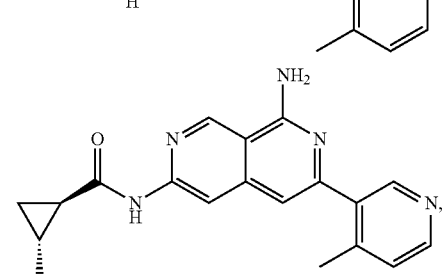
1456
-continued
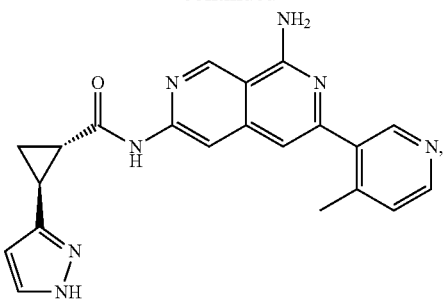
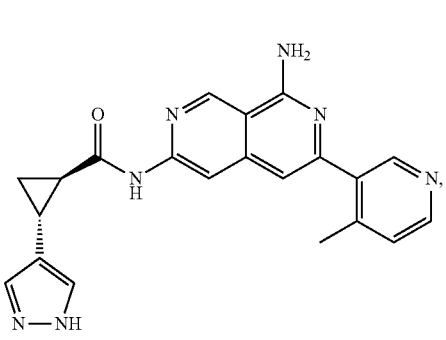
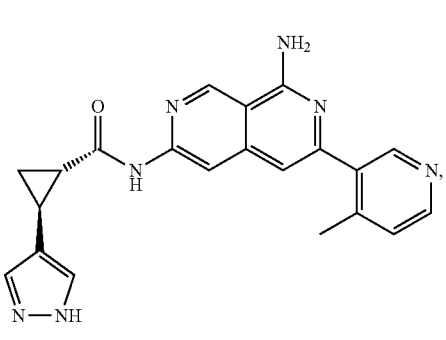
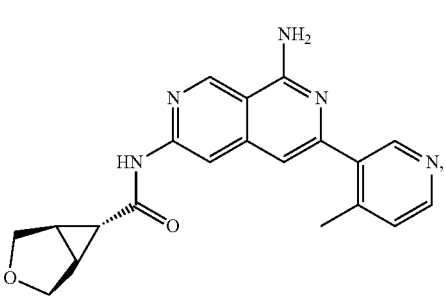
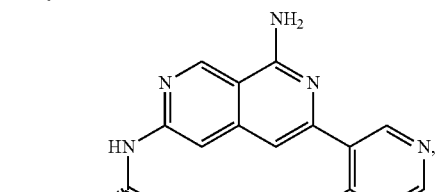
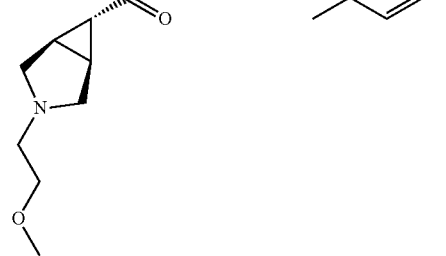

1457
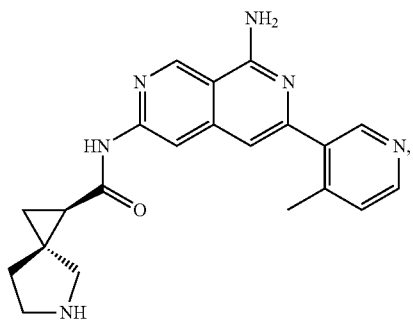
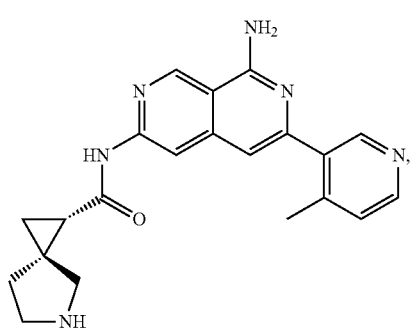
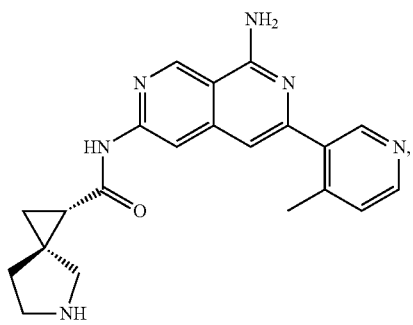
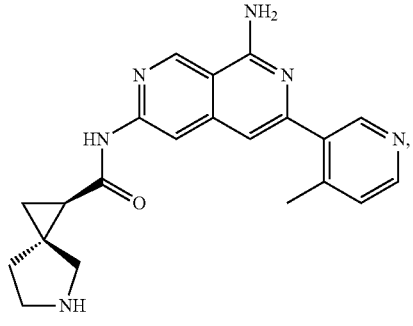
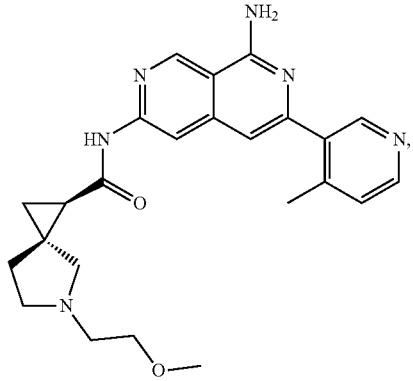
1458
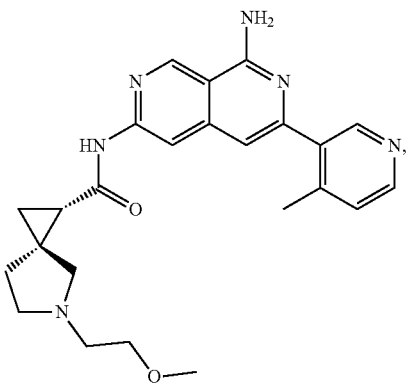
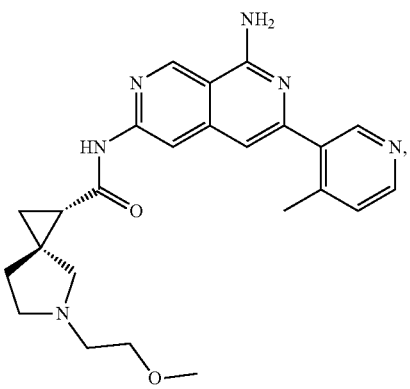
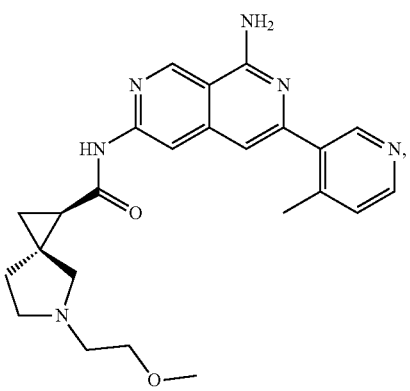
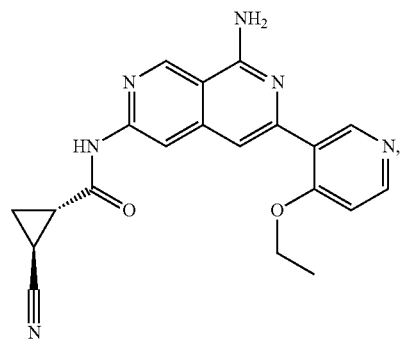

| 1459 | 1460 |
|---|---|
| 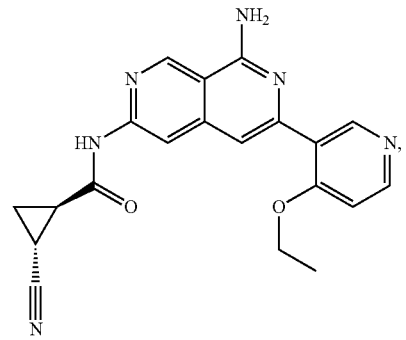 | 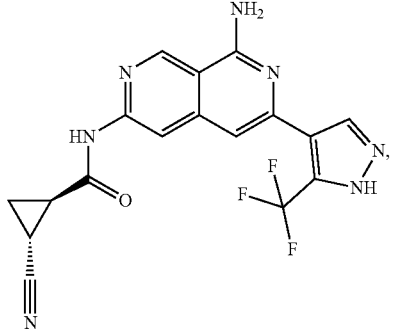 |
| 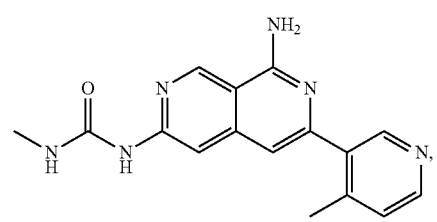 | 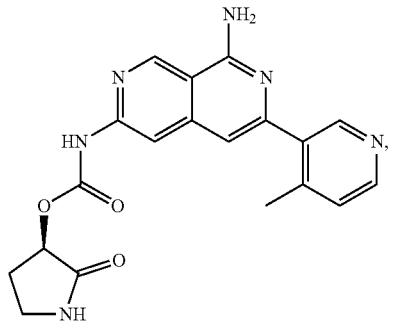 |
| 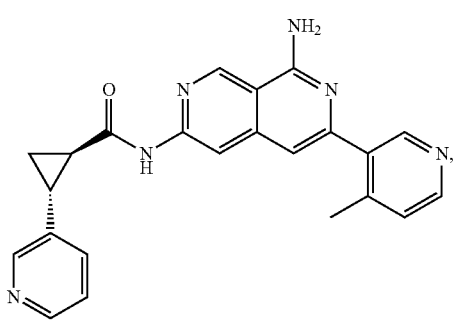 | 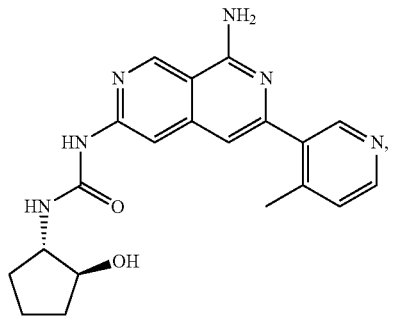 |
| 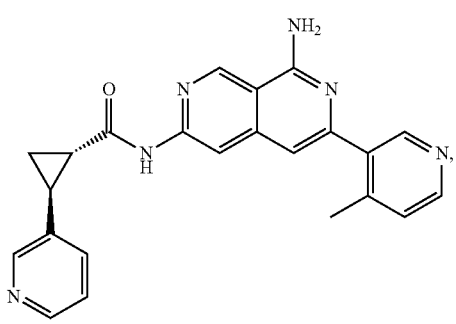 | 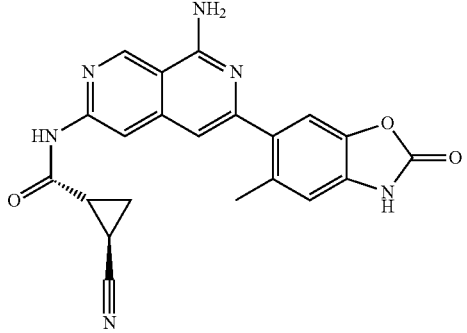 |
| 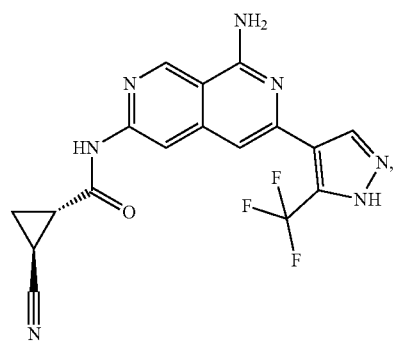 | 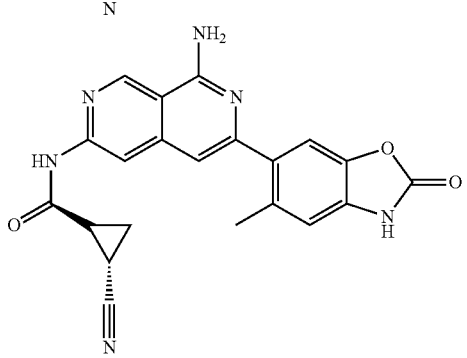 |

-continued
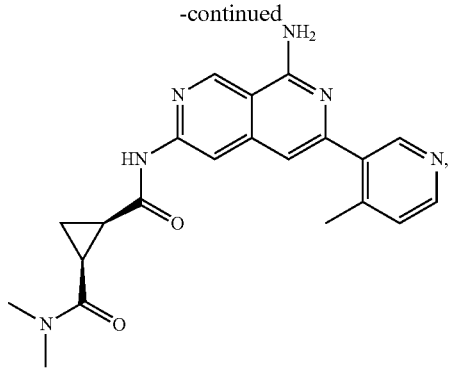
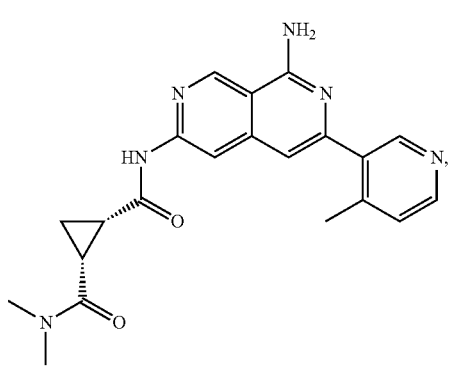
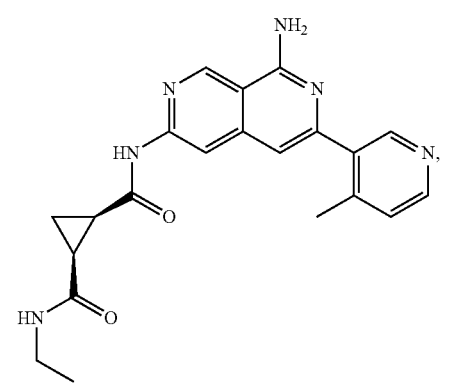
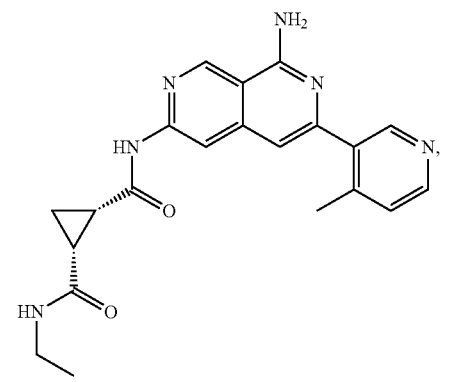
-continued
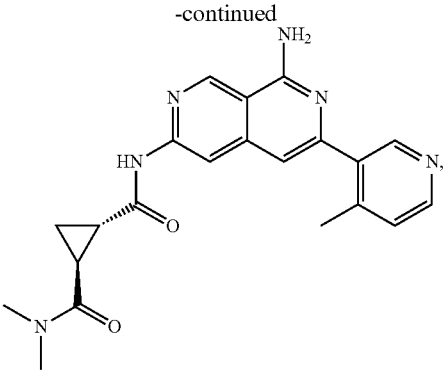
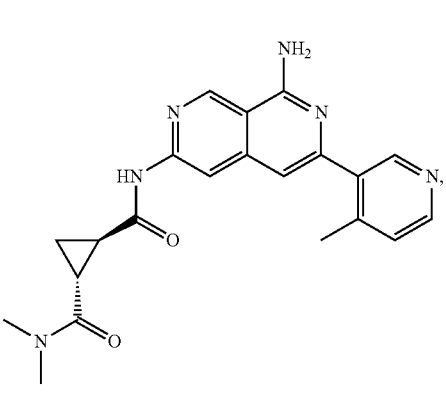
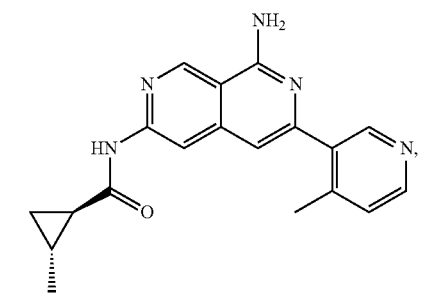
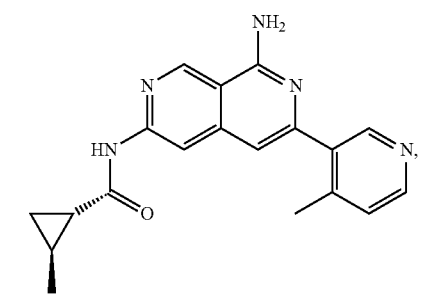
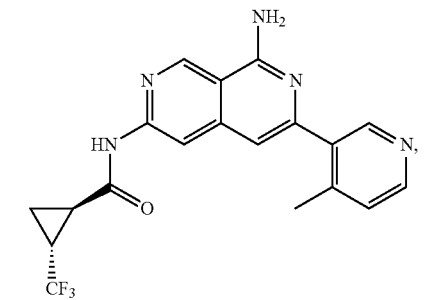

1463
-continued
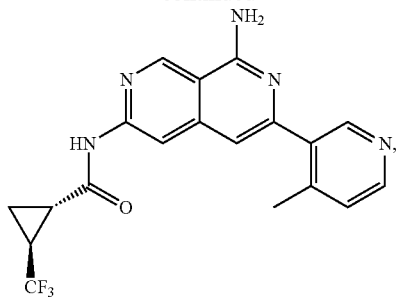
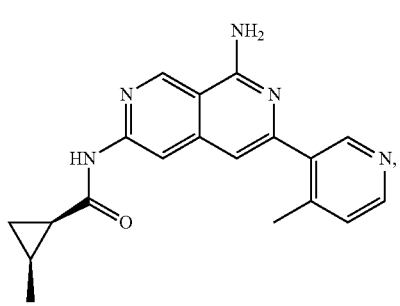
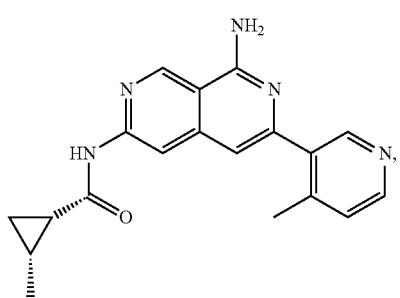
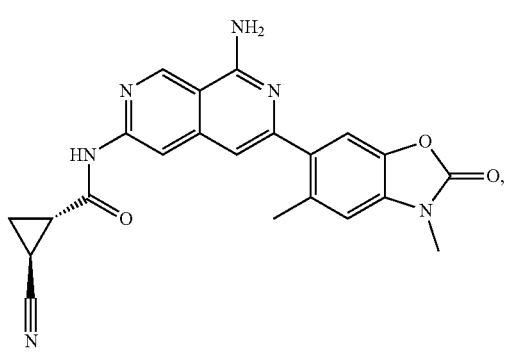
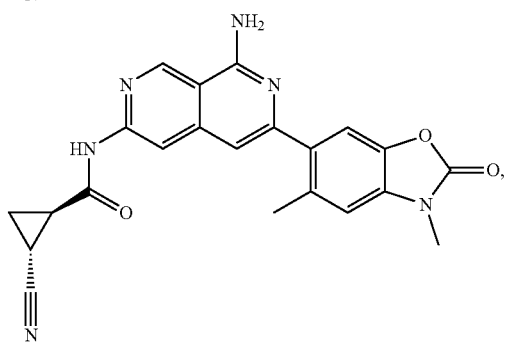
1464
-continued
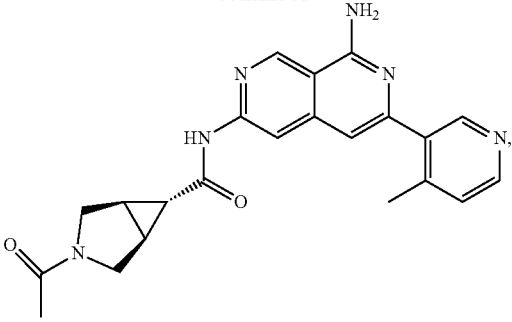
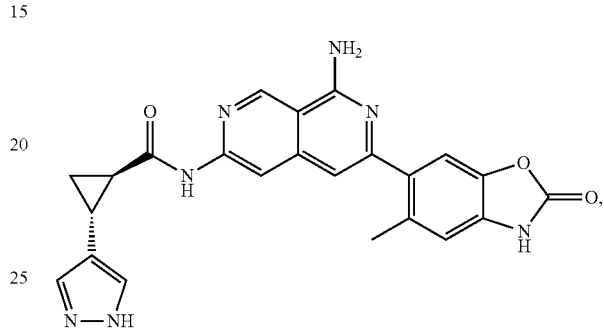
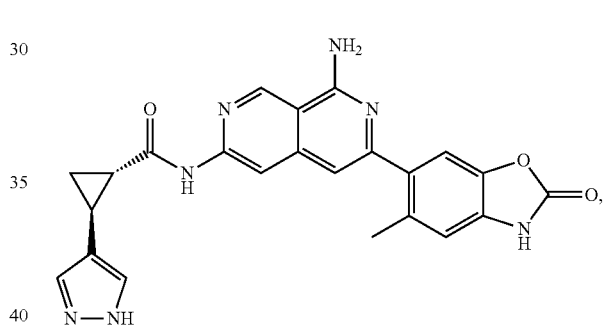
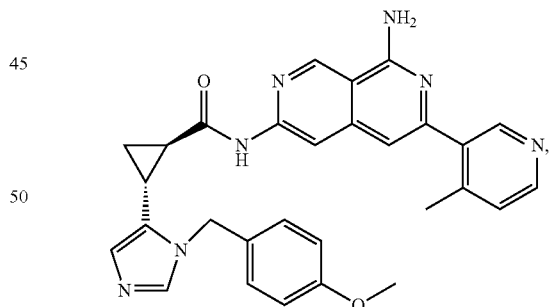
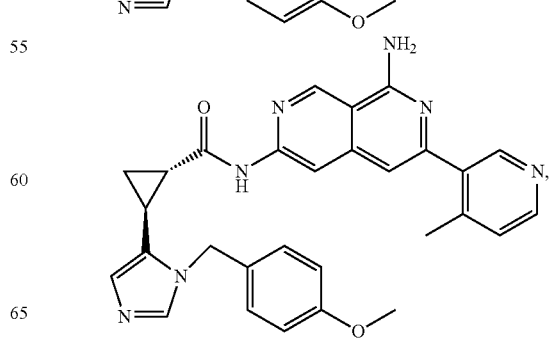

1465
-continued
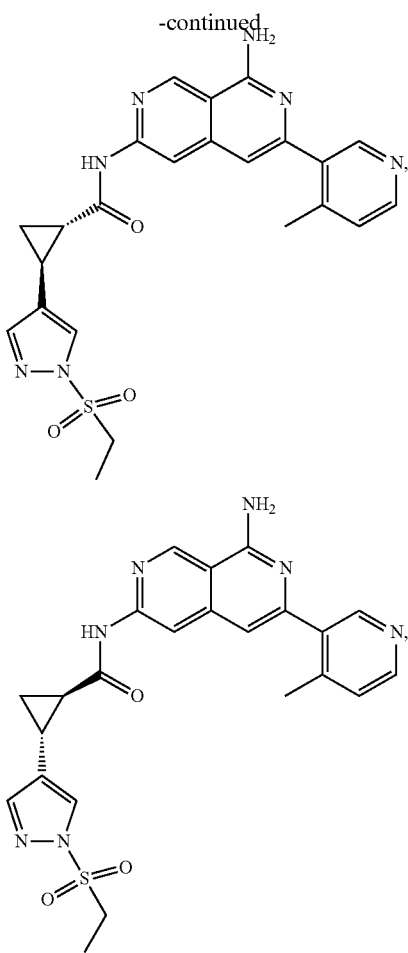
1466
-continued
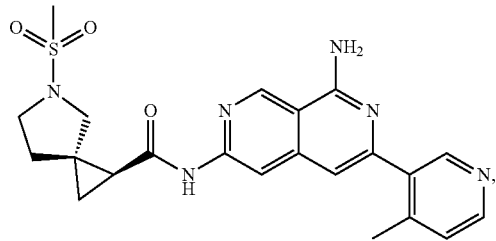
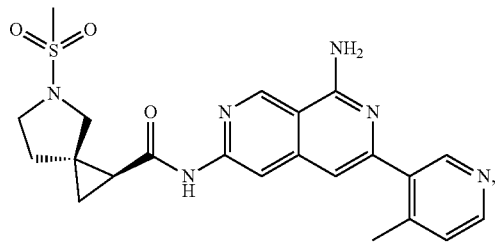
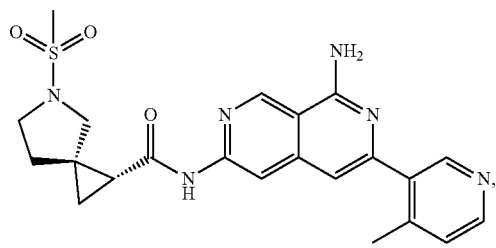
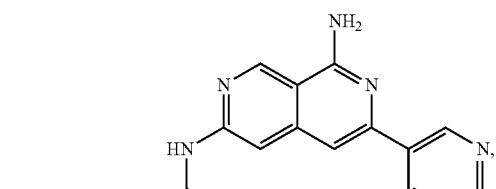
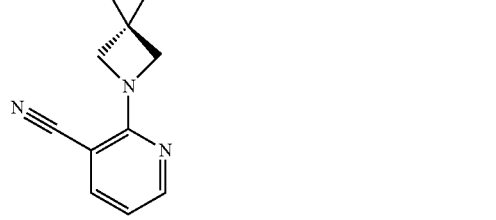
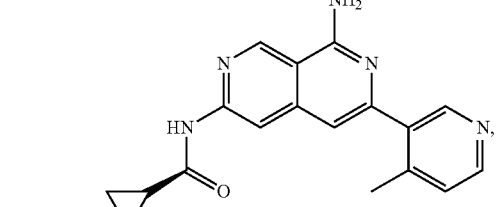

1467
-continued
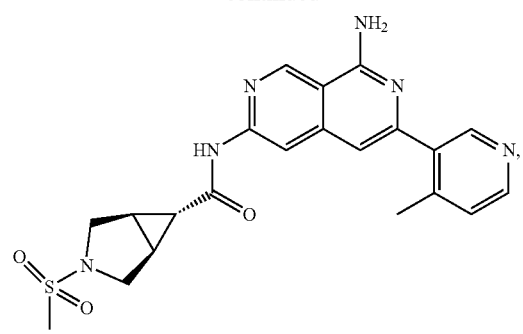
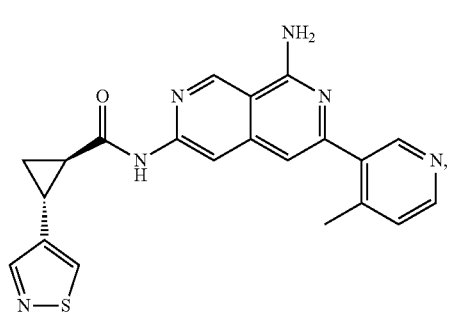
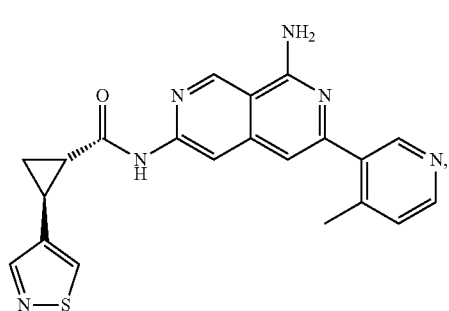
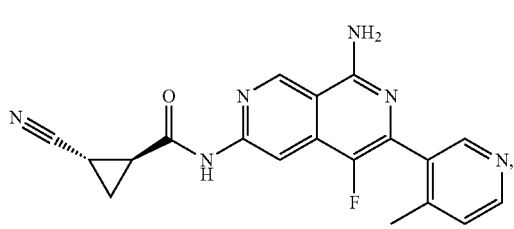
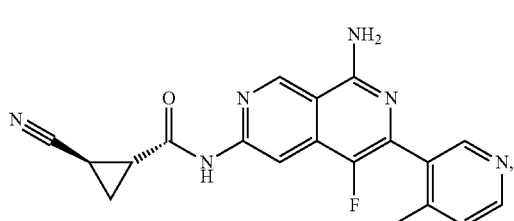
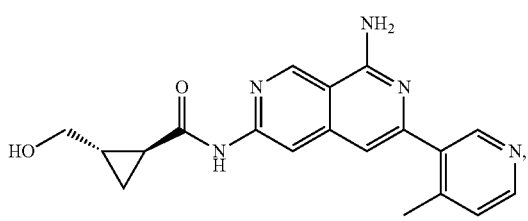
1468
-continued
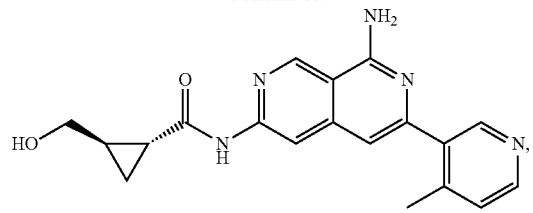
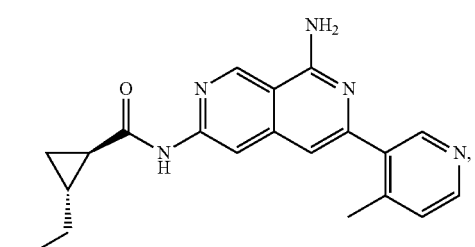
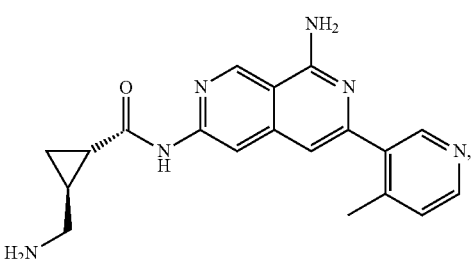
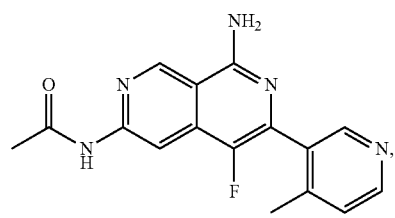
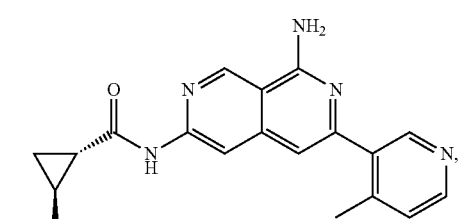
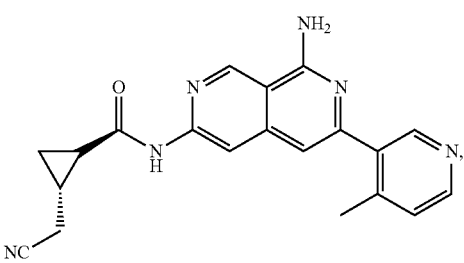

1469
-continued
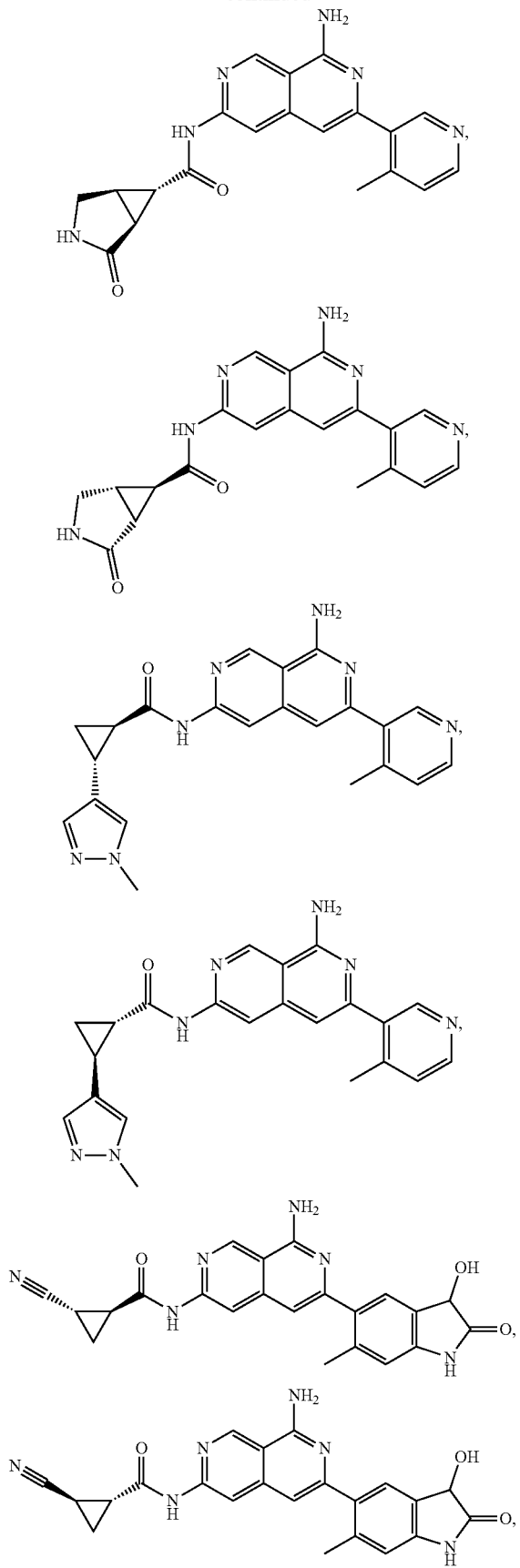
1470
-continued
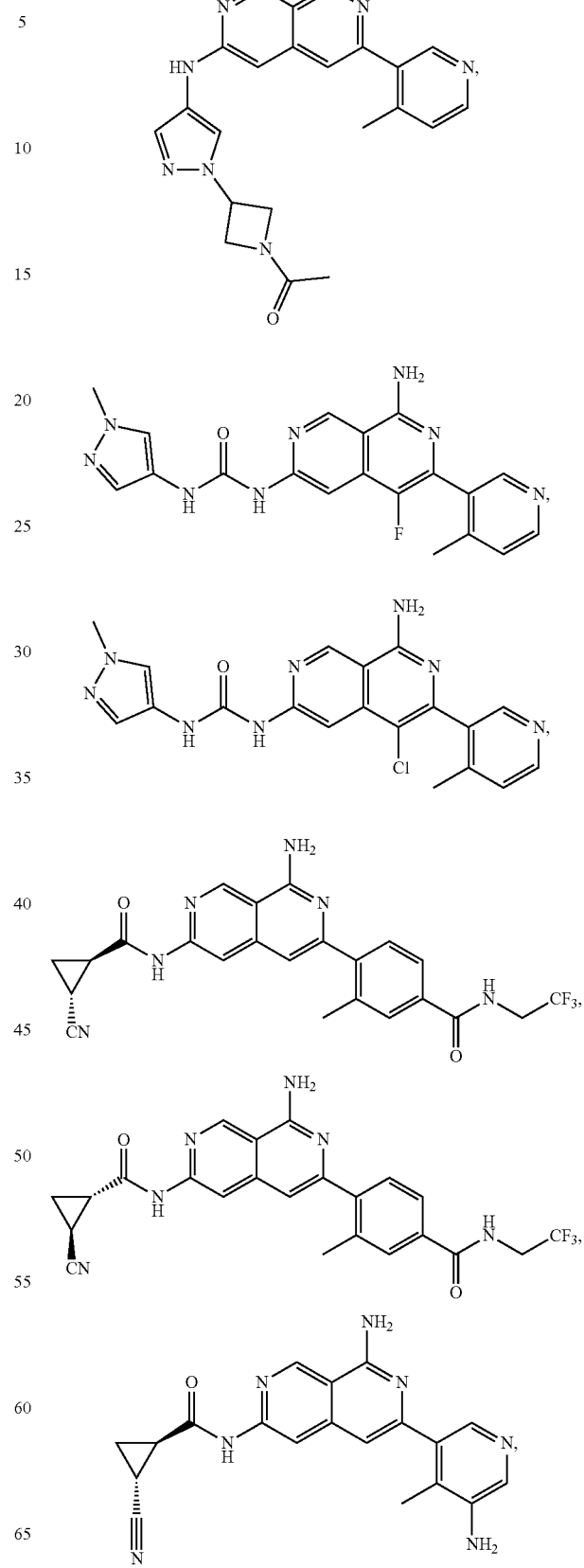

1471
-continued
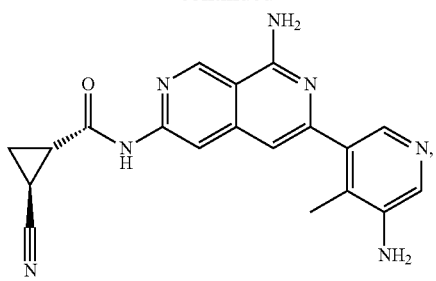
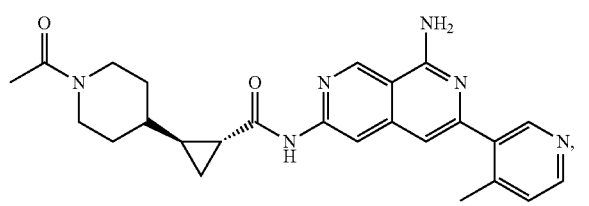
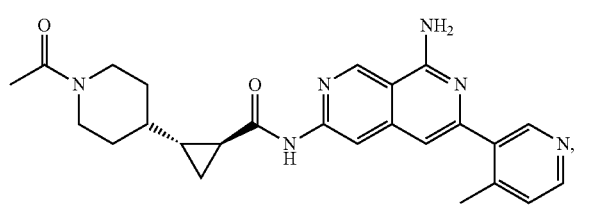
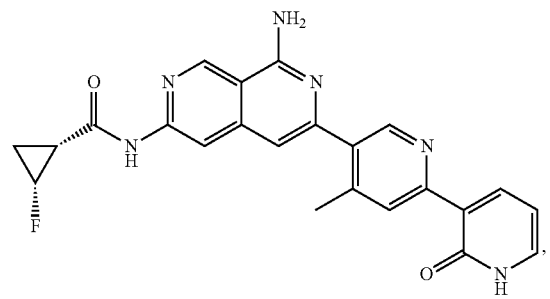
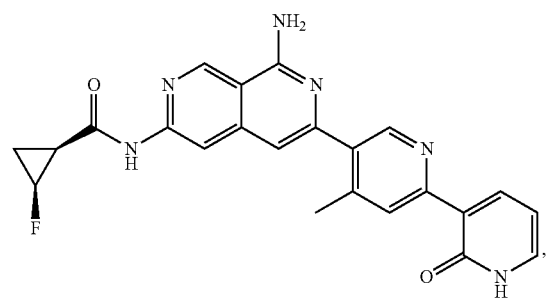
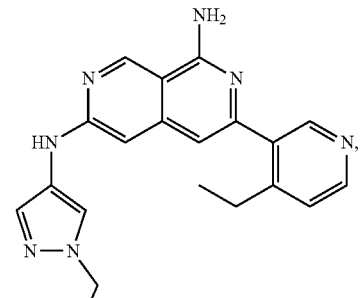
1472
-continued
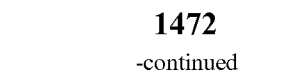
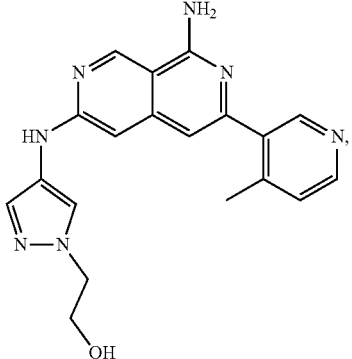
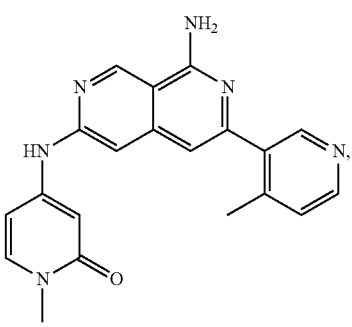
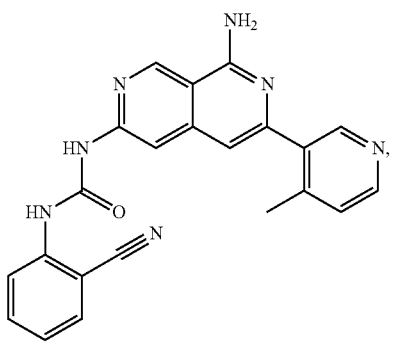
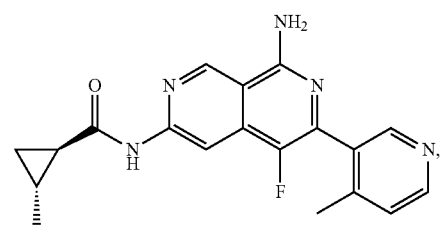
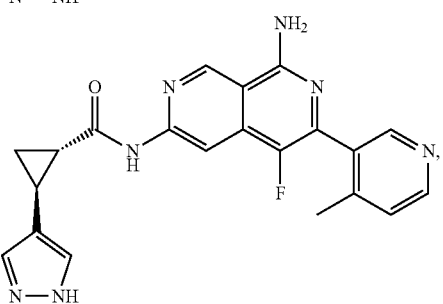

1473
-continued
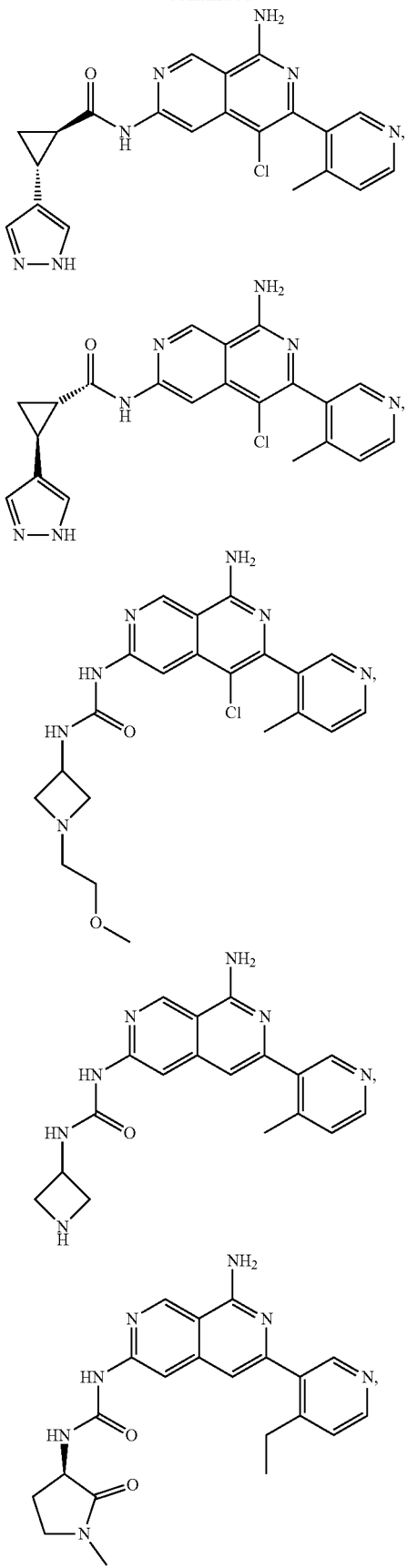
1474
-continued
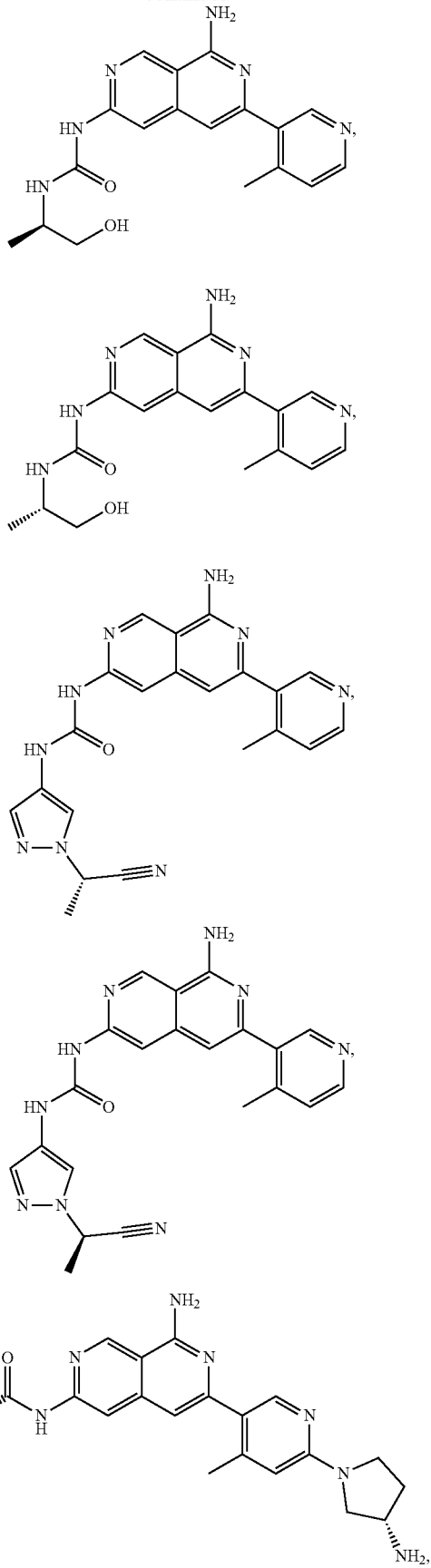

1475
-continued
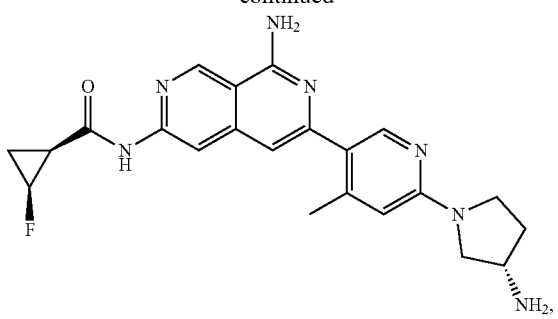
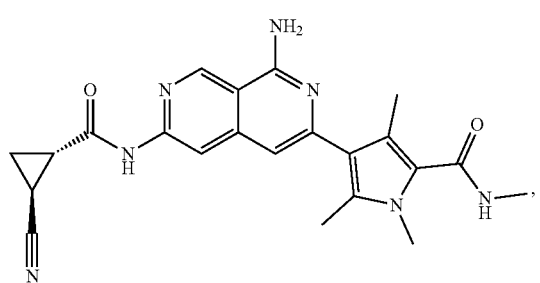
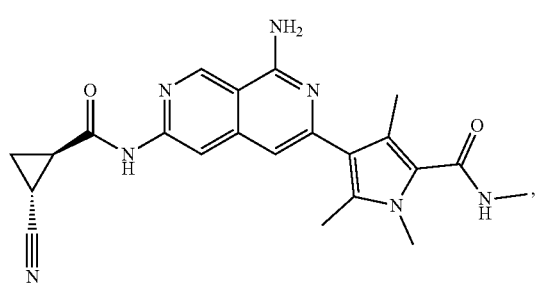
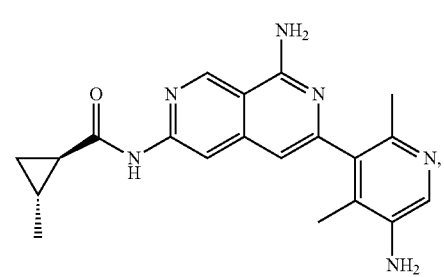
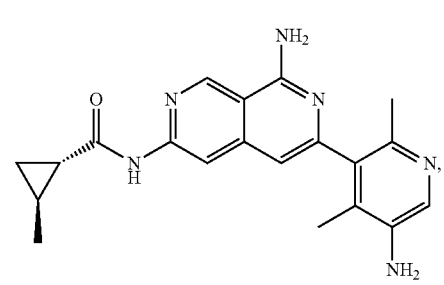
1476
-continued
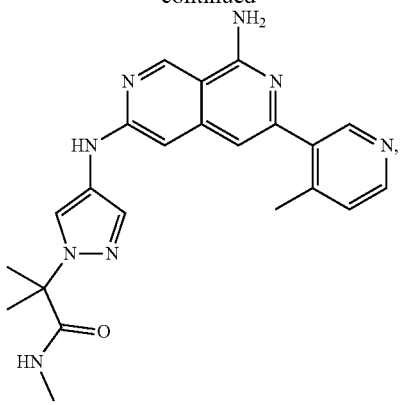
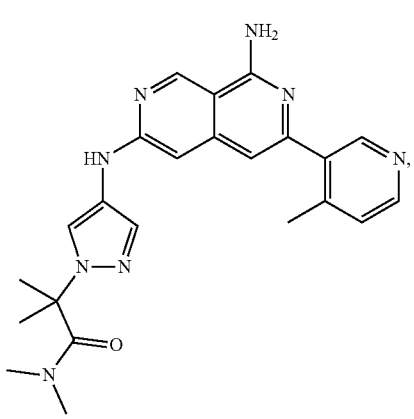
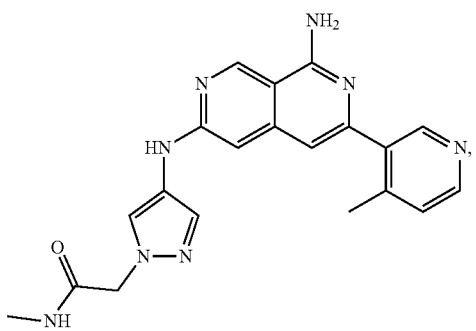
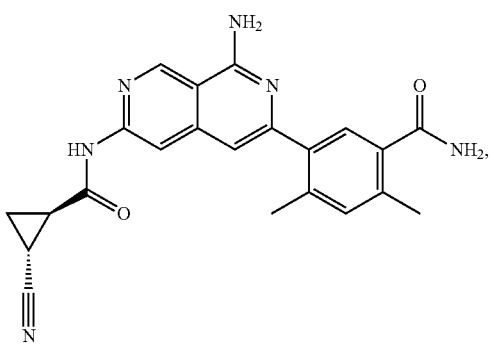

1477
-continued
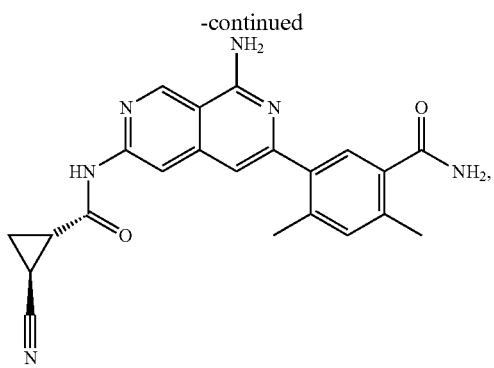
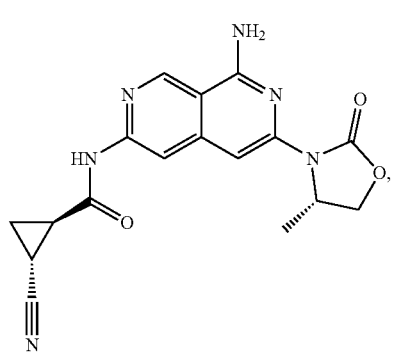
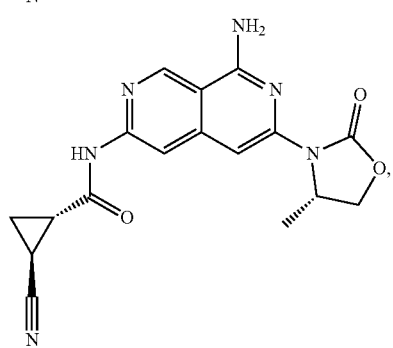
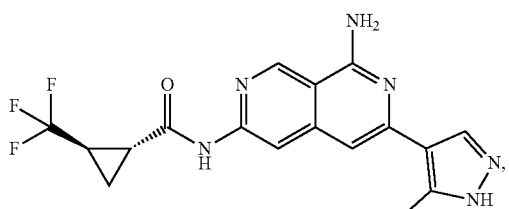
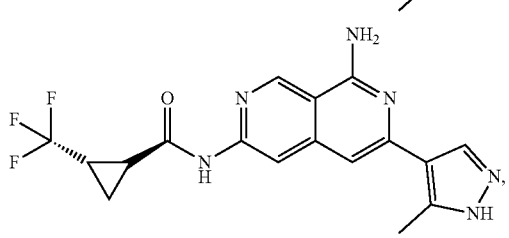
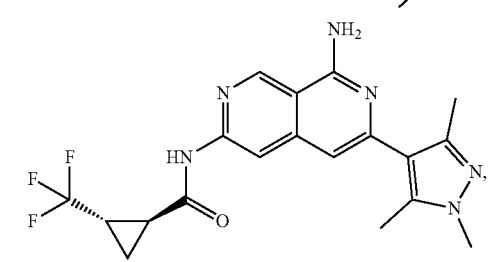
1478
-continued
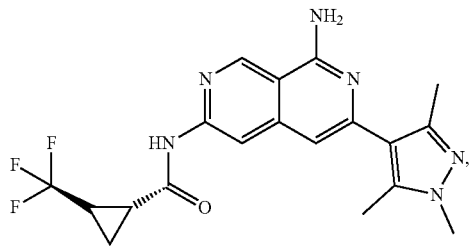
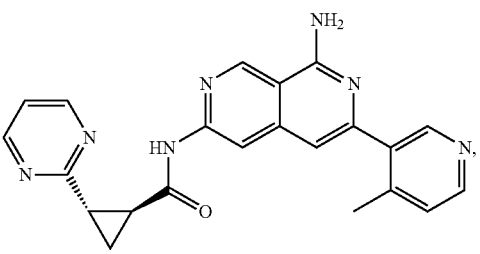
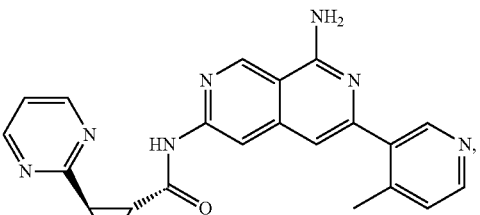
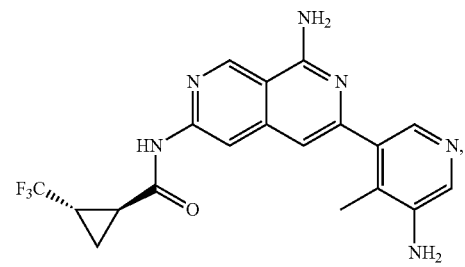
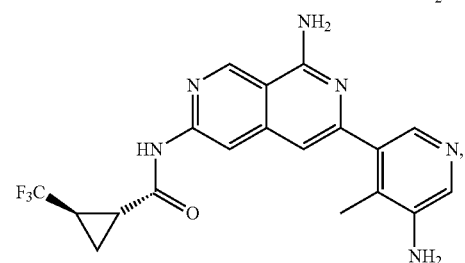
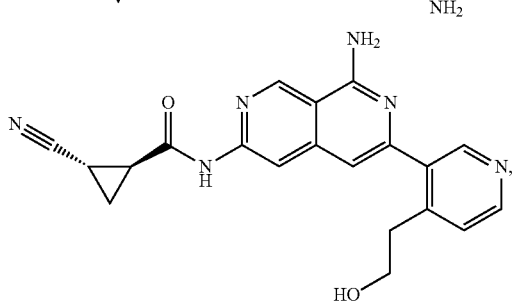

1479
-continued
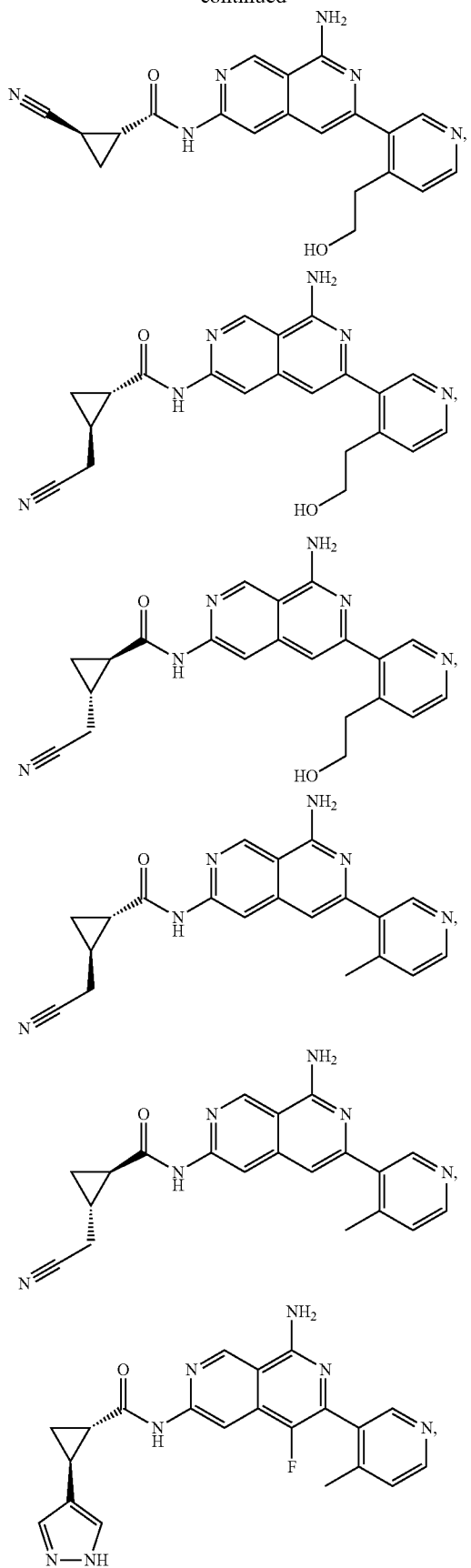
1480
-continued
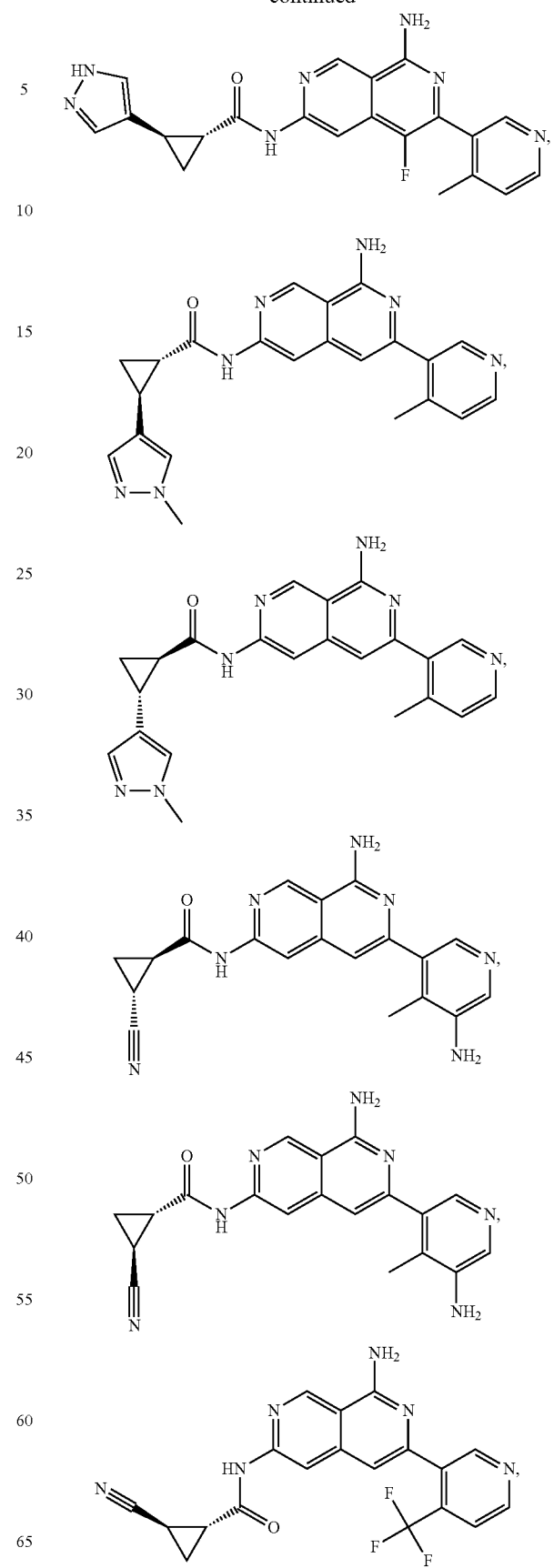

1481
-continued
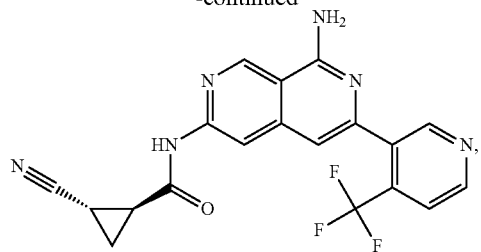
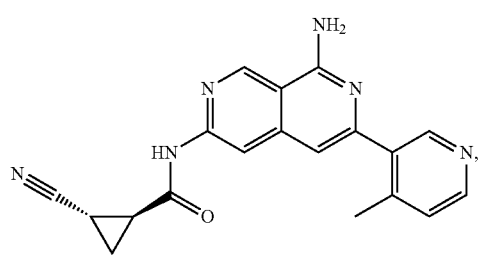
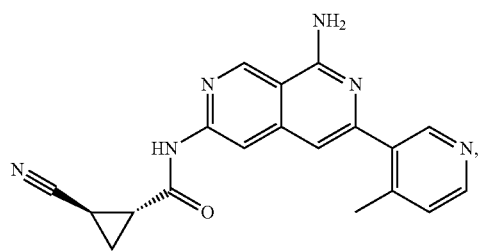
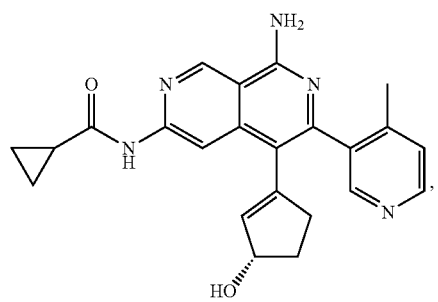
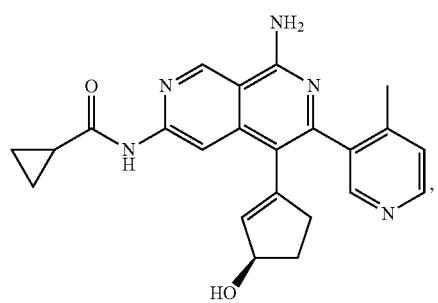
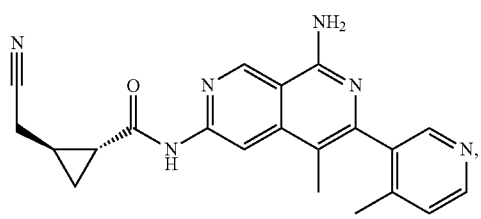
1482
-continued
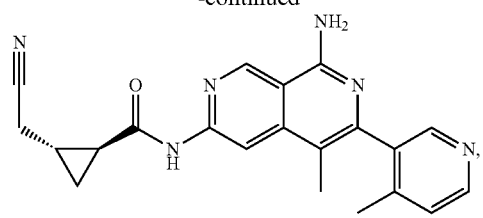
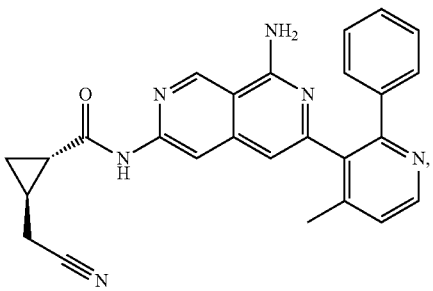
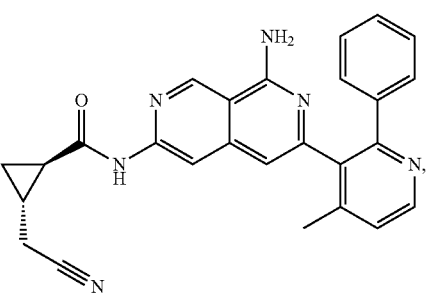
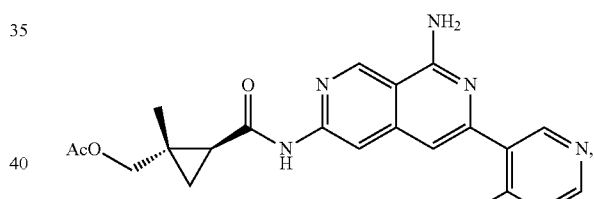
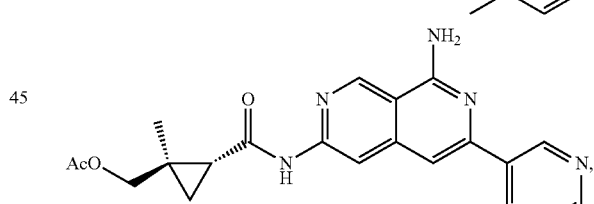
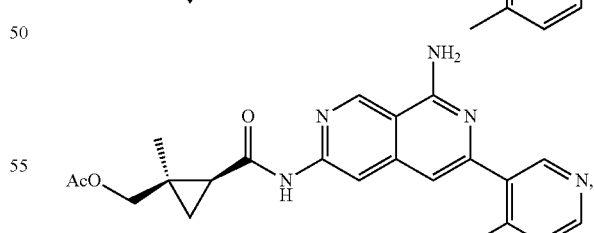
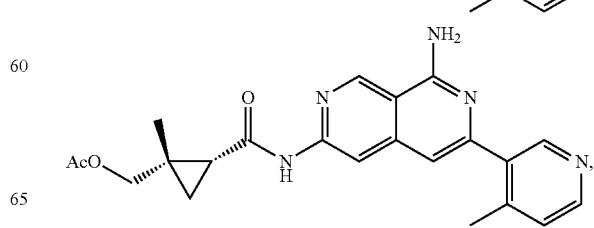

1483
-continued
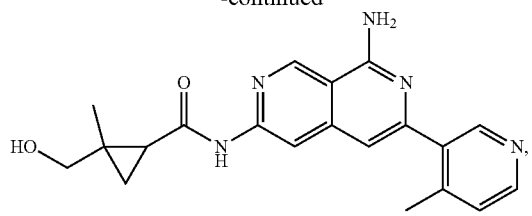
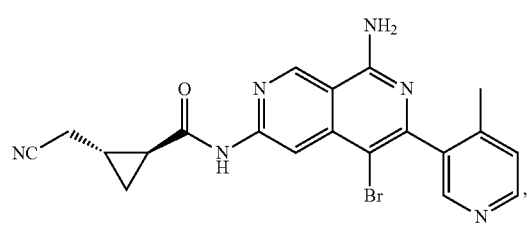
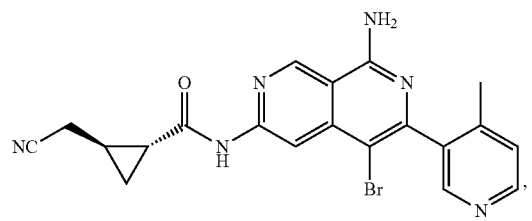
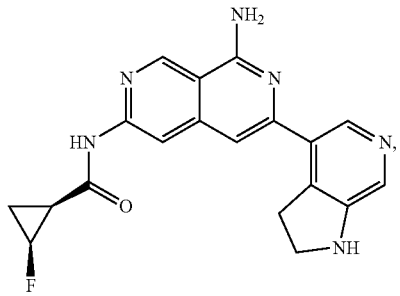
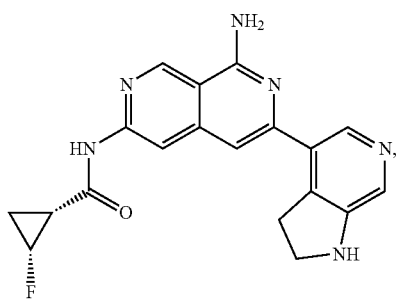
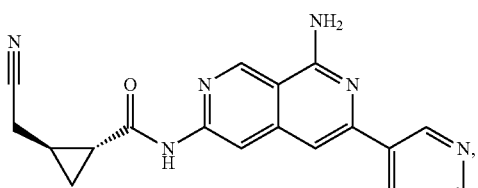
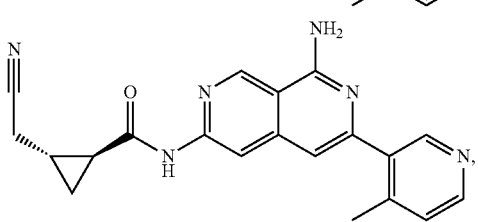
1484
-continued
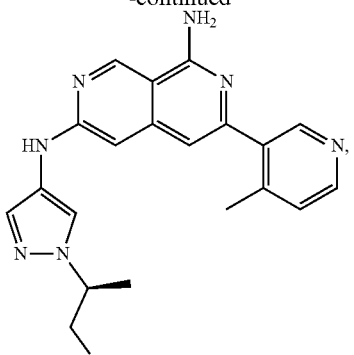
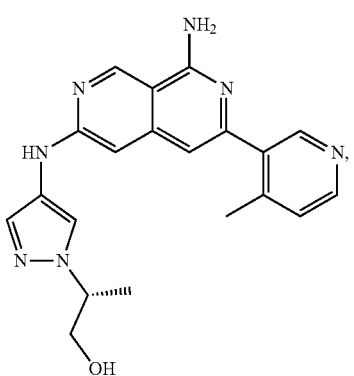
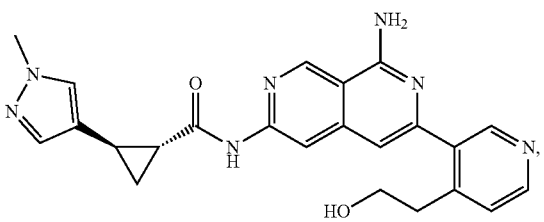
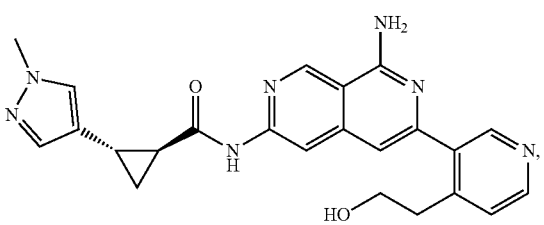
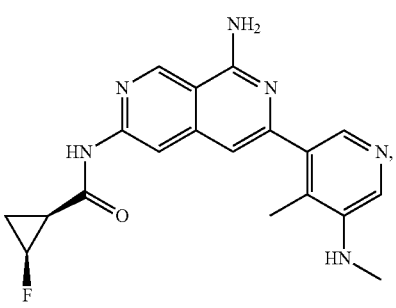

1485
-continued
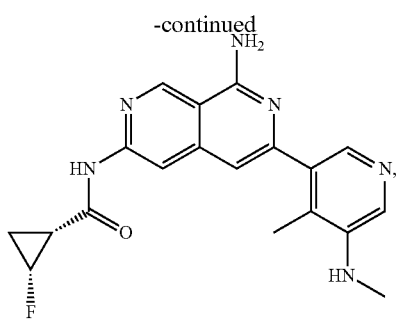
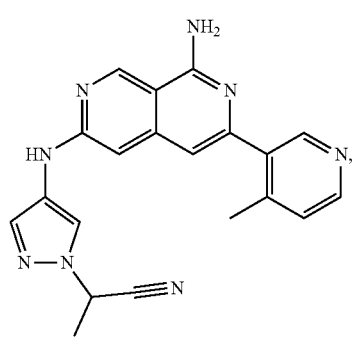
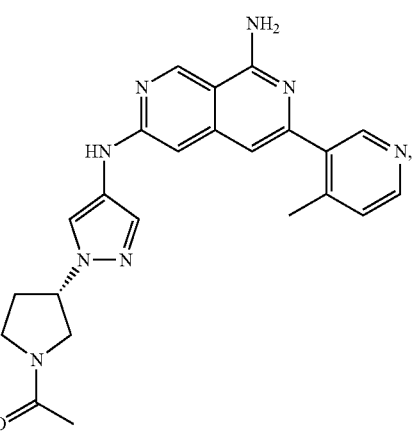
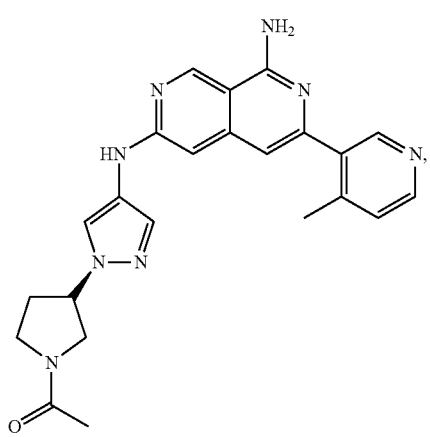
1486
-continued
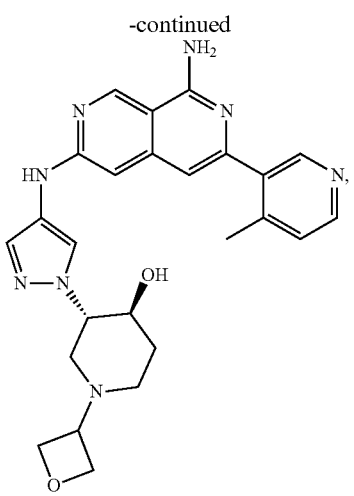
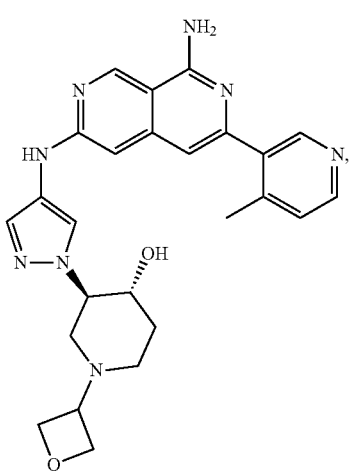
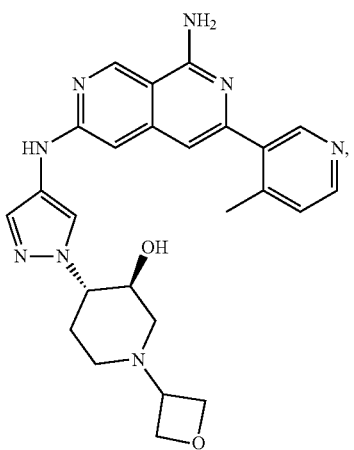

1487
-continued
1488
-continued
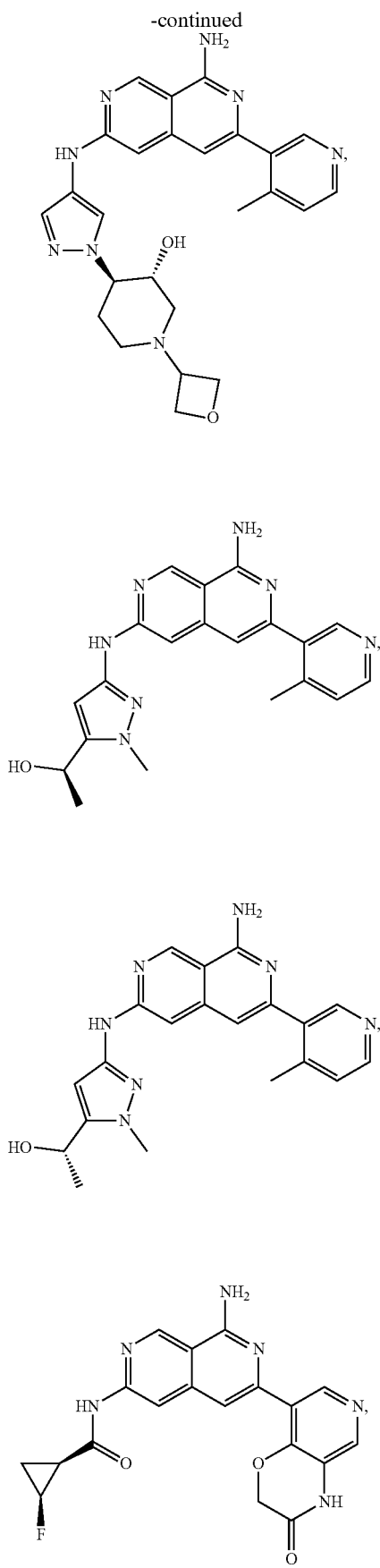
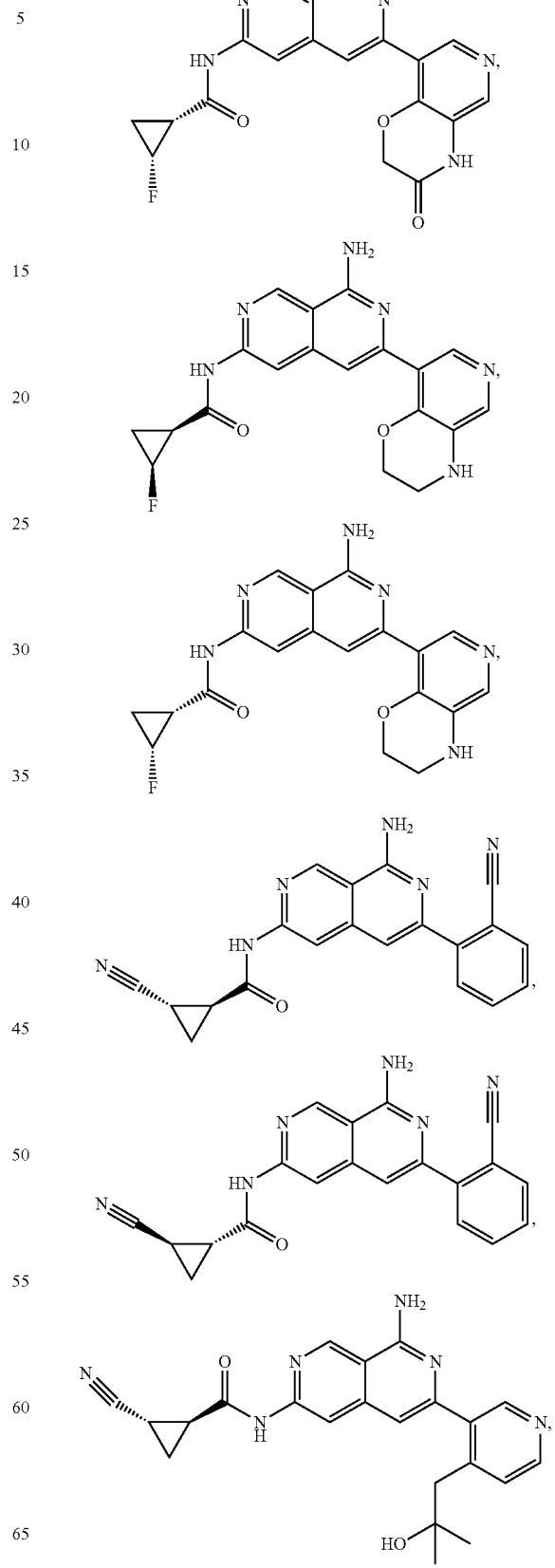

1489
-continued
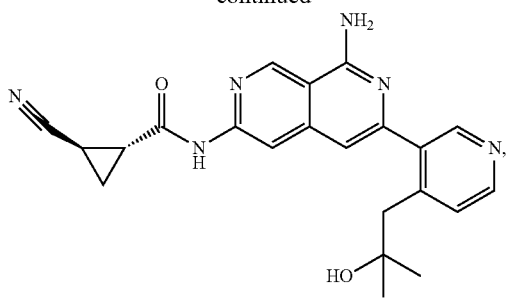
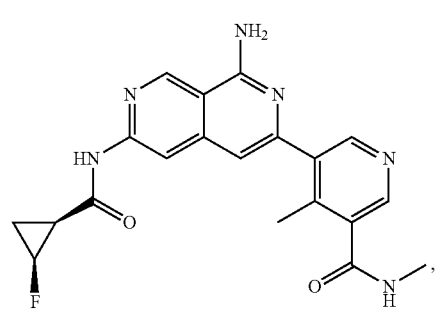
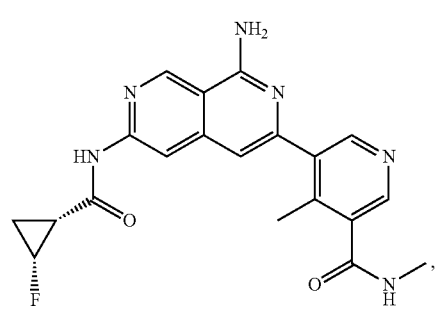
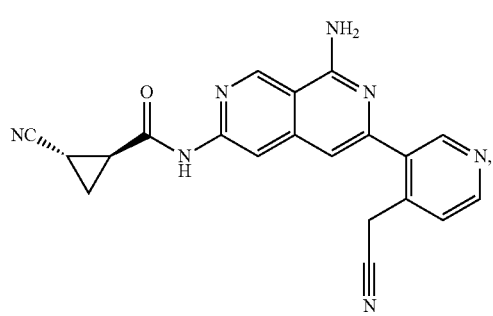
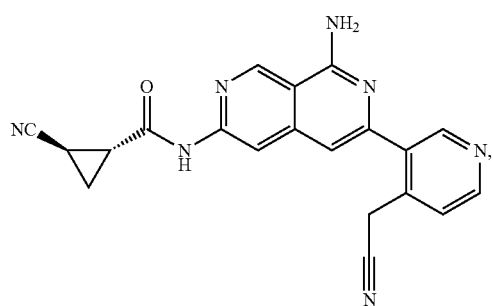
1490
-continued
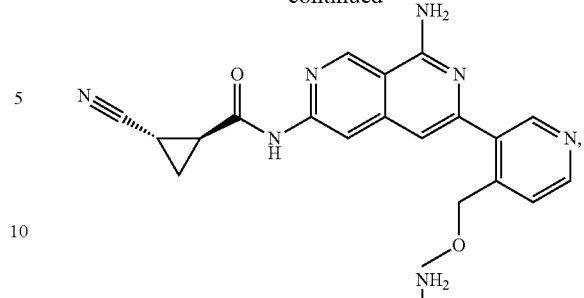
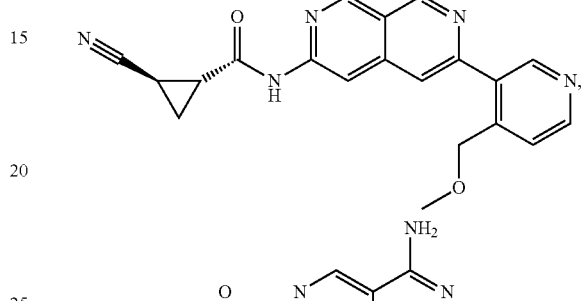
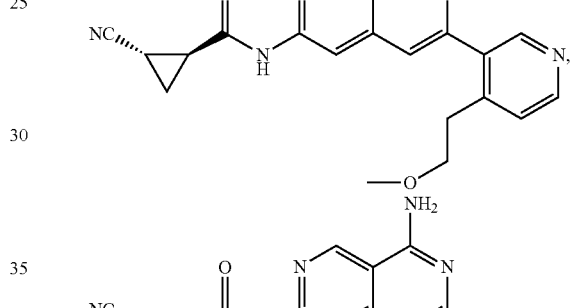
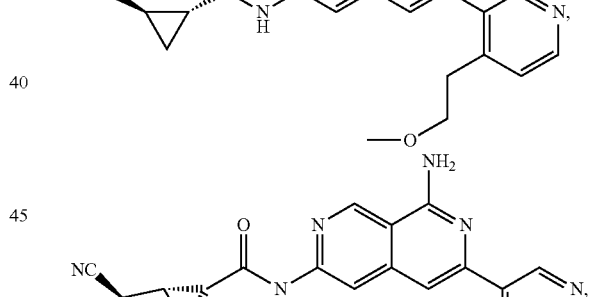
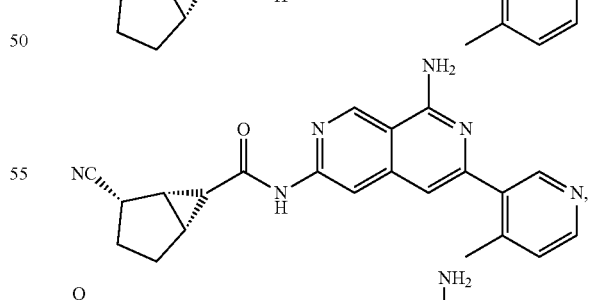
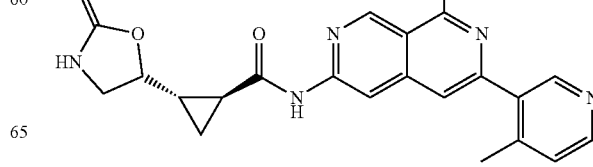

1491 -continued
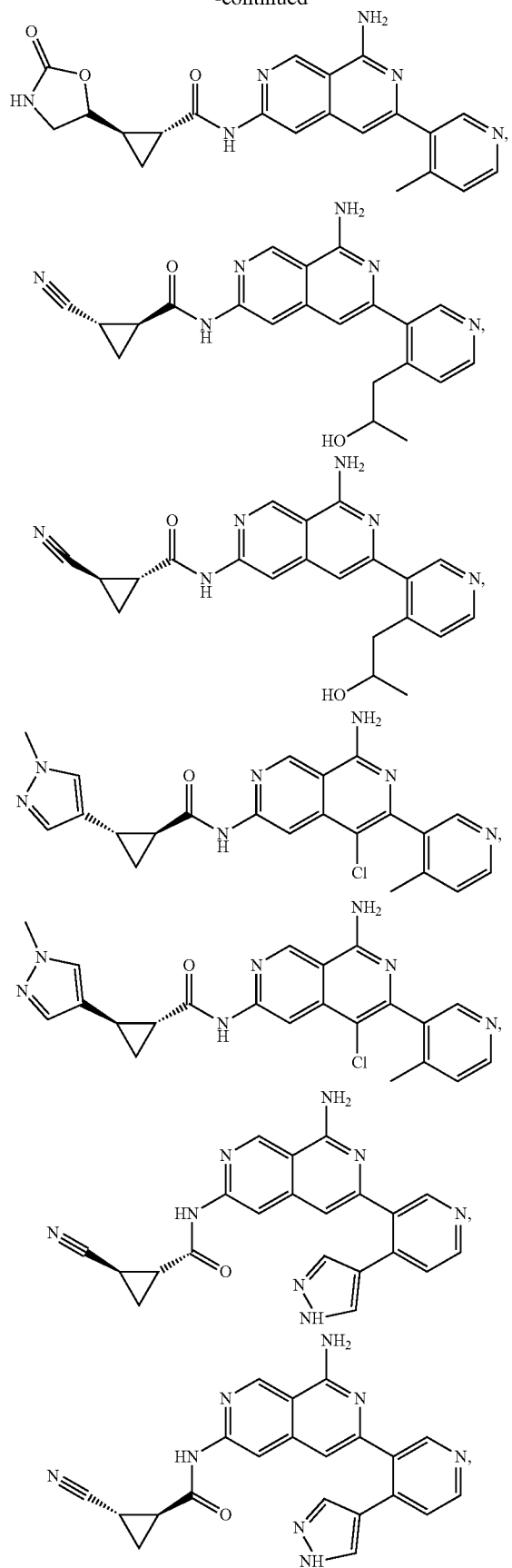
1492 -continued
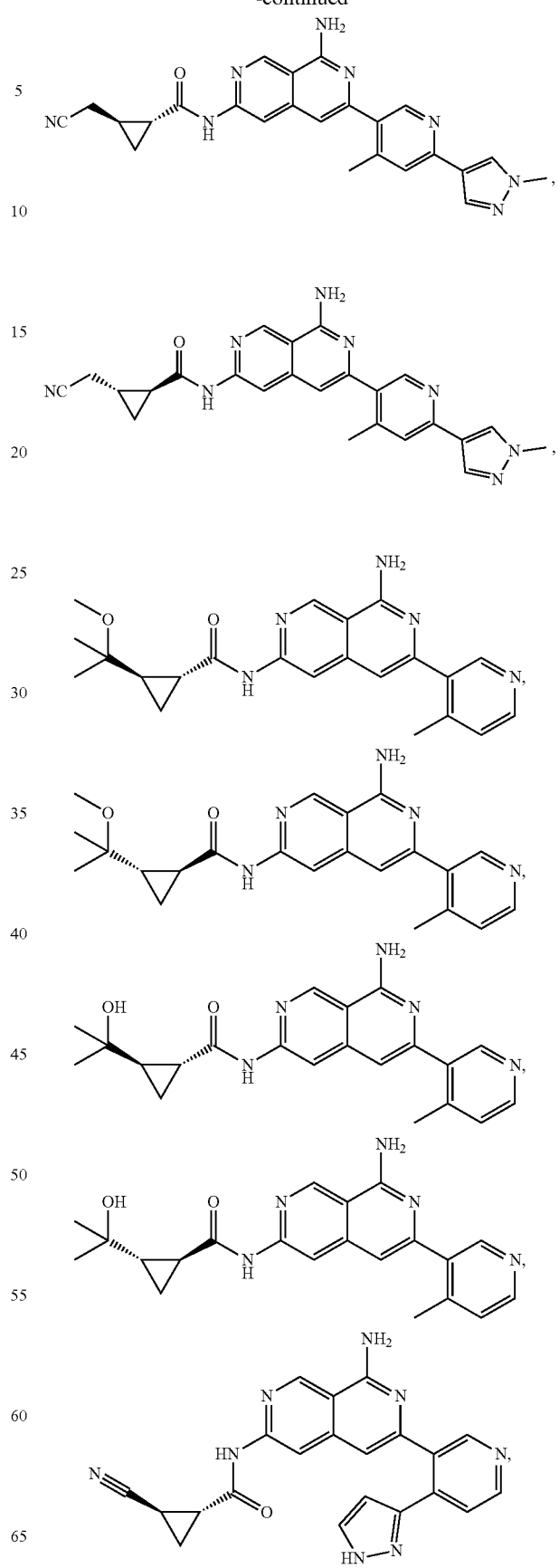

1493
-continued
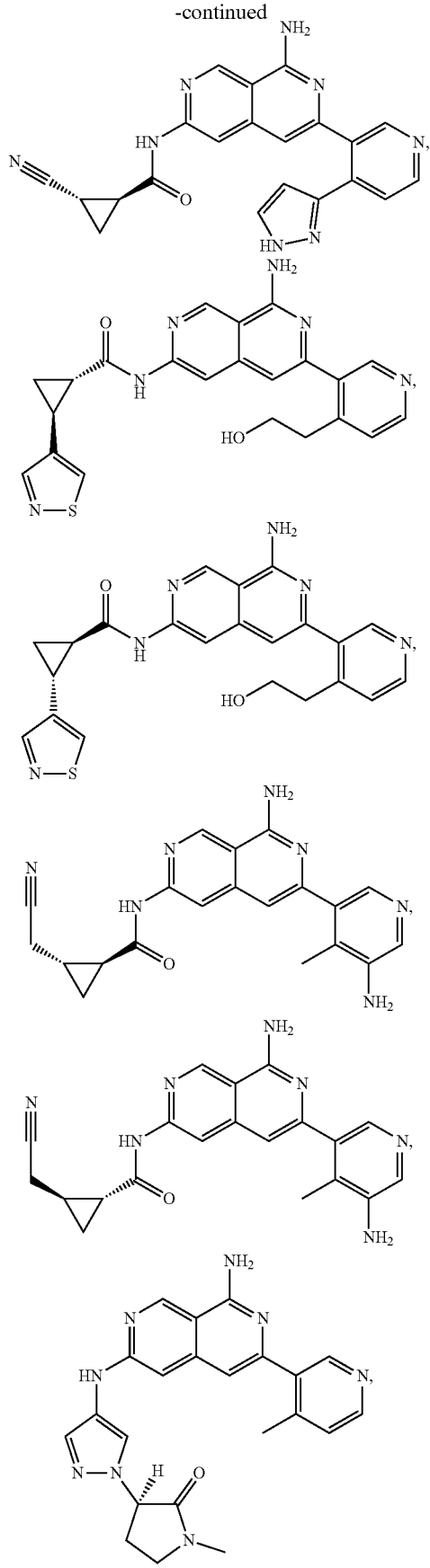
1494
-continued
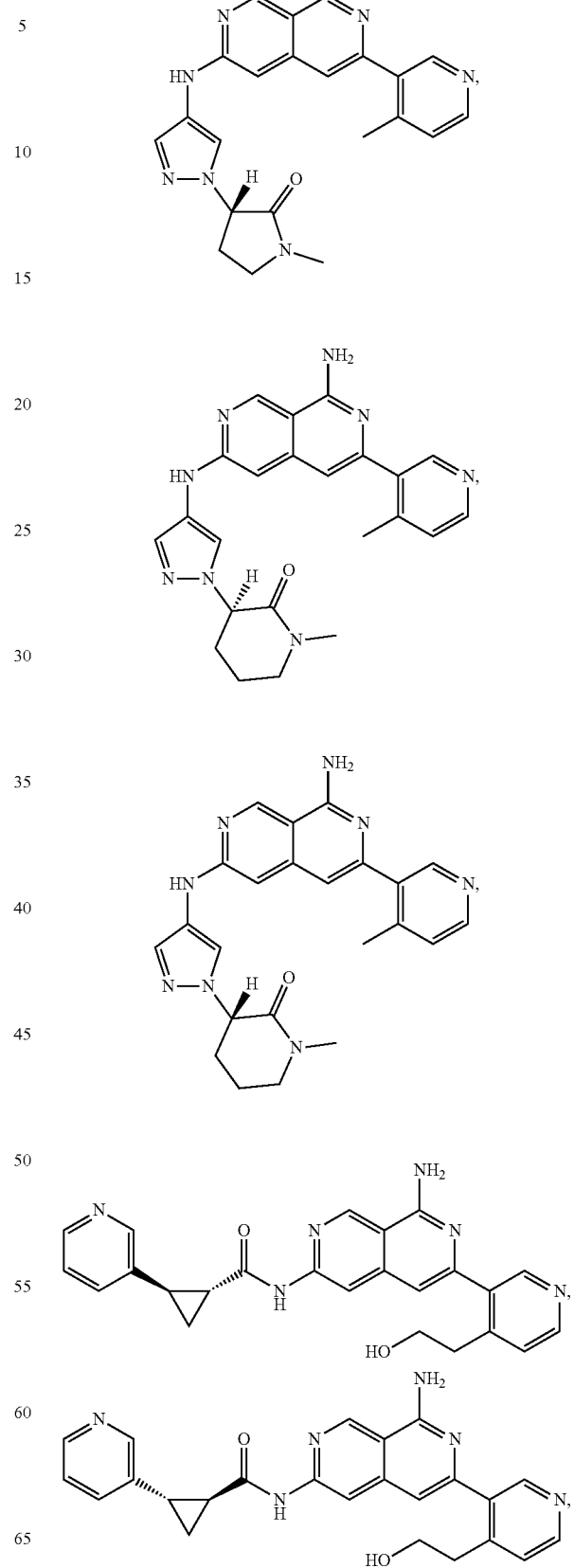

1495
-continued
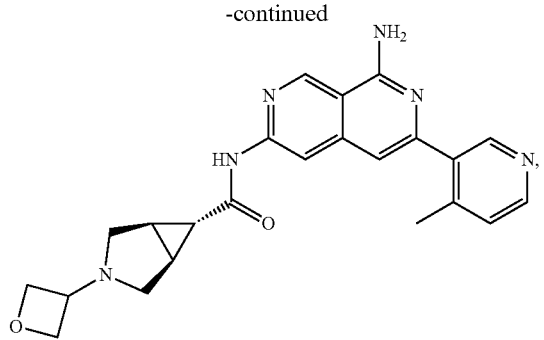
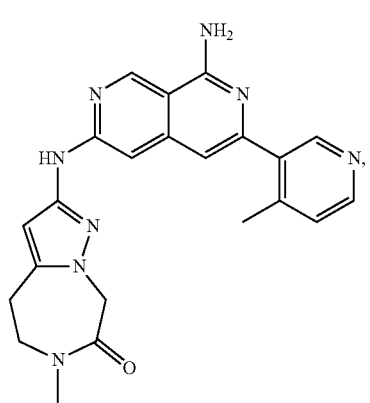
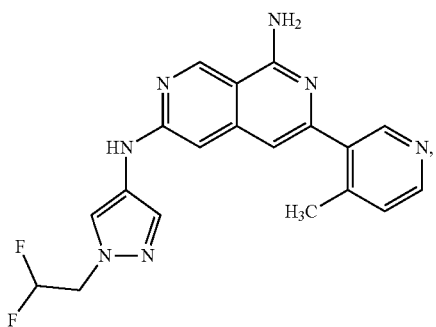
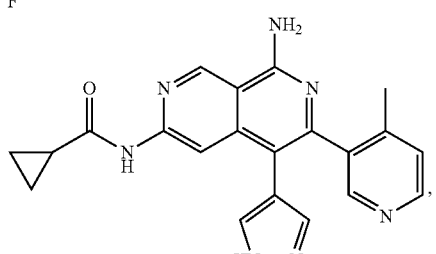
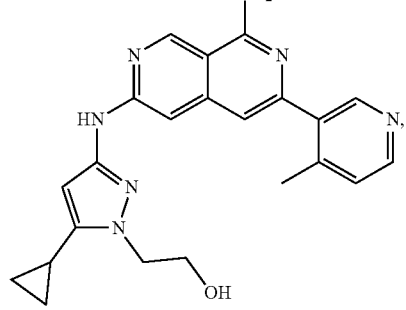
1496
-continued
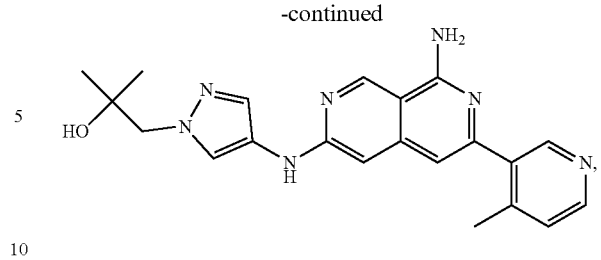
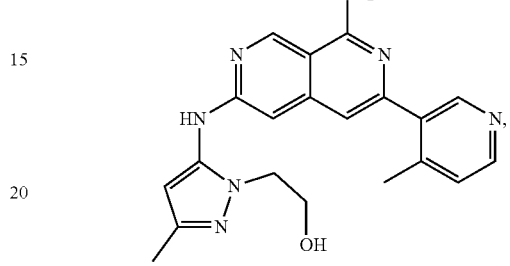
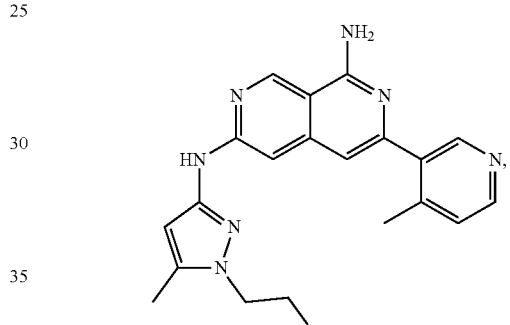
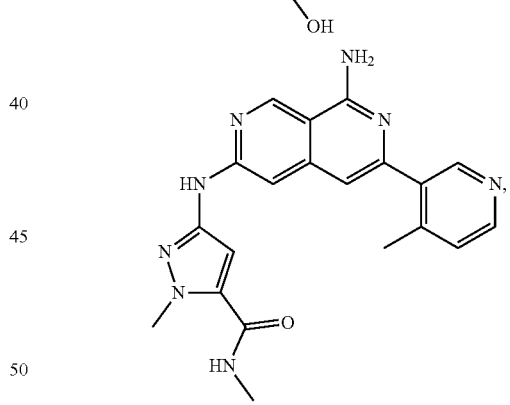
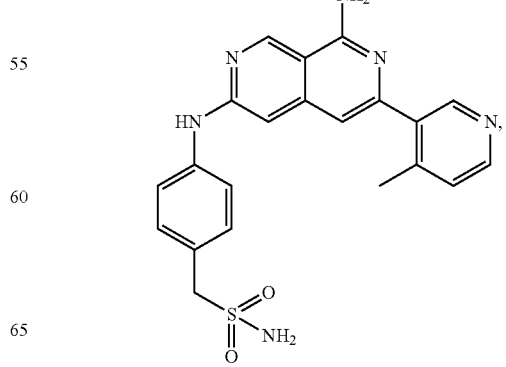

1497
-continued
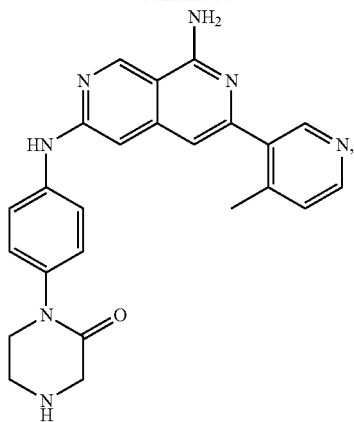
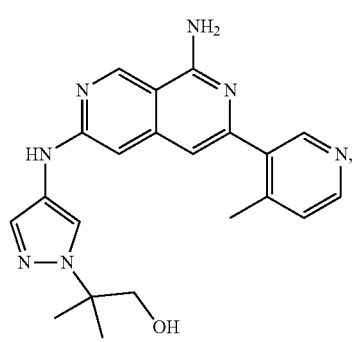
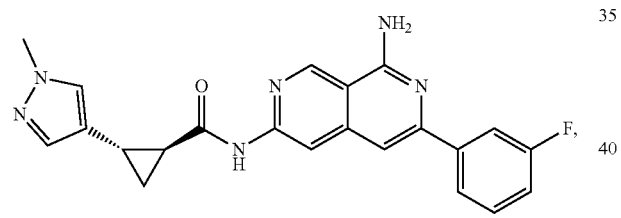
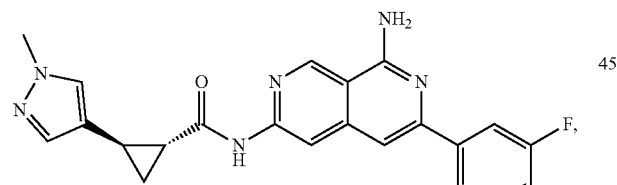
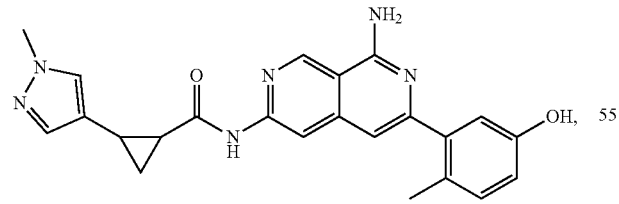
1498
-continued
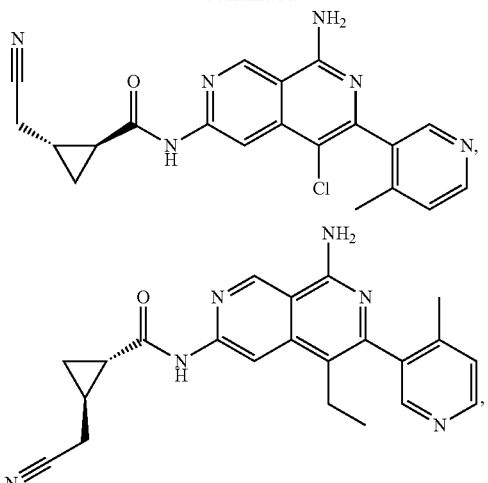
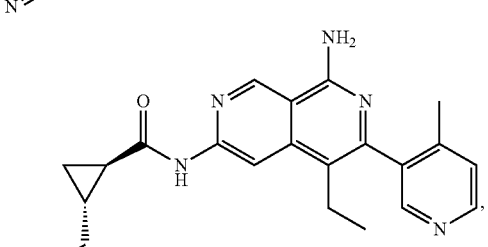
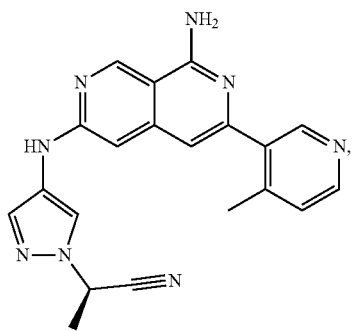
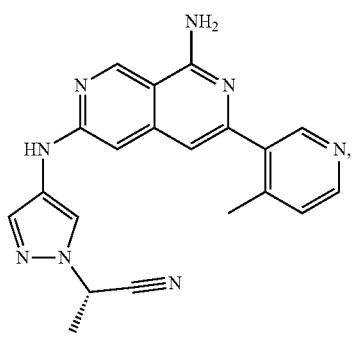
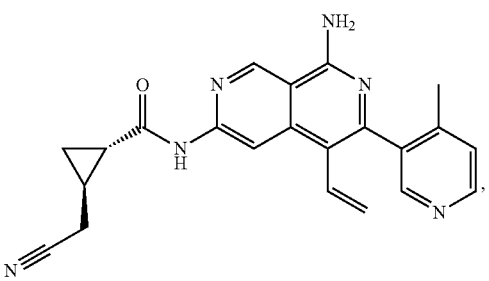

1499
-continued
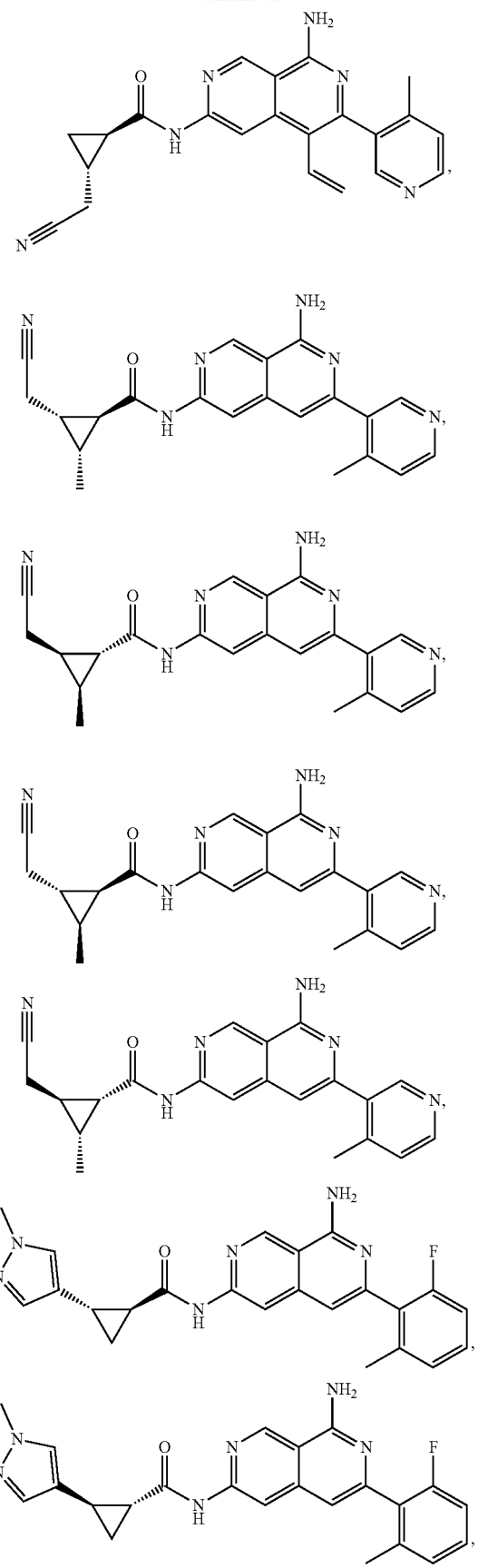
1500
-continued
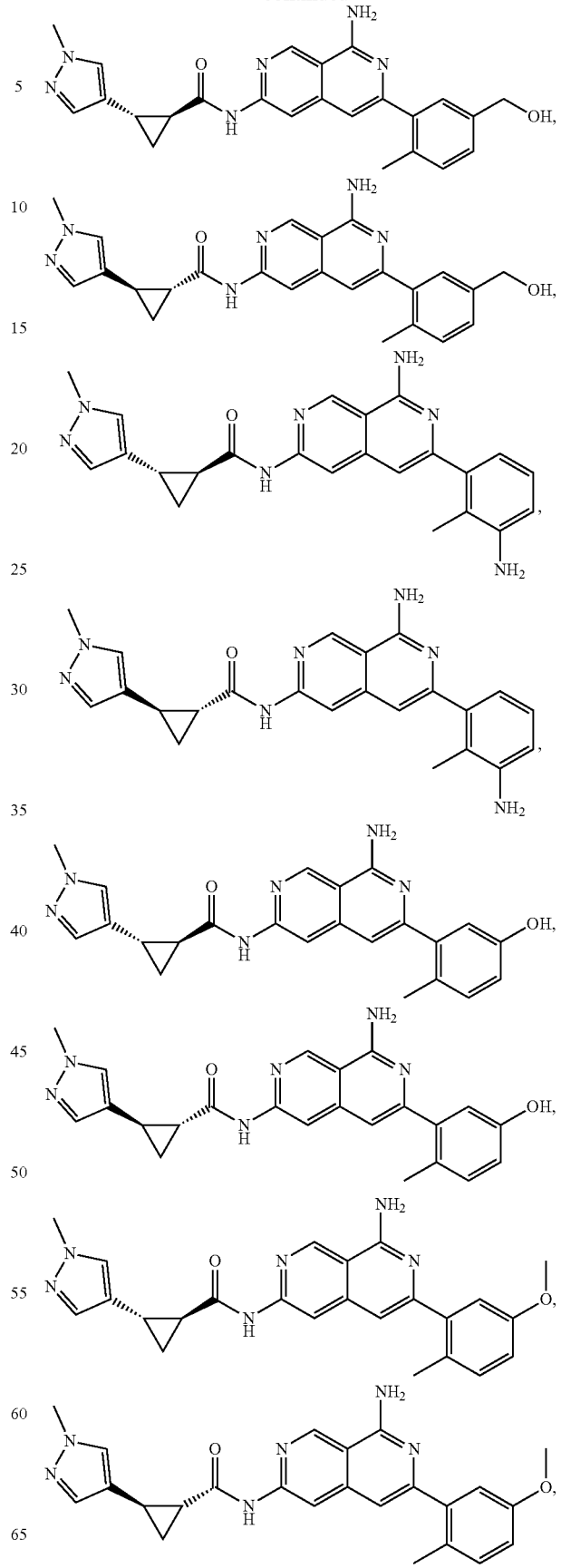

1501
-continued
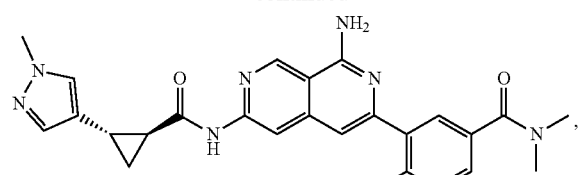
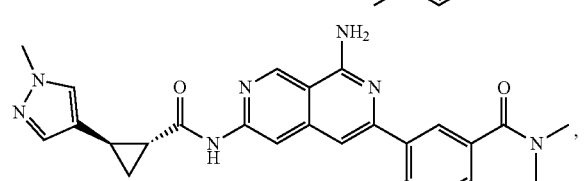
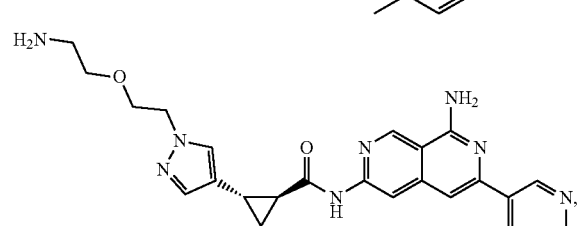
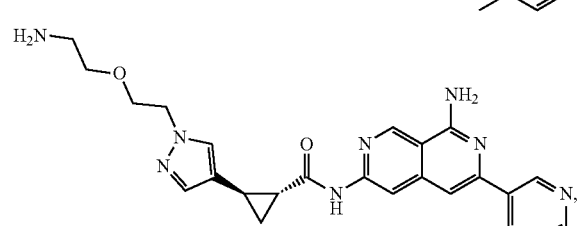
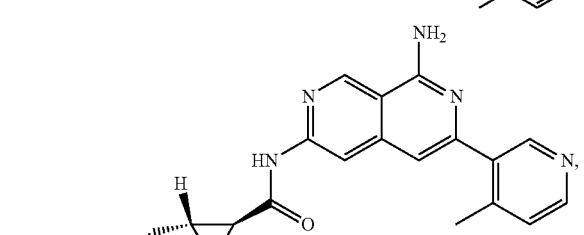
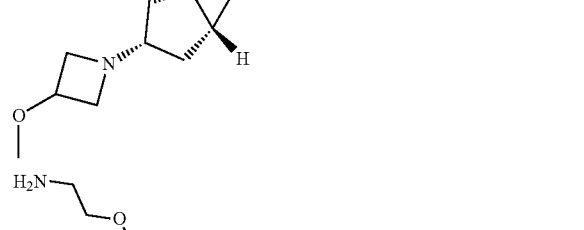
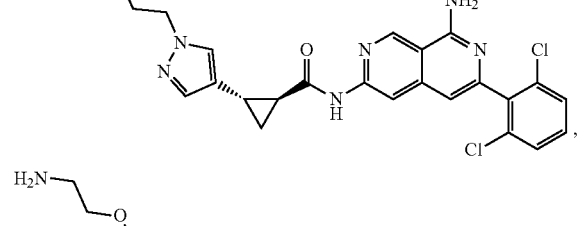
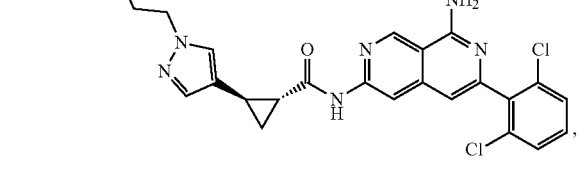
1502
-continued
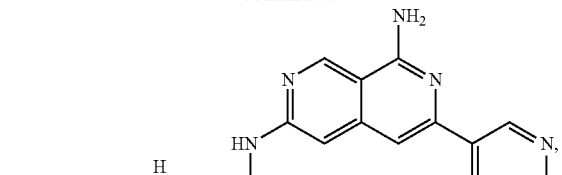
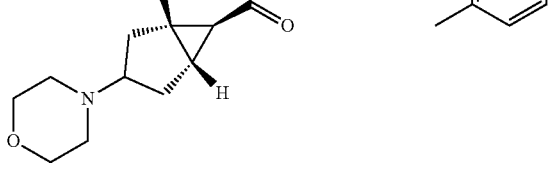
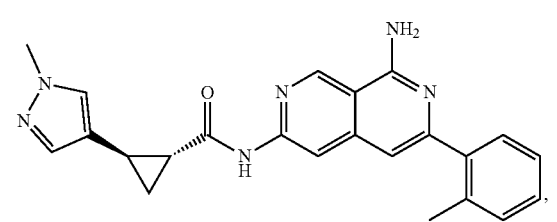
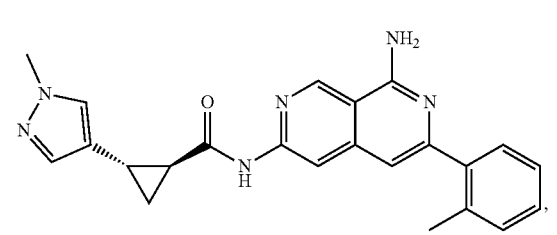
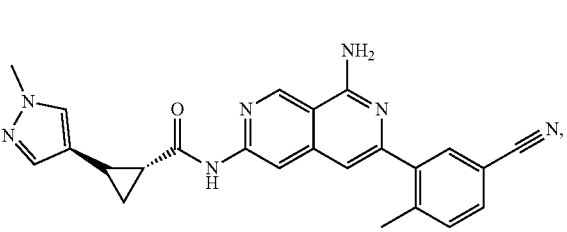
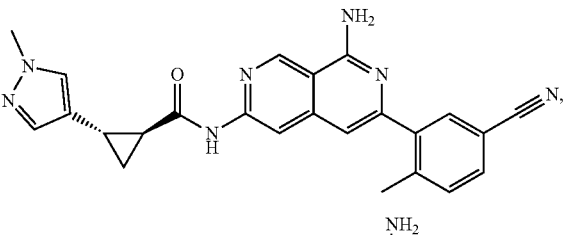
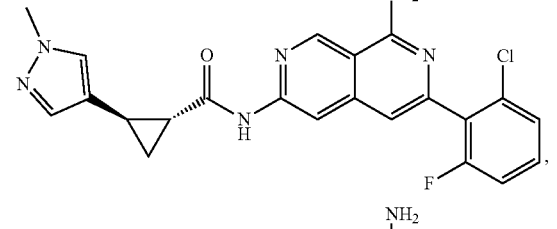
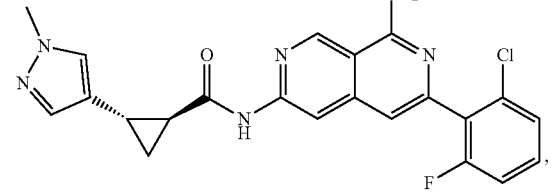

1503
-continued
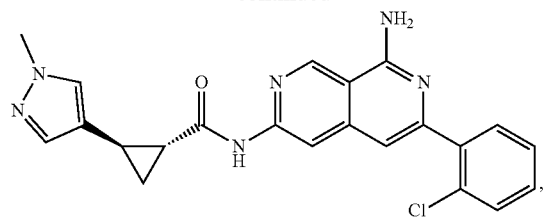
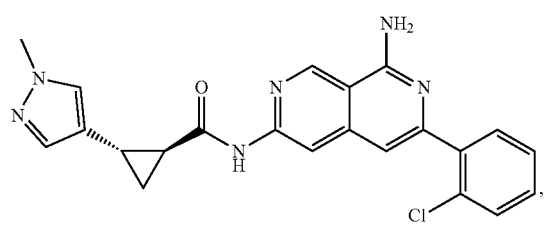
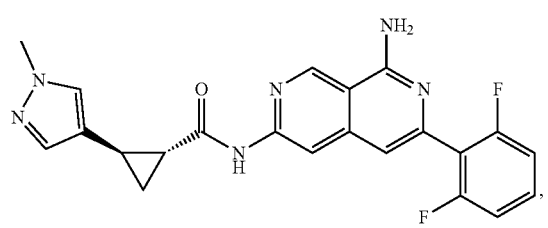
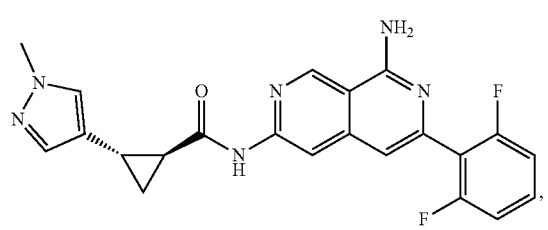
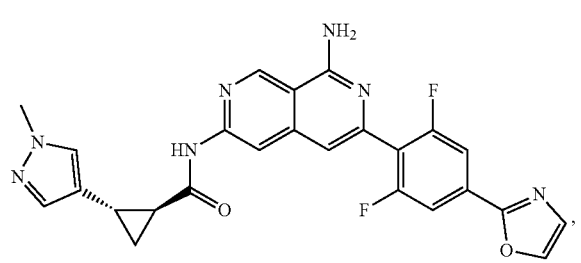
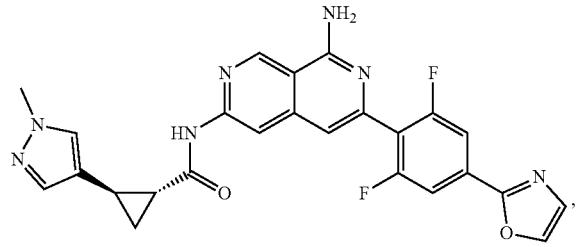
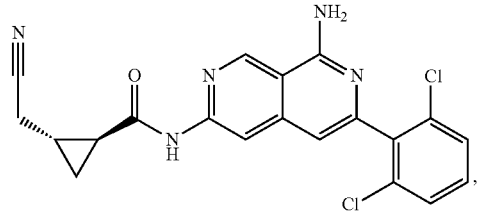
1504
-continued
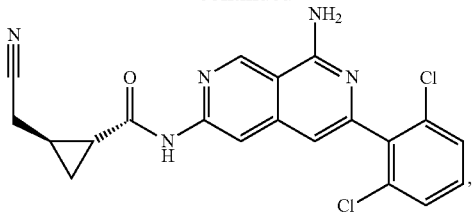
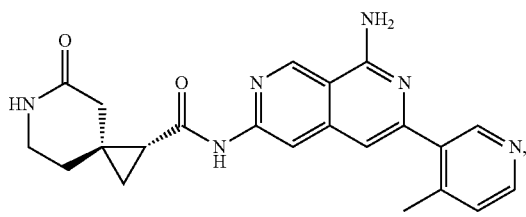
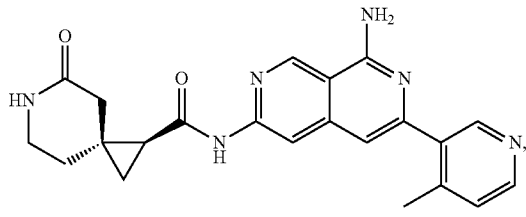
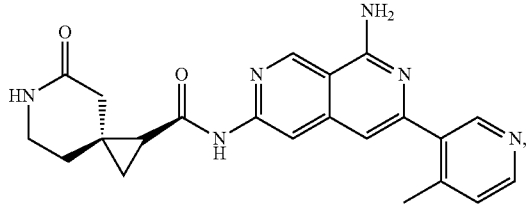
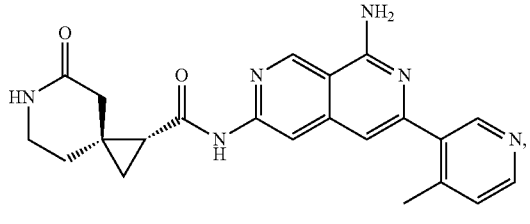
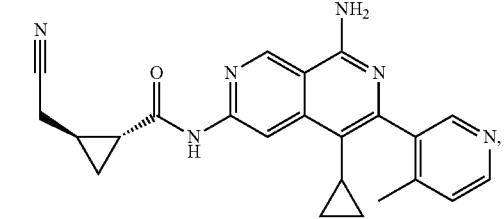
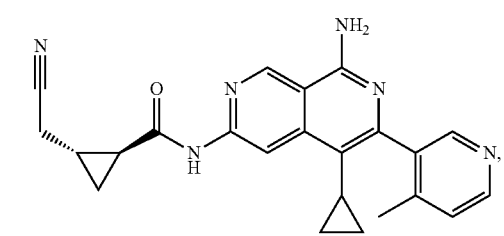

1505
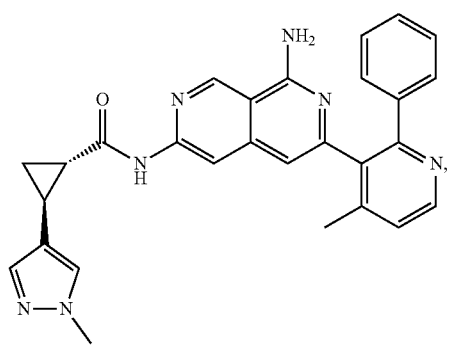
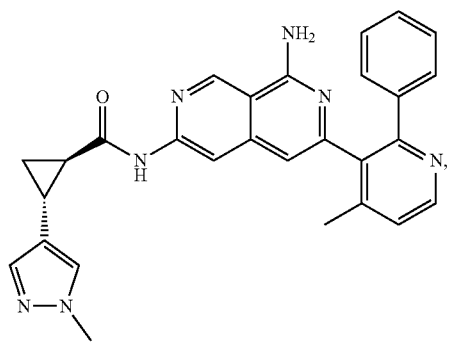
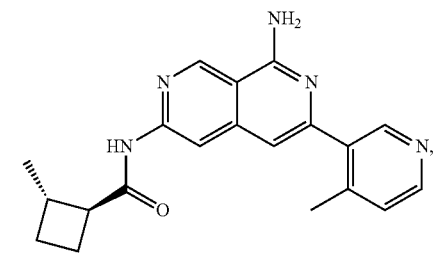
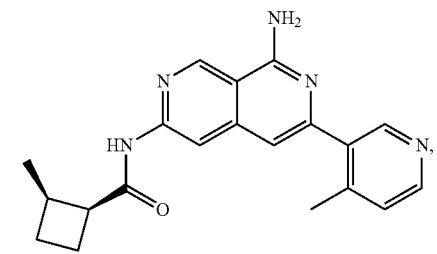
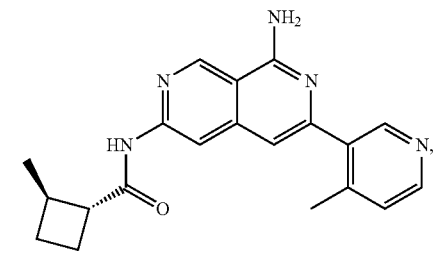
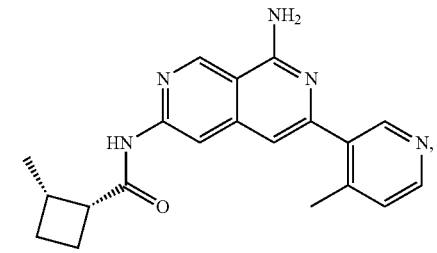
1506
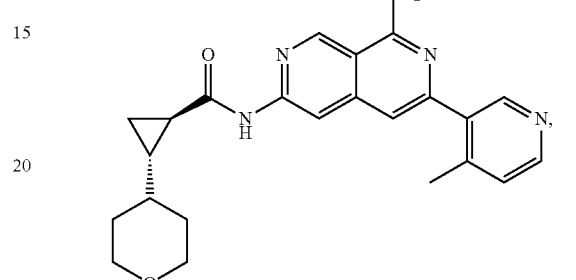
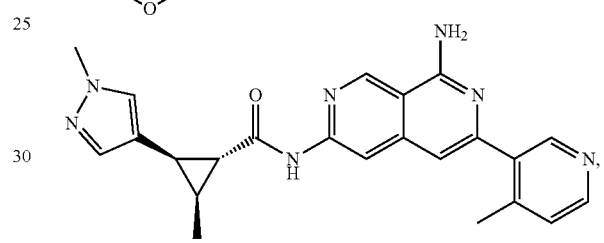
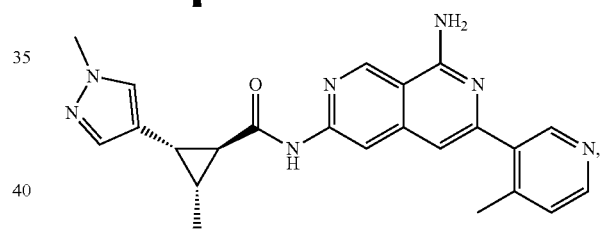
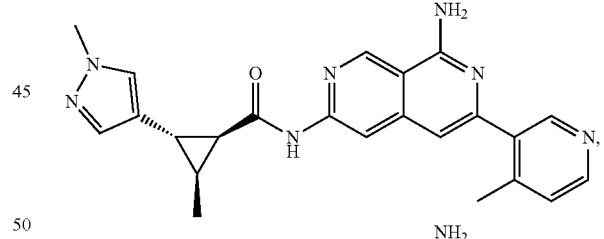
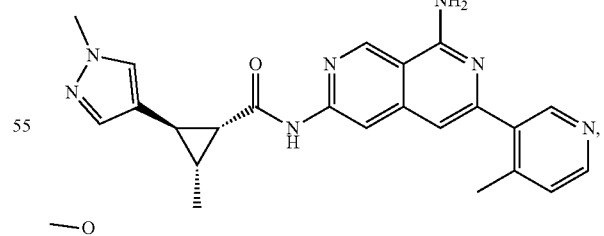
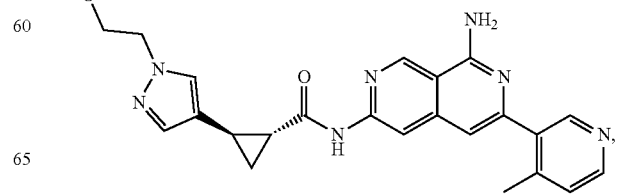

| 1507 | 1508 |
|---|---|
| -continued | -continued |
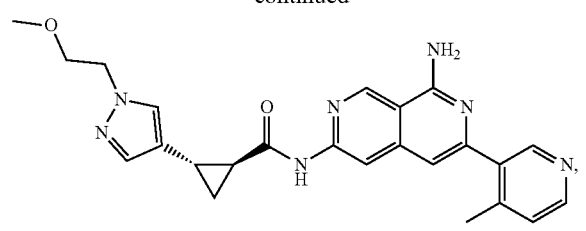
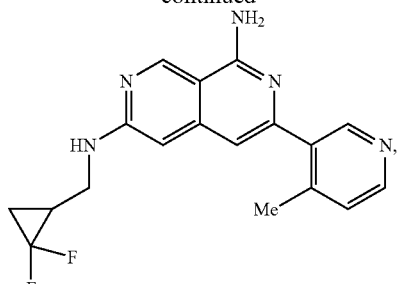
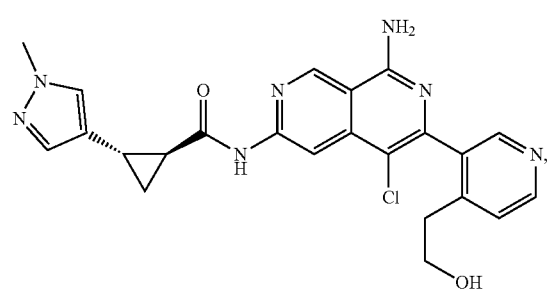
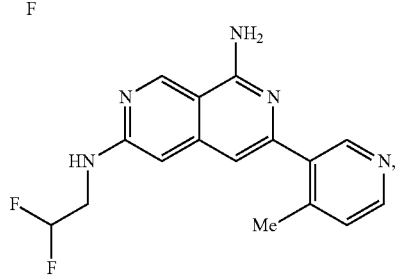
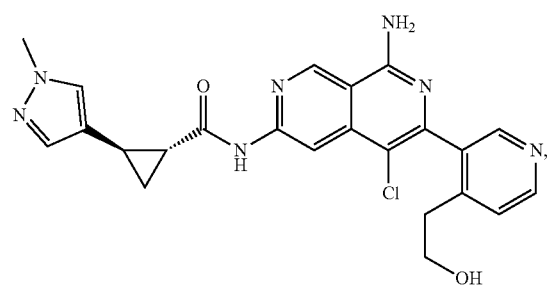
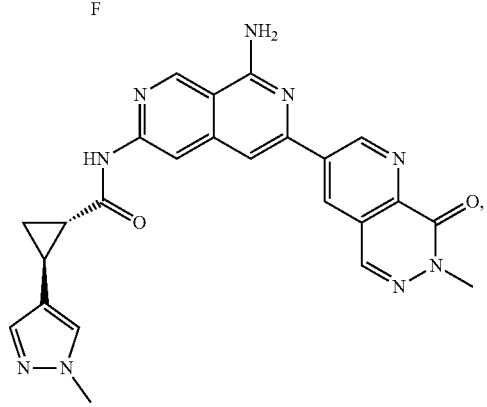
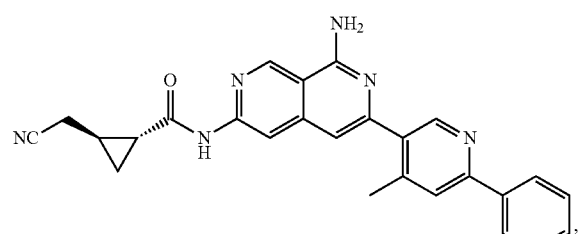
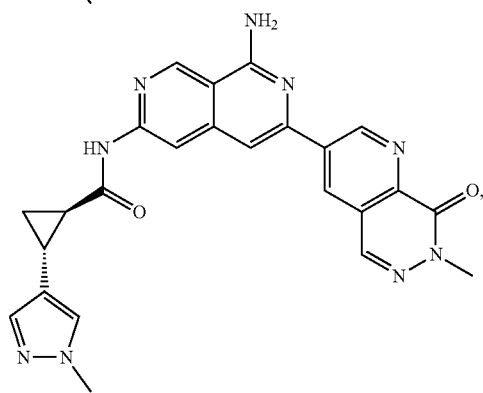
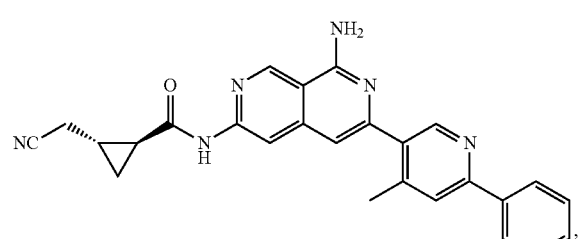
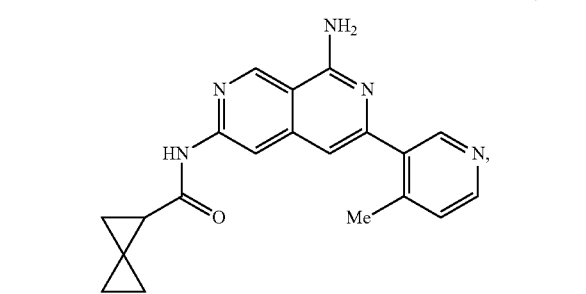
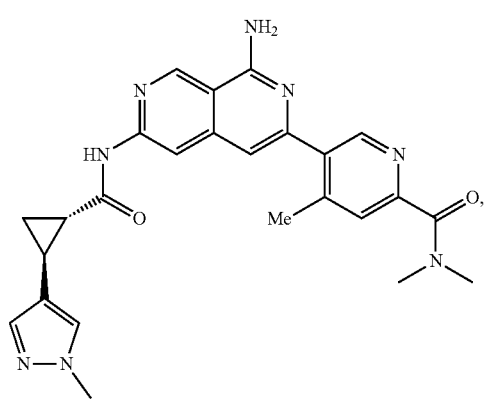

1509
-continued
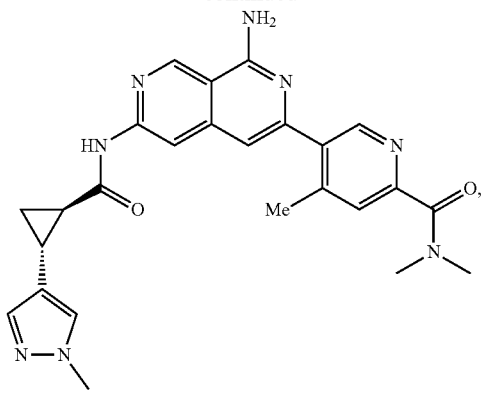
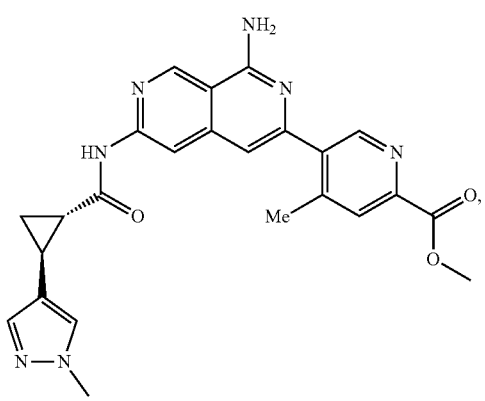
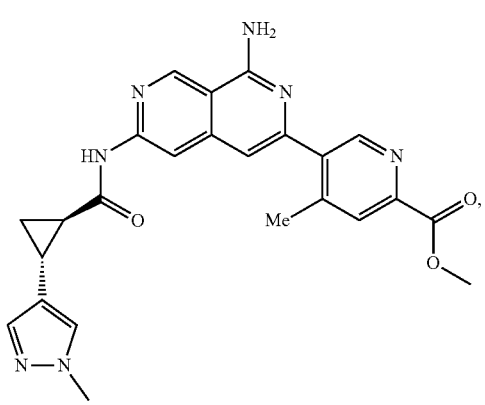
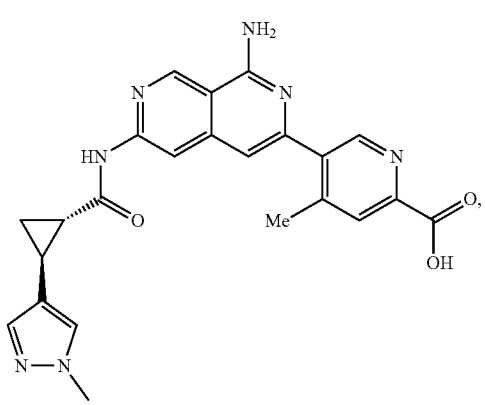
1510
-continued
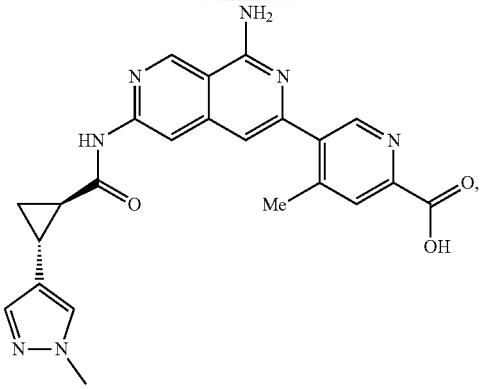
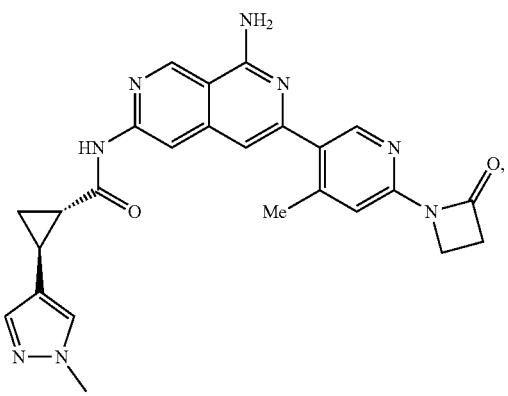
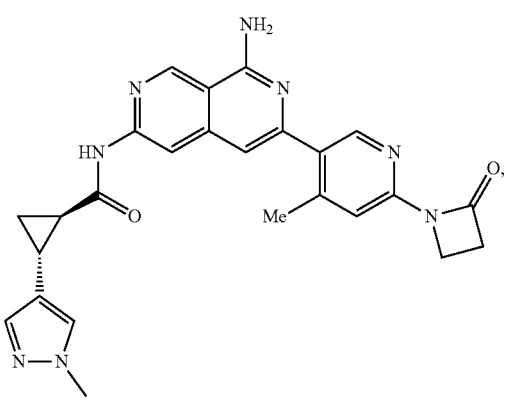
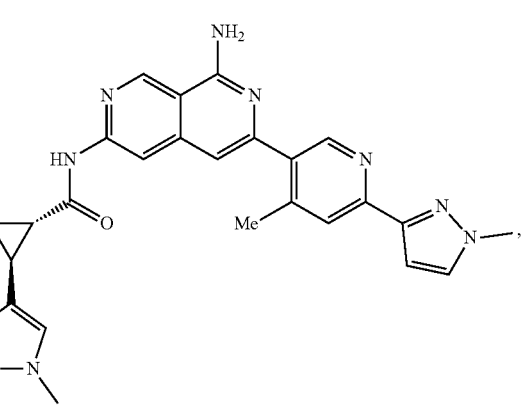

1511
-continued
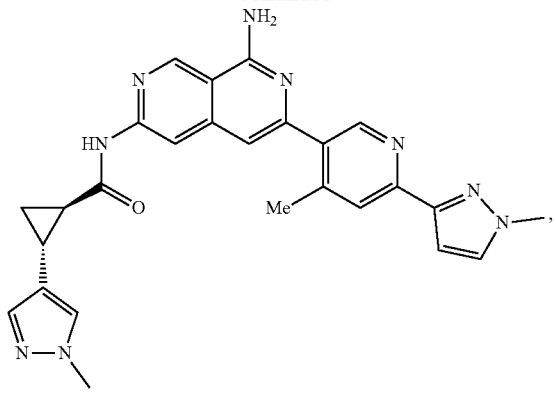
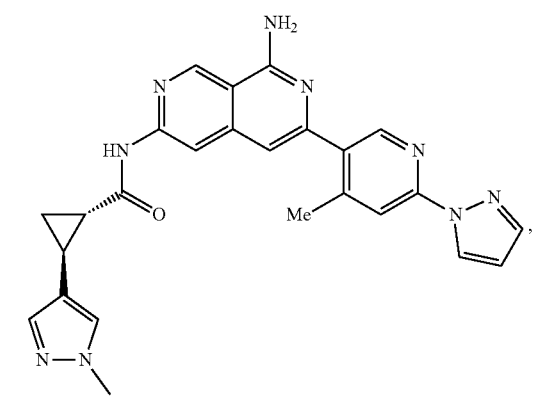
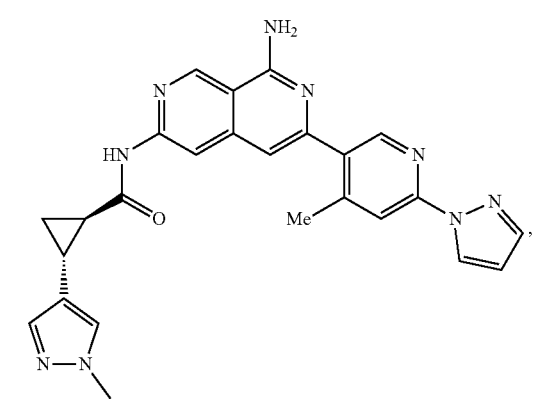
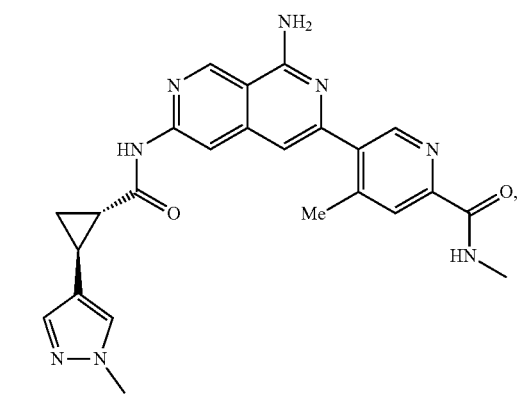
1512
-continued
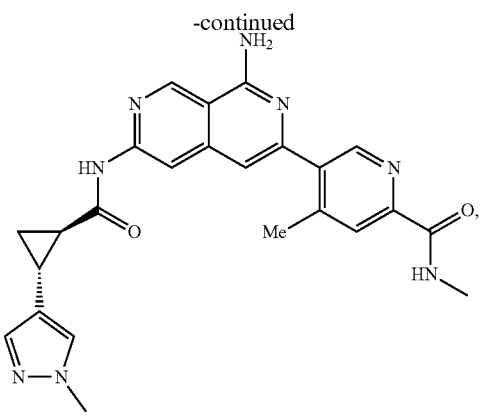
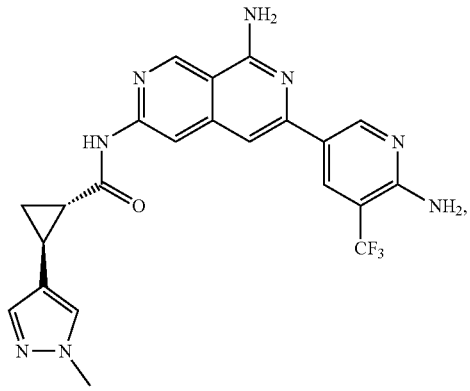
, and

1513
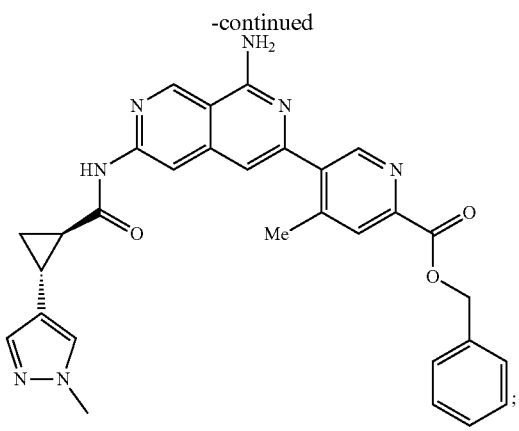
or a pharmaceutically acceptable salt thereof.
19. The method of claim 1, wherein the compound is selected from the group consisting of Compound Nos. 349-429 in Table 2, having the structures:
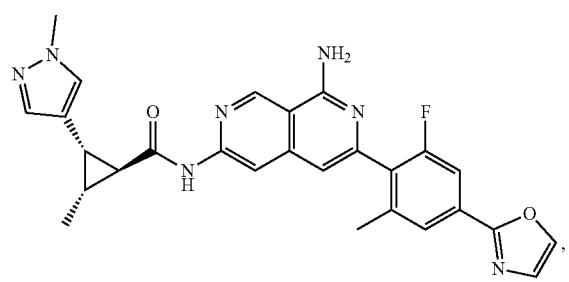
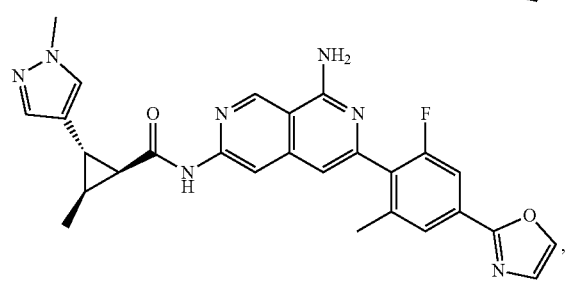
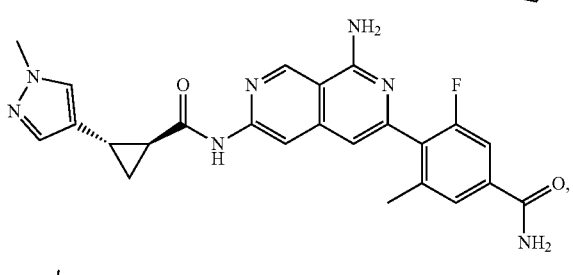
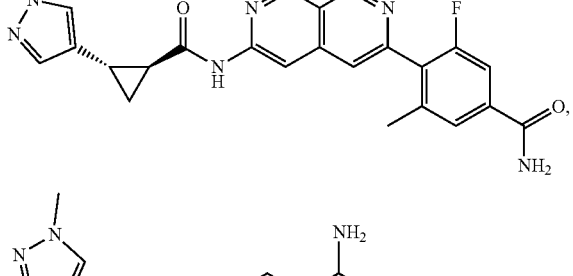
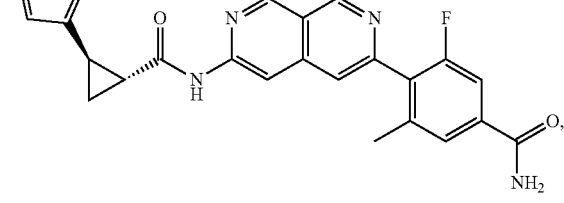
1514
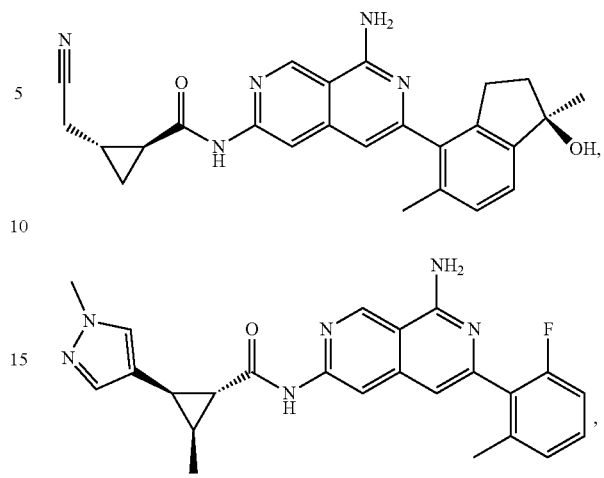
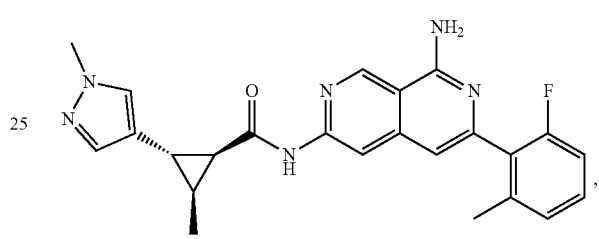
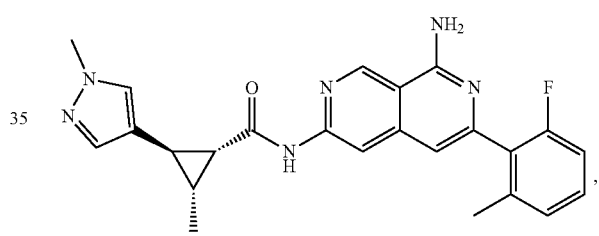
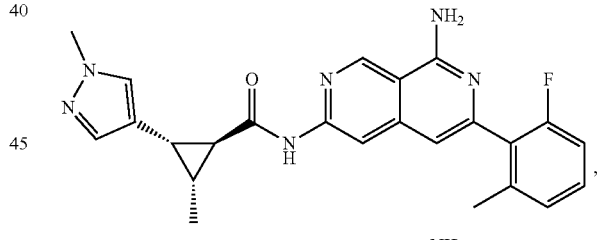
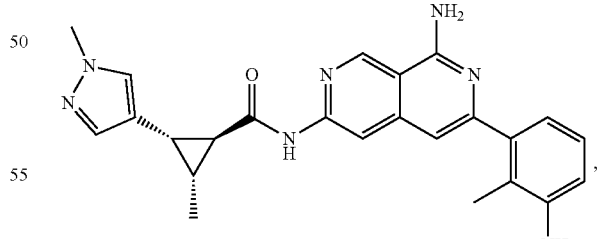
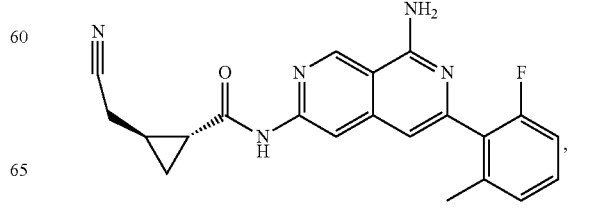

1515
-continued
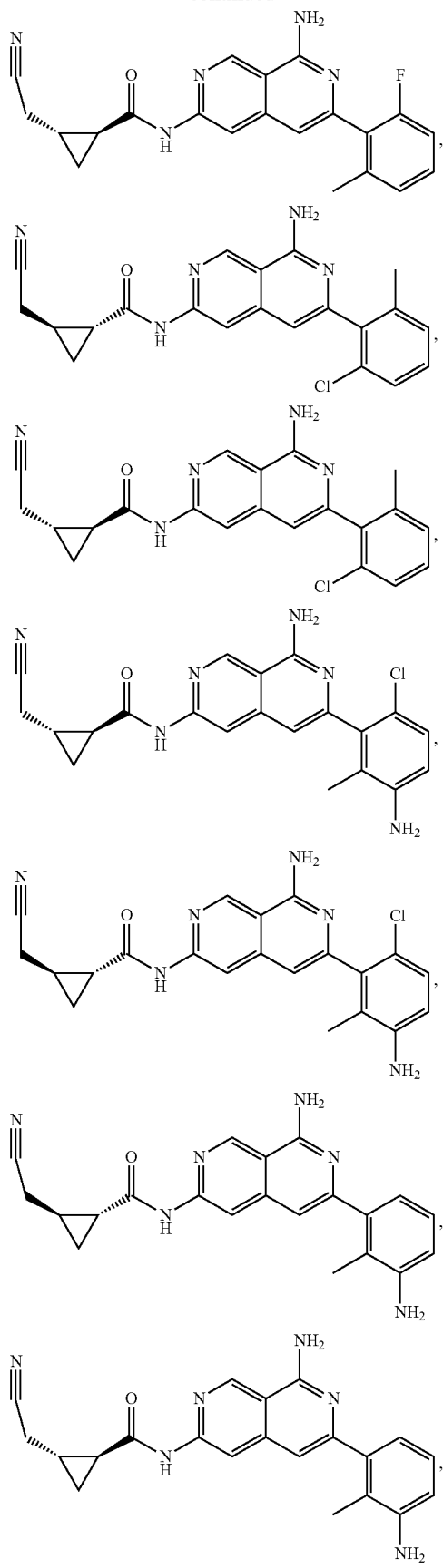
1516
-continued
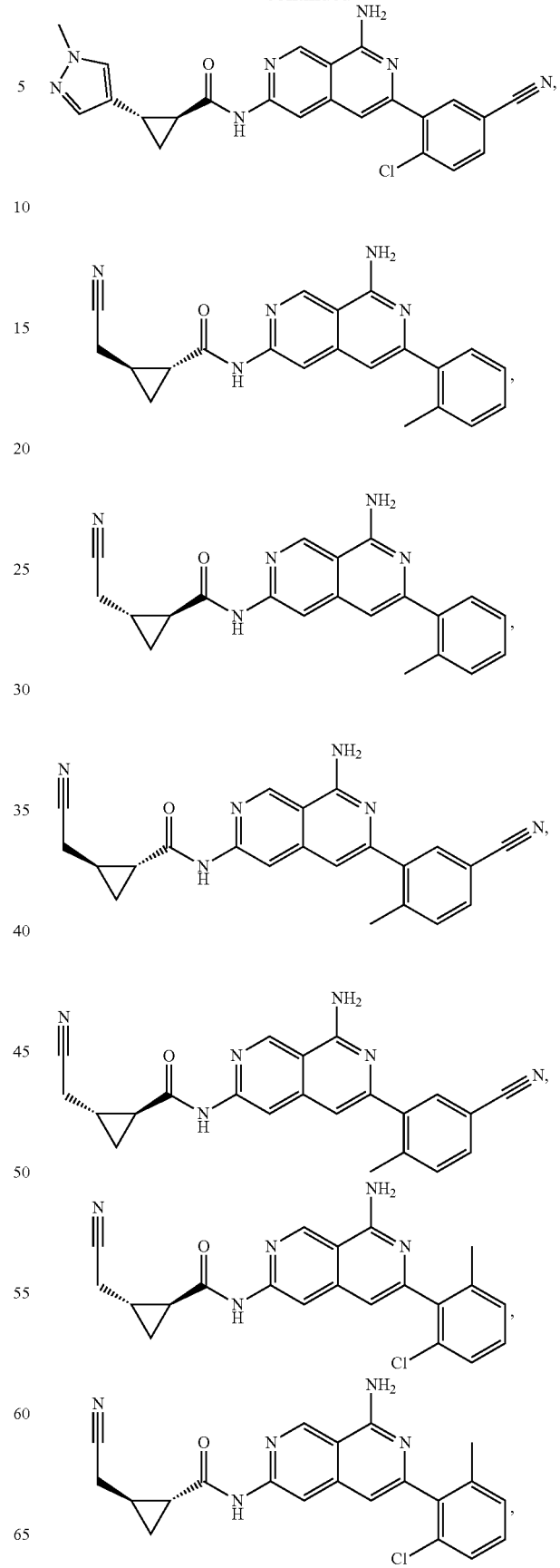

1517
-continued
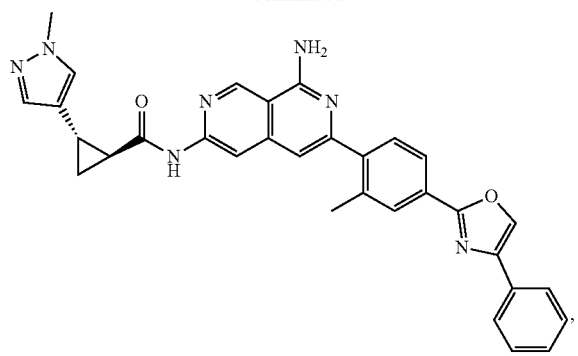
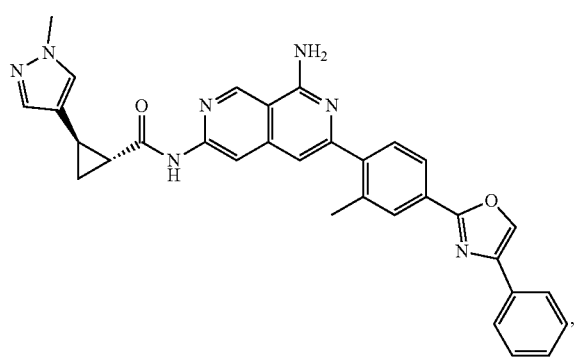
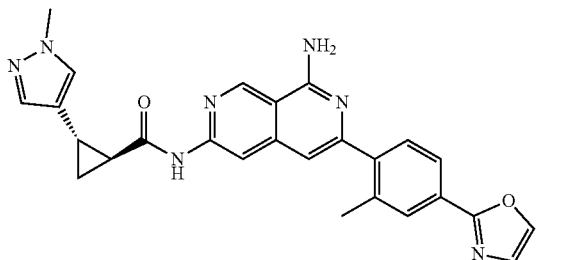
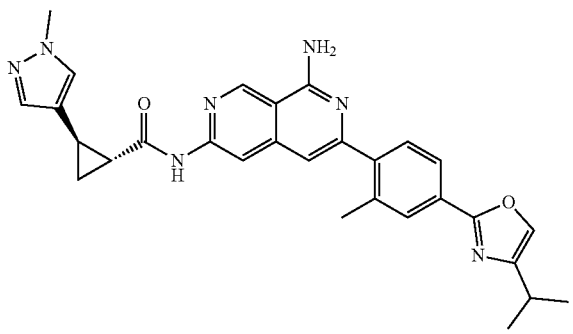
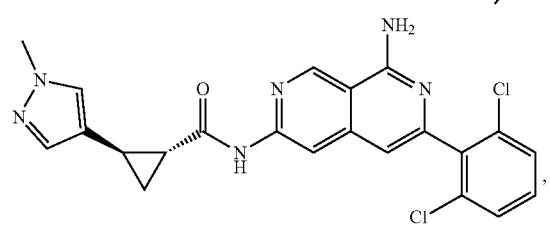
1518
-continued
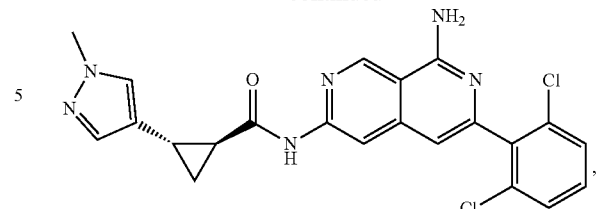
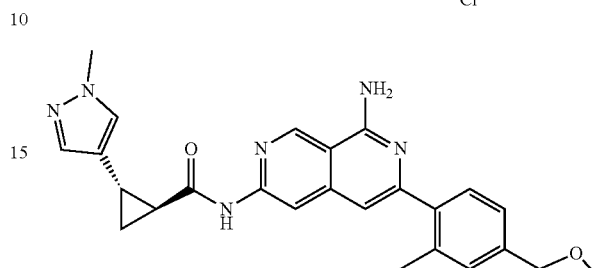
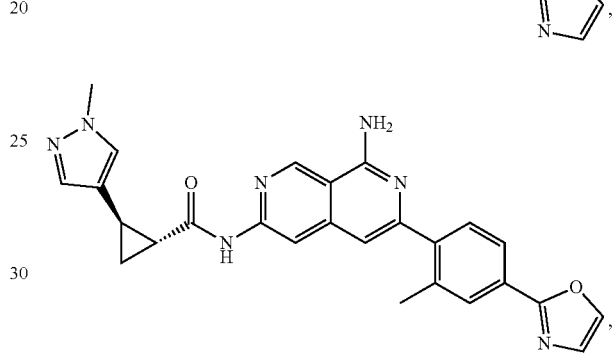
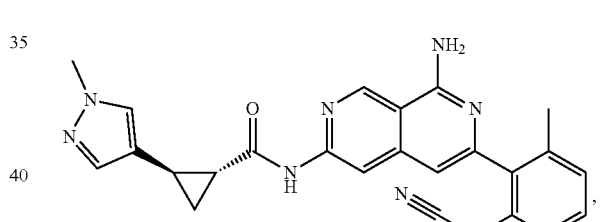
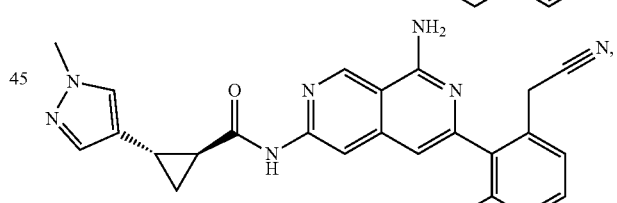
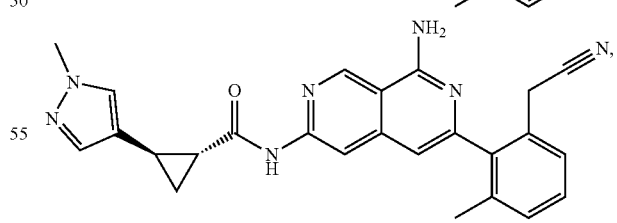
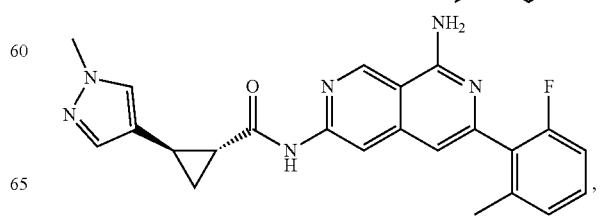

1519
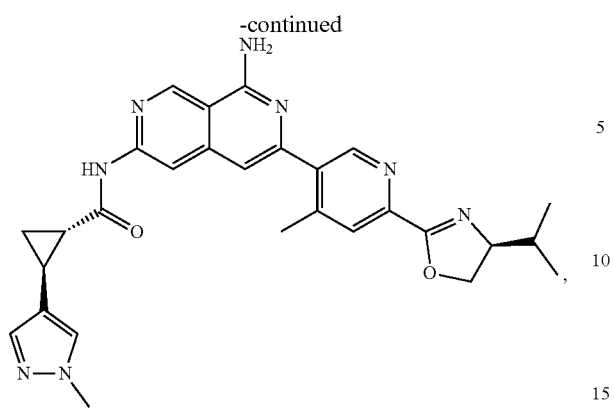
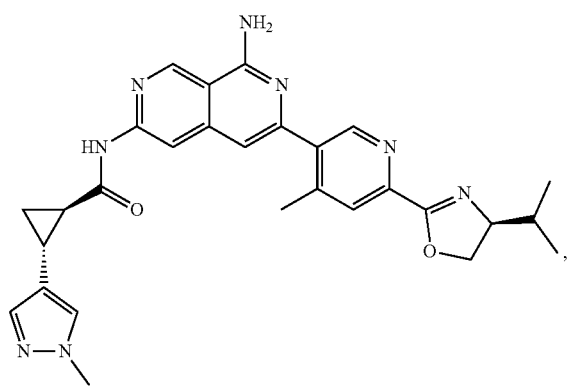
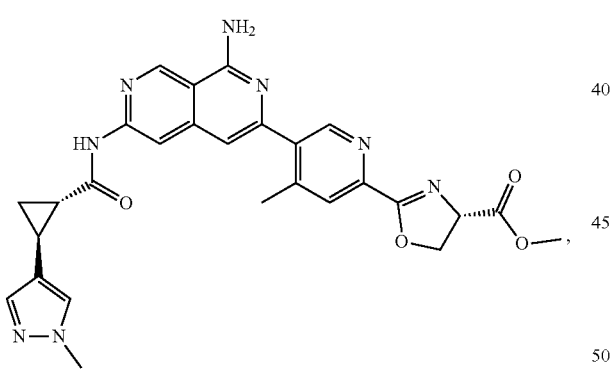
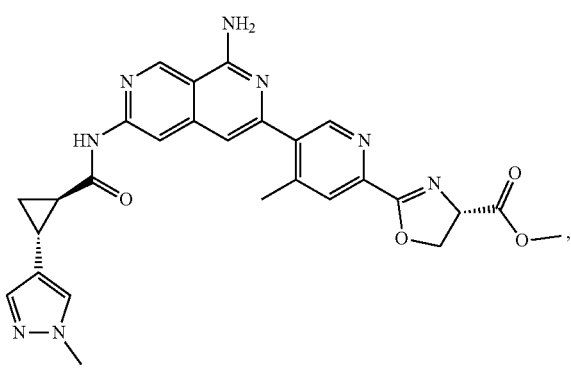
1520
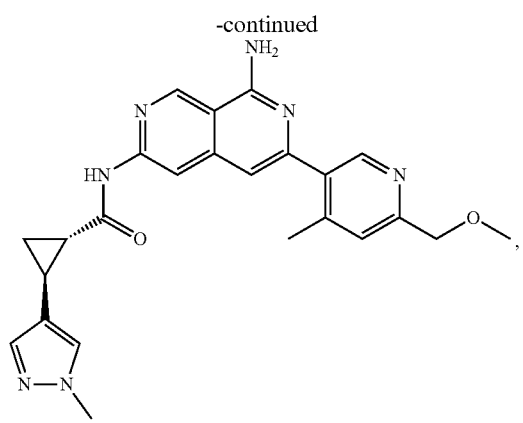
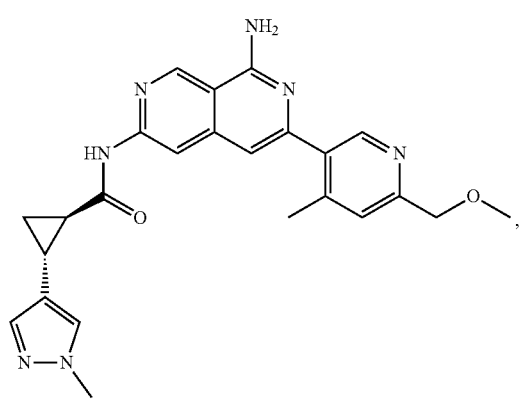
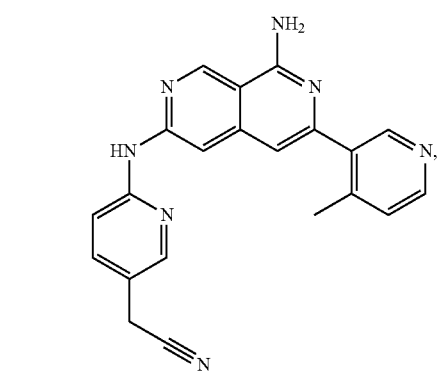
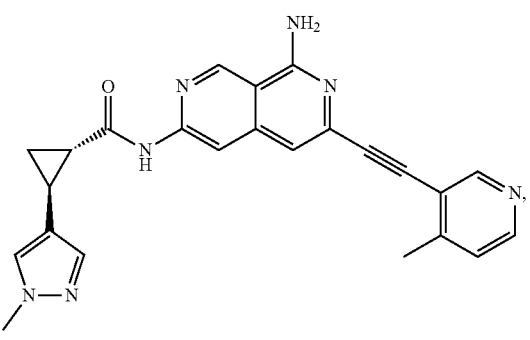

1521
-continued
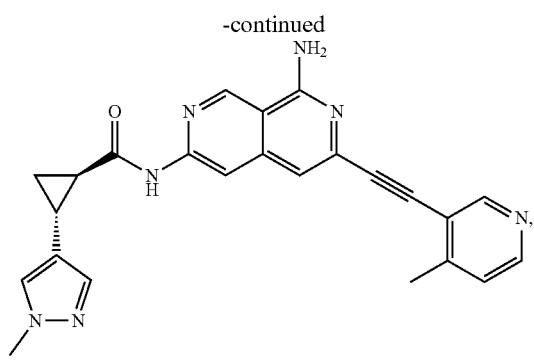
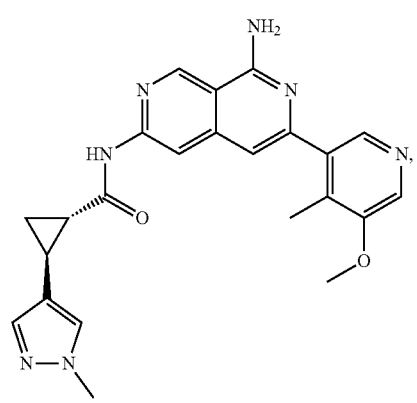
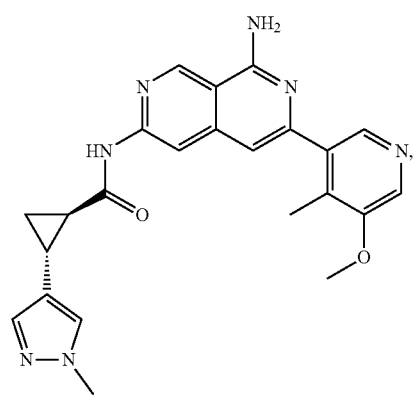
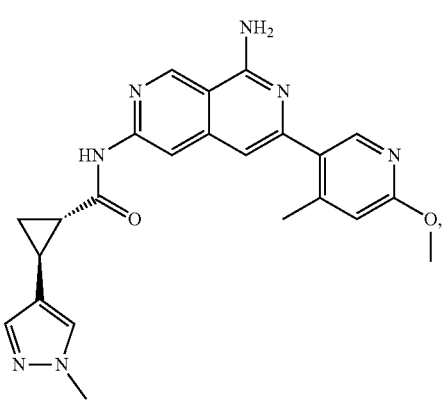
1522
-continued
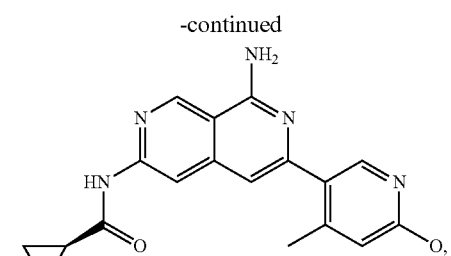
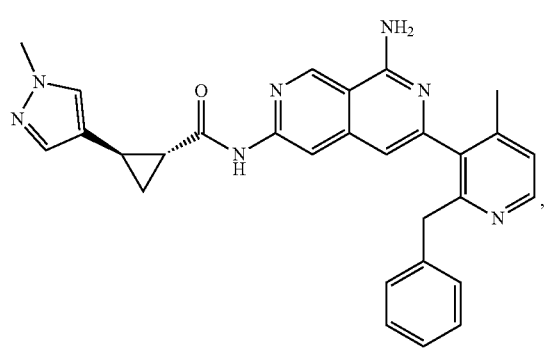
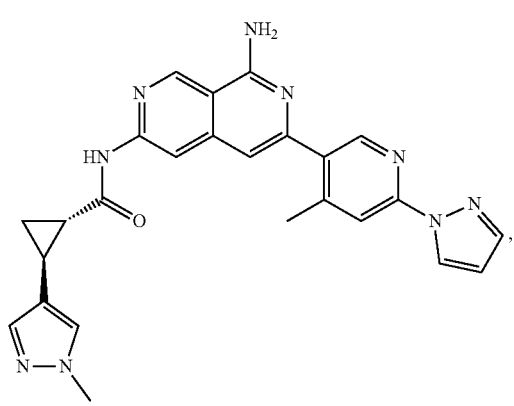
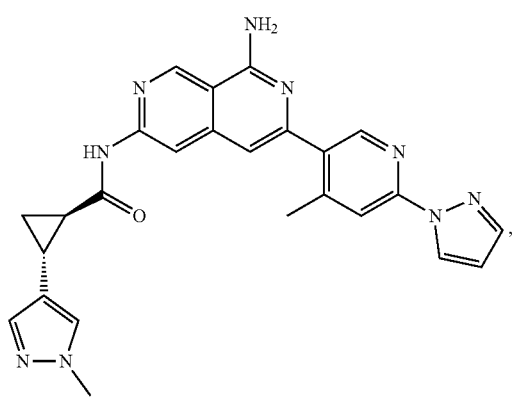

1523
-continued
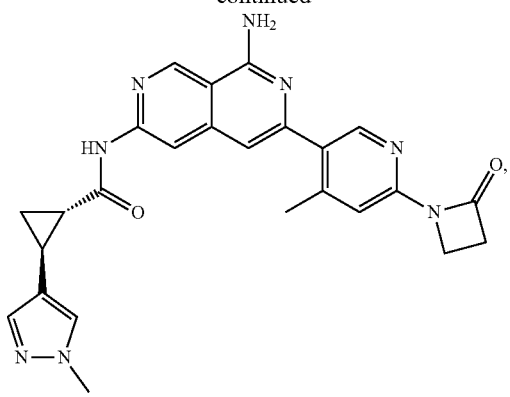
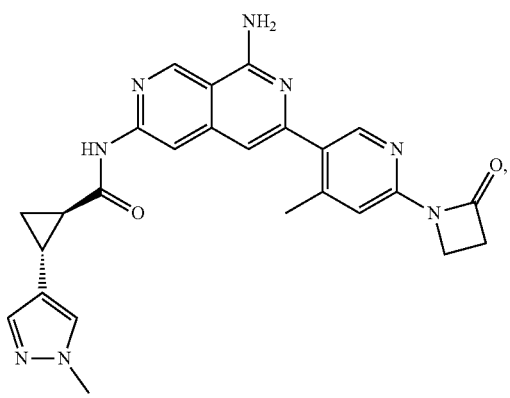
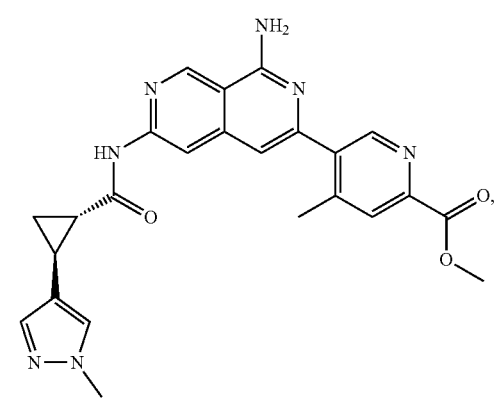
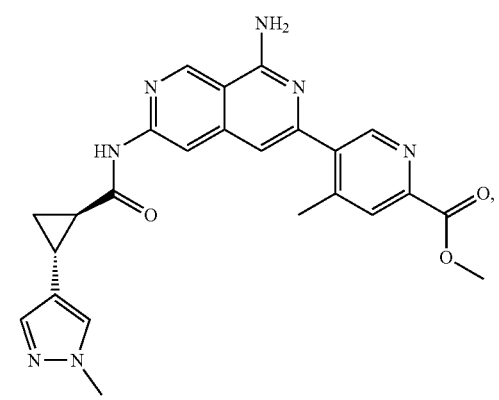
1524
-continued
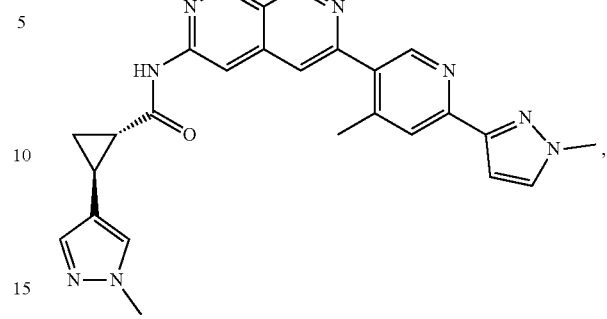
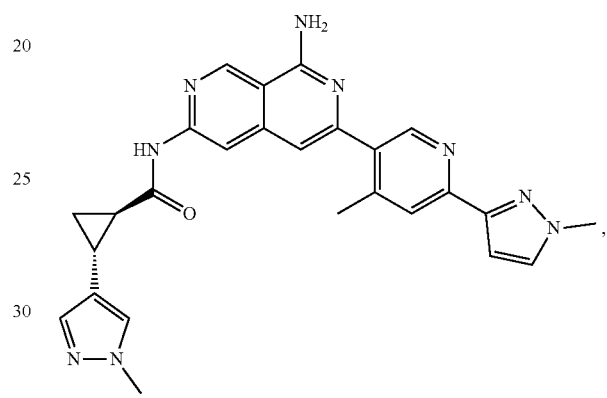
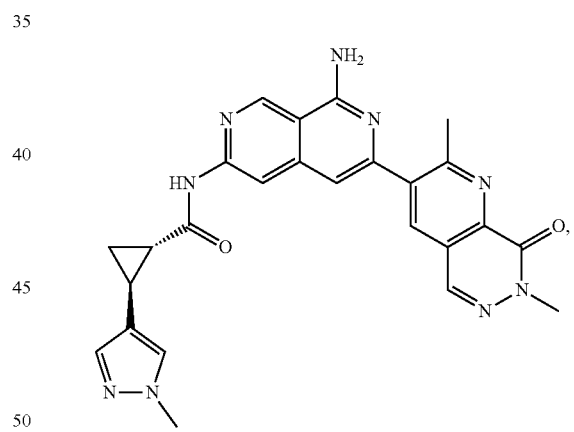
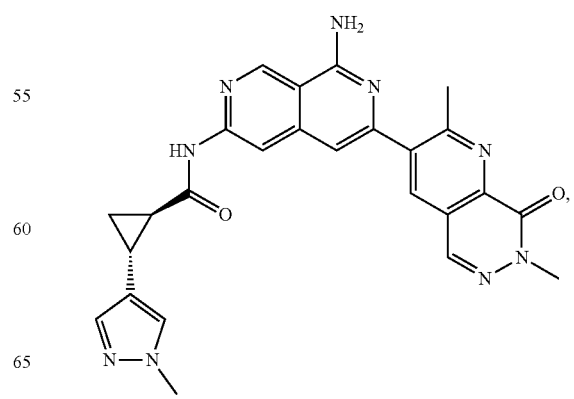

1525
-continued
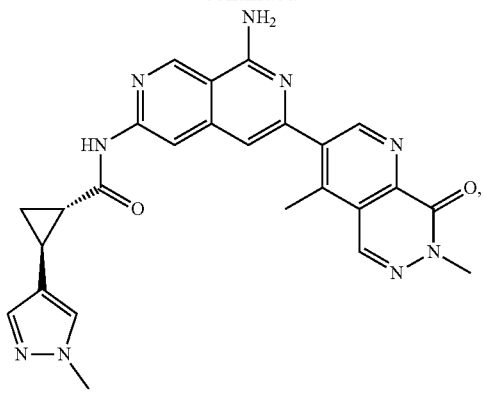
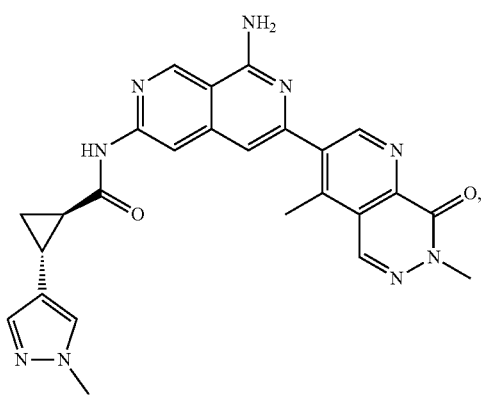
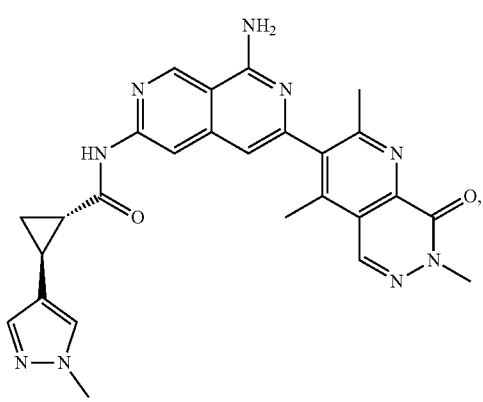
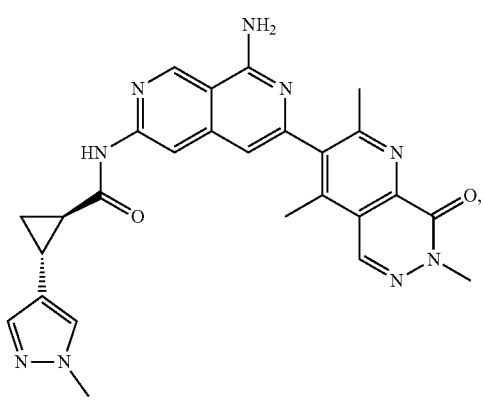
1526
-continued
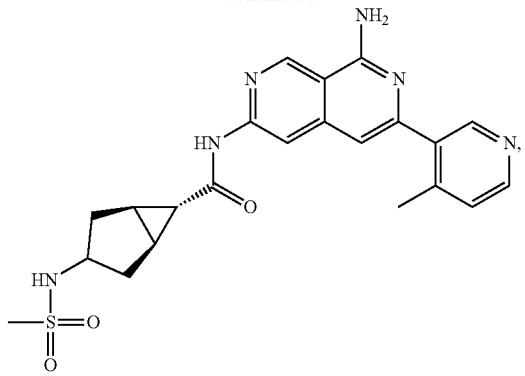
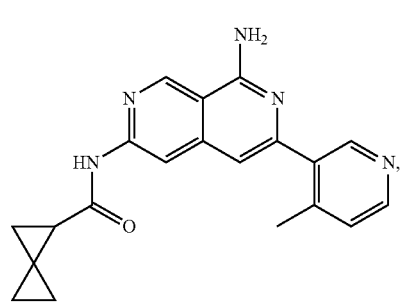
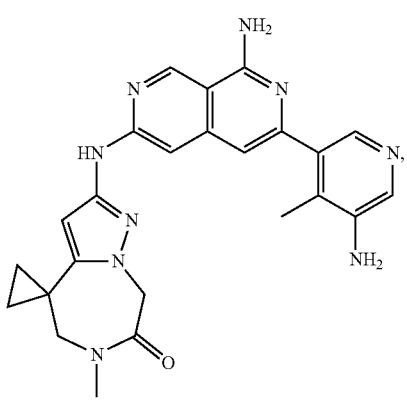
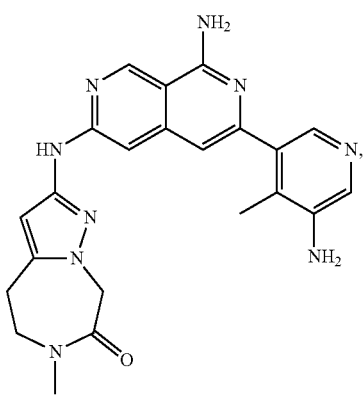

1527
-continued
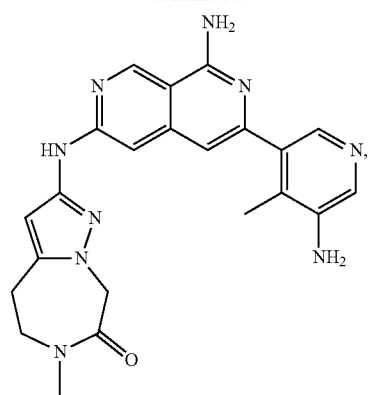
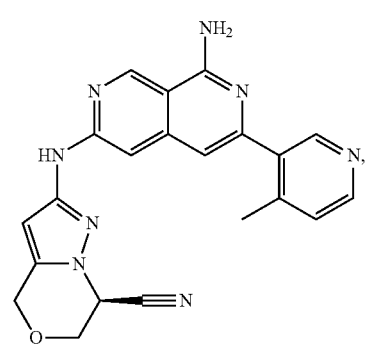
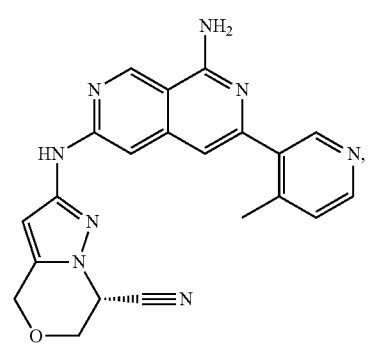
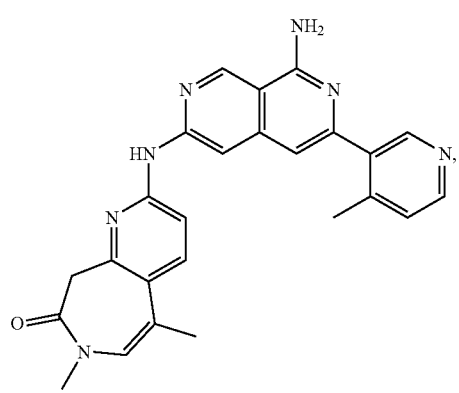
1528
-continued
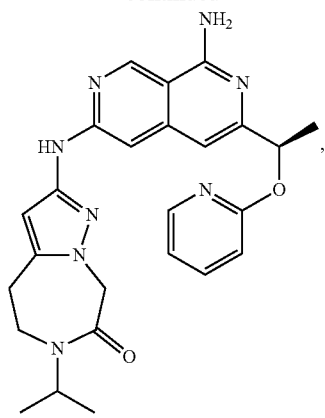
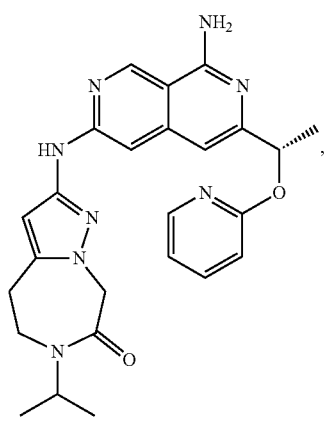
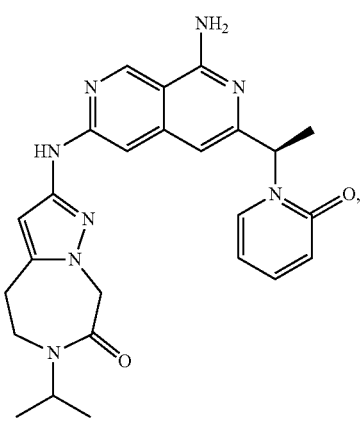
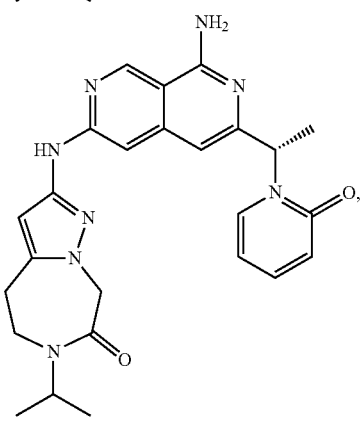

1529
-continued
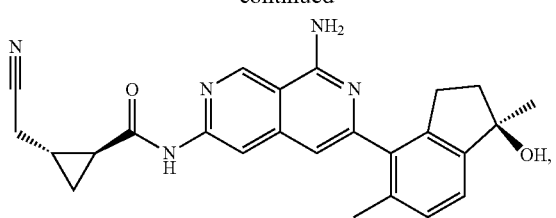
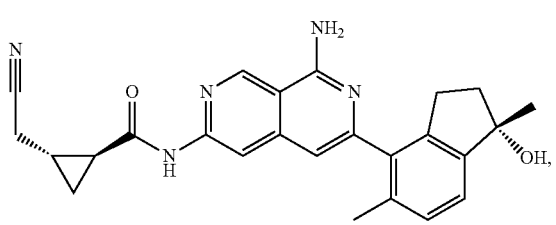
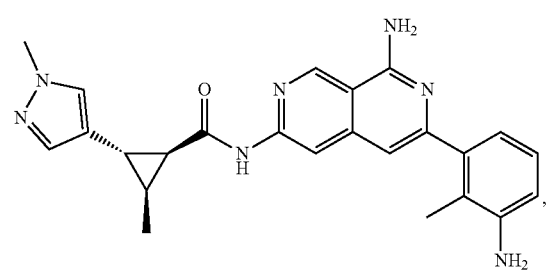
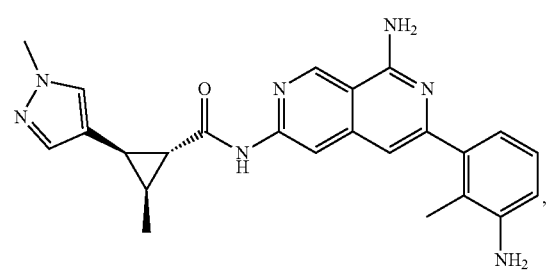
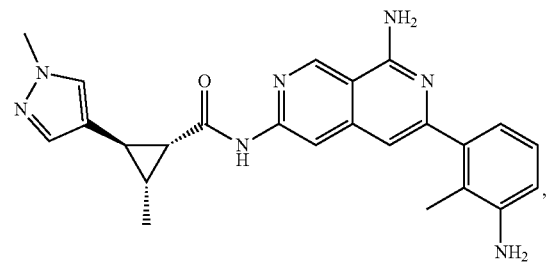
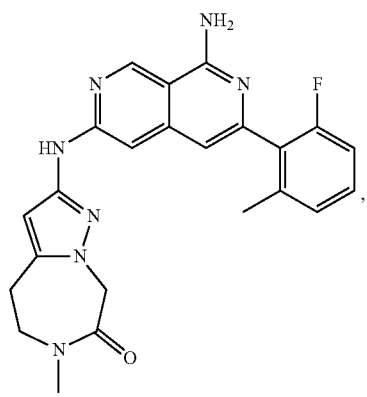
1530
-continued
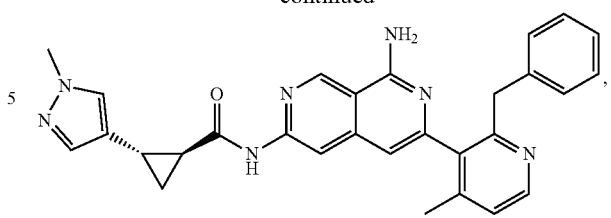
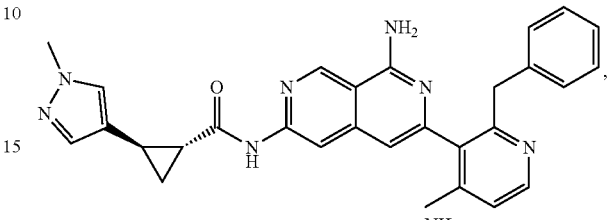
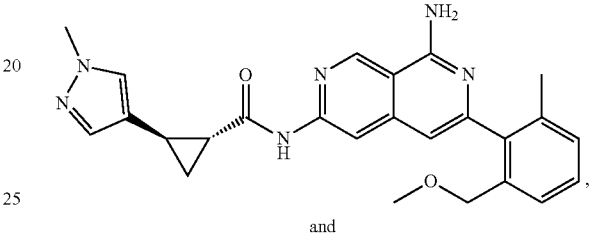
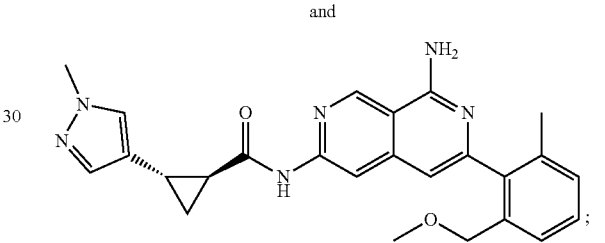
and
or a pharmaceutically acceptable salt thereof.
20. The method of claim 1, wherein the compound is selected from the group consisting of Compound Nos. 430-572 in Table 3, having the structures:
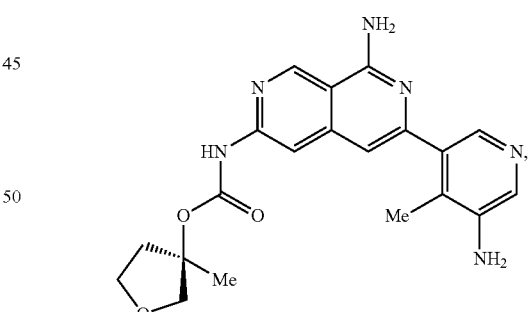
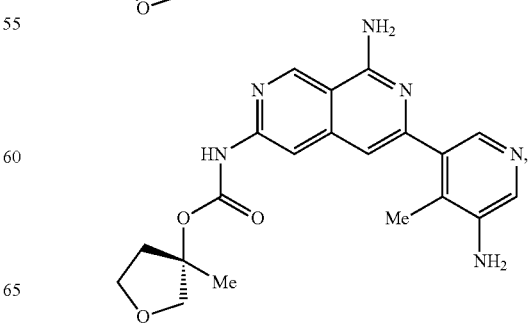

1531
-continued
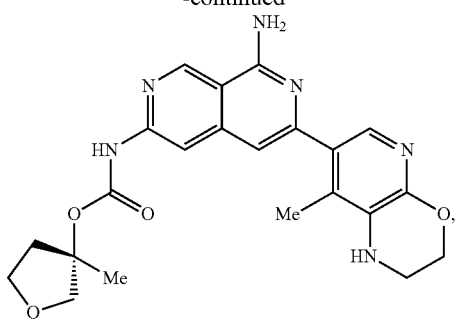
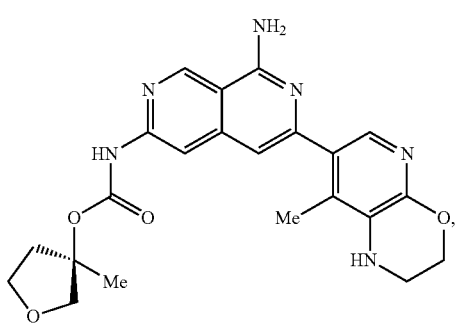
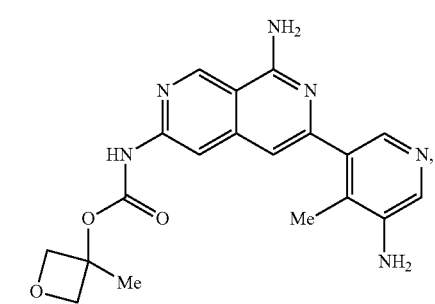
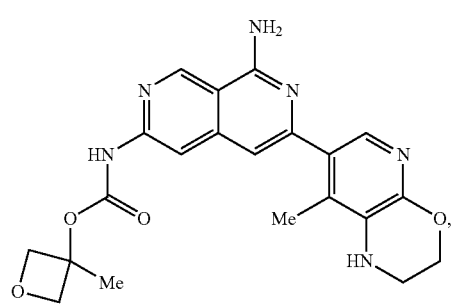
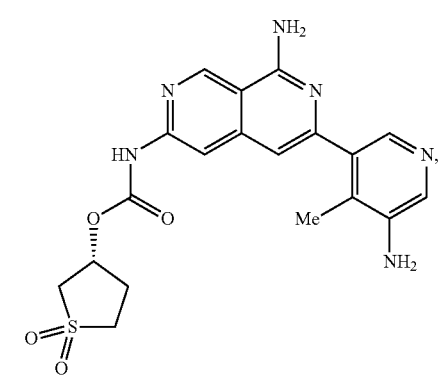
1532
-continued
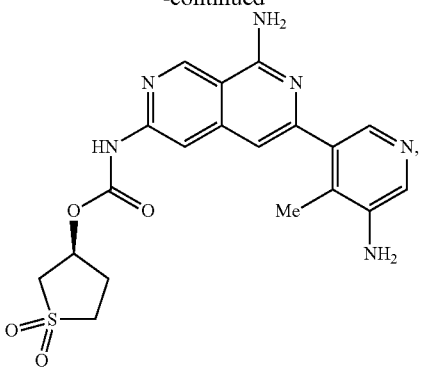
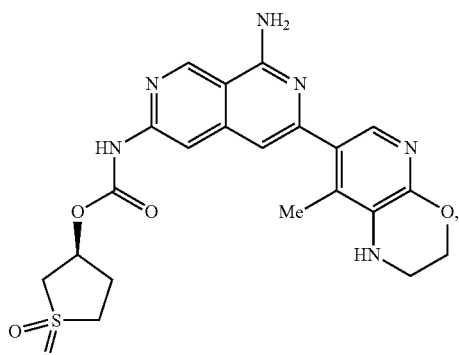
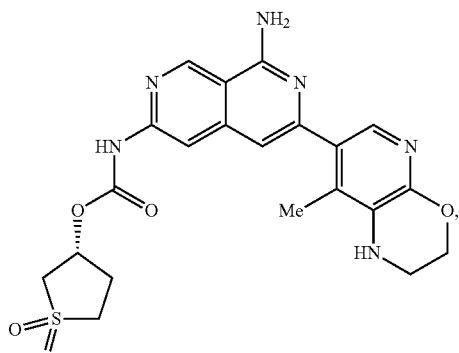
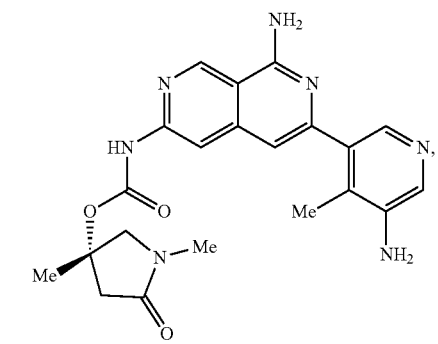

1533
-continued
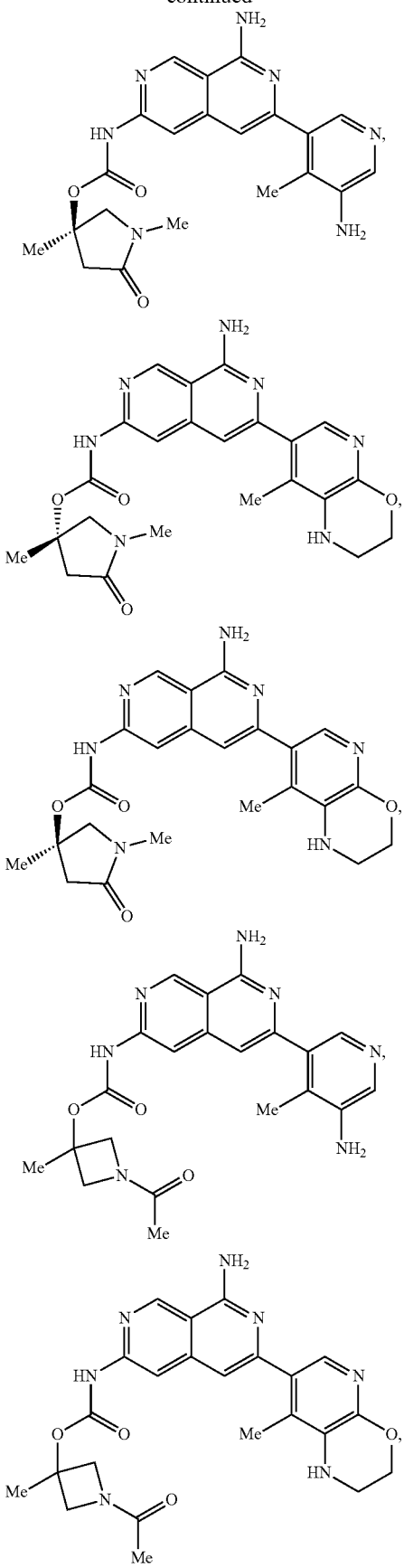
1534
-continued
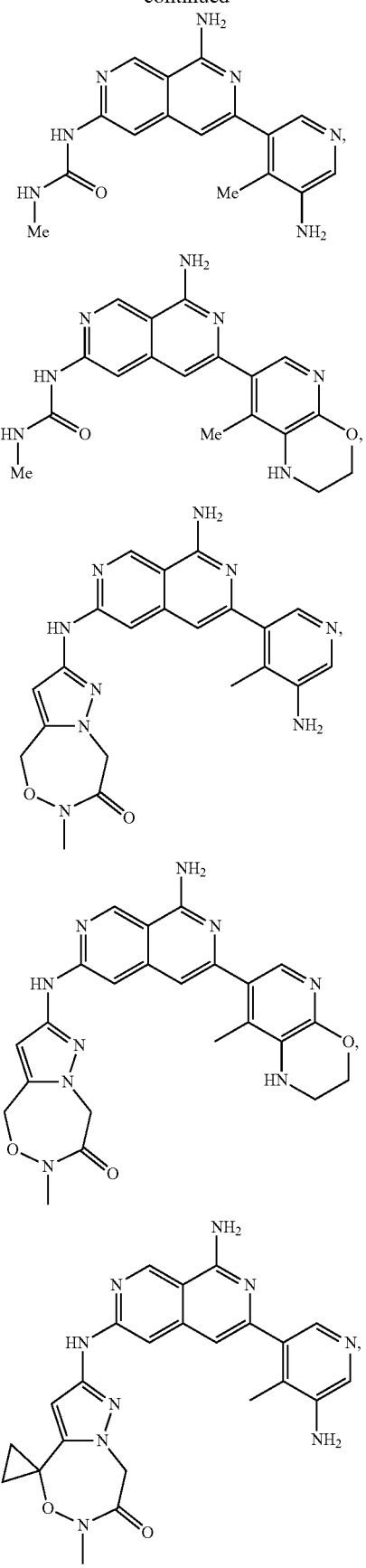

1535
-continued
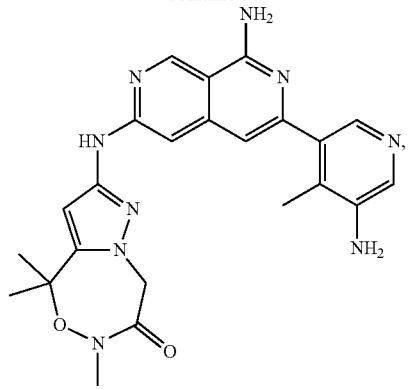
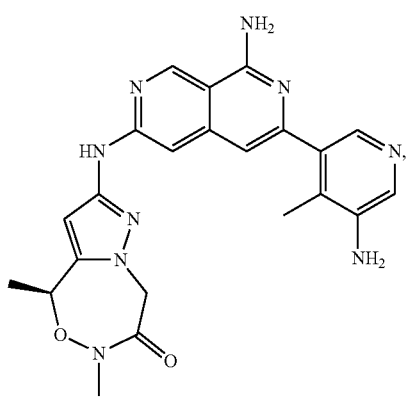
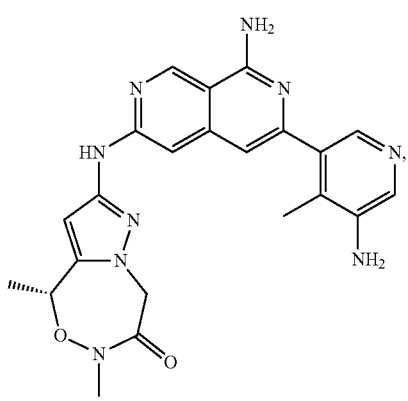
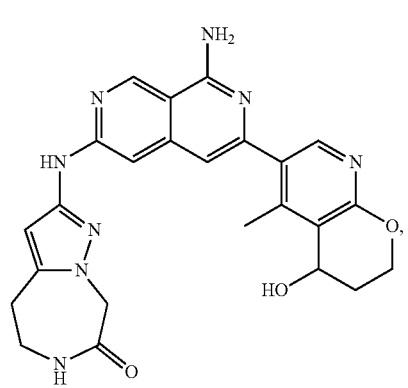
1536
-continued
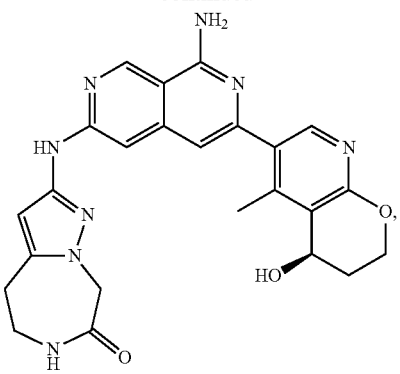
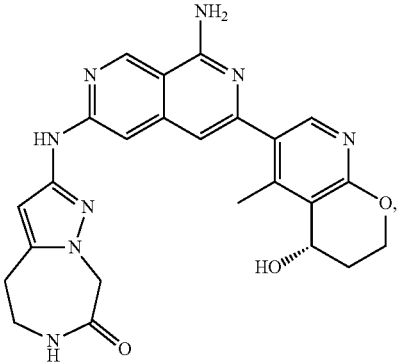
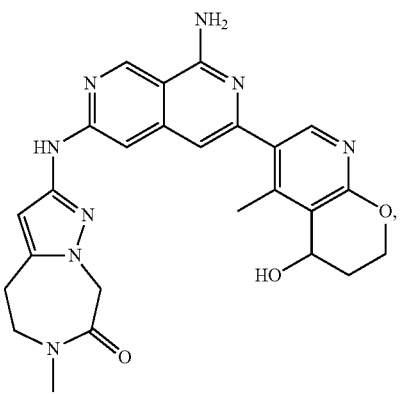
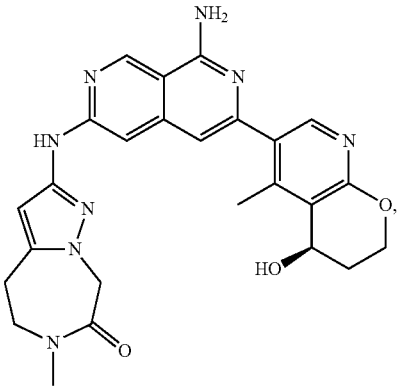

1537
-continued
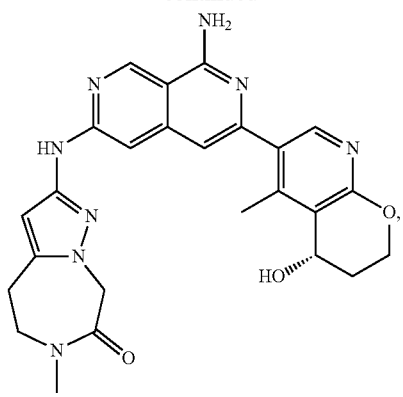
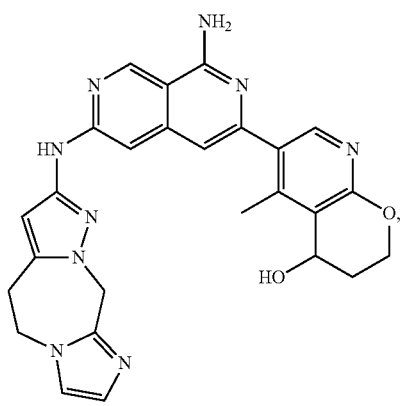
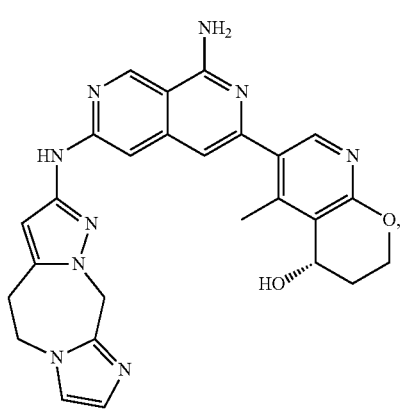
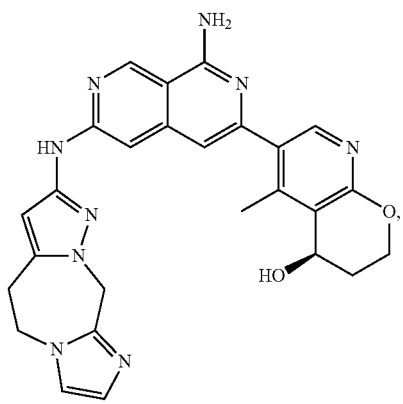
1538
-continued
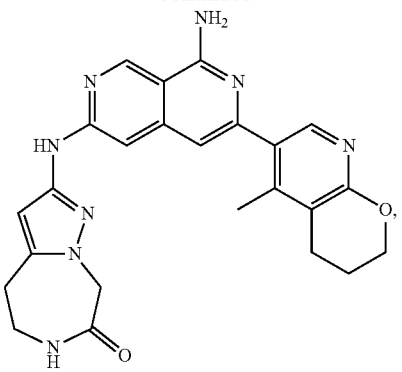
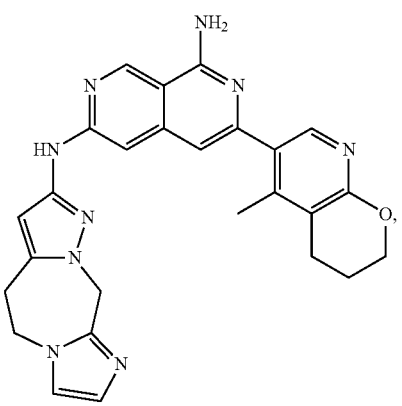
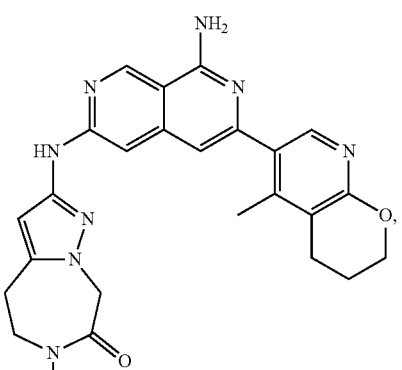
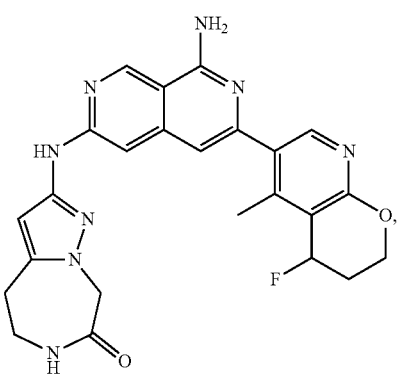

1539
-continued
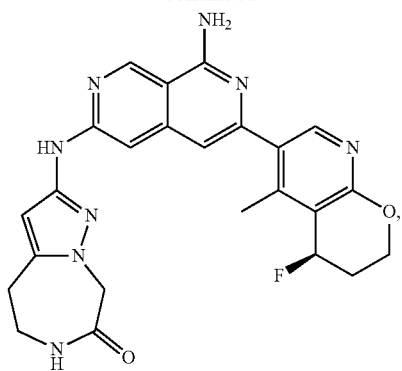
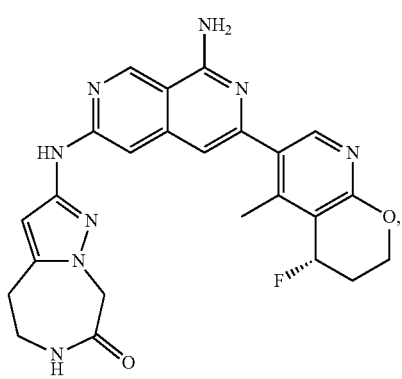
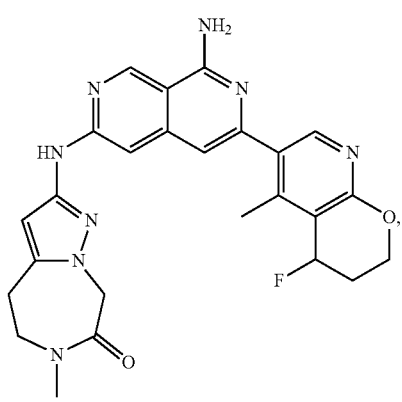
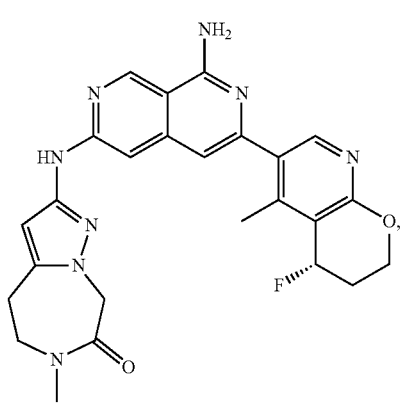
1540
-continued
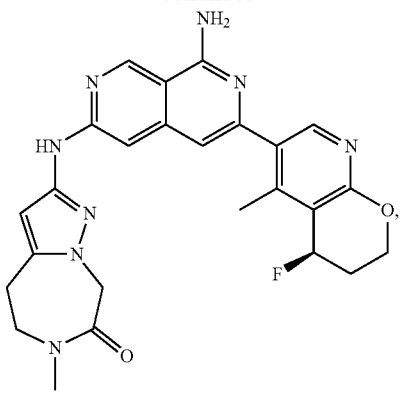
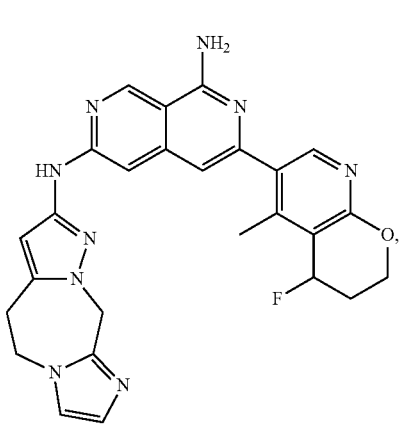
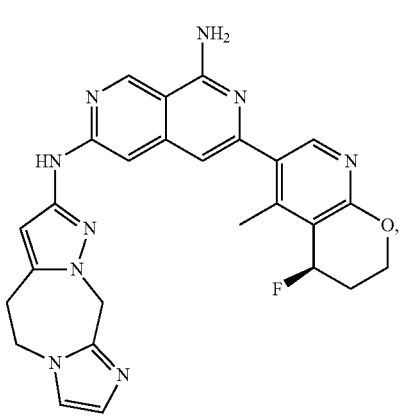
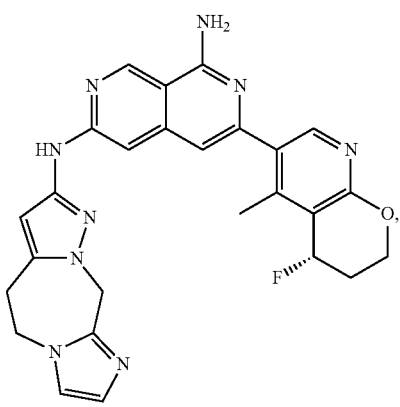

1541
-continued
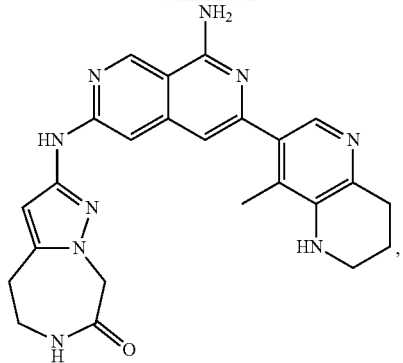
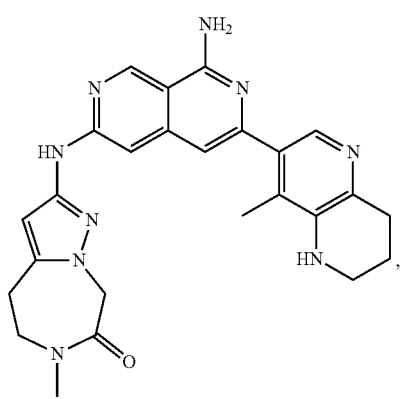
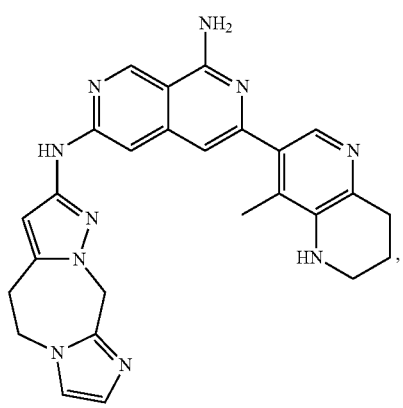
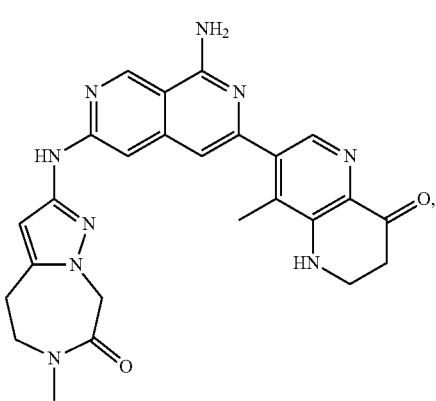
1542
-continued
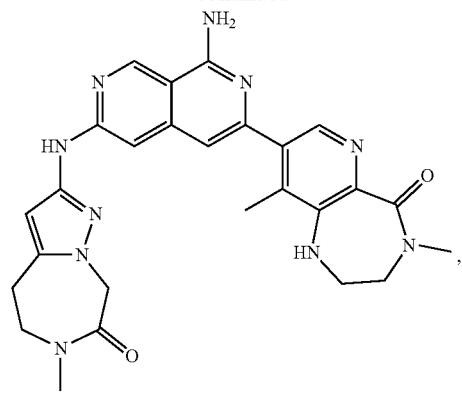
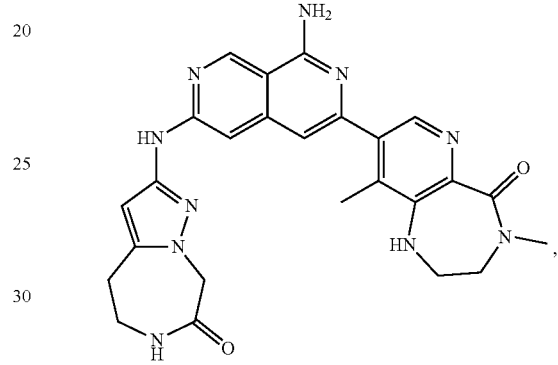
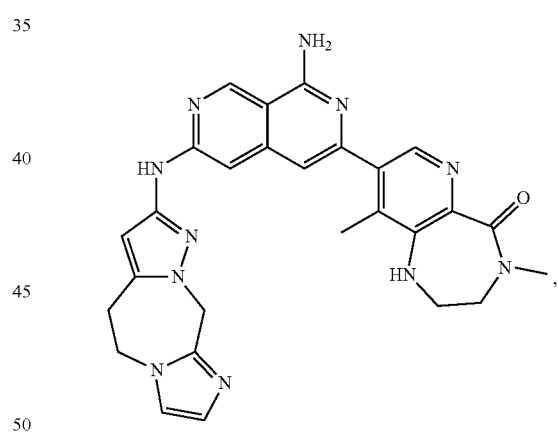
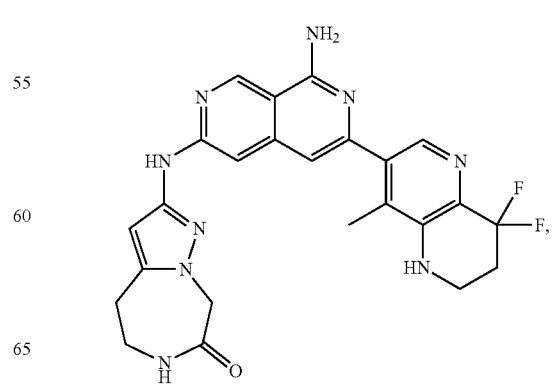

1543
-continued
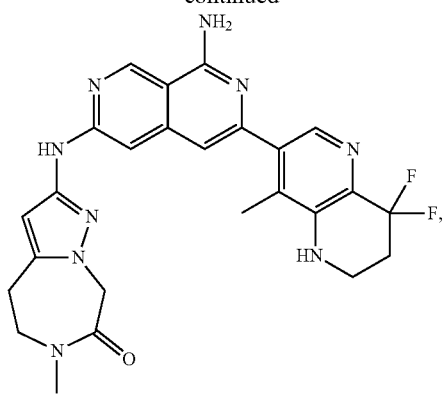
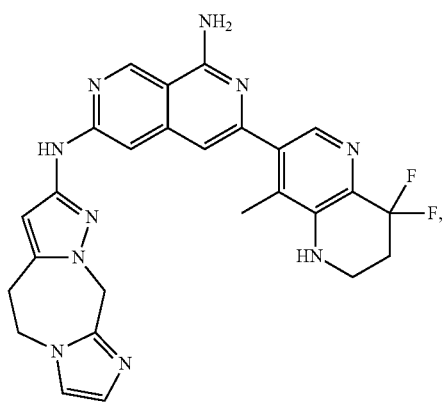
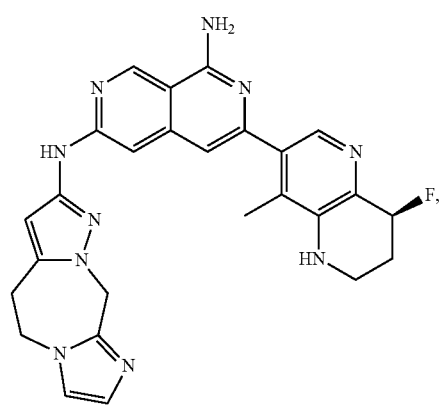
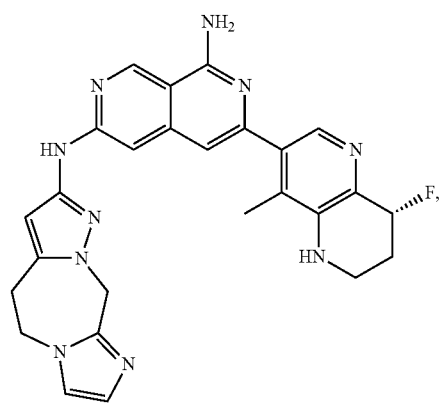
1544
-continued
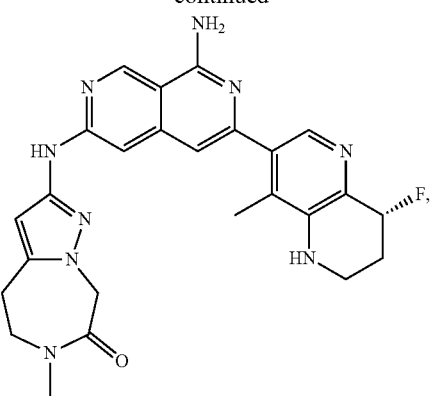
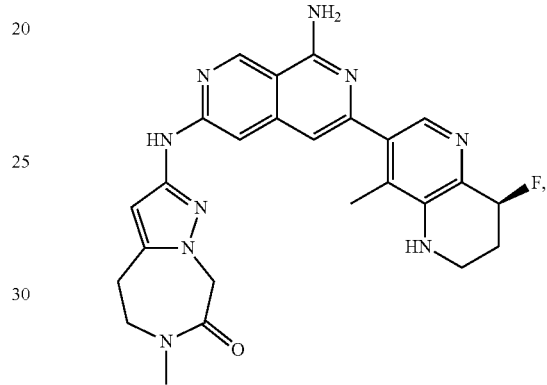
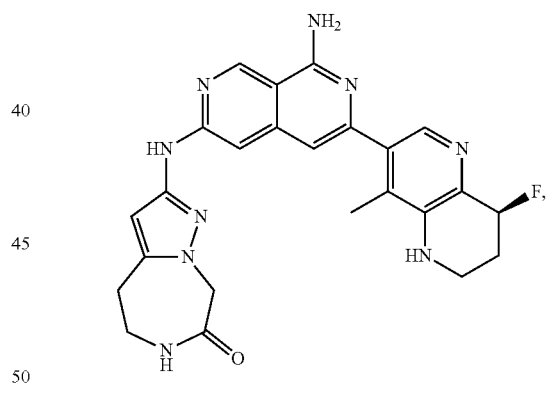
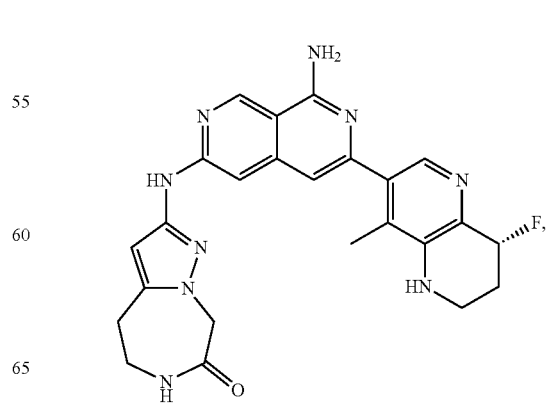

1545
-continued
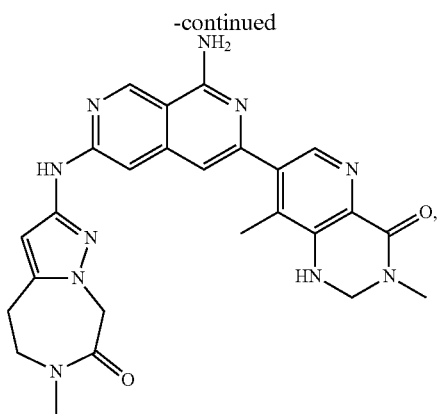
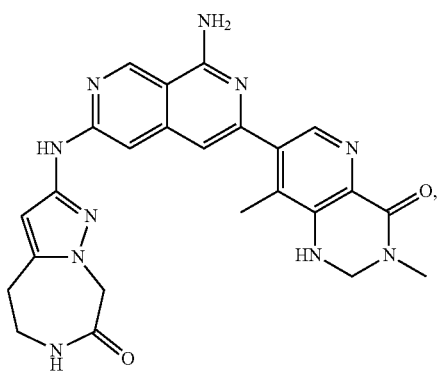
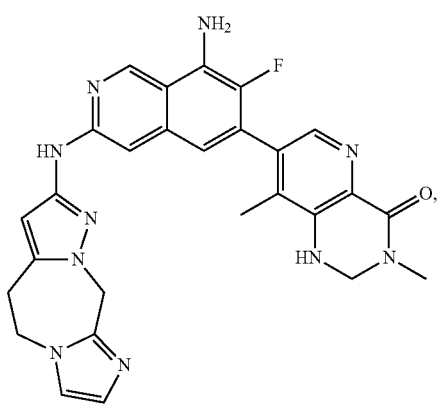
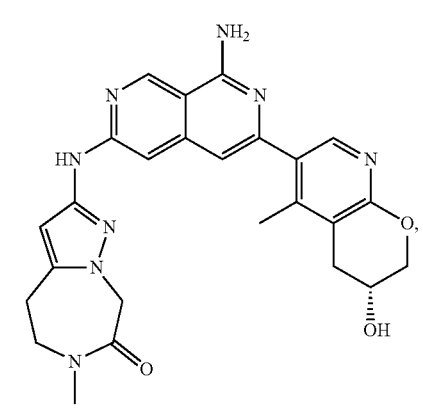
1546
-continued
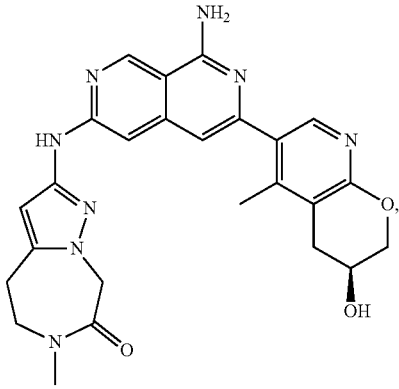
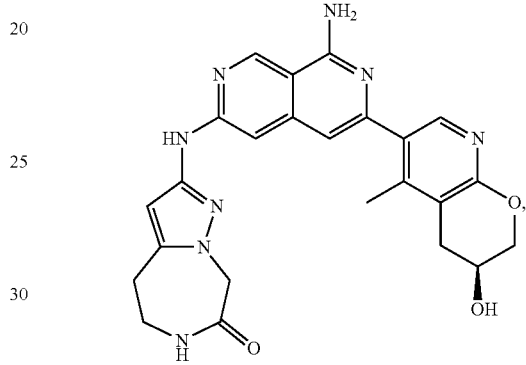
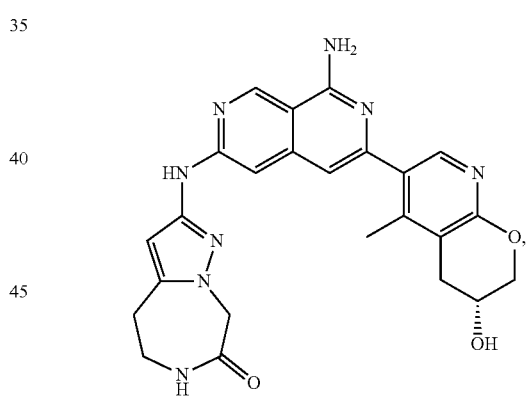
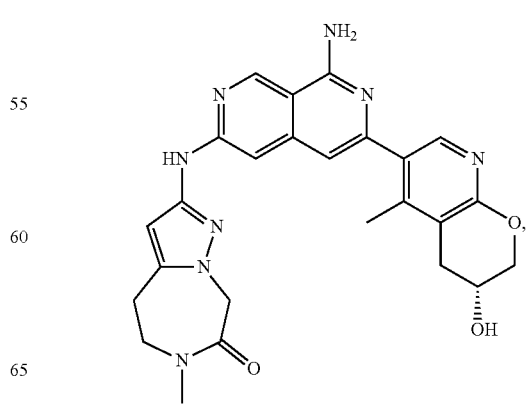

1547
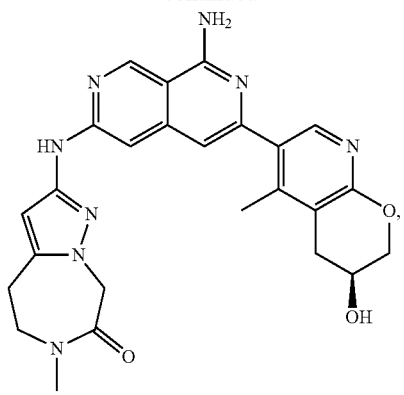
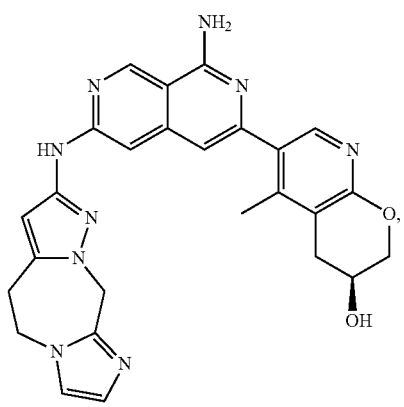
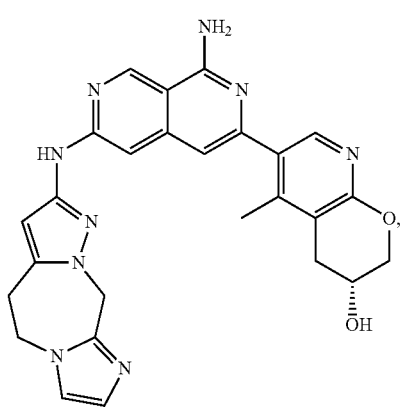
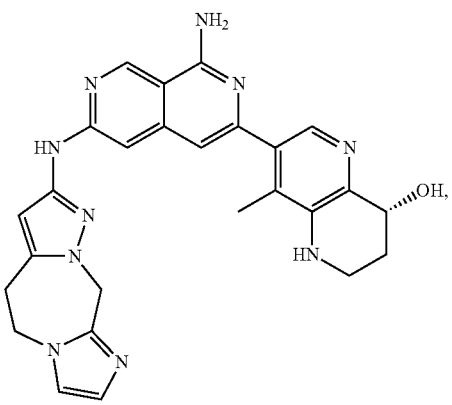
1548
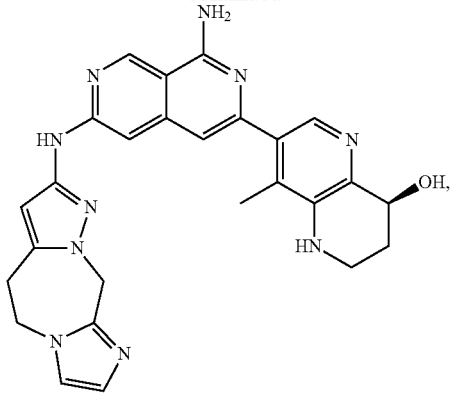
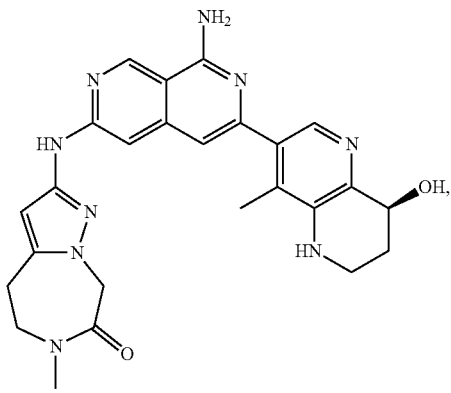
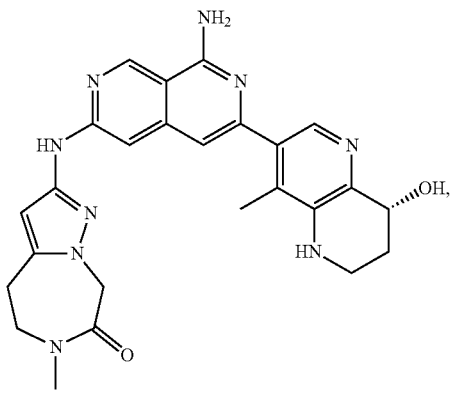
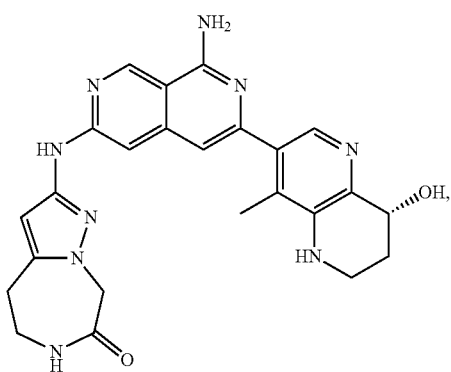

1549
-continued
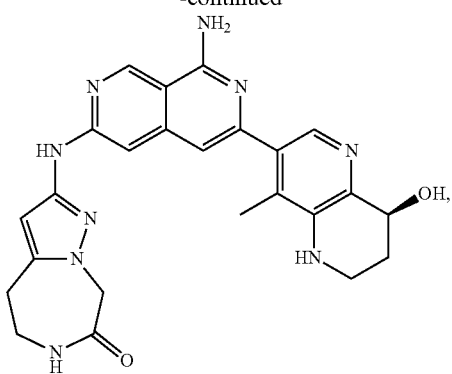
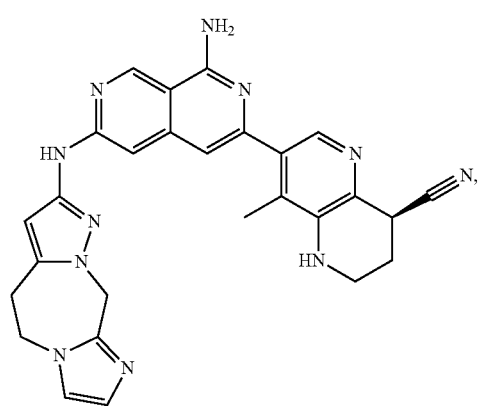
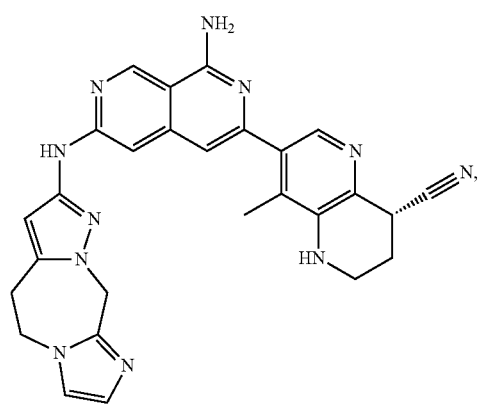
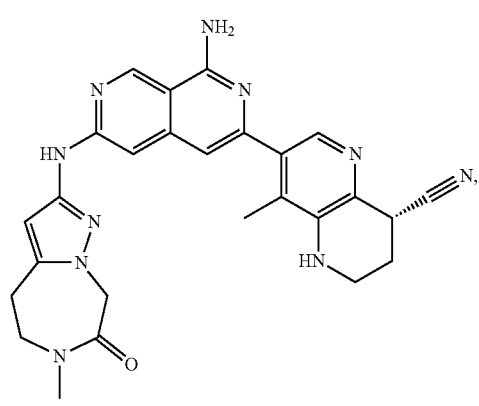
1550
-continued
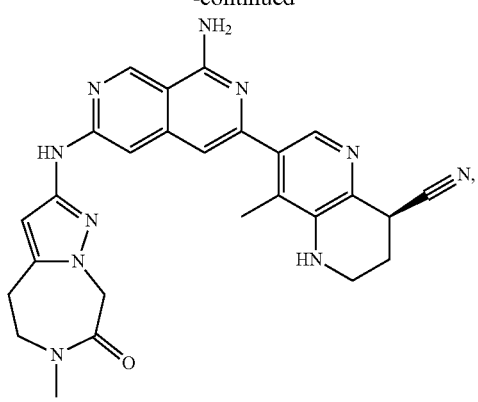
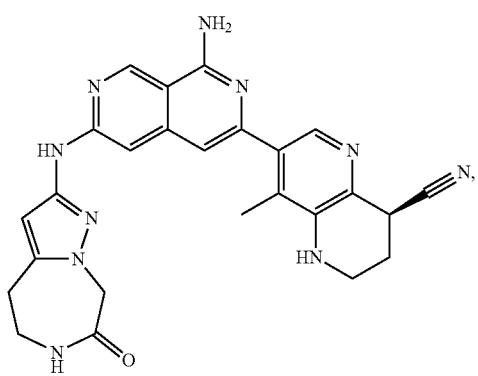
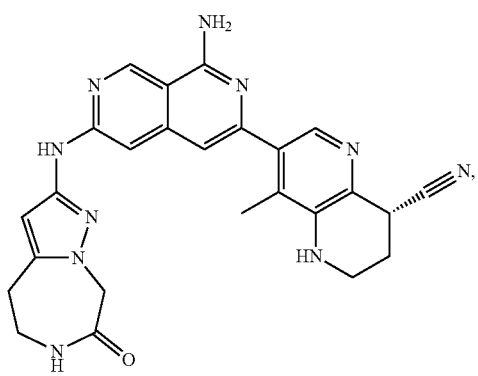
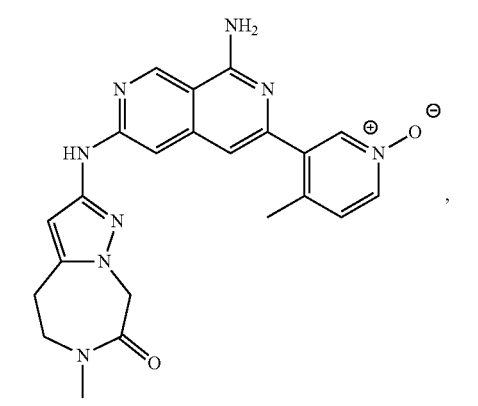

1551
-continued
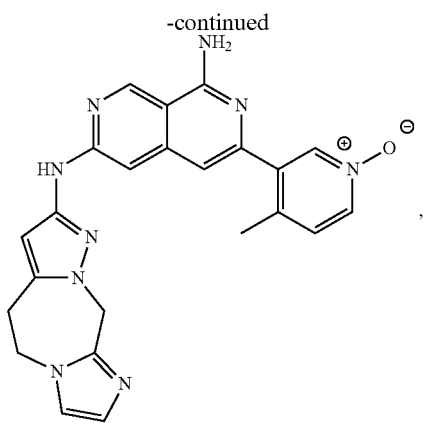
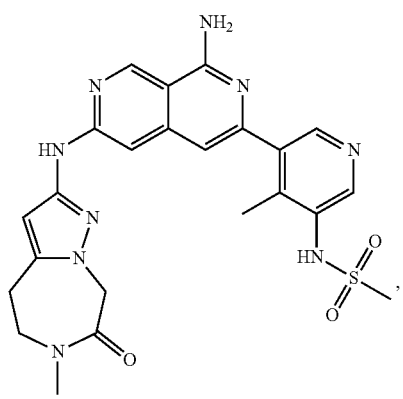
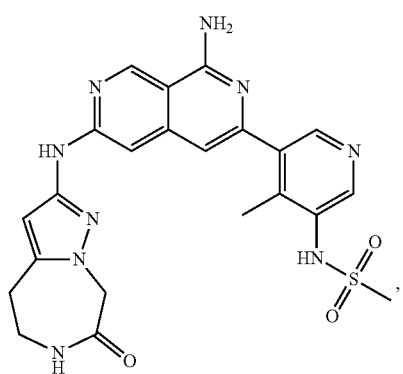
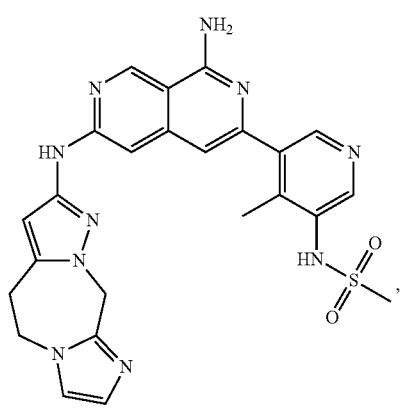
1552
-continued
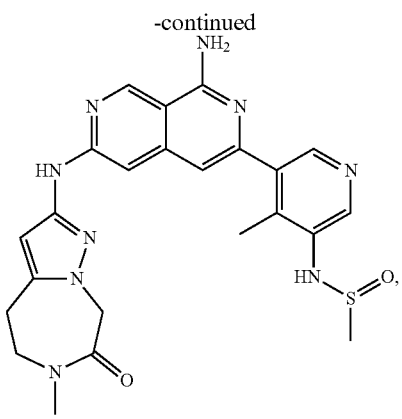
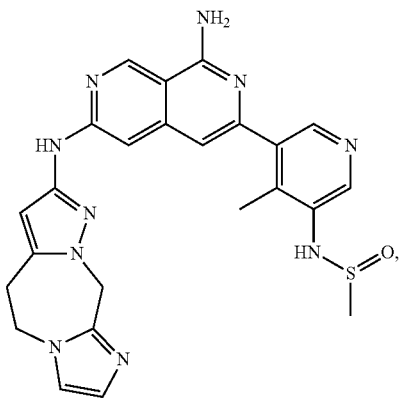
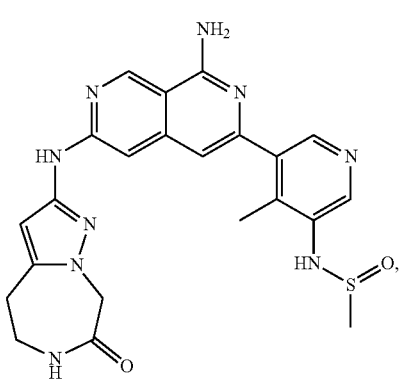
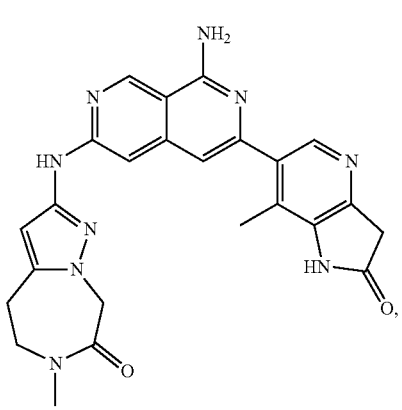

1553
-continued
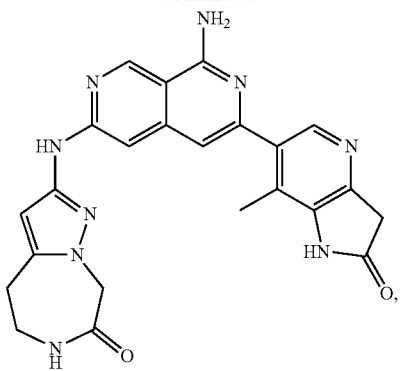
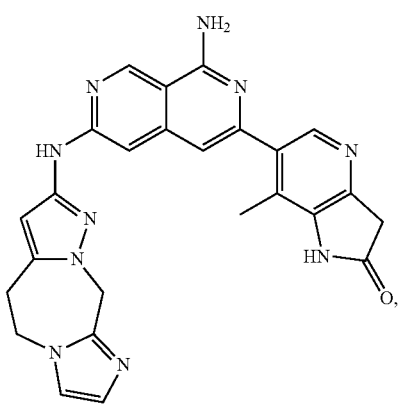
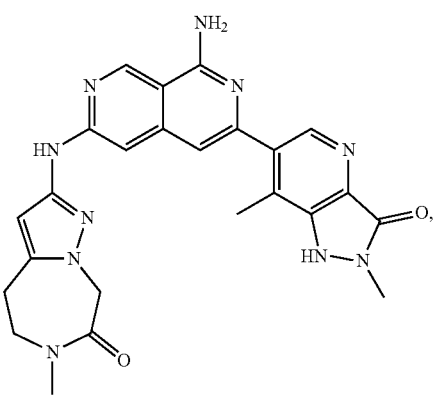
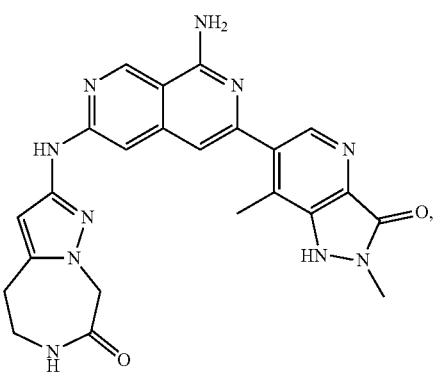
1554
-continued
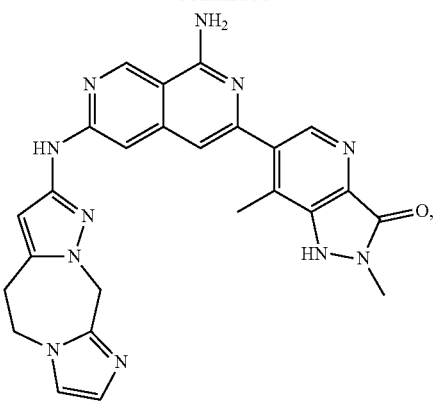
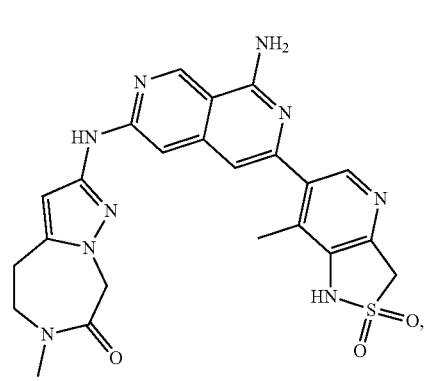
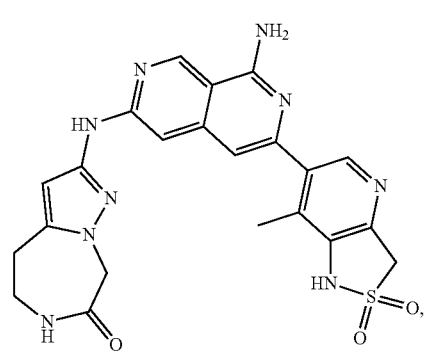
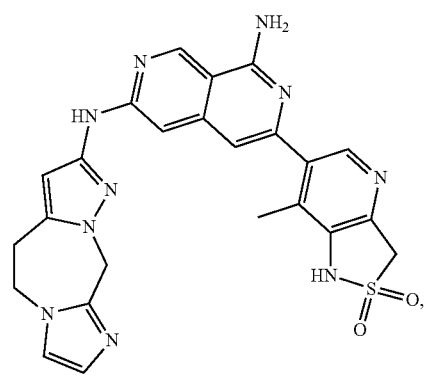

1555 -continued
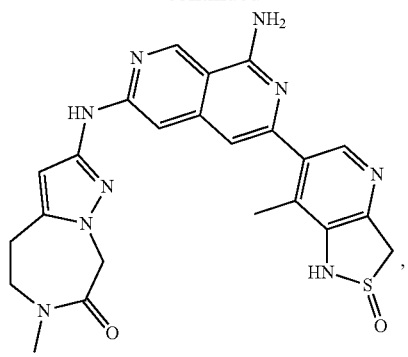
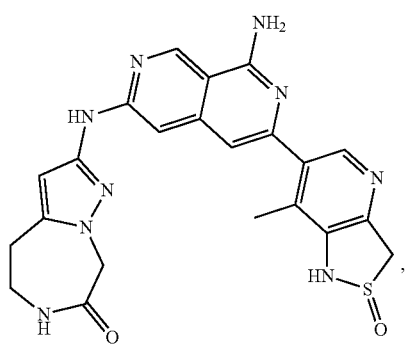
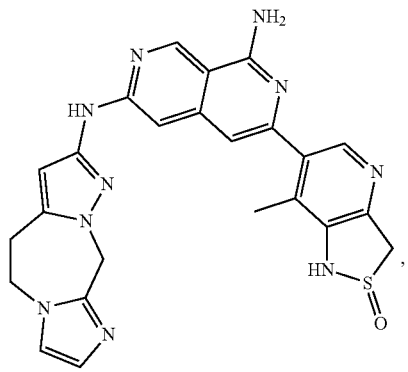
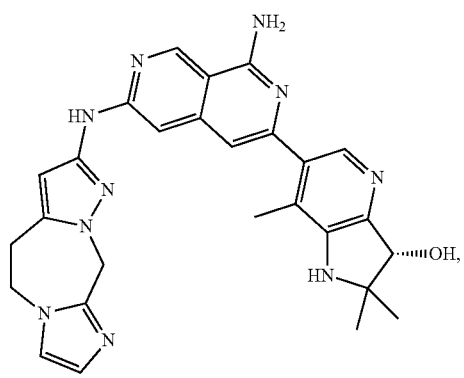
1556 -continued
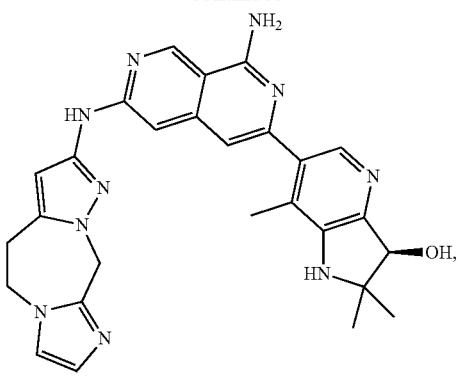
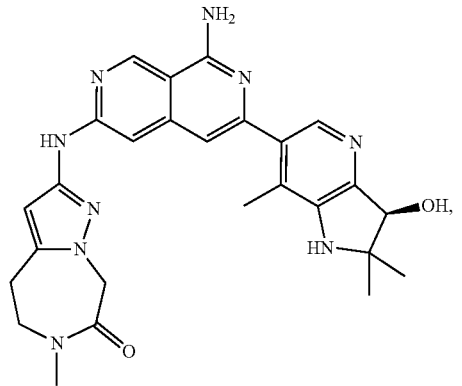
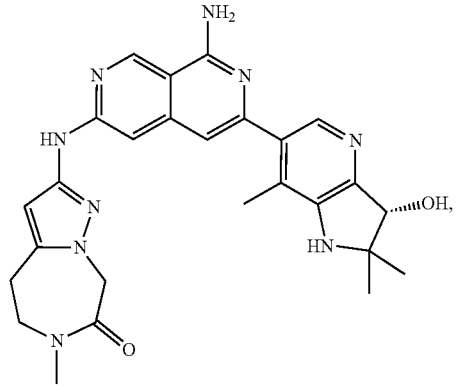
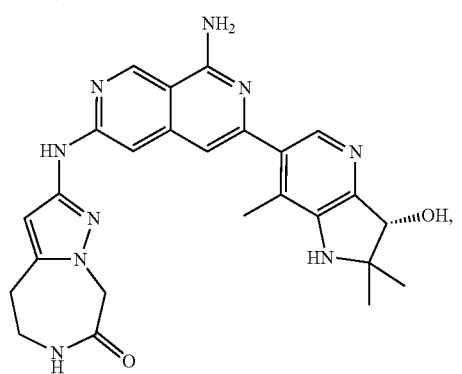

1557
-continued
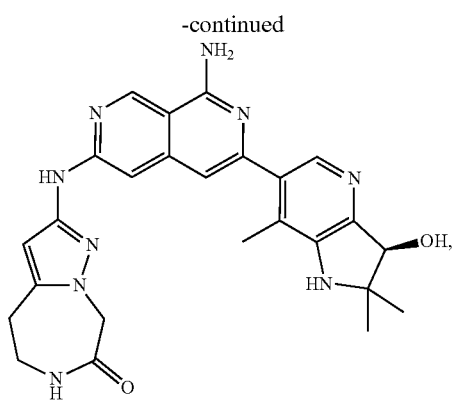
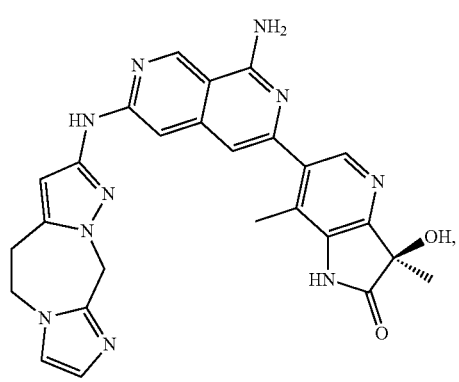
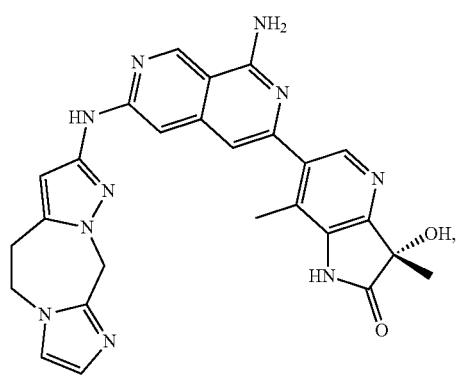
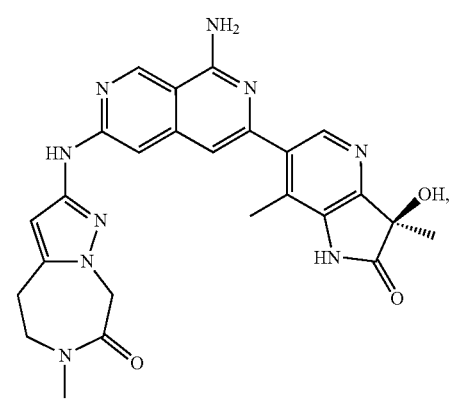
1558
-continued
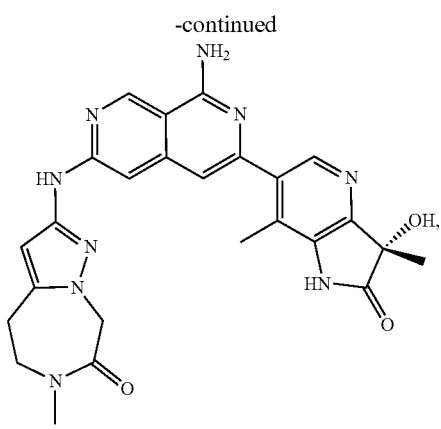
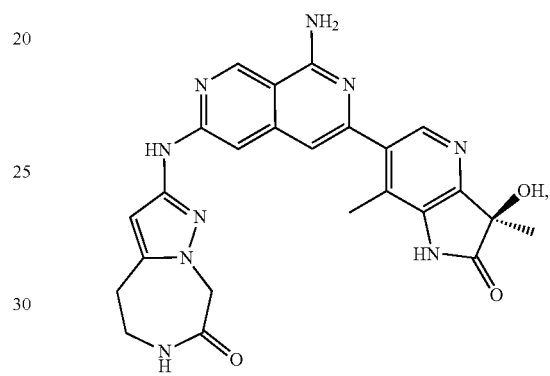
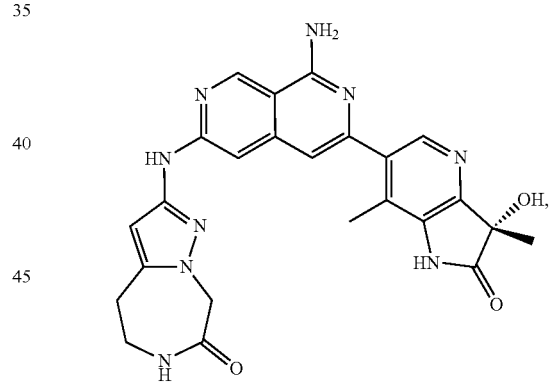
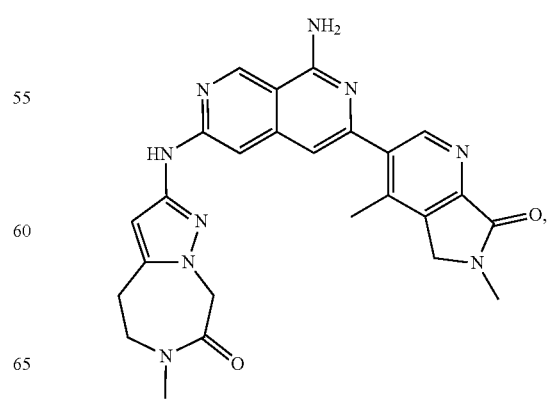

1559
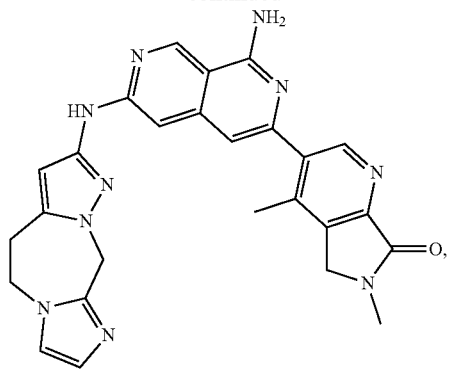
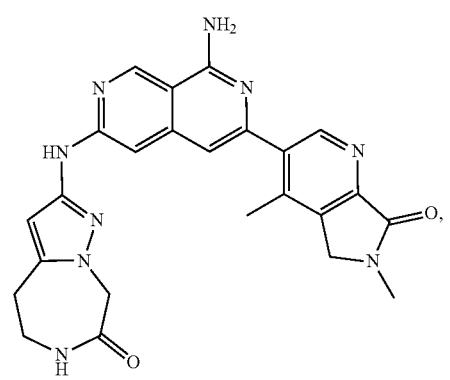
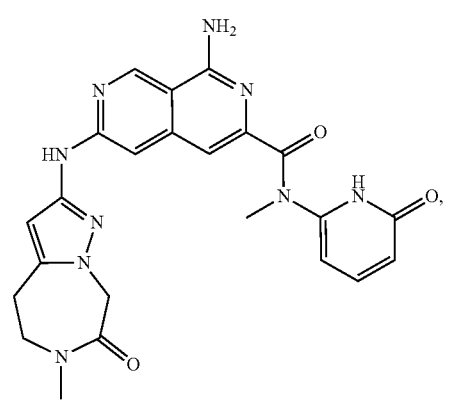
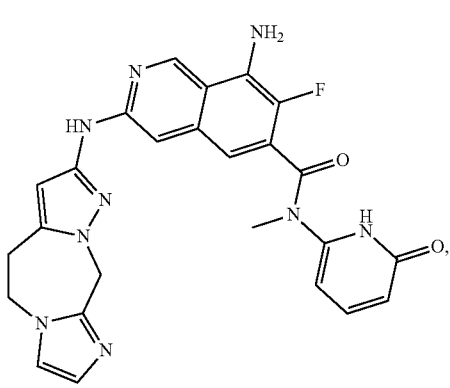
1560
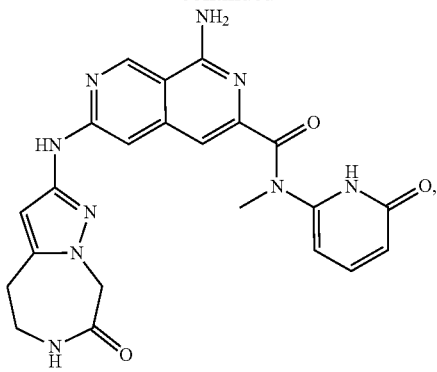
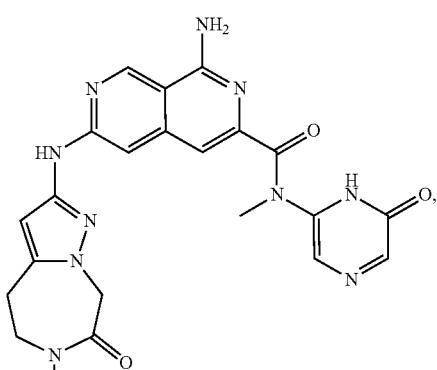
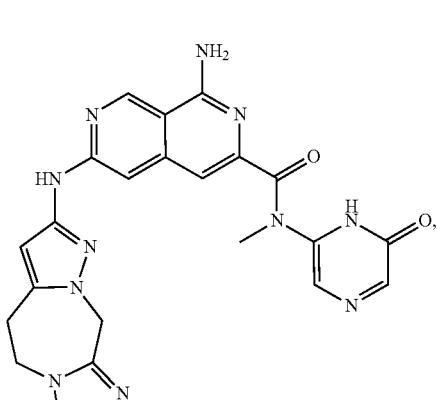
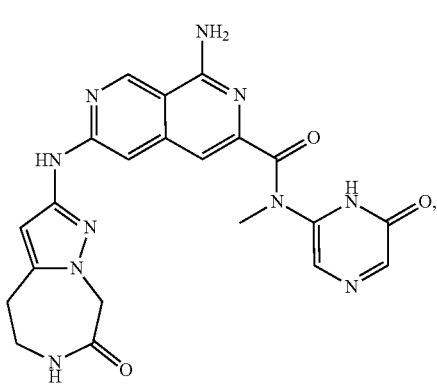

1561
-continued
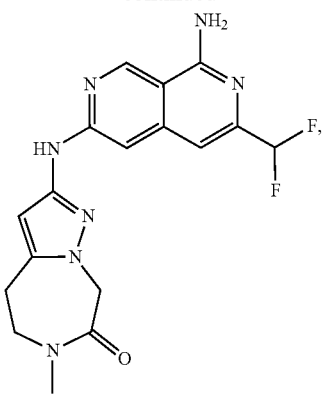
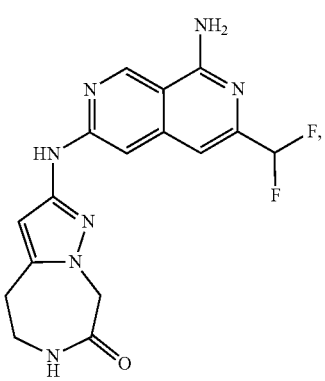
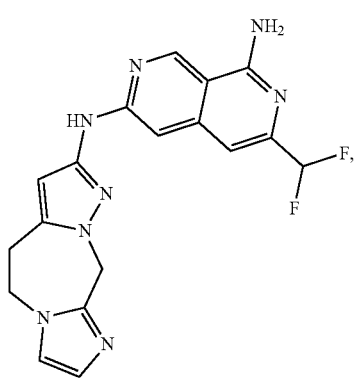
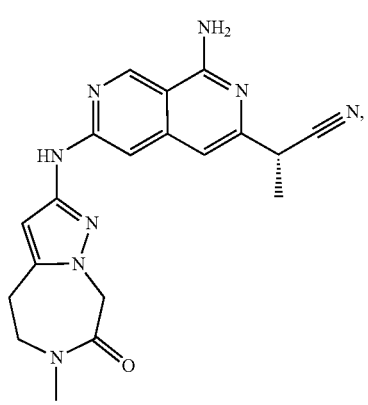
1562
-continued
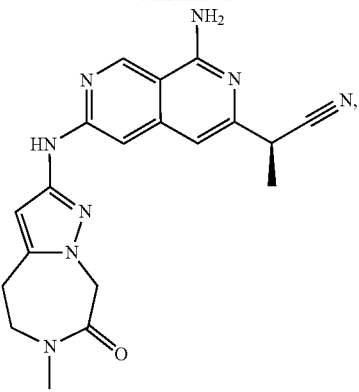
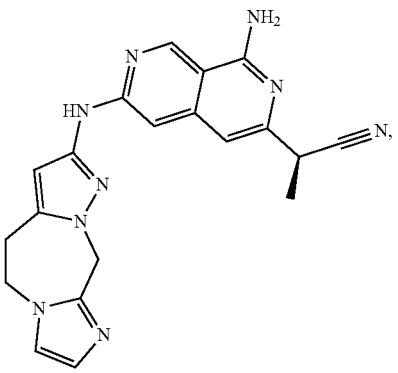
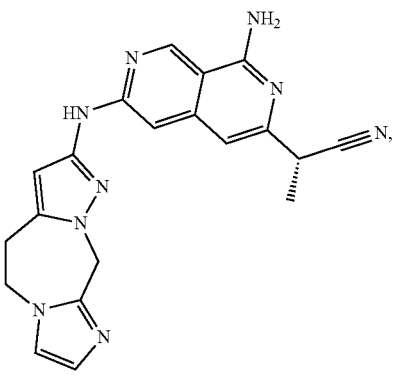
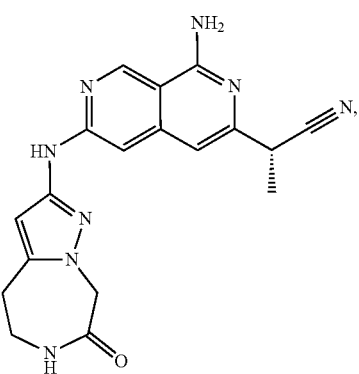

1563
-continued
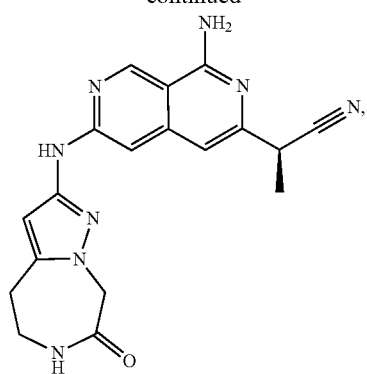
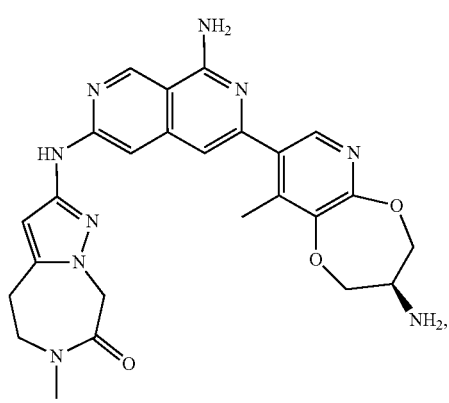
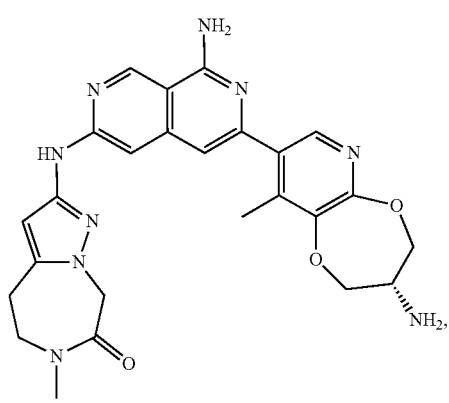
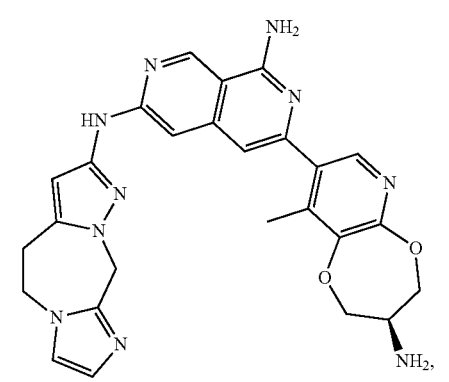
1564
-continued
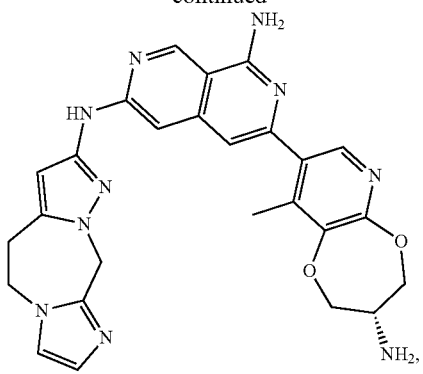
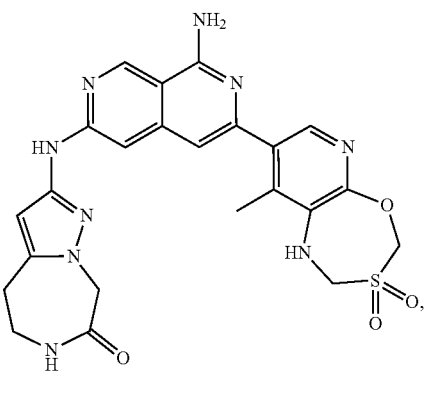
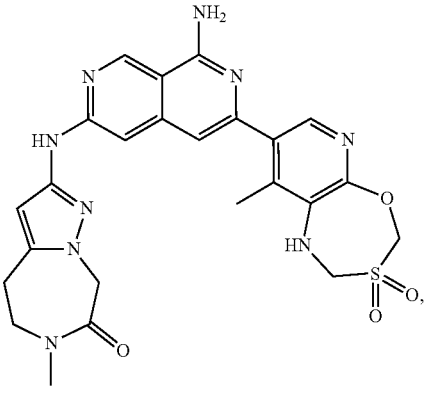
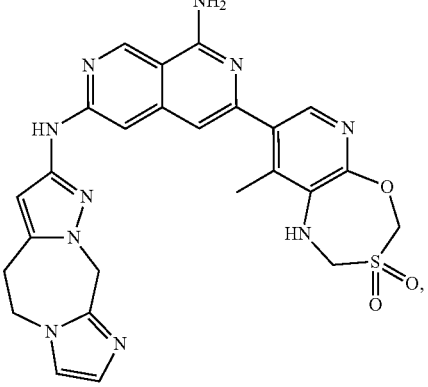

1565
-continued
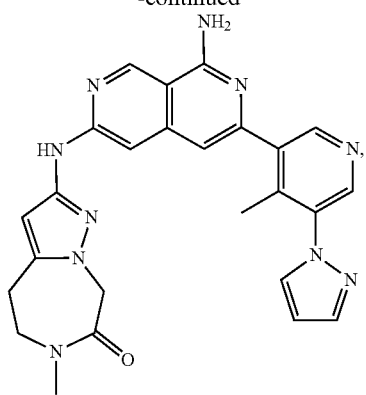
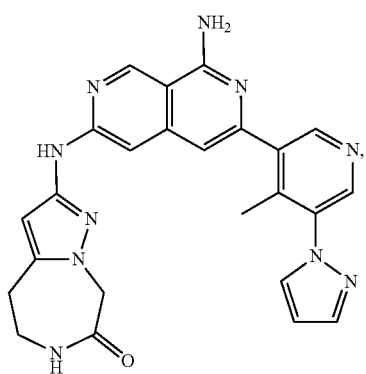
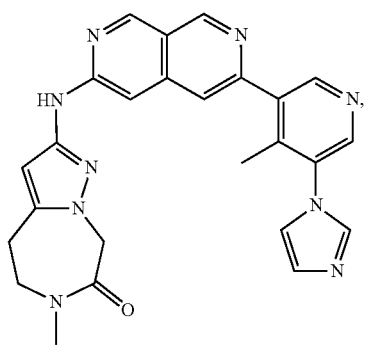
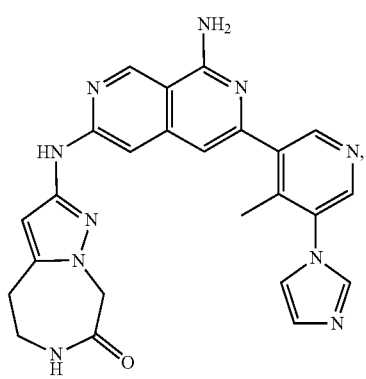
1566
-continued
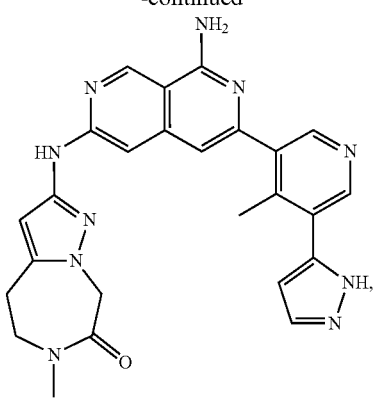
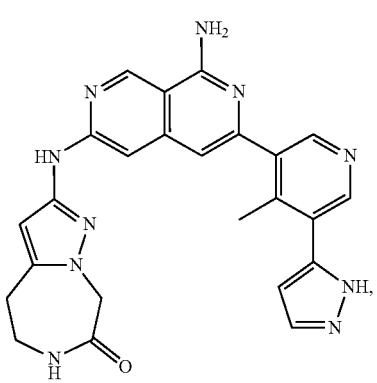
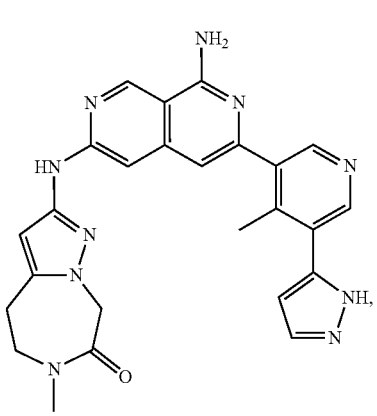
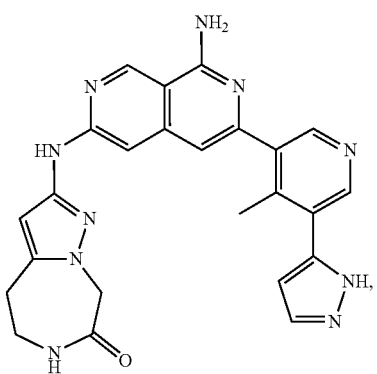

1567
-continued
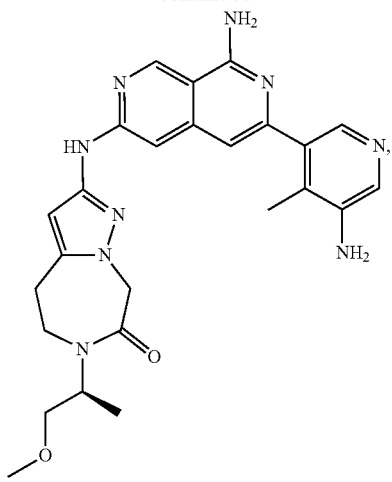
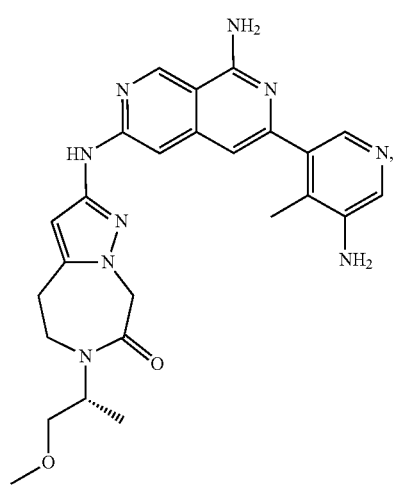
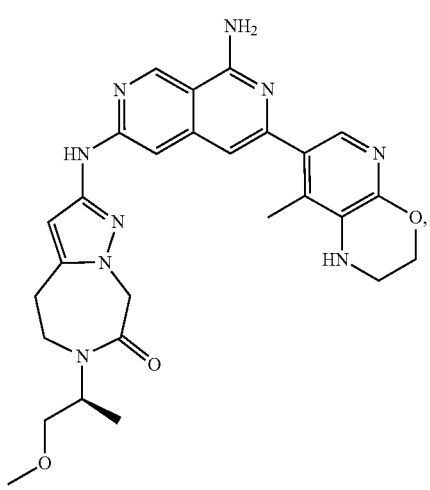
1568
-continued
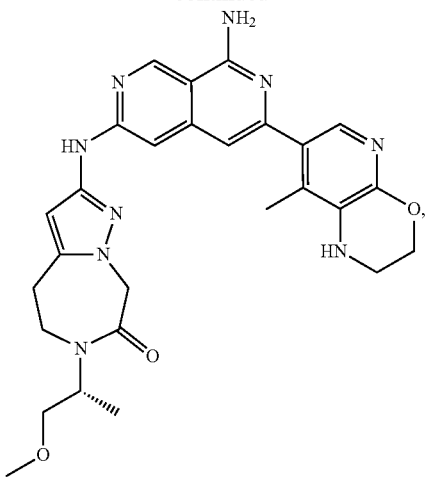
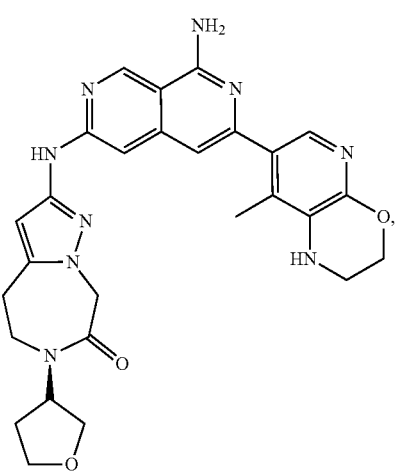
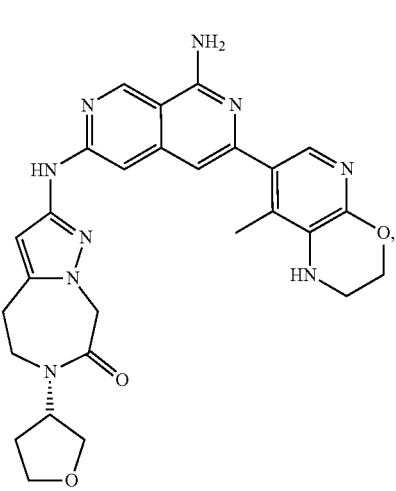

1569
-continued
1570
-continued
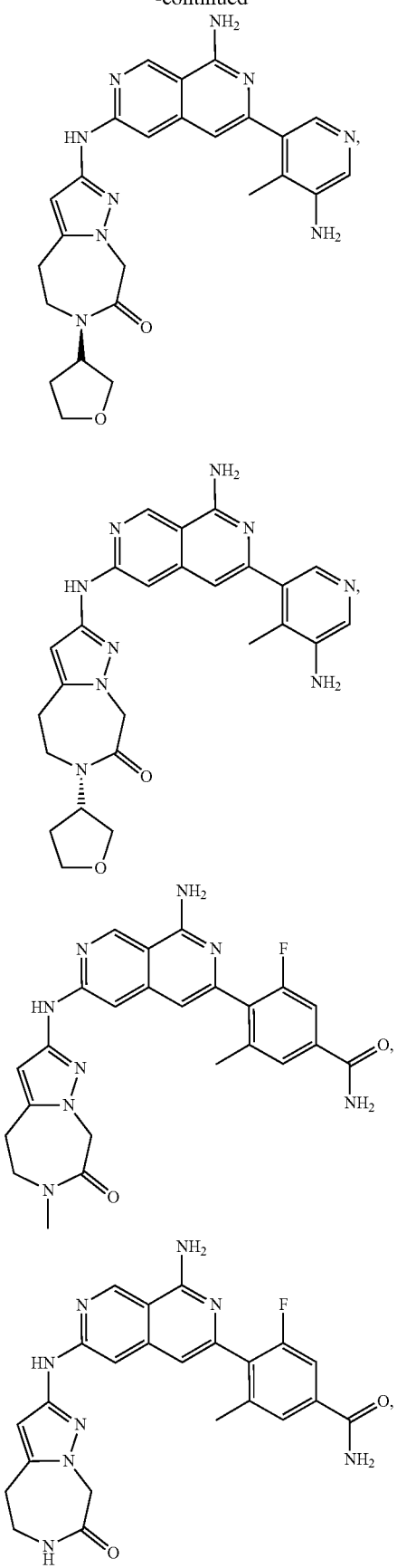
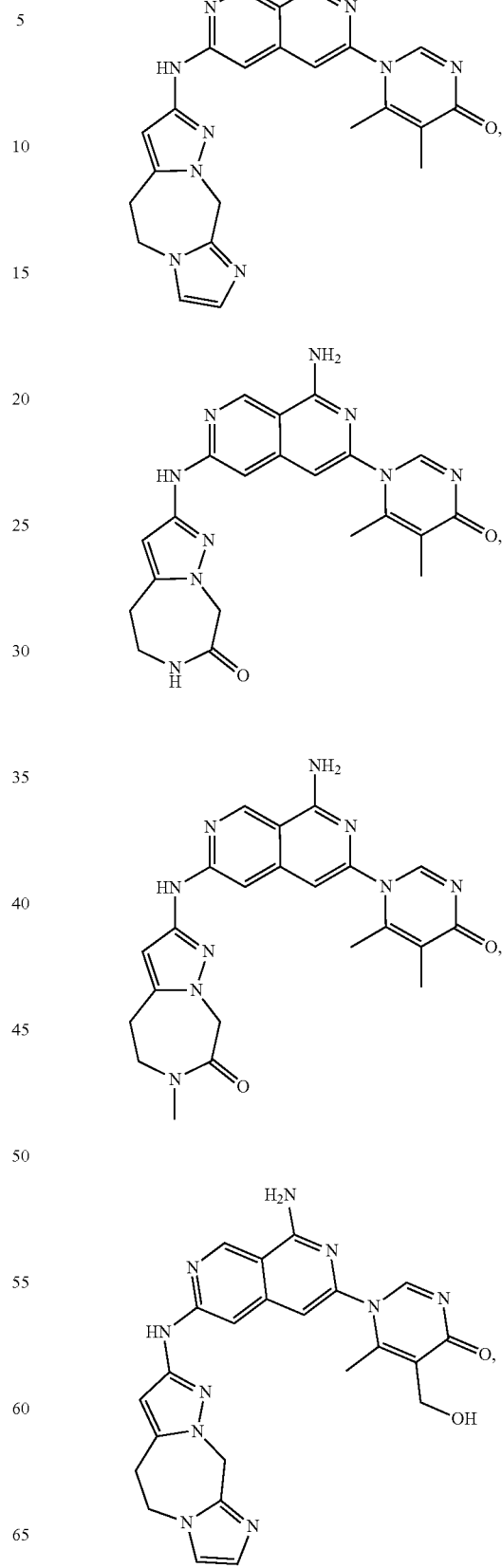

1571
-continued
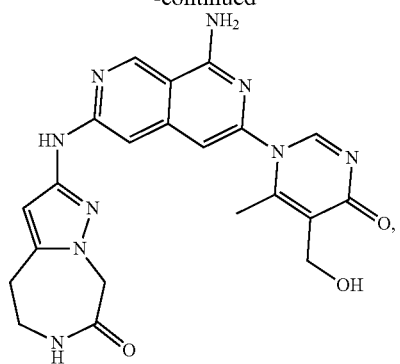
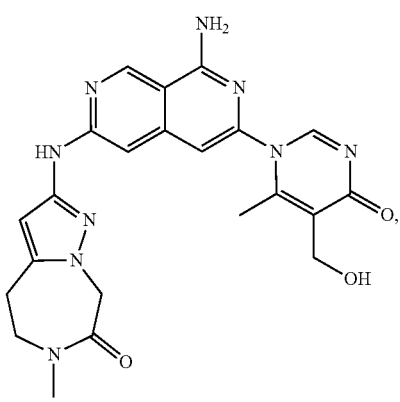
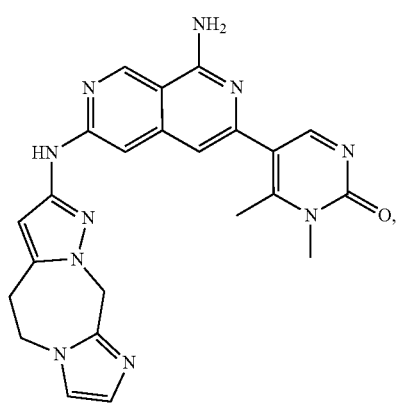
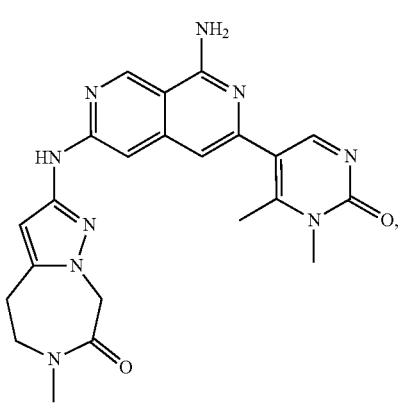
1572
-continued
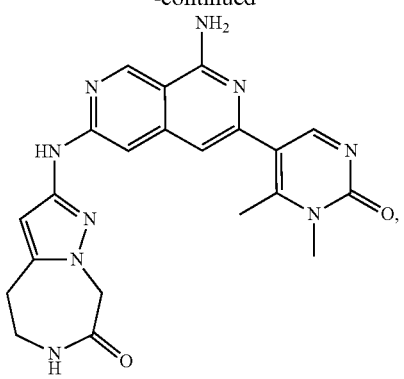
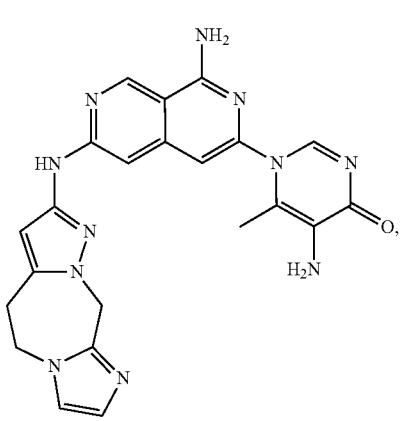
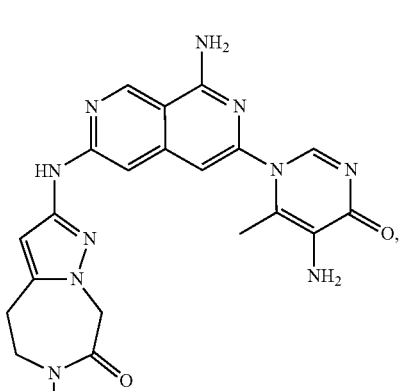
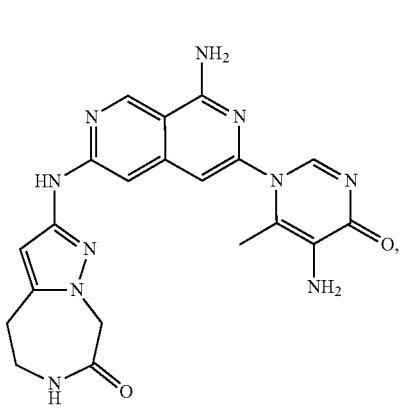

1573
-continued
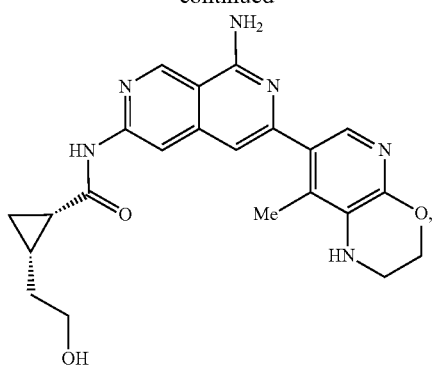
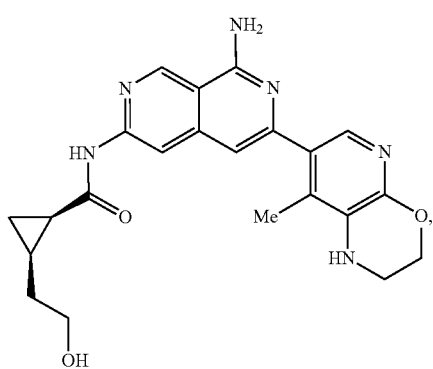
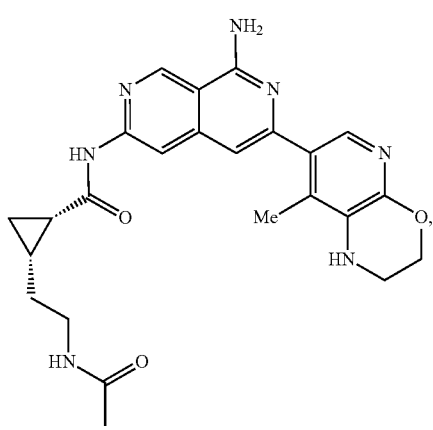
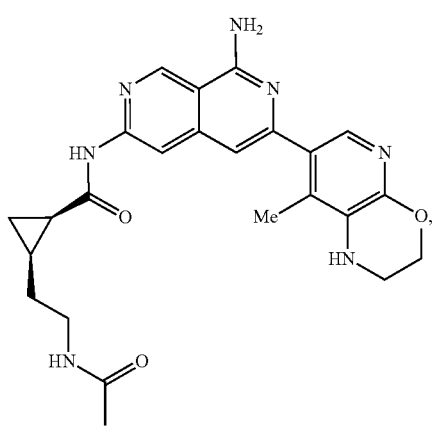
1574
-continued
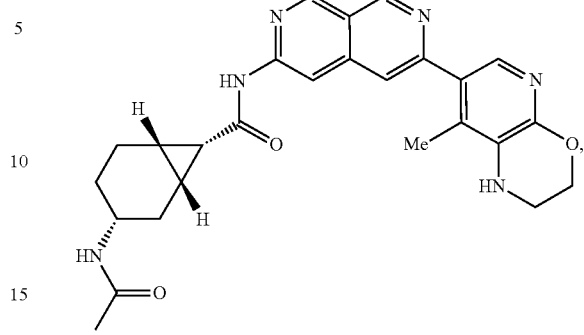
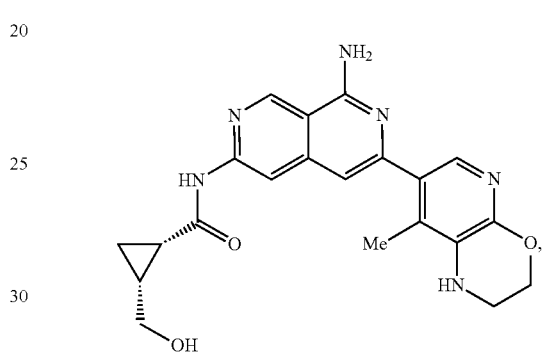
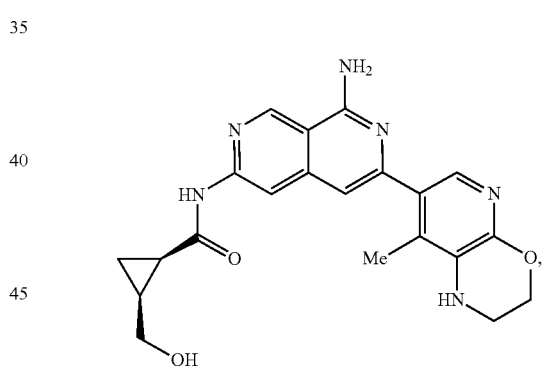
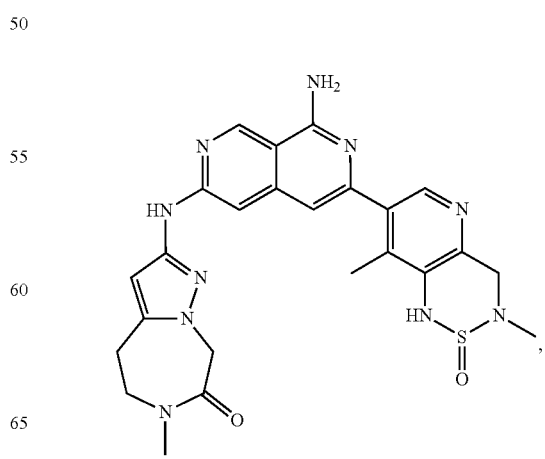

1575
-continued
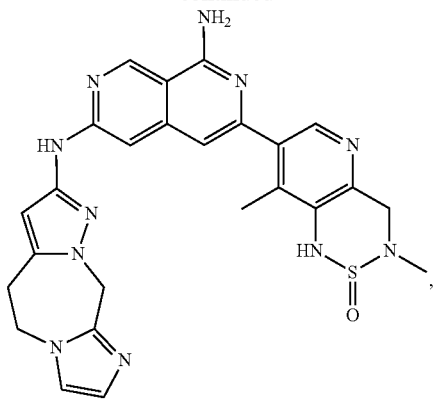
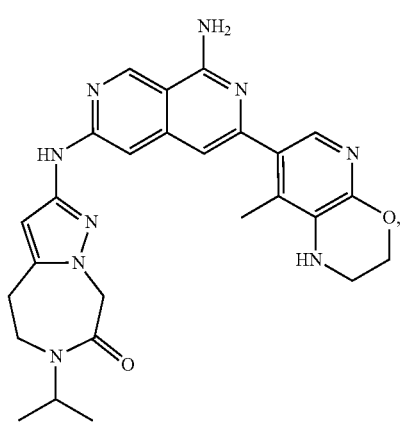
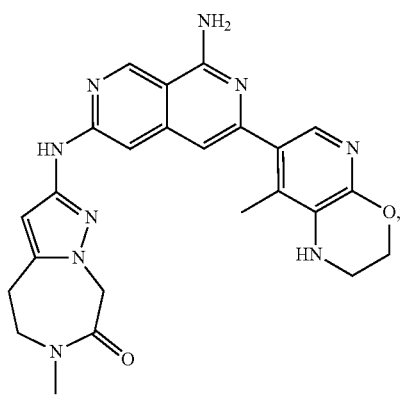
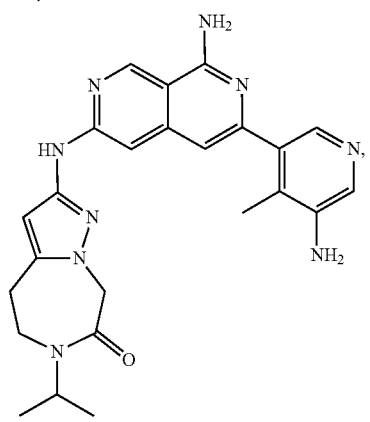
1576
-continued
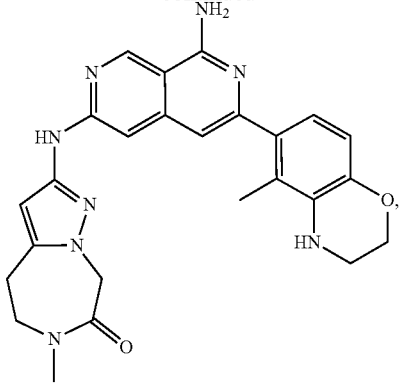
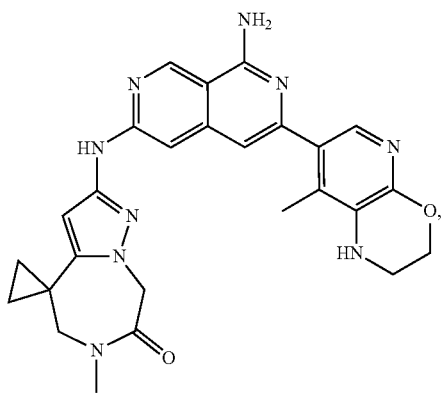
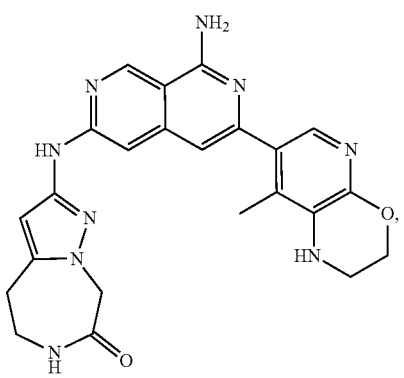
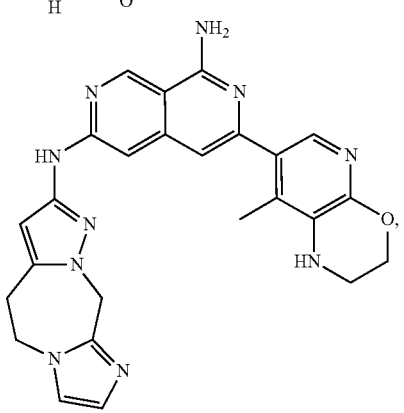

1577
-continued
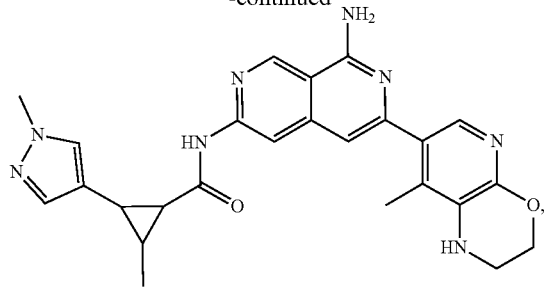
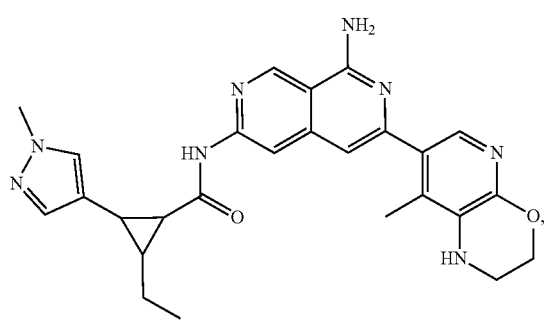
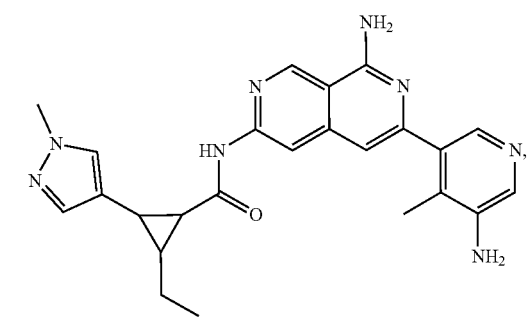
1578
-continued
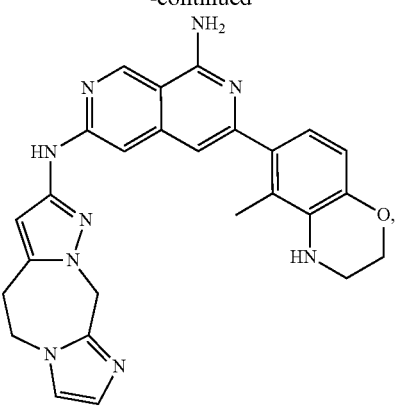
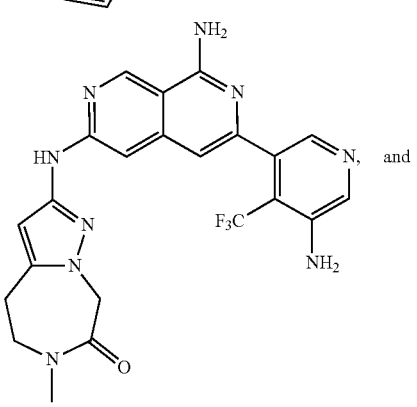
and
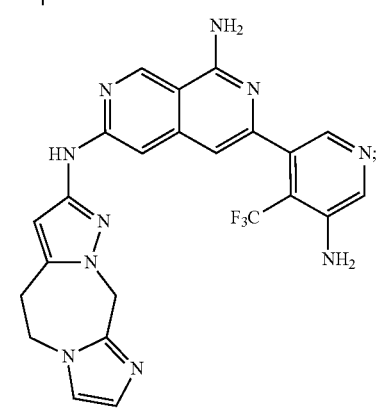
or a pharmaceutically acceptable salt, thereof.
* * * * *